(12) United States Patent
Bartlett et al.

(10) Patent No.: US 12,110,294 B2
(45) Date of Patent: Oct. 8, 2024

(54) CD73 COMPOUNDS

(71) Applicant: Gilead Sciences, Inc., Foster City, CA (US)

(72) Inventors: Mark J. Bartlett, Castro Valley, CA (US); Gregory F. Chin, San Francisco, CA (US); Michael O. Clarke, Redwood City, CA (US); Jennifer L. Cosman, Foster City, CA (US); Deeba Ensan, Foster City, CA (US); Bindu Goyal, Fremont, CA (US); Stephen Ho, Redwood City, CA (US); Hon C. Hui, San Mateo, CA (US); Richard L. Mackman, Millbrae, CA (US); Michael R. Mish, Foster City, CA (US); Scott D. Schroeder, Union City, CA (US); Nathan D. Shapiro, Belmont, CA (US); Dustin S. Siegel, Half Moon Bay, CA (US); Doris T. Tang, Burlingame, CA (US); Hai Yang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 91 days.

(21) Appl. No.: 17/243,911

(22) Filed: Apr. 29, 2021

(65) Prior Publication Data

US 2023/0039553 A1    Feb. 9, 2023

Related U.S. Application Data

(60) Provisional application No. 63/149,803, filed on Feb. 16, 2021, provisional application No. 63/018,774, filed on May 1, 2020.

(51) Int. Cl.
| | |
|---|---|
| *C07D 487/04* | (2006.01) |
| *A61K 45/06* | (2006.01) |
| *C07D 519/00* | (2006.01) |
| *C07K 16/28* | (2006.01) |

(52) U.S. Cl.
CPC .......... *C07D 487/04* (2013.01); *A61K 45/06* (2013.01); *C07D 519/00* (2013.01); *C07K 16/2818* (2013.01); *C07K 16/2827* (2013.01)

(58) Field of Classification Search
CPC .......................... C07D 487/04; C07D 519/00
See application file for complete search history.

(56) References Cited

U.S. PATENT DOCUMENTS

2023/0183189 A1    6/2023    Bartlett et al.

FOREIGN PATENT DOCUMENTS

| | | |
|---|---|---|
| CN | 1592624 A | 3/2005 |
| WO | WO-2006/015123 A1 | 2/2006 |
| WO | WO-2011031979 A1 | 3/2011 |
| WO | WO-2011082270 A2 | 7/2011 |
| WO | WO-2012005805 A1 | 1/2012 |
| WO | WO-2012/025187 A2 | 3/2012 |
| WO | WO-2019168744 A1 | 9/2019 |
| WO | WO-2021222522 A1 | 11/2021 |
| WO | WO-2022068929 A1 * | 4/2022 |
| WO | WO-2022121914 A1 * | 6/2022 |

OTHER PUBLICATIONS

Google translation of WO 2022068929, downloaded on Mar. 11, 2023, <https://patents.google.com/patent/WO2022068929A1/en?oq=WO+2022068929>, pp. 1-71.*
International Search Report and Written Opinion mailed Jul. 12, 2021 for PCT/US2021/029828.
Intl. Search Report-Written Opinion dated Feb. 9, 2023 for Intl. Appl. No. PCT/US2022/078822, 12 pages.
Office Action dated Apr. 6, 2022 for Taiwanese Appl. No. 110115754, 6 pages.
Office Action dated Jan. 12, 2023 for Panamanian Appl. No. PI/2022/94196-01, 2 pages.
Examination Report dated Feb. 22, 2023 for Indian Appl. No. 202217063551, 6 pages.
International Preliminary Report on Patentability dated Oct. 27, 2022 for Intl. Appl. No. PCT/US2021/029828, 7 pages.
Examination Report dated Apr. 19, 2023 for Australian Appl. No. 2021264550, 2 pages.
Koledova et al. (2018) "European Network of Breast Development and Cancer turned 10 years: a growing family of mammary gland researchers", Breast Cancer Research, 20(1), p. 1-5.
Office Action dated Oct. 12, 2023 for Chinese Appl. No. 202180039029.0, 19 pages.
Office Action dated Dec. 26, 2023 for Japanese Appl. No. 2022-566359, 5 pages.

* cited by examiner

*Primary Examiner* — Susanna Moore

(57) ABSTRACT

The present disclosure provides pyrimidine dione compounds of Formula I

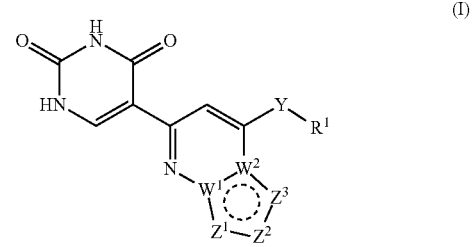

and pharmaceutical compositions thereof, for treating cancer, including solid tumors either-used alone or in combination with other anti-cancer agents.

7 Claims, No Drawings

Specification includes a Sequence Listing.

CD73 COMPOUNDS

CROSS-REFERENCES TO RELATED APPLICATIONS

This application claims the benefit under 35 U.S.C. § 119(e) of U.S. Provisional Application No. 63/018,774, filed on May 1, 2020, and of U.S. Provisional Application No. 63/149,803, filed on Feb. 16, 2021, which are hereby incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Sep. 21, 2021, is named 1339-US-NP_SL.txt and is 873 bytes in size.

BACKGROUND OF THE INVENTION

The glycosyl-phosphatidylinositol-anchored CD73 antigen (also known as Cluster of Differentiation 73, ecto-5'-nucleotidase, ecto-5'-NT, 5'-NT, and NTSE) is considered the rate-limitin enzyme in the generation of extracellular adenosine (Stagg J, Smyth M J. Extracellular adenosine triphosphate and adenosine in cancer. Oncogene. 2010; 29:5346-58. doi:10.1038/onc.2010.292). CD73 is a 70-kDa glycosylphosphatidylinositol (GPI)-anchored protein normally expressed on endothelial cells and subsets of hematopoietic cells. CD73, together with CD39, regulates adenosine triphosphate (ATP) metabolism. CD39 (NTPDase-1) converts ATP into AMP, with only trace amounts of ADP being released, while CD73 catalyzes the conversion of AMP to adenosine (Ado).

Extracellular Ado accumulates in cancerous tissues and constitutes an important mechanism of tumor immune escape. Among other effects, tumor-derived Ado profoundly inhibits infiltrating effector T cells. ATP degradation into Ado through CD39 and CD73 co-expressed on murine Treg (regulatory CD4+ T cells) has been shown as responsible for tumor immunosuppression.

CD73 can be found constitutively expressed at high levels on various types of cancer cells. CD73-generated adenosine is assumed to suppress adaptive anti-tumor immune responses thereby promoting tumor growth and metastasis. And studies in animal models have shown that blockade of CD73 activity suppresses tumor growth and prolongs survival by promoting anti-tumor adaptive immunity (Forte et al. (2012) J Immunol. 189(5):2226-33). Given the need for cancer treatments, new compositions and methods for regulating CD73 activity and related therapeutic agents is needed. This disclosure meets this and other needs.

BRIEF SUMMARY OF THE INVENTION

In one embodiment, the present disclosure provides a compound of Formula (I):

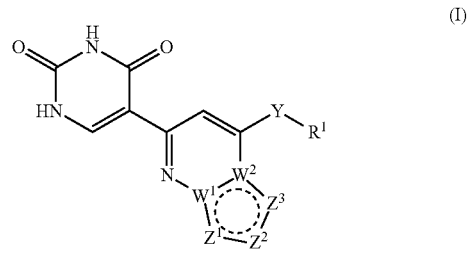

or a pharmaceutically acceptable salt thereof, wherein
Y is a bond, —$C_{1-6}$alkyl, —$C_{2-6}$alkenyl, —$C_{2-6}$alkynyl, —$C_{3-7}$cycloalkyl, —$C_{1-6}$alkyl-O—, —$C_{1-6}$alkyl-O—$C_{1-6}$alkyl, —O—$C_{1-6}$alkyl, —O—$C_{1-6}$alkyl-O—, —$C_{3-7}$cycloalkyl-O—, —O—$C_{3-7}$cycloalkyl, —$C_{3-7}$cycloalkyl-$C_{1-3}$alkyl, —S(=O)$_2$—, —S(=O)$_2$CH$_2$—, —CH$_2$S(=O)$_2$—, —N($R^a$)—, —N($R^a$)CH$_2$—, —$C_{1-6}$alkyl-N($R^b$)—, —$C_{3-7}$cycloalkyl-N($R^b$)—, —N($R^a$)C(=O)—, —$C_{1-3}$alkylN($R^a$)C(=O)—, heterocycloalkyl-C(=O)—, heterocycloalkyl-N(H)C(=O)—, heterocycloalkyl, heterocycloalkyl-$C_{1-6}$alkyl-O—, or heterocycloalkyl-O—, wherein each alkyl, cycloalkyl, or heterocycloalkyl is optionally substituted with one to four halogens and is further optionally substituted with one or two groups independently selected from —CN, —$C_{1-3}$alkyl and —$C_{1-3}$ haloalkyl;
one or two of $Z^1$, $Z^2$ and $Z^3$ is $CR^2$ and the remaining one or two of $Z^1$, $Z^2$, and $Z^3$ is N;
one of $W^1$ and $W^2$ is N and the other is C;
$R^1$ is hydrogen, —CN, —$C_{1-6}$alkyl, —$C_{3-7}$cycloalkyl, —$C_{6-12}$aryl, —$C_{1-6}$alkyl-$C_{6-12}$aryl, —$C_{1-6}$alkyl-heteroaryl, heterocycloalkyl, heteroaryl, or —$C_{1-6}$alkyl-O—$C_{1-6}$alkyl, wherein each alkyl, cycloalkyl, aryl, heterocycloalkyl, or heteroaryl is optionally substituted with one to three halogens and is further optionally substituted with one or two $R^3$;
$R^2$ is each independently hydrogen, halogen, —CN, —$C_{1-6}$alkyl, —$C_{3-10}$cycloalkyl, —O—$C_{1-6}$alkyl, —C(=O)O$R^a$, —C(=O)heterocycloalkyl, —C(=O)N($R^b$)$C_{6-12}$aryl, —C(=O)N($R^b$)heteroaryl, —C(=O)N($R^b$)($R^b$), —$C_{1-6}$alkyl-S(=O)$_2C_{6-12}$aryl, —N($R^b$)($R^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$;
$R^3$ is halogen, —CN, —$C_{1-6}$alkyl, —$C_{3-7}$cycloalkyl, —$C_{1-3}$alkyl-$C_{3-7}$cycloalkyl, —$C_{1-3}$alkyl-heterocycloalkyl, —N($R^b$)($R^b$), —N(H)C(=O)O—$R^c$, —C(=O)N($R^b$)($R^b$), —C(=O)O$C_{1-6}$alkyl, —C(=O)O$C_{1-6}$alkyl$C_{6-12}$aryl, —C(=O)O$C_{1-3}$alkyl, —C(=O)$C_{3-7}$cycloalkyl, —C(=O)heterocycloalkyl, —OC(=O)heterocycloalkyl, —OC(=O)N(H)$C_{1-6}$alkyl, —OC(=O)N(H)$C_{3-7}$cycloalkyl, —OC(=O)O$C_{1-6}$alkyl, —OC(=O)N(H)$C_{6-12}$aryl, or —O$R^c$, wherein each alkyl, cycloalkyl, heterocycloalkyl, or aryl is optionally substituted with one to three halogens and is further optionally substituted with one or two $R^c$;

R⁴ is halogen, —CN, —ORᶜ, —C₁₋₆alkyl, —N(Rᵇ)(Rᵇ), or —C₁₋₆haloalkyl;
Rᵃ is each independently hydrogen, or —C₁₋₃alkyl;
Rᵇ is each independently hydrogen, —C₁₋₆alkyl, —C₁₋₆haloalkyl, —C₁₋₆alkyl-C₃₋₇cycloalkyl, —C₃₋₇cycloalkyl-C₁₋₆ haloalkyl, —C₃₋₇cycloalkyl, —C₃₋₇ halocycloalkyl, or —C(=O)C₁₋₆alkyl; and
Rᶜ is each independently hydrogen, —C₁₋₆alkyl, —C₁₋₆ haloalkyl, —C₃₋₇cycloalkyl, —C₁₋₃alkyl-C₃₋₇cycloalkyl, —C₁₋₃alkyl-C₃₋₇cyclohaloalkyl, —OC₁₋₆alkyl, or —C₃₋₇ halocycloalkyl; and
wherein each heterocycloalkyl or heteroaryl bears one to four heteroatoms each independently selected from N, O, and S;
wherein each heterocycloalkyl has 4 to 15 ring members; and
wherein each heteroaryl has 5 to 15 ring members.

In another embodiment, the present disclosure provides a compound of Formula (I):

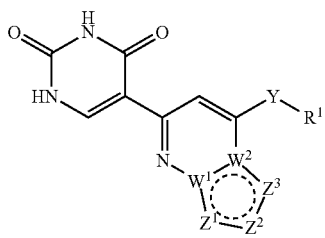

(I)

or a pharmaceutically acceptable salt thereof, wherein
Y is a bond, —C₁₋₆alkyl, —C₂₋₆alkenyl, —C₂₋₆alkynyl, —C₃₋₇cycloalkyl, —C₁₋₆alkyl-O—, —C₁₋₆alkyl-O—C₁₋₆alkyl, —O—C₁₋₆alkyl, —C₃₋₇cycloalkyl-O—, —O—C₃₋₇cycloalkyl, —C₃₋₇cycloalkyl-C₁₋₃alkyl-, —S(=O)₂—, —S(=O)₂CH₂—, —CH₂S(=O)₂—, —N(Rᵃ)—, —N(Rᵃ)CH₂—, —C₁₋₆alkyl-N(Rᵇ)—, —C₃₋₇cycloalkyl-N(Rᵇ)—, —N(Rᵃ)C(=O)—, —C₁₋₃alkylN(Rᵃ)C(=O)—, heterocycloalkyl-C(=O)—, heterocycloalkyl or heterocycloalkyl-O—, wherein each alkyl, cycloalkyl, or heterocycloalkyl is optionally substituted with one to four halogens and is further optionally substituted with one or two groups independently selected from —CN and —C₁₋₃alkyl;
one or two of Z¹, Z² and Z³ is CR² and the remaining one or two of Z¹, Z², and Z³ is N;
one of W¹ and W² is N and the other is C;
R¹ is hydrogen, —CN, —C₁₋₆alkyl, —C₃₋₇cycloalkyl, —C₆₋₁₂aryl, heterocycloalkyl, heteroaryl, or —C₁₋₆alkyl-O—C₁₋₆alkyl, wherein each alkyl, cycloalkyl, aryl, heterocycloalkyl, or heteroaryl is optionally substituted with one to three halogens and is further optionally substituted with one or two R³;
R² is each independently hydrogen, halogen, —CN, —C₁₋₆alkyl, —C₃₋₁₀cycloalkyl, —O—C₁₋₆alkyl, —C(=O)ORᵃ, —C(=O)N(Rᵇ)C₆₋₁₂aryl, —C(=O)N(Rᵇ)heteroaryl, —C(=O)N(Rᵇ)(Rᵇ), —C₁₋₆alkyl-S(=O)₂C₆aryl, —N(Rᵇ)(Rᵇ), —C₆₋₁₂aryl, heterocycloalkyl, or heteroaryl, wherein each alkyl, cycloalkyl, heterocycloalkyl, aryl, or heteroaryl is optionally substituted with one to three halogens and is further optionally substituted with one to three R⁴;

R³ is halogen, —CN, —C₁₋₆alkyl, —C₁₋₆haloalkyl, —C₃₋₇cycloalkyl, —N(Rᵇ)(Rᵇ), —C(=O)OC₁₋₆alkyl, —OC(=O)N(H)C₁₋₆alkyl, —OC(=O)OC₁₋₆alkyl, or —ORᶜ;
R⁴ is halogen, —CN, —ORᶜ, —C₁₋₆alkyl, —N(Rᵇ)(Rᵇ), or —C₁₋₆haloalkyl;
Rᵃ is each independently hydrogen, or —C₁₋₃alkyl;
Rᵇ is each independently hydrogen, —C₁₋₆alkyl, —C₁₋₆haloalkyl, —C₁₋₆alkyl-C₃₋₇cycloalkyl, —C₃₋₇cycloalkyl, —C₃₋₇ halocycloalkyl, or —C(=O)C₁₋₆alkyl; and
Rᶜ is each independently hydrogen, —C₁₋₆alkyl, —C₁₋₆ haloalkyl, —C₃₋₇cycloalkyl, or —C₃₋₇halocycloalkyl; and
wherein each heterocycloalkyl or heteroaryl bears one to four heteroatoms each independently selected from N, O, and S;
wherein each heterocycloalkyl has 4 to 10 ring members; and
wherein each heteroaryl has 5 to 10 ring members.

In another embodiment, the present disclosure provides a pharmaceutical composition comprising a pharmaceutically effective amount of a compound of the present disclosure, or a pharmaceutically acceptable salt thereof, and a pharmaceutically acceptable carrier or excipient.

In another embodiment, the present disclosure provides a method of inhibiting CD73 in a subject in need thereof, the method comprising administering to the subject a therapeutically effective amount of a compound of the present disclosure, or a pharmaceutically acceptable salt thereof, or a pharmaceutical composition of the present disclosure.

In another embodiment, the present disclosure provides a method of treating cancer in a subject in need thereof, the method comprising administering to the subject a therapeutically effective amount of a compound of the present disclosure, or a pharmaceutically acceptable salt thereof, or a pharmaceutical composition of the present disclosure.

DETAILED DESCRIPTION OF THE INVENTION

I. Definitions

"Alkyl" is a linear or branched saturated monovalent hydrocarbon. For example, an alkyl group can have 1 to 18 carbon atoms (i.e., $C_{1-18}$ alkyl) or 1 to 8 carbon atoms (i.e., $C_{1-8}$alkyl) or 1 to 6 carbon atoms (i.e., $C_{1-6}$alkyl) or 1 to 4 carbon atoms (i.e., $C_{1-4}$alkyl). Examples of alkyl groups include, but are not limited to, methyl (Me, —CH₃), ethyl (Et, —CH₂CH₃), 1-propyl (n-Pr, n-propyl, —CH₂CH₂CH₃), 2-propyl (i-Pr, i-propyl, —CH(CH₃)₂), 1-butyl (n-Bu, n-butyl, —CH₂CH₂CH₂CH₃), 2-methyl-1-propyl (i-Bu, i-butyl, —CH₂CH(CH₃)₂), 2-butyl (s-Bu, s-butyl, —CH(CH₃)CH₂CH₃), 2-methyl-2-propyl (t-Bu, t-butyl, —C(CH₃)₃), 1-pentyl (n-pentyl, —CH₂CH₂CH₂CH₂CH₃), 2-pentyl (—CH(CH₃)CH₂CH₂CH₃), 3-pentyl (—CH(CH₂CH₃)₂), 2-methyl-2-butyl (—C(CH₃)₂CH₂CH₃), 3-methyl-2-butyl (—CH(CH₃)CH(CH₃)₂), 3-methyl-1-butyl (—CH₂CH₂CH(CH₃)₂), 2-methyl-1-butyl (—CH₂CH(CH₃)CH₂CH₃), 1-hexyl (—CH₂CH₂CH₂CH₂CH₂CH₃), 2-hexyl (—CH(CH₃)CH₂CH₂CH₂CH₃), 3-hexyl (—CH(CH₂CH₃)(CH₂CH₂CH₃)), 2-methyl-2-pentyl (—C(CH₃)₂CH₂CH₂CH₃), 3-methyl-2-pentyl (—CH(CH₃)CH(CH₃)CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C(CH₃)₂CH(CH₃)₂), and 3,3-dimethyl-2- butyl (—CH(CH$_3$)C(CH$_3$)$_3$, Other alkyl groups include heptyl, octyl, nonyl, decyl, undecyl, dodecyl, pentadcyl, hexadecyl, heptadecyl and octadecyl.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$ and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers an alkoxy group linked to an alkyl group which is linked to the remainder of the compound such that the alkyl group is divalent. Alkoxyalkyl can have any suitable number of carbon, such as from 2 to 6 ($C_{2-6}$alkoxyalkyl), 2 to 5 ($C_{2-5}$alkoxyalkyl), 2 to 4 ($C_{2-4}$alkoxyalkyl), or 2 to 3 ($C_{2-3}$alkoxyalkyl). Alkoxy and alkyl are as defined above where the alkyl is divalent, and can include, but is not limited to, methoxymethyl (CH$_3$OCH$_2$—), methoxyethyl (CH$_3$OCH$_2$CH$_2$—) and others.

"Alkoxy-alkoxy" refers an alkoxy group linked to a second alkoxy group which is linked to the remainder of the compound. Alkoxy is as defined above, and can include, but is not limited to, methoxy-methoxy (CH$_3$OCH$_2$O—), methoxy-ethoxy (CH$_3$OCH$_2$CH$_2$O—) and others.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, $C_{1-4}$haloalkyl is a $C_{1-4}$alkyl wherein one or more of the hydrogen atoms of the $C_{1-4}$alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having 6 to 12 annular carbon atoms such as bicyclo[3.1.0]hexane and bicyclo[2.1.1]hexane), and polycyclic carbocycles (e.g., tricyclic and tetracyclic carbocycles with up to 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocyclyl" or "heterocycle" or "heterocycloalkyl" as used herein refers to a single saturated or partially unsaturated non-aromatic ring or a multiple ring system having at least one heteroatom in the ring (i.e., at least one annular heteroatom selected from oxygen, nitrogen, and sulfur) wherein the multiple ring system includes at least non-aromatic ring containing at least one heteroatom. The multiple ring system can also include other aromatic rings and non-aromatic rings. Unless otherwise specified, a heterocyclyl group has from 3 to 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from 1 to 6 annular carbon atoms and from 1 to 3 annular heteroatoms selected from the group consisting of oxygen, nitrogen and sulfur in the ring. The heteroatoms can optionally be oxidized to form N(—OH)—, =N(—O⁻)—, —S(=O)— or S(=O)₂—. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, pyrazolidin-3-one, piperazin-2-one, oxazolidin-2-one, and the like.

Heterocycloalkyl rings also include 9 to 15 membered fused ring heterocycloalkyls having 2, 3, or more rings wherein at least one ring is an aryl ring and at least one ring is a non-aromatic ring containing at least one heteroatom. Representative fused bicyclic heterocycloalkyls include, but are not limited to, indoline (dihydroindole), isoindoline (dihydroisoindole), indazoline (dihydroindazole), benzo[d]imidazole, dihydroquinoline, dihydroisoquinoline, dihydrobenzofuran, dihydroisobenzofuran, benzo[d][1,3]dioxol, dihydrobenzo[b]dioxine, dihydrobenzo[d]oxazole, dihydrobenzo[b]thiophene, dihydroisobenzo[c]thiophene, dihydrobenzo[d]thiazole, dihydrobenzo[c]isothiazole, spiro[cyclobutane-1,3'-indolin]-2'-one, spiro[cyclopropane-1,3'-indolin]-2'-one, 2,3-dihydro-1H-benzo[d]pyrrolo[1,2-a]imidazole, benzo[d][1,3]dioxole, and benzo[b][1,4]thiazine, as shown in the structures below:

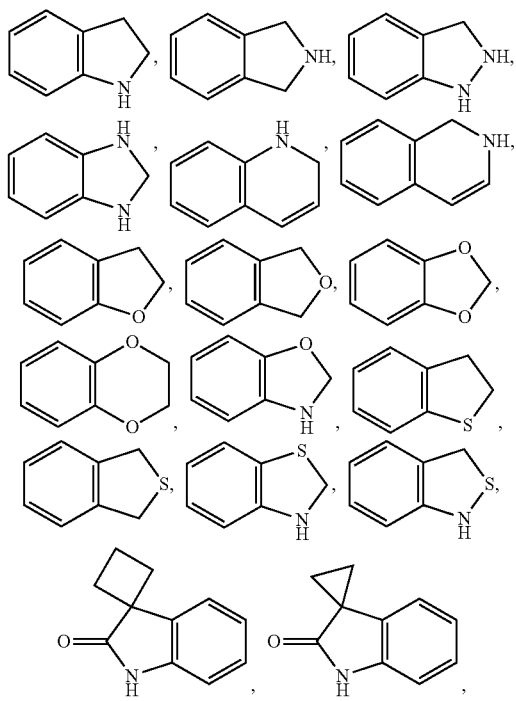

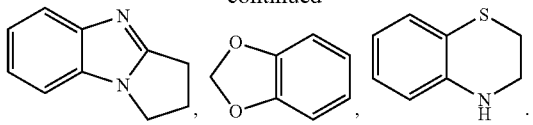

Fused bicyclic heterocycloalkyls can also be represented by the following structures:

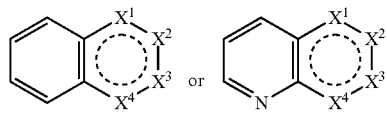

wherein $X^1$, $X^2$, $X^3$ and $X^4$ are each independently absent, $CH_2$—, —NH—, —O— or —S—, at least one of $X^1$, $X^2$, $X^3$ and $X^4$ is —NH—, —O— or —S—, and the dashed circle represents a saturated or partially unsaturated non-aromatic ring. The fused bicyclic heterocycloalkyls are optionally substituted.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heterocycloalkyl component is as defined above. Alkyl-heterocycloalkyl groups can be substituted or unsubstituted.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from 1 to 6 carbon atoms and 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1-20 carbon atoms and 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, pyridin-2(1H)-one, isoquinolin-1(2H)-one, and triazolyl.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within. Alkyl-heteroaryl groups can be substituted or unsubstituted.

A "compound of the present disclosure" includes compounds disclosed herein, for example a compound of the present disclosure includes compounds of Formula (I), (II-a), (II-b), (II-c), (II-d), (II-e), (II-f), (II-g), (II-h), (III-a), (III-b), (III-c), or (III-d), including the compounds of the Examples.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically effective amount" refers to an amount of a compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount can vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject. The administration can be carried out according to a schedule specifying frequency of administration, dose for administration, and other factors.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

"Subject" refers to animals such as mammals, including, but not limited to, primates (e.g., humans), cows, sheep, goats, horses, dogs, cats, rabbits, rats, mice and the like. In certain embodiments, the subject is a human.

"Disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

"Cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma.

Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

"Leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

"Sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms'tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

"Melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

"Carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basal oid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

"Metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Substitution with positron emitting isotopes, such as $^{11}$C, $^{18}$F, $^{15}$O and $^{13}$N, and can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)-for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring =N— such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—$SO_2CH_2$—" is equivalent to "—$CH_2SO_2$—" and both may be connected in either direction. Similarly, an "arylalkyl" group, for example, may be attached to the remainder of the molecule at either an aryl or an alkyl portion of the group. A prefix such as "$C_{u-v}$" or ($C_u$-$C_v$) indicates that the following group has from u to v carbon atoms. For example, "$C_{1-6}$alkyl" and "$C_1$-$C_6$ alkyl" both indicate that the alkyl group has from 1 to 6 carbon atoms.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

II. Compounds

The present disclosure provides compounds that are inhibitors of CD73. In some embodiments, the disclosure provides compounds of Formula (I) as described herein, and/or pharmaceutically acceptable salt(s) thereof. In some embodiments, a compound is provided having the structure of Formula (I),

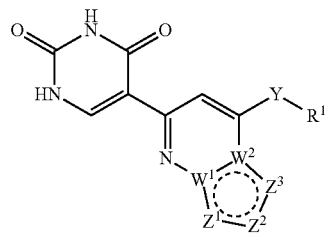

(I)

and/or pharmaceutically acceptable salt(s) thereof. Some embodiments provide a compound having the structure of Formula (I).

In some embodiments, the compound of Formula (I) is

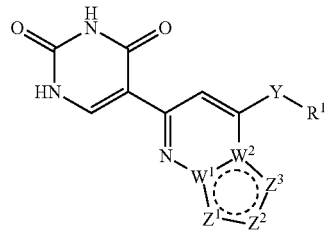

(I)

or a pharmaceutically acceptable salt thereof, wherein
Y is a bond, —$C_{1-6}$alkyl, —$C_{2-6}$alkenyl, —$C_{2-6}$alkynyl, —$C_{3-7}$cycloalkyl, —$C_{1-6}$alkyl-O—, —$C_{1-6}$alkyl-O—$C_{1-6}$alkyl, —O—$C_{1-6}$alkyl, —O—$C_{1-6}$alkyl-O—, —$C_{3-7}$cycloalkyl-O—, —O—$C_{3-7}$cycloalkyl, —$C_{3-7}$cycloalkyl-$C_{1-3}$alkyl, —S(=O)$_2$—, —S(=O)$_2$CH$_2$—, —CH$_2$S(=O)$_2$—, —N(R$^a$)—, —N(R$^a$)CH$_2$—, —$C_{1-6}$alkyl-N(R$^b$)—, —$C_{3-7}$cycloalkyl-N(R$^b$)—, —N(R$^a$)C(=O)—, —$C_{1-3}$alkylN(R$^a$)C(=O)—, heterocycloalkyl-C(=O)—, heterocycloalkyl-N(H)C(=O)—, heterocycloalkyl, heterocycloalkyl-$C_{1-6}$alkyl-O—, or heterocycloalkyl-O—, wherein each alkyl, cycloalkyl, or heterocycloalkyl is optionally substituted with one to four halogens and is further optionally substituted with one or two groups independently selected from —CN, —$C_{1-3}$alkyl and —$C_{1-3}$ haloalkyl;
one or two of $Z^1$, $Z^2$ and $Z^3$ is CR$^2$ and the remaining one or two of $Z^1$, $Z^2$, and $Z^3$ is N;
one of $W^1$ and $W^2$ is N and the other is C;
R$^1$ is hydrogen, —CN, —$C_{1-6}$alkyl, —$C_{3-7}$cycloalkyl, —$C_{6-12}$aryl, —$C_{1-6}$alkyl-$C_{6-12}$aryl, —$C_{1-6}$alkyl-heteroaryl, heterocycloalkyl, heteroaryl, or —$C_{1-6}$alkyl-O—$C_{1-6}$alkyl, wherein each alkyl, cycloalkyl, aryl, heterocycloalkyl, or heteroaryl is optionally substituted with one to three halogens and is further optionally substituted with one or two R$^3$;
R$^2$ is each independently hydrogen, halogen, —CN, —$C_{1-6}$alkyl, —$C_{3-10}$cycloalkyl, —O—$C_{1-6}$alkyl, —C(=O)OR$^a$, —C(=O)heterocycloalkyl, —C(=O)N(R$^b$)$C_{6-12}$aryl, —C(=O)N(R$^b$)heteroaryl, —C(=O)N(R$^b$)(R$^b$), —$C_{1-6}$alkyl-S(=O)$_2C_{6-12}$aryl, —N(R$^b$)(R$^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three R$^4$;
R$^3$ is halogen, —CN, —$C_{1-6}$alkyl, —$C_{3-7}$cycloalkyl, —$C_{1-3}$alkyl-$C_{3-7}$cycloalkyl, —$C_{1-3}$alkyl-heterocycloalkyl, —N(R$^b$)(R$^b$), —N(H)C(=O)O—R$^c$, —C(=O)N(R$^b$)(R$^b$), —C(=O)OC$_{1-6}$alkyl, —C(=O)OC$_{1-6}$alkylC$_{6-12}$aryl, —C(=O)C$_{1-3}$alkyl, —C(=O)C$_{3-7}$cycloalkyl, —C(=O)heterocycloalkyl, —OC(=O)heterocycloalkyl, —OC(=O)N(H)C$_{1-6}$alkyl, —OC(=O)N(H)C$_{3-7}$cycloalkyl, —OC(=O)OC$_{1-6}$alkyl, —OC(=O)N(H)C$_{6-12}$aryl, or —OR$^c$, wherein each alkyl, cycloalkyl, heterocycloalkyl, or aryl is optionally substituted with one to three halogens and is further optionally substituted with one or two R$^c$;
R$^4$ is halogen, —CN, —OR$^c$, —$C_{1-6}$alkyl, —N(R$^b$)(R$^b$), or —$C_{1-6}$haloalkyl;
R$^a$ is each independently hydrogen, or —$C_{1-3}$alkyl;
R$^b$ is each independently hydrogen, —$C_{1-6}$alkyl, —$C_{1-6}$haloalkyl, —$C_{1-6}$alkyl-$C_{3-7}$cycloalkyl, $C_{3-7}$cycloalkyl-$C_{1-6}$ haloalkyl, —$C_{3-7}$cycloalkyl, —$C_{3-7}$ halocycloalkyl, or —C(=O)C$_{1-6}$alkyl; and
R$^c$ is each independently hydrogen, —$C_{1-6}$alkyl, —$C_{1-6}$ haloalkyl, —$C_{3-7}$cycloalkyl, —$C_{1-3}$alkyl-$C_{3-7}$cycloalkyl, —$C_{1-3}$alkyl-$C_{3-7}$cyclohaloalkyl, —OC$_{1-6}$alkyl, or —$C_{3-7}$ halocycloalkyl; and
wherein each heterocycloalkyl or heteroaryl bears one to four heteroatoms each independently selected from N, O, and S;
wherein each heterocycloalkyl has 4 to 15 ring members; and
wherein each heteroaryl has 5 to 15 ring members.

In some embodiments, the compound of Formula (I) is

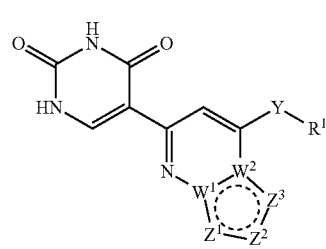

(I)

and/or a pharmaceutically acceptable salt thereof, wherein
Y is a bond, —$C_{1-6}$alkyl, —$C_{2-6}$alkenyl, —$C_{2-6}$alkynyl, —$C_{3-7}$cycloalkyl, —$C_{1-6}$alkyl-O—, —$C_{1-6}$alkyl-O—$C_{1-6}$alkyl, —O—$C_{1-6}$alkyl, —$C_{3-7}$cycloalkyl-O—, —O—$C_{3-7}$cycloalkyl, —$C_{3-7}$cycloalkyl-$C_{1-3}$alkyl-, —S(=O)$_2$—, —S(=O)$_2$CH$_2$—, —CH$_2$S(=O)$_2$—, —N(R$^a$)—, —N(R$^a$)CH$_2$—, —$C_{1-6}$alkyl-N(R$^b$)—, —$C_{3-7}$cycloalkyl-N(R$^b$)—, —N(R$^a$)C(=O)—, —C$_{1-3}$alkylN(R$^a$)C(=O)—, heterocycloalkyl-C(=O)—, heterocycloalkyl or heterocycloalkyl-O—, wherein each alkyl, cycloalkyl, or heterocycloalkyl is optionally substituted with one to four halogens and is further optionally substituted with one or two groups independently selected from —CN and —C$_{1-3}$alkyl;

one or two of Z$^1$, Z$^2$ and Z$^3$ is CR$^2$ and the remaining one or two of Z$^1$, Z$^2$, and Z$^3$ is N;

one of W$^1$ and W$^2$ is N and the other is C;

R$^1$ is hydrogen, —CN, —C$_{1-6}$alkyl, —C$_{3-7}$cycloalkyl, —C$_{6-12}$aryl, heterocycloalkyl, heteroaryl, or —C$_{1-6}$alkyl-O—C$_{1-6}$alkyl, wherein each alkyl, cycloalkyl, aryl, heterocycloalkyl, or heteroaryl is optionally substituted with one to three halogens and is further optionally substituted with one or two R$^3$;

R$^2$ is each independently hydrogen, halogen, —CN, —C$_{1-6}$alkyl, —C$_{3-10}$cycloalkyl, —O—C$_{1-6}$alkyl, —C(=O)OR$^a$, —C(=O)N(R$^b$)C$_{6-12}$aryl, —C(=O)N(R$^b$)heteroaryl, —C(=O)N(R$^b$)(R$^b$), —C$_{1-6}$alkyl-S(=O)$_2$C$_6$aryl, —N(R$^b$)(R$^b$), —C$_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three R$^4$;

R$^3$ is halogen, —CN, —C$_{1-6}$alkyl, —C$_{1-6}$haloalkyl, —C$_{3-7}$cycloalkyl, —N(R$^b$)(R$^b$), —C(=O)OC$_{1-6}$alkyl, —OC(=O)N(H)C$_{1-6}$alkyl, —OC(=O)OC$_{1-6}$alkyl, or —OR$^c$;

R$^4$ is halogen, —CN, —OR$^c$, —C$_{1-6}$alkyl, —N(R$^b$)(R$^b$), or —C$_{1-6}$haloalkyl;

R$^a$ is each independently hydrogen, or —C$_{1-3}$alkyl;

R$^b$ is each independently hydrogen, —C$_{1-6}$alkyl, —C$_{1-6}$haloalkyl, —C$_{1-6}$alkyl-C$_{3-7}$cycloalkyl, —C$_{3-7}$cycloalkyl, —C$_{3-7}$ halocycloalkyl, or —C(=O)C$_{1-6}$alkyl; and R$^c$ is each independently hydrogen, —C$_{1-6}$alkyl, —C$_{1-6}$ haloalkyl, —C$_{3-7}$cycloalkyl, or —C$_{3-7}$halocycloalkyl; and wherein each heterocycloalkyl or heteroaryl bears one to four heteroatoms each independently selected from N, O, and S;

wherein each heterocycloalkyl has 4 to 10 ring members; and wherein each heteroaryl has 5 to 10 ring members.

In some embodiments, the disclosure provides a compound having the structure of Formula (I), and/or a pharmaceutically acceptable salt thereof, wherein Y is a bond, —C$_{1-6}$alkyl, —C$_{2-6}$alkenyl, —C$_{2-6}$alkynyl, —C$_{3-7}$cycloalkyl, —C$_{1-6}$alkyl-O—, —O—C$_{1-6}$alkyl, —C$_{3-7}$cycloalkyl-O—, —O—C$_{3-7}$cycloalkyl, —C$_{3-7}$cycloalkyl-C$_{1-3}$alkyl-, —S(=O)$_2$—, —S(=O)$_2$CH$_2$—, —CH$_2$S(=O)$_2$—, —N(R$^a$)—, —N(R$^a$)CH$_2$—, —C$_{1-6}$alkyl-N(R$^b$)—, —C$_{3-7}$cycloalkyl-N(R$^b$)—, —N(R$^a$)C(=O)—, —C$_{1-3}$alkylN(R$^a$)C(=O)—, heterocycloalkyl-C(=O)—, —O—C$_{1-6}$alkyl-O—, heterocycloalkyl-N(H)C(=O)—, heterocycloalkyl-C$_{1-6}$alkyl-O—, or heterocycloalkyl, wherein each alkyl, cycloalkyl, or heterocycloalkyl is optionally substituted with one to four halogens and is further optionally substituted with one or two groups independently selected from —CN—C$_{1-3}$alkyl and —C$_{1-3}$ haloalkyl;

R$^1$ is hydrogen, —CN, —C$_{1-6}$alkyl, —C$_{3-7}$cycloalkyl, —C$_{6-12}$aryl, —C$_{1-6}$alkyl-C$_{6-12}$aryl, —C$_{1-6}$alkyl-heteroaryl, heterocycloalkyl, heteroaryl, or —C$_{1-6}$alkyl-O—C$_{1-6}$alkyl, wherein each alkyl, cycloalkyl, aryl, heterocycloalkyl, or heteroaryl is optionally substituted with one to three halogens and is further optionally substituted with one or two R$^3$;

R$^3$ is halogen, —CN, —C$_{1-6}$alkyl, —C$_{1-6}$haloalkyl, —C$_{3-7}$cycloalkyl, —C$_{1-3}$alkyl-C$_{3-7}$cycloalkyl, —C$_{1-3}$alkyl-heterocycloalkyl, —N(R$^b$)(R$^b$), —N(H)C(=O)O—R$^c$, —C(=O)N(R$^b$)(R$^b$), —C(=O)OC$_{1-6}$alkylC$_{6-12}$aryl, —C(=O)C$_{1-3}$alkyl, —C(=O)C$_{3-7}$cycloalkyl, —C(=O)heterocycloalkyl, —OC(=O)heterocycloalkyl, —OC(=O)N(H)C$_{3-7}$cycloalkyl, —OC(=O)N(H)C$_{6-12}$aryl, or —OR$^c$;

R$^b$ is each independently hydrogen, —C$_{1-6}$alkyl, —C$_{1-6}$haloalkyl, —C$_{3-7}$cycloalkyl, —C$_{3-7}$halocycloalkyl, or —C(=O)C$_{1-6}$alkyl; and wherein Z$^1$, Z$^2$, Z$^3$, W$^1$, W$^2$, R$^2$, R$^4$, R$^a$, and R$^c$ are as described herein.

In some embodiments, the disclosure provides a compound having the structure of Formula (I), and/or a pharmaceutically acceptable salt thereof, wherein Y is a bond, —C$_{1-6}$alkyl, —C$_{2-6}$alkenyl, —C$_{2-6}$alkynyl, —C$_{3-7}$cycloalkyl, —C$_{1-6}$alkyl-O—, —O—C$_{1-6}$alkyl, —C$_{3-7}$cycloalkyl-O—, —O—C$_{3-7}$cycloalkyl, —C$_{3-7}$cycloalkyl-C$_{1-3}$alkyl-, —S(=O)$_2$—, —S(=O)$_2$CH$_2$—, —CH$_2$S(=O)$_2$—, —N(R$^a$)—, —N(R$^a$)CH$_2$—, —C$_{1-6}$alkyl-N(R$^b$)—, —C$_{3-7}$cycloalkyl-N(R$^b$)—, —N(R$^a$)C(=O)—, —C$_{1-3}$alkylN(R$^a$)C(=O)—, heterocycloalkyl-C(=O)—, or heterocycloalkyl, wherein each alkyl, cycloalkyl, or heterocycloalkyl is optionally substituted with one to four halogens and is further optionally substituted with one or two groups independently selected from —CN and —C$_{1-3}$alkyl;

R$^1$ is hydrogen, —CN, —C$_{1-6}$alkyl, —C$_{3-7}$cycloalkyl, —C$_6$aryl, heterocycloalkyl, heteroaryl, or —C$_{1-6}$alkyl-O—C$_{1-6}$alkyl, wherein each alkyl, cycloalkyl, aryl, heterocycloalkyl, or heteroaryl is optionally substituted with one to three halogens and is further optionally substituted with one or two R$^3$;

R$^3$ is halogen, —CN, —C$_{1-6}$alkyl, —C$_{1-6}$haloalkyl, —C$_{3-7}$cycloalkyl, —N(R$^b$)(R$^b$), or or —OR$^c$;

R$^b$ is each independently hydrogen, —C$_{1-6}$alkyl, —C$_{1-6}$haloalkyl, —C$_{3-7}$cycloalkyl, —C$_{3-7}$halocycloalkyl, or —C(=O)C$_{1-6}$alkyl; and wherein Z$^1$, Z$^2$, Z$^3$, W$^1$, W$^2$, R$^2$, R$^4$, R$^a$, and R$^c$ are as described herein.

In some embodiments, the disclosure provides a compound having the structure of Formula (II-a):

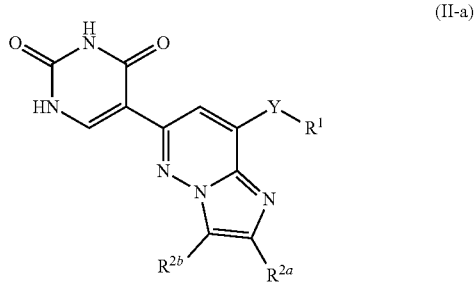

(II-a)

and/or pharmaceutically acceptable salt(s) thereof, wherein Y, R$^1$, R$^{2a}$, and R$^{2b}$, are as described herein.

In some embodiments, the disclosure provides a compound having the structure of Formula (II-a):

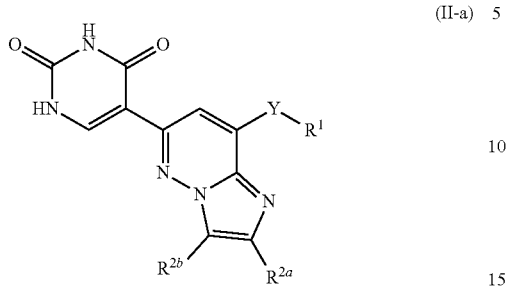

(II-a)

wherein $R^{2a}$ and $R^{2b}$ are each independently hydrogen, halogen, —CN, —$C_{1-6}$alkyl, —$C_{3-10}$cycloalkyl, —O—$C_{1-6}$alkyl, —C(=O)OR$^a$, —C(=O)heterocycloalkyl, —C(=O)N(R$^b$)$C_{6-12}$aryl, —C(=O)N(R$^b$)(R$^b$), —$C_{1-6}$alkyl-S(=O)$_2$$C_{6-12}$aryl, —N(R$^b$)(R$^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$, and wherein $R^1$ and Y are as described herein.

In some embodiments, the disclosure provides a compound having the structure of Formula (II-a):

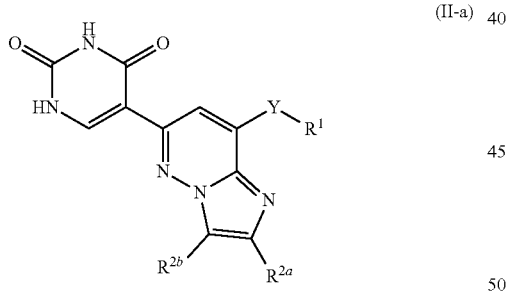

(II-a)

and/or pharmaceutically acceptable salt(s) thereof, wherein $R^{2a}$ and $R^{2b}$ are each independently hydrogen, halogen, —CN, —$C_{1-6}$alkyl, —$C_{3-10}$cycloalkyl, —O—$C_{1-6}$alkyl, —C(=O)OR$^a$, —C(=O)N(R$^b$)$C_{6-12}$aryl, —C(=O)N(R$^b$)(R$^b$), —$C_{1-6}$alkyl-S(=O)$_2$$C_6$aryl, —N(R$^b$)(R$^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$, and wherein $R^1$ and Y are as described herein.

In some embodiments, the disclosure provides a compound having the structure of Formula (II-b):

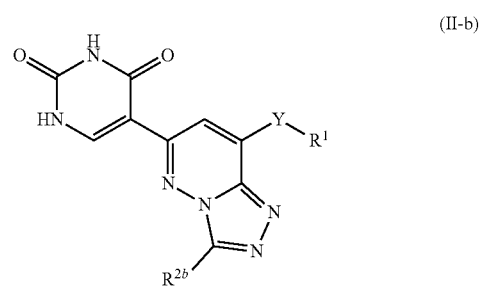

(II-b)

and/or pharmaceutically acceptable salt(s) thereof,
wherein Y, $R^1$, and $R^{2b}$, are as described herein.

In some embodiments, the disclosure provides a compound having the structure of Formula (II-b):

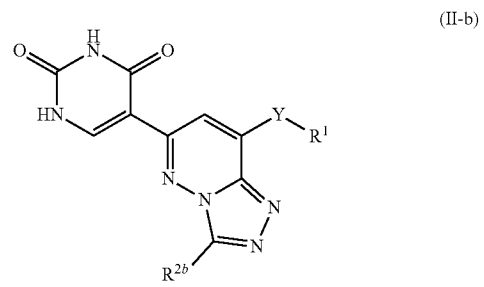

(II-b)

and/or pharmaceutically acceptable salt(s) thereof, wherein $R^{2b}$ is hydrogen, halogen, —CN, —$C_{1-6}$alkyl, —$C_{3-10}$cycloalkyl, —O—$C_{1-6}$alkyl, —C(=O)OR$^a$, —C(=O)N(R$^b$)$C_{6-12}$aryl, —C(=O)N(R$^b$)heteroaryl, —C(=O)N(R$^b$)(R$^b$), —$C_{1-6}$alkyl-S(=O)$_2$$C_6$aryl, —N(R$^b$)(R$^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$, and wherein $R^1$ and Y are as described herein.

In some embodiments, the disclosure provides a compound having the structure of Formula (II-c):

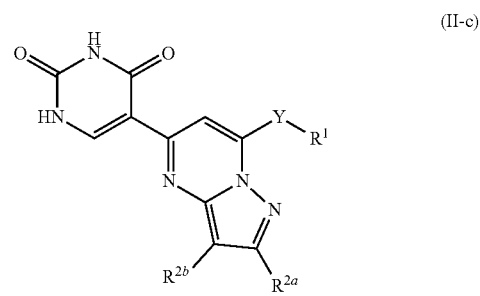

(II-c)

and/or pharmaceutically acceptable salt(s) thereof,
wherein Y, $R^1$, $R^{2a}$, and $R^{2b}$, are as described herein.

In some embodiments, the disclosure provides a compound having the structure of Formula (II-c):


(II-c)

and/or pharmaceutically acceptable salt(s) thereof,
wherein $R^{2a}$ and $R^{2b}$ are each independently hydrogen, halogen, —CN, —$C_{1-6}$alkyl, —$C_{3-10}$cycloalkyl, —O—$C_{1-6}$alkyl, —C(=O)O$R^a$, —C(=O)N($R^b$)$C_{6-12}$aryl, —C(=O)N($R^b$)($R^b$), —$C_{1-6}$alkyl-S(=O)$_2C_6$aryl, —N($R^b$)($R^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$,
and wherein $R^1$ and Y are as described herein.

In some embodiments, the disclosure provides a compound having the structure of Formula (II-d):

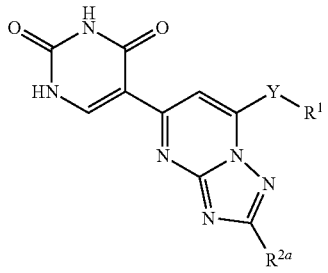

(II-d)

and/or pharmaceutically acceptable salt(s) thereof, wherein Y, $R^1$, and $R^{2a}$ are as described herein.

In some embodiments, the disclosure provides a compound having the structure of Formula (II-d):


(II-d)

and/or pharmaceutically acceptable salt(s) thereof,
wherein $R^{2a}$ is hydrogen, halogen, —CN, —$C_{1-6}$alkyl, —$C_{3-10}$cycloalkyl, —O—$C_{1-6}$alkyl, —C(=O)O$R^a$, —C(=O)N($R^b$)$C_{6-12}$aryl, —C(=O)N($R^b$)($R^b$), —$C_{1-6}$alkyl-S(=O)$_2C_6$aryl, —N($R^b$)($R^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$,
and wherein $R^1$ and Y are as described herein.

In some embodiments, the disclosure provides a compound having the structure of Formula (II-e):

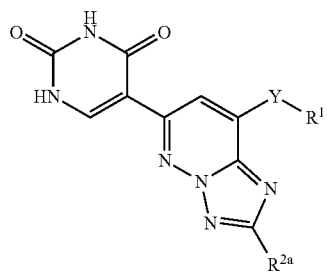

(II-e)

and/or pharmaceutically acceptable salt(s) thereof, wherein Y, $R^1$, and $R^{2a}$ are as described herein.

In some embodiments, the disclosure provides a compound having the structure of Formula (II-e):

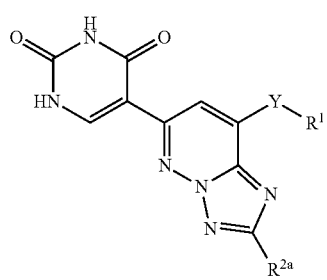

(II-e)

and/or pharmaceutically acceptable salt(s) thereof,
wherein $R^{2a}$ is independently hydrogen, halogen, —CN, —$C_{1-6}$alkyl, —$C_{3-10}$cycloalkyl, —O—$C_{1-6}$alkyl, —C(=O)O$R^a$, —C(=O)N($R^b$)$C_{6-12}$aryl, —C(=O)N($R^b$)($R^b$), —$C_{1-6}$alkyl-S(=O)$_2C_6$aryl, —N($R^b$)($R^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$,
and wherein $R^1$ and Y are as described herein.

Some embodiments provide a compound having the structure of Formula (II-a), (II-b), (II-c), (II-d), or (II-e), wherein $R^1$ is optionally substituted with one or two $R^3$; and wherein $R^{2a}$ and $R^{2b}$ are each independently hydrogen, halogen, —CN, —$C_{1-6}$alkyl, —$C_{3-10}$cycloalkyl, —O—$C_{1-6}$alkyl, —C(=O)O$R^a$, —C(=O)N($R^b$)$C_{6-12}$aryl, —C(=O)N($R^b$)($R^b$), —$C_{1-6}$alkyl-S(=O)$_2C_6$aryl, —N($R^b$)($R^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$.

In some embodiments, a compound of the disclosure is a compound wherein $R^1$ is —$C_{1-6}$alkyl, —$C_{3-7}$cycloalkyl, —$C_{6-12}$aryl, heterocycloalkyl, heteroaryl, or —$C_{1-6}$alkyl-O—$C_{1-6}$alkyl, wherein each alkyl, cycloalkyl, aryl, or heteroaryl is optionally substituted with one to three halogens and is further optionally substituted with one or two $R^3$. In some embodiments, a compound of the disclosure is a compound wherein $R^1$ is —$C_{1-6}$alkyl, —$C_{3-7}$cycloalkyl, —$C_{6-12}$aryl, heterocycloalkyl, heteroaryl, or —$C_{1-6}$alkyl-O—$C_{1-6}$alkyl, wherein each alkyl, cycloalkyl, aryl, or heteroaryl is optionally substituted with one to four halogens.

In some embodiments, a compound of the disclosure is a compound wherein $R^1$ is —$C_{1-6}$alkyl, —$C_{3-7}$cycloalkyl, —$C_6$aryl, heterocycloalkyl, heteroaryl, or —$C_{1-6}$alkyl-O—$C_{1-6}$alkyl, wherein each alkyl, cycloalkyl, aryl, or heteroaryl is optionally substituted with one to three halogens and is further optionally substituted with one or two $R^3$. In some embodiments, a compound of the disclosure is a compound wherein $R^1$ is —$C_{1-6}$alkyl, —$C_{3-7}$cycloalkyl, —$C_6$aryl, heterocycloalkyl, heteroaryl, or —$C_{1-6}$alkyl-O—$C_{1-6}$alkyl, wherein each alkyl, cycloalkyl, aryl, or heteroaryl is optionally substituted with one to four halogens.

In some embodiments, a compound of the disclosure is a compound wherein $R^1$ is isopropyl, —F, —$CF_3$, pyrrolidinyl, morpholinyl, imidazolyl, phenyl, pyridinyl, —$CH_2OCH_3$, —$C(CH_3)_3$ or cyclopropyl, each of which is optionally substituted, to the extent valency permits, with one to three halogens and is further optionally substituted with one or two $R^3$. In some embodiments, a compound of the disclosure is a compound, or pharmaceutically acceptable salt thereof, wherein $R^1$ is isopropyl, —F, —$CF_3$, pyrrolidinyl, morpholinyl, imidazolyl, phenyl, pyridinyl, —$CH_2OCH_3$, —$C(CH_3)_3$ or cyclopropyl, each of which is optionally substituted, to the extent valency permits, with one to three halogens. In some embodiments, a compound of the disclosure is a compound, or pharmaceutically acceptable salt thereof, wherein $R^1$ is isopropyl, —F, —$CF_3$, pyrrolidinyl, morpholinyl, imidazolyl, phenyl, pyridinyl, —$CH_2OCH_3$, —$C(CH_3)_3$ or cyclopropyl.

In some embodiments, a compound of the disclosure is a compound wherein $R^1$ is:

In some embodiments, a compound of the disclosure is a compound wherein $R^1$ is:

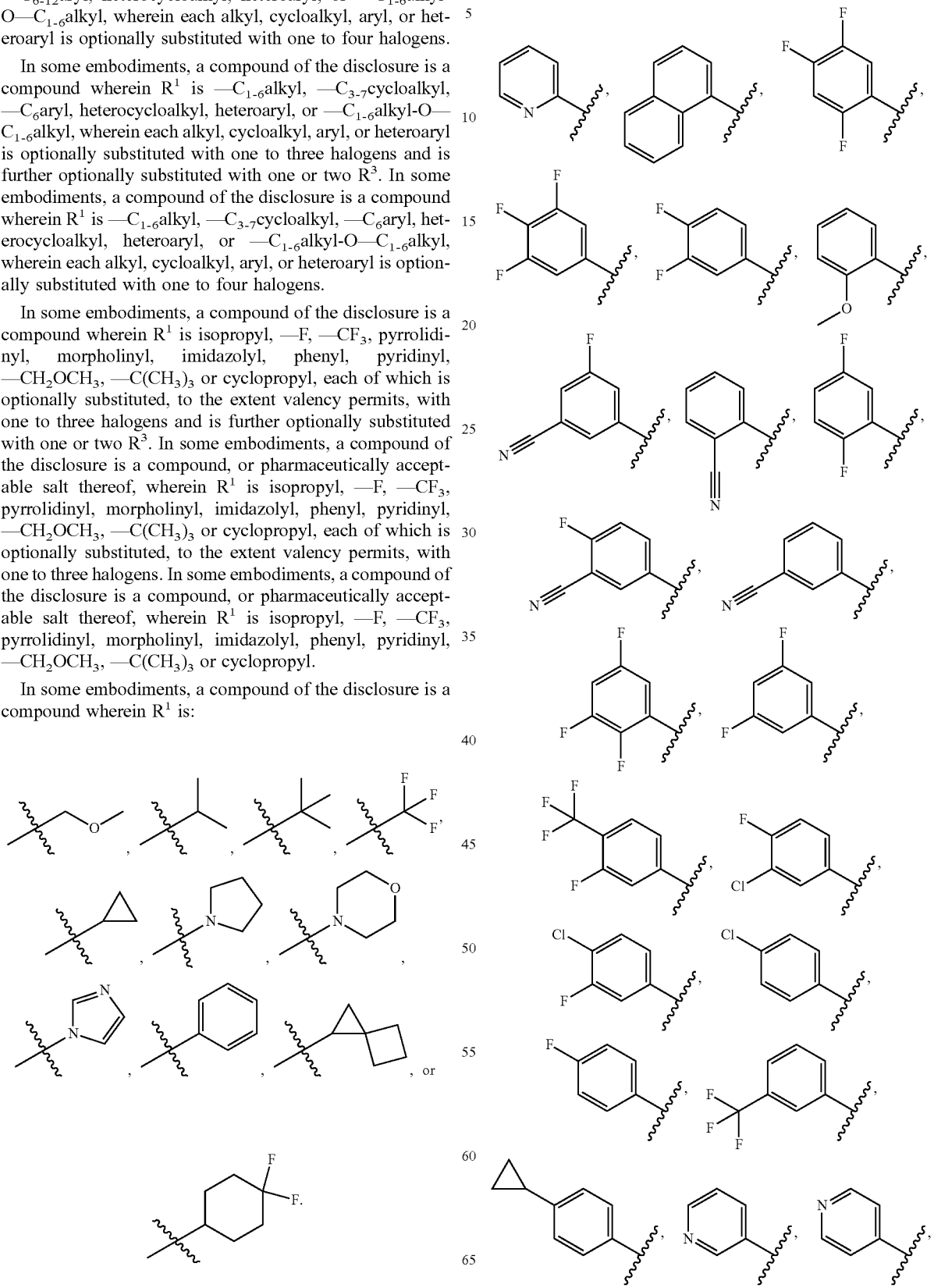

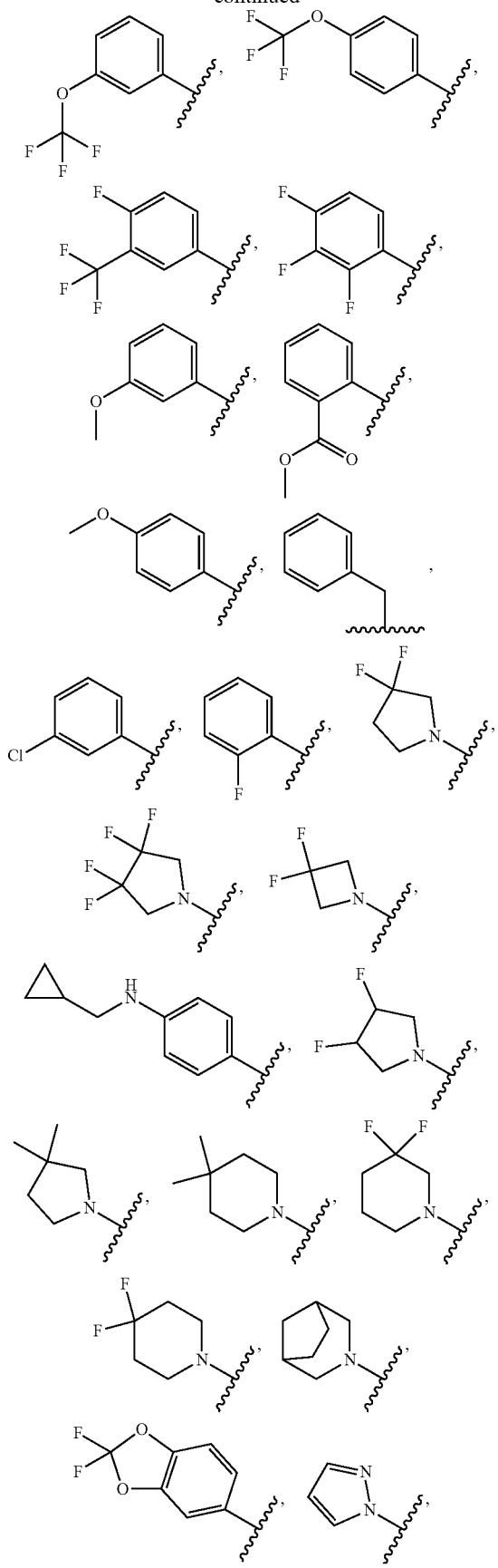

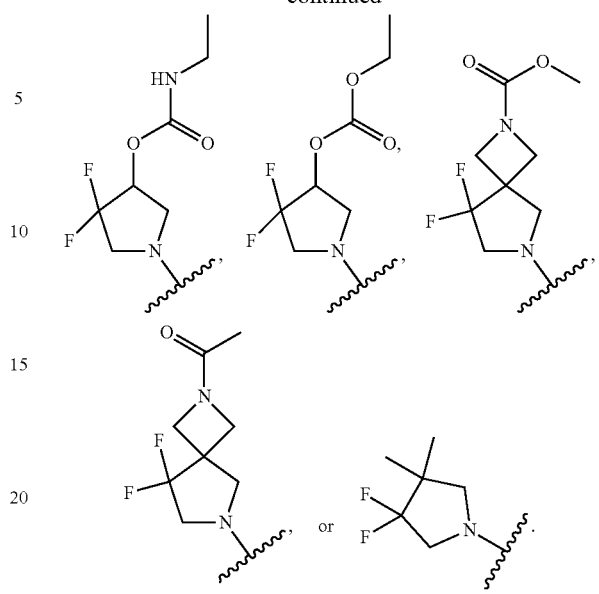

In some embodiments, a compound of the disclosure is a compound wherein $R^2$ is selected from hydrogen, halogen, —CN, —$C_{1-6}$alkyl, —$C_{3-10}$cycloalkyl, —O—$C_{1-6}$alkyl, —C(=O)OR$^a$, —C(=O)N(R$^b$)$C_{6-12}$aryl, —C(=O)N(R$^b$)heteroaryl, —C(=O)N(R$^b$)(R$^b$), —$C_{1-6}$alkyl-S(=O)$_2C_6$aryl, —N(R$^b$)(R$^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$.

In some embodiments, a compound of the disclosure is a compound wherein $R^{2a}$ and $R^{2b}$ are each selected from hydrogen, halogen, —CN, —$C_{1-6}$alkyl, —$C_{3-10}$cycloalkyl, —O—$C_{1-6}$alkyl, —C(=O)OR$^a$, —C(=O)N(R$^b$)$C_{6-12}$aryl, —C(=O)N(R$^b$)heteroaryl, —C(=O)N(R$^b$)(R$^b$), —$C_{1-6}$alkyl-S(=O)$_2C_6$aryl, —N(R$^b$)(R$^b$), —$C_{6-12}$aryl, heterocycloalkyl, or heteroaryl, wherein each alkyl, cycloalkyl, heterocycloalkyl, aryl, or heteroaryl is optionally substituted with one to three halogens and is further optionally substituted with one to three $R^4$.

In some embodiments, a compound of the disclosure is a compound wherein $R^2$, $R^{2a}$ and $R^{2b}$ are each independently hydrogen, halogen, —$C_{1-6}$alkyl, —$C_{3-10}$cycloalkyl, —C(=O)OR$^a$, —$C_{1-6}$alkyl-S(=O)$_2C_6$aryl, heteroaryl or —$C_6$aryl, wherein each alkyl, cycloalkyl, heteroaryl or aryl is optionally substituted with one to three halogens and is further optionally substituted with one or two $R^4$.

In some embodiments, a compound of the disclosure is a compound wherein $R^2$, $R^{2a}$ and $R^{2b}$ are each independently —H, —F, —$CH_3$, —$CH_2CH_3$, —$CF_3$, phenyl, —$CH_2SO_2Ph$, —C(=O)OCH$_2$CH$_3$, cyclopropyl, or

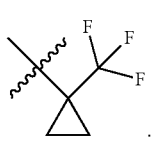

In some embodiments, a compound of the disclosure is a compound wherein $R^2$, $R^{2a}$, or $R^{2b}$ is:

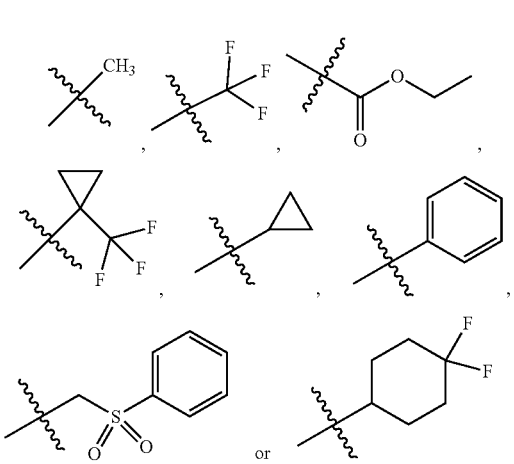

In some embodiments, a compound of the disclosure is a compound wherein $R^2$, $R^{2a}$, or $R^{2b}$ is:

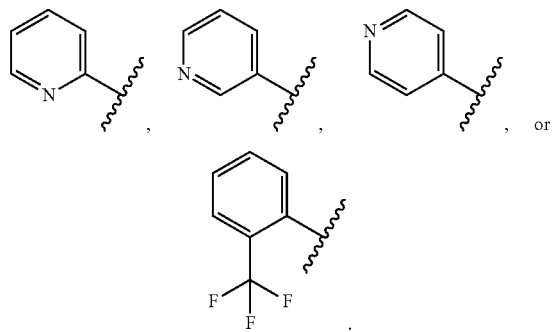

In some embodiments, a compound of the disclosure is a compound wherein $R^2$, $R^{2a}$, or $R^{2b}$ is:

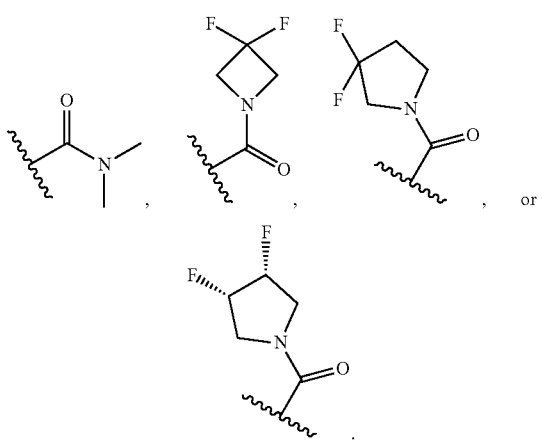

In some embodiments, a compound of the disclosure is a compound wherein $R^3$ is —CH$_3$, —CH$_2$CH$_3$, —F, —Cl, —CF$_3$, cyclopropyl, —OCF$_3$ or —CN.

In some embodiments, a compound of the disclosure is a compound wherein $R^3$ is —O—CH$_3$ or

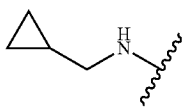

In some embodiments, a compound of the disclosure is a compound wherein $R^4$ is —F or —CF$_3$.

In some embodiments, a compound of the disclosure is a compound wherein Y is a bond.

In some embodiments, a compound of the disclosure is a compound wherein Y is:

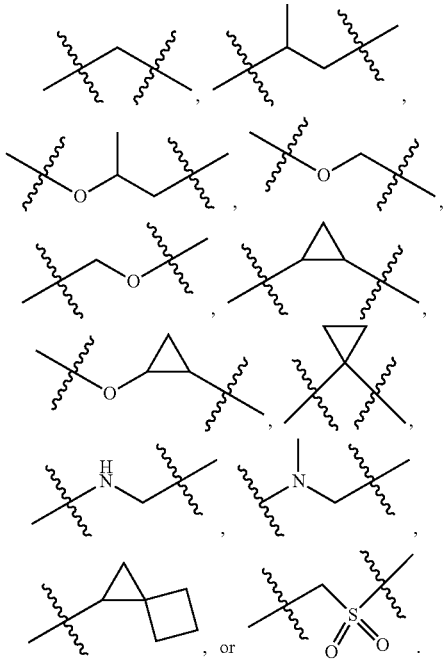

In some embodiments, a compound of the disclosure is a compound Y—$R^1$ is: —CH$_3$, —CH$_2$CH$_3$, isopropyl, —O-isopropyl, —OPh,

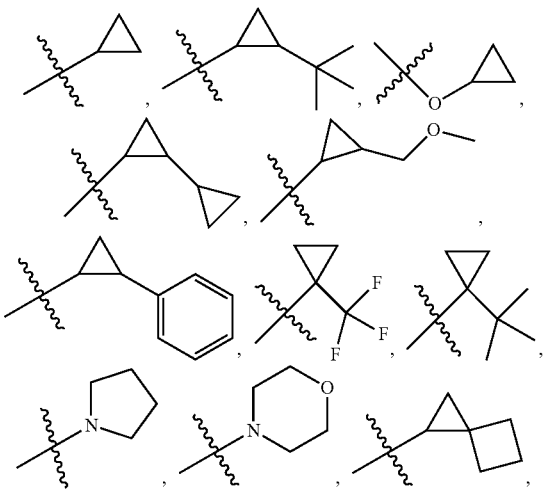

-continued
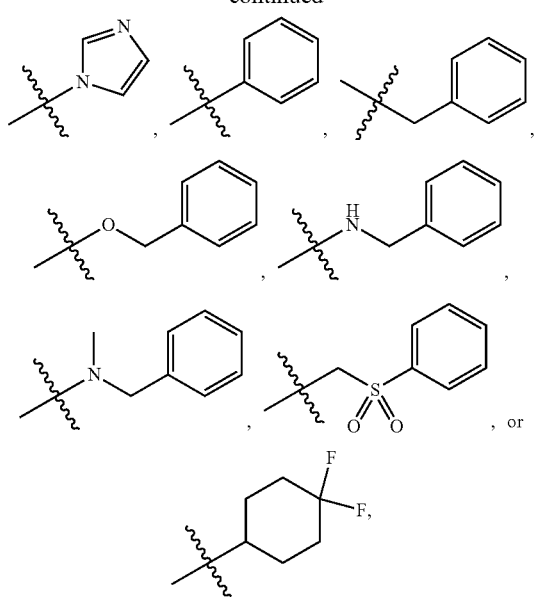
each of which is optionally substituted with one or two $R^3$.
In some embodiments, a compound of the disclosure is a compound Y—$R^1$ is:
-continued
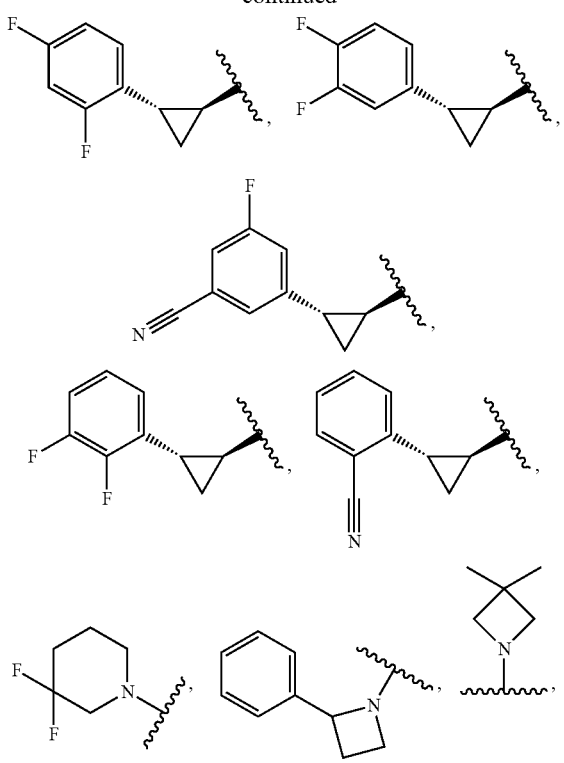

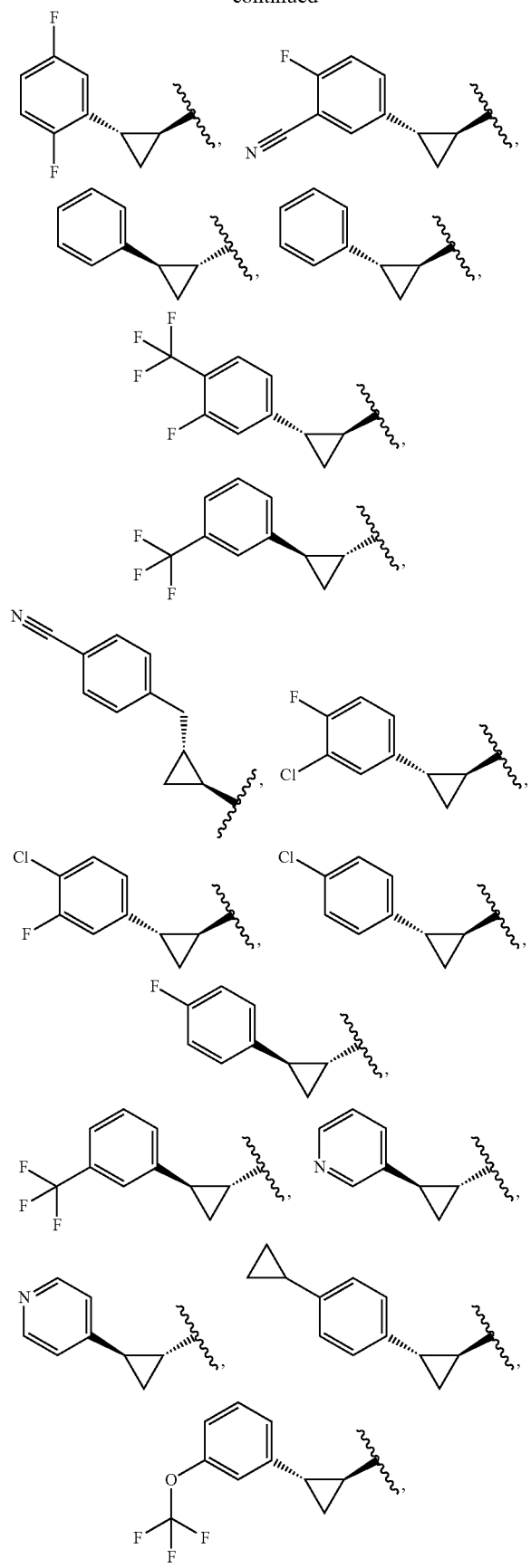
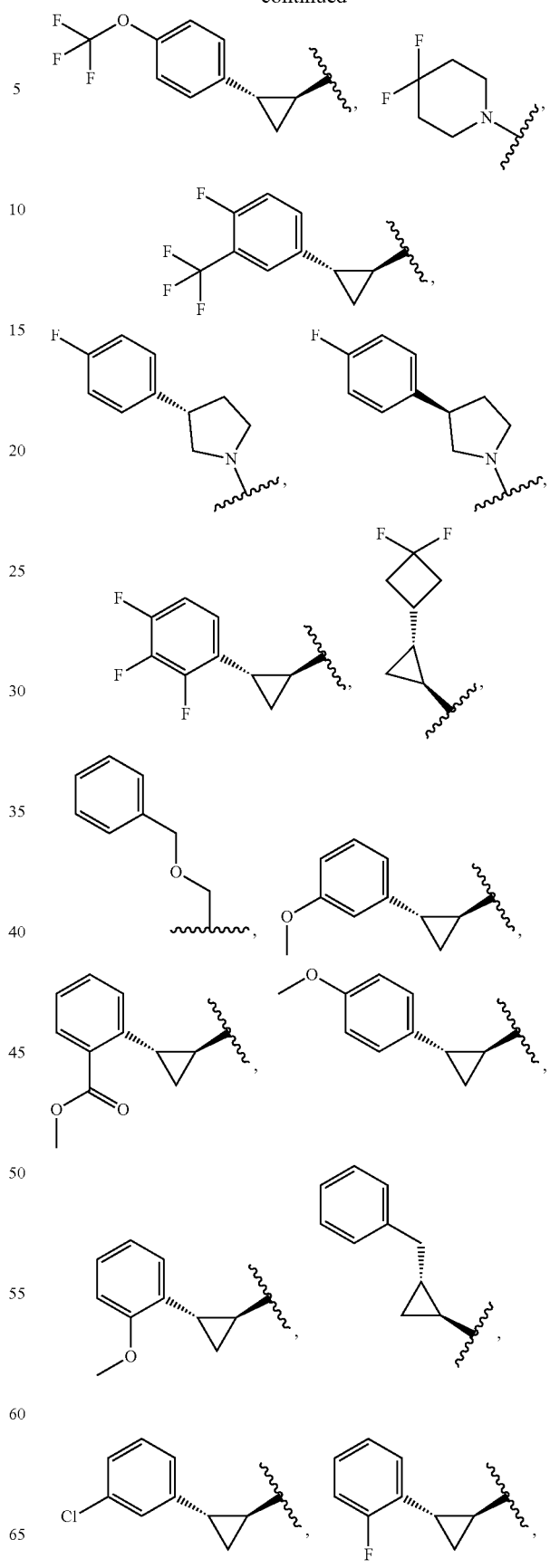

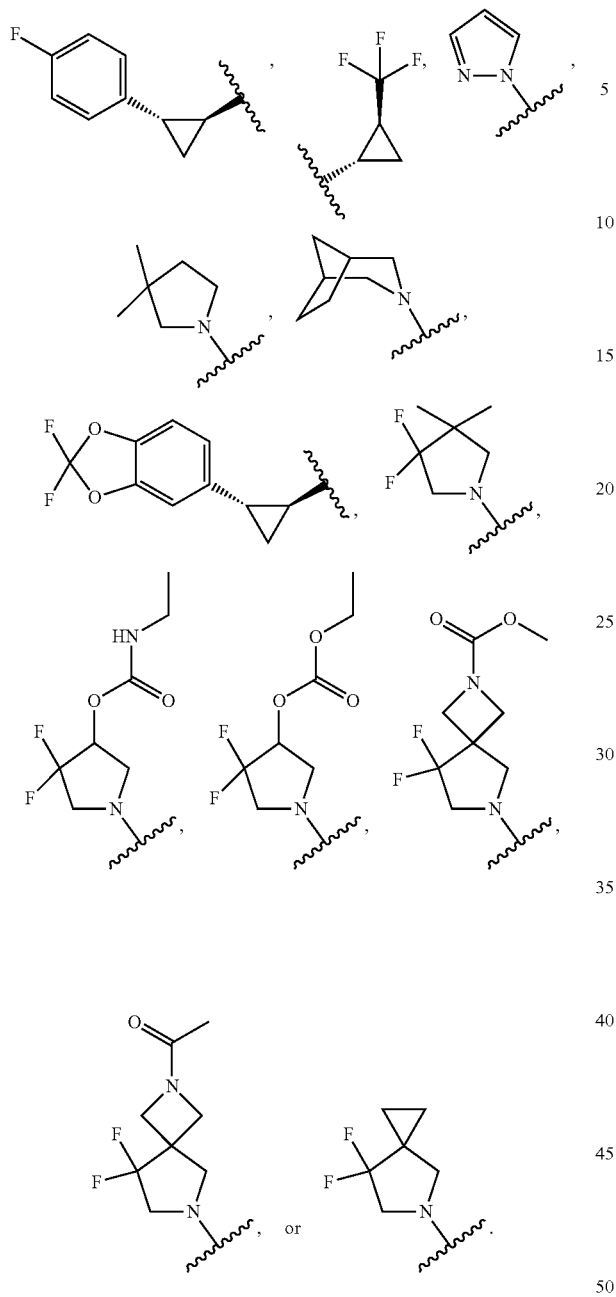
In some embodiments, a compound of the disclosure is a compound Y—R¹ is:
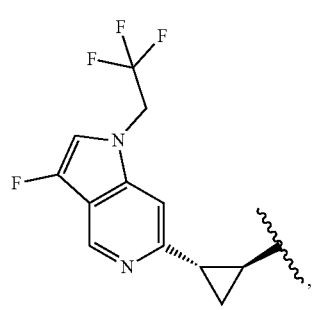
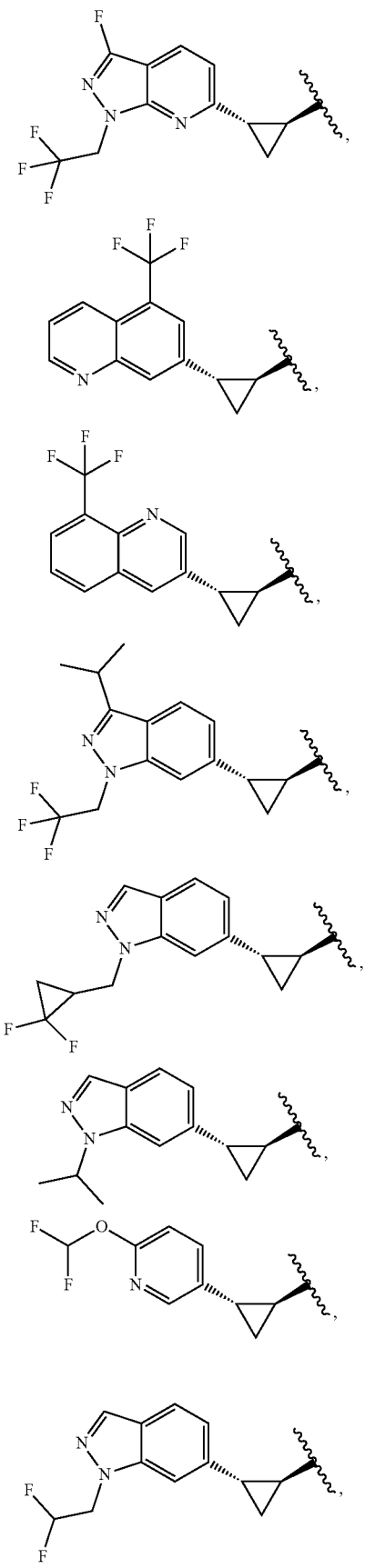

-continued
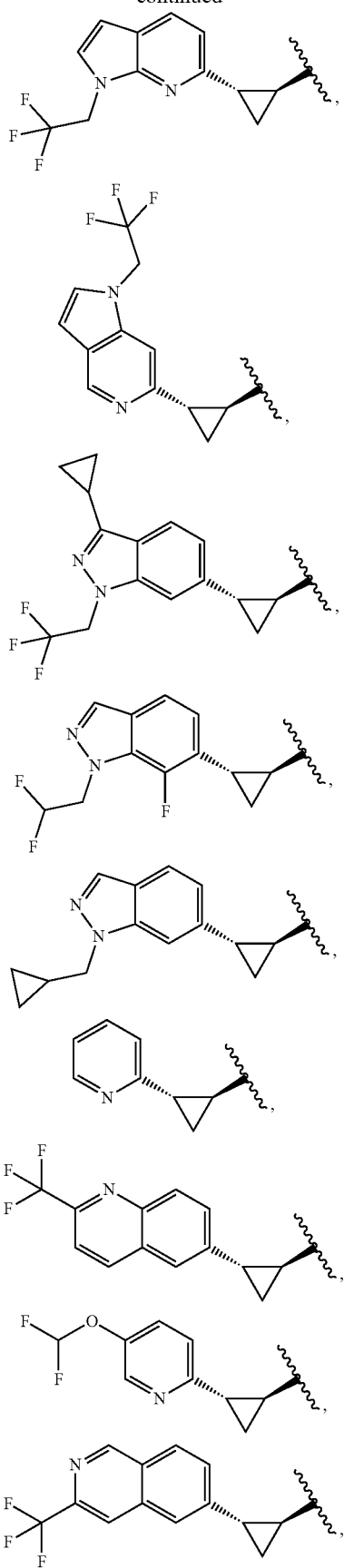
-continued
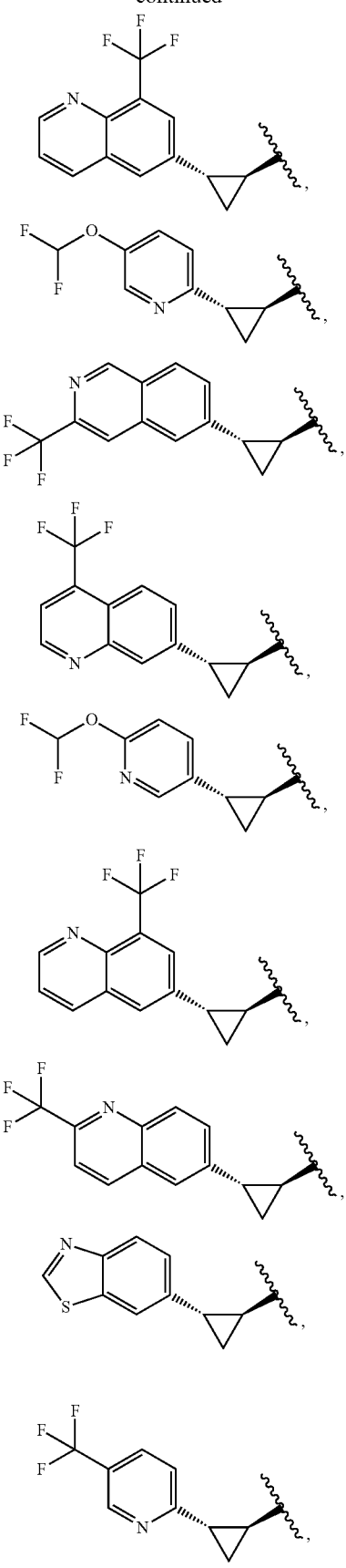

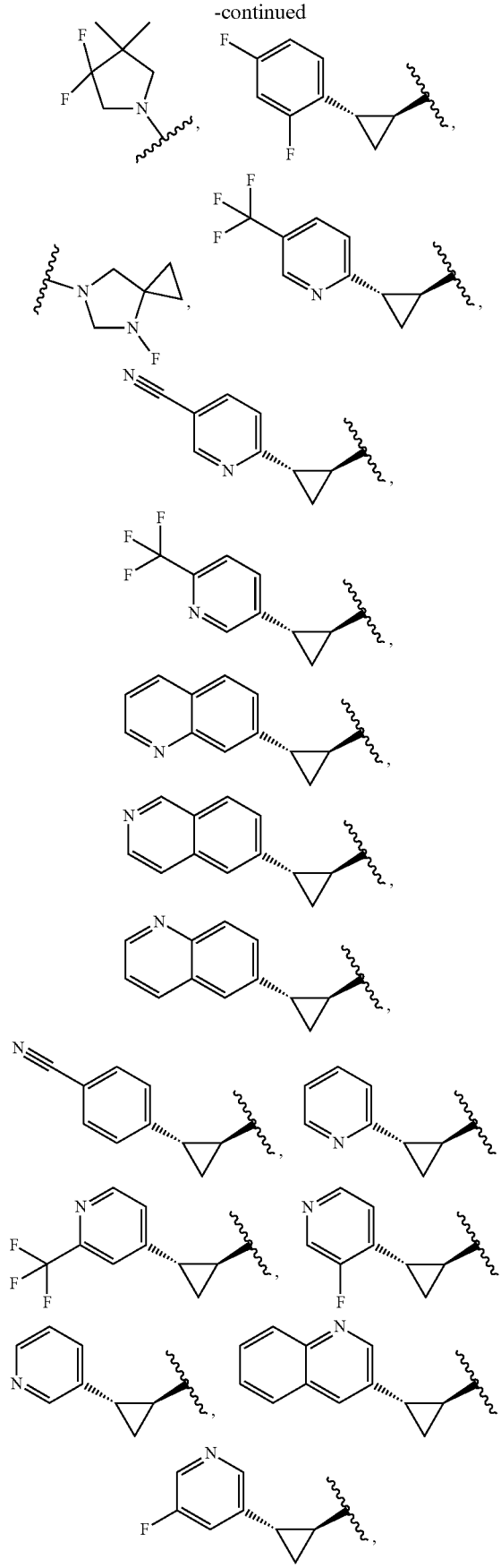
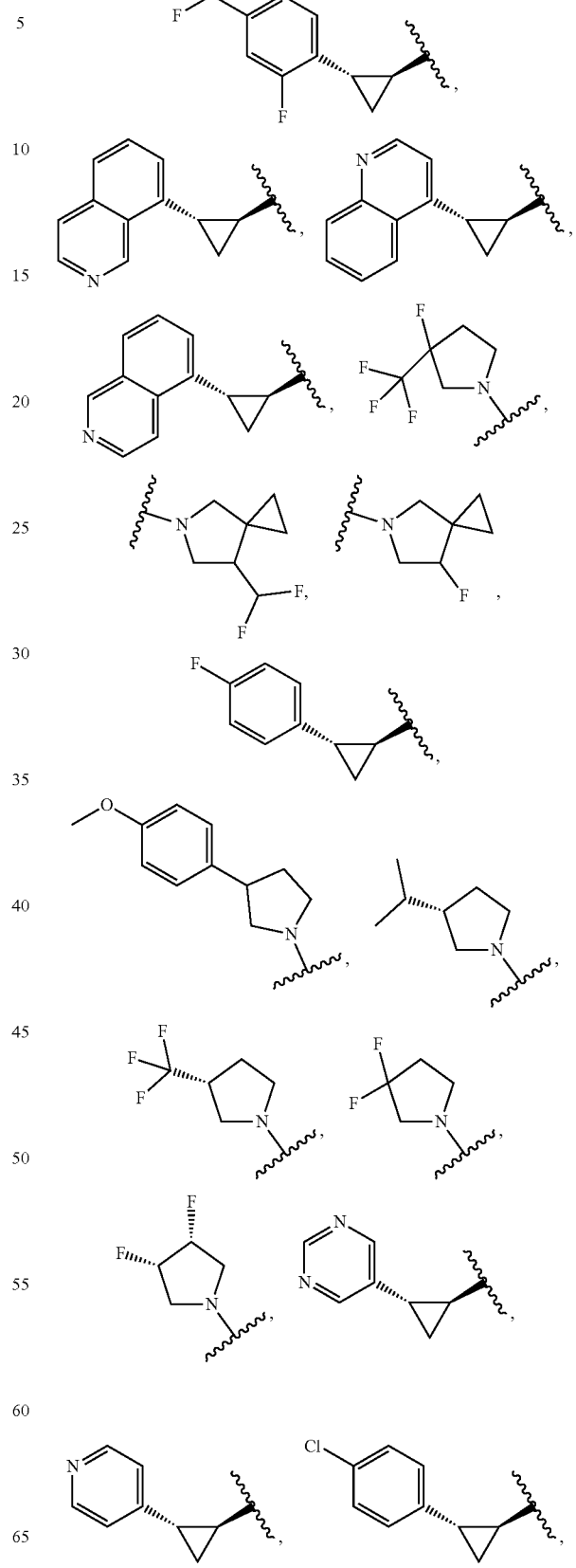

-continued
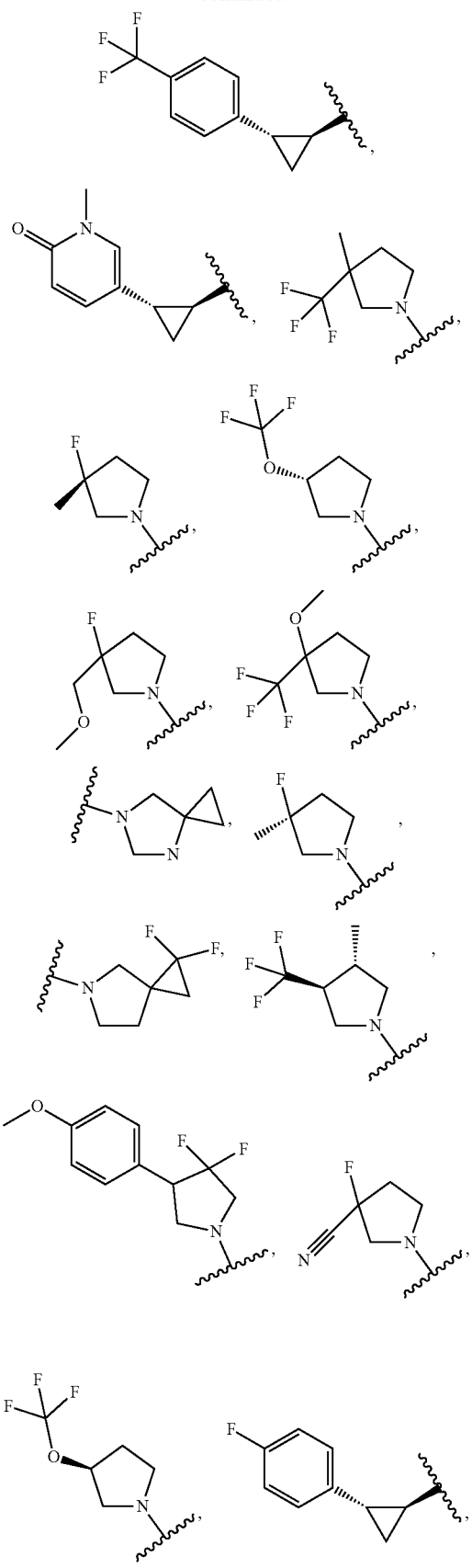
-continued
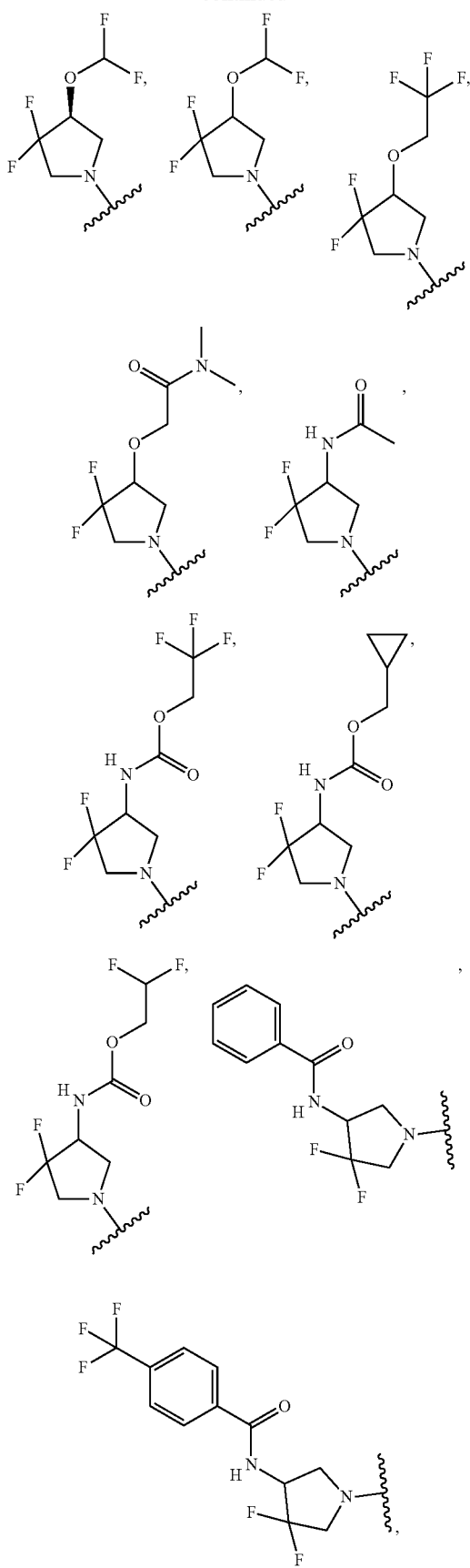

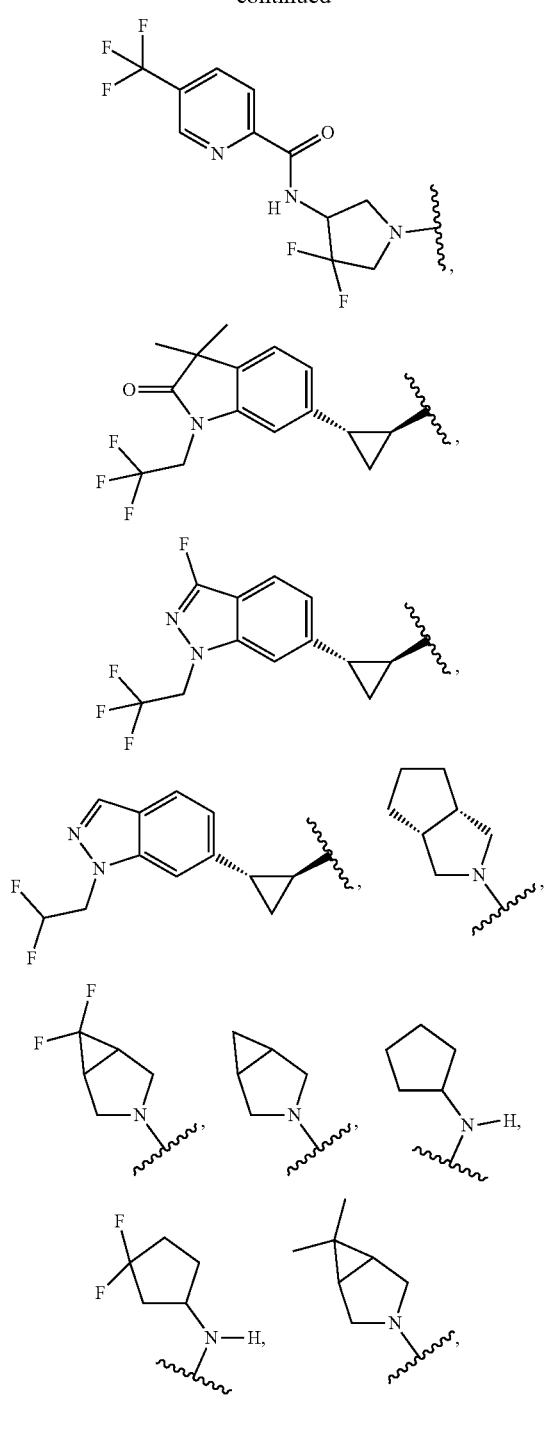

-continued
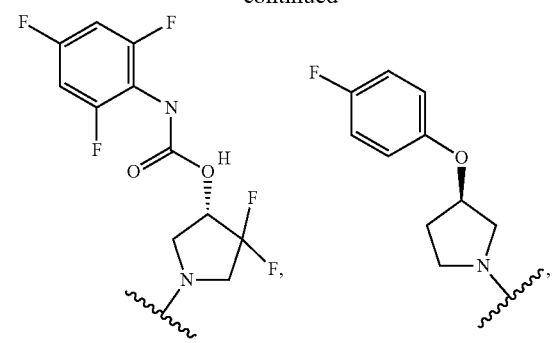
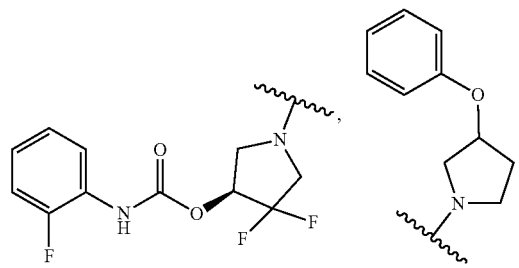
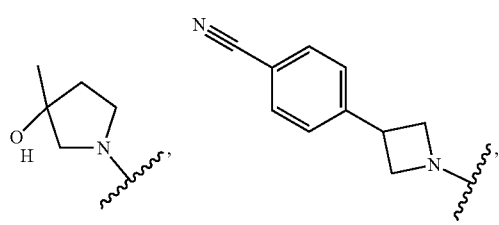
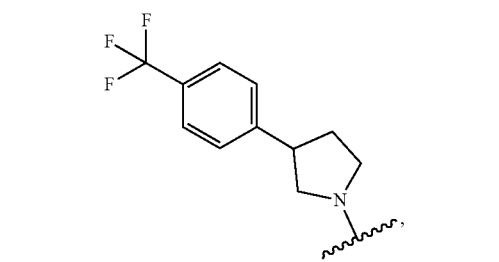
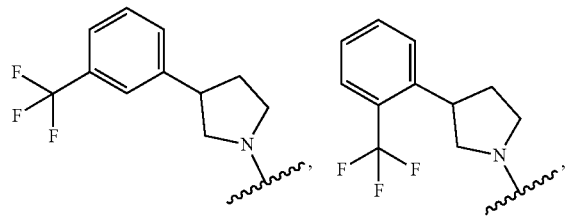
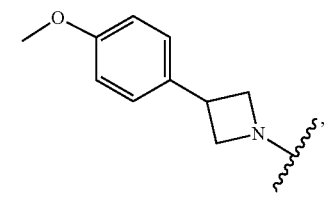
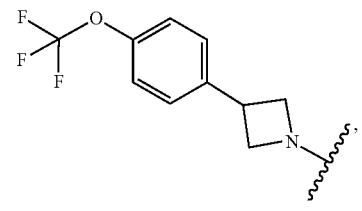
-continued
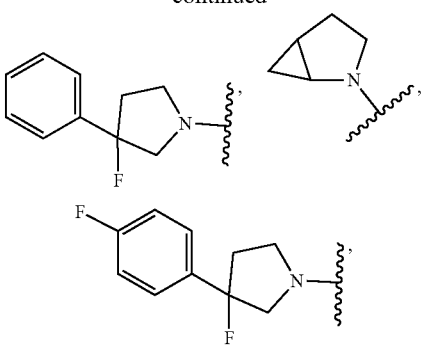
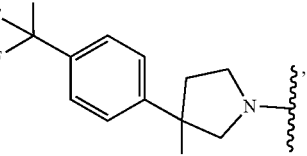
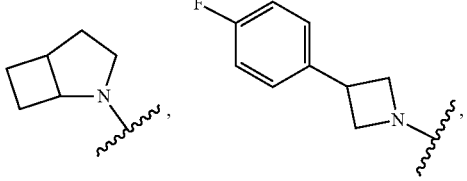
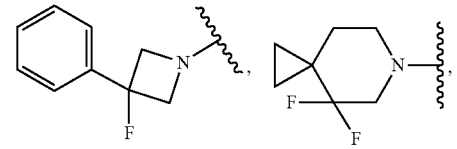
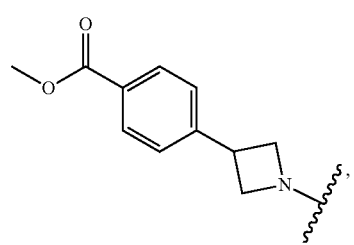
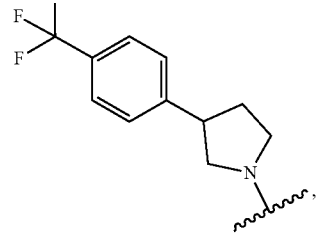
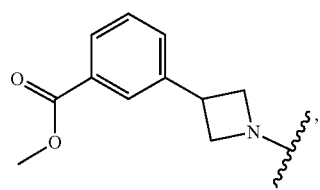

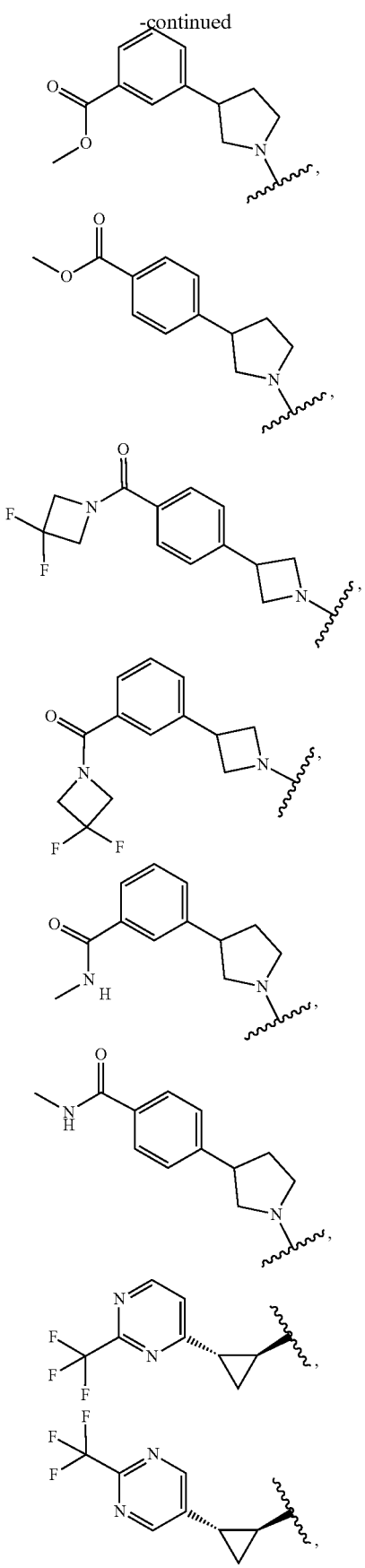
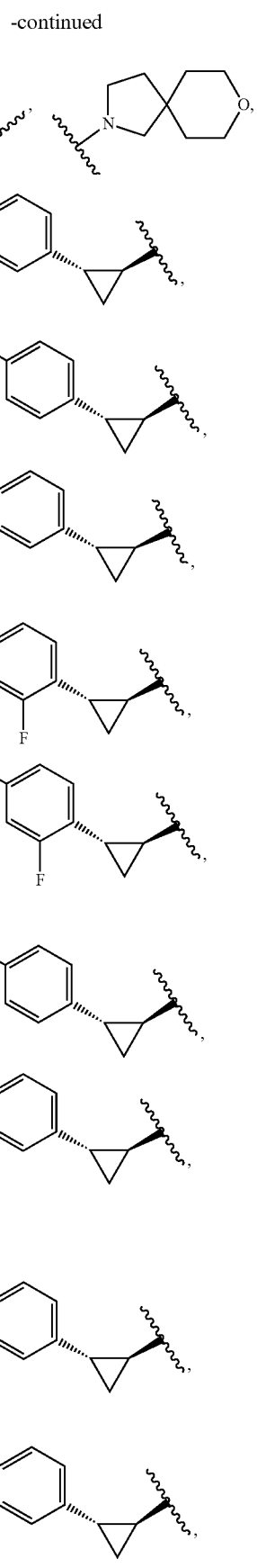

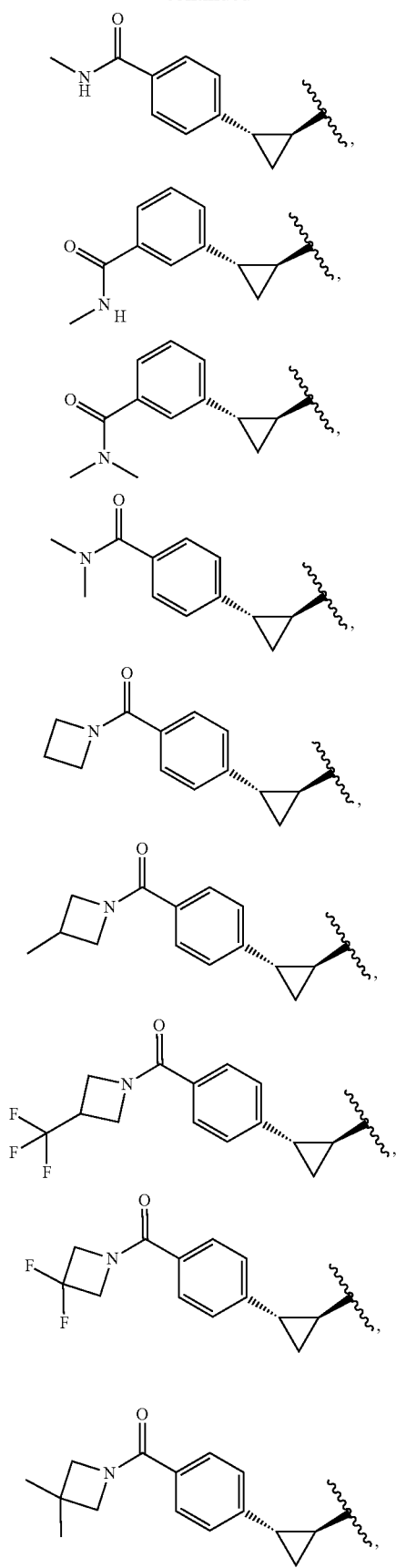
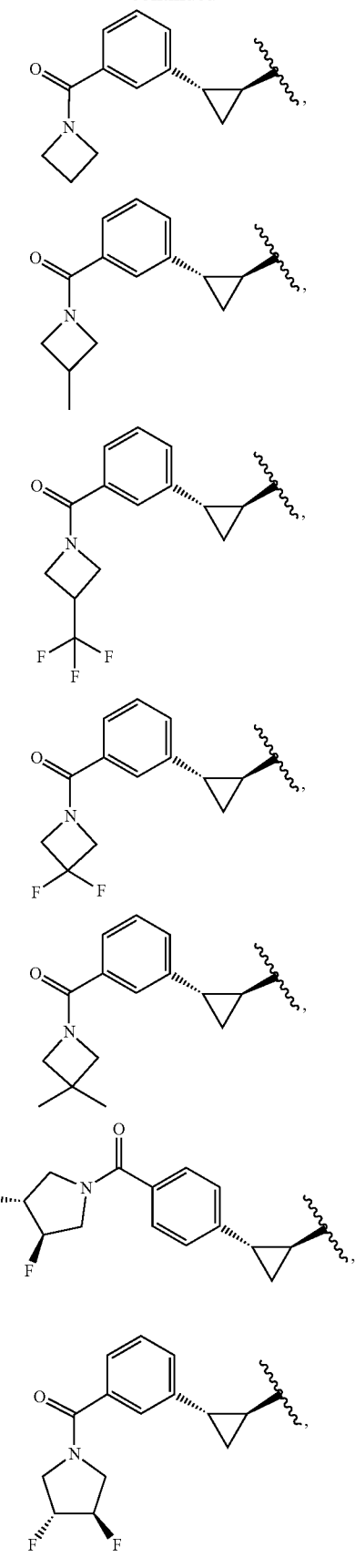

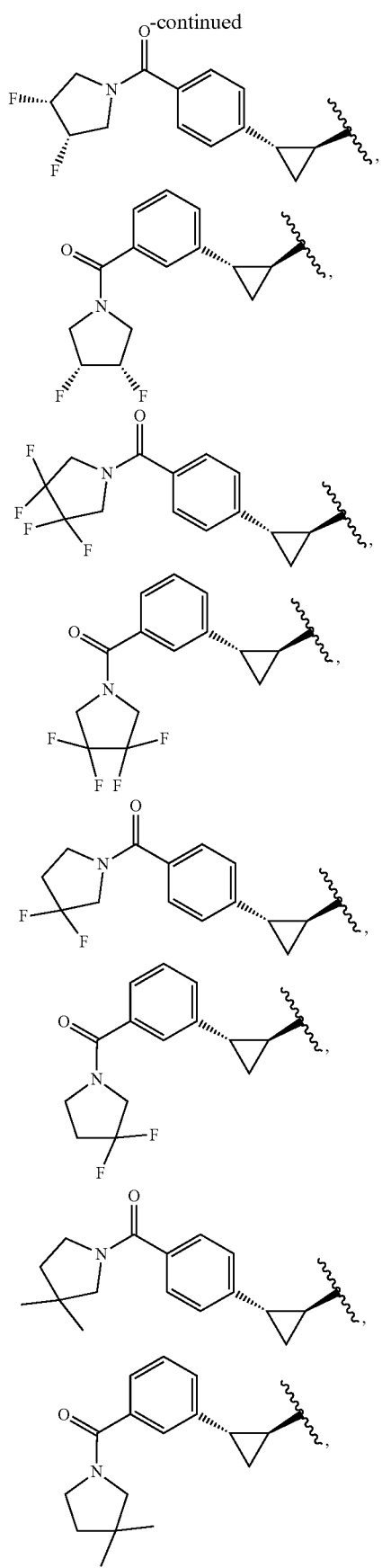
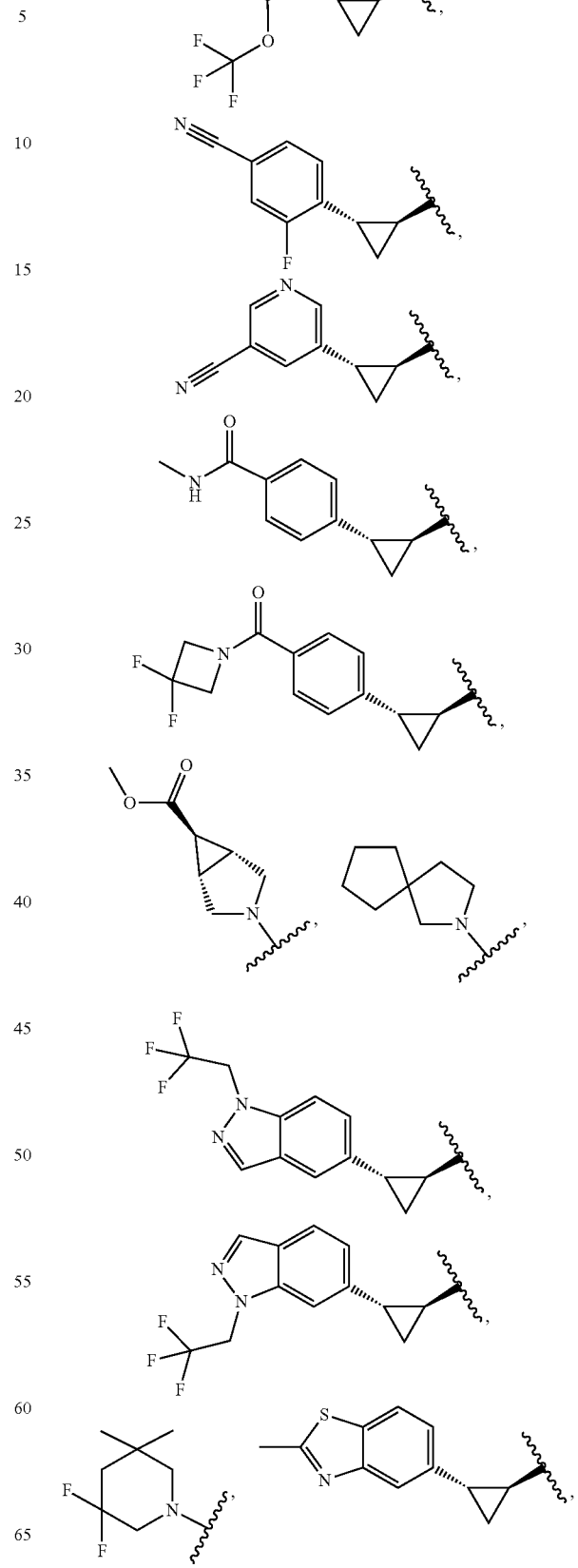

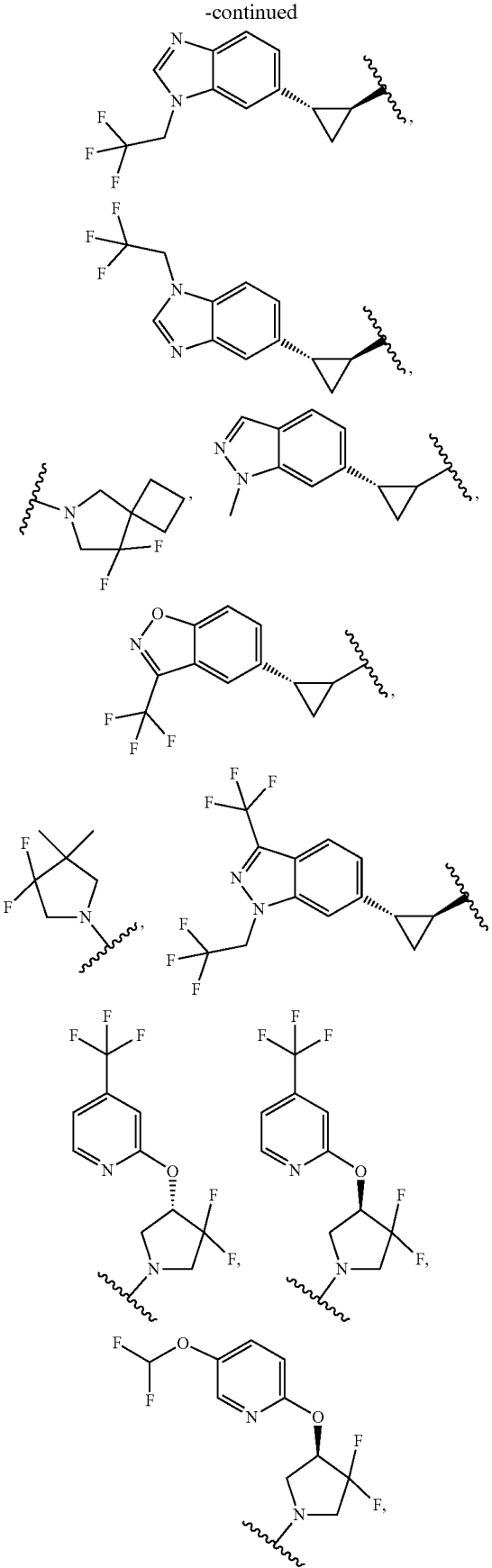
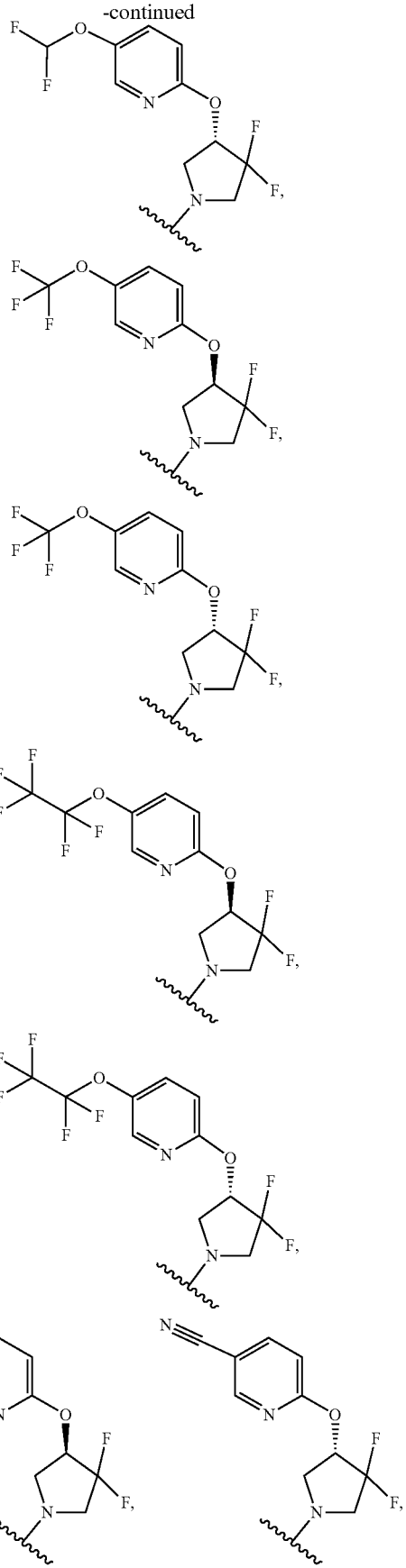

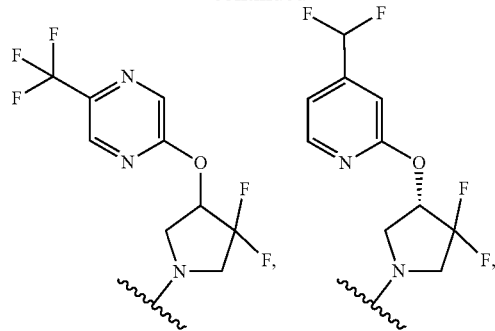
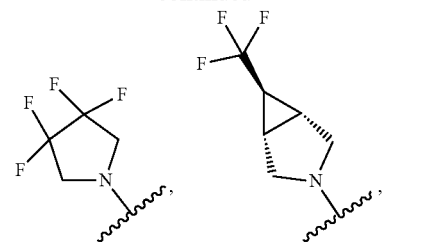
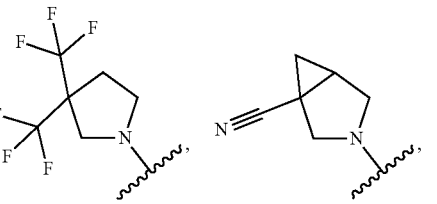
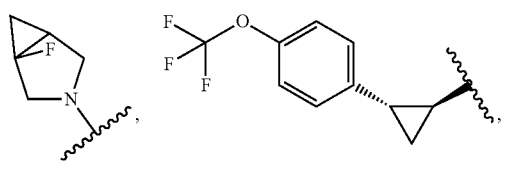
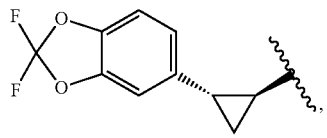
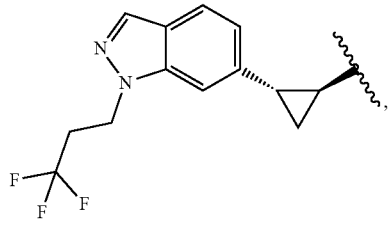
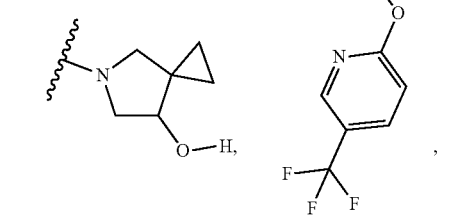
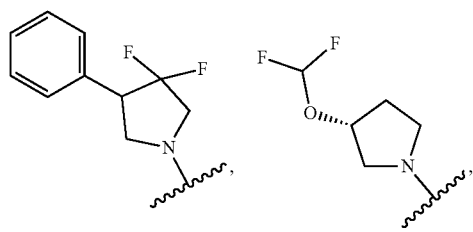
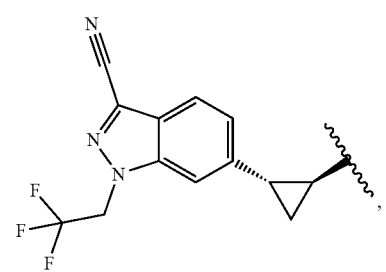
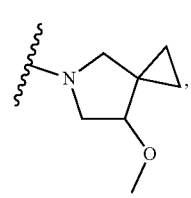
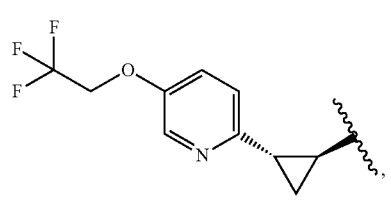

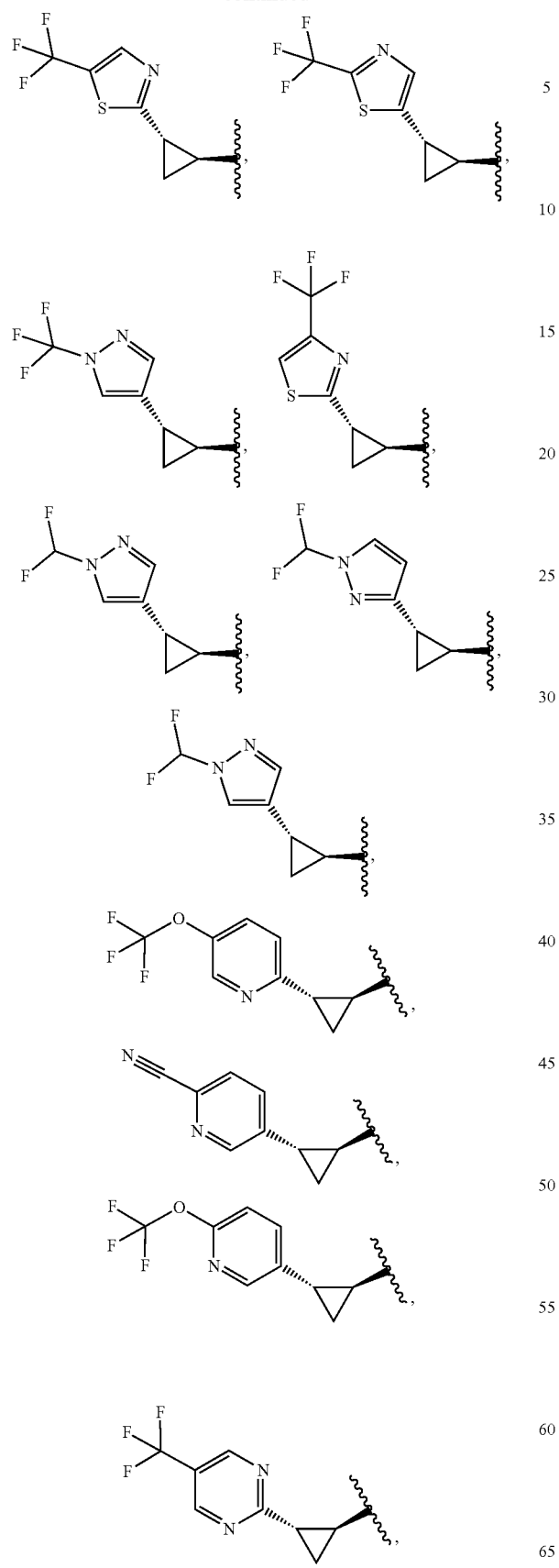
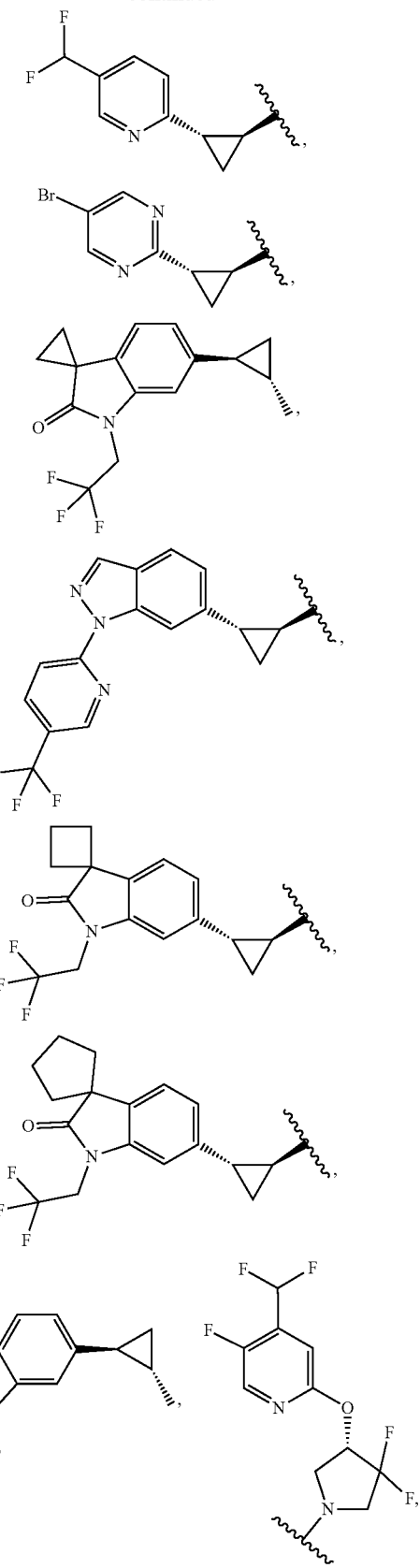

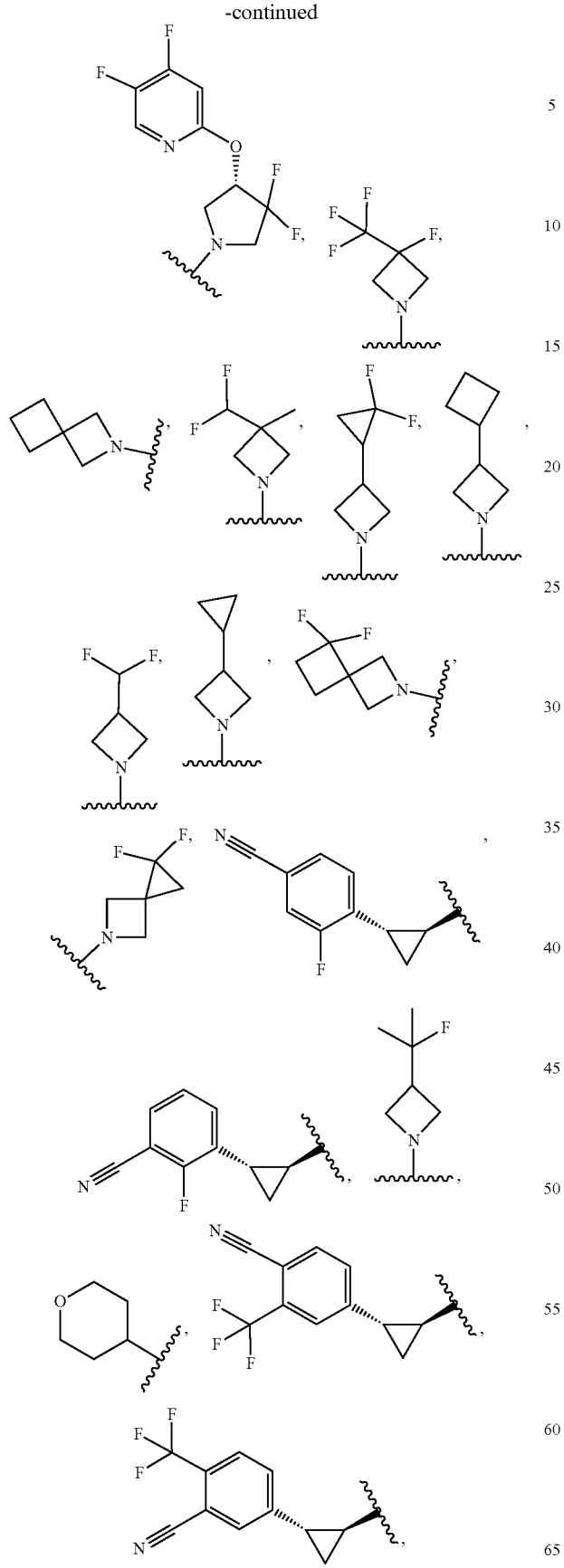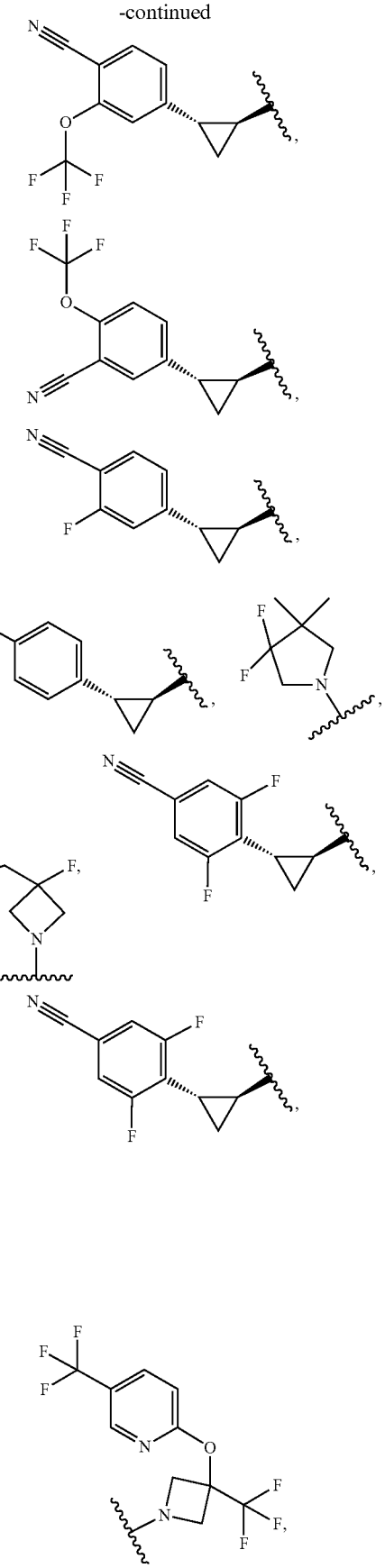

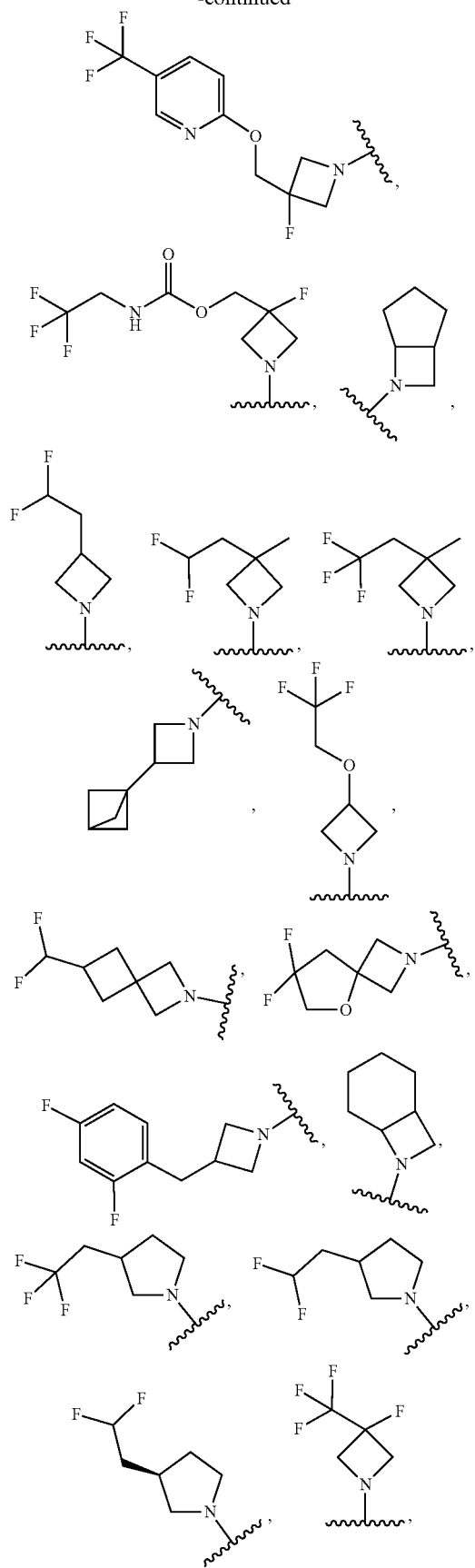
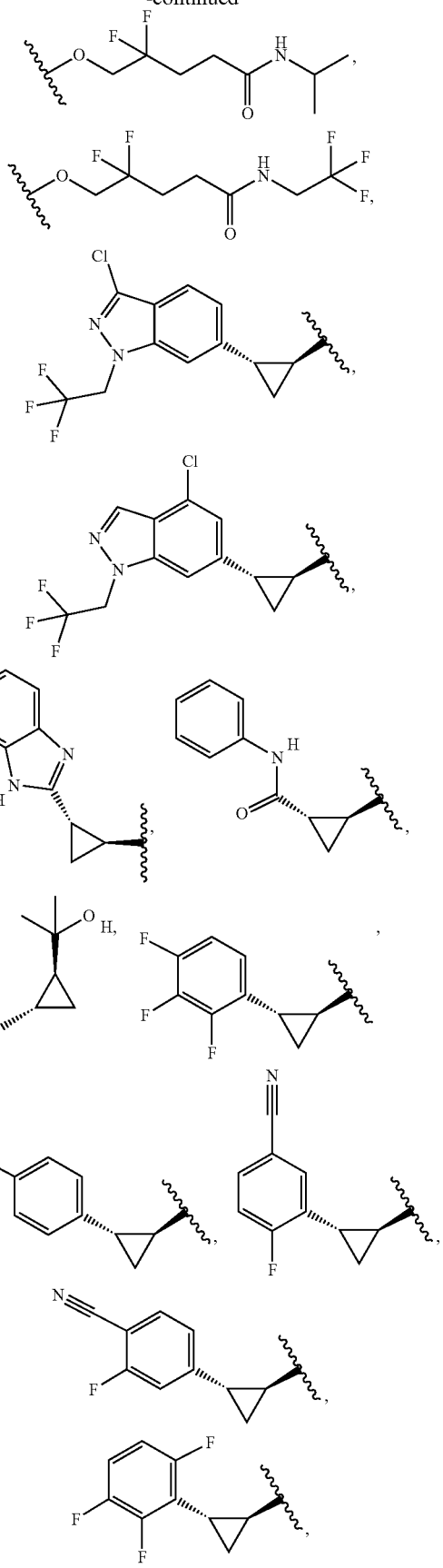

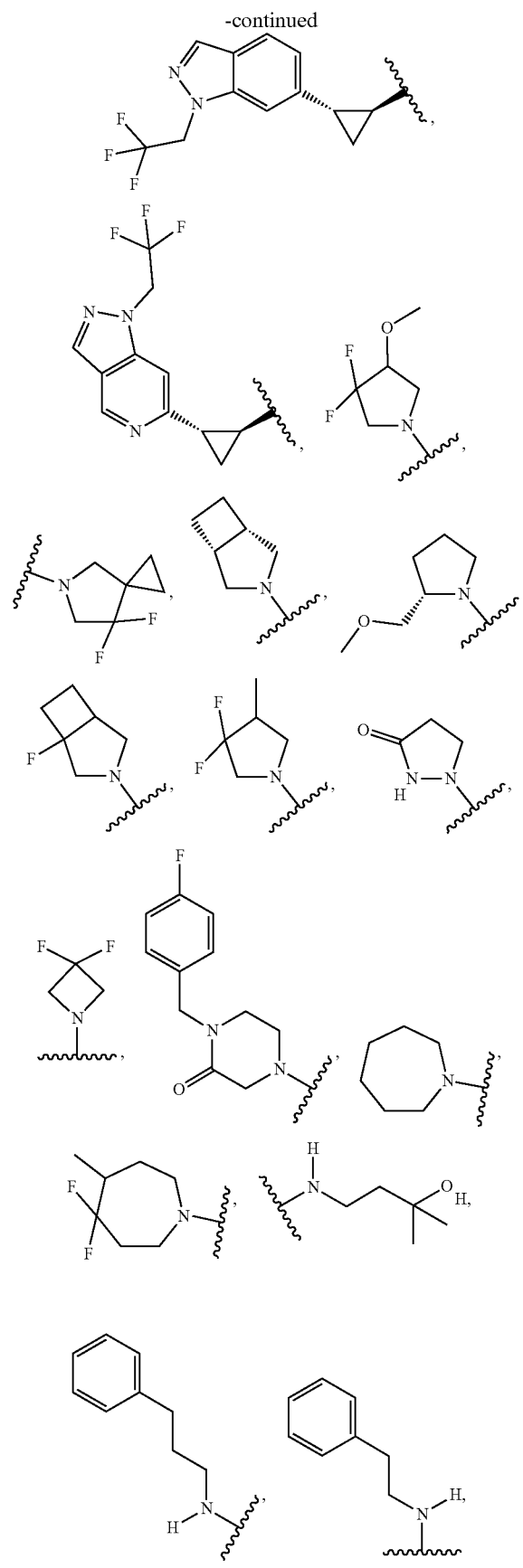
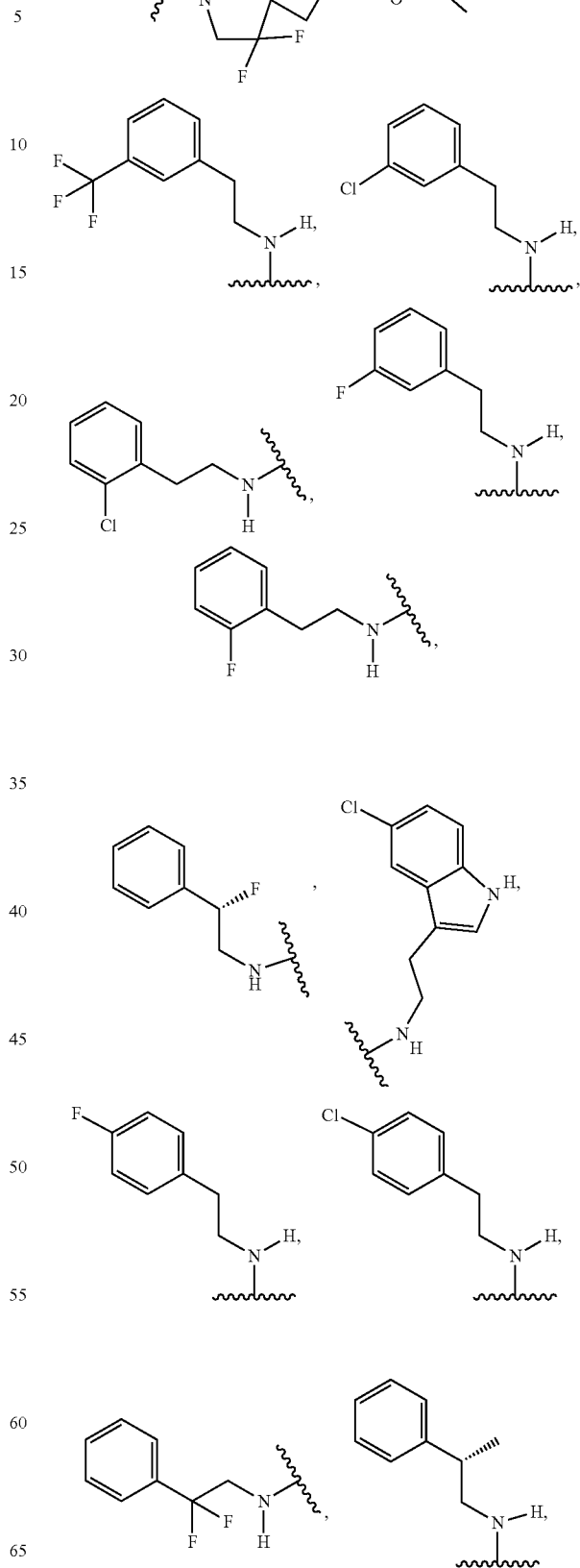

-continued
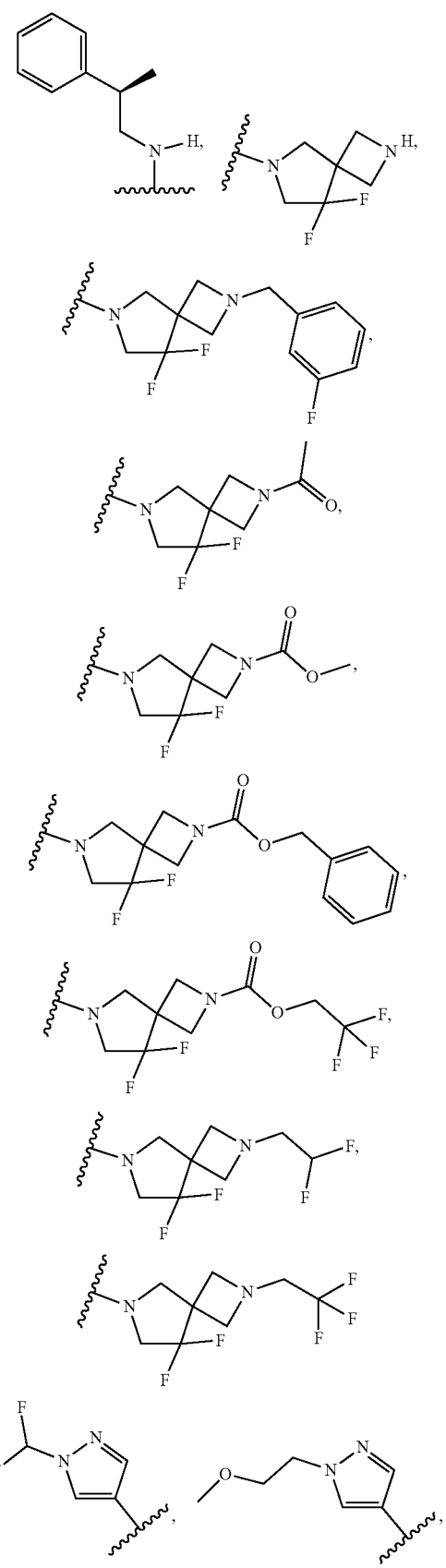
-continued
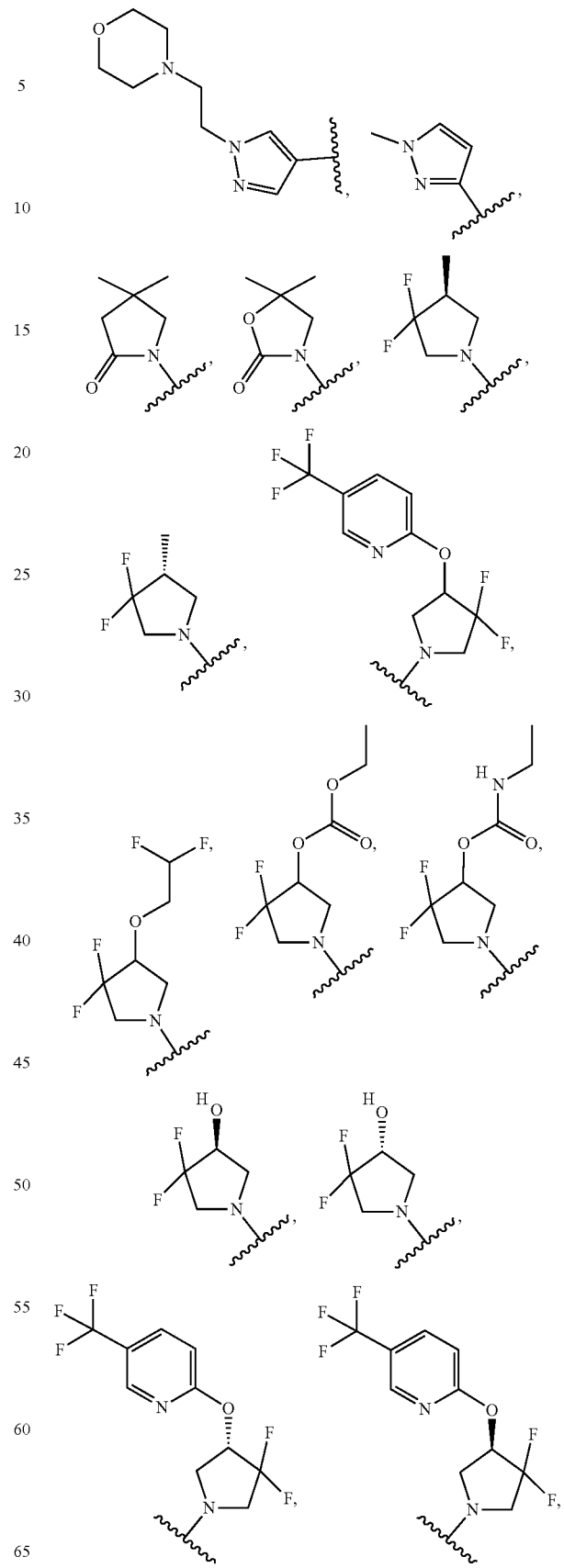

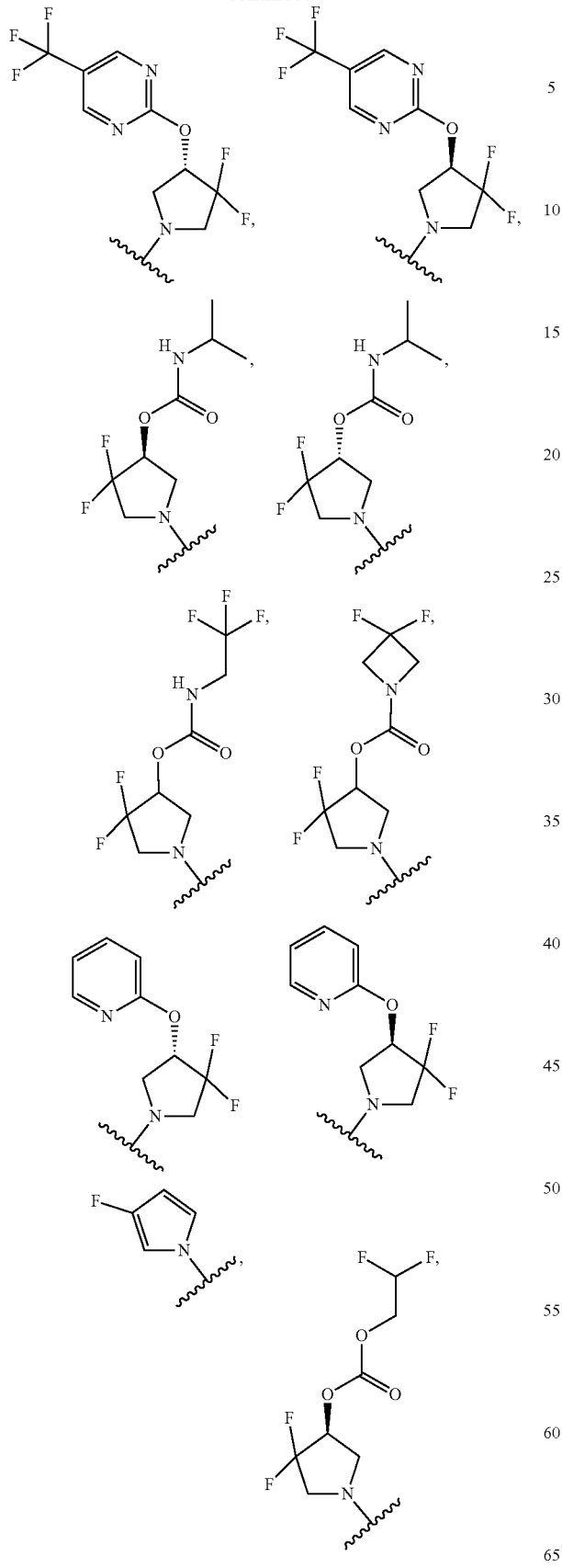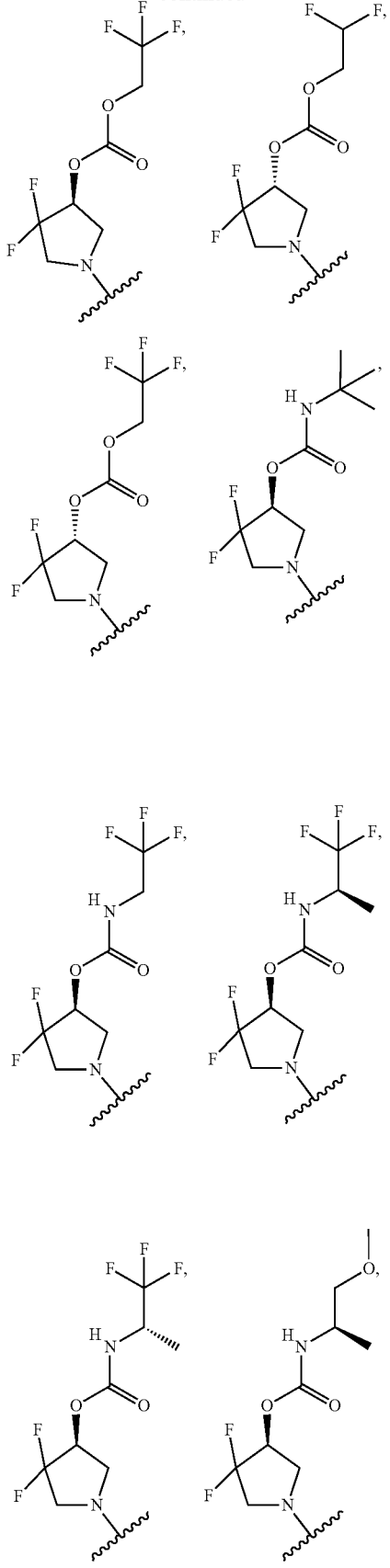

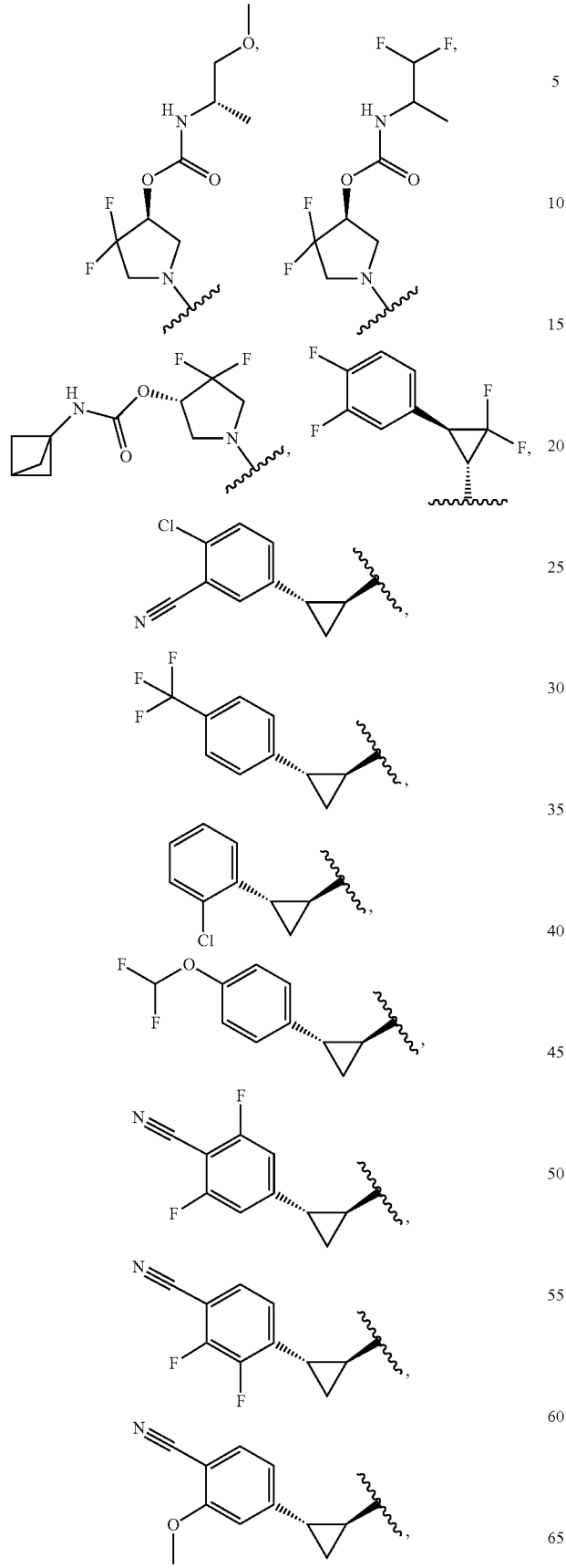
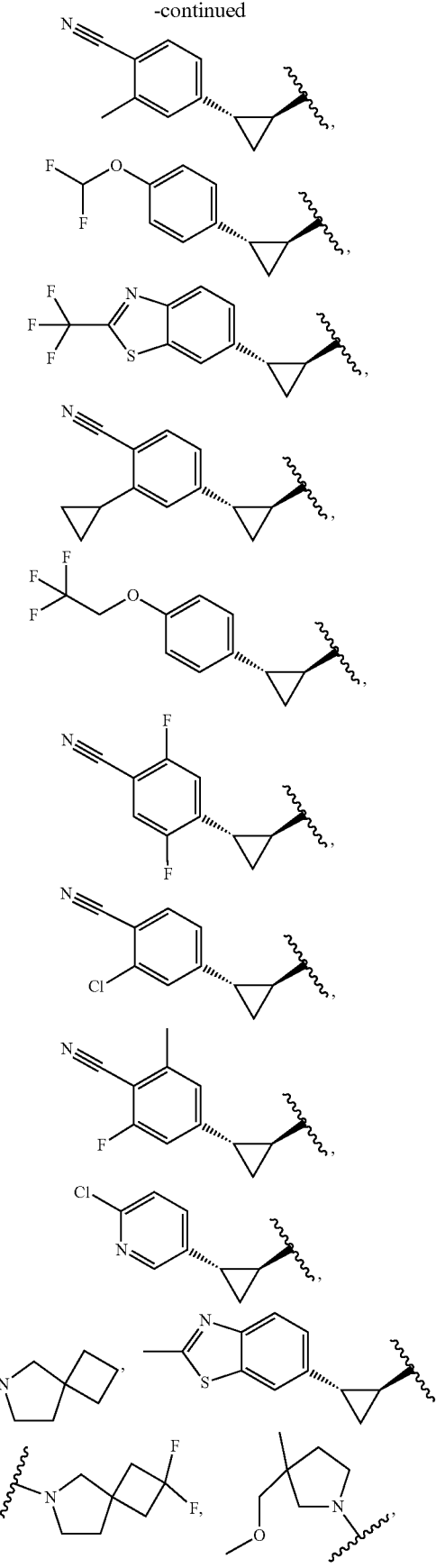

71
-continued
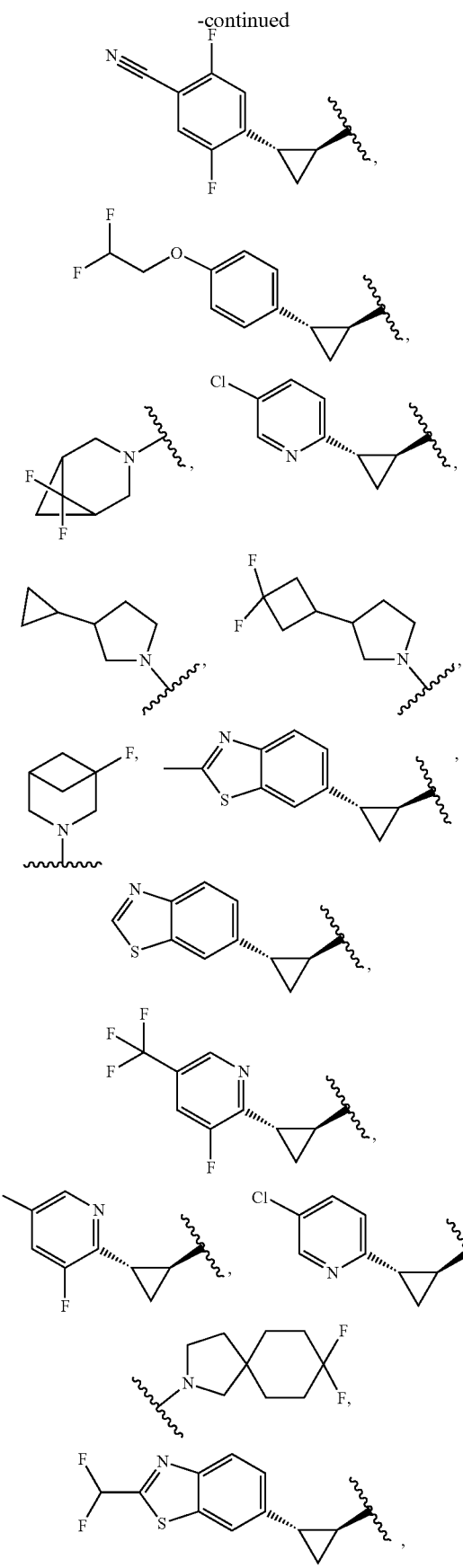
72
-continued
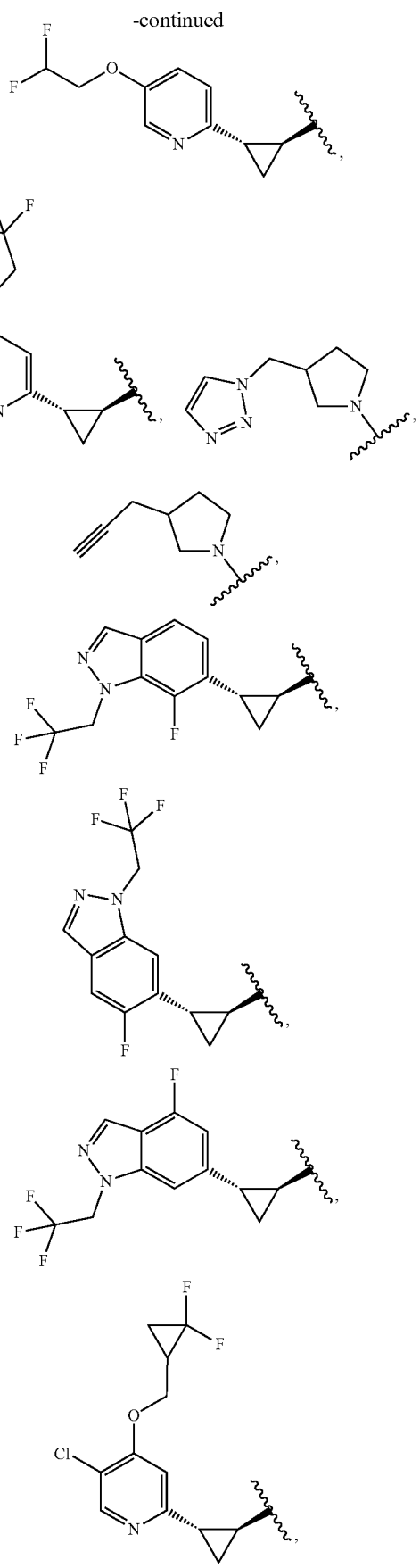

-continued
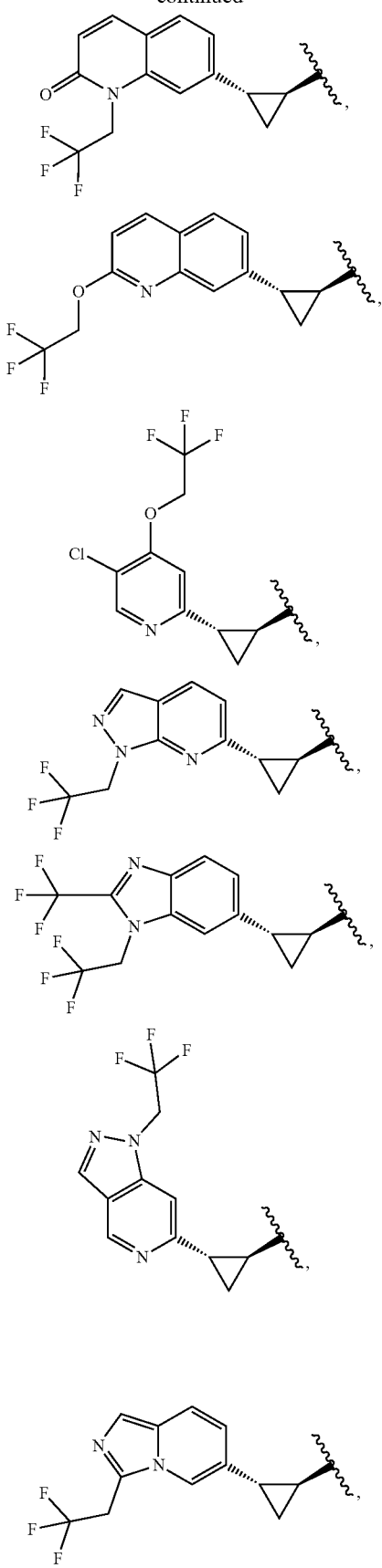
-continued
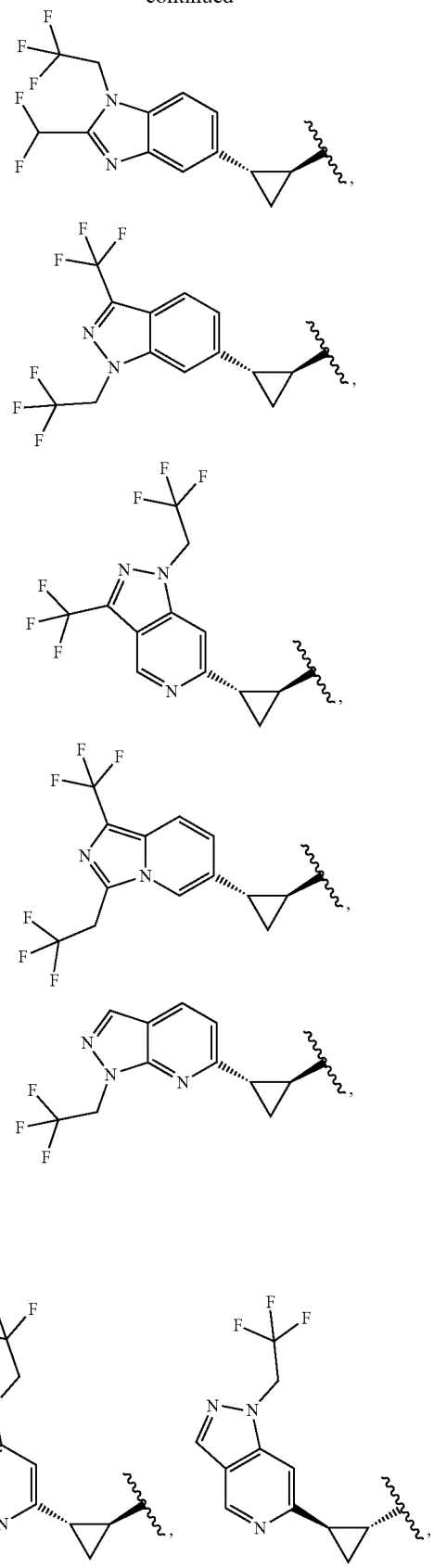

-continued
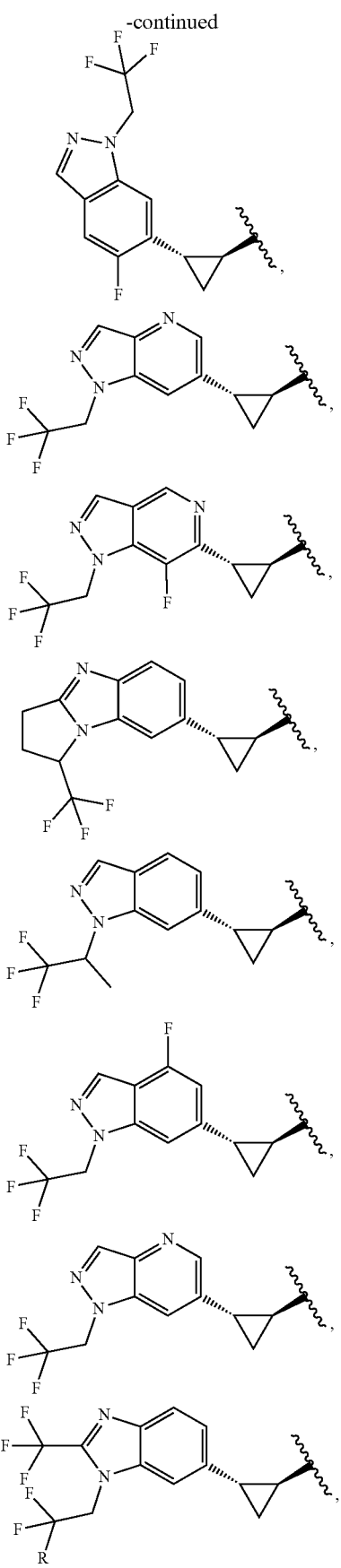
-continued
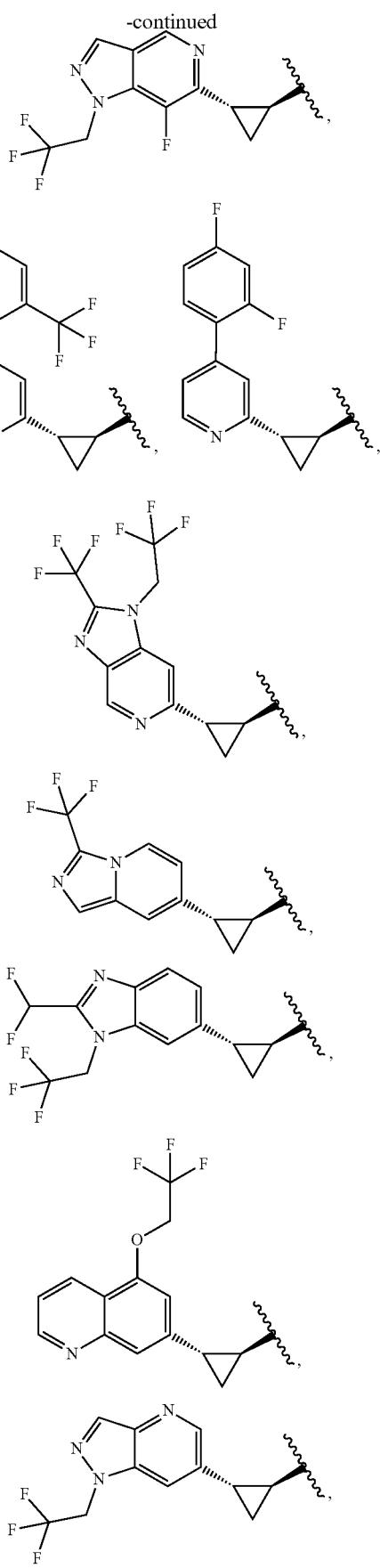

-continued
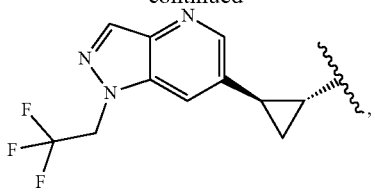
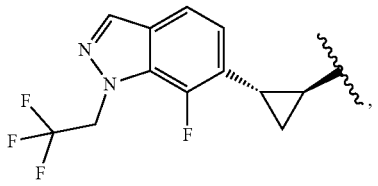
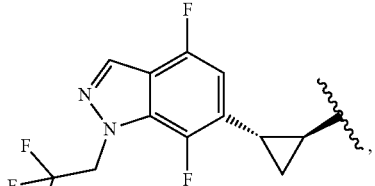
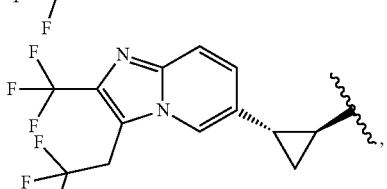
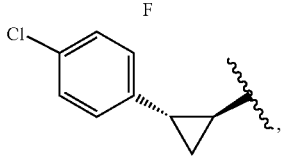
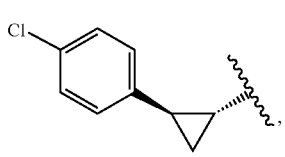
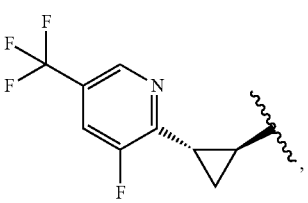
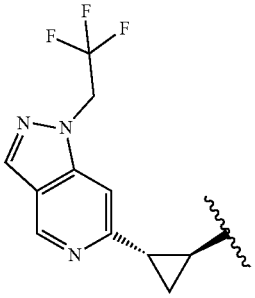
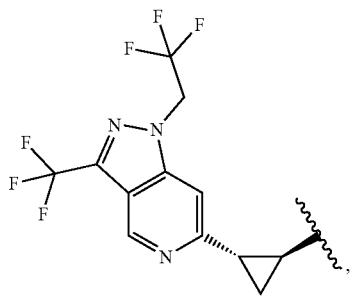
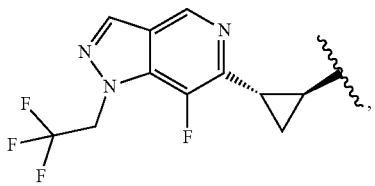
-continued
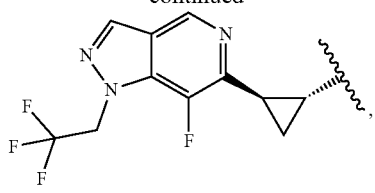
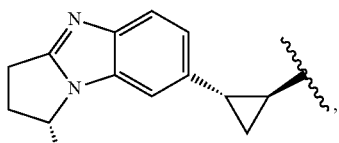
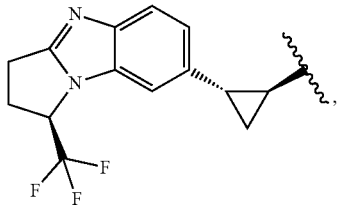
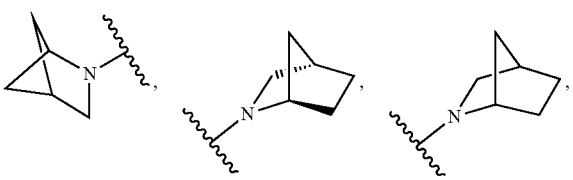
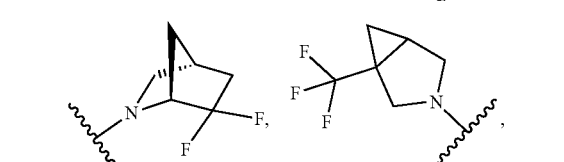
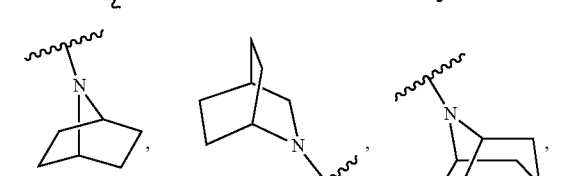
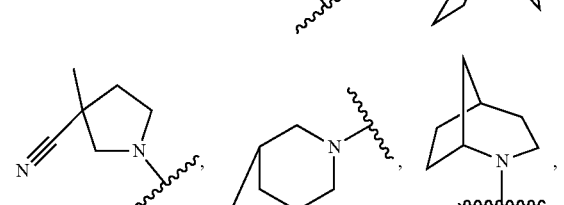
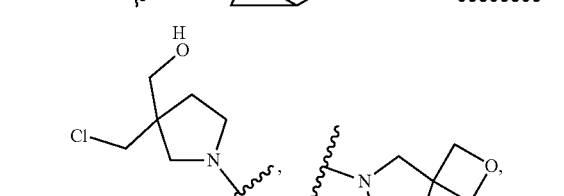
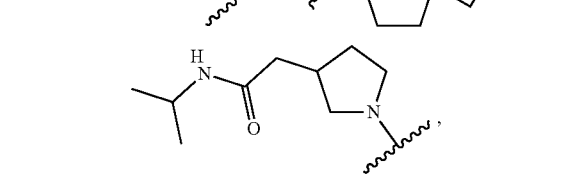

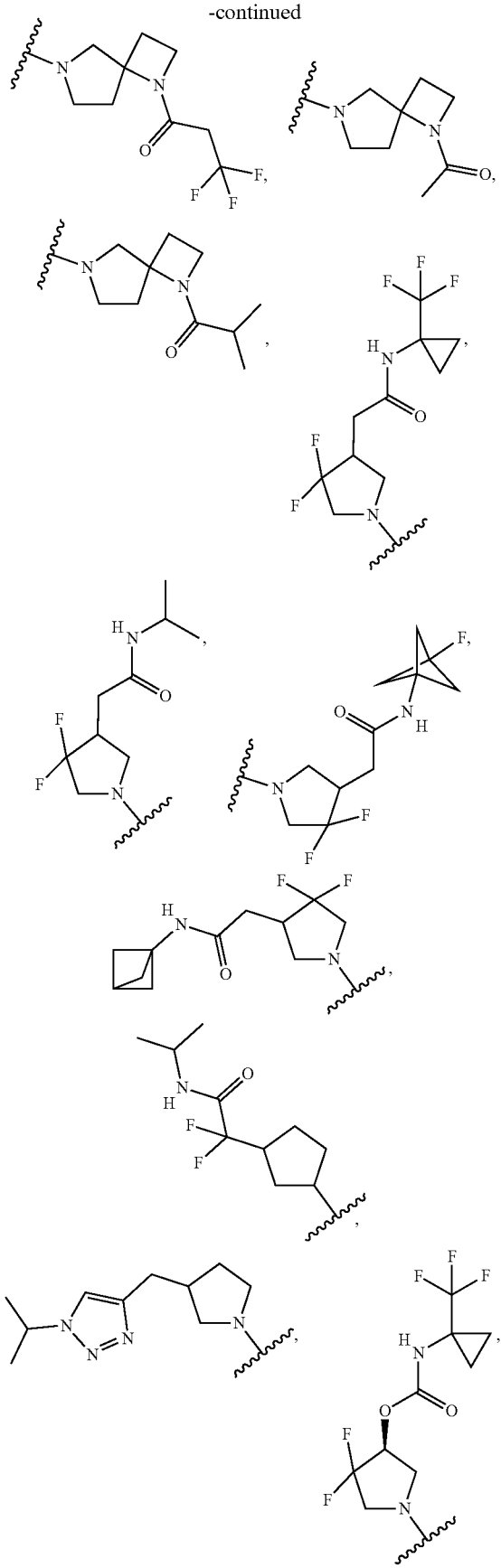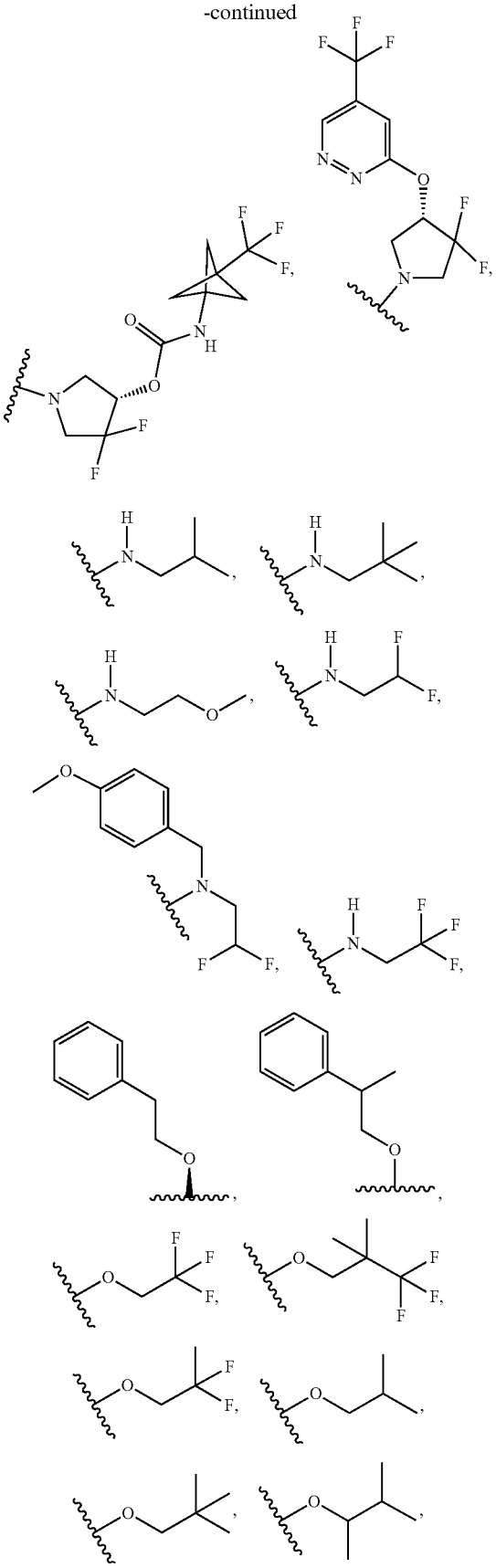

81
-continued
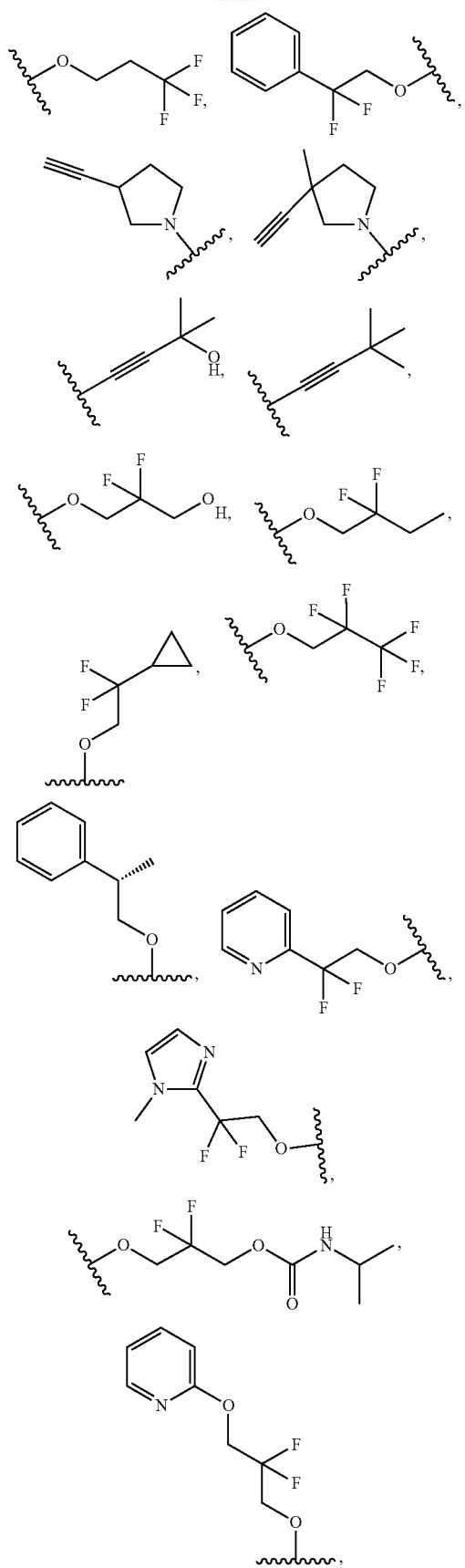
82
-continued
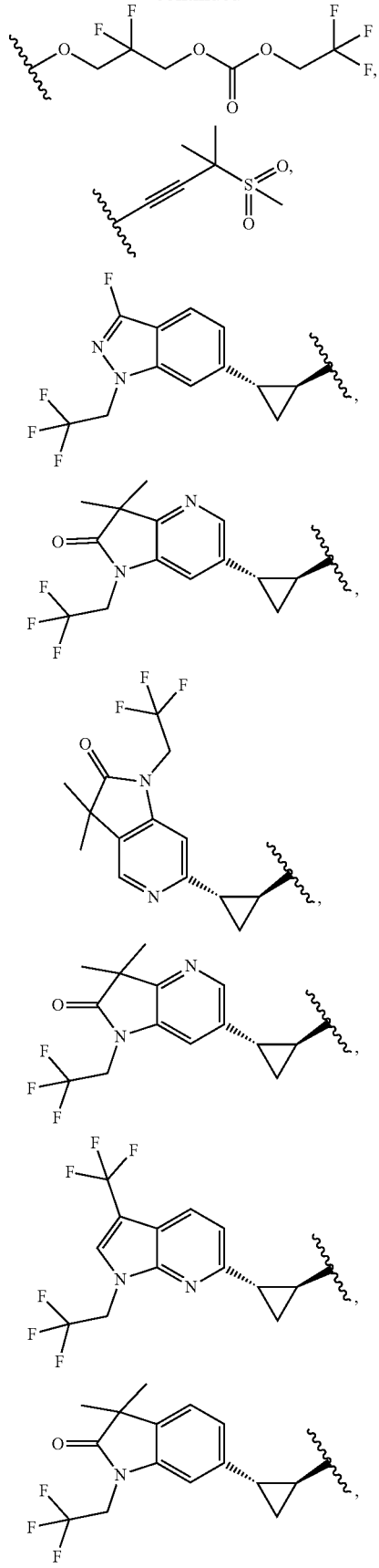

-continued
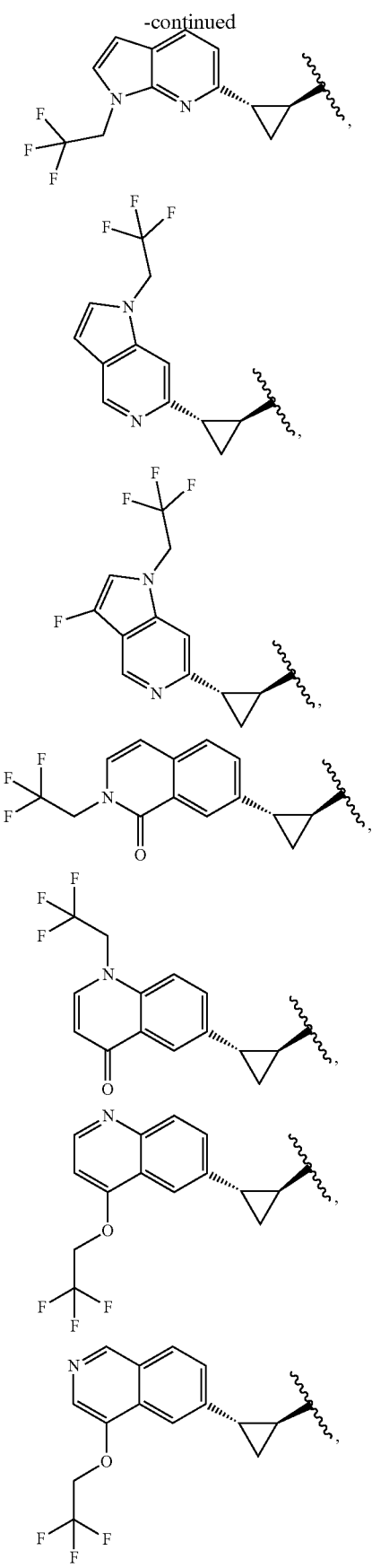
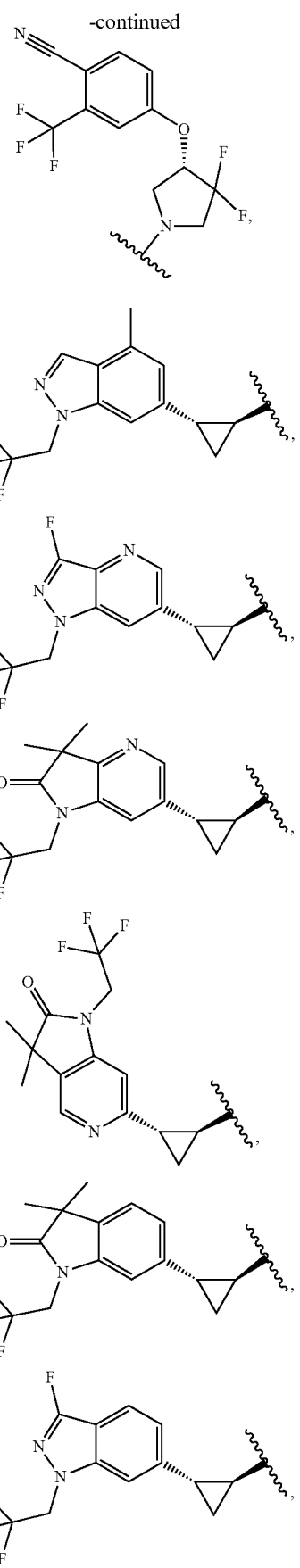

-continued
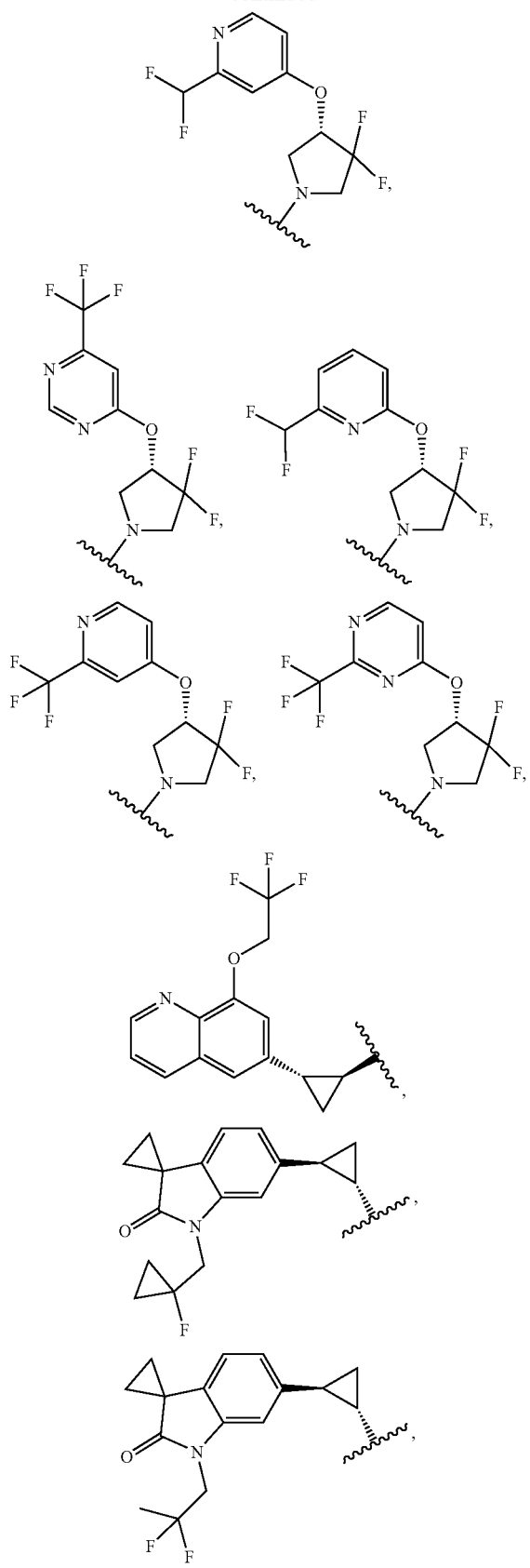
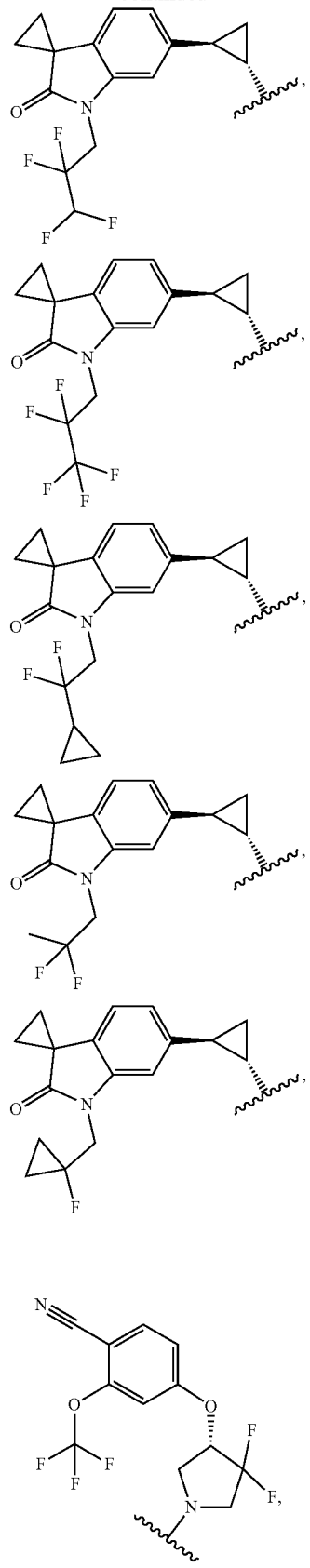

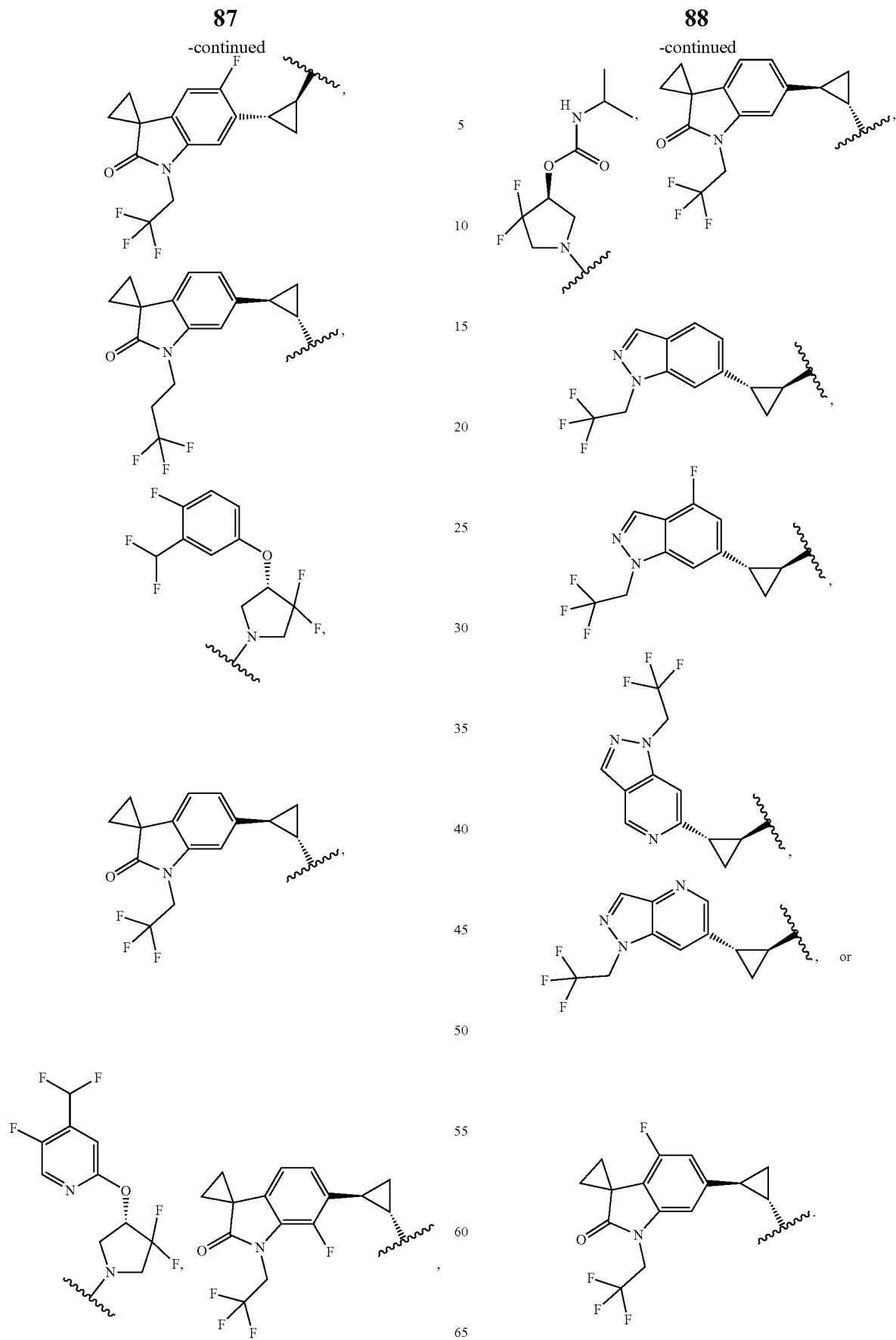

In some embodiments, a compound of the disclosure is a compound having the structure of Formula (II-f):

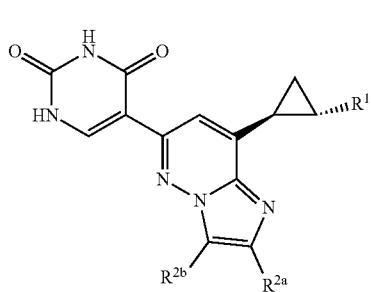
(II-f)

or a pharmaceutically acceptable salt thereof, wherein $R^1$, $R^{2a}$ and $R^{2b}$ are as described herein.

In some embodiments, a compound of the disclosure is a compound having the structure of Formula (II-f):

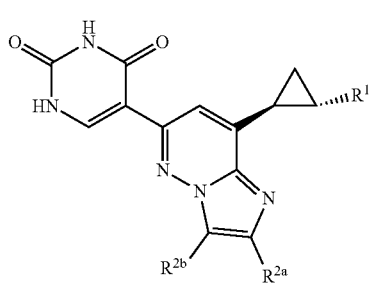
(II-f)

or a pharmaceutically acceptable salt thereof,
wherein $R^1$ is phenyl or heteroaryl, each of which is optionally substituted with one to three halogens and is further optionally substituted with one or two $R^3$, $R^{2a}$ and $R^{2b}$ are each independently hydrogen or halogen.

In some embodiments, a compound of the disclosure is a compound having the structure of Formula (III-a):

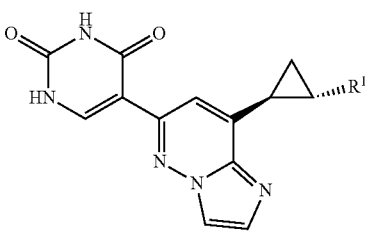
(III-a)

or a pharmaceutically acceptable salt thereof, wherein $R^1$ is as described herein.

In some embodiments, a compound of the disclosure is a compound having the structure of Formula (III-a):

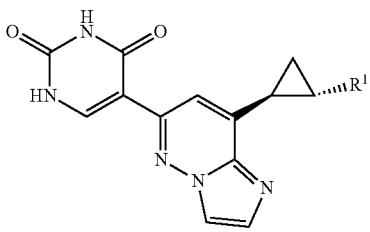
(III-a)

or a pharmaceutically acceptable salt thereof,
wherein $R^1$ is phenyl or heteroaryl, each of which is optionally substituted with one to three halogens and is further optionally substituted with one or two $R^3$.

In some embodiments, a compound of the disclosure is a compound having the structure of Formula (II-g):

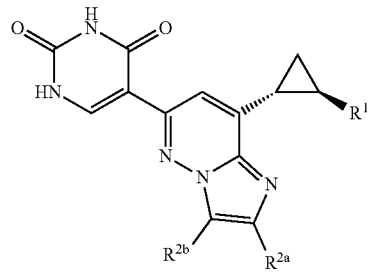
(II-g)

or a pharmaceutically acceptable salt thereof, wherein $R^1$, $R^{2a}$ and $R^{2b}$ are as described herein.

In some embodiments, a compound of the disclosure is a compound having the structure of Formula (II-g):

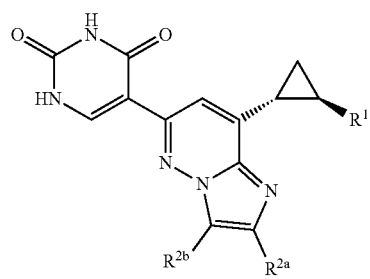
(II-g)

or a pharmaceutically acceptable salt thereof,
wherein $R^1$ is phenyl or heteroaryl, each of which is optionally substituted with one to three halogens and is further optionally substituted with one or two $R^3$, $R^{2a}$ and $R^{2b}$ are each independently hydrogen or halogen.

In some embodiments, a compound of the disclosure is a compound having the structure of Formula (III-b):

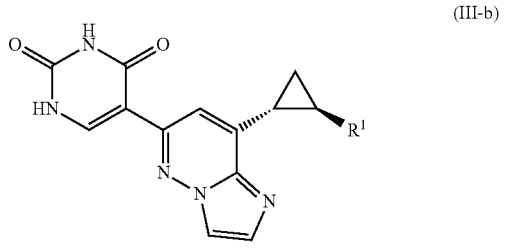
(III-b)

or a pharmaceutically acceptable salt thereof, wherein R¹ is as described herein.

In some embodiments, a compound of the disclosure is a compound having the structure of Formula (III-b):

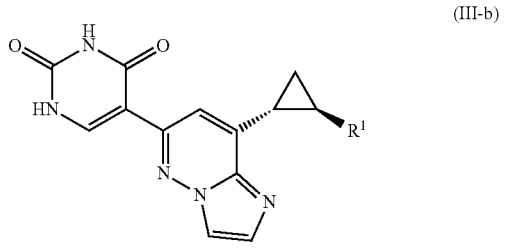
(III-b)

or a pharmaceutically acceptable salt thereof,
wherein R¹ is phenyl or heteroaryl, each of which is optionally substituted with one to three halogens and is further optionally substituted with one or two R³.

In some embodiments, a compound of the disclosure is a compound having the structure of Formula (II-h):

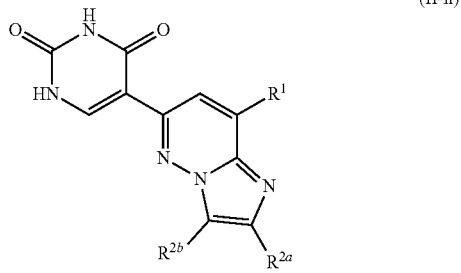
(II-h)

or a pharmaceutically acceptable salt thereof, wherein R¹, R$^{2a}$ and R$^{2b}$ are as described herein.

In some embodiments, a compound of the disclosure is a compound having the structure of Formula (II-h):

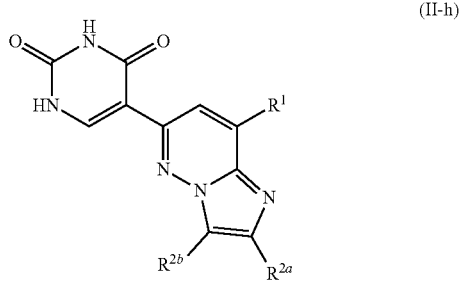
(II-h)

or a pharmaceutically acceptable salt thereof, wherein R¹ is C$_{3-7}$cycloalkyl or heterocycloalkyl, each of which is optionally substituted with one to three halogens and is further optionally substituted with one or two R³, R$^{2a}$ and R$^{2b}$ are each independently hydrogen or halogen.

In some embodiments, a compound of the disclosure is a compound having the structure of Formula (III-c):

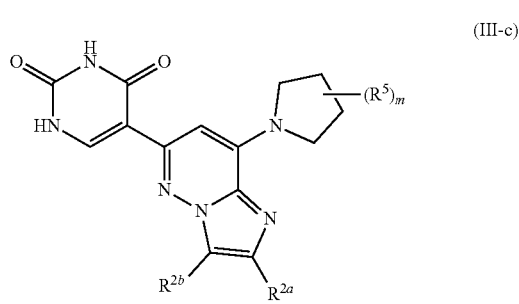
(III-c)

or a pharmaceutically acceptable salt thereof, wherein m, R⁵, R$^{2a}$ and R$^{2b}$ are as described herein.

In some embodiments, a compound of the disclosure is a compound having the structure of Formula (III-c):

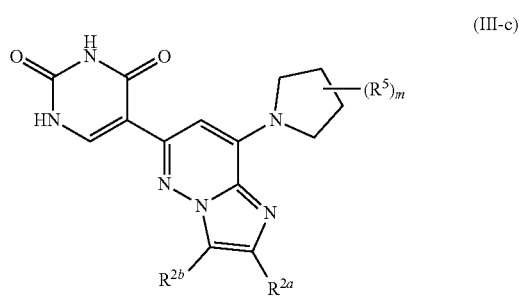
(III-c)

wherein each R⁵ is independently halogen, —CN, —C$_{1-6}$alkyl, —C$_{3-7}$cycloalkyl, —C$_{1-6}$alkyl-N(R$^d$)(R$^d$), —OR$^c$, —N(R$^b$)(R$^b$), —C(═O)C$_{1-6}$alkyl, —C(═O)OC$_{1-6}$alkyl, —OC(═O)N(H)C$_{1-6}$alkyl, —OC(═O)OC$_{1-6}$alkyl, —O—C$_{6-12}$aryl, —O-heteroaryl, or —C$_{1-6}$haloalkyl, or the two R⁵ moieties join together to form a 3 to 6 membered cycloalkyl or heterocycloalkyl ring, wherein the ring is optionally substituted with one to three halogens and is further optionally substituted with one to three R⁶;

R⁶ is halogen, —CN, —C$_{1-6}$alkyl, —C$_{1-6}$ haloalkyl, —C$_{3-7}$cycloalkyl, —N(R$^b$)(R$^b$), —C(═O)C$_{1-6}$alkyl, —C(═O)OC$_{1-6}$alkyl, —OC(═O)N(H)C$_{1-6}$alkyl, —OC(═O)OC$_{1-6}$alkyl, or —OR$^c$; and m is 0, 1, 2, 3 or 4;

and wherein R$^{2a}$ and R$^{2b}$ are as described herein.

In some embodiments, a compound of the disclosure is a compound having the structure of Formula (III-c):

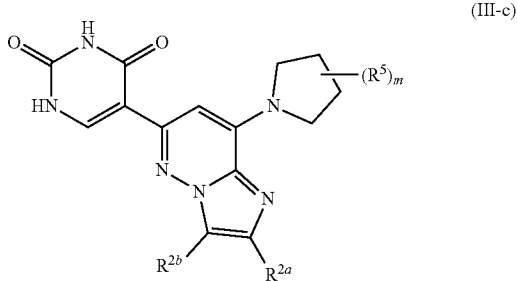

(III-c)

or a pharmaceutically acceptable salt thereof,
wherein
each $R^5$ is independently halogen, —CN, —$C_{1-6}$alkyl, —$C_{3-7}$cycloalkyl, —$C_{1-6}$alkyl-N($R^d$)($R^d$), —$OR^c$, —N($R^b$)($R^b$), —C(=O)$C_{1-6}$alkyl, —C(=O)O$C_{1-6}$alkyl, —OC(=O)N(H)$C_{1-6}$alkyl, —OC(=O)O$C_{1-6}$alkyl, or —$C_{1-6}$haloalkyl, or the two $R^5$ moieties join together to form a 3 to 6 membered cycloalkyl or heterocycloalkyl ring, wherein the ring is optionally substituted with one to three halogens and is further optionally substituted with one to three $R^6$;
$R^6$ is halogen, —CN, —$C_{1-6}$alkyl, —$C_{1-6}$haloalkyl, —$C_{3-7}$cycloalkyl, —N($R^b$)($R^b$), —C(=O)$C_{1-6}$alkyl, —C(=O)O$C_{1-6}$alkyl, —OC(=O)N(H)$C_{1-6}$alkyl, —OC(=O)O$C_{1-6}$alkyl, or —$OR^c$; and
m is 0, 1, 2, 3 or 4;
and wherein $R^{2a}$ and $R^{2b}$ are as described herein.

In some embodiments, a compound of the disclosure is a compound having the structure of Formula (III-d):

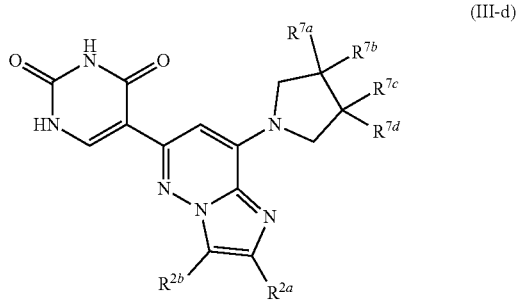

(III-d)

or a pharmaceutically acceptable salt thereof, wherein $R^{7a}$, $R^{7b}$, $R^{7c}$, $R^{7d}$, $R^{2a}$ and $R^{2b}$ are as described herein.

In some embodiments, a compound of the disclosure is a compound having the structure of Formula (III-d):

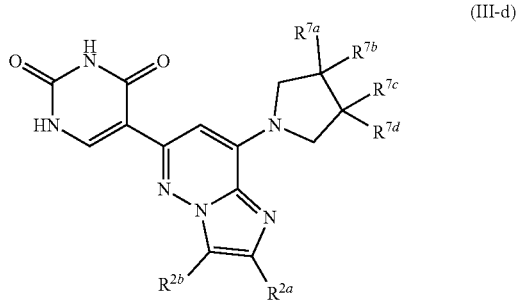

(III-d)

or a pharmaceutically acceptable salt thereof,
wherein $R^{7a}$, $R^{7b}$, $R^{7c}$, and $R^{7d}$ are independently halogen, —$C_{1-6}$alkyl or —$C_{1-6}$haloalkyl, or the two of the $R^{7a}$, $R^{7b}$, $R^{7c}$, or $R^{7d}$ moieties join together to form a 3 to 6 membered cycloalkyl ring, wherein the ring is optionally substituted with one to three halogens,
and wherein $R^{2a}$ and $R^{2b}$ are as described herein.

In some embodiments, a compound of the disclosure is a compound having the structure of Formula (II-f), (II-g), (III-a) or (III-b), or a pharmaceutically acceptable salt thereof, wherein $R^1$ is phenyl or heteroaryl, each of which is optionally substituted with one to three halogens. In some embodiments, a compound of the disclosure is a compound having the structure of Formula (II-f), (II-g), (III-a) or (III-b), or a pharmaceutically acceptable salt thereof, wherein $R^1$ is phenyl or heteroaryl, each of which is optionally substituted with one or two $R^3$. In some embodiments, a compound of the disclosure is a compound having the structure of Formula (II-f), (II-g), (III-a) or (III-b), wherein $R^1$ is phenyl or heteroaryl substituted with one or two $R^3$.

In some embodiments, a compound of the disclosure is a compound having the structure of Formula (II-h), or a pharmaceutically acceptable salt thereof, wherein $R^1$ is $C_{3-7}$cycloalkyl or heterocycloalkyl, each of which is optionally substituted with one to three halogens. In some embodiments, a compound of the disclosure is a compound having the structure of Formula (II-h), or a pharmaceutically acceptable salt thereof, wherein $R^1$ is $C_{3-7}$cycloalkyl or heterocycloalkyl, each of which is optionally substituted with one or two $R^3$. In some embodiments, a compound of the disclosure is a compound having the structure of Formula (II-h), wherein $R^1$ is $C_{3-7}$cycloalkyl or heterocycloalkyl substituted with one or two $R^3$.

In some embodiments, a compound of the disclosure is a compound having the structure of Formula (III-c), or a pharmaceutically acceptable salt thereof, wherein $R^5$ is independently halogen, —CN, —$C_{1-6}$alkyl, —$C_{3-7}$cycloalkyl, —$C_{1-6}$alkyl-N($R^d$)($R^d$), —$OR^c$, —N($R^b$)($R^b$), —C(=O)$C_{1-6}$alkyl, —C(=O)O$C_{1-6}$alkyl, —OC(=O)N(H)$C_{1-6}$alkyl, —OC(=O)O$C_{1-6}$alkyl, —O—$C_{6-12}$aryl, —O-heteroaryl, or —$C_{1-6}$haloalkyl. In some embodiments, a compound of the disclosure is a compound having the structure of Formula (III-c), or a pharmaceutically acceptable salt thereof, wherein $R^5$ is independently halogen, —$C_{1-6}$alkyl, —C(=O)O$C_{1-6}$alkyl, or —OC(=O)N(H)$C_{1-6}$alkyl. In some embodiments, a compound of the disclosure is a compound having the structure of Formula (III-c), or a pharmaceutically acceptable salt thereof, wherein two $R^5$ moieties join together to form a 3 to 6 membered cycloalkyl or heterocycloalkyl ring, wherein the ring is optionally substituted with one to three halogens and is further optionally substituted with one to three $R^6$. In some embodiments, a compound of the disclosure is a compound having the structure of Formula (III-c), wherein two $R^5$ moieties join together to form a 3 to 6 membered cycloalkyl or heterocycloalkyl ring.

In some embodiments, a compound of the disclosure is a compound having the structure of Formula (III-d), or a pharmaceutically acceptable salt thereof, wherein $R^{7a}$, $R^{7b}$, $R^{7c}$, and $R^{7d}$ are independently halogen, —$C_{1-6}$alkyl or —$C_{1-6}$haloalkyl. In some embodiments, a compound of the disclosure is a compound having the structure of Formula (III-d), or a pharmaceutically acceptable salt thereof, wherein $R^{7a}$, $R^{7b}$, $R^{7c}$, and $R^{7d}$ are independently halogen, —$C_{1-6}$alkyl or —$C_{1-6}$haloalkyl, and the two of the $R^{7a}$, $R^{7b}$, $R^{7c}$, or $R^{7d}$ moieties join together to form a 3 to 6 membered cycloalkyl ring, wherein the ring is optionally substituted with one to three halogens. In some embodiments, a compound of the disclosure is a compound having the structure of Formula (III-d), or a pharmaceutically acceptable salt thereof, wherein the two of the $R^{7a}$, $R^{7b}$, $R^{7c}$, or $R^{7d}$ moieties join together to form a 3 to 6 membered cycloalkyl or heterocycloalkyl ring.

In some embodiments, the compound of Formula (I), (II-a), (II-b), (II-c), (II-d), (II-e), (II-f), (II-g), (II-h), (III-a), (III-b), (III-c), or (III-d) is a compound described in Table 2, or a pharmaceutically acceptable salt thereof. In some embodiments, the compound of Formula (I), (II-a), (II-b), (II-c), (II-d), (II-e), (II-f), (II-g), (III-a), (III-b), (III-c), or (III-d) is a compound described in Table 2.

In some embodiments, the compound of Formula (I), (II-a), (II-b), (II-c), (II-d), (II-e), (II-f), (II-g), (II-h), (III-a), (III-b), (III-c), or (III-d) is the compound having the structure:

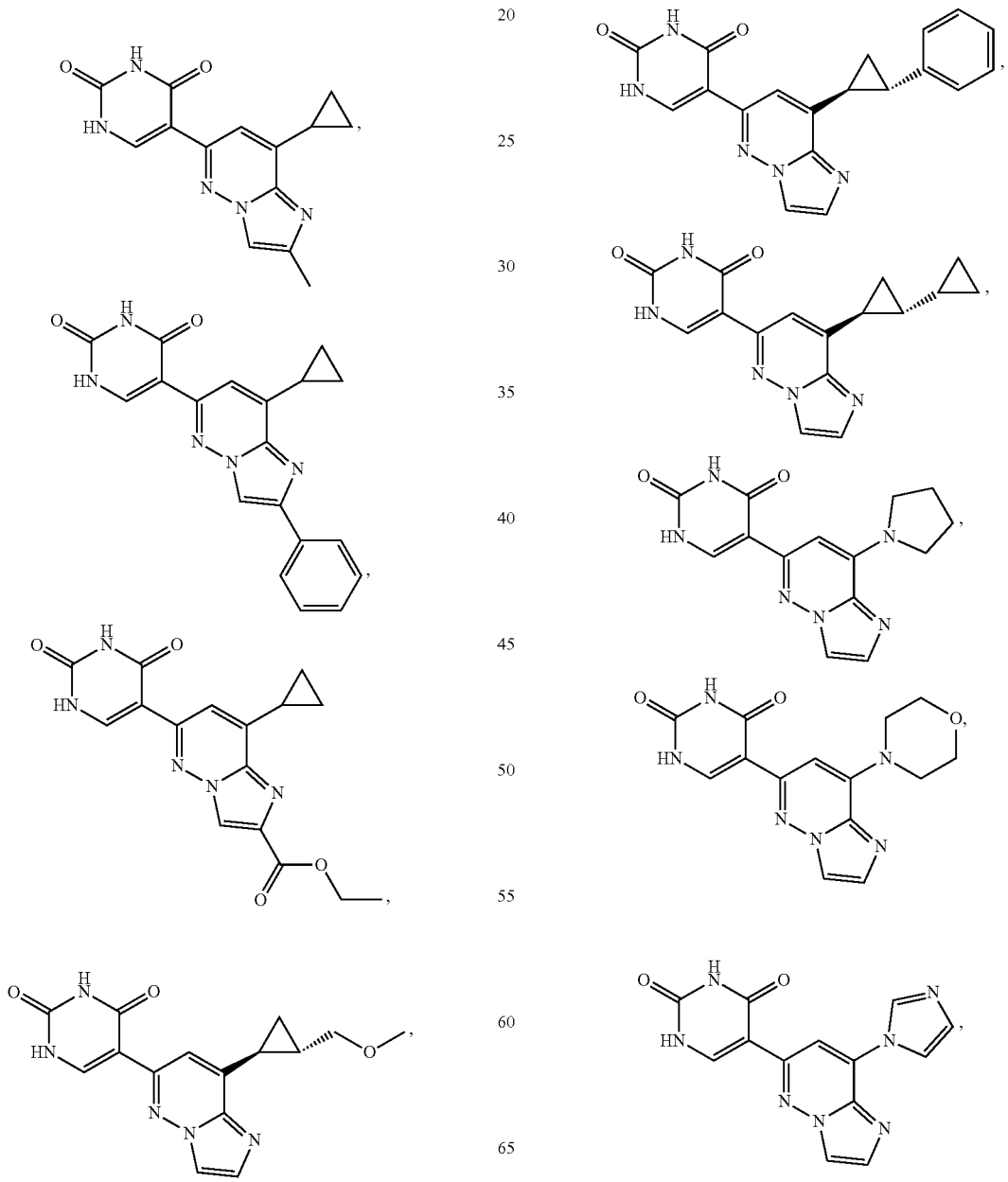

97
-continued
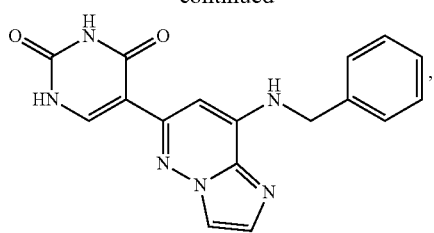
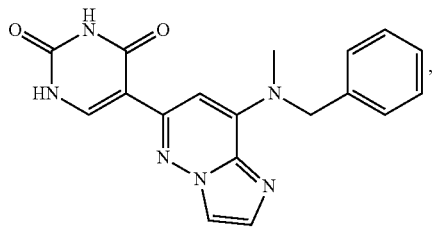
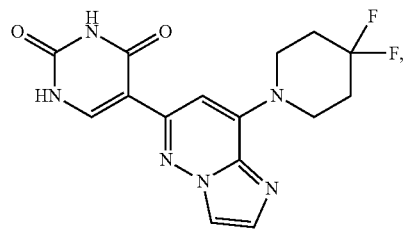
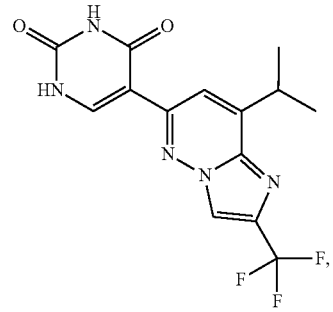
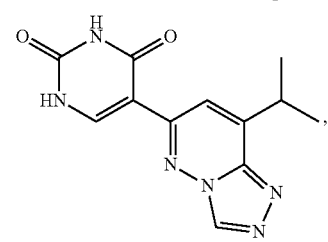
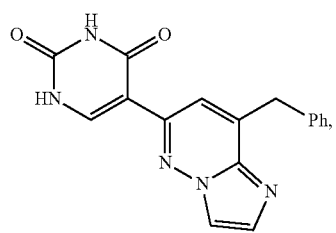
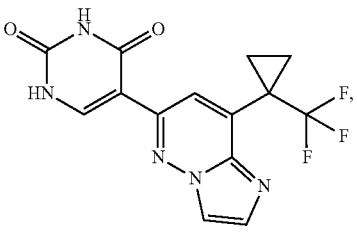
98
-continued
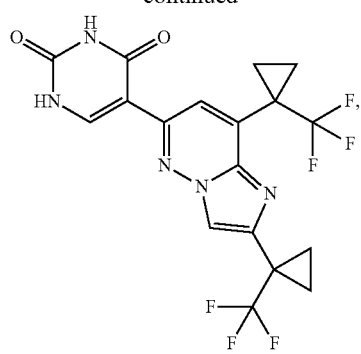
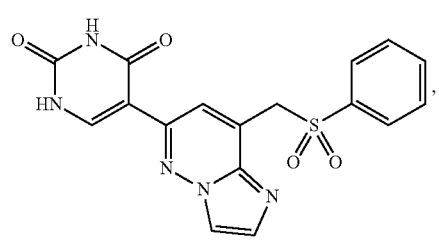
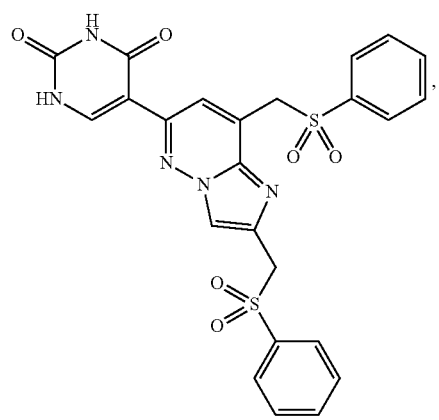
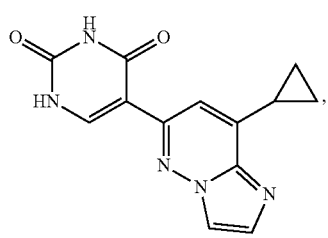
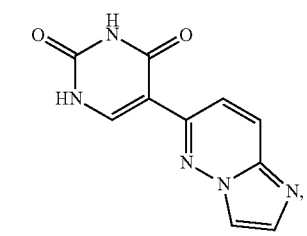
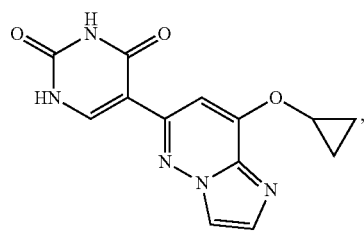

-continued
or a pharmaceutically acceptable salt thereof.
In some embodiments, the compound of Formula (I), (II-a), (II-b), (II-c), (II-d), (II-e), (II-f), (II-g), (II-h), (III-a), (III-b), (III-c), or (III-d) is the compound having the structure:
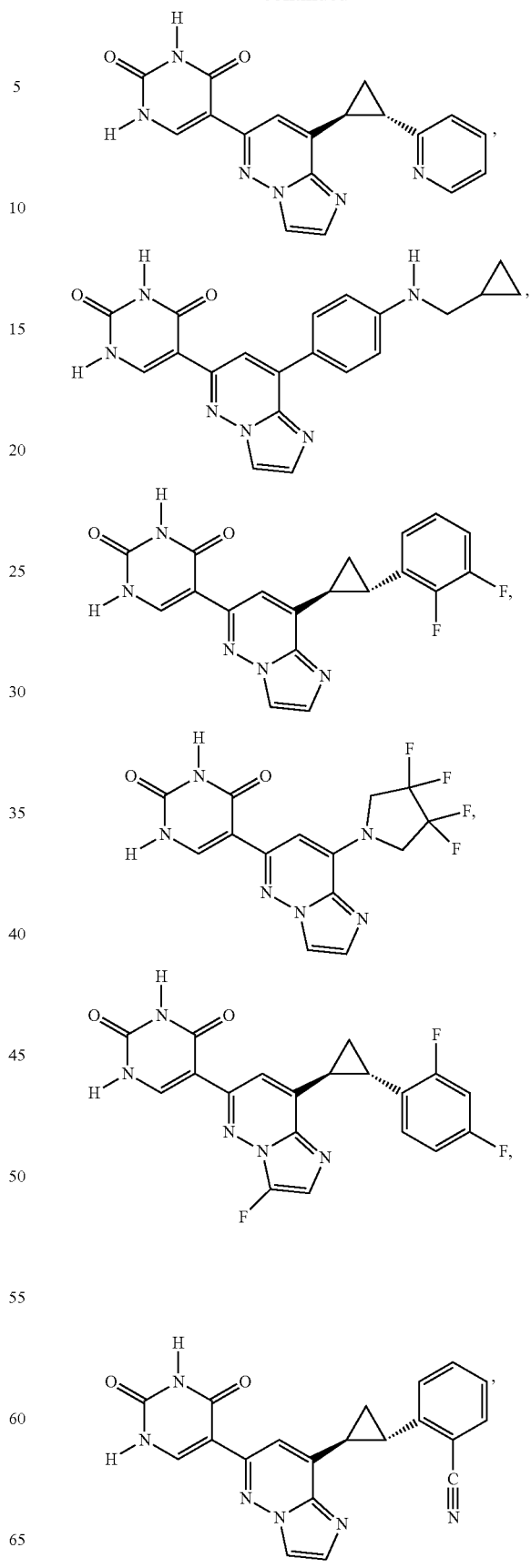

101
-continued
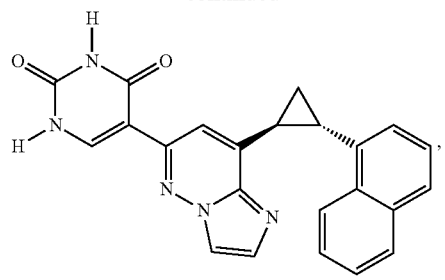
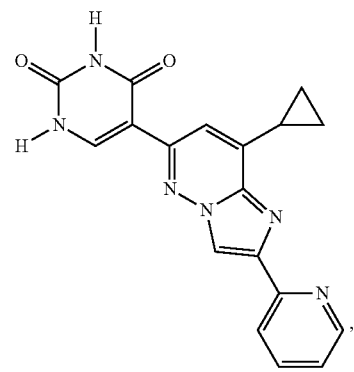
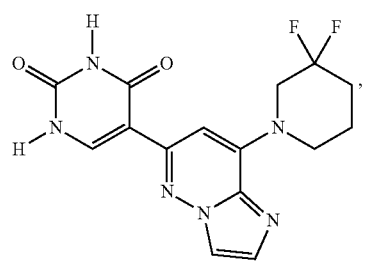
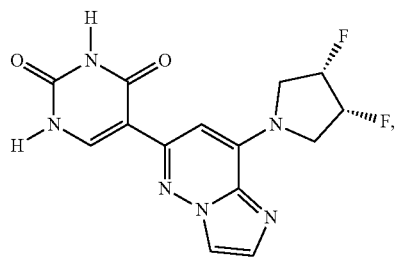
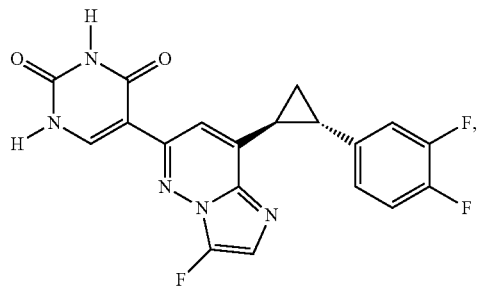
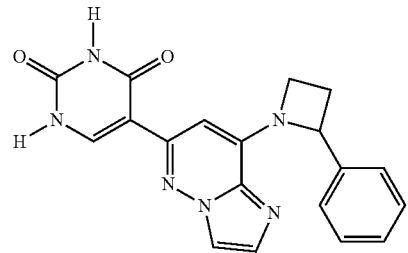
102
-continued
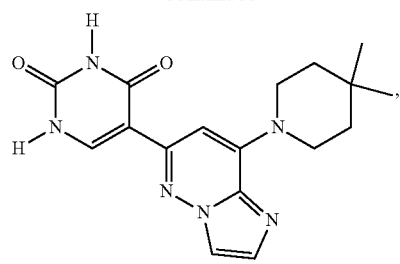
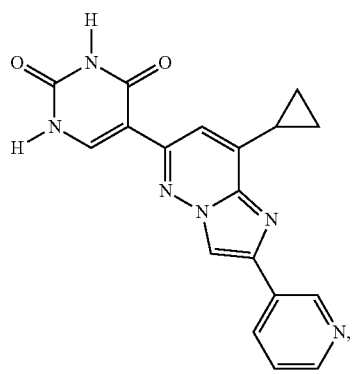
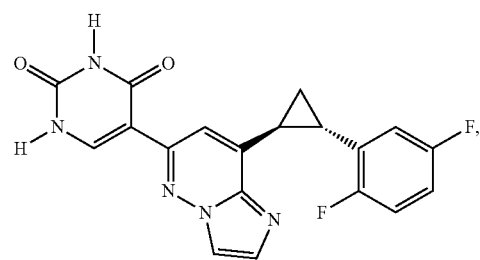
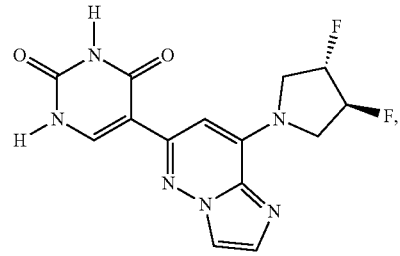
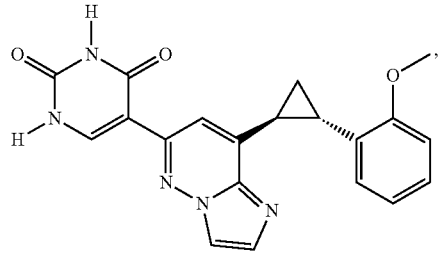
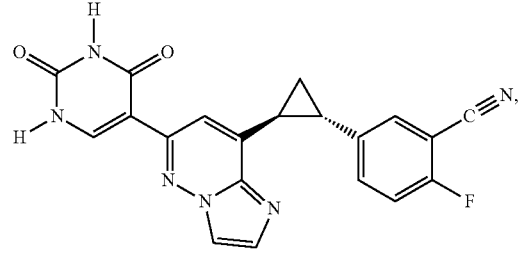

103
-continued
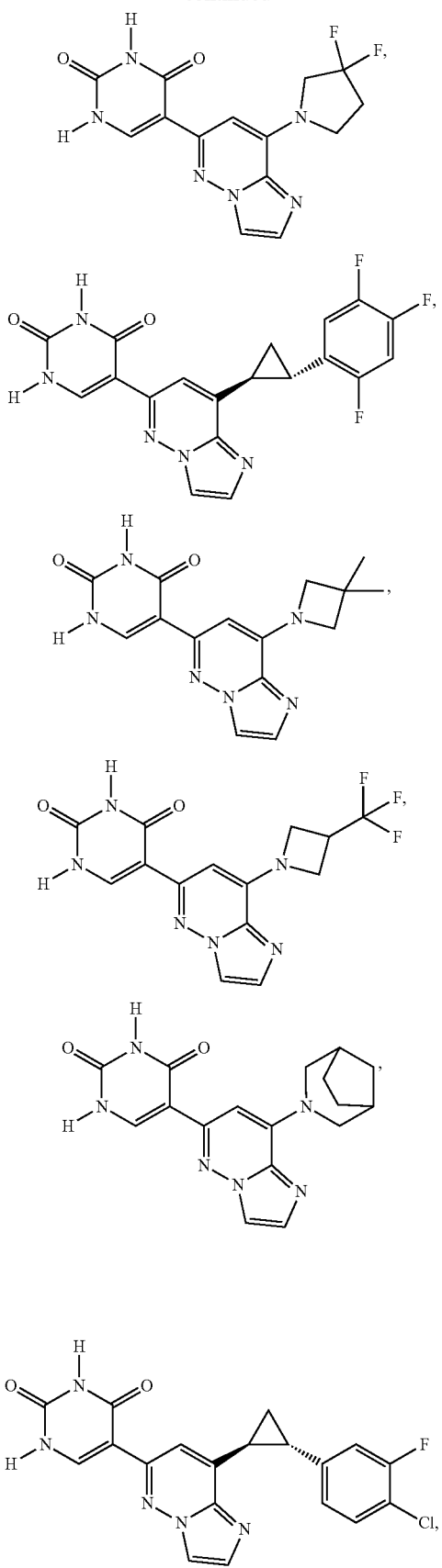
104
-continued
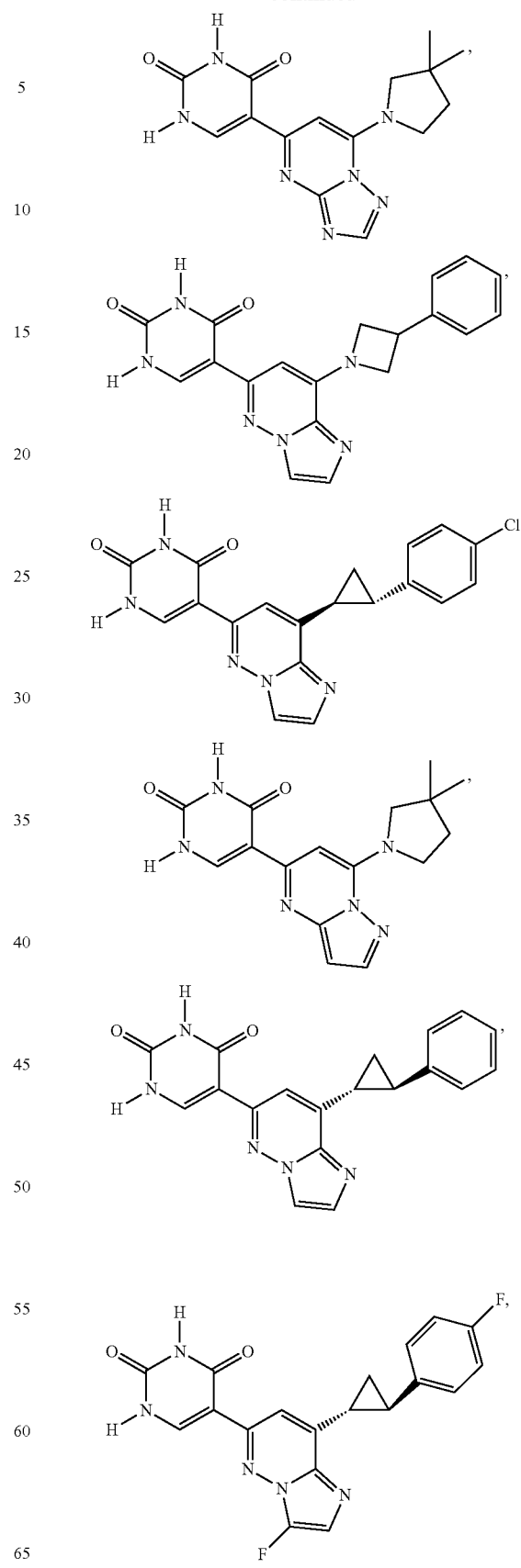

105
-continued
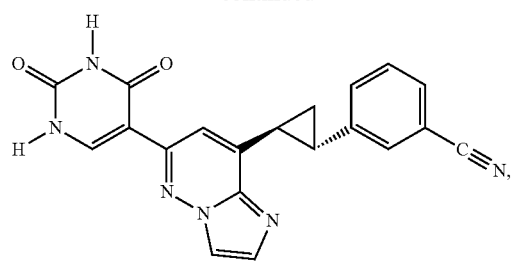
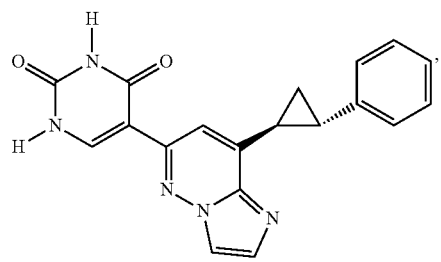
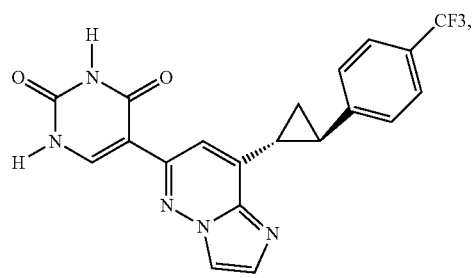
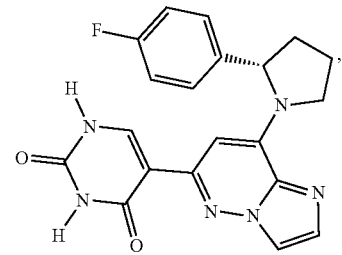
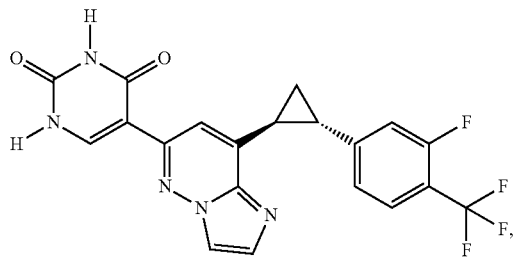
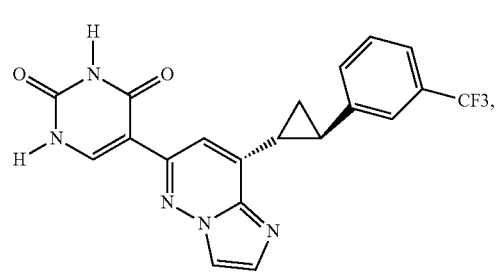
106
-continued
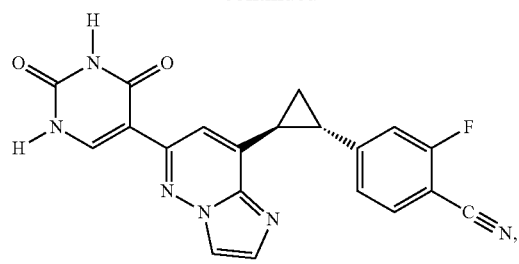
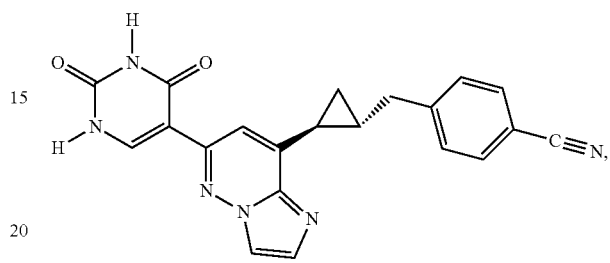
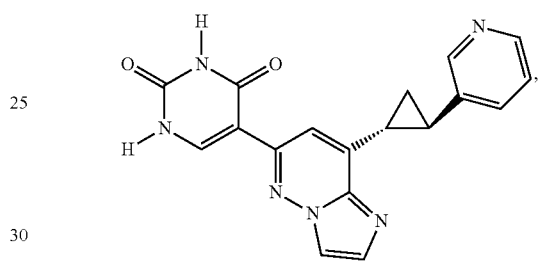
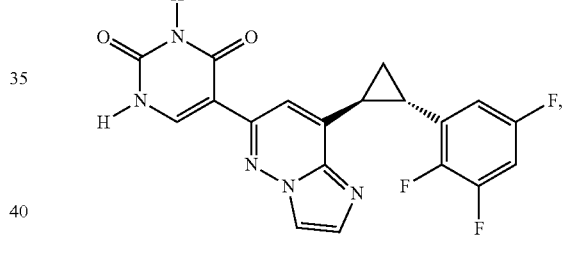
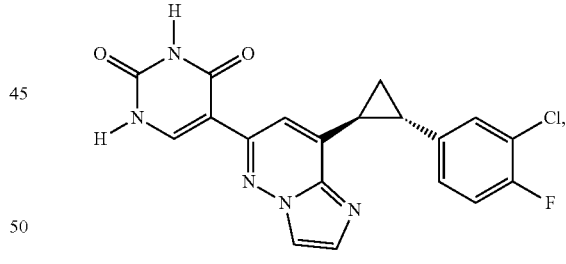
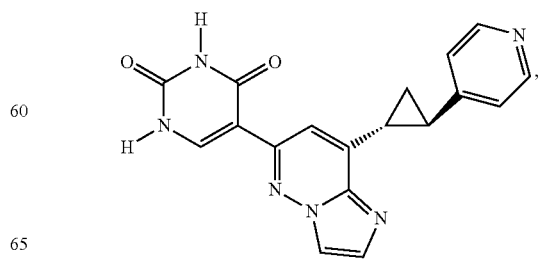

107
-continued
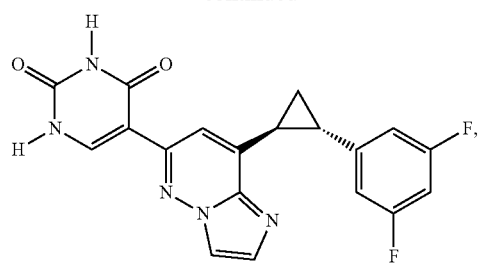
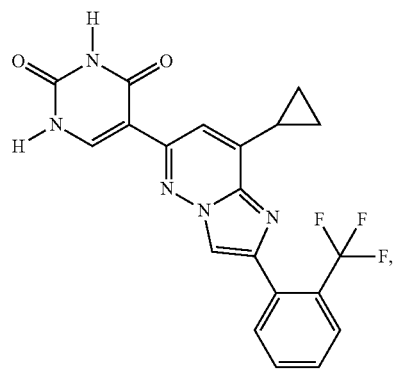
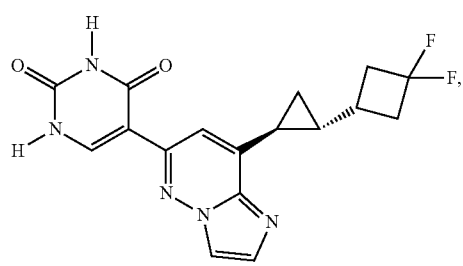
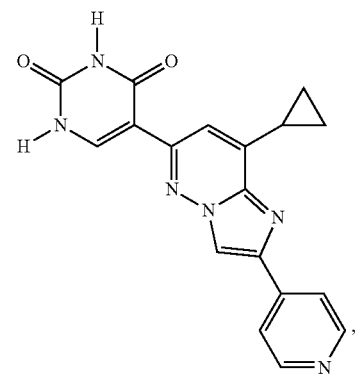
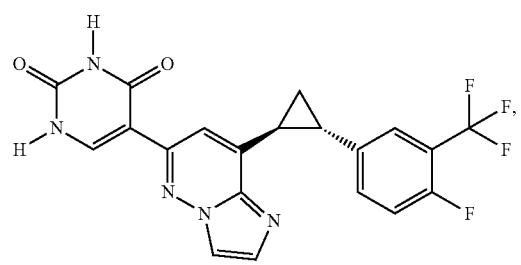
108
-continued
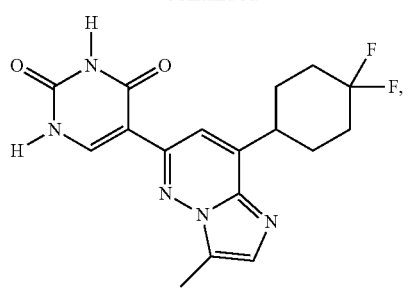
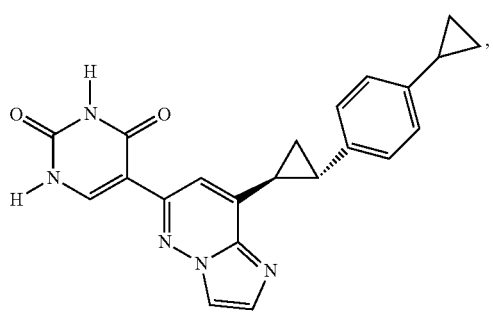
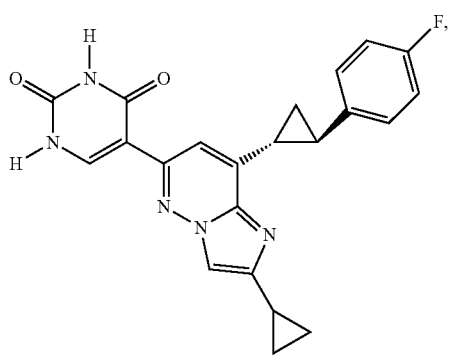
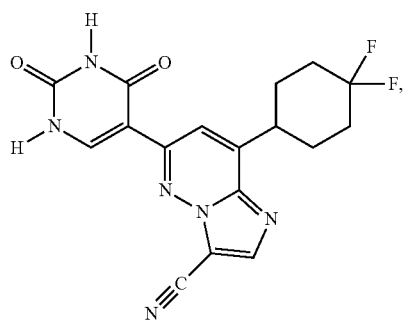
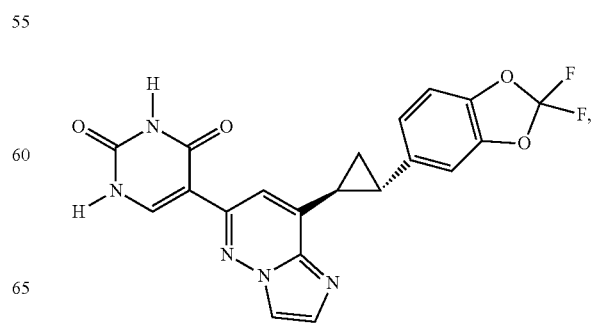

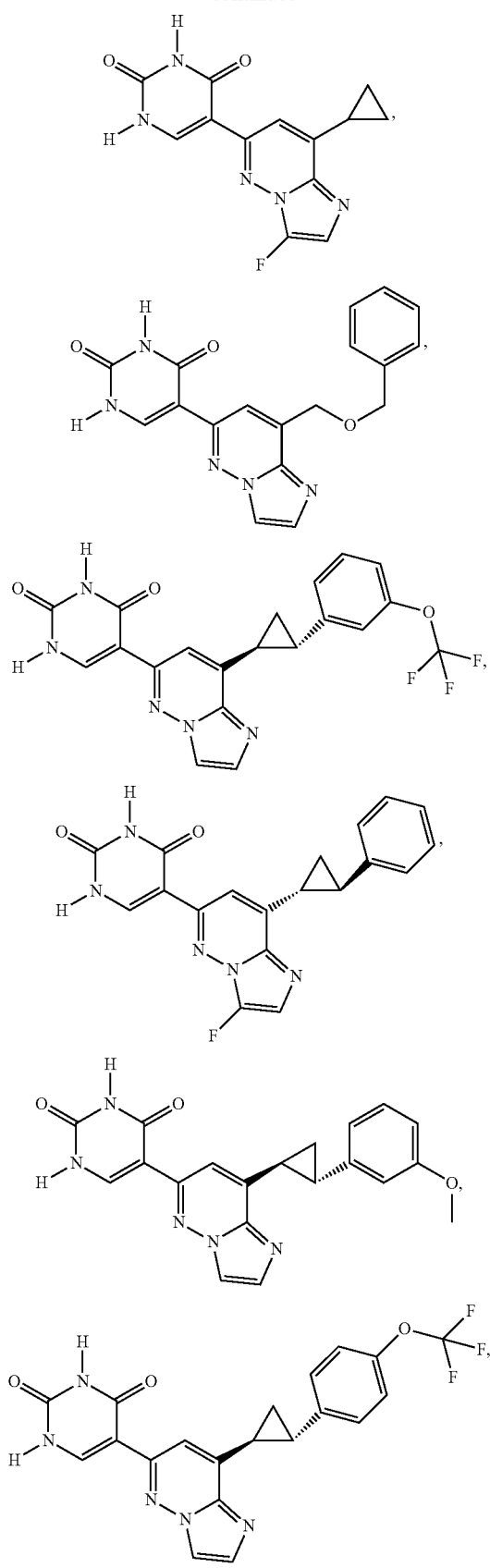
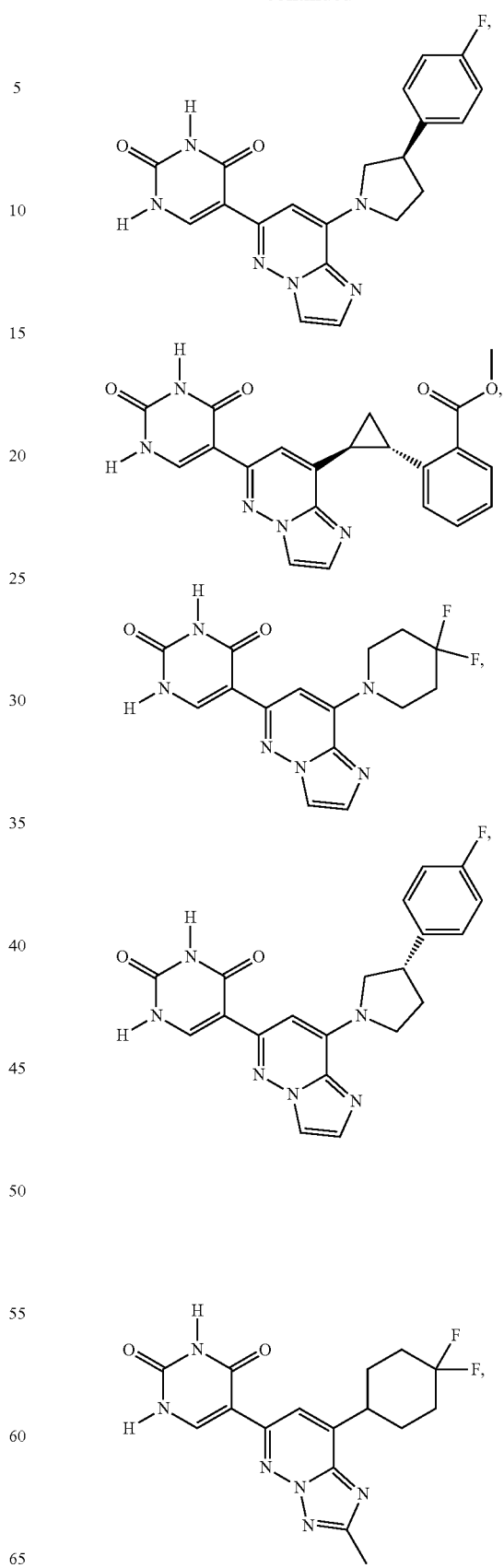

-continued
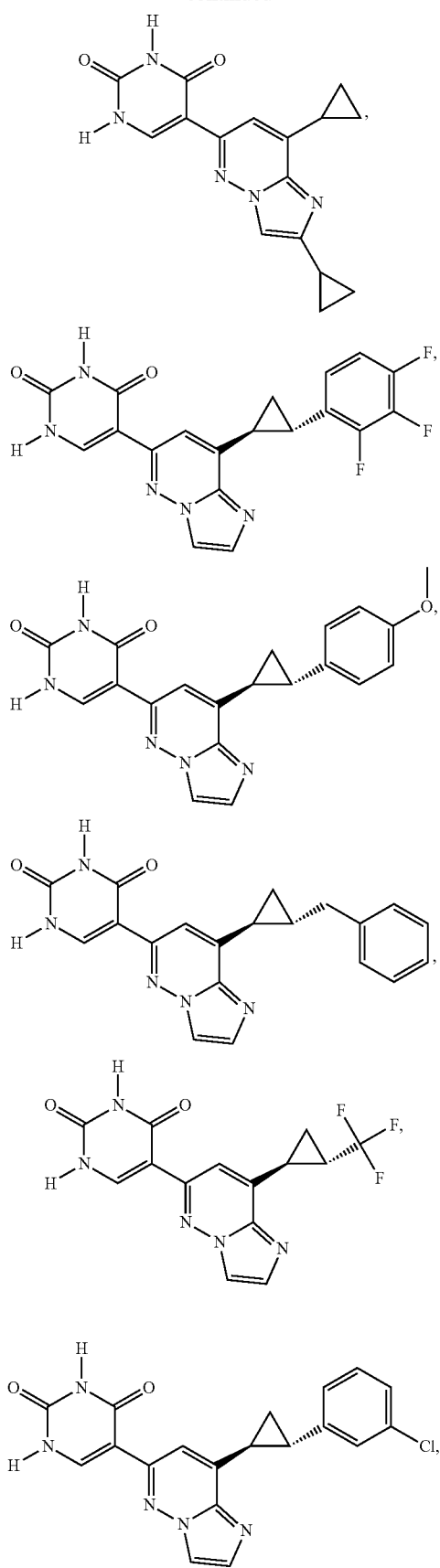
-continued
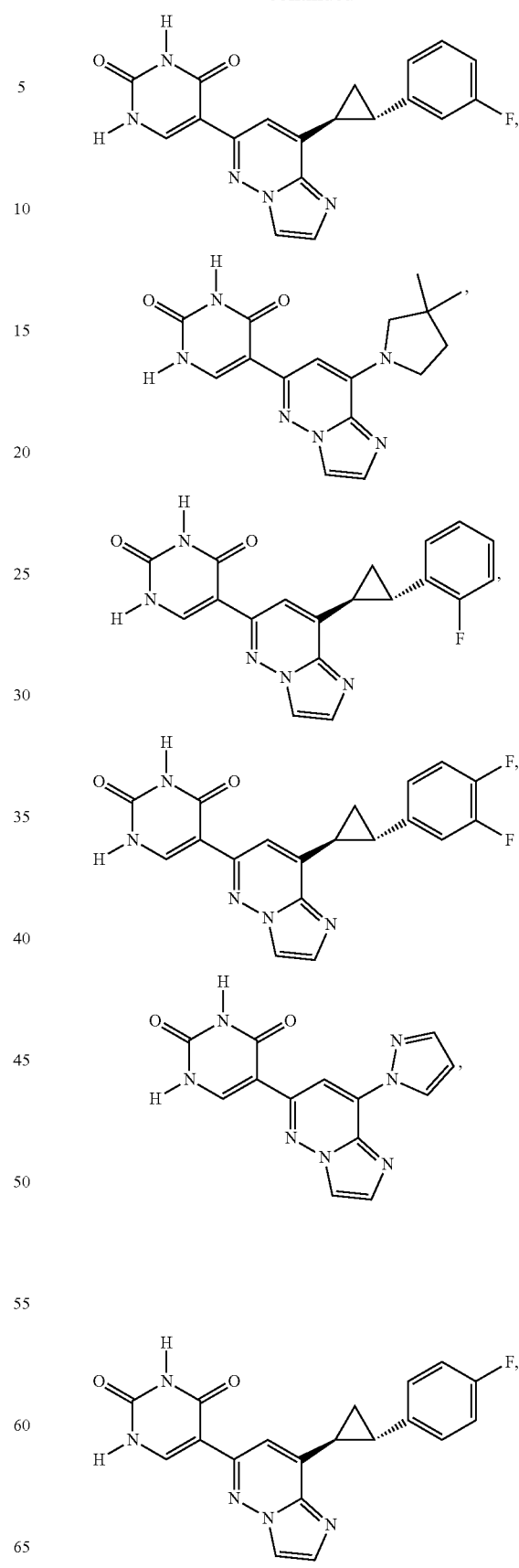

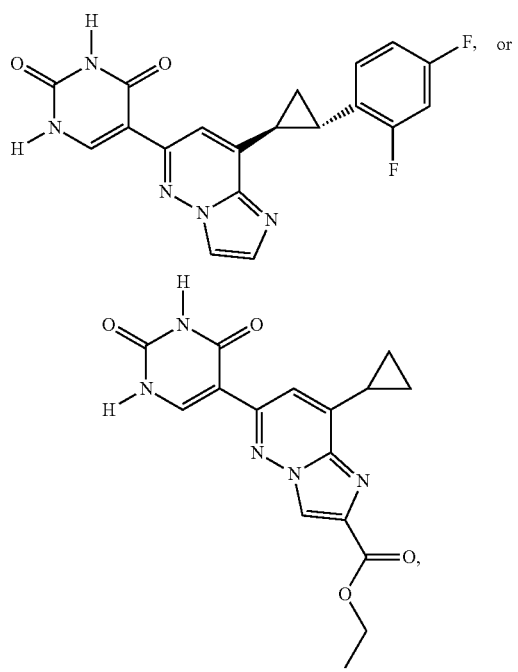
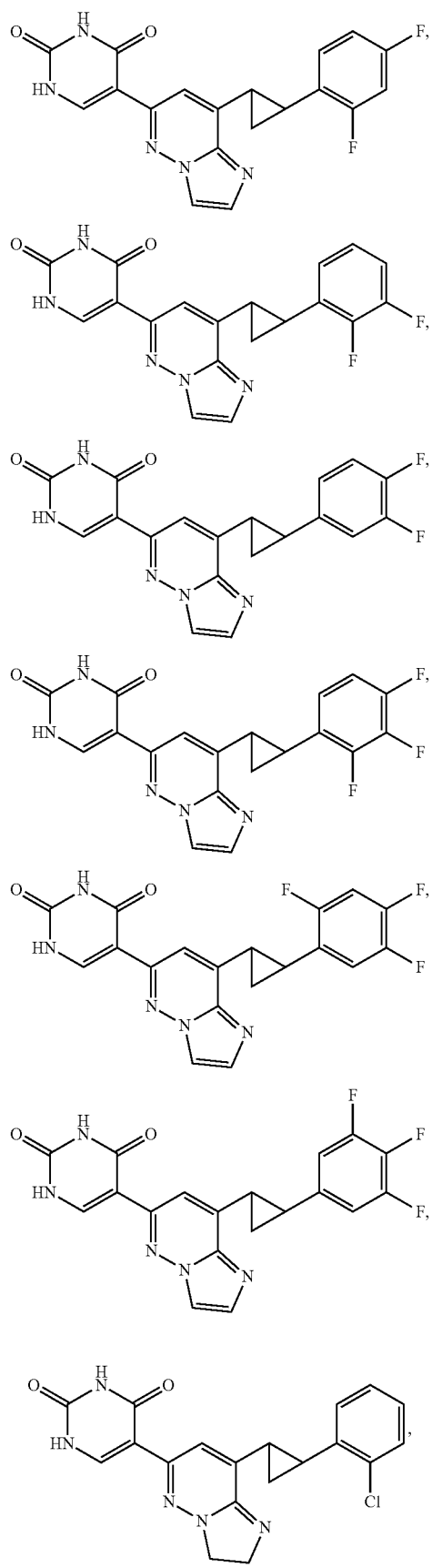
or a pharmaceutically acceptable salt thereof.
In some embodiments, the compound of Formula (I), (II-a), (II-b), (II-c), (II-d), (II-e), (II-f), (II-g), (II-h), (III-a), (III-b), (III-c), or (III-d) is the compound having the structure:
In some embodiments, the compound of Formula (I), (II-a), (II-b), (II-c), (II-d), (II-e), (II-f), (II-g), (II-h), (III-a), (III-b), (III-c), or (III-d) is the compound having the structure:
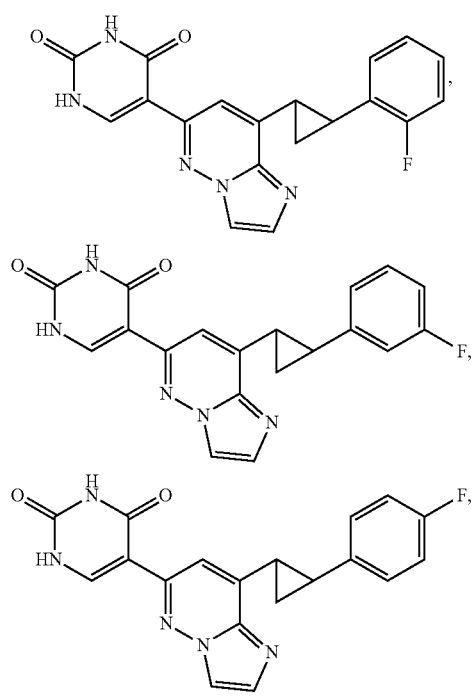

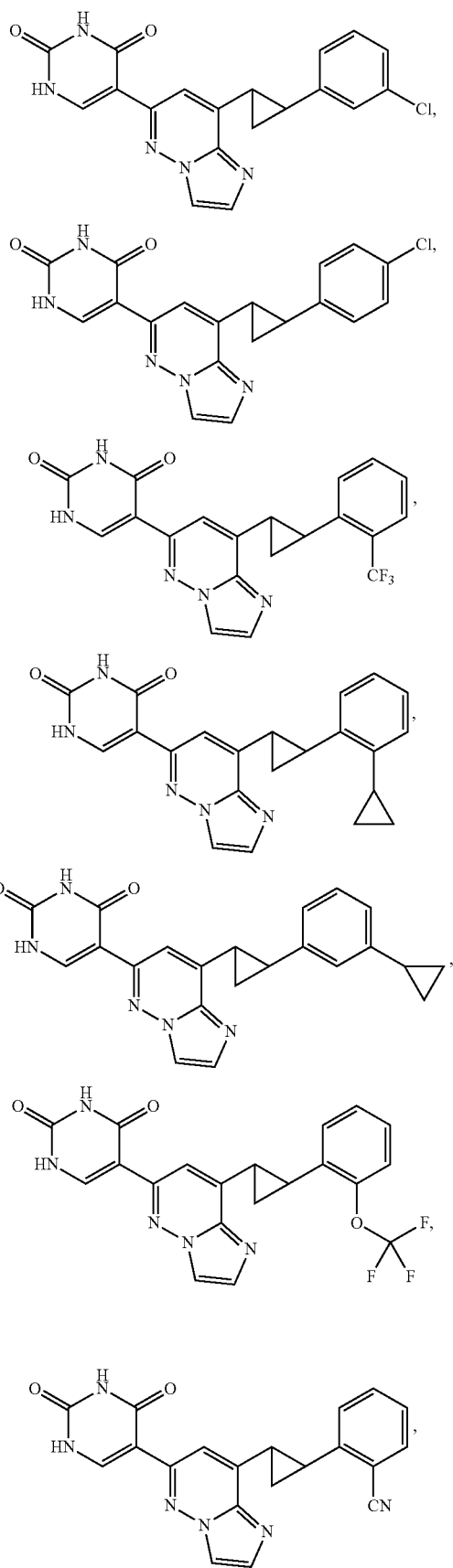
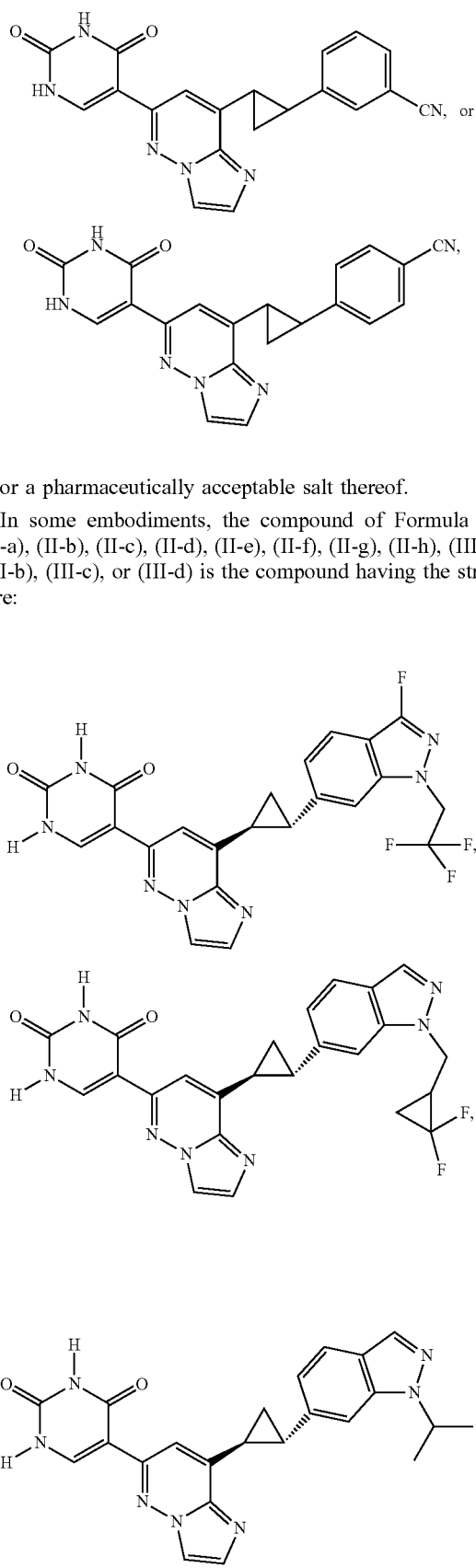
or a pharmaceutically acceptable salt thereof.
In some embodiments, the compound of Formula (I), (II-a), (II-b), (II-c), (II-d), (II-e), (II-f), (II-g), (II-h), (III-a), (III-b), (III-c), or (III-d) is the compound having the structure:

117
-continued
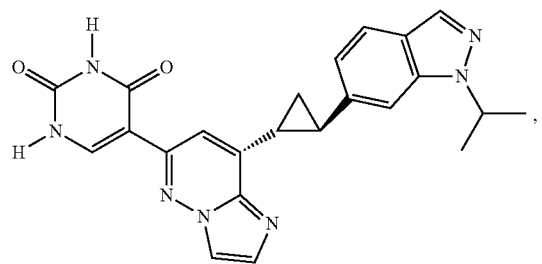
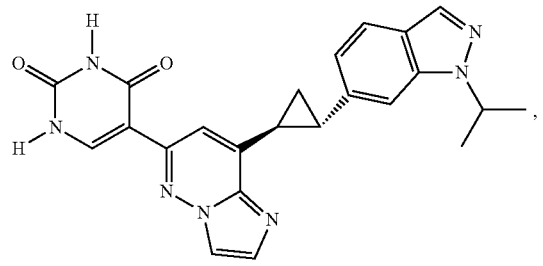
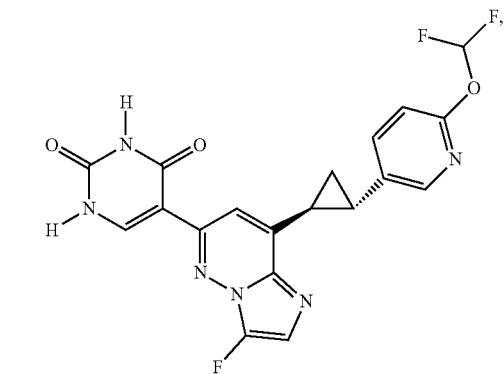
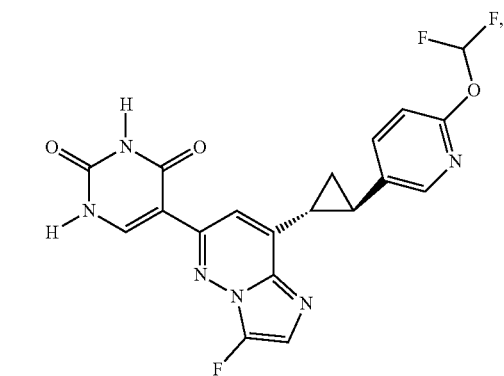
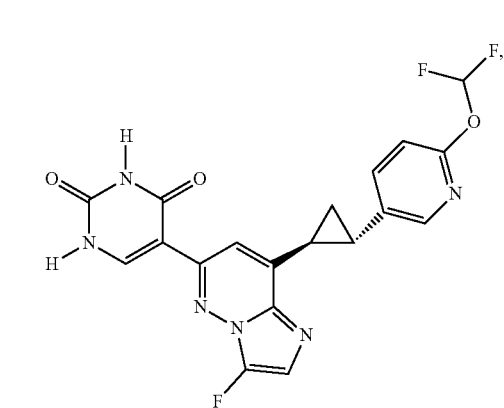
118
-continued
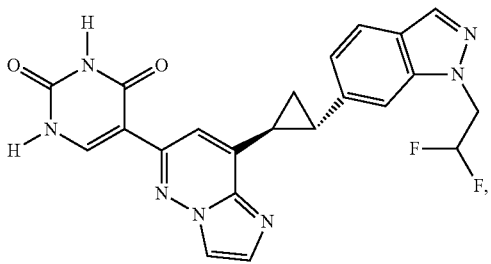
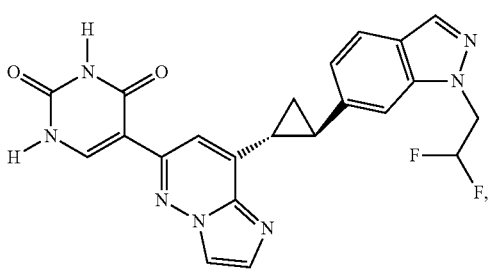
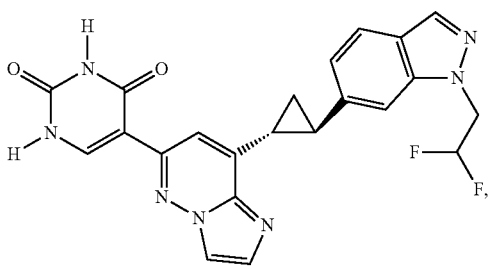
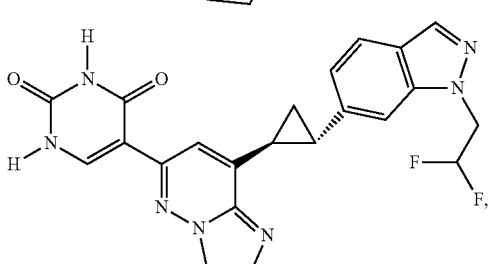
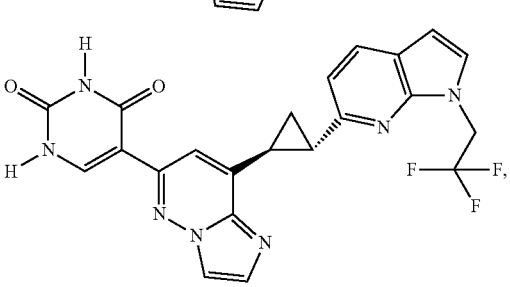
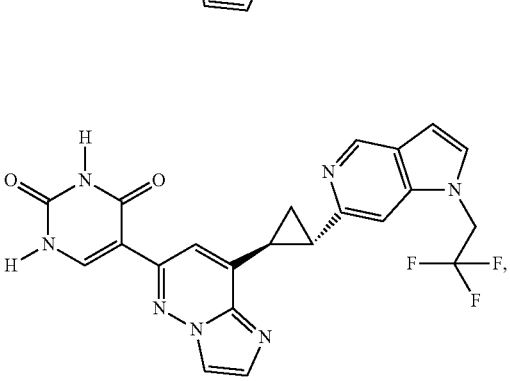

119
-continued
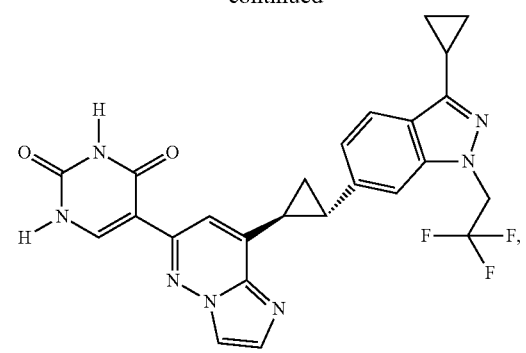
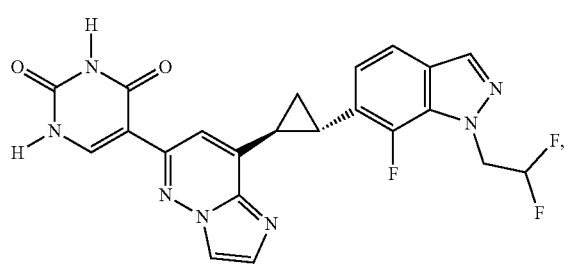
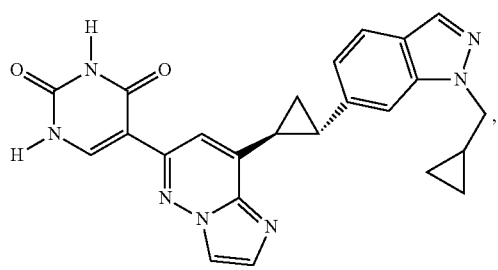
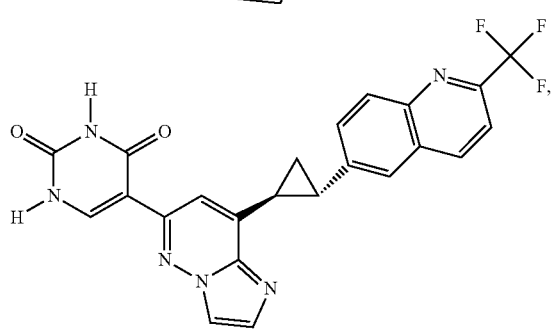
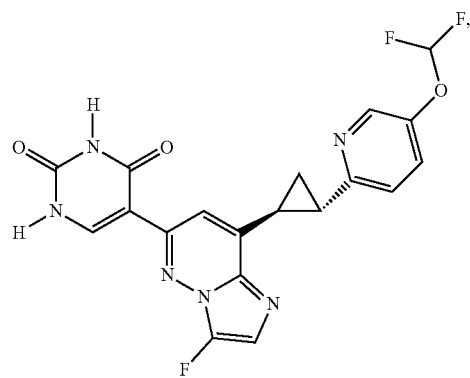
120
-continued
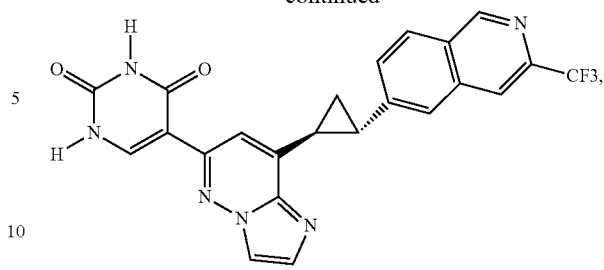
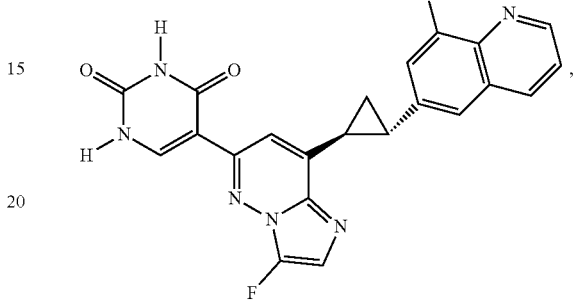
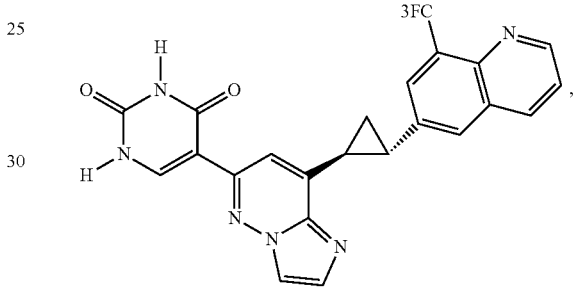
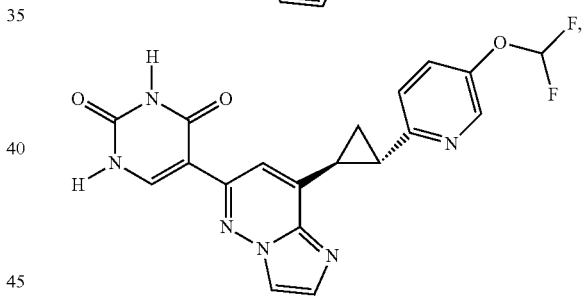
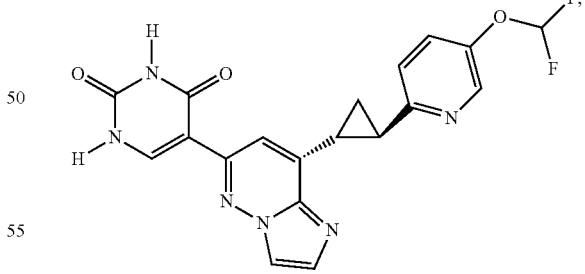
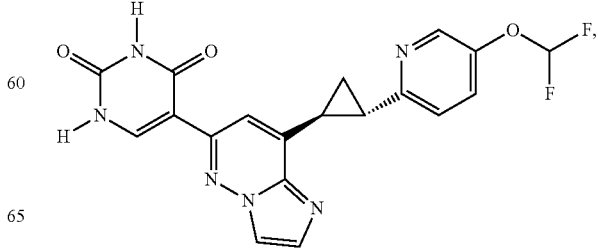

121
-continued
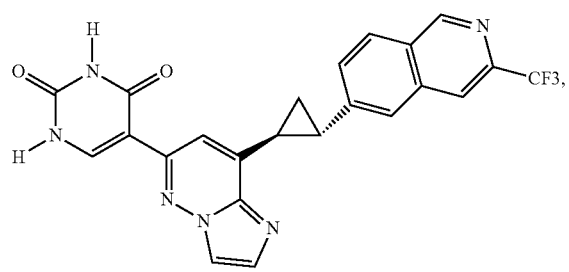
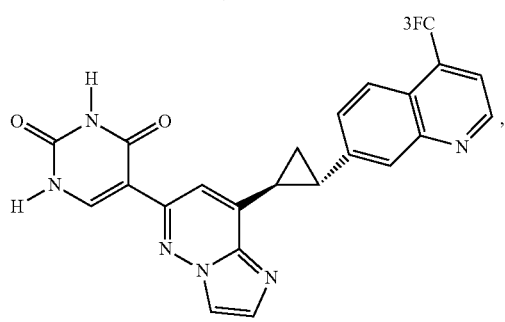
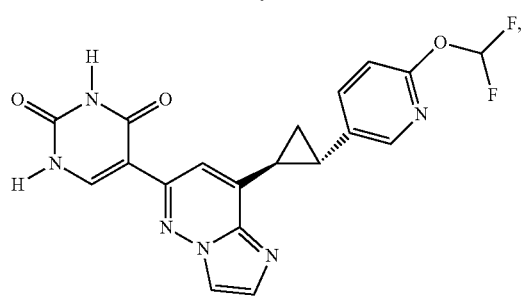
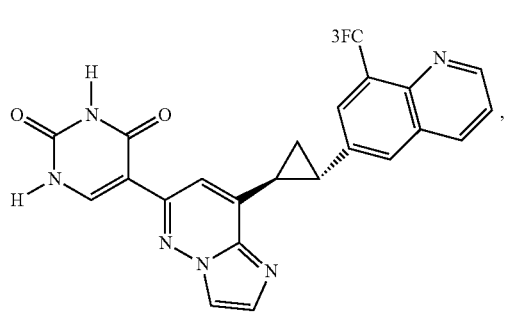
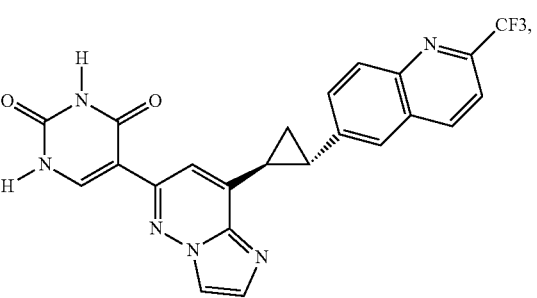
122
-continued
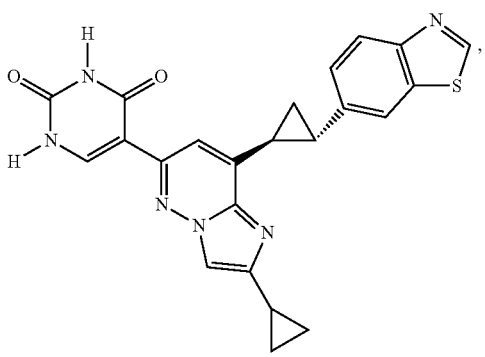
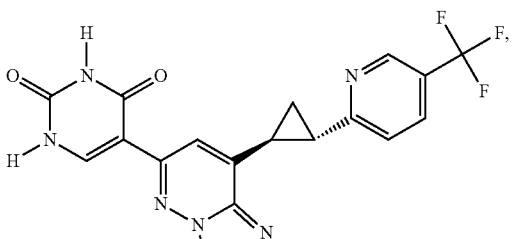
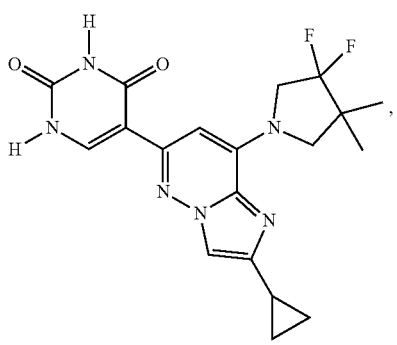
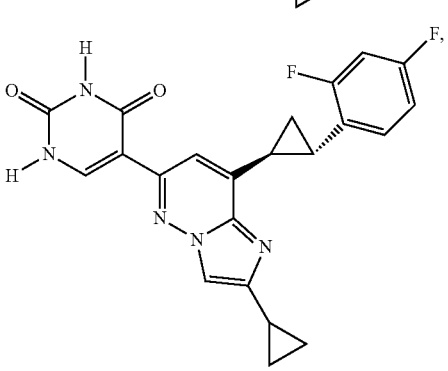
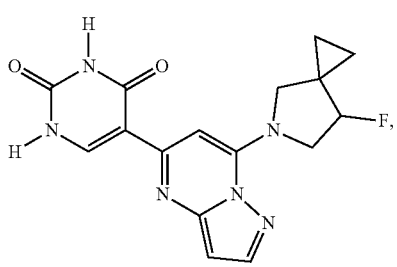

123
-continued
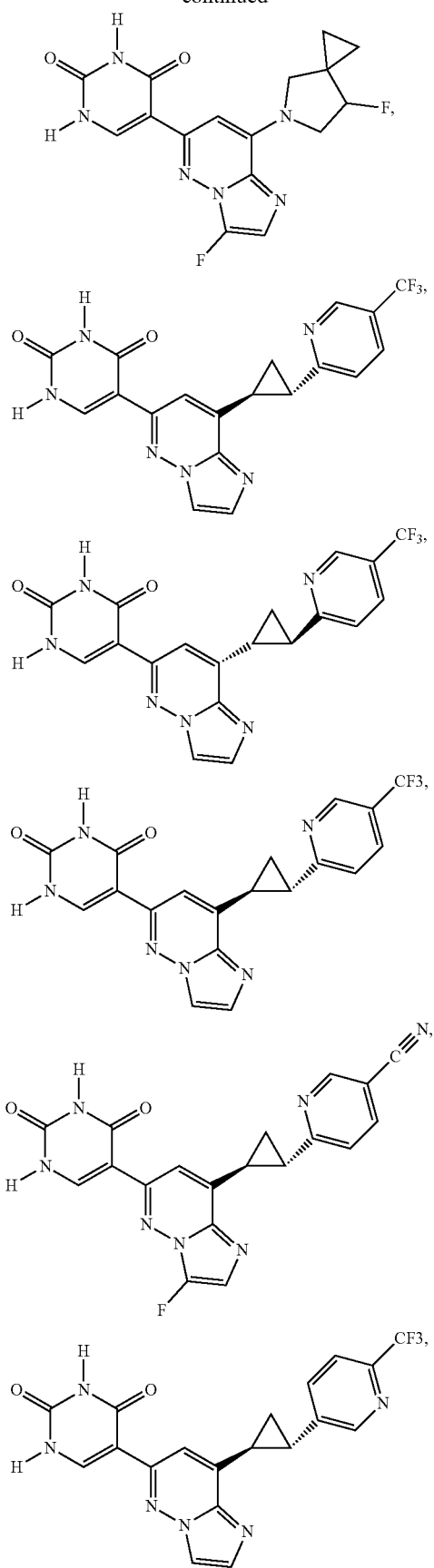
124
-continued
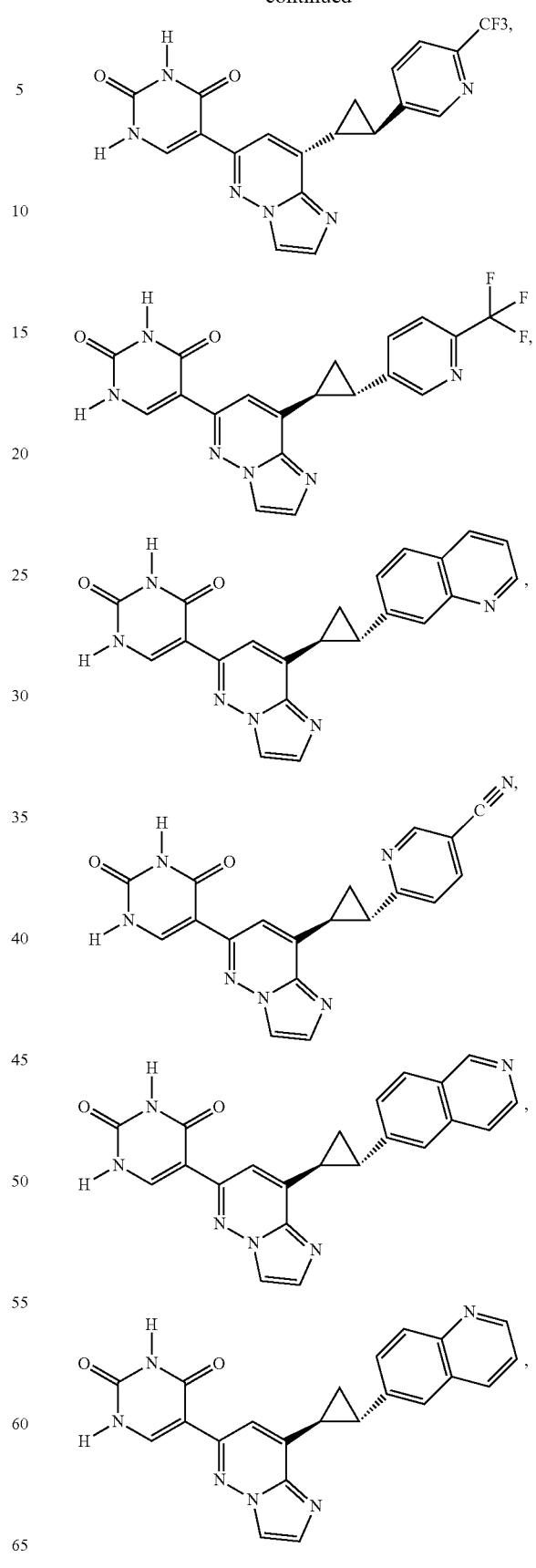

125
-continued
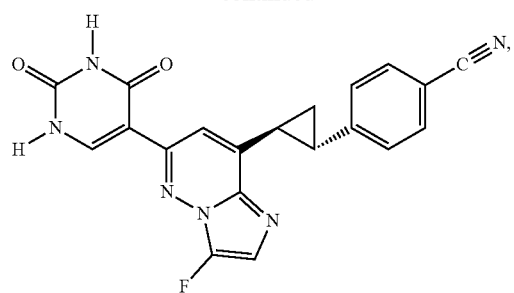
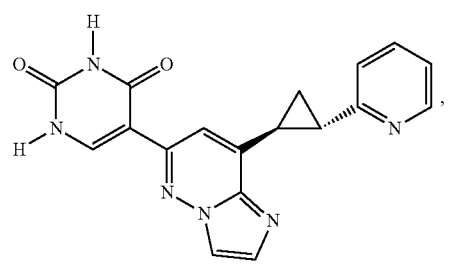
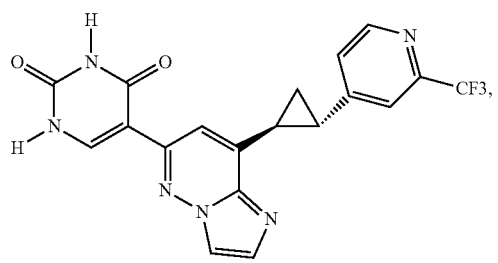
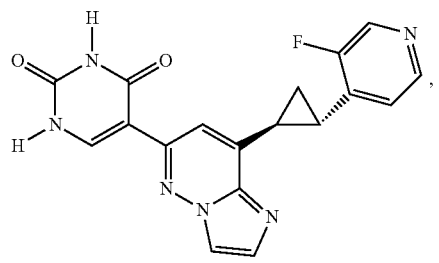
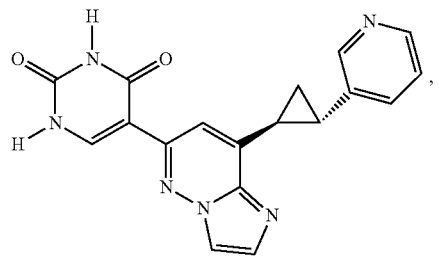
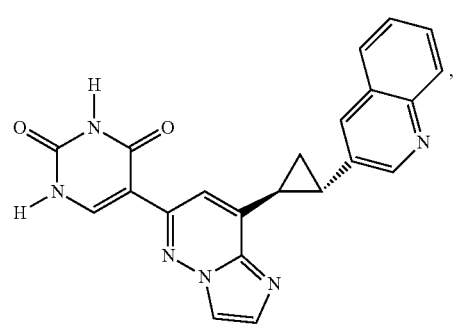
126
-continued
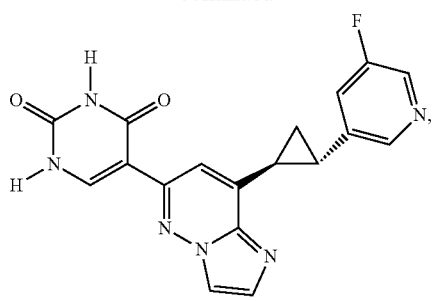
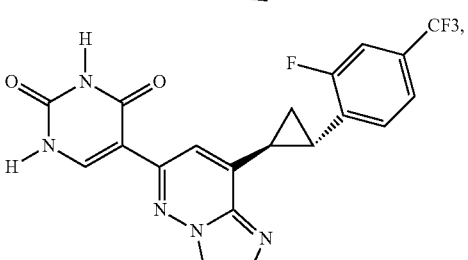
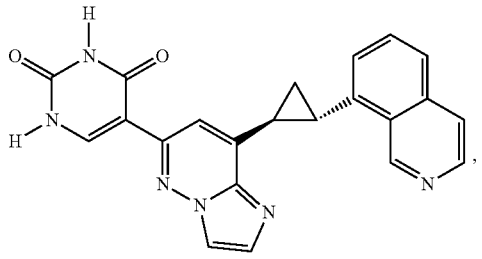
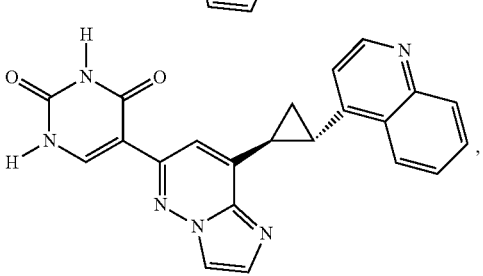
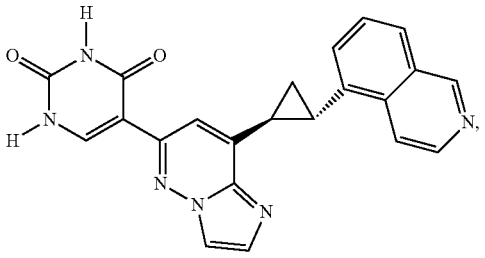
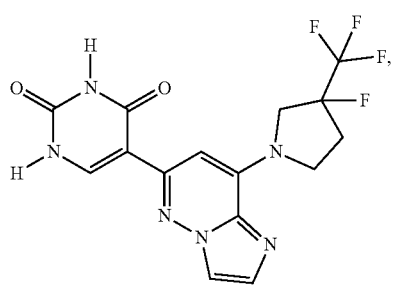

127
-continued
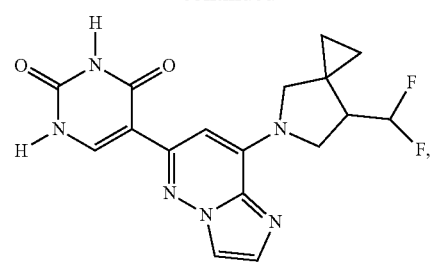
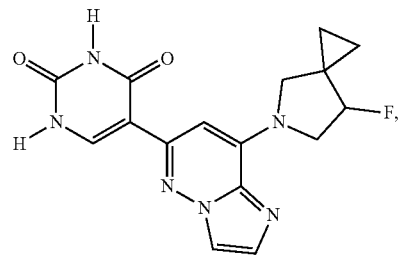
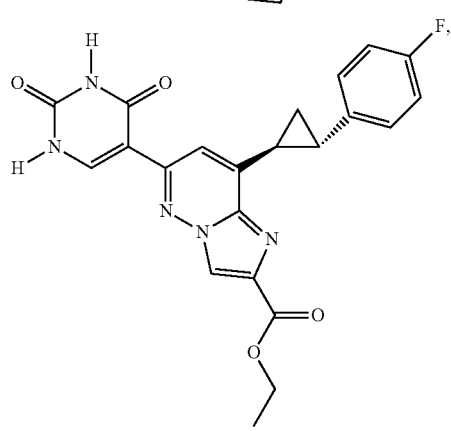
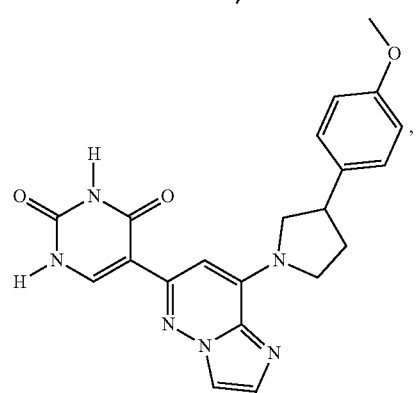
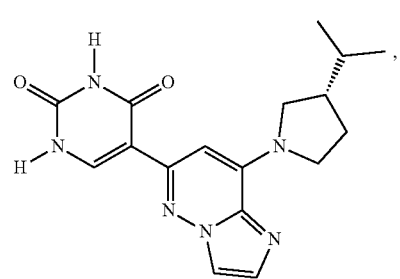
128
-continued
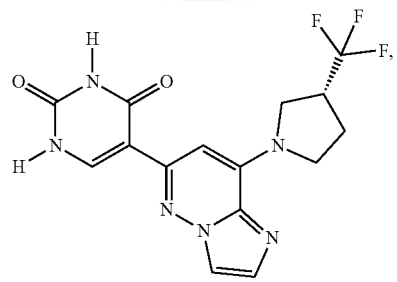
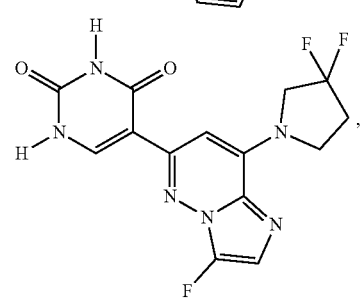
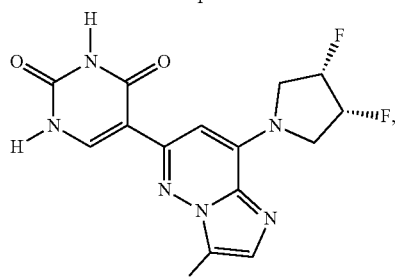
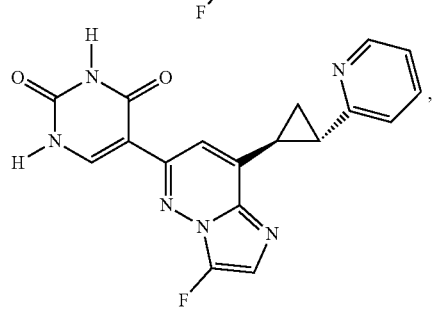
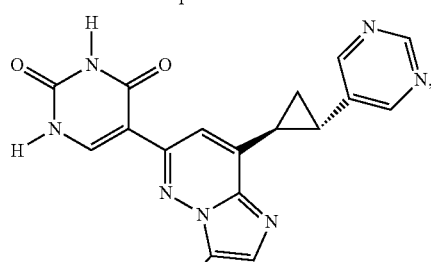
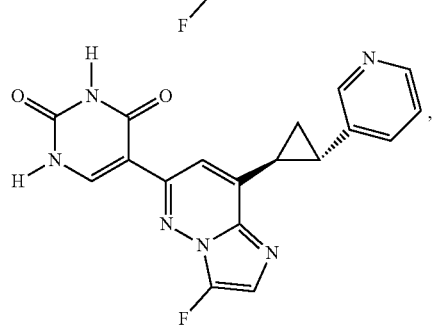

129
-continued
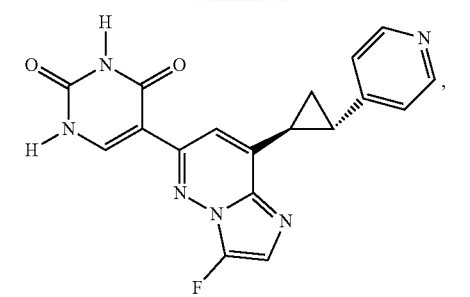
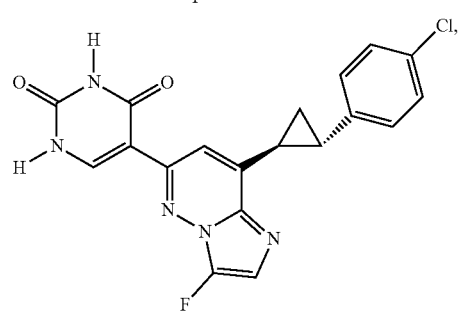
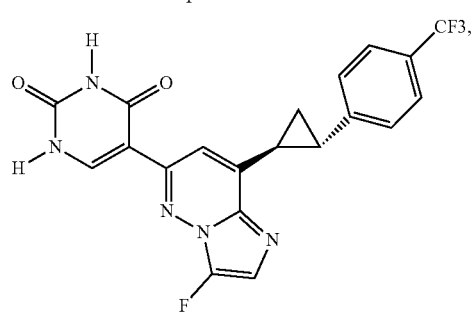
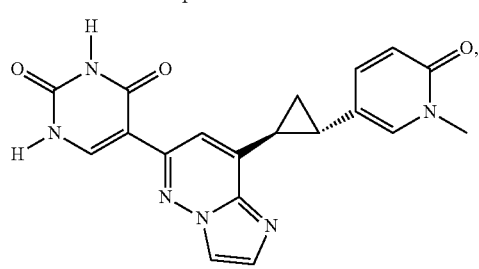
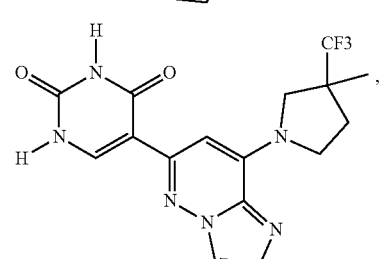
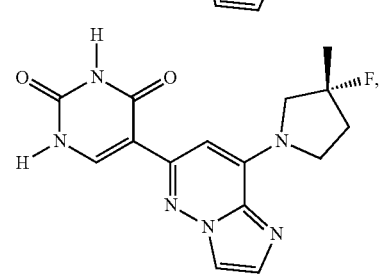
130
-continued
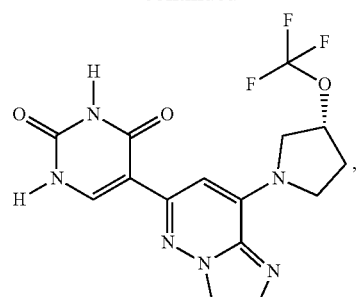
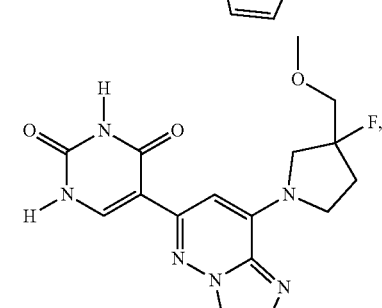
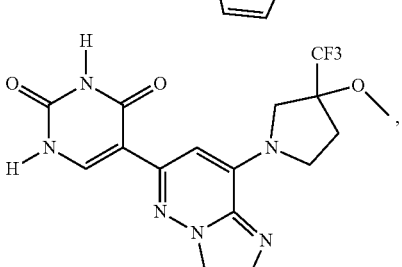
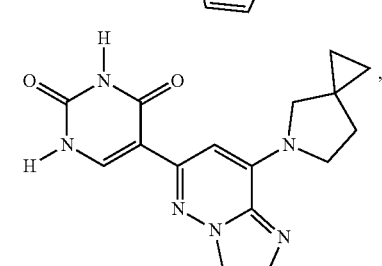
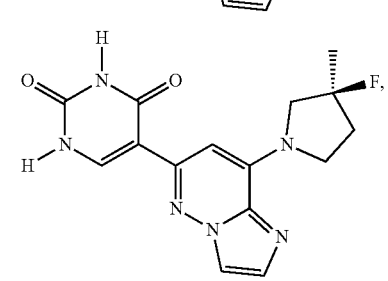
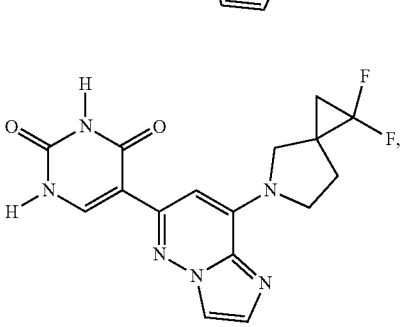

131
-continued
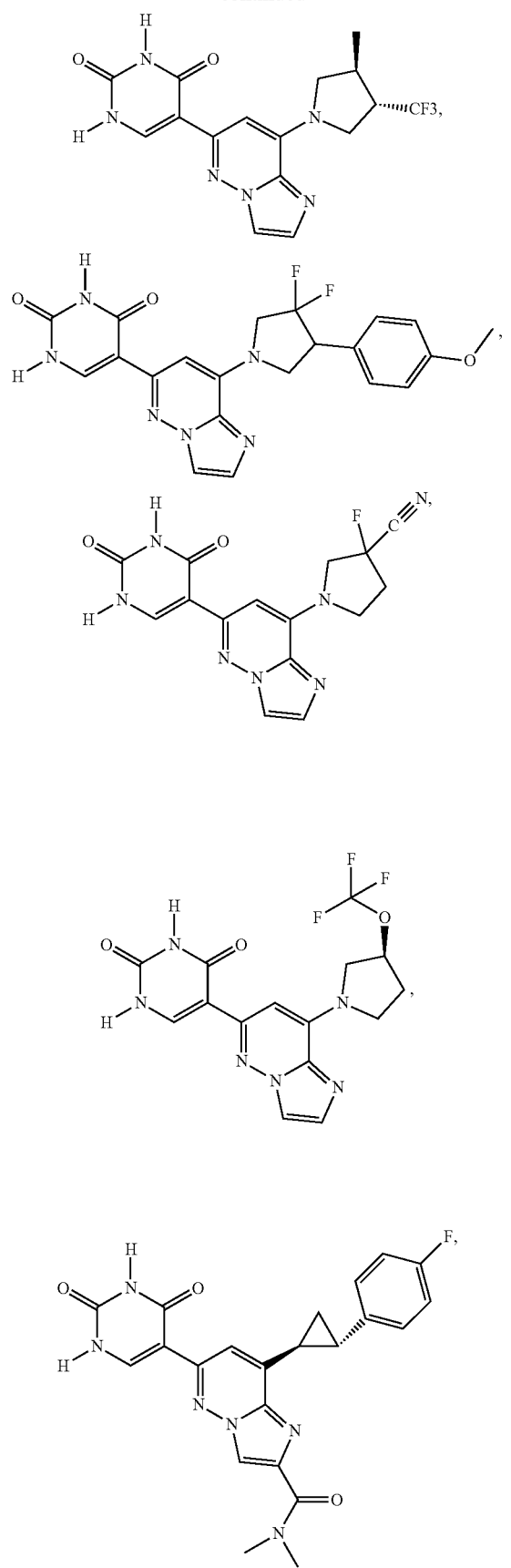
132
-continued
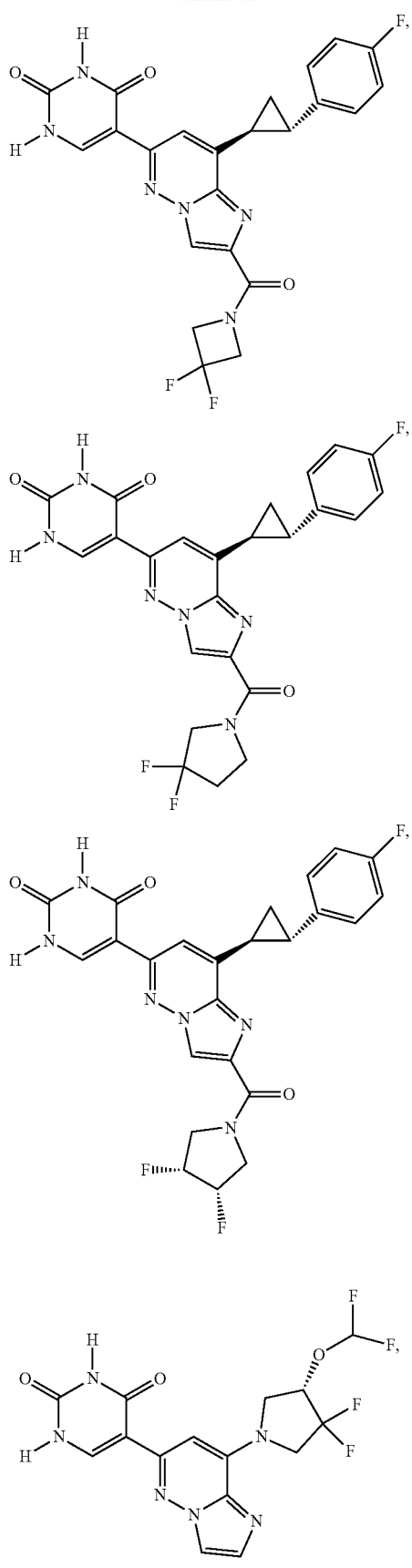

133
-continued
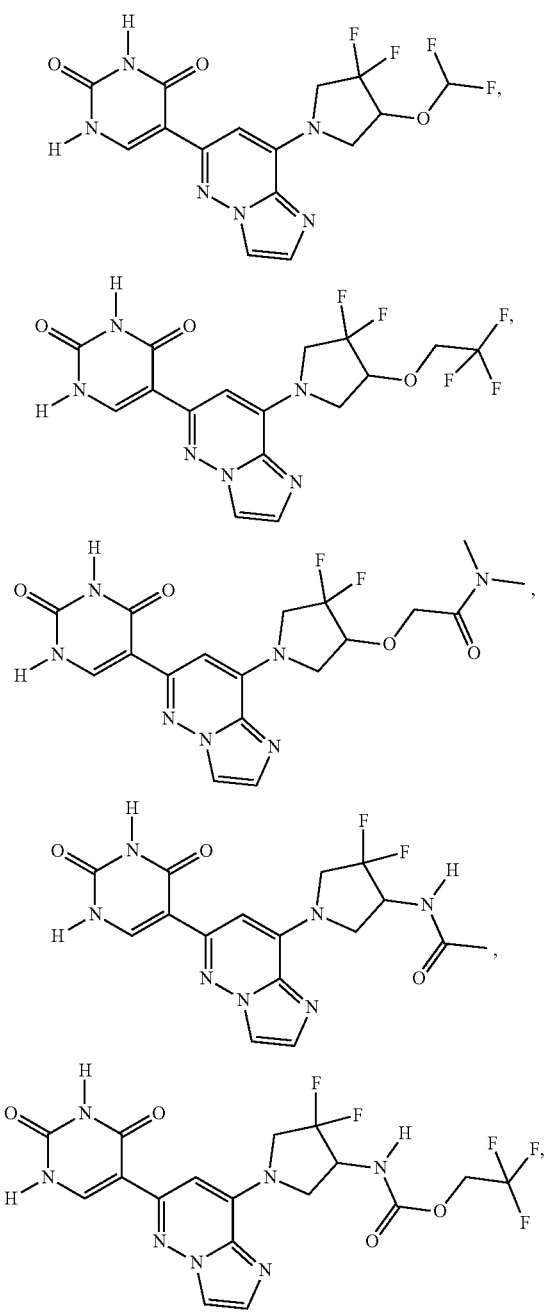
134
-continued
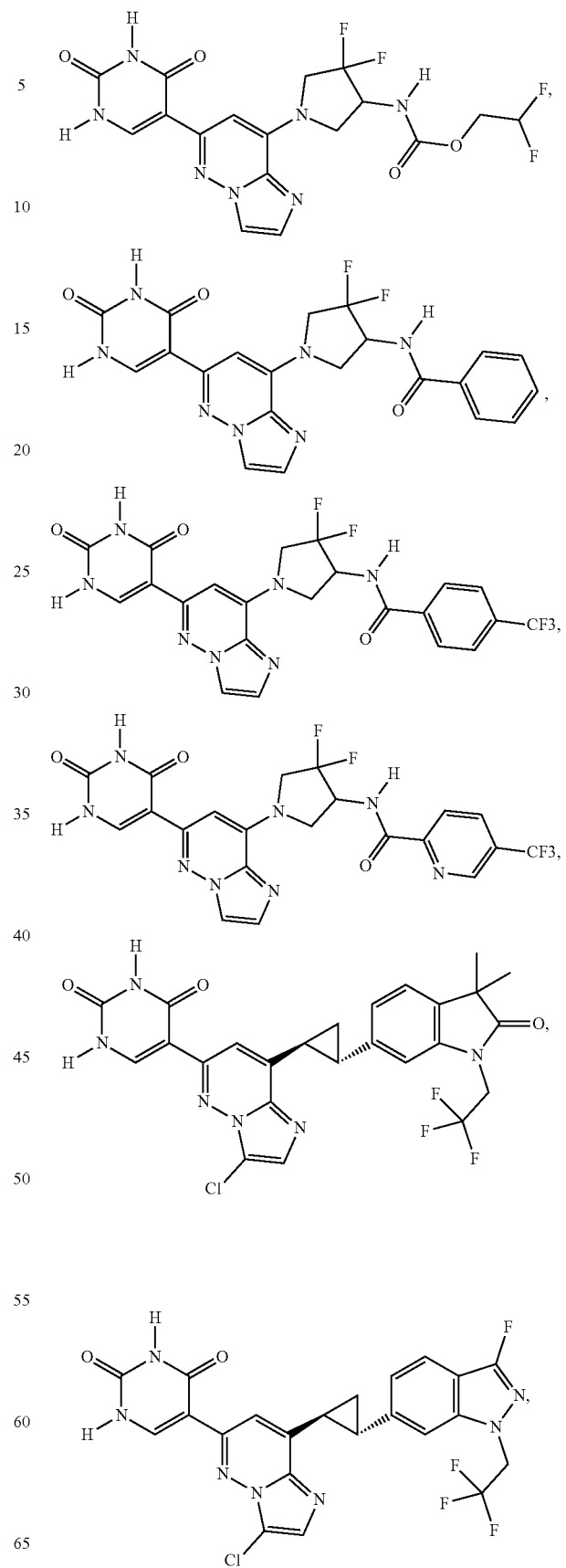

135
-continued
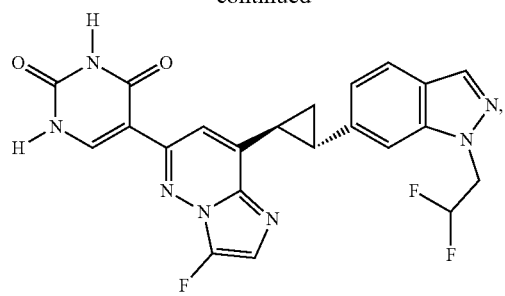
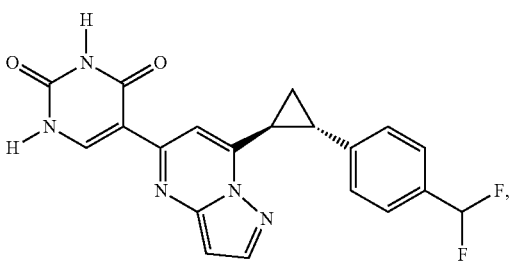
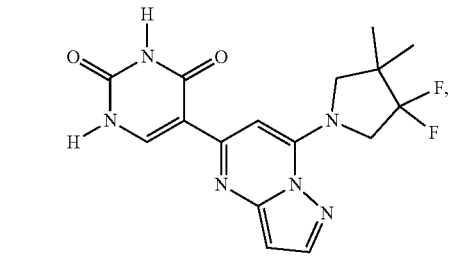
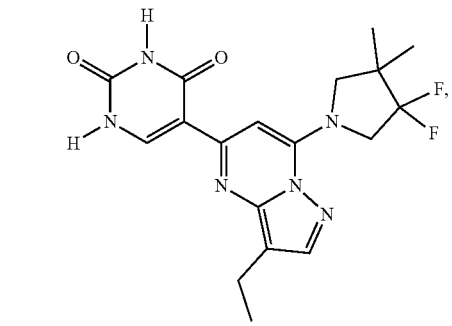
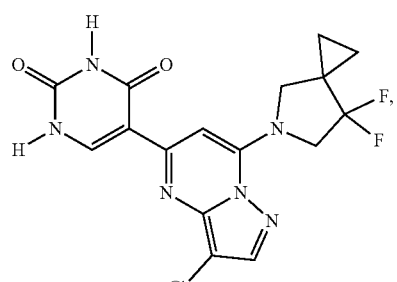
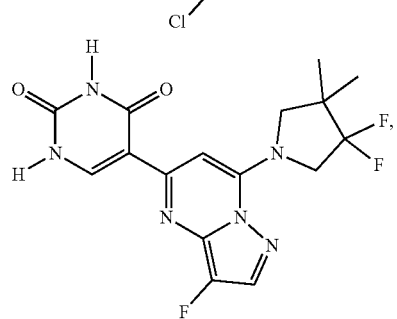
136
-continued
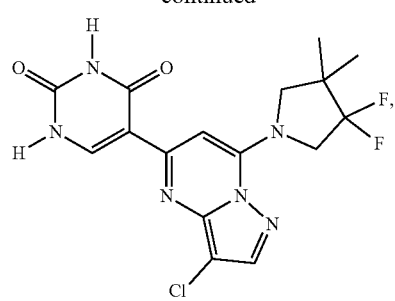
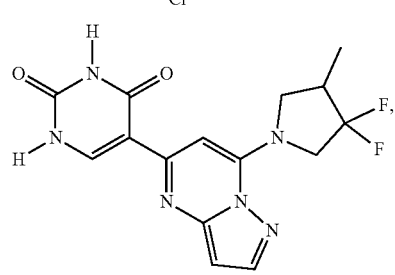
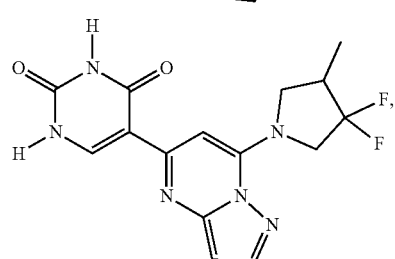
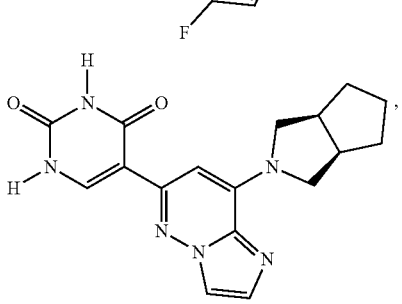
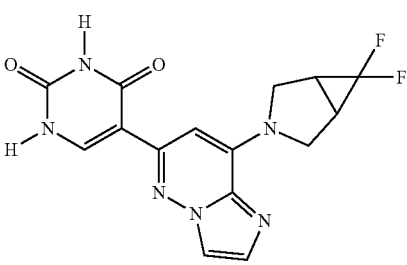
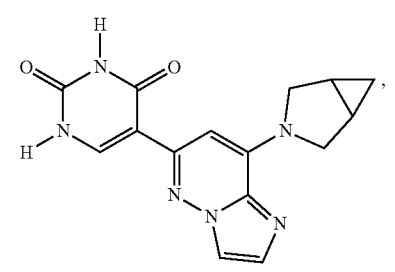

137
-continued
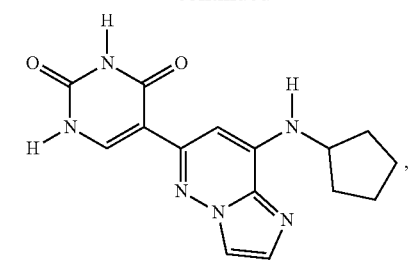
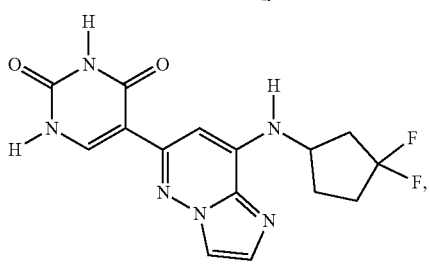
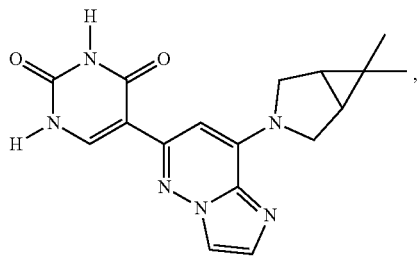
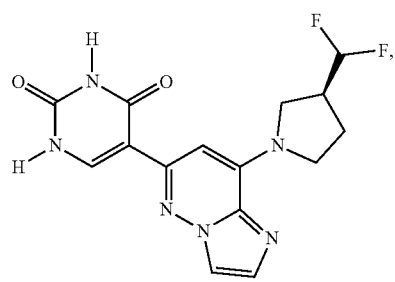
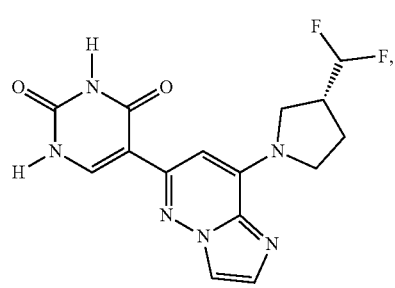
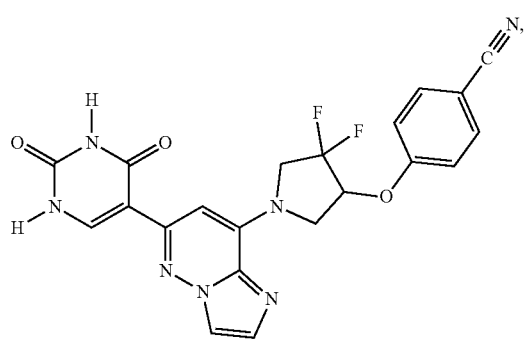
138
-continued
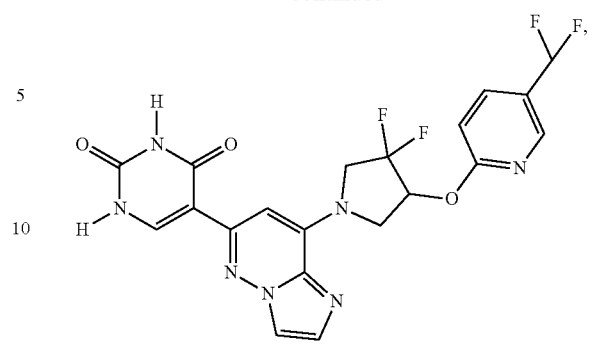
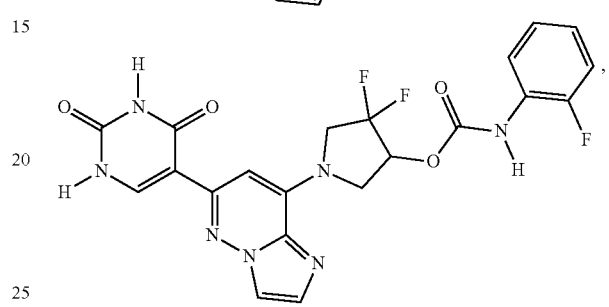
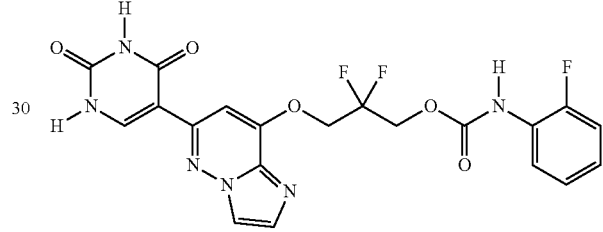
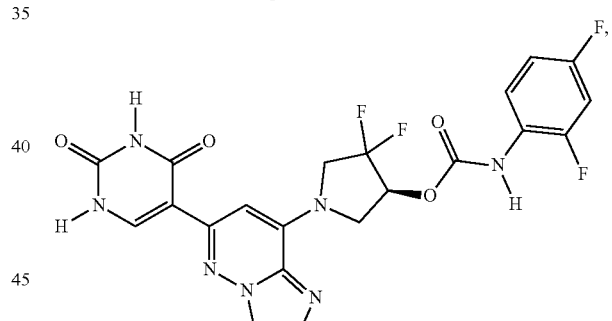
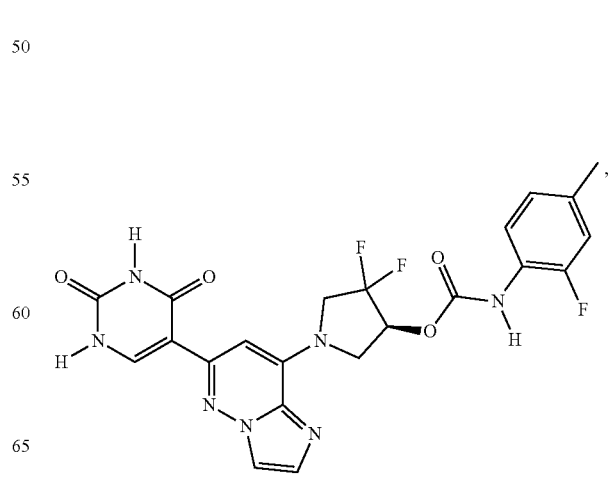

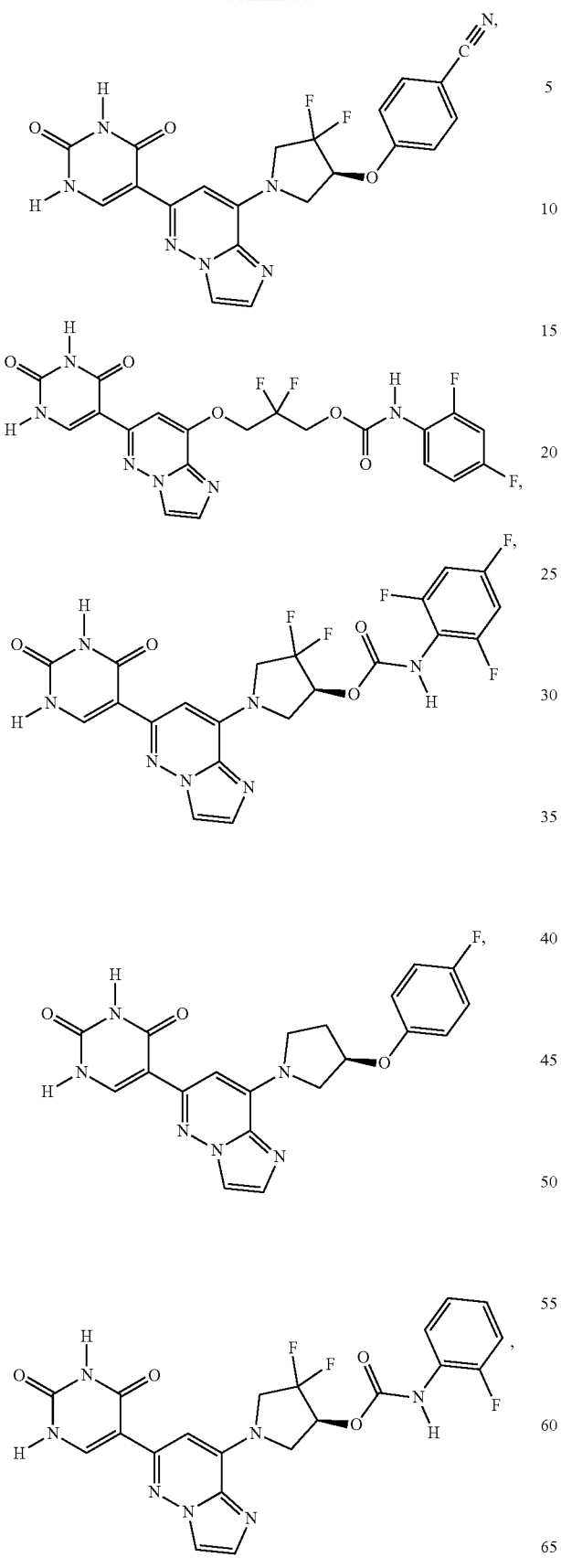
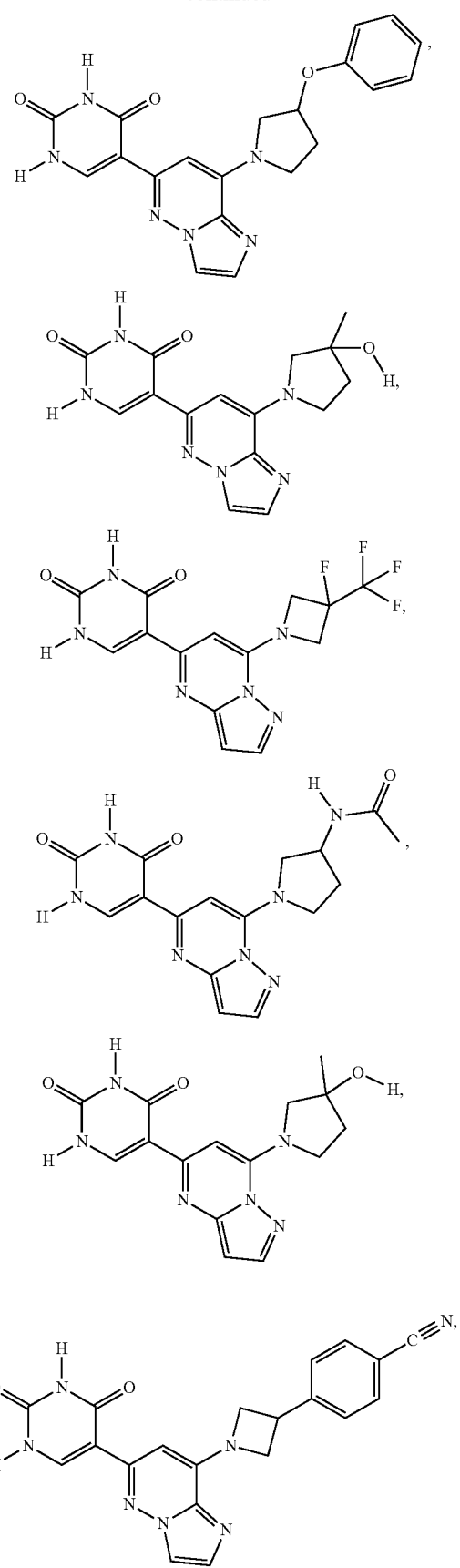

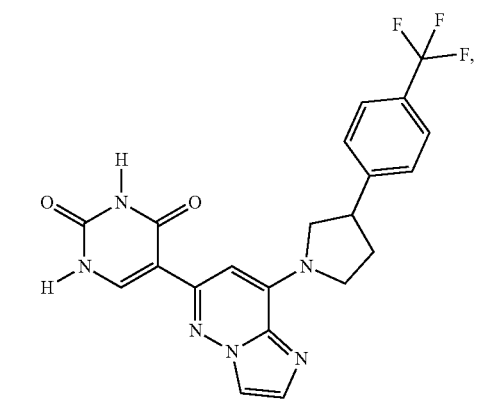
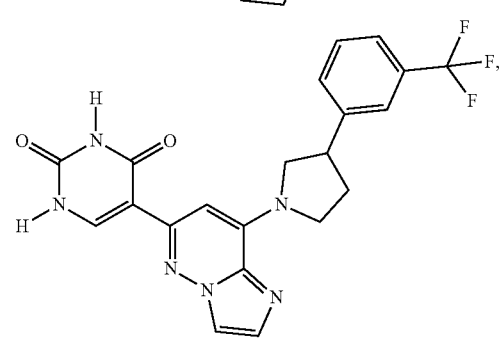
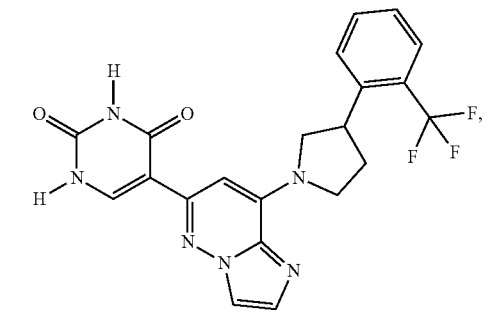
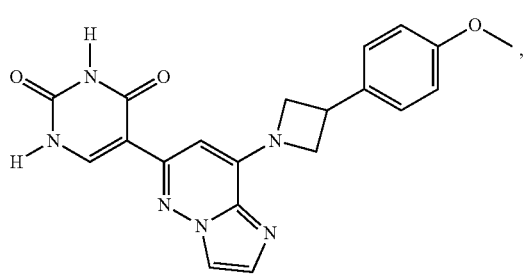
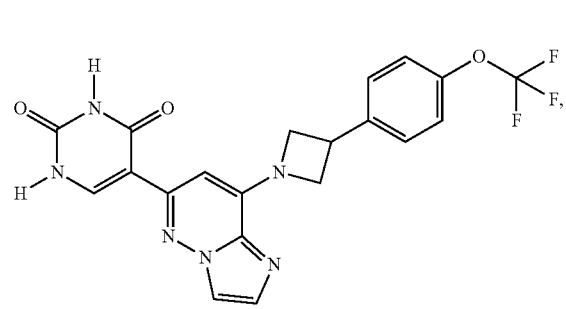
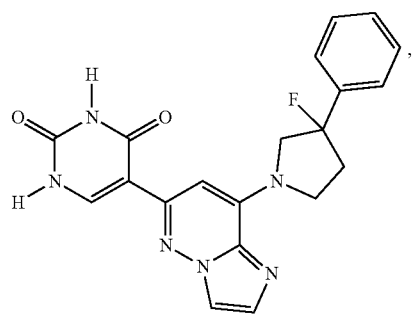
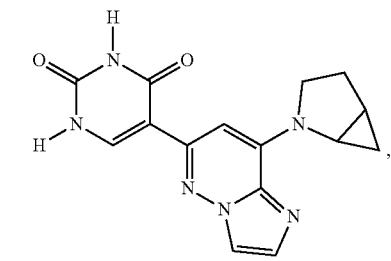
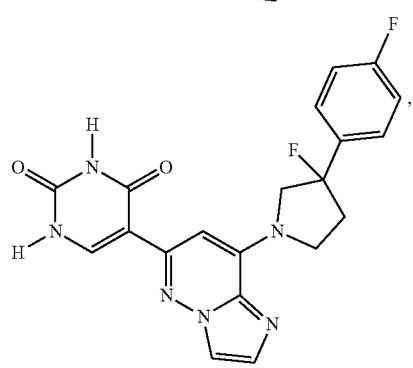
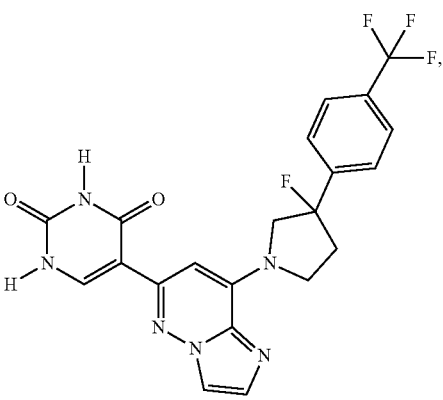
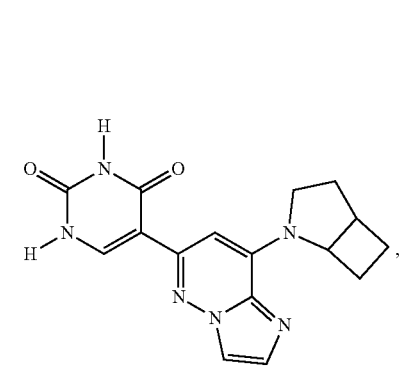

143
-continued
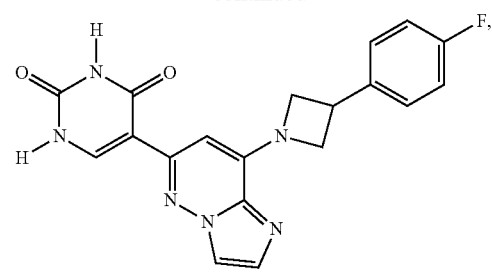
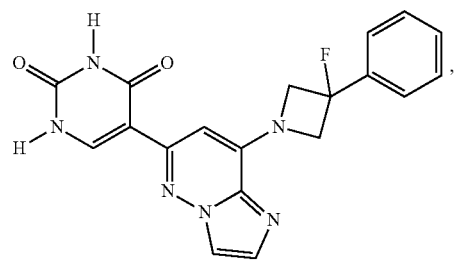
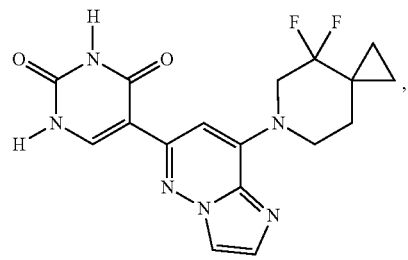
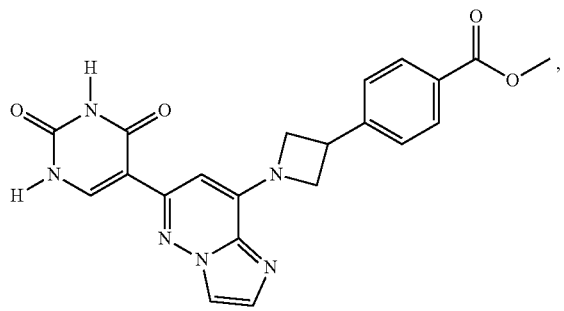
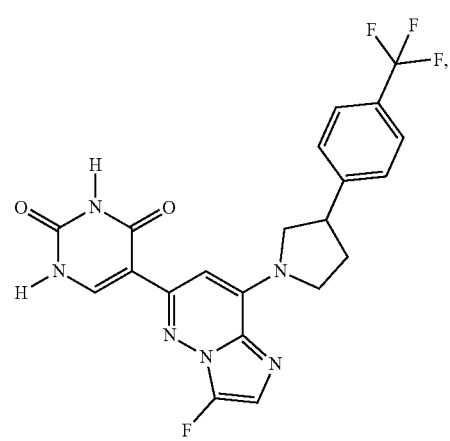
144
-continued
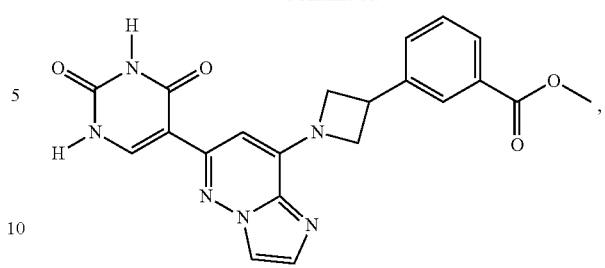
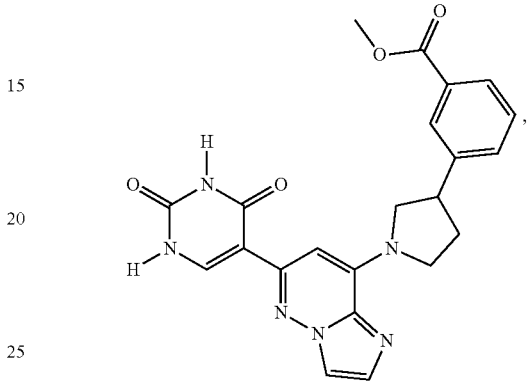
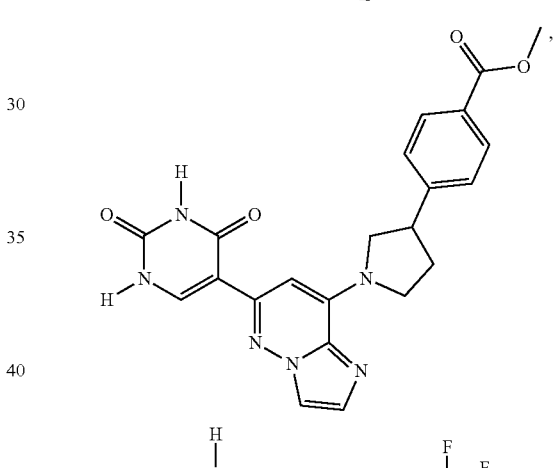
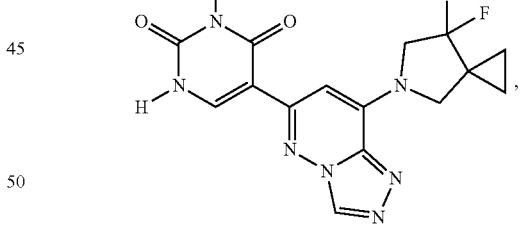
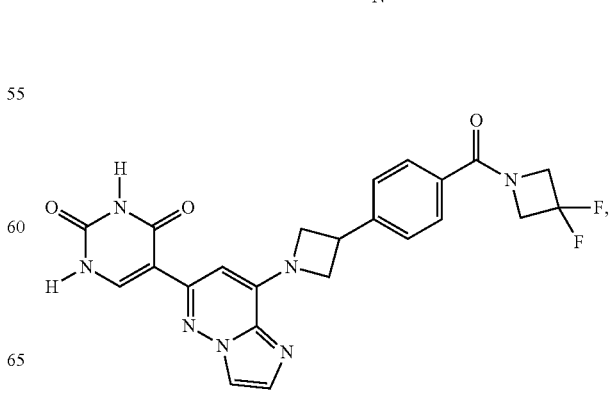

145
-continued
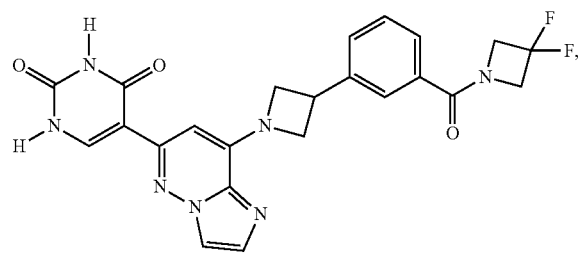
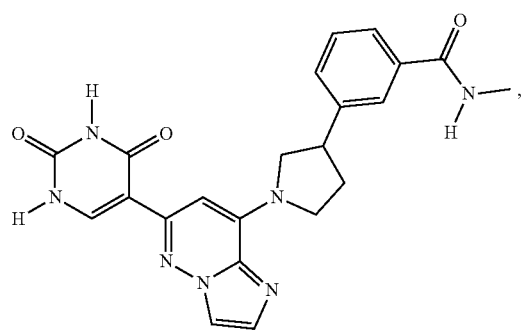
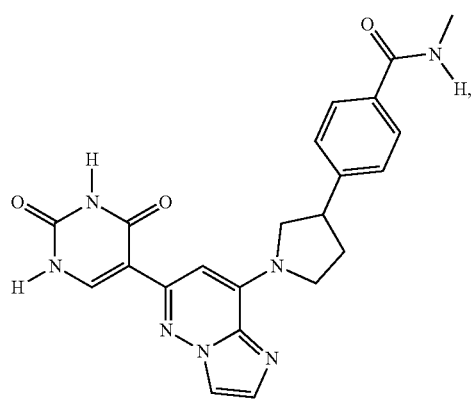
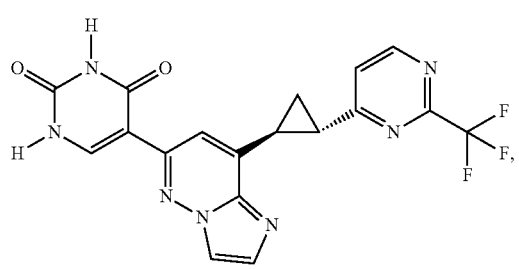
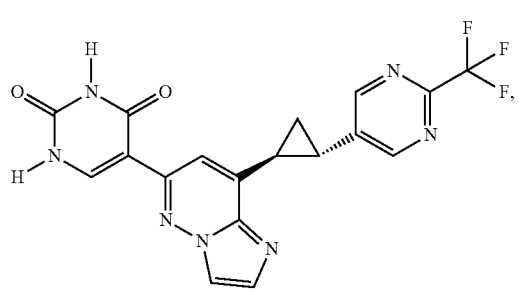
146
-continued
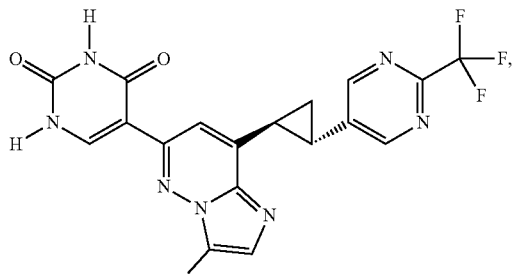
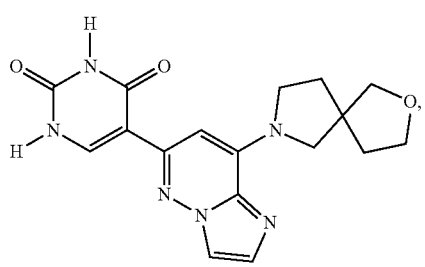
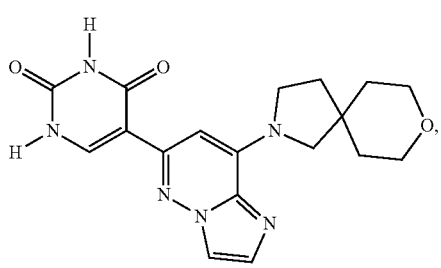
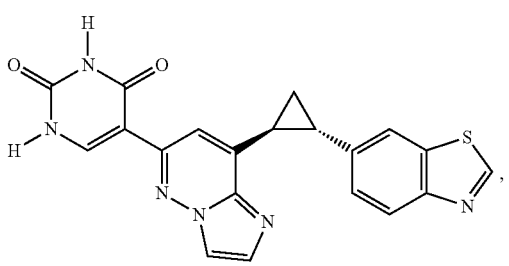
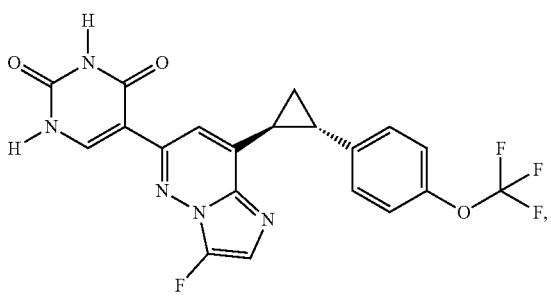
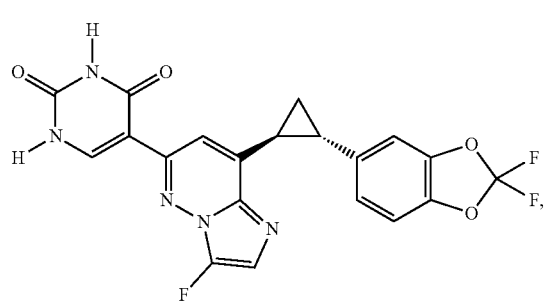

147
-continued
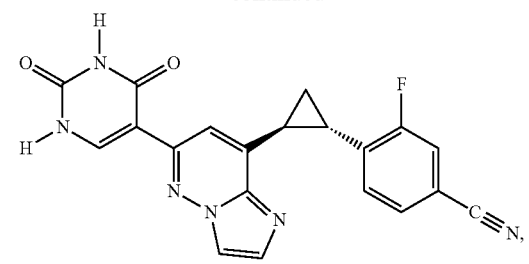
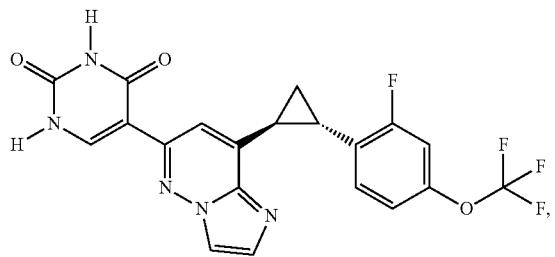
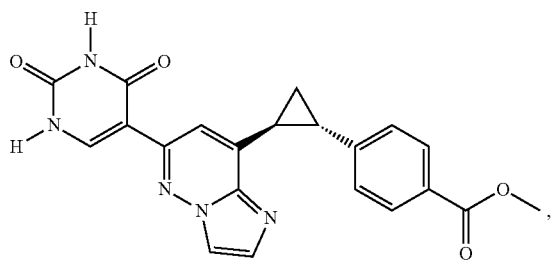
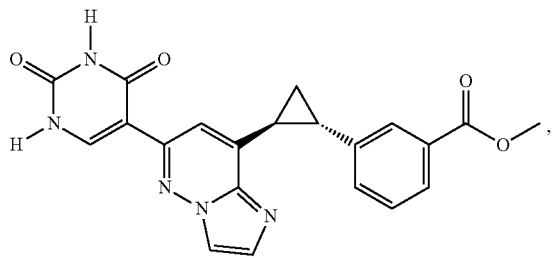
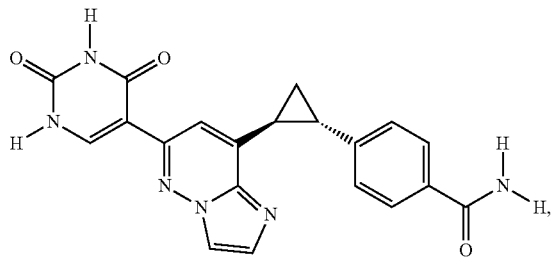
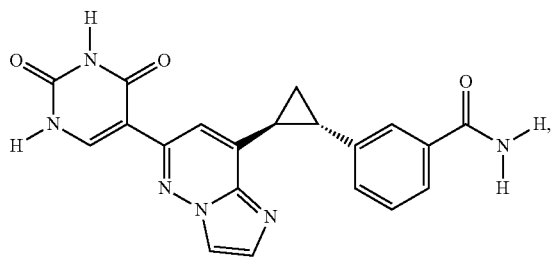
148
-continued

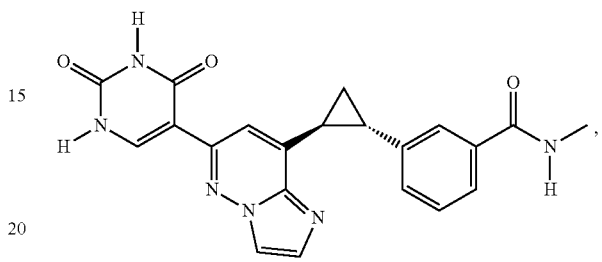

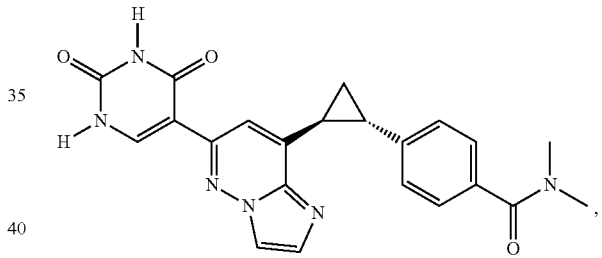
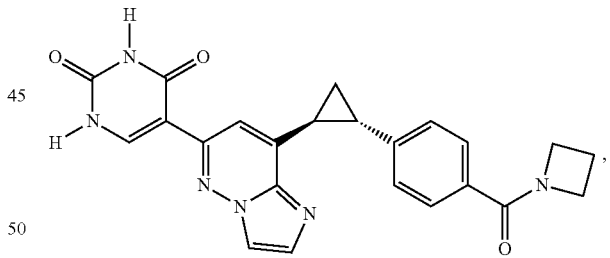
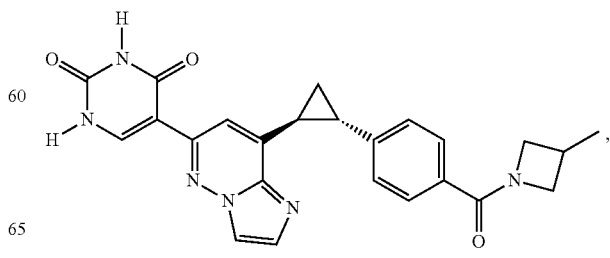

149
-continued
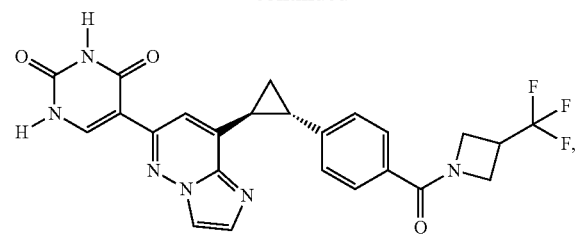
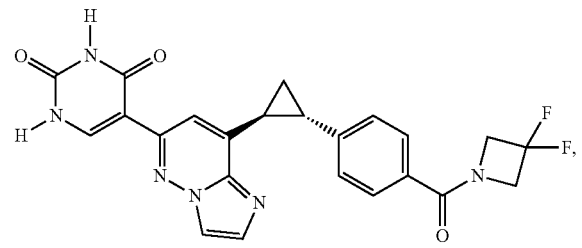
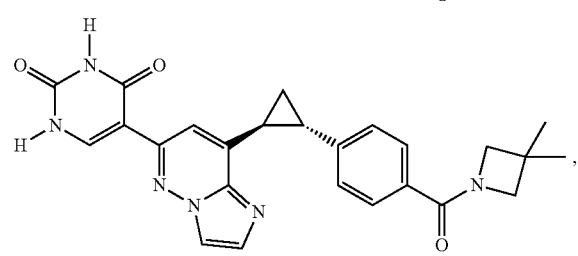
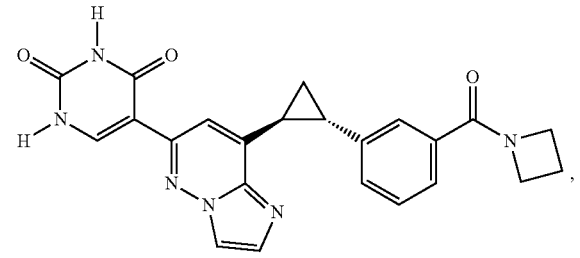
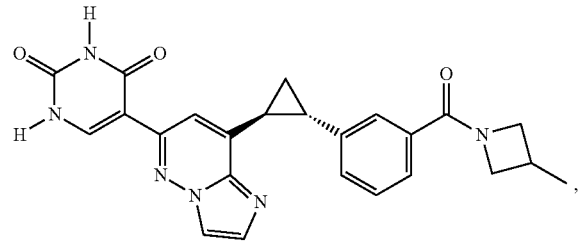
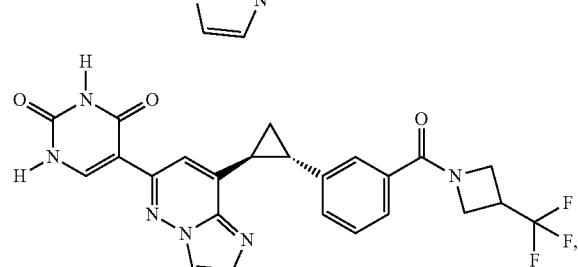
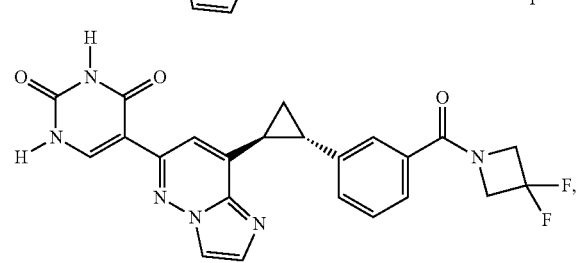
150
-continued
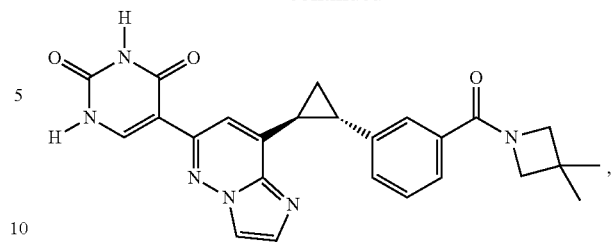

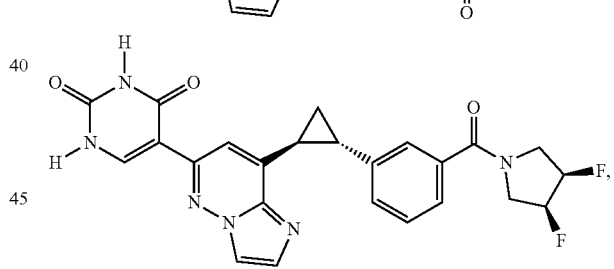
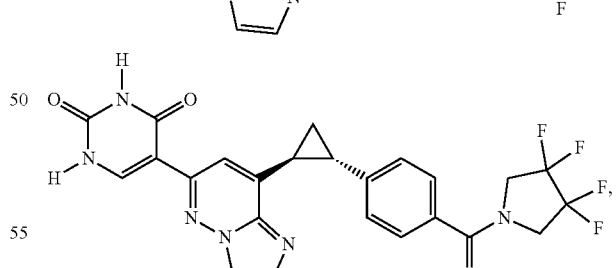
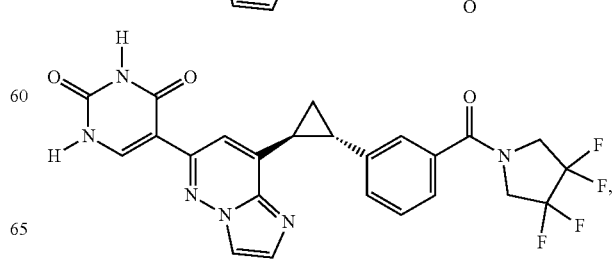

151
-continued
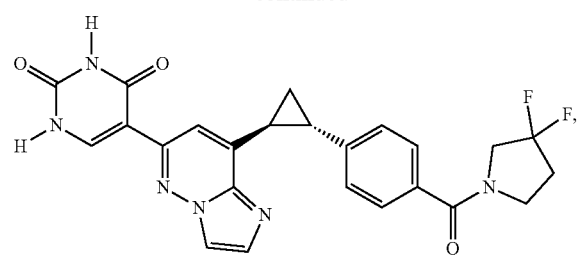
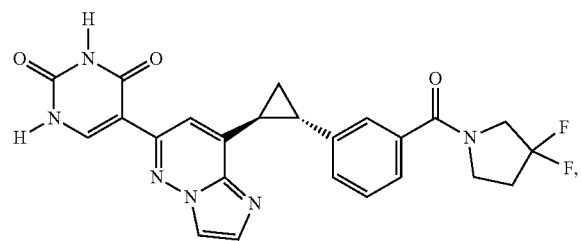
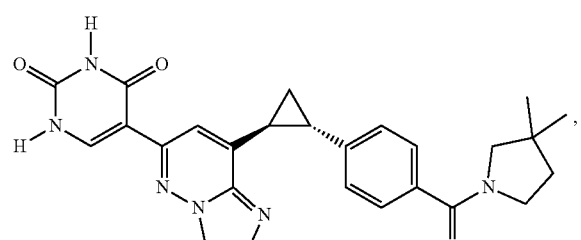
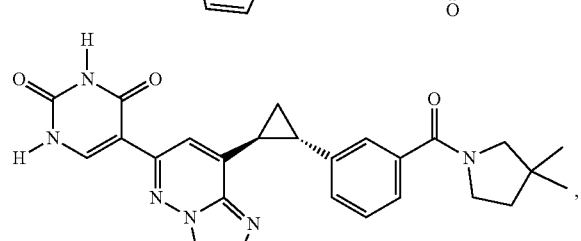
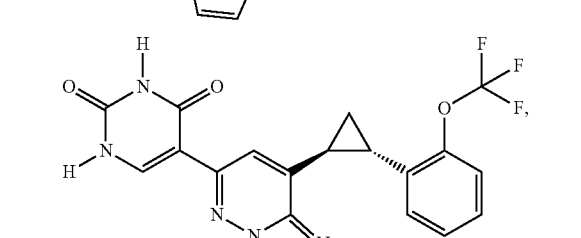
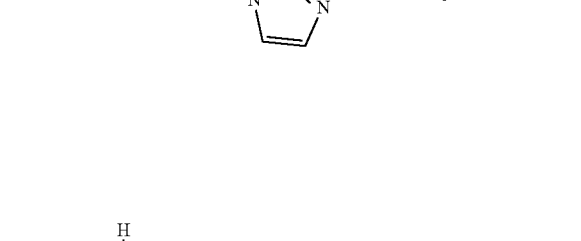
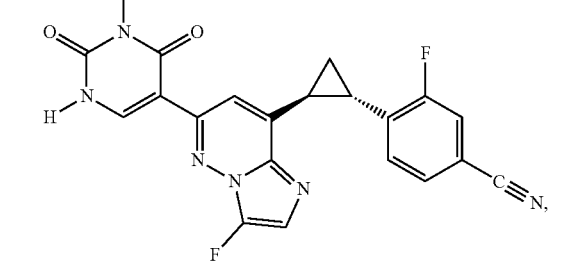
152
-continued
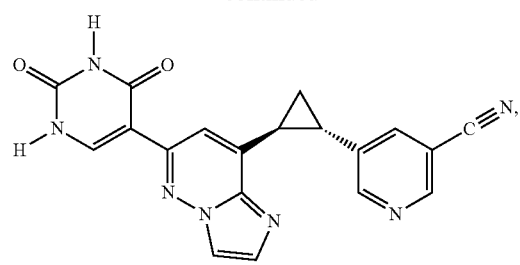
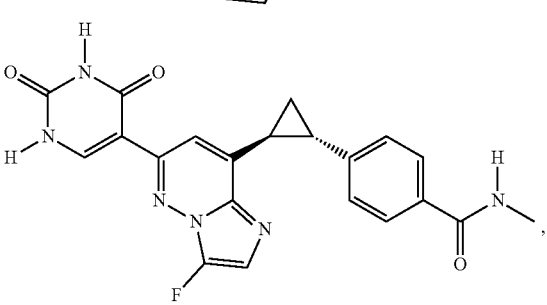
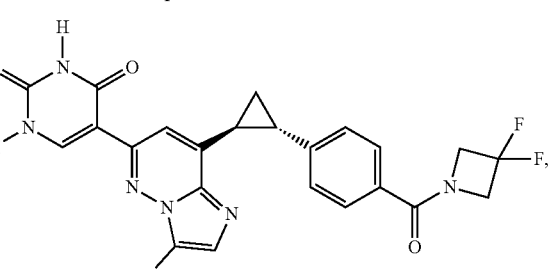
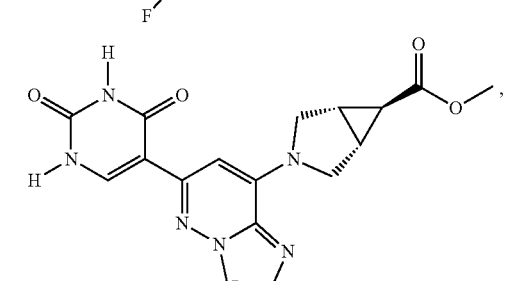
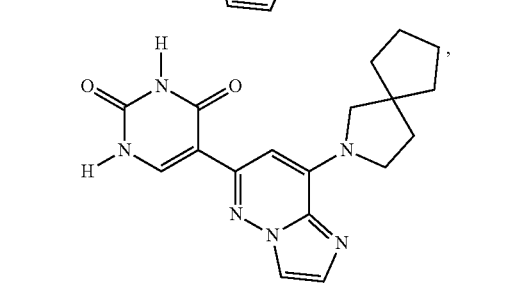
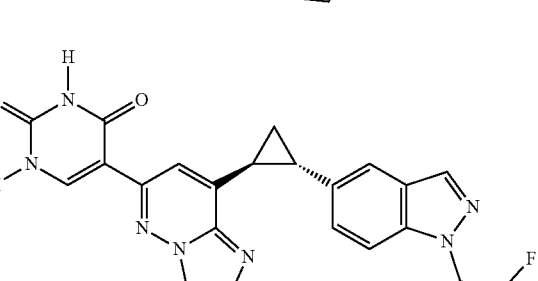

153
-continued
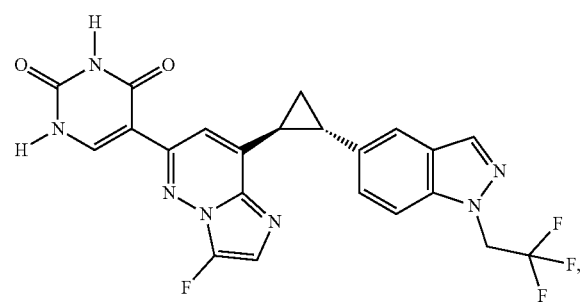
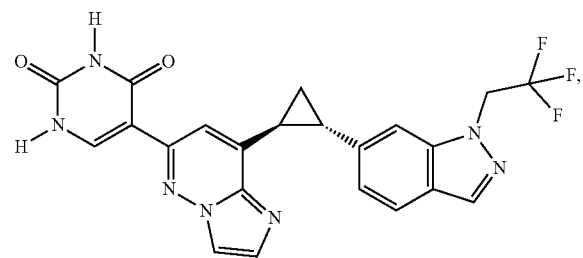
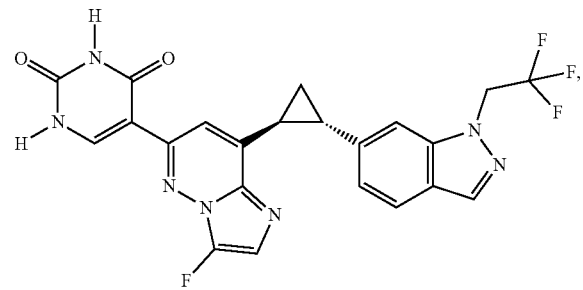
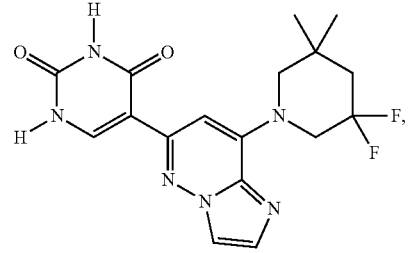
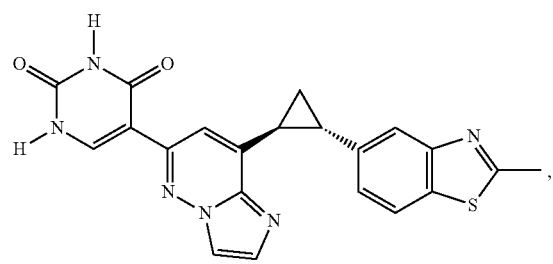
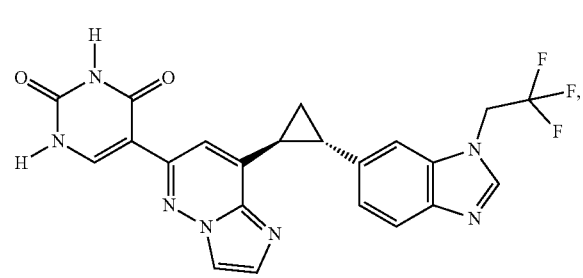
154
-continued
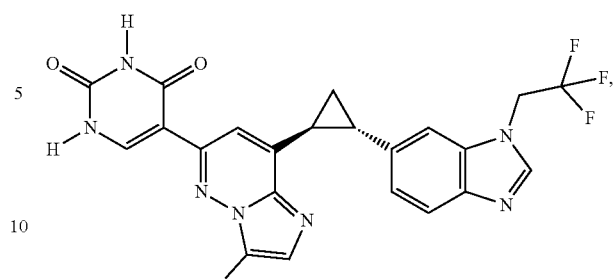
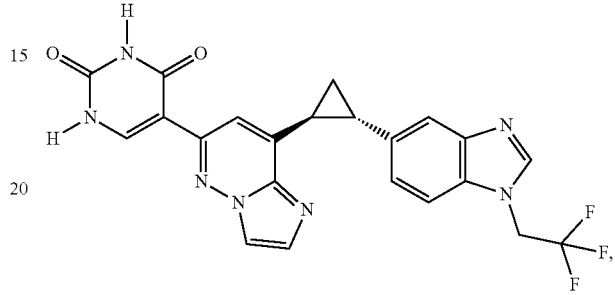
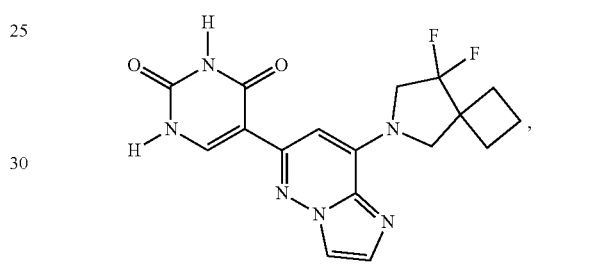
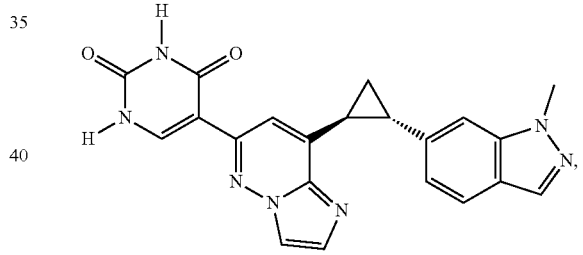
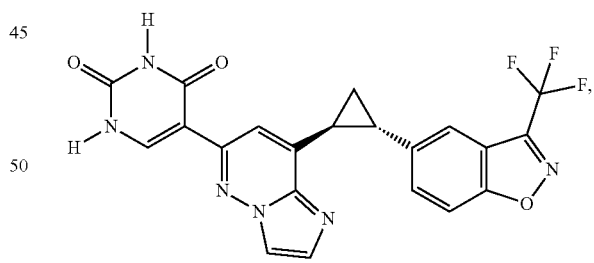
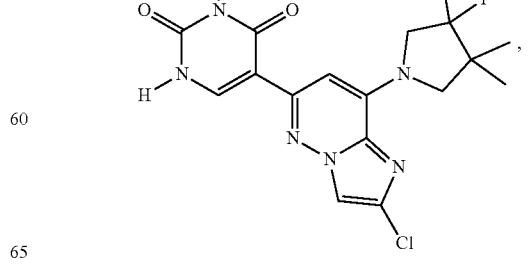

155
-continued
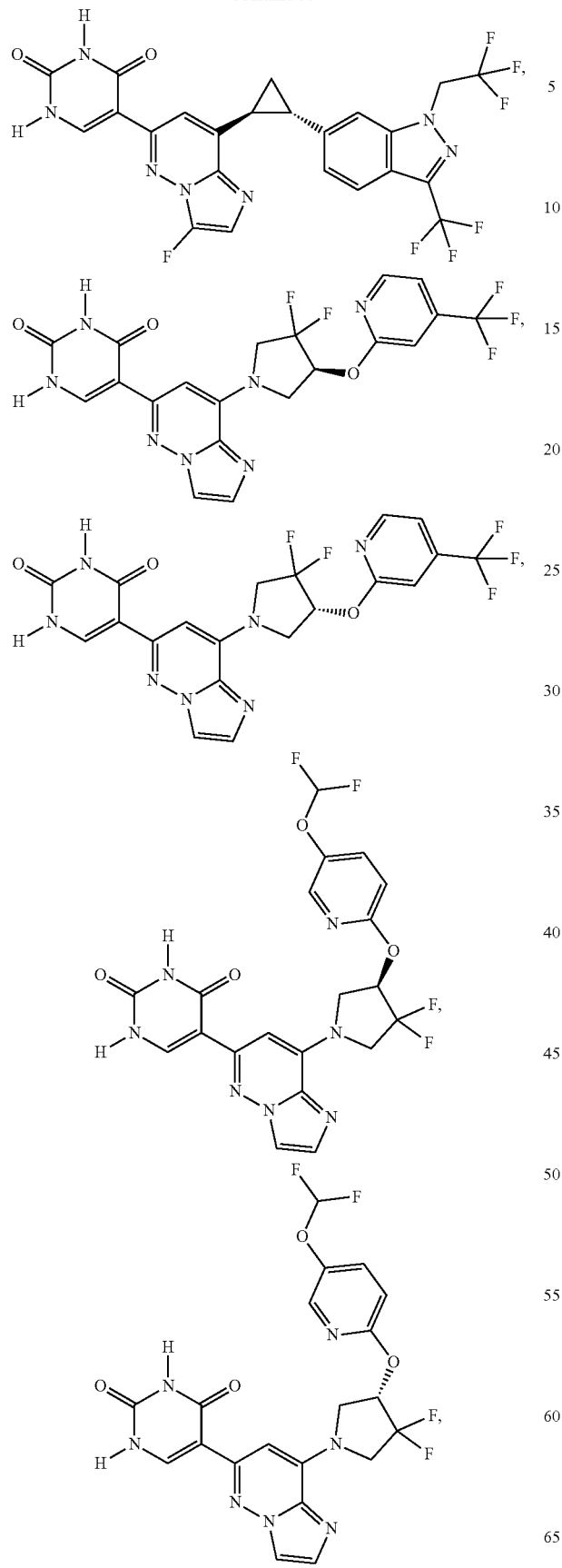
156
-continued
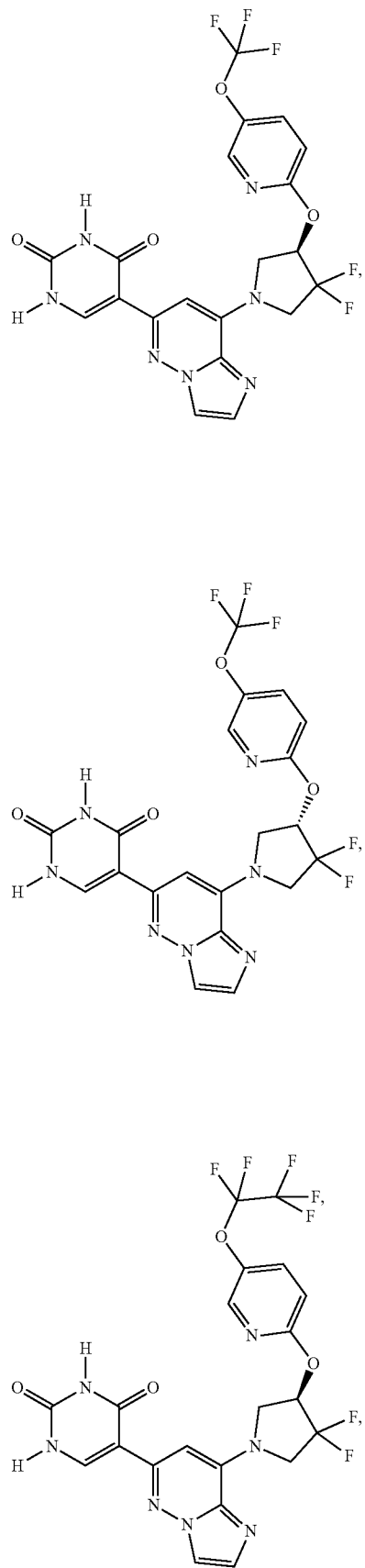

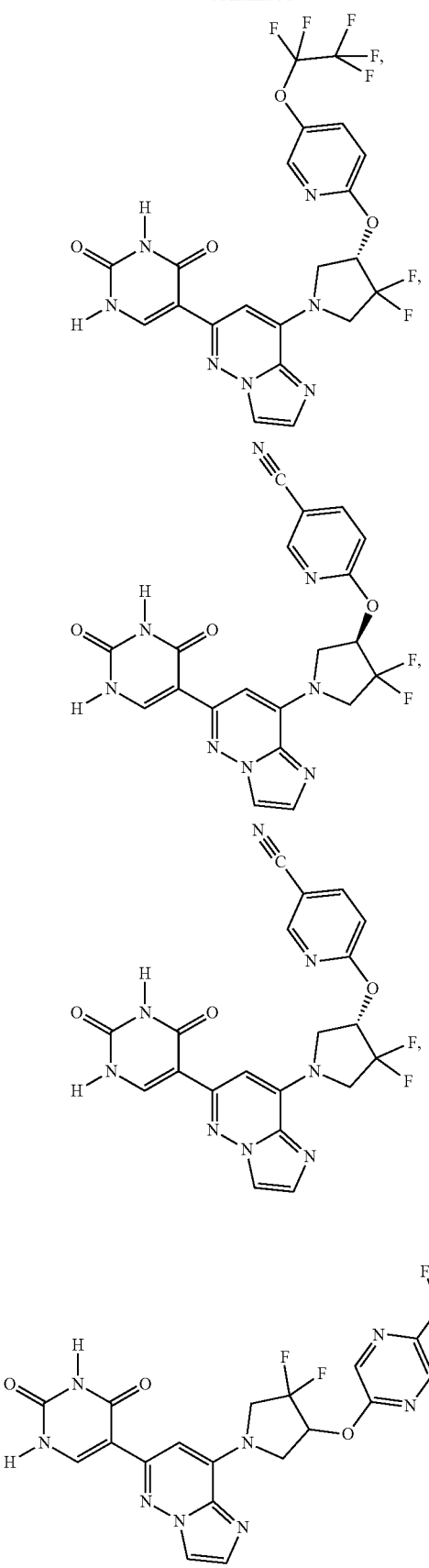
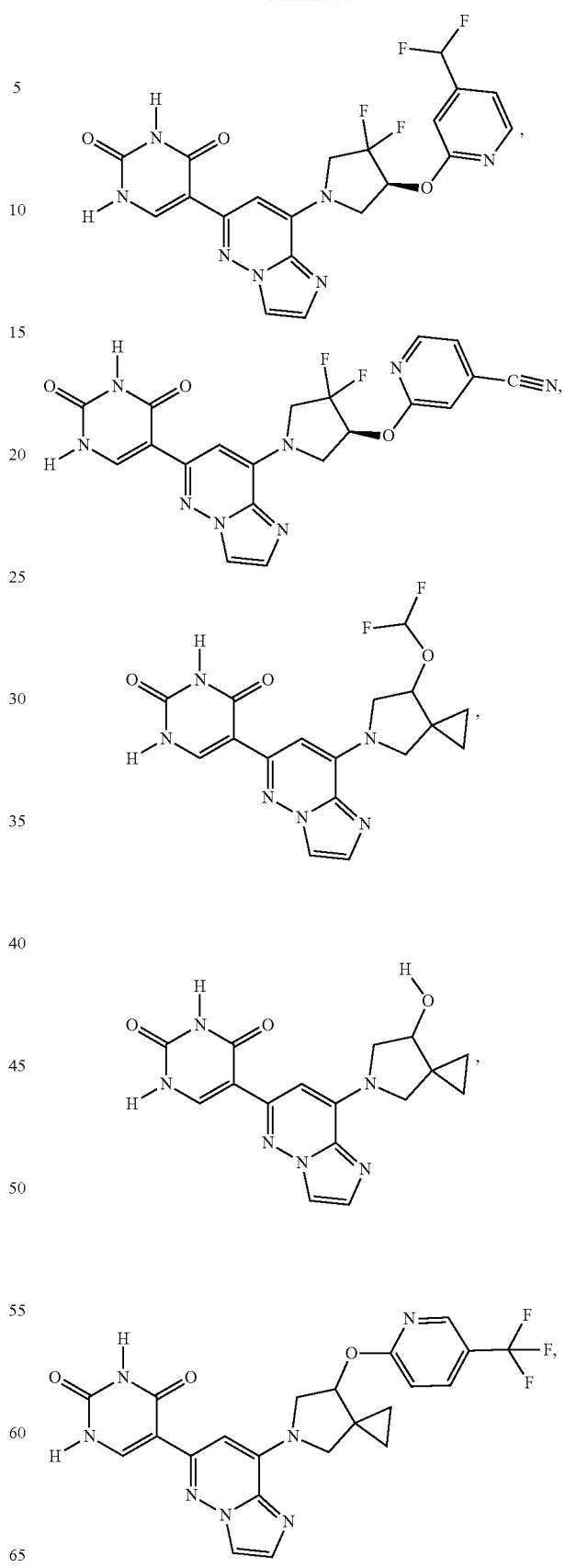

159
-continued
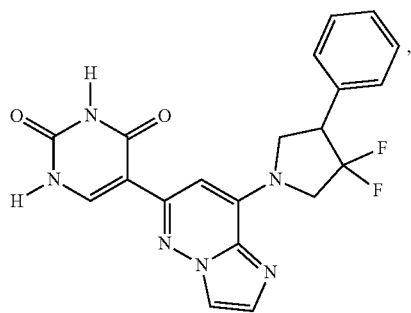
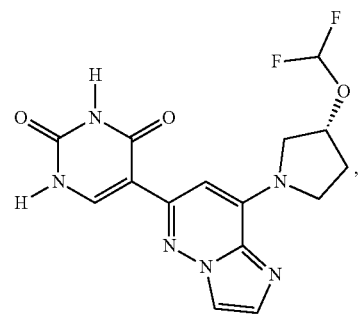
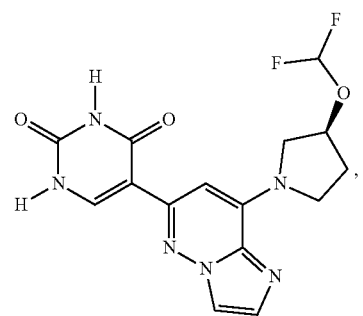
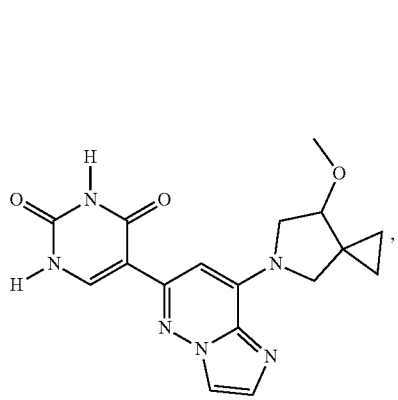
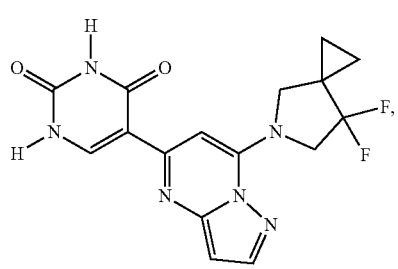
160
-continued
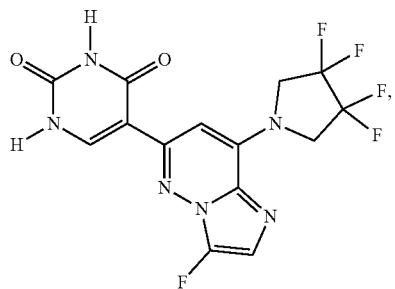
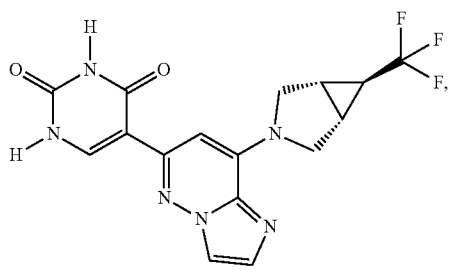
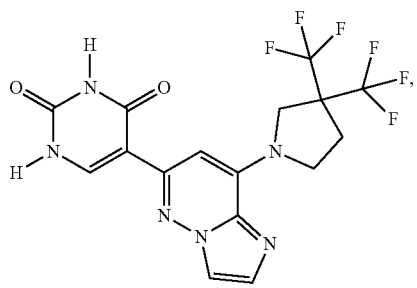
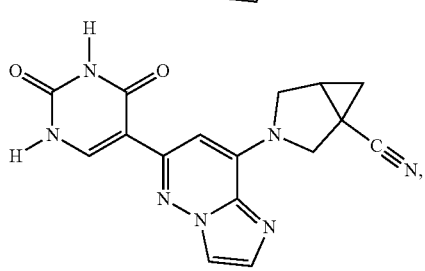
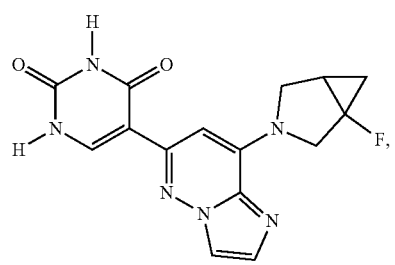
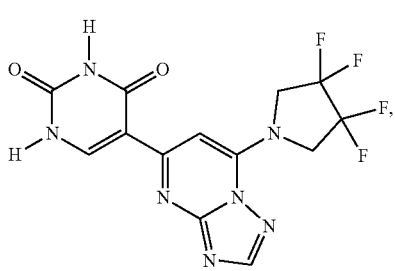

161
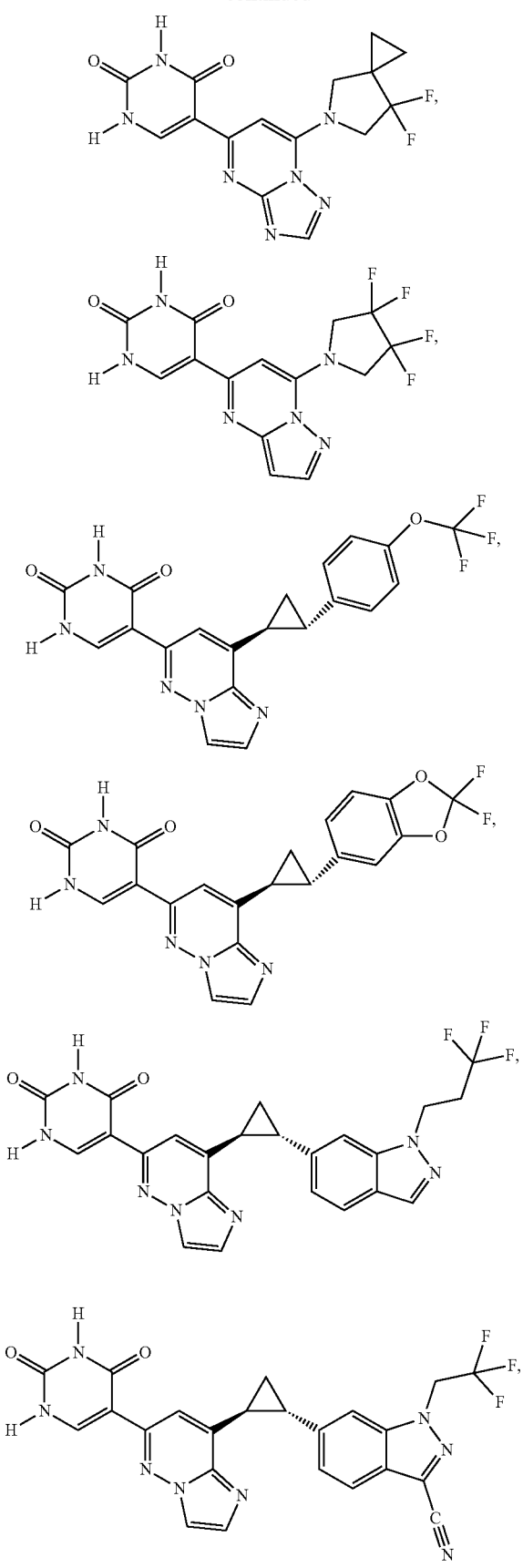
162
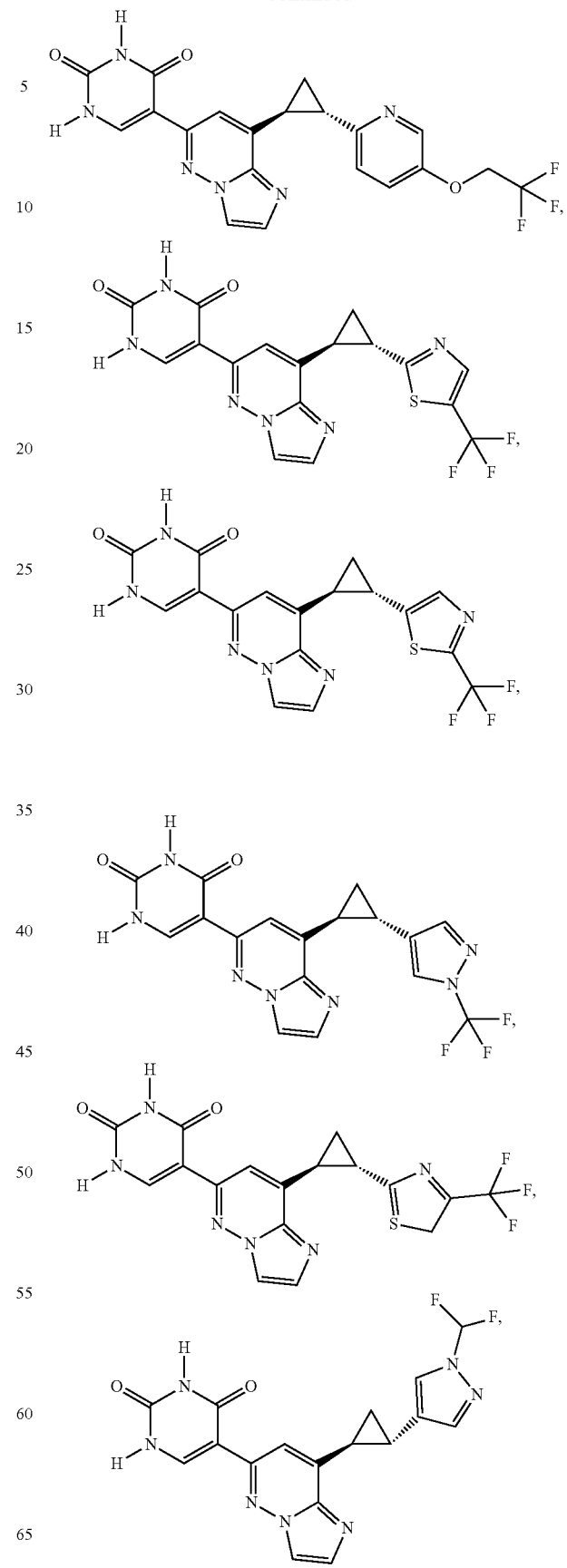

163
-continued
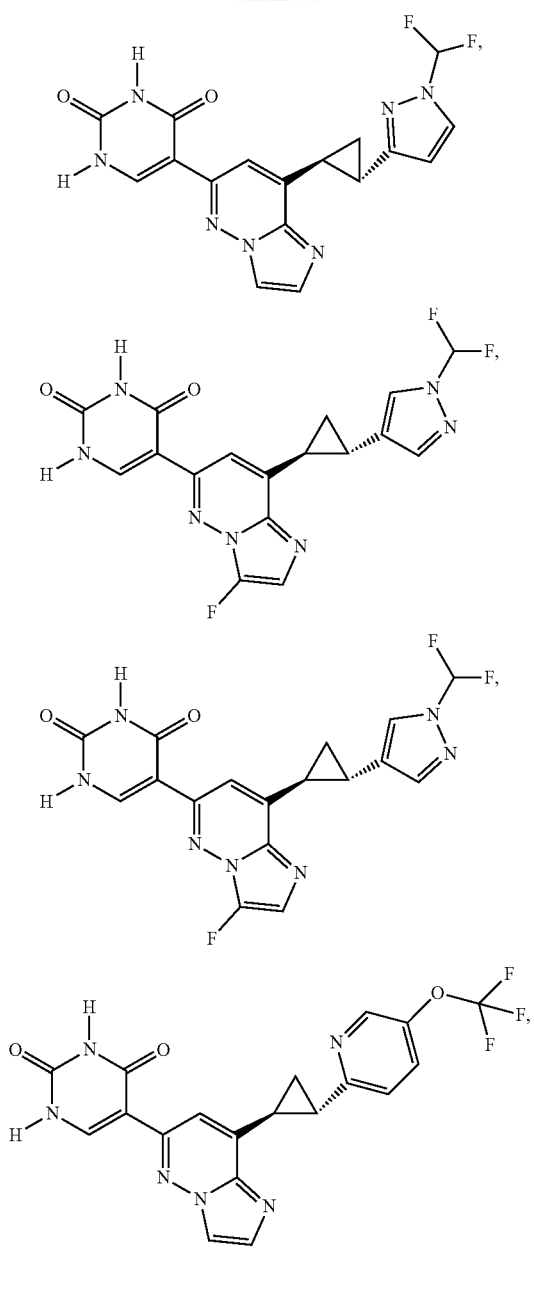
164
-continued
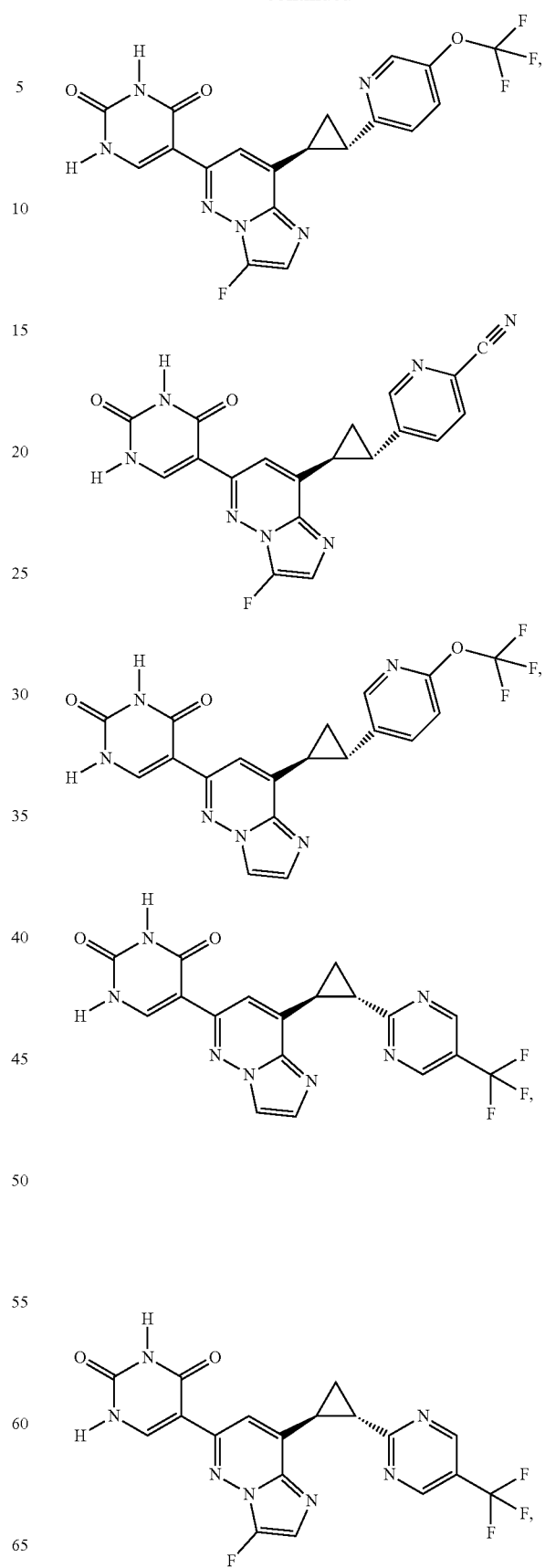

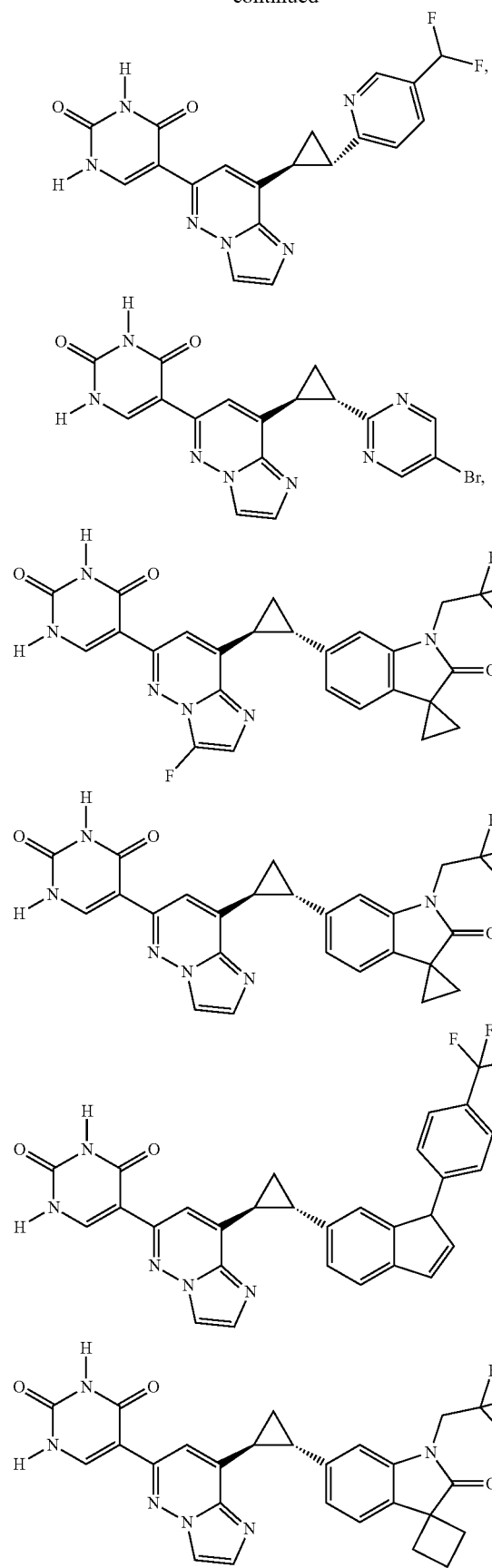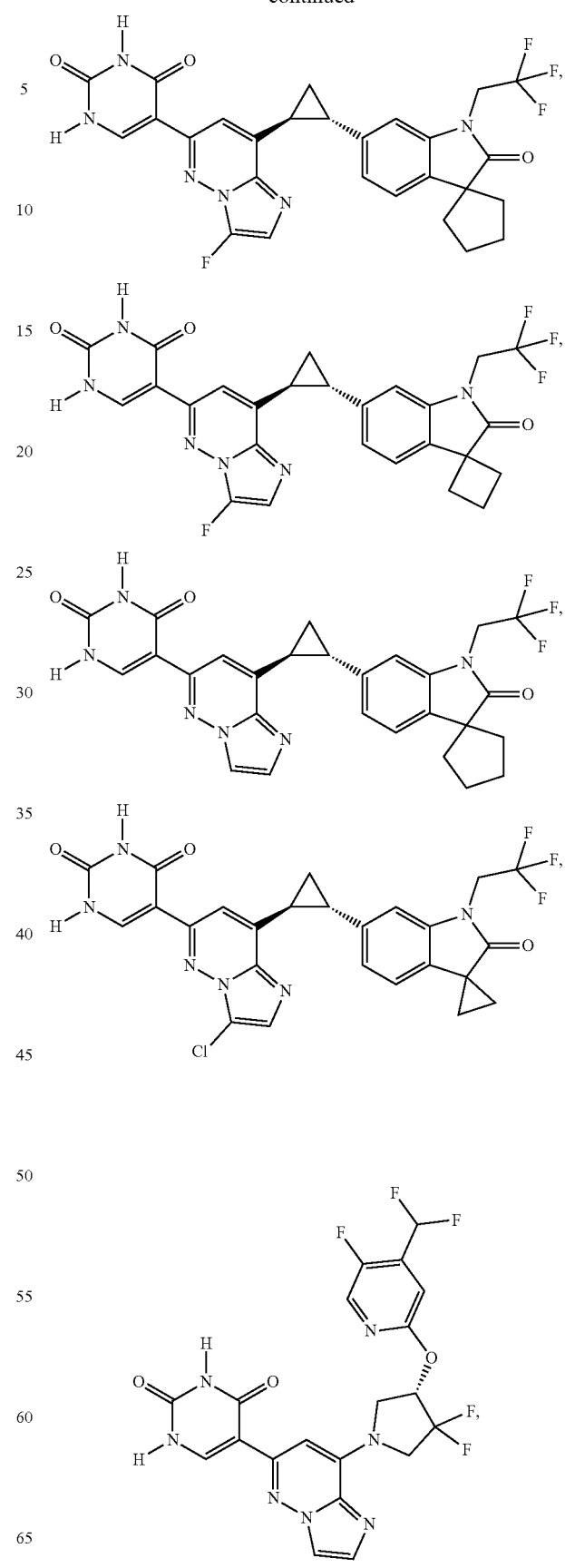

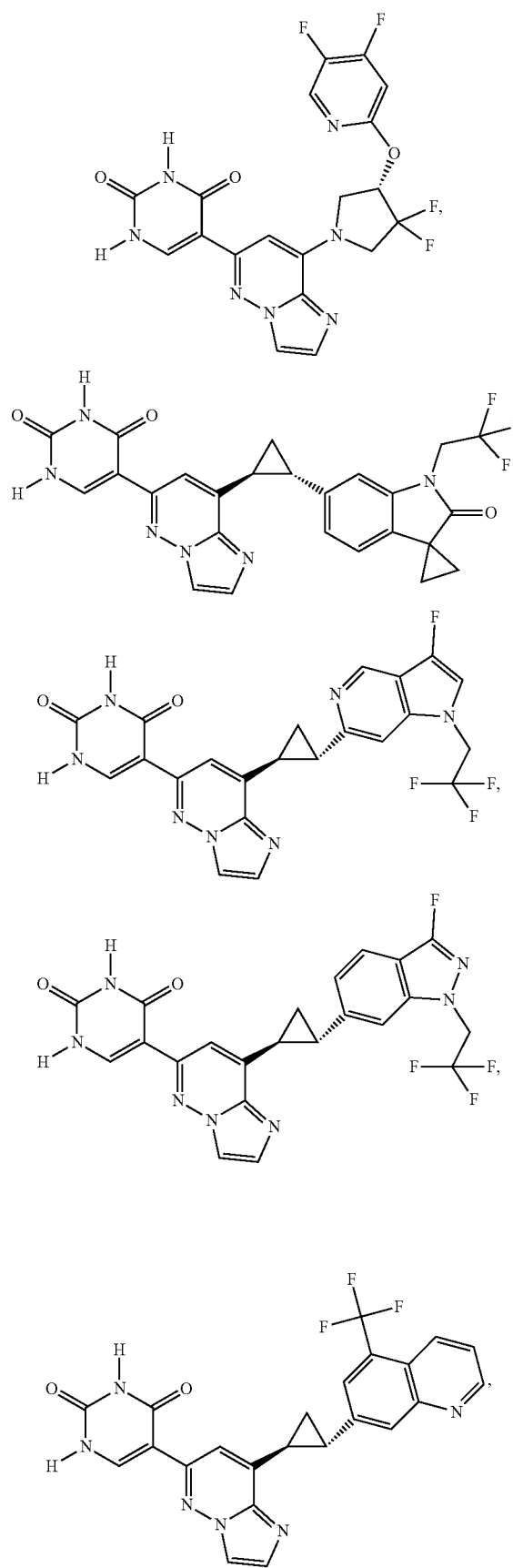
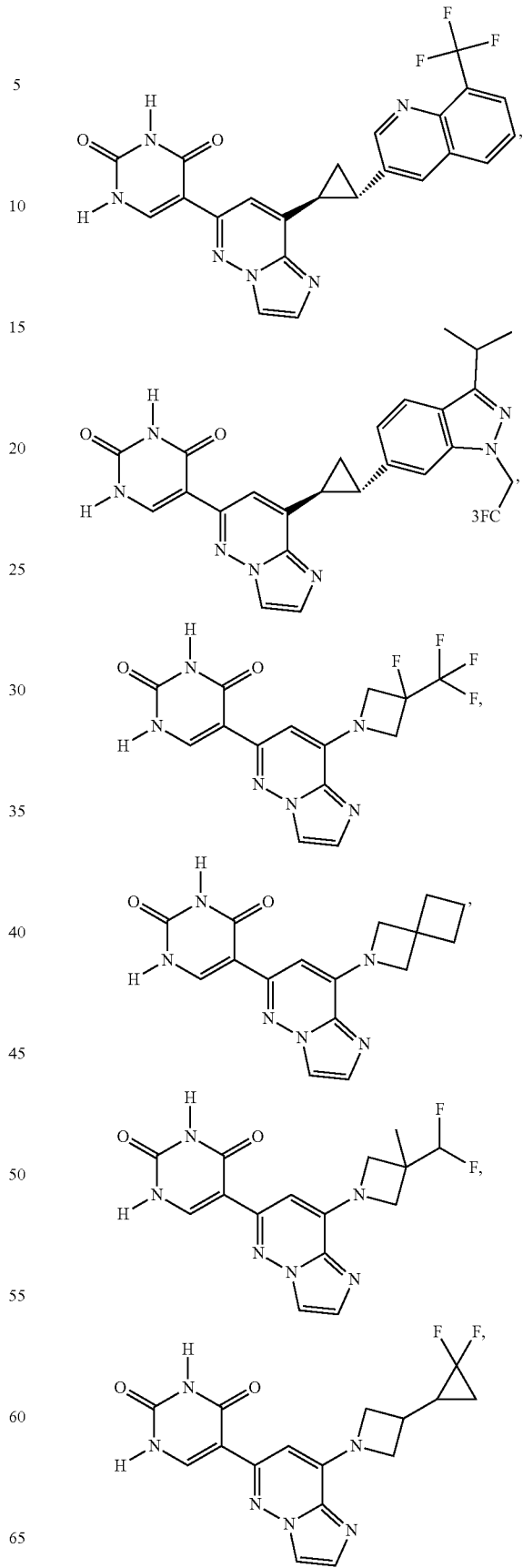

169
-continued
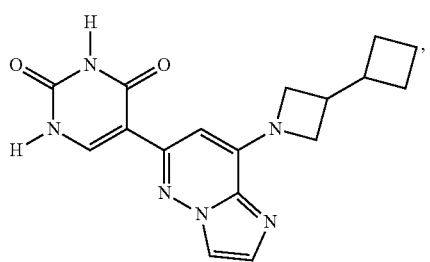
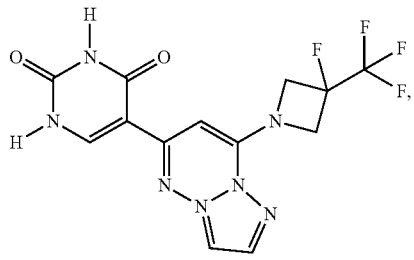
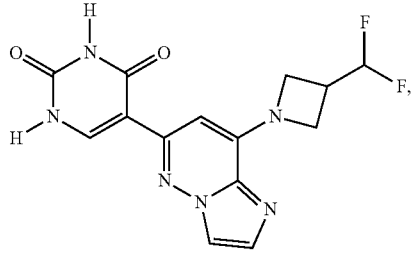
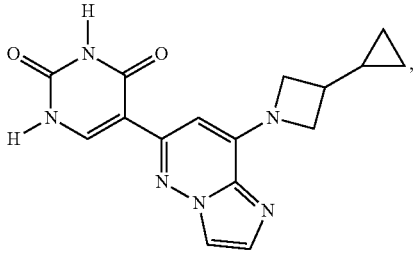
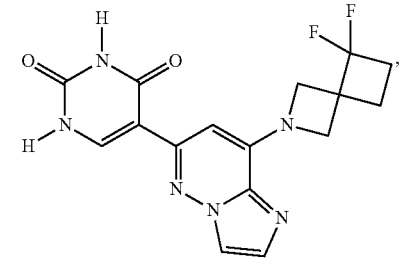
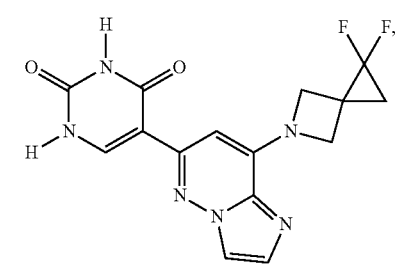
170
-continued
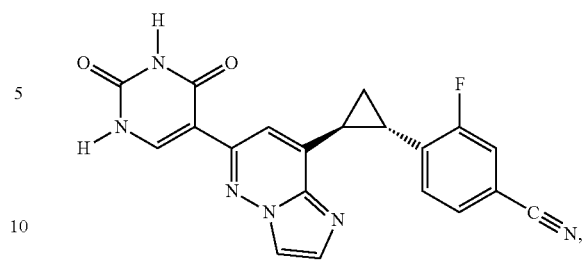
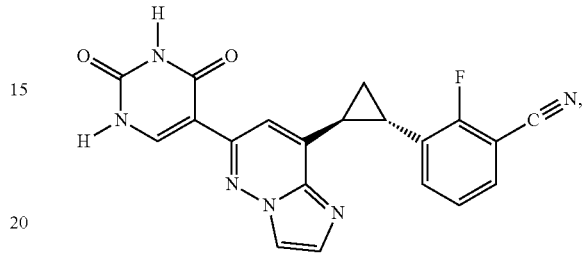
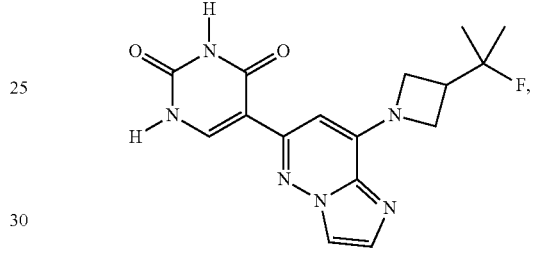
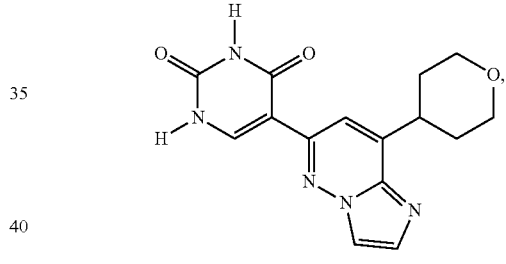
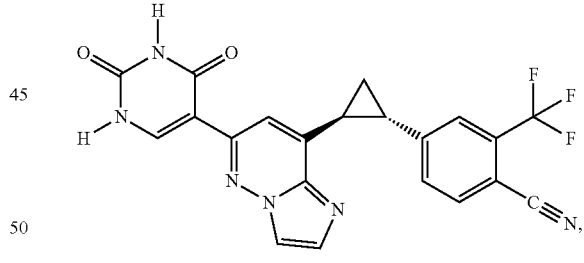
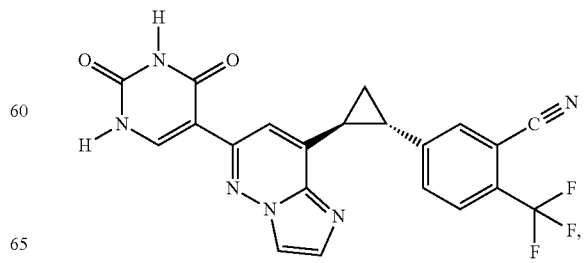

171
-continued
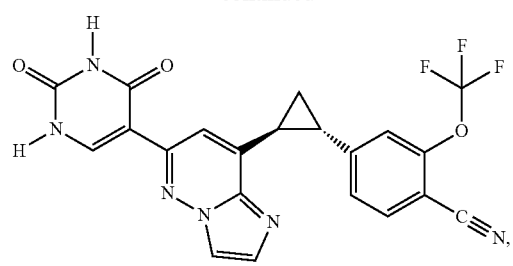
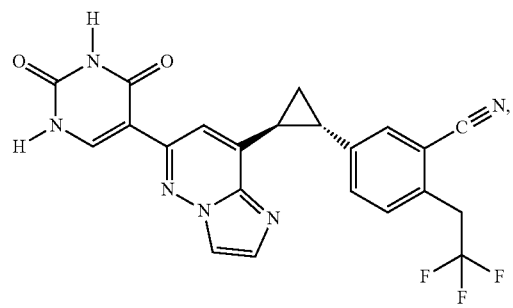
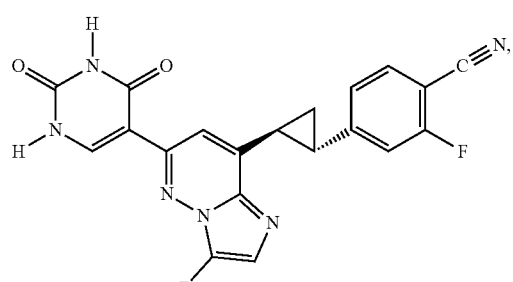
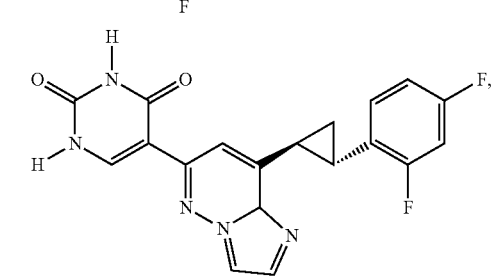
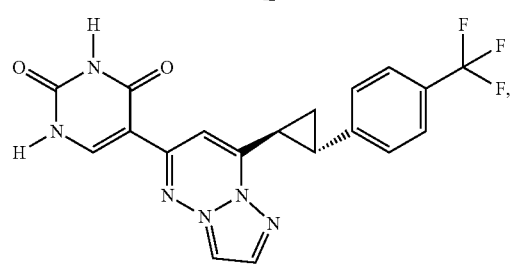
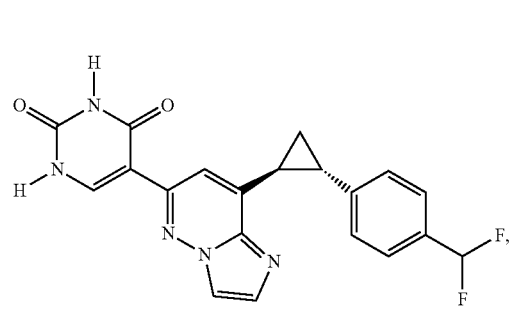
172
-continued
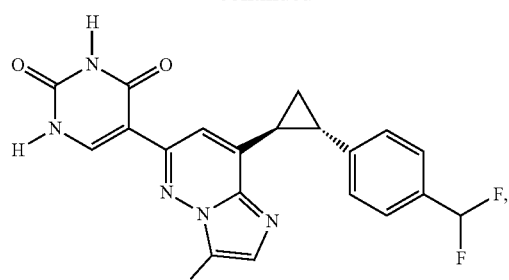
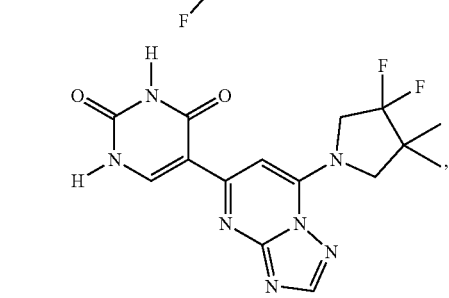
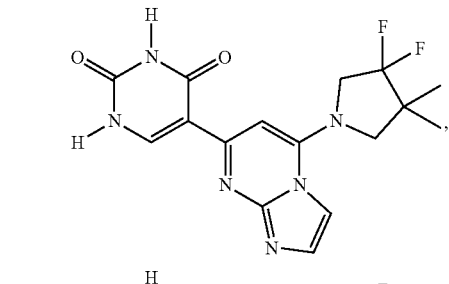
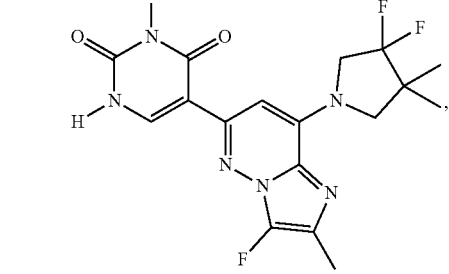
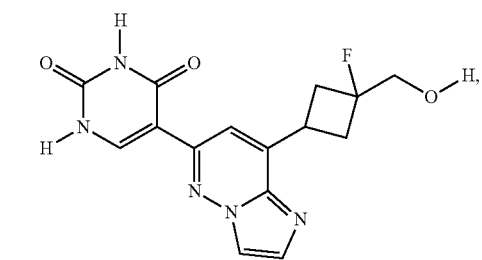
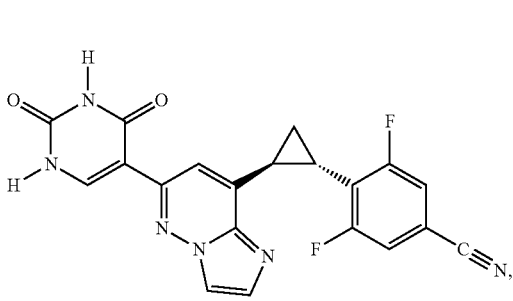

-continued
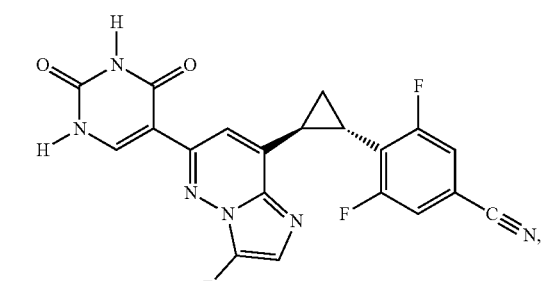
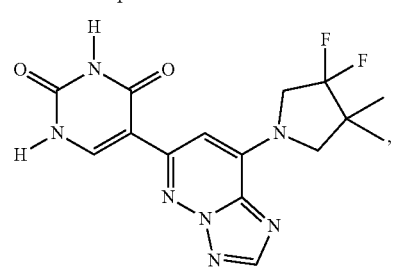
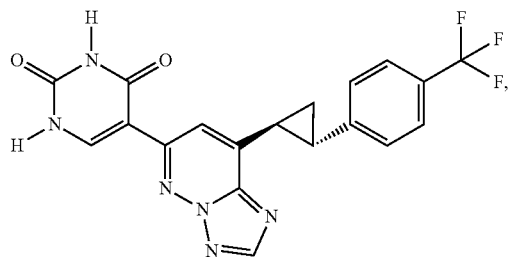
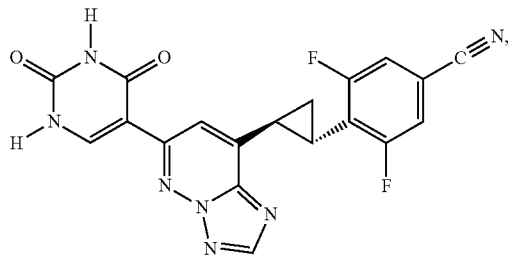
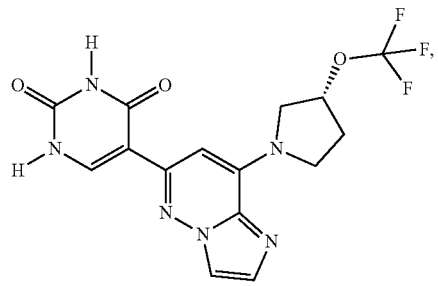
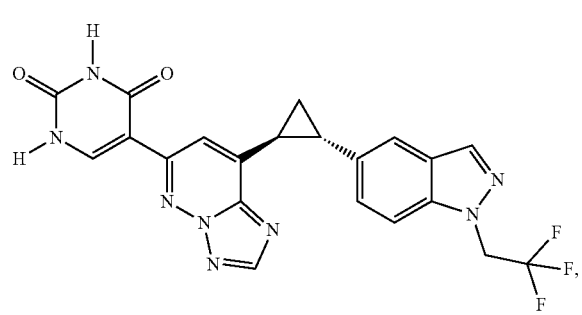
-continued
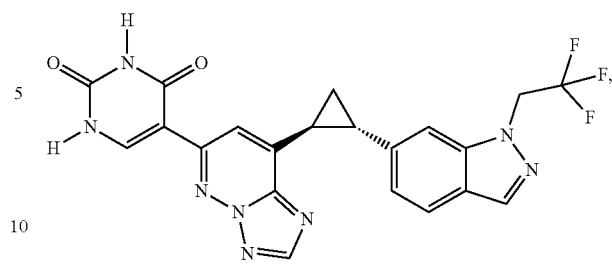
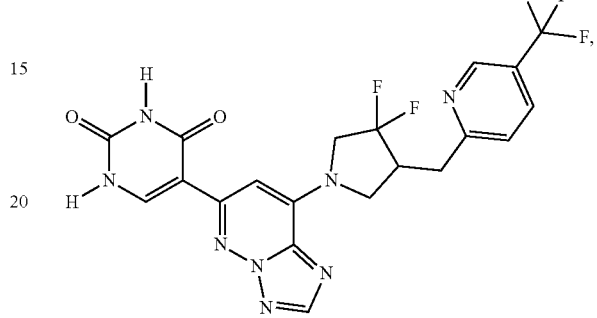
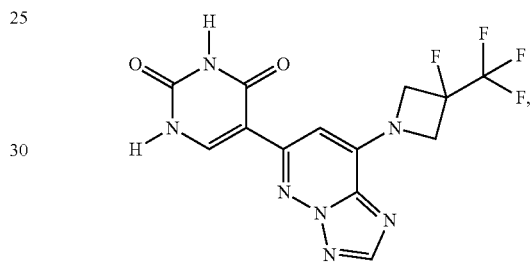
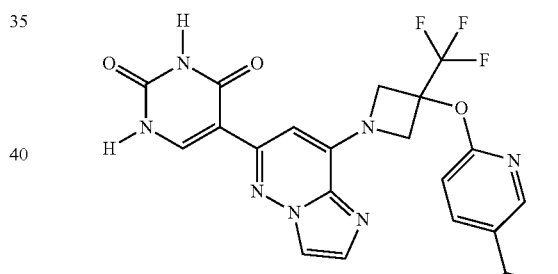
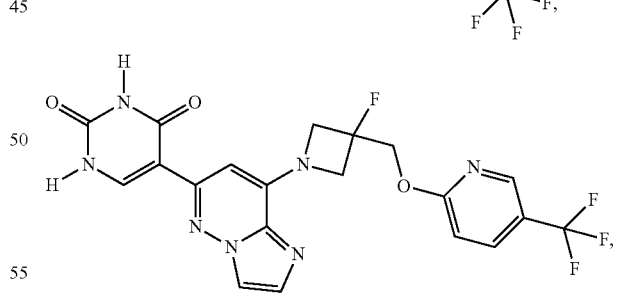
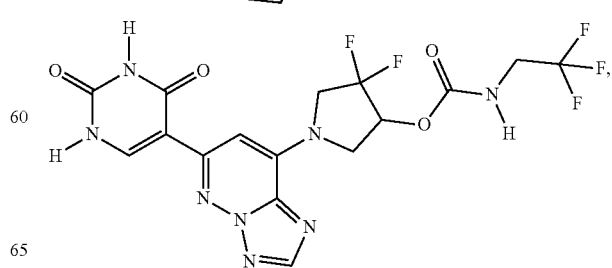

175
-continued
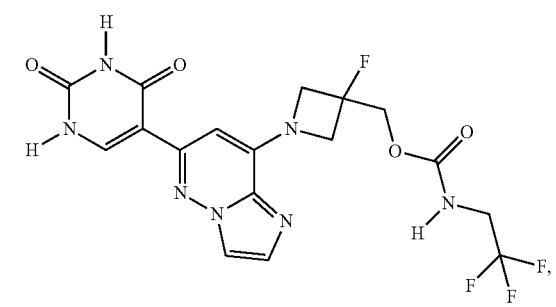
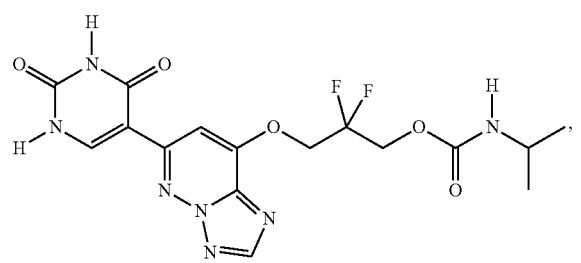
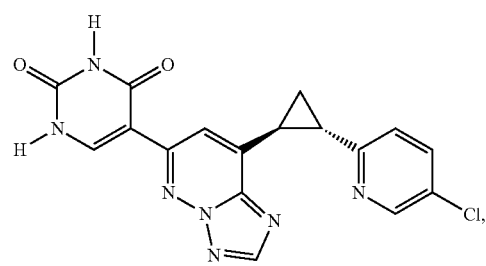
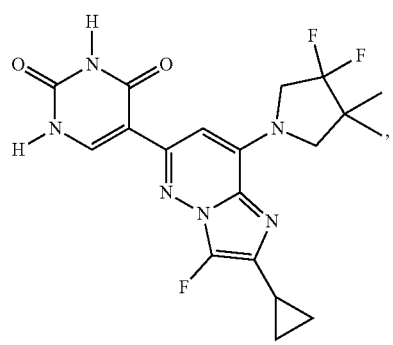
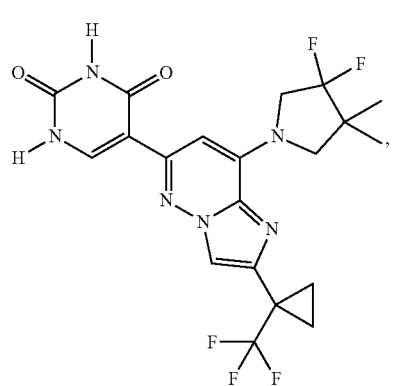
176
-continued
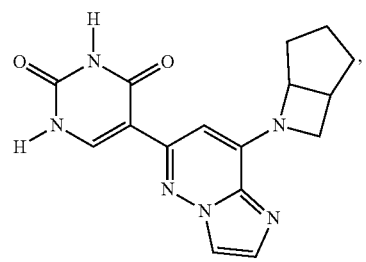
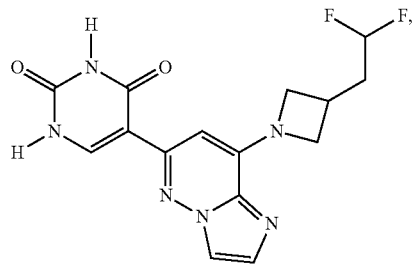 [SMILES: O=c1[nH]cc(-c2cc(N3CC(CC(F)F)C3)c3nccn3n2)c(=O)[nH]1]
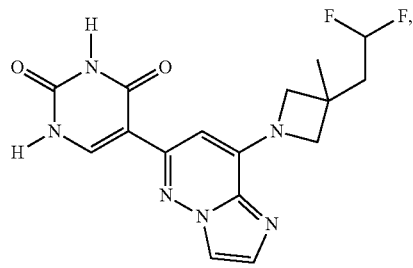
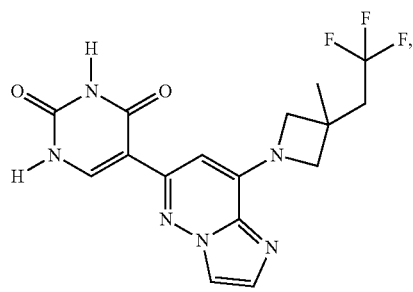
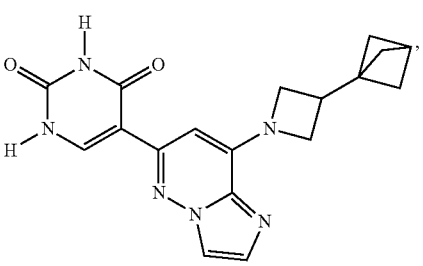
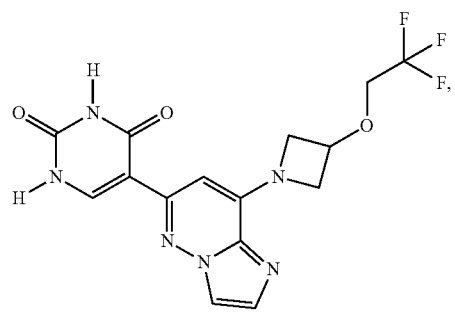

177
-continued
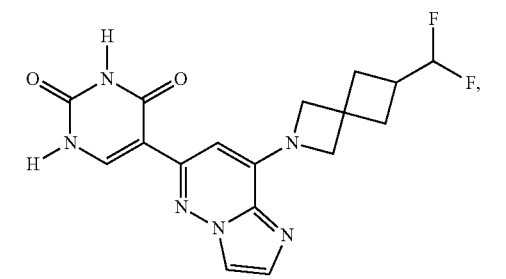
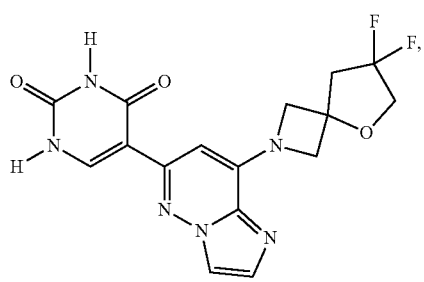
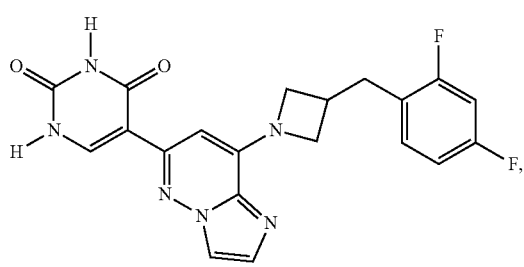
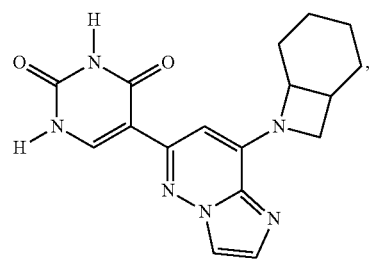
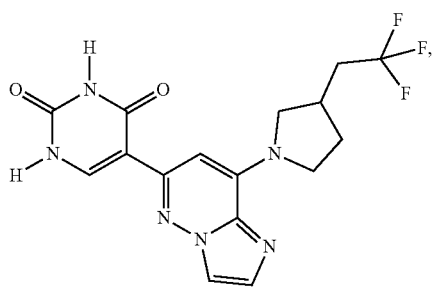
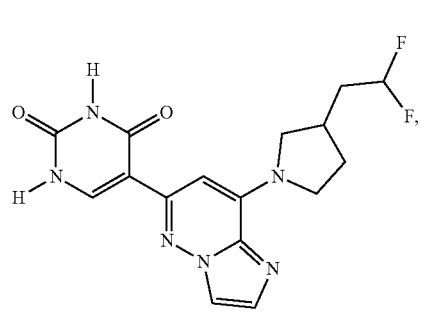
178
-continued
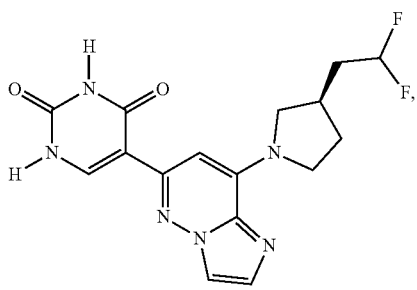
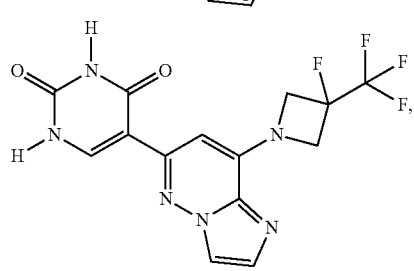
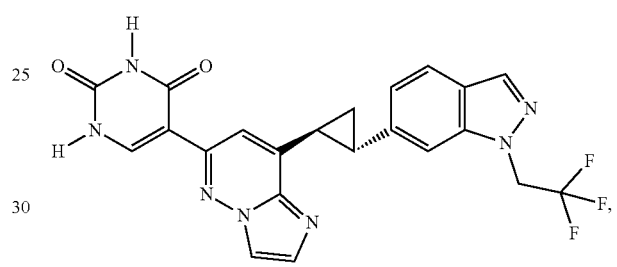

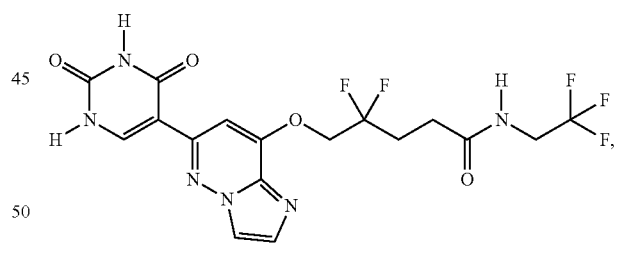
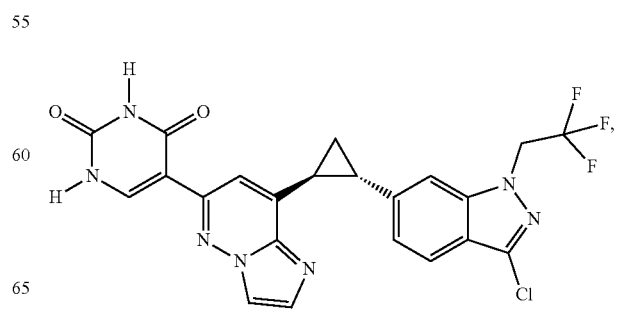

179
-continued
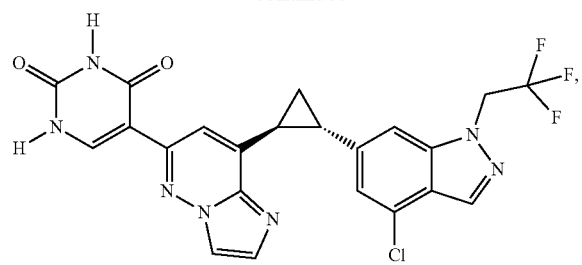
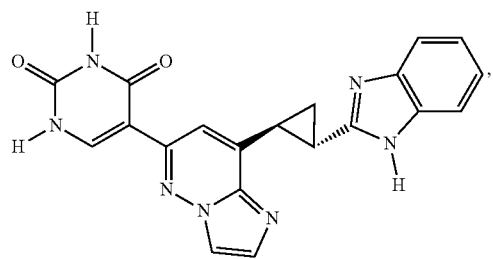
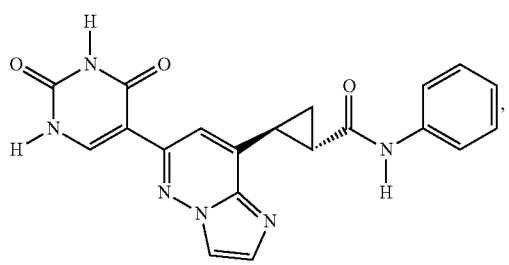
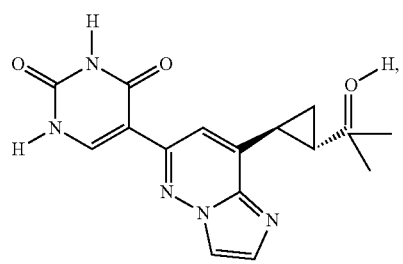
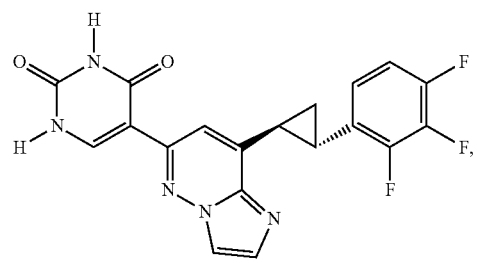
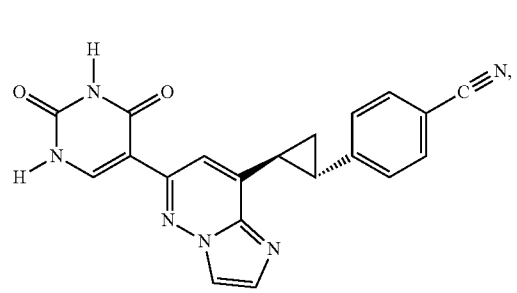
180
-continued
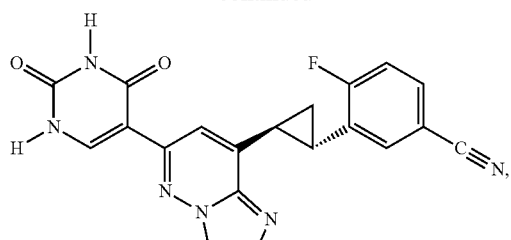
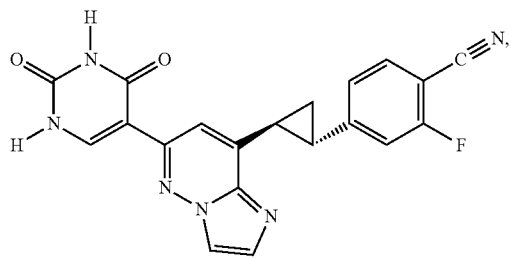
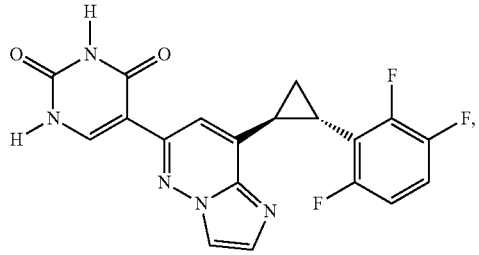
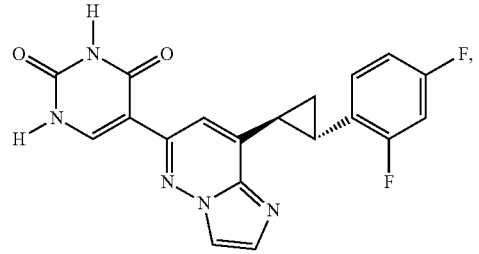
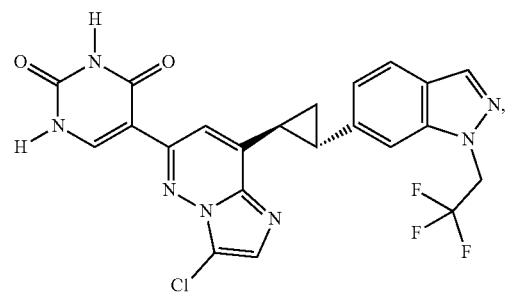
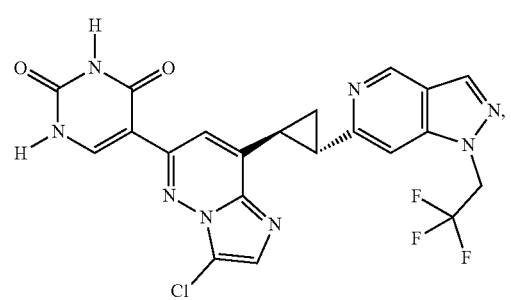

-continued
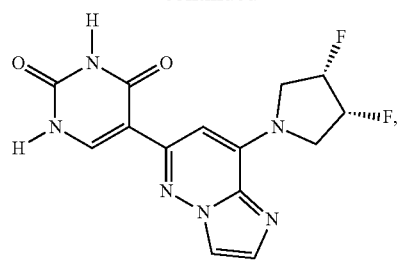
-continued
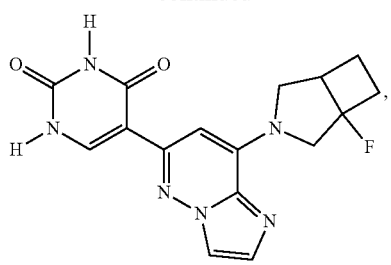

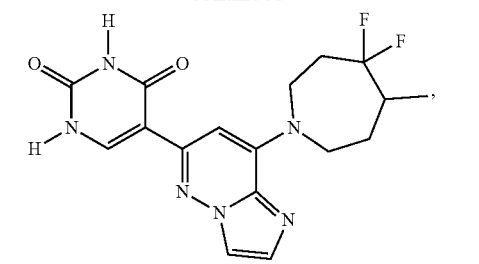
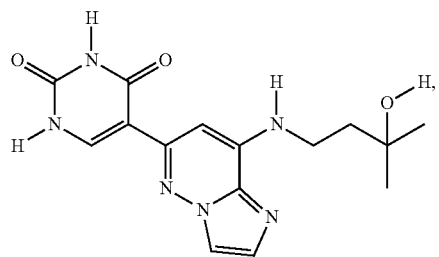
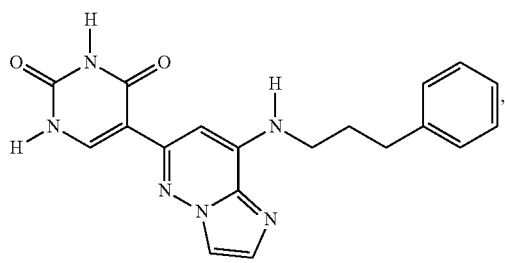
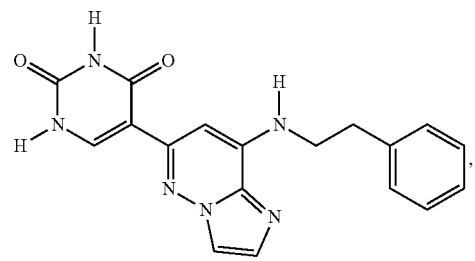
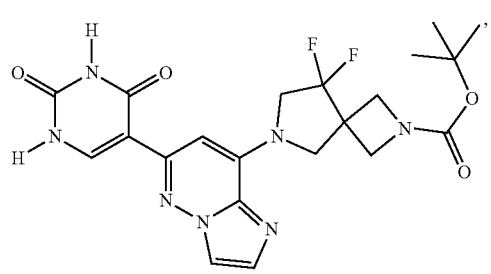
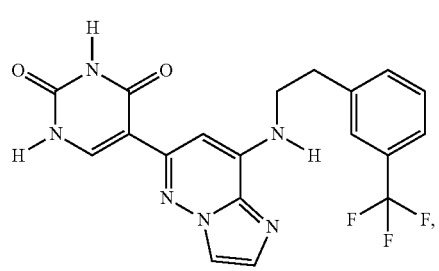
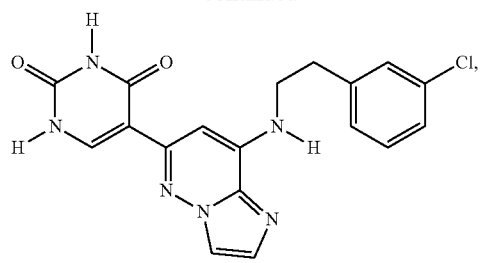
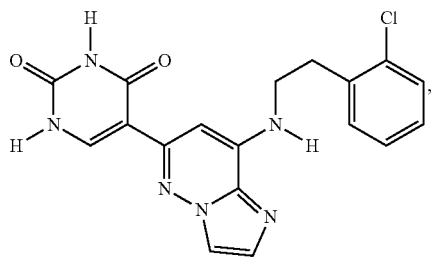
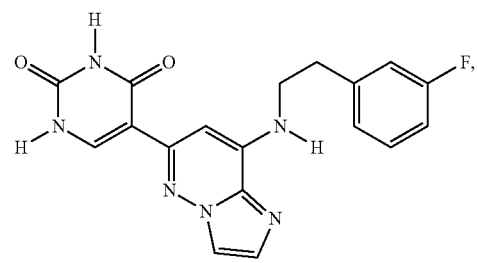
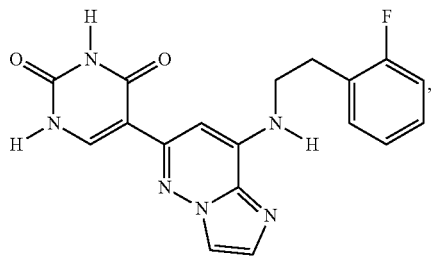
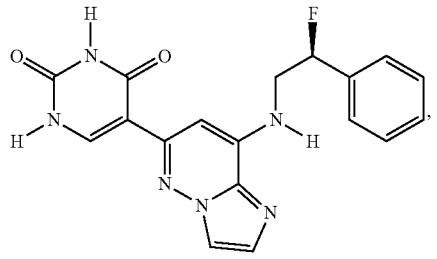
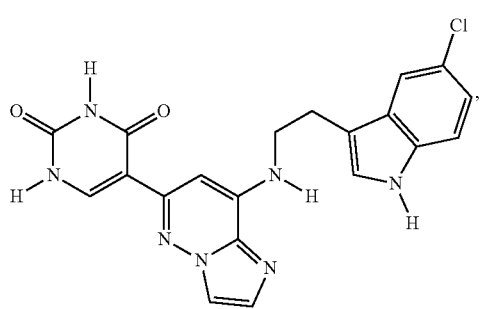

-continued
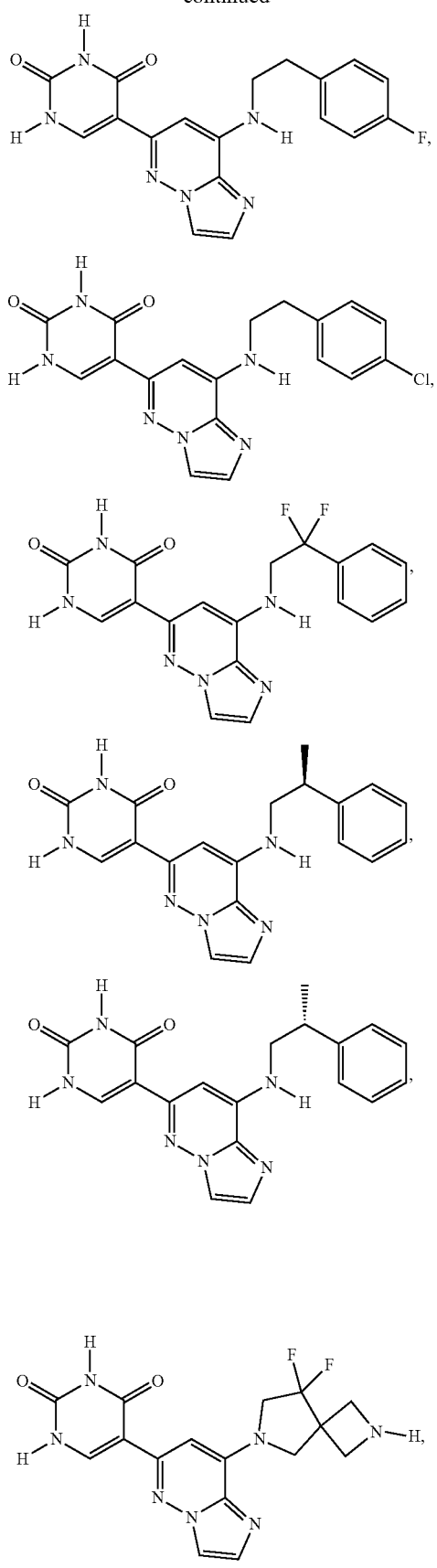
-continued
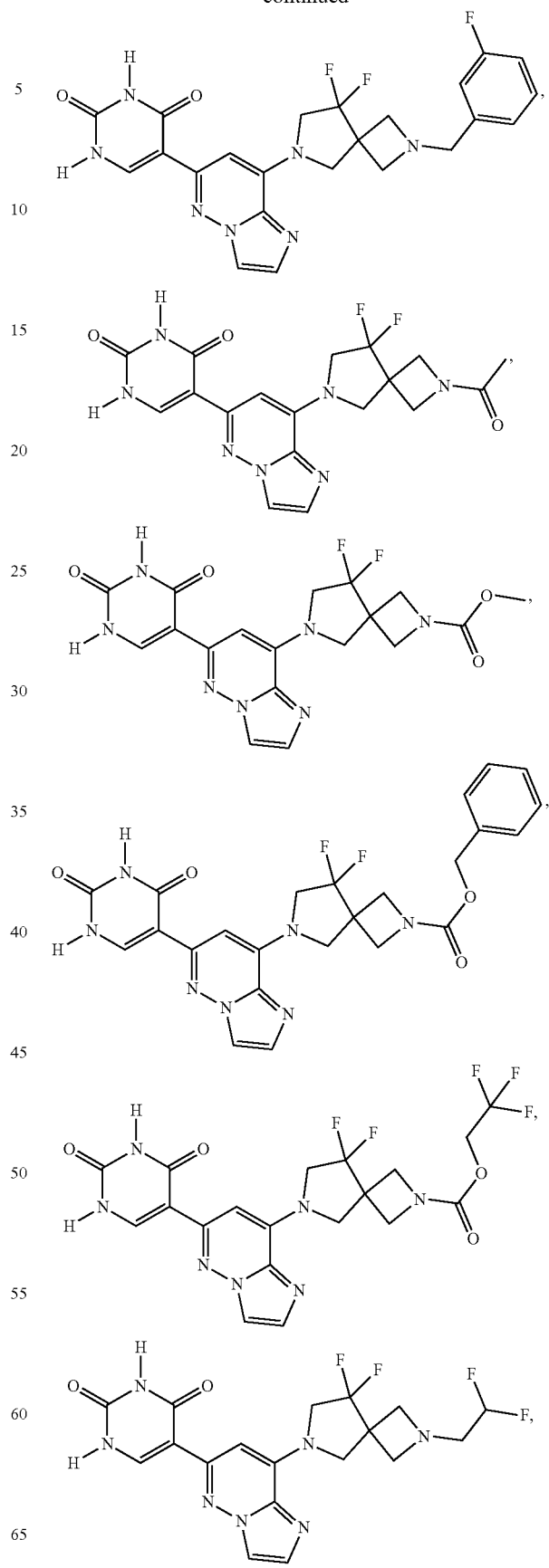

187
-continued
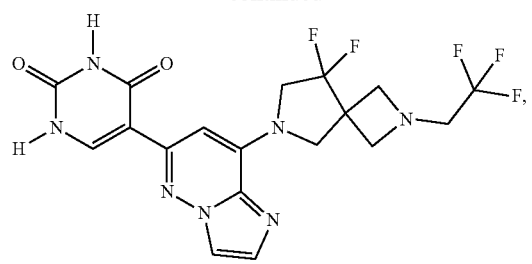
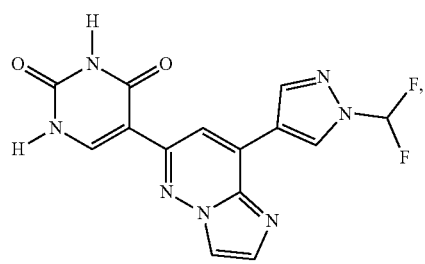
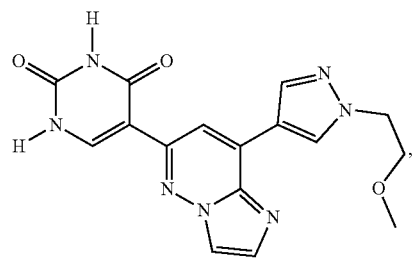
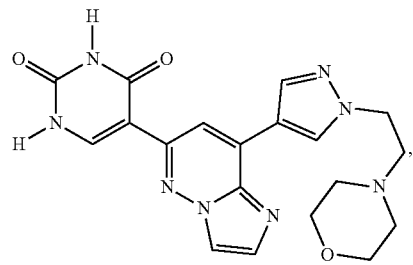
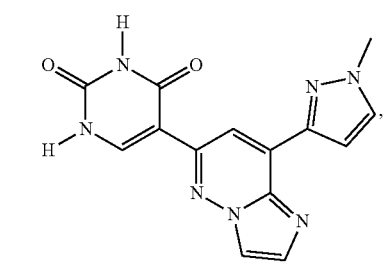
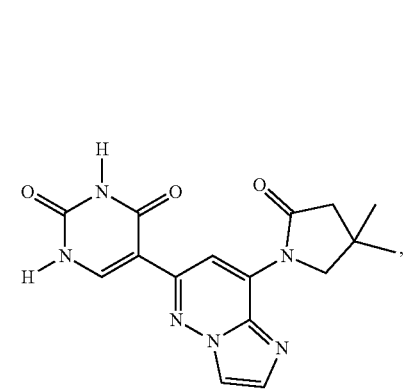
188
-continued
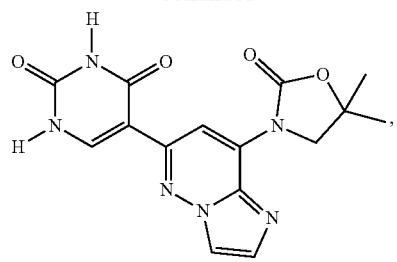
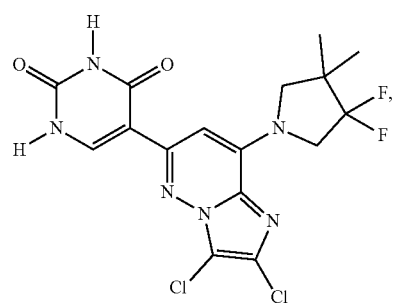
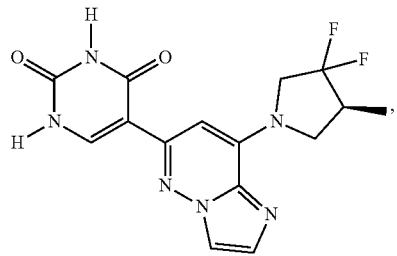
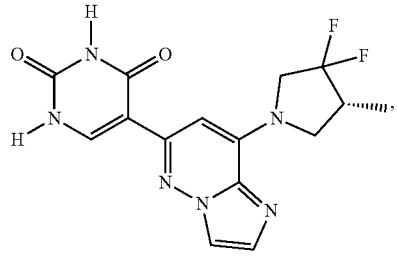
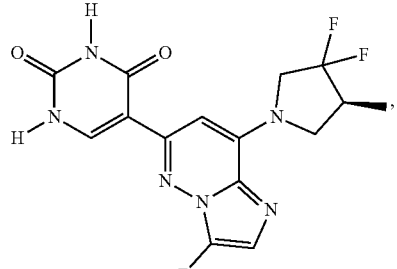
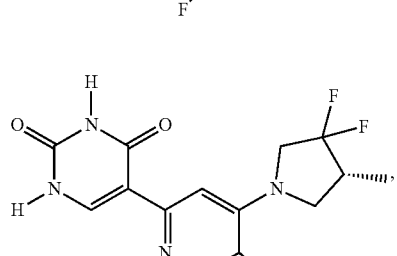

189
-continued
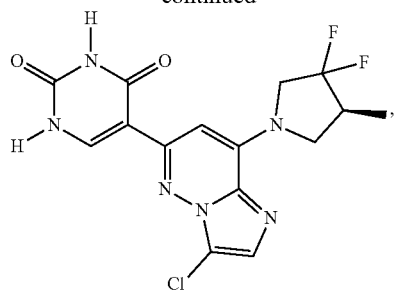
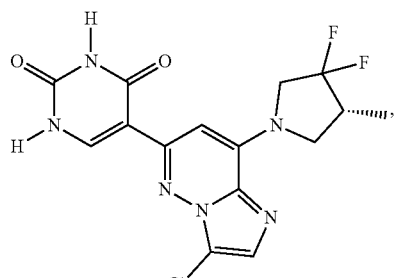
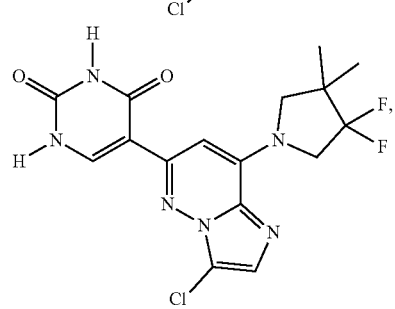
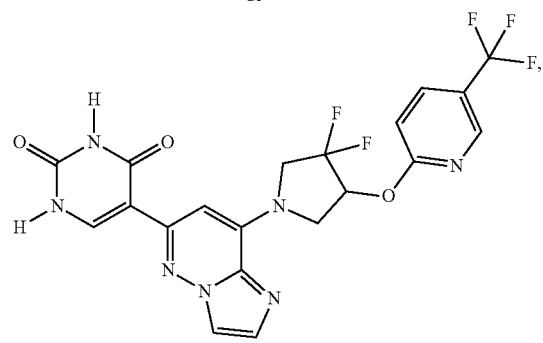
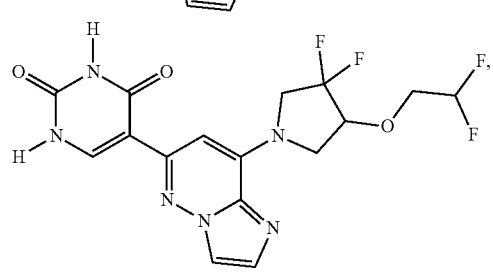
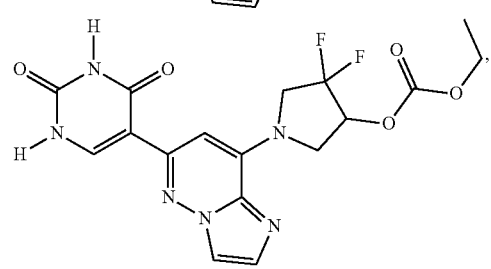
190
-continued
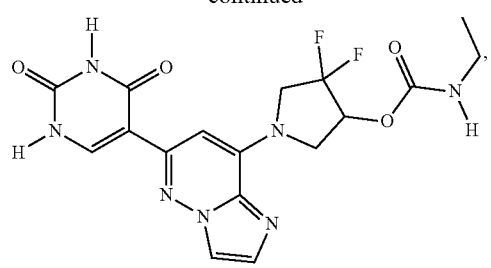
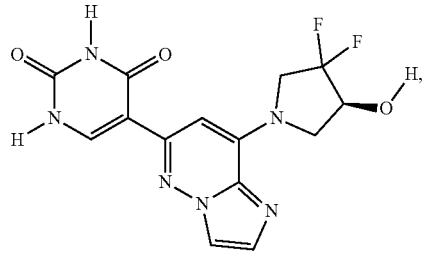
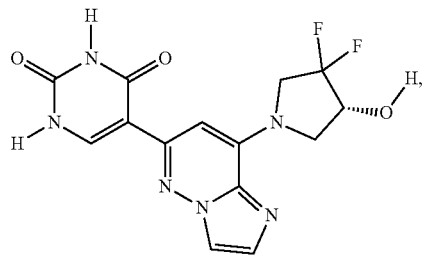
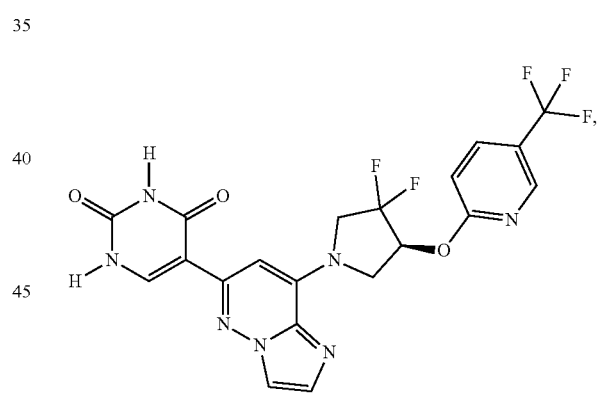
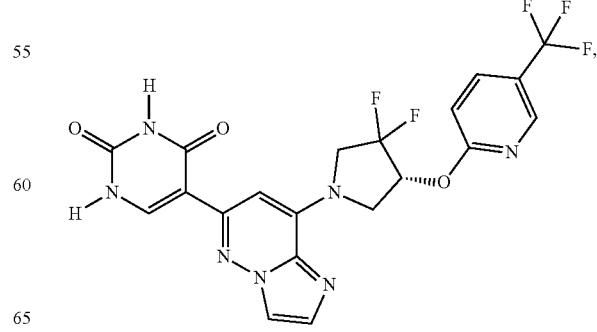

191
-continued
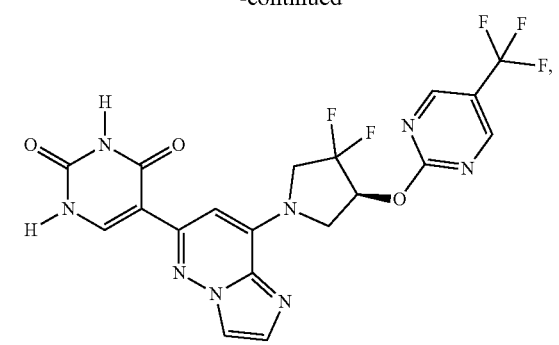
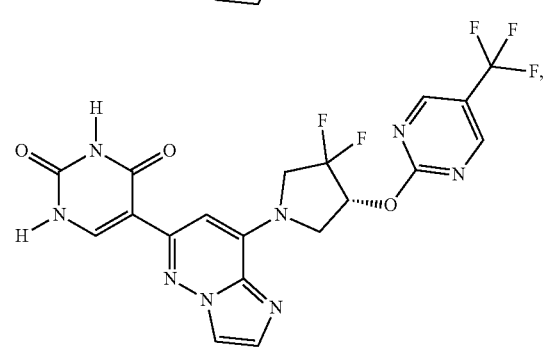
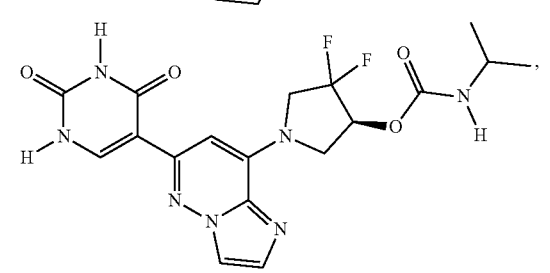
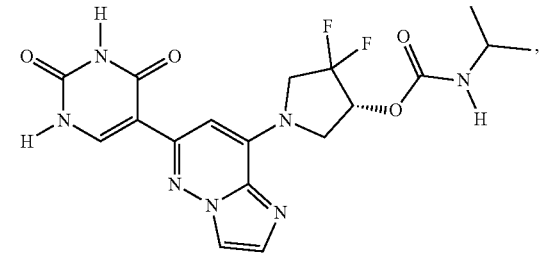
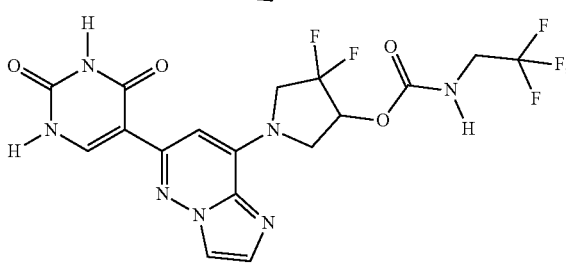
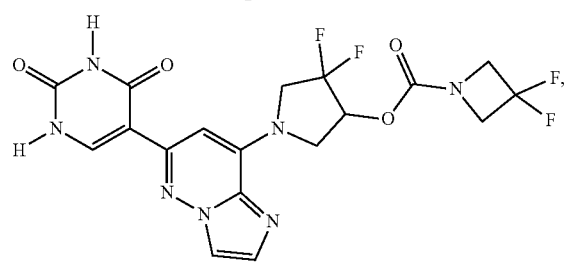
192
-continued
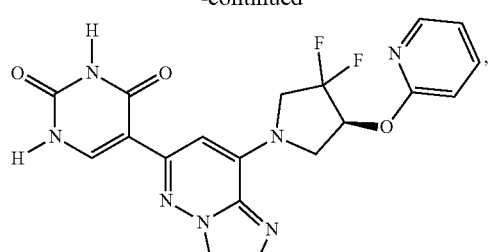
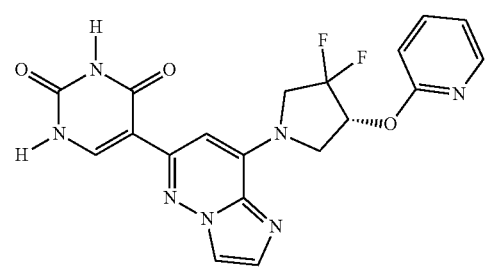
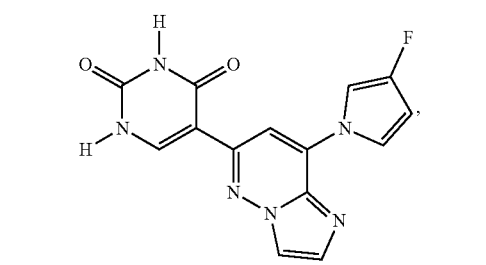
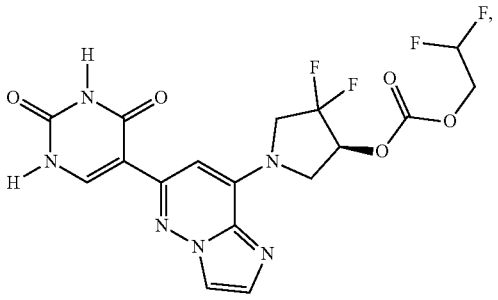
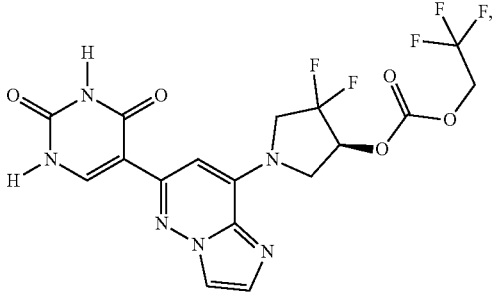
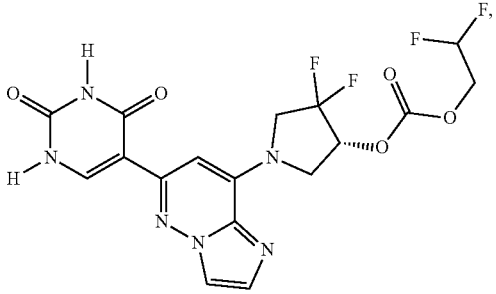

193
-continued
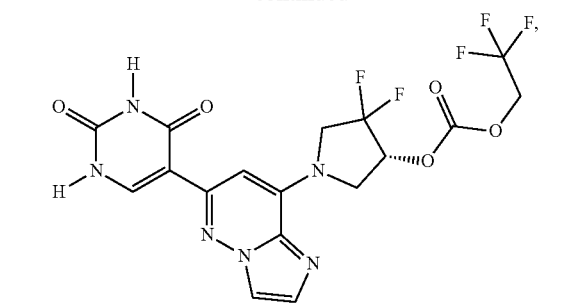
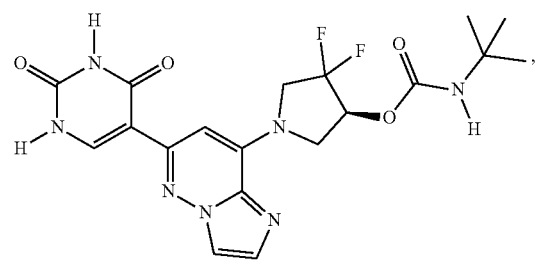
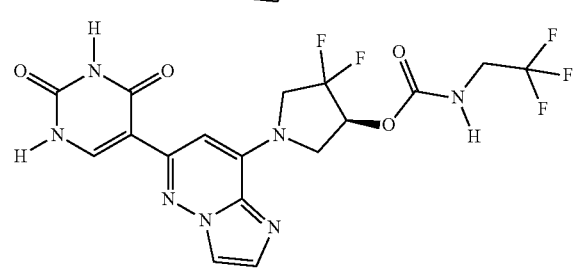
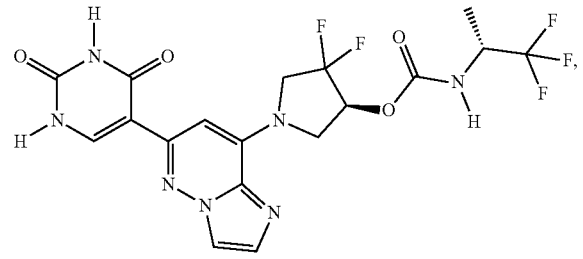
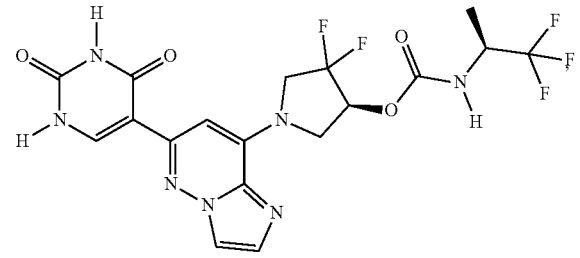
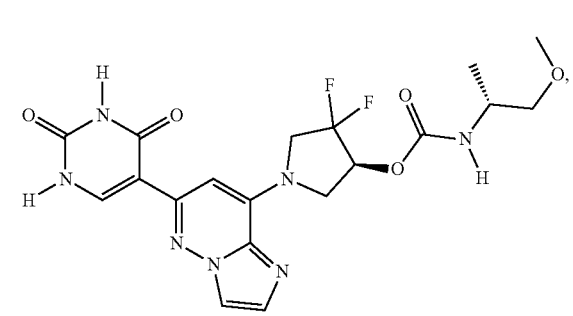
194
-continued
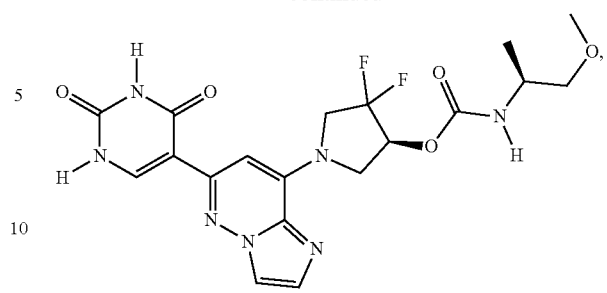
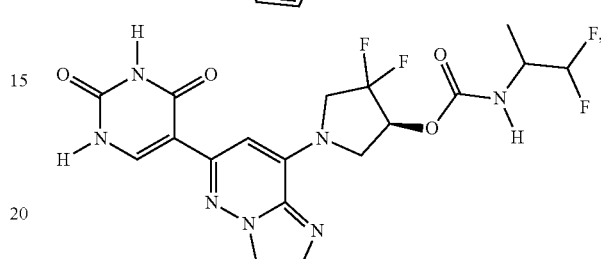
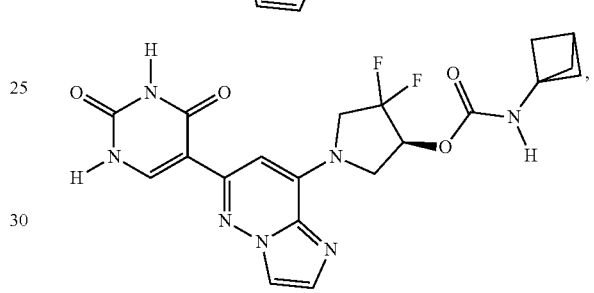
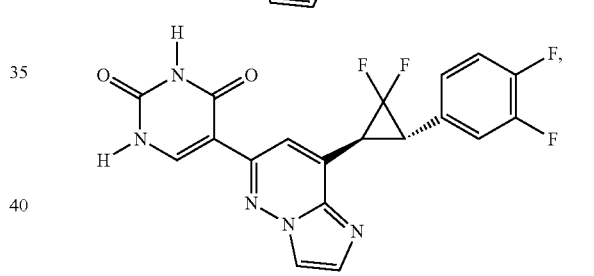

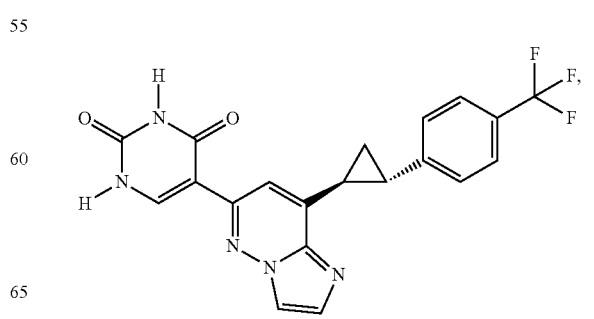

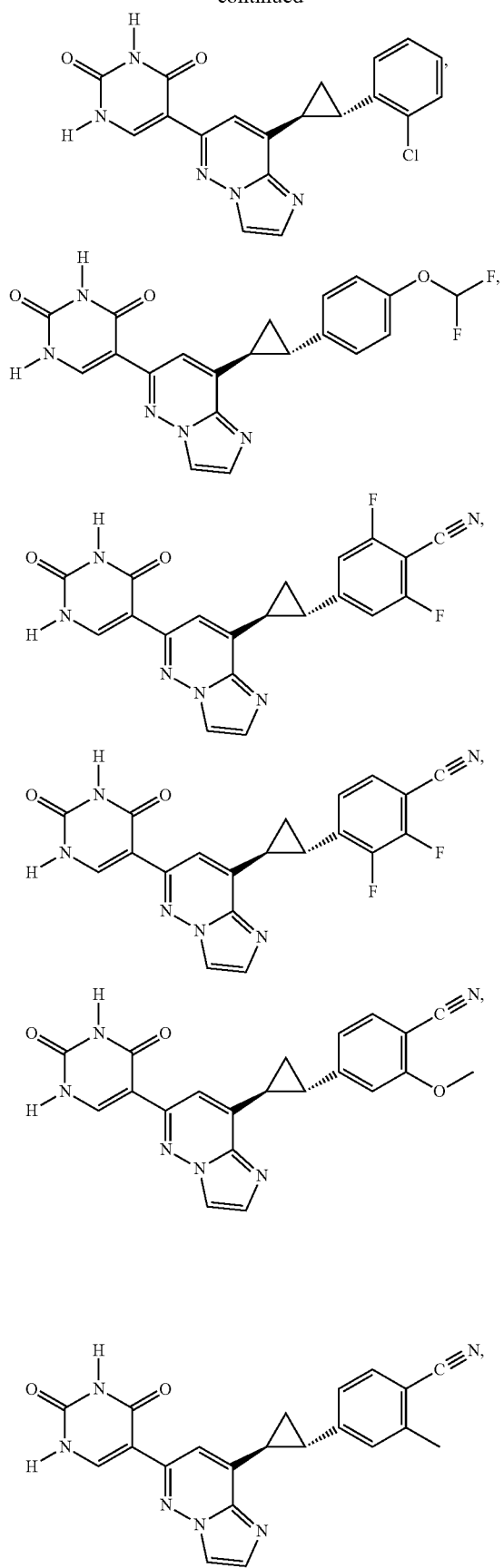
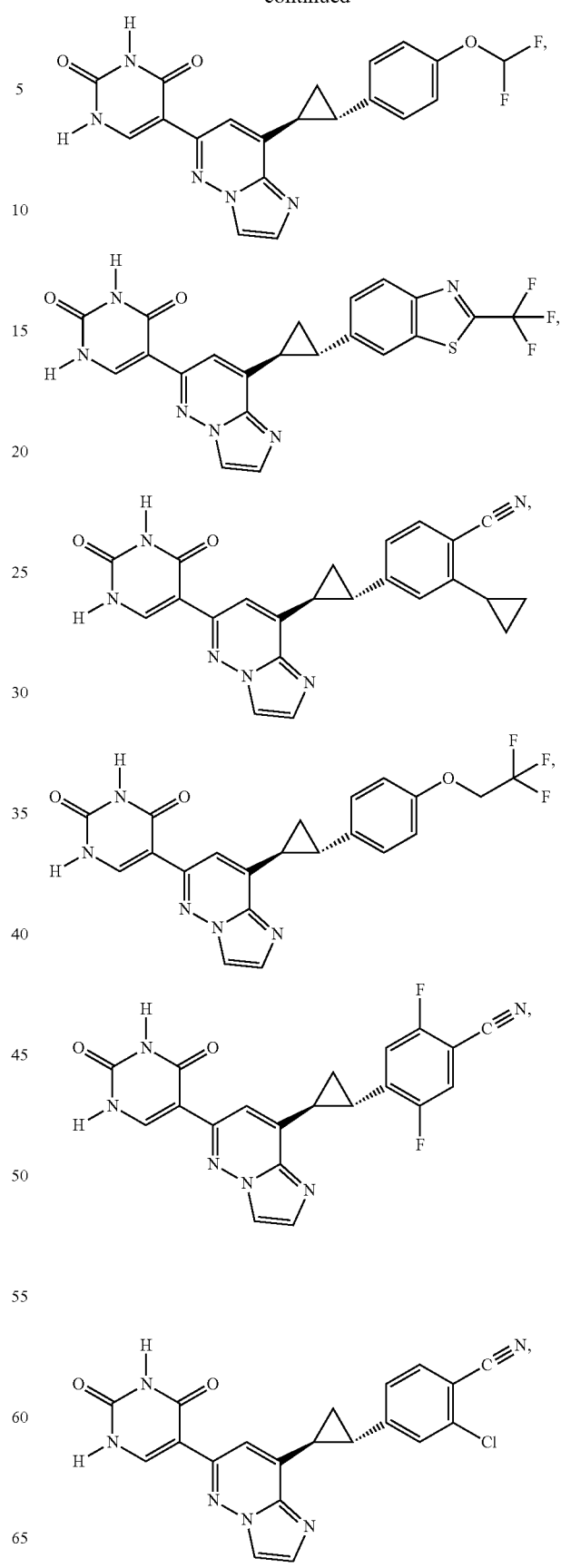

197
-continued
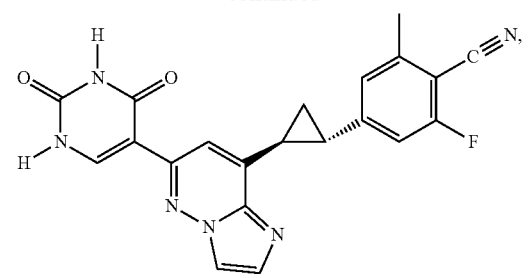
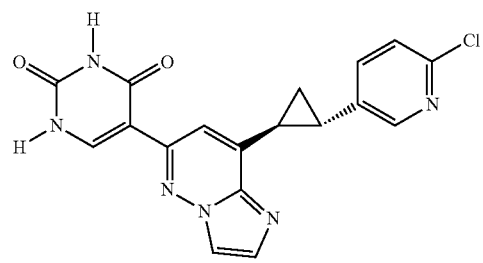
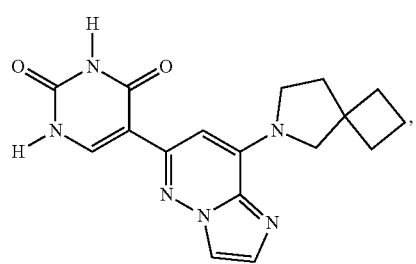
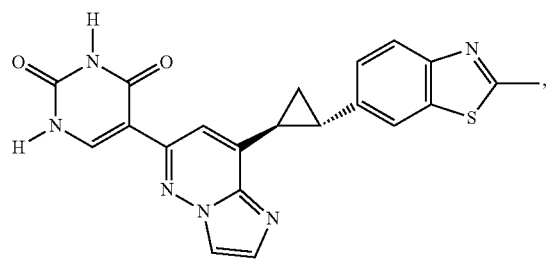
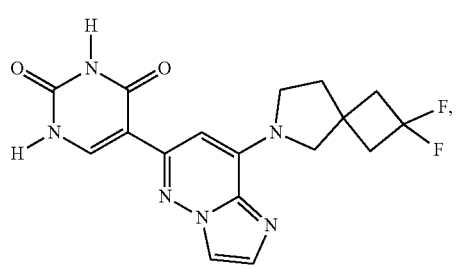
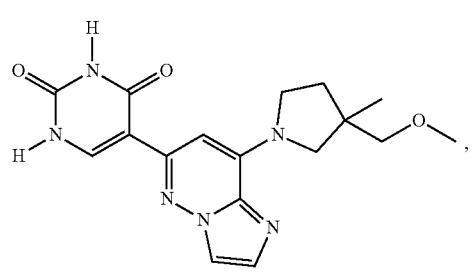
198
-continued
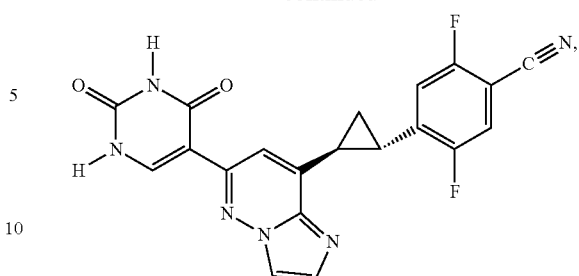
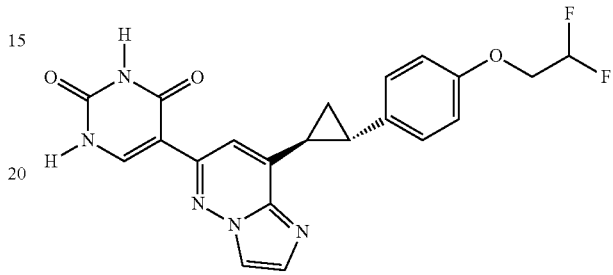
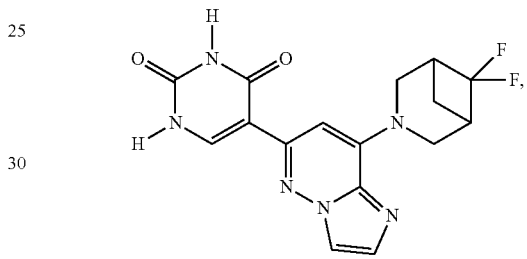
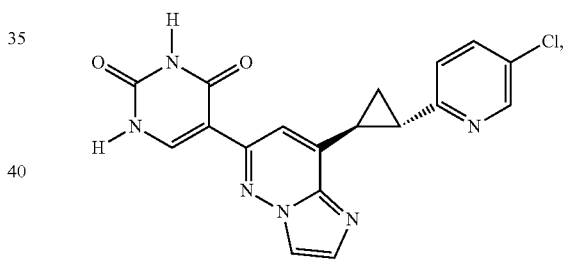
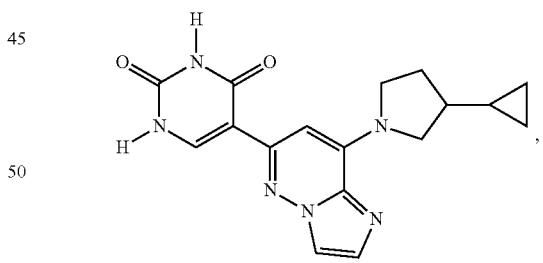
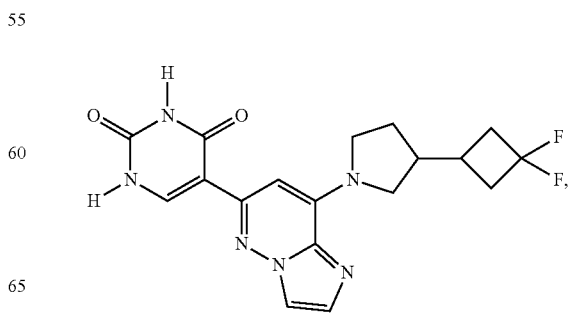

199
-continued
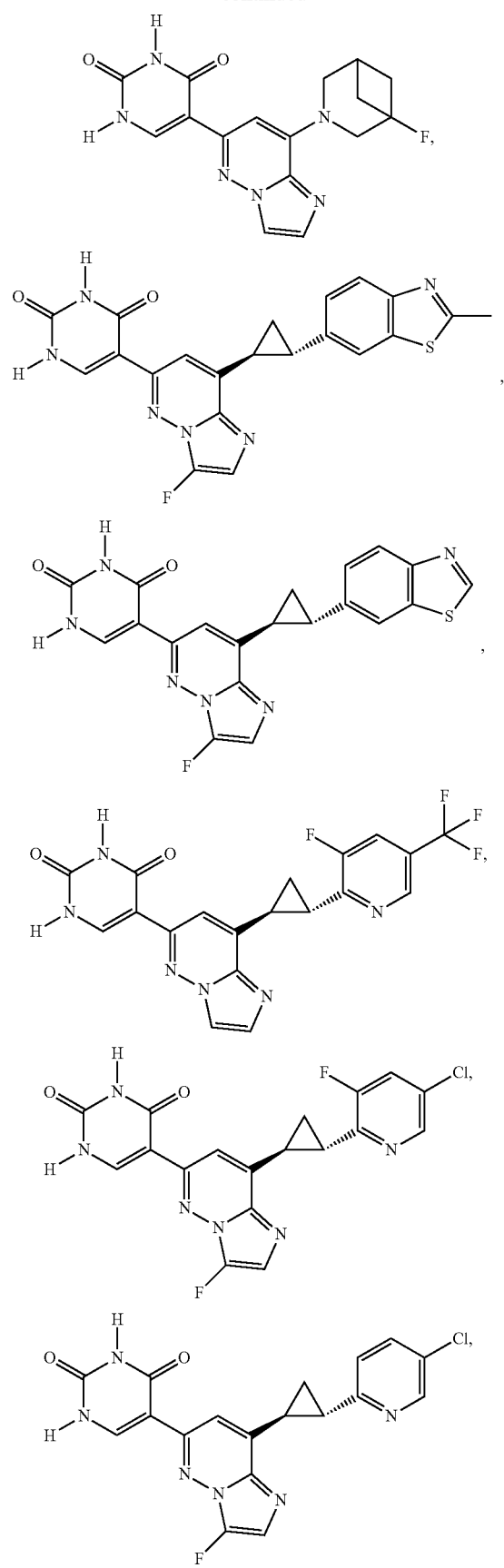
200
-continued
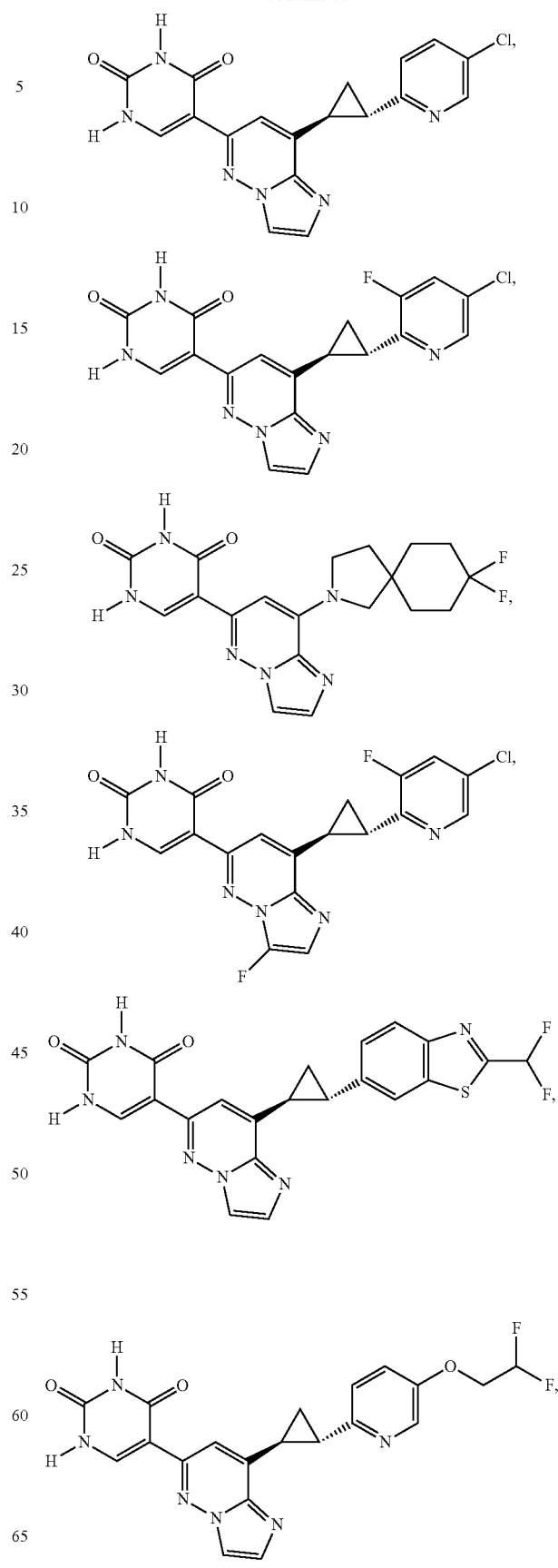

201
-continued
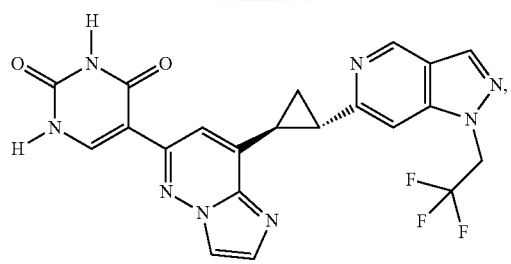
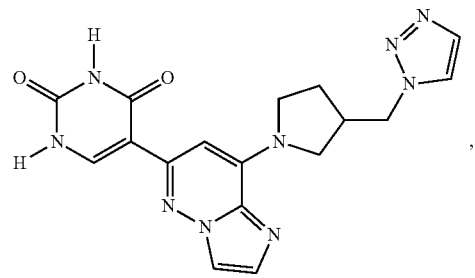
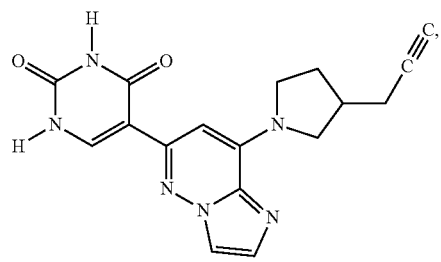
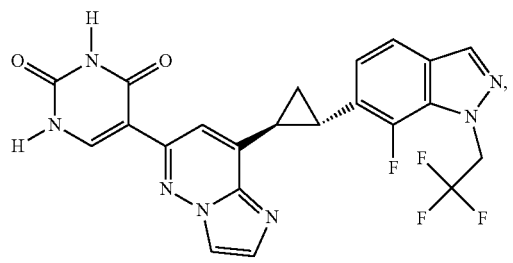
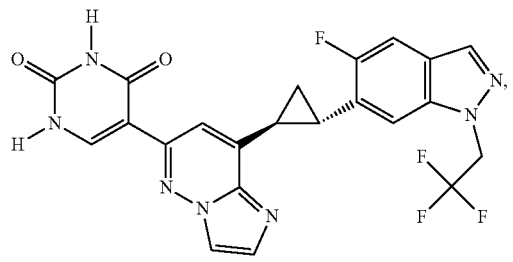
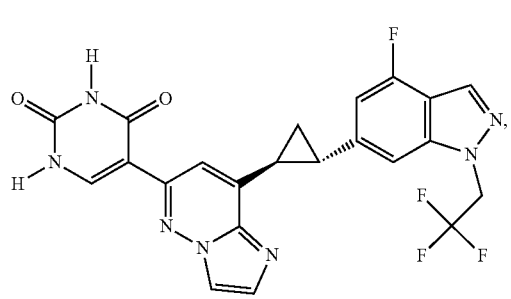
202
-continued
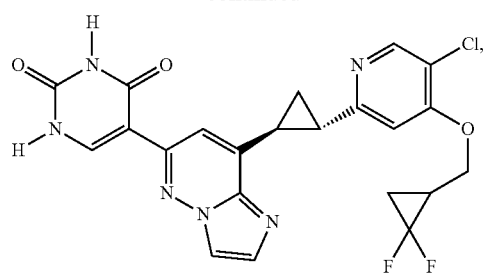
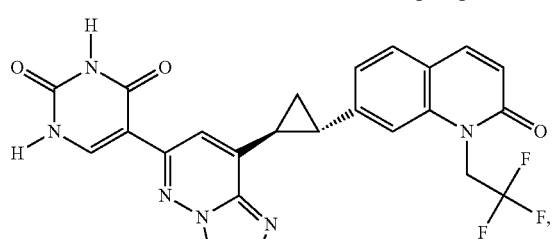
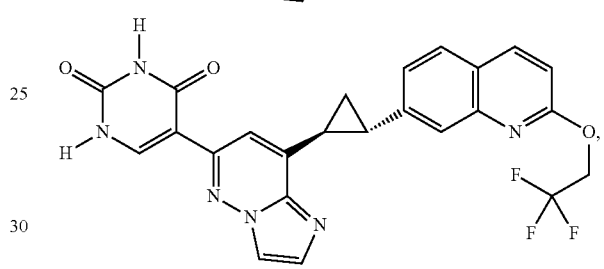
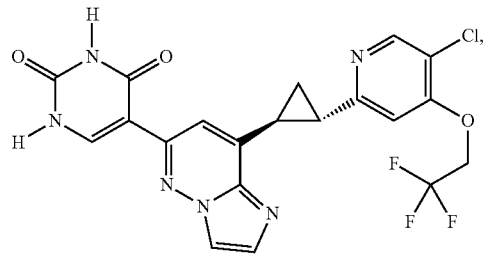
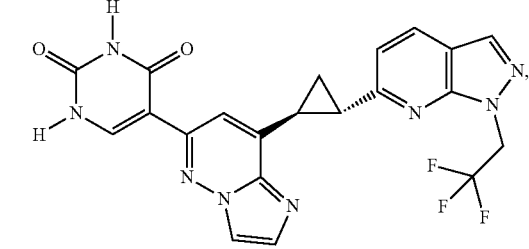
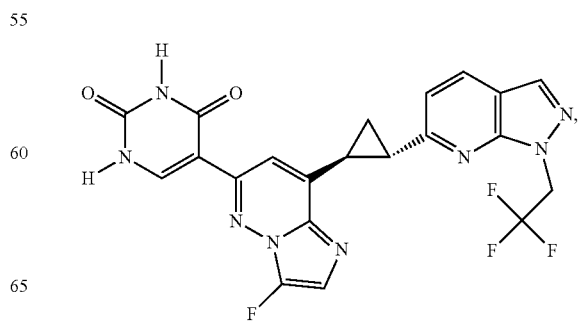

203
-continued
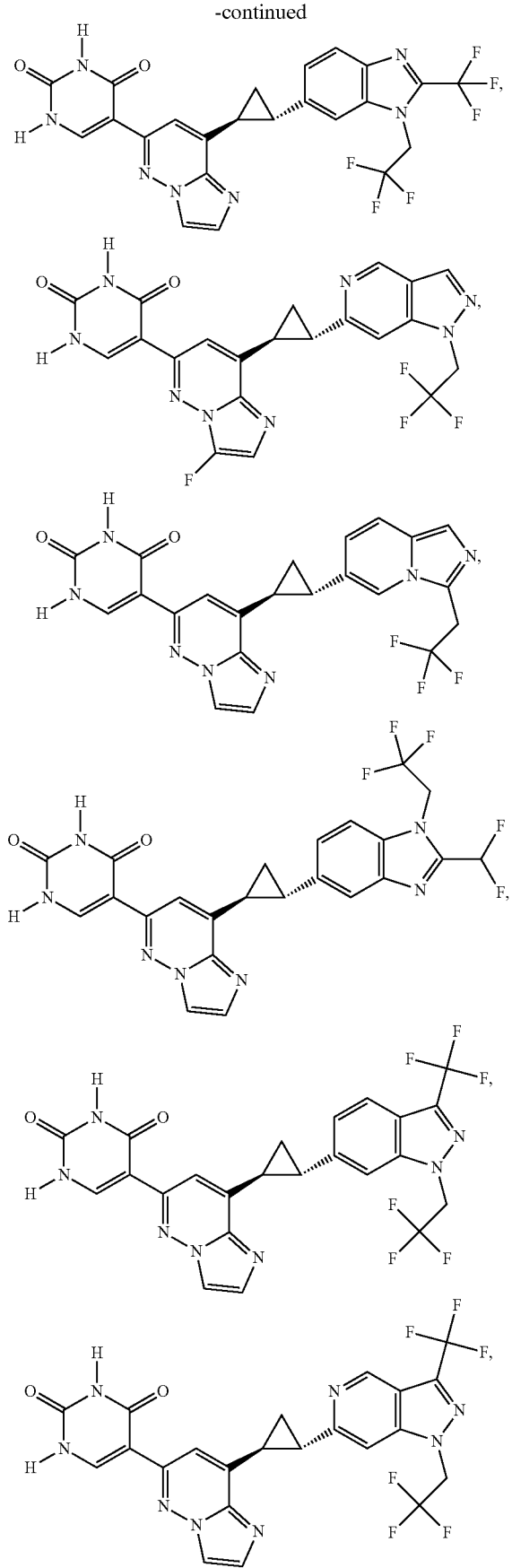
204
-continued
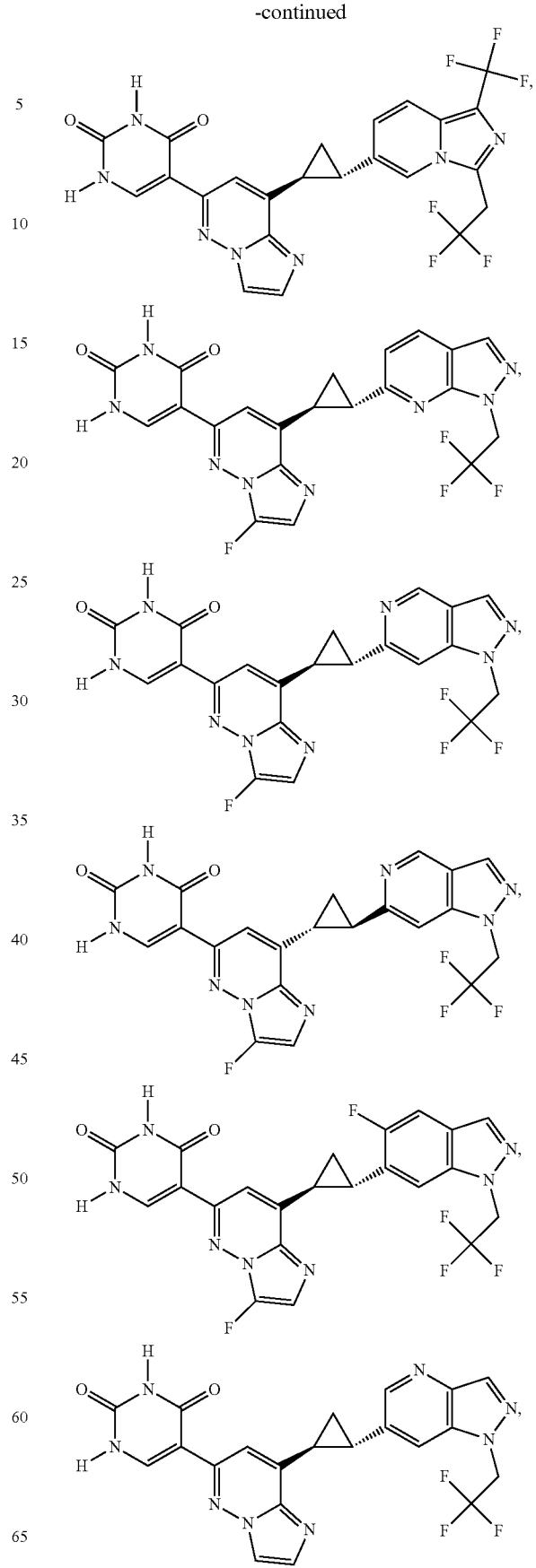

205
-continued
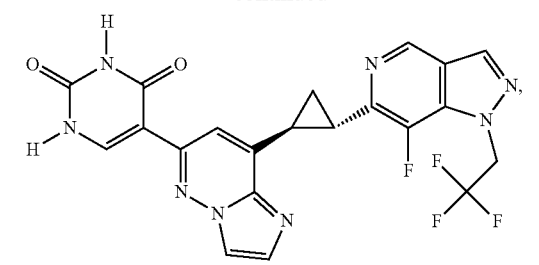
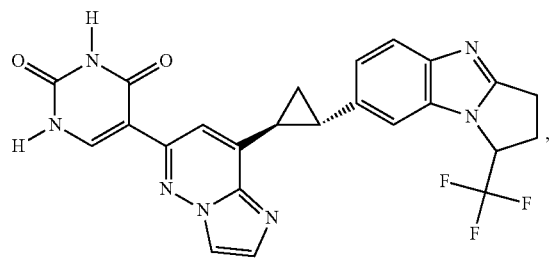
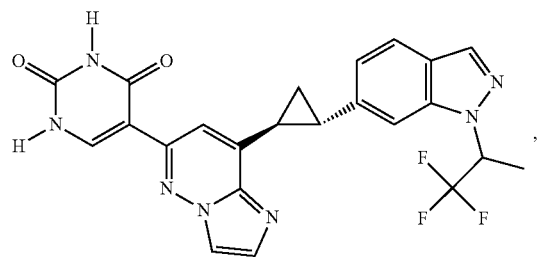
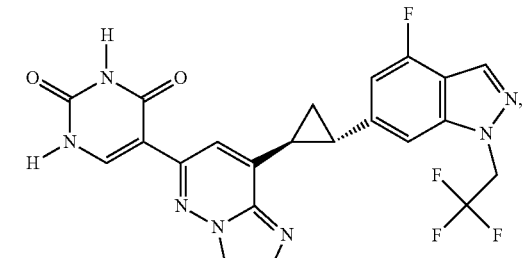
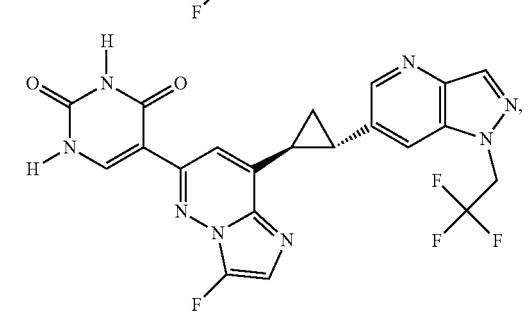
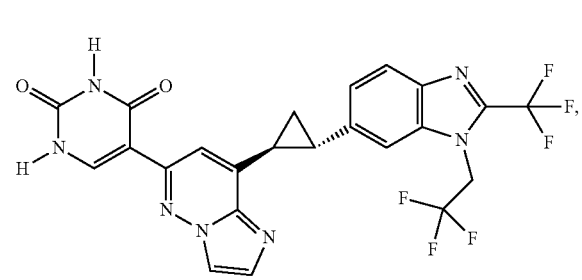
206
-continued
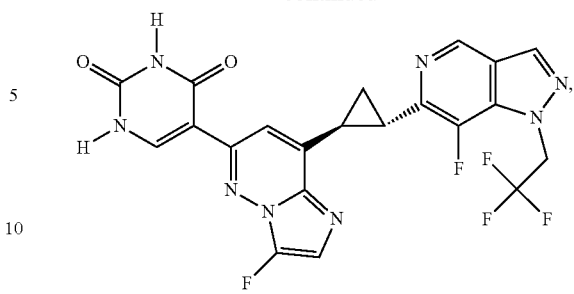
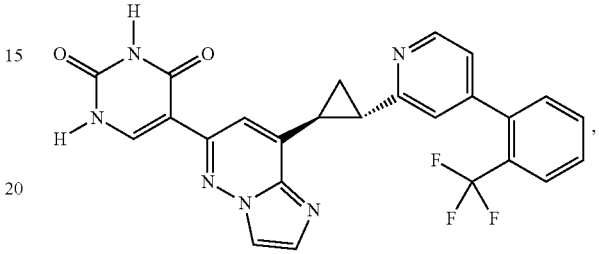
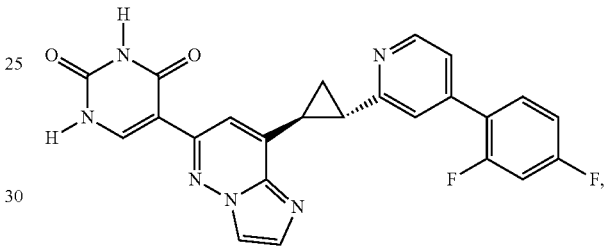
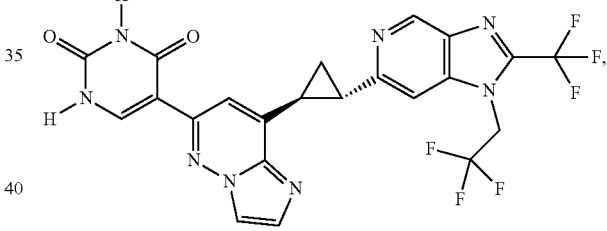
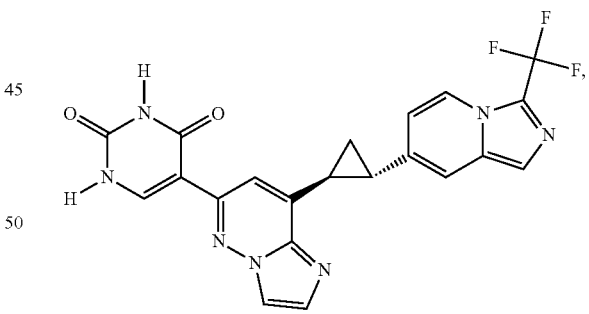
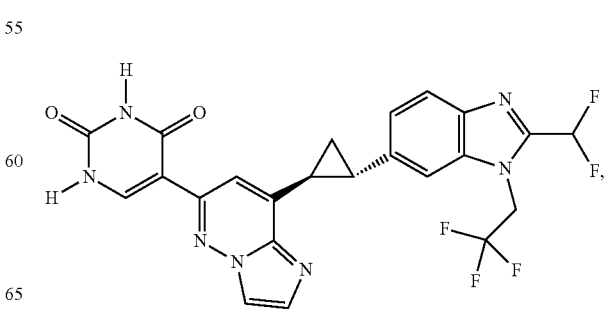

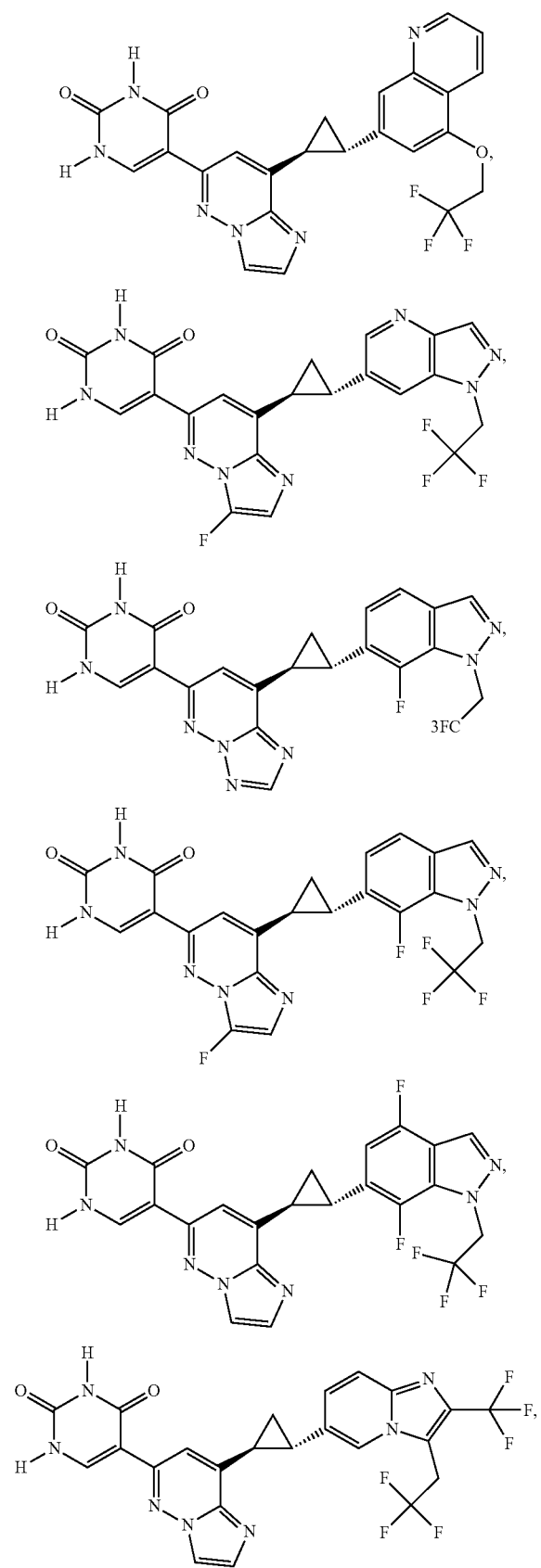
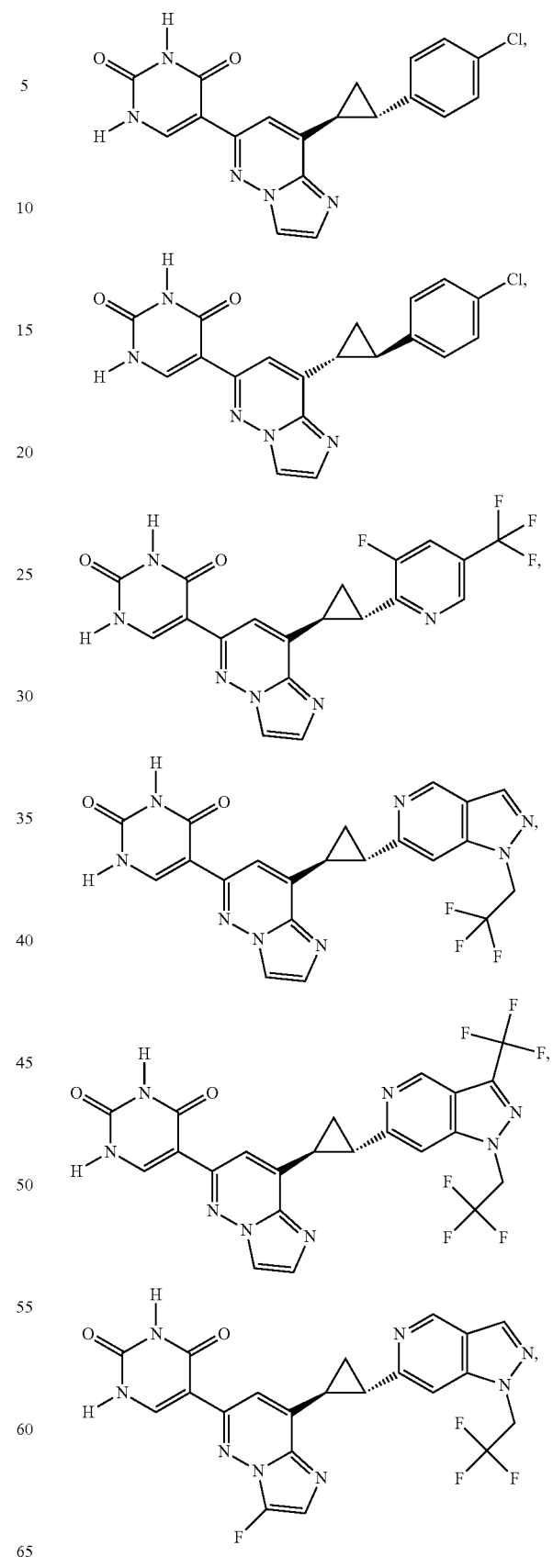

-continued
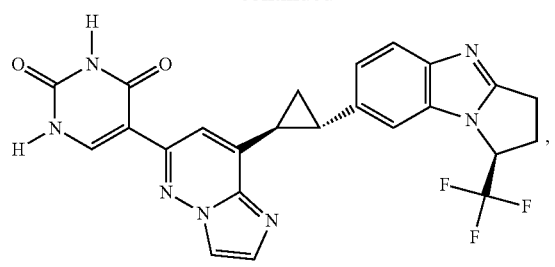
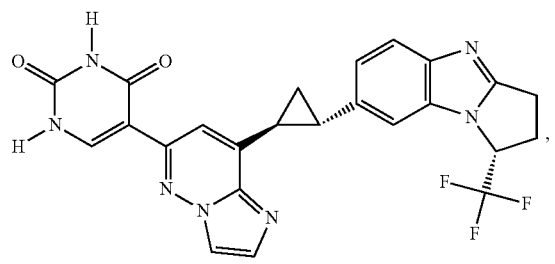
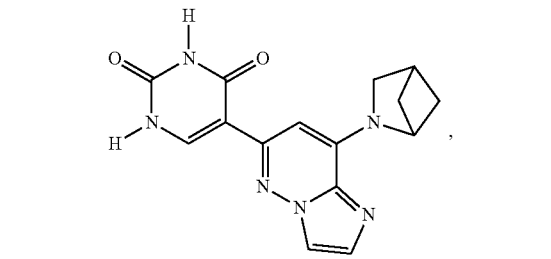
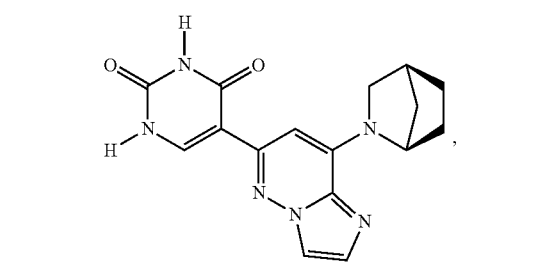
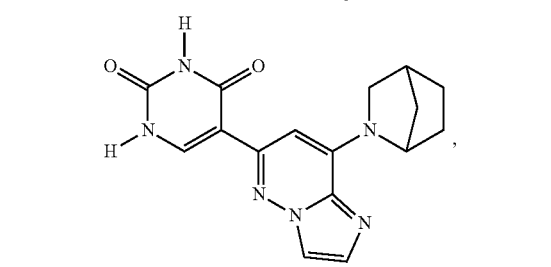
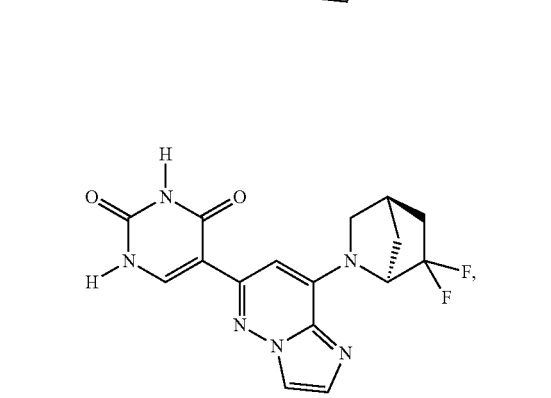
-continued
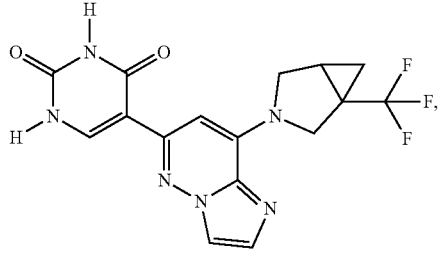
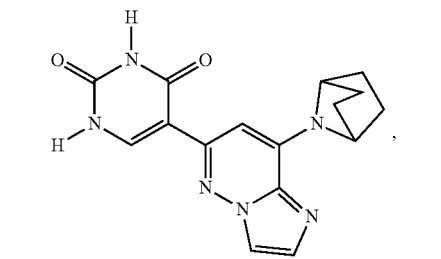
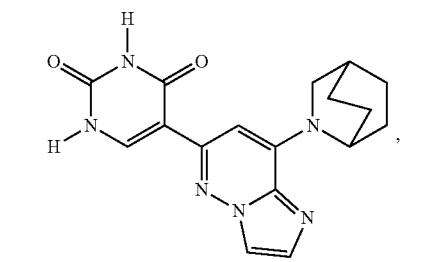
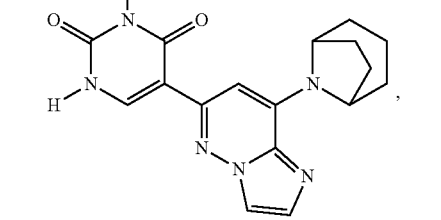
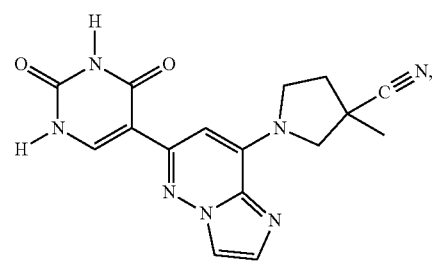
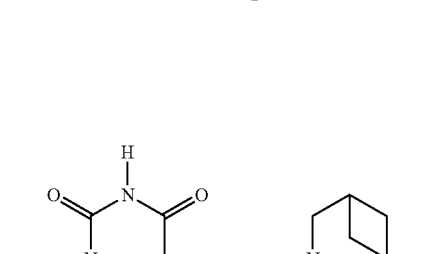

211
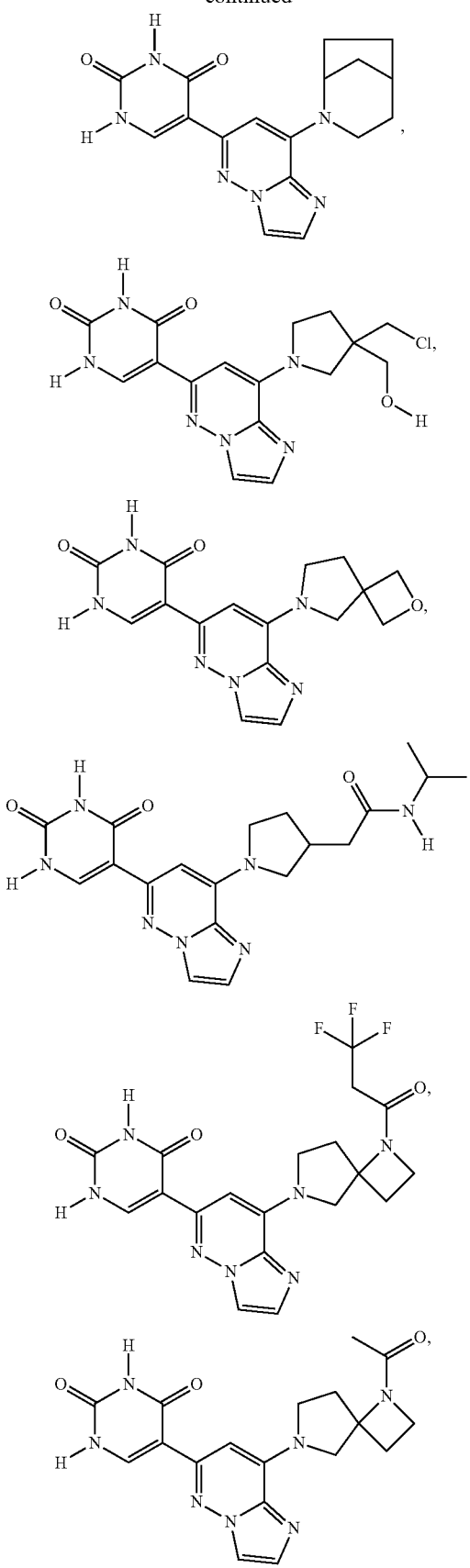
212
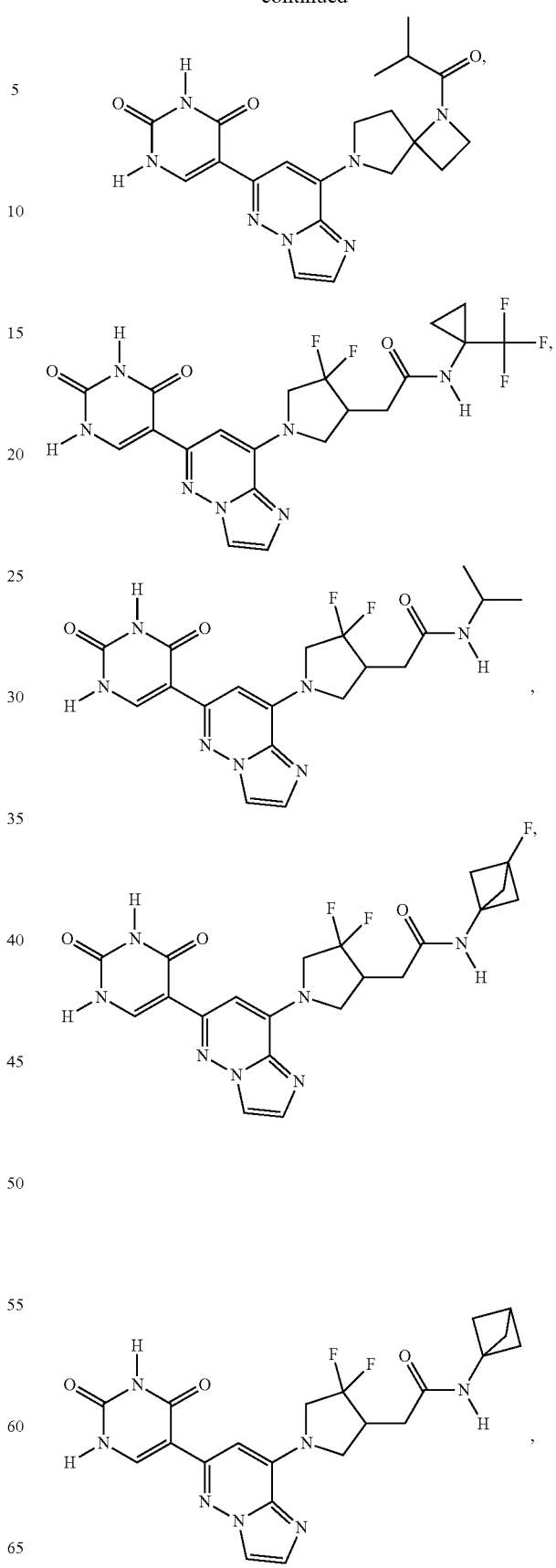

213
-continued
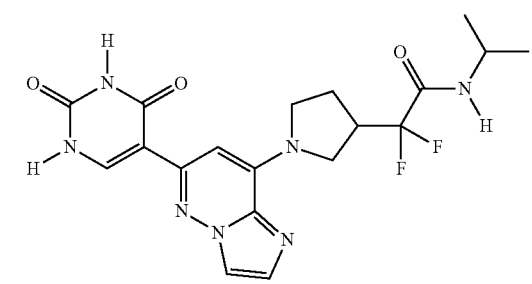
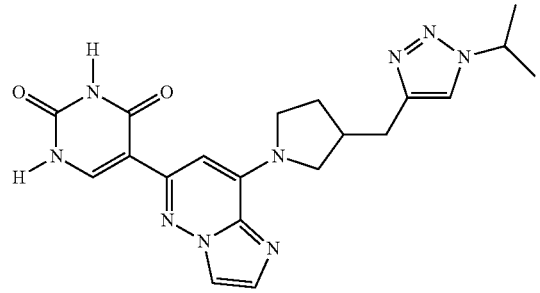
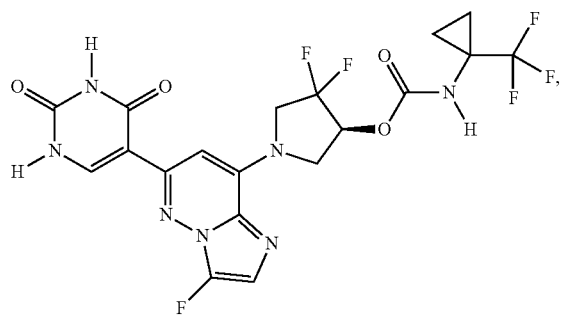
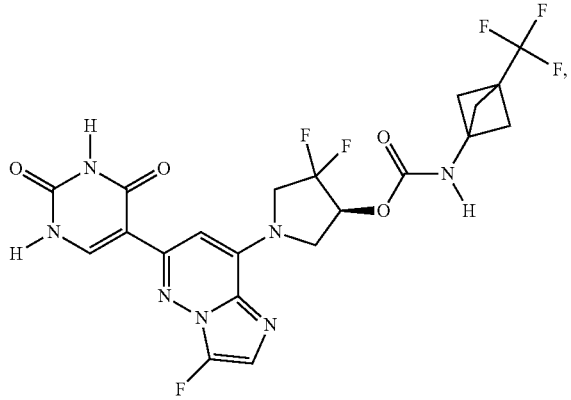
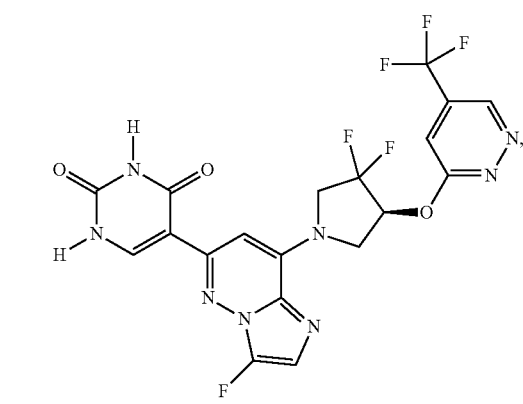
214
-continued
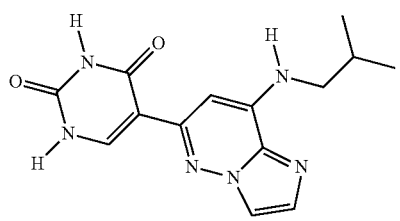
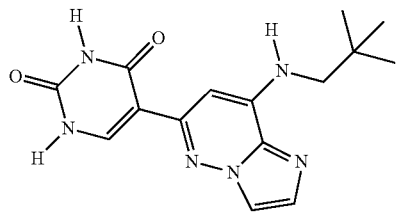
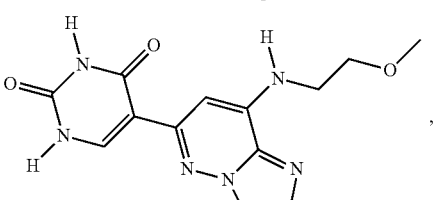
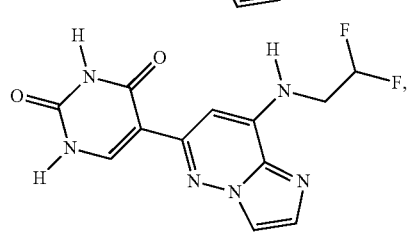
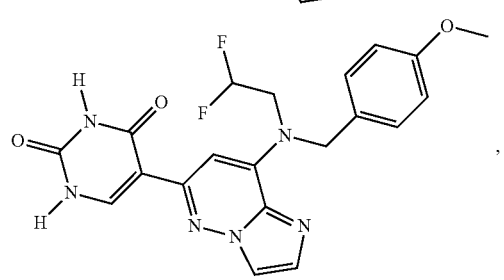
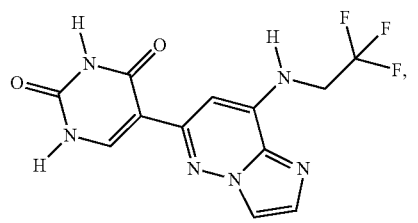
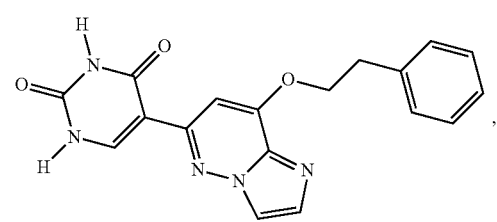

215
-continued
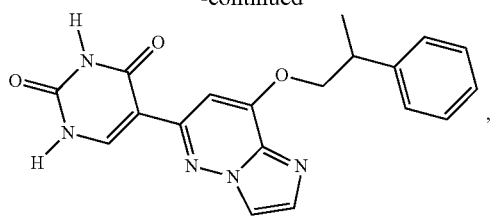
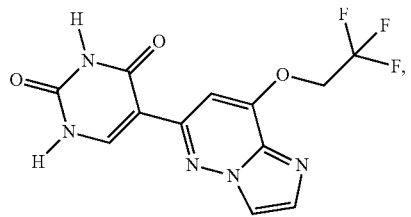
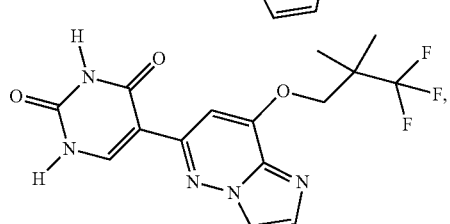
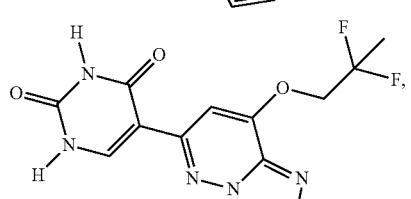
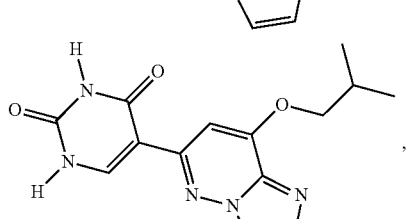
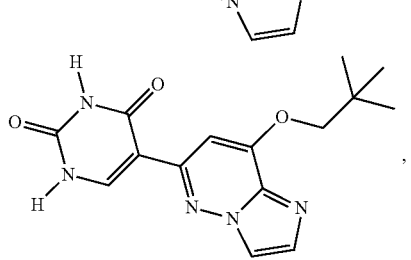
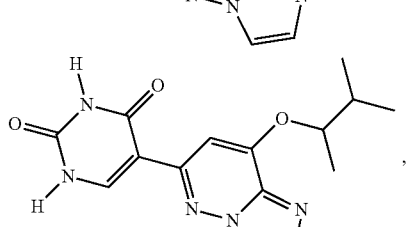
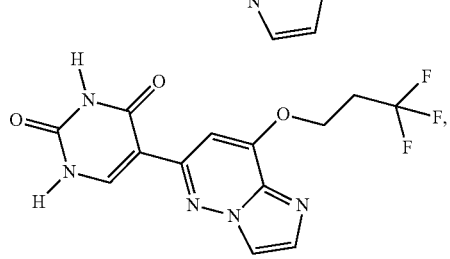
216
-continued
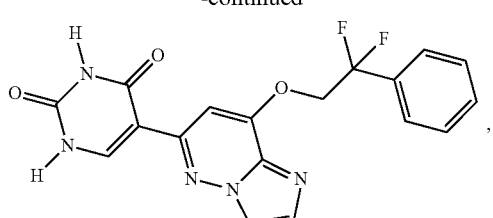
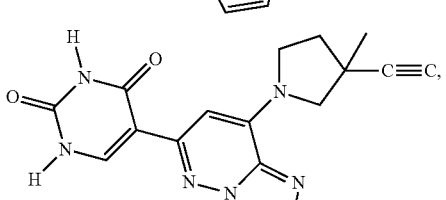
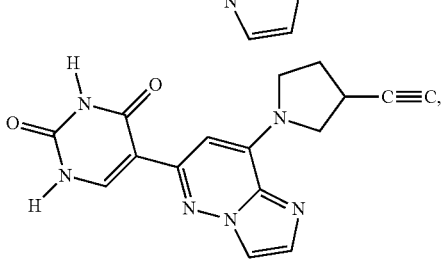
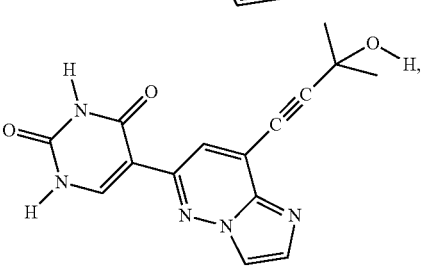
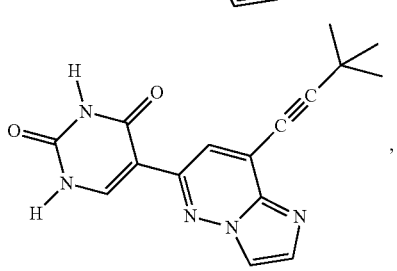
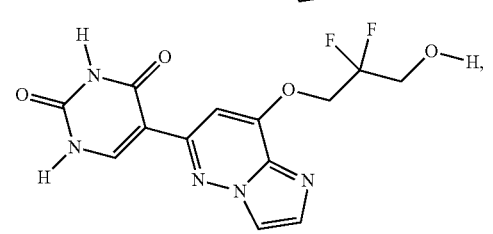
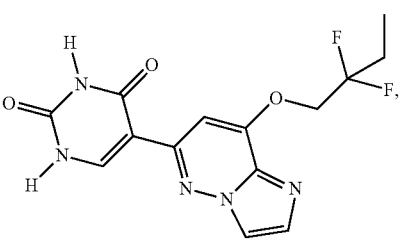

217
-continued
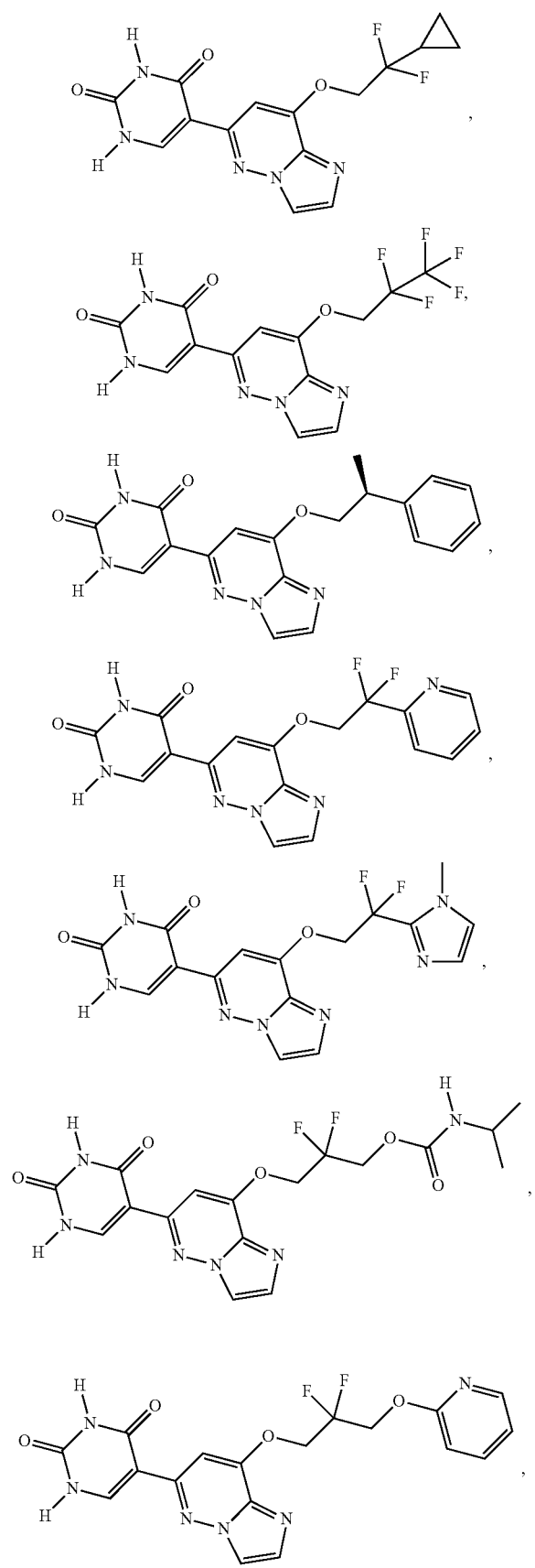
218
-continued
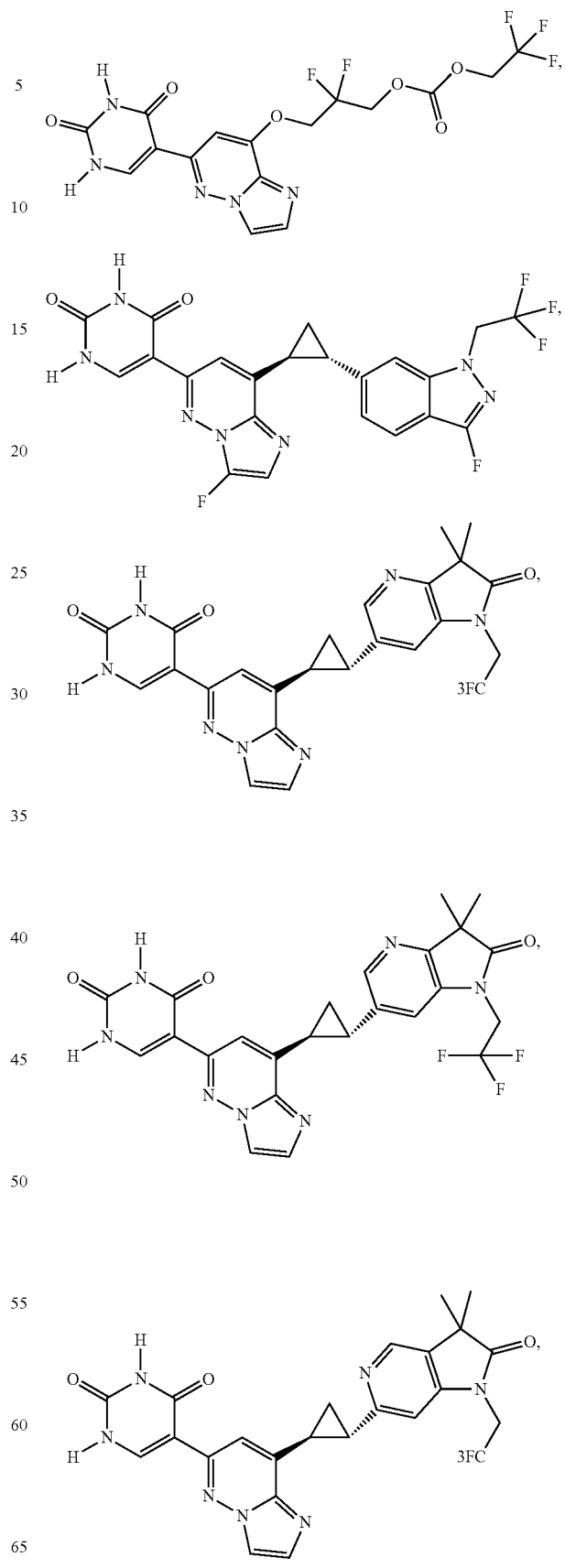

-continued
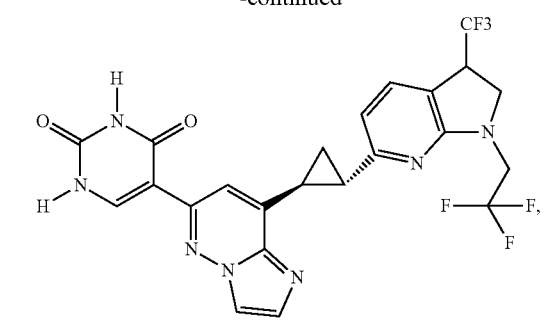
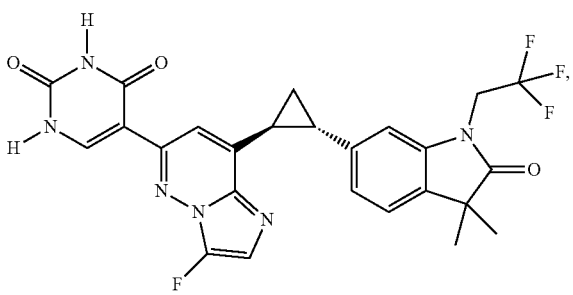
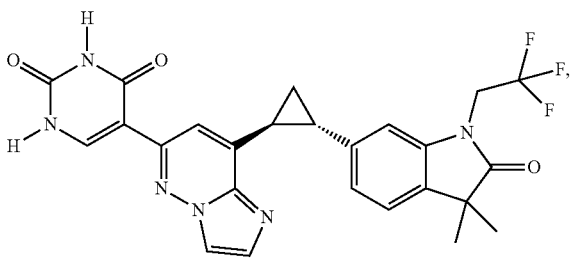
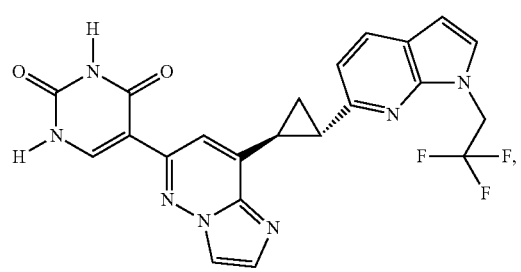
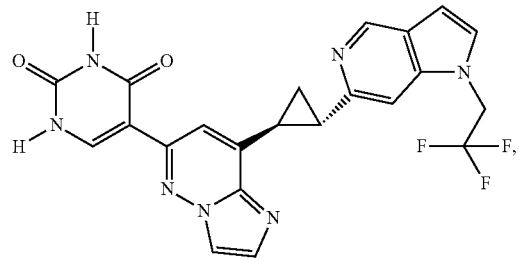
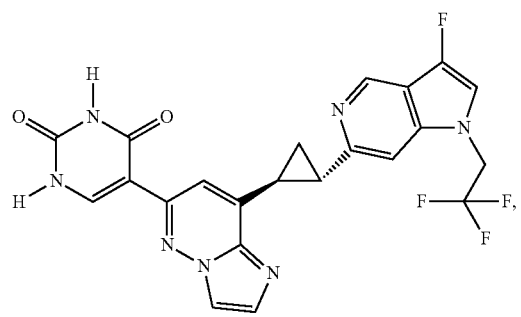
-continued
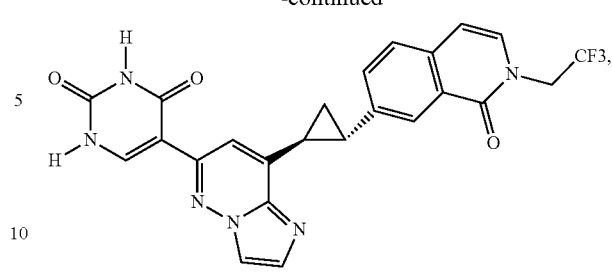
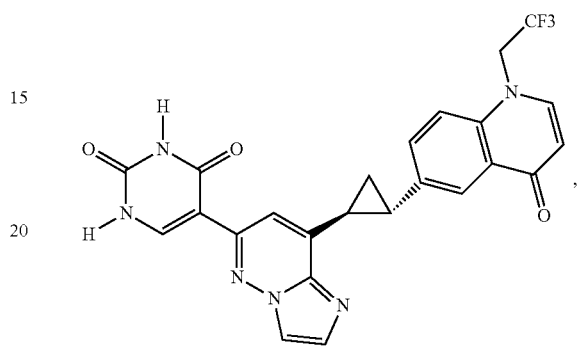
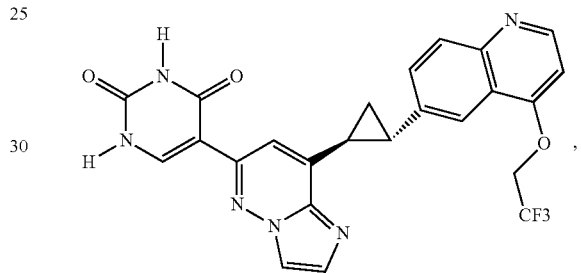
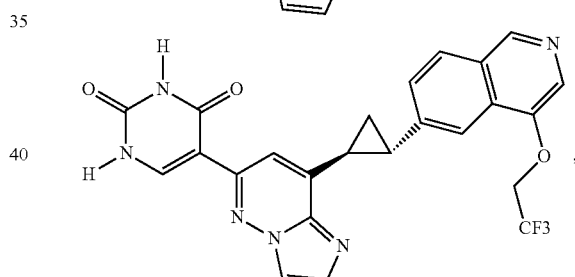
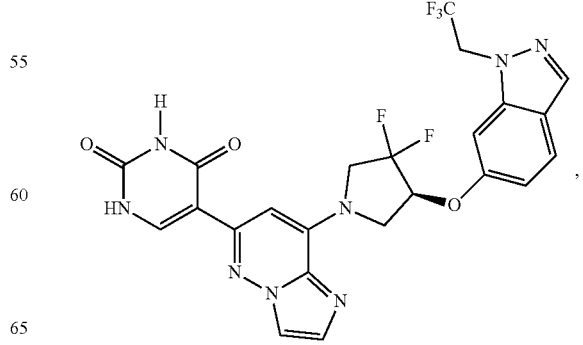

221
-continued
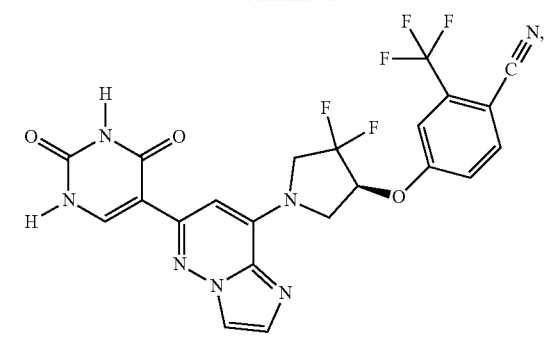
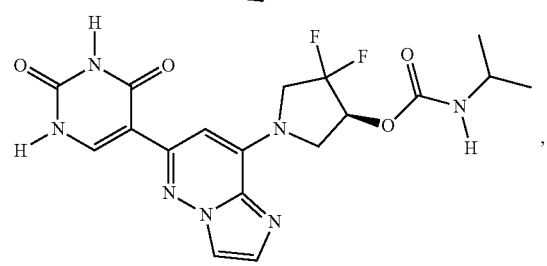
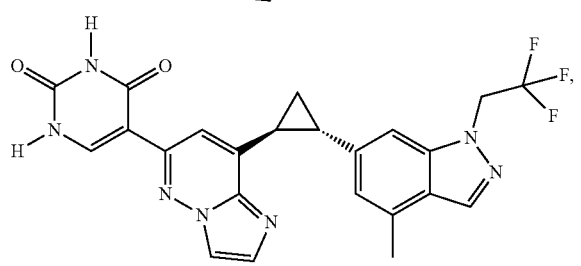
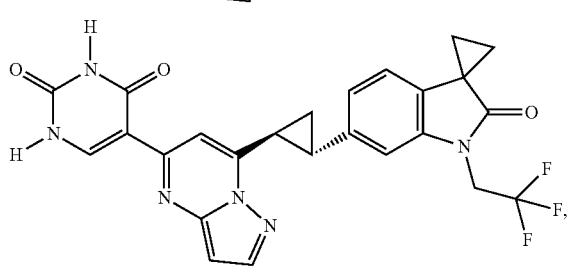
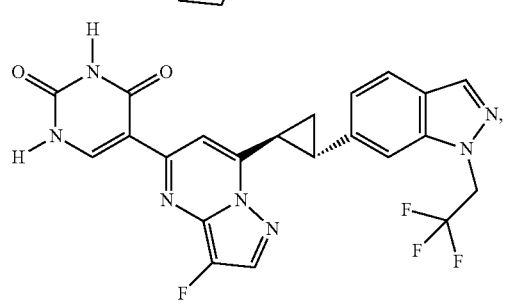
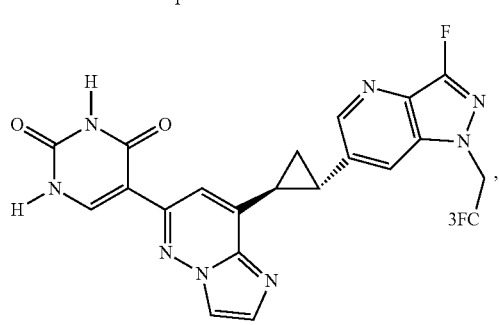
222
-continued
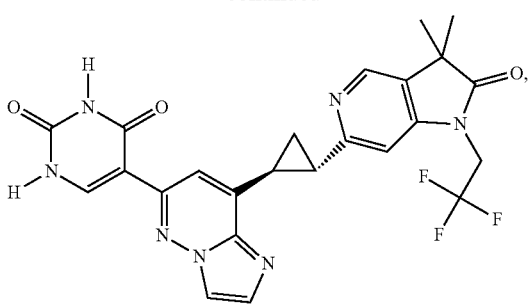
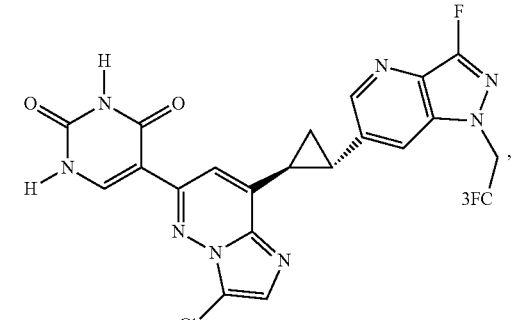
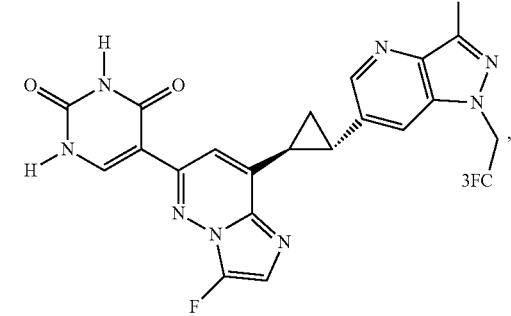
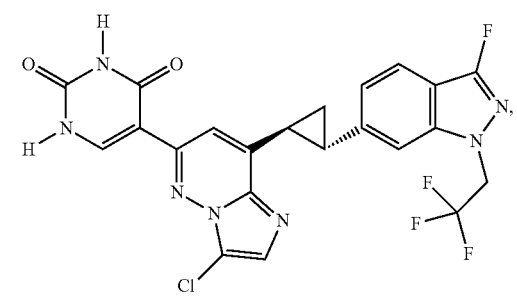
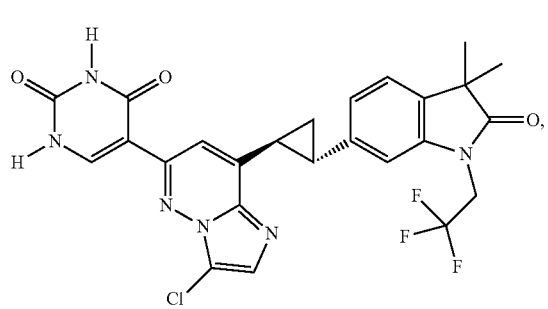

223
-continued
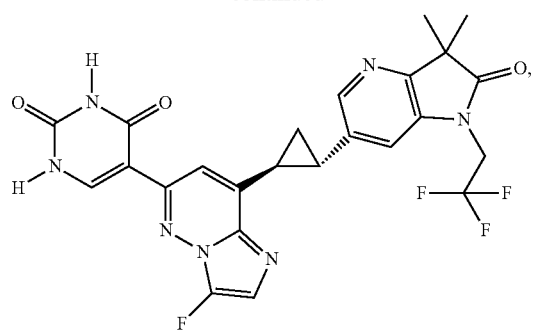
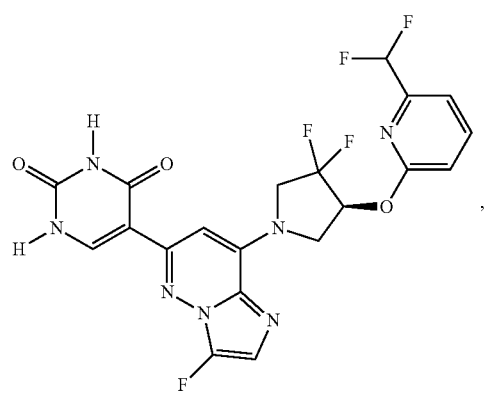

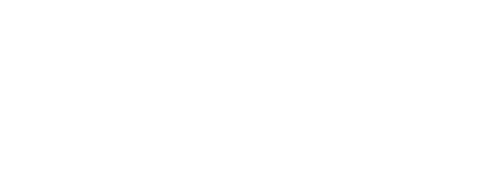
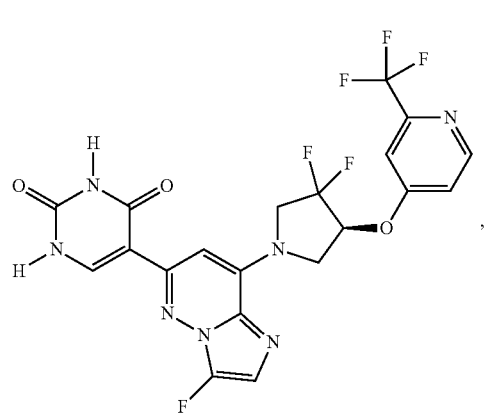
224
-continued
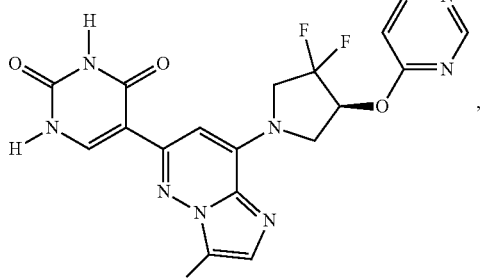
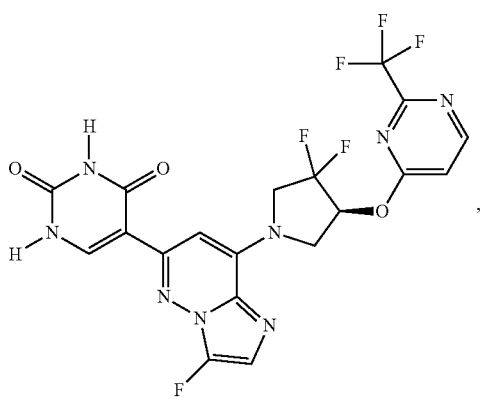
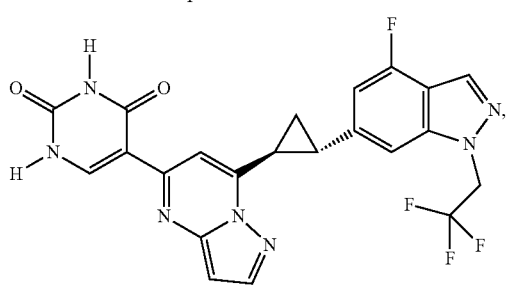
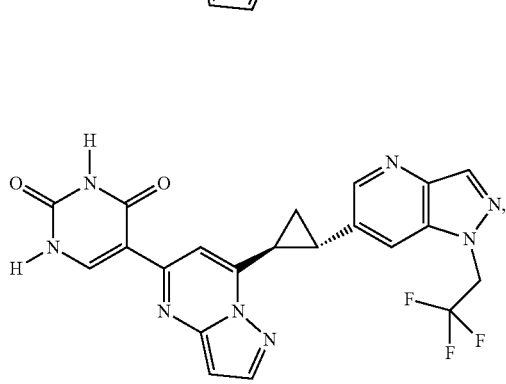

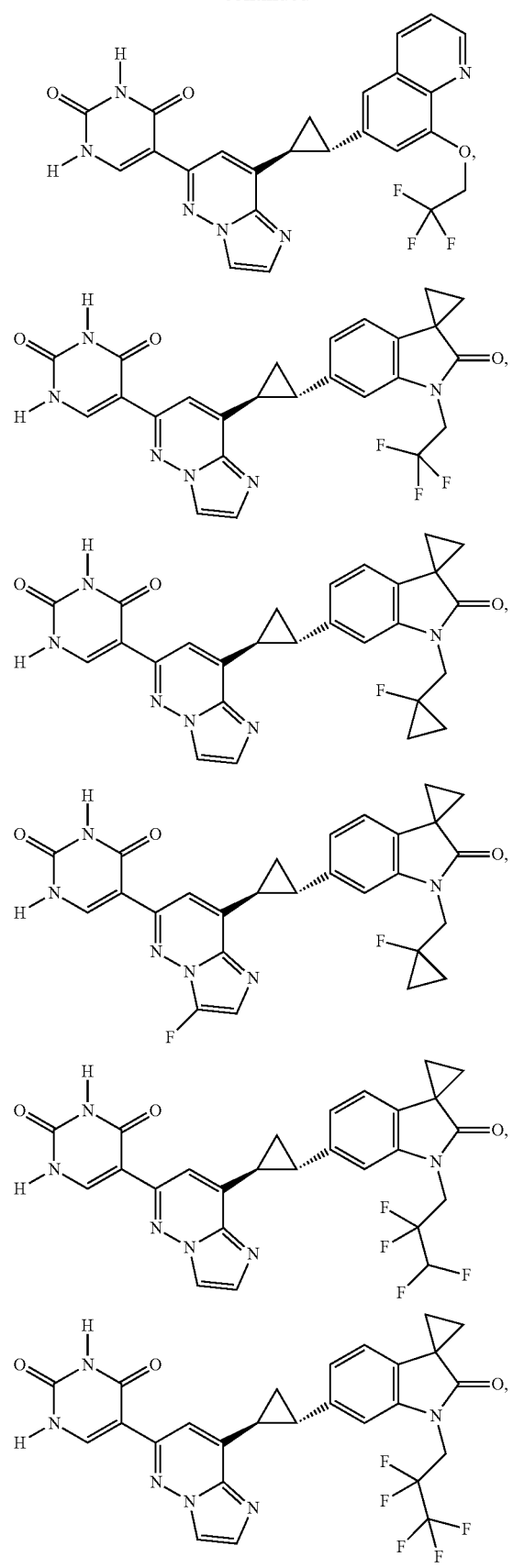
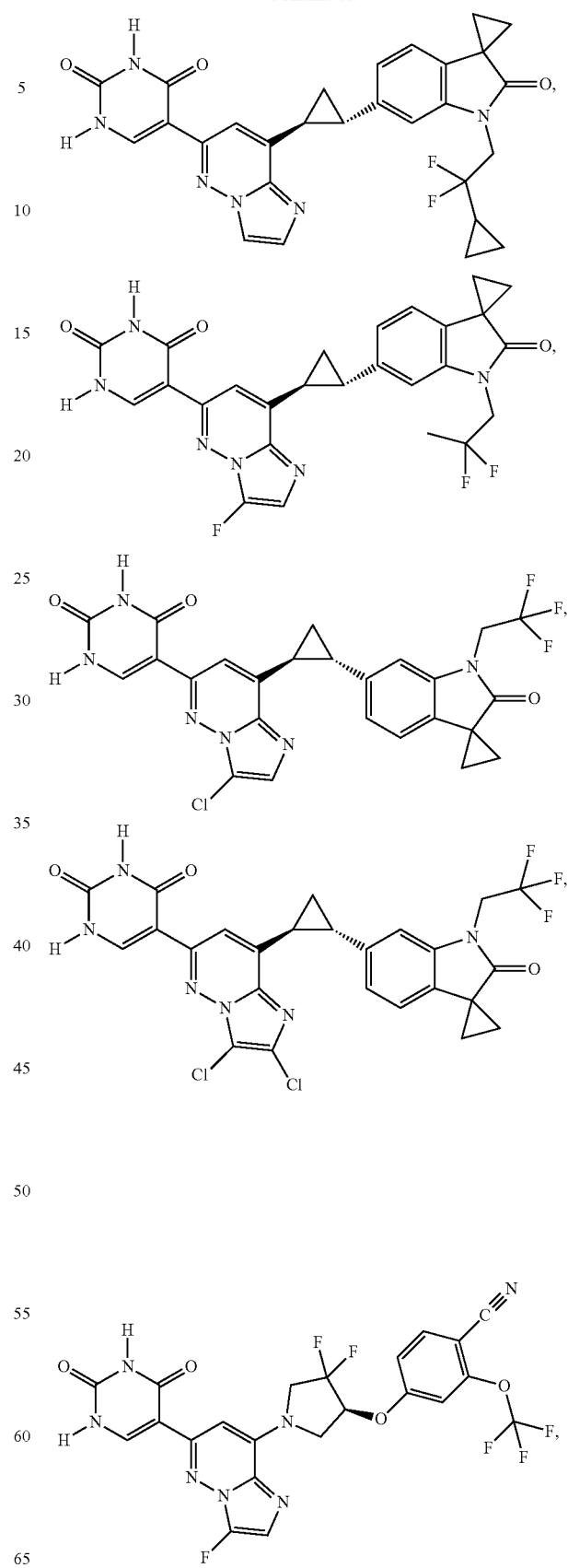

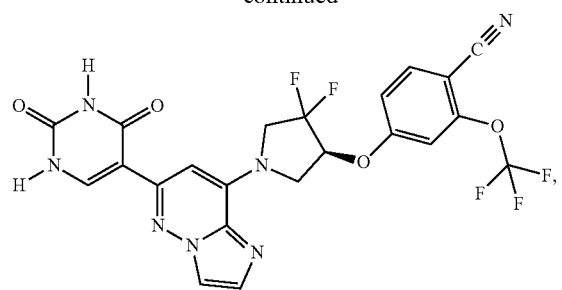

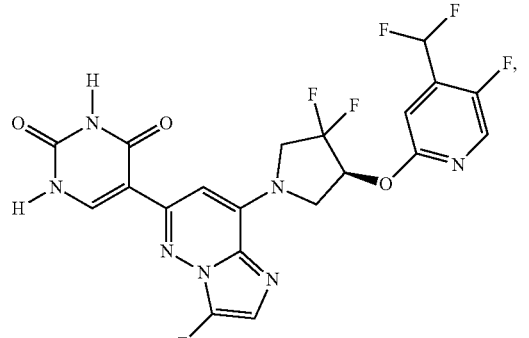

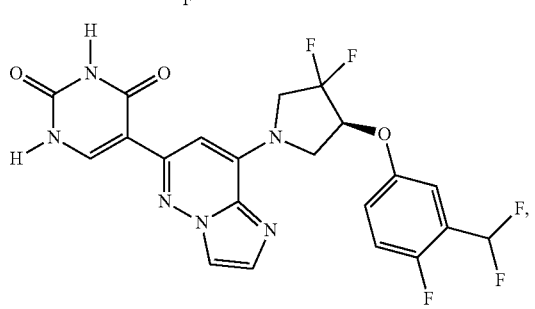

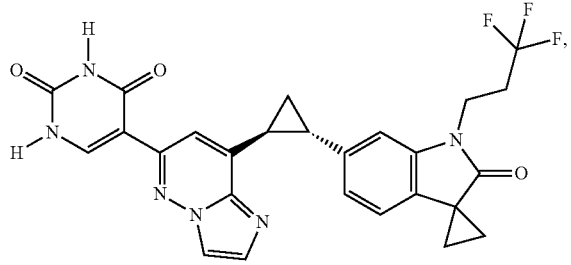

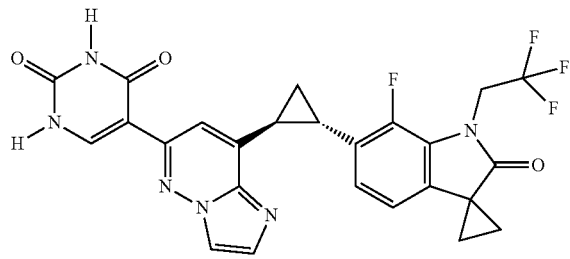

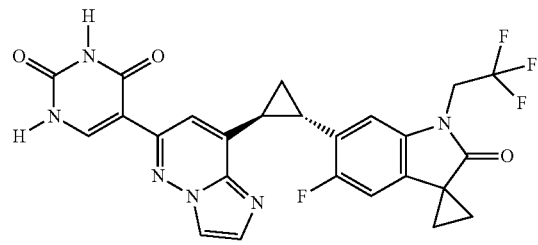

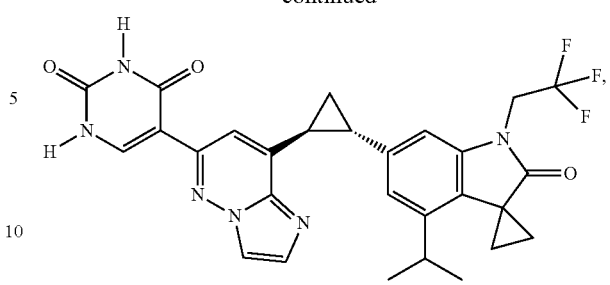

or a pharmaceutically acceptable salt thereof.

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g. $^{14}C$ or $^3H$) compound, administering it parenterally in a detectable dose (e.g. greater than about 0.5 mg/kg) to an animal such as rat, mouse, guinea pig, monkey, or to man, allowing sufficient time for metabolism to occur (typically about about 30 seconds to about 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art.

III. Methods of Preparing

The compounds of the present disclosure can be prepared by a variety of methods. For example, Schemes 1-4 show representative syntheses of the compounds of the present disclosure.

Scheme 1.

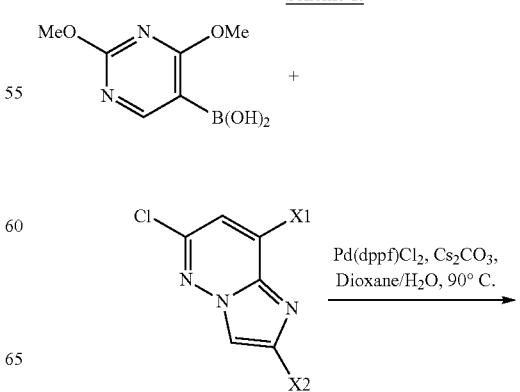

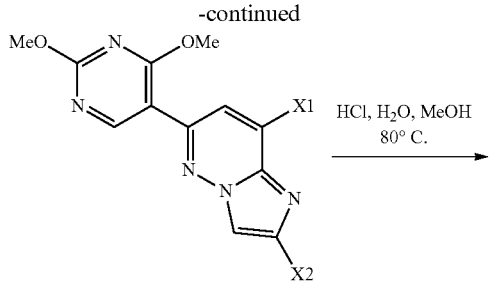

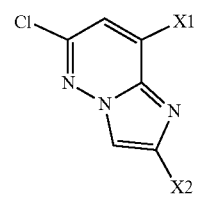

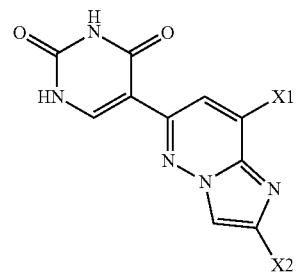

Representative synthetic Scheme 2 shows a general synthesis of the compounds of the embodiments. The methodology is compatible with a wide variety of functionalities. In Representative synthetic Scheme 2, a suitably substituted bromoimidazopyridazine (or the corresponding chloro- or iodo-compound) is combined with an alkyl boronic acid or boronic acid derivate (e.g. boronate ester or trifluoroborate salt) in a suitable solvent system (e.g. water+dioxane, THF, DME, toluene etc.) in the presence of a palladium catalyst (e.g. Pd(dppf)Cl$_2$, cataCXium-A-Pd G3 etc.) and base (e.g. Cs$_2$CO$_3$, K$_2$CO$_3$, K$_3$PO$_4$ etc.) at elevated temperature (e.g., ranging from about 90-150° C.), which can be performed in microwave reactor or with conventional heating).

Representative synthetic Scheme 1 shows a general synthesis of compounds of the disclosure. The methodology is compatible with a wide variety of functionalities. In Representative Synthesis 1, a suitably substituted chloroimidazopyridazine (or the corresponding bromo- or iodo-compound) is combined with (2,4-dimethoxypyrimidin-5-yl) boronic acid in a suitable solvent system (e.g. water+ dioxane, THF, DME, toluene etc.) in the presence of a palladium catalyst (e.g. Pd(dppf)Cl$_2$, Pd(PPh$_3$)$_4$ etc.) and base (e.g. Cs$_2$CO$_3$, K$_2$CO$_3$, K$_3$PO$_4$ etc.) at elevated temperature (e.g., ranging from about 80-120° C.), which can be performed, for example, in a microwave reactor or with conventional heating. Subsequently, the resultant suitably substituted 2,4-dimethoxypyrimidine can be treated with an acid (e.g hydrochloric acid) in a suitable solvent system (e.g. water+methanol, ethanol etc.) at elevated temperature (e.g., ranging from about 50-80° C.).

Scheme 3.

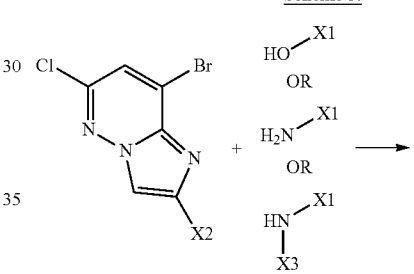

Scheme 2.

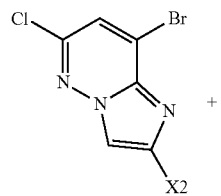

+

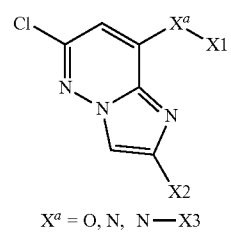

$X^a$ = O, N, N—X3

Representative synthetic Scheme 3 shows a general synthesis of the compounds of the embodiments. The methodology is compatible with a wide variety of functionalities. In representative synthetic Scheme 3, a suitably substituted bromoimidazopyridazine (or the corresponding chloro- or fluoro-compound) is combined with a nucleophile (e.g. amine, alcohol, heterocycle etc.) in a suitable solvent system (e.g. acetonitrile, EtOH, THF, NMP etc.) in the presence of a base (e.g. Cs$_2$CO$_3$, K$_2$CO$_3$ triethylamine, DIPEA, NaH etc.) at ambient or elevated temperature (e.g., ranging from about 20-90° C.).

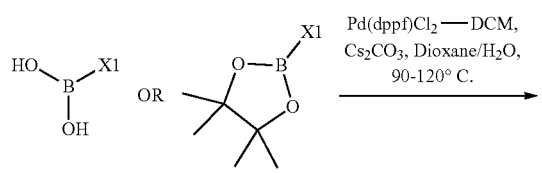

Scheme 4.

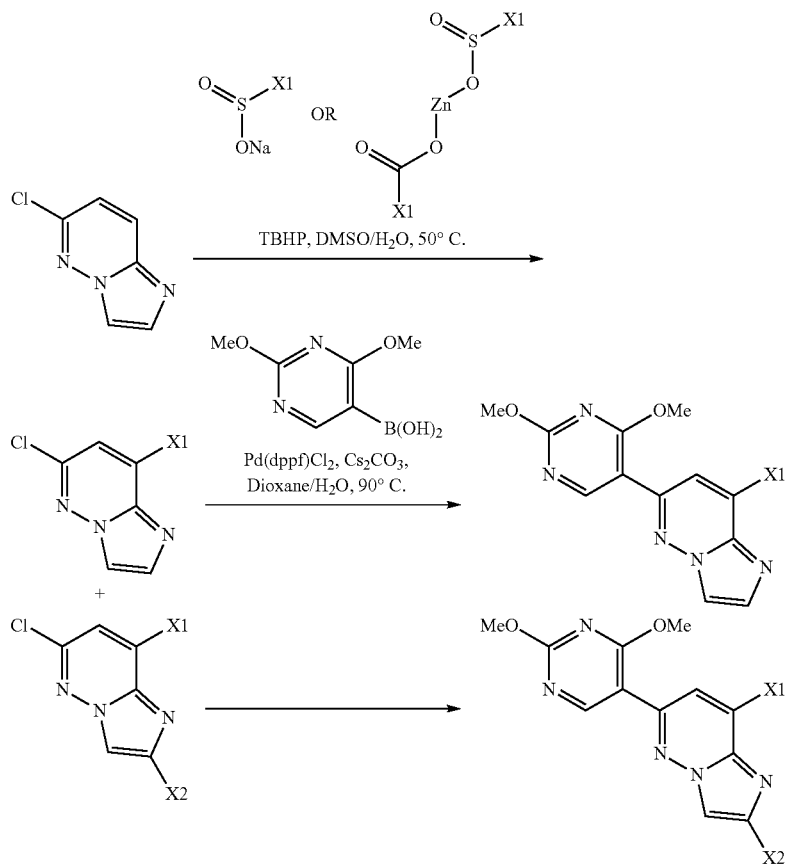

Representative synthetic Scheme 4 shows a general synthesis of the compounds of the embodiments. The methodology is compatible with a wide variety of functionalities. In representative synthetic Scheme 4, a suitably substituted chloroimidazopyridazine is combined with a radical precursor, such as a sodium or zinc alkyl sulfinate, in a suitable solvent system (e.g. DMSO/$H_2O$, DCE/$H_2O$ etc.) in the presence of an oxidant (e.g. TBHP) at ambient or elevated temperature (e.g., ranging from about 20-60° C.). A variety of radical precursor and reaction conditions can be used to generate the appropriate alkyl radical intermediate, including Minisci conditions (i.e. alkyl carboxylic acid, $(NH_4)_2S_2O_9$, $AgNO_3$, TFA).

Scheme 5.

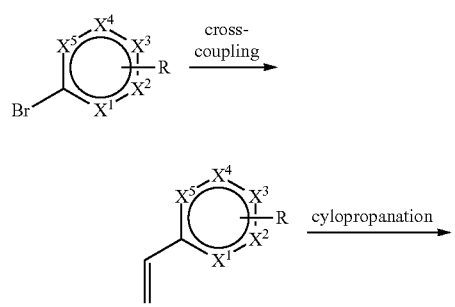

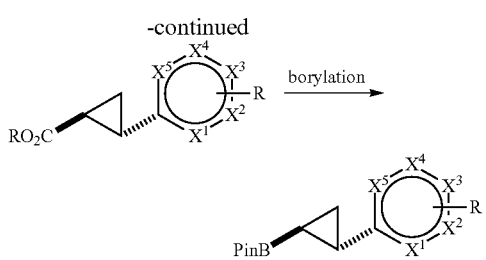

$X^1$, $X^2$, $X^3$, $X^4$, and $X^5$ are independently N or C.

Representative synthetic Scheme 5 shows a general synthesis of the compounds of the embodiments. The methodology is compatible with a wide variety of functionalities. In representative synthetic Scheme 5, a suitably substituted aryl or heteroaryl halide is combined with potassium vinyltrifluoroborate (or the analogous -Bpin, -BMIDA or —B(OH)$_2$ reagent) in a suitable solvent system (e.g. water+ THF, dioxane, DME, toluene etc.) in the presence of a palladium catalyst (e.g. Pd(dppf)Cl$_2$, Pd(PPh$_3$)$_4$ etc.) and base (e.g. K$_2$CO$_3$, Cs$_2$CO$_3$, K$_3$PO$_4$ etc.) at elevated temperature (e.g., ranging from about 80-120° C., can be performed in microwave reactor or with conventional heating). Subsequently, the suitably substituted alkene, in a suitable solvent system (e. g. DCM), is treated with tetrakis (acetonitrile)[2-[(4R)-4,5-dihydro-4-phenyl-2-oxazolyl-N] phenyl]ruthenium(II) hexafluorophosphate (or another suitable transition metal catalyst) and 1,3-dioxoisoindolin-2-yl 2-diazoacetate at low temperature (e.g., ranging from about −20° C.-5° C.). The resulting, suitably substituted, N-hydroxyphthalimide ester is combined with methyl isonicotinate (or another suitable isonicotinate derivative, e.g. isonicotinate t-butyl ester, etc.) and bis(pinacolato)diboron in a suitable solvent (e. g. EtOAc, CF$_3$Ph, etc.isonicotinate t-butyl ester) at elevated temperature (e.g., ranging from about 60-100° C.). Alternatively, the borylation reaction can be performed by combining a suitably substituted, N-hydroxyphthalimide ester with bis(catecholato)diboron in a suitable solvent system (e. g. DMF) under blue LED lights, and the resulting boronate ester combined with pinacol and triethylamine.

Alternatively, this reaction sequence can provide racemic mixtures of the compounds by combining a suitably substituted alkene with ethyl diazoacetate in a suitable solvent system (i.e. Toluene) at elevated temperature (e.g. ranging from about 80-120° C.). Subsequently, the ethyl ester can be hydrolyzed under basic aqueous conditions (e.g. LiOH or NaOMe), and the resulting acid can be combined with N-hydroxyphthalmide with a suitable coupling reagent (e.g. DIC, EDC). The final borylation step can be performed as above.

Pharmaceutical Formulations

In some embodiments, the present disclosure provides a pharmaceutical formulation comprising a pharmaceutically effective amount of a compound of the present disclosure, or a pharmaceutically acceptable salt thereof, and a pharmaceutically acceptable carrier or excipient. Also provided herein is a pharmaceutical formulation comprising a pharmaceutically effective amount of a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, and a pharmaceutically acceptable carrier or excipient.

In some embodiments, the pharmaceutical composition is for use in treating a cancer.

In some embodiments, the pharmaceutical composition further comprises one or more additional therapeutic agents. Any suitable additional therapeutic agent or combination therapy can be used with the compounds of Formula (I), (II-a), (II-b), (II-c), (II-d), (II-e), (II-f), (II-g), (II-h), (III-a), (III-b), (III-c), or (III-d), or a pharmaceutically acceptable salt thereof, such as the agents and therapies described within.

In some embodiments, the pharmaceutical composition comprises a compound of Formula (I), (II-a), (II-b), (II-c), (II-d), (II-e), (II-f), (II-g), (II-h), (III-a), (III-b), (III-c), or (III-d), and an additional therapeutic agent, wherein the additional therapeutic agent is an anticancer agent. In some embodiments, the pharmaceutical composition is the pharmaceutical composition wherein the additional therapeutic agent is independently an anti-neoplastic agent, chemotherapy, radiation therapy, or resection therapy. In some embodiments, the pharmaceutical composition is the pharmaceutical composition wherein the additional therapeutic agent is independently rituxan, doxorubicin, gemcitabine, nivolumab, pembrolizumab, nivolumab, pembrolizumab, atezolizumab, or ipilimumab. In some embodiments, the pharmaceutical composition is the pharmaceutical composition wherein the additional therapeutic agent is a PD-1/PD-L1 inhibitor.

In some embodiments, the pharmaceutical composition is the pharmaceutical composition wherein the additional therapeutic agent comprises one or more populations of immune cells, such as natural killer (NK) cells, NK-T cells, T cells, cytokine-induced killer (CIK) cells, macrophage (MAC) cells, tumor infiltrating lymphocytes (TILs) and dendritic cell (DCs).

In some embodiments, the pharmaceutical composition is the pharmaceutical composition wherein the additional therapeutic agent comprises one or more chimeric antigen receptors (CARs).

In some embodiments, the pharmaceutical composition is the pharmaceutical composition wherein the additional therapeutic agent comprises an immunotherapy, an immunostimulatory therapy, a cytokine therapy, a chemokine therapy, a cellular therapy, a gene therapy, or combinations thereof. In some embodiments, the immunotherapy includes co-administering one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins directed against one or more targets or tumor associated antigens (TAAs).

In some embodiments, compounds disclosed herein are formulated with conventional carriers and excipients, which can be selected in accord with ordinary practice. Tablets can contain excipients, glidants, fillers, binders and the like. Aqueous formulations can be prepared in sterile form, and can be isotonic, for instance when intended for delivery by other than oral administration. In some embodiments, formulations can optionally contain excipients such as those set forth in the "Handbook of Pharmaceutical Excipients" (1986). Excipients can include, for example, ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, for example from about 7 to about 10.

In some embodiments, the compounds disclosed herein are administered alone. In some embodiments, compounds disclosed herein are administered in pharmaceutical formulations. In some embodiments a formulation, for veterinary and/or for human use, comprises at least one compound of Formula (I), (II-a), (II-b), (II-c), (II-d), (II-e), (II-f), (II-g), (II-h), (III-a), (III-b), (III-c), or (III-d), or a pharmaceutically acceptable salt thereof, together with one or more acceptable carriers and optionally other therapeutic ingredients, such as those additional therapeutic ingredients discussed herein. In some embodiments, carrier(s) are "acceptable" in the sense of being compatible with the other ingredients of the formulation and physiologically innocuous to the recipient thereof.

In some embodiments, formulations of the disclosure include those suitable for the foregoing administration routes. In some embodiments, formulations are presented in unit dosage form. Formulations may be prepared by methods known in the art of pharmacy. Techniques and formulations can be found, for example, in Remington's Pharmaceutical Sciences (Mack Publishing Co., Easton, PA). Such methods include, for instance, a step of bringing into association the active ingredient with a carrier comprising one or more accessory ingredients. In some embodiments, formulations are prepared by bringing into association the active ingredient with liquid carriers or finely divided solid carriers or both, and then, in some embodiments, shaping the product.

Formulations suitable for oral administration may be presented as discrete units such as capsules, cachets or tablets each containing a predetermined amount of active ingredient, such as a compound of Formula (I), (II-a), (II-b), (II-c), (II-d), (II-e), (II-f), (II-g), (II-h), (III-a), (III-b), (III-c), or (III-d), or a pharmaceutically acceptable salt thereof; as a powder or granules; as a solution or a suspension in an aqueous or non-aqueous liquid; or as an oil-in-water liquid emulsion or a water-in-oil liquid emulsion. In some embodiments, an active ingredient is administered as a bolus, electuary or paste.

A tablet can be made, for example, by compression or molding, optionally with one or more accessory ingredients. Compressed tablets may be prepared, for example, by compressing in a suitable machine the active ingredient in a free-flowing form such as a powder or granules, optionally mixed with a binder, lubricant, inert diluent, preservative, surface active or dispersing agent. Molded tablets may be made, for instance, by molding in a suitable machine a mixture of the powdered active ingredient moistened with an inert liquid diluent. The tablets may optionally be coated or scored. In some embodiments, tablets are formulated so as to provide slow or controlled release of the active ingredient therefrom.

For infections of the eye or other external tissues e.g. mouth and skin, the formulations can be applied as a topical ointment or cream containing a compound of Formula (I), (II-a), (II-b), (II-c), (II-d), (II-e), (II-f), (II-g), (II-h), (III-a), (III-b), (III-c), or (III-d), in an amount of, for example, about 0.075 to about 20% w/w (including active ingredient(s) in a range between about 0.1% and about 20% in increments of about 0.1% w/w such as about 0.6% w/w, about 0.7% w/w, etc.), such as about 0.2 to about 15% w/w and such as about 0.5 to about 10% w/w. When formulated in an ointment, a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, may be employed with either a paraffinic or a water-miscible ointment base. Alternatively, a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, may be formulated in a cream with an oil-in-water cream base.

If desired, the aqueous phase of the cream base may include, for example, at least about 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may in some embodiments include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise merely an emulsifier (otherwise known as an emulgent), it can comprise, for example, a mixture of at least one emulsifier with a fat or an oil or with both a fat and an oil. In some embodiments, a hydrophilic emulsifier is included together with a lipophilic emulsifier which acts as a stabilizer. In some embodiments, an emulsion includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include, for instance, Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired properties. The cream can be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

In some embodiments, pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparation, such as a sterile injectable aqueous or oleaginous suspension. Such suspensions may be formulated according to the known art using those suitable dispersing or wetting agents and suspending agents which have been mentioned above. Sterile injectable or intravenous preparations may also include a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed, including synthetic mono- or diglycerides. In addition, fatty acids such as oleic acid may likewise be used in the preparation of injectables.

The amount of active ingredient that may be combined with the carrier material to produce a single dosage form can vary depending upon the host treated and the particular mode of administration. For example, a time-release formulation intended for oral administration to humans may contain about 1 to about 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to about 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient can be present in such formulations in a concentration of about 0.5 to about 20%, such as about 0.5 to about 10%, for example about 1.5% w/w.

Formulations suitable for topical administration in the mouth include, for example, lozenges comprising the active ingredient in a flavored basis, such as sucrose and acacia or tragacanth; pastilles comprising the active ingredient in an inert basis, such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for intrapulmonary or nasal administration have a particle size, for example, in the range of about 0.1 to about 500 microns, such as about 0.5, about 1, about 30, or about 35, etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment of cancer as described below.

Another embodiment provides an inhalable composition comprising a compound of Formula (I), (II-a), (II-b), (II-c), (IIIa), or (IIIb), or a pharmaceutically acceptable salt thereof. In some embodiments, the inhalable composition is suitable for treating cancer. In some embodiments, pharmaceutically acceptable salts are inorganic acid salts including hydrochloride, hydrobromide, sulfate or phosphate salts. For example, such salts may cause less pulmonary irritation relative to other salts. In some embodiments, an inhalable composition is delivered to the endobronchial space in an aerosol comprising particles with a mass median aerodynamic diameter (MMAD) between about 1 and about 5 μm. In some embodiments, the compound of Formula (I), (II-a), (II-b), (II-c), (IIIa), or (IIIb), or a pharmaceutically acceptable salt thereof, is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezo-electric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In another embodiment, a formulation for nebulization is delivered to the endobronchial space in an aerosol comprising particles with a MMAD predominantly between about 1 μm and about 5 μm using a nebulizer able to aerosolize the formulation of the compound of Formula (I), (II-a), (II-b), (II-c), (II-d), (II-e), (II-f), (II-g), (II-h), (III-a), (III-b), (III-c), or (III-d), or a pharmaceutically acceptable salt thereof, into particles of the required MMAD. To be optimally therapeutically effective and to avoid upper respiratory and systemic side effects, the majority of aerosolized particles should not have a MMAD greater than about 5 μm. If an aerosol contains a large number of particles with a MMAD larger than about 5 µm, the particles are deposited in the upper airways decreasing the amount of drug delivered to the site of inflammation and bronchoconstriction in the lower respiratory tract. If the MMAD of the aerosol is smaller than about 1 µm, then the particles can in some cases remain suspended in the inhaled air and may be subsequently exhaled during expiration.

When formulated and delivered according to methods herein, the aerosol formulation for nebulization delivers a therapeutically efficacious dose of the compound of Formula (I), (II-a), (II-b), (II-c), (II-d), (II-e), (II-f), (II-g), (II-h), (III-a), (III-b), (III-c), or (III-d), or a pharmaceutically acceptable salt thereof, to a therapeutic target, such as the site of a cancer. The amount of drug administered can be adjusted to reflect the efficiency of the delivery of a therapeutically efficacious dose of the compound of Formula (I), (II-a), (II-b), (II-c), (II-d), (II-e), (II-f), (II-g), (II-h), (III-a), (III-b), (III-c), or (III-d), or a pharmaceutically acceptable salt thereof. In an embodiment, a combination of the aqueous aerosol formulation with the atomizing, jet, pressurized, vibrating porous plate, or ultrasonic nebulizer permits, depending on the nebulizer, from about 20 to about 90%, such as about 70% delivery of the administered dose of the compound of Formula (I), (II-a), (II-b), (II-c), (II-d), (II-e), (II-f), (II-g), (II-h), (III-a), (III-b), (III-c), or (III-d), or a pharmaceutically acceptable salt thereof, into the airways. In an embodiment, from about 30 to about 50% of the active compound is delivered. For example, from about 70 to about 90% of the active compound can be delivered.

In another embodiment, a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, is delivered as a dry inhalable powder. The compounds are administered endobronchially as a dry powder formulation to efficacious deliver fine particles of compound into the endobronchial space using dry powder or metered dose inhalers. For delivery by DPI, the compound of Formula (I), (II-a), (II-b), (II-c), (II-d), (II-e), (II-f), (II-g), (II-h), (III-a), (III-b), (III-c), or (III-d), or a pharmaceutically acceptable salt thereof, is processed into particles with, predominantly, MMAD between about 1 µm and about 5 µm by milling spray drying, critical fluid processing, or precipitation from solution. Media milling, jet milling and spray-drying devices and procedures capable of producing the particle sizes with a MMAD between about 1 µm and about 5 µm are well known in the art. In one embodiment, excipients are added to the compound of Formula (I), (II-a), (II-b), (II-c), (II-d), (II-e), (II-f), (II-g), (II-h), (III-a), (III-b), (III-c), or (III-d), or a pharmaceutically acceptable salt thereof, before processing into particles of the required sizes. In another embodiment, excipients are blended with the particles of the required size to aid in dispersion of the drug particles, for example by using lactose as an excipient.

Particle size determinations are made using devices well known in the art. For example, a multi-stage Anderson cascade impactor or other suitable method such as those specifically cited within the US Pharmacopoeia Chapter 601 as characterizing devices for aerosols within metered-dose and dry powder inhalers.

In another embodiment, a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, can be delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from about 1 µm to about 5 µm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In some embodiments, a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, is delivered as a dry powder using either type of dry powder inhaler as described herein, wherein the MMAD of the dry powder, exclusive of any excipients, is predominantly in the range of about 1 µm to about 5 µm.

In another embodiment, a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361306 and 6,116,234. In some embodiments, a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, is delivered as a dry powder using a metered dose inhaler wherein the MMAD of the dry powder, exclusive of any excipients, is predominantly in the range of about 1 to about 5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Unit dosage formulations include those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient is controlled and regulated to allow less frequency dosing or to improve the pharmacokinetic or toxicity profile of a given active ingredient.

Effective dose of active ingredient depends at least on the nature of the condition being treated, toxicity, the method of delivery, and the pharmaceutical formulation, and can be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of about 70 kg body weight can range from about 1 mg to about 1000 mg, such as between about 5 mg and about 500 mg, and may take the form of single or multiple doses.

Some embodiments provide a method for manufacturing a medicament for treating cancer in a subject in need thereof. In some embodiments, the method for manufacturing a medicament for treating cancer includes using a compound having the structure of Formula (I), (II-a), (II-b), (II-c), (II-d), (II-e), (II-f), (II-g), (II-h), (III-a), (III-b), (III-c), or (III-d), or a pharmaceutically acceptable salt thereof. Some embodiments provide a method for manufacturing a medicament for inhibiting cancer metastasis in a subject in need thereof. In some embodiments, the method for manufacturing a medicament for inhibiting cancer metastasis includes using a compound having the structure of Formula (I), (II-a), (II-b), (II-c), (II-d), (II-e), (II-f), (II-g), (II-h), (III-a), (III-b), (III-c), or (III-d), or a pharmaceutically acceptable salt thereof.

In some embodiments, the disclosure provides a use of compound having the structure of Formula (I), (II-a), (II-b), (II-c), (II-d), (II-e), (II-f), (II-g), (II-h), (III-a), (III-b), (III-c), or (III-d), or a pharmaceutically acceptable salt thereof, in the treatment of cancer in a subject in need thereof. In some embodiments, the disclosure provides a use of compound having the structure of Formula (I), (II-a), (II-b), (II-c), (II-d), (II-e), (II-f), (II-g), (II-h), (III-a), (III-b), (III-c), or (III-d), or a pharmaceutically acceptable salt thereof, in inhibiting cancer metastasis in a subject in need thereof. In some embodiments, the disclosure provides a compound having the structure of Formula (I), (II-a), (II-b), (II-c), (II-d), (II-e), (II-f), (II-g), (II-h), (III-a), (III-b), (III-c), or (III-d), or a pharmaceutically acceptable salt thereof, for use in theapy.

IV. Routes of Administration

One or more of the compounds of Formula (I), (II-a), (II-b), (II-c), (II-d), (II-e), (II-f), (II-g), (II-h), (III-a), (III-b), (III-c), or (III-d), or a pharmaceutically acceptable salt thereof, (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the route may vary with for example the condition of the recipient. In some embodiments, compounds disclosed herein are orally bioavailable and can be dosed orally.

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the route may vary with for example the condition of the recipient. An advantage of certain compounds disclosed herein is that they are orally bioavailable and can be dosed orally.

A compound of the present disclosure, may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from about 1 mg to about 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, about 125, about 150, about 175, about 200, about 225, about 250, about 275, about 300, about 325, about 350, about 375, about 400, about 425, about 450, about 475, or about 500 mg per dose. Other therapeutically effective amounts of the compound of the present disclosure are about 100 mg per dose, or about 125, about 150, about 175, about 200, about 225, about 250, about 275, about 300, about 325, about 350, about 375, about 400, about 425, about 450, or about 500 mg per dose. A single dose can be administered hourly, daily, or weekly. For example, a single dose can be administered once about every 1 hour, about 2, about 3, about 4, about 6, about 8, about 12, about 16 or once about every 24 hours. A single dose can also be administered once about every 1 day, about 2, about 3, about 4, about 5, about 6, or once about every 7 days. A single dose can also be administered once about every 1 week, about 2, about 3, or once about every 4 weeks. In some embodiments, a single dose can be administered once about every week. A single dose can also be administered once about every month.

Other therapeutically effective amounts of the compound of the present disclosure are about 20, about 25, about 30, about 35, about 40, about 45, about 50, about 55, about 60, about 65, about 70, about 75, about 80, about 85, about 90, about 95, or about 100 mg per dose.

The frequency of dosage of the compound of the present disclosure can be determined by the needs of the individual patient and can be, for example, once per day or twice, or more times, per day. Administration of the compound continues for as long as necessary to treat the disease or condition. For example, a compound can be administered to a human having cancer for a period of from about 20 days to about 180 days or, for example, for a period of from about 20 days to about 90 days or, for example, for a period of from about 30 days to about 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from about 1 to about 14 days, followed by a period of about 7 to about 21 days during which the patient does not receive a dose of the compound, followed by a subsequent period (e.g., from about 1 to about 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

In order to prolong the effect of a compound of the present disclosure, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

V. Combination Therapy

The compounds of Formula (I), (II-a), (II-b), (II-c), (II-d), (II-e), (II-f), (II-g), (II-h), (III-a), (III-b), (III-c), or (III-d), pharmaceutically acceptable salts thereof, and/or compositions provided herein can also used in combination with other active therapeutic agents for the treatment of cancer.

A. COMBINATION THERAPIES

In various embodiments, a compound as described herein, is combined with one or more additional therapeutic agents, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (mono- and multi-specific antibodies and fragments thereof in any format (e.g., including without limitation DARTs®, Duobodies®, BiTEs®, BiKEs, TriKEs, XmAbs®, TandAbs®, scFvs, Fabs, Fab derivatives), bi-specific antibodies, non-immunoglobulin antibody mimetics (e.g., including without limitation adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs), antibody-drug conjugates (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, without limitation, an inhibitor, agonist, antagonist, ligand, modulator, stimulator, blocker, activator or suppressor of a target (e.g., polypeptide or polynucleotide) including without limitation: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2BR, A2aR, A3aR), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, 4-1BB ligand (CD137L), Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain-containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK$_2$), chemokine (C-C motif) receptor (such as CCR2, CCR4, CCR5, CCR8), chemokine (C-X-C motif) receptor (such as CXCR1, CXCR2, CXCR3 and CXCR4), Chemokine CC21 ligand, Cholecystokinin CCK2 receptor, Chorionic gonadotropin, c-Kit (tyrosine-protein kinase Kit or CD117), CISH (Cytokine-inducible SH2-containing protein), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e (CEACAM6), CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COPS signalosome subunit 5, CSF-1 (colony-stimulating factor 1 receptor), CSF2 gene, CTLA-4 (cytotoxic T-lymphocyte protein 4) receptor, C-type lectin domain protein 9A (CLEC9A), Cyclin D1, Cyclin G1, cyclin-dependent kinases (CDK, such as CDK1, CDK12, CDK1B, CDK2-9), cyclooxygenase (such as COX1, COX2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, DEAD-box helicase 6 (DDX6), Death receptor 5 (DR5, TRAILR2), Death receptor 4 (DR4, TRAILR1), Delta-like protein ligand (such as 3, 4), Deoxyribonuclease, Deubiquitinating enzymes (DUB s), Dickkopf-1 ligand, dihydrofolate reductase (DHFR), Dihydropyrimidine dehydrogenase, Dipeptidyl peptidase IV, discoidin domain receptor (DDR, such as DDR1), Diacylglycerol kinase zeta (DGKZ), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, E3 ubiquitin-protein ligase (such as RNF128, CBL-B), echinoderm microtubule like protein 4, EGFR tyrosine kinase receptor, Elastase, Elongation factor 1 alpha 2, Elongation factor 2, Endoglin, Endonuclease, endoplasmic reticulum aminopeptidase (ERAP, such as ERAP 1, ERAP2), Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Hypoxia-inducible factor prolyl hydroxylase (HIF-PH or EGLN), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, focal adhesion kinase (FAK, such as FAK$_2$), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HO1), Heme oxygenase 2 (HO2), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone $H_3$, HLA class I antigen (A-2 alpha), HLA class II antigen, HLA class I antigen alpha G (HLA-G), Non-classical HLA, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIFIα), Imprinted Maternally Expressed Transcript (H19) gene, mitogen-activated protein kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1 and IDO2), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, Interleukin 35 (IL-35), isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukocyte immunoglobulin-like receptor subfamily B member 1 (ILT2), Leukocyte immunoglobulin-like receptor subfamily B member 2 (ILT4), Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), 5-Lipoxygenase (5-LOX), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mc1-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, NLRP3 (NACHT LRR PYD domain protein 3) modulators, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly (ADP-ribose) polymerase (PARP, such as PARP1, PARP2 and PARP3, PARP7, and mono-PARPs), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), Prostaglandin E2 synthase, prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, puringergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Secreted phospholipase A2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, Stabilin-1 (STAB1), STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Suppressor of cytokine signaling modulators (SOCS), Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, Three prime repair exonuclease 1 (TREX1), Three prime repair exonuclease 2 (TREX2), Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, transferrin (TF), transforming growth factor alpha (TGFα), transforming growth factor beta (TGFB) and isoforms thereof, TGF beta 2 ligand, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), tryptophan 2,3-dioxygenase (TDO), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tumor specific neoantigens, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Ubiquitin-specific-processing protease 7 (USP7), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase, Mer (Mer tyrosine kinase receptor modulators), YAP (Yes-associated protein modulators)es, Wee-1 protein kinase, Werner Syndrome RecQ Like Helicase (WRN), Wilms' tumor antigen 1, Wilms' tumor protein, WW domain containing transcription regulator protein 1 (TAZ), X-linked inhibitor of apoptosis protein, Zinc finger protein transcription factor or any combination thereof.

Illustrative Mechanisms of Action

In various embodiments, the one or more additional therapeutic agents may be categorized by their mechanism of action into, for example, the following groups:

anti-metabolites/anti-cancer agents, such as pyrimidine analogs floxuridine, capecitabine, cytarabine, CPX-351 (liposomal cytarabine, daunorubicin), and TAS-118;

Alpha 1 adrenoceptor/Alpha 2 adrenoceptor antagonists, such as phenoxybenzamine hydrochloride (injectable, pheochromocytoma);

Androgen receptor antagonists, such as nilutamide;

anti-cadherin antibodies, such as HKT-288;

anti-leucine-rich repeat containing 15 (LRRC15) antibodies, such as ABB V-085. ARGX-110;

angiotensin receptor blockers, nitric oxide donors;

antisense oligonucleotides, such as AEG35156, IONIS-KRAS-2.5 Rx, EZN-3042, RX-0201, IONIS-AR-2.5 Rx, BP-100 (prexigebersen), IONIS-STAT3-2.5 Rx;

anti-angiopoietin (ANG)-2 antibodies, such as MEDI3617, and LY3127804;

anti-ANG-1/ANG-2 antibodies, such as AMG-780;

anti-CSF1R antibodies, such as emactuzumab, LY3022855, AMG-820, FPA-008 (cabiralizumab);

anti-endoglin antibodies, such as TRC105 (carotuximab);

anti-ERBB antibodies, such as CDX-3379, HLX-02, seribantumab;

anti-HER2 antibodies, such as HERCEPTIN® (trastuzumab), trastuzumab biosimimar, margetuximab, MEDI4276, BAT-8001, Pertuzumab (Perjeta), RG6264, ZW25 (a bispecific HER2-directed antibody targeting the extracellular domains 2 and 4; Cancer Discov. 2019 January; 9(1):8; PMID: 30504239);

anti-HLA-DR antibodies, such as IMMU-114;

anti-IL-3 antibodies, such as JNJ-56022473;

anti-TNF receptor superfamily member 18 (TNFRSF18, GITR; NCBI Gene ID: 8784) antibodies, such as MK-4166, MEDI1873, FPA-154, INCAGN-1876, TRX-518, BMS-986156, MK-1248, GWN-323; and those described, e.g. in Intl. Patent Publ. Nos. WO 2017/096179, WO 2017/096276, WO 2017/096189; and WO 2018/089628;

anti-EphA3 antibodies, such as KB-004;

anti-CD37 antibodies, such as otlertuzumab (TRU-016);

anti-FGFR-3 antibodies, such as LY3076226, B-701;

anti-FGFR-2 antibodies, such as GAL-F2;

anti-C5 antibodies, such as ALXN-1210;

anti-EpCAM antibodies, such as VB4-845;

anti-CEA antibodies, such as RG-7813;

anti-Carcinoembryonic-antigen-related-cell-adhesion-molecule-6 (CEACAM6, CD66C) antibodies, such as BAY-1834942, NEO-201 (CEACAM 5/6);

anti-GD2 antibodies, such as APN-301;

anti-interleukin-17 (IL-17) antibodies, such as CJM-112;

anti-interleukin-1 beta antibodies, such as canakinumab (ACZ885), VPM087;

anti-carbonic anhydrase 9 (CA9, CAIX) antibodies, such as TX-250;

anti-CD38 antibodies, such as isatuximab, MOR-202, TAK-079;

anti-CD38-attenukine, such as TAK573;

anti-Mucin 1 (MUC1) antibodies, such as gatipotuzumab, Mab-AR-20.5;

anti-CD33 antibodies, such as IMGN-779;

anti-KMA antibodies, such as MDX-1097;
anti-CD55 antibodies, such as PAT-SC1;
anti-c-Met antibodies, such as ABBV-399;
anti-PSMA antibodies, such as ATL-101;
anti-CD100 antibodies, such as VX-15;
anti-EPHA3 antibodies, such as fibatuzumab;
anti-APRIL antibodies, such as BION-1301;
anti-fibroblast activation protein (FAP)/IL-2R antibodies, such as RG7461;
anti-fibroblast activation protein (FAP)/TRAIL-R2 antibodies, such as RG7386;
anti-fucosyl-GM1 antibodies, such as BMS-986012;
anti-IL-8 (Interleukin-8) antibodies, such as HuMax-Inflam;
anti-myostatin inhibitors, such as landogrozumab;
anti-delta-like protein ligand 3 (DDL3) antibodies, such as rovalpituzumab tesirine;
anti-DLL4 (delta like ligand 4) antibodies, such as demcizumab;
anti-clusterin antibodies, such as AB-16B5;
anti-Ephrin-A4 (EFNA4) antibodies, such as PF-06647263;
anti-RANKL antibodies, such as denosumab;
anti-mesothelin antibodies, such as BMS-986148, Anti-MSLN-MMAE;
anti-sodium phosphate cotransporter 2B (NaP2B) antibodies, such as lifastuzumab
anti-TGFb antibodies, such as SAR439459;
anti-transforming growth factor-beta (TGF-beta) antibodies, such as ABB V-151,
LY3022859, NIS793, XOMA 089;
purine analogs, folate antagonists (such as pralatrexate), cladribine, pentostatin, fludarabine and related inhibitors;
antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);
DNA damaging agents, such as actinomycin, amsacrine, busulfan, carboplatin, chlorambucil, cisplatin, cyclophosphamide (CYTOXAN®), dactinomycin, daunorubicin, doxorubicin, DEBDOX, epirubicin, iphosphamide, melphalan, merchlorethamine, mitomycin C, mitoxantrone, nitrosourea, procarbazine, taxol, Taxotere, teniposide, etoposide, and triethylenethiophosphoramide;
DNA-hypomethylating agents, such as guadecitabine (SGI-110), ASTX727;
antibiotics such as dactinomycin, daunorubicin, doxorubicin, idarubicin, anthracyclines, mitoxantrone, bleomycins, plicamycin (mithramycin);
enzymes such as L-asparaginase which systemically metabolizes L-asparagine and deprives cells which do not have the capacity to synthesize their own asparagine;
DNAi oligonucleotides targeting Bcl-2, such as PNT2258; agents that activate or reactivate latent human immunodeficiency virus (HIV), such as panobinostat and romidepsin;
asparaginase stimulators, such as crisantaspase (Erwinase®) and GRASPA (ERY-001, ERY-ASP), calaspargase pegol, pegaspargase;
pan-Trk, ROS1 and ALK inhibitors, such as entrectinib, TPX-0005;

anaplastic lymphoma kinase (ALK) inhibitors, such as alectinib, ceritinib, alecensa (RG7853), ALUNBRIG® (brigatinib);
antiproliferative/antimitotic alkylating agents, such as nitrogen mustard cyclophosphamide and analogs (e.g., melphalan, chlorambucil, hexamethylmelamine, thiotepa), alkyl nitrosoureas (e.g., carmustine) and analogs, streptozocin, and triazenes (e.g., dacarbazine);
antiproliferative/antimitotic antimetabolites, such as folic acid analogs (methotrexate);
platinum coordination complexes (e.g., cisplatin, oxiloplatinim, and carboplatin), procarbazine, hydroxyurea, mitotane, and aminoglutethimide;
hormones, hormone analogs (e.g., estrogen, tamoxifen, goserelin, bicalutamide, and nilutamide), and aromatase inhibitors (e.g., letrozole and anastrozole);
antiplatelet agents; anticoagulants such as heparin, synthetic heparin salts, and other inhibitors of thrombin;
fibrinolytic agents such as tissue plasminogen activator, streptokinase, urokinase, aspirin, dipyridamole, ticlopidine, and clopidogrel;
antimigratory agents; antisecretory agents (e.g., breveldin);
immunosuppressives, such as tacrolimus, sirolimus, azathioprine, and mycophenolate;
growth factor inhibitors, and vascular endothelial growth factor inhibitors;
fibroblast growth factor inhibitors, such as FPA14;
AMP activated protein kinase stimulators, such as metformin hydrochloride;
ADP ribosyl cyclase-1 inhibitors, such as daratumumab (DARZALEX®);
Caspase recruitment domain protein-15 stimulators, such as mifamurtide (liposomal);
CCR5 chemokine antagonists, such as MK-7690 (vicriviroc);
CDC7 protein kinase inhibitors, such as TAK-931;
Cholesterol side-chain cleavage enzyme inhibitors, such as ODM-209;
Dihydropyrimidine dehydrogenase/Orotate phosphoribosyltransferase inhibitors, such as Cefesone (tegafur+gimeracil+oteracil potassium);
DNA polymerase/Ribonucleotide reductase inhibitors, such as clofarabine;
DNA interference oligonucleotides, such as PNT2258, AZD-9150;
Estrogen receptor modulators, such as bazedoxifene;
Estrogen receptor agonists/Progesterone receptor antagonists, such as TRI-CYCLEN LO (norethindrone+ethinyl estradiol);
HLA class I antigen A-2 alpha modulators, such as FH-MCVA2TCR;
HLA class I antigen A-2 alpha/MART-1 melanoma antigen modulators, such as MART-1 F5 TCR engineered PBMC;
Human Granulocyte Colony Stimulating Factors, such as PF-06881894;
GNRH receptor agonists, such as leuprorelin acetate, leuprorelin acetate sustained release depot (ATRIGEL), triptorelin pamoate, go serelin acetate;
GNRH receptor antagonists, such as elagolix, relugolix, degarelix;
Endoplasmin modulators, such as anlotinib;
H+K+ATPase inhibitors, such as omeprazole, esomeprazole;
ICAM-1/CD55 modulators, such as cavatak (V-937);
IL-15/IL-12 modulators, such as SAR441000;

Interleukin 23A inhibitors, such as guselkumab;
Lysine specific histone demethylase 1 inhibitors, such as CC-90011;
IL-12 Mrna, such as MEDI1191;
RIG-I modulators, such as RGT-100;
NOD2 modulators, such as SB-9200, and IR-103.
Progesterone receptor agonists, such as levonorgestrel;
Protein cereblon modulators, such as CC-92480, CC-90009;
Protein cereblon modulators/DNA binding protein Ikaros inhibitors/Zinc finger binding protein Aiolos inhibitors, such as iberdomide;
Retinoid X receptor modulators, such as alitretinoin, bexarotene (oral formulation);
RIP-1 kinase inhibitors, such as GSK-3145095;
selective oestrogen receptor degraders, such as AZD9833;
SUMO inhibitors, such as TAK-981;
Thrombopoietin receptor agonists, such as eltrombopag;
Thyroid hormone receptor agonists, such as levothyroxine sodium;
TNF agonists, such as tasonermin;
Tyrosine phosphatase substrate 1 inhibitors, such as CC-95251;
HER2 inhibitors, such as neratinib, tucatinib (ONT-380);
EGFR/ErbB2/Ephb4 inhibitors, such as tesevatinib;
EGFR/HER2 inhibitors, such as TAK-788;
EGFR family tyrosine kinase receptor inhibitors, such as DZD-9008;
EGFR/ErbB-2 inhibitors, such as varlitinib;
Mutant selective EGFR inhibitors, such as PF-06747775, EGF816 (nazartinib), ASP8273, ACEA-0010, BI-1482694;
epha2 inhibitors, such as MM-310;
polycomb protein (EED) inhibitors, such as MAK683;
DHFR inhibitor/Folate transporter 1 modulator/Folate receptor antagonist, such as pralatrexate;
DHFR/GAR transformylase/Thymidylate synthase/Transferase inhibitors, such as pemetrexed disodium;
p38 MAP kinase inhibitors, such as ralimetinib;
PRMT inhibitors, such as MS203, PF-06939999, GSK3368715, GSK3326595;
Sphingosine kinase 2 ($SK_2$) inhibitors, such as opaganib;
Nuclear erythroid 2-related factor 2 stimulators, such as omaveloxolone (RTA-408);
Tropomyosin receptor kinase (TRK) inhibitors, such as LOXO-195, ONO-7579;
Mucin 1 inhibitors, such as GO-203-2C;
MARCKS protein inhibitors, such as BIO-11006;
Folate antagonists, such as arfolitixorin;
Galectin-3 inhibitors, such as GR-MD-02;
Phosphorylated P68 inhibitors, such as RX-5902;
CD95/TNF modulators, such as ofranergene obadenovec;
pan-PIM kinase inhibitors, such as INCB-053914;
IL-12 gene stimulators, such as EGEN-001, tavokinogene telseplasmid;
Heat shock protein HSP90 inhibitors, such as TAS-116, PEN-866;
VEGF/HGF antagonists, such as MP-0250;
VEGF ligand inhibitors, such as bevacizumab biosimilar;
VEGF receptor antagonists/VEGF ligand inhibitors, such as ramucirumab;
VEGF-1/VEGF-2/VEGF-3 receptor antagonists; such as fruquintinib;
VEGF-1/VEGF-2 receptor modulators, such as HLA-A2402/HLA-A0201 restricted epitope peptide vaccine;
Placenta growth factor ligand inhibitor/VEGF-A ligand inhibitor, such as aflibercept;
SYK tyrosine kinase/JAK tyrosine kinase inhibitors, such as ASN-002;
Trk tyrosine kinase receptor inhibitors, such as larotrectinib sulfate;
JAK3/JAK1/TBK1 kinase inhibitors, such as CS-12912;
IL-24 antagonist, such as AD-IL24;
NLRP3 (NACHT LRR PYD domain protein 3) modulators, such as BMS-986299;
RIG-I agonists, such as RGT-100;
Aerolysin stimulators, such as topsalysin;
P-Glycoprotein 1 inhibitors, such as HM-30181A;
CSF-1 antagonists, such as ARRY-382, BLZ-945;
CCR8 inhibitors, such as 1-309, SB-649701, HG-1013, RAP-310;
anti-Mesothelin antibodies, such as SEL-403;
Thymidine kinase stimulators, such as aglatimagene besadenovec;
Polo-like kinase 1 inhibitors, such as PCM-075, onvansertib;
NAE inhibitors, such as pevonedistat (MLN-4924), TAS-4464; Pleiotropic pathway modulators, such as avadomide (CC-122);
Amyloid protein binding protein-1 inhibitorS/Ubiquitin ligase modulators, such as pevonedistat;
FoxMl inhibitors, such as thiostrepton;
UBA1 inhibitors, such as TAK-243;
Src tyrosine kinase inhibitors, such as VAL-201;
VDAC/HK inhibitors, such as VDA-1102;
Elf4a inhibitors, such as rohinitib, eFT226;
TP53 gene stimulators, such as ad-p53;
Retinoic acid receptor agonists, such as tretinoin;
Retinoic acid receptor alpha (RARa) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitors, such as irinotecan hydrochloride, Onivyde;
Topoisomerase I inhibitor/hypoxia inducible factor-1 alpha inhibitors, such as PEG-SN38 (firtecan pegol);
Hypoxia inducible factor-1 alpha inhibitors, such as PT-2977, PT-2385;
CD122 (IL-2 receptor) agonists, such as proleukin (aldesleukin, IL-2); pegylated IL-2 (eg NKTR-214); modified variants of IL-2 (eg THOR-707);
TLR7/TLR8 agonist, such as NKTR-262;
TLR7 agonists, such as DS-0509, GS-9620, LHC-165, TMX-101 (imiquimod);
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as Pegilodecakin (AM-0010);
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);

Second mitochondria-derived activator of caspases (SMAC) protein inhibitors, such as BI-891065;
Lactoferrin modulators, such as LTX-315;
KIT proto-oncogene, receptor tyrosine kinase (KIT) inhibitors, such as PLX-9486;
platelet derived growth factor receptor alpha (PDGFRA)/KIT proto-oncogene, receptor tyrosine kinase (KIT) mutant-specific antagonists/inhibitors such as BLU-285, DCC-2618;
Exportin 1 inhibitors, such as eltanexor;
CHST15 gene inhibitors, such as STNM-01;
Somatostatin receptor antagonist, such as OPS-201;
CEBPA gene stimulators, such as MTL-501;
DKK3 gene modulators, such as MTG-201;
Chemokine (CXCR1/CXCR2) inhibitors, such as SX-682;
p70s6k inhibitors, such as MSC2363318A;
methionine aminopeptidase 2 (MetAP2) inhibitors, such as M8891, APL-1202;
arginine N-methyltransferase 5 inhibitors, such as GSK-3326595;
CD71 modulators, such as CX-2029 (ABBV-2029);
ATM (ataxia telangiectasia) inhibitors, such as AZD0156, AZD1390;
CHK1 inhibitors, such as GDC-0575, LY2606368 (prexasertib), SRA737, RG7741 (CHK1/2);
CXCR4 antagonists, such as BL-8040, LY2510924, burixafor (TG-0054), X4P-002, X4P-00140, Plerixafor;
EXH2 inhibitors, such as GSK2816126;
KDM1 inhibitors, such as ORY-1001, IMG-7289, INCB-59872, GSK-2879552;
CXCR2 antagonists, such as AZD-5069;
GM-CSF antibodies, such as lenzilumab;
DNA dependent protein kinase inhibitors, such as MSC2490484A (nedisertib), VX-984, AsiDNA (DT-01); protein kinase C (PKC) inhibitors, such as LXS-196, sotrastaurin;
Selective estrogen receptor downregulators (SERD), such as fulvestrant (Faslodex®), RG6046, RG6047, RG6171, elacestrant (RAD-1901), SAR439859 and AZD9496;
Selective estrogen receptor covalent antagonists (SERCAs), such as H3B-6545;
selective androgen receptor modulator (SARM), such as GTX-024, darolutamide;
transforming growth factor-beta (TGF-beta) kinase antagonists, such as galunisertib, LY3200882; TGF-beta inhibitors described in WO 2019/103203;
TGF beta receptor 1 inhibitors, such as PF-06952229;
bispecific antibodies, such as ABT-165 (DLL4/VEGF), MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vanzicumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLECl₂A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3), AGEN1223, IMCgp100 (CD3/gp100), AGEN-1423, ATOR-1015 (CTLA-4/0X40), LY-3415244 (TIM-3/PDL1), INHIBRX-105 (4-1BB/PDL1), faricimab (VEGF-A/ANG-2), FAP-4-IBBL (4-1BB/FAP), XmAb-13676 (CD3/CD20), TAK-252 (PD-1/0X40L), TG-1801 (CD19/CD47), XmAb-18087 (SSTR2/CD3), catumaxomab (CD3/EpCAM), SAR-156597 (IL4/IL13), EMB-01 (EGFR/cMET), REGN-4018 (MUC16/CD3), REGN-1979 (CD20/CD3), RG-7828 (CD20/CD3), CC-93269 (CD3/BCMA), REGN-5458 (CD3/BCMA), navicixizumab (DLL4/VEGF), GRB-1302 (CD3/Erbb2), vanuci-zumab (VEGF-A/ANG-2), GRB-1342 (CD38/CD3), GEM-333 (CD3/CD33), IMM-0306 (CD47/CD20), RG6076, MEDI5752 (PD-1/CTLA-4), LY3164530 (MET/EGFR);
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2), IDH-305, BAY-1436032;
IDH1 gene inhibitors, such as ivosidenib;
interleukin-3 receptor (IL-3R) modulators, such as SL-401;
Arginine deiminase stimulators, such as pegargiminase (ADI-PEG-20);
claudin-18 inhibitors, such as claudiximab;
β-catenin inhibitors, such as CWP-291;
chemokine receptor 2 (CCR) inhibitors, such as PF-04136309, CCX-872, BMS-813160 (CCR2/CCR5);
thymidylate synthase inhibitors, such as ONX-0801;
ALK/ROS1 inhibtors, such as lorlatinib;
tankyrase inhibitors, such as G007-LK;
Mdm2 p53-binding protein inhibitors, such as CMG-097, HDM-201; c-PIM inhibitors, such as PIM447;
sphingosine kinase-2 (SK₂) inhibitors, such as Yeliva® (ABC294640);
DNA polymerase inhibitors, such as sapacitabine;
Cell cycle/Microtubule inhibitors, such as eribulin mesylate;
c-MET inhibitors, such as AMG-337, savolitinib, tivantinib (ARQ-197), capmatinib, and tepotinib, ABT-700, AG213, AMG-208, JNJ-38877618 (OMO-1), merestinib, HQP-8361;
c-Met/VEGFR inhibitors, such as BMS-817378, TAS-115;
c-Met/RON inhibitors, such as BMS-777607;
BCR/ABL inhibitors, such as rebastinib, asciminib, ponatinib (ICLUSIG®);
MNK1/MNK2 inhibitors, such as eFT-508;
Cytochrome P450 11B2/Cytochrome P450 17/AKT protein kinase inhibitors, such as LAE-201;
Cytochrome P450 3A4 stimulators, such as mitotane;
lysine-specific demethylase-1 (LSD1) inhibitors, such as CC-90011;
CSF1R/KIT and FLT3 inhibitors, such as pexidartinib (PLX3397);
Flt3 tyrosine kinase/Kit tyrosine kinase inhibitor and PDGF receptor antagonists, such as quizartinib dihydrochloride;
kinase inhibitors, such as vandetanib;
E selectin antagonists, such as GMI-1271;
differentiation inducers, such as tretinoin;

epidermal growth factor receptor (EGFR) inhibitors, such as osimertinib (AZD-9291), cetuximab;

topoisomerase inhibitors, such as Adriamycin, doxorubicin, daunorubicin, dactinomycin, DaunoXome, Caelyx, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114);

corticosteroids, such as cortisone, dexamethasone, hydrocortisone, methylprednisolone, prednisone, prednisolone;

growth factor signal transduction kinase inhibitors;

nucleoside analogs, such as DFP-10917;

Ax1 inhibitors, such as BGB-324 (bemcentinib), SLC-0211;

Ax1/Flt3 inhibitors, such as gilteritinib;

Inhibitors of bromodomain and extraterminal motif (BET) proteins, including ABBV-744, BRD2 (NCBI Gene ID: 6046), BRD3 (NCBI Gene ID: 8019), BRD4 (NCBI Gene ID: 23476), and bromodomain testis-specific protein (BRDT; NCBI Gene ID: 676), such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, CC-95775, mivebresib, BI-894999, PLX-2853, PLX-51107, CPI-0610, GS-5829;

PARP inhibitors, such as olaparib (MK7339), rucaparib, veliparib, talazoparib, ABT-767, BGB-290, fluzolepali (SHR-3162), niraparib (JNJ-64091742), bendamustine hydrochloride, PARP/Tankyrase inhibitors such as 2X-121 (e-7499);

IMP-4297, SC-10914, IDX-1197, HWH-340, CK-102, simmiparib;

Proteasome inhibitors, such as ixazomib (NINLARO®), carfilzomib (Kyprolis®), marizomib, bortezomib;

Glutaminase inhibitors, such as CB-839 (telaglenastat), bis-2-(5-phenylacetamido-1,3,4-thiadiazol-2-yl)ethyl sulfide (BPTES);

mitochondrial complex I inhibitors, such as metformin, phenformin;

Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131, peptide subunit vaccine (acute lymphoblastic leukemia, University Children's Hospital Tuebingen); bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, tapuldencel-T, eltrapuldencel-T, SL-701, BSKO1TM, rocapuldencel-T (AGS-003), DCVAC, CVactm, stapuldencel-T, eltrapuldencel-T, SL-701, BSKO1TM, ADXS31-142, autologous dendritic cell vaccine (metastatic malignant melanoma, intradermal/intravenous, Universitatsklinikum Erlangen); oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, CreaVax-BC, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000; 10-103; Neoantigen peptide vaccines, such as AGEN-2017, GEN-010, NeoVax, RG-6180, GEN-009, PGV-001 (TLR-3 agonist), GRANITE-001, NEO-PV-01; Peptide vaccines that target heat shock proteins, such as PhosphoSynVax™; Vitespen (HSPPC-96-C), NANT Colorectal Cancer Vaccine containing aldoxorubicin, autologous tumor cell vaccine+systemic CpG-B+IFN-alpha (cancer), IO-120+IO-103 (PD-L1/PD-L2 vaccines), HB-201, HB-202, HB-301, TheraT®*-based vaccines, TLR-3 agonist/interferon inducers, such as Poly-ICLC (NSC-301463);

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);

interferon gamma ligand modulators, such as interferon gamma (OH-6000, Ogamma 100);

IL-6 receptor modulators, such as tocilizumab, AS-101 (CB-06-02, IVX-Q-101);

Heat shock protein inhibitors/IL-6 receptor antagonists, such as siltuximab;

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacytidine (CC-486);

DNA gyrase inhibitors, such as pixantrone and sobuzoxane;

DNA gyrase inhibitors/Topoisimerase II inhibitors, such as amrubicin;

Bcl-2 family protein inhibitors, such as ABT-263, venetoclax (ABT-199), ABT-737, RG7601, and AT-101;

Bcl-2/Bcl-XL inhibitors, such as novitoclax;

Notch inhibitors, such as LY3039478 (crenigacestat), tarextumab (anti-Notch2/3), BMS-906024;

hyaluronidase stimulators, such as PEGPH-20;

Erbb2 tyrosine kinase receptor inhibitors/Hyaluronidase stimulators, such as Herceptin Hylecta;

Wnt pathway inhibitors, such as SM-04755, PRI-724, WNT-974;
gamma-secretase inhibitors, such as PF-03084014, MK-0752, RO-4929097;
Grb-2 (growth factor receptor bound protein-2) inhibitors, such as BP1001;
TRAIL pathway-inducing compounds, such as ONC201, ABBV-621;
TRAIL modulators, such as SCB-313;
Focal adhesion kinase inhibitors, such as VS-4718, defactinib, GSK2256098;
hedgehog inhibitors, such as saridegib, sonidegib (LDE225), glasdegib;
Aurora kinase inhibitors, such as alisertib (MLN-8237), and AZD-2811, AMG-900, barasertib, ENMD-2076;
HSPB1 modulators (heat shock protein 27, HSP27), such as brivudine, apatorsen;
ATR inhibitors, such as BAY-937, AZD6738, AZD6783, VX-803, VX-970 (berzosertib) and VX-970;
Hsp90 inhibitors, such as AUY922, onalespib (AT13387), SNX-2112, SNX5422;
Murine double minute (mdm2) oncogene inhibitors, such as DS-3032b, RG7775, AMG-232, HDM201, and idasanutlin (RG7388);
CD137 agonists, such as urelumab, utomilumab (PF-05082566), AGEN2373, ADG-106, BT-7480;
STING agonists, such as ADU-S100 (MIW-815), SB-11285, MK-1454, SR-8291, AdVCA0848, GSK-532, SYN-STING, MSA-1, SR-8291, GSK3745417;
FGFR inhibitors, such as FGF-401, INCB-054828, BAY-1163877, AZD4547, JNJ-42756493, LY2874455, Debio-1347;
fatty acid synthase (FASN) inhibitors, such as TVB-2640;
Antigen CD19 inhibitors, such as MOR208, MEDI-551, AFM-11, inebilizumab;
CD44 binders, such as A6;
protein phosphatase 2A (PP2A) inhibitors, such as LB-100;
CYP17 inhibitors, such as seviteronel (VT-464), ASN-001, ODM-204, CFG920, abiraterone acetate;
RXR agonists, such as IRX4204;
hedgehog/smoothened (hh/Smo) antagonists, such as taladegib, patidegib, vismodegib;
complement C3 modulators, such as Imprime PGG;
IL-15 agonists, such as ALT-803, NKTR-255, interleukin-15/Fc fusion protein, AM-0015, NIZ-985, and hetIL-15;
EZH2 (enhancer of zeste homolog 2) inhibitors, such as tazemetostat, CPI-1205, GSK-2816126, PF-06821497;
Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301, IMLYGIC®;
DOT1L (histone methyltransferase) inhibitors, such as pinometostat (EPZ-5676);
toxins such as Cholera toxin, ricin, Pseudomonas exotoxin, Bordetella pertussis adenylate cyclase toxin, diphtheria toxin, and caspase activators;
DNA plasmids, such as BC-819;
PLK inhibitors of PLK 1, 2, and 3, such as volasertib (PLK1);
WEE1 inhibitors, such as AZD-1775 (adavosertib); Rho kinase (ROCK) inhibitors, such as AT13148, KD025;
Inhibition of Apoptosis Protein (IAP) inhibitors, such as ASTX660, debio-1143, birinapant, APG-1387, LCL-161;
RNA polymerase inhibitors, such has lurbinectedin (PM-1183), CX-5461;
Tubulin inhibitors, such as PM-184, BAL-101553 (lisavanbulin), and OXI-4503, fluorapacin (AC-0001), plinabulin, vinflunine;
Toll-like receptor 4 (TLR-4) agonists, such as G100, GSK1795091, and PEPA-10;
Elongation factor 1 alpha 2 inhibitors, such as plitidepsin;
Elongation factor 2 inhibitors/Interleukin-2 ligands/NAD ADP ribosyltransferase stimulators, such as denileukin diftitox;
CD95 inhibitors, such as APG-101, APO-010, asunercept;
WT1 inhibitors, such as DSP-7888;
splicing factor 3B subunitl (SF3B1) inhibitors, such as H3B-8800
retinoid Z receptor gamma (RORy) agonists, such as LYC-55716; and
Microbiome modulators, such as SER-401, EDP-1503, MRx-0518.

In some embodiments, a compound as described herein, is co-administered with one or more additional therapeutic agents comprising an inhibitor or antagonist of: myeloid cell leukemia sequence 1 (MCL1) apoptosis regulator (NCBI Gene ID: 4170); mitogen-activated protein kinase 1 (MAP4K1) (also called Hematopoietic Progenitor Kinase 1 (HPK1), NCBI Gene ID: 11184); diacylglycerol kinase alpha (DGKA, DAGK, DAGK1 or DGK-alpha; NCBI Gene ID: 1606); 5'-nucleotidase ecto (NT5E or CD73; NCBI Gene ID: 4907); ectonucleoside triphosphate diphosphohydrolase 1 (ENTPD1 or CD39; NCBI Gene ID: 593); transforming growth factor beta 1 (TGFBβ or TGFβ; NCBI Gene ID: 7040); heme oxygenase 1 (HMOX1, HO-1 or HO1; NCBI Gene ID: 3162); heme oxygenase 2 (HMOX2, HO-2 or H02; NCBI Gene ID: 3163); vascular endothelial growth factor A (VEGFA or VEGF; NCBI Gene ID: 7422); erb-b2 receptor tyrosine kinase 2 (ERBB2, HER2, HER2/neu or CD340; NCBI Gene ID: 2064), epidermal growth factor receptor (EGFR, ERBB, ERBB1 or HER1; NCBI Gene ID: 1956); ALK receptor tyrosine kinase (ALK, CD246; NCBI Gene ID: 238); poly(ADP-ribose) polymerase 1 (PARP1; NCBI Gene ID: 142); poly(ADP-ribose) polymerase 2 (PARP2; NCBI Gene ID: 10038); TCDD inducible poly(ADP-ribose) polymerase (TIPARP, PARP7; NCBI Gene ID: 25976); cyclin dependent kinase 4 (CDK4; NCBI Gene ID: 1019); cyclin dependent kinase 6 (CDK6; NCBI Gene ID: 1021); TNF receptor superfamily member 14 (TNFRSF14, HVEM, CD270; NCBI Gene ID: 8764); T cell immunoreceptor with Ig and ITIM domains (TIGIT; NCBI Gene ID: 201633); X-linked inhibitor of apoptosis (XIAP, BIRC4, IAP-3; NCBI Gene ID: 331); baculoviral IAP repeat containing 2 (BIRC2, cIAP1; NCBI Gene ID: 329); baculoviral IAP repeat containing 3 (BIRC3, cIAP2; NCBI Gene ID: 330); baculoviral IAP repeat containing 5 (BIRC5, surviving; NCBI Gene ID: 332); C-C motif chemokine receptor 2 (CCR2, CD192; NCBI Gene ID: 729230); C-C motif chemokine receptor 5 (CORS, CD195; NCBI Gene ID: 1234); C-C motif chemokine receptor 8 (CCR8, CDw198; NCBI Gene ID: 1237); C-X-C motif chemokine receptor 2 (CXCR2, CD182; NCBI Gene ID: 3579); C-X-C motif chemokine receptor 3 (CXCR3, CD182, CD183; NCBI Gene ID: 2833); C-X-C motif chemokine receptor 4 (CXCR4, CD184; NCBI Gene ID: 7852); arginase (ARG1 (NCBI Gene ID: 383), ARG2 (NCBI Gene ID: 384)), carbonic anhydrase (CA1 (NCBI Gene ID: 759), CA2 (NCBI Gene ID: 760) CA3 (NCBI Gene ID: 761), CA4 (NCBI Gene ID: 762), CASA (NCBI Gene ID: 763), CA5B (NCBI Gene ID: 11238), CA6 (NCBI Gene ID: 765), CA7

(NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOXS, 5-LOX; NCBI Gene ID: 240) and/or soluble epoxide hydrolase 2 (EPHX2, SEH; NCBI Gene ID: 2053); a secreted phospholipase A2 (e.g., PLA2G1B (NCBI Gene ID: 5319); PLA2G7 (NCBI Gene ID: 7941), PLA2G3 (NCBI Gene ID: 50487), PLA2G2A (NCBI Gene ID: 5320); PLA2G4A (NCBI Gene ID: 5321); PLA2G12A (NCBI Gene ID: 81579); PLA2G12B (NCBI Gene ID: 84647); PLA2G10 (NCBI Gene ID: 8399); PLA2G5 (NCBI Gene ID: 5322); PLA2G2D (NCBI Gene ID: 26279); PLA2G15 (NCBI Gene ID: 23659)); indoleamine 2,3-dioxygenase 1 (IDO1; NCBI Gene ID: 3620); indoleamine 2,3-dioxygenase 2 (IDO2; NCBI Gene ID: 169355); hypoxia inducible factor 1 subunit alpha (HIF1A; NCBI Gene ID: 3091); angiopoietin 1 (ANGPT1; NCBI Gene ID: 284); Endothelial TEK tyrosine kinase (TIE-2, TEK, CD202B; NCBI Gene ID: 7010); Janus kinase 1 (JAK1; NCBI Gene ID: 3716); catenin beta 1 (CTNNB1; NCBI Gene ID: 1499); histone deacetylase 9 (HDAC9; NCBI Gene ID: 9734) and/or 5'-3' exoribonuclease 1 (XRN1; NCBI Gene ID: 54464).

TCR Signaling Modulators

In various embodiments, a compound as described herein, is combined with one or more agonist or antagonist of T-Cell Receptor (TCR) signaling modulators. Activation of T cells through the TCR and is essential for thymocyte development and effector T cell function. TCR activation promotes signaling cascades that ultimately determine cell fate through regulating cytokine production, cell survival, proliferation, and differentiation. Examples of TCR signaling modulators include without limitation CD2 (cluster of differentiation 2, LFA-2, T11, LFA-3 receptor), CD3 (cluster of differentiation 3), CD4 (cluster of differentiation 4), CD8 (cluster of differentiation 8), CD28 (cluster of differentiation 28), CD45 (PTPRC, B220, GP180), LAT (Linker for activation of T cells, LAT1), Lck, LFA-1 (ITGB2, CD18, LAD, LCAMB), Src, Zap-70, SLP-76, DGKalpha, CBL-b, CISH, HPK1.

Examples of agonist of cluster of differentiation 3 (CD3) that can be co-administered include without limitation MGD015.

In various embodiments, a compound as described herein, is combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In various embodiments, the immune checkpoint proteins or receptors regulate T cell responses (e.g., reviewed in Xu, et al., *J Exp Clin Cancer Res*. (2018) 37:110). In various embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (PDL1, PD-L1); programmed cell death 1 (PDCD1, PD-1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM-3); galectin 9 (LGALS9); lymphocyte activating 3 (LAG-3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor(KIR); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1).

In various embodiments, a compound as described herein, is combined with one or more blockers or inhibitors of one or more T-cell inhibitory immune checkpoint proteins or receptors. Illustrative T-cell inhibitory immune checkpoint proteins or receptors include without limitation CD274 (PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H$_3$); V-set domain containing T cell activation inhibitor 1 (VTCN1, B7H4); V-set immunoregulatory receptor (VSIR, B7H5, VISTA); immunoglobulin superfamily member 11 (IGSF11, VSIG3);

TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG-3, CD223); hepatitis A virus cellular receptor 2 (HAVCR2, TIMD3, TIM-3); galectin 9 (LGALS9); killer cell immunoglobulin like receptor(KIR); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, a compound as described herein, is combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In various embodiments, a compound as described herein, is combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, a compound as described herein, is combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In various embodiments, a compound as described herein, is combined with an inhibitor of CD47 (IAP, MER6, OA3; NCBI Gene ID: 961). Examples of CD47 inhibitors include without limitation to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, ALX-148, TTI-621, RRx-001, DSP-107, VT-1021, TTI-621, TTI-622, IMM-02 SGN-CD47M. Examples bi-specific antibodies targeting CD47, such as IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33). Examples of anti-CD47antibodies, such as IBI-188, TJC-4, SHR-1603, HLX-24, LQ-001, IMC-002, ZL-1201, IMM-01, B6H12, GenSci-059, TAY-018, PT-240, 1F8-GMCSF, SY-102, KD-015

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, HBM-4003, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors/antibodies of PD-L1 (CD274) or PD-1 (PDCD1) that can be co-administered include without limitation pembrolizumab, nivolumab, cemiplimab, pidilizumab, AMG-404, AMP-224, MEDI0680 (AMP-514), spartalizumab, atezolizumab, avelumab, durvalumab, BMS-936559, CK-301, PF-06801591, BGB-A317 (tislelizumab), GEN-1046 (PD-L1/4-1BB), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), RO-7247669 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM-3/PDL1), RG7769 (PD-1/TIM-3) and INBRX-105 (4-1BB/PDL1), GNS-1480 (PD-L1/EGFR), RG-7446 (Tecentriq, atezolizumab), ABBV-181, nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317 (tislelizumab), GLS-010 (WBP-3055), AK-103 (HX-008), CS-1003, HLX-10, MGA-012, BI-754091, REGN-2810 (cemiplimab), AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, AK-105, PD1-PIK, BAT-1306, BMS-936559, atezolizumab (MPDL3280A), durvalumab (MEDI-4736), avelumab, CK-301,(MSB0010718C), MEDI-0680, CX-072, CBT-502, PDR-001 (spartalizumab), PDR001+Tafinlar®+Mekinist®, MSB-2311, JTX-4014, BGB-A333, SHR-1316, CS-1001

(WBP-3155, KN-035, IBI-308 (sintilimab), HLX-20, KL-A167, STI-A1014, STI-A1015 (IMC-001), BCD-135, FAZ-053, TQB-2450, and MDX1105-01.

Examples of inhibitors of PVRIG that can be co-administered include without limitation: COM-701.

Examples of inhibitors of TIGIT that can be co-administered include without limitation: BMS-986207, RG-6058, AGEN-1307, COM-902.

Examples of inhibitors of TIM-3 that can be co-administered include without limitation: TSR-022, LY-3321367, MBG-453, INCAGN-2390, RO-7121661 (PD-1/TIM-3), LY-3415244 (TIM-3/PDL1), RG7769 (PD-1/TIM-3).

Examples of inhibitors of LAG-3 that can be co-administered include without limitation: relatlimab (ONO-4482), LAG-525, MK-4280, REGN-3767, INCAGN2385, TSR-033, MGD-013 (PD-1/LAG-3), FS-118 (LAG-3/PD-L1).

Examples of anti-killer cell immunoglobulin like receptor, three Ig domains and long cytoplasmic tail 1 (KIR3DL1; KIR; NCBI Gene ID: 3811) monoclonal antibodies, such as lirilumab (IPH-2102), IPH-4102.

Examples of anti-NKG2a antibodies that can be co-administered include without limitation: monalizumab.

Examples of anti-VISTA antibodies that can be co-administered include without limitation: HMBD-002, CA-170 (PD-L1/VISTA).

Examples of anti-CD70 antibodies that can be co-administered include without limitation: AMG-172.

Examples of anti-CD20 antibodies that can be co-administered include without limitation: obinutuzumab, IGN-002, PF-05280586.

Examples of anti-ICOS antibodies that can be co-administered include without limitation: JTX-2011, GSK3359609.

Examples of ICOS agonists that can be co-administered include without limitation: ICOS-L.COMP (Gariepy, J. et al. 106th Annu Meet Am Assoc Immunologists (AAI) (May 9-13, San Diego) 2019, Abst 71.5).

TNF Receptor Superfamily (TNFRSF) Member Agonists or Activators

In various embodiments, a compound as described herein, is combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Examples anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Examples anti-TNF receptor superfamily member 10b (TNFRSF10B, DR5, TRAILR2) antibodies that can be co-administered include without limitation, such as DS-8273, CTB-006, INB RX-109, GEN-1029;

Examples of anti-TNFRSF5 (CD40) antibodies that can be co-administered include without limitation RG7876, SEA-CD40, APX-005M and ABBV-428, ABBV-927, JNJ-64457107.

Examples of anti-TNFRSF7 (CD27) that can be co-administered include without limitation varlilumab (CDX-1127).

Example anti-TNFRSF9 (4-1BB, CD137) antibodies that can be co-administered include without limitation urelumab, utomilumab (PF-05082566), AGEN2373 and ADG-106.

Examples of anti-TNFRSF17 (BCMA) that can be co-administered include without limitation GSK-2857916.

Examples of anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Example anti-TRAILR1, anti-TRAILR2, anti-TRAILR3, anti-TRAILR4 antibodies that can be co-administered include without limitation ABBV-621.

Examples of Bi-specific antibodies targeting TNFRSF family members that can be co-administered include without limitation PRS-343 (CD-137/HER2), AFM26 (BCMA/CD16A), AFM-13 (CD16/CD30), REGN-1979 (CD20/CD3), AMG-420 (BCMA/CD3), INHIBRX-105 (4-1BB/PDL1), FAP-4-IBBL (4-1BB/FAP), XmAb-13676 (CD3/CD20), RG-7828 (CD20/CD3), CC-93269 (CD3/BCMA), REGN-5458 (CD3/BCMA), and IMM-0306 (CD47/CD20), AMG-424 (CD38.CD3).

Adenosine Generation and Signaling

In various embodiments, a compound as described herein, is combined with an agonist or antagonist of A1R, A2AR, A2BR, A3R, CD73, CD39, CD26.

Examples of Adenosine A3 receptor (A3R) agonists include namodenoson (CF102);

Examples of A2aR/A2bR antagonists include AB928;

Examples of anti-CD73 antibodies include MEDI-9447 (oleclumab), CPX-006, IPH-53, BMS-986179, NZV-930, CPI-006;

Examples of CD73 inhibitors include AB-680, PSB-12379, PSB-12441, PSB-12425, CB-708;

Examples of CD39/CD73 inhibitors include PBF-1662;

Examples of anti-CD39 antibodies include TTX-030;

Examples of Adenosine A2A receptor antagonists include CPI-444, AZD-4635, preladenant, PBF-509;

Examples of Adenosine deaminase inhibitors include pentostatin, cladribine;

Examples of Adenosine deaminase inhibitors include pentostatin, cladribine.

FLT3 Agonist

In various embodiments, a compound as described herein, is combined with an agonist of FLT3 (FLK2, STK1, CD135, FLK-2, Gene ID: 2322).

Examples of FLT3 agonist include without limitation, GS-3583, Sym-027, FLT3 agonist antibody (solid tumors), RIVAL-01, CDX-301, ONCR-177.

c-kit Targeting Agents

In various embodiments, a compound as described herein, is combined with an inhibitor of c-kit (PBT, SCFR, CD117, MASTC; NCBI Gene ID:3815).

Examples of c-kit inhibitors include imatinib mesylate, JSP-191, BLU-263, CD117-ADC, AZD3229 (c-kit/PDGFR inhibitor), telatinib (c-kit/PDGF/VEGF2 inhibitor), quizartinib dihydrochloride (FLT3/c-kit), pexidartinib hydrochloride (CSF1R/FLT3/c-kit), avapritinib (PDGFR/c-Kit inhibitor), vorolanib (multikinase VEGF/PDGFR/c-kit inhibitor), and ripretinib (c-kit/PDGFRα inhibitor);

Examples of c-kit multi-kinase inhibitors include dasatinib, imatinib, nilotinib, sorafenib, lenvatinib mesylate, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, HQP-1351, cabozantinib, ponatinib, and famitinib L-malate. Examples of anti-c-kit antibodies include CDX-0158, CDX-0159 and FSI-174.

SIRPalpha Targeting Agents

In various embodiments, a compound as described herein, is combined with an inhibitor of SIRPalpha (NCBI Gene ID: 140885).

Examples of SIRPalpha inhibitors include AL-008, RRx-001, and CTX-5861.

Examples of anti-SIRPalpha-antibodies include FSI-189, ES-004, BI765063, ADU1805, and CC-95251.

Bi-Specific T-Cell Engagers

In various embodiments, a compound as described herein, is combined with a bi-specific T-cell engager (e.g., not having an Fc) or an anti-CD3 bi-specific antibody (e.g., having an Fc). Illustrative anti-CD3 bi-specific antibodies or BiTEs that can be co-administered include AMG-160 (PSMA/CD3), AMG-212 (PSMA/CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), JNJ-64052781 (CD19/CD3), AMG-211 (CEA/CD3), BLINCYTO® (CD19/CD3), RG7802 (CEA/CD3), ERY-974 (CD3/GPC3), huGD2-BsAb (CD3/GD2), PF-06671008 (Cadherins/CD3), APV0436 (CD123/CD3), ERY974, flotetuzumab (CD123/CD3), GEM333 (CD3/CD33), GEMoab (CD3/PSCA), REGN-1979 (CD20/CD3), REGN-5678 (PSMA/CD28), MCLA-117 (CD3/CLEC1₂A), JNJ-0819, JNJ-7564 (CD3/heme), JNJ-63709178 (CD123/CD3), MGD-007 (CD3/gpA33), MGD-009 (CD3/B7H₃), IMCgp100 (CD3/gp100), XmAb-14045 (CD123/CD3), XmAb-13676 (CD3/CD20), XmAb-18087 (SSTR2/CD3), catumaxomab (CD3/EpCAM), REGN-4018 (MUC16/CD3), RG6026, RG6076, RG6194, RG-7828 (CD20/CD3), CC-93269 (CD3/BCMA), REGN-5458 (CD3/BCMA), GRB-1302 (CD3/Erbb2), GRB-1342 (CD38/CD3), GEM-333 (CD3/CD33), PF-06863135 (BCMA/CD3), SAR440234 (CD3/CDw123). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology*. (2017) May 17; 6(7):e1326437); PD-L1 (Horn, et al., *Oncotarget*. 2017 Aug. 3; 8(35):57964-57980); and EGFRvIII (Yang, et al., *Cancer Lett*. 2017 Sep. 10; 403:224-230).

Bi- and Tri-Specific Natural Killer (NK)-Cell Engagers

In various embodiments, a compound as described herein, is combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol*. (2016) 1441:333-346; Fang, et al., *Semin Immunol*. (2017) 31:37-54.

MCL1 Apoptosis Regulator, BCL2 Family Member (MCL1) Inhibitors

In various embodiments, a compound as described herein, is combined with an inhibitor of MCL1 apoptosis regulator, BCL2 family member (MCL1, TM; EAT; MCL1L; MCL1S; Mcl-1; BCL2L3; MCL1-ES; bcl2-L-3; mcll/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, and WO2017147410.

Hematopoietic Progenitor Kinase 1 (HPK1) Inhibitors

In various embodiments, a compound as described herein, is combined with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO-2018183956, WO-2018183964, WO-2018167147, WO-2018183964, WO-2016205942, WO-2018049214, WO-2018049200, WO-2018049191, WO-2018102366, WO-2018049152 and WO-2016090300.

Apoptosis Signal-Regulating Kinase (ASK) Inhibitors

In various embodiments, a compound as described herein, is combined with an inhibitor of an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include without limitation, those described in WO 2011/008709 (Gilead Sciences) and WO2013/112741 (Gilead Sciences).

Bruton Tyrosine Kinase (BTK) Inhibitors

In various embodiments, a compound as described herein, is combined with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, Calquence+AZD6738, and Calquence+danvatirsen.

Cyclin-Dependent Kinase (CDK) Inhibitors

In various embodiments, a compound as described herein, is combined with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3, NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; M015; STK1; CDKN7; p39MO15; NCBI Gene ID: 1022); cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include without limitation abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, PF-06873600, AZD4573, and TG-02.

Discoidin Domain Receptor (DDR) Inhibitors

In various embodiments, a compound as described herein, is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include without limitation, dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Histone Deacetylase (HDAC) Inhibitors

In various embodiments, a compound as described herein, is combined with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat, romidepsin, tucidinostat.

Indoleamine-pyrrole-2,3-dioxygenase (IDO1) Inhibitors

In various embodiments, a compound as described herein, is combined with an inhibitor of indoleamine 2,3-dioxygenase 1 (ID01; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Janus Kinase (JAK) Inhibitors

In various embodiments, a compound as described herein, is combined with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3 HUMAN, JAKL, L-JAK, LJAK; NCBI Gene ID: 3718). Examples of JAK inhibitors include without limitation, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

Matrix Metalloprotease (MMP) Inhibitors

In various embodiments, a compound as described herein, is combined with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP1 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include without limitation, marimastat (BB-2516), cipemastat (Ro 32-3555), GS-5745 (andecaliximab) and those described in WO 2012/027721 (Gilead Biologics).

RAS and RAS Pathway Inhibitors

In various embodiments, a compound as described herein, is combined with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893); HRas proto-oncogene, GTPase (HRAS; a.k.a., CTLO; KRAS; HAMSV; HRAS1; KRAS2; RASH1; RASK2; Ki-Ras; p21ras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR.

In various embodiments, a compound as described herein, is combined with an inhibitor of KRAS. Examples of KRAS inhibitors include AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2) (SEQ ID NO:1) and KRpep-2d (Ac-RRRRCPLYISYDPVCRRRR-NH2) (SEQ ID NO:2).

In various embodiments, a compound as described herein, is combined with an inhibitor of KRAS mRNA. Illustrative KRAS mRNA inhibitors include anti-KRAS U1 adaptor, AZD-4785, siG12D-LODER™, and siG12D exosomes.

In various embodiments, a compound as described herein, is combined with an inhibitor of MEK. Illustrative MEK inhibitors that can be co-administered include binimetinib, cobimetinib, PD-0325901, pimasertib, RG-7304, selumetinib, and trametinib.

In various embodiments, a compound as described herein, is combined with an inhibitor of AKT. Illustrative AKT inhibitors that can be co-administered include RG7440, MK-2206, ipatasertib, afuresertib, AZD5363, and ARQ-092, capivasertib, triciribine, ABTL-0812 (PI3K/Akt/mTOR).

In various embodiments, a compound as described herein, is combined with an inhibitor of Raf. Illustrative Raf inhibitors that can be co-administered BGB-283 (Raf/EGFR), HM-95573, LXH-254, LY-3009120, RG7304, TAK-580, dabrafenib, vemurafenib, encorafenib (LGX818), PLX8394. RAF-265 (Raf/VEGFR), ASN-003 (Raf/PI3K).

In various embodiments, a compound as described herein, is combined with an inhibitor of ERK. Illustrative ERK inhibitors that can be co-administered include LTT-462, LY-3214996, MK-8353, ravoxertinib, GDC-0994, and ulixertinib.

In various embodiments, a compound as described herein, is combined with an inhibitor of PI3K. Illustrative PI3K inhibitors that can be co-administered include idelalisib (Zydelig®), alpelisib, buparlisib, and pictilisib. Illustrative PI3K/mTOR inhibitors that can be co-administered include dactolisib, omipalisib, voxtalisib, gedatolisib, GSK2141795, and RG6114.

In various embodiments, a compound as described herein, is combined with an inhibitor of mTOR. Illustrative mTOR inhibitors that can be co-administered include as sapanisertib, vistusertib (AZD2014), ME-344, sirolimus (oral nano-amorphous formulation, cancer), and TYME-88 (mTOR/cytochrome P450 3A4).

In certain embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

In various embodiments, a compound as described herein, is combined with an inhibitor of RAS. Examples of RAS inhibitors include NEO-100, and rigosertib.

In various embodiments, a compound as described herein, is combined with an antagonist of EGFR, such as AMG-595, necitumumab, ABBV-221, depatuxizumab mafodotin (ABT-414), tomuzotuximab, ABT-806, vectibix, modotuximab, or RM-1929.

In various embodiments, a compound as described herein, is combined with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TN0155 (SHP-099), RMC-4550, JAB-3068, RMC-4630, SAR442720 and those described in WO2018172984 and WO2017211303.

In various embodiments, a compound as described herein, is combined with an inhibitor of mitogen-activated protein kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, CK-127, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib, TAK-733, CI-1040, RG7421.

Phosphatidylinositol 3-kinase (PI3K) Inhibitors

In various embodiments, a compound as described herein, is combined with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110 gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Mitogen-Activated Protein Kinase (MEK) Inhibitors

In various embodiments, a compound as described herein, is combined with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib.

Spleen Tyrosine Kinase (SYK) Inhibitors

In various embodiments, a compound as described herein, is combined with an inhibitor of spleen associated tyrosine kinase (SYK, p72-Syk, Gene ID: 6850). Examples of SYK inhibitors include without limitation, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

Toll-Like Receptor (TLR) Agonists

In various embodiments, a compound as described herein, is combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation DS-0509, GS-9620, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Examples of TLR8 inhibitors include, but are not limited to, E-6887, IMO-8400, IMO-9200 and VTX-763.

Examples of TLR8 agonists include, but are not limited to, MCT-465, motolimod, GS-9688, and VTX-1463.

Examples of TLR9 inhibitors include but are not limited to, AST-008, IMO-2055, IMO-2125, lefitolimod, litenimod, MGN-1601, and PUL-042.

Examples of TLR7/TLR8 agonist, such as NKTR-262, IMO-4200, MEDI-9197 (telratolimod), resiquimod;

Examples of TLR agonists include without limitation: lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.

Stimulator of Interferon Genes (STING)

Some embodiments, the therapeutic agent is a stimulator of interferon genes (STING) In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

Tyrosine-Kinase Inhibitors (TKIs)

In various embodiments, a compound as described herein, is combined with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation, axitinib, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, olmutinib, osimertinib (AZD-9291), pazopanib, ponatinib, poziotinib, quizartinib, radotinib, rociletinib, sulfatinib (HMPL-012), sunitinib, famitinib L-malate, (MAC-4), tivoanib, TH-4000, tivoanib, and MEDI-575 (anti-PDGFR antibody), TAK-659, Cabozantinib.

Indoleamine-pyrrole-2,3-dioxygenase (IDO1) Inhibitors

In various embodiments, a compound as described herein, is combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Chemotherapeutic Agents

In various embodiments, a compound as described herein, is combined with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiII), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223, 177-Lu-PSMA-617; trichothecenes, especially T-2 toxin, verracurin A, roridin A, and anguidine; taxoids such as paclitaxel (TAXOL®), abraxane,docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; phenamet; pirarubicin; losoxantrone; fluoropyrimidine; folinic acid; podophyllinic acid; 2-ethylhydrazide; procarbazine; poly saccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

An example progesterone receptor antagonist includes onapristone.

Anti-Angiogenic Agents

In various embodiments, a compound as described herein, is combined with an anti-angiogenic agent. Anti-angiogenic agents that can be co-administered include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, α,α'-dipyridyl, beta-aminopropionitrile fumarate, 4-propyl-5-(4-pyridinyl)-2(3 h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In various embodiments, a compound as described herein, is combined with an anti-fibrotic agent. Anti-fibrotic agents that can be co-administered include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl- 2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In various embodiments, a compound as described herein, is combined with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOXS, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include without limitation mofezolac, GLY-230, and TRK-700.

Examples of inhibitors of prostaglandin-endoperoxide synthase 2 (PTGS2, COX-2; NCBI Gene ID: 5743) that can be co-administered include without limitation diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, Anitrazafen, Apricoxib, Cimicoxib, Deracoxib, Flumizole, Firocoxib, Mavacoxib, NS-398, Pamicogrel, Parecoxib, Robenacoxib, Rofecoxib, Rutecarpine, Tilmacoxib, and Zaltoprofen. Examples of dual COX1/COX2 inhibitors that can be co-administered include without limitation, HP-5000, lornoxicam, ketorolac tromethamine, bromfenac sodium, ATB-346, HP-5000. Examples of dual COX-2/ carbonic anhydrase (CA) inhibitors that can be co-administered include without limitation polmacoxib and imrecoxib.

Examples of inhibitors of secreted phospholipase A2, prostaglandin E synthase (PTGES, PGES; Gene ID: 9536) that can be co-administered include without limitation LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., *Oncotarget.* (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include without limitation acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOXS, 5-LOX; NCBI Gene ID: 240) that can be co-administered include without limitation meclofenamate sodium, zileuton.

Examples of inhibitors of soluble epoxide hydrolase 2 (EPHX2, SEH; NCBI Gene ID: 2053) that can be co-administered include without limitation compounds described in WO2015148954. Dual inhibitors of COX-2/ SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include without limitation GS-4875, GS-5290, BHM-078 and those described, e.g., in WO2006124944, WO2006124692, WO2014064215, WO2018005435, Teli, et al., *J Enzyme Inhib Med Chem.* (2012) 27(4):558-70; Gangwall, et al., *Curr Top Med Chem.* (2013) 13(9):1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In various embodiments, a compound as described herein, is combined with an agent that promotes or increases tumor oxygenation or reoxygenation, or prevents or reduces tumor hypoxia. Illustrative agents that can be co-administered include, e.g., Hypoxia inducible factor-1 alpha (HIF-1a) inhibitors, such as PT-2977, PT-2385; VEGF inhibitors, such as bevasizumab, IMC-3C$_5$, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO 2007/137767, WO 2007/139791, WO 2014/107171, and WO 2016/149562.

Immunotherapeutic Agents

In various embodiments, a compound as described herein, is combined with an immunotherapeutic agent. Example immunotherapeutic agents that can be co-administered include without limitation abagovomab, ABP-980, adecatumumab, afutuzumab, alemtuzumab, altumomab, amatuximab, anatumomab, arcitumomab, bavituximab, bectumomab, bevacizumab, bevacizumab biosimilar, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, moxetumomab pasudotox, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, trastuzumab biosimilar, tucotuzumab, ubilituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein (e.g., in Table B). Example ADCs that can be co-administered include without limitation gemtuzumab, brentuximab, trastuzumab, inotuzumab, glembatumumab, anetumab, mirvetuximab, depatuxizumab, rovalpituzumab, vadastuximab, labetuzumab, sacituzumab, lifastuzumab, indusatumab, polatzumab, pinatuzumab, coltuximab, indatuximab, milatuzumab, rovalpituzumab, ABBV-011, ABBV-2029, ABBV-321, ABBV-647, MLN0264 (anti-GCC, guanylyl cyclase C), T-DM1 (trastuzumab emtansine, Kadcycla); SYD985 (anti-HER2, Duocarmycin), milatuzumab-doxorubicin (hCD74-DOX), brentuximab vedotin (ADCETRISC), DCDT2980S, belantamab mafodotin (GSK2857916), polatuzumab vedotin (RG-7596), SGN-CD70A, SGN-CD19A, inotuzumab ozogamicin (CMC-544), lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tetraxetan-tetuloma, tisotumab vedotin, anetumab ravtansine, CX-2009, SAR-566658, W-0101, ABBV-085, gemtuzumab ozogamicin, ABT-414, glembatumumab vedotin (CDX-011), labetuzumab govitecan (IMMU-130), sacituzumab govitecan (IMMU-132), lifastuzumab vedotin, (RG-7599), milatuzumab-doxorubicin (IMMU-110), indatuximab ravtansine (BT-062), pinatuzumab vedotin (RG-7593), SGN-LIV1A, SGN-CD33A, SAR566658, MLN2704, SAR408701, rovalpituzumab tesirine, ABBV-399, AGS-16C3F, ASG-22ME, AGS67E, AMG 172, AMG 595, AGS-15E, BAY1129980, BAY1187982, BAY94-934 (anetumab ravtansine), GSK2857916, Humax-TF-ADC (tisotumab vedotin), IMGN289, IMGN529, IMGN853 (mirvetuximab soravtansine), LOP628, PCA062, MDX-1203, MEDI-547, PF-06263507, PF-06647020, PF-06647263, PF-06664178, PF-06688992, PF-06804103, RG7450, RG7458, RG7598, SAR566658, SGN-CD33A, DS-1602 and DS-7300, DS-6157, DS-6000, TAK-164, MEDI2228, MEDI7247, AMG575. ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein.

Cancer Gene Therapy and Cell Therapy

In various embodiments, a compound as described herein, is combined with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In various embodiments, a compound as described herein, is combined with one or more cellular therapies. Illustrative cellular therapies include without limitation co-administration of one or more of a population of natural killer (NK) cells, NK-T cells, T cells, gamma delta T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments, the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H$_3$, a ligand that specifically binds with CD83, CDS, ICAM-1, GITR, BAFFR, HVEM (LIGHTR), SLAMF7, NKp80 (KLRFI), CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (αNeuSAc(2-8)αNeuSAc(2-3)βDGaip(1-4)bDGlcp(1-1) Cer); ganglioside GM3 (αNeuSAc(2-3)βDGalp(1-4) (βDGlcp(1-1)Cer); GM-CSF receptor; TNF receptor superfamily member 17 (TNFRSF17, BCMA); B-lymphocyte cell adhesion molecule; Tn antigen ((Tn Ag) or (GaINAcu-Ser/Thr)); prostate-specific membrane antigen (PSMA); Receptor tyrosine kinase-like orphan receptor 1 (RORI); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); HLA class I antigen A-2 alpha; HLA antigen; Lewis(Y)antigen; CD24; Platelet-derived growth factor receptor beta (PDGFR-beta); Stage-specificembryonic antigen-4 (SSEA-4); CD20; delta like 3 (DLL3); Folate receptor alpha; Folate receptor beta, GDNF alpha 4 receptor, Receptor tyrosine-protein kinase, ERBB2 (Her2/neu); Mucin 1, cell surface associated (MUC1); APRIL receptor; ADP ribosyl cyclase-1; Ephb4 tyrosine kinase receptor, DCAMKL1 serine threonine kinase, Aspartate beta-hydroxylase, epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Ab1) (bcr-abl); tyrosinase; ephrin type-A receptor 2 (EphA2); ephrin type-A receptor 3 (EphA3), Fucosyl GM1; sialyl Lewis adhesion molecule (sLe); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); IL-15 receptor (IL-15); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK$_2$); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma associated antigen 1 (MAGE-A1); Melanoma associated antigen 3 (MAGE-A3); Melanoma associated antigen 4 (MAGE-A4); T cell receptor beta 2 chain C; ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin-A1; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1(CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAXS); proacrosin binding protein sp32

(OY-TES I); lymphocyte-specific protein tyrosine kinase (LCK); A kinase anchor protein 4 (AKAP-4); Peptidoglycan recognition protein, synovial sarcoma, X breakpoint 2 (SSX2); Receptor for Advanced Glycation Endproducts (RAGE-I); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A ($CLECl_2A$); bone marrow stromal cell antigen 2 (BST2); EGF-like module containing mucin-like hormone receptor-like 2 (EMR2); lymphocyte antigen 75 (LY75); Glypican-2 (GPC2); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HERS in combination, HERV-K, HIV-1 envelope glycoprotein gp120, HIV-1 envelope glycoprotein gp41, HLA-DR, HLA class I antigen alpha G, HM1.24, K-Ras GTPase, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, Epstein-Barr nuclear antigen 1, Latent membrane protein 1, Secreted protein BARF1, P2X7 purinoceptor, Syndecan-1, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

Examples of cell therapies include without limitation: AMG-119, Algenpantucel-L, ALOFISEL®, Sipuleucel-T, (BPX-501) rivogenlecleucel US9089520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, SNK-01, NEXI-001, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, CSG-005, LAAP T-cell therapy, PD-1 knockout T cell therapy (esophageal cancer/NSCLC), anti-MUC1 CAR T-cell therapy (esophageal cancer/NSCLC), anti-MUC1 CAR T-cell therapy+PD-1 knockout T cell therapy (esophageal cancer/NSCLC), anti-KRAS G12D mTCR PBL, anti-CD123 CAR T-cell therapy, anti-mutated neoantigen TCR T-cell therapy, tumor lysate/MUC1/survivin PepTivator-loaded dendritic cell vaccine, autologous dendritic cell vaccine (metastatic malignant melanoma, intradermal/intravenous), anti-LeY-scFv-CD28-zeta CAR T-cells, PRGN-3005, iC9-GD2-CAR-IL-15 T-cells, HSC-100, ATL-DC-101, MIDRIX4-LUNG, MIDRIXNEO, anti-CD20 CAR T-cell therapy (non-Hodgkin's lymphoma), Additional Agents for Targeting Tumors Include Without Limitation:

Alpha-fetoprotein modulators, such as ET-1402, and AFP-TCR;

Anthrax toxin receptor 1 modulator, such as anti-TEM8 CAR T-cell therapy;

TNF receptor superfamily member 17 (TNFRSF17, BCMA), such as bb-2121 (ide-cel), bb-21217, JCARH125, UCART-BCMA, ET-140, KITE-585, MCM-998, LCAR-B38M, CART-BCMA, SEA-BCMA, BB212, ET-140, P-BCMA-101, AUTO-2 (APRIL-CAR), JNJ-68284528;

Anti-CLL-1 antibodies, such as KITE-796;

Anti-PD-L1-CAR tank cell therapy, such as KD-045

Anti-PD-L1 t-haNK, such as PD-L1 t-haNK;

anti-CD45 antibodies, such as 131I-BC8 (lomab-B);

anti-HER3 antibodies, such as LJM716, GSK2849330;

anti-CD52 antibodies, such as alemtuzumab;

APRIL receptor modulator, such as anti-BCMA CAR T-cell therapy, Descartes-011;

ADP ribosyl cyclase-1/APRIL receptor modulator, such as dual anti-BCMA/anti-CD38 CAR T-cell therapy; CART-ddBCMA;

B7 homolog 6, such as CAR-NKp30 and CAR-B7H6;

B-lymphocyte antigen CD19, such as TBI-1501, CTL-119 huCART-19 T cells,1 iso-cel, JCAR-015 US7446190, JCAR-014, JCAR-017, (WO2016196388, WO2016033570, WO2015157386), axicabtagene ciloleucel (KTE-C19, Yescarta®), KTE-X19, US7741465, US6319494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110; anti-CD19 CAR T-cell therapy (B-cell acute lymphoblastic leukemia, Universiti Kebangsaan Malaysia); anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem; UCAR-011, ICTCAR-014, GC-007F, PTG-01, CC-97540;
Allogeneic anti-CD19 CART cells, such as GC-007G;
APRIL receptor modulator; SLAM family member 7 modulator, BCMA-CS1 cCAR;
Autologous dendritic cell tumor antigen (ADCTA), such as ADCTA-SSI-G;
B-lymphocyte antigen CD20, such as ACTR707 ATTCK-20, PBCAR-20A;
Allogenic T cells expressing CD20 CAR, such as LB-1905;
B-lymphocyte antigen CD19/B-lymphocyte antigen 22, such as TC-310;
B-lymphocyte antigen 22 cell adhesion, such as UCART-22, JCAR-018 WO2016090190;
NY-ESO-1 modulators, such as GSK-3377794, TBI-1301, GSK3537142;
Carbonic anhydrase, such as DC-Ad-GMCAIX;
Caspase 9 suicide gene, such as CaspaClDe DLI, BPX-501;
CCR5, such as SB-728;
CCR5 gene inhibitor/TAT gene/TRIM5 gene stimulator, such as lentivirus vector CCR5 shRNA/TRIM5alpha/TAR decoy-transduced autologous CD34-positive hematopoietic progenitor cells;
CDw123, such as MB-102, IM-23, JEZ-567, UCART-123;
CD4, such as ICG-122;
CD5 modulators, such as CD5.28z CART cells;
Anti-CD22, such as anti-CD22 CART;
Anti-CD30, such as TT-11;
CD33, such as CIK-CAR.CD33, CD33CART;
Dual anti-CD33/anti-CLL1, such as LB-1910;
CD38, such as T-007, UCART-38;
CD40 ligand, such as BPX-201, MEDI5083;
CD56, such as allogeneic CD56-positive CD3-negative natural killer cells (myeloid malignancies);
CD19/CD7 modulator, such as GC-197;
T-cell antigen CD7 modulator, such as anti-CD7 CAR T-cell therapy (CD7-positive hematological malignancies);
CD123 modulator, such as UniCAR02-T-CD123;
CEACAM protein 5 modulators, such as MG7-CART;
Claudin 6, such as CSG-002; Claudin 18.2, such as LB-1904;
Chlorotoxin, such as CLTX-CART;
EBV targeted, such as CMD-003;
MUC16EGFR, such as autologous 4H11-28z/fIL-12/EFGRt T cell;
Endonuclease, such as PGN-514, PGN-201;
Epstein-Barr virus specific T-lymphocytes, such as TT-10;
Epstein-Barr nuclear antigen 1/Latent membrane protein 1/Secreted protein BARF1 modulator, such as TT-10X;
Erbb2, such as CST-102, CIDeCAR;
Ganglioside (GD2), such as 4SCAR-GD2;
Gamma delta T cells, such as ICS-200;
folate hydrolase 1 (FOLH1, Glutamate carboxypeptidase II, PSMA; NCBI Gene ID: 2346), such as CIK-CAR.PSMA, CART-PSMA-TGFPRDN, P-PSMA-101;
Glypican-3(GPC3), such as TT-16, GLYCAR;
Hemoglobin, such as PGN-236;
Hepatocyte growth factor receptor, such as anti-cMet RNA CAR T;
HLA class I antigen A-2 alpha modulator, such as FH-MCVA2TCR;
HLA class I antigen A-2 alpha/Melanoma associated antigen 4 modulator, such as ADP-A2M4CD8;
HLA antigen modulator, such as FIT-001, NeoTCR-P1;
Human papillomavirus E7 protein, such as KITE-439;
ICAM-1 modulator, such as AIC-100;
Immunoglobulin gamma Fc receptor III, such as ACTR087;
IL-12, such as DC-RTS-IL-12;
IL-12 agonist/mucin 16, such as JCAR-020;
IL-13 alpha 2, such as MB-101;
IL-15 receptor agonist, such as PRGN-3006;
IL-2, such as CST-101;
Interferon alpha ligand, such as autologous tumor cell vaccine+systemic CpG-B+IFN-alpha (cancer);
K-Ras GTPase, such as anti-KRAS G12V mTCR cell therapy;
Neural cell adhesion molecule L1 L1CAM (CD171), such as JCAR-023;
Latent membrane protein 1/Latent membrane protein 2, such as Ad5f35-LMPd1-2-transduced autologous dendritic cells;
MART-1 melanoma antigen modulator, such as MART-1 F5 TCR engineered PBMC;
Melanoma associated antigen 10, such as MAGE-A10C796T MAGE-A10 TCR;
Melanoma associated antigen 3/Melanoma associated antigen 6 (MAGE A3/A6) such as KITE-718;
Mesothelin, such as CSG-MESO, TC-210;
Mucin 1 modulator, such as ICTCAR-052, Tn MUC-1 CAR-T, ICTCAR-053;
Anti-MICA/MICB, such as CYAD-02;
NKG2D, such as NKR-2;
Ntrkrl tyrosine kinase receptor, such as JCAR-024;
PRAMET cell receptor, such as BPX-701;
Prostate stem cell antigen modulator, such as MB-105;
Roundabout homolog 1 modulator, such as ATCG-427;
Peptidoglycan recognition protein modulator, such as Tag-7 gene modified autologous tumor cell vaccine;
PSMA, such as PSMA-CAR T-cell therapy (lentiviral vector, castrate-resistant prostate cancer)
SLAM family member 7 modulator, such as IC9-Luc90-CD828Z;
TGF beta receptor modulator, such as DNR.NPC T-cells;
T-lymphocyte, such as TT-12;
T-lymphocyte stimulator, such as ATL-001;
TSH receptor modulator, such as ICTCAR-051;
Tumor infiltrating lymphocytes, such as LN-144, LN-145;
Wilms tumor protein, such as JTCR-016, WT1-CTL, ASP-7517;

Gene Editors

In various embodiments, a compound as described herein, is combined with gene editor. Illustrative gene editing system that can be co-administered include without limitation a CRISPR/Cas9 system, a zinc finger nuclease system, a TALEN system, a homing endonucleases system (e.g., an ARCUS), and a homing meganuclease system.

Other Targets

In various embodiments, a compound as described herein, is combined with human immunoglobulin (10% liquid formulation), Cuvitru (human immunoglobulin (20% solution), levofolinate disodium, IMSA-101, BMS-986288, IMUNO BGC Moreau RJ, R-OKY-034F, GP-2250, AR-23, calcium levofolinate, porfimer sodium, RG6160, ABBV-155, CC-99282, polifeprosan 20 with carmustine, Veregen, gadoxetate disodium, gadobutrol, gadoterate meglumine, gadoteridol, 99mTc-sestamibi, pomalidomide, pacibanil, valrubicin, Exemplified Combination Therapies
Lymphoma or Leukemia Combination Therapy Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), pomalidomide (POMALYST®/IMNOVID®)lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf C)), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VEL-CADE®, or other chemotherapeutic agents.

Other recent therapies for MCL have been disclosed. Such examples include flavopiridol, palbociclib (PD0332991), R-roscovitine (seliciclib, CYC202), styryl sulphones, obatoclax (GX15-070), TRAIL, Anti-TRAIL death receptors DR4 and DR5 antibodies, temsirolimus (TORISEL®, CCl-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and R ICE.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, radotinib, and cabozantinib.

Hyperproliferative Disorder Combination Therapy

Gemcitabine, nab-paclitaxel, and gemcitabine/nab-paclitaxel may be used with a JAK inhibitor and/or PI3Kδ inhibitor to treat hyperproliferative disorders.

Bladder Cancer Combination Therapy

Therapeutic agents used to treat bladder cancer include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast Cancer Combination Therapy

Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

Therapeutic agents used to treat triple negative breast cancer include cyclophosphamide, docetaxel, doxorubicin, epirubicin, fluorouracil, paclitaxel, and combinations thereof.

Colorectal Cancer Combination Therapy

Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

Therapeutic agents used to treat castration-resistant prostate cancer include abiraterone, cabazitaxel, docetaxel, enzalutamide, prednisone, sipuleucel-T, and any combinations thereof.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.
Hepatobiliary Cancer Combination Therapy
Therapeutic agents used to treat hepatobiliary cancer include capecitabine, cisplatin, fluoropyrimidine, 5-fluorourcil, gemecitabine, oxaliplatin, sorafenib, and any combinations thereof.
Hepatocellular Carcinoma Combination Therapy
Therapeutic agents used to treat hepatocellular carcinoma include capecitabine, doxorubicin, gemcitabine, sorafenib, and any combinations thereof.
Non-Small Cell Lung Cancer Combination Therapy
Therapeutic agents used to treat non-small cell lung cancer (NSCLC) include afatinib, albumin-bound paclitaxel, alectinib, bevacizumab, bevacizumab biosimilar, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.
Small Cell Lung Cancer Combination Therapy
Therapeutic agents used to treat small cell lung cancer (SCLC) include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.
Melanoma Combination Therapy
Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.
Ovarian Cancer Combination Therapy
Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.
Pancreatic Cancer Combination Therapy
Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.
Renal Cell Carcinoma Combination Therapy
Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

VI. Methods of Treatment

In some embodiments, the present disclosure provides method of inhibiting CD73 in a subject in need thereof, the method comprising administering to the subject a therapeutically effective amount of a compound of the present disclosure, or a pharmaceutically acceptable salt thereof, or a pharmaceutical composition of the present disclosure. In some embodiments, the present disclosure provides method of inhibiting CD73 in a subject in need thereof, the method comprising administering to the subject a therapeutically effective amount of a compound of Formula (I), (II-a), (II-b), (II-c), (II-d), (II-e), (II-f), (II-g), (II-h), (III-a), (III-b), (III-c), or (III-d) or a pharmaceutically acceptable salt thereof, or a pharmaceutical composition of the present disclosure.

In some embodiments, the present disclosure provides method of treating cancer in a subject in need thereof, the method comprising administering to the subject a therapeutically effective amount of a compound of the present disclosure, or a pharmaceutically acceptable salt thereof, or a pharmaceutical composition of the present disclosure. In some embodiments, the present disclosure provides method of treating cancer in a subject in need thereof, the method comprising administering to the subject a therapeutically effective amount of a compound of Formula (I), (II-a), (II-b), (II-c), (II-d), (II-e), (II-f), (II-g), (II-h), (III-a), (III-b), (III-c), or (III-d), or a pharmaceutically acceptable salt thereof, or a pharmaceutical composition of the present disclosure.

In some embodiments, the cancer is pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer, thyroid cancer or colon cancer. In some embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma or diffuse large B-cell lymphoma (DLBCL). In some embodiments, the cancer is brain (gliomas), glioblastomas, astrocytomas, glioblastoma multiforme, Bannayan-Zonana syndrome, Cowden disease, Lhermitte-Duclos disease, breast, colon, head and neck, kidney, lung, liver, melanoma, ovarian, pancreatic, adenocarcinoma, ductal adenocarcinoma, adenosquamous carcinoma, acinar cell carcinoma, glucagonoma, insulinoma, prostate, sarcoma or thyroid.

In some embodiments, the cancer is a solid tumor, a hematological cancer, or a metastatic lesion. In some embodiments, the solid tumor is a sarcoma, a fibroblastic sarcoma, a carcinoma, or an adenocarcinoma. In some embodiments, the hematological cancer is a leukemia, a lymphoma, or a myeloma.

In some embodiments, the cancer is a lung cancer, a melanoma, a renal cancer, a liver cancer, a myeloma, a prostate cancer, a breast cancer, an ovarian cancer, a colorectal cancer, a pancreatic cancer, a head and neck cancer, an anal cancer, a gastro-esophageal cancer, a mesothelioma, a nasopharyngeal cancer, a thyroid cancer, a cervical cancer, an epithelial cancer, a peritoneal cancer, a lymphoproliferative disease, an acute lymphoblastic leukemia (ALL), an acute myelogenous leukemia (AML), a chronic lymphocytic leukemia (CLL), a chronic myelogenous leukemia (CML), a chronic myelomonocytic leukemia (CMML), a hairy cell leukemia, a B cell lymphoma, a diffuse large B-cell lymphoma (DLBCL), an activated B-cell like (ABC) diffuse large B cell lymphoma, a germinal center B cell (GCB) diffuse large B cell lymphoma, a mantle cell lymphoma, a Hodgkin lymphoma, a non-Hodgkin lymphoma, a relapsed non-Hodgkin lymphoma, a refractory non-Hodgkin lymphoma, a recurrent follicular non-Hodgkin lymphoma, a Burkitt lymphoma, a small lymphocytic lymphoma, a follicular lymphoma, a lymphoplasmacytic lymphoma, or an extranodal marginal zone lymphoma.

In some embodiments, the cancer is an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), or a lymphoma.

In some embodiments, the cancer is a solid tumor in or arising from a tissue or organ selected from the group consisting of: bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma); lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors); esophagus (e.g., Barrett's esophagus, dysplasia and adenocarcinoma); gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus; pancreas (e.g., serous neoplasms, including microcystic or macrocystic serous cystadenoma, solid serous cystadenoma, Von Hippel-Landau (VHL)-associated serous cystic neoplasm, serous cystadenocarcinoma, mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma); gall bladder (e.g. carcinoma of the gallbladder and extrahepatic bile ducts, intrahepatic cholangiocarcinoma); neuro-endocrine (e.g., adrenal cortical carcinoma, carcinoid tumors, phaeochromocytoma, pituitary adenomas); thyroid (e.g., anaplastic (undifferentiated) carcinoma, medullary carcinoma, oncocytic tumors, papillary carcinoma, adenocarcinoma); liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma, hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor); kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma); breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma, lobular carcinoma, including without limitation, pleomorphic carcinoma, signet ring cell carcinoma, peritoneum (e.g., mesothelioma, primary peritoneal cancer)); female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, mullerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina; male sex organ tissues, including prostate, testis (e.g., germ cell tumors, spermatocytic seminoma), penis; bladder (e.g., squamous cell carcinoma, urothelial carcinoma, bladder urothelial carcinoma); brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas, pituitary tumors; eye (e.g., retinoma, retinoblastoma, ocular melanoma, posterior uveal melanoma, iris hamartoma); head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal); thymus (e.g., thymoma); heart (e.g., cardiac myxoma); lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma); lymph (e.g., lymphomas, including Hodgkin's lymphoma, non-Hodgkin's lymphoma, Epstein-Barr virus (EBV)-associated lymphoproliferative diseases, including B cell lymphomas and T cell lymphomas (e.g., Burkitt lymphoma, large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis); central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, pituitary adenomas, cranial and paraspinal nerve tumors, stellar region tumors), neurofibroma, meningioma, peripheral nerve sheath tumors, peripheral neuroblastic tumours (including without limitation neuroblastoma, ganglioneuroblastoma, ganglioneuroma), trisomy 19 ependymoma); neuroendocrine tissues (e.g., paraganglionic system including adrenal medulla (pheochromocytomas) and extra-adrenal paraganglia ((extra-adrenal) paragangliomas); skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, bpoblastoma, lipoma, chondroid lipoma, bposarcoma/malignant lipomatous tumors, bposarcoma, myxoid bposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non rhabdomyosarcoma soft tissue sarcoma (NRSTS), soft tissue leiomyosarcoma, undifferentiated sarcoma, well-differentiated bposarcoma.

In some embodiments, the cancer is a melanoma, a gastric cancer, a triple-negative breast cancer (TNBC), a non-small cell lung cancer (NSCLC), a rectal adenocarcinoma, a colorectal cancer, a renal cell carcinoma, an ovarian cancer, a prostate cancer, an oral squamous cell carcinoma (SCC), a head and neck squamous cell carcinoma (HNSCC), a urothelial bladder cancer, a glioblastoma (GBM), a meningioma, adrenal cancer, or an endometrial cancer.

In some embodiments, the method further comprises administering one or more additional therapeutic agents to the subject. The additional therapeutic agent can include any therapeutic agent described above for combination therapy. In some embodiments, the additional therapeutic agent is independently an anti-neoplastic agent, nivolumab, pembrolizumab, atezolizumab, ipilimumab, chemotherapy, radiation therapy, or resection therapy. In some embodiments, the additional therapeutic agent is independently rituxan, doxorubicin, gemcitabine, nivolumab, pembrolizumab, nivolumab, pembrolizumab, atezolizumab, or ipilimumab.

In some embodiments, the additional therapeutic agent is a PD-1/PD-L1 inhibitor.

In some embodiments, the anti-neoplastic agent is an anti-microtubule agent, a platinum coordination complex, an alkylating agent, an antibiotic agent, a topoisomerase II inhibitor, an antimetabolite, a topoisomerase I inhibitor, a hormone or hormonal analogue, a signal transduction pathway inhibitor, a non-receptor tyrosine kinase angiogenesi, an inhibitor, an immunotherapeutic agent, a proapoptotic agent, a cell cycle signaling inhibitor, a proteasome inhibitor, a inhibitor of cancer metabolism, an anti-PD-L1 agent, a PD-1 antagonist, an immuno-modulator, a STING modulating compound, a CD39 inhibitor, an A2a and A2a adenosine antagonist, a TLR4 antagonist, an antibody to ICOS, or OX40.

In some embodiments, the compound or pharmaceutical composition is co-administered with one or more additional therapeutic agents comprising an activator or agonist of a fins related tyrosine kinase 3 (FLT3; CD 135) receptor, a toll-like receptor (TLR) or a stimulator of interferon genes (STING) receptor.

In some embodiments, the TLR agonist or activator is a TLR2 agonist, a TLR3 agonist, a TLR7 agonist, a TLR8 agonist and a TLR9 agonist.

In some embodiments, the STING receptor agonist or activator is ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

In some embodiments, the compound or pharmaceutical composition is co-administered with one or more additional therapeutic agents comprising an inhibitor or antagonist of: protein tyrosine phosphatase, non-receptor type 11 (PTPN11 or SHP2), myeloid cell leukemia sequence 1 (MCL1) apoptosis regulator; mitogen-activated protein kinase kinase kinase kinase 1 (MAP4K1) (also called Hematopoietic Progenitor Kinase 1 (HPK1)); diacylglycerol kinase alpha (DGKA, DAGK, DAGK1 or DGK-alpha); 5'-nucleotidase ecto (NTSE or CD73); transforming growth factor beta 1 (TGFB1 or TGF); heme oxygenase 1 (HMOX1, HO-1 or HO1); vascular endothelial growth factor A (VEGFA or VEGF); erb-b2 receptor tyrosine kinase 2 (ERBB2 HER2, HER2/neu or CD340); epidermal growth factor receptor (EGFR, ERBB, ERBB1 or HER1); ALK receptor tyrosine kinase (ALK, CD246); poly(ADP-ribose) polymerase 1 (PARP1 or PARP); cyclin dependent kinase 4 (CDK4); cyclin dependent kinase 6 (CDK6); C-C motif chemokine receptor 8 (CCR8, CDw198); CD274 molecule (CD274, PDL1 or PD-L1); programmed cell death 1 (PDCD1, PD1 or PD-1); and/or cytotoxic T-lymphocyte associated protein 4 (CTLA4, CTLA-4, CD 152).

In some embodiments, the inhibitor comprises an antigen binding molecule, an antibody or an antigen-binding fragment thereof.

In some embodiments, the inhibitor of MCL1 is AMG-176, AMG-397, S-64315, AZD-5991, 483-LM, A1210477, UMI-77, or JKY-5-037.

In some embodiments, the inhibitor of PTPN11 or SHP2 is TN0155 (SHP-099), RMC-4550, JAB-3068 and RMC-4630.

In some embodiments, the additional therapeutic agent is a chemotherapeutic, an anti-neoplastic, a radiotherapeutic, or a checkpoint targeting agent. In some embodiments, the one or more anti-neoplastic or chemotherapeutic agents are a nucleoside analog (e.g., 5-fluorouracil, gemcitabine, cytarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, al doxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), or mixtures thereof.

In some embodiments, the checkpoint targeting agent is an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an antagonist anti-TIGIT antibody, an antagonist anti-VISTA antibody, an agonist anti-CD 137 antibody, or an agonist anti-OX40 antibody.

In some embodiments, the additional therapeutic agent comprises one or more cellular therapies. In some embodiments, the cellular therapy comprises one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. A cellular therapy can entail the co-administration of cells that are autologous, syngeneic or allogeneic to the subject. In some embodiments, the cells are allogeneic to an intended recipient. In some embodiments, the one or more of a population of immune cells comprise one or more chimeric antigen receptors (CARs).

In some embodiments, the checkpoint targeting agent is an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an antagonist anti-TIGIT antibody, an antagonist anti-VISTA antibody, an agonist anti-CD 137 antibody, or an agonist anti-OX40 antibody.

VII. EXAMPLES

Abbreviations. Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Definition |
| --- | --- |
| Ac | acetate |
| Ar | argon |
| ACN | acetonitrile |
| cat | catalyst |
| DCM | dichloromethane |
| DIPEA | N,N-diisopropylethylamine |
| DMSO | dimethylsulfoxide |
| DMF | dimethylformamide |
| ES/MS | electro spray mass spectrometry |
| Et | ethyl |
| EtOAc | ethyl acetate |
| HPLC | high performance liquid chromatography |
| LC | liquid chromatography |
| Me | methyl |
| MeCN | acetonitrile |
| m/z | mass to charge ratio |
| NMP | N-methyl-2-pyrrolidone |
| NMR | Nuclear Magnetic Resonance |
| Ph | phenyl |
| Pd(dppf)Cl$_2$ or PdCl$_2$(dppf) | [1,1'-Bis(diphenylphosphino)ferrocene]dichloropalladium(II) |
| Pr | propyl |
| RP | reverse phase |
| TFA | trifluoroacetic acid |
| THF | tetrahydrofuran |
| TBHP | tert-butyl hydroperoxide |
| δ | parts per million referenced to residual non-deuterated solvent peak |

A. Intermediates
Suzuki Cross Coupling with Cyclopropyl Boronic Acids

Intermediate 1. 6-chloro-8-cyclopropyl-2-methyl-imidazo[1,2-b]pyridazine

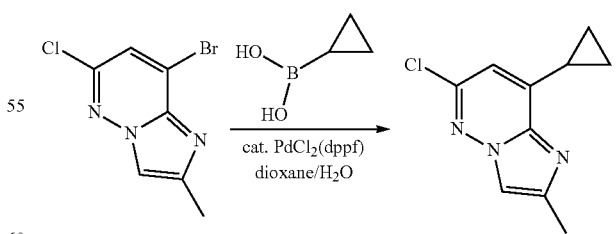

6-chloro-8-cyclopropyl-2-methyl-imidazo[1,2-b] pyridazine was prepared as follows: A microwave vial was charged with 8-bromo-6-chloro-2-methyl-imidazo[1,2-b] pyridazine (200 mg, 0.81 mmol, 1 equiv), cyclopropylboronic acid (73.2 mg, 0.85 mmol, 1.05 equiv), cesium carbonate (529 mg, 1.62 mmol, 2 equiv), and Pd(dppf)

Cl₂CH₂Cl₂ (66.3 mg, 10 mol %). The reaction mixture was dissolved in 1:1 dioxane/H₂O (4 mL total), purged with argon, and heated in a microwave reactor at 120° C. After 1 hour, the reaction mixture was directly purified by silica gel chromatography (0-10% MeOH/CH₂Cl₂). Fractions obtained were mixtures of mono and bis-alkylated products. Compound was repurified by silica gel chromatography (0-100% EtOAc/Hexanes), affording 6-chloro-8-cyclopropyl-2-methyl-imidazo[1,2-b]pyridazine. ES/MS m/z: 208.10 [M+H].

Intermediate 2. 6-chloro-8-cyclopropyl-2-phenyl-imidazo[1,2-b]pyridazine

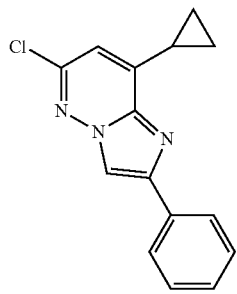

6-chloro-8-cyclopropyl-2-phenyl-imidazo[1,2-b] pyridazine was prepared in the manner described for Intermediate 1, but replacing 8-bromo-6-chloro-2-methyl-imidazo[1,2-b]pyridazine with 8-bromo-6-chloro-2-phenylimidazo[1,2-b]pyridazine. ES/MS m/z: 270.10 [M+H].

Intermediate 3. Ethyl 6-chloro-8-cyclopropyl-imidazo[1,2-b]pyridazine-2-carboxylate

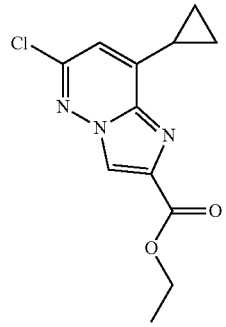 [SMILES: CCOC(=O)c1cn2nc(Cl)cc(C3CC3)c2n1]

Ethyl 6-chloro-8-cyclopropyl-imidazo[1,2-b]pyridazine-2-carboxylate was prepared in the manner described for Intermediate 1, but replacing 8-bromo-6-chloro-2-methyl-imidazo[1,2-b]pyridazine with ethyl 8-bromo-6-chloro-imidazo[1,2-b]pyridazine-2-carboxylate. ES/MS m/z: 266.10 [M+H].

Intermediate 4. 6-chloro-8-cyclopropylimidazo[1,2-b]pyridazine

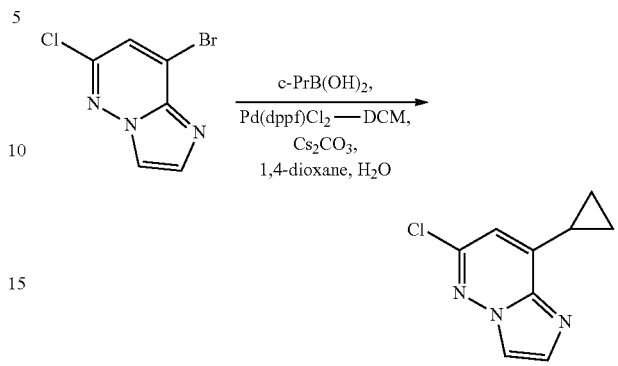

8-bromo-6-chloroimidazo[1,2-b]pyridazine (103 mg, 0.43 mmol, 1 equiv), cyclopropylboronic acid (81 mg, 0.92 mmol, 2.1 equiv), Pd(dppf)Cl₂-DCM complex (9 mg, 0.01 mmol, 0.02 equiv), and Cs₂CO₃ (357 mg, 1.08 mmol, 2.5 equiv) were diluted with 1,4-dioxane (1 mL) and water (1 mL). The mixture was purged with Ar and heated in a microwave reactor at 150° C. for 1 h. The reaction mixture was filtered through Celite, diluted with EtOAC (30 mL), washed with water (25 mL) and brine (25 mL), dried over Na₂SO₄, and concentrated in vacuo. Purification of the reaction product by silica gel chromatography (0-100% EtOAc/DCM) afforded 6-chloro-8-cyclopropylimidazo[1,2-b]pyridazine. ES/MS: 194.09 [M+1].

Suzuki Cross Coupling with Cyclopropyl Boronate Esters

Intermediate 5. 6-chloro-8-((1S,2S)-2-phenylcyclopropyl)imidazo[1,2-b]-pyridazine (Racemic Mixture)

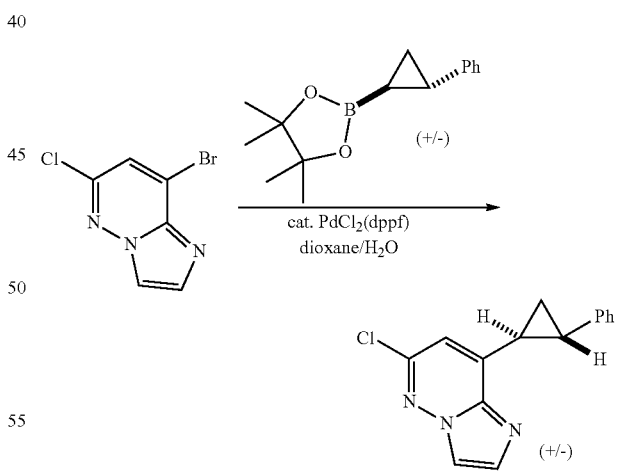

6-chloro-8-((1S,2S)-2-phenylcyclopropyl)imidazo[1,2-b]-pyridazine was prepared as a racemic mixture follows: A microwave vial was charged with 8-bromo-6-chloroimidazo[1,2-b]pyridazine (100 mg, 0.43 mmol, 1 equiv), racemic 4,4,5,5-tetramethyl-2-((2S,2S)-2-phenylcyclopropyl)-1,3,2-dioxaborolane (105 mg, 0.43 mmol, 1 equiv), cesium carbonate (280 mg, 0.86 mmol, 2 equiv), and Pd(dppf)Cl₂CH₂Cl₂ (32 mg, 10 mol %). The solids were dissolved in 2:1 dioxane/H₂O (2 mL), purged with argon, and heated in a microwave reactor at 120° C. After 1 hour, the reaction mixture was directly purified by silica gel chromatography (0-10% MeOH/CH₂Cl₂), affording 6-chloro-8-((1S,2S)-2-phenylcyclopropyl)-imidazo[1,2-b]pyridazine. ES/MS m/z: 270.10 [M+H].

Intermediate 6. 6-chloro-8-((1S,2S)-2-(methoxymethyl)cyclopropyl)imidazo[1,2-b]pyridazine

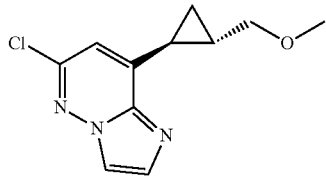 [SMILES: COC[C@H]1C[C@@H]1c1cc(Cl)nn2ccnc12]

6-chloro-8-((1S,2S)-2-(methoxymethyl)cyclopropyl)imidazo[1,2-b]pyridazine was prepared in the manner described for Intermediate 5, but replacing racemic 4,4,5,5-tetramethyl-2-((2S,2S)-2-phenylcyclopropyl)-1,3,2-dioxaborolane with 2-((1S,2S)-2-(methoxymethyl)cyclopropyl)-4,4,5,5-tetramethyl-1,3,2-dioxaborolane. ES/MS m/z: 238.10 [M+H].

Intermediate 7. 6-chloro-8-(spiro[2.31]hexan-1-yl)imidazo[1,2-b]pyridazine

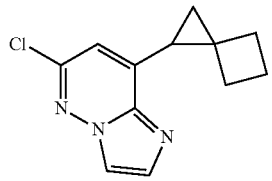 [SMILES: Clc1cc(C2CC23CCC3)c2nccn2n1]

6-chloro-8-(spiro[2.3]hexan-1-yl)imidazo[1,2-b]pyridazine was prepared in the manner described for Intermediate 5 modified as follows. Racemic 4,4,5,5-tetramethyl-2-((2S,2S)-2-phenylcyclopropyl)-1,3,2-dioxaborolane and Pd(dppf)Cl₂—CH₂Cl₂ were replaced with potassium spiro[2.3]hexan-1-yl trifluoroborate and cataCXium-A-PdG3, respectively. The reaction mixture was dissolved in 10:1 Toluene/H₂O, rather than in 2:1 dioxane/H₂O, and heated at 100° C. for 18 hours. ES/MS m/z: 234.10 [M+H].

Intermediate 8. 8-((1S,2S)-2-(tert-butyl)cyclopropyl)-6-chloroimidazo[1,2-b]pyridazine

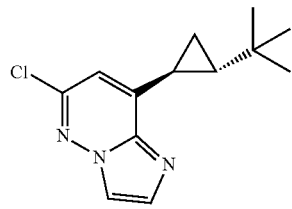 [SMILES: CC(C)(C)[C@H]1C[C@@H]1c1cc(Cl)nn2ccnc12]

8-((1S,2S)-2-(tert-butyl)cyclopropyl)-6-chloroimidazo[1,2-b]pyridazine was prepared as a racemic mixture in the manner described for Intermediate 5, but replacing racemic 4,4,5,5-tetramethyl-2-((1S,2S)-2-phenylcyclopropyl)-1,3,2-dioxaborolane with racemic 2-((1S,2S)-2-(tert-butyl)cyclopropyl)-4,4,5,5-tetramethyl-1,3,2-dioxa-borolane. ES/MS m/z: 250.10 [M+H].

Intermediate 9. 8-((1R,2S)-[1,1'-bi(cyclopropan)]-2-yl)-6-chloroimidazo[1,2-b]pyridazine

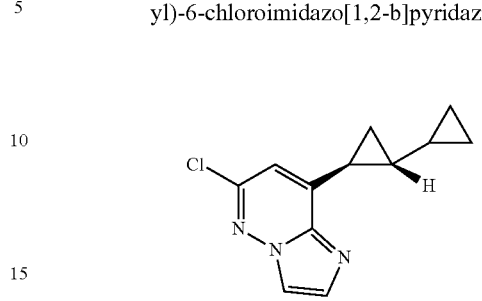

8-((1R,2S)-[1,1'-bi(cyclopropan)]-2-yl)-6-chloroimidazo[1,2-b]pyridazine was prepared as a racemic mixture in the manner described for Intermediate 5, but replacing racemic 4,4,5,5-tetramethyl-2-((2S,2S)-2-phenylcyclopropyl)-1,3,2-dioxaborolane with racemic 2-((1S,2S)-[1,1'-bi(cyclopropan)]-2-yl)-4,4,5,5-tetramethyl-1,3,2-dioxaborolane. ES/MS m/z: 234.10 [M+H].

SNAr Reaction of Cyclic Amines with 8-bromo-6-chloroimidazo[1,2-b]pyridazine

Intermediate 10. 6-chloro-8-pyrrolidin-1-yl-imidazo[1,2-b]pyridazine

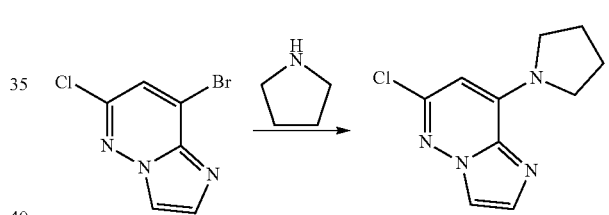

6-chloro-8-pyrrolidin-1-yl-imidazo[1,2-b]pyridazine was prepared as follows: A microwave vial was charged with 8-bromo-6-chloroimidazo[1,2-b]pyridazine (200 mg, 0.86 mmol, 1 equiv), pyrrolidine (0.086 mL, 1.03 mmol, 1.2 equiv), DIPEA (0.246 mL, 1.38 mmol, 1.6 equiv), and MeCN (5 mL). The reaction mixture was heated to 85° C. After 24 hours, the reaction mixture was concentrated. The residue obtained was triturated with water, the resulting solids were filtered, washed with water, and dried affording 6-chloro-8-pyrrolidin-1-yl-imidazo[1,2-b]pyridazine. ES/MS m/z: 223.10.

Intermediate 11. 4-(6-chloroimidazo[1,2-b]pyridazin-8-yl)morpholine

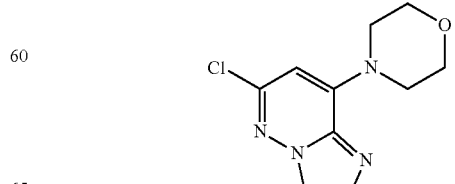

4-(6-chloroimidazo[1,2-b]pyridazin-8-yl)morpholine was prepared in the manner described for Intermediate 10, but replacing pyrrolidine with morpholine. ES/MS m/z: 239.10 [M+H].

SNAr Reaction of Benzylamines with 8-bromo-6-chloroimidazo-[1,2-b]pyridazine

Intermediate 12. N-benzyl-6-chloroimidazo[1,2-b]-pyridazin-8-amine

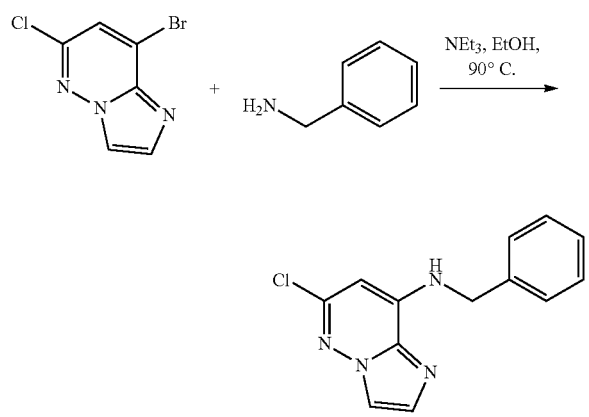

N-benzyl-6-chloroimidazo[1,2-b]-pyridazin-8-amine was prepared as follows: To a solution of 8-bromo-6-chloroimidazo[1,2-b]pyridazine (200 mg, 0.860 mmol, 1 equiv) and triethylamine (0.361 mL, 2.58 mmol, 3 equiv) in EtOH (1.6 mL) was added benzylamine (0.094 mL, 0.860 mmol, 1 equiv). The reaction mixture was heated to 90° C., in a sealed microwave vial, and stirred overnight. The reaction mixture was diluted with EtOAc/water and extracted twice with EtOAc. The combined organic layers were dried over MgSO₄, filtered and concentrated in vacuo to provide N-benzyl-6-chloroimidazo[1,2-b]pyridazin-8-amine. The product was used directly in subsequent reaction(s) without further purification. ES/MS m/z: 259.1 [M+1].

Intermediate 13. N-benzyl-6-chloro-N-methylimidazo[1,2-b]pyridazin-8-amine

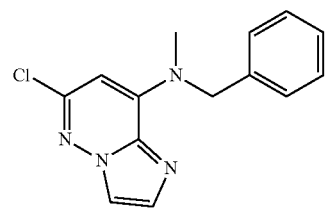 [SMILES: CN(Cc1ccccc1)c1cc(Cl)nn2ccnc12]

N-benzyl-6-chloro-N-methylimidazo[1,2-b]pyridazin-8-amine was prepared in the manner described for Intermediate 12, but replacing benzylamine with N-methyl-1-phenylmethanamine (0.111 mL, 0.860 mmol, 1 equiv). ES/MS m/z: 273.1 [M+1].

Intermediate 14. 6-chloro-8-imidazol-1-yl-imidazo[1,2-b]pyridazine

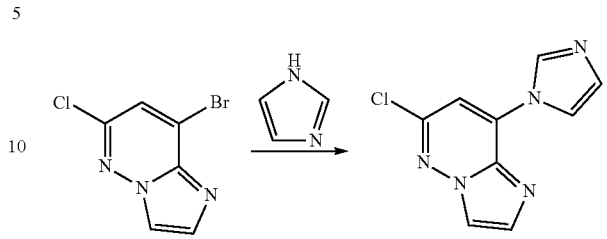

A microwave vial was charged with 8-bromo-6-chloroimidazo[1,2-b]pyridazine (250 mg, 1.08 mmol, 1 equiv), imidazole (80.5 mg, 1.18 mmol, 1.1 equiv), potassium carbonate (233 mg, 1.61 mmol, 1.5 equiv), and NMP (5 mL). The reaction mixture was heated to 90° C. After 8 hours, the reaction mixture was diluted with water, the resulting solids were filtered, washed with water and dried to provide 6-chloro-8-imidazol-1-yl-imidazo[1,2-b]pyridazine. ES/MS m/z: 220.10 [M+H].

SnAr Reaction of Alcohols with 8-Bromo-6-chloroimidazo-[1,2-b]pyridazine

Intermediate 15. 6-chloro-8-cyclopropoxyimidazo[1,2-b]pyridazine 8-bromo-6-chloroimidazo[1,2-b]pyridazine (528 mg, 2.27 mmol) and cyclopropanol (119 mg, 2.04 mmol) were dissolved in ACN (5 mL). To the reaction mixture was added cesium carbonate (1.1 g, 3.41 mmol) and heated at 80° C. overnight. The reaction mixture was then concentrated in vacuo and purified by silica gel chromatography to afford 6-chloro-8-cyclopropoxyimidazo-[1,2-b]pyridazine. ES/MS m/z: 210.10 [M+H].

Intermediate 16. 5-(8-isopropoxyimidazo[1,2-b]pyridazin-6-yl)pyrimidine-2,4(1H,3H)-dione

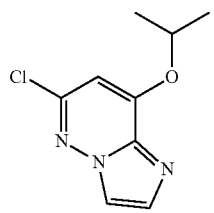

5-(8-isopropoxyimidazo[1,2-b]pyridazin-6-yl)pyrimidine-2,4(1H,3H)-dione was prepared as follows. A microwave vial was charged with 8-bromo-6-chloroimidazo[1,2-b]pyridazine (300 mg, 1.29 mmol, 1 equiv), 2-propanol (0.296 mL, 3.87 mmol, 3 equiv), cesium carbonate (841 mg, 2.58 mmol, 2 equiv), and MeCN (5 mL). The reaction mixture was heated to 80° C. After 24 hours, the reaction mixture was directly purified by silica gel chromatography (0-100% EtOAc/Hexanes), affording 6-chloro-8-isopropoxyimidazo[1,2-b]pyridazine. ES/MS m/z: 212.00.

Intermediate 17. 8-benzyloxy-6-chloro-imidazo[1,2-b]pyridazine

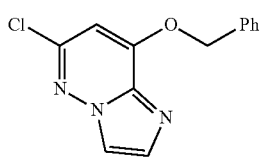 [SMILES: Clc1cc(OCc2ccccc2)c2nccn2n1]

8-benzyloxy-6-chloro-imidazo[1,2-b]pyridazine was prepared as follows. To a solution of phenylmethanol (47 uL, 0.452 mmol) in THF (1.5 mL) at 0° C. was added sodium hydride (18 mg, 0.473 mmol). The reaction mixture was stirred for 30 min, after which 8-bromo-6-chloro-imidazo[1,2-b]pyridazine (100 mg, 0.430 mmol) as added as a solution in THF (0.5 mL). The mixture was stirred overnight and slowly warmed to room temperature. The mixture was then quenched with $H_2O$ and extracted with EtOAc. Combined organics were dried over $MgSO_4$, filtered, and concentrated in vacuo. The resulting residue was purified by silica gel chromatography (0-100% EtOAc/hexanes) to provide the title compound. ES/MS m/z: 260.1 [M+1].

Suzuki Cross Coupling Reaction with (2,4-dimethoxypyrimidin-5-yl)boronic acid

Intermediate 18. 8-cyclopropyl-6-(2,4-dimethoxypyrimidin-5-yl)-2-methyl-imidazo[1,2-b]pyridazine

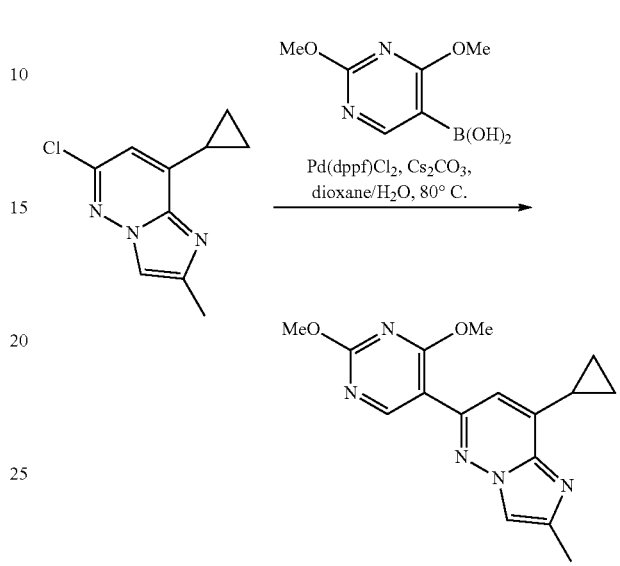

8-cyclopropyl-6-(2,4-dimethoxypyrimidin-5-yl)-2-methyl-imidazo[1,2-b]pyridazine was prepared as follows: A microwave vial was charged with (2,4-dimethoxypyrimidin-5-yl)boronic acid (59.4 mg, 0.323 mmol, 1.0 equiv), Pd(dppf)Cl$_2$—CH$_2$Cl$_2$ (23.6 mg, 0.032 mmol, 10 mol %), Cs$_2$CO$_3$ (210 mg, 0.645 mmol, 2 equiv) and 6-chloro-8-cyclopropyl-2-methyl-imidazo[1,2-b]pyridazine (67 mg, 0.323 mmol, 1 equiv). The reaction mixture was dissolved in 3:1 dioxane/H$_2$O (4 mL), purged with argon, and was stirred at 80° C. for 5 h. The reaction mixture was directly purified by silica gel chromatography (0-15% MeOH/CH$_2$Cl$_2$). Compound was repurified by SiO$_2$ chromatography (0-100% EtOAc/Hexanes), affording 8-cyclopropyl-6-(2,4-dimethoxypyrimidin-5-yl)-2-methyl-imidazo[1,2-b]pyridazine. ES/MS m/z: 312.20 [M+H].

Intermediate 19. 8-cyclopropyl-6-(2,4-dimethoxypyrimidin-5-yl)-2-phenyl-imidazo[1,2-b]pyridazine

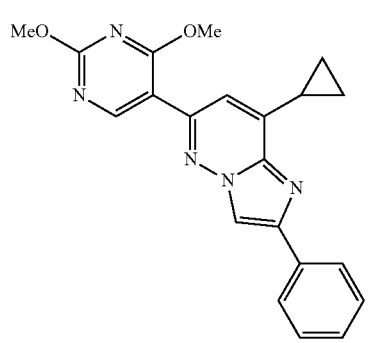 [SMILES: COc1ncc(-c2cc(C3CC3)c3nc(-c4ccccc4)cn3n2)c(OC)n1]

8-cyclopropyl-6-(2,4-dimethoxypyrimidin-5-yl)-2-phenyl-imidazo[1,2-b]pyridazine was prepared in the manner described for Intermediate 18, but replacing 6-chloro-8- cyclopropyl-2-methyl-imidazo[1,2-b]pyridazine with 6-chloro-8-cyclopropyl-2-phenyl-imidazo[1,2-b]pyridazine. ES/MS m/z: 374.20 [M+H].

Intermediate 20. Ethyl 8-cyclopropyl-6-(2,4-dimethoxypyrimidin-5-yl)imidazo[1,2-b]pyridazine-2-carboxylate

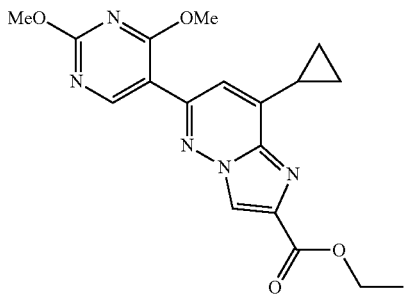 [SMILES: CCOC(=O)c1cn2nc(-c3cnc(OC)nc3OC)cc(C3CC3)c2n1]

Ethyl 8-cyclopropyl-6-(2,4-dimethoxypyrimidin-5-yl)imidazo[1,2-b]pyridazine-2-carboxylate was prepared in the manner described for Intermediate 18, but replacing 6-chloro-8-cyclopropyl-2-methyl-imidazo[1,2-b]pyridazine with ethyl 6-chloro-8-cyclopropyl-imidazo[1,2-b]pyridazine-2-carboxylate. ES/MS m/z: 370.10 [M+H].

Intermediate 21. 6-(2,4-dimethoxypyrimidin-5-yl)-8-((1S,2S)-2-(methoxymethyl)cyclopropyl)imidazo[1,2-b]pyridazine

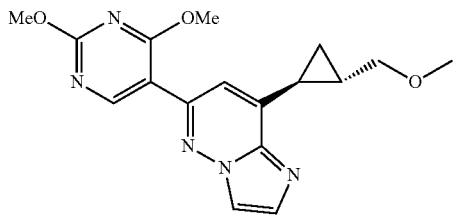 [SMILES: COC[C@H]1C[C@@H]1c1cc(-c2cnc(OC)nc2OC)nn2ccnc12]

6-(2,4-dimethoxypyrimidin-5-yl)-8-((1S,2S)-2-(methoxymethyl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(methoxymethyl)cyclopropyl)imidazo[1,2-b]pyridazine (Racemic Mixture). ES/MS m/z: 342.10 [M+H].

Intermediate 22. 6-(2,4-dimethoxypyrimidin-5-yl)-8-(spiro[2.3]hexan-1-yl)imidazo[1,2-b]pyridazine

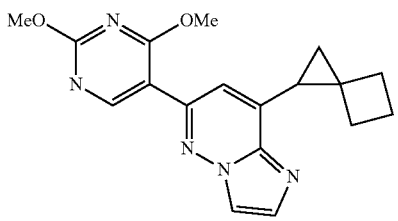

6-(2,4-dimethoxypyrimidin-5-yl)-8-(spiro[2.3]hexan-1-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-(spiro[2.3]hexan-1-yl)imidazo[1,2-b]pyridazine (Racemic Mixture). ES/MS m/z: 338.20 [M+H].

Intermediate 23. 8-((1S,2S)-2-(tert-butyl)cyclopropyl)-6-(2,4-dimethoxypyrimidin-5-yl)imidazo[1,2-b]pyridazine

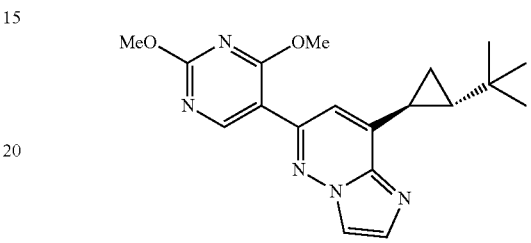

8-((1S,2S)-2-(tert-butyl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 8-((1S,2S)-2-(tert-butyl)cyclopropyl)-6-chloroimidazo[1,2-b]pyridazine (Racemic Mixture). ES/MS m/z: 354.10 [M+H].

Intermediate 24. 6-(2,4-dimethoxypyrimidin-5-yl)-8-((1S,2S)-2-phenylcyclopropyl)imidazo[1,2-b]pyridazine

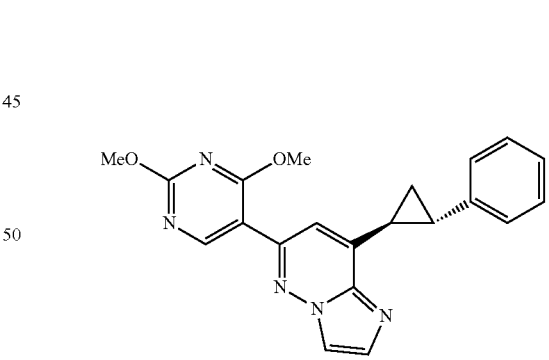

6-(2,4-dimethoxypyrimidin-5-yl)-8-((1S,2S)-2-phenylcyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-phenylcyclopropyl)imidazo[1,2-b]pyridazine (Racemic Mixture). ES/MS m/z: 374.20 [M+H].

Intermediate 25. 8-((1R,2S)-[1,1'-bi(cyclopropan)]-2-yl)-6-(2,4-dimethoxypyrimidin-5-yl)imidazo[1,2-b]pyridazine

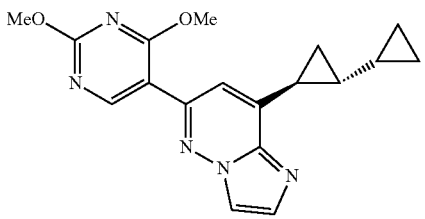 [SMILES: COc1ncc(-c2cc([C@H]3C[C@@H]3C3CC3)c3nccn3n2)c(OC)n1]

8-((1R,2S)-[1,1'-bi(cyclopropan)]-2-yl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 8-((1R,2S)-[1,1'-bi(cyclopropan)]-2-yl)-6-chloroimidazo[1,2-b]pyridazine (Racemic Mixture). ES/MS m/z: 338.20 [M+H].

Intermediate 26. 6-(2,4-dimethoxypyrimidin-5-yl)-8-pyrrolidin-1-yl-imidazo[1,2-b]pyridazine

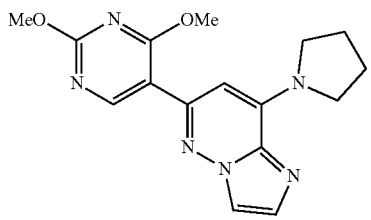 [SMILES: COc1ncc(-c2cc(N3CCCC3)c3nccn3n2)c(OC)n1]

6-(2,4-dimethoxypyrimidin-5-yl)-8-pyrrolidin-1-yl-imidazo[1,2-b]pyridazine was prepared in the manner described for Intermediate 18, but replacing 6-chloro-8-cyclopropyl-2-methyl-imidazo[1,2-b]pyridazine with 6-chloro-8-pyrrolidin-1-yl-imidazo[1,2-b]pyridazine. ES/MS m/z: 327.20 [M+H].

Intermediate 27. 4-[6-(2,4-dimethoxypyrimidin-5-yl)imidazo[1,2-b]pyridazin-8-yl]morpholine

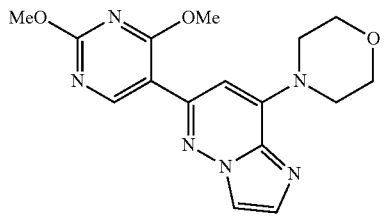

4-[6-(2,4-dimethoxypyrimidin-5-yl)imidazo[1,2-b]pyridazin-8-yl]morpholine was prepared in the manner described for Intermediate 18, but replacing 6-chloro-8-cyclopropyl-2-methyl-imidazo[1,2-b]pyridazine with 4-(6-chloroimidazo[1,2-b]pyridazin-8-yl)morpholine. ES/MS m/z: 343.20 [M+H].

Intermediate 28. 6-(2,4-dimethoxypyrimidin-5-yl)-8-imidazol-1-yl-imidazo[1,2-b]pyridazine

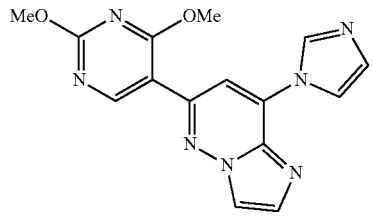 [SMILES: COc1ncc(-c2cc(-n3ccnc3)c3nccn3n2)c(OC)n1]

6-(2,4-dimethoxypyrimidin-5-yl)-8-imidazol-1-yl-imidazo[1,2-b]pyridazine was prepared in the manner described for Intermediate 18, but replacing 6-chloro-8-cyclopropyl-2-methyl-imidazo[1,2-b]pyridazine with 6-chloro-8-imidazol-1-yl-imidazo[1,2-b]pyridazine. ES/MS m/z: 324.10 [M+H].

Intermediate 29. N-benzyl-6-(2,4-dimethoxypyrimidin-5-yl)imidazo[1,2-b]pyridazin-8-amine

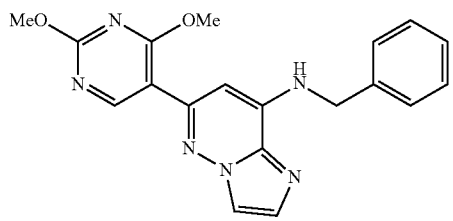 [SMILES: COc1ncc(-c2cc(NCc3ccccc3)c3nccn3n2)c(OC)n1]

N-benzyl-6-(2,4-dimethoxypyrimidin-5-yl)imidazo[1,2-b]pyridazin-8-amine was prepared in the manner described for Intermediate 18, but replacing 6-chloro-8-cyclopropyl-2-methyl-imidazo[1,2-b]pyridazine with N-benzyl-6-chloroimidazo[1,2-b]pyridazin-8-amine (60 mg, 0.232 mmol, 1 equiv). ES/MS m/z: 363.2 [M+1].

Intermediate 30. N-benzyl-6-(2,4-dimethoxypyrimidin-5-yl)-N-methylimidazo[1,2-b]pyridazin-8-amine

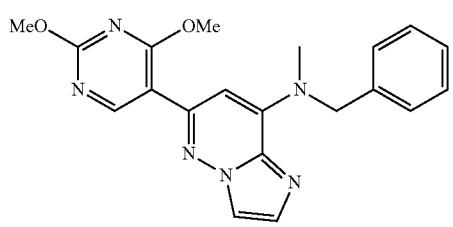 [SMILES: COc1ncc(-c2cc(N(C)Cc3ccccc3)c3nccn3n2)c(OC)n1]

N-benzyl-6-(2,4-dimethoxypyrimidin-5-yl)-N-methylimidazo[1,2-b]pyridazin-8-amine was prepared in the manner described for Intermediate 18, but replacing 6-chloro-8-cyclopropyl-2-methyl-imidazo[1,2-b]pyridazine with N-benzyl-6-chloro-N-methylimidazo[1,2-b]pyridazin-8-amine (90 mg, 0.330 mmol, 1 equiv). ES/MS m/z: 377.2 [M+1].

Intermediate 31. 6-(2,4-dimethoxypyrimidin-5-yl)imidazo[1,2-b]pyridazine

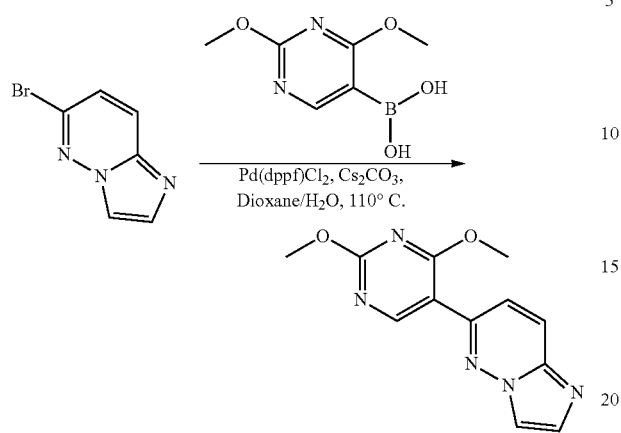

6-bromoimidazo[1,2-b]pyridazine (200 mg, 1 mmol) and (2,4-dimethoxypyrimidin-5-yl)boronic acid (252 mg, 1.62 mmol) were dissolved in dioxane/water (2/1, 4 mL). To the reaction mixture was added cesium carbonate (823 mg, 2.52 mmol) and Pd(dppf)Cl₂ (82 mg, 0.1 mmol). The reaction mixture was then purged with Argon for 10 mins and then heated at 110° C. overnight. The reaction mixture was then filtered and purified with reverse phase HPLC (ACN/water with 0.1% TFA) to afford 6-(2,4-dimethoxypyrimidin-5-yl)imidazo[1,2-b]pyridazine. ES/MS m/z: 230.10 [M+H].

Intermediate 32. 8-cyclopropyl-6-(2,4-dimethoxypyrimidin-5-yl)imidazo[1,2-b]pyridazine

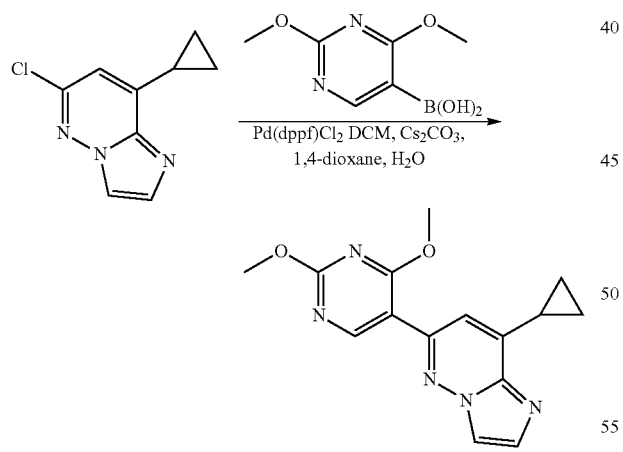

6-chloro-8-cyclopropylimidazo[1,2-b]pyridazine (37 mg, 0.19 mmol, 1 equiv), (2,4-dimethoxypyrimidin-5-yl)boronic acid (37 mg, 0.19 mmol, 1 equiv), Pd(dppf)Cl₂ DCM complex (15 mg, 0.02 mmol, 0.1 equiv), and Cs₂CO₃ (157 mg, 0.48 mmol, 2.5 equiv) were diluted with 1,4-dioxane (1.0 mL) and water (0.5 mL). The mixture was purged with Ar and set into a microwave reactor to 120° C. for 1 h. The mixture was filtered through celite, diluted with EtOAC (30 mL), washed with water (30 mL) and brine (30 mL), dried over Na₂SO₄, and concentrated in vacuo. Purification by column chromatography (0-30% MeOH/DCM) afforded 8-cyclopropyl-6-(2,4-dimethoxypyrimidin-5-yl)imidazo[1,2-b]pyridazine. ES/MS: 298.15 [M+1].

Intermediate 33. 8-cyclopropoxy-6-(2,4-dimethoxypyrimidin-5-yl)imidazo[1,2-b]pyridazine

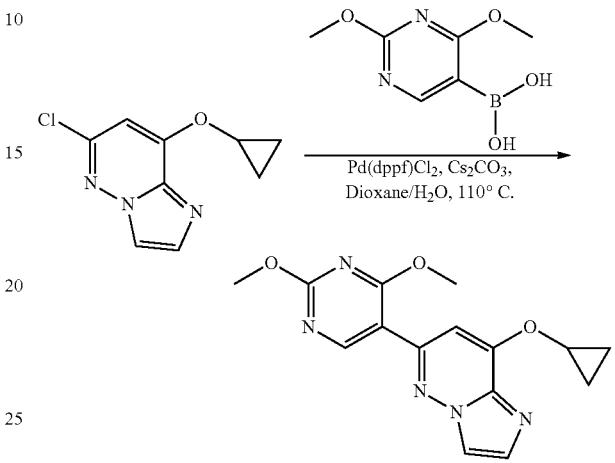

6-chloro-8-cyclopropoxyimidazo[1,2-b]pyridazine (131 mg, 0.625 mmol) and (2,4-dimethoxypyrimidin-5-yl)boronic acid (230 mg, 1.25 mmol) were dissolved in dioxane/water (2/1, 4 mL). To the reaction mixture was added cesium carbonate (509 mg, 1.56 mmol) and Pd(dppf)Cl₂ (46 mg, 0.06 mmol). The reaction mixture was then purged with argon for 10 mins and then heated at 110° C. overnight. The reaction mixture was then filtered and purified with a combi-flash column to afford 8-cyclopropoxy-6-(2,4-dimethoxypyrimidin-5-yl)imidazo[1,2-b]. ES/MS m/z: 314.20 [M+H].

Intermediate 34. 5-(8-isopropoxyimidazo[1,2-b]pyridazin-6-yl)pyrimidine-2,4(1H,3H)-dione

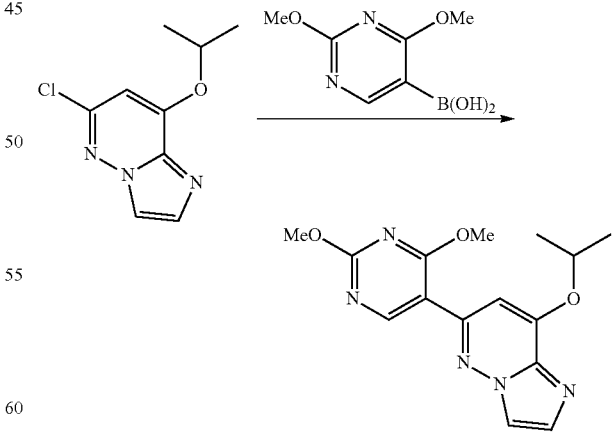

5-(8-isopropoxyimidazo[1,2-b]pyridazin-6-yl)pyrimidine-2,4(1H,3H)-dione was prepared as follows. A microwave vial was charged with 6-chloro-8-isopropoxyimidazo[1,2-b]pyridazine (91 mg, 0.43 mmol, 1 equiv), (2,4-dimethoxypyrimidin-5-yl)boronic acid (119 mg, 0.65 mmol, 1.5 equiv), cesium carbonate (280 mg, 0.86 mmol, 2 equiv), and Pd(dppf)Cl$_2$—CH$_2$Cl$_2$ (32 mg, 10 mol %). The reaction mixture was dissolved in 2:1 dioxane/H$_2$O (4 mL), purged with argon, and heated at 80° C. After 30 minutes, the reaction mixture was directly purified by SiO$_2$ chromatography (0-30% EtOAc/CH$_2$Cl$_2$), affording 6-(2,4-dimethoxypyrimidin-5-yl)-8-isopropoxyimidazo[1,2-b]pyridazine. ES/MS m/z: 316.20 [M+H].

Intermediate 35. 8-benzyloxy-6-(2,4-dimethoxypyrimidin-5-yl)imidazo[1,2-b]pyridazine

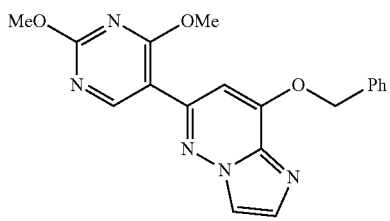 [SMILES: COc1ncc(-c2cc(OCc3ccccc3)c3nccn3n2)c(OC)n1]

8-benzyloxy-6-chloro-imidazo[1,2-b]pyridazine (54 mg, 0.208 mmol), (2,4-dimethoxypyrimidin-5-yl) boronic acid (46 mg, 0.250 mmol), Pd(dppf)Cl$_2$—CH$_2$Cl$_2$ (17 mg, 0.0208 mmol), and Cs$_2$CO$_3$ (203 mg, 0.624 mmol) were combined in a microwave vial. Dioxane (1 mL) and H$_2$O (0.2 mL) were then added and the mixture was degassed with N$_2$ for 5 min. The vial was then sealed and heated to 90° C. overnight. The mixture was concentrated in vacuo and purified by silica gel chromatography (0-100% EtOAc/hexanes) to provide the title compound. ES/MS m/z: 364.1 [M+1].

Two-step C-H Alkylation and Suzuki Sequence with 6-Chloroimidazo[1,2-b]pyridazine Intermediate 36. 8-(4,4-difluorocyclohexyl)-6-(2,4-dimethoxypyrimidin-5-yl)imidazo[1,2-b]pyridazine

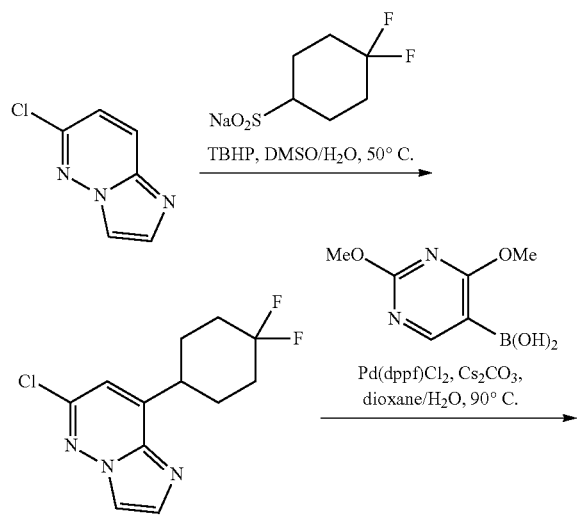

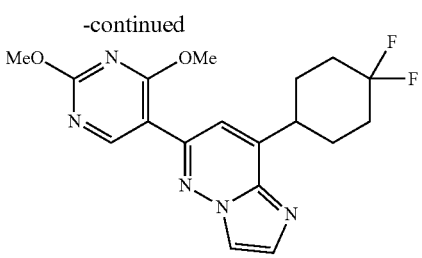

8-(4,4-difluorocyclohexyl)-6-(2,4-dimethoxypyrimidin-5-yl)imidazo[1,2-b]pyridazine was prepared as follows Preparation of 6-chloro-8-(4,4-difluorocyclohexyl)imidazo[1,2-b]pyridazine To a solution of 6-chloroimidazo[1,2-b]pyridazine (75 mg, 0.488 mmol, 1 equiv) and sodium 4,4-difluorocyclohexane sulfinate (252 mg, 1.22 mmol, 2.5 equiv) in DMSO/water (5:1, 1.5 mL total) was added tert-butylhydroperoxide (0.349 mL 70% in H$_2$O, 2.44 mmol, 5 equiv). The reaction mixture was heated to 50° C. and stirred overnight. Subsequently, the reaction mixture was diluted with EtOAc/water and extracted twice with EtOAc. The combined organic layers were dried over MgSO$_4$, filtered and concentrated in vacuo. The resulting product was used directly in the next step without further purification. ES/MS m/z: 272.1 [M+1].

Preparation of 8-(4,4-difluorocyclohexyl)-6-(2,4-dimethoxypyrimidin-5-yl)imidazo[1,2-b]pyridazine A freshly degassed solution of the resulting product from the reaction above, 6-chloro-8-(4,4-difluorocyclohexyl)imidazo[1,2-b]pyridazine (133 mg, 0.504 mmol, 1 equiv), in dioxane/water (5:1, 3 mL total) was added to the solid reagents (2,4-dimethoxypyrimidin-5-yl)boronic acid (111 mg, 0.605 mmol, 1.2 equiv), Pd(dppf)Cl$_2$—CH$_2$Cl$_2$ (41 mg, 0.050 mmol, 10 mol %), and Cs$_2$CO$_3$ (493 mg, 1.51 mmol, 3 equiv) under an atmosphere of nitrogen. The reaction mixture was heated to 90° C. and stirred overnight. The reaction mixture was diluted with EtOAc/water and extracted twice with EtOAc. The combined organic layers were dried over MgSO$_4$, filtered, and concentrated in vacuo. The resulting product was purified by silica gel chromatography (0-100% EtOAc/hexanes) to provide 8-(4,4-difluorocyclohexyl)-6-(2,4-dimethoxypyrimidin-5-yl)imidazo[1,2-b]pyridazine. ES/MS m/z: 376.2 [M+1].

Intermediate 37. 6-chloro-8-isopropyl-2-(trifluoromethyl)imidazo[1,2-b]pyridazine

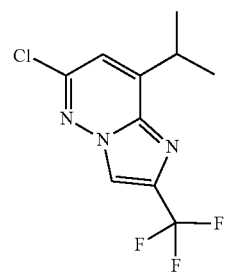 [SMILES: CC(C)c1cc(Cl)nn2cc(C(F)(F)F)nc12]

6-chloro-8-isopropyl-2-(trifluoromethyl)imidazo[1,2-b]pyridazine was prepared in the manner described for Intermediate 36 with the following modifications. 6-chloroimidazo[1,2-b]pyridazine, of the Intermediate 36 procedure, was replaced with 6-chloro-2-(trifluoromethyl)imidazo[1,2-a]pyridine (100 mg, 0.451 mmol, 1 equiv) and sodium 4,4-difluorocyclohexane sulfinate was replaced with zinc diisopropyl sulfinate (252 mg, 0.903 mmol, 2 equiv). ES/MS m/z: 264.1 [M+1].

Intermediate 38. 6-(2,4-dimethoxypyrimidin-5-yl)-8-isopropyl-2-(trifluoromethyl)imidazo[1,2-b]pyridazine

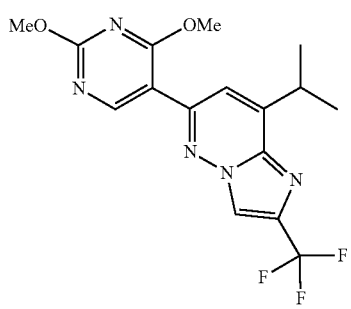 [SMILES: COc1ncc(-c2cc(C(C)C)c3nc(C(F)(F)F)cn3n2)c(OC)n1]

6-(2,4-dimethoxypyrimidin-5-yl)-8-isopropyl-2-(trifluoromethyl)imidazo[1,2-b]pyridazine was prepared in the manner described for Intermediate 36, but using 6-chloro-8-isopropyl-2-(trifluoromethyl)imidazo[1,2-b]pyridazine (89 mg, 0.338 mmol, 1 equiv) in place of 6-chloro-8-(4,4-difluorocyclohexyl)imidazo[1,2-b]pyridazine. ES/MS m/z: 368.1 [M+1].

Intermediate 39. 6-chloro-8-isopropyl-[1,2,4]triazolo[4,3-a]pyridazine

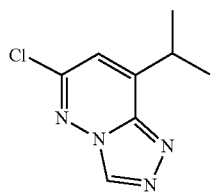

6-chloro-8-isopropyl-[1,2,4]triazolo[4,3-a]pyridazine was prepared in the manner described for Intermediate 36, but using 6-chloro-[1,2,4]triazolo[4,3-b]pyridazine (75 mg, 0.485 mmol, 1 equiv) in place of 6-chloroimidazo[1,2-b]pyridazine and zinc diisopropyl sulfinate (271 mg, 0.971 mmol, 2 equiv) in place of sodium 4,4-difluorocyclohexane sulfinate. ES/MS m/z: 197.1 [M+1].

Intermediate 40. 6-(2,4-dimethoxypyrimidin-5-yl)-8-isopropyl-[1,2,4]triazolo[4,3-b]pyridazine

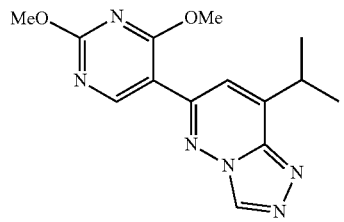 [SMILES: COc1ncc(-c2cc(C(C)C)c3nncn3n2)c(OC)n1]

6-(2,4-dimethoxypyrimidin-5-yl)-8-isopropyl-[1,2,4]triazolo[4,3-b]pyridazine was prepared in the manner described for Intermediate 36, but using 6-chloro-8-isopropyl-[1,2,4]triazolo[4,3-a]pyridazine (83 mg, 0.422 mmol, 1 equiv) in place of 6-chloro-8-(4,4-difluorocyclohexyl)imidazo[1,2-b]pyridazine. ES/MS m/z: 301.2 [M+1].

Intermediate 41. 8-benzyl-6-chloro-imidazo[1,2-b]pyridazine

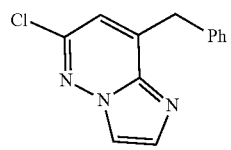 [SMILES: Clc1cc(Cc2ccccc2)c2nccn2n1]

8-benzyl-6-chloro-imidazo[1,2-b]pyridazine was prepared in the manner described for Intermediate 36, but using zinc benzylsulfinate (367 mg, 0.977 mmol, 2 equiv) in place of sodium 4,4-difluorocyclohexane sulfinate. ES/MS m/z: 244.1 [M+1].

Intermediate 42. 8-benzyl-6-(2,4-dimethoxypyrimidin-5-yl)imidazo[1,2-b]pyridazine

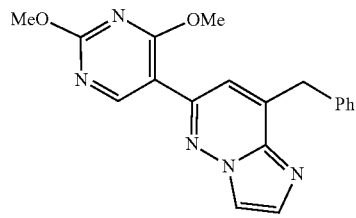 [SMILES: COc1ncc(-c2cc(Cc3ccccc3)c3nccn3n2)c(OC)n1]

8-benzyl-6-(2,4-dimethoxypyrimidin-5-yl)imidazo[1,2-b]pyridazine was prepared in the manner described for Intermediate 36, but using 8-benzyl-6-chloro-imidazo[1,2-b]pyridazine (37 mg, 0.152 mmol) in place of 6-chloro-8-(4,4-difluorocyclohexyl)imidazo[1,2-b]pyridazine. ES/MS m/z: 348.2 [M+1].

Intermediates 43 and 44. 6-chloro-8-[1-(trifluoromethyl)cyclopropyl]imidazo[1,2-b]pyridazine and 6-chloro-2,8-bis[1-(trifluoromethyl)cyclopropyl]imidazo[1,2-b]pyridazine

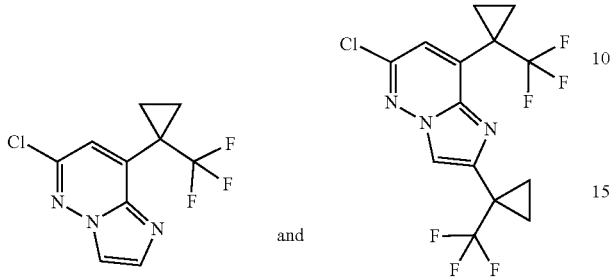

and 6-chloro-8-[1-(trifluoromethyl)cyclopropyl]imidazo[1,2-b]pyridazine (Intermediate 43) and 6-chloro-2,8-bis[1-(trifluoromethyl)cyclopropyl]imidazo[1,2-b]pyridazine (Intermediate 44) were prepared in the manner described for Intermediate 36, but using sodium 1-(trifluoromethyl)cyclopropanesulfinate (239 mg, 1.22 mmol, 2.5 equiv) in place of sodium 4,4-difluorocyclohexane sulfinate. The two products were isolated separately using via silica gel chromatography.

Intermediate 43: 6-chloro-8-[1-(trifluoromethyl)cyclopropyl]imidazo[1,2-b]pyridazine ES/MS m/z: 262.1 [M+1]

Intermediate 44: 6-chloro-2,8-bis[1-(trifluoromethyl)cyclopropyl]imidazo[1,2-b]pyridazine ES/MS m/z: 370.1 [M+1]

Intermediate 45. 6-(2,4-dimethoxypyrimidin-5-yl)-8-[1-(trifluoromethyl)cyclopropyl]imidazo[1,2-b]pyridazine

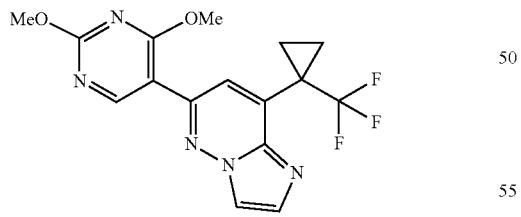

6-(2,4-dimethoxypyrimidin-5-yl)-8-[1-(trifluoromethyl)cyclopropyl]imidazo[1,2-b]pyridazine was prepared in the manner described for Intermediate 36, but using 6-chloro-8-[1-(trifluoromethyl)cyclopropyl]imidazo[1,2-b]pyridazine (12 mg, 0.046 mmol, 1 equiv) in place of 6-chloro-8-(4,4-difluorocyclohexyl)imidazo[1,2-b]pyridazine. ES/MS m/z: 366.1 [M+1].

Intermediate 46. 6-(2,4-dimethoxypyrimidin-5-yl)-2,8-bis[1-(trifluoromethyl)cyclopropyl]imidazo[1,2-b]pyridazine

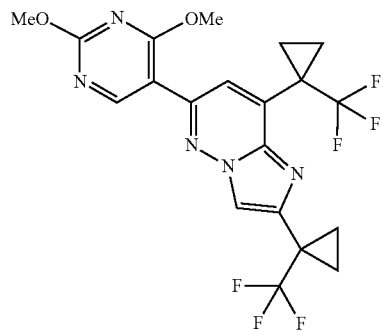 [SMILES: COc1ncc(-c2cc(C3(C(F)(F)F)CC3)c3nc(C4(C(F)(F)F)CC4)cn3n2)c(OC)n1]

6-(2,4-dimethoxypyrimidin-5-yl)-2,8-bis[1-(trifluoromethyl)cyclopropyl]imidazo[1,2-b]pyridazine was prepared in the manner described for Intermediate 36, but 6-chloro-8-(4,4-difluorocyclohexyl)imidazo[1,2-b]pyridazine with 6-chloro-2,8-bis[1-(trifluoromethyl)cyclopropyl]imidazo[1,2-b]pyridazine (23 mg, 0.062 mmol, 1 equiv). ES/MS m/z: 474.1 [M+1].

Intermediates 47 and 48. 8-(benzenesulfonylmethyl)-6-chloro-imidazo[1,2-b]pyridazine and 2,8-bis(benzenesulfonylmethyl)-6-chloro-imidazo[1,2-b]pyridazine

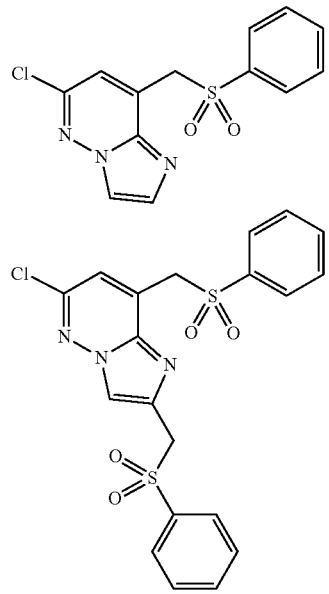

8-(benzenesulfonylmethyl)-6-chloro-imidazo[1,2-b]pyridazine (Intermediate 47) and 2,8-bis(benzenesulfonylmethyl)-6-chloro-imidazo[1,2-b]pyridazine (Intermediate 48) were prepared in the manner described for Intermediate 36, but using zinc bis[(phenylsulfonyl)methanesulfinate] (492 mg, 0.977 mmol, 2 equiv) in place of sodium 4,4-difluorocyclohexane sulfinate. The two products were isolated separately using via silica gel chromatography.

Intermediate 47: 8-(benzenesulfonylmethyl)-6-chloro-imidazo[1,2-b]pyridazine ES/MS m/z: 308.0 [M+1]

Intermediate 48: 2,8-bis(benzenesulfonylmethyl)-6-chloro-imidazo[1,2-b]pyridazine ES/MS m/z: 462.0 [M+1]

Intermediate 49. 8-(benzenesulfonylmethyl)-6-(2,4-dimethoxypyrimidin-5-yl)imidazo[1,2-b]pyridazine

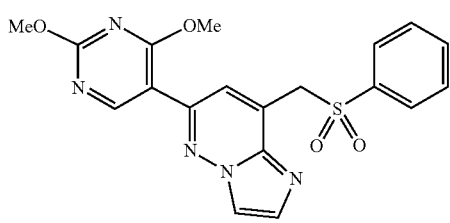 [SMILES: COc1ncc(-c2cc(CS(=O)(=O)c3ccccc3)c3nccn3n2)c(OC)n1]

8-(benzenesulfonylmethyl)-6-(2,4-dimethoxypyrimidin-5-yl)imidazo[1,2-b]pyridazine was prepared in the manner described for Intermediate 36, but replacing 6-chloro-8-(4,4-difluorocyclohexyl)imidazo[1,2-b]pyridazine with 8-(benzenesulfonylmethyl)-6-chloro-imidazo[1,2-b]pyridazine (30 mg, 0.098 mmol, 1 equiv). ES/MS m/z: 412.1 [M+1].

Intermediate 50. 2,8-bis(benzenesulfonylmethyl)-6-(2,4-dimethoxypyrimidin-5-yl)imidazo[1,2-b]pyridazine

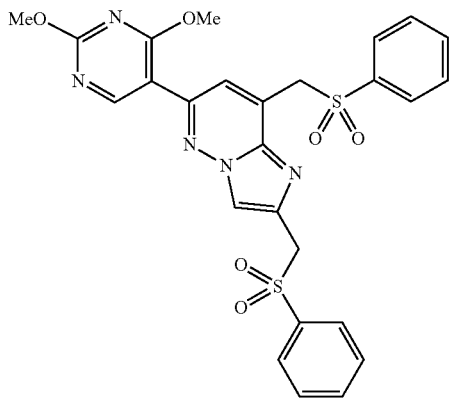 [SMILES: COc1ncc(-c2cc(CS(=O)(=O)c3ccccc3)c3nc(CS(=O)(=O)c4ccccc4)cn3n2)c(OC)n1]

2,8-bis(benzenesulfonylmethyl)-6-(2,4-dimethoxypyrimidin-5-yl)imidazo[1,2-b]pyridazine was prepared in the manner described for Intermediate 36, but replacing 6-chloro-8-(4,4-difluorocyclohexyl)imidazo[1,2-b]pyridazine with 2,8-bis(benzenesulfonylmethyl)-6-chloro-imidazo[1,2-b]pyridazine (13 mg, 0.028 mmol, 1 equiv). ES/MS m/z: 566.1 [M+1].

C—H Alkylation Reactions

Intermediate 51. 6-chloro-8-(4,4-difluorocyclohexyl)-2-methyl-[1,2,4]triazolo[1,5-b]pyridazine

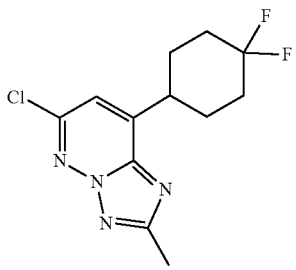 [SMILES: Cc1nc2c(C3CCC(F)(F)CC3)cc(Cl)nn2n1]

To a mixture of 6-chloro-2-methyl-[1,2,4]triazolo[1,5-b]pyridazine (75 mg, 0.445 mmol) and sodium 4,4-difluorocyclohexanesulfinate (229 mg, 1.11 mmol) in DMSO (1.26 mL) and water (0.252 mL) was added tert-butyl hydroperoxide solution (70% in water, 0.318 mL, 2.22 mmol). The mixture was heated to 50° C. and stirred for 2 h. The mixture was then diluted with water and extracted with EtOAc. The combined organics were dried over MgSO₄, filtered, and concentrated in vacuo. The resulting residue was purified by silica gel chromatography (0-100% EtOAc/hexanes) to afford 6-chloro-8-(4,4-difluorocyclohexyl)-2-methyl-[1,2,4]triazolo[1,5-b]pyridazine. ES/MS m/z: 287.1 [M+1].

Intermediate 52. 6-chloro-8-(4,4-difluorocyclohexyl)imidazo[1,2-b]pyridazine-3-carbonitrile

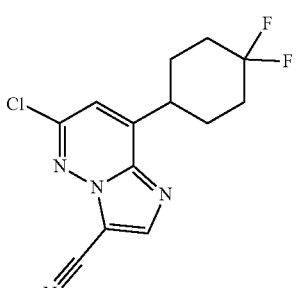

6-chloro-8-(4,4-difluorocyclohexyl)imidazo[1,2-b]pyridazine-3-carbonitrile was prepared in the manner described for Intermediate 51, but replacing 6-chloro-2-methyl-[1,2,4]triazolo[1,5-b]pyridazine with 6-chloroimidazo[1,2-b]pyridazine-3-carbonitrile. ES/MS m/z: 297.1 [M+1].

Intermediate 53. 6-chloro-8-(4,4-difluorocyclo-hexyl)-3-methyl-imidazo[1,2-b]pyridazine

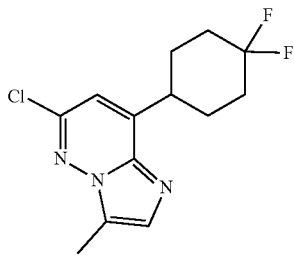 [SMILES: Cc1cnc2c(C3CCC(F)(F)CC3)cc(Cl)nn12]

6-chloro-8-(4,4-difluorocyclohexyl)-3-methyl-imidazo[1,2-b]pyridazine was prepared in the manner described for Intermediate 51, but replacing 6-chloro-2-methyl-[1,2,4]triazolo[1,5-b]pyridazine with 6-chloro-3-methyl-imidazo[1,2-b]pyridazine. ES/MS m/z: 286.1 [M+1].

Intermediate 54. 8-((benzyloxy)methyl)-6-chloro-imidazo[1,2-b]pyridazine

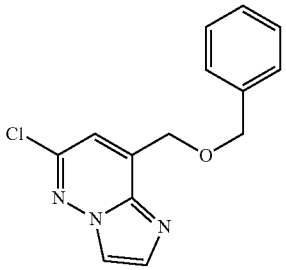 [SMILES: Clc1cc(COCc2ccccc2)c2nccn2n1]

To the solids 6-chloroimidazo[1,2-b]pyridazine (0.150 g, 0.977 mmol, 1 equiv), ((benzyloxy)methyl)trifluoroborane potassium salt (0.178 g, 1.47 mmol, 1.5 equiv), K2S2O8 (0.528 g, 1.95 mmol, 2 equiv) and 9-Mesityl-10-methylacridinium tetrafluoroborate (0.0195 g, 0.049 mmol, 5 mol %) was added acetonitrile (4.8 mL), water (4.8 mL) and TFA (0.075 mL, 0.977 mmol, 1 equiv). The reaction mixture was stirred in a fan cooled, Blue LED photoreactor for 16 hours. The reaction was quenched with saturated aqueous NaHCO₃, extracted twice with EtOAc, the combined organic layers were dried over MgSO4, filtered and concentrated in vacuo. The product was purified by silica gel chromatography to provide 8-((benzyloxy)methyl)-6-chloroimidazo[1,2-b]pyridazine. ES/MS m/z: 274.05 [M+H].

SNAr Reaction with Cyclic Amines

Intermediate 55. 6-chloro-8-(3-phenylazetidin-1-yl)imidazo[1,2-b]pyridazine

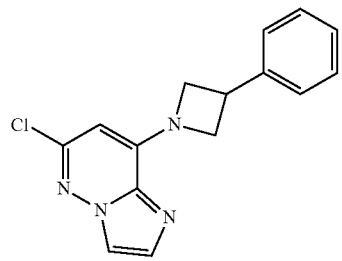 [SMILES: Clc1cc(N2CC(c3ccccc3)C2)c2nccn2n1]

To a mixture of 8-bromo-6-chloro-imidazo[1,2-b]pyridazine (150 mg, 0.645 mmol) and 3-phenylazetidine hydrochloride (109 mg, 0.645 mmol) in MeCN (2 mL) was added N,N-diisopropylethylamine (0.337 mL, 1.94 mmol). The mixture was heated to 100° C. and stirred for 4 h. The mixture was then concentrated in vacuo and the resulting residue was purified by silica gel chromatography (0-100% EtOAc/hexanes) to afford 6-chloro-8-(3-phenylazetidin-1-yl)imidazo[1,2-b]pyridazine. ES/MS m/z: 285.1 [M+1].

Intermediate 56. 6-chloro-8-[3-(trifluoromethyl)azetidin-1-yl]imidazo[1,2-b]pyridazine

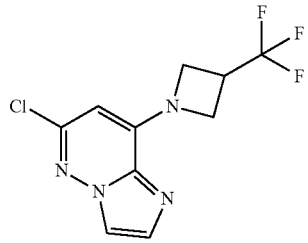 [SMILES: FC(F)(F)C1CN(c2cc(Cl)nn3ccnc23)C1]

6-chloro-8-[3-(trifluoromethyl)azetidin-1-yl]imidazo[1,2-b]pyridazine was prepared in the manner described for Intermediate 55, but replacing 3-phenylazetidine hydrochloride with 3-(trifluoromethyl)azetidine. ES/MS m/z: 277.1 [M+1].

Intermediate 57. 6-chloro-8-(3,3-dimethylazetidin-1-yl)imidazo[1,2-b]pyridazine

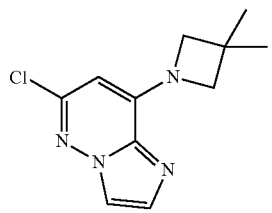 [SMILES: CC1(C)CN(c2cc(Cl)nn3ccnc23)C1]

6-chloro-8-(3,3-dimethylazetidin-1-yl)imidazo[1,2-b]pyridazine was prepared in the manner described for Intermediate 55, but replacing 3-phenylazetidine hydrochloride with 3,3-dimethylazetidine hydrochloride. ES/MS m/z: 237.1 [M+1].

Intermediate 58. 6-chloro-8-(2-phenylazetidin-1-yl)imidazo[1,2-b]pyridazine (Rracemic Mixture)

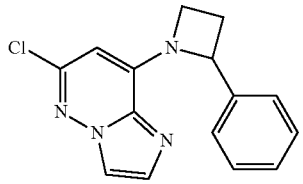 [SMILES: Clc1cc(N2CCC2c2ccccc2)c2nccn2n1]

6-chloro-8-(2-phenylazetidin-1-yl)imidazo[1,2-b]pyridazine was prepared as a racemic mixture in the manner described for Intermediate 55, but replacing 3-phenylazetidine hydrochloride with 2-phenylazetidine. ES/MS m/z: 285.1 [M+1].

Intermediate 59. 6-chloro-8-(3,3-dimethylpyrrolidin-1-yl)imidazo[1,2-b]pyridazine

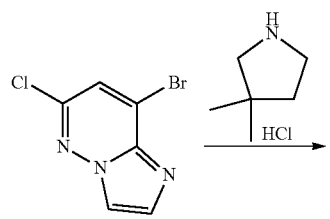

A microwave vial was charged with 8-bromo-6-chloro-imidazo[1,2-b]pyridazine (250 mg, 1.08 mmol, 1 equiv), 3,3-dimethylpyrrolidine hydrochloride (160 mg, 1.18 mmol, 1.1 equiv), DIPEA (0.481 mL, 2.69 mmol, 2.5 equiv), and MeCN (5 mL). The reaction mixture was heated to 85° C. After 24 hours, the reaction mixture was concentrated. The residue obtained was triturated with water, the resulting solids were filtered, washed with water, and dried affording 6-chloro-8-(3,3-dimethylpyrrolidin-1-yl)imidazo[1,2-b]pyridazine. ES/MS m/z: 251.10 [M+1].

Intermediate 60. 6-chloro-8-(3,3-difluoro-4,4-dimethyl-pyrrolidin-1-yl)imidazo[1,2-b]pyridazine

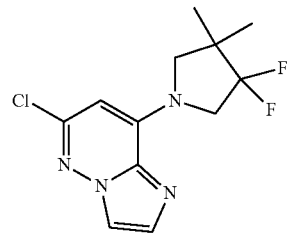 [SMILES: CC1(C)CN(c2cc(Cl)nn3ccnc23)CC1(F)F]

6-chloro-8-(3,3-difluoro-4,4-dimethyl-pyrrolidin-1-yl)imidazo[1,2-b]pyridazine was prepared in the manner described for Intermediate 59, but replacing 3,3-dimethylpyrrolidine hydrochloride with 3,3-difluoro-4,4-dimethyl-pyrrolidine hydrochloride. ES/MS m/z: 287.10 [M+H].

Intermediate 61. 6-chloro-8-[(3S,4R)-3,4-difluoro-pyrrolidin-1-yl]imidazo[1,2-b]pyridazine

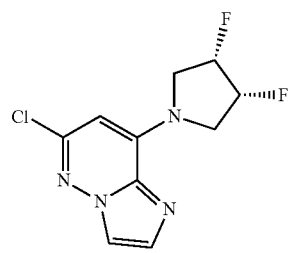 [SMILES: F[C@@H]1CN(c2cc(Cl)nn3ccnc23)C[C@@H]1F]

6-chloro-8-[(3S,4R)-3,4-difluoropyrrolidin-1-yl]imidazo[1,2-b]pyridazine(cis) was prepared in the manner described for Intermediate 59, but replacing 3,3-dimethylpyrrolidine hydrochloride with (3S,4R)-3,4-difluoropyrrolidine hydrochloride(cis). ES/MS m/z: 259.10 [M+H].

Intermediate 62. 6-chloro-8-[(3S,4S)-3,4-difluoro-pyrrolidin-1-yl]imidazo[1,2-b]pyridazine

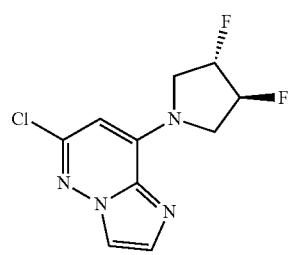 [SMILES: F[C@H]1CN(c2cc(Cl)nn3ccnc23)C[C@@H]1F]

6-chloro-8-[(3S,4S)-3,4-difluoropyrrolidin-1-yl]imidazo[1,2-b]pyridazine(trans relative) was prepared in the manner described for Intermediate 59, but replacing 3,3-dimethylpyrrolidine hydrochloride with (3S,4S)-3,4-difluoropyrrolidine hydrochloride. ES/MS m/z: 259.10 [M+H].

Intermediate 63. 6-chloro-8-(3,3-difluoropyrrolidin-1-yl)imidazo[1,2-b]pyridazine

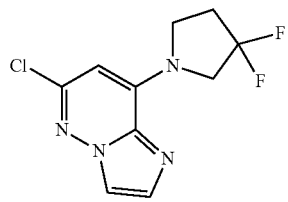 [SMILES: FC1(F)CCN(c2cc(Cl)nn3ccnc23)C1]

6-chloro-8-(3,3-difluoropyrrolidin-1-yl)imidazo[1,2-b]pyridazine was prepared in the manner described for Intermediate 59, but replacing 3,3-dimethylpyrrolidine hydrochloride with 3,3-difluoropyrrolidine. ES/MS m/z: 259.10 [M+H].

Intermediate 64. 6-chloro-8-(4,4-dimethyl-1-piperidyl)imidazo[1,2-b]pyridazine

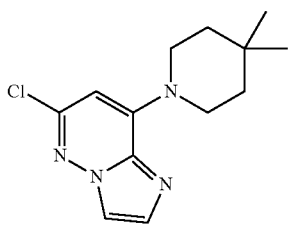 [SMILES: CC1(C)CCN(c2cc(Cl)nn3ccnc23)CC1]

6-chloro-8-(4,4-dimethyl-1-piperidyl)imidazo[1,2-b]pyridazine was prepared in the manner described for Intermediate 59, but replacing 3,3-dimethylpyrrolidine hydrochloride with 4,4-dimethylpiperidine hydrochloride. ES/MS m/z: 265.20 [M+H].

Intermediate 65. 5-chloro-7-(3,3-dimethylpyrrolidin-1-yl)pyrazolo[1,5-a]pyrimidine

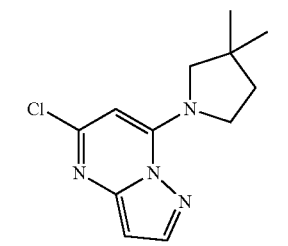 [SMILES: CC1(C)CCN(c2cc(Cl)nc3ccnn23)C1]

To a solution of 5,7-dichloropyrazolo[1,5-a]pyrimidine (0.200 g, 1.06 mmol, 1 equiv) in ethanol (1.6 mL) was added K$_2$CO$_3$ (0.296 g, 2.13 mmol, 2 equiv) and 3,3-dimethylpyrrolidine (0.116 g, 1.17 mmol, 1.1 equiv). The reaction mixture was stirred overnight at 90° C. before being diluted with EtOAc, filtered and concentrated in vacuo. The resulting 5-chloro-7-(3,3-dimethylpyrrolidin-1-yl)pyrazolo[1,5-a]pyrimidine was used without further purification. ES/MS m/z: 251.08 [M+H].

Intermediate 66. 5-chloro-7-(3,3-dimethylpyrrolidin-1-yl)-[1,2,4]triazolo[1,5-a]pyrimidine

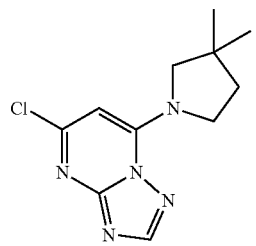 [SMILES: CC1(C)CCN(c2cc(Cl)nc3ncnn23)C1]

5-chloro-7-(3,3-dimethylpyrrolidin-1-yl)-[1,2,4]triazolo[1,5-a]pyrimidine was prepared in the manner described for Intermediate 65, but replacing 5,7-dichloropyrazolo[1,5-a]pyrimidine with 5,7-dichloro-[1,2,4]triazolo[1,5-a]pyrimidine. ES/MS m/z: 252.10 [M+H].

Intermediate 67. 6-chloro-8-(3,3-difluoropiperidin-1-yl)imidazo[1,2-b]pyridazine

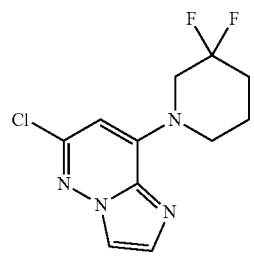 [SMILES: FC1(F)CCCN(c2cc(Cl)nn3ccnc23)C1]

6-chloro-8-(3,3-difluoropiperidin-1-yl)imidazo[1,2-b]pyridazine was prepared in the manner described for Intermediate 65, but replacing 5,7-dichloropyrazolo[1,5-a]pyrimidine with 8-bromo-6-chloroimidazo[1,2-b]pyridazine, and 3,3-dimethylpyrrolidine with 3,3-difluoropiperidine hydrochloride. ES/MS m/z: 273.10 [M+H].

Intermediate 68. 8-(3-azabicyclo[3.2.1]octan-3-yl)-6-chloroimidazo[1,2-b]pyridazine

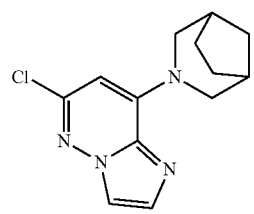 [SMILES: Clc1cc(N2CC3CCC(C3)C2)c2nccn2n1]

8-(3-azabicyclo[3.2.1]octan-3-yl)-6-chloroimidazo[1,2-b]pyridazine was prepared in the manner described for Intermediate 65, but replacing 5,7-dichloropyrazolo[1,5-a]pyrimidine with 8-bromo-6-chloroimidazo[1,2-b]pyridazine, and 3,3-dimethylpyrrolidine with 3-azabicyclo[3.2.1]octane. ES/MS m/z: 263.00 [M+H].

Intermediate 69. 6-chloro-8-(3,3,4,4-tetrafluoropyrrolidin-1-yl)imidazo[1,2-b]pyridazine

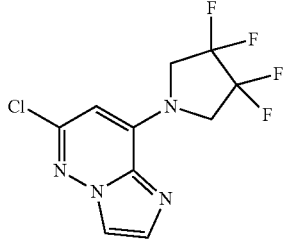 [SMILES: FC1(F)CN(c2cc(Cl)nn3ccnc23)CC1(F)F]

To a mixture of 8-bromo-6-chloro-imidazo[1,2-b]pyridazine (0.2 g, 0.86 mmol) and potassium carbonate (0.24 g, 1.72 mmol) in EtOH (2 mL) was added 3,3,4,4-tetrafluoropyrrolidine;hydrochloride (154 mg, 0.86 mmol). The reaction mixture was heated at 90° C. overnight. The solvent was then evaporated and the residue was purified by Prep HPLC (10-90% ACN/water with TFA) to afford 6-chloro-8-(3,3,4,4-tetrafluoropyrrolidin-1-yl)imidazo[1,2-b]pyridazine. ES/MS m/z: 392.20 [M+H].

Intermediate 70. 6-chloro-8-pyrazol-1-yl-imidazo[1,2-b]pyridazine

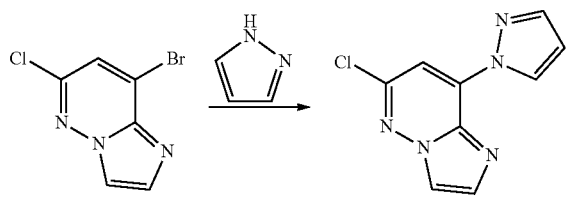

A microwave vial was charged with 8-bromo-6-chloro-imidazo[1,2-b]pyridazine (250 mg, 1.08 mmol, 1 equiv), 1H-pyrazole (80.5 mg, 1.18 mmol, 1.1 equiv), potassium carbonate (233 mg, 1.61 mmol, 1.5 equiv), and NMP (5 mL). The reaction mixture was heated to 90° C. After 8 hours, the reaction mixture was diluted with water, the resulting solids were filtered, washed with water and dried to provide 6-chloro-8-pyrazol-1-yl-imidazo[1,2-b]pyridazine. ES/MS m/z: 220.10 [M+H].

Intermediate 71. 2-(2-fluoro-2-phenylcyclopropyl)-4,4,5,5-tetramethyl-1,3,2-dioxaborolane

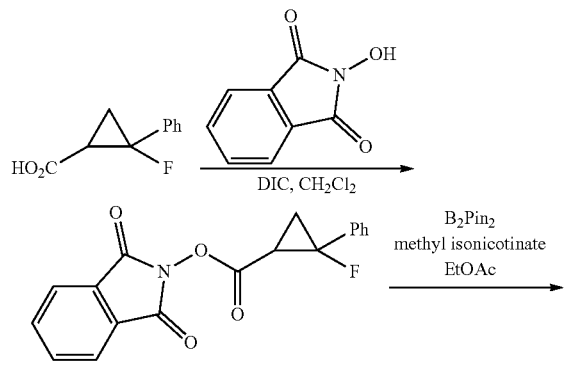

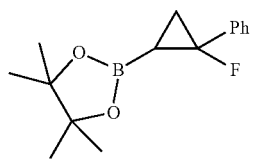

Step 1: To a solution of 2-fluoro-2-phenyl-cyclopropanecarboxylic acid (500 mg, 2.78 mmol, 1 equiv) in CH$_2$Cl$_2$ (10 mL) was added diisopropylmethanediimine (0.48 mL, 3.05 mmol, 1.1 equiv), N,N-dimethylpyridin-4-amine (34 mg, 10 mol %), and 2-hydroxyisoindoline-1,3-dione (498 mg, 3.05 mmol, 1.1 equiv). After 6 hours, the reaction mixture was filtered over celite with CH$_2$Cl$_2$ washings and concentrated. The residue was purified by SiO$_2$ chromatography (0-100% EtOAc/Hex), affording 1,3-dioxoisoindolin-2-yl 2-fluoro-2-phenylcyclopropane-1-carboxylate (mixture of cis and trans diastereomers). $^1$H NMR of diastereomeric mixture (400 MHz, Chloroform-d) δ 7.94-7.33 (m), 2.99-2.84 (m, 1H), 2.58-2.36 (m, 2H), 2.22-2.06 (m, 2H), 2.01-1.90 (m, 1H).

Step 2: To a solution of 1,3-dioxoisoindolin-2-yl 2-fluoro-2-phenylcyclopropane-1-carboxylate (1.00 g, 3.07 mmol, 1 equiv) in EtOAc (15 mL, 0.2M) was added B2Pin2 (1.56 g, 6.15 mmol, 2 equiv) and methyl isonicotinate (0.18 mL, 1.54 mmol, 0.5 equiv). The resulting mixture was heated to 80° C. under an atmosphere of argon. After 20 hours, the reaction mixture was filtered, concentrated, and purified by SiO$_2$ chromatography (0-50% EtOAc/Hex), affording 2-(2-fluoro-2-phenylcyclopropyl)-4,4,5,5-tetramethyl-1,3,2-dioxaborolane.

Preparation of Chiral Cyclopropyl Boronate Esters

Intermediate 72. 2-chloro-5-((2S,2S)-2-(4,4,5,5-tetramethyl-1,3,2-dioxaborolan-2-yl)cyclopropyl)benzonitrile

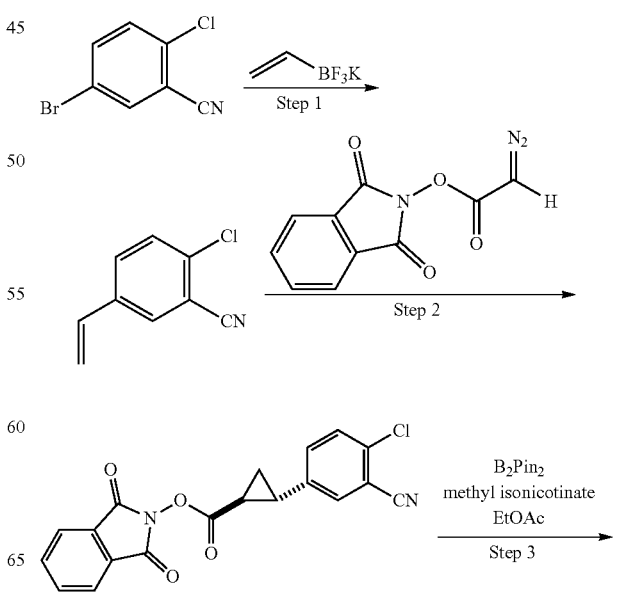

-continued

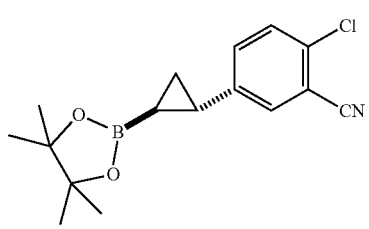

Step 1: A solution of 5-bromo-2-chlorobenzonitrile (1000 mg, 4.62 mmol, 1 equiv), potassium vinyltrifluoroborate (681 mg, 5.08 mmol, 1.1 equiv), and potassium carbonate (1.92 g, 13.9 mmol, 3 equiv) in 9:1 THF/H$_2$O (10 mL) was degassed with Argon. Then, PdCl$_2$(dppf)-CH$_2$Cl$_2$ (169 mg, 5 mol %) was added, and the reaction mixture was heated to 85° C. After 18 hours, the reaction mixture was cooled to room temperature, diluted with H$_2$O (5 mL), and extracted with CH$_2$Cl$_2$ (3×20 mL). The combined organic layers were dried over Na$_2$SO$_4$, filtered, and concentrated. Purification was accomplished by SiO$_2$ chromatography (0-20% EtOAc/Hex), affording 2-chloro-5-vinylbenzonitrile. $^1$H NMR (400 MHz, Chloroform-d) δ 7.67 (d, J=2.2 Hz, 1H), 7.60-7.43 (m, 2H), 6.65 (dd, J=17.6, 10.9 Hz, 1H), 5.80 (d, J=17.6 Hz, 1H), 5.42 (d, J=10.9 Hz, 1H).

Step 2: To a cooled (0° C.) solution of 2-chloro-5-vinylbenzonitrile (600 mg, 3.67 mmol, 1 equiv) and tetrakis(acetonitrile)[2-[(4R)-4,5-dihydro-4-phenyl-2-oxazolyl-N]phenyl]ruthenium(II) hexafluorophosphate (23.2 mg, 1 mol %; also known as Ru(II)-(R)-Pheox catalyst) in CH$_2$Cl$_2$ (37 mL, 0.1M) was added a solution of 1,3-dioxoisoindolin-2-yl 2-diazoacetate (1.02 g, 4.40 mmol, 1.2 equiv) in CH$_2$Cl$_2$ (15 mL) over 40 minutes. After an additional 4 hours at 0° C., the reaction mixture was quenched with MeOH (5 mL), concentrated to ~10 mL, and directly purified by SiO$_2$ chromatography (0-70% EtOAc/Hex), affording 1,3-dioxoisoindolin-2-yl (1S,2S)-2-(4-chloro-3-cyanophenyl)cyclopropane-1-carboxylate. The enantiomeric excess was determined by chiral SFC analysis. $^1$H NMR (400 MHz, Chloroform-d) δ7.94-7.87 (m, 2H), 7.84-7.78 (m, 2H), 7.52-7.45 (m, 2H), 7.36 (dd, J=8.4, 2.3 Hz, 1H), 2.82-2.74 (m, 1H), 2.27-2.18 (m, 1H), 1.94-1.85 (m, 1H), 1.65-1.58 (m, 1H).

Step 3: To a solution of 1,3-dioxoisoindolin-2-yl (1S,2S)-2-(4-chloro-3-cyanophenyl)cyclopropane-1-carboxylate (1.35 g, 3.68 mmol, 1 equiv) and bis(pinacolato)diboron (1.87 g, 7.36 mmol, 2 equiv) in EtOAc (74 mL) was added methyl isonicotinate (0.22 mL, 1.84 mmol, 0.5 equiv). The reaction mixture was heated to 80° C. After 16 hours, the reaction mixture was filtered and concentrated. Purification was accomplished by SiO$_2$ chromatography (0-20% EtOAc/Hex), affording 2-chloro-5-((2S,2S)-2-(4,4,5,5-tetramethyl-1,3,2-dioxaborolan-2-yl)cyclopropyl)benzonitrile. $^1$H NMR (400 MHz, Chloroform-d) δ7.38-7.32 (m, 2H), 7.19 (dd, J=8.5, 2.3 Hz, 1H), 2.11-2.05 (m, 1H), 1.26-1.23 (m, 13H), 1.03-0.96 (m, 1H), 0.32-0.23 (m, 1H).

Intermediate 73. 4-((1S,2S)-2-(4,4,5,5-tetramethyl-1,3,2-dioxaborolan-2-yl)cyclopropyl)benzonitrile

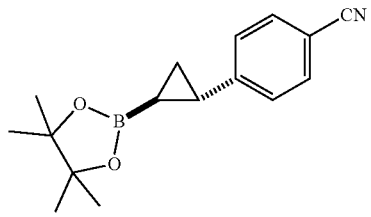

4-((1S,2S)-2-(4,4,5,5-tetramethyl-1,3,2-dioxaborolan-2-yl)cyclopropyl)benzonitrile was prepared in the manner described for Intermediate 72, but replacing 2-chloro-5-vinylbenzonitrile with 4-vinylbenzonitrile. $^1$H NMR (400 MHz, Chloroform-d) δ 7.54-7.48 (m, 2H), 7.16-7.10 (m, 2H), 2.12 (dt, J=8.1, 5.3 Hz, 1H), 1.29-1.24 (m, 13H), 1.05 (ddd, J=9.9, 5.2, 3.9 Hz, 1H), 0.36 (ddd, J=10.0, 7.1, 5.5 Hz, 1H).

Intermediate 74. 3-fluoro-4-((1S,2S)-2-(4,4,5,5-tetramethyl-1,3,2-dioxaborolan-2-yl)cyclopropyl)benzonitrile

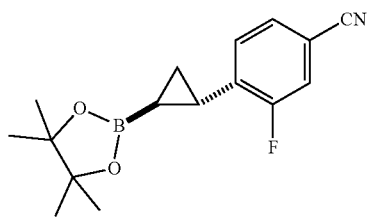

3-fluoro-4-((1S,2S)-2-(4,4,5,5-tetramethyl-1,3,2-dioxaborolan-2-yl)cyclopropyl)benzonitrile was prepared in the manner described for Intermediate 72, but replacing 5-bromo-2-chlorobenzonitrile with 4-bromo-3-fluorobenzonitrile. $^1$H NMR (400 MHz, DMSO-d$_6$) δ 7.76 (dd, J=10.3, 1.7 Hz, 1H), 7.58 (dd, J=8.0, 1.6 Hz, 1H), 7.21 (t, J=7.9 Hz, 1H), 2.18 (dt, J=8.1, 5.4 Hz, 1H), 1.29-1.21 (m, 1H), 1.17 (s, 12H), 0.86-0.79 (m, 1H), 0.34 (ddd, J=9.9, 7.0, 5.6 Hz, 1H). $^{19}$F NMR (376 MHz, DMSO-d6) δ −119.16 (dd, J=10.3, 7.7 Hz).

Intermediate 75. 4,4,5,5-tetramethyl-2-((1S,2S)-2-(4-(trifluoromethyl)phenyl)cyclopropyl)-1,3,2-dioxaborolane

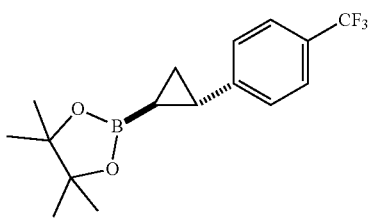

4,4,5,5-tetramethyl-2-((2S,2S)-2-(4-(trifluoromethyl)phenyl)cyclopropyl)-1,3,2-dioxaborolane was prepared in the manner described for Intermediate 72, but replacing 5-bromo-2-chlorobenzonitrile with 1-bromo-4-(trifluoromethyl)benzene. ¹H NMR (400 MHz, Chloroform-d) δ 7.50 (d, J=8.1 Hz, 2H), 7.18 (d, J=8.1 Hz, 2H), 2.20-2.11 (m, 1H), 1.31-1.20 (m, 13H), 1.11-1.02 (m, 1H), 0.41-0.31 (m, 1H).

Intermediate 76. 4,4,5,5-tetramethyl-2-((1S,2S)-2-(4-(trifluoromethoxy)phenyl)cyclopropyl)-1,3,2-dioxaborolane

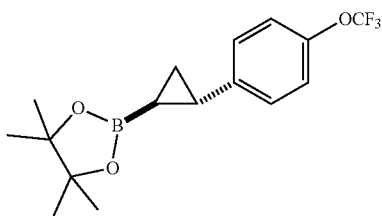

4,4,5,5-tetramethyl-2-((2S,2S)-2-(4-(trifluoromethoxy)phenyl)cyclopropyl)-1,3,2-dioxaborolane was prepared in the manner described for Intermediate 72, but replacing 5-bromo-2-chlorobenzonitrile with 1-bromo-4-(trifluoromethoxy)benzene. ¹H NMR (400 MHz, Chloroform-d) δ 7.10 (s, 4H), 2.16-2.09 (m, 1H), 1.28 (s, 6H), 1.27 (s, 6H), 1.23-1.16 (m, 1H), 1.03-0.96 (m, 1H), 0.34-0.26 (m, 1H).

Intermediate 77. 2-fluoro-4-((2S,2S)-2-(4,4,5,5-tetramethyl-1,3,2-dioxaborolan-2-yl)cyclopropyl)benzonitrile

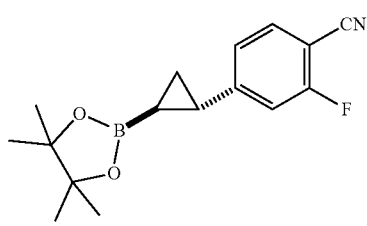

2-fluoro-4-(1S,2S)-2-(4,4,5,5-tetramethyl-1,3,2-dioxaborolan-2-yl)cyclopropyl)benzonitrile was prepared in the manner described for Intermediate 72, but replacing 5-bromo-2-chlorobenzonitrile with 4-bromo-2-fluoro-benzonitrile. ¹H NMR (400 MHz, Chloroform-d) δ 7.46 (dd, J=8.1, 6.7 Hz, 1H), 6.93 (dd, J=8.1, 1.6 Hz, 1H), 6.86 (dd, J=10.4, 1.6 Hz, 1H), 2.15-2.06 (m, 1H), 1.34-1.18 (m, 13H), 1.09-1.00 (m, 1H), 0.42-0.31 (m, 1H).

Intermediate 78. 2,3-difluoro-4-((2S,2S)-2-(4,4,5,5-tetramethyl-1,3,2-dioxaborolan-2-yl)cyclopropyl)benzonitrile

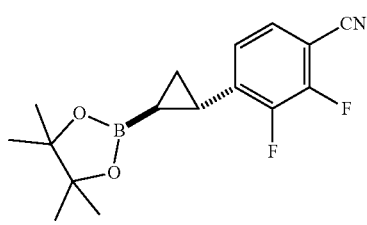

2,3-difluoro-4-(1S,2S)-2-(4,4,5,5-tetramethyl-1,3,2-dioxaborolan-2-yl)cyclopropyl)benzonitrile was prepared in the manner described for Intermediate 72, but replacing 5-bromo-2-chlorobenzonitrile with 4-bromo-2,3-difluoro-benzonitrile. ¹H NMR (400 MHz, Chloroform-d) δ 7.27-7.19 (m, 1H), 6.74-6.63 (m, 1H), 2.40-2.30 (m, 1H), 1.37-1.19 (m, 13H), 1.14-1.08 (m, 1H), 0.44-0.34 (m, 1H).

Intermediate 79. 2-methoxy-4-((2S,2S)-2-(4,4,5,5-tetramethyl-1,3,2-dioxaborolan-2-yl)cyclopropyl)benzonitrile

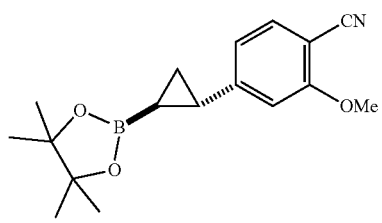

2-methoxy-4-(1S,2S)-2-(4,4,5,5-tetramethyl-1,3,2-dioxaborolan-2-yl)cyclopropyl)benzonitrile was prepared in the manner described for Intermediate 72, but replacing 5-bromo-2-chlorobenzonitrile with 4-bromo-2-methoxybenzonitrile. ¹H NMR (400 MHz, Chloroform-d) δ 7.43 (d, J=8.3 Hz, 1H), 6.71-6.64 (m, 2H), 3.92 (s, 3H), 2.18-2.09 (m, 1H), 1.32-1.19 (m, 13H), 1.11-1.01 (m, 1H), 0.44-0.35 (m, 1H).

Intermediate 80. 2-methyl-4-((2S,2S)-2-(4,4,5,5-tetramethyl-1,3,2-dioxaborolan-2-yl)cyclopropyl)benzonitrile

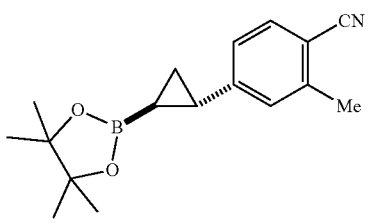

2-methyl-4-((2S,2S)-2-(4,4,5,5-tetramethyl-1,3,2-dioxaborolan-2-yl)cyclopropyl)benzonitrile was prepared in the manner described for Intermediate 72, but replacing 5-bromo-2-chlorobenzonitrile with 4-bromo-2-methyl-benzonitrile. ¹H NMR (400 MHz, Chloroform-d) δ 7.47 (d, J=8.1 Hz, 1H), 7.02 (s, 1H), 6.97-6.90 (m, 1H), 2.51 (s, 3H), 2.13-2.07 (m, 1H), 1.28-1.25 (m, 13H), 1.10-1.02 (m, 1H), 0.40-0.31 (m, 1H).

Suzuki Cross Coupling with Cyclopropyl Boronate Esters

Intermediate 81. 6-chloro-8-[(1S,2S)-2-(3,5-difluorophenyl)cyclopropyl]imidazo[1,2-b]pyridazine (Racemic Mixture)

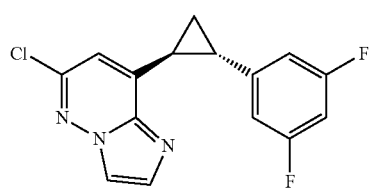 [SMILES: Fc1cc(F)cc([C@H]2C[C@@H]2c2cc(Cl)nn3ccnc23)c1]

6-chloro-8-[(1S,2S)-2-(3,5-difluorophenyl)cyclopropyl]imidazo[1,2-b]pyridazine was prepared as a racemic mixture as follows: A microwave vial was charged with 8-bromo-6-chloro-imidazo[1,2-b]pyridazine (299 mg, 1.29 mmol, 1.2 equiv), racemic 2-((1S,2S)-2-(3,5-difluorophenyl)cyclopropyl1-4,4,5,5-tetramethyl-1,3,2-dioxaborolane (300 mg, 1.07 mmol, 1 equiv), cesium carbonate (698 mg, 2.14 mmol, 2 equiv), and Pd(dppf)Cl$_2$CH$_2$Cl$_2$ (88 mg, 10 mol %). The solids were dissolved in dioxane (3 mL) and H$_2$O (1.5 mL), and the mixture was degassed with N2. The vial was sealed and heated to 120° C. for 4 h. The reaction mixture was then cooled and filtered through celite, washing with EtOAc. The filtrate was concentrated in vacuo, and the resulting residue purified by silica gel chromatography (0-100% EtOAc/hexanes), affording 6-chloro-8-[(1S,2S)-2-(3,5-difluorophenyl)cyclopropyl]imidazo[1,2-b]pyridazine. ES/MS m/z: 306.0 [M+H].

Intermediate 82. 6-chloro-8-[(1S,2S)-2-(2,3,5-trifluorophenyl)cyclopropyl]imidazo[1,2-b]pyridazine (Racemic Mixture)

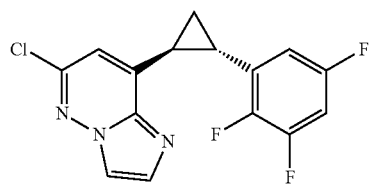 [SMILES: Fc1cc(F)c(F)c([C@H]2C[C@@H]2c2cc(Cl)nn3ccnc23)c1]

6-chloro-8-[(1S,2S)-2-(2,3,5-trifluorophenyl)cyclopropyl]imidazo[1,2-b]pyridazine was prepared as a racemic mixture in the manner described for Intermediate 81, but replacing 2-[(1S,2S)-2-(3,5-difluorophenyl)cyclopropyl]-4,4,5,5-tetramethyl-1,3,2-dioxaborolane with 4,4,5,5-tetramethyl-2-[(1S,2S)-2-(2,3,5-trifluorophenyl)cyclopropyl]-1,3,2-dioxaborolane. ES/MS m/z: 324.0 [M+1].

Intermediate 83. 4-[(1S,2S)-2-(6-chloroimidazo[1,2-b]pyridazin-8-yl)cyclopropyl]-2-fluoro-benzonitrile (Racemic Mixture)

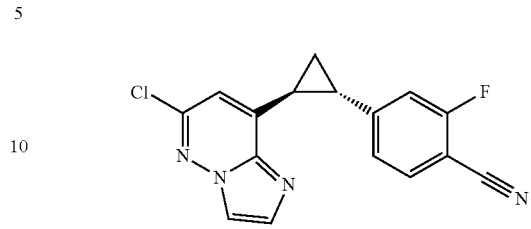

4-[(1S,2S)-2-(6-chloroimidazo[1,2-b]pyridazin-8-yl)cyclopropyl]-2-fluoro-benzonitrile was prepared as a racemic mixture in the manner described for Intermediate 81, but replacing 2-[(1S,2S)-2-(3,5-difluorophenyl)cyclopropyl]-4,4,5,5-tetramethyl-1,3,2-dioxaborolane with 2-fluoro-4-[(1S,2S)-2-(4,4,5,5-tetramethyl-1,3,2-dioxaborolan-2-yl)cyclopropyl]benzonitrile. ES/MS m/z: 313.1 [M+1].

Intermediate 84. 5-[(1S,2S)-2-(6-chloroimidazo[1,2-b]pyridazin-8-yl)cyclopropyl]-2-fluoro-benzonitrile (Racemic Mixture)

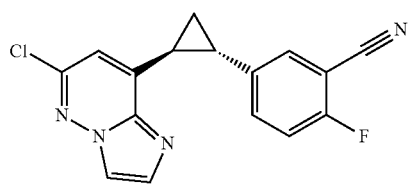 [SMILES: N#Cc1cc([C@H]2C[C@@H]2c2cc(Cl)nn3ccnc23)ccc1F]

5-[(1S,2S)-2-(6-chloroimidazo[1,2-b]pyridazin-8-yl)cyclopropyl]-2-fluoro-benzonitrile was prepared as a racemic mixture in the manner described for Intermediate 81, but replacing 2-[(1S,2S)-2-(3,5-difluorophenyl)cyclopropyl]-4,4,5,5-tetramethyl-1,3,2-dioxaborolane with 2-fluoro-5-[(1S,2S)-2-(4,4,5,5-tetramethyl-1,3,2-dioxaborolan-2-yl)cyclopropyl]benzonitrile. ES/MS m/z: 313.1 [M+1].

Intermediate 85. 6-chloro-8-[(1S,2S)-2-(2,5-difluorophenyl)cyclopropyl]imidazo[1,2-b]pyridazine (Racemic Mixture)

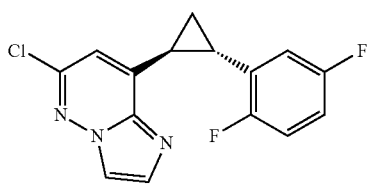 [SMILES: Fc1ccc(F)c([C@H]2C[C@@H]2c2cc(Cl)nn3ccnc23)c1]

6-chloro-8-[(1S,2S)-2-(2,5-difluorophenyl)cyclopropyl]imidazo[1,2-b]pyridazine was prepared as a racemic mixture in the manner described for Intermediate 81, but replacing 2-[(1S,2S)-2-(3,5-difluorophenyl)cyclopropyl]-4,4,5,5-tetramethyl-1,3,2-dioxaborolane with 2-[(1S,2S)-2-(2,5-difluorophenyl)cyclopropyl]-4,4,5,5-tetramethyl-1,3,2-dioxaborolane. ES/MS m/z: 306.1 [M+1].

Intermediate 86. 6-chloro-8-[(1S,2S)-2-(2-pyridyl)cyclopropyl]imidazo[1,2-b]pyridazine (Racemic Mixture)

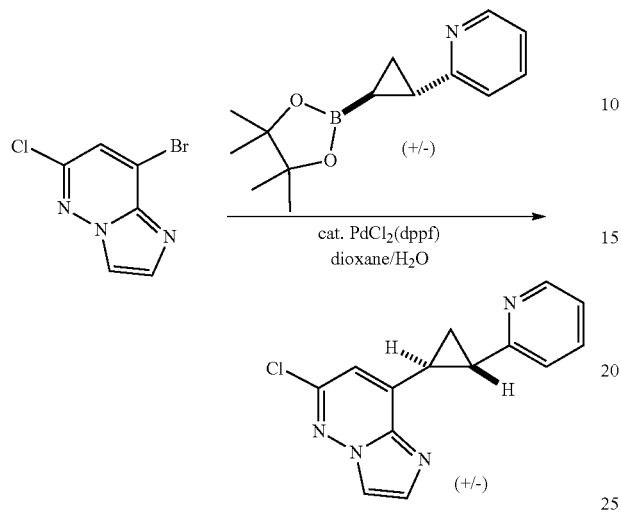

6-chloro-8-[(1S,2S)-2-(2-pyridyl)cyclopropyl]imidazo[1,2-b]pyridazine was prepared as a racemic mixture as follows: A microwave vial was charged with 8-bromo-6-chloroimidazo[1,2-b]pyridazine (200 mg, 0.86 mmol, 1 equiv), racemic 2-[(1S,2S)-2-(4,4,5,5-tetramethyl-1,3,2-dioxaborolan-2-yl)cyclopropyl]pyridine (211 mg, 0.86 mmol, 1 equiv), cesium carbonate (561 mg, 1.72 mmol, 2 equiv), and Pd(dppf)Cl$_2$CH$_2$Cl$_2$ (70.3 mg, 10 mol %). The solids were dissolved in 3:1 dioxane/H$_2$O (4 mL), purged with argon, and heated at 115° C. After 14 hour, the reaction mixture was then filtered and purified with reverse phase HPLC (ACN/water with 0.1% TFA) to afford 6-chloro-8-[(1S,2S)-2-(2-pyridyl)cyclopropyl]imidazo[1,2-b]pyridazine (Racemic Mixture). ES/MS m/z: 271.10 [M+H].

Intermediate 87. 6-chloro-8-[(1S,2S)-2-[4-(trifluoromethyl)phenyl]cyclopropyl]imidazo[1,2-b]pyridazine (Racemic Mixture)

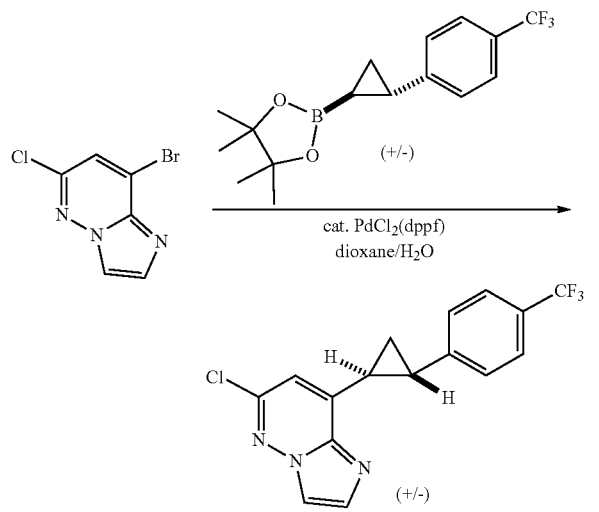

6-chloro-8-[(1S,2S)-2-[4-(trifluoromethyl)phenyl]cyclopropyl]imidazo[1,2-b]pyridazine was prepared as a racemic mixture as follows: A microwave vial was charged with 8-bromo-6-chloroimidazo[1,2-b]pyridazine (150 mg, 0.645 mmol, 1 equiv), racemic 4,4,5,5-tetramethyl-2-[(1S,2S)-2-[4-(trifluoromethyl)phenyl]cyclopropyl]-1,3,2-dioxaborolane (201 mg, 0.645 mmol, 1 equiv), cesium carbonate (420 mg, 1.29 mmol, 2 equiv), and Pd(dppf)Cl$_2$CH$_2$Cl$_2$ (53 mg, 10 mol %). The solids were dissolved in 3:1 dioxane/H$_2$O (4 mL), purged with argon, and heated in a microwave reactor at 110° C. After 1.5 hour, the reaction mixture was directly purified by silica gel chromatography (0-15% MeOH/CH$_2$Cl$_2$), affording 6-chloro-8-[(1S,2S)-2-[4-(trifluoromethyl)phenyl]cyclopropyl]imidazo[1,2-b]pyridazine. ES/MS m/z: 338.00 [M+H].

Intermediate 88. 3-[(1S,2S)-2-(6-chloroimidazo[1,2-b]pyridazin-8-yl)cyclopropyl]-5-fluoro-benzonitrile (Racemic Mixture)

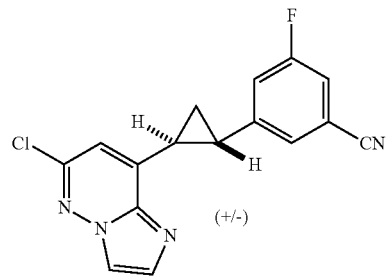 [SMILES: N#Cc1cc(F)cc([C@H]2C[C@@H]2c2cc(Cl)nn3ccnc23)c1]

3-[(1S,2S)-2-(6-chloroimidazo[1,2-b]pyridazin-8-yl)cyclopropyl]-5-fluoro-benzonitrile was prepared as a racemic mixture in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with racemic 3-fluoro-5-[(1S,2S)-2-(4,4,5,5-tetramethyl-1,3,2-dioxaborolan-2-yl)cyclopropyl]benzonitrile. ES/MS m/z: 313.10 [M+H].

Intermediate 89. 6-chloro-8-[(2S,2S)-2-[3-(trifluoromethyl)phenyl]cyclopropyl]imidazo[1,2-b]pyridazine (Racemic Mixture)

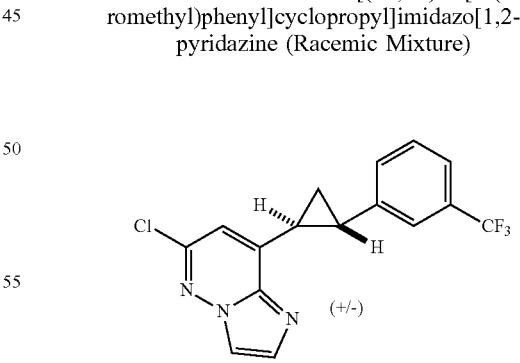

6-chloro-8-[(1S,2S)-2-[3-(trifluoromethyl)phenyl]cyclopropyl]imidazo[1,2-b]pyridazine was prepared as a racemic mixture in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with racemic 4,4,5,5-tetramethyl-2-[(1S,2S)-2-[3-(trifluoromethyl)phenyl]cyclopropyl]-1,3,2-dioxaborolane. ES/MS m/z: 338.10 [M+H].

Intermediate 90. 6-chloro-8-[(1S,2S)-2-(3-pyridyl)cyclopropyl]imidazo[1,2-b]pyridazine (Racemic Mixture)

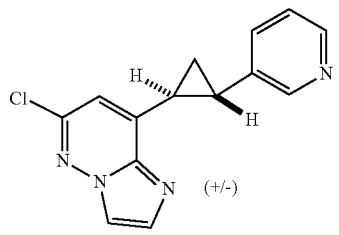 [SMILES: Clc1cc([C@H]2C[C@@H]2c2cccnc2)c2nccn2n1]

6-chloro-8-[(1S,2S)-2-(3-pyridyl)cyclopropyl]imidazo[1,2-b]pyridazine was prepared as a racemic mixture in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with racemic 3-[(1S,2S)-2-(4,4,5,5-tetramethyl-1,3,2-dioxaborolan-2-yl)cyclopropyl]pyridine. ES/MS m/z: 271.10 [M+H].

Intermediate 91. 6-chloro-8-[(1S,2S)-2-(4-pyridyl)cyclopropyl]imidazo[1,2-b]pyridazine (Racemic Mixture)

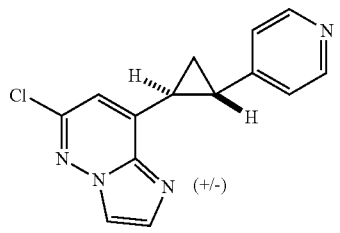 [SMILES: Clc1cc([C@H]2C[C@@H]2c2ccncc2)c2nccn2n1]

6-chloro-8-[(1S,2S)-2-(4-pyridyl)cyclopropyl]imidazo[1,2-b]pyridazine was prepared as a racemic mixture in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with racemic 4-[(1S,2S)-2-(4,4,5,5-tetramethyl-1,3,2-dioxaborolan-2-yl)cyclopropyl]pyridine. ES/MS m/z: 271.10 [M+H].

Intermediate 92. 6-chloro-3-fluoro-8-[(1S,2S)-2-(4-fluorophenyl)cyclopropyl]imidazo[1,2-b]pyridazine (Racemic Mixture)

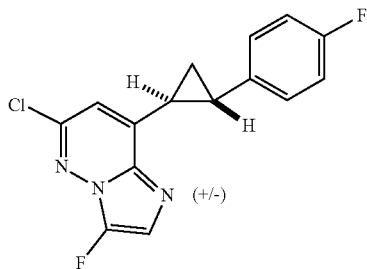 [SMILES: Fc1ccc([C@H]2C[C@@H]2c2cc(Cl)nn3c(F)cnc23)cc1]

6-chloro-3-fluoro-8-[(1S,2S)-2-(4-fluorophenyl)cyclopropyl]imidazo[1,2-b]pyridazine was prepared as a racemic mixture in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with racemic 2-[(1S,2S)-2-(4-fluorophenyl)cyclopropyl]-4,4,5,5-tetramethyl-1,3,2-dioxaborolane and 8-bromo-6-chloroimidazo[1,2-b]pyridazine with 8-bromo-6-chloro-3-fluoro-imidazo[1,2-b]pyridazine. ES/MS m/z: 306.10 [M+H].

Intermediate 93. 6-chloro-3-fluoro-8-[(1S,2S)-2-phenylcyclopropyl]imidazo[1,2-b]pyridazine (Racemic Mixture)

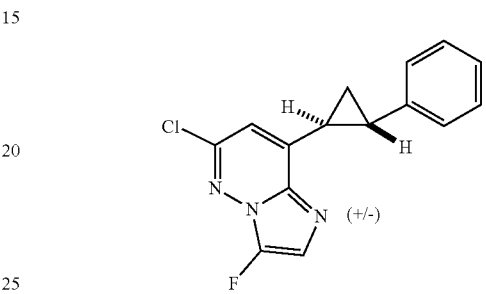

6-chloro-3-fluoro-8-[(1S,2S)-2-phenylcyclopropyl]imidazo[1,2-b]pyridazine was prepared as a racemic mixture in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with racemic 4,4,5,5-tetramethyl-2-[(1S,2S)-2-phenylcyclopropyl]-1,3,2-dioxaborolane and 8-bromo-6-chloroimidazo[1,2-b]pyridazine with 8-bromo-6-chloro-3-fluoro-imidazo[1,2-b]pyridazine. ES/MS m/z: 288.00 [M+H].

Intermediate 94. 6-chloro-8-[(1S,2S)-2-(2,4-difluorophenyl)cyclopropyl]-3-fluoro-imidazo[1,2-b]pyridazine

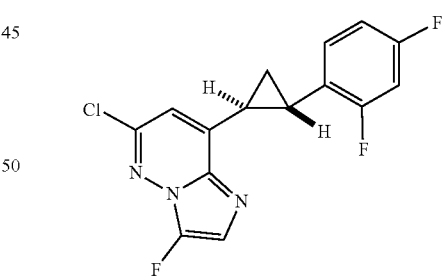

6-chloro-8-[(1S,2S)-2-(2,4-difluorophenyl)cyclopropyl]-3-fluoro-imidazo[1,2-b]pyridazine was prepared in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with 2-[(1S,2S)-2-(2,4-difluorophenyl)cyclopropyl]-4,4,5,5-tetramethyl-1,3,2-dioxaborolane and 8-bromo-6-chloroimidazo[1,2-b]pyridazine with 8-bromo-6-chloro-3-fluoro-imidazo[1,2-b]pyridazine. ES/MS m/z: 324.10 [M+H].

Intermediate 95. 6-chloro-8-[(1S,2S)-2-(3,4-difluorophenyl)cyclopropyl]-3-fluoro-imidazo[1,2-b]pyridazine

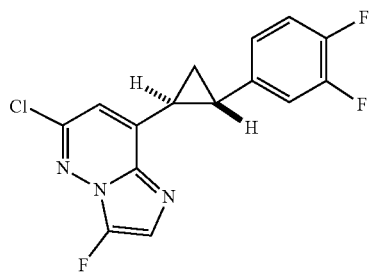 [SMILES: Fc1ccc([C@H]2C[C@@H]2c2cc(Cl)nn3c(F)cnc23)cc1F]

6-chloro-8-[(1S,2S)-2-(3,4-difluorophenyl)cyclopropyl]-3-fluoro-imidazo[1,2-b]pyridazine was prepared in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with 2-[(1S,2S)-2-(3,4-difluorophenyl)cyclopropyl]-4,4,5,5-tetramethyl-1,3,2-dioxaborolane and 8-bromo-6-chloroimidazo[1,2-b]pyridazine with 8-bromo-6-chloro-3-fluoro-imidazo[1,2-b]pyridazine. ES/MS m/z: 324.10 [M+H].

Intermediate 96. 6-chloro-8-[(2S,2S)-2-(1-naphthyl)cyclopropyl]imidazo[1,2-b]pyridazine (Racemic Mixture)

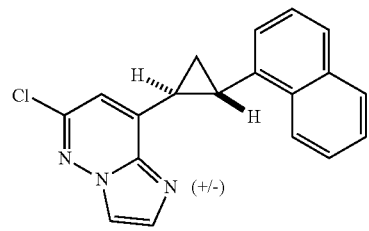 [SMILES: Clc1cc([C@H]2C[C@@H]2c2cccc3ccccc23)c2nccn2n1]

6-chloro-8-[(1S,2S)-2-(1-naphthyl)cyclopropyl]imidazo[1,2-b]pyridazine was prepared as a racemic mixture in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with racemic 4,4,5,5-tetramethyl-2-[(1S,2S)-2-(1-naphthyl)cyclopropyl]-1,3,2-dioxaborolane. ES/MS m/z: 320.10 [M+H].

Intermediate 97. 6-chloro-2-cyclopropyl-8-[(1S,2S)-2-(4-fluorophenyl)cyclopropyl]imidazo[1,2-b]pyridazine (Racemic Mixture)

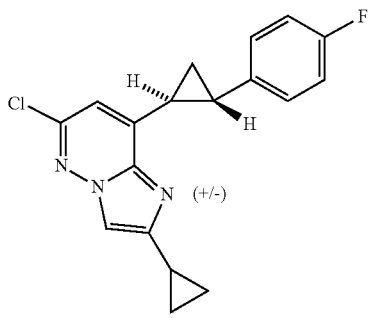 [SMILES: Fc1ccc([C@H]2C[C@@H]2c2cc(Cl)nn3cc(C4CC4)nc23)cc1]

6-chloro-2-cyclopropyl-8-[(1S,2S)-2-(4-fluorophenyl)cyclopropyl]imidazo[1,2-b]pyridazine was prepared as a racemic mixture in the manner described for Intermediate 87, but replacing racemic 4,4,5,5-tetramethyl-2-[(1S,2S)-2-[4-(trifluoromethyl)phenyl]cyclopropyl]-1,3,2-dioxaborolane with racemic 2-[(1S,2S)-2-(4-fluorophenyl)cyclopropyl]-4,4,5,5-tetramethyl-1,3,2-dioxaborolane and 8-bromo-6-chloroimidazo[1,2-b]pyridazine with 8-bromo-6-chloro-2-cyclopropyl-imidazo[1,2-b]pyridazine. ES/MS m/z: 328.10 [M+H].

Intermediate 98. 6-chloro-8-((2S,2S)-2-(4-fluoro-3-(trifluoromethyl)phenyl)cyclopropyl)imidazo[1,2-b]pyridazine (Racemic Mixture)

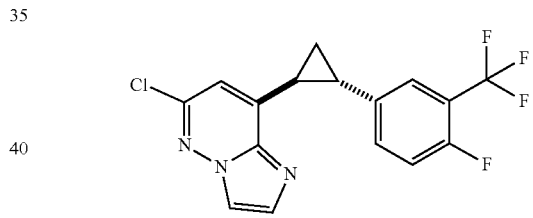

6-chloro-8-((1S,2S)-2-(4-fluoro-3-(trifluoromethyl)phenyl)cyclopropyl)imidazo[1,2-b]pyridazine was prepared as a racemic mixture in the manner described for Intermediate 5, but replacing racemic 4,4,5,5-tetramethyl-2-((2S,2S)-2-phenylcyclopropyl)-1,3,2-dioxaborolane with racemic 2-((2S,2S)-2-(4-fluoro-3-(trifluoromethyl)phenyl)cyclopropyl)-4,4,5,5-tetramethyl-1,3,2-dioxaborolane. ES/MS m/z: 356.01 [M+H].

Intermediate 99. 6-chloro-8-((2S,2S)-2-(4-chloro-3-fluorophenyl)cyclopropyl)imidazo[1,2-b]pyridazine (Racemic Mixture)

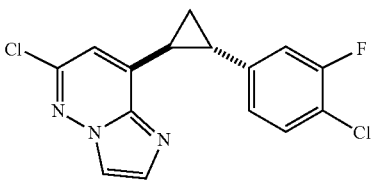 [SMILES: Fc1cc([C@H]2C[C@@H]2c2cc(Cl)nn3ccnc23)ccc1Cl]

6-chloro-8-((1S,2S)-2-(4-chloro-3-fluorophenyl)cyclopropyl)imidazo[1,2-b]pyridazine was prepared as a racemic mixture in the manner described for Intermediate 5, but replacing racemic 4,4,5,5-tetramethyl-2-((2S,2S)-2-phenylcyclopropyl)-1,3,2-dioxaborolane with racemic 2-((1S,2S)-2-(4-chloro-3-fluorophenyl)cyclopropyl)-4,4,5,5-tetramethyl-1,3,2-dioxaborolane. ES/MS m/z: 322.02 [M+H].

Intermediate 100. 6-chloro-8-((2S,2S)-2-(3-chloro-4-fluorophenyl)cyclopropyl)imidazo[1,2-b]pyridazine (Racemic Mixture)

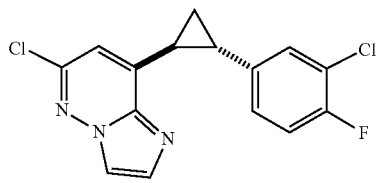 [SMILES: Fc1ccc([C@H]2C[C@@H]2c2cc(Cl)nn3ccnc23)cc1Cl]

6-chloro-8-((1S,2S)-2-(3-chloro-4-fluorophenyl)cyclopropyl)imidazo[1,2-b]pyridazine was prepared as a racemic mixture in the manner described for Intermediate 5, but replacing racemic 4,4,5,5-tetramethyl-2-((1S,2S)-2-phenylcyclopropyl)-1,3,2-dioxaborolane with racemic 2-((1S,2S)-2-(3-chloro-4-fluorophenyl)cyclopropyl)-4,4,5,5-tetramethyl-1,3,2-dioxaborolane. ES/MS m/z: 322.03 [M+H].

Intermediate 101. 6-chloro-8-((1S,2S)-2-(3-fluoro-4-(trifluoromethyl)phenyl)cyclopropyl)imidazo[1,2-b]pyridazine (Racemic Mixture)

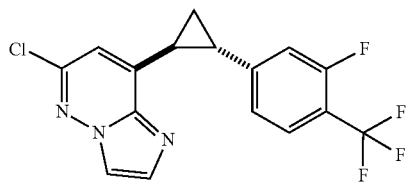 [SMILES: Fc1cc([C@H]2C[C@@H]2c2cc(Cl)nn3ccnc23)ccc1C(F)(F)F]

6-chloro-8-((1S,2S)-2-(3-fluoro-4-(trifluoromethyl)phenyl)cyclopropyl)imidazo[1,2-b]pyridazine was prepared as a racemic mixture in the manner described for Intermediate 5, but replacing racemic 4,4,5,5-tetramethyl-2-((1S,2S)-2-phenylcyclopropyl)-1,3,2-dioxaborolane with racemic 2-((1S,2S)-2-(3-fluoro-4-(trifluoromethyl)phenyl)cyclopropyl)-4,4,5,5-tetramethyl-1,3,2-dioxaborolane. ES/MS m/z: 356.00 [M+H].

Intermediate 102. 6-chloro-8-((1S,2S)-2-(2-methoxyphenyl)cyclopropyl)imidazo[1,2-b]pyridazine (Racemic Mixture)

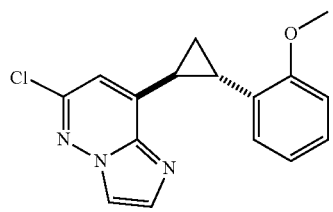 [SMILES: COc1ccccc1[C@H]1C[C@@H]1c1cc(Cl)nn2ccnc12]

6-chloro-8-((1S,2S)-2-(2-methoxyphenyl)cyclopropyl)imidazo[1,2-b]pyridazine was prepared as a racemic mixture in the manner described for Intermediate 5, but replacing racemic 4,4,5,5-tetramethyl-2-((2S,2S)-2-phenylcyclopropyl)-1,3,2-dioxaborolane with racemic 2-((1S,2S)-2-(2-methoxyphenyl)cyclopropyl)-4,4,5,5-tetramethyl-1,3,2-dioxaborolane. ES/MS m/z: 300.10 [M+1].

Intermediate 103. 6-chloro-8-((1S,2S)-2-(4-cyclopropylphenyl)cyclopropyl)imidazo[1,2-b]pyridazine (Racemic Mixture)

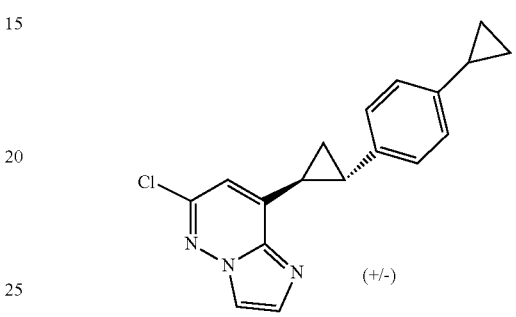

6-chloro-8-((1S,2S)-2-(4-cyclopropylphenyl)cyclopropyl)imidazo[1,2-b]pyridazine was prepared as a racemic mixture as follows: A microwave vial was charged with 8-bromo-6-chloro-imidazo[1,2-b]pyridazine (300 mg, 1.29 mmol), racemic 2-[(1S,2S)-2-(4-cyclopropylphenyl)cyclopropyl]-4,4,5,5-tetramethyl-1,3,2-dioxaborolane (367 mg, 1.29 mmol), cesium carbonate (841 mg, 2.58 mmol), and Pd(dppf)Cl$_2$CH$_2$Cl$_2$ (105 mg, 0.13 mmol). The solids were dissolved in dioxane (4 mL) and H$_2$O (2 mL), and the mixture was degassed with N2. The vial was sealed and heated to 120° C. for 1 h. The reaction mixture was then cooled and filtered through celite, washing with EtOAc. The filtrate was concentrated in vacuo, and the resulting residue purified by silica gel chromatography (0-100% EtOAc/hexanes), affording 6-chloro-8-((1S,2S)-2-(4-cyclopropylphenyl)cyclopropyl)imidazo[1,2-b]pyridazine. ES/MS m/z: 310.10 [M+1].

Intermediate 104. 6-chloro-8-((1S,2S)-2-(3-(trifluoromethoxy)phenyl)cyclopropyl)imidazo[1,2-b]pyridazine (Racemic Mixture)

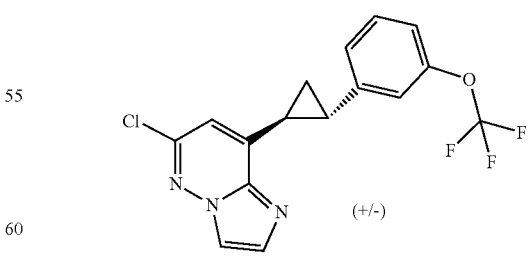

6-chloro-8-((1S,2S)-2-(3-(trifluoromethoxy)phenyl)cyclopropyl)imidazo[1,2-b]pyridazine was prepared as a racemic mixture in the manner described for Intermediate 103, but replacing racemic 2-[(1S,2S)-2-(4-cyclopropylphenyl)cyclopropyl]-4,4,5,5-tetramethyl-1,3,2-dioxaborolane with 4,4,5,5-tetramethyl-2-((1S,2S)-2-(3-(trifluoromethoxy)phenyl)cyclopropyl)-1,3,2-dioxaborolane. ES/MS m/z: 354.20 [M+1].

Intermediate 105. 6-chloro-8-((2S,2S)-2-(4-(trifluoromethoxy)phenyl)cyclopropyl)imidazo[1,2-b]pyridazine (Racemic Mixture)

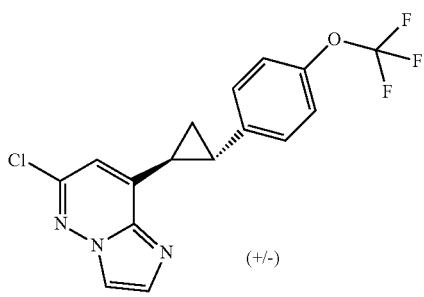 [SMILES: FC(F)(F)Oc1ccc([C@H]2C[C@@H]2c2cc(Cl)nn3ccnc23)cc1]

6-chloro-8-((1S,2S)-2-(4-(trifluoromethoxy)phenyl)cyclopropyl)imidazo[1,2-b]pyridazine was prepared as a racemic mixture in the manner described for Intermediate 103, but replacing racemic 2-[(1S,2S)-2-(4-cyclopropylphenyl)cyclopropyl]-4,4,5,5-tetramethyl-1,3,2-dioxaborolane with 4,4,5,5-tetramethyl-2-((1S,2S)-2-(4-(trifluoromethoxy)phenyl)cyclopropyl)-1,3,2-dioxaborolane. ES/MS m/z: 354.20 [M+1].

Intermediate 106. 6-chloro-8-((2S,2S)-2-(2,2-difluorobenzo[d][1,3]dioxol-5-yl)cyclopropyl)imidazo[1,2-b]pyridazine (Racemic Mixture)

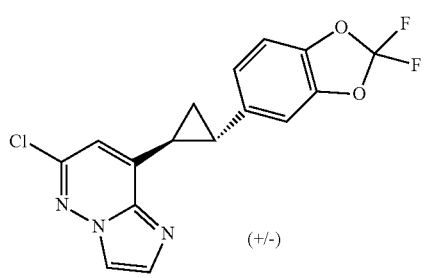 [SMILES: FC1(F)Oc2ccc([C@H]3C[C@@H]3c3cc(Cl)nn4ccnc34)cc2O1]

6-chloro-8-((1S,2S)-2-(2,2-difluorobenzo[d][1,3]dioxol-5-yl)cyclopropyl)imidazo[1,2-b]pyridazine was prepared as a racemic mixture in the manner described for Intermediate 103, but replacing racemic 2-[(1S,2S)-2-(4-cyclopropylphenyl)cyclopropyl]-4,4,5,5-tetramethyl-1,3,2-dioxaborolane with 2-((2S,2S)-2-(2,2-difluorobenzo[d][1,3]dioxol-5-yl)cyclopropyl)-4,4,5,5-tetramethyl-1,3,2-dioxaborolane. ES/MS m/z: 350.20 [M+1].

Intermediate 107. 4-(((1R,2S)-2-(6-chloroimidazo[1,2-b]pyridazin-8-yl)cyclopropyl)methyl)benzonitrile (Racemic Mixture)

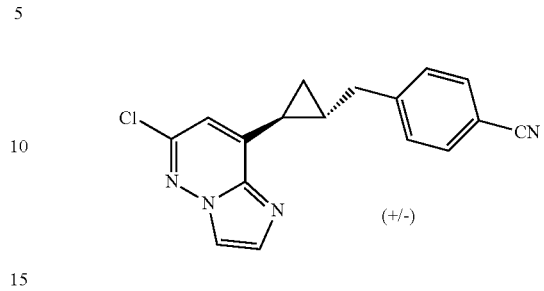

4-(((1R,2S)-2-(6-chloroimidazo[1,2-b]pyridazin-8-yl)cyclopropyl)methyl)benzonitrile was prepared as a racemic mixture in the manner described for Intermediate 103, but replacing racemic 2-[(1S,2S)-2-(4-cyclopropylphenyl)cyclopropyl]-4,4,5,5-tetramethyl-1,3,2-dioxaborolane with 4-(((1R,2S)-2-(trifluoro-14-boraneyl)cyclopropyl)methyl)benzonitrile, potassium salt. ES/MS m/z: 309.10 [M+1].

Suzuki Cross Coupling with Cyclopropyl Boronic Acids

Intermediate 108. 6-chloro-2,8-dicyclopropyl-imidazo[1,2-b]pyridazine

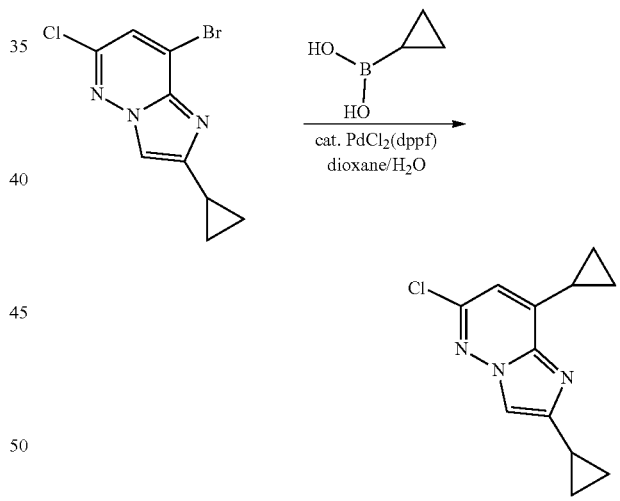

6-chloro-2,8-dicyclopropyl-imidazo[1,2-b]pyridazine was prepared as follows: A microwave vial was charged with 8-bromo-6-chloro-2-cyclopropyl-imidazo[1,2-b]pyridazine (200 mg, 0.734 mmol, 1 equiv), cyclopropylboronic acid (180 mg, 2.09 mmol, 2.85 equiv), cesium carbonate (478 mg, 1.47 mmol, 2 equiv), and Pd(dppf)Cl$_2$CH$_2$Cl$_2$ (60 mg, 10 mol %). The reaction mixture was dissolved in 1:1 dioxane/H$_2$O (4 mL total), purged with argon, and heated in a microwave reactor at 110° C. After 1.5 hour, the reaction mixture was then filtered and purified with reverse phase HPLC (ACN/water with 0.1% TFA) to afford 6-chloro-2,8-dicyclopropyl-imidazo[1,2-b]pyridazine. ES/MS m/z: 234.10 [M+H].

Condensation of 3-Amino Pyridazine with Bromomethyl Aryl Ketones

Intermediate 109. 8-bromo-6-chloro-2-(2-(trifluoromethyl)phenyl)imidazo[1,2-b]pyridazine

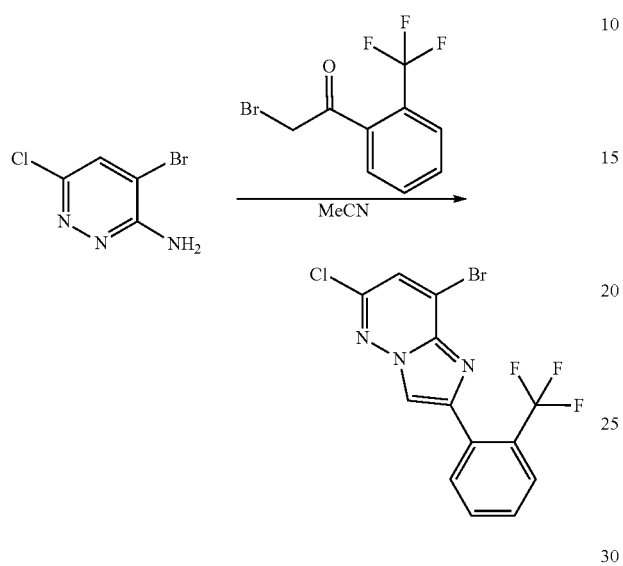

A mixture of 4-bromo-6-chloropyridazin-3-amine (207.0 mg, 0.99 mmol, 1.0 equiv.) and 2-bromo-1-(2-(trifluoromethyl)phenyl)ethan-1-one (647.7 mg, 2.42 mmol, 2.5 equiv.) in MeCN (6.5 mL) in a sealed vessel was heated to 80° C. After 24 h, the mixture was filtered through celite, rinsed with EtOAc, and the filtrate was concentrated in vacuo. Purification by column chromatography (0-100% DCM in hexanes) afforded 8-bromo-6-chloro-2-(2-(trifluoromethyl)phenyl)imidazo[1,2-b]pyridazine. ES/MS m/z: 377.90 [M+H].

Intermediate 110. 8-bromo-6-chloro-2-(pyridin-2-yl)imidazo[1,2-b]pyridazine

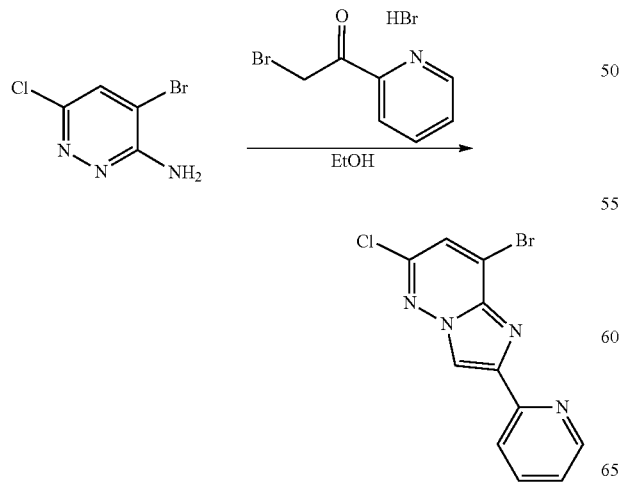

To 4-bromo-6-chloropyridazin-3-amine (503.1 mg, 2.41 mmol, 1.0 equiv.) in EtOH (15 mL) was added 2-bromo-1-(pyridin-2-yl)ethan-1-one hydrobromide (1685.7 mg, 6.00 mmol, 2.5 equiv.) and the mixture was heated to 85° C. After 24 h, the mixture was concentrated in vacuo. The resulting solids were triturated with MeOH and EtOAc, filtered, rinsed with Et₂O, and dried under vacuum. The solids were diluted with EtOAc, filtered, and rinsed with EtOAc and sat. NaHCO3(aq). The layers were separated and the organics were washed with brine (50 mL), dried over Na₂SO₄, and concentrated in vacuo to afford 8-bromo-6-chloro-2-(pyridin-2-yl)imidazo[1,2-b]pyridazine. ES/MS m/z: 309.00 [M+H].

Intermediate 111. 8-bromo-6-chloro-2-(pyridin-3-yl)imidazo[1,2-b]pyridazine

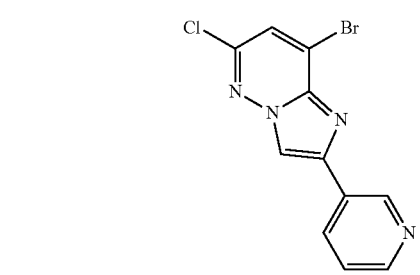 [SMILES: Clc1cc(Br)c2nc(-c3cccnc3)cn2n1]

8-bromo-6-chloro-2-(pyridin-3-yl)imidazo[1,2-b]pyridazine was prepared as a in the manner described for Intermediate 110, but replacing 2-bromo-1-(pyridin-2-yl)ethan-1-one hydrobromide with 2-bromo-1-(pyridin-3-yl)ethan-1-one hydrobromide. ES/MS m/z: 309.00 [M+H].

Intermediate 112. 8-bromo-6-chloro-2-(pyridin-4-yl)imidazo[1,2-b]pyridazine

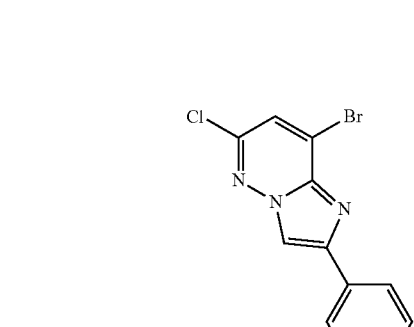

8-bromo-6-chloro-2-(pyridin-4-yl)imidazo[1,2-b]pyridazine was prepared as a in the manner described for Intermediate 110, but replacing 2-bromo-1-(pyridin-2-yl)ethan-1-one hydrobromide with 2-bromo-1-(pyridin-4-yl)ethan-1-one hydrobromide. ES/MS m/z: 309.00 [M+H].

Negishi Cross Coupling with Cyclopropyl Zinc Bromide

Intermediate 113. 6-chloro-8-cyclopropyl-2-(2-(trifluoromethyl)phenyl)imidazo[1,2-b]pyridazine

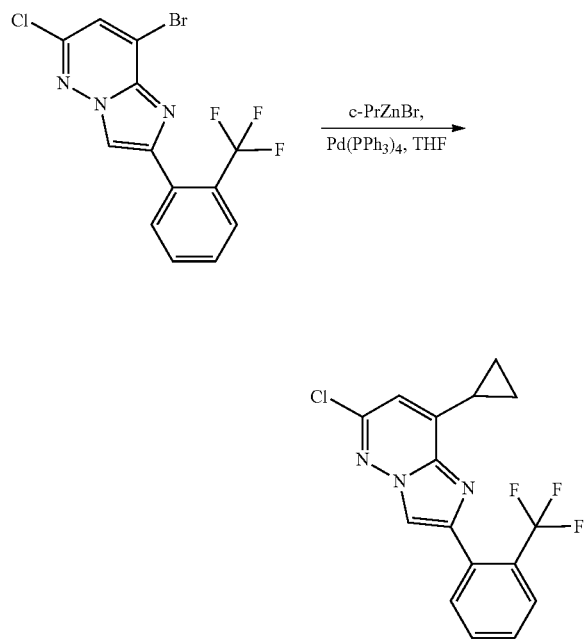 [SMILES: FC(F)(F)c1ccccc1-c1cn2nc(Cl)cc(Br)c2n1 ; FC(F)(F)c1ccccc1-c1cn2nc(Cl)cc(C3CC3)c2n1]

To a solution of 8-bromo-6-chloro-2-(2-(trifluoromethyl)phenyl)imidazo[1,2-b]pyridazine (163.9 mg, 0.43 mmol, 1.0 equiv.) and Pd(PPh$_3$)$_4$ (25.4 mg, 0.02 mmol, 0.05 equiv.) in THF (1 mL) was added 0.5 M cyclopropylzinc bromide in THF (1.3 mL, 0.65 mmol, 1.5 equiv.). After 21 h, the reaction was quenched with sat. NaHCO3(aq) (5 mL) and extracted with EtOAc (15 mL). The organics were washed with brine (10 mL), dried over Na$_2$SO$_4$, and concentrated in vacuo. Purification by column chromatography (0-100% EtOAc in hexanes) afforded 6-chloro-8-cyclopropyl-2-(2-(trifluoromethyl)phenyl)imidazo[1,2-b]pyridazine. ES/MS m/z: 338.04 [M+H].

Intermediate 114. 6-chloro-8-cyclopropyl-2-(pyridin-4-yl)imidazo[1,2-b]pyridazine

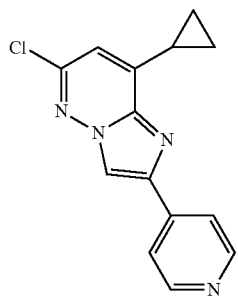 [SMILES: Clc1cc(C2CC2)c2nc(-c3ccncc3)cn2n1]

6-chloro-8-cyclopropyl-2-(pyridin-4-yl)imidazo[1,2-b]pyridazine was prepared as a in the manner described for Intermediate 113, but replacing 8-bromo-6-chloro-2-(2-(trifluoromethyl)phenyl)imidazo[1,2-b]pyridazine with 8-bromo-6-chloro-2-(pyridin-4-yl)imidazo[1,2-b]pyridazine. ES/MS m/z: 271.10 [M+H].

Intermediate 115. 6-chloro-8-cyclopropyl-2-(pyridin-3-yl)imidazo[1,2-b]pyridazine

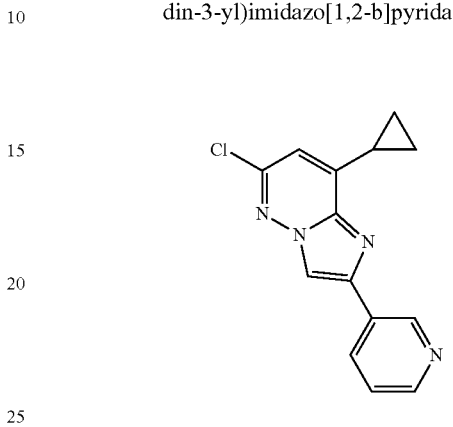

6-chloro-8-cyclopropyl-2-(pyridin-3-yl)imidazo[1,2-b]pyridazine was prepared as a in the manner described for Intermediate 113, but replacing 8-bromo-6-chloro-2-(2-(trifluoromethyl)phenyl)imidazo[1,2-b]pyridazine with 8-bromo-6-chloro-2-(pyridin-3-yl)imidazo[1,2-b]pyridazine. ES/MS m/z: 271.10 [M+H].

Intermediate 116. 6-chloro-8-cyclopropyl-2-(pyridin-2-yl)imidazo[1,2-b]pyridazine

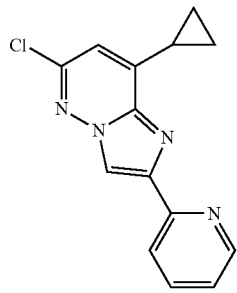 [SMILES: Clc1cc(C2CC2)c2nc(-c3ccccn3)cn2n1]

6-chloro-8-cyclopropyl-2-(pyridin-2-yl)imidazo[1,2-b]pyridazine was prepared as a in the manner described for Intermediate 113, but replacing 8-bromo-6-chloro-2-(2-(trifluoromethyl)phenyl)imidazo[1,2-b]pyridazine with 8-bromo-6-chloro-2-(pyridin-2-yl)imidazo[1,2-b]pyridazine. ES/MS m/z: 271.10 [M+H].

Intermediate 117. 8-((1S,2R)-2-benzylcyclopropyl)-6-chloroimidazo[1,2-b]pyridazine (Racemic Mixture)

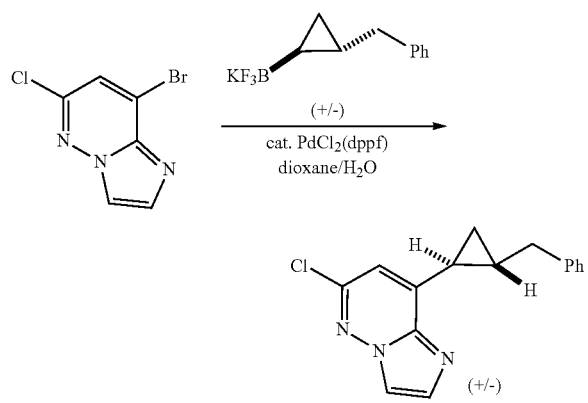

8-((1S,2R)-2-benzylcyclopropyl)-6-chloroimidazo[1,2-b]pyridazine was prepared as a racemic mixture as follows: A microwave vial was charged with 8-bromo-6-chloroimidazo[1,2-b]pyridazine (300 mg, 1.29 mmol, 1 equiv), racemic potassium trans-(2-benzylcyclopropyl)trifluoroborate (169 mg, 1.29 mmol, 1 equiv), cesium carbonate (841 mg, 2.58 mmol, 2 equiv), and Pd(dppf)Cl$_2$CH$_2$Cl$_2$ (94 mg, 10 mol %). The solids were dissolved in 2:1 dioxane/H$_2$O (5 mL), purged with argon, and heated at 120° C. After 3 hours, the reaction mixture was directly purified by silica gel chromatography (0-100% EtOAc/Hex), affording 8-((1S,2R)-2-benzylcyclopropyl)-6-chloroimidazo[1,2-b]pyridazine (Racemic Mixture). ES/MS m/z: 284.10 [M+H].

Intermediate 118. 6-chloro-8-((1S,2R)-2-(3,3-difluorocyclobutyl)cyclopropyl)imidazo[1,2-b]pyridazine (Racemic Mixture)

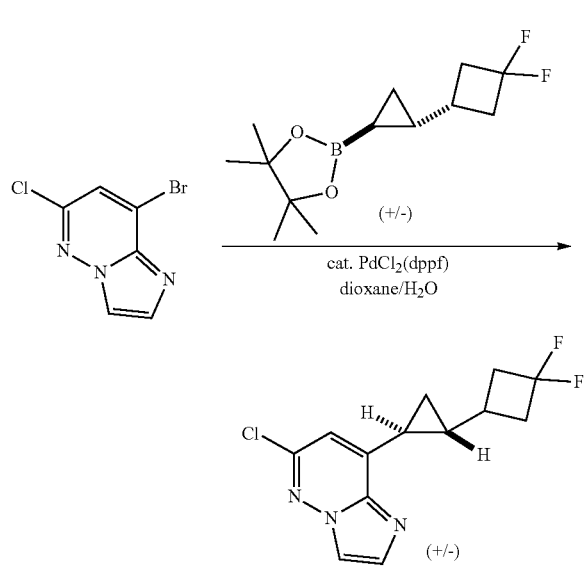

6-chloro-8-((1S,2R)-2-(3,3-difluorocyclobutyl)cyclopropyl)imidazo[1,2-b]pyridazine was prepared as a racemic mixture as follows: A microwave vial was charged with 8-bromo-6-chloroimidazo[1,2-b]pyridazine (200 mg, 0.86 mmol, 1 equiv), racemic 2-((2S,2S)-2-(3,3-difluorocyclobutyl)cyclopropyl)-4,4,5,5-tetramethyl-1,3,2-dioxaborolane (222 mg, 0.86 mmol, 1 equiv), cesium carbonate (561 mg, 1.72 mmol, 2 equiv), and Pd(dppf)Cl$_2$CH$_2$Cl$_2$ (63 mg, 10 mol %). The solids were dissolved in 2:1 dioxane/H$_2$O (4 mL), purged with argon, and heated at 120° C. After 14 hours, the reaction mixture was directly purified by silica gel chromatography (0-100% EtOAc/Hex), affording 6-chloro-8-((1S,2R)-2-(3,3-difluorocyclobutyl)cyclopropyl)imidazo[1,2-b]pyridazine (Racemic Mixture). ES/MS m/z: 283.70 [M+H].

Intermediate 119. 6-chloro-8-((2S,2S)-2-(trifluoromethyl)cyclopropyl)imidazo[1,2-b]pyridazine (Racemic Mixture)

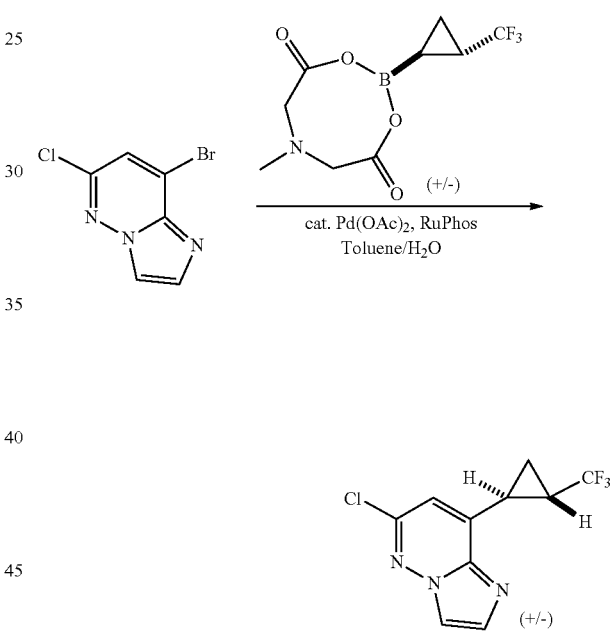

6-chloro-8-((2S,2S)-2-(trifluoromethyl)cyclopropyl)imidazo[1,2-b]pyridazine was prepared as a racemic mixture as follows: A microwave vial was charged with 8-bromo-6-chloroimidazo[1,2-b]pyridazine (80 mg, 0.34 mmol, 1 equiv), racemic 6-methyl-2-((2S,2S)-2-(trifluoromethyl)cyclopropyl)-1,3,6,2-dioxazaborocane-4,8-dione (100 mg, 0.38 mmol, 1.1 equiv), potassium carbonate (143 mg, 1.03 mmol, 3 equiv), palladium(II) acetate (7.7 mg, 10 mol %), and RuPhos (32 mg, 20 mol %). The solids were dissolved in 3:1 Toluene/H$_2$O (2 mL), purged with argon, and heated at 115° C. After 20 hours, the reaction mixture was directly purified by silica gel chromatography (0-80% EtOAc/CH$_2$Cl$_2$), affording 6-chloro-8-((2S,2S)-2-(trifluoromethyl)cyclopropyl)imidazo[1,2-b]pyridazine (Racemic Mixture). ES/MS m/z: 262.10 [M+H].

Intermediate 120. 6-chloro-8-((1R,2R)-2-fluoro-2-phenylcyclopropyl)imidazo[1,2-b]pyridazine (Racemic Mixture)

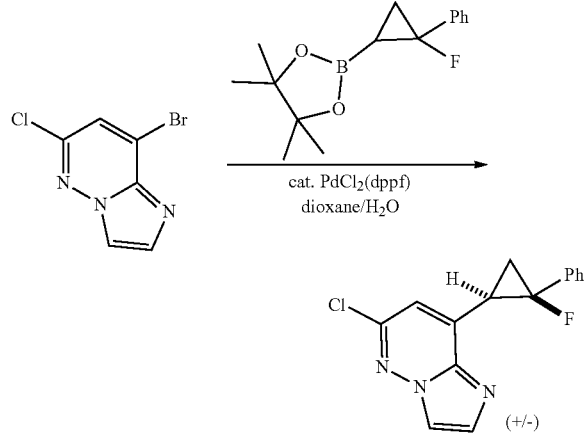

6-chloro-8-((1R,2R)-2-fluoro-2-phenylcyclopropyl)imidazo[1,2-b]pyridazine was prepared as a racemic mixture as follows: A microwave vial was charged with 8-bromo-6-chloroimidazo[1,2-b]pyridazine (300 mg, 1.29 mmol, 1 equiv), 2-(2-fluoro-2-phenylcyclopropyl)-4,4,5,5-tetramethyl-1,3,2-dioxaborolane (338 mg, 1.29 mmol, 1 equiv), cesium carbonate (841 mg, 2.58 mmol, 2 equiv), and Pd(dppf)Cl$_2$CH$_2$Cl$_2$ (94 mg, 10 mol %). The solids were dissolved in 2:1 dioxane/H$_2$O (4 mL), purged with argon, and heated at 120° C. After 2 hours, the reaction mixture was directly purified by silica gel chromatography (0-100% EtOAc/Hex), affording 6-chloro-8-((1R,2R)-2-fluoro-2-phenylcyclopropyl)imidazo[1,2-b]pyridazine (Racemic Mixture). ES/MS m/z: 288.10 [M+H].

Suzuki Cross Coupling Reaction with (2,4-dimethoxypyrimidin-5-yl)boronic acid

Intermediate 121. 8-(4,4-difluorocyclohexyl)-6-(2,4-dimethoxypyrimidin-5-yl)-2-methyl-[1,2,4]triazolo[1,5-b]pyridazine

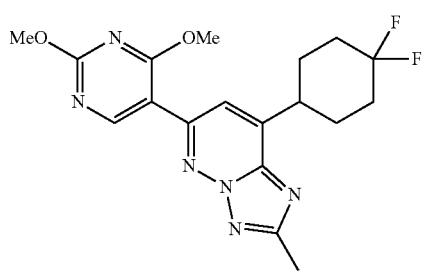 [SMILES: COc1ncc(-c2cc(C3CCC(F)(F)CC3)c3nc(C)nn3n2)c(OC)n1]

8-(4,4-difluorocyclohexyl)-6-(2,4-dimethoxypyrimidin-5-yl)-2-methyl-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-(4,4-difluorocyclohexyl)-2-methyl-[1,2,4]triazolo[1,5-b]pyridazine. ES/MS m/z: 391.1 [M+1].

Intermediate 122. 8-(4,4-difluorocyclohexyl)-6-(2,4-dimethoxypyrimidin-5-yl)imidazo[1,2-b]pyridazine-3-carbonitrile

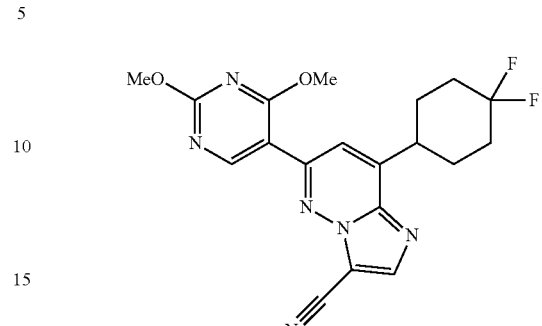

8-(4,4-difluorocyclohexyl)-6-(2,4-dimethoxypyrimidin-5-yl)imidazo[1,2-b]pyridazine-3-carbonitrile was prepared in the manner described for Intermediate 18, but replacing 6-chloro-8-cyclopropyl-2-methyl-imidazo[1,2-b]pyridazine with 6-chloro-8-(4,4-difluorocyclohexyl)imidazo[1,2-b]pyridazine-3-carbonitrile. ES/MS m/z: 401.1 [M+1].

Intermediate 123. 8-(4,4-difluorocyclohexyl)-6-(2,4-dimethoxypyrimidin-5-yl)-3-methyl-imidazo[1,2-b]pyridazine

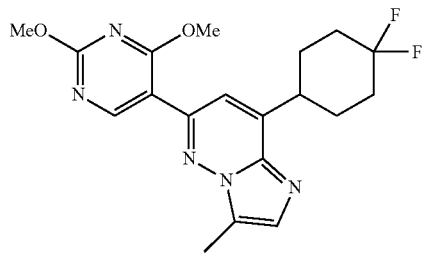 [SMILES: COc1ncc(-c2cc(C3CCC(F)(F)CC3)c3ncc(C)n3n2)c(OC)n1]

8-(4,4-difluorocyclohexyl)-6-(2,4-dimethoxypyrimidin-5-yl)-3-methyl-imidazo[1,2-b]pyridazine was prepared in the manner described for Intermediate 18, but replacing 6-chloro-8-cyclopropyl-2-methyl-imidazo[1,2-b]pyridazine with 6-chloro-8-(4,4-difluorocyclohexyl)-3-methyl-imidazo[1,2-b]pyridazine. ES/MS m/z: 390.1 [M+1].

Intermediate 124. 8-((benzyloxy)methyl)-6-(2,4-dimethoxypyrimidin-5-yl)imidazo[1,2-b]pyridazine

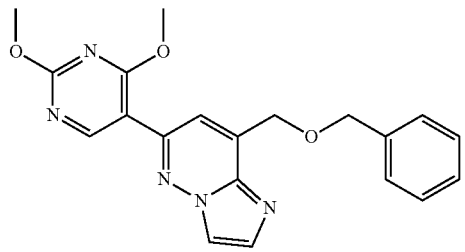 [SMILES: COc1ncc(-c2cc(COCc3ccccc3)c3nccn3n2)c(OC)n1]

8-((benzyloxy)methyl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 8-((benzyloxy)methyl)-6-chloroimidazo[1,2-b]pyridazine. ES/MS m/z: 378.18 [M+H].

Intermediate 125. 6-(2,4-dimethoxypyrimidin-5-yl)-8-(3-phenylazetidin-1-yl)imidazo[1,2-b]pyridazine

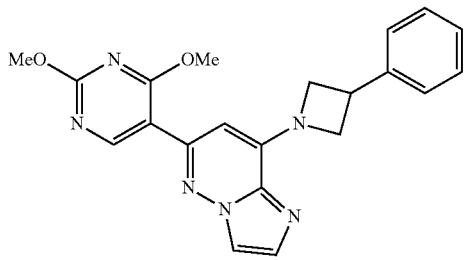 [SMILES: COc1ncc(-c2cc(N3CC(c4ccccc4)C3)c3nccn3n2)c(OC)n1]

6-(2,4-dimethoxypyrimidin-5-yl)-8-(3-phenylazetidin-1-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-phenylazetidin-1-yl)imidazo[1,2-b]pyridazine. ES/MS m/z: 389.1 [M+1].

Intermediate 126. 8-[(1S,2S)-2-(3,5-difluorophenyl)cyclopropyl]-6-(2,4-dimethoxypyrimidin-5-yl)imidazo[1,2-b]pyridazine (Racemic Mixture)

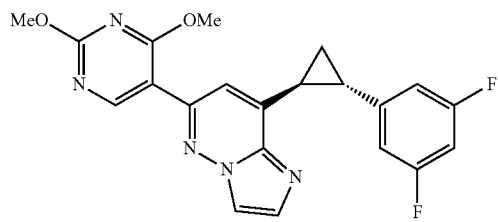 [SMILES: COc1ncc(-c2cc([C@H]3C[C@@H]3c3cc(F)cc(F)c3)c3nccn3n2)c(OC)n1]

8-[(1S,2S)-2-(3,5-difluorophenyl)cyclopropyl]-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-[(1S,2S)-2-(3,5-difluorophenyl)cyclopropyl]imidazo[1,2-b]pyridazine. ES/MS m/z: 410.1 [M+1].

Intermediate 127. 6-(2,4-dimethoxypyrimidin-5-yl)-8-[(1S,2S)-2-(2,3,5-trifluorophenyl)cyclopropyl]imidazo[1,2-b]pyridazine (Racemic Mixture)

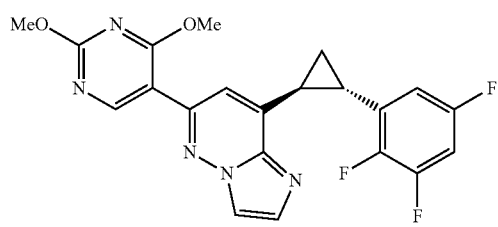 [SMILES: COc1ncc(-c2cc([C@H]3C[C@@H]3c3cc(F)cc(F)c3F)c3nccn3n2)c(OC)n1]

6-(2,4-dimethoxypyrimidin-5-yl)-8-[(1S,2S)-2-(2,3,5-trifluorophenyl)cyclopropyl]imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-[(1S,2S)-2-(2,3,5-trifluorophenyl)cyclopropyl]imidazo[1,2-b]pyridazine. ES/MS m/z: 428.1 [M+1].

Intermediate 128. 4-[(1S,2S)-2-[6-(2,4-dimethoxypyrimidin-5-yl)imidazo[1,2-b]pyridazin-8-yl]cyclopropyl]-2-fluoro-benzonitrile

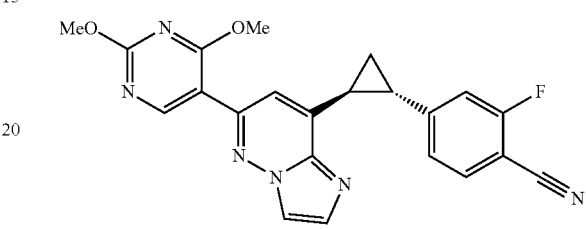

4-[(1S,2S)-2-(6-(2,4-dimethoxypyrimidin-5-yl)imidazo[1,2-b]pyridazin-8-yl)cyclopropyl]-2-fluoro-benzonitrile was prepared as a racemic mixture in the manner described for Intermediate 18, but replacing 6-chloro-8-cyclopropyl-2-methyl-imidazo[1,2-b]pyridazine with 4-[(1S,2S)-2-(6-chloroimidazo[1,2-b]pyridazin-8-yl)cyclopropyl]-2-fluoro-benzonitrile. ES/MS m/z: 417.1 [M+1].

Intermediate 129. 6-(2,4-dimethoxypyrimidin-5-yl)-8-[3-(trifluoromethyl)azetidin-1-yl]imidazo[1,2-b]pyridazine

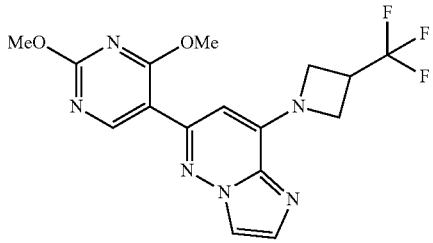 [SMILES: COc1ncc(-c2cc(N3CC(C(F)(F)F)C3)c3nccn3n2)c(OC)n1]

6-(2,4-dimethoxypyrimidin-5-yl)-8-[3-(trifluoromethyl)azetidin-1-yl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[3-(trifluoromethyl)azetidin-1-yl]imidazo[1,2-b]pyridazine. ES/MS m/z: 381.1 [M+1].

Intermediate 130. 6-(2,4-dimethoxypyrimidin-5-yl)-8-(3,3-dimethylazetidin-1-yl)imidazo[1,2-b]pyridazine

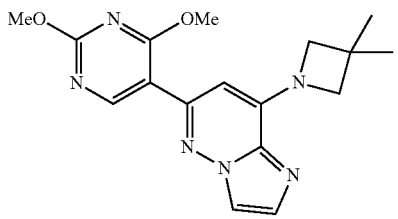 [SMILES: COc1ncc(-c2cc(N3CC(C)(C)C3)c3nccn3n2)c(OC)n1]

6-(2,4-dimethoxypyrimidin-5-yl)-8-(3,3-dimethylazetidin-1-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3,3-dimethylazetidin-1-yl)imidazo[1,2-b]pyridazine. ES/MS m/z: 341.2 [M+1].

Intermediate 131. 5-[(1S,2S)-2-[6-(2,4-dimethoxy-pyrimidin-5-yl)imidazo[1,2-b]pyridazin-8-yl]cyclopropyl]-2-fluoro-benzonitrile (Racemic Mixture)

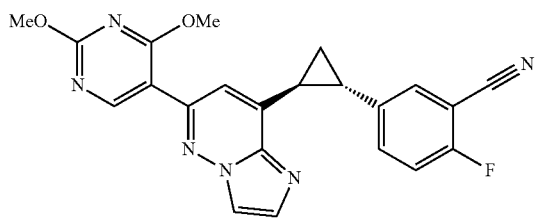 [SMILES: COc1ncc(-c2cc([C@H]3C[C@@H]3c3ccc(F)c(C#N)c3)c3nccn3n2)c(OC)n1]

5-[(1S,2S)-2-[6-(2,4-dimethoxypyrimidin-5-yl)imidazo[1,2-b]pyridazin-8-yl]cyclopropyl]-2-fluoro-benzonitrile was prepared as a racemic mixture in the manner described for Intermediate 18, but replacing 6-chloro-8-cyclopropyl-2-methyl-imidazo[1,2-b]pyridazine with 5-[(1S,2S)-2-(6-chloroimidazo[1,2-b]pyridazin-8-yl)cyclopropyl]-2-fluoro-benzonitrile. ES/MS m/z: 417.1 [M+1].

Intermediate 132. 8-[(1S,2S)-2-(2,5-difluorophenyl)cyclopropyl]-6-(2,4-dimethoxypyrimidin-5-yl)imidazo[1,2-b]pyridazine (Racemic Mixture)

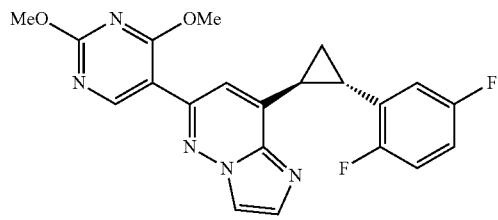 [SMILES: COc1ncc(-c2cc([C@H]3C[C@@H]3c3cc(F)ccc3F)c3nccn3n2)c(OC)n1]

8-[(1S,2S)-2-(2,5-difluorophenyl)cyclopropyl]-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-[(1S,2S)-2-(2,5-difluorophenyl)cyclopropyl]imidazo[1,2-b]pyridazine. ES/MS m/z: 410.2 [M+1].

Intermediate 133. 6-(2,4-dimethoxypyrimidin-5-yl)-8-(2-phenylazetidin-1-yl)imidazo[1,2-b]pyridazine

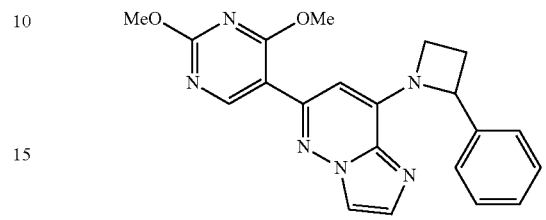

6-(2,4-dimethoxypyrimidin-5-yl)-8-(2-phenylazetidin-1-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(2-phenylazetidin-1-yl)imidazo[1,2-b]pyridazine. ES/MS m/z: 389.1 [M+1].

Intermediate 134. 8-cyclopropyl-6-(2,4-dimethoxypyrimidin-5-yl)-3-fluoro-imidazo[1,2-b]pyridazine

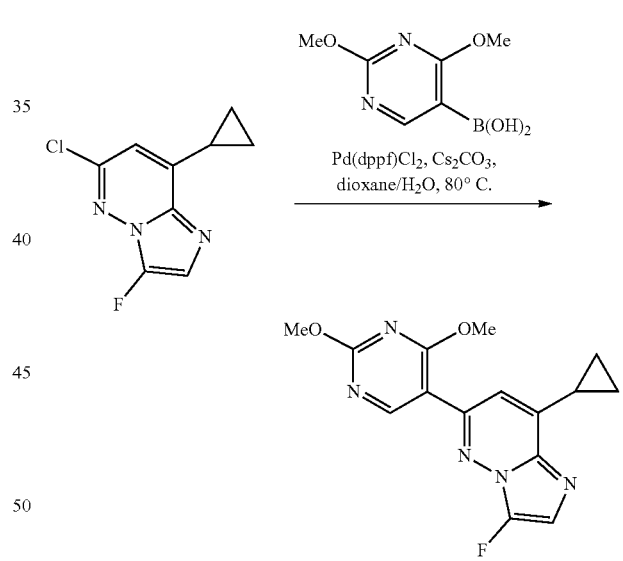

8-cyclopropyl-6-(2,4-dimethoxy-pyrimidin-5-yl)-3-fluoro-imidazo[1,2-b]pyridazine was prepared as follows: A microwave vial was charged with (2,4-dimethoxypyrimidin-5-yl)boronic acid (143 mg, 0.78 mmol, 1.1 equiv), Pd(dppf)Cl$_2$—CH$_2$Cl$_2$ (52 mg, 10 mol %), Cs$_2$CO$_3$ (462 mg, 1.42 mmol, 2 equiv) and 6-chloro-8-cyclopropyl-3-fluoro-imidazo[1,2-b]pyridazine (150 mg, 0.709 mmol, 1 equiv). The reaction mixture was dissolved in 3:1 dioxane/H$_2$O (4 mL), purged with argon, and was stirred at 80° C. for 3 h. The reaction mixture was then filtered and purified with reverse phase HPLC (ACN/water with 0.1% TFA) to afford 8-cyclopropyl-6-(2,4-dimethoxy-pyrimidin-5-yl)-3-fluoro-imidazo[1,2-b]pyridazine. ES/MS m/z: 316.10 [M+H].

Intermediate 135. 8-(4,4-difluoro-1-piperidyl)-6-(2,4-dimethoxypyrimidin-5-yl)imidazo[1,2-b]pyridazine

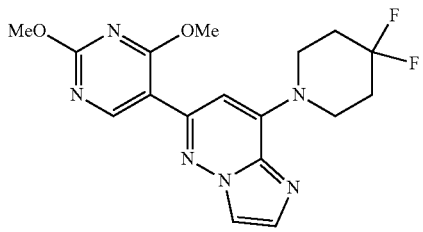 [SMILES: COc1ncc(-c2cc(N3CCC(F)(F)CC3)c3nccn3n2)c(OC)n1]

8-(4,4-difluoro-1-piperidyl)-6-(2,4-dimethoxypyrimidin-5-yl)imidazo[1,2-b]pyridazine was prepared in the manner described for Intermediate 134, but replacing 6-chloro-8-cyclopropyl-3-fluoro-imidazo[1,2-b]pyridazine with 6-chloro-8-(4,4-difluoro-1-piperidyl)imidazo[1,2-b]pyridazine. ES/MS m/z: 377.10 [M+H].

Intermediate 136. 8-(3,3-difluoro-4,4-dimethyl-pyrrolidin-1-yl)-6-(2,4-dimethoxypyrimidin-5-yl)imidazo[1,2-b]pyridazine

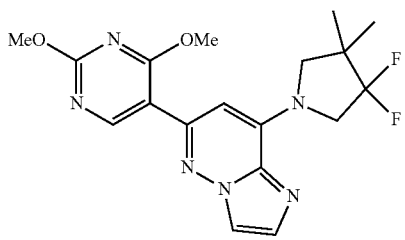 [SMILES: COc1ncc(-c2cc(N3CC(C)(C)C(F)(F)C3)c3nccn3n2)c(OC)n1]

8-(3,3-difluoro-4,4-dimethyl-pyrrolidin-1-yl)-6-(2,4-dimethoxypyrimidin-5-yl)imidazo[1,2-b]pyridazine was prepared in the manner described for Intermediate 134, but replacing 6-chloro-8-cyclopropyl-3-fluoro-imidazo[1,2-b]pyridazine with 6-chloro-8-(3,3-difluoro-4,4-dimethyl-pyrrolidin-1-yl)imidazo[1,2-b]pyridazine. ES/MS m/z: 391.20 [M+H].

Intermediate 137. 6-(2,4-dimethoxypyrimidin-5-yl)-8-(3,3-dimethylpyrrolidin-1-yl)imidazo[1,2-b]pyridazine

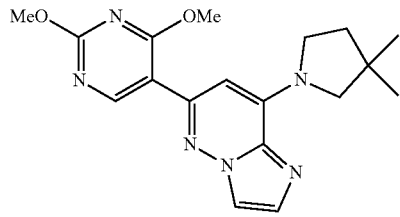 [SMILES: COc1ncc(-c2cc(N3CCC(C)(C)C3)c3nccn3n2)c(OC)n1]

6-(2,4-dimethoxypyrimidin-5-yl)-8-(3,3-dimethylpyrrolidin-1-yl)imidazo[1,2-b]pyridazine was prepared in the manner described for Intermediate 134, but replacing 6-chloro-8-cyclopropyl-3-fluoro-imidazo[1,2-b]pyridazine with 6-chloro-8-(3,3-dimethylpyrrolidin-1-yl)imidazo[1,2-b]pyridazine. ES/MS m/z: 355.20 [M+H].

Intermediate 138. 8-[(3S,4S)-3,4-difluoropyrrolidin-1-yl]-6-(2,4-dimethoxypyrimidin-5-yl)imidazo[1,2-b]pyridazine

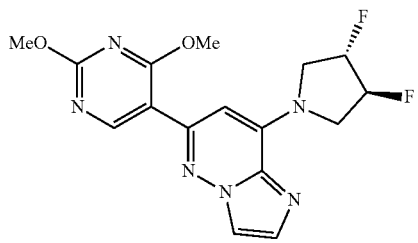 [SMILES: COc1ncc(-c2cc(N3C[C@H](F)[C@@H](F)C3)c3nccn3n2)c(OC)n1]

8-[(3S,4S)-3,4-difluoropyrrolidin-1-yl]-6-(2,4-dimethoxypyrimidin-5-yl)imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-8-[(3S,4S)-3,4-difluoropyrrolidin-1-yl]imidazo[1,2-b]pyridazine (Racemic Mixture). ES/MS m/z: 363.20 [M+H].

Intermediate 139. 8-[(3S,4R)-3,4-difluoropyrrolidin-1-yl]-6-(2,4-dimethoxypyrimidin-5-yl)imidazo[1,2-b]pyridazine (cis)

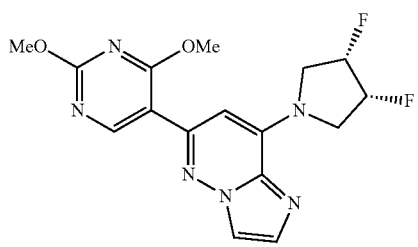 [SMILES: COc1ncc(-c2cc(N3C[C@@H](F)[C@@H](F)C3)c3nccn3n2)c(OC)n1]

8-[(3S,4R)-3,4-difluoropyrrolidin-1-yl]-6-(2,4-dimethoxypyrimidin-5-yl)imidazo[1,2-b]pyridazine (cis) was prepared in the manner described for Intermediate 134, but replacing 6-chloro-8-cyclopropyl-3-fluoro-imidazo[1,2-b]pyridazine with 6-chloro-8-[(3S,4R)-3,4-difluoropyrrolidin-1-yl]imidazo[1,2-b]pyridazine (cis). ES/MS m/z: 363.20 [M+H].

Intermediate 140. 6-(2,4-dimethoxypyrimidin-5-yl)-8-pyrazol-1-yl-imidazo[1,2-b]pyridazine

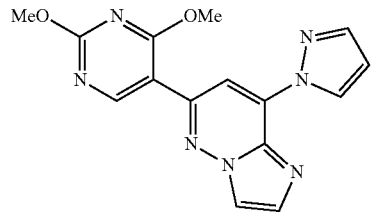 [SMILES: COc1ncc(-c2cc(-n3cccn3)c3nccn3n2)c(OC)n1]

6-(2,4-dimethoxypyrimidin-5-yl)-8-pyrazol-1-yl-imidazo[1,2-b]pyridazine was prepared in the manner described for Intermediate 134, but replacing 6-chloro-8-cyclopropyl-3-fluoro-imidazo[1,2-b]pyridazine with 6-chloro-8-pyrazol-1-yl-imidazo[1,2-b]pyridazine. ES/MS m/z: 324.10 [M+H].

Intermediate 141. 8-(3,3-difluoropyrrolidin-1-yl)-6-(2,4-dimethoxypyrimidin-5-yl)imidazo[1,2-b]pyridazine

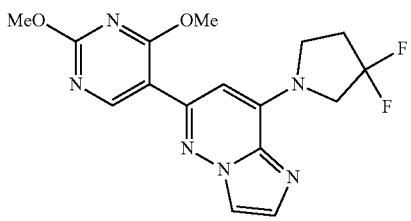 [SMILES: COc1ncc(-c2cc(N3CCC(F)(F)C3)c3nccn3n2)c(OC)n1]

8-(3,3-difluoropyrrolidin-1-yl)-6-(2,4-dimethoxypyrimidin-5-yl)imidazo[1,2-b]pyridazine was prepared in the manner described for Intermediate 134, but replacing 6-chloro-8-cyclopropyl-3-fluoro-imidazo[1,2-b]pyridazine with 6-chloro-8-(3,3-difluoropyrrolidin-1-yl)imidazo[1,2-b]pyridazine. ES/MS m/z: 363.10 [M+H].

Intermediate 142. 6-(2,4-dimethoxypyrimidin-5-yl)-8-[(1S,2S)-2-(2-pyridyl)cyclopropyl]imidazo[1,2-b]pyridazine

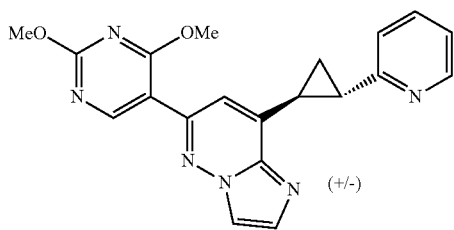 [SMILES: COc1ncc(-c2cc([C@H]3C[C@@H]3c3ccccn3)c3nccn3n2)c(OC)n1]

6-(2,4-dimethoxypyrimidin-5-yl)-8-[(1S,2S)-2-(2-pyridyl)cyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-8-[(1S,2S)-2-(2-pyridyl)cyclopropyl]imidazo[1,2-b]pyridazine (Racemic Mixture). ES/MS m/z: 375.20 [M+H].

Intermediate 143. 6-(2,4-dimethoxypyrimidin-5-yl)-8-[(1S,2S)-2-[4-(trifluoromethyl)phenyl]cyclopropyl]imidazo[1,2-b]pyridazine

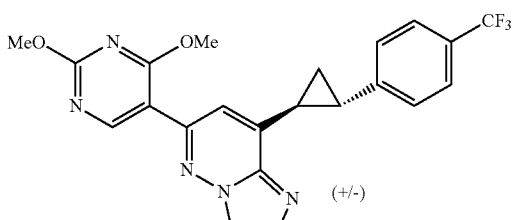

6-(2,4-dimethoxypyrimidin-5-yl)-8-[(1S,2S)-2-[4-(trifluoromethyl)phenyl]cyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-8-[(1S,2S)-2-[4-(trifluoromethyl)phenyl]cyclopropyl]imidazo[1,2-b]pyridazine (Racemic Mixture). ES/MS m/z: 442.10 [M+H].

Intermediate 144. 6-(2,4-dimethoxypyrimidin-5-yl)-8-[(1S,2S)-2-[3-(trifluoromethyl)phenyl]cyclopropyl]imidazo[1,2-b]pyridazine

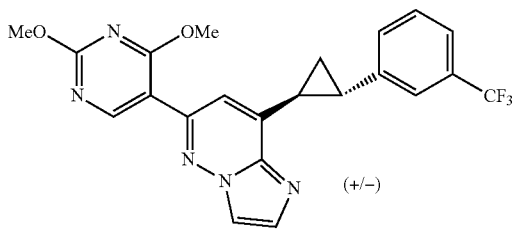 [SMILES: COc1ncc(-c2cc([C@H]3C[C@@H]3c3cccc(C(F)(F)F)c3)c3nccn3n2)c(OC)n1]

6-(2,4-dimethoxypyrimidin-5-yl)-8-[(1S,2S)-2-[3-(trifluoromethyl)phenyl]cyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-8-[(1S,2S)-2-[3-(trifluoromethyl)phenyl]cyclopropyl]imidazo[1,2-b]pyridazine (Racemic Mixture). ES/MS m/z: 442.10 [M+H].

Intermediate 145. 6-(2,4-dimethoxypyrimidin-5-yl)-8-[(1S,2S)-2-(1-naphthyl)cyclopropyl]imidazo[1,2-b]pyridazine

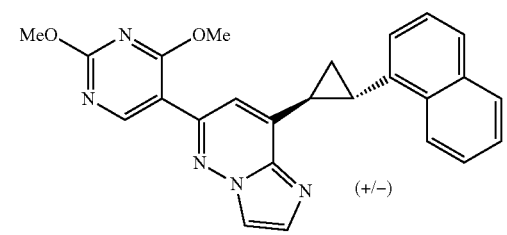 [SMILES: COc1ncc(-c2cc([C@H]3C[C@@H]3c3cccc4ccccc34)c3nccn3n2)c(OC)n1]

6-(2,4-dimethoxypyrimidin-5-yl)-8-[(1S,2S)-2-(1-naphthyl)cyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-8-[(1S,2S)-2-(1-naphthyl)cyclopropyl]imidazo[1,2-b]pyridazine (Racemic Mixture). ES/MS m/z: 424.20 [M+H].

Intermediate 146. 6-(2,4-dimethoxypyrimidin-5-yl)-3-fluoro-8-[(1S,2S)-2-(4-fluorophenyl)cyclopropyl]imidazo[1,2-b]pyridazine

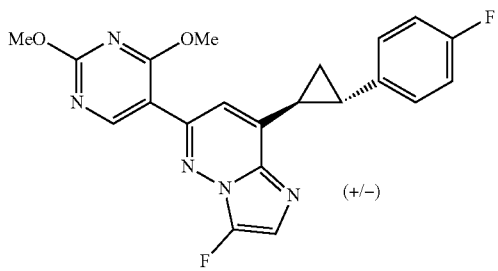 [SMILES: COc1ncc(-c2cc([C@H]3C[C@@H]3c3ccc(F)cc3)c3ncc(F)n3n2)c(OC)n1]

6-(2,4-dimethoxypyrimidin-5-yl)-3-fluoro-8-[(1S,2S)-2-(4-fluorophenyl)cyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-3-fluoro-8-[(1S,2S)-2-(4-fluorophenyl)cyclopropyl]imidazo[1,2-b]pyridazine (Racemic Mixture). ES/MS m/z: 410.10 [M+H].

Intermediate 147. N-(cyclopropylmethyl)-4-[6-(2,4-dimethoxypyrimidin-5-yl)imidazo[1,2-b]pyridazin-8-yl]aniline

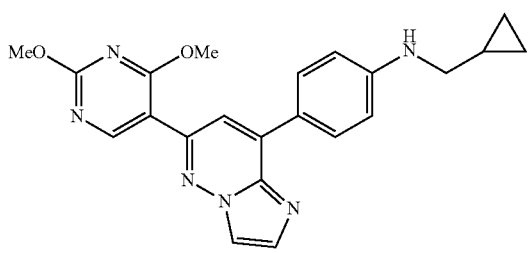 [SMILES: COc1ncc(-c2cc(-c3ccc(NCC4CC4)cc3)c3nccn3n2)c(OC)n1]

N-(cyclopropylmethyl)-4-[6-(2,4-dimethoxypyrimidin-5-yl)imidazo[1,2-b]pyridazin-8-yl]aniline was prepared in the manner described for Intermediate 134, but replacing 6-chloro-8-cyclopropyl-3-fluoro-imidazo[1,2-b]pyridazine with 4-(6-chloroimidazo[1,2-b]pyridazin-8-yl)-N-(cyclopropylmethyl)aniline. ES/MS m/z: 403.20 [M+H].

Intermediate 148. 2,8-dicyclopropyl-6-(2,4-dimethoxypyrimidin-5-yl)imidazo[1,2-b]pyridazine

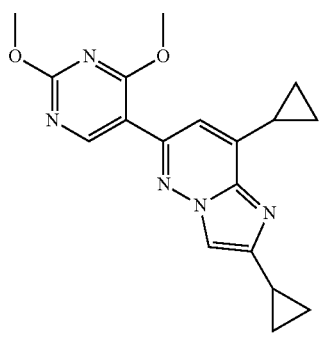 [SMILES: COc1ncc(-c2cc(C3CC3)c3nc(C4CC4)cn3n2)c(OC)n1]

2,8-dicyclopropyl-6-(2,4-dimethoxypyrimidin-5-yl)imidazo[1,2-b]pyridazine was prepared in the manner described for Intermediate 134, but replacing 6-chloro-8-cyclopropyl-3-fluoro-imidazo[1,2-b]pyridazine with 6-chloro-2,8-dicyclopropyl-imidazo[1,2-b]pyridazine. ES/MS m/z: 338.20 [M+H].

Intermediate 149. 3-[(1S,2S)-2-[6-(2,4-dimethoxy-pyrimidin-5-yl)imidazo[1,2-b]pyridazin-8-yl]cyclopropyl]-5-fluoro-benzonitrile

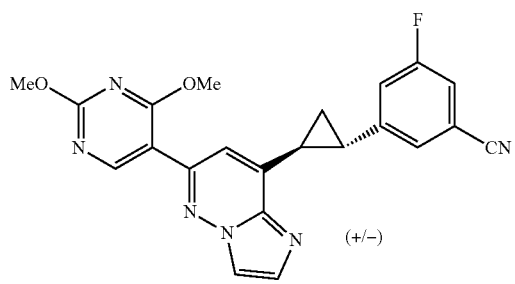 [SMILES: COc1ncc(-c2cc([C@H]3C[C@@H]3c3cc(F)cc(C#N)c3)c3nccn3n2)c(OC)n1]

3-[(1S,2S)-2-[6-(2,4-dimethoxypyrimidin-5-yl)imidazo[1,2-b]pyridazin-8-yl]cyclopropyl]-5-fluoro-benzonitrile was prepared as a racemic mixture in the manner described for Intermediate 134, but replacing 6-chloro-8-cyclopropyl-3-fluoro-imidazo[1,2-b]pyridazine with 3-[(1S,2S)-2-(6-chloroimidazo[1,2-b]pyridazin-8-yl)cyclopropyl]-5-fluoro-benzonitrile (Racemic Mixture). ES/MS m/z: 417.10 [M+H].

Intermediate 150. 2-cyclopropyl-6-(2,4-dimethoxy-pyrimidin-5-yl)-8-[(1S,2S)-2-(4-fluorophenyl)cyclopropyl]imidazo[1,2-b]pyridazine

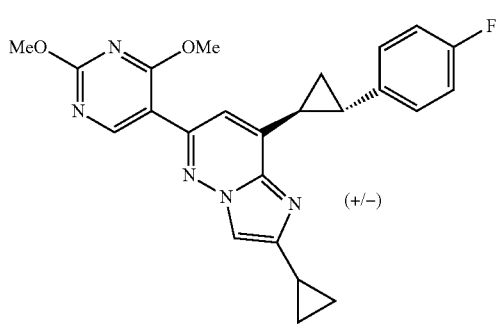 [SMILES: COc1ncc(-c2cc([C@H]3C[C@@H]3c3ccc(F)cc3)c3nc(C4CC4)cn3n2)c(OC)n1]

2-cyclopropyl-6-(2,4-dimethoxypyrimidin-5-yl)-8-[(1S,2S)-2-(4-fluorophenyl)cyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-2-cyclopropyl-8-[(1R,2R)-2-(4-fluorophenyl)cyclopropyl]imidazo[1,2-b]pyridazine (Racemic Mixture). ES/MS m/z: 432.10 [M+H].

Intermediate 151. 6-(2,4-dimethoxypyrimidin-5-yl)-3-fluoro-8-[(1S,2S)-2-phenylcyclopropyl]imidazo[1,2-b]pyridazine

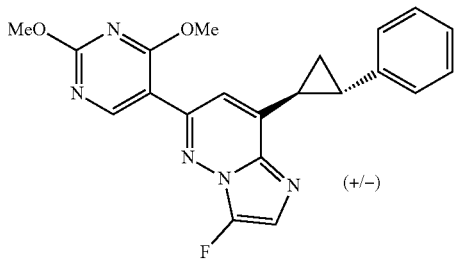 [SMILES: COc1ncc(-c2cc([C@H]3C[C@@H]3c3ccccc3)c3ncc(F)n3n2)c(OC)n1]

(+/−)

6-(2,4-dimethoxypyrimidin-5-yl)-3-fluoro-8-[(1S,2S)-2-phenylcyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-3-fluoro-8-[(1R,2R)-2-phenylcyclopropyl]imidazo[1,2-b]pyridazine (Racemic Mixture). ES/MS m/z: 392.10 [M+H].

Intermediate 152. 8-[(1S,2S)-2-(2,4-difluorophenyl)cyclopropyl]-6-(2,4-dimethoxypyrimidin-5-yl)-3-fluoro-imidazo[1,2-b]pyridazine

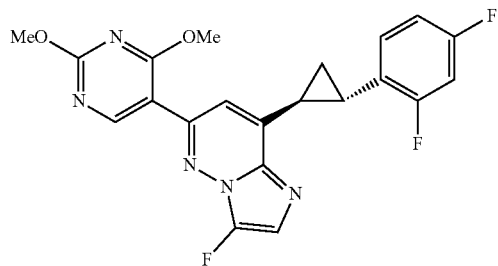 [SMILES: COc1ncc(-c2cc([C@H]3C[C@@H]3c3ccc(F)cc3F)c3ncc(F)n3n2)c(OC)n1]

8-[(1S,2S)-2-(2,4-difluorophenyl)cyclopropyl]-6-(2,4-dimethoxypyrimidin-5-yl)-3-fluoro-imidazo[1,2-b]pyridazine was prepared in the manner described for Intermediate 134, but replacing 6-chloro-8-cyclopropyl-3-fluoro-imidazo[1,2-b]pyridazine with 6-chloro-8-[(1S,2S)-2-(2,4-difluorophenyl)cyclopropyl]-3-fluoro-imidazo[1,2-b]pyridazine. ES/MS m/z: 428.10 [M+H].

Intermediate 153. 6-(2,4-dimethoxypyrimidin-5-yl)-8-(4,4-dimethyl-1-piperidyl)imidazo[1,2-b]pyridazine

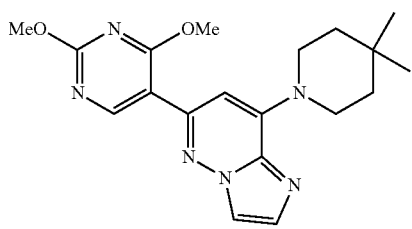 [SMILES: COc1ncc(-c2cc(N3CCC(C)(C)CC3)c3nccn3n2)c(OC)n1]

6-(2,4-dimethoxypyrimidin-5-yl)-8-(4,4-dimethyl-1-piperidyl)imidazo[1,2-b]pyridazine was prepared in the manner described for Intermediate 134, but replacing 6-chloro-8-cyclopropyl-3-fluoro-imidazo[1,2-b]pyridazine with 6-chloro-8-(4,4-dimethyl-1-piperidyl)imidazo[1,2-b]pyridazine. ES/MS m/z: 369.20 [M+H].

Intermediate 154. 8-[(1S,2S)-2-(3,4-difluorophenyl)cyclopropyl]-6-(2,4-dimethoxypyrimidin-5-yl)-3-fluoro-imidazo[1,2-b]pyridazine

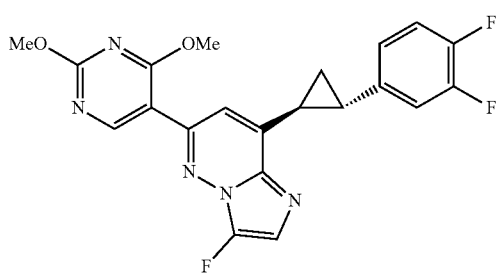 [SMILES: COc1ncc(-c2cc([C@H]3C[C@@H]3c3ccc(F)c(F)c3)c3ncc(F)n3n2)c(OC)n1]

8-[(1S,2S)-2-(3,4-difluorophenyl)cyclopropyl]-6-(2,4-dimethoxypyrimidin-5-yl)-3-fluoro-imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-8-[(1S,2S)-2-(3,4-difluorophenyl)cyclopropyl]-3-fluoro-imidazo[1,2-b]pyridazine. ES/MS m/z: 428.20 [M+H].

Intermediate 155. 6-(2,4-dimethoxypyrimidin-5-yl)-8-[(1S,2S)-2-(3-pyridyl)cyclopropyl]imidazo[1,2-b]pyridazine

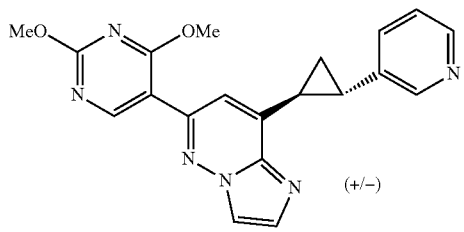 [SMILES: COc1ncc(-c2cc([C@H]3C[C@@H]3c3cccnc3)c3nccn3n2)c(OC)n1]

(+/−)

6-(2,4-dimethoxypyrimidin-5-yl)-8-[(1S,2S)-2-(3-pyridyl)cyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-8-[(1S,2S)-2-(3-pyridyl)cyclopropyl]imidazo[1,2-b]pyridazine (Racemic Mixture). ES/MS m/z: 375.10 [M+H].

Intermediate 156. 6-(2,4-dimethoxypyrimidin-5-yl)-8-[(1S,2S)-2-(4-pyridyl)cyclopropyl]imidazo[1,2-b]pyridazine

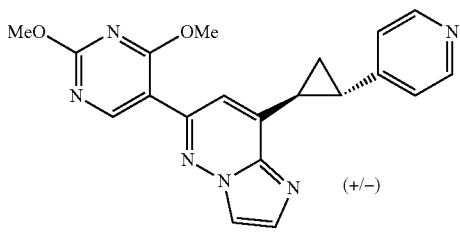 [SMILES: COc1ncc(-c2cc([C@H]3C[C@@H]3c3ccncc3)c3nccn3n2)c(OC)n1]

(+/−)

6-(2,4-dimethoxypyrimidin-5-yl)-8-[(1S,2S)-2-(4-pyridyl)cyclopropyl]imidazo[1,2-b]pyridazine was prepared as a racemic mixture in the manner described for Intermediate 134, but replacing 6-chloro-8-cyclopropyl-3-fluoro-imidazo[1,2-b]pyridazine with 6-chloro-8-[(1S,2S)-2-(4-pyridyl)cyclopropyl]imidazo[1,2-b]pyridazine (Racemic Mixture). ES/MS m/z: 375.10 [M+H].

Intermediate 157. 5-(2,4-dimethoxypyrimidin-5-yl)-7-(3,3-dimethylpyrrolidin-1-yl)pyrazolo[1,5-a]pyrimidine

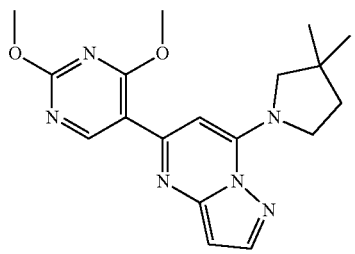 [SMILES: COc1ncc(-c2cc(N3CCC(C)(C)C3)n3nccc3n2)c(OC)n1]

5-(2,4-dimethoxypyrimidin-5-yl)-7-(3,3-dimethylpyrrolidin-1-yl)pyrazolo[1,5-a]pyrimidine was prepared in the manner described for Intermediate 18, but replacing 6-chloro-8-cyclopropyl-2-methyl-imidazo[1,2-b]pyridazine with 5-chloro-7-(3,3-dimethylpyrrolidin-1-yl)pyrazolo[1,5-a]pyrimidine. ES/MS m/z: 355.16 [M+H].

Intermediate 158. 5-(2,4-dimethoxypyrimidin-5-yl)-7-(3,3-dimethylpyrrolidin-1-yl)-[1,2,4]triazolo[1,5-a]pyrimidine

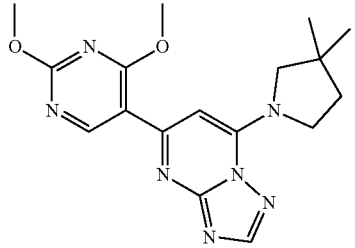 [SMILES: COc1ncc(-c2cc(N3CCC(C)(C)C3)n3ncnc3n2)c(OC)n1]

5-(2,4-dimethoxypyrimidin-5-yl)-7-(3,3-dimethylpyrrolidin-1-yl)-[1,2,4]triazolo[1,5-a]pyrimidine was prepared in the manner described for Intermediate 18, but replacing 6-chloro-8-cyclopropyl-2-methyl-imidazo[1,2-b]pyridazine with 5-chloro-7-(3,3-dimethylpyrrolidin-1-yl)-[1,2,4]triazolo[1,5-a]pyrimidine. ES/MS m/z: 356.20 [M+H].

Intermediate 159. 8-(3,3-difluoropiperidin-1-yl)-6-(2,4-dimethoxypyrimidin-5-yl)imidazo[1,2-b]pyridazine

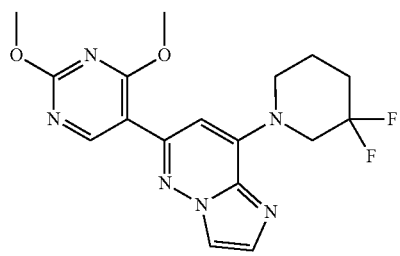 [SMILES: COc1ncc(-c2cc(N3CCCC(F)(F)C3)c3nccn3n2)c(OC)n1]

8-(3,3-difluoropiperidin-1-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3,3-difluoropiperidin-1-yl)imidazo[1,2-b]pyridazine. ES/MS m/z: 377.17 [M+H].

Intermediate 160. 8-(3-aza bicyclo[3.2.1]octan-3-yl)-6-(2,4-dimethoxypyrimidin-5-yl)imidazo[1,2-b]pyridazine

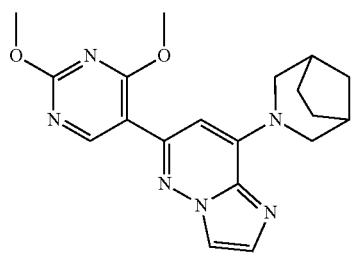 [SMILES: COc1ncc(-c2cc(N3CC4CCC(C4)C3)c3nccn3n2)c(OC)n1]

Bicyclo[3.2.1]octan-3-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 8-(3-azabicyclo[3.2.1]octan-3-yl)-6-chloroimidazo[1,2-b]pyridazine. ES/MS m/z: 367.14 [M+H].

Intermediate 161. 6-(2,4-dimethoxypyrimidin-5-yl)-8-((1S,2S)-2-(4-fluoro-3-(trifluoromethyl)phenyl)cyclopropyl)imidazo[1,2-b]pyridazine (Racemic Mixture)

Intermediate 163. 8-cyclopropyl-6-(2,4-dimethoxypyrimidin-5-yl)-2-(pyridin-4-yl)imidazo[1,2-b]pyridazine

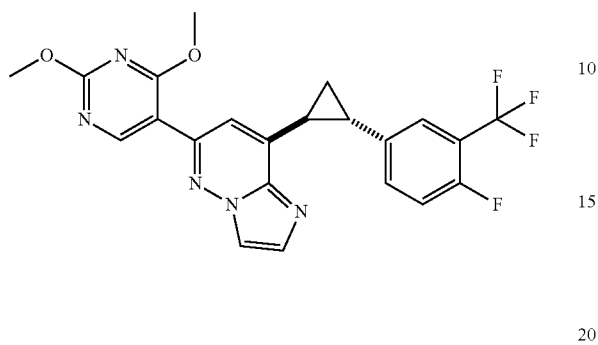

6-(2,4-dimethoxypyrimidin-5-yl)-8-((1S,2S)-2-(4-fluoro-3-(trifluoromethyl)phenyl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with racemic 6-chloro-8-((1S,2S)-2-(4-fluoro-3-(trifluoromethyl)phenyl)cyclopropyl)imidazo[1,2-b]pyridazine. ES/MS m/z: 460.10 [M+H].

8-cyclopropyl-6-(2,4-dimethoxypyrimidin-5-yl)-2-(pyridin-4-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-cyclopropyl-2-(pyridin-4-yl)imidazo[1,2-b]pyridazine. ES/MS m/z: 375.10 [M+H].

Intermediate 162. 8-cyclopropyl-6-(2,4-dimethoxypyrimidin-5-yl)-2-(2-(trifluoromethyl)phenyl)imidazo[1,2-b]pyridazine

Intermediate 164. 8-((1S,2S)-2-(4-chloro-3-fluorophenyl)cyclopropyl)-6-(2,4-dimethoxypyrimidin-5-yl)imidazo[1,2-b]pyridazine (Racemic Mixture)

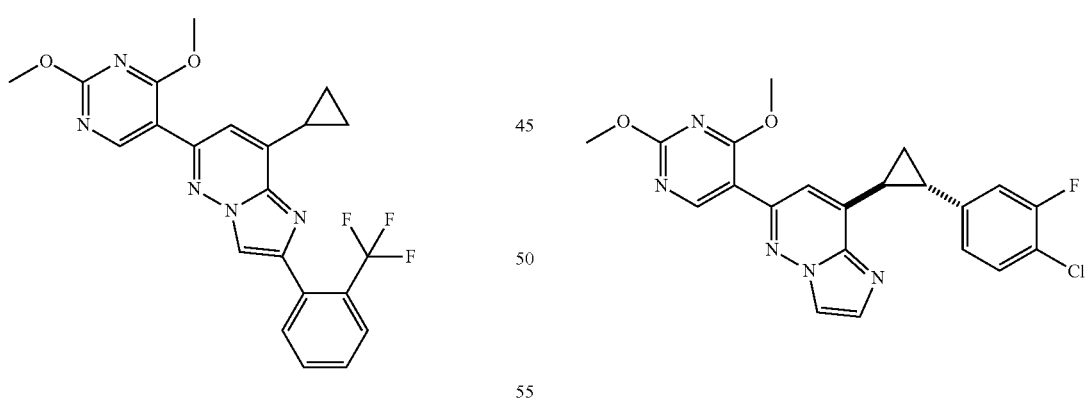

8-cyclopropyl-6-(2,4-dimethoxypyrimidin-5-yl)-2-(2-(trifluoromethyl)phenyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-cyclopropyl-2-(2-(trifluoromethyl)phenyl)imidazo[1,2-b]pyridazine. ES/MS m/z: 442.10 [M+H].

8-((1S,2S)-2-(4-chloro-3-fluorophenyl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with racemic 6-chloro-8-((1S,2S)-2-(4-chloro-3-fluorophenyl)cyclopropyl)imidazo[1,2-b]pyridazine. ES/MS m/z: 426.10 [M+H].

Intermediate 165. 8-((2S,2S)-2-(3-chloro-4-fluoro-phenyl)cyclopropyl)-6-(2,4-dimethoxypyrimidin-5-yl)imidazo[1,2-b]pyridazine (Racemic Mixture)

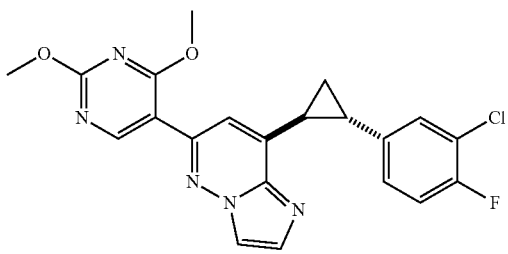

8-((1S,2S)-2-(3-chloro-4-fluorophenyl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with racemic 6-chloro-8-((1S,2S)-2-(3-chloro-4-fluorophenyl)cyclopropyl)imidazo[1,2-b]pyridazine. ES/MS m/z: 426.10 [M+H].

Intermediate 166. 6-(2,4-dimethoxypyrimidin-5-yl)-8-((1S,2S)-2-(3-fluoro-4-(trifluoromethyl)phenyl)cyclopropyl)imidazo[1,2-b]pyridazine (Racemic Mixture)

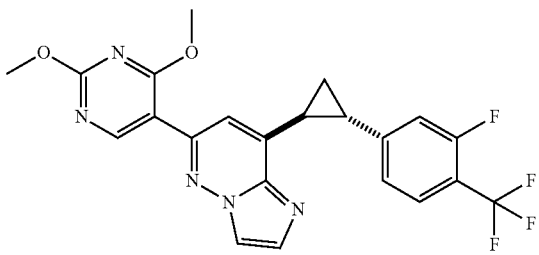

6-(2,4-dimethoxypyrimidin-5-yl)-8-((1S,2S)-2-(3-fluoro-4-(trifluoromethyl)phenyl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with racemic 6-chloro-8-((1S,2S)-2-(3-fluoro-4-(trifluoromethyl)phenyl)cyclopropyl)imidazo[1,2-b]pyridazine. ES/MS m/z: 460.10 [M+H].

Intermediate 167. 6-(2,4-dimethoxypyrimidin-5-yl)-8-((1S,2S)-2-(2-methoxyphenyl)cyclopropyl)imidazo[1,2-b]pyridazine (Racemic Mixture)

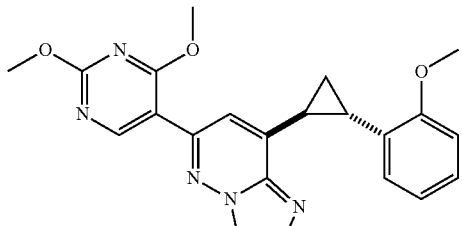

6-(2,4-dimethoxypyrimidin-5-yl)-8-((2S,2S)-2-(2-methoxyphenyl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with racemic 6-chloro-8-((1S,2S)-2-(2-methoxyphenyl)cyclopropyl)imidazo[1,2-b] pyridazine. ES/MS m/z: 404.20 [M+H].

Intermediate 168. 8-cyclopropyl-6-(2,4-dimethoxy-pyrimidin-5-yl)-2-(pyridin-3-yl)imidazo[1,2-b]pyridazine

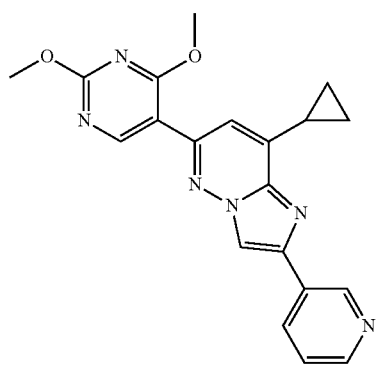 [SMILES: COc1ncc(-c2cc(C3CC3)c3nc(-c4cccnc4)cn3n2)c(OC)n1]

8-cyclopropyl-6-(2,4-dimethoxypyrimidin-5-yl)-2-(pyridin-3-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-cyclopropyl-2-(pyridin-3-yl)imidazo[1,2-b]pyridazine. ES/MS m/z: 375.19 [M+H].

Intermediate 169. 8-cyclopropyl-6-(2,4-dimethoxy-pyrimidin-5-yl)-2-(pyridin-2-yl)imidazo[1,2-b]pyridazine

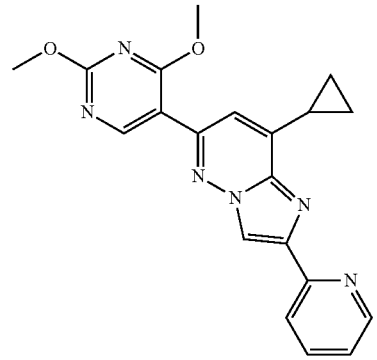 [SMILES: COc1ncc(-c2cc(C3CC3)c3nc(-c4ccccn4)cn3n2)c(OC)n1]

8-cyclopropyl-6-(2,4-dimethoxypyrimidin-5-yl)-2-(pyridin-2-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-cyclopropyl-2-(pyridin-2-yl)imidazo[1,2-b]pyridazine. ES/MS m/z: 375.20 [M+H].

Intermediate 170. 8-((1S,2R)-2-benzylcyclopropyl)-6-(2,4-dimethoxypyrimidin-5-yl)imidazo[1,2-b]pyridazine

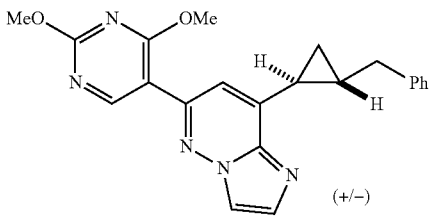 [SMILES: COc1ncc(-c2cc([C@H]3C[C@@H]3Cc3ccccc3)c3nccn3n2)c(OC)n1]

(+/−)

8-((1S,2R)-2-benzylcyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 8-((1S,2R)-2-benzylcyclopropyl)-6-chloroimidazo[1,2-b]pyridazine (Racemic Mixture). ES/MS m/z: 388.20 [M+H].

Intermediate 171. 8-((1S,2R)-2-(3,3-difluorocyclobutyl)cyclopropyl)-6-(2,4-dimethoxypyrimidin-5-yl)imidazo[1,2-b]pyridazine

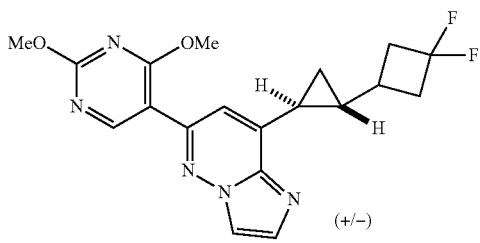 [SMILES: COc1ncc(-c2cc([C@H]3C[C@@H]3C3CC(F)(F)C3)c3nccn3n2)c(OC)n1]

(+/−)

8-((1S,2R)-2-(3,3-difluorocyclobutyl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2R)-2-(3,3-difluorocyclobutyl)cyclopropyl)imidazo[1,2-b]pyridazine (racemic mixture). ES/MS m/z: 388.10 [M+H].

Intermediate 172. 6-(2,4-dimethoxypyrimidin-5-yl)-8-((1S,2S)-2-(trifluoromethyl)cyclopropyl)imidazo[1,2-b]pyridazine

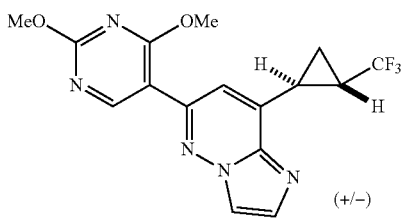 [SMILES: COc1ncc(-c2cc([C@H]3C[C@@H]3C(F)(F)F)c3nccn3n2)c(OC)n1]

(+/−)

6-(2,4-dimethoxypyrimidin-5-yl)-8-((1S,2S)-2-(trifluoromethyl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(trifluoromethyl)cyclopropyl)imidazo[1,2-b]pyridazine (Racemic Mixture). ES/MS m/z: 366.10 [M+H].

Intermediate 173. 6-(2,4-dimethoxypyrimidin-5-yl)-8-((1R,2R)-2-fluoro-2-phenylcyclopropyl)imidazo[1,2-b]pyridazine

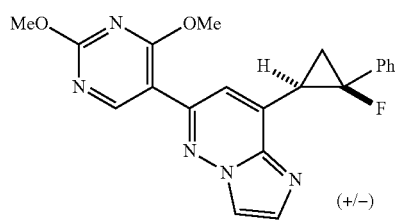 [SMILES: COc1ncc(-c2cc([C@H]3C[C@]3(F)c3ccccc3)c3nccn3n2)c(OC)n1]

(+/−)

6-(2,4-dimethoxypyrimidin-5-yl)-8-((1R,2R)-2-fluoro-2-phenylcyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1R,2R)-2-fluoro-2-phenylcyclopropyl)imidazo[1,2-b]pyridazine (Racemic Mixture). ES/MS m/z: 392.20 [M+H].

Intermediate 174. 6-(2,4-dimethoxypyrimidin-5-yl)-8-(3,3,4,4-tetrafluoropyrrolidin-1-yl)imidazo[1,2-b]pyridazine

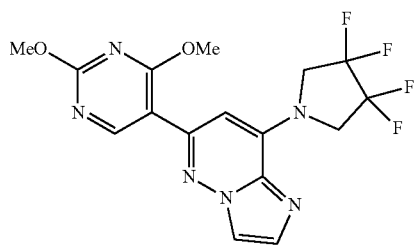 [SMILES: COc1ncc(-c2cc(N3CC(F)(F)C(F)(F)C3)c3nccn3n2)c(OC)n1]

6-(2,4-dimethoxypyrimidin-5-yl)-8-(3,3,4,4-tetrafluoropyrrolidin-1-yl)imidazo[1,2-b]pyridazine was prepared as follows: To a mixture of 6-chloro-8-(3,3,4,4-tetrafluoropyrrolidin-1-yl)imidazo[1,2-b]pyridazine (24 mg, 0.082 mmol) and (2,4-dimethoxypyrimidin-5-yl)boronic acid (30 mg, 0.16 mmol) in 1,4-dioxane (1.5 mL) and water (0.75 mL) were added ferrous; cyclopenta-2,4-dien-1-yl(diphenyl)phosphane; dichloromethane; dichloropalladium (7 mg, 0.008 mmol) and cesium carbonate (53 mg, 0.16 mmol). The reaction mixture was heated at 80° C. for 1 h. The reaction mixture was then filtered and was purified with Prep HPLC to afford 6-(2,4-dimethoxypyrimidin-5-yl)-8-(3,3,4,4-tetrafluoropyrrolidin-1-yl)imidazo[1,2-b]pyridazine. ES/MS m/z: 399.10 [M+H].

Intermediate 175. 8-((2S,2S)-2-(4-cyclopropylphenyl)cyclopropyl)-6-(2,4-dimethoxypyrimidin-5-yl)imidazo[1,2-b]pyridazine

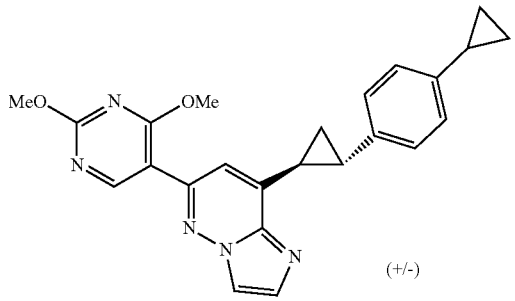 [SMILES: COc1ncc(-c2cc([C@H]3C[C@@H]3c3ccc(C4CC4)cc3)c3nccn3n2)c(OC)n1]

(+/-)

8-((1S,2S)-2-(4-cyclopropylphenyl)cyclopropyl)-6-(2,4-dimethoxypyrimidin-5-yl)imidazo[1,2-b]pyridazine was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(4-cyclopropylphenyl)cyclopropyl)imidazo[1,2-b]pyridazine. ES/MS m/z: 414.20 [M+1].

Intermediate 176. 6-(2,4-dimethoxypyrimidin-5-yl)-8-((1S,2S)-2-(3-(trifluoromethoxy)phenyl)cyclopropyl)imidazo[1,2-b]pyridazine

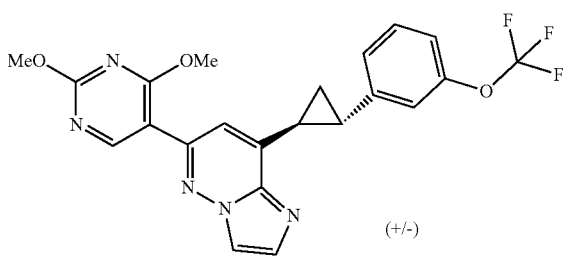 [SMILES: COc1ncc(-c2cc([C@H]3C[C@@H]3c3cccc(OC(F)(F)F)c3)c3nccn3n2)c(OC)n1]

(+/-)

6-(2,4-dimethoxypyrimidin-5-yl)-8-((2S,2S)-2-(3-(trifluoromethoxy)phenyl)cyclopropyl)imidazo[1,2-b]pyridazine was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(3-(trifluoromethoxy)phenyl)cyclopropyl)imidazo[1,2-b]pyridazine. ES/MS m/z: 458.20 [M+1].

Intermediate 177. 6-(2,4-dimethoxypyrimidin-5-yl)-8-((1S,2S)-2-(4-(trifluoromethoxy)phenyl)cyclopropyl)imidazo[1,2-b]pyridazine

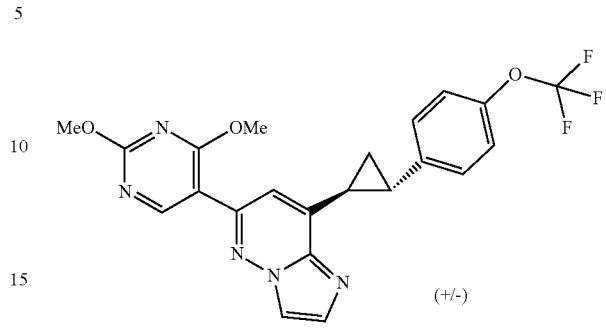

(+/-)

6-(2,4-dimethoxypyrimidin-5-yl)-8-((1S,2S)-2-(4-(trifluoromethoxy)phenyl)cyclopropyl)imidazo[1,2-b]pyridazine was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(4-(trifluoromethoxy)phenyl)cyclopropyl)imidazo[1,2-b]pyridazine. ES/MS m/z: 458.20 [M+1].

Intermediate 178. 8-((2S,2S)-2-(2,2-difluorobenzo[d][1,3]dioxol-5-yl)cyclopropyl)-6-(2,4-dimethoxypyrimidin-5-yl)imidazo[1,2-b]pyridazine

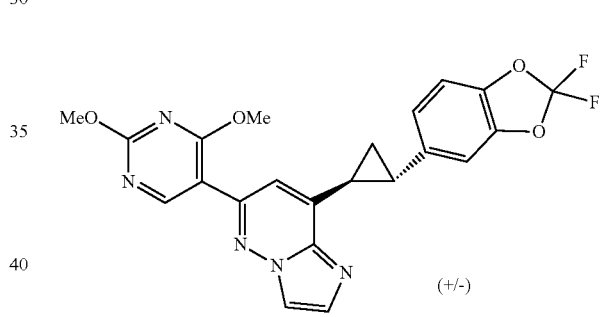

(+/-)

8-((1S,2S)-2-(2,2-difluorobenzo[d][1,3]dioxol-5-yl)cyclopropyl)-6-(2,4-dimethoxypyrimidin-5-yl)imidazo[1,2-b]pyridazine was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(2,2-difluorobenzo[d][1,3]dioxol-5-yl)cyclopropyl)imidazo[1,2-b]pyridazine. ES/MS m/z: 454.20 [M+1].

Intermediate 179. 4-(((1R,2S)-2-(6-(2,4-dimethoxypyrimidin-5-yl)imidazo[1,2-b]pyridazin-8-yl)cyclopropyl)methyl)benzonitrile

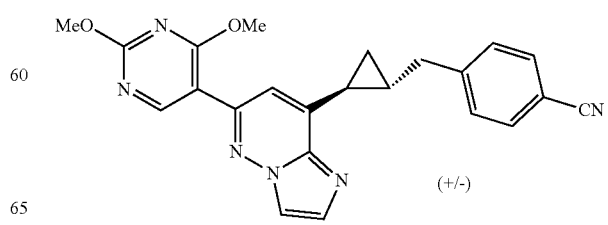

(+/-)

4-(((1R,2S)-2-(6-(2,4-dimethoxypyrimidin-5-yl)imidazo[1,2-b]pyridazin-8-yl)cyclopropyl)methyl)benzonitrile was prepared in the manner described for Intermediate 174, but replacing 6-chloro-8-(3,3,4,4-tetrafluoropyrrolidin-1-yl)imidazo[1,2-b]pyridazine with 4-(((1R,2S)-2-(6-chloroimidazo[1,2-b]pyridazin-8-yl)cyclopropyl)methyl)benzonitrile. ES/MS m/z: 413.20 [M+1].

Synthesis of Heterocycles via Pyridazine Cyclization

Intermediate 180. (Z)-N-(4-bromo-6-chloro-pyridazin-3-yl)-N'-hydroxyformimidamide

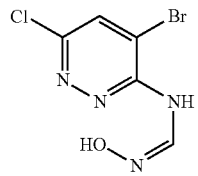 [SMILES: O/N=C\Nc1nnc(Cl)cc1Br]

To a mixture of 4-bromo-6-chloro-pyridazin-3-amine (200 mg, 0.959 mmol) in dry iPrOH (2 mL) was added N,N-dimethylformamide dimethyl acetal (0.332 mL, 2.49 mmol). The mixture was heated to 80° C. and stirred for 3 h. The mixture was then cooled to rt, and hydroxylamine hydrochloride (100 mg, 1.44 mmol) was added. The mixture was heated to 50° C. and stirred for another 3 h. The reaction mixture was quenched with 10% NaHCO$_3$ solution and extracted with 2-MeTHF (2×5 mL). Combined organics were dried over MgSO$_4$, filtered, and concentrated in vacuo. The resulting residue was purified by silica gel chromatography (0-100% EtOAc/hexanes) to afford N-(4-bromo-6-chloropyridazin-3-yl)-N'-hydroxyformimidamide.

ES/MS m/z: 251.0 [M+1]. $^1$H NMR (400 MHz, DMSO-d$_6$) δ 10.99 (s, 1H), 8.39 (d, J=1.2 Hz, 1H), 8.24 (d, J=9.6 Hz, 1H), 8.04 (d, J=9.4 Hz, 1H).

Intermediate 181. 8-bromo-6-chloro-[1,2,4]triazolo[1,5-b]pyridazine

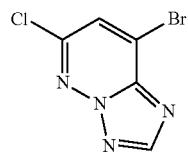

To a mixture of N-(4-bromo-6-chloropyridazin-3-yl)-N'-hydroxyformimidamide (44 mg, 0.175 mmol) in THF (0.5 mL) was added T3P (50% in EtOAc, 0.156 mL, 0.262 mmol). The mixture was heated to 55° C. and stirred for 2 h. The mixture was quenched with 10% NaHCO$_3$ solution and extracted with EtOAc (2×5 mL). Combined organics were dried over MgSO$_4$, filtered, and concentrated in vacuo. The resulting residue was purified by silica gel chromatography (0-100% EtOAc/hexanes) to afford 8-bromo-6-chloro-[1,2,4]triazolo[1,5-b]pyridazine. ES/MS m/z: 233.0 [M+1]. $^1$H NMR (400 MHz, DMSO-d6) δ 8.76 (s, 1H), 8.41 (s, 1H).

Intermediate 182. 6-chloro-8-(7,7-difluoro-5-azaspiro[2.4]heptan-5-yl)-[1,2,4]triazolo[1,5-b]pyridazine

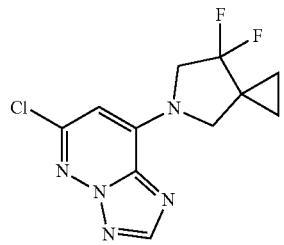 [SMILES: FC1(F)CN(c2cc(Cl)nn3ncnc23)CC12CC2]

To a mixture of 8-bromo-6-chloro-[1,2,4]triazolo[1,5-b]pyridazine (37 mg, 0.158 mmol) and 7,7-difluoro-5-azaspiro[2.4]heptane (23 mg, 0.174 mmol) in MeCN (1 mL) was added N,N-diisopropylethylamine (0.036 mL, 0.206 mmol). The mixture was stirred for 30 min at rt, then heated to 40° C. and stirred for 1 h. The mixture was then concentrated in vacuo and the resulting residue was purified by silica gel chromatography (0-100% EtOAc/hexanes) to afford 6-chloro-8-(7,7-difluoro-5-azaspiro[2.4]heptan-5-yl)-[1,2,4]triazolo[1,5-b]pyridazine. ES/MS m/z: 286.1 [M+1].

Intermediate 183. 6-chloro-8-(7,7-difluoro-5-azaspiro[2.4]heptan-5-yl)imidazo[1,2-b]pyridazine

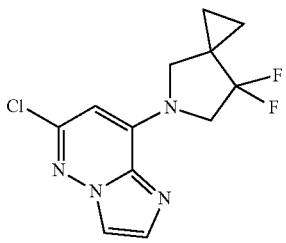 [SMILES: FC1(F)CN(c2cc(Cl)nn3ccnc23)CC12CC2]

A solution of 8-bromo-6-chloro-imidazo[1,2-b]pyridazine (250 mg, 1.08 mmol), 7,7-difluoro-5-azaspiro[2.4]heptane hydrochloride (158 mg, 1.18 mmol), and N,N-diisopropylethylamine (0.22 mL, 1.29 mmol) in MeCN (3 mL) was heated to 85° C. After 2 hours, the reaction mixture was directly purified by SiO$_2$ chromatography (0-80% EtOAc/Hex), 6-chloro-8-(7,7-difluoro-5-azaspiro[2.4]heptan-5-yl)imidazo[1,2-b]pyridazine. ES/MS m/z: 285.10 [M+H].

Intermediate 184. 6-chloro-8-(3,3-difluoro-4,4-dimethyl-pyrrolidin-1-yl)-3-fluoro-imidazo[1,2-b]pyridazine

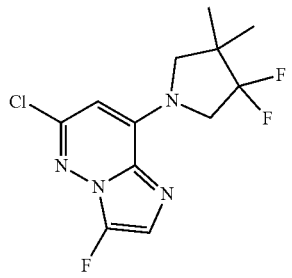 [SMILES: CC1(C)CN(c2cc(Cl)nn3c(F)cnc23)CC1(F)F]

6-chloro-8-(3,3-difluoro-4,4-dimethyl-pyrrolidin-1-yl)-3-fluoro-imidazo[1,2-b]pyridazine was prepared in the manner described for Intermediate 59, but replacing 3,3-dimethylpyrrolidine hydrochloride with 3,3-difluoro-4,4-dimethyl-pyrrolidine hydrochloride and 8-bromo-6-chloroimidazo[1,2-b]pyridazine with 8-bromo-6-chloro-3-fluoro-imidazo[1,2-b]pyridazine. ES/MS m/z: 305.10 [M+H].

Intermediate 185. 6-chloro-8-(7,7-difluoro-5-azaspiro[2.4]heptan-5-yl)-3-fluoroimidazo[1,2-b]pyridazine

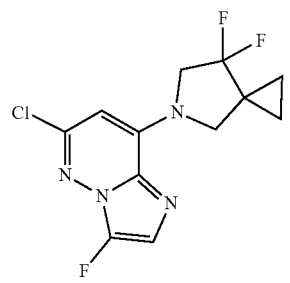 [SMILES: Fc1cnc2c(N3CC(F)(F)C4(CC4)C3)cc(Cl)nn12]

A solution of 8-bromo-6-chloro-3-fluoroimidazo[1,2-b]pyridazine (250 mg, 1 mmol, 1 equiv), 7,7-difluoro-5-azaspiro[2.4]heptane hydrochloride (146 mg, 1.1 mmol, 1.1 equiv), and N,N-diisopropylethylamine (0.42 mL, 2.4 mmol, 2.4 equiv) in MeCN (5 mL, 0.2M) was heated to 85° C. After 7 hours, the reaction mixture was directly purified by $SiO_2$ chromatography (0-80% EtOAc/Hex), affording 6-chloro-8-(7,7-difluoro-5-azaspiro[2.4]heptan-5-yl)-3-fluoroimidazo[1,2-b]pyridazine. ES/MS m/z: 303.10 [M+H].

Intermediate 186. 8-(7,7-difluoro-5-azaspiro[2.4]hentan-5-yl)-6-(2,4-dimethoxypyrimidin-5-yl)-[1,2,4]triazolo[1,5-b]pyridazine

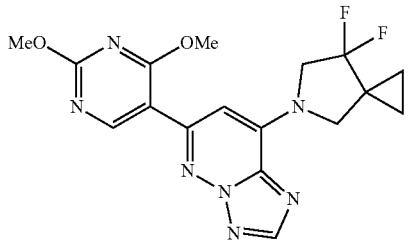 [SMILES: COc1ncc(-c2cc(N3CC(F)(F)C4(CC4)C3)c3ncnn3n2)c(OC)n1]

8-(7,7-difluoro-5-azaspiro[2.4]heptan-5-yl)-6-(2,4-dimethoxypyrimidin-5-yl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-(7,7-difluoro-5-azaspiro[2.4]heptan-5-yl)[1,2,4]triazolo[1,5-b]pyridazine. ES/MS m/z: 390.2 [M+1].

Intermediate 187. 8-(7,7-difluoro-5-azaspiro[2.4]heptan-5-yl)-6-(2,4-dimethoxypyrimidin-5-yl)imidazo[1,2-b]pyridazine

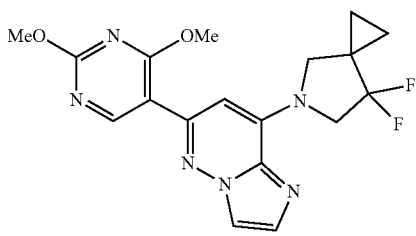 [SMILES: COc1ncc(-c2cc(N3CC(F)(F)C4(CC4)C3)c3nccn3n2)c(OC)n1]

8-(7,7-difluoro-5-azaspiro[2.4]heptan-5-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(7,7-difluoro-5-azaspiro[2.4]heptan-5-yl)imidazo[1,2-b]pyridazine. ES/MS m/z: 389.20 [M+H].

Intermediate 188. 8-(3,3-difluoro-4,4-dimethyl-pyrrolidin-1-yl)-6-(2,4-dimethoxypyrimidin-5-yl)-3-fluoro-imidazo[1,2-b]pyridazine

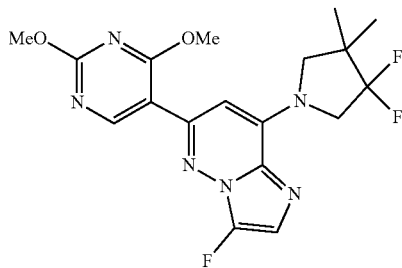 [SMILES: COc1ncc(-c2cc(N3CC(C)(C)C(F)(F)C3)c3ncc(F)n3n2)c(OC)n1]

8-(3,3-difluoro-4,4-dimethyl-pyrrolidin-1-yl)-6-(2,4-dimethoxypyrimidin-5-yl)-3-fluoro-imidazo[1,2-b]pyridazine was prepared in the manner described for Intermediate 134, but replacing 6-chloro-8-cyclopropyl-3-fluoro-imidazo[1,2-b]pyridazine with 6-chloro-8-(3,3-difluoro-4,4-dimethyl-pyrrolidin-1-yl)-3-fluoro-imidazo[1,2-b]pyridazine. ES/MS m/z: 409.20 [M+H].

Intermediate 189. 8-(7,7-difluoro-5-azaspiro[2.4]heptan-5-yl)-6-(2,4-dimethoxypyrimidin-5-yl)-3-fluoroimidazo[1,2-b]pyridazine

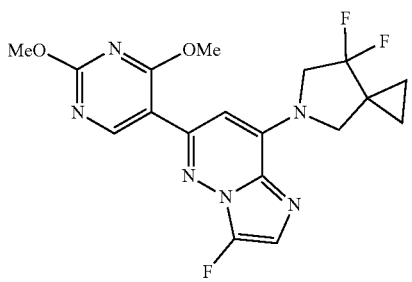 [SMILES: COc1ncc(-c2cc(N3CC(F)(F)C4(CC4)C3)c3ncc(F)n3n2)c(OC)n1]

8-(7,7-difluoro-5-azaspiro[2.4]heptan-5-yl)-6-(2,4-dimethoxypyrimidin-5-yl)-3-fluoroimidazo[1,2-b]pyridazine was prepared in the manner described for Intermediate 18, but replacing 6-chloro-8-cyclopropyl-2-methyl-imidazo[1,2-b]pyridazine with 6-chloro-8-(7,7-difluoro-5-azaspiro[2.4]heptan-5-yl)-3-fluoroimidazo[1,2-b]pyridazine. ES/MS m/z: 407.20 [M+H].

Intermediate 190.
6-bromo-1-(2,2-difluoroethyl)indazole

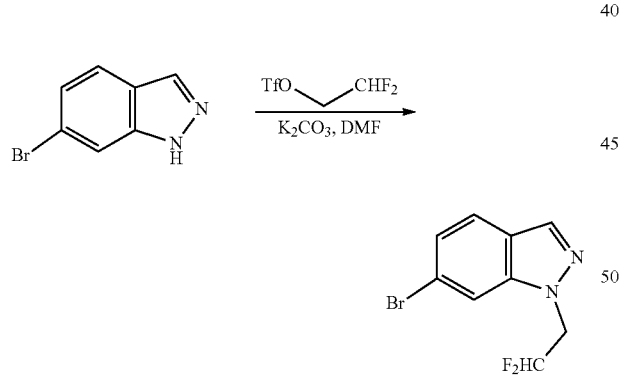

To a solution of 6-bromo-1H-indazole (1 g, 5.05 mmol, 1 equiv) in DMF (20 mL) was added potassium carbonate (2104 mg, 15.2 mmol, 3 equiv) and 2,2-difluoroethyl trifluoromethanesulfonate (1.63 g, 7.61 mmol, 1.5 equiv). The reaction mixture was heated to 80° C. After 2 hours, the reaction mixture was diluted with brine (50 mL) and extracted with EtOAc. The combined organic layers were dried over Na₂SO₄, filtered, and concentrated.

Purification was accomplished by SiO₂ chromatography (0-100% EtOAc/Hex), affording 6-bromo-1-(2,2-difluoroethyl)indazole. ES/MS m/z: 261.10 [M+H].

Intermediate 191.
6-bromo-3-fluoro-1-(2,2,2-trifluoroethyl)indazole

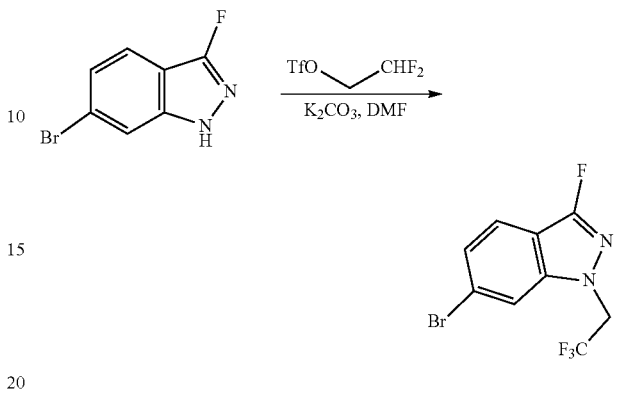

To a solution of 6-bromo-3-fluoro-1H-indazole (0.59 g, 2.74 mmol, 1 equiv) in DMF (4 mL) was added potassium carbonate (1138 mg, 8.23 mmol, 3 equiv) and 2,2,2-trifluoroethyl trifluoromethanesulfonate (955 mg, 4.12 mmol, 1.5 equiv). The reaction mixture was heated to 80° C. After 1 hour, the reaction mixture was diluted with brine (50 mL) and extracted with EtOAc. The combined organic layers were dried over Na₂SO₄, filtered, and concentrated. Purification was accomplished by SiO₂ chromatography (0-50% EtOAc/Hex), affording 6-bromo-3-fluoro-1-(2,2,2-trifluoroethyl)indazole. ES/MS m/z: 297.10 [M+H].

Intermediate 192.
6-bromo-1-(2,2-difluoroethyl)-7-fluoro-indazole

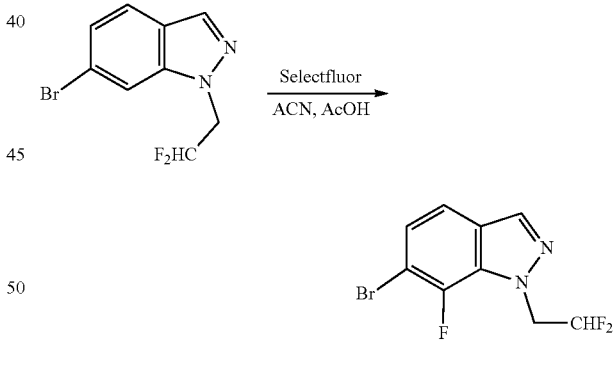

To a solution of 6-bromo-1-(2,2-difluoroethyl)indazole (0.3 g, 1.15 mmol, 1 equiv) in ACN (5 mL) and acetic acid (0.25 mL) was added N-Fluoro-N'-chloromethyltriethylenediamine (814 mg, 2.3 mmol, 2 equiv). The reaction mixture was heated to 90° C. After 16 hours, the reaction mixture was directly purified by RP-HPLC (10-90% MeCN/H₂O with TFA modifier). Pure fractions were combined and concentrated. Residue obtained was diluted with water, neutralized with aqueous sodium sulfate and extracted with DCM. Organic layer was separated, dried over sodium sulfate, filtered and concentrated. Solids obtained was dried at high vacuum overnight affording 6-bromo-1-(2,2-difluoroethyl)-7-fluoro-indazole. ES/MS m/z: 279.10 [M+H].

Intermediate 193. 6-bromo-3-fluoro-1H-indazole

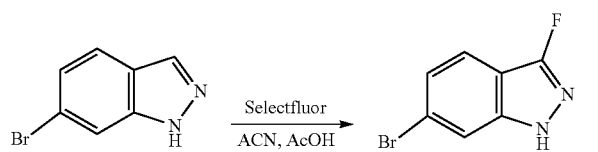 [SMILES: Brc1ccc2cn[nH]c2c1 ; Fc1n[nH]c2cc(Br)ccc12]

To a solution of 6-bromo-1H-indazole (4.4 g, 22.3 mmol, 1 equiv) in ACN (60 mL) and acetic acid (3 mL) was added N-Fluoro-N'-chloromethyltriethylenediamine (15.82 g, 44.7 mmol, 2 equiv). The reaction mixture was heated to 90° C. After 16 hours, the reaction mixture was directly purified by RP-HPLC (10-90% MeCN/H$_2$O with TFA modifier). Pure fractions were combined and concentrated. Residue obtained was diluted with water, neutralized with aqueous sodium sulfate and extracted with DCM. Organic layer was separated, dried over sodium sulfate, filtered and concentrated. Solids obtained was dried at high vacuum overnight affording 6-bromo-3-fluoro-1H-indazole. ES/MS m/z: 215.00 [M+H].

Intermediate 194. 6-bromo-2-(cyclopropylmethyl)indazole

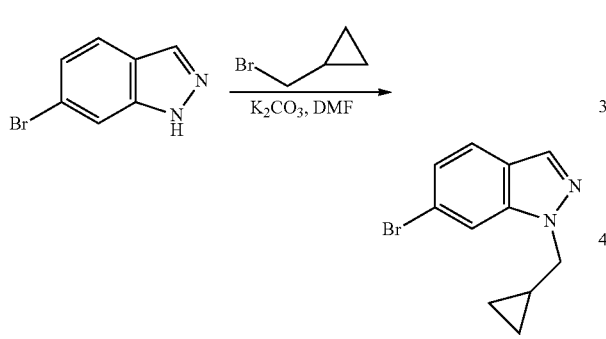

To a solution of 6-bromo-1H-indazole (1 g, 5.05 mmol, 1 equiv) in DMF (20 mL) was added potassium carbonate (2104 mg, 15.2 mmol, 3 equiv) and bromomethylcyclopropane (1.03 g, 7.61 mmol, 1.5 equiv). The reaction mixture was heated to 80° C. After 2 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-1-(cyclopropylmethyl)indazole. ES/MS m/z: 251.10 [M+H].

Intermediate 195. 6-bromo-1-(2,2,2-trifluoroethyl)pyrrolo[3,2-c]pyridine

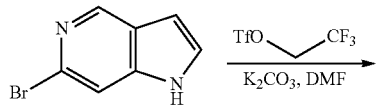

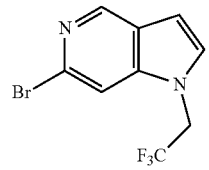

To a solution of 6-bromo-1H-pyrrolo[3,2-c]pyridine (1 g, 5.08 mmol, 1 equiv) in DMF (20 mL) was added potassium carbonate (2104 mg, 15.2 mmol, 3 equiv) and 2,2,2-trifluoroethyl trifluoromethanesulfonate (1.77 g, 7.61 mmol, 1.5 equiv). The reaction mixture was heated to 80° C. After 2 hours, the reaction mixture was diluted with brine (50 mL) and extracted with EtOAc. The combined organic layers were dried over Na$_2$SO$_4$, filtered, and concentrated.

Purification was accomplished by SiO$_2$ chromatography (0-100% EtOAc/Hex), affording 6-bromo-1-(2,2,2-trifluoroethyl)pyrrolo[3,2-c]pyridine. ES/MS m/z: 279.00 [M+H].

Intermediate 196. 6-bromo-1-(2,2,2-trifluoroethyl)pyrrolo[2,3-b]pyridine

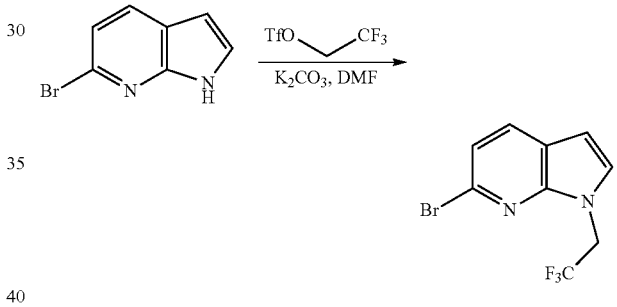

To a solution of 6-bromo-1H-pyrrolo[2,3-b]pyridine (1 g, 5.08 mmol, 1 equiv) in DMF (20 mL) was added potassium carbonate (2104 mg, 15.2 mmol, 3 equiv) and 2,2,2-trifluoroethyl trifluoromethanesulfonate (1.77 g, 7.61 mmol, 1.5 equiv). The reaction mixture was heated to 80° C. After 2 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-1-(2,2,2-trifluoroethyl)pyrrolo[2,3-b]pyridine. ES/MS m/z: 279.00 [M+H].

Intermediate 197. 6-bromo-3-cyclopropyl-1-(2,2,2-trifluoroethyl)indazole

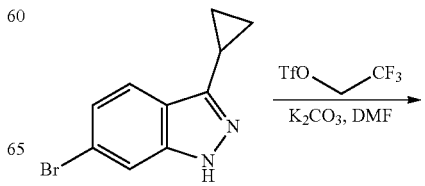

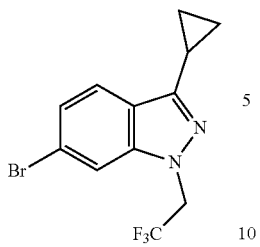

To a solution of 6-bromo-3-cyclopropyl-1H-indazole (1 g, 4.22 mmol, 1 equiv) in DMF (20 mL) was added potassium carbonate (1749 mg, 12.7 mmol, 3 equiv) and 2,2,2-trifluoroethyl trifluoromethanesulfonate (1.77 g, 7.61 mmol, 1.5 equiv). The reaction mixture was heated to 80° C. After 3 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-3-cyclopropyl-1-(2,2,2-trifluoroethyl)indazole. ES/MS m/z: 319.20 [M+H].

Intermediate 198. 6-bromo-2-[(2,2-difluorocyclopropyl)methyl]indazole

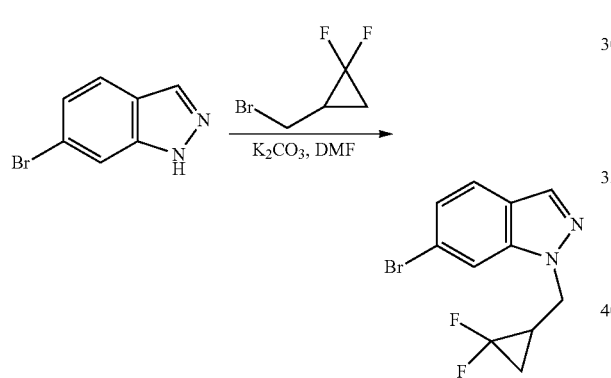

To a solution of 6-bromo-1H-indazole (0.5 g, 2.54 mmol, 1 equiv) in DMF (8 mL) was added potassium carbonate (877 mg, 6.34 mmol, 2.5 equiv) and 2-(bromomethyl)-1,1-difluoro-cyclopropane (521 mg, 3.05 mmol, 1.2 equiv). The reaction mixture was heated to 80° C. After 3 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-2-[(2,2-difluorocyclopropyl)methyl]indazole. ES/MS m/z: 287.00 [M+H].

Intermediate 199. 6-bromo-3-fluoro-1-(2,2,2-trifluoroethyl)pyrrolo[3,2-c]pyridine

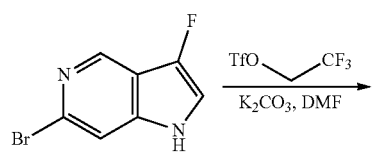

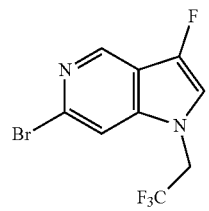

To a solution of 6-bromo-3-fluoro-1H-pyrrolo[3,2-c]pyridine (0.5 g, 2.33 mmol, 1 equiv) in DMF (8 mL) was added potassium carbonate (964 mg, 6.98 mmol, 3 equiv) and 2,2,2-trifluoroethyl trifluoromethanesulfonate (1767 mg, 7.61 mmol, 1.5 equiv). The reaction mixture was heated to 80° C. After 3 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-3-fluoro-1-(2,2,2-trifluoroethyl)pyrrolo[3,2-c]pyridine. ES/MS m/z: 297.00 [M+H].

Intermediate 200. 6-bromo-3-isopropyl-1-(2,2,2-trifluoroethyl)indazole

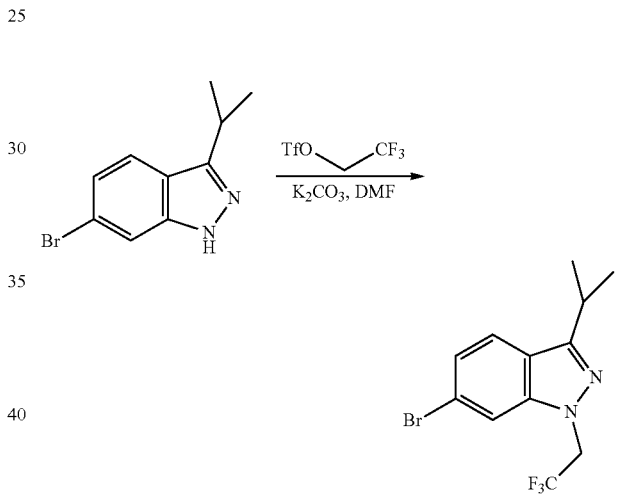

To a solution of 6-bromo-3-isopropyl-1H-indazole (0.5 g, 2.09 mmol, 1 equiv) in DMF (8 mL) was added potassium carbonate (867 mg, 6.27 mmol, 3 equiv) and 2,2,2-trifluoroethyl trifluoromethanesulfonate (883 mg, 3.81 mmol, 1.5 equiv). The reaction mixture was heated to 80° C. After 3 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-3-isopropyl-1-(2,2,2-trifluoroethyl)indazole. ES/MS m/z: 321.20 [M+H].

Intermediate 201. 6-bromo-4-(2,2,2-trifluoroethoxy)isouuinoline

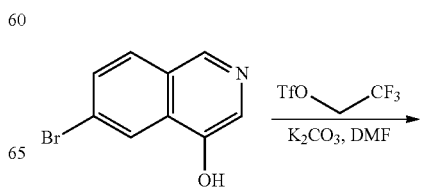

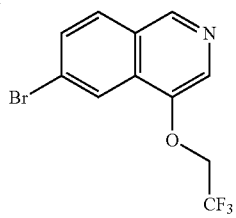

To a solution of 6-bromoisoquinolin-4-ol (0.5 g, 2.23 mmol, 1 equiv) in DMF (5 mL) was added potassium carbonate (925 mg, 6.69 mmol, 3 equiv) and 2,2,2-trifluoroethyl trifluoromethanesulfonate (777 mg, 3.35 mmol, 1.5 equiv). The reaction mixture was heated to 80° C. After 3 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-4-(2,2,2-trifluoroethoxy)isoquinoline. ES/MS m/z: 306.00 [M+H]; $^1$H NMR (400 MHz, Chloroform-d) δ 8.98 (s, 1H), 8.42-8.37 (m, 1H), 8.13 (s, 1H), 7.87 (d, J=8.7 Hz, 1H), 7.78 (dd, J=8.7, 1.9 Hz, 1H), 4.63 (q, J=7.9 Hz, 2H). $^{19}$F NMR (376 MHz, Chloroform-d) δ −74.28 (t, J=7.9 Hz).

Intermediate 202. 6-bromo-4-(2,2,2-trifluoroethoxy)quinoline and 6-bromo-1-(2,2,2-trifluoroethyl)quinolin-4-one

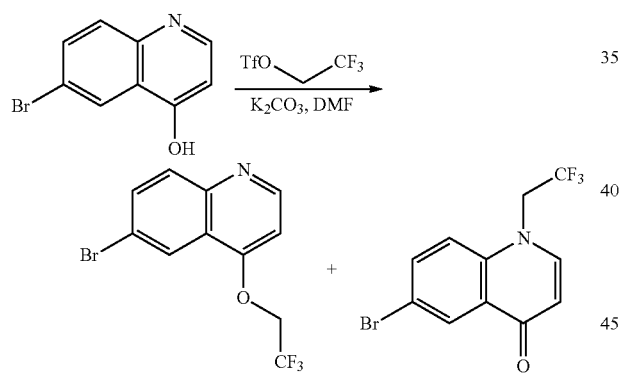

To a solution of 6-bromoquinolin-4-ol (1 g, 4.46 mmol, 1 equiv) in DMF (10 mL) was added potassium carbonate (1851 mg, 13.4 mmol, 3 equiv) and 2,2,2-trifluoroethyl trifluoromethanesulfonate (1554 mg, 6.69 mmol, 1.5 equiv). The reaction mixture was heated to 80° C. After 3 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-4-(2,2,2-trifluoroethoxy)quinoline ES/MS m/z: 306.00 [M+H]; 1H NMR (400 MHz, Chloroform-d) δ 8.82 (d, J=5.1 Hz, 1H), 8.38 (d, J=2.2 Hz, 1H), 7.96 (d, J=9.0 Hz, 1H), 7.84 (dd, J=9.0, 2.2 Hz, 1H), 6.76 (d, J=5.1 Hz, 1H), 4.61 (q, J=7.8 Hz, 2H); 19F NMR (376 MHz, Chloroform-d) δ −73.90 (t, J=7.9 Hz) and 6-bromo-1-(2,2,2-trifluoroethyl)quinolin-4-one ES/MS m/z: 306.00 [M+H]; $^1$H NMR (400 MHz, Chloroform-d) δ 8.60 (d, J=2.4 Hz, 1H), 7.79 (dd, J=9.1, 2.4 Hz, 1H), 7.50 (d, J=7.9 Hz, 1H), 7.32 (d, J=9.1 Hz, 1H), 6.37 (d, J=7.9 Hz, 1H), 4.65 (q, J=8.0 Hz, 2H); $^{19}$F NMR (376 MHz, Chloroform-d) δ −70.63 (t, J=8.0 Hz).

Intermediate 203. 7-bromo-2-(2,2,2-trifluoroethyl)isoquinolin-1-one

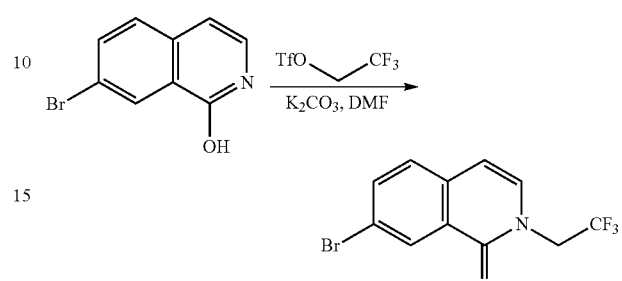

To a solution of 7-bromoisoquinolin-1-ol (1 g, 4.46 mmol, 1 equiv) in DMF (10 mL) was added potassium carbonate (1851 mg, 13.4 mmol, 3 equiv) and 2,2,2-trifluoroethyl trifluoromethanesulfonate (1554 mg, 6.69 mmol, 1.5 equiv). The reaction mixture was heated to 80° C. After 3 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 7-bromo-2-(2,2,2-trifluoroethyl)isoquinolin-1-one. ES/MS m/z: 306.00 [M+H]; $^1$H NMR (400 MHz, Chloroform-d) δ 8.60 (d, J=2.1 Hz, 1H), 7.79 (dd, J=8.5, 2.2 Hz, 1H), 7.43 (d, J=8.4 Hz, 1H), 7.10 (dd, J=7.4, 1.1 Hz, 1H), 6.53 (d, J=7.5 Hz, 1H), 4.68 (q, J=8.6 Hz, 2H); $^{19}$F NMR (376 MHz, Chloroform-d) δ −71.09 (t, J=8.7 Hz).

Intermediate 204. 6-bromo-3,3-dimethyl-1-(2,2,2-trifluoroethyl)indolin-2-one

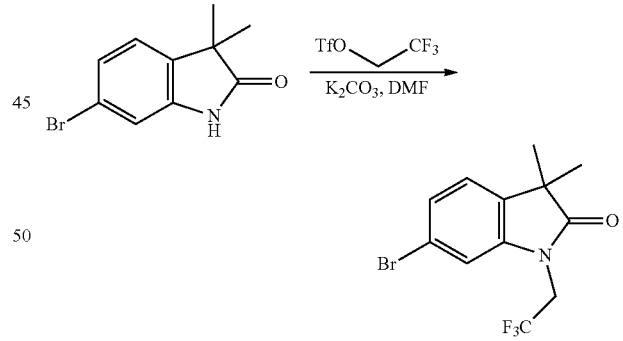

To a solution of 6-bromo-3,3-dimethyl-indolin-2-one (0.877 g, 3.65 mmol, 1 equiv) in DMF (10 mL) was added potassium carbonate (1514 mg, 11 mmol, 3 equiv) and 2,2,2-trifluoroethyl trifluoromethanesulfonate (1450 mg, 6.25 mmol, 1.5 equiv). The reaction mixture was heated to 80° C. After 20 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 7 6-bromo-3,3-dimethyl-1-(2,2,2-trifluoroethyl)indolin-2-one. ES/MS m/z: 322.00 [M+H]

Intermediate 205. 6-bromo-3,3-dimethyl-1-(2,2,2-trifluoroethyl)pyrrolo[3,2-b]pyridin-2-one

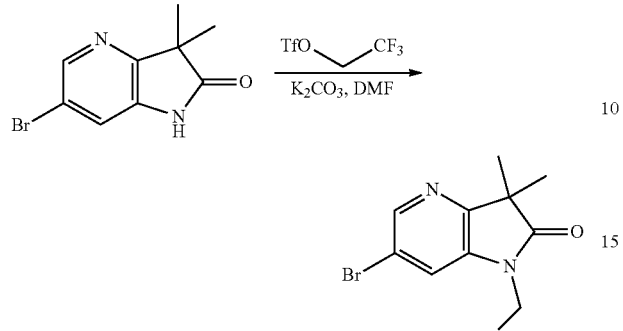

To a solution of 6-bromo-3,3-dimethyl-1H-pyrrolo[3,2-b]pyridin-2-one (0.5 g, 2.07 mmol, 1 equiv) in DMF (4 mL) was added potassium carbonate (860 mg, 6.22 mmol, 3 equiv) and 2,2,2-trifluoroethyl trifluoromethanesulfonate (722 mg, 3.11 mmol, 1.5 equiv). The reaction mixture was heated to 80° C. After 2 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-bromo-3,3-dimethyl-1-(2,2,2-trifluoroethyl)pyrrolo[3,2-b]pyridin-2-one. ES/MS m/z: 323.00 [M+H]

Intermediate 206. 6-chloro-3,3-dimethyl-1-(2,2,2-trifluoroethyl)pyrrolo[3,2-c]pyridin-2-one

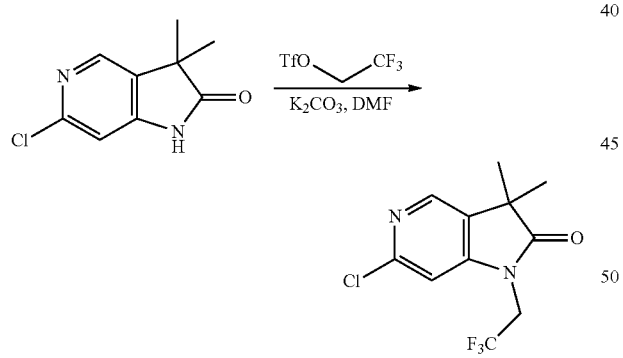

To a solution of 6-chloro-3,3-dimethyl-1H-pyrrolo[3,2-c]pyridin-2-one (0.25 g, 1.27 mmol, 1 equiv) in DMF (8 mL) was added potassium carbonate (527 mg, 3.81 mmol, 3 equiv) and 2,2,2-trifluoroethyl trifluoromethanesulfonate (443 mg, 1.91 mmol, 1.5 equiv). The reaction mixture was heated to 80° C. After 2 hours, the reaction mixture was diluted with brine (50 mL) and extracted with EtOAc. The combined organic layers were dried over Na$_2$SO$_4$, filtered, and concentrated. Purification was accomplished by SiO$_2$ chromatography (0-100% EtOAc/Hex), affording 6-chloro-3,3-dimethyl-1-(2,2,2-trifluoroethyl)pyrrolo[3,2-c]pyridin-2-one. ES/MS m/z: 279.10 [M+H]

Intermediate 207. N-(4,4-difluoropyrrolidin-3-yl)acetamide; hydrochloride

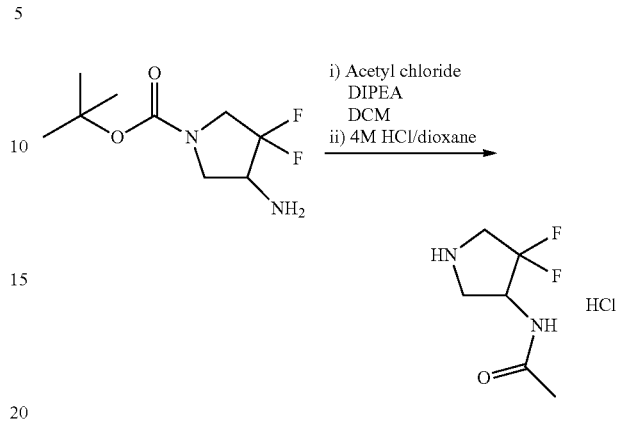

To an ice cold solution of tert-butyl 4-amino-3,3-difluoropyrrolidine-1-carboxylate (0.1 g, 0.45 mmol, 1 equiv) in DCM (2 mL) was added N,N-Diisopropylethylamine (0.086 mL, 0.495 mmol, 1.1 equiv) and acetyl chloride (0.035 mL, 0.495 mmol, 1.1 equiv). After stirring at 0° C. for 20 min, the reaction mixture was treated with 4M HCl/dioxane (10 mL) and was further stirred for 4 h at room temperature. The reaction mixture was concentrated and residue obtained was dried at high vacuum overnight to afford N-(4,4-difluoropyrrolidin-3-yl)acetamide; hydrochloride. ES/MS m/z: 201.20 [M+H].

Intermediate 208. 2,2,2-trifluoroethyl N-(4,4-difluoropyrrolidin-3-yl)carbamate; hydrochloride

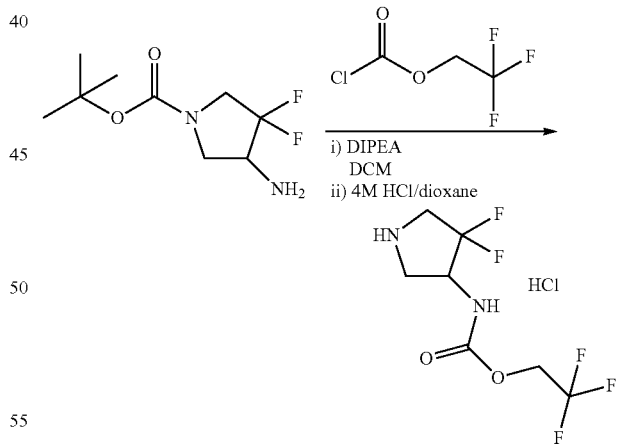

To an ice cold solution of tert-butyl 4-amino-3,3-difluoropyrrolidine-1-carboxylate (0.258 g, 1.16 mmol, 1 equiv) in DCM (5 mL) was added N,N-Diisopropylethylamine (0.243 mL, 1.39 mmol, 1.2 equiv) and 2,2,2-trifluoroethyl carbonochloridate (0.201 g, 1.24 mmol, 1.07 equiv). After stirring at 0° C. for 20 min, the reaction mixture was purified by SiO$_2$ chromatography (0-50% EtOAc/Hex). Fractions were combined and concentrated. The residue obtained was treated with 4M HCl/dioxane (10 mL) and was further stirred for 8 h at room temperature. The reaction mixture was concentrated and was dried at high vacuum overnight to afford 2,2,2-trifluoroethyl N-(4,4-difluoropyrrolidin-3-yl)carbamate; hydrochloride. ES/MS m/z: 249.10 [M+H].

Intermediate 209. cyclopropylmethyl N-(4,4-difluoropyrrolidin-3-yl)carbamate; hydrochloride

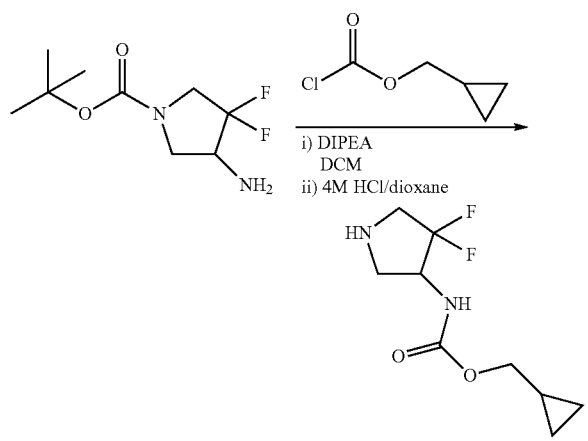

To an ice cold solution of tert-butyl 4-amino-3,3-difluoropyrrolidine-1-carboxylate (0.25 g, 1.12 mmol, 1 equiv) in DCM (5 mL) was added N,N-Diisopropylethylamine (0.24 mL, 1.35 mmol, 1.2 equiv) and cyclopropylmethyl carbonochloridate (0.167 g, 1.24 mmol, 1.1 equiv). After stirring at 0° C. for 20 min, the reaction mixture was purified by SiO₂ chromatography (0-50% EtOAc/Hex). Fractions were combined and concentrated. The residue obtained was treated with 4M HCl/dioxane (10 mL) and was further stirred for 8 h at room temperature. The reaction mixture was concentrated and was dried at high vacuum overnight to afford cyclopropylmethyl N-(4,4-difluoropyrrolidin-3-yl) carbamate; hydrochloride. ES/MS m/z: 221.10 [M+H].

Intermediate 210. 2,2-difluoroethyl N-(4,4-difluoropyrrolidin-3-yl)carbamate; hydrochloride

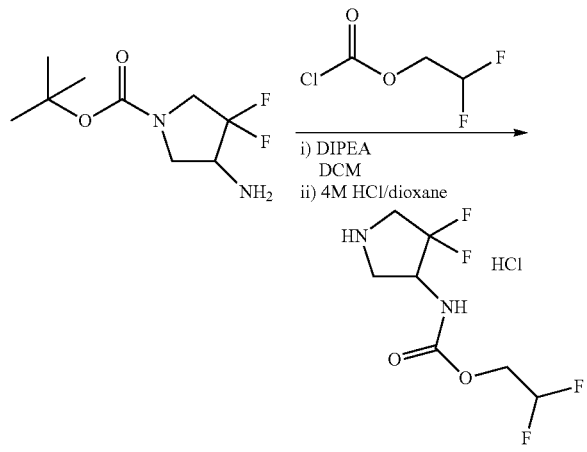

To an ice cold solution of tert-butyl 4-amino-3,3-difluoropyrrolidine-1-carboxylate (0.285 g, 1.28 mmol, 1 equiv) in DCM (5 mL) was added N,N-Diisopropylethylamine (0.29 mL, 1.67 mmol, 1.3 equiv) and 2,2-difluoroethyl carbonochloridate (0.222 g, 1.54 mmol, 1.2 equiv). After stirring at 0° C. for 20 min, the reaction mixture was purified by SiO₂ chromatography (0-50% EtOAc/Hex). Fractions were combined and concentrated. The residue obtained was treated with 4M HCl/dioxane (10 mL) and was further stirred for 8 h at room temperature. The reaction mixture was concentrated and was dried at high vacuum overnight to afford 2,2-difluoroethyl N-(4,4-difluoropyrrolidin-3-yl)carbamate; hydrochloride. ES/MS m/z: 231.10 [M+H].

Intermediate 211. N-(4,4-difluoropyrrolidin-3-yl)benzamide; hydrochloride

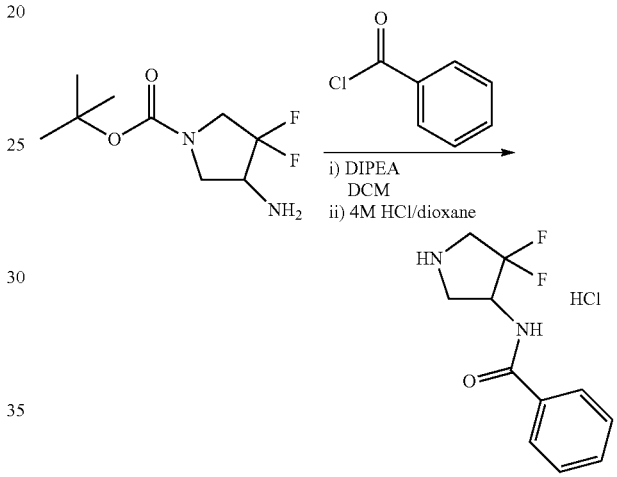

To an ice cold solution of tert-butyl 4-amino-3,3-difluoropyrrolidine-1-carboxylate (0.1 g, 0.45 mmol, 1 equiv) in DCM (5 mL) was added N,N-Diisopropylethylamine (0.09 mL, 0.5 mmol, 1.1 equiv) and benzoyl chloride (0.07 g, 0.5 mmol, 1.1 equiv). After stirring at 0° C. for 20 min, the reaction mixture was purified by SiO₂ chromatography (0-50% EtOAc/Hex). Fractions were combined and concentrated. The residue obtained was treated with 4M HCl/dioxane (10 mL) and was further stirred for 8 h at room temperature. The reaction mixture was concentrated and was dried at high vacuum overnight to afford N-(4,4-difluoropyrrolidin-3-yl)benzamide; hydrochloride. ES/MS m/z: 227.20 [M+H].

Intermediate 212. N-(4,4-difluoropyrrolidin-3-yl)-4-(trifluoromethyl)benzamide; hydrochloride

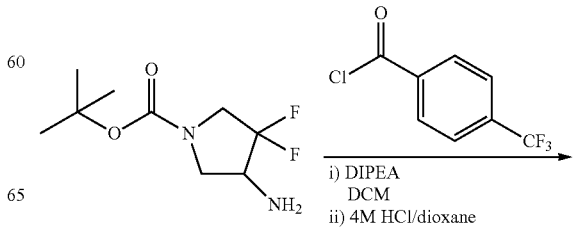

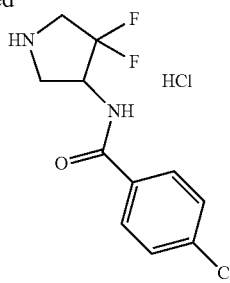

To an ice cold solution of tert-butyl 4-amino-3,3-difluoropyrrolidine-1-carboxylate (0.175 g, 0.79 mmol, 1 equiv) in DCM (5 mL) was added N,N-Diisopropylethylamine (0.15 mL, 0.87 mmol, 1.1 equiv) and 4-(trifluoromethyl)benzoyl chloride (0.18 g, 0.87 mmol, 1.1 equiv). After stirring at 0° C. for 20 min, the reaction mixture was purified by SiO₂ chromatography (0-50% EtOAc/Hex). Fractions were combined and concentrated. The residue obtained was treated with 4M HCl/dioxane (10 mL) and was further stirred for 8 h at room temperature. The reaction mixture was concentrated and was dried at high vacuum overnight to afford N-(4,4-difluoropyrrolidin-3-yl)-4-(trifluoromethyl)benzamide; hydrochloride. ES/MS m/z: 295.10 [M+H].

Intermediate 213. N-(4,4-difluoropyrrolidin-3-yl)-5-(trifluoromethyl)pyridine-2-carboxamide; hydrochloride

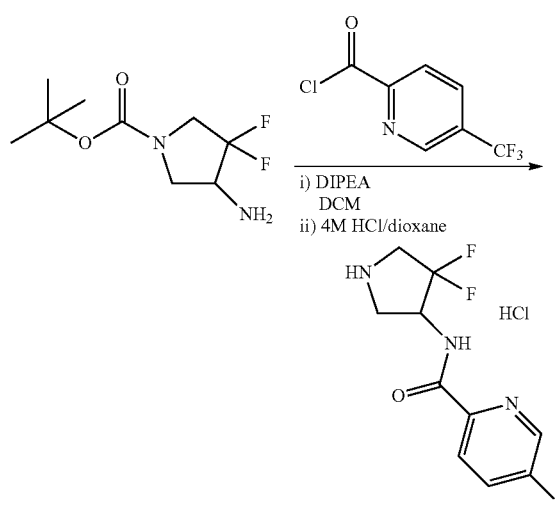

To an ice cold solution of tert-butyl 4-amino-3,3-difluoropyrrolidine-1-carboxylate (0.2 g, 0.9 mmol, 1 equiv) in DCM (5 mL) was added N,N-Diisopropylethylamine (0.17 mL, 0.99 mmol, 1.1 equiv) and 5-(trifluoromethyl)pyridine-2-carbonyl chloride (0.18 g, 0.87 mmol, 0.96 equiv). After stirring at 0° C. for 20 min, the reaction mixture was purified by SiO₂ chromatography (0-70% EtOAc/Hex). Fractions were combined and concentrated. The residue obtained was treated with 4M HCl/dioxane (10 mL) and was further stirred for 8 h at room temperature. The reaction mixture was concentrated and was dried at high vacuum overnight to afford N-(4,4-difluoropyrrolidin-3-yl)-5-(trifluoromethyl)pyridine-2-carboxamide; hydrochloride. ES/MS m/z: 296.10 [M+H].

Intermediate 214. 6-bromo-1-(2,2,2-trifluoroethyl)-3-(trifluoromethyl)pyrrolo[2,3-b]pyridine

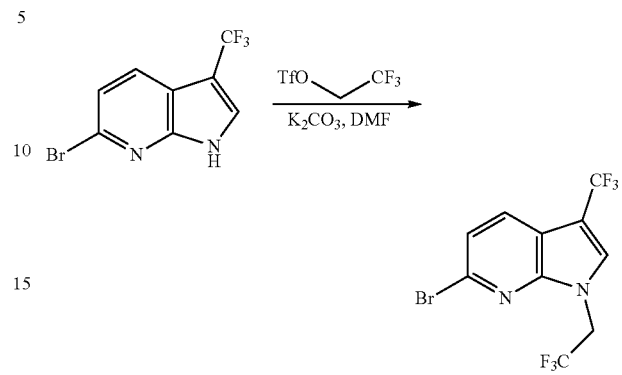

To a solution of 6-bromo-3-(trifluoromethyl)-1H-pyrrolo[2,3-b]pyridine (0.5 g, 1.89 mmol, 1 equiv) in DMF (4 mL) was added potassium carbonate (782 mg, 5.66 mmol, 3 equiv) and 2,2,2-trifluoroethyl trifluoromethanesulfonate (0.66 g, 2.83 mmol, 1.5 equiv). The reaction mixture was heated to 80° C. After 3 hours, the reaction mixture was diluted with brine (50 mL) and extracted with EtOAc. The combined organic layers were dried over Na₂SO₄, filtered, and concentrated. Purification was accomplished by SiO₂ chromatography (0-100% EtOAc/Hex), affording 6-bromo-1-(2,2,2-trifluoroethyl)-3-(trifluoromethyl)pyrrolo[2,3-b]pyridine. ¹H NMR (400 MHz, Chloroform-d) δ 7.95 (dt, J=8.3, 0.8 Hz, 1H), 7.63 (s, 1H), 7.45 (d, J=8.3 Hz, 1H), 4.94 (q, J=8.5 Hz, 2H). ¹⁹F NMR (376 MHz, Chloroform-d) δ −58.46, −71.77 (t, J=8.6 Hz).

Intermediate 215. 4-[(1S,2S)-2-(4,4,5,5-tetramethyl-1,3,2-dioxaborolan-2-yl)cyclopropyl]benzonitrile

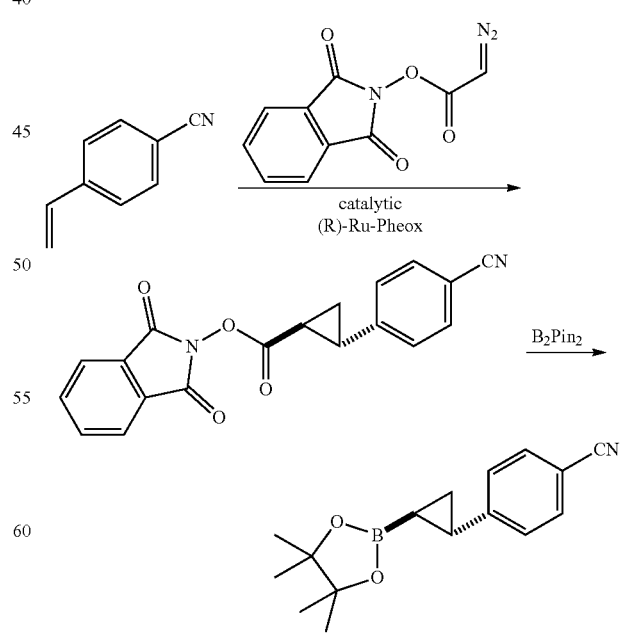

Step 1: To a cooled (0° C.) solution of 4-vinylbenzonitrile (1000 mg, 7.74 mmol, 1 equiv) and Ru(II)-(R)-Pheox catalyst [Tetrakis(acetonitrile)[2-[(4R)-4,5-dihydro-4-phenyl-2-oxazolyl-N]phenyl]ruthenium(II) Hexafluorophosphate](49 mg, 1 mol %) in CH$_2$Cl$_2$ (78 mL, 0.1M) was added a 0.2M solution of 1,3-dioxoisoindolin-2-yl 2-diazoacetate (1969 mg, 8.52 mmol, 1.1 equiv) in CH$_2$Cl$_2$ over 40 minutes. After an additional 3 hours at 0° C., the reaction mixture was diluted with MeOH (5 mL) and concentrated to 10 mL. Purification was accomplished by SiO$_2$ chromatography (0-70% EtOAc/Hex), affording (1,3-dioxoisoindolin-2-yl) (1S,2S)-2-(4-cyanophenyl)cyclopropanecarboxylate. ES/MS m/z: 333.10 [M+H].

Step 2: To a solution of 1 (1,3-dioxoisoindolin-2-yl) (1S,2S)-2-(4-cyanophenyl)cyclopropanecarboxylate (1140 mg, 3.43 mmol, 1 equiv) in EtOAc (15 mL) was added B2Pin2 (1742 mg, 6.86 mmol, 2 equiv) and methyl isonicotinate (0.2 mL, 1.72 mmol, 0.5 equiv). The resulting mixture was heated to 80° C. under an atmosphere of argon. After 16 hours, the reaction mixture was filtered, concentrated, and purified by SiO$_2$ chromatography (0-40% EtOAc/Hex), affording 4-[(1S,2S)-2-(4,4,5,5-tetramethyl-1,3,2-dioxaborolan-2-yl)cyclopropyl]benzonitrile. ES/MS m/z: 270.10 [M+H].

Intermediate 216. 3,3-dimethyl-6-[(1S,2S)-2-(4,4,5,5-tetramethyl-1,3,2-dioxaborolan-2-yl)cyclopropyl]-1-(2,2,2-trifluoroethyl)indolin-2-one Step 1: 6-bromo-3,3-dimethyl-1-(2,2,2-trifluoroethyl)indolin-2-one (2000 mg, 6.21 mmol, 1 equiv), vinyl trifluoroborate (873 mg, 6.52 mmol, 1.05 equiv), potassium carbonate (1890 mg, 13.7 mmol, 2.2 equiv), and (dppf)PdCl$_2$—CH$_2$Cl$_2$ (454 mg, 10 mol %) in 9:1 THF/H$_2$O (10 mL) was heated to 85° C. After 20 hours, the reaction mixture was cooled to room temperature and purification was accomplished by SiO$_2$ chromatography (0-100% EtOAc/Hex), affording 3,3-dimethyl-1-(2,2,2-trifluoroethyl)-6-vinyl-indolin-2-one. ES/MS m/z: 270.10 [M+H].

Step 2: To a cooled (0° C.) solution of 3,3-dimethyl-1-(2,2,2-trifluoroethyl)-6-vinyl-indolin-2-one (1425 mg, 5.29 mmol, 1 equiv) and Ru(II)-(R)-Pheox catalyst [Tetrakis(acetonitrile) [2-[(4R)-4,5-dihydro-4-phenyl-2-oxazolyl-N]phenyl]ruthenium(II) Hexafluorophosphate](167 mg, 5 mol %) in CH$_2$Cl$_2$ (30 mL) was added a 0.2M solution of 1,3-dioxoisoindolin-2-yl 2-diazoacetate (1346 mg, 5.82 mmol, 1.1 equiv) in CH$_2$Cl$_2$ over 3 h. After an additional 1 hour at 0° C., the reaction mixture was diluted with MeOH (1 mL) and concentrated to 10 mL. Purification was accomplished by SiO$_2$ chromatography (0-100% EtOAc/Hex), affording (1,3-dioxoisoindolin-2-yl) (1S,2S)-2-[3,3-dimethyl-2-oxo-1-(2,2,2-trifluoroethyl)indolin-6-yl]cyclopropanecarboxylate. ES/MS m/z: 473.20 [M+H].

Step 3: To a solution of 1 (1,3-dioxoisoindolin-2-yl) (1S,2S)-2-[3,3-dimethyl-2-oxo-1-(2,2,2-trifluoroethyl)indolin-6-yl]cyclopropanecarboxylate (2318 mg, 4.91 mmol, 1 equiv) in EtOAc (25 mL) was added B2Pin2 (1869 mg, 7.36 mmol, 1.5 equiv) and methyl isonicotinate (0.29 mL, 2.45 mmol, 0.5 equiv). The resulting mixture was heated to 80° C. under an atmosphere of argon. After 4 hours, the reaction mixture was filtered, concentrated, and purified by SiO$_2$ chromatography (0-50% EtOAc/Hex), affording 3,3-dimethyl-6-[(1S,2S)-2-(4,4,5,5-tetramethyl-1,3,2-dioxaborolan-2-yl)cyclopropyl]-1-(2,2,2-trifluoroethyl)indolin-2-one. ES/MS m/z: 410.20 [M+H].

Intermediate 217. 3-fluoro-6-[(1S,2S)-2-(4,4,5,5-tetramethyl-1,3,2-dioxaborolan-2-yl)cyclopropyl]-1-(2,2,2-trifluoroethyl)indazole

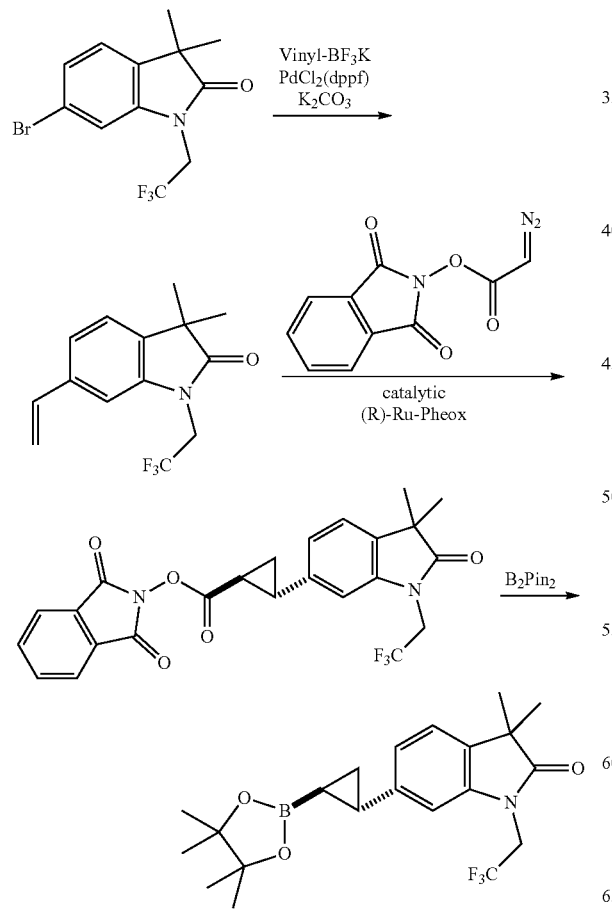

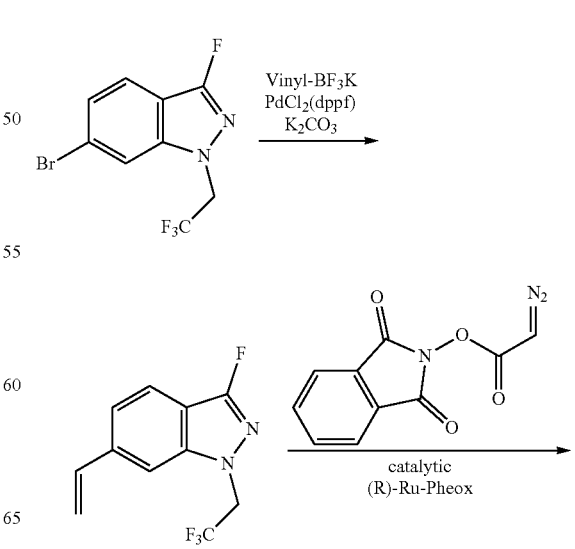

-continued

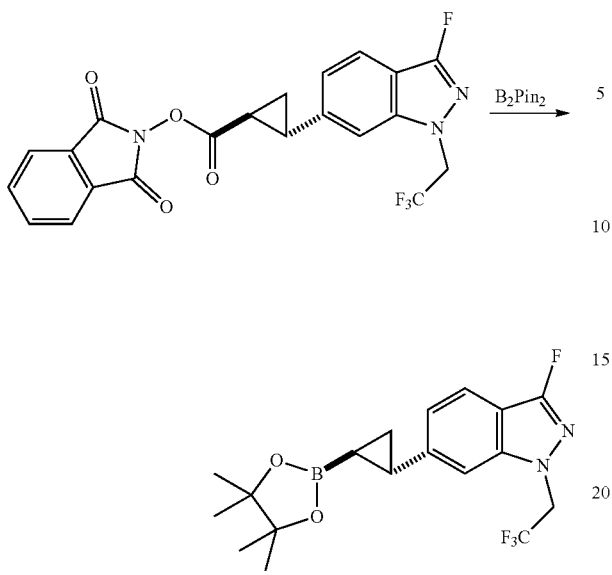

Step 1: 6-bromo-3-fluoro-1-(2,2,2-trifluoroethyl)indazole (1420 mg, 4.78 mmol, 1 equiv), vinyl trifluoroborate (672 mg, 5.02 mmol, 1.05 equiv), potassium carbonate (1450 mg, 10.5 mmol, 2.2 equiv), and (dppf)PdCl$_2$—CH$_2$Cl$_2$ (350 mg, 10 mol %) in 9:1 THF/H$_2$O (10 mL) was heated to 85° C. After 20 hours, the reaction mixture was cooled to room temperature and purification was accomplished by SiO$_2$ chromatography (0-50% EtOAc/Hex), affording 3-fluoro-1-(2,2,2-trifluoroethyl)-6-vinyl-indazole. $^1$H NMR (400 MHz, Chloroform-d) δ 7.65 (d, J=8.5 Hz, 1H), 7.39 (dd, J=8.4, 1.2 Hz, 1H), 7.29 (d, J=2.0 Hz, 1H), 6.86 (dd, J=17.5, 10.9 Hz, 1H), 5.91 (d, J=17.5 Hz, 1H), 5.44 (d, J=10.9 Hz, 1H), 4.79 (qd, J=8.3, 1.0 Hz, 2H). $^{19}$F NMR (376 MHz, Chloroform-d) δ −71.42 (t, J=8.3 Hz), −132.61.

Step 2: To a cooled (0° C.) solution of 3-fluoro-1-(2,2,2-trifluoroethyl)-6-vinyl-indazole (780 mg, 3.19 mmol, 1 equiv) and Ru(II)-(R)-Pheox catalyst [Tetrakis(acetonitrile) [2-[(4R)-4,5-dihydro-4-phenyl-2-oxazolyl-N]phenyl]ruthenium(II) Hexafluorophosphate](101 mg, 5 mol %) in CH$_2$Cl$_2$ (18 mL) was added a 0.2M solution of 1,3-dioxoisoindolin-2-yl 2-diazoacetate (812 mg, 3.51 mmol, 1.1 equiv) in CH$_2$Cl$_2$ over 2 h. After an additional 1 hour at 0° C., the reaction mixture was diluted with MeOH (1 mL) and concentrated to ~10 mL. Purification was accomplished by SiO$_2$ chromatography (0-100% EtOAc/Hex), affording (1,3-dioxoisoindolin-2-yl) (1S,2S)-2-[3-fluoro-1-(2,2,2-trifluoroethyl)indazol-6-yl]cyclopropanecarboxylate. ES/MS m/z: 448.20 [M+H].

Step 3: To a solution of (1,3-dioxoisoindolin-2-yl) (1S, 2S)-2-[3-fluoro-1-(2,2,2-trifluoroethyl)indazol-6-yl]cyclopropanecarboxylate (1328 mg, 2.97 mmol, 1 equiv) in EtOAc (12 mL) was added B2Pin2 (1131 mg, 4.45 mmol, 1.5 equiv) and methyl isonicotinate (0.29 mL, 2.45 mmol, 0.5 equiv). The resulting mixture was heated to 80° C. under an atmosphere of argon. After 4 hours, the reaction mixture was filtered, concentrated, and purified by SiO$_2$ chromatography (0-50% EtOAc/Hex), affording 3-fluoro-6-[(1S,2S)-2-(4,4,5,5-tetramethyl-1,3,2-dioxaborolan-2-yl)cyclopropyl]-1-(2,2,2-trifluoroethyl)indazole. ES/MS m/z: 385.20 [M+H].

Intermediate 218. 6-chloro-3-fluoro-8-[(1S,2S)-2-[4-(trifluoromethyl)phenyl]cyclopropyl]imidazo[1,2-b]pyridazine

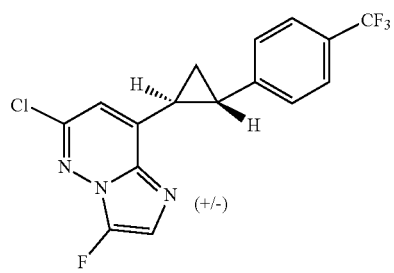 [SMILES: Fc1cnc2c([C@H]3C[C@@H]3c3ccc(C(F)(F)F)cc3)cc(Cl)nn12]

6-chloro-3-fluoro-8-[(1S,2S)-2-[4-(trifluoromethyl)phenyl]cyclopropyl]imidazo[1,2-b]pyridazine (Racemic Mixture) was prepared in the manner described for Intermediate 5, but replacing racemic 4,4,5,5-tetramethyl-2-((2S,2S)-2-phenylcyclopropyl)-1,3,2-dioxaborolane with 4,4,5,5-tetramethyl-2-[(1S,2S)-2-[4-(trifluoromethyl)phenyl]cyclopropyl]-1,3,2-dioxaborolane (Racemic Mixture) and 8-bromo-6-chloroimidazo[1,2-b]pyridazine with 8-bromo-6-chloro-3-fluoroimidazo[1,2-b]pyridazine. ES/MS m/z: 356.10 [M+H].

Intermediate 219. 5-[(1S,2S)-2-(6-chloroimidazo[1,2-b]pyridazin-8-yl)cyclopropyl]-1-methyl-pyridin-2-one

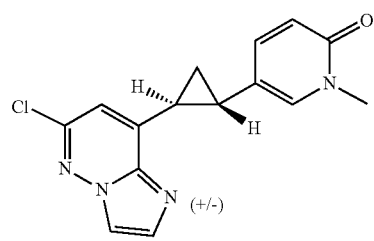 [SMILES: Cn1cc([C@H]2C[C@@H]2c2cc(Cl)nn3ccnc23)ccc1=O]

5-[(1S,2S)-2-(6-chloroimidazo[1,2-b]pyridazin-8-yl)cyclopropyl]-1-methyl-pyridin-2-one (Racemic Mixture) was prepared in the manner described for Intermediate 5, but replacing racemic 4,4,5,5-tetramethyl-2-((1S,2S)-2-phenylcyclopropyl)-1,3,2-dioxaborolane with 1-methyl-5-[(1S,2S)-2-(4,4,5,5-tetramethyl-1,3,2-dioxaborolan-2-yl)cyclopropyl]pyridin-2-one (Racemic Mixture). ES/MS m/z: 301.10 [M+H].

Intermediate 220. 6-chloro-8-[(1S,2S)-2-(4-chlorophenyl)cyclopropyl]-3-fluoro-imidazo[1,2-b]pyridazine

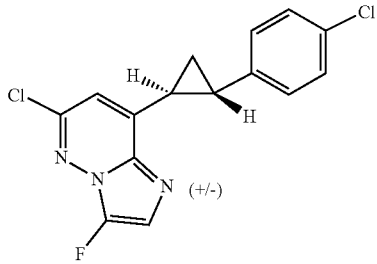 [SMILES: Fc1cnc2c([C@H]3C[C@@H]3c3ccc(Cl)cc3)cc(Cl)nn12]

6-chloro-8-[(1S,2S)-2-(4-chlorophenyl)cyclopropyl]-3-fluoro-imidazo[1,2-b]pyridazine (Racemic Mixture) was prepared in the manner described for Intermediate 5, but replacing racemic 4,4,5,5-tetramethyl-2-((1S,2S)-2-phenylcyclopropyl)-1,3,2-dioxaborolane with 2-[(1S,2S)-2-(4-chlorophenyl)cyclopropyl]-4,4,5,5-tetramethyl-1,3,2-dioxaborolane (Racemic Mixture) and 8-bromo-6-chloroimidazo[1,2-b]pyridazine with 8-bromo-6-chloro-3-fluoroimidazo[1,2-b]pyridazine. ES/MS m/z: 322.10 [M+H].

Intermediate 221. 6-chloro-3-fluoro-8-[(1S,2S)-2-(4-pyridyl)cyclopropyl]imidazo[1,2-b]pyridazine

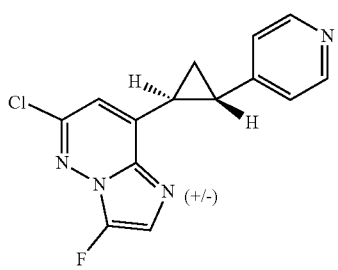 [SMILES: Fc1cnc2c([C@H]3C[C@@H]3c3ccncc3)cc(Cl)nn12]

6-chloro-3-fluoro-8-[(1S,2S)-2-(4-pyridyl)cyclopropyl]imidazo[1,2-b]pyridazine (Racemic Mixture) was prepared in the manner described for Intermediate 5, but replacing racemic 4,4,5,5-tetramethyl-2-((1S,2S)-2-phenylcyclopropyl)-1,3,2-dioxaborolane with 4-[(1S,2S)-2-(4,4,5,5-tetramethyl-1,3,2-dioxaborolan-2-yl)cyclopropyl]pyridine (Racemic Mixture) and 8-bromo-6-chloroimidazo[1,2-b]pyridazine with 8-bromo-6-chloro-3-fluoroimidazo[1,2-b]pyridazine. ES/MS m/z: 289.10 [M+H].

Intermediate 222. 6-chloro-3-fluoro-8-[(1S,2S)-2-(3-pyridyl)cyclopropyl]imidazo[1,2-b]pyridazine

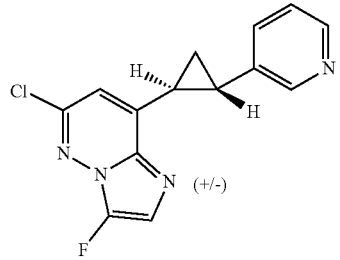 [SMILES: Fc1cnc2c([C@H]3C[C@@H]3c3cccnc3)cc(Cl)nn12]

6-chloro-3-fluoro-8-[(1S,2S)-2-(3-pyridyl)cyclopropyl]imidazo[1,2-b]pyridazine (Racemic Mixture) was prepared in the manner described for Intermediate 5, but replacing racemic 4,4,5,5-tetramethyl-2-((2S,2S)-2-phenylcyclopropyl)-1,3,2-dioxaborolane with 3-[(1S,2S)-2-(4,4,5,5-tetramethyl-1,3,2-dioxaborolan-2-yl)cyclopropyl]pyridine (Racemic Mixture) and 8-bromo-6-chloroimidazo[1,2-b]pyridazine with 8-bromo-6-chloro-3-fluoroimidazo[1,2-b]pyridazine. ES/MS m/z: 289.10 [M+H].

Intermediate 223. 6-chloro-3-fluoro-8-[(1S,2S)-2-pyrimidin-5-ylcyclopropyl]imidazo[1,2-b]pyridazine

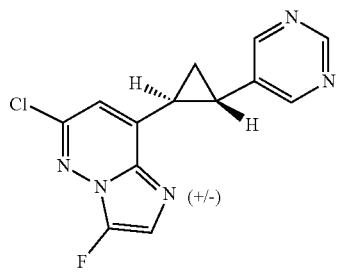 [SMILES: Fc1cnc2c([C@H]3C[C@@H]3c3cncnc3)cc(Cl)nn12]

6-chloro-3-fluoro-8-[(1S,2S)-2-pyrimidin-5-ylcyclopropyl]imidazo[1,2-b]pyridazine (Racemic Mixture) was prepared in the manner described for Intermediate 5, but replacing racemic 4,4,5,5-tetramethyl-2-((2S,2S)-2-phenylcyclopropyl)-1,3,2-dioxaborolane with 5-[(1S,2S)-2-(4,4,5,5-tetramethyl-1,3,2-dioxaborolan-2-yl)cyclopropyl]pyrimidine (racemic mixture) and 8-bromo-6-chloroimidazo[1,2-b]pyridazine with 8-bromo-6-chloro-3-fluoroimidazo[1,2-b]pyridazine. ES/MS m/z: 290.10[M+H].

Intermediate 224. 6-chloro-3-fluoro-8-[(1S,2S)-2-(2-pyridyl)cyclopropyl]imidazo[1,2-b]pyridazine

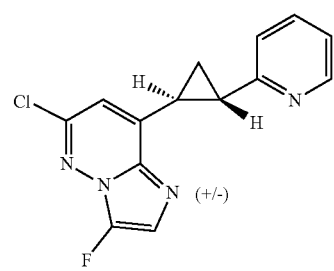 [SMILES: Fc1cnc2c([C@H]3C[C@@H]3c3ccccn3)cc(Cl)nn12]

6-chloro-3-fluoro-8-[(1S,2S)-2-(2-pyridyl)cyclopropyl]imidazo[1,2-b]pyridazine (Racemic Mixture) was prepared in the manner described for Intermediate 5, but replacing racemic 4,4,5,5-tetramethyl-2-((2S,2S)-2-phenylcyclopropyl)-1,3,2-dioxaborolane with 2-[(1S,2S)-2-(4,4,5,5-tetramethyl-1,3,2-dioxaborolan-2-yl)cyclopropyl]pyridine (Racemic Mixture) and 8-bromo-6-chloroimidazo[1,2-b]pyridazine with 8-bromo-6-chloro-3-fluoroimidazo[1,2-b]pyridazine. ES/MS m/z: 289.10 [M+H].

Intermediate 225. Ethyl 6-chloro-8-[(1S,2S)-2-(4-fluorophenyl)cyclopropyl]imidazo[1,2-b]pyridazine-2-carboxylate

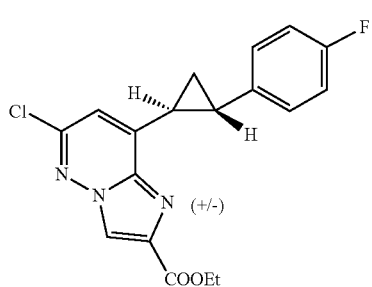 [SMILES: CCOC(=O)c1cn2nc(Cl)cc([C@H]3C[C@@H]3c3ccc(F)cc3)c2n1]

Ethyl 6-chloro-8-[(1S,2S)-2-(4-fluorophenyl)cyclopropyl]imidazo[1,2-b]pyridazine-2-carboxylate (Racemic Mixture) was prepared in the manner described for Intermediate 5, but replacing racemic 4,4,5,5-tetramethyl-2-((2S,2S)-2-phenylcyclopropyl)-1,3,2-dioxaborolane with 2-[(1S,2S)-2-(4-fluorophenyl)cyclopropyl]-4,4,5,5-tetramethyl-1,3,2-dioxaborolane (Racemic Mixture) and 8-bromo-6-chloroimidazo[1,2-b]pyridazine with ethyl 8-bromo-6-chloroimidazo[1,2-b]pyridazine-2-carboxylate. ES/MS m/z: 360.10 [M+H].

Intermediate 226. 5-[(1S,2S)-2-(6-chloroimidazo[1,2-b]pyridazin-8-1/1)cyclopropyl]isoquinoline

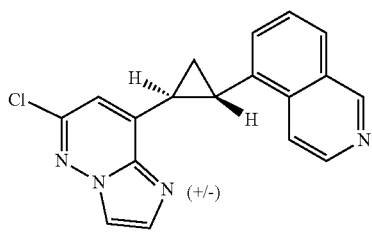 [SMILES: Clc1cc([C@H]2C[C@@H]2c2cccc3cnccc23)c2nccn2n1]

5-[(1S,2S)-2-(6-chloroimidazo[1,2-b]pyridazin-8-yl)cyclopropyl]isoquinoline (racemic mixture) was prepared in the manner described for Intermediate 5, but replacing racemic 4,4,5,5-tetramethyl-2-((1S,2S)-2-phenylcyclopropyl)-1,3,2-dioxaborolane with 5-[(1S,2S)-2-(4,4,5,5-tetramethyl-1,3,2-dioxaborolan-2-yl)cyclopropyl]isoquinoline (Racemic Mixture). ES/MS m/z: 321.10 [M+H].

Intermediate 227. 4-[(1S,2S)-2-(6-chloroimidazo[1,2-b]pyridazin-8-1/1)cyclopropyl]quinoline

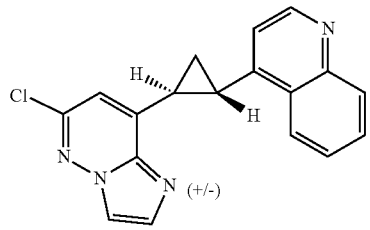 [SMILES: Clc1cc([C@H]2C[C@@H]2c2ccnc3ccccc23)c2nccn2n1]

4-[(1S,2S)-2-(6-chloroimidazo[1,2-b]pyridazin-8-yl)cyclopropyl]quinoline (racemic mixture) was prepared in the manner described for Intermediate 5, but replacing racemic 4,4,5,5-tetramethyl-2-((1S,2S)-2-phenylcyclopropyl)-1,3,2-dioxaborolane with 4-[(1S,2S)-2-(4,4,5,5-tetramethyl-1,3,2-dioxaborolan-2-yl)cyclopropyl]quinoline (Racemic Mixture). ES/MS m/z: 321.10 [M+H].

Intermediate 228. 8-[(1S,2S)-2-(6-chloroimidazo[1,2-b]pyridazin-8-yl)cyclopropyl]isoquinoline

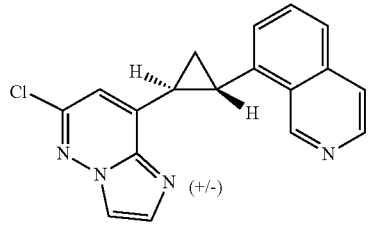 [SMILES: Clc1cc([C@H]2C[C@@H]2c2cccc3ccncc23)c2nccn2n1]

8-[(1S,2S)-2-(6-chloroimidazo[1,2-b]pyridazin-8-yl)cyclopropyl]isoquinoline (racemic mixture) was prepared in the manner described for Intermediate 5, but replacing racemic 4,4,5,5-tetramethyl-2-((1S,2S)-2-phenylcyclopropyl)-1,3,2-dioxaborolane with 8-[(1S,2S)-2-(4,4,5,5-tetramethyl-1,3,2-dioxaborolan-2-yl)cyclopropyl]isoquinoline (Racemic Mixture). ES/MS m/z: 321.10 [M+H].

Intermediate 229. 6-chloro-8-[(1S,2S)-2-[2-fluoro-4-(trifluoromethyl)phenyl]cyclopropyl]imidazo[1,2-b]pyridazine

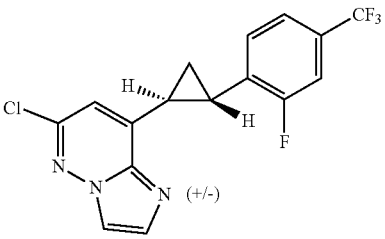 [SMILES: Fc1cc(C(F)(F)F)ccc1[C@H]1C[C@@H]1c1cc(Cl)nn2ccnc12]

6-chloro-8-[(1S,2S)-2-[2-fluoro-4-(trifluoromethyl)phenyl]cyclopropyl]imidazo[1,2-b]pyridazine (Racemic Mixture) was prepared in the manner described for Intermediate 5, but replacing racemic 4,4,5,5-tetramethyl-2-((1S,2S)-2-phenylcyclopropyl)-1,3,2-dioxaborolane with 2-[(1S,2S)-2-

[2-fluoro-4-(trifluoromethyl)phenyl]cyclopropyl]-4,4,5,5-tetramethyl-1,3,2-dioxaborolane (Racemic Mixture). ES/MS m/z: 356.10 [M+H].

Intermediate 230. 6-chloro-8-[(1S,2S)-2-(5-fluoro-3-pyridyl)cyclopropyl]imidazo[1,2-b]pyridazine

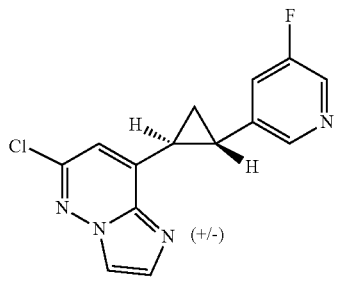 [SMILES: Fc1cncc([C@H]2C[C@@H]2c2cc(Cl)nn3ccnc23)c1]

6-chloro-8-[(1S,2S)-2-(5-fluoro-3-pyridyl)cyclopropyl]imidazo[1,2-b]pyridazine (Racemic Mixture) was prepared in the manner described for Intermediate 5, but replacing racemic 4,4,5,5-tetramethyl-2-((2S,2S)-2-phenylcyclopropyl)-1,3,2-dioxaborolane with 3-fluoro-5-[(1S,2S)-2-(4,4,5,5-tetramethyl-1,3,2-dioxaborolan-2-yl)cyclopropyl]pyridine (racemic mixture). ES/MS m/z: 289.10 [M+H].

Intermediate 231. 6-chloro-8-[(1S,2S)-2-[6-(trifluoromethyl)-3-pyridyl]cyclopropyl]imidazo[1,2-b]pyridazine

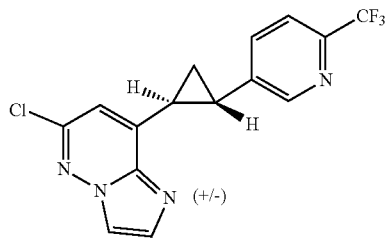 [SMILES: FC(F)(F)c1ccc([C@H]2C[C@@H]2c2cc(Cl)nn3ccnc23)cn1]

6-chloro-8-[(1S,2S)-2-[6-(trifluoromethyl)-3-pyridyl]cyclopropyl]imidazo[1,2-b]pyridazine (Racemic Mixture) was prepared in the manner described for Intermediate 5, but replacing racemic 4,4,5,5-tetramethyl-2-((1S,2S)-2-phenylcyclopropyl)-1,3,2-dioxaborolane with 5-[(1S,2S)-2-(4,4,5,5-tetramethyl-1,3,2-dioxaborolan-2-yl)cyclopropyl]-2-(trifluoromethyl)pyridine (Racemic Mixture). ES/MS m/z: 339.00 [M+H].

Intermediate 232. 3-[(1S,2S)-2-(6-chloroimidazo[1,2-b]pyridazin-8-yl)cyclopropyl]quinoline

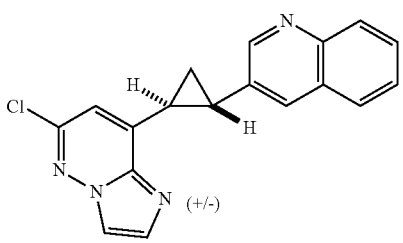 [SMILES: Clc1cc([C@H]2C[C@@H]2c2cnc3ccccc3c2)c2nccn2n1]

3-[(1S,2S)-2-(6-chloroimidazo[1,2-b]pyridazin-8-yl)cyclopropyl]quinoline (racemic mixture) was prepared in the manner described for Intermediate 5, but replacing racemic 4,4,5,5-tetramethyl-2-((2S,2S)-2-phenylcyclopropyl)-1,3,2-dioxaborolane with 3-[(1S,2S)-2-(4,4,5,5-tetramethyl-1,3,2-dioxaborolan-2-yl)cyclopropyl]quinoline (Racemic Mixture). ES/MS m/z: 321.10 [M+H].

Intermediate 233. 6-chloro-8-[(1S,2S)-2-(3-pyridyl)cyclopropyl]imidazo[1,2-b]pyridazine

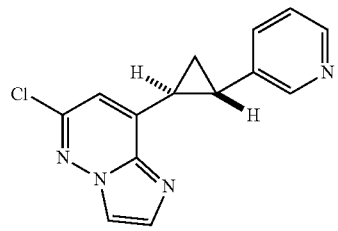 [SMILES: Clc1cc([C@H]2C[C@@H]2c2cccnc2)c2nccn2n1]

6-chloro-8-[(1S,2S)-2-(3-pyridyl)cyclopropyl]imidazo[1,2-b]pyridazine was prepared in the manner described for Intermediate 5, but replacing racemic 4,4,5,5-tetramethyl-2-((1S,2S)-2-phenylcyclopropyl)-1,3,2-dioxaborolane with 3-[(1S,2S)-2-(4,4,5,5-tetramethyl-1,3,2-dioxaborolan-2-yl)cyclopropyl]pyridine. ES/MS m/z: 271.10 [M+H].

Intermediate 234. 6-chloro-8-[(1S,2S)-2-(3-fluoro-4-pyridyl)cyclopropyl]imidazo[1,2-b]pyridazine

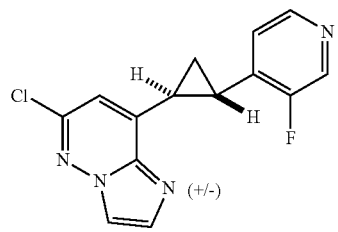 [SMILES: Fc1cnccc1[C@H]1C[C@@H]1c1cc(Cl)nn2ccnc12]

6-chloro-8-[(1S,2S)-2-(3-fluoro-4-pyridyl)cyclopropyl]imidazo[1,2-b]pyridazine (Racemic Mixture) was prepared in the manner described for Intermediate 5, but replacing racemic 4,4,5,5-tetramethyl-2-((2S,2S)-2-phenylcyclopropyl)-1,3,2-dioxaborolane with 3-fluoro-4-[(1S,2S)-2-(4,4,5,5-tetramethyl-1,3,2-dioxaborolan-2-yl)cyclopropyl]pyridine (racemic mixture). ES/MS m/z: 289.10 [M+H].

Intermediate 235. 6-chloro-8-[(1S,2S)-2-[2-(trifluoromethyl)-4-pyridyl]cyclopropyl]imidazo[1,2-b]pyridazine

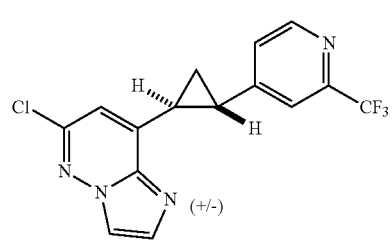 [SMILES: FC(F)(F)c1cc([C@H]2C[C@@H]2c2cc(Cl)nn3ccnc23)ccn1]

6-chloro-8-[(1S,2S)-2-[2-(trifluoromethyl)-4-pyridyl]cyclopropyl]imidazo[1,2-b]pyridazine (Racemic Mixture) was prepared in the manner described for Intermediate 5, but replacing racemic 4,4,5,5-tetramethyl-2-((1S,2S)-2-phenylcyclopropyl)-1,3,2-dioxaborolane with 3[(1S,2S)-2-[2-(trifluoromethyl)-4-pyridyl]cyclopropyl]boronic acid (Racemic Mixture). ES/MS m/z: 339.10 [M+H].

Intermediate 236. 6-chloro-8-[(1S,2S)-2-[5-(trifluoromethyl)-2-pyridyl]cyclopropyl]imidazo[1,2-b]pyridazine

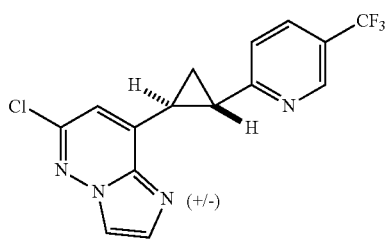 [SMILES: FC(F)(F)c1ccc([C@H]2C[C@@H]2c2cc(Cl)nn3ccnc23)nc1]

6-chloro-8-[(1S,2S)-2-[5-(trifluoromethyl)-2-pyridyl]cyclopropyl]imidazo[1,2-b]pyridazine (Racemic Mixture) was prepared in the manner described for Intermediate 5, but replacing racemic 4,4,5,5-tetramethyl-2-((1S,2S)-2-phenylcyclopropyl)-1,3,2-dioxaborolane with 6-chloro-8-[(1S,2S)-2-[5-(trifluoromethyl)-2-pyridyl]cyclopropyl]imidazo[1,2-b]pyridazine (Racemic Mixture). ES/MS m/z: 339.10 [M+H].

Intermediate 237. 4-[(1S,2S)-2-(6-chloro-3-fluoro-imidazo[1,2-b]pyridazin-8-yl)cyclopropyl]benzonitrile

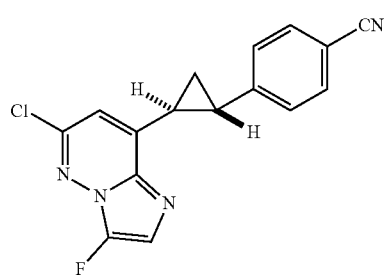 [SMILES: N#Cc1ccc([C@H]2C[C@@H]2c2cc(Cl)nn3c(F)cnc23)cc1]

4-[(1S,2S)-2-(6-chloro-3-fluoro-imidazo[1,2-b]pyridazin-8-yl)cyclopropyl]benzonitrile was prepared in the manner described for Intermediate 5, but replacing racemic 4,4,5,5-tetramethyl-2-((2S,2S)-2-phenylcyclopropyl)-1,3,2-dioxaborolane with 4-[(1S,2S)-2-(4,4,5,5-tetramethyl-1,3,2-dioxaborolan-2-yl)cyclopropyl]benzonitrile. ES/MS m/z: 313.10 [M+H].

Intermediate 238. 4-((1S,2S)-2-(6-chloroimidazo[1,2-b]pyridazin-8-yl)cyclopropyl)-2-(trifluoromethyl)benzonitrile

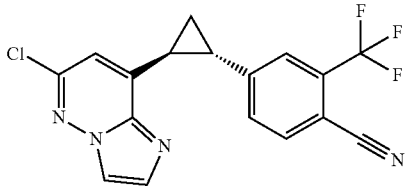 [SMILES: N#Cc1ccc([C@H]2C[C@@H]2c2cc(Cl)nn3ccnc23)cc1C(F)(F)F]

8-bromo-6-chloro-imidazo[1,2-b]pyridazine (124 mg, 0.534 mmol), 4-((2S,2S)-2-(4,4,5,5-tetramethyl-1,3,2-dioxaborolan-2-yl)cyclopropyl)-2-(trifluoromethyl)benzonitrile (150 mg, 0.445 mmol), cataCXium A Pd G3 (32 mg, 0.0445 mmol), and potassium phosphate tribasic (283 mg, 1.33 mmol) were weighed into a microwave vial, which was then evacuated and refilled with N₂ 3 times. Pre-degassed dioxane (2.5 mL) and water (0.5 mL) were added, and the vial was sealed and heated to 110° C. for 3 h. The mixture was then filtered through celite, washing with EtOAc. The filtrate was concentrated in vacuo and purified by silica gel chromatography (0-100% EtOAc in hexanes) to afford 4-((2S,2S)-2-(6-chloroimidazo[1,2-b]pyridazin-8-yl)cyclopropyl)-2-(trifluoromethyl)benzonitrile (Racemic Mixture). ES/MS m/z: 363.1 [M+H].

Intermediate 239. 6-[(1S,2S)-2-(6-chloroimidazo[1,2-b]pyridazin-8-yl)cyclopropyl]isoquinoline

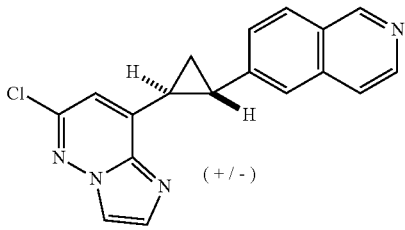

6-[(1S,2S)-2-(6-chloroimidazo[1,2-b]pyridazin-8-yl)cyclopropyl]isoquinoline (racemic mixture) was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitril with 6-[(1S,2S)-2-(4,4,5,5-tetramethyl-1,3,2-dioxaborolan-2-yl)cyclopropyl]isoquinoline (racemic mixture). ES/MS m/z: 321.10 [M+H].

Intermediate 240. 6-[(1S,2S)-2-(6-chloroimidazo[1,2-b]pyridazin-8-yl)cyclopropyl]pyridine-3-carbonitrile

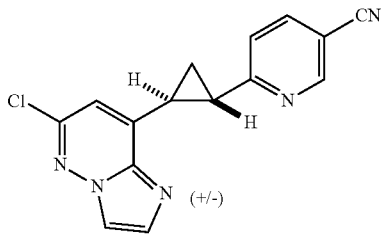 [SMILES: N#Cc1ccc([C@H]2C[C@@H]2c2cc(Cl)nn3ccnc23)nc1]

6-[(1S,2S)-2-(6-chloroimidazo[1,2-b]pyridazin-8-yl)cyclopropyl]pyridine-3-carbonitrile (Racemic Mixture) was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitril with 6-[(1S,2S)-2-(4,4,5,5-tetramethyl-1,3,2-dioxaborolan-2-yl)cyclopropyl]pyridine-3-carbonitrile (Racemic Mixture). ES/MS m/z: 296.10 [M+H].

Intermediate 241. 6-[(1S,2S)-2-(6-chloroimidazo[1,2-b]pyridazin-8-yl)cyclopropyl]quinoline

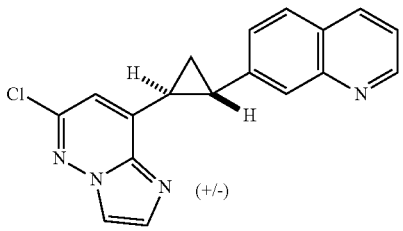 [SMILES: Clc1cc([C@H]2C[C@@H]2c2ccc3cccnc3c2)c2nccn2n1]

6-[(1S,2S)-2-(6-chloroimidazo[1,2-b]pyridazin-8-yl)cyclopropyl]quinoline (racemic mixture) was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitril with 7-[(1S,2S)-2-(4,4,5,5-tetramethyl-1,3,2-dioxaborolan-2-yl)cyclopropyl]quinoline (racemic mixture). ES/MS m/z: 321.10 [M+H].

Intermediate 242. 6-chloro-3-fluoro-8-[(1S,2S)-2-[5-(trifluoromethyl)-2-pyridyl]cyclopropyl]imidazo[1,2-b]pyridazine

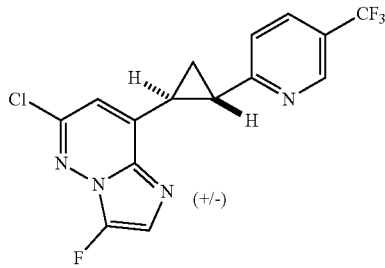 [SMILES: Fc1cnc2c([C@H]3C[C@@H]3c3ccc(C(F)(F)F)cn3)cc(Cl)nn12]

6-chloro-3-fluoro-8-[(1S,2S)-2-[5-(trifluoromethyl)-2-pyridyl]cyclopropyl]imidazo[1,2-b]pyridazine (Racemic Mixture) was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitril with 2-[(1S,2S)-2-(4,4,5,5-tetramethyl-1,3,2-dioxaborolan-2-yl)cyclopropyl]-5-(trifluoromethyl)pyridine (Racemic Mixture) and 8-bromo-6-chloroimidazo[1,2-b]pyridazine with 8-bromo-6-chloro-3-fluoroimidazo[1,2-b]pyridazine. ES/MS m/z: 357.10 [M+H].

Intermediate 243. 6-[(1S,2S)-2-(6-chloro-3-fluoro-imidazo[1,2-b]pyridazin-8-yl)cyclopropyl]pyridine-3-carbonitrile

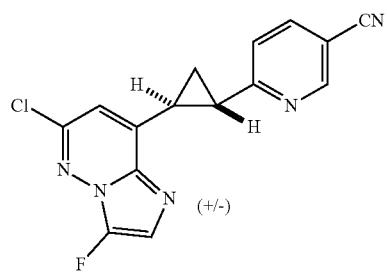 [SMILES: N#Cc1ccc([C@H]2C[C@@H]2c2cc(Cl)nn3c(F)cnc23)nc1]

6-[(1S,2S)-2-(6-chloro-3-fluoro-imidazo[1,2-b]pyridazin-8-yl)cyclopropyl]pyridine-3-carbonitrile (Racemic Mixture) was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitril with 6-[(1S,2S)-2-(4,4,5,5-tetramethyl-1,3,2-dioxaborolan-2-yl)cyclopropyl]pyridine-3-carbonitrile (Racemic Mixture) and 8-bromo-6-chloroimidazo[1,2-b]pyridazine with 8-bromo-6-chloro-3-fluoroimidazo[1,2-b]pyridazine. ES/MS m/z: 314.10 [M+H].

Intermediate 244. 6-[(1S,2S)-2-(6-chloroimidazo[1,2-b]pyridazin-8-yl)cyclopropyl]-8-(trifluoromethyl)quinoline

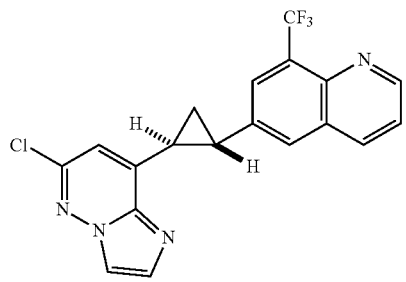 [SMILES: FC(F)(F)c1cc([C@H]2C[C@@H]2c2cc(Cl)nn3ccnc23)cc2cccnc12]

6-[(1S,2S)-2-(6-chloroimidazo[1,2-b]pyridazin-8-yl)cyclopropyl]-8-(trifluoromethyl)quinoline was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitril with 6-[(1S,2S)-2-(4,4,5,5-tetramethyl-1,3,2-dioxaborolan-2-yl)cyclopropyl]-8-(trifluoromethyl)quinoline. ES/MS m/z: 389.10 [M+H].

Intermediate 245. 6-[(1S,2S)-2-(6-chloro-3-fluoro-imidazo[1,2-b]pyridazin-8-yl)cyclopropyl]-8-(trifluoromethyl)quinoline

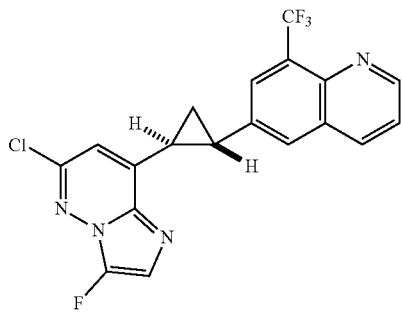 [SMILES: Fc1cnc2c([C@H]3C[C@@H]3c3cc(C(F)(F)F)c4ncccc4c3)cc(Cl)nn12]

6-[(1S,2S)-2-(6-chloro-3-fluoro-imidazo[1,2-b]pyridazin-8-yl)cyclopropyl]-8-(trifluoromethyl)quinoline was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitril with 6-[(1S,2S)-2-(4,4,5,5-tetramethyl-1,3,2-dioxaborolan-2-yl)cyclopropyl]-8-(trifluoromethyl)quinoline and 8-bromo-6-chloroimidazo[1,2-b]pyridazine with 8-bromo-6-chloro-3-fluoroimidazo[1,2-b]pyridazine. ES/MS m/z: 407.10 [M+H].

Intermediate 246. 6-chloro-8-[(1S,2S)-2-[6-(difluoromethoxy)-3-pyridyl]cyclopropyl]-3-fluoro-imidazo[1,2-b]pyridazine

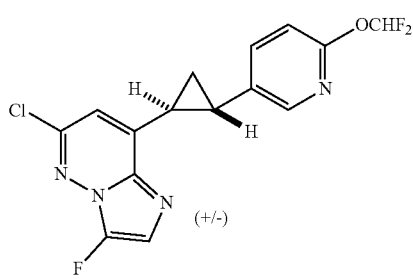 [SMILES: Fc1cnc2c([C@H]3C[C@@H]3c3ccc(OC(F)F)nc3)cc(Cl)nn12]

6-chloro-8-[(1S,2S)-2-[6-(difluoromethoxy)-3-pyridyl]cyclopropyl]-3-fluoro-imidazo[1,2-b]pyridazine (Racemic Mixture) was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitril with 2-(difluoromethoxy)-5-[(1S,2S)-2-(4,4,5,5-tetramethyl-1,3,2-dioxaborolan-2-yl)cyclopropyl]pyridine (Racemic Mixture) and 8-bromo-6-chloroimidazo[1,2-b]pyridazine with 8-bromo-6-chloro-3-fluoroimidazo[1,2-b]pyridazine. ES/MS m/z: 355.10 [M+H].

Intermediate 247. 6-chloro-8-[(1S,2S)-2-[5-(difluoromethoxy)-2-pyridyl]cyclopropyl]-3-fluoro-imidazo[1,2-b]pyridazine

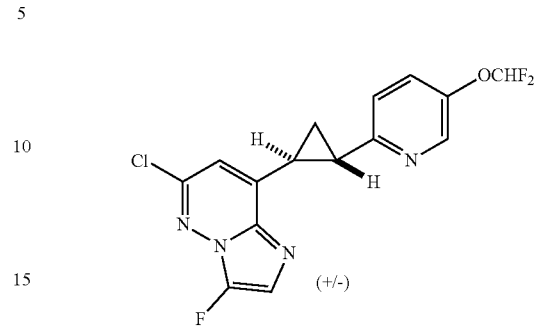

6-chloro-8-[(1S,2S)-2-[5-(difluoromethoxy)-2-pyridyl]cyclopropyl]-3-fluoro-imidazo[1,2-b]pyridazine (Racemic Mixture) was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitril with 5-(difluoromethoxy)-2-[(1S,2S)-2-(4,4,5,5-tetramethyl-1,3,2-dioxaborolan-2-yl)cyclopropyl]pyridine (Racemic Mixture) and 8-bromo-6-chloroimidazo[1,2-b]pyridazine with 8-bromo-6-chloro-3-fluoroimidazo[1,2-b]pyridazine. ES/MS m/z: 355.10 [M+H].

Intermediate 248. 3-[(1R,2R)-2-(6-chloroimidazo[1,2-b]pyridazin-8-yl)cyclopropyl]-8-(trifluoromethyl)quinoline

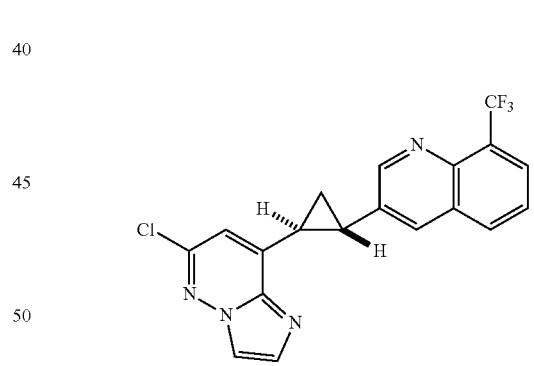

3-[(1R,2R)-2-(6-chloroimidazo[1,2-b]pyridazin-8-yl)cyclopropyl]-8-(trifluoromethyl)quinoline was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitril with 3-[(1S,2S)-2-(4,4,5,5-tetramethyl-1,3,2-dioxaborolan-2-yl)cyclopropyl]-8-(trifluoromethyl)quinoline. ES/MS m/z: 389.10 [M+H].

Intermediate 249. 7-[(1R,2R)-2-(6-chloroimidazo[1,2-b]pyridazin-8-yl)cyclopropyl]-5-(trifluoromethyl)quinoline

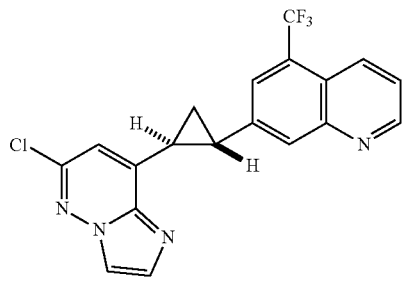 [SMILES: FC(F)(F)c1cc([C@H]2C[C@@H]2c2cc(Cl)nn3ccnc23)cc2ncccc12]

7-[(1R,2R)-2-(6-chloroimidazo[1,2-b]pyridazin-8-yl)cyclopropyl]-5-(trifluoromethyl)quinoline was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitril with 7-[(1S,2S)-2-(4,4,5,5-tetramethyl-1,3,2-dioxaborolan-2-yl)cyclopropyl]-5-(trifluoromethyl)quinoline. ES/MS m/z: 389.10 [M+H].

Intermediate 250. 6-chloro-2-cyclopropyl-8-[(1S,2S)-2-(2,4-difluorophenyl)cyclopropyl]imidazo[1,2-b]pyridazine

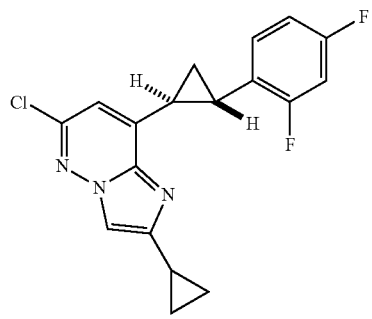 [SMILES: Fc1ccc([C@H]2C[C@@H]2c2cc(Cl)nn3cc(C4CC4)nc23)c(F)c1]

6-chloro-2-cyclopropyl-8-[(1S,2S)-2-(2,4-difluorophenyl)cyclopropyl]imidazo[1,2-b]pyridazine was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitril with 2-[(1S,2S)-2-(2,4-difluorophenyl)cyclopropyl]-4,4,5,5-tetramethyl-1,3,2-dioxaborolane and 8-bromo-6-chloroimidazo[1,2-b]pyridazine with 8-bromo-6-chloro-2-cyclopropyl-imidazo[1,2-b]pyridazine. ES/MS m/z: 346.20 [M+H].

Intermediate 251. 5-[(1S,2S)-2-(6-chloro-2-cyclopropyl-imidazo[1,2-b]pyridazin-8-yl)cyclopropyl]-1,3-benzothiazole

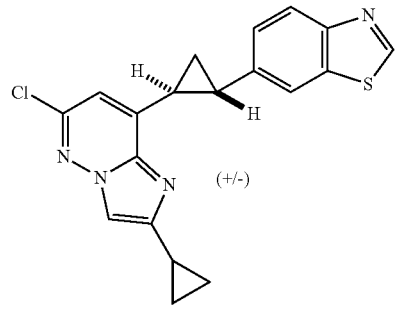 [SMILES: Clc1cc([C@H]2C[C@@H]2c2ccc3ncsc3c2)c2nc(C3CC3)cn2n1]

5-[(1S,2S)-2-(6-chloro-2-cyclopropyl-imidazo[1,2-b]pyridazin-8-yl)cyclopropyl]-1,3-benzothiazole (Racemic Mixture) was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitril with 6-[(1S,2S)-2-(4,4,5,5-tetramethyl-1,3,2-dioxaborolan-2-yl)cyclopropyl]-1,3-benzothiazole (Racemic Mixture) and 8-bromo-6-chloroimidazo[1,2-b]pyridazine with 8-bromo-6-chloro-2-cyclopropyl-imidazo[1,2-b]pyridazine. ES/MS m/z: 367.10 [M+H].

Intermediates 252 and 253. 6-chloro-3-fluoro-8-[(1S,2S)-2-[5-(trifluoromethyl)-2-pyridyl]cyclopropyl]imidazo[1,2-b]pyridazine and 6-chloro-3-fluoro-8-[(1R,2R)-2-[5-(trifluoromethyl)-2-pyridyl]cyclopropyl]imidazo[1,2-b]pyridazine

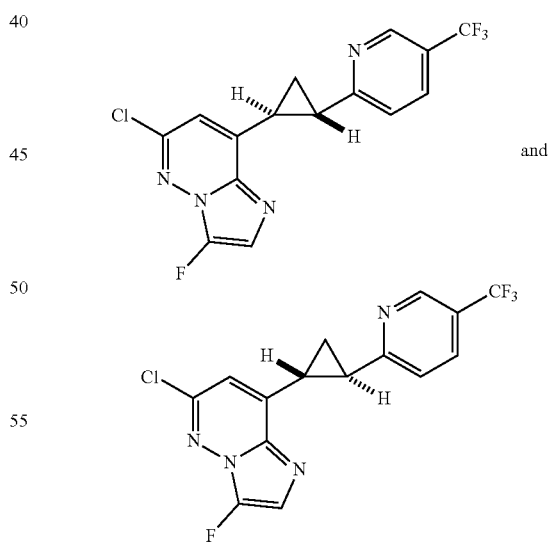

6-chloro-3-fluoro-8-[(1S,2S)-2-[5-(trifluoromethyl)-2-pyridyl]cyclopropyl]imidazo[1,2-b]pyridazine and 6-chloro-3-fluoro-8-[(1R,2R)-2-[5-(trifluoromethyl)-2-pyridyl]cyclopropyl]imidazo[1,2-b]pyridazine were chirally separated from the racemic mixture by SFC OJ-H column (10% EtOH).

Intermediate 254. 6-[(1S,2S)-2-(6-chloro-3-fluoro-imidazo[1,2-b]pyridazin-8-yl)cyclopropyl]-3,3-dimethyl-1-(2,2,2-trifluoroethyl)indolin-2-one

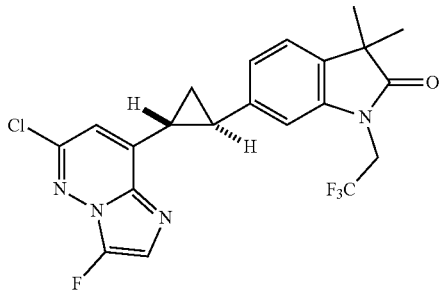 [SMILES: CC1(C)C(=O)N(CC(F)(F)F)c2cc([C@@H]3C[C@H]3c3cc(Cl)nn4c(F)cnc34)ccc21]

6-[(1S,2S)-2-(6-chloro-3-fluoro-imidazo[1,2-b]pyridazin-8-yl)cyclopropyl]-3,3-dimethyl-1-(2,2,2-trifluoroethyl)indolin-2-one was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitril with 3,3-dimethyl-6-[(1S,2S)-2-(4,4,5,5-tetramethyl-1,3,2-dioxaborolan-2-yl)cyclopropyl]-1-(2,2,2-trifluoroethyl)indolin-2-one and 8-bromo-6-chloro-3-fluoro-imidazo[1,2-b]pyridazine. ES/MS m/z: 453.10 [M+H].

Intermediate 255. 6-chloro-3-fluoro-8-[(1S,2S)-2-[3-fluoro-1-(2,2,2-trifluoroethyl)indazol-6-yl]cyclopropyl]imidazo[1,2-b]pyridazine

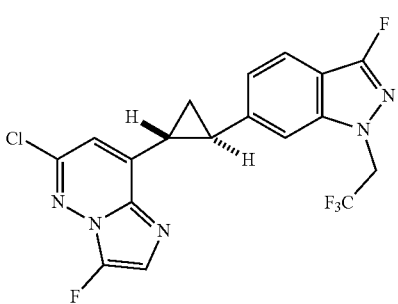 [SMILES: Fc1nn(CC(F)(F)F)c2cc([C@@H]3C[C@H]3c3cc(Cl)nn4c(F)cnc34)ccc12]

6-chloro-3-fluoro-8-[(1S,2S)-2-[3-fluoro-1-(2,2,2-trifluoroethyl)indazol-6-yl]cyclopropyl]imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitril with 3-fluoro-6-[(1S,2S)-2-(4,4,5,5-tetramethyl-1,3,2-dioxaborolan-2-yl)cyclopropyl]-1-(2,2,2-trifluoroethyl)indazole and 8-bromo-6-chloro-3-fluoro-imidazo[1,2-b]pyridazine. ES/MS m/z: 428.110 [M+H].

Intermediate 256. 6-chloro-8-[(3S,4R)-3,4-difluoropyrrolidin-1-yl]-3-fluoro-imidazo[1,2-b]pyridazine

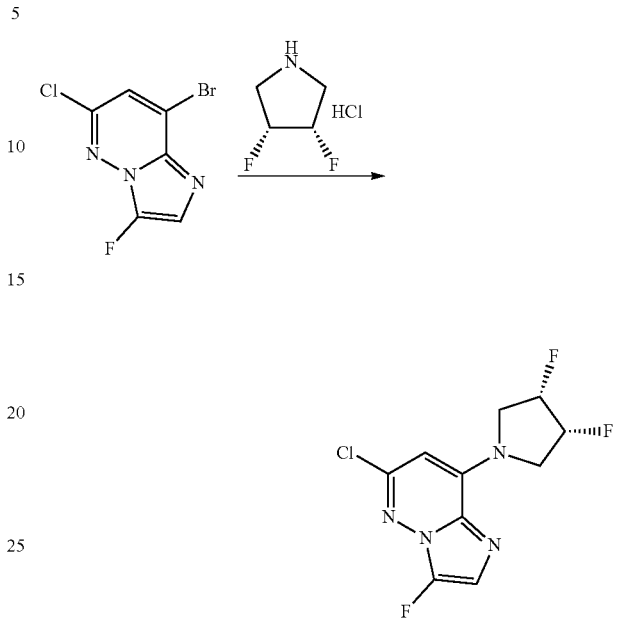

6-chloro-8-[(3S,4R)-3,4-difluoropyrrolidin-1-yl]-3-fluoro-imidazo[1,2-b]pyridazine was prepared as follows: A microwave vial was charged with 8-bromo-6-chloro-3-fluoro-imidazo[1,2-b]pyridazine (200 mg, 0.799 mmol, 1 equiv), (3S,4R)-3,4-difluoropyrrolidine hydrochloride (138 mg, 0.958 mmol, 1.2 equiv), DIPEA (0.343 mL, 1.92 mmol, 2.4 equiv), and MeCN (5 mL). The reaction mixture was heated to 85° C. After 24 hours, the reaction mixture was concentrated. The residue obtained was triturated with water, the resulting solids were filtered, washed with water, and dried affording 6-chloro-8-[(3S,4R)-3,4-difluoropyrrolidin-1-yl]-3-fluoro-imidazo[1,2-b]pyridazine. ES/MS m/z: 277.10.

Intermediate 257. 6-chloro-8-(3,3-difluoropyrrolidin-1-yl)-3-fluoro-imidazo[1,2-b]pyridazine

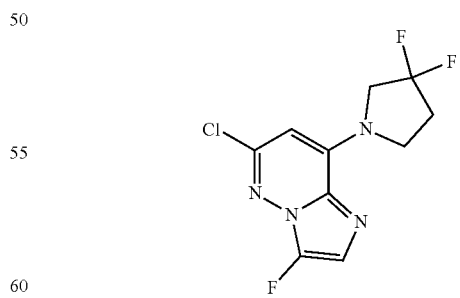

6-chloro-8-(3,3-difluoropyrrolidin-1-yl)-3-fluoro-imidazo[1,2-b]pyridazine was prepared in the manner described for Intermediate 256, but replacing (3S,4R)-3,4-difluoropyrrolidine hydrochloride with 3,3-difluoropyrrolidine. ES/MS m/z: 277.10.

Intermediate 258. 6-chloro-8-[(3R)-3-(trifluoromethyl)pyrrolidin-1-yl]imidazo[1,2-b]pyridazine

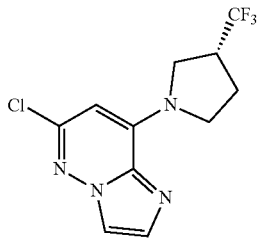 [SMILES: FC(F)(F)[C@@H]1CCN(c2cc(Cl)nn3ccnc23)C1]

6-chloro-8-[(3R)-3-(trifluoromethyl)pyrrolidin-1-yl]imidazo[1,2-b]pyridazine was prepared in the manner described for Intermediate 256, but replacing (3S,4R)-3,4-difluoropyrrolidine hydrochloride with (3R)-3-(trifluoromethyl)pyrrolidine; hydrochloride. ES/MS m/z: 291.10.

Intermediate 259. 6-chloro-8-[(3S)-3-isopropylpyrrolidin-1-yl]imidazo[1,2-b]pyridazine

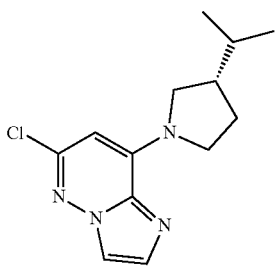 [SMILES: CC(C)[C@@H]1CCN(c2cc(Cl)nn3ccnc23)C1]

6-chloro-8-[(3S)-3-isopropylpyrrolidin-1-yl]imidazo[1,2-b]pyridazine was prepared in the manner described for Intermediate 256, but replacing (3S,4R)-3,4-difluoropyrrolidine hydrochloride with (3S)-3-isopropylpyrrolidine; hydrochloride. ES/MS m/z: 265.20.

Intermediate 260. 6-chloro-8-(7-fluoro-5-azaspiro[2.4]heptan-5-yl)imidazo[1,2-b]pyridazine

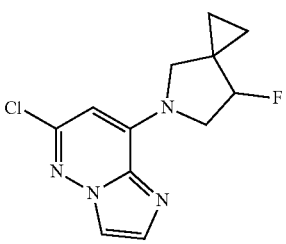 [SMILES: FC1CN(c2cc(Cl)nn3ccnc23)CC12CC2]

6-chloro-8-(7-fluoro-5-azaspiro[2.4]heptan-5-yl)imidazo[1,2-b]pyridazine was prepared in the manner described for Intermediate 256, but replacing (3S,4R)-3,4-difluoropyrrolidine hydrochloride with 7-fluoro-5-azaspiro[2.4]heptane; hydrochloride. ES/MS m/z: 267.10.

Intermediate 261. 6-chloro-8-[7-(difluoromethyl)-5-azaspiro[2.4]heptan-5-yl]imidazo[1,2-b]pyridazine

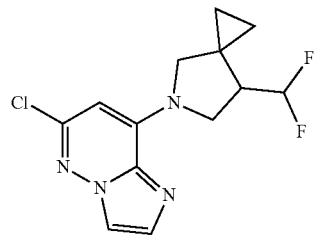 [SMILES: FC(F)C1CN(c2cc(Cl)nn3ccnc23)CC12CC2]

6-chloro-8-[7-(difluoromethyl)-5-azaspiro[2.4]heptan-5-yl]imidazo[1,2-b]pyridazine was prepared in the manner described for Intermediate 256, but replacing (3S,4R)-3,4-difluoropyrrolidine hydrochloride with 7-(difluoromethyl)-5-azaspiro[2.4]heptane; hydrochloride. ES/MS m/z: 299.10.

Intermediate 262. 6-chloro-8-[3-fluoro-3-(trifluoromethyl)pyrrolidin-1-yl]imidazo[1,2-b]pyridazine

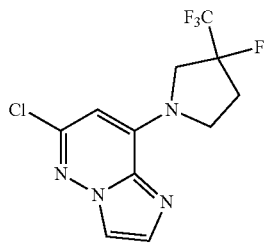 [SMILES: FC(F)(F)C1(F)CCN(c2cc(Cl)nn3ccnc23)C1]

6-chloro-8-[3-fluoro-3-(trifluoromethyl)pyrrolidin-1-yl]imidazo[1,2-b]pyridazine was prepared in the manner described for Intermediate 256, but replacing (3S,4R)-3,4-difluoropyrrolidine hydrochloride with 3-fluoro-3-(trifluoromethyl)pyrrolidine; hydrochloride. ES/MS m/z: 309.10.

Intermediate 263. 6-chloro-8-(3,3-difluoro-4,4-dimethyl-pyrrolidin-1-yl)-3-fluoro-imidazo[1,2-b]pyridazine

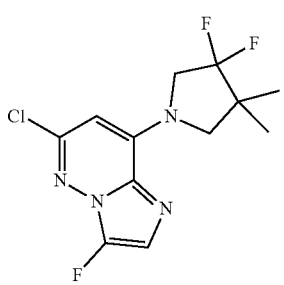 [SMILES: CC1(C)CN(c2cc(Cl)nn3c(F)cnc23)CC1(F)F]

6-chloro-8-(3,3-difluoro-4,4-dimethyl-pyrrolidin-1-yl)-3-fluoro-imidazo[1,2-b]pyridazine was prepared in the manner described for Intermediate 256, but replacing (3S,4R)-3,4-difluoropyrrolidine hydrochloride with 3,3-difluoro-4,4-dimethyl-pyrrolidine; hydrochloride. ES/MS m/z: 305.00.

Intermediate 264. 6-chloro-3-fluoro-8-(7-fluoro-5-azaspiro[2.4]heptan-5-yl)imidazo[1,2-b]pyridazine

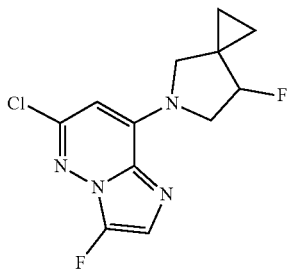 [SMILES: Fc1cnc2c(N3CC(F)C4(CC4)C3)cc(Cl)nn12]

6-chloro-3-fluoro-8-(7-fluoro-5-azaspiro[2.4]heptan-5-yl)imidazo[1,2-b]pyridazine was prepared in the manner described for Intermediate 256, but replacing (3S,4R)-3,4-difluoropyrrolidine hydrochloride with 7-fluoro-5-azaspiro[2.4]heptane; hydrochloride. ES/MS m/z: 285.10.

Intermediate 265. 6-chloro-7-(7-fluoro-5-azaspiro[2.4]heptan-5-yl)pyrazolo[1,5-a]pyrimidine

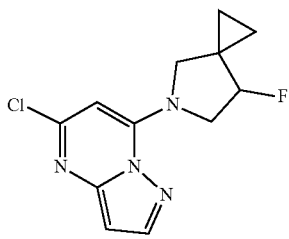 [SMILES: FC1CN(c2cc(Cl)nc3ccnn23)CC12CC2]

6-chloro-7-(7-fluoro-5-azaspiro[2.4]heptan-5-yl)pyrazolo[1,5-a]pyrimidine was prepared in the manner described for Intermediate 256, but replacing (3S,4R)-3,4-difluoropyrrolidine hydrochloride with 7-fluoro-5-azaspiro[2.4]heptane; hydrochloride and 5,7-dichloropyrazolo[1,5-a]pyrimidine. ES/MS m/z: 267.10.

Intermediate 266. 6-chloro-2-cyclopropyl-8-(3,3-difluoro-4,4-dimethyl-pyrrolidin-1-yl)imidazo[1,2-b]pyridazine

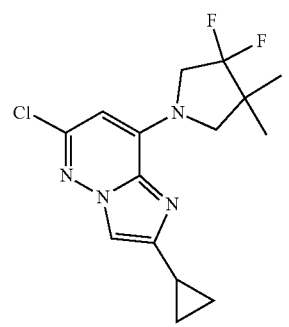 [SMILES: CC1(C)CN(c2cc(Cl)nn3cc(C4CC4)nc23)CC1(F)F]

6-chloro-2-cyclopropyl-8-(3,3-difluoro-4,4-dimethyl-pyrrolidin-1-yl)imidazo[1,2-b]pyridazine was prepared in the manner described for Intermediate 256, but replacing (3S,4R)-3,4-difluoropyrrolidine hydrochloride with 3,3-difluoro-4,4-dimethyl-pyrrolidine;hydrochloride and 8-bromo-6-chloro-2-cyclopropyl-imidazo[1,2-b]pyridazine. ES/MS m/z: 327.10.

Intermediate 267. 1-(6-chloroimidazo[1,2-b]pyridazin-8-yl)-4,4-difluoro-pyrrolidin-3-ol

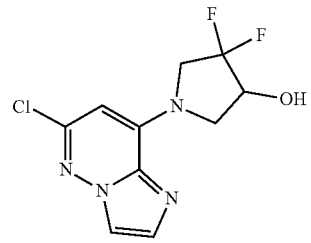 [SMILES: OC1CN(c2cc(Cl)nn3ccnc23)CC1(F)F]

1-(6-chloroimidazo[1,2-b]pyridazin-8-yl)-4,4-difluoro-pyrrolidin-3-ol was prepared in the manner described for Intermediate 256, but replacing (3S,4R)-3,4-difluoropyrrolidine hydrochloride with 4,4-difluoropyrrolidin-3-ol; hydrochloride. ES/MS m/z: 275.10.

Intermediate 268. 6-(2,4-dimethoxypyrimidin-5-yl)-3-fluoro-8-[(1S,2S)-2-[4-(trifluoromethyl)phenyl]cyclopropyl]imidazo[1,2-b]pyridazine (Racemic Mixture)

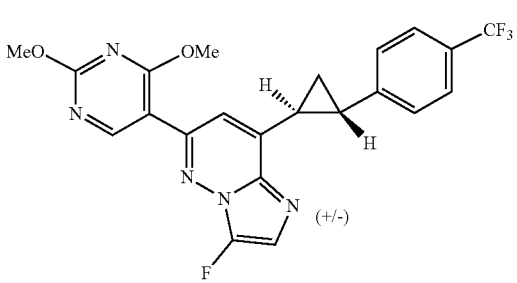 [SMILES: COc1ncc(-c2cc([C@H]3C[C@@H]3c3ccc(C(F)(F)F)cc3)c3ncc(F)n3n2)c(OC)n1]

6-(2,4-dimethoxypyrimidin-5-yl)-3-fluoro-8-[(1S,2S)-2-[4-(trifluoromethyl)phenyl]cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-3-fluoro-8-[(1S,2S)-2-[4-(trifluoromethyl)phenyl]cyclopropyl]imidazo[1,2-b]pyridazine(Racemic Mixture). ES/MS m/z: 460.20 [M+H].

Intermediate 269. 5-[(1S,2S)-2-[6-(2,4-dimethoxypyrimidin-5-yl)imidazo[1,2-b]pyridazin-8-yl]cyclopropyl]-1-methyl-pyridin-2-one

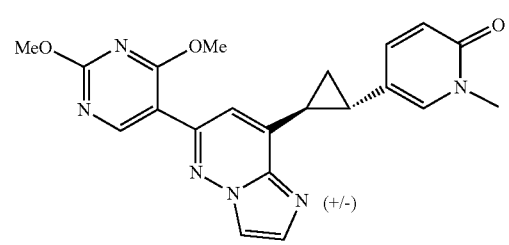 [SMILES: COc1ncc(-c2cc([C@H]3C[C@@H]3c3ccc(=O)n(C)c3)c3nccn3n2)c(OC)n1]

5-[(1S,2S)-2-[6-(2,4-dimethoxypyrimidin-5-yl)imidazo[1,2-b]pyridazin-8-yl]cyclopropyl]-1-methyl-pyridin-2-one was prepared as a racemic mixture using 5-[(1S,2S)-2-(6-chloroimidazo[1,2-b]pyridazin-8-yl)cyclopropyl]-1-methyl-pyridin-2-one (Racemic Mixture). ES/MS m/z: 405.20 [M+H].

Intermediate 270. 8-[(1S,2S)-2-(4-chlorophenyl)cyclopropyl]-6-(2,4-dimethoxypyrimidin-5-yl)-3-fluoro-imidazo[1,2-b]pyridazine (Racemic Mixture)

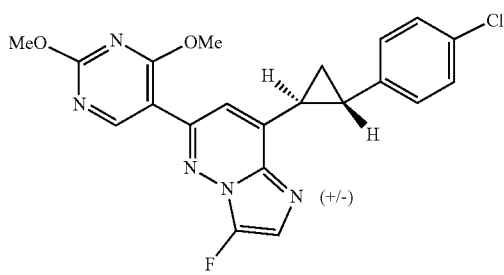 [SMILES: COc1ncc(-c2cc([C@H]3C[C@@H]3c3ccc(Cl)cc3)c3ncc(F)n3n2)c(OC)n1]

8-[(1S,2S)-2-(4-chlorophenyl)cyclopropyl]-6-(2,4-dimethoxypyrimidin-5-yl)-3-fluoro-imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-(4-chlorophenyl)cyclopropyl]-3-fluoro-imidazo[1,2-b]pyridazine (Racemic Mixture). ES/MS m/z: 426.20 [M+H].

Intermediate 271. 6-(2,4-dimethoxypyrimidin-5-yl)-3-fluoro-8-[(1S,2S)-2-(4-pyridyl)cyclopropyl]imidazo[1,2-b]pyridazine (Racemic Mixture)

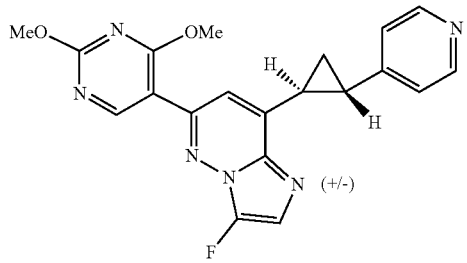 [SMILES: COc1ncc(-c2cc([C@H]3C[C@@H]3c3ccncc3)c3ncc(F)n3n2)c(OC)n1]

6-(2,4-dimethoxypyrimidin-5-yl)-3-fluoro-8-[(1S,2S)-2-(4-pyridyl)cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-3-fluoro-8-[(1S,2S)-2-(4-pyridyl)cyclopropyl]imidazo[1,2-b]pyridazine (Racemic Mixture). ES/MS m/z: 393.20 [M+H].

Intermediate 272. 6-(2,4-dimethoxypyrimidin-5-yl)-3-fluoro-8-[(1S,2S)-2-(3-pyridyl)cyclopropyl]imidazo[1,2-b]pyridazine (Racemic Mixture)

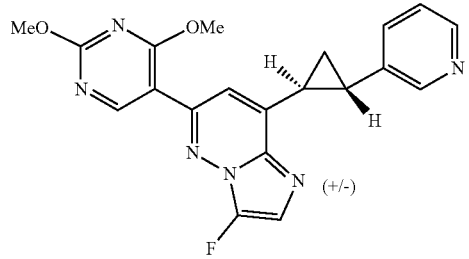 [SMILES: COc1ncc(-c2cc([C@H]3C[C@@H]3c3cccnc3)c3ncc(F)n3n2)c(OC)n1]

6-(2,4-dimethoxypyrimidin-5-yl)-3-fluoro-8-[(1S,2S)-2-(3-pyridyl)cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-3-fluoro-8-[(1S,2S)-2-(3-pyridyl)cyclopropyl]imidazo[1,2-b]pyridazine (Racemic Mixture). ES/MS m/z: 393.20 [M+H].

Intermediate 273. 6-(2,4-dimethoxypyrimidin-5-yl)-3-fluoro-8-[(1S,2S)-2-pyrimidin-5-ylcyclopropyl]imidazo[1,2-b]pyridazine (Racemic Mixture)

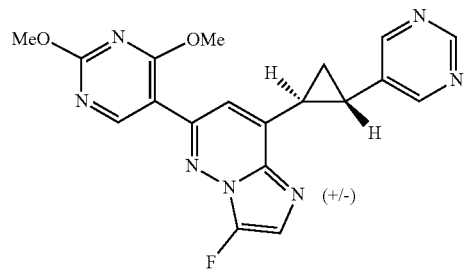 [SMILES: COc1ncc(-c2cc([C@H]3C[C@@H]3c3cncnc3)c3ncc(F)n3n2)c(OC)n1]

6-(2,4-dimethoxypyrimidin-5-yl)-3-fluoro-8-[(1S,2S)-2-pyrimidin-5-ylcyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-3-fluoro-8-[(1S,2S)-2-pyrimidin-5-ylcyclopropyl]imidazo[1,2-b]pyridazine (Racemic Mixture). ES/MS m/z: 394.20 [M+H].

Intermediate 274. 6-(2,4-dimethoxypyrimidin-5-yl)-3-fluoro-8-[(1S,2S)-2-(2-pyridyl)cyclopropyl]imidazo[1,2-b]pyridazine (Racemic Mixture)

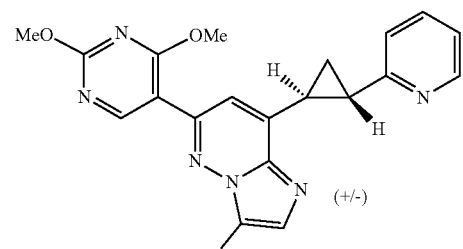

6-(2,4-dimethoxypyrimidin-5-yl)-3-fluoro-8-[(1S,2S)-2-(2-pyridyl)cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-3-fluoro-8-[(1S, 2S)-2-(2-pyridyl)cyclopropyl]imidazo[1,2-b]pyridazine (Racemic Mixture). ES/MS m/z: 393.20 [M+H].

Intermediate 275. 8-[(3S,4R)-3,4-difluoropyrrolidin-1-yl]-6-(2,4-dimethoxypyrimidin-5-yl)-3-fluoro-imidazo[1,2-b]pyridazine

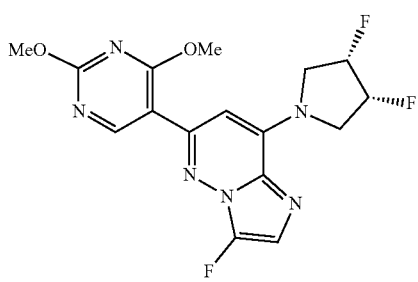 [SMILES: COc1ncc(-c2cc(N3C[C@@H](F)[C@@H](F)C3)c3ncc(F)n3n2)c(OC)n1]

8-[(3S,4R)-3,4-difluoropyrrolidin-1-yl]-6-(2,4-dimethoxypyrimidin-5-yl)-3-fluoro-imidazo[1,2-b]pyridazine was prepared in the manner described for Intermediate 18, but replacing 6-chloro-8-cyclopropyl-2-methyl-imidazo[1,2-b]pyridazine with 6-chloro-8-[(3S,4R)-3,4-difluoropyrrolidin-1-yl]-3-fluoro-imidazo[1,2-b]pyridazine. ES/MS m/z: 381.20 [M+H].

Intermediate 276. 8-(3,3-difluoropyrrolidin-1-yl)-6-(2,4-dimethoxypyrimidin-5-yl)-3-fluoro-imidazo[1,2-b]pyridazine

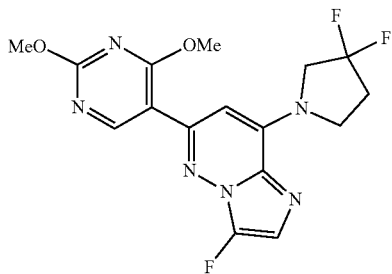 [SMILES: COc1ncc(-c2cc(N3CCC(F)(F)C3)c3ncc(F)n3n2)c(OC)n1]

8-(3,3-difluoropyrrolidin-1-yl)-6-(2,4-dimethoxypyrimidin-5-yl)-3-fluoro-imidazo[1,2-b]pyridazine was prepared in the manner described for Intermediate 18, but replacing 6-chloro-8-cyclopropyl-2-methyl-imidazo[1,2-b]pyridazine with 6-chloro-8-(3,3-difluoropyrrolidin-1-yl)-3-fluoro-imidazo[1,2-b]pyridazine. ES/MS m/z: 381.20 [M+H].

Intermediate 277. 6-(2,4-dimethoxypyrimidin-5-yl)-8-[(3R)-3-(trifluoromethyl)pyrrolidin-1-yl]imidazo[1,2-b]pyridazine

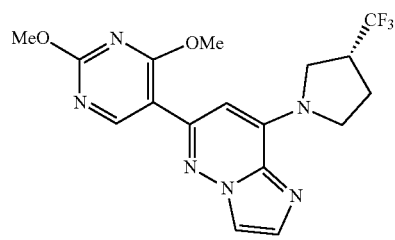 [SMILES: COc1ncc(-c2cc(N3CC[C@@H](C(F)(F)F)C3)c3nccn3n2)c(OC)n1]

6-(2,4-dimethoxypyrimidin-5-yl)-8-[(3R)-3-(trifluoromethyl)pyrrolidin-1-yl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[(3R)-3-(trifluoromethyl)pyrrolidin-1-yl]imidazo[1,2-b]pyridazine. ES/MS m/z: 395.10 [M+H].

Intermediate 278. 6-(2,4-dimethoxypyrimidin-5-yl)-8-[(3S)-3-isopropylpyrrolidin-1-yl]imidazo[1,2-b]pyridazine

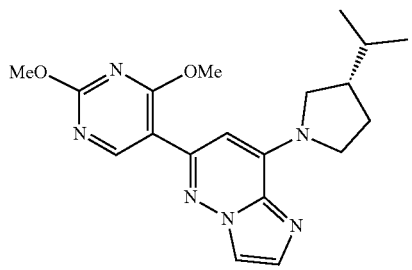 [SMILES: COc1ncc(-c2cc(N3CC[C@@H](C(C)C)C3)c3nccn3n2)c(OC)n1]

6-(2,4-dimethoxypyrimidin-5-yl)-8-[(3S)-3-isopropylpyrrolidin-1-yl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[(3S)-3-isopropylpyrrolidin-1-yl]imidazo[1,2-b]pyridazine. ES/MS m/z: 369.20 [M+H].

Intermediate 279. 6-(2,4-dimethoxypyrimidin-5-yl)-8-[3-(4-methoxyphenyl)pyrrolidin-1-yl]imidazo[1,2-b]pyridazine

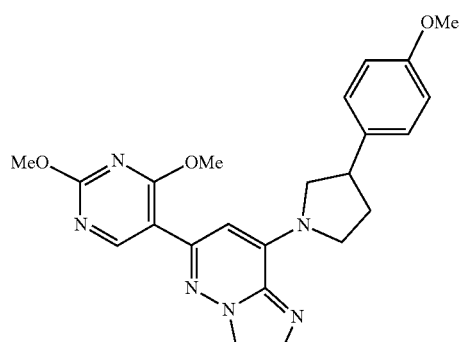

6-(2,4-dimethoxypyrimidin-5-yl)-8-[3-(4-methoxyphenyl)pyrrolidin-1-yl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[3-(4-methoxyphenyl)pyrrolidin-1-yl]imidazo[1,2-b]pyridazine. ES/MS m/z: 433.20 [M+H].

Intermediate 280. 6-(2,4-dimethoxypyrimidin-5-yl)-8-(7-fluoro-5-azaspiro[2.4]heptan-5-yl)imidazo[1,2-b]pyridazine

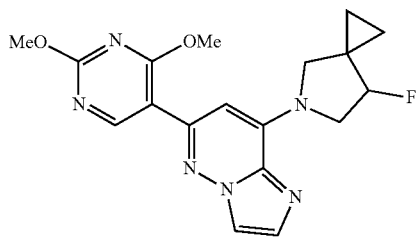 [SMILES: COc1ncc(-c2cc(N3CC(F)C4(CC4)C3)c3nccn3n2)c(OC)n1]

6-(2,4-dimethoxypyrimidin-5-yl)-8-(7-fluoro-5-azaspiro[2.4]heptan-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(7-fluoro-5-azaspiro[2.4]heptan-5-yl)imidazo[1,2-b]pyridazine. ES/MS m/z: 371.20 [M+H].

Intermediate 281. Ethyl 6-(2,4-dimethoxypyrimidin-5-yl)-8-[(1S,2S)-2-(4-fluorophenyl)cyclopropyl]imidazo[1,2-b]pyridazine-2-carboxylate (Racemic Mixture)

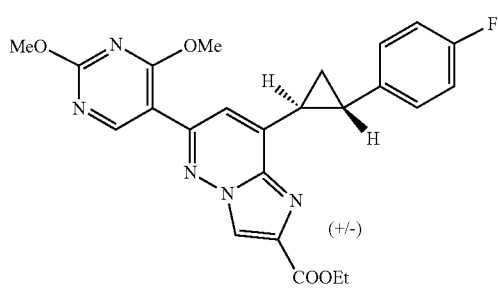 [SMILES: CCOC(=O)c1cn2nc(-c3cnc(OC)nc3OC)cc([C@H]3C[C@@H]3c3ccc(F)cc3)c2n1]

Ethyl 6-(2,4-dimethoxypyrimidin-5-yl)-8-[(1S,2S)-2-(4-fluorophenyl)cyclopropyl]imidazo[1,2-b]pyridazine-2-carboxylate (Racemic Mixture) was prepared in the manner described for Intermediate 18, but replacing 6-chloro-8-cyclopropyl-2-methyl-imidazo[1,2-b]pyridazine with ethyl 6-chloro-8-[(1S,2S)-2-(4-fluorophenyl)cyclopropyl]imidazo[1,2-b]pyridazine-2-carboxylate (Racemic Mixture). ES/MS m/z: 464.20 [M+H].

Intermediate 282. 8-[7-(difluoromethyl)-5-azaspiro[2.4]heptan-5-yl]-6-(2,4-dimethoxypyrimidin-5-yl)imidazo[1,2-b]pyridazine

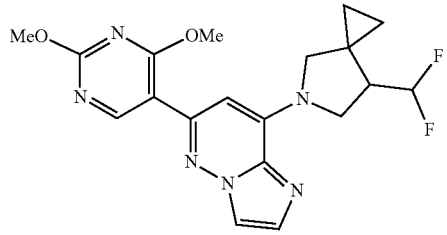 [SMILES: COc1ncc(-c2cc(N3CC(C(F)F)C4(CC4)C3)c3nccn3n2)c(OC)n1]

8-[7-(difluoromethyl)-5-azaspiro[2.4]heptan-5-yl]-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-[7-(difluoromethyl)-5-azaspiro[2.4]heptan-5-yl]imidazo[1,2-b]pyridazine. ES/MS m/z: 403.10 [M+H].

Intermediate 283. 6-(2,4-dimethoxypyrimidin-5-yl)-8-[3-fluoro-3-(trifluoromethyl)pyrrolidin-1-yl]imidazo[1,2-b]pyridazine

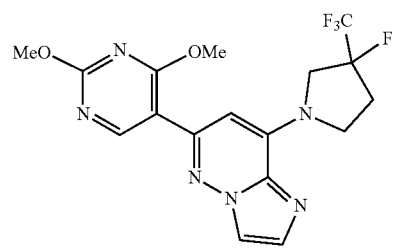 [SMILES: COc1ncc(-c2cc(N3CCC(F)(C(F)(F)F)C3)c3nccn3n2)c(OC)n1]

6-(2,4-dimethoxypyrimidin-5-yl)-8-[3-fluoro-3-(trifluoromethyl)pyrrolidin-1-yl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[3-fluoro-3-(trifluoromethyl)pyrrolidin-1-yl]imidazo[1,2-b]pyridazine. ES/MS m/z: 413.20 [M+H].

Intermediate 284. 5-[(1S,2S)-2-[6-(2,4-dimethoxypyrimidin-5-yl)imidazo[1,2-b]pyridazin-8-yl]cyclopropyl]isoquinoline (Racemic Mixture)

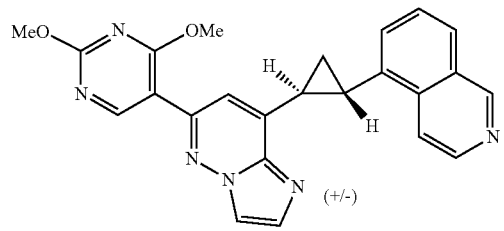 [SMILES: COc1ncc(-c2cc([C@H]3C[C@@H]3c3cccc4cnccc34)c3nccn3n2)c(OC)n1]

5-[(1S,2S)-2-[6-(2,4-dimethoxypyrimidin-5-yl)imidazo[1,2-b]pyridazin-8-yl]cyclopropyl]isoquinoline (Racemic Mixture) was prepared in the manner described for Intermediate 18, but replacing 6-chloro-8-cyclopropyl-2-methyl-imidazo[1,2-b]pyridazine with 5-[(1S,2S)-2-(6-chloroimidazo[1,2-b]pyridazin-8-yl)cyclopropyl]isoquinoline (racemic mixture). ES/MS m/z: 425.20 [M+H].

Intermediate 285. 4-[(1S,2S)-2-[6-(2,4-dimethoxypyrimidin-5-yl)imidazo[1,2-b]pyridazin-8-yl]cyclopropyl]quinoline (Racemic Mixture)

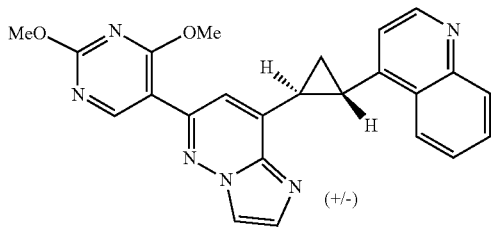 [SMILES: COc1ncc(-c2cc([C@H]3C[C@@H]3c3ccnc4ccccc34)c3nccn3n2)c(OC)n1]

4-[(1S,2S)-2-[6-(2,4-dimethoxypyrimidin-5-yl)imidazo[1,2-b]pyridazin-8-yl]cyclopropyl]quinoline (Racemic Mixture) was prepared in the manner described for Intermediate 18, but replacing 6-chloro-8-cyclopropyl-2-methyl-imidazo[1,2-b]pyridazine with 4-[(1S,2S)-2-(6-chloroimidazo[1,2-b]pyridazin-8-yl)cyclopropyl]quinoline (Racemic Mixture). ES/MS m/z: 425.20 [M+H].

Intermediate 286. 5-[(1S,2S)-2-[6-(2,4-dimethoxypyrimidin-5-yl)imidazo[1,2-b]pyridazin-8-yl]cyclopropyl]quinoline (Racemic Mixture)

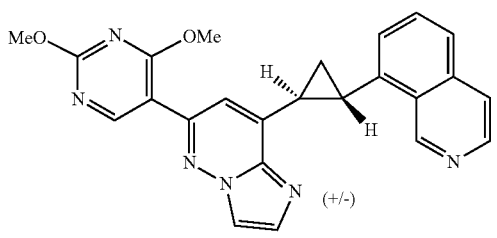 [SMILES: COc1ncc(-c2cc([C@H]3C[C@@H]3c3cccc4ccncc34)c3nccn3n2)c(OC)n1]

5-[(1S,2S)-2-[6-(2,4-dimethoxypyrimidin-5-yl)imidazo[1,2-b]pyridazin-8-yl]cyclopropyl]quinoline (Racemic Mixture) was prepared in the manner described for Intermediate 18, but replacing 6-chloro-8-cyclopropyl-2-methyl-imidazo[1,2-b]pyridazine with 5-[(1S,2S)-2-(6-chloroimidazo[1,2-b]pyridazin-8-yl)cyclopropyl]quinoline (Racemic Mixture). ES/MS m/z: 425.20 [M+H].

Intermediate 287. 6-(2,4-dimethoxypyrimidin-5-yl)-8-[(1S,2S)-2-[2-fluoro-4-(trifluoromethyl)phenyl]cyclopropyl]imidazo[1,2-b]pyridazine (Racemic Mixture)

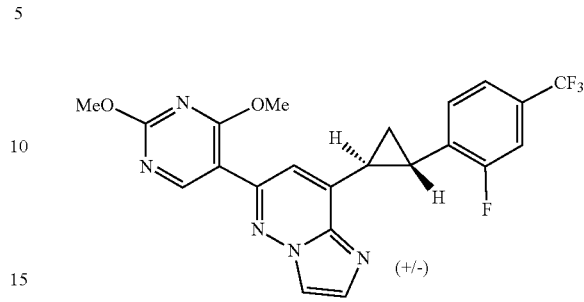

6-(2,4-dimethoxypyrimidin-5-yl)-8-[(1S,2S)-2-[2-fluoro-4-(trifluoromethyl)phenyl]cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[2-fluoro-4-(trifluoromethyl)phenyl]cyclopropyl]imidazo[1,2-b]pyridazine (Racemic Mixture). ES/MS m/z: 460.20 [M+H].

Intermediate 288. 6-(2,4-dimethoxypyrimidin-5-yl)-8-[(1S,2S)-2-(5-fluoro-3-pyridyl)cyclopropyl]imidazo[1,2-b]pyridazine (Racemic Mixture)

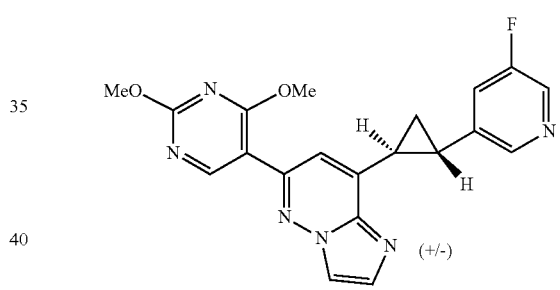

6-(2,4-dimethoxypyrimidin-5-yl)-8-[(1S,2S)-2-(5-fluoro-3-pyridyl)cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-(5-fluoro-3-pyridyl)cyclopropyl]imidazo[1,2-b]pyridazine (Racemic Mixture). ES/MS m/z: 393.20 [M+H].

Intermediate 289. 6-(2,4-dimethoxypyrimidin-5-yl)-8-[(1S,2S)-2-[6-(trifluoromethyl)-3-pyridyl]cyclopropyl]imidazo[1,2-b]pyridazine (Racemic Mixture)

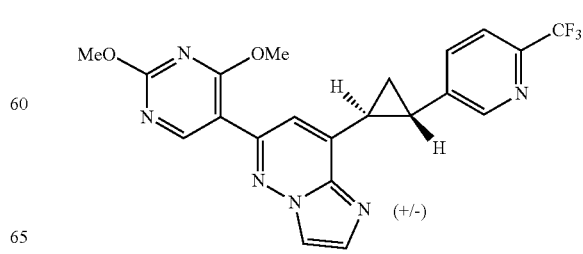

6-(2,4-dimethoxypyrimidin-5-yl)-8-[(1S,2S)-2-[6-(trifluoromethyl)-3-pyridyl]cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[6-(trifluoromethyl)-3-pyridyl]cyclopropyl]imidazo[1,2-b]pyridazine (Racemic Mixture). ES/MS m/z: 443.10 [M+H].

Intermediate 290. 3-[(1S,2S)-2-[6-(2,4-dimethoxypyrimidin-5-yl)imidazo[1,2-b]pyridazin-8-yl]cyclopropyl]quinoline (Racemic Mixture)

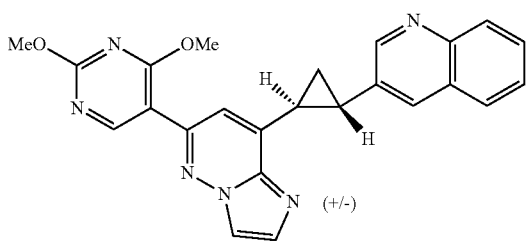 [SMILES: COc1ncc(-c2cc([C@H]3C[C@@H]3c3cnc4ccccc4c3)c3nccn3n2)c(OC)n1]

3-[(1S,2S)-2-[6-(2,4-dimethoxypyrimidin-5-yl)imidazo[1,2-b]pyridazin-8-yl]cyclopropyl]quinoline (Racemic Mixture) was prepared in the manner described for Intermediate 18, but replacing 6-chloro-8-cyclopropyl-2-methyl-imidazo[1,2-b]pyridazine with 3-[(1S,2S)-2-(6-chloroimidazo[1,2-b]pyridazin-8-yl)cyclopropyl]quinoline (Racemic Mixture). ES/MS m/z: 425.20 [M+H].

Intermediate 291. 6-(2,4-dimethoxypyrimidin-5-yl)-8-[(1S,2S)-2-(3-pyridyl)cyclopropyl]imidazo[1,2-b]pyridazine

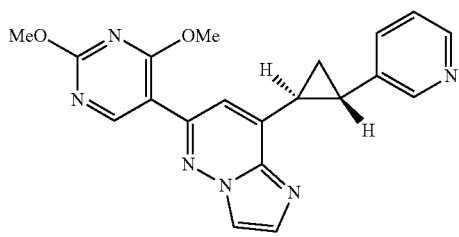 [SMILES: COc1ncc(-c2cc([C@H]3C[C@@H]3c3cccnc3)c3nccn3n2)c(OC)n1]

6-(2,4-dimethoxypyrimidin-5-yl)-8-[(1S,2S)-2-(3-pyridyl)cyclopropyl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[(1S,2S)-2-(3-pyridyl)cyclopropyl]imidazo[1,2-b]pyridazine. ES/MS m/z: 393.20 [M+H].

Intermediate 292. 6-(2,4-dimethoxypyrimidin-5-yl)-8-[(1S,2S)-2-(3-fluoro-4-pyridyl)cyclopropyl]imidazo[1,2-b]pyridazine (Racemic Mixture)

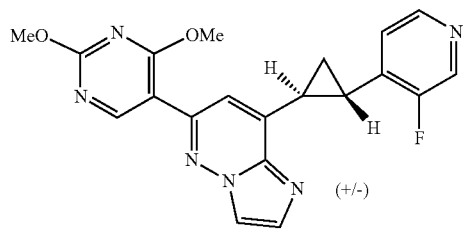 [SMILES: COc1ncc(-c2cc([C@H]3C[C@@H]3c3ccncc3F)c3nccn3n2)c(OC)n1]

6-(2,4-dimethoxypyrimidin-5-yl)-8-[(1S,2S)-2-(3-fluoro-4-pyridyl)cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-(3-fluoro-4-pyridyl)cyclopropyl]imidazo[1,2-b]pyridazine (Racemic Mixture). ES/MS m/z: 393.20 [M+H].

Intermediate 293. 6-(2,4-dimethoxypyrimidin-5-yl)-8-[(1S,2S)-2-[2-(trifluoromethyl)-4-pyridyl]cyclopropyl]imidazo[1,2-b]pyridazine (Racemic Mixture)

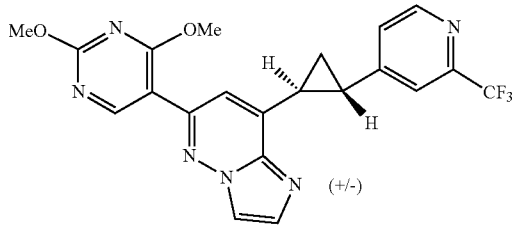 [SMILES: COc1ncc(-c2cc([C@H]3C[C@@H]3c3ccnc(C(F)(F)F)c3)c3nccn3n2)c(OC)n1]

6-(2,4-dimethoxypyrimidin-5-yl)-8-[(1S,2S)-2-[2-(trifluoromethyl)-4-pyridyl]cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[2-(trifluoromethyl)-4-pyridyl]cyclopropyl]imidazo[1,2-b]pyridazine (Racemic Mixture). ES/MS m/z: 443.20 [M+H].

Intermediate 294. 6-(2,4-dimethoxypyrimidin-5-yl)-8-[(1S,2S)-2-[5-(trifluoromethyl)-2-pyridyl]cyclopropyl]imidazo[1,2-b]pyridazine (Racemic Mixture)

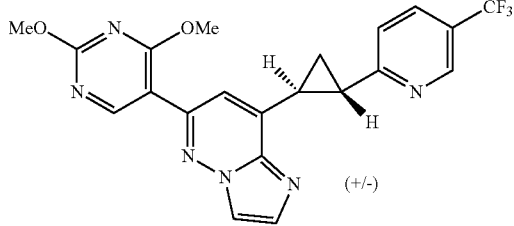 [SMILES: COc1ncc(-c2cc([C@H]3C[C@@H]3c3ccc(C(F)(F)F)cn3)c3nccn3n2)c(OC)n1]

6-(2,4-dimethoxypyrimidin-5-yl)-8-[(1S,2S)-2-[5-(trifluoromethyl)-2-pyridyl]cyclopropyl]imidazo[1,2-b]

pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[5-(trifluoromethyl)-2-pyridyl]cyclopropyl]imidazo[1,2-b]pyridazine (Racemic Mixture). ES/MS m/z: 443.20 [M+H].

Intermediate 295. 6-[(1S,2S)-2-[6-(2,4-dimethoxy-pyrimidin-5-yl)imidazo[1,2-b]pyridazin-8-yl]cyclopropyl]quinoline (Racemic Mixture)

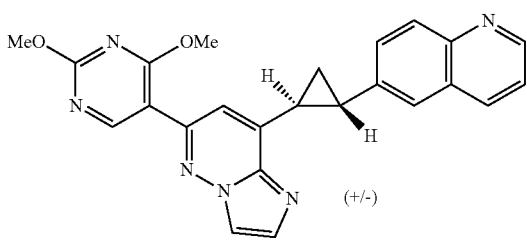 [SMILES: COc1ncc(-c2cc([C@H]3C[C@@H]3c3ccc4ncccc4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]quinoline (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]quinoline (Racemic Mixture). ES/MS m/z: 425.20 [M+H].

Intermediate 296. 6-[(1S,2S)-2-[6-(2,4-dimethoxy-pyrimidin-5-yl)imidazo[1,2-b]pyridazin-8-yl]cyclopropyl]isoquinoline (Racemic Mixture)

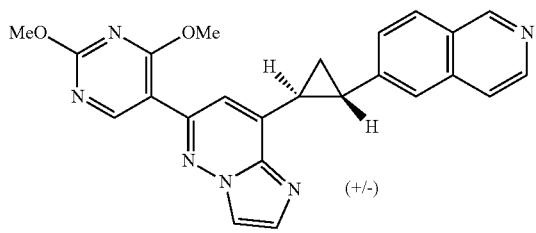 [SMILES: COc1ncc(-c2cc([C@H]3C[C@@H]3c3ccc4cnccc4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]isoquinoline (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]isoquinoline (racemic mixture). ES/MS m/z: 425.20 [M+H].

Intermediate 297. 6-[(1S,2S)-2-[6-(2,4-dimethoxy-pyrimidin-5-yl)imidazo[1,2-b]pyridazin-8-yl]cyclopropyl]pyridine-3-carbonitrile (Racemic Mixture)

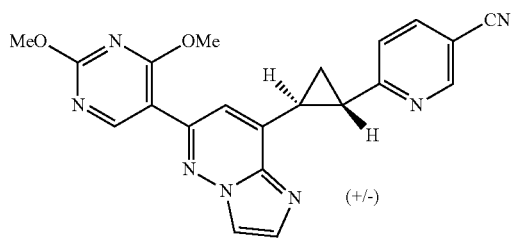 [SMILES: COc1ncc(-c2cc([C@H]3C[C@@H]3c3ccc(C#N)cn3)c3nccn3n2)c(OC)n1]

6-[(1S,2S)-2-[6-(2,4-dimethoxypyrimidin-5-yl)imidazo[1,2-b]pyridazin-8-yl]cyclopropyl]pyridine-3-carbonitrile (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]pyridine-3-carbonitrile (Racemic Mixture). ES/MS m/z: 400.20 [M+H].

Intermediate 298. 7-[(1S,2S)-2-[6-(2,4-dimethoxy-pyrimidin-5-yl)imidazo[1,2-b]pyridazin-8-yl]cyclopropyl]quinoline (Racemic Mixture)

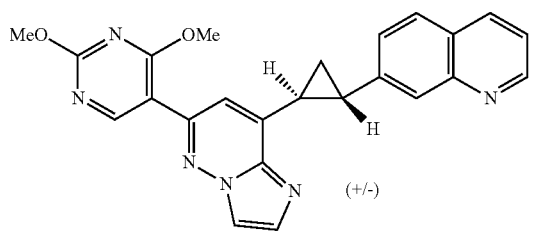 [SMILES: COc1ncc(-c2cc([C@H]3C[C@@H]3c3ccc4cccnc4c3)c3nccn3n2)c(OC)n1]

7-[(1S,2S)-2-[6-(2,4-dimethoxypyrimidin-5-yl)imidazo[1,2-b]pyridazin-8-yl]cyclopropyl]quinoline (Racemic Mixture) was prepared in the manner described for Intermediate 18, but replacing 6-chloro-8-cyclopropyl-2-methyl-imidazo[1,2-b]pyridazine with 7-[(1S,2S)-2-(6-chloroimidazo[1,2-b]pyridazin-8-yl)cyclopropyl]quinoline (Racemic Mixture). ES/MS m/z: 425.20 [M+H].

Intermediate 299. 6-[(1S,2S)-2-[6-(2,4-dimethoxy-pyrimidin-5-yl)-3-fluoro-imidazo[1,2-b]pyridazin-8-yl]cyclopropyl]pyridine-3-carbonitrile (Racemic Mixture)

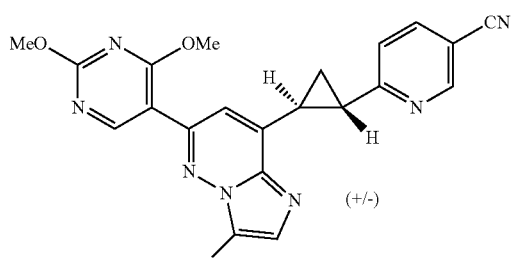

6-[(1S,2S)-2-[6-(2,4-dimethoxypyrimidin-5-yl)-3-fluoro-imidazo[1,2-b]pyridazin-8-yl]cyclopropyl]pyridine-3-carbonitrile (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloro-3-fluoro-imidazo[1,2-b]pyridazin-8-yl)cyclopropyl]pyridine-3-carbonitrile (Racemic Mixture). ES/MS m/z: 418.10 [M+H].

Intermediate 300. 8-(3,3-difluoro-4,4-dimethyl-pyrrolidin-1-yl)-6-(2,4-dimethoxypyrimidin-5-yl)-3-fluoro-imidazo[1,2-b]pyridazine

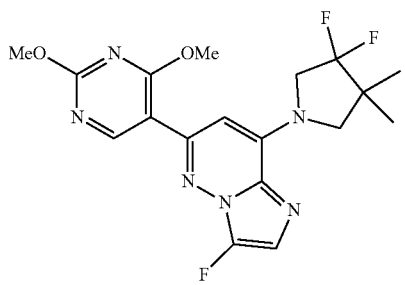 [SMILES: COc1ncc(-c2cc(N3CC(C)(C)C(F)(F)C3)c3ncc(F)n3n2)c(OC)n1]

8-(3,3-difluoro-4,4-dimethyl-pyrrolidin-1-yl)-6-(2,4-dimethoxypyrimidin-5-yl)-3-fluoro-imidazo[1,2-b]pyridazine was prepared in the manner described for Intermediate 18, but replacing 6-chloro-8-cyclopropyl-2-methyl-imidazo[1,2-b]pyridazine with 6-chloro-8-(3,3-difluoro-4,4-dimethyl-pyrrolidin-1-yl)-3-fluoro-imidazo[1,2-b]pyridazine. ES/MS m/z: 409.20 [M+H].

Intermediate 301. 6-(2,4-dimethoxypyrimidin-5-yl)-3-fluoro-8-(7-fluoro-5-azaspiro[2.4]heptan-5-yl)imidazo[1,2-b]pyridazine

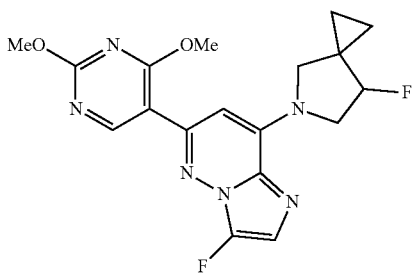 [SMILES: COc1ncc(-c2cc(N3CC(F)C4(CC4)C3)c3ncc(F)n3n2)c(OC)n1]

6-(2,4-dimethoxypyrimidin-5-yl)-3-fluoro-8-(7-fluoro-5-azaspiro[2.4]heptan-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-(7-fluoro-5-azaspiro[2.4]heptan-5-yl)imidazo[1,2-b]pyridazine. ES/MS m/z: 389.20 [M+H].

Intermediate 302. 5-(2,4-dimethoxypyrimidin-5-yl)-7-(7-fluoro-5-azaspiro[2.4]heptan-5-yl)pyrazolo[1,5-a]pyrimidine

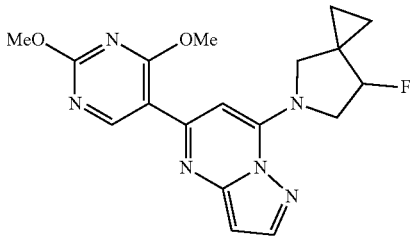 [SMILES: COc1ncc(-c2cc(N3CC(F)C4(CC4)C3)n3nccc3n2)c(OC)n1]

5-(2,4-dimethoxypyrimidin-5-yl)-7-(7-fluoro-5-azaspiro[2.4]heptan-5-yl)pyrazolo[1,5-a]pyrimidine was prepared in the manner described for Intermediate 18, but replacing 6-chloro-8-cyclopropyl-2-methyl-imidazo[1,2-b]pyridazine with 5-chloro-7-(7-fluoro-5-azaspiro[2.4]heptan-5-yl)pyrazolo[1,5-a]pyrimidine. ES/MS m/z: 371.20 [M+H].

Intermediate 303. 8-[(1S,2S)-2-[5-(difluoromethoxy)-2-pyridyl]cyclopropyl]-6-(2,4-dimethoxypyrimidin-5-yl)imidazo[1,2-b]pyridazine (Racemic Mixture)

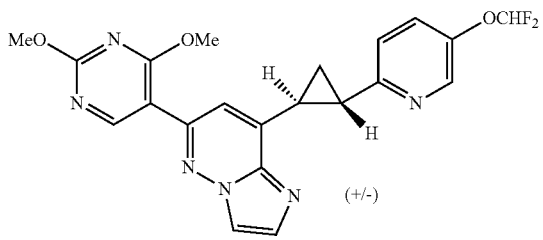 [SMILES: COc1ncc(-c2cc([C@H]3C[C@@H]3c3ccc(OC(F)F)cn3)c3nccn3n2)c(OC)n1]

8-[(1S,2S)-2-[5-(difluoromethoxy)-2-pyridyl]cyclopropyl]-6-(2,4-dimethoxypyrimidin-5-yl)imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[5-(difluoromethoxy)-2-pyridyl]cyclopropyl]imidazo[1,2-b]pyridazine (Racemic Mixture). ES/MS m/z: 441.20 [M+H].

Intermediate 304. 6-[(1S,2S)-2-[6-(2,4-dimethoxypyrimidin-5-yl)imidazo[1,2-b]pyridazin-8-yl]cyclopropyl]-2-(trifluoromethyl)quinoline (Racemic Mixture)

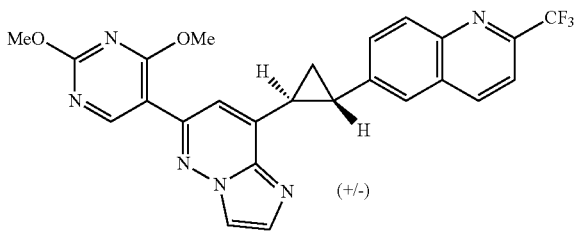 [SMILES: COc1ncc(-c2cc([C@H]3C[C@@H]3c3ccc4nc(C(F)(F)F)ccc4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]-2-(trifluoromethyl)quinoline (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-2-(trifluoromethyl)quinoline (Racemic Mixture). ES/MS m/z: 493.10 [M+H].

Intermediate 305. 6-[(1S,2S)-2-[6-(2,4-dimethoxypyrimidin-5-yl)imidazo[1,2-b]pyridazin-8-yl]cyclopropyl]-8-(trifluoromethyl)quinoline (Racemic Mixture)

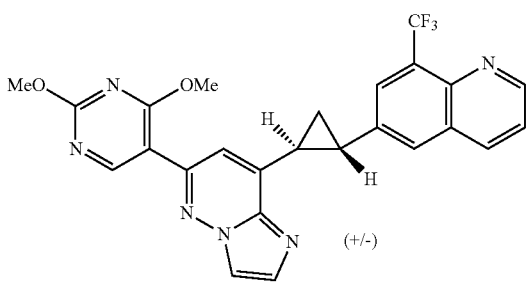 [SMILES: COc1ncc(-c2cc([C@H]3C[C@@H]3c3cc(C(F)(F)F)c4ncccc4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]-8-(trifluoromethyl)quinoline (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-8-(trifluoromethyl)quinoline (Racemic Mixture). ES/MS m/z: 493.10 [M+H].

Intermediate 306. 8-[(1S,2S)-2-[6-(difluoromethoxy)-3-pyridyl]cyclopropyl]-6-(2,4-dimethoxypyrimidin-5-yl)imidazo[1,2-b]pyridazine (Racemic Mixture)

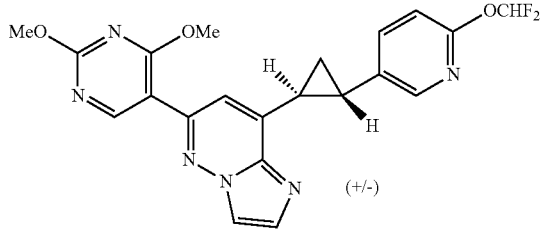

8-[(1S,2S)-2-[6-(difluoromethoxy)-3-pyridyl]cyclopropyl]-6-(2,4-dimethoxypyrimidin-5-yl)imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[6-(difluoromethoxy)-3-pyridyl]cyclopropyl]imidazo[1,2-b]pyridazine (Racemic Mixture). ES/MS m/z: 441.20 [M+H].

Intermediate 307. 7-[(1S,2S)-2-[6-(2,4-dimethoxypyrimidin-5-yl)imidazo[1,2-b]pyridazin-8-yl]cyclopropyl]-4-(trifluoromethyl)quinoline (Racemic Mixture)

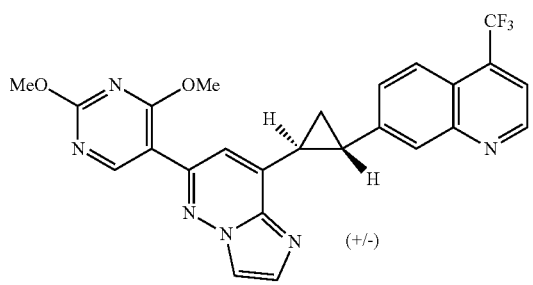 [SMILES: COc1ncc(-c2cc([C@H]3C[C@@H]3c3ccc4c(C(F)(F)F)ccnc4c3)c3nccn3n2)c(OC)n1]

7-[(1S,2S)-2-[6-(2,4-dimethoxypyrimidin-5-yl)imidazo[1,2-b]pyridazin-8-yl]cyclopropyl]-4-(trifluoromethyl)quinoline (Racemic Mixture) was prepared in the manner described for Intermediate 18, but replacing 6-chloro-8-cyclopropyl-2-methyl-imidazo[1,2-b]pyridazine with 7-[(1S,2S)-2-(6-chloroimidazo[1,2-b]pyridazin-8-yl)cyclopropyl]-4-(trifluoromethyl)quinoline (Racemic Mixture). ES/MS m/z: 493.20 [M+H].

Intermediate 308. 6-[(1S,2S)-2-[6-(2,4-dimethoxypyrimidin-5-yl)imidazo[1,2-b]pyridazin-8-yl]cyclopropyl]-3-(trifluoromethyl)isoquinoline (Racemic Mixture)

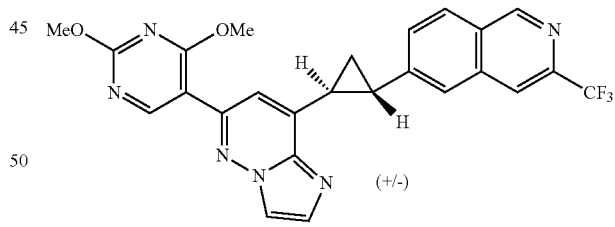

6-[(1S,2S)-2-[6-(2,4-dimethoxypyrimidin-5-yl)imidazo[1,2-b]pyridazin-8-yl]cyclopropyl]-3-(trifluoromethyl)isoquinoline (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-3-(trifluoromethyl)isoquinoline (Racemic Mixture). ES/MS m/z: 493.20 [M+H].

Intermediate 309. 6-[(1S,2S)-2-[6-(2,4-dimethoxy-pyrimidin-5-yl)imidazo[1,2-b]pyridazin-8-yl]cyclopropyl]-8-(trifluoromethyl)quinoline

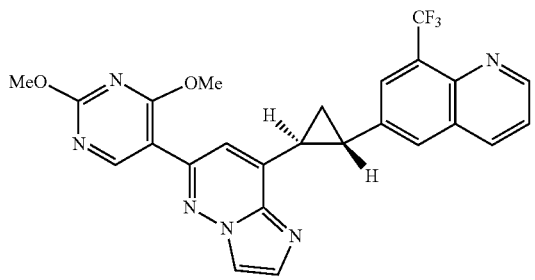 [SMILES: COc1ncc(-c2cc([C@H]3C[C@@H]3c3cc(C(F)(F)F)c4ncccc4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]-8-(trifluoromethyl)quinoline was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-8-(trifluoromethyl)quinoline. ES/MS m/z: 493.10 [M+H].

Intermediate 310. 6-[(1S,2S)-2-[6-(2,4-dimethoxy-pyrimidin-5-yl)-3-fluoro-imidazo[1,2-b]pyridazin-8-yl]cyclopropyl]-8-(trifluoromethyl)quinoline

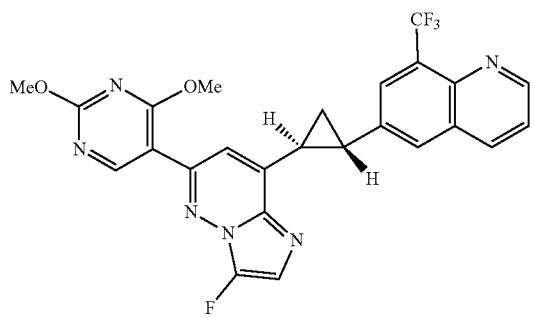 [SMILES: COc1ncc(-c2cc([C@H]3C[C@@H]3c3cc(C(F)(F)F)c4ncccc4c3)c3ncc(F)n3n2)c(OC)n1]

6-[(1S,2S)-2-[6-(2,4-dimethoxypyrimidin-5-yl)-3-fluoro-imidazo[1,2-b]pyridazin-8-yl]cyclopropyl]-8-(trifluoromethyl)quinoline was prepared in the manner described for Intermediate 18, but replacing 6-chloro-8-cyclopropyl-2-methyl-imidazo[1,2-b]pyridazine with 6-[(1S,2S)-2-(6-chloro-3-fluoro-imidazo[1,2-b]pyridazin-8-yl)cyclopropyl]-8-(trifluoromethyl)quinoline. ES/MS m/z: 511.20 [M+H].

Intermediate 311. 6-[(1S,2S)-2-[6-(2,4-dimethoxy-pyrimidin-5-yl)imidazo[1,2-b]pyridazin-8-yl]cyclopropyl]-3-(trifluoromethyl)isoquinoline

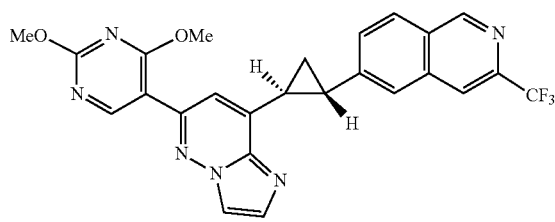 [SMILES: COc1ncc(-c2cc([C@H]3C[C@@H]3c3ccc4cnc(C(F)(F)F)cc4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]-3-(trifluoromethyl)isoquinoline was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-3-(trifluoromethyl)isoquinoline. ES/MS m/z: 493.20 [M+H].

Intermediate 312. 8-[(1S,2S)-2-[1-(2,2-difluoro-ethyl)indazol-6-yl]cyclopropyl]-6-(2,4-dimethoxy-pyrimidin-5-yl)imidazo[1,2-b]pyridazine (Racemic Mixture)

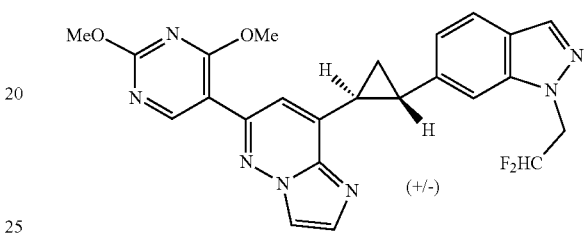

8-[(1S,2S)-2-[1-(2,2-difluoroethyl)indazol-6-yl]cyclopropyl]-6-(2,4-dimethoxypyrimidin-5-yl)imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[1-(2,2-difluoroethyl)indazol-6-yl]cyclopropyl]imidazo[1,2-b]pyridazine (Racemic Mixture). ES/MS m/z: 478.20 [M+H].

Intermediate 313. 6-(2,4-dimethoxypyrimidin-5-yl)-8-[(1S,2S)-2-(1-isopropylindazol-6-yl)cyclopropyl]imidazo[1,2-b]pyridazine (Racemic Mixture)

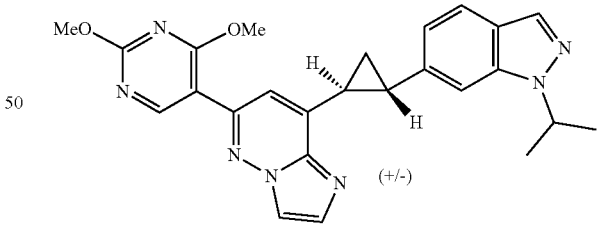

6-(2,4-dimethoxypyrimidin-5-yl)-8-[(1S,2S)-2-(1-isopropylindazol-6-yl)cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-(1-isopropylindazol-6-yl)cyclopropyl]imidazo[1,2-b]pyridazine (Racemic Mixture). ES/MS m/z: 456.20 [M+H].

Intermediate 314. 8-[(1S,2S)-2-[6-(difluoromethoxy)-3-pyridyl]cyclopropyl]-6-(2,4-dimethoxypyrimidin-5-yl)-3-fluoro-imidazo[1,2-b]pyridazine (Racemic Mixture)

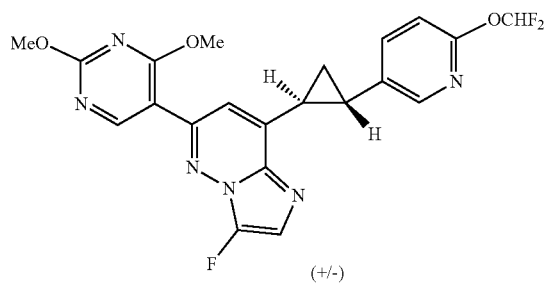 [SMILES: COc1ncc(-c2cc([C@H]3C[C@@H]3c3ccc(OC(F)F)nc3)c3ncc(F)n3n2)c(OC)n1]

8-[(1S,2S)-2-[6-(difluoromethoxy)-3-pyridyl]cyclopropyl]-6-(2,4-dimethoxypyrimidin-5-yl)-3-fluoro-imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[6-(difluoromethoxy)-3-pyridyl]cyclopropyl]-3-fluoro-imidazo[1,2-b]pyridazine (Racemic Mixture). ES/MS m/z: 459.20 [M+H].

Intermediate 315. 8-[(1S,2S)-2-[5-(difluoromethoxy)-2-pyridyl]cyclopropyl]-6-(2,4-dimethoxypyrimidin-5-yl)-3-fluoro-imidazo[1,2-b]pyridazine (Racemic Mixture)

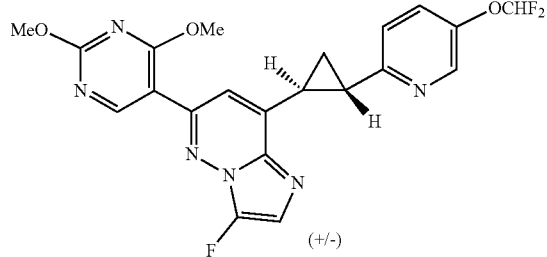 [SMILES: COc1ncc(-c2cc([C@H]3C[C@@H]3c3ccc(OC(F)F)cn3)c3ncc(F)n3n2)c(OC)n1]

8-[(1S,2S)-2-[5-(difluoromethoxy)-2-pyridyl]cyclopropyl]-6-(2,4-dimethoxypyrimidin-5-yl)-3-fluoro-imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[5-(difluoromethoxy)-2-pyridyl]cyclopropyl]-3-fluoro-imidazo[1,2-b]pyridazine (Racemic Mixture). ES/MS m/z: 459.20 [M+H].

Intermediate 316. 6-[(1S,2S)-2-[6-(2,4-dimethoxypyrimidin-5-yl)imidazo[1,2-b]pyridazin-8-yl]cyclopropyl]-2-(trifluoromethyl)quinoline

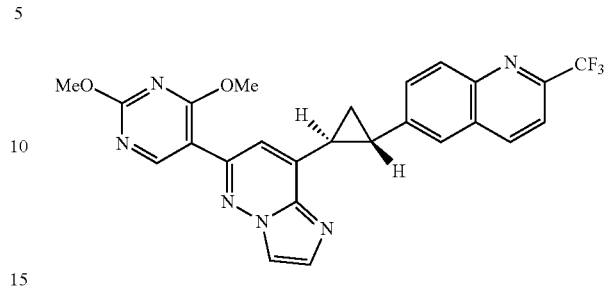

6-[(1S,2S)-2-[6-(2,4-dimethoxypyrimidin-5-yl)imidazo[1,2-b]pyridazin-8-yl]cyclopropyl]-2-(trifluoromethyl)quinoline was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-2-(trifluoromethyl)quinoline. ES/MS m/z: 493.10 [M+H].

Intermediate 317. 8-[(1S,2S)-2-[1-(cyclopropylmethyl)indazol-6-yl]cyclopropyl]-6-(2,4-dimethoxypyrimidin-5-yl)imidazo[1,2-b]pyridazine (Racemic Mixture)

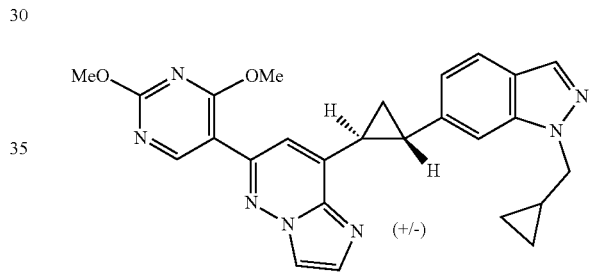

8-[(1S,2S)-2-[1-(cyclopropylmethyl)indazol-6-yl]cyclopropyl]-6-(2,4-dimethoxypyrimidin-5-yl)imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[1-(cyclopropylmethyl)indazol-6-yl]cyclopropyl]imidazo[1,2-b]pyridazine (Racemic Mixture). ES/MS m/z: 468.20 [M+H].

Intermediate 318. 6-(2,4-dimethoxypyrimidin-5-yl)-8-[(1S,2S)-2-[1-(2,2,2-trifluoroethyl)pyrrolo[3,2-c]pyridin-6-yl]cyclopropyl]imidazo[1,2-b]pyridazine (Racemic Mixture)

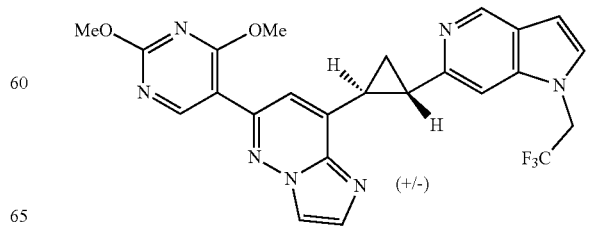

6-(2,4-dimethoxypyrimidin-5-yl)-8-[(1S,2S)-2-[1-(2,2,2-trifluoroethyl)pyrrolo[3,2-c]pyridin-6-yl]cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[1-(2,2,2-trifluoroethyl)pyrrolo[3,2-c]pyridin-6-yl]cyclopropyl]imidazo[1,2-b]pyridazine (Racemic Mixture). ES/MS m/z: 496.20 [M+H].

Intermediate 319. 6-(2,4-dimethoxypyrimidin-5-yl)-8-[(1S,2S)-2-[1-(2,2,2-trifluoroethyl)pyrrolo[2,3-b]pyridin-6-yl]cyclopropyl]imidazo[1,2-b]pyridazine (Racemic Mixture)

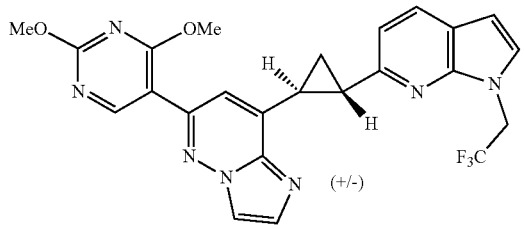 [SMILES: COc1ncc(-c2cc([C@H]3C[C@@H]3c3ccc4ccn(CC(F)(F)F)c4n3)c3nccn3n2)c(OC)n1]

6-(2,4-dimethoxypyrimidin-5-yl)-8-[(1S,2S)-2-[1-(2,2,2-trifluoroethyl)pyrrolo[2,3-b]pyridin-6-yl]cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[1-(2,2,2-trifluoroethyl)pyrrolo[2,3-b]pyridin-6-yl]cyclopropyl]imidazo[1,2-b]pyridazine (Racemic Mixture). ES/MS m/z: 496.20 [M+H].

Intermediate 320. 8-[(1S,2S)-2-[3-cyclopropyl-1-(2,2,2-trifluoroethyl)indazol-6-yl]cyclopropyl]-6-(2,4-dimethoxypyrimidin-5-yl)imidazo[1,2-b]pyridazine (Racemic Mixture)

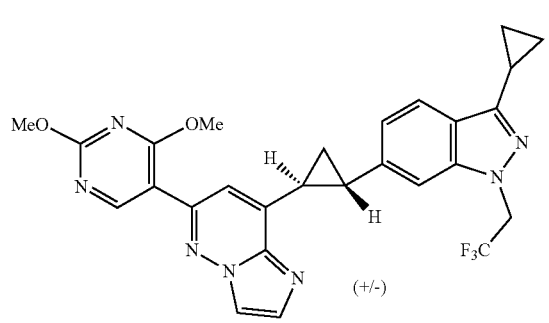 [SMILES: COc1ncc(-c2cc([C@H]3C[C@@H]3c3ccc4c(C5CC5)nn(CC(F)(F)F)c4c3)c3nccn3n2)c(OC)n1]

8-[(1S,2S)-2-[3-cyclopropyl-1-(2,2,2-trifluoroethyl)indazol-6-yl]cyclopropyl]-6-(2,4-dimethoxypyrimidin-5-yl)imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[3-cyclopropyl-1-(2,2,2-trifluoroethyl)indazol-6-yl]cyclopropyl]imidazo[1,2-b]pyridazine (Racemic Mixture). ES/MS m/z: 536.20 [M+H].

Intermediate 321. 8-[(1S,2S)-2-[1-[(2,2-difluorocyclopropyl)methyl]indazol-6-yl]cyclopropyl]-6-(2,4-dimethoxypyrimidin-5-yl)imidazo[1,2-b]pyridazine (Racemic Mixture)

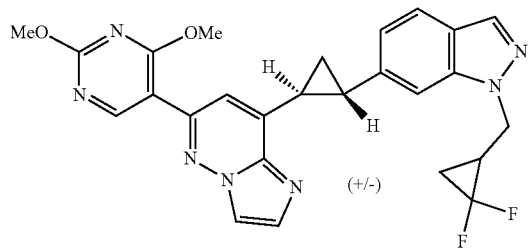 [SMILES: COc1ncc(-c2cc([C@H]3C[C@@H]3c3ccc4cnn(CC5CC5(F)F)c4c3)c3nccn3n2)c(OC)n1]

8-[(1S,2S)-2-[(2,2-difluorocyclopropyl)methyl]indazol-6-yl]cyclopropyl]-6-(2,4-dimethoxypyrimidin-5-yl)imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[1-[(2,2-difluorocyclopropyl)methyl]indazol-6-yl]cyclopropyl]imidazo[1,2-b]pyridazine (racemic mixture). ES/MS m/z: 504.20 [M+H].

Intermediate 322. 6-(2,4-dimethoxypyrimidin-5-yl)-8-[(1S,2S)-2-[3-fluoro-1-(2,2,2-trifluoroethyl)pyrrolo[3,2-c]pyridin-6-yl]cyclopropyl]imidazo[1,2-b]pyridazine (racemic mixture)

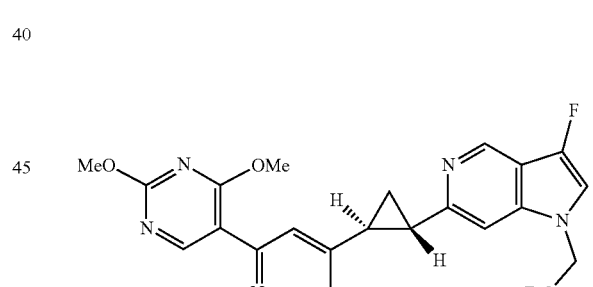

6-(2,4-dimethoxypyrimidin-5-yl)-8-[(1S,2S)-2-[3-fluoro-1-(2,2,2-trifluoroethyl)pyrrolo[3,2-c]pyridin-6-yl]cyclopropyl]imidazo[1,2-b]pyridazine (racemic mixture) was prepared in the manner described for Intermediate 18, but replacing 6-chloro-8-cyclopropyl-2-methyl-imidazo[1,2-b]pyridazine with 6-chloro-8-[(1S,2S)-2-[3-fluoro-1-(2,2,2-trifluoroethyl)pyrrolo[3,2-c]pyridin-6-yl]cyclopropyl]imidazo[1,2-b]pyridazine (racemic mixture). ES/MS m/z: 514.20 [M+H].

Intermediate 323. 6-(2,4-dimethoxypyrimidin-5-yl)-8-[(1S,2S)-2-[1-(2,2,2-trifluoroethyl)pyrrolo[3,2-c]pyridin-6-yl]cyclopropyl]imidazo[1,2-b]pyridazine

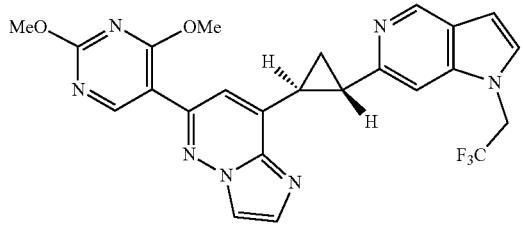 [SMILES: COc1ncc(-c2cc([C@H]3C[C@@H]3c3cc4c(ccn4CC(F)(F)F)cn3)c3nccn3n2)c(OC)n1]

6-(2,4-dimethoxypyrimidin-5-yl)-8-[(1S,2S)-2-[1-(2,2,2-trifluoroethyl)pyrrolo[3,2-c]pyridin-6-yl]cyclopropyl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[(1S,2S)-2-[1-(2,2,2-trifluoroethyl)pyrrolo[3,2-c]pyridin-6-yl]cyclopropyl]imidazo[1,2-b]pyridazine. ES/MS m/z: 496.20 [M+H].

Intermediate 324. 6-(2,4-dimethoxypyrimidin-5-yl)-8-[(1S,2S)-2-[3-isopropyl-1-(2,2,2-trifluoroethyl)indazol-6-yl]cyclopropyl]imidazo[1,2-b]pyridazine (Racemic Mixture)

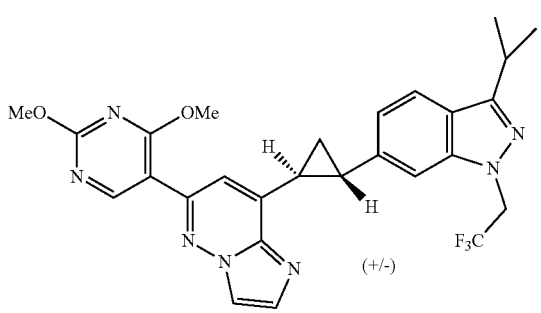 [SMILES: COc1ncc(-c2cc([C@H]3C[C@@H]3c3ccc4c(C(C)C)nn(CC(F)(F)F)c4c3)c3nccn3n2)c(OC)n1]

6-(2,4-dimethoxypyrimidin-5-yl)-8-[(1S,2S)-2-[3-isopropyl-1-(2,2,2-trifluoroethyl)indazol-6-yl]cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[3-isopropyl-1-(trifluoroethyl)indazol-2,2,2-6-yl]cyclopropyl]imidazo[1,2-b]pyridazine (Racemic Mixture). ES/MS m/z: 536.20 [M+H].

Intermediate 325. 3-[(1R,2R)-2-[6-(2,4-dimethoxypyrimidin-5-yl)imidazo[1,2-b]pyridazin-8-yl]cyclopropyl]-8-(trifluoromethyl)quinoline

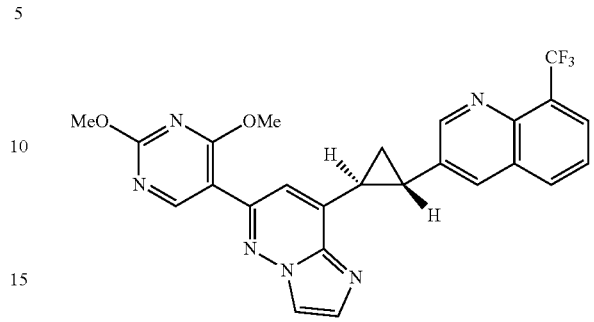

3-[(1R,2R)-2-[6-(2,4-dimethoxypyrimidin-5-yl)imidazo[1,2-b]pyridazin-8-yl]cyclopropyl]-8-(trifluoromethyl)quinoline was prepared in the manner described for Intermediate 18, but replacing 6-chloro-8-cyclopropyl-2-methyl-imidazo[1,2-b]pyridazine with 3-[(1S,2S)-2-(6-chloroimidazo[1,2-b]pyridazin-8-yl)cyclopropyl]-8-(trifluoromethyl)quinoline. ES/MS m/z: 493.10 [M+H].

Intermediate 326. 7-[(1R,2R)-2-[6-(2,4-dimethoxypyrimidin-5-yl)imidazo[1,2-b]pyridazin-8-yl]cyclopropyl]-5-(trifluoromethyl)quinoline

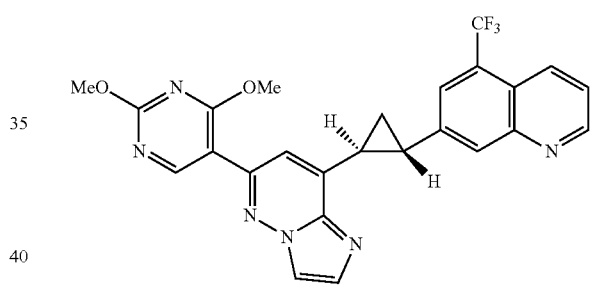

7-[(1R,2R)-2-[6-(2,4-dimethoxypyrimidin-5-yl)imidazo[1,2-b]pyridazin-8-yl]cyclopropyl]-5-(trifluoromethyl)quinoline was prepared in the manner described for Intermediate 18, but replacing 6-chloro-8-cyclopropyl-2-methyl-imidazo[1,2-b]pyridazine with 7-[(1S,2S)-2-(6-chloroimidazo[1,2-b]pyridazin-8-yl)cyclopropyl]-5-(trifluoromethyl)quinoline. ES/MS m/z: 493.10 [M+H].

Intermediate 327 and 328. 6-(2,4-dimethoxypyrimidin-5-yl)-8-[(1S,2S)-2-(2-pyridyl)cyclopropyl]imidazo[1,2-b]pyridazine and 6-(2,4-dimethoxypyrimidin-5-yl)-8-[(1R,2R)-2-(2-pyridyl)cyclopropyl]imidazo[1,2-b]pyridazine

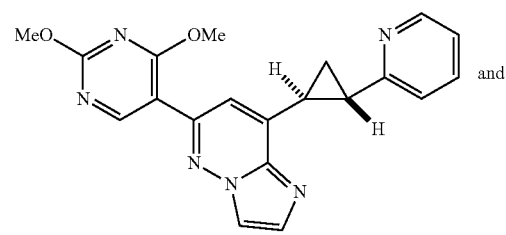

and

-continued

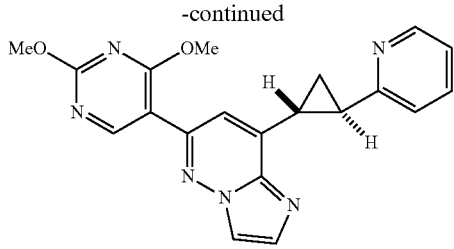

6-(2,4-dimethoxypyrimidin-5-yl)-8-[(1S,2S)-2-(2-pyridyl)cyclopropyl]imidazo[1,2-b]pyridazine and 6-(2,4-dimethoxypyrimidin-5-yl)-8-[(1R,2R)-2-(2-pyridyl)cyclopropyl]imidazo[1,2-b]pyridazine were chirally separated from the racemic mixture by SFC AD-H column (20% EtOH).

Intermediate 329. 2-cyclopropyl-8-[(1S,2S)-2-(2,4-difluorophenyl)cyclopropyl]-6-(2,4-dimethoxypyrimidin-5-yl)imidazo[1,2-b]pyridazine

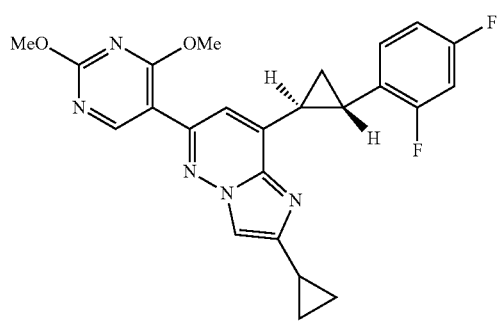 [SMILES: COc1ncc(-c2cc([C@H]3C[C@@H]3c3ccc(F)cc3F)c3nc(C4CC4)cn3n2)c(OC)n1]

2-cyclopropyl-8-[(1S,2S)-2-(2,4-difluorophenyl)cyclopropyl]-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-2-cyclopropyl-8-[(1S,2S)-2-(2,4-difluorophenyl)cyclopropyl]imidazo[1,2-b]pyridazine. ES/MS m/z: 450.10 [M+H].

Intermediate 330. 6-[(1S,2S)-2-[2-cyclopropyl-6-(2,4-dimethoxypyrimidin-5-yl)imidazo[1,2-b]pyridazin-8-yl]cyclopropyl]-1,3-benzothiazole (Racemic Mixture)

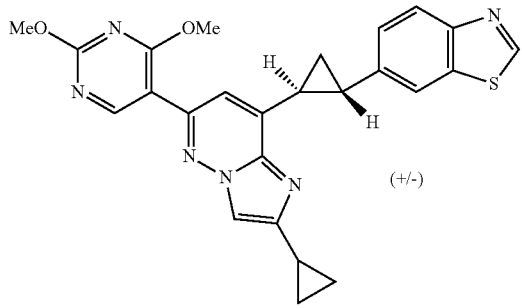 [SMILES: COc1ncc(-c2cc([C@H]3C[C@@H]3c3ccc4ncsc4c3)c3nc(C4CC4)cn3n2)c(OC)n1]

6-[(1S,2S)-2-[2-cyclopropyl-6-(2,4-dimethoxypyrimidin-5-yl)imidazo[1,2-b]pyridazin-8-yl]cyclopropyl]-1,3-benzothiazole (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloro-2-cyclopropyl-imidazo[1,2-b]pyridazin-8-yl)cyclopropyl]-1,3-benzothiazole (Racemic Mixture). ES/MS m/z: 450.10 [M+H].

Intermediate 331. 6-(2,4-dimethoxypyrimidin-5-yl)-3-fluoro-8-[(1S,2S)-2-[5-(trifluoromethyl)-2-pyridyl]cyclopropyl]imidazo[1,2-b]pyridazine

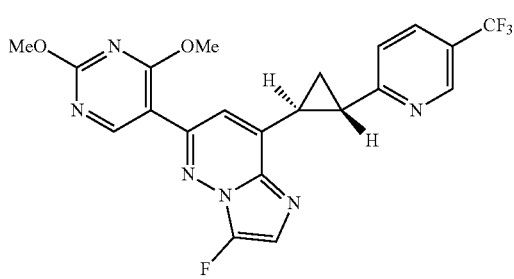 [SMILES: COc1ncc(-c2cc([C@H]3C[C@@H]3c3ccc(C(F)(F)F)cn3)c3ncc(F)n3n2)c(OC)n1]

6-(2,4-dimethoxypyrimidin-5-yl)-3-fluoro-8-[(1S,2S)-2-[5-(trifluoromethyl)-2-pyridyl]cyclopropyl]imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-[(1S,2S)-2-[5-(trifluoromethyl)-2-pyridyl]cyclopropyl]imidazo[1,2-b]pyridazine ES/MS m/z: 461.20 [M+H].

Intermediate 332. 6-(2,4-dimethoxypyrimidin-5-yl)-3-fluoro-8-[(1R,2R)-2-[5-(trifluoromethyl)-2-pyridyl]cyclopropyl]imidazo[1,2-b]pyridazine

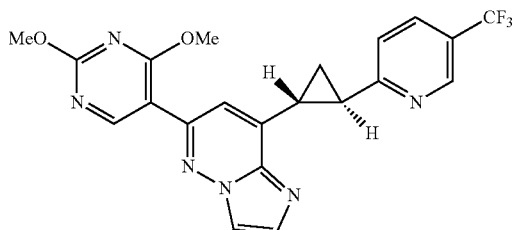

6-(2,4-dimethoxypyrimidin-5-yl)-3-fluoro-8-[(1R,2R)-2-[5-(trifluoromethyl)-2-pyridyl]cyclopropyl]imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-[(1R,2R)-2-[5-(trifluoromethyl)-2-pyridyl]cyclopropyl]imidazo[1,2-b]pyridazine ES/MS m/z: 461.20 [M+H].

Intermediate 333. 2-cyclopropyl-8-(3,3-difluoro-4,4-dimethyl-pyrrolidin-1-yl)-6-(2,4-dimethoxypyrimidin-5-yl)imidazo[1,2-b]pyridazine

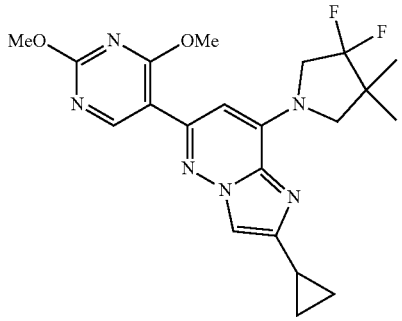 [SMILES: COc1ncc(-c2cc(N3CC(C)(C)C(F)(F)C3)c3nc(C4CC4)cn3n2)c(OC)n1]

2-cyclopropyl-8-(3,3-difluoro-4,4-dimethyl-pyrrolidin-1-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-2-cyclopropyl-8-(3,3-difluoro-4,4-dimethyl-pyrrolidin-1-yl)imidazo[1,2-b]pyridazine. ES/MS m/z: 431.20 [M+H].

Intermediate 334. 4-[(1S,2S)-2-[6-(2,4-dimethoxy-pyrimidin-5-yl)-3-fluoro-imidazo[1,2-b]pyridazin-8-yl]cyclopropyl]benzonitrile

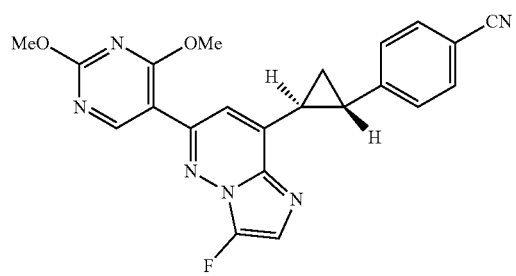 [SMILES: COc1ncc(-c2cc([C@H]3C[C@@H]3c3ccc(C#N)cc3)c3ncc(F)n3n2)c(OC)n1]

4-[(1S,2S)-2-[6-(2,4-dimethoxypyrimidin-5-yl)-3-fluoro-imidazo[1,2-b]pyridazin-8-yl]cyclopropyl]benzonitrile was prepared in the manner described for Intermediate 18, but replacing 6-chloro-8-cyclopropyl-2-methyl-imidazo[1,2-b]pyridazine with 4-[(1S,2S)-2-(6-chloro-3-fluoro-imidazo[1,2-b]pyridazin-8-yl)cyclopropyl]benzonitrile. ES/MS m/z: 417.10 [M+H].

Intermediate 335. 1-[6-(2,4-dimethoxypyrimidin-5-yl)imidazo[1,2-b]pyridazin-8-yl]-4,4-difluoro-pyrrolidin-3-ol was

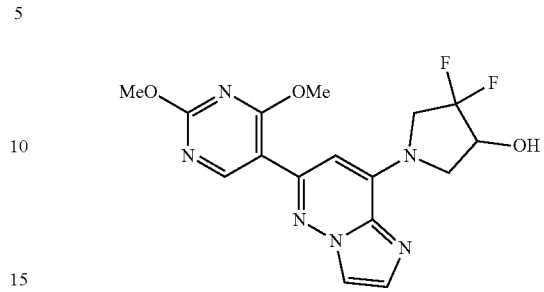

1-[6-(2,4-dimethoxypyrimidin-5-yl)imidazo[1,2-b]pyridazin-8-yl]-4,4-difluoro-pyrrolidin-3-ol was prepared in the manner described for Intermediate 18, but replacing 6-chloro-8-cyclopropyl-2-methyl-imidazo[1,2-b]pyridazine with 1-(6-chloroimidazo[1,2-b]pyridazin-8-yl)-4,4-difluoro-pyrrolidin-3-ol. ES/MS m/z: 379.10 [M+H].

Intermediate 336. 8-[(1S,2S)-2-[1-(2,2-difluoro-ethyl)-7-fluoro-indazol-6-yl]cyclopropyl]-6-(2,4-dimethoxypyrimidin-5-yl)imidazo[1,2-b]pyridazine (Racemic Mixture)

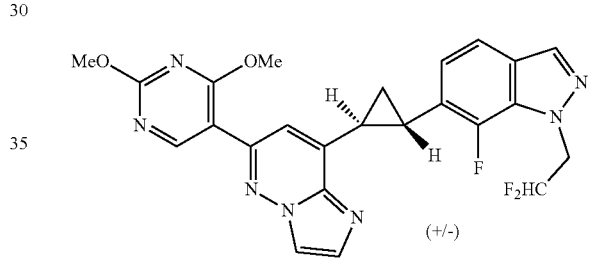

8-[(1S,2S)-[2-(2,2-difluoroethyl)-7-fluoro-indazol-6-yl]cyclopropyl]-6-(2,4-dimethoxypyrimidin-5-yl)imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1S,2S)-2-[1-(2,2-difluoroethyl)-7-fluoro-indazol-6-yl]cyclopropyl]imidazo[1,2-b]pyridazine (Racemic Mixture). ES/MS m/z: 496.20 [M+H].

Intermediate 337. 6-(2,4-dimethoxypyrimidin-5-yl)-8-[(1R,2R)-2-[3-fluoro-1-(2,2,2-trifluoroethyl)indazol-6-yl]cyclopropyl]imidazo[1,2-b]pyridazine

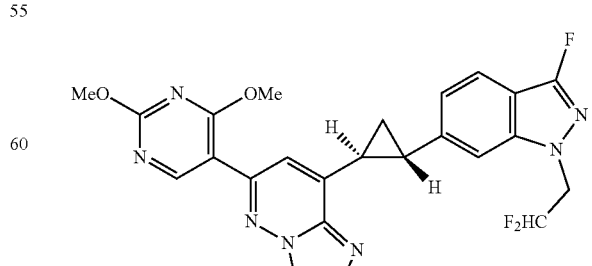

6-(2,4-dimethoxypyrimidin-5-yl)-8-[(1R,2R)-2-[3-fluoro-1-(2,2,2-trifluoroethyl)indazol-6-yl]cyclopropyl]imidazo[1,2-b]pyridazine (Racemic Mixture) was prepared in the manner described for Intermediate 18, but replacing 6-chloro-8-cyclopropyl-2-methyl-imidazo[1,2-b]pyridazine with 6-chloro-8-[(1R,2R)-2-[3-fluoro-1-(2,2,2-trifluoroethyl)indazol-6-yl]cyclopropyl]imidazo[1,2-b]pyridazine (Racemic Mixture).

6-(2,4-dimethoxypyrimidin-5-yl)-8-[(1R,2R)-2-[3-fluoro-1-(2,2,2-trifluoroethyl)indazol-6-yl]cyclopropyl]imidazo[1,2-b]pyridazine was chirally separated from the racemic mixture. ES/MS m/z: 514.20 [M+H].

Intermediate 338. 6-[(1S,2S)-2-[6-(2,4-dimethoxypyrimidin-5-yl)imidazo[1,2-b]pyridazin-8-yl]cyclopropyl]-4-(2,2,2-trifluoroethoxy)isoquinoline (Racemic Mixture)

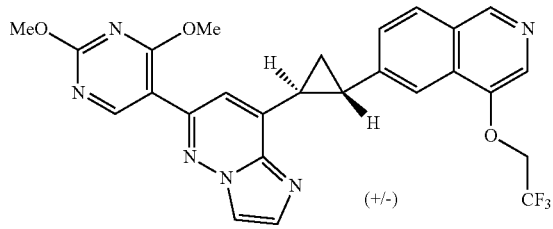 [SMILES: COc1ncc(-c2cc([C@H]3C[C@@H]3c3ccc4cncc(OCC(F)(F)F)c4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]-4-(2,2,2-trifluoroethoxy)isoquinoline (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-4-(2,2,2-trifluoroethoxy)isoquinoline (Racemic Mixture). ES/MS m/z: 523.20 [M+H].

Intermediate 339. 6-[(1S,2S)-2-[6-(2,4-dimethoxypyrimidin-5-yl)imidazo[1,2-b]pyridazin-8-yl]cyclopropyl]-4-(2,2,2-trifluoroethoxy)quinoline (Racemic Mixture)

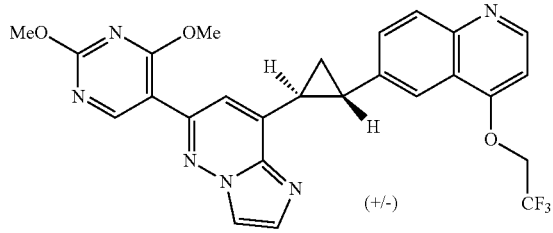 [SMILES: COc1ncc(-c2cc([C@H]3C[C@@H]3c3ccc4nccc(OCC(F)(F)F)c4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]-4-(2,2,2-trifluoroethoxy)quinoline (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-4-(2,2,2-trifluoroethoxy)quinoline (Racemic Mixture). ES/MS m/z: 523.20 [M+H].

Intermediate 340. 6-[(1S,2S)-2-[6-(2,4-dimethoxypyrimidin-5-yl)imidazo[1,2-b]pyridazin-8-yl]cyclopropyl]-1-(2,2,2-trifluoroethyl)quinolin-4-one (Racemic Mixture)

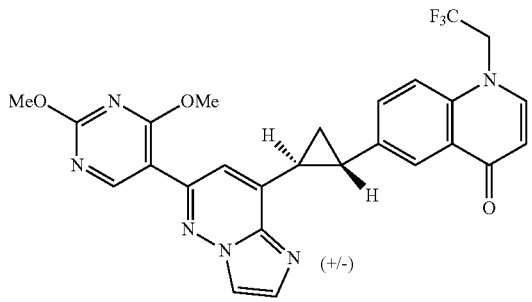 [SMILES: COc1ncc(-c2cc([C@H]3C[C@@H]3c3ccc4c(c3)c(=O)ccn4CC(F)(F)F)c3nccn3n2)c(OC)n1]

6-[(1S,2S)-2-[6-(2,4-dimethoxypyrimidin-5-yl)imidazo[1,2-b]pyridazin-8-yl]cyclopropyl]-1-(2,2,2-trifluoroethyl)quinolin-4-one (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-1-(2,2,2-trifluoroethyl)quinolin-4-one (Racemic Mixture). ES/MS m/z: 523.20 [M+H].

Intermediate 341. 7-[(1S,2S)-2-[6-(2,4-dimethoxypyrimidin-5-yl)imidazo[1,2-b]pyridazin-8-yl]cyclopropyl]-2-(2,2,2-trifluoroethyl)isoquinolin-1-one (Racemic Mixture)

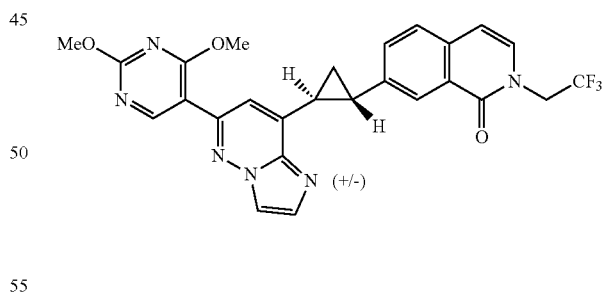

7-[(1S,2S)-2-[6-(2,4-dimethoxypyrimidin-5-yl)imidazo[1,2-b]pyridazin-8-yl]cyclopropyl]-2-(2,2,2-trifluoroethyl)isoquinolin-1-one (Racemic Mixture) was prepared in the manner described for Intermediate 18, but replacing 6-chloro-8-cyclopropyl-2-methyl-imidazo[1,2-b]pyridazine with 7-[(1S,2S)-2-(6-chloroimidazo[1,2-b]pyridazin-8-yl)cyclopropyl]-2-(2,2,2-trifluoroethyl)isoquinolin-1-one (Racemic Mixture). ES/MS m/z: 523.20 [M+H].

Intermediate 342. 6-(2,4-dimethoxypyrimidin-5-yl)-8-[(1S,2S)-2-[3-fluoro-1-(2,2,2-trifluoroethyl)pyrrolo[3,2-c]pyridin-6-yl]cyclopropyl]imidazo[1,2-b]pyridazine

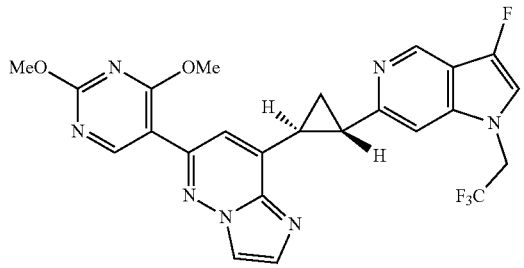 [SMILES: COc1ncc(-c2cc([C@H]3C[C@@H]3c3cc4c(cn3)c(F)cn4CC(F)(F)F)c3nccn3n2)c(OC)n1]

6-(2,4-dimethoxypyrimidin-5-yl)-8-[(1S,2S)-2-[3-fluoro-1-(2,2,2-trifluoroethyl)pyrrolo[3,2-c]pyridin-6-yl]cyclopropyl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[(1S,2S)-2-[3-fluoro-1-(2,2,2-trifluoroethyl)pyrrolo[3,2-c]pyridin-6-yl]cyclopropyl]imidazo[1,2-b]pyridazine. ES/MS m/z: 514.20 [M+H].

Intermediate 343. 6-(2,4-dimethoxypyrimidin-5-yl)-8-[(1S,2S)-2-[1-(2,2,2-trifluoroethyl)pyrrolo[2,3-b]pyridin-6-yl]cyclopropyl]imidazo[1,2-b]pyridazine

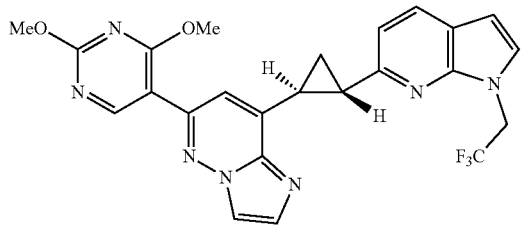 [SMILES: COc1ncc(-c2cc([C@H]3C[C@@H]3c3ccc4ccn(CC(F)(F)F)c4n3)c3nccn3n2)c(OC)n1]

6-(2,4-dimethoxypyrimidin-5-yl)-8-[(1S,2S)-[2-(2,2,2-trifluoroethyl)pyrrolo[2,3-b]pyridin-6-yl]cyclopropyl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[(1S,2S)-[2-(2,2,2-trifluoroethyl)pyrrolo[2,3-b]pyridin-6-yl]cyclopropyl]imidazo[1,2-b]pyridazine. ES/MS m/z: 496.20 [M+H].

Intermediate 344. 6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)indolin-2-one (Racemic Mixture)

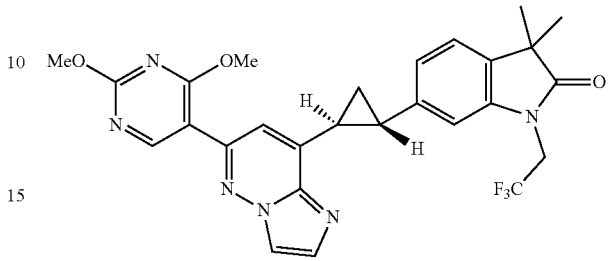

6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)indolin-2-one (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-3,3-dimethyl-1-(2,2,2-trifluoroethyl)indolin-2-one (Racemic Mixture). 6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)indolin-2-one was chirally separated from the racemic mixture by SFC IB column (10% IPA-NH3). ES/MS m/z: 539.20 [M+H].

Intermediate 345. 6-(2,4-dimethoxypyrimidin-5-yl)-8-[(1S,2S)-2-[1-(2,2,2-trifluoroethyl)-3-(trifluoromethyl)pyrrolo[2,3-b]pyridin-6-yl]cyclopropyl]imidazo[1,2-b]pyridazine (Racemic Mixture)

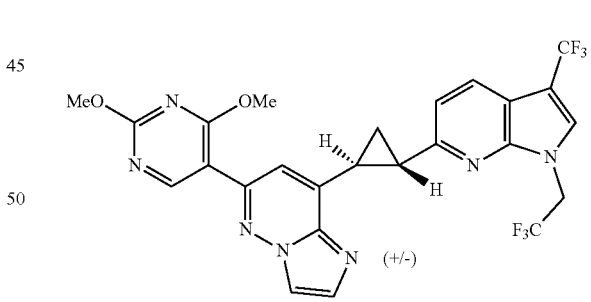

6-(2,4-dimethoxypyrimidin-5-yl)-8-[(1S,2S)-2-[1-(2,2,2-trifluoroethyl)-3-(trifluoromethyl)pyrrolo[2,3-b]pyridin-6-yl]cyclopropyl]imidazo[1,2-b]pyridazine (racemic mixture) was prepared in the manner described for Intermediate 18, but replacing 6-chloro-8-cyclopropyl-2-methyl-imidazo[1,2-b]pyridazine with 6-chloro-8-[(1S,2S)-2-[1-(2,2,2-trifluoroethyl)-3-(trifluoromethyl)pyrrolo[2,3-b]pyridin-6-yl]cyclopropyl]imidazo[1,2-b]pyridazine (Racemic Mixture). ES/MS m/z: 564.20 [M+H].

Intermediate 346. 6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)pyrrolo[3,2-b]pyridin-2-one (Racemic Mixture)

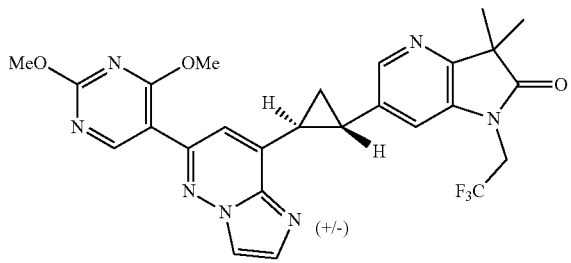 [SMILES: COc1ncc(-c2cc([C@H]3C[C@@H]3c3cnc4c(c3)N(CC(F)(F)F)C(=O)C4(C)C)c3nccn3n2)c(OC)n1]

6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)pyrrolo[3,2-b]pyridin-2-one (racemic mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-3,3-dimethyl-1-(2,2,2-trifluoroethyl)pyrrolo[3,2-b]pyridin-2-one (Racemic Mixture). ES/MS m/z: 540.20 [M+H].

Intermediate 347. 6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)pyrrolo[3,2-b]pyridin-2-one

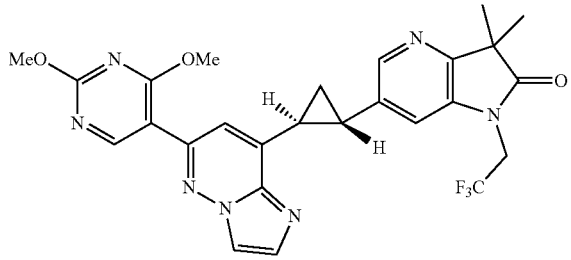 [SMILES: COc1ncc(-c2cc([C@H]3C[C@@H]3c3cnc4c(c3)N(CC(F)(F)F)C(=O)C4(C)C)c3nccn3n2)c(OC)n1]

6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)pyrrolo[3,2-b]pyridin-2-one was chirally separated from Intermediate 346 by SFC Cell 2 column (20% EtOH). ES/MS m/z: 540.20 [M+H].

Intermediate 348. 6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)pyrrolo[3,2-c]pyridin-2-one (Racemic Mixture)

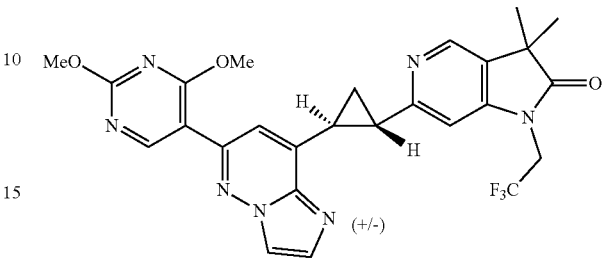

6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)pyrrolo[3,2-c]pyridin-2-one (racemic mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-3,3-dimethyl-1-(2,2,2-trifluoroethyl)pyrrolo[3,2-c]pyridin-2-one (Racemic Mixture). ES/MS m/z: 540.20 [M+H].

Intermediate 349. 6-[(1S,2S)-2-[6-(2,4-dimethoxypyrimidin-5-yl)-3-fluoro-imidazo[1,2-b]pyridazin-8-yl]cyclopropyl]-3,3-dimethyl-1-(2,2,2-trifluoroethyl)indolin-2-one

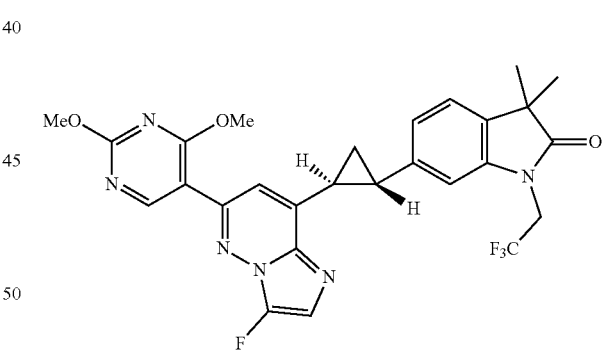

6-[(1S,2S)-2-[6-(2,4-dimethoxypyrimidin-5-yl)-3-fluoro-imidazo[1,2-b]pyridazin-8-yl]cyclopropyl]-3,3-dimethyl-1-(2,2,2-trifluoroethyl)indolin-2-one was prepared in the manner described for Intermediate 18, but replacing 6-chloro-8-cyclopropyl-2-methyl-imidazo[1,2-b]pyridazine with 6-[(1S,2S)-2-(6-chloro-3-fluoro-imidazo[1,2-b]pyridazin-8-yl)cyclopropyl]-3,3-dimethyl-1-(2,2,2-trifluoroethyl)indolin-2-one. ES/MS m/z: 557.20 [M+H].

Intermediate 350. 6-(2,4-dimethoxypyrimidin-5-yl)-3-fluoro-8-[(1S,2S)-2-[3-fluoro-1-(2,2,2-trifluoroethyl)indazol-6-yl]cyclopropyl]imidazo[1,2-b]pyridazine

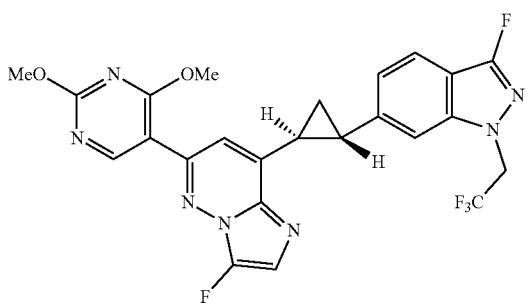 [SMILES: COc1ncc(-c2cc([C@H]3C[C@@H]3c3ccc4c(F)nn(CC(F)(F)F)c4c3)c3ncc(F)n3n2)c(OC)n1]

6-(2,4-dimethoxypyrimidin-5-yl)-3-fluoro-8-[(1S,2S)-2-[3-fluoro-1-(2,2,2-trifluoroethyl)indazol-6-yl]cyclopropyl]imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-[(1S,2S)-2-[3-fluoro-1-(2,2,2-trifluoroethyl)indazol-6-yl]cyclopropyl]imidazo[1,2-b]. ES/MS m/z: 532.20 [M+H].

Intermediate 351. 6-(2,4-dimethoxypyrimidin-5-yl)-8-[(1S,2S)-2-[3-fluoro-1-(2,2,2-trifluoroethyl)indazol-6-yl]cyclopropyl]imidazo[1,2-b]pyridazine

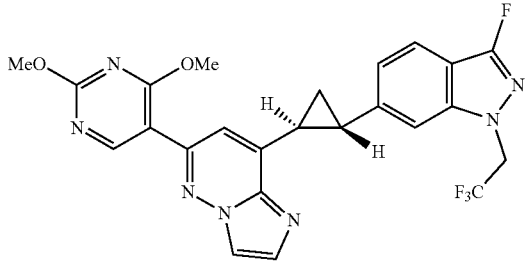 [SMILES: COc1ncc(-c2cc([C@H]3C[C@@H]3c3ccc4c(F)nn(CC(F)(F)F)c4c3)c3nccn3n2)c(OC)n1]

6-(2,4-dimethoxypyrimidin-5-yl)-8-[(1S,2S)-2-[3-fluoro-1-(2,2,2-trifluoroethyl)indazol-6-yl]cyclopropyl]imidazo[1,2-b]pyridazine was chirally separated from the racemic mixture by SFC AD-H column (15% ETOH). ES/MS m/z: 514.20 [M+H].

Intermediate 352. 6-chloro-8-[(1S,2S)-2-[5-(difluoromethoxy)-2-pyridyl]cyclopropyl]imidazo[1,2-b]pyridazine

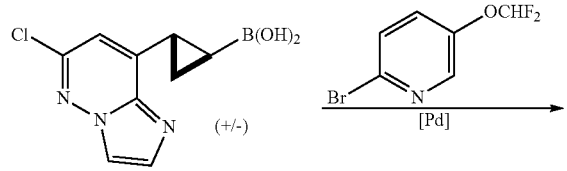

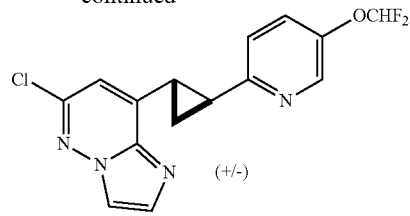

A solution of racemic ((1S,2S)-2-(6-chloroimidazo[1,2-b]pyridazin-8-yl)cyclopropyl)boronic acid (200 mg, 0.84 mmol, 1 equiv), 2-bromo-5-(difluoromethoxy)pyridine (226 mg, 1.01 mmol, 1.2 equiv), potassium phosphate tribasic (536 mg, 2.53 mmol, 3 equiv), and cataCXium-A-Pd-G3 (61 mg, 10 mol %) in 1:5 water:1,4-dioxane (2.5 mL) was degassed with Argon for one minute and heated to 100° C. After 1 hour, the reaction mixture was directly purified by SiO$_2$ chromatography (0-100% EtOAc/Hex), affording racemic 6-chloro-8-[(1S,2S)-2-[5-(difluoromethoxy)-2-pyridyl]cyclopropyl]imidazo[1,2-b]pyridazine. ES/MS m/z: 337.00 [M+H].

Intermediate 353. 6-[(1S,2S)-2-(6-chloroimidazo[1,2-b]pyridazin-8-yl)cyclopropyl]-2-(trifluoromethyl)quinoline

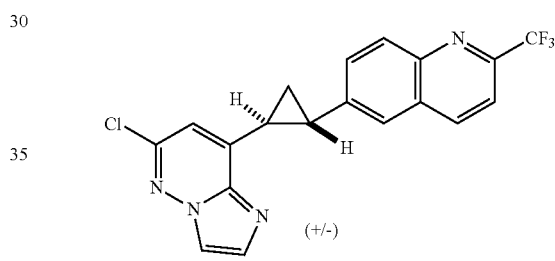

6-[(1S,2S)-2-(6-chloroimidazo[1,2-b]pyridazin-8-yl)cyclopropyl]-2-(trifluoromethyl)quinoline was prepared as a racemic mixture in the manner described for Intermediate 352, but replacing 2-bromo-5-(difluoromethoxy)pyridine with 6-bromo-2-(trifluoromethyl)quinoline. ES/MS m/z: 389.10 [M+H].

Intermediate 354. 6-[(1S,2S)-2-(6-chloroimidazo[1,2-b]pyridazin-8-yl)cyclopropyl]-2-(trifluoromethyl)quinoline

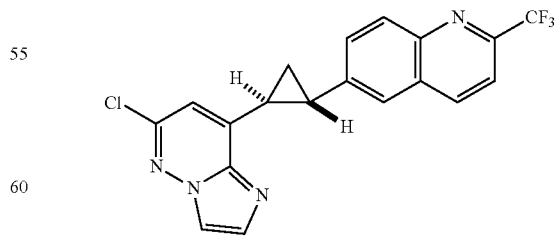

6-[(1S,2S)-2-(6-chloroimidazo[1,2-b]pyridazin-8-yl)cyclopropyl]-2-(trifluoromethyl)quinoline was chirally separated from the racemic Intermediate 353 by SFC OJ-H column (35% EtOH).

Intermediate 355. 6-[(1S,2S)-2-(6-chloroimidazo[1,2-b]pyridazin-8-yl)cyclopropyl]-8-(trifluoromethyl)quinoline

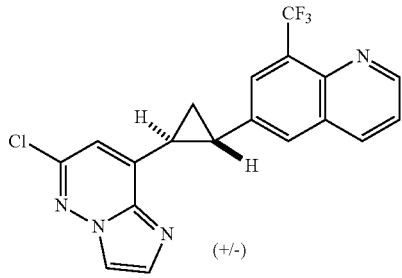 [SMILES: FC(F)(F)c1cc([C@H]2C[C@@H]2c2cc(Cl)nn3ccnc23)cc2cccnc12]

6-[(1S,2S)-2-(6-chloroimidazo[1,2-b]pyridazin-8-yl)cyclopropyl]-8-(trifluoromethyl)quinoline was prepared as a racemic mixture in the manner described for Intermediate 352, but replacing 2-bromo-5-(difluoromethoxy)pyridine with 6-bromo-8-(trifluoromethyl)quinoline. ES/MS m/z: 389.10 [M+H].

Intermediate 356. 6-chloro-8-[(1S,2S)-2-[6-(difluoromethoxy)-3-pyridyl]cyclopropyl]imidazo[1,2-b]pyridazine

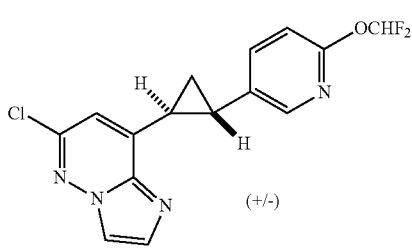 [SMILES: FC(F)Oc1ccc([C@H]2C[C@@H]2c2cc(Cl)nn3ccnc23)cn1]

6-chloro-8-[(1S,2S)-2-[6-(difluoromethoxy)-3-pyridyl]cyclopropyl]imidazo[1,2-b]pyridazine was prepared as a racemic mixture in the manner described for Intermediate 352, but replacing 2-bromo-5-(difluoromethoxy)pyridine with 5-bromo-2-(difluoromethoxy)pyridine. ES/MS m/z: 337.10 [M+H].

Intermediate 357. 7-[(1S,2S)-2-(6-chloroimidazo[1,2-b]pyridazin-8-yl)cyclopropyl]-4-(trifluoromethyl)quinolin

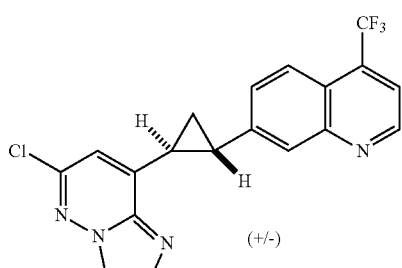

7-[(1S,2S)-2-(6-chloroimidazo[1,2-b]pyridazin-8-yl)cyclopropyl]-4-(trifluoromethyl)quinoline was prepared as a racemic mixture in the manner described for Intermediate 352, but replacing 2-bromo-5-(difluoromethoxy)pyridine with 7-bromo-4-(trifluoromethyl)quinoline. ES/MS m/z: 389.10 [M+H].

Intermediate 358. 6-[(1S,2S)-2-(6-chloroimidazo[1,2-b]pyridazin-8-yl)cyclopropyl]-3-(trifluoromethyl)isoquinoline

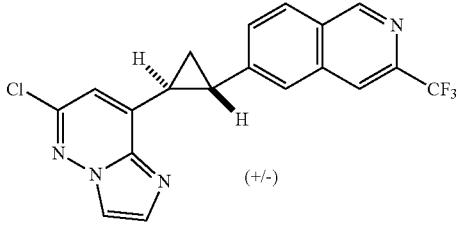 [SMILES: FC(F)(F)c1cc2cc([C@H]3C[C@@H]3c3cc(Cl)nn4ccnc34)ccc2cn1]

6-[(1S,2S)-2-(6-chloroimidazo[1,2-b]pyridazin-8-yl)cyclopropyl]-3-(trifluoromethyl)isoquinoline was prepared as a racemic mixture in the manner described for Intermediate 352, but replacing 2-bromo-5-(difluoromethoxy)pyridine with 6-bromo-3-(trifluoromethyl)isoquinoline. ES/MS m/z: 389.10 [M+H].

Intermediate 359. 6-[(1S,2S)-2-(6-chloroimidazo[1,2-b]pyridazin-8-yl)cyclopropyl]-3-(trifluoromethyl)isoquinoline

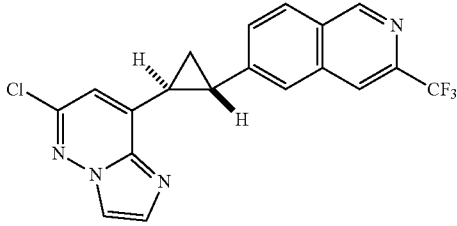 [SMILES: FC(F)(F)c1cc2cc([C@H]3C[C@@H]3c3cc(Cl)nn4ccnc34)ccc2cn1]

6-[(1S,2S)-2-(6-chloroimidazo[1,2-b]pyridazin-8-yl)cyclopropyl]-3-(trifluoromethyl)isoquinoline was chirally separated from the racemic Intermediate 358 by SFC AD-H column (35% MeOH).

Intermediate 360. 6-chloro-8-[(1S,2S)-2-[1-(2,2-difluoroethyl)indazol-6-yl]cyclopropyl]imidazo[1,2-b]pyridazine

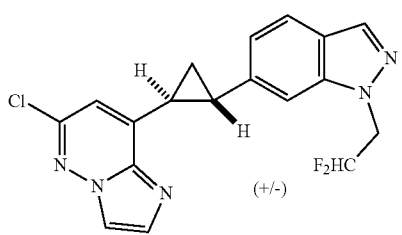 [SMILES: FC(F)Cn1ncc2ccc([C@H]3C[C@@H]3c3cc(Cl)nn4ccnc34)cc21]

6-chloro-8-[(1S,2S)-2-[2-(2,2-difluoroethyl)indazol-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-(2,2-difluoroethyl)indazole. ES/MS m/z: 374.10 [M+H]. and Intermediate 361. 6-chloro-8-[(1S,2S)-2-(1-isopropylindazol-6-yl)cyclopropyl]imidazo[1,2-b]pyridazine

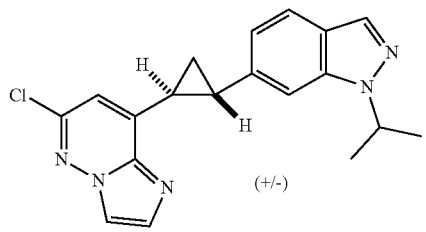 [SMILES: CC(C)n1ncc2ccc([C@H]3C[C@@H]3c3cc(Cl)nn4ccnc34)cc21]

6-chloro-8-[(1S,2S)-2-(1-isopropylindazol-6-yl)cyclopropyl]imidazo[1,2-b]pyridazine was prepared as a racemic mixture in the manner described for Intermediate 352, but replacing 2-bromo-5-(difluoromethoxy)pyridine with 6-bromo-1-isopropyl-indazole. ES/MS m/z: 352.20 [M+H].

Intermediate 362. 6-chloro-8-[(1S,2S)-2-[1-(cyclopropylmethyl)indazol-6-yl]cyclopropyl]imidazo[1,2-b]pyridazine

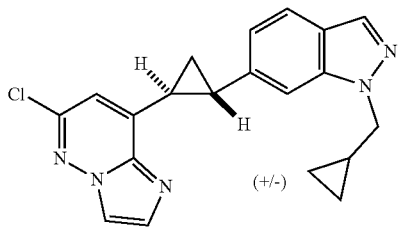 [SMILES: Clc1cc([C@H]2C[C@@H]2c2ccc3cnn(CC4CC4)c3c2)c2nccn2n1]

6-chloro-8-[(1S,2S)-[2-(cyclopropylmethyl)indazol-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-(cyclopropylmethyl)indazole. ES/MS m/z: 364.20 [M+H].

Intermediate 363. 6-chloro-8-[(1S,2S)-2-[1-(2,2,2-trifluoroethyl)pyrrolo[3,2-c]pyridin-6-yl]cyclopropyl]imidazo[1,2-b]pyridazine

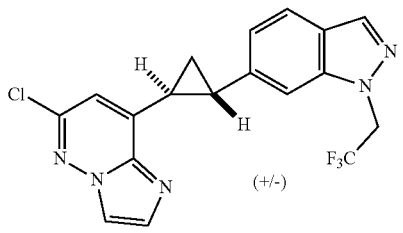 [SMILES: FC(F)(F)Cn1ncc2ccc([C@H]3C[C@@H]3c3cc(Cl)nn4ccnc34)cc21]

6-chloro-8-[(1S,2S)-[2-(2,2,2-trifluoroethyl)pyrrolo[3,2-c]pyridin-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-(2,2,2-trifluoroethyl)pyrrolo[3,2-c]pyridine. ES/MS m/z: 392.10 [M+H].

Intermediate 364. 6-chloro-8-[(1S,2S)-2-[1-(2,2,2-trifluoroethyl)pyrrolo[2,3-b]pyridin-6-yl]cyclopropyl]imidazo[1,2-b]pyridazine

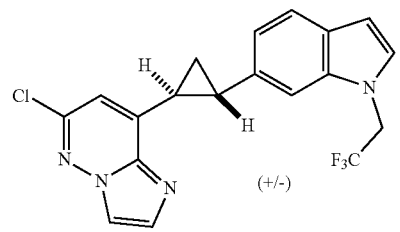 [SMILES: FC(F)(F)Cn1ccc2ccc([C@H]3C[C@@H]3c3cc(Cl)nn4ccnc34)cc21]

6-chloro-8-[(1S,2S)-[2-(2,2,2-trifluoroethyl)pyrrolo[2,3-b]pyridin-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-(2,2,2-trifluoroethyl)pyrrolo[2,3-b]pyridine. ES/MS m/z: 392.10 [M+H].

Intermediate 365. 6-chloro-8-[(1S,2S)-2-[3-cyclopropyl-1-(2,2,2-trifluoroethyl)indazol-6-yl]cyclopropyl]imidazo[1,2-b]pyridazine

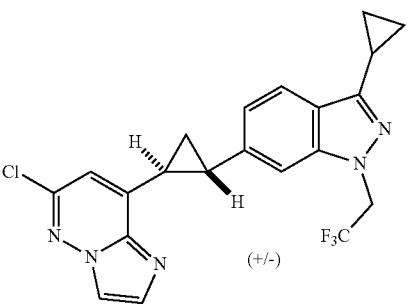 [SMILES: FC(F)(F)Cn1nc(C2CC2)c2ccc([C@H]3C[C@@H]3c3cc(Cl)nn4ccnc34)cc21]

6-chloro-8-[(1S,2S)-2-[3-cyclopropyl-1-(2,2,2-trifluoroethyl)indazol-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-3-cyclopropyl-1-(2,2,2-trifluoroethyl)indazole. ES/MS m/z: 432.10 [M+H].

Intermediate 366. 6-chloro-8-[(1S,2S)-2-[1-[(2,2-difluorocyclopropyl)methyl]indazol-6-yl]cyclopropyl]imidazo[1,2-b]pyridazine

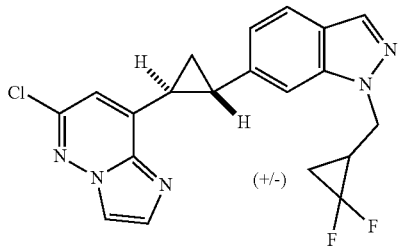 [SMILES: FC1(F)CC1Cn1ncc2ccc([C@H]3C[C@@H]3c3cc(Cl)nn4ccnc34)cc21]

6-chloro-8-[(1S,2S)-2-[2-[(2,2-difluorocyclopropyl)methyl]indazol-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-[(2,2-difluorocyclopropyl)methyl]indazole. ES/MS m/z: 400.10 [M+H].

Intermediate 367. 6-chloro-8-[(1S,2S)-2-[3-fluoro-1-(2,2,2-trifluoroethyl)pyrrolo[3,2-c]pyridin-6-yl]cyclopropyl]imidazo[1,2-b]pyridazine

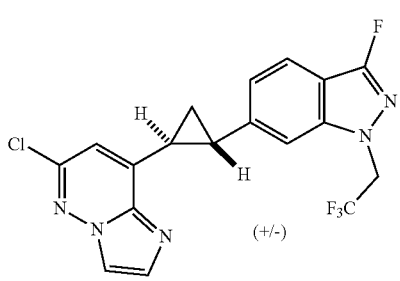 [SMILES: Fc1nn(CC(F)(F)F)c2cc([C@H]3C[C@@H]3c3cc(Cl)nn4ccnc34)ccc12]

6-chloro-8-[(1S,2S)-2-[3-fluoro-1-(2,2,2-trifluoroethyl)pyrrolo[3,2-c]pyridin-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-3-fluoro-1-(2,2,2-trifluoroethyl)pyrrolo[3,2-c]pyridine. ES/MS m/z: 410.10 [M+H].

Intermediate 368. 6-chloro-8-[(1S,2S)-2-[3-fluoro-1-(2,2,2-trifluoroethyl)pyrrolo[3,2-c]pyridin-6-yl]cyclopropyl]imidazo[1,2-b]pyridazine

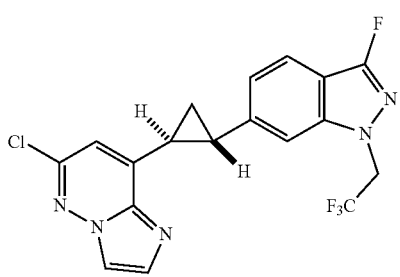 [SMILES: Fc1nn(CC(F)(F)F)c2cc([C@H]3C[C@@H]3c3cc(Cl)nn4ccnc34)ccc12]

6-chloro-8-[(1S,2S)-2-[3-fluoro-1-(2,2,2-trifluoroethyl)pyrrolo[3,2-c]pyridin-6-yl]cyclopropyl]imidazo[1,2-b]pyridazine was chirally separated from the racemic Intermediate 367 by SFC AD-H column (20% IPA-NH3). ES/MS m/z: 410.10 [M+H].

Intermediate 369. 6-chloro-8-[(1S,2S)-2-[1-(2,2,2-trifluoroethyl)pyrrolo[3,2-c]pyridin-6-yl]cyclopropyl]imidazo[1,2-b]pyridazine

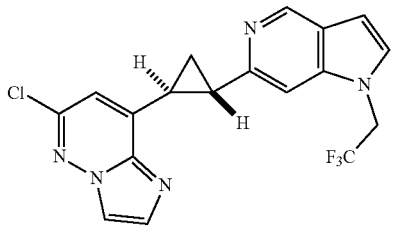 [SMILES: FC(F)(F)Cn1ccc2cnc([C@H]3C[C@@H]3c3cc(Cl)nn4ccnc34)cc21]

6-chloro-8-[(1S,2S)-2-[1-(2,2,2-trifluoroethyl)pyrrolo[3,2-c]pyridin-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-(2,2,2-trifluoroethyl)pyrrolo[3,2-c]pyridine.

Single enantiomer 6-chloro-8-[(1S,2S)-2-[1-(2,2,2-trifluoroethyl)pyrrolo[3,2-c]pyridin-6-yl]cyclopropyl]imidazo[1,2-b]pyridazine was chirally separated from the racemic by SFC AD-H column (20% IPA-NH3). ES/MS m/z: 392.10 [M+H].

Intermediate 370. 6-chloro-8-[(1S,2S)-2-[3-isopropyl-1-(2,2,2-trifluoroethyl)indazol-6-yl]cyclopropyl]imidazo[1,2-b]pyridazine

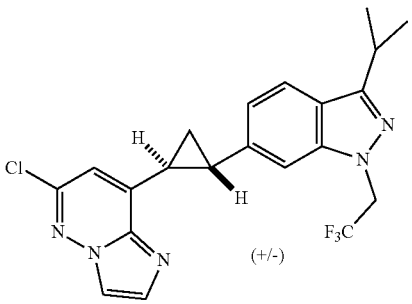 [SMILES: CC(C)c1nn(CC(F)(F)F)c2cc([C@H]3C[C@@H]3c3cc(Cl)nn4ccnc34)ccc12]

6-chloro-8-[(1S,2S)-2-[3-isopropyl-1-(2,2,2-trifluoroethyl)indazol-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-3-isopropyl-1-(2,2,2-trifluoroethyl)indazole. ES/MS m/z: 434.10 [M+H].

Intermediate 371. 6-chloro-8-[(1S,2S)-2-[1-(2,2-difluoroethyl)-7-fluoro-indazol-6-yl]cyclopropyl]imidazo[1,2-b]pyridazine

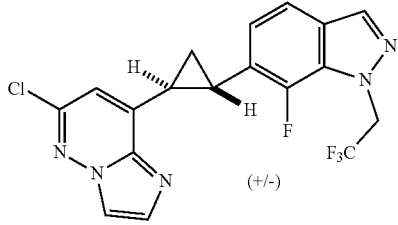 [SMILES: Fc1c([C@H]2C[C@@H]2c2cc(Cl)nn3ccnc23)ccc2cnn(CC(F)(F)F)c12]

6-chloro-8-[(1S,2S)-[2-(2,2-difluoroethyl)-7-fluoro-indazol-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-(2,2-difluoroethyl)-7-fluoro-indazole. ES/MS m/z: 392.10 [M+H].

Intermediate 372. 6-chloro-8-[(1S,2S)-2-[3-fluoro-1-(2,2,2-trifluoroethyl)indazol-6-yl]cyclopropyl]imidazo[1,2-b]pyridazine

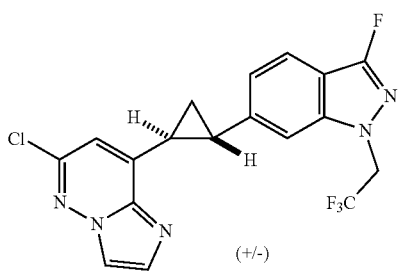 [SMILES: Fc1nn(CC(F)(F)F)c2cc([C@H]3C[C@@H]3c3cc(Cl)nn4ccnc34)ccc12]

6-chloro-8-[(1S,2S)-2-[3-fluoro-1-(2,2,2-trifluoroethyl)indazol-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-3-fluoro-1-(2,2,2-trifluoroethyl)indazole. ES/MS m/z: 410.10 [M+H]. and Intermediate 373. 6-[(1S,2S)-2-(6-chloroimidazo[1,2-b]pyridazin-8-yl)cyclopropyl]-4-(2,2,2-trifluoroethoxy)isoquinoline

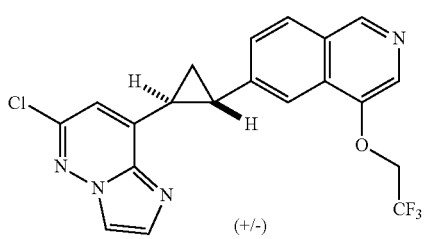 [SMILES: FC(F)(F)COc1cncc2ccc([C@H]3C[C@@H]3c3cc(Cl)nn4ccnc34)cc12]

6-[(1S,2S)-2-(6-chloroimidazo[1,2-b]pyridazin-8-yl)cyclopropyl]-4-(2,2,2-trifluoroethoxy)isoquinoline was prepared as a racemic mixture in the manner described for Intermediate 352, but replacing 2-bromo-5-(difluoromethoxy)pyridine with 6-bromo-4-(2,2,2-trifluoroethoxy)isoquinoline and [(1S,2S)-2-(6-chloroimidazo[1,2-b]pyridazin-8-yl)cyclopropyl]boronic acid. ES/MS m/z: 419.10 [M+H].

Intermediate 374. 6-[(1S,2S)-2-(6-chloroimidazo[1,2-b]pyridazin-8-yl)cyclopropyl]-4-(2,2,2-trifluoroethoxy)quinoline

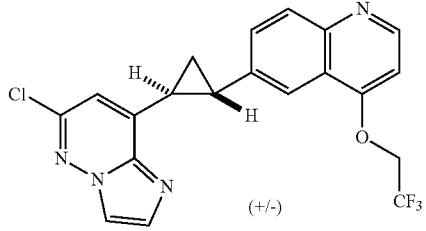 [SMILES: FC(F)(F)COc1ccnc2ccc([C@H]3C[C@@H]3c3cc(Cl)nn4ccnc34)cc12]

6-[(1S,2S)-2-(6-chloroimidazo[1,2-b]pyridazin-8-yl)cyclopropyl]-4-(2,2,2-trifluoroethoxy)quinoline was prepared as a racemic mixture in the manner described for Intermediate 352, but replacing 2-bromo-5-(difluoromethoxy)pyridine with 6-bromo-4-(2,2,2-trifluoroethoxy)quinoline. ES/MS m/z: 419.10 [M+H].

Intermediate 375. 6-[(1S,2S)-2-(6-chloroimidazo[1,2-b]pyridazin-8-yl)cyclopropyl]-1-(2,2,2-trifluoroethyl)quinolin-4-one

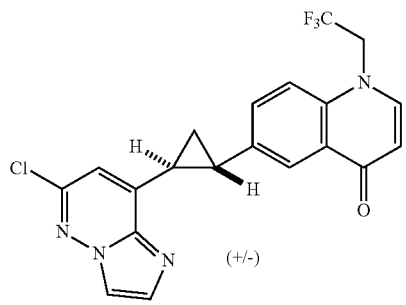 [SMILES: O=c1ccn(CC(F)(F)F)c2ccc([C@H]3C[C@@H]3c3cc(Cl)nn4ccnc34)cc12]

6-[(1S,2S)-2-(6-chloroimidazo[1,2-b]pyridazin-8-yl)cyclopropyl]-1-(2,2,2-trifluoroethyl)quinolin-4-one was prepared as a racemic mixture in the manner described for Intermediate 352, but replacing 2-bromo-5-(difluoromethoxy)pyridine with 6-bromo-1-(2,2,2-trifluoroethyl)quinolin-4-one. ES/MS m/z: 419.10 [M+H].

Intermediate 376. 7-[(1S,2S)-2-(6-chloroimidazo[1,2-b]pyridazin-8-yl)cyclopropyl]-2-(2,2,2-trifluoroethyl)isoquinolin-1-one

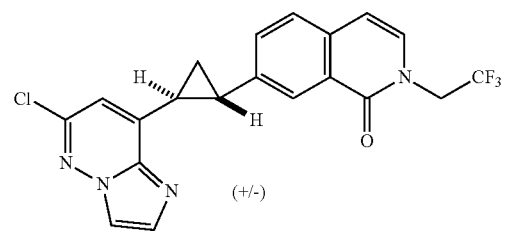 [SMILES: O=c1c2cc([C@H]3C[C@@H]3c3cc(Cl)nn4ccnc34)ccc2ccn1CC(F)(F)F]

7-[(1S,2S)-2-(6-chloroimidazo[1,2-b]pyridazin-8-yl)cyclopropyl]-2-(2,2,2-trifluoroethyl)isoquinolin-1-one was prepared as a racemic mixture in the manner described for Intermediate 352, but replacing 2-bromo-5-(difluoromethoxy)pyridine with 7-bromo-2-(2,2,2-trifluoroethyl)isoquinolin-1-one. ES/MS m/z: 419.10 [M+H].

Intermediate 377. 6-[(1S,2S)-2-(6-chloroimidazo[1,2-b]pyridazin-8-yl)cyclopropyl]-3,3-dimethyl-1-(2,2,2-trifluoroethyl)indolin-2-one

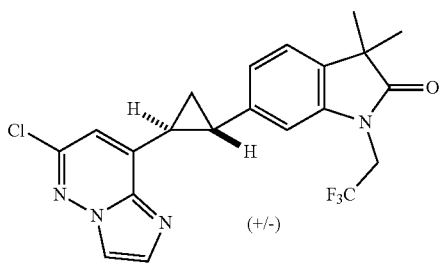 [SMILES: CC1(C)C(=O)N(CC(F)(F)F)c2cc([C@H]3C[C@@H]3c3cc(Cl)nn4ccnc34)ccc21]

(+/-)

6-[(1S,2S)-2-(6-chloroimidazo[1,2-b]pyridazin-8-yl)cyclopropyl]-3,3-dimethyl-1-(2,2,2-trifluoroethyl)indolin-2-one was prepared as a racemic mixture in the manner described for Intermediate 352, but replacing 2-bromo-5-(difluoromethoxy)pyridine with 6-bromo-3,3-dimethyl-1-(2,2,2-trifluoroethyl)indolin-2-one. ES/MS m/z: 435.10 [M+H].

Intermediate 378. 6-chloro-8-[(1S,2S)-2-[1-(2,2,2-trifluoroethyl)pyrrolo[2,3-b]pyridin-6-yl]cyclopropyl]imidazo[1,2-b]pyridazine

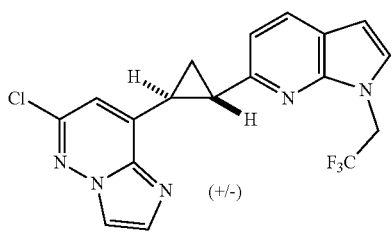 [SMILES: FC(F)(F)Cn1ccc2ccc([C@H]3C[C@@H]3c3cc(Cl)nn4ccnc34)nc21]

(+/-)

6-chloro-8-[(1S,2S)-2-[2-(2,2,2-trifluoroethyl)pyrrolo[2,3-b]pyridin-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-(2,2,2-trifluoroethyl)pyrrolo[2,3-b]pyridine. ES/MS m/z: 392.10 [M+H].

Intermediate 379. 6-chloro-8-[(1S,2S)-2-[1-(2,2,2-trifluoroethyl)pyrrolo[2,3-b]pyridin-6-yl]cyclopropyl]imidazo[1,2-b]pyridazine

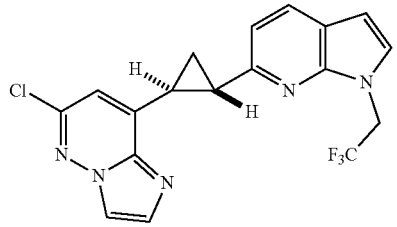 [SMILES: FC(F)(F)Cn1ccc2ccc([C@H]3C[C@@H]3c3cc(Cl)nn4ccnc34)nc21]

6-chloro-8-[(1S,2S)-2-[1-(2,2,2-trifluoroethyl)pyrrolo[2,3-b]pyridin-6-yl]cyclopropyl]imidazo[1,2-b]pyridazine was chirally separated from the racemic Intermediate 378 by SFC TB column (5% EtOH). ES/MS m/z: 392.10 [M+H].

Intermediate 380. 6-chloro-8-[(1S,2S)-2-[1-(2,2,2-trifluoroethyl)-3-(trifluoromethyl)pyrrolo[2,3-b]pyridin-6-yl]cyclopropyl]imidazo[1,2-b]pyridazine

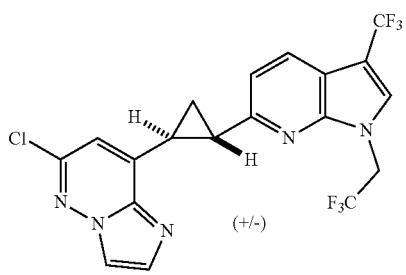 [SMILES: FC(F)(F)Cn1cc(C(F)(F)F)c2ccc([C@H]3C[C@@H]3c3cc(Cl)nn4ccnc34)nc21]

(+/-)

6-chloro-8-[(1S,2S)-2-[1-(2,2,2-trifluoroethyl)-3-(trifluoromethyl)pyrrolo[2,3-b]pyridin-6-yl]cyclopropyl]imidazo[1,2-b]pyridazine was prepared as a racemic mixture in the manner described for Intermediate 352, but replacing 2-bromo-5-(difluoromethoxy)pyridine with 6-bromo-1-(2,2,2-trifluoroethyl)-3-(trifluoromethyl)pyrrolo[2,3-b]pyridine. ES/MS m/z: 460.20 [M+H].

Intermediate 381. 6-[(1S,2S)-2-(6-chloroimidazo[1,2-b]pyridazin-8-yl)cyclopropyl]-3,3-dimethyl-1-(2,2,2-trifluoroethyl)pyrrolo[3,2-b]pyridin-2-one

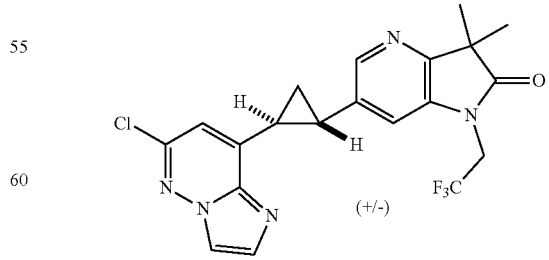

(+/-)

6-[(1S,2S)-2-(6-chloroimidazo[1,2-b]pyridazin-8-yl)cyclopropyl]-3,3-dimethyl-1-(2,2,2-trifluoroethyl)pyrrolo[3,2-b]pyridin-2-one was prepared as a racemic mixture in the Intermediate 382. 6-[(1S,2S)-2-(6-chloroimidazo[1,2-b]pyridazin-8-yl)cyclopropyl]-3,3-dimethyl-1-(2,2,2-trifluoroethyl)pyrrolo[3,2-c]pyridin-2-one

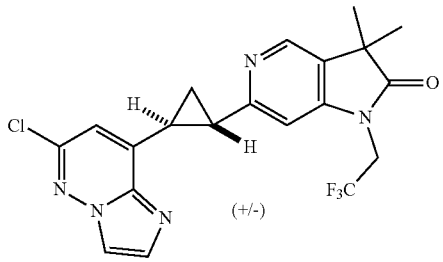 [SMILES: CC1(C)C(=O)N(CC(F)(F)F)c2cc([C@H]3C[C@@H]3c3cc(Cl)nn4ccnc34)ncc21]

6-[(1S,2S)-2-(6-chloroimidazo[1,2-b]pyridazin-8-yl)cyclopropyl]-3,3-dimethyl-1-(2,2,2-trifluoroethyl)pyrrolo[3,2-c]pyridin-2-one was prepared as a racemic mixture in the manner described for Intermediate 352, but replacing 2-bromo-5-(difluoromethoxy)pyridine with 6-chloro-3,3-dimethyl-1-(2,2,2-trifluoroethyl)pyrrolo[3,2-c]pyridin-2-one. ES/MS m/z: 436.40 [M+H].

Intermediate 383. 5-chloro-7-(3,3-difluoro-4,4-dimethylpyrrolidin-1-yl)pyrazolo[1,5-a]pyrimidine

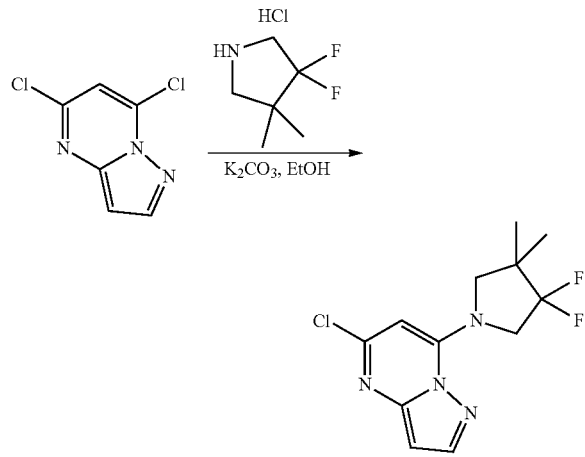

5-chloro-7-(3,3-difluoro-4,4-dimethylpyrrolidin-1-yl)pyrazolo[1,5-a]pyrimidine was prepared as follows: A solution of 5,7-dichloropyrazolo[1,5-a]pyrimidine (200 mg, 1.06 mmol, 1 equiv), 3,3-difluoro-4,4-dimethylpyrrolidine hydrochloride (201 mg, 1.17 mmol, 1.1 equiv) and potassium carbonate (296 mg, 2.13 mmol, 2 equiv) in EtOH (1.6 mL) was heated to 85° C. and stirred for 1 h. The reaction mixture was diluted with water and extracted with EtOAc (3×). The organic layers were combined, washed with brine, dried over Na$_2$SO$_4$, filtered and concentrated in vacuo to afford the title compound. ES/MS m/z: 287.0 [M+H]. $^1$H NMR (400 MHz, DMSO-d6) δ 8.09 (d, J=2.3 Hz, 1H), 6.41 (d, J=2.3 Hz, 1H), 6.07 (s, 1H), 4.52 (t, J=13.7 Hz, 2H), 3.98 (s, 2H), 1.19 (s, 6H). $^{19}$F NMR (376 MHz, DMSO-d6) δ −115.43.

Intermediate 384. 5-chloro-7-(3,3-difluoro-4,4-dimethylpyrrolidin-1-yl)-3-ethylpyrazolo[1,5-a]pyrimidine

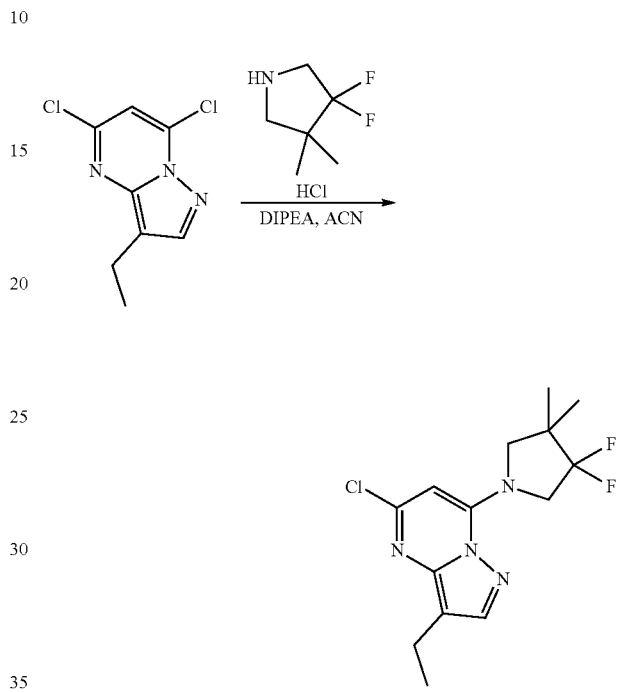

5-chloro-7-(3,3-difluoro-4,4-dimethylpyrrolidin-1-yl)-3-ethylpyrazolo[1,5-a]pyrimidine was prepared as follows: To a solution of 5,7-dichloro-3-ethylpyrazolo[1,5-a]pyrimidine (155 mg, 0.717 mmol, 1 equiv) and 3,3-difluoro-4,4-dimethylpyrrolidine hydrochloride (135 mg, 0.789 mmol, 1.1 equiv) in ACN (4.0 mL) was added DIPEA (0.30 mL, 1.72 mmol, 2.4 equiv). The solution was heated to 85° C. and stirred for 3 h and 20 min. The reaction mixture was diluted with water, the resulting solids filtered, washed with water and dried to afford the title compound. ES/MS m/z: 315.1 [M+H]. $^1$H NMR (400 MHz, Chloroform-d) δ 7.81 (s, 1H), 5.64 (s, 1H), 4.51 (t, J=13.4 Hz, 2H), 3.77 (s, 2H), 2.74 (q, J=7.6 Hz, 2H), 1.29-1.21 (m, 9H). $^{19}$F NMR (376 MHz, Chloroform-d) δ −116.66.

Intermediate 385. 3,5-dichloro-7-(7,7-difluoro-5-azaspiro[2.4]heptan-5-yl)pyrazolo[1,5-a]pyrimidine

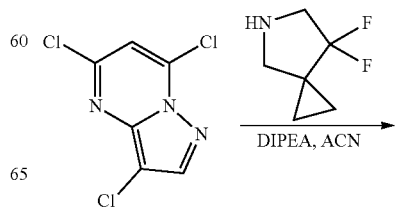

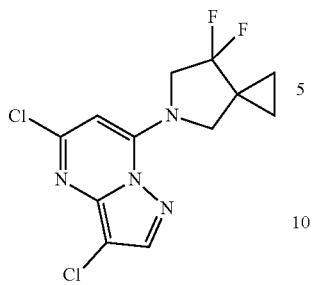

3,5-dichloro-7-(7,7-difluoro-5-azaspiro[2.4]heptan-5-yl) pyrazolo[1,5-a]pyrimidine was prepared as follows: A solution of 3,5,7-trichloropyrazolo[1,5-a]pyrimidine (200 mg, 0.899 mmol, 1 equiv), DIPEA (0.17 mL, 0.989 mmol, 1.1 equiv) and 7,7-difluoro-5-azaspiro[2.4]heptane (132 mg, 0.989 mmol, 1.1 equiv) in ACN (4.0 mL) was stirred at room temperature for 2 h and 40 min prior to dilution with water, filtering the resulting solids, washing further with water and drying to afford the title compound. ES/MS m/z: 319.0 [M+H]. ¹H NMR (400 MHz, Chloroform-d) δ 7.89 (s, 1H), 5.72 (s, 1H), 4.58 (t, J=12.1 Hz, 2H), 4.06 (s, 2H), 1.25-1.18 (m, 2H), 0.92-0.85 (m, 2H). ¹⁹F NMR (376 MHz, Chloroform-d) δ −110.06.

Intermediates 386 and 387. 5-chloro-7-(3,3-difluoro-4,4-dimethylpyrrolidin-1-yl)-3-fluoropyrazolo [1,5-a]pyrimidine and 3,5-dichloro-7-(3,3-difluoro-4,4-dimethylpyrrolidin-1-yl)pyrazolo[1,5-a] pyrimidine

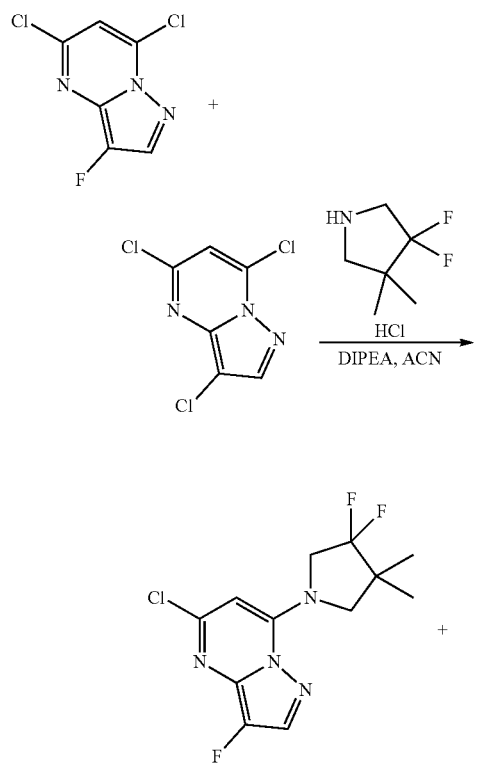

5-chloro-7-(3,3-difluoro-4,4-dimethylpyrrolidin-1-yl)-3-fluoropyrazolo[1,5-a]pyrimidine and 3,5-dichloro-7-(3,3-difluoro-4,4-dimethylpyrrolidin-1-yl)pyrazolo[1,5-a]pyrimidine were prepared in the manner described for Intermediate 385, but replacing 3,5,7-trichloropyrazolo[1,5-a]pyrimidine with a mixture of 5,7-dichloro-3-fluoropyrazolo[1,5-a]pyrimidine and 3,5,7-trichloropyrazolo[1,5-a]pyrimidine and 7,7-difluoro-5-azaspiro[2.4]heptane with 3,3-difluoro-4,4-dimethylpyrrolidine hydrochloride. The reaction mixture was stirred at room temperature for 4 h and 20 min prior to dilution with water, filtering the resulting solids, washing with water and drying to afford the title compounds as a mixture.

Intermediate 386: 5-chloro-7-(3,3-difluoro-4,4-dimethylpyrrolidin-1-yl)-3-fluoropyrazolo[1,5-a]pyrimidine ES/MS m/z: 305.0 [M+H]

Intermediate 387: 3,5-dichloro-7-(3,3-difluoro-4,4-dimethylpyrrolidin-1-yl)pyrazolo[1,5-a]pyrimidine ES/MS m/z: 321.0 [M+H]

Intermediate 388. 5-chloro-7-(3,3-difluoro-4-methylpyrrolidin-1-yl)pyrazolo[1,5-a]pyrimidine

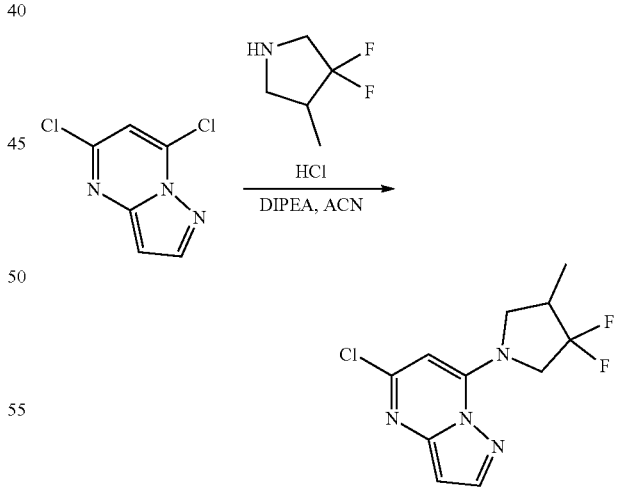

5-chloro-7-(3,3-difluoro-4-methylpyrrolidin-1-yl)pyrazolo[1,5-a]pyrimidine was prepared as follows: A solution of 5,7-dichloropyrazolo[1,5-a]pyrimidine (200 mg, 1.06 mmol, 1 equiv), 3,3-difluoro-4-methylpyrrolidine hydrochloride (184 mg, 1.17 mmol, 1.1 equiv) and DIPEA (0.44 mL, 2.55 mmol, 2.4 equiv) in ACN (4.0 mL) was heated to 85° C. and stirred overnight prior to dilution with water, filtering the resulting solids, washing with water and drying to afford the title compound. ES/MS m/z: 273.0 [M+H]. $^1$H NMR (400 MHz, DMSO-d6) δ8.10 (d, J=2.2 Hz, 1H), 6.41 (d, J=2.2 Hz, 1H), 6.08 (s, 1H), 4.54-4.42 (m, 2H), 4.42-4.31 (m, 1H), 3.74-3.63 (m, 1H), 2.92-2.73 (m, 1H), 1.13 (d, J=6.8 Hz, 3H). $^{19}$F NMR (376 MHz, DMSO-d6) δ −110.05 (d, J=227.9 Hz), −113.87 (d, J=227.8 Hz).

Intermediate 389. 5-chloro-7-(3,3-difluoro-4-methylpyrrolidin-1-yl)-3-fluoropyrazolo[1,5-a]pyrimidine

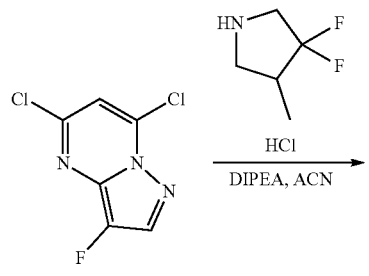

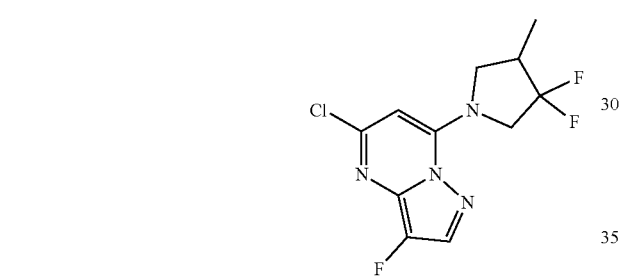

5-chloro-7-(3,3-difluoro-4-methylpyrrolidin-1-yl)-3-fluoropyrazolo[1,5-a]pyrimidine was prepared in the manner described for Intermediate 385, but replacing 3,5,7-trichloropyrazolo[1,5-a]pyrimidine with 5,7-dichloro-3-fluoropyrazolo[1,5-a]pyrimidine and 7,7-difluoro-5-azaspiro[2.4]heptane with 3,3-difluoro-4-methylpyrrolidine hydrochloride. The solution was stirred at room temperature for 4 h and 30 min. The reaction mixture was diluted with water and the resulting solids filtered. The solids were dissolved in EtOAc and the filtrate was concentrated in vacuo to afford the title compound. ES/MS m/z: 291.0 [M+H].

Intermediate 390: 5-chloro-7-(7,7-difluoro-5-azaspiro[2.4]heptan-5-yl)-1H-imidazo[4,5-b]pyridine

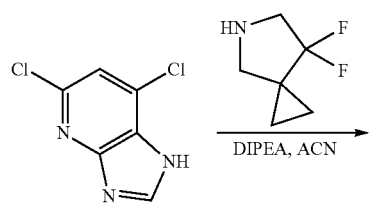

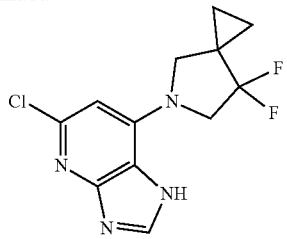

5-chloro-7-(7,7-difluoro-5-azaspiro[2.4]heptan-5-yl)-1H-imidazo[4,5-b]pyridine was prepared as follows: To a solution of 5,7-dichloro-1H-imidazo[4,5-b]pyridine (400 mg, 2.13 mmol, 1 equiv) and 7,7-difluoro-5-azaspiro[2.4]heptane (340 mg, 2.55 mmol, 1.2 equiv) in ACN (10.0 mL) was added DIPEA (0.74 mL, 4.25 mmol, 2 equiv). The solution was heated to 140° C. and stirred overnight. Additional 7,7-difluoro-5-azaspiro[2.4]heptane (340 mg, 2.55 mmol, 1.2 equiv) was added and the reaction mixture was stirred at 140° C. for 3 days. The solution was diluted with water and the resulting solids filtered. The filtrate was re-filtered and the two filter cakes were combined and dried to afford the title compound. ES/MS m/z: 285.1 [M+H]. $^1$H NMR (400 MHz, DMSO-d6) δ 12.91 (s, 1H), 8.11 (s, 1H), 6.25 (s, 1H), 4.40 (t, J=12.7 Hz, 2H), 3.99 (s, 2H), 1.07-1.01 (m, 2H), 0.97-0.92 (m, 2H). $^{19}$F NMR (376 MHz, DMSO-d6) δ −107.25.

Intermediate 391. 5-bromo-7-((1S,2S)-2-(4-(difluoromethyl)phenyl)cyclopropyl)pyrazolo[1,5-a]pyrimidine

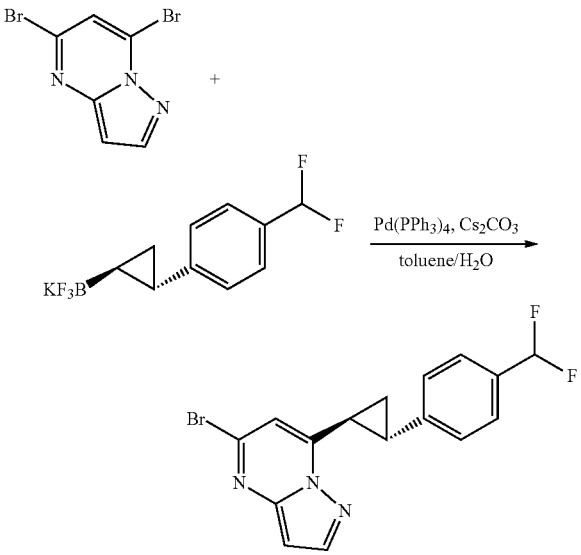

5-bromo-7-((1S,2S)-2-(4-(difluoromethyl)phenyl)cyclopropyl)pyrazolo[1,5-a]pyrimidine was prepared as follows: A microwave vial was charged with potassium ((2S,2S)-2-(4-(difluoromethyl)phenyl)cyclopropyl)trifluoroborate (99 mg, 0.361 mmol, 1 equiv), 5,7-dibromopyrazolo[1,5-a]pyrimidine (110 mg, 0.397 mmol, 1.1 equiv), palladium-tetrakis(triphenylphosphine) (21 mg, 0.018 mmol, 0.05 equiv) and cesium carbonate (353 mg, 1.08 mmol, 3 equiv). To this was added toluene (3.0 mL) and water (0.60 mL).

The reaction mixture was heated to 90° C. and stirred for 2 h and 15 min before turning off the heat and letting the solution stir. The solution was heated again to 90° C. and stirred for 4 h and 15 min before turning off the heat again and leaving to stir overnight. The reaction mixture was diluted with EtOAc and filtered through a pad of Celite. The filtrate was diluted with water and the aqueous layer was extracted with EtOAc (2×). The organic fractions were combined, dried over MgSO$_4$, filtered and concentrated in vacuo prior to purification by silica gel chromatography (0-30% EtOAc in hexanes) to afford the title compound. ES/MS m/z: 363.9 [M+H]. $^1$H NMR (400 MHz, Chloroform-d) δ 8.11 (d, J=2.3 Hz, 1H), 7.48 (d, J=7.9 Hz, 2H), 7.35 (d, J=7.9 Hz, 2H), 6.81-6.42 (m, 3H), 3.17-3.06 (m, 1H), 2.73-2.60 (m, 1H), 1.92-1.74 (m, 2H). $^{19}$F NMR (376 MHz, Chloroform-d) δ −110.88.

Intermediate 392. 7-(3,3-difluoro-4,4-dimethylpyrrolidin-1-yl)-5-(2,4-dimethoxypyrimidin-5-yl)pyrazolo[1,5-a]pyrimidine

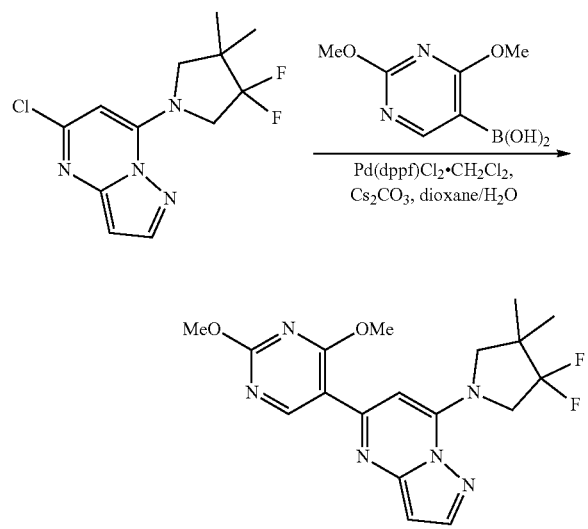

7-(3,3-difluoro-4,4-dimethylpyrrolidin-1-yl)-5-(2,4-dimethoxypyrimidin-5-yl)pyrazolo[1,5-a]pyrimidine was prepared as follows: A microwave vial was charged with 5-chloro-7-(3,3-difluoro-4,4-dimethylpyrrolidin-1-yl)pyrazolo[1,5-a]pyrimidine (150 mg, 0.523 mmol, 1 equiv), (2,4-dimethoxypyrimidin-5-yl)boronic acid (130 mg, 0.707 mmol, 1.35 equiv), Pd(dppf)Cl$_2$CH$_2$Cl$_2$ (43 mg, 0.052 mmol, 0.1 equiv) and cesium carbonate (511 mg, 1.57 mmol, 3 equiv). To this was added 1,4 dioxane (2.0 mL) and water (0.40 mL). The reaction mixture was heated to 90° C. and stirred overnight. After cooling to room temperature, the mixture was diluted with EtOAc and filtered through a pad of Celite. The filtrate was concentrated under reduced pressure and the crude material was purified by silica gel chromatography (0-100% EtOAc in hexanes) to afford the title compound. ES/MS m/z: 391.1 [M+H]. $^1$H NMR (400 MHz, DMSO-d6) δ 8.83 (s, 1H), 8.09 (d, J=2.3 Hz, 1H), 6.50-6.46 (m, 2H), 4.55 (t, J=13.8 Hz, 2H), 4.05 (s, 3H), 3.98 (s, 3H), 3.95 (s, 2H), 1.22 (s, 6H). $^{19}$F NMR (376 MHz, DMSO-d6) δ −115.16.

Intermediate 393. 7-(3,3-difluoro-4,4-dimethylpyrrolidin-1-yl)-5-(2,4-dimethoxypyrimidin-5-yl)-3-ethylpyrazolo[1,5-a]pyrimidine

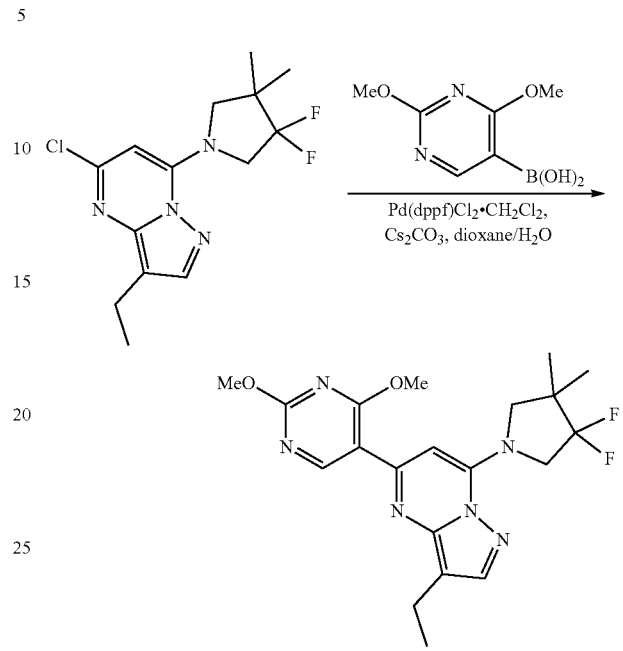

7-(3,3-difluoro-4,4-dimethylpyrrolidin-1-yl)-5-(2,4-dimethoxypyrimidin-5-yl)-3-ethylpyrazolo[1,5-a]pyrimidine was prepared as follows: A microwave vial was charged with 5-chloro-7-(3,3-difluoro-4,4-dimethylpyrrolidin-1-yl)-3-ethylpyrazolo[1,5-a]pyrimidine (150 mg, 0.477 mmol, 1 equiv), (2,4-dimethoxypyrimidin-5-yl)boronic acid (139 mg, 0.756 mmol, 1.59 equiv), Pd(dppf)Cl$_2$CH$_2$Cl$_2$ (39 mg, 0.048 mmol, 0.1 equiv) and cesium carbonate (311 mg, 0.953 mmol, 2 equiv). To this was added 1,4 dioxane (2.0 mL) and water (0.40 mL). The reaction mixture was heated to 90° C. and stirred overnight. After cooling to room temperature, the mixture was diluted with EtOAc and filtered through a pad of Celite. The filtrate was concentrated under reduced pressure and the crude material was purified by silica gel chromatography (0-100% EtOAc in hexanes) to afford the title compound. ES/MS m/z: 419.0 [M+H]. $^1$H NMR (400 MHz, Chloroform-d) δ 8.99 (s, 1H), 7.84 (s, 1H), 6.26 (s, 1H), 4.62-4.45 (m, 2H), 4.16-4.04 (m, 6H), 3.84 (s, 2H), 2.88-2.75 (m, 2H), 1.37-1.25 (m, 9H). $^{19}$F NMR (376 MHz, DMSO-d6) δ −116.32.

Intermediate 394. 3-chloro-7-(7,7-difluoro-5-azaspiro[2.4]heptan-5-yl)-5-(2,4-dimethoxypyrimidin-5-yl)pyrazolo[1,5-a]pyrimidine

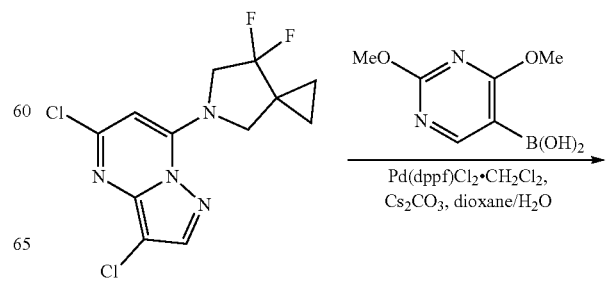

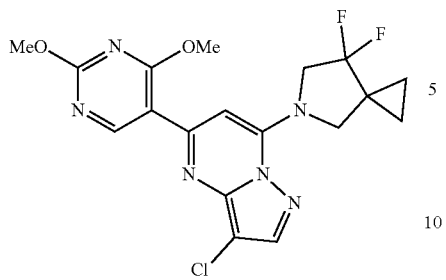

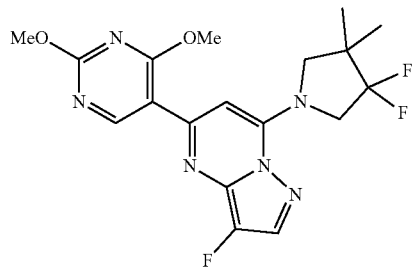

3-chloro-7-(7,7-difluoro-5-azaspiro[2.4]heptan-5-yl)-5-(2,4-dimethoxypyrimidin-5-yl)pyrazolo[1,5-a]pyrimidine was prepared as follows: A microwave vial was charged with (2,4-dimethoxypyrimidin-5-yl)boronic acid (140 mg, 0.762 mmol, 1.3 equiv), 3,5-dichloro-7-(7,7-difluoro-5-azaspiro [2.4]heptan-5-yl)pyrazolo[1,5-a]pyrimidine (187 mg, 0.586 mmol, 1 equiv), Pd(dppf)Cl$_2$CH$_2$Cl$_2$ (48 mg, 0.059 mmol, 0.1 equiv) and cesium carbonate (572 mg, 1.76 mmol, 3 equiv). To this was added 1,4 dioxane (2.0 mL) and water (0.40 mL). The reaction mixture was heated to 90° C. and stirred overnight. After cooling to room temperature, the mixture was diluted with EtOAc and filtered through a pad of Celite. The filtrate was concentrated under reduced pressure and the crude material was purified by silica gel chromatography (0-100% EtOAc in hexanes) to afford the title compound. ES/MS m/z: 423.0 [M+H]. $^1$H NMR (400 MHz, DMSO-d6) δ 8.89 (s, 1H), 8.26 (s, 1H), 6.59 (s, 1H), 4.63 (t, J=12.4 Hz, 2H), 4.16 (s, 2H), 4.06 (s, 3H), 3.99 (s, 3H), 1.10-0.98 (m, 4H). $^{19}$F NMR (376 MHz, DMSO-d6) δ −107.57.

Intermediates 395 and 396. 7-(3,3-difluoro-4,4-dimethylpyrrolidin-1-yl)-5-(2,4-dimethoxypyrimidin-5-yl)-3-fluoropyrazolo[1,5-a]pyrimidine and 3-chloro-7-(3,3-difluoro-4,4-dimethylpyrrolidin-1-yl)-5-(2,4-dimethoxypyrimidin-5-yl)pyrazolo[1,5-a] pyrimidine

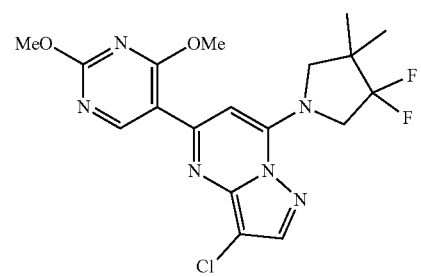

7-(3,3-difluoro-4,4-dimethylpyrrolidin-1-yl)-5-(2,4-dimethoxypyrimidin-5-yl)-3-fluoropyrazolo[1,5-a]pyrimidine and 3-chloro-7-(3,3-difluoro-4,4-dimethylpyrrolidin-1-yl)-5-(2,4-dimethoxypyrimidin-5-yl)pyrazolo[1,5-a]pyrimidine were prepared in the manner described for Intermediate 394, but replacing 3,5-dichloro-7-(7,7-difluoro-5-azaspiro[2.4] heptan-5-yl)pyrazolo[1,5-a]pyrimidine with a mixture of 5-chloro-7-(3,3-difluoro-4,4-dimethylpyrrolidin-1-yl)-3-fluoropyrazolo[1,5-a]pyrimidine and 3,5-dichloro-7-(3,3-difluoro-4,4-dimethylpyrrolidin-1-yl)pyrazolo[1,5-a]pyrimidine.

Intermediate 395: 7-(3,3-difluoro-4,4-dimethylpyrrolidin-1-yl)-5-(2,4-dimethoxypyrimidin-5-yl)-3-fluoropyrazolo[1,5-a]pyrimidine ES/MS m/z: 409.1 [M+H]

Intermediate 396: 3-chloro-7-(3,3-difluoro-4,4-dimethylpyrrolidin-1-yl)-5-(2,4-dimethoxypyrimidin-5-yl)pyrazolo[1,5-a]pyrimidine ES/MS m/z: 425.0 [M+H]

Intermediate 397. 7-(3,3-difluoro-4-methylpyrrolidin-1-yl)-5-(2,4-dimethoxypyrimidin-5-yl)pyrazolo [1,5-a]pyrimidine

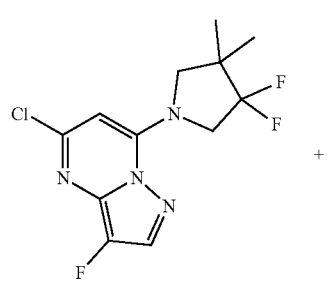

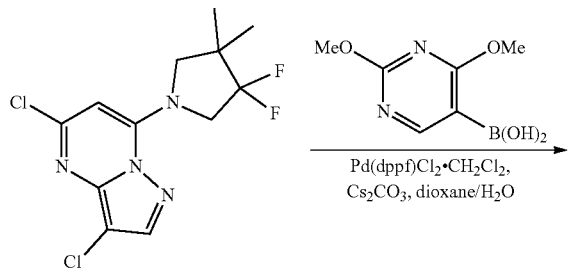

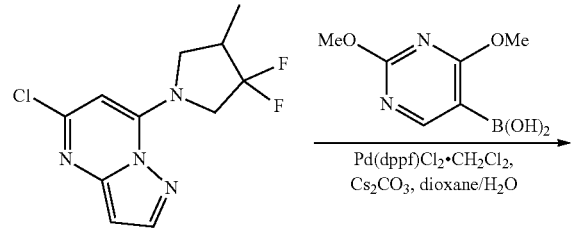

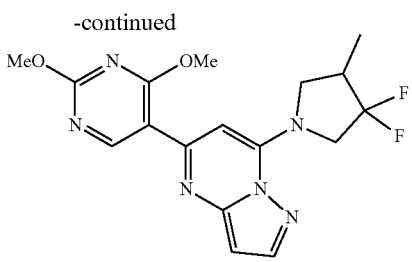

7-(3,3-difluoro-4-methylpyrrolidin-1-yl)-5-(2,4-dimethoxypyrimidin-5-yl)pyrazolo[1,5-a]pyrimidine was prepared as follows: A microwave vial was charged with (2,4-dimethoxypyrimidin-5-yl)boronic acid (219 mg, 1.19 mmol, 1.35 equiv), 5-chloro-7-(3,3-difluoro-4-methylpyrrolidin-1-yl)pyrazolo[1,5-a]pyrimidine (240 mg, 0.880 mmol, 1 equiv), Pd(dppf)Cl$_2$·CH$_2$Cl$_2$ (72 mg, 0.088 mmol, 0.1 equiv) and cesium carbonate (860 mg, 2.64 mmol, 3 equiv). To this was added 1,4 dioxane (4.0 mL) and water (0.80 mL). The reaction mixture was heated to 90° C. and stirred for 6 h and 30 min. After cooling to room temperature, the mixture was diluted with EtOAc and filtered through a pad of Celite. The filtrate was concentrated under reduced pressure and the crude material was purified by silica gel chromatography (0-100% EtOAc in hexanes) to afford the title compound. ES/MS m/z: 377.1 [M+H]. $^1$H NMR (400 MHz, DMSO-d6) δ 8.83 (s, 1H), 8.09 (d, J=2.3 Hz, 1H), 6.49 (s, 1H), 6.48 (d, J=2.3 Hz, 1H), 4.59-4.44 (m, 2H), 4.37-4.29 (m, 1H), 4.04 (s, 3H), 3.98 (s, 3H), 3.71-3.63 (m, 1H), 2.95-2.77 (m, 1H), 1.16 (d, J=6.8 Hz, 3H). $^{19}$F NMR (376 MHz, DMSO-d6) δ −109.34 (d, J=227.4 Hz), −113.60 (d, J=227.4 Hz).

Intermediate 398. 7-(3,3-difluoro-4-methylpyrrolidin-1-yl)-5-(2,4-dimethoxypyrimidin-5-yl)-3-fluoropyrazolo[1,5-a]pyrimidine

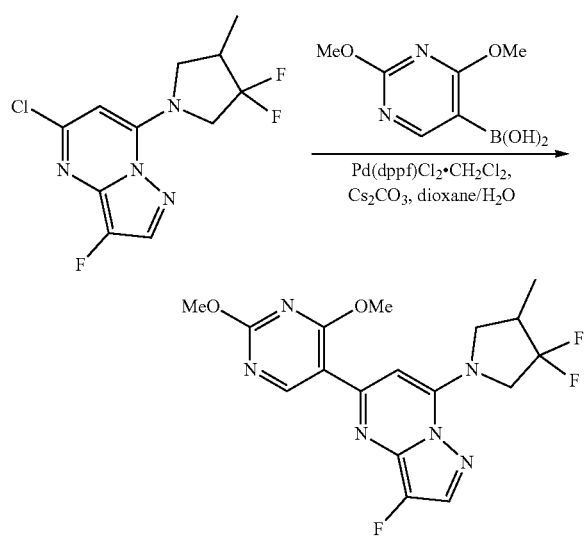

7-(3,3-difluoro-4-methylpyrrolidin-1-yl)-5-(2,4-dimethoxypyrimidin-5-yl)-3-fluoropyrazolo[1,5-a]pyrimidine was prepared in the manner described for Intermediate 397, but replacing 5-chloro-7-(3,3-difluoro-4-methylpyrrolidin-1-yl)pyrazolo[1,5-a]pyrimidine with 5-chloro-7-(3,3-difluoro-4-methylpyrrolidin-1-yl)-3-fluoropyrazolo[1,5-a]pyrimidine. ES/MS m/z: 395.1 [M+H].

Intermediates 399 and 400 5,7-dichloro-3-fluoropyrazolo[1,5-a]pyrimidine and 3,5,7-trichloropyrazolo[1,5-a]pyrimidine

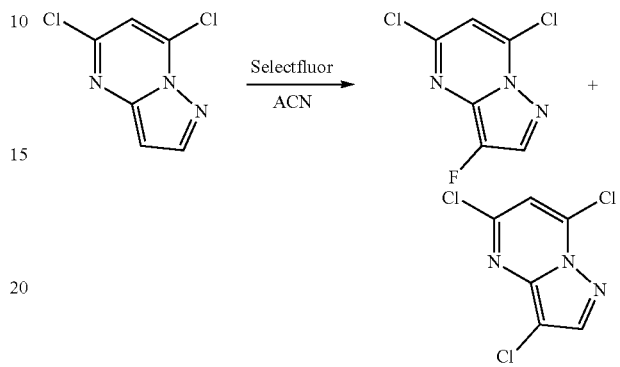

5,7-dichloro-3-fluoropyrazolo[1,5-a]pyrimidine and 3,5,7-trichloropyrazolo[1,5-a]pyrimidine were prepared as follows: To a solution of 5,7-dichloropyrazolo[1,5-a]pyrimidine (500 mg, 2.66 mmol, 1 equiv) in ACN (12.0 mL) was added Selectfluor™ (942 mg, 2.66 mmol, 1 equiv). The reaction mixture was heated to 60° C. and stirred overnight. The reaction was then stirred at 70° C. for 1 h and 45 min. Additional Selectfluor™ (300 mg, 0.847 mmol) was added and the solution was stirred at 70° C. for 3 days. Additional Selectfluor™ (300 mg, 0.847 mmol) was again added and the reaction was stirred at 70° C. for 1 h and 30 minutes. After cooling to room temperature, the reaction mixture was quenched carefully with saturated sodium bicarbonate until gas formation ceased. The solution was diluted with water and extracted with EtOAc (3×). The organic fractions were combined, dried over MgSO$_4$, filtered and concentrated in vacuo. The crude material was purified by silica gel chromatography (0-80% DCM in hexanes) to afford the title compounds as a mixture. 3,5,7-trichloropyrazolo[1,5-a]pyrimidine was carried through the proceeding reactions as a side-product.

Intermediate 399 5,7-dichloro-3-fluoropyrazolo[1,5-a]pyrimidine ES/MS m/z: 206.0 [M+H]. $^1$H NMR (400 MHz, DMSO-d6) δ 8.57 (d, J=3.3 Hz, 1H), 7.71 (s, 1H). $^{19}$F NMR (376 MHz, DMSO-d6) δ −180.70.

Intermediate 400 3,5,7-trichloropyrazolo[1,5-a]pyrimidine ES/MS m/z: 221.9 [M+H].

Intermediate 401
5,7-dibromopyrazolo[1,5-a]pyrimidine

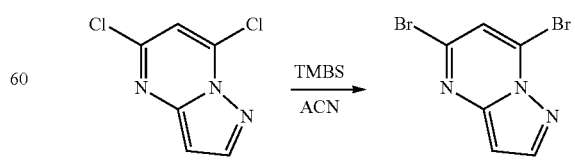

5,7-dibromopyrazolo[1,5-a]pyrimidine was prepared as follows: A solution of 5,7-dichloropyrazolo[1,5-a]pyrimidine (200 mg, 1.06 mmol, 1 equiv) and bromotrimethylsilane (0.70 mL, 5.32 mmol, 5 equiv) in ACN (5.0 mL) was stirred at room temperature for 2 h and 40 min. The reaction mixture was heated to 50° C. and stirred for 1 h. It was then heated to 120° C. and stirred for an additional 1 h. The reaction mixture was loaded onto Celite and purified by silica gel chromatography (0-10% MeOH in DCM) to afford the title compound. ES/MS m/z: 275.8 [M+H]. $^1$H NMR (400 MHz, Chloroform-d) δ 8.21 (d, J=2.4 Hz, 1H), 7.28 (s, 1H), 6.79 (d, J=2.3 Hz, 1H).

Intermediate 402. Potassium ((2S,2S)-2-(4-(difluoromethyl)phenyl)cyclopropyl)trifluoroborate

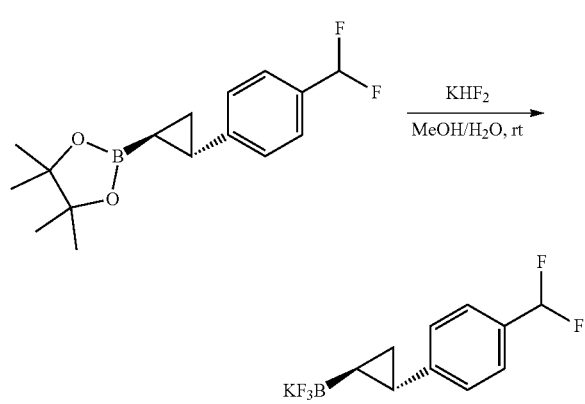

Potassium ((2S,2S)-2-(4-(difluoromethyl)phenyl)cyclopropyl)trifluoroborate was prepared as follows: To a solution of 24(1S,2S)-2-(4-(difluoromethyl)phenyl)cyclopropyl)-4,4,5,5-tetramethyl-1,3,2-dioxaborolane (169 mg, 0.575 mmol, 1 equiv) in 5:1 MeOH/H$_2$O (3.0 mL) was added potassium bifluoride (314 mg, 4.02 mmol, 7 equiv). The solution was stirred at room temperature for 4 h prior to concentrating in vacuo. The mixture was diluted with ACN and filtered. The filtrate was concentrated in vacuo and the resulting solids were washed with Et$_2$O, filtered and dried to afford the title compound. $^1$H NMR (400 MHz, Acetonitrile-d3) δ 7.34 (d, J=8.1 Hz, 2H), 7.12 (d, J=8.0 Hz, 2H), 6.69 (t, J=56.6 Hz, 1H), 1.64-1.57 (m, 1H), 0.83-0.74 (m, 1H), 0.59-0.50 (m, 1H), −0.05-−0.16 (m, 1H). $^{19}$F NMR (376 MHz, Acetonitrile-d3) δ −109.92, −143.89-−145.90 (m).

Intermediate 403. 4,4-difluoropyrrolidin-3-ol hydrochloride

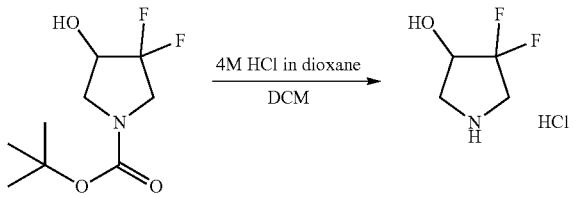

4,4-difluoropyrrolidin-3-ol hydrochloride was prepared as follows: To a solution of tert-butyl 3,3-difluoro-4-hydroxy-pyrrolidine-1-carboxylate in DCM (5.0 mL) was added 4.0 M HCl in dioxane (5.0 mL, 20.2 mmol, 9 equiv). The reaction mixture was stirred at room temperature. Upon completion, the solution was concentrated in vacuo to afford the title compound. $^1$H NMR (400 MHz, DMSO-d6) δ 10.04 (s, 2H), 6.60 (d, J=4.8 Hz, 1H), 4.36-4.27 (m, 1H), 3.72-3.51 (m, 2H), 3.50-3.42 (m, 1H), 3.26-3.19 (m, 1H). $^{19}$F NMR (376 MHz, DMSO-d6) δ −106.59 (d, J=237.6 Hz), −121.44 (d, J=237.6 Hz).

Intermediate 404. 1-(6-chloroimidazo[1,2-b]pyridazin-8-yl)-4,4-difluoropyrrolidin-3-ol

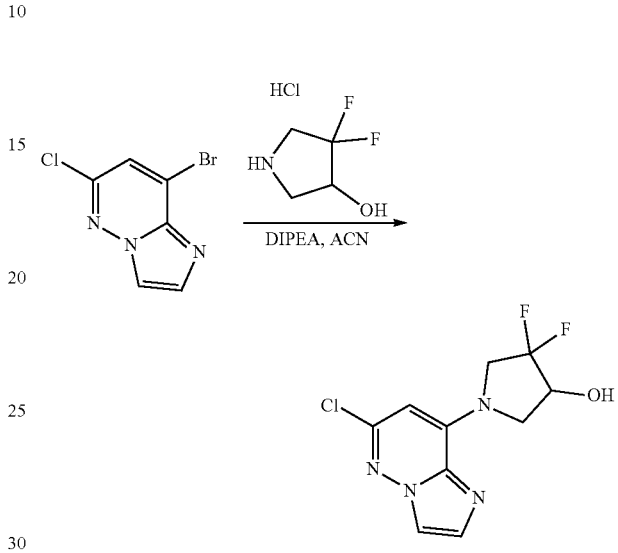

1-(6-chloroimidazo[1,2-b]pyridazin-8-yl)-4,4-difluoropyrrolidin-3-ol was prepared as follows: A solution of 8-bromo-6-chloroimidazo[1,2-b]pyridazine (523 mg, 2.25 mmol, 1 equiv), 4,4-difluoropyrrolidin-3-ol hydrochloride (359 mg, 2.25 mmol, 1 equiv) and DIPEA (0.94 mL, 5.40 mmol, 2.4 equiv) in ACN (10.0 mL) was stirred at 70° C. for 1 h and 30 min. The heat was turned off and the reaction was left to stir for 3 days. The reaction was heated to 70° C. and stirred for an additional 2 h and 30 min prior to cooling to room temperature, diluting with water and extracting the aqueous layer with EtOAc (2×). The organic fractions were combined, dried over MgSO$_4$, filtered and concentrated in vacuo to afford the title compound. ES/MS m/z: 275.0 [M+H]. $^1$H NMR (400 MHz, DMSO-d6) δ 8.09-8.06 (m, 1H), 7.60-7.58 (m, 1H), 6.27 (d, J=5.2 Hz, 1H), 6.13 (s, 1H), 4.55-3.90 (m, 5H). $^{19}$F NMR (376 MHz, DMSO-d6) δ −108.31-−111.78 (m), −122.76 (d, J=233.4 Hz).

Intermediate 405. 1-(6-(2,4-dimethoxypyrimidin-5-yl)imidazo[1,2-b]pyridazin-8-yl)-4,4-difluoropyrrolidin-3-ol

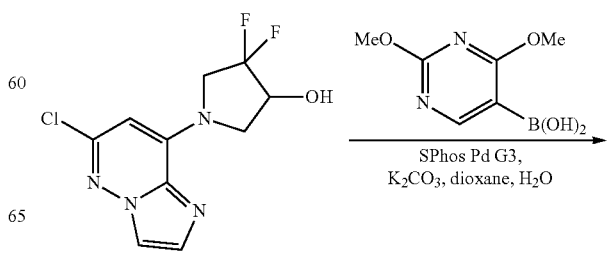

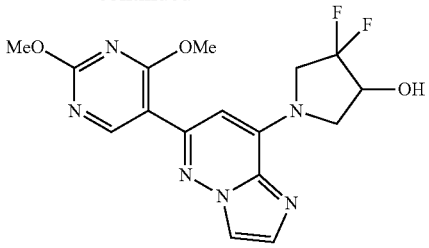

1-(6-(2,4-dimethoxypyrimidin-5-yl)imidazo[1,2-b]pyridazin-8-yl)-4,4-difluoropyrrolidin-3-ol was prepared as follows: A microwave vial was charged with 1-(6-chloro-imidazo[1,2-b]pyridazin-8-yl)-4,4-difluoropyrrolidin-3-ol (650 mg, 2.37 mmol, 1 equiv), (2,4-dimethoxypyrimidin-5-yl)boronic acid (653 mg, 3.55 mmol, 1.5 equiv), SPhos Pd G3 (277 mg, 0.355 mmol, 0.15 equiv) and potassium carbonate (654 mg, 4.73 mmol, 2 equiv). To this was added 1,4 dioxane (10.0 mL) and water (1.0 mL). The reaction mixture was heated to 90° C. and stirred overnight. After cooling to room temperature, the solution was diluted with water and extracted with EtOAc (3×). The organic fractions were combined, dried over MgSO4, filtered and concentrated in vacuo. The crude material was purified by silica gel chromatography (0-100% EtOAc in hexanes then 0-30% MeOH in EtOAc) to afford the title compound. ES/MS m/z: 379.1 [M+H]. $^1$H NMR (400 MHz, DMSO-d6) δ 8.57 (s, 1H), 8.12 (d, J=1.2 Hz, 1H), 7.59 (d, J=1.2 Hz, 1H), 6.28-6.23 (m, 2H), 4.53-4.06 (m, 5H), 4.00-3.96 (m, 6H). $^{19}$F NMR (376 MHz, DMSO-d6) δ −109.26−−110.86 (m), −122.68 (d, J=232.8 Hz).

Intermediate 406. 4-((1-(6-(2,4-dimethoxypyrimidin-5-yl)imidazo[1,2-b]pyridazin-8-yl)-4,4-difluoropyrrolidin-3-yl)oxy)benzonitrile

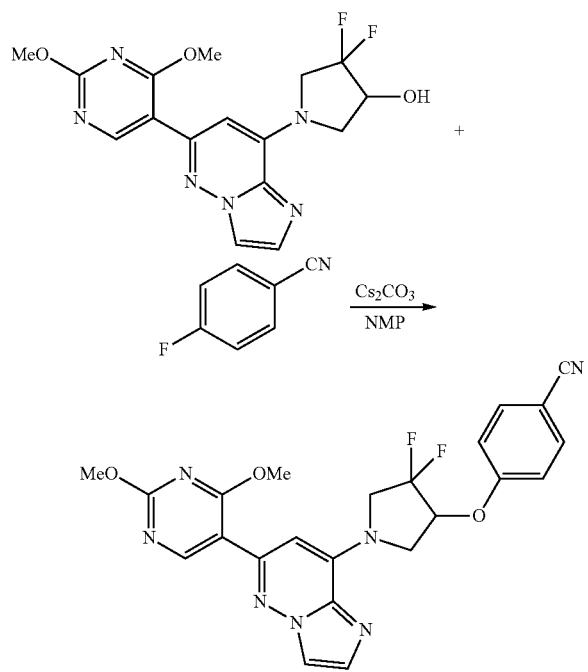

4-((1-(6-(2,4-dimethoxypyrimidin-5-yl)imidazo[1,2-b]pyridazin-8-yl)-4,4-difluoropyrrolidin-3-yl)oxy)benzonitrile was prepared as follows: A solution of 1-(6-(2,4-dimethoxypyrimidin-5-yl)imidazo[1,2-b]pyridazin-8-yl)-4,4-difluoropyrrolidin-3-ol (50 mg, 0.132 mmol, 1 equiv), 4-fluorobenzonitrile (32 mg, 0.264 mmol, 2 equiv) and cesium carbonate (129 mg, 0.396 mmol, 3 equiv) in NMP (1.0 mL) was heated to 85° C. and stirred for 2 h. The reaction mixture was diluted with a solution of saturated sodium bicarbonate and water. The aqueous layer was extracted with EtOAc. The organic fractions were combined, dried over MgSO4, filtered and concentrated in vacuo prior to purification by silica gel chromatography (0-100% EtOAc in hexanes) to afford the title compound. ES/MS m/z: 480.1 [M+H].

Intermediate 407. 8-(4-((5-(difluoromethyl)pyridin-2-yl)oxy)-3,3-difluoropyrrolidin-1-yl)-6-(2,4-dimethoxypyrimidin-5-yl)imidazo[1,2-b]pyridazine

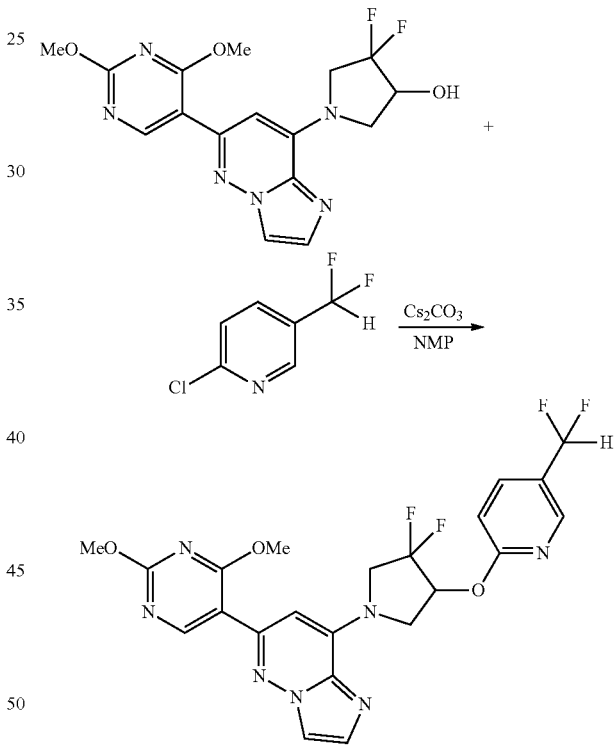

8-(4-(5-(difluoromethyl)pyridin-2-yl)oxy)-3,3-difluoropyrrolidin-1-yl)-6-(2,4-dimethoxypyrimidin-5-yl)imidazo[1,2-b]pyridazine was prepared as follows: A solution of 1-(6-(2,4-dimethoxypyrimidin-5-yl)imidazo[1,2-b]pyridazin-8-yl)-4,4-difluoropyrrolidin-3-ol (30 mg, 0.079 mmol, 1 equiv), 2-chloro-5-(difluoromethyl)pyridine (26 mg, 0.159 mmol, 2 equiv) and cesium carbonate (78 mg, 0.238 mmol, 3 equiv) in NMP (1.0 mL) was heated to 85° C. and stirred for 45 min. The temperature was increased to 110° C. and the solution was left to stir for 3 days. The reaction mixture was diluted with a saturated solution of sodium bicarbonate and water. The aqueous layer was extracted with EtOAc. The organic fractions were combined, dried over MgSO4 and concentrated in vacuo prior to Intermediate 408. 1-(6-(2,4-dimethoxypyrimidin-5-yl)imidazo[1,2-b]pyridazin-8-yl)-4,4-difluoropyrrolidin-3-yl (2-fluorophenyl)carbamate Intermediate 409. 3-((6-(2,4-di-tert-butoxypyrimidin-5-yl)imidazo[1,2-b]pyridazin-8-yl)oxy)-2,2-difluoropropyl (2-fluorophenyl)carbamate

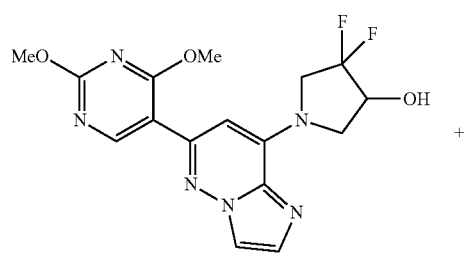

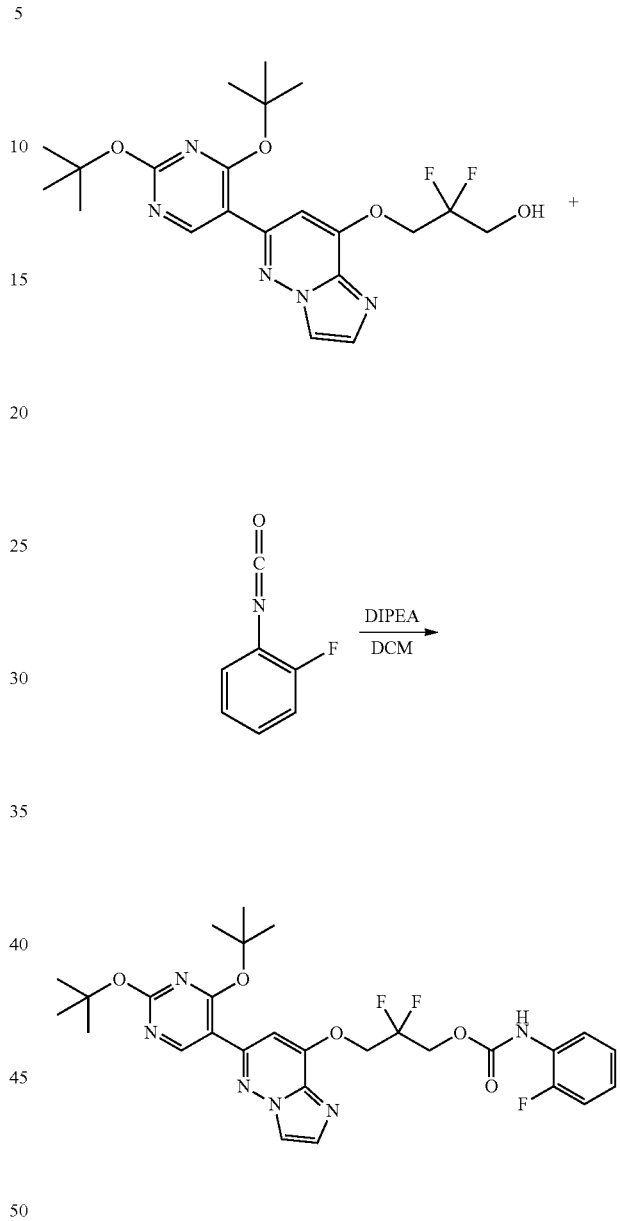

1-(6-(2,4-dimethoxypyrimidin-5-yl)imidazo[1,2-b]pyridazin-8-yl)-4,4-difluoropyrrolidin-3-yl (2-fluorophenyl)carbamate was prepared as follows: To a solution of 1-(6-(2,4-dimethoxypyrimidin-5-yl)imidazo[1,2-b]pyridazin-8-yl)-4,4-difluoropyrrolidin-3-ol (60 mg, 0.159 mmol, 1 equiv) in THF (2.0 mL) in an ice bath was gradually added NaH (60% dispersion in mineral oil) (19 mg, 0.476 mmol, 3 equiv). 1-fluoro-2-isocyanatobenzene (0.04 mL, 0.317 mmol, 2 equiv) was subsequently added. The reaction mixture was stirred at room temperature for 2 h. The reaction mixture was quenched with water and the aqueous layer was extracted with EtOAc (2×). The organic fractions were combined, dried over MgSO₄, filtered and concentrated in vacuo prior to purification by silica gel chromatography (0-100% EtOAc in hexanes) to afford the title compound. ES/MS m/z: 516.1 [M+H].

3-((6-(2,4-di-tert-butoxypyrimidin-5-yl)imidazo[1,2-b]pyridazin-8-yl)oxy)-2,2-difluoropropyl (2-fluorophenyl)carbamate was prepared as follows: To a solution of 3-((6-(2,4-di-tert-butoxypyrimidin-5-yl)imidazo[1,2-b]pyridazin-8-yl)oxy)-2,2-difluoropropan-1-ol (66 mg, 0.15 mmol, 1 equiv) in DCM (2.0 mL) was added DIPEA (0.25 mL, 1.5 mmol, 10 equiv), followed by 1-fluoro-2-isocyanatobenzene (0.16 mL, 1.5 mmol, 10 equiv). The reaction mixture was heated to 60° C. and stirred for 1 h and 50 min. The temperature was increased to 70° C. and the solution was stirred overnight. The solution was diluted with water and extracted with EtOAc (2×). Organic fractions were combined, dried over NaSO4, filtered and concentrated prior to purification by silica gel chromatography (0-100% EtOAc in hexanes) to afford the title compound. ES/MS m/z: 589.1 [M+H].

Intermediate 410. (S)-1-(6-(2,4-di-tert-butoxypyrimidin-5-yl)imidazo[1,2-b]pyridazin-8-yl)-4,4-difluoropyrrolidin-3-yl (2,4-difluorophenyl)carbamate Intermediate 411. (S)-1-(6-(2,4-di-tert-butoxypyrimidin-5-yl)imidazo[1,2-b]pyridazin-8-yl)-4,4-difluoropyrrolidin-3-yl (2-fluoro-4-methylphenyl)carbamate

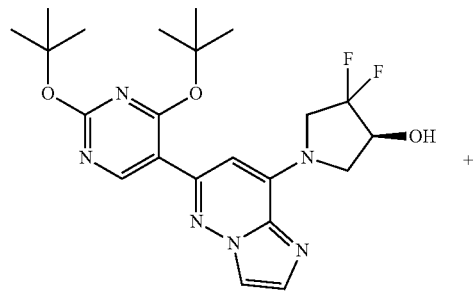

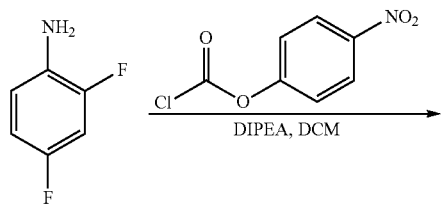

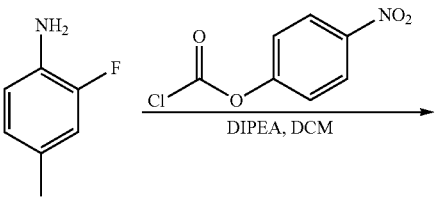

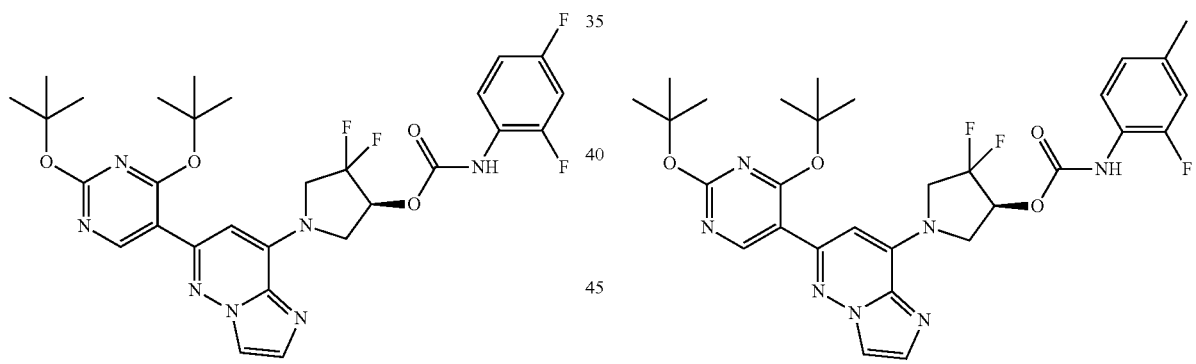

(S)-1-(6-(2,4-di-tert-butoxypyrimidin-5-yl)imidazo[1,2-b]pyridazin-8-yl)-4,4-difluoropyrrolidin-3-yl (2,4-difluorophenyl)carbamate was prepared as follows: To a solution of (S)-1-(6-(2,4-di-tert-butoxypyrimidin-5-yl)imidazo[1,2-b]pyridazin-8-yl)-4,4-difluoropyrrolidin-3-ol (42 mg, 0.091 mmol, 1 equiv) in DCM (0.75 mL) was added DIPEA (0.08 mL, 0.454 mmol, 5 equiv). 4-nitrophenyl chloroformate (52 mg, 0.258 mmol, 2.84 equiv) was subsequently added. The solution was stirred at room temperature for 50 min. 2,4-difluoroaniline (0.02 mL, 0.182 mmol, 2 equiv) was then added and the solution was left to stir overnight. The reaction mixture was treated with a saturated solution of sodium bicarbonate and water and extracted with DCM. Organic fractions were combined, dried over MgSO$_4$, filtered and concentrated prior to purification by silica gel chromatography (0-100% EtOAc in hexanes) to afford the title compound. ES/MS m/z: 506.0 [M+H].

(S)-1-(6-(2,4-di-tert-butoxypyrimidin-5-yl)imidazo[1,2-b]pyridazin-8-yl)-4,4-difluoropyrrolidin-3-yl (2-fluoro-4-methylphenyl)carbamate was prepared as follows: To a solution of (S)-1-(6-(2,4-di-tert-butoxypyrimidin-5-yl)imidazo[1,2-b]pyridazin-8-yl)-4,4-difluoropyrrolidin-3-ol (46 mg, 0.100 mmol, 1 equiv) in DCM (0.83 mL) was added DIPEA (0.17 mL, 0.995 mmol, 10 equiv). 4-nitrophenyl chloroformate (46 mg, 0.228 mmol, 2.29 equiv) was subsequently added. The solution was stirred at room temperature for 45 min. 2-fluoro-4-methylaniline (0.02 mL, 0.199 mmol, 2 equiv) was then added and the solution was left to stir overnight. The reaction mixture was treated with a saturated solution of sodium bicarbonate and water and extracted with DCM (2×). Organic fractions were combined, dried over MgSO$_4$ and concentrated prior to purification by silica gel chromatography (0-100% EtOAc in hexanes) to afford the title compound. ES/MS m/z: 502.0 [M+H].

483

Intermediate 412. 3-((6-(2,4-di-tert-butoxypyrimidin-5-yl)imidazo[1,2-b]pyridazin-8-yl)oxy)-2,2-difluoropropyl (2,4-difluorophenyl)carbamate

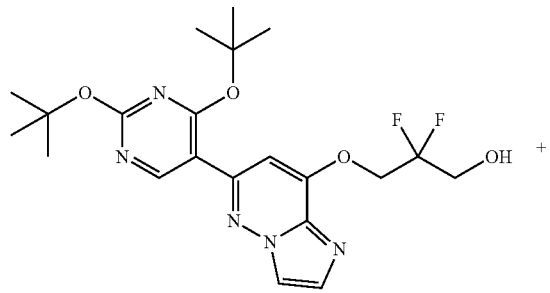

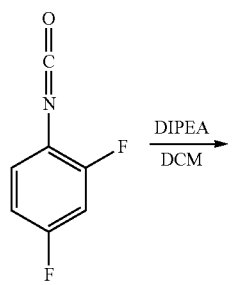

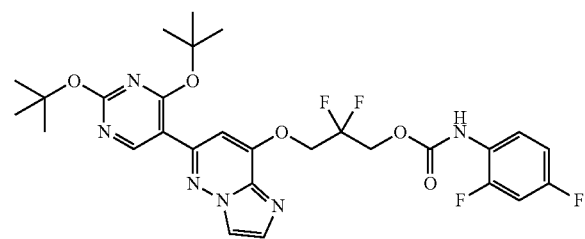

3-((6-(2,4-di-tert-butoxypyrimidin-5-yl)imidazo[1,2-b]pyridazin-8-yl)oxy)-2,2-difluoropropyl (2,4-difluorophenyl)carbamate was prepared as follows: To a solution of 3-((6-(2,4-di-tert-butoxypyrimidin-5-yl)imidazo[1,2-b]pyridazin-8-yl)oxy)-2,2-difluoropropan-1-ol (66 mg, 0.15 mmol, 1 equiv) in DCM (2.0 mL) was added DIPEA (0.25 mL, 1.5 mmol, 10 equiv), followed by 2,4-difluoro-1-isocyanatobenzene (0.17 mL, 1.5 mmol, 10 equiv). The reaction mixture was heated to 70° C. and stirred for 3 h and 20 min. The solution was diluted with water and extracted with EtOAc (2×). Organic fractions were combined, dried over NaSO4, filtered and concentrated prior to purification by silica gel chromatography (0-100% EtOAc in hexanes) to afford the title compound. ES/MS m/z: 607.1 [M+H].

484

Intermediate 413. (S)-1-(6-(2,4-di-tert-butoxypyrimidin-5-yl)imidazo[1,2-b]pyridazin-8-yl)-4,4-difluoropyrrolidin-3-yl (2,4,6-trifluorophenyl)carbamate

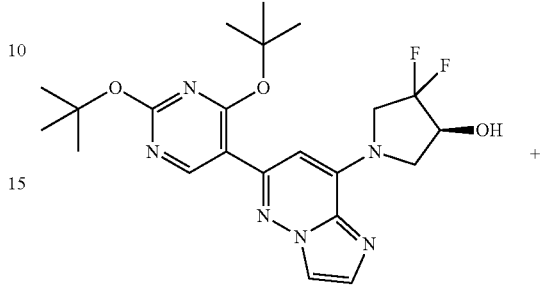

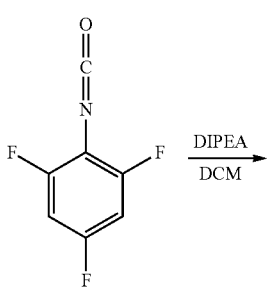

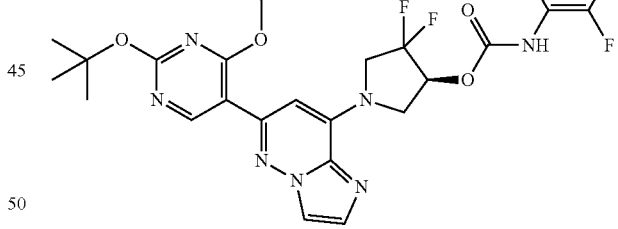

(S)-1-(6-(2,4-di-tert-butoxypyrimidin-5-yl)imidazo[1,2-b]pyridazin-8-yl)-4,4-difluoropyrrolidin-3-yl (2,4,6-trifluorophenyl)carbamate was prepared as follows: To a solution of (S)-1-(6-(2,4-di-tert-butoxypyrimidin-5-yl)imidazo[1,2-b]pyridazin-8-yl)-4,4-difluoropyrrolidin-3-ol (32 mg, 0.069 mmol, 1 equiv) in DCM (2.0 mL) was added DIPEA (0.12 mL, 0.69 mmol, 10 equiv), followed by 1,3,5-trifluoro-2-isocyanatobenzene (0.05 mL, 0.35 mmol, 5 equiv). The reaction mixture was heated to 60° C. and stirred for 4 h. The solution was diluted with water and extracted with EtOAc (2×). Organic fractions were combined, dried over NaSO4, filtered and concentrated prior to purification by silica gel chromatography (0-100% EtOAc in hexanes) to afford the title compound. ES/MS m/z: 524.0 [M+H].

Intermediate 414. 6-chloro-8-(3-(4-fluorophenyl)azetidin-1-yl)imidazo[1,2-b]pyridazine

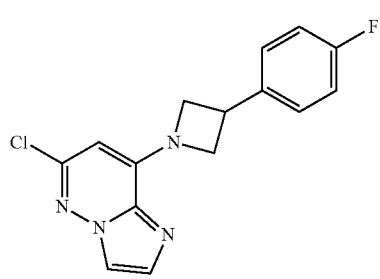 [SMILES: Fc1ccc(C2CN(c3cc(Cl)nn4ccnc34)C2)cc1]

6-chloro-8-(3-(4-fluorophenyl)azetidin-1-yl)imidazo[1,2-b]pyridazine was prepared in the manner described for Intermediate 10, but replacing pyrrolidine with 3-(4-fluorophenyl)azetidine hydrochloride. ES/MS m/z: 303.1 [M+H].

Intermediate 415. 6-chloro-8-(3-fluoro-3-phenylazetidin-1-yl)imidazo[1,2-b]pyridazine

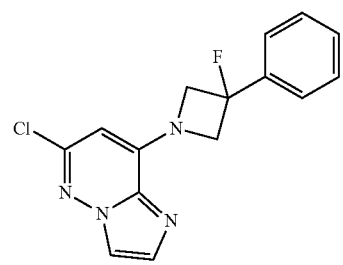 [SMILES: FC1(c2ccccc2)CN(c2cc(Cl)nn3ccnc23)C1]

6-chloro-8-(3-fluoro-3-phenylazetidin-1-yl)imidazo[1,2-b]pyridazine was prepared in the manner described for Intermediate 10, but replacing pyrrolidine with 3-fluoro-3-phenylazetidine hydrochloride. ES/MS m/z: 303.0 [M+H].

Intermediate 416. 6-chloro-8-(4,4-difluoro-6-azaspiro[2.5]octan-6-yl)imidazo[1,2-b]pyridazine

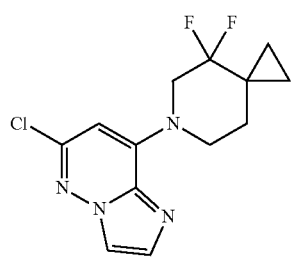 [SMILES: FC1(F)CN(c2cc(Cl)nn3ccnc23)CCC12CC2]

6-chloro-8-(4,4-difluoro-6-azaspiro[2.5]octan-6-yl)imidazo[1,2-b]pyridazine was prepared in the manner described for Intermediate 10, but replacing pyrrolidine with 4,4-difluoro-6-azaspiro[2.5]octane hydrochloride. ES/MS m/z: 299.0 [M+H].

Intermediate 417. Methyl 4-(1-(6-chloroimidazo[1,2-b]pyridazin-8-yl)azetidin-3-yl)benzoate

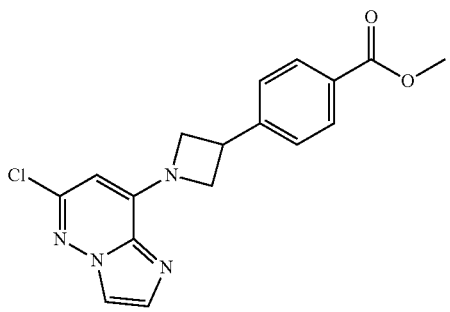 [SMILES: COC(=O)c1ccc(C2CN(c3cc(Cl)nn4ccnc34)C2)cc1]

Methyl 4-(1-(6-chloroimidazo[1,2-b]pyridazin-8-yl)azetidin-3-yl)benzoate was prepared in the manner described for Intermediate 10, but replacing pyrrolidine with methyl 4-(azetidin-3-yl)benzoate hydrochloride. ES/MS m/z: 343.1 [M+H].

Intermediate 418. 6-chloro-3-fluoro-8-(3-(4-(trifluoromethyl)phenyl)pyrrolidin-1-yl)imidazo[1,2-b]pyridazine

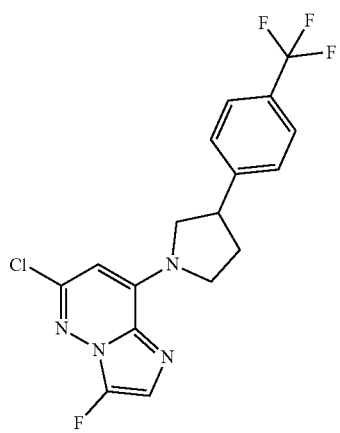 [SMILES: Fc1cnc2c(N3CCC(c4ccc(C(F)(F)F)cc4)C3)cc(Cl)nn12]

6-chloro-3-fluoro-8-(3-(4-(trifluoromethyl)phenyl)pyrrolidin-1-yl)imidazo[1,2-b]pyridazine was prepared in the manner described for Intermediate 10, but replacing 8-bromo-6-chloroimidazo[1,2-b]pyridazine with 8-bromo-6-chloro-3-fluoroimidazo[1,2-b]pyridazine, and pyrrolidine with 3-(4-(trifluoromethyl)phenyl)pyrrolidine. ES/MS m/z: 385.1 [M+H].

Intermediate 419. Methyl 3-(1-(6-chloroimidazo[1,2-b]pyridazin-8-yl)azetidin-3-yl)benzoate

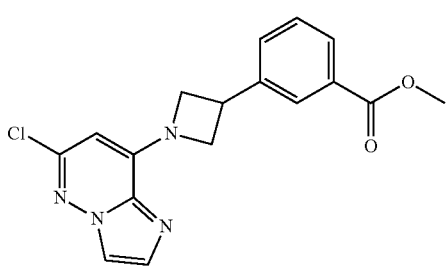 [SMILES: COC(=O)c1cccc(C2CN(c3cc(Cl)nn4ccnc34)C2)c1]

Methyl 3-(1-(6-chloroimidazo[1,2-b]pyridazin-8-yl)azetidin-3-yl)benzoate was prepared in the manner described for Intermediate 10, but replacing pyrrolidine with methyl 3-(azetidin-3-yl)benzoate hydrochloride. ES/MS m/z: 343.1 [M+H].

Intermediate 420. Methyl 3-(1-(6-chloroimidazo[1,2-b]pyridazin-8-yl)pyrrolidin-3-yl)benzoate

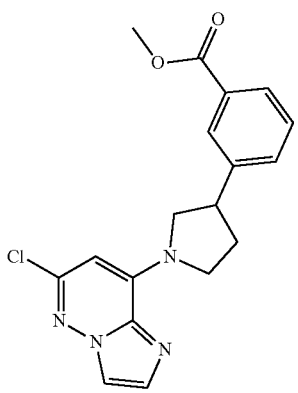 [SMILES: COC(=O)c1cccc(C2CCN(c3cc(Cl)nn4ccnc34)C2)c1]

Methyl 3-(1-(6-chloroimidazo[1,2-b]pyridazin-8-yl)pyrrolidin-3-yl)benzoate was prepared in the manner described for Intermediate 10, but replacing pyrrolidine with methyl 3-(pyrrolidin-3-yl)benzoate hydrochloride. ES/MS m/z: 357.1 [M+H].

Intermediate 421. Methyl 4-(1-(6-chloroimidazo[1,2-b]pyridazin-8-yl)pyrrolidin-3-yl)benzoate

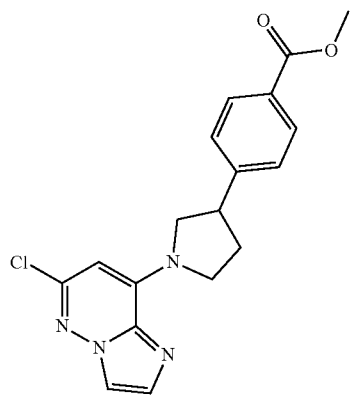 [SMILES: COC(=O)c1ccc(C2CCN(c3cc(Cl)nn4ccnc34)C2)cc1]

Methyl 4-(1-(6-chloroimidazo[1,2-b]pyridazin-8-yl)pyrrolidin-3-yl)benzoate was prepared in the manner described for Intermediate 10, but replacing pyrrolidine with methyl 4-(pyrrolidin-3-yl)benzoate hydrochloride. ES/MS m/z: 357.1 [M+H].

Intermediate 422. 6-chloro-8-(7,7-difluoro-5-azaspiro[2.4]heptan-5-yl)-[1,2,4]triazolo[4,3-b]pyridazine

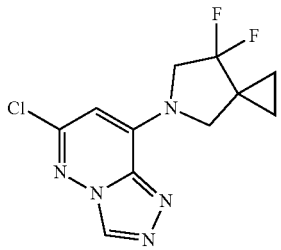 [SMILES: FC1(F)CN(c2cc(Cl)nn3cnnc23)CC12CC2]

6-chloro-8-(7,7-difluoro-5-azaspiro[2.4]heptan-5-yl)-[1,2,4]triazolo[4,3-b]pyridazine was prepared in the manner described for Intermediate 10, but replacing 8-bromo-6-chloroimidazo[1,2-b]pyridazine with 8-bromo-6-chloro-[1,2,4]triazolo[4,3-b]pyridazine, and pyrrolidine with 7,7-difluoro-5-azaspiro[2.4]heptane hydrochloride. ES/MS m/z: 286.0 [M+H].

Intermediate 423. 6-(2,4-dimethoxypyrimidin-5-yl)-8-(3-(4-fluorophenyl)azetidin-1-yl)imidazo[1,2-b]pyridazine

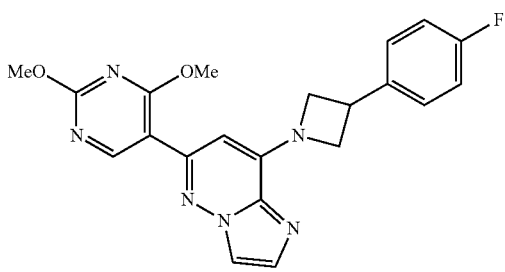 [SMILES: COc1ncc(-c2cc(N3CC(c4ccc(F)cc4)C3)c3nccn3n2)c(OC)n1]

6-(2,4-dimethoxypyrimidin-5-yl)-8-(3-(4-fluorophenyl)azetidin-1-yl)imidazo[1,2-b]pyridazine was prepared in the manner described for Intermediate 18, but replacing 8-cyclopropyl-6-(2,4-dimethoxypyrimidin-5-yl)-2-methyl-imidazo[1,2-b]pyridazine with 6-chloro-8-(3-(4-fluorophenyl)azetidin-1-yl)imidazo[1,2-b]pyridazine. ES/MS m/z: 407.2 [M+H].

Intermediate 424. 6-(2,4-dimethoxypyrimidin-5-yl)-8-(3-fluoro-3-phenylazetidin-1-yl)imidazo[1,2-b]pyridazine

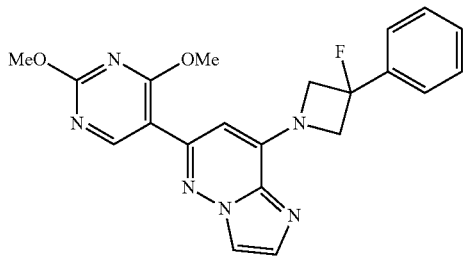 [SMILES: COc1ncc(-c2cc(N3CC(F)(c4ccccc4)C3)c3nccn3n2)c(OC)n1]

6-(2,4-dimethoxypyrimidin-5-yl)-8-(3-fluoro-3-phenylazetidin-1-yl)imidazo[1,2-b]pyridazine was prepared in the manner described for Intermediate 18, but replacing 8-cyclopropyl-6-(2,4-dimethoxypyrimidin-5-yl)-2-methyl-imidazo[1,2-b]pyridazine with 6-chloro-8-(3-fluoro-3-phenylazetidin-1-yl)imidazo[1,2-b]pyridazine. ES/MS m/z: 407.1 [M+H].

Intermediate 425. 8-(4,4-difluoro-6-azaspiro[2.5]octan-6-yl)-6-(2,4-dimethoxypyrimidin-5-yl)imidazo[1,2-b]pyridazine

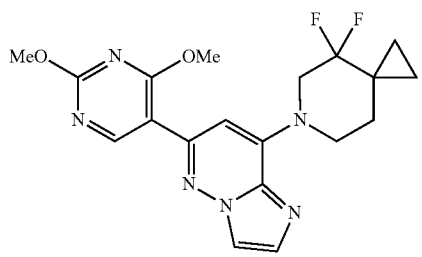 [SMILES: COc1ncc(-c2cc(N3CCC4(CC4)C(F)(F)C3)c3nccn3n2)c(OC)n1]

8-(4,4-difluoro-6-azaspiro[2.5]octan-6-yl)-6-(2,4-dimethoxypyrimidin-5-yl)imidazo[1,2-b]pyridazine was prepared in the manner described for Intermediate 18, but replacing 8-cyclopropyl-6-(2,4-dimethoxypyrimidin-5-yl)-2-methyl-imidazo[1,2-b]pyridazine with 6-chloro-8-(4,4-difluoro-6-azaspiro[2.5]octan-6-yl)imidazo[1,2-b]pyridazine. ES/MS m/z: 403.1 [M+H].

Intermediate 426. Methyl 4-(1-(6-(2,4-dimethoxypyrimidin-5-yl)imidazo[1,2-b]pyridazin-8-yl)azetidin-3-yl)benzoate

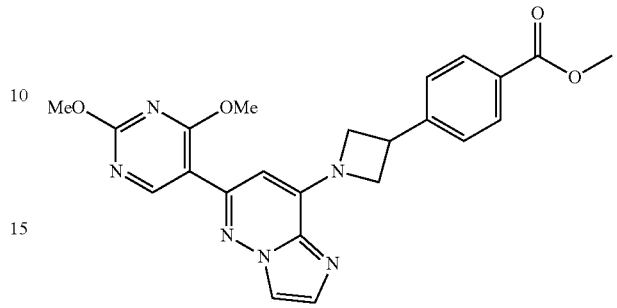

Methyl 4-(1-(6-(2,4-dimethoxypyrimidin-5-yl)imidazo[1,2-b]pyridazin-8-yl)azetidin-3-yl)benzoate was prepared in the manner described for Intermediate 18, but replacing 8-cyclopropyl-6-(2,4-dimethoxypyrimidin-5-yl)-2-methyl-imidazo[1,2-b]pyridazine with methyl 4-(1-(6-chloroimidazo[1,2-b]pyridazin-8-yl)azetidin-3-yl)benzoate. ES/MS m/z: 447.2 [M+H].

Intermediate 427. 6-(2,4-dimethoxypyrimidin-5-yl)-3-fluoro-8-(3-(4-(trifluoromethyl)phenyl)pyrrolidin-1-yl)imidazo[1,2-b]pyridazine

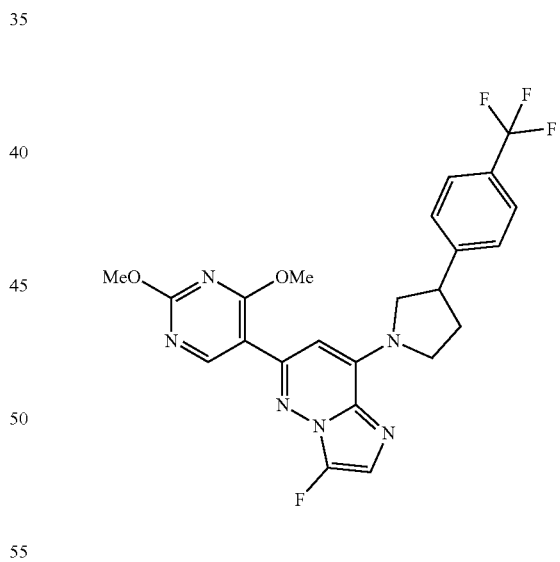

6-(2,4-dimethoxypyrimidin-5-yl)-3-fluoro-8-(3-(4-(trifluoromethyl)phenyl)pyrrolidin-1-yl)imidazo[1,2-b]pyridazine was prepared in the manner described for Intermediate 18, but replacing 8-cyclopropyl-6-(2,4-dimethoxypyrimidin-5-yl)-2-methyl-imidazo[1,2-b]pyridazine with 6-chloro-3-fluoro-8-(3-(4-(trifluoromethyl)phenyl)pyrrolidin-1-yl)imidazo[1,2-b]pyridazine. ES/MS m/z: 489.2 [M+H].

Intermediate 428. Methyl 3-(1-(6-(2,4-dimethoxy-pyrimidin-5-yl)imidazo[1,2-b]pyridazin-8-yl)azetidin-3-yl)benzoate

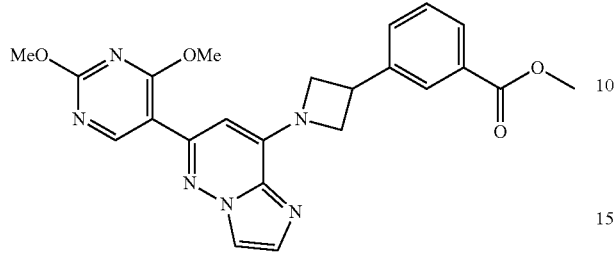

Methyl 3-(1-(6-(2,4-dimethoxypyrimidin-5-yl)imidazo[1,2-b]pyridazin-8-yl)azetidin-3-yl)benzoate was prepared in the manner described for Intermediate 18, but replacing 8-cyclopropyl-6-(2,4-dimethoxypyrimidin-5-yl)-2-methyl-imidazo[1,2-b]pyridazine with methyl 3-(1-(6-chloroimidazo[1,2-b]pyridazin-8-yl)azetidin-3-yl)benzoate. ES/MS m/z: 447.2 [M+H].

Intermediate 429. Methyl 3-(1-(6-(2,4-dimethoxy-pyrimidin-5-yl)imidazo[1,2-b]pyridazin-8-yl)pyrrolidin-3-yl)benzoate

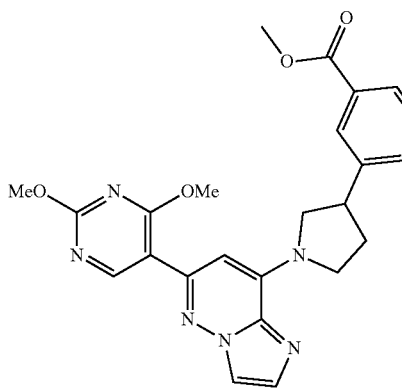

Methyl 3-(1-(6-(2,4-dimethoxypyrimidin-5-yl)imidazo[1,2-b]pyridazin-8-yl)pyrrolidin-3-yl)benzoate was prepared in the manner described for Intermediate 18, but replacing 8-cyclopropyl-6-(2,4-dimethoxypyrimidin-5-yl)-2-methyl-imidazo[1,2-b]pyridazine with methyl 3-(1-(6-chloroimidazo[1,2-b]pyridazin-8-yl)pyrrolidin-3-yl)benzoate. ES/MS m/z: 461.2 [M+H].

Intermediate 430. Methyl 4-(1-(6-(2,4-dimethoxy-pyrimidin-5-yl)imidazo[1,2-b]pyridazin-8-yl)pyrrolidin-3-yl)benzoate

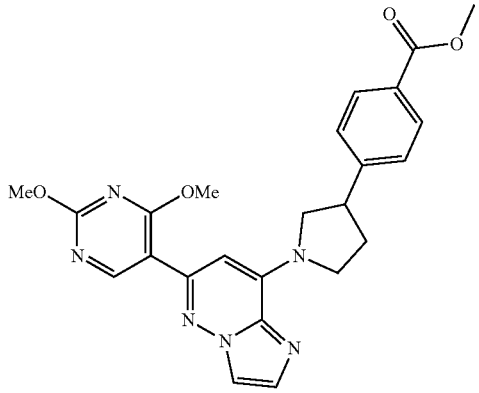 [SMILES: COC(=O)c1ccc(C2CCN(c3cc(-c4cnc(OC)nc4OC)nn4ccnc34)C2)cc1]

Methyl 4-(1-(6-(2,4-dimethoxypyrimidin-5-yl)imidazo[1,2-b]pyridazin-8-yl)pyrrolidin-3-yl)benzoate was prepared in the manner described for Intermediate 18, but replacing 8-cyclopropyl-6-(2,4-dimethoxypyrimidin-5-yl)-2-methyl-imidazo[1,2-b]pyridazine with methyl 4-(1-(6-chloroimidazo[1,2-b]pyridazin-8-yl)pyrrolidin-3-yl)benzoate. ES/MS m/z: 461.2 [M+H].

Intermediate 431. 8-(7,7-difluoro-5-azaspiro[2.4]heptan-5-yl)-6-(2,4-dimethoxypyrimidin-5-yl)-[1,2,4]triazolo[4,3-b]pyridazine

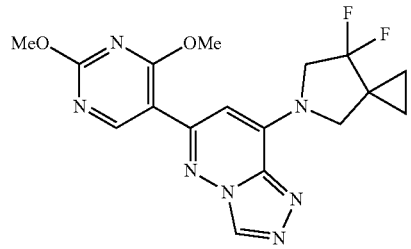 [SMILES: COc1ncc(-c2cc(N3CC(F)(F)C4(CC4)C3)c3nncn3n2)c(OC)n1]

8-(7,7-difluoro-5-azaspiro[2.4]heptan-5-yl)-6-(2,4-dimethoxypyrimidin-5-yl)-[1,2,4]triazolo[4,3-b]pyridazine was prepared in the manner described for Intermediate 18, but replacing 8-cyclopropyl-6-(2,4-dimethoxypyrimidin-5-yl)-2-methyl-imidazo[1,2-b]pyridazine with 6-chloro-8-(7,7-difluoro-5-azaspiro[2.4]heptan-5-yl)-[1,2,4]triazolo[4,3-b]pyridazine. ES/MS m/z: 390.2 [M+H].

Intermediate 432. 6-chloro-8-((1R,2R)-2-(2-(trifluoromethyl)pyrimidin-5-yl)cyclopropyl)imidazo[1,2-b]pyridazine (single enantiomer arbitrarily assigned)

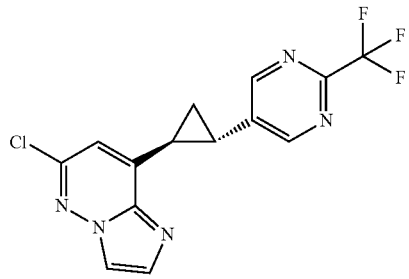 [SMILES: FC(F)(F)c1ncc([C@H]2C[C@@H]2c2cc(Cl)nn3ccnc23)cn1]

6-chloro-8-((1S,2S)-2-(2-(trifluoromethyl)pyrimidin-5-yl)cyclopropyl)imidazo[1,2-b]pyridazine was prepared in the manner described for Intermediate 5, but replacing 4,4,5,5-tetramethyl-2-((1S,2S)-2-phenylcyclopropyl)-1,3,2-dioxaborolane with 5-((1S,2S)-2-(4,4,5,5-tetramethyl-1,3,2-dioxaborolan-2-yl)cyclopropyl)-2-(trifluoromethyl)pyrimidine. ES/MS m/z: 340.1 [M+H].

Intermediate 433. 6-chloro-3-fluoro-8-((1R,2R)-2-(2-(trifluoromethyl)pyrimidin-5-yl)cyclopropyl)imidazo[1,2-b]pyridazine

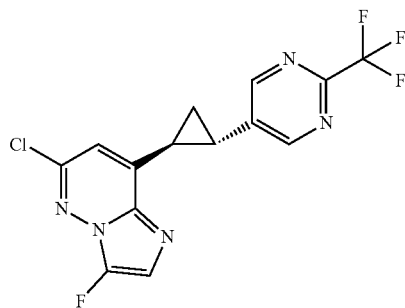 [SMILES: Fc1cnc2c([C@H]3C[C@@H]3c3cnc(C(F)(F)F)nc3)cc(Cl)nn12]

6-chloro-3-fluoro-8-((1R,2R)-2-(2-(trifluoromethyl)pyrimidin-5-yl)cyclopropyl)imidazo[1,2-b]pyridazine was prepared in the manner described for Intermediate 5, but replacing 4,4,5,5-tetramethyl-2-((2S,2S)-2-phenylcyclopropyl)-1,3,2-dioxaborolane with 54(1S,2S)-2-(4,4,5,5-tetramethyl-1,3,2-dioxaborolan-2-yl)cyclopropyl)-2-(trifluoromethyl)pyrimidine and 8-bromo-6-chloroimidazo[1,2-b]pyridazine with 8-bromo-6-chloro-3-fluoroimidazo[1,2-b]pyridazine. ES/MS m/z: 358.0 [M+H].

Intermediate 434. 6-(2,4-dimethoxypyrimidin-5-yl)-8-((1R,2R)-2-(2-(trifluoromethyl)pyrimidin-5-yl)cyclopropyl)imidazo[1,2-b]pyridazine

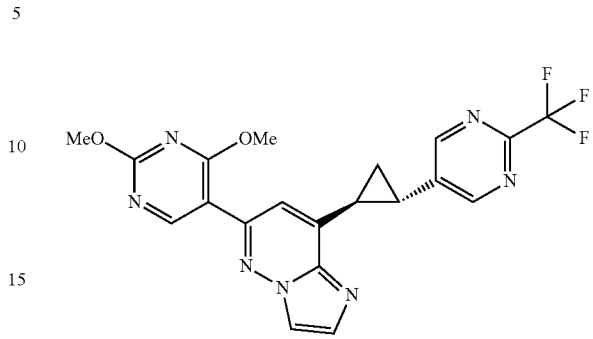

6-(2,4-dimethoxypyrimidin-5-yl)-8-((1S,2S)-2-(2-(trifluoromethyl)pyrimidin-5-yl)cyclopropyl)imidazo[1,2-b]pyridazine was prepared in the manner described for Intermediate 18, but replacing 8-cyclopropyl-6-(2,4-dimethoxypyrimidin-5-yl)-2-methyl-imidazo[1,2-b]pyridazine with 6-chloro-8-((2S,2S)-2-(2-(trifluoromethyl)pyrimidin-5-yl)cyclopropyl)imidazo[1,2-b]pyridazine. ES/MS m/z: 444.2 [M+H].

Intermediate 435. 6-(2,4-dimethoxypyrimidin-5-yl)-3-fluoro-8-((1R,2R)-2-(2-(trifluoromethyl)pyrimidin-5-yl)cyclopropyl)imidazo[1,2-b]pyridazine

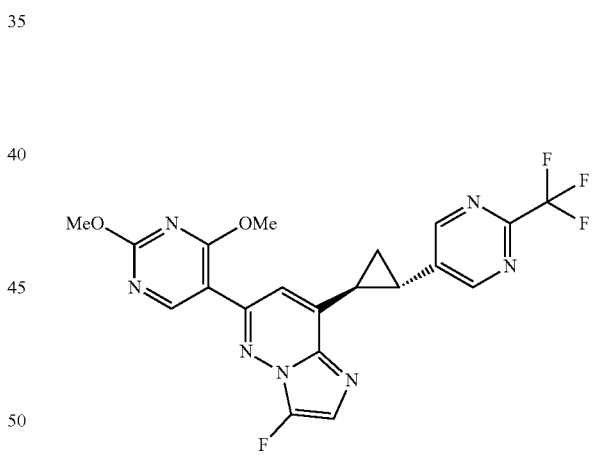

6-(2,4-dimethoxypyrimidin-5-yl)-3-fluoro-8-((2S,2S)-2-(2-(trifluoromethyl)pyrimidin-5-yl)cyclopropyl)imidazo[1,2-b]pyridazine was prepared in the manner described for Intermediate 18, but replacing 8-cyclopropyl-6-(2,4-dimethoxypyrimidin-5-yl)-2-methyl-imidazo[1,2-b]pyridazine with 6-chloro-3-fluoro-8-((1R,2R)-2-(2-(trifluoromethyl)pyrimidin-5-yl)cyclopropyl)imidazo[1,2-b]pyridazine. ES/MS m/z: 462.1 [M+H].

Intermediate 436. 8-bromo-6-chloro-2-isobutylimidazo[1,2-b]pyridazine

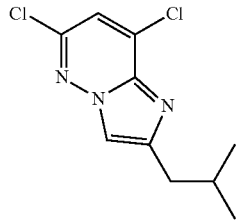

To a solution of 4-bromo-6-chloropyridazin-3-amine (400 mg, 1.9 mmol, 1 equiv.) in DMF (3.8 mL) was added 1-chloro-4-methylpentan-2-one (310 mg, 2.3 mmol, 1.2 equiv.). The reaction was heated to 70° C. and stirred overnight. The reaction was subsequently cooled to room temperature and diluted with EtOAc/water. The resulting mixture was extracted twice with EtOAc, the combined organics were dried over MgSO$_4$, filtered and conc. in vacuo. The title compound was purified by silica gel chromatography (0-100% EtOAc/hexanes). ES/MS m/z: 244.10 [M+H].

Intermediate 437. 6-chloro-8-(7,7-difluoro-5-azaspiro[2.4]heptan-5-yl)-2-isobutylimidazo[1,2-b]pyridazine

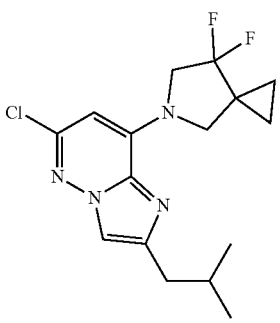 [SMILES: CC(C)Cc1cn2nc(Cl)cc(N3CC(F)(F)C4(CC4)C3)c2n1]

6-chloro-8-(7,7-difluoro-5-azaspiro[2.4]heptan-5-yl)-2-isobutylimidazo[1,2-b]pyridazine was prepared in the manner described for Intermediate 59, but replacing 3,3-dimethylpyrrolidine hydrochloride with 7,7-difluoro-5-azaspiro[2.4]heptane and 8-bromo-6-chloroimidazo[1,2-b]pyridazine with 8-bromo-6-chloro-2-isobutylimidazo[1,2-b]pyridazine. ES/MS m/z: 341.12 [M+H].

Intermediate 438. 8-(7,7-difluoro-5-azaspiro[2.4]heptan-5-yl)-6-(2,4-dimethoxypyrimidin-5-yl)-2-isobutylimidazo[1,2-b]pyridazine

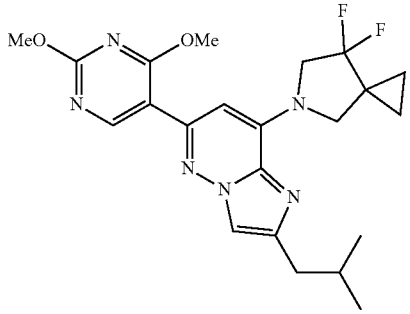 [SMILES: COc1ncc(-c2cc(N3CC(F)(F)C4(CC4)C3)c3nc(CC(C)C)cn3n2)c(OC)n1]

8-(7,7-difluoro-5-azaspiro[2.4]heptan-5-yl)-6-(2,4-dimethoxypyrimidin-5-yl)-2-isobutylimidazo[1,2-b]pyridazine was prepared in the manner described for Intermediate 18, but replacing 6-chloro-8-cyclopropyl-2-methyl-imidazo[1,2-b]pyridazine with 6-chloro-8-(7,7-difluoro-5-azaspiro[2.4]heptan-5-yl)-2-isobutylimidazo[1,2-b]pyridazine. ES/MS m/z: 445.20 [M+H].

Intermediate 439. 8-((2S,2S)-2-(1H-benzo[d]imidazol-2-yl)cyclopropyl)-6-(2,4-dimethoxypyrimidin-5-yl)imidazo[1,2-b]pyridazine

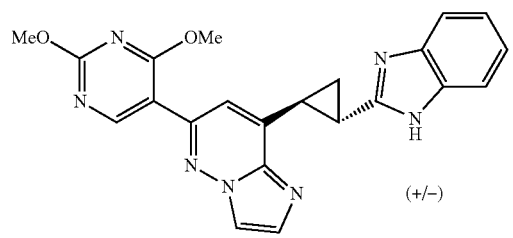 [SMILES: COc1ncc(-c2cc([C@H]3C[C@@H]3c3nc4ccccc4[nH]3)c3nccn3n2)c(OC)n1]

(+/−)

8-((2S,2S)-2-(1H-benzo[d]imidazol-2-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-6-(2,4-dimethoxypyrimidin-5-yl)-2-methyl-imidazo[1,2-b]pyridazine with 8-((2S,2S)-2-(1H-benzo[d]imidazol-2-yl)cyclopropyl)-6-chloroimidazo[1,2-b]pyridazine. ES/MS m/z: 414.20 [M+H].

Intermediate 440. (1S,2S)-2-(6-(2,4-dimethoxypyrimidin-5-yl)imidazo[1,2-b]pyridazin-8-yl)-N-phenylcyclopropane-1-carboxamide

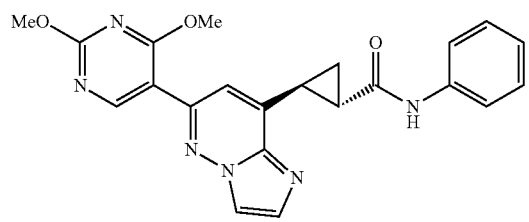 [SMILES: COc1ncc(-c2cc([C@H]3C[C@@H]3C(=O)Nc3ccccc3)c3nccn3n2)c(OC)n1]

(1S,2S)-2-(6-(2,4-dimethoxypyrimidin-5-yl)imidazo[1,2-b]pyridazin-8-yl)-N-phenylcyclopropane-1-carboxamide was prepared as a racemic mixture in the manner described for Intermediate 18, but replacing 6-chloro-8-cyclopropyl-6-(2,4-dimethoxypyrimidin-5-yl)-2-methyl-imidazo[1,2-b]pyridazine with (1S,2S)-2-(6-chloroimidazo[1,2-b]pyridazin-8-yl)-N-phenylcyclopropane-1-carboxamide. ES/MS m/z: 417.20 [M+H].

Intermediate 441. 2-((1S,2S)-2-(6-(2,4-dimethoxypyrimidin-5-yl)imidazo[1,2-b]pyridazin-8-yl)cyclopropyl)propan-2-ol

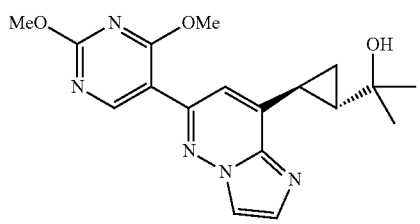 [SMILES: COc1ncc(-c2cc([C@H]3C[C@@H]3C(C)(C)O)c3nccn3n2)c(OC)n1]

2-((1S,2S)-2-(6-(2,4-dimethoxypyrimidin-5-yl)imidazo[1,2-b]pyridazin-8-yl)cyclopropyl)propan-2-ol was prepared as a racemic mixture in the manner described for Intermediate 18, but replacing 6-chloro-8-cyclopropyl-6-(2,4-dimethoxypyrimidin-5-yl)-2-methyl-imidazo[1,2-b]pyridazine with 2-((1S,2S)-2-(6-chloroimidazo[1,2-b]pyridazin-8-yl)cyclopropyl)propan-2-ol. ES/MS m/z: 356.17 [M+H].

Intermediate 442. 4-((1S,2S)-2-(6-chloroimidazo[1,2-b]pyridazin-8-yl)cyclopropyl)benzonitrile

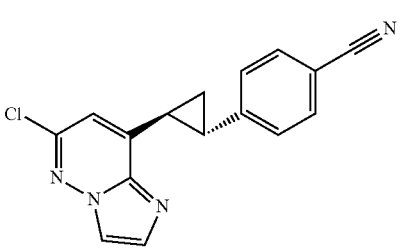 [SMILES: N#Cc1ccc([C@H]2C[C@@H]2c2cc(Cl)nn3ccnc23)cc1]

4-((2S,2S)-2-(6-chloroimidazo[1,2-b]pyridazin-8-yl)cyclopropyl)benzonitrile was prepared in the manner described for Intermediate 81, but replacing 2-[(1S,2S)-2-(3,5-difluorophenyl)cyclopropyl]-4,4,5,5-tetramethyl-1,3,2-dioxaborolane with 4-((2S,2S)-2-(4,4,5,5-tetramethyl-1,3,2-dioxaborolan-2-yl)cyclopropyl)benzonitrile. ES/MS m/z: 295.10 [M+1].

Intermediate 443. 4-((1S,2S)-2-(6-(2,4-dimethoxypyrimidin-5-yl)imidazo[1,2-b]pyridazin-8-yl)cyclopropyl)benzonitrile

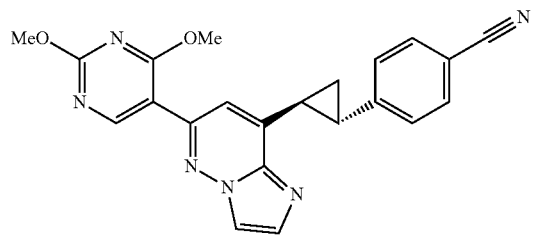 [SMILES: COc1ncc(-c2cc([C@H]3C[C@@H]3c3ccc(C#N)cc3)c3nccn3n2)c(OC)n1]

4-((1S,2S)-2-(6-(2,4-dimethoxypyrimidin-5-yl)imidazo[1,2-b]pyridazin-8-yl)cyclopropyl)benzonitrile was prepared in the manner described for Intermediate 18, but replacing 6-chloro-8-cyclopropyl-6-(2,4-dimethoxypyrimidin-5-yl)-2-methyl-imidazo[1,2-b]pyridazine with 4-((1S,2S)-2-(6-chloroimidazo[1,2-b]pyridazin-8-yl)cyclopropyl)benzonitrile. ES/MS m/z: 399.19 [M+H].

Intermediate 444. 3-((2S,2S)-2-(6-chloroimidazo[1,2-b]pyridazin-8-yl)cyclopropyl)-4-fluorobenzonitrile

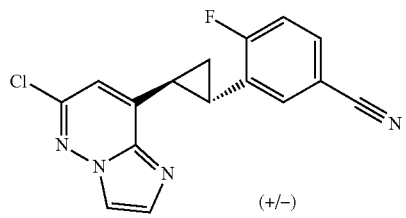 [SMILES: N#Cc1ccc(F)c([C@H]2C[C@@H]2c2cc(Cl)nn3ccnc23)c1]

(+/-)

3-((2S,2S)-2-(6-chloroimidazo[1,2-b]pyridazin-8-yl)cyclopropyl)-4-fluorobenzonitrile was prepared as a racemic mixture in the manner described for Intermediate 81, but replacing 2-[(1S,2S)-2-(3,5-difluorophenyl)cyclopropyl]-4,4,5,5-tetramethyl-1,3,2-dioxaborolane with 4-fluoro-3-((2S,2S)-2-(4,4,5,5-tetramethyl-1,3,2-dioxaborolan-2-yl)cyclopropyl)benzonitrile. ES/MS m/z: 313.10 [M+1].

Intermediate 445. 3-((2S,2S)-2-(6-(2,4-dimethoxypyrimidin-5-yl)imidazo[1,2-b]pyridazin-8-yl)cyclopropyl)-4-fluorobenzonitrile

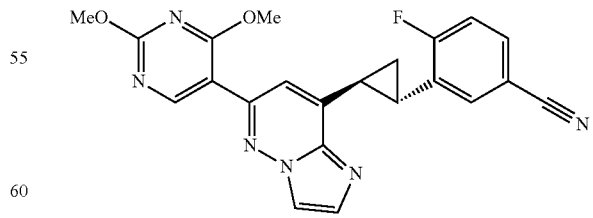

3-((2S,2S)-2-(6-(2,4-dimethoxypyrimidin-5-yl)imidazo[1,2-b]pyridazin-8-yl)cyclopropyl)-4-fluorobenzonitrile was prepared as a racemic mixture in the manner described for Intermediate 18, but replacing 6-chloro-8-cyclopropyl-6-(2,4-dimethoxypyrimidin-5-yl)-2-methyl-imidazo[1,2-b]

pyridazine with 3-((2S,2S)-2-(6-chloroimidazo[1,2-b]pyridazin-8-yl)cyclopropyl)-4-fluorobenzonitrile. ES/MS m/z: 417.16 [M+H].

Intermediate 446. 4-((2S,2S)-2-(6-chloroimidazo[1,2-b]pyridazin-8-yl)cyclopropyl)-2-fluorobenzonitrile

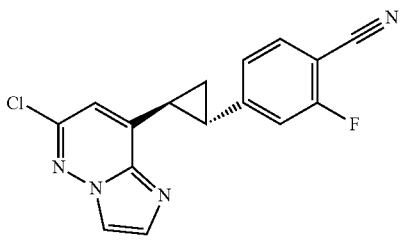 [SMILES: N#Cc1ccc([C@H]2C[C@@H]2c2cc(Cl)nn3ccnc23)cc1F]

4-((2S,2S)-2-(6-chloroimidazo[1,2-b]pyridazin-8-yl)cyclopropyl)-2-fluorobenzonitrile was prepared in the manner described for Intermediate 81, but replacing 2-[(1S,2S)-2-(3,5-difluorophenyl)cyclopropyl]-4,4,5,5-tetramethyl-1,3,2-dioxaborolane with 2-fluoro-4-((1S,2S)-2-(4,4,5,5-tetramethyl-1,3,2-dioxaborolan-2-yl)cyclopropyl)benzonitrile. ES/MS m/z: 313.07 [M+1].

Intermediate 447. 4-((1S,2S)-2-(6-(2,4-dimethoxypyrimidin-5-yl)imidazo[1,2-b]pyridazin-8-yl)cyclopropyl)-2-fluorobenzonitrile

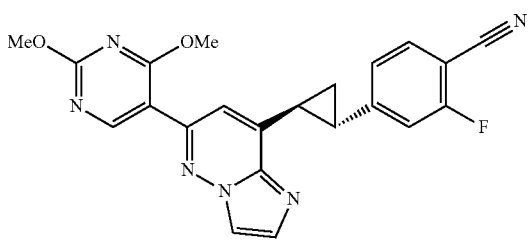 [SMILES: COc1ncc(-c2cc([C@H]3C[C@@H]3c3ccc(C#N)c(F)c3)c3nccn3n2)c(OC)n1]

4-((1S,2S)-2-(6-(2,4-dimethoxypyrimidin-5-yl)imidazo[1,2-b]pyridazin-8-yl)cyclopropyl)-2-fluorobenzonitrile was prepared in the manner described for Intermediate 18, but replacing 6-chloro-8-cyclopropyl-6-(2,4-dimethoxypyrimidin-5-yl)-2-methyl-imidazo[1,2-b]pyridazine with 4-((2S,2S)-2-(6-chloroimidazo[1,2-b]pyridazin-8-yl)cyclopropyl)-2-fluorobenzonitrile. ES/MS m/z: 417.19 [M+H].

Intermediate 448. potassium trifluoro((1S,2S)-2-(4-(trifluoromethyl)phenyl)cyclopropyl)borate

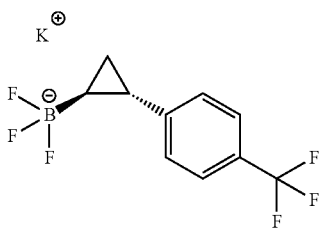 [SMILES: [K+] ; F[B-](F)(F)[C@H]1C[C@@H]1c1ccc(C(F)(F)F)cc1]

4,4,5,5-tetramethyl-2-((2S,2S)-2-(4-(trifluoromethyl)phenyl)cyclopropyl)-1,3,2-dioxaborolane (600 mg, 1.92 mmol) and KHF2 (1.05 g, 13.5 mmol) were weighed into a vial, and MeOH (10 mL) and water (2 mL) were added. The mixture was stirred at rt overnight, and then solvent was removed in vacuo. The resulting residue was taken up in MeCN, and filtered to remove solids, washing with MeCN. The filtrate was concentrated in vacuo, then the solid was washed with diethyl ether and dried to afford potassium trifluoro((2S,2S)-2-(4-(trifluoromethyl)phenyl)cyclopropyl)borate. $^1$H NMR (400 MHz, Acetone-d6) δ 7.45 (d, J=8.1 Hz, 2H), 7.15 (d, J=8.1 Hz, 2H), 1.74-1.62 (m, 1H), 0.88 (td, J=7.5, 2.7 Hz, 1H), 0.52 (d, J=9.8 Hz, 1H), 0.07-0.06 (m, 1H). $^{19}$F NMR (376 MHz, Acetone-d6) δ −62.88, −146.65 (d, J=87.8 Hz).

Intermediate 449. 5-bromo-7-((1S,2S)-2-(2,4-difluorophenyl)cyclopropyl)pyrazolo[1,5-a]pyrimidine

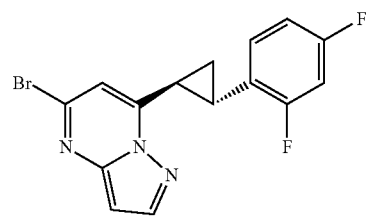 [SMILES: Fc1ccc([C@H]2C[C@@H]2c2cc(Br)nc3ccnn23)c(F)c1]

To a reaction vessel containing 5,7-dibromopyrazolo[1,5-a]pyrimidine (256 mg, 0.92 mmol, 1.2 equiv.), ((1S,2S)-2-(2,4-difluorophenyl)cyclopropyl)trifluoro-14-borane, potassium salt (200 mg, 0.77 mmol, 1 equiv.), Pd(PPh$_3$)$_4$ (44 mg, 0.039 mmol, 5 mol %) and Cs$_2$CO$_3$ (752 mg, 2.3 mmol, 3 equiv) was added a freshly degassed mixture of toluene/water (4.2 mL, 5:1 ratio) under an atmosphere of nitrogen. The reaction was heated to 90° C. for 4 hours. The reaction mixture was cooled to room temperature and diluted with EtOAc/water. The resulting mixture was extracted twice with EtOAc, the combined organics were dried over MgSO$_4$, filtered and conc. in vacuo. The title compound was purified by FCC (0-30% EtOAc/hexanes). ES/MS m/z: 350.00 [M+H].

Intermediate 450. 7-((2S,2S)-2-(2,4-difluorophenyl)cyclopropyl)-5-(2,4-dimethoxypyrimidin-5-yl)pyrazolo[1,5-a]pyrimidine

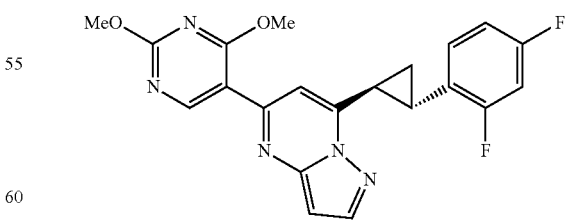

7-((1S,2S)-2-(2,4-difluorophenyl)cyclopropyl)-5-(2,4-dimethoxypyrimidin-5-yl)pyrazolo[1,5-a]pyrimidine was prepared in the manner described for Intermediate 18, but replacing 6-chloro-8-cyclopropyl-6-(2,4-dimethoxypyrimidin-5-yl)-2-methyl-imidazo[1,2-b]pyridazine with 5-bromo- 7-((2S,2S)-2-(2,4-difluorophenyl)cyclopropyl)pyrazolo[1,5-a]pyrimidine. ES/MS m/z: 410.20 [M+H].

Intermediate 451. 5-chloro-74(3R,4S)-3,4-difluoro-pyrrolidin-1-yl)-[1,2,4]triazolo[1,5-a]pyrimidine

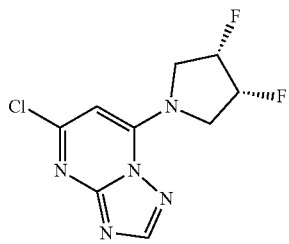 [SMILES: F[C@@H]1CN(c2cc(Cl)nc3ncnn23)C[C@@H]1F]

5-chloro-7-((3R,4S)-3,4-difluoropyrrolidin-1-yl)-[1,2,4]triazolo[1,5-a]pyrimidine was prepared in the manner described for Intermediate 65, but replacing 5,7-dichloro-pyrazolo[1,5-a]pyrimidine with 5,7-dichloro-[1,2,4]triazolo[1,5-a]pyrimidine and 3,3-dimethylpyrrolidine with (3R,4S)-3,4-difluoropyrrolidine-HCl. ES/MS m/z: 260.10 [M+H].

Intermediate 452. 7-((3R,4S)-3,4-difluoropyrrolidin-1-yl)-5-(2,4-dimethoxypyrimidin-5-yl)-[1,2,4]triazolo[1,5-a]pyrimidine

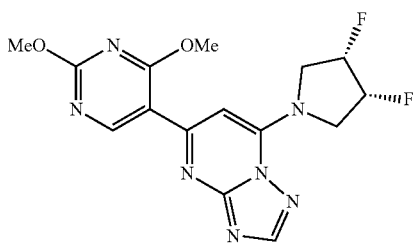 [SMILES: COc1ncc(-c2cc(N3C[C@@H](F)[C@@H](F)C3)n3ncnc3n2)c(OC)n1]

7-((3R,4S)-3,4-difluoropyrrolidin-1-yl)-5-(2,4-dimethoxypyrimidin-5-yl)-[1,2,4]triazolo[1,5-a]pyrimidine was prepared in the manner described for Intermediate 18, but replacing 6-chloro-8-cyclopropyl-2-methyl-imidazo[1,2-b]pyridazine with 5-chloro-7-((3R,4S)-3,4-difluoropyrrolidin-1-yl)-[1,2,4]triazolo[1,5-a]pyrimidine. ES/MS m/z: 364.10 [M+H].

Intermediate 453. 6-chloro-8-(3,3-difluoro-4-methoxypyrrolidin-1-yl)-3-fluoroimidazo[1,2-b]pyridazine

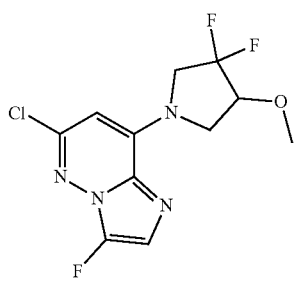 [SMILES: COC1CN(c2cc(Cl)nn3c(F)cnc23)CC1(F)F]

6-chloro-8-(3,3-difluoro-4-methoxypyrrolidin-1-yl)-3-fluoroimidazo[1,2-b]pyridazine was prepared in the manner described for Intermediate 59, but replacing 3,3-dimethylpyrrolidine hydrochloride with 3,3-difluoro-4-methoxypyrrolidine hydrochloride. ES/MS m/z: 307.00 [M+H].

Intermediate 454. 8-(3,3-difluoro-4-methoxypyrrolidin-1-yl)-6-(2,4-dimethoxypyrimidin-5-yl)-3-fluoroimidazo[1,2-b]pyridazine

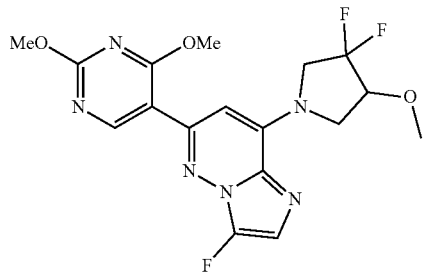 [SMILES: COc1ncc(-c2cc(N3CC(OC)C(F)(F)C3)c3ncc(F)n3n2)c(OC)n1]

8-(3,3-difluoro-4-methoxypyrrolidin-1-yl)-6-(2,4-dimethoxypyrimidin-5-yl)-3-fluoroimidazo[1,2-b]pyridazine was prepared in the manner described for Intermediate 18, but replacing 6-chloro-8-cyclopropyl-2-methyl-imidazo[1,2-b]pyridazine with 6-chloro-8-(3,3-difluoro-4-methoxypyrrolidin-1-yl)-3-fluoroimidazo[1,2-b]pyridazine. ES/MS m/z: 411.15 [M+H].

Intermediate 455. 6-chloro-8-((2S,2S)-2-(4-chloro-3-fluorophenyl)cyclopropyl)imidazo[1,2-b]pyridazine

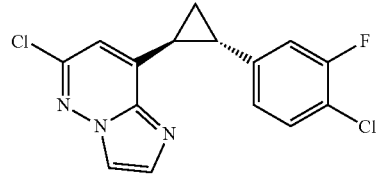 [SMILES: Fc1cc([C@H]2C[C@@H]2c2cc(Cl)nn3ccnc23)ccc1Cl]

6-chloro-8-((2S,2S)-2-(4-chloro-3-fluorophenyl)cyclopropyl)imidazo[1,2-b]pyridazine as a racemate was prepared in the manner described for Intermediate 1, but replacing cyclopropylboronic acid with racemic 2-((1S,2S)-2-(4-chloro-3-fluorophenyl)cyclopropyl)-4,4,5,5-tetramethyl-1,3,2-dioxaborolane. ES/MS m/z: 322.02 [M+H].

Intermediate 456. 8-((1S,2S)-2-(4-chloro-3-fluorophenyl)cyclopropyl)-6-(2,4-dimethoxypyrimidin-5-yl)imidazo[1,2-b]pyridazine

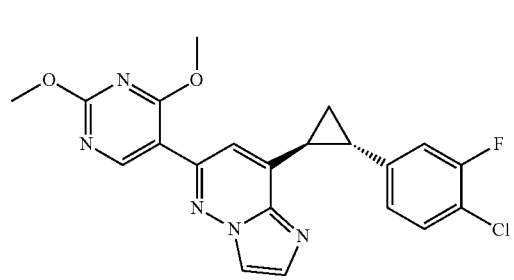 [SMILES: COc1ncc(-c2cc([C@H]3C[C@@H]3c3ccc(Cl)c(F)c3)c3nccn3n2)c(OC)n1]

8-((1S,2S)-2-(4-chloro-3-fluorophenyl)cyclopropyl)-6-(2,4-dimethoxypyrimidin-5-yl)imidazo[1,2-b]pyridazine as a racemate was prepared in the manner described for Intermediate 18, but replacing 6-chloro-8-cyclopropyl-2-methyl-imidazo[1,2-b]pyridazine with racemic 6-chloro-8-((1S,2S)-2-(4-chloro-3-fluorophenyl)cyclopropyl)imidazo[1,2-b]pyridazine. ES/MS m/z: 426.10 [M+H].

Intermediate 457. 7-(6-chloroimidazo[1,2-b]pyridazin-8-yl)-2-oxa-7-azaspiro[4.4]nonane

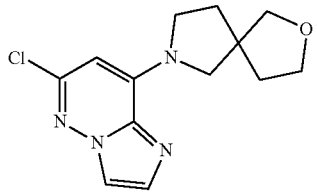 [SMILES: Clc1cc(N2CCC3(CCOC3)C2)c2nccn2n1]

7-(6-chloroimidazo[1,2-b]pyridazin-8-yl)-2-oxa-7-azaspiro[4.4]nonane was prepared in the manner described for Intermediate 10, but replacing pyrrolidine with 2-oxa-7-azaspiro[4.4]nonane. ES/MS m/z: 279.16 [M+H].

Intermediate 458. 7-(6-(2,4-dimethoxypyrimidin-5-yl)imidazo[1,2-b]pyridazin-8-yl)-2-oxa-7-azaspiro[4.4]nonane

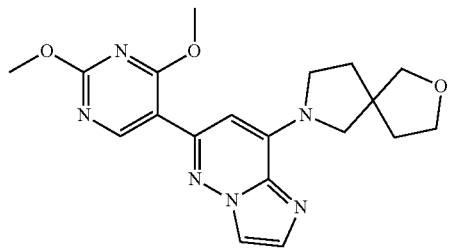 [SMILES: COc1ncc(-c2cc(N3CCC4(CCOC4)C3)c3nccn3n2)c(OC)n1]

7-(6-(2,4-dimethoxypyrimidin-5-yl)imidazo[1,2-b]pyridazin-8-yl)-2-oxa-7-azaspiro[4.4]nonane was prepared in the manner described for Intermediate 18, but replacing 6-chloro-8-cyclopropyl-2-methyl-imidazo[1,2-b]pyridazine with 7-(6-chloroimidazo[1,2-b]pyridazin-8-yl)-2-oxa-7-azaspiro[4.4]nonane. ES/MS m/z: 383.20 [M+H].

Intermediate 459. 2-(6-chloroimidazo[1,2-b]pyridazin-8-yl)-8-oxa-2-azaspiro[4.5]decane

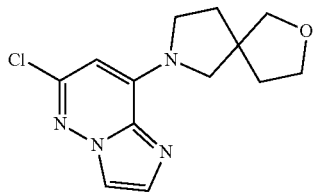 [SMILES: Clc1cc(N2CCC3(CCOC3)C2)c2nccn2n1]

2-(6-chloroimidazo[1,2-b]pyridazin-8-yl)-8-oxa-2-azaspiro[4.5]decane was prepared in the manner described for Intermediate 10, but replacing pyrrolidine with 8-oxa-2-azaspiro[4.5]decane. ES/MS m/z: 293.19 [M+H].

Intermediate 460. 2-(6-(2,4-dimethoxypyrimidin-5-yl)imidazo[1,2-b]pyridazin-8-yl)-8-oxa-2-azaspiro[4.5]decane

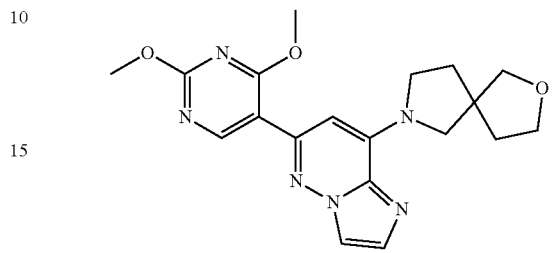

2-(6-(2,4-dimethoxypyrimidin-5-yl)imidazo[1,2-b]pyridazin-8-yl)-8-oxa-2-azaspiro[4.5]decane was prepared in the manner described for Intermediate 18, but replacing 6-chloro-8-cyclopropyl-2-methyl-imidazo[1,2-b]pyridazine with 2-(6-chloroimidazo[1,2-b]pyridazin-8-yl)-8-oxa-2-azaspiro[4.5]decane. ES/MS m/z: 397.20 [M+H].

Intermediate 461. 6-((1S,2S)-2-(6-chloroimidazo[1,2-b]pyridazin-8-yl)cyclopropyl)benzo[d]thiazole

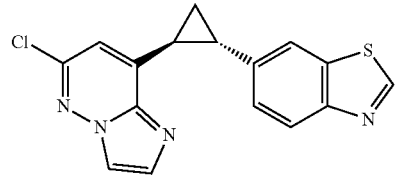 [SMILES: Clc1cc([C@H]2C[C@@H]2c2ccc3ncsc3c2)c2nccn2n1]

6(1S,2S)-2-(6-chloroimidazo[1,2-b]pyridazin-8-yl)cyclopropyl)benzo[d]thiazole as a racemate was prepared in the manner described for Intermediate 1, but replacing cyclopropylboronic acid with racemic 64(1S,2S)-2-(4,4,5,5-tetramethyl-1,3,2-dioxaborolan-2-yl)cyclopropyl)benzo[d]thiazole. ES/MS m/z: 327.01 [M+H].

Intermediate 462. 6-((2S,2S)-2-(6-(2,4-dimethoxypyrimidin-5-yl)imidazo[1,2-b]pyridazin-8-yl)cyclopropyl)benzo[d]thiazole

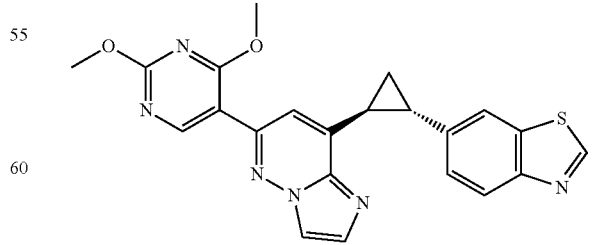

6-((1S,2S)-2-(6-(2,4-dimethoxypyrimidin-5-yl)imidazo[1,2-b]pyridazin-8-yl)cyclopropyl)benzo[d]thiazole as a racemate was prepared in the manner described for Intermediate 18, but replacing 6-chloro-8-cyclopropyl-2-methyl-imidazo[1,2-b]pyridazine with racemic 64(1S,2S)-2-(6-chloroimidazo[1,2-b]pyridazin-8-yl)cyclopropyl)benzo[d]thiazole. ES/MS m/z: 431.10 [M+H].

Intermediate 463. 6-chloro-3-fluoro-8-((2S,2S)-2-(4-(trifluoromethoxy)phenyl)cyclopropyl)imidazo[1,2-b]pyridazine

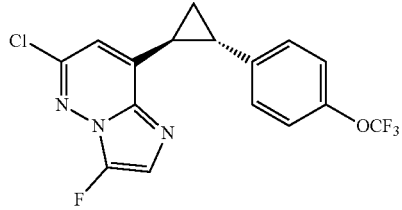 [SMILES: Fc1cnc2c([C@H]3C[C@@H]3c3ccc(OC(F)(F)F)cc3)cc(Cl)nn12]

6-chloro-3-fluoro-8-((1S,2S)-2-(4-(trifluoromethoxy)phenyl)cyclopropyl)imidazo[1,2-b]pyridazine as a racemate was prepared in the manner described for Intermediate 1, but replacing 8-bromo-6-chloro-2-methyl-imidazo[1,2-b]pyridazine with 8-bromo-6-chloro-3-fluoroimidazo[1,2-b]pyridazine and cyclopropylboronic acid with racemic 4,4,5,5-tetramethyl-2-((2S,2S)-2-(4-(trifluoromethoxy)phenyl)cyclopropyl)-1,3,2-dioxaborolane and 8-bromo-6-chloroimidazo[1,2-b]pyridazine with 8-bromo-6-chloro-3-fluoroimidazo[1,2-b]pyridazine. ES/MS m/z: 372.10 [M+H].

Intermediate 464. 6-(2,4-dimethoxypyrimidin-5-yl)-3-fluoro-8-((1S,2S)-2-(4-(trifluoromethoxy)phenyl)cyclopropyl)imidazo[1,2-b]pyridazine

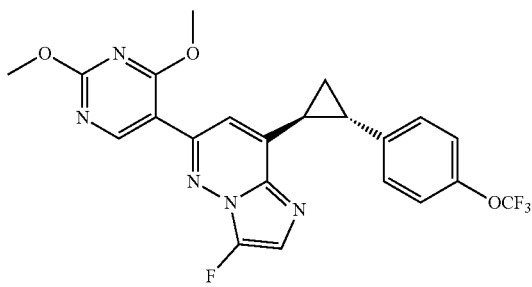 [SMILES: COc1ncc(-c2cc([C@H]3C[C@@H]3c3ccc(OC(F)(F)F)cc3)c3ncc(F)n3n2)c(OC)n1]

6-(2,4-dimethoxypyrimidin-5-yl)-3-fluoro-8-((2S,2S)-2-(4-(trifluoromethoxy)phenyl)cyclopropyl)imidazo[1,2-b]pyridazine as a racemate was prepared in the manner described for Intermediate 18, but replacing 6-chloro-8-cyclopropyl-2-methyl-imidazo[1,2-b]pyridazine with racemic 6-chloro-3-fluoro-8-((2S,2S)-2-(4-(trifluoromethoxy)phenyl)cyclopropyl)imidazo[1,2-b]pyridazine. ES/MS m/z: 476.17 [M+H].

Intermediate 465. 6-chloro-8-((2S,2S)-2-(2,2-difluorobenzo[d][1,3]dioxol-5-yl)cyclopropyl)-3-fluoro-imidazo[1,2-b]pyridazine

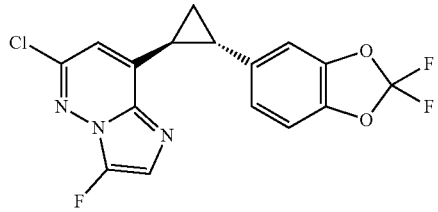 [SMILES: Fc1cnc2c([C@H]3C[C@@H]3c3ccc4c(c3)OC(F)(F)O4)cc(Cl)nn12]

6-chloro-8-((1S,2S)-2-(2,2-difluorobenzo[d][1,3]dioxol-5-yl)cyclopropyl)-3-fluoroimidazo[1,2-b]pyridazine as a racemate was prepared in the manner described for Intermediate 1, but replacing 8-bromo-6-chloro-2-methyl-imidazo[1,2-b]pyridazine with 8-bromo-6-chloro-3-fluoroimidazo[1,2-b]pyridazine and cyclopropylboronic acid with racemic 2-((1S,2S)-2-(2,2-difluorobenzo[d][1,3]dioxol-5-yl)cyclopropyl)-4,4,5,5-tetramethyl-1,3,2-dioxaborolane and 8-bromo-6-chloroimidazo[1,2-b]pyridazine with 8-bromo-6-chloro-3-fluoroimidazo[1,2-b]pyridazine. ES/MS m/z: 368.09 [M+H].

Intermediate 466. 8-((2S,2S)-2-(2,2-difluorobenzo[d][1,3]dioxol-5-yl)cyclopropyl)-6-(2,4-dimethoxypyrimidin-5-yl)-3-fluoro-5/3-imidazo[1,2-b][1,2]fluorazine

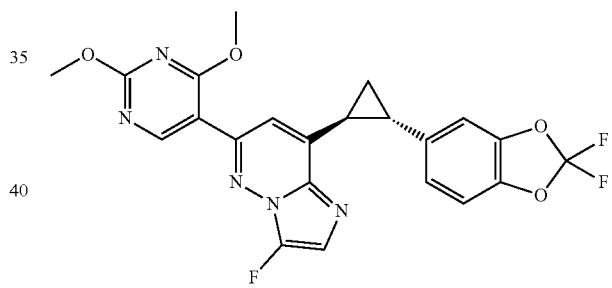

8-((1S,2S)-2-(2,2-difluorobenzo[d][1,3]dioxol-5-yl)cyclopropyl)-6-(2,4-dimethoxypyrimidin-5-yl)-3-fluoro-5-yl)-imidazo[1,2-b][1,2]fluorazine as a racemate was prepared in the manner described for Intermediate 18, but replacing 6-chloro-8-cyclopropyl-2-methyl-imidazo[1,2-b]pyridazine with racemic 6-chloro-8-((2S,2S)-2-(2,2-difluorobenzo[d][1,3]dioxol-5-yl)cyclopropyl)-3-fluoroimidazo[1,2-b]pyridazine. ES/MS m/z: 472.18 [M+H].

Intermediate 467. 3-fluoro-4-(1S,2S)-2-(4,4,5,5-tetramethyl-1,3,2-dioxaborolan-2-yl)cyclopropyl)benzonitrile

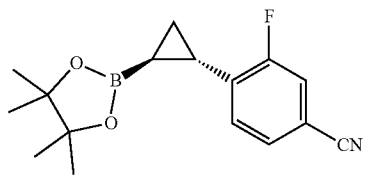 [SMILES: CC1(C)OB([C@H]2C[C@@H]2c2ccc(C#N)cc2F)OC1(C)C]

3-fluoro-4-(1S,2S)-2-(4,4,5,5-tetramethyl-1,3,2-dioxaborolan-2-yl)cyclopropyl)benzonitrile was prepared in the manner described for Intermediate 72, but replacing 5-bromo-2-chlorobenzonitrile with 4-bromo-3-fluorobenzonitrile. $^1$H NMR (400 MHz, DMSO-d6) δ 7.77 (dd, J=10.3, 1.6 Hz, 1H), 7.59 (dd, J=8.1, 1.6 Hz, 1H), 7.22 (t, J=7.9 Hz, 1H), 2.18 (dt, J=8.1, 5.5 Hz, 1H), 1.25-1.21 (m, 1H), 1.20 (d, J=2.3 Hz, 12H), 1.16-1.10 (m, 1H), 0.35 (ddd, J=9.9, 7.0, 5.6 Hz, 1H). $^{19}$F NMR (376 MHz, DMSO-d6) δ −119.15 (dd, J=10.3, 7.7 Hz).

Intermediate 468. 4-((2S,2S)-2-(6-chloroimidazo[1,2-b]pyridazin-8-yl)cyclopropyl)-3-fluorobenzonitrile

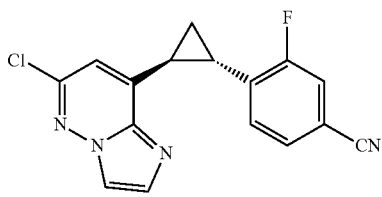 [SMILES: N#Cc1ccc([C@H]2C[C@@H]2c2cc(Cl)nn3ccnc23)c(F)c1]

4-(1S,2S)-2-(6-chloroimidazo[1,2-b]pyridazin-8-yl)cyclopropyl)-3-fluorobenzonitrile was prepared in the manner described for Intermediate 1, but replacing cyclopropylboronic acid with 3-fluoro-4-((2S,2S)-2-(4,4,5,5-tetramethyl-1,3,2-dioxaborolan-2-yl)cyclopropyl)benzonitrile. ES/MS m/z: 313.08 [M+H].

Intermediate 469. 4-((2S,2S)-2-(6-(2,4-dimethoxypyrimidin-5-yl)imidazo[1,2-b]pyridazin-8-yl)cyclopropyl)-3-fluorobenzonitrile

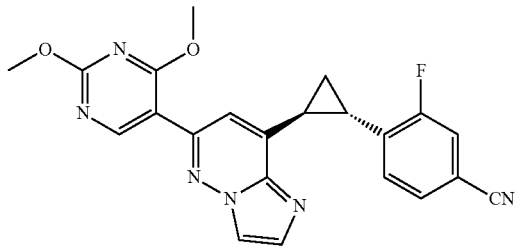 [SMILES: COc1ncc(-c2cc([C@H]3C[C@@H]3c3ccc(C#N)cc3F)c3nccn3n2)c(OC)n1]

4-((1S,2S)-2-(6-(2,4-dimethoxypyrimidin-5-yl)imidazo[1,2-b]pyridazin-8-yl)cyclopropyl)-3-fluorobenzonitrile was prepared in the manner described for Intermediate 18, but replacing 6-chloro-8-cyclopropyl-2-methyl-imidazo[1,2-b]pyridazine with 4-((1S,2S)-2-(6-chloroimidazo[1,2-b]pyridazin-8-yl)cyclopropyl)-3-fluorobenzonitrile. ES/MS m/z: 417.14 [M+H].

Intermediate 470. 6-chloro-8-((2S,2S)-2-(2-fluoro-4-(trifluoromethoxy)phenyl)cyclopropyl)imidazo[1,2-b]pyridazine

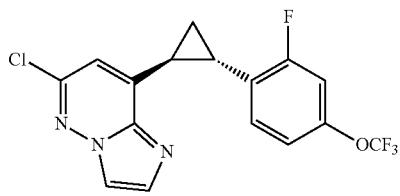 [SMILES: Fc1cc(OC(F)(F)F)ccc1[C@H]1C[C@@H]1c1cc(Cl)nn2ccnc12]

To racemic 2-((1S,2S)-2-(2-fluoro-4-(trifluoromethoxy)phenyl)cyclopropyl)-4,4,5,5-tetramethyl-1,3,2-dioxaborolane (150 mg, 0.43 mmol) in 1,4-dioxane (1.7 mL) was added 8-bromo-6-chloro--imidazo[1,2-b]pyridazine (100 mg, 0.43 mmol, 1 equiv), cataCXium A Pd G3 (31 mg, 0.04 mmol, 10 mol %), potassium phosphate tribasic (228 mg, 1.1 mmol, 2.5 equiv), and water (0.36 mL). The mixture was sparged with Ar, sealed, and heated to 120° C. After 16 h, the mixture was cooled to ambient temperature, filtered through celite, rinsed with EtOAc, and concentrated in vacuo. Purification by silica gel chromatography (0-100% EtOAc/hexanes) affording 6-chloro-8-((1S,2S)-2-(2-fluoro-4-(trifluoromethoxy)phenyl)cyclopropyl)imidazo[1,2-b]pyridazine as a racemate. ES/MS m/z: 372.08 [M+H].

Intermediate 471. 6-(2,4-dimethoxypyrimidin-5-yl)-8-((1S,2S)-2-(2-fluoro-4-(trifluoromethoxy)phenyl)cyclopropyl)imidazo[1,2-b]pyridazine

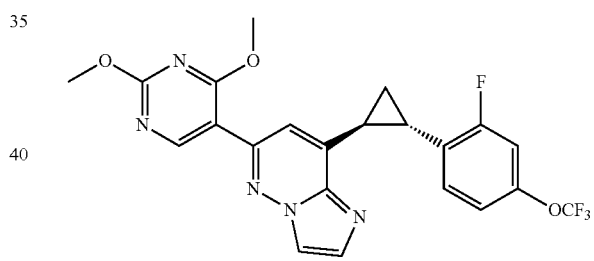

6-(2,4-dimethoxypyrimidin-5-yl)-8-((2S,2S)-2-(2-fluoro-4-(trifluoromethoxy)phenyl)cyclopropyl)imidazo[1,2-b]pyridazine as a racemate was prepared in the manner described for Intermediate 18, but replacing 6-chloro-8-cyclopropyl-2-methyl-imidazo[1,2-b]pyridazine with racemic 6-chloro-8-((1S,2S)-2-(2-fluoro-4-(trifluoromethoxy)phenyl)cyclopropyl)imidazo[1,2-b]pyridazine. ES/MS m/z: 476.18 [M+H].

Intermediate 472. methyl 4-((1S,2S)-2-(6-chloroimidazo[1,2-b]pyridazin-8-yl)cyclopropyl)benzoate

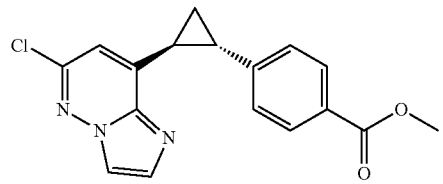 [SMILES: COC(=O)c1ccc([C@H]2C[C@@H]2c2cc(Cl)nn3ccnc23)cc1]

methyl 4-(1S,2S)-2-(6-chloroimidazo[1,2-b]pyridazin-8-yl)cyclopropyl)benzoate as a racemate was prepared in the manner described for Intermediate 470, but replacing 2-((2S,2S)-2-(2-fluoro-4-(trifluoromethoxy)phenyl)cyclopropyl)-4,4,5,5-tetramethyl-1,3,2-dioxaborolane with racemic methyl 4-((1S,2S)-2-(4,4,5,5-tetramethyl-1,3,2-dioxaborolan-2-yl)cyclopropyl)benzoate. ES/MS m/z: 328.10 [M+H].

Intermediate 473. methyl 4-((1S,2S)-2-(6-(2,4-dimethoxypyrimidin-5-yl)imidazo[1,2-b]pyridazin-8-yl)cyclopropyl)benzoate

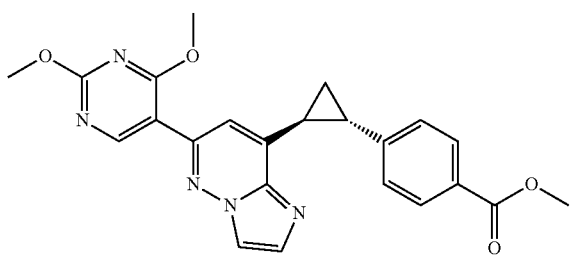

methyl 4-((1S,2S)-2-(6-(2,4-dimethoxypyrimidin-5-yl)imidazo[1,2-b]pyridazin-8-yl)cyclopropyl)benzoate as a racemate was prepared in the manner described for Intermediate 18, but replacing 6-chloro-8-cyclopropyl-2-methyl-imidazo[1,2-b]pyridazine with racemic methyl 4-(1S,2S)-2-(6-chloroimidazo[1,2-b]pyridazin-8-yl)cyclopropyl)benzoate. ES/MS m/z: 432.17 [M+H].

Intermediate 474. methyl 3-((2S,2S)-2-(6-chloroimidazo[1,2-b]pyridazin-8-yl)cyclopropyl)benzoate

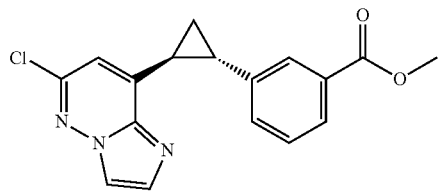 [SMILES: COC(=O)c1cccc([C@H]2C[C@@H]2c2cc(Cl)nn3ccnc23)c1]

methyl 3-((1S,2S)-2-(6-chloroimidazo[1,2-b]pyridazin-8-yl)cyclopropyl)benzoate as a racemate was prepared in the manner described for Intermediate 470, but replacing 2-((2S,2S)-2-(2-fluoro-4-(trifluoromethoxy)phenyl)cyclopropyl)-4,4,5,5-tetramethyl-1,3,2-dioxaborolane with racemic methyl 3-((2S,2S)-2-(4,4,5,5-tetramethyl-1,3,2-dioxaborolan-2-yl)cyclopropyl)benzoate. ES/MS m/z: 328.10 [M+H].

Intermediate 475. methyl 3-((2S,2S)-2-(6-(2,4-dimethoxypyrimidin-5-yl)imidazo[1,2-b]pyridazin-8-yl)cyclopropyl)benzoate

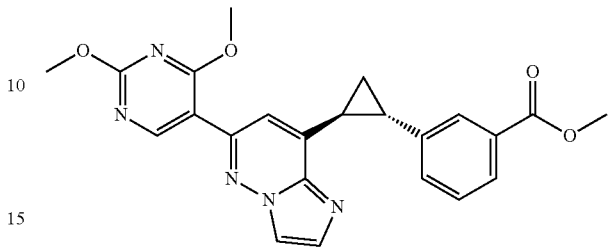

methyl 3-((1S,2S)-2-(6-(2,4-dimethoxypyrimidin-5-yl)imidazo[1,2-b]pyridazin-8-yl)cyclopropyl)benzoate as a racemate was prepared in the manner described for Intermediate 18, but replacing 6-chloro-8-cyclopropyl-2-methyl-imidazo[1,2-b]pyridazine with racemic methyl 3-((1S,2S)-2-(6-chloroimidazo[1,2-b]pyridazin-8-yl)cyclopropyl)benzoate. ES/MS m/z: 432.20 [M+H].

Intermediate 476. 4-((2S,2S)-2-(6-(2,4-dimethoxy-pyrimidin-5-yl)imidazo[1,2-b]pyridazin-8-yl)cyclopropyl)benzoic acid

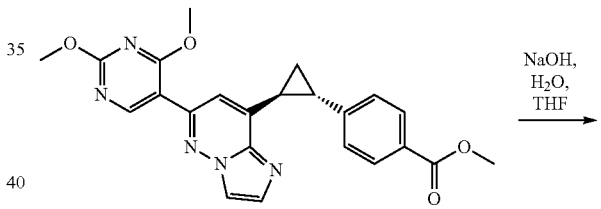

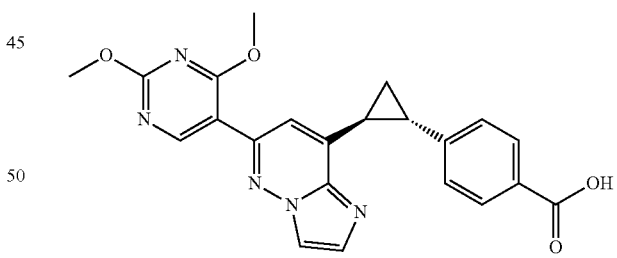

To methyl 4-((2S,2S)-2-(6-(2,4-dimethoxypyrimidin-5-yl)imidazo[1,2-b]pyridazin-8-yl)cyclopropyl)benzoate (1.0 g, 2.5 mmol) in THF (15 mL) was added 2 M aqueous sodium hydroxide (6 mL, 12 mmol, 5 equiv) and the mixture was heated to 60° C. After 7.5 h, the mixture was cooled to ambient temperature and acidified with 4M HCl in dioxane (6 mL). The volatiles were then removed under reduced pressure and the suspension was cooled to 0° C. overnight. The solids were filtered, rinsed with water, and dried under N2 to afford racemic 4-((1S,2S)-2-(6-(2,4-dimethoxypyrimidin-5-yl)imidazo[1,2-b]pyridazin-8-yl)cyclopropyl)benzoic acid. ES/MS m/z: 418.20 [M+H].

Intermediate 477. 4-((1S,2S)-2-(6-(2,4-dioxo-1,2,3,4-tetrahydropyrimidin-5-yl)imidazo[1,2-b]pyridazin-8-yl)cyclopropyl)benzoic acid

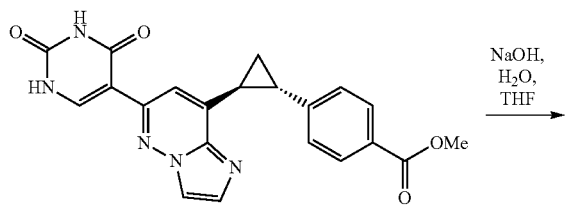

To methyl 4-((2S,2S)-2-(6-(2,4-dioxo-1,2,3,4-tetrahydropyrimidin-5-yl)imidazo[1,2-b]pyridazin-8-yl)cyclopropyl)benzoate (1.0 g, 2.5 mmol) in THF (15 mL) was added 2 M aqueous sodium hydroxide (6 mL, 12 mmol, 5 equiv) and the mixture was heated to 60° C. After 7.5 h, the mixture was cooled to ambient temperature and acidified with 4M HCl in dioxane (6 mL). The volatiles were then removed under reduced pressure and the suspension was cooled to 0° C. overnight. The solids were filtered, rinsed with water, and dried under N2 to afford 4-((1S,2S)-2-(6-(2,4-dioxo-1,2,3,4-tetrahydropyrimidin-5-yl)imidazo[1,2-b]pyridazin-8-yl)cyclopropyl)benzoic acid. ES/MS m/z: 390.10 [M+H].

Intermediate 478. 3-((1S,2S)-2-(6-(2,4-dioxo-1,2,3,4-tetrahydropyrimidin-5-yl)imidazo[1,2-b]pyridazin-8-yl)cyclopropyl)benzoic acid

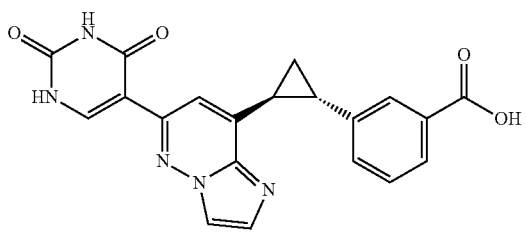 [SMILES: O=C(O)c1cccc([C@H]2C[C@@H]2c2cc(-c3c[nH]c(=O)[nH]c3=O)nn3ccnc23)c1]

3-((2S,2S)-2-(6-(2,4-dioxo-1,2,3,4-tetrahydropyrimidin-5-yl)imidazo[1,2-b]pyridazin-8-yl)cyclopropyl)benzoic acid as a racemate was prepared in the manner described for Intermediate 479, but replacing methyl 4-((2S,2S)-2-(6-(2,4-dioxo-1,2,3,4-tetrahydropyrimidin-5-yl)imidazo[1,2-b]pyridazin-8-yl)cyclopropyl)benzoate with racemic methyl 3-((1S,2S)-2-(6-(2,4-dioxo-1,2,3,4-tetrahydropyrimidin-5-yl)imidazo[1,2-b]pyridazin-8-yl)cyclopropyl)benzoate. ES/MS m/z: 390.14 [M+H].

Intermediate 479. 2-chloro-8-(3,3-difluoro-4,4-dimethylpyrrolidin-1-yl)-6-(2,4-dimethoxypyrimidin-5-yl)imidazo[1,2-b]pyridazine

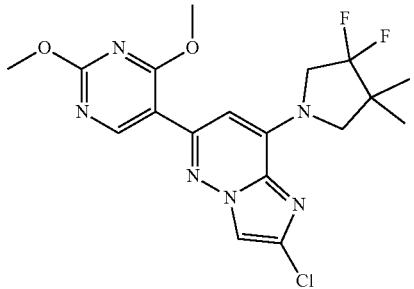

2-chloro-8-(3,3-difluoro-4,4-dimethylpyrrolidin-1-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 2,6-dichloro-8-(3,3-difluoro-4,4-dimethylpyrrolidin-1-yl)imidazo[1,2-b]pyridazine. ES/MS m/z: 425.01 [M+H].

Intermediate 480. 3-((2S,2S)-2-(6-(2,4-dimethoxypyrimidin-5-yl)imidazo[1,2-b]pyridazin-8-yl)cyclopropyl)benzoic acid

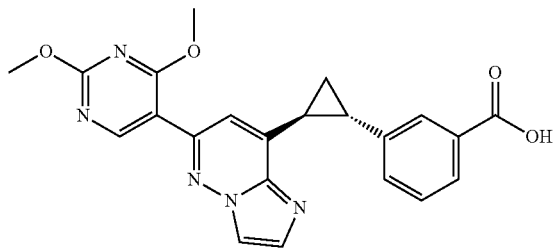 [SMILES: COc1ncc(-c2cc([C@H]3C[C@@H]3c3cccc(C(=O)O)c3)c3nccn3n2)c(OC)n1]

3-((1S,2S)-2-(6-(2,4-dimethoxypyrimidin-5-yl)imidazo[1,2-b]pyridazin-8-yl)cyclopropyl)benzoic acid as a racemate was prepared in the manner described for Intermediate 476, but replacing methyl 4-((2S,2S)-2-(6-(2,4-dimethoxypyrimidin-5-yl)imidazo[1,2-b]pyridazin-8-yl)cyclopropyl)benzoate with racemic methyl 3-((2S,2S)-2-(6-(2,4-dimethoxypyrimidin-5-yl)imidazo[1,2-b]pyridazin-8-yl)cyclopropyl)benzoate. ES/MS m/z: 418.16 [M+H].

Intermediate 481. 6-chloro-8-((1S,2S)-2-(2-(trifluoromethoxy)phenyl)cyclopropyl)imidazo[1,2-b]pyridazine

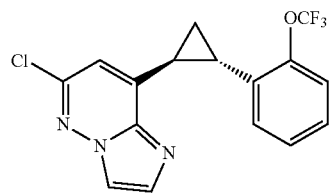 [SMILES: FC(F)(F)Oc1ccccc1[C@H]1C[C@@H]1c1cc(Cl)nn2ccnc12]

6-chloro-8-((1S,2S)-2-(2-(trifluoromethoxy)phenyl)cyclopropyl)imidazo[1,2-b]pyridazineas a racemate was prepared in the manner described for Intermediate 470, but replacing 2-((1S,2S)-2-(2-fluoro-4-(trifluoromethoxy)phenyl)cyclopropyl)-4,4,5,5-tetramethyl-1,3,2-dioxaborolane with racemic 4,4,5,5-tetramethyl-2-((2S,2S)-2-(2-(trifluoromethoxy)phenyl)cyclopropyl)-1,3,2-dioxaborolane. ES/MS m/z: 353.99 [M+H].

Intermediate 482. 6-(2,4-dimethoxypyrimidin-5-yl)-8-((1S,2S)-2-(2-(trifluoromethoxy)phenyl)cyclopropyl)imidazo[1,2-b]pyridazine

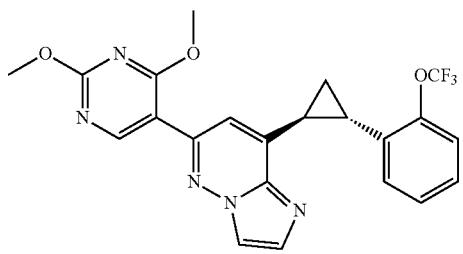 [SMILES: COc1ncc(-c2cc([C@H]3C[C@@H]3c3ccccc3OC(F)(F)F)c3nccn3n2)c(OC)n1]

6-(2,4-dimethoxypyrimidin-5-yl)-8-((1S,2S)-2-(2-(trifluoromethoxy)phenyl)cyclopropyl)imidazo[1,2-b]pyridazine as a racemate was prepared in the manner described for Intermediate 18, but replacing 6-chloro-8-cyclopropyl-2-methyl-imidazo[1,2-b]pyridazine with racemic 6-chloro-8-((1S,2S)-2-(2-(trifluoromethoxy)phenyl)cyclopropyl)imidazo[1,2-b]pyridazine. ES/MS m/z: 458.07 [M+H].

Intermediate 483. 4-((2S,2S)-2-(6-chloro-3-fluoroimidazo[1,2-b]pyridazin-8-yl)cyclopropyl)-3-fluorobenzonitrile

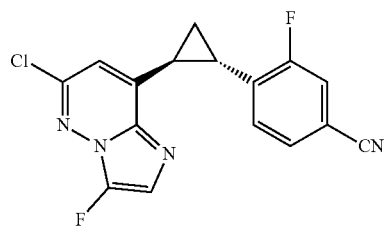 [SMILES: N#Cc1ccc([C@H]2C[C@@H]2c2cc(Cl)nn3c(F)cnc23)c(F)c1]

4-(1S,2S)-2-(6-chloro-3-fluoroimidazo[1,2-b]pyridazin-8-yl)cyclopropyl)-3-fluorobenzonitrile was prepared in the manner described for Intermediate 470, but replacing 2-((1S,2S)-2-(2-fluoro-4-(trifluoromethoxy)phenyl)cyclopropyl)-4,4,5,5-tetramethyl-1,3,2-dioxaborolane with 8-bromo-6-chloro-3-fluoroimidazo[1,2-b]pyridazine and cyclopropylboronic acid with 3-fluoro-4-(1S,2S)-2-(4,4,5,5-tetramethyl-1,3,2-dioxaborolan-2-yl)cyclopropyl)benzonitrile. ES/MS m/z: 331.00 [M+H].

Intermediate 484. 4-((2S,2S)-2-(6-(2,4-dimethoxypyrimidin-5-yl)-3-fluoroimidazo[1,2-b]pyridazin-8-yl)cyclopropyl)-3-fluorobenzonitrile

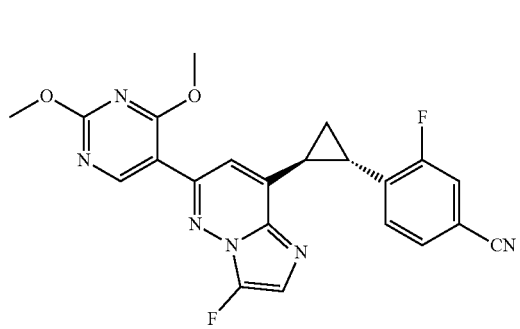 [SMILES: COc1ncc(-c2cc([C@H]3C[C@@H]3c3ccc(C#N)cc3F)c3ncc(F)n3n2)c(OC)n1]

4-((1S,2S)-2-(6-(2,4-dimethoxypyrimidin-5-yl)-3-fluoroimidazo[1,2-b]pyridazin-8-yl)cyclopropyl)-3-fluorobenzonitrile was prepared in the manner described for Intermediate 18, but replacing 6-chloro-8-cyclopropyl-2-methyl-imidazo[1,2-b]pyridazine with 4-((1S,2S)-2-(6-chloro-3-fluoroimidazo[1,2-b]pyridazin-8-yl)cyclopropyl)-3-fluorobenzonitrile. ES/MS m/z: 435.00 [M+H].

Intermediate 485. 5-((1S,2S)-2-(6-chloroimidazo[1,2-b]pyridazin-8-yl)cyclopropyl)nicotinonitrile

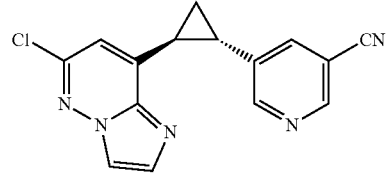 [SMILES: N#Cc1cncc([C@H]2C[C@@H]2c2cc(Cl)nn3ccnc23)c1]

5-((1S,2S)-2-(6-chloroimidazo[1,2-b]pyridazin-8-yl)cyclopropyl)nicotinonitrile as a racemate was prepared in the manner described for Intermediate 470, but replacing 2-((2S,2S)-2-(2-fluoro-4-(trifluoromethoxy)phenyl)cyclopropyl)-4,4,5,5-tetramethyl-1,3,2-dioxaborolane with racemic 5-((1S,2S)-2-(4,4,5,5-tetramethyl-1,3,2-dioxaborolan-2-yl)cyclopropyl)nicotinonitrile. ES/MS m/z: 296.00 [M+H].

Intermediate 486. 5-((2S,2S)-2-(6-(2,4-dimethoxypyrimidin-5-yl)imidazo[1,2-b]pyridazin-8-yl)cyclopropyl)nicotinonitrile

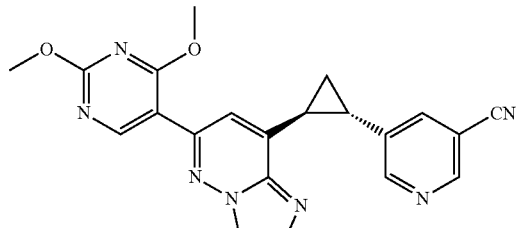

5-((1S,2S)-2-(6-(2,4-dimethoxypyrimidin-5-yl)imidazo[1,2-b]pyridazin-8-yl)cyclopropyl)nicotinonitrile as a racemate was prepared in the manner described for Intermediate 18, but replacing 6-chloro-8-cyclopropyl-2-methyl-imidazo[1,2-b]pyridazine with racemic 5-((1S,2S)-2-(6-chloroimidazo[1,2-b]pyridazin-8-yl)cyclopropyl)nicotinonitrile. ES/MS m/z: 400.12 [M+H].

Intermediate 487. methyl 4-((2S,2S)-2-(6-chloro-3-fluoroimidazo[1,2-b]pyridazin-8-yl)cyclopropyl)benzoate

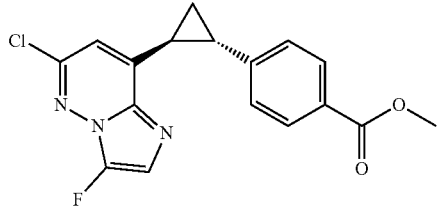 [SMILES: COC(=O)c1ccc([C@H]2C[C@@H]2c2cc(Cl)nn3c(F)cnc23)cc1]

methyl 4-((1S,2S)-2-(6-chloro-3-fluoroimidazo[1,2-b]pyridazin-8-yl)cyclopropyl)benzoate as a racemate was prepared in the manner described for Intermediate 470, but replacing 8-bromo-6-chloro-2-methyl-imidazo[1,2-b]pyridazine with 8-bromo-6-chloro-3-fluoroimidazo[1,2-b]pyridazine and 2-((1S,2S)-2-(2-fluoro-4-(trifluoromethoxy)phenyl)cyclopropyl)-4,4,5,5-tetramethyl-1,3,2-dioxaborolane with racemic methyl 4-((2S,2S)-2-(4,4,5,5-tetramethyl-1,3,2-dioxaborolan-2-yl)cyclopropyl)benzoate. ES/MS m/z: 346.00 [M+H].

Intermediate 488. methyl 4-(1S,2S)-2-(6-(2,4-dimethoxypyrimidin-5-yl)-3-fluoroimidazo[1,2-b]pyridazin-8-yl)cyclopropyl)benzoate

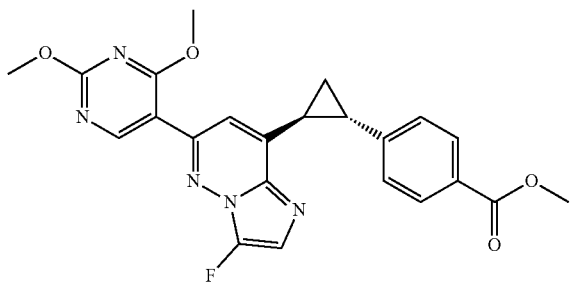

methyl 4-((1S,2S)-2-(6-(2,4-dimethoxypyrimidin-5-yl)-3-fluoroimidazo[1,2-b]pyridazin-8-yl)cyclopropyl)benzoate as a racemate was prepared in the manner described for Intermediate 18, but replacing 6-chloro-8-cyclopropyl-2-methyl-imidazo[1,2-b]pyridazine with racemic methyl 4-((1S,2S)-2-(6-chloro-3-fluoroimidazo[1,2-b]pyridazin-8-yl)cyclopropyl)benzoate. ES/MS m/z: 450.06 [M+H].

Intermediate 489. 4-((2S,2S)-2-(6-(2,4-dioxo-1,2,3,4-tetrahydropyrimidin-5-yl)-3-fluoroimidazo[1,2-b]pyridazin-8-yl)cyclopropyl)benzoic acid

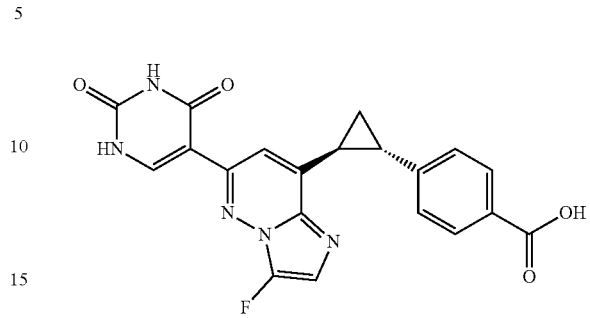

To methyl 4-((1S,2S)-2-(6-(2,4-dimethoxypyrimidin-5-yl)-3-fluoroimidazo[1,2-b]pyridazin-8-yl)cyclopropyl)benzoate (488 mg, 1.1 mmol) in THF (2.2 mL) and MeOH (1.0 mL was added 2 M aqueous lithium hydroxide (2.7 mL, 5.4 mmol, 5 equiv) and the mixture was heated to 60° C.

After 1 h, the reaction was cooled to ambient temperature, 4 M HCl in 1,4-dioxane was added (2 mL), and the resulting mixture was concentrated in vacuo. To the crude material was added MeOH (10 mL) and 1 M aqueous HCl (10 mL) and the mixture was heated to 80° C. After 24 h, the mixture was diluted with water (50 mL) and cooled to 0° C. Isolation by filtration afforded 4-((1S,2S)-2-(6-(2,4-dioxo-1,2,3,4-tetrahydropyrimidin-5-yl)-3-fluoroimidazo[1,2-b]pyridazin-8-yl)cyclopropyl)benzoic acid. ES/MS m/z: 408.00 [M+H].

Intermediate 490. 6-chloro-8-((1S,2S)-2-(1-(2,2,2-trifluoroethyl)-1H-indazol-5-yl)cyclopropyl)imidazo[1,2-b]pyridazine

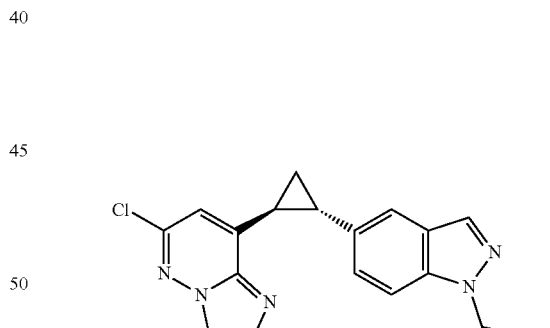

6-chloro-8-((1S,2S)-2-(1-(2,2,2-trifluoroethyl)-1H-indazol-5-yl)cyclopropyl)imidazo[1,2-b]pyridazine was prepared in the manner described for Intermediate 470, but replacing 2-((2S,2S)-2-(2-fluoro-4-(trifluoromethoxy)phenyl)cyclopropyl)-4,4,5,5-tetramethyl-1,3,2-dioxaborolane acid with 5-((2S,2S)-2-(4,4,5,5-tetramethyl-1,3,2-dioxaborolan-2-yl)cyclopropyl)-1-(2,2,2-trifluoroethyl)-1H-indazole. ES/MS m/z: 392.00 [M+H].

Intermediate 491. 6-(2,4-dimethoxypyrimidin-5-yl)-8-((1S,2S)-2-(1-(2,2,2-trifluoroethyl)-1H-indazol-5-yl)cyclopropyl)imidazo[1,2-b]pyridazine

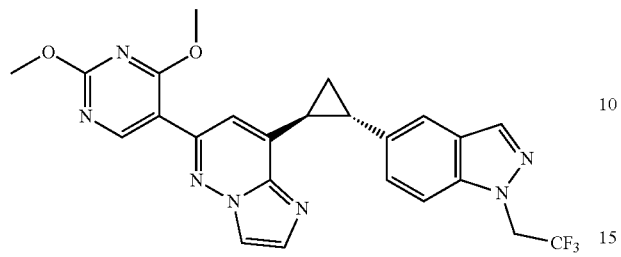

6-(2,4-dimethoxypyrimidin-5-yl)-8-((2S,2S)-2-(1-(2,2,2-trifluoroethyl)-1H-indazol-5-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(1-(2,2,2-trifluoroethyl)-1H-indazol-5-yl)cyclopropyl)imidazo[1,2-b]pyridazine. ES/MS m/z: 496.05 [M+H].

Intermediate 492. 6-chloro-3-fluoro-8-((2S,2S)-2-(1-(2,2,2-trifluoroethyl)-1H-indazol-5-yl)cyclopropyl)imidazo[1,2-b]pyridazine

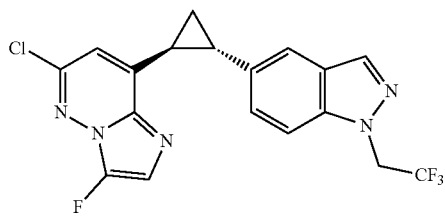 [SMILES: Fc1cnc2c([C@H]3C[C@@H]3c3ccc4c(cnn4CC(F)(F)F)c3)cc(Cl)nn12]

6-chloro-3-fluoro-8-((1S,2S)-2-(1-(2,2,2-trifluoroethyl)-1H-indazol-5-yl)cyclopropyl)imidazo[1,2-b]pyridazine was prepared in the manner described for Intermediate 470, but replacing 8-bromo-6-chloro-2-methyl-imidazo[1,2-b]pyridazine with 8-bromo-6-chloro-3-fluoroimidazo[1,2-b]pyridazine and 2-((2S,2S)-2-(2-fluoro-4-(trifluoromethoxy)phenyl)cyclopropyl)-4,4,5,5-tetramethyl-1,3,2-dioxaborolane with 5-((1S,2S)-2-(4,4,5,5-tetramethyl-1,3,2-dioxaborolan-2-yl)cyclopropyl)-1-(2,2,2-trifluoroethyl)-1H-indazole. ES/MS m/z: 409.96 [M+H].

Intermediate 493. 6-(2,4-dimethoxypyrimidin-5-yl)-3-fluoro-8-((1S,2S)-2-(1-(2,2,2-trifluoroethyl)-1H-indazol-5-yl)cyclopropyl)imidazo[1,2-b]pyridazine

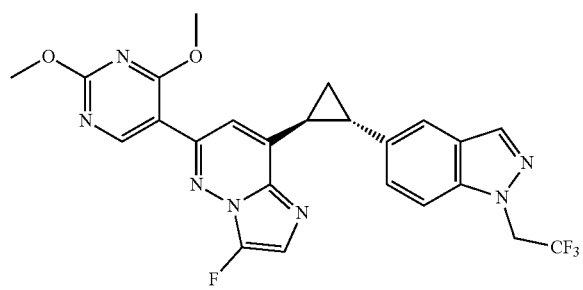 [SMILES: COc1ncc(-c2cc([C@H]3C[C@@H]3c3ccc4c(cnn4CC(F)(F)F)c3)c3ncc(F)n3n2)c(OC)n1]

6-(2,4-dimethoxypyrimidin-5-yl)-3-fluoro-8-((1S,2S)-2-(1-(2,2,2-trifluoroethyl)-1H-indazol-5-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-((2S,2S)-2-(1-(2,2,2-trifluoroethyl)-1H-indazol-5-yl)cyclopropyl)imidazo[1,2-b]pyridazine. ES/MS m/z: 514.09 [M+H].

Intermediate 494. 6-chloro-8-((2S,2S)-2-(1-(2,2,2-trifluoroethyl)-1H-indazol-6-yl)cyclopropyl)imidazo[1,2-b]pyridazine

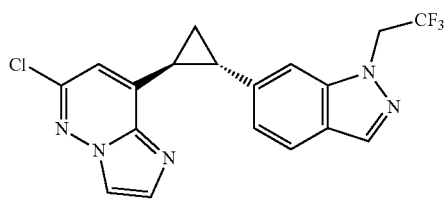 [SMILES: FC(F)(F)Cn1ncc2ccc([C@H]3C[C@@H]3c3cc(Cl)nn4ccnc34)cc21]

6-chloro-8-((1S,2S)-2-(1-(2,2,2-trifluoroethyl)-1H-indazol-6-yl)cyclopropyl)imidazo[1,2-b]pyridazine was prepared in the manner described for Intermediate 470, but replacing 2-((2S,2S)-2-(2-fluoro-4-(trifluoromethoxy)phenyl)cyclopropyl)-4,4,5,5-tetramethyl-1,3,2-dioxaborolane with 6-((2S,2S)-2-(4,4,5,5-tetramethyl-1,3,2-dioxaborolan-2-yl)cyclopropyl)-1-(2,2,2-trifluoroethyl)-1H-indazole. ES/MS m/z: 392.00 [M+H].

Intermediate 495. 6-(2,4-dimethoxypyrimidin-5-yl)-8-((1S,2S)-2-(1-(2,2,2-trifluoroethyl)-1H-indazol-6-yl)cyclopropyl)imidazo[1,2-b]pyridazine

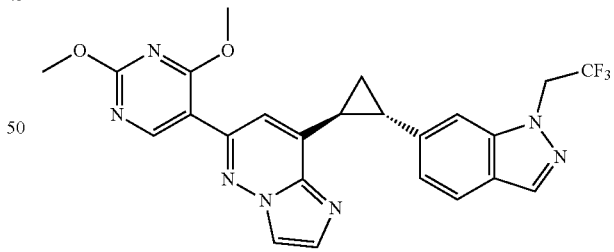

6-(2,4-dimethoxypyrimidin-5-yl)-8-((2S,2S)-2-(1-(2,2,2-trifluoroethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(1-(2,2,2-trifluoroethyl)-1H-indazol-6-yl)cyclopropyl)imidazo[1,2-b]pyridazine. ES/MS m/z: 496.05 [M+H].

Intermediate 496. 6-chloro-3-fluoro-8-((2S,2S)-2-(1-(2,2,2-trifluoroethyl)-1H-indazol-6-yl)cyclopropyl)imidazo[1,2-b]pyridazine

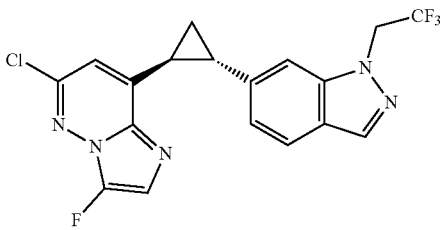 [SMILES: Fc1cnc2c([C@H]3C[C@@H]3c3ccc4cnn(CC(F)(F)F)c4c3)cc(Cl)nn12]

6-chloro-3-fluoro-8-((1S,2S)-2-(1-(2,2,2-trifluoroethyl)-1H-indazol-6-yl)cyclopropyl)imidazo[1,2-b]pyridazine was prepared in the manner described for Intermediate 470, but replacing 8-bromo-6-chloro-2-methyl-imidazo[1,2-b]pyridazine with 8-bromo-6-chloro-3-fluoroimidazo[1,2-b]pyridazine and 2-((1S,2S)-2-(2-fluoro-4-(trifluoromethoxy)phenyl)cyclopropyl)-4,4,5,5-tetramethyl-1,3,2-dioxaborolane with 6-((1S,2S)-2-(4,4,5,5-tetramethyl-1,3,2-dioxaborolan-2-yl)cyclopropyl)-1-(2,2,2-trifluoroethyl)-1H-indazole. ES/MS m/z: 409.96 [M+H].

Intermediate 497. 6-(2,4-dimethoxypyrimidin-5-yl)-3-fluoro-8-((1S,2S)-2-(1-(2,2,2-trifluoroethyl)-1H-indazol-6-yl)cyclopropyl)imidazo[1,2-b]pyridazine

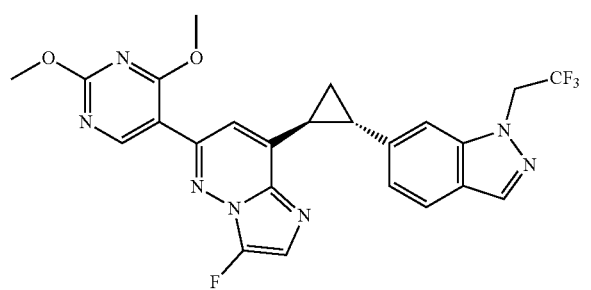 [SMILES: COc1ncc(-c2cc([C@H]3C[C@@H]3c3ccc4cnn(CC(F)(F)F)c4c3)c3ncc(F)n3n2)c(OC)n1]

6-(2,4-dimethoxypyrimidin-5-yl)-3-fluoro-8-((1S,2S)-2-(1-(2,2,2-trifluoroethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-((1S,2S)-2-(1-(2,2,2-trifluoroethyl)-1H-indazol-6-yl)cyclopropyl)imidazo[1,2-b]pyridazine. ES/MS m/z: 514.09 [M+H].

Intermediate 498. 5-((1S,2S)-2-(6-chloroimidazo[1,2-b]pyridazin-8-yl)cyclopropyl)-2-methylbenzo[d]thiazole

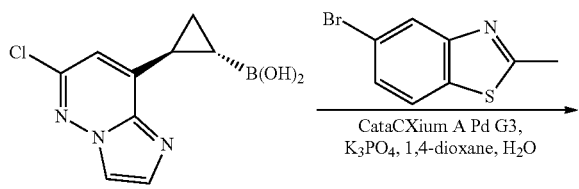

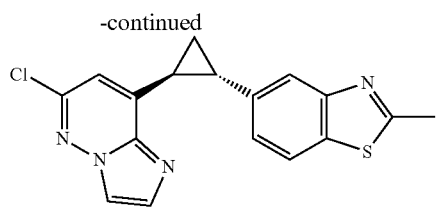

To racemic ((2S,2S)-2-(6-chloroimidazo[1,2-b]pyridazin-8-yl)cyclopropyl)boronic acid (50 mg, 0.21 mmol), 5-bromo-2-methylbenzo[d]thiazole (96 mg, 0.42 mmol, 2 equiv), cataCXium A Pd G3 (31 mg, 0.04 mmol, 0.2 equiv), and potassium phosphate tribasic (112 mg, 0.53 mmol, 2.5 equiv) in 1,4-dioxane (1 mL) and water (0.2 mL) was sparged with Ar, sealed, and heated 85° C. After 2 h, the mixture was filtered through celite, rinsed with EtOAc, and concentrated in vacuo. Purification by silica gel chromatography (0-100% EtOAc/hexanes) afforded 5-((1S,2S)-2-(6-chloroimidazo[1,2-b]pyridazin-8-yl)cyclopropyl)-2-methylbenzo[d]thiazole as a racemate. ES/MS m/z: 341.00 [M+H].

Intermediate 499. 5-((2S,2S)-2-(6-(2,4-dimethoxypyrimidin-5-yl)imidazo[1,2-b]pyridazin-8-yl)cyclopropyl)-2-methylbenzo[d]thiazole

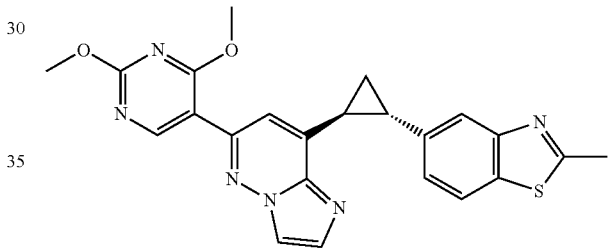

5-((1S,2S)-2-(6-(2,4-dimethoxypyrimidin-5-yl)imidazo[1,2-b]pyridazin-8-yl)cyclopropyl)-2-methylbenzo[d]thiazole as a racemate was prepared in the manner described for Intermediate 18, but replacing 6-chloro-8-cyclopropyl-2-methyl-imidazo[1,2-b]pyridazine with racemic 5-((2S,2S)-2-(6-chloroimidazo[1,2-b]pyridazin-8-yl)cyclopropyl)-2-methylbenzo[d]thiazole. ES/MS m/z: 445.08 [M+H].

Intermediate 500. 6-chloro-8-((1S,2S)-2-(1-(2,2,2-trifluoroethyl)-1H-benzo[d]imidazol-6-yl)cyclopropyl)imidazo[1,2-b]pyridazine

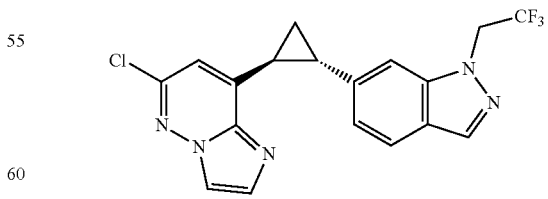

6-chloro-8-((2S,2S)-2-(1-(2,2,2-trifluoroethyl)-1H-benzo[d]imidazol-6-yl)cyclopropyl)imidazo[1,2-b]pyridazine was prepared in the manner described for Intermediate 470, but replacing 2-((2S,2S)-2-(2-fluoro-4-(trifluoromethoxy)phenyl)cyclopropyl)-4,4,5,5-tetramethyl-1,3,2-dioxaborolane with 6-((2S,2S)-2-(4,4,5,5-tetramethyl-1,3,2-dioxaborolan-2-yl)cyclopropyl)-1-(2,2,2-trifluoroethyl)-1H-benzo[d]imidazole. ES/MS m/z: 392.00 [M+H].

Intermediate 501. 6-(2,4-dimethoxypyrimidin-5-yl)-8-((1S,2S)-2-(1-(2,2,2-trifluoroethyl)-1H-benzo[d]imidazol-6-yl)cyclopropyl)imidazo[1,2-b]pyridazine

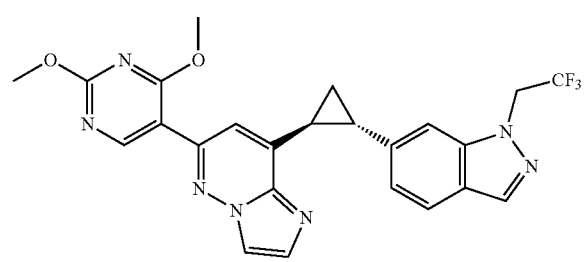 [SMILES: COc1ncc(-c2cc([C@H]3C[C@@H]3c3ccc4cnn(CC(F)(F)F)c4c3)c3nccn3n2)c(OC)n1]

6-(2,4-dimethoxypyrimidin-5-yl)-8-((1S,2S)-2-(1-(2,2,2-trifluoroethyl)-1H-benzo[d]imidazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(1-(2,2,2-trifluoroethyl)-1H-benzo[d]imidazol-6-yl)cyclopropyl)imidazo[1,2-b]pyridazine. ES/MS m/z: 496.10 [M+H].

Intermediate 502. 6-chloro-3-fluoro-8-((2S,2S)-2-(1-(2,2,2-trifluoroethyl)-1H-benzo[d]imidazol-6-yl)cyclopropyl)imidazo[1,2-b]pyridazine

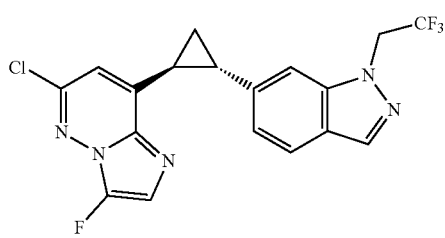 [SMILES: Fc1cnc2c([C@H]3C[C@@H]3c3ccc4cnn(CC(F)(F)F)c4c3)cc(Cl)nn12]

6-chloro-3-fluoro-8-((1S,2S)-2-(1-(2,2,2-trifluoroethyl)-1H-benzo[d]imidazol-6-yl)cyclopropyl)imidazo[1,2-b]pyridazine was prepared in the manner described for Intermediate 470, but replacing 8-bromo-6-chloro-2-methyl-imidazo[1,2-b]pyridazine with 8-bromo-6-chloro-3-fluoroimidazo[1,2-b]pyridazine and 2-((1S,2S)-2-(2-fluoro-4-(trifluoromethoxy)phenyl)cyclopropyl)-4,4,5,5-tetramethyl-1,3,2-dioxaborolane with 6-((1S,2S)-2-(4,4,5,5-tetramethyl-1,3,2-dioxaborolan-2-yl)cyclopropyl)-1-(2,2,2-trifluoroethyl)-1H-benzo[d]imidazole. ES/MS m/z: 410.00 [M+H].

Intermediate 503. 6-(2,4-dimethoxypyrimidin-5-yl)-3-fluoro-8-((1S,2S)-2-(1-(2,2,2-trifluoroethyl)-1H-benzo[d]imidazol-6-yl)cyclopropyl)imidazo[1,2-b]pyridazine

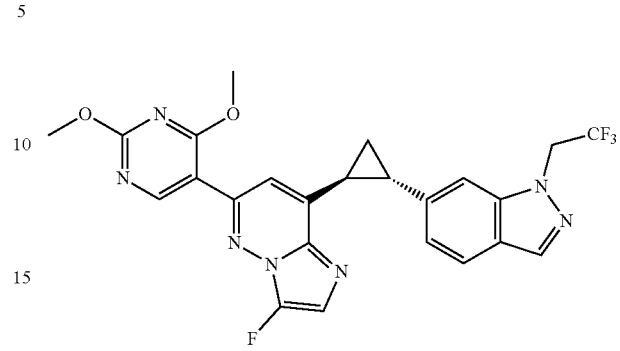

6-(2,4-dimethoxypyrimidin-5-yl)-3-fluoro-8-((1S,2S)-2-(1-(2,2,2-trifluoroethyl)-1H-benzo[d]imidazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-((2S,2S)-2-(1-(2,2,2-trifluoroethyl)-1H-benzo[d]imidazol-6-yl)cyclopropyl)imidazo[1,2-b]pyridazine. ES/MS m/z: 514.10 [M+H].

Intermediate 504. 6-chloro-8-((1S,2S)-2-(1-(2,2,2-trifluoroethyl)-1H-benzo[d]imidazol-5-yl)cyclopropyl)imidazo[1,2-b]pyridazine

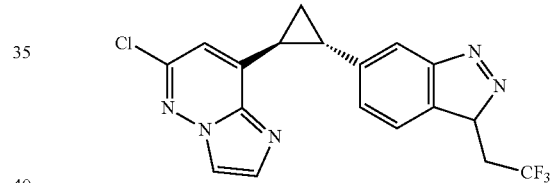

6-chloro-8-((2S,2S)-2-(1-(2,2,2-trifluoroethyl)-1H-benzo[d]imidazol-5-yl)cyclopropyl)imidazo[1,2-b]pyridazine was prepared in the manner described for Intermediate 470, but replacing 2-((2S,2S)-2-(2-fluoro-4-(trifluoromethoxy)phenyl)cyclopropyl)-4,4,5,5-tetramethyl-1,3,2-dioxaborolane with 5-((2S,2S)-2-(4,4,5,5-tetramethyl-1,3,2-dioxaborolan-2-yl)cyclopropyl)-1-(2,2,2-trifluoroethyl)-1H-benzo[d]imidazole. ES/MS m/z: 392.00 [M+H].

Intermediate 505. 6-(2,4-dimethoxypyrimidin-5-yl)-8-((1S,2S)-2-(1-(2,2,2-trifluoroethyl)-1H-benzo[d]imidazol-5-yl)cyclopropyl)imidazo[1,2-b]pyridazine

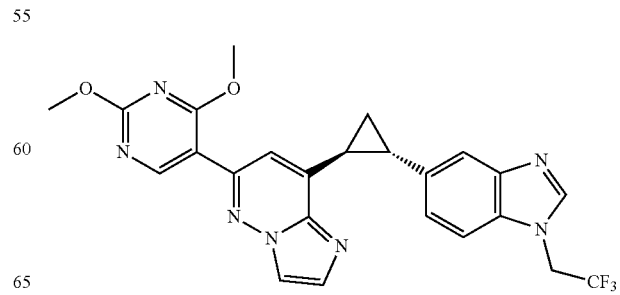

6-(2,4-dimethoxypyrimidin-5-yl)-8-((1S,2S)-2-(1-(2,2,2-trifluoroethyl)-1H-benzo[d]imidazol-5-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(1-(2,2,2-trifluoroethyl)-1H-benzo[d]imidazol-5-yl)cyclopropyl)imidazo[1,2-b]pyridazine. ES/MS m/z: 496.10 [M+H].

Intermediate 506. 6-chloro-8-((1S,2S)-2-(1-methyl-1H-indazol-6-yl)cyclopropyl)imidazo[1,2-b]pyridazine

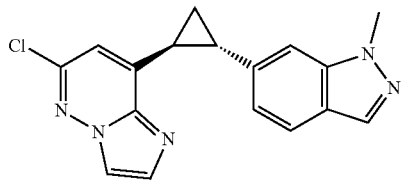 [SMILES: Cn1ncc2ccc([C@H]3C[C@@H]3c3cc(Cl)nn4ccnc34)cc21]

6-chloro-8-((1S,2S)-2-(1-methyl-1H-indazol-6-yl)cyclopropyl)imidazo[1,2-b]pyridazine as a racemate was prepared in the manner described for Intermediate 498, but replacing 5-bromo-2-methylbenzo[d]thiazole with 6-bromo-1-methyl-1H-indazole. ES/MS m/z: 324.00 [M+H].

Intermediate 508. 6-(2,4-dimethoxypyrimidin-5-yl)-8-((1S,2S)-2-(1-methyl-1H-indazol-6-yl)cyclopropyl)imidazo[1,2-b]pyridazine

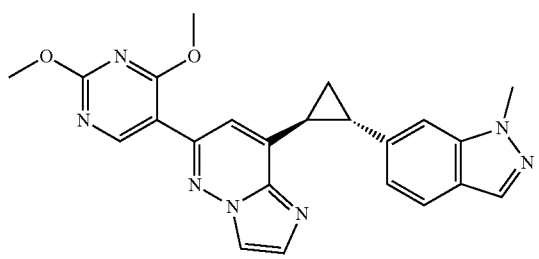 [SMILES: COc1ncc(-c2cc([C@H]3C[C@@H]3c3ccc4cnn(C)c4c3)c3nccn3n2)c(OC)n1]

6-(2,4-dimethoxypyrimidin-5-yl)-8-((1S,2S)-2-(1-methyl-1H-indazol-6-yl)cyclopropyl)imidazo[1,2-b]pyridazine as a racemate was prepared in the manner described for Intermediate 18, but replacing 6-chloro-8-cyclopropyl-2-methyl-imidazo[1,2-b]pyridazine with racemic 6-chloro-8-((1S,2S)-2-(1-methyl-1H-indazol-6-yl)cyclopropyl)imidazo[1,2-b]pyridazine. ES/MS m/z: 428.10 [M+H].

Intermediate 509. 5-((2S,2S)-2-(6-chloroimidazo[1,2-b]pyridazin-8-yl)cyclopropyl)-3-(trifluoromethyl)benzo[d]isoxazole

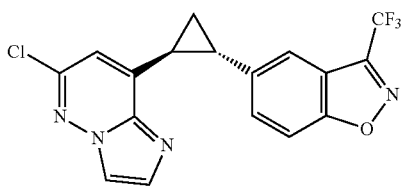 [SMILES: FC(F)(F)c1noc2ccc([C@H]3C[C@@H]3c3cc(Cl)nn4ccnc34)cc12]

5-((1S,2S)-2-(6-chloroimidazo[1,2-b]pyridazin-8-yl)cyclopropyl)-3-(trifluoromethyl)benzo[d]isoxazole as a racemate was prepared in the manner described for Intermediate 498, but replacing 5-bromo-2-methylbenzo[d]thiazole with 5-bromo-3-(trifluoromethyl)benzo[d]isoxazole. ES/MS m/z: 379.00 [M+H].

Intermediate 510. 5-((2S,2S)-2-(6-(2,4-dimethoxypyrimidin-5-yl)imidazo[1,2-b]pyridazin-8-yl)cyclopropyl)-3-(trifluoromethyl)benzo[d]isoxazole

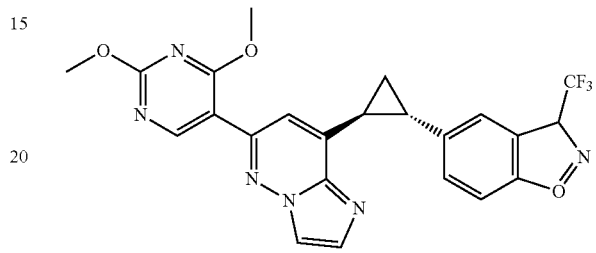

5-((2S,2S)-2-(6-(2,4-dimethoxypyrimidin-5-yl)imidazo[1,2-b]pyridazin-8-yl)cyclopropyl)-3-(trifluoromethyl)benzo[d]isoxazole as a racemate was prepared in the manner described for Intermediate 18, but replacing 6-chloro-8-cyclopropyl-2-methyl-imidazo[1,2-b]pyridazine with racemic 5-((2S,2S)-2-(6-chloroimidazo[1,2-b]pyridazin-8-yl)cyclopropyl)-3-(trifluoromethyl)benzo[d]isoxazole. ES/MS m/z: 483.00 [M+H].

Intermediate 511. 2,6-dichloro-8-(3,3-difluoro-4,4-dimethylpyrrolidin-1-yl)imidazo[1,2-b]pyridazine

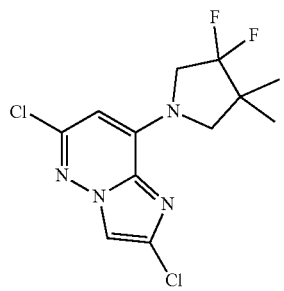 [SMILES: CC1(C)CN(c2cc(Cl)nn3cc(Cl)nc23)CC1(F)F]

2,6-dichloro-8-(3,3-difluoro-4,4-dimethylpyrrolidin-1-yl)imidazo[1,2-b]pyridazine was prepared in the manner described for Intermediate 10, but replacing 8-bromo-6-chloroimidazo[1,2-b]pyridazine with 2,6,8-trichloroimidazo[1,2-b]pyridazine and pyrrolidine with 3,3-difluoro-4,4-dimethylpyrrolidine. ES/MS m/z: 320.98 [M+H].

Intermediate 512. 8-((1S,2S)-2-(2,2-difluorobenzo[d][1,3]dioxol-5-yl)cyclopropyl)-6-(2,4-dimethoxypyrimidin-5-yl)imidazo[1,2-b]pyridazine

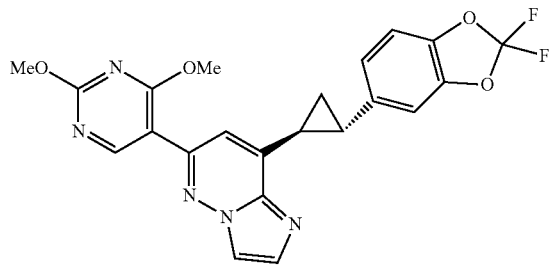 [SMILES: COc1ncc(-c2cc([C@H]3C[C@@H]3c3ccc4c(c3)OC(F)(F)O4)c3nccn3n2)c(OC)n1]

8-((1S,2S)-2-(2,2-difluorobenzo[d][1,3]dioxol-5-yl)cyclopropyl)-6-(2,4-dimethoxypyrimidin-5-yl)imidazo[1,2-b]pyridazine was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(2,2-difluorobenzo[d][1,3]dioxol-5-yl)cyclopropyl)imidazo[1,2-b]pyridazine. ES/MS m/z: 454.20 [M+H].

Intermediate 513. 1-(6-(2,4-dimethoxypyrimidin-5-yl)imidazo[1,2-b]pyridazin-8-yl)-4,4-difluoropyrrolidin-3-ol

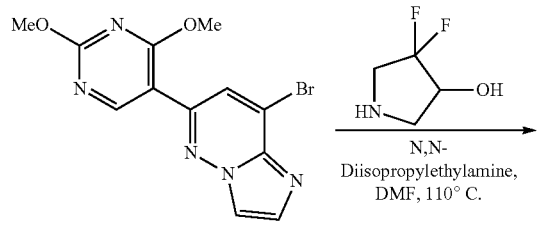

A solution of 8-bromo-6-(2,4-dimethoxypyrimidin-5-yl)imidazo[1,2-b]pyridazine (1800 mg, 5.35 mmol), 4,4-difluoropyrrolidin-3-ol (1.07 g, 5.35 mmol), DIPEA (2.8 mL, 16.1 mmol) in DMF (10 mL) was heated to 110° C. After 20 hours, the reaction mixture was diluted with EtOAc washed with brine, dried over Na$_2$SO$_4$, filtered, organic residue was purified by SiO$_2$ chromatography (0-100% EtOAc/Hex), affording 1-(6-(2,4-dimethoxypyrimidin-5-yl)imidazo[1,2-b]pyridazin-8-yl)-4,4-difluoropyrrolidin-3-ol. ES/MS m/z: 379.20 [M+H].

Intermediate 514. 8-(3,3-difluoro-4-((4-(trifluoromethyl)pyridin-2-yl)oxy)pyrrolidin-1-yl)-6-(2,4-dimethoxypyrimidin-5-yl)imidazo[1,2-b]pyridazine

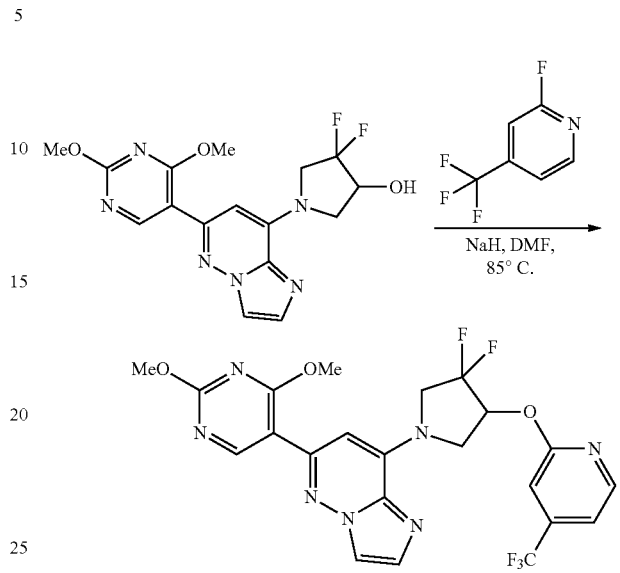

NaH (16 mg, 0.42 mmol, 60% in mineral oil) was added to the solution of 1-(6-(2,4-dimethoxypyrimidin-5-yl)imidazo[1,2-b]pyridazin-8-yl)-4,4-difluoropyrrolidin-3-ol (80 mg, 0.21 mmol) in DMF (3 ml), then 2-fluoro-4-(trifluoromethyl)pyridine (70 mg, 0.42 mol) was added to the reaction mixture and was heated to 85oC for 4 hours, the reaction mixture was cooled to room temperature. The layers were separated, and the aqueous layer was extracted with EtOAc (3×200 mL). The combined organic layers were dried over Na$_2$SO$_4$, filtered, and concentrated. Purification was accomplished by SiO$_2$ chromatography (0-100% EtOAc/Hex), affording 8-(3,3-difluoro-4-((4-(trifluoromethyl)pyridin-2-yl)oxy)pyrrolidin-1-yl)-6-(2,4-dimethoxypyrimidin-5-yl)imidazo[1,2-b]pyridazine. ES/MS m/z: 524.20 [M+H].

Intermediate 515. 8-(4-((5-(difluoromethoxy)pyridin-2-yl)oxy)-3,3-difluoropyrrolidin-1-yl)-6-(2,4-dimethoxypyrimidin-5-yl)imidazo[1,2-b]pyridazine

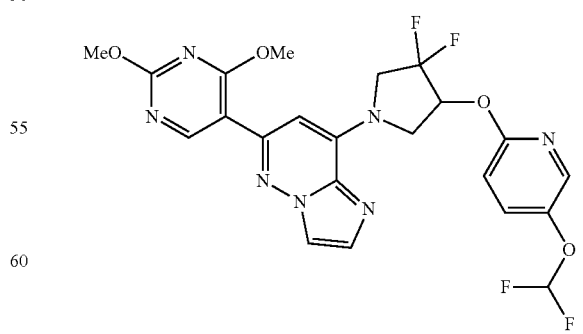

8-(4-((5-(difluoromethoxy)pyridin-2-yl)oxy)-3,3-difluoropyrrolidin-1-yl)-6-(2,4-dimethoxypyrimidin-5-yl)imidazo[1,2-b]pyridazine was prepared in the manner described for Intermediate 514, but replacing fluoro-4-(trifluoromethyl)pyridine with 5-(difluoromethoxy)-2-fluoropyridine. ES/MS m/z: 522.20 [M+H].

Intermediate 516. 8-(3,3-difluoro-4-((5-(trifluoromethoxy)pyridin-2-yl)oxy)pyrrolidin-1-yl)-6-(2,4-dimethoxypyrimidin-5-yl)imidazo[1,2-b]pyridazine

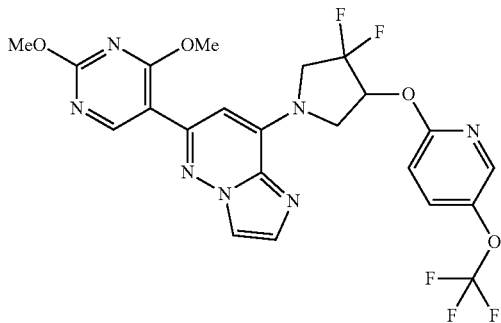 [SMILES: COc1ncc(-c2cc(N3CC(Oc4ccc(OC(F)(F)F)cn4)C(F)(F)C3)c3nccn3n2)c(OC)n1]

8-(3,3-difluoro-4-((5-(trifluoromethoxy)pyridin-2-yl)oxy)pyrrolidin-1-yl)-6-(2,4-dimethoxypyrimidin-5-yl)imidazo[1,2-b]pyridazine was prepared in the manner described for Intermediate 514, but replacing fluoro-4-(trifluoromethyl)pyridine with 2-fluoro-4-(trifluoromethoxy)pyridine. ES/MS m/z: 540.20 [M+H].

Intermediate 517. 8-(3,3-difluoro-4-((5-(perfluoroethoxy)pyridin-2-yl)oxy)pyrrolidin-1-yl)-6-(2,4-dimethoxypyrimidin-5-yl)imidazo[1,2-b]pyridazine

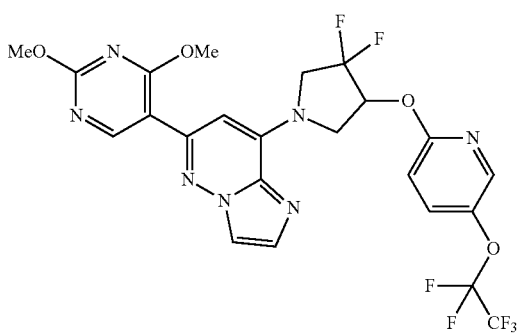 [SMILES: COc1ncc(-c2cc(N3CC(Oc4ccc(OC(F)(F)C(F)(F)F)cn4)C(F)(F)C3)c3nccn3n2)c(OC)n1]

8-(3,3-difluoro-4-(5-(perfluoroethoxy)pyridin-2-yl)oxy)pyrrolidin-1-yl)-6-(2,4-dimethoxypyrimidin-5-yl)imidazo[1,2-b]pyridazine was prepared in the manner described for Intermediate 514, but replacing fluoro-4-(trifluoromethyl)pyridine with 2-fluoro-5-(perfluoroethoxy)pyridine. ES/MS m/z: 590.20 [M+H].

Intermediate 518. 6-((1-(6-(2,4-dimethoxypyrimidin-5-yl)imidazo[1,2-b]pyridazin-8-yl)-4,4-difluoropyrrolidin-3-yl)oxy)nicotinonitrile

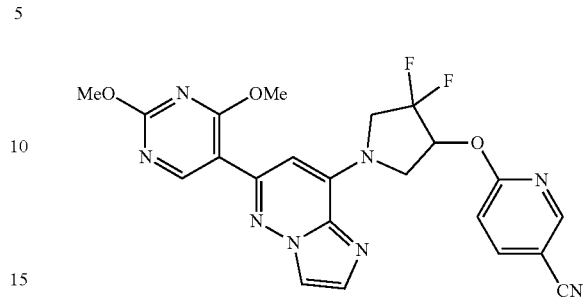

6-((1-(6-(2,4-dimethoxypyrimidin-5-yl)imidazo[1,2-b]pyridazin-8-yl)-4,4-difluoropyrrolidin-3-yl)oxy)nicotinonitrile was prepared in the manner described for Intermediate 514, but replacing fluoro-4-(trifluoromethyl)pyridine with 6-fluoronicotinonitrile. ES/MS m/z: 481.20 [M+H].

Intermediate 519. 8-(3,3-difluoro-4-((5-(trifluoromethyl)pyrazin-2-yl)oxy)pyrrolidin-1-yl)-6-(2,4-dimethoxypyrimidin-5-yl)imidazo[1,2-b]pyridazine

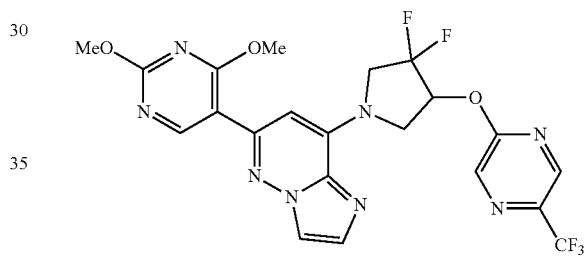

8-(3,3-difluoro-4-((5-(trifluoromethyl)pyrazin-2-yl)oxy)pyrrolidin-1-yl)-6-(2,4-dimethoxypyrimidin-5-yl)imidazo[1,2-b]pyridazine was prepared in the manner described for Intermediate 514, but replacing fluoro-4-(trifluoromethyl)pyridine with 2-fluoro-5-(trifluoromethyl)pyrazine. ES/MS m/z: 525.20 [M+H].

Intermediate 520. S)-8-(4-((4-(difluoromethyl)pyridin-2-yl)oxy)-3,3-difluoropyrrolidin-1-yl)-6-(2,4-dimethoxypyrimidin-5-yl)imidazo[1,2-b]pyridazine

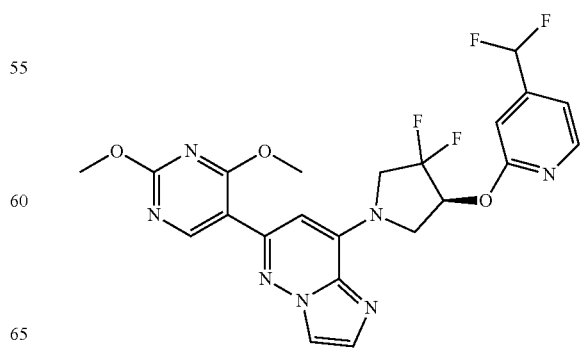

(S)-8-(4-((4-(difluoromethyl)pyridin-2-yl)oxy)-3,3-difluoropyrrolidin-1-yl)-6-(2,4-dimethoxypyrimidin-5-yl)imidazo[1,2-b]pyridazine was prepared in the manner described for Intermediate 514, but replacing fluoro-4-(trifluoromethyl)pyridine with 4-(difluoromethyl)-2-fluoropyridine. ES/MS m/z: 506.20 [M+H].

Intermediate 521. (S)-2-((1-(6-(2,4-dimethoxypyrimidin-5-yl)imidazo[1,2-b]pyridazin-8-yl)-4,4-difluoropyrrolidin-3-yl)oxy)isonicotinonitrile

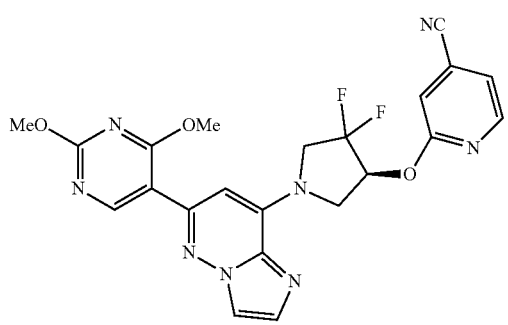 [SMILES: COc1ncc(-c2cc(N3C[C@H](Oc4cc(C#N)ccn4)C(F)(F)C3)c3nccn3n2)c(OC)n1]

(S)-2-((1-(6-(2,4-dimethoxypyrimidin-5-yl)imidazo[1,2-b]pyridazin-8-yl)-4,4-difluoropyrrolidin-3-yl)oxy)isonicotinonitrile was prepared in the manner described for Intermediate 514, but replacing fluoro-4-(trifluoromethyl)pyridine with 2-fluoroisonicotinonitrile. ES/MS m/z: 481.20 [M+H].

Intermediate 522. 6-chloro-8-(3,3,4,4-tetrafluoropyrrolidin-1-yl)imidazo[1,2-b]pyridazine

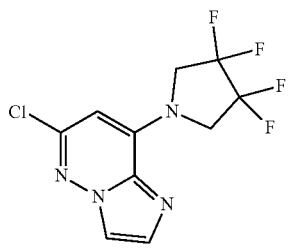 [SMILES: FC1(F)CN(c2cc(Cl)nn3ccnc23)CC1(F)F]

6-chloro-8-(3,3,4,4-tetrafluoropyrrolidin-1-yl)imidazo[1,2-b]pyridazine was prepared as follows: To a mixture of 8-bromo-6-chloro-imidazo[1,2-b]pyridazine (0.2 g, 0.86 mmol) and potassium carbonate (0.24 g, 1.72 mmol) in EtOH (2 mL) was added 3,3,4,4-tetrafluoropyrrolidine hydrochloride (154 mg, 0.86 mmol). The reaction mixture was heated at 90° C. overnight. The solvent was then evaporated and the residue was purified with Prep HPLC to afford 6-chloro-8-(3,3,4,4-tetrafluoropyrrolidin-1-yl)imidazo[1,2-b]pyridazine. ES/MS m/z: 392.20 [M+H].

Intermediate 523. 6-(2,4-dimethoxypyrimidin-5-yl)-8-(3,3,4,4-tetrafluoropyrrolidin-1-yl)imidazo[1,2-b]pyridazine

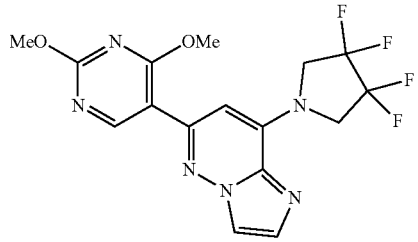 [SMILES: COc1ncc(-c2cc(N3CC(F)(F)C(F)(F)C3)c3nccn3n2)c(OC)n1]

6-(2,4-dimethoxypyrimidin-5-yl)-8-(3,3,4,4-tetrafluoropyrrolidin-1-yl)imidazo[1,2-b]pyridazine was prepared as follows: To a mixture of 6-chloro-8-(3,3,4,4-tetrafluoropyrrolidin-1-yl)imidazo[1,2-b]pyridazine (24 mg, 0.082 mmol) and (2,4-dimethoxypyrimidin-5-yl)boronic acid (30 mg, 0.16 mmol) in 1,4-dioxane (1.5 mL) and water (0.75 mL) were added Pd(dppf)Cl$_2$—CH$_2$Cl$_2$ (7 mg, 0.008 mmol) and cesium carbonate (53 mg, 0.16 mmol). The reaction mixture was heated at 80° C. for 1 h. The reaction mixture was then filtered and was purified with Prep HPLC to afford 6-(2,4-dimethoxypyrimidin-5-yl)-8-(3,3,4,4-tetrafluoropyrrolidin-1-yl)imidazo[1,2-b]pyridazine. ES/MS m/z: 399.10 [M+H].

Intermediate 524. 5-(6-(2,4-dimethoxypyrimidin-5-yl)imidazo[1,2-b]pyridazin-8-yl)-5-azaspiro[2.4]heptan-7-ol

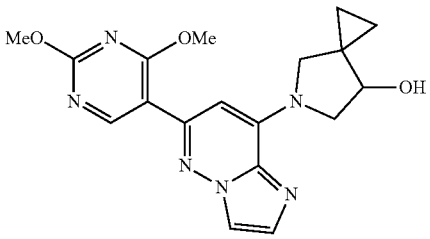 [SMILES: COc1ncc(-c2cc(N3CC(O)C4(CC4)C3)c3nccn3n2)c(OC)n1]

5-(6-(2,4-dimethoxypyrimidin-5-yl)imidazo[1,2-b]pyridazin-8-yl)-5-azaspiro[2.4]heptan-7-ol was prepared in the manner described for Intermediate 513, but replacing 4,4-difluoropyrrolidin-3-ol with 5-azaspiro[2.4]heptan-7-ol. ES/MS m/z: 369.20.

Intermediate 525. 6-(2,4-dimethoxypyrimidin-5-yl)-8-(7-((5-(trifluoromethyl)pyridin-2-yl)oxy)-5-azaspiro[2.4]heptan-5-yl)imidazo[1,2-b]

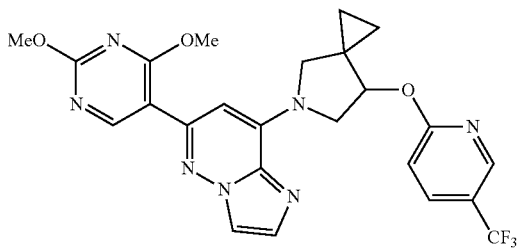 [SMILES: COc1ncc(-c2cc(N3CC(Oc4ccc(C(F)(F)F)cn4)C4(CC4)C3)c3nccn3n2)c(OC)n1]

5-(6-(2,4-dimethoxypyrimidin-5-yl)imidazo[1,2-b]pyridazin-8-yl)-5-azaspiro[2.4]heptan-7-ol (60 mg, 0.16 mmol) was dissolved in NMP (1 mL), to the reaction mixture was added 2-fluoro-5-(trifluoromethyl)pyridine (54 mg, 0.326 mmol). The reaction mixture was heated at 85oC for 4 h, the reaction mixture was then filtered and purified with Prep HPLC to afford 6-(2,4-dimethoxypyrimidin-5-yl)-8-(7-((5-(trifluoromethyl)pyridin-2-yl)oxy)-5-azaspiro[2.4]heptan-5-yl)imidazo[1,2-b]. ES/MS m/z: 514.20.

Intermediate 526. 5-chloro-7-(3,3,4,4-tetrafluoropyrrolidin-1-yl)-[1,2,4]triazolo[1,5-a]pyrimidine

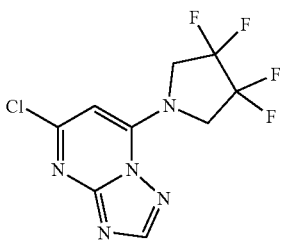 [SMILES: FC1(F)CN(c2cc(Cl)nc3ncnn23)CC1(F)F]

5-chloro-7-(3,3,4,4-tetrafluoropyrrolidin-1-yl)-[1,2,4]triazolo[1,5-a]pyrimidine was prepared in the manner described for Intermediate 522, but replacing 8-bromo-6-chloroimidazo[1,2-b]pyridazine with 5,7-dichloro-[1,2,4]triazolo[1,5-a]pyrimidine. ES/MS m/z: 296.00.

Intermediate 527. 5-(2,4-dimethoxypyrimidin-5-yl)-7-(3,3,4,4-tetrafluoropyrrolidin-1-yl)-[1,2,4]triazolo[1,5-a]pyrimidine

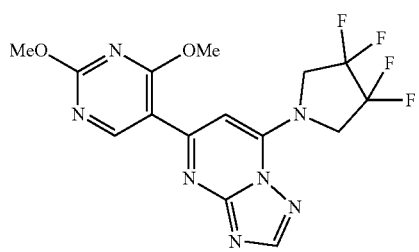 [SMILES: COc1ncc(-c2cc(N3CC(F)(F)C(F)(F)C3)n3ncnc3n2)c(OC)n1]

5-(2,4-dimethoxypyrimidin-5-yl)-7-(3,3,4,4-tetrafluoropyrrolidin-1-yl)-[1,2,4]triazolo[1,5-a]pyrimidine was prepared in the manner described for Intermediate 523, but replacing 6-chloro-8-(3,3,4,4-tetrafluoropyrrolidin-1-yl)imidazo[1,2-b]pyridazine with 5-chloro-7-(3,3,4,4-tetrafluoropyrrolidin-1-yl)-[1,2,4]triazolo[1,5-a]pyrimidine. ES/MS m/z: 400.10.

Intermediate 528. 5-chloro-7-(7,7-difluoro-5-azaspiro[2.4]heptan-5-yl)-[1,2,4]triazolo[1,5-a]pyrimidine

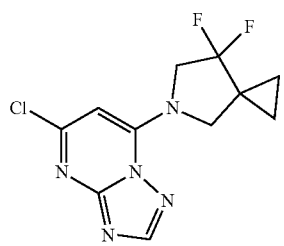 [SMILES: FC1(F)CN(c2cc(Cl)nc3ncnn23)CC12CC2]

5-chloro-7-(7,7-difluoro-5-azaspiro[2.4]heptan-5-yl)-[1,2,4]triazolo[1,5-a]pyrimidine was prepared in the manner described for Intermediate 522, but replacing 8-bromo-6-chloroimidazo[1,2-b]pyridazine with 7,7-difluoro-5-azaspiro[2.4]heptane. ES/MS m/z: 286.00

Intermediate 529. 7-(7,7-difluoro-5-azaspiro[2.4]heptan-5-yl)-5-(2,4-dimethoxypyrimidin-5-yl)-[1,2,4]triazolo[1,5-a]pyrimidine

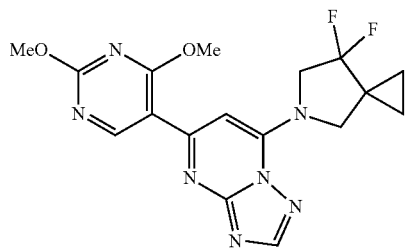 [SMILES: COc1ncc(-c2cc(N3CC(F)(F)C4(CC4)C3)n3ncnc3n2)c(OC)n1]

7-(7,7-difluoro-5-azaspiro[2.4]heptan-5-yl)-5-(2,4-dimethoxypyrimidin-5-yl)-[1,2,4]triazolo[1,5-a]pyrimidine was prepared in the manner described for Intermediate 523, but replacing 6-chloro-8-(3,3,4,4-tetrafluoropyrrolidin-1-yl)imidazo[1,2-b]pyridazine with 5-chloro-7-(7,7-difluoro-5-azaspiro[2.4]heptan-5-yl)-[1,2,4]triazolo[1,5-a]pyrimidine. ES/MS m/z: 390.20.

Intermediate 530. 5-chloro-7-(3,3,4,4-tetrafluoropyrrolidin-1-yl)pyrazolo[1,5-a]pyrimidine

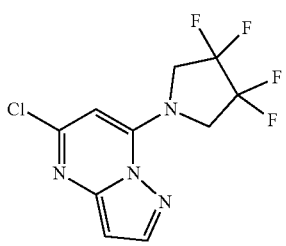 [SMILES: FC1(F)CN(c2cc(Cl)nc3ccnn23)CC1(F)F]

5-chloro-7-(3,3,4,4-tetrafluoropyrrolidin-1-yl)pyrazolo[1,5-a]pyrimidine was prepared in the manner described for Intermediate 522, but replacing 8-bromo-6-chloroimidazo[1,2-b]pyridazine with 5,7-dichloropyrazolo[1,5-a]pyrimidine. ES/MS m/z: 295.00.

Intermediate 531. 5-(2,4-dimethoxypyrimidin-5-yl)-7-(3,3,4,4-tetrafluoropyrrolidin-1-yl)pyrazolo[1,5-a]pyrimidine

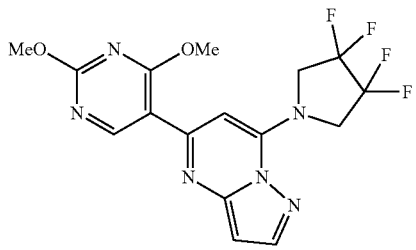 [SMILES: COc1ncc(-c2cc(N3CC(F)(F)C(F)(F)C3)n3nccc3n2)c(OC)n1]

5-(2,4-dimethoxypyrimidin-5-yl)-7-(3,3,4,4-tetrafluoropyrrolidin-1-yl)pyrazolo[1,5-a]pyrimidine was prepared in the manner described for Intermediate 523, but replacing 6-chloro-8-(3,3,4,4-tetrafluoropyrrolidin-1-yl)imidazo[1,2-b]pyridazine with 5-chloro-7-(3,3,4,4-tetrafluoropyrrolidin-1-yl)pyrazolo[1,5-a]pyrimidine. ES/MS m/z:399.20.

Intermediate 532. 6-chloro-8-((2S,2S)-2-(2,2-difluorobenzo[d][1,3]dioxol-5-yl)cyclopropyl)imidazo[1,2-b]pyridazine

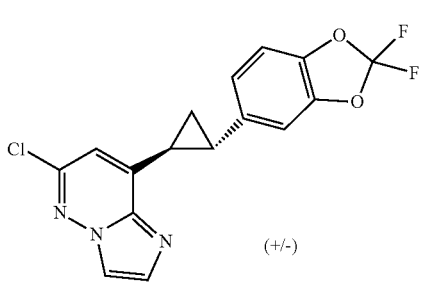 [SMILES: FC1(F)Oc2ccc([C@H]3C[C@@H]3c3cc(Cl)nn4ccnc34)cc2O1]

6-chloro-8-((1S,2S)-2-(2,2-difluorobenzo[d][1,3]dioxol-5-yl)cyclopropyl)imidazo[1,2-b]pyridazine (Racemic Mixture) was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitril with 2-((2S,2S)-2-(2,2-difluorobenzo[d][1,3]dioxol-5-yl)cyclopropyl)-4,4,5,5-tetramethyl-1,3,2-dioxaborolane. ES/MS m/z: 350.20 [M+H].

Intermediate 533. 8-((2S,2S)-2-(2,2-difluorobenzo[d][1,3]dioxol-5-yl)cyclopropyl)-6-(2,4-dimethoxypyrimidin-5-yl)imidazo[1,2-b]pyridazine

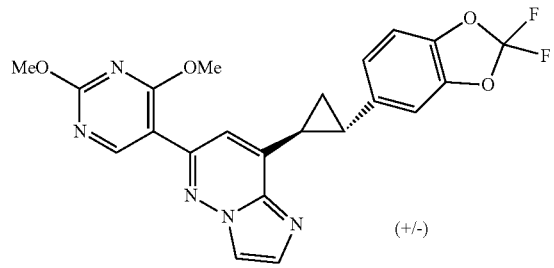 [SMILES: COc1ncc(-c2cc([C@H]3C[C@@H]3c3ccc4c(c3)OC(F)(F)O4)c3nccn3n2)c(OC)n1]

8-((1S,2S)-2-(2,2-difluorobenzo[d][1,3]dioxol-5-yl)cyclopropyl)-6-(2,4-dimethoxypyrimidin-5-yl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(2,2-difluorobenzo[d][1,3]dioxol-5-yl)cyclopropyl)imidazo[1,2-b]pyridazine. ES/MS m/z: 454.20 [M+H].

Intermediate 534. 6-chloro-8-((2S,2S)-2-(4-(trifluoromethoxy)phenyl)cyclopropyl)imidazo[1,2-b]pyridazine (Racemic Mixture)

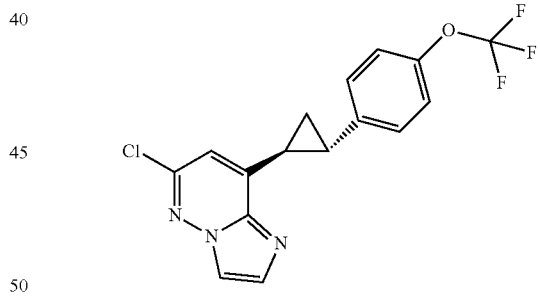

6-chloro-8-((2S,2S)-2-(4-(trifluoromethoxy)phenyl)cyclopropyl)imidazo[1,2-b]pyridazine (Racemic Mixture) was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitril with 4,4,5,5-tetramethyl-2-((2S,2S)-2-(4-(trifluoromethoxy)phenyl)cyclopropyl)-1,3,2-dioxaborolane. ES/MS m/z: 354.20 [M+H].

Intermediate 535. 6-(2,4-dimethoxypyrimidin-5-yl)-8-((1S,2S)-2-(4-(trifluoromethoxy)phenyl)cyclopropyl)imidazo[1,2-b]pyridazine

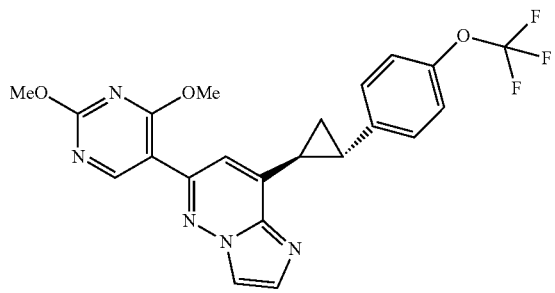 [SMILES: COc1ncc(-c2cc([C@H]3C[C@@H]3c3ccc(OC(F)(F)F)cc3)c3nccn3n2)c(OC)n1]

6-(2,4-dimethoxypyrimidin-5-yl)-8-((2S,2S)-2-(4-(trifluoromethoxy)phenyl)cyclopropyl)imidazo[1,2-b]pyridazine was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(4-(trifluoromethoxy)phenyl)cyclopropyl)imidazo[1,2-b]pyridazine. ES/MS m/z: 458.20 [M+H].

Intermediate 536. 6-chloro-8-((1S,2S)-2-(2,2-difluorobenzo[d][1,3]dioxol-5-yl)cyclopropyl)imidazo[1,2-b]pyridazine

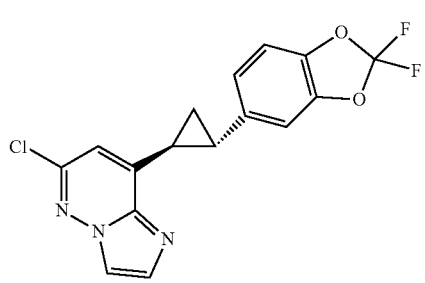 [SMILES: FC1(F)Oc2ccc([C@H]3C[C@@H]3c3cc(Cl)nn4ccnc34)cc2O1]

6-chloro-8-((1S,2S)-2-(2,2-difluorobenzo[d][1,3]dioxol-5-yl)cyclopropyl)imidazo[1,2-b]pyridazine was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitril with 2-((1S,2S)-2-(2,2-difluorobenzo[d][1,3]dioxol-5-yl)cyclopropyl)-4,4,5,5-tetramethyl-1,3,2-dioxaborolane. ES/MS m/z: 350.20 [M+H].

Intermediate 537. 6-bromo-1-(3,3,3-trifluoropropyl)-1H-indazole

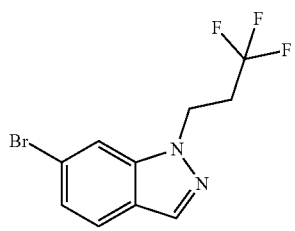 [SMILES: FC(F)(F)CCn1ncc2ccc(Br)cc21]

6-bromo-1-(3,3,3-trifluoropropyl)-1H-indazole was prepared in the manner described for Intermediate 191, but replacing 2,2,2-trifluoroethyl trifluoromethanesulfonate with 3,3,3-trifluoropropyl trifluoromethanesulfonate. ES/MS m/z: 293.00 [M+H].

Intermediate 538. 6-chloro-8-((1S,2S)-2-(1-(3,3,3-trifluoropropyl)-1H-indazol-6-yl)cyclopropyl)imidazo[1,2-b]pyridazine

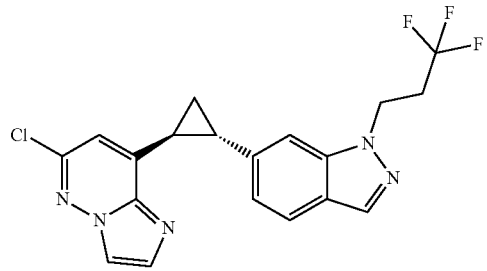 [SMILES: FC(F)(F)CCn1ncc2ccc([C@H]3C[C@@H]3c3cc(Cl)nn4ccnc34)cc21]

6-chloro-8-((1S,2S)-2-(1-(3,3,3-trifluoropropyl)-1H-indazol-6-yl)cyclopropyl)imidazo[1,2-b]pyridazine was prepared in the manner described for Intermediate 498, but replacing 5-bromo-2-methylbenzo[d]thiazole with 6-bromo-1-(3,3,3-trifluoropropyl)-1H-indazole. ES/MS m/z: 406.10 [M+H].

Intermediate 539. 6-(2,4-dimethoxypyrimidin-5-yl)-8-((1S,2S)-2-(1-(3,3,3-trifluoropropyl)-1H-indazol-6-yl)cyclopropyl)imidazo[1,2-b]pyridazine

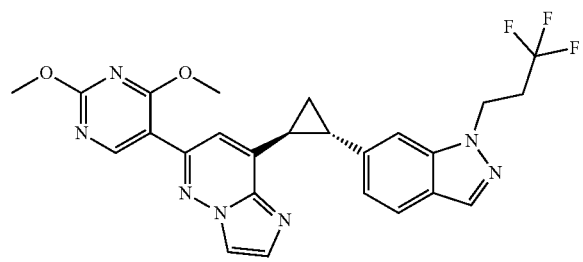 [SMILES: COc1ncc(-c2cc([C@H]3C[C@@H]3c3ccc4cnn(CCC(F)(F)F)c4c3)c3nccn3n2)c(OC)n1]

6-(2,4-dimethoxypyrimidin-5-yl)-8-((2S,2S)-2-(1-(3,3,3-trifluoropropyl)-1H-indazol-6-yl)cyclopropyl)imidazo[1,2-b]pyridazine was prepared in the manner described for Intermediate 523, but replacing 6-chloro-8-(3,3,4,4-tetrafluoropyrrolidin-1-yl)imidazo[1,2-b]pyridazine with 6-chloro-8-((1 S,2S)-2-(1-(3,3,3-trifluoropropyl)-1H-indazol-6-yl)cyclopropyl)imidazo[1,2-b]pyridazine. ES/MS m/z: 510.20 [M+H].

Intermediate 540. 6-bromo-1-(2,2,2-trifluoroethyl)-1H-indazole-3-carbonitrile

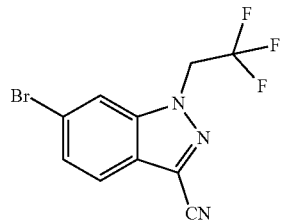 [SMILES: N#Cc1nn(CC(F)(F)F)c2cc(Br)ccc12]

6-bromo-1-(2,2,2-trifluoroethyl)-1H-indazole-3-carbonitrile was prepared in the manner described for Intermediate 191, but replacing 6-bromo-1H-indazole with 6-bromo-1H-indazole-3-carbonitrile. ES/MS m/z: 304.00 [M+H].

Intermediate 541. 6-((2S,2S)-2-(6-chloroimidazo[1,2-b]pyridazin-8-yl)cyclopropyl)-1-(2,2,2-trifluoroethyl)-1H-indazole-3-carbonitrile

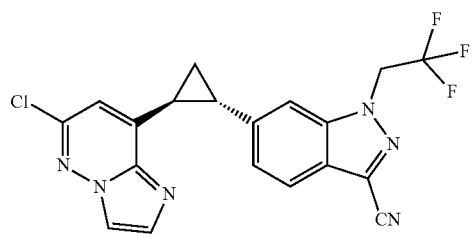 [SMILES: N#Cc1nn(CC(F)(F)F)c2cc([C@H]3C[C@@H]3c3cc(Cl)nn4ccnc34)ccc12]

6-((1S,2S)-2-(6-chloroimidazo[1,2-b]pyridazin-8-yl)cyclopropyl)-1-(2,2,2-trifluoroethyl)-1H-indazole-3-carbonitrile was prepared in the manner described for Intermediate 498, but replacing 5-bromo-2-methylbenzo[d]thiazole with 6-bromo-1-(2,2,2-trifluoroethyl)-1H-indazole-3-carbonitrile ES/MS m/z: 417.10 [M+H].

Intermediate 542. 6-((2S,2S)-2-(6-(2,4-dimethoxypyrimidin-5-yl)imidazo[1,2-b]pyridazin-8-yl)cyclopropyl)-1-(2,2,2-trifluoroethyl)-1H-indazole-3-carbonitrile

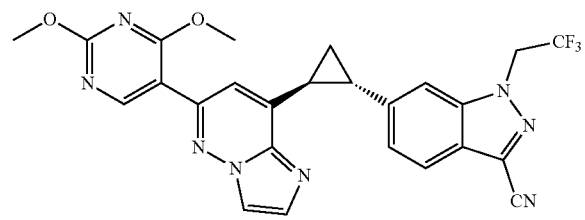 [SMILES: COc1ncc(-c2cc([C@H]3C[C@@H]3c3ccc4c(C#N)nn(CC(F)(F)F)c4c3)c3nccn3n2)c(OC)n1]

6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-indazole-3-carbonitrile was prepared in the manner described for Intermediate 523, but replacing 6-chloro-8-(3,3,4,4-tetrafluoropyrrolidin-1-yl)imidazo[1,2-b]pyridazine with 6-((2S,2S)-2-(6-chloroimidazo[1,2-b]pyridazin-8-yl)cyclopropyl)-1-(2,2,2-trifluoroethyl)-1H-indazole-3-carbonitrile. ES/MS m/z: 521.20 [M+H].

Intermediate 543. 6-chloro-8-((2S,2S)-2-(5-(2,2,2-trifluoroethoxy)pyridin-2-yl)cyclopropyl)imidazo[1,2-b]pyridazine

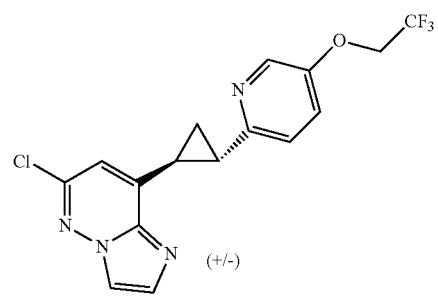 [SMILES: FC(F)(F)COc1ccc([C@H]2C[C@@H]2c2cc(Cl)nn3ccnc23)nc1]

6-chloro-8-((1S,2S)-2-(5-(2,2,2-trifluoroethoxy)pyridin-2-yl)cyclopropyl)imidazo[1,2-b]pyridazine (Racemic Mixture) was prepared in the manner described for Intermediate 498, but replacing 5-bromo-2-methylbenzo[d]thiazole with 2-bromo-5-(2,2,2-trifluoroethoxy)pyridine. ES/MS m/z: 369.10 [M+H].

Intermediate 544. 6-(2,4-dimethoxypyrimidin-5-yl)-8-((1S,2S)-2-(5-(2,2,2-trifluoroethoxy)pyridin-2-yl)cyclopropyl)imidazo[1,2-b]pyridazine

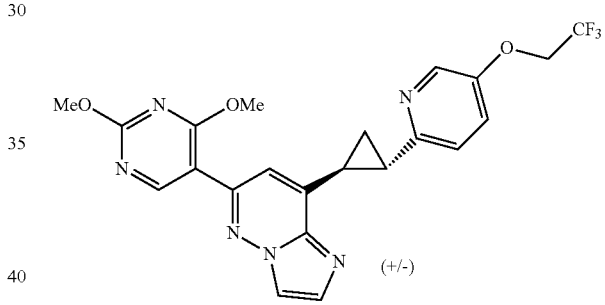

6-(2,4-dimethoxypyrimidin-5-yl)-8-((1S,2S)-2-(5-(2,2,2-trifluoroethoxy)pyridin-2-yl)cyclopropyl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(5-(2,2,2-trifluoroethoxy)pyridin-2-yl)cyclopropyl)imidazo[1,2-b]pyridazine (Racemic Mixture). ES/MS m/z: 473.20 [M+H].

Intermediate 545. 2-((1S,2S)-2-(6-chloroimidazo[1,2-b]pyridazin-8-yl)cyclopropyl)-5-(trifluoromethyl)thiazole

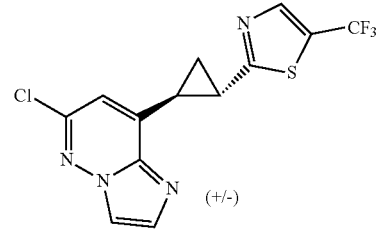 [SMILES: FC(F)(F)c1cnc([C@H]2C[C@@H]2c2cc(Cl)nn3ccnc23)s1]

2-((1S,2S)-2-(6-chloroimidazo[1,2-b]pyridazin-8-yl)cyclopropyl)-5-(trifluoromethyl)thiazole (Racemic Mixture) was prepared in the manner described for Intermediate 498 but replacing 5-bromo-2-methylbenzo[d]thiazole with 2-bromo-5-(trifluoromethyl)thiazole. ES/MS m/z: 345.00 [M+H].

Intermediate 546. 2-((1S,2S)-2-(6-(2,4-dimethoxypyrimidin-5-yl)imidazo[1,2-b]pyridazin-8-yl)cyclopropyl)-5-(trifluoromethyl)thiazole

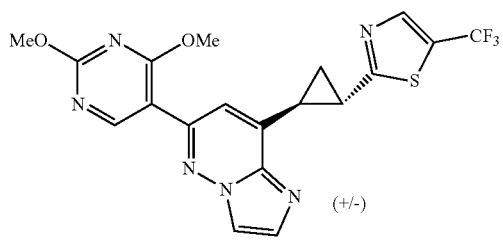 [SMILES: COc1ncc(-c2cc([C@H]3C[C@@H]3c3ncc(C(F)(F)F)s3)c3nccn3n2)c(OC)n1]

2-((1S,2S)-2-(6-(2,4-dimethoxypyrimidin-5-yl)imidazo[1,2-b]pyridazin-8-yl)cyclopropyl)-5-(trifluoromethyl)thiazole as racemic mixture was prepared in the manner described for Intermediate 174, but replacing 6-chloro-8-(3,3,4,4-tetrafluoropyrrolidin-1-yl)imidazo[1,2-b]pyridazine with 24(1S,2S)-2-(6-chloroimidazo[1,2-b]pyridazin-8-yl)cyclopropyl)-5-(trifluoromethyl)thiazole (Racemic Mixture). ES/MS m/z: 449.10 [M+H].

Intermediate 547. 5-((1S,2S)-2-(6-chloroimidazo[1,2-b]pyridazin-8-yl)cyclopropyl)-2-(trifluoromethyl)thiazole

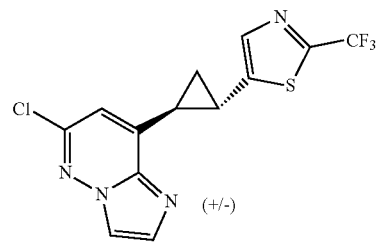 [SMILES: FC(F)(F)c1ncc([C@H]2C[C@@H]2c2cc(Cl)nn3ccnc23)s1]

5-((1S,2S)-2-(6-chloroimidazo[1,2-b]pyridazin-8-yl)cyclopropyl)-2-(trifluoromethyl)thiazole (Racemic Mixture) was prepared in the manner described for Intermediate 498, but replacing 5-bromo-2-methylbenzo[d]thiazole with 5-bromo-2-(trifluoromethyl)thiazole. ES/MS m/z: 345.00 [M+H].

Intermediate 548. 5-((1S,2S)-2-(6-(2,4-dimethoxypyrimidin-5-yl)imidazo[1,2-b]pyridazin-8-yl)cyclopropyl)-2-(trifluoromethyl)thiazole

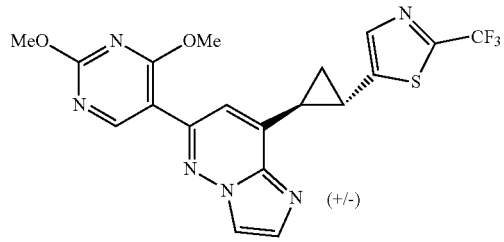 [SMILES: COc1ncc(-c2cc([C@H]3C[C@@H]3c3cnc(C(F)(F)F)s3)c3nccn3n2)c(OC)n1]

5-((1S,2S)-2-(6-(2,4-dimethoxypyrimidin-5-yl)imidazo[1,2-b]pyridazin-8-yl)cyclopropyl)-2-(trifluoromethyl)thiazole as racemic mixture was prepared in the manner described for Intermediate 174, but replacing 6-chloro-8-(3,3,4,4-tetrafluoropyrrolidin-1-yl)imidazo[1,2-b]pyridazine with 5-((1S,2S)-2-(6-chloroimidazo[1,2-b]pyridazin-8-yl)cyclopropyl)-2-(trifluoromethyl)thiazole (Racemic Mixture). ES/MS m/z: 449.10 [M+H].

Intermediate 549. 6-chloro-8-((1S,2S)-2-(1-(trifluoromethyl)-1H-pyrazol-4-yl)cyclopropyl)imidazo[1,2-b]pyridazine

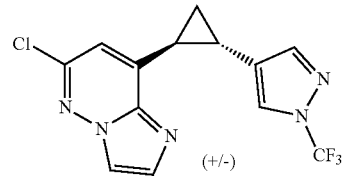 [SMILES: FC(F)(F)n1cc([C@H]2C[C@@H]2c2cc(Cl)nn3ccnc23)cn1]

6-chloro-8-((1S,2S)-2-(1-(trifluoromethyl)-1H-pyrazol-4-yl)cyclopropyl)imidazo[1,2-b]pyridazine (Racemic Mixture) was prepared in the manner described for Intermediate 498, but replacing 5-bromo-2-methylbenzo[d]thiazole with 4-bromo-1-(trifluoromethyl)pyrazole. ES/MS m/z: 328.10 [M+H].

Intermediate 550. 6-(2,4-dimethoxypyrimidin-5-yl)-8-((1S,2S)-2-(1-(trifluoromethyl)-1H-pyrazol-4-yl)cyclopropyl)imidazo[1,2-b]pyridazine

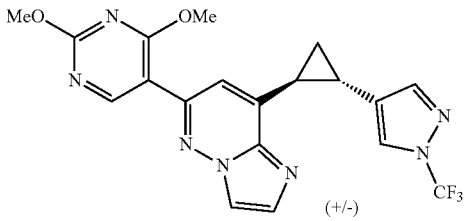 [SMILES: COc1ncc(-c2cc([C@H]3C[C@@H]3c3cnn(C(F)(F)F)c3)c3nccn3n2)c(OC)n1]

6-(2,4-dimethoxypyrimidin-5-yl)-8-((1S,2S)-2-(1-(trifluoromethyl)-1H-pyrazol-4-yl)cyclopropyl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(1-(trifluoromethyl)-1H-pyrazol-4-yl)cyclopropyl)imidazo[1,2-b]pyridazine (Racemic Mixture). ES/MS m/z: 432.20 [M+H].

Intermediate 551. 2-((1S,2S)-2-(6-chloroimidazo[1,2-b]pyridazin-8-yl)cyclopropyl)-4-(trifluoromethyl)thiazole

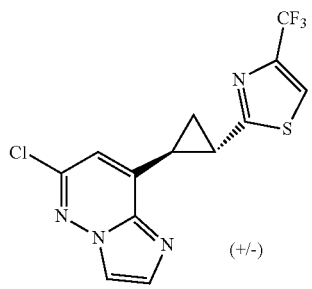 [SMILES: FC(F)(F)c1csc([C@H]2C[C@@H]2c2cc(Cl)nn3ccnc23)n1]

2-((1S,2S)-2-(6-chloroimidazo[1,2-b]pyridazin-8-yl)cyclopropyl)-4-(trifluoromethyl)thiazole (Racemic Mixture) was prepared in the manner described for Intermediate 498, but replacing 5-bromo-2-methylbenzo[d]thiazole with 2-bromo-4-(trifluoromethyl)thiazole. ES/MS m/z: 345.00 [M+H].

Intermediate 552. 2-((2S,2S)-2-(6-(2,4-dimethoxypyrimidin-5-yl)imidazo[1,2-b]pyridazin-8-yl)cyclopropyl)-4-(trifluoromethyl)thiazole

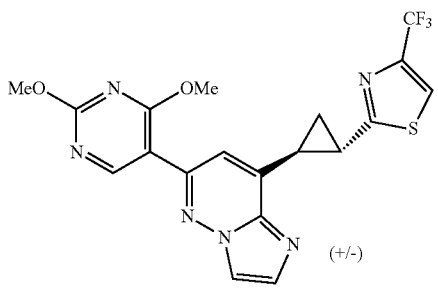 [SMILES: COc1ncc(-c2cc([C@H]3C[C@@H]3c3nc(C(F)(F)F)cs3)c3nccn3n2)c(OC)n1]

2-((1S,2S)-2-(6-(2,4-dimethoxypyrimidin-5-yl)imidazo[1,2-b]pyridazin-8-yl)cyclopropyl)-4-(trifluoromethyl)thiazole as racemic mixture was prepared in the manner described for Intermediate 174, but replacing 6-chloro-8-(3,3,4,4-tetrafluoropyrrolidin-1-yl)imidazo[1,2-b]pyridazine with 24(1S,2S)-2-(6-chloroimidazo[1,2-b]pyridazin-8-yl)cyclopropyl)-4-(trifluoromethyl)thiazole (Racemic Mixture). ES/MS m/z: 449.10 [M+H].

Intermediate 553. 6-chloro-8-((2S,2S)-2-(1-(difluoromethyl)-1H-pyrazol-4-yl)cyclopropyl)imidazo[1,2-b]pyridazine

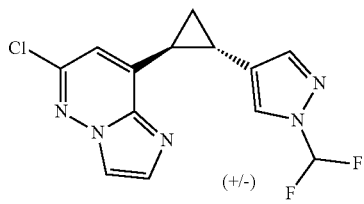 [SMILES: FC(F)n1cc([C@H]2C[C@@H]2c2cc(Cl)nn3ccnc23)cn1]

8-bromo-6-chloro-imidazo[1,2-b]pyridazine (250 mg, 1.08 mmol) and 1-(difluoromethyl)-4-([[(1S,2S)-2-(4,4,5,5-tetramethyl-1,3-dioxolan-2-yl)cyclopropyl]pyrazole (342 mg, 1.08 mmol) were dissolved in 1,4-dioxane (4 ml) and water (2 ml). To the above mixture were added [1,1'-Bis(diphenylphosphino)ferrocene]dichloropalladium(II), complex with dichloromethane (88 mg, 0.1 mmol) and Cs$_2$CO$_3$ (701 mg, 2.15 mmol). The reaction mixture was then heated at 120 degrees for 1 hour. The reaction mixture was then filtered and purified with Prep HPLC to afford 6-chloro-8-((1S,2S)-2-(1-(difluoromethyl)-1H-pyrazol-4-yl)cyclopropyl)imidazo[1,2-b]pyridazine (Racemic Mixture). ES/MS m/z: 310.10 [M+H].

Intermediate 554. 8-((2S,2S)-2-(1-(difluoromethyl)-1H-pyrazol-4-yl)cyclopropyl)-6-(2,4-dimethoxypyrimidin-5-yl)imidazo[1,2-b]pyridazine

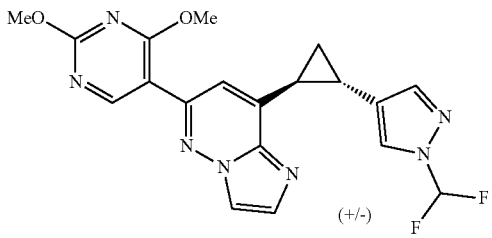 [SMILES: COc1ncc(-c2cc([C@H]3C[C@@H]3c3cnn(C(F)F)c3)c3nccn3n2)c(OC)n1]

8-((1S,2S)-2-(1-(difluoromethyl)-1H-pyrazol-4-yl)cyclopropyl)-6-(2,4-dimethoxypyrimidin-5-yl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((2S,2S)-2-(1-(difluoromethyl)-1H-pyrazol-4-yl)cyclopropyl)imidazo[1,2-b]pyridazine (Racemic Mixture). ES/MS m/z: 414.20 [M+H].

Intermediate 555. 6-chloro-8-((2S,2S)-2-(1-(difluoromethyl)-1H-pyrazol-3-yl)cyclopropyl)imidazo[1,2-b]pyridazine

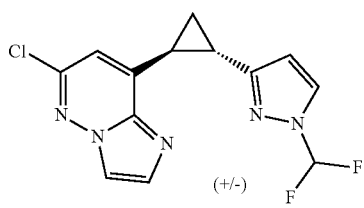 [SMILES: FC(F)n1ccc([C@H]2C[C@@H]2c2cc(Cl)nn3ccnc23)n1]

6-chloro-8-((1S,2S)-2-(1-(difluoromethyl)-1H-pyrazol-3-yl)cyclopropyl)imidazo[1,2-b]pyridazine (Racemic Mixture) was prepared in the manner described for Intermediate 238, but replacing racemic 2-[(1S,2S)-2-(4-cyclopropylphenyl)cyclopropyl]-4,4,5,5-tetramethyl-1,3,2-dioxaborolane with racemic [(1S,2S)-2-[1-(difluoromethyl)pyrazol-3-yl]cyclopropyl]boronic acid. ES/MS m/z: 310.10 [M+H].

Intermediate 556. 8-((2S,2S)-2-(1-(difluoromethyl)-1H-pyrazol-3-yl)cyclopropyl)-6-(2,4-dimethoxypyrimidin-5-yl)imidazo[1,2-b]pyridazine

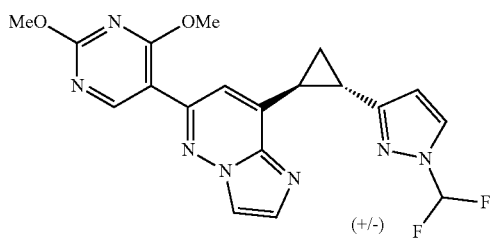 [SMILES: COc1ncc(-c2cc([C@H]3C[C@@H]3c3ccn(C(F)F)n3)c3nccn3n2)c(OC)n1]

8-((1S,2S)-2-(1-(difluoromethyl)-1H-pyrazol-3-yl)cyclopropyl)-6-(2,4-dimethoxypyrimidin-5-yl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((2S,2S)-2-(1-(difluoromethyl)-1H-pyrazol-3-yl)cyclopropyl)imidazo[1,2-b]pyridazine (Racemic Mixture). ES/MS m/z: 414.20 [M+H].

Intermediate 557. 6-chloro-8-((1S,2S)-2-(1-(difluoromethyl)-1H-pyrazol-4-yl)cyclopropyl)-3-fluoroimidazo[1,2-b]pyridazine

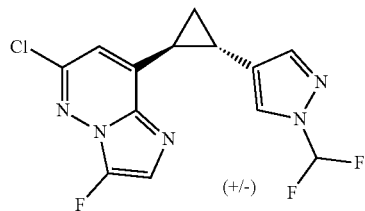 [SMILES: Fc1cnc2c([C@H]3C[C@@H]3c3cnn(C(F)F)c3)cc(Cl)nn12]

6-chloro-8-((1S,2S)-2-(1-(difluoromethyl)-1H-pyrazol-4-yl)cyclopropyl)-3-fluoroimidazo[1,2-b]pyridazine (Racemic Mixture) was prepared in the manner described Intermediate 238, but replacing 4-((1S,2S)-2-(4,4,5,5-tetramethyl-1,3,2-dioxaborolan-2-yl)cyclopropyl)-2-(trifluoromethyl)benzonitrile with racemic 1-(difluoromethyl)-4-(1S,2S)-2-(4,4,5,5-tetramethyl-1,3,2-dioxaborolan-2-yl)cyclopropyl)-1H-pyrazole and 8-bromo-6-chloro-imidazo[1,2-b]pyridazine with 8-bromo-6-chloro-3-fluoroimidazo[1,2-b]pyridazine. ES/MS m/z: 328.10 [M+H].

Intermediate 558. 8-((2S,2S)-2-(1-(difluoromethyl)-1H-pyrazol-4-yl)cyclopropyl)-6-(2,4-dimethoxypyrimidin-5-yl)-3-fluoroimidazo[1,2-b]pyridazine

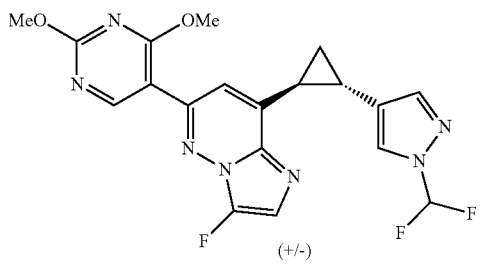 [SMILES: COc1ncc(-c2cc([C@H]3C[C@@H]3c3cnn(C(F)F)c3)c3ncc(F)n3n2)c(OC)n1]

8-((1S,2S)-2-(1-(difluoromethyl)-1H-pyrazol-4-yl)cyclopropyl)-6-(2,4-dimethoxypyrimidin-5-yl)-3-fluoroimidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((2S,2S)-2-(1-(difluoromethyl)-1H-pyrazol-4-yl)cyclopropyl)-3-fluoroimidazo[1,2-b]pyridazine (racemic mixture) (Racemic Mixture). ES/MS m/z: 432.20 [M+H].

Intermediate 559. 6-chloro-8-((2S,2S)-2-(5-(trifluoromethoxy)pyridin-2-yl)cyclopropyl)imidazo[1,2-b]pyridazine

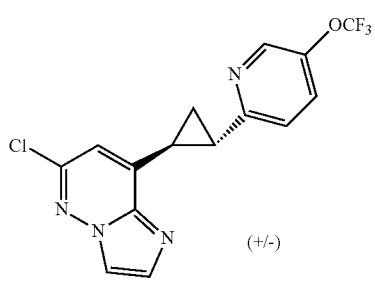 [SMILES: FC(F)(F)Oc1ccc([C@H]2C[C@@H]2c2cc(Cl)nn3ccnc23)nc1]

6-chloro-8-((1S,2S)-2-(5-(trifluoromethoxy)pyridin-2-yl)cyclopropyl)imidazo[1,2-b]pyridazine (Racemic Mixture) was prepared in the manner described Intermediate 238, but replacing 4-((2S,2S)-2-(4,4,5,5-tetramethyl-1,3,2-dioxaborolan-2-yl)cyclopropyl)-2-(trifluoromethyl)benzonitrile with racemic 2-((1S,2S)-2-(4,4,5,5-tetramethyl-1,3,2-dioxaborolan-2-yl)cyclopropyl)-5-(trifluoromethoxy)pyridine. ES/MS m/z: 355.10 [M+H].

Intermediate 560. 6-(2,4-dimethoxypyrimidin-5-yl)-8-((1S,2S)-2-(5-(trifluoromethoxy)pyridin-2-yl)cyclopropyl)imidazo[1,2-b]pyridazine

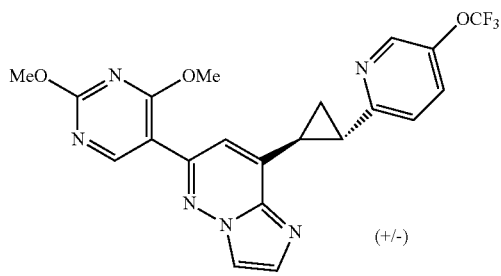

(+/-)

6-(2,4-dimethoxypyrimidin-5-yl)-8-((1S,2S)-2-(5-(trifluoromethoxy)pyridin-2-yl)cyclopropyl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(5-(trifluoromethoxy)pyridin-2-yl)cyclopropyl)imidazo[1,2-b]pyridazine (Racemic Mixture). ES/MS m/z: 459.20 [M+H].

Intermediate 561. 6-chloro-3-fluoro-8-((1S,2S)-2-(5-(trifluoromethoxy)pyridin-2-yl)cyclopropyl)imidazo[1,2-b]pyridazine

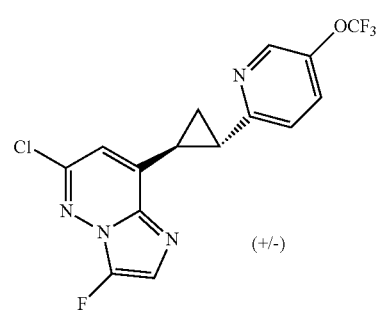 [SMILES: Fc1cnc2c([C@H]3C[C@@H]3c3ccc(OC(F)(F)F)cn3)cc(Cl)nn12]

(+/-)

6-chloro-3-fluoro-8-((1S,2S)-2-(5-(trifluoromethoxy)pyridin-2-yl)cyclopropyl)imidazo[1,2-b]pyridazine (Racemic Mixture) was prepared in the manner described Intermediate 238, but replacing 4-((2S,2S)-2-(4,4,5,5-tetramethyl-1,3,2-dioxaborolan-2-yl)cyclopropyl)-2-(trifluoromethyl)benzonitrile with racemic 2-((2S,2S)-2-(4,4,5,5-tetramethyl-1,3,2-dioxaborolan-2-yl)cyclopropyl)-5-(trifluoromethoxy)pyridine. ES/MS m/z: 373.10 [M+H].

Intermediate 562. 6-(2,4-dimethoxypyrimidin-5-yl)-3-fluoro-8-((1S,2S)-2-(5-(trifluoromethoxy)pyridin-2-yl)cyclopropyl)imidazo[1,2-b]pyridazine

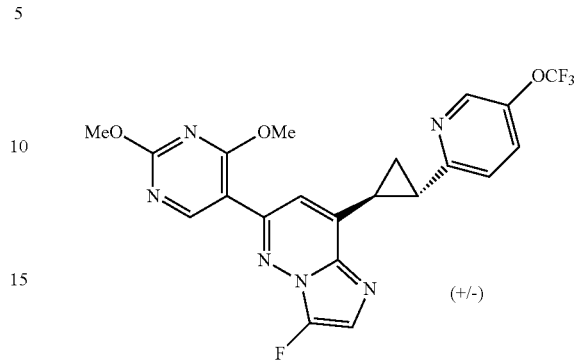

(+/-)

6-(2,4-dimethoxypyrimidin-5-yl)-3-fluoro-8-((1S,2S)-2-(5-(trifluoromethoxy)pyridin-2-yl)cyclopropyl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-3-fluoro-8-((1S,2S)-2-(5-(trifluoromethoxy)pyridin-2-yl)cyclopropyl)imidazo[1,2-b]pyridazine (Racemic Mixture). ES/MS m/z: 477.20 [M+H].

Intermediate 563. 5-((1S,2S)-2-(6-chloro-3-fluoroimidazo[1,2-b]pyridazin-8-yl)cyclopropyl)picolinonitrile

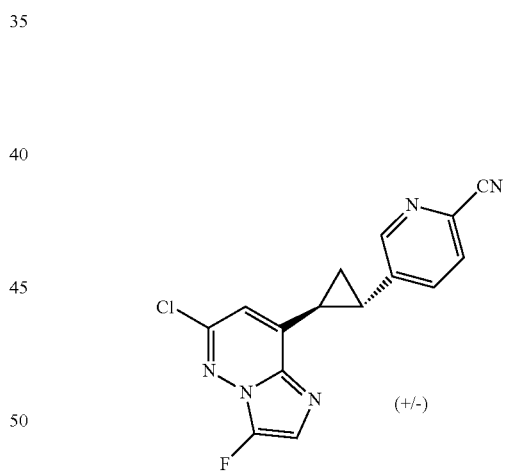

(+/-)

5-((1S,2S)-2-(6-chloro-3-fluoroimidazo[1,2-b]pyridazin-8-yl)cyclopropyl)picolinonitrile (Racemic Mixture) was prepared in the manner described Intermediate 238, but replacing 4-((1S,2S)-2-(4,4,5,5-tetramethyl-1,3,2-dioxaborolan-2-yl)cyclopropyl)-2-(trifluoromethyl)benzonitrile with racemic 5-((1S,2S)-2-(4,4,5,5-tetramethyl-1,3,2-dioxaborolan-2-yl)cyclopropyl)picolinonitrile. ES/MS m/z: 314.10 [M+H].

Intermediate 564. 5-((2S,2S)-2-(6-(2,4-dimethoxy-pyrimidin-5-yl)-3-fluoroimidazo[1,2-b]pyridazin-8-yl)cyclopropyl)picolinonitrile

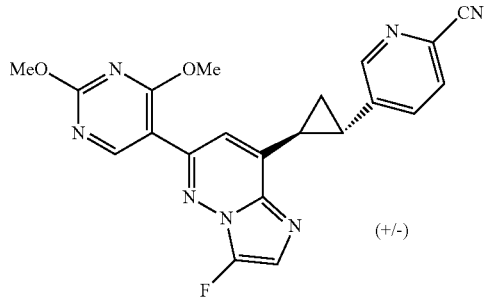 [SMILES: COc1ncc(-c2cc([C@H]3C[C@@H]3c3ccc(C#N)nc3)c3ncc(F)n3n2)c(OC)n1]

(+/-)

5-((1S,2S)-2-(6-(2,4-dimethoxypyrimidin-5-yl)-3-fluoro-imidazo[1,2-b]pyridazin-8-yl)cyclopropyl)picolinonitrile as racemic mixture was prepared in the manner described for Intermediate 174, but replacing 6-chloro-8-(3,3,4,4-tet-rafluoropyrrolidin-1-yl)imidazo[1,2-b]pyridazine with 5-((1S,2S)-2-(6-chloro-3-fluoroimidazo[1,2-b]pyridazin-8-yl)cyclopropyl)picolinonitrile (Racemic Mixture). ES/MS m/z: 418.20 [M+H].

Intermediate 565. 6-chloro-8-((2S,2S)-2-(6-(trifluo-romethoxy)pyridin-3-yl)cyclopropyl)imidazo[1,2-b]pyridazine

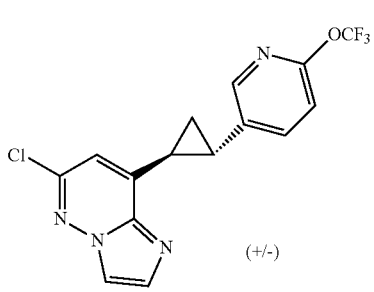 [SMILES: FC(F)(F)Oc1ccc([C@H]2C[C@@H]2c2cc(Cl)nn3ccnc23)cn1]

(+/-)

6-chloro-8-((1S,2S)-2-(6-(trifluoromethoxy)pyridin-3-yl)cyclopropyl)imidazo[1,2-b]pyridazine (Racemic Mixture) was prepared in the manner described Intermediate 238, but replacing 4-((2S,2S)-2-(4,4,5,5-tetramethyl-1,3,2-dioxa-borolan-2-yl)cyclopropyl)-2-(trifluoromethyl)benzonitrile with 5-((2S,2S)-2-(4,4,5,5-tetramethyl-1,3,2-dioxaborolan-2-yl)cyclopropyl)-2-(trifluoromethoxy)pyridine. ES/MS m/z: 355.10 [M+H].

Intermediate 566. 6-(2,4-dimethoxypyrimidin-5-yl)-8-((1S,2S)-2-(6-(trifluoromethoxy)pyridin-3-yl)cy-clopropyl)imidazo[1,2-b]pyridazine

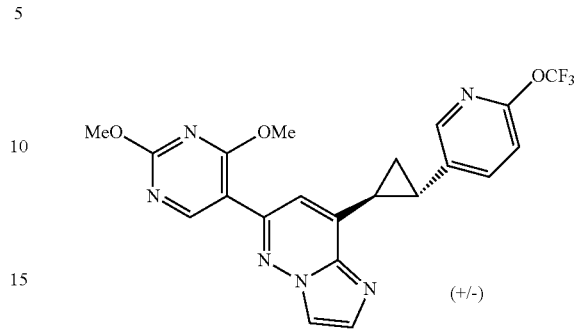

(+/-)

6-(2,4-dimethoxypyrimidin-5-yl)-8-((1S,2S)-2-(6-(trif-luoromethoxy)pyridin-3-yl)cyclopropyl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(6-(trifluoromethoxy)pyridin-3-yl)cyclopropyl)imidazo[1,2-b]pyridazine (Racemic Mixture). ES/MS m/z: 459.20 [M+H].

Intermediate 567. 6-chloro-8-((2S,2S)-2-(5-(trifluo-romethyl)pyrimidin-2-yl)cyclopropyl)imidazo[1,2-b]pyridazine

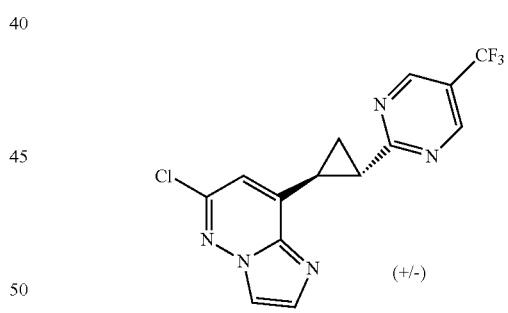

(+/-)

6-chloro-8-((1S,2S)-2-(5-(trifluoromethyl)pyrimidin-2-yl)cyclopropyl)imidazo[1,2-b]pyridazine (Racemic Mixture) was prepared in the manner described Intermediate 238, but replacing 4-((1S,2S)-2-(4,4,5,5-tetramethyl-1,3,2-dioxaborolan-2-yl)cyclopropyl)-2-(trifluoromethyl)benzo-nitrile with racemic 2-((1S,2S)-2-(4,4,5,5-tetramethyl-1,3,2-dioxaborolan-2-yl)cyclopropyl)-5-(trifluoromethyl) pyrimidine. ES/MS m/z: 340.10 [M+H].

Intermediate 568. 6-(2,4-dimethoxypyrimidin-5-yl)-8-((1S,2S)-2-(5-(trifluoromethyl)pyrimidin-2-yl)cyclopropyl)imidazo[1,2-b]pyridazine

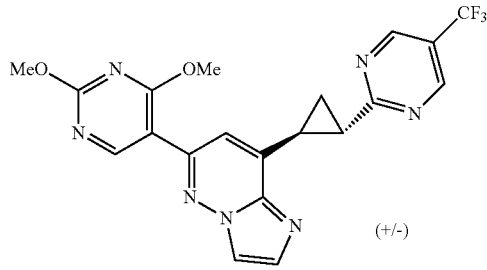 [SMILES: COc1ncc(-c2cc([C@H]3C[C@@H]3c3ncc(C(F)(F)F)cn3)c3nccn3n2)c(OC)n1]

6-(2,4-dimethoxypyrimidin-5-yl)-8-((1S,2S)-2-(5-(trifluoromethyl)pyrimidin-2-yl)cyclopropyl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((2S,2S)-2-(5-(trifluoromethyl)pyrimidin-2-yl)cyclopropyl)imidazo[1,2-b]pyridazine (Racemic Mixture). ES/MS m/z: 444.20 [M+H].

Intermediate 569. 6-chloro-3-fluoro-8-((2S,2S)-2-(5-(trifluoromethyl)pyrimidin-2-yl)cyclopropyl)imidazo[1,2-b]pyridazine

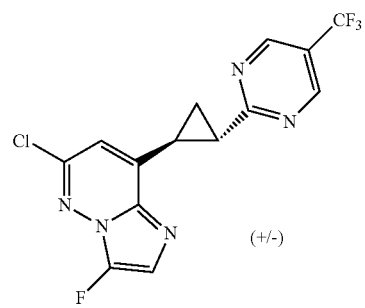 [SMILES: Fc1cnc2c([C@H]3C[C@@H]3c3ncc(C(F)(F)F)cn3)cc(Cl)nn12]

6-chloro-3-fluoro-8-((1S,2S)-2-(5-(trifluoromethyl)pyrimidin-2-yl)cyclopropyl)imidazo[1,2-b]pyridazine (Racemic Mixture) was prepared in the manner described Intermediate 238, but replacing 4-((2S,2S)-2-(4,4,5,5-tetramethyl-1,3,2-dioxaborolan-2-yl)cyclopropyl)-2-(trifluoromethyl)benzonitrile with racemic 2-((1S,2S)-2-(4,4,5,5-tetramethyl-1,3,2-dioxaborolan-2-yl)cyclopropyl)-5-(trifluoromethyl)pyrimidine and 8-bromo-6-chloro-imidazo[1,2-b]pyridazine with 8-bromo-6-chloro-3-fluoroimidazo[1,2-b]pyridazine. ES/MS m/z: 358.10 [M+H].

Intermediate 570. 6-(2,4-dimethoxypyrimidin-5-yl)-3-fluoro-8-((1S,2S)-2-(5-(trifluoromethyl)pyrimidin-2-yl)cyclopropyl)imidazo[1,2-b]pyridazine

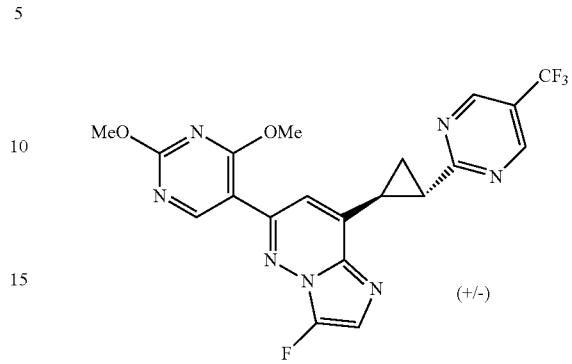

6-(2,4-dimethoxypyrimidin-5-yl)-3-fluoro-8-((1S,2S)-2-(5-(trifluoromethyl)pyrimidin-2-yl)cyclopropyl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-3-fluoro-8-((1S,2S)-2-(5-(trifluoromethyl)pyrimidin-2-yl)cyclopropyl)imidazo[1,2-b]pyridazine (Racemic Mixture). ES/MS m/z: 462.20 [M+H].

Intermediate 571. 6-chloro-8-((2S,2S)-2-(5-(difluoromethyl)pyridin-2-yl)cyclopropyl)imidazo[1,2-b]pyridazine

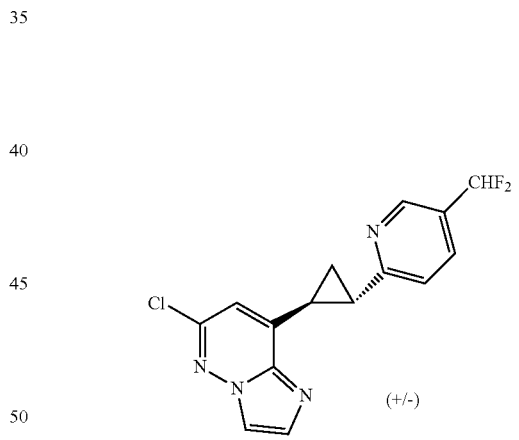

6-chloro-8-((1S,2S)-2-(5-(difluoromethyl)pyridin-2-yl)cyclopropyl)imidazo[1,2-b]pyridazine (Racemic Mixture) was prepared in the manner described Intermediate 238, but replacing 4-((2S,2S)-2-(4,4,5,5-tetramethyl-1,3,2-dioxaborolan-2-yl)cyclopropyl)-2-(trifluoromethyl)benzonitrile with racemic 5-(difluoromethyl)-2-((1S,2S)-2-(4,4,5,5-tetramethyl-1,3,2-dioxaborolan-2-yl)cyclopropyl)pyridine. ES/MS m/z: 321.10 [M+H].

Intermediate 572. 8-((2S,2S)-2-(5-(difluoromethyl)pyridin-2-yl)cyclopropyl)-6-(2,4-dimethoxypyrimidin-5-yl)imidazo[1,2-b]pyridazine

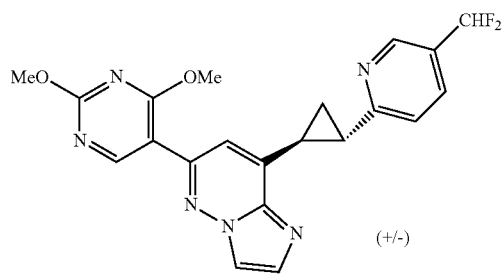 [SMILES: COc1ncc(-c2cc([C@H]3C[C@@H]3c3ccc(C(F)F)cn3)c3nccn3n2)c(OC)n1]

(+/-)

8-((1S,2S)-2-(5-(difluoromethyl)pyridin-2-yl)cyclopropyl)-6-(2,4-dimethoxypyrimidin-5-yl)imidazo[1,2-b]pyridazine as racemic mixture was prepared in the manner described for Intermediate 174, but replacing 6-chloro-8-(3,3,4,4-tetrafluoropyrrolidin-1-yl)imidazo[1,2-b]pyridazine with 6-chloro-8-((1S,2S)-2-(5-(difluoromethyl)pyridin-2-yl)cyclopropyl)imidazo[1,2-b]pyridazine (Racemic Mixture). ES/MS m/z: 425.20 [M+H].

Intermediate 573. 6'-((2S,2S)-2-(4,4,5,5-tetramethyl-1,3,2-dioxaborolan-2-yl)cyclopropyl)-1'-(2,2,2-trifluoroethyl)spiro[cyclopropane-1,3'-indolin]-2'-one

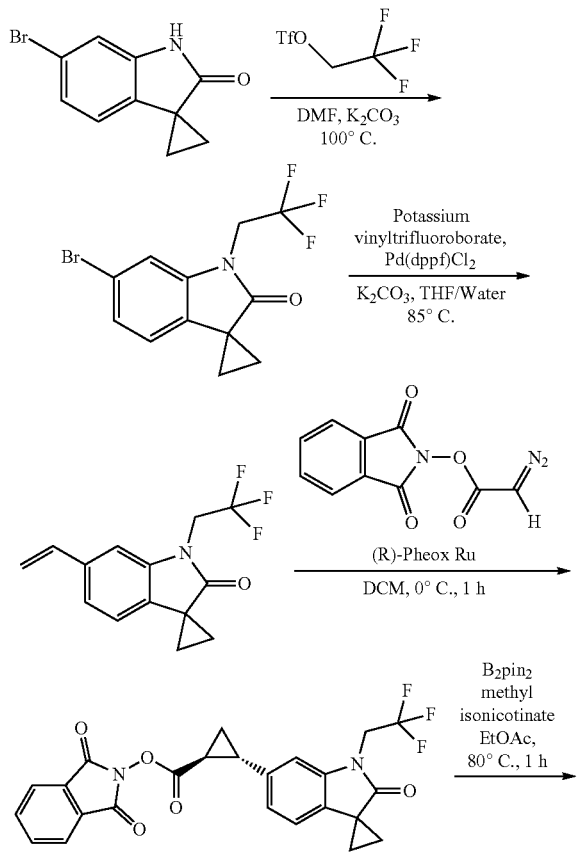

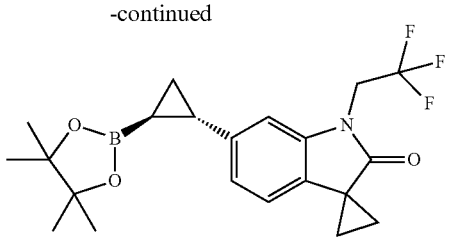

Step 1: To a solution of 6'-bromospiro[cyclopropane-1,3'-indolin]-2'-one (2 g, 8.4 mmol) in DMF was added potassium carbonate (2.3 g, 16.8 mmol) and 2,2,2-Trifluoroethyl trifluoromethanesulfonate (2.9 g, 12.6 mmol). The reaction mixture was heated to 100° C. overnight. Then the reaction mixture was cooled to RT, diluted with brine (50 mL), and extracted with 80% EtOAc/Hex (2×100 mL). The combined organic layers were concentrated and purified by $SiO_2$ chromatography to afford 6'-bromo-1'-(2,2,2-trifluoroethyl)spiro[cyclopropane-1,3'-indolin]-2'-one. ES/MS m/z: 320.20.

Step 2: A solution of Potassium vinyltrifluoroborate (3.52 g, 26.2 mmol), [1,1'-Bis(diphenylphosphino)ferrocene]dichloropalladium(II) (1.8 g, 2.5 mmol), potassium carbonate (7.6 g, 55 mmol) and 6'-bromospiro[cyclopropane-1,3'-indolin]-2'-one (8 g, 25 mmol) were added to $THF/H_2O$(9/1, 45 mL). The reaction mixture was heated to 85oC. After 20 hours, the reaction mixture was cooled to RT. Reaction mixture was filtered and diluted with EtOAc, organic layer was washed with brine and then evaporated under vacuum. The residue was purified with Combi-Flash column to afford 1'-(2,2,2-trifluoroethyl)-6'-vinylspiro[cyclopropane-1,3'-indolin]-2'-one. ES/MS m/z: 268.10. $^1$H NMR (400 MHz, DMSO-d6) δ 7.45 (s, 1H), 7.14 (dd, J=7.7, 1.4 Hz, 1H), 7.09-6.95 (m, 1H), 6.75 (dd, J=17.6, 10.9 Hz, 1H), 5.89 (dd, J=17.6, 1.0 Hz, 1H), 5.28 (dd, J=10.9, 1.0 Hz, 1H), 4.82-4.60 (m, 2H), 1.78-1.66 (m, 2H), 1.61 (q, J=4.8, 4.0 Hz, 2H). $^{19}$F NMR (376 MHz, DMSO-d6) δ −69.25 (td, J=9.5, 6.1 Hz).

Step 3: To a cooled (0° C.) solution of 1'-(2,2,2-trifluoroethyl)-6'-vinylspiro[cyclopropane-1,3'-indolin]-2'-one (759 mg, 2.84 mmol) and (R)-Pheox Ru catalyst (90 mg, 0.14 mmol) in 4 mL $CH_2Cl_2$ was added a 0.2M solution of 1,3-dioxoisoindolin-2-yl 2-diazoacetate (722 mg, 3.12 mmol) in $CH_2Cl_2$ over 20 minutes. The reaction mixture was stirred at 0° C. for 1 h. The reaction was then quenched with MeOH, evaporated solvent and the residue was purified with Combi-Flash column to afford 1,3-dioxoisoindolin-2-yl(1S,2S)-2-(2'-oxo-1'-(2,2,2-trifluoroethyl)spiro[cyclopropane-1,3'-indolin]-6'-yl)cyclopropane-1-carboxylate. ES/MS m/z: 471.10. $^1$H NMR (400 MHz, DMSO-d6) δ 8.08-7.89 (m, 4H), 7.19 (s, 1H), 7.06-7.01 (m, 2H), 4.70 (q, J=9.6, 9.1 Hz, 2H), 2.76 (ddd, J=9.3, 7.0, 4.1 Hz, 1H), 1.76 (ddt, J=14.4, 10.2, 4.9 Hz, 2H), 1.69 (q, J=4.0, 3.2 Hz, 2H), 1.60 (dt, J=4.7, 2.8 Hz, 2H), 1.18 (t, J=7.1 Hz, 1H). $^{19}$F NMR (376 MHz, DMSO-d6) δ −69.29 (t, J=9.4 Hz).

Step 4: Under Argon, a microwave vial was charged with (1,3-dioxoisoindolin-2-yl) (1S,2S)-2-[2'-oxo-1'-(2,2,2-trifluoroethyl)spiro[cyclopropane-1,3'-indoline]-6'-yl]cyclopropanecarboxylate (325 mg, 0.69 mmol), Bis(pinacolato)diboron (263 mg, 1.04 mmol), methyl isonicotinate (47 mg, 0.345 mmol) and EtOAc (3 ml). The resulting mixture was heated to 80° C. for 1 h. Then the solvent was evaporated and the residue was purified with combi-flash to afford 6'-((2S,2S)-2-(4,4,5,5-tetramethyl-1,3,2-dioxaborolan-2-yl)

cyclopropyl)-1'-(2,2,2-trifluoroethyl)spiro[cyclopropane-1,3'-indolin]-2'-one. ES/MS m/z: 408.20.

Intermediate 574. 6'-((1S,2S)-2-(6-chloro-3-fluoro-imidazo[1,2-b]pyridazin-8-yl)cyclopropyl)-1'-(2,2,2-trifluoroethyl)spiro[cyclopropane-1,3'-indolin]-2'-one

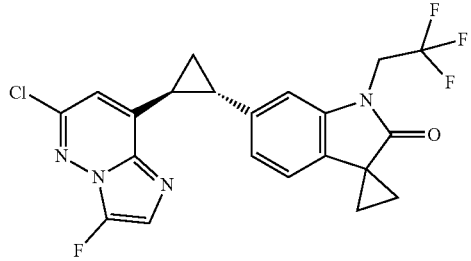 [SMILES: O=C1N(CC(F)(F)F)c2cc([C@H]3C[C@@H]3c3cc(Cl)nn4c(F)cnc34)ccc2C12CC2]

6'-((1S,2S)-2-(6-chloro-3-fluoroimidazo[1,2-b]pyridazin-8-yl)cyclopropyl)-1'-(2,2,2-trifluoroethyl)spiro[cyclopropane-1,3'-indolin]-2'-one was prepared in the manner described for Intermediate 470, but replacing 2-((2S,2S)-2-(2-fluoro-4-(trifluoromethoxy)phenyl)cyclopropyl)-4,4,5,5-tetramethyl-1,3,2-dioxaborolane with 6'-((1S,2S)-2-(4,4,5,5-tetramethyl-1,3,2-dioxaborolan-2-yl)cyclopropyl)-1'-(2,2,2-trifluoroethyl)spiro[cyclopropane-1,3'-indolin]-2'-one and 8-bromo-6-chloro-2-methyl-imidazo[1,2-b]pyridazine with 8-bromo-6-chloro-3-fluoroimidazo[1,2-b]pyridazine. ES/MS m/z: 451.10.

Intermediate 575. 6'-((2S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclopropane-1,3'-indolin]-2'-one

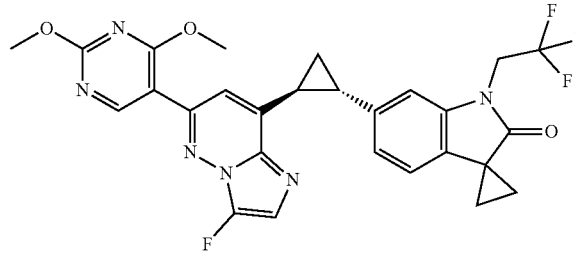

6'-((1S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclopropane-1,3'-indolin]-2'-one was prepared in the manner described for 523, but replacing 6-chloro-8-(3,3,4,4-tetrafluoropyrrolidin-1-yl)imidazo[1,2-b]pyridazine with 6'-((1S,2S)-2-(6-chloro-3-fluoroimidazo[1,2-b]pyridazin-8-yl)cyclopropyl)-1'-(2,2,2-trifluoroethyl)spiro[cyclopropane-1,3'-indolin]-2'-one. ES/MS m/z: 555.20.

Intermediate 576. 6'-((2S,2S)-2-(6-chloroimidazo[1,2-b]pyridazin-8-yl)cyclopropyl)-1'-(2,2,2-trifluoroethyl)spiro[cyclopropane-1,3'-indolin]-2'-one

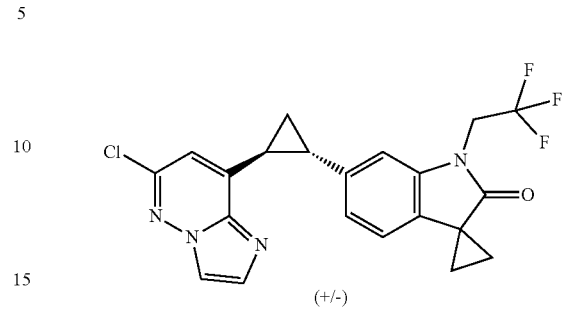

(+/-)

6'-((1S,2S)-2-(6-chloroimidazo[1,2-b]pyridazin-8-yl)cyclopropyl)-F-(2,2,2-trifluoroethyl)spiro[cyclopropane-1,3'-indolin]-2'-one (racemate) was prepared as a racemic mixture in the manner described for Intermediate 498, but replacing 5-bromo-2-methylbenzo[d]thiazole with 6'-bromo-1'-(2,2,2-trifluoroethyl)spiro[cyclopropane-1,3'-indolin]-2'-one. ES/MS m/z: 433.10.

Intermediate 577. 6'-((2S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclopropane-1,3'-indolin]-2'-one

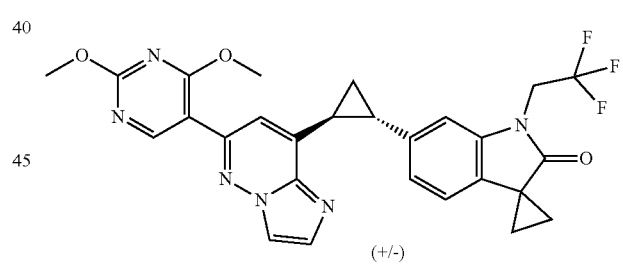

(+/-)

6'-((1S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclopropane-1,3'-indolin]-2'-one (racemate) was prepared in the manner described for 523, but replacing 6-chloro-8-(3,3,4,4-tetrafluoropyrrolidin-1-yl)imidazo[1,2-b]pyridazine with 6'-((1S,2S)-2-(6-chloroimidazo[1,2-b]pyridazin-8-yl)cyclopropyl)-1'-(2,2,2-trifluoroethyl)spiro[cyclopropane-1,3'-indolin]-2'-one (racemate). ES/MS m/z: 537.20.

Intermediate 578. 6'-bromo-1'-(2,2,2-trifluoroethyl)spiro[cyclopropane-1,3'-indolin]-2'-one

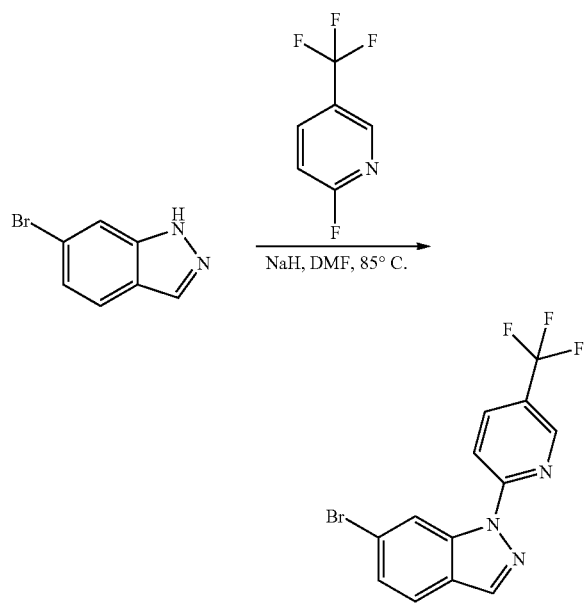

Added NaH (167 mg, 4.36 mmol, 60% in mineral oil) to the solution of 6-bromo-1H-indazole (537 mg, 2.73 mmol) in DMF (6 mL), stirred at RT for 10 mins, then to the reaction mixture was added 2-fluoro-5-(trifluoromethyl)pyridine (900 mg, 5.45 mmol) and the reaction mixture was stirred at 85 C for 4 h. Then the reaction mixture was diluted with EtOAc, washed with brine, purified with combi-flash column to afford 6'-bromo-1'-(2,2,2-trifluoroethyl)spiro[cyclopropane-1,3'-indolin]-2'-one.

Intermediate 579. 6-chloro-8-((2S,2S)-2-(1-(5-(trifluoromethyl)pyridin-2-yl)-1H-indazol-6-yl)cyclopropyl)imidazo[1,2-b]pyridazine

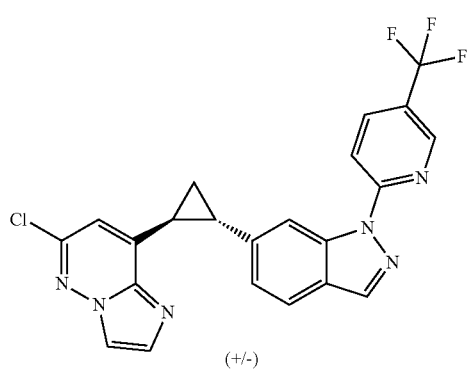 [SMILES: FC(F)(F)c1ccc(-n2ncc3ccc([C@H]4C[C@@H]4c4cc(Cl)nn5ccnc45)cc32)nc1]

6-chloro-8-((1S,2S)-2-(1-(5-(trifluoromethyl)pyridin-2-yl)-1H-indazol-6-yl)cyclopropyl)imidazo[1,2-b]pyridazine (racemate) was prepared in the manner described for Intermediate 498, but replacing 5-bromo-2-methylbenzo[d]thiazole with 6-bromo-1-(5-(trifluoromethyl)pyridin-2-yl)-1H-indazole. ES/MS m/z: 455.10.

Intermediate 580. 6-(2,4-dimethoxypyrimidin-5-yl)-8-((1S,2S)-2-(1-(5-(trifluoromethyl)pyridin-2-yl)-1H-indazol-6-yl)cyclopropyl)imidazo[1,2-b]pyridazine

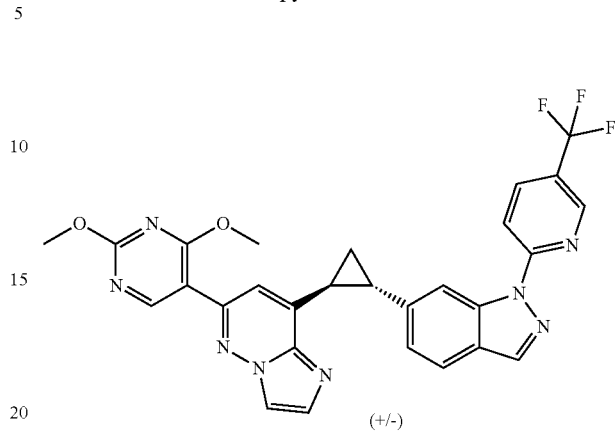

6-(2,4-dimethoxypyrimidin-5-yl)-8-((2S,2S)-2-(1-(5-(trifluoromethyl)pyridin-2-yl)-1H-indazol-6-yl)cyclopropyl)imidazo[1,2-b]pyridazine (racemate) was prepared in the manner described for 523, but replacing 6-chloro-8-(3,3,4,4-tetrafluoropyrrolidin-1-yl)imidazo[1,2-b]pyridazine with 6-chloro-8-((2S,2S)-2-(1-(5-(trifluoromethyl)pyridin-2-yl)-1H-indazol-6-yl)cyclopropyl)imidazo[1,2-b]pyridazine (racemate). ES/MS m/z: 559.20.

Intermediate 581. 6'-((2S,2S)-2-(4,4,5,5-tetramethyl-1,3,2-dioxaborolan-2-yl)cyclopropyl)-1'-(2,2,2-trifluoroethyl)spiro[cyclobutane-1,3'-indolin]-2'-one

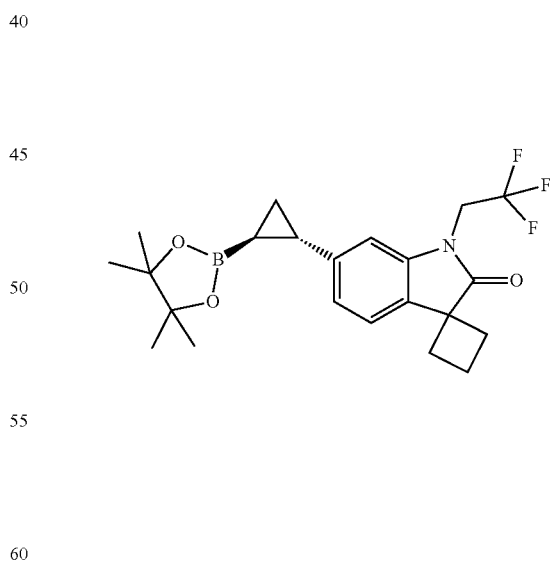

6'-((1S,2S)-2-(4,4,5,5-tetramethyl-1,3,2-dioxaborolan-2-yl)cyclopropyl)-F-(2,2,2-trifluoroethyl)spiro[cyclobutane-1,3'-indolin]-2'-one was prepared in the manner described for Intermediate 573, but replacing 6'-bromospiro[cyclopropane-1,3'-indolin]-2'-one with 6'-bromospiro[cyclobutane-1,3'-indolin]-2'-one. ES/MS m/z: 422.20.

Intermediate 582. 6'-((2S,2S)-2-(6-chloroimidazo[1,2-b]pyridazin-8-yl)cyclopropyl)-1'-(2,2,2-trifluoroethyl)spiro[cyclobutane-1,3'-indolin]-2'-one

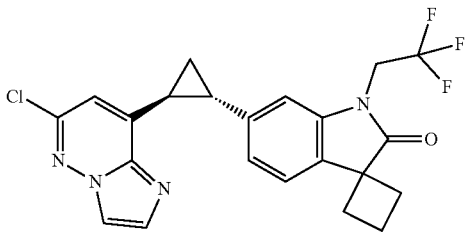 [SMILES: O=C1N(CC(F)(F)F)c2cc([C@H]3C[C@@H]3c3cc(Cl)nn4ccnc34)ccc2C12CCC2]

6'-((1S,2S)-2-(6-chloroimidazo[1,2-b]pyridazin-8-yl)cyclopropyl)-1'-(2,2,2-trifluoroethyl)spiro[cyclobutane-1,3'-indolin]-2'-one prepared in the manner described Intermediate 238, but replacing 4-((1S,2S)-2-(4,4,5,5-tetramethyl-1,3,2-dioxaborolan-2-yl)cyclopropyl)-2-(trifluoromethyl)benzonitrile with 6'4-(1S,2S)-2-(4,4,5,5-tetramethyl-1,3,2-dioxaborolan-2-yl)cyclopropyl)-1'-(2,2,2-trifluoroethyl)spiro[cyclobutane-1,3'-indolin]-2'-one. ES/MS m/z: 447.10.

Intermediate 583. 6'-((2S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclobutane-1,3'-indolin]-2'-one

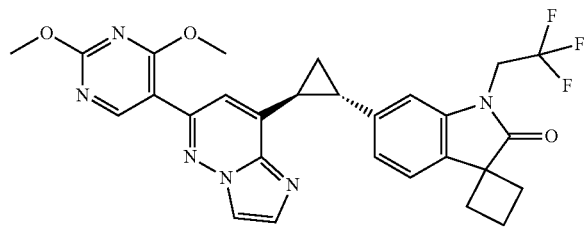 [SMILES: COc1ncc(-c2cc([C@H]3C[C@@H]3c3ccc4c(c3)N(CC(F)(F)F)C(=O)C43CCC3)c3nccn3n2)c(OC)n1]

6'-((1S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclobutane-1,3'-indolin]-2'-one was prepared in the manner described for 523, but replacing 6-chloro-8-(3,3,4,4-tetrafluoropyrrolidin-1-yl)imidazo[1,2-b]pyridazine with 6'-((1S,2S)-2-(6-chloroimidazo[1,2-b]pyridazin-8-yl)cyclopropyl)-1'-(2,2,2-trifluoroethyl)spiro[cyclobutane-1,3'-indolin]-2'-one. ES/MS m/z: 551.20.

Intermediate 584. 6'-((2S,2S)-2-(6-chloro-3-fluoroimidazo[1,2-b]pyridazin-8-yl)cyclopropyl)-1'-(2,2,2-trifluoroethyl)spiro[cyclobutane-1,3'-indolin]-2'-one

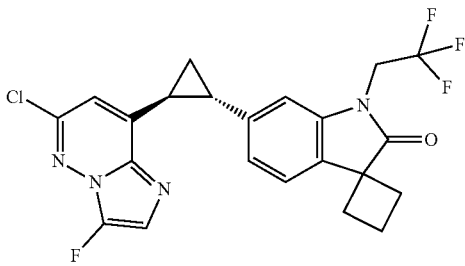 [SMILES: O=C1N(CC(F)(F)F)c2cc([C@H]3C[C@@H]3c3cc(Cl)nn4c(F)cnc34)ccc2C12CCC2]

6'-((2S,2S)-2-(6-chloro-3-fluoroimidazo[1,2-b]pyridazin-8-yl)cyclopropyl)-F-(2,2,2-trifluoroethyl)spiro[cyclobutane-1,3'-indolin]-2'-one was prepared in the manner described Intermediate 238, but replacing 4-((2S,2S)-2-(4,4,5,5-tetramethyl-1,3,2-dioxaborolan-2-yl)cyclopropyl)-2-(trifluoromethyl)benzonitrile with 6'-((2S,2S)-2-(4,4,5,5-tetramethyl-1,3,2-dioxaborolan-2-yl)cyclopropyl)-1'-(2,2,2-trifluoroethyl)spiro[cyclobutane-1,3'-indolin]-2'-one. ES/MS m/z: 465.10.

Intermediate 585. 6'-((1S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclobutane-1,3'-indolin]-2'-one

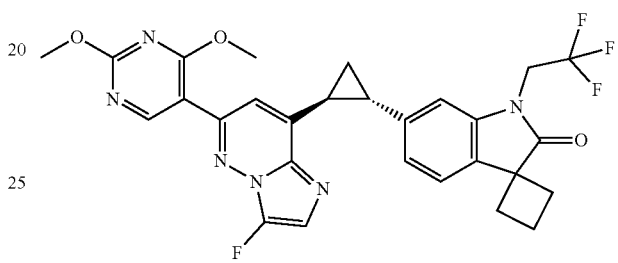

6'-((1S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclobutane-1,3'-indolin]-2'-one was prepared in the manner described for 523, but replacing 6-chloro-8-(3,3,4,4-tetrafluoropyrrolidin-1-yl)imidazo[1,2-b]pyridazine with 6'-((1S,2S)-2-(6-chloro-3-fluoroimidazo[1,2-b]pyridazin-8-yl)cyclopropyl)-1'-(2,2,2-trifluoroethyl)spiro[cyclobutane-1,3'-indolin]-2'-one. ES/MS m/z: 569.20.

Intermediate 586. 6'-((1S,2S)-2-(4,4,5,5-tetramethyl-1,3,2-dioxaborolan-2-yl)cyclopropyl)-1'-(2,2,2-trifluoroethyl)spiro[cyclopentane-1,3'-indolin]-2'-one

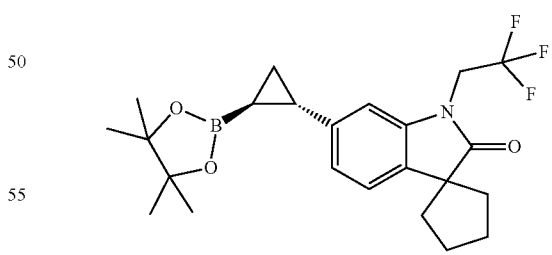

6'-((1S,2S)-2-(4,4,5,5-tetramethyl-1,3,2-dioxaborolan-2-yl)cyclopropyl)-1'-(2,2,2-trifluoroethyl)spiro[cyclopentane-1,3'-indolin]-2'-one was prepared in the manner described for Intermediate 573, but replacing 6'-bromospiro[cyclopropane-1,3'-indolin]-2'-one with 6'-bromospiro[cyclopentane-1,3'-indolin]-2'-one. ES/MS m/z: 436.20.

Intermediate 587. 6'-((1S,2S)-2-(6-chloroimidazo[1,2-b]pyridazin-8-yl)cyclopropyl)-1'-(2,2,2-trifluoroethyl)spiro[cyclopentane-1,3'-indolin]-2'-one

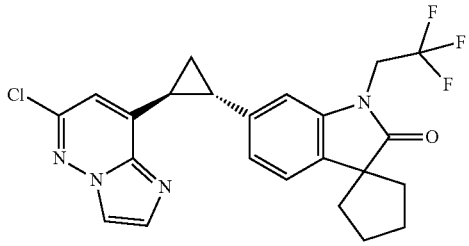 [SMILES: O=C1N(CC(F)(F)F)c2cc([C@H]3C[C@@H]3c3cc(Cl)nn4ccnc34)ccc2C12CCCC2]

6'-((1S,2S)-2-(6-chloroimidazo[1,2-b]pyridazin-8-yl)cyclopropyl)-1'-(2,2,2-trifluoroethyl)spiro[cyclopentane-1,3'-indolin]-2'-one was prepared in the manner described Intermediate 238 but replacing 4-((1S,2S)-2-(4,4,5,5-tetramethyl-1,3,2-dioxaborolan-2-yl)cyclopropyl)-2-(trifluoromethyl)benzonitrile with 6'-((2S,2S)-2-(4,4,5,5-tetramethyl-1,3,2-dioxaborolan-2-yl)cyclopropyl)-1'-(2,2,2-trifluoroethyl)spiro[cyclopentane-1,3'-indolin]-2'-one. ES/MS m/z: 461.10.

Intermediate 588. 6'-((2S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclopentane-1,3'-indolin]-2'-one

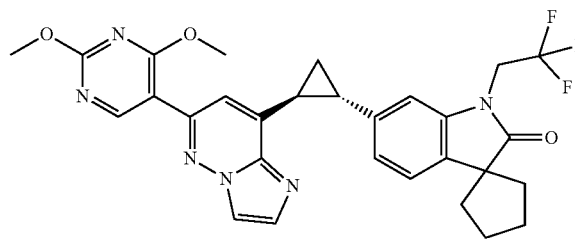

6'-((1S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclopentane-1,3'-indolin]-2'-one was prepared in the manner described for 523, but replacing 6-chloro-8-(3,3,4,4-tetrafluoropyrrolidin-1-yl)imidazo[1,2-b]pyridazine with 6'-((1S,2S)-2-(6-chloroimidazo[1,2-b]pyridazin-8-yl)cyclopropyl)-1'-(2,2,2-trifluoroethyl)spiro[cyclopentane-1,3'-indolin]-2'-one. ES/MS m/z: 565.20.

Intermediate 589. 6'-((2S,2S)-2-(6-chloro-3-fluoroimidazo[1,2-b]pyridazin-8-yl)cyclopropyl)-1'-(2,2,2-trifluoroethyl)spiro[cyclopentane-1,3'-indolin]-2'-one

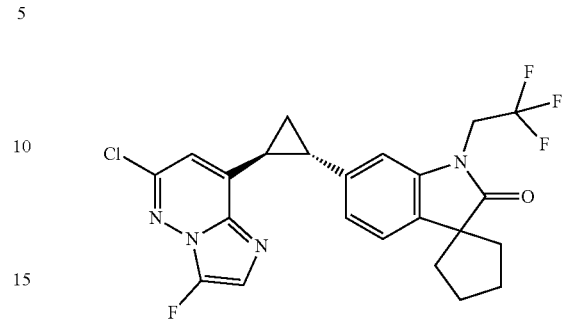

6'-((1S,2S)-2-(6-chloro-3-fluoroimidazo[1,2-b]pyridazin-8-yl)cyclopropyl)-1'-(2,2,2-trifluoroethyl)spiro[cyclopentane-1,3'-indolin]-2'-one was prepared in the manner described Intermediate 238, but replacing 4-((2S,2S)-2-(4,4,5,5-tetramethyl-1,3,2-dioxaborolan-2-yl)cyclopropyl)-2-(trifluoromethyl)benzonitrile with 6'-((2S,2S)-2-(4,4,5,5-tetramethyl-1,3,2-dioxaborolan-2-yl)cyclopropyl)-1'-(2,2,2-trifluoroethyl)spiro[cyclopentane-1,3'-indolin]-2'-one and 8-bromo-6-chloro-2-methyl-imidazo[1,2-b]pyridazine with 8-bromo-6-chloro-3-fluoroimidazo[1,2-b]pyridazine. ES/MS m/z: 479.10.

Intermediate 590. 6'-((2S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclopentane-1,3'-indolin]-2'-one

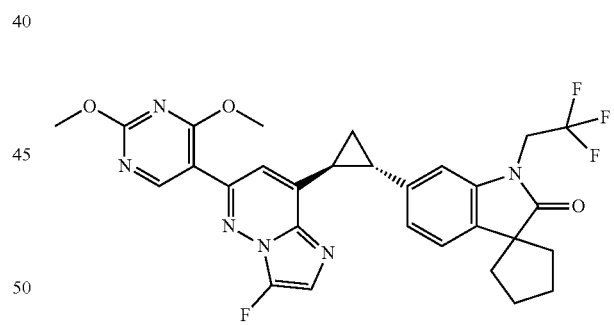

6'-((2S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclopentane-1,3'-indolin]-2'-one was prepared in the manner described for 523, but replacing 6-chloro-8-(3,3,4,4-tetrafluoropyrrolidin-1-yl)imidazo[1,2-b]pyridazine with 6'-((1S,2S)-2-(6-chloro-3-fluoroimidazo[1,2-b]pyridazin-8-yl)cyclopropyl)-1'-(2,2,2-trifluoroethyl)spiro[cyclopentane-1,3'-indolin]-2'-one. ES/MS m/z: 583.20.

Intermediate 591. 6-[(1S,2S)-2-(6-chloroimidazo[1,2-b]pyridazin-8-yl)cyclopropyl]quinoline

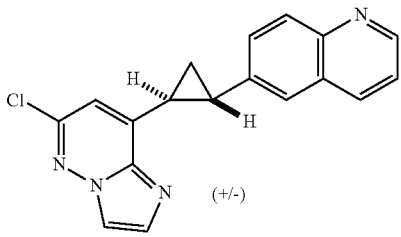 [SMILES: Clc1cc([C@H]2C[C@@H]2c2ccc3ncccc3c2)c2nccn2n1]

6-[(1S,2S)-2-(6-chloroimidazo[1,2-b]pyridazin-8-yl)cyclopropyl]quinoline (racemic mixture) was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 6-[(1S,2S)-2-(4,4,5,5-tetramethyl-1,3,2-dioxaborolan-2-yl)cyclopropyl]quinoline (racemic mixture). ES/MS m/z: 321.10 [M+H].

Intermediate 592. 8-bromo-6-chloro-[1,2,4]triazolo[1,5-b]pyridazine

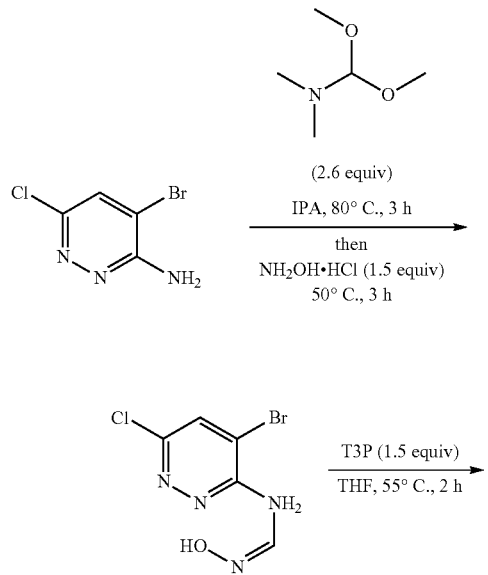

To a solution of 4-bromo-6-chloro-pyridazin-3-amine (200 mg, 0.959 mmol) in IPA (2 mL) was added N,N-dimethylformamide dimethyl acetal (0.332 mL, 2.49 mmol). The resulting mixture was heated to 80° C. for 3 h, then cooled to rt and hydroxylamine hydrochloride (100 mg, 1.44 mmol) was added. The mixture was heated to 50° C. and stirred for 3 h, then cooled to rt, quenched with 10% NaHCO₃ aqueous solution, and extracted twice with 2-MeTHF. Combined organics were dried over MgSO₄, filtered, and concentrated in vacuo. The resulting residue was purified by silica gel chromatography (0-100% EtOAc/hexanes) to afford N-(4-bromo-6-chloropyridazin-3-yl)-N'-hydroxyformimidamide. ES/MS m/z: 251.0 [M+H]. $^1$H NMR (400 MHz, DMSO-d6) δ 10.99 (s, 1H), 8.39 (d, J=1.2 Hz, 1H), 8.24 (d, J=9.6 Hz, 1H), 8.04 (d, J=9.4 Hz, 1H).

T3P (0.156 mL, 0.262 mmol) was added to a solution of N-(4-bromo-6-chloropyridazin-3-yl)-N'-hydroxyformimidamide (44 mg, 0.175 mmol) in THF (0.5 mL), and the mixture was heated to 55° C. for 2 h. The reaction mixture was allowed to cool to rt, quenched with 10% NaHCO₃ aqueous solution, and extracted twice with EtOAc. Combined organics were dried over MgSO₄, filtered, and concentrated in vacuo. The resulting residue was purified by silica gel chromatography (0-100% EtOAc/hexanes) to afford 8-bromo-6-chloro-[1,2,4]triazolo[1,5-b]pyridazine. ES/MS m/z: 233.0 [M+H]. $^1$H NMR (400 MHz, DMSO-d6) δ 8.76 (s, 1H), 8.41 (s, 1H).

Intermediate 593. 4,4,5,5-tetramethyl-2-((1S,2S)-2-(4-(trifluoromethyl)phenyl)cyclopropyl)-1,3,2-dioxaborolane

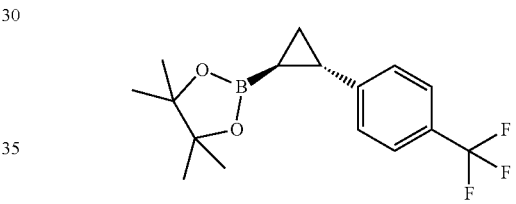

4,4,5,5-tetramethyl-2-((1S,2S)-2-(4-(trifluoromethyl)phenyl)cyclopropyl)-1,3,2-dioxaborolane was prepared in the manner described for Intermediate 72, but replacing 2-chloro-5-vinylbenzonitrile with 1-(trifluoromethyl)-4-vinyl-benzene. $^1$H NMR (400 MHz, DMSO-d6) δ 7.58 (d, J=8.1 Hz, 2H), 7.32 (d, J=8.1 Hz, 2H), 2.16-2.07 (m, 1H), 1.20 (d, J=4.6 Hz, 12H), 1.14-1.08 (m, 2H), 0.32-0.21 (m, 1H).

Intermediate 594. ((1S,2S)-2-(2,4-difluorophenyl)cyclopropyl)trifluoro-14-borane, potassium salt

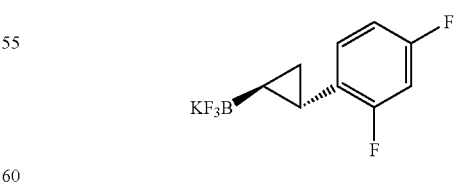

((1S,2S)-2-(2,4-difluorophenyl)cyclopropyl)trifluoro-14-borane, potassium salt was prepared in the manner described for Intermediate 448, but replacing 4,4,5,5-tetramethyl-2-((2S,2S)-2-(4-(trifluoromethyl)phenyl)cyclopropyl)-1,3,2-dioxaborolane with 2-((1S,2S)-2-(2,4-difluorophenyl)cyclopropyl)-4,4,5,5-tetramethyl-1,3,2-dioxaborolane.

Intermediate 595. 2-((2S,2S)-2-(4-(difluoromethyl)phenyl)cyclopropyl)-4,4,5,5-tetramethyl-1,3,2-dioxaborolane

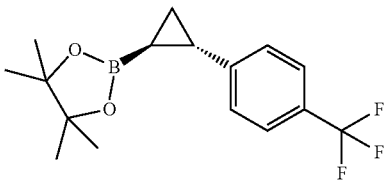 [SMILES: CC1(C)OB([C@H]2C[C@@H]2c2ccc(C(F)(F)F)cc2)OC1(C)C]

2-((1S,2S)-2-(4-(difluoromethyl)phenyl)cyclopropyl)-4,4,5,5-tetramethyl-1,3,2-dioxaborolane was prepared in the manner described for Intermediate 72, but replacing 5-bromo-2-chlorobenzonitrile with 1-bromo-4-(difluoromethyl)benzene. $^1$H NMR (400 MHz, DMSO-d6) δ 7.47-7.38 (m, 2H), 7.22 (d, J=8.0 Hz, 2H), 6.96 (t, J=56.0 Hz, 1H), 2.09-2.02 (m, 1H), 1.19 (d, J=4.5 Hz, 12H), 1.10-1.01 (m, 2H), 0.23 (ddd, J=8.9, 7.5, 5.4 Hz, 1H).

Intermediate 596. 6-chloro-8-(3-phenylazetidin-1-yl)imidazo[1,2-b]pyridazine

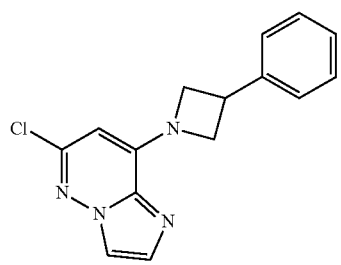 [SMILES: Clc1cc(N2CC(c3ccccc3)C2)c2nccn2n1]

6-chloro-8-(3-phenylazetidin-1-yl)imidazo[1,2-b]pyridazine was prepared as follows: To a mixture of 8-bromo-6-chloro-imidazo[1,2-b]pyridazine (150 mg, 0.645 mmol) and 3-phenylazetidine hydrochloride (109 mg, 0.645 mmol) in MeCN (2 mL) was added N,N-diisopropylethylamine (0.337 mL, 1.94 mmol). The mixture was heated to 100° C. and stirred for 4 h. The mixture was then concentrated in vacuo and the resulting residue was purified by silica gel chromatography (0-100% EtOAc/hexanes) to afford 6-chloro-8-(3-phenylazetidin-1-yl)imidazo[1,2-b]pyridazine. ES/MS m/z: 285.1 [M+H].

Intermediate 597. 6-chloro-8-[3-(trifluoromethyl)azetidin-1-yl]imidazo[1,2-b]pyridazine

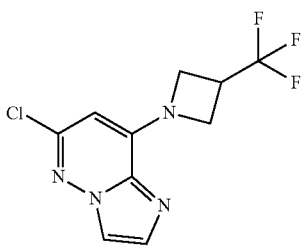 [SMILES: FC(F)(F)C1CN(c2cc(Cl)nn3ccnc23)C1]

6-chloro-8-[3-(trifluoromethyl)azetidin-1-yl]imidazo[1,2-b]pyridazine was prepared in the manner described for Intermediate 596, but replacing 3-phenylazetidine hydrochloride with 3-(trifluoromethyl)azetidine. ES/MS m/z: 277.1 [M+H].

Intermediate 598. 6-chloro-8-(3,3-dimethylazetidin-1-yl)imidazo[1,2-b]pyridazine

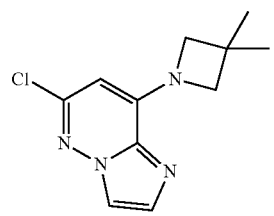 [SMILES: CC1(C)CN(c2cc(Cl)nn3ccnc23)C1]

6-chloro-8-(3,3-dimethylazetidin-1-yl)imidazo[1,2-b]pyridazine was prepared in the manner described for Intermediate 596, but replacing 3-phenylazetidine hydrochloride with 3,3-dimethylazetidine hydrochloride. ES/MS m/z: 237.1 [M+H].

Intermediate 599. 6-chloro-8-(3-fluoro-3-(trifluoromethyl)azetidin-1-yl)imidazo[1,2-b]pyridazine

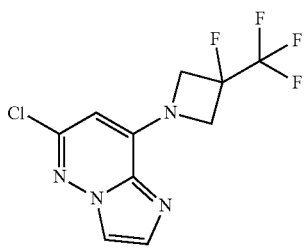 [SMILES: FC(F)(F)C1(F)CN(c2cc(Cl)nn3ccnc23)C1]

6-chloro-8-(3-fluoro-3-(trifluoromethyl)azetidin-1-yl)imidazo[1,2-b]pyridazine was prepared in the manner described for Intermediate 596, but replacing 3-phenylazetidine hydrochloride with 3-fluoro-3-(trifluoromethyl)azetidine hydrochloride. ES/MS m/z: 295.0 [M+H].

Intermediate 600. 6-chloro-8-(3-fluoro-3-(trifluoromethyl)azetidin-1-yl)imidazo[1,2-b]pyridazine

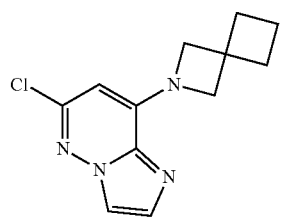 [SMILES: Clc1cc(N2CC3(CCC3)C2)c2nccn2n1]

6-chloro-8-(3-fluoro-3-(trifluoromethyl)azetidin-1-yl)imidazo[1,2-b]pyridazine was prepared in the manner described for Intermediate 596, but replacing 3-phenylazetidine hydrochloride with 2-azaspiro[3.3]heptane. ES/MS m/z: 249.1 [M+H].

Intermediate 601. 6-chloro-8-(3-(difluoromethyl)-3-methylazetidin-1-yl)imidazo[1,2-b]pyridazine

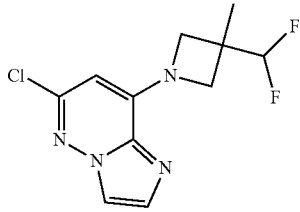 [SMILES: CC1(C(F)F)CN(c2cc(Cl)nn3ccnc23)C1]

6-chloro-8-(3-(difluoromethyl)-3-methylazetidin-1-yl)imidazo[1,2-b]pyridazine was prepared in the manner described for Intermediate 596, but replacing 3-phenylazetidine hydrochloride with 3-(difluoromethyl)-3-methylazetidine hydrochloride. ES/MS m/z: 273.1 [M+H].

Intermediate 602. 6-chloro-8-(3-(2,2-difluorocyclopropyl)azetidin-1-yl)imidazo[1,2-b]pyridazine

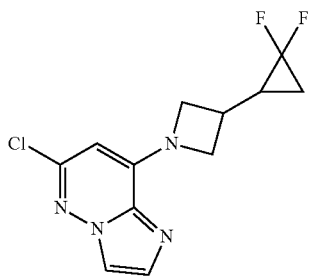 [SMILES: FC1(F)CC1C1CN(c2cc(Cl)nn3ccnc23)C1]

6-chloro-8-(3-(2,2-difluorocyclopropyl)azetidin-1-yl)imidazo[1,2-b]pyridazine was prepared in the manner described for Intermediate 596, but replacing 3-phenylazetidine hydrochloride with 3-(2,2-difluorocyclopropyl)azetidine 2,2,2-trifluoroacetate. ES/MS m/z: 285.1 [M+H].

Intermediate 603. 6-chloro-8-(3-cyclobutylazetidin-1-yl)imidazo[1,2-b]pyridazine

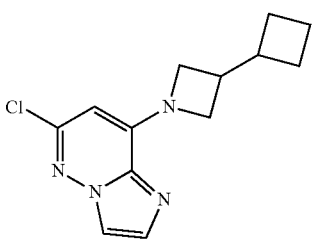 [SMILES: Clc1cc(N2CC(C3CCC3)C2)c2nccn2n1]

6-chloro-8-(3-cyclobutylazetidin-1-yl)imidazo[1,2-b]pyridazine was prepared in the manner described for Intermediate 596, but replacing 3-phenylazetidine hydrochloride with 3-cyclobutylazetidine hydrochloride. ES/MS m/z: 263.1 [M+H].

Intermediate 604. 5-chloro-7-(3-fluoro-3-(trifluoromethyl)azetidin-1-yl)-[1,2,4]triazolo[1,5-a]pyrimidine

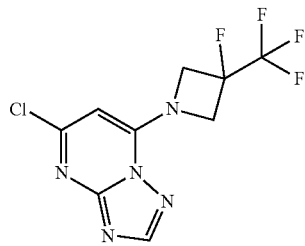 [SMILES: FC(F)(F)C1(F)CN(c2cc(Cl)nc3ncnn23)C1]

5-chloro-7-(3-fluoro-3-(trifluoromethyl)azetidin-1-yl)-[1,2,4]triazolo[1,5-a]pyrimidine was prepared in the manner described for Intermediate 596, but replacing 3-phenylazetidine hydrochloride and 8-bromo-6-chloro-imidazo[1,2-b]pyridazine with 3-fluoro-3-(trifluoromethyl)azetidine hydrochloride and 5,7-dichloro-[1,2,4]triazolo[1,5-a]pyrimidine, respectively. ES/MS m/z: 296.1 [M+H].

Intermediate 605. 6-chloro-8-(3-(difluoromethyl)azetidin-1-yl)imidazo[1,2-b]pyridazine

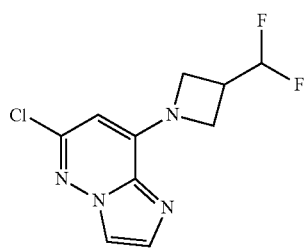 [SMILES: FC(F)C1CN(c2cc(Cl)nn3ccnc23)C1]

6-chloro-8-(3-(difluoromethyl)azetidin-1-yl)imidazo[1,2-b]pyridazine was prepared in the manner described for Intermediate 596, but replacing 3-phenylazetidine hydrochloride with 3-(difluoromethyl)azetidine hydrochloride. ES/MS m/z: 259.1 [M+H].

Intermediate 606. 6-chloro-8-(3-cyclopropylazetidin-1-yl)imidazo[1,2-b]pyridazine

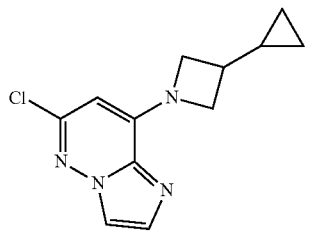 [SMILES: Clc1cc(N2CC(C3CC3)C2)c2nccn2n1]

6-chloro-8-(3-cyclopropylazetidin-1-yl)imidazo[1,2-b] pyridazine was prepared in the manner described for Intermediate 596, but replacing 3-phenylazetidine hydrochloride with 3-cyclopropylazetidine hydrochloride. ES/MS m/z: 349.1 [M+H].

Intermediate 607. 6-chloro-8-(5,5-difluoro-2-azaspiro[3.3]heptan-2-yl)imidazo[1,2-b]pyridazine

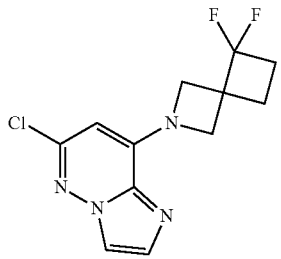 [SMILES: FC1(F)CCC12CN(c1cc(Cl)nn3ccnc13)C2]

6-chloro-8-(5,5-difluoro-2-azaspiro[3.3]heptan-2-yl)imidazo[1,2-b]pyridazine was prepared in the manner described for Intermediate 596, but replacing 3-phenylazetidine hydrochloride with 5,5-difluoro-2-azaspiro[3.3]heptane 2,2,2-trifluoroacetate. ES/MS m/z: 285.1 [M+H].

Intermediate 608. 6-chloro-8-(1,1-difluoro-5-azaspiro[2.3]hexan-5-yl)imidazo[1,2-b]pyridazine

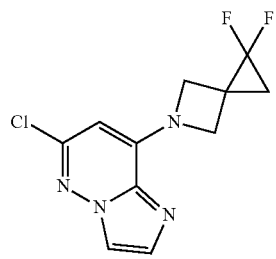 [SMILES: FC1(F)CC12CN(c1cc(Cl)nn3ccnc13)C2]

6-chloro-8-(1,1-difluoro-5-azaspiro[2.3]hexan-5-yl)imidazo[1,2-b]pyridazine was prepared in the manner described for Intermediate 596, but replacing 3-phenylazetidine hydrochloride with 1,1-difluoro-5-azaspiro[2.3]hexane hydrochloride. ES/MS m/z: 271.1 [M+H].

Intermediate 609. 6-chloro-8-(3-(2-fluoropropan-2-yl)azetidin-1-yl)imidazo[1,2-b]pyridazine

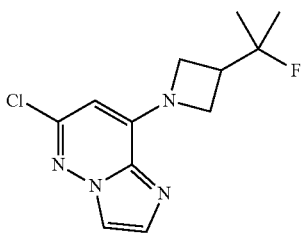 [SMILES: CC(C)(F)C1CN(c2cc(Cl)nn3ccnc23)C1]

6-chloro-8-(3-(2-fluoropropan-2-yl)azetidin-1-yl)imidazo[1,2-b]pyridazine was prepared in the manner described for Intermediate 596, but replacing 3-phenylazetidine hydrochloride with 3-(2-fluoropropan-2-yl)azetidine hydrochloride. ES/MS m/z: 269.1 [M+H].

Intermediate 610. 5-chloro-7-(3,3-difluoro-4,4-dimethylpyrrolidin-1-yl)-[1,2,4]triazolo[1,5-a]pyrimidine

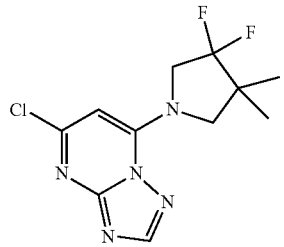 [SMILES: CC1(C)CN(c2cc(Cl)nc3ncnn23)CC1(F)F]

5-chloro-7-(3,3-difluoro-4,4-dimethylpyrrolidin-1-yl)-[1,2,4]triazolo[1,5-a]pyrimidine was prepared in the manner described for Intermediate 596, but replacing 3-phenylazetidine hydrochloride and 8-bromo-6-chloro-imidazo[1,2-b]pyridazine with 3,3-difluoro-4,4-dimethylpyrrolidine hydrochloride and 5,7-dichloro-[1,2,4]triazolo[1,5-a]pyrimidine, respectively, and running the reaction at rt for 1 h. ES/MS m/z: 288.1 [M+H].

Intermediate 611. 7-chloro-5-(3,3-difluoro-4,4-dimethylpyrrolidin-1-yl)imidazo[1,2-a]pyrimidine

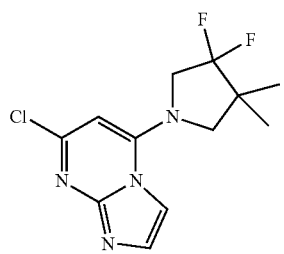 [SMILES: CC1(C)CN(c2cc(Cl)nc3nccn23)CC1(F)F]

7-chloro-5-(3,3-difluoro-4,4-dimethylpyrrolidin-1-yl)imidazo[1,2-a]pyrimidine was prepared in the manner described for Intermediate 596, but replacing 3-phenylazetidine hydrochloride and 8-bromo-6-chloro-imidazo[1,2-b]pyridazine with 3,3-difluoro-4,4-dimethylpyrrolidine hydrochloride and 5,7-dichloroimidazo[1,2-a]pyrimidine, respectively, and running the reaction at 0° C. for 10 min. ES/MS m/z: 287.1 [M+H].

Intermediate 612. 8-bromo-6-chloro-2-cyclopropyl-3-fluoroimidazo[1,2-b]pyridazine

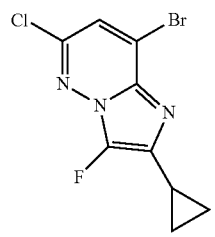 [SMILES: Fc1c(C2CC2)nc2c(Br)cc(Cl)nn12]

To a solution of 8-bromo-6-chloro-2-cyclopropylimidazo[1,2-b]pyridazine (400 mg, 1.47 mmol, 1 equiv) in acetonitrile (6.3 mL) was added SelectFluor (520 mg, 1.47 mmol, 1 equiv). The reaction mixture was heated to 40° C. and stirred for 16 h. The reaction mixture was subsequently concentrated in vacuo. The resulting residue was dissolved in a mixture of EtOAc/water, extracted twice with EtOAc, the combined organics were dried over MgSO₄, filtered and concentrated in vacuo. 8-bromo-6-chloro-2-cyclopropyl-3-fluoroimidazo[1,2-b]pyridazine was purified by silica gel chromatography (0-50% EtOAc/hexanes). ES/MS m/z: 290.00 [M+H].

Intermediate 613. 6-chloro-2-cyclopropyl-8-(3,3-difluoro-4,4-dimethylpyrrolidin-1-yl)-3-fluoroimidazo[1,2-b]pyridazine

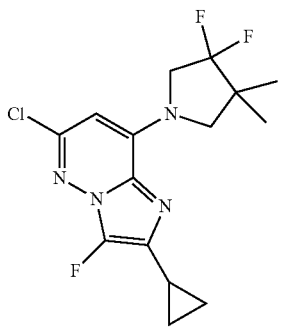 [SMILES: CC1(C)CN(c2cc(Cl)nn3c(F)c(C4CC4)nc23)CC1(F)F]

6-chloro-2-cyclopropyl-8-(3,3-difluoro-4,4-dimethylpyrrolidin-1-yl)-3-fluoroimidazo[1,2-b]pyridazine was prepared in the manner described for Intermediate 596, but replacing 3-phenylazetidine hydrochloride and 8-bromo-6-chloro-imidazo[1,2-b]pyridazine with 3,3-difluoro-4,4-dimethylpyrrolidine hydrochloride and 8-bromo-6-chloro-2-cyclopropyl-3-fluoroimidazo[1,2-b]pyridazine, respectively. ES/MS m/z: 345.1 [M+H].

Intermediate 614. 8-bromo-6-chloro-3-fluoro-2-methylimidazo[1,2-b]pyridazine

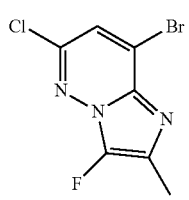

8-bromo-6-chloro-3-fluoro-2-methylimidazo[1,2-b]pyridazine was prepared in the manner described for Intermediate 612, but replacing 8-bromo-6-chloro-2-cyclopropylimidazo[1,2-b]pyridazine with 8-bromo-6-chloro-2-methylimidazo[1,2-b]pyridazine. ES/MS m/z: 263.93 [M+H].

Intermediate 615. 6-chloro-8-(3,3-difluoro-4,4-dimethylpyrrolidin-1-yl)-3-fluoro-2-methylimidazo[1,2-b]pyridazine

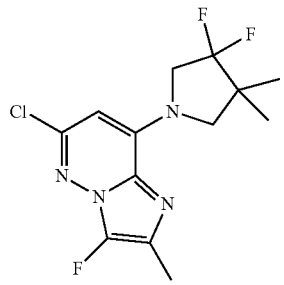 [SMILES: Cc1nc2c(N3CC(C)(C)C(F)(F)C3)cc(Cl)nn2c1F]

6-chloro-8-(3,3-difluoro-4,4-dimethylpyrrolidin-1-yl)-3-fluoro-2-methylimidazo[1,2-b]pyridazine was prepared in the manner described for Intermediate 596, but replacing 3-phenylazetidine hydrochloride and 8-bromo-6-chloro-imidazo[1,2-b]pyridazine with 3,3-difluoro-4,4-dimethylpyrrolidine hydrochloride and 8-bromo-6-chloro-3-fluoro-2-methylimidazo[1,2-b]pyridazine, respectively. ES/MS m/z: 319.1 [M+H].

Intermediate 616. 8-bromo-6-chloro-2-isobutylimidazo[1,2-b]pyridazine

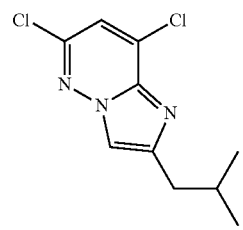

To a solution of 4-bromo-6-chloropyridazin-3-amine (400 mg, 1.9 mmol, 1 equiv.) in DMF (3.8 mL) was added 1-chloro-4-methylpentan-2-one (310 mg, 2.3 mmol, 1.2 equiv.). The reaction was heated to 70° C. and stirred overnight. The reaction was subsequently cooled to room temperature and diluted with EtOAc/water. The resulting mixture was extracted twice with EtOAc, the combined organics were dried over MgSO₄, filtered and conc. in vacuo. The title compound was purified by silica gel chromatography (0-100% EtOAc/hexanes). ES/MS m/z: 244.10 [M+H].

Intermediate 617. 8-bromo-6-chloro-2-(1-(trifluoromethyl)cyclopropyl)imidazo[1,2-b]pyridazine

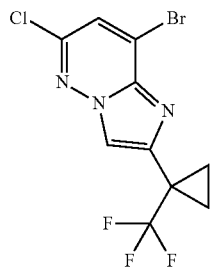 [SMILES: FC(F)(F)C1(c2cn3nc(Cl)cc(Br)c3n2)CC1]

8-bromo-6-chloro-2-(1-(trifluoromethyl)cyclopropyl)imidazo[1,2-b]pyridazine was prepared in the manner described for Intermediate 616, but replacing 1-chloro-4-methylpentan-2-one with 2-bromo-1-(1-(trifluoromethyl)cyclopropyl)ethan-1-one. ES/MS m/z: 339.90 [M+H].

Intermediate 618. 6-chloro-8-(3,3-difluoro-4,4-dimethylpyrrolidin-1-yl)-2-(1-(trifluoromethyl)cyclopropyl)imidazo[1,2-b]pyridazine

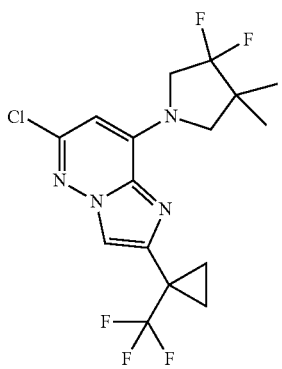 [SMILES: CC1(C)CN(c2cc(Cl)nn3cc(C4(C(F)(F)F)CC4)nc23)CC1(F)F]

6-chloro-8-(3,3-difluoro-4,4-dimethylpyrrolidin-1-yl)-2-(1-(trifluoromethyl)cyclopropyl)imidazo[1,2-b]pyridazine was prepared in the manner described for Intermediate 596, but replacing 3-phenylazetidine hydrochloride and 8-bromo-6-chloro-imidazo[1,2-b]pyridazine with 3,3-difluoro-4,4-dimethylpyrrolidine hydrochloride and 8-bromo-6-chloro-2-(1-(trifluoromethyl)cyclopropyl)imidazo[1,2-b]pyridazine, respectively. ES/MS m/z: 395.1 [M+H].

Intermediate 619. 6-chloro-8-(7,7-difluoro-5-azaspiro[2.4]heptan-5-yl)-[1,2,4]triazolo[1,5-b]pyridazine

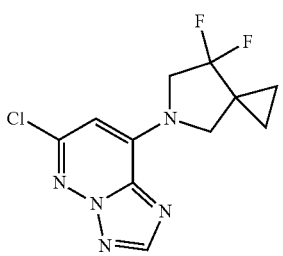 [SMILES: FC1(F)CN(c2cc(Cl)nn3ncnc23)CC12CC2]

6-chloro-8-(7,7-difluoro-5-azaspiro[2.4]heptan-5-yl)-[1,2,4]triazolo[1,5-b]pyridazine was prepared in the manner described for Intermediate 596, but replacing 3-phenylazetidine hydrochloride and 8-bromo-6-chloro-imidazo[1,2-b]pyridazine with 7,7-difluoro-5-azaspiro[2.4]heptane and 8-bromo-6-chloro-[1,2,4]triazolo[1,5-b]pyridazine, respectively, and running the reaction at 40° C. for 1 h. ES/MS m/z: 286.1 [M+H].

Intermediate 620. 6-chloro-8-(3,3-difluoro-4,4-dimethylpyrrolidin-1-yl)-[1,2,4]triazolo[1,5-b]pyridazin

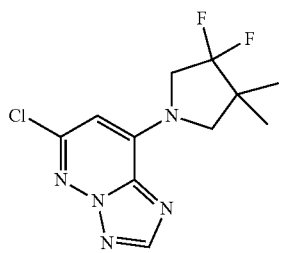 [SMILES: CC1(C)CN(c2cc(Cl)nn3ncnc23)CC1(F)F]

6-chloro-8-(3,3-difluoro-4,4-dimethylpyrrolidin-1-yl)-[1,2,4]triazolo[1,5-b]pyridazine was prepared in the manner described for Intermediate 596, but replacing 3-phenylazetidine hydrochloride and 8-bromo-6-chloro-imidazo[1,2-b]pyridazine with 3,3-difluoro-4,4-dimethyl-pyrrolidine hydrochloride and 8-bromo-6-chloro-[1,2,4]triazolo[1,5-b]pyridazine, respectively, and running the reaction at 40° C. for 1 h. ES/MS m/z: 288.1 [M+H].

Intermediate 621. (R)-6-chloro-8-(3-(trifluoromethoxy)pyrrolidin-1-yl)-[1,2,4]triazolo[1,5-b]pyridazine

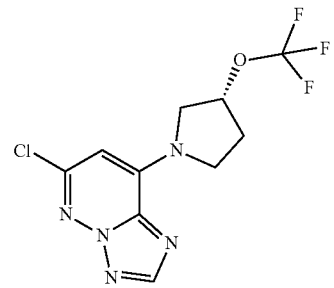 [SMILES: FC(F)(F)O[C@@H]1CCN(c2cc(Cl)nn3ncnc23)C1]

(R)-6-chloro-8-(3-(trifluoromethoxy)pyrrolidin-1-yl)-[1,2,4]triazolo[1,5-b]pyridazine was prepared in the manner described for Intermediate 596, but replacing 3-phenylazetidine hydrochloride and 8-bromo-6-chloro-imidazo[1,2-b]pyridazine with (3R)-3-(trifluoromethoxy)pyrrolidine hydrochloride and 8-bromo-6-chloro-[1,2,4]triazolo[1,5-b]pyridazine, respectively, and running the reaction at 40° C. for 1 h. ES/MS m/z: 308.0 [M+H].

Intermediate 622. 1-(6-chloro-[1,2,4]triazolo[1,5-b]pyridazin-8-0)-4,4-difluoropyrrolidin-3-ol

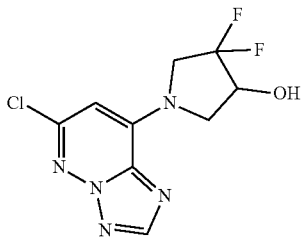 [SMILES: OC1CN(c2cc(Cl)nn3ncnc23)CC1(F)F]

1-(6-chloro-[1,2,4]triazolo[1,5-b]pyridazin-8-yl)-4,4-difluoropyrrolidin-3-ol was prepared in the manner described for Intermediate 596, but replacing 3-phenylazetidine hydrochloride and 8-bromo-6-chloro-imidazo[1,2-b]pyridazine with 4,4-difluoropyrrolidin-3-ol hydrochloride and 8-bromo-6-chloro-[1,2,4]triazolo[1,5-b]pyridazine, respectively, and running the reaction at 40° C. for 1 h. ES/MS m/z: 276.1 [M+H].

Intermediate 623. 6-chloro-8-(3-fluoro-3-(trifluoromethyl)azetidin-1-yl)-[1,2,4]triazolo[1,5-b]pyridazine

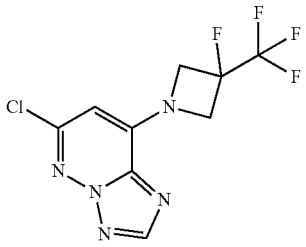 [SMILES: FC(F)(F)C1(F)CN(c2cc(Cl)nn3ncnc23)C1]

6-chloro-8-(3-fluoro-3-(trifluoromethyl)azetidin-1-yl)-[1,2,4]triazolo[1,5-b]pyridazine was prepared in the manner described for Intermediate 596, but replacing 3-phenylazetidine hydrochloride and 8-bromo-6-chloro-imidazo[1,2-b]pyridazine with 3-fluoro-3-(trifluoromethyl)azetidine hydrochloride and 8-bromo-6-chloro-[1,2,4]triazolo[1,5-b]pyridazine, respectively, and running the reaction at 40° C. for 1 h. ES/MS m/z: 296.1 [M+H].

Intermediate 624. 1-(6-chloroimidazo[1,2-b]pyridazin-8-yl)-3-(trifluoromethyl)azetidin-3-ol

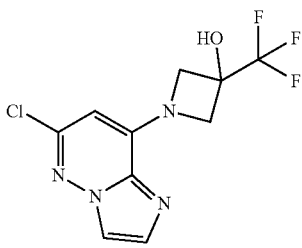 [SMILES: OC1(C(F)(F)F)CN(c2cc(Cl)nn3ccnc23)C1]

1-(6-chloroimidazo[1,2-b]pyridazin-8-yl)-3-(trifluoromethyl)azetidin-3-ol was prepared in the manner described for Intermediate 596, but replacing 3-phenylazetidine hydrochloride with 3-(trifluoromethyl)azetidin-3-ol hydrochloride, and running the reaction at 85° C. for 1 h. ES/MS m/z: 293.1 [M+H].

Intermediate 625. (1-(6-chloroimidazo[1,2-b]pyridazin-8-yl)-3-fluoroazetidin-3-yl)methanol

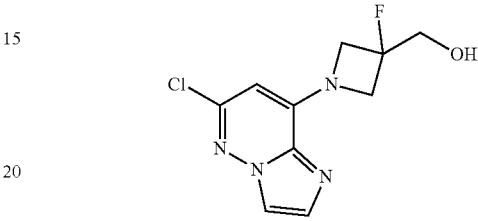

(1-(6-chloroimidazo[1,2-b]pyridazin-8-yl)-3-fluoroazetidin-3-yl)methanol was prepared in the manner described for Intermediate 596, but replacing 3-phenylazetidine hydrochloride with (3-fluoroazetidin-3-yl)methanol, and running the reaction at 85° C. for 1 h. ES/MS m/z: 257.1 [M+H].

Intermediate 626. 6-chloro-8-(3,3-difluoro-4-((5-(trifluoromethyl)pyridin-2-yl)oxy)pyrrolidin-1-yl)-[1,2,4]triazolo[1,5-b]pyridazine

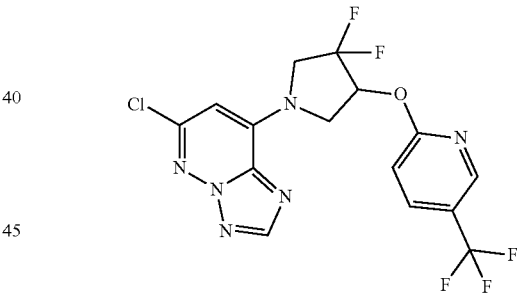

6-chloro-8-(3,3-difluoro-4-((5-(trifluoromethyl)pyridin-2-yl)oxy)pyrrolidin-1-yl)-[1,2,4]triazolo[1,5-b]pyridazine was prepared as follows: To a mixture of 1-(6-chloro-[1,2,4]triazolo[1,5-b]pyridazin-8-yl)-4,4-difluoropyrrolidin-3-ol (44 mg, 0.160 mmol) and cesium carbonate (130 mg, 0.399 mmol) in NMP (1 mL) was added 2-fluoro-5-(trifluoromethyl)pyridine (0.039 mL, 0.319 mmol), and the mixture heated to 60° C. for 1 h. The mixture was then cooled to rt, diluted with EtOAc, and washed with brine. Combined organics were dried over MgSO$_4$, filtered, and concentrated in vacuo. The resulting residue was purified by silica gel chromatography (0-100% EtOAc/hexanes) to afford 6-chloro-8-(3,3-difluoro-4-((5-(trifluoromethyl)pyridin-2-yl)oxy)pyrrolidin-1-yl)-[1,2,4]triazolo[1,5-b]pyridazine. ES/MS m/z: 421.1 [M+H].

Intermediate 627. 6-chloro-8-(3-(trifluoromethyl)-3-((5-(trifluoromethyl)pyridin-2-yl)oxy)azetidin-1-yl)imidazo[1,2-b]pyridazine

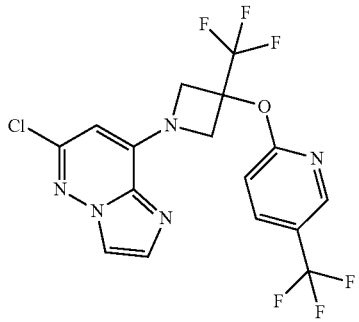 [SMILES: FC(F)(F)c1ccc(OC2(C(F)(F)F)CN(c3cc(Cl)nn4ccnc34)C2)nc1]

6-chloro-8-(3-(trifluoromethyl)-3-((5-(trifluoromethyl)pyridin-2-yl)oxy)azetidin-1-yl)imidazo[1,2-b]pyridazine was prepared in the manner described for Intermediate 626, but replacing 1-(6-chloro-[1,2,4]triazolo[1,5-b]pyridazin-8-yl)-4,4-difluoropyrrolidin-3-ol with 1-(6-chloroimidazo[1,2-b]pyridazin-8-yl)-3-(trifluoromethyl)azetidin-3-ol. ES/MS m/z: 438.1 [M+H].

Intermediate 628. 6-chloro-8-(3-fluoro-3-(((5-(trifluoromethyl)pyridin-2-yl)oxy)methyl)azetidin-1-yl)imidazo[1,2-b]pyridazine

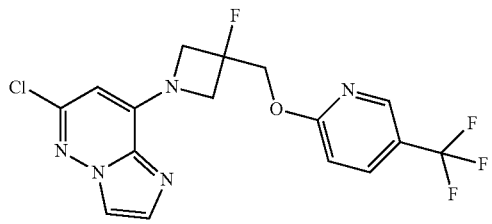 [SMILES: FC1(COc2ccc(C(F)(F)F)cn2)CN(c2cc(Cl)nn3ccnc23)C1]

6-chloro-8-(3-fluoro-3-(((5-(trifluoromethyl)pyridin-2-yl)oxy)methyl)azetidin-1-yl)imidazo[1,2-b]pyridazine was prepared in the manner described for Intermediate 626, but replacing 1-(6-chloro-[1,2,4]triazolo[1,5-b]pyridazin-8-yl)-4,4-difluoropyrrolidin-3-ol with (1-(6-chloroimidazo[1,2-b]pyridazin-8-yl)-3-fluoroazetidin-3-yl)methanol. ES/MS m/z: 402.1 [M+H].

Intermediate 629. 1-(6-chloro-[1,2,4]triazolo[1,5-b]pyridazin-8-yl)-4,4-difluoropyrrolidin-3-yl (2,2,2-trifluoroethyl)carbamate

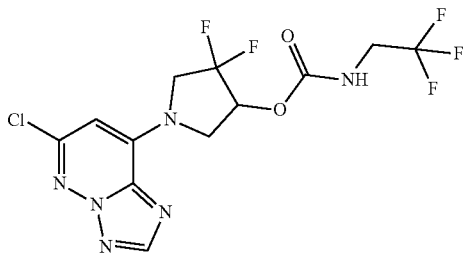 [SMILES: O=C(NCC(F)(F)F)OC1CN(c2cc(Cl)nn3ncnc23)CC1(F)F]

1-(6-chloro-[1,2,4]triazolo[1,5-b]pyridazin-8-yl)-4,4-difluoropyrrolidin-3-yl (2,2,2-trifluoroethyl)carbamate was prepared as follows: To a solution of 1-(6-chloro-[1,2,4]triazolo[1,5-b]pyridazin-8-yl)-4,4-difluoropyrrolidin-3-ol (44 mg, 0.160 mmol) in DMF (1 mL) at 0° C. was added NaH (7.3 mg, 0.192 mmol). The mixture was stirred at 0° C. for 30 min, after which 1,1,1-trifluoro-2-isocyanato-ethane (30 mg, 0.239 mmol) was added. The mixture was stirred overnight, allowing to warm to rt. Additional NaH (15 mg, 0.375 mmol) was added, followed by additional 1,1,1-trifluoro-2-isocyanato-ethane (60 mg, 0.480 mmol), and the mixture stirred for 1 h. Another portion of both NaH (15 mg, 0.375 mmol) and 1,1,1-trifluoro-2-isocyanato-ethane (60 mg, 0.480 mmol) were added, and the mixture stirred at rt for 16 h. The mixture was then quenched with H$_2$O and extracted with EtOAc. Combined organics were dried over MgSO$_4$, filtered, and concentrated in vacuo. The resulting residue was purified by silica gel chromatography (0-100% EtOAc/hexanes) to afford 1-(6-chloro-[1,2,4]triazolo[1,5-b]pyridazin-8-yl)-4,4-difluoropyrrolidin-3-yl(2,2,2-trifluoroethyl)carbamate. ES/MS m/z: 401.1 [M+H].

Intermediate 630. (1-(6-chloroimidazo[1,2-b]pyridazin-8-yl)-3-fluoroazetidin-3-yl)methyl (2,2,2-trifluoroethyl)carbamate

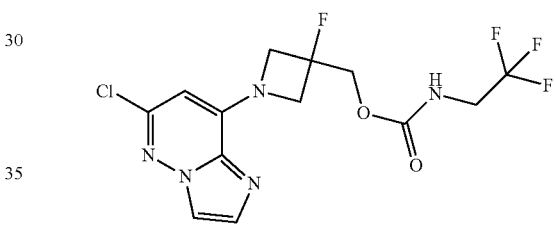

(1-(6-chloroimidazo[1,2-b]pyridazin-8-yl)-3-fluoroazetidin-3-yl)methyl (2,2,2-trifluoroethyl)carbamate was prepared in the manner described for Intermediate 629, but replacing 1-(6-chloro-[1,2,4]triazolo[1,5-b]pyridazin-8-yl)-4,4-difluoropyrrolidin-3-ol with (1-(6-chloroimidazo[1,2-b]pyridazin-8-yl)-3-fluoroazetidin-3-yl)methanol. ES/MS m/z: 382.1 [M+H].

Intermediate 631. 3-((6-chloro-[1,2,4]triazolo[1,5-b]pyridazin-8-yl)oxy)-2,2-difluoropropyl isopropylcarbamate

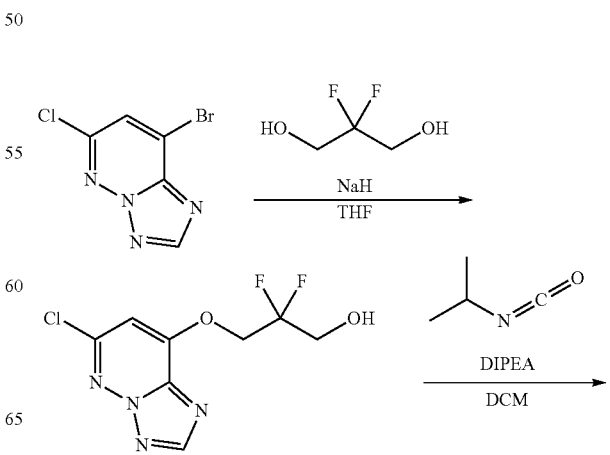

-continued

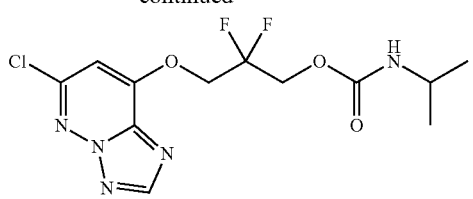

To a solution of 8-bromo-6-chloro[1,2,4]triazolo[1,5-b]pyridazine (200 mg, 0.86 mmol) and 2,2-difluoropropane-1,3-diol (288 mg, 2.6 mmol) in THF (10 mL) at 0° C. was added NaH (39 mg, 1.70 mmol). The mixture was stirred overnight, allowing to warm to rt, then quenched with $H_2O$ and extracted with EtOAc. Combined organics were dried over $MgSO_4$, filtered, and concentrated in vacuo. The residue was purified by silica gel chromatography (0-100% EtOAc/hexanes) to afford 3-((6-chloro[1,2,4]triazolo[1,5-b]pyridazin-8-yl)oxy)-2,2-difluoropropan-1-ol. ES/MS m/z: 265.1 [M+H].

To a solution of 3-((6-chloro[1,2,4]triazolo[1,5-b]pyridazin-8-yl)oxy)-2,2-difluoropropan-1-ol (90 mg, 0.34 mmol) in DCM (2 mL) was added DIPEA (0.59 mL, 3.4 mmol), followed by 2-isocyanatopropane (0.33 mL, 3.4 mmol). The mixture was stirred at 50° C. for 2 h, then cooled to rt, concentrated in vacuo, and purified by silica gel chromatography (0-100% EtOAc/hexanes) to afford 3-((6-chloro-[1,2,4]triazolo[1,5-b]pyridazin-8-yl)oxy)-2,2-difluoropropyl isopropylcarbamate. ES/MS m/z: 350.1 [M+H].

Intermediate 632. 6-chloro-8-[(1S,2S)-2-(3,5-difluorophenyl)cyclopropyl]imidazo[1,2-b]pyridazine

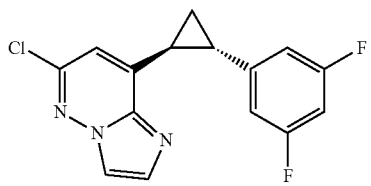 [SMILES: Fc1cc(F)cc([C@H]2C[C@@H]2c2cc(Cl)nn3ccnc23)c1]

6-chloro-8-[(1S,2S)-2-(3,5-difluorophenyl)cyclopropyl]imidazo[1,2-b]pyridazine (Racemic Mixture) was prepared as follows: A microwave vial was charged with 8-bromo-6-chloro-imidazo[1,2-b]pyridazine (299 mg, 1.29 mmol, 1.2 equiv), racemic 2-[(1S,2S)-2-(3,5-difluorophenyl)cyclopropyl]-4,4,5,5-tetramethyl-1,3,2-dioxaborolane (300 mg, 1.07 mmol, 1 equiv), cesium carbonate (698 mg, 2.14 mmol, 2 equiv), and $Pd(dppf)Cl_2CH_2Cl_2$ (88 mg, 10 mol %). The solids were dissolved in dioxane (3 mL) and $H_2O$ (1.5 mL), and the mixture was degassed with N2. The vial was sealed and heated to 120° C. for 4 h. The reaction mixture was then cooled and filtered through celite, washing with EtOAc. The filtrate was concentrated in vacuo, and the resulting residue purified by silica gel chromatography (0-100% EtOAc/hexanes), affording 6-chloro-8-[(1S,2S)-2-(3,5-difluorophenyl)cyclopropyl]imidazo[1,2-b]pyridazine. ES/MS m/z: 306.0 [M+H].

Intermediate 633. 4-[(1S,2S)-2-(6-chloroimidazo[1,2-b]pyridazin-8-yl)cyclopropyl]-2-fluoro-benzonitrile

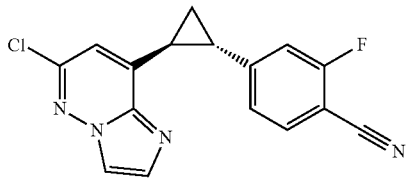 [SMILES: N#Cc1ccc([C@H]2C[C@@H]2c2cc(Cl)nn3ccnc23)cc1F]

4-[(1S,2S)-2-(6-chloroimidazo[1,2-b]pyridazin-8-yl)cyclopropyl]-2-fluoro-benzonitrile (Racemic Mixture) was prepared in the manner described for Intermediate 628, but replacing 2-[(1S,2S)-2-(3,5-difluorophenyl)cyclopropyl]-4,4,5,5-tetramethyl-1,3,2-dioxaborolane with 2-fluoro-4-[(1S,2S)-2-(4,4,5,5-tetramethyl-1,3,2-dioxaborolan-2-yl)cyclopropyl]benzonitrile. ES/MS m/z: 313.1 [M+H].

Intermediate 634. 5-[(1S,2S)-2-(6-chloroimidazo[1,2-b]pyridazin-8-yl)cyclopropyl]-2-fluoro-benzonitrile

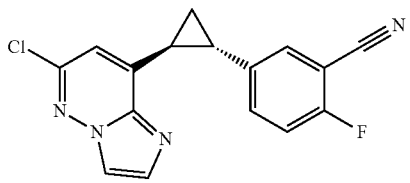 [SMILES: N#Cc1cc([C@H]2C[C@@H]2c2cc(Cl)nn3ccnc23)ccc1F]

5-[(1S,2S)-2-(6-chloroimidazo[1,2-b]pyridazin-8-yl)cyclopropyl]-2-fluoro-benzonitrile (Racemic Mixture) was prepared in the manner described for Intermediate 628, but replacing 2-[(1S,2S)-2-(3,5-difluorophenyl)cyclopropyl]-4,4,5,5-tetramethyl-1,3,2-dioxaborolane with 2-fluoro-5-[(1S,2S)-2-(4,4,5,5-tetramethyl-1,3,2-dioxaborolan-2-yl)cyclopropyl]benzonitrile. ES/MS m/z: 313.1 [M+H].

Intermediate 635. 4-((1S,2S)-2-(6-chloroimidazo[1,2-b]pyridazin-8-yl)cyclopropyl)-3-fluorobenzonitrile

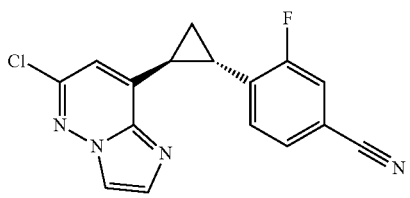 [SMILES: N#Cc1ccc([C@H]2C[C@@H]2c2cc(Cl)nn3ccnc23)c(F)c1]

4-((1S,2S)-2-(6-chloroimidazo[1,2-b]pyridazin-8-yl)cyclopropyl)-3-fluorobenzonitrile (Racemic Mixture) was prepared in the manner described for Intermediate 628, but replacing 2-[(1S,2S)-2-(3,5-difluorophenyl)cyclopropyl]-4,4,5,5-tetramethyl-1,3,2-dioxaborolane with 3-fluoro-4-((1S,2S)-2-(4,4,5,5-tetramethyl-1,3,2-dioxaborolan-2-yl)cyclopropyl)benzonitrile. ES/MS m/z: 313.1 [M+H].

Intermediate 636. 3-((1S,2S)-2-(6-chloroimidazo[1,2-b]pyridazin-8-yl)cyclopropyl)-2-fluorobenzonitrile

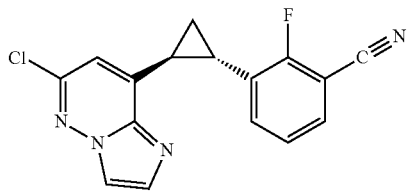 [SMILES: N#Cc1cccc([C@H]2C[C@@H]2c2cc(Cl)nn3ccnc23)c1F]

3-((1S,2S)-2-(6-chloroimidazo[1,2-b]pyridazin-8-yl)cyclopropyl)-2-fluorobenzonitrile (Racemic Mixture) was prepared in the manner described for Intermediate 628, but replacing 2-[(1S,2S)-2-(3,5-difluorophenyl)cyclopropyl]-4,4,5,5-tetramethyl-1,3,2-dioxaborolane with 2-fluoro-3-((1S,2S)-2-(4,4,5,5-tetramethyl-1,3,2-dioxaborolan-2-yl)cyclopropyl)benzonitrile. ES/MS m/z: 313.1 [M+H].

Intermediate 637. 5-((1S,2S)-2-(6-chloroimidazo[1,2-b]pyridazin-8-yl)cyclopropyl)-2-(trifluoromethyl)benzonitrile

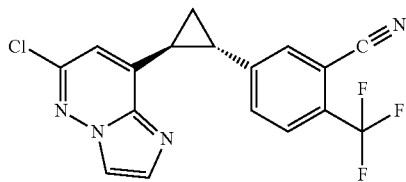 [SMILES: N#Cc1cc([C@H]2C[C@@H]2c2cc(Cl)nn3ccnc23)ccc1C(F)(F)F]

5-((1S,2S)-2-(6-chloroimidazo[1,2-b]pyridazin-8-yl)cyclopropyl)-2-(trifluoromethyl)benzonitrile (Racemic Mixture) was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 5-((2S,2S)-2-(4,4,5,5-tetramethyl-1,3,2-dioxaborolan-2-yl)cyclopropyl)-2-(trifluoromethyl)benzonitrile. ES/MS m/z: 363.0 [M+H].

Intermediate 638. 4-((1S,2S)-2-(6-chloroimidazo[1,2-b]pyridazin-8-yl)cyclopropyl)-2-(trifluoromethoxy)benzonitrile

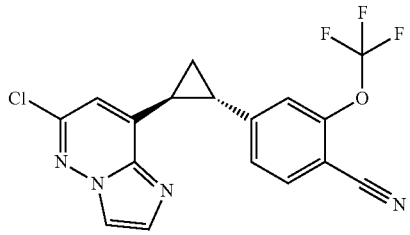 [SMILES: N#Cc1ccc([C@H]2C[C@@H]2c2cc(Cl)nn3ccnc23)cc1OC(F)(F)F]

4-(1S,2S)-2-(6-chloroimidazo[1,2-b]pyridazin-8-yl)cyclopropyl)-2-(trifluoromethoxy)benzonitrile (Racemic Mixture) was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 4-((1S,2S)-2-(4,4,5,5-tetramethyl-1,3,2-dioxaborolan-2-yl)cyclopropyl)-2-(trifluoromethoxy)benzonitrile. ES/MS m/z: 379.0 [M+H].

Intermediate 639. 5-((1S,2S)-2-(6-chloroimidazo[1,2-b]pyridazin-8-yl)cyclopropyl)-2-(trifluoromethoxy)benzonitrile

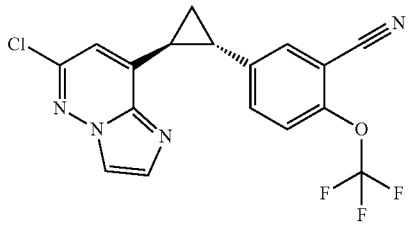 [SMILES: N#Cc1cc([C@H]2C[C@@H]2c2cc(Cl)nn3ccnc23)ccc1OC(F)(F)F]

5-((1S,2S)-2-(6-chloroimidazo[1,2-b]pyridazin-8-yl)cyclopropyl)-2-(trifluoromethoxy)benzonitrile (Racemic Mixture) was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 5-((2S,2S)-2-(4,4,5,5-tetramethyl-1,3,2-dioxaborolan-2-yl)cyclopropyl)-2-(trifluoromethoxy)benzonitrile. ES/MS m/z: 379.0 [M+H].

Intermediate 640. 4-((1S,2S)-2-(6-chloro-3-fluoroimidazo[1,2-b]pyridazin-8-yl)cyclopropyl)-2-fluorobenzonitrile

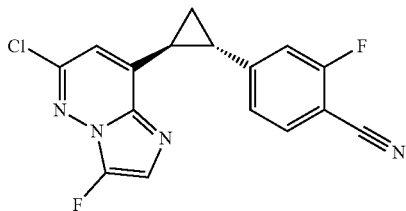 [SMILES: N#Cc1ccc([C@H]2C[C@@H]2c2cc(Cl)nn3c(F)cnc23)cc1F]

4-(1S,2S)-2-(6-chloro-3-fluoroimidazo[1,2-b]pyridazin-8-yl)cyclopropyl)-2-fluorobenzonitrile was prepared in the manner described for Intermediate 238, but replacing 8-bromo-6-chloro-imidazo[1,2-b]pyridazine and 4-((1S,2S)-2-(4,4,5,5-tetramethyl-1,3,2-dioxaborolan-2-yl)cyclopropyl)-2-(trifluoromethyl)benzonitrile with 8-bromo-6-chloro-3-fluoroimidazo[1,2-b]pyridazine and 2-fluoro-4-((1S,2S)-2-(4,4,5,5-tetramethyl-1,3,2-dioxaborolan-2-yl)cyclopropyl)benzonitrile, respectively. ES/MS m/z: 331.1 [M+H].

Intermediate 641. 6-chloro-8-((1S,2S)-2-(4-(difluoromethyl)phenyl)cyclopropyl)imidazo[1,2-b]pyridazine

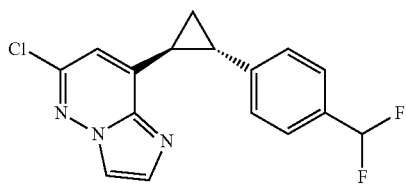 [SMILES: FC(F)c1ccc([C@H]2C[C@@H]2c2cc(Cl)nn3ccnc23)cc1]

6-chloro-8-((1S,2S)-2-(4-(difluoromethyl)phenyl)cyclopropyl)imidazo[1,2-b]pyridazine was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 2-((1S,2S)-2-(4-(difluoromethyl)phenyl)cyclopropyl)-4,4,5,5-tetramethyl-1,3,2-dioxaborolane. ES/MS m/z: 320.1 [M+H].

Intermediate 642. 6-chloro-8-((1S,2S)-2-(4-(difluoromethyl)phenyl)cyclopropyl)-3-fluoroimidazo[1,2-b]pyridazine

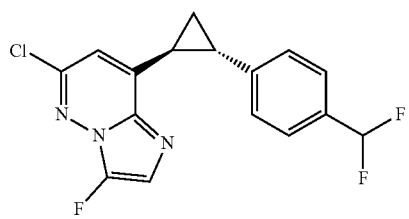 [SMILES: Fc1cnc2c([C@H]3C[C@@H]3c3ccc(C(F)F)cc3)cc(Cl)nn12]

6-chloro-8-((1S,2S)-2-(4-(difluoromethyl)phenyl)cyclopropyl)-3-fluoroimidazo[1,2-b]pyridazine was prepared in the manner described for Intermediate 238, but replacing 8-bromo-6-chloro-imidazo[1,2-b]pyridazine and 4-((2S,2S)-2-(4,4,5,5-tetramethyl-1,3,2-dioxaborolan-2-yl)cyclopropyl)-2-(trifluoromethyl)benzonitrile with 8-bromo-6-chloro-3-fluoroimidazo[1,2-b]pyridazine and 2-((2S,2S)-2-(4-(difluoromethyl)phenyl)cyclopropyl)-4,4,5,5-tetramethyl-1,3,2-dioxaborolane, respectively. ES/MS m/z: 338.1 [M+H].

Intermediate 643. 4-((2S,2S)-2-(6-chloroimidazo[1,2-b]pyridazin-8-yl)cyclopropyl)-3,5-difluorobenzonitrile

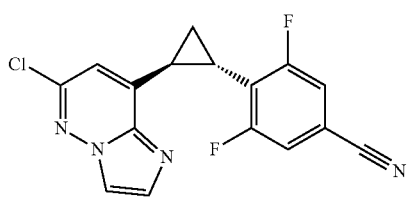 [SMILES: N#Cc1cc(F)c([C@H]2C[C@@H]2c2cc(Cl)nn3ccnc23)c(F)c1]

4-(1S,2S)-2-(6-chloroimidazo[1,2-b]pyridazin-8-yl)cyclopropyl)-3,5-difluorobenzonitrile was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 3,5-difluoro-4-((1S,2S)-2-(4,4,5,5-tetramethyl-1,3,2-dioxaborolan-2-yl)cyclopropyl)benzonitrile. ES/MS m/z: 331.1 [M+H].

Intermediate 644. 4-((2S,2S)-2-(6-chloro-3-fluoroimidazo[1,2-b]pyridazin-8-yl)cyclopropyl)-3,5-difluorobenzonitrile

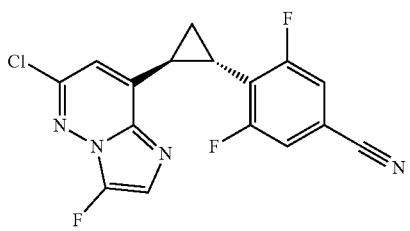 [SMILES: N#Cc1cc(F)c([C@H]2C[C@@H]2c2cc(Cl)nn3c(F)cnc23)c(F)c1]

4-(1S,2S)-2-(6-chloro-3-fluoroimidazo[1,2-b]pyridazin-8-yl)cyclopropyl)-3,5-difluorobenzonitrile was prepared in the manner described for Intermediate 238, but replacing 8-bromo-6-chloro-imidazo[1,2-b]pyridazine and 4-((1S,2S)-2-(4,4,5,5-tetramethyl-1,3,2-dioxaborolan-2-yl)cyclopropyl)-2-(trifluoromethyl)benzonitrile with 8-bromo-6-chloro-3-fluoroimidazo[1,2-b]pyridazine and 3,5-difluoro-4-((2S,2S)-2-(4,4,5,5-tetramethyl-1,3,2-dioxaborolan-2-yl)cyclopropyl)benzonitrile, respectively. ES/MS m/z: 349.1 [M+H].

Intermediate 645. 4-((2S,2S)-2-(6-chloro-[1,2,4]triazolo[1,5-b]pyridazin-8-yl)cyclopropyl)-3,5-difluorobenzonitrile

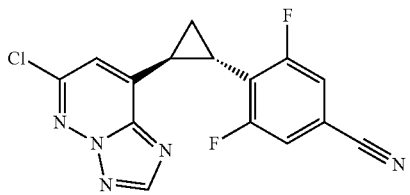 [SMILES: N#Cc1cc(F)c([C@H]2C[C@@H]2c2cc(Cl)nn3ncnc23)c(F)c1]

4-(1S,2S)-2-(6-chloro-[1,2,4]triazolo[1,5-b]pyridazin-8-yl)cyclopropyl)-3,5-difluorobenzonitrile was prepared in the manner described for Intermediate 238, but replacing 8-bromo-6-chloro-imidazo[1,2-b]pyridazine and 4-((1S,2S)-2-(4,4,5,5-tetramethyl-1,3,2-dioxaborolan-2-yl)cyclopropyl)-2-(trifluoromethyl)benzonitrile with 8-bromo-6-chloro-[1,2,4]triazolo[1,5-b]pyridazine and 3,5-difluoro-4-((1S,2S)-2-(4,4,5,5-tetramethyl-1,3,2-dioxaborolan-2-yl)cyclopropyl)benzonitrile, respectively. ES/MS m/z: 332.0 [M+H].

Intermediate 646. 6-chloro-8-((2S,2S)-2-(1-(2,2,2-trifluoroethyl)-1H-indazol-5-yl)cyclopropyl)-[1,2,4]triazolo[1,5-b]pyridazine

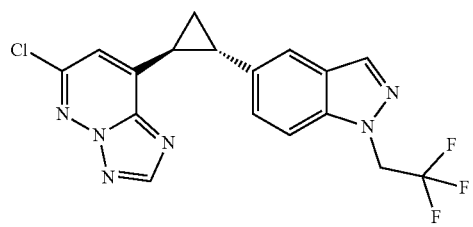 [SMILES: FC(F)(F)Cn1ncc2cc([C@H]3C[C@@H]3c3cc(Cl)nn4ncnc34)ccc21]

6-chloro-8-((1S,2S)-2-(1-(2,2,2-trifluoroethyl)-1H-indazol-5-yl)cyclopropyl)-[1,2,4]triazolo[1,5-b]pyridazine was prepared in the manner described for Intermediate 238, but replacing 8-bromo-6-chloro-imidazo[1,2-b]pyridazine and 4-((1S,2S)-2-(4,4,5,5-tetramethyl-1,3,2-dioxaborolan-2-yl)cyclopropyl)-2-(trifluoromethyl)benzonitrile with 8-bromo-6-chloro-[1,2,4]triazolo[1,5-b]pyridazine and 5-((2S,2S)-2-(4,4,5,5-tetramethyl-1,3,2-dioxaborolan-2-yl)cyclopropyl)-1-(2,2,2-trifluoroethyl)-1H-indazole, respectively, and running the reaction at 90° C. ES/MS m/z: 393.1 [M+H].

Intermediate 647. 6-chloro-8-((2S,2S)-2-(1-(2,2,2-trifluoroethyl)-1H-indazol-6-yl)cyclopropyl)-[1,2,4]triazolo[1,5-b]pyridazine

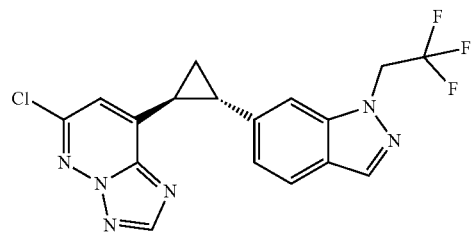 [SMILES: FC(F)(F)Cn1ncc2ccc([C@H]3C[C@@H]3c3cc(Cl)nn4ncnc34)cc21]

6-chloro-8-((2S,2S)-2-(1-(2,2,2-trifluoroethyl)-1H-indazol-6-yl)cyclopropyl)-[1,2,4]triazolo[1,5-b]pyridazine was prepared in the manner described for Intermediate 238, but replacing 8-bromo-6-chloro-imidazo[1,2-b]pyridazine and 4-((2S,2S)-2-(4,4,5,5-tetramethyl-1,3,2-dioxaborolan-2-yl)cyclopropyl)-2-(trifluoromethyl)benzonitrile with 8-bromo-6-chloro-[1,2,4]triazolo[1,5-b]pyridazine and 6-((2S,2S)-2-(4,4,5,5-tetramethyl-1,3,2-dioxaborolan-2-yl)cyclopropyl)-1-(2,2,2-trifluoroethyl)-1H-indazole, respectively, and running the reaction at 80° C. ES/MS m/z: 393.1 [M+H].

Intermediate 648. 6-chloro-8-((2S,2S)-2-(5-chloropyridin-2-yl)cyclopropyl)-[1,2,4]triazolo[1,5-b]pyridazine

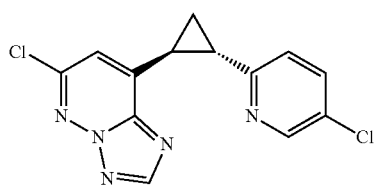 [SMILES: Clc1ccc([C@H]2C[C@@H]2c2cc(Cl)nn3ncnc23)nc1]

6-chloro-8-((1S,2S)-2-(5-chloropyridin-2-yl)cyclopropyl)[1,2,4]triazolo[1,5-b]pyridazine was prepared in the manner described for Intermediate 238, but replacing 8-bromo-6-chloro-imidazo[1,2-b]pyridazine and 4-((1S,2S)-2-(4,4,5,5-tetramethyl-1,3,2-dioxaborolan-2-yl)cyclopropyl)-2-(trifluoromethyl)benzonitrile with 8-bromo-6-chloro[1,2,4]triazolo[1,5-b]pyridazine and 5-chloro-2-((1S,2S)-2-(4,4,5,5-tetramethyl-1,3,2-dioxaborolan-2-yl)cyclopropyl)pyridine, respectively, and running the reaction at 80° C. ES/MS m/z: 306.0 [M+H].

Intermediate 649. 5-chloro-7-((2S,2S)-2-(2,4-difluorophenyl)cyclopropyl)-[1,2,4]triazolo[1,5-a]pyrimidine

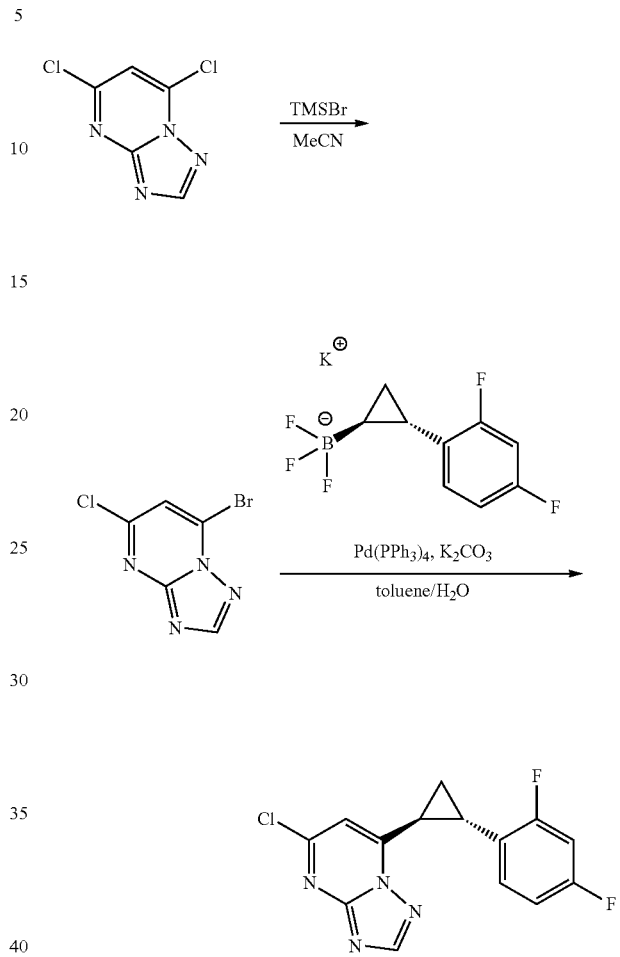

5-chloro-7-((1S,2S)-2-(2,4-difluorophenyl)cyclopropyl)-[1,2,4]triazolo[1,5-a]pyrimidine was prepared as follows: To a solution of 5,7-dichloro-[1,2,4]triazolo[1,5-a]pyrimidine (1.0 g, 5.29 mmol) in MeCN (25 mL) was added bromotrimethylsilane (3.49 mL, 26.5 mmol). The mixture was stirred at rt for 1 h. The suspension was filtered, washing with MeCN, and the solids were then purified by silica gel chromatography (0-15% MeOH/DCM) to afford 7-bromo-5-chloro-[1,2,4]triazolo[1,5-a]pyrimidine. ES/MS m/z: 233.0 [M+H].

A microwave vial was charged with 7-bromo-5-chloro-[1,2,4]triazolo[1,5-a]pyrimidine (117 mg, 0.50 mmol), potassium ((1S,2S)-2-(2,4-difluorophenyl)cyclopropyl)trifluoroborate (100 mg, 0.385 mmol), potassium carbonate (159 mg, 1.15 mmol), and Pd(PPh$_3$)$_4$ (22 mg, 0.019 mmol). The solids were dissolved in toluene (2 mL) and H$_2$O (0.4 mL), and the mixture was degassed with N$_2$. The vial was sealed and heated to 80° C. for 1 h. The reaction mixture was then cooled and filtered through celite, washing with EtOAc. The filtrate was concentrated in vacuo, and the resulting residue purified by silica gel chromatography (0-100% EtOAc/hexanes), affording 5-chloro-7-((1S,2S)-2-(2,4-difluorophenyl)cyclopropyl)-[1,2,4]triazolo[1,5-a]pyrimidine. ES/MS m/z: 307.0 [M+H].

Intermediate 650. 5-chloro-7-((2S,2S)-2-(2,4-difluorophenyl)cyclopropyl)-[1,2,4]triazolo[1,5-a]pyrimidine

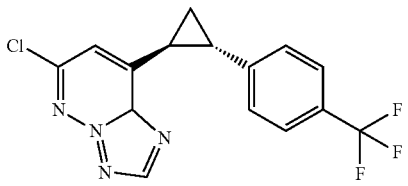

5-chloro-7-((1S,2S)-2-(2,4-difluorophenyl)cyclopropyl)-[1,2,4]triazolo[1,5-a]pyrimidine was prepared in the manner described for Intermediate 649, but replacing potassium ((1S,2S)-2-(2,4-difluorophenyl)cyclopropyl)trifluoroborate with potassium trifluoro((2S,2S)-2-(4-(trifluoromethyl)phenyl)cyclopropyl)borate. ES/MS m/z: 339.1 [M+H].

Intermediate 651. 6-chloro-8-((2S,2S)-2-(4-(trifluoromethyl)phenyl)cyclopropyl)-[1,2,4]triazolo[1,5-b]pyridazine

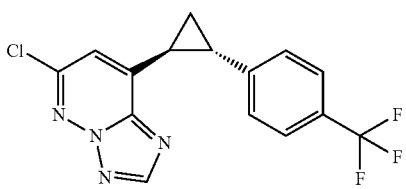 [SMILES: FC(F)(F)c1ccc([C@H]2C[C@@H]2c2cc(Cl)nn3ncnc23)cc1]

6-chloro-8-((1S,2S)-2-(4-(trifluoromethyl)phenyl)cyclopropyl)-[1,2,4]triazolo[1,5-b]pyridazine was prepared as follows: A microwave vial was charged with 8-bromo-6-chloro-[1,2,4]triazolo[1,5-b]pyridazine (50 mg, 0.214 mmol), potassium trifluoro((1S,2S)-2-(4-(trifluoromethyl)phenyl)cyclopropyl)borate (48 mg, 0.164 mmol), potassium carbonate (68 mg, 0.493 mmol), and Pd(PPh$_3$)$_4$ (10 mg, 0.0082 mmol). The solids were dissolved in toluene (1 mL) and H$_2$O (0.2 mL), and the mixture was degassed with N$_2$. The vial was sealed and heated to 110° C. for 1 h. The reaction mixture was then cooled and filtered through celite, washing with EtOAc. The filtrate was concentrated in vacuo, and the resulting residue purified by silica gel chromatography (0-100% EtOAc/hexanes), affording 6-chloro-8-((2S,2S)-2-(4-(trifluoromethyl)phenyl)cyclopropyl)-[1,2,4]triazolo[1,5-b]pyridazine. ES/MS m/z: 339.0 [M+H].

Intermediate 652. 4-[(1S,2S)-2-[6-(2,4-dimethoxypyrimidin-5-yl)imidazo[1,2-b]pyridazin-8-yl]cyclopropyl]-2-fluoro-benzonitrile

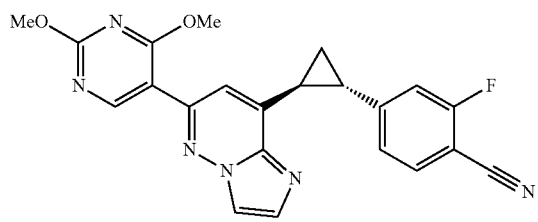 [SMILES: COc1ncc(-c2cc([C@H]3C[C@@H]3c3ccc(C#N)c(F)c3)c3nccn3n2)c(OC)n1]

4-[(1S,2S)-2-[6-(2,4-dimethoxypyrimidin-5-yl)imidazo[1,2-b]pyridazin-8-yl]cyclopropyl]-2-fluoro-benzonitrile (Racemic Mixture) was prepared in the manner described for Intermediate 18, but replacing 6-chloro-8-cyclopropyl-2-methyl-imidazo[1,2-b]pyridazine with 4-[(1S,2S)-2-(6-chloroimidazo[1,2-b]pyridazin-8-yl)cyclopropyl]-2-fluoro-benzonitrile. ES/MS m/z: 417.1 [M+H].

Intermediate 653. 6-(2,4-dimethoxypyrimidin-5-yl)-8-[3-(trifluoromethyl)azetidin-1-yl]imidazo[1,2-b]pyridazine

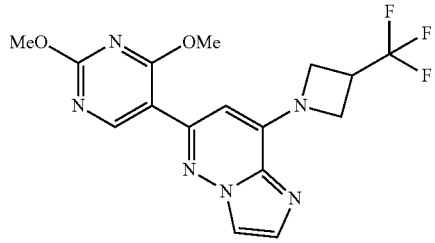 [SMILES: COc1ncc(-c2cc(N3CC(C(F)(F)F)C3)c3nccn3n2)c(OC)n1]

6-(2,4-dimethoxypyrimidin-5-yl)-8-[3-(trifluoromethyl)azetidin-1-yl]imidazo[1,2-b]pyridazine was prepared in the manner described for Intermediate 18, but replacing 6-chloro-8-cyclopropyl-2-methyl-imidazo[1,2-b]pyridazine with 6-chloro-8-[3-(trifluoromethyl)azetidin-1-yl]imidazo[1,2-b]pyridazine. ES/MS m/z: 381.1 [M+H].

Intermediate 654. 6-(2,4-dimethoxypyrimidin-5-yl)-8-(3,3-dimethylazetidin-1-yl)imidazo[1,2-b]pyridazine

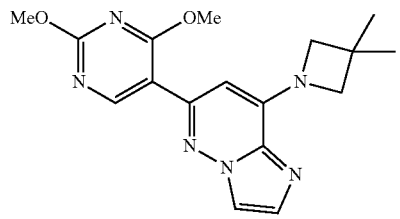

6-(2,4-dimethoxypyrimidin-5-yl)-8-(3,3-dimethylazetidin-1-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3,3-dimethylazetidin-1-yl)imidazo[1,2-b]pyridazine. ES/MS m/z: 341.2 [M+H].

Intermediate 655. 5-[(1S,2S)-2-[6-(2,4-dimethoxypyrimidin-5-yl)imidazo[1,2-b]pyridazin-8-yl]cyclopropyl]-2-fluoro-benzonitrile

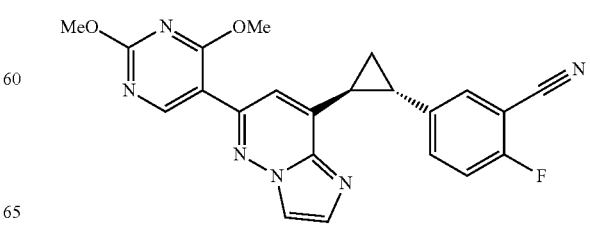

5-[(1S,2S)-2-[6-(2,4-dimethoxypyrimidin-5-yl)imidazo[1,2-b]pyridazin-8-yl]cyclopropyl]-2-fluoro-benzonitrile (Racemic Mixture) was prepared in the manner described for Intermediate 18, but replacing 6-chloro-8-cyclopropyl-2-methyl-imidazo[1,2-b]pyridazine with 5-[(1S,2S)-2-(6-chloroimidazo[1,2-b]pyridazin-8-yl)cyclopropyl]-2-fluoro-benzonitrile. ES/MS m/z: 417.1 [M+H].

Intermediate 656. 6-(2,4-dimethoxypyrimidin-5-yl)-8-(3-fluoro-3-(trifluoromethyl)azetidin-1-yl)imidazo[1,2-b]pyridazine

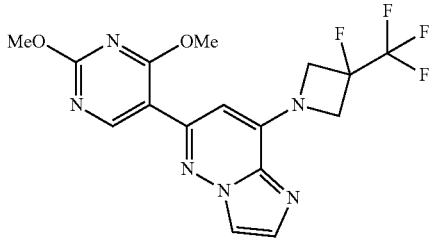 [SMILES: COc1ncc(-c2cc(N3CC(F)(C(F)(F)F)C3)c3nccn3n2)c(OC)n1]

6-(2,4-dimethoxypyrimidin-5-yl)-8-(3-fluoro-3-(trifluoromethyl)azetidin-1-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-fluoro-3-(trifluoromethyl)azetidin-1-yl)imidazo[1,2-b]pyridazine. ES/MS m/z: 399.1 [M+H].

Intermediate 657. 6-(2,4-dimethoxypyrimidin-5-yl)-8-(2-azaspiro[3.3]heptan-2-yl)imidazo[1,2-b]pyridazine

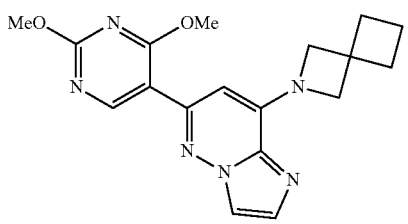 [SMILES: COc1ncc(-c2cc(N3CC4(CCC4)C3)c3nccn3n2)c(OC)n1]

6-(2,4-dimethoxypyrimidin-5-yl)-8-(2-azaspiro[3.3]heptan-2-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(2-azaspiro[3.3]heptan-2-yl)imidazo[1,2-b]pyridazine. ES/MS m/z: 353.2 [M+H].

Intermediate 658. 8-(3-(difluoromethyl)-3-methylazetidin-1-yl)-6-(2,4-dimethoxypyrimidin-5-yl)imidazo[1,2-b]pyridazine

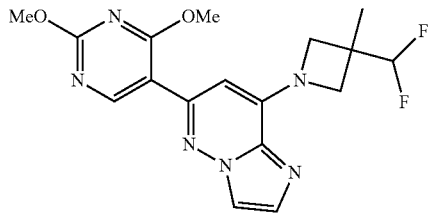 [SMILES: COc1ncc(-c2cc(N3CC(C)(C(F)F)C3)c3nccn3n2)c(OC)n1]

8-(3-(difluoromethyl)-3-methylazetidin-1-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-(difluoromethyl)-3-methyl-azetidin-1-yl)imidazo[1,2-b]pyridazine. ES/MS m/z: 377.2 [M+H].

Intermediate 659. 8-(3-(2,2-difluorocyclopropyl)azetidin-1-yl)-6-(2,4-dimethoxypyrimidin-5-yl)imidazo[1,2-b]pyridazine

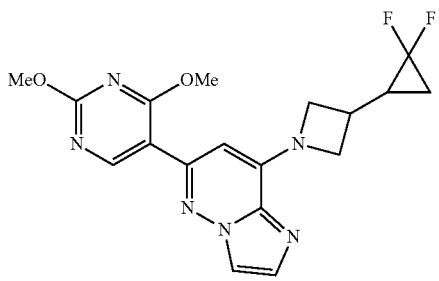 [SMILES: COc1ncc(-c2cc(N3CC(C4CC4(F)F)C3)c3nccn3n2)c(OC)n1]

8-(3-(2,2-difluorocyclopropyl)azetidin-1-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-(2,2-difluorocyclopropyl)azetidin-1-yl)imidazo[1,2-b]pyridazine. ES/MS m/z: 389.2 [M+H].

Intermediate 660. 8-(3-cyclobutylazetidin-1-yl)-6-(2,4-dimethoxypyrimidin-5-yl)imidazo[1,2-b]pyridazine

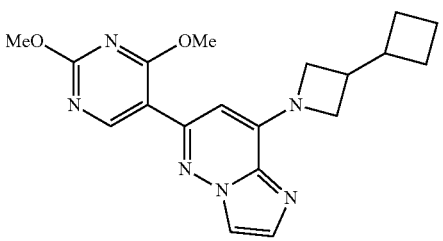 [SMILES: COc1ncc(-c2cc(N3CC(C4CCC4)C3)c3nccn3n2)c(OC)n1]

8-(3-cyclobutylazetidin-1-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-cyclobutylazetidin-1-yl)imidazo[1,2-b]pyridazine. ES/MS m/z: 367.2 [M+H].

Intermediate 661. 5-(2,4-dimethoxypyrimidin-5-yl)-7-(3-fluoro-3-(trifluoromethyl)azetidin-1-0)-[1,2,4]triazolo[1,5-a]pyrimidine

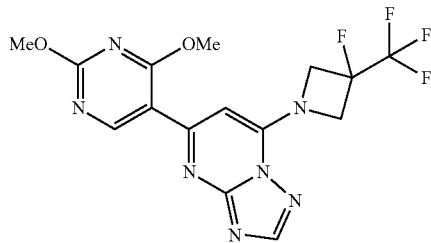 [SMILES: COc1ncc(-c2cc(N3CC(F)(C(F)(F)F)C3)n3ncnc3n2)c(OC)n1]

5-(2,4-dimethoxypyrimidin-5-yl)-7-(3-fluoro-3-(trifluoromethyl)azetidin-1-yl)-[1,2,4]triazolo[1,5-a]pyrimidine was prepared in the manner described for Intermediate 18, but replacing 6-chloro-8-cyclopropyl-2-methyl-imidazo[1,2-b]pyridazine with 5-chloro-7-(3-fluoro-3-(trifluoromethyl)azetidin-1-yl)-[1,2,4]triazolo[1,5-a]pyrimidine. ES/MS m/z: 400.1 [M+H].

Intermediate 662. 8-(3-(difluoromethyl)azetidin-1-yl)-6-(2,4-dimethoxypyrimidin-5-yl)imidazo[1,2-b]pyridazine

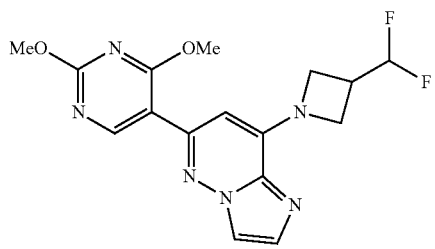 [SMILES: COc1ncc(-c2cc(N3CC(C(F)F)C3)c3nccn3n2)c(OC)n1]

8-(3-(difluoromethyl)azetidin-1-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-(difluoromethyl)azetidin-1-yl)imidazo[1,2-b]pyridazine. ES/MS m/z: 363.1 [M+H].

Intermediate 663. 8-(3-cyclopropylazetidin-1-yl)-6-(2,4-dimethoxypyrimidin-5-yl)imidazo[1,2-b]pyridazine

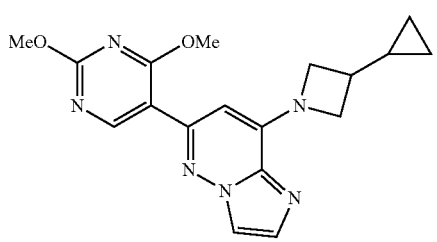 [SMILES: COc1ncc(-c2cc(N3CC(C4CC4)C3)c3nccn3n2)c(OC)n1]

8-(3-cyclopropylazetidin-1-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-cyclopropylazetidin-1-yl)imidazo[1,2-b]pyridazine. ES/MS m/z: 353.2 [M+H].

Intermediate 664. 8-(5,5-difluoro-2-azaspiro[3.3]heptan-2-yl)-6-(2,4-dimethoxypyrimidin-5-yl)imidazo[1,2-b]pyridazine

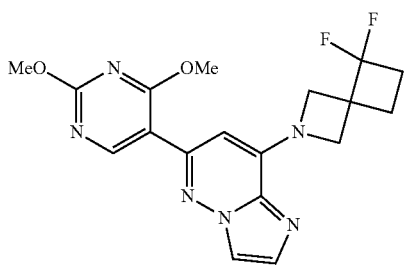 [SMILES: COc1ncc(-c2cc(N3CC4(CCC4(F)F)C3)c3nccn3n2)c(OC)n1]

8-(5,5-difluoro-2-azaspiro[3.3]heptan-2-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(5,5-difluoro-2-azaspiro[3.3]heptan-2-yl)imidazo[1,2-b]pyridazine. ES/MS m/z: 389.2 [M+H].

Intermediate 665. 8-(1,1-difluoro-5-azaspiro[2.3]hexan-5-yl)-6-(2,4-dimethoxypyrimidin-5-yl)imidazo[1,2-b]pyridazine

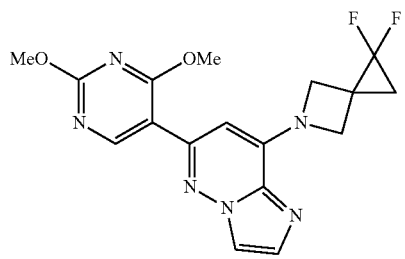 [SMILES: COc1ncc(-c2cc(N3CC4(C3)CC4(F)F)c3nccn3n2)c(OC)n1]

8-(1,1-difluoro-5-azaspiro[2.3]hexan-5-yl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(1,1-difluoro-5-azaspiro[2.3]hexan-5-yl)imidazo[1,2-b]pyridazine. ES/MS m/z: 375.2 [M+H].

Intermediate 666. 4-((2S,2S)-2-(6-(2,4-dimethoxy-pyrimidin-5-yl)imidaz[1,2-b]pyridazin-8-yl)cyclopropyl)-3-fluorobenzonitrile

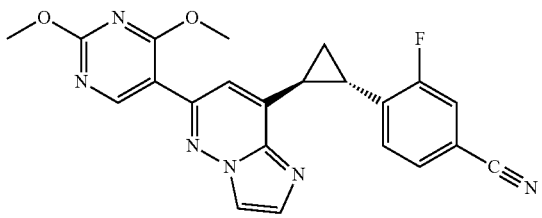 [SMILES: COc1ncc(-c2cc([C@H]3C[C@@H]3c3ccc(C#N)cc3F)c3nccn3n2)c(OC)n1]

4-((1S,2S)-2-(6-(2,4-dimethoxypyrimidin-5-yl)imidazo[1,2-b]pyridazin-8-yl)cyclopropyl)-3-fluorobenzonitrile (Racemic Mixture) was prepared in the manner described for Intermediate 18, but replacing 6-chloro-8-cyclopropyl-2-methyl-imidazo[1,2-b]pyridazine with 4-((2S,2S)-2-(6-chloroimidazo[1,2-b]pyridazin-8-yl)cyclopropyl)-3-fluorobenzonitrile. ES/MS m/z: 417.1 [M+H].

Intermediate 667. 3-((2S,2S)-2-(6-(2,4-dimethoxy-pyrimidin-5-yl)imidazo[1,2-b]pyridazin-8-yl)cyclopropyl)-2-fluorobenzonitrile

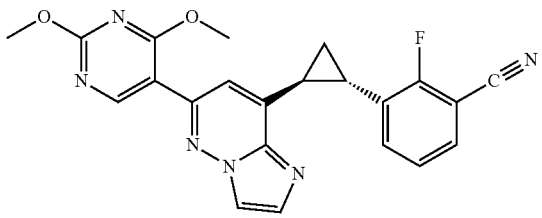 [SMILES: COc1ncc(-c2cc([C@H]3C[C@@H]3c3cccc(C#N)c3F)c3nccn3n2)c(OC)n1]

3-((2S,2S)-2-(6-(2,4-dimethoxypyrimidin-5-yl)imidazo[1,2-b]pyridazin-8-yl)cyclopropyl)-2-fluorobenzonitrile (Racemic Mixture) was prepared in the manner described for Intermediate 18, but replacing 6-chloro-8-cyclopropyl-2-methyl-imidazo[1,2-b]pyridazine with 3-((2S,2S)-2-(6-chloroimidazo[1,2-b]pyridazin-8-yl)cyclopropyl)-2-fluorobenzonitrile. ES/MS m/z: 417.2 [M+H].

Intermediate 668. 6-(2,4-dimethoxypyrimidin-5-yl)-8-(3-(2-fluoropropan-2-yl)azetidin-1-yl)imidazo[1,2-b]pyridazine

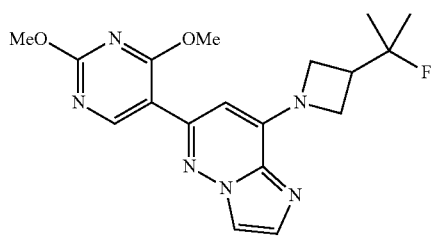 [SMILES: COc1ncc(-c2cc(N3CC(C(C)(C)F)C3)c3nccn3n2)c(OC)n1]

6-(2,4-dimethoxypyrimidin-5-yl)-8-(3-(2-fluoropropan-2-yl)azetidin-1-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-(2-fluoropropan-2-yl)azetidin-1-yl)imidazo[1,2-b]pyridazine. ES/MS m/z: 373.2 [M+H].

Intermediate 669. 6-(2,4-dimethoxypyrimidin-5-yl)-8-(tetrahydro-2H-pyran-4-yl)imidazo[1,2-b]pyridazine

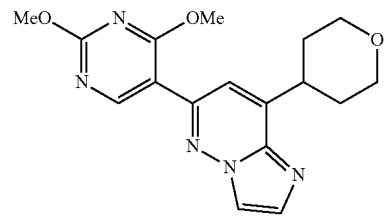

6-(2,4-dimethoxypyrimidin-5-yl)-8-(tetrahydro-2H-pyran-4-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(tetrahydro-2H-pyran-4-yl)imidazo[1,2-b]pyridazine. ES/MS m/z: 342.1 [M+H].

Intermediate 670. 4-((2S,2S)-2-(6-(2,4-dimethoxy-pyrimidin-5-yl)imidazo[1,2-b]pyridazin-8-ylcyclopropyl)-2-(trifluoromethyl)benzonitrile

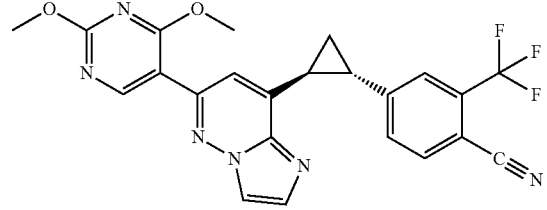 [SMILES: COc1ncc(-c2cc([C@H]3C[C@@H]3c3ccc(C#N)c(C(F)(F)F)c3)c3nccn3n2)c(OC)n1]

4-((1S,2S)-2-(6-(2,4-dimethoxypyrimidin-5-yl)imidazo[1,2-b]pyridazin-8-yl)cyclopropyl)-2-(trifluoromethyl)benzonitrile (Racemic Mixture) was prepared in the manner described for Intermediate 18, but replacing 6-chloro-8-cyclopropyl-2-methyl-imidazo[1,2-b]pyridazine with 4-(1S,2S)-2-(6-chloroimidazo[1,2-b]pyridazin-8-yl)cyclopropyl)-2-(trifluoromethyl)benzonitrile. ES/MS m/z: 467.2 [M+H].

Intermediate 671. 5-((2S,2S)-2-(6-(2,4-dimethoxy-pyrimidin-5-yl)imidazo[1,2-b]pyridazin-8-yl)cyclopropyl)-2-(trifluoromethyl)benzonitrile

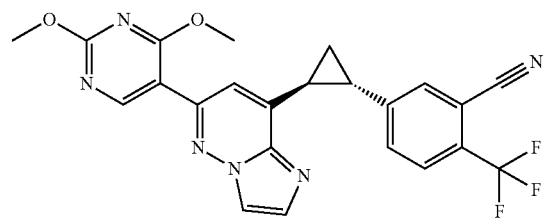 [SMILES: COc1ncc(-c2cc([C@H]3C[C@@H]3c3ccc(C(F)(F)F)c(C#N)c3)c3nccn3n2)c(OC)n1]

5-((1S,2S)-2-(6-(2,4-dimethoxypyrimidin-5-yl)imidazo[1,2-b]pyridazin-8-yl)cyclopropyl)-2-(trifluoromethyl)benzonitrile (Racemic Mixture) was prepared in the manner described for Intermediate 18, but replacing 6-chloro-8-cyclopropyl-2-methyl-imidazo[1,2-b]pyridazine with 54(1S,2S)-2-(6-chloroimidazo[1,2-b]pyridazin-8-yl)cyclopropyl)-2-(trifluoromethyl)benzonitrile. ES/MS m/z: 467.1 [M+H].

Intermediate 672. 4-((2S,2S)-2-(6-(2,4-dimethoxy-pyrimidin-5-yl)imidazo[1,2-b]pyridazin-8-yl)cyclopropyl)-2-(trifluoromethoxy)benzonitrile

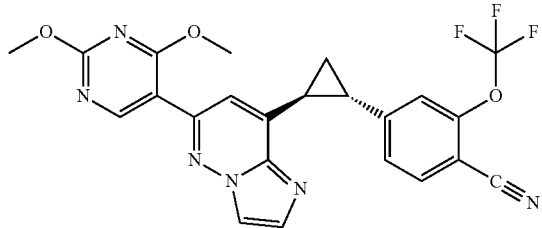 [SMILES: COc1ncc(-c2cc([C@H]3C[C@@H]3c3ccc(C#N)c(OC(F)(F)F)c3)c3nccn3n2)c(OC)n1]

4-((1S,2S)-2-(6-(2,4-dimethoxypyrimidin-5-yl)imidazo[1,2-b]pyridazin-8-yl)cyclopropyl)-2-(trifluoromethoxy)benzonitrile (Racemic Mixture) was prepared in the manner described for Intermediate 18, but replacing 6-chloro-8-cyclopropyl-2-methyl-imidazo[1,2-b]pyridazine with 4-(1S,2S)-2-(6-chloroimidazo[1,2-b]pyridazin-8-yl)cyclopropyl)-2-(trifluoromethoxy)benzonitrile. ES/MS m/z: 483.1 [M+H].

Intermediate 673. 5-((2S,2S)-2-(6-(2,4-dimethoxy-pyrimidin-5-yl)imidazo[1,2-b]pyridazin-8-yl)cyclopropyl)-2-(trifluoromethoxy)benzonitrile

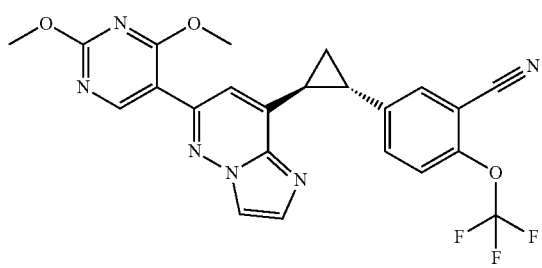 [SMILES: COc1ncc(-c2cc([C@H]3C[C@@H]3c3ccc(OC(F)(F)F)c(C#N)c3)c3nccn3n2)c(OC)n1]

5-((1S,2S)-2-(6-(2,4-dimethoxypyrimidin-5-yl)imidazo[1,2-b]pyridazin-8-yl)cyclopropyl)-2-(trifluoromethoxy)benzonitrile (Racemic Mixture) was prepared in the manner described for Intermediate 18, but replacing 6-chloro-8-cyclopropyl-2-methyl-imidazo[1,2-b]pyridazine with 5-((1S,2S)-2-(6-chloroimidazo[1,2-b]pyridazin-8-yl)cyclopropyl)-2-(trifluoromethoxy)benzonitrile. ES/MS m/z: 483.1 [M+H].

Intermediate 674. 4-((2S,2S)-2-(6-(2,4-dimethoxy-pyrimidin-5-yl)-3-fluoroimidazo[1,2-b]pyridazin-8-yl)cyclopropyl)-2-fluorobenzonitrile

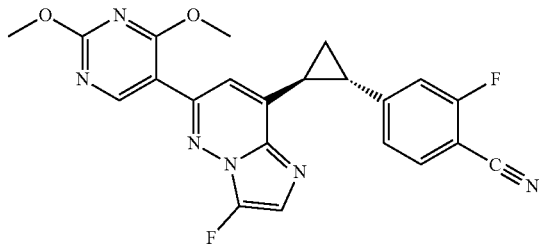 [SMILES: COc1ncc(-c2cc([C@H]3C[C@@H]3c3ccc(C#N)c(F)c3)c3ncc(F)n3n2)c(OC)n1]

4-((2S,2S)-2-(6-(2,4-dimethoxypyrimidin-5-yl)-3-fluoro-imidazo[1,2-b]pyridazin-8-yl)cyclopropyl)-2-fluorobenzonitrile was prepared in the manner described for Intermediate 18, but replacing 6-chloro-8-cyclopropyl-2-methyl-imidazo[1,2-b]pyridazine with 4-((2S,2S)-2-(6-chloro-3-fluoroimidazo[1,2-b]pyridazin-8-yl)cyclopropyl)-2-fluorobenzonitrile. ES/MS m/z: 435.1 [M+H].

Intermediate 675. 7-((2S,2S)-2-(2,4-difluorophenyl)cyclopropyl)-5-(2,4-dimethoxypyrimidin-5-yl)-[1,2,4]triazolo[1,5-a]pyrimidine

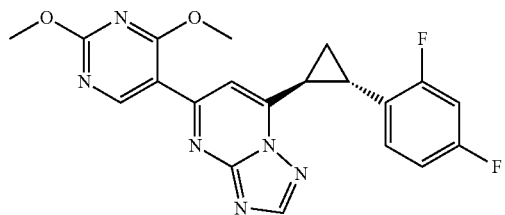 [SMILES: COc1ncc(-c2cc([C@H]3C[C@@H]3c3ccc(F)cc3F)n3ncnc3n2)c(OC)n1]

7-((1S,2S)-2-(2,4-difluorophenyl)cyclopropyl)-5-(2,4-dimethoxypyrimidin-5-yl)-[1,2,4]triazolo[1,5-a]pyrimidine was prepared in the manner described for Intermediate 18, but replacing 6-chloro-8-cyclopropyl-2-methyl-imidazo[1,2-b]pyridazine with 5-chloro-7-((1S,2S)-2-(2,4-difluorophenyl)cyclopropyl)-[1,2,4]triazolo[1,5-a]pyrimidine. ES/MS m/z: 411.1 [M+H].

Intermediate 676. 5-(2,4-dimethoxypyrimidin-5-yl)-7-((1S,2S)-2-(4-(trifluoromethyl)phenyl)cyclopropyl)-[1,2,4]triazolo[1,5-a]pyrimidine

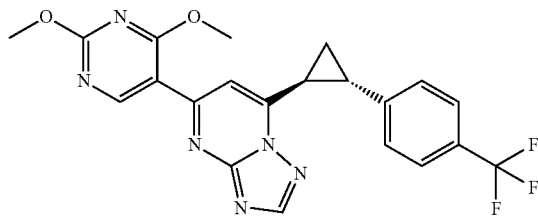 [SMILES: COc1ncc(-c2cc([C@H]3C[C@@H]3c3ccc(C(F)(F)F)cc3)n3ncnc3n2)c(OC)n1]

5-(2,4-dimethoxypyrimidin-5-yl)-7-((1S,2S)-2-(4-(trifluoromethyl)phenyl)cyclopropyl)-[1,2,4]triazolo[1,5-a]pyrimidine was prepared in the manner described for Intermediate 18, but replacing 6-chloro-8-cyclopropyl-2-methylimidazo[1,2-b]pyridazine with 5-chloro-7-((1S,2S)-2-(4-(trifluoromethyl)phenyl)cyclopropyl)-[1,2,4]triazolo[1,5-a]pyrimidine. ES/MS m/z: 443.2 [M+H].

Intermediate 677. 8-((2S,2S)-2-(4-(difluoromethyl)phenyl)cyclopropyl)-6-(2,4-dimethoxypyrimidin-5-yl)imidazo[1,2-b]pyridazine

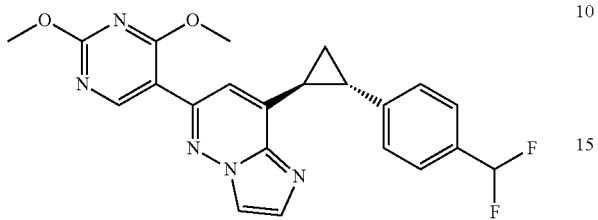

8-((1S,2S)-2-(4-(difluoromethyl)phenyl)cyclopropyl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((2S,2S)-2-(4-(difluoromethyl)phenyl)cyclopropyl)imidazo[1,2-b]pyridazine. ES/MS m/z: 424.2 [M+H].

Intermediate 678. 8-((2S,2S)-2-(4-(difluoromethyl)phenyl)cyclopropyl)-6-(2,4-dimethoxypyrimidin-5-yl)-3-fluoroimidazo[1,2-b]pyridazine

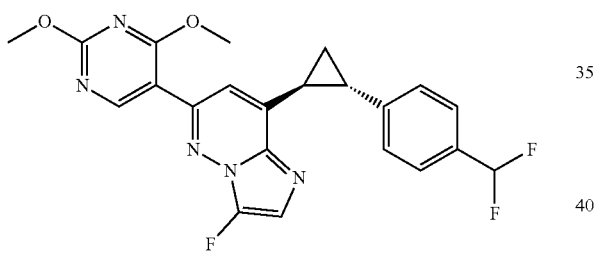

8-((1S,2S)-2-(4-(difluoromethyl)phenyl)cyclopropyl)-6-(2,4-dimethoxypyrimidin-5-yl)-3-fluoroimidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(4-(difluoromethyl)phenyl)cyclopropyl)-3-fluoroimidazo[1,2-b]pyridazine. ES/MS m/z: 442.2 [M+H].

Intermediate 679. 7-(3,3-difluoro-4,4-dimethylpyrrolidin-1-yl)-5-(2,4-dimethoxypyrimidin-5-yl)-[1,2,4]triazolo[1,5-a]pyrimidine

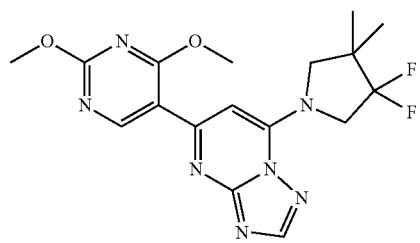 [SMILES: COc1ncc(-c2cc(N3CC(C)(C)C(F)(F)C3)n3ncnc3n2)c(OC)n1]

7-(3,3-difluoro-4,4-dimethylpyrrolidin-1-yl)-5-(2,4-dimethoxypyrimidin-5-yl)-[1,2,4]triazolo[1,5-a]pyrimidine was prepared in the manner described for Intermediate 18, but replacing 6-chloro-8-cyclopropyl-2-methyl-imidazo[1,2-b]pyridazine with 5-chloro-7-(3,3-difluoro-4,4-dimethylpyrrolidin-1-yl)-[1,2,4]triazolo[1,5-a]pyrimidine. ES/MS m/z: 392.2 [M+H].

Intermediate 680. 5-(3,3-difluoro-4,4-dimethylpyrrolidin-1-yl)-7-(2,4-dimethoxypyrimidin-5-yl)imidazo[1,2-a]pyrimidine

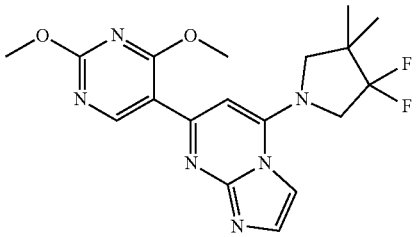 [SMILES: COc1ncc(-c2cc(N3CC(C)(C)C(F)(F)C3)n3ccnc3n2)c(OC)n1]

5-(3,3-difluoro-4,4-dimethylpyrrolidin-1-yl)-7-(2,4-dimethoxypyrimidin-5-yl)imidazo[1,2-a]pyrimidine was prepared in the manner described for Intermediate 18, but replacing 6-chloro-8-cyclopropyl-2-methyl-imidazo[1,2-b]pyridazine with 7-chloro-5-(3,3-difluoro-4,4-dimethylpyrrolidin-1-yl)imidazo[1,2-a]pyrimidine. ES/MS m/z: 391.2 [M+H].

Intermediate 681. 2-cyclopropyl-8-(3,3-difluoro-4,4-dimethylpyrrolidin-1-yl)-6-(2,4-dimethoxypyrimidin-5-yl)-3-fluoroimidazo[1,2-b]pyridazine

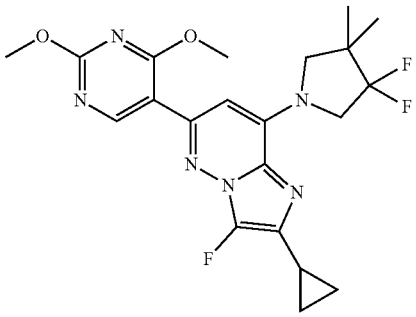 [SMILES: COc1ncc(-c2cc(N3CC(C)(C)C(F)(F)C3)c3nc(C4CC4)c(F)n3n2)c(OC)n1]

2-cyclopropyl-8-(3,3-difluoro-4,4-dimethylpyrrolidin-1-yl)-6-(2,4-dimethoxypyrimidin-5-yl)-3-fluoroimidazo[1,2-b]pyridazine was prepared in the manner described for Intermediate 18, but replacing 6-chloro-8-cyclopropyl-2-methyl-imidazo[1,2-b]pyridazine with 6-chloro-2-cyclopropyl-8-(3,3-difluoro-4,4-dimethylpyrrolidin-1-yl)-3-fluoro-imidazo[1,2-b]pyridazine. ES/MS m/z: 449.2 [M+H].

Intermediate 682. 8-(3,3-difluoro-4,4-dimethylpyr-rolidin-1-yl)-6-(2,4-dimethoxypyrimidin-5-yl)-3-fluoro-2-methylimidazo[1,2-b]pyridazine

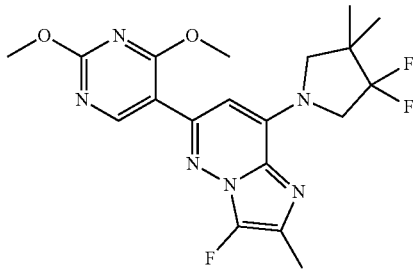 [SMILES: COc1ncc(-c2cc(N3CC(C)(C)C(F)(F)C3)c3nc(C)c(F)n3n2)c(OC)n1]

8-(3,3-difluoro-4,4-dimethylpyrrolidin-1-yl)-6-(2,4-dimethoxypyrimidin-5-yl)-3-fluoro-2-methylimidazo[1,2-b]pyridazine was prepared in the manner described for Intermediate 18, but replacing 6-chloro-8-cyclopropyl-2-methyl-imidazo[1,2-b]pyridazine with 6-chloro-8-(3,3-difluoro-4,4-dimethylpyrrolidin-1-yl)-3-fluoro-2-methylimidazo[1,2-b]pyridazine. ES/MS m/z: 423.2 [M+H].

Intermediate 683. 8-(3,3-difluoro-4,4-dimethylpyr-rolidin-1-yl)-6-(2,4-dimethoxypyrimidin-5-yl)-2-(1-(trifluoromethyl)cyclopropyl)imidazo[1,2-b]pyridazine

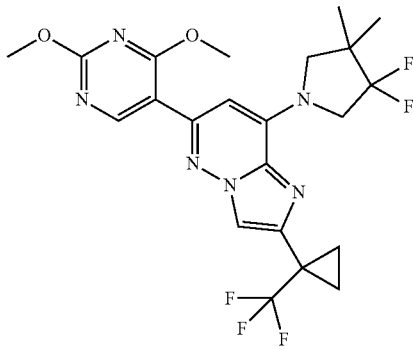 [SMILES: COc1ncc(-c2cc(N3CC(C)(C)C(F)(F)C3)c3nc(C4(C(F)(F)F)CC4)cn3n2)c(OC)n1]

8-(3,3-difluoro-4,4-dimethylpyrrolidin-1-yl)-6-(2,4-dimethoxypyrimidin-5-yl)-2-(1-(trifluoromethyl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3,3-difluoro-4,4-dimethylpyrrolidin-1-yl)-2-(1-(trifluoromethyl)cyclopropyl)imidazo[1,2-b]pyridazine. ES/MS m/z: 499.2 [M+H].

Intermediate 684. 8-(7,7-difluoro-5-azaspiro[2.4]heptan-5-yl)-6-(2,4-dimethoxypyrimidin-5-yl)-[1,2,4]triazolo[1,5-b]pyridazine

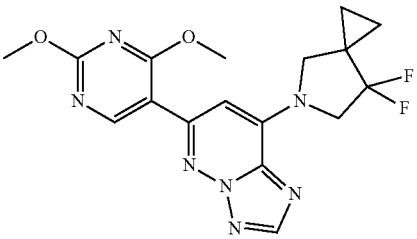 [SMILES: COc1ncc(-c2cc(N3CC(F)(F)C4(CC4)C3)c3ncnn3n2)c(OC)n1]

8-(7,7-difluoro-5-azaspiro[2.4]heptan-5-yl)-6-(2,4-dimethoxypyrimidin-5-yl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-(7,7-difluoro-5-azaspiro[2.4]heptan-5-yl)[1,2,4]triazolo[1,5-b]pyridazine. ES/MS m/z: 390.2 [M+H].

Intermediate 685. 4-((2S,2S)-2-(6-(2,4-dimethoxy-pyrimidin-5-yl)imidazo[1,2-b]pyridazin-8-yl)cyclo-propyl)-3,5-difluorobenzonitrile

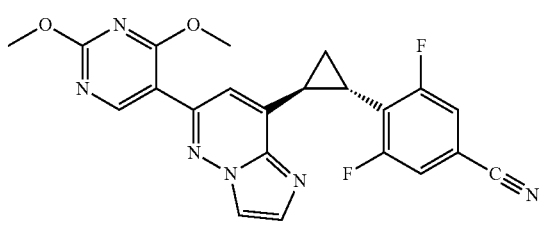 [SMILES: COc1ncc(-c2cc([C@H]3C[C@@H]3c3c(F)cc(C#N)cc3F)c3nccn3n2)c(OC)n1]

4-((1S,2S)-2-(6-(2,4-dimethoxypyrimidin-5-yl)imidazo[1,2-b]pyridazin-8-yl)cyclopropyl)-3,5-difluorobenzonitrile was prepared in the manner described for Intermediate 18, but replacing 6-chloro-8-cyclopropyl-2-methyl-imidazo[1,2-b]pyridazine with 4-((1S,2S)-2-(6-chloroimidazo[1,2-b]pyridazin-8-yl)cyclopropyl)-3,5-difluorobenzonitrile. ES/MS m/z: 435.1 [M+H].

Intermediate 686. 4-((2S,2S)-2-(6-(2,4-dimethoxy-pyrimidin-5-yl)-3-fluoroimidazo[1,2-b]pyridazin-8-yl)cyclopropyl)-3,5-difluorobenzonitrile

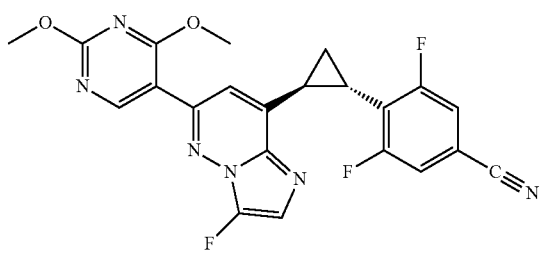 [SMILES: COc1ncc(-c2cc([C@H]3C[C@@H]3c3c(F)cc(C#N)cc3F)c3ncc(F)n3n2)c(OC)n1]

4-((2S,2S)-2-(6-(2,4-dimethoxypyrimidin-5-yl)-3-fluoro-imidazo[1,2-b]pyridazin-8-yl)cyclopropyl)-3,5-difluo-robenzonitrile was prepared in the manner described for Intermediate 18, but replacing 6-chloro-8-cyclopropyl-2-methyl-imidazo[1,2-b]pyridazine with 4-((2S,2S)-2-(6-chloro-3-fluoroimidazo[1,2-b]pyridazin-8-yl)cyclopropyl)-3,5-difluorobenzonitrile. ES/MS m/z: 453.2 [M+H].

Intermediate 687. 8-(3,3-difluoro-4,4-dimethylpyrrolidin-1-yl)-6-(2,4-dimethoxypyrimidin-5-yl)-[1,2,4]triazolo[1,5-b]pyridazine

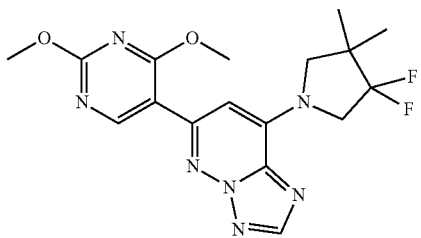 [SMILES: COc1ncc(-c2cc(N3CC(C)(C)C(F)(F)C3)c3ncnn3n2)c(OC)n1]

8-(3,3-difluoro-4,4-dimethylpyrrolidin-1-yl)-6-(2,4-dimethoxypyrimidin-5-yl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-(3,3-difluoro-4,4-dimethylpyrrolidin-1-yl)-[1,2,4]triazolo[1,5-b]pyridazine. ES/MS m/z: 392.2 [M+H].

Intermediate 688. 6-(2,4-dimethoxypyrimidin-5-yl)-8-((1S,2S)-2-(4-(trifluoromethyl)phenyl)cyclopropyl)-[1,2,4]triazolo[1,5-b]pyridazine

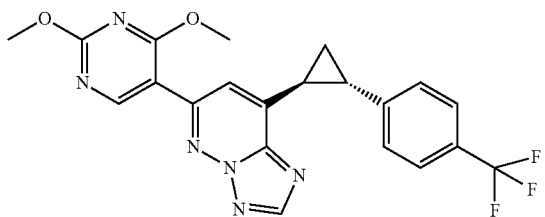 [SMILES: COc1ncc(-c2cc([C@H]3C[C@@H]3c3ccc(C(F)(F)F)cc3)c3ncnn3n2)c(OC)n1]

6-(2,4-dimethoxypyrimidin-5-yl)-8-((2S,2S)-2-(4-(trifluoromethyl)phenyl)cyclopropyl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-((2S,2S)-2-(4-(trifluoromethyl)phenyl)cyclopropyl)-[1,2,4]triazolo[1,5-b]pyridazine. ES/MS m/z: 443.2 [M+H].

Intermediate 689. 4-((2S,2S)-2-(6-(2,4-dimethoxypyrimidin-5-yl)-[1,2,4]triazolo[1,5-b]pyridazin-8-yl)cyclopropyl)-3,5-difluorobenzonitrile

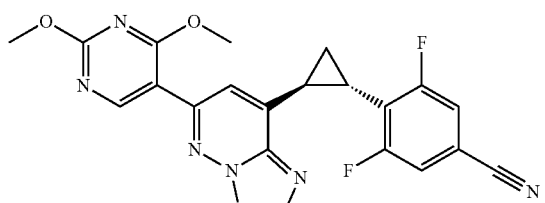

4-(1S,2S)-2-(6-(2,4-dimethoxypyrimidin-5-yl)-[1,2,4]triazolo[1,5-b]pyridazin-8-yl)cyclopropyl)-3,5-difluorobenzonitrile was prepared in the manner described for Intermediate 18, but replacing 6-chloro-8-cyclopropyl-2-methyl-imidazo[1,2-b]pyridazine with 4-((1S,2S)-2-(6-chloro-[1,2,4]triazolo[1,5-b]pyridazin-8-yl)cyclopropyl)-3,5-difluorobenzonitrile. ES/MS m/z: 436.2 [M+H].

Intermediate 690. (R)-6-(2,4-dimethoxypyrimidin-5-yl)-8-(3-(trifluoromethoxy)pyrrolidin-1-yl)-[1,2,4]triazolo[1,5-b]pyridazine

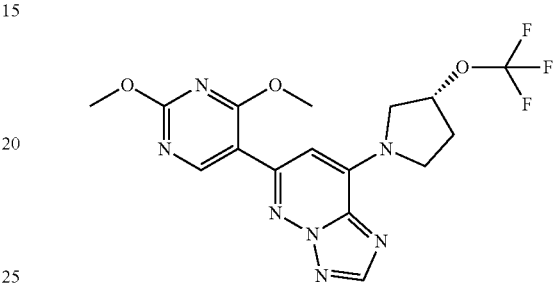

(R)-6-(2,4-dimethoxypyrimidin-5-yl)-8-(3-(trifluoromethoxy)pyrrolidin-1-yl)-[1,2,4]triazolo[1,5-b]pyridazine was prepared in the manner described for Intermediate 18, but replacing 6-chloro-8-cyclopropyl-2-methyl-imidazo[1,2-b]pyridazine with (R)-6-chloro-8-(3-(trifluoromethoxy)pyrrolidin-1-yl)-[1,2,4]triazolo[1,5-b]pyridazine. ES/MS m/z: 412.1 [M+H].

Intermediate 691. 6-(2,4-dimethoxypyrimidin-5-yl)-8-((1S,2S)-2-(1-(2,2,2-trifluoroethyl)-1H-indazol-5-yl)cyclopropyl)-[1,2,4]triazolo[1,5-b]pyridazine

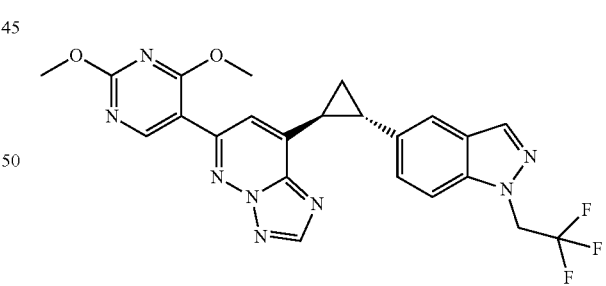

6-(2,4-dimethoxypyrimidin-5-yl)-8-((1S,2S)-2-(1-(2,2,2-trifluoroethyl)-1H-indazol-5-yl)cyclopropyl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-((1s,2S)-2-(1-(2,2,2-trifluoroethyl)-1H-indazol-5-yl)cyclopropyl)-[1,2,4]triazolo[1,5-b]pyridazine. ES/MS m/z: 497.2 [M+H].

Intermediate 692. 6-(2,4-dimethoxypyrimidin-5-yl)-8-((1S,2S)-2-(1-(2,2,2-trifluoroethyl)-1H-indazol-6-yl)cyclopropyl)-[1,2,4]triazolo[1,5-b]pyridazine

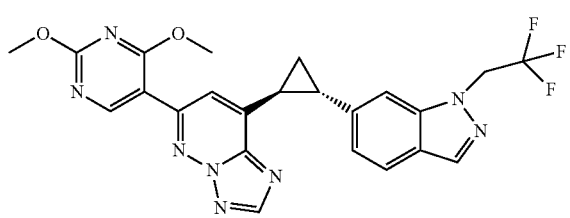 [SMILES: COc1ncc(-c2cc([C@H]3C[C@@H]3c3ccc4cnn(CC(F)(F)F)c4c3)c3ncnn3n2)c(OC)n1]

6-(2,4-dimethoxypyrimidin-5-yl)-8-((1S,2S)-2-(1-(2,2,2-trifluoroethyl)-1H-indazol-6-yl)cyclopropyl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(1-(2,2,2-trifluoroethyl)-1H-indazol-6-yl)cyclopropyl)-[1,2,4]triazolo[1,5-b]pyridazine. ES/MS m/z: 497.2 [M+H].

Intermediate 693. 8-(3,3-difluoro-4-((5-(trifluoromethyl)pyridin-2-yl)oxy)pyrrolidin-1-yl)-6-(2,4-dimethoxypyrimidin-5-yl)-[1,2,4]triazolo[1,5-b]pyridazine

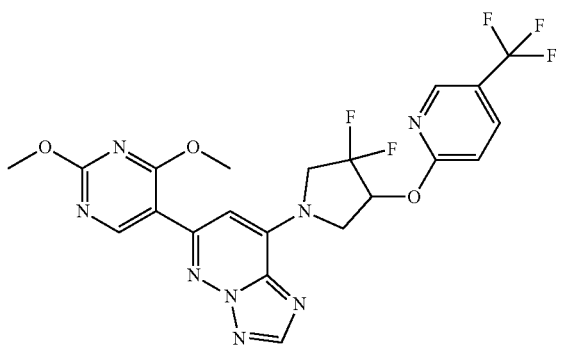 [SMILES: COc1ncc(-c2cc(N3CC(Oc4ccc(C(F)(F)F)cn4)C(F)(F)C3)c3ncnn3n2)c(OC)n1]

8-(3,3-difluoro-4-((5-(trifluoromethyl)pyridin-2-yl)oxy)pyrrolidin-1-yl)-6-(2,4-dimethoxypyrimidin-5-yl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-(3,3-difluoro-4-((5-(trifluoromethyl)pyridin-2-yl)oxy)pyrrolidin-1-yl)-[1,2,4]triazolo[1,5-b]pyridazine. ES/MS m/z: 525.2 [M+H].

Intermediate 694. 6-(2,4-dimethoxypyrimidin-5-yl)-8-(3-fluoro-3-(trifluoromethyl)azetidin-1-0)-[1,2,4]triazolo[1,5-b]pyridazine 6-(2,4-dimethoxypyrimidin-5-yl)-8-(3-fluoro-3-(trifluoromethyl)azetidin-1-yl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-(3-fluoro-3-(trifluoromethyl)azetidin-1-yl)-[1,2,4]triazolo[1,5-b]pyridazine. ES/MS m/z: 400.2 [M+H].

Intermediate 695. 6-(2,4-dimethoxypyrimidin-5-yl)-8-(3-(trifluoromethyl)-3-((5-(trifluoromethyl)pyridin-2-yl)oxy)azetidin-1-yl)imidazo[1,2-b]pyridazine

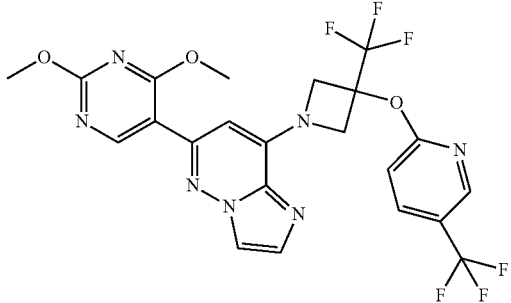 [SMILES: COc1ncc(-c2cc(N3CC(Oc4ccc(C(F)(F)F)cn4)(C(F)(F)F)C3)c3nccn3n2)c(OC)n1]

6-(2,4-dimethoxypyrimidin-5-yl)-8-(3-(trifluoromethyl)-3-((5-(trifluoromethyl)pyridin-2-yl)oxy)azetidin-1-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-(trifluoromethyl)-3-((5-(trifluoromethyl)pyridin-2-yl)oxy)azetidin-1-yl)imidazo[1,2-b]pyridazine. ES/MS m/z: 542.2 [M+H].

Intermediate 696. 6-(2,4-dimethoxypyrimidin-5-yl)-8-(3-fluoro-3-(((5-(trifluoromethyl)pyridin-2-yl)oxy)methyl)azetidin-1-yl)imidazo[1,2-b]pyridazine

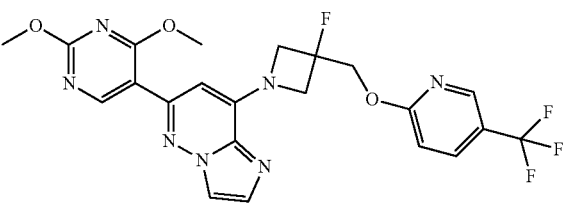 [SMILES: COc1ncc(-c2cc(N3CC(F)(COc4ccc(C(F)(F)F)cn4)C3)c3nccn3n2)c(OC)n1]

6-(2,4-dimethoxypyrimidin-5-yl)-8-(3-fluoro-3-(((5-(trifluoromethyl)pyridin-2-yl)oxy)methyl)azetidin-1-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-(3-fluoro-3-(((5-(trifluoromethyl)pyridin-2-yl)oxy)methyl)azetidin-1-yl)imidazo[1,2-b]pyridazine. ES/MS m/z: 506.2 [M+H].

Intermediate 697. 1-(6-(2,4-dimethoxypyrimidin-5-yl)-[1,2,4]triazolo[1,5-b]pyridazin-8-yl)-4,4-difluoropyrrolidin-3-yl (2,2,2-trifluoroethyl)carbamate

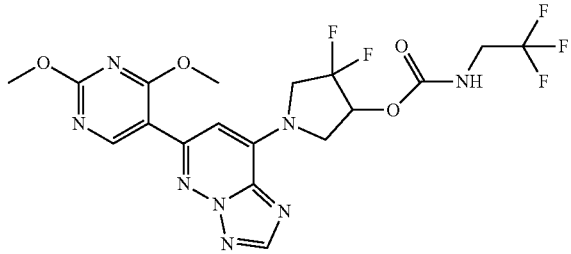 [SMILES: COc1ncc(-c2cc(N3CC(OC(=O)NCC(F)(F)F)C(F)(F)C3)c3ncnn3n2)c(OC)n1]

1-(6-(2,4-dimethoxypyrimidin-5-yl)-[1,2,4]triazolo[1,5-b]pyridazin-8-yl)-4,4-difluoropyrrolidin-3-yl (2,2,2-trifluoroethyl)carbamate was prepared in the manner described for Intermediate 18, but replacing 6-chloro-8-cyclopropyl-2-methyl-imidazo[1,2-b]pyridazine with 1-(6-chloro-[1,2,4]triazolo[1,5-b]pyridazin-8-yl)-4,4-difluoropyrrolidin-3-yl (2,2,2-trifluoroethyl)carbamate. ES/MS m/z: 505.2 [M+H].

Intermediate 698. (1-(6-(2,4-dimethoxypyrimidin-5-yl)imidazo[1,2-b]pyridazin-8-yl)-3-fluoroazetidin-3-ylmethyl (2,2,2-trifluoroethyl)carbamate

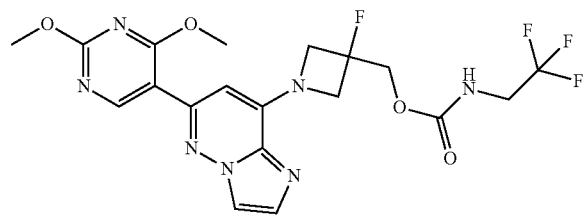 [SMILES: COc1ncc(-c2cc(N3CC(F)(COC(=O)NCC(F)(F)F)C3)c3nccn3n2)c(OC)n1]

(1-(6-(2,4-dimethoxypyrimidin-5-yl)imidazo[1,2-b]pyridazin-8-yl)-3-fluoroazetidin-3-yl)methyl (2,2,2-trifluoroethyl)carbamate was prepared in the manner described for Intermediate 18, but replacing 6-chloro-8-cyclopropyl-2-methyl-imidazo[1,2-b]pyridazine with (1-(6-chloroimidazo[1,2-b]pyridazin-8-yl)-3-fluoroazetidin-3-yl)methyl (2,2,2-trifluoroethyl)carbamate. ES/MS m/z: 486.2 [M+H].

Intermediate 699. 3-((6-(2,4-dimethoxypyrimidin-5-yl)-[1,2,4]triazolo[1,5-b]pyridazin-8-yl)oxy)-2,2-difluoropropyl (2,2,2-trifluoroethyl)carbamate

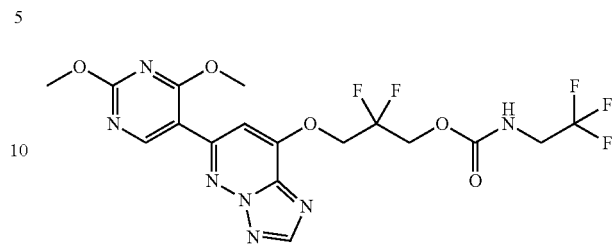

3-((6-(2,4-dimethoxypyrimidin-5-yl)-[1,2,4]triazolo[1,5-b]pyridazin-8-yl)oxy)-2,2-difluoropropyl (2,2,2-trifluoroethyl)carbamate was prepared in the manner described for Intermediate 18, but replacing 6-chloro-8-cyclopropyl-2-methyl-imidazo[1,2-b]pyridazine with 3-((6-chloro-[1,2,4]triazolo[1,5-b]pyridazin-8-yl)oxy)-2,2-difluoropropyl isopropylcarbamate. ES/MS m/z: 454.2 [M+H].

Intermediate 700. 8-((2S,2S)-2-(5-chloropyridin-2-yl)cyclopropyl)-6-(2,4-dimethoxypyrimidin-5-yl)-[1,2,4]triazolo[1,5-b]pyridazine

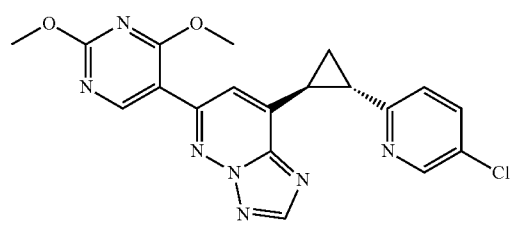 [SMILES: COc1ncc(-c2cc([C@H]3C[C@@H]3c3ccc(Cl)cn3)c3ncnn3n2)c(OC)n1]

8-((1S,2S)-2-(5-chloropyridin-2-yl)cyclopropyl)-6-(2,4-dimethoxypyrimidin-5-yl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(5-chloropyridin-2-yl)cyclopropyl)-[1,2,4]triazolo[1,5-b]pyridazine. ES/MS m/z: 410.0 [M+H].

Intermediate 701. (1-(6-(2,4-dimethoxypyrimidin-5-yl)imidazo[1,2-b]pyridazin-8-yl)-3-fluoroazetidin-3-yl)methanol

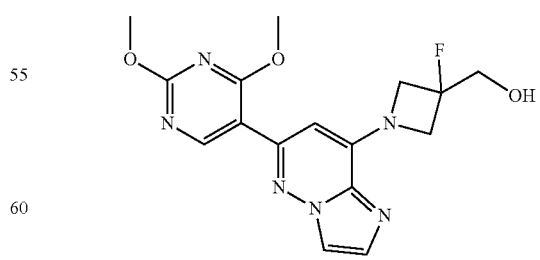

(1-(6-(2,4-dimethoxypyrimidin-5-yl)imidazo[1,2-b]pyridazin-8-yl)-3-fluoroazetidin-3-yl)methanol was prepared as follows: To a solution of 8-bromo-6-(2,4-dimethoxypyrimidin-5-yl)imidazo[1,2-b]pyridazine (150 mg, 0.446 mmol) and (3-fluoroazetidin-3-yl)methanol (70 mg, 0.669 mmol) in NMP (2 mL) was added DIPEA (0.117 mL, 0.669 mmol), and the mixture heated to 120° C. for 2 h. The mixture was then cooled, diluted with EtOAc, and washed with brine. Organics were dried over MgSO$_4$, filtered, and concentrated. The resulting residue was purified by silica gel chromatography (0-20% MeOH/DCM) to afford (1-(6-(2,4-dimethoxypyrimidin-5-yl)imidazo[1,2-b]pyridazin-8-yl)-3-fluoroazetidin-3-yl)methanol. ES/MS m/z: 361.2 [M+H].

Intermediate 702. 5-(8-bromo-3-chloroimidazo[1,2-b]pyridazin-6-yl)pyrimidine-2,4(1H,3H)-dione

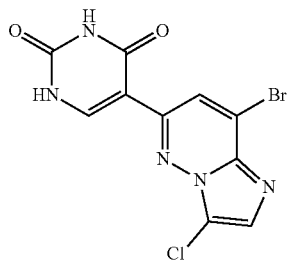 [SMILES: O=c1[nH]cc(-c2cc(Br)c3ncc(Cl)n3n2)c(=O)[nH]1]

5-(8-bromo-3-chloroimidazo[1,2-b]pyridazin-6-yl)pyrimidine-2,4(1H,3H)-dione was prepared as follows: To a mixture of 5-(8-bromoimidazo[1,2-b]pyridazin-6-yl)pyrimidine-2,4(1H,3H)-dione (100 mg, 0.290 mmol) and N-chlorosuccinimide (37 mg, 0.276 mmol) in DMF (1 mL) was added DIPEA (0.076 mL, 0.435 mmol). The mixture was stirred 30° C. for 16 h, after which aqueous Na$_2$SO$_3$ and water were added. The mixture was stirred for 2 min, then filtered, rinsing with MeCN/water. Solids were dried in vacuo to afford 5-(8-bromo-3-chloroimidazo[1,2-b]pyridazin-6-yl)pyrimidine-2,4(1H,3H)-dione. ES/MS m/z: 341.9 [M+H]. $^1$H NMR (400 MHz, DMSO-d6) δ 11.59 (s, 2H), 8.24 (s, 1H), 8.11 (s, 1H), 7.97 (s, 1H).

Intermediate 703. 6-bromo-3-chloro-1-(2,2,2-trifluoroethyl)-1H-indazole

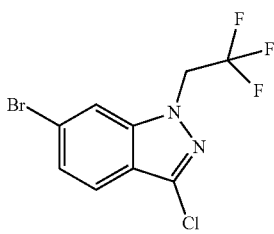 [SMILES: FC(F)(F)Cn1nc(Cl)c2ccc(Br)cc21]

To a mixture of 6-bromo-3-chloro-1H-indazole (500 mg, 2.16 mmol) and cesium carbonate (704 mg, 2.16 mmol) was added 2,2,2-trifluoroethyl trifluoromethanesulfonate (0.358 mL, 2.48 mmol). The mixture was stirred at room temperature for 16 h, then diluted with EtOAc and washed twice with brine. Combined organics were dried over MgSO$_4$, filtered, and concentrated. The resulting residue was purified by silica gel chromatography (0-100% EtOAc/hexanes) to afford 6-bromo-3-chloro-1-(2,2,2-trifluoroethyl)-1H-indazole. $^1$H NMR (400 MHz, Chloroform-d) δ 7.62-7.54 (m, 2H), 7.40 (dd, J=8.6, 1.4 Hz, 1H), 4.84 (q, J=8.3 Hz, 2H).

Intermediate 704. 6-bromo-4-chloro-1-(2,2,2-trifluoroethyl)-1H-indazole

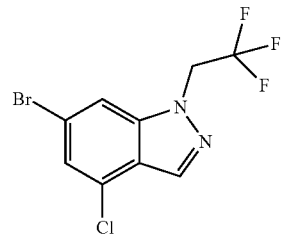 [SMILES: FC(F)(F)Cn1ncc2c(Cl)cc(Br)cc21]

6-bromo-4-chloro-1-(2,2,2-trifluoroethyl)-1H-indazole was prepared in the manner described for Intermediate 703, but replacing 6-bromo-3-chloro-1H-indazole with 6-bromo-4-chloro-1H-indazole. $^1$H NMR (400 MHz, Chloroform-d) δ 8.13 (d, J=1.0 Hz, 1H), 7.53 (s, 1H), 7.36 (d, J=1.3 Hz, 1H), 4.90 (q, J=8.3 Hz, 2H).

Intermediate 705. 1,3-dioxoisoindolin-2-yl (1S,2S)-2-(3-chloro-1-(2,2,2-trifluoroethyl)-1H-indazol-6-yl)cyclopropane-1-carboxylate

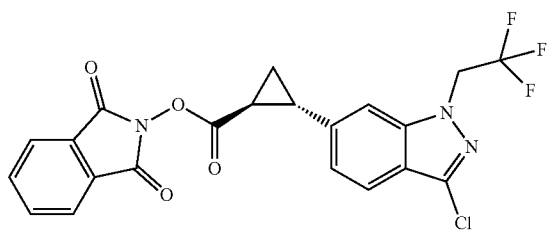 [SMILES: O=C(ON1C(=O)c2ccccc2C1=O)[C@H]1C[C@@H]1c1ccc2c(Cl)nn(CC(F)(F)F)c2c1]

1,3-dioxoisoindolin-2-yl(1S,2S)-2-(3-chloro-1-(2,2,2-trifluoroethyl)-1H-indazol-6-yl)cyclopropane-1-carboxylate was prepared in the manner described for Steps 1 and 2 of Intermediate 72, but replacing 5-bromo-2-chlorobenzonitrile with 6-bromo-3-chloro-1-(2,2,2-trifluoroethyl)-1H-indazole, and running Step 1 at 70° C. ES/MS m/z: 464.1 [M+H].

Intermediate 706. 3-chloro-6-((2S,2S)-2-(4,4,5,5-tetramethyl-1,3,2-dioxaborolan-2-yl)cyclopropyl)-1-(2,2,2-trifluoroethyl)-1H-indazole

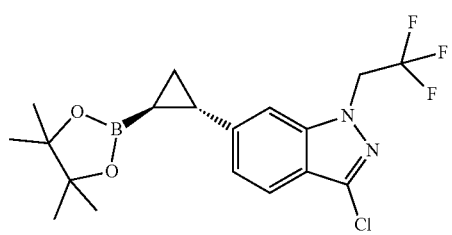 [SMILES: CC1(C)OB([C@H]2C[C@@H]2c2ccc3c(Cl)nn(CC(F)(F)F)c3c2)OC1(C)C]

3-chloro-6-((2S,2S)-2-(4,4,5,5-tetramethyl-1,3,2-dioxaborolan-2-yl)cyclopropyl)-1-(2,2,2-trifluoroethyl)-1H-indazole was prepared as follows: To a solution of 1,3-dioxoisoindolin-2-yl (1S,2S)-2-(3-chloro-1-(2,2,2-trifluoroethyl)-1H-indazol-6-yl)cyclopropane-1-carboxylate (385 mg, 0.830 mmol) and B2pin2 (632 mg, 2.49 mmol) in trifluorotoluene (4 mL) was added tert-butyl isonicotinate (0.071 mL, 0.415 mmol). The mixture was heated to 105° C. for 5 h, then cooled to room temperature, concentrated in vacuo, and the resulting residue purified by silica gel chromatography (0-100% EtOAc/hexanes) to afford 3-chloro-6-((1S,2S)-2-(4,4,5,5-tetramethyl-1,3,2-dioxaborolan-2-yl)cyclopropyl)-1-(2,2,2-trifluoroethyl)-1H-indazole. ES/MS m/z: 401.2 [M+H].

Intermediate 707. 1,3-dioxoisoindolin-2-yl (1S,2S)-2-(4-chloro-1-(2,2,2-trifluoroethyl)-1H-indazol-6-yl)cyclopropane-1-carboxylate

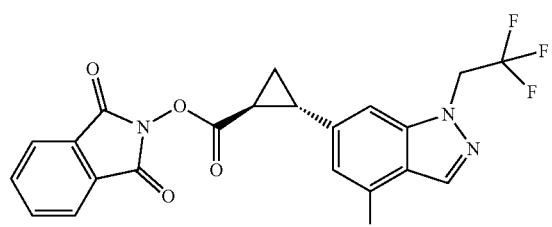

1,3-dioxoisoindolin-2-yl (1S,2S)-2-(4-chloro-1-(2,2,2-trifluoroethyl)-1H-indazol-6-yl)cyclopropane-1-carboxylate was prepared in the manner described for Steps 1 and 2 of Intermediate 72, but replacing 5-bromo-2-chlorobenzonitrile with 6-bromo-4-chloro-1-(2,2,2-trifluoroethyl)-1H-indazole, and running Step 1 at 70° C. ES/MS m/z: 464.1 [M+H].

Intermediate 708. 4-chloro-6-((2S,2S)-2-(4,4,5,5-tetramethyl-1,3,2-dioxaborolan-2-yl)cyclopropyl)-1-(2,2,2-trifluoroethyl)-1H-indazole

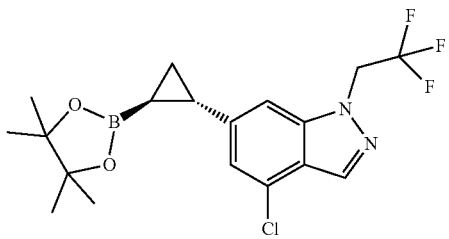 [SMILES: CC1(C)OB([C@H]2C[C@@H]2c2cc(Cl)c3cnn(CC(F)(F)F)c3c2)OC1(C)C]

4-chloro-6-((2S,2S)-2-(4,4,5,5-tetramethyl-1,3,2-dioxaborolan-2-yl)cyclopropyl)-1-(2,2,2-trifluoroethyl)-1H-indazole was prepared in the manner described for Intermediate 706, but replacing 1,3-dioxoisoindolin-2-yl (1S,2S)-2-(3-chloro-1-(2,2,2-trifluoroethyl)-1H-indazol-6-yl)cyclopropane-1-carboxylate with 1,3-dioxoisoindolin-2-yl (1S,2S)-2-(4-chloro-1-(2,2,2-trifluoroethyl)-1H-indazol-6-yl)cyclopropane-1-carboxylate. ES/MS m/z: 401.1 [M+H].

Intermediate 709. Potassium trifluoro((1S,2S)-2-(1-(2,2,2-trifluoroethyl)-1H-indazol-6-yl)cyclopropyl)borate

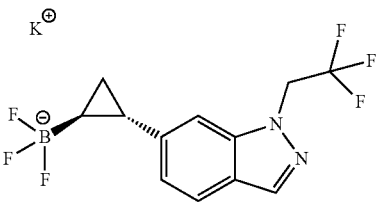 [SMILES: [K+] ; F[B-](F)(F)[C@H]1C[C@@H]1c1ccc2cnn(CC(F)(F)F)c2c1]

Potassium trifluoro((2S,2S)-2-(1-(2,2,2-trifluoroethyl)-1H-indazol-6-yl)cyclopropyl)borate was prepared in the manner described for Intermediate 448, but replacing 4,4,5,5-tetramethyl-2-((1S,2S)-2-(4-(trifluoromethyl)phenyl)cyclopropyl)-1,3,2-dioxaborolane with 6-((1S,2S)-2-(4,4,5,5-tetramethyl-1,3,2-dioxaborolan-2-yl)cyclopropyl)-1-(2,2,2-trifluoroethyl)-1H-indazole. ¹H NMR (400 MHz, Acetone-d6) δ 7.92 (d, J=1.0 Hz, 1H), 7.53 (d, J=8.4 Hz, 1H), 7.26 (s, 1H), 6.87 (dd, J=8.4, 1.3 Hz, 1H), 5.21 (q, J=9.0 Hz, 2H), 1.80-1.72 (m, 1H), 0.85 (td, J=7.4, 2.6 Hz, 1H), 0.52 (d, J=10.2 Hz, 1H), 0.09-0.02 (m, 1H). ¹⁹F NMR (376 MHz, Acetone-d6) δ −71.97 (t, J=9.0 Hz), −145.46 (d, J=77.9 Hz).

Intermediate 710. 5-bromo-7-((2S,2S)-2-(1-(2,2,2-trifluoroethyl)-1H-indazol-6-yl)cyclopropyl)pyrazolo[1,5-a]pyrimidine

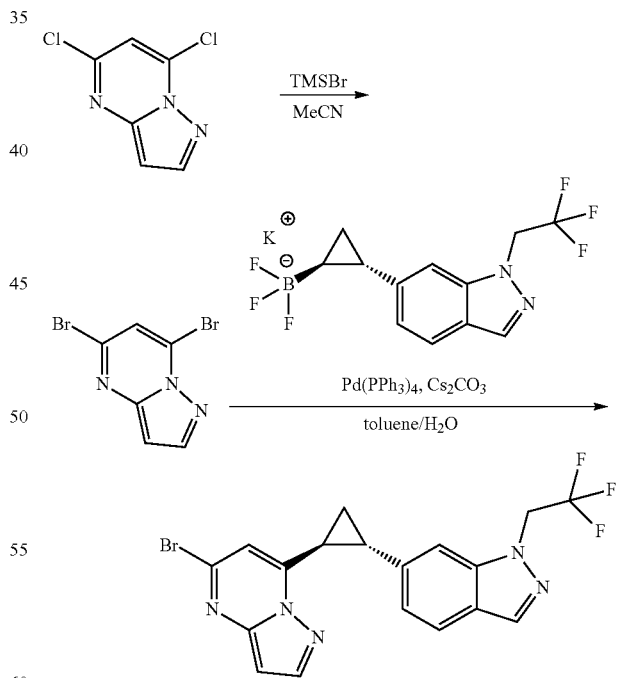

5-bromo-74(1S,2S)-2-(1-(2,2,2-trifluoroethyl)-1H-indazol-6-yl)cyclopropyl)pyrazolo[1,5-a]pyrimidine was prepared as follows: To a solution of 5,7-dichloropyrazolo[1,5-a]pyrimidine (0.500 g, 2.66 mmol) in MeCN (13 mL) was added bromotrimethylsilane (1.75 mL, 13.3 mmol). The mixture was stirred at 60° C. for 3 h. The suspension was filtered, washing with MeCN, and the solids were dried under vacuum to afford 5,7-dibromopyrazolo[1,5-a]pyrimidine. ES/MS m/z: 276.0 [M+H].

A microwave vial was charged with 5,7-dibromopyrazolo[1,5-a]pyrimidine (354 mg, 1.28 mmol), potassium trifluoro((2S,2S)-2-(1-(2,2,2-trifluoroethyl)-1H-indazol-6-yl)cyclopropyl)borate (295 mg, 0.852 mmol), cesium carbonate (833 mg, 2.56 mmol), and Pd(PPh$_3$)$_4$ (49 mg, 0.043 mmol). The solids were dissolved in toluene (5 mL) and H$_2$O (1 mL), and the mixture was degassed with N$_2$. The vial was sealed and heated to 100° C. for 5 h. The reaction mixture was then cooled and filtered through celite, washing with EtOAc. The filtrate was concentrated in vacuo, and the resulting residue purified by silica gel chromatography (0-100% EtOAc/hexanes), affording 5-bromo-7-((2S,2S)-2-(1-(2,2,2-trifluoroethyl)-1H-indazol-6-yl)cyclopropyl)pyrazolo[1,5-a]pyrimidine. ES/MS m/z: 436.1 [M+H].

Intermediate 711. 5-((6-chloroimidazo[1,2-b]pyridazin-8-yl)oxy)-4,4-difluoropentanoic acid

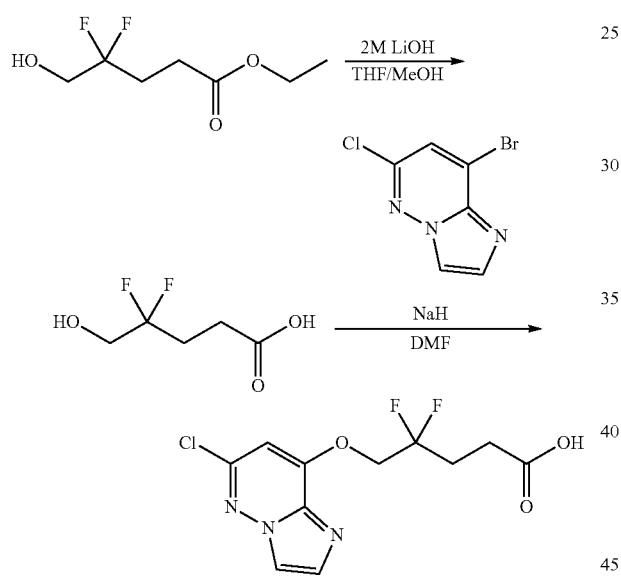

To a solution of ethyl 4,4-difluoro-5-hydroxy-pentanoate (500 mg, 2.74 mmol) in THF (8 mL) and MeOH (4 mL) was added 2 M LiOH (4 mL, 8 mmol). The mixture was stirred overnight, allowing to warm to room temperature, then diluted with water and washed with EtOAc. Aqueous phase was acidified using 2 M HCl, then extracted twice with EtOAc. Combined organics were dried over MgSO$_4$, filtered, and concentrated in vacuo to afford 4,4-difluoro-5-hydroxypentanoic acid, which was used without further purification.

To a solution of 4,4-difluoro-5-hydroxypentanoic acid (423 mg, 2.74 mmol) in DMF (10 mL) at 0° C. was added NaH (231 mg, 6.04 mmol). The mixture was stirred for 20 min, after which 8-bromo-6-chloro-imidazo[1,2-b]pyridazine (638 mg, 2.74 mmol) was added. The mixture was stirred for 2 h, allowing to warm to room temperature, then quenched with water and washed with EtOAc. Aqueous phase was acidified using 2 M HCl, then extracted twice with EtOAc. Combined organics were dried over MgSO$_4$, filtered, and concentrated in vacuo to afford 5-((6-chloroimidazo[1,2-b]pyridazin-8-yl)oxy)-4,4-difluoropentanoic acid, which was used without further purification. ES/MS m/z: 305.5 [M+H].

Intermediate 712. 5-((6-chloroimidazo[1,2-b]pyridazin-8-yl)oxy)-4,4-difluoro-N-isopropylpentanamide

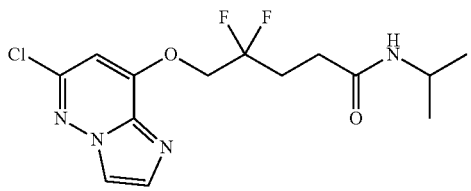 [SMILES: CC(C)NC(=O)CCC(F)(F)COc1cc(Cl)nn2ccnc12]

5-((6-chloroimidazo[1,2-b]pyridazin-8-yl)oxy)-4,4-difluoro-N-isopropylpentanamide was prepared as follows: To a solution of 54(6-chloroimidazo[1,2-b]pyridazin-8-yl)oxy)-4,4-difluoropentanoic acid (75 mg, 0.245 mmol) and HATU (112 mg, 0.294 mmol) in DMF (1 mL) was added isopropylamine (0.032 mL, 0.368 mmol), followed by DIPEA (0.128 mL, 0.736 mmol). The mixture was stirred at room temperature for 16 h, then diluted with EtOAc and washed twice with brine. Combined organics were then dried over MgSO$_4$, filtered, and concentrated in vacuo. The resulting residue was purified by silica gel chromatography (0-100% EtOAc/hexanes) to afford 5-((6-chloroimidazo[1,2-b]pyridazin-8-yl)oxy)-4,4-difluoro-N-isopropylpentanamide. ES/MS m/z: 347.1 [M+H].

Intermediate 713. 5-((6-chloroimidazo[1,2-b]pyridazin-8-yl)oxy)-4,4-difluoro-N-(2,2,2-trifluoroethyl)pentanamide

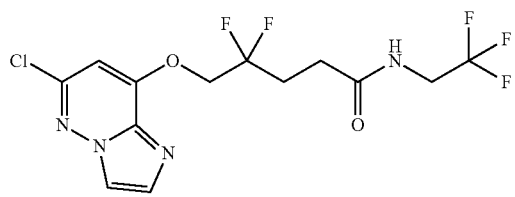 [SMILES: O=C(CCC(F)(F)COc1cc(Cl)nn2ccnc12)NCC(F)(F)F]

5-((6-chloroimidazo[1,2-b]pyridazin-8-yl)oxy)-4,4-difluoro-N-(2,2,2-trifluoroethyl)pentanamide was prepared in the manner described for Intermediate 712, but replacing isopropylamine with 2,2,2-trifluoroethanamine. ES/MS m/z: 387.1 [M+H].

Intermediate 714. 6-chloro-8-((2S,2S)-2-(3-chloro-1-(2,2,2-trifluoroethyl)-1H-indazol-6-yl)cyclopropyl)imidazo[1,2-b]pyridazine

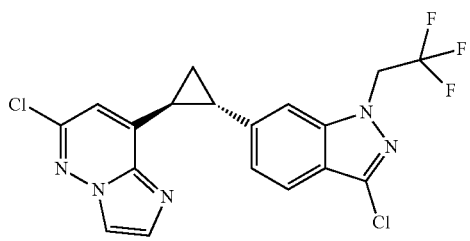 [SMILES: FC(F)(F)Cn1nc(Cl)c2ccc([C@H]3C[C@@H]3c3cc(Cl)nn4ccnc34)cc21]

6-chloro-8-((2S,2S)-2-(3-chloro-1-(2,2,2-trifluoroethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 3-chloro-6-((2S,2S)-2-(4,4,5,5-tetramethyl-1,3,2-dioxaborolan-2-yl)cyclopropyl)-1-(2,2,2-trifluoroethyl)-1H-indazole, and running the reaction at 90° C. for 16 h. ES/MS m/z: 426.1 [M+H].

Intermediate 715. 6-chloro-8-((2S,2S)-2-(4-chloro-1-(2,2,2-trifluoroethyl)-1H-indazol-6-yl)cyclopropyl)imidazo[1,2-b]pyridazine

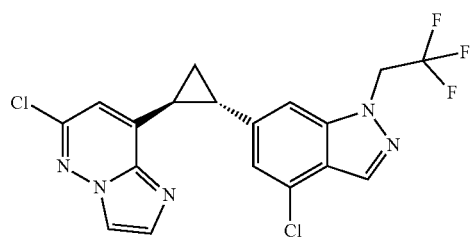 [SMILES: FC(F)(F)Cn1ncc2c(Cl)cc([C@H]3C[C@@H]3c3cc(Cl)nn4ccnc34)cc21]

6-chloro-8-((2S,2S)-2-(4-chloro-1-(2,2,2-trifluoroethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 4-chloro-6-((2S,2S)-2-(4,4,5,5-tetramethyl-1,3,2-dioxaborolan-2-yl)cyclopropyl)-1-(2,2,2-trifluoroethyl)-1H-indazole, and running the reaction at 90° C. for 16 h. ES/MS m/z: 426.0 [M+H].

Intermediate 716. 5-((6-(2,4-dimethoxypyrimidin-5-yl)imidazo[1,2-b]pyridazin-8-yl)oxy)-4,4-difluoro-N-isopropylpentanamide

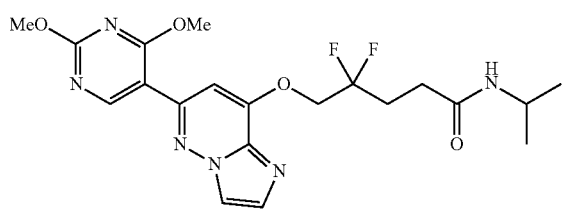 [SMILES: COc1ncc(-c2cc(OCC(F)(F)CCC(=O)NC(C)C)c3nccn3n2)c(OC)n1]

5-((6-(2,4-dimethoxypyrimidin-5-yl)imidazo[1,2-b]pyridazin-8-yl)oxy)-4,4-difluoro-N-isopropylpentanamide was prepared in the manner described for Intermediate 18, but replacing 6-chloro-8-cyclopropyl-2-methyl-imidazo[1,2-b]pyridazine with 5-((6-chloroimidazo[1,2-b]pyridazin-8-yl)oxy)-4,4-difluoro-N-isopropylpentanamide. ES/MS m/z: 451.2 [M+H].

Intermediate 717. 5-((6-(2,4-dimethoxypyrimidin-5-yl)imidazo[1,2-b]pyridazin-8-yl)oxy)-4,4-difluoro-N-(2,2,2-trifluoroethyl)pentanamide

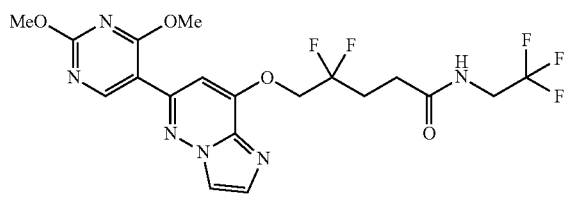 [SMILES: COc1ncc(-c2cc(OCC(F)(F)CCC(=O)NCC(F)(F)F)c3nccn3n2)c(OC)n1]

5-((6-(2,4-dimethoxypyrimidin-5-yl)imidazo[1,2-b]pyridazin-8-yl)oxy)-4,4-difluoro-N-(2,2,2-trifluoroethyl)pentanamide was prepared in the manner described for Intermediate 18, but replacing 6-chloro-8-cyclopropyl-2-methyl-imidazo[1,2-b]pyridazine with 5-((6-chloroimidazo[1,2-b]pyridazin-8-yl)oxy)-4,4-difluoro-N-(2,2,2-trifluoroethyl)pentanamide. ES/MS m/z: 491.1 [M+H].

Intermediate 718. 8-((2S,2S)-2-(3-chloro-1-(2,2,2-trifluoroethyl)-1H-indazol-6-yl)cyclopropyl)-6-(2,4-dimethoxypyrimidin-5-yl)imidazo[1,2-b]pyridazine

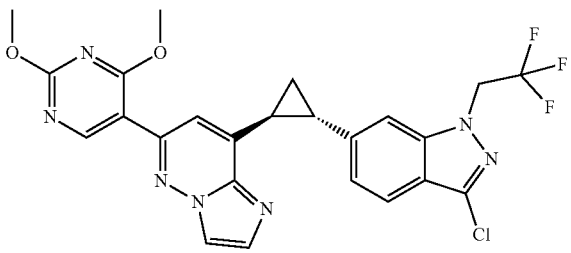 [SMILES: COc1ncc(-c2cc([C@H]3C[C@@H]3c3ccc4c(Cl)nn(CC(F)(F)F)c4c3)c3nccn3n2)c(OC)n1]

8-((1S,2S)-2-(3-chloro-1-(2,2,2-trifluoroethyl)-1H-indazol-6-yl)cyclopropyl)-6-(2,4-dimethoxypyrimidin-5-yl)imidazo[1,2-b]pyridazine was prepared as follows: 6-chloro-8-((1S,2S)-2-(3-chloro-1-(2,2,2-trifluoroethyl)-1H-indazol-6-yl)cyclopropyl)imidazo[1,2-b]pyridazine (40 mg, 0.0938 mmol), cesium carbonate (61 mg, 0.118 mmol), and Pd(dppf)Cl$_2$—CH$_2$Cl$_2$ (8 mg, 0.00938 mmol) were weighed into a microwave vial, and dioxane (0.4 mL) and water (0.2 mL) were added. The mixture was degassed with N$_2$, then the vial was sealed and heated to 70° C. In a separate vial, (2,4-dimethoxypyrimidin-5-yl)boronic acid (26 mg, 0.141 mmol) was sonicated with dioxane (0.4 mL), and the mixture degassed with N$_2$. The suspension was then added dropwise to the heated solution of aryl chloride, catalyst, and base, over the span of 45 min. The mixture was stirred at 70° C. for an additional 30 min, then cooled to room temperature and filtered through celite, washing with DCM. The filtrate was concentrated in vacuo and purified by silica gel chromatography (0-20% MeOH/DCM) to afford 8-((1S,2S)-2-(3-chloro-1-(2,2,2-trifluoroethyl)-1H-indazol-6-yl)cyclopropyl)-6-(2,4-dimethoxypyrimidin-5-yl)imidazo[1,2-b]pyridazine. ES/MS m/z: 530.2 [M+H].

Intermediate 719. 8-((2S,2S)-2-(4-chloro-1-(2,2,2-trifluoroethyl)-1H-indazol-6-yl)cyclopropyl)-6-(2,4-dimethoxypyrimidin-5-yl)imidazo[1,2-b]pyridazine

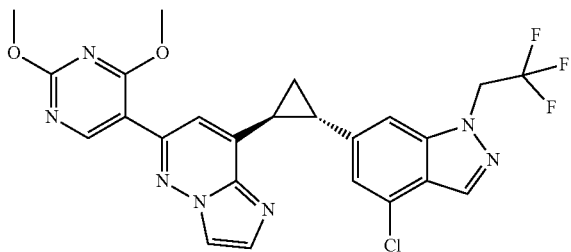 [SMILES: COc1ncc(-c2cc([C@H]3C[C@@H]3c3cc(Cl)c4cnn(CC(F)(F)F)c4c3)c3nccn3n2)c(OC)n1]

8-((1S,2S)-2-(4-chloro-1-(2,2,2-trifluoroethyl)-1H-indazol-6-yl)cyclopropyl)-6-(2,4-dimethoxypyrimidin-5-yl)imidazo[1,2-b]pyridazine was prepared in the manner described for Intermediate 718, but replacing 6-chloro-8-((1S,2S)-2-(3-chloro-1-(2,2,2-trifluoroethyl)-1H-indazol-6-yl)cyclopropyl)imidazo[1,2-b]pyridazine with 6-chloro-8-((1S,2S)-2-(4-chloro-1-(2,2,2-trifluoroethyl)-1H-indazol-6-yl)cyclopropyl)imidazo[1,2-b]pyridazine. ES/MS m/z: 530.2 [M+H].

Intermediate 720. (S)-4,4-difluoropyrrolidin-3-ol hydrochloride

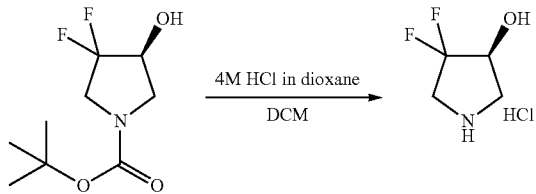

(S)-4,4-difluoropyrrolidin-3-ol hydrochloride was prepared as follows: To a solution of tert-butyl (S)-3,3-difluoro-4-hydroxypyrrolidine-1-carboxylate (5.20 g, 23.3 mmol, 1 equiv) in DCM (20.0 mL) was gradually added 4.0 M HCl in dioxane (16.0 mL, 64.0 mmol, 2.75 equiv). The reaction mixture was stirred at room temperature overnight. The solution was concentrated in vacuo to afford the title compound in quantitative yield. 1H NMR (400 MHz, DMSO-d6) δ 10.21 (s, 2H), 6.68-6.51 (m, 1H), 4.36-4.24 (m, 1H), 3.71-3.12 (m, 4H). 19F NMR (376 MHz, DMSO-d6) δ −106.08−−107.51 (m), −120.49−−122.00 (m).

Intermediate 721. (S)-1-(6-chloroimidazo[1,2-b]pyridazin-8-yl)-4,4-difluoropyrrolidin-3-ol

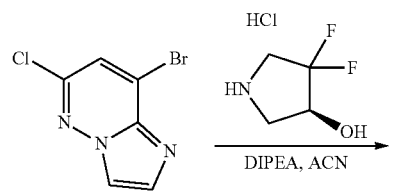

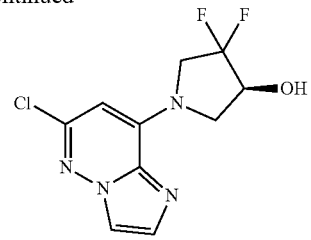

(S)-1-(6-chloroimidazo[1,2-b]pyridazin-8-yl)-4,4-difluoropyrrolidin-3-ol was prepared as follows: A solution of 8-bromo-6-chloroimidazo[1,2-b]pyridazine (3.64 g, 15.7 mmol, 1 equiv), (S)-4,4-difluoropyrrolidin-3-ol hydrochloride (2.50 g, 15.7 mmol, 1 equiv) and DIPEA (6.55 mL, 37.6 mmol, 2.4 equiv) in ACN (50.0 mL) was stirred at 85° C. for 7 h. The solution was diluted with water (150 mL) and extracted with EtOAc (3×100 mL). The organic fractions were combined, dried over Na₂SO₄, filtered and concentrated in vacuo. The crude material was loaded onto Celite and purified by silica gel chromatography (0-100% EtOAc in hexanes). ES/MS m/z: 275.0 [M+H].

Intermediate 722. (S)-1-(6-(2,4-dimethoxypyrimidin-5-yl)imidazo[1,2-b]pyridazin-8-yl)-4,4-difluoropyrrolidin-3-ol

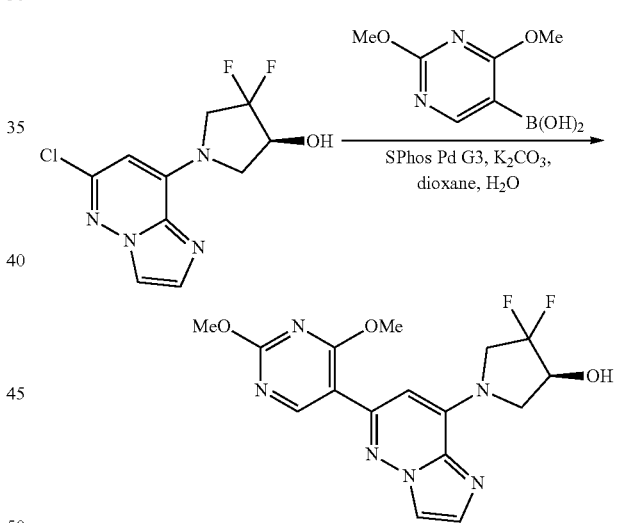

(S)-1-(6-(2,4-dimethoxypyrimidin-5-yl)imidazo[1,2-b]pyridazin-8-yl)-4,4-difluoropyrrolidin-3-ol was prepared as follows: A 500 mL round-bottom flask was charged with (2,4-dimethoxypyrimidin-5-yl)boronic acid (2.54 g, 13.8 mmol, 1.2 equiv), SPhos Pd G3 (350 mg, 0.449 mmol, 0.039 equiv) and potassium carbonate (3.18 g, 23.0 mmol, 2 equiv). To this was added (S)-1-(6-chloroimidazo[1,2-b]pyridazin-8-yl)-4,4-difluoropyrrolidin-3-ol (3.16 g, 11.5 mmol, 1 equiv) dissolved in 1,4 dioxane (60.0 mL). This was followed by the addition of water (10.0 mL). The reaction mixture was heated to 85° C. and stirred under Argon overnight. After cooling to room temperature, the solution was diluted with water (150 mL) and extracted with EtOAc (2×150 mL). The organic fractions were combined, dried over Na₂SO₄, filtered and concentrated in vacuo. The crude material was loaded onto Celite and purified by silica gel chromatography (0-100% EtOAc in hexanes) to afford the title compound. ES/MS m/z: 379.0 [M+H]. 1H NMR (400 MHz, DMSO-d6) δ 8.57 (s, 1H), 8.12 (d, J=1.2 Hz, 1H), 7.59 (d, J=1.2 Hz, 1H), 6.28-6.23 (m, 2H), 4.54-4.06 (m, 5H), 4.00-3.96 (m, 6H). 19F NMR (376 MHz, DMSO-d6) δ −109.29−−111.10 (m), −122.68 (d, J=233.0 Hz).

Intermediate 723. (S)-4-((1-(6-(2,4-dimethoxypyrimidin-5-yl)imidazo[1,2-b]pyridazin-8-yl)-4,4-difluoropyrrolidin-3-yl)oxy)-2-(trifluoromethyl)benzonitrile

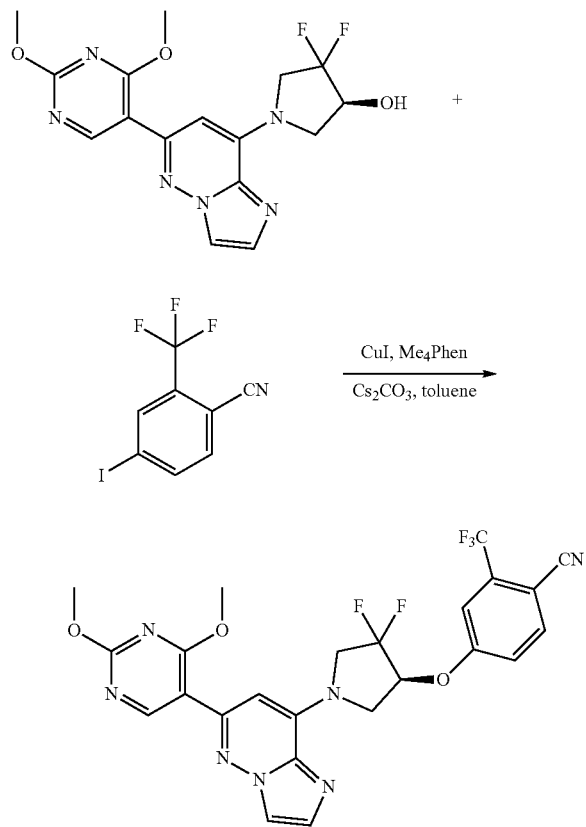

(S)-4-((1-(6-(2,4-dimethoxypyrimidin-5-yl)imidazo[1,2-b]pyridazin-8-yl)-4,4-difluoropyrrolidin-3-yl)oxy)-2-(trifluoromethyl)benzonitrile was prepared as follows: A microwave vial was charged with copper(I) iodide (41 mg, 0.215 mmol, 1.63 equiv), 3,4,7,8-tetramethyl-1,10-phenanthroline (6 mg, 0.026 mmol, 0.2 equiv), cesium carbonate (65 mg, 0.198 mmol, 1.5 equiv), (S)-1-(6-(2,4-dimethoxypyrimidin-5-yl)imidazo[1,2-b]pyridazin-8-yl)-4,4-difluoropyrrolidin-3-ol (50 mg, 0.132 mmol, 1 equiv) and 4-iodo-2-(trifluoromethyl)benzonitrile (43 mg, 0.145 mmol, 1.1 equiv). The vial was sealed and toluene (3.0 mL) was added under an Argon atmosphere. The reaction mixture was gradually heated to 120° C. and stirred overnight. After cooling to room temperature, the mixture was diluted with EtOAc and filtered through a pad of Celite. The filtrate was concentrated under reduced pressure and the crude material was purified by silica gel chromatography (0-100% EtOAc in hexanes) to afford the title compound. ES/MS m/z: 548.0 [M+H].

Intermediate 724. (S)-1-(5-chloropyrazolo[1,5-a]pyrimidin-7-yl)-4,4-difluoropyrrolidin-3-ol

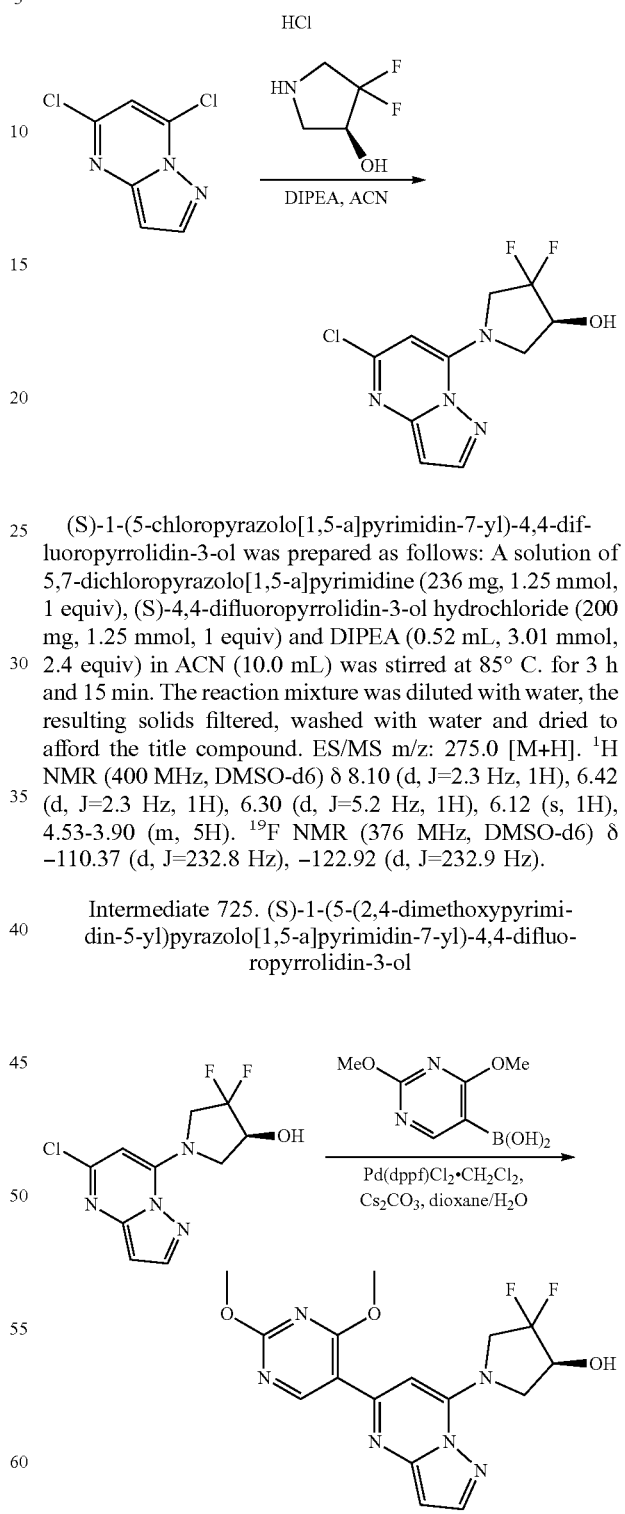

(S)-1-(5-chloropyrazolo[1,5-a]pyrimidin-7-yl)-4,4-difluoropyrrolidin-3-ol was prepared as follows: A solution of 5,7-dichloropyrazolo[1,5-a]pyrimidine (236 mg, 1.25 mmol, 1 equiv), (S)-4,4-difluoropyrrolidin-3-ol hydrochloride (200 mg, 1.25 mmol, 1 equiv) and DIPEA (0.52 mL, 3.01 mmol, 2.4 equiv) in ACN (10.0 mL) was stirred at 85° C. for 3 h and 15 min. The reaction mixture was diluted with water, the resulting solids filtered, washed with water and dried to afford the title compound. ES/MS m/z: 275.0 [M+H]. ¹H NMR (400 MHz, DMSO-d6) δ 8.10 (d, J=2.3 Hz, 1H), 6.42 (d, J=2.3 Hz, 1H), 6.30 (d, J=5.2 Hz, 1H), 6.12 (s, 1H), 4.53-3.90 (m, 5H). ¹⁹F NMR (376 MHz, DMSO-d6) δ −110.37 (d, J=232.8 Hz), −122.92 (d, J=232.9 Hz).

Intermediate 725. (S)-1-(5-(2,4-dimethoxypyrimidin-5-yl)pyrazolo[1,5-a]pyrimidin-7-yl)-4,4-difluoropyrrolidin-3-ol (S)-1-(5-(2,4-dimethoxypyrimidin-5-yl)pyrazolo[1,5-a]pyrimidin-7-yl)-4,4-difluoropyrrolidin-3-ol was prepared as follows: A solution of (S)-1-(5-chloropyrazolo[1,5-a]pyrimidin-7-yl)-4,4-difluoropyrrolidin-3-ol (263 mg, 0.958 mmol, 1 equiv), Pd(dppf)Cl₂CH₂Cl₂ (78 mg, 0.096 mmol, 0.1 equiv) and cesium carbonate (624 mg, 1.92 mmol, 2 equiv) in 1,4 dioxane (6.0 mL) and water (0.80 mL) was gradually heated to 70° C. In a separate vial, (2,4-dimethoxypyrimidin-5-yl)boronic acid (238 mg, 1.29 mmol, 1.35 equiv) was sonicated in 1,4 dioxane (6.0 mL). The suspension was added gradually to the reaction mixture over a period of 40 min. The solution was stirred at 70° C. for an additional 2 h prior to diluting with EtOAc and filtering through a pad of Celite. The filtrate was concentrated under reduced pressure and the crude material was purified by silica gel chromatography (0-100% EtOAc in hexanes) to afford the title compound. ES/MS m/z: 379.1 [M+H].

Intermediate 726. (S)-1-(5-(2,4-dimethoxypyrimidin-5-yl)pyrazolo[1,5-a]pyrimidin-7-yl)-4,4-difluoropyrrolidin-3-yl isopropylcarbamate

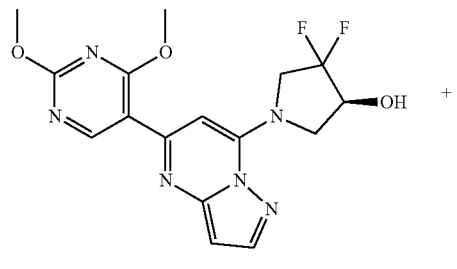

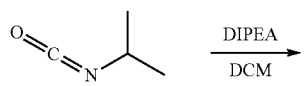

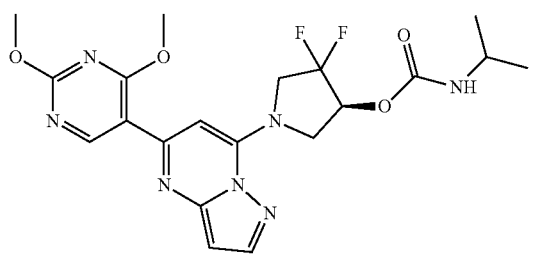

(S)-1-(5-(2,4-dimethoxypyrimidin-5-yl)pyrazolo[1,5-a]pyrimidin-7-yl)-4,4-difluoropyrrolidin-3-yl isopropylcarbamate was prepared as follows: To a solution of (S)-1-(5-(2,4-dimethoxypyrimidin-5-yl)pyrazolo[1,5-a]pyrimidin-7-yl)-4,4-difluoropyrrolidin-3-ol (30 mg, 0.079 mmol, 1 equiv) in DCM (2.0 mL) was added DIPEA (0.14 mL, 0.793 mmol, 10 equiv), followed by 2-isocyanatopropane (0.04 mL, 0.396 mmol, 5 equiv). The reaction mixture was heated to 60° C. and stirred overnight. The solution was diluted with water and extracted with EtOAc (2×). Organic fractions were dried over MgSO₄ and concentrated prior to purification by silica gel chromatography (0-100% EtOAc in hexanes) to afford the title compound. ES/MS m/z: 464.1 [M+H].

Intermediate 727. 6-bromo-4-methyl-1-(2,2,2-trifluoroethyl)-1H-indazole

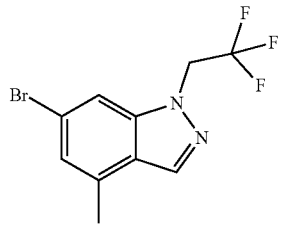 [SMILES: Cc1cc(Br)cc2c1cnn2CC(F)(F)F]

6-bromo-4-methyl-1-(2,2,2-trifluoroethyl)-1H-indazole was prepared in the manner described for Intermediate 703, but replacing 6-bromo-3-chloro-1H-indazole with 6-bromo-4-methyl-1H-indazole. ES/MS m/z: 293.1 [M+H]. ¹H NMR (400 MHz, Chloroform-d) δ 8.06 (d, J=1.0 Hz, 1H), 7.45 (s, 1H), 7.14 (t, J=1.2 Hz, 1H), 4.89 (q, J=8.4 Hz, 2H), 2.58 (s, 3H).

Intermediate 728. 5,7-dibromo-3-fluoropyrazolo[1,5-a]pyrimidine

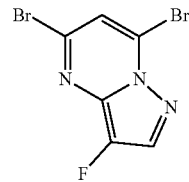

5,7-dibromo-3-fluoropyrazolo[1,5-a]pyrimidine was prepared as follows: To a mixture of 5,7-dibromopyrazolo[1,5-a]pyrimidine (0.800 g, 2.89 mmol) in MeCN (15 mL) was added SelectFluor (1.126 g, 3.18 mmol). The mixture was stirred at 60° C. for 2.5 h, after which additional SelectFluor (512 mg, 1.44 mmol) was added. The mixture was stirred at 60° C. for 8 h, after which it was cooled to rt, concentrated in vacuo, and the residue purified by RP-HPLC (10-90% MeCN/H₂O with TFA modifier, Gemini column). NaHCO₃ sat. solution was added to the purified residue, and the aqueous phase extracted twice with DCM. The combined organics were dried over MgSO₄, filtered, and concentrated in vacuo to afford 5,7-dibromo-3-fluoropyrazolo[1,5-a]pyrimidine. ES/MS m/z: 293.9 [M+H]. ¹H NMR (400 MHz, Chloroform-d) δ8.13 (d, J=3.7 Hz, 1H), 7.27 (s, 1H).

Intermediate 729. ((1S,2S)-2-(2,4-difluorophenyl)cyclopropyl)trifluoro-14-borane, potassium salt

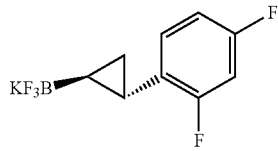

((1S,2S)-2-(2,4-difluorophenyl)cyclopropyl)trifluoro-14-borane, potassium salt was prepared in the manner described for Intermediate 448, but replacing 4,4,5,5-tetramethyl-2-

((2S,2S)-2-(4-(trifluoromethyl)phenyl)cyclopropyl)-1,3,2-dioxaborolane with 2-((2S,2S)-2-(2,4-difluorophenyl)cyclopropyl)-4,4,5,5-tetramethyl-1,3,2-dioxaborolane.

Intermediate 730. 1,3-dioxoisoindolin-2-yl (1S,2S)-2-(4-methyl-1-(2,2,2-trifluoroethyl)-1H-indazol-6-yl)cyclopropane-1-carboxylate

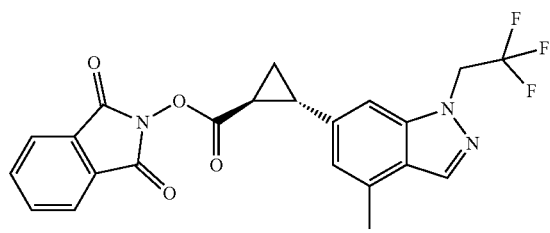 [SMILES: Cc1cc([C@H]2C[C@@H]2C(=O)ON2C(=O)c3ccccc3C2=O)cc2c1cnn2CC(F)(F)F]

1,3-dioxoisoindolin-2-yl(1S,2S)-2-(4-methyl-1-(2,2,2-trifluoroethyl)-1H-indazol-6-yl)cyclopropane-1-carboxylate was prepared in the manner described for Steps 1 and 2 of Intermediate 72, but replacing 5-bromo-2-chlorobenzonitrile with 6-bromo-4-methyl-1-(2,2,2-trifluoroethyl)-1H-indazole, and running Step 1 at 70° C. ES/MS m/z: 444.1 [M+H].

Intermediate 731. 4-methyl-6-((1S,2S)-2-(4,4,5,5-tetramethyl-1,3,2-dioxaborolan-2-yl)cyclopropyl)-1-(2,2,2-trifluoroethyl)-1H-indazole

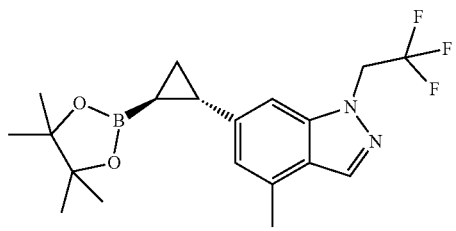 [SMILES: Cc1cc([C@H]2C[C@@H]2B2OC(C)(C)C(C)(C)O2)cc2c1cnn2CC(F)(F)F]

4-methyl-6-((2S,2S)-2-(4,4,5,5-tetramethyl-1,3,2-dioxaborolan-2-yl)cyclopropyl)-1-(2,2,2-trifluoroethyl)-1H-indazole was prepared in the manner described for Intermediate 706, but replacing 1,3-dioxoisoindolin-2-yl (1S,2S)-2-(3-chloro-1-(2,2,2-trifluoroethyl)-1H-indazol-6-yl)cyclopropane-1-carboxylate with 1,3-dioxoisoindolin-2-yl (1S,2S)-2-(4-methyl-1-(2,2,2-trifluoroethyl)-1H-indazol-6-yl)cyclopropane-1-carboxylate. ES/MS m/z: 381.3 [M+H].

Intermediate 732. Potassium trifluoro((1S,2S)-2-(2'-oxo-1'-(2,2,2-trifluoroethyl)spiro[cyclopropane-1,3'-indolin]-6'-yl)cyclopropyl)borate

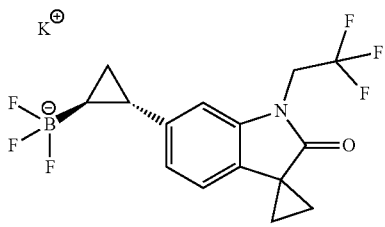 [SMILES: O=C1N(CC(F)(F)F)c2cc([C@H]3C[C@@H]3[B-](F)(F)F)ccc2C12CC2 ; [K+]]

Potassium trifluoro((1S,2S)-2-(2'-oxo-1'-(2,2,2-trifluoroethyl)spiro[cyclopropane-1,3'-indolin]-6'-yl)cyclopropyl)borate was prepared in the manner described for Intermediate 448, but replacing 4,4,5,5-tetramethyl-2-((2S,2S)-2-(4-(trifluoromethyl)phenyl)cyclopropyl)-1,3,2-dioxaborolane with 6'-((2S,2S)-2-(4,4,5,5-tetramethyl-1,3,2-dioxaborolan-2-yl)cyclopropyl)-1'-(2,2,2-trifluoroethyl)spiro[cyclopropane-1,3'-indolin]-2'-one. 1H NMR (400 MHz, Acetone-d6) δ6.82-6.62 (m, 3H), 4.60 (q, J=9.3 Hz, 2H), 1.68-1.59 (m, 1H), 1.53 (dt, J=4.9, 3.4 Hz, 4H), 0.78 (td, J=7.3, 2.5 Hz, 1H), 0.42 (d, J=10.2 Hz, 1H), -0.07 (ddd, J=7.1, 5.7, 3.0 Hz, 1H). 19F NMR (376 MHz, Acetone-d6) δ -71.03 (t, J=9.3 Hz), -145.57 (d, J=75.9 Hz).

Intermediate 733. 6'-((2S,2S)-2-(5-bromopyrazolo[1,5-a]pyrimidin-7-yl)cyclopropyl)-1'-(2,2,2-trifluoroethyl)spiro[cyclopropane-1,3'-indolin]-2'-one

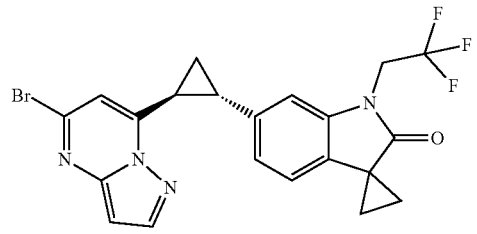 [SMILES: O=C1N(CC(F)(F)F)c2cc([C@H]3C[C@@H]3c3cc(Br)nc4ccnn34)ccc2C12CC2]

6'-((1S,2S)-2-(5-bromopyrazolo[1,5-a]pyrimidin-7-yl)cyclopropyl)-1'-(2,2,2-trifluoroethyl)spiro[cyclopropane-1,3'-indolin]-2'-one was prepared in the manner described for Intermediate 710, but replacing potassium trifluoro((2S,2S)-2-(1-(2,2,2-trifluoroethyl)-1H-indazol-6-yl)cyclopropyl)borate with potassium trifluoro((2S,2S)-2-(2'-oxo-1'-(2,2,2-trifluoroethyl)spiro[cyclopropane-1,3'-indolin]-6'-yl)cyclopropyl)borate. ES/MS m/z: 477.1 [M+H].

Intermediate 734. 6-chloro-8-((2S,2S)-2-(4-methyl-1-(2,2,2-trifluoroethyl)-1H-indazol-6-yl)cyclopropyl)imidazo[1,2-b]pyridazine

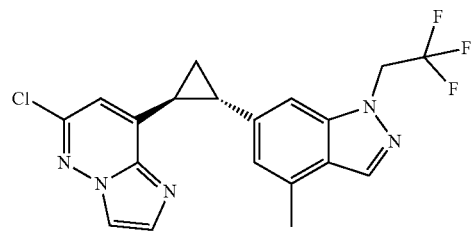 [SMILES: Cc1cc([C@H]2C[C@@H]2c2cc(Cl)nn3ccnc23)cc2c1cnn2CC(F)(F)F]

6-chloro-8-((1S,2S)-2-(4-methyl-1-(2,2,2-trifluoroethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 4-methyl-6-((1S,2S)-2-(4,4,5,5-tetramethyl-1,3,2-dioxaborolan-2-yl)cyclopropyl)-1-(2,2,2-trifluoroethyl)-1H-indazole, and running the reaction at 100° C. for 16 h. ES/MS m/z: 406.1 [M+H].

Intermediate 735. 5-bromo-3-fluoro-7-((2S,2S)-2-(1-(2,2,2-trifluoroethyl)-1H-indazol-6-yl)cyclopropyl)pyrazolo[1,5-a]pyrimidine

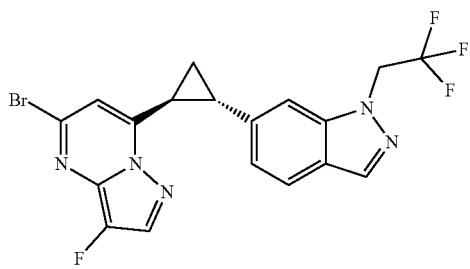 [SMILES: Fc1cnn2c([C@H]3C[C@@H]3c3ccc4cnn(CC(F)(F)F)c4c3)cc(Br)nc12]

5-bromo-3-fluoro-74(1S,2S)-2-(1-(2,2,2-trifluoroethyl)-1H-indazol-6-yl)cyclopropyl)pyrazolo[1,5-a]pyrimidine was prepared in the manner described for Step 2 of Intermediate 710, but replacing 5,7-dibromopyrazolo[1,5-a]pyrimidine with 5,7-dibromo-3-fluoropyrazolo[1,5-a]pyrimidine. ES/MS m/z: 454.0 [M+H].

Intermediate 736. 6-bromo-3-fluoro-1H-pyrazolo[4,3-b]pyridine

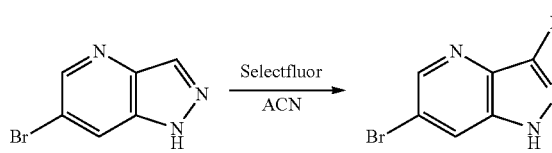

To a solution of 6-bromo-1H-pyrazolo[4,3-b]pyridine (2.5 g, 12.6 mmol, 1 equiv) in ACN (60 mL) was added N-Fluoro-N'-chloromethyltriethylenediamine (6.71 g, 18.9 mmol, 1.5 equiv). The reaction mixture was heated to 90 C. After 2.5 hours, the reaction mixture was filtered, and the filtrate was concentrated. Purification was accomplished by SiO₂ chromatography (0-100% EtOAc/Hex), affording 6-bromo-3-fluoro-1H-pyrazolo[4,3-b]pyridine. ES/MS m/z: 216.00 [M+H].

Intermediate 737. 6-bromo-3-fluoro-1-(2,2,2-trifluoroethyl)pyrazolo[4,3-b]pyridine

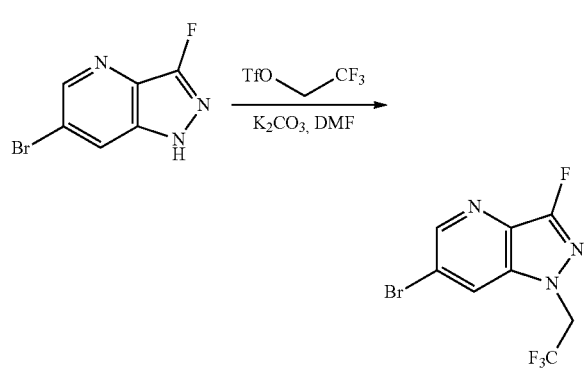

To a solution of 6-bromo-3-fluoro-1H-pyrazolo[4,3-b]pyridine (0.59 g, 2.74 mmol, 1 equiv) in DMF (4 mL) was added potassium carbonate (1138 mg, 8.23 mmol, 3 equiv) and 2,2,2-trifluoroethyl trifluoromethanesulfonate (955 mg, 4.12 mmol, 1.5 equiv). The reaction mixture was heated to 80° C. After 1 hour, the reaction mixture was diluted with brine (50 mL) and extracted with EtOAc. The combined organic layers were dried over Na₂SO₄, filtered, and concentrated. Purification was accomplished by SiO₂ chromatography (0-50% EtOAc/Hex), affording 6-bromo-3-fluoro-1-(2,2,2-trifluoroethyl)pyrazolo[4,3-b]pyridine. ES/MS m/z: 298.00 [M+H].

Intermediate 738. 8-bromo-6-(2,4-dimethoxypyrimidin-5-yl)imidazo[1,2-b]pyridazine

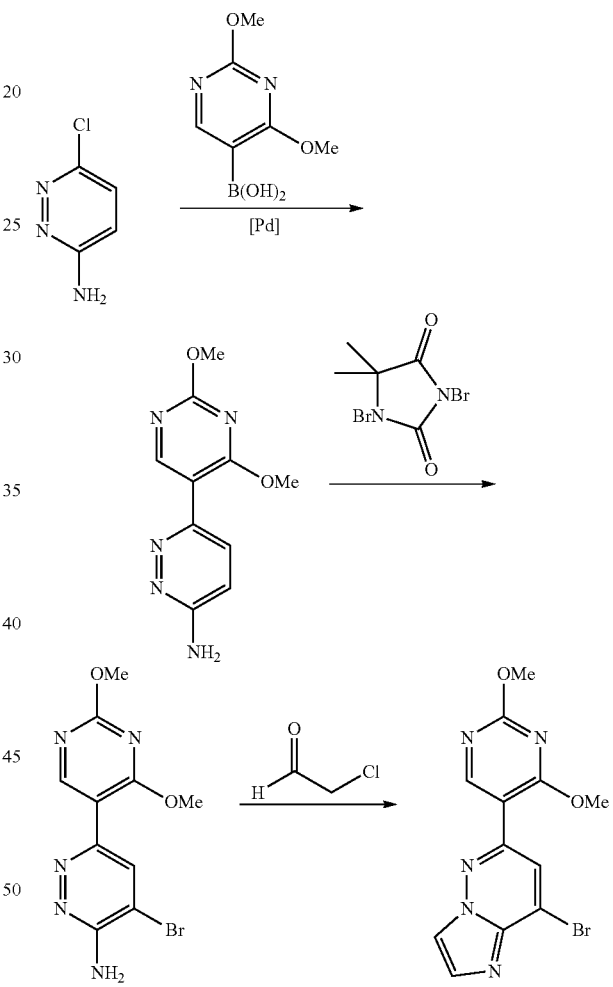

Step 1: To a stirred solution of 6-chloropyridazin-3-amine (200 g, 1.55 mol, 1 equiv) and (2,4-dimethoxypyrimidin-5-yl)boronic acid (312.4 g, 1.69 mol, 1.1 equiv) in 1,4-dioxane (4 L) and water (2 L) was added potassium carbonate (427.90 g, 3.1 mol, 2 equiv) and degassed for 10 minutes using Argon. PdCl₂(dppf)-CH₂Cl₂ (25.3 g, 2 mol %) was added to the reaction mixture, which was degassed for 10 minutes using Argon. The reaction mixture was heated to 80° C. After 2 hours, the reaction mixture was cooled to 50° C., filtered over celite with 1,4-dioxane washings, and concentrated. The resulting residue was diluted with water (1.6 L), stirred for 30 minutes, and filtered. The remaining solids were triturated with IPA (1 L) and dried under vacuum to afford 6-(2,4-dimethoxypyrimidin-5-yl)pyridazin-3-amine. This material was used in the next step without further purification.

Step 2: To a stirred suspension of 6-(2,4-dimethoxypyrimidin-5-yl)pyridazin-3-amine (25 g, 0.107 mol, 1 equiv) in MeOH (250 mL) was added sodium acetate (7.04 g, 0.085 mol, 0.8 equiv) and acetic acid (1.72 g, 0.028 mol, 0.26 equiv). To this resulting heterogeneous reaction mixture was added 1,3-dibromo-5,5-dimethylimidazolidine-2,4-dione (18.4 g, 0.064 mol, 0.6 equiv) portionwise. After 2 hours, the reaction mixture was quenched with a 38% aqueous solution of NaHSO$_3$ and concentrated. The resulting residue was diluted with water (250 mL) and filtered. The remaining solids were purified by SiO$_2$ chromatography (2-3% MeOH/ CH$_2$Cl$_2$), affording 4-bromo-6-(2,4-dimethoxypyrimidin-5-yl)pyridazin-3-amine.

Step 3: To a stirred suspension of 4-bromo-6-(2,4-dimethoxypyrimidin-5-yl)pyridazin-3-amine (80 g, 0.256 mol, 1 equiv) in MeOH (2.4 L) was added 55% aqueous 2-chloroacetaldehyde (183 g, 1.28 mol, 5 equiv). The reaction mixture was heated to 60° C. After 24 hours, the heterogeneous reaction mixture was filtered. The remaining solids were purified by SiO$_2$ chromatography (2-3% MeOH/ CH$_2$Cl$_2$), affording 8-bromo-6-(2,4-dimethoxypyrimidin-5-yl)imidazo[1,2-b]pyridazine.

Intermediate 739. 6-bromo-1-(2,2,2-trifluoroethyl)-1H-pyrazolo[4,3-c]pyridine

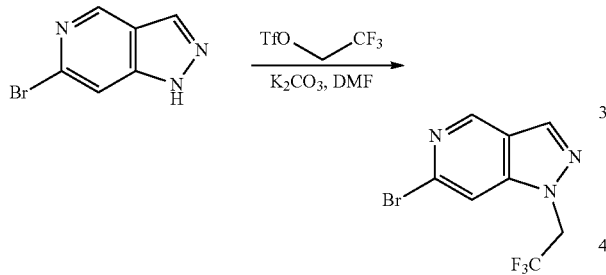

To a solution of 6-bromo-1H-pyrazolo[4,3-c]pyridine (1 g, 5.05 mmol, 1 equiv) in DMF (20 mL) was added potassium carbonate (2094 mg, 15.1 mmol, 3 equiv) and 2,2,2-trifluoroethyl trifluoromethanesulfonate (1.09 mL, 7.57 mmol, 1.5 equiv). The reaction mixture was heated to 80° C. After 2 hours, the reaction mixture was diluted with brine (50 mL) and extracted with 80% EtOAc/Hex (2×100 mL). The combined organic layers were dried over Na$_2$SO$_4$, filtered, and concentrated. Purification was accomplished by SiO$_2$ chromatography (0-100% EtOAc/Hex), affording 6-bromo-1-(2,2,2-trifluoroethyl)-1H-pyrazolo[4,3-c]pyridine. $^1$H NMR (400 MHz, DMSO-d6) δ 8.98 (s, 1H), 8.50 (s, 1H), 8.25 (s, 1H), 5.52 (q, J=9.1 Hz, 2H). ES/MS m/z: 280.00 [M+H].

Intermediate 740. 6-bromo-1-(2,2,2-trifluoroethyl)-1H-pyrazolo[3,4-b]pyridine

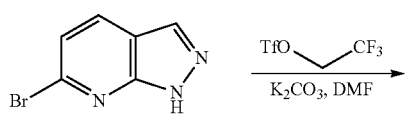

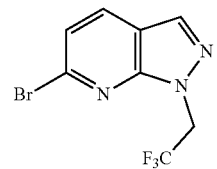

To a solution of 6-bromo-1H-pyrazolo[3,4-b]pyridine (400 mg, 2.02 mmol, 1 equiv) in DMF (6 mL) was added potassium carbonate (838 mg, 6.06 mmol, 3 equiv) and 2,2,2-trifluoroethyl trifluoromethanesulfonate (0.44 mL, 3.03 mmol, 1.5 equiv). The reaction mixture was heated to 80° C. After 1 hour, the reaction mixture was directly purified by SiO$_2$ chromatography (0-100% EtOAc/Hex), affording 6-bromo-1-(2,2,2-trifluoroethyl)-1H-pyrazolo[3,4-b]pyridine. $^1$H NMR (400 MHz, Chloroform-d) δ 8.10 (s, 1H), 7.94 (d, J=8.3 Hz, 1H), 7.37 (d, J=8.3 Hz, 1H), 5.08 (q, J=8.3 Hz, 2H). ES/MS m/z: 280.00 [M+H].

Intermediate 741. 6-bromo-1-(2,2,2-trifluoroethyl)-1H-pyrazolo[4,3-b]pyridine

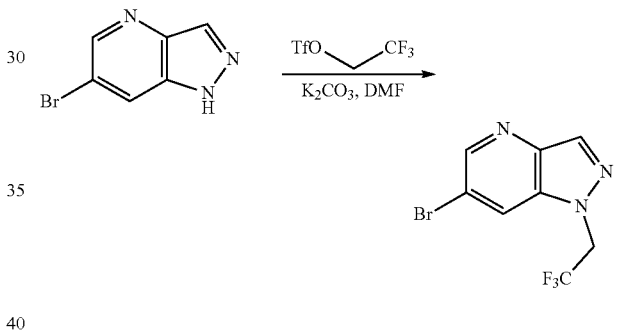

To a solution of 6-bromo-1H-pyrazolo[4,3-b]pyridine (4000 mg, 20.2 mmol, 1 equiv) in DMF (30 mL) was added potassium carbonate (8375 mg, 60.6 mmol, 3 equiv) and 2,2,2-trifluoroethyl trifluoromethanesulfonate (4.37 mL, 30.3 mmol, 1.5 equiv). The reaction mixture was heated to 80° C. After 1 hour, the reaction mixture was diluted with water (30 mL) and extracted with 50% EtOAc/Hex (3×50 mL). The combined organic layers were concentrated and purified by SiO$_2$ chromatography, affording 6-bromo-1-(2,2,2-trifluoroethyl)-1H-pyrazolo[4,3-b]pyridine. $^1$H NMR (400 MHz, DMSO-d6) δ 8.74 (bs, 1H), 8.68 (d, J=2.0 Hz, 1H), 8.50 (s, 1H), 5.51 (q, J=9.1 Hz, 2H). ES/MS m/z: 282.00 [M+H].

Intermediate 742. 6-bromo-1-(2,2,2-trifluoroethyl)-3-(trifluoromethyl)-1H-indazole

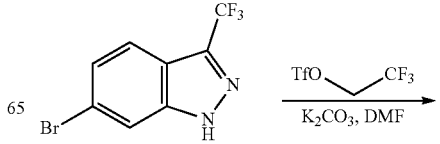

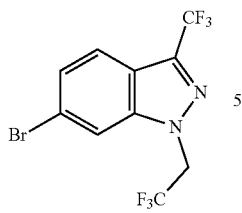

To a solution of 6-bromo-3-(trifluoromethyl)-1H-indazole (1000 mg, 3.77 mmol, 1 equiv) in DMF (10 mL) was added potassium carbonate (1043 mg, 7.55 mmol, 2 equiv) and 2,2,2-trifluoroethyl trifluoromethanesulfonate (0.82 mL, 5.66 mmol, 1.5 equiv). The reaction mixture was heated to 80° C. After 1 hour, the reaction mixture was directly purified by SiO₂ chromatography (0-100% EtOAc/Hex), affording 6-bromo-1-(2,2,2-trifluoroethyl)-3-(trifluoromethyl)-1H-indazole. ¹H NMR (400 MHz, DMSO-d6) δ 8.43 (s, 1H), 7.84 (d, J=8.7 Hz, 1H), 7.66-7.55 (m, 1H), 5.67 (q, J=9.1 Hz, 2H).

Intermediate 743. 6-chloro-1-(2,2,2-trifluoroethyl)-3-(trifluoromethyl)-1H-pyrazolo[4,3-c]pyridine

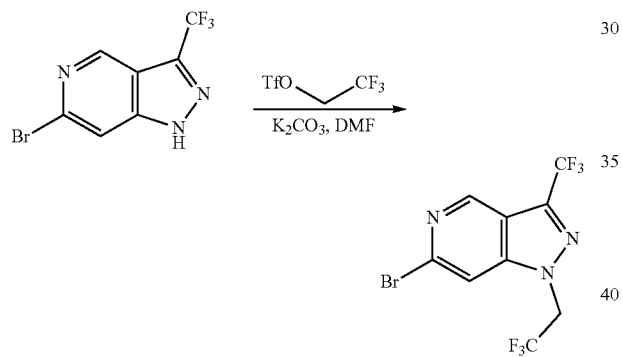

To a solution of 6-chloro-3-(trifluoromethyl)-1H-pyrazolo[4,3-c]pyridine (1000 mg, 4.51 mmol, 1 equiv) in DMF (12 mL) was added potassium carbonate (1871 mg, 13.5 mmol, 3 equiv) and 2,2,2-trifluoroethyl trifluoromethanesulfonate (0.78 mL, 5.42 mmol, 1.1 equiv). The reaction mixture was heated to 80° C. After 30 minutes, the reaction mixture was directly purified by SiO₂ chromatography (0-100% EtOAc/Hex), affording 6-chloro-1-(2,2,2-trifluoroethyl)-3-(trifluoromethyl)-1H-pyrazolo[4,3-c]pyridine. ¹H NMR (400 MHz, DMSO-d6) δ9.13 (s, 1H), 8.32 (s, 1H), 5.70 (q, J=9.0 Hz, 2H). ES/MS m/z: 304.00 [M+H].

Intermediate 744. 6-bromo-1-(2,2,2-trifluoroethyl)-2-(trifluoromethyl)-1H-benzo[d]imidazole

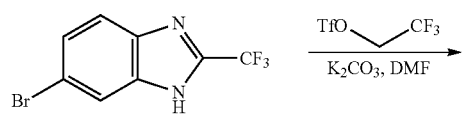

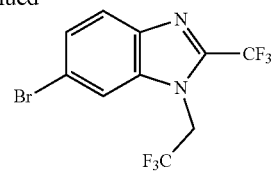

To a solution of 6-bromo-2-(trifluoromethyl)-1H-benzo[d]imidazole (1500 mg, 5.66 mmol, 1 equiv) in DMF (12 mL) was added potassium carbonate (1564 mg, 11.3 mmol, 2 equiv) and 2,2,2-trifluoroethyl trifluoromethanesulfonate (1.22 mL, 8.49 mmol, 1.5 equiv). The reaction mixture was heated to 80° C. After 1 hour, the reaction mixture was directly purified by SiO₂ chromatography (0-100% EtOAc/Hex), affording 6-bromo-1-(2,2,2-trifluoroethyl)-2-(trifluoromethyl)-1H-benzo[d]imidazole. ¹H NMR (400 MHz, DMSO-d6) δ 8.30 (s, 1H), 7.86 (d, J=8.7 Hz, 1H), 7.62 (dd, J=8.7, 1.8 Hz, 1H), 5.52 (q, J=8.9 Hz, 2H). ES/MS m/z: 347.00 [M+H].

Intermediates 745 and 746. 6-bromo-2-(difluoromethyl)-1-(2,2,2-trifluoroethyl)-1H-benzo[d]imidazole and 5-bromo-2-(difluoromethyl)-1-(2,2,2-trifluoroethyl)-1H-benzo[d]imidazole and

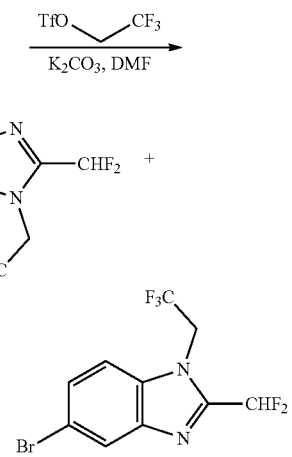

To a solution of 6-bromo-2-(difluoromethyl)-1H-benzo[d]imidazole (1000 mg, 4.05 mmol, 1 equiv) in DMF (12 mL) was added potassium carbonate (1119 mg, 8.10 mmol, 2 equiv) and 2,2,2-trifluoroethyl trifluoromethanesulfonate (0.88 mL, 6.07 mmol, 1.5 equiv). The reaction mixture was heated to 80° C. After 1 hour, the reaction mixture was directly purified by SiO₂ chromatography (0-100% EtOAc/Hex), affording a mixture of 6-bromo-2-(difluoromethyl)-1-(2,2,2-trifluoroethyl)-1H-benzo[d]imidazole and 5-bromo-2-(difluoromethyl)-1-(2,2,2-trifluoroethyl)-1H-benzo[d]imidazole. This mixture was separated by RP-HPLC (10-100% MeCN/H₂O with TFA modifier). Characterization data for Intermediate 745 6-bromo-2-(difluoromethyl)-1-(2,2,2-trifluoroethyl)-1H-benzo[d]imidazole: ¹H NMR (400 MHz, DMSO-d6) δ 8.18 (bs, 1H), 7.78 (d, J=8.7 Hz, 1H), 7.54 (dd, J=8.7, 1.8 Hz, 1H), 7.46 (t, J=51.4 Hz, 1H), 5.49 (q, J=8.8 Hz, 2H). Characterization data for Intermediate 746 5-bromo-2-(difluoromethyl)-1-(2,2,2-trifluoroethyl)-1H-benzo[d]imidazole: ¹H NMR (400 MHz, DMSO-d6) δ

8.06 (d, J=1.9 Hz, 1H), 7.83 (d, J=8.8 Hz, 1H), 7.65 (dd, J=8.8, 1.9 Hz, 1H), 7.47 (t, J=51.4 Hz, 1H), 5.51 (q, J=8.7 Hz, 2H).

Intermediate 747. 6-chloro-1-(2,2,2-trifluoroethyl)-2-(trifluoromethyl)-1H-imidazo[4,5-c]pyridine

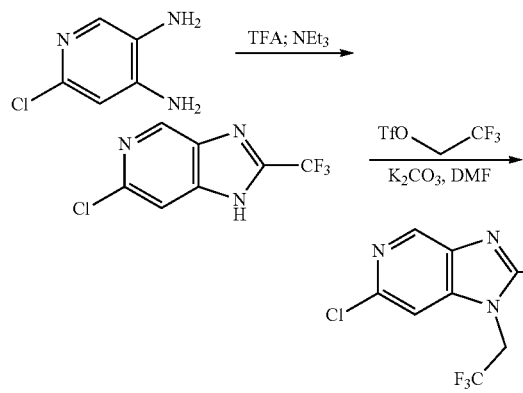

Step 1: A solution of 6-chloropyridine-3,4-diamine (1000 mg, 6.97 mmol, 1 equiv) in TFA (14 mL) was heated to 70° C. After 16 hours, the reaction mixture was concentrated. Triethylamine (10 mL) was added, and after an additional 24 hours at 70° C., the reaction mixture was again concentrated. Purification was accomplished by SiO₂ chromatography (0-20% MeOH/CH₂Cl₂), affording 6-chloro-2-(trifluoromethyl)-1H-imidazo[4,5-c]pyridine. ES/MS m/z: 222.00 [M+H].

Step 2: To a solution of 6-chloro-2-(trifluoromethyl)-1H-imidazo[4,5-c]pyridine (1000 mg, 4.51 mmol, 1 equiv) in DMF (15 mL) was added potassium carbonate (1871 mg, 13.5 mmol, 3 equiv) and 2,2,2-trifluoroethyl trifluoromethanesulfonate (1.95 mL, 13.5 mmol, 3 equiv). The reaction mixture was heated to 80° C. After 24 hours, the reaction mixture was diluted with brine (50 mL) and extracted with EtOAc (3×50 mL). The combined organic layers were dried over Na₂SO₄, filtered and concentrated. Purification was accomplished by SiO₂ chromatography (0-100% EtOAc/Hex), affording 6-chloro-1-(2,2,2-trifluoroethyl)-2-(trifluoromethyl)-1H-imidazo[4,5-c]pyridine. ¹H NMR (400 MHz, DMSO-d6) δ 9.08 (s, 1H), 8.24 (s, 1H), 5.54 (q, J=8.8 Hz, 2H). ES/MS m/z: 304.10 [M+H].

Intermediate 748.
2-bromo-5-chloro-4-(2,2,2-trifluoroethoxy)pyridine

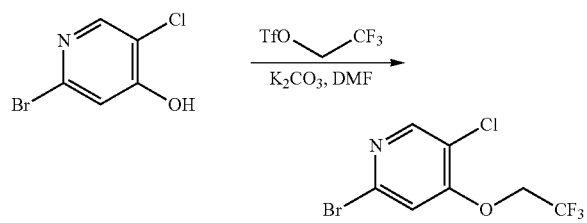

To a solution of 2-bromo-5-chloropyridin-4-ol (1000 mg, 4.8 mmol, 1 equiv) in DMF (15 mL) was added potassium carbonate (1989 mg, 14.4 mmol, 3 equiv) and 2,2,2-trifluoroethyl trifluoromethanesulfonate (1.04 mL, 7.2 mmol, 1.5 equiv). The reaction mixture was heated to 80° C. After 2 hours, the reaction mixture was directly purified by SiO₂ chromatography (0-100% EtOAc/Hex), affording 2-bromo-5-chloro-4-(2,2,2-trifluoroethoxy)pyridine. ¹H NMR (400 MHz, Chloroform-d) δ 8.30 (s, 1H), 7.01 (s, 1H), 4.48 (q, J=7.6 Hz, 2H). ES/MS m/z: 291.90 [M+H].

Intermediate 749. 2-bromo-5-chloro-4-((2,2-difluorocyclopropyl)methoxy)pyridine

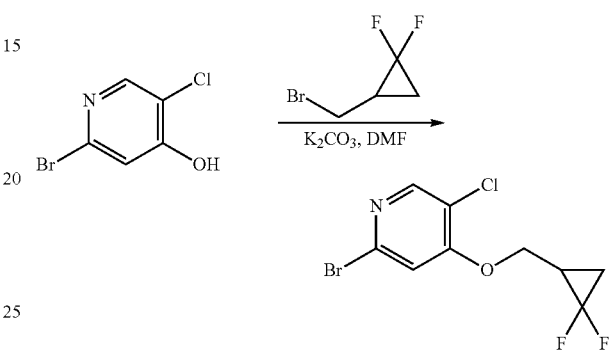

To a solution of 2-bromo-5-chloropyridin-4-ol (150 mg, 0.72 mmol, 1 equiv) in DMF (1.5 mL) was added potassium carbonate (298 mg, 2.16 mmol, 3 equiv) and 2-(bromomethyl)-1,1-difluorocyclopropane (0.16 mL, 1.08 mmol, 1.5 equiv). The reaction mixture was heated to 80° C. After 90 minutes, the reaction mixture was directly purified by SiO₂ chromatography (0-100% EtOAc/Hex), affording 2-bromo-5-chloro-4-((2,2-difluorocyclopropyl)methoxy)pyridine. ¹H NMR (400 MHz, Chloroform-d) δ 8.23 (s, 1H), 6.98 (s, 1H), 4.26-4.06 (m, 2H), 2.21-2.08 (m, 1H), 1.75-1.62 (m, 1H), 1.44-1.29 (m, 1H). ES/MS m/z: 299.90 [M+H].

Intermediates 750 and 751. 7-bromo-2-(2,2,2-trifluoroethoxy)quinoline and 7-bromo-1-(2,2,2-trifluoroethyl)quinolin-2(1H)-one

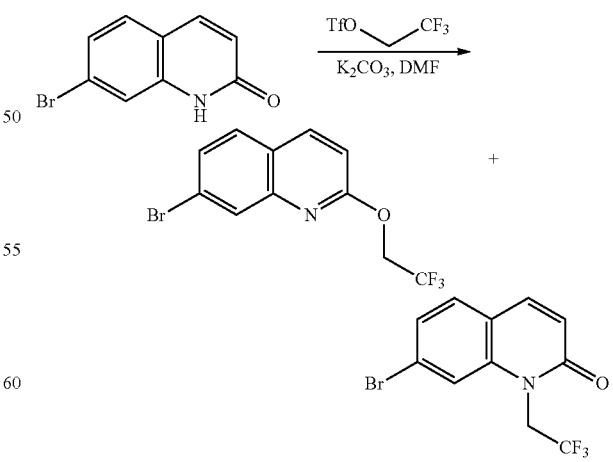

To a solution of 7-bromoquinolin-2(1H)-one (500 mg, 2.23 mmol, 1 equiv) in DMF (6 mL) was added potassium carbonate (925 mg, 6.69 mmol, 3 equiv) and 2,2,2-trifluoroethyl trifluoromethanesulfonate (4.83 mL, 3.35 mmol, 1.5 equiv). The reaction mixture was heated to 80° C. After 1 hour, the reaction mixture was directly purified by SiO₂ chromatography (0-100% EtOAc/Hex), affording 7-bromo-2-(2,2,2-trifluoroethoxy)quinoline and 7-bromo-1-(2,2,2-trifluoroethyl)quinolin-2(1H)-one. Characterization data for 7-bromo-2-(2,2,2-trifluoroethoxy)quinoline: ¹H NMR (400 MHz, Chloroform-d) δ 8.07-8.00 (m, 2H), 7.62 (d, J=8.6 Hz, 1H), 7.56-7.48 (m, 1H), 7.02 (d, J=8.9 Hz, 1H), 4.91 (q, J=8.6 Hz, 2H). Characterization data for 7-bromo-1-(2,2,2-trifluoroethyl)quinolin-2(1H)-one: ¹H NMR (400 MHz, Chloroform-d) δ 7.67 (d, J=9.6 Hz, 1H), 7.54 (s, 1H), 7.46-7.37 (m, 2H), 6.73 (d, J=9.6 Hz, 1H), 5.07-4.84 (m, 2H).

Intermediate 752. 6-bromo-4-fluoro-1-(2,2,2-trifluoroethyl)-1H-indazole

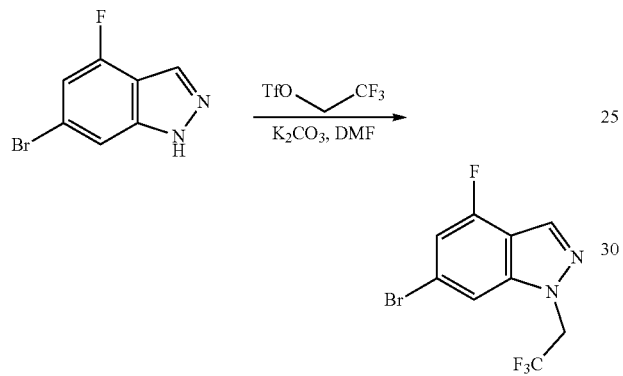

To a solution of 6-bromo-4-fluoro-1H-indazole (1 g, 4.65 mmol, 1 equiv) in DMF (12 mL) was added potassium carbonate (1285 mg, 9.30 mmol, 2 equiv) and 2,2,2-trifluoroethyl trifluoromethanesulfonate (1.01 mL, 6.98 mmol, 1.5 equiv). The reaction mixture was heated to 80° C. After 1 hour, the reaction mixture was directly purified by SiO₂ chromatography (0-100% EtOAc/Hex), affording 6-bromo-4-fluoro-1-(2,2,2-trifluoroethyl)-1H-indazole. ¹H NMR (400 MHz, Chloroform-d) δ 8.12 (s, 1H), 7.43 (s, 1H), 7.05 (d, J=9.0 Hz, 1H), 4.91 (q, J=8.3 Hz, 2H). ES/MS m/z: 297.00 [M+H].

Intermediate 753. 6-bromo-5-fluoro-1-(2,2,2-trifluoroethyl)-1H-indazole

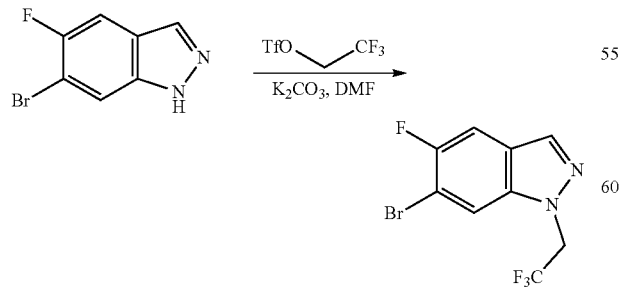

To a solution of 6-bromo-5-fluoro-1H-indazole (1 g, 4.65 mmol, 1 equiv) in DMF (12 mL) was added potassium carbonate (1285 mg, 9.30 mmol, 2 equiv) and 2,2,2-trifluoroethyl trifluoromethanesulfonate (1.01 mL, 6.98 mmol, 1.5 equiv). The reaction mixture was heated to 80° C. After 1 hour, the reaction mixture was directly purified by SiO₂ chromatography (0-100% EtOAc/Hex), affording 6-bromo-5-fluoro-1-(2,2,2-trifluoroethyl)-1H-indazole. ¹H NMR (400 MHz, Chloroform-d) δ 8.04 (d, J=1.0 Hz, 1H), 7.69 (d, J=5.2 Hz, 1H), 7.46 (d, J=7.9 Hz, 1H), 4.91 (q, J=8.4 Hz, 2H). ES/MS m/z: 297.00 [M+H].

Intermediate 754. 6-bromo-7-fluoro-1-(2,2,2-trifluoroethyl)-1H-indazole

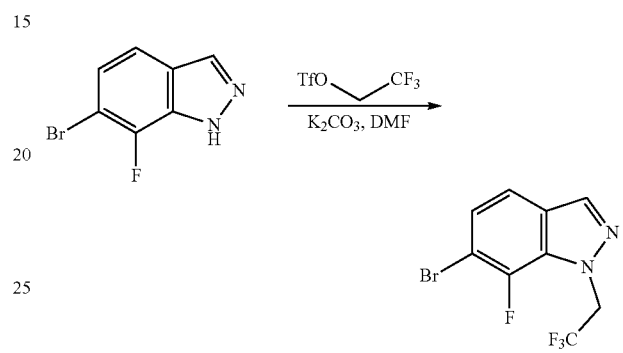

To a solution of 6-bromo-7-fluoro-1H-indazole (1 g, 4.65 mmol, 1 equiv) in DMF (12 mL) was added potassium carbonate (1285 mg, 9.30 mmol, 2 equiv) and 2,2,2-trifluoroethyl trifluoromethanesulfonate (1.01 mL, 6.98 mmol, 1.5 equiv). The reaction mixture was heated to 80° C. After 1 hour, the reaction mixture was directly purified by SiO₂ chromatography (0-100% EtOAc/Hex), affording 6-bromo-7-fluoro-1-(2,2,2-trifluoroethyl)-1H-indazole. ¹H NMR (400 MHz, Chloroform-d) δ 8.07 (d, J=2.3 Hz, 1H), 7.42-7.38 (m, 1H), 7.35-7.29 (m, 1H), 5.08 (q, J=8.1 Hz, 2H). ES/MS m/z: 297.00 [M+H].

Intermediate 755. 6-bromo-4,7-difluoro-1-(2,2,2-trifluoroethyl)-1H-indazole

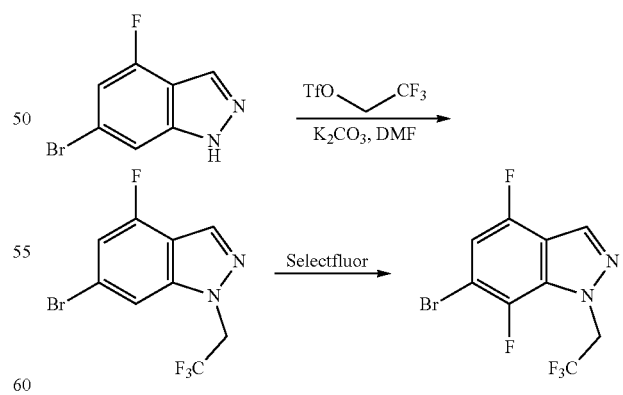

Step 1: To a solution of 6-bromo-4-fluoro-1H-indazole (1 g, 4.65 mmol, 1 equiv) in DMF (12 mL) was added potassium carbonate (1285 mg, 9.30 mmol, 2 equiv) and 2,2,2-trifluoroethyl trifluoromethanesulfonate (1.01 mL, 6.98 mmol, 1.5 equiv). The reaction mixture was heated to 80° C. After 1 hour, the reaction mixture was directly purified by SiO₂ chromatography (0-100% EtOAc/Hex), affording 6-bromo-4-fluoro-1-(2,2,2-trifluoroethyl)-1H-indazole. ¹H NMR (400 MHz, Chloroform-d) δ 8.12 (s, 1H), 7.43 (s, 1H), 7.05 (d, J=9.0 Hz, 1H), 4.91 (q, J=8.3 Hz, 2H). ES/MS m/z: 297.00 [M+H].

Step 2: To a solution of 6-bromo-4-fluoro-1-(2,2,2-trifluoroethyl)-1H-indazole (2.32 g, 7.81 mmol, 1 equiv) in 20:1 MeCN/AcOH (50 mL) was added 1-chloromethyl-4-fluoro-1,4-diazoniabicyclo[2.2.2]octane bis(tetrafluoroborate) (5534 mg, 15.6 mmol, 2 equiv). The reaction mixture was heated to 70° C. After 14 hours, the reaction mixture was heated to 100° C. After an additional 4 hours, the reaction mixture was cooled to room temperature and concentrated. Purification was accomplished by SiO₂ chromatography (0-30% EtOAc/Hex), affording 6-bromo-4,7-difluoro-1-(2,2,2-trifluoroethyl)-1H-indazole. ¹H NMR (400 MHz, DMSO-d6) δ 8.50 (d, J=2.1 Hz, 1H), 7.44 (dd, J=8.8, 4.0 Hz, 1H), 5.46 (q, J=8.9 Hz, 2H). ¹⁹F NMR (376 MHz, DMSO-d6) δ -70.90 (td, J=8.8, 6.4 Hz), -121.45 (dd, J=21.9, 8.8 Hz), -132.17--132.36 (m).

Intermediate 756. 6-bromo-3-(2,2,2-trifluoroethyl)imidazo[1,5-a]pyridine

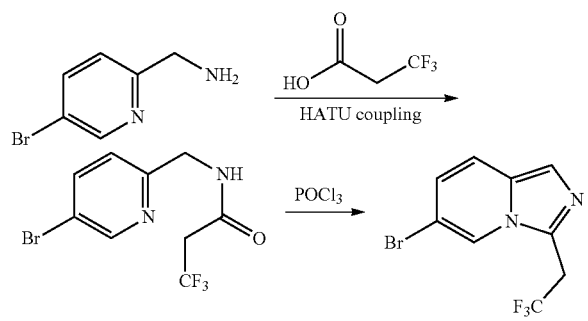

Step 1: To a solution of (5-bromopyridin-2-yl)methanamine (1000 mg, 5.35 mmol, 1 equiv), 3,3,3-trifluoropropanoic acid (822 mg, 6.42 mmol, 1.2 equiv), and HATU (3049 mg, 8.02 mmol, 1.5 equiv) in DMF (10 mL) was added DIPEA (2.38 mL, 13.4 mmol, 2.5 equiv). After 3 hours, the reaction mixture was quenched with H₂O (10 mL) and extracted with EtOAc (3×10 mL). The combined organic layers were concentrated and purified by SiO₂ chromatography (0-100% EtOAc/Hex), affording N-((5-bromopyridin-2-yl)methyl)-3,3,3-trifluoropropanamide. ¹H NMR (400 MHz, DMSO-d6) δ 8.87 (t, J=5.9 Hz, 1H), 8.64 (d, J=2.4 Hz, 1H), 8.04 (dd, J=8.4, 2.4 Hz, 1H), 7.28 (d, J=8.4 Hz, 1H), 4.37 (d, J=5.9 Hz, 2H), 3.36 (q, J=11.4 Hz, 2H). ES/MS m/z: 297.00 [M+H].

Step 2: To a suspension of N-((5-bromopyridin-2-yl)methyl)-3,3,3-trifluoropropanamide (150 mg, 0.51 mmol, 1 equiv) in Toluene (2 mL) was added phosphoryl trichloride (0.19 mL, 2.02 mmol, 4 equiv). The reaction mixture was heated to 90° C. After 6 hours, the reaction mixture was cooled to 0° C. and quenched with saturated aqueous NaHCO₃ (3 mL). The reaction mixture was directly purified by SiO₂ chromatography (0-30% MeOH/CH₂Cl₂), affording 6-bromo-3-(2,2,2-trifluoroethyl)imidazo[1,5-a]pyridine. ¹H NMR (400 MHz, DMSO-d6) δ 8.85 (s, 1H), 7.63 (d, J=9.6 Hz, 1H), 7.56 (s, 1H), 6.97 (d, J=9.6 Hz, 1H), 4.34 (q, J=10.8 Hz, 2H). ES/MS m/z: 279.00 [M+H].

Intermediate 757. 6-bromo-3-(2,2,2-trifluoroethyl)-1-(trifluoromethyl)imidazo[1,5-a]pyridine

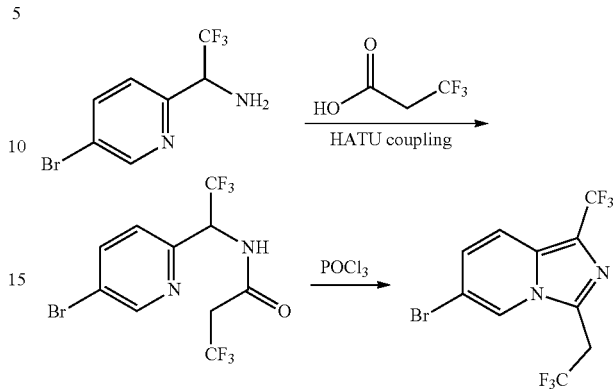

Step 1: To a solution of 1-(5-bromopyridin-2-yl)-2,2,2-trifluoroethan-1-amine hydrochloride (1000 mg, 3.92 mmol, 1 equiv), 3,3,3-trifluoropropanoic acid (527 mg, 4.12 mmol, 1.05 equiv), and HATU (2236 mg, 5.88 mmol, 1.5 equiv) in DMF (10 mL) was added DIPEA (1.75 mL, 9.80 mmol, 2.5 equiv). After 3 hours, the reaction mixture was quenched with H₂O (10 mL) and extracted with EtOAc (3×10 mL). The combined organic layers were concentrated and purified by SiO₂ chromatography (0-100% EtOAc/Hex), affording N-(1-(5-bromopyridin-2-yl)-2,2,2-trifluoroethyl)-3,3,3-trifluoropropanamide. ¹H NMR (400 MHz, DMSO-d6) δ 9.53 (d, J=9.3 Hz, 1H), 8.80 (d, J=2.4 Hz, 1H), 8.21 (dd, J=8.4, 2.4 Hz, 1H), 7.69 (d, J=8.4 Hz, 1H), 6.01 (p, J=8.3 Hz, 1H), 3.61-3.44 (m, 2H). ES/MS m/z: 367.00 [M+H].

Step 2: To a suspension of N-(1-(5-bromopyridin-2-yl)-2,2,2-trifluoroethyl)-3,3,3-trifluoropropanamide (200 mg, 0.55 mmol, 1 equiv) in Toluene (2 mL) was added phosphoryl trichloride (0.26 mL, 2.74 mmol, 5 equiv). The reaction mixture was heated to 90° C. After 30 hours, the reaction mixture was cooled to 0° C. and quenched with saturated aqueous NaHCO₃ (3 mL). The reaction mixture was directly purified by SiO₂ chromatography (0-100% EtOAc/Hex), affording 6-bromo-3-(2,2,2-trifluoroethyl)-1-(trifluoromethyl)imidazo[1,5-a]pyridine. ¹H NMR (400 MHz, DMSO-d6) δ 9.06 (s, 1H), 7.72-7.64 (m, 1H), 7.37-7.28 (m, 1H), 4.41 (q, J=10.7 Hz, 2H). ES/MS m/z: 347.00 [M+H].

Intermediate 758. 7-chloro-3-(trifluoromethyl)imidazo[1,5-a]pyridine

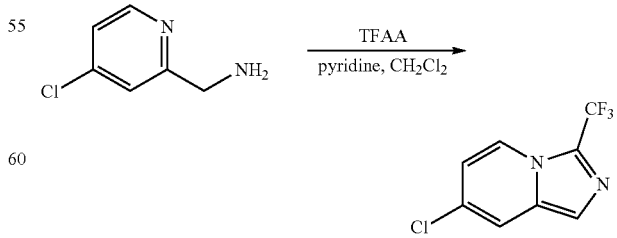

To a cooled (~10° C.) solution of (4-chloropyridin-2-yl)methanamine (1000 mg, 7.01 mmol, 1 equiv) and pyridine (2.43 mL, 30.2 mmol, 4.3 equiv) in CH₂Cl₂ (10 mL) was added a solution of trifluoroacetic anhydride (3.12 mL, 22.4 mmol, 3.2 equiv) in CH$_2$Cl$_2$ (14 mL) dropwise. After 23 hours, the reaction mixture was warmed to room temperature and concentrated. Purification was accomplished by SiO$_2$ chromatography (0-100% EtOAc/Hex), affording 7-chloro-3-(trifluoromethyl)imidazo[1,5-a]pyridine. $^1$H NMR (400 MHz, DMSO-d6) δ8.45 (d, J=7.5 Hz, 1H), 8.04 (d, J=2.1 Hz, 1H), 7.61 (s, 1H), 7.04 (dd, J=7.5, 2.1 Hz, 1H).

Intermediate 759. 6-bromo-3-(2,2,2-trifluoroethyl)-2-(trifluoromethyl)imidazo[1,2-a]pyridine

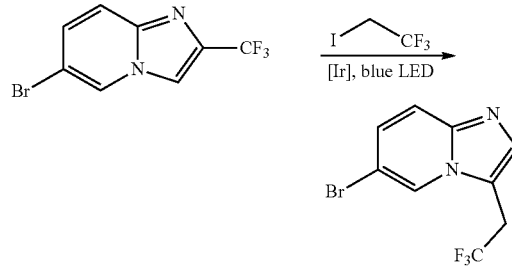

To a solution of 6-bromo-2-(trifluoromethyl)imidazo[1,2-a]pyridine (200 mg, 0.76 mmol, 1 equiv) in DMSO (6 mL) was added 1,1,1-trifluoro-2-iodoethane (0.223 mL, 2.26 mmol, 3 equiv), potassium carbonate (209 mg, 1.51 mmol, 2 equiv), and Ir(ppy)$_3$ (25 mg, 5 mol %). The reaction mixture was stirred at room temperature under blue LED irradiation. After 48 hours, the reaction mixture was directly purified by SiO$_2$ chromatography (0-100% EtOAc/Hex), affording 6-bromo-3-(2,2,2-trifluoroethyl)-2-(trifluoromethyl)imidazo[1,2-a]pyridine. $^1$H NMR (400 MHz, Chloroform-d) δ 7.95 (s, 1H), 7.63 (d, J=9.7 Hz, 1H), 7.52 (d, J=9.7 Hz, 1H), 4.08 (q, J=9.5 Hz, 2H). $^{19}$F NMR (376 MHz, DMSO-d6) δ −61.86, −62.31 (t, J=10.2 Hz). ES/MS m/z: 347.00 [M+H].

Intermediate 760. 6-chloro-7-fluoro-1-(2,2,2-trifluoroethyl)-1H-pyrazolo[4,3-c]pyridine

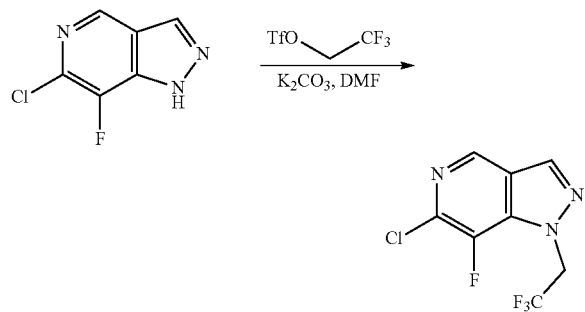

To a solution of 6-chloro-7-fluoro-1H-pyrazolo[4,3-c]pyridine (1000 mg, 5.83 mmol, 1 equiv) in DMF (10 mL) was added potassium carbonate (2417 mg, 17.5 mmol, 3 equiv) and 2,2,2-trifluoroethyl trifluoromethanesulfonate (1.01 mL, 6.99 mmol, 1.2 equiv). The reaction mixture was heated to 80° C. After 1 hour, the reaction mixture was diluted with water (50 mL) and extracted with 50% EtOAc/Hex (3×50 mL). The combined organic layers were dried over Na$_2$SO$_4$, filtered, and concentrated. Purification was accomplished by SiO$_2$ chromatography (0-100% EtOAc/Hex), affording 6-chloro-7-fluoro-1-(2,2,2-trifluoroethyl)-1H-pyrazolo[4,3-c]pyridine. $^1$H NMR (400 MHz, DMSO-d6) δ 8.87 (s, 1H), 8.60 (d, J=2.3 Hz, 1H), 5.49 (q, J=8.9 Hz, 2H). ES/MS m/z: 254.00 [M+H].

Intermediate 761. 7-bromo-1-(trifluoromethyl)-2,3-dihydro-1H-benzo[d]pyrrolo[1,2-a]imidazole

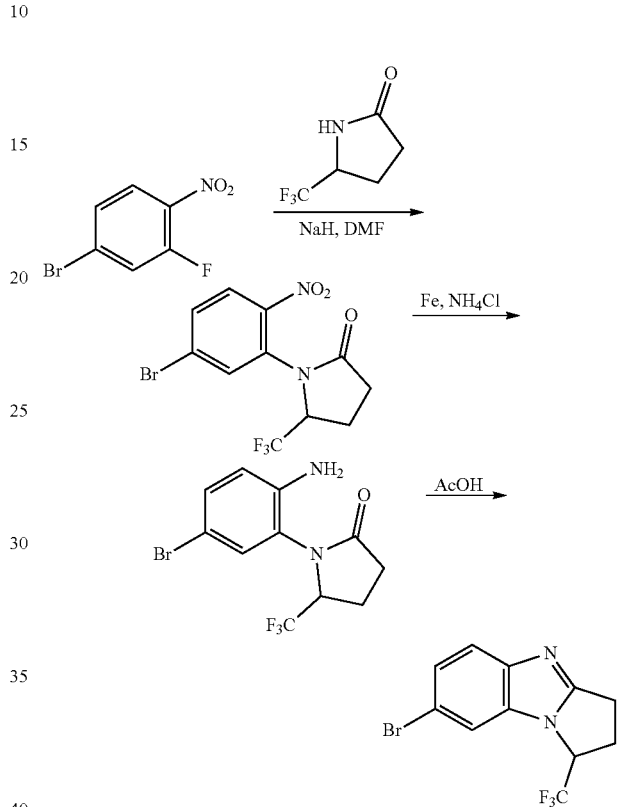

Step 1: To a cooled (0° C.) solution of 5-(trifluoromethyl)pyrrolidin-2-one (835 mg, 5.45 mmol, 2 equiv) in DMF (5 mL) was added 60% sodium hydride (209 mg, 5.45 mmol, 2 equiv). After 5 minutes, 4-bromo-2-fluoro-1-nitrobenzene (600 mg, 2.73 mmol, 1 equiv) was added. After stirring for 1 hour at 0° C. and an additional 1 hour at room temperature, the reaction mixture was quenched with saturated aqueous NaHCO$_3$ (5 mL) and directly purified by SiO$_2$ chromatography (0-100% EtOAc/Hex), affording 1-(5-bromo-2-nitrophenyl)-5-(trifluoromethyl)pyrrolidin-2-one. $^1$H NMR (400 MHz, DMSO-d6, diagnostic peaks) δ 8.12 (d, J=2.1 Hz, 1H), 7.98 (d, J=8.7 Hz, 1H), 7.78 (dd, J=8.7, 2.1 Hz, 1H), 5.47-5.34 (m, 1H).

Step 2: To a solution of 1-(5-bromo-2-nitrophenyl)-5-(trifluoromethyl)pyrrolidin-2-one (1240 mg, 3.51 mmol, 1 equiv) in 3:1 EtOH/H$_2$O (8 mL) was added iron (981 mg, 17.6 mmol, 5 equiv) and ammonium chloride (564 mg, 10.5 mmol, 3 equiv). The reaction mixture was heated to 80° C. After 3 hours, the reaction mixture was filtered with EtOAc washings (10 mL). The layers were separated, and the aqueous layer was extracted with EtOAc (3×20 mL). The combined organic layers were dried over Na$_2$SO$_4$, filtered, and concentrated to afford 1-(2-amino-5-bromophenyl)-5-(trifluoromethyl)pyrrolidin-2-one. This material was used in the next step without purification. ES/MS m/z: 323.00 [M+H].

Step 3: A solution of 1-(2-amino-5-bromophenyl)-5-(tri-fluoromethyl)pyrrolidin-2-one (1135 mg) in AcOH (10 mL) was heated to 110° C. After 3 hours, the reaction mixture was cooled to room temperature and concentrated. The resulting residue was dissolved in EtOAc (20 mL) and washed with saturated aqueous NaHCO₃ (20 mL). The layers were separated, and the organic layer was concentrated and purified by SiO₂ chromatography (0-100% EtOAc/Hex), affording 7-bromo-1-(trifluoromethyl)-2,3-dihydro-1H-benzo[d]pyrrolo[1,2-a]imidazole. ¹H NMR (400 MHz, DMSO-d6, diagnostic peaks) δ 7.70 (bs, 1H), 7.57 (d, J=8.6 Hz, 1H), 7.37 (dd, J=8.6, 2.0 Hz, 1H), 5.60-5.47 (m, 1H). ES/MS m/z: 307.00 [M+H].

Intermediate 762.
2-chloro-4-(2-(trifluoromethyl)phenyl)pyridine

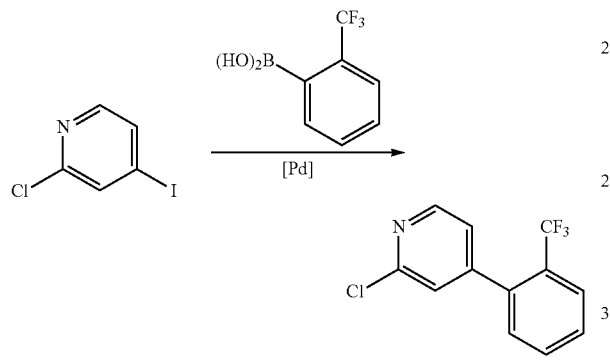

A solution of 2-chloro-4-iodopyridine (200 mg, 0.84 mmol, 1 equiv), (2-(trifluoromethyl)phenyl)boronic acid (175 mg, 0.92 mmol, 1.1 equiv), potassium carbonate (346 mg, 2.51 mmol, 3 equiv), and (dppf)PdCl₂—CH₂Cl₂ (15 mg, 2.5 mol %) in 4:1 THF/H₂O (2 mL) was heated to 80° C. After 1 hour, the reaction mixture was directly purified by SiO₂ chromatography (0-100% EtOAc/Hex), affording 2-chloro-4-(2-(trifluoromethyl)phenyl)pyridine. ¹H NMR (400 MHz, DMSO-d6) δ 8.50 (d, J=5.1 Hz, 1H), 7.90 (d, J=7.9 Hz, 1H), 7.82-7.76 (m, 1H), 7.75-7.66 (m, 1H), 7.54 (s, 1H), 7.50 (d, J=7.6 Hz, 1H), 7.43-7.40 (m, 1H). ¹⁹F NMR (376 MHz, DMSO-d6) δ -55.90. ES/MS m/z: 258.10 [M+H].

Intermediate 763.
2-chloro-4-(2,4-difluorophenyl)pyridine

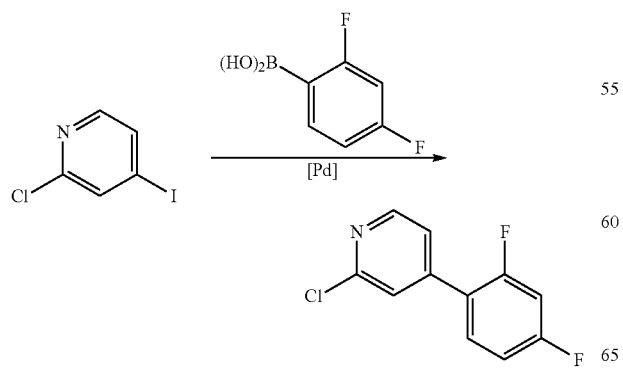

A solution of 2-chloro-4-iodopyridine (200 mg, 0.84 mmol, 1 equiv), (2,4-difluorophenyl)boronic acid (145 mg, 0.92 mmol, 1.1 equiv), potassium carbonate (346 mg, 2.51 mmol, 3 equiv), and (dppf)PdCl₂—CH₂Cl₂ (15 mg, 2.5 mol %) in 4:1 THF/H₂O (2 mL) was heated to 80° C. After 1 hour, the reaction mixture was directly purified by SiO₂ chromatography (0-100% EtOAc/Hex), affording 2-chloro-4-(2,4-difluorophenyl)pyridine. ¹H NMR (400 MHz, DMSO-d6) δ 8.51 (d, J=5.2 Hz, 1H), 7.82-7.74 (m, 1H), 7.73-7.70 (m, 1H), 7.64-7.60 (m, 1H), 7.54-7.43 (m, 1H), 7.33-7.22 (m, 1H). ¹⁹F NMR (376 MHz, DMSO-d6) δ -108.24-108.36 (m), -112.98--113.13 (m). ES/MS m/z: 226.00 [M+H].

Intermediate 764.
7-chloro-5-(2,2,2-trifluoroethoxy)quinoline

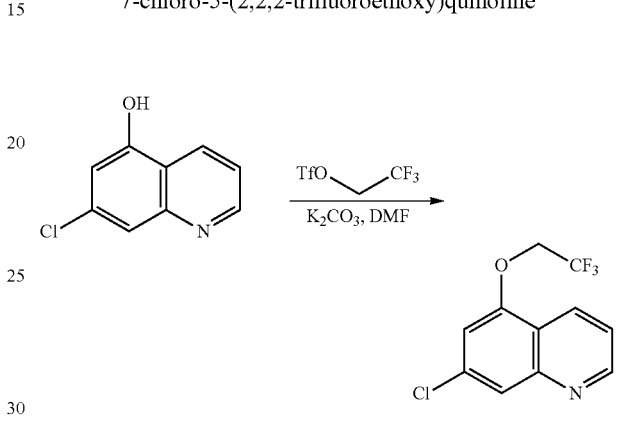

To a solution of 7-chloroquinolin-5-ol (500 mg, 2.78 mmol, 1 equiv) in DMF (6 mL) was added potassium carbonate (1154 mg, 8.35 mmol, 3 equiv) and 2,2,2-trifluoroethyl trifluoromethanesulfonate (0.602 mL, 4.18 mmol, 1.5 equiv). The reaction mixture was heated to 80° C. After 1 hour, the reaction mixture was directly purified by SiO₂ chromatography (0-100% EtOAc/Hex), affording 7-chloro-5-(2,2,2-trifluoroethoxy)quinoline. ¹H NMR (400 MHz, DMSO-d6) δ 9.00-8.94 (m, 1H), 8.50-8.43 (m, 1H), 7.80-7.73 (m, 1H), 7.61 (dd, J=8.5, 4.3 Hz, 1H), 7.36 (d, J=1.9 Hz, 1H), 5.08 (q, J=8.8 Hz, 2H). ES/MS m/z: 262.10 [M+H].

Intermediate 765. racemic potassium
(3-(3,4-difluorophenyl)-2,2-difluorocyclopropyl)
trifluoroborate

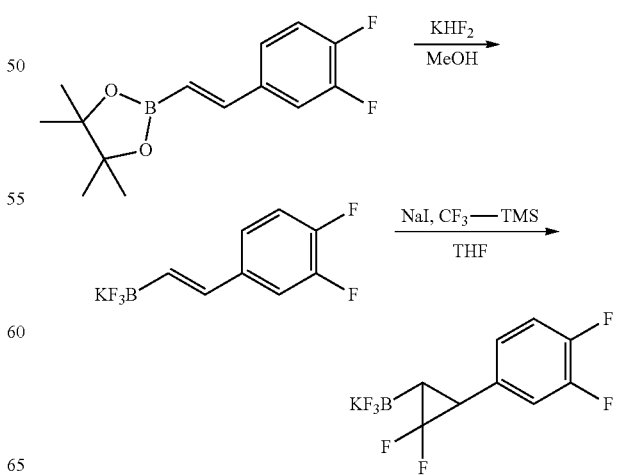

Step 1: To a solution of (E)-2-(3,4-difluorostyryl)-4,4,5,5-tetramethyl-1,3,2-dioxaborolane (1000 mg, 3.76 mmol, 1 equiv) in MeOH (15 mL) was added potassium hydrogen difluoride (1761 mg, 22.5 mmol, 6 equiv) and heated to 80° C. After 8 hours, the reaction mixture was cooled to room temperature and concentrated. The resulting residue was triturated with 50% Et$_2$O in heptane (10 mL). After 10 minutes, the precipitate was collected by filtration, rinsing with Et$_2$O (10 mL), and dried under reduced pressure, affording crude potassium (E)-(3,4-difluorostyryl)trifluoroborate. This material was used in the next step without purification.

Step 2: A solution of potassium (E)-(3,4-difluorostyryl)trifluoroborate (100 mg, 0.72 mmol, 1 equiv) and sodium iodide (43 mg, 0.29 mmol, 0.4 equiv) in THF (15 mL) was heated to reflux. 2M THF (Trifluoromethyl)trimethylsilane (1.8 mL, 3.6 mmol, 5 equiv) was added dropwise. After 30 minutes, the reaction mixture was cooled to room temperature and filtered. The filtrate was concentrated affording crude potassium (3-(3,4-difluorophenyl)-2,2-difluorocyclopropyl) trifluoroborate. This material was used without purification. $^1$H NMR (400 MHz, DMSO-d6) δ 7.37-7.24 (m, 1H), 7.23-7.12 (m, 1H), 7.03-6.95 (m, 1H), 2.44-2.31 (m, 1H), 0.88-0.70 (m, 1H).

Intermediate 766. racemic 4,4,5,5-tetramethyl-24 (1S,2S)-2-(4-(2,2,2-trifluoroethoxy)phenyl)cyclopropyl)-1,3,2-dioxaborolane

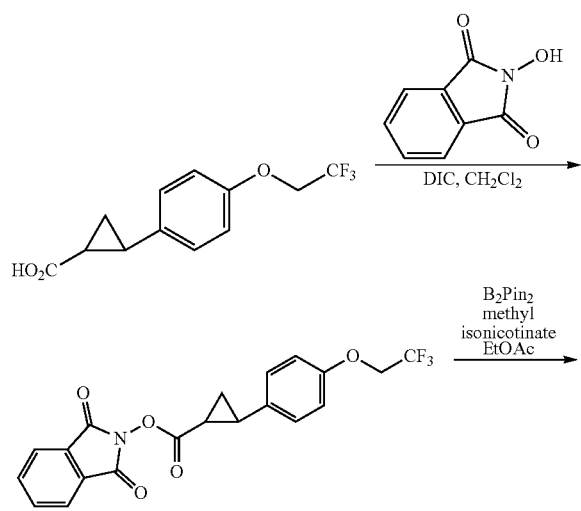

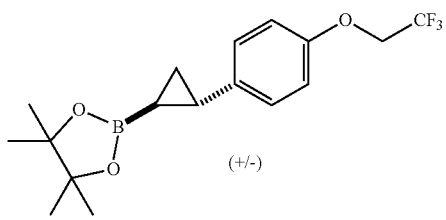

Step 1: To a solution of 2-(4-(2,2,2-trifluoroethoxy)phenyl)cyclopropane-1-carboxylic acid (1000 mg, 3.84 mmol, 1 equiv) in CH$_2$Cl$_2$ (10 mL) was added diisopropylmethanediimine (0.66 mL, 4.23 mmol, 1.1 equiv), N,N-dimethylpyridin-4-amine (47 mg, 10 mol %), and 2-hydroxyisoindoline-1,3-dione (690 mg, 4.23 mmol, 1.1 equiv). After 18 hours, the reaction mixture was filtered over celite with CH$_2$Cl$_2$ washings and concentrated. The residue was purified by SiO$_2$ chromatography (0-100% EtOAc/Hex), affording 1,3-dioxoisoindolin-2-yl 2-(4-(2,2,2-trifluoroethoxy)phenyl)cyclopropane-1-carboxylate (mixture of cis and trans diastereomers).

Step 2: To a solution of 1,3-dioxoisoindolin-2-yl 2-(4-(2,2,2-trifluoroethoxy)phenyl)cyclopropane-1-carboxylate (781 mg, 1.73 mmol, 1 equiv) in EtOAc (10 mL) was added B$_2$Pin$_2$ (881 mg, 3.47 mmol, 2 equiv) and methyl isonicotinate (0.10 mL, 0.87 mmol, 0.5 equiv). The resulting mixture was heated to 80° C. under an atmosphere of argon. After 16 hours, the reaction mixture was filtered, concentrated, and purified by SiO$_2$ chromatography (0-50% EtOAc/Hex), affording racemic 4,4,5,5-tetramethyl-2-((2S,2S)-2-(4-(2,2,2-trifluoroethoxy)phenyl)cyclopropyl)-1,3,2-dioxaborolane. $^1$H NMR (400 MHz, Chloroform-d) δ 7.08-6.98 (m, 2H), 6.89-6.78 (m, 2H), 4.31 (q, J=8.2 Hz, 2H), 2.10-2.05 (m, 1H), 1.25-1.23 (m, 12H), 1.17-1.09 (m, 1H), 0.98-0.89 (m, 1H), 0.29-0.15 (m, 1H).

Intermediate 767. 2-((1S,2S)-2-(4-(2,2-difluoroethoxy)phenyl)cyclopropyl)-4,4,5,5-tetramethyl-1,3,2-dioxaborolane

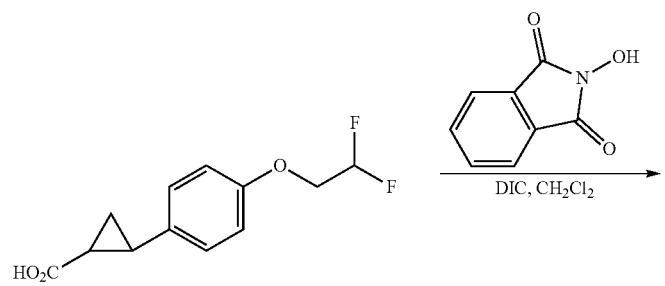

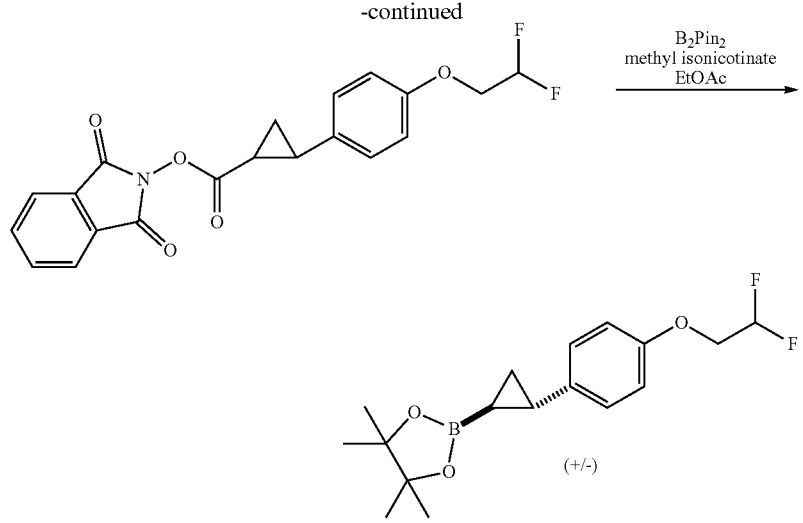

Step 1: To a solution of 2-(4-(2,2-difluoroethoxy)phenyl)cyclopropane-1-carboxylic acid (1000 mg, 4.13 mmol, 1 equiv) in CH$_2$Cl$_2$ (10 mL) was added diisopropylmethanediimine (0.71 mL, 4.54 mmol, 1.1 equiv), N,N-dimethylpyridin-4-amine (50 mg, 10 mol %), and 2-hydroxyisoindoline-1,3-dione (741 mg, 4.54 mmol, 1.1 equiv). After 3 hours, the reaction mixture was filtered over celite with CH$_2$Cl$_2$ washings and concentrated. The residue was purified by SiO$_2$ chromatography (0-100% EtOAc/Hex), affording 1,3-dioxoisoindolin-2-yl 2-(4-(2,2-difluoroethoxy)phenyl)cyclopropane-1-carboxylate (mixture of cis and trans diastereomers).

Step 2: To a solution of 1,3-dioxoisoindolin-2-yl 2-(4-(2,2-difluoroethoxy)phenyl)cyclopropane-1-carboxylate (1500 mg, 3.49 mmol, 1 equiv) in EtOAc (20 mL) was added B2Pin2 (1770 mg, 6.97 mmol, 2 equiv) and methyl isonicotinate (0.21 mL, 1.74 mmol, 0.5 equiv). The resulting mixture was heated to 80° C. under an atmosphere of argon. After 16 hours, the reaction mixture was filtered, concentrated, and purified by SiO$_2$ chromatography (0-50% EtOAc/Hex), affording racemic 2-((2S,2S)-2-(4-(2,2-difluoroethoxy)phenyl)cyclopropyl)-4,4,5,5-tetramethyl-1,3,2-dioxaborolane. $^1$H NMR (400 MHz, Chloroform-d) δ 7.08-7.00 (m, 2H), 6.86-6.79 (m, 2H), 6.08 (tt, J=55.2, 4.1 Hz, 1H), 4.24-4.09 (m, 2H), 2.14-2.04 (m, 1H), 1.31-1.23 (m, 12H), 1.18-1.10 (m, 1H), 1.00-0.92 (m, 1H), 0.30-0.19 (m, 1H).

Intermediate 768. 2-((1S,2S)-2-(4-(difluoromethoxy)phenyl)cyclopropyl)-4,4,5,5-tetramethyl-1,3,2-dioxaborolane

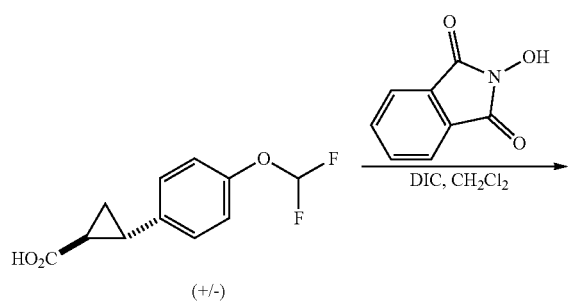

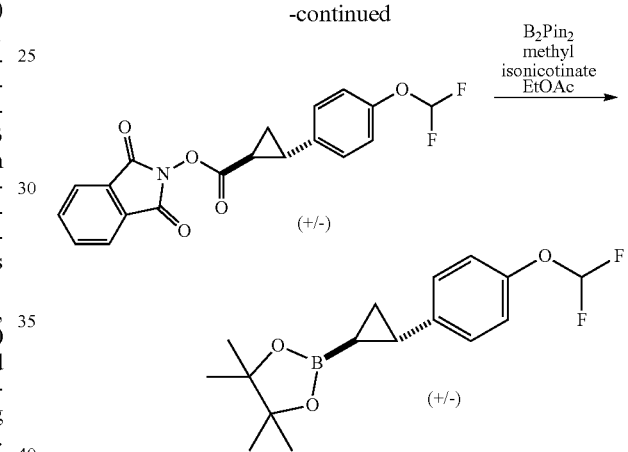

Step 1: To a solution of racemic (1S,2S)-2-(4-(difluoromethoxy)phenyl)cyclopropane-1-carboxylic acid (857 mg, 3.76 mmol, 1 equiv) in CH$_2$Cl$_2$ (12 mL) was added diisopropylmethanediimine (0.64 mL, 4.13 mmol, 1.1 equiv), N,N-dimethylpyridin-4-amine (46 mg, 10 mol %), and 2-hydroxyisoindoline-1,3-dione (674 mg, 4.13 mmol, 1.1 equiv). After 2 hours, the reaction mixture was filtered over celite with CH$_2$Cl$_2$ washings and concentrated. The residue was purified by SiO$_2$ chromatography (0-100% EtOAc/Hex), affording racemic 1,3-dioxoisoindolin-2-yl (1S,2S)-2-(4-(difluoromethoxy)phenyl)cyclopropane-1-carboxylate. $^1$H NMR (400 MHz, Chloroform-d) δ 7.92-7.86 (m, 2H), 7.84-7.77 (m, 2H), 7.21-7.15 (m, 2H), 7.12-7.05 (m, 2H), 6.50 (t, J=73.8 Hz, 1H), 2.83-2.73 (m, 1H), 2.22-2.15 (m, 1H), 1.88-1.78 (m, 1H), 1.62-1.57 (m, 1H).

Step 2: To a solution of racemic 1,3-dioxoisoindolin-2-yl (1S,2S)-2-(4-(difluoromethoxy)phenyl)cyclopropane-1-carboxylate (1301 mg, 3.14 mmol, 1 equiv) in EtOAc (15 mL) was added B$_2$Pin$_2$ (1593 mg, 6.27 mmol, 2 equiv) and methyl isonicotinate (0.19 mL, 1.57 mmol, 0.5 equiv). The resulting mixture was heated to 80° C. under an atmosphere of argon. After 8 hours, the reaction mixture was filtered, concentrated, and purified by SiO$_2$ chromatography (0-50% EtOAc/Hex), affording racemic 2-((2S,2S)-2-(4-(difluoromethoxy)phenyl)cyclopropyl)-4,4,5,5-tetramethyl-1,3,2- dioxaborolane. ¹H NMR (400 MHz, Chloroform-d) δ 7.09-6.95 (m, 4H), 6.44 (t, J=74.3 Hz, 1H), 2.13-2.05 (m, 1H), 1.25 (s, 6H), 1.24 (s, 6H), 1.19-1.13 (m, 1H), 1.00-0.93 (m, 1H), 0.29-0.19 (m, 1H).

Intermediate 769. 2-fluoro-4-((1S,2S)-2-(4,4,5,5-tetramethyl-1,3,2-dioxaborolan-2-yl)cyclopropyl)benzonitrile

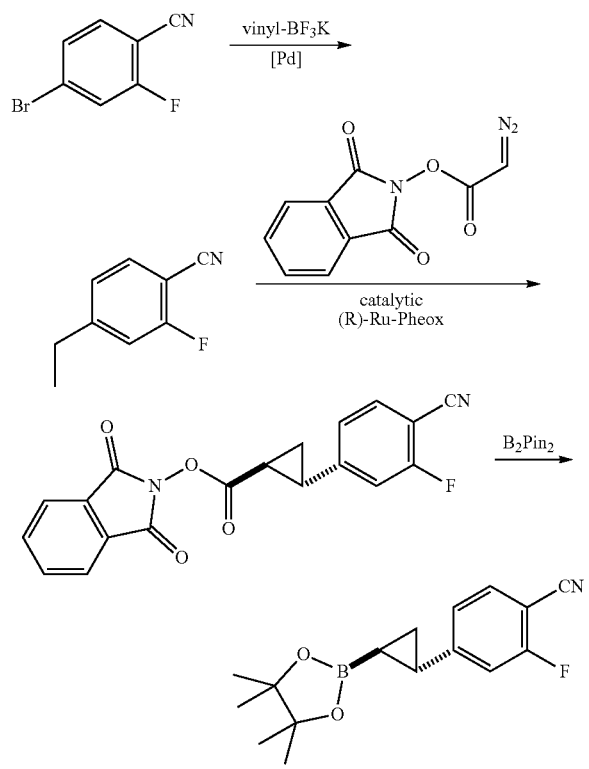

Step 1: A solution of 4-bromo-2-fluorobenzonitrile (2500 mg, 12.5 mmol, 1 equiv), vinyl trifluoroborate (1842 mg, 13.7 mmol, 1.1 equiv), potassium carbonate (5183 mg, 37.5 mmol, 3 equiv), and (dppf)PdCl₂—CH₂Cl₂ (457 mg, 5 mol %) in 9:1 THF/H₂O (32 mL) was heated to 85° C. After 20 hours, the reaction mixture was cooled to room temperature, diluted with H₂O (25 mL), and extracted with CH₂Cl₂ (3×50 mL). The combined organic layers were dried over Na₂SO₄, filtered, and concentrated. Purification was accomplished by SiO₂ chromatography (0-50% EtOAc/Hex), affording 2-fluoro-4-vinylbenzonitrile. ¹H NMR (400 MHz, Chloroform-d) δ 7.61-7.53 (m, 1H), 7.30-7.19 (m, 2H), 6.70 (dd, J=17.5, 10.9 Hz, 1H), 5.89 (d, J=17.5 Hz, 1H), 5.52 (d, J=10.9 Hz, 1H).

Step 2: To a cooled (0° C.) solution of 2-fluoro-4-vinylbenzonitrile (1670 mg, 11.3 mmol, 1 equiv) and Ru(II)-(R)-Pheox catalyst [Tetrakis(acetonitrile)[2-[(4R)-4,5-dihydro-4-phenyl-2-oxazolyl-/V]phenyl]ruthenium(II) Hexafluorophosphate](72 mg, 1 mol %) in CH₂Cl₂ (113 mL, 0.1M) was added a 0.2M solution of 1,3-dioxoisoindolin-2-yl 2-diazoacetate (2886 mg, 12.5 mmol, 1.1 equiv) in CH₂Cl₂ over 40 minutes. After an additional 5 hours at 0° C., the reaction mixture was diluted with MeOH (10 mL) and concentrated to ~10 mL. Purification was accomplished by SiO₂ chromatography (0-70% EtOAc/Hex), affording 1,3-dioxoisoindolin-2-yl (1S,2S)-2-(4-cyano-3-fluorophenyl)cyclopropane-1-carboxylate. The enantiomeric excess was determined to be 95% ee via SFC chiral analysis. ¹H NMR (400 MHz, Chloroform-d) δ 7.93-7.88 (m, 2H), 7.84-7.79 (m, 2H), 7.59 (dd, J=8.1, 6.6 Hz, 1H), 7.07 (dd, J=8.1, 1.7 Hz, 1H), 7.01 (dd, J=9.8, 1.7 Hz, 1H), 2.84-2.75 (m, 1H), 2.34-2.26 (m, 1H), 1.98-1.89 (m, 1H), 1.69-1.61 (m, 1H). ES/MS m/z: 373.00 [M+Na].

Step 3: To a solution of 1,3-dioxoisoindolin-2-yl (1S,2S)-2-(4-cyano-3-fluorophenyl)cyclopropane-1-carboxylate (2830 mg, 8.08 mmol, 1 equiv) in EtOAc (50 mL) was added B2Pin2 (4103 mg, 16.2 mmol, 2 equiv) and methyl isonicotinate (0.48 mL, 4.04 mmol, 0.5 equiv). The resulting mixture was heated to 80° C. under an atmosphere of argon. After 16 hours, the reaction mixture was filtered, concentrated, and purified by SiO₂ chromatography (0-20% EtOAc/Hex), affording 2-fluoro-4-((2S,2S)-2-(4,4,5,5-tetramethyl-1,3,2-dioxaborolan-2-yl)cyclopropyl)benzonitrile. ¹H NMR (400 MHz, Chloroform-d) δ 7.46 (dd, J=8.1, 6.7 Hz, 1H), 6.93 (dd, J=8.1, 1.6 Hz, 1H), 6.86 (dd, J=10.4, 1.6 Hz, 1H), 2.15-2.06 (m, 1H), 1.34-1.18 (m, 13H), 1.09-1.00 (m, 1H), 0.42-0.31 (m, 1H).

Intermediate 770. 4,4,5,5-tetramethyl-24(1S,2S)-2-(4-(trifluoromethoxy)phenyl)cyclopropyl)-1,3,2-dioxaborolane

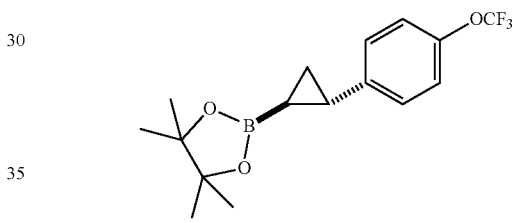

4,4,5,5-tetramethyl-2-((2S,2S)-2-(4-(trifluoromethoxy)phenyl)cyclopropyl)-1,3,2-dioxaborolane was prepared in the manner described for Intermediate 769 (steps 2-3), but replacing 2-fluoro-4-vinylbenzonitrile with 1-(trifluoromethoxy)-4-vinyl-benzene. ¹H NMR (400 MHz, Chloroform-d) δ 7.10 (s, 4H), 2.16-2.09 (m, 1H), 1.28 (s, 6H), 1.27 (s, 6H), 1.23-1.16 (m, 1H), 1.03-0.96 (m, 1H), 0.34-0.26 (m, 1H). Passed to Hai for Suzuki reactions.

Intermediate 771. 2-chloro-5-((1S,2S)-2-(4,4,5,5-tetramethyl-1,3,2-dioxaborolan-2-yl)cyclopropyl)benzonitrile

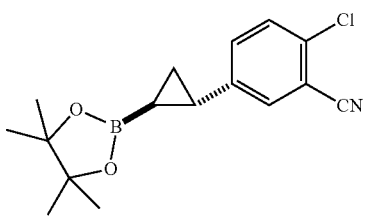

2-chloro-54(1S,2S)-2-(4,4,5,5-tetramethyl-1,3,2-dioxaborolan-2-yl)cyclopropyl)benzonitrile was prepared in the manner described for Intermediate 769 (steps 1-3), but replacing 4-bromo-2-fluorobenzonitrile with 5-bromo-2-chloro-benzonitrile. ¹H NMR (400 MHz, Chloroform-d) δ

7.38-7.32 (m, 2H), 7.19 (dd, J=8.5, 2.3 Hz, 1H), 2.11-2.05 (m, 1H), 1.26-1.23 (m, 13H), 1.03-0.96 (m, 1H), 0.32-0.23 (m, 1H).

Intermediate 772. 4,4,5,5-tetramethyl-2-((1S,2S)-2-(4-(trifluoromethyl)phenyl)cyclopropyl)-1,3,2-dioxaborolane

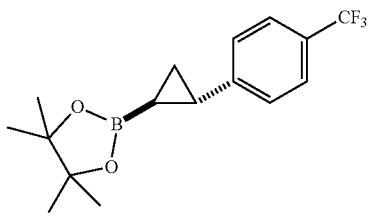

4,4,5,5-tetramethyl-2-((2S,2S)-2-(4-(trifluoromethyl)phenyl)cyclopropyl)-1,3,2-dioxaborolane was prepared in the manner described for Intermediate 769 (steps 2-3), but replacing 2-fluoro-4-vinylbenzonitrile with 1-(trifluoromethyl)-4-vinyl-benzene. ¹H NMR (400 MHz, Chloroform-d) δ 7.50 (d, J=8.1 Hz, 2H), 7.18 (d, J=8.1 Hz, 2H), 2.20-2.11 (m, 1H), 1.31-1.20 (m, 13H), 1.11-1.02 (m, 1H), 0.41-0.31 (m, 1H).

Intermediate 773. 2-((2S,2S)-2-(4-(difluoromethoxy)phenyl)cyclopropyl)-4,4,5,5-tetramethyl-1,3,2-dioxaborolane

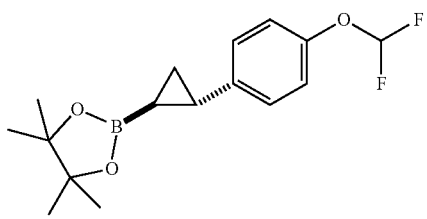

2-((2S,2S)-2-(4-(difluoromethoxy)phenyl)cyclopropyl)-4,4,5,5-tetramethyl-1,3,2-dioxaborolane was prepared in the manner described for Intermediate 769 (steps 1-3), but replacing 4-bromo-2-fluorobenzonitrile with 1-bromo-4-(difluoromethoxy)benzene. ¹H NMR (400 MHz, Chloroform-d) δ 7.09-6.95 (m, 4H), 6.44 (t, J=74.3 Hz, 1H), 2.13-2.05 (m, 1H), 1.25 (s, 6H), 1.24 (s, 6H), 1.19-1.13 (m, 1H), 1.00-0.93 (m, 1H), 0.29-0.19 (m, 1H).

Intermediate 774. 2,6-difluoro-4-((2S,2S)-2-(4,4,5,5-tetramethyl-1,3,2-dioxaborolan-2-yl)cyclopropyl)benzonitrile

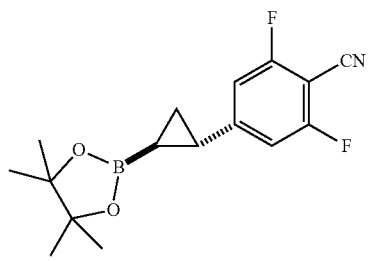

2,6-difluoro-4-(1S,2S)-2-(4,4,5,5-tetramethyl-1,3,2-dioxaborolan-2-yl)cyclopropyl)benzonitrile was prepared in the manner described for Intermediate 769 (steps 1-3), but replacing 4-bromo-2-fluorobenzonitrile with 4-bromo-2,6-difluoro-benzonitrile. ¹H NMR (400 MHz, Chloroform-d) δ 6.74-6.67 (m, 2H), 2.12-2.06 (m, 1H), 1.35-1.20 (m, 13H), 1.11-1.01 (m, 1H), 0.42-0.32 (m, 1H).

Intermediate 775. 2,3-difluoro-4-((2S,2S)-2-(4,4,5,5-tetramethyl-1,3,2-dioxaborolan-2-yl)cyclopropyl)benzonitrile

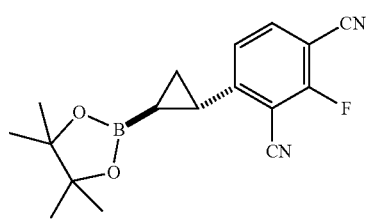

2,3-difluoro-4-(1S,2S)-2-(4,4,5,5-tetramethyl-1,3,2-dioxaborolan-2-yl)cyclopropyl)benzonitrile was prepared in the manner described for Intermediate 769 (steps 1-3), but replacing 4-bromo-2-fluorobenzonitrile with 4-bromo-2,3-difluoro-benzonitrile. ¹H NMR (400 MHz, Chloroform-d) δ 7.27-7.19 (m, 1H), 6.74-6.63 (m, 1H), 2.40-2.30 (m, 1H), 1.37-1.19 (m, 13H), 1.14-1.08 (m, 1H), 0.44-0.34 (m, 1H).

Intermediate 776. 2-methoxy-4-((1S,2S)-2-(4,4,5,5-tetramethyl-1,3,2-dioxaborolan-2-yl)cyclopropyl)benzonitrile

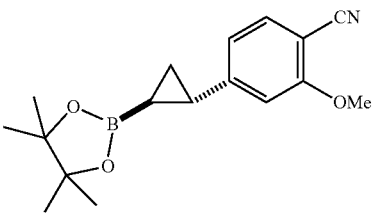

2-methoxy-4-(1S,2S)-2-(4,4,5,5-tetramethyl-1,3,2-dioxaborolan-2-yl)cyclopropyl)benzonitrile was prepared in the manner described for Intermediate 769 (steps 2-3), but replacing 2-fluoro-4-vinylbenzonitrile with 2-methoxy-4-vinyl-benzonitrile. ¹H NMR (400 MHz, Chloroform-d) δ 7.43 (d, J=8.3 Hz, 1H), 6.71-6.64 (m, 2H), 3.92 (s, 3H), 2.18-2.09 (m, 1H), 1.32-1.19 (m, 13H), 1.11-1.01 (m, 1H), 0.44-0.35 (m, 1H).

Intermediate 777. 2-methyl-4-(1S,2S)-2-(4,4,5,5-tetramethyl-1,3,2-dioxaborolan-2-yl)cyclopropyl)benzonitrile

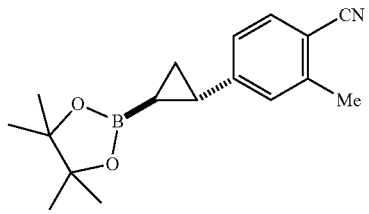

2-methyl-4-(1S,2S)-2-(4,4,5,5-tetramethyl-1,3,2-dioxaborolan-2-yl)cyclopropyl)benzonitrile was prepared in the manner described for Intermediate 769 (steps 1-3), but replacing 4-bromo-2-fluorobenzonitrile with 4-bromo-2-methyl-benzonitrile. $^1$H NMR (400 MHz, Chloroform-d) δ 7.47 (d, J=8.1 Hz, 1H), 7.02 (s, 1H), 6.97-6.90 (m, 1H), 2.51 (s, 3H), 2.13-2.07 (m, 1H), 1.28-1.25 (m, 13H), 1.10-1.02 (m, 1H), 0.40-0.31 (m, 1H).

Intermediate 778. 2-cyclopropyl-4-(1S,2S)-2-(4,4,5,5-tetramethyl-1,3,2-dioxaborolan-2-yl)cyclopropyl)benzonitrile

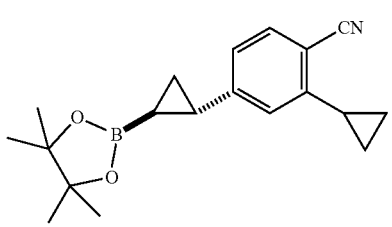

2-cyclopropyl-4-(1S,2S)-2-(4,4,5,5-tetramethyl-1,3,2-dioxaborolan-2-yl)cyclopropyl)benzonitrile was prepared in the manner described for Intermediate 769 (steps 1-3), but replacing 4-bromo-2-fluorobenzonitrile with 4-bromo-2-cyclopropyl-benzonitrile.

Intermediate 779. 2-fluoro-6-methyl-4-(1S,2S)-2-(4,4,5,5-tetramethyl-1,3,2-dioxaborolan-2-yl)cyclopropyl)benzonitrile

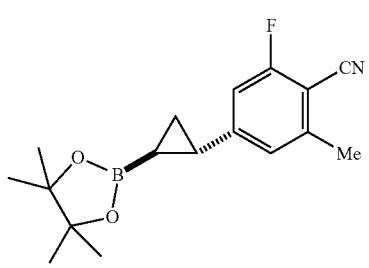

2-fluoro-6-methyl-4-((1S,2S)-2-(4,4,5,5-tetramethyl-1,3,2-dioxaborolan-2-yl)cyclopropyl)benzonitrile was prepared in the manner described for Intermediate 769 (steps 1-3), but replacing 4-bromo-2-fluorobenzonitrile with 4-bromo-2-fluoro-6-methyl-benzonitrile. $^1$H NMR (400 MHz, Chloroform-d) δ 6.80 (s, 1H), 6.69-6.59 (m, 1H), 2.48 (s, 3H), 2.11-2.03 (m, 1H), 1.30-1.21 (m, 13H), 1.07-0.99 (m, 1H), 0.38-0.28 (m, 1H).

Intermediate 780. 2-chloro-4-((2S,2S)-2-(4,4,5,5-tetramethyl-1,3,2-dioxaborolan-2-yl)cyclopropyl)benzonitrile

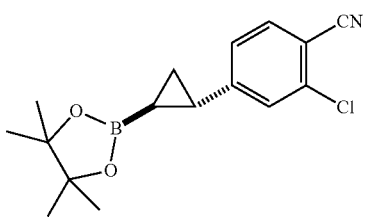

2-chloro-4-(1S,2S)-2-(4,4,5,5-tetramethyl-1,3,2-dioxaborolan-2-yl)cyclopropyl)benzonitrile was prepared in the manner described for Intermediate 769 (steps 1-3), but replacing 4-bromo-2-fluorobenzonitrile with 4-bromo-2-chloro-benzonitrile. $^1$H NMR (400 MHz, Chloroform-d) δ 7.51 (d, J=8.0 Hz, 1H), 7.18 (d, J=1.7 Hz, 1H), 7.00 (dd, J=8.0, 1.7 Hz, 1H), 2.13-2.05 (m, 1H), 1.33-1.20 (m, 13H), 1.10-1.01 (m, 1H), 0.42-0.30 (m, 1H).

Intermediate 781. 2,5-difluoro-4-((2S,2S)-2-(4,4,5,5-tetramethyl-1,3,2-dioxaborolan-2-yl)cyclopropyl)benzonitrile

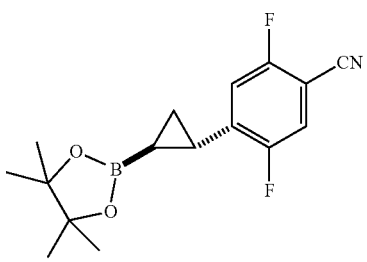

2,5-difluoro-4-(1S,2S)-2-(4,4,5,5-tetramethyl-1,3,2-dioxaborolan-2-yl)cyclopropyl)benzonitrile was prepared in the manner described for Intermediate 769 (steps 1-3), but replacing 4-bromo-2-fluorobenzonitrile with 4-bromo-2,5-difluoro-benzonitrile. $^1$H NMR (400 MHz, Chloroform-d) δ 7.25-7.18 (m, 1H), 6.75-6.61 (m, 1H), 2.37-2.27 (m, 1H), 1.37 1.21 (m, 13H), 1.13-1.04 (m, 1H), 0.41-0.31 (m, 1H).

Intermediate 782. 6-((2S,2S)-2-(4,4,5,5-tetramethyl-1,3,2-dioxaborolan-2-yl)cyclopropyl)-2-(trifluoromethyl)benzo[d]thiazole

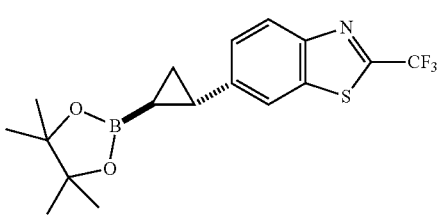

6-((1S,2S)-2-(4,4,5,5-tetramethyl-1,3,2-dioxaborolan-2-yl)cyclopropyl)-2-(trifluoromethyl)benzo[d]thiazole was prepared in the manner described for Intermediate 769 (steps 1-3), but replacing 4-bromo-2-fluorobenzonitrile with 6-bromo-2-(trifluoromethyl)-1,3-benzothiazole. $^1$H NMR (400 MHz, Chloroform-d) δ 8.05 (d, J=8.6 Hz, 1H), 7.69 (d, J=1.8 Hz, 1H), 7.30 (dd, J=8.6, 1.8 Hz, 1H), 2.32-2.22 (m, 1H), 1.32-1.21 (m, 13H), 1.15-1.04 (m, 1H), 0.46-0.33 (m, 1H).

Intermediate 783. 4-fluoro-6-((1S,2S)-2-(4,4,5,5-tetramethyl-1,3,2-dioxaborolan-2-yl)cyclopropyl)-1-(2,2,2-trifluoroethyl)-1H-indazole

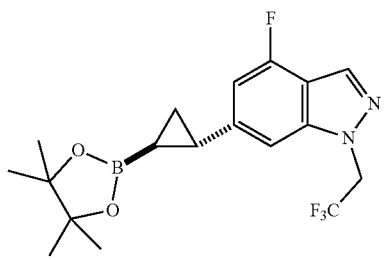

4-fluoro-6-((2S,2S)-2-(4,4,5,5-tetramethyl-1,3,2-dioxaborolan-2-yl)cyclopropyl)-1-(2,2,2-trifluoroethyl)-1H-indazole was prepared in the manner described for Intermediate 769 (steps 1-3), but replacing 4-bromo-2-fluorobenzonitrile with 6-bromo-4-fluoro-1-(2,2,2-trifluoroethyl)-1H-indazole. $^1$H NMR (400 MHz, Chloroform-d) δ 8.05 (s, 1H), 6.95 (s, 1H), 6.55 (d, J=11.0 Hz, 1H), 4.88 (q, J=8.4 Hz, 2H), 2.31-2.15 (m, 1H), 1.32-1.20 (m, 13H), 1.12-1.01 (m, 1H), 0.44-0.32 (m, 1H). ES/MS m/z: 385.10 [M+H].

Intermediate 784. 5-fluoro-6-((1S,2S)-2-(4,4,5,5-tetramethyl-1,3,2-dioxaborolan-2-yl)cyclopropyl)-1-(2,2,2-trifluoroethyl)-1H-indazole

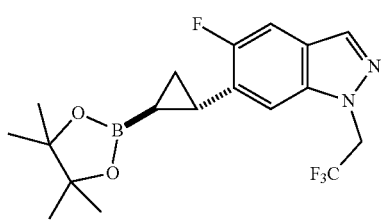

5-fluoro-6-((1S,2S)-2-(4,4,5,5-tetramethyl-1,3,2-dioxaborolan-2-yl)cyclopropyl)-1-(2,2,2-trifluoroethyl)-1H-indazole was prepared in the manner described for Intermediate 769 (steps 1-3), but replacing 4-bromo-2-fluorobenzonitrile with 6-bromo-5-fluoro-1-(2,2,2-trifluoroethyl)-1H-indazole. $^1$H NMR (400 MHz, Chloroform-d) δ 7.97 (s, 1H), 7.31 (d, J=9.6 Hz, 1H), 6.97 (d, J=5.7 Hz, 1H), 4.87 (q, J=8.4 Hz, 2H), 2.45-2.34 (m, 1H), 1.33-1.19 (m, 13H), 1.11-1.02 (m, 1H), 0.42-0.30 (m, 1H). ES/MS m/z: 385.20 [M+H].

Intermediate 785. 7-fluoro-6-((1S,2S)-2-(4,4,5,5-tetramethyl-1,3,2-dioxaborolan-2-yl)cyclopropyl)-1-(2,2,2-trifluoroethyl)-1H-indazole

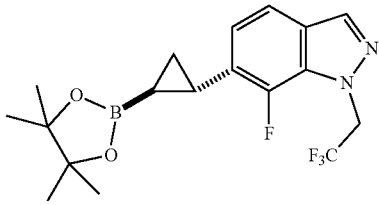

7-fluoro-6-((1S,2S)-2-(4,4,5,5-tetramethyl-1,3,2-dioxaborolan-2-yl)cyclopropyl)-1-(2,2,2-trifluoroethyl)-1H-indazole was prepared in the manner described for Intermediate 769 (steps 1-3), but replacing 4-bromo-2-fluorobenzonitrile with 7-bromo-5-fluoro-1-(2,2,2-trifluoroethyl)-1H-indazole. ES/MS m/z: 385.10 [M+H].

Intermediate 786. 6-((2S,2S)-2-(4,4,5,5-tetramethyl-1,3,2-dioxaborolan-2-yl)cyclopropyl)-1-(2,2,2-trifluoroethyl)-3-(trifluoromethyl)-1H-indazole

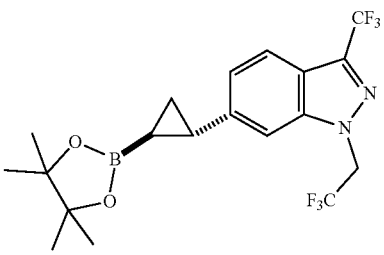 [SMILES: CC1(C)OB([C@H]2C[C@@H]2c2ccc3c(C(F)(F)F)nn(CC(F)(F)F)c3c2)OC1(C)C]

6-((2S,2S)-2-(4,4,5,5-tetramethyl-1,3,2-dioxaborolan-2-yl)cyclopropyl)-1-(2,2,2-trifluoroethyl)-3-(trifluoromethyl)-1H-indazole was prepared in the manner described for Intermediate 769 (steps 1-3), but replacing 4-bromo-2-fluorobenzonitrile with 6-bromo-1-(2,2,2-trifluoroethyl)-3-(trifluoromethyl)-1H-indazole. $^1$H NMR (400 MHz, Chloroform-d) δ 7.71 (d, J=8.3 Hz, 1H), 7.18 (s, 1H), 7.09-7.02 (m, 1H), 4.94 (q, J=8.3 Hz, 2H), 2.33-2.22 (m, 1H), 1.30-1.21 (m, 13H), 1.14-1.04 (m, 1H), 0.46-0.35 (m, 1H).

Intermediate 787. 6-((2S,2S)-2-(4,4,5,5-tetramethyl-1,3,2-dioxaborolan-2-yl)cyclopropyl)-1-(1,1,1-trifluoropropan-2-yl)-1H-indazole

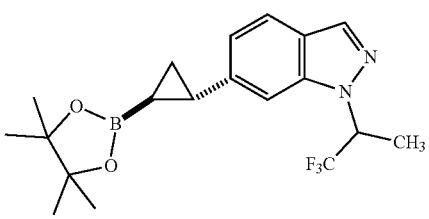 [SMILES: CC(n1ncc2ccc([C@H]3C[C@@H]3B3OC(C)(C)C(C)(C)O3)cc21)C(F)(F)F]

6-((1S,2S)-2-(4,4,5,5-tetramethyl-1,3,2-dioxaborolan-2-yl)cyclopropyl)-1-(1,1,1-trifluoropropan-2-yl)-1H-indazole was prepared in the manner described for Intermediate 769

(steps 1-3), but replacing 4-bromo-2-fluorobenzonitrile with 1-(2,2,2-trifluoro-1-methyl-ethyl)-6-vinyl-indazole. ES/MS m/z: 381.20 [M+H].

Intermediate 788. 2-chloro-5-((2S,2S)-2-(4,4,5,5-tetramethyl-1,3,2-dioxaborolan-2-yl)cyclopropyl)pyridine

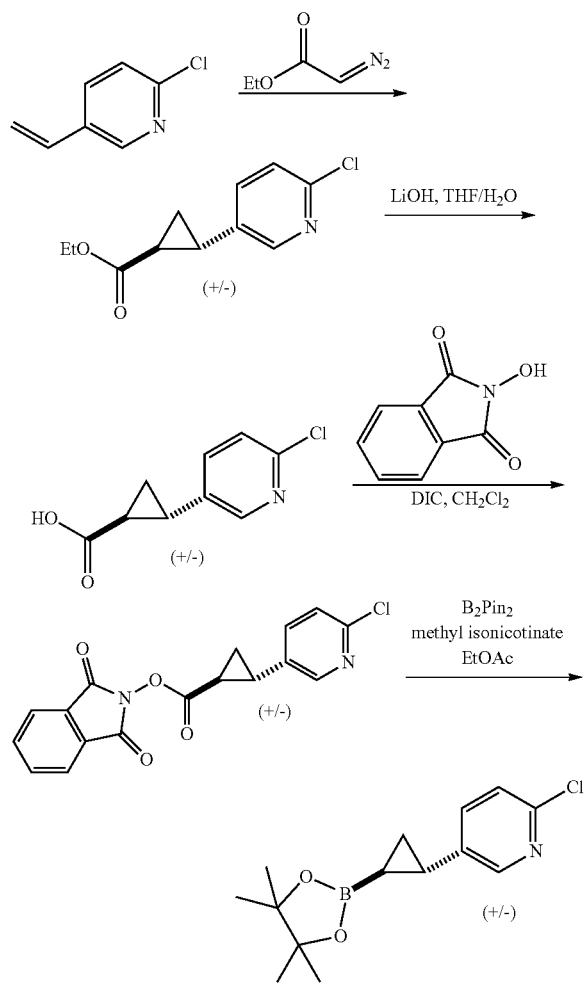

Step 1: To a solution of 2-chloro-5-vinyl-pyridine (1360 mg, 9.74 mmol, 1 equiv) in toluene (20 mL) was added ethyl diazoacetate (1 mL, 9.74 mmol, 1 equiv). The reaction mixture was heated to 80° C. After 24 hours, the reaction mixture was diluted with MeOH (5 mL) and concentrated to 5 mL. Purification was accomplished by SiO₂ chromatography (0-100% EtOAc/Hex), affording racemic ethyl (1S,2S)-2-(6-chloropyridin-3-yl)cyclopropane-1-carboxylate. $^1$H NMR (400 MHz, Chloroform-d) δ 8.22 (d, J=2.6 Hz, 1H), 7.35-7.29 (m, 1H), 7.24 (d, J=8.4 Hz, 1H), 4.22-4.15 (m, 2H), 2.54-2.45 (m, 1H), 1.94-1.86 (m, 1H), 1.70 1.63 (m, 1H), 1.35-1.25 (m, 4H). ES/MS m/z: 226.10 [M+H].

Step 2: To a solution of racemic ethyl (1S,2S)-2-(6-chloropyridin-3-yl)cyclopropane-1-carboxylate (738 mg, 3.27 mmol, 1 equiv) in 5:1 THF:H₂O (5 mL) was added LiOH—H₂O (274 mg, 6.54 mmol, 2 equiv). The reaction mixture was heated to 45 C. At t=2 hours, an additional 2 equiv of LiOH—H₂O was added. At t=20 hours, the reaction mixture was neutralized at 0° C. with 2M HCl, then exhaustively extracted with EtOAc. The combined organic layers were dried over Na₂SO₄, filtered, and concentrated to afford racemic (1S,2S)-2-(6-chloropyridin-3-yl)cyclopropane-1-carboxylic acid. A small portion of crude material was purified by SiO₂ chromatography (0-50% MeOH/CH₂Cl₂) for characterization purposes. $^1$H NMR (400 MHz, Chloroform-d) δ 8.24 (d, J=2.5 Hz, 1H), 7.39-7.31 (m, 1H), 7.30-7.23 (m, 1H), 2.63-2.48 (m, 1H), 1.99-1.87 (m, 1H), 1.79-1.66 (m, 1H), 1.45-1.34 (m, 1H). ES/MS m/z: 198.10 [M+H].

Step 3: To a solution of racemic (1S,2S)-2-(6-chloropyridin-3-yl)cyclopropane-1-carboxylic acid (290 mg, 1.47 mmol, 1 equiv) in CH₂Cl₂ (10 mL) was added diisopropylmethanediimine (0.27 mL, 1.76 mmol, 1.2 equiv), DMAP (36 mg, 10 mol %), and 2-hydroxyisoindoline-1,3-dione (287 mg, 1.76 mmol, 1.2 equiv). After 5 hours, the reaction mixture was filtered with CH₂Cl₂ washings and concentrated. The residue was purified by SiO₂ chromatography (0-20% MeOH/CH₂Cl₂), affording racemic 1,3-dioxoisoindolin-2-yl (1S,2S)-2-(6-chloropyridin-3-yl)cyclopropane-1-carboxylate. $^1$H NMR (400 MHz, Chloroform-d) δ 8.29 (d, J=2.5 Hz, 1H), 7.98-7.87 (m, 2H), 7.85-7.77 (m, 2H), 7.47-7.39 (m, 1H), 7.31 (d, J=8.2 Hz, 1H), 2.81-2.72 (m, 1H), 2.30-2.19 (m, 1H), 1.94-1.86 (m, 1H), 1.67-1.59 (m, 1H). ES/MS m/z: 343.00 [M+H].

Step 4: To a solution of racemic 1,3-dioxoisoindolin-2-yl (1S,2S)-2-(6-chloropyridin-3-yl)cyclopropane-1-carboxylate (525 mg, 1.53 mmol, 1 equiv) in EtOAc (8 mL) was added B₂Pin₂ (778 mg, 3.06 mmol, 2 equiv) and methyl isonicotinate (0.091 mL, 0.77 mmol, 0.5 equiv). The resulting mixture was heated to 80° C. under an atmosphere of argon. After 12 hours, the reaction mixture was filtered, concentrated, and purified by SiO₂ chromatography (0-20% EtOAc/Hex), affording racemic 2-chloro-5-((2S,2S)-2-(4,4,5,5-tetramethyl-1,3,2-dioxaborolan-2-yl)cyclopropyl)pyridine. $^1$H NMR (400 MHz, Chloroform-d) δ 8.20 (d, J=2.5 Hz, 1H), 7.31-7.24 (m, 1H), 7.24-7.18 (m, 1H), 2.11-2.05 (m, 1H), 1.31-1.18 (m, 13H), 1.04-0.97 (m, 1H), 0.33-0.23 (m, 1H). ES/MS m/z: 280.00 [M+H].

Intermediate 789. 6-((1S,2S)-2-(4,4,5,5-tetramethyl-1,3,2-dioxaborolan-2-yl)cyclopropyl)benzo[d]thiazole

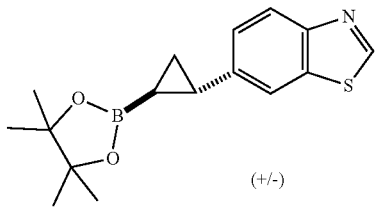 [SMILES: CC1(C)OB([C@H]2C[C@@H]2c2ccc3ncsc3c2)OC1(C)C]

6-((1S,2S)-2-(4,4,5,5-tetramethyl-1,3,2-dioxaborolan-2-yl)cyclopropyl)benzo[d]thiazole was prepared as a racemic mixture in the manner described for Intermediate 788, but replacing 2-chloro-5-vinyl-pyridine with 6-vinyl-1,3-benzothiazole. $^1$H NMR (400 MHz, Chloroform-d) δ 8.90 (s, 1H), 8.00 (d, J=8.5 Hz, 1H), 7.68 (d, J=1.8 Hz, 1H), 7.23 (dd, J=8.5, 1.8 Hz, 1H), 2.30-2.22 (m, 1H), 1.29-1.20 (m, 13H), 1.14-1.03 (m, 1H), 0.43-0.31 (m, 1H). ES/MS m/z: 302.20 [M+H].

Intermediate 790. 2-methyl-6-((1S,2S)-2-(4,4,5,5-tetramethyl-1,3,2-dioxaborolan-2-yl)cyclopropyl)benzo[d]thiazole

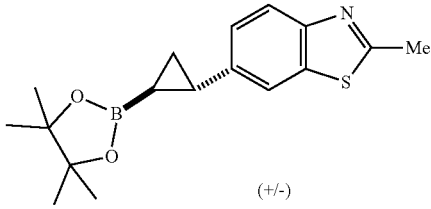 [SMILES: Cc1nc2ccc([C@H]3C[C@@H]3B3OC(C)(C)C(C)(C)O3)cc2s1]

(+/-)

2-methyl-6-((2S,2S)-2-(4,4,5,5-tetramethyl-1,3,2-dioxaborolan-2-yl)cyclopropyl)benzo[d]thiazole was prepared as a racemic mixture in the manner described for Intermediate 788, but replacing 2-chloro-5-vinyl-pyridine with 2-methyl-6-vinyl-1,3-benzothiazole. ¹H NMR (400 MHz, Chloroform-d) δ 7.81 (d, J=8.4 Hz, 1H), 7.57-7.51 (m, 1H), 7.16 (dd, J=8.4, 1.9 Hz, 1H), 2.82 (s, 3H), 2.29-2.15 (m, 1H), 1.30-1.16 (m, 13H), 1.13-0.98 (m, 1H), 0.42-0.27 (m, 1H). ES/MS m/z: 316.20 [M+H].

Intermediate 791. 5-chloro-3-fluoro-2-((2S,2S)-2-(4,4,5,5-tetramethyl-1,3,2-dioxaborolan-2-yl)cyclopropyl)pyridine

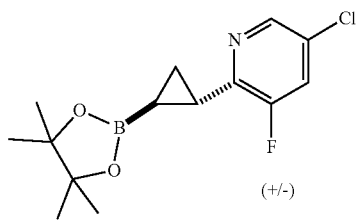 [SMILES: CC1(C)OB([C@H]2C[C@@H]2c2ncc(Cl)cc2F)OC1(C)C]

(+/-)

5-chloro-3-fluoro-2-((1S,2S)-2-(4,4,5,5-tetramethyl-1,3,2-dioxaborolan-2-yl)cyclopropyl)pyridine was prepared as a racemic mixture in the manner described for Intermediate 788, but replacing 2-chloro-5-vinyl-pyridine with 5-chloro-3-fluoro-2-vinyl-pyridine. ¹H NMR (400 MHz, Chloroform-d) δ 8.20 (d, J=2.0 Hz, 1H), 7.32 (dd, J=9.2, 2.0 Hz, 1H), 2.53-2.41 (m, 1H), 1.47-1.36 (m, 1H), 1.31-1.16 (m, 13H), 0.75-0.64 (m, 1H). ES/MS m/z: 298.10 [M+H].

Intermediate 792 and 793. 5-chloro-3-fluoro-2-((2S,2S)-2-(4,4,5,5-tetramethyl-1,3,2-dioxaborolan-2-yl)cyclopropyl)pyridine and 5-chloro-3-fluoro-24(1R,2R)-2-(4,4,5,5-tetramethyl-1,3,2-dioxaborolan-2-yl)cyclopropyl)pyridine

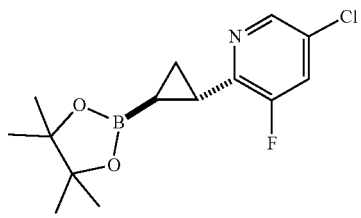

and

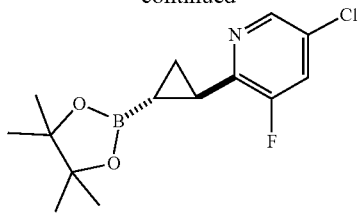

5-chloro-3-fluoro-24(1S,2S)-2-(4,4,5,5-tetramethyl-1,3,2-dioxaborolan-2-yl)cyclopropyl)pyridine and 5-chloro-3-fluoro-24(1R,2R)-2-(4,4,5,5-tetramethyl-1,3,2-dioxaborolan-2-yl)cyclopropyl)pyridine were obtained via SFC chiral separation of racemic ethyl (1S,2S)-2-(5-chloro-3-fluoro-2-pyridyl)cyclopropanecarboxylate (in the manner described for step 1 of Intermediate 788) and subsequent processing in the manner described for steps 2-4 of Intermediate 788.

Intermediate 794. 5-chloro-2-((2S,2S)-2-(4,4,5,5-tetramethyl-1,3,2-dioxaborolan-2-yl)cyclopropyl)pyridine

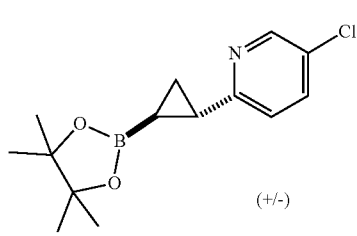 [SMILES: CC1(C)OB([C@H]2C[C@@H]2c2ccc(Cl)cn2)OC1(C)C]

(+/-)

5-chloro-2-((1S,2S)-2-(4,4,5,5-tetramethyl-1,3,2-dioxaborolan-2-yl)cyclopropyl)pyridine was prepared as a racemic mixture in the manner described for Intermediate 788, but replacing 2-chloro-5-vinyl-pyridine with 5-chloro-2-vinyl-pyridine. ¹H NMR (400 MHz, Chloroform-d) δ 8.38 (d, J=2.5 Hz, 1H), 7.52 (dd, J=8.4, 2.5 Hz, 1H), 7.09 (d, J=8.4 Hz, 1H), 2.27-2.17 (m, 1H), 1.36-1.15 (m, 14H), 0.66-0.55 (m, 1H). ES/MS m/z: 280.10 [M+H].

Intermediate 795. 3-fluoro-2-((1S,2S)-2-(4,4,5,5-tetramethyl-1,3,2-dioxaborolan-2-yl)cyclopropyl)-5-(trifluoromethyl)pyridine

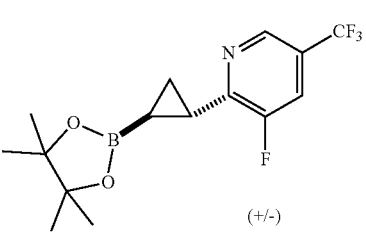 [SMILES: CC1(C)OB([C@H]2C[C@@H]2c2ncc(C(F)(F)F)cc2F)OC1(C)C]

(+/-)

3-fluoro-24(1S,2S)-2-(4,4,5,5-tetramethyl-1,3,2-dioxaborolan-2-yl)cyclopropyl)-5-(trifluoromethyl)pyridine was prepared as a racemic mixture in the manner described for Intermediate 788, but replacing 2-chloro-5-vinyl-pyridine with 3-fluoro-5-(trifluoromethyl)-2-vinyl-pyridine. ¹H NMR (400 MHz, Chloroform-d) δ 8.49 (bs, 1H), 7.48 (dd, J=9.3, 1.9 Hz, 1H), 2.60-2.51 (m, 1H), 1.53-1.43 (m, 1H), 1.33-1.18 (m, 13H), 0.84-0.75 (m, 1H). ES/MS m/z: 332.10 [M+H].

Intermediate 796. 6-((2S,2S)-2-(4,4,5,5-tetramethyl-1,3,2-dioxaborolan-2-yl)cyclopropyl)-1-(2,2,2-trifluoroethyl)-1H-pyrazolo[4,3-c]pyridine

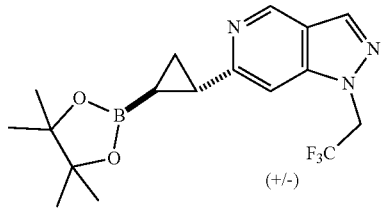 [SMILES: CC1(C)OB([C@H]2C[C@@H]2c2cc3c(cn2)cnn3CC(F)(F)F)OC1(C)C]

6-((2S,2S)-2-(4,4,5,5-tetramethyl-1,3,2-dioxaborolan-2-yl)cyclopropyl)-1-(2,2,2-trifluoroethyl)-1H-pyrazolo[4,3-c]pyridine was prepared as a racemic mixture in the manner described for Intermediate 788, but replacing 2-chloro-5-vinyl-pyridine with 1-(2,2,2-trifluoroethyl)-6-vinyl-pyrazolo[4,3-c]pyridine. ES/MS m/z: 368.20 [M+H].

Intermediate 797. 7-fluoro-6-((1S,2S)-2-(4,4,5,5-tetramethyl-1,3,2-dioxaborolan-2-yl)cyclopropyl)-1-(2,2,2-trifluoroethyl)-1H-pyrazolo[4,3-c]pyridine

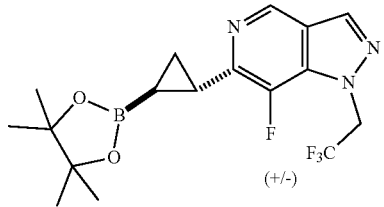 [SMILES: CC1(C)OB([C@H]2C[C@@H]2c2ncc3cnn(CC(F)(F)F)c3c2F)OC1(C)C]

7-fluoro-6-((2S,2S)-2-(4,4,5,5-tetramethyl-1,3,2-dioxaborolan-2-yl)cyclopropyl)-1-(2,2,2-trifluoroethyl)-1H-pyrazolo[4,3-c]pyridine was prepared as a racemic mixture in the manner described for Intermediate 788, but replacing 2-chloro-5-vinyl-pyridine with 7-fluoro-1-(2,2,2-trifluoroethyl)-6-vinyl-pyrazolo[4,3-c]pyridine. ES/MS m/z: 386.20 [M+H].

Intermediate 798. 6-((2S,2S)-2-(4,4,5,5-tetramethyl-1,3,2-dioxaborolan-2-yl)cyclopropyl)-1-(2,2,2-trifluoroethyl)-1H-pyrazolo[3,4-b]pyridine

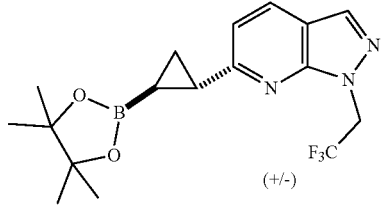 [SMILES: CC1(C)OB([C@H]2C[C@@H]2c2ccc3cnn(CC(F)(F)F)c3n2)OC1(C)C]

6-((2S,2S)-2-(4,4,5,5-tetramethyl-1,3,2-dioxaborolan-2-yl)cyclopropyl)-1-(2,2,2-trifluoroethyl)-1H-pyrazolo[3,4-b]pyridine was prepared as a racemic mixture in the manner described for Intermediate 788, but replacing 2-chloro-5-vinyl-pyridine with 1-(2,2,2-trifluoroethyl)-6-vinyl-pyrazolo[3,4-b]pyridine. ES/MS m/z: 368.20 [M+H].

Intermediate 799. 6-((2S,2S)-2-(4,4,5,5-tetramethyl-1,3,2-dioxaborolan-2-yl)cyclopropyl)-1-(2,2,2-trifluoroethyl)-1H-pyrazolo[4,3-b]pyridine

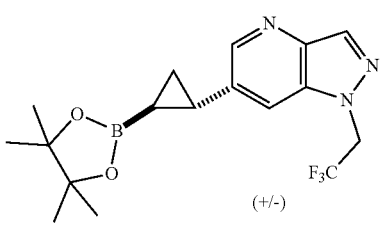 [SMILES: CC1(C)OB([C@H]2C[C@@H]2c2cnc3cnn(CC(F)(F)F)c3c2)OC1(C)C]

6-((1S,2S)-2-(4,4,5,5-tetramethyl-1,3,2-dioxaborolan-2-yl)cyclopropyl)-1-(2,2,2-trifluoroethyl)-1H-pyrazolo[4,3-b]pyridine was prepared as a racemic mixture in the manner described for Intermediate 788, but replacing 2-chloro-5-vinyl-pyridine with 1-(2,2,2-trifluoroethyl)-6-vinyl-pyrazolo[4,3-b]pyridine. ES/MS m/z: 368.20 [M+H].

Intermediate 800. 6-chloro-8-((1S,2S)-2-(2-chlorophenyl)cyclopropyl)imidazo[1,2-b]pyridazine was prepared

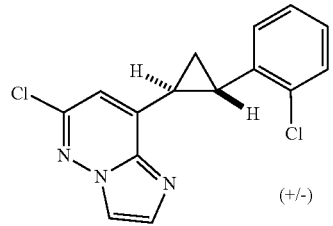 [SMILES: Clc1cc([C@H]2C[C@@H]2c2ccccc2Cl)c2nccn2n1]

6-chloro-8-((1S,2S)-2-(2-chlorophenyl)cyclopropyl)imidazo[1,2-b]pyridazine was prepared as a racemic mixture in the manner described for Intermediate 5, but replacing racemic 4,4,5,5-tetramethyl-2-((1S,2S)-2-phenylcyclopropyl)-1,3,2-dioxaborolane with 2-((1S,2S)-2-(2-chlorophenyl)cyclopropyl)-4,4,5,5-tetramethyl-1,3,2-dioxaborolane (Racemic Mixture). ES/MS m/z: 304.00 [M+H].

Intermediate 801. 2-chloro-5-((2S,2S)-2-(6-chloroimidazo[1,2-b]pyridazin-8-yl)cyclopropyl)benzonitrile

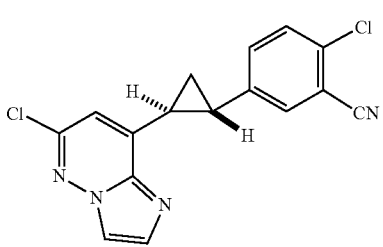 [SMILES: N#Cc1cc([C@H]2C[C@@H]2c2cc(Cl)nn3ccnc23)ccc1Cl]

2-chloro-5-((1S,2S)-2-(6-chloroimidazo[1,2-b]pyridazin-8-yl)cyclopropyl)benzonitrile was prepared in the manner described for Intermediate 5, but replacing racemic 4,4,5,5-tetramethyl-2-((2S,2S)-2-phenylcyclopropyl)-1,3,2-dioxaborolane with 2-chloro-5-((2S,2S)-2-(4,4,5,5-tetramethyl-1,3,2-dioxaborolan-2-yl)cyclopropyl)benzonitrile. ES/MS m/z: 329.05 [M+H].

Intermediate 802. 6-chloro-8-((2S,2S)-2-(4-(trifluoromethyl)phenyl)cyclopropyl)imidazo[1,2-b]pyridazine

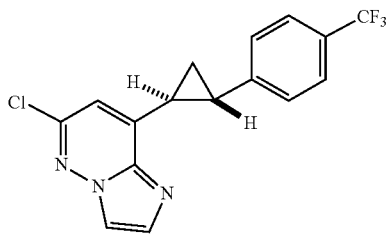 [SMILES: FC(F)(F)c1ccc([C@H]2C[C@@H]2c2cc(Cl)nn3ccnc23)cc1]

6-chloro-8-((1S,2S)-2-(4-(trifluoromethyl)phenyl)cyclopropyl)imidazo[1,2-b]pyridazine was prepared in the manner described for Intermediate 5, but replacing racemic 4,4,5,5-tetramethyl-2-((1S,2S)-2-phenylcyclopropyl)-1,3,2-dioxaborolane with 4,4,5,5-tetramethyl-2-((2S,2S)-2-(4-(trifluoromethyl)phenyl)cyclopropyl)-1,3,2-dioxaborolane. ES/MS m/z: 338.10 [M+H].

Intermediate 803. 6-chloro-8-((2S,2S)-2-(4-(difluoromethoxy)phenyl)cyclopropyl)imidazo[1,2-b]pyridazine

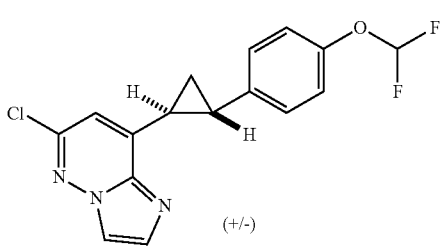 [SMILES: FC(F)Oc1ccc([C@H]2C[C@@H]2c2cc(Cl)nn3ccnc23)cc1]

(+/−)

6-chloro-8-((1S,2S)-2-(4-(difluoromethoxy)phenyl)cyclopropyl)imidazo[1,2-b]pyridazine was prepared as a racemic mixture in the manner described for Intermediate 5, but replacing racemic 4,4,5,5-tetramethyl-2-((1S,2S)-2-phenylcyclopropyl)-1,3,2-dioxaborolane with 2-((1S,2S)-2-(4-(difluoromethoxy)phenyl)cyclopropyl)-4,4,5,5-tetramethyl-1,3,2-dioxaborolane (Racemic Mixture). ES/MS m/z: 336.00 [M+H].

Intermediate 804. 6-chloro-8-((2S,2S)-2-(4-(difluoromethoxy)phenyl)cyclopropyl)imidazo[1,2-b]pyridazine

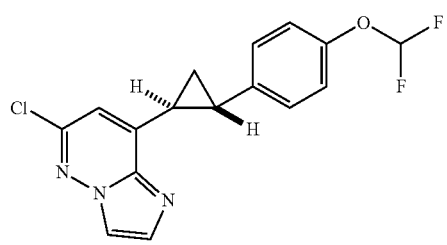 [SMILES: FC(F)Oc1ccc([C@H]2C[C@@H]2c2cc(Cl)nn3ccnc23)cc1]

6-chloro-8-((1S,2S)-2-(4-(difluoromethoxy)phenyl)cyclopropyl)imidazo[1,2-b]pyridazine was prepared in the manner described for Intermediate 5, but replacing racemic 4,4,5,5-tetramethyl-2-((1S,2S)-2-phenylcyclopropyl)-1,3,2-dioxaborolane with 2-((1S,2S)-2-(4-(difluoromethoxy)phenyl)cyclopropyl)-4,4,5,5-tetramethyl-1,3,2-dioxaborolane. ES/MS m/z: 336.00 [M+H].

Intermediate 805. 4-((2S,2S)-2-(6-chloroimidazo[1,2-b]pyridazin-8-yl)cyclopropyl)-2,6-difluorobenzonitrile

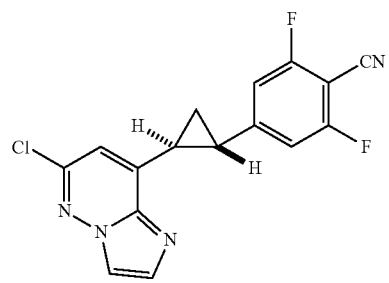 [SMILES: N#Cc1c(F)cc([C@H]2C[C@@H]2c2cc(Cl)nn3ccnc23)cc1F]

4-(1S,2S)-2-(6-chloroimidazo[1,2-b]pyridazin-8-yl)cyclopropyl)-2,6-difluorobenzonitrile was prepared in the manner described for Intermediate 5, but replacing racemic 4,4,5,5-tetramethyl-2-((2S,2S)-2-phenylcyclopropyl)-1,3,2-dioxaborolane with 2,6-difluoro-4-((1S,2S)-2-(4,4,5,5-tetramethyl-1,3,2-dioxaborolan-2-yl)cyclopropyl)benzonitrile. ES/MS m/z: 331.10 [M+H].

Intermediate 806. 4-((2S,2S)-2-(6-chloroimidazo[1,2-b]pyridazin-8-yl)cyclopropyl)-2,3-difluorobenzonitrile

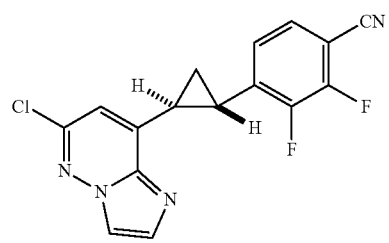 [SMILES: N#Cc1ccc([C@H]2C[C@@H]2c2cc(Cl)nn3ccnc23)c(F)c1F]

4-(1S,2S)-2-(6-chloroimidazo[1,2-b]pyridazin-8-yl)cyclopropyl)-2,3-difluorobenzonitrile was prepared in the manner described for Intermediate 5, but replacing racemic 4,4,5,5-tetramethyl-2-((1S,2S)-2-phenylcyclopropyl)-1,3,2-dioxaborolane with 2,3-difluoro-4-((1S,2S)-2-(4,4,5,5-tetramethyl-1,3,2-dioxaborolan-2-yl)cyclopropyl)benzonitrile. ES/MS m/z: 331.10 [M+H].

Intermediate 807. 4-((2S,2S)-2-(6-chloroimidazo[1,2-b]pyridazin-8-yl)cyclopropyl)-2-methoxybenzonitrile

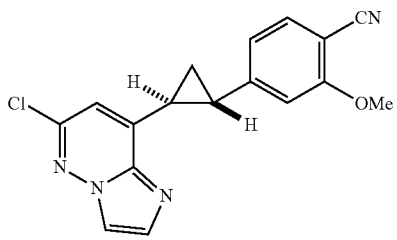 [SMILES: COc1cc([C@H]2C[C@@H]2c2cc(Cl)nn3ccnc23)ccc1C#N]

4-(1S,2S)-2-(6-chloroimidazo[1,2-b]pyridazin-8-yl)cyclopropyl)-2-methoxybenzonitrile was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 2-methoxy-4-(1S,2S)-2-(4,4,5,5-tetramethyl-1,3,2-dioxaborolan-2-yl)cyclopropyl)benzonitrile. ES/MS m/z: 325.20 [M+H].

Intermediate 808. 4-((2S,2S)-2-(6-chloroimidazo[1,2-b]pyridazin-8-yl)cyclopropyl)-2-methylbenzonitrile

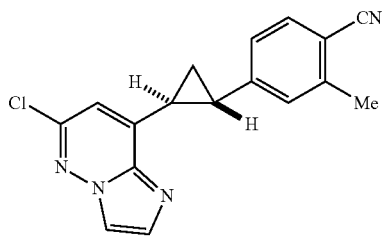 [SMILES: Cc1cc([C@H]2C[C@@H]2c2cc(Cl)nn3ccnc23)ccc1C#N]

4-((2S,2S)-2-(6-chloroimidazo[1,2-b]pyridazin-8-yl)cyclopropyl)-2-methylbenzonitrile was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 2-methyl-4-((1S,2S)-2-(4,4,5,5-tetramethyl-1,3,2-dioxaborolan-2-yl)cyclopropyl)benzonitrile. ES/MS m/z: 309.10 [M+H].

Intermediate 809. 4-((2S,2S)-2-(6-chloroimidazo[1,2-b]pyridazin-8-yl)cyclopropyl)-2-cyclopropylbenzonitrile

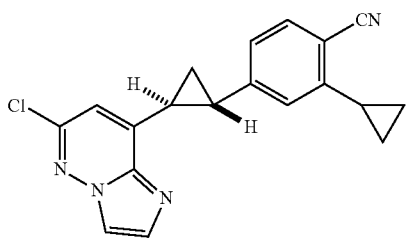 [SMILES: N#Cc1ccc([C@H]2C[C@@H]2c2cc(Cl)nn3ccnc23)cc1C1CC1]

4-(1S,2S)-2-(6-chloroimidazo[1,2-b]pyridazin-8-yl)cyclopropyl)-2-cyclopropylbenzonitrile was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 2-cyclopropyl-4-((1S,2S)-2-(4,4,5,5-tetramethyl-1,3,2-dioxaborolan-2-yl)cyclopropyl)benzonitrile. ES/MS m/z: 335.10 [M+H].

Intermediate 810. 6-chloro-8-((1S,2S)-2-(4-(2,2,2-trifluoroethoxy)phenyl)cyclopropyl)imidazo[1,2-b]pyridazine

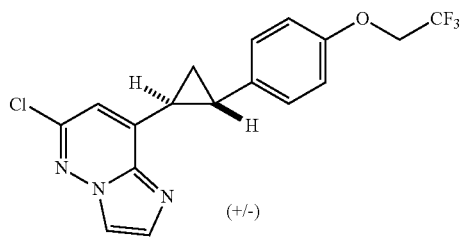 [SMILES: FC(F)(F)COc1ccc([C@H]2C[C@@H]2c2cc(Cl)nn3ccnc23)cc1]

6-chloro-8-((1S,2S)-2-(4-(2,2,2-trifluoroethoxy)phenyl)cyclopropyl)imidazo[1,2-b]pyridazine was prepared as a racemic mixture in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 4,4,5,5-tetramethyl-2-((2S,2S)-2-(4-(2,2,2-trifluoroethoxy)phenyl)cyclopropyl)-1,3,2-dioxaborolane (Racemic Mixture). ES/MS m/z: 368.10 [M+H].

Intermediate 811. 6-chloro-8-((2S,2S)-2-(4-(2,2-difluoroethoxy)phenyl)cyclopropyl)imidazo[1,2-b]pyridazine

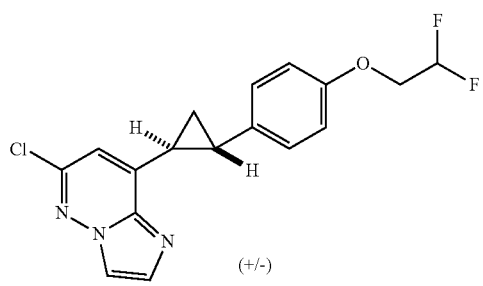 [SMILES: FC(F)COc1ccc([C@H]2C[C@@H]2c2cc(Cl)nn3ccnc23)cc1]

6-chloro-8-((1S,2S)-2-(4-(2,2-difluoroethoxy)phenyl)cyclopropyl)imidazo[1,2-b]pyridazine was prepared as a racemic mixture in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 2-((1S,2S)-2-(4-(2,2-difluoroethoxy)phenyl)cyclopropyl)-4,4,5,5-tetramethyl-1,3,2-dioxaborolane (Racemic Mixture). ES/MS m/z: 350.10 [M+H].

Intermediate 812. 4-((1S,2S)-2-(6-chloroimidazo[1,2-b]pyridazin-8-yl)cyclopropyl)-2-fluoro-6-methylbenzonitrile

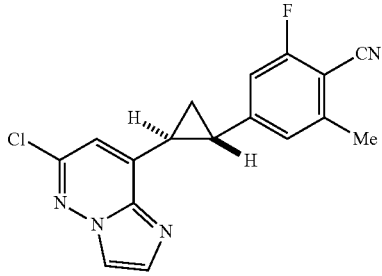 [SMILES: Cc1cc([C@H]2C[C@@H]2c2cc(Cl)nn3ccnc23)cc(F)c1C#N]

4-(1S,2S)-2-(6-chloroimidazo[1,2-b]pyridazin-8-yl)cyclopropyl)-2-fluoro-6-methylbenzonitrile was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 2-fluoro-6-methyl-4-(1S,2S)-2-(4,4,5,5-tetramethyl-1,3,2-dioxaborolan-2-yl)cyclopropyl)benzonitrile. ES/MS m/z: 327.10 [M+H].

Intermediate 813. 2-chloro-4-((2S,2S)-2-(6-chloroimidazo[1,2-b]pyridazin-8-yl)cyclopropyl)benzonitrile

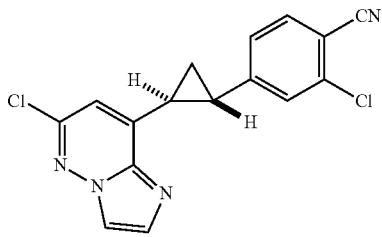 [SMILES: N#Cc1ccc([C@H]2C[C@@H]2c2cc(Cl)nn3ccnc23)cc1Cl]

2-chloro-4-((1S,2S)-2-(6-chloroimidazo[1,2-b]pyridazin-8-yl)cyclopropyl)benzonitrile was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 2-chloro-4-((1S,2S)-2-(4,4,5,5-tetramethyl-1,3,2-dioxaborolan-2-yl)cyclopropyl)benzonitrile. ES/MS m/z: 329.10 [M+H].

Intermediate 814. 4-((2S,2S)-2-(6-chloroimidazo[1,2-b]pyridazin-8-yl)cyclopropyl)-2,5-difluorobenzonitrile

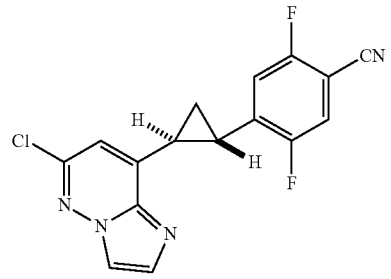 [SMILES: N#Cc1cc(F)c([C@H]2C[C@@H]2c2cc(Cl)nn3ccnc23)cc1F]

4-(1S,2S)-2-(6-chloroimidazo[1,2-b]pyridazin-8-yl)cyclopropyl)-2,5-difluorobenzonitrile was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 2,5-difluoro-4-((1S,2S)-2-(4,4,5,5-tetramethyl-1,3,2-dioxaborolan-2-yl)cyclopropyl)benzonitrile. ES/MS m/z: 331.10 [M+H].

Intermediate 815. 4-((2S,2S)-2-(6-chloro-3-fluoroimidazo[1,2-b]pyridazin-8-yl)cyclopropyl)-2,5-difluorobenzonitrile

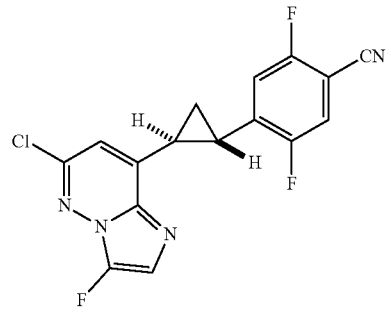 [SMILES: N#Cc1cc(F)c([C@H]2C[C@@H]2c2cc(Cl)nn3c(F)cnc23)cc1F]

4-(1S,2S)-2-(6-chloro-3-fluoroimidazo[1,2-b]pyridazin-8-yl)cyclopropyl)-2,5-difluorobenzonitrile was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 2,5-difluoro-4-((2S,2S)-2-(4,4,5,5-tetramethyl-1,3,2-dioxaborolan-2-yl)cyclopropyl)benzonitrile, and 8-bromo-6-chloroimidazo[1,2-b]pyridazine with 8-bromo-6-chloro-3-fluoroimidazo[1,2-b]pyridazine. ES/MS m/z: 349.10 [M+H].

Intermediate 816. 6-((1S,2S)-2-(6-chloroimidazo[1,2-b]pyridazin-8-yl)cyclopropyl)-2-(trifluoromethyl)benzo[d]thiazole

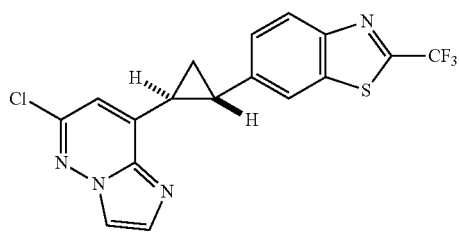 [SMILES: FC(F)(F)c1nc2ccc([C@H]3C[C@@H]3c3cc(Cl)nn4ccnc34)cc2s1]

6-((1S,2S)-2-(6-chloroimidazo[1,2-b]pyridazin-8-yl)cyclopropyl)-2-(trifluoromethyl)benzo [d]thiazole was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 6-((2S,2S)-2-(4,4,5,5-tetramethyl-1,3,2-dioxaborolan-2-yl)cyclopropyl)-2-(trifluoromethyl)benzo[d]thiazole. ES/MS m/z: 395.10 [M+H].

Intermediate 817. 6-chloro-8-((1S,2S)-2-(6-chloropyridin-3-yl)cyclopropyl)imidazo[1,2-b]pyridazine

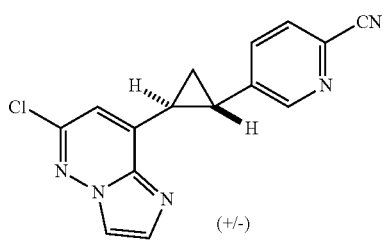 [SMILES: N#Cc1ccc([C@H]2C[C@@H]2c2cc(Cl)nn3ccnc23)cn1]

6-chloro-8-((2S,2S)-2-(6-chloropyridin-3-yl)cyclopropyl)imidazo[1,2-b]pyridazine was prepared as a racemic mixture in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 2-chloro-5-((2S,2S)-2-(4,4,5,5-tetramethyl-1,3,2-dioxaborolan-2-yl)cyclopropyl)pyridine (Racemic Mixture). ES/MS m/z: 305.00 [M+H].

Intermediate 818. 6-((1S,2S)-2-(6-chloroimidazo[1,2-b]pyridazin-8-yl)cyclopropyl)-2-methylbenzo[d]thiazole

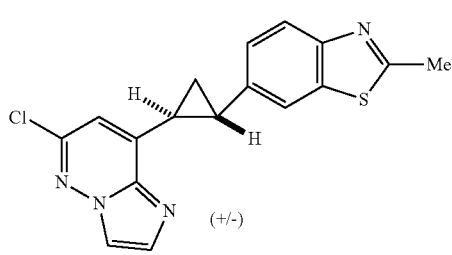 [SMILES: Cc1nc2ccc([C@H]3C[C@@H]3c3cc(Cl)nn4ccnc34)cc2s1]

6-((1S,2S)-2-(6-chloroimidazo[1,2-b]pyridazin-8-yl)cyclopropyl)-2-methylbenzo[d]thiazole was prepared as a racemic mixture in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 2-methyl-6-((2S,2S)-2-(4,4,5,5-tetramethyl-1,3,2-dioxaborolan-2-yl)cyclopropyl)benzo[d]thiazole. ES/MS m/z: 341.00 [M+H].

Intermediate 819. 6-((2S,2S)-2-(6-chloro-3-fluoroimidazo[1,2-b]pyridazin-8-yl)cyclopropyl)-2-methylbenzo[d]thiazole

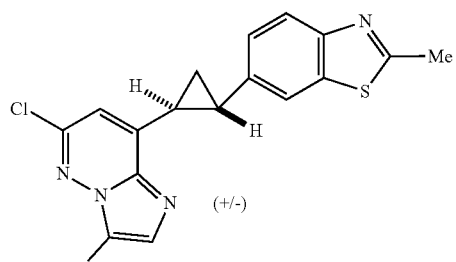

6-((1S,2S)-2-(6-chloro-3-fluoroimidazo[1,2-b]pyridazin-8-yl)cyclopropyl)-2-methylbenzo[d]thiazole was prepared as a racemic mixture in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 2-methyl-6-((1S,2S)-2-(4,4,5,5-tetramethyl-1,3,2-dioxaborolan-2-yl)cyclopropyl)benzo[d]thiazole, and 8-bromo-6-chloro-imidazo[1,2-b]pyridazine with 8-bromo-6-chloro-3-fluoro-imidazo[1,2-b]pyridazine. ES/MS m/z: 359.10 [M+H].

Intermediate 820. 6-((2S,2S)-2-(6-chloro-3-fluoroimidazo[1,2-b]pyridazin-8-yl)cyclopropyl)benzo[d]thiazole

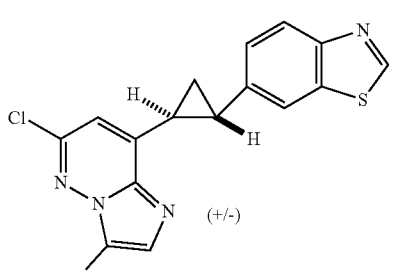

6-((2S,2S)-2-(6-chloro-3-fluoroimidazo[1,2-b]pyridazin-8-yl)cyclopropyl)benzo[d]thiazole was prepared as a racemic mixture in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 6-((1S,2S)-2-(4,4,5,5-tetramethyl-1,3,2-dioxaborolan-2-yl)cyclopropyl)benzo[d]thiazole (Racemic Mixture), and 8-bromo-6-chloro-imidazo[1,2-b]pyridazine with 8-bromo-6-chloro-3-fluoro-imidazo[1,2-b]pyridazine. ES/MS m/z: 345.10 [M+H].

Intermediate 821. 6-chloro-8-((2S,2S)-2-(5-chloro-3-fluoropyridin-2-yl)cyclopropyl)imidazo[1,2-b]pyridazine

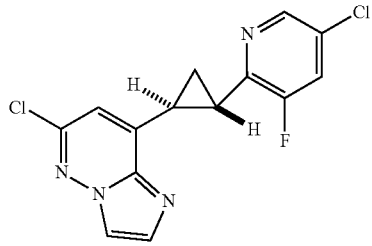 [SMILES: Fc1cc(Cl)cnc1[C@H]1C[C@@H]1c1cc(Cl)nn2ccnc12]

6-chloro-8-((1S,2S)-2-(5-chloro-3-fluoropyridin-2-yl)cyclopropyl)imidazo[1,2-b]pyridazine was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 5-chloro-3-fluoro-2-((2S,2S)-2-(4,4,5,5-tetramethyl-1,3,2-dioxaborolan-2-yl)cyclopropyl)pyridine. ES/MS m/z: 323.10 [M+H].

Intermediate 822. 6-chloro-8-((2S,2S)-2-(5-chloro-3-fluoropyridin-2-yl)cyclopropyl)-3-fluoroimidazo[1,2-b]pyridazine

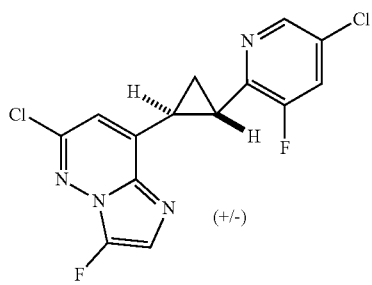 [SMILES: Fc1cc(Cl)cnc1[C@H]1C[C@@H]1c1cc(Cl)nn2c(F)cnc12]

6-chloro-8-((1S,2S)-2-(5-chloro-3-fluoropyridin-2-yl)cyclopropyl)-3-fluoroimidazo[1,2-b]pyridazine was prepared as a racemic mixture in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 5-chloro-3-fluoro-2-((2S,2S)-2-(4,4,5,5-tetramethyl-1,3,2-dioxaborolan-2-yl)cyclopropyl)pyridine (Racemic Mixture), and 8-bromo-6-chloro-imidazo[1,2-b]pyridazine with 8-bromo-6-chloro-3-fluoro-imidazo[1,2-b]pyridazine. ES/MS m/z: 341.00 [M+H].

Intermediate 823. 6-chloro-8-((2S,2S)-2-(5-chloro-3-fluoropyridin-2-yl)cyclopropyl)-3-fluoroimidazo[1,2-b]pyridazine

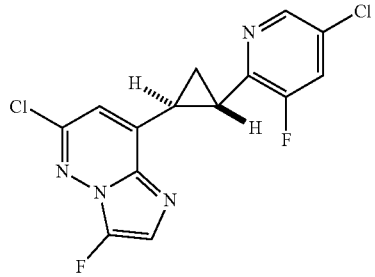 [SMILES: Fc1cc(Cl)cnc1[C@H]1C[C@@H]1c1cc(Cl)nn2c(F)cnc12]

6-chloro-8-((1S,2S)-2-(5-chloro-3-fluoropyridin-2-yl)cyclopropyl)-3-fluoroimidazo[1,2-b]pyridazine was chirally separated from the racemic Intermediate 822 by SFC AD-H column (35% MeOH).and

Intermediate 824. 6-chloro-8-((2S,2S)-2-(5-chloropyridin-2-yl)cyclopropyl)imidazo[1,2-b]pyridazine

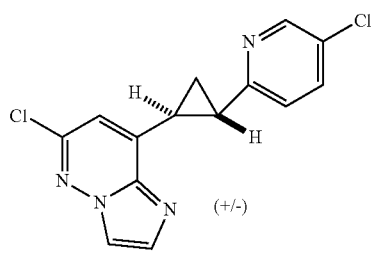 [SMILES: Clc1ccc([C@H]2C[C@@H]2c2cc(Cl)nn3ccnc23)nc1]

6-chloro-8-((1S,2S)-2-(5-chloropyridin-2-yl)cyclopropyl)imidazo[1,2-b]pyridazine was prepared as a racemic mixture in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 5-chloro-2-((1S,2S)-2-(4,4,5,5-tetramethyl-1,3,2-dioxaborolan-2-yl)cyclopropyl)pyridine (Racemic Mixture). ES/MS m/z: 305.10 [M+H].

Intermediate 825. 6-chloro-8-((2S,2S)-2-(5-chloropyridin-2-yl)cyclopropyl)-3-fluoroimidazo[1,2-b]pyridazine

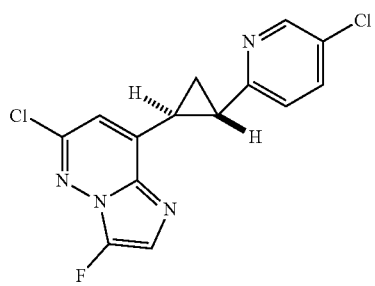 [SMILES: Fc1cnc2c([C@H]3C[C@@H]3c3ccc(Cl)cn3)cc(Cl)nn12]

6-chloro-8-((1S,2S)-2-(5-chloropyridin-2-yl)cyclopropyl)-3-fluoroimidazo[1,2-b]pyridazine was prepared as a

Intermediate 826. 6-chloro-8-((2S,2S)-2-(3-fluoro-5-(trifluoromethyl)pyridin-2-yl)cyclopropyl)imidazo[1,2-b]pyridazine

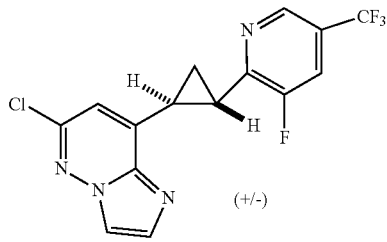 [SMILES: Fc1cc(C(F)(F)F)cnc1[C@H]1C[C@@H]1c1cc(Cl)nn2ccnc12]

6-chloro-8-((2S,2S)-2-(3-fluoro-5-(trifluoromethyl)pyridin-2-yl)cyclopropyl)imidazo[1,2-b]pyridazine was prepared as a racemic mixture in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 3-fluoro-24(1S,2S)-2-(4,4,5,5-tetramethyl-1,3,2-dioxaborolan-2-yl)cyclopropyl)-5-(trifluoromethyl)pyridine. ES/MS m/z: 357.00 [M+H].

Intermediate 827. 6-chloro-8-((2S,2S)-2-(4-fluoro-1-(2,2,2-trifluoroethyl)-1H-indazol-6-yl)cyclopropyl)imidazo[1,2-b]pyridazine

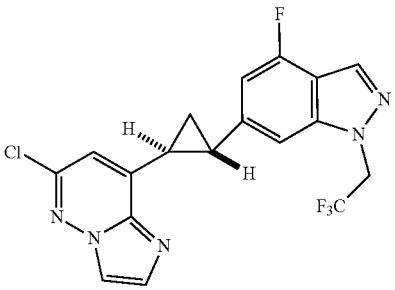 [SMILES: Fc1cc([C@H]2C[C@@H]2c2cc(Cl)nn3ccnc23)cc2c1cnn2CC(F)(F)F]

6-chloro-8-((1S,2S)-2-(4-fluoro-1-(2,2,2-trifluoroethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 4-fluoro-6-((1S,2S)-2-(4,4,5,5-tetramethyl-1,3,2-dioxaborolan-2-yl)cyclopropyl)-1-(2,2,2-trifluoroethyl)-1H-indazole. ES/MS m/z: 410.10 [M+H].

Intermediate 828. 6-chloro-3-fluoro-8-((1S,2S)-2-(4-fluoro-1-(2,2,2-trifluoroethyl)-1H-indazol-6-yl)cyclopropyl)imidazo[1,2-b]pyridazine

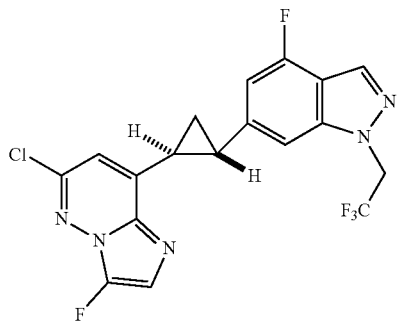 [SMILES: Fc1cc([C@H]2C[C@@H]2c2cc(Cl)nn3c(F)cnc23)cc2c1cnn2CC(F)(F)F]

6-chloro-3-fluoro-8-((1S,2S)-2-(4-fluoro-1-(2,2,2-trifluoroethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 4-fluoro-6-((1S,2S)-2-(4,4,5,5-tetramethyl-1,3,2-dioxaborolan-2-yl)cyclopropyl)-1-(2,2,2-trifluoroethyl)-1H-indazole, and 8-bromo-6-chloro-imidazo[1,2-b]pyridazine with 8-bromo-6-chloro-3-fluoro-imidazo[1,2-b]pyridazine. ES/MS m/z: 428.10 [M+H].

Intermediate 829. 6-chloro-8-((2S,2S)-2-(5-fluoro-1-(2,2,2-trifluoroethyl)-1H-indazol-6-yl)cyclopropyl)imidazo[1,2-b]pyridazine

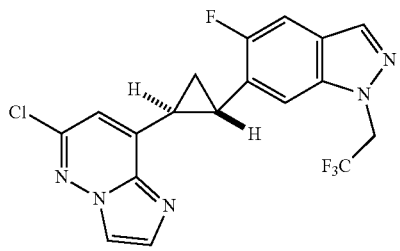 [SMILES: Fc1cc2cnn(CC(F)(F)F)c2cc1[C@H]1C[C@@H]1c1cc(Cl)nn2ccnc12]

6-chloro-8-((1S,2S)-2-(5-fluoro-1-(2,2,2-trifluoroethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 5-fluoro-6-((1S,2S)-2-(4,4,5,5-tetramethyl-1,3,2-dioxaborolan-2-yl)cyclopropyl)-1-(2,2,2-trifluoroethyl)-1H-indazole. ES/MS m/z: 410.10 [M+H].

--- racemic mixture in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 5-chloro-2-((1S,2S)-2-(4,4,5,5-tetramethyl-1,3,2-dioxaborolan-2-yl)cyclopropyl)pyridine (Racemic Mixture), and 8-bromo-6-chloro-imidazo[1,2-b]pyridazine with 8-bromo-6-chloro-3-fluoroimidazo[1,2-b]pyridazine, and was chirally separated from the racemic mixture by SFC AD-H column (30% IPA-NH₃).

Intermediate 830. 6-chloro-3-fluoro-8-((2S,2S)-2-(5-fluoro-1-(2,2,2-trifluoroethyl)-1H-indazol-6-yl)cyclopropyl)imidazo[1,2-b]pyridazine

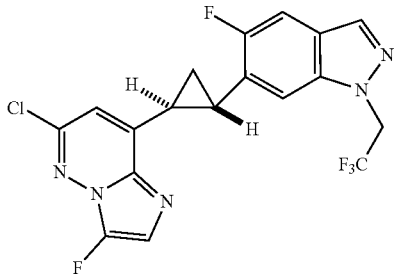 [SMILES: Fc1cc2cnn(CC(F)(F)F)c2cc1[C@H]1C[C@@H]1c1cc(Cl)nn2c(F)cnc12]

6-chloro-3-fluoro-8-((1S,2S)-2-(5-fluoro-1-(2,2,2-trifluoroethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 5-fluoro-6-((1S,2S)-2-(4,4,5,5-tetramethyl-1,3,2-dioxaborolan-2-yl)cyclopropyl)-1-(2,2,2-trifluoroethyl)-1H-indazole, and 8-bromo-6-chloro-imidazo[1,2-b]pyridazine with 8-bromo-6-chloro-3-fluoro-imidazo[1,2-b]pyridazine. ES/MS m/z: 428.10 [M+H].

Intermediate 831. 6-chloro-8-((2S,2S)-2-(7-fluoro-1-(2,2,2-trifluoroethyl)-1H-indazol-6-yl)cyclopropyl)imidazo[1,2-b]pyridazine

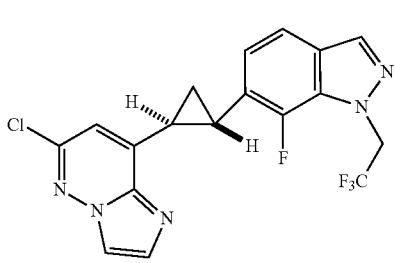 [SMILES: Fc1c([C@H]2C[C@@H]2c2cc(Cl)nn3ccnc23)ccc2cnn(CC(F)(F)F)c12]

6-chloro-8-((1S,2S)-2-(7-fluoro-1-(2,2,2-trifluoroethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 7-fluoro-6-((1S,2S)-2-(4,4,5,5-tetramethyl-1,3,2-dioxaborolan-2-yl)cyclopropyl)-1-(2,2,2-trifluoroethyl)-1H-indazole. ES/MS m/z: 410.10 [M+H].

Intermediate 832. 6-chloro-3-fluoro-8-((1S,2S)-2-(7-fluoro-1-(2,2,2-trifluoroethyl)-1H-indazol-6-yl)cyclopropyl)imidazo[1,2-b]pyridazine

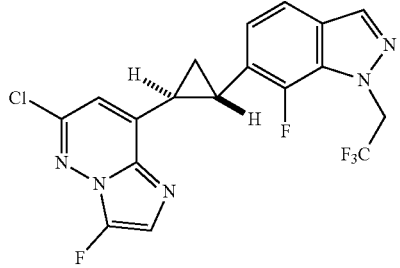 [SMILES: Fc1c([C@H]2C[C@@H]2c2cc(Cl)nn3c(F)cnc23)ccc2cnn(CC(F)(F)F)c12]

6-chloro-3-fluoro-8-((1S,2S)-2-(7-fluoro-1-(2,2,2-trifluoroethyl)-1H-indazol-6-yl)cyclopropyl)imidazo[1,2-b]pyridazine was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 7-fluoro-6-((1S,2S)-2-(4,4,5,5-tetramethyl-1,3,2-dioxaborolan-2-yl)cyclopropyl)-1-(2,2,2-trifluoroethyl)-1H-indazole, and 8-bromo-6-chloro-imidazo[1,2-b]pyridazine with 8-bromo-6-chloro-3-fluoro-imidazo[1,2-b]pyridazine. ES/MS m/z: 428.10 [M+H].

Intermediate 833. 6-chloro-8-((2S,2S)-2-(7-fluoro-1-(2,2,2-trifluoroethyl)-1H-indazol-6-yl)cyclopropyl)-[1,2,4]triazolo[1,5-b]pyridazine

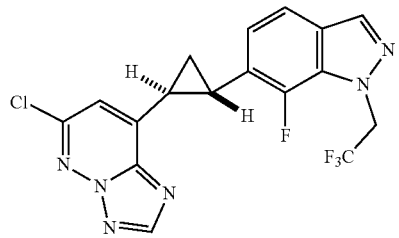 [SMILES: Fc1c([C@H]2C[C@@H]2c2cc(Cl)nn3ncnc23)ccc2cnn(CC(F)(F)F)c12]

6-chloro-8-((2S,2S)-2-(7-fluoro-1-(2,2,2-trifluoroethyl)-1H-indazol-6-yl)cyclopropyl)-[1,2,4]triazolo[1,5-b]pyridazine was prepared in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 7-fluoro-6-((1S,2S)-2-(4,4,5,5-tetramethyl-1,3,2-dioxaborolan-2-yl)cyclopropyl)-1-(2,2,2-trifluoroethyl)-1H-indazole, and 8-bromo-6-chloro-imidazo[1,2-b]pyridazine with 8-bromo-6-chloro-[1,2,4]triazolo[1,5-b]pyridazine. ES/MS m/z: 411.10 [M+H].

Intermediate 834. 6-((1S,2S)-2-(6-chloro-3-fluoroimidazo[1,2-b]pyridazin-8-yl)cyclopropyl)-1-(2,2,2-trifluoroethyl)-1H-pyrazolo[4,3-c]pyridine

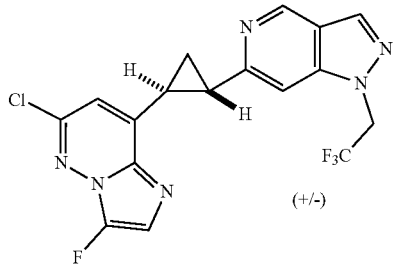 [SMILES: Fc1cnc2c([C@H]3C[C@@H]3c3cc4c(cn3)cnn4CC(F)(F)F)cc(Cl)nn12]

(+/-)

6-((1S,2S)-2-(6-chloro-3-fluoroimidazo[1,2-b]pyridazin-8-yl)cyclopropyl)-1-(2,2,2-trifluoroethyl)-1H-pyrazolo[4,3-c]pyridine was prepared as a racemic mixture in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 6-((2S,2S)-2-(4,4,5,5-tetramethyl-1,3,2-dioxaborolan-2-yl)cyclopropyl)-1-(2,2,2-trifluoroethyl)-1H-pyrazolo[4,3-c]pyridine (Racemic Mixture), and 8-bromo-6-chloro-imidazo[1,2-b]pyridazine with 8-bromo-6-chloro-3-fluoro-imidazo[1,2-b]pyridazine. ES/MS m/z: 411.10 [M+H].

Intermediates 835 and 836. 6-((1S,2S)-2-(6-chloro-3-fluoroimidazo[1,2-b]pyridazin-8-yl)cyclopropyl)-1-(2,2,2-trifluoroethyl)-1H-pyrazolo[4,3-c]pyridine and 6-((1R,2R)-2-(6-chloro-3-fluoroimidazo[1,2-b]pyridazin-8-yl)cyclopropyl)-1-(2,2,2-trifluoroethyl)-1H-pyrazolo[4,3-c]pyridine

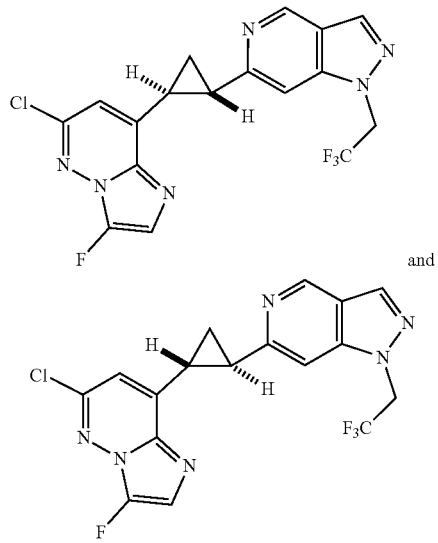

and 6-((1S,2S)-2-(6-chloro-3-fluoroimidazo[1,2-b]pyridazin-8-yl)cyclopropyl)-1-(2,2,2-trifluoroethyl)-1H-pyrazolo[4,3-c]pyridine and 6-((1R,2R)-2-(6-chloro-3-fluoroimidazo[1,2-b]pyridazin-8-yl)cyclopropyl)-1-(2,2,2-trifluoroethyl)-1H-pyrazolo[4,3-c]pyridine were chirally separated from the racemic Intermediate 834 by SFC AD-H column (20% EtOH).

Intermediate 837. 6-((1S,2S)-2-(6-chloro-3-fluoroimidazo[1,2-b]pyridazin-8-yl)cyclopropyl)-7-fluoro-1-(2,2,2-trifluoroethyl)-1H-pyrazolo[4,3-c]pyridine

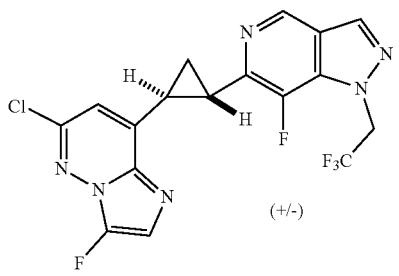 [SMILES: Fc1c([C@H]2C[C@@H]2c2cc(Cl)nn3c(F)cnc23)ncc2cnn(CC(F)(F)F)c12]

(+/-)

6-((1S,2S)-2-(6-chloro-3-fluoroimidazo[1,2-b]pyridazin-8-yl)cyclopropyl)-7-fluoro-1-(2,2,2-trifluoroethyl)-1H-pyrazolo[4,3-c]pyridine was prepared as a racemic mixture in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 7-fluoro-6-((1S,2S)-2-(4,4,5,5-tetramethyl-1,3,2-dioxaborolan-2-yl)cyclopropyl)-1-(2,2,2-trifluoroethyl)-1H-pyrazolo[4,3-c]pyridine (Racemic Mixture), and 8-bromo-6-chloro-imidazo[1,2-b]pyridazine with 8-bromo-6-chloro-3-fluoro-imidazo[1,2-b]pyridazine. ES/MS m/z: 429.10 [M+H].

Intermediate 838. 6-((1S,2S)-2-(6-chloro-3-fluoroimidazo[1,2-b]pyridazin-8-yl)cyclopropyl)-1-(2,2,2-trifluoroethyl)-1H-pyrazolo[3,4-b]pyridine

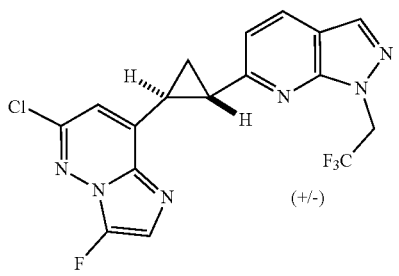 [SMILES: Fc1cnc2c([C@H]3C[C@@H]3c3ccc4cnn(CC(F)(F)F)c4n3)cc(Cl)nn12]

(+/-)

6-((1S,2S)-2-(6-chloro-3-fluoroimidazo[1,2-b]pyridazin-8-yl)cyclopropyl)-1-(2,2,2-trifluoroethyl)-1H-pyrazolo[3,4-b]pyridine was prepared as a racemic mixture in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 6-((2S,2S)-2-(4,4,5,5-tetramethyl-1,3,2-dioxaborolan-2-yl)cyclopropyl)-1-(2,2,2-trifluoroethyl)-1H-pyrazolo[3,4-b]pyridine (Racemic Mixture), and 8-bromo-6-chloro-imidazo[1,2-b]pyridazine with 8-bromo-6-chloro-3-fluoro-imidazo[1,2-b]pyridazine. ES/MS m/z: 411.10 [M+H].

Intermediate 839. 6-((2S,2S)-2-(6-chloro-3-fluoro-imidazo[1,2-b]pyridazin-8-yl)cyclopropyl)-1-(2,2,2-trifluoroethyl)-1H-pyrazolo[3,4-b]pyridine

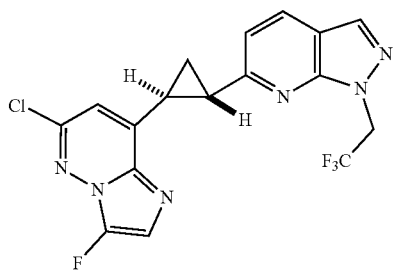 [SMILES: Fc1cnc2c([C@H]3C[C@@H]3c3ccc4cnn(CC(F)(F)F)c4n3)cc(Cl)nn12]

6-((1S,2S)-2-(6-chloro-3-fluoroimidazo[1,2-b]pyridazin-8-yl)cyclopropyl)-1-(2,2,2-trifluoroethyl)-1H-pyrazolo[3,4-b]pyridine was chirally separated from the racemic Intermediate 838 by SFC OJ-H column (15% EtOH).

Intermediate 840. 6-((2S,2S)-2-(6-chloro-3-fluoro-imidazo[1,2-b]pyridazin-8-yl)cyclopropyl)-1-(2,2,2-trifluoroethyl)-1H-pyrazolo[4,3-b]pyridine

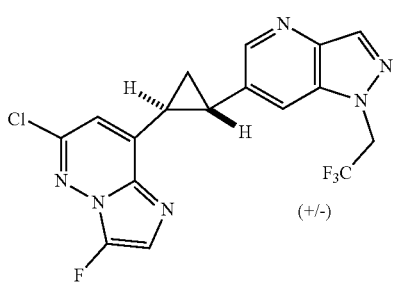 [SMILES: Fc1cnc2c([C@H]3C[C@@H]3c3cnc4cnn(CC(F)(F)F)c4c3)cc(Cl)nn12]

6-((1S,2S)-2-(6-chloro-3-fluoroimidazo[1,2-b]pyridazin-8-yl)cyclopropyl)-1-(2,2,2-trifluoroethyl)-1H-pyrazolo[4,3-b]pyridine was prepared as a racemic mixture in the manner described for Intermediate 238, but replacing 4-((2S,2S)-2-(4,4,5,5-tetramethyl-1,3,2-dioxaborolan-2-yl)cyclopropyl)-2-(trifluoromethyl)benzonitrile with 6-((2S,2S)-2-(4,4,5,5-tetramethyl-1,3,2-dioxaborolan-2-yl)cyclopropyl)-1-(2,2,2-trifluoroethyl)-1H-pyrazolo[4,3-b]pyridine (Racemic Mixture), and 8-bromo-6-chloro-imidazo[1,2-b]pyridazine with 8-bromo-6-chloro-3-fluoro-imidazo[1,2-b]pyridazine. ES/MS m/z: 411.10 [M+H].

Intermediates 841 and 842. 6-((1S,2S)-2-(6-chloro-3-fluoroimidazo[1,2-b]pyridazin-8-yl)cyclopropyl)-1-(2,2,2-trifluoroethyl)-1H-pyrazolo[4,3-b]pyridine and 6((1R,2R)-2-(6-chloro-3-fluoroimidazo[1,2-b]pyridazin-8-yl)cyclopropyl)-1-(2,2,2-trifluoroethyl)-1H-pyrazolo[4,3-b]pyridine

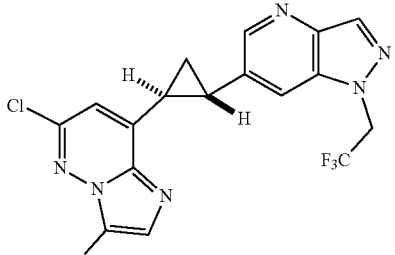

and

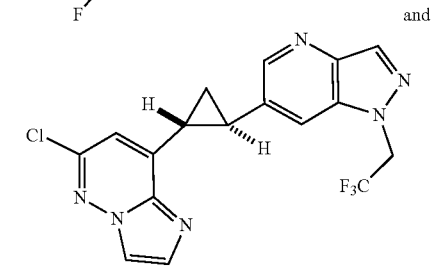

6-((1S,2S)-2-(6-chloro-3-fluoroimidazo[1,2-b]pyridazin-8-yl)cyclopropyl)-1-(2,2,2-trifluoroethyl)-1H-pyrazolo[4,3-b]pyridine and 6-((1R,2R)-2-(6-chloro-3-fluoroimidazo[1,2-b]pyridazin-8-yl)cyclopropyl)-1-(2,2,2-trifluoroethyl)-1H-pyrazolo[4,3-b]pyridine were chirally separated from the racemic Intermediate 840 by SFC AD-H column (15% IPA-NH$_3$).

Intermediate 843. 6-chloro-8-((2S,2S)-2-(1-(2,2,2-trifluoroethyl)-3-(trifluoromethyl)-1H-indazol-6-yl)cyclopropyl)imidazo[1,2-b]pyridazine

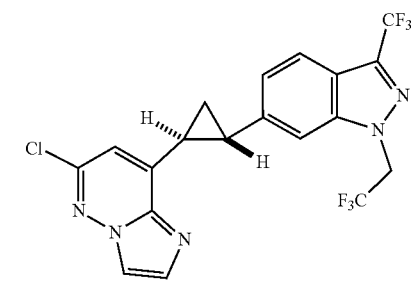 [SMILES: FC(F)(F)Cn1nc(C(F)(F)F)c2ccc([C@H]3C[C@@H]3c3cc(Cl)nn4ccnc34)cc21]

6-chloro-8-((1S,2S)-2-(1-(2,2,2-trifluoroethyl)-3-(trifluoromethyl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 6-((1S,2S)-2-(4,4,5,5-tetramethyl-1,3,2-dioxaborolan-2-yl)cyclopropyl)-1-(2,2,2-trifluoroethyl)-3-(trifluoromethyl)-1H-indazole. ES/MS m/z: 460.00 [M+H].

Intermediate 844. 6-chloro-8-((2S,2S)-2-(1-(1,1,1-trifluoropropan-2-yl)-1H-indazol-6-yl)cyclopropyl)imidazo[1,2-b]pyridazine

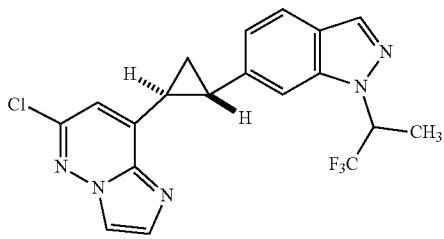 [SMILES: CC(n1ncc2ccc([C@H]3C[C@@H]3c3cc(Cl)nn4ccnc34)cc21)C(F)(F)F]

6-chloro-8-((1S,2S)-2-(1-(1,1,1-trifluoropropan-2-yl)-1H-indazol-6-yl)cyclopropyl)imidazo[1,2-b]pyridazine was prepared in the manner described for Intermediate 238, but replacing 4-(1S,2S)-2-(4,4,5,5-tetramethyl-1,3,2-dioxaborolan-2-yl)cyclopropyl)-2-(trifluoromethyl)benzonitrile with 6-((1S,2S)-2-(4,4,5,5-tetramethyl-1,3,2-dioxaborolan-2-yl)cyclopropyl)-1-(1,1,1-trifluoropropan-2-yl)-1H-indazole. ES/MS m/z: 406.20 [M+H].

Intermediate 845. 6-chloro-8-((2S,2S)-2-(3,4-difluorophenyl)cyclopropyl)imidazo[1,2-b]pyridazine

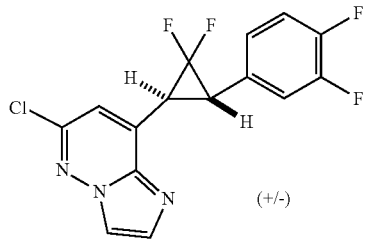 [SMILES: Fc1ccc([C@@H]2[C@@H](c3cc(Cl)nn4ccnc34)C2(F)F)cc1F]

6-chloro-8-((1S,2S)-2-(3,4-difluorophenyl)cyclopropyl)imidazo[1,2-b]pyridazine was prepared as a racemic mixture in the manner described for Intermediate 5, but replacing racemic 4,4,5,5-tetramethyl-2-((2S,2S)-2-phenylcyclopropyl)-1,3,2-dioxaborolane with potassium (3-(3,4-difluorophenyl)-2,2-difluorocyclopropyl) trifluoroborate (Racemic Mixture). ES/MS m/z: 342.10 [M+H].

Intermediate 846. 6-((2S,2S)-2-(6-chloroimidazo[1,2-b]pyridazin-8-yl)cyclopropyl)-2-(difluoromethyl)benzo[d]thiazole

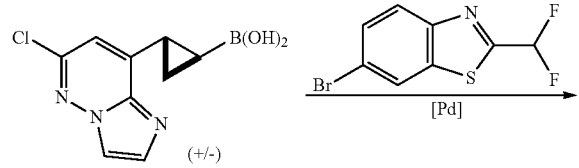

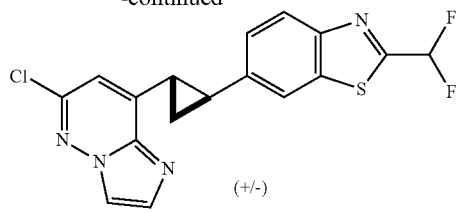

A solution of racemic ((1S,2S)-2-(6-chloroimidazo[1,2-b]pyridazin-8-yl)cyclopropyl)boronic acid (40 mg, 0.17 mmol, 1 equiv), 6-bromo-2-(difluoromethyl)benzo[d]thiazole (53 mg, 0.20 mmol, 1.2 equiv), potassium phosphate tribasic (107 mg, 0.51 mmol, 3 equiv), and cataCXium-A-Pd-G3 (12 mg, 10 mol %) in 1:5 water:1,4-dioxane (2.5 mL) was degassed with Argon for one minute and heated to 80° C. After 1 hour, the reaction mixture was directly purified by SiO₂ chromatography (0-100% EtOAc/Hex), affording racemic 6-((2S,2S)-2-(6-chloroimidazo[1,2-b]pyridazin-8-yl)cyclopropyl)-2-(difluoromethyl)benzo[d]thiazole. ES/MS m/z: 377.00 [M+H].

Intermediate 847. 6-chloro-8-((2S,2S)-2-(5-(2,2-difluoroethoxy)pyridin-2-yl)cyclopropyl)imidazo[1,2-b]pyridazine

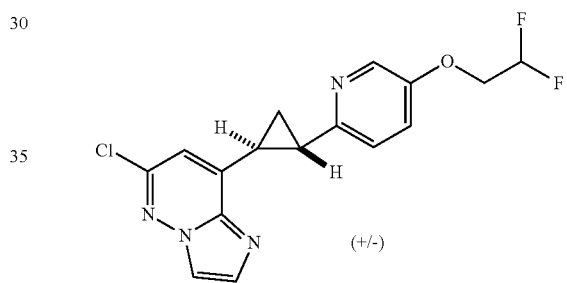

6-chloro-84(1S,2S)-2-(5-(2,2-difluoroethoxy)pyridin-2-yl)cyclopropyl)imidazo[1,2-b]pyridazine was prepared as a racemic mixture in the manner described for Intermediate 846, but replacing 6-bromo-2-(difluoromethyl)benzo[d]thiazole with 2-bromo-5-(2,2-difluoroethoxy)pyridine. ES/MS m/z: 351.10 [M+H].

Intermediate 848. 6-((1S,2S)-2-(6-chloroimidazo[1,2-b]pyridazin-8-yl)cyclopropyl)-1-(2,2,2-trifluoroethyl)-1H-pyrazolo[4,3-c]pyridine

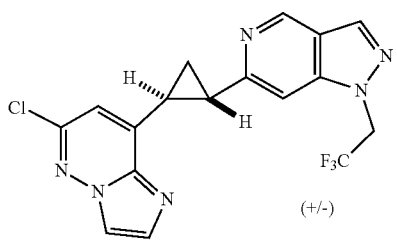 [SMILES: FC(F)(F)Cn1ncc2cnc([C@H]3C[C@@H]3c3cc(Cl)nn4ccnc34)cc21]

6-((1S,2S)-2-(6-chloroimidazo[1,2-b]pyridazin-8-yl)cyclopropyl)-1-(2,2,2-trifluoroethyl)-1H-pyrazolo[4,3-c]pyridine was prepared as a racemic mixture in the manner described for Intermediate 846, but replacing 6-bromo-2-(difluoromethyl)benzo[d]thiazole with 6-bromo-1-(2,2,2-trifluoroethyl)-1H-pyrazolo[4,3-c]pyridine. ES/MS m/z: 393.10 [M+H].

Intermediate 849. 6-((1S,2S)-2-(6-chloroimidazo[1,2-b]pyridazin-8-yl)cyclopropyl)-1-(2,2,2-trifluoroethyl)-1H-pyrazolo[3,4-b]pyridine

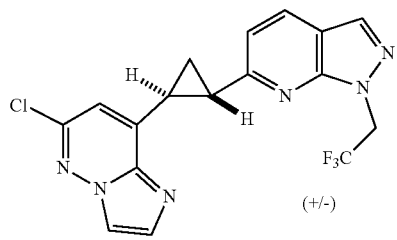 [SMILES: FC(F)(F)Cn1ncc2ccc([C@H]3C[C@@H]3c3cc(Cl)nn4ccnc34)nc21]

(+/−)

6-((1S,2S)-2-(6-chloroimidazo[1,2-b]pyridazin-8-yl)cyclopropyl)-1-(2,2,2-trifluoroethyl)-1H-pyrazolo[3,4-b]pyridine was prepared as a racemic mixture in the manner described for Intermediate 846, but replacing 6-bromo-2-(difluoromethyl)benzo[d]thiazole with 6-bromo-1-(2,2,2-trifluoroethyl)-1H-pyrazolo[3,4-b]pyridine. ES/MS m/z: 393.10 [M+H].

Intermediate 850. 6-((1S,2S)-2-(6-chloroimidazo[1,2-b]pyridazin-8-yl)cyclopropyl)-1-(2,2,2-trifluoroethyl)-1H-pyrazolo[4,3-b]pyridine

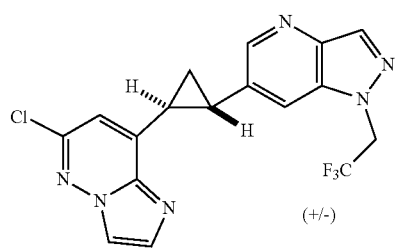 [SMILES: FC(F)(F)Cn1ncc2ncc([C@H]3C[C@@H]3c3cc(Cl)nn4ccnc34)cc21]

(+/−)

6-((1S,2S)-2-(6-chloroimidazo[1,2-b]pyridazin-8-yl)cyclopropyl)-1-(2,2,2-trifluoroethyl)-1H-pyrazolo[4,3-b]pyridine was prepared as a racemic mixture in the manner described for Intermediate 846, but replacing 6-bromo-2-(difluoromethyl)benzo[d]thiazole with 6-bromo-1-(2,2,2-trifluoroethyl)-1H-pyrazolo[4,3-b]pyridine. ES/MS m/z: 393.10 [M+H].

Intermediate 851. 6-chloro-8-((2S,2S)-2-(1-(2,2,2-trifluoroethyl)-2-(trifluoromethyl)-1H-benzo[d]imidazol-6-yl)cyclopropyl)imidazo[1,2-b]pyridazine

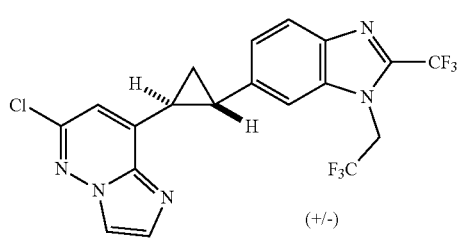 [SMILES: FC(F)(F)Cn1c(C(F)(F)F)nc2ccc([C@H]3C[C@@H]3c3cc(Cl)nn4ccnc34)cc21]

(+/−)

6-chloro-8-((1S,2S)-2-(1-(2,2,2-trifluoroethyl)-2-(trifluoromethyl)-1H-benzo[d]imidazol-6-yl)cyclopropyl)imidazo[1,2-b]pyridazine was prepared as a racemic mixture in the manner described for Intermediate 846, but replacing 6-bromo-2-(difluoromethyl)benzo[d]thiazole with 6-bromo-1-(2,2,2-trifluoroethyl)-2-(trifluoromethyl)-1H-benzo[d]imidazole. ES/MS m/z: 460.00 [M+H].

Intermediate 852. 6-chloro-8-((2S,2S)-2-(1-(2,2,2-trifluoroethyl)-2-(trifluoromethyl)-1H-benzo[d]imidazol-6-yl)cyclopropyl)imidazo[1,2-b]pyridazine

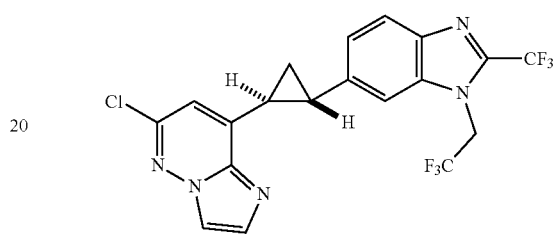

6-chloro-8-((1S,2S)-2-(1-(2,2,2-trifluoroethyl)-2-(trifluoromethyl)-1H-benzo[d]imidazol-6-yl)cyclopropyl)imidazo[1,2-b]pyridazine was chirally separated from the racemic Intermediate 851 by SFC Cell 2 column (15% IPA-NH₃).

Intermediate 853. 6-chloro-8-((2S,2S)-2-(2-(difluoromethyl)-1-(2,2,2-trifluoroethyl)-1H-benzo[d]imidazol-6-yl)cyclopropyl)imidazo[1,2-b]pyridazine

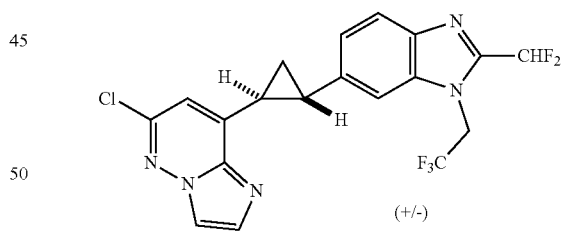

(+/−)

6-chloro-8-((1S,2S)-2-(2-(difluoromethyl)-1-(2,2,2-trifluoroethyl)-1H-benzo[d]imidazol-6-yl)cyclopropyl)imidazo[1,2-b]pyridazine was prepared as a racemic mixture in the manner described for Intermediate 846, but replacing 6-bromo-2-(difluoromethyl)benzo[d]thiazole with 6-bromo-2-(difluoromethyl)-1-(2,2,2-trifluoroethyl)-1H-benzo[d]imidazole. ES/MS m/z: 442.10 [M+H].

Intermediate 854. 6-chloro-8-((1S,2S)-2-(2-(difluoromethyl)-1-(2,2,2-trifluoroethyl)-1H-benzo[d]imidazol-5-yl)cyclopropyl)imidazo[1,2-b]pyridazine

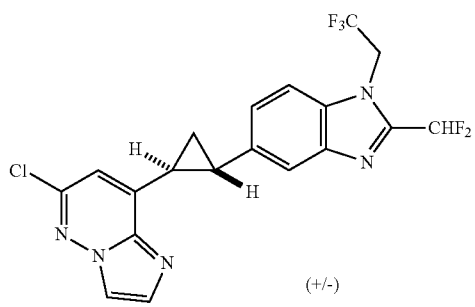 [SMILES: FC(F)c1nc2cc([C@H]3C[C@@H]3c3cc(Cl)nn4ccnc34)ccc2n1CC(F)(F)F]

6-chloro-8-((1S,2S)-2-(2-(difluoromethyl)-1-(2,2,2-trifluoroethyl)-1H-benzo[d]imidazol-5-yl)cyclopropyl)imidazo[1,2-b]pyridazine was prepared as a racemic mixture in the manner described for Intermediate 846, but replacing 6-bromo-2-(difluoromethyl)benzo[d]thiazole with 5-bromo-2-(difluoromethyl)-1-(2,2,2-trifluoroethyl)-1H-benzo[d]imidazole. ES/MS m/z: 442.10 [M+H].

Intermediate 855. 6-chloro-8-((1S,2S)-2-(5-chloro-4-(2,2,2-trifluoroethoxy)pyridin-2-yl)cyclopropyl)imidazo[1,2-b]pyridazine

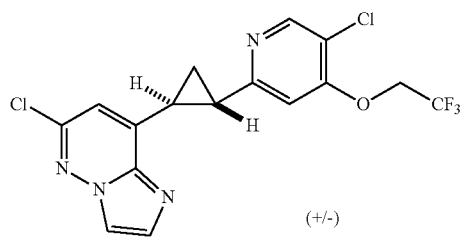 [SMILES: FC(F)(F)COc1cc([C@H]2C[C@@H]2c2cc(Cl)nn3ccnc23)ncc1Cl]

6-chloro-8-((1S,2S)-2-(5-chloro-4-(2,2,2-trifluoroethoxy)pyridin-2-yl)cyclopropyl)imidazo[1,2-b]pyridazine was prepared as a racemic mixture in the manner described for Intermediate 846, but replacing 6-bromo-2-(difluoromethyl)benzo[d]thiazole with 2-bromo-5-chloro-4-(2,2,2-trifluoroethoxy)pyridine. ES/MS m/z: 403.10 [M+H].

Intermediate 856. 6-chloro-8-((2S,2S)-2-(5-chloro-4-(2,2-difluorocyclopropyl)methoxy)pyridin-2-yl)cyclopropyl)imidazo[1,2-b]pyridazine

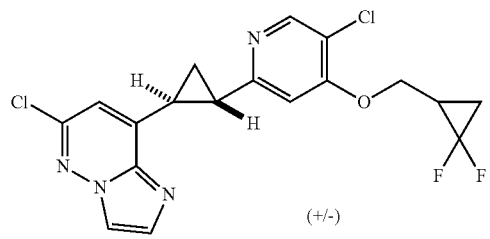 [SMILES: FC1(F)CC1COc1cc([C@H]2C[C@@H]2c2cc(Cl)nn3ccnc23)ncc1Cl]

6-chloro-8-((2S,2S)-2-(5-chloro-4-(2,2-difluorocyclopropyl)methoxy)pyridin-2-yl)cyclopropyl)imidazo[1,2-b]pyridazine was prepared as a racemic mixture in the manner described for Intermediate 846, but replacing 6-bromo-2-(difluoromethyl)benzo[d]thiazole with 2-bromo-5-chloro-4-((2,2-difluorocyclopropyl)methoxy)pyridine. ES/MS m/z: 411.10 [M+H].

Intermediate 857. 7-((2S,2S)-2-(6-chloroimidazo[1,2-b]pyridazin-8-yl)cyclopropyl)-1-(2,2,2-trifluoroethyl)quinolin-2(1H)-one

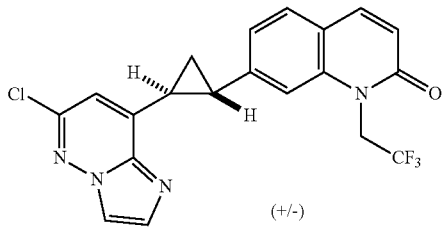 [SMILES: O=c1ccc2ccc([C@H]3C[C@@H]3c3cc(Cl)nn4ccnc34)cc2n1CC(F)(F)F]

7-((1S,2S)-2-(6-chloroimidazo[1,2-b]pyridazin-8-yl)cyclopropyl)-1-(2,2,2-trifluoroethyl)quinolin-2(1H)-one was prepared as a racemic mixture in the manner described for Intermediate 846, but replacing 6-bromo-2-(difluoromethyl)benzo[d]thiazole with 7-bromo-1-(2,2,2-trifluoroethyl)quinolin-2(1H)-one. ES/MS m/z: 419.10 [M+H].

Intermediate 858. 7-((2S,2S)-2-(6-chloroimidazo[1,2-b]pyridazin-8-yl)cyclopropyl)-2-(2,2,2-trifluoroethoxy)quinoline

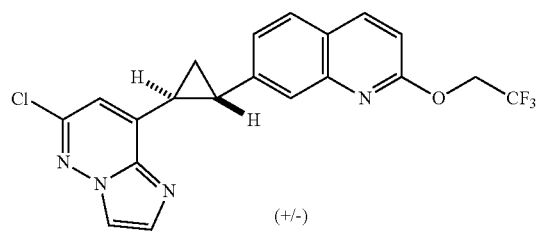 [SMILES: FC(F)(F)COc1ccc2ccc([C@H]3C[C@@H]3c3cc(Cl)nn4ccnc34)cc2n1]

7-((1S,2S)-2-(6-chloroimidazo[1,2-b]pyridazin-8-yl)cyclopropyl)-2-(2,2,2-trifluoroethoxy)quinoline was prepared as a racemic mixture in the manner described for Intermediate 846, but replacing 6-bromo-2-(difluoromethyl)benzo[d]thiazole with 7-bromo-2-(2,2,2-trifluoroethoxy)quinoline. ES/MS m/z: 419.10 [M+H].

Intermediate 859. 6-chloro-8-((2S,2S)-2-(3-(2,2,2-trifluoroethyl)imidazo[1,5-a]pyridin-6-yl)cyclopropyl)imidazo[1,2-b]pyridazine

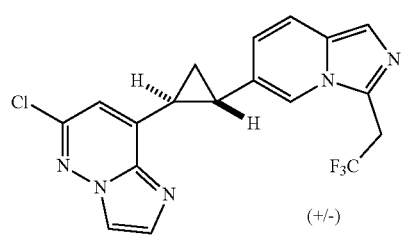 [SMILES: FC(F)(F)Cc1ncc2ccc([C@H]3C[C@@H]3c3cc(Cl)nn4ccnc34)cn12]

6-chloro-8-((1S,2S)-2-(3-(2,2,2-trifluoroethyl)imidazo[1,5-a]pyridin-6-yl)cyclopropyl)imidazo[1,2-b]pyridazine was prepared as a racemic mixture in the manner described for Intermediate 846, but replacing 6-bromo-2-(difluoromethyl)benzo[d]thiazole with 6-bromo-3-(2,2,2-trifluoroethyl)imidazo[1,5-a]pyridine. ES/MS m/z: 392.10 [M+H].

Intermediate 860. 6-chloro-8-((1S,2S)-2-(3-(2,2,2-trifluoroethyl)-1-(trifluoromethyl)imidazo[1,5-a]pyridin-6-yl)cyclopropyl)imidazo[1,2-b]pyridazine

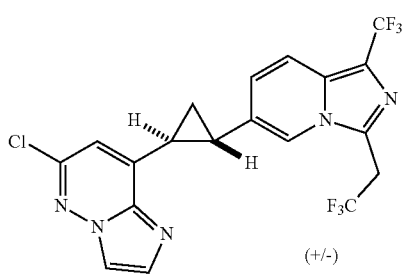 [SMILES: FC(F)(F)Cc1nc(C(F)(F)F)c2ccc([C@H]3C[C@@H]3c3cc(Cl)nn4ccnc34)cn12]

6-chloro-8-((1S,2S)-2-(3-(2,2,2-trifluoroethyl)-1-(trifluoromethyl)imidazo[1,5-a]pyridin-6-yl)cyclopropyl)imidazo[1,2-b]pyridazine was prepared as racemic mixture in the manner described for Intermediate 846, but replacing 6-bromo-2-(difluoromethyl)benzo[d]thiazole with 6-bromo-3-(2,2,2-trifluoroethyl)-1-(trifluoromethyl)imidazo[1,5-a]pyridine. ES/MS m/z: 460.10 [M+H].

Intermediate 861. 6-((1S,2S)-2-(6-chloroimidazo[1,2-b]pyridazin-8-yl)cyclopropyl)-1-(2,2,2-trifluoroethyl)-3-(trifluoromethyl)-1H-pyrazolo[4,3-c]pyridine

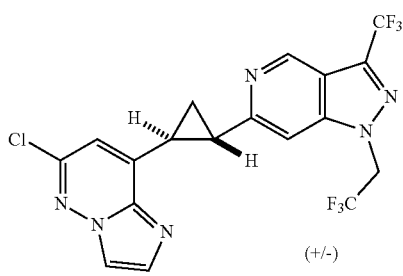 [SMILES: FC(F)(F)Cn1nc(C(F)(F)F)c2cnc([C@H]3C[C@@H]3c3cc(Cl)nn4ccnc34)cc21]

6-((1S,2S)-2-(6-chloroimidazo[1,2-b]pyridazin-8-yl)cyclopropyl)-1-(2,2,2-trifluoroethyl)-3-(trifluoromethyl)-1H-pyrazolo[4,3-c]pyridine was prepared as a racemic mixture in the manner described for Intermediate 846, but replacing 6-bromo-2-(difluoromethyl)benzo[d]thiazole with 6-chloro-1-(2,2,2-trifluoroethyl)-3-(trifluoromethyl)-1H-pyrazolo[4,3-c]pyridine. ES/MS m/z: 461.10 [M+H].

Intermediate 862. 6-((1S,2S)-2-(6-chloroimidazo[1,2-b]pyridazin-8-yl)cyclopropyl)-7-fluoro-1-(2,2,2-trifluoroethyl)-1H-pyrazolo[4,3-c]pyridine

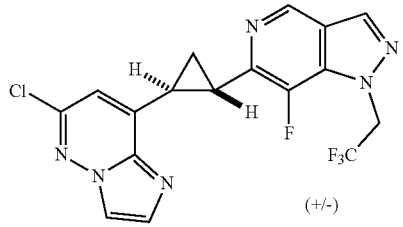 [SMILES: Fc1c([C@H]2C[C@@H]2c2cc(Cl)nn3ccnc23)ncc2cnn(CC(F)(F)F)c12]

6-((1S,2S)-2-(6-chloroimidazo[1,2-b]pyridazin-8-yl)cyclopropyl)-7-fluoro-1-(2,2,2-trifluoroethyl)-1H-pyrazolo[4,3-c]pyridine was prepared as a racemic mixture in the manner described for Intermediate 846, but replacing 6-bromo-2-(difluoromethyl)benzo[d]thiazole with 6-chloro-7-fluoro-1-(2,2,2-trifluoroethyl)-1H-pyrazolo[4,3-c]pyridine. ES/MS m/z: 411.10 [M+H].

Intermediate 863. 7-((2S,2S)-2-(6-chloroimidazo[1,2-b]pyridazin-8-yl)cyclopropyl)-1-(trifluoromethyl)-2,3-dihydro-1H-benzo[d]pyrrolo[1,2-a]imidazole

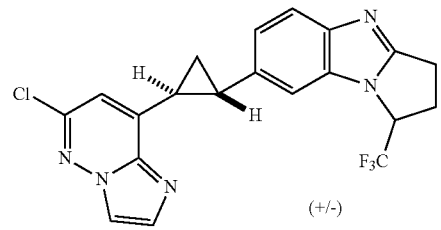 [SMILES: FC(F)(F)C1CCc2nc3ccc([C@H]4C[C@@H]4c4cc(Cl)nn5ccnc45)cc3n21]

7-((1S,2S)-2-(6-chloroimidazo[1,2-b]pyridazin-8-yl)cyclopropyl)-1-(trifluoromethyl)-2,3-dihydro-1H-benzo[d]pyrrolo[1,2-a]imidazole was prepared as a racemic mixture in the manner described for Intermediate 846, but replacing 6-bromo-2-(difluoromethyl)benzo[d]thiazole with 7-bromo-1-(trifluoromethyl)-2,3-dihydro-1H-benzo[d]pyrrolo[1,2-a]imidazole. ES/MS m/z: 418.10 [M+H].

Intermediate 864. 6-chloro-8-((2S,2S)-2-(4-(2-(trifluoromethyl)phenyl)pyridin-2-yl)cyclopropyl)imidazo[1,2-b]pyridazine

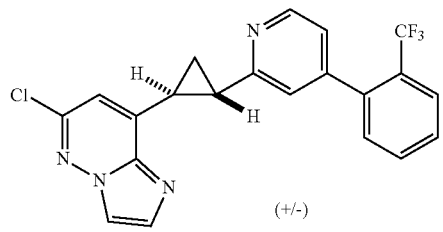 [SMILES: FC(F)(F)c1ccccc1-c1ccnc([C@H]2C[C@@H]2c2cc(Cl)nn3ccnc23)c1]

6-chloro-8-((1S,2S)-2-(4-(2-(trifluoromethyl)phenyl)pyridin-2-yl)cyclopropyl)imidazo[1,2-b]pyridazine was prepared as a racemic mixture in the manner described for Intermediate 846, but replacing 6-bromo-2-(difluoromethyl)benzo[d]thiazole with 2-chloro-4-(2-(trifluoromethyl)phenyl)pyridine. ES/MS m/z: 415.10 [M+H].

Intermediate 865. 6-chloro-8-((2S,2S)-2-(4-(2,4-difluorophenyl)pyridin-2-yl)cyclopropyl)imidazo[1,2-b]pyridazine

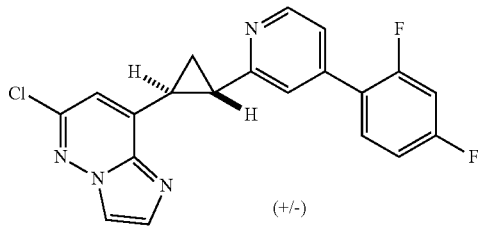 [SMILES: Fc1ccc(-c2ccnc([C@H]3C[C@@H]3c3cc(Cl)nn4ccnc34)c2)c(F)c1]

6-chloro-84(1S,2S)-2-(4-(2,4-difluorophenyl)pyridin-2-yl)cyclopropyl)imidazo[1,2-b]pyridazine was prepared as a racemic mixture in the manner described for Intermediate 846, but replacing 6-bromo-2-(difluoromethyl)benzo[d]thiazole with 2-chloro-4-(2,4-difluorophenyl)pyridine. ES/MS m/z: 383.10 [M+H].

Intermediate 866. 6-((1S,2S)-2-(6-chloroimidazo[1,2-b]pyridazin-8-yl)cyclopropyl)-1-(2,2,2-trifluoroethyl)-2-(trifluoromethyl)-1H-imidazo[4,5-c]pyridine

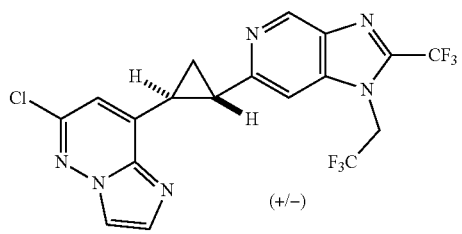 [SMILES: FC(F)(F)Cn1c(C(F)(F)F)nc2cnc([C@H]3C[C@@H]3c3cc(Cl)nn4ccnc34)cc21]

6-((1S,2S)-2-(6-chloroimidazo[1,2-b]pyridazin-8-yl)cyclopropyl)-1-(2,2,2-trifluoroethyl)-2-(trifluoromethyl)-1H-imidazo[4,5-c]pyridine was prepared as a racemic mixture in the manner described for Intermediate 846, but replacing 6-bromo-2-(difluoromethyl)benzo[d]thiazole with 6-chloro-1-(2,2,2-trifluoroethyl)-2-(trifluoromethyl)-1H-imidazo[4,5-c]pyridine. ES/MS m/z: 461.10 [M+H].

Intermediate 867. 6-chloro-8-((1S,2S)-2-(3-(trifluoromethyl)imidazo[1,5-a]pyridin-7-yl)cyclopropyl)imidazo[1,2-b]pyridazine

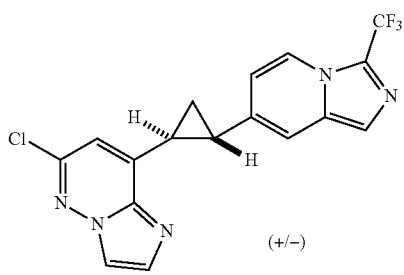 [SMILES: FC(F)(F)c1ncc2cc([C@H]3C[C@@H]3c3cc(Cl)nn4ccnc34)ccn12]

6-chloro-8-((2S,2S)-2-(3-(trifluoromethyl)imidazo[1,5-a]pyridin-7-yl)cyclopropyl)imidazo[1,2-b]pyridazine was prepared as a racemic mixture in the manner described for Intermediate 846, but replacing 6-bromo-2-(difluoromethyl)benzo[d]thiazole with 7-chloro-3-(trifluoromethyl)imidazo[1,5-a]pyridine. ES/MS m/z: 378.10 [M+H].

Intermediate 868. 7-((1S,2S)-2-(6-chloroimidazo[1,2-b]pyridazin-8-yl)cyclopropyl)-5-(2,2,2-trifluoroethoxy)quinoline

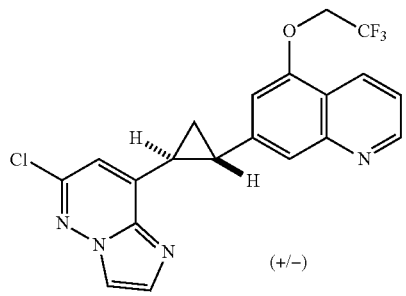 [SMILES: FC(F)(F)COc1cc([C@H]2C[C@@H]2c2cc(Cl)nn3ccnc23)cc2ncccc12]

7-((1S,2S)-2-(6-chloroimidazo[1,2-b]pyridazin-8-yl)cyclopropyl)-5-(2,2,2-trifluoroethoxy)quinoline was prepared as a racemic mixture in the manner described for Intermediate 846, but replacing 6-bromo-2-(difluoromethyl)benzo[d]thiazole with 7-chloro-5-(2,2,2-trifluoroethoxy)quinoline. ES/MS m/z: 419.10 [M+H].

Intermediate 869. 6-chloro-8-((2S,2S)-2-(4,7-difluoro-1-(2,2,2-trifluoroethyl)-1H-indazol-6-yl)cyclopropyl)imidazo[1,2-b]pyridazine

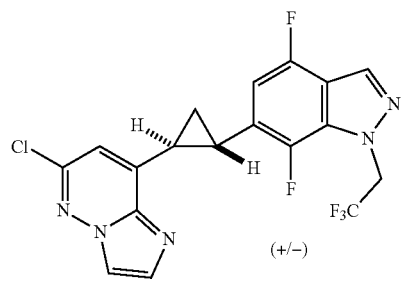 [SMILES: Fc1cc([C@H]2C[C@@H]2c2cc(Cl)nn3ccnc23)c(F)c2c1cnn2CC(F)(F)F]

6-chloro-8-((2S,2S)-2-(4,7-difluoro-1-(2,2,2-trifluoroethyl)-1H-indazol-6-yl)cyclopropyl)imidazo[1,2-b]pyridazine was prepared as a racemic mixture in the manner described for Intermediate 846, but replacing 6-bromo-2-(difluoromethyl)benzo[d]thiazole with 6-bromo-4,7-difluoro-1-(2,2,2-trifluoroethyl)-1H-indazole. ES/MS m/z: 428.10 [M+H].

Intermediate 870. 6-chloro-8-((2S,2S)-2-(3-(2,2,2-trifluoroethyl)-2-(trifluoromethyl)imidazo[1,2-a]pyridin-6-yl)cyclopropyl)imidazo[1,2-b]pyridazine

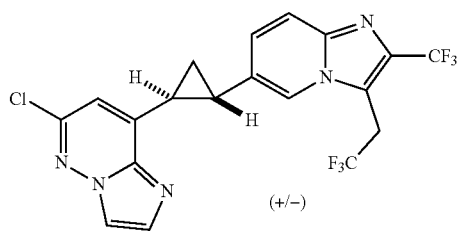 [SMILES: FC(F)(F)Cc1c(C(F)(F)F)nc2ccc([C@H]3C[C@@H]3c3cc(Cl)nn4ccnc34)cn12]

6-chloro-8-((1S,2S)-2-(3-(2,2,2-trifluoroethyl)-2-(trifluoromethyl)imidazo[1,2-a]pyridin-6-yl)cyclopropyl)imidazo[1,2-b]pyridazine was prepared as a racemic mixture in the manner described for Intermediate 846, but replacing 6-bromo-2-(difluoromethyl)benzo[d]thiazole with 6-bromo-3-(2,2,2-trifluoroethyl)-2-(trifluoromethyl)imidazo[1,2-a]pyridine. ES/MS m/z: 460.10 [M+H].

Intermediate 871. 8-((1S,3S)-3-(3,4-difluorophenyl)-2,2-difluorocyclopropyl)-6-(2,4-dimethoxypyrimidin-5-yl)imidazo[1,2-b]pyridazine

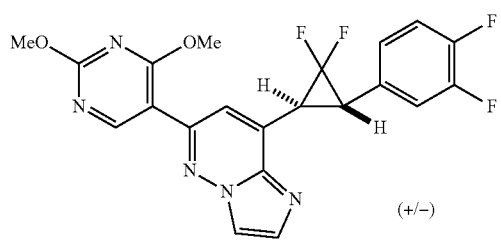 [SMILES: COc1ncc(-c2cc([C@@H]3[C@@H](c4ccc(F)c(F)c4)C3(F)F)c3nccn3n2)c(OC)n1]

8-((1S,3S)-3-(3,4-difluorophenyl)-2,2-difluorocyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(3,4-difluorophenyl)cyclopropyl)imidazo[1,2-b]pyridazine (Racemic Mixture). ES/MS m/z: 446.10 [M+H].

Intermediate 872. 8-((2S,2S)-2-(2-chlorophenyl)cyclopropyl)-6-(2,4-dimethoxypyrimidin-5-yl)imidazo[1,2-b]pyridazine

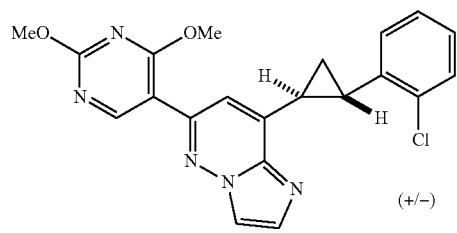 [SMILES: COc1ncc(-c2cc([C@H]3C[C@@H]3c3ccccc3Cl)c3nccn3n2)c(OC)n1]

8-((1S,2S)-2-(2-chlorophenyl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(2-chlorophenyl)cyclopropyl)imidazo[1,2-b]pyridazine (racemic mixture). ES/MS m/z: 408.10 [M+H].

Intermediate 873. 2-chloro-5-((2S,2S)-2-(6-(2,4-dimethoxypyrimidin-5-yl)imidazo[1,2-b]pyridazin-8-yl)cyclopropyl)benzonitrile

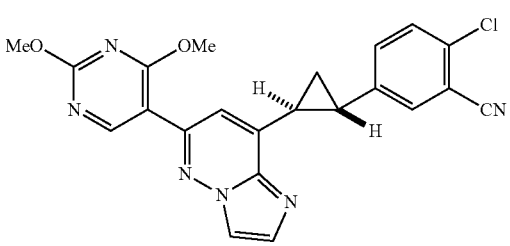 [SMILES: COc1ncc(-c2cc([C@H]3C[C@@H]3c3ccc(Cl)c(C#N)c3)c3nccn3n2)c(OC)n1]

2-chloro-5-((1S,2S)-2-(6-(2,4-dimethoxypyrimidin-5-yl)imidazo[1,2-b]pyridazin-8-yl)cyclopropyl)benzonitrile was prepared in the manner described for Intermediate 18, but replacing 6-chloro-8-cyclopropyl-2-methyl-imidazo[1,2-b]pyridazine with 2-chloro-5-((1S,2S)-2-(6-chloroimidazo[1,2-b]pyridazin-8-yl)cyclopropyl)benzonitrile. ES/MS m/z: 433.10 [M+H].

Intermediate 874. 6-(2,4-dimethoxypyrimidin-5-yl)-8-((1S,2S)-2-(4-(trifluoromethyl)phenyl)cyclopropyl)imidazo[1,2-b]pyridazine

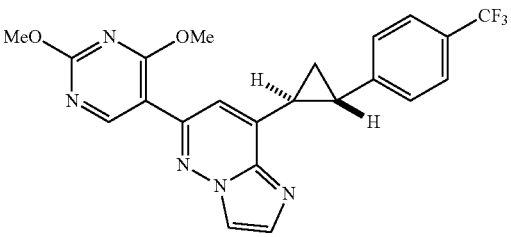 [SMILES: COc1ncc(-c2cc([C@H]3C[C@@H]3c3ccc(C(F)(F)F)cc3)c3nccn3n2)c(OC)n1]

6-(2,4-dimethoxypyrimidin-5-yl)-8-((2S,2S)-2-(4-(trifluoromethyl)phenyl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((2S,2S)-2-(4-(trifluoromethyl)phenyl)cyclopropyl)imidazo[1,2-b]pyridazine. ES/MS m/z: 442.10 [M+H].

Intermediate 875. 8-((2S,2S)-2-(4-(difluoromethoxy)phenyl)cyclopropyl)-6-(2,4-dimethoxypyrimidin-5-yl)imidazo[1,2-b]pyridazine

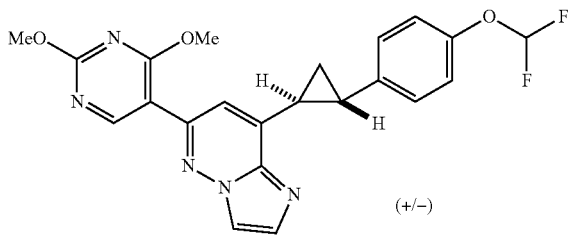 [SMILES: COc1ncc(-c2cc([C@H]3C[C@@H]3c3ccc(OC(F)F)cc3)c3nccn3n2)c(OC)n1]

(+/−)

8-((1S,2S)-2-(4-(difluoromethoxy)phenyl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(4-(difluoromethoxy)phenyl)cyclopropyl)imidazo[1,2-b]pyridazine (Racemic Mixture). ES/MS m/z: 440.20 [M+H].

Intermediate 876. 8-((2S,2S)-2-(4-(difluoromethoxy)phenyl)cyclopropyl)-6-(2,4-dimethoxypyrimidin-5-yl)imidazo[1,2-b]pyridazine

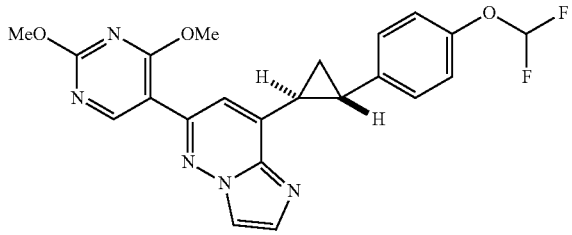 [SMILES: COc1ncc(-c2cc([C@H]3C[C@@H]3c3ccc(OC(F)F)cc3)c3nccn3n2)c(OC)n1]

8-((1S,2S)-2-(4-(difluoromethoxy)phenyl)cyclopropyl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(4-(difluoromethoxy)phenyl)cyclopropyl)imidazo[1,2-b]pyridazine. ES/MS m/z: 440.20 [M+H].

Intermediate 877. 4-((2S,2S)-2-(6-(2,4-dimethoxypyrimidin-5-yl)imidazo[1,2-b]pyridazin-8-yl)cyclopropyl)-2,6-difluorobenzonitrile

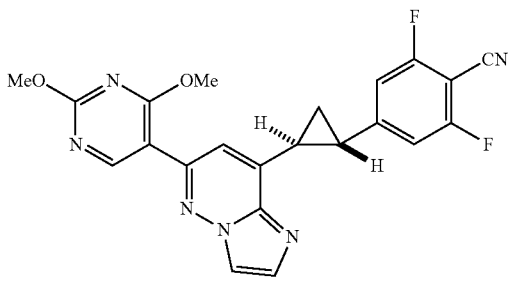 [SMILES: COc1ncc(-c2cc([C@H]3C[C@@H]3c3cc(F)c(C#N)c(F)c3)c3nccn3n2)c(OC)n1]

4-((1S,2S)-2-(6-(2,4-dimethoxypyrimidin-5-yl)imidazo[1,2-b]pyridazin-8-yl)cyclopropyl)-2,6-difluorobenzonitrile was prepared in the manner described for Intermediate 18, but replacing 6-chloro-8-cyclopropyl-2-methyl-imidazo[1,2-b]pyridazine with 4-(1S,2S)-2-(6-chloroimidazo[1,2-b]pyridazin-8-yl)cyclopropyl)-2,6-difluorobenzonitrile. ES/MS m/z: 435.10 [M+H].

Intermediate 878. 4-((2S,2S)-2-(6-(2,4-dimethoxypyrimidin-5-yl)imidazo[1,2-b]pyridazin-8-yl)cyclopropyl)-2,3-difluorobenzonitrile

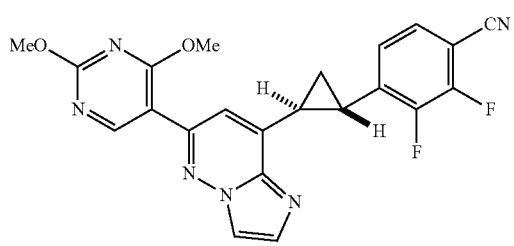 [SMILES: COc1ncc(-c2cc([C@H]3C[C@@H]3c3ccc(C#N)c(F)c3F)c3nccn3n2)c(OC)n1]

4-((1S,2S)-2-(6-(2,4-dimethoxypyrimidin-5-yl)imidazo[1,2-b]pyridazin-8-yl)cyclopropyl)-2,3-difluorobenzonitrile was prepared in the manner described for Intermediate 18, but replacing 6-chloro-8-cyclopropyl-2-methyl-imidazo[1,2-b]pyridazine with 4-(1S,2S)-2-(6-chloroimidazo[1,2-b]pyridazin-8-yl)cyclopropyl)-2,3-difluorobenzonitrile. ES/MS m/z: 435.10 [M+H].

Intermediate 879. 4-((2S,2S)-2-(6-(2,4-dimethoxypyrimidin-5-yl)imidazo[1,2-b]pyridazin-8-yl)cyclopropyl)-2-methoxybenzonitrile

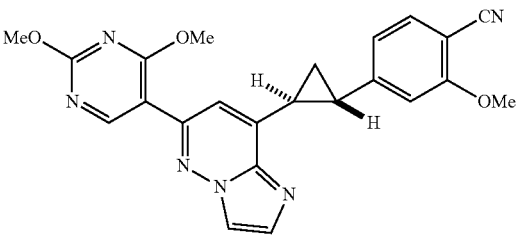 [SMILES: COc1ncc(-c2cc([C@H]3C[C@@H]3c3ccc(C#N)c(OC)c3)c3nccn3n2)c(OC)n1]

4-(1S,2S)-2-(6-(2,4-dimethoxypyrimidin-5-yl)imidazo[1,2-b]pyridazin-8-yl)cyclopropyl)-2-methoxybenzonitrile was prepared in the manner described for Intermediate 18, but replacing 6-chloro-8-cyclopropyl-2-methyl-imidazo[1,2-b]pyridazine with 4-((1S,2S)-2-(6-chloroimidazo[1,2-b]pyridazin-8-yl)cyclopropyl)-2-methoxybenzonitrile. ES/MS m/z: 429.20 [M+H].

Intermediate 880. 4-((2S,2S)-2-(6-(2,4-dimethoxypyrimidin-5-yl)imidazo[1,2-b]pyridazin-8-yl)cyclopropyl)-2-methylbenzonitrile

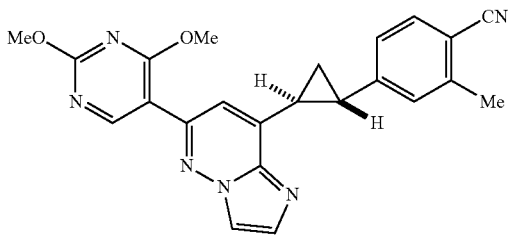 [SMILES: COc1ncc(-c2cc([C@H]3C[C@@H]3c3ccc(C#N)c(C)c3)c3nccn3n2)c(OC)n1]

4-((2S,2S)-2-(6-(2,4-dimethoxypyrimidin-5-yl)imidazo[1,2-b]pyridazin-8-yl)cyclopropyl)-2-methylbenzonitrile was prepared in the manner described for Intermediate 18, but replacing 6-chloro-8-cyclopropyl-2-methyl-imidazo[1,2-b]pyridazine with 4-((2S,2S)-2-(6-chloroimidazo[1,2-b]pyridazin-8-yl)cyclopropyl)-2-methylbenzonitrile. ES/MS m/z: 413.20 [M+H].

Intermediate 881. 2-cyclopropyl-4-(1S,2S)-2-(6-(2,4-dimethoxypyrimidin-5-yl)imidazo[1,2-b]pyridazin-8-yl)cyclopropyl)benzonitrile

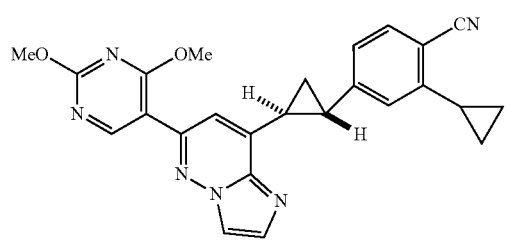 [SMILES: COc1ncc(-c2cc([C@H]3C[C@@H]3c3ccc(C#N)c(C4CC4)c3)c3nccn3n2)c(OC)n1]

2-cyclopropyl-4-((2S,2S)-2-(6-(2,4-dimethoxypyrimidin-5-yl)imidazo[1,2-b]pyridazin-8-yl)cyclopropyl)benzonitrile was prepared in the manner described for Intermediate 18, but replacing 6-chloro-8-cyclopropyl-2-methyl-imidazo[1,2-b]pyridazine with 4-((1S,2S)-2-(6-chloroimidazo[1,2-b]pyridazin-8-yl)cyclopropyl)-2-cyclopropylbenzonitrile. ES/MS m/z: 439.20 [M+H].

Intermediate 882. 6-(2,4-dimethoxypyrimidin-5-yl)-8-((1S,2S)-2-(4-(2,2,2-trifluoroethoxy)phenyl)cyclopropyl)imidazo[1,2-b]pyridazine

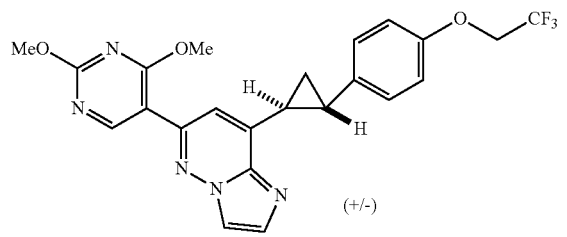 [SMILES: COc1ncc(-c2cc([C@H]3C[C@@H]3c3ccc(OCC(F)(F)F)cc3)c3nccn3n2)c(OC)n1]

6-(2,4-dimethoxypyrimidin-5-yl)-8-((1S,2S)-2-(4-(2,2,2-trifluoroethoxy)phenyl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(4-(2,2,2-trifluoroethoxy)phenyl)cyclopropyl)imidazo[1,2-b]pyridazine (Racemic Mixture). ES/MS m/z: 472.20 [M+H].

Intermediate 883. 8-((2S,2S)-2-(4-(2,2-difluoroethoxy)phenyl)cyclopropyl)-6-(2,4-dimethoxypyrimidin-5-yl)imidazo[1,2-b]pyridazine

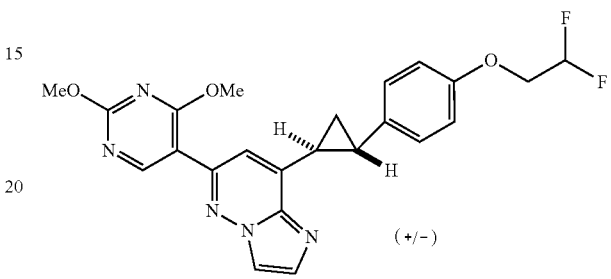

8-((1S,2S)-2-(4-(2,2-difluoroethoxy)phenyl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(4-(2,2-difluoroethoxy)phenyl)cyclopropyl)imidazo[1,2-b]pyridazine (Racemic Mixture). ES/MS m/z: 454.20 [M+H].

Intermediate 884. 8-((2S,2S)-2-(5-(2,2-difluoroethoxy)pyridin-2-yl)cyclopropyl)-6-(2,4-dimethoxypyrimidin-5-yl)imidazo[1,2-b]pyridazine

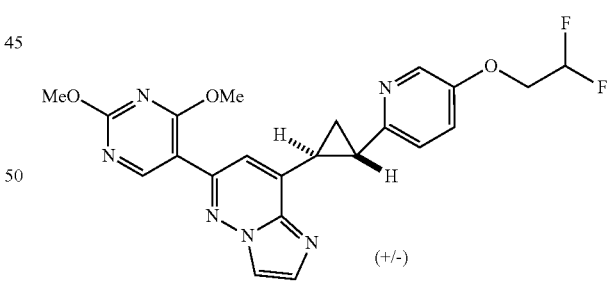

8-((1S,2S)-2-(5-(2,2-difluoroethoxy)pyridin-2-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(5-(2,2-difluoroethoxy)pyridin-2-yl)cyclopropyl)imidazo[1,2-b]pyridazine (Racemic Mixture). ES/MS m/z: 455.20 [M+H].

Intermediate 885. 4-((2S,2S)-2-(6-(2,4-dimethoxy-pyrimidin-5-yl)imidazo[1,2-b]pyridazin-8-yl)cyclopropyl)-2-fluoro-6-methylbenzonitrile

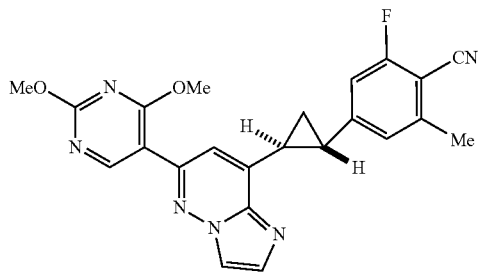 [SMILES: COc1ncc(-c2cc([C@H]3C[C@@H]3c3cc(C)c(C#N)c(F)c3)c3nccn3n2)c(OC)n1]

4-((2S,2S)-2-(6-(2,4-dimethoxypyrimidin-5-yl)imidazo[1,2-b]pyridazin-8-yl)cyclopropyl)-2-fluoro-6-methylbenzonitrile was prepared in the manner described for Intermediate 18, but replacing 6-chloro-8-cyclopropyl-2-methyl-imidazo[1,2-b]pyridazine with 4-((1S,2S)-2-(6-chloroimidazo[1,2-b]pyridazin-8-yl)cyclopropyl)-2-fluoro-6-methylbenzonitrile. ES/MS m/z: 431.20 [M+H].

Intermediate 886. 2-chloro-4-((2S,2S)-2-(6-(2,4-dimethoxypyrimidin-5-yl)imidazo[1,2-b]pyridazin-8-yl)cyclopropyl)benzonitrile

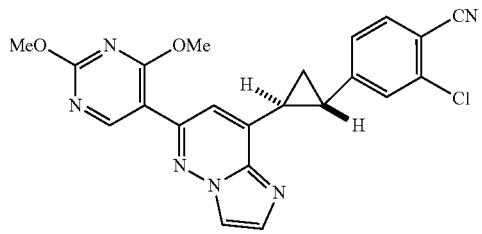 [SMILES: COc1ncc(-c2cc([C@H]3C[C@@H]3c3ccc(C#N)c(Cl)c3)c3nccn3n2)c(OC)n1]

2-chloro-4-((2S,2S)-2-(6-(2,4-dimethoxypyrimidin-5-yl)imidazo[1,2-b]pyridazin-8-yl)cyclopropyl)benzonitrile was prepared in the manner described for Intermediate 18, but replacing 6-chloro-8-cyclopropyl-2-methyl-imidazo[1,2-b]pyridazine with 2-chloro-4-((1S,2S)-2-(6-chloroimidazo[1,2-b]pyridazin-8-yl)cyclopropyl)benzonitrile. ES/MS m/z: 433.10 [M+H].

Intermediate 887. 4-((2S,2S)-2-(6-(2,4-dimethoxy-pyrimidin-5-yl)imidazo[1,2-b]pyridazin-8-yl)cyclopropyl)-2,5-difluorobenzonitrile

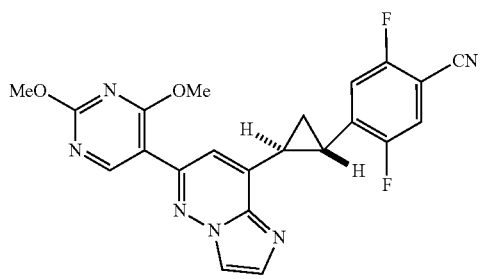 [SMILES: COc1ncc(-c2cc([C@H]3C[C@@H]3c3cc(F)c(C#N)cc3F)c3nccn3n2)c(OC)n1]

4-((1S,2S)-2-(6-(2,4-dimethoxypyrimidin-5-yl)imidazo[1,2-b]pyridazin-8-yl)cyclopropyl)-2,5-difluorobenzonitrile was prepared in the manner described for Intermediate 18, but replacing 6-chloro-8-cyclopropyl-2-methyl-imidazo[1,2-b]pyridazine with 4-(1S,2S)-2-(6-chloroimidazo[1,2-b]pyridazin-8-yl)cyclopropyl)-2,5-difluorobenzonitrile. ES/MS m/z: 435.10 [M+H].

Intermediate 888. 4-((1S,2S)-2-(6-(2,4-dimethoxy-pyrimidin-5-yl)-3-fluoroimidazo[1,2-b]pyridazin-8-yl)cyclopropyl)-2,5-difluorobenzonitrile

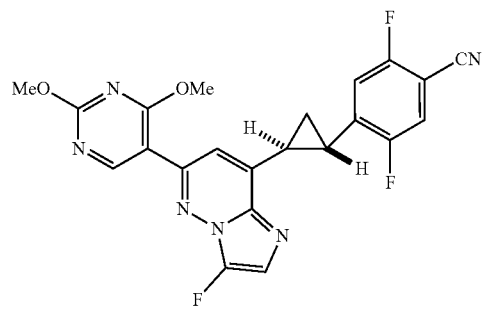 [SMILES: COc1ncc(-c2cc([C@H]3C[C@@H]3c3cc(F)c(C#N)cc3F)c3ncc(F)n3n2)c(OC)n1]

4-((1S,2S)-2-(6-(2,4-dimethoxypyrimidin-5-yl)-3-fluoro-imidazo[1,2-b]pyridazin-8-yl)cyclopropyl)-2,5-difluorobenzonitrile was prepared in the manner described for Intermediate 18, but replacing 6-chloro-8-cyclopropyl-2-methyl-imidazo[1,2-b]pyridazine with 4-(1S,2S)-2-(6-chloro-3-fluoroimidazo[1,2-b]pyridazin-8-yl)cyclopropyl)-2,5-difluorobenzonitrile. ES/MS m/z: 453.10 [M+H].

Intermediate 889. 6-((1S,2S)-2-(6-(2,4-dimethoxy-pyrimidin-5-yl)imidazo[1,2-b]pyridazin-8-yl)cyclopropyl)-2-(trifluoromethyl)benzo[d]thiazole

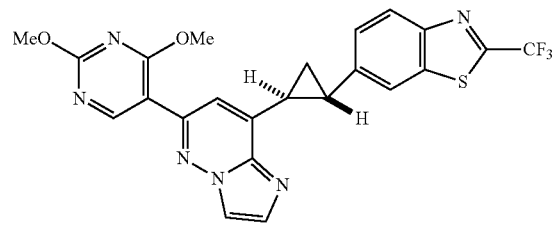 [SMILES: COc1ncc(-c2cc([C@H]3C[C@@H]3c3ccc4nc(C(F)(F)F)sc4c3)c3nccn3n2)c(OC)n1]

6-((1S,2S)-2-(6-(2,4-dimethoxypyrimidin-5-yl)imidazo[1,2-b]pyridazin-8-yl)cyclopropyl)-2-(trifluoromethyl)benzo[d]thiazole was prepared in the manner described for Intermediate 18, but replacing 6-chloro-8-cyclopropyl-2-methyl-imidazo[1,2-b]pyridazine with 64(1S,2S)-2-(6-chloroimidazo[1,2-b]pyridazin-8-yl)cyclopropyl)-2-(trifluoromethyl)benzo[d]thiazole. ES/MS m/z: 499.20 [M+H].

Intermediate 890. 8-((1S,2S)-2-(6-chloropyridin-3-yl)cyclopropyl)-6-(2,4-dimethoxypyrimidin-5-yl)imidazo[1,2-b]pyridazine

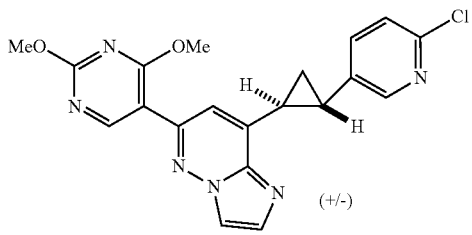 [SMILES: COc1ncc(-c2cc([C@H]3C[C@@H]3c3ccc(Cl)nc3)c3nccn3n2)c(OC)n1]

8-((1S,2S)-2-(6-chloropyridin-3-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(6-chloropyridin-3-yl)cyclopropyl)imidazo[1,2-b]pyridazine (racemic mixture). ES/MS m/z: 409.20 [M+H].

Intermediate 891. 2-(difluoromethyl)-6-((1S,2S)-2-(6-(2,4-dimethoxypyrimidin-5-yl)imidazo[1,2-b]pyridazin-8-yl)cyclopropyl)benzo[d]thiazole

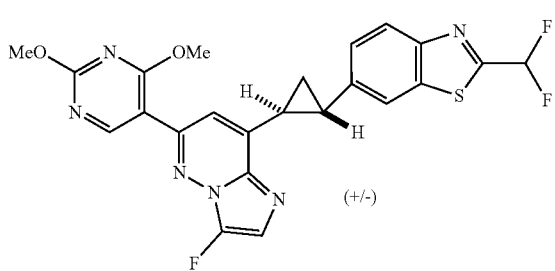 [SMILES: COc1ncc(-c2cc([C@H]3C[C@@H]3c3ccc4nc(C(F)F)sc4c3)c3ncc(F)n3n2)c(OC)n1]

2-(difluoromethyl)-6-((1S,2S)-2-(6-(2,4-dimethoxypyrimidin-5-yl)imidazo[1,2-b]pyridazin-8-yl)cyclopropyl)benzo[d]thiazole was prepared as racemic mixture in the manner described for Intermediate 18, but replacing 6-chloro-8-cyclopropyl-2-methyl-imidazo[1,2-b]pyridazine with 64(1S,2S)-2-(6-chloroimidazo[1,2-b]pyridazin-8-yl)cyclopropyl)-2-(difluoromethyl)benzo[d]thiazole (Racemic Mixture).

Intermediate 892. 6-((2S,2S)-2-(6-(2,4-dimethoxypyrimidin-5-yl)imidazo[1,2-b]pyridazin-8-yl)cyclopropyl)-2-methylbenzo[d]thiazole

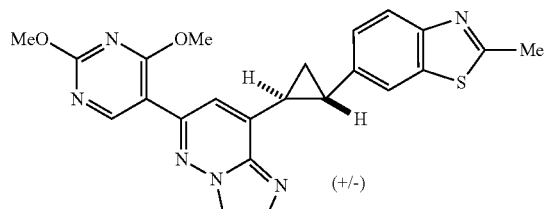

6-((1S,2S)-2-(6-(2,4-dimethoxypyrimidin-5-yl)imidazo[1,2-b]pyridazin-8-yl)cyclopropyl)-2-methylbenzo[d]thiazole was prepared as a racemic mixture in the manner described for Intermediate 18, but replacing 6-chloro-8-cyclopropyl-2-methyl-imidazo[1,2-b]pyridazine with 64(1S,2S)-2-(6-chloroimidazo[1,2-b]pyridazin-8-yl)cyclopropyl)-2-methylbenzo[d]thiazole (Racemic Mixture). ES/MS m/z: 445.20 [M+H].

Intermediate 893. 6-((2S,2S)-2-(6-(2,4-dimethoxypyrimidin-5-yl)-3-fluoroimidazo[1,2-b]pyridazin-8-yl)cyclopropyl)-2-methylbenzo[d]thiazole

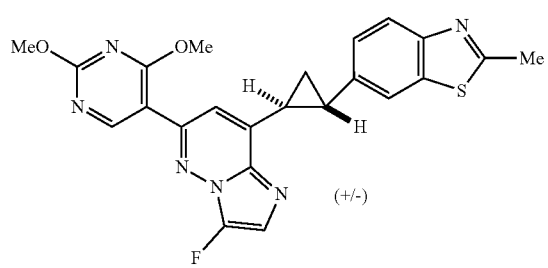 [SMILES: COc1ncc(-c2cc([C@H]3C[C@@H]3c3ccc4nc(C)sc4c3)c3ncc(F)n3n2)c(OC)n1]

6-((1S,2S)-2-(6-(2,4-dimethoxypyrimidin-5-yl)-3-fluoroimidazo[1,2-b]pyridazin-8-yl)cyclopropyl)-2-methylbenzo[d]thiazole was prepared as a racemic mixture in the manner described for Intermediate 18, but replacing 6-chloro-8-cyclopropyl-2-methyl-imidazo[1,2-b]pyridazine with 6-((1S,2S)-2-(6-chloro-3-fluoroimidazo[1,2-b]pyridazin-8-yl)cyclopropyl)-2-methylbenzo[d]thiazole (Racemic Mixture). ES/MS m/z: 463.20 [M+H].

Intermediate 894. 6-((2S,2S)-2-(6-(2,4-dimethoxypyrimidin-5-yl)-3-fluoroimidazo[1,2-b]pyridazin-8-yl)cyclopropyl)benzo[d]thiazole

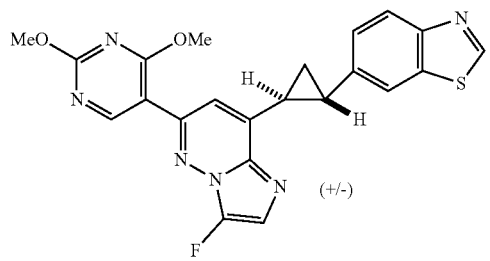 [SMILES: COc1ncc(-c2cc([C@H]3C[C@@H]3c3ccc4ncsc4c3)c3ncc(F)n3n2)c(OC)n1]

6-((1S,2S)-2-(6-(2,4-dimethoxypyrimidin-5-yl)-3-fluoroimidazo[1,2-b]pyridazin-8-yl)cyclopropyl)benzo[d]thiazole was prepared as a racemic mixture in the manner described for Intermediate 18, but replacing 6-chloro-8-cyclopropyl-2-methyl-imidazo[1,2-b]pyridazine with 6-((1S,2S)-2-(6-chloro-3-fluoroimidazo[1,2-b]pyridazin-8-yl)cyclopropyl)benzo[d]thiazole (Racemic Mixture). ES/MS m/z: 449.10 [M+H].

Intermediate 895. 8-((1S,2S)-2-(5-chloro-3-fluoro-pyridin-2-yl)cyclopropyl)-6-(2,4-dimethoxypyrimidin-5-yl)imidazo[1,2-b]pyridazine

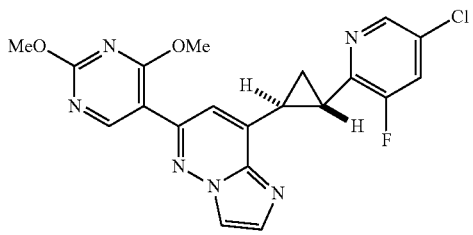 [SMILES: COc1ncc(-c2cc([C@H]3C[C@@H]3c3ncc(Cl)cc3F)c3nccn3n2)c(OC)n1]

8-((1S,2S)-2-(5-chloro-3-fluoropyridin-2-yl)cyclopropyl)-6-(2,4-dimethoxypyrimidin-5-yl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((2S,2S)-2-(5-chloro-3-fluoropyridin-2-yl)cyclopropyl)imidazo[1,2-b]pyridazine. ES/MS m/z: 427.10 [M+H].

Intermediate 896. 8-((1S,2S)-2-(5-chloro-3-fluoro-pyridin-2-yl)cyclopropyl)-6-(2,4-dimethoxypyrimidin-5-yl)-3-fluoroimidazo[1,2-b]pyridazine

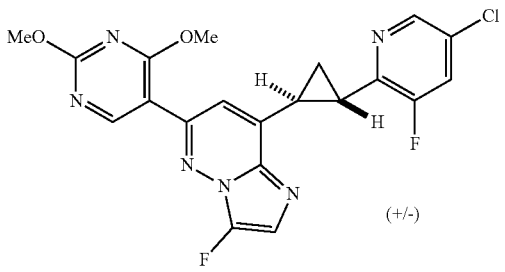 [SMILES: COc1ncc(-c2cc([C@H]3C[C@@H]3c3ncc(Cl)cc3F)c3ncc(F)n3n2)c(OC)n1]

(+/-)

8-((1S,2S)-2-(5-chloro-3-fluoropyridin-2-yl)cyclopropyl)-6-(2,4-dimethoxypyrimidin-5-yl)-3-fluoroimidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(5-chloro-3-fluoropyridin-2-yl)cyclopropyl)-3-fluoroimidazo[1,2-b]pyridazine (Racemic Mixture). ES/MS m/z: 445.10 [M+H].

Intermediate 897. 8-((1S,2S)-2-(5-chloro-3-fluoro-pyridin-2-yl)cyclopropyl)-6-(2,4-dimethoxypyrimidin-5-yl)-3-fluoroimidazo[1,2-b]pyridazine

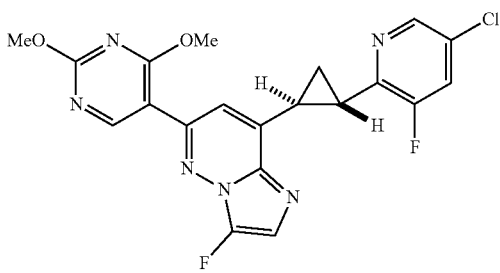 [SMILES: COc1ncc(-c2cc([C@H]3C[C@@H]3c3ncc(Cl)cc3F)c3ncc(F)n3n2)c(OC)n1]

8-((1S,2S)-2-(5-chloro-3-fluoropyridin-2-yl)cyclopropyl)-6-(2,4-dimethoxypyrimidin-5-yl)-3-fluoroimidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(5-chloro-3-fluoropyridin-2-yl)cyclopropyl)-3-fluoroimidazo[1,2-b]pyridazine. ES/MS m/z: 445.10 [M+H].

Intermediate 898. 8-((2S,2S)-2-(5-chloropyridin-2-yl)cyclopropyl)-6-(2,4-dimethoxypyrimidin-5-yl)imidazo[1,2-b]pyridazine

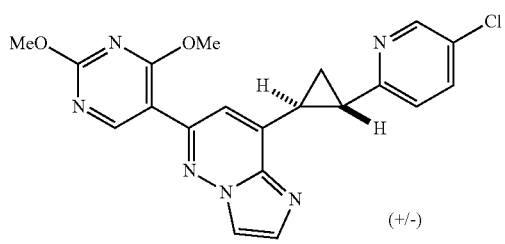 [SMILES: COc1ncc(-c2cc([C@H]3C[C@@H]3c3ccc(Cl)cn3)c3nccn3n2)c(OC)n1]

(+/-)

8-((1S,2S)-2-(5-chloropyridin-2-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(5-chloropyridin-2-yl)cyclopropyl)imidazo[1,2-b]pyridazine (racemic mixture). ES/MS m/z: 409.20 [M+H].

Intermediate 899 and 900. 8-((1S,2S)-2-(5-chloro-pyridin-2-yl)cyclopropyl)-6-(2,4-dimethoxypyrimidin-5-yl)imidazo[1,2-b]pyridazine and 8-((1R,2R)-2-(5-chloropyridin-2-yl)cyclopropyl)-6-(2,4-dimethoxypyrimidin-5-yl)imidazo[1,2-b]pyridazine

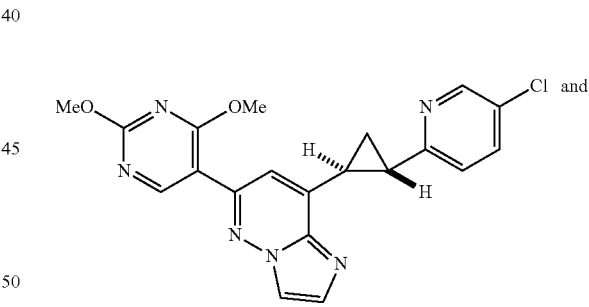

and

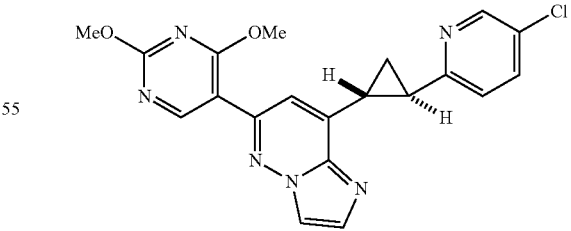

8-((1S,2S)-2-(5-chloropyridin-2-yl)cyclopropyl)-6-(2,4-dimethoxypyrimidin-5-yl)imidazo[1,2-b]pyridazine and 8-((1R,2R)-2-(5-chloropyridin-2-yl)cyclopropyl)-6-(2,4-dimethoxypyrimidin-5-yl)imidazo[1,2-b]pyridazine were chirally separated from the racemic mixture by SFC AD-H column (35% EtOH).

Intermediate 901. 8-((2S,2S)-2-(5-chloropyridin-2-yl)cyclopropyl)-6-(2,4-dimethoxypyrimidin-5-yl)-3-fluoroimidazo[1,2-b]pyridazine

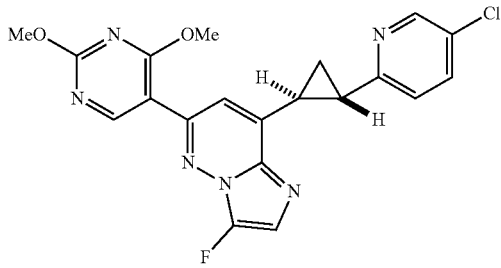 [SMILES: COc1ncc(-c2cc([C@H]3C[C@@H]3c3ccc(Cl)cn3)c3ncc(F)n3n2)c(OC)n1]

8-((1S,2S)-2-(5-chloropyridin-2-yl)cyclopropyl)-6-(2,4-dimethoxypyrimidin-5-yl)-3-fluoroimidazo[1,2-b]pyridazine was prepared in the manner described for Intermediate 18, but replacing 6-chloro-8-cyclopropyl-2-methyl-imidazo[1,2-b]pyridazine with 6-chloro-8-((2S,2S)-2-(5-chloropyridin-2-yl)cyclopropyl)-3-fluoroimidazo[1,2-b]pyridazine. ES/MS m/z: 427.10 [M+H].

Intermediate 902. 6-(2,4-dimethoxypyrimidin-5-yl)-8-((1S,2S)-2-(3-fluoro-5-(trifluoromethyl)pyridin-2-yl)cyclopropyl)imidazo[1,2-b]pyridazine

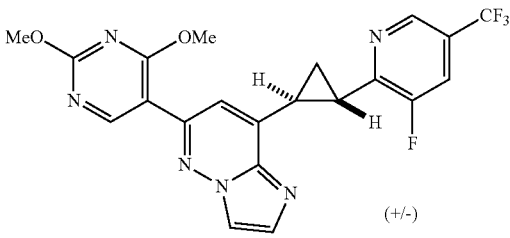 [SMILES: COc1ncc(-c2cc([C@H]3C[C@@H]3c3ncc(C(F)(F)F)cc3F)c3nccn3n2)c(OC)n1]

6-(2,4-dimethoxypyrimidin-5-yl)-8-((1S,2S)-2-(3-fluoro-5-(trifluoromethyl)pyridin-2-yl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(3-fluoro-5-(trifluoromethyl)pyridin-2-yl)cyclopropyl)imidazo[1,2-b]pyridazine (Racemic Mixture). ES/MS m/z: 461.10 [M+H].

Intermediate 903. 6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[4,3-c]pyridine

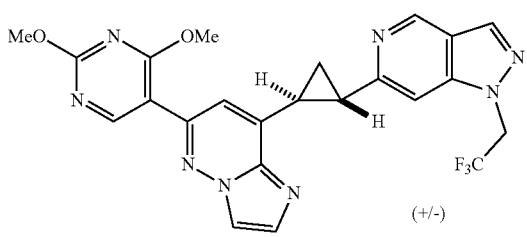 [SMILES: COc1ncc(-c2cc([C@H]3C[C@@H]3c3cc4c(cn3)cnn4CC(F)(F)F)c3nccn3n2)c(OC)n1]

6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[4,3-c]pyridine was prepared as a racemic mixture in the manner described for Intermediate 18, but replacing 6-chloro-8-cyclopropyl-2-methyl-imidazo[1,2-b]pyridazine with 6-((2S,2S)-2-(6-chloroimidazo[1,2-b]pyridazin-8-yl)cyclopropyl)-1-(2,2,2-trifluoroethyl)-1H-pyrazolo[4,3-c]pyridine (Racemic Mixture). ES/MS m/z: 497.20 [M+H].

Intermediate 904. 6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[3,4-b]pyridine

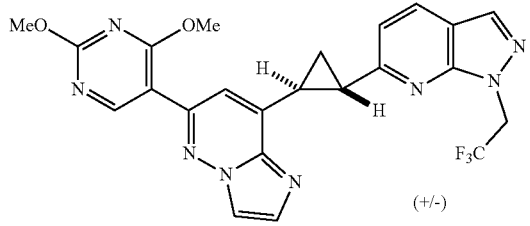 [SMILES: COc1ncc(-c2cc([C@H]3C[C@@H]3c3ccc4cnn(CC(F)(F)F)c4n3)c3nccn3n2)c(OC)n1]

6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[3,4-b]pyridine was prepared as a racemic mixture in the manner described for Intermediate 18, but replacing 6-chloro-8-cyclopropyl-2-methyl-imidazo[1,2-b]pyridazine with 6-((1S,2S)-2-(6-chloroimidazo[1,2-b]pyridazin-8-yl)cyclopropyl)-1-(2,2,2-trifluoroethyl)-1H-pyrazolo[3,4-b]pyridine (Racemic Mixture). ES/MS m/z: 497.20 [M+H].

Intermediate 905. 6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[4,3-b]pyridine

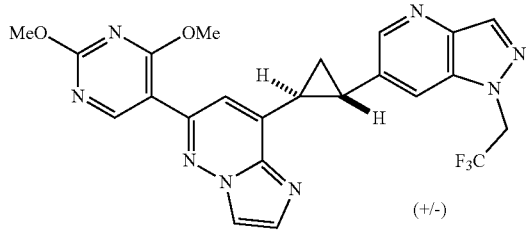 [SMILES: COc1ncc(-c2cc([C@H]3C[C@@H]3c3cnc4cnn(CC(F)(F)F)c4c3)c3nccn3n2)c(OC)n1]

6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[4,3-b]pyridine was prepared as a racemic mixture in the manner described for Intermediate 18, but replacing 6-chloro-8-cyclopropyl-2-methyl-imidazo[1,2-b]pyridazine with 6-((2S,2S)-2-(6-chloroimidazo[1,2-b]pyridazin-8-yl)cyclopropyl)-1-(2,2,2-trifluoroethyl)-1H-pyrazolo[4,3-b]pyridine (Racemic Mixture). ES/MS m/z: 497.10 [M+H].

Intermediate 906. 6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine

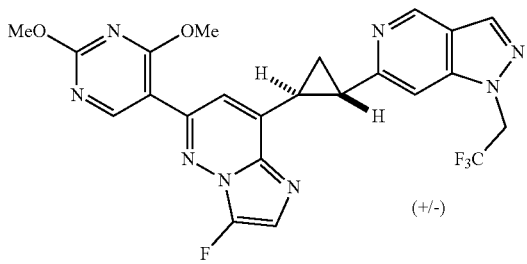 [SMILES: COc1ncc(-c2cc([C@H]3C[C@@H]3c3cc4c(cn3)cnn4CC(F)(F)F)c3ncc(F)n3n2)c(OC)n1]

(+/-)

6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine was prepared as a racemic mixture in the manner described for Intermediate 18, but replacing 6-chloro-8-cyclopropyl-2-methyl-imidazo[1,2-b]pyridazine with 6-((1S,2S)-2-(6-chloro-3-fluoroimidazo[1,2-b]pyridazin-8-yl)cyclopropyl)-1-(2,2,2-trifluoroethyl)-1H-pyrazolo[4,3-c]pyridine (Racemic Mixture). ES/MS m/z: 515.10 [M+H].

Intermediate 907. 6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine

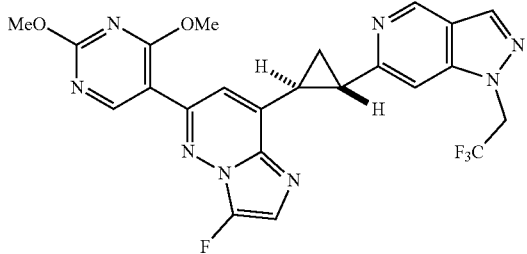 [SMILES: COc1ncc(-c2cc([C@H]3C[C@@H]3c3cc4c(cn3)cnn4CC(F)(F)F)c3ncc(F)n3n2)c(OC)n1]

6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine was prepared in the manner described for Intermediate 18, but replacing 6-chloro-8-cyclopropyl-2-methyl-imidazo[1,2-b]pyridazine with 6-((2S,2S)-2-(6-chloro-3-fluoroimidazo[1,2-b]pyridazin-8-yl)cyclopropyl)-1-(2,2,2-trifluoroethyl)-1H-pyrazolo[4,3-c]pyridine. ES/MS m/z: 515.10 [M+H].

Intermediate 908. 6-((1R,2R)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine

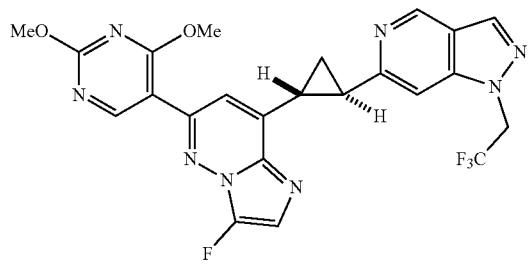 [SMILES: COc1ncc(-c2cc([C@@H]3C[C@H]3c3cc4c(cn3)cnn4CC(F)(F)F)c3ncc(F)n3n2)c(OC)n1]

6-((1R,2R)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine was prepared in the manner described for Intermediate 18, but replacing 6-chloro-8-cyclopropyl-2-methyl-imidazo[1,2-b]pyridazine with 64(1R,2R)-2-(6-chloro-3-fluoroimidazo[1,2-b]pyridazin-8-yl)cyclopropyl)-1-(2,2,2-trifluoroethyl)-1H-pyrazolo[4,3-c]pyridine. ES/MS m/z: 515.10 [M+H].

Intermediate 909. 6-((2S,2S)-2-(6-(2,4-dimethoxypyrimidin-5-yl)-3-fluoroimidazo[1,2-b]pyridazin-8-yl)cyclopropyl)-7-fluoro-1-(2,2,2-trifluoroethyl)-1H-pyrazolo[4,3-c]pyridine

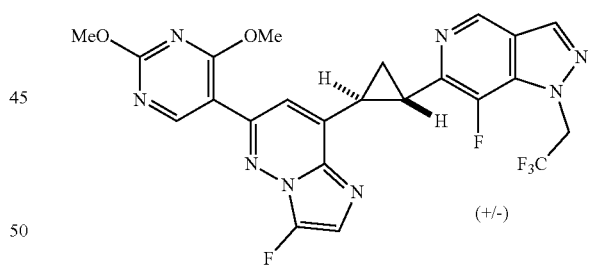

(+/-)

6-((1S,2S)-2-(6-(2,4-dimethoxypyrimidin-5-yl)-3-fluoroimidazo[1,2-b]pyridazin-8-yl)cyclopropyl)-7-fluoro-1-(2,2,2-trifluoroethyl)-1H-pyrazolo[4,3-c]pyridine was prepared as a racemic mixture in the manner described for Intermediate 18, but replacing 6-chloro-8-cyclopropyl-2-methyl-imidazo[1,2-b]pyridazine with 6-((1S,2S)-2-(6-chloro-3-fluoroimidazo[1,2-b]pyridazin-8-yl)cyclopropyl)-7-fluoro-1-(2,2,2-trifluoroethyl)-1H-pyrazolo[4,3-c]pyridine (Racemic Mixture). ES/MS m/z: 533.20 [M+H].

Intermediate 910. 6-((2S,2S)-2-(6-(2,4-dimethoxy-pyrimidin-5-yl)-3-fluoroimidazo[1,2-b]pyridazin-8-yl)cyclopropyl)-1-(2,2,2-trifluoroethyl)-1H-pyrazolo[3,4-b]pyridine

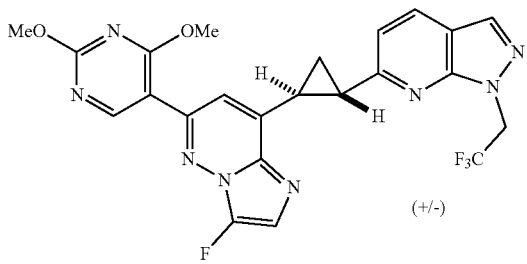 [SMILES: COc1ncc(-c2cc([C@H]3C[C@@H]3c3ccc4cnn(CC(F)(F)F)c4n3)c3ncc(F)n3n2)c(OC)n1]

(+/-)

6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[3,4-b]pyridine was prepared as a racemic mixture in the manner described for Intermediate 18, but replacing 6-chloro-8-cyclopropyl-2-methyl-imidazo[1,2-b]pyridazine with 6-((2S,2S)-2-(6-chloro-3-fluoroimidazo[1,2-b]pyridazin-8-yl)cyclopropyl)-1-(2,2,2-trifluoroethyl)-1H-pyrazolo[3,4-b]pyridine (Racemic Mixture). ES/MS m/z: 515.10 [M+H].

Intermediate 911. 6-((2S,2S)-2-(6-(2,4-dimethoxy-pyrimidin-5-yl)-3-fluoroimidazo[1,2-b]pyridazin-8-yl)cyclopropyl)-1-(2,2,2-trifluoroethyl)-1H-pyrazolo[3,4-b]pyridine

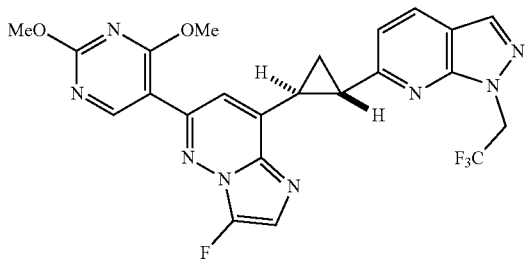 [SMILES: COc1ncc(-c2cc([C@H]3C[C@@H]3c3ccc4cnn(CC(F)(F)F)c4n3)c3ncc(F)n3n2)c(OC)n1]

6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[3,4-b]pyridine was prepared in the manner described for Intermediate 18, but replacing 6-chloro-8-cyclopropyl-2-methyl-imidazo[1,2-b]pyridazine with 6-((1S,2S)-2-(6-chloro-3-fluoroimidazo[1,2-b]pyridazin-8-yl)cyclopropyl)-1-(2,2,2-trifluoroethyl)-1H-pyrazolo[3,4-b]pyridine. ES/MS m/z: 515.10 [M+H].

Intermediate 912. 6-((2S,2S)-2-(6-(2,4-dimethoxy-pyrimidin-5-yl)-3-fluoroimidazo[1,2-b]pyridazin-8-yl)cyclopropyl)-1-(2,2,2-trifluoroethyl)-1H-pyrazolo[4,3-b]pyridine

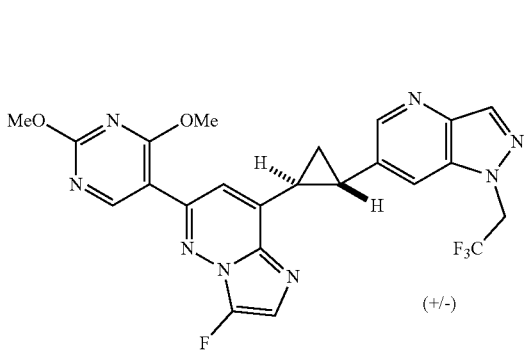 [SMILES: COc1ncc(-c2cc([C@H]3C[C@@H]3c3cnc4cnn(CC(F)(F)F)c4c3)c3ncc(F)n3n2)c(OC)n1]

(+/-)

6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-b]pyridine was prepared as a racemic mixture in the manner described for Intermediate 18, but replacing 6-chloro-8-cyclopropyl-2-methyl-imidazo[1,2-b]pyridazine with 6-((1S,2S)-2-(6-chloro-3-fluoroimidazo[1,2-b]pyridazin-8-yl)cyclopropyl)-1-(2,2,2-trifluoroethyl)-1H-pyrazolo[4,3-b]pyridine (Racemic Mixture). ES/MS m/z: 515.20 [M+H].

Intermediate 913. 6-((1S,2S)-2-(6-(2,4-dimethoxy-pyrimidin-5-yl)-3-fluoroimidazo[1,2-b]pyridazin-8-yl)cyclopropyl)-1-(2,2,2-trifluoroethyl)-1H-pyrazolo[4,3-b]pyridine

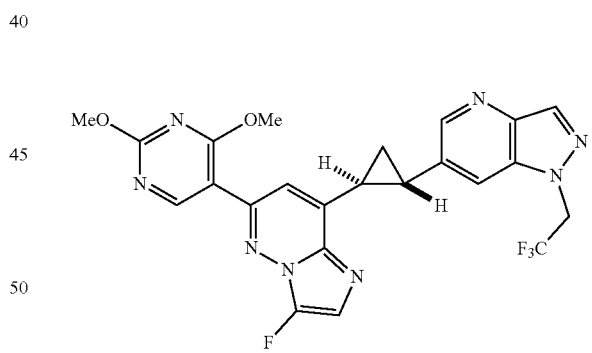

6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-b]pyridine was prepared in the manner described for Intermediate 18, but replacing 6-chloro-8-cyclopropyl-2-methyl-imidazo[1,2-b]pyridazine with 6-((1S,2S)-2-(6-chloro-3-fluoroimidazo[1,2-b]pyridazin-8-yl)cyclopropyl)-1-(2,2,2-trifluoroethyl)-1H-pyrazolo[4,3-b]pyridine. ES/MS m/z: 515.20 [M+H].

Intermediate 914. 6-((1R,2R)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-b]pyridine

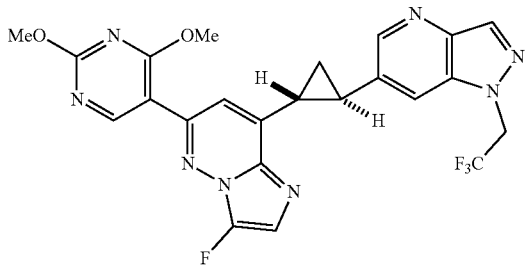 [SMILES: COc1ncc(-c2cc([C@@H]3C[C@H]3c3cnc4cnn(CC(F)(F)F)c4c3)c3ncc(F)n3n2)c(OC)n1]

6-((1R,2R)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-b]pyridine was prepared in the manner described for Intermediate 18, but replacing 6-chloro-8-cyclopropyl-2-methyl-imidazo[1,2-b]pyridazine with 6-((1R,2R)-2-(6-chloro-3-fluoroimidazo[1,2-b]pyridazin-8-yl)cyclopropyl)-1-(2,2,2-trifluoroethyl)-1H-pyrazolo[4,3-b]pyridine. ES/MS m/z: 515.20 [M+H].

Intermediate 915. 6-(2,4-dimethoxypyrimidin-5-yl)-8-((1S,2S)-2-(1-(2,2,2-trifluoroethyl)-2-(trifluoromethyl)-1H-benzo[d]imidazol-6-yl)cyclopropyl)imidazo[1,2-b]pyridazine

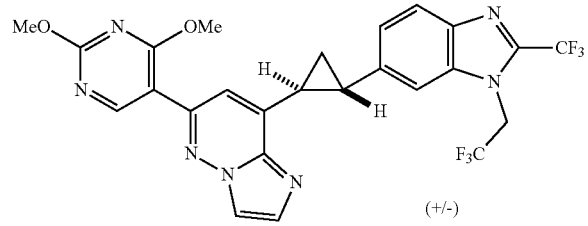 [SMILES: COc1ncc(-c2cc([C@H]3C[C@@H]3c3ccc4nc(C(F)(F)F)n(CC(F)(F)F)c4c3)c3nccn3n2)c(OC)n1]

6-(2,4-dimethoxypyrimidin-5-yl)-8-((1S,2S)-2-(1-(2,2,2-trifluoroethyl)-2-(trifluoromethyl)-1H-benzo[d]imidazol-6-yl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(1-(2,2,2-trifluoroethyl)-2-(trifluoromethyl)-1H-benzo[d]imidazol-6-yl)cyclopropyl)imidazo[1,2-b]pyridazine (Racemic Mixture). ES/MS m/z: 564.20 [M+H].

Intermediate 916. 6-(2,4-dimethoxypyrimidin-5-yl)-8-((1S,2S)-2-(1-(2,2,2-trifluoroethyl)-2-(trifluoromethyl)-1H-benzo[d]imidazol-6-yl)cyclopropyl)imidazo[1,2-b]pyridazine

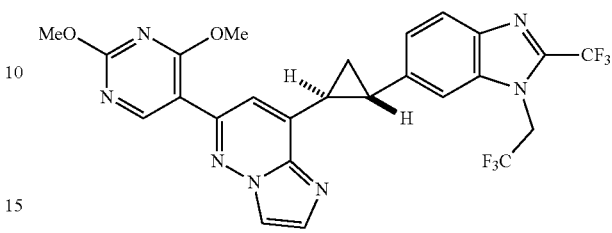

6-(2,4-dimethoxypyrimidin-5-yl)-8-((1S,2S)-2-(1-(2,2,2-trifluoroethyl)-2-(trifluoromethyl)-1H-benzo[d]imidazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(1-(2,2,2-trifluoroethyl)-2-(trifluoromethyl)-1H-benzo[d]imidazol-6-yl)cyclopropyl)imidazo[1,2-b]pyridazine. ES/MS m/z: 564.20 [M+H].

Intermediate 917. 8-((2S,2S)-2-(2-(difluoromethyl)-1-(2,2,2-trifluoroethyl)-1H-benzo[d]imidazol-6-yl)cyclopropyl)-6-(2,4-dimethoxypyrimidin-5-yl)imidazo[1,2-b]pyridazine

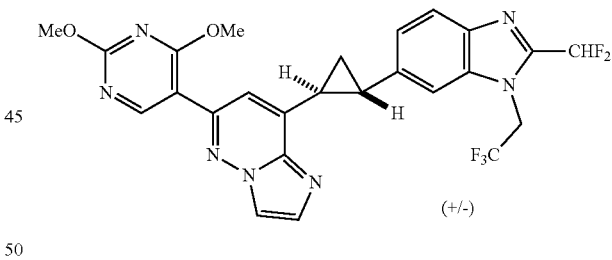

8-((1S,2S)-2-(2-(difluoromethyl)-1-(2,2,2-trifluoroethyl)-1H-benzo[d]imidazol-6-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(2-(difluoromethyl)-1-(2,2,2-trifluoroethyl)-1H-benzo[d]imidazol-6-yl)cyclopropyl)imidazo[1,2-b]pyridazine (Racemic Mixture). ES/MS m/z: 546.10 [M+H].

Intermediate 918. 8-((2S,2S)-2-(2-(difluoromethyl)-1-(2,2,2-trifluoroethyl)-1H-benzo[d]imidazol-5-yl)cyclopropyl)-6-(2,4-dimethoxypyrimidin-5-yl)imidazo[1,2-b]pyridazine

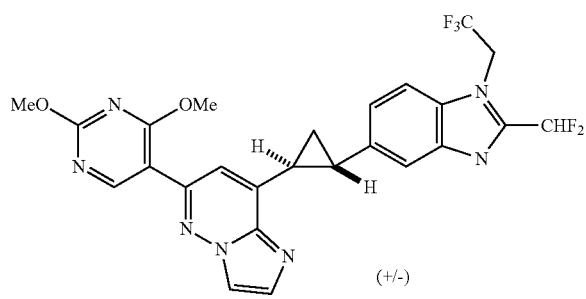

8-((1S,2S)-2-(2-(difluoromethyl)-1-(2,2,2-trifluoroethyl)-1H-benzo[d]imidazol-5-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(2-(difluoromethyl)-1-(2,2,2-trifluoroethyl)-1H-benzo[d]imidazol-5-yl)cyclopropyl)imidazo[1,2-b]pyridazine (Racemic Mixture). ES/MS m/z: 546.10 [M+H].

Intermediate 919. 8-((2S,2S)-2-(5-chloro-4-(2,2,2-trifluoroethoxy)pyridin-2-yl)cyclopropyl)-6-(2,4-dimethoxypyrimidin-5-yl)imidazo[1,2-b]pyridazine

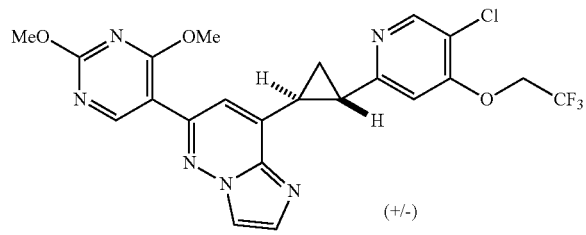 [SMILES: COc1ncc(-c2cc([C@H]3C[C@@H]3c3cc(OCC(F)(F)F)c(Cl)cn3)c3nccn3n2)c(OC)n1]

8-((1S,2S)-2-(5-chloro-4-(2,2,2-trifluoroethoxy)pyridin-2-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(5-chloro-4-(2,2,2-trifluoroethoxy)pyridin-2-yl)cyclopropyl)imidazo[1,2-b]pyridazine (Racemic Mixture). ES/MS m/z: 507.10 [M+H].

Intermediate 920. 8-((2S,2S)-2-(5-chloro-4-(2,2-difluorocyclopropyl)methoxy)pyridin-2-yl)cyclopropyl)-6-(2,4-dimethoxypyrimidin-5-yl)imidazo[1,2-b]pyridazine

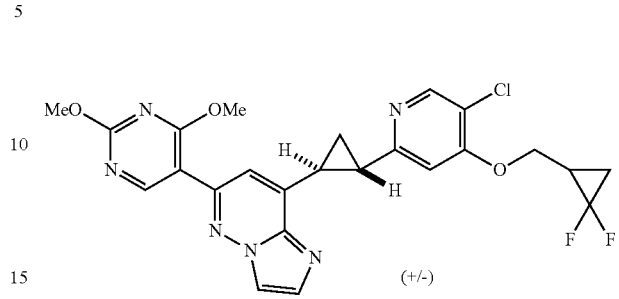

8-((1S,2S)-2-(5-chloro-4-(2,2-difluorocyclopropyl)methoxy)pyridin-2-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(5-chloro-4-((2,2-difluorocyclopropyl)methoxy)pyridin-2-yl)cyclopropyl)imidazo[1,2-b]pyridazine (racemic mixture). ES/MS m/z: 515.10 [M+H].

Intermediate 921. 7-((1S,2S)-2-(6-(2,4-dimethoxypyrimidin-5-yl)imidazo[1,2-b]pyridazin-8-yl)cyclopropyl)-1-(2,2,2-trifluoroethyl)quinolin-2(1H)-one

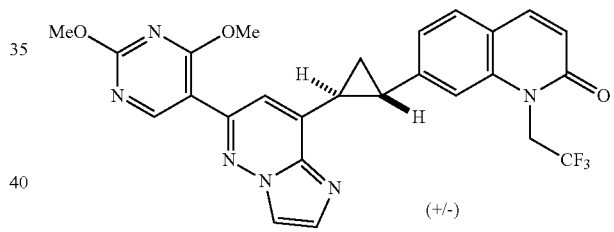

7-((1S,2S)-2-(6-(2,4-dimethoxypyrimidin-5-yl)imidazo[1,2-b]pyridazin-8-yl)cyclopropyl)-1-(2,2,2-trifluoroethyl)quinolin-2(1H)-one was prepared as a racemic mixture in the manner described for Intermediate 18, but replacing 6-chloro-8-cyclopropyl-2-methyl-imidazo[1,2-b]pyridazine with 7-((2S,2S)-2-(6-chloroimidazo[1,2-b]pyridazin-8-yl)cyclopropyl)-1-(2,2,2-trifluoroethyl)quinolin-2(1H)-one (Racemic Mixture). ES/MS m/z: 523.20 [M+H].

Intermediate 922. 7-((1S,2S)-2-(6-(2,4-dimethoxypyrimidin-5-yl)imidazo[1,2-b]pyridazin-8-yl)cyclopropyl)-2-(2,2,2-trifluoroethoxy)quinoline

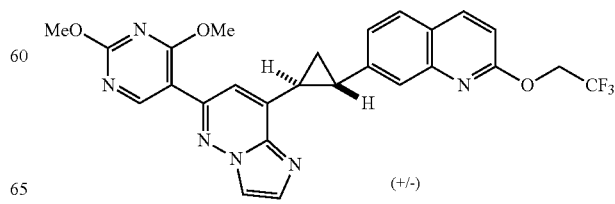

7-((1S,2S)-2-(6-(2,4-dimethoxypyrimidin-5-yl)imidazo[1,2-b]pyridazin-8-yl)cyclopropyl)-2-(2,2,2-trifluoroethoxy)quinoline was prepared as a racemic mixture in the manner described for Intermediate 18, but replacing 6-chloro-8-cyclopropyl-2-methyl-imidazo[1,2-b]pyridazine with 7-((1S,2S)-2-(6-chloroimidazo[1,2-b]pyridazin-8-yl)cyclopropyl)-2-(2,2,2-trifluoroethoxy)quinoline (Racemic Mixture). ES/MS m/z: 523.20 [M+H].

Intermediate 923. 6-(2,4-dimethoxypyrimidin-5-yl)-8-((1S,2S)-2-(4-fluoro-1-(2,2,2-trifluoroethyl)-1H-indazol-6-yl)cyclopropyl)imidazo[1,2-b]pyridazine

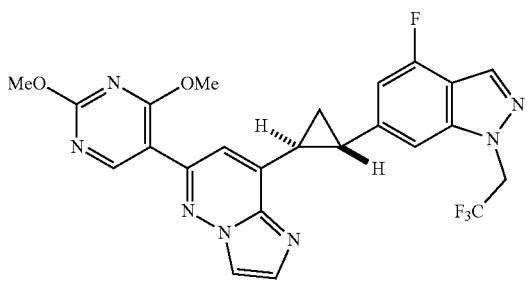 [SMILES: COc1ncc(-c2cc([C@H]3C[C@@H]3c3cc(F)c4cnn(CC(F)(F)F)c4c3)c3nccn3n2)c(OC)n1]

6-(2,4-dimethoxypyrimidin-5-yl)-8-((2S,2S)-2-(4-fluoro-1-(2,2,2-trifluoroethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(4-fluoro-1-(2,2,2-trifluoroethyl)-1H-indazol-6-yl)cyclopropyl)imidazo[1,2-b]pyridazine. ES/MS m/z: 514.20 [M+H].

Intermediate 924. 6-(2,4-dimethoxypyrimidin-5-yl)-3-fluoro-8-((1S,2S)-2-(4-fluoro-1-(2,2,2-trifluoroethyl)-1H-indazol-6-yl)cyclopropyl)imidazo[1,2-b]pyridazine

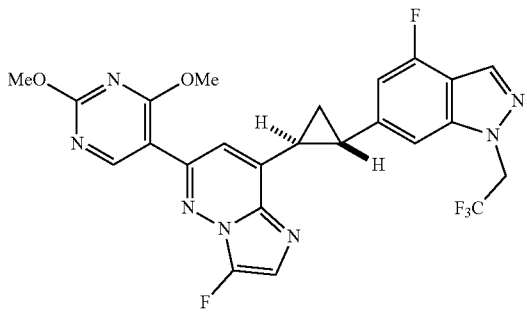 [SMILES: COc1ncc(-c2cc([C@H]3C[C@@H]3c3cc(F)c4cnn(CC(F)(F)F)c4c3)c3ncc(F)n3n2)c(OC)n1]

6-(2,4-dimethoxypyrimidin-5-yl)-3-fluoro-8-((1S,2S)-2-(4-fluoro-1-(2,2,2-trifluoroethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-((1S,2S)-2-(4-fluoro-1-(2,2,2-trifluoroethyl)-1H-indazol-6-yl)cyclopropyl)imidazo[1,2-b]pyridazine. ES/MS m/z: 532.20 [M+H].

Intermediate 925. 6-(2,4-dimethoxypyrimidin-5-yl)-8-((1S,2S)-2-(5-fluoro-1-(2,2,2-trifluoroethyl)-1H-indazol-6-yl)cyclopropyl)imidazo[1,2-b]pyridazine

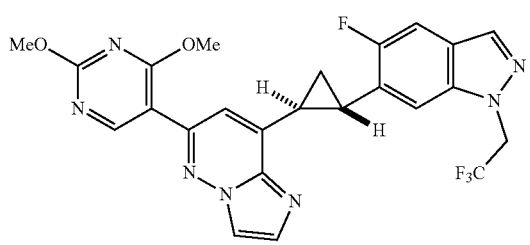 [SMILES: COc1ncc(-c2cc([C@H]3C[C@@H]3c3cc4c(cnn4CC(F)(F)F)cc3F)c3nccn3n2)c(OC)n1]

6-(2,4-dimethoxypyrimidin-5-yl)-8-((2S,2S)-2-(5-fluoro-1-(2,2,2-trifluoroethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(5-fluoro-1-(2,2,2-trifluoroethyl)-1H-indazol-6-yl)cyclopropyl)imidazo[1,2-b]pyridazine. ES/MS m/z: 514.20 [M+H].

Intermediate 926. 6-(2,4-dimethoxypyrimidin-5-yl)-3-fluoro-8-((1S,2S)-2-(5-fluoro-1-(2,2,2-trifluoroethyl)-1H-indazol-6-yl)cyclopropyl)imidazo[1,2-b]pyridazine

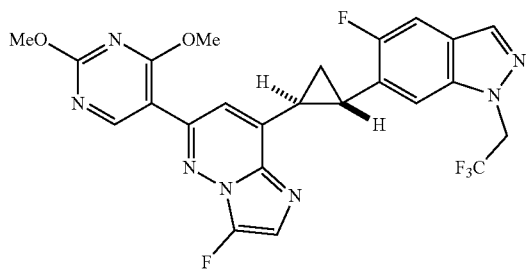 [SMILES: COc1ncc(-c2cc([C@H]3C[C@@H]3c3cc4c(cnn4CC(F)(F)F)cc3F)c3ncc(F)n3n2)c(OC)n1]

6-(2,4-dimethoxypyrimidin-5-yl)-3-fluoro-8-((2S,2S)-2-(5-fluoro-1-(2,2,2-trifluoroethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-((1S,2S)-2-(5-fluoro-1-(2,2,2-trifluoroethyl)-1H-indazol-6-yl)cyclopropyl)imidazo[1,2-b]pyridazine. ES/MS m/z: 532.20 [M+H].

Intermediate 927. 6-(2,4-dimethoxypyrimidin-5-yl)-8-((1S,2S)-2-(7-fluoro-1-(2,2,2-trifluoroethyl)-1H-indazol-6-yl)cyclopropyl)imidazo[1,2-b]pyridazine

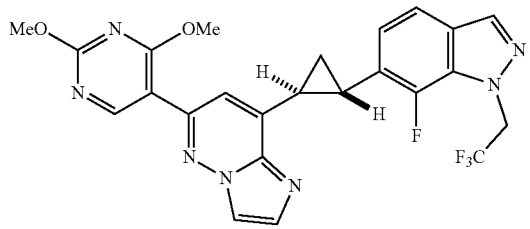 [SMILES: COc1ncc(-c2cc([C@H]3C[C@@H]3c3ccc4cnn(CC(F)(F)F)c4c3F)c3nccn3n2)c(OC)n1]

6-(2,4-dimethoxypyrimidin-5-yl)-8-((1S,2S)-2-(7-fluoro-1-(2,2,2-trifluoroethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(7-fluoro-1-(2,2,2-trifluoroethyl)-1H-indazol-6-yl)cyclopropyl)imidazo[1,2-b]pyridazine. ES/MS m/z: 514.20 [M+H].

Intermediate 928. 6-(2,4-dimethoxypyrimidin-5-yl)-3-fluoro-8-((1S,2S)-2-(7-fluoro-1-(2,2,2-trifluoroethyl)-1H-indazol-6-yl)cyclopropyl)imidazo[1,2-b]pyridazine

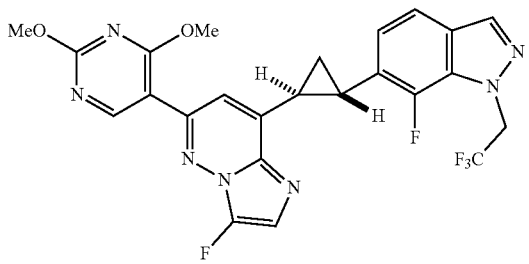 [SMILES: COc1ncc(-c2cc([C@H]3C[C@@H]3c3ccc4cnn(CC(F)(F)F)c4c3F)c3ncc(F)n3n2)c(OC)n1]

6-(2,4-dimethoxypyrimidin-5-yl)-3-fluoro-8-((2S,2S)-2-(7-fluoro-1-(2,2,2-trifluoroethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-3-fluoro-8-((2S,2S)-2-(7-fluoro-1-(2,2,2-trifluoroethyl)-1H-indazol-6-yl)cyclopropyl)imidazo[1,2-b]pyridazine. ES/MS m/z: 532.20 [M+H].

Intermediate 929. 6-(2,4-dimethoxypyrimidin-5-yl)-8-((1S,2S)-2-(7-fluoro-1-(2,2,2-trifluoroethyl)-1H-indazol-6-yl)cyclopropyl)-[1,2,4]triazolo[1,5-b]pyridazine

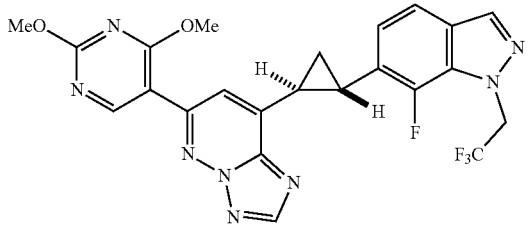 [SMILES: COc1ncc(-c2cc([C@H]3C[C@@H]3c3ccc4cnn(CC(F)(F)F)c4c3F)c3ncnn3n2)c(OC)n1]

6-(2,4-dimethoxypyrimidin-5-yl)-8-((2S,2S)-2-(7-fluoro-1-(2,2,2-trifluoroethyl)-1H-indazol-6-yl)cyclopropyl)-[1,2,4]triazolo[1,5-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(7-fluoro-1-(2,2,2-trifluoroethyl)-1H-indazol-6-yl)cyclopropyl)-[1,2,4]triazolo[1,5-b]pyridazine. ES/MS m/z: 515.20 [M+H].

Intermediate 930. 6-(2,4-dimethoxypyrimidin-5-yl)-8-((1S,2S)-2-(3-(2,2,2-trifluoroethyl)imidazo[1,5-a]pyridin-6-yl)cyclopropyl)imidazo[1,2-b]pyridazine

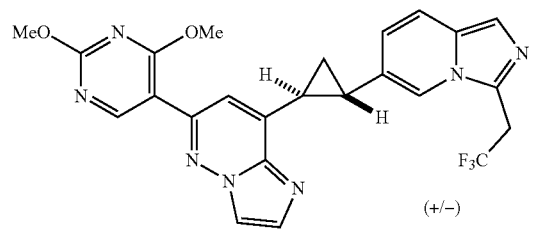 [SMILES: COc1ncc(-c2cc([C@H]3C[C@@H]3c3ccc4cnc(CC(F)(F)F)n4c3)c3nccn3n2)c(OC)n1]

6-(2,4-dimethoxypyrimidin-5-yl)-8-((2S,2S)-2-(3-(2,2,2-trifluoroethyl)imidazo[1,5-a]pyridin-6-yl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(3-(2,2,2-trifluoroethyl)imidazo[1,5-a]pyridin-6-yl)cyclopropyl)imidazo[1,2-b]pyridazine (Racemic Mixture). ES/MS m/z: 495.40 [M+H].

Intermediate 931. 6-(2,4-dimethoxypyrimidin-5-yl)-8-((1S,2S)-2-(3-(2,2,2-trifluoroethyl)-1-(trifluoromethyl)imidazo[1,5-a]pyridin-6-yl)cyclopropyl)imidazo[1,2-b]pyridazine

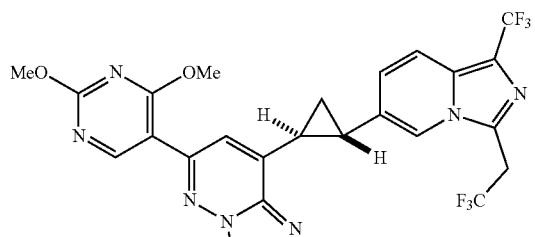

6-(2,4-dimethoxypyrimidin-5-yl)-8-((1S,2S)-2-(3-(2,2,2-trifluoroethyl)-1-(trifluoromethyl)imidazo[1,5-a]pyridin-6-yl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(3-(2,2,2-trifluoroethyl)-1-(trifluoromethyl)imidazo[1,5-a]pyridin-6-yl)cyclopropyl)imidazo[1,2-b]pyridazine (Racemic Mixture). ES/MS m/z: 564.20 [M+H].

709

Intermediate 932. 6-(2,4-dimethoxypyrimidin-5-yl)-8-((1S,2S)-2-(1-(2,2,2-trifluoroethyl)-3-(trifluoromethyl)-1H-indazol-6-yl)cyclopropyl)imidazo[1,2-b]pyridazine

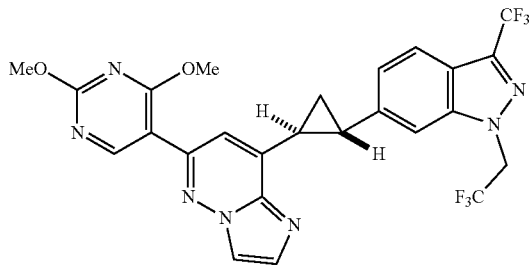 [SMILES: COc1ncc(-c2cc([C@H]3C[C@@H]3c3ccc4c(C(F)(F)F)nn(CC(F)(F)F)c4c3)c3nccn3n2)c(OC)n1]

6-(2,4-dimethoxypyrimidin-5-yl)-8-((1S,2S)-2-(1-(2,2,2-trifluoroethyl)-3-(trifluoromethyl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((2S,2S)-2-(1-(2,2,2-trifluoroethyl)-3-(trifluoromethyl)-1H-indazol-6-yl)cyclopropyl)imidazo[1,2-b]pyridazine. ES/MS m/z: 564.10 [M+H].

Intermediate 933. 6-((2S,2S)-2-(6-(2,4-dimethoxypyrimidin-5-yl)imidazo[1,2-b]pyridazin-8-yl)cyclopropyl)-1-(2,2,2-trifluoroethyl)-3-(trifluoromethyl)-1H-pyrazolo[4,3-c]pyridine

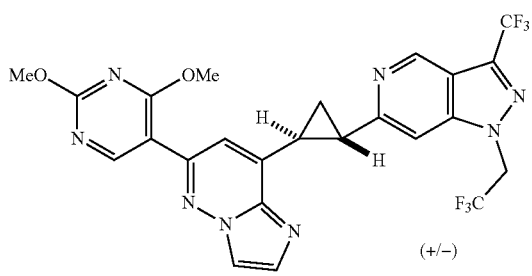 [SMILES: COc1ncc(-c2cc([C@H]3C[C@@H]3c3cc4c(cn3)c(C(F)(F)F)nn4CC(F)(F)F)c3nccn3n2)c(OC)n1]

6-((1S,2S)-2-(6-(2,4-dimethoxypyrimidin-5-yl)imidazo[1,2-b]pyridazin-8-yl)cyclopropyl)-1-(2,2,2-trifluoroethyl)-3-(trifluoromethyl)-1H-pyrazolo[4,3-c]pyridine was prepared as a racemic mixture in the manner described for Intermediate 18, but replacing 6-chloro-8-cyclopropyl-2-methyl-imidazo[1,2-b]pyridazine with 6-((1S,2S)-2-(6-chloroimidazo[1,2-b]pyridazin-8-yl)cyclopropyl)-1-(2,2,2-trifluoroethyl)-3-(trifluoromethyl)-1H-pyrazolo[4,3-c]pyridine (Racemic Mixture). ES/MS m/z: 565.20 [M+H].

710

Intermediate 934. 6-((2S,2S)-2-(6-(2,4-dimethoxypyrimidin-5-yl)imidazo[1,2-b]pyridazin-8-yl)cyclopropyl)-7-fluoro-1-(2,2,2-trifluoroethyl)-1H-pyrazolo[4,3-c]pyridine

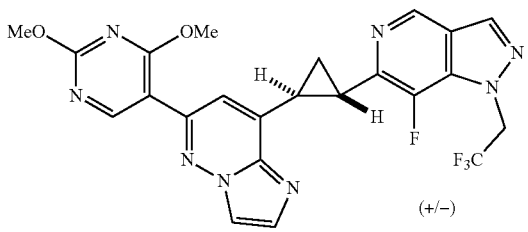

6-((1S,2S)-2-(6-(2,4-dimethoxypyrimidin-5-yl)imidazo[1,2-b]pyridazin-8-yl)cyclopropyl)-7-fluoro-1-(2,2,2-trifluoroethyl)-1H-pyrazolo[4,3-c]pyridine was prepared as a racemic mixture in the manner described for Intermediate 18, but replacing 6-chloro-8-cyclopropyl-2-methyl-imidazo[1,2-b]pyridazine with 6-((1S,2S)-2-(6-chloroimidazo[1,2-b]pyridazin-8-yl)cyclopropyl)-7-fluoro-1-(2,2,2-trifluoroethyl)-1H-pyrazolo[4,3-c]pyridine (Racemic Mixture). ES/MS m/z: 515.10 [M+H].

Intermediate 935. 7-((2S,2S)-2-(6-(2,4-dimethoxypyrimidin-5-yl)imidazo[1,2-b]pyridazin-8-yl)cyclopropyl)-1-(trifluoromethyl)-2,3-dihydro-1H-benzo[d]pyrrolo[1,2-a]imidazole

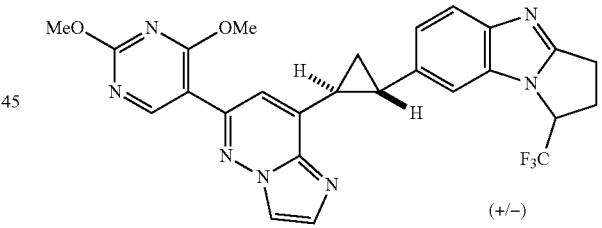

7-((1S,2S)-2-(6-(2,4-dimethoxypyrimidin-5-yl)imidazo[1,2-b]pyridazin-8-yl)cyclopropyl)-1-(trifluoromethyl)-2,3-dihydro-1H-benzo[d]pyrrolo[1,2-a]imidazole was prepared as a racemic mixture in the manner described for Intermediate 18, but replacing 6-chloro-8-cyclopropyl-2-methyl-imidazo[1,2-b]pyridazine with 7-((1S,2S)-2-(6-chloroimidazo[1,2-b]pyridazin-8-yl)cyclopropyl)-1-(trifluoromethyl)-2,3-dihydro-1H-benzo[d]pyrrolo[1,2-a]imidazole (Racemic Mixture). ES/MS m/z: 522.20 [M+H].

Intermediate 936. 6-(2,4-dimethoxypyrimidin-5-yl)-8-((1S,2S)-2-(1-(1,1,1-trifluoropropan-2-yl)-1H-indazol-6-yl)cyclopropyl)imidazo[1,2-b]pyridazine

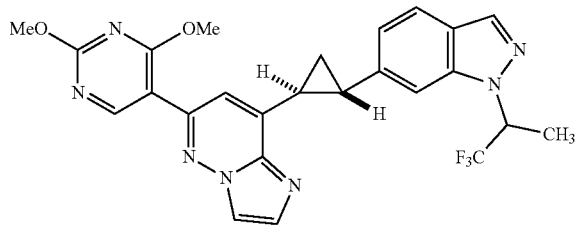 [SMILES: COc1ncc(-c2cc([C@H]3C[C@@H]3c3ccc4cnn(C(C)C(F)(F)F)c4c3)c3nccn3n2)c(OC)n1]

6-(2,4-dimethoxypyrimidin-5-yl)-8-((2S,2S)-2-(1-(1,1,1-trifluoropropan-2-yl)-1H-indazol-6-yl)cyclopropyl)imidazo[1,2-b]pyridazine was prepared in the manner described for Intermediate 18, but replacing 6-chloro-8-cyclopropyl-2-methyl-imidazo[1,2-b]pyridazine with 6-chloro-8-((1S,2S)-2-(1-(1,1,1-trifluoropropan-2-yl)-1H-indazol-6-yl)cyclopropyl)imidazo[1,2-b]pyridazine. ES/MS m/z: 510.20 [M+H].

Intermediate 937. 6-(2,4-dimethoxypyrimidin-5-yl)-8-((1S,2S)-2-(4-(2-(trifluoromethyl)phenyl)pyridin-2-yl)cyclopropyl)imidazo[1,2-b]pyridazine

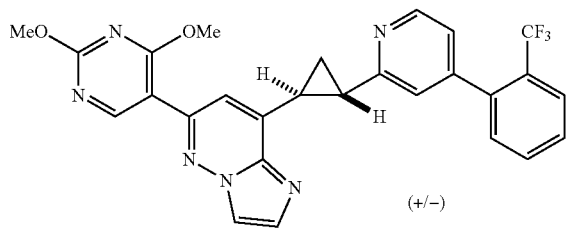 [SMILES: COc1ncc(-c2cc([C@H]3C[C@@H]3c3cc(-c4ccccc4C(F)(F)F)ccn3)c3nccn3n2)c(OC)n1]

6-(2,4-dimethoxypyrimidin-5-yl)-8-((1S,2S)-2-(4-(2-(trifluoromethyl)phenyl)pyridin-2-yl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(4-(2-(trifluoromethyl)phenyl)pyridin-2-yl)cyclopropyl)imidazo[1,2-b]pyridazine (Racemic Mixture). ES/MS m/z: 519.20 [M+H].

Intermediate 938. 8-((1S,2S)-2-(4-(2,4-difluorophenyl)pyridin-2-yl)cyclopropyl)-6-(2,4-dimethoxypyrimidin-5-yl)imidazo[1,2-b]pyridazine

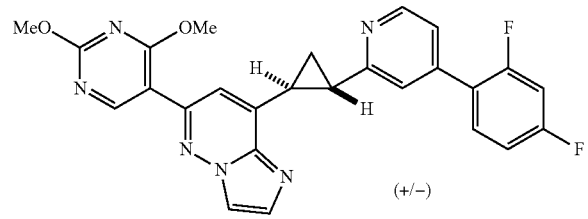 [SMILES: COc1ncc(-c2cc([C@H]3C[C@@H]3c3cc(-c4ccc(F)cc4F)ccn3)c3nccn3n2)c(OC)n1]

8-((1S,2S)-2-(4-(2,4-difluorophenyl)pyridin-2-yl)cyclopropyl)-6-(2,4-dimethoxypyrimidin-5-yl)imidazo[1,2-b]

pyridazine was prepared as a racemic mixture in the manner described for Intermediate 18, but replacing 6-chloro-8-cyclopropyl-2-methyl-imidazo[1,2-b]pyridazine with 6-chloro-8-((2S,2S)-2-(4-(2,4-difluorophenyl)pyridin-2-yl)cyclopropyl)imidazo[1,2-b]pyridazine (Racemic Mixture). ES/MS m/z: 487.10 [M+H].

Intermediate 939. 6-((1S,2S)-2-(6-(2,4-dimethoxypyrimidin-5-yl)imidazo[1,2-b]pyridazin-8-yl)cyclopropyl)-1-(2,2,2-trifluoroethyl)-2-(trifluoromethyl)-1H-imidazo[4,5-c]pyridine

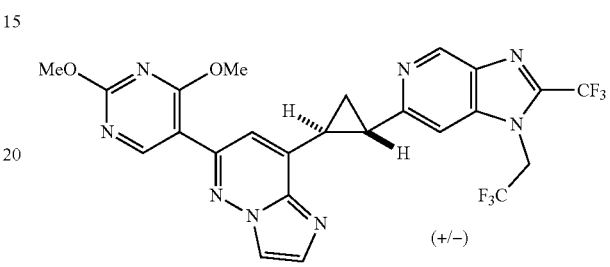

6-((1S,2S)-2-(6-(2,4-dimethoxypyrimidin-5-yl)imidazo[1,2-b]pyridazin-8-yl)cyclopropyl)-1-(2,2,2-trifluoroethyl)-2-(trifluoromethyl)-1H-imidazo[4,5-c]pyridine was prepared as a racemic mixture in the manner described for Intermediate 18, but replacing 6-chloro-8-cyclopropyl-2-methyl-imidazo[1,2-b]pyridazine with 6-((1S,2S)-2-(6-chloroimidazo[1,2-b]pyridazin-8-yl)cyclopropyl)-1-(2,2,2-trifluoroethyl)-2-(trifluoromethyl)-1H-imidazo[4,5-c]pyridine (Racemic Mixture). ES/MS m/z: 565.20 [M+H].

Intermediate 940. 6-(2,4-dimethoxypyrimidin-5-yl)-8-((1S,2S)-2-(3-(trifluoromethyl)imidazo[1,5-a]pyridin-7-yl)cyclopropyl)imidazo[1,2-b]pyridazine

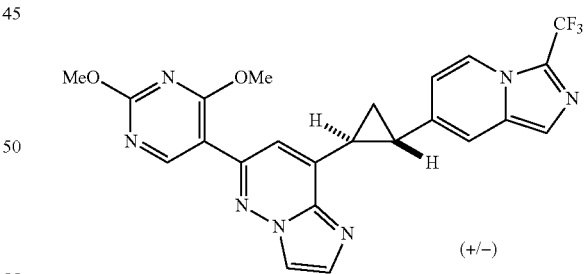

6-(2,4-dimethoxypyrimidin-5-yl)-8-((1S,2S)-2-(3-(trifluoromethyl)imidazo[1,5-a]pyridin-7-yl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(3-(trifluoromethyl)imidazo[1,5-a]pyridin-7-yl)cyclopropyl)imidazo[1,2-b]pyridazine (Racemic Mixture). ES/MS m/z: 482.20 [M+H].

713

Intermediate 941. 7-((1S,2S)-2-(6-(2,4-dimethoxy-pyrimidin-5-yl)imidazo[1,2-b]pyridazin-8-yl)cyclopropyl)-5-(2,2,2-trifluoroethoxy)quinoline

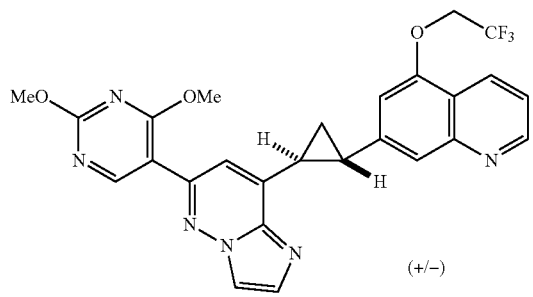 [SMILES: COc1ncc(-c2cc([C@H]3C[C@@H]3c3cc(OCC(F)(F)F)c4cccnc4c3)c3nccn3n2)c(OC)n1]

(+/−)

7-((1S,2S)-2-(6-(2,4-dimethoxypyrimidin-5-yl)imidazo[1,2-b]pyridazin-8-yl)cyclopropyl)-5-(2,2,2-trifluoroethoxy)quinoline was prepared as a racemic mixture in the manner described for Intermediate 18, but replacing 6-chloro-8-cyclopropyl-2-methyl-imidazo[1,2-b]pyridazine with 74(1S,2S)-2-(6-chloroimidazo[1,2-b]pyridazin-8-yl)cyclopropyl)-5-(2,2,2-trifluoroethoxy)quinoline (Racemic Mixture). ES/MS m/z: 523.20 [M+H].

Intermediate 942. 8-((2S,2S)-2-(4,7-difluoro-1-(2,2,2-trifluoroethyl)-1H-indazol-6-yl)cyclopropyl)-6-(2,4-dimethoxypyrimidin-5-yl)imidazo[1,2-b]pyridazine

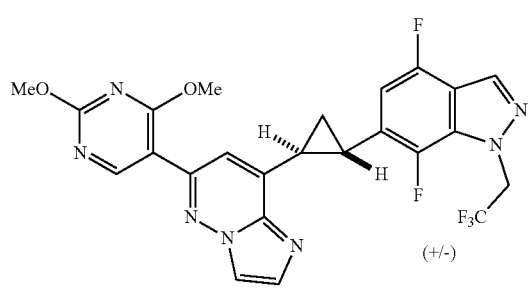 [SMILES: COc1ncc(-c2cc([C@H]3C[C@@H]3c3cc(F)c4cnn(CC(F)(F)F)c4c3F)c3nccn3n2)c(OC)n1]

(+/−)

8-((1S,2S)-2-(4,7-difluoro-1-(2,2,2-trifluoroethyl)-1H-indazol-6-yl)cyclopropyl)-6-(2,4-dimethoxypyrimidin-5-yl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(4,7-difluoro-1-(2,2,2-trifluoroethyl)-1H-indazol-6-yl)cyclopropyl)imidazo[1,2-b]pyridazine (Racemic Mixture). ES/MS m/z: 532.10 [M+H].

714

Intermediate 943. 6-(2,4-dimethoxypyrimidin-5-yl)-8-((1S,2S)-2-(3-(2,2,2-trifluoroethyl)-2-(trifluoromethyl)imidazo[1,2-a]pyridin-6-yl)cyclopropyl)imidazo[1,2-b]pyridazine

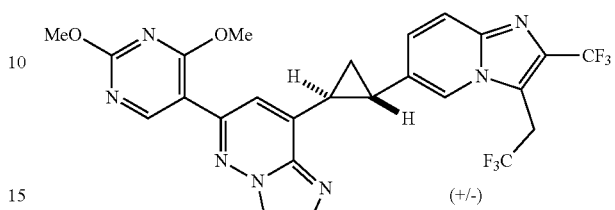

(+/−)

6-(2,4-dimethoxypyrimidin-5-yl)-8-((1S,2S)-2-(3-(2,2,2-trifluoroethyl)-2-(trifluoromethyl)imidazo[1,2-a]pyridin-6-yl)cyclopropyl)imidazo[1,2-b]pyridazine was prepared as a racemic mixture in the manner described for Intermediate 18, but replacing 6-chloro-8-cyclopropyl-2-methyl-imidazo[1,2-b]pyridazine with 6-chloro-8-((1S,2S)-2-(3-(2,2,2-trifluoroethyl)-2-(trifluoromethyl)imidazo[1,2-a]pyridin-6-yl)cyclopropyl)imidazo[1,2-b]pyridazine (Racemic Mixture). ES/MS m/z: 564.20 [M+H].

Intermediate 944. 6-(2,4-dimethoxypyrimidin-5-yl)-8-(6-azaspiro[3.4]octan-6-yl)imidazo[1,2-b]pyridazine

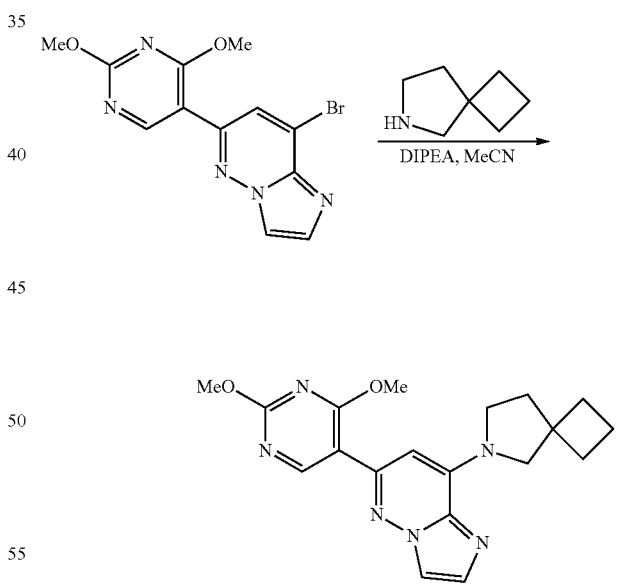

A solution of 8-bromo-6-(2,4-dimethoxypyrimidin-5-yl)imidazo[1,2-b]pyridazine (120 mg, 0.36 mmol, 1 equiv), 6-azaspiro[3.4]octane hydrochloride (60 mg, 0.54 mmol, 1.5 equiv), and DIPEA (0.19 mL, 1.07 mmol, 3 equiv) in MeCN (3 mL) was heated to 100° C. After 3 hours, the reaction mixture was directly purified by SiO₂ chromatography (0-100% EtOAc/Hex), affording 6-(2,4-dimethoxypyrimidin-5-yl)-8-(6-azaspiro[3.4]octan-6-yl)imidazo[1,2-b]pyridazine. ES/MS m/z: 367.20 [M+H].

Intermediate 945. 8-(2,2-difluoro-6-azaspiro[3.4]
octan-6-yl)-6-(2,4-dimethoxypyrimidin-5-yl)imidazo
[1,2-b]pyridazine

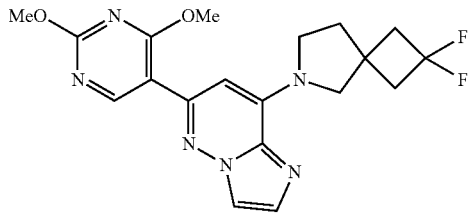 [SMILES: COc1ncc(-c2cc(N3CCC4(C3)CC(F)(F)C4)c3nccn3n2)c(OC)n1]

8-(2,2-difluoro-6-azaspiro[3.4]octan-6-yl)-6-(2,4-dimethoxypyrimidin-5-yl)imidazo[1,2-b]pyridazine was prepared in the manner described for Intermediate 944, but replacing 6-azaspiro[3.4]octane hydrochloride with 2,2-difluoro-6-azaspiro[3.4]octane hydrochloride. ES/MS m/z: 403.20 [M+H].

Intermediate 946. 6-(2,4-dimethoxypyrimidin-5-yl)-
8-(3-(methoxymethyl)-3-methylpyrrolidin-1-yl)imidazo[1,2-b]pyridazine

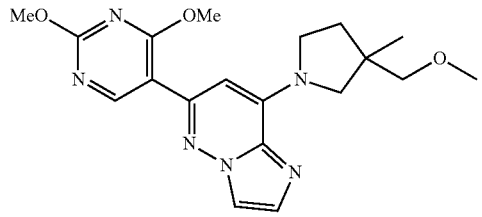 [SMILES: COCC1(C)CCN(c2cc(-c3cnc(OC)nc3OC)nn3ccnc23)C1]

6-(2,4-dimethoxypyrimidin-5-yl)-8-(3-(methoxymethyl)-3-methylpyrrolidin-1-yl)imidazo[1,2-b]pyridazine was prepared in the manner described for Intermediate 944, but replacing 6-azaspiro[3.4]octane hydrochloride with 3-(methoxymethyl)-3-methyl-pyrrolidine hydrochloride. ES/MS m/z: 385.20 [M+H].

Intermediate 947. 3-(6-(2,4-dimethoxypyrimidin-5-
yl)imidazo[1,2-b]pyridazin-8-yl)-6,6-difluoro-3-
azabicyclo[3.1.1]heptane

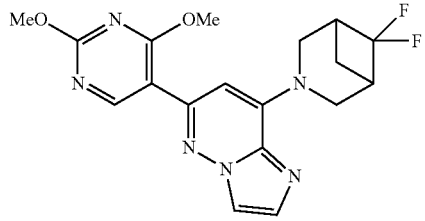 [SMILES: COc1ncc(-c2cc(N3CC4CC(C3)C4(F)F)c3nccn3n2)c(OC)n1]

3-(6-(2,4-dimethoxypyrimidin-5-yl)imidazo[1,2-b]pyridazin-8-yl)-6,6-difluoro-3-azabicyclo[3.1.1]heptane was prepared in the manner described for Intermediate 944, but replacing 6-azaspiro[3.4]octane hydrochloride with 6,6-difluoro-3-azabicyclo[3.1.1]heptane hydrochloride. ES/MS m/z: 389.20 [M+H].

Intermediate 948. 8-(3-cyclopropylpyrrolidin-1-yl)-
6-(2,4-dimethoxypyrimidin-5-yl)imidazo[1,2-b]
pyridazine

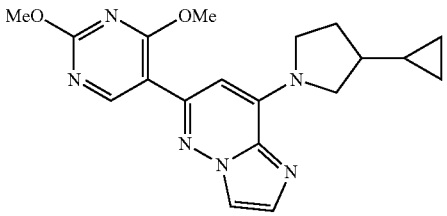 [SMILES: COc1ncc(-c2cc(N3CCC(C4CC4)C3)c3nccn3n2)c(OC)n1]

8-(3-cyclopropylpyrrolidin-1-yl)-6-(2,4-dimethoxypyrimidin-5-yl)imidazo[1,2-b]pyridazine was prepared in the manner described for Intermediate 944, but replacing 6-azaspiro[3.4]octane hydrochloride with 3-cyclopropylpyrrolidine. ES/MS m/z: 367.20 [M+H].

Intermediate 949. 8-(3-(3,3-difluorocyclobutyl)pyrrolidin-1-yl)-6-(2,4-dimethoxypyrimidin-5-yl)imidazo[1,2-b]pyridazine

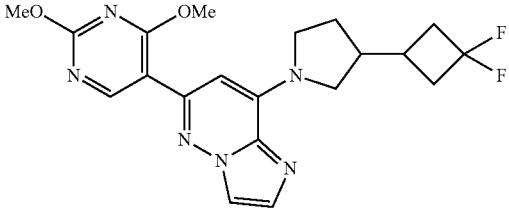 [SMILES: COc1ncc(-c2cc(N3CCC(C4CC(F)(F)C4)C3)c3nccn3n2)c(OC)n1]

8-(3-(3,3-difluorocyclobutyl)pyrrolidin-1-yl)-6-(2,4-dimethoxypyrimidin-5-yl)imidazo[1,2-b]pyridazine was prepared in the manner described for Intermediate 944, but replacing 6-azaspiro[3.4]octane hydrochloride with 3-(3,3-difluorocyclobutyl)pyrrolidine. ES/MS m/z: 417.20 [M+H].

Intermediate 950. 3-(6-(2,4-dimethoxypyrimidin-5-
yl)imidazo[1,2-b]pyridazin-8-yl)-1-fluoro-3-azabicyclo[3.1.1]heptane

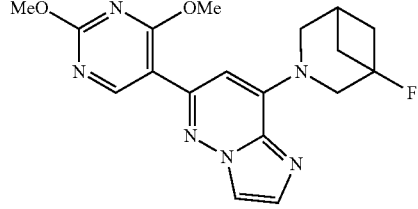 [SMILES: COc1ncc(-c2cc(N3CC4CC(F)(C4)C3)c3nccn3n2)c(OC)n1]

3-(6-(2,4-dimethoxypyrimidin-5-yl)imidazo[1,2-b]pyridazin-8-yl)-1-fluoro-3-azabicyclo[3.1.1]heptane was prepared in the manner described for Intermediate 944, but replacing 6-azaspiro[3.4]octane hydrochloride with 1-fluoro-3-azabicyclo[3.1.1]heptane hydrochloride. ES/MS m/z: 371.20 [M+H].

Intermediate 951. 2-(6-(2,4-dimethoxypyrimidin-5-yl)imidazo[1,2-b]pyridazin-8-yl)-8,8-difluoro-2-azaspiro[4.5]decane

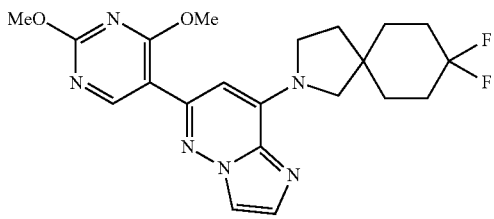 [SMILES: COc1ncc(-c2cc(N3CCC4(CCC(F)(F)CC4)C3)c3nccn3n2)c(OC)n1]

2-(6-(2,4-dimethoxypyrimidin-5-yl)imidazo[1,2-b]pyridazin-8-yl)-8,8-difluoro-2-azaspiro[4.5]decane was prepared in the manner described for Intermediate 944, but replacing 6-azaspiro[3.4]octane hydrochloride with 8,8-difluoro-2-azaspiro[4.5]decane hydrochloride. ES/MS m/z: 431.20 [M+H].

Intermediate 952. 8-(3-((1H-1,2,3-triazol-1-yl)methyl)pyrrolidin-1-yl)-6-(2,4-dimethoxypyrimidin-5-yl)imidazo[1,2-b]pyridazine

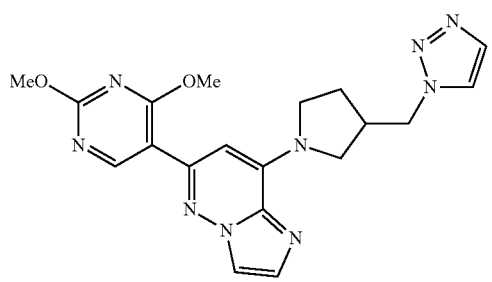 [SMILES: COc1ncc(-c2cc(N3CCC(Cn4ccnn4)C3)c3nccn3n2)c(OC)n1]

8-(3-((1H-1,2,3-triazol-1-yl)methyl)pyrrolidin-1-yl)-6-(2,4-dimethoxypyrimidin-5-yl)imidazo[1,2-b]pyridazine was prepared in the manner described for Intermediate 944, but replacing 6-azaspiro[3.4]octane hydrochloride with 1-(pyrrolidin-3-ylmethyl)triazole. ES/MS m/z: 408.20 [M+H].

Intermediate 953. 6-(2,4-dimethoxypyrimidin-5-yl)-8-(3-(prop-2-yn-1-yl)pyrrolidin-1-yl)imidazo[1,2-b]pyridazine

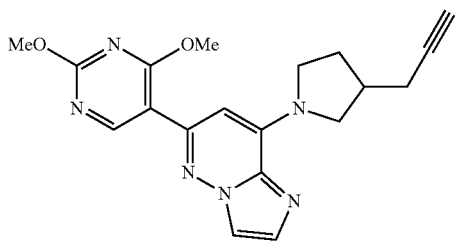 [SMILES: C#CCC1CCN(c2cc(-c3cnc(OC)nc3OC)nn3ccnc23)C1]

6-(2,4-dimethoxypyrimidin-5-yl)-8-(3-(prop-2-yn-1-yl)pyrrolidin-1-yl)imidazo[1,2-b]pyridazine was prepared in the manner described for Intermediate 944, but replacing 6-azaspiro[3.4]octane hydrochloride with 3-prop-2-ynylpyrrolidine. ES/MS m/z: 365.20 [M+H].

Intermediate 954. tert-butyl 6-(6-(2,4-dimethoxypyrimidin-5-yl)imidazo[1,2-b]pyridazin-8-yl)-1,6-diazaspiro[3.4]octane-1-carboxylate

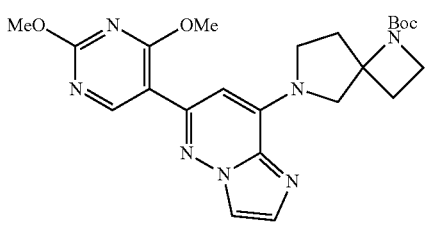 [SMILES: COc1ncc(-c2cc(N3CCC4(CCN4C(=O)OC(C)(C)C)C3)c3nccn3n2)c(OC)n1]

tert-butyl 6-(6-(2,4-dimethoxypyrimidin-5-yl)imidazo[1,2-b]pyridazin-8-yl)-1,6-diazaspiro[3.4]octane-1-carboxylate was prepared in the manner described for Intermediate 944, but replacing 6-azaspiro[3.4]octane hydrochloride with tert-butyl 1,7-diazaspiro[3.4]octane-1-carboxylate. ES/MS m/z: 468.20 [M+H].

Intermediate 955. 6-chloro-N-isobutylimidazo[1,2-b]pyridazin-8-amine

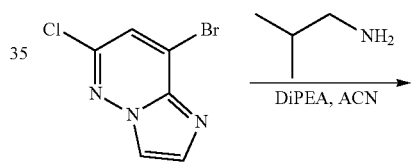

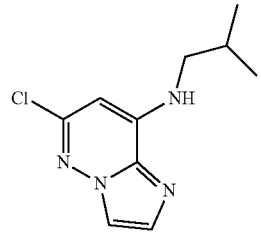

6-chloro-N-isobutylimidazo[1,2-b]pyridazin-8-amine was prepared as follows: A microwave vial was charged with 8-bromo-6-chloroimidazo[1,2-b]pyridazine (168 mg, 0.72 mmol, 1 equiv), isobutylamine (0.11 mL, 1.1 mmol, 1.5 equiv), DIPEA (0.19 mL, 1.1 mmol, 1.1 equiv), and MeCN (4 mL). The reaction mixture was heated to 80° C., until done, 1 hour. The mixture was cooled diluted with EtOAc and water and the layers separated. The organic layer was dried over sodium sulfate, concentrated and purified by flash column chromatagraphy to give 6-chloro-N-isobutylimidazo[1,2-b]pyridazin-8-amine. ES/MS m/z: 225.24.

719

Intermediate 956. 6-(2,4-di-tert-butoxypyrimidin-5-yl)-N-isobutylimidazo[1,2-b]pyridazin-8-amine

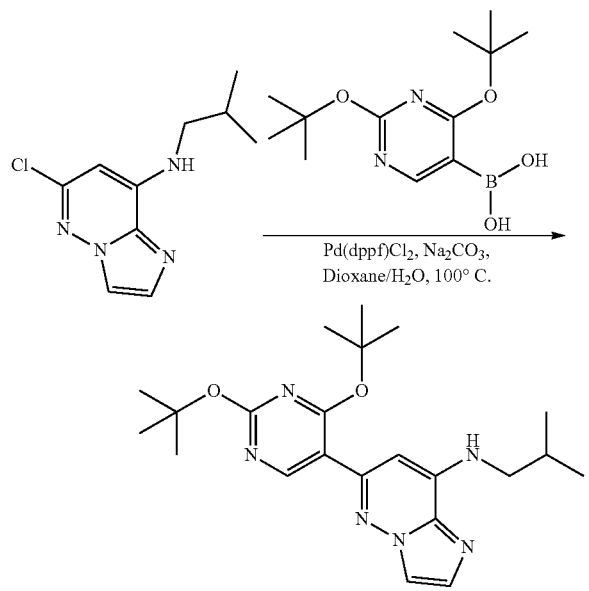

6-chloro-N-isobutylimidazo[1,2-b]pyridazin-8-amine (152 mg, 0.68 mmol) and (2,4-di-tert-butoxypyrimidin-5-yl)boronic acid (272 mg, 1.0 mmol) were dissolved in dioxane/water (3/1, 5 mL). To the reaction mixture was added sodium carbonate (215 mg, 2.0 mmol) and Pd(dppf)Cl$_2$ (41 mg, 0.1 mmol). The reaction mixture was then purged with argon for 10 mins and then heated at 100° C. for 30 minutes. The reaction mixture was cooled, diluted with EtOAc and water, the organic layer was dried over sodium sulfate, concentrated, and purified by flash column chromatography to afford 6-(2,4-di-tert-butoxypyrimidin-5-yl)-N-isobutylimidazo[1,2-b]pyridazin-8-amine. ES/MS m/z: 413.03 [M+H].

Intermediate 957. 6-chloro-N-(4-methoxybenzyl)imidazo[1,2-b]pyridazin-8-amine

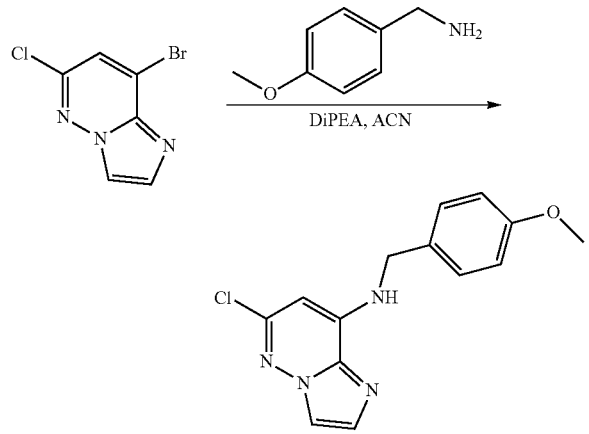

720

6-chloro-N-(4-methoxybenzyl)imidazo[1,2-b]pyridazin-8-amine was prepared as follows: A microwave vial was charged with 8-bromo-6-chloroimidazo[1,2-b]pyridazine (200 mg, 0.86 mmol, 1 equiv), (4-methoxyphenyl)methanamine (0.11 mL, 1.3 mmol, 1.5 equiv), DIPEA (0.22 mL, 1.3 mmol, 1.5 equiv), and MeCN (4 mL). The reaction mixture was heated to 80° C., until done, 1 hour. The mixture was cooled diluted with EtOAc and water and the layers separated. The organic layer was dried over sodium sulfate, concentrated and purified by flash column chromatagraphy to give 6-chloro-N-(4-methoxybenzyl)imidazo[1,2-b]pyridazin-8-amine. ES/MS m/z: 289.11.

Intermediate 958. 6-chloro-N-(2,2-difluoroethyl)-N-(4-methoxybenzyl)imidazo[1,2-b]pyridazin-8-amine

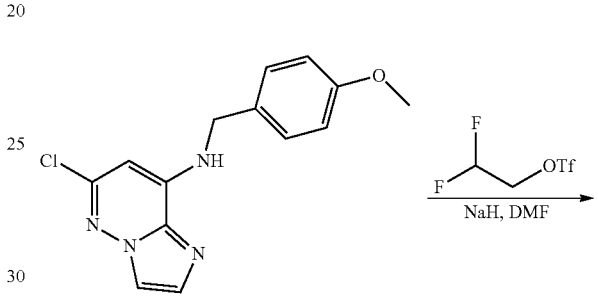

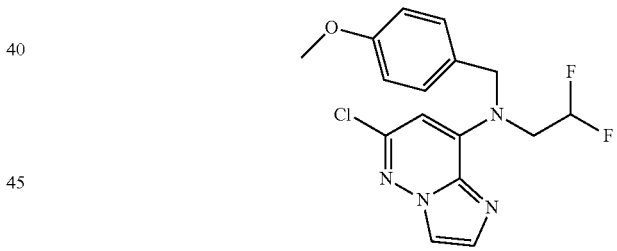

6-chloro-N-(2,2-difluoroethyl)-N-(4-methoxybenzyl)imidazo[1,2-b]pyridazin-8-amine was prepared as follows: A microwave vial was charged with 6-chloro-N-(4-methoxybenzyl)imidazo[1,2-b]pyridazin-8-amine (80 mg, 0.28 mmol, 1 equiv), DMF (2 mL) followed by sodium hydride 60% dispersion in mineral oil (13 mg, 0.33 mmol, 1.2 equiv). After the mixture was stirred for 10 minutes then 2,2-difluoroethyl trifluoromethanesulfonate (119 mg, 0.55 mmol, 2 equiv) was added the mixture was heated was heated to 60° C., until done, 1 hour. The mixture was cooled diluted with EtOAc and water and the layers separated. The organic layer was dried over sodium sulfate, concentrated and purified by flash column chromatagraphy to give 6-chloro-N-(2,2-difluoroethyl)-N-(4-methoxybenzyl)imidazo[1,2-b]pyridazin-8-amine. ES/MS m/z: 353.02.

Intermediate 959. 6-(2,4-di-tert-butoxypyrimidin-5-yl)-N-(2,2-difluoroethyl)-N-(4-methoxybenzyl)imidazo[1,2-b]pyridazin-8-amine

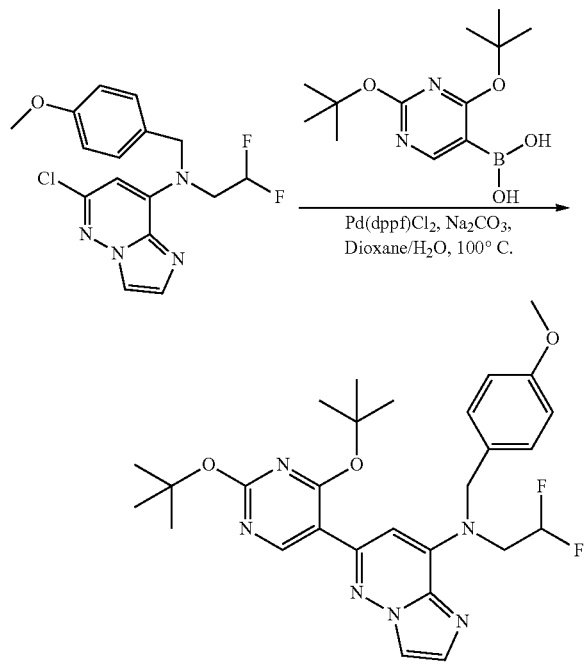

6-chloro-N-(4-methoxybenzyl)imidazo[1,2-b]pyridazin-8-amine (82 mg, 0.23 mmol) and (2,4-di-tert-butoxypyrimidin-5-yl)boronic acid (93 mg, 1.5 mmol) were dissolved in dioxane/water (3/1, 2 mL). To the reaction mixture was added sodium carbonate (74 mg, 3.0 mmol) and Pd(dppf)Cl$_2$ (14 mg, 0.1 mmol). The reaction mixture was then purged with argon for 10 mins and then heated at 100° C. for 30 minutes. The reaction mixture was cooled, diluted with EtOAc and water, the organic layer was dried over sodium sulfate, concentrated, and purified by flash column chromatography to afford 6-(2,4-di-tert-butoxypyrimidin-5-yl)-N-(2,2-difluoroethyl)-N-(4-methoxybenzyl)imidazo[1,2-b]pyridazin-8-amine. ES/MS m/z: 541.77 [M+H].

Intermediate 960. 6-chloro-8-(3,3,3-trifluoro-2,2-dimethylpropoxy)imidazo[1,2-b]pyridazine

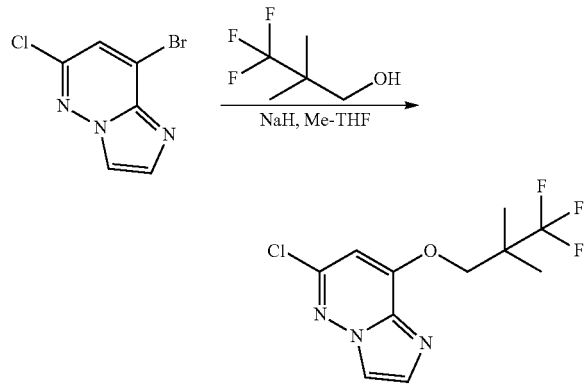

6-chloro-8-(3,3,3-trifluoro-2,2-dimethylpropoxy)imidazo[1,2-b]pyridazine was prepared as follows: To a vial add 3,3,3-trifluoro-2,2-dimethyl-propan-1-ol (153 mg, 1.1 mmol) and Me-THF (2 ml) then carefully add sodium hydride 60% dispersion in mineral oil (16.5 mg, 0.43 mmol) allowing to stir for 10 minutes then add 8-bromo-6-chloro-imidazo[1,2-b]pyridazine (50 mg, 0.22 mmol) then cap and heat to 70° C. for 2 hr. The reaction was cooled quenched with water, extracted 2×EtOAc, the organic layer was dried over sodium sulfate, concentrated, and used crude in the next reaction. ES/MS m/z: 294.21 [M+H].

Intermediate 961. 6-(2,4-di-tert-butoxypyrimidin-5-yl)-8-(3,3,3-trifluoro-2,2-dimethylpropoxy)imidazo[1,2-b]pyridazine

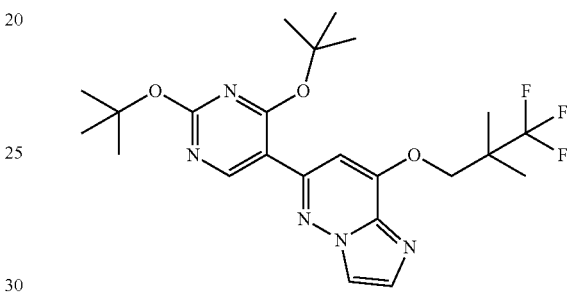

6-(2,4-di-tert-butoxypyrimidin-5-yl)-8-(3,3,3-trifluoro-2,2-dimethylpropoxy)imidazo[1,2-b]pyridazine was prepared in the manner described for Intermediate 959, but replacing 6-chloro-N-(4-methoxybenzyl)imidazo[1,2-b]pyridazin-8-amine with 6-chloro-8-(3,3,3-trifluoro-2,2-dimethylpropoxy)imidazo[1,2-b]pyridazine. ES/MS m/z: 482.53 [M+H].

Intermediate 962. 6-chloro-8-fluoroimidazo[1,2-b]pyridazine

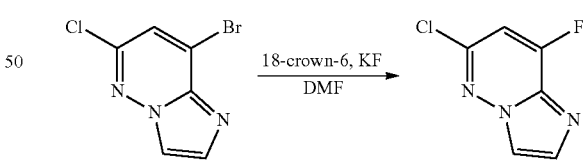

8-bromo-6-chloroimidazo[1,2-b]pyridazine (3 g, 13 mmol), potassium fluoride (4.4 g, 75 mmol), 18-crown-6 (3.4 g, 13 mmol) and DMF (15 ml) the reaction was stirred for 7 hours at 100° C. The reaction is then cooled to RT, diluted with DCM and filtered to remove solids. The cake is rinsed with DCM, the resulting mixture is purified by flash column chromatography to 6-chloro-8-fluoroimidazo[1,2-b]pyridazine. ES/MS m/z: 172.09 [M+H].

723

Intermediate 963. 6-(2,4-di-tert-butoxypyrimidin-5-yl)-8-fluoroimidazo[1,2-b]pyridazine

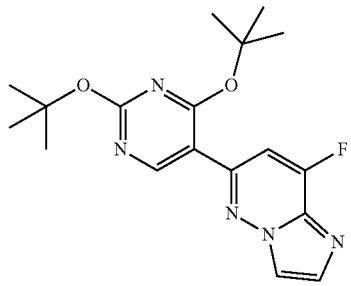 [SMILES: CC(C)(C)Oc1ncc(-c2cc(F)c3nccn3n2)c(OC(C)(C)C)n1]

6-(2,4-di-tert-butoxypyrimidin-5-yl)-8-fluoroimidazo[1,2-b]pyridazine was prepared in the manner described for Intermediate 959, but replacing 6-chloro-N-(4-methoxybenzyl)imidazo[1,2-b]pyridazin-8-amine with to 6-chloro-8-fluoroimidazo[1,2-b]pyridazine. ES/MS m/z: 359.84 [M+H].

Intermediate 964. 3-ethynyl-3-methyl-pyrrolidine

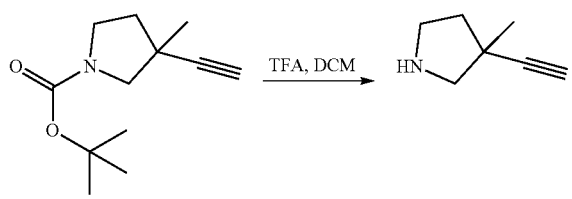

3-ethynyl-3-methyl-pyrrolidine was prepared as follows: To a solution of tert-butyl 3-ethynyl-3-methyl-pyrrolidine-1-carboxylate (50 mg, 0.24 mmol, 1 equiv) in DCM (1 mL) was added TFA solution (0.5 mL). The reaction vessel was stirred until complete (0.5 hr), the mixture is then concentrated and used as is in next reaction. ES/MS: 110.22 [M+1].

Intermediate 965. 6-(2,4-di-tert-butoxypyrimidin-5-yl)-8-(3-ethynyl-3-methylpyrrolidin-1-yl)imidazo[1,2-b]pyridazine

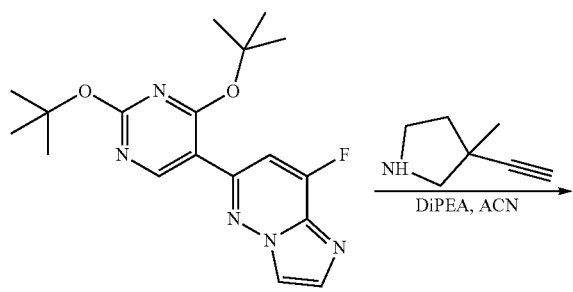

724

-continued

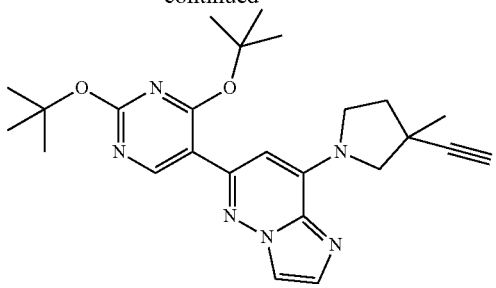

6-(2,4-di-tert-butoxypyrimidin-5-yl)-8-(3-ethynyl-3-methylpyrrolidin-1-yl)imidazo[1,2-b]pyridazine was prepared as follows: A microwave vial was charged with 3-ethynyl-3-methyl-pyrrolidine (13 mg, 0.12 mmol), DIPEA (0.1 mL, 0.56 mmol), and MeCN (2 mL) then 6-(2,4-di-tert-butoxypyrimidin-5-yl)-8-fluoroimidazo[1,2-b]pyridazine (44 mg, 0.12 mmol). The reaction mixture was heated to 80° C., until done, 2 hour. The mixture was cooled diluted with EtOAc and water and the layers separated. The organic layer was dried over sodium sulfate, concentrated and purified by flash column chromatagraphy to give 6-(2,4-di-tert-butoxypyrimidin-5-yl)-8-(3-ethynyl-3-methylpyrrolidin-1-yl)imidazo[1,2-b]pyridazine. ES/MS m/z: 449.06 [M+1].

Intermediate 966. 6-(2,4-di-tert-butoxypyrimidin-5-yl)-8-bromoimidazo[1,2-b]pyridazine

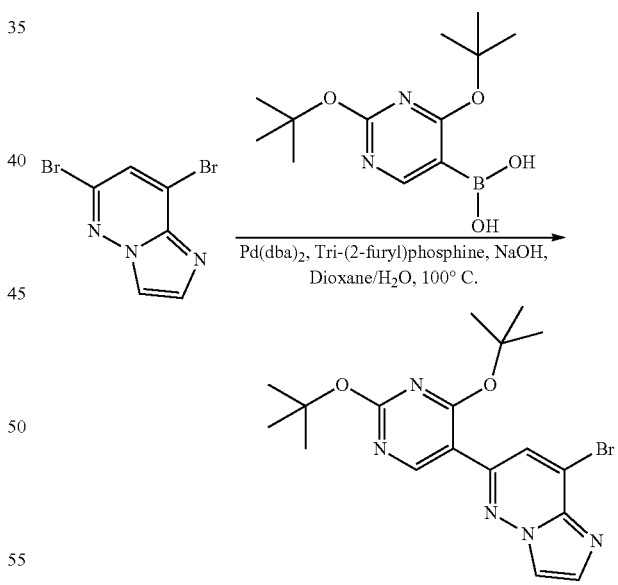

6,8-dibromoimidazo[1,2-b]pyridazine (100 mg, 0.36 mmol), (2,4-di-tert-butoxypyrimidin-5-yl)boronic acid (85 mg, 0.32 mmol) were dissolved in dioxane (1.5 ml) and 1 N NaOH (0.5 ml). To the reaction mixture was added tri-(2-furyl)phosphine (17 mg, 0.07 mmol) and Pd(dba)₂ (21 mg, 0.11 mmol). The reaction mixture was then purged with argon for 10 mins and then heated at 80° C. for 60 minutes. The reaction mixture was cooled, diluted with EtOAc and water, the organic layer was dried over sodium sulfate, concentrated, and purified by flash column chromatography to afford 6-(2,4-di-tert-butoxypyrimidin-5-yl)-8-bromoimidazo[1,2-b]pyridazine. ES/MS m/z: 419.86 and 421.88 [M+H].

Intermediate 967. 4-(6-(2,4-di-tert-butoxypyrimidin-5-yl)imidazo[1,2-b]pyridazin-8-yl)-2-methylbut-3-yn-2-ol

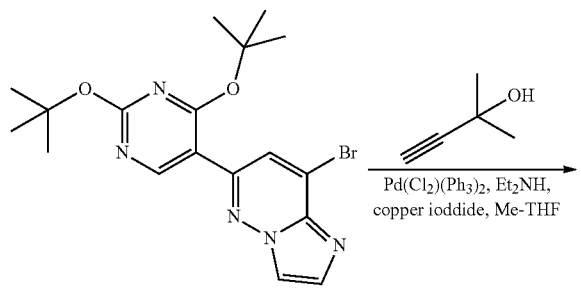

8-bromo-6-(2,4-di-tert-butoxypyrimidin-5-yl)imidazo[1,2-b]pyridazine (15 mg, 0.04 mmol), 2-Methyl-3-butyn-2-ol (0.007 ml, 0.07 mmol) were dissolved in Me-THF (2 ml). To the reaction mixture was added diethylamine (0.04 ml, 0.36 mmol), copper iodide (0.68 mg, 0.004 mmol) and Pd(Cl)$_2$(Ph$_3$)$_2$ (2.5 mg, 0.004 mmol). The reaction mixture was then purged with argon for 10 mins and then heated at 80° C. for 30 minutes. The reaction mixture was cooled, diluted with EtOAc and water, the organic layer was dried over sodium sufate, concentrated, and purified by flash column chromatography to afford 4-(6-(2,4-di-tert-butoxypyrimidin-5-yl)imidazo[1,2-b]pyridazin-8-yl)-2-methylbut-3-yn-2-ol. ES/MS m/z: 424.80 [M+H].

Intermediate 968 and 969. 3-((6-(2,4-di-tert-butoxypyrimidin-5-yl)imidazo[1,2-b]pyridazin-8-yl)oxy)-2,2-difluoropropan-1-ol and 8,8'-((2,2-difluoropropane-1,3-diyl)bis(oxy))bis(6-(2,4-di-tert-butoxypyrimidin-5-yl)imidazo[1,2-b]pyridazine)

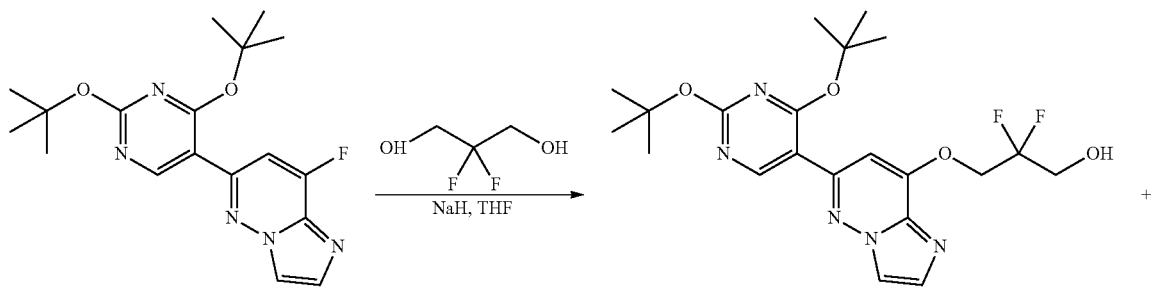

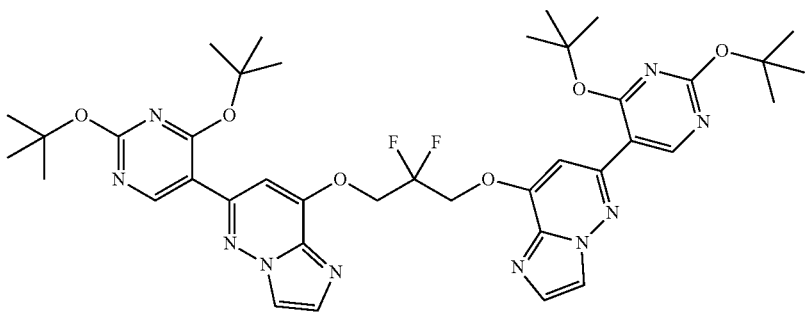

-continued

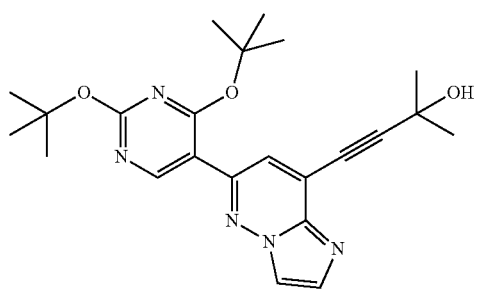

3-((6-(2,4-di-tert-butoxypyrimidin-5-yl)imidazo[1,2-b]pyridazin-8-yl)oxy)-2,2-difluoropropan-1-ol and 8,8'-((2,2-difluoropropane-1,3-diyl)bis(oxy))bis(6-(2,4-di-tert-butoxypyrimidin-5-yl)imidazo[1,2-b]pyridazine) were prepared as follows: To a vial add 2,2-difluoropropane-1,3-diol (468 mg, 4.2 mmol) and THF (10 ml) then carefully add sodium hydride 60% dispersion in mineral oil (64 mg, 1.7 mmol) allowing to stir for 10 minutes then add 6-(2,4-di-tert-butoxypyrimidin-5-yl)-8-fluoroimidazo[1,2-b]pyridazine (300 mg, 0.83 mmol) the reaction was complete after 10 minutes. The reaction was quenched with water, extracted 2×EtOAc, the organic layer was dried over sodium sulfate, concentrated, and purified by flash column chromatography to give the two title compounds. ES/MS m/z: product 1: 452.07 and product 2: 791.23 [M+H].

Intermediate 970. 6-(2,4-di-tert-butoxypyrimidin-5-yl)-8-(2,2-difluorobutoxy)imidazo[1,2-b]pyridazine

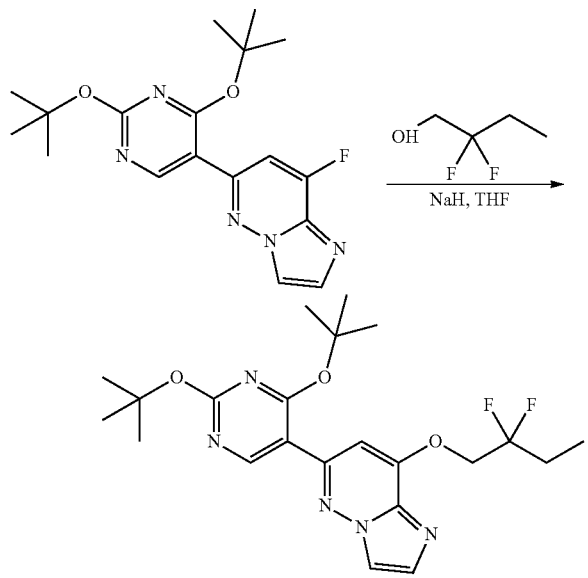

6-(2,4-di-tert-butoxypyrimidin-5-yl)-8-(2,2-difluorobutoxy)imidazo[1,2-b]pyridazine was prepared as follows: To a vial add 2,2-difluorobutan-1-ol (23 mg, 0.21 mmol) and THF (2 ml) then carefully add sodium hydride 60% dispersion in mineral oil (3.2 mg, 0.08 mmol) allowing to stir for 10 minutes then add 6-(2,4-di-tert-butoxypyrimidin-5-yl)-8-fluoroimidazo[1,2-b]pyridazine (15 mg, 0.04 mmol) the reaction was complete after 10 minutes. The reaction was quenched with water, extracted 2×EtOAc, the organic layer was dried over sodium sulfate, concentrated, and used crude in the next reaction. ES/MS m/z: 450.22 [M+H].

Intermediate 971. 3-((6-(2,4-di-tert-butoxypyrimidin-5-yl)imidazo[1,2-b]pyridazin-8-yl)oxy)-2,2-difluoropropyl isopropylcarbamate

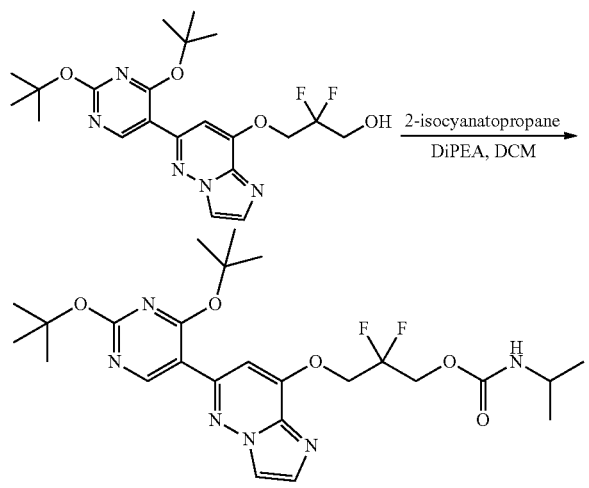

3-((6-(2,4-di-tert-butoxypyrimidin-5-yl)imidazo[1,2-b]pyridazin-8-yl)oxy)-2,2-difluoropropyl isopropylcarbamate was prepared as follows: To a vial add 3-((6-(2,4-di-tert-butoxypyrimidin-5-yl)imidazo[1,2-b]pyridazin-8-yl)oxy)-2,2-difluoropropan-1-ol (15 mg, 0.03 mmol) and DCM (2 ml) then add DiPEA (0.18 ml, 0.10 mmol) and 2-isocyanatopropane (0.03 ml, 0.33 mmol) the mixture was then heated at 60° C. overnight. The reaction was quenched with water, extracted 2×EtOAc, the organic layer was dried over sodium sulfate, concentrated, and purified by flash column chromatography to give the title compound. ES/MS m/z: 537.23 [M+H].

Intermediate 972. 6-(2,4-di-tert-butoxypyrimidin-5-yl)-8-(2,2-difluoro-3-(pyridin-2-yloxy)propoxy)imidazo[1,2-b]pyridazine

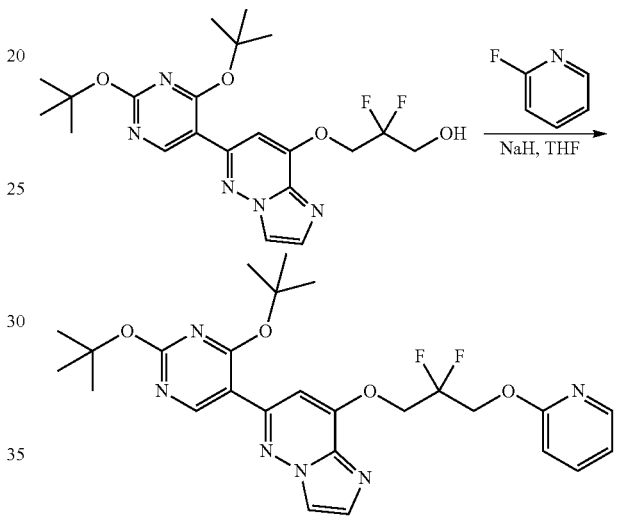

6-(2,4-di-tert-butoxypyrimidin-5-yl)-8-(2,2-difluoro-3-(pyridin-2-yloxy)propoxy)imidazo[1,2-b]pyridazine was prepared as follows: To a vial add 3-((6-(2,4-di-tert-butoxypyrimidin-5-yl)imidazo[1,2-b]pyridazin-8-yl)oxy)-2,2-difluoropropan-1-ol (15 mg, 0.03 mmol) and THF (2 ml) then carefully add sodium hydride 60% dispersion in mineral oil (2.5 mg, 0.07 mmol) allowing to stir for 10 minutes then add 2-fluoropyridine (16 mg, 0.17 mmol) the reaction was heated at 60° C. for 1.5 hours. The reaction was quenched with water, extracted 2×EtOAc, the organic layer was dried over sodium sulfate, concentrated, and, and purified by flash column chromatography to give the title compound. ES/MS m/z: 529.10 [M+H].

Intermediate 973. 3-((6-(2,4-di-tert-butoxypyrimidin-5-yl)imidazo[1,2-b]pyridazin-8-yl)oxy)-2,2-difluoropropyl (2,2,2-trifluoroethyl) carbonate

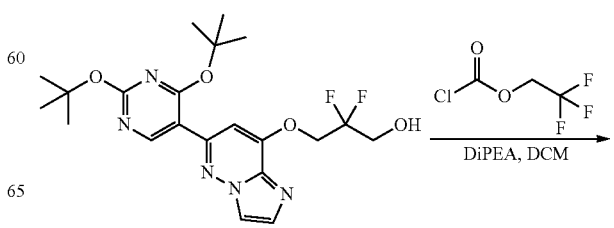

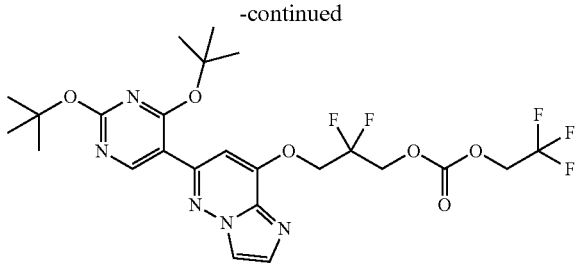

3-((6-(2,4-di-tert-butoxypyrimidin-5-yl)imidazo[1,2-b]pyridazin-8-yl)oxy)-2,2-difluoropropyl (2,2,2-trifluoroethyl) carbonate was prepared as follows: To a vial add 3-((6-(2,4-di-tert-butoxypyrimidin-5-yl)imidazo[1,2-b]pyridazin-8-yl)oxy)-2,2-difluoropropan-1-ol (15 mg, 0.03 mmol) and DCM (2 ml) then add DiPEA (0.06 ml, 0.33 mmol) and 2,2,2-trifluoroethyl carbonochloridate (54 mg, 0.33 mmol) the mixture was then heated at 60° C. overnight. The reaction was quenched with water, extracted 2×EtOAc, the organic layer was dried over sodium sulfate, concentrated, and purified by flash column chromatography to give the title compound. ES/MS m/z: 578.09 [M+H].

Intermediate 974. Tert-butyl (S)-3,3-difluoro-4-(1-(2,2,2-trifluoroethyl)-1H-indazol-6-yl)oxy)pyrrolidine-1-carboxylate

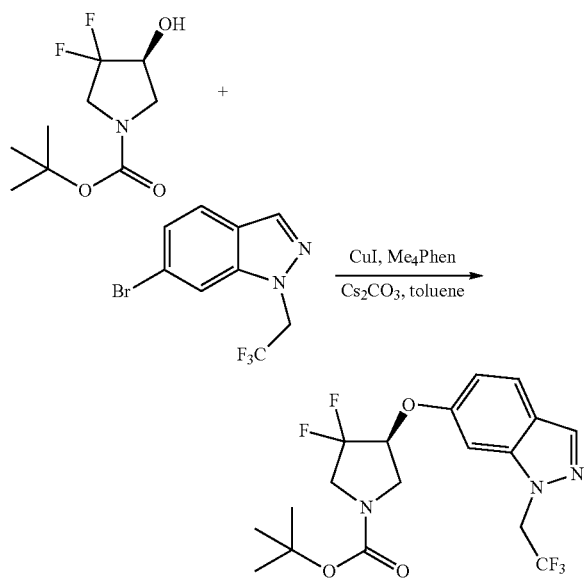

Tert-butyl (S)-3,3-difluoro-4-((1-(2,2,2-trifluoroethyl)-1H-indazol-6-yl)oxy)pyrrolidine-1-carboxylate was prepared as follows: A microwave vial was charged with copper(I) iodide (32 mg, 0.168 mmol, 0.25 equiv), 3,4,7,8-tetramethyl-1,10-phenanthroline (32 mg, 0.134 mmol, 0.2 equiv), cesium carbonate (328 mg, 1.01 mmol, 1.5 equiv), tert-butyl (S)-3,3-difluoro-4-hydroxypyrrolidine-1-carboxylate (150 mg, 0.672 mmol, 1 equiv) and 6-bromo-1-(2,2,2-trifluoroethyl)-1H-indazole (188 mg, 0.672 mmol, 1 equiv). The vial was sealed and toluene (2.0 mL) was added under an Argon atmosphere. The reaction mixture was gradually heated to 120° C. and stirred overnight. After cooling to room temperature, the mixture was diluted with EtOAc and filtered through a pad of Celite. The filtrate was concentrated under reduced pressure and the crude material was purified by silica gel chromatography (0-100% EtOAc in hexanes) to afford the title compound. ES/MS m/z: 422.1 [M+H]. $^1$H NMR (400 MHz, Chloroform-d) δ 8.01 (s, 1H), 7.67 (d, J=8.7 Hz, 1H), 6.91 (dd, J=8.8, 2.1 Hz, 1H), 6.87 (s, 1H), 4.95-4.79 (m, 3H), 3.95-3.60 (m, 4H), 1.51-1.46 (m, 9H). $^{19}$F NMR (376 MHz, Chloroform-d) δ −71.17, −105.56-−107.02 (m), −120.14-−121.91 (m).

Intermediate 975. (S)-6-((4,4-difluoropyrrolidin-3-yl)oxy)-1-(2,2,2-trifluoroethyl)-1H-indazole hydrochloride

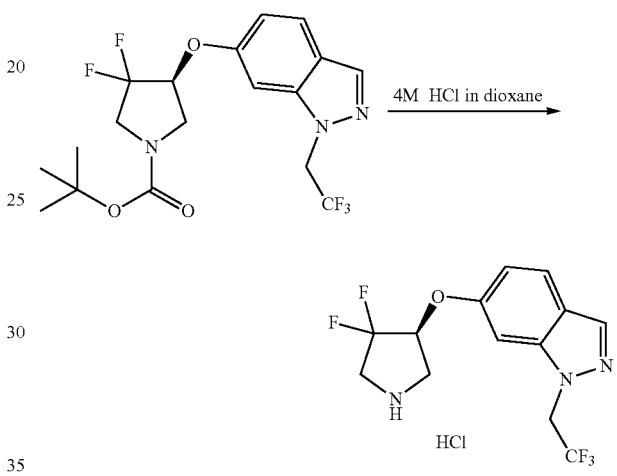

(S)-6-((4,4-difluoropyrrolidin-3-yl)oxy)-1-(2,2,2-trifluoroethyl)-1H-indazole hydrochloride was prepared as follows: A solution of tert-butyl (S)-3,3-difluoro-4-((1-(2,2,2-trifluoroethyl)-1H-indazol-6-yl)oxy)pyrrolidine-1-carboxylate (100 mg, 0.237 mmol, 1 equiv) in 4 M HCl in dioxane (2.0 mL, 34 equiv) was stirred at room temperature for 2 h and 30 min prior to concentration in vacuo to afford the title compound in quantitative yield. ES/MS m/z: 322.0 [M+H]. $^1$H NMR (400 MHz, DMSO-d6) δ 10.33 (s, 3H), 8.16-8.12 (m, 1H), 7.76 (d, J=8.8 Hz, 1H), 7.55-7.51 (m, 1H), 6.98-6.92 (m, 1H), 5.44-5.30 (m, 3H), 3.95-3.29 (m, 4H).

The title compound was purified by RP-HPLC (10-90% MeCN/H$_2$O with TFA, Gemini-NX column) to afford it as the TFA salt, which was used in the subsequent reaction.

Intermediate 976. (S)-6-chloro-8-(3,3-difluoro-4-((1-(2,2,2-trifluoroethyl)-1H-indazol-6-yl)oxy)pyrrolidin-1-yl)imidazo[1,2-b]pyridazine

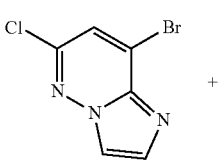

-continued

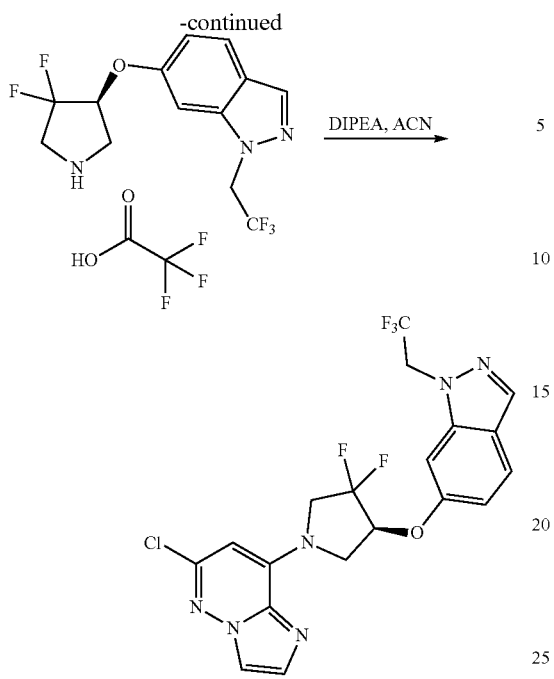

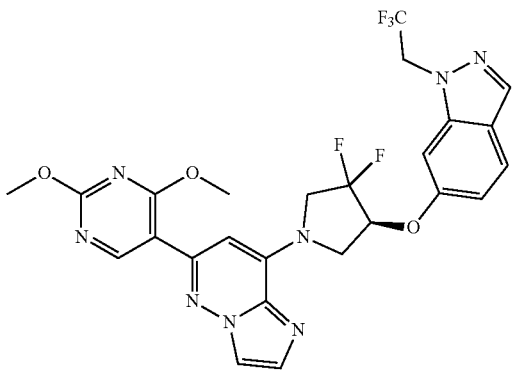

(S)-6-chloro-8-(3,3-difluoro-4-((1-(2,2,2-trifluoroethyl)-1H-indazol-6-yl)oxy)pyrrolidin-1-yl)imidazo[1,2-b]pyridazine was prepared as follows: A solution of 8-bromo-6-chloroimidazo[1,2-b]pyridazine (10 mg, 0.041 mmol, 1 equiv) and (S)-6-((4,4-difluoropyrrolidin-3-yl)oxy)-1-(2,2,2-trifluoroethyl)-1H-indazole trifluoroacetate (18 mg, 0.041 mmol, 1 equiv) in ACN (2.0 mL) was added DIPEA (0.02 mL, 0.099 mmol, 2.4 equiv). The solution was heated to 85° C. and stirred overnight. The temperature was increased to 100° C. and the reaction mixture was stirred for an additional 6 h. Additional DIPEA (0.20 mL, 1.15 mmol) was added and the solution was stirred at 120° C. overnight. The reaction mixture was diluted with water and the resulting solids filtered. The solids were dissolved in EtOAc and the filtrate concentrated to afford the title compound. ES/MS m/z: 473.0 [M+H]. $^1$H NMR (400 MHz, DMSO-d6) δ 8.15-8.08 (m, 2H), 7.74 (d, J=8.7 Hz, 1H), 7.61-7.54 (m, 2H), 6.98 (dd, J=8.8, 2.0 Hz, 1H), 6.23 (s, 1H), 5.52-5.30 (m, 3H), 4.75-3.86 (m, 4H).

Intermediate 977. (S)-8-(3,3-difluoro-4-((1-(2,2,2-trifluoroethyl)-1H-indazol-6-yl)oxy)pyrrolidin-1-0)-6-(2,4-dimethoxypyrimidin-5-yl)imidazo[1,2-b]pyridazine

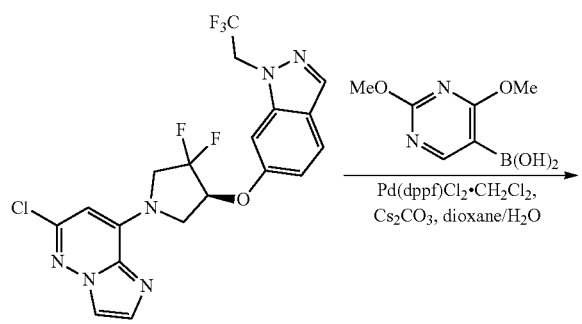

(5)-8-(3,3-difluoro-4-(1-(2,2,2-trifluoroethyl)-1H-indazol-6-yl)oxy)pyrrolidin-1-yl)-6-(2,4-dimethoxypyrimidin-5-yl)imidazo[1,2-b]pyridazine was prepared as follows: A microwave vial was charged with (S)-6-chloro-8-(3,3-difluoro-4-((1-(2,2,2-trifluoroethyl)-1H-indazol-6-yl)oxy)pyrrolidin-1-yl)imidazo[1,2-b]pyridazine (10 mg, 0.022 mmol, 1 equiv), (2,4-dimethoxypyrimidin-5-yl)boronic acid (5 mg, 0.030 mmol, 1.35 equiv), Pd(dppf)Cl$_2$CH$_2$Cl$_2$ (2 mg, 0.002 mmol, 0.1 equiv) and cesium carbonate (14 mg, 0.044 mmol, 2 equiv). To this was added 1,4 dioxane (3.0 mL) and water (0.50 mL). The reaction mixture was heated at 80° C. and stirred overnight. Additional (2,4-dimethoxypyrimidin-5-yl)boronic acid (14 mg, 0.076 mmol) and Pd(dppf)Cl$_2$CH$_2$Cl$_2$ (20 mg, 0.024 mmol) was added and the solution was stirred at 85° C. for an additional 5 h and 40 min. After cooling to room temperature, the mixture was diluted with EtOAc and filtered through a pad of Celite. The filtrate was concentrated under reduced pressure and the crude material was purified by silica gel chromatography (0-100% EtOAc in hexanes) to afford the title compound. ES/MS m/z: 577.1 [M+H].

Intermediate 978. 6-bromo-3,3-dimethyl-1-(2,2,2-trifluoroethyl)pyrrolo[3,2-b]pyridin-2-one

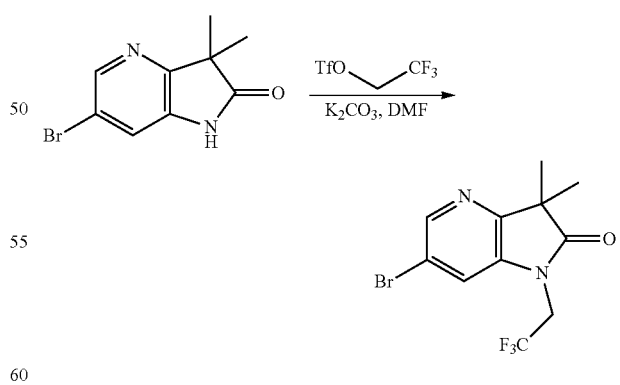

To a solution of 6-bromo-3,3-dimethyl-1H-pyrrolo[3,2-b]pyridin-2-one (0.5 g, 2.07 mmol, 1 equiv) in DMF (4 mL) was added potassium carbonate (860 mg, 6.22 mmol, 3 equiv) and 2,2,2-trifluoroethyl trifluoromethanesulfonate (722 mg, 3.11 mmol, 1.5 equiv). The reaction mixture was heated to 80 C. After 2 hours, the reaction mixture was diluted with brine (50 mL) and extracted with EtOAc. The combined organic layers were dried over $Na_2SO_4$, filtered, and concentrated. Purification was accomplished by $SiO_2$ chromatography (0-100% EtOAc/Hex), affording 6-bromo-3,3-dimethyl-1-(2,2,2-trifluoroethyl)pyrrolo[3,2-b]pyridin-2-one. ES/MS m/z: 323.10 [M+H]

Intermediate 979. 6-[(1S,2S)-2-(6-chloroimidazo[1,2-b]pyridazin-8-yl)cyclopropyl]-3-fluoro-1-(2,2,2-trifluoroethyl)pyrazolo[4,3-b]pyridine

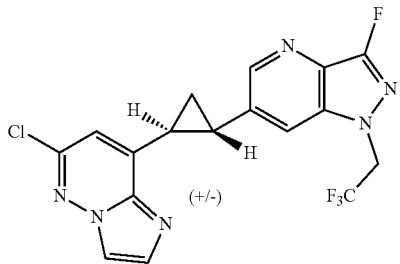 [SMILES: Fc1nn(CC(F)(F)F)c2cc([C@H]3C[C@@H]3c3cc(Cl)nn4ccnc34)cnc12]

6-[(1S,2S)-2-(6-chloroimidazo[1,2-b]pyridazin-8-yl)cyclopropyl]-3-fluoro-1-(2,2,2-trifluoroethyl)pyrazolo[4,3-b]pyridine was prepared as a racemic mixture in the manner described for Intermediate 352, but replacing 2-bromo-5-(difluoromethoxy)pyridine with 6-bromo-3-fluoro-1-(2,2,2-trifluoroethyl)pyrazolo[4,3-b]pyridine. ES/MS m/z: 411.10 [M+H].

Intermediate 980. 6-[(1S,2S)-2-(6-chloroimidazo[1,2-b]pyridazin-8-yl)cyclopropyl]-3,3-dimethyl-1-(2,2,2-trifluoroethyl)pyrrolo[3,2-b]pyridin-2-one

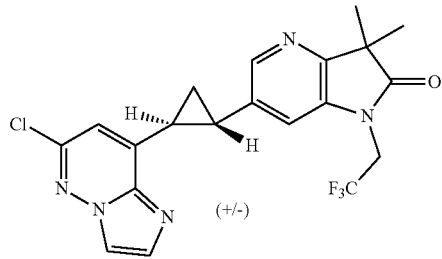 [SMILES: CC1(C)C(=O)N(CC(F)(F)F)c2cc([C@H]3C[C@@H]3c3cc(Cl)nn4ccnc34)cnc21]

6-[(1S,2S)-2-(6-chloroimidazo[1,2-b]pyridazin-8-yl)cyclopropyl]-3,3-dimethyl-1-(2,2,2-trifluoroethyl)pyrrolo[3,2-b]pyridin-2-one was prepared as a racemic mixture in the manner described for Intermediate 352, but replacing 2-bromo-5-(difluoromethoxy)pyridine with 6-bromo-3,3-dimethyl-1-(2,2,2-trifluoroethyl)pyrrolo[3,2-b]pyridin-2-one. ES/MS m/z: 436.40 [M+H].

Intermediate 981. 6-[(1S,2S)-2-[6-(2,4-dimethoxypyrimidin-5-yl)imidazo[1,2-b]pyridazin-8-yl]cyclopropyl]-3-fluoro-1-(2,2,2-trifluoroethyl)pyrazolo[4,3-b]pyridine

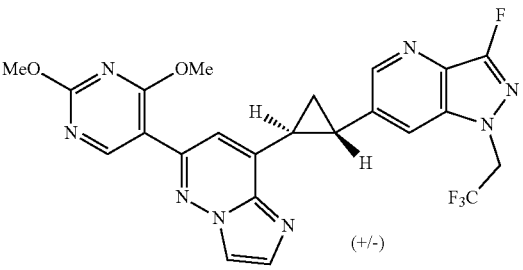 [SMILES: COc1ncc(-c2cc([C@H]3C[C@@H]3c3cnc4c(F)nn(CC(F)(F)F)c4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]-3-fluoro-1-(2,2,2-trifluoroethyl)pyrazolo[4,3-b]pyridine (Racemic Mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-3-fluoro-1-(2,2,2-trifluoroethyl)pyrazolo[4,3-b]pyridine (Racemic Mixture). ES/MS m/z: 515.10 [M+H].

Intermediate 982. 6-[(1S,2S)-2-[6-(2,4-dimethoxypyrimidin-5-yl)imidazo[1,2-b]pyridazin-8-yl]cyclopropyl]-3-fluoro-1-(2,2,2-trifluoroethyl)pyrazolo[4,3-b]pyridine

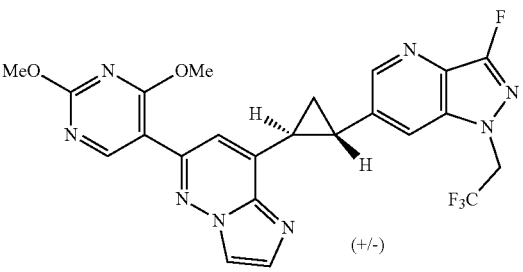 [SMILES: COc1ncc(-c2cc([C@H]3C[C@@H]3c3cnc4c(F)nn(CC(F)(F)F)c4c3)c3nccn3n2)c(OC)n1]

6-[(1S,2S)-2-[6-(2,4-dimethoxypyrimidin-5-yl)imidazo[1,2-b]pyridazin-8-yl]cyclopropyl]-3-fluoro-1-(2,2,2-trifluoroethyl)pyrazolo[4,3-b]pyridine was chirally separated from the racemic Intermediate 981 by SFC AD-H column (20% EtOH). ES/MS m/z: 514.20 [M+H].

Intermediate 983. 6-[(1S,2S)-2-[6-(2,4-dimethoxy-pyrimidin-5-yl)imidazo[1,2-b]pyridazin-8-yl]cyclopropyl]-3,3-dimethyl-1-(2,2,2-trifluoroethyl)pyrrolo[3,2-b]pyridin-2-one (Racemic Mixture)

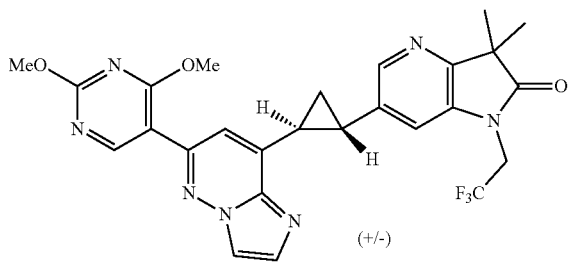 [SMILES: COc1ncc(-c2cc([C@H]3C[C@@H]3c3cnc4c(c3)N(CC(F)(F)F)C(=O)C4(C)C)c3nccn3n2)c(OC)n1]

6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)pyrrolo[3,2-b]pyridin-2-one (racemic mixture) was prepared in the manner described for Intermediate 18, but replacing 6-chloro-8-cyclopropyl-2-methyl-imidazo[1,2-b]pyridazine with 6-[(1S,2S)-2-(6-chloroimidazo[1,2-b]pyridazin-8-yl)cyclopropyl]-3,3-dimethyl-1-(2,2,2-trifluoroethyl)pyrrolo[3,2-b]pyridin-2-one (Racemic Mixture). ES/MS m/z: 540.20 [M+H].

Intermediate 984. 6-[(1S,2S)-2-[6-(2,4-dimethoxy-pyrimidin-5-yl)imidazo[1,2-b]pyridazin-8-yl]cyclopropyl]-3,3-dimethyl-1-(2,2,2-trifluoroethyl)pyrrolo[3,2-b]pyridin-2-one

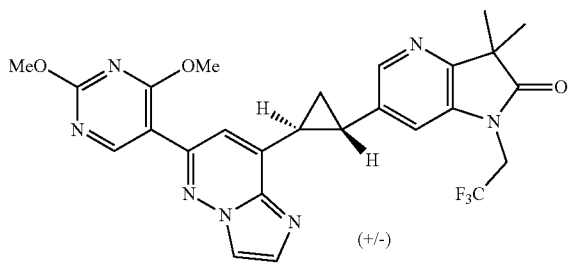 [SMILES: COc1ncc(-c2cc([C@H]3C[C@@H]3c3cnc4c(c3)N(CC(F)(F)F)C(=O)C4(C)C)c3nccn3n2)c(OC)n1]

6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)pyrrolo[3,2-b]pyridin-2-one was chirally separated from the racemic Intermediate 983 by SFC Cell 2 column (20% EtOH). ES/MS m/z: 540.20 [M+H].

Intermediate 985. 6-bromo-8-(2,2,2-trifluoroethoxy)quinoline

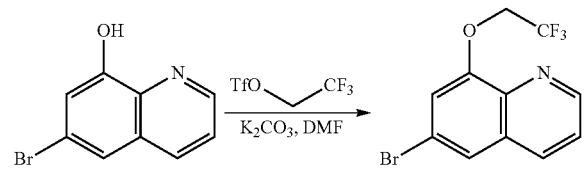

To a solution of 6-bromoquinolin-8-ol (300 mg, 1.34 mmol, 1 equiv) in DMF (4 mL) was added potassium carbonate (555 mg, 4.02 mmol, 3 equiv) and 2,2,2-trifluoroethyl trifluoromethanesulfonate (0.290 mL, 2.01 mmol, 1.5 equiv). The reaction mixture was heated to 80° C. After 2 hours, the reaction mixture was directly purified by SiO₂ chromatography (0-100% EtOAc/Hex), affording 6-bromo-8-(2,2,2-trifluoroethoxy)quinoline. ¹H NMR (400 MHz, DMSO-d6) δ 8.94 (dd, J=4.2, 1.7 Hz, 1H), 8.34 (dd, J=8.4, 1.7 Hz, 1H), 7.95 (d, J=2.0 Hz, 1H), 7.63 (dd, J=8.4, 4.2 Hz, 1H), 7.52 (d, J=2.0 Hz, 1H), 5.03 (q, J=8.8 Hz, 2H). ES/MS m/z: 306.00 [M+H].

Intermediate 986. 6-((2S,2S)-2-(6-chloroimidazo[1,2-b]pyridazin-8-yl)cyclopropyl)-8-(2,2,2-trifluoroethoxy)quinoline

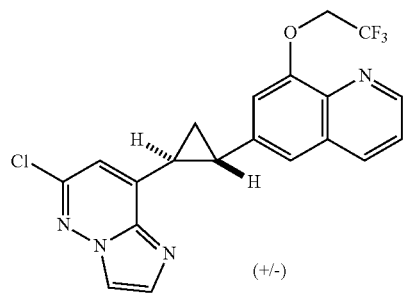 [SMILES: FC(F)(F)COc1cc([C@H]2C[C@@H]2c2cc(Cl)nn3ccnc23)cc2cccnc12]

6-((1S,2S)-2-(6-chloroimidazo[1,2-b]pyridazin-8-yl)cyclopropyl)-8-(2,2,2-trifluoroethoxy)quinoline was prepared as a racemic mixture in the manner described for Intermediate 846, but replacing 6-bromo-2-(difluoromethyl)benzo[d]thiazole with 6-bromo-8-(2,2,2-trifluoroethoxy)quinoline. ES/MS m/z: 419.10 [M+H].

Intermediate 987. 6-((2S,2S)-2-(6-(2,4-dimethoxy-pyrimidin-5-yl)imidazo[1,2-b]pyridazin-8-yl)cyclopropyl)-8-(2,2,2-trifluoroethoxy)quinoline

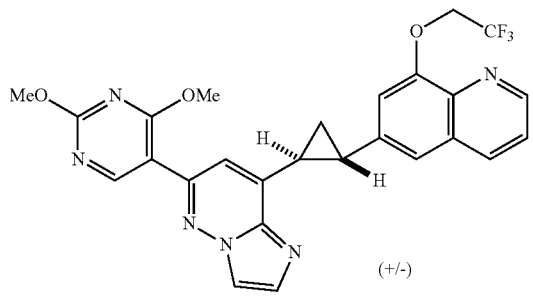 [SMILES: COc1ncc(-c2cc([C@H]3C[C@@H]3c3cc(OCC(F)(F)F)c4ncccc4c3)c3nccn3n2)c(OC)n1]

6-((1S,2S)-2-(6-(2,4-dimethoxypyrimidin-5-yl)imidazo[1,2-b]pyridazin-8-yl)cyclopropyl)-8-(2,2,2-trifluoroethoxy)quinoline was prepared as a racemic mixture in the manner described for Intermediate 18, but replacing 6-chloro-8-cyclopropyl-2-methyl-imidazo[1,2-b]pyridazine with 6-((1S,2S)-2-(6-chloroimidazo[1,2-b]pyridazin-8-yl)cyclopropyl)-8-(2,2,2-trifluoroethoxy)quinoline. ES/MS m/z: 523.20 [M+H].

Intermediate 988. 6'-bromo-1'-(2,2-difluoropropyl)spiro[cyclopropane-1,3'-indolin]-2'-one

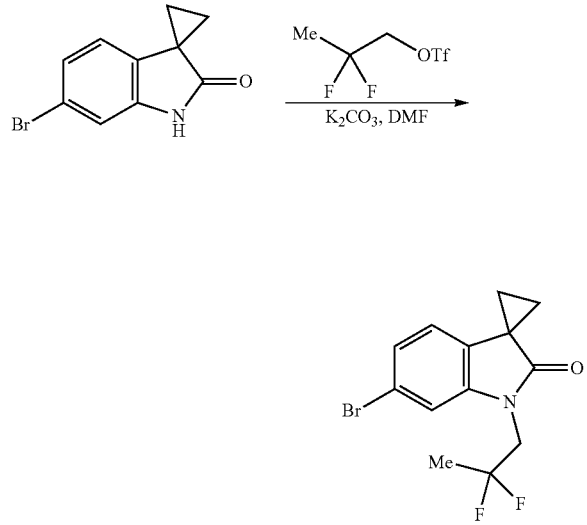

To a solution of 6'-bromospiro[cyclopropane-1,3'-indolin]-2'-one (200 mg, 0.84 mmol, 1 equiv) in DMF (3 mL) was added potassium carbonate (348 mg, 2.52 mmol, 3 equiv) and 2,2-difluoropropyl trifluoromethanesulfonate (287 mg, 1.26 mmol, 1.5 equiv). The reaction mixture was heated to 80° C. After 2 hours, the reaction mixture was directly purified by SiO$_2$ chromatography (0-100% EtOAc/Hex), affording 6'-bromo-1'-(2,2-difluoropropyl)spiro[cyclopropane-1,3'-indolin]-2'-one. $^1$H NMR (400 MHz, DMSO-d6) δ 7.40 (d, J=1.7 Hz, 1H), 7.21 (dd, J=8.0, 1.7 Hz, 1H), 7.01 (d, J=8.0 Hz, 1H), 4.27 (t, J=14.8 Hz, 2H), 1.78-1.51 (m, 7H).

Intermediate 989. 6'-((1S,2S)-2-(6-chloroimidazo[1,2-b]pyridazin-8-yl)cyclopropyl)-1'-(2,2-difluoropropyl)spiro[cyclopropane-1,3'-indolin]-2'-one (Racemic Mixture)

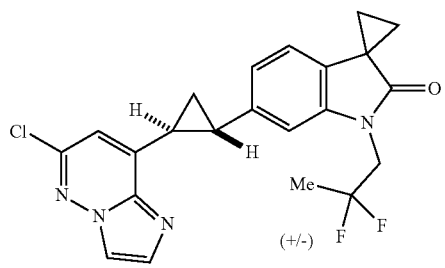 [SMILES: CC(F)(F)CN1C(=O)C2(CC2)c2ccc([C@H]3C[C@@H]3c3cc(Cl)nn4ccnc34)cc21]

6'-((1S,2S)-2-(6-chloroimidazo[1,2-b]pyridazin-8-yl)cyclopropyl)-1'-(2,2-difluoropropyl)spiro[cyclopropane-1,3'-indolin]-2'-one was prepared as a racemic mixture in the manner described for Intermediate 846, but replacing 6-bromo-2-(difluoromethyl)benzo[d]thiazole with 6'-bromo-1'-(2,2-difluoropropyl)spiro[cyclopropane-1,3'-indolin]-2'-one. ES/MS m/z: 429.10 [M+H].

Intermediate 990. 1'-(2,2-difluoropropyl)-6'-((1S,2S)-2-(6-(2,4-dimethoxypyrimidin-5-yl)imidazo[1,2-b]pyridazin-8-yl)cyclopropyl)spiro[cyclopropane-1,3'-indolin]-2'-one (Racemic Mixture)

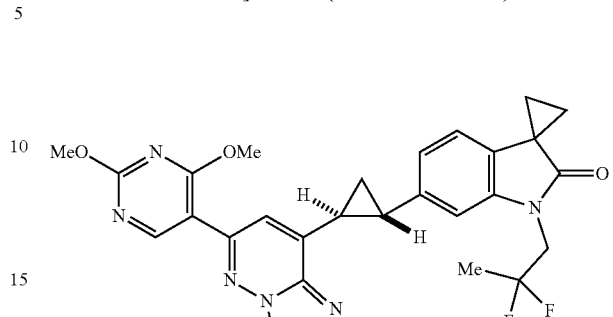

1'-(2,2-difluoropropyl)-6'-((1S,2S)-2-(6-(2,4-dimethoxypyrimidin-5-yl)imidazo[1,2-b]pyridazin-8-yl)cyclopropyl)spiro[cyclopropane-1,3'-indolin]-2'-one was prepared as a racemic mixture in the manner described for Intermediate 18, but replacing 6-chloro-8-cyclopropyl-2-methyl-imidazo[1,2-b]pyridazine with 6'-((2S,2S)-2-(6-chloroimidazo[1,2-b]pyridazin-8-yl)cyclopropyl)-1'-(2,2-difluoropropyl)spiro[cyclopropane-1,3'-indolin]-2'-one (racemic mixture). ES/MS m/z: 533.20 [M+H].

Intermediate 991. 6'-bromo-1'-((1-fluorocyclopropyl)methyl)spiro[cyclopropane-1,3'-indolin]-2'-one

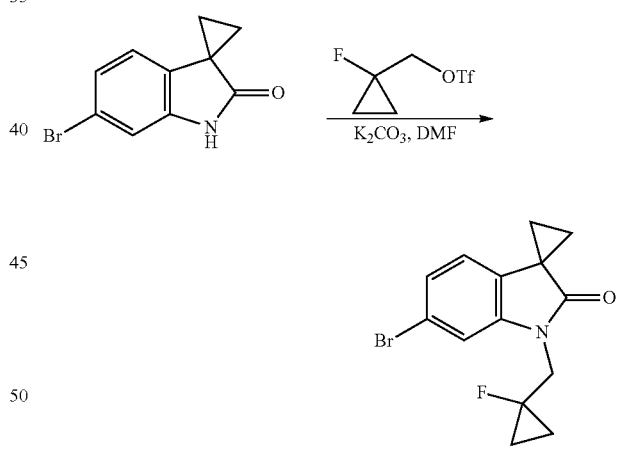

To a solution of 6'-bromospiro[cyclopropane-1,3'-indolin]-2'-one (190 mg, 0.80 mmol, 1 equiv) in DMF (3 mL) was added potassium carbonate (331 mg, 2.39 mmol, 3 equiv) and 1-(bromomethyl)-1-fluorocyclopropane (122 mg, 0.80 mmol, 1 equiv). The reaction mixture was heated to 80° C. After 20 hours, the reaction mixture was directly purified by SiO$_2$ chromatography (0-100% EtOAc/Hex), affording 6'-bromo-1'-((1-fluorocyclopropyl)methyl)spiro[cyclopropane-1,3'-indolin]-2'-one. $^1$H NMR (400 MHz, DMSO-d6) δ 7.40 (t, J=1.5 Hz, 1H), 7.19 (dd, J=7.9, 1.8 Hz, 1H), 7.00 (d, J=7.9 Hz, 1H), 4.19 (d, J=21.8 Hz, 2H), 1.71-1.65 (m, 2H), 1.60-1.54 (m, 2H), 1.10-0.98 (m, 2H), 0.93-0.84 (m, 2H). 19F NMR (376 MHz, DMSO-d6) δ −181.67-182.22 (m).

Intermediate 992. 6'-((1S,2S)-2-(6-chloroimidazo[1,2-b]pyridazin-8-yl)cyclopropyl)-1'-((1-fluorocyclopropyl)methyl)spiro[cyclopropane-1,3'-indolin]-2'-one (Racemic Mixture)

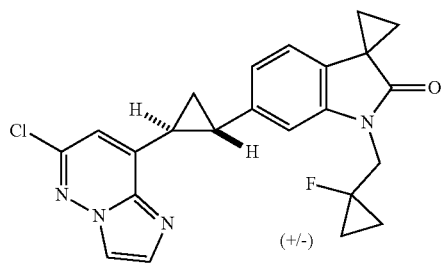 [SMILES: O=C1N(CC2(F)CC2)c2cc([C@H]3C[C@@H]3c3cc(Cl)nn4ccnc34)ccc2C12CC2]

6'-((1S,2S)-2-(6-chloroimidazo[1,2-b]pyridazin-8-yl)cyclopropyl)-1'-((1-fluorocyclopropyl)methyl)spiro[cyclopropane-1,3'-indolin]-2'-one was prepared as a racemic mixture in the manner described for Intermediate 846, but replacing 6-bromo-2-(difluoromethyl)benzo[d]thiazole with 6'-bromo-1'-((1-fluorocyclopropyl)methyl)spiro[cyclopropane-1,3'-indolin]-2'-one. ES/MS m/z: 423.10 [M+H].

Intermediate 993. 6'-((1S,2S)-2-(6-(2,4-dimethoxypyrimidin-5-yl)imidazo[1,2-b]pyridazin-8-yl)cyclopropyl)-1'-((1-fluorocyclopropyl)methyl)spiro[cyclopropane-1,3'-indolin]-2'-one (Racemic Mixture)

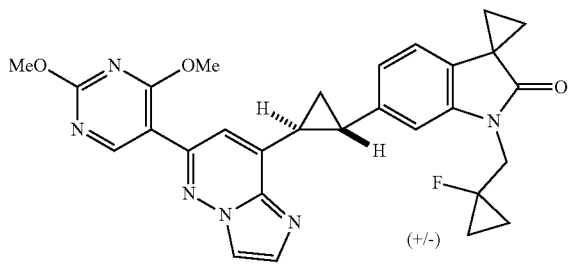 [SMILES: COc1ncc(-c2cc([C@H]3C[C@@H]3c3ccc4c(c3)N(CC3(F)CC3)C(=O)C43CC3)c3nccn3n2)c(OC)n1]

6'-((1S,2S)-2-(6-(2,4-dimethoxypyrimidin-5-yl)imidazo[1,2-b]pyridazin-8-yl)cyclopropyl)-1'-((1-fluorocyclopropyl)methyl)spiro[cyclopropane-1,3'-indolin]-2'-one was prepared as a racemic mixture in the manner described for Intermediate 18, but replacing 6-chloro-8-cyclopropyl-2-methyl-imidazo[1,2-b]pyridazine with 6'-((1S,2S)-2-(6-chloroimidazo[1,2-b]pyridazin-8-yl)cyclopropyl)-1'-((1-fluorocyclopropyl)methyl)spiro[cyclopropane-1,3'-indolin]-2'-one (Racemic Mixture). ES/MS m/z: 527.30 [M+H].

Intermediate 994. 6'-bromo-1'-(2,2,3,3-tetrafluoropropyl)spiro[cyclopropane-1,3'-indolin]-2'-one

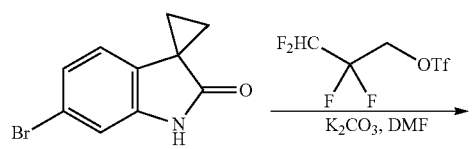

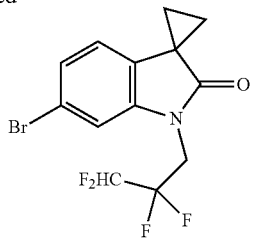

To a solution of 6'-bromospiro[cyclopropane-1,3'-indolin]-2'-one (190 mg, 0.80 mmol, 1 equiv) in DMF (3 mL) was added potassium carbonate (331 mg, 2.39 mmol, 3 equiv) and 2,2,3,3-tetrafluoropropyl trifluoromethanesulfonate (211 mg, 0.80 mmol, 1 equiv). The reaction mixture was heated to 80° C. After 1 hour, the reaction mixture was directly purified by SiO₂ chromatography (0-100% EtOAc/Hex), affording 6'-bromo-1'-(2,2,3,3-tetrafluoropropyl)spiro[cyclopropane-1,3'-indolin]-2'-one. ES/MS m/z: 352.00 [M+H].

Intermediate 995. 6'-((2S,2S)-2-(6-chloroimidazo[1,2-b]pyridazin-8-yl)cyclopropyl)-1'-(2,2,3,3-tetrafluoropropyl)spiro[cyclopropane-1,3'-indolin]-2'-one (Racemic Mixture)

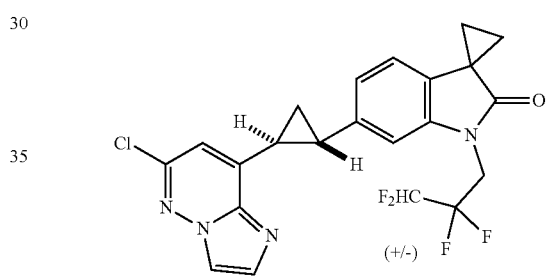

6'-((1S,2S)-2-(6-chloroimidazo[1,2-b]pyridazin-8-yl)cyclopropyl)-F-(2,2,3,3-tetrafluoropropyl)spiro[cyclopropane-1,3'-indolin]-2'-one was prepared as a racemic mixture in the manner described for Intermediate 846, but replacing 6-bromo-2-(difluoromethyl)benzo[d]thiazole with 6'-bromo-1'-(2,2,3,3-tetrafluoropropyl)spiro[cyclopropane-1,3'-indolin]-2'-one. ES/MS m/z: 465.20 [M+H].

Intermediate 996. 6'-((1S,2S)-2-(6-(2,4-dimethoxypyrimidin-5-yl)imidazo[1,2-b]pyridazin-8-yl)cyclopropyl)-1'-(2,2,3,3-tetrafluoropropyl)spiro[cyclopropane-1,3'-indolin]-2'-one (Racemic Mixture)

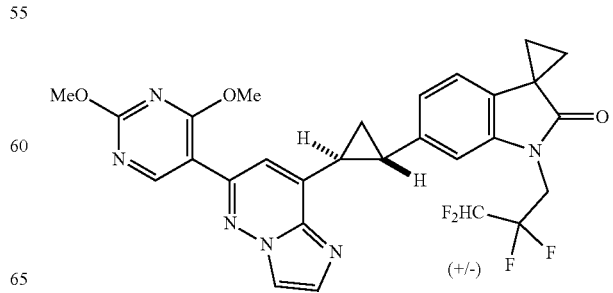

6'-((1S,2S)-2-(6-(2,4-dimethoxypyrimidin-5-yl)imidazo[1,2-b]pyridazin-8-yl)cyclopropyl)-1'-(2,2,3,3-tetrafluoropropyl)spiro[cyclopropane-1,3'-indolin]-2'-one was prepared as a racemic mixture in the manner described for Intermediate 18, but replacing 6-chloro-8-cyclopropyl-2-methyl-imidazo[1,2-b]pyridazine with 6'-((2S,2S)-2-(6-chloroimidazo[1,2-b]pyridazin-8-yl)cyclopropyl)-1'-(2,2,3,3-tetrafluoropropyl)spiro[cyclopropane-1,3'-indolin]-2'-one (Racemic Mixture). ES/MS m/z: 569.20 [M+H].

Intermediate 997. 6'-bromo-1'-(2,2,3,3,3-pentafluoropropyl)spiro[cyclopropane-1,3'-indolin]-2'-one

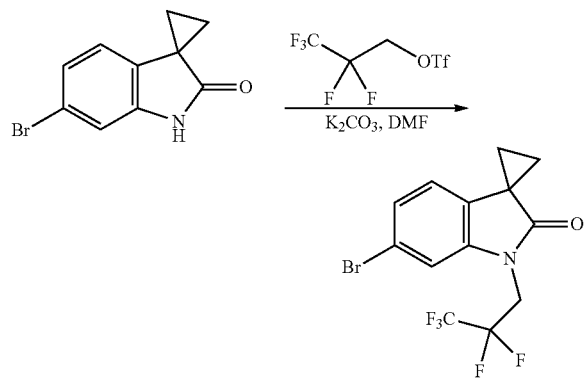

To a solution of 6'-bromospiro[cyclopropane-1,3'-indolin]-2'-one (150 mg, 0.63 mmol, 1 equiv) in DMF (3 mL) was added potassium carbonate (261 mg, 1.89 mmol, 3 equiv) and 2,2,3,3,3-pentafluoropropyl trifluoromethanesulfonate (178 mg, 0.63 mmol, 1 equiv). The reaction mixture was heated to 80° C. After 2 hours, the reaction mixture was directly purified by SiO₂ chromatography (0-100% EtOAc/Hex), affording 6'-bromo-1'-(2,2,3,3,3-pentafluoropropyl)spiro[cyclopropane-1,3'-indolin]-2'-one. ES/MS m/z: 370.00 [M+H].

Intermediate 998. 6'-((1S,2S)-2-(6-chloroimidazo[1,2-b]pyridazin-8-yl)cyclopropyl)-1'-(2,2,3,3,3-pentafluoropropyl)spiro[cyclopropane-1,3'-indolin]-2'-one (Racemic Mixture)

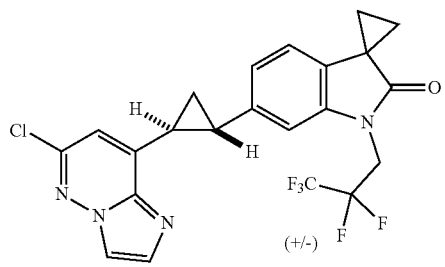 [SMILES: O=C1N(CC(F)(F)C(F)(F)F)c2cc([C@H]3C[C@@H]3c3cc(Cl)nn4ccnc34)ccc2C12CC2]

6'-((1S,2S)-2-(6-chloroimidazo[1,2-b]pyridazin-8-yl)cyclopropyl)-1'-(2,2,3,3,3-pentafluoropropyl)spiro[cyclopropane-1,3'-indolin]-2'-one was prepared as a racemic mixture in the manner described for Intermediate 846, but replacing 6-bromo-2-(difluoromethyl)benzo[d]thiazole with 6'-bromo-1'-(2,2,3,3,3-pentafluoropropyl)spiro[cyclopropane-1,3'-indolin]-2'-one. ES/MS m/z: 483.10 [M+H].

Intermediate 999. 6'-((2S,2S)-2-(6-(2,4-dimethoxypyrimidin-5-yl)imidazo[1,2-b]pyridazin-8-yl)cyclopropyl)-1'-(2,2,3,3,3-pentafluoropropyl)spiro[cyclopropane-1,3'-indolin]-2'-one (Racemic Mixture)

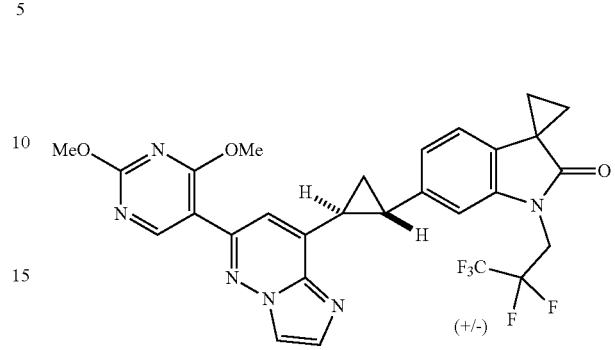

6'-((2S,2S)-2-(6-(2,4-dimethoxypyrimidin-5-yl)imidazo[1,2-b]pyridazin-8-yl)cyclopropyl)-1'-(2,2,3,3,3-pentafluoropropyl)spiro[cyclopropane-1,3'-indolin]-2'-one was prepared as a racemic mixture in the manner described for Intermediate 18, but replacing 6-chloro-8-cyclopropyl-2-methyl-imidazo[1,2-b]pyridazine with 6'-((1S,2S)-2-(6-chloroimidazo[1,2-b]pyridazin-8-yl)cyclopropyl)-1'-(2,2,3,3,3-pentafluoropropyl)spiro[cyclopropane-1,3'-indolin]-2'-one (Racemic Mixture). ES/MS m/z: 587.20 [M+H].

Intermediate 1000. 6'-bromo-1'-(2-cyclopropyl-2,2-difluoroethyl)spiro[cyclopropane-1,3'-indolin]-2'-one

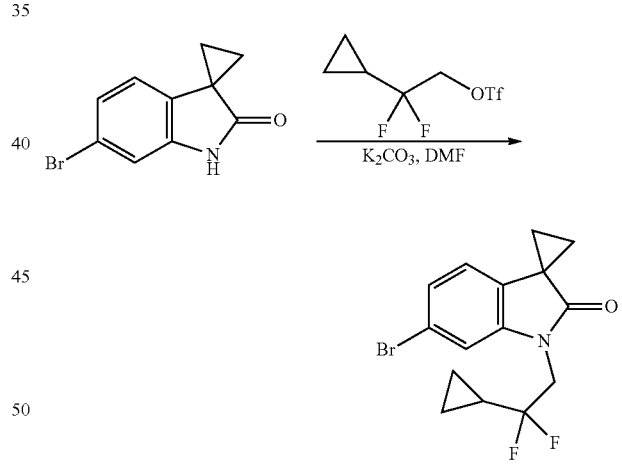

To a solution of 6'-bromospiro[cyclopropane-1,3'-indolin]-2'-one (100 mg, 0.42 mmol, 1 equiv) in DMF (3 mL) was added potassium carbonate (261 mg, 1.89 mmol, 3 equiv) and 2-cyclopropyl-2,2-difluoroethyl trifluoromethanesulfonate (107 mg, 0.42 mmol, 1 equiv). The reaction mixture was heated to 80° C. After 2 hours, the reaction mixture was directly purified by SiO₂ chromatography (0-100% EtOAc/Hex), affording 6'-bromo-1'-(2-cyclopropyl-2,2-difluoroethyl)spiro[cyclopropane-1,3'-indolin]-2'-one. ¹H NMR (400 MHz, DMSO-d6) δ 7.39 (s, 1H), 7.20 (dd, J=8.0, 1.7 Hz, 1H), 7.00 (d, J=8.0 Hz, 1H), 4.35 (t, J=14.5 Hz, 2H), 1.72 1.65 (m, 2H), 1.61-1.53 (m, 2H), 1.54-1.38 (m, 1H), 0.64-0.49 (m, 4H).

Intermediate 1001. 6'-((1S,2S)-2-(6-chloroimidazo[1,2-b]pyridazin-8-yl)cyclopropyl)-1'-(2-cyclopropyl-2,2-difluoroethyl)spiro[cyclopropane-1,3'-indolin]-2'-one (Racemic Mixture)

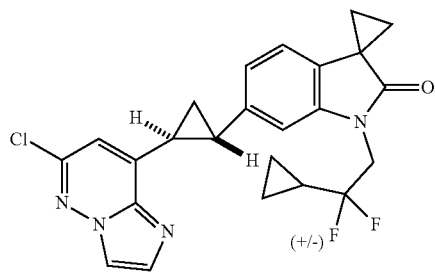 [SMILES: O=C1N(CC(F)(F)C2CC2)c2cc([C@H]3C[C@@H]3c3cc(Cl)nn4ccnc34)ccc2C12CC2]

6'-((1S,2S)-2-(6-chloroimidazo[1,2-b]pyridazin-8-yl)cyclopropyl)-1'-(2-cyclopropyl-2,2-difluoroethyl)spiro[cyclopropane-1,3'-indolin]-2'-one was prepared as a racemic mixture in the manner described for Intermediate 846, but replacing 6-bromo-2-(difluoromethyl)benzo[d]thiazole with 6'-bromo-1'-(2-cyclopropyl-2,2-difluoroethyl)spiro[cyclopropane-1,3'-indolin]-2'-one. ES/MS m/z: 455.20 [M+H].

Intermediate 1002. 1'-(2-cyclopropyl-2,2-difluoroethyl)-6'-((1S,2S)-2-(6-(2,4-dimethoxypyrimidin-5-yl)imidazo[1,2-b]pyridazin-8-yl)cyclopropyl)spiro[cyclopropane-1,3'-indolin]-2'-one (Racemic Mixture)

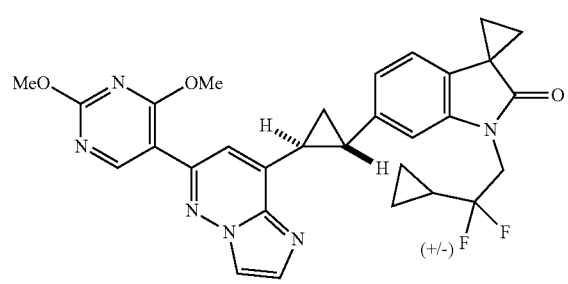 [SMILES: COc1ncc(-c2cc([C@H]3C[C@@H]3c3ccc4c(c3)N(CC(F)(F)C3CC3)C(=O)C43CC3)c3nccn3n2)c(OC)n1]

1'-(2-cyclopropyl-2,2-difluoroethyl)-6'-((1S,2S)-2-(6-(2,4-dimethoxypyrimidin-5-yl)imidazo[1,2-b]pyridazin-8-yl)cyclopropyl)spiro[cyclopropane-1,3'-indolin]-2'-one was prepared as a racemic mixture in the manner described for Intermediate 18, but replacing 6-chloro-8-cyclopropyl-2-methyl-imidazo[1,2-b]pyridazine with 1'-(2-cyclopropyl-2,2-difluoroethyl)-6'-((1S,2S)-2-(6-(2,4-dimethoxypyrimidin-5-yl)imidazo[1,2-b]pyridazin-8-yl)cyclopropyl)spiro[cyclopropane-1,3'-indolin]-2'-one (Racemic Mixture). ES/MS m/z: 559.20 [M+H].

Intermediate 1003. 1'-(2,2-difluoropropyl)-6'-((2S,2S)-2-(4,4,5,5-tetramethyl-1,3,2-dioxaborolan-2-yl)cyclopropyl)spiro[cyclopropane-1,3'-indolin]-2'-one

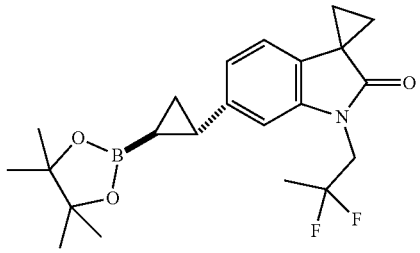

1'-(2,2-difluoropropyl)-6'-((1S,2S)-2-(4,4,5,5-tetramethyl-1,3,2-dioxaborolan-2-yl)cyclopropyl)spiro[cyclopropane-1,3'-indolin]-2'-one was prepared in the manner described for Intermediate 769 (steps 1-3), but replacing 4-bromo-2-fluorobenzonitrile with 6'-bromo-1'-(2,2-difluoropropyl)spiro[cyclopropane-1,3'-indolin]-2'-one. ES/MS m/z: 404.20 [M+H].

Intermediate 1004. 6'-((2S,2S)-2-(6-chloro-3-fluoroimidazo[1,2-b]pyridazin-8-yl)cyclopropyl)-1'-(2,2-difluoropropyl)spiro[cyclopropane-1,3'-indolin]-2'-one

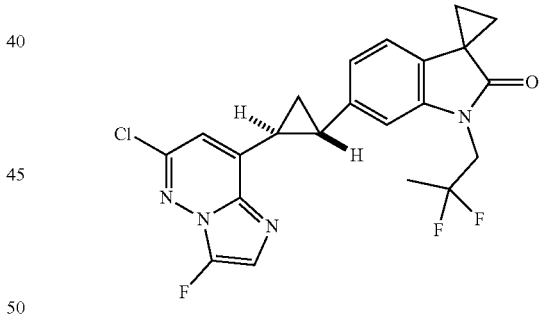

6'-((1S,2S)-2-(6-chloro-3-fluoroimidazo[1,2-b]pyridazin-8-yl)cyclopropyl)-1'-(2,2-difluoropropyl)spiro[cyclopropane-1,3'-indolin]-2'-one was prepared in the manner described for Intermediate 238, but replacing 4-((1S,2S)-2-(4,4,5,5-tetramethyl-1,3,2-dioxaborolan-2-yl)cyclopropyl)-2-(trifluoromethyl)benzonitrile with 1'-(2,2-difluoropropyl)-6'-((2S,2S)-2-(4,4,5,5-tetramethyl-1,3,2-dioxaborolan-2-yl)cyclopropyl)spiro[cyclopropane-1,3'-indolin]-2'-one, and 8-bromo-6-chloro-imidazo[1,2-b]pyridazine with 8-bromo-6-chloro-3-fluoro-imidazo[1,2-b]pyridazine. ES/MS m/z: 447.10 [M+H].

Intermediate 1005. 1'-(2,2-difluoropropyl)-6'-((2S,2S)-2-(6-(2,4-dimethoxypyrimidin-5-yl)-3-fluoro-imidazo[1,2-b]pyridazin-8-yl)cyclopropyl)spiro[cyclopropane-1,3'-indolin]-2'-one

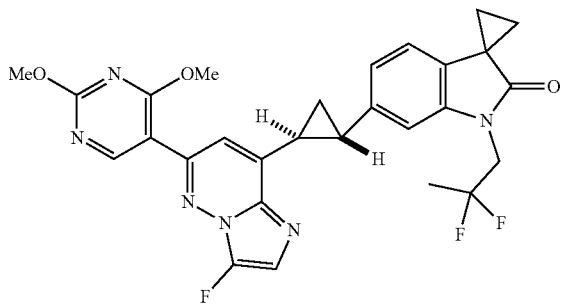 [SMILES: COc1ncc(-c2cc([C@H]3C[C@@H]3c3ccc4c(c3)N(CC(C)(F)F)C(=O)C43CC3)c3ncc(F)n3n2)c(OC)n1]

1'-(2,2-difluoropropyl)-6'-((2S,2S)-2-(6-(2,4-dimethoxypyrimidin-5-yl)-3-fluoroimidazo[1,2-b]pyridazin-8-yl)cyclopropyl)spiro[cyclopropane-1,3'-indolin]-2'-one was prepared in the manner described for Intermediate 18, but replacing 6-chloro-8-cyclopropyl-2-methyl-imidazo[1,2-b]pyridazine with 6'-((2S,2S)-2-(6-chloro-3-fluoroimidazo[1,2-b]pyridazin-8-yl)cyclopropyl)-1'-(2,2-difluoropropyl)spiro[cyclopropane-1,3'-indolin]-2'-one. ES/MS m/z: 551.20 [M+H].

Intermediate 1006. (S)-4-(1-(6-(2,4-dimethoxypyrimidin-5-yl)-3-fluoroimidazo[1,2-b]pyridazin-8-yl)-4,4-difluoropyrrolidin-3-yl)oxy)-2-(trifluoromethoxy)benzonitrile

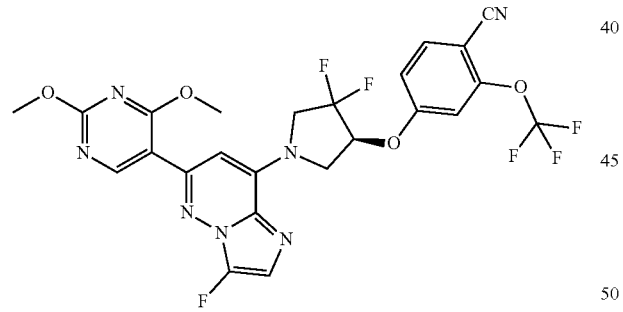

(3S)-1-[6-(2,4-dimethoxypyrimidin-5-yl)-3-fluoro-imidazo[1,2-b]pyridazin-8-yl]-4,4-difluoro-pyrrolidin-3-ol (58 mg, 0.15 mmol) was dissolved in NMP (2 mL), to the reaction mixture was added 4-fluoro-2-(trifluoromethoxy)benzonitrile (60 mg, 0.29 mmol) and cesium carbonate (143 mg, 0.44 mmol). The reaction mixture was heated at 85° C. overnight. The reaction mixture was then diluted with EtOAc, washed with brine, evaporated organic solvent and purified the residue with combi-flash column to afford (S)-4-((1-(6-(2,4-dimethoxypyrimidin-5-yl)-3-fluoroimidazo[1,2-b]pyridazin-8-yl)-4,4-difluoropyrrolidin-3-yl)oxy)-2-(trifluoromethoxy)benzonitrile. ES/MS m/z: 582.10.

Intermediate 1007. (S)-4-((1-(6-(2,4-dimethoxypyrimidin-5-yl)imidazo[1,2-b]pyridazin-8-yl)-4,4-difluoropyrrolidin-3-yl)oxy)-2-(trifluoromethoxy)benzonitrile

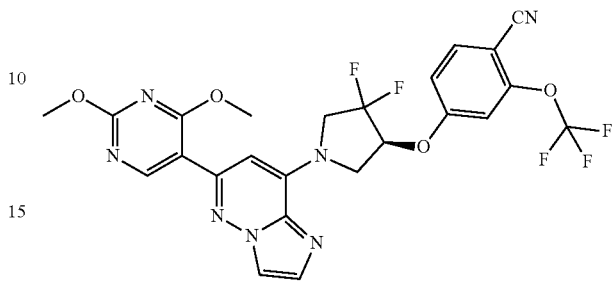

(3S)-1-[6-(2,4-dimethoxypyrimidin-5-yl)imidazo[1,2-b]pyridazin-8-yl]-4,4-difluoro-pyrrolidin-3-ol (55 mg, 0.145 mmol) was dissolved in NMP (2 mL), to the reaction mixture was added 4-fluoro-2-(trifluoromethoxy)benzonitrile (60 mg, 0.29 mmol) and cesium carbonate (142 mg, 0.44 mmol). The reaction mixture was heated at 85° C. overnight. The reaction mixture was then diluted with EtOAc, washed with brine, evaporated organic solvent and purified the residue with combi-flash column to afford (S)-4-((1-(6-(2,4-dimethoxypyrimidin-5-yl)imidazo[1,2-b]pyridazin-8-yl)-4,4-difluoropyrrolidin-3-yl)oxy)-2-(trifluoromethoxy)benzonitrile. ES/MS m/z: 564.10.

Intermediate 1008. (S)-8-(4-(4-(difluoromethyl)-5-fluoropyridin-2-yl)oxy)-3,3-difluoropyrrolidin-1-yl)-6-(2,4-dimethoxypyrimidin-5-yl)-3-fluoroimidazo[1,2-b]pyridazine

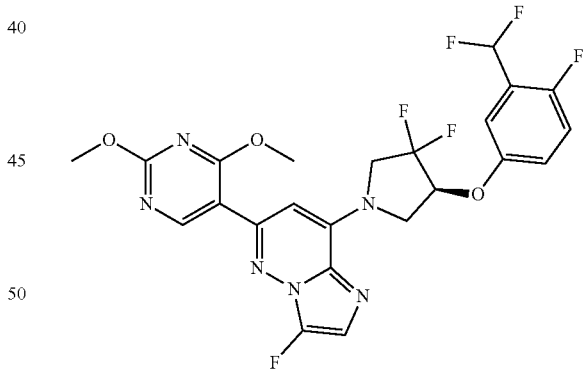

(3S)-1-[6-(2,4-dimethoxypyrimidin-5-yl)-3-fluoro-imidazo[1,2-b]pyridazin-8-yl]-4,4-difluoro-pyrrolidin-3-ol (103 mg, 0.26 mmol) was dissolved in DMF (4 mL), to the reaction mixture was added NaH (60% dispersion in mineral oil, 30 mg, 0.78 mmol) and stirred for 10 min at RT. Then 4-(difluoromethyl)-2,5-difluoro-pyridine (86 mg, 0.52 mmol) was added and the reaction mixture was heated at 85° C. for 30 mins. The reaction mixture was then diluted with EtOAc, washed with brine, evaporated organic solvent and purified the residue with combi-flash column to afford (S)-8-(4-((4-(difluoromethyl)-5-fluoropyridin-2-yl)oxy)-3,3-difluoropyrrolidin-1-yl)-6-(2,4-dimethoxypyrimidin-5-yl)-3-fluoroimidazo[1,2-b]pyridazine. ES/MS m/z: 542.10.

747

Intermediate 1009. (S)-8-(4-(3-(difluoromethyl)-4-fluorophenoxy)-3,3-difluoropyrrolidin-1-yl)-6-(2,4-dimethoxypyrimidin-5-yl)imidazo[1,2-b]pyridazine

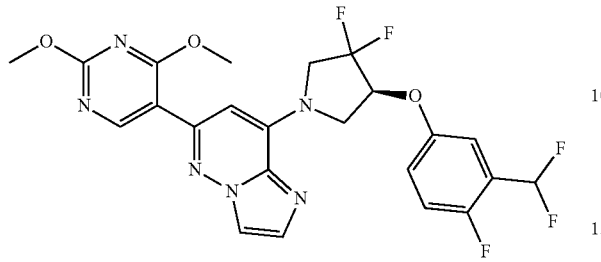

(3S)-1-[6-(2,4-dimethoxypyrimidin-5-yl)imidazo[1,2-b]pyridazin-8-yl]-4,4-difluoro-pyrrolidin-3-ol (107 mg, 0.28 mmol) was dissolved in toluene (2 mL), cesium carbonate (138 mg, 0.42 mmol), copper iodide (13.5 mg, 0.07 mmol) and 3,4,7,8-Tetramethyl-1,10-phenanthroline (13.4 mg, 0.057 mmol) were added to the reaction mixture and the reaction mixture was heated at 110° C. for 30 mins. The reaction mixture was then diluted with EtOAc, washed with brine, evaporated organic solvent and purified the residue with combi-flash column to afford (S)-8-(4-(3-(difluoromethyl)-4-fluorophenoxy)-3,3-difluoropyrrolidin-1-yl)-6-(2,4-dimethoxypyrimidin-5-yl)imidazo[1,2-b]pyridazine. ES/MS m/z: 523.20.

Intermediate 1010. 6'-bromo-1'-(3,3,3-trifluoropropyl)spiro[cyclopropane-1,3'-indolin]-2'-one

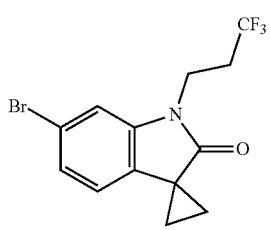 [SMILES: O=C1N(CCC(F)(F)F)c2cc(Br)ccc2C12CC2]

To a solution of 6'-bromospiro[cyclopropane-1,3'-indoline]-2'-one (600 mg, 2.52 mmol) in DMF was added NaH (97 mg, 2.52 mmol) and 3,3,3-trifluoropropyl trifluoromethanesulfonate (930 mg, 3.78 mmol). The reaction mixture was heated to 110° C. for 3 h. The reaction mixture was cooled to RT, diluted with brine (50 mL), and extracted with 80% EtOAc/Hex (2×100 mL). The combined organic layers were concentrated and purified by Combi-Flash column chromatography to afford 6'-bromo-1'-(3,3,3-trifluoropropyl)spiro[cyclopropane-1,3'-indolin]-2'-one. ES/MS m/z: 344.00.

748

Intermediate 1011. 6'-((2S,2S)-2-(6-chloroimidazo[1,2-b]pyridazin-8-yl)cyclopropyl)-1'-(3,3,3-trifluoropropyl)spiro[cyclopropane-1,3'-indolin]-2'-one

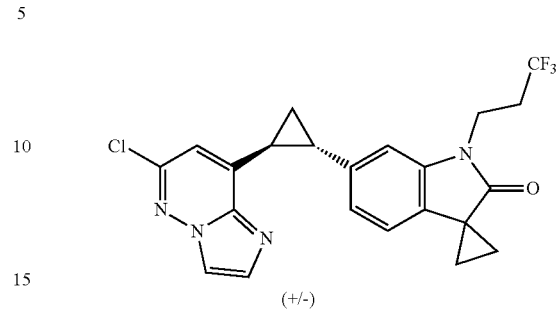

6'-((2S,2S)-2-(6-chloroimidazo[1,2-b]pyridazin-8-yl)cyclopropyl)-1'-(3,3,3-trifluoropropyl)spiro[cyclopropane-1,3'-indolin]-2'-one (racemate) was prepared as a racemic mixture in the manner described for Intermediate 498, but replacing 5-bromo-2-methylbenzo[d]thiazole with 6'-bromo-1'-(3,3,3-trifluoropropyl)spiro[cyclopropane-1,3'-indolin]-2'-one. ES/MS m/z: 447.10.

Intermediate 1012. 6'-((2S,2S)-2-(6-(2,4-dimethoxypyrimidin-5-yl)imidazo[1,2-b]pyridazin-8-yl)cyclopropyl)-1'-(3,3,3-trifluoropropyl)spiro[cyclopropane-1,3'-indolin]-2'-one

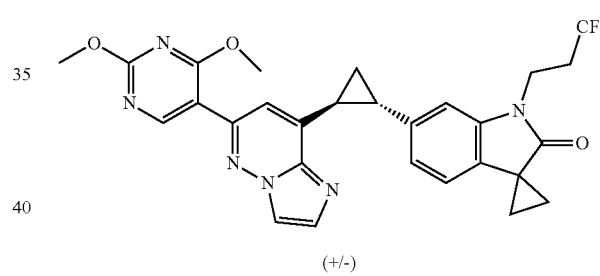

6'-((1S,2S)-2-(6-(2,4-dimethoxypyrimidin-5-yl)imidazo[1,2-b]pyridazin-8-yl)cyclopropyl)-1'-(3,3,3-trifluoropropyl)spiro[cyclopropane-1,3'-indolin]-2'-one (racemate) was prepared in the manner described for Intermediate 523, but replacing 6-chloro-8-(3,3,4,4-tetrafluoropyrrolidin-1-yl)imidazo[1,2-b]pyridazine with 6'-((1S,2S)-2-(6-chloroimidazo[1,2-b]pyridazin-8-yl)cyclopropyl)-1'-(3,3,3-trifluoropropyl)spiro[cyclopropane-1,3'-indolin]-2'-one (racemate). ES/MS m/z: 551.20.

Intermediate 1013. 6'-bromo-7'-fluorospiro[cyclopropane-1,3'-indolin]-2'-one

6-bromo-4-fluoro-indolin-2-one (1.5 g, 6.52 mmol) was dissolved in THF (5 mL), to the mixture was added LDA (1M in THF/hexane) at −78 degree followed by addition of 1,2-dibromoethane (0.72 g, 3.83 mmol). The reaction mixture was allowed to slowly warm up to RT and stirred at RT overnight. Then the reaction was diluted with EtOAc, washed with brine, evaporated organic solvent, the residue was purified with Combi-Flash column to afford 6'-bromo-7'-fluorospiro[cyclopropane-1,3'-indolin]-2'-one. ES/MS m/z: 256.00.

Intermediate 1014. 6'-bromo-7'-fluoro-1'-(2,2,2-trifluoroethyl)spiro[cyclopropane-1,3'-indolin]-2'-one

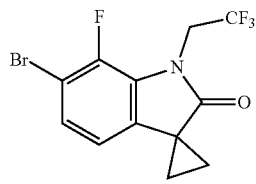 [SMILES: O=C1N(CC(F)(F)F)c2c(ccc(Br)c2F)C12CC2]

6'-bromo-7'-fluorospiro[cyclopropane-1,3'-indolin]-2'-one (130 mg, 051 mmol) was dissolved in DMF (3 mL). To the above solution were added 2,2,2-trifluoroethyl trifluoromethanesulfonate (177 mg, 0.76 mmol), potassium carbonate (140 mg, 1.02 mmol) and the reaction mixture was heated at 100° C. overnight. Then the reaction was diluted with EtOAc, washed with brine, evaporated organic solvent, the residue was purified with Combi-Flash column to afford 6'-bromo-7'-fluoro-1'-(2,2,2-trifluoroethyl)spiro[cyclopropane-1,3'-indolin]-2'-one. ES/MS m/z: 338.00.

Intermediate 1015. 6'-((1S,2S)-2-(6-chloroimidazo[1,2-b]pyridazin-8-yl)cyclopropyl)-7'-fluoro-1'-(2,2,2-trifluoroethyl)spiro[cyclopropane-1,3'-indolin]-2'-one

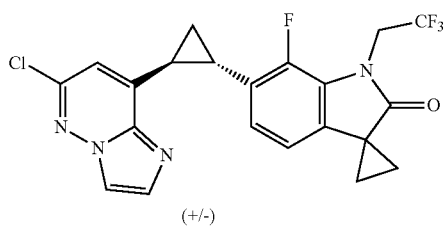 [SMILES: O=C1N(CC(F)(F)F)c2c(ccc([C@H]3C[C@@H]3c3cc(Cl)nn4ccnc34)c2F)C12CC2]

6'-((1S,2S)-2-(6-chloroimidazo[1,2-b]pyridazin-8-yl)cyclopropyl)-7'-fluoro-1'-(2,2,2-trifluoroethyl)spiro[cyclopropane-1,3'-indolin]-2'-one (racemate) was prepared as a racemic mixture in the manner described for Intermediate 498, but replacing 5-bromo-2-methylbenzo[d]thiazole with 6'-bromo-7'-fluoro-1'-(2,2,2-trifluoroethyl)spiro[cyclopropane-1,3'-indolin]-2'-one. ES/MS m/z: 451.10.

Intermediate 1016. 6'-((1S,2S)-2-(6-(2,4-dimethoxypyrimidin-5-yl)imidazo[1,2-b]pyridazin-8-yl)cyclopropyl)-7'-fluoro-1'-(2,2,2-trifluoroethyl)spiro[cyclopropane-1,3'-indolin]-2'-one

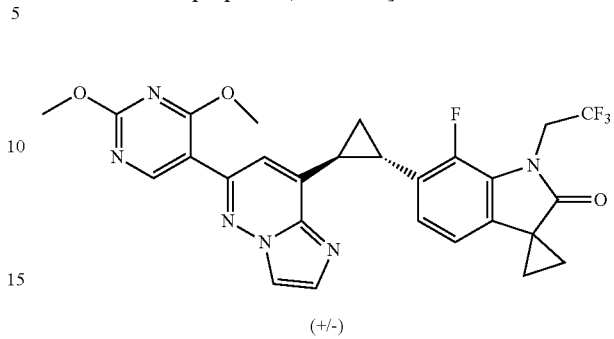

6'-((2S,2S)-2-(6-(2,4-dimethoxypyrimidin-5-yl)imidazo[1,2-b]pyridazin-8-yl)cyclopropyl)-7'-fluoro-1'-(2,2,2-trifluoroethyl)spiro[cyclopropane-1,3'-indolin]-2'-one (racemate) was prepared in the manner described for intermediate 523, but replacing 6-chloro-8-(3,3,4,4-tetrafluoropyrrolidin-1-yl)imidazo[1,2-b]pyridazine with 6'-((1S,2S)-2-(6-chloroimidazo[1,2-b]pyridazin-8-yl)cyclopropyl)-7'-fluoro-1'-(2,2,2-trifluoroethyl)spiro[cyclopropane-1,3'-indolin]-2'-one (racemate). ES/MS m/z: 555.20.

Intermediate 1017. 6'-bromo-5'-fluorospiro[cyclopropane-1,3'-indolin]-2'-one

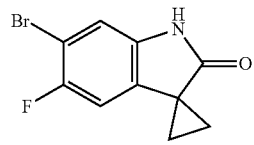

6'-bromo-5'-fluorospiro[cyclopropane-1,3'-indolin]-2'-one was prepared in the manner described for Intermediate 1013, but replacing 6-bromo-7-fluoroindolin-2-one with 6-bromo-5-fluoroindolin-2-one. ES/MS m/z: 256.00.

Intermediate 1018. 6'-bromo-5'-fluoro-1'-(2,2,2-trifluoroethyl)spiro[cyclopropane-1,3'-indolin]-2'-one

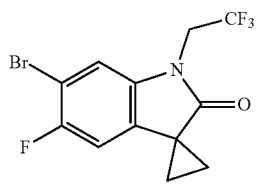 [SMILES: O=C1N(CC(F)(F)F)c2cc(Br)c(F)cc2C12CC2]

6'-bromo-5'-fluoro-1'-(2,2,2-trifluoroethyl)spiro[cyclopropane-1,3'-indolin]-2'-one was prepared in the manner described for Intermediate 1014, but replacing 6'-bromo-7'-fluorospiro[cyclopropane-1,3'-indolin]-2'-one with 6'-bromo-5'-fluorospiro[cyclopropane-1,3'-indolin]-2'-one. ES/MS m/z: 338.00.

Intermediate 1019. 6'-((1S,2S)-2-(6-chloroimidazo[1,2-b]pyridazin-8-yl)cyclopropyl)-5'-fluoro-1'-(2,2,2-trifluoroethyl)spiro[cyclopropane-1,3'-indolin]-2'-one

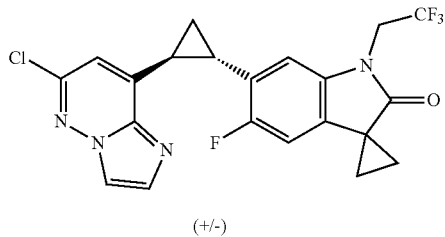 [SMILES: O=C1N(CC(F)(F)F)c2cc([C@H]3C[C@@H]3c3cc(Cl)nn4ccnc34)c(F)cc2C12CC2]

(+/-)

6'-((1S,2S)-2-(6-chloroimidazo[1,2-b]pyridazin-8-yl)cyclopropyl)-5'-fluoro-1'-(2,2,2-trifluoroethyl)spiro[cyclopropane-1,3'-indolin]-2'-one (racemate) was prepared as a racemic mixture in the manner described for Intermediate 498, but replacing 5-bromo-2-methylbenzo[d]thiazole with 6'-bromo-5'-fluoro-1'-(2,2,2-trifluoroethyl)spiro[cyclopropane-1,3'-indolin]-2'-one. ES/MS m/z: 451.10.

Intermediate 1020. 6'-((2S,2S)-2-(6-(2,4-dimethoxypyrimidin-5-yl)imidazo[1,2-b]pyridazin-8-yl)cyclopropyl)-5'-fluoro-1'-(2,2,2-trifluoroethyl)spiro[cyclopropane-1,3'-indolin]-2'-one

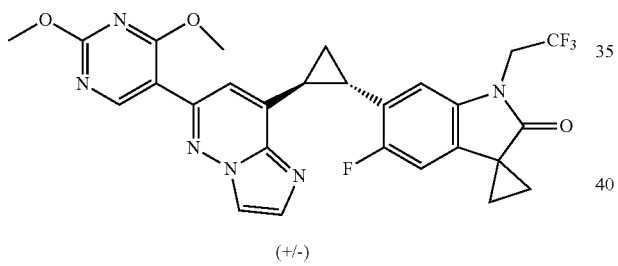

(+/-)

6'-((2S,2S)-2-(6-(2,4-dimethoxypyrimidin-5-yl)imidazo[1,2-b]pyridazin-8-yl)cyclopropyl)-5'-fluoro-1'-(2,2,2-trifluoroethyl)spiro[cyclopropane-1,3'-indolin]-2'-one (racemate) was prepared in the manner described for intermediate 523, but replacing 6-chloro-8-(3,3,4,4-tetrafluoropyrrolidin-1-yl)imidazo[1,2-b]pyridazine with 6'-((1S,2S)-2-(6-chloroimidazo[1,2-b]pyridazin-8-yl)cyclopropyl)-5'-fluoro-1'-(2,2,2-trifluoroethyl)spiro[cyclopropane-1,3'-indolin]-2'-one (racemate). ES/MS m/z: 555.20.

Intermediate 1021. 6'-bromo-4'-fluorospiro[cyclopropane-1,3'-indolin]-2'-one

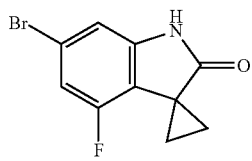 [SMILES: O=C1Nc2cc(Br)cc(F)c2C12CC2]

6'-bromo-4'-fluorospiro[cyclopropane-1,3'-indolin]-2'-one was prepared in the manner described for Intermediate 1013, but replacing 6-bromo-7-fluoroindolin-2-one with 6-bromo-4-fluoroindolin-2-one. ES/MS m/z: 256.00.

Intermediate 1022. 6'-bromo-4'-fluoro-1'-(2,2,2-trifluoroethyl)spiro[cyclopropane-1,3'-indolin]-2'-one

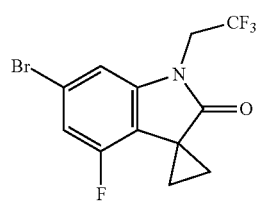 [SMILES: O=C1N(CC(F)(F)F)c2cc(Br)cc(F)c2C12CC2]

6'-bromo-4'-fluoro-1'-(2,2,2-trifluoroethyl)spiro[cyclopropane-1,3'-indolin]-2'-one was prepared in the manner described for Intermediate 1014, but replacing 6'-bromo-7'-fluorospiro[cyclopropane-1,3'-indolin]-2'-one with 6'-bromo-4'-fluorospiro[cyclopropane-1,3'-indolin]-2'-one. ES/MS m/z: 338.00.

Intermediate 1023. 6'-((1S,2S)-2-(6-chloroimidazo[1,2-b]pyridazin-8-yl)cyclopropyl)-4'-fluoro-1'-(2,2,2-trifluoroethyl)spiro[cyclopropane-1,3'-indolin]-2'-one

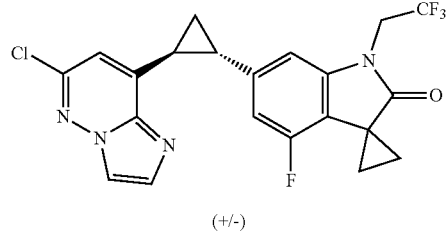 [SMILES: O=C1N(CC(F)(F)F)c2cc([C@H]3C[C@@H]3c3cc(Cl)nn4ccnc34)cc(F)c2C12CC2]

(+/-)

6'-((1S,2S)-2-(6-chloroimidazo[1,2-b]pyridazin-8-yl)cyclopropyl)-4'-fluoro-1'-(2,2,2-trifluoroethyl)spiro[cyclopropane-1,3'-indolin]-2'-one (racemate) was prepared as a racemic mixture in the manner described for Intermediate 498, but replacing 5-bromo-2-methylbenzo[d]thiazole with 6'-bromo-4'-fluoro-1'-(2,2,2-trifluoroethyl)spiro[cyclopropane-1,3'-indolin]-2'-one. ES/MS m/z: 451.10.

Intermediate 1024. 6'-((1S,2S)-2-(6-(2,4-dimethoxypyrimidin-5-yl)imidazo[1,2-b]pyridazin-8-yl)cyclopropyl)-4'-fluoro-1'-(2,2,2-trifluoroethyl)spiro[cyclopropane-1,3'-indolin]-2'-one

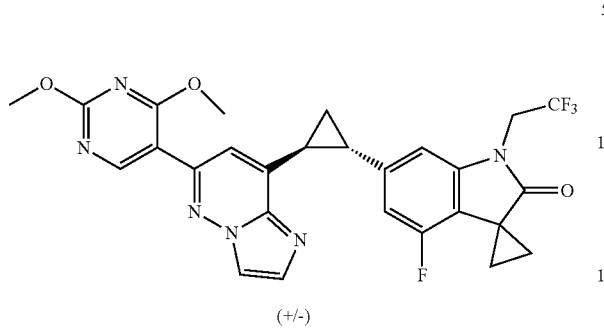

(+/-)

6'-((1S,2S)-2-(6-(2,4-dimethoxypyrimidin-5-yl)imidazo[1,2-b]pyridazin-8-yl)cyclopropyl)-4'-fluoro-1'-(2,2,2-trifluoroethyl)spiro[cyclopropane-1,3'-indolin]-2'-one (racemate) was prepared in the manner described for intermediate 523, but replacing 6-chloro-8-(3,3,4,4-tetrafluoropyrrolidin-1-yl)imidazo[1,2-b]pyridazine with 6'-((1S,2S)-2-(6-chloro-imidazo[1,2-b]pyridazin-8-yl)cyclopropyl)-4'-fluoro-1'-(2,2,2-trifluoroethyl)spiro[cyclopropane-1,3'-indolin]-2'-one (racemate). ES/MS m/z: 555.10.

B. EXAMPLES

The following examples describe preparation of compounds of the present invention.

Demethylation of 2,4-Dimethoxypyrimidines

Example 1. 5-(8-cyclopropyl-2-methyl-imidazo[1,2-b]pyridazin-6-yl)-1H-pyrimidine-2,4-dione

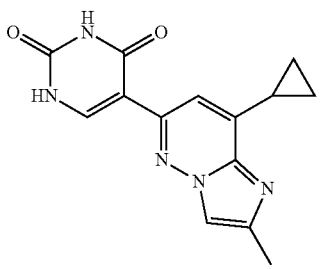 [SMILES: Cc1cn2nc(-c3c[nH]c(=O)[nH]c3=O)cc(C3CC3)c2n1]

5-(8-cyclopropyl-2-methyl-imidazo[1,2-b]pyridazin-6-yl)-1H-pyrimidine-2,4-dione was prepared as follows: To a solution of 8-cyclopropyl-6-(2,4-dimethoxypyrimidin-5-yl)-2-methyl-imidazo[1,2-b]pyridazine (54 mg, 0.17 mmol, 1 equiv) in MeOH (1.5 mL) was added 1.5 M $HCl_{(aq)}$ solution (1 mL). The reaction vessel was heated to 80° C. for 6 h. Solids separated were filtered, washed with water and dried affording 5-(8-cyclopropyl-2-methyl-imidazo[1,2-b]pyridazin-6-yl)-1H-pyrimidine-2,4-dione as an HCl salt. Some subsequent examples prepared in accordance with this method were purified by HPLC in place of the aforementioned solid separation according to standard methods. ES/MS: 284.10 [M+1]. $^1$H NMR (400 MHz, DMSO-d6) δ 11.71 (d, J=6.4 Hz, 1H), 11.62 (s, 1H), 8.34 (s, 1H), 8.08 (d, J=6.2 Hz, 1H), 7.65 (s, 1H), 2.53 (s, 3H), 1.34-1.30 (m, 2H), 1.15-1.06 (m, 2H).

Example 2. 5-(8-cyclopropyl-2-phenyl-imidazo[1,2-b]pyridazin-6-yl)-1H-pyrimidine-2,4-dione

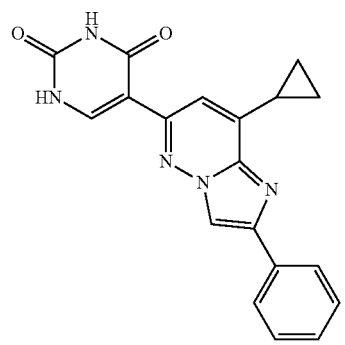 [SMILES: O=c1[nH]cc(-c2cc(C3CC3)c3nc(-c4ccccc4)cn3n2)c(=O)[nH]1]

5-(8-cyclopropyl-2-phenyl-imidazo[1,2-b]pyridazin-6-yl)-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 8-cyclopropyl-6-(2,4-dimethoxypyrimidin-5-yl)-2-phenyl-imidazo[1,2-b]pyridazine and isolated by filtration as an HCl salt. ES/MS m/z: 346.20 [M+H]. $^1$H NMR (400 MHz, DMSO-d6) δ 11.66-11.54 (m, 2H), 8.91 (s, 1H), 8.14-8.06 (m, 2H), 8.04 (d, J=6.2 Hz, 1H), 7.52 (dd, J=8.4, 6.9 Hz, 2H), 7.48 7.37 (m, 2H), 2.67 (td, J=8.4, 4.2 Hz, 1H), 1.35-1.20 (m, 4H).

Example 3. Ethyl 8-cyclopropyl-6-(2,4-dioxo-1H-pyrimidin-5-yl)imidazo[1,2-b]pyridazine-2-carboxylate

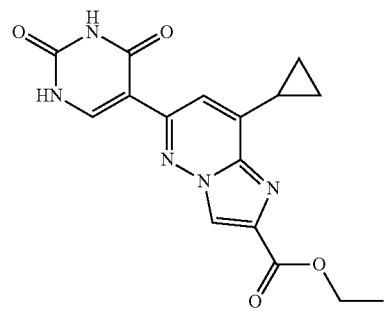

Ethyl 8-cyclopropyl-6-(2,4-dioxo-1H-pyrimidin-5-yl)imidazo[1,2-b]pyridazine-2-carboxylate was prepared in the manner described for Example 1, but replacing 8-cyclopropyl-6-(2,4-dimethoxypyrimidin-5-yl)-2-methyl-imidazo[1,2-b]pyridazine with ethyl 8-cyclopropyl-6-(2,4-dimethoxypyrimidin-5-yl)imidazo[1,2-b]pyridazine-2-carboxylate. The reaction mixture was purified by RP-HPLC (5-100% MeCN/$H_2O$ with TFA modifier, Gemini column) affording ethyl 8-cyclopropyl-6-(2,4-dioxo-1H-pyrimidin-5-yl)imidazo-[1,2-b]pyridazine-2-carboxylate as a TFA salt. ES/MS m/z: 342.10 [M+H]. $^1$H NMR (400 MHz, DMSO-d6) δ 11.56 (d, J=4.9 Hz, 2H), 8.74 (s, 1H), 8.00 (d, J=6.3 Hz, 1H), 7.38 (s, 1H), 4.34 (q, J=7.1 Hz, 2H), 1.34 (t, J=7.1 Hz, 3H), 1.22 (ddt, J=15.3, 5.1, 2.5 Hz, 4H).

Example 4. 5-(8-((2S,2S)-2-(methoxymethyl)cyclopropyl)imidazo[1,2-b]pyridazin-6-yl)pyrimidine-2,4 (1H,3H)-dione and 5-(8-((1R,2R)-2-(methoxymethyl)cyclopropyl)imidazo[1,2-b]pyridazin-6-yl) pyrimidine-2,4(1H,3H)-dione

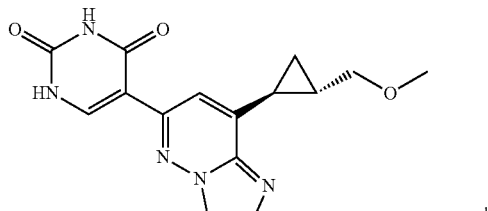

and

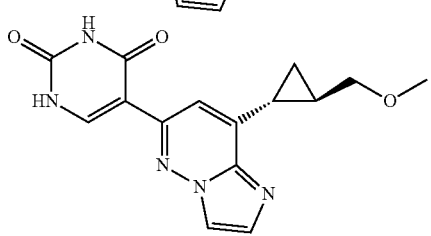

5-(8-((1S,2S)-2-(methoxymethyl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(methoxymethyl)cyclopropyl)imidazo[1,2-b]pyridazine (Racemic Mixture) and purified by RP-HPLC (5-100% MeCN/H₂O without TFA, Gemini column). ES/MS m/z: 314.10 [M+H]. ¹H NMR (400 MHz, Methanol-d4) δ 8.12 (s, 1H), 8.08 (d, J=1.3 Hz, 1H), 7.69 (d, J=1.3 Hz, 1H), 7.40 (s, 1H), 3.60-3.53 (m, 1H), 3.50-3.43 (m, 1H), 3.38 (s, 3H), 2.53-2.46 (m, 1H), 1.90-1.81 (m, 1H), 1.42-1.34 (m, 1H), 1.30-1.22 (m, 1H).

Example 5. (S)-5-(8-(spiro[2.3]hexan-1-yl)imidazo[1,2-b]pyridazin-6-yl)pyrimidine-2,4(1H,3H)-dione and (R)-5-(8-(spiro[2.3]hexan-1-yl)imidazo[1,2-b]pyridazin-6-yl)pyrimidine-2,4(1H,3H)-dione

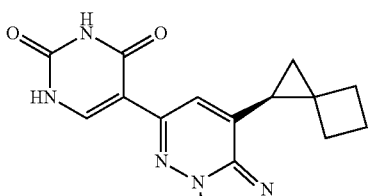

and

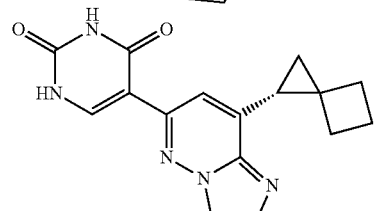

5-(8-(spiro[2.3]hexan-1-yl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(spiro[2.3]hexan-1-yl)imidazo[1,2-b] pyridazine. Purification was accomplished via RP-HPLC (5-90% MeCN/H₂O with TFA modifier, Gemini column). ES/MS m/z: 310.20 [M+H]. ¹H NMR (400 MHz, Methanol-d4) δ 8.38 (d, J=2.0 Hz, 1H), 8.28 (s, 1H), 8.13 (d, J=2.0 Hz, 1H), 7.65 (s, 1H), 2.56-2.44 (m, 1H), 2.42 (dd, J=8.6, 5.7 Hz, 1H), 2.38 2.26 (m, 1H), 2.27-2.10 (m, 2H), 2.08-1.92 (m, 2H), 1.60 (dd, J=8.6, 5.7 Hz, 1H), 1.42 (t, J=5.7 Hz, 1H).

Example 6. 5-(8-((2S,2S)-2-(tert-butyl)cyclopropyl)imidazo[1,2-b]pyridazin-6-yl)pyrimidine-2,4-(1H,3H)-dione and 5-(8-((1R,2R)-2-(tert-butyl)cyclopropyl)imidazo[1,2-b]pyridazin-6-yl)pyrimidine-2,4-(1H,3H)-dione

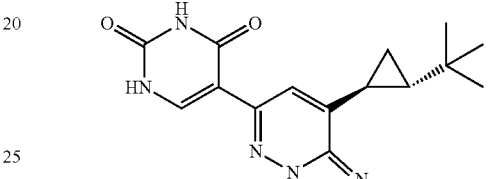

and

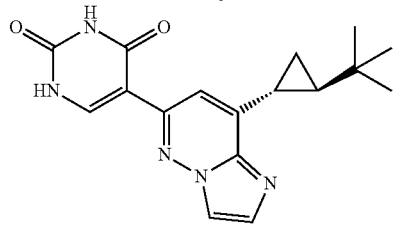

5-(8-((1S,2S)-2-(tert-butyl)cyclopropyl)imidazo[1,2-b]pyridazin-6-yl)pyrimidine-2,4-(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((1S,2S)-2-(tert-butyl)cyclopropyl)-6-(2,4-dimethoxypyrimidin-5-yl) imidazo[1,2-b]pyridazine (Racemic Mixture). Purification was accomplished via RP-HPLC (5-90% MeCN/H₂O with TFA modifier, Gemini column). ES/MS m/z: 326.20 [M+H]. ¹H NMR (400 MHz, Methanol-d4) δ 8.34-8.30 (m, 1H), 8.24 (s, 1H), 8.06-8.02 (m, 1H), 7.78 (s, 1H), 2.44 2.36 (m, 1H), 1.60-1.51 (m, 1H), 1.47-1.39 (m, 1H), 1.31-1.22 (m, 1H), 1.01 (s, 9H).

Example 7. 5-(8-((2S,2S)-2-phenylcyclopropyl)imidazo[1,2-b]pyridazin-6-yl)pyrimidine-2,4-(1H,3H)-dione and 5-(8-((1R,2R)-2-phenylcyclopropyl)imidazo[1,2-b]pyridazin-6-yl)pyrimidine-2,4-(1H,3H)-dione

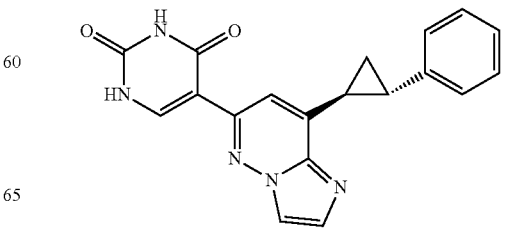

and

-continued

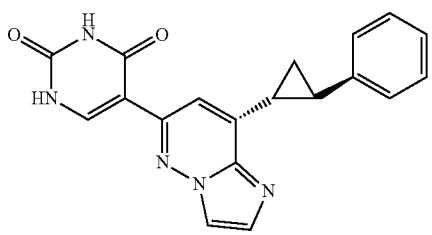

5-(8-((1S,2S)-2-phenylcyclopropyl)imidazo[1,2-b]pyridazin-6-yl)pyrimidine-2,4-(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-phenylcyclopropyl)imidazo[1,2-b]pyridazine (Racemic Mixture). Purification was accomplished via RP-HPLC (10-90% MeCN/H$_2$O with TFA modifier, Gemini column). ES/MS m/z: 346.10 [M+H]. $^1$H NMR (400 MHz, Methanol-d4) δ 8.38 (d, J=1.9 Hz, 1H), 8.30 (s, 1H), 8.07 (d, J=1.9 Hz, 1H), 8.01 (s, 1H), 7.38-7.22 (m, 5H), 2.74 (t, J=7.5 Hz, 2H), 1.93 (tt, J=7.5, 3.7 Hz, 2H).

Example 8. 5-(8-((1R,2S)-[1,1'-bi(cyclopropan)]-2-yl)imidazo[1,2-b]pyridazin-6-yl)pyrimidine-2,4(1H,3H)-dione and 5-(8-((1S,2R)-[1,1'-bi(cyclopropan)]-2-yl)imidazo[1,2-b]pyridazin-6-yl)pyrimidine-2,4(1H,3H)-dione

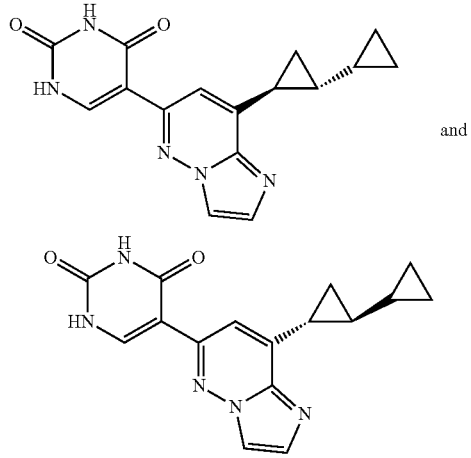

5-(8-((1R,2S)-[1,1'-bi(cyclopropan)]-2-yl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((1R,2S)-[1,1'-bi(cyclopropan)]-2-yl)-6-(2,4-dimethoxypyrimidin-5-yl)imidazo[1,2-b]pyridazine (Racemic Mixture) and purified by RP-HPLC (5-100% MeCN/H$_2$O without TFA, Gemini column). ES/MS m/z: 310.10 [M+H]; $^1$H NMR (400 MHz, Methanol-d4) δ 8.14 (s, 1H), 8.06 (d, J=1.3 Hz, 1H), 7.68 (d, J=1.3 Hz, 1H), 7.32 (s, 1H), 2.43-2.34 (m, 1H), 1.63-1.52 (m, 1H), 1.28-1.21 (m, 1H), 1.15-1.10 (m, 1H), 1.12-0.99 (m, 1H), 0.55-0.43 (m, 2H), 0.32-0.21 (m, 2H).

Example 9. 5-(8-pyrrolidin-1-ylimidazo[1,2-b]pyridazin-6-yl)-1H-pyrimidine-2,4-dione

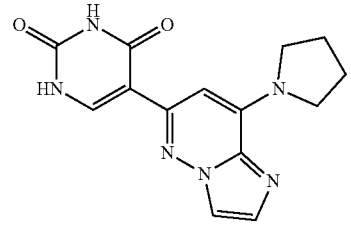 [SMILES: O=c1[nH]cc(-c2cc(N3CCCC3)c3nccn3n2)c(=O)[nH]1]

5-(8-pyrrolidin-1-ylimidazo[1,2-b]pyridazin-6-yl)-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-pyrrolidin-1-ylimidazo[1,2-b]pyridazine and purified by filtration. ES/MS m/z: 299.20 [M+H]. $^1$H NMR (400 MHz, DMSO-d6) δ 11.61 (dd, J=6.4, 2.0 Hz, 1H), 11.49 (d, J=2.0 Hz, 1H), 8.31 (d, J=1.7 Hz, 1H), 8.03 (d, J=6.2 Hz, 1H), 7.93 (s, 1H), 6.95 (s, 1H), 3.79 (brs, 4H), 2.08-1.95 (m, 4H).

Example 10. 5-(8-morpholinoimidazo[1,2-b]pyridazin-6-yl)-1H-pyrimidine-2,4-dione

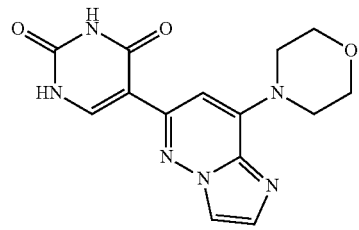 [SMILES: O=c1[nH]cc(-c2cc(N3CCOCC3)c3nccn3n2)c(=O)[nH]1]

5-(8-morpholinoimidazo[1,2-b]pyridazin-6-yl)-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 4-[6-(2,4-dimethoxypyrimidin-5-yl)imidazo[1,2-b]pyridazin-8-yl]morpholine and purified by filtration. ES/MS m/z: 315.20 [M+H]. $^1$H NMR (400 MHz, DMSO-d6) δ 11.60 (dd, J=6.2, 2.0 Hz, 1H), 11.52 (d, J=2.0 Hz, 1H), 8.26 (d, J=1.5 Hz, 1H), 8.02 (d, J=6.2 Hz, 1H), 7.83 (s, 1H), 7.18 (s, 1H), 3.85-3.73 (m, 8H).

Example 11. 5-(8-imidazol-1-ylimidazo[1,2-b]pyridazin-6-yl)-1H-pyrimidine-2,4-dione

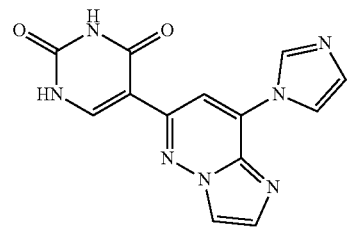 [SMILES: O=c1[nH]cc(-c2cc(-n3ccnc3)c3nccn3n2)c(=O)[nH]1]

5-(8-imidazol-1-ylimidazo[1,2-b]pyridazin-6-yl)-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-imidazol-1-yl-imidazo[1,2-b]pyridazine and purified by filtration. ES/MS m/z: 296.10 [M+H]. $^1$H NMR (400 MHz, DMSO-d6) δ 11.82 (dd, J=6.3, 2.0 Hz, 1H), 11.67 (d, J=1.9 Hz, 1H), 10.06 (t, J=1.4 Hz, 1H), 8.66 (t, J=1.8 Hz, 1H), 8.55 (d, J=1.3 Hz, 1H), 8.24 (s, 1H), 8.14 (d, J=6.2 Hz, 1H), 7.96 (d, J=1.3 Hz, 1H), 7.90 (dd, J=2.0, 1.2 Hz, 1H).

Example 12. 5-(8-(benzylamino)imidazo[1,2-b]pyridazin-6-yl)pyrimidine-2,4(1H,3H)-dione

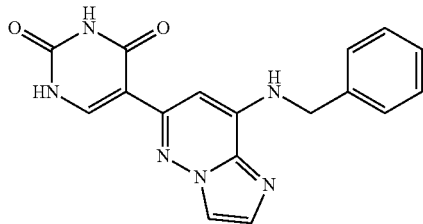

5-(8-(benzylamino)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with N-benzyl-6-(2,4-dimethoxypyrimidin-5-yl)imidazo[1,2-b]pyridazin-8-amine (41 mg, 0.113 mmol, 1 equiv) to provide the title compound. The resultant compound was purified by HPLC (10-90% MeCN/H$_2$O with 0.1% TFA). ES/MS m/z: 335.1 [M+1]. $^1$H NMR (400 MHz, DMSO-d6) δ11.52-11.40 (m, 2H), 8.18 (dd, J=8.0, 3.9 Hz, 2H), 7.97 (d, J=6.1 Hz, 1H), 7.79 (s, 1H), 7.44-7.38 (m, 2H), 7.38-7.31 (m, 2H), 7.31-7.23 (m, 1H), 6.99 (s, 1H), 4.56 (d, J=5.9 Hz, 2H).

Example 13. 5-(8-(benzyl(methyl)amino)imidazo[1,2-b]pyridazin-6-yl)pyrimidine-2,4(1H,3H)-dione

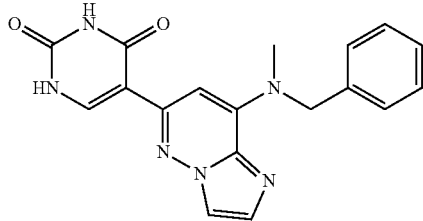 [SMILES: CN(Cc1ccccc1)c1cc(-c2c[nH]c(=O)[nH]c2=O)nn2ccnc12]

5-(8-(benzyl(methyl)amino)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with N-benzyl-6-(2,4-dimethoxypyrimidin-5-yl)-N-methylimidazo[1,2-b]pyridazin-8-amine (90 mg, 0.239 mmol, 1 equiv) to provide the title compound. The resultant compound was purified by HPLC (10-90% MeCN/H$_2$O with 0.1% TFA). ES/MS m/z: 349.1 [M+1]. $^1$H NMR (400 MHz, DMSO-d6) δ 11.38 (d, J=6.6 Hz, 2H), 8.05 (d, J=1.2 Hz, 1H), 7.96 (d, J=6.0 Hz, 1H), 7.56 (d, J=1.2 Hz, 1H), 7.35-7.27 (m, 2H), 7.27-7.20 (m, 3H), 6.80 (s, 1H), 5.55 (s, 2H), 3.14 (s, 3H).

Example 14. 5-(8-(4,4-difluorocyclohexyl)imidazo[1,2-b]pyridazin-6-yl)pyrimidine-2,4(1H,3H)-dione

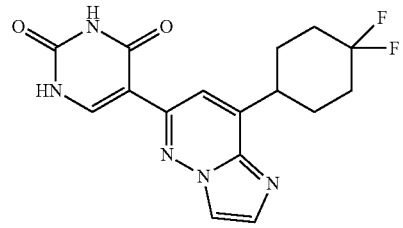 [SMILES: O=c1[nH]cc(-c2cc(C3CCC(F)(F)CC3)c3nccn3n2)c(=O)[nH]1]

5-(8-(4,4-difluorocyclohexyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(4,4-difluorocyclohexyl)-6-(2,4-dimethoxypyrimidin-5-yl)imidazo[1,2-b]-pyridazine (20 mg, 0.053 mmol, 1 equiv) to provide the title compound. The resultant compound was purified by HPLC (10-90% MeCN/H$_2$O with 0.1% TFA). ES/MS m/z: 348.1 [M+1]. $^1$H NMR (400 MHz, DMSO-d6) δ11.63 (dd, J=6.2, 2.0 Hz, 1H), 11.59 (d, J=2.0 Hz, 1H), 8.40 (d, J=1.6 Hz, 1H), 8.07 (d, J=6.2 Hz, 1H), 8.04-7.96 (m, 1H), 7.81 (s, 1H), 3.39-3.27 (m, 1H), 2.25-1.95 (m, 6H), 1.87 (dt, J=14.5, 11.1 Hz, 2H). $^{19}$F NMR (376 MHz, DMSO-d6) δ −75.13 (s, 3F), −89.97 (d, J=233.5 Hz, 1F), −99.92--101.11 (m, 1F).

Example 15. 5-(8-isopropyl-2-(trifluoromethyl)imidazo[1,2-b]pyridazin-6-yl)pyrimidine-2,4(1H,3H)-dione

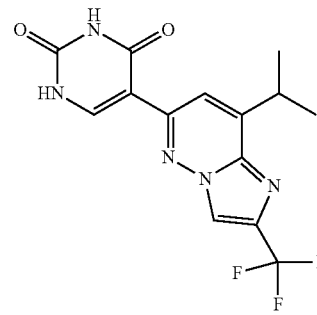

5-(8-isopropyl-2-(trifluoromethyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-isopropyl-2-(trifluoromethyl)imidazo[1,2-b]-pyridazine (53 mg, 0.145 mmol, 1 equiv) to provide the title compound. The resultant compound was purified by HPLC (10-90% MeCN/H$_2$O with 0.1% TFA). ES/MS m/z: 340.1 [M+1]. $^1$H NMR (400 MHz, DMSO-d6) δ 11.61 (d, J=1.9 Hz, 1H), 11.59 (s, 1H), 8.90 (d, J=1.0 Hz, 1H), 8.03 (d, J=6.0 Hz, 1H), 7.76 (s, 1H), 3.51 (p, J=6.9 Hz, 1H), 1.36 (d, J=6.9 Hz, 6H). $^{19}$F NMR (376 MHz, DMSO-d6) δ −61.57 (s, 3F).

Example 16. 5-(8-isopropyl-[1,2,4]triazolo[4,3-b]pyridazin-6-yl)pyrimidine-2,4(1H,3H)-dione

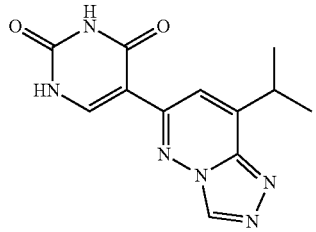 [SMILES: CC(C)c1cc(-c2c[nH]c(=O)[nH]c2=O)nn2cnnc12]

5-(8-isopropyl[1,2,4]triazolo[4,3-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-isopropyl[1,2,4]triazolo[4,3-b]pyridazine (60 mg, 0.198 mmol, 1 equiv) to provide the title compound. The resultant compound was purified by HPLC (10-90% MeCN/H$_2$O with 0.1% TFA). ES/MS m/z: 273.1 [M+1]. $^1$H NMR (400 MHz, DMSO-d6) δ 11.64-11.58 (m, 1H), 11.57 (d, J=2.0 Hz, 1H), 9.59 (s, 1H), 8.05 (d, J=6.2 Hz, 1H), 7.65 (d, J=0.9 Hz, 1H), 3.52-3.45 (m, 2H), 1.41 (d, J=6.9 Hz, 6H).

Example 17. 5-(8-benzylimidazo[1,2-b]pyridazin-6-yl)-1H-pyrimidine-2,4-dione

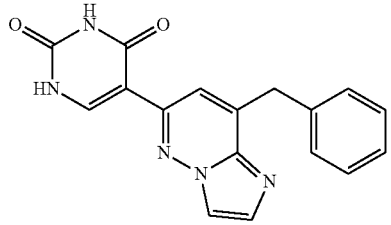 [SMILES: O=c1[nH]cc(-c2cc(Cc3ccccc3)c3nccn3n2)c(=O)[nH]1]

5-(8-benzylimidazo[1,2-b]pyridazin-6-yl)-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 8-benzyl-6-(2,4-dimethoxypyrimidin-5-yl)imidazo[1,2-b]pyridazine (16 mg, 0.046 mmol, 1 equiv) to provide the title compound. The resultant compound was purified by HPLC (10-90% MeCN/H$_2$O with 0.1% TFA). ES/MS m/z: 320.1 [M+1]. $^1$H NMR (400 MHz, DMSO-d6) δ 11.59-11.53 (m, 1H), 11.51 (d, J=2.0 Hz, 1H), 8.37 (d, J=1.4 Hz, 1H), 8.01 (d, J=6.2 Hz, 1H), 7.94 (d, J=10.9 Hz, 1H), 7.64 (s, 1H), 7.44-7.35 (m, 2H), 7.31 (dd, J=8.3, 6.6 Hz, 2H), 7.27-7.19 (m, 1H), 4.34 (s, 2H).

Example 18. 5-[8-[1-(trifluoromethyl)cyclopropyl]imidazo[1,2-b]pyridazin-6-yl]-1H-pyrimidine-2,4-dione

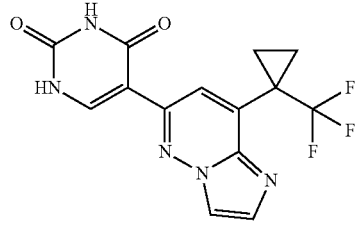 [SMILES: O=c1[nH]cc(-c2cc(C3(C(F)(F)F)CC3)c3nccn3n2)c(=O)[nH]1]

5-[8-[1-(trifluoromethyl)cyclopropyl]imidazo[1,2-b]pyridazin-6-yl]-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[1-(trifluoromethyl)cyclopropyl]imidazo[1,2-b]pyridazine (5 mg, 0.014 mmol, 1 equiv) to provide the title compound. The resultant compound was purified by HPLC (10-90% MeCN/H$_2$O with 0.1% TFA). ES/MS m/z: 338.1 [M+1]. $^1$H NMR (400 MHz, DMSO-d6) δ 11.60 (d, J=10.0 Hz, 2H), 8.35 (s, 1H), 8.07 (d, J=6.1 Hz, 1H), 7.95 (s, 1H), 7.84 (s, 1H), 1.60-1.52 (m, 2H), 1.49 (d, J=12.1 Hz, 2H).

Example 19. 5-[2,8-bis[1-(trifluoromethyl)cyclopropyl]imidazo[1,2-b]pyridazin-6-yl]-1H-pyrimidine-2,4-dione

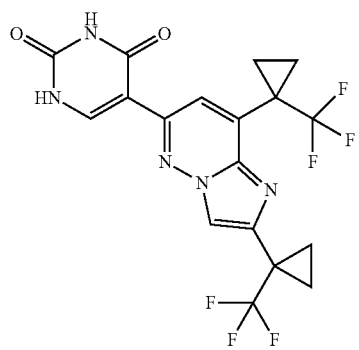 [SMILES: O=c1[nH]cc(-c2cc(C3(C(F)(F)F)CC3)c3nc(C4(C(F)(F)F)CC4)cn3n2)c(=O)[nH]1]

5-[2,8-bis[1-(trifluoromethyl)cyclopropyl]imidazo[1,2-b]pyridazin-6-yl]-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-2,8-bis[1-(trifluoromethyl)cyclopropyl]imidazo[1,2-b]pyridazine (12 mg, 0.025 mmol, 1 equiv) to provide the title compound. The resultant compound was purified by HPLC (10-90% MeCN/H$_2$O with 0.1% TFA). ES/MS m/z: 446.1 [M+1]. $^1$H NMR (400 MHz, DMSO-d6) δ 11.62 (d, J=2.0 Hz, 1H), 11.54 (dd, J=6.3, 2.0 Hz, 1H), 8.03 (s, 1H), 8.01 (d, J=6.3 Hz, 1H), 7.93 (s, 1H), 1.55 (td, J=7.5, 5.1 Hz, 4H), 1.48-1.36 (m, 4H).

Example 20. 5-[8-(benzenesulfonylmethyl)imidazo[1,2-b]pyridazin-6-yl]-1H-pyrimidine-2,4-dione

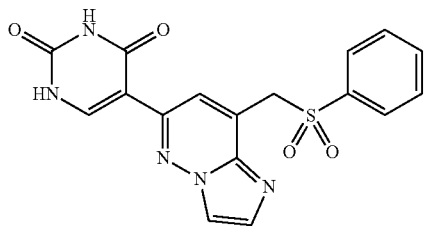 [SMILES: O=c1[nH]cc(-c2cc(CS(=O)(=O)c3ccccc3)c3nccn3n2)c(=O)[nH]1]

5-[8-(benzenesulfonylmethyl)imidazo[1,2-b]pyridazin-6-yl]-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 8-(benzenesulfonylmethyl)-6-(2,4-dimethoxypyrimidin-5-yl)imidazo[1,2-b]pyridazine (22 mg, 0.054 mmol, 1 equiv) to provide the title compound. The resultant compound was purified by HPLC (10-90% MeCN/H$_2$O with 0.1% TFA). ES/MS m/z: 384.0 [M+1]. $^1$H NMR (400 MHz, DMSO-d6) δ11.71-11.63 (m, 1H), 11.57 (d, J=2.0 Hz, 1H), 8.09 (d, J=9.7 Hz, 1H), 7.98 (d, J=6.2 Hz, 1H), 7.88 (d, J=9.6 Hz, 1H), 7.69 (s, 1H), 7.64-7.55 (m, 3H), 7.45 (t, J=7.6 Hz, 2H), 5.27 (s, 2H).

Example 21. 5-[2,8-bis(benzenesulfonylmethyl)imidazo[1,2-b]pyridazin-6-yl]-1H-pyrimidine-2,4-dione

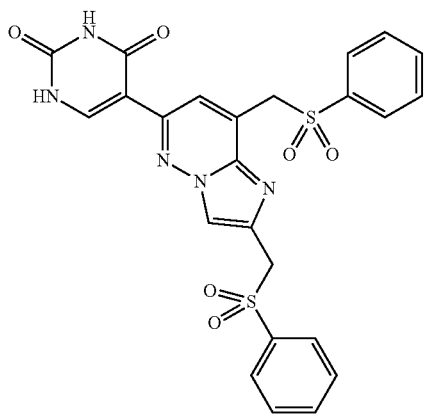 [SMILES: O=c1[nH]cc(-c2cc(CS(=O)(=O)c3ccccc3)c3nc(CS(=O)(=O)c4ccccc4)cn3n2)c(=O)[nH]1]

5-[2,8-bis(benzenesulfonylmethyl)imidazo[1,2-b]pyridazin-6-yl]-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 2,8-bis(benzenesulfonylmethyl)-6-(2,4-dimethoxypyrimidin-5-yl)imidazo[1,2-b]-pyridazine (4 mg, 0.0071 mmol, 1 equiv) to provide the title compound. The resultant compound was purified by HPLC (10-90% MeCN/H$_2$O with 0.1% TFA). ES/MS m/z: 538.1 [M+1]. $^1$H NMR (400 MHz, DMSO-d6) δ 11.67 (d, J=6.0 Hz, 1H), 11.55 (s, 1H), 7.96 (d, J=6.3 Hz, 1H), 7.84 (s, 1H), 7.79-7.74 (m, 2H), 7.73-7.66 (m, 1H), 7.62-7.51 (m, 5H), 7.49-7.41 (m, 3H), 5.21 (s, 2H), 5.08 (s, 2H).

Example 22. 5-(8-cyclopropylimidazo[1,2-b]pyridazin-6-yl)pyrimidine-2,4(1H,3H)-dione

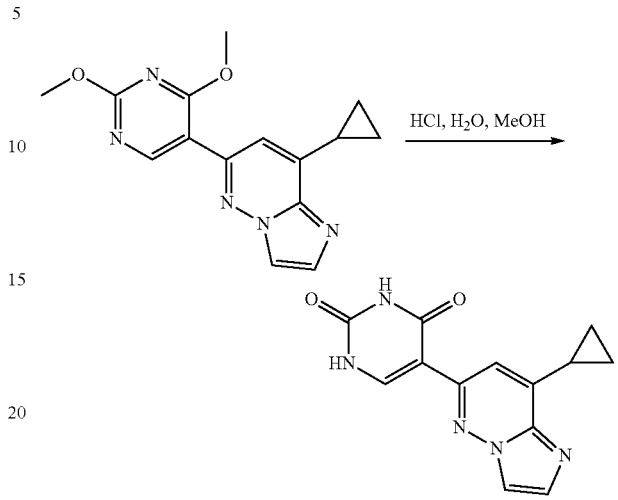

To a solution of 8-cyclopropyl-6-(2,4-dimethoxypyrimidin-5-yl)imidazo[1,2-b]pyridazine (22 mg, 0.07 mmol, 1 equiv) in MeOH (1 mL) was added 1M HCl aqueous solution (1 mL). The vessel was sealed and heated to 70° C. for 16 h. Purification was accomplished by reverse phase HPLC (10-90% MeCN/H$_2$O with 0.1% TFA) affording 5-(8-cyclopropylimidazo[1,2-b]pyridazin-6-yl) pyrimidine-2,4(1H,3H)-dione as a TFA salt. ES/MS: 270.10 [M+1]. $^1$H NMR (400 MHz, DMSO-d6) δ 11.68-11.28 (m, 2H), 8.33 (s, 1H), 8.01 (d, J=6.2 Hz, 1H), 7.89 (s, 1H), 7.45 (s, 1H), 2.47-2.42 (m, 1H), 1.27-1.15 (m, 4H).

Example 23. 5-(imidazo[1,2-b]pyridazin-6-yl)pyrimidine-2,4(1H,3H)-dione

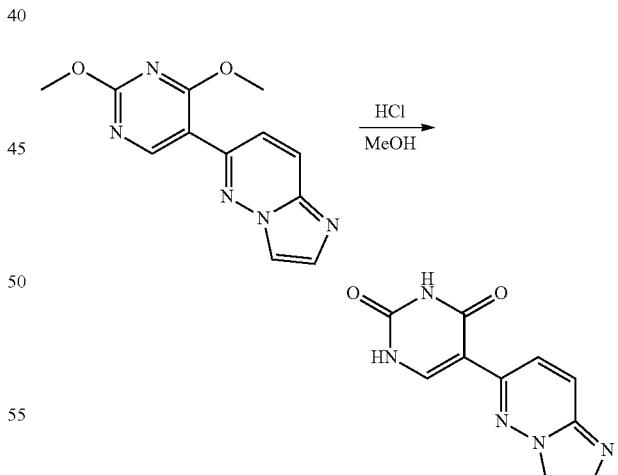

6-(2,4-dimethoxypyrimidin-5-yl)imidazo[1,2-b]pyridazine (66 mg, 0.26 mmol was dissolved in MeOH (1 ML). To the reaction mixture was added 1N aqueous HCl (1 mL). The reaction mixture was then heated at 50° C. for 2 h. The reaction mixture was then neutralized with NaHCO$_3$ and evaporated. The residue was washed with MeOH and water to afford 5-(imidazo[1,2-b]pyridazin-6-yl)pyrimidine-2,4(1H,3H)-dione. ES/MS m/z: 230.10 [M+H]. $^1$H NMR (400 MHz, DMSO-d6) δ 9.65 (s, 1H), 8.41 (s, 1H), 8.13 (d, J=9.7 Hz, 1H), 8.09 (s, 1H), 7.85 (d, J=9.7 Hz, 1H), 7.58 (d, J=1.1 Hz, 1H).

Example 24. 5-(8-cyclopropoxyimidazo[1,2-b]pyridazin-6-yl)pyrimidine-2,4(1H,3H)-dione

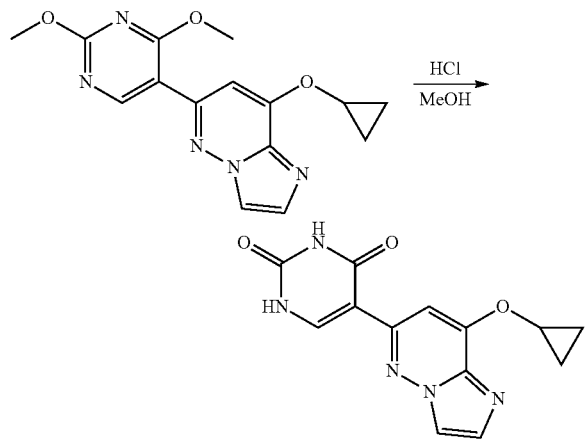

8-cyclopropoxy-6-(2,4-dimethoxypyrimidin-5-yl)imidazo[1,2-b]pyridazine (87 mg, 0.278 mmol was dissolved in MeOH (2 mL). To the reaction mixture was added aqueous 1N HCl (1 mL). The reaction mixture was then heated at 50° C. for 2 h. The reaction mixture was then neutralized with NaHCO₃ and evaporated. The residue was washed with MeOH and water to afford 5-(8-cyclopropoxyimidazo[1,2-b]pyridazin-6-yl)pyrimidine-2,4(1H,3H)-dione. ES/MS m/z: 286.10 [M+H]. ¹H NMR (400 MHz, DMSO-d6) δ 9.57 (s, 1H), 8.43 (s, 1H), 8.09-7.99 (m, 2H), 7.44 (d, J=1.1 Hz, 1H), 4.08 (tt, J=6.2, 3.0 Hz, 1H), 0.94-0.78 (m, 4H).

Example 25. 5-(8-isopropoxyimidazo[1,2-b]pyridazin-6-yl)pyrimidine-2,4(1H,3H)-dione

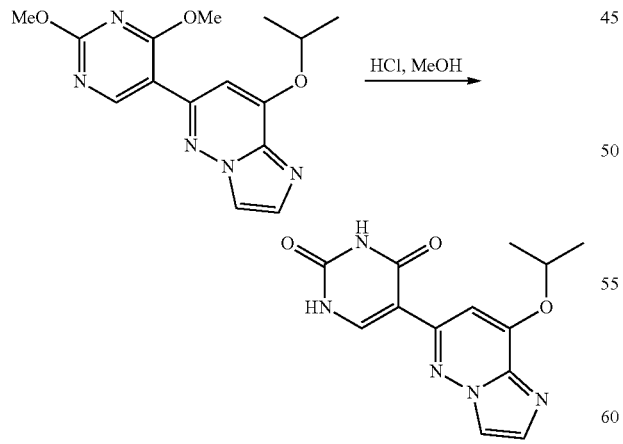

A solution of 6-(2,4-dimethoxypyrimidin-5-yl)-8-isopropoxyimidazo[1,2-b]pyridazine (70 mg, 0.22 mmol, 1 equiv) in 1:1 1N HCl/MeOH (2.5 mL) was heated at 70° C. After 6 hours, the reaction mixture was purified by RP-HPLC (5-80% MeCN/H₂O with TFA modifier, Gemini column), affording 5-(8-isopropoxyimidazo[1,2-b]pyridazin-6-yl)pyrimidine-2,4(1H,3H)-dione. ES/MS m/z: 288.10 [M+H]; ¹H NMR (400 MHz, Methanol-d4) δ 8.34 (d, J=2.0 Hz, 1H), 8.33 (s, 1H), 8.02 (d, J=2.0 Hz, 1H), 7.95 (s, 1H), 5.19-5.08 (m, 1H), 1.58 (d, J=6.1 Hz, 6H).

Example 26. 5-(8-benzylimidazo[1,2-b]pyridazin-6-yl)-1H-pyrimidine-2,4-dione

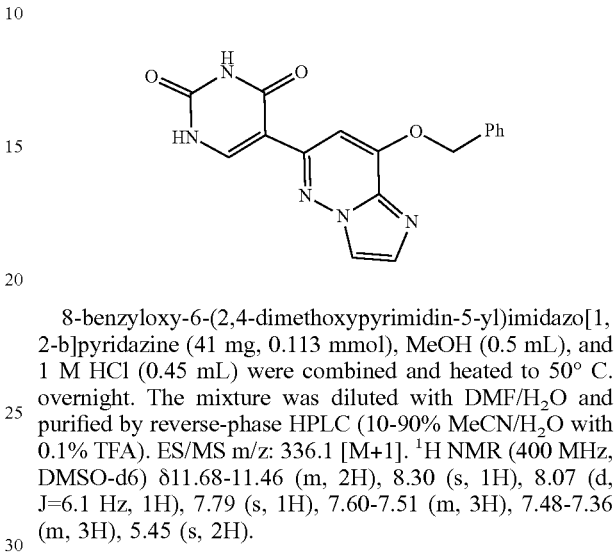

8-benzyloxy-6-(2,4-dimethoxypyrimidin-5-yl)imidazo[1,2-b]pyridazine (41 mg, 0.113 mmol), MeOH (0.5 mL), and 1 M HCl (0.45 mL) were combined and heated to 50° C. overnight. The mixture was diluted with DMF/H₂O and purified by reverse-phase HPLC (10-90% MeCN/H₂O with 0.1% TFA). ES/MS m/z: 336.1 [M+1]. ¹H NMR (400 MHz, DMSO-d6) δ11.68-11.46 (m, 2H), 8.30 (s, 1H), 8.07 (d, J=6.1 Hz, 1H), 7.79 (s, 1H), 7.60-7.51 (m, 3H), 7.48-7.36 (m, 3H), 5.45 (s, 2H).

Example 27. 5-(7-cyclopropylpyrazolo[1,5-a]pyrimidin-5-yl)pyrimidine-2,4(1H,3H)-dione

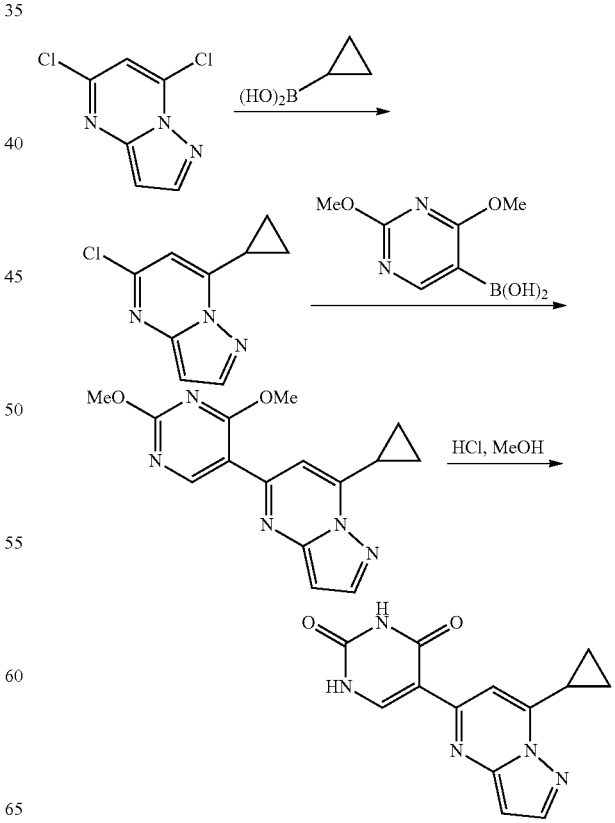

a) A microwave vial was charged with 5,7-dichloropyrazolo[1,5-a]pyrimidine (100 mg, 0.53 mmol, 1 equiv), cyclopropylboronic acid (69 mg, 0.80 mmol, 1.5 equiv), cesium carbonate (347 mg, 1.1 mmol, 2 equiv), and Pd(dppf)Cl₂—CH₂Cl₂ (39 mg, 10 mol %). The reaction mixture was dissolved in 2:1 dioxane/H₂O (2 mL), purged with argon, and microwaved at 120° C. After 1 hour, the reaction mixture was directly purified by SiO₂ chromatography (0-30% MeOH/CH₂Cl₂), affording 5-chloro-7-cyclopropylpyrazolo[1,5-a]pyrimidine. ES/MS m/z: 194.10 [M+H]; $^1$H NMR (400 MHz, DMSO-d6) δ 8.29 (d, J=2.3 Hz, 1H), 6.81 (s, 1H), 6.70 (d, J=2.3 Hz, 1H), 2.86-2.77 (m, 1H), 1.35-1.22 (m, 4H).

b) A microwave vial was charged with 5-chloro-7-cyclopropylpyrazolo[1,5-a]pyrimidine (27 mg, 0.14 mmol, 1 equiv), (2,4-dimethoxypyrimidin-5-yl)boronic acid (39 mg, 0.21 mmol, 1.5 equiv), cesium carbonate (91 mg, 0.28 mmol, 2 equiv), and Pd(dppf)Cl₂—CH₂Cl₂ (10 mg, 10 mol %). The reaction mixture was dissolved in 2:1 dioxane/H₂O (2 mL), purged with argon, and heated at 80° C. After 30 minutes, the reaction mixture was directly purified by SiO₂ chromatography (0-30% MeOH/CH₂Cl₂), affording 7-cyclopropyl-5-(2,4-dimethoxypyrimidin-5-yl)pyrazolo[1,5-a]pyrimidine. ES/MS m/z: 298.20 [M+H]; $^1$H NMR (400 MHz, DMSO-d6) δ8.83 (s, 1H), 8.26 (d, J=2.3 Hz, 1H), 7.07 (s, 1H), 6.75 (d, J=2.3 Hz, 1H), 4.04 (s, 3H), 3.98 (s, 3H), 2.89-2.78 (m, 1H), 1.36-1.12 (m, 4H).

c) A solution of 7-cyclopropyl-5-(2,4-dimethoxypyrimidin-5-yl)pyrazolo[1,5-a]pyrimidine (38 mg, 0.13 mmol, 1 equiv) in 1:1 1N HCl/MeOH (1.5 mL) was heated at 50° C. After 14 hours, the reaction mixture was purified by RP-HPLC (10-90% MeCN/H₂O with TFA modifier, Gemini column), affording 5-(7-cyclopropylpyrazolo[1,5-a]pyrimidin-5-yl)pyrimidine-2,4(1H,3H)-dione. ES/MS m/z: 270.10 [M+H]; $^1$H NMR (400 MHz, DMSO-d6) δ11.63-11.57 (m, 1H), 11.50 (s, 1H), 8.32 (d, J=6.3 Hz, 1H), 8.21 (d, J=2.3 Hz, 1H), 7.51 (s, 1H), 6.62 (d, J=2.3 Hz, 1H), 2.85-2.74 (m, 1H), 1.34-1.27 (m, 2H), 1.10-1.03 (m, 2H).

Example 41. 5-[8-[(1S,2S)-2-[3-(trifluoromethyl)phenyl]cyclopropyl]imidazo[1,2-b]pyridazin-6-yl]-1H-pyrimidine-2,4-dione and 5-[8-[(1R,2R)-2-[3-(trifluoromethyl)phenyl]cyclopropyl]imidazo[1,2-b]pyridazin-6-yl]-1H-pyrimidine-2,4-dione

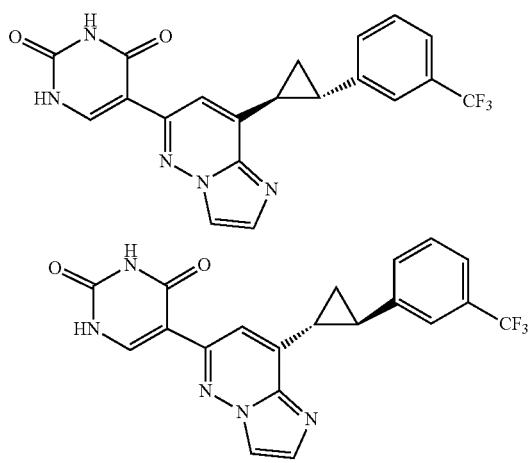

and

5-[8-[(1S,2S)-2-[3-(trifluoromethyl)phenyl]cyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-[(1S,2S)-2-[4-(trifluoromethyl)phenyl]cyclopropyl]imidazo[1,2-b]pyridazine (Racemic Mixture) and purified by RP-HPLC (5-90% MeCN/H₂O with TFA, Gemini column). ES/MS m/z: 414.10 [M+H]. $^1$H NMR (400 MHz, Methanol-d4) δ 8.39-8.38 (m, 1H), 8.31-8.30 (m, 1H), 8.11-8.02 (m, 2H), 7.64-7.53 (m, 4H), 2.89-2.80 (m, 2H), 1.99-1.96 (m, 2H). $^{19}$F NMR (376 MHz, Methanol-d4) δ −64.67 (s, 3F), −77.72 (s, 3F).

Example 42. 5-[8-[(1S,2S)-2-[4-(trifluoromethyl)phenyl]cyclopropyl]imidazo[1,2-b]pyridazin-6-yl]-1H-pyrimidine-2,4-dione and 5-[8-[(1R,2R)-2-[4-(trifluoromethyl)phenyl]cyclopropyl]imidazo[1,2-b]pyridazin-6-yl]-1H-pyrimidine-2,4-dione

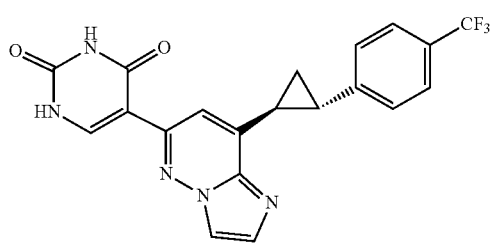

and

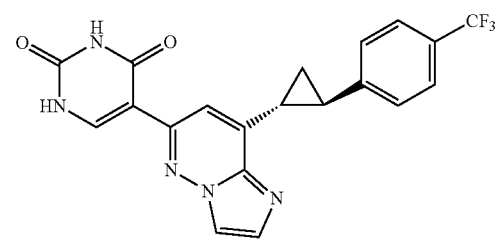

5-[8-[(1S,2S)-2-[4-(trifluoromethyl)phenyl]cyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-[(1S,2S)-2-[4-(trifluoromethyl)phenyl]cyclopropyl]imidazo[1,2-b]pyridazine (Racemic Mixture) and purified by RP-HPLC (5-90% MeCN/H₂O with TFA, Gemini column). ES/MS m/z: 414.10 [M+H]. $^1$H NMR (400 MHz, Methanol-d4) δ 8.40 (d, J=2.0 Hz, 1H), 8.31 (s, 1H), 8.12-8.04 (m, 2H), 7.69-7.62 (m, 2H), 7.49-7.47 (m, 2H), 2.85-2.81 (m, 2H), 2.03-1.96 (td, J=7.4, 2.1 Hz, 2H). $^{19}$F NMR (376 MHz, Methanol-d4) δ −64.47 (s, 3F), −77.75 (s, 3F).

Example 45. 5-(8-((2S,2S)-2-(4-cyclopropylphenyl)cyclopropyl)imidazo[1,2-b]pyridazin-6-yl)pyrimidine-2,4(1H,3H)-dione and 5-(8-((1R,2R)-2-(4-cyclopropylphenyl)cyclopropyl)imidazo[1,2-b]pyridazin-6-yl)pyrimidine-2,4(1H,3H)-dione

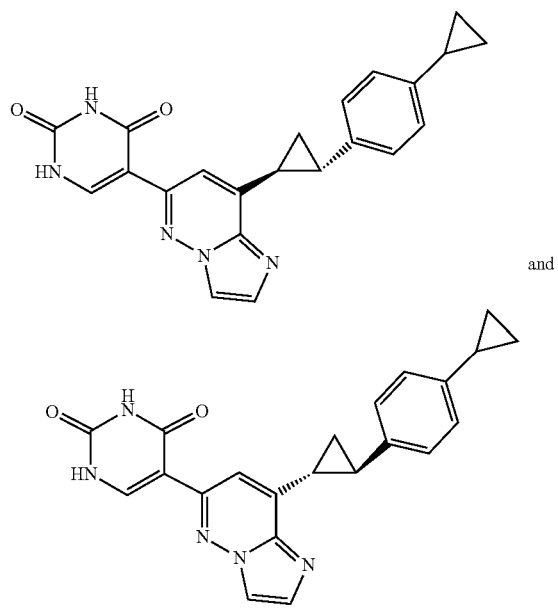

5-(8-((1S,2S)-2-(4-cyclopropylphenyl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((2S,2S)-2-(4-cyclopropylphenyl)cyclopropyl)-6-(2,4-dimethoxypyrimidin-5-yl)imidazo[1,2-b]pyridazine (Racemic Mixture). Purification was accomplished via RP-HPLC (10-90% MeCN/H$_2$O with TFA modifier, Gemini column). ES/MS m/z: 386.10 [M+H]. $^1$H NMR (400 MHz, Acetonitrile-d3) δ 7.06 (d, J=2.1 Hz, 1H), 6.96 (s, 1H), 6.77 (d, J=2.1 Hz, 1H), 6.72 (s, 1H), 5.87-5.76 (m, 2H), 5.75-5.64 (m, 2H), 1.40-1.18 (m, 2H), 0.67-0.43 (m, 3H), −0.34-0.52 (m, 2H), −0.60-0.81 (m, 2H).

Example 47. 5-(8-((2S,2S)-2-(3-(trifluoromethoxy)phenyl)cyclopropyl)imidazo[1,2-b]pyridazin-6-yl)pyrimidine-2,4(1H,3H)-dione and 5-(8-((1R,2R)-2-(3-(trifluoromethoxy)phenyl)cyclopropyl)imidazo[1,2-b]pyridazin-6-yl) pyrimidine-2,4(1H,3H)-dione

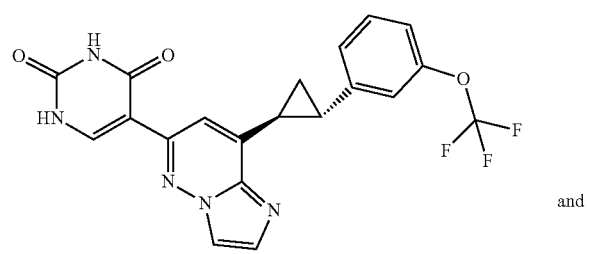

and

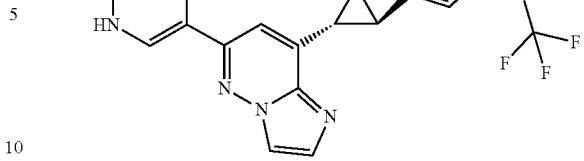

5-(8-((1S,2S)-2-(3-(trifluoromethoxy)phenyl)cyclopropyl)imidazo[1,2-b]pyridazin-6-yl) pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(3-(trifluoromethoxy)phenyl)cyclopropyl)imidazo[1,2-b]pyridazine (Racemic Mixture). Purification was accomplished via RP-HPLC (10-90% MeCN/H$_2$O with TFA modifier, Gemini column). ES/MS m/z: 430.10 [M+H]. $^1$H NMR (400 MHz, Methanol-d4) δ 8.37 (d, J=1.9 Hz, 1H), 8.29 (s, 1H), 8.06 (d, J=1.9 Hz, 1H), 8.00 (s, 1H), 7.45 (t, J=8.0 Hz, 1H), 7.30 (dt, J=7.9, 1.3 Hz, 1H), 7.22 (s, 1H), 7.18 (ddt, J=8.0, 2.3, 1.1 Hz, 1H), 2.81 (ddt, J=9.0, 6.4, 3.5 Hz, 2H), 2.04 1.86 (m, 2H). $^{19}$F NMR (376 MHz, Methanol-d4) δ −59.86 (s, 3F), −77.69 (s, 3F).

Example 48. 5-(8-((2S,2S)-2-(4-(trifluoromethoxy)phenyl)cyclopropyl)imidazo[1,2-b]pyridazin-6-yl)pyrimidine-2,4(1H,3H)-dione and 5-(8-((1R,2R)-2-(4-(trifluoromethoxy)phenyl)cyclopropyl)imidazo[1,2-b]pyridazin-6-yl)pyrimidine-2,4(1H,3H)-dione

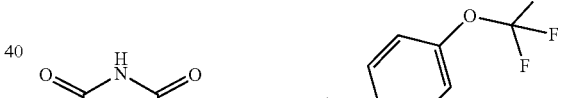

and

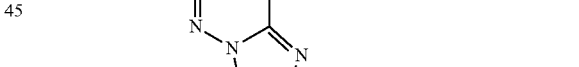

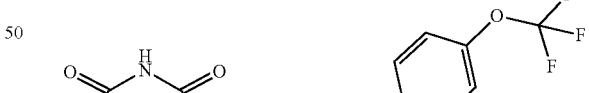

5-(8-((1S,2S)-2-(4-(trifluoromethoxy)phenyl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(4-(trifluoromethoxy)phenyl)cyclopropyl)imidazo[1, 2-b]pyridazine (Racemic Mixture). Purification was accomplished via RP-HPLC (10-90% MeCN/H₂O with TFA modifier, Gemini column). ES/MS m/z: 430.10 [M+H]. ¹H NMR (400 MHz, Methanol-d4) δ 8.38 (d, J=1.9 Hz, 1H), 8.30 (s, 1H), 8.07 (d, J=1.9 Hz, 1H), 8.02 (s, 1H), 7.46-7.34 (m, 2H), 7.27 (d, J=8.2 Hz, 2H), 2.89-2.70 (m, 2H), 2.01-1.86 (m, 2H). ¹⁹F NMR (376 MHz, Methanol-d4) δ −60.15 (s, 3F), −77.77 (s, 3F).

Example 52. 5-[8-[(1S,2S)-2-(2-pyridyl)cyclopropyl]imidazo[1,2-b]pyridazin-6-yl]-1H-pyrimidine-2,4-dione and 5-[8-[(1R,2R)-2-(2-pyridyl)cyclopropyl]imidazo[1,2-b]pyridazin-6-yl]-1H-pyrimidine-2,4-dione

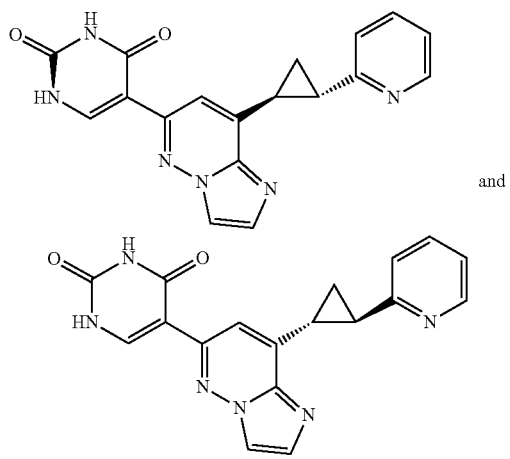

and

5-[8-[(1S,2S)-2-(2-pyridyl)cyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-[(1S,2S)-2-(2-pyridyl)cyclopropyl]imidazo[1,2-b]pyridazine (Racemic Mixture) and isolated by filtration as an HCl salt after trituration with acetonitrile and ethylacetate. ES/MS m/z: 347.10 [M+H]. ¹H NMR (400 MHz, DMSO-d6) δ 11.78-11.76 (m, 1H), 11.64-11.63 (m, 1H), 8.69-8.67 (m, 1H), 8.56-8.55 (m, 1H), 8.24-8.14 (m, 2H), 8.13-8.11 (m, 1H), 7.88 (s, 1H), 7.76-7.74 (m, 1H), 7.64-7.61 (m, 1H), 3.25-3.21 (m, 1H), 3.13-3.10 (m, 1H), 2.23-2.11 (m, 2H).

Example 53. 5-[8-[(1S,2S)-2-(3-pyridyl)cyclopropyl]imidazo[1,2-b]pyridazin-6-yl]-1H-pyrimidine-2,4-dione and 5-[8-[(1R,2R)-2-(3-pyridyl)cyclopropyl]imidazo[1,2-b]pyridazin-6-yl]-1H-pyrimidine-2,4-dione

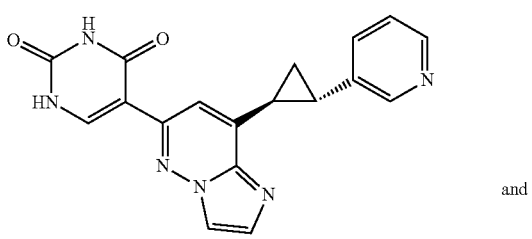

and

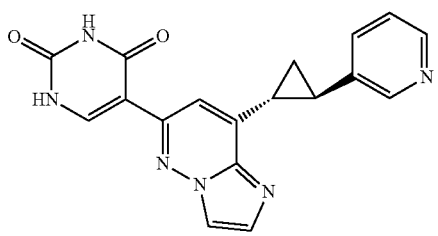

5-[8-[(1S,2S)-2-(3-pyridyl)cyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-[(1S,2S)-2-(3-pyridyl)cyclopropyl]imidazo[1,2-b]pyridazine (Racemic Mixture) and purified by RP-HPLC (5-70% MeCN/H₂O with TFA, Gemini column). ES/MS m/z: 347.10 [M+H]. ¹H NMR (400 MHz, Methanol-d4) δ 8.84-8.83 (m, 1H), 8.74-8.67 (m, 1H), 8.42-8.39 (m, 1H), 8.37-8.24 (m, 2H), 7.98-7.95 (m, 3H), 3.03-2.91 (m, 2H), 2.17-2.12 (m, 1H), 2.06-2.01 (m, 1H).

Example 54. 5-[8-[(1S,2S)-2-(4-pyridyl)cyclopropyl]imidazo[1,2-b]pyridazin-6-yl]-1H-pyrimidine-2,4-dione and 5-[8-[(1R,2R)-2-(4-pyridyl)cyclopropyl]imidazo[1,2-b]pyridazin-6-yl]-1H-pyrimidine-2,4-dione

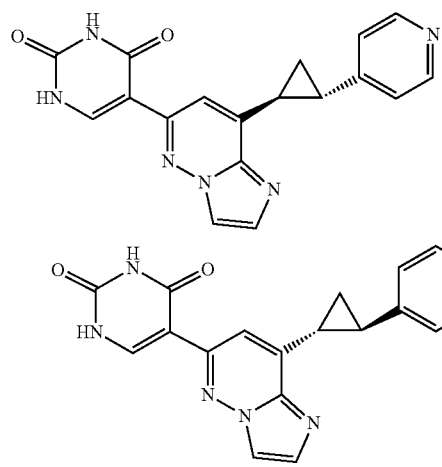

and

5-[8-[(1S,2S)-2-(4-pyridyl)cyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-[(1S,2S)-2-(4-pyridyl)cyclopropyl]imidazo[1,2-b]pyridazine (Racemic Mixture) and purified by RP-HPLC (5-70% MeCN/H₂O with TFA, Gemini column). ES/MS m/z: 347.10 [M+H]. ¹H NMR (400 MHz, Methanol-d4) 8.75-8.73 (m, 2H), 8.31-8.27 (m, 2H), 7.96-7.94 (m, 4H), 3.23-3.18 (m, 1H), 3.05-3.01 (m, 1H), 2.38-2.32 (m, 1H), 2.18-2.13 (m, 1H).

Example 55. 5-(8-(4,4-difluorocyclohexyl)-2-methyl-[1,2,4]triazolo[1,5-b]pyridazin-6-yl)pyrimidine-2,4(1H,3H)-dione

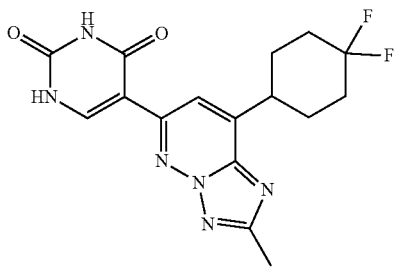 [SMILES: Cc1nc2c(C3CCC(F)(F)CC3)cc(-c3c[nH]c(=O)[nH]c3=O)nn2n1]

5-(8-(4,4-difluorocyclohexyl)-2-methyl[1,2,4]triazolo[1,5-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(4,4-difluorocyclohexyl)-6-(2,4-dimethoxypyrimidin-5-yl)-2-methyl-[1,2,4]triazolo[1,5-b]pyridazine. Purification was accomplished by RP-HPLC (10-90% MeCN/H$_2$O with TFA modifier, Gemini column). ES/MS m/z: 363.1 [M+1]. $^1$H NMR (400 MHz, DMSO-d6) δ 11.60 (d, J=3.9 Hz, 2H), 8.09 (d, J=6.5 Hz, 1H), 7.97 (s, 1H), 3.31-3.24 (m, 1H), 2.53 (s, 3H), 2.20-1.86 (m, 8H). $^{19}$F NMR (376 MHz, DMSO-d6) δ −90.03 (d, J=233.5 Hz, 1F), −99.94 (m, 1F).

Example 56. 8-(4,4-difluorocyclohexyl)-6-(2,4-dioxo-1,2,3,4-tetrahydropyrimidin-5-yl)imidazo[1,2-b]pyridazine-3-carbonitrile

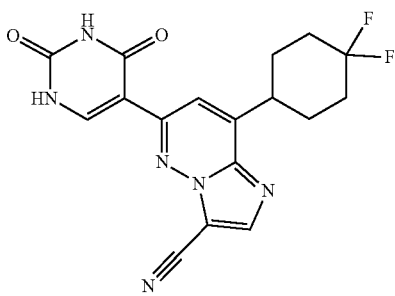 [SMILES: N#Cc1cnc2c(C3CCC(F)(F)CC3)cc(-c3c[nH]c(=O)[nH]c3=O)nn12]

8-(4,4-difluorocyclohexyl)-6-(2,4-dioxo-1,2,3,4-tetrahydropyrimidin-5-yl)imidazo[1,2-b]pyridazine-3-carbonitrile was prepared in the manner described for Example 1, but replacing 8-cyclopropyl-6-(2,4-dimethoxypyrimidin-5-yl)-2-methyl-imidazo[1,2-b]pyridazine with 8-(4,4-difluorocyclohexyl)-6-(2,4-dimethoxypyrimidin-5-yl)imidazo[1,2-b]pyridazine-3-carbonitrile. Purification was accomplished by RP-HPLC (10-90% MeCN/H$_2$O with TFA modifier, Gemini column). ES/MS m/z: 373.1 [M+1]. $^1$H NMR (400 MHz, DMSO-d6) δ 11.64 (d, J=6.8 Hz, 2H), 8.55 (s, 1H), 8.12 (d, J=6.1 Hz, 1H), 7.94 (s, 1H), 3.32-3.23 (m, 1H), 2.24-1.86 (m, 8H). $^{19}$F NMR (376 MHz, DMSO-d6) δ −90.04 (d, J=233.4 Hz, 1F), −101.02 (m, 1F).

Example 57. 5-(8-(4,4-difluorocyclohexyl)-3-methylimidazo[1,2-b]pyridazin-6-yl)pyrimidine-2,4(1H,3H)-dione

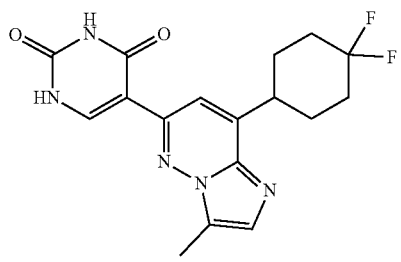 [SMILES: Cc1cnc2c(C3CCC(F)(F)CC3)cc(-c3c[nH]c(=O)[nH]c3=O)nn12]

5-(8-(4,4-difluorocyclohexyl)-3-methylimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(4,4-difluorocyclohexyl)-6-(2,4-dimethoxypyrimidin-5-yl)-3-methyl-imidazo[1,2-b]pyridazine. Purification was accomplished by RP-HPLC (10-90% MeCN/H$_2$O with TFA modifier, Gemini column). ES/MS m/z: 362.1 [M+1]. $^1$H NMR (400 MHz, DMSO-d6) δ 11.67 (d, J=6.3 Hz, 1H), 11.61 (d, J=2.0 Hz, 1H), 8.19 (d, J=6.2 Hz, 1H), 7.90 (s, 2H), 3.32 (t, J=12.1 Hz, 2H), 2.55 (d, J=1.0 Hz, 3H), 2.26-2.13 (m, 2H), 2.13-2.03 (m, 3H), 2.03-1.93 (m, 1H), 1.93-1.78 (m, 2H). $^{19}$F NMR (376 MHz, DMSO-d6) δ −74.95 (s, 3F), −90.00 (d, J=233.9 Hz, 1F), −99.99 (m, 1F).

Example 58. 5-(8-((benzyloxy)methyl)imidazo[1,2-b]pyridazin-6-yl)pyrimidine-2,4(1H,3H)-dione

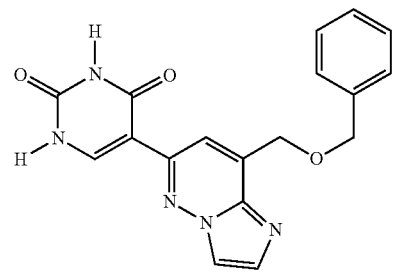 [SMILES: O=c1[nH]cc(-c2cc(COCc3ccccc3)c3nccn3n2)c(=O)[nH]1]

5-(8-((benzyloxy)methyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-((benzyloxy)methyl)-6-(2,4-dimethoxypyrimidin-5-yl)imidazo[1,2-b]pyridazine. Purification was accomplished via RP-HPLC (10-90% MeCN/H$_2$O with TFA modifier, Gemini column). ES/MS m/z: 350.10 [M+H]. $^1$H NMR (400 MHz, DMSO-d6) δ 11.64 (dd, J=6.2, 2.0 Hz, 1H), 11.60 (d, J=2.0 Hz, 1H), 8.42 (d, J=1.5 Hz, 1H), 8.09 (d, J=6.2 Hz, 1H), 8.04 (s, 1H), 7.95 (d, J=1.5 Hz, 1H), 7.46-7.41 (m, 2H), 7.41-7.35 (m, 2H), 7.35-7.28 (m, 1H), 4.96 (s, 2H), 4.72 (s, 2H).

Example 59. 5-(8-(3-phenylazetidin-1-yl)imidazo[1,2-b]pyridazin-6-yl)pyrimidine-2,4(1H,3H)-dione

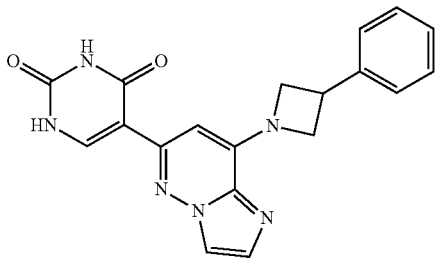 [SMILES: O=c1[nH]cc(-c2cc(N3CC(c4ccccc4)C3)c3nccn3n2)c(=O)[nH]1]

5-(8-(3-phenylazetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-phenylazetidin-1-yl)imidazo[1,2-b]pyridazine, and running the reaction at 70° C. for 4 h. Purification was accomplished by RP-HPLC (10-90% MeCN/H₂O with TFA modifier, Gemini column). ES/MS m/z: 361.1 [M+1]. ¹H NMR (400 MHz, DMSO-d6) δ 11.47-11.33 (m, 2H), 8.07 (d, J=1.3 Hz, 1H), 7.94 (d, J=6.1 Hz, 1H), 7.61 (s, 1H), 7.47-7.41 (m, 2H), 7.38 (dd, J=8.4, 6.8 Hz, 2H), 7.31-7.25 (m, 1H), 6.54 (s, 1H), 4.87-4.74 (m, 2H), 4.41-4.31 (m, 2H), 4.11 (tt, J=8.6, 6.1 Hz, 1H).

Example 60. 5-(8-((2S,2S)-2-(3,5-difluorophenyl)cyclopropyl)imidazo[1,2-b]pyridazin-6-yl)pyrimidine-2,4(1H,3H)-dione and 5-(8-((1R,2R)-2-(3,5-difluorophenyl)cyclopropyl)imidazo[1,2-b]pyridazin-6-yl)pyrimidine-2,4(1H,3H)-dione

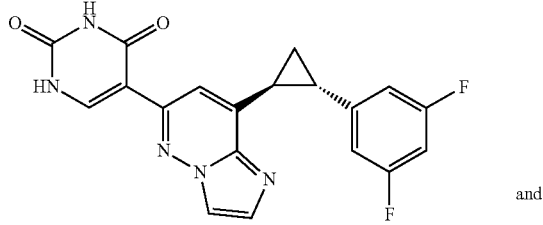

and

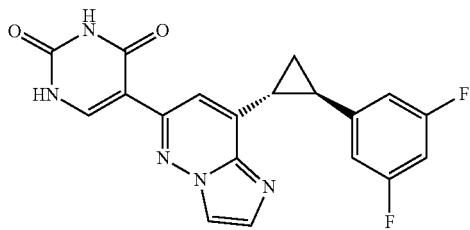

5-(8-((1S,2S)-2-(3,5-difluorophenyl)cyclopropyl)imidazo[1,2-b]pyridazin-6-yl)pyrimidine-2,4(1H,3H)-dione (Racemic Mixture) was prepared in the manner described for Example 1, but replacing 8-cyclopropyl-6-(2,4-dimethoxypyrimidin-5-yl)-2-methyl-imidazo[1,2-b]pyridazine with 8-[(1S,2S)-2-(3,5-difluorophenyl)cyclopropyl]-6-(2,4-dimethoxypyrimidin-5-yl)imidazo[1,2-b]pyridazine (Racemic Mixture). Purification was accomplished by RP-HPLC (10-90% MeCN/H₂O with TFA modifier, Gemini column). ES/MS m/z: 382.1 [M+1]. ¹H NMR (400 MHz, DMSO-d6) δ 11.52 (d, J=4.1 Hz, 2H), 8.30 (d, J=1.3 Hz, 1H), 8.01 (d, J=6.4 Hz, 1H), 7.81 (s, 1H), 7.54 (s, 1H), 7.05 (td, J=8.2, 7.4, 3.2 Hz, 3H), 2.88 (dt, J=9.3, 5.5 Hz, 1H), 2.77 (ddd, J=8.8, 6.1, 4.3 Hz, 1H), 2.14 (dt, J=8.7, 5.4 Hz, 1H), 1.81 (dt, J=8.7, 5.3 Hz, 1H). ¹⁹F NMR (376 MHz, DMSO-d6) δ −74.90 (m, 3F), −110.76 (dd, J=10.3, 7.6 Hz, 2F).

Example 61. 5-(8-((2S,2S)-2-(2,3,5-trifluorophenyl)cyclopropyl)imidazo[1,2-b]pyridazin-6-yl)pyrimidine-2,4(1H,3H)-dione and 5-(8-((1R,2R)-2-(2,3,5-trifluorophenyl)cyclopropyl)imidazo[1,2-b]pyridazin-6-yl)pyrimidine-2,4(1H,3H)-dione

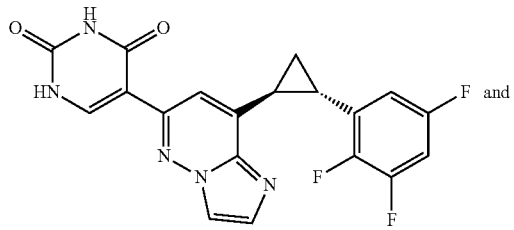

and

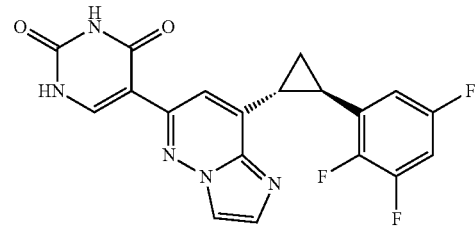

5-(8-((1S,2S)-2-(2,3,5-trifluorophenyl)cyclopropyl)imidazo[1,2-b]pyridazin-6-yl)pyrimidine-2,4(1H,3H)-dione and 5-(8-((1R,2R)-2-(2,3,5-trifluorophenyl)cyclopropyl)imidazo[1,2-b]pyridazin-6-yl)pyrimidine-2,4(1H,3H)-dione were prepared as a racemic mixture in the manner described for Example 1, but replacing 8-cyclopropyl-6-(2,4-dimethoxypyrimidin-5-yl)-2-methyl-imidazo[1,2-b]pyridazine with 4-[(1S,2S)-2-[6-(2,4-dimethoxypyrimidin-5-yl)imidazo[1,2-b]pyridazin-8-yl]cyclopropyl]-2-fluoro-benzonitrile (Racemic Mixture). Purification was accomplished by RP-HPLC (10-90% MeCN/H₂O with TFA modifier, Gemini column). ES/MS m/z: 389.1 [M+1]. ¹H NMR (400 MHz, DMSO-d6) δ 11.54 (d, J=3.7 Hz, 2H), 8.31 (d, J=1.4 Hz, 1H), 8.02 (d, J=6.4 Hz, 1H), 7.88-7.79 (m, 2H), 7.58 (s, 1H), 7.47 (dd, J=11.1, 1.5 Hz, 1H), 7.34 (dd, J=8.2, 1.6 Hz, 1H), 2.96 (dd, J=8.8, 5.1 Hz, 1H), 2.86 (ddd, J=8.9, 6.2, 4.4 Hz, 1H), 2.24 (dt, J=8.7, 5.4 Hz, 1H), 1.89 (dt, J=8.8, 5.5 Hz, 1H). ¹⁹F NMR (376 MHz, DMSO-d6) δ −75.04 (s, 3F), −109.50 (dd, J=11.0, 7.2 Hz, 1F).

Example 62. 5-(8-(3-(trifluoromethyl)azetidin-1-yl) imidazo[1,2-b]pyridazin-6-yl)pyrimidine-2,4(1H,3H)-dione

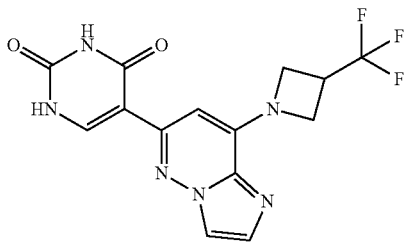 [SMILES: O=c1[nH]cc(-c2cc(N3CC(C(F)(F)F)C3)c3nccn3n2)c(=O)[nH]1]

5-(8-(3-(trifluoromethyl)azetidin-1-yl)imidazo[1,2-b] pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[3-(trifluoromethyl)azetidin-1-yl]imidazo[1,2-b] pyridazine, and running the reaction at 70° C. for 4 h. Purification was accomplished by RP-HPLC (10-90% MeCN/H$_2$O with TFA modifier, Gemini column). ES/MS m/z: 353.1 [M+1]. $^1$H NMR (400 MHz, DMSO-d6) δ 11.43 (dt, J=6.1, 2.0 Hz, 2H), 8.09 (d, J=1.3 Hz, 1H), 7.94 (d, J=6.1 Hz, 1H), 7.62 (d, J=1.3 Hz, 1H), 6.53 (s, 1H), 4.62 (t, J=9.2 Hz, 2H), 4.41-4.33 (m, 2H), 3.83 (dh, J=14.1, 5.0 Hz, 1H). $^{19}$F NMR (376 MHz, DMSO-d6) δ −72.74 (d, J=9.3 Hz, 3F), −75.39 (s, 3F).

Example 63. 5-(8-(3,3-dimethylazetidin-1-yl)imidazo[1,2-b]pyridazin-6-yl)pyrimidine-2,4(1H,3H)-dione

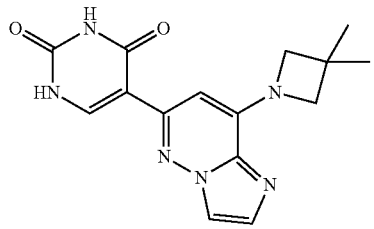 [SMILES: CC1(C)CN(c2cc(-c3c[nH]c(=O)[nH]c3=O)nn3ccnc23)C1]

5-(8-(3,3-dimethylazetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3,3-dimethylazetidin-1-yl)imidazo[1,2-b]pyridazine, and running the reaction at 70° C. for 4 h. Purification was accomplished by RP-HPLC (10-90% MeCN/H$_2$O with TFA modifier, Gemini column). ES/MS m/z: 313.2 [M+1]. $^1$H NMR (400 MHz, DMSO-d6) δ 11.42 (d, J=6.7 Hz, 2H), 8.09 (d, J=1.3 Hz, 1H), 7.94 (d, J=6.0 Hz, 1H), 7.64 (d, J=1.3 Hz, 1H), 6.50 (s, 1H), 4.10-4.03 (m, 4H), 1.32 (s, 6H).

Example 64. 5-((2S,2S)-2-(6-(2,4-dioxo-1,2,3,4-tetrahydropyrimidin-5-yl)imidazo[1,2-b]pyridazin-8-yl)cyclopropyl)-2-fluorobenzonitrile and 54(1R,2R)-2-(6-(2,4-dioxo-1,2,3,4-tetrahydropyrimidin-5-yl) imidazo[1,2-b]pyridazin-8-yl)cyclopropyl)-2-fluorobenzonitrile

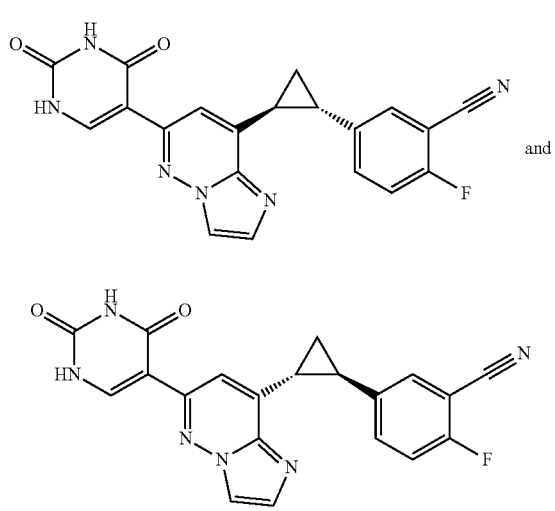

5-((2S,2S)-2-(6-(2,4-dioxo-1,2,3,4-tetrahydropyrimidin-5-yl)imidazo[1,2-b]pyridazin-8-yl)cyclopropyl)-2-fluoro-robenzonitrile was prepared as a racemic mixture in the manner described for Example 1, but replacing 8-cyclopropyl-6-(2,4-dimethoxypyrimidin-5-yl)-2-methyl-imidazo[1,2-b]pyridazine with 5-[(1S,2S)-2-[6-(2,4-dimethoxypyrimidin-5-yl)imidazo[1,2-b]pyridazin-8-yl]cyclopropyl]-2-fluoro-benzonitrile (Racemic Mixture). Purification was accomplished by RP-HPLC (10-90% MeCN/H$_2$O with TFA modifier, Gemini column). ES/MS m/z: 389.1 [M+1]. $^1$H NMR (400 MHz, DMSO-d6) δ 11.59 (d, J=7.5 Hz, 2H), 8.37 (d, J=1.5 Hz, 1H), 8.04 (d, J=6.0 Hz, 1H), 7.91 (s, 1H), 7.85 (dd, J=6.1, 2.4 Hz, 1H), 7.71 (ddd, J=7.9, 5.2, 2.4 Hz, 1H), 7.60 (s, 1H), 7.49 (t, J=9.0 Hz, 1H), 2.88 (ddd, J=9.3, 6.2, 4.4 Hz, 1H), 2.81-2.73 (m, 1H), 2.10 (dt, J=9.0, 5.4 Hz, 1H), 1.85 (dt, J=8.6, 5.5 Hz, 1H). $^{19}$F NMR (376 MHz, DMSO-d6) δ −75.13 (s, 3F), −113.01 (q, J=6.2 Hz, 1F).

Example 65. 5-(8-((2S,2S)-2-(2,5-difluorophenyl) cyclopropyl)imidazo[1,2-b]pyridazin-6-yl)pyrimidine-2,4(1H,3H)-dione and 5-(8-((1R,2R)-2-(2,5-difluorophenyl)cyclopropyl)imidazo[1,2-b] pyridazin-6-yl)pyrimidine-2,4(1H,3H)-dione

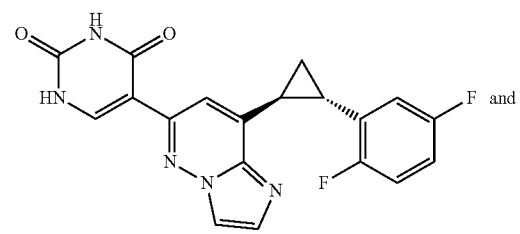

-continued

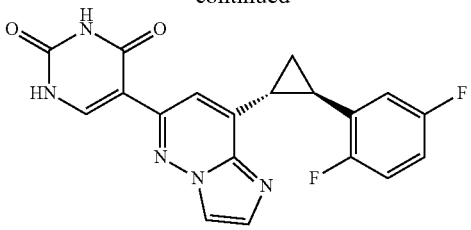

5-(8-((1S,2S)-2-(2,5-difluorophenyl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-[(1S,2S)-2-(2,5-difluorophenyl)cyclopropyl]-6-(2,4-dimethoxypyrimidin-5-yl)imidazo[1,2-b]pyridazine (Racemic Mixture). Purification was accomplished by RP-HPLC (10-90% MeCN/H$_2$O with TFA modifier, Gemini column). ES/MS m/z:

Example 66. 5-(8-(2-phenylazetidin-1-yl)imidazo[1,2-b]pyridazin-6-yl)pyrimidine-2,4(1H,3H)-dione

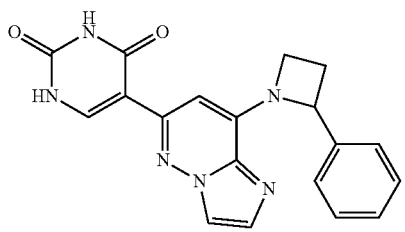 [SMILES: O=c1[nH]cc(-c2cc(N3CCC3c3ccccc3)c3nccn3n2)c(=O)[nH]1]

To a solution of 6-(2,4-dimethoxypyrimidin-5-yl)-8-(2-phenylazetidin-1-yl)imidazo[1,2-b]pyridazine (50 mg, 0.129 mmol) in MeCN (3 mL) was added iodotrimethylsilane (0.183 mL, 1.29 mmol). The mixture was stirred at rt for 3 h, then concentrated in vacuo. The resulting residue was diluted with THF (2.5 mL), and potassium tert-butoxide (58 mg, 0.516 mmol) was added. The mixture was heated to 70° C. for 1 h. The mixture was then quenched with water, and diluted with water/MeCN. Purification was accomplished by RP-HPLC (10-90% MeCN/H$_2$O with TFA modifier, Gemini column). ES/MS m/z: 361.1 [M+1]. $^1$H NMR (400 MHz, Methanol-d4) δ 8.25 (s, 1H), 8.23 (d, J=2.3 Hz, 1H), 7.70 (s, 1H), 7.60 (d, J=2.4 Hz, 1H), 7.46-7.39 (m, 3H), 7.26-7.22 (m, 2H), 5.87 (dd, J=7.4, 3.7 Hz, 1H), 3.61-3.51 (m, 2H), 2.75-2.65 (m, 2H).

Example 67. 5-[8-[(3R)-3-(4-fluorophenyl)pyrrolidin-1-yl]imidazo[1,2-b]pyridazin-6-yl]-1H-pyrimidine-2,4-dione

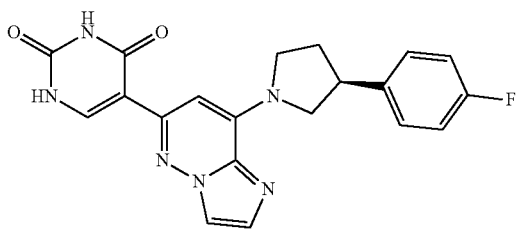 [SMILES: O=c1[nH]cc(-c2cc(N3CC[C@@H](c4ccc(F)cc4)C3)c3nccn3n2)c(=O)[nH]1]

5-[8-[(3R)-3-(4-fluorophenyl)pyrrolidin-1-yl]imidazo[1,2-b]pyridazin-6-yl]-1H-pyrimidine-2,4-dione was prepared as follows: To a solution of 6-(2,4-dimethoxypyrimidin-5-yl)-8-[(3R)-3-(4-fluorophenyl)pyrrolidin-1-yl]imidazo[1,2-b]pyridazine (93 mg, 0.22 mmol, 1 equiv) in MeOH (2.5 mL) was added 1 M HCl (aq) solution (1.5 mL). The reaction vessel was heated to 80° C. for 6 h. Solids separated were filtered, washed with water and dried affording 5-[8-[(3R)-3-(4-fluorophenyl)pyrrolidin-1-yl]imidazo[1,2-b]pyridazin-6-yl]-1H-pyrimidine-2,4-dione as an HCl salt. Some subsequent examples prepared in accordance with this method were purified by HPLC in place of the aforementioned solid separation according to standard methods. ES/MS: 393.10 [M+1]. $^1$H NMR (400 MHz, DMSO-d6) δ 11.58-11.51 (m, 1H), 11.46-11.45 (m, 1H), 8.26-8.25 (m, 1H), 8.03-8.01 (m, 1H), 7.86 (s, 1H), 7.50-7.40 (m, 2H), 7.25-7.14 (m, 2H), 6.92 (s, 1H), 4.38 (brs, 1H), 4.00 (brs, 1H), 3.82 (brs, 2H), 3.68-3.56 (m, 1H), 2.45-2.42 (m, 1H), 2.22-2.07 (m, 1H). $^{19}$F NMR (376 MHz, DMSO-d6) δ −116.67 (m, 1F).

Example 68. 5-[8-[(3S)-3-(4-fluorophenyl)pyrrolidin-1-yl]imidazo[1,2-b]pyridazin-6-yl]-1H-pyrimidine-2,4-dione

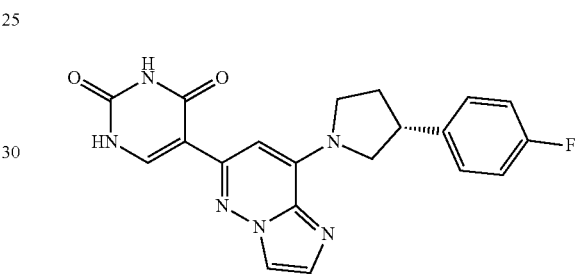

5-[8-[(3S)-3-(4-fluorophenyl)pyrrolidin-1-yl]imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-[(3S)-3-(4-fluorophenyl)pyrrolidin-1-yl]imidazo[1,2-b]pyridazine and isolated by filtration as an HCl salt. ES/MS: 393.10 [M+1]. $^1$H NMR (400 MHz, DMSO-d6) δ 11.56-11.54 (m, 1H), 11.46-11.45 (m, 1H), 8.27-8.26 (m, 1H), 8.03-8.01 (m, 1H), 7.87 (s, 1H), 7.47-7.43 (m, 2H), 7.22-7.17 (m, 2H), 6.92 (s, 1H), 4.38 (brs, 1H), 3.96 (brs, 1H), 3.81 (brs, 2H), 3.68-3.56 (m, 1H), 2.47-2.42 (m, 1H), 2.19-2.09 (m, 1H). $^{19}$F NMR (376 MHz, DMSO-d6) δ −116.67 (m, 1F).

Example 69. 5-(8-cyclopropyl-3-fluoro-imidazo[1,2-b]pyridazin-6-yl)-1H-pyrimidine-2,4-dione

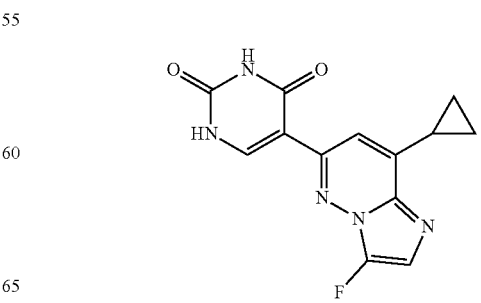

5-(8-cyclopropyl-3-fluoro-imidazo[1,2-b]pyridazin-6-yl)-1H-pyrimidine-2,4-dione was prepared in the manner described for Example 67, but replacing 6-(2,4-dimethoxy-pyrimidin-5-yl)-8-[(3R)-3-(4-fluorophenyl)pyrrolidin-1-yl]imidazo[1,2-b]pyridazine with 8-cyclopropyl-6-(2,4-dimethoxypyrimidin-5-yl)-3-fluoro-imidazo[1,2-b]pyridazine. The reaction mixture was purified by RP-HPLC (5-100% MeCN/H$_2$O with TFA modifier, Gemini column) affording 5-(8-cyclopropyl-3-fluoro-imidazo[1,2-b]pyridazin-6-yl)-1H-pyrimidine-2,4-dione as a TFA salt. ES/MS m/z: 288.10 [M+H]. $^1$H NMR (400 MHz, DMSO-d6) δ 11.60-11.58 (m, 1H), 11.53-11.52 (m, 1H), 8.03-8.02 (m, 1H), 7.68-7.66 (m, 1H), 7.40 (s, 1H), 2.51-2.42 (m, 1H), 1.26-1.23 (m, 4H). $^{19}$F NMR (376 MHz, DMSO-d6) δ −155.46 (d, J=6.9 Hz, 1F).

Example 70. 5-[8-(4,4-difluoro-1-piperidyl)imidazo[1,2-b]pyridazin-6-yl]-1H-pyrimidine-2,4-dione

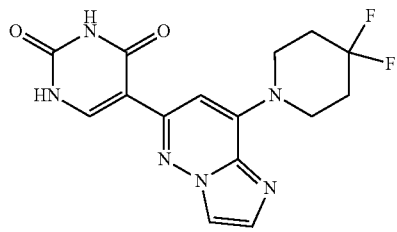 [SMILES: O=c1[nH]cc(-c2cc(N3CCC(F)(F)CC3)c3nccn3n2)c(=O)[nH]1]

5-[8-(4,4-difluoro-1-piperidyl)imidazo[1,2-b]pyridazin-6-yl]-1H-pyrimidine-2,4-dione was prepared in the manner described for Example 67, but replacing 6-(2,4-dimethoxy-pyrimidin-5-yl)-8-[(3R)-3-(4-fluorophenyl)pyrrolidin-1-yl]imidazo[1,2-b]pyridazine with 8-(4,4-difluoro-1-piperidyl)-6-(2,4-dimethoxypyrimidin-5-yl)imidazo[1,2-b]pyridazine and isolated by filtration as an HCl salt. ES/MS: 349.10 [M+1]. $^1$H NMR (400 MHz, DMSO-d6) δ11.55-11.54 (m, 1H), 11.48-11.47 (m, 1H), 8.22-8.21 (m, 1H), 8.01-7.97 (m, 1H), 7.80-7.75 (m, 1H), 7.18 (s, 1H), 4.00-3.98 (m, 4H), 2.22-2.12 (m, 4H). $^{19}$F NMR (376 MHz, DMSO-d6) δ −95.83 (m, 2F).

Example 71. 5-[8-[4-(cyclopropylmethylamino)phenyl]imidazo[1,2-b]pyridazin-6-yl]-1H-pyrimidine-2,4-dione

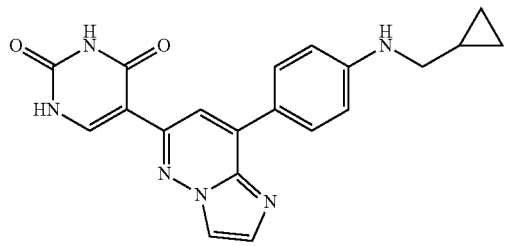 [SMILES: O=c1[nH]cc(-c2cc(-c3ccc(NCC4CC4)cc3)c3nccn3n2)c(=O)[nH]1]

5-[8-[4-(cyclopropylmethylamino)phenyl]imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with N-(cyclopropylmethyl)-4-[6-(2,4-dimethoxypyrimidin-5-yl)imidazo[1,2-b]pyridazin-8-yl]aniline and isolated by filtration as an HCl salt. ES/MS: 375.20 [M+1]. $^1$H NMR (400 MHz, DMSO-d6) δ 11.84-11.82 (m, 1H), 11.63-11.62 (m, 1H), 8.61-8.60 (m, 1H), 8.28-8.08 (m, 3H), 7.87-7.85 (m, 2H), 6.98-6.96 (m, 2H), 3.07-3.06 (m, 2H), 1.18-1.06 (m, 1H), 0.56-0.47 (m, 2H), 0.35-0.22 (m, 2H).

Example 72. 5-[8-(3,3-dimethylpyrrolidin-1-yl)imidazo[1,2-b]pyridazin-6-yl]-1H-pyrimidine-2,4-dione

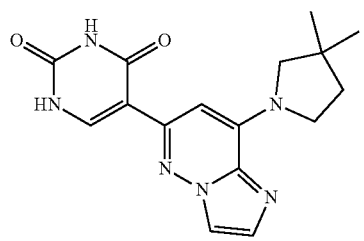 [SMILES: CC1(C)CCN(c2cc(-c3c[nH]c(=O)[nH]c3=O)nn3ccnc23)C1]

5-[8-(3,3-dimethylpyrrolidin-1-yl)imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-(3,3-dimethylpyrrolidin-1-yl)imidazo[1,2-b]pyridazine and purified by RP-HPLC (5-100% MeCN/H$_2$O with TFA, Gemini column). ES/MS: 327.20 [M+1]. $^1$H NMR (400 MHz, DMSO-d6) δ 11.43-11.40 (m, 2H), 8.09-8.08 (m, 1H), 7.95-7.94 (m, 1H), 7.63-7.62 (m, 1H), 6.63 (s, 1H), 3.84-3.68 (m, 4H), 1.85-1.77 (m, 2H), 1.13 (s, 6H).

Example 73. 5-[8-[(3S,4S)-3,4-difluoropyrrolidin-1-yl]imidazo[1,2-b]pyridazin-6-yl]-1H-pyrimidine-2,4-dione and 5-[8-[(3R,4R)-3,4-difluoropyrrolidin-1-yl]imidazo[1,2-b]pyridazin-6-yl]-1H-pyrimidine-2,4-dione

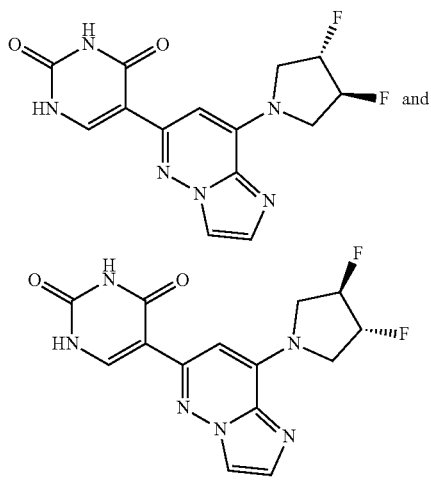

5-[8-[(3S,4S)-3,4-difluoropyrrolidin-1-yl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 8-[(3S,4S)-3,4-difluoropyrrolidin-1-yl]-6-(2,4-dimethoxypyrimidin-5-yl)imidazo[1,2-b]pyridazine (Racemic Mixture) and isolated by filtration as an HCl salt. ES/MS m/z: 335.10 [M+H]. ¹H NMR (400 MHz, DMSO-d6) δ 11.59-11.57 (m, 1H), 11.47-1.46 (m, 1H), 8.28-8.23 (m, 1H), 8.03-8.01 (m, 1H), 7.83-7.82 (m, 1H), 6.89 (s, 1H), 5.71-5.45 (m, 2H), 4.41-4.05 (m, 4H). ¹⁹F NMR (377 MHz, DMSO-d6) δ −188.83 (m, 2F).

Example 74. 5-[8-[(1S,2S)-2-(1-naphthyl)cyclopropyl]imidazo[1,2-b]pyridazin-6-yl]-1H-pyrimidine-2,4-dione and 5-[8-[(1R,2R)-2-(1-naphthyl)cyclopropyl]imidazo[1,2-b]pyridazin-6-yl]-1H-pyrimidine-2,4-dione

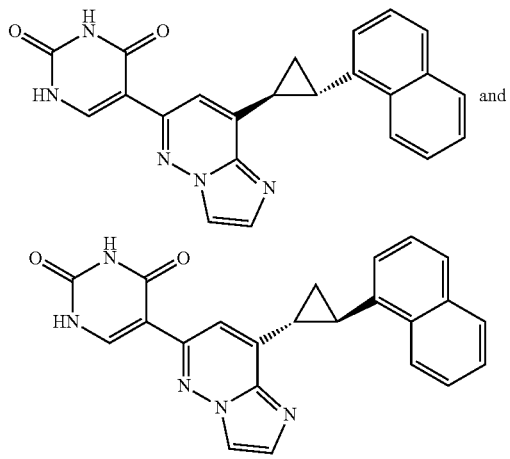

and

5-[8-[(1S,2S)-2-(1-naphthyl)cyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-[(1S,2S)-2-(1-naphthyl)cyclopropyl]imidazo[1,2-b]pyridazine (Racemic Mixture) and purified by RP-HPLC (10-90% MeCN/H₂O with TFA, Gemini column). ES/MS m/z: 396.20 [M+H]. ¹H NMR (400 MHz, Methanol-d4) δ 8.46-8.45 (m, 1H), 8.36 (s, 1H), 8.24 (s, 1H), 8.16-8.08 (m, 2H), 7.96-7.88 (m, 1H), 7.85-7.83 m, 1H), 7.56-7.42 (m, 4H), 3.30-3.26 (m, 1H), 2.68-2.63 (m, 1H), 2.17-2.11 (m, 1H), 2.08-1.93 (m, 1H).

Example 75. 5-(2,8-dicyclopropylimidazo[1,2-b]pyridazin-6-yl)-1H-pyrimidine-2,4-dione

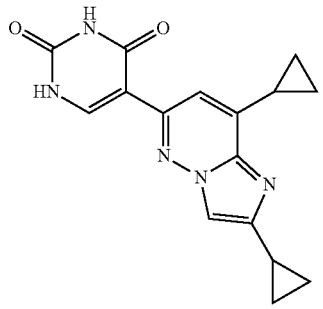 [SMILES: O=c1[nH]cc(-c2cc(C3CC3)c3nc(C4CC4)cn3n2)c(=O)[nH]1]

5-(2,8-dicyclopropylimidazo[1,2-b]pyridazin-6-yl)-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 2,8-dicyclopropyl-6-(2,4-dimethoxypyrimidin-5-yl)imidazo[1,2-b]pyridazine and purified by RP-HPLC (5-90% MeCN/H₂O with TFA, Gemini column). ES/MS: 310.20 [M+1]. ¹H NMR (400 MHz, DMSO-d6) δ 11.62-11.55 (m, 2H), 8.27 (s, 1H), 8.02-8.01 (m, 1H), 7.53 (s, 1H), 2.58-2.51 (m, 1H), 2.20-2.08 (m, 1H), 1.34-1.22 (m, 2H), 1.17-1.08 (m, 4H), 1.05-0.93 (m, 2H). ¹⁹F NMR (376 MHz, DMSO-d6) δ −75.35.

Example 76. 5-[3-fluoro-8-[(1S,2S)-2-(4-fluorophenyl)cyclopropyl]imidazo[1,2-b]pyridazin-6-yl]-1H-pyrimidine-2,4-dione and 5-[3-fluoro-8-[(1R,2R)-2-(4-fluorophenyl)cyclopropyl]imidazo[1,2-b]pyridazin-6-yl]-1H-pyrimidine-2,4-dione

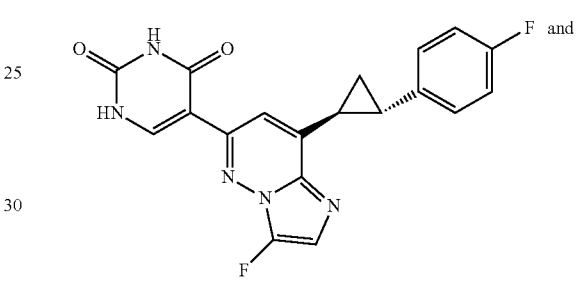

and

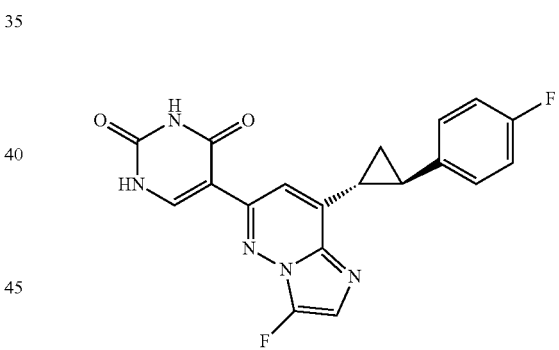

5-[3-fluoro-8-[(1S,2S)-2-(4-fluorophenyl)cyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-3-fluoro-8-[(1S,2S)-2-(4-fluorophenyl)cyclopropyl]imidazo[1,2-b]pyridazine (Racemic Mixture) and isolated by filtration as an HCl salt. ES/MS m/z: 382.10 [M+H]. ¹H NMR (400 MHz, DMSO-d6) δ 11.63-11.61 (m, 1H), 11.55-1.54 (m, 1H), 8.05-8.04 (m, 1H), 7.66-7.64 (m, 1H), 7.51 (s, 1H), 7.36-7.25 (m, 2H), 7.19-7.08 (m, 2H), 2.85-2.80 (m, 1H), 2.73-2.68 (m, 1H), 2.06-2.01 (m, 1H), 1.77-1.72 (m, 1H). ¹⁹F NMR (376 MHz, DMSO-d6) δ −117.32 (m, 1F), −155.36 (d, J=7.1 Hz, 1F).

Example 77. 5-[8-[(3S,4R)-3,4-difluoropyrrolidin-1-yl]imidazo[1,2-b]pyridazin-6-yl]-1H-pyrimidine-2,4-dione and 5-[8-[(3R,4S)-3,4-difluoropyrrolidin-1-yl]imidazo[1,2-b]pyridazin-6-yl]-1H-pyrimidine-2,4-dione

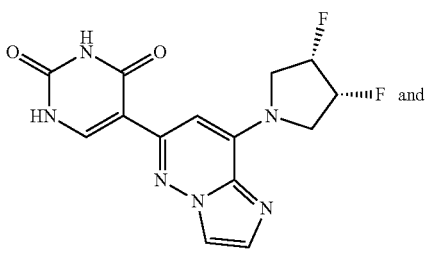

and

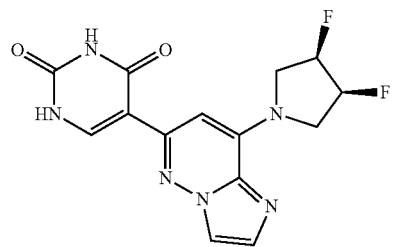

5-[8-[(3S,4R)-3,4-difluoropyrrolidin-1-yl]imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 8-[(3S,4R)-3,4-difluoropyrrolidin-1-yl]-6-(2,4-dimethoxypyrimidin-5-yl)imidazo[1,2-b]pyridazine (meso) and isolated by filtration as an HCl salt. ES/MS m/z: 335.10 [M+H]. $^1$H NMR (400 MHz, DMSO-d6) δ 11.59-11.57 (m, 1H), 11.46-11.45 (m, 1H), 8.25-8.22 (m, 1H), 8.02-7.97 (m, 1H), 7.83-7.82 (m, 1H), 6.86 (s, 1H), 5.64-5.40 (m, 2H), 4.37-3.95 (m, 4H). $^{19}$F NMR (377 MHz, DMSO-d6) δ −205.69 (m, 2F).

Example 78. 5-(8-pyrazol-1-ylimidazo[1,2-b]pyridazin-6-yl)-1H-pyrimidine-2,4-dione

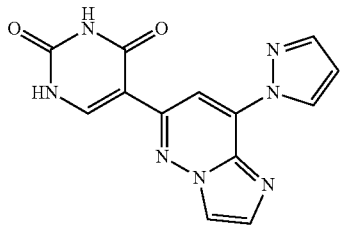 [SMILES: O=c1[nH]cc(-c2cc(-n3cccn3)c3nccn3n2)c(=O)[nH]1]

5-(8-pyrazol-1-ylimidazo[1,2-b]pyridazin-6-yl)-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-pyrazol-1-yl-imidazo[1,2-b]pyridazine and isolated by filtration as an HCl salt. ES/MS: 296.10 [M+1]. $^1$H NMR (400 MHz, DMSO-d6) δ 11.63-11.61 (m, 2H), 9.58-9.57 (m, 1H), 8.48-8.37 (m, 2H), 8.14-8.11 (m, 1H), 8.04-8.03 (m, 1H), 7.91-7.88 (m, 1H), 6.75-6.74 (m, 1H).

Example 79. 5-[8-(3,3-difluoropyrrolidin-1-yl)imidazo[1,2-b]pyridazin-6-yl]-1H-pyrimidine-2,4-dione

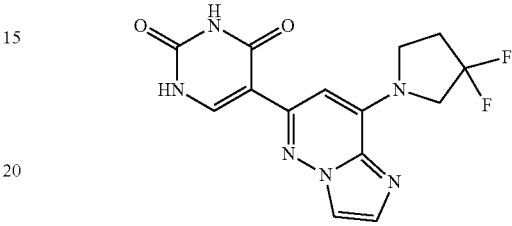

5-[8-(3,3-difluoropyrrolidin-1-yl)imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 8-(3,3-difluoropyrrolidin-1-yl)-6-(2,4-dimethoxypyrimidin-5-yl)imidazo[1,2-b]pyridazine and isolated by filtration as an HCl salt. ES/MS: 335.10 [M+1]. $^1$H NMR (400 MHz, DMSO-d6) δ 11.57-11.43 (m, 2H), 8.18-8.17 (m, 1H), 7.99-7.96 (m, 1H), 7.73-7.71 (m, 1H), 6.77 (s, 1H), 4.40-4.37 (m, 2H), 4.00-3.96 (m, 2H), 2.67-2.56 (m, 2H). $^{19}$F NMR (377 MHz, DMSO-d6) δ −101.14 (m, 2F).

Example 80. 5-[8-(3,3-difluoro-4,4-dimethyl-pyrrolidin-1-yl)imidazo[1,2-b]pyridazin-6-yl]-1H-pyrimidine-2,4-dione

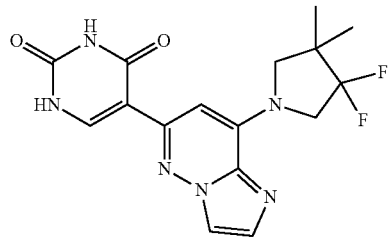 [SMILES: CC1(C)CN(c2cc(-c3c[nH]c(=O)[nH]c3=O)nn3ccnc23)CC1(F)F]

5-[8-(3,3-difluoro-4,4-dimethyl-pyrrolidin-1-yl)imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 8-(3,3-difluoro-4,4-dimethyl-pyrrolidin-1-yl)-6-(2,4-dimethoxypyrimidin-5-yl)imidazo[1,2-b]pyridazine and isolated by filtration as an HCl salt. ES/MS: 363.10 [M+1]. $^1$H NMR (400 MHz, DMSO-d6) δ 11.58-11.46 (m, 2H), 8.23-8.22 (m, 1H), 8.01-7.97 (m, 1H), 7.81-7.80 (m, 1H), 6.81 (s, 1H), 4.47-4.41 (m, 2H), 3.83-3.82 (m, 2H), 1.22-1.20 (m, 6H). $^{19}$F NMR (377 MHz, DMSO-d6) δ −115.19 (m, 2F).

Example 81. 5-[8-(3,3-difluoro-4,4-dimethyl-pyrrolidin-1-yl)-3-fluoro-imidazo[1,2-b]pyridazin-6-yl]-1H-pyrimidine-2,4-dione

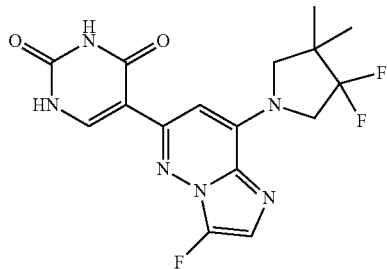 [SMILES: CC1(C)CN(c2cc(-c3c[nH]c(=O)[nH]c3=O)nn3c(F)cnc23)CC1(F)F]

5-[8-(3,3-difluoro-4,4-dimethyl-pyrrolidin-1-yl)-3-fluoro-imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 8-(3,3-difluoro-4,4-dimethyl-pyrrolidin-1-yl)-6-(2,4-dimethoxypyrimidin-5-yl)-3-fluoro-imidazo[1,2-b]pyridazine and isolated by filtration as an HCl salt. ES/MS: 381.10 [M+1]. $^1$H NMR (400 MHz, DMSO-d6) δ 11.50-11.36 (m, 2H), 7.98-7.96 (m, 1H), 7.42-7.40 (m, 1H), 6.59-6.58 (m, 1H), 4.40 (brs, 2H), 3.85 (brs, 2H), 1.21 (s, 6H). $^{19}$F NMR (377 MHz, DMSO-d6) δ −115.42 (m, 2F), −155.50 (d, J=7.4 Hz, 1F).

Example 82. 5-(8-(7,7-difluoro-5-azaspiro[2.4]heptan-5-yl)-3-fluoroimidazo[1,2-b]pyridazin-6-yl)pyrimidine-2,4(1H,3H)-dione

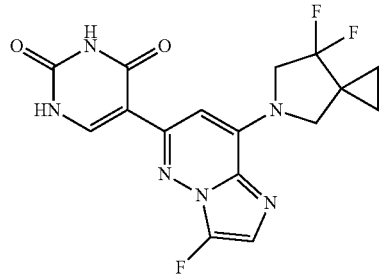 [SMILES: O=c1[nH]cc(-c2cc(N3CC(F)(F)C4(CC4)C3)c3ncc(F)n3n2)c(=O)[nH]1]

A solution of 8-(7,7-difluoro-5-azaspiro[2.4]heptan-5-yl)-6-(2,4-dimethoxypyrimidin-5-yl)-3-fluoroimidazo[1,2-b]pyridazine (377 mg) in 1:1 1N HCl/MeOH (5 mL) was heated to 80° C. After 20 hours, the reaction mixture was filtered. The resulting solids were washed with MeCN (10 mL) and dried under reduced pressure to afford the hydrochloride salt of 5-(8-(7,7-difluoro-5-azaspiro[2.4]heptan-5-yl)-3-fluoroimidazo[1,2-b]pyridazin-6-yl)pyrimidine-2,4(1H,3H)-dione. $^1$H NMR (400 MHz, Methanol-d4) δ 8.13 (s, 1H), 7.24 (d, J=7.1 Hz, 1H), 6.70 (s, 1H), 4.56 (t, J=12.5 Hz, 2H), 4.06 (s, 2H), 1.19-1.14 (m, 2H), 1.01-0.91 (m, 3H). $^{19}$F NMR (376 MHz, Methanol-d4) δ −111.24 (t, J=12.4 Hz, 2F), −157.79 (d, J=7.4 Hz, 1F). ES/MS m/z: 379.10 [M+H].

Example 83. 5-(8-(7,7-difluoro-5-azaspiro[2.4]heptan-5-yl)imidazo[1,2-b]pyridazin-6-yl)pyrimidine-2,4(1H,3H)-dione

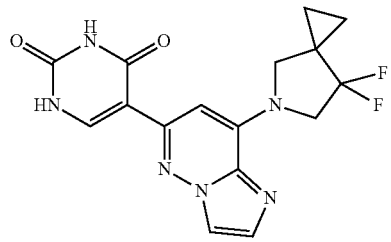 [SMILES: O=c1[nH]cc(-c2cc(N3CC(F)(F)C4(CC4)C3)c3nccn3n2)c(=O)[nH]1]

A solution of 8-(7,7-difluoro-5-azaspiro[2.4]heptan-5-yl)-6-(2,4-dimethoxypyrimidin-5-yl)imidazo[1,2-b]pyridazine (55 mg) in 1:1 1N HCl/MeOH (2 mL) was heated to 80 C. After 14 hours, the solvent was evaporated and purified with Prep HPLC to afford 5-(8-(7,7-difluoro-5-azaspiro[2.4]heptan-5-yl)imidazo[1,2-b]pyridazin-6-yl)pyrimidine-2,4(1H,3H)-dione trifluoroacetic acid salt. ES/MS m/z: 361.10 [M+H]. $^1$H NMR (400 MHz, DMSO-d6) δ 11.40 (dd, J=9.5, 4.1 Hz, 2H), 8.08 (d, J=1.1 Hz, 1H), 7.95 (d, J=6.1 Hz, 1H), 7.58 (d, J=1.1 Hz, 1H), 6.61 (s, 1H), 4.57 (t, J=12.4 Hz, 2H), 4.02 (s, 2H), 1.10-0.96 (m, 4H). $^{19}$F NMR (376 MHz, DMSO-d6) δ −75.28 (s, 3F), −107.45 (t, J=12.6 Hz, 2F).

Example 84. 5-(8-(7,7-difluoro-5-azaspiro[2.4]heptan-5-yl)-[1,2,4]triazolo[1,5-b]pyridazin-6-yl)pyrimidine-2,4(1H,3H)-dione

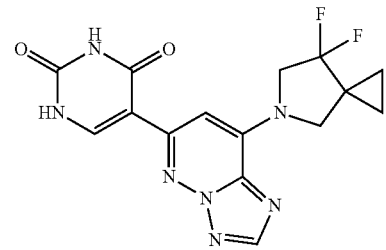 [SMILES: O=c1[nH]cc(-c2cc(N3CC(F)(F)C4(CC4)C3)c3ncnn3n2)c(=O)[nH]1]

5-(8-(7,7-difluoro-5-azaspiro[2.4]heptan-5-yl)-[1,2,4]triazolo[1,5-b]pyridazin-6-yl)pyrimidine-2,4(1H,3H)-dione was prepared in the manner described for Example 67, but replacing 8-cyclopropyl-6-(2,4-dimethoxypyrimidin-5-yl)-2-methyl-imidazo[1,2-b]pyridazine with 8-(7,7-difluoro-5-azaspiro[2.4]heptan-5-yl)-6-(2,4-dimethoxypyrimidin-5-yl)-[1,2,4]triazolo[1,5-b]pyridazine. Purification was accomplished by RP-HPLC (10-90% MeCN/H$_2$O with TFA modifier, Gemini column). ES/MS m/z: 362.1 [M+1]. $^1$H NMR (400 MHz, DMSO-d6) δ 11.48 (d, J=3.6 Hz, 2H), 8.45 (s, 1H), 8.06 (d, J=6.4 Hz, 1H), 7.00 (s, 1H), 4.53 (s, 2H), 4.03 (s, 2H), 1.12-0.91 (m, 4H). $^{19}$F NMR (376 MHz, DMSO-d6) δ −107.36 (t, J=12.6 Hz, 2F).

Example 85. 3-[(1S,2S)-2-[6-(2,4-dioxo-1H-pyrimidin-5-yl)imidazo[1,2-b]pyridazin-8-yl]cyclopropyl]-5-fluoro-benzonitrile and 3-[(1R,2R)-2-[6-(2,4-dioxo-1H-pyrimidin-5-yl)imidazo[1,2-b]pyridazin-8-yl]cyclopropyl]-5-fluoro-benzonitrile

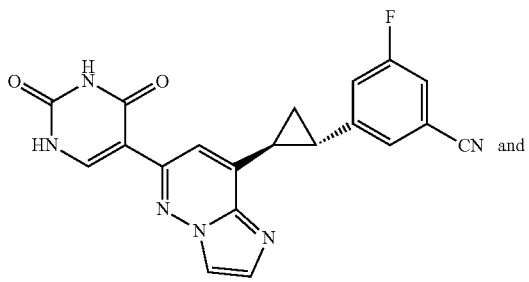

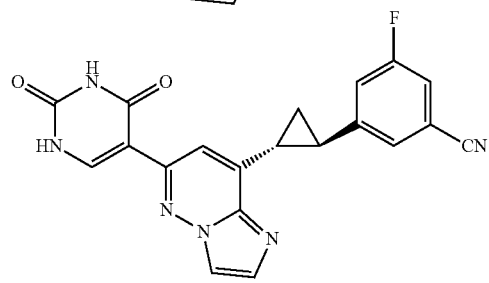

3-[(1S,2S)-2-[6-(2,4-dioxo-1H-pyrimidin-5-yl)imidazo[1,2-b]pyridazin-8-yl]cyclopropyl]-5-fluoro-benzonitrile was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 3-[(1S,2S)-2-[6-(2,4-dimethoxypyrimidin-5-yl)imidazo[1,2-b]pyridazin-8-yl]cyclopropyl]-5-fluoro-benzonitrile (Racemic Mixture) and isolated by filtration as an HCl salt. ES/MS m/z: 389.10 [M+H]. $^1$H NMR (400 MHz, DMSO-d6) δ 11.78-11.74 (m, 1H), 11.63-11.62 (m, 1H), 8.57-8.56 (m, 1H), 8.22 (s, 1H), 8.12-8.11 (m, 1H), 7.81 (s, 1H), 7.75-7.65 (m, 2H), 7.60-7.57 (m, 1H), 3.13-3.03 (m, 1H), 2.87-2.82 (m, 1H), 2.06-1.95 (m, 2H). $^{19}$F NMR (377 MHz, DMSO-d6) δ −111.39 (m, 1F).

Example 86. 5-[2-cyclopropyl-8-[(1S,2S)-2-(4-fluorophenyl)cyclopropyl]imidazo[1,2-b]pyridazin-6-yl]-1H-pyrimidine-2,4-dione and 5-[2-cyclopropyl-8-[(1R,2R)-2-(4-fluorophenyl)cyclopropyl]imidazo[1,2-b]pyridazin-6-yl]-1H-pyrimidine-2,4-dione

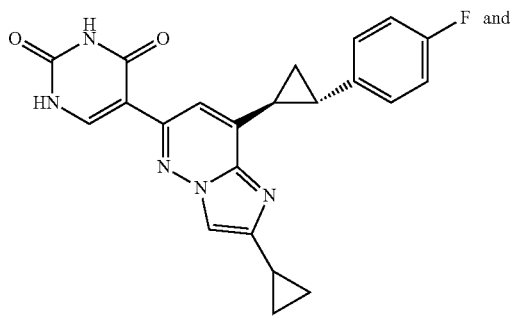

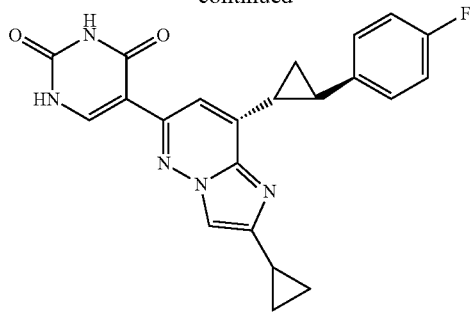

5-[2-cyclopropyl-8-[(1S,2S)-2-(4-fluorophenyl)cyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 2-cyclopropyl-6-(2,4-dimethoxypyrimidin-5-yl)-8-[(1S,2S)-2-(4-fluorophenyl)cyclopropyl]imidazo[1,2-b]pyridazine (Racemic Mixture) and isolated by filtration as an HCl salt. ES/MS m/z: 404.10 [M+H]. $^1$H NMR (400 MHz, DMSO-d6) δ 11.74-11.73 (m, 1H), 11.60-11.59 (m, 1H), 8.34 (s, 1H), 8.07-8.06 (m, 1H), 7.72 (s, 1H), 7.39-7.29 (m, 2H), 7.22-7.11 (m, 2H), 3.03-3.02 (m, 1H), 2.76-2.71 (m, 1H), 2.22-2.15 (m, 1H), 1.83-1.80 (m, 2H), 1.15-1.10 (m, 2H), 1.06-1.00 (m, 2H). $^{19}$F NMR (376 MHz, DMSO-d6) δ −117.27 (m, 1F).

Example 87. 5-[3-fluoro-8-[(1S,2S)-2-phenylcyclopropyl]imidazo[1,2-b]pyridazin-6-yl]-1H-pyrimidine-2,4-dione and 5-[3-fluoro-8-[(1R,2R)-2-phenylcyclopropyl]imidazo[1,2-b]pyridazin-6-yl]-1H-pyrimidine-2,4-dione

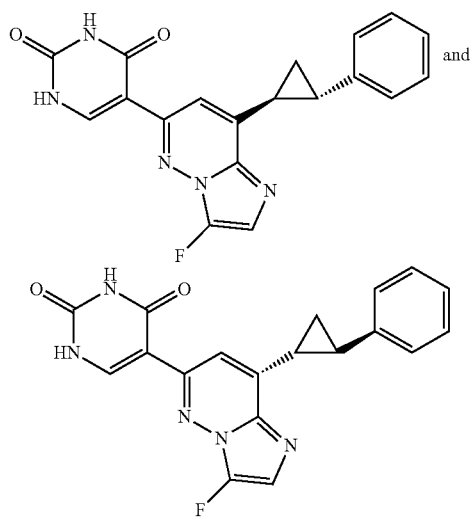

5-[3-fluoro-8-[(1S,2S)-2-phenylcyclopropyl]imidazo[1,2-b]pyridazin-6-yl]-1H-pyrimidine-2,4-dione was prepared as a racemic mixture in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-3-fluoro-8-[(1S,2S)-2-phenylcyclopropyl]imidazo[1,2-b]pyridazine (Racemic Mixture) and purified by RP-HPLC (5-100% MeCN/H$_2$O with TFA, Gemini column). ES/MS m/z: 364.10 [M+H]. $^1$H NMR (400 MHz, DMSO-d6) δ 11.53-11.52 (m, 2H), 8.04-8.02 (m, 1H), 7.55-7.50 (m, 1H), 7.46 (s, 1H), 7.36-7.13 (m, 5H), 2.84-2.79 (m, 1H), 2.74-2.64 (m, 1H), 2.13-2.03 (m, 1H), 1.78-1.73 (m, 1H). $^{19}$F NMR (376 MHz, DMSO-d6) δ −74.87 (s, 3F), −155.60 (d, J=7.0 Hz, 1F).

Example 88. 5-[8-[(1S,2S)-2-(2,4-difluorophenyl)cyclopropyl]-3-fluoro-imidazo[1,2-b]pyridazin-6-yl]-1H-pyrimidine-2,4-dione

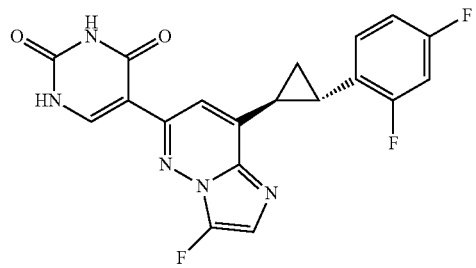 [SMILES: O=c1[nH]cc(-c2cc([C@H]3C[C@@H]3c3ccc(F)cc3F)c3ncc(F)n3n2)c(=O)[nH]1]

5-[8-[(1S,2S)-2-(2,4-difluorophenyl)cyclopropyl]-3-fluoro-imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 8-[(1S,2S)-2-(2,4-difluorophenyl)cyclopropyl]-6-(2,4-dimethoxypyrimidin-5-yl)-3-fluoro-imidazo[1,2-b]pyridazine and isolated by filtration as an HCl salt. ES/MS: 400.10 [M+1]. $^1$H NMR (400 MHz, DMSO-d6) δ 11.64-11.48 (m, 2H), 8.06-8.02 (m, 1H), 7.63-7.61 (m, 1H), 7.55 (s, 1H), 7.36-7.32 (m, 1H), 7.25-7.19 (m, 1H), 7.14-7.04 (m, 1H), 3.02-2.92 (m, 1H), 2.79-2.66 (m, 1H), 2.13-2.05 (m, 1H), 1.82-1.77 (m, 1H). $^{19}$F NMR (377 MHz, DMSO-d6) δ −113.39 (m, 1F), −115.89 (m, 1F), −155.44 (d, J=7.1 Hz, 1F).

Example 89. 5-[8-(4,4-dimethyl-1-piperidyl)imidazo[1,2-b]pyridazin-6-yl]-1H-pyrimidine-2,4-dione

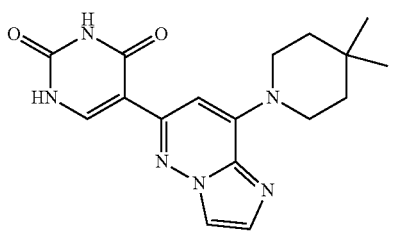 [SMILES: CC1(C)CCN(c2cc(-c3c[nH]c(=O)[nH]c3=O)nn3ccnc23)CC1]

5-[8-(4,4-dimethyl-1-piperidyl)imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 6-(2,4-dimethoxypyrimidin-5-yl)-8-(4,4-dimethyl-1-piperidyl)imidazo[1,2-b]pyridazine and isolated by filtration as an HCl salt. ES/MS: 341.20 [M+1]. $^1$H NMR (400 MHz, DMSO-d6) δ 11.61-11.54 (m, 1H), 11.48-11.47 (m, 1H), 8.48-8.47 (m, 2H), 8.24-8.23 (m, 1H), 8.03-8.01 (m, 1H), 7.86-7.81 (m, 1H), 7.22 (s, 1H), 3.82-3.74 (m, 4H), 2.08 (s, OH), 1.54-1.46 (m, 4H), 1.01 (s, 6H).

Example 90. 5-[8-[(1S,2S)-2-(3,4-difluorophenyl)cyclopropyl]-3-fluoro-imidazo[1,2-b]pyridazin-6-yl]-1H-pyrimidine-2,4-dione

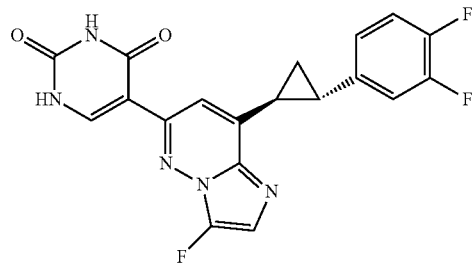 [SMILES: O=c1[nH]cc(-c2cc([C@H]3C[C@@H]3c3ccc(F)c(F)c3)c3ncc(F)n3n2)c(=O)[nH]1]

5-[8-[(1S,2S)-2-(3,4-difluorophenyl)cyclopropyl]-3-fluoro-imidazo[1,2-b]pyridazin-6-yl]-1H-pyrimidine-2,4-dione was prepared in the manner described for Example 67, but replacing 6-(2,4-dimethoxypyrimidin-5-yl)-8-[(3R)-3-(4-fluorophenyl)pyrrolidin-1-yl]imidazo[1,2-b]pyridazine with 8-[(1S,2S)-2-(2,4-difluorophenyl)cyclopropyl]-6-(3,4-dimethoxypyrimidin-5-yl)-3-fluoro-imidazo[1,2-b]pyridazine and isolated by filtration as an HCl salt. ES/MS: 400.10 [M+1]. $^1$H NMR (400 MHz, DMSO-d6) δ 11.56-11.54 (s, 2H), 8.04-8.02 (m, 1H), 7.56-7.53 (m, 1H), 7.48 (s, 1H), 7.42-7.29 (m, 2H), 7.18-7.09 (m, 1H), 2.89-2.84 (m, 1H), 2.71-2.67 (m, 1H), 2.13-2.08 (m, 1H), 1.78-1.73 (m, 1H). $^{19}$F NMR (377 MHz, DMSO-d6) δ −139.37 (m, 1F), −142.87 (m, 1F), −155.62 (d, J=7.0 Hz, 1F).

Example 91. 5-(7-(3,3-dimethylpyrrolidin-1-yl)pyrazolo[1,5-a]pyrimidin-5-yl)pyrimidine-2,4(1H,3H)-dione

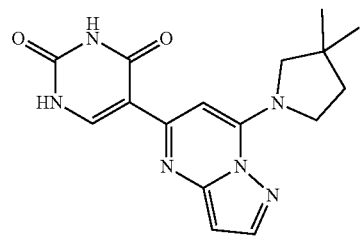 [SMILES: CC1(C)CCN(c2cc(-c3c[nH]c(=O)[nH]c3=O)nc3ccnn23)C1]

5-(7-(3,3-dimethylpyrrolidin-1-yl)pyrazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-(2,4-dimethoxypyrimidin-5-yl)-7-(3,3-dimethylpyrrolidin-1-yl)pyrazolo[1,5-a]pyrimidine. ES/MS m/z: 327.20 [M+H]. $^1$H NMR (400 MHz, DMSO-d6) δ 12.13 (s, 1H), 11.82 (s, 1H), 8.56 (d, J=6.0 Hz, 1H), 8.16 (d, J=2.2 Hz, 1H), 6.71 (s, 1H), 6.53 (s, 1H), 3.98 (m, 4H), 1.90-1.78 (m, 2H), 1.14 (s, 6H).

Example 92. 5-(7-(3,3-dimethylpyrrolidin-1-yl)-[1,2,4]triazolo[1,5-a]pyrimidin-5-yl)pyrimidine-2,4(1H,3H)-dione

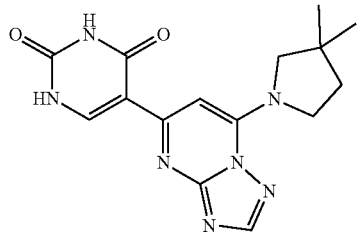 [SMILES: CC1(C)CCN(c2cc(-c3c[nH]c(=O)[nH]c3=O)nc3ncnn23)C1]

5-(7-(3,3-dimethylpyrrolidin-1-yl)-[1,2,4]triazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-(2,4-dimethoxypyrimidin-5-yl)-7-(3,3-dimethylpyrrolidin-1-yl)-[1,2,4]triazolo[1,5-a]pyrimidine. Purification was accomplished via RP-HPLC (10-90% MeCN/H$_2$O with TFA modifier, Gemini column). ES/MS m/z: 328.13 [M+H]. $^1$H NMR (400 MHz, DMSO-d6) δ 11.66 (dd, J=6.4, 2.0 Hz, 1H), 11.53 (d, J=1.9 Hz, 1H), 8.53-8.39 (m, 2H), 7.41 (s, 1H), 3.87-3.55 (m, 4H), 1.82 (t, J=7.1 Hz, 2H), 1.13 (s, 6H).

Example 93. 5-(8-(3,3-difluoropiperidin-1-yl)imidazo[1,2-b]pyridazin-6-yl)pyrimidine-2,4(1H,3H)-dione

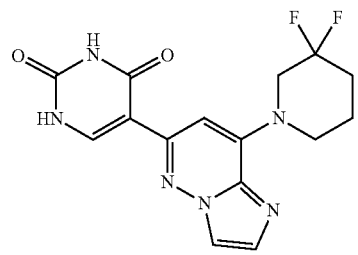 [SMILES: O=c1[nH]cc(-c2cc(N3CCCC(F)(F)C3)c3nccn3n2)c(=O)[nH]1]

5-(8-(3,3-difluoropiperidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(3,3-difluoropiperidin-1-yl)-6-(2,4-dimethoxypyrimidin-5-yl)imidazo[1,2-b]pyridazine. Purification was accomplished via RP-HPLC (10-90% MeCN/H$_2$O with TFA modifier, Gemini column). ES/MS m/z: 349.10 [M+H]. $^1$H NMR (400 MHz, DMSO-d6) δ 11.50-11.37 (m, 2H), 8.07 (d, J=1.2 Hz, 1H), 7.95 (d, J=6.0 Hz, 1H), 7.59 (d, J=1.2 Hz, 1H), 6.96 (s, 1H), 4.68 (t, J=12.0 Hz, 2H), 3.80 (t, J=5.3 Hz, 2H), 2.14 (tt, J=14.4, 6.6 Hz, 2H), 1.91-1.79 (m, 2H). $^{19}$F NMR (376 MHz, DMSO-d6) δ −75.42 (s, 3F), −100.53 (p, J=13.2 Hz, 2F).

Example 94. 5-(8-(3-azabicyclo[3.2.1]octan-3-yl)imidazo[1,2-b]pyridazin-6-yl)pyrimidine-2,4(1H,3H)-dione

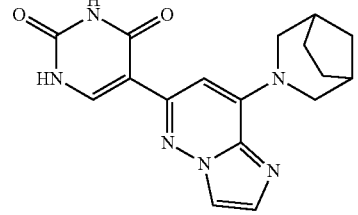

5-(8-(3-azabicyclo[3.2.1]octan-3-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with bicyclo[3.2.1]octan-3-yl)-6-(2,4-dimethoxypyrimidin-5-yl)imidazo[1,2-b]pyridazine. Purification was accomplished via RP-HPLC (10-90% MeCN/H$_2$O with TFA modifier, Gemini column). ES/MS m/z: 339.1 [M+H]. $^1$H NMR (400 MHz, DMSO-d6) δ 11.44-11.34 (m, 2H), 8.04 (d, J=1.2 Hz, 1H), 7.93 (d, J=6.1 Hz, 1H), 7.58 (t, J=1.4 Hz, 1H), 6.84 (d, J=1.5 Hz, 1H), 4.57 (d, J=11.7 Hz, 2H), 3.07 (dd, J=12.0, 1.5 Hz, 2H), 2.37 (d, J=5.0 Hz, 2H), 1.73-1.53 (m, 6H).

Example 95. 5-(8-((2S,2S)-2-(4-fluoro-3-(trifluoromethyl)phenyl)cyclopropyl)imidazo[1,2-b]pyridazin-6-yl)pyrimidine-2,4(1H,3H)-dione and 5-(8-((1R,2R)-2-(4-fluoro-3-(trifluoromethyl)phenyl)cyclopropyl)imidazo[1,2-b]pyridazin-6-yl)pyrimidine-2,4(1H,3H)-dione

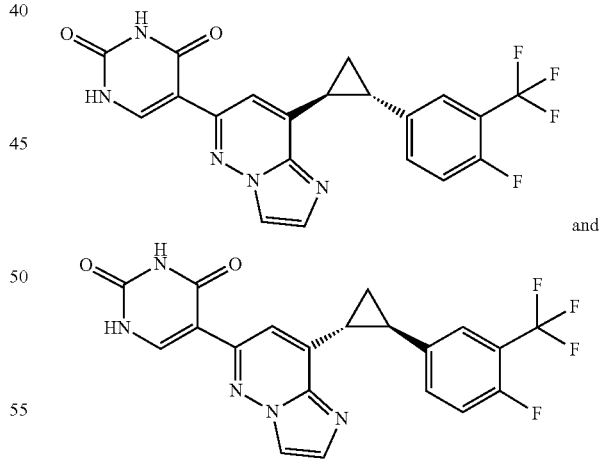

and 5-(8-((1S,2S)-2-(4-fluoro-3-(trifluoromethyl)phenyl)cyclopropyl)imidazo[1,2-b]pyridazin-6-yl)pyrimidine-2,4(1H,3H)-dione was prepared as a racemic mixture of TFA salts in the manner described for Example 1, but replacing 8-cyclopropyl-6-(2,4-dimethoxypyrimidin-5-yl)-2-methyl-imidazo[1,2-b]pyridazine with racemic 6-(2,4-dimethoxy-pyrimidin-5-yl)-8-((1S,2S)-2-(4-fluoro-3-(trifluoromethyl)phenyl)cyclopropyl)imidazo[1,2-b]pyridazine (racemic mixture). Purification was accomplished via RP-HPLC (10-

90% MeCN/H₂O with TFA modifier, Gemini column). ES/MS m/z: 432.07 [M+H]. ¹H NMR (400 MHz, DMSO-d6) δ11.60-11.51 (m, 2H), 8.36 (d, J=1.4 Hz, 1H), 8.04 (d, J=6.1 Hz, 1H), 7.90 (d, J=1.5 Hz, 1H), 7.70-7.62 (m, 2H), 7.61 (s, 1H), 7.47 (dd, J=10.7, 8.5 Hz, 1H), 2.93 (ddd, J=9.1, 6.3, 4.4 Hz, 1H), 2.78 (ddd, J=9.0, 6.0, 4.4 Hz, 1H), 2.08 (q, J=5.0, 4.4 Hz, 1H), 1.86 (ddd, J=8.8, 6.4, 5.1 Hz, 1H). ¹⁹F NMR (376 MHz, DMSO-d6) δ −60.42 (d, J=12.5 Hz, 3F), −75.14, −120.29 (dtq, J=17.1, 11.6, 6.0, 5.4 Hz, 1F).

Example 96. 5-(8-cyclopropyl-2-(2-(trifluoromethyl)phenyl)imidazo[1,2-b]pyridazin-6-yl)pyrimidine-2,4(1H,3H)-dione

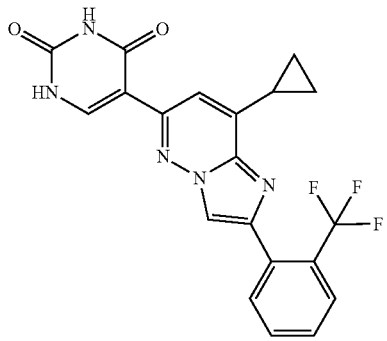 [SMILES: O=c1[nH]cc(-c2cc(C3CC3)c3nc(-c4ccccc4C(F)(F)F)cn3n2)c(=O)[nH]1]

5-(8-cyclopropyl-2-(2-(trifluoromethyl)phenyl)imidazo[1,2-b]pyridazin-6-yl)pyrimidine-2,4(1H,3H)-dione as a TFA salt was prepared in the manner described for Example 1, but replacing 8-cyclopropyl-6-(2,4-dimethoxypyrimidin-5-yl)-2-methyl-imidazo[1,2-b]pyridazine with 8-cyclopropyl-6-(2,4-dimethoxypyrimidin-5-yl)-2-(2-(trifluoromethyl)phenyl)imidazo[1,2-b]pyridazine. Purification was accomplished via RP-HPLC (10-90% MeCN/H₂O with TFA modifier, Gemini column). ES/MS m/z: 414.10 [M+H]. ¹H NMR (400 MHz, DMSO-d6) δ 11.50 (s, 2H), 8.37 (s, 1H), 8.02 (s, 1H), 7.89 (t, J=7.8 Hz, 2H), 7.78 (t, J=7.6 Hz, 1H), 7.64 (t, J=7.7 Hz, 1H), 7.41 (s, 1H), 2.44 (td, J=8.6, 4.4 Hz, 1H), 1.39 (dt, J=6.1, 3.2 Hz, 2H), 1.21 (dt, J=8.4, 3.3 Hz, 2H). ¹⁹F NMR (376 MHz, DMSO-d6) δ −57.14 (s, 3F).

Example 97. 5-(8-cyclopropyl-2-(pyridin-4-yl)imidazo[1,2-b]pyridazin-6-yl)pyrimidine-2,4(1H,3H)-dione

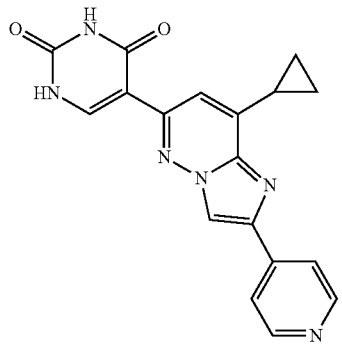 [SMILES: O=c1[nH]cc(-c2cc(C3CC3)c3nc(-c4ccncc4)cn3n2)c(=O)[nH]1]

5-(8-cyclopropyl-2-(pyridin-4-yl)imidazo[1,2-b]pyridazin-6-yl)pyrimidine-2,4(1H,3H)-dione was prepared as an HCl salt in the manner described for Example 1, but replacing 8-cyclopropyl-6-(2,4-dimethoxypyrimidin-5-yl)-2-methyl-imidazo[1,2-b]pyridazine with 8-cyclopropyl-6-(2,4-dimethoxypyrimidin-5-yl)-2-(pyridin-4-yl)imidazo[1,2-b]pyridazine. Isolation was accomplished via filtration. ES/MS m/z: 347.10 [M+H]. ¹H NMR (400 MHz, DMSO-d6) δ 11.59 (d, J=6.3 Hz, 1H), 11.54 (d, J=1.9 Hz, 1H), 9.31 (d, J=1.2 Hz, 1H), 8.90 (d, J=6.6 Hz, 2H), 8.48 (d, J=6.7 Hz, 2H), 8.04 (d, J=6.2 Hz, 1H), 7.45 (s, 1H), 2.56 (ddd, J=8.4, 6.3, 4.1 Hz, 1H), 1.38-1.21 (m, 4H).

Example 98. 5-(8-((2S,2S)-2-(4-chloro-3-fluorophenyl)cyclopropyl)imidazo[1,2-b]pyridazin-6-yl)pyrimidine-2,4(1H,3H)-dione and 5-(8-((1R,2R)-2-(4-chloro-3-fluorophenyl)cyclopropyl)imidazo[1,2-b]pyridazin-6-yl)pyrimidine-2,4(1H,3H)-dione

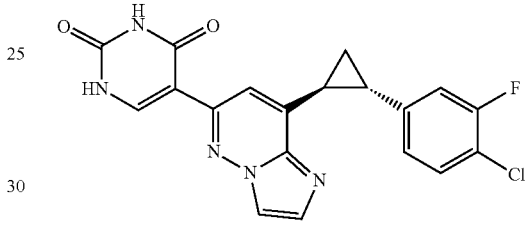

and

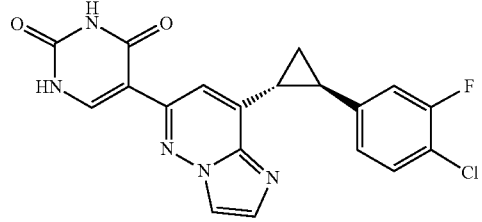

5-(8-((1S,2S)-2-(4-chloro-3-fluorophenyl)cyclopropyl)imidazo[1,2-b]pyridazin-6-yl)pyrimidine-2,4(1H,3H)-dione was prepared as a racemic mixture of TFA salts in the manner described for Example 1, but replacing 8-cyclopropyl-6-(2,4-dimethoxypyrimidin-5-yl)-2-methyl-imidazo[1,2-b]pyridazine with racemic 8-((1S,2S)-2-(4-chloro-3-fluorophenyl)cyclopropyl)-6-(2,4-dimethoxypyrimidin-5-yl)imidazo[1,2-b]pyridazine (racemic mixture). Purification was accomplished via RP-HPLC (10-90% MeCN/H₂O with TFA modifier, Gemini column). ES/MS m/z: 398.10 [M+H]. ¹H NMR (400 MHz, DMSO-d6) δ11.59-11.51 (m, 2H), 8.34 (d, J=1.5 Hz, 1H), 8.03 (d, J=6.1 Hz, 1H), 7.89 (s, 1H), 7.59 (s, 1H), 7.51 (t, J=8.2 Hz, 1H), 7.35 (dd, J=10.9, 2.1 Hz, 1H), 7.16 (dd, J=8.4, 2.0 Hz, 1H), 2.84 (ddd, J=9.0, 6.2, 4.4 Hz, 1H), 2.76 (ddd, J=8.8, 6.0, 4.3 Hz, 1H), 2.09 (dt, J=8.8, 5.3 Hz, 1H), 1.81 (ddd, J=8.7, 6.3, 5.0 Hz, 1H). ¹⁹F NMR (376 MHz, DMSO-d6) δ −75.15 (s, 3F), −117.14 (dd, J=10.8, 8.0 Hz, 1F).

Example 99. 5-(8-((2S,2S)-2-(3-chloro-4-fluorophenyl)cyclopropyl)imidazo[1,2-b]pyridazin-6-yl)pyrimidine-2,4(1H,3H)-dione and 5-(8-((1R,2R)-2-(3-chloro-4-fluorophenyl)cyclopropyl)imidazo[1,2-b]pyridazin-6-yl)pyrimidine-2,4(1H,3H)-dione

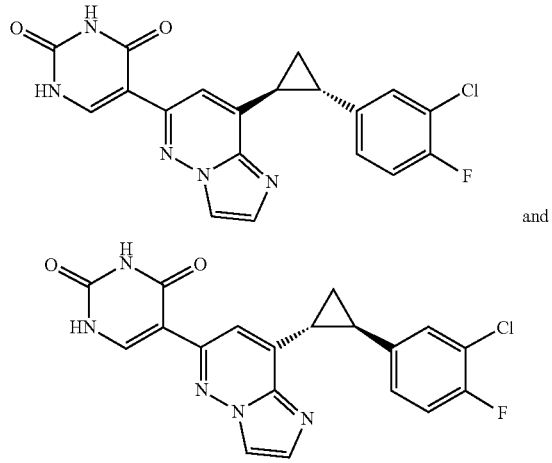

and 5-(8-((1S,2S)-2-(3-chloro-4-fluorophenyl)cyclopropyl)imidazo[1,2-b]pyridazin-6-yl)pyrimidine-2,4(1H,3H)-dione was prepared as a racemic mixture of TFA salts in the manner described for Example 1, but replacing 8-cyclopropyl-6-(2,4-dimethoxypyrimidin-5-yl)-2-methyl-imidazo[1,2-b]pyridazine with racemic 8-((1S,2S)-2-(3-chloro-4-fluorophenyl)cyclopropyl)-6-(2,4-dimethoxypyrimidin-5-yl)imidazo[1,2-b]pyridazine (racemic mixture). Purification was accomplished via RP-HPLC (10-90% MeCN/H₂O with TFA modifier, Gemini column). ES/MS m/z: 398.08 [M+H]. ¹H NMR (400 MHz, DMSO-d6) δ11.60 (dd, J=6.3, 1.9 Hz, 1H), 11.56 (d, J=1.9 Hz, 1H), 8.39 (d, J=1.5 Hz, 1H), 8.05 (d, J=6.2 Hz, 1H), 7.96 (d, J=1.6 Hz, 1H), 7.63 (s, 1H), 7.50 (dd, J=7.1, 2.2 Hz, 1H), 7.35 (t, J=8.9 Hz, 1H), 7.29 (ddd, J=8.6, 4.8, 2.2 Hz, 1H), 2.78 (dddd, J=19.0, 8.8, 6.1, 4.4 Hz, 2H), 2.02 (dt, J=8.8, 5.4 Hz, 1H), 1.82 (ddd, J=8.7, 6.4, 5.0 Hz, 1H). ¹⁹F NMR (376 MHz, DMSO-d6) δ−75.19 (s, 3F), −120.53 (ddd, J=9.0, 7.0, 4.7 Hz, 1F).

Example 100. 5-(8-((2S,2S)-2-(3-fluoro-4-(trifluoromethyl)phenyl)cyclopropyl)imidazo[1,2-b]pyridazin-6-yl)pyrimidine-2,4(1H,3H)-dione and 5-(8-((1R,2R)-2-(3-fluoro-4-(trifluoromethyl)phenyl)cyclopropyl)imidazo[1,2-b]pyridazin-6-yl)pyrimidine-2,4(1H,3H)-dione

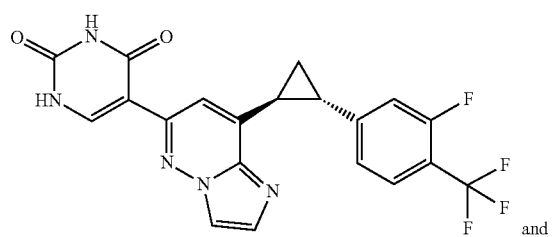

and

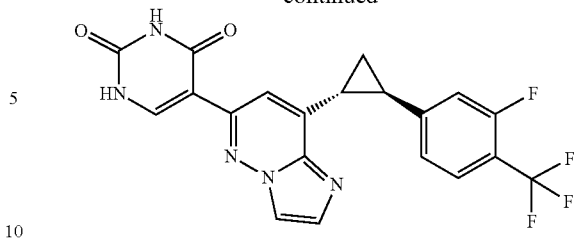

5-(8-((1S,2S)-2-(3-fluoro-4-(trifluoromethyl)phenyl)cyclopropyl)imidazo[1,2-b]pyridazin-6-yl)pyrimidine-2,4(1H,3H)-dione was prepared as a racemic mixture of TFA salts in the manner described for Example 1, but replacing 8-cyclopropyl-6-(2,4-dimethoxypyrimidin-5-yl)-2-methyl-imidazo[1,2-b]pyridazine with racemic 6-(2,4-dimethoxypyrimidin-5-yl)-8-((1S,2S)-2-(3-fluoro-4-(trifluoromethyl)phenyl)cyclopropyl)imidazo[1,2-b]pyridazine (racemic mixture). Purification was accomplished via RP-HPLC (10-90% MeCN/H₂O with TFA modifier, Gemini column). ES/MS m/z: 432.10 [M+H]. ¹H NMR (400 MHz, DMSO-d6) δ 11.53 (s, 2H), 8.30 (s, 1H), 8.01 (d, J=6.3 Hz, 1H), 7.81 (s, 1H), 7.69 (t, J=8.0 Hz, 1H), 7.57 (s, 1H), 7.44 (d, J=12.4 Hz, 1H), 7.33 (d, J=8.1 Hz, 1H), 2.97 (dt, J=9.6, 5.5 Hz, 1H), 2.84 (dt, J=9.7, 5.6 Hz, 1H), 2.21 (dt, J=9.0, 5.5 Hz, 1H), 1.86 (dt, J=8.7, 5.4 Hz, 1H). ¹⁹F NMR (376 MHz, DMSO-d6) δ −60.12 (d, J=12.0 Hz, 3F), −74.93, −116.77 (pd, J=12.0, 7.6 Hz, 1F).

Example 101. 5-(8-((2S,2S)-2-(2-methoxyphenyl)cyclopropyl)imidazo[1,2-b]pyridazin-6-yl)pyrimidine-2,4(1H,3H)-dione and 5-(8-((1R,2R)-2-(2-methoxyphenyl)cyclopropyl)imidazo[1,2-b]pyridazin-6-yl)pyrimidine-2,4(1H,3H)-dione

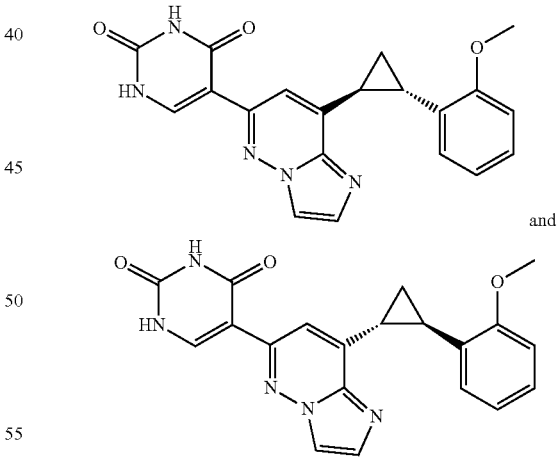

5-(8-((1S,2S)-2-(2-methoxyphenyl)cyclopropyl)imidazo[1,2-b]pyridazin-6-yl)pyrimidine-2,4(1H,3H)-dione was prepared as a racemic mixture of TFA salts in the manner described for Example 1, but replacing 8-cyclopropyl-6-(2,4-dimethoxypyrimidin-5-yl)-2-methyl-imidazo[1,2-b]pyridazine with racemic 6-(2,4-dimethoxypyrimidin-5-yl)-8-((1S,2S)-2-(2-methoxyphenyl)cyclopropyl)imidazo[1,2-b]pyridazine (Racemic Mixture). Purification was accomplished via RP-HPLC (10-90% MeCN/H₂O with TFA modifier, Gemini column). ES/MS m/z: 376.20 [M+H]. ¹H NMR (400 MHz, DMSO-d6) δ 11.61-11.47 (m, 2H), 8.37 (s, 1H), 8.04 (d, J=6.0 Hz, 1H), 7.93 (s, 1H), 7.61 (s, 1H), 7.22 (ddd, J=8.5, 7.4, 1.7 Hz, 1H), 7.11 (dd, J=7.7, 1.7 Hz, 1H), 7.01-6.88 (m, 2H), 3.74 (s, 3H), 2.91 (td, J=9.2, 5.6 Hz, 1H), 2.65 (dt, J=8.8, 5.3 Hz, 1H), 1.96 (dt, J=9.8, 5.1 Hz, 1H), 1.74 (ddd, J=8.6, 6.6, 4.7 Hz, 1H).

Example 102. 5-(8-cyclopropyl-2-(pyridin-3-yl)imidazo[1,2-b]pyridazin-6-yl)pyrimidine-2,4(1H,3H)-dione

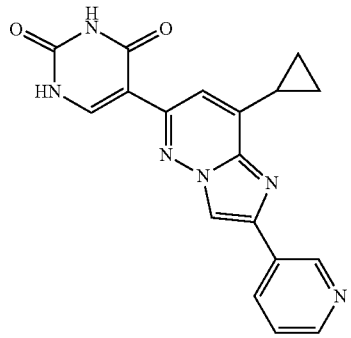 [SMILES: O=c1[nH]cc(-c2cc(C3CC3)c3nc(-c4cccnc4)cn3n2)c(=O)[nH]1]

5-(8-cyclopropyl-2-(pyridin-3-yl)imidazo[1,2-b]pyridazin-6-yl)pyrimidine-2,4(1H,3H)-dione was prepared as a TFA salt in the manner described for Example 1, but replacing 8-cyclopropyl-6-(2,4-dimethoxypyrimidin-5-yl)-2-methyl-imidazo[1,2-b]pyridazine with racemic 8-cyclopropyl-6-(2,4-dimethoxypyrimidin-5-yl)-2-(pyridin-3-yl)imidazo[1,2-b]pyridazine. Purification was accomplished via RP-HPLC (10-90% MeCN/H$_2$O with TFA modifier, Gemini column). ES/MS m/z: 347.11 [M+H]. $^1$H NMR (400 MHz, DMSO-d6) δ11.49 (d, J=7.0 Hz, 2H), 9.27 (d, J=2.1 Hz, 1H), 8.91 (s, 1H), 8.59 (d, J=4.7 Hz, 1H), 8.47 (d, J=8.0 Hz, 1H), 8.00 (d, J=6.0 Hz, 1H), 7.59 (dd, J=7.6, 5.2 Hz, 1H), 7.35 (s, 1H), 2.60-2.53 (m, 1H), 1.35-1.20 (m, 4H).

Example 103. 5-(8-cyclopropyl-2-(pyridin-2-yl)imidazo[1,2-b]pyridazin-6-yl)pyrimidine-2,4(1H,3H)-dione

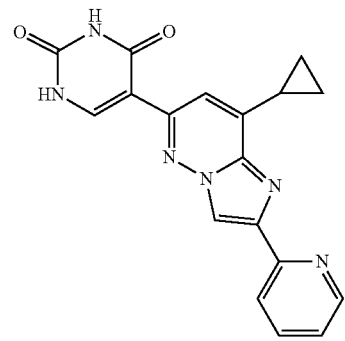 [SMILES: O=c1[nH]cc(-c2cc(C3CC3)c3nc(-c4ccccn4)cn3n2)c(=O)[nH]1]

5-(8-cyclopropyl-2-(pyridin-2-yl)imidazo[1,2-b]pyridazin-6-yl)pyrimidine-2,4(1H,3H)-dione was prepared as a TFA salt in the manner described for Example 1, but replacing 8-cyclopropyl-6-(2,4-dimethoxypyrimidin-5-yl)-2-methyl-imidazo[1,2-b]pyridazine with racemic 8-cyclopropyl-6-(2,4-dimethoxypyrimidin-5-yl)-2-(pyridin-2-yl)imidazo[1,2-b]pyridazine. Purification was accomplished via RP-HPLC (10-90% MeCN/H$_2$O with TFA modifier, Gemini column). ES/MS m/z: 347.14 [M+H]. $^1$H NMR (400 MHz, DMSO-d6) δ11.63-11.38 (m, 2H), 8.66 (s, 1H), 8.64 (ddd, J=4.9, 1.6, 0.9 Hz, 1H), 8.19 (d, J=7.8 Hz, 1H), 8.01 (d, J=6.4 Hz, 1H), 7.95 (td, J=7.9, 1.6 Hz, 1H), 7.40 (ddd, J=7.5, 5.1, 1.2 Hz, 1H), 7.36 (s, 1H), 2.57-2.54 (m, 1H), 1.35-1.20 (m, 4H).

Example 104. 5-(8-((2S,2S)-2-phenylcyclopropyl)imidazo[1,2-b]pyridazin-6-yl)pyrimidine-2,4-(1H,3H)-dione and 5-(8-((1R,2R)-2-phenylcyclopropyl)imidazo[1,2-b]pyridazin-6-yl)pyrimidine-2,4-(1H,3H)-dione

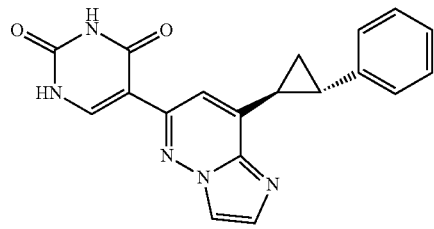

and

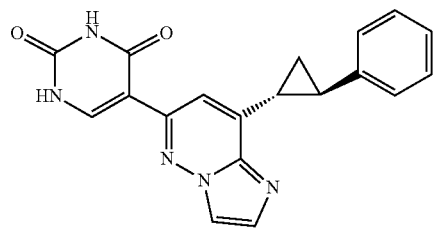

5-(8-((1S,2S)-2-phenylcyclopropyl)imidazo[1,2-b]pyridazin-6-yl)pyrimidine-2,4-(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-phenylcyclopropyl)imidazo[1,2-b]pyridazine (Racemic Mixture). Purification was accomplished via RP-HPLC (10-90% MeCN/H$_2$O with TFA modifier, Gemini column). ES/MS m/z: 346.10 [M+H]. $^1$H NMR (400 MHz, Methanol-d4) δ 8.38 (d, J=1.9 Hz, 1H), 8.30 (s, 1H), 8.07 (d, J=1.9 Hz, 1H), 8.01 (s, 1H), 7.38-7.22 (m, 5H), 2.74 (t, J=7.5 Hz, 2H), 1.93 (tt, J=7.5, 3.7 Hz, 2H).

5-(8-((1S,2S)-2-phenylcyclopropyl)imidazo[1,2-b]pyridazin-6-yl)pyrimidine-2,4-(1H,3H)-dione and 5-(8-((1R,2R)-2-phenylcyclopropyl)imidazo[1,2-b]pyridazin-6-yl)pyrimidine-2,4-(1H,3H)-dione were chirally separated by SFC AD-H column (35% MeOH).

Example 105. 5-(8-((1S,2R)-2-benzylcyclopropyl) imidazo[1,2-b]pyridazin-6-yl)pyrimidine-2,4(1H, 3H)-dione and 5-(8-((1R,2S)-2-benzylcyclopropyl) imidazo[1,2-b]pyridazin-6-yl)pyrimidine-2,4(1H, 3H)-dione

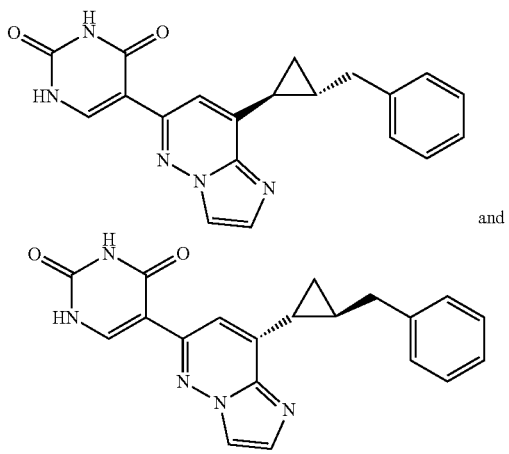

and 5-(8-((1S,2R)-2-benzylcyclopropyl)imidazo[1,2-b] pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((1S,2R)-2-benzylcyclopropyl)-6-(2,4-dimethoxypyrimidin-5-yl)imidazo[1,2-b]pyridazine (Racemic Mixture). Purification was accomplished by RP-HPLC (10-90% MeCN/H₂O with TFA modifier, Gemini column). ES/MS m/z: 360.20 [M+H]. ¹H NMR (400 MHz, Methanol-d4) δ 8.34 (d, J=2.0 Hz, 1H), 8.24 (s, 1H), 8.08 (d, J=1.6 Hz, 1H), 7.82 (s, 1H), 7.34-7.14 (m, 5H), 3.02-2.78 (m, 2H), 2.42-2.32 (m, 1H), 1.93-1.85 (m, 1H), 1.50-1.38 (m, 2H).

Example 106. 5-(8-((1S,2R)-2-(3,3-difluorocyclobutyl)cyclopropyl)imidazo[1,2-b]pyridazin-6-yl) pyrimidine-2,4(1H,3H)-dione and 5-(8-((1R,2S)-2-(3,3-difluorocyclobutyl)cyclopropyl)imidazo[1,2-b] pyridazin-6-yl)pyrimidine-2,4(1H,3H)-dione

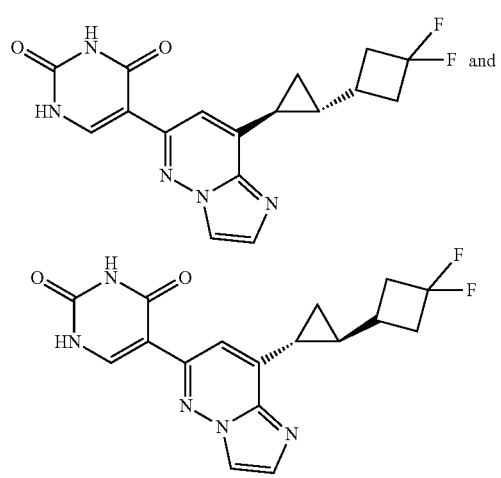

and 5-(8-((1S,2R)-2-(3,3-difluorocyclobutyl)cyclopropyl) imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((1S,2R)-2-(3,3-difluorocyclobutyl)cyclopropyl)-6-(2,4-dimethoxypyrimidin-5-yl)imidazo[1,2-b]pyridazine (Racemic Mixture). Purification was accomplished by RP-HPLC (10-90% MeCN/H₂O with TFA modifier, Gemini column). ES/MS m/z 360.10 [M+H]. ¹H NMR (400 MHz, Methanol-d4) δ 8.36 (d, J=2.0 Hz, 1H), 8.27 (s, 1H), 8.09 (d, J=2.0 Hz, 1H), 7.86 (s, 1H), 2.85-2.66 (m, 2H), 2.51-2.35 (m, 2H), 2.36-2.28 (m, 1H), 2.26-2.11 (m, 1H), 1.86-1.75 (m, 1H), 1.48-1.33 (m, 2H). ¹⁹F NMR (376 MHz, Methanol-d4) δ -77.71 (s, 3F), -84.96-85.76 (m, 1F), -98.02-98.82 (m, 1F).

Example 107. 5-(8-((2S,2S)-2-(trifluoromethyl)cyclopropyl)imidazo[1,2-b]pyridazin-6-yl)pyrimidine-2,4(1H,3H)-dione and 5-(8-((1R,2R)-2-(trifluoromethyl)cyclopropyl)imidazo[1,2-b]pyridazin-6-yl) pyrimidine-2,4(1H,3H)-dione

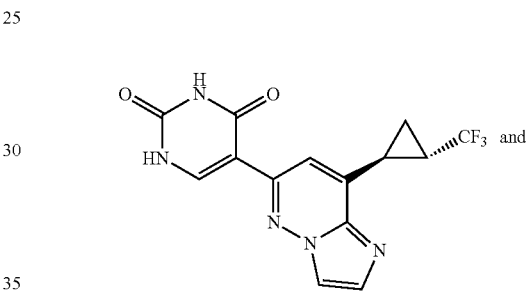

and

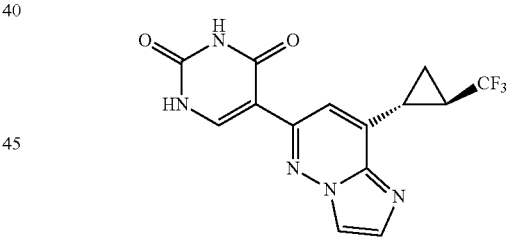

5-(8-((1S,2S)-2-(trifluoromethyl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(trifluoromethyl)cyclopropyl)imidazo[1,2-b]pyridazine (Racemic Mixture). Purification was accomplished by RP-HPLC (5-100% MeCN/H₂O with TFA modifier, Gemini column). ES/MS m/z 338.10 [M+H]. ¹H NMR (400 MHz, Methanol-d4) δ 8.22 (s, 1H), 8.10 (s, 1H), 7.69 (s, 1H), 7.59 (s, 1H), 2.96-2.85 (m, 1H), 2.72-2.62 (m, 1H), 1.72-1.57 (m, 2H). ¹⁹F NMR (376 MHz, Methanol-d4) δ -69.25 (d, J=6.6 Hz, 3F), -77.49 (s, 3F).

Example 108. 5-(8-((1R,2R)-2-fluoro-2-phenylcyclopropyl)imidazo[1,2-b]pyridazin-6-yl)pyrimidine-2,4(1H,3H)-dione and 5-(8-((1S,2S)-2-fluoro-2-phenylcyclopropyl)imidazo[1,2-b]pyridazin-6-yl)pyrimidine-2,4(1H,3H)-dione

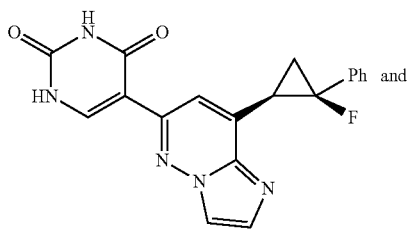

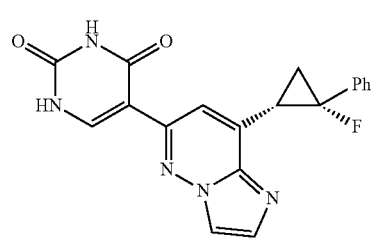

5-(8-((1R,2R)-2-fluoro-2-phenylcyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1R,2R)-2-fluoro-2-phenylcyclopropyl)imidazo[1,2-b]pyridazine (Racemic Mixture). Purification was accomplished by RP-HPLC (10-90% MeCN/H₂O with TFA modifier, Gemini column). ES/MS m/z: 364.10 [M+H]. ¹H NMR (400 MHz, Methanol-d4) δ 8.35 (d, J=1.9 Hz, 1H), 8.30 (s, 1H), 8.22 (s, 1H), 8.00 (d, J=1.9 Hz, 1H), 7.50-7.35 (m, 5H), 3.10-2.99 (m, 1H), 2.36 (dt, J=20.8, 8.0 Hz, 1H), 2.29-2.19 (m, 1H). ¹⁹F NMR (377 MHz, Methanol-d4) δ −77.80 (s, 3F), −188.55 (m, 1F).

Example 109. 5-(8-(3,3,4,4-tetrafluoropyrrolidin-1-yl)imidazo[1,2-b]pyridazin-6-yl)pyrimidine-2,4(1H,3H)-dione

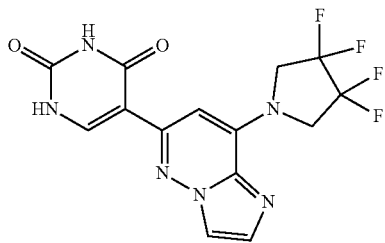 [SMILES: O=c1[nH]cc(-c2cc(N3CC(F)(F)C(F)(F)C3)c3nccn3n2)c(=O)[nH]1]

5-(8-(3,3,4,4-tetrafluoropyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3,3,4,4-tetrafluoropyrrolidin-1-yl)imidazo[1,2-b]pyridazine. Purification was accomplished via RP-HPLC (10-90% MeCN/H₂O with TFA modifier, Gemini column). ES/MS m/z: 371.10 [M+H]. ¹H NMR (400 MHz, DMSO-d6) δ 11.44 (s, 1H), 8.12 (d, J=1.2 Hz, 1H), 7.95 (td, J=3.1, 1.1 Hz, 1H), 7.62 (d, J=1.2 Hz, 1H), 6.69 (s, 1H), 4.65 (t, J=13.1 Hz, 4H). ¹⁹F NMR (376 MHz, DMSO-d6) δ −74.15 (s, 3F), −122.65 (td, J=13.9, 12.3, 5.2 Hz, 4F).

Example 110. 5-(8-((2S,2S)-2-(2,2-difluorobenzo[d][1,3]dioxol-5-yl)cyclopropyl)imidazo[1,2-b]pyridazin-6-yl)pyrimidine-2,4(1H,3H)-dione and 5-(8-(1R,2R)-2-(2,2-difluorobenzo[d][1,3]dioxol-5-yl)cyclopropyl)imidazo[1,2-b]pyridazin-6-yl)pyrimidine-2,4(1H,3H)-dione

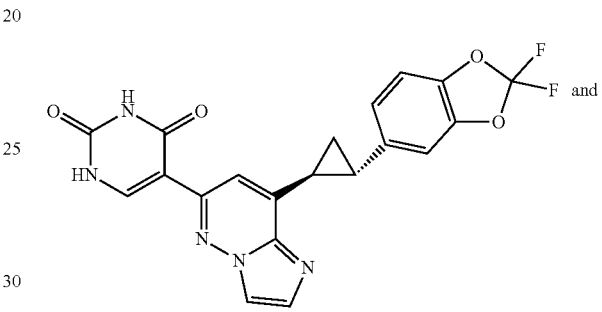

5-(8-((1S,2S)-2-(2,2-difluorobenzo[d][1,3]dioxol-5-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((2S,2S)-2-(2,2-difluorobenzo[d][1,3]dioxol-5-yl)cyclopropyl)-6-(2,4-dimethoxypyrimidin-5-yl)imidazo[1,2-b]pyridazine (Racemic Mixture). Purification was accomplished via RP-HPLC (10-90% MeCN/H₂O with TFA modifier, Gemini column). ES/MS m/z: 426.10 [M+H]. ¹H NMR (400 MHz, Methanol-d4) δ 8.39 (d, J=2.0 Hz, 1H), 8.30 (s, 1H), 8.09 (d, J=2.0 Hz, 1H), 8.02 (s, 1H), 7.21-7.09 (m, 3H), 2.84-2.67 (m, 2H), 1.93 (ddd, J=8.1, 6.6, 1.4 Hz, 2H). ¹⁹F NMR (376 MHz, DMSO-d6) δ −52.99 (d, J=4.1 Hz, 2F), −77.78 (s, 3F)

Example 111. 4-(41R,2S)-2-(6-(2,4-dioxo-1,2,3,4-tetrahydropyrimidin-5-yl)imidazo[1,2-b]pyridazin-8-yl)cyclopropyl)methyl)benzonitrile and 4-(((1S,2R)-2-(6-(2,4-dioxo-1,2,3,4-tetrahydropyrimidin-5-yl)imidazo[1,2-b]pyridazin-8-yl)cyclopropyl)methyl)benzonitrile

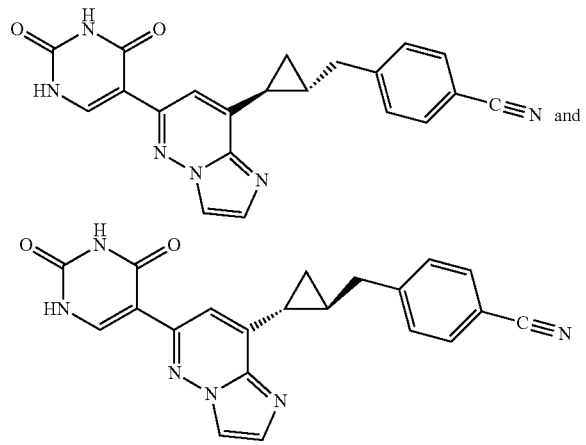

4-(((1R,2S)-2-(6-(2,4-dioxo-1,2,3,4-tetrahydropyrimidin-5-yl)imidazo[1,2-b]pyridazin-8-yl)cyclopropyl)methyl)benzonitrile was prepared as a racemic mixture in the manner described for Example 1, but replacing 8-cyclopropyl-6-(2,4-dimethoxypyrimidin-5-yl)-2-methyl-imidazo[1,2-b]pyridazine with 4-(((1R,2S)-2-(6-(2,4-dimethoxypyrimidin-5-yl)imidazo[1,2-b]pyridazin-8-yl)cyclopropyl)methyl) benzonitrile (Racemic Mixture). Purification was accomplished via RP-HPLC (10-90% MeCN/H$_2$O with TFA modifier, Gemini column). ES/MS m/z: 385.10 [M+H]. $^1$H NMR (400 MHz, Acetonitrile-d3) δ 8.15 (d, J=1.9 Hz, 1H), 8.08 (d, J=6.5 Hz, 1H), 7.97 (d, J=1.9 Hz, 1H), 7.76 (s, 1H), 7.72-7.61 (m, 2H), 7.57-7.42 (m, 2H), 3.08-2.88 (m, 3H), 1.86-1.75 (m, 1H), 1.54-1.37 (m, 2H).

Example 115. 4-((2S,2S)-2-(6-(2,4-dioxo-1,2,3,4-tetrahydropyrimidin-5-yl)imidazo[1,2-b]pyridazin-8-yl)cyclopropyl)-2-fluorobenzonitrile (Racemic Mixture)

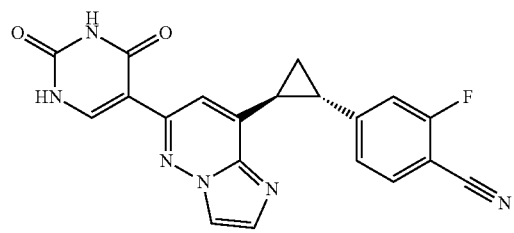 [SMILES: N#Cc1ccc([C@H]2C[C@@H]2c2cc(-c3c[nH]c(=O)[nH]c3=O)nn3ccnc23)cc1F]

4-((2S,2S)-2-(6-(2,4-dioxo-1,2,3,4-tetrahydropyrimidin-5-yl)imidazo[1,2-b]pyridazin-8-yl)cyclopropyl)-2-fluorobenzonitrile (Racemic Mixture) was prepared in the manner described for Example 1, but replacing 8-cyclopropyl-6-(2,4-dimethoxypyrimidin-5-yl)-2-methyl-imidazo[1,2-b]pyridazine with 4-[(1S,2S)-2-[6-(2,4-dimethoxypyrimidin-5-yl)imidazo[1,2-b]pyridazin-8-yl]cyclopropyl]-2-fluorobenzonitrile. Purification was accomplished by RP-HPLC (10-90% MeCN/H$_2$O with TFA modifier, Gemini column). ES/MS m/z: 389.1 [M+H]. $^1$H NMR (400 MHz, DMSO-d6) δ 11.54 (d, J=3.7 Hz, 2H), 8.31 (d, J=1.4 Hz, 1H), 8.02 (d, J=6.4 Hz, 1H), 7.88-7.79 (m, 2H), 7.58 (s, 1H), 7.47 (dd, J=11.1, 1.5 Hz, 1H), 7.34 (dd, J=8.2, 1.6 Hz, 1H), 2.96 (dd, J=8.8, 5.1 Hz, 1H), 2.86 (ddd, J=8.9, 6.2, 4.4 Hz, 1H), 2.24 (dt, J=8.7, 5.4 Hz, 1H), 1.89 (dt, J=8.8, 5.5 Hz, 1H). $^{19}$F NMR (376 MHz, DMSO-d6) δ −75.04, −109.50 (dd, J=11.0, 7.2 Hz).

Example 117. 5-(8-((2S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione

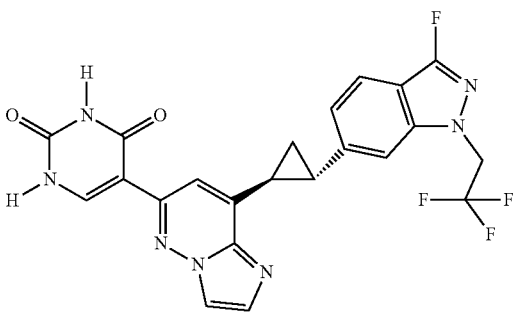 [SMILES: O=c1[nH]cc(-c2cc([C@H]3C[C@@H]3c3ccc4c(F)nn(CC(F)(F)F)c4c3)c3nccn3n2)c(=O)[nH]1]

5-(8-((1S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[3-fluoro-1-(2,2,2-trifluoroethyl)indazol-6-yl]cyclopropyl]imidazo[1,2-b]pyridazine(racemic). ES/MS m/z: 486.20 [M+H]. $^1$H NMR (400 MHz, DMSO-d6) δ 11.54 (s, 2H), 8.31 (s, 1H), 8.03 (d, J=6.3 Hz, 1H), 7.85-7.80 (m, 1H), 7.78-7.67 (m, 2H), 7.58 (s, 1H), 7.24-7.17 (m, 1H), 5.31 (q, J=9.0 Hz, 2H), 3.03 (dt, J=9.6, 5.7 Hz, 1H), 2.83 (dt, J=9.6, 5.3 Hz, 1H), 2.18 (dt, J=10.0, 5.3 Hz, 1H), 1.91 (q, J=6.3 Hz, 1H).

Example 118. 5-(8-((2S,2S)-2-(1-((2,2-difluorocyclopropyl)methyl)-1H-indazol-6-yl)cyclopropyl)imidazo[1,2-b]pyridazin-6-yl)pyrimidine-2,4(1H,3H)-dione

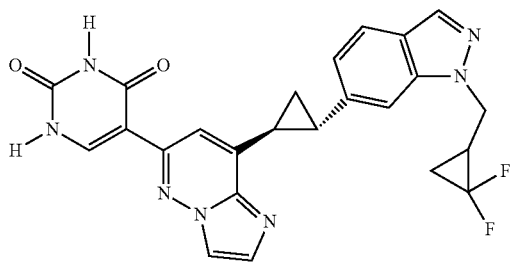 [SMILES: O=c1[nH]cc(-c2cc([C@H]3C[C@@H]3c3ccc4cnn(CC5CC5(F)F)c4c3)c3nccn3n2)c(=O)[nH]1]

5-(8-((1S,2S)-2-(1-((2,2-difluorocyclopropyl)methyl)-1H-indazol-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2- methyl-imidazo[1,2-b]pyridazine with 8-[(1S,2S)-2-[1-[(2,2-difluorocyclopropyl)methyl]indazol-6-yl]cyclopropyl]-6-(2,4-dimethoxypyrimidin-5-yl)imidazo[1,2-b]pyridazine (racemic). ES/MS m/z: 476.10 [M+H]. ¹H NMR (400 MHz, DMSO-d6) δ 11.58 (d, J=8.3 Hz, 2H), 8.38 (d, J=4.5 Hz, 1H), 8.06 (q, J=3.5, 2.7 Hz, 2H), 7.94 (d, J=7.9 Hz, 1H), 7.71 (d, J=8.3 Hz, 1H), 7.63 (d, J=3.5 Hz, 2H), 7.06 (d, J=8.4 Hz, 1H), 4.62-4.45 (m, 2H), 3.02-2.92 (m, 1H), 2.88-2.79 (m, 1H), 2.29 (ddq, J=14.8, 12.0, 7.3 Hz, 1H), 2.11 (dt, J=11.0, 5.6 Hz, 1H), 1.99-1.91 (m, 1H), 1.66 (dq, J=11.4, 5.3 Hz, 1H), 1.55-1.42 (m, 1H).

Example 119. 5-(8-((2S,2S)-2-(1-isopropyl-1H-indazol-6-yl)cyclopropyl)imidazo[1,2-b]pyridazin-6-yl)pyrimidine-2,4(1H,3H)-dione and 5-(8-((1R,2R)-2-(1-isopropyl-1H-indazol-6-yl)cyclopropyl)imidazo[1,2-b]pyridazin-6-yl)pyrimidine-2,4(1H,3H)-dione

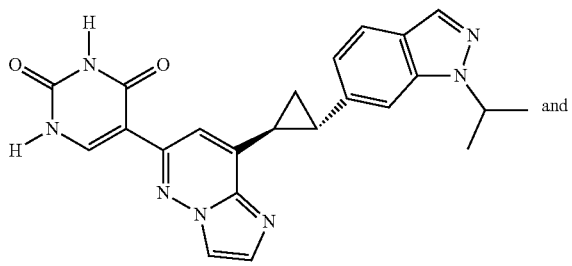

5-(8-((1S,2S)-2-(1-isopropyl-1H-indazol-6-yl)cyclopropyl)imidazo[1,2-b]pyridazin-6-yl)pyrimidine-2,4(1H,3H)-dione and 5-(8-((1R,2R)-2-(1-isopropyl-1H-indazol-6-yl)cyclopropyl)imidazo[1,2-b]pyridazin-6-yl)pyrimidine-2,4(1H,3H)-dione were prepared a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-(1-isopropylindazol-6-yl)cyclopropyl]imidazo[1,2-b]pyridazine (racemic). ES/MS m/z: 428.20 [M+H]. ¹H NMR (400 MHz, DMSO-d6) δ 11.58-11.52 (m, 2H), 8.36-8.31 (m, 1H), 8.07-7.98 (m, 2H), 7.86 (s, 1H), 7.68 (d, J=8.4 Hz, 1H), 7.62-7.56 (m, 2H), 7.02 (dd, J=8.5, 1.4 Hz, 1H), 5.00 (p, J=6.6 Hz, 1H), 2.97 (ddd, J=9.0, 6.2, 4.2 Hz, 1H), 2.87-2.77 (m, 1H), 2.16-2.06 (m, 1H), 1.93 (dt, J=8.8, 5.6 Hz, 1H), 1.47 (dd, J=9.3, 6.6 Hz, 6H).

Example 120. 5-(8-((2S,2S)-2-(1-isopropyl-1H-indazol-6-yl)cyclopropyl)imidazo[1,2-b]pyridazin-6-yl)pyrimidine-2,4(1H,3H)-dione

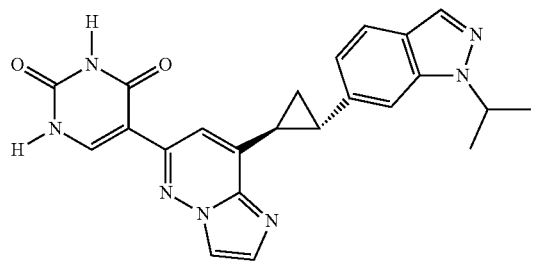 [SMILES: CC(C)n1ncc2ccc([C@H]3C[C@@H]3c3cc(-c4c[nH]c(=O)[nH]c4=O)nn4ccnc34)cc21]

5-[8-[(1S,2S)-2-(1-isopropylindazol-6-yl)cyclopropyl]imidazo[1,2-b]pyridazin-6-yl]-1H-pyrimidine-2,4-dione was chirally separated from the Example 119 by SFC AD-H column (35% EtOH). ES/MS m/z: 428.20 [M+H]. ¹H NMR (400 MHz, DMSO-d6) δ 11.54 (s, 2H), 8.33 (d, J=1.4 Hz, 1H), 8.07-7.98 (m, 2H), 7.85 (s, 1H), 7.68 (d, J=8.3 Hz, 1H), 7.59 (d, J=4.8 Hz, 2H), 7.02 (dd, J=8.4, 1.3 Hz, 1H), 5.00 (p, J=6.6 Hz, 1H), 3.03-2.93 (m, 1H), 2.86-2.77 (m, 1H), 2.11 (dq, J=9.5, 4.8 Hz, 1H), 1.93 (dt, J=8.6, 5.5 Hz, 1H), 1.47 (dd, J=9.3, 6.6 Hz, 6H).

Example 121. 5-(8-((1S,2S)-2-(6-(difluoromethoxy)pyridin-3-yl)cyclopropyl)-3-fluoroimidazo[1,2-b]pyridazin-6-yl)pyrimidine-2,4(1H,3H)-dione and 5-(8-((1R,2R)-2-(6-(difluoromethoxy)pyridin-3-yl)cyclopropyl)-3-fluoroimidazo[1,2-b]pyridazin-6-yl)pyrimidine-2,4(1H,3H)-dione

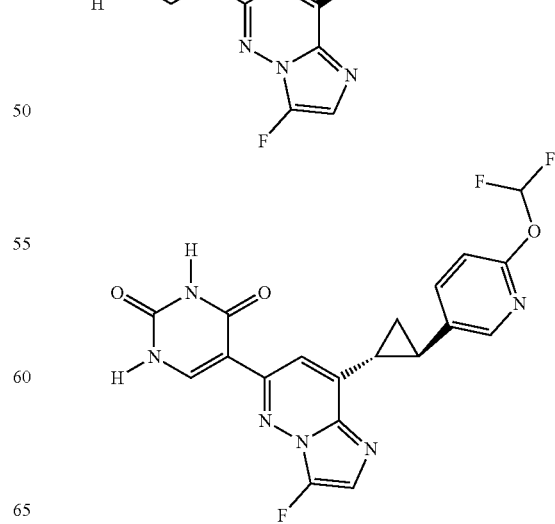

809

5-(8-((1S,2S)-2-(6-(difluoromethoxy)pyridin-3-yl)cyclopropyl)-3-fluoroimidazo[1,2-b]pyridazin-6-yl)pyrimidine-2,4(1H,3H)-dione and 5-(8-((1R,2R)-2-(6-(difluoromethoxy)pyridin-3-yl)cyclopropyl)-3-fluoroimidazo[1,2-b]pyridazin-6-yl)pyrimidine-2,4(1H,3H)-dione were prepared a racemic mixture in the manner described for Example 1, but replacing 8-cyclopropyl-6-(2,4-dimethoxy-pyrimidin-5-yl)-2-methyl-imidazo[1,2-b]pyridazine with 8-[(1S,2S)-2-[6-(difluoromethoxy)-3-pyridyl]cyclopropyl]-6-(2,4-dimethoxypyrimidin-5-yl)-3-fluoro-imidazo[1,2-b]pyridazine (racemic). ES/MS m/z: 431.20 [M+H]. $^1$H NMR (400 MHz, DMSO-d6) δ 11.54 (d, J=4.0 Hz, 2H), 8.24 (d, J=2.5 Hz, 1H), 8.03 (d, J=6.4 Hz, 1H), 7.86-7.50 (m, 1H), 7.80 (dd, J=8.5, 2.5 Hz, 1H), 7.55 (d, J=7.1 Hz, 1H), 7.52-7.50 (m, 1H), 7.06 (d, J=8.5 Hz, 1H), 2.92-2.87 (m, 1H), 2.79-2.66 (m, 1H), 2.14 (dt, J=9.1, 5.4 Hz, 1H), 1.79 (ddd, J=8.8, 6.3, 4.8 Hz, 1H).

Example 122. 5-(8-((2S,2S)-2-(6-(difluoromethoxy)pyridin-3-yl)cyclopropyl)-3-fluoroimidazo[1,2-b]pyridazin-6-yl)pyrimidine-2,4(1H,3H)-dione

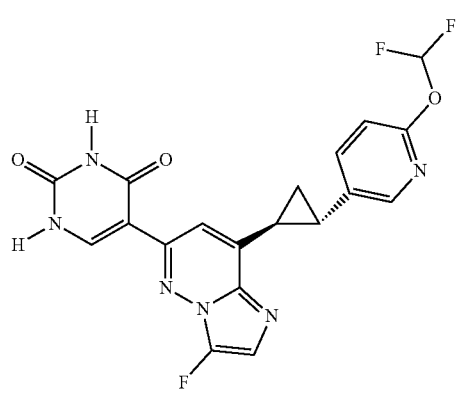 [SMILES: O=c1[nH]cc(-c2cc([C@H]3C[C@@H]3c3ccc(OC(F)F)nc3)c3ncc(F)n3n2)c(=O)[nH]1]

5-[8-[(1S,2S)-2-[5-(difluoromethoxy)-2-pyridyl]cyclopropyl]imidazo[1,2-b]pyridazin-6-yl]-1H-pyrimidine-2,4-dione was chirally separated from the Example 121 by SFC OJ-H column (25% EtOH). ES/MS m/z: 431.10 [M+H]. $^1$H NMR (400 MHz, DMSO-d6) δ 11.55 (d, J=4.7 Hz, 2H), 8.24 (d, J=2.4 Hz, 1H), 8.03 (d, J=6.3 Hz, 1H), 7.86-7.49 (m, 1H), 7.80 (dd, J=8.6, 2.6 Hz, 1H), 7.56 (d, J=7.1 Hz, 1H), 7.51 (s, 1H), 7.06 (d, J=8.5 Hz, 1H), 2.91 (ddd, J=9.0, 6.3, 4.4 Hz, 1H), 2.71 (ddd, J=8.9, 5.9, 4.5 Hz, 1H), 2.14 (dt, J=8.9, 5.3 Hz, 1H), 1.84-1.74 (m, 1H).

810

Example 123. 5-(8-((2S,2S)-2-(1-(2,2-difluoroethyl)-1H-indazol-6-yl)cyclopropyl)imidazo[1,2-b]pyridazin-6-yl)pyrimidine-2,4(1H,3H)-dione and 5-(8-((1R,2R)-2-(1-(2,2-difluoroethyl)-1H-indazol-6-yl)cyclopropyl)imidazo[1,2-b]pyridazin-6-yl)pyrimidine-2,4(1H,3H)-dione

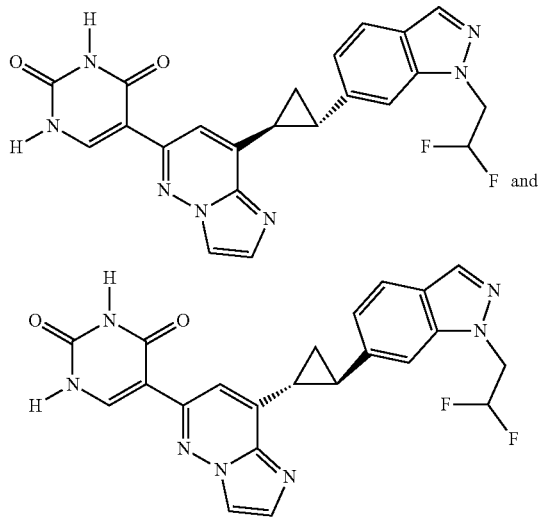

5-(8-((1S,2S)-2-(1-(2,2-difluoroethyl)-1H-indazol-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-[(1S,2S)-2-[1-(2,2-difluoroethyl)indazol-6-yl]cyclopropyl]-6-(2,4-dimethoxypyrimidin-5-yl)imidazo[1,2-b]pyridazine(racemic). ES/MS m/z: 450.20 [M+H]. $^1$H NMR (400 MHz, DMSO-d6) δ 11.55 (s, 2H), 8.34 (s, 1H), 8.14-7.99 (m, 2H), 7.86 (s, 1H), 7.77-7.54 (m, 3H), 7.09 (d, J=8.4 Hz, 1H), 6.43 (t, J=54.9 Hz, 1H), 4.91 (t, J=14.9 Hz, 2H), 3.00 (s, 1H), 2.82 (d, J=7.9 Hz, 1H), 2.13 (d, J=8.2 Hz, 1H), 1.93 (s, 1H).

Example 124. 5-(8-((1R,2R)-2-(1-(2,2-difluoroethyl)-1H-indazol-6-yl)cyclopropyl)imidazo[1,2-b]pyridazin-6-yl)pyrimidine-2,4(1H,3H)-dione

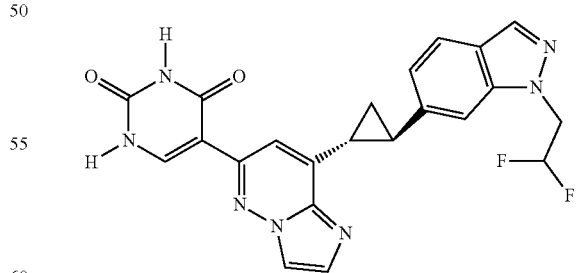

5-[8-[(1R,2R)-2-[1-(2,2-difluoroethyl)indazol-6-yl]cyclopropyl]imidazo[1,2-b]pyridazin-6-yl]-1H-pyrimidine-2,4-dione was chirally separated from the Example 123 by SFC AD-H column (35% EtOH). ES/MS m/z: 450.20 [M+H]. $^1$H NMR (400 MHz, DMSO-d6) δ11.53 (d, J=4.7 Hz, 2H), 8.31 (d, J=1.3 Hz, 1H), 8.10 (d, J=0.9 Hz, 1H), 8.06-7.99 (m, 1H), 7.82 (s, 1H), 7.75-7.64 (m, 2H), 7.56 (s, 1H), 7.08 (dd, J=8.4, 1.3 Hz, 1H), 6.57-6.29 (t, J=3.9 Hz, 1H), 4.91 (td, J=15.0, 3.8 Hz, 2H), 3.05-2.96 (m, 1H), 2.81 (dt, J=8.9, 5.4 Hz, 1H), 2.19-2.06 (m, 1H), 1.91 (dt, J=8.5, 5.3 Hz, 1H)

Example 125. 5-(8-((1S,2S)-2-(1-(2,2-difluoro-ethyl)-1H-indazol-6-yl)cyclopropyl)imidazo[1,2-b]pyridazin-6-yl)pyrimidine-2,4(1H,3H)-dione

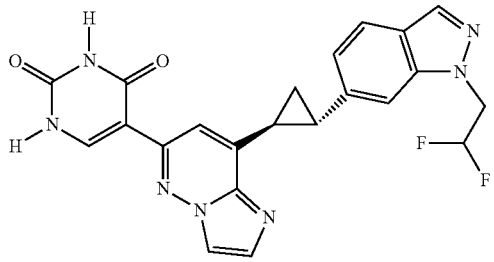 [SMILES: O=c1[nH]cc(-c2cc([C@H]3C[C@@H]3c3ccc4cnn(CC(F)F)c4c3)c3nccn3n2)c(=O)[nH]1]

5-(8-((1S,2S)-2-(1-(2,2-difluoroethyl)-1H-indazol-6-yl)cyclopropyl)imidazo[1,2-b]pyridazin-6-yl)pyrimidine-2,4(1H,3H)-dione was chirally separated from the Example 123 by SFC AD-H column (35% EtOH). ES/MS m/z: 450.20 [M+H]. $^1$H NMR (400 MHz, DMSO-d6) δ11.53 (s, 2H), 8.30 (s, 1H), 8.10 (s, 1H), 8.02 (d, J=6.2 Hz, 1H), 7.85-7.65 (m, 3H), 7.55 (s, 1H), 7.08 (dd, J=8.4, 1.3 Hz, 1H), 6.43 (tt, J=54.9, 3.7 Hz, 1H), 4.91 (td, J=15.1, 3.8 Hz, 2H), 3.05-2.93 (m, 1H), 2.86-2.77 (m, 1H), 2.20-2.10 (m, 1H), 1.96-1.83 (m, 1H).

Example 126. 5-(8-((2S,2S)-2-(1-(2,2,2-trifluoro-ethyl)-1H-pyrrolo[2,3-b]pyridin-6-yl)cyclopropyl)imidazo[1,2-b]pyridazin-6-yl)pyrimidine-2,4(1H,3H)-dione

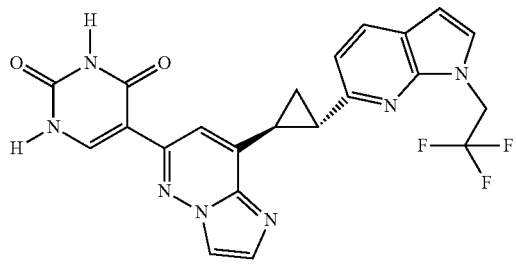 [SMILES: O=c1[nH]cc(-c2cc([C@H]3C[C@@H]3c3ccc4ccn(CC(F)(F)F)c4n3)c3nccn3n2)c(=O)[nH]1]

5-(8-((1S,2S)-2-(1-(2,2,2-trifluoroethyl)-1H-pyrrolo[2,3-b]pyridin-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[1-(2,2,2-trifluoroethyl)pyrrolo[2,3-b]pyridin-6-yl]cyclopropyl]imidazo[1,2-b]pyridazine. ES/MS m/z: 468.20 [M+H]. $^1$H NMR (400 MHz, DMSO-d6) δ 11.55 (s, 2H), 8.33 (d, J=1.5 Hz, 1H), 8.07-8.00 (m, 1H), 7.94 (d, J=8.0 Hz, 1H), 7.86 (s, 1H), 7.59 (s, 1H), 7.53 (d, J=3.7 Hz, 1H), 7.22 (d, J=8.0 Hz, 1H), 6.57 (d, J=3.6 Hz, 1H), 5.18 (h, J=8.3 Hz, 2H), 3.04 (dddd, J=28.6, 9.7, 6.0, 4.1 Hz, 2H), 2.13-1.98 (m, 2H).

Example 127. 5-(8-((2S,2S)-2-(1-(2,2,2-trifluoro-ethyl)-1H-pyrrolo[3,2-c]pyridin-6-yl)cyclopropyl)imidazo[1,2-b]pyridazin-6-yl)pyrimidine-2,4(1H,3H)-dione

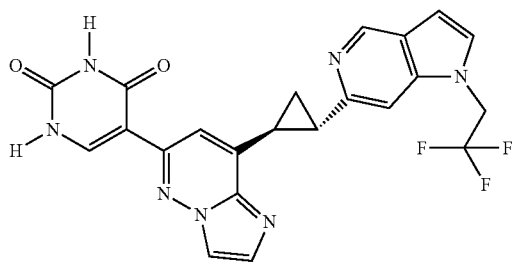 [SMILES: O=c1[nH]cc(-c2cc([C@H]3C[C@@H]3c3cc4c(ccn4CC(F)(F)F)cn3)c3nccn3n2)c(=O)[nH]1]

5-(8-((1S,2S)-2-(1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-[2-(2,2,2-trifluoroethyl)pyrrolo[3,2-c]pyridin-6-yl]cyclopropyl]imidazo[1,2-b]pyridazine (racemic). ES/MS m/z: 468.10 [M+H]. $^1$H NMR (400 MHz, DMSO-d6) δ 11.59-11.51 (m, 2H), 9.21 (s, 1H), 8.31 (d, J=1.3 Hz, 1H), 8.24 (s, 1H), 8.04 (d, J=6.1 Hz, 1H), 7.93 (d, J=3.5 Hz, 1H), 7.78 (d, J=1.3 Hz, 1H), 7.65 (s, 1H), 7.10 (d, J=3.5 Hz, 1H), 5.46 (q, J=9.0 Hz, 2H), 3.53 (dd, J=9.2, 5.0 Hz, 1H), 3.05-2.95 (m, 1H), 2.43 (dd, J=9.4, 5.6 Hz, 1H), 2.11 (dt, J=9.5, 5.5 Hz, 1H).

Example 128. 5-(8-((2S,2S)-2-(3-cyclopropyl-1-(2,2,2-trifluoroethyl)-1H-indazol-6-yl)cyclopropyl)imidazo[1,2-b]pyridazin-6-yl)pyrimidine-2,4(1H,3H)-dione

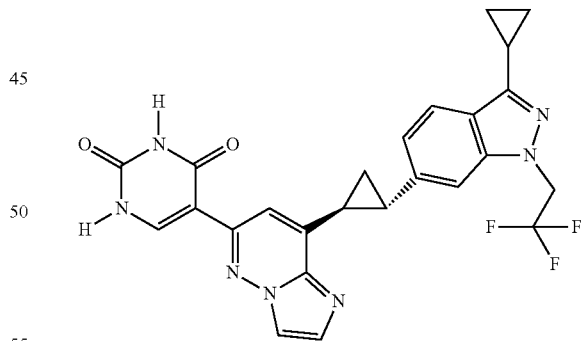

5-(8-((1S,2S)-2-(3-cyclopropyl-1-(2,2,2-trifluoroethyl)-1H-indazol-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-[(1S,2S)-2-[3-cyclopropyl-1-(2,2,2-trifluoroethyl)indazol-6-yl]cyclopropyl]-6-(2,4-dimethoxypyrimidin-5-yl)imidazo[1,2-b]pyridazine (racemic). ES/MS m/z: 508.20 [M+H]. $^1$H NMR (400 MHz, DMSO-d6) δ 11.54 (s, 2H), 8.32 (s, 1H), 8.06-7.99 (m, 1H), 7.83 (s, 1H), 7.74 (d, J=8.4 Hz, 1H), 7.63 (s, 1H), 7.56 (s, 1H), 7.07 (dd, J=8.4, 1.4 Hz, 1H), 5.27 (q, J=9.1 Hz, 2H), 2.99 (dt, J=9.2, 5.5 Hz, 1H), 2.79 (dt, J=9.6, 5.4 Hz, 1H), 2.34-2.23 (m, 1H), 2.18-2.06 (m, 1H), 1.90 (dd, J=8.8, 5.3 Hz, 1H), 1.07-0.91 (m, 4H).

Example 129. 5-(8-((2S,2S)-2-(1-(2,2-difluoro-ethyl)-7-fluoro-1H-indazol-6-yl)cyclopropyl)imidazo[1,2-b]pyridazin-6-yl)pyrimidine-2,4(1H,3H)-dione

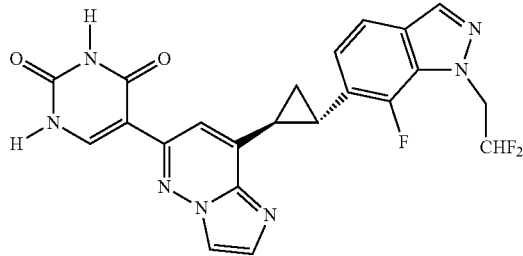 [SMILES: O=c1[nH]cc(-c2cc([C@H]3C[C@@H]3c3ccc4cnn(CC(F)F)c4c3F)c3nccn3n2)c(=O)[nH]1]

5-(8-((1S,2S)-2-(1-(2,2-difluoroethyl)-7-fluoro-1H-indazol-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-((1S,2S)-2-(1-(2,2-difluoroethyl)-7-fluoro-1H-indazol-6-yl)cyclopropyl)-6-(2,4-dimethoxypyrimidin-5-yl)imidazo[1,2-b]pyridazine. ES/MS m/z: 468.20 [M+H]. ¹H NMR (400 MHz, DMSO-d6) δ 11.57 (d, J=6.0 Hz, 2H), 8.38 (d, J=1.5 Hz, 1H), 8.22 (d, J=2.3 Hz, 1H), 8.04 (d, J=6.0 Hz, 1H), 7.92 (s, 1H), 7.69-7.56 (m, 2H), 7.02 (dd, J=8.5, 6.0 Hz, 1H), 6.44 (tt, J=54.7, 3.6 Hz, 1H), 4.91 (td, J=15.0, 3.6 Hz, 2H), 3.16 (dt, J=8.7, 5.4 Hz, 1H), 2.85 (dt, J=8.9, 5.4 Hz, 1H), 2.15 (dt, J=8.9, 5.3 Hz, 1H), 1.98-1.85 (m, 1H).

Example 130. 5-(8-((2S,2S)-2-(1-(cyclopropylmethyl)-1H-indazol-6-yl)cyclopropyl)imidazo[1,2-b]pyridazin-6-yl)pyrimidine-2,4(1H,3H)-dione

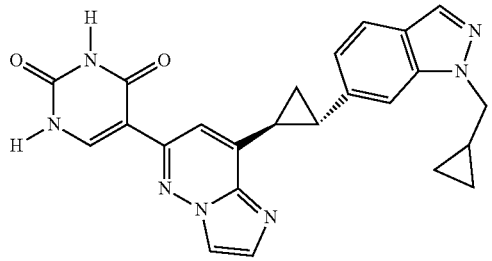 [SMILES: O=c1[nH]cc(-c2cc([C@H]3C[C@@H]3c3ccc4cnn(CC5CC5)c4c3)c3nccn3n2)c(=O)[nH]1]

5-(8-((1S,2S)-2-(1-(cyclopropylmethyl)-1H-indazol-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-[(1S,2S)-2-[1-(cyclopropylmethyl)indazol-6-yl]cyclopropyl]-6-(2,4-dimethoxypyrimidin-5-yl)imidazo[1,2-b]pyridazine(racemic). ES/MS m/z: 440.20 [M+H]. ¹H NMR (400 MHz, DMSO-d6) δ 11.57 (d, J=5.5 Hz, 2H), 8.36 (d, J=1.4 Hz, 1H), 8.08-7.97 (m, 2H), 7.90 (s, 1H), 7.69 (d, J=8.4 Hz, 1H), 7.61 (s, 2H), 7.02 (dd, J=8.4, 1.3 Hz, 1H), 4.28 (d, J=6.9 Hz, 2H), 2.97 (ddd, J=9.4, 6.3, 4.4 Hz, 1H), 2.87-2.77 (m, 1H), 2.10 (dt, J=8.9, 5.3 Hz, 1H), 1.99-1.89 (m, 1H), 1.28 (tq, J=7.4, 4.8 Hz, 1H), 0.54-0.42 (m, 2H), 0.46-0.34 (m, 2H).

Example 131. 5-(8-((2S,2S)-2-(2-(trifluoromethyl)quinolin-6-yl)cyclopropyl)imidazo[1,2-b]pyridazin-6-yl)pyrimidine-2,4(1H,3H)-dione

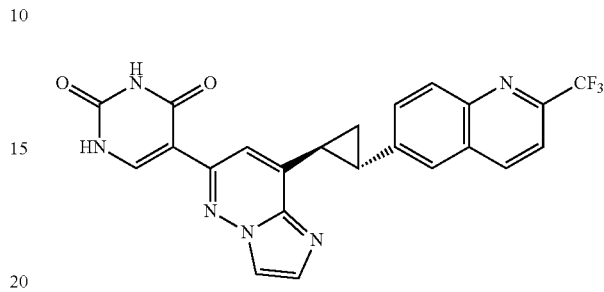

5-(8-((1S,2S)-2-(2-(trifluoromethyl)quinolin-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]-2-(trifluoromethyl)quinoline. ES/MS m/z: 465.10 [M+H]. ¹H NMR (400 MHz, DMSO-d6) δ 11.57 (d, J=6.1 Hz, 2H), 8.63 (d, J=8.6 Hz, 1H), 8.36 (d, J=1.5 Hz, 1H), 8.14 (d, J=8.8 Hz, 1H), 8.09-8.02 (m, 2H), 7.97 (d, J=8.6 Hz, 1H), 7.92-7.81 (m, 2H), 7.66 (s, 1H), 3.09 (ddd, J=9.0, 6.2, 4.4 Hz, 1H), 2.94 (ddd, J=8.9, 6.0, 4.4 Hz, 1H), 2.22 (dt, J=8.8, 5.4 Hz, 1H), 1.99 (dt, J=8.7, 5.4 Hz, 1H).

Example 132. 5-(8-((2S,2S)-2-(5-(difluoromethoxy)pyridin-2-yl)cyclopropyl)-3-fluoroimidazo[1,2-b]pyridazin-6-yl)pyrimidine-2,4(1H,3H)-dione

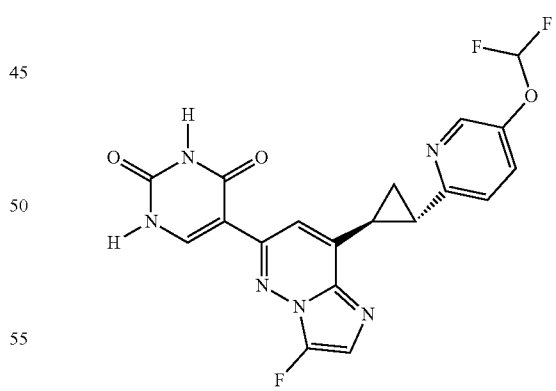

5-(8-((1S,2S)-2-(5-(difluoromethoxy)pyridin-2-yl)cyclopropyl)-3-fluoroimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-[(1S,2S)-2-[5-(difluoromethoxy)-2-pyridyl]cyclopropyl]-6-(2,4-dimethoxypyrimidin-5-yl)-3-fluoro-imidazo[1,2-b]pyridazine. ES/MS m/z: 431.20 [M+H]. ¹H NMR (400 MHz, DMSO-d6) δ 11.65-11.46 (m, 2H), 8.44 (d, J=2.8 Hz, 1H), 8.04 (d, J=6.2 Hz, 1H), 7.65-7.49 (m, 4H), 7.28 (t, J=73.6 Hz, 1H), 3.06 (ddd, J=8.7, 5.9, 4.2 Hz, 1H), 2.93 (ddd, J=8.9, 6.0, 4.1 Hz, 1H), 2.08 (ddd, J=8.4, 6.0, 4.0 Hz, 1H), 1.91-1.84 (m, 1H).

Example 133. 5-(8-((2S,2S)-2-(3-(trifluoromethyl)isoquinolin-6-yl)cyclopropyl)imidazo[1,2-b]pyridazin-6-yl)pyrimidine-2,4(1H,3H)-dione

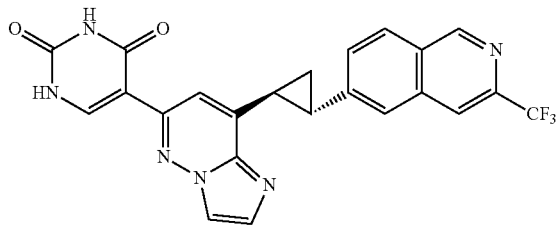 [SMILES: O=c1[nH]cc(-c2cc([C@H]3C[C@@H]3c3ccc4cnc(C(F)(F)F)cc4c3)c3nccn3n2)c(=O)[nH]1]

5-(8-((1S,2S)-2-(3-(trifluoromethyl)isoquinolin-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]-3-(trifluoromethyl)isoquinoline. ES/MS m/z: 465.10 [M+H]. ¹H NMR (400 MHz, DMSO-d6) δ 11.63 (dd, J=23.1, 4.1 Hz, 2H), 9.45 (s, 1H), 8.47 (s, 1H), 8.36 (s, 1H), 8.27 (d, J=8.6 Hz, 1H), 8.14-8.04 (m, 3H), 7.84-7.75 (m, 2H), 3.05 (t, J=7.4 Hz, 2H), 2.24-2.14 (m, 1H), 2.03 (td, J=7.7, 5.1 Hz, 1H).

Example 134. 5-(3-fluoro-8-((1S,2S)-2-(8-(trifluoromethyl)quinolin-6-yl)cyclopropyl)imidazo[1,2-b]pyridazin-6-yl)pyrimidine-2,4(1H,3H)-dione

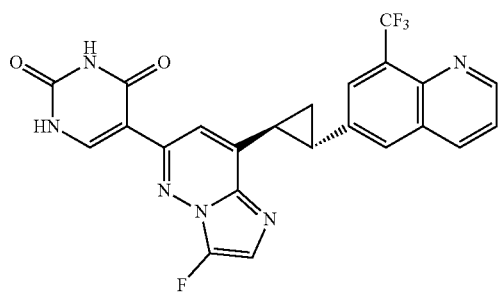 [SMILES: O=c1[nH]cc(-c2cc([C@H]3C[C@@H]3c3cc(C(F)(F)F)c4ncccc4c3)c3ncc(F)n3n2)c(=O)[nH]1]

5-(3-fluoro-8-((1S,2S)-2-(8-(trifluoromethyl)quinolin-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)-3-fluoro-imidazo[1,2-b]pyridazin-8-yl]cyclopropyl]-8-(trifluoromethyl)quinoline. ES/MS m/z: 483.10 [M+H]. ¹H NMR (400 MHz, DMSO-d6) δ 11.60-11.53 (m, 2H), 9.00 (dd, J=4.4, 1.5 Hz, 1H), 8.44 (dd, J=8.4, 1.7 Hz, 1H), 8.19 (d, J=1.9 Hz, 1H), 8.11 (d, J=1.9 Hz, 1H), 8.05 (d, J=6.0 Hz, 1H), 7.68 (dd, J=8.4, 4.2 Hz, 1H), 7.58 (d, J=7.4 Hz, 2H), 3.25-3.15 (m, 1H), 2.91 (dt, J=10.0, 5.4 Hz, 1H), 2.24 (dt, J=9.0, 5.4 Hz, 1H), 1.99 (dt, J=8.8, 5.5 Hz, 1H).

Example 135. 5-(8-((2S,2S)-2-(8-(trifluoromethyl)quinolin-6-yl)cyclopropyl)imidazo[1,2-b]pyridazin-6-yl)pyrimidine-2,4(1H,3H)-dione

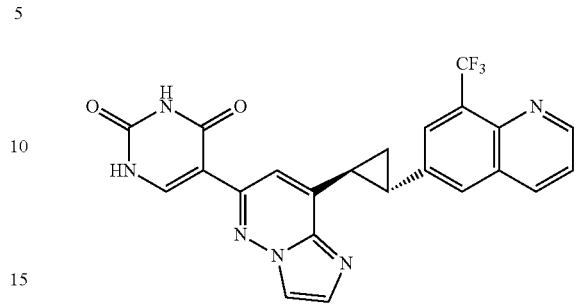

5-(8-((1S,2S)-2-(8-(trifluoromethyl)quinolin-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]-8-(trifluoromethyl)quinoline. ES/MS m/z: 465.10 [M+H]. ¹H NMR (400 MHz, DMSO-d6) δ 11.58 (d, J=7.1 Hz, 2H), 9.04-8.98 (m, 1H), 8.45 (dd, J=8.5, 1.6 Hz, 1H), 8.38 (s, 1H), 8.19 (s, 1H), 8.13-8.02 (m, 2H), 7.91 (s, 1H), 7.73-7.65 (m, 2H), 3.15 (dt, J=10.0, 5.7 Hz, 1H), 2.93 (dt, J=10.0, 5.2 Hz, 1H), 2.20 (dt, J=10.4, 5.6 Hz, 1H), 2.03 (dt, J=11.1, 5.7 Hz, 1H).

Example 136. 5-(8-((2S,2S)-2-(5-(difluoromethoxy)pyridin-2-yl)cyclopropyl)imidazo[1,2-b]pyridazin-6-yl)pyrimidine-2,4(1H,3H)-dione and 5-(8-((1R,2R)-2-(5-(difluoromethoxy)pyridin-2-yl)cyclopropyl)imidazo[1,2-b]pyridazin-6-yl)pyrimidine-2,4(1H,3H)-dione

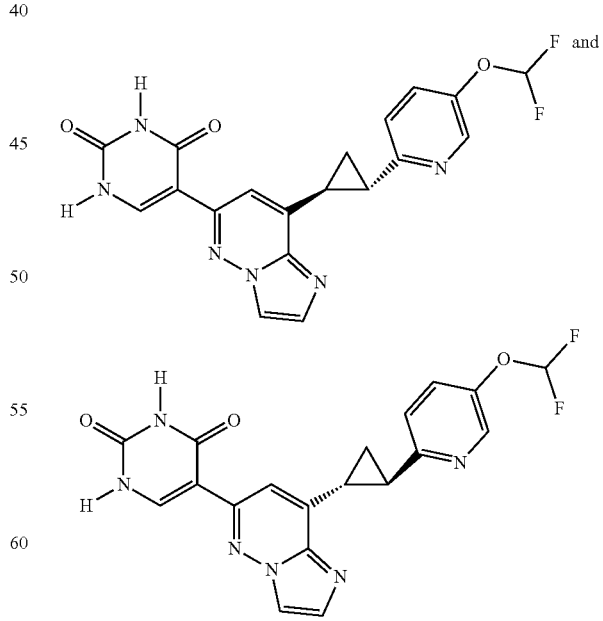

5-(8-((1S,2S)-2-(5-(difluoromethoxy)pyridin-2-yl)cyclopropyl)imidazo[1,2-b]pyridazin-6-yl)pyrimidine-2,4(1H,3H)-dione and 5-(8-((1R,2R)-2-(5-(difluoromethoxy)pyridin-2-yl)cyclopropyl)imidazo[1,2-b]pyridazin-6-yl)pyrimidine-2,4(1H,3H)-dione were prepared as a racemic mixture in the manner described for Example 1, but replacing 8-cyclopropyl-6-(2,4-dimethoxypyrimidin-5-yl)-2-methyl-imidazo[1,2-b]pyridazine with 8-[(1S,2S)-2-[5-(difluoromethoxy)-2-pyridyl]cyclopropyl]-6-(2,4-dimethoxypyrimidin-5-yl)imidazo[1,2-b]pyridazine (racemic). ES/MS m/z: 413.10 [M+H]. $^1$H NMR (400 MHz, DMSO-d6) δ 11.85-11.61 (m, 2H), 8.59 (d, J=1.9 Hz, 1H), 8.46 (d, J=2.8 Hz, 1H), 8.23 (d, J=1.9 Hz, 1H), 8.12 (d, J=6.3 Hz, 1H), 7.86 (s, 1H), 7.69-7.54 (m, 2H), 7.30 (t, J=73.5 Hz, 1H), 3.12-2.92 (m, 2H), 1.94 (m, 2H).

Example 137. 5-(8-((2S,2S)-2-(5-(difluoromethoxy)pyridin-2-yl)cyclopropyl)imidazo[1,2-b]pyridazin-6-yl)pyrimidine-2,4(1H,3H)-dione

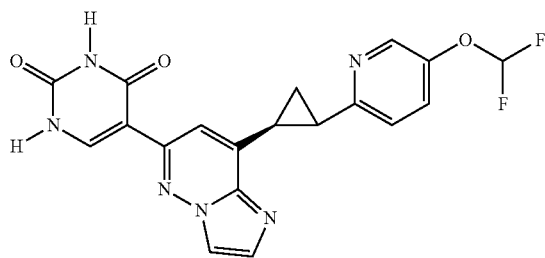

5-[8-[(1S,2S)-2-[5-(difluoromethoxy)-2-pyridyl]cyclopropyl]imidazo[1,2-b]pyridazin-6-yl]-1H-pyrimidine-2,4-dione was chirally separated from the Example 136 by SFC AD-H column (35% MeOH-DEA). ES/MS m/z: 413.10 [M+H]. $^1$H NMR (400 MHz, DMSO-d6) δ11.63-11.54 (m, 2H), 8.42 (dd, J=17.0, 2.1 Hz, 2H), 8.06 (d, J=6.2 Hz, 1H), 7.95 (s, 1H), 7.70-7.50 (m, 3H), 7.28 (t, J=73.6 Hz, 1H), 3.05-2.92 (m, 2H), 2.02-1.89 (m, 2H).

Example 138. 5-(8-((2S,2S)-2-(3-(trifluoromethyl)isoquinolin-6-yl)cyclopropyl)imidazo[1,2-b]pyridazin-6-yl)pyrimidine-2,4(1H,3H)-dione and 5-(8-((1R,2R)-2-(3-(trifluoromethyl)isoquinolin-6-yl)cyclopropyl)imidazo[1,2-b]pyridazin-6-yl)pyrimidine-2,4(1H,3H)-dione

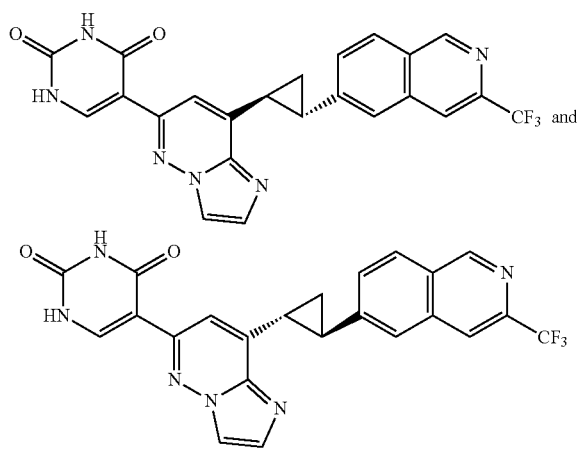

5-(8-((1S,2S)-2-(3-(trifluoromethyl)isoquinolin-6-yl)cyclopropyl)imidazo[1,2-b]pyridazin-6-yl)pyrimidine-2,4(1H,3H)-dione and 5-(8-((1R,2R)-2-(3-(trifluoromethyl)isoquinolin-6-yl)cyclopropyl)imidazo[1,2-b]pyridazin-6-yl)pyrimidine-2,4(1H,3H)-dione were prepared as a racemic mixture in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]-3-(trifluoromethyl)isoquinoline. ES/MS m/z: 465.10 [M+H]. $^1$H NMR (400 MHz, DMSO-d6) δ 11.62 (dd, J=20.3, 4.1 Hz, 2H), 9.45 (s, 1H), 8.46 (s, 1H), 8.36 (s, 1H), 8.27 (d, J=8.6 Hz, 1H), 8.13-8.02 (m, 3H), 7.84-7.72 (m, 2H), 3.05 (ddd, J=9.0, 6.6, 2.4 Hz, 2H), 2.24-2.14 (m, 1H), 2.03 (td, J=8.3, 7.8, 5.1 Hz, 1H).

Example 139. 5-(8-((2S,2S)-2-(4-(trifluoromethyl)quinolin-7-yl)cyclopropyl)imidazo[1,2-b]pyridazin-6-yl)pyrimidine-2,4(1H,3H)-dione

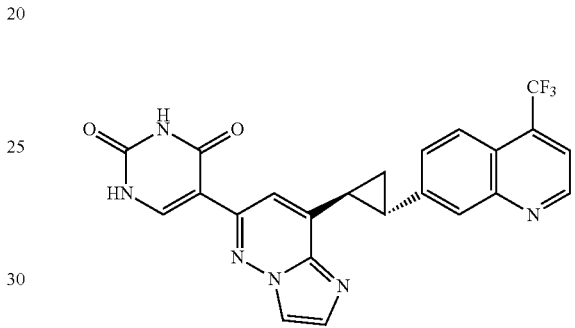

5-(8-((1S,2S)-2-(4-(trifluoromethyl)quinolin-7-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-[(1S,2S)-2-[6-(2,4-dimethoxypyrimidin-5-yl)imidazo[1,2-b]pyridazin-8-yl]cyclopropyl]-4-(trifluoromethyl)quinoline. ES/MS m/z: 465.10 [M+H]. $^1$H NMR (400 MHz, DMSO-d6) δ 11.65-11.56 (m, 2H), 9.06 (dd, J=4.3, 1.5 Hz, 1H), 8.51-8.40 (m, 2H), 8.21 (s, 1H), 8.08 (d, J=6.2 Hz, 1H), 8.05-7.97 (m, 2H), 7.76-7.67 (m, 2H), 3.15 (ddd, J=9.0, 6.3, 4.4 Hz, 1H), 3.05-2.95 (m, 1H), 2.20 (dt, J=9.0, 5.5 Hz, 1H), 2.10 (dt, J=8.6, 5.6 Hz, 1H).

Example 140. 5-(8-((2S,2S)-2-(6-(difluoromethoxy)pyridin-3-yl)cyclopropyl)imidazo[1,2-b]pyridazin-6-yl)pyrimidine-2,4(1H,3H)-dione

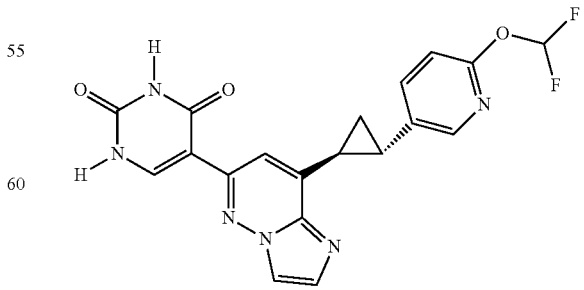

5-(8-((1S,2S)-2-(6-(difluoromethoxy)pyridin-3-yl)cyclopropyl)imidazo[1,2-b]pyridazin-6-yl)pyrimidine-2,4(1H, 3H)-dione was prepared in the manner described for Example 1, but replacing 8-cyclopropyl-6-(2,4-dimethoxypyrimidin-5-yl)-2-methyl-imidazo[1,2-b]pyridazine with 8-[(1S,2S)-2-[6-(difluoromethoxy)-3-pyridyl]cyclopropyl]-6-(2,4-dimethoxypyrimidin-5-yl)imidazo[1,2-b]pyridazine. ES/MS m/z: 413.10 [M+H]. ¹H NMR (400 MHz, DMSO-d6) δ 11.62 (m, 2H), 8.46 (s, 1H), 8.25 (d, J=2.5 Hz, 1H), 8.08-8.07 (m, 2H), 7.87-7.51 (m, 1H), 7.81 (dd, J=8.6, 2.6 Hz, 1H), 7.71 (s, 1H), 7.08 (d, J=8.5 Hz, 1H), 2.83 (dt, J=8.6, 5.5 Hz, 2H), 2.04 (dt, J=8.9, 5.4 Hz, 1H), 1.92-1.82 (m, 1H).

Example 141. 5-(8-((2S,2S)-2-(8-(trifluoromethyl)quinolin-6-yl)cyclopropyl)imidazo[1,2-b]pyridazin-6-yl)pyrimidine-2,4(1H,3H)-dione and 5-(8-((1R,2R)-2-(8-(trifluoromethyl)quinolin-6-yl)cyclopropyl)imidazo[1,2-b]pyridazin-6-yl)pyrimidine-2,4(1H,3H)-dione

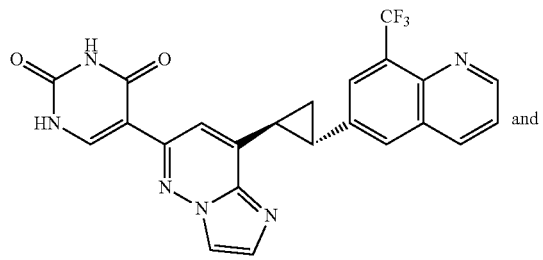

and

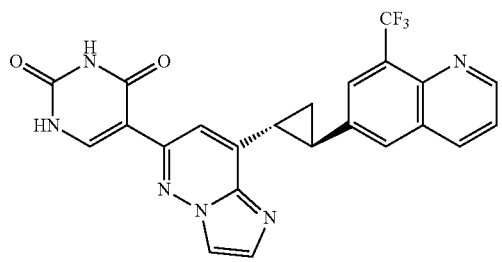 [SMILES: O=c1[nH]cc(-c2cc([C@H]3C[C@@H]3c3cc(C(F)(F)F)c4ncccc4c3)c3nccn3n2)c(=O)[nH]1]

5-(8-((1S,2S)-2-(8-(trifluoromethyl)quinolin-6-yl)cyclopropyl)imidazo[1,2-b]pyridazin-6-yl)pyrimidine-2,4(1H,3H)-dione and 5-(8-((1R,2R)-2-(8-(trifluoromethyl)quinolin-6-yl)cyclopropyl)imidazo[1,2-b]pyridazin-6-yl)pyrimidine-2,4(1H,3H)-dione were prepared as a racemic mixture in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]-8-(trifluoromethyl)quinoline. ES/MS m/z: 465.10 [M+H]. ¹H NMR (400 MHz, DMSO-d6) δ 11.58 (d, J=6.8 Hz, 2H), 9.01 (dd, J=4.2, 1.8 Hz, 1H), 8.45 (dd, J=8.5, 1.8 Hz, 1H), 8.38 (d, J=1.5 Hz, 1H), 8.19 (d, J=2.0 Hz, 1H), 8.14-8.03 (m, 2H), 7.92 (s, 1H), 7.73-7.65 (m, 2H), 3.14 (ddd, J=8.9, 6.2, 4.4 Hz, 1H), 2.93 (ddd, J=8.8, 6.0, 4.4 Hz, 1H), 2.19 (dt, J=8.9, 5.5 Hz, 1H), 2.04 (dt, J=8.7, 5.5 Hz, 1H).

Example 142. 5-(8-((1S,2S)-2-(2-(trifluoromethyl)quinolin-6-yl)cyclopropyl)imidazo[1,2-b]pyridazin-6-yl)pyrimidine-2,4(1H,3H)-dione and 5-(8-((1R,2R)-2-(2-(trifluoromethyl)quinolin-6-yl)cyclopropyl)imidazo[1,2-b]pyridazin-6-yl)pyrimidine-2,4(1H,3H)-dione

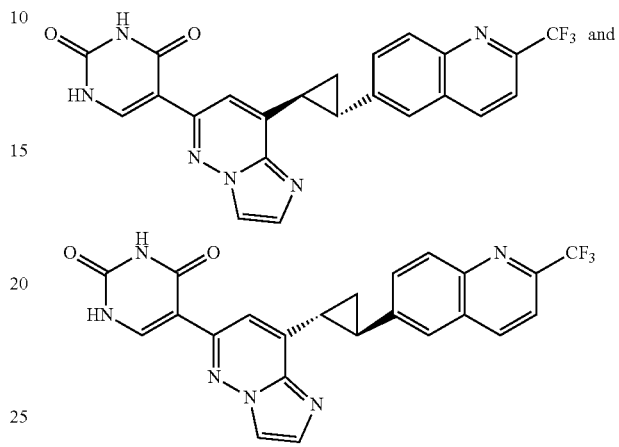

5-(8-((1S,2S)-2-(2-(trifluoromethyl)quinolin-6-yl)cyclopropyl)imidazo[1,2-b]pyridazin-6-yl)pyrimidine-2,4(1H,3H)-dione and 5-(8-((1R,2R)-2-(2-(trifluoromethyl)quinolin-6-yl)cyclopropyl)imidazo[1,2-b]pyridazin-6-yl)pyrimidine-2,4(1H,3H)-dione were prepared as a racemic mixture in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]-2-(trifluoromethyl)quinoline. ES/MS m/z: 465.10 [M+H]. ¹H NMR (400 MHz, DMSO-d6) δ 11.56 (s, 2H), 8.63 (d, J=8.6 Hz, 1H), 8.36 (d, J=1.4 Hz, 1H), 8.14 (d, J=8.8 Hz, 1H), 8.08-8.02 (m, 2H), 7.97 (d, J=8.6 Hz, 1H), 7.91-7.81 (m, 2H), 7.65 (s, 1H), 3.09 (ddd, J=9.0, 6.2, 4.4 Hz, 1H), 2.94 (ddd, J=8.8, 5.9, 4.3 Hz, 1H), 2.22 (dt, J=8.8, 5.3 Hz, 1H), 1.99 (dt, J=8.6, 5.3 Hz, 1H).

Example 143. 5-(8-((2S,2S)-2-(benzo[d]thiazol-6-yl)cyclopropyl)-2-cyclopropylimidazo[1,2-b]pyridazin-6-yl)pyrimidine-2,4(1H,3H)-dione

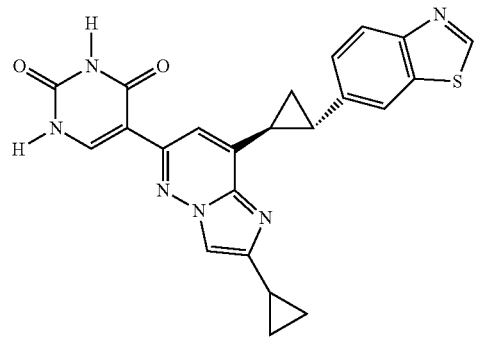 [SMILES: O=c1[nH]cc(-c2cc([C@H]3C[C@@H]3c3ccc4ncsc4c3)c3nc(C4CC4)cn3n2)c(=O)[nH]1]

5-(8-((1S,2S)-2-(benzo[d]thiazol-6-yl)cyclopropyl)-2-cyclopropylimidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-[(1S,2S)-2-[2-cyclopropyl-6-(2,4-dimethoxypyrimidin-5-yl)imidazo[1,2-b]pyridazin-8-yl]cyclopropyl]-1,3-benzothiazole(racemic). ES/MS m/z: 443.20 [M+H]. ¹H NMR (400 MHz, Methanol-d4) δ 9.24 (s, 1H), 8.28 (s, 1H), 8.15 (s, 1H), 8.10-8.01 (m, 3H), 7.51 (dd, J=8.5, 1.9 Hz, 1H), 2.96-2.86 (m, 1H), 2.82 (dt, J=9.9, 5.1 Hz, 1H), 2.23-2.11 (m, 1H), 2.11-1.93 (m, 2H), 1.26-1.16 (m, 2H), 1.02 (dt, J=6.6, 4.4 Hz, 2H).

Example 144. 5-(3-fluoro-8-((1S,2S)-2-(5-(trifluoromethyl)pyridin-2-yl)cyclopropyl)imidazo[1,2-b]pyridazin-6-yl)pyrimidine-2,4(1H,3H)-dione

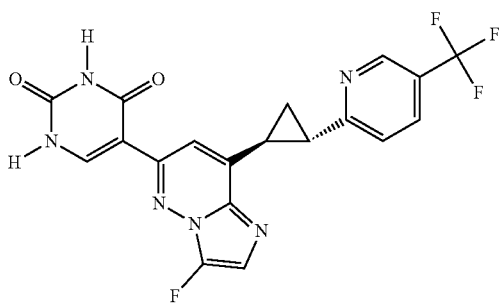 [SMILES: O=c1[nH]cc(-c2cc([C@H]3C[C@@H]3c3ccc(C(F)(F)F)cn3)c3ncc(F)n3n2)c(=O)[nH]1]

5-(3-fluoro-8-((1S,2S)-2-(5-(trifluoromethyl)pyridin-2-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-[(1S,2S)-2-[5-(trifluoromethyl)-2-pyridyl]cyclopropyl]imidazo[1,2-b]pyridazine. ES/MS m/z: 433.10 [M+H]. ¹H NMR (400 MHz, DMSO-d6) δ 11.55 (d, J=4.3 Hz, 2H), 8.90 (dd, J=2.3, 1.2 Hz, 1H), 8.14-7.98 (m, 2H), 7.70 (d, J=8.2 Hz, 1H), 7.58-7.43 (m, 2H), 3.18 (ddd, J=8.7, 5.8, 4.1 Hz, 1H), 3.03 (ddd, J=8.9, 6.2, 4.1 Hz, 1H), 2.19 (ddd, J=8.6, 6.2, 4.0 Hz, 1H), 1.93 (ddd, J=9.3, 5.8, 3.9 Hz, 1H).

Example 145. 5-(2-cyclopropyl-8-(3,3-difluoro-4,4-dimethylpyrrolidin-1-yl)imidazo[1,2-b]pyridazin-6-yl)pyrimidine-2,4(1H,3H)-dione

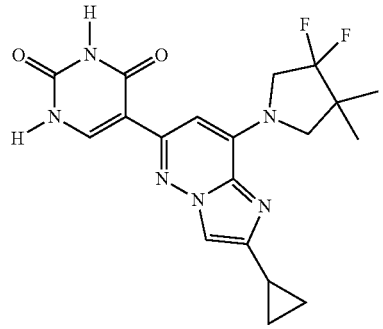 [SMILES: CC1(C)CN(c2cc(-c3c[nH]c(=O)[nH]c3=O)nn3cc(C4CC4)nc23)CC1(F)F]

5-(2-cyclopropyl-8-(3,3-difluoro-4,4-dimethylpyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 2-cyclopropyl-8-(3,3-difluoro-4,4-dimethyl-pyrrolidin-1-yl)-6-(2,4-dimethoxypyrimidin-5-yl)imidazo[1,2-b]pyridazine. ES/MS m/z: 403.20 [M+H]. ¹H NMR (400 MHz, DMSO-d6) δ11.41-11.30 (m, 2H), 7.89 (d, J=6.2 Hz, 1H), 7.81 (s, 1H), 6.53 (s, 1H), 4.40 (s, 2H), 3.78 (s, 2H), 2.00 (tt, J=8.3, 5.0 Hz, 1H), 1.21 (s, 6H), 0.96-0.85 (m, 2H), 0.88-0.77 (m, 2H).

Example 146. 5-(2-cyclopropyl-8-((1S,2S)-2-(2,4-difluorophenyl)cyclopropyl)imidazo[1,2-b]pyridazin-6-yl)pyrimidine-2,4(1H,3H)-dione

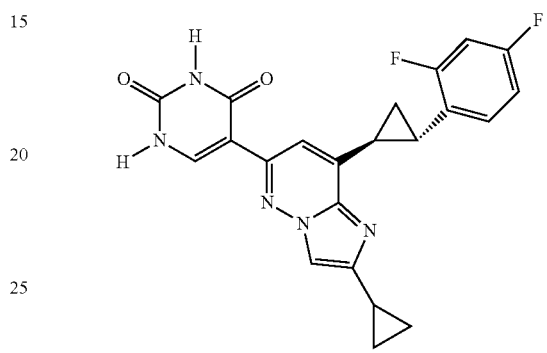

5-(2-cyclopropyl-8-((2S,2S)-2-(2,4-difluorophenyl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 2-cyclopropyl-8-[(1S,2S)-2-(2,4-difluorophenyl)cyclopropyl]-6-(2,4-dimethoxypyrimidin-5-yl)imidazo[1,2-b]pyridazine. ES/MS m/z: 422.10 [M+H]. ¹H NMR (400 MHz, DMSO-d6) δ 11.67-11.61 (m, 1H), 11.57 (d, J=2.0 Hz, 1H), 8.28 (s, 1H), 8.03 (d, J=6.2 Hz, 1H), 7.69 (s, 1H), 7.39 (td, J=8.8, 6.4 Hz, 1H), 7.25 (ddd, J=10.7, 9.3, 2.6 Hz, 1H), 7.16-7.06 (m, 1H), 2.83-2.75 (m, 2H), 2.21-2.06 (m, 1H), 1.88 (dt, J=15.4, 6.2 Hz, 2H), 1.09 (dq, J=6.2, 3.8 Hz, 2H), 0.96 (dq, J=7.1, 4.5, 4.1 Hz, 2H).

Example 147. 5-(7-(7-fluoro-5-azaspiro[2.4]heptan-5-yl)pyrazolo[1,5-a]pyrimidin-5-yl)pyrimidine-2,4(1H,3H)-dione

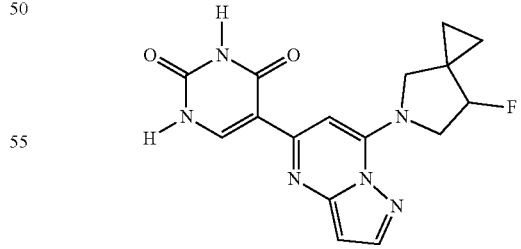

5-(7-(7-fluoro-5-azaspiro[2.4]heptan-5-yl)pyrazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-(2,4-dimethoxypyrimidin-5-yl)-7-(7-fluoro-5-azaspiro[2.4]heptan-5-yl)pyrazolo[1,5-a]pyrimidine. ES/MS m/z: 343.10 [M+H]. ¹H NMR (400

MHz, DMSO-d6) δ 11.68 (d, J=63.9 Hz, 2H), 8.43 (d, J=6.1 Hz, 1H), 8.09 (d, J=2.3 Hz, 1H), 6.92 (s, 1H), 6.43 (s, 1H), 4.59-4.21 (m, 2H), 3.93-3.70 (m, 3H), 1.20-0.81 (m, 4H).

Example 148. 5-(3-fluoro-8-(7-fluoro-5-azaspiro[2.4]heptan-5-yl)imidazo[1,2-b]pyridazin-6-yl)pyrimidine-2,4(1H,3H)-dione

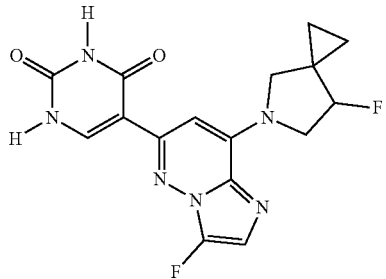 [SMILES: O=c1[nH]cc(-c2cc(N3CC(F)C4(CC4)C3)c3ncc(F)n3n2)c(=O)[nH]1]

5-(3-fluoro-8-(7-fluoro-5-azaspiro[2.4]heptan-5-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-(7-fluoro-5-azaspiro[2.4]heptan-5-yl)imidazo[1,2-b]pyridazine. ES/MS m/z: 361.20 [M+H]. $^1$H NMR (400 MHz, DMSO-d6) δ11.54-11.29 (m, 2H), 7.97 (d, J=6.1 Hz, 1H), 7.38 (d, J=7.3 Hz, 1H), 6.56 (s, 1H), 3.88-3.86 (m, 5H), 1.16-0.66 (m, 4H).

Example 149. 5-(8-((2S,2S)-2-(5-(trifluoromethyl)pyridin-2-yl)cyclopropyl)imidazo[1,2-b]pyridazin-6-yl)pyrimidine-2,4(1H,3H)-dione and 5-(8-((1R,2R)-2-(5-(trifluoromethyl)pyridin-2-yl)cyclopropyl)imidazo[1,2-b]pyridazin-6-yl)pyrimidine-2,4(1H,3H)-dione

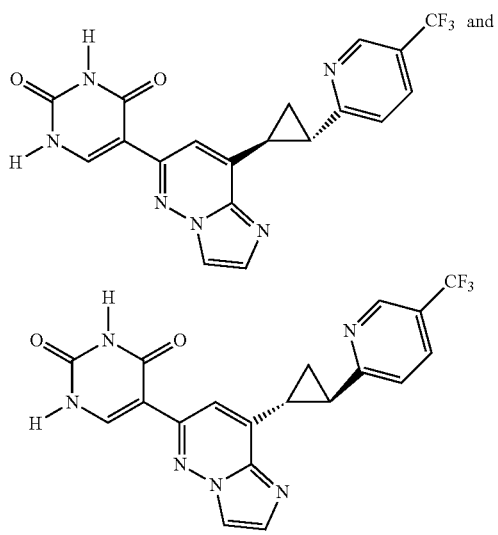

5-(8-((2S,2S)-2-(5-(trifluoromethyl)pyridin-2-yl)cyclopropyl)imidazo[1,2-b]pyridazin-6-yl)pyrimidine-2,4(1H,3H)-dione and 5-(8-((1R,2R)-2-(5-(trifluoromethyl)pyridin-2-yl)cyclopropyl)imidazo[1,2-b]pyridazin-6-yl)pyrimidine-2,4(1H,3H)-dione were prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[5-(trifluoromethyl)-2-pyridyl]cyclopropyl]imidazo[1,2-b]pyridazine(racemic). ES/MS m/z: 415.10 [M+H]. $^1$H NMR (400 MHz, DMSO-d6) δ 11.56 (d, J=4.8 Hz, 2H), 8.91 (s, 1H), 8.34 (s, 1H), 8.12 (d, J=8.4 Hz, 1H), 8.04 (d, J=6.1 Hz, 1H), 7.86 (s, 1H), 7.71 (d, J=8.2 Hz, 1H), 7.62 (s, 1H), 3.15 (dt, J=9.3, 5.0 Hz, 1H), 3.05 (dt, J=9.7, 5.2 Hz, 1H), 2.15 (dt, J=9.6, 4.9 Hz, 1H), 1.96 (dt, J=9.4, 4.8 Hz, 1H).

Example 150. 5-(8-((2S,2S)-2-(5-(trifluoromethyl)pyridin-2-yl)cyclopropyl)imidazo[1,2-b]pyridazin-6-yl)pyrimidine-2,4(1H,3H)-dione

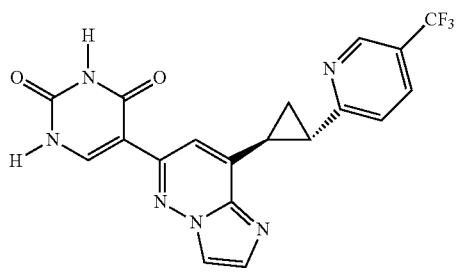 [SMILES: O=c1[nH]cc(-c2cc([C@H]3C[C@@H]3c3ccc(C(F)(F)F)cn3)c3nccn3n2)c(=O)[nH]1]

5-(8-((1S,2S)-2-(5-(trifluoromethyl)pyridin-2-yl)cyclopropyl)imidazo[1,2-b]pyridazin-6-yl)pyrimidine-2,4(1H,3H)-dione was chirally separated from the Example 149 by SFC AD-H column (20% EtOH). ES/MS m/z: 415.10 [M+H]. $^1$H NMR (400 MHz, DMSO-d6) δ 11.53 (d, J=4.7 Hz, 2H), 8.97-8.84 (m, 1H), 8.31 (d, J=1.4 Hz, 1H), 8.11 (dd, J=8.4, 2.4 Hz, 1H), 8.02 (d, J=6.3 Hz, 1H), 7.81 (s, 1H), 7.71 (d, J=8.2 Hz, 1H), 7.58 (s, 1H), 3.20-3.02 (m, 2H), 2.18 (ddd, J=9.0, 6.1, 3.9 Hz, 1H), 1.95 (ddd, J=9.2, 5.7, 4.0 Hz, 1H).

Example 151. 6-((1S,2S)-2-(6-(2,4-dioxo-1,2,3,4-tetrahydropyrimidin-5-yl)-3-fluoroimidazo[1,2-b]pyridazin-8-yl)cyclopropyl)nicotinonitrile

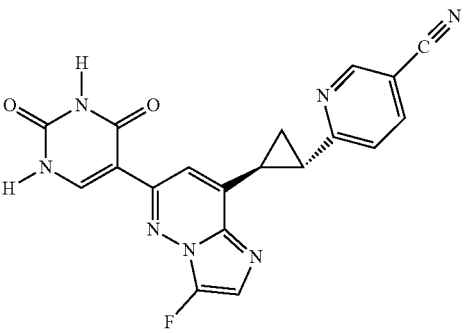 [SMILES: N#Cc1ccc([C@H]2C[C@@H]2c2cc(-c3c[nH]c(=O)[nH]c3=O)nn3c(F)cnc23)nc1]

6-((1S,2S)-2-(6-(2,4-dioxo-1,2,3,4-tetrahydropyrimidin-5-yl)-3-fluoroimidazo[1,2-b]pyridazin-8-yl)cyclopropyl)nicotinonitrile was prepared as a racemic mixture in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)-3-fluoro-imidazo[1,2-b]pyridazin-8-yl] cyclopropyl]pyridine-3-carbonitrile(racemic). ES/MS m/z: 390.10 [M+H]. ¹H NMR (400 MHz, DMSO-d6) δ 11.57-11.51 (m, 2H), 8.96 (d, J=2.2 Hz, 1H), 8.20 (dd, J=8.2, 2.2 Hz, 1H), 8.03 (d, J=6.4 Hz, 1H), 7.69 (dd, J=8.3, 0.9 Hz, 1H), 7.59-7.50 (m, 2H), 3.16 (ddd, J=8.6, 5.7, 4.1 Hz, 1H), 3.02 (ddd, J=9.1, 6.3, 4.1 Hz, 1H), 2.23 (ddd, J=8.6, 6.3, 4.0 Hz, 1H), 1.93 (ddd, J=9.3, 5.7, 4.0 Hz, 1H).

Example 152. 5-(8-((1S,2S)-2-(6-(trifluoromethyl) pyridin-3-yl)cyclopropyl)imidazo[1,2-b]pyridazin-6-yl)pyrimidine-2,4(1H,3H)-dione and 5-(8-((1R,2R)-2-(6-(trifluoromethyl)pyridin-3-yl)cyclopropyl) imidazo[1,2-b]pyridazin-6-yl)pyrimidine-2,4(1H, 3H)-dione

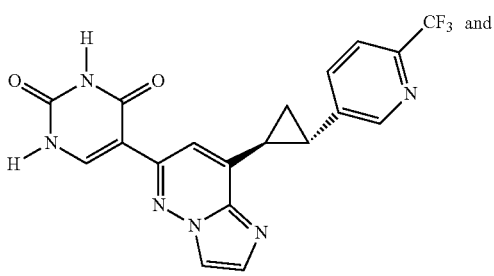

5-(8-((1S,2S)-2-(6-(trifluoromethyl)pyridin-3-yl)cyclopropyl)imidazo[1,2-b]pyridazin-6-yl)pyrimidine-2,4(1H, 3H)-dione and 5-(8-((1R,2R)-2-(6-(trifluoromethyl)pyridin-3-yl)cyclopropyl)imidazo[1,2-b]pyridazin-6-yl)pyrimidine-2,4(1H,3H)-dione were prepared as a racemic mixture in the manner described for Example 1, but replacing 8-cyclopropyl-6-(2,4-dimethoxypyrimidin-5-yl)-2-methyl-imidazo[1, 2-b]pyridazine with 6-(2,4-dimethoxypyrimidin-5-yl)-8-[(1S,2S)-2-[6-(trifluoromethyl)-3-pyridyl]cyclopropyl] imidazo[1,2-b]pyridazine(racemic). ES/MS m/z: 415.10 [M+H]. ¹H NMR (400 MHz, DMSO-d6) δ) δ 11.59-11.56 (m, 2H), 8.74 (d, J=2.1 Hz, 1H), 8.37 (d, J=1.5 Hz, 1H), 8.05 (d, J=6.1 Hz, 1H), 7.98-7.88 (m, 2H), 7.86 (d, J=8.2 Hz, 1H), 7.66 (s, 1H), 2.99 (ddd, J=9.0, 6.2, 4.4 Hz, 1H), 2.89 (ddd, J=8.8, 6.1, 4.5 Hz, 1H), 2.22 (dt, J=8.9, 5.4 Hz, 1H), 1.99-1.89 (m, 1H).

Example 153. 5-(8-((2S,2S)-2-(6-(trifluoromethyl) pyridin-3-yl)cyclopropyl)imidazo[1,2-b]pyridazin-6-yl)pyrimidine-2,4(1H,3H)-dione

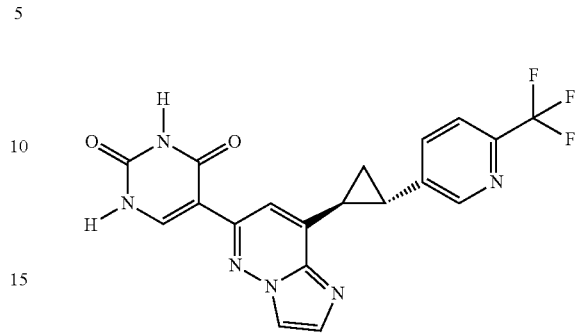

5-(8-((1S,2S)-2-(6-(trifluoromethyl)pyridin-3-yl)cyclopropyl)imidazo[1,2-b]pyridazin-6-yl)pyrimidine-2,4(1H, 3H)-dione was chirally separated from the Example 152 by SFC OD-H column (20% IPA-NH3). ES/MS m/z: 415.10 [M+H]. ¹H NMR (400 MHz, DMSO-d6) δ 11.56 (d, J=4.7 Hz, 2H), 8.75 (d, J=2.1 Hz, 1H), 8.34 (d, J=1.4 Hz, 1H), 8.04 (d, J=6.3 Hz, 1H), 7.94 (dd, J=8.2, 2.2 Hz, 1H), 7.89-7.82 (m, 2H), 7.63 (s, 1H), 3.01 (ddd, J=9.3, 6.2, 4.4 Hz, 1H), 2.89 (ddd, J=8.9, 6.1, 4.3 Hz, 1H), 2.24 (dt, J=8.9, 5.3 Hz, 1H), 1.93 (dt, J=8.7, 5.3 Hz, 1H).

Example 154. 5-(8-((2S,2S)-2-(quinolin-7-yl)cyclopropyl)imidazo[1,2-b]pyridazin-6-yl)pyrimidine-2,4 (1H,3H)-dione

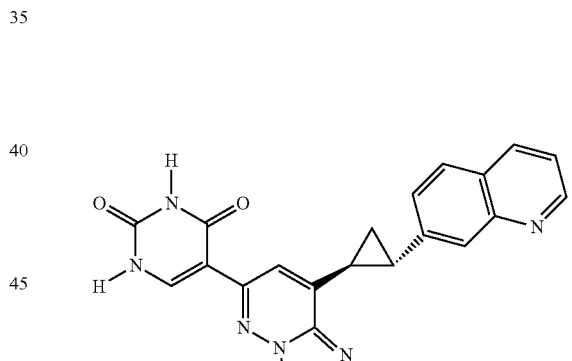

5-(8-((1S,2S)-2-(quinolin-7-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 7-[(1S,2S)-2-[6-(2,4-dimethoxypyrimidin-5-yl)imidazo[1,2-b]pyridazin-8-yl]cyclopropyl]quinoline(racemic). ES/MS m/z: 397.10 [M+H]. ¹H NMR (400 MHz, DMSO-d6) δ 11.71 (d, J=6.2 Hz, 1H), 11.61 (d, J=2.0 Hz, 1H), 9.18 (dd, J=5.1, 1.6 Hz, 1H), 8.97 (d, J=8.3 Hz, 1H), 8.50 (d, J=1.7 Hz, 1H), 8.27 (d, J=8.6 Hz, 1H), 8.18-8.07 (m, 3H), 7.91 (dd, J=8.3, 5.1 Hz, 1H), 7.83-7.75 (m, 2H), 3.20-3.08 (m, 2H), 2.25-2.15 (m, 1H), 2.05 (dt, J=8.5, 5.5 Hz, 1H).

Example 155. 6-((1S,2S)-2-(6-(2,4-dioxo-1,2,3,4-tetrahydropyrimidin-5-yl)imidazo[1,2-b]pyridazin-8-yl)cyclopropyl)nicotinonitrile

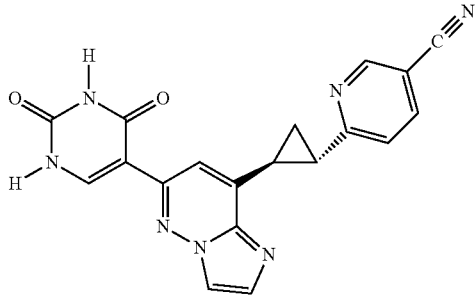 [SMILES: N#Cc1ccc([C@H]2C[C@@H]2c2cc(-c3c[nH]c(=O)[nH]c3=O)nn3ccnc23)nc1]

6-((2S,2S)-2-(6-(2,4-dioxo-1,2,3,4-tetrahydropyrimidin-5-yl)imidazo[1,2-b]pyridazin-8-yl)cyclopropyl)nicotinonitrile was prepared as a racemic mixture in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]pyridine-3-carbonitrile(racemic). ES/MS m/z: 372.10 [M+H]. $^1$H NMR (400 MHz, DMSO-d6) δ 11.71-11.65 (m, 1H), 11.60 (d, J=2.0 Hz, 1H), 8.99 (dd, J=2.3, 0.8 Hz, 1H), 8.49 (d, J=1.7 Hz, 1H), 8.23 (dd, J=8.2, 2.2 Hz, 1H), 8.09 (d, J=6.3 Hz, 2H), 7.78 (s, 1H), 7.69 (dd, J=8.2, 0.9 Hz, 1H), 3.10 (ddt, J=8.9, 6.4, 3.4 Hz, 2H), 2.05 (dddd, J=31.9, 8.2, 6.4, 4.1 Hz, 2H).

Example 156. 5-(8-((1S,2S)-2-(isoquinolin-6-yl)cyclopropyl)imidazo[1,2-b]pyridazin-6-yl)pyrimidine-2,4(1H,3H)-dione

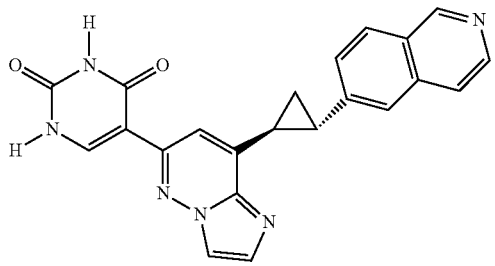 [SMILES: O=c1[nH]cc(-c2cc([C@H]3C[C@@H]3c3ccc4cnccc4c3)c3nccn3n2)c(=O)[nH]1]

5-(8-((1S,2S)-2-(isoquinolin-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]isoquinoline(racemic). ES/MS m/z: 397.20 [M+H]. $^1$H NMR (400 MHz, DMSO-d6) δ 11.84-11.76 (m, 1H), 11.63 (d, J=2.0 Hz, 1H), 9.21 (dd, J=5.2, 1.5 Hz, 1H), 8.97 (d, J=8.3 Hz, 1H), 8.57 (d, J=1.8 Hz, 1H), 8.38-8.25 (m, 2H), 8.21 (s, 1H), 8.13 (d, J=6.2 Hz, 1H), 8.03 (ddd, J=16.3, 8.7, 3.5 Hz, 2H), 7.87 (s, 1H), 3.28 (dt, J=9.8, 5.2 Hz, 1H), 3.11-3.01 (m, 1H), 2.12 (dt, J=8.9, 5.5 Hz, 1H), 2.04 (dt, J=8.6, 5.6 Hz, 1H).

Example 157. 5-(8-((2S,2S)-2-(quinolin-6-yl)cyclopropyl)imidazo[1,2-b]pyridazin-6-yl)pyrimidine-2,4(1H,3H)-dione

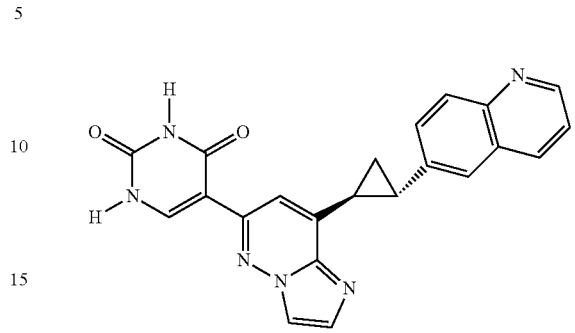

5-(8-((2S,2S)-2-(quinolin-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]quinoline(racemic). ES/MS m/z: 397.20 [M+H]. $^1$H NMR (400 MHz, DMSO-d6) δ 11.82 (dd, J=6.4, 2.0 Hz, 1H), 11.63 (d, J=2.0 Hz, 1H), 9.86 (s, 1H), 8.66 (d, J=6.6 Hz, 1H), 8.58-8.48 (m, 2H), 8.37 (d, J=6.5 Hz, 1H), 8.28 (d, J=1.6 Hz, 1H), 8.20-8.09 (m, 2H), 7.96 (dd, J=8.7, 1.7 Hz, 1H), 7.87 (s, 1H), 3.39 (dd, J=8.8, 4.9 Hz, 1H), 3.11 (ddd, J=9.1, 6.3, 4.3 Hz, 1H), 2.21 (dt, J=8.7, 5.4 Hz, 1H), 2.11 (dt, J=8.8, 5.5 Hz, 1H).

Example 158. 4-((2S,2S)-2-(6-(2,4-dioxo-1,2,3,4-tetrahydropyrimidin-5-yl)-3-fluoroimidazo[1,2-b]pyridazin-8-yl)cyclopropyl)benzonitrile

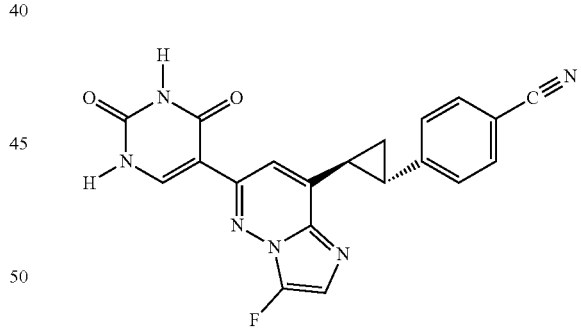

4-((1S,2S)-2-(6-(2,4-dioxo-1,2,3,4-tetrahydropyrimidin-5-yl)-3-fluoroimidazo[1,2-b]pyridazin-8-yl)cyclopropyl)benzonitrile was prepared in the manner described for Example 1, but replacing 8-cyclopropyl-6-(2,4-dimethoxypyrimidin-5-yl)-2-methyl-imidazo[1,2-b]pyridazine with 4-[(1S,2S)-2-[6-(2,4-dimethoxypyrimidin-5-yl)-3-fluoroimidazo[1,2-b]pyridazin-8-yl]cyclopropyl]benzonitrile. ES/MS m/z: 389.10 [M+H]. $^1$H NMR (400 MHz, DMSO-d6) δ 11.63 (dd, J=6.2, 2.0 Hz, 1H), 11.55 (d, J=2.0 Hz, 1H), 8.04 (d, J=6.2 Hz, 1H), 7.77 (d, J=8.3 Hz, 2H), 7.64 (d, J=6.9 Hz, 1H), 7.55 (s, 1H), 7.51-7.44 (m, 2H), 2.93 (ddd, J=9.0, 6.2, 4.4 Hz, 1H), 2.84 (ddd, J=8.9, 6.1, 4.4 Hz, 1H), 2.18 (dt, J=8.7, 5.3 Hz, 1H), 1.90-1.80 (m, 1H).

Example 159. 5-(8-((2S,2S)-2-(pyridin-2-yl)cyclopropyl)imidazo[1,2-b]pyridazin-6-yl)pyrimidine-2,4(1H,3H)-dione

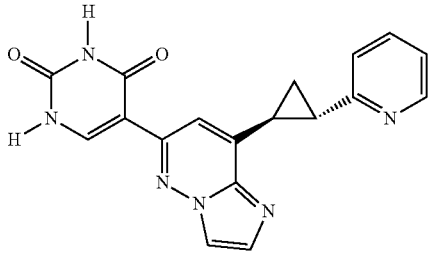 [SMILES: O=c1[nH]cc(-c2cc([C@H]3C[C@@H]3c3ccccn3)c3nccn3n2)c(=O)[nH]1]

5-(8-((1S,2S)-2-(pyridin-2-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-(2-pyridyl)cyclopropyl]imidazo[1,2-b]pyridazine. ES/MS m/z: 347.10 [M+H]. $^1$H NMR (400 MHz, DMSO-d6) δ 11.76 (dd, J=6.3, 2.0 Hz, 1H), 11.62 (d, J=2.0 Hz, 1H), 8.67 (dd, J=5.5, 1.6 Hz, 1H), 8.54 (d, J=1.7 Hz, 1H), 8.21-8.08 (m, 3H), 7.86 (s, 1H), 7.74 (d, J=8.0 Hz, 1H), 7.61 (t, J=6.5 Hz, 1H), 3.27-3.17 (m, 1H), 3.13 (ddd, J=8.7, 6.3, 4.3 Hz, 1H), 2.22-2.10 (m, 2H).

Example 160. 5-(8-((2S,2S)-2-(2-(trifluoromethyl)pyridin-4-yl)cyclopropyl)imidazo[1,2-b]pyridazin-6-yl)pyrimidine-2,4(1H,3H)-dione

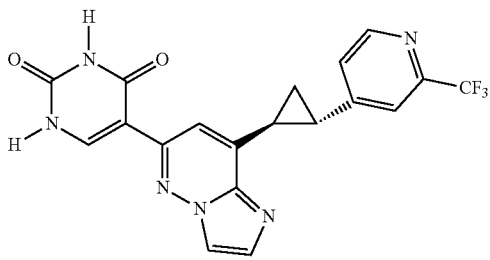 [SMILES: O=c1[nH]cc(-c2cc([C@H]3C[C@@H]3c3ccnc(C(F)(F)F)c3)c3nccn3n2)c(=O)[nH]1]

5-(8-((2S,2S)-2-(2-(trifluoromethyl)pyridin-4-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[2-(trifluoromethyl)-4-pyridyl]cyclopropyl]imidazo[1,2-b]pyridazine(racemic). ES/MS m/z: 415.10 [M+H]. $^1$H NMR (400 MHz, DMSO-d6) δ 11.74-11.66 (m, 1H), 11.61 (d, J=2.0 Hz, 1H), 8.67 (d, J=5.1 Hz, 1H), 8.51 (d, J=1.7 Hz, 1H), 8.15-8.06 (m, 2H), 7.86-7.77 (m, 2H), 7.63 (dd, J=5.2, 1.7 Hz, 1H), 3.20-3.05 (m, 1H), 2.96 (ddd, J=9.0, 6.2, 4.3 Hz, 1H), 2.15 (dt, J=8.9, 5.6 Hz, 1H), 2.03 (dt, J=8.8, 5.6 Hz, 1H).

Example 161. 5-(8-((2S,2S)-2-(3-fluoropyridin-4-yl)cyclopropyl)imidazo[1,2-b]pyridazin-6-yl)pyrimidine-2,4(1H,3H)-dione

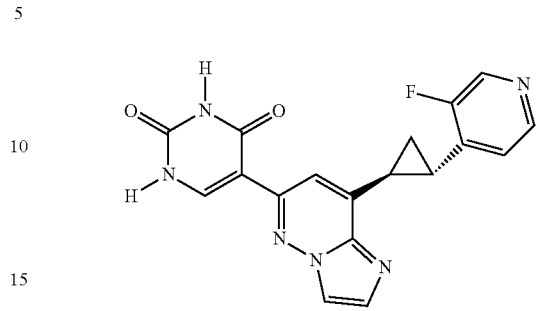

5-(8-((1S,2S)-2-(3-fluoropyridin-4-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-(3-fluoro-4-pyridyl)cyclopropyl]imidazo[1,2-b]pyridazine(racemic). ES/MS m/z: 365.10 [M+H]. $^1$H NMR (400 MHz, DMSO-d6) δ 11.77 (d, J=6.3 Hz, 1H), 11.63 (d, J=1.9 Hz, 1H), 8.65 (d, J=2.2 Hz, 1H), 8.59 (d, J=1.8 Hz, 1H), 8.50 (d, J=5.2 Hz, 1H), 8.25 (s, 1H), 8.11 (d, J=6.2 Hz, 1H), 7.91 (s, 1H), 7.51 (t, J=6.0 Hz, 1H), 3.20 (d, J=10.3 Hz, 1H), 2.97-2.87 (m, 1H), 2.13 (dt, J=8.9, 5.5 Hz, 1H), 2.02 (dt, J=8.7, 5.5 Hz, 1H).

Example 162. 5-(8-((2S,2S)-2-(pyridin-3-yl)cyclopropyl)imidazo[1,2-b]pyridazin-6-yl)pyrimidine-2,4(1H,3H)-dione

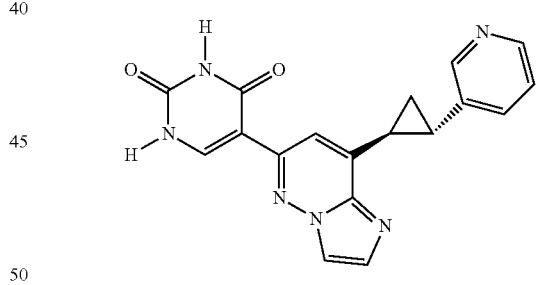

5-(8-((1S,2S)-2-(pyridin-3-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-(3-pyridyl)cyclopropyl]imidazo[1,2-b]pyridazine. ES/MS m/z: 347.10 [M+H]. $^1$H NMR (400 MHz, DMSO-d6) δ 11.55 (d, J=6.8 Hz, 2H), 8.78 (d, J=2.1 Hz, 1H), 8.64 (dd, J=5.3, 1.4 Hz, 1H), 8.32 (d, J=1.3 Hz, 1H), 8.14 (d, J=8.0 Hz, 1H), 8.03 (d, J=6.0 Hz, 1H), 7.83 (d, J=1.3 Hz, 1H), 7.75 (dd, J=8.1, 5.3 Hz, 1H), 7.61 (s, 1H), 3.05 (dt, J=9.5, 5.7 Hz, 1H), 2.88 (ddd, J=8.9, 6.1, 4.5 Hz, 1H), 2.25 (dt, J=8.8, 5.3 Hz, 1H), 1.91 (dt, J=8.7, 5.3 Hz, 1H).

Example 163. 5-(8-((2S,2S)-2-(quinolin-3-yl)cyclopropyl)imidazo[1,2-b]pyridazin-6-yl)pyrimidine-2,4(1H,3H)-dione

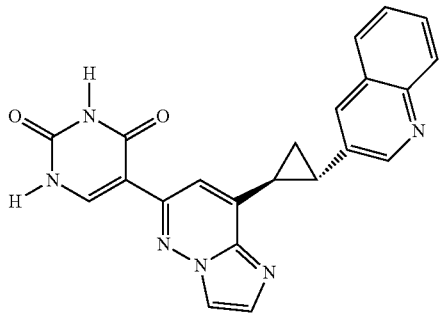 [SMILES: O=c1[nH]cc(-c2cc([C@H]3C[C@@H]3c3cnc4ccccc4c3)c3nccn3n2)c(=O)[nH]1]

5-(8-((1S,2S)-2-(quinolin-3-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 3-[(1S,2S)-2-[6-(2,4-dimethoxypyrimidin-5-yl)imidazo[1,2-b]pyridazin-8-yl]cyclopropyl]quinoline(racemic). ES/MS m/z: 397.20 [M+H]. $^1$H NMR (400 MHz, DMSO-d6) δ 11.64-11.55 (m, 2H), 9.06 (d, J=2.1 Hz, 1H), 8.47 (s, 1H), 8.40 (s, 1H), 8.11-7.97 (m, 3H), 7.94 (s, 1H), 7.84 (dd, J=8.5, 6.8 Hz, 1H), 7.76-7.68 (m, 2H), 3.13 (ddd, J=9.4, 6.1, 4.4 Hz, 1H), 3.01-2.91 (m, 1H), 2.24 (dt, J=8.8, 5.4 Hz, 1H), 2.06 (dt, J=8.5, 5.5 Hz, 1H).

Example 164. 5-(8-((2S,2S)-2-(5-fluoropyridin-3-yl)cyclopropyl)imidazo[1,2-b]pyridazin-6-yl)pyrimidine-2,4(1H,3H)-dione

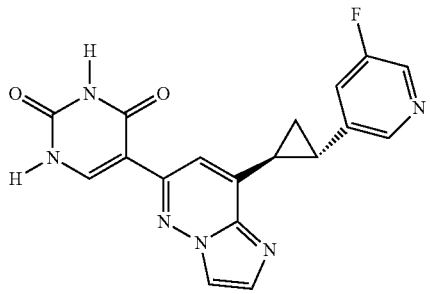 [SMILES: O=c1[nH]cc(-c2cc([C@H]3C[C@@H]3c3cncc(F)c3)c3nccn3n2)c(=O)[nH]1]

5-(8-((1S,2S)-2-(5-fluoropyridin-3-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-(5-fluoro-3-pyridyl)cyclopropyl]imidazo[1,2-b]pyridazine(racemic). ES/MS m/z: 365.20 [M+H]. $^1$H NMR (400 MHz, DMSO-d6) δ 11.81 (d, J=6.2 Hz, 1H), 11.64 (d, J=1.8 Hz, 1H), 8.62 (d, J=1.8 Hz, 1H), 8.51 (d, J=2.4 Hz, 2H), 8.31 (s, 1H), 8.14 (d, J=6.2 Hz, 1H), 7.88 (s, 1H), 7.74 (dt, J=10.4, 2.1 Hz, 1H), 3.16 (dt, J=9.7, 5.4 Hz, 1H), 2.88-2.78 (m, 1H), 2.00 (dq, J=11.7, 5.3 Hz, 2H).

Example 165. 5-(8-((2S,2S)-2-(2-fluoro-4-(trifluoromethyl)phenyl)cyclopropyl)imidazo[1,2-b]pyridazin-6-yl)pyrimidine-2,4(1H,3H)-dione

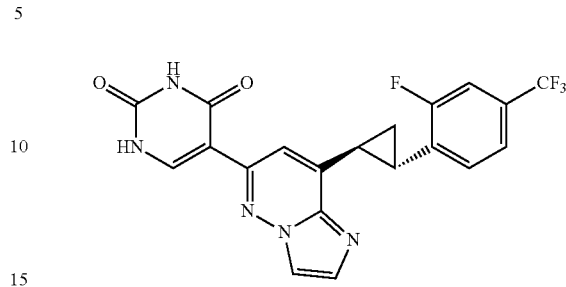

5-(8-((1S,2S)-2-(2-fluoro-4-(trifluoromethyl)phenyl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[2-fluoro-4-(trifluoromethyl)phenyl]cyclopropyl]imidazo[1,2-b]pyridazine(racemic). ES/MS m/z: 432.10 [M+H]. $^1$H NMR (400 MHz, DMSO-d6) δ 11.72 (dd, J=6.4, 2.0 Hz, 1H), 11.61 (d, J=1.9 Hz, 1H), 8.54 (d, J=1.8 Hz, 1H), 8.22-8.06 (m, 2H), 7.84 (s, 1H), 7.71-7.47 (m, 3H), 2.98 (ddt, J=39.4, 10.2, 5.4 Hz, 2H), 2.13-1.90 (m, 2H).

Example 166. 5-(8-((1S,2S)-2-(isoquinolin-8-yl)cyclopropyl)imidazo[1,2-b]pyridazin-6-yl)pyrimidine-2,4(1H,3H)-dione

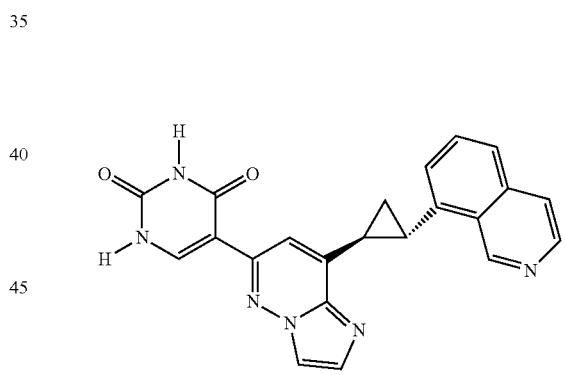

5-(8-((1S,2S)-2-(isoquinolin-8-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-[(1S,2S)-2-[6-(2,4-dimethoxypyrimidin-5-yl)imidazo[1,2-b]pyridazin-8-yl]cyclopropyl]isoquinoline(racemic). ES/MS m/z: 397.20 [M+H]. $^1$H NMR (400 MHz, DMSO-d6) δ 11.65-11.54 (m, 2H), 9.80 (s, 1H), 8.65 (d, J=6.1 Hz, 1H), 8.40 (d, J=1.4 Hz, 1H), 8.30 (d, J=6.2 Hz, 1H), 8.12 (d, J=8.3 Hz, 1H), 8.11-8.01 (m, 2H), 7.93-7.81 (m, 2H), 7.74 (s, 1H), 3.56 (dt, J=8.7, 5.8 Hz, 1H), 2.90 (dt, J=8.8, 5.5 Hz, 1H), 2.19 (dt, J=8.8, 5.3 Hz, 1H), 2.01 (ddd, J=8.8, 6.4, 4.8 Hz, 1H).

Example 167. 5-(8-((2S,2S)-2-(quinolin-4-yl)cyclopropyl)imidazo[1,2-b]pyridazin-6-yl)pyrimidine-2,4(1H,3H)-dione

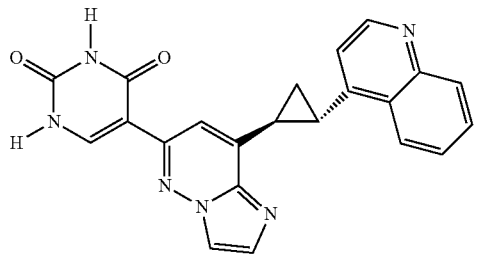 [SMILES: O=c1[nH]cc(-c2cc([C@H]3C[C@@H]3c3ccnc4ccccc34)c3nccn3n2)c(=O)[nH]1]

5-(8-((1S,2S)-2-(quinolin-4-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 4-[(1S,2S)-2-[6-(2,4-dimethoxypyrimidin-5-yl)imidazo[1,2-b]pyridazin-8-yl]cyclopropyl]quinoline(racemic). ES/MS m/z: 397.20 [M+H]. $^1$H NMR (400 MHz, DMSO-d6) δ 11.63-11.54 (m, 2H), 9.13 (d, J=5.2 Hz, 1H), 8.43-8.35 (m, 2H), 8.20 (d, J=8.5 Hz, 1H), 8.07 (d, J=6.1 Hz, 1H), 7.99 (dd, J=8.4, 6.8 Hz, 1H), 7.88 (s, 1H), 7.83-7.71 (m, 3H), 3.75-3.73 (m, 1H), 3.04 (dt, J=9.0, 5.7 Hz, 1H), 2.40-2.30 (m, 1H), 2.17 (dt, J=8.7, 5.2 Hz, 1H).

Example 168. 5-(8-((2S,2S)-2-(isoquinolin-5-yl)cyclopropyl)imidazo[1,2-b]pyridazin-6-yl)pyrimidine-2,4(1H,3H)-dione

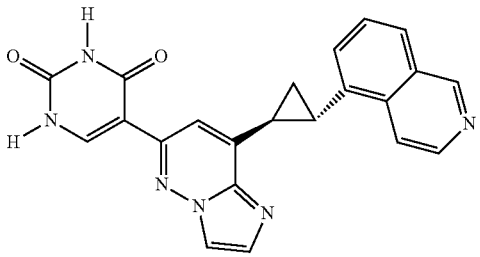 [SMILES: O=c1[nH]cc(-c2cc([C@H]3C[C@@H]3c3cccc4cnccc34)c3nccn3n2)c(=O)[nH]1]

5-(8-((1S,2S)-2-(isoquinolin-5-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 5-[(1S,2S)-2-[6-(2,4-dimethoxypyrimidin-5-yl)imidazo[1,2-b]pyridazin-8-yl]cyclopropyl]isoquinoline(racemic). ES/MS m/z: 397.20 [M+H]. $^1$H NMR (400 MHz, DMSO-d6) δ 11.64-11.54 (m, 2H), 9.70 (s, 1H), 8.60 (d, J=6.4 Hz, 1H), 8.40 (d, J=1.4 Hz, 1H), 8.34-8.27 (m, 2H), 8.08 (d, J=6.1 Hz, 1H), 8.01 (d, J=7.2 Hz, 1H), 7.95-7.86 (m, 2H), 7.75 (s, 1H), 3.46 (dt, J=9.0, 6.0 Hz, 1H), 2.82 (dt, J=8.9, 5.4 Hz, 1H), 2.17 (dt, J=8.9, 5.2 Hz, 1H), 1.99 (ddd, J=8.7, 6.4, 4.8 Hz, 1H).

Example 169. 5-(8-(3-fluoro-3-(trifluoromethyl)pyrrolidin-1-yl)imidazo[1,2-b]pyridazin-6-yl)pyrimidine-2,4(1H,3H)-dione

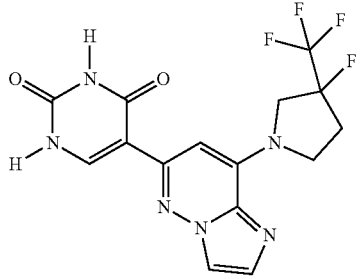 [SMILES: O=c1[nH]cc(-c2cc(N3CCC(F)(C(F)(F)F)C3)c3nccn3n2)c(=O)[nH]1]

5-(8-(3-fluoro-3-(trifluoromethyl)pyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[3-fluoro-3-(trifluoromethyl)pyrrolidin-1-yl]imidazo[1,2-b]pyridazine. ES/MS m/z: 385.10 [M+H]. $^1$H NMR (400 MHz, DMSO-d6) δ11.55 (dd, J=6.2, 2.0 Hz, 1H), 11.45 (d, J=2.0 Hz, 1H), 8.21 (d, J=1.4 Hz, 1H), 8.00 (d, J=6.2 Hz, 1H), 7.78 (d, J=1.5 Hz, 1H), 6.85 (s, 1H), 4.64-4.39 (m, 2H), 4.12 (d, J=9.9 Hz, 1H), 4.02-3.86 (m, 1H), 2.77-2.52 (m, 2H).

Example 170. 5-(8-(7-(difluoromethyl)-5-azaspiro[2.4]heptan-5-yl)imidazo[1,2-b]pyridazin-6-yl)pyrimidine-2,4(1H,3H)-dione

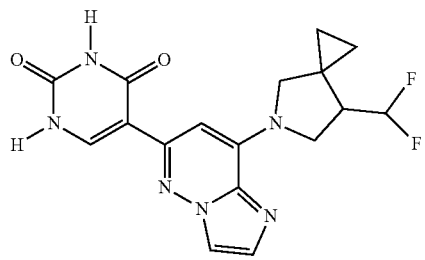 [SMILES: O=c1[nH]cc(-c2cc(N3CC(C(F)F)C4(CC4)C3)c3nccn3n2)c(=O)[nH]1]

5-(8-(7-(difluoromethyl)-5-azaspiro[2.4]heptan-5-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-[7-(difluoromethyl)-5-azaspiro[2.4]heptan-5-yl]-6-(2,4-dimethoxypyrimidin-5-yl)imidazo[1,2-b]pyridazine. ES/MS m/z: 375.10 [M+H]. $^1$H NMR (400 MHz, DMSO-d6) δ11.56-11.37 (m, 2H), 8.20 (d, J=1.5 Hz, 1H), 8.00 (d, J=6.2 Hz, 1H), 7.82-7.74 (m, 1H), 6.78 (s, 1H), 6.24 (td, J=55.8, 4.2 Hz, 1H), 4.15 (s, 2H), 3.95-3.88 (m, 1H), 3.64 (s, 1H), 1.08 (dt, J=9.9, 5.5 Hz, 1H), 0.90-0.68 (m, 4H).

Example 171. 5-(8-(7-fluoro-5-azaspiro[2.4]heptan-5-yl)imidazo[1,2-b]pyridazin-6-yl)pyrimidine-2,4(1H,3H)-dione

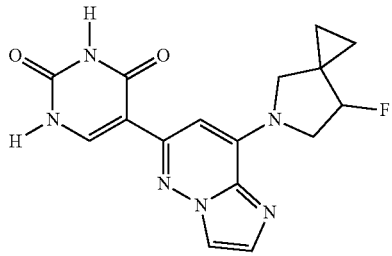 [SMILES: O=c1[nH]cc(-c2cc(N3CC(F)C4(CC4)C3)c3nccn3n2)c(=O)[nH]1]

5-(8-(7-fluoro-5-azaspiro[2.4]heptan-5-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(7-fluoro-5-azaspiro[2.4]heptan-5-yl)imidazo[1,2-b]pyridazine. ES/MS m/z: 343.10 [M+H]. $^1$H NMR (400 MHz, DMSO-d6) δ 11.44-11.30 (m, 2H), 8.07 (q, J=1.3 Hz, 1H), 7.95 (d, J=6.0 Hz, 1H), 7.60 (dt, J=2.4, 1.4 Hz, 1H), 6.61 (t, J=2.0 Hz, 1H), 4.83 (dd, J=54.5, 3.3 Hz, 1H), 4.62-3.98 (m, 3H), 3.70 (s, 1H), 1.11-0.73 (m, 4H).

Example 172. ethyl 6-(2,4-dioxo-1,2,3,4-tetrahydro-pyrimidin-5-yl)-8-((1S,2S)-2-(4-fluorophenyl)cyclopropyl)imidazo[1,2-b]pyridazine-2-carboxylate

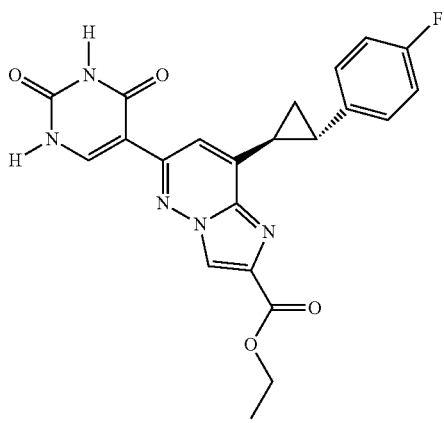 [SMILES: CCOC(=O)c1cn2nc(-c3c[nH]c(=O)[nH]c3=O)cc([C@H]3C[C@@H]3c3ccc(F)cc3)c2n1]

ethyl 6-(2,4-dioxo-1,2,3,4-tetrahydropyrimidin-5-yl)-8-((1S,2S)-2-(4-fluorophenyl)cyclopropyl)imidazo[1,2-b]pyridazine-2-carboxylate was prepared as a racemic mixture in the manner described for Example 1, but replacing 8-cyclopropyl-6-(2,4-dimethoxypyrimidin-5-yl)-2-methyl-imidazo[1,2-b]pyridazine with ethyl 6-(2,4-dimethoxypyrimidin-5-yl)-8-[(1S,2S)-2-(4-fluorophenyl)cyclopropyl]imidazo[1,2-b]pyridazine-2-carboxylate(racemic). ES/MS m/z: 436.10 [M+H]. $^1$H NMR (400 MHz, DMSO-d6) δ 11.57-11.55 (m, 2H), 8.75 (s, 1H), 8.02 (d, J=6.3 Hz, 1H), 7.52 (s, 1H), 7.32 (ddd, J=8.6, 5.4, 2.6 Hz, 1H), 7.20-7.09 (m, 2H), 4.34 (q, J=7.1 Hz, 2H), 2.74 (dddd, J=19.7, 8.8, 6.1, 4.4 Hz, 2H), 2.01 (dt, J=9.0, 5.3 Hz, 1H), 1.84-1.74 (m, 1H), 1.33 (t, J=7.1 Hz, 3H).

Example 173. 5-(8-(3-(4-methoxyphenyl)pyrrolidin-1-yl)imidazo[1,2-b]pyridazin-6-yl)pyrimidine-2,4(1H,3H)-dione

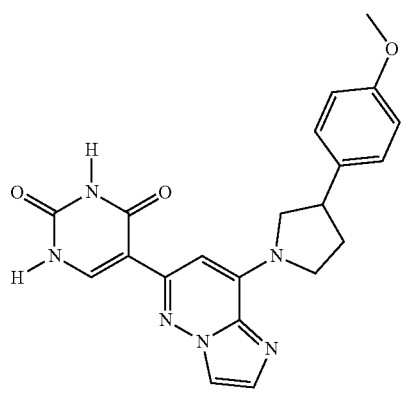 [SMILES: COc1ccc(C2CCN(c3cc(-c4c[nH]c(=O)[nH]c4=O)nn4ccnc34)C2)cc1]

5-(8-(3-(4-methoxyphenyl)pyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[3-(4-methoxyphenyl)pyrrolidin-1-yl]imidazo[1,2-b]pyridazine. ES/MS m/z: 405.20 [M+H]. $^1$H NMR (400 MHz, DMSO-d6) δ 11.58 (d, J=6.3 Hz, 1H), 11.46 (d, J=2.0 Hz, 1H), 8.29 (d, J=1.7 Hz, 1H), 8.03 (d, J=6.2 Hz, 1H), 7.90 (s, 1H), 7.38-7.28 (m, 2H), 6.94 (dd, J=9.4, 7.4 Hz, 3H), 4.33 (s, 2H), 3.75 (s, 5H), 3.60-3.47 (m, 1H), 2.47-2.35 (m, 1H), 2.17-2.05 (m, 1H).

Example 174. (S)-5-(8-(3-isopropylpyrrolidin-1-yl)imidazo[1,2-b]pyridazin-6-yl)pyrimidine-2,4(1H,3H)-dione

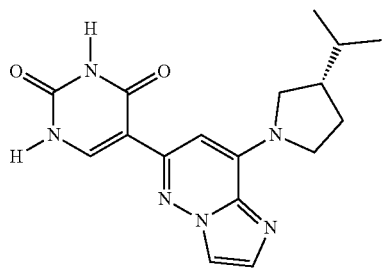 [SMILES: CC(C)[C@@H]1CCN(c2cc(-c3c[nH]c(=O)[nH]c3=O)nn3ccnc23)C1]

(S)-5-(8-(3-isopropylpyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(3S)-3-isopropylpyrrolidin-1-yl]imidazo[1,2-b]pyridazine. ES/MS m/z: 341.20 [M+H]. $^1$H NMR (400 MHz, DMSO-d6) δ 11.58 (d, J=6.3 Hz, 1H), 11.46 (d, J=2.0 Hz, 1H), 8.29 (s, 1H), 8.02 (d, J=6.2 Hz, 1H), 7.92 (s, 1H), 6.92 (s, 1H), 4.18-3.82 (m, 2H), 3.68 (s, 1H), 3.44 (s, 1H), 2.18 (dt, J=12.3, 6.3 Hz, 1H), 2.01 (p, J=8.9 Hz, 1H), 1.74 1.55 (m, 2H), 0.99 (t, J=7.2 Hz, 6H).

Example 175. (R)-5-(8-(3-(trifluoromethyl)pyrrolidin-1-yl)imidazo[1,2-b]pyridazin-6-yl)pyrimidine-2,4(1H,3H)-dione

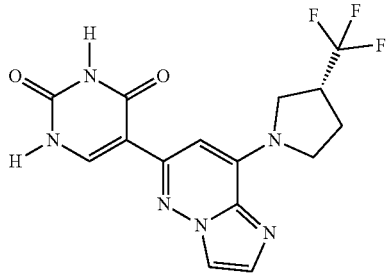 [SMILES: O=c1[nH]cc(-c2cc(N3CC[C@@H](C(F)(F)F)C3)c3nccn3n2)c(=O)[nH]1]

(R)-5-(8-(3-(trifluoromethyl)pyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(3R)-3-(trifluoromethyl)pyrrolidin-1-yl]imidazo[1,2-b]pyridazine. ES/MS m/z: 367.10 [M+H]. $^1$H NMR (400 MHz, DMSO-d6) δ 11.57 (d, J=6.2 Hz, 1H), 11.45 (d, J=1.9 Hz, 1H), 8.24 (s, 1H), 8.01 (d, J=6.1 Hz, 1H), 7.83 (s, 1H), 6.88 (s, 1H), 4.19 (t, J=10.0 Hz, 1H), 4.07-3.75 (m, 3H), 3.49 (h, J=8.4 Hz, 1H), 2.37 (dtd, J=12.7, 7.6, 5.0 Hz, 1H), 2.23-2.09 (m, 1H).

Example 176. 5-(8-(3,3-difluoropyrrolidin-1-yl)-3-fluoroimidazo[1,2-b]pyridazin-6-yl)pyrimidine-2,4(1H,3H)-dione

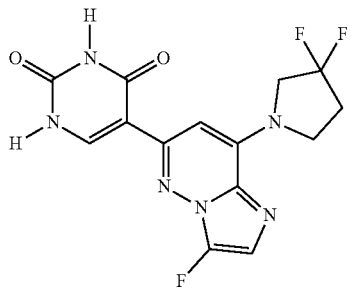 [SMILES: O=c1[nH]cc(-c2cc(N3CCC(F)(F)C3)c3ncc(F)n3n2)c(=O)[nH]1]

5-(8-(3,3-difluoropyrrolidin-1-yl)-3-fluoroimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(3,3-difluoropyrrolidin-1-yl)-6-(2,4-dimethoxypyrimidin-5-yl)-3-fluoro-imidazo[1,2-b]pyridazine. ES/MS m/z: 353.10 [M+H]. $^1$H NMR (400 MHz, DMSO-d6) δ 11.46-11.37 (m, 2H), 7.97 (d, J=6.1 Hz, 1H), 7.40 (d, J=7.2 Hz, 1H), 6.63 (s, 1H), 4.37 (d, J=13.8 Hz, 2H), 3.97 (d, J=7.7 Hz, 2H), 2.60 (tt, J=14.5, 7.4 Hz, 2H).

Example 177. 5-(8-((3R,4S)-3,4-difluoropyrrolidin-1-yl)-3-fluoroimidazo[1,2-b]pyridazin-6-yl)pyrimidine-2,4(1H,3H)-dione

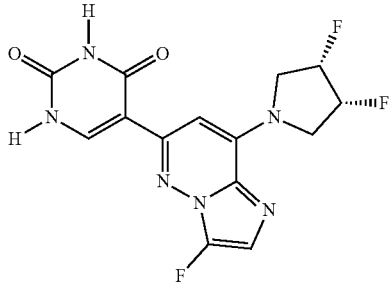 [SMILES: O=c1[nH]cc(-c2cc(N3C[C@@H](F)[C@@H](F)C3)c3ncc(F)n3n2)c(=O)[nH]1]

5-(8-((3R,4S)-3,4-difluoropyrrolidin-1-yl)-3-fluoroimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-[(3S,4R)-3,4-difluoropyrrolidin-1-yl]-6-(2,4-dimethoxypyrimidin-5-yl)-3-fluoro-imidazo[1,2-b]pyridazine. ES/MS m/z: 353.10 [M+H]. $^1$H NMR (400 MHz, DMSO-d6) δ 11.46-11.37 (m, 2H), 7.97 (d, J=6.1 Hz, 1H), 7.41 (d, J=7.2 Hz, 1H), 6.60 (s, 1H), 5.60-5.50 (m, 1H), 5.47-5.37 (m, 1H), 4.27 (s, 2H), 4.00 (d, J=29.5 Hz, 2H), 3.58 (s, 2H).

Example 178. 5-(3-fluoro-8-((2S,2S)-2-(pyridin-2-yl)cyclopropyl)imidazo[1,2-b]pyridazin-6-yl)pyrimidine-2,4(1H,3H)-dione

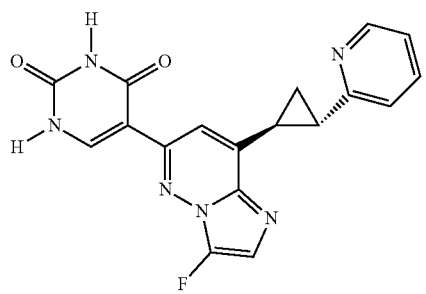 [SMILES: O=c1[nH]cc(-c2cc([C@H]3C[C@@H]3c3ccccn3)c3ncc(F)n3n2)c(=O)[nH]1]

5-(3-fluoro-8-((1S,2S)-2-(pyridin-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-[(1S,2S)-2-(2-pyridyl)cyclopropyl]imidazo[1,2-b]pyridazine(racemic). ES/MS m/z: 365.20 [M+H]. $^1$H NMR (400 MHz, DMSO-d6) δ 11.65 (dd, J=6.2, 1.9 Hz, 1H), 11.56 (d, J=2.0 Hz, 1H), 8.69 (dd, J=5.6, 1.5 Hz, 1H), 8.31 (t, J=8.0 Hz, 1H), 8.06 (d, J=6.2 Hz, 1H), 7.84 (d, J=8.1 Hz, 1H), 7.72 (t, J=6.6 Hz, 1H), 7.66-7.58 (m, 2H), 3.38 (dt, J=9.5, 5.5 Hz, 1H), 3.13 (ddd, J=9.2, 6.4, 4.3 Hz, 1H), 2.40 (dt, J=8.6, 5.3 Hz, 1H), 2.18-2.08 (m, 1H).

Example 179. 5-(3-fluoro-8-((2S,2S)-2-(pyrimidin-5-yl)cyclopropyl)imidazo[1,2-b]pyridazin-6-yl)pyrimidine-2,4(1H,3H)-dione

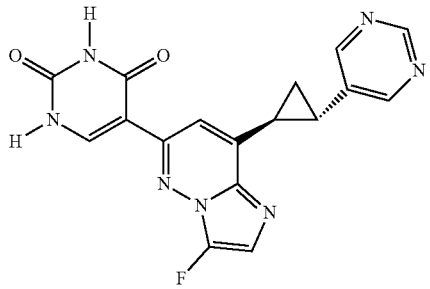 [SMILES: O=c1[nH]cc(-c2cc([C@H]3C[C@@H]3c3cncnc3)c3ncc(F)n3n2)c(=O)[nH]1]

5-(3-fluoro-8-((1S,2S)-2-(pyrimidin-5-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-[(1S,2S)-2-pyrimidin-5-ylcyclopropyl]imidazo[1,2-b]pyridazine(racemic). ES/MS m/z: 366.10 [M+H]. $^1$H NMR (400 MHz, DMSO-d6) δ 11.62 (d, J=6.3 Hz, 1H), 11.55 (d, J=1.9 Hz, 1H), 9.07 (s, 1H), 8.78 (s, 2H), 8.05 (d, J=6.1 Hz, 1H), 7.68-7.57 (m, 2H), 2.91 (ddt, J=14.6, 10.6, 5.4 Hz, 2H), 2.20 (dt, J=8.9, 5.5 Hz, 1H), 1.92 (dt, J=8.6, 5.4 Hz, 1H).

Example 180. 5-(3-fluoro-8-((2S,2S)-2-(pyridin-3-yl)cyclopropyl)imidazo[1,2-b]pyridazin-6-yl)pyrimidine-2,4(1H,3H)-dione

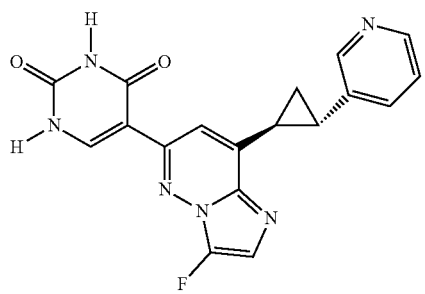 [SMILES: O=c1[nH]cc(-c2cc([C@H]3C[C@@H]3c3cccnc3)c3ncc(F)n3n2)c(=O)[nH]1]

5-(3-fluoro-8-((1S,2S)-2-(pyridin-3-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-[(1S,2S)-2-(3-pyridyl)cyclopropyl]imidazo[1,2-b]pyridazine(racemic). ES/MS m/z: 365.20 [M+H]. $^1$H NMR (400 MHz, DMSO-d6) δ 11.63 (dd, J=6.3, 2.0 Hz, 1H), 11.55 (d, J=1.9 Hz, 1H), 8.94 (d, J=2.0 Hz, 1H), 8.77 (dd, J=5.6, 1.2 Hz, 1H), 8.48 (dt, J=8.3, 1.6 Hz, 1H), 8.09-7.96 (m, 2H), 7.60 (t, J=3.5 Hz, 2H), 3.19 (ddd, J=9.0, 6.1, 4.5 Hz, 1H), 2.96 (ddd, J=9.0, 6.2, 4.5 Hz, 1H), 2.32 (dt, J=8.9, 5.4 Hz, 1H), 1.98 (dt, J=8.8, 5.4 Hz, 1H).

Example 181. 5-(3-fluoro-8-((2S,2S)-2-(pyridin-4-yl)cyclopropyl)imidazo[1,2-b]pyridazin-6-yl)pyrimidine-2,4(1H,3H)-dione

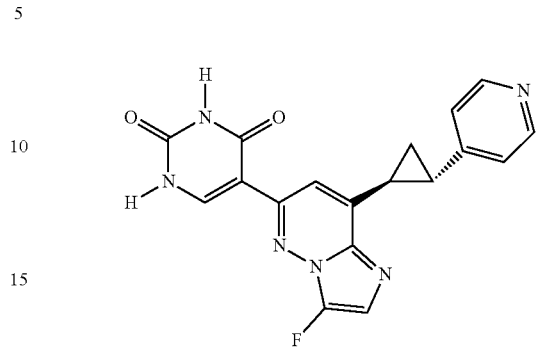

5-(3-fluoro-8-((1S,2S)-2-(pyridin-4-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-[(1S,2S)-2-(4-pyridyl)cyclopropyl]imidazo[1,2-b]pyridazine(racemic). ES/MS m/z: 365.20 [M+H]. $^1$H NMR (400 MHz, DMSO-d6) δ 11.62 (dd, J=6.3, 2.0 Hz, 1H), 11.56 (d, J=2.0 Hz, 1H), 8.84-8.78 (m, 2H), 8.05 (d, J=6.2 Hz, 1H), 8.02-7.95 (m, 2H), 7.64-7.55 (m, 2H), 3.24 (ddd, J=8.8, 5.9, 4.2 Hz, 1H), 3.10 (ddd, J=9.1, 6.6, 4.3 Hz, 1H), 2.54 (s, 1H), 2.08 (dt, J=9.0, 5.3 Hz, 1H).

Example 182. 5-(8-((2S,2S)-2-(4-chlorophenyl)cyclopropyl)-3-fluoroimidazo[1,2-b]pyridazin-6-yl)pyrimidine-2,4(1H,3H)-dione

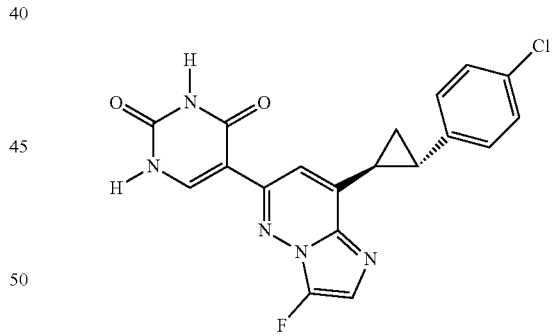

5-(8-((2S,2S)-2-(4-chlorophenyl)cyclopropyl)-3-fluoro-imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-[(1S,2S)-2-(4-chlorophenyl)cyclopropyl]-6-(2,4-dimethoxypyrimidin-5-yl)-3-fluoro-imidazo[1,2-b]pyridazine (racemic). ES/MS m/z: 398.10 [M+H]. $^1$H NMR (400 MHz, DMSO-d6) δ 11.63-11.51 (m, 2H), 8.04 (d, J=6.2 Hz, 1H), 7.62 (d, J=6.9 Hz, 1H), 7.51 (s, 1H), 7.40-7.32 (m, 2H), 7.29 (d, J=8.6 Hz, 2H), 2.83 (ddd, J=9.0, 6.2, 4.4 Hz, 1H), 2.76-2.66 (m, 1H), 2.08 (dt, J=8.8, 5.3 Hz, 1H), 1.75 (ddd, J=8.7, 6.3, 4.9 Hz, 1H).

Example 183. 5-(3-fluoro-8-((2S,2S)-2-(4-(trifluoromethyl)phenyl)cyclopropyl)imidazo[1,2-b]pyridazin-6-yl)pyrimidine-2,4(1H,3H)-dione

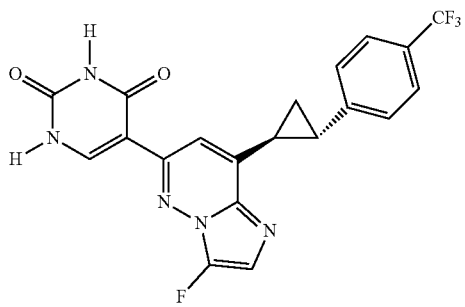 [SMILES: O=c1[nH]cc(-c2cc([C@H]3C[C@@H]3c3ccc(C(F)(F)F)cc3)c3ncc(F)n3n2)c(=O)[nH]1]

5-(3-fluoro-8-((1S,2S)-2-(4-(trifluoromethyl)phenyl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-[(1S,2S)-2-[4-(trifluoromethyl)phenyl]cyclopropyl]imidazo[1,2-b]pyridazine(racemic). ES/MS m/z: 432.10 [M+H]. $^1$H NMR (400 MHz, DMSO-d6) δ 11.56 (dd, J=10.4, 4.1 Hz, 2H), 8.04 (d, J=6.1 Hz, 1H), 7.66 (d, J=8.1 Hz, 2H), 7.58 (d, J=7.0 Hz, 1H), 7.54-7.46 (m, 3H), 2.95 (ddd, J=9.0, 6.2, 4.4 Hz, 1H), 2.84-2.74 (m, 1H), 2.18 (dt, J=8.7, 5.3 Hz, 1H), 1.83 (dt, J=8.6, 5.2 Hz, 1H).

Example 184. 5-(8-((2S,2S)-2-(1-methyl-6-oxo-1,6-dihydropyridin-3-yl)cyclopropyl)imidazo[1,2-b]pyridazin-6-yl)pyrimidine-2,4(1H,3H)-dione

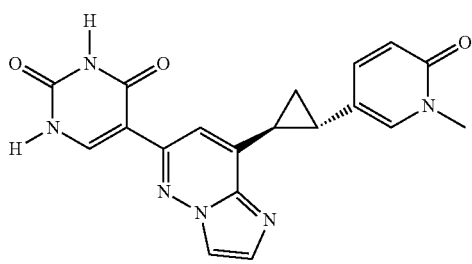 [SMILES: Cn1cc([C@H]2C[C@@H]2c2cc(-c3c[nH]c(=O)[nH]c3=O)nn3ccnc23)ccc1=O]

5-(8-((1S,2S)-2-(1-methyl-6-oxo-1,6-dihydropyridin-3-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 5-[(1S,2S)-2-[6-(2,4-dimethoxypyrimidin-5-yl)imidazo[1,2-b]pyridazin-8-yl]cyclopropyl]-1-methyl-pyridin-2-one(racemic). ES/MS m/z: 377.20 [M+H]. $^1$H NMR (400 MHz, DMSO-d6) δ 11.69-11.62 (m, 1H), 11.59 (d, J=1.9 Hz, 1H), 8.47 (s, 1H), 8.12-8.04 (m, 2H), 7.72 (d, J=2.6 Hz, 1H), 7.67 (s, 1H), 7.37 (dd, J=9.4, 2.6 Hz, 1H), 6.39 (d, J=9.3 Hz, 1H), 3.41 (s, 3H), 2.74-2.66 (m, 1H), 2.55 (t, J=5.5 Hz, 1H), 1.87 (dt, J=9.0, 5.3 Hz, 1H), 1.73 (dt, J=8.4, 5.5 Hz, 1H).

Example 185. 5-[8-[3-methyl-3-(trifluoromethyl)pyrrolidin-1-yl]imidazo[1,2-b]pyridazin-6-yl]-1H-pyrimidine-2,4-dione

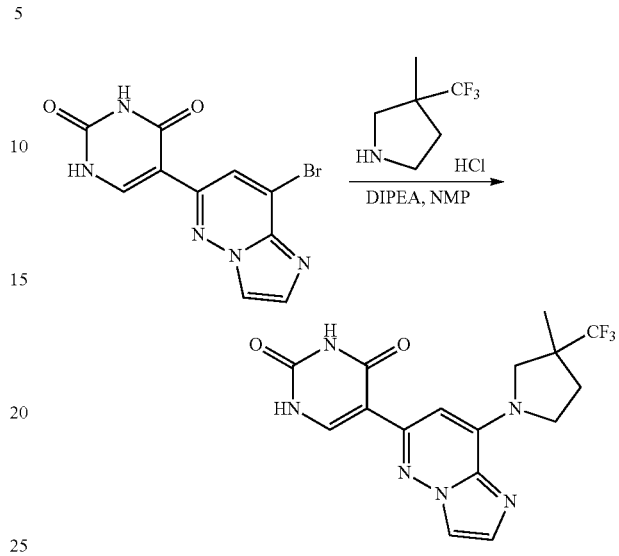

A solution of 5-(8-bromoimidazo[1,2-b]pyridazin-6-yl)pyrimidine-2,4(1H,3H)-dione (50 mg, 0.16 mmol, 1 equiv), 3-methyl-3-(trifluoromethyl)pyrrolidine; hydrochloride (40 mg, 0.21 mmol, 1.3 equiv), and DIPEA (0.073 mL, 0.42 mmol, 2.6 equiv) in NMP (1 mL) was heated at 100° C. After 4 h, the reaction mixture was directly purified by RP-HPLC (5-75% MeCN/H$_2$O with TFA modifier), affording 5-[8-[3-methyl-3-(trifluoromethyl)pyrrolidin-1-yl]imidazo[1,2-b]pyridazin-6-yl]-1H-pyrimidine-2,4-dione. ES/MS m/z: 381.10 [M+H]. $^1$H NMR (400 MHz, DMSO-d6) δ 11.43-11.33 (m, 2H), 8.05 (s, 1H), 7.94 (d, J=6.1 Hz, 1H), 7.57 (s, 1H), 6.61 (s, 1H), 4.26-3.99 (m, 4H), 2.41-2.29 (m, 1H), 2.06 (ddd, J=13.0, 7.9, 5.2 Hz, 1H), 1.37 (s, 3H).

Example 186. 5-[8-[(3R)-3-fluoro-3-methyl-pyrrolidin-1-yl]imidazo[1,2-b]pyridazin-6-yl]-1H-pyrimidine-2,4-dione

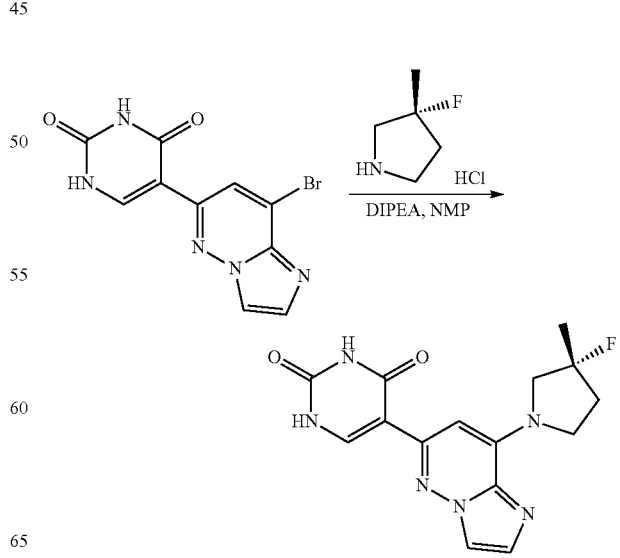

A solution of 5-(8-bromoimidazo[1,2-b]pyridazin-6-yl)pyrimidine-2,4(1H,3H)-dione (50 mg, 0.16 mmol, 1 equiv), (3R)-3-fluoro-3-methyl-pyrrolidine; hydrochloride (29.5 mg, 0.21 mmol, 1.3 equiv), and DIPEA (0.073 mL, 0.42 mmol, 2.6 equiv) in NMP (1 mL) was heated at 100° C. After 4 h, the reaction mixture was directly purified by RP-HPLC (5-75% MeCN/H$_2$O with TFA modifier), affording 5-[8-[(3R)-3-fluoro-3-methyl-pyrrolidin-1-yl]imidazo[1,2-b]pyridazin-6-yl]-1H-pyrimidine-2,4-dione. ES/MS m/z: 331.10 [M+H]. $^1$H NMR (400 MHz, DMSO-d6) δ 11.38 (dd, J=12.4, 4.1 Hz, 2H), 8.05 (d, J=1.3 Hz, 1H), 7.94 (d, J=6.1 Hz, 1H), 7.58 (t, J=1.4 Hz, 1H), 6.60 (d, J=2.3 Hz, 1H), 4.57-3.71 (m, 4H), 2.38-2.06 (m, 2H), 1.62 (d, J=20.9 Hz, 3H).

Example 187. 5-[8-[(3R)-3-(trifluoromethoxy)pyrrolidin-1-yl]imidazo[1,2-b]pyridazin-6-yl]-1H-pyrimidine-2,4-dione

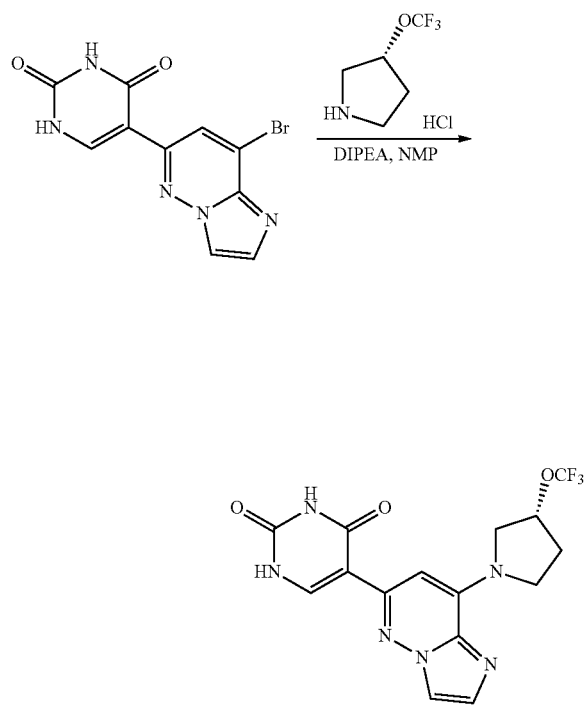

A solution of 5-(8-bromoimidazo[1,2-b]pyridazin-6-yl)pyrimidine-2,4(1H,3H)-dione (50 mg, 0.16 mmol, 1 equiv), (3R)-3-(trifluoromethoxy)pyrrolidine; hydrochloride (40.4 mg, 0.21 mmol, 1.3 equiv), and DIPEA (0.073 mL, 0.42 mmol, 2.6 equiv) in NMP (1 mL) was heated at 100° C. After 4 h, the reaction mixture was directly purified by RP-HPLC (5-75% MeCN/H$_2$O with TFA modifier), affording 5-[8-[(3R)-3-(trifluoromethoxy)pyrrolidin-1-yl]imidazo[1,2-b]pyridazin-6-yl]-1H-pyrimidine-2,4-dione. ES/MS m/z: 383.10 [M+H]. $^1$H NMR (400 MHz, DMSO-d6) δ 11.38 (dd, J=14.7, 4.1 Hz, 2H), 8.04 (d, J=1.2 Hz, 1H), 7.94 (d, J=6.1 Hz, 1H), 7.56 (d, J=1.2 Hz, 1H), 6.61 (s, 1H), 5.30 (d, J=4.0 Hz, 1H), 4.40-4.14 (m, 4H), 2.32 (s, 2H).

Example 188. 5-[8-[3-fluoro-3-(methoxymethyl)pyrrolidin-1-yl]imidazo[1,2-b]pyridazin-6-yl]-1H-pyrimidine-2,4-dione

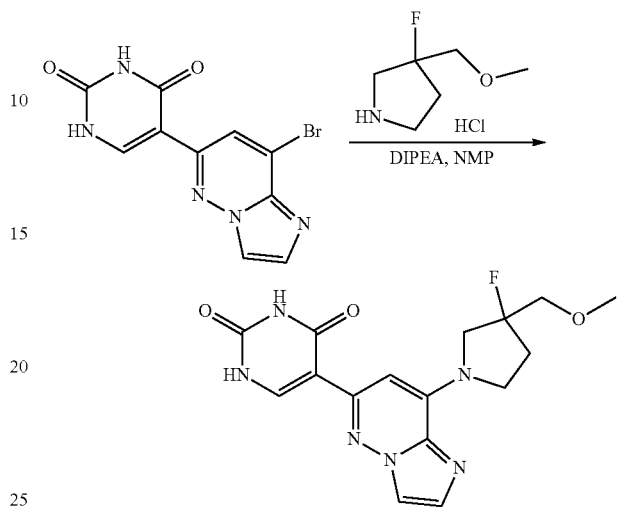

A solution of 5-(8-bromoimidazo[1,2-b]pyridazin-6-yl)pyrimidine-2,4(1H,3H)-dione (50 mg, 0.16 mmol, 1 equiv), 3-fluoro-3-(methoxymethyl)pyrrolidine; hydrochloride (36 mg, 0.21 mmol, 1.3 equiv), and DIPEA (0.073 mL, 0.42 mmol, 2.6 equiv) in NMP (1 mL) was heated at 130° C. After 2 h, the reaction mixture was directly purified by RP-HPLC (5-75% MeCN/H$_2$O with TFA modifier), affording 5-[8-[3-fluoro-3-(methoxymethyl)pyrrolidin-1-yl]imidazo[1,2-b]pyridazin-6-yl]-1H-pyrimidine-2,4-dione. ES/MS m/z: 361.10 [M+H]. $^1$H NMR (400 MHz, DMSO-d6) δ 11.43-11.33 (m, 2H), 8.04 (d, J=1.1 Hz, 1H), 7.95 (d, J=6.1 Hz, 1H), 7.57 (d, J=1.1 Hz, 1H), 6.60 (s, 1H), 4.04-3.71 (m, 6H), 3.39 (s, 3H), 2.31-2.13 (m, 2H).

Example 189. 5-[8-[3-methoxy-3-(trifluoromethyl)pyrrolidin-1-yl]imidazo[1,2-b]pyridazin-6-yl]-1H-pyrimidine-2,4-dione

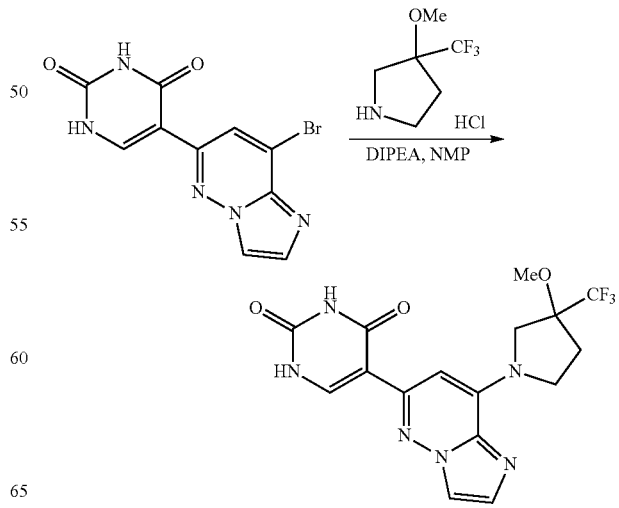

A solution of 5-(8-bromoimidazo[1,2-b]pyridazin-6-yl)pyrimidine-2,4(1H,3H)-dione (50 mg, 0.16 mmol, 1 equiv), 3-methoxy-3-(trifluoromethyl)pyrrolidine; hydrochloride (43.4 mg, 0.21 mmol, 1.3 equiv), and DIPEA (0.073 mL, 0.42 mmol, 2.6 equiv) in NMP (1 mL) was heated at 100° C. After 4 h, the reaction mixture was directly purified by RP-HPLC (5-75% MeCN/H$_2$O with TFA modifier), affording 5-[8-[3-methoxy-3-(trifluoromethyl)pyrrolidin-1-yl]imidazo[1,2-b]pyridazin-6-yl]-1H-pyrimidine-2,4-dione. ES/MS m/z: 397.10 [M+H]. $^1$H NMR (400 MHz, DMSO-d6) δ 11.39 (dd, J=14.1, 4.0 Hz, 2H), 8.05 (d, J=1.2 Hz, 1H), 7.94 (d, J=6.1 Hz, 1H), 7.57 (d, J=1.1 Hz, 1H), 6.62 (s, 1H), 4.56 (s, 2H), 4.14 (d, J=12.9 Hz, 2H), 3.42 (s, 3H), 2.44-2.33 (m, 2H)

Example 190. 5-[8-(5-azaspiro[2.4]heptan-5-yl)imidazo[1,2-b]pyridazin-6-yl]-1H-pyrimidine-2,4-dione

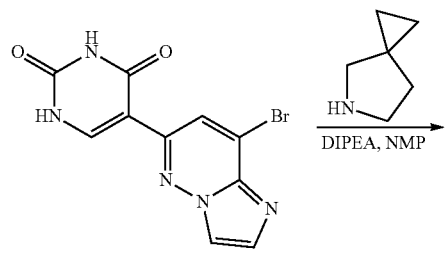

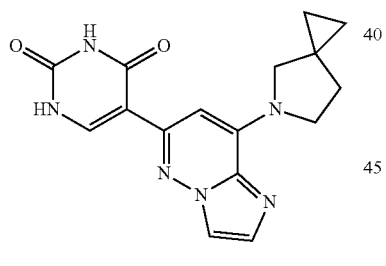

A solution of 5-(8-bromoimidazo[1,2-b]pyridazin-6-yl)pyrimidine-2,4(1H,3H)-dione (50 mg, 0.16 mmol, 1 equiv), 5-azaspiro[2.4]heptane (20.5 mg, 0.21 mmol, 1.3 equiv), and DIPEA (0.043 mL, 0.25 mmol, 1.5 equiv) in NMP (1 mL) was heated at 130° C. After 2 h, the reaction mixture was directly purified by RP-HPLC (5-75% MeCN/H$_2$O with TFA modifier), affording 5-[8-(5-azaspiro[2.4]heptan-5-yl)imidazo[1,2-b]pyridazin-6-yl]-1H-pyrimidine-2,4-dione. ES/MS m/z: 325.10 [M+H]. $^1$H NMR (400 MHz, DMSO-d6) δ 11.41-11.33 (m, 2H), 8.05 (d, J=1.3 Hz, 1H), 7.95 (d, J=6.1 Hz, 1H), 7.58 (d, J=1.3 Hz, 1H), 6.60 (s, 1H), 3.87-3.80 (m, 4H), 1.95 (t, J=6.9 Hz, 2H), 0.74-0.61 (m, 4H).

Example 191. 5-[8-[(3S)-3-fluoro-3-methyl-pyrrolidin-1-yl]imidazo[1,2-b]pyridazin-6-yl]-1H-pyrimidine-2,4-dione

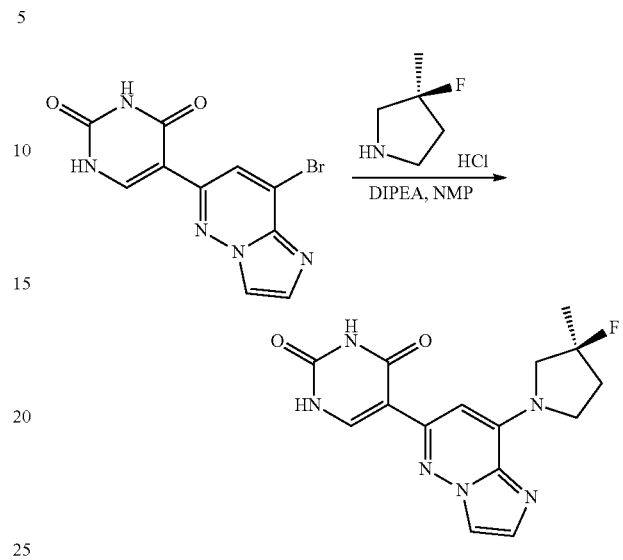

A solution of 5-(8-bromoimidazo[1,2-b]pyridazin-6-yl)pyrimidine-2,4(1H,3H)-dione (50 mg, 0.16 mmol, 1 equiv), (3S)-3-fluoro-3-methyl-pyrrolidine; hydrochloride (29.5 mg, 0.21 mmol, 1.3 equiv), and DIPEA (0.073 mL, 0.42 mmol, 2.6 equiv) in NMP (1 mL) was heated at 100° C. After 4 h, the reaction mixture was directly purified by RP-HPLC (5-75% MeCN/H$_2$O with TFA modifier), affording 5-[8-[(3S)-3-fluoro-3-methyl-pyrrolidin-1-yl]imidazo[1,2-b]pyridazin-6-yl]-1H-pyrimidine-2,4-dione. ES/MS m/z: 331.10 [M+H]. $^1$H NMR (400 MHz, DMSO-d6) δ 11.43-11.31 (m, 2H), 8.05 (d, J=1.2 Hz, 1H), 7.94 (d, J=6.1 Hz, 1H), 7.58 (d, J=1.2 Hz, 1H), 6.60 (s, 1H), 4.10-3.71 (m, 4H), 2.36-2.06 (m, 2H), 1.62 (d, J=20.9 Hz, 3H).

Example 192. 5-[8-(5-azaspiro[2.4]heptan-5-yl)imidazo[1,2-b]pyridazin-6-yl]-1H-pyrimidine-2,4-dione

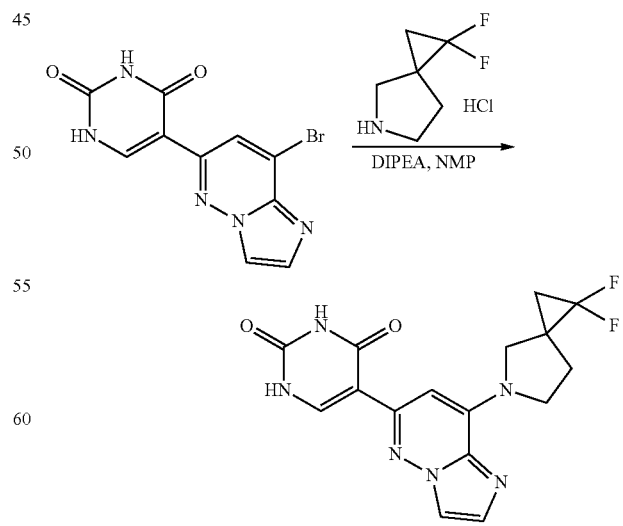

A solution of 5-(8-bromoimidazo[1,2-b]pyridazin-6-yl)pyrimidine-2,4(1H,3H)-dione (50 mg, 0.16 mmol, 1 equiv), 2,2-difluoro-5-azaspiro[2.4]heptane; hydrochloride (36 mg, 0.21 mmol, 1.3 equiv), and DIPEA (0.073 mL, 0.42 mmol, 2.6 equiv) in NMP (1 mL) was heated at 130° C. After 2 h, the reaction mixture was directly purified by RP-HPLC (5-75% MeCN/H$_2$O with TFA modifier), affording 5-[8-(5-azaspiro[2.4]heptan-5-yl)imidazo[1,2-b]pyridazin-6-yl]-1H-pyrimidine-2,4-dione. ES/MS m/z: 361.10 [M+H]. $^1$H NMR (400 MHz, DMSO-d6) δ 11.43-11.30 (m, 2H), 8.05 (d, J=1.1 Hz, 1H), 7.95 (d, J=6.1 Hz, 1H), 7.57 (d, J=1.2 Hz, 1H), 6.62 (s, 1H), 4.28-3.85 (m, 4H), 2.21 (ddt, J=33.2, 12.5, 6.2 Hz, 2H), 1.74 (dddd, J=41.4, 13.3, 8.4, 4.6 Hz, 2H).

Example 193. 5-[8-[(3S,4S)-3-methyl-4-(trifluoromethyl)pyrrolidin-1-yl]imidazo[1,2-b]pyridazin-6-yl]-1H-pyrimidine-2,4-dione

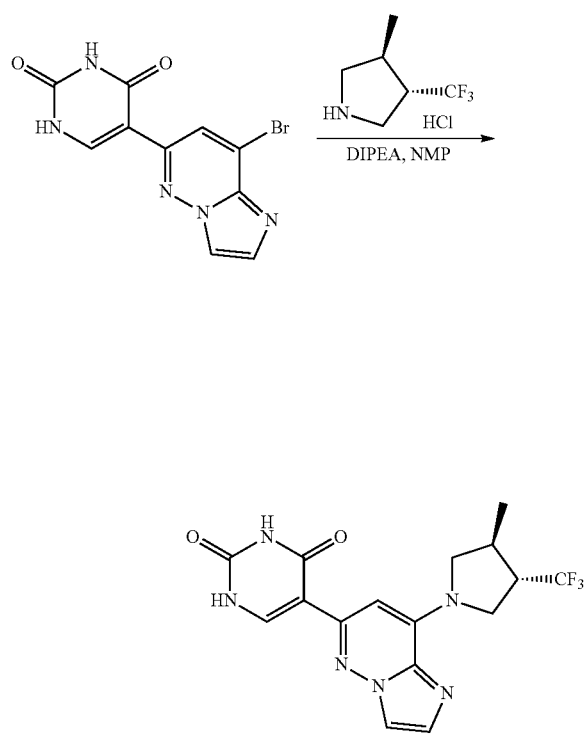

A solution of 5-(8-bromoimidazo[1,2-b]pyridazin-6-yl)pyrimidine-2,4(1H,3H)-dione (50 mg, 0.16 mmol, 1 equiv), (3S,4S)-3-methyl-4-(trifluoromethyl)pyrrolidine; hydrochloride (40 mg, 0.21 mmol, 1.3 equiv), and DIPEA (0.073 mL, 0.42 mmol, 2.6 equiv) in NMP (1 mL) was heated at 100° C. After 4 h, the reaction mixture was directly purified by RP-HPLC (5-75% MeCN/H$_2$O with TFA modifier), affording 5-[8-[(3S,4S)-3-methyl-4-(trifluoromethyl)pyrrolidin-1-yl]imidazo[1,2-b]pyridazin-6-yl]-1H-pyrimidine-2, 4-dione. ES/MS m/z: 381.10 [M+H]. $^1$H NMR (400 MHz, DMSO-d6) δ 11.43-11.33 (m, 2H), 8.04 (d, J=1.2 Hz, 1H), 7.94 (d, J=6.1 Hz, 1H), 7.57 (d, J=1.1 Hz, 1H), 6.60 (s, 1H), 4.30-4.01 (m, 4H), 3.11 (h, J=8.7 Hz, 1H), 2.59 (p, J=7.6 Hz, 1H), 1.21 (d, J=6.6 Hz, 3H).

Example 194. 5-[8-[3,3-difluoro-4-(4-methoxyphenyl)pyrrolidin-1-yl]imidazo[1,2-b]pyridazin-6-yl]-1H-pyrimidine-2,4-dione

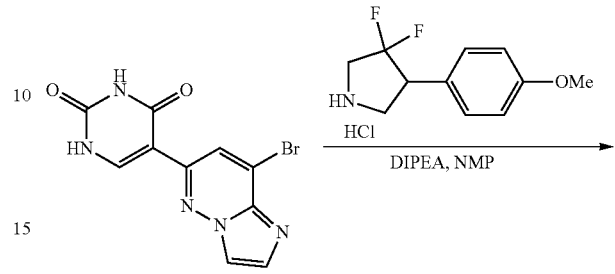

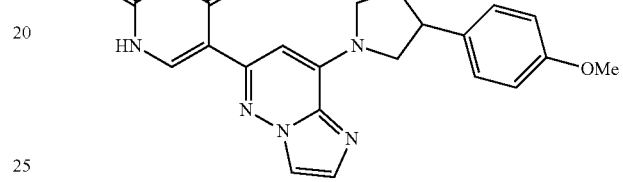

A solution of 5-(8-bromoimidazo[1,2-b]pyridazin-6-yl)pyrimidine-2,4(1H,3H)-dione (50 mg, 0.16 mmol, 1 equiv), 3,3-difluoro-4-(4-methoxyphenyl)pyrrolidine; hydrochloride (52.7 mg, 0.21 mmol, 1.3 equiv), and DIPEA (0.073 mL, 0.42 mmol, 2.6 equiv) in NMP (1 mL) was heated at 100° C. After 4 h, the reaction mixture was directly purified by RP-HPLC (5-75% MeCN/H$_2$O with TFA modifier), affording 5-[8-[3,3-difluoro-4-(4-methoxyphenyl)pyrrolidin-1-yl]imidazo[1,2-b]pyridazin-6-yl]-1H-pyrimidine-2,4-dione. ES/MS m/z: 441.10 [M+H]. $^1$H NMR (400 MHz, DMSO-d6) δ 11.44-11.35 (m, 2H), 8.09 (d, J=1.1 Hz, 1H), 7.95 (d, J=6.1 Hz, 1H), 7.59 (d, J=1.1 Hz, 1H), 7.39-7.27 (m, 2H), 7.03-6.94 (m, 2H), 6.67 (s, 1H), 4.52-4.47 (m, 3H), 4.12-4.10 (m, 2H), 3.33 (s, 3H).

Example 195. 1-[6-(2,4-dioxo-1H-pyrimidin-5-yl)imidazo[1,2-b]pyridazin-8-yl]-3-fluoro-pyrrolidine-3-carbonitrile

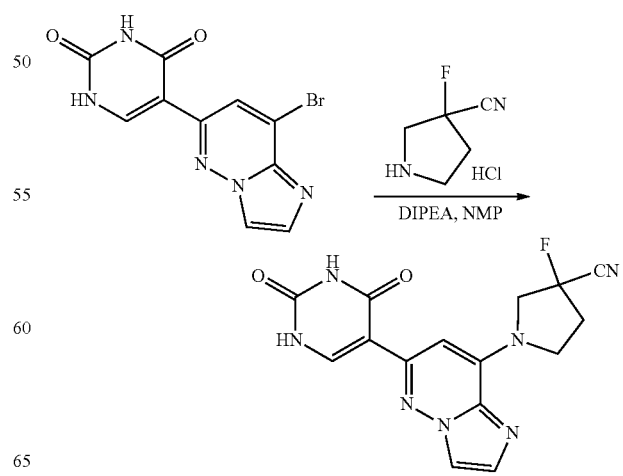

A solution of 5-(8-bromoimidazo[1,2-b]pyridazin-6-yl)pyrimidine-2,4(1H,3H)-dione (100 mg, 0.325 mmol, 1 equiv), 3-fluoropyrrolidine-3-carbonitrile; hydrochloride (63.5 mg, 0.42 mmol, 1.3 equiv), and DIPEA (0.153 mL, 0.84 mmol, 2.6 equiv) in NMP (1 mL) was heated at 100° C. After 16 h, the reaction mixture was directly purified by RP-HPLC (5-75% MeCN/H₂O with TFA modifier), affording 1-[6-(2,4-dioxo-1H-pyrimidin-5-yl)imidazo[1,2-b]pyridazin-8-yl]-3-fluoro-pyrrolidine-3-carbonitrile. ES/MS m/z: 342.10 [M+H]. ¹H NMR (400 MHz, DMSO-d6) δ 11.40 (dd, J=14.1, 4.2 Hz, 2H), 8.08 (d, J=1.2 Hz, 1H), 7.95 (d, J=6.1 Hz, 1H), 7.59 (d, J=1.2 Hz, 1H), 6.64 (s, 1H), 4.92 (s, 2H), 4.47 (dd, J=34.8, 13.6 Hz, 1H), 4.10 (s, 1H), 3.81 (d, J=10.0 Hz, 1H), 2.91-2.66 (m, 2H).

Example 196. 5-[8-[(3S)-3-(trifluoromethoxy)pyrrolidin-1-yl]imidazo[1,2-b]pyridazin-6-yl]-1H-pyrimidine-2,4-dione

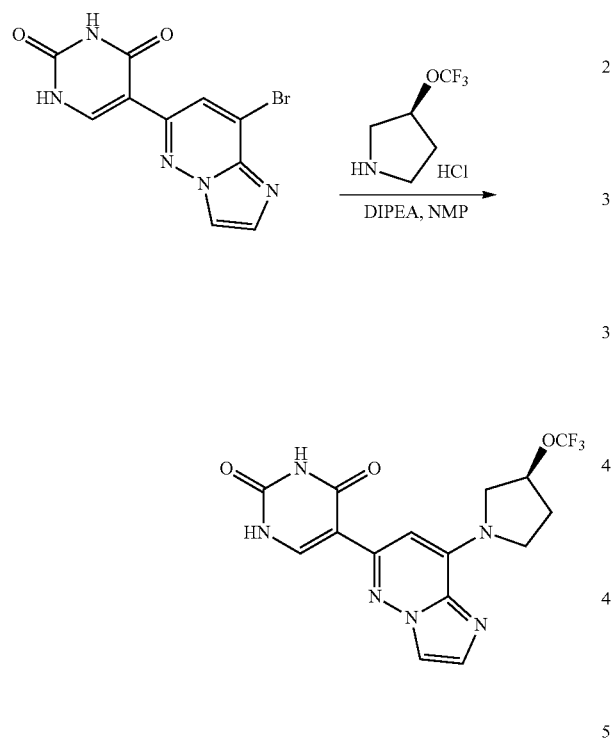

A solution of 5-(8-bromoimidazo[1,2-b]pyridazin-6-yl)pyrimidine-2,4(1H,3H)-dione (45 mg, 0.15 mmol, 1 equiv), (3S)-3-(trifluoromethoxy)pyrrolidine; hydrochloride (36 mg, 0.19 mmol, 1.3 equiv), and DIPEA (0.066 mL, 0.38 mmol, 2.6 equiv) in NMP (1 mL) was heated at 100° C. After 4 h, the reaction mixture was directly purified by RP-HPLC (5-75% MeCN/H₂O with TFA modifier), affording 5-[8-[(3S)-3-(trifluoromethoxy)pyrrolidin-1-yl]imidazo[1,2-b]pyridazin-6-yl]-1H-pyrimidine-2,4-dione. ES/MS m/z: 383.10 [M+H]. ¹H NMR (400 MHz, DMSO-d6) δ 11.42-11.33 (m, 2H), 8.05 (s, 1H), 7.94 (d, J=5.9 Hz, 1H), 7.58 (s, 1H), 6.62 (s, 1H), 5.30 (s, 1H), 4.14 (d, J=12.8 Hz, 1H), 3.95 (s, 1H), 3.78 (s, 1H), 2.41-2.26 (m, 2H).

Example 197. 6-(2,4-dioxo-1H-pyrimidin-5-yl)-8-[(1S,2S)-2-(4-fluorophenyl)cyclopropyl]-N,N-dimethyl-imidazo[1,2-b]pyridazine-2-carboxamide (Racemic Mixture)

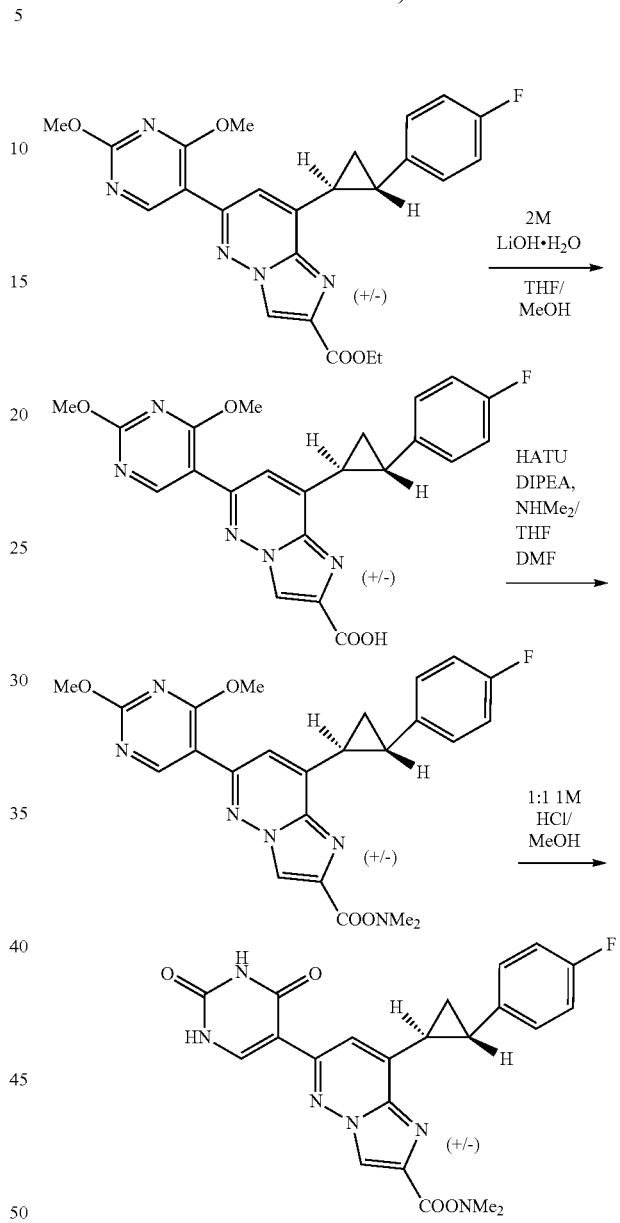

Step 1: To a solution of ethyl 6-(2,4-dimethoxypyrimidin-5-yl)-8-[(1S,2S)-2-(4-fluorophenyl)cyclopropyl]imidazo[1,2-b]pyridazine-2-carboxylate (50 mg, 0.108 mmol, 1 equiv) in THF (3 mL) was added 1 ml methanol and 2M aqueous lithium hydroxide solution (0.27 mL, 0.539 mmol, 5 equiv). After stirring for 1 h at room temperature, the reaction mixture was concentrated. Residue obtained was dissolved in water and neutralized with 1N HCl. Solids separated were filtered and dried at high vacuum overnight affording 6-(2,4-dimethoxypyrimidin-5-yl)-8-[(1S,2S)-2-(4-fluorophenyl)cyclopropyl]imidazo[1,2-b]pyridazine-2-carboxylic acid. ES/MS m/z: 436.20 [M+H].

Step 2: To a solution of 6-(2,4-dimethoxypyrimidin-5-yl)-8-[(1S,2S)-2-(4-fluorophenyl)cyclopropyl]imidazo[1,2-b]pyridazine-2-carboxylic acid (45 mg, 0.103 mmol, 1 equiv)

in DMF (2 mL) was added HATU (157 mg, 0.413 mmol, 4 equiv), N,N-Diisopropylethylamine (0.07 mL, 0.41 mmol, 4 equiv) and Dimethylamine solution/2M THF (0.41 mL, 0.83 mmol, 8 equiv). After stirring for 3 h at room temperature, the reaction mixture was quenched with methanol and purified with RP-HPLC (10-90% MeCN/H₂O with TFA modifier) affording 6-(2,4-dimethoxypyrimidin-5-yl)-8-[(1S,2S)-2-(4-fluorophenyl)cyclopropyl]-N,N-dimethyl-imidazo[1,2-b]pyridazine-2-carboxamide. ES/MS m/z: 463.20 [M+H].

Step 3: A solution of 6-(2,4-dimethoxypyrimidin-5-yl)-8-[(1S,2S)-2-(4-fluorophenyl)cyclopropyl]-N,N-dimethyl-imidazo[1,2-b]pyridazine-2-carboxamide (35 mg) in 1:1 1N HCl:MeOH (3 mL) was heated to 80° C. After 6 hours, the solids separated was filtered, washed with acetonitrile and dried at high vacuum overnight to afford 6-(2,4-dioxo-1H-pyrimidin-5-yl)-8-[(1S,2S)-2-(4-fluorophenyl)cyclopropyl]-N,N-dimethyl-imidazo[1,2-b]pyridazine-2-carboxamide. ES/MS m/z: 435.20 [M+H]. ¹H NMR (400 MHz, DMSO-d6) δ11.53 (s, 2H), 8.48 (d, J=1.7 Hz, 1H), 8.01 (d, J=6.2 Hz, 1H), 7.55 (s, 1H), 7.36-7.27 (m, 2H), 7.14 (t, J=8.7 Hz, 2H), 3.38 (s, 3H), 3.02 (s, 3H), 2.89 (dd, J=9.1, 5.3 Hz, 1H), 2.63 (dt, J=10.0, 5.5 Hz, 1H), 2.12 (dt, J=9.9, 5.6 Hz, 1H), 1.74 (dt, J=8.0, 5.6 Hz, 1H).

Example 198. 5-[2-(3,3-difluoroazetidine-1-carbonyl)-8-[(1S,2S)-2-(4-fluorophenyl)cyclopropyl]imidazo[1,2-b]pyridazin-6-yl]-1H-pyrimidine-2,4-dione (Racemic Mixture)

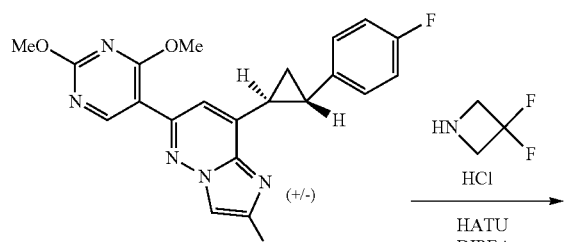

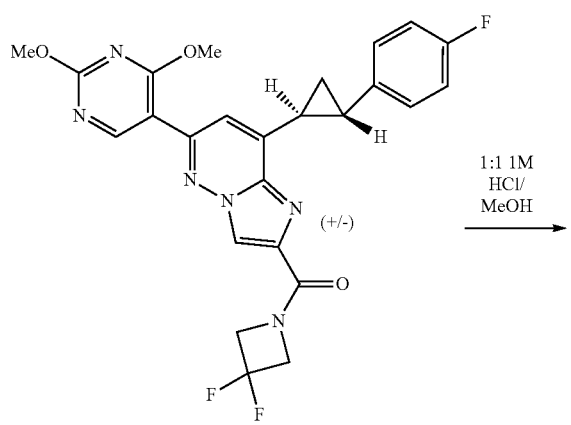

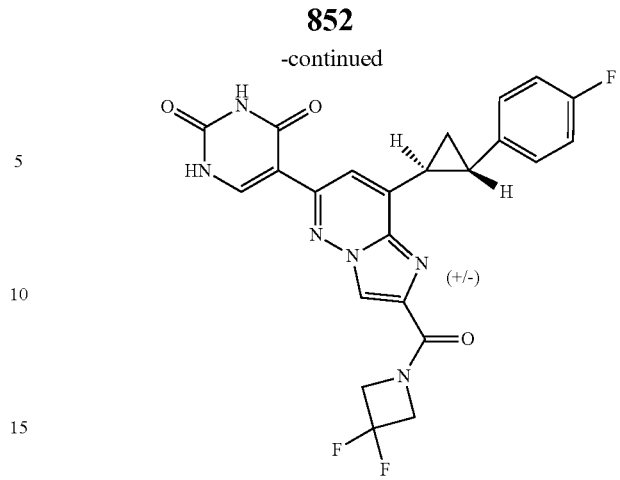

Step 1: To a solution of 6-(2,4-dimethoxypyrimidin-5-yl)-8-[(1S,2S)-2-(4-fluorophenyl)cyclopropyl]imidazo[1,2-b]pyridazine-2-carboxylic acid (50 mg, 0.115 mmol, 1 equiv) in DMF (2 mL) was added HATU (218 mg, 0.574 mmol, 5 equiv), N,N-Diisopropylethylamine (0.1 mL, 0.574 mmol, 5 equiv) and 3,3-difluoroazetidine hydrochloride (59 mg, 0.46 mmol, 4 equiv). After stirring for 3 h at room temperature, the reaction mixture was quenched with methanol and purified with RP-HPLC (15-90% MeCN/H₂O with TFA modifier) affording (3,3-difluoroazetidin-1-yl)-[6-(2,4-dimethoxypyrimidin-5-yl)-8-[(1S,2S)-2-(4-fluorophenyl)cyclopropyl]imidazo[1,2-b]pyridazin-2-yl]methanone. ES/MS m/z: 511.20 [M+H].

Step 2: A solution of (3,3-difluoroazetidin-1-yl)-[6-(2,4-dimethoxypyrimidin-5-yl)-8-[(1S,2S)-2-(4-fluorophenyl)cyclopropyl]imidazo[1,2-b]pyridazin-2-yl]methanone (50 mg) in 1:1 1N HCl:MeOH (3 mL) was heated to 80° C. After 6 hours, the solids separated was filtered, washed with acetonitrile and dried at high vacuum overnight to afford 5-[2-(3,3-difluoroazetidine-1-carbonyl)-8-[(1S,2S)-2-(4-fluorophenyl)cyclopropyl]imidazo[1,2-b]pyridazin-6-yl]-1H-pyrimidine-2,4-dione. ES/MS m/z: 483.10 [M+H]. ¹H NMR (400 MHz, DMSO-d6) δ 11.54 (s, 2H), 8.66 (s, 1H), 8.02 (s, 1H), 7.63 (s, 1H), 7.38-7.28 (m, 2H), 7.21-7.06 (m, 2H), 5.03 (p, J=12.4 Hz, 2H), 4.51 (t, J=12.6 Hz, 2H), 3.01 (dd, J=6.3, 3.1 Hz, 1H), 2.63 (dt, J=9.0, 5.4 Hz, 1H), 2.33-2.17 (m, 1H), 1.74-1.68 (m, 1H).

Example 199. 5-[2-(3,3-difluoropyrrolidine-1-carbonyl)-8-[(1S,2S)-2-(4-fluorophenyl)cyclopropyl]imidazo[1,2-b]pyridazin-6-yl]-1H-pyrimidine-2,4-dione (Racemic Mixture)

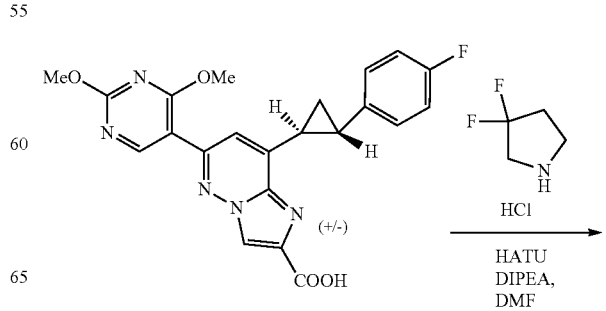

-continued

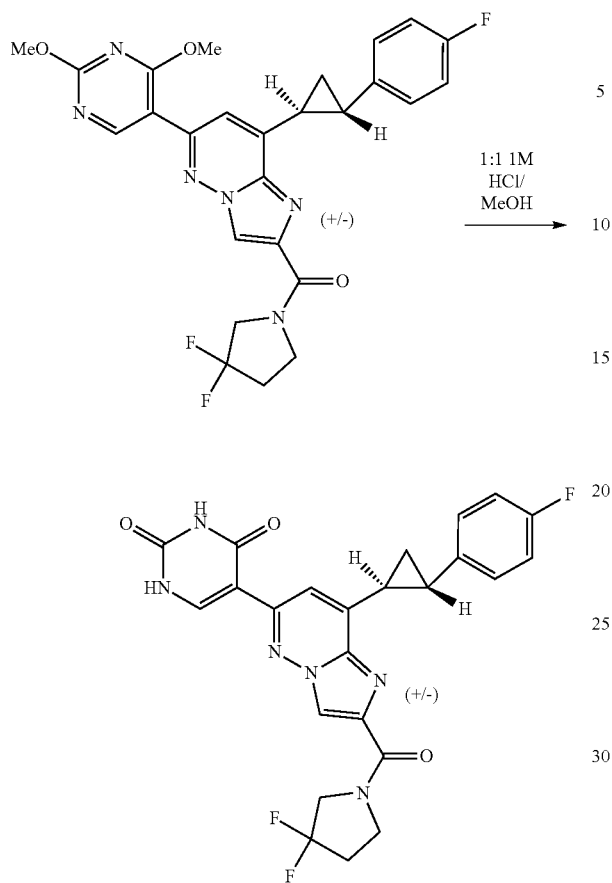

Step 1: To a solution of 6-(2,4-dimethoxypyrimidin-5-yl)-8-[(1S,2S)-2-(4-fluorophenyl)cyclopropyl]imidazo[1,2-b]pyridazine-2-carboxylic acid (50 mg, 0.115 mmol, 1 equiv) in DMF (2 mL) was added HATU (218 mg, 0.574 mmol, 5 equiv), N,N-Diisopropylethylamine (0.1 mL, 0.574 mmol, 5 equiv) and 3,3-difluoropyrolidine hydrochloride (49.5 mg, 0.345 mmol, 3 equiv). After stirring for 3 h at room temperature, the reaction mixture was quenched with methanol and purified with RP-HPLC (15-90% MeCN/H₂O with TFA modifier) affording (3,3-difluoropyrrolidin-1-yl)-[6-(2,4-dimethoxypyrimidin-5-yl)-8-[(1S,2S)-2-(4-fluorophenyl)cyclopropyl]imidazo[1,2-b]pyridazin-2-yl]methanone. ES/MS m/z: 525.20 [M+H].

Step 2: A solution of ((3,3-difluoropyrrolidin-1-yl)-[6-(2,4-dimethoxypyrimidin-5-yl)-8-[(1S,2S)-2-(4-fluorophenyl)cyclopropyl]imidazo[1,2-b]pyridazin-2-yl]methanone (51 mg) in 1:1 1N HCl:MeOH (3 mL) was heated to 80° C. After 6 hours, the solids separated was filtered, washed with acetonitrile and dried at high vacuum overnight to afford 5-[2-(3,3-difluoropyrrolidine-1-carbonyl)-8-[(1S,2S)-2-(4-fluorophenyl)cyclopropyl]imidazo[1,2-b]pyridazin-6-yl]-1H-pyrimidine-2,4-dione. ES/MS m/z: 497.10 [M+H]. ¹H NMR (400 MHz, DMSO-d6) δ 11.54 (s, 2H), 8.62 (s, 1H), 8.02 (d, J=4.9 Hz, 1H), 7.61 (d, J=2.1 Hz, 1H), 7.32 (ddd, J=8.9, 5.5, 3.3 Hz, 2H), 7.14 (t, J=8.8 Hz, 2H), 4.55-4.45 (m, 1H), 4.30 (td, J=7.4, 2.8 Hz, 1H), 4.08-3.86 (m, 1H), 3.77 (t, J=7.5 Hz, 1H), 3.08-2.87 (m, OH), 2.72-2.55 (m, 1H), 2.43 (dd, J=14.4, 7.2 Hz, 1H), 2.22-2.14 (m, 1H), 1.74 (ddd, J=8.8, 6.4, 4.8 Hz, 1H).

Example 200. 5-[2-[(3S,4R)-3,4-difluoropyrrolidine-1-carbonyl]-8-[(1S,2S)-2-(4-fluorophenyl)cyclopropyl]imidazo[1,2-b]pyridazin-6-yl]-1H-pyrimidine-2,4-dione (Racemic Mixture)

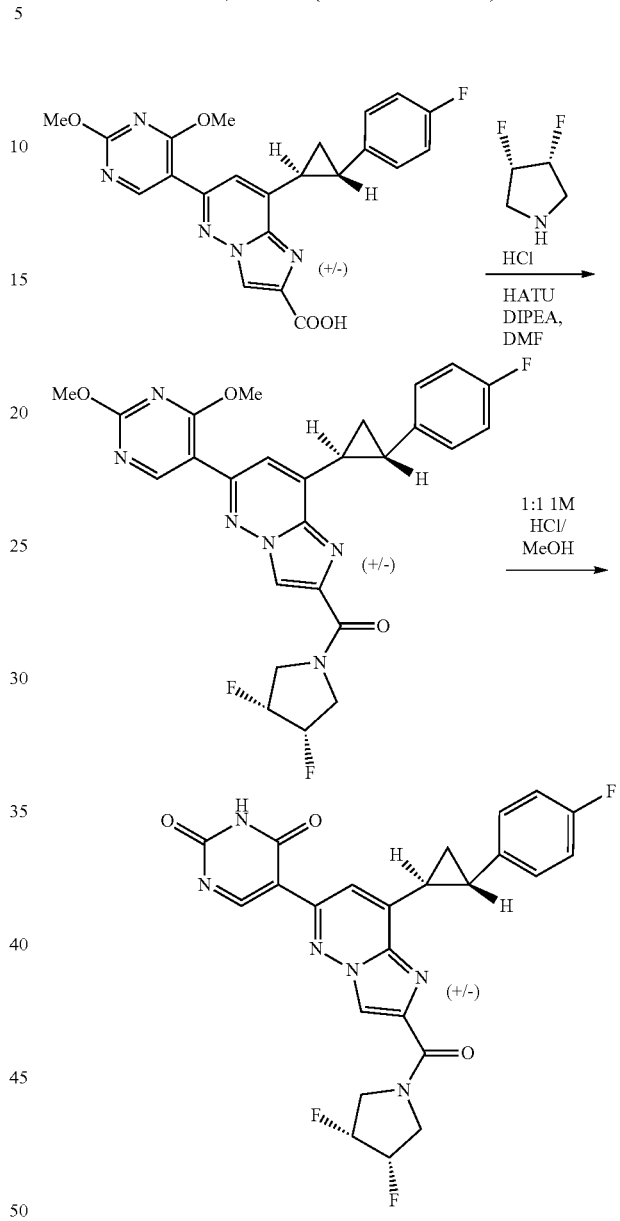

Step 1: To a solution of 6-(2,4-dimethoxypyrimidin-5-yl)-8-[(1S,2S)-2-(4-fluorophenyl)cyclopropyl]imidazo[1,2-b]pyridazine-2-carboxylic acid (50 mg, 0.115 mmol, 1 equiv) in DMF (2 mL) was added HATU (218 mg, 0.574 mmol, 5 equiv), N,N-Diisopropylethylamine (0.1 mL, 0.574 mmol, 5 equiv) and (3S,4R)-3,4-difluoropyrrolidine;hydrochloride (49.5 mg, 0.345 mmol, 3 equiv). After stirring for 3 h at room temperature, the reaction mixture was quenched with methanol and purified with RP-HPLC (15-90% MeCN/H₂O with TFA modifier) affording [(3S,4R)-3,4-difluoropyrrolidin-1-yl]-[6-(2,4-dimethoxypyrimidin-5-yl)-8-[(1S,2S)-2-(4-fluorophenyl)cyclopropyl]imidazo[1,2-b]pyridazin-2-yl]methanone. ES/MS m/z: 525.20 [M+H].

Step 2: A solution of [(3S,4R)-3,4-difluoropyrrolidin-1-yl]-[6-(2,4-dimethoxypyrimidin-5-yl)-8-[(1S,2S)-2-(4-fluorophenyl)cyclopropyl]imidazo[1,2-b]pyridazin-2-yl]methanone (50 mg) in 1:1 1N HCl:MeOH (3 mL) was heated to 80° C. After 6 hours, the solids separated was filtered, washed with acetonitrile and dried at high vacuum overnight to afford 5-[2-[(3S,4R)-3,4-difluoropyrrolidine-1-carbonyl]-8-[(1S,2S)-2-(4-fluorophenyl)cyclopropyl]imidazo[1,2-b]pyridazin-6-yl]-1H-pyrimidine-2,4-dione. ES/MS m/z: 497.10 [M+H]. ¹H NMR (400 MHz, DMSO-d6) δ 11.54 (s, 2H), 8.62 (s, 1H), 8.02 (s, 1H), 7.62 (d, J=3.7 Hz, 1H), 7.33 (ddd, J=8.5, 5.4, 2.7 Hz, 2H), 7.14 (td, J=8.8, 1.3 Hz, 2H), 5.40 (ddd, J=49.4, 11.9, 6.3 Hz, 2H), 4.51 (ddt, J=19.9, 13.3, 6.4 Hz, 1H), 4.30-4.07 (m, 1H), 4.06-3.65 (m, 2H), 2.98 (td, J=9.9, 9.1, 5.1 Hz, 1H), 2.62 (tt, J=9.1, 4.1 Hz, 1H), 2.19 (dt, J=10.0, 5.4 Hz, 1H), 1.74 (dtd, J=8.8, 4.8, 2.6 Hz, 1H).

Example 201. 5-[8-[(4S)-4-(difluoromethoxy)-3,3-difluoro-pyrrolidin-1-yl]imidazo[1,2-b]pyridazin-6-yl]-1H-pyrimidine-2,4-dione

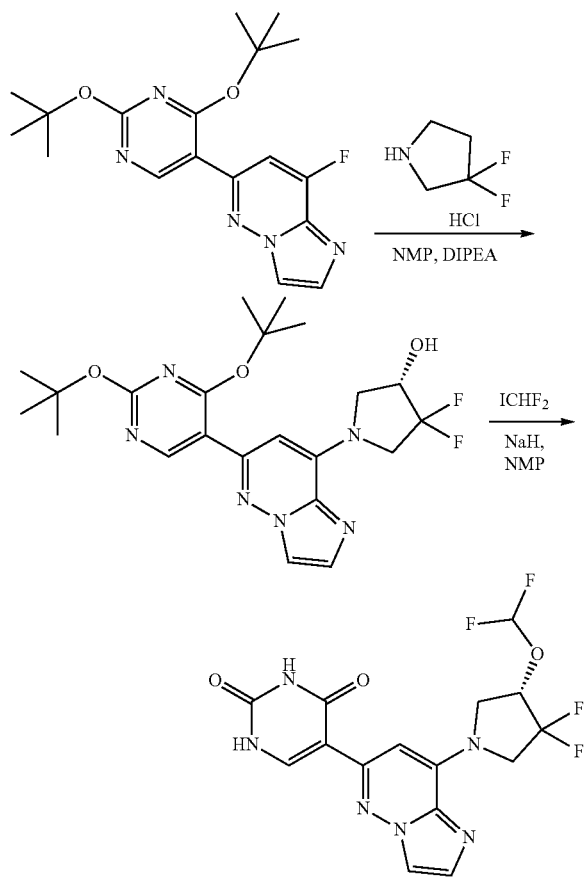

Step 1: A microwave vial was charged with (3S)-4,4-difluoropyrrolidin-3-ol;hydrochloride (289 mg, 1.81 mmol, 1.3 equiv), DIPEA (0.73 mL, 4.17 mmol, 3 equiv), and NMP (2 mL) then 6-(2,4-di-tert-butoxypyrimidin-5-yl)-8-fluoro-imidazo[1,2-b]pyridazine (500 mg, 1.39 mmol, 1 equiv). The reaction mixture was heated to 100° C. for 2 hour. The mixture was cooled diluted with EtOAc and water and the layers separated. The organic layer was dried over sodium sulfate, concentrated and purified by flash column chromatagraphy to give (3S)-1-[6-(2,4-ditert-butoxypyrimidin-5-yl)imidazo[1,2-b]pyridazin-8-yl]-4,4-difluoro-pyrrolidin-3-ol. ES/MS m/z: 463.10 [M+H].

Step 2: (3S)-1-[6-(2,4-ditert-butoxypyrimidin-5-yl)imidazo[1,2-b]pyridazin-8-yl]-4,4-difluoro-pyrrolidin-3-ol (100 mg, 0.216 mmol, 1 equiv) and sodium hydride (60% dispersion in oil, 25 mg, 0.65 mmol, 3 equiv) were combined in THF (2 mL) at 5° C. After 15 minutes, difluoro(iodo)methane (5.41 mL, 0.54 mmol, 2.5 equiv) was added. After stirring at 0° C. for 6 h, the reaction was treated with water (0.2 mL) and TFA (0.2 mL), concentrated to dryness, then purified by RP-HPLC (10-70% MeCN/H₂O gradient with TFA modifier) affording 5-[8-[(4S)-4-(difluoromethoxy)-3,3-difluoro-pyrrolidin-1-yl]imidazo[1,2-b]pyridazin-6-yl]-1H-pyrimidine-2,4-dione. ES/MS m/z: 401.10 [M+H]. ¹H NMR (400 MHz, DMSO-d6) δ 11.41 (dd, J=13.2, 4.1 Hz, 2H), 8.09 (d, J=1.2 Hz, 1H), 7.94 (d, J=6.1 Hz, 1H), 7.59 (d, J=1.1 Hz, 1H), 7.16 (s, OH), 6.98 (s, OH), 6.80 (s, OH), 6.62 (s, 1H), 5.25 (q, J=7.4, 6.6 Hz, 1H), 4.41 (q, J=15.4 Hz, 3H), 4.06 (d, J=12.2 Hz, 1H), 3.45 (q, J=7.0 Hz, 1H).

Example 202. 5-[8-[4-(difluoromethoxy)-3,3-difluoro-pyrrolidin-1-yl]imidazo[1,2-b]pyridazin-6-yl]-1H-pyrimidine-2,4-dione

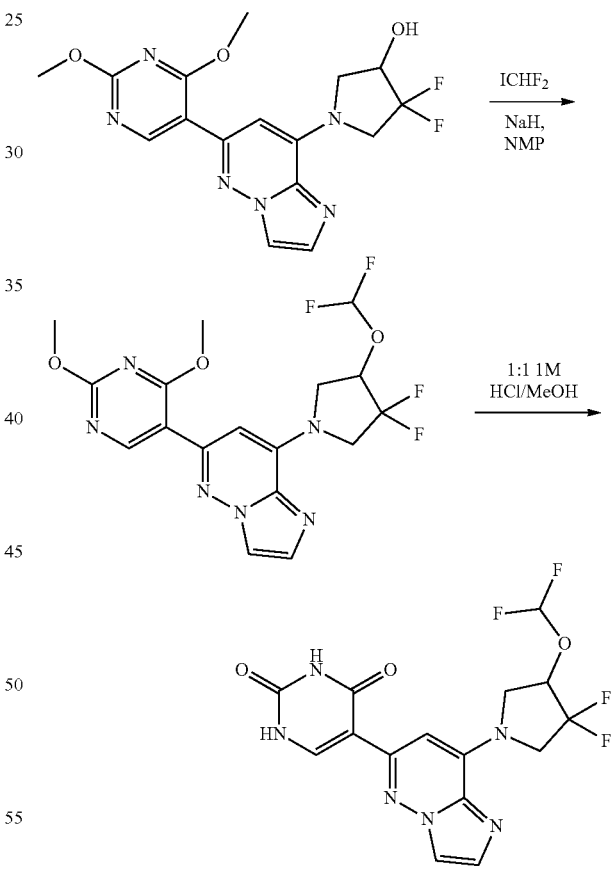

Step 1: 1-[6-(2,4-dimethoxypyrimidin-5-yl)imidazo[1,2-b]pyridazin-8-yl]-4,4-difluoro-pyrrolidin-3-ol (75 mg, 0.198 mmol, 1 equiv) and sodium hydride (60% dispersion in oil, 23 mg, 0.595 mmol, 3 equiv) were combined in THF (2 mL) at 5° C. After 15 minutes, difluoro(iodo)methane (4.96 mL, 0.496 mmol, 2.5 equiv) was added. After stirring at 0° C. for 6 h, the reaction was treated with water (0.2 mL) purified by flash column chromatagraphy using 0-100% ethylacetae/hexanes, affording 8-[4-(difluoromethoxy)-3,3-difluoropyrrolidin-1-yl]-6-(2,4-dimethoxypyrimidin-5-yl)imidazo[1,2-b]pyridazine. ES/MS m/z: 429.10 [M+H].

Step 2: A solution of 8-[4-(difluoromethoxy)-3,3-difluoro-pyrrolidin-1-yl]-6-(2,4-dimethoxypyrimidin-5-yl)imidazo[1,2-b]pyridazine (21 mg) in 1:1 1N HCl:MeOH (5 mL) was heated to 80° C. After 2 hours, the reaction mixture was concentrated and residue obtained was purified by RP-HPLC (5-80% MeCN/H₂O gradient with TFA modifier) affording 5-[8-[4-(difluoromethoxy)-3,3-difluoro-pyrrolidin-1-yl]imidazo[1,2-b]pyridazin-6-yl]-1H-pyrimidine-2,4-dione. ES/MS m/z: 401.10 [M+H]. ¹H NMR (400 MHz, DMSO-d6) δ 11.45-11.36 (m, 2H), 8.09 (s, 1H), 7.95 (d, J=5.9 Hz, 1H), 7.60 (s, 1H), 7.16 (s, OH), 6.98 (s, OH), 6.80 (s, OH), 6.63 (s, 1H), 5.31-5.22 (m, 1H), 4.39 (t, J=15.0 Hz, 3H), 4.06 (d, J=11.8 Hz, 1H).

Example 203. 8-[3,3-difluoro-4-(2,2,2-trifluoroethoxy)pyrrolidin-1-yl]-6-(2,4-dimethoxypyrimidin-5-yl)imidazo[1,2-b]pyridazine

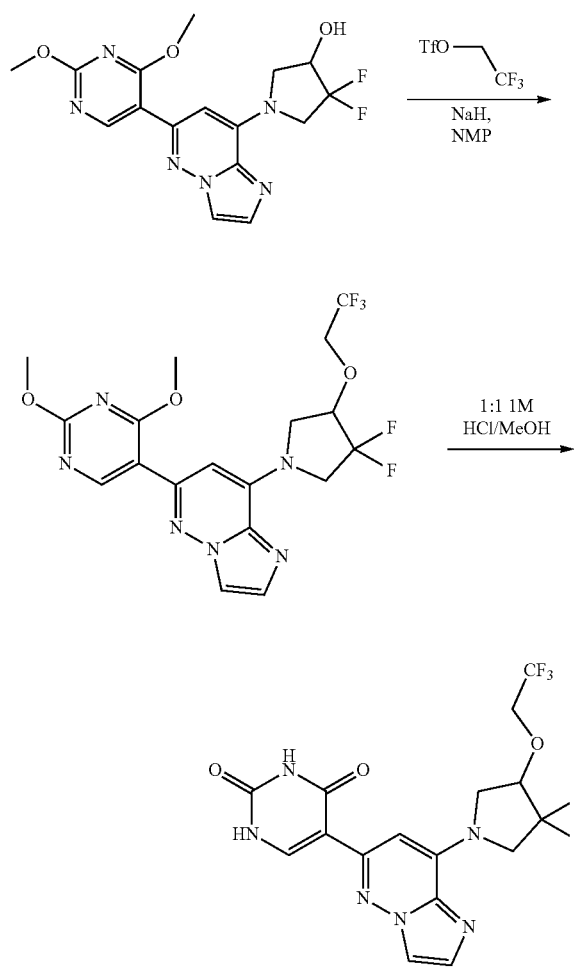

Step 1: 1-[6-(2,4-dimethoxypyrimidin-5-yl)imidazo[1,2-b]pyridazin-8-yl]-4,4-difluoro-pyrrolidin-3-ol (50 mg, 0.132 mmol, 1 equiv) and sodium hydride (60% dispersion in oil, 15 mg, 0.396 mmol, 3 equiv) were combined in THF (2 mL) at 5° C. After 15 minutes, 2,2,2-trifluoroethyl trifluoromethanesulfonate (61.3 mg, 0.264 mmol, 2 equiv) was added. After stirring at 0° C. for 6 h, the reaction was treated with water (0.2 mL) purified by flash column chromatagraphy using 0-100% ethylacetae/hexanes, affording 8-[3,3-difluoro-4-(2,2,2-trifluoroethoxy)pyrrolidin-1-yl]-6-(2,4-dimethoxypyrimidin-5-yl)imidazo[1,2-b]pyridazine. ES/MS m/z: 461.20 [M+H].

Step 2: A solution of 8-[3,3-difluoro-4-(2,2,2-trifluoroethoxy)pyrrolidin-1-yl]-6-(2,4-dimethoxypyrimidin-5-yl)imidazo[1,2-b]pyridazine (15 mg) in 1:1 1N HCl:MeOH (5 mL) was heated to 80° C. After 2 hours, the reaction mixture was concentrated and residue obtained was purified by RP-HPLC (5-80% MeCN/H₂O gradient with TFA modifier) affording 8-[3,3-difluoro-4-(2,2,2-trifluoroethoxy)pyrrolidin-1-yl]-6-(2,4-dimethoxypyrimidin-5-yl)imidazo[1,2-b]pyridazine. ES/MS m/z: 433.10 [M+H]. ¹H NMR (400 MHz, DMSO-d6) δ 11.45-11.35 (m, 2H), 8.08 (d, J=1.1 Hz, 1H), 7.94 (d, J=6.1 Hz, 1H), 7.58 (d, J=1.1 Hz, 1H), 6.61 (s, 1H), 4.73-4.62 (m, 1H), 4.57-4.18 (m, 4H), 4.06 (s, 1H).

Example 204. 2-[1-[6-(2,4-dioxo-1H-pyrimidin-5-yl)imidazo[1,2-b]pyridazin-8-yl]-4,4-difluoro-pyrrolidin-3-yl]oxy-N,N-dimethyl-acetamide

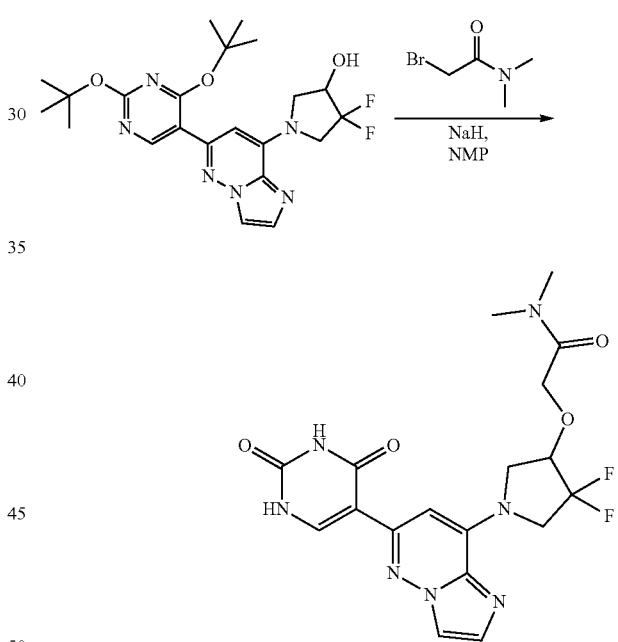

1-[6-(2,4-ditert-butoxypyrimidin-5-yl)imidazo[1,2-b]pyridazin-8-yl]-4,4-difluoro-pyrrolidin-3-ol (80 mg, 0.173 mmol, 1 equiv) and sodium hydride (60% dispersion in oil, 20 mg, 0.52 mmol, 3 equiv) were combined in THF (2 mL) at 5° C. After 15 minutes, 2-bromo-N,N-dimethyl-acetamide (57.4 mg, 0.346 mmol, 2 equiv) was added. After stirring at 0° C. for 1 h, the reaction was treated with 1M HCl (0.2 mL), concentrated to dryness, then purified by RP-HPLC (5-80% MeCN/H₂O gradient with TFA modifier) affording 2-[1-[6-(2,4-dioxo-1H-pyrimidin-5-yl)imidazo[1,2-b]pyridazin-8-yl]-4,4-difluoro-pyrrolidin-3-yl]oxy-N,N-dimethyl-acetamide. ES/MS m/z: 436.20 [M+H]. ¹H NMR (400 MHz, DMSO-d6) δ 11.46-11.35 (m, 2H), 8.08 (s, 1H), 7.95 (d, J=6.0 Hz, 1H), 7.58 (s, 1H), 6.61 (s, 1H), 4.54-4.09 (m, 7H), 2.87 (d, J=25.8 Hz, 6H).

Example 205. N-[1-[6-(2,4-dioxo-1H-pyrimidin-5-yl)imidazo[1,2-b]pyridazin-8-yl]-4,4-difluoro-pyrrolidin-3-yl]acetamide

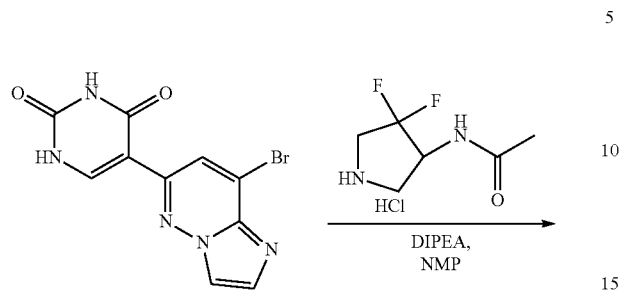

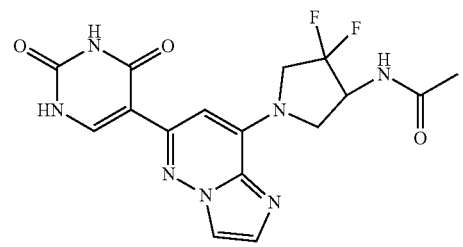

A solution of 5-(8-bromoimidazo[1,2-b]pyridazin-6-yl)-1H-pyrimidine-2,4-dione (70 mg, 0.16 mmol, 1 equiv), N-(4,4-difluoropyrrolidin-3-yl)acetamide;hydrochloride (91 mg, 0.454 mmol, 2 equiv), and DIPEA (0.16 mL, 0.91 mmol, 4 equiv) in NMP (1 mL) was heated at 110° C. After 6 h, the reaction mixture was directly purified by RP-HPLC (5-70% MeCN/H$_2$O with TFA modifier), affording N-[1-[6-(2,4-dioxo-1H-pyrimidin-5-yl)imidazo[1,2-b]pyridazin-8-yl]-4,4-difluoro-pyrrolidin-3-yl]acetamide. ES/MS m/z: 392.10 [M+H]. $^1$H NMR (400 MHz, DMSO-d6) δ 11.45-11.31 (m, 2H), 8.50 (d, J=8.6 Hz, 1H), 8.08 (d, J=1.2 Hz, 1H), 7.95 (d, J=6.1 Hz, 1H), 7.59 (d, J=1.2 Hz, 1H), 6.62 (s, 1H), 5.00-4.84 (m, 1H), 4.39 (t, J=27.3 Hz, 3H), 3.85-3.65 (m, 1H), 1.92 (d, J=3.2 Hz, 3H).

Example 206. 2,2,2-trifluoroethyl N-[1-[6-(2,4-dioxo-1H-pyrimidin-5-yl)imidazo[1,2-b]pyridazin-8-yl]-4,4-difluoro-pyrrolidin-3-yl]carbamate

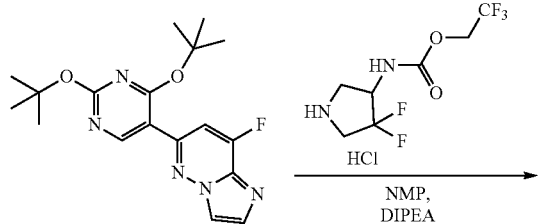

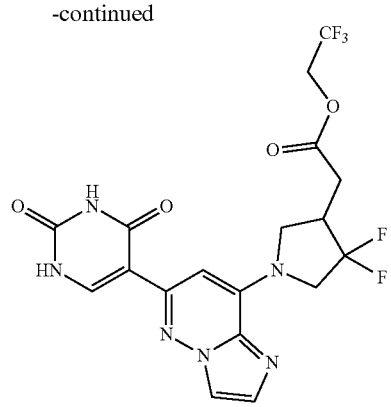

A microwave vial was charged with 2,2,2-trifluoroethyl N-(4,4-difluoropyrrolidin-3-yl)carbamate; hydrochloride (71 mg, 0.25 mmol, 2 equiv), DIPEA (0.09 mL, 0.50 mmol, 4 equiv), and NMP (2 mL) then 6-(2,4-di-tert-butoxypyrimidin-5-yl)-8-fluoroimidazo[1,2-b]pyridazine (45 mg, 0.125 mmol, 1 equiv). The reaction mixture was heated to 100° C. for 3 hours. The mixture was purified by RP-HPLC (5-80% MeCN/H$_2$O with TFA modifier), to give 2,2,2-trifluoroethyl N-[1-[6-(2,4-dioxo-1H-pyrimidin-5-yl)imidazo[1,2-b]pyridazin-8-yl]-4,4-difluoro-pyrrolidin-3-yl]carbamate. ES/MS m/z: 476.10 [M+H]. $^1$H NMR (400 MHz, DMSO-d6) δ 11.52-11.30 (m, 2H), 8.50 (d, J=8.7 Hz, 1H), 8.08 (d, J=1.1 Hz, 1H), 7.95 (d, J=6.1 Hz, 1H), 7.62-7.56 (m, 1H), 6.61 (s, 1H), 4.75 (q, J=9.1 Hz, 3H), 4.39 (d, J=32.5 Hz, 3H), 3.76 (d, J=38.3 Hz, 1H).

Example 207. cyclopropylmethyl N-[1-[6-(2,4-dioxo-1H-pyrimidin-5-yl)imidazo[1,2-b]pyridazin-8-yl]-4,4-difluoro-pyrrolidin-3-yl]carbamate

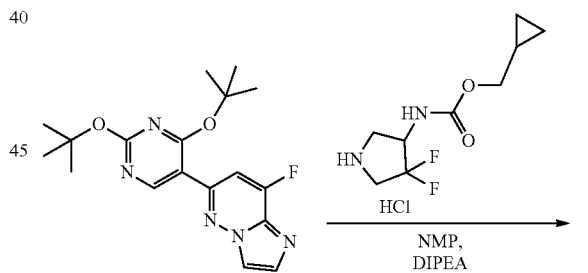

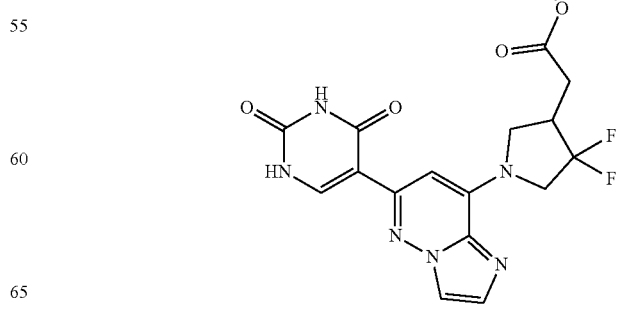

A microwave vial was charged with cyclopropylmethyl N-(4,4-difluoropyrrolidin-3-yl)carbamate; hydrochloride (50 mg, 0.20 mmol, 2 equiv), DIPEA (0.07 mL, 0.39 mmol, 4 equiv), and NMP (2 mL) then 6-(2,4-di-tert-butoxypyrimidin-5-yl)-8-fluoroimidazo[1,2-b]pyridazine (35 mg, 0.1 mmol, 1 equiv). The reaction mixture was heated to 100° C. for 2 hours. The mixture was purified by by RP-HPLC (5-80% MeCN/H₂O with TFA modifier), affording cyclopropylmethyl N-[1-[6-(2,4-dioxo-1H-pyrimidin-5-yl)imidazo[1,2-b]pyridazin-8-yl]-4,4-difluoro-pyrrolidin-3-yl]carbamate. ES/MS m/z: 448.20 [M+H]. ¹H NMR (400 MHz, DMSO-d6) δ 11.50-11.33 (m, 2H), 8.07 (d, J=1.1 Hz, 1H), 7.96 (dd, J=7.8, 5.4 Hz, 2H), 7.58 (d, J=1.2 Hz, 1H), 6.60 (s, 1H), 4.72 (dt, J=15.2, 8.0 Hz, 1H), 4.37 (d, J=48.8 Hz, 3H), 3.94-3.68 (m, 3H), 1.18-1.08 (m, 1H), 0.58-0.48 (m, 2H), 0.35-0.24 (m, 2H).

Example 208. 2,2-difluoroethyl N-[1-[6-(2,4-dioxo-1H-pyrimidin-5-yl]imidazo[1,2-b]pyridazin-8-yl]-4,4-difluoro-pyrrolidin-3-yl]carbamate

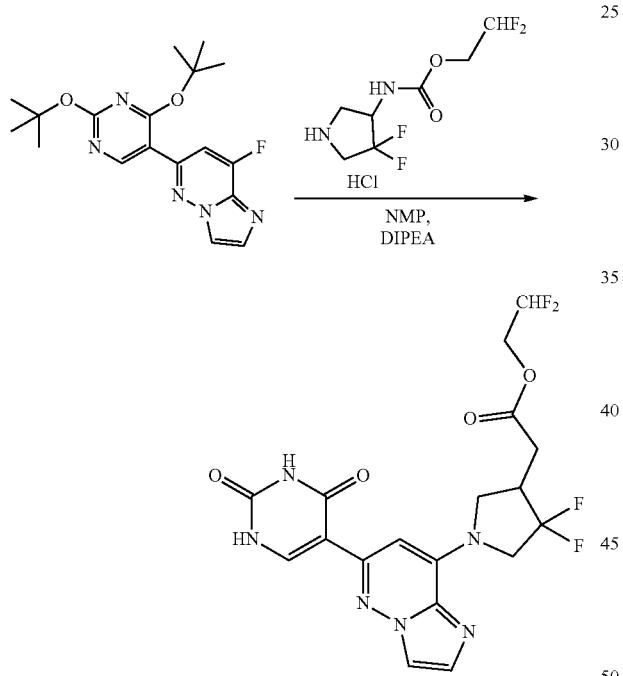

A microwave vial was charged with 2,2-difluoroethyl N-(4,4-difluoropyrrolidin-3-yl)carbamate; hydrochloride (46 mg, 0.17 mmol, 2 equiv), DIPEA (0.06 mL, 0.33 mmol, 4 equiv), and NMP (2 mL) then 6-(2,4-di-tert-butoxypyrimidin-5-yl)-8-fluoroimidazo[1,2-b]pyridazine (30 mg, 0.08 mmol, 1 equiv). The reaction mixture was heated to 100° C. for 3 hours. The mixture was purified by RP-HPLC (5-80% MeCN/H₂O with TFA modifier), to give 2,2-difluoroethyl N-[1-[6-(2,4-dioxo-1H-pyrimidin-5-yl)imidazo[1,2-b]pyridazin-8-yl]-4,4-difluoro-pyrrolidin-3-yl]carbamate.
ES/MS m/z: 458.10 [M+H]. ¹H NMR (400 MHz, DMSO-d6) δ 11.46-11.36 (m, 2H), 8.32 (d, J=8.7 Hz, 1H), 8.08 (d, J=1.1 Hz, 1H), 7.95 (d, J=6.1 Hz, 1H), 7.58 (d, J=1.1 Hz, 1H), 6.61 (s, 1H), 6.27 (tt, J=54.3, 3.3 Hz, 1H), 4.73 (dq, J=16.1, 8.2 Hz, 1H), 4.52-4.29 (m, 5H), 3.86-3.70 (m, 1H).

Example 209. N-[1-[6-(2,4-dioxo-1H-pyrimidin-5-yl)imidazo[1,2-b]pyridazin-8-yl]-4,4-difluoro-pyrrolidin-3-yl]benzamide

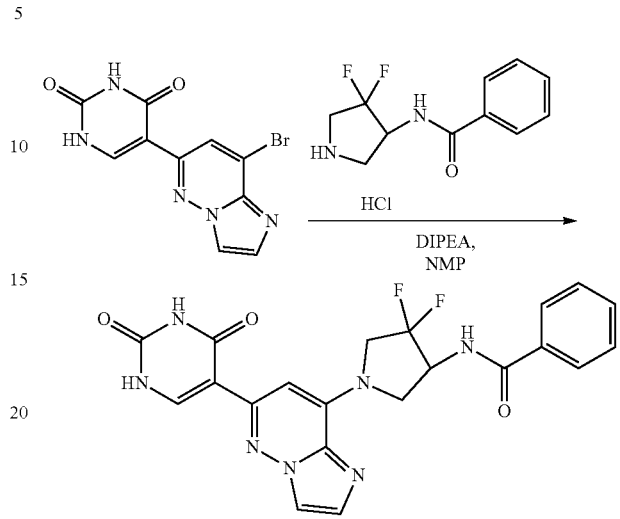

A solution of 5-(8-bromoimidazo[1,2-b]pyridazin-6-yl)-1H-pyrimidine-2,4-dione (70 mg, 0.23 mmol, 1 equiv), N-(4,4-difluoropyrrolidin-3-yl)benzamide; hydrochloride (119 mg, 0.454 mmol, 2 equiv), and DIPEA (0.16 mL, 0.91 mmol, 4 equiv) in NMP (1 mL) was heated at 110° C. After 6 h, the reaction mixture was directly purified by RP-HPLC (5-80% MeCN/H₂O with TFA modifier), affording N-[1-[6-(2,4-dioxo-1H-pyrimidin-5-yl)imidazo[1,2-b]pyridazin-8-yl]-4,4-difluoro-pyrrolidin-3-yl]benzamide. ES/MS m/z: 454.20 [M+H]. ¹H NMR (400 MHz, DMSO-d6) δ 11.45-11.36 (m, 2H), 8.91 (d, J=8.4 Hz, 1H), 8.08 (s, 1H), 7.99-7.88 (m, 3H), 7.63-7.52 (m, 2H), 7.50 (t, J=7.5 Hz, 2H), 6.65 (s, 1H), 5.26-5.16 (m, 1H), 4.52 (s, 3H), 4.02 (s, 1H)

Example 210. N-[1-[6-(2,4-dioxo-1H-pyrimidin-5-yl)imidazo[1,2-b]pyridazin-8-yl]-4,4-difluoro-pyrrolidin-3-yl]-4-(trifluoromethyl)benzamide

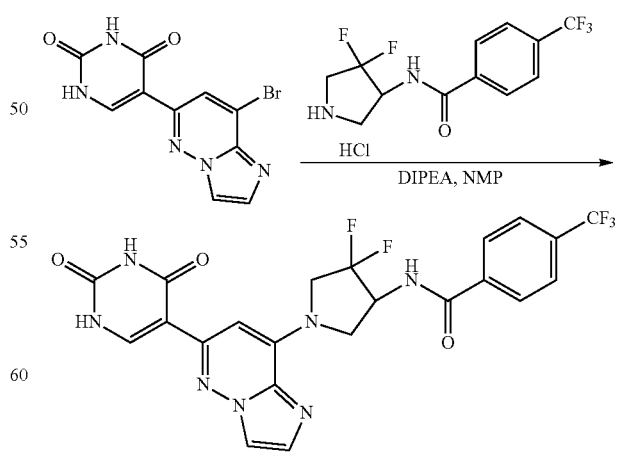

A solution of 5-(8-bromoimidazo[1,2-b]pyridazin-6-yl)-1H-pyrimidine-2,4-dione (70 mg, 0.23 mmol, 1 equiv), N-(4,4-difluoropyrrolidin-3-yl)-4-(trifluoromethyl)benzamide; hydrochloride (140 mg, 0.424 mmol, 1.9 equiv), and DIPEA (0.16 mL, 0.91 mmol, 4 equiv) in NMP (1 mL) was heated at 110° C. After 6 h, the reaction mixture was directly purified by RP-HPLC (5-80% MeCN/H$_2$O with TFA modifier), affording N-[1-[6-(2,4-dioxo-1H-pyrimidin-5-yl)imidazo[1,2-b]pyridazin-8-yl]-4,4-difluoro-pyrrolidin-3-yl]-4-(trifluoromethyl)benzamide. ES/MS m/z: 522.20 [M+H]. $^1$H NMR (400 MHz, DMSO-d6) δ 11.41 (d, J=14.6 Hz, 2H), 9.16 (d, J=8.3 Hz, 1H), 8.15-8.03 (m, 3H), 7.93 (dd, J=25.6, 7.1 Hz, 3H), 7.59 (s, 1H), 6.65 (s, 1H), 5.26-5.17 (m, 1H), 4.53 (s, 2H), 4.40 (s, 1H), 4.04 (s, 1H).

Example 211. N-[1-[6-(2,4-dioxo-1H-pyrimidin-5-yl)imidazo[1,2-b]pyridazin-8-yl]-4,4-difluoro-pyrrolidin-3-yl]-5-(trifluoromethyl)pyridine-2-carboxamide

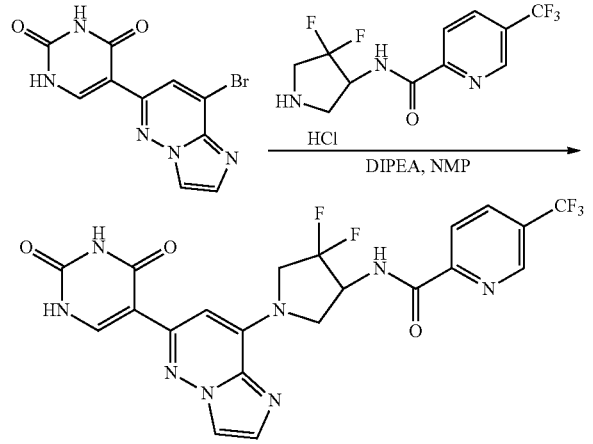

A solution of 5-(8-bromoimidazo[1,2-b]pyridazin-6-yl)-1H-pyrimidine-2,4-dione (70 mg, 0.23 mmol, 1 equiv), N-(4,4-difluoropyrrolidin-3-yl)-5-(trifluoromethyl)pyridine-2-carboxamide; hydrochloride (151 mg, 0.45 mmol, 2 equiv), and DIPEA (0.16 mL, 0.91 mmol, 4 equiv) in NMP (1 mL) was heated at 110° C. After 6 h, the reaction mixture was directly purified by RP-HPLC (5-80% MeCN/H$_2$O with TFA modifier), affording N-[1-[6-(2,4-dioxo-1H-pyrimidin-5-yl)imidazo[1,2-b]pyridazin-8-yl]-4,4-difluoro-pyrrolidin-3-yl]-5-(trifluoromethyl)pyridine-2-carboxamide. ES/MS m/z: 523.20 [M+H]. $^1$H NMR (400 MHz, DMSO-d6) δ 11.45-11.36 (m, 2H), 9.54 (d, J=8.9 Hz, 1H), 9.13-9.05 (m, 1H), 8.48 (dd, J=8.2, 2.3 Hz, 1H), 8.29 (d, J=8.2 Hz, 1H), 8.09 (d, J=1.2 Hz, 1H), 7.96 (d, J=6.1 Hz, 1H), 7.59 (d, J=1.2 Hz, 1H), 6.65 (s, 1H), 5.24 (q, J=9.4 Hz, 1H), 5.09 (s, OH), 4.54 (s, 2H), 4.42 (s, 1H), 4.12 (s, 1H).

Example 212. 5-[3-chloro-8-[(1S,2S)-2-[3,3-dimethyl-2-oxo-1-(2,2,2-trifluoroethyl)indolin-6-yl]cyclopropyl]imidazo[1,2-b]pyridazin-6-yl]-1H-pyrimidine-2,4-dione

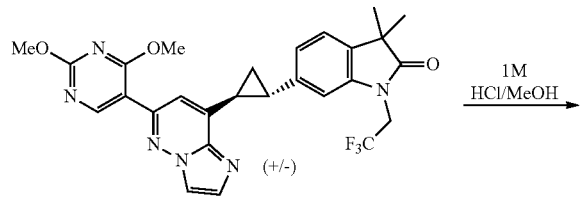

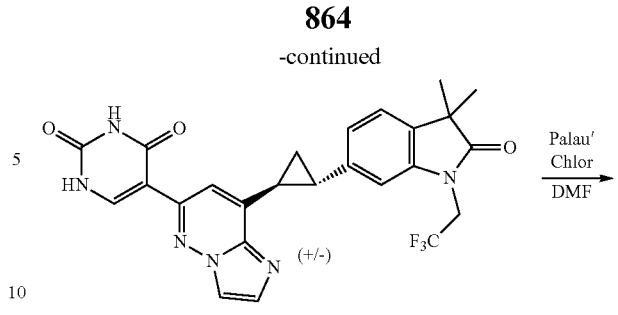

Step 1: A solution of 6-[(1S,2S)-2-[6-(2,4-dimethoxypyrimidin-5-yl)imidazo[1,2-b]pyridazin-8-yl]cyclopropyl]-3,3-dimethyl-1-(2,2,2-trifluoroethyl)indolin-2-one (racemic Mixture) (48 mg) in 1:1 1N HCl:MeOH (10 mL) was heated to 80° C. After 4 hours, the reaction mixture was concentrated and residue obtained was diluted with water and acetonitrile and lyophilized, affording 5-[8-[(1S,2S)-2-[3,3-dimethyl-2-oxo-1-(2,2,2-trifluoroethyl)indolin-6-yl]cyclopropyl]imidazo[1,2-b]pyridazin-6-yl]-1H-pyrimidine-2,4-dione (Racemic Mixture). $^1$H NMR (400 MHz, DMSO-d6) δ 11.56 (d, J=7.0 Hz, 2H), 8.36 (d, J=1.4 Hz, 1H), 8.04 (d, J=6.0 Hz, 1H), 7.90 (s, 1H), 7.58 (s, 1H), 7.33 (d, J=7.6 Hz, 1H), 7.14 (s, 1H), 7.00 (dd, J=7.8, 1.4 Hz, 1H), 4.63 (q, J=9.4 Hz, 2H), 2.83 (ddd, J=9.2, 6.3, 4.4 Hz, 1H), 2.75 (dt, J=9.6, 5.4 Hz, 1H), 2.07 (dt, J=8.9, 5.2 Hz, 1H), 1.90-1.80 (m, 1H), 1.30 (s, 6H). $^{19}$F NMR (376 MHz, DMSO-d6) δ −69.28 (t, J=9.4 Hz), −75.24

Step 2: Palau'Chlor (20 mg, 0.095 mmol, 1 equiv) was added to a solution of 5-[8-[(1S,2S)-2-[3,3-dimethyl-2-oxo-1-(2,2,2-trifluoroethyl)indolin-6-yl]cyclopropyl]imidazo[1,2-b]pyridazin-6-yl]-1H-pyrimidine-2,4-dione;hydrochloride (Racemic Mixture) (52 mg, 0.095 mmol, 1 equiv) in DMF (1 mL). After 16 h, the reaction mixture was directly purified by RP-HPLC (10-80% MeCN/H$_2$O with TFA modifier), affording 5-[3-chloro-8-[(1S,2S)-2-[3,3-dimethyl-2-oxo-1-(2,2,2-trifluoroethyl)indolin-6-yl]cyclopropyl]imidazo[1,2-b]pyridazin-6-yl]-1H-pyrimidine-2,4-dione (Racemic Mixture). ES/MS m/z: 545.10 [M+H]. $^1$H NMR (400 MHz, DMSO-d6) δ 11.58-11.50 (m, 2H), 8.08-8.01 (m, 1H), 7.85 (s, 1H), 7.56 (s, 1H), 7.31 (d, J=7.6 Hz, 1H), 7.13 (s, 1H), 7.01 (dd, J=7.7, 1.5 Hz, 1H), 4.63 (q, J=9.4 Hz, 2H), 2.86 (dt, J=9.3, 5.8 Hz, 1H), 2.76 (dd, J=8.9, 5.1 Hz, 1H), 2.17-2.06 (m, 1H), 1.87-1.74 (m, 1H), 1.30 (s, 6H). $^{19}$F NMR (376 MHz, DMSO-d6) δ −69.31 (t, J=9.3 Hz), −74.69.

Example 213. 5-[3-chloro-8-[(1S,2S)-2-[3-fluoro-1-(2,2,2-trifluoroethyl)indazol-6-yl]cyclopropyl]imidazo[1,2-b]pyridazin-6-yl]-1H-pyrimidine-2,4-dione

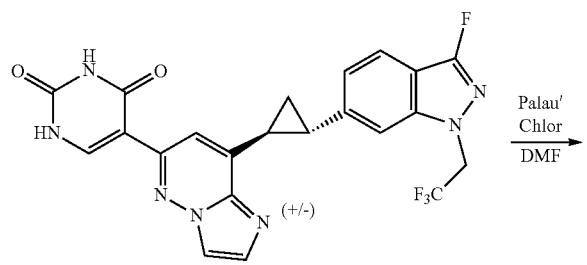

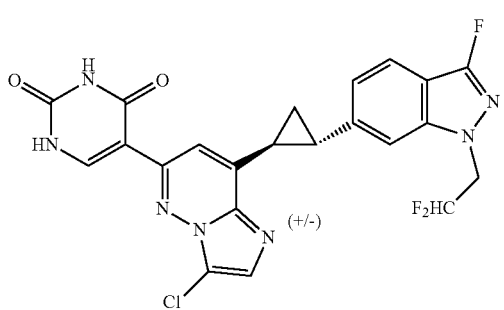

Palau'Chlor (11 mg, 0.05 mmoL, 1 equiv) was added to a solution of 5-[8-[(1S,2S)-2-[3-fluoro-1-(2,2,2-trifluoroethyl)indazol-6-yl]cyclopropyl]imidazo[1,2-b]pyridazin-6-yl]-1H-pyrimidine-2,4-dione;2,2,2-trifluoroacetic acid (Racemic Mixture) (30 mg, 0.05 mmol, 1 equiv) in DMF (1 mL). After 1 h, the reaction mixture was directly purified by RP-HPLC (15-95% MeCN/H$_2$O with TFA modifier), affording 5-[3-chloro-8-[(1S,2S)-2-[3-fluoro-1-(2,2,2-trifluoroethyl)indazol-6-yl]cyclopropyl]imidazo[1,2-b]pyridazin-6-yl]-1H-pyrimidine-2,4-dione. ES/MS m/z: 520.10 [M+H]. $^1$H NMR (400 MHz, Acetonitrile-d3) δ 9.24 (s, 2H), 8.13 (d, J=6.4 Hz, 1H), 7.78 (d, J=4.3 Hz, 2H), 7.66 (d, J=8.5 Hz, 1H), 7.45 (d, J=2.1 Hz, 1H), 7.17 (dd, J=8.5, 1.3 Hz, 1H), 4.98 (q, J=8.7 Hz, 2H), 2.98-2.78 (m, 2H), 2.11 (dt, J=9.1, 5.7 Hz, 1H), 1.90 (dt, J=8.9, 5.8 Hz, 1H). $^{19}$F NMR (376 MHz, Acetonitrile-d3) δ -72.34 (t, J=8.8 Hz), -77.32, -135.42 (d, J=2.1 Hz).

Example 214. 5-[8-[(1S,2S)-2-[1-(2,2-difluoroethyl)indazol-6-yl]cyclopropyl]-3-fluoro-imidazo[1,2-b]pyridazin-6-yl]-1H-pyrimidine-2,4-dione

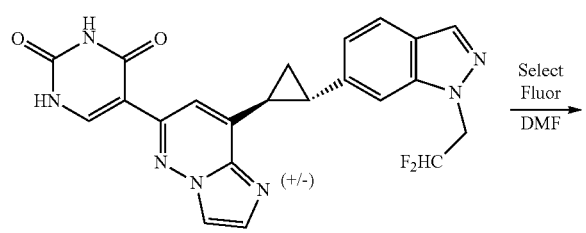

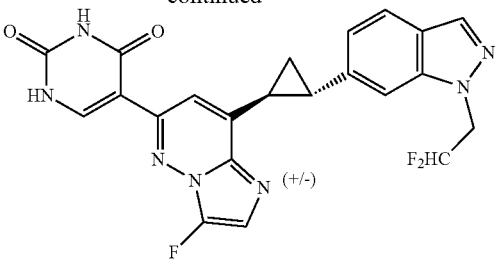

SelectFluor (253 mg, 0.71 mmoL, 1 equiv) was added to a solution of 5-[8-[(1S,2S)-2-[1-(2,2-difluoroethyl)indazol-6-yl]cyclopropyl]imidazo[1,2-b]pyridazin-6-yl]-1H-pyrimidine-2,4-dione;2,2,2-trifluoroacetic acid (Racemic Mixture) (310 mg, 0.55 mmol, 1 equiv) in DMF (10 mL). After 16 h, the reaction mixture was directly purified by RP-HPLC (15-95% MeCN/H$_2$O with TFA modifier), affording 5-[8-[(1S,2S)-2-[1-(2,2-difluoroethyl)indazol-6-yl]cyclopropyl]-3-fluoro-imidazo[1,2-b]pyridazin-6-yl]-1H-pyrimidine-2,4-dione (Racemic Mixture). ES/MS m/z: 468.20 [M+H]. $^1$H NMR (400 MHz, DMSO-d6) δ 11.53 (d, J=4.6 Hz, 2H), 8.14-8.02 (m, 2H), 7.78-7.63 (m, 2H), 7.61-7.46 (m, 2H), 7.08 (dd, J=8.4, 1.4 Hz, 1H), 6.61-6.25 (m, 1H), 4.91 (td, J=15.0, 3.8 Hz, 2H), 3.02 (ddd, J=9.1, 6.2, 4.4 Hz, 1H), 2.79 (dt, J=9.6, 5.5 Hz, 1H), 2.17 (dt, J=8.7, 5.2 Hz, 1H), 1.90 (dt, J=8.7, 5.5 Hz, 1H). $^{19}$F NMR (376 MHz, DMSO-d6) δ -74.68, -122.27 (t, J=15.0 Hz), -122.41 (t, J=15.1 Hz), -155.59 (d, J=7.4 Hz).

Example 215. 5-(7-((2S,2S)-2-(4-(difluoromethyl)phenyl)cyclopropyl)pyrazolo[1,5-a]pyrimidin-5-yl)pyrimidine-2,4(1H,3H)-dione

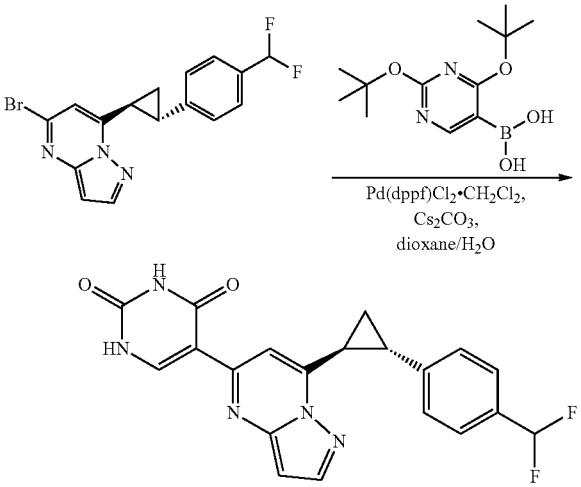

5-(7-((1S,2S)-2-(4-(difluoromethyl)phenyl)cyclopropyl)pyrazolo[1,5-a]pyrimidin-5-yl)pyrimidine-2,4(1H,3H)-dione was prepared as follows: A microwave vial was charged with 5-bromo-7-((1S,2S)-2-(4-(difluoromethyl)phenyl)cyclopropyl)pyrazolo[1,5-a]pyrimidine (33 mg, 0.090 mmol, 1 equiv), (2,4-di-tert-butoxypyrimidin-5-yl)boronic acid (29 mg, 0.108 mmol, 1.2 equiv), Pd(dppf)Cl$_2$CH$_2$Cl$_2$ (7 mg, 0.009 mmol, 0.1 equiv) and cesium carbonate (88 mg, 0.269 mmol, 3 equiv). To this was added 1,4 dioxane (2.0 mL) and water (0.50 mL). The reaction mixture was heated to 90° C.

and stirred overnight. After cooling to room temperature, the mixture was diluted with EtOAc and filtered through a pad of Celite. The filtrate was concentrated under reduced pressure and the crude material was purified by silica gel chromatography (0-100% EtOAc in hexanes), then by RP-HPLC (10-90% MeCN/H$_2$O with TFA, Gemini-NX column) to afford the title compound as the TFA salt. ES/MS m/z: 396.0 [M+H]. $^1$H NMR (400 MHz, DMSO-d6) δ 11.64-11.48 (m, 2H), 8.34 (d, J=6.3 Hz, 1H), 8.16 (d, J=2.3 Hz, 1H), 7.68 (s, 1H), 7.52 (d, J=8.1 Hz, 2H), 7.45 (d, J=8.1 Hz, 2H), 7.01 (t, J=56.0 Hz, 1H), 6.63 (d, J=2.3 Hz, 1H), 3.14-3.05 (m, 1H), 2.72-2.61 (m, 1H), 1.98-1.79 (m, 2H). $^{19}$F NMR (376 MHz, DMSO-d6) δ −75.10, −109.35.

Example 216. 5-(7-(3,3-difluoro-4,4-dimethylpyrrolidin-1-yl)pyrazolo[1,5-a]pyrimidin-5-yl)pyrimidine-2,4(1H,3H)-dione

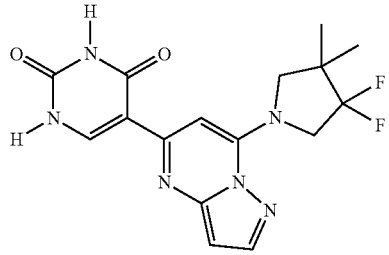 [SMILES: CC1(C)CN(c2cc(-c3c[nH]c(=O)[nH]c3=O)nc3ccnn23)CC1(F)F]

5-(7-(3,3-difluoro-4,4-dimethylpyrrolidin-1-yl)pyrazolo[1,5-a]pyrimidin-5-yl)pyrimidine-2,4(1H,3H)-dione was prepared as follows: To a solution of 7-(3,3-difluoro-4,4-dimethylpyrrolidin-1-yl)-5-(2,4-dimethoxypyrimidin-5-yl)pyrazolo[1,5-a]pyrimidine (110 mg, 0.282 mmol, 1 equiv) in MeOH (2.5 mL) was added 1 N HCl (2.5 mL). The solution was heated to 80° C. and stirred for 25 min. The heat was turned off and the solution was left to stir overnight. The mixture was purified by RP-HPLC (10-90% MeCN/H$_2$O with TFA, Gemini-NX column) to afford the title compound as the TFA. ES/MS m/z: 363.1 [M+H]. $^1$H NMR (400 MHz, DMSO-d6) δ 11.65 (s, 1H), 11.52 (s, 1H), 8.38 (d, J=6.0 Hz, 1H), 8.07 (s, 1H), 7.00 (s, 1H), 6.41 (s, 1H), 4.59 (t, J=13.7 Hz, 2H), 3.91 (s, 2H), 1.22 (s, 6H). $^{19}$F NMR (376 MHz, DMSO-d6) δ −74.85, −115.20.

Example 217. 5-(7-(3,3-difluoro-4,4-dimethylpyrrolidin-1-yl)-3-ethylpyrazolo[1,5-a]pyrimidin-5-yl)pyrimidine-2,4(1H,3H)-dione

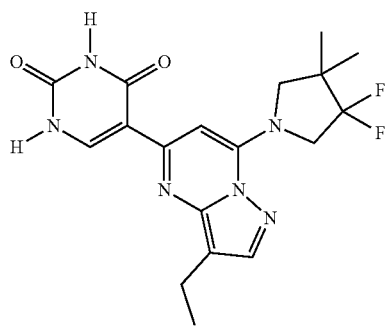 [SMILES: CCc1cnn2c(N3CC(C)(C)C(F)(F)C3)cc(-c3c[nH]c(=O)[nH]c3=O)nc12]

5-(7-(3,3-difluoro-4,4-dimethylpyrrolidin-1-yl)-3-ethylpyrazolo[1,5-a]pyrimidin-5-yl)pyrimidine-2,4(1H,3H)-dione was prepared as follows: To a solution of 7-(3,3-difluoro-4,4-dimethylpyrrolidin-1-yl)-5-(2,4-dimethoxypyrimidin-5-yl)-3-ethylpyrazolo[1,5-a]pyrimidine (60 mg, 0.143 mmol, 1 equiv) in MeOH (1.5 mL) was added 1 N HCl (1.5 mL). The solution was heated to 80° C. and stirred for 3 h prior to purification by RP-HPLC (10-90% MeCN/H$_2$O with TFA, Gemini-NX column) to afford the title compound as the TFA salt. ES/MS m/z: 391.1 [M+H]. $^1$H NMR (400 MHz, DMSO-d6) δ 11.75-11.45 (m, 2H), 8.40 (d, J=5.9 Hz, 1H), 7.98 (s, 1H), 6.92 (s, 1H), 4.58 (t, J=13.8 Hz, 2H), 3.90 (s, 2H), 2.67 (q, J=7.6 Hz, 2H), 1.27-1.18 (m, 9H). $^{19}$F NMR (376 MHz, DMSO-d6) δ −75.18, −115.17.

Example 218. 5-(3-chloro-7-(7,7-difluoro-5-azaspiro[2.4]heptan-5-yl)pyrazolo[1,5-a]pyrimidin-5-yl)pyrimidine-2,4(1H,3H)-dione

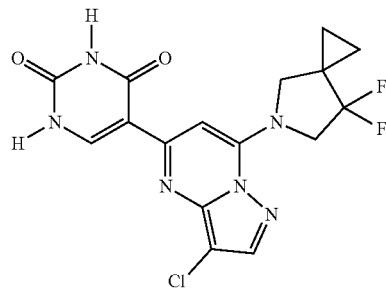 [SMILES: O=c1[nH]cc(-c2cc(N3CC(F)(F)C4(CC4)C3)n3ncc(Cl)c3n2)c(=O)[nH]1]

5-(3-chloro-7-(7,7-difluoro-5-azaspiro[2.4]heptan-5-yl)pyrazolo[1,5-a]pyrimidin-5-yl)pyrimidine-2,4(1H,3H)-dione was prepared as follows: To a solution of 3-chloro-7-(7,7-difluoro-5-azaspiro[2.4]heptan-5-yl)-5-(2,4-dimethoxypyrimidin-5-yl)pyrazolo[1,5-a]pyrimidine (32 mg, 0.077 mmol, 1 equiv) in MeOH (2.0 mL) was added 1 N HCl (2.0 mL). The solution was heated to 80° C. and stirred for 2 h prior to isolation by filtration as the HCl salt. ES/MS m/z: 395.0 [M+H]. $^1$H NMR (400 MHz, DMSO-d6) δ 11.55 (d, J=6.4 Hz, 1H), 11.47 (s, 1H), 8.40 (d, J=6.3 Hz, 1H), 8.19 (s, 1H), 7.21 (s, 1H), 4.64 (t, J=12.5 Hz, 2H), 4.06 (s, 2H), 1.08 1.00 (m, 4H). $^{19}$F NMR (376 MHz, DMSO-d6) δ −107.33.

Examples 219 and 220. 5-(7-(3,3-difluoro-4,4-dimethylpyrrolidin-1-yl)-3-fluoropyrazolo[1,5-a]pyrimidin-5-yl)pyrimidine-2,4(1H,3H)-dione and 5-(3-chloro-7-(3,3-difluoro-4,4-dimethylpyrrolidin-1-yl)pyrazolo[1,5-a]pyrimidin-5-yl)pyrimidine-2,4(1H,3H)-dione

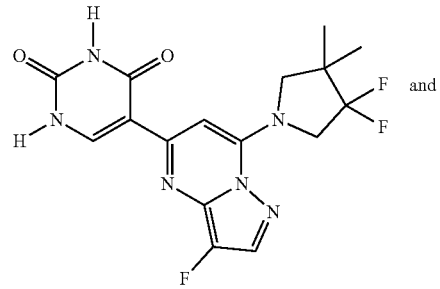

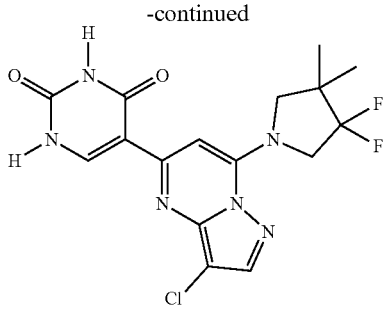

5-(7-(3,3-difluoro-4,4-dimethylpyrrolidin-1-yl)-3-fluoropyrazolo[1,5-a]pyrimidin-5-yl)pyrimidine-2,4(1H,3H)-dione and 5-(3-chloro-7-(3,3-difluoro-4,4-dimethylpyrrolidin-1-yl)pyrazolo[1,5-a]pyrimidin-5-yl)pyrimidine-2,4(1H,3H)-dione as the TFA salts were prepared in the manner described for Example 1, but replacing 7-(3,3-difluoro-4,4-dimethylpyrrolidin-1-yl)-5-(2,4-dimethoxypyrimidin-5-yl)pyrazolo[1,5-a]pyrimidine with a mixture of 7-(3,3-difluoro-4,4-dimethylpyrrolidin-1-yl)-5-(2,4-dimethoxypyrimidin-5-yl)-3-fluoropyrazolo[1,5-a]pyrimidine and 3-chloro-7-(3,3-difluoro-4,4-dimethylpyrrolidin-1-yl)-5-(2,4-dimethoxypyrimidin-5-yl)pyrazolo[1,5-a]pyrimidine.

Example 219 5-(7-(3,3-difluoro-4,4-dimethylpyrrolidin-1-yl)-3-fluoropyrazolo[1,5-a]pyrimidin-5-yl)pyrimidine-2,4(1H,3H)-dione ES/MS m/z: 381.1 [M+H]. $^1$H NMR (400 MHz, DMSO-d6) δ 11.58-11.43 (m, 2H), 8.35 (d, J=6.3 Hz, 1H), 8.19 (d, J=3.5 Hz, 1H), 7.08 (s, 1H), 4.56 (t, J=13.8 Hz, 2H), 3.84 (s, 2H), 1.21 (s, 6H). $^{19}$F NMR (376 MHz, DMSO-d6) δ −75.35, −115.25, −187.82.

Example 220 5-(3-chloro-7-(3,3-difluoro-4,4-dimethylpyrrolidin-1-yl)pyrazolo[1,5-a]pyrimidin-5-yl)pyrimidine-2,4(1H,3H)-dione ES/MS m/z: 397.1 [M+H]. $^1$H NMR (400 MHz, DMSO-d6) δ 11.57-11.45 (m, 2H), 8.39 (d, J=6.4 Hz, 1H), 8.19 (s, 1H), 7.19 (s, 1H), 4.56 (t, J=13.7 Hz, 2H), 3.85 (s, 2H), 1.22 (s, 6H). $^{19}$F NMR (376 MHz, DMSO-d6) δ −74.85, −115.25.

Example 221. 5-(7-(3,3-difluoro-4-methylpyrrolidin-1-yl)pyrazolo[1,5-a]pyrimidin-5-yl)pyrimidine-2,4(1H,3H)-dione

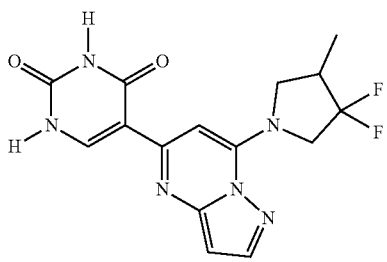 [SMILES: CC1CN(c2cc(-c3c[nH]c(=O)[nH]c3=O)nc3ccnn23)CC1(F)F]

5-(7-(3,3-difluoro-4-methylpyrrolidin-1-yl)pyrazolo[1,5-a]pyrimidin-5-yl)pyrimidine-2,4(1H,3H)-dione was prepared as follows: To a solution of 7-(3,3-difluoro-4-methylpyrrolidin-1-yl)-5-(2,4-dimethoxypyrimidin-5-yl)pyrazolo[1,5-a]pyrimidine (240 mg, 0.638 mmol, 1 equiv) in MeOH (3.0 mL) was added 1 N HCl (3.0 mL). The solution was heated to 80° C. and stirred for 5 h prior to purification by RP-HPLC (10-90% MeCN/H$_2$O with TFA, Gemini-NX column) to afford the title compound as the TFA salt. ES/MS m/z: 349.1 [M+H]. $^1$H NMR (400 MHz, DMSO-d6) δ 11.73 (s, 1H), 11.58 (s, 1H), 8.42 (d, J=6.1 Hz, 1H), 8.10 (d, J=2.3 Hz, 1H), 6.97 (s, 1H), 6.44 (d, J=2.3 Hz, 1H), 4.63-4.51 (m, 2H), 4.37-4.30 (m, 1H), 3.71-3.63 (m, 1H), 2.97-2.79 (m, 1H), 1.16 (d, J=6.8 Hz, 3H). $^{19}$F NMR (376 MHz, DMSO-d6) δ −75.07, −109.83 (d, J=226.5 Hz), −113.68 (d, J=227.8 Hz).

Example 222. 5-(7-(3,3-difluoro-4-methylpyrrolidin-1-yl)-3-fluoropyrazolo[1,5-a]pyrimidin-5-yl)pyrimidine-2,4(1H,3H)-dione

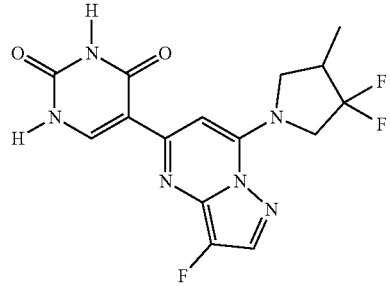 [SMILES: CC1CN(c2cc(-c3c[nH]c(=O)[nH]c3=O)nc3c(F)cnn23)CC1(F)F]

5-(7-(3,3-difluoro-4-methylpyrrolidin-1-yl)-3-fluoropyrazolo[1,5-a]pyrimidin-5-yl)pyrimidine-2,4(1H,3H)-dione as the TFA salt was prepared in the manner described for Example 1, but replacing 7-(3,3-difluoro-4,4-dimethylpyrrolidin-1-yl)-5-(2,4-dimethoxypyrimidin-5-yl)pyrazolo[1,5-a]pyrimidine with 7-(3,3-difluoro-4-methylpyrrolidin-1-yl)-5-(2,4-dimethoxypyrimidin-5-yl)-3-fluoropyrazolo[1,5-a]pyrimidine. The solution was heated to 80° C. and stirred for 2 h and 20 min prior to purification. ES/MS m/z: 367.0 [M+H]. $^1$H NMR (400 MHz, DMSO-d6) δ 11.57-11.42 (m, 2H), 8.35 (d, J=6.3 Hz, 1H), 8.19 (d, J=3.5 Hz, 1H), 7.09 (s, 1H), 4.59-4.44 (m, 2H), 4.28-4.17 (m, 1H), 3.62-3.52 (m, 1H), 2.93-2.75 (m, 1H), 1.15 (d, J=6.8 Hz, 3H). $^{19}$F NMR (376 MHz, DMSO-d6) δ −75.30, −109.72 (d, J=227.4 Hz), −113.69 (d, J=227.5 Hz), −187.84.

Example 223. 5-(8-((3aR,6aS)-hexahydrocyclopenta[c]pyrrol-2(1H)-yl)imidazo[1,2-b]pyridazin-6-yl)pyrimidine-2,4(1H,3H)-dione

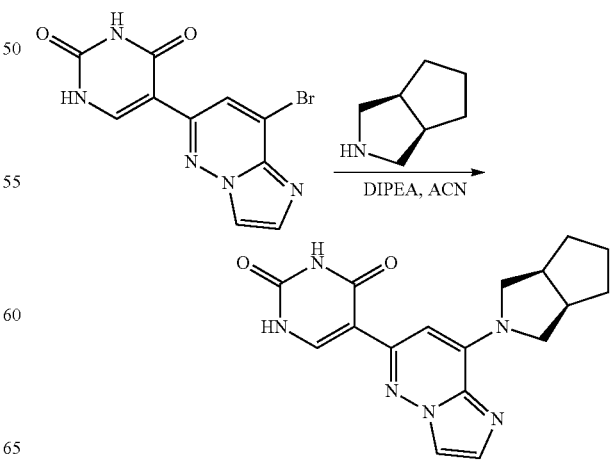

5-(8-((3aR,6aS)-hexahydrocyclopenta[c]pyrrol-2(1H)-yl) imidazo[1,2-b]pyridazin-6-yl)pyrimidine-2,4(1H,3H)-dione was prepared as follows: To a solution of 5-(8-bromoimidazo[1,2-b]pyridazin-6-yl)pyrimidine-2,4(1H,3H)-dione (67 mg, 0.217 mmol, 1 equiv) and (3aR,6aS)-octahydrocyclopenta[c]pyrrole (41 mg, 0.369 mmol, 1.7 equiv) in ACN (2.0 mL) was added DIPEA (0.08 mL, 0.435 mmol, 2 equiv). The reaction mixture was heated to 130° C. and stirred for 5 h. The crude material was purified by RP-HPLC (10-90% MeCN/H$_2$O with TFA, Gemini-NX column) to afford the title compound as the TFA salt. ES/MS m/z: 339.1 [M+H]. $^1$H NMR (400 MHz, DMSO-d6) δ 11.44-11.32 (m, 2H), 8.06 (s, 1H), 7.94 (d, J=6.0 Hz, 1H), 7.61 (s, 1H), 6.65 (s, 1H), 4.10-3.95 (m, 2H), 3.77-3.55 (m, 2H), 2.83-2.74 (m, 2H), 1.90-1.46 (m, 6H). $^{19}$F NMR (376 MHz, DMSO-d6) δ −75.27.

Example 224. 5-(8-(6,6-difluoro-3-azabicyclo[3.1.0] hexan-3-yl)imidazo[1,2-b]pyridazin-6-yl)pyrimidine-2,4(1H,3H)-dione

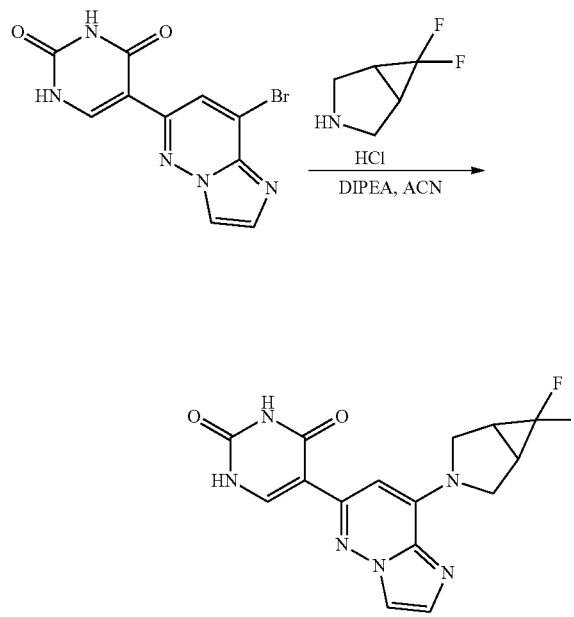

5-(8-(6,6-difluoro-3-azabicyclo[3.1.0]hexan-3-yl)imidazo[1,2-b]pyridazin-6-yl)pyrimidine-2,4(1H,3H)-dione was prepared as follows: To a solution of 5-(8-bromoimidazo[1,2-b]pyridazin-6-yl)pyrimidine-2,4(1H,3H)-dione (64 mg, 0.208 mmol, 1 equiv) and 6,6-difluoro-3-azabicyclo[3.1.0]hexane hydrochloride (39 mg, 0.249 mmol, 1.2 equiv) in ACN (2.0 mL) was added DIPEA (0.09 mL, 0.499 mmol, 2.4 equiv). The reaction mixture was stirred at 95° C. for 2 h, then at 120° C. overnight. The solution was stirred for an additional 5 h at 140° C. prior to purification by RP-HPLC (10-90% MeCN/H$_2$O with TFA, Gemini-NX column) to afford the title compound as the TFA salt. ES/MS m/z: 347.0 [M+H]. $^1$H NMR (400 MHz, DMSO-d6) δ 11.44-11.31 (m, 2H), 8.04 (s, 1H), 7.92 (d, J=6.1 Hz, 1H), 7.55 (s, 1H), 6.55 (s, 1H), 4.56-3.91 (m, 4H), 2.81-2.72 (m, 2H). $^{19}$F NMR (376 MHz, DMSO-d6) δ −75.29, −129.84 (d, J=157.9 Hz), −155.12 (d, J=158.0 Hz).

Example 225. 5-(8-(3-azabicyclo[3.1.0]hexan-3-yl) imidazo[1,2-b]pyridazin-6-yl)pyrimidine-2,4(1H, 3H)-dione

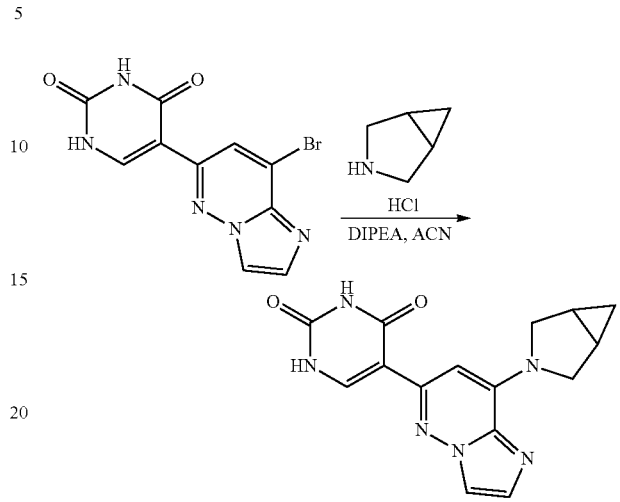

5-(8-(3-azabicyclo[3.1.0]hexan-3-yl)imidazo[1,2-b] pyridazin-6-yl)pyrimidine-2,4(1H,3H)-dione was prepared as follows: To a solution of 5-(8-bromoimidazo[1,2-b] pyridazin-6-yl)pyrimidine-2,4(1H,3H)-dione (50 mg, 0.162 mmol, 1 equiv) and 3-azabicyclo[3.1.0]hexane hydrochloride (21 mg, 0.179 mmol, 1.1 equiv) in ACN (2.0 mL) was added DIPEA (0.07 mL, 0.389 mmol, 2.4 equiv). The reaction mixture was stirred at 120° C. for 3 days, then at 135° C. overnight. The crude material was purified by RP-HPLC (10-90% MeCN/H$_2$O with TFA, Gemini-NX column) twice to afford the title compound as the TFA salt. ES/MS m/z: 311.1 [M+H]. $^1$H NMR (400 MHz, Methanol-d4) δ 8.17 (s, 1H), 8.11 (d, J=1.8 Hz, 1H), 7.79 (d, J=1.8 Hz, 1H), 7.10 (s, 1H), 4.15-4.06 (m, 2H), 3.91-3.84 (m, 2H), 1.91-1.84 (m, 2H), 0.98-0.87 (m, 1H), 0.36-0.28 (m, 1H). $^{19}$F NMR (376 MHz, Methanol-d4) δ −77.78.

Example 226. 5-(8-(cyclopentylamino)imidazo[1,2-b]pyridazin-6-yl)pyrimidine-2,4(1H,3H)-dione

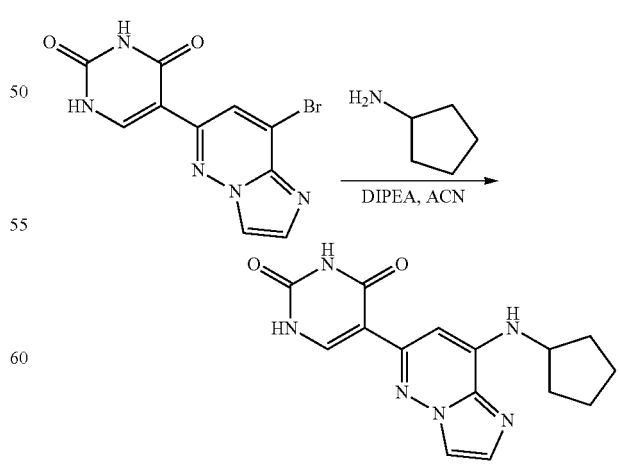

5-(8-(cyclopentylamino)imidazo[1,2-b]pyridazin-6-yl) pyrimidine-2,4(1H,3H)-dione was prepared as follows: To a solution of 5-(8-bromoimidazo[1,2-b]pyridazin-6-yl)pyrimidine-2,4(1H,3H)-dione (50 mg, 0.162 mmol, 1 equiv) and cyclopentanamine (0.02 mL, 0.179 mmol, 1.1 equiv) in ACN (2.0 mL) was added DIPEA (0.07 mL, 0.389 mmol, 2.4 equiv). The reaction mixture was stirred at 120° C. for 3 days, then at 135° C. overnight. NMP (2.0 mL) was added and the reaction was stirred again at 135° C. overnight prior to purification by RP-HPLC (10-90% MeCN/H$_2$O with TFA, Gemini-NX column) to afford the title compound as the TFA salt. ES/MS m/z: 313.1 [M+H]. $^1$H NMR (400 MHz, DMSO-d6) δ 11.51-11.43 (m, 2H), 8.19 (d, J=1.6 Hz, 1H), 8.00 (d, J=6.1 Hz, 1H), 7.84 (s, 1H), 7.33 (d, J=6.6 Hz, 1H), 7.02 (s, 1H), 4.05-3.94 (m, 1H), 2.10-1.98 (m, 2H), 1.78-1.58 (m, 6H). $^{19}$F NMR (376 MHz, DMSO-d6) δ −74.80.

Example 227. 5-(8-((3,3-difluorocyclopentyl)amino)imidazo[1,2-b]pyridazin-6-yl)pyrimidine-2,4(1H,3H)-dione

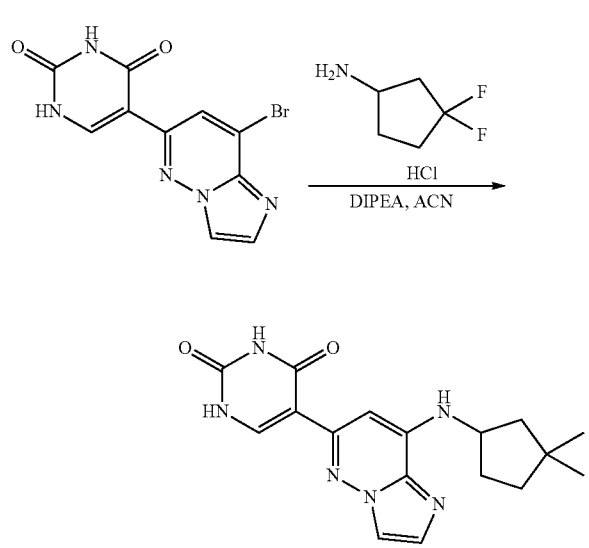 [SMILES: O=c1[nH]cc(-c2cc(Br)c3nccn3n2)c(=O)[nH]1 ; NC1CCC(F)(F)C1 ; Cl ; CC1(C)CCC(Nc2cc(-c3c[nH]c(=O)[nH]c3=O)nn3ccnc23)C1]

5-(8-((3,3-difluorocyclopentyl)amino)imidazo[1,2-b]pyridazin-6-yl)pyrimidine-2,4(1H,3H)-dione was prepared as follows: To a solution of 5-(8-bromoimidazo[1,2-b]pyridazin-6-yl)pyrimidine-2,4(1H,3H)-dione (50 mg, 0.162 mmol, 1 equiv) and 3,3-difluorocyclopentan-1-amine hydrochloride (28 mg, 0.179 mmol, 1.1 equiv) in ACN (2.0 mL) was added DIPEA (0.07 mL, 0.389 mmol, 2.4 equiv). The reaction mixture was stirred at 120° C. for 3 days, then at 135° C. overnight. NMP (2.0 mL) was added and the reaction was stirred again at 135° C. overnight. Additional 3,3-difluorocyclopentan-1-amine hydrochloride (28 mg, 0.179 mmol, 1.1 equiv) and DIPEA (0.07 mL, 0.389 mmol, 2.4 equiv) were added and the reaction was stirred at 150° C. overnight prior to purification by RP-HPLC (10-90% MeCN/H$_2$O with TFA, Gemini-NX column) to afford the title compound as the TFA salt. ES/MS m/z: 349.1 [M+H]. $^1$H NMR (400 MHz, DMSO-d6) δ 11.50-11.38 (m, 2H), 8.14 (s, 1H), 7.97 (d, J=5.8 Hz, 1H), 7.74 (s, 1H), 7.59 (d, J=7.0 Hz, 1H), 6.90 (s, 1H), 4.30-4.23 (m, 1H), 2.73-2.59 (m, 1H), 2.37-2.09 (m, 4H), 2.00-1.85 (m, 1H). $^{19}$F NMR (376 MHz, DMSO-d6) δ −74.99, −88.82.

Example 228. 5-(8-(6,6-dimethyl-3-azabicyclo[3.1.0]hexan-3-yl)imidazo[1,2-b]pyridazin-6-yl)pyrimidine-2,4(1H,3H)-dione

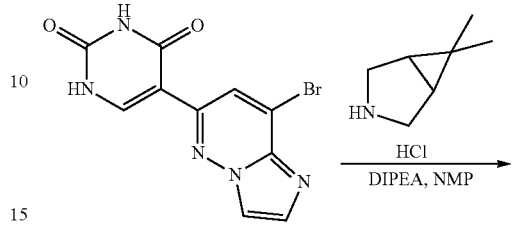

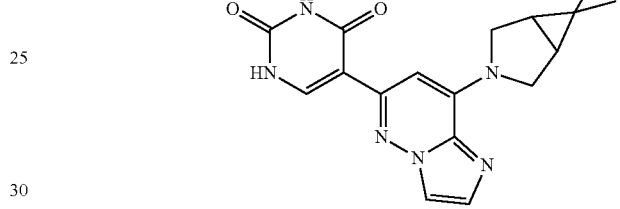

5-(8-(6,6-dimethyl-3-azabicyclo[3.1.0]hexan-3-yl)imidazo[1,2-b]pyridazin-6-yl)pyrimidine-2,4(1H,3H)-dione was prepared as follows: To a solution of 5-(8-bromoimidazo[1,2-b]pyridazin-6-yl)pyrimidine-2,4(1H,3H)-dione (50 mg, 0.162 mmol, 1 equiv) and 6,6-dimethyl-3-azabicyclo[3.1.0]hexane hydrochloride (56 mg, 0.379 mmol, 2.34 equiv) in NMP (2.0 mL) was added DIPEA (0.07 mL, 0.389 mmol, 2.4 equiv). The solution was heated to 130° C. and stirred overnight. The crude material was purified by RP-HPLC (10-90% MeCN/H$_2$O with TFA, Gemini-NX column) to afford the title compound as the TFA salt. ES/MS m/z: 339.1 [M+H]. $^1$H NMR (400 MHz, DMSO-d6) δ 11.40-11.32 (m, 2H), 8.03 (d, J=1.2 Hz, 1H), 7.93 (d, J=6.1 Hz, 1H), 7.57 (d, J=1.2 Hz, 1H), 6.54 (s, 1H), 4.91-3.47 (m, 4H), 1.63-1.59 (m, 2H), 1.07 (s, 3H), 0.86 (s, 3H). $^{19}$F NMR (376 MHz, DMSO-d6) δ −75.23.

Example 229. (S)-5-(8-(3-(difluoromethyl)pyrrolidin-1-yl)imidazo[1,2-b]pyridazin-6-yl)pyrimidine-2,4(1H,3H)-dione

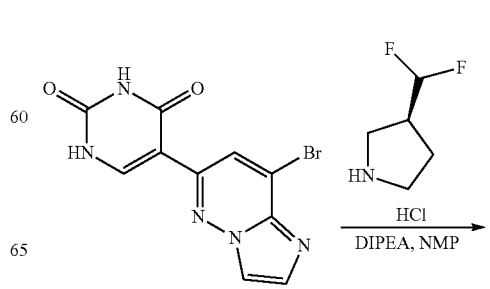

-continued

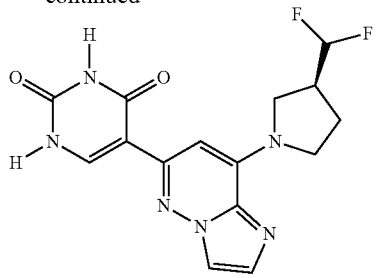

(S)-5-(8-(3-(difluoromethyl)pyrrolidin-1-yl)imidazo[1,2-b]pyridazin-6-yl)pyrimidine-2,4(1H,3H)-dione was prepared as follows: A solution of 5-(8-bromoimidazo[1,2-b]pyridazin-6-yl)pyrimidine-2,4(1H,3H)-dione (50 mg, 0.162 mmol, 1 equiv), (S)-3-(difluoromethyl)pyrrolidine hydrochloride (28 mg, 0.179 mmol, 1.1 equiv) and DIPEA (0.07 mL, 0.389 mmol, 2.4 equiv) in NMP (2.0 mL) was heated to 130° C. and stirred overnight. The crude material was purified by RP-HPLC (10-90% MeCN/H$_2$O with TFA, Gemini-NX column) twice to afford the title compound as the TFA salt. ES/MS m/z: 349.1 [M+H]. $^1$H NMR (400 MHz, Methanol-d4) δ 8.15 (s, 1H), 8.06 (d, J=1.7 Hz, 1H), 7.72 (d, J=1.7 Hz, 1H), 7.00 (s, 1H), 6.22-5.87 (m, 1H), 4.14-3.85 (m, 4H), 3.02-2.88 (m, 1H), 2.36-2.26 (m, 1H), 2.24-2.11 (m, 1H). $^{19}$F NMR (376 MHz, Methanol-d4) δ −77.70, −121.85—124.29 (m).

Example 230. (R)-5-(8-(3-(difluoromethyl)pyrrolidin-1-yl)imidazo[1,2-b]pyridazin-6-yl)pyrimidine-2,4(1H,3H)-dione

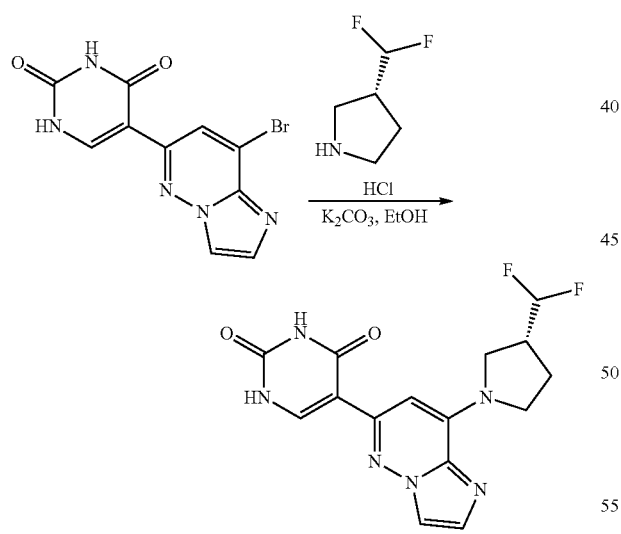

(R)-5-(8-(3-(difluoromethyl)pyrrolidin-1-yl)imidazo[1,2-b]pyridazin-6-yl)pyrimidine-2,4(1H,3H)-dione was prepared as follows: A solution of 5-(8-bromoimidazo[1,2-b]pyridazin-6-yl)pyrimidine-2,4(1H,3H)-dione (50 mg, 0.162 mmol, 1 equiv), (R)-3-(difluoromethyl)pyrrolidine hydrochloride (28 mg, 0.179 mmol, 1.1 equiv) and potassium carbonate (65 mg, 0.470 mmol, 2.9 equiv) in EtOH (2.0 mL) was heated to 85° C. and stirred for 3 days. The reaction mixture was then heated to 120° C. and stirred overnight. The solution was diluted with water and extracted with EtOAc (5×). The organic layers were combined, dried over Na$_2$SO$_4$, filtered and concentrated in vacuo prior to purification by RP-HPLC (10-90% MeCN/H$_2$O with TFA, Gemini-NX column) to afford the title compound as the TFA salt. ES/MS m/z: 349.1 [M+H]. $^1$H NMR (400 MHz, DMSO-d6) δ 11.42-11.33 (m, 2H), 8.03 (d, J=1.2 Hz, 1H), 7.94 (d, J=6.1 Hz, 1H), 7.57 (d, J=1.2 Hz, 1H), 6.61 (s, 1H), 6.38-6.05 (m, 1H), 4.19-3.54 (m, 4H), 2.99-2.82 (m, 1H), 2.24-2.12 (m, 1H), 2.09-1.96 (m, 1H). $^{19}$F NMR (376 MHz, DMSO-d6) δ −75.14, −120.45—120.63 (m).

Example 231. 4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)benzonitrile

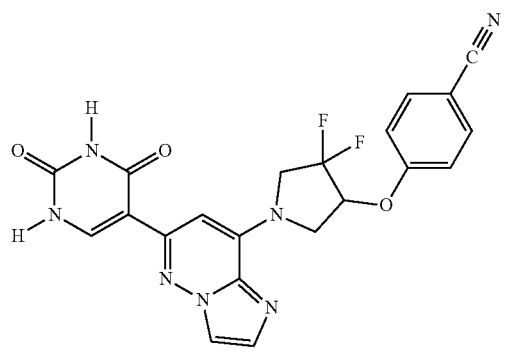 [SMILES: N#Cc1ccc(OC2CN(c3cc(-c4c[nH]c(=O)[nH]c4=O)nn4ccnc34)CC2(F)F)cc1]

4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)benzonitrile was prepared as follows: To a solution of 4-((1-(6-(2,4-dimethoxypyrimidin-5-yl)imidazo[1,2-b]pyridazin-8-yl)-4,4-difluoropyrrolidin-3-yl)oxy)benzonitrile (32 mg, 0.066 mmol, 1 equiv) in MeOH (0.5 mL) was added 1 N HCl (0.5 mL). The solution was heated to 70° C. and stirred. Upon completion, the reaction mixture was purified by RP-HPLC (10-90% MeCN/H$_2$O with TFA, Gemini-NX column) to afford the title compound as the TFA salt. ES/MS m/z: 452.0 [M+H]. $^1$H NMR (400 MHz, DMSO-d6) δ 11.45-11.33 (m, 2H), 8.08 (d, J=1.2 Hz, 1H), 7.93 (d, J=6.1 Hz, 1H), 7.88-7.82 (m, 2H), 7.57 (d, J=1.2 Hz, 1H), 7.33-7.28 (m, 2H), 6.63 (s, 1H), 5.68-5.56 (m, 1H), 4.71-4.06 (m, 4H). $^{19}$F NMR (376 MHz, DMSO-d6) δ −75.16, −106.94 (d, J=242.9 Hz), −120.26 (d, J=238.8 Hz).

Example 232. 5-(8-(4-(5-(difluoromethyl)pyridin-2-yl)oxy)-3,3-difluoropyrrolidin-1-yl)imidazo[1,2-b]pyridazin-6-yl)pyrimidine-2,4(1H,3H)-dione

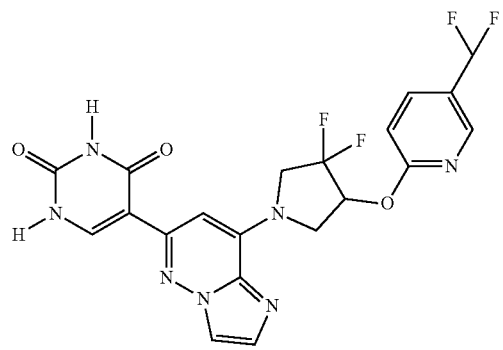 [SMILES: O=c1[nH]cc(-c2cc(N3CC(Oc4ccc(C(F)F)cn4)C(F)(F)C3)c3nccn3n2)c(=O)[nH]1]

5-(8-(4-((5-(difluoromethyl)pyridin-2-yl)oxy)-3,3-difluoropyrrolidin-1-yl)imidazo[1,2-b]pyridazin-6-yl)pyrimidine-2,4(1H,3H)-dione was prepared as follows: To a solution of 8-(4-((5-(difluoromethyl)pyridin-2-yl)oxy)-3,3-difluoropyrrolidin-1-yl)-6-(2,4-dimethoxypyrimidin-5-yl)imidazo[1,2-b]pyridazine (6.9 mg, 0.014 mmol, 1 equiv) in MeOH (0.5 mL) was added 1 N HCl (0.5 mL). The solution was heated to 70° C. and stirred. Upon completion, the reaction mixture was purified by RP-HPLC (10-90% MeCN/H₂O with TFA, Gemini-NX column) to afford the title compound as the TFA salt. ES/MS m/z: 478.0 [M+H]. ¹H NMR (400 MHz, Methanol-d4) δ 8.40-8.37 (m, 1H), 8.12 (s, 1H), 8.02 (d, J=1.5 Hz, 1H), 7.93 (dd, J=8.7, 2.4 Hz, 1H), 7.66 (d, J=1.5 Hz, 1H), 7.02 (d, J=8.6 Hz, 1H), 6.99-6.69 (m, 2H), 6.04-5.97 (m, 1H), 4.62-4.39 (m, 3H), 4.27-4.19 (m, 1H). ¹⁹F NMR (376 MHz, Methanol-d4) δ −77.92, −109.78 (d, J=242.6 Hz), −112.51, −123.83 (d, J=242.6 Hz).

Example 233. 1-(6-(2,4-dioxo-1,2,3,4-tetrahydropyrimidin-5-yl)imidazo[1,2-b]pyridazin-8-yl)-4,4-difluoropyrrolidin-3-yl (2-fluorophenyl)carbamate

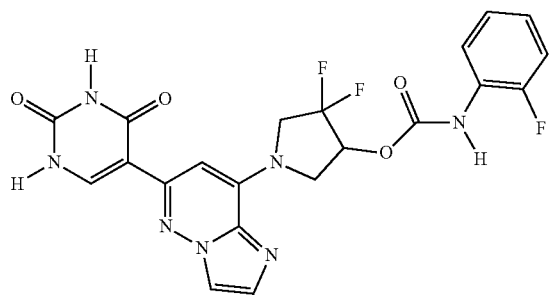 [SMILES: O=C(Nc1ccccc1F)OC1CN(c2cc(-c3c[nH]c(=O)[nH]c3=O)nn3ccnc23)CC1(F)F]

1-(6-(2,4-dioxo-1,2,3,4-tetrahydropyrimidin-5-yl)imidazo[1,2-b]pyridazin-8-yl)-4,4-difluoropyrrolidin-3-yl (2-fluorophenyl)carbamate was prepared as follows: To a solution of 1-(6-(2,4-dimethoxypyrimidin-5-yl)imidazo[1,2-b]pyridazin-8-yl)-4,4-difluoropyrrolidin-3-yl (2-fluorophenyl)carbamate (66 mg, 0.128 mmol, 1 equiv) in MeOH (2.0 mL) was added 1 N HCl (2.0 mL). The solution was heated to 70° C. and stirred. Upon completion, the reaction mixture was purified by RP-HPLC (10-90% MeCN/H₂O with TFA, Gemini-NX column) to afford the title compound as the TFA salt. ES/MS m/z: 488.0 [M+H]. ¹H NMR (400 MHz, DMSO-d6) δ 11.46-11.35 (m, 2H), 9.79 (s, 1H), 8.11-8.07 (m, 1H), 7.97-7.91 (m, 1H), 7.67-7.56 (m, 2H), 7.29-7.13 (m, 3H), 6.67-6.62 (m, 1H), 5.62-5.53 (m, 1H), 4.60-4.14 (m, 4H). ¹⁹F NMR (376 MHz, DMSO-d6) δ −75.32−−75.49 (m), −107.37−−108.88 (m), −120.37 (d, J=239.0 Hz), −124.64.

Example 234. 3-((6-(2,4-dioxo-1,2,3,4-tetrahydropyrimidin-5-yl)imidazo[1,2-b]pyridazin-8-yl)oxy)-2,2-difluoropropyl (2-fluorophenyl)carbamate

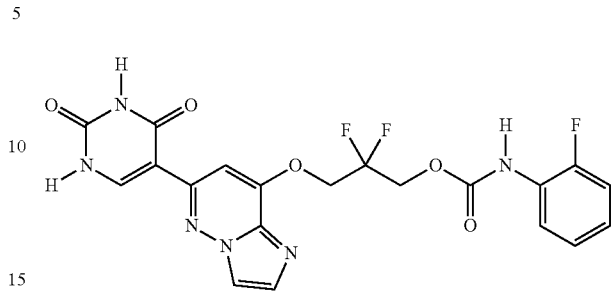

3-((6-(2,4-dioxo-1,2,3,4-tetrahydropyrimidin-5-yl)imidazo[1,2-b]pyridazin-8-yl)oxy)-2,2-difluoropropyl (2-fluorophenyl)carbamate was prepared as follows: To a solution of 3-((6-(2,4-di-tert-butoxypyrimidin-5-yl)imidazo[1,2-b]pyridazin-8-yl)oxy)-2,2-difluoropropyl (2-fluorophenyl)carbamate (16 mg, 0.028 mmol, 1 equiv) in ACN (2.0 mL) was added TFA (0.04 mL, 0.550 mmol, 20 equiv). The solution was stirred at room temperature for 15 min prior to purification by RP-HPLC (10-90% MeCN/H₂O with TFA, Gemini-NX column) to afford the title compound as the TFA salt. ES/MS m/z: 477.0 [M+H]. ¹H NMR (400 MHz, DMSO-d6) δ 11.58-11.52 (m, 2H), 9.70 (s, 1H), 8.29 (s, 1H), 8.03 (d, J=6.4 Hz, 1H), 7.75 (s, 1H), 7.64-7.54 (m, 1H), 7.42 (s, 1H), 7.27-7.13 (m, 3H), 4.90 (t, J=12.8 Hz, 2H), 4.66 (t, J=13.8 Hz, 2H).

Example 235. (S)-1-(6-(2,4-dioxo-1,2,3,4-tetrahydropyrimidin-5-yl)imidazo[1,2-b]pyridazin-8-yl)-4,4-difluoropyrrolidin-3-yl (2,4-difluorophenyl)carbamate

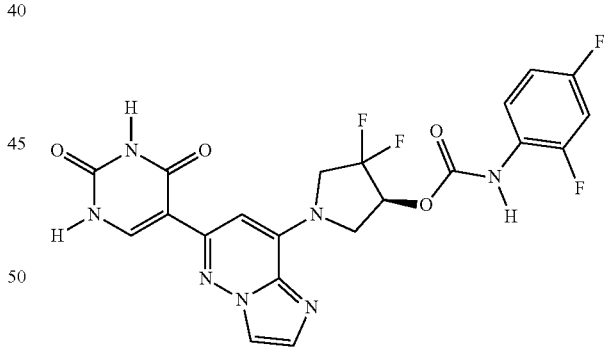

(S)-1-(6-(2,4-dioxo-1,2,3,4-tetrahydropyrimidin-5-yl)imidazo[1,2-b]pyridazin-8-yl)-4,4-difluoropyrrolidin-3-yl (2,4-difluorophenyl)carbamate was prepared as follows: To a solution of (S)-1-(6-(2,4-di-tert-butoxypyrimidin-5-yl)imidazo[1,2-b]pyridazin-8-yl)-4,4-difluoropyrrolidin-3-yl (2,4-difluorophenyl)carbamate (23 mg, 0.037 mmol, 1 equiv) in ACN (1.0 mL) was added TFA (0.1 mL, 0.0015 mmol, 40 equiv). The solution was stirred at room temperature. Upon completion, the crude material was purified by RP-HPLC (10-90% MeCN/H₂O with TFA, Gemini-NX column) to afford the title compound as the TFA salt. ES/MS m/z: 506.0 [M+H]. ¹H NMR (400 MHz, DMSO-d6) δ 11.45-11.36 (m, 2H), 9.79 (s, 1H), 8.09 (s, 1H), 7.94 (d, J=6.1 Hz, 1H), 7.66-7.54 (m, 2H), 7.31 (ddd, J=11.2, 9.0, 2.9 Hz, 1H), 7.12-7.04 (m, 1H), 6.63 (s, 1H), 5.61-5.51 (m, 1H), 4.63-3.60 (m, 4H).

Example 236. (S)-1-(6-(2,4-dioxo-1,2,3,4-tetrahydropyrimidin-5-yl)imidazo[1,2-b]pyridazin-8-yl)-4,4-difluoropyrrolidin-3-yl (2-fluoro-4-methylphenyl)carbamate

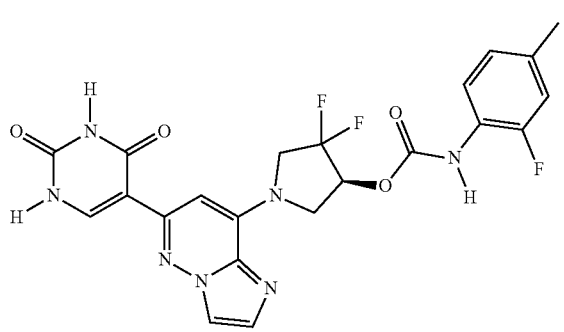 [SMILES: Cc1ccc(NC(=O)O[C@H]2CN(c3cc(-c4c[nH]c(=O)[nH]c4=O)nn4ccnc34)CC2(F)F)c(F)c1]

(S)-1-(6-(2,4-dioxo-1,2,3,4-tetrahydropyrimidin-5-yl)imidazo[1,2-b]pyridazin-8-yl)-4,4-difluoropyrrolidin-3-yl (2-fluoro-4-methylphenyl)carbamate as the TFA salt was prepared in the manner described for Example 235, but replacing (S)-1-(6-(2,4-di-tert-butoxypyrimidin-5-yl)imidazo[1,2-b]pyridazin-8-yl)-4,4-difluoropyrrolidin-3-yl (2,4-difluorophenyl)carbamate with (S)-1-(6-(2,4-di-tert-butoxypyrimidin-5-yl)imidazo[1,2-b]pyridazin-8-yl)-4,4-difluoropyrrolidin-3-yl (2-fluoro-4-methylphenyl)carbamate. ES/MS m/z: 502.0 [M+H]. $^1$H NMR (400 MHz, DMSO-d6) δ 11.44-11.36 (m, 2H), 9.65 (s, 1H), 8.09 (d, J=1.2 Hz, 1H), 7.94 (d, J=6.1 Hz, 1H), 7.59 (d, J=1.2 Hz, 1H), 7.50-7.39 (m, 1H), 7.10-7.03 (m, 1H), 6.98 (d, J=7.6 Hz, 1H), 6.63 (s, 1H), 5.60-5.51 (m, 1H), 4.60-3.51 (m, 4H), 2.28 (s, 3H).

Example 237. (S)-4-(1-(6-(2,4-dioxo-1,2,3,4-tetrahydropyrimidin-5-yl)imidazo[1,2-b]pyridazin-8-yl)-4,4-difluoropyrrolidin-3-yl)oxy)benzonitrile

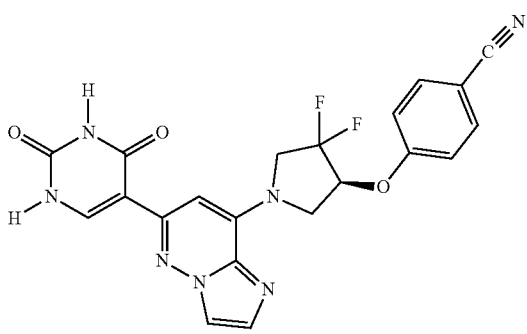 [SMILES: N#Cc1ccc(O[C@H]2CN(c3cc(-c4c[nH]c(=O)[nH]c4=O)nn4ccnc34)CC2(F)F)cc1]

(S)-4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)benzonitrile as the TFA salt was separated from Example 231 by SFC AD-H column (co-solvent: 40% EtOH). ES/MS m/z: 452.0 [M+H]. $^1$H NMR (400 MHz, DMSO-d6) δ 11.43-11.35 (m, 2H), 8.07 (d, J=1.2 Hz, 1H), 7.93 (d, J=5.2 Hz, 1H), 7.88-7.82 (m, 2H), 7.57 (d, J=1.2 Hz, 1H), 7.33-7.27 (m, 2H), 6.62 (s, 1H), 5.67-5.56 (m, 1H), 4.63-4.13 (m, 4H). $^{19}$F NMR (376 MHz, DMSO-d6) δ -73.96, -106.93 (d, J=240.7 Hz), -120.26 (d, J=238.7 Hz).

Example 238. 3-((6-(2,4-dioxo-1,2,3,4-tetrahydropyrimidin-5-yl)imidazo[1,2-b]pyridazin-8-yl)oxy)-2,2-difluoropropyl (2,4-difluorophenyl)carbamate

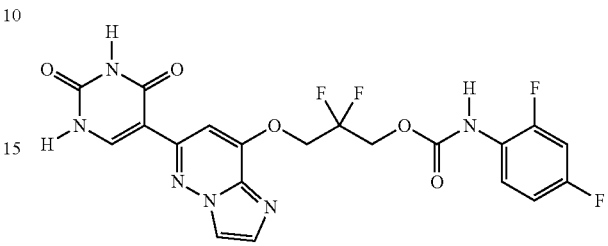

3-((6-(2,4-dioxo-1,2,3,4-tetrahydropyrimidin-5-yl)imidazo[1,2-b]pyridazin-8-yl)oxy)-2,2-difluoropropyl (2,4-difluorophenyl)carbamate as the TFA salt was prepared in the manner described for Example 234, but replacing 3-((6-(2,4-di-tert-butoxypyrimidin-5-yl)imidazo[1,2-b]pyridazin-8-yl)oxy)-2,2-difluoropropyl (2-fluorophenyl)carbamate with 3-((6-(2,4-di-tert-butoxypyrimidin-5-yl)imidazo[1,2-b]pyridazin-8-yl)oxy)-2,2-difluoropropyl (2,4-difluorophenyl)carbamate. ES/MS m/z: 495.0 [M+H]. $^1$H NMR (400 MHz, DMSO-d6) δ11.58-11.46 (m, 2H), 9.71 (s, 1H), 8.23 (s, 1H), 8.02 (d, J=5.8 Hz, 1H), 7.67 (s, 1H), 7.63 7.51 (m, 1H), 7.39-7.24 (m, 2H), 7.14-7.02 (m, 1H), 4.88 (t, J=13.1 Hz, 2H), 4.64 (t, J=14.0 Hz, 2H). $^{19}$F NMR (376 MHz, DMSO-d6) δ -74.04, -113.53, -115.01, -119.65.

Example 239. (S)-1-(6-(2,4-dioxo-1,2,3,4-tetrahydropyrimidin-5-yl)imidazo[1,2-b]pyridazin-8-yl)-4,4-difluoropyrrolidin-3-yl (2,4,6-trifluorophenyl)carbamate

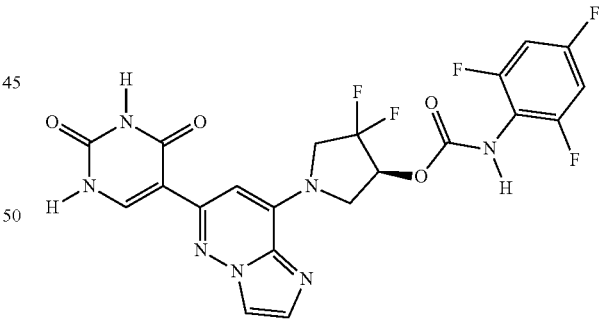

(S)-1-(6-(2,4-dioxo-1,2,3,4-tetrahydropyrimidin-5-yl)imidazo[1,2-b]pyridazin-8-yl)-4,4-difluoropyrrolidin-3-yl (2,4,6-trifluorophenyl)carbamate as the TFA salt was prepared in the manner described for Example 235, but replacing (S)-1-(6-(2,4-di-tert-butoxypyrimidin-5-yl)imidazo[1,2-b]pyridazin-8-yl)-4,4-difluoropyrrolidin-3-yl (2,4-difluorophenyl)carbamate with (S)-1-(6-(2,4-di-tert-butoxypyrimidin-5-yl)imidazo[1,2-b]pyridazin-8-yl)-4,4-difluoropyrrolidin-3-yl (2,4,6-trifluorophenyl)carbamate. ES/MS m/z: 524.0 [M+H]. $^1$H NMR (400 MHz, DMSO-d6) δ 11.46-11.35 (m, 2H), 9.69 (s, 1H), 8.09 (d, J=1.2 Hz, 1H), 7.94 (d, J=6.1 Hz, 1H), 7.59 (d, J=1.2 Hz, 1H), 7.36-7.24 (m, 2H), 6.63 (s, 1H), 5.61-5.50 (m, 1H), 4.59-4.08 (m, 4H). ¹⁹F NMR (376 MHz, DMSO-d6) δ −75.35, −108.09 (d, J=247.5 Hz), −109.72, −116.20, −119.87 (d, J=241.9 Hz).

Example 240. (R)-5-(8-(3-(4-fluorophenoxy)pyrrolidin-1-yl)imidazo[1,2-b]pyridazin-6-yl)pyrimidine-2,4(1H,3H)-dione

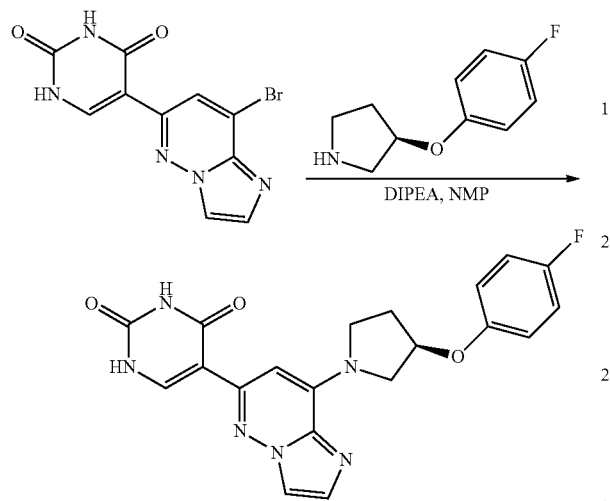

(R)-5-(8-(3-(4-fluorophenoxy)pyrrolidin-1-yl)imidazo[1,2-b]pyridazin-6-yl)pyrimidine-2,4(1H,3H)-dione was prepared as follows: A solution of 5-(8-bromoimidazo[1,2-b]pyridazin-6-yl)pyrimidine-2,4(1H,3H)-dione (70 mg, 0.227 mmol, 1 equiv), (R)-3-(4-fluorophenoxy)pyrrolidine (45 mg, 0.250 mmol, 1.1 equiv) and DIPEA (0.08 mL, 0.454 mmol, 2 equiv) in NMP (2.0 mL) was stirred at 110° C. for 6 h. The crude material was purified by RP-HPLC (10-90% MeCN/H₂O with TFA, Gemini-NX column) to afford the title compound as the TFA salt. ES/MS m/z: 409.1 [M+H]. ¹H NMR (400 MHz, DMSO-d6) δ 11.41-11.31 (m, 2H), 8.03 (s, 1H), 7.93 (d, J=6.0 Hz, 1H), 7.55 (s, 1H), 7.18-7.10 (m, 2H), 7.05-6.98 (m, 2H), 6.60 (s, 1H), 5.22-5.14 (m, 1H), 4.26-3.64 (m, 4H), 2.36-2.19 (m, 2H). ¹⁹F NMR (376 MHz, DMSO-d6) δ −75.21, −123.95.

Example 241. (S)-1-(6-(2,4-dioxo-1,2,3,4-tetrahydropyrimidin-5-yl)imidazo[1,2-b]pyridazin-8-yl)-4,4-difluoropyrrolidin-3-yl (2-fluorophenyl)carbamate

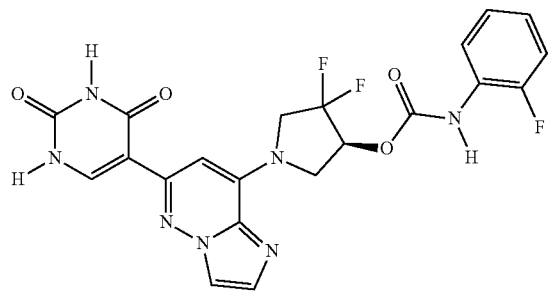 [SMILES: O=C(Nc1ccccc1F)O[C@H]1CN(c2cc(-c3c[nH]c(=O)[nH]c3=O)nn3ccnc23)CC1(F)F]

(S)-1-(6-(2,4-dioxo-1,2,3,4-tetrahydropyrimidin-5-yl)imidazo[1,2-b]pyridazin-8-yl)-4,4-difluoropyrrolidin-3-yl (2-fluorophenyl)carbamate as the TFA salt was separated from Example 233 by SFC CCO-F2 column (co-solvent: 45% EtOH) and was further purified by RP-HPLC (10-90% MeCN/H₂O with TFA, Gemini-NX column). ES/MS m/z: 488.0 [M+H]. ¹H NMR (400 MHz, DMSO-d6) δ 11.46-11.36 (m, 2H), 9.79 (s, 1H), 8.09 (d, J=1.2 Hz, 1H), 7.94 (d, J=6.1 Hz, 1H), 7.69-7.55 (m, 2H), 7.30-7.13 (m, 3H), 6.64 (s, 1H), 5.61-5.53 (m, 1H), 4.58-4.15 (m, 4H). ¹⁹F NMR (376 MHz, DMSO-d6) δ −75.21, −107.21−−109.15 (m), −120.37 (d, J=239.0 Hz), −124.63.

Example 242. 5-(8-(3-phenoxypyrrolidin-1-yl)imidazo[1,2-b]pyridazin-6-yl)pyrimidine-2,4(1H,3H)-dione

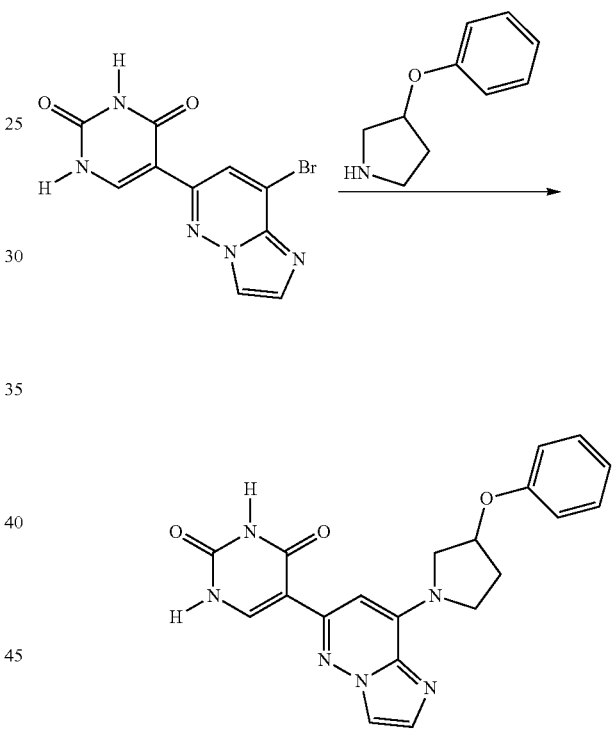

Step 1: A solution of 5-(8-bromoimidazo[1,2-b]pyridazin-6-yl)-1H-pyrimidine-2,4-dione (23 mg, 0.075 mmol, 1 equiv), 3-phenoxypyrrolidine hydrochloride (45 mg, 0.23 mmol, 3 equiv), and N,N-diisopropylethylamine (0.013 mL, 0.075 mmol, 1 equiv) in N-methyl-2-pyrrolidone (0.5 mL) was heated to 65° C. After 1h, the reaction mixture was allowed to cool to rt and was purified by prep-HPLC (10-90% MeCN/H₂O with TFA modifier) to afford 5-(8-(3-phenoxypyrrolidin-1-yl)imidazo[1,2-b]pyridazin-6-yl)pyrimidine-2,4(1H,3H)-dione as an off-white solid (TFA Salt). ES/MS m/z: 391.1 [M+H]. ¹H NMR (400 MHz, DMSO-d6) δ 11.47-11.23 (m, 2H), 8.03 (s, 1H), 7.93 (d, J=6.1 Hz, 1H), 7.55 (s, 1H), 7.39-7.23 (m, 2H), 7.05-6.89 (m, 3H), 6.60 (s, 1H), 5.23 (s, 1H), 4.28-3.70 (m, 4H), 2.39-2.18 (m, 2H). ¹⁹F NMR (400 MHz, DMSO-d6) δ −75.10.

Example 243. 5-(8-(3-hydroxy-3-methylpyrrolidin-1-yl)imidazo[1,2-b]pyridazin-6-yl)pyrimidine-2,4(1H,3H)-dione BJ3634

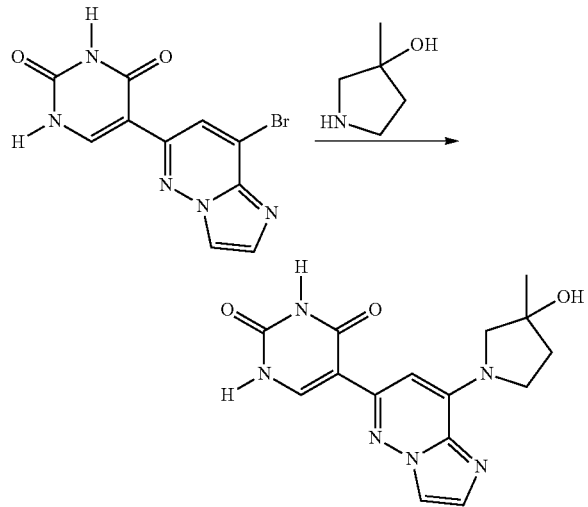

Step 1: A solution of 5-(8-bromoimidazo[1,2-b]pyridazin-6-yl)-1H-pyrimidine-2,4-dione (58 mg, 0.19 mmol, 1 equiv), 3-hydroxy-3-methylpyrrolidine hydrochloride (21 mg, 0.21 mmol, 1.1 equiv), and N,N-diisopropylethylamine (0.033 mL, 0.19 mmol, 1 equiv) in N-methyl-2-pyrrolidone (0.5 mL) was heated to 100° C. After 1 h, the reaction mixture was allowed to cool to rt and was purified by prep-HPLC (10-90% MeCN/H$_2$O with TFA modifier) to afford 5-(8-(3-hydroxy-3-methylpyrrolidin-1-yl)imidazo[1,2-b]pyridazin-6-yl)pyrimidine-2,4(1H,3H)-dione as an off-white solid (TFA Salt). ES/MS m/z: 329.1 [M+H]. $^1$H NMR (400 MHz, DMSO-d6) δ 11.40-11.27 (m, 2H), 8.01 (s, 1H), 7.93 (d, J=6.1 Hz, 1H), 7.54 (s, 1H), 6.54 (s, 1H), 4.14-3.46 (m, 4H), 2.03-1.86 (m, 2H), 1.39 (s, 3H). $^{19}$F NMR (400 MHz, DMSO-d6) δ −74.89.

Example 244. 5-(7-(3-fluoro-3-(trifluoromethyl)azetidin-1-yl)pyrazolo[1,5-a]pyrimidin-5-yl)pyrimidine-2,4(1H,3H)-dione BJ3631

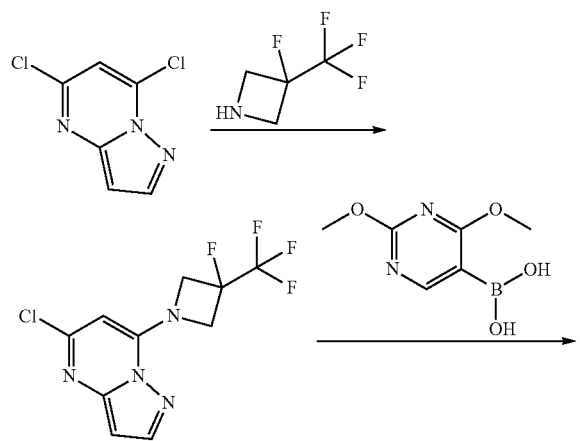

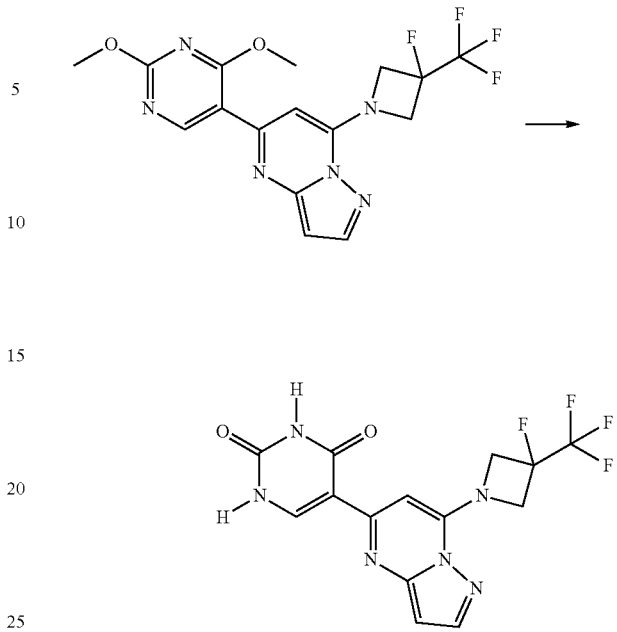

Step 1: A solution of 5,7-dichloropyrazolo[1,5-a]pyrimidine (100 mg, 0.53 mmol, 1 equiv), 3-fluoro-3-(trifluoromethyl)azetidine;hydrochloride (105 mg, 0.59 mmol, 1.1 equiv), DIPEA (0.095 mL, 0.53 mmol, 1 equiv), and MeCN (1 mL) was heated to 85° C. After 1 h, the reaction mixture was filtered, concentrated and directly purified by SiO$_2$ chromatography (0-20% MeOH/DCM), affording 5-chloro-7-(3-fluoro-3-(trifluoromethyl)azetidin-1-yl)pyrazolo[1,5-a]pyrimidine. ES/MS m/z: 295.1 [M+H].

Step 2: A solution of 5-chloro-7-(3-fluoro-3-(trifluoromethyl)azetidin-1-yl)pyrazolo[1,5-a]pyrimidine (15 mg, 0.05 mmol, 1 equiv), (2,4-dimethoxypyrimidin-5-yl)boronic acid (11 mg, 0.06 mmol, 1.2 equiv), cesium carbonate (50 mg, 0.15 mmol, 3 equiv), and PdCl$_2$(dppf)-CH$_2$Cl$_2$ (4 mg, 0.005 mmol, 0.1 equiv) in 1:4 water/1,4-dioxane (2.5 mL) was heated to 90° C. After 24 hours, the reaction mixture was cooled to room temperature. The layers were separated, and the aqueous layer was extracted with EtOAc (3×200 mL). The combined organic layers were dried over Na$_2$SO$_4$, filtered, and concentrated. Purification was accomplished by SiO$_2$ chromatography (0-100% EtOAc/Hex), affording 5-(2,4-dimethoxypyrimidin-5-yl)-7-(3-fluoro-3-(trifluoromethyl)azetidin-1-yl)pyrazolo[1,5-a]pyrimidine. ES/MS m/z: 399.1 [M+H].

Step 3: A solution of 5-(2,4-dimethoxypyrimidin-5-yl)-7-(3-fluoro-3-(trifluoromethyl)azetidin-1-yl)pyrazolo[1,5-a]pyrimidine (10 mg, 0.025 mmol, 1 equiv) in 1:1 1N HCl:MeOH (0.5 mL) was heated to 80° C. After 6 h, the reaction mixture was allowed to cool to rt and was purified by prep-HPLC (10-90% MeCN/H$_2$O with TFA modifier) to afford 5-(7-(3-fluoro-3-(trifluoromethyl)azetidin-1-yl)pyrazolo[1,5-a]pyrimidin-5-yl)pyrimidine-2,4(1H,3H)-dione as an white solid (TFA Salt). ES/MS m/z: 371.00 [M+H]. $^1$H NMR (400 MHz, DMSO-d6) δ 11.44 (s, 2H), 8.33 (d, J=6.3 Hz, 1H), 8.07 (d, J=2.3 Hz, 1H), 7.04 (s, 1H), 6.53 (s, 1H), 6.40 (d, J=2.3 Hz, 1H), 5.01-4.82 (m, 4H). $^{19}$F NMR (400 MHz, DMSO-d6) δ −73.95, −82.72.

Example 245. N-(1-(5-(2,4-dioxo-1,2,3,4-tetrahydropyrimidin-5-yl)pyrazolo[1,5-a]pyrimidin-7-yl)pyrrolidin-3-yl)acetamide BJ3633

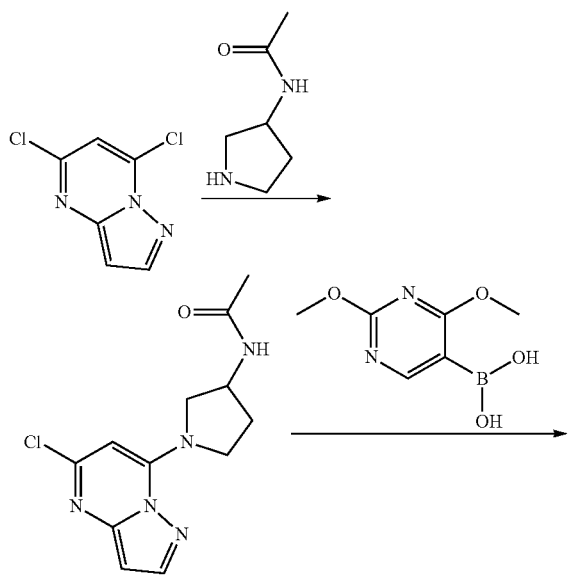

heated to 90° C. After 24 hours, the reaction mixture was cooled to room temperature. The layers were separated, and the aqueous layer was extracted with EtOAc (3×200 mL). The combined organic layers were dried over $Na_2SO_4$, filtered, and concentrated. Purification was accomplished by $SiO_2$ chromatography (0-100% EtOAc/Hex), affording N-(1-(5-(2,4-dimethoxypyrimidin-5-yl)pyrazolo[1,5-a]pyrimidin-7-yl)pyrrolidin-3-yl)acetamide. ES/MS m/z: 384.1 [M+H].

Step 3: A solution of N-(1-(5-(2,4-dimethoxypyrimidin-5-yl)pyrazolo[1,5-a]pyrimidin-7-yl)pyrrolidin-3-yl)acetamide (69 mg, 0.18 mmol, 1 equiv) in 1:1 1N HCl:MeOH (0.5 mL) was heated to 80° C. After 6 h, the reaction mixture was allowed to cool to rt and was purified by prep-HPLC (10-90% $MeCN/H_2O$ with TFA modifier) to afford N-(1-(5-(2,4-dioxo-1,2,3,4-tetrahydropyrimidin-5-yl)pyrazolo[1,5-a]pyrimidin-7-yl)pyrrolidin-3-yl)acetamide as an white solid (TFA Salt). ES/MS m/z: 356.1 [M+H]. $^1$H NMR (400 MHz, DMSO-d6) δ 11.98-11.41 (m, 2H), 8.46 (d, J=6.1 Hz, 1H), 8.23 (d, J=6.4 Hz, 1H), 8.10 (s, 1H), 6.87 (s, 1H), 6.43 (s, 1H), 4.45-3.81 (m, 5H), 2.30-2.12 (m, 1H), 2.05-1.88 (m, 1H)), 1.83 (s, 3H). $^{19}$F NMR (400 MHz, DMSO-d6) δ −74.71.

Example 246. 5-(7-(3-hydroxy-3-methylpyrrolidin-1-yl)pyrazolo[1,5-a]pyrimidin-5-yl)pyrimidine-2,4(1H,3H)-dione BJ3630

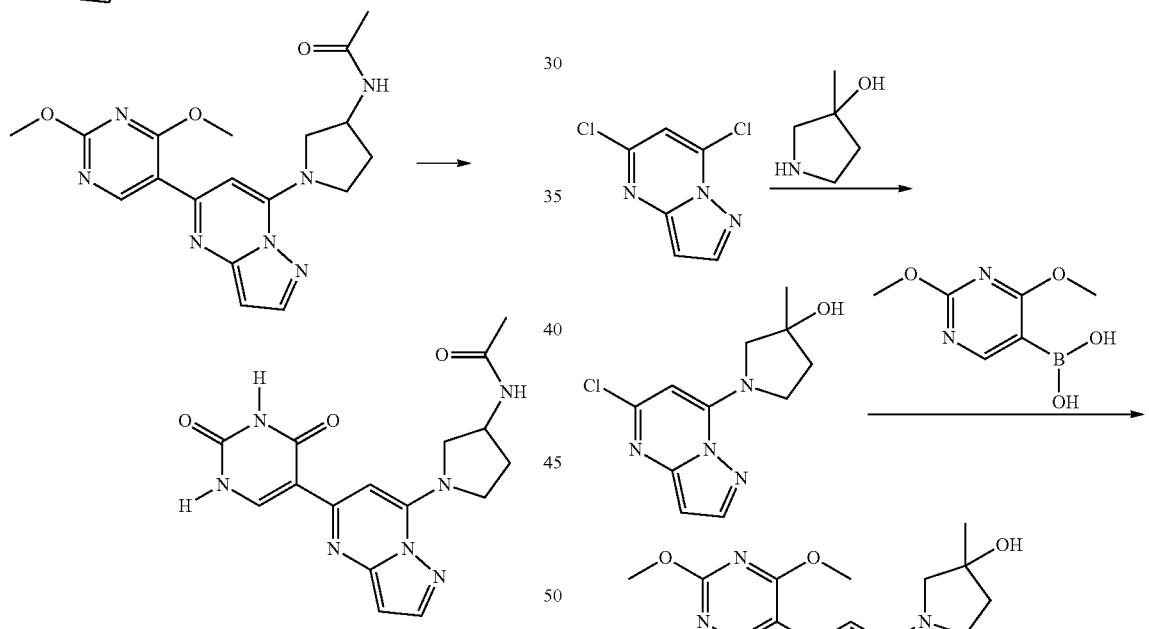

Step 1: A solution of 5,7-dichloropyrazolo[1,5-a]pyrimidine (100 mg, 0.53 mmol, 1 equiv), N-pyrrolidin-3-ylacetamide (75 mg, 0.59 mmol, 1.1 equiv), DIPEA (0.095 mL, 0.53 mmol, 1 equiv), and MeCN (1 mL) was heated to 85° C. After 1 h, the reaction mixture was filtered, concentrated and directly purified by $SiO_2$ chromatography (0-20% MeOH/DCM), affording N-(1-(5-chloropyrazolo[1,5-a]pyrimidin-7-yl)pyrrolidin-3-yl)acetamide. ES/MS m/z: 280.1 [M+H].

Step 2: A solution of N-(1-(5-chloropyrazolo[1,5-a]pyrimidin-7-yl)pyrrolidin-3-yl)acetamide (120 mg, 0.43 mmol, 1 equiv), (2,4-dimethoxypyrimidin-5-yl)boronic acid (95 mg, 0.51 mol, 1.2 equiv), cesium carbonate (500 mg, 1.29 mmol, 3 equiv), and $PdCl_2(dppf)\text{-}CH_2Cl_2$ (35 mg, 0.18 mmol, 0.1 equiv) in 1:4 water/1,4-dioxane (2.5 mL) was Step 1: A solution of 5,7-dichloropyrazolo[1,5-a]pyrimidine (100 mg, 0.53 mmol, 1 equiv), 3-Hydroxy-3-methylpyrrolidine hydrochloride (59 mg, 0.59 mmol, 1.1 equiv), DIPEA (0.095 mL, 0.53 mmol, 1 equiv), and MeCN (1 mL) was heated to 85° C. After 1 h, the reaction mixture was filtered, concentrated and directly purified by SiO$_2$ chromatography (0-20% MeOH/DCM), affording 1-(5-chloropyrazolo[1,5-a]pyrimidin-7-yl)-3-methylpyrrolidin-3-ol. ES/MS m/z: 254.1 [M+H].

Step 2: A solution of 1-(5-chloropyrazolo[1,5-a]pyrimidin-7-yl)-3-methyl-pyrrolidin-3-ol (100 mg, 0.47 mmol, 1 equiv), (2,4-dimethoxypyrimidin-5-yl)boronic acid (105 mg, 0.57 mol, 1.2 equiv), cesium carbonate (464 mg, 1.42 mmol, 3 equiv), and PdCl$_2$(dppf-CH$_2$Cl$_2$ (38 mg, 0.05 mmol, 0.1 equiv) in 1:4 water/1,4-dioxane (2.5 mL) was heated to 90° C. After 24 hours, the reaction mixture was cooled to room temperature. The layers were separated, and the aqueous layer was extracted with EtOAc (3×200 mL). The combined organic layers were dried over Na$_2$SO$_4$, filtered, and concentrated. Purification was accomplished by SiO$_2$ chromatography (0-100% EtOAc/Hex), affording 1-[5-(2,4-dimethoxypyrimidin-5-yl)pyrazolo[1,5-a]pyrimidin-7-yl]-3-methyl-pyrrolidin-3-ol. ES/MS m/z: 357.1 [M+H].

Step 3: A solution of 1-[5-(2,4-dimethoxypyrimidin-5-yl) pyrazolo[1,5-a]pyrimidin-7-yl]-3-methyl-pyrrolidin-3-ol (68 mg, 0.19 mmol, 1 equiv) in 1:1 1N HCl:MeOH (0.5 mL) was heated to 80° C. After 6 h, the reaction mixture was allowed to cool to rt and was purified by prep-HPLC (10-90% MeCN/H$_2$O with TFA modifier) to afford 5-(7-(3-hydroxy-3-methylpyrrolidin-1-yl)pyrazolo[1,5-a]pyrimidin-5-yl)pyrimidine-2,4(1H,3H)-dione as an white solid (TFA Salt). ES/MS m/z: 329.1 [M+H]. $^1$H NMR (400 MHz, DMSO-d6) δ 12.03-11.45 (m, 2H), 8.46 (d, J=5.9 Hz, 1H), 8.10 (s, 1H), 6.81 (s, 1H), 6.44 (s, 1H), 4.62-3.07 (m, 4H), 2.07-1.86 (m, 2H), 1.40 (s, 3H). $^{19}$F NMR (400 MHz, DMSO-d6) 43-74.63.

Example 247. 4-(1-(6-(2,4-dioxo-1,2,3,4-tetrahydropyrimidin-5-yl)imidazo[1,2-b]pyridazin-8-yl)azetidin-3-yl)benzonitrile

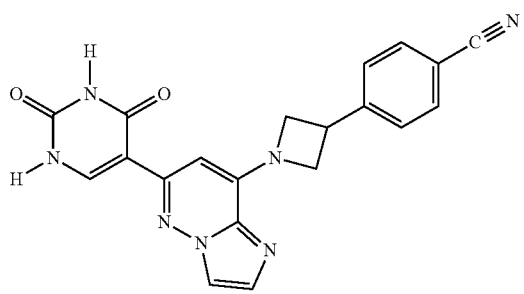 [SMILES: N#Cc1ccc(C2CN(c3cc(-c4c[nH]c(=O)[nH]c4=O)nn4ccnc34)C2)cc1]

5-(8-bromoimidazo[1,2-b]pyridazin-6-yl)pyrimidine-2,4 (1H,3H)-dione (54 mg, 0.18 mmol, 1 equiv), 4-(azetidin-3-yl)benzonitrile (31 mg, 0.19 mmol, 1.1 equiv), and DIPEA (0.05 mL, 0.26 mmol, 1.5 equiv) were combined in NMP (0.5 mL) and stirred at 120° C. for 4 hours. The mixture was cooled, diluted with water, TFA, and MeCN, and purified by RP-HPLC (10-80% MeCN/H$_2$O with TFA modifier) affording 4-(1-(6-(2,4-dioxo-1,2,3,4-tetrahydropyrimidin-5-yl) imidazo[1,2-b]pyridazin-8-yl)azetidin-3-yl)benzonitrile as a TFA salt. ES/MS m/z: 386.1 [M+H]. $^1$H NMR (400 MHz, DMSO-d6) δ 11.51-11.22 (m, 2H), 8.03 (d, J=1.2 Hz, 1H), 7.93 (d, J=6.1 Hz, 1H), 7.89-7.81 (m, 2H), 7.73-7.60 (m, 2H), 7.55 (d, J=1.2 Hz, 1H), 6.50 (s, 1H), 4.81 (s, 2H), 4.37 (s, 2H), 4.25-4.15 (m, 1H).

Example 248. 5-(8-(3-(4-(trifluoromethyl)phenyl) pyrrolidin-1-yl)imidazo[1,2-b]pyridazin-6-yl)pyrimidine-2,4(1H,3H)-dione

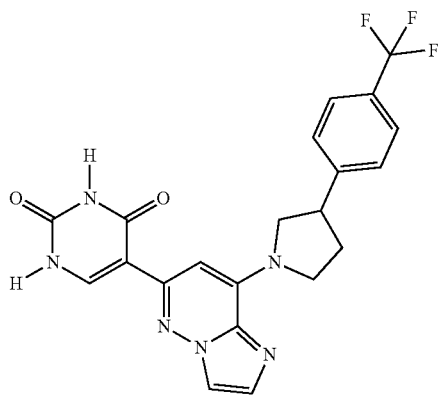 [SMILES: O=c1[nH]cc(-c2cc(N3CCC(c4ccc(C(F)(F)F)cc4)C3)c3nccn3n2)c(=O)[nH]1]

5-(8-(3-(4-(trifluoromethyl)phenyl)pyrrolidin-1-yl)imidazo[1,2-b]pyridazin-6-yl)pyrimidine-2,4(1H,3H)-dione was prepared in the manner described for Example 247, but replacing 4-(azetidin-3-yl)benzonitrile with 3-(4-(trifluoromethyl)phenyl)pyrrolidine. ES/MS m/z: 443.2 [M+H]. $^1$H NMR (400 MHz, DMSO-d6) δ 11.37 (d, J=2.0 Hz, 1H), 11.34 (d, J=6.2 Hz, 1H), 8.01 (d, J=1.1 Hz, 1H), 7.94 (d, J=6.1 Hz, 1H), 7.72 (d, J=8.1 Hz, 2H), 7.61 (d, J=8.1 Hz, 2H), 7.53 (s, 1H), 6.61 (s, 1H), 4.35-3.74 (m, 2H), 3.75-3.40 (m, 3H), 2.43 (s, 1H), 2.17 (p, J=9.4 Hz, 1H).

Example 249. 5-(8-(3-(3-(trifluoromethyl)phenyl) pyrrolidin-1-yl)imidazo[1,2-b]pyridazin-6-yl)pyrimidine-2,4(1H,3H)-dione

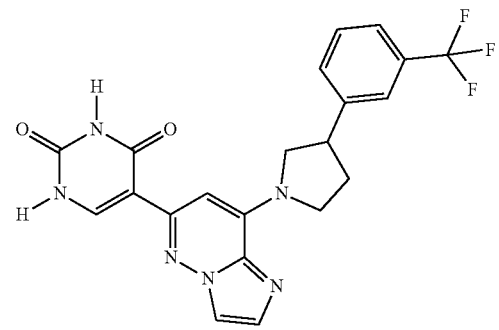 [SMILES: O=c1[nH]cc(-c2cc(N3CCC(c4cccc(C(F)(F)F)c4)C3)c3nccn3n2)c(=O)[nH]1]

5-(8-(3-(3-(trifluoromethyl)phenyl)pyrrolidin-1-yl)imidazo[1,2-b]pyridazin-6-yl)pyrimidine-2,4(1H,3H)-dione was prepared in the manner described for Example 247, but replacing 4-(azetidin-3-yl)benzonitrile with 3-(3-(trifluoromethyl)phenyl)pyrrolidine. ES/MS m/z: 443.2 [M+H]. $^1$H NMR (400 MHz, Methanol-d4) δ 8.09 (s, 1H), 7.95 (d, J=1.4 Hz, 1H), 7.71 (s, 1H), 7.67 (d, J=6.9 Hz, 1H), 7.62-7.52 (m, 3H), 6.81 (s, 1H), 4.51 (s, 1H), 4.15 (s, 1H), 3.95 (s, 2H), 3.83-3.61 (m, 1H), 2.67-2.44 (m, 1H), 2.27 (q, J=10.2 Hz, 1H).

Example 250. 5-(8-(3-(2-(trifluoromethyl)phenyl)pyrrolidin-1-yl)imidazo[1,2-b]pyridazin-6-yl)pyrimidine-2,4(1H,3H)-dione

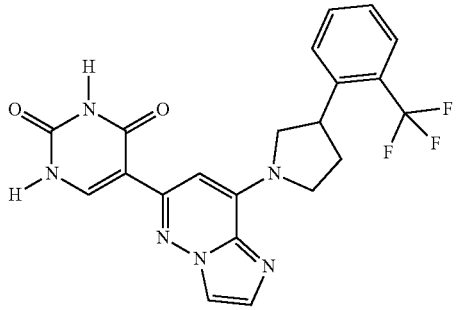 [SMILES: O=c1[nH]cc(-c2cc(N3CCC(c4ccccc4C(F)(F)F)C3)c3nccn3n2)c(=O)[nH]1]

5-(8-(3-(2-(trifluoromethyl)phenyl)pyrrolidin-1-yl)imidazo[1,2-b]pyridazin-6-yl)pyrimidine-2,4(1H,3H)-dione was prepared in the manner described for Example 247, but replacing 4-(azetidin-3-yl)benzonitrile with 3-(2-(trifluoromethyl)phenyl)pyrrolidine. ES/MS m/z: 443.2 [M+H]. $^1$H NMR (400 MHz, Methanol-d4) δ 8.20 (s, 1H), 8.14 (d, J=1.8 Hz, 1H), 7.79 (d, J=1.9 Hz, 1H), 7.77-7.71 (m, 2H), 7.67 (t, J=7.6 Hz, 1H), 7.47 (t, J=7.6 Hz, 1H), 7.16 (s, 1H), 4.34 (s, 1H), 4.15 (t, J=9.0 Hz, 1H), 4.01 (h, J=9.4, 8.9 Hz, 3H), 2.53 (d, J=5.5 Hz, 1H), 2.37 (t, J=10.8 Hz, 1H).

Example 251. 5-(8-(3-(4-methoxyphenyl)azetidin-1-yl)imidazo[1,2-b]pyridazin-6-yl)pyrimidine-2,4(1H,3H)-dione

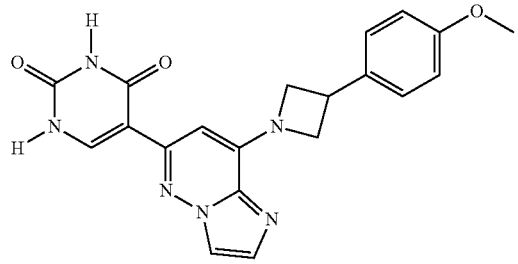 [SMILES: COc1ccc(C2CN(c3cc(-c4c[nH]c(=O)[nH]c4=O)nn4ccnc34)C2)cc1]

5-(8-(3-(4-methoxyphenyl)azetidin-1-yl)imidazo[1,2-b]pyridazin-6-yl)pyrimidine-2,4(1H,3H)-dione was prepared in the manner described for Example 247, but replacing 4-(azetidin-3-yl)benzonitrile with 3-(4-methoxyphenyl)azetidine. ES/MS m/z: 391.1 [M+H]. $^1$H NMR (400 MHz, Methanol-d4) δ 8.15 (s, 1H), 8.07 (s, 1H), 7.74 (s, 1H), 7.37 (d, J=8.6 Hz, 2H), 6.94 (d, J=8.7 Hz, 2H), 6.88 (s, 1H), 4.91-4.87 (m, 2H), 4.45 (t, J=7.7 Hz, 2H), 4.12 (q, J=7.1, 6.5 Hz, 1H), 3.79 (s, 3H).

Example 252. 5-(8-(3-(4-(trifluoromethoxy)phenyl)azetidin-1-yl)imidazo[1,2-b]pyridazin-6-yl)pyrimidine-2,4(1H,3H)-dione

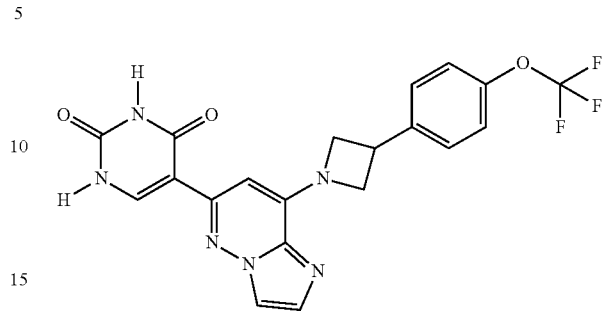

5-(8-(3-(4-(trifluoromethoxy)phenyl)azetidin-1-yl)imidazo[1,2-b]pyridazin-6-yl)pyrimidine-2,4(1H,3H)-dione was prepared in the manner described for Example 247, but replacing 4-(azetidin-3-yl)benzonitrile with 3-(4-(trifluoromethoxy)phenyl)azetidine. ES/MS m/z: 445.1 [M+H]. $^1$H NMR (400 MHz, Methanol-d4) δ 8.10 (s, 1H), 7.99 (d, J=1.4 Hz, 1H), 7.64 (s, 1H), 7.57 (d, J=8.6 Hz, 2H), 7.33-7.23 (m, 2H), 6.75 (s, 1H), 4.90 (d, J=9.0 Hz, 2H), 4.46 (d, J=8.1 Hz, 2H), 4.24-4.09 (m, 1H).

Example 253. 5-(8-(3-fluoro-3-phenylpyrrolidin-1-yl)imidazo[1,2-b]pyridazin-6-yl)pyrimidine-2,4(1H,3H)-dione

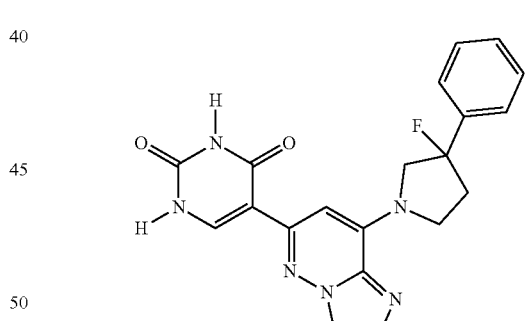

5-(8-(3-fluoro-3-phenylpyrrolidin-1-yl)imidazo[1,2-b]pyridazin-6-yl)pyrimidine-2,4(1H,3H)-dione was prepared in the manner described for Example 247, but replacing 4-(azetidin-3-yl)benzonitrile with 3-fluoro-3-phenylpyrrolidine. ES/MS m/z: 392.9 [M+H]. $^1$H NMR (400 MHz, DMSO-d6) δ 11.45-11.28 (m, 2H), 8.04 (d, J=1.1 Hz, 1H), 7.94 (d, J=6.1 Hz, 1H), 7.61 (d, J=7.2 Hz, 2H), 7.55 (d, J=1.1 Hz, 1H), 7.51-7.40 (m, 3H), 6.64 (s, 1H), 5.23-3.49 (m, 4H), 2.81-2.54 (m, 2H).

Example 254. 5-(8-(2-azabicyclo[3.1.0]hexan-2-yl)imidazo[1,2-b]pyridazin-6-yl)pyrimidine-2,4(1H,3H)-dione

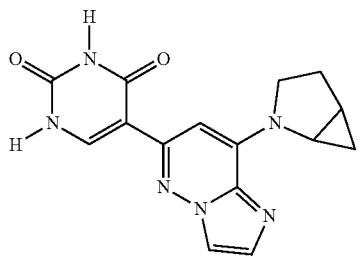 [SMILES: O=c1[nH]cc(-c2cc(N3CCC4CC43)c3nccn3n2)c(=O)[nH]1]

5-(8-(2-azabicyclo[3.1.0]hexan-2-yl)imidazo[1,2-b]pyridazin-6-yl)pyrimidine-2,4(1H,3H)-dione was prepared in the manner described for Example 247, but replacing 4-(azetidin-3-yl)benzonitrile with 2-azabicyclo[3.1.0]hexane. ES/MS m/z: 311.1 [M+H]. $^1$H NMR (400 MHz, Methanol-d4) δ 8.20 (s, 1H), 8.15 (d, J=1.8 Hz, 1H), 7.84 (d, J=1.8 Hz, 1H), 7.33 (s, 1H), 4.26 (td, J=10.6, 3.8 Hz, 1H), 3.95 (d, J=6.7 Hz, 1H), 3.52-3.37 (m, 1H), 2.54-2.38 (m, 1H), 2.21 (ddd, J=12.7, 8.6, 3.8 Hz, 1H), 1.96 (dt, J=14.9, 6.2 Hz, 1H), 1.09 (dt, J=8.7, 5.6 Hz, 1H), 0.74 (td, J=5.4, 2.5 Hz, 1H).

Example 255. 5-(8-(3-fluoro-3-(4-fluorophenyl)pyrrolidin-1-yl)imidazo[1,2-b]pyridazin-6-yl)pyrimidine-2,4(1H,3H)-dione

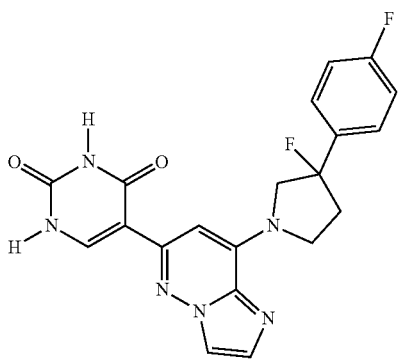 [SMILES: O=c1[nH]cc(-c2cc(N3CCC(F)(c4ccc(F)cc4)C3)c3nccn3n2)c(=O)[nH]1]

5-(8-(3-fluoro-3-(4-fluorophenyl)pyrrolidin-1-yl)imidazo[1,2-b]pyridazin-6-yl)pyrimidine-2,4(1H,3H)-dione was prepared in the manner described for Example 247, but replacing 4-(azetidin-3-yl)benzonitrile with 3-fluoro-3-(4-fluorophenyl)pyrrolidine. ES/MS m/z: 410.9 [M+H]. $^1$H NMR (400 MHz, Methanol-d4) δ 8.06 (s, 1H), 7.90 (d, J=1.3 Hz, 1H), 7.64 (dd, J=8.6, 5.2 Hz, 2H), 7.51 (d, J=1.3 Hz, 1H), 7.19 (t, J=8.7 Hz, 2H), 6.70 (s, 1H), 4.77-4.51 (m, 1H), 4.29 (dd, J=36.5, 13.1 Hz, 2H), 4.04 (s, 1H), 2.81-2.50 (m, 2H).

Example 256. 5-(8-(3-fluoro-3-(4-(trifluoromethyl)phenyl)pyrrolidin-1-yl)imidazo[1,2-b]pyridazin-6-yl)pyrimidine-2,4(1H,3H)-dione

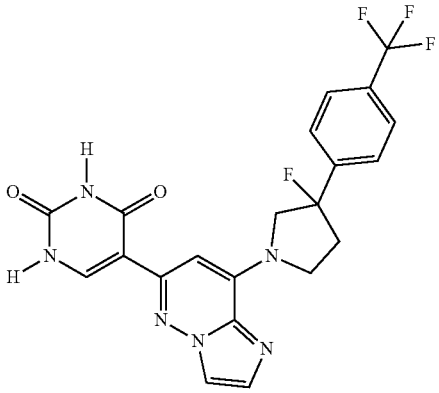 [SMILES: O=c1[nH]cc(-c2cc(N3CCC(F)(c4ccc(C(F)(F)F)cc4)C3)c3nccn3n2)c(=O)[nH]1]

5-(8-(3-fluoro-3-(4-(trifluoromethyl)phenyl)pyrrolidin-1-yl)imidazo[1,2-b]pyridazin-6-yl)pyrimidine-2,4(1H,3H)-dione was prepared in the manner described for Example 247, but replacing 4-(azetidin-3-yl)benzonitrile with 3-fluoro-3-(4-(trifluoromethyl)phenyl)pyrrolidine. ES/MS m/z: 461.1 [M+H]. $^1$H NMR (400 MHz, Methanol-d4) δ 8.22 (s, 1H), 8.17 (d, J=1.8 Hz, 1H), 7.85 (s, 1H), 7.82 (q, J=8.6, 7.3 Hz, 4H), 7.23 (s, 1H), 4.65-4.32 (m, 2H), 4.31-4.07 (m, 2H), 2.93-2.60 (m, 2H).

Example 257. 5-(8-(2-azabicyclo[3.2.0]heptan-2-yl)imidazo[1,2-b]pyridazin-6-yl)pyrimidine-2,4(1H,3H)-dione

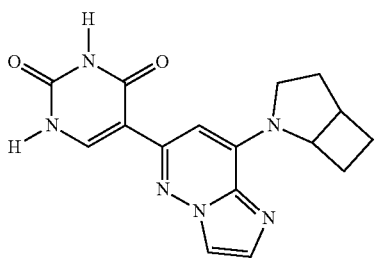 [SMILES: O=c1[nH]cc(-c2cc(N3CCC4CCC43)c3nccn3n2)c(=O)[nH]1]

5-(8-(2-azabicyclo[3.2.0]heptan-2-yl)imidazo[1,2-b]pyridazin-6-yl)pyrimidine-2,4(1H,3H)-dione was prepared in the manner described for Example 247, but replacing 4-(azetidin-3-yl)benzonitrile with 2-azabicyclo[3.2.0]heptane. ES/MS m/z: 325.1 [M+H]. $^1$H NMR (400 MHz, DMSO-d6) δ 11.35 (s, 2H), 7.98 (d, J=1.1 Hz, 1H), 7.93 (s, 1H), 7.51 (d, J=1.1 Hz, 1H), 6.57 (s, 1H), 4.23-3.49 (m, 2H), 3.32 (s, 1H), 3.18 (h, J=6.4, 6.0 Hz, 1H), 2.36 (dq, J=11.7, 6.6, 5.8 Hz, 1H), 2.09 (d, J=10.8 Hz, 1H), 2.05-1.95 (m, 1H), 1.93-1.82 (m, 1H), 1.71 (d, J=14.7 Hz, 2H).

Example 258. 5-(8-(3-(4-fluorophenyl)azetidin-1-yl) imidazo[1,2-b]pyridazin-6-yl)pyrimidine-2,4(1H, 3H)-dione

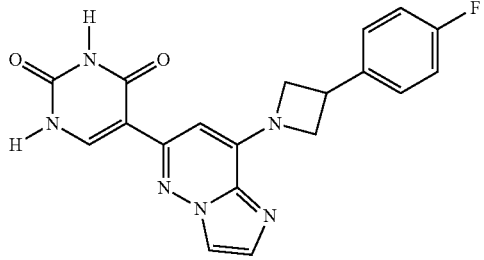 [SMILES: O=c1[nH]cc(-c2cc(N3CC(c4ccc(F)cc4)C3)c3nccn3n2)c(=O)[nH]1]

5-(8-(3-(4-fluorophenyl)azetidin-1-yl)imidazo[1,2-b] pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-(4-fluorophenyl)azetidin-1-yl)imidazo[1,2-b] pyridazine and isolated by filtration as an HCl salt. ES/MS m/z: 379.1 [M+H]. $^1$H NMR (400 MHz, Methanol-d4) δ 8.13 (s, 1H), 8.04 (s, 1H), 7.70 (s, 1H), 7.54-7.41 (m, 2H), 7.18-7.05 (m, 2H), 6.82 (s, 1H), 4.89 (d, J=9.3 Hz, 2H), 4.46 (t, J=7.5 Hz, 2H), 4.22-4.07 (m, 1H).

Example 259. 5-(8-(3-fluoro-3-phenylazetidin-1-yl) imidazo[1,2-b]pyridazin-6-yl)pyrimidine-2,4(1H, 3H)-dione

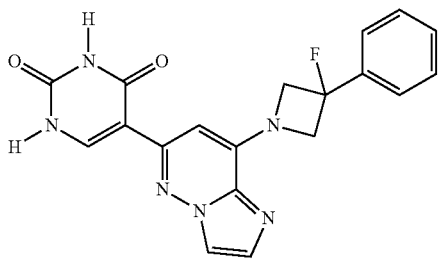 [SMILES: O=c1[nH]cc(-c2cc(N3CC(F)(c4ccccc4)C3)c3nccn3n2)c(=O)[nH]1]

5-(8-(3-fluoro-3-phenylazetidin-1-yl)imidazo[1,2-b] pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-fluoro-3-phenylazetidin-1-yl)imidazo[1,2-b] pyridazine and isolated by filtration as an HCl salt. ES/MS m/z: 379.1 [M+H]. $^1$H NMR (400 MHz, Methanol-d4) δ 8.29-8.13 (m, 2H), 7.91 (d, J=1.8 Hz, 1H), 7.62 (d, J=7.9 Hz, 2H), 7.47 (dt, J=23.4, 7.2 Hz, 3H), 7.18 (s, 1H), 4.96 (s, 2H), 4.90 (s, 2H).

Example 260. 5-(8-(4,4-difluoro-6-azaspiro[2.5] octan-6-yl)imidazo[1,2-b]pyridazin-6-yl)pyrimidine-2,4(1H,3H)-dione

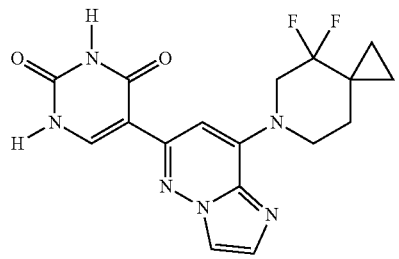 [SMILES: O=c1[nH]cc(-c2cc(N3CCC4(CC4)C(F)(F)C3)c3nccn3n2)c(=O)[nH]1]

5-(8-(4,4-difluoro-6-azaspiro[2.5]octan-6-yl)imidazo[1, 2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(4,4-difluoro-6-azaspiro [2.5]octan-6-yl)-6-(2,4-dimethoxypyrimidin-5-yl)imidazo [1,2-b]pyridazine and isolated by filtration as an HCl salt. ES/MS m/z: 375.1 [M+H]. $^1$H NMR (400 MHz, Methanol-d4) δ 8.26 (d, J=2.5 Hz, 2H), 7.96 (d, J=1.9 Hz, 1H), 7.76 (s, 1H), 4.06 (t, J=10.8 Hz, 2H), 3.88-3.71 (m, 2H), 1.97-1.85 (m, 2H), 1.07-0.89 (m, 2H), 0.72-0.50 (m, 2H).

Example 261. Methyl 4-(1-(6-(2,4-dioxo-1,2,3,4-tetrahydropyrimidin-5-yl)imidazo[1,2-b]pyridazin-8-yl)azetidin-3-yl)benzoate

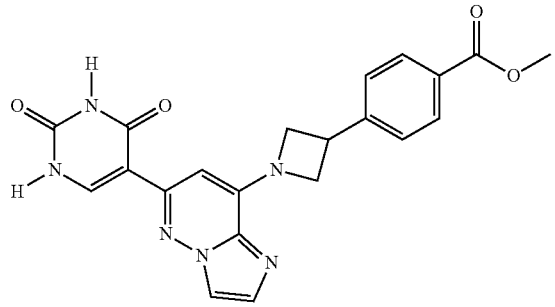 [SMILES: COC(=O)c1ccc(C2CN(c3cc(-c4c[nH]c(=O)[nH]c4=O)nn4ccnc34)C2)cc1]

Methyl 4-(1-(6-(2,4-dioxo-1,2,3,4-tetrahydropyrimidin-5-yl)imidazo[1,2-b]pyridazin-8-yl)azetidin-3-yl)benzoate was prepared in the manner described for Example 1, but replacing 8-cyclopropyl-6-(2,4-dimethoxypyrimidin-5-yl)-2-methyl-imidazo[1,2-b]pyridazine with methyl 4-(1-(6-(2, 4-dimethoxypyrimidin-5-yl)imidazo[1,2-b]pyridazin-8-yl) azetidin-3-yl)benzoate and isolated by filtration as an HCl salt. ES/MS m/z: 419.1 [M+H]. $^1$H NMR (400 MHz, Methanol-d4) δ 8.10 (s, 1H), 8.04 (d, J=8.1 Hz, 2H), 7.98 (s, 1H), 7.62 (s, 1H), 7.58 (d, J=8.2 Hz, 2H), 6.72 (s, 1H), 4.94-4.87 (m, 2H), 4.56-4.42 (m, 2H), 4.22 (d, J=7.9 Hz, 1H), 3.91 (s, 3H).

Example 262. 5-(3-fluoro-8-(3-(4-(trifluoromethyl)phenyl)pyrrolidin-1-yl)imidazo[1,2-b]pyridazin-6-yl)pyrimidine-2,4(1H,3H)-dione

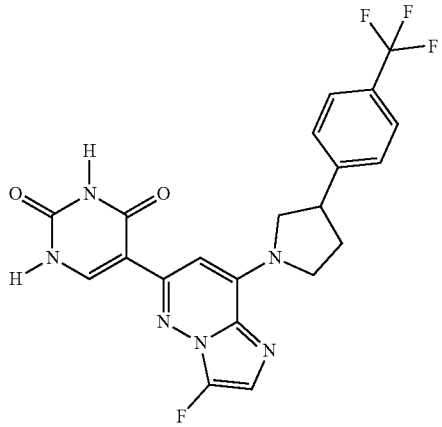 [SMILES: O=c1[nH]cc(-c2cc(N3CCC(c4ccc(C(F)(F)F)cc4)C3)c3ncc(F)n3n2)c(=O)[nH]1]

5-(3-fluoro-8-(3-(4-(trifluoromethyl)phenyl)pyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-(3-(4-(trifluoromethyl)phenyl)pyrrolidin-1-yl)imidazo[1,2-b]pyridazine and isolated by filtration as an HCl salt. ES/MS m/z: 461.1 [M+H]. $^1$H NMR (400 MHz, Methanol-d4) δ 8.22 (s, 1H), 7.68 (d, J=8.1 Hz, 2H), 7.63-7.56 (m, 3H), 7.12 (s, 1H), 4.43 (s, 1H), 4.12 (s, 1H), 3.95 (s, 2H), 3.83-3.69 (m, 1H), 2.58 (s, 1H), 2.29 (p, J=9.7 Hz, 1H).

Example 263. Methyl 3-(1-(6-(2,4-dioxo-1,2,3,4-tetrahydropyrimidin-5-yl)imidazo[1,2-b]pyridazin-8-yl)azetidin-3-yl)benzoate

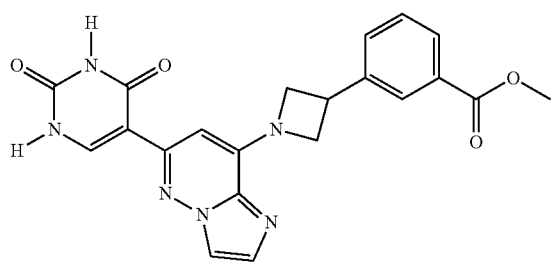 [SMILES: COC(=O)c1cccc(C2CN(c3cc(-c4c[nH]c(=O)[nH]c4=O)nn4ccnc34)C2)c1]

Methyl 3-(1-(6-(2,4-dioxo-1,2,3,4-tetrahydropyrimidin-5-yl)imidazo[1,2-b]pyridazin-8-yl)azetidin-3-yl)benzoate was prepared in the manner described for Example 1, but replacing 8-cyclopropyl-6-(2,4-dimethoxypyrimidin-5-yl)-2-methyl-imidazo[1,2-b]pyridazine with methyl 3-(1-(6-(2,4-dimethoxypyrimidin-5-yl)imidazo[1,2-b]pyridazin-8-yl)azetidin-3-yl)benzoate and isolated by filtration as an HCl salt. ES/MS m/z: 419.1 [M+H]. $^1$H NMR (400 MHz, Methanol-d4) δ 8.18 (s, 1H), 8.13 (q, J=1.9 Hz, 2H), 7.96 (dt, J=7.7, 1.4 Hz, 1H), 7.80 (d, J=1.8 Hz, 1H), 7.73 (d, J=7.7 Hz, 1H), 7.53 (t, J=7.8 Hz, 1H), 6.98 (s, 1H), 4.92 (q, J=8.3, 7.7 Hz, 2H), 4.59-4.46 (m, 2H), 4.26 (ddd, J=14.6, 8.6, 5.9 Hz, 1H), 3.91 (s, 3H).

Example 264. Methyl 3-(1-(6-(2,4-dioxo-1,2,3,4-tetrahydropyrimidin-5-yl)imidazo[1,2-b]pyridazin-8-yl)pyrrolidin-3-yl)benzoate

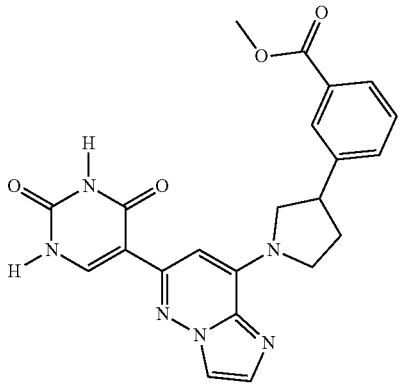 [SMILES: COC(=O)c1cccc(C2CCN(c3cc(-c4c[nH]c(=O)[nH]c4=O)nn4ccnc34)C2)c1]

Methyl 3-(1-(6-(2,4-dioxo-1,2,3,4-tetrahydropyrimidin-5-yl)imidazo[1,2-b]pyridazin-8-yl)pyrrolidin-3-yl)benzoate was prepared in the manner described for Example 1, but replacing 8-cyclopropyl-6-(2,4-dimethoxypyrimidin-5-yl)-2-methyl-imidazo[1,2-b]pyridazine with methyl 3-(1-(6-(2,4-dimethoxypyrimidin-5-yl)imidazo[1,2-b]pyridazin-8-yl)pyrrolidin-3-yl)benzoate and isolated by filtration as an HCl salt. ES/MS m/z: 433.1 [M+H]. $^1$H NMR (400 MHz, Methanol-d4) δ 8.26 (s, 1H), 8.23 (d, J=2.0 Hz, 1H), 8.11-8.05 (m, 1H), 7.96 (dt, J=7.8, 1.4 Hz, 1H), 7.92 (d, J=2.0 Hz, 1H), 7.68 (dt, J=7.7, 1.5 Hz, 1H), 7.51 (t, J=7.7 Hz, 1H), 7.35 (s, 1H), 4.37 (t, J=8.8 Hz, 1H), 4.09 (t, J=9.3 Hz, 1H), 4.03-3.91 (m, 2H), 3.92 (s, 3H), 3.84-3.72 (m, 1H), 2.67-2.52 (m, 1H), 2.35 (p, J=10.3 Hz, 1H).

Example 265. Methyl 4-(1-(6-(2,4-dioxo-1,2,3,4-tetrahydropyrimidin-5-yl)imidazo[1,2-b]pyridazin-8-yl)pyrrolidin-3-yl)benzoate

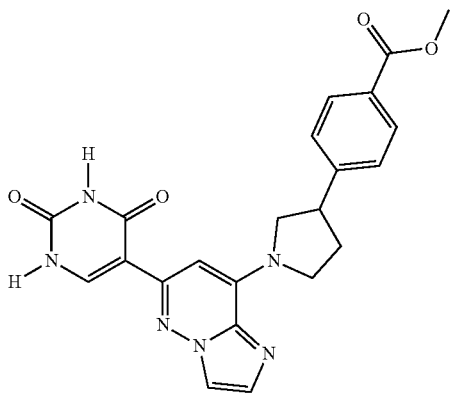 [SMILES: COC(=O)c1ccc(C2CCN(c3cc(-c4c[nH]c(=O)[nH]c4=O)nn4ccnc34)C2)cc1]

Methyl 4-(1-(6-(2,4-dioxo-1,2,3,4-tetrahydropyrimidin-5-yl)imidazo[1,2-b]pyridazin-8-yl)pyrrolidin-3-yl)benzoate was prepared in the manner described for Example 1, but replacing 8-cyclopropyl-6-(2,4-dimethoxypyrimidin-5-yl)-2-methyl-imidazo[1,2-b]pyridazine with methyl 4-(1-(6-(2,4-dimethoxypyrimidin-5-yl)imidazo[1,2-b]pyridazin-8-yl)pyrrolidin-3-yl)benzoate and isolated by filtration as an HCl salt. ES/MS m/z: 433.2 [M+H]. $^1$H NMR (400 MHz, Methanol-d4) δ 8.24 (s, 1H), 8.21 (d, J=2.0 Hz, 1H), 8.08-7.99 (m, 2H), 7.89 (d, J=2.0 Hz, 1H), 7.60-7.49 (m, 2H), 7.30 (s, 1H), 4.37 (t, J=8.9 Hz, 1H), 4.08 (d, J=5.6 Hz, 1H), 3.98 (dd, J=17.3, 9.0 Hz, 2H), 3.91 (s, 3H), 3.77 (td, J=15.6, 14.3, 7.1 Hz, 1H), 2.66-2.53 (m, 1H), 2.33 (p, J=10.0 Hz, 1H).

Example 266. 5-(8-(7,7-difluoro-5-azaspiro[2.4]heptan-5-yl)-[1,2,4]triazolo[4,3-b]pyridazin-6-yl)pyrimidine-2,4(1H,3H)-dione

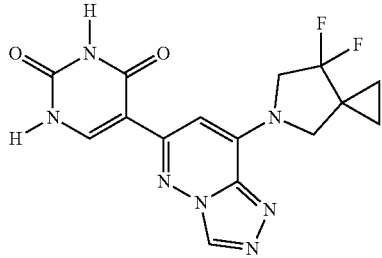 [SMILES: O=c1[nH]cc(-c2cc(N3CC(F)(F)C4(CC4)C3)c3nncn3n2)c(=O)[nH]1]

5-(8-(7,7-difluoro-5-azaspiro[2.4]heptan-5-yl)-[1,2,4]triazolo[4,3-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(7,7-difluoro-5-azaspiro[2.4]heptan-5-yl)-6-(2,4-dimethoxypyrimidin-5-yl)-[1,2,4]triazolo[4,3-b]pyridazine and isolated by filtration as an HCl salt. ES/MS m/z: 362.1 [M+H]. $^1$H NMR (400 MHz, DMSO-d6) δ 11.47 (s, 2H), 9.45 (s, 1H), 7.99 (s, 1H), 6.60 (s, 1H), 4.56 (s, 2H), 4.09 (q, J=5.2 Hz, 2H), 1.06 (d, J=3.6 Hz, 2H), 1.03 (d, J=3.7 Hz, 2H).

Example 267. 5-(8-(3-(4-(3,3-difluoroazetidine-1-carbonyl)phenyl)azetidin-1-yl)imidazo[1,2-b]pyridazin-6-yl)pyrimidine-2,4(1H,3H)-dione

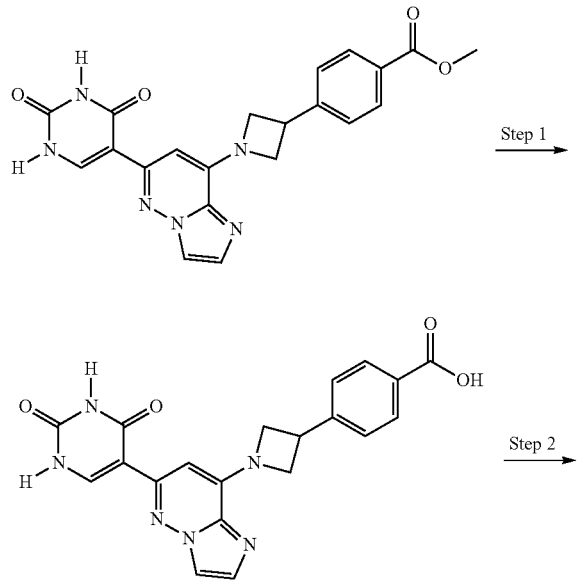

-continued

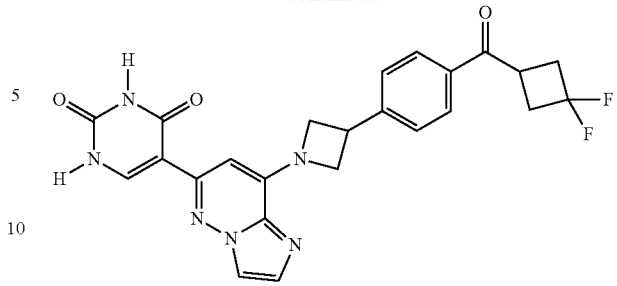

Step 1. To a suspension of methyl 4-(1-(6-(2,4-dioxo-1,2,3,4-tetrahydropyrimidin-5-yl)imidazo[1,2-b]pyridazin-8-yl)azetidin-3-yl)benzoate (240 mg, 0.57 mmol, 1 equiv) in 1:1 MeOH/THF (6 mL) was added 1M lithium hydroxide (2.9 mL, 2.8 mmol, 5 equiv). The reaction was stirred at room temperature for 3 hours, then quenched with 1M HCl (3 mL) and concentrated, affording 4-(1-(6-(2,4-dioxo-1,2,3,4-tetrahydropyrimidin-5-yl)imidazo[1,2-b]pyridazin-8-yl)azetidin-3-yl)benzoic acid. This material was taken forward without further purification. ES/MS m/z: 405.1 [M+H].

Step 2. To a mixture of 4-(1-(6-(2,4-dioxo-1,2,3,4-tetrahydropyrimidin-5-yl)imidazo[1,2-b]pyridazin-8-yl)azetidin-3-yl)benzoic acid (30 mg, 0.07 mmol, 1 equiv) in pyridine (1 mL) was added 3,3-difluoroazetidine hydrochloride (10.4 mg, 0.08 mmol, 1.1 equiv) and N-Ethyl-N'-(3-dimethylaminopropyl) carbodiimide hydrochloride (16.8 mg, 0.087 mmol, 1.2 equiv). The reaction mixture was stirred for 15 h then concentrated. The residue was taken up in acetonitrile and water (2 mL) and purified by RP-HPLC (10-80% MeCN/H$_2$O with TFA modifier) to provide 5-(8-(3-(4-(3,3-difluoroazetidine-1-carbonyl)phenyl)azetidin-1-yl)imidazo[1,2-b]pyridazin-6-yl)pyrimidine-2,4(1H,3H)-dione as the TFA salt. ES/MS m/z: 480.1 [M+H]. $^1$H NMR (400 MHz, Methanol-d4) δ 8.19 (s, 1H), 8.14 (d, J=1.7 Hz, 1H), 7.82 (d, J=1.7 Hz, 1H), 7.78-7.69 (m, 2H), 7.60 (d, J=8.2 Hz, 2H), 7.01 (s, 1H), 4.92 (t, J=8.9 Hz, 2H), 4.77-4.40 (m, 6H), 4.32-4.18 (m, 1H).

Example 268. 5-(8-(3-(3-(3,3-difluoroazetidine-1-carbonyl)phenyl)azetidin-1-yl)imidazo[1,2-b]pyridazin-6-yl)pyrimidine-2,4(1H,3H)-dione 5-(8-(3-(3-(3,3-difluoroazetidine-1-carbonyl)phenyl)azetidin-1-yl)imidazo[1,2-b]pyridazin-6-yl)pyrimidine-2,4(1H,3H)-dione was prepared in the manner described for Example 267, but replacing methyl 4-(1-(6-(2,4-dioxo-1,2,3,4-tetrahydropyrimidin-5-yl)imidazo[1,2-b]pyridazin-8-yl)azetidin-3-yl)benzoate with methyl 3-(1-(6-(2,4-dioxo-1,2,3,4-tetrahydropyrimidin-5-yl)imidazo[1,2-b]pyridazin-8-yl)azetidin-3-yl)benzoate. ES/MS m/z: 480.1 [M+H]. $^1$H NMR (400 MHz, Methanol-d4) δ 8.06 (s, 1H), 7.90 (d, J=1.3 Hz, 1H), 7.77 (s, 1H), 7.66 (d, J=7.6 Hz, 1H), 7.63-7.58 (m, 1H), 7.55-7.48 (m, 2H), 6.59 (s, 1H), 4.73 4.43 (m, 8H), 4.25-4.10 (m, 1H).

Example 269. 3-(1-(6-(2,4-dioxo-1,2,3,4-tetrahydropyrimidin-5-yl)imidazo[1,2-b]pyridazin-8-yl)pyrrolidin-3-yl)-N-methylbenzamide

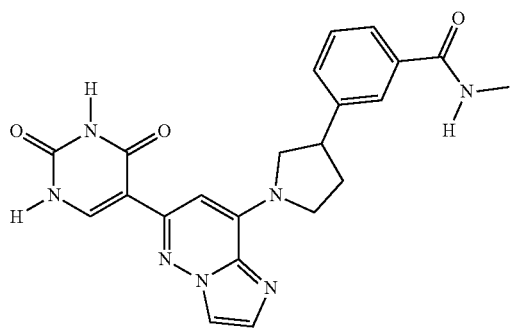 [SMILES: CNC(=O)c1cccc(C2CCN(c3cc(-c4c[nH]c(=O)[nH]c4=O)nn4ccnc34)C2)c1]

3-(1-(6-(2,4-dioxo-1,2,3,4-tetrahydropyrimidin-5-yl)imidazo[1,2-b]pyridazin-8-yl)pyrrolidin-3-yl)-N-methylbenzamide was prepared in the manner described for Example 267, but replacing methyl 4-(1-(6-(2,4-dioxo-1,2,3,4-tetrahydropyrimidin-5-yl)imidazo[1,2-b]pyridazin-8-yl)azetidin-3-yl)benzoate with methyl 3-(1-(6-(2,4-dioxo-1,2,3,4-tetrahydropyrimidin-5-yl)imidazo[1,2-b]pyridazin-8-yl)pyrrolidin-3-yl)benzoate in step 1, and replacing 3,3-difluoroazetidine hydrochloride with methylamine in step 2. ES/MS m/z: 432.1 [M+H]. $^1$H NMR (400 MHz, DMSO-d6) δ 11.34 (s, 2H), 8.45 (d, J=4.8 Hz, 1H), 7.99 (d, J=1.2 Hz, 1H), 7.94 (s, 1H), 7.84 (d, J=1.8 Hz, 1H), 7.72 (dt, J=7.6, 1.4 Hz, 1H), 7.57-7.48 (m, 2H), 7.43 (t, J=7.6 Hz, 1H), 6.59 (s, 1H), 4.03-3.69 (m, 3H), 3.61 (p, J=8.2 Hz, 1H), 2.78 (d, J=4.5 Hz, 3H), 2.47-2.37 (m, 2H), 2.17 (p, J=10.2 Hz, 1H).

Example 270. 4-(1-(6-(2,4-dioxo-1,2,3,4-tetrahydropyrimidin-5-yl)imidazo[1,2-b]pyridazin-8-yl)pyrrolidin-3-yl)-N-methylbenzamide

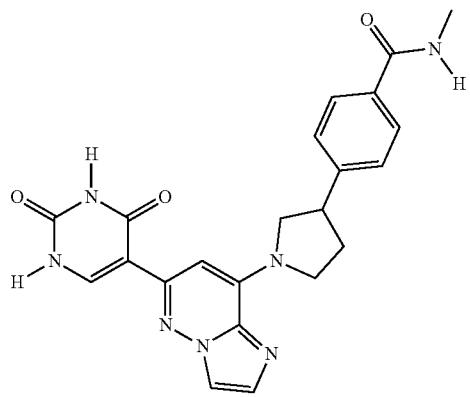 [SMILES: CNC(=O)c1ccc(C2CCN(c3cc(-c4c[nH]c(=O)[nH]c4=O)nn4ccnc34)C2)cc1]

4-(1-(6-(2,4-dioxo-1,2,3,4-tetrahydropyrimidin-5-yl)imidazo[1,2-b]pyridazin-8-yl)pyrrolidin-3-yl)-N-methylbenzamide was prepared in the manner described for Example 267, but replacing methyl 4-(1-(6-(2,4-dioxo-1,2,3,4-tetrahydropyrimidin-5-yl)imidazo[1,2-b]pyridazin-8-yl)azetidin-3-yl)benzoate with methyl 4-(1-(6-(2,4-dioxo-1,2,3,4-tetrahydropyrimidin-5-yl)imidazo[1,2-b]pyridazin-8-yl)pyrrolidin-3-yl)benzoate in step 1, and replacing 3,3-difluoroazetidine hydrochloride with methylamine in step 2. ES/MS m/z: 432.1 [M+H]. $^1$H NMR (400 MHz, DMSO-d6) δ 11.36 (s, 1H), 11.33 (d, J=6.0 Hz, 1H), 8.39 (d, J=4.7 Hz, 1H), 7.99 (d, J=1.1 Hz, 1H), 7.93 (d, J=6.1 Hz, 1H), 7.85-7.75 (m, 2H), 7.50 (d, J=1.2 Hz, 1H), 7.45 (d, J=8.3 Hz, 2H), 6.58 (s, 1H), 3.82 (s, 3H), 3.62 (q, J=8.3 Hz, 1H), 2.78 (d, J=4.5 Hz, 3H), 2.46-2.36 (m, 2H), 2.24-2.07 (m, 1H).

Example 271. 5-(8-((2S,2S)-2-(2-(trifluoromethyl)pyrimidin-4-yl)cyclopropyl)imidazo[1,2-b]pyridazin-6-yl)pyrimidine-2,4(1H,3H)-dione (RACEMIC)

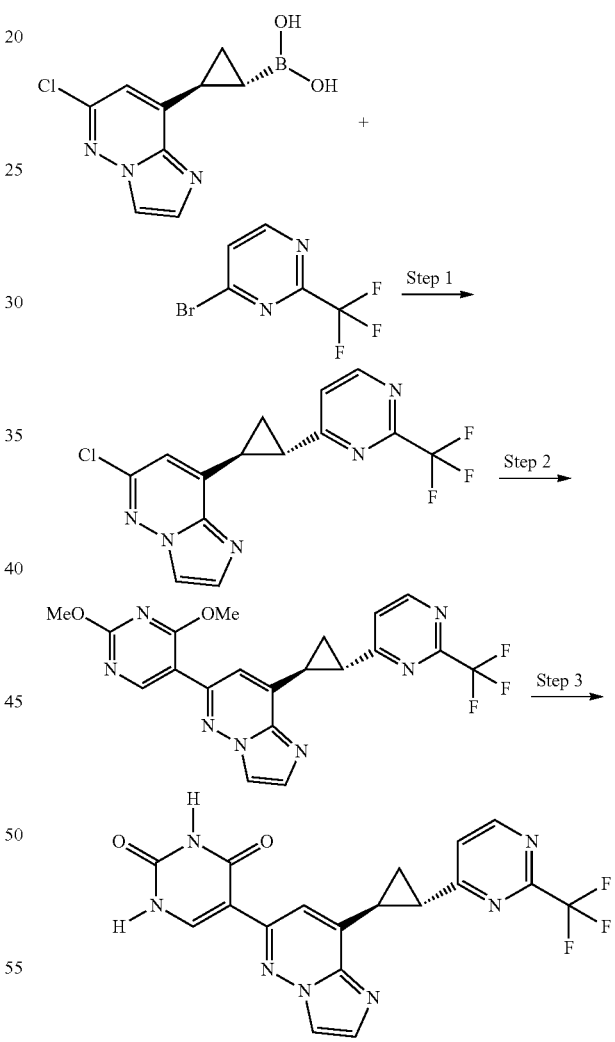

Step 1. To a mixture of ((1S,2S)-2-(6-chloroimidazo[1,2-b]pyridazin-8-yl)cyclopropyl)boronic acid (115 mg, 0.48 mmol, 1 equiv), 4-bromo-2-(trifluoromethyl)pyrimidine (176 mg, 0.78 mmol, 1.6 equiv), and potassium phosphate tribasic (308 mg, 1.45 mmol, 3 equiv) in 3:1 dioxane/H$_2$O (2.5 mL) was added mesylate[(di(1-adamantyl)-n-butylphosphine)-2-(2'-amino-1,1'-biphenyl)]palladium(II) (35 mg, 0.05 mmol, 0.1 equiv). The reaction was purged with Argon and stirred at 110° C. for 5 h. The reaction mixture was directly purified by silica gel chromatography (0-100% EtOAc/hexanes), affording 6-chloro-8-((1S,2S)-2-(2-(trifluoromethyl)pyrimidin-4-yl)cyclopropyl)imidazo[1,2-b]pyridazine. ES/MS m/z: 340.1 [M+H].

Step 2. A mixture of 6-chloro-8-((1S,2S)-2-(2-(trifluoromethyl)pyrimidin-4-yl)cyclopropyl)imidazo[1,2-b]pyridazine (10 mg, 0.03 mmol, 1 equiv), (2,4-dimethoxypyrimidin-5-yl)boronic acid (6.5 mg, 0.04 mmol, 1.2 equiv), Pd(dppf)Cl₂—CH₂Cl₂ (2.2 mg, 0.003 mmol, 0.1 equiv), and cesium carbonate (24 mg, 0.07 mmol, 2.5 equiv) in 3:1 dioxane/.H₂O (1.2 mL) was purged with Argon and stirred at 80° C. for 1 h. The reaction mixture was purified directly by silica gel chromatography (0-100% EtOAc/hexanes), affording 6-(2,4-dimethoxypyrimidin-5-yl)-8-((2S,2S)-2-(2-(trifluoromethyl)pyrimidin-4-yl)cyclopropyl)imidazo[1,2-b]pyridazine. ES/MS m/z: 444.2 [M+H].

Step 3. To a solution of 6-(2,4-dimethoxypyrimidin-5-yl)-8-((2S,2S)-2-(2-(trifluoromethyl)pyrimidin-4-yl)cyclopropyl)imidazo[1,2-b]pyridazine (3.8 mg, 0.009 mmol, 1 equiv) in MeOH (2.5 mL) was added aqueous 1 M HCl (2.5 mL). The reaction was stirred at 80° C. for 4.5 h. The reaction was concentrated and purified by RP-HPLC (10-70% MeCN/H₂O with AcOH modifier) to afford 5-(8-((1S,2S)-2-(2-(trifluoromethyl)pyrimidin-4-yl)cyclopropyl)imidazo[1,2-b]pyridazin-6-yl)pyrimidine-2,4(1H,3H)-dione. ES/MS m/z: 416.2 [M+H]. ¹H NMR (400 MHz, Methanol-d4) δ 8.76 (d, J=5.2 Hz, 1H), 8.17 (s, 1H), 8.09 (d, J=1.3 Hz, 1H), 7.70 (d, J=5.2 Hz, 1H), 7.66 (d, J=1.3 Hz, 1H), 7.64 (s, 1H), 3.27-3.19 (m, 1H), 3.03-2.91 (m, 1H), 2.12 (dd, J=8.2, 6.6 Hz, 2H).

Example 272. 5-(8-((1S,2S)-2-(2-(trifluoromethyl)pyrimidin-5-yl)cyclopropyl)imidazo[1,2-b]pyridazin-6-yl)pyrimidine-2,4(1H,3H)-dione

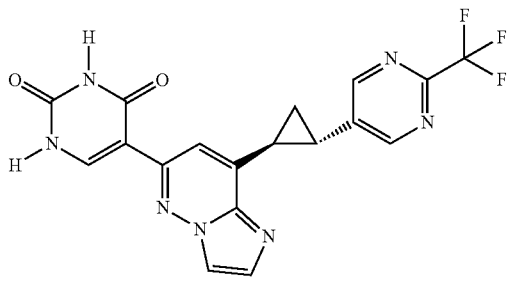 [SMILES: O=c1[nH]cc(-c2cc([C@H]3C[C@@H]3c3cnc(C(F)(F)F)nc3)c3nccn3n2)c(=O)[nH]1]

5-(8-((1S,2S)-2-(2-(trifluoromethyl)pyrimidin-5-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(2-(trifluoromethyl)pyrimidin-5-yl)cyclopropyl)imidazo[1,2-b]pyridazine and purified by RP-HPLC (10-70% MeCN/H₂O with TFA modifier). ES/MS m/z: 416.1 [M+H]. ¹H NMR (400 MHz, DMSO-d6) δ 11.55 (d, J=4.5 Hz, 2H), 9.01 (s, 2H), 8.34 (d, J=1.3 Hz, 1H), 8.03 (d, J=6.3 Hz, 1H), 7.86 (s, 1H), 7.66 (s, 1H), 3.05 (dt, J=9.2, 5.6 Hz, 1H), 2.97 (ddd, J=8.8, 6.1, 4.4 Hz, 1H), 2.36-2.26 (m, 1H), 2.02 (dt, J=8.9, 5.5 Hz, 1H).

Example 273. 5-(3-fluoro-8-((1R,2R)-2-(2-(trifluoromethyl)pyrimidin-5-yl)cyclopropyl)imidazo[1,2-b]pyridazin-6-yl)pyrimidine-2,4(1H,3H)-dione

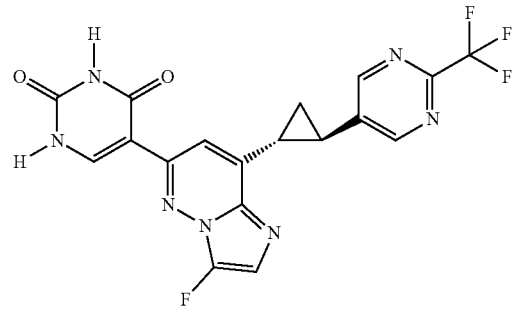 [SMILES: O=c1[nH]cc(-c2cc([C@@H]3C[C@H]3c3cnc(C(F)(F)F)nc3)c3ncc(F)n3n2)c(=O)[nH]1]

5-(3-fluoro-8-((1R,2R)-2-(2-(trifluoromethyl)pyrimidin-5-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((1R,2R)-2-(2-(trifluoromethyl)pyrimidin-5-yl)cyclopropyl)imidazo[1,2-b]pyridazine and purified by RP-HPLC (10-70% MeCN/H₂O with TFA modifier). ES/MS m/z: 434.0 [M+H]. ¹H NMR (400 MHz, DMSO-d6) δ 11.55 (d, J=3.7 Hz, 2H), 9.02 (s, 2H), 8.03 (d, J=6.5 Hz, 1H), 7.59 (s, 1H), 7.56 (d, J=7.1 Hz, 1H), 3.12 (ddd, J=9.0, 6.1, 4.5 Hz, 1H), 2.96 (ddd, J=8.9, 6.0, 4.4 Hz, 1H), 2.37-2.28 (m, 1H), 2.06-1.95 (m, 1H).

Example 274. 5-(8-(2-oxa-7-azaspiro[4.4]nonan-7-yl)imidazo[1,2-b]pyridazin-6-yl)pyrimidine-2,4(1H,3H)-dione

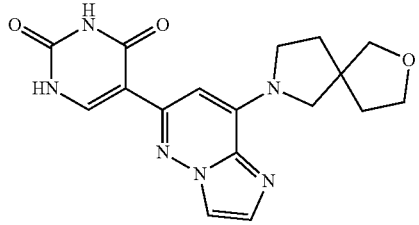 [SMILES: O=c1[nH]cc(-c2cc(N3CCC4(CCOC4)C3)c3nccn3n2)c(=O)[nH]1]

5-(8-(2-oxa-7-azaspiro[4.4]nonan-7-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-(6-(2,4-dimethoxypyrimidin-5-yl)imidazo[1,2-b]pyridazin-8-yl)-2-oxa-7-azaspiro[4.4]nonane and purified by RP-HPLC (10-90% MeCN/H₂O with TFA, Gemini-NX column) as a TFA salt. ES/MS m/z: 355.17 [M+H]. ¹H NMR (400 MHz, DMSO-d6) δ 11.38 (s, 1H), 11.35 (d, J=6.1 Hz, 1H), 8.02 (s, 1H), 7.93 (d, J=6.1 Hz, 1H), 7.55 (s, 1H), 6.58 (s, 1H), 3.85-3.80 (m, 4H), 3.66-3.57 (m, 4H), 2.02 (td, J=7.1, 2.6 Hz, 2H), 1.99-1.86 (m, 2H). ¹⁹F NMR (376 MHz, DMSO-d6) δ −75.03.

Example 275. 5-(8-(8-oxa-2-azaspiro[4.5]decan-2-yl)imidazo[1,2-b]pyridazin-6-yl)pyrimidine-2,4(1H,3H)-dione

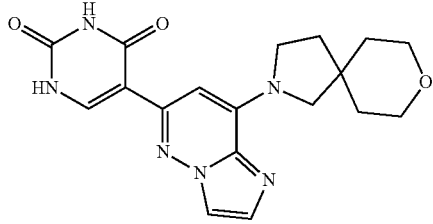 [SMILES: O=c1[nH]cc(-c2cc(N3CCC4(CCOCC4)C3)c3nccn3n2)c(=O)[nH]1]

5-(8-(8-oxa-2-azaspiro[4.5]decan-2-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 2-(6-(2,4-dimethoxypyrimidin-5-yl)imidazo[1,2-b]pyridazin-8-yl)-8-oxa-2-azaspiro[4.5]decane and purified by RP-HPLC (10-90% MeCN/H$_2$O with TFA, Gemini-NX column) as a TFA salt. ES/MS m/z: 369.20 [M+H]. $^1$H NMR (400 MHz, DMSO-d6) δ 11.45-11.34 (m, 2H), 8.09 (d, J=1.3 Hz, 1H), 7.94 (d, J=6.0 Hz, 1H), 7.67 (d, J=1.4 Hz, 1H), 6.66 (s, 1H), 4.05-3.68 (m, 4H), 3.61 (qdd, J=11.4, 6.4, 4.2 Hz, 4H), 1.95 (t, J=7.1 Hz, 2H), 1.66-1.48 (m, 4H). $^{19}$F NMR (376 MHz, DMSO-d6) δ −75.38.

Example 276. 5-(8-((1S,2S)-2-(benzo[d]thiazol-6-yl)cyclopropyl)imidazo[1,2-b]pyridazin-6-yl)pyrimidine-2,4(1H,3H)-dione

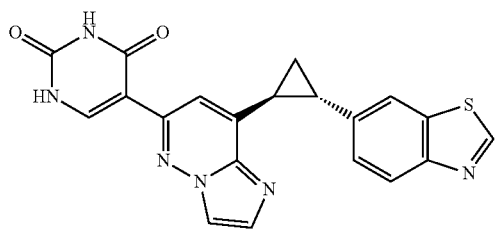 [SMILES: O=c1[nH]cc(-c2cc([C@H]3C[C@@H]3c3ccc4ncsc4c3)c3nccn3n2)c(=O)[nH]1]

5-(8-((1S,2S)-2-(benzo[d]thiazol-6-yl)cyclopropyl)imidazo[1,2-b]pyridazin-6-yl)pyrimidine-2,4(1H,3H)-dione as a racemate was prepared in the manner described for Example 1, but replacing 8-cyclopropyl-6-(2,4-dimethoxypyrimidin-5-yl)-2-methyl-imidazo[1,2-b]pyridazine with racemic 6-((2S,2S)-2-(6-(2,4-dimethoxypyrimidin-5-yl)imidazo[1,2-b]pyridazin-8-yl)cyclopropyl)benzo[d]thiazole and purified by RP-HPLC (10-90% MeCN/H$_2$O with TFA, Gemini-NX column) as a TFA salt. ES/MS m/z: 403.10 [M+H]. $^1$H NMR (400 MHz, DMSO-d6) δ 11.60-11.44 (m, 2H), 9.33 (s, 1H), 8.30 (s, 1H), 8.07 (d, J=1.7 Hz, 1H), 8.03 (s, 1H), 8.01 (d, J=2.6 Hz, 1H), 7.81 (s, 1H), 7.55 (s, 1H), 7.45 (dd, J=8.5, 1.8 Hz, 1H), 2.97 (ddd, J=9.3, 6.1, 4.4 Hz, 1H), 2.81 (dt, J=9.0, 5.3 Hz, 1H), 2.15 (dt, J=8.7, 5.4 Hz, 1H), 1.87 (dt, J=8.6, 5.5 Hz, 1H). $^{19}$F NMR (376 MHz, DMSO-d6) δ −74.83.

Example 277. 5-(3-fluoro-8-((2S,2S)-2-(4-(trifluoromethoxy)phenyl)cyclopropyl)imidazo[1,2-b]pyridazin-6-yl)pyrimidine-2,4(1H,3H)-dione

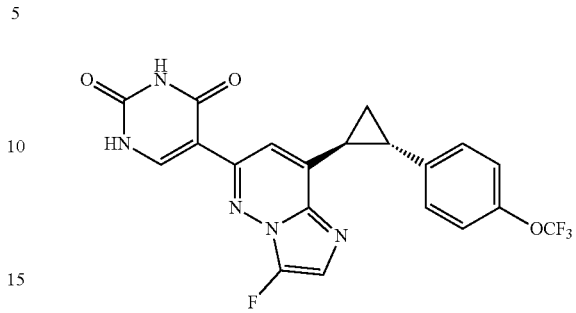

5-(3-fluoro-8-((1S,2S)-2-(4-(trifluoromethoxy)phenyl)cyclopropyl)imidazo[1,2-b]pyridazin-6-yl)pyrimidine-2,4(1H,3H)-dione as a racemate was prepared in the manner described for Example 1, but replacing 8-cyclopropyl-6-(2,4-dimethoxypyrimidin-5-yl)-2-methyl-imidazo[1,2-b]pyridazine with racemic 6-(2,4-dimethoxypyrimidin-5-yl)-3-fluoro-8-((1S,2S)-2-(4-(trifluoromethoxy)phenyl)cyclopropyl)imidazo[1,2-b]pyridazine and isolated by filtration as an HCl salt. ES/MS m/z: 446.13 [M+H]. $^1$H NMR (400 MHz, DMSO-d6) δ 11.52 (s, 2H), 8.02 (s, 1H), 7.53 (d, J=7.1 Hz, 1H), 7.47 (s, 1H), 7.42-7.34 (m, 2H), 7.34-7.26 (m, 2H), 2.88 (ddd, J=9.0, 6.2, 4.4 Hz, 1H), 2.70 (ddd, J=8.9, 6.0, 4.5 Hz, 1H), 2.12 (dt, J=8.9, 5.1 Hz, 1H), 1.76 (ddd, J=8.8, 6.2, 4.8 Hz, 1H). $^{19}$F NMR (376 MHz, DMSO-d6) δ −57.40, −155.61 (d, J=7.2 Hz).

Example 278. 5-(8-((2S,2S)-2-(2,2-difluorobenzo[d][1,3]dioxol-5-yl)cyclopropyl)-3-fluoroimidazo[1,2-b]pyridazin-6-yl)pyrimidine-2,4(1H,3H)-dione

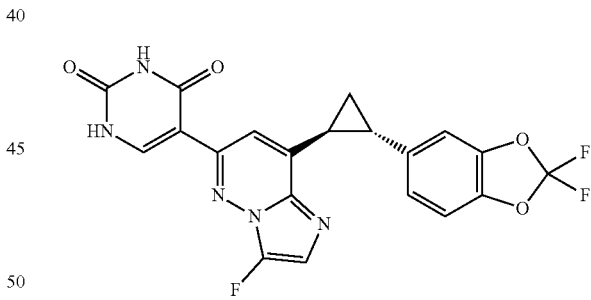

5-(8-((1S,2S)-2-(2,2-difluorobenzo[d][1,3]dioxol-5-yl)cyclopropyl)-3-fluoroimidazo[1,2-b]pyridazin-6-yl)pyrimidine-2,4(1H,3H)-dione as a racemate was prepared in the manner described for Example 1, but replacing 8-cyclopropyl-6-(2,4-dimethoxypyrimidin-5-yl)-2-methyl-imidazo[1,2-b]pyridazine with racemic 8-((1S,2S)-2-(2,2-difluorobenzo[d][1,3]dioxol-5-yl)cyclopropyl)-6-(2,4-dimethoxypyrimidin-5-yl)-3-fluoro-5-yl)-3-imidazo[1,2-b][1,2]fluorazine and purified by RP-HPLC (5-100% MeCN/H$_2$O with TFA, Gemini-NX column) as a TFA salt. ES/MS m/z: 444.10 [M+H]. $^1$H NMR (400 MHz, DMSO-d6) δ 11.63-11.47 (m, 2H), 8.02 (d, J=6.4 Hz, 1H), 7.54 (d, J=7.1 Hz, 1H), 7.47 (s, 1H), 7.35 (d, J=1.8 Hz, 1H), 7.32 (d, J=8.3 Hz, 1H), 7.13 (dd, J=8.4, 1.8 Hz, 1H), 2.89 (ddd, J=9.0, 6.3, 4.4 Hz, 1H), 2.68 (ddd, J=8.9, 5.9, 4.3 Hz, 1H), 2.11 (dt, J=8.9, 5.3 Hz, 1H), 1.76 (ddd, J=8.8, 6.1, 4.8 Hz, 1H). $^{19}$F NMR (376 MHz, DMSO-d6) δ −49.74, −75.33, −155.61 (d, J=7.1 Hz).

Example 279. 4-((2S,2S)-2-(6-(2,4-dioxo-1,2,3,4-tetrahydropyrimidin-5-yl)imidazo[1,2-b]pyridazin-8-yl)cyclopropyl)-3-fluorobenzonitrile

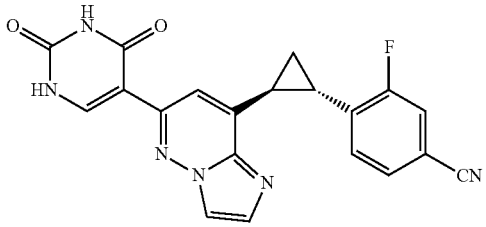 [SMILES: N#Cc1ccc([C@H]2C[C@@H]2c2cc(-c3c[nH]c(=O)[nH]c3=O)nn3ccnc23)c(F)c1]

4-((2S,2S)-2-(6-(2,4-dioxo-1,2,3,4-tetrahydropyrimidin-5-yl)imidazo[1,2-b]pyridazin-8-yl)cyclopropyl)-3-fluorobenzonitrile was prepared in the manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)imidazo[1,2-b]pyridazin-8-yl)cyclopropyl)-3-fluorobenzonitrile and purified by RP-HPLC (10-90% MeCN/H$_2$O with TFA, Gemini-NX column) as a TFA salt. ES/MS m/z: 389.10 [M+H]. $^1$H NMR (400 MHz, DMSO-d6) δ 11.62-11.46 (m, 2H), 8.36 (d, J=1.5 Hz, 1H), 8.03 (d, J=6.1 Hz, 1H), 7.91 (s, 1H), 7.83 (dd, J=10.2, 1.6 Hz, 1H), 7.71 (dd, J=8.1, 1.6 Hz, 1H), 7.66 (s, 1H), 7.49 (t, J=7.9 Hz, 1H), 3.09-2.97 (m, 1H), 2.86 (ddd, J=8.9, 6.1, 4.5 Hz, 1H), 2.17 (dt, J=9.0, 5.4 Hz, 1H), 1.97-1.84 (m, 1H). $^{19}$F NMR (376 MHz, DMSO-d6) δ −75.27, −117.79--118.08 (m).

Example 280. 5-(8-((1S,2S)-2-(2-fluoro-4-(trifluoromethoxy)phenyl)cyclopropyl)imidazo[1,2-b]pyridazin-6-yl)pyrimidine-2,4(1H,3H)-dione

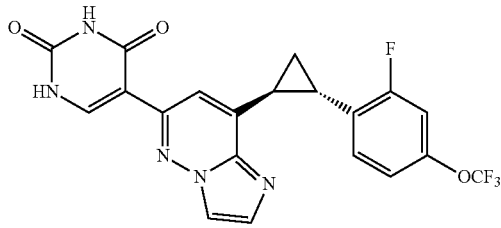 [SMILES: O=c1[nH]cc(-c2cc([C@H]3C[C@@H]3c3ccc(OC(F)(F)F)cc3F)c3nccn3n2)c(=O)[nH]1]

5-(8-((1S,2S)-2-(2-fluoro-4-(trifluoromethoxy)phenyl)cyclopropyl)imidazo[1,2-b]pyridazin-6-yl)pyrimidine-2,4(1H,3H)-dione as a racemate was prepared in the manner described for Example 1, but replacing 8-cyclopropyl-6-(2,4-dimethoxypyrimidin-5-yl)-2-methyl-imidazo[1,2-b]pyridazine with racemic 6-(2,4-dimethoxypyrimidin-5-yl)-8-((1S,2S)-2-(2-fluoro-4-(trifluoromethoxy)phenyl)cyclopropyl)imidazo[1,2-b]pyridazine and purified by RP-HPLC (10-90% MeCN/H$_2$O with TFA, Gemini-NX column) as a TFA salt. ES/MS m/z: 448.11 [M+H]. $^1$H NMR (400 MHz, DMSO-d6) δ 11.58 (d, J=6.2 Hz, 1H), 11.56 (s, 1H), 8.40 (d, J=1.6 Hz, 1H), 8.05 (d, J=6.2 Hz, 1H), 7.97 (d, J=1.5 Hz, 1H), 7.68 (s, 1H), 7.43 (t, J=8.6 Hz, 1H), 7.38 (dd, J=10.5, 2.5 Hz, 1H), 7.29-7.20 (m, 1H), 2.97-2.86 (m, 1H), 2.79 (dt, J=8.9, 5.6 Hz, 1H), 2.07 (dt, J=9.0, 5.4 Hz, 1H), 1.87 (ddd, J=8.7, 6.3, 5.0 Hz, 1H). $^{19}$F NMR (376 MHz, DMSO-d6) δ −57.65, −75.32, −115.92 (t, J=9.6 Hz).

Example 281. methyl 4-((2S,2S)-2-(6-(2,4-dioxo-1,2,3,4-tetrahydropyrimidin-5-yl)imidazo[1,2-b]pyridazin-8-yl)cyclopropyl)benzoate

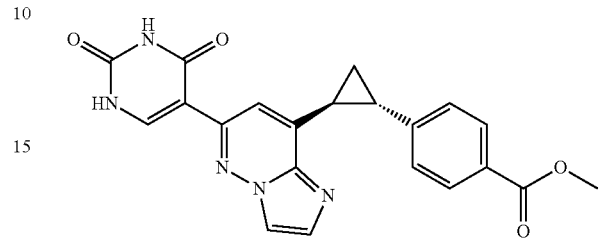

methyl 4-((1S,2S)-2-(6-(2,4-dioxo-1,2,3,4-tetrahydropyrimidin-5-yl)imidazo[1,2-b]pyridazin-8-yl)cyclopropyl)benzoate as a racemate was prepared in the manner described for Example 1, but replacing 8-cyclopropyl-6-(2,4-dimethoxypyrimidin-5-yl)-2-methyl-imidazo[1,2-b]pyridazine with racemic methyl 4-((1S,2S)-2-(6-(2,4-dimethoxypyrimidin-5-yl)imidazo[1,2-b]pyridazin-8-yl)cyclopropyl)benzoate and purified by RP-HPLC (10-90% MeCN/H$_2$O with TFA, Gemini-NX column) as a TFA salt. ES/MS m/z: 404.13 [M+H]. $^1$H NMR (400 MHz, Acetonitrile-d3) δ 9.43 (s, 1H), 9.32 (s, 1H), 8.19 (d, J=2.0 Hz, 1H), 8.16 (d, J=6.4 Hz, 1H), 8.01 (s, 1H), 7.98-7.91 (m, 3H), 7.39-7.33 (m, 2H), 3.89 (s, 3H), 2.94 (dt, J=8.7, 5.4 Hz, 1H), 2.68 (ddd, J=9.0, 6.7, 4.4 Hz, 1H), 1.93-1.86 (m, 2H). $^{19}$F NMR (376 MHz, Acetonitrile-d3) δ −77.13.

Example 282. methyl 3-((2S,2S)-2-(6-(2,4-dioxo-1,2,3,4-tetrahydropyrimidin-5-yl)imidazo[1,2-b]pyridazin-8-yl)cyclopropyl)benzoate

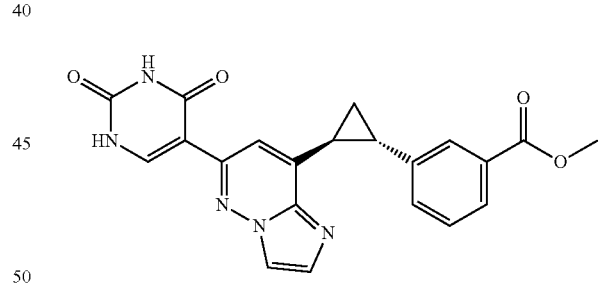

methyl 3-((2S,2S)-2-(6-(2,4-dioxo-1,2,3,4-tetrahydropyrimidin-5-yl)imidazo[1,2-b]pyridazin-8-yl)cyclopropyl)benzoate as a racemate was prepared in the manner described for Example 1, but replacing 8-cyclopropyl-6-(2,4-dimethoxypyrimidin-5-yl)-2-methyl-imidazo[1,2-b]pyridazine with racemic methyl 3-((2S,2S)-2-(6-(2,4-dimethoxypyrimidin-5-yl)imidazo[1,2-b]pyridazin-8-yl)cyclopropyl)benzoate and purified by RP-HPLC (10-90% MeCN/H$_2$O with TFA, Gemini-NX column) as a TFA salt. ES/MS m/z: 404.19 [M+H]. $^1$H NMR (400 MHz, Acetonitrile-d3) δ 9.39 (s, 1H), 9.29 (s, 1H), 8.18 (d, J=1.8 Hz, 1H), 8.15 (d, J=6.5 Hz, 1H), 7.99 (s, 1H), 7.95 (d, J=1.9 Hz, 1H), 7.93-7.84 (m, 2H), 7.53 (d, J=7.7 Hz, 1H), 7.48 (t, J=7.6 Hz, 1H), 3.90 (s, 3H), 2.91 (q, J=6.9 Hz, 1H), 2.73 (dq, J=7.6, 4.4 Hz, 1H), 1.94-1.87 (m, 2H). $^{19}$F NMR (376 MHz, Acetonitrile-d3) δ −77.19.

Example 283. 4-((2S,2S)-2-(6-(2,4-dioxo-1,2,3,4-tetrahydropyrimidin-5-yl)imidazo[1,2-b]pyridazin-8-yl)cyclopropyl)benzamide

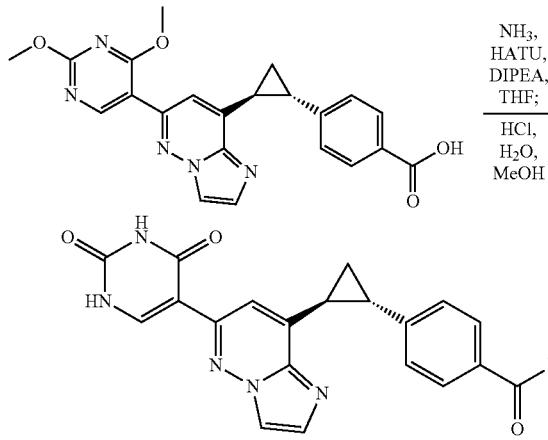

To 4-((2S,2S)-2-(6-(2,4-dimethoxypyrimidin-5-yl)imidazo[1,2-b]pyridazin-8-yl)cyclopropyl)benzoic acid (0.195 g, 0.47 mmol) in DMF (1 mL) was added HATU (464 mg, 1.2 mmol, 2.6 equiv) followed by DIPEA (0.21 ml, 1.2 mmol, 2.5 equiv) and ammonia solution (4.8 mL, 0.5 M in THF, 2.4 mmol, 5 equiv). After 4 h, MeOH (5 mL) was added and the volatiles were removed under reduced pressure. To the resulting mixture was added MeOH (1 mL) and 1 M HCl aqueous solution (1 mL), and heated to 60° C. for 16 h. Purification was accomplished by RP-HPLC (10-90% MeCN/H$_2$O with TFA, Gemini-NX column) affording racemic 4-((1S,2S)-2-(6-(2,4-dioxo-1,2,3,4-tetrahydropyrimidin-5-yl)imidazo[1,2-b]pyridazin-8-yl)cyclopropyl)benzamide as a TFA salt. ES/MS m/z: 389.10 [M+H]. $^1$H NMR (400 MHz, DMSO-d6) δ 11.60-11.42 (m, 2H), 8.30 (d, J=1.4 Hz, 1H), 8.01 (d, J=6.3 Hz, 1H), 7.92 (s, 1H), 7.86-7.76 (m, 3H), 7.53 (s, 1H), 7.37-7.30 (m, 2H), 7.29 (s, 1H), 2.86 (ddd, J=9.3, 6.3, 4.4 Hz, 1H), 2.82-2.73 (m, 1H), 2.11 (dt, J=8.9, 5.2 Hz, 1H), 1.81 (dt, J=8.6, 5.2 Hz, 1H). $^{19}$F NMR (376 MHz, DMSO-d6) δ −74.84.

Example 284. 3-((1S,2S)-2-(6-(2,4-dioxo-1,2,3,4-tetrahydropyrimidin-5-yl)imidazo[1,2-b]pyridazin-8-yl)cyclopropyl)benzamide

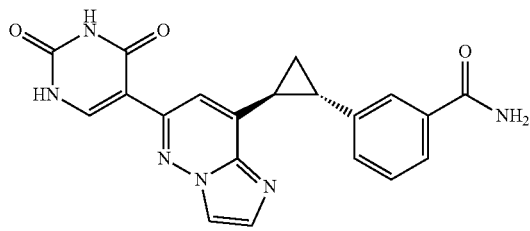 [SMILES: NC(=O)c1cccc([C@H]2C[C@@H]2c2cc(-c3c[nH]c(=O)[nH]c3=O)nn3ccnc23)c1]

3-((2S,2S)-2-(6-(2,4-dioxo-1,2,3,4-tetrahydropyrimidin-5-yl)imidazo[1,2-b]pyridazin-8-yl)cyclopropyl)benzamide as a racemate was prepared in the manner described for Example 283, but replacing racemic 4-((2S,2S)-2-(6-(2,4-dimethoxypyrimidin-5-yl)imidazo[1,2-b]pyridazin-8-yl)cyclopropyl)benzoic acid with racemic 3-((2S,2S)-2-(6-(2,4-dimethoxypyrimidin-5-yl)imidazo[1,2-b]pyridazin-8-yl)cyclopropyl)benzoic acid and purified by RP-HPLC (10-90% MeCN/H$_2$O with TFA, Gemini-NX column) as a TFA salt. ES/MS m/z: 389.11 [M+H]. $^1$H NMR (400 MHz, DMSO-d6) δ 11.64-11.51 (m, 2H), 8.41 (d, J=1.5 Hz, 1H), 8.05 (d, J=6.1 Hz, 1H), 7.98 (s, 2H), 7.76-7.69 (m, 2H), 7.66 (s, 1H), 7.45-7.33 (m, 3H), 2.88-2.77 (m, 2H), 2.03 (dt, J=8.6, 5.3 Hz, 1H), 1.92-1.82 (m, 1H). $^{19}$F NMR (376 MHz, DMSO-d6) δ −75.30.

Example 285. 4-((2S,2S)-2-(6-(2,4-dioxo-1,2,3,4-tetrahydropyrimidin-5-yl)imidazo[1,2-b]pyridazin-8-yl)cyclopropyl)-N-methylbenzamide

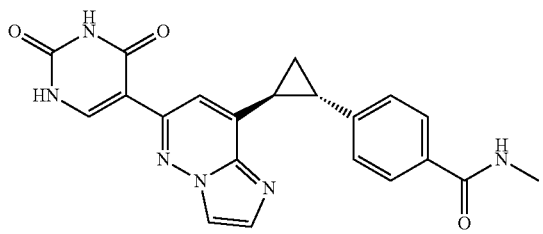 [SMILES: CNC(=O)c1ccc([C@H]2C[C@@H]2c2cc(-c3c[nH]c(=O)[nH]c3=O)nn3ccnc23)cc1]

4-((1S,2S)-2-(6-(2,4-dioxo-1,2,3,4-tetrahydropyrimidin-5-yl)imidazo[1,2-b]pyridazin-8-yl)cyclopropyl)-N-methylbenzamide as a racemate was prepared in the manner described for Example 283, but replacing 0.5 M ammonia in THF with 2 M methylamine in THF and purified by RP-HPLC (10-90% MeCN/H$_2$O with TFA, Gemini-NX column) as a TFA salt. ES/MS m/z: 403.10 [M+H]. $^1$H NMR (400 MHz, DMSO-d6) δ 11.57-11.45 (m, 2H), 8.46-8.32 (m, 1H), 8.26 (s, 1H), 8.00 (d, J=6.0 Hz, 1H), 7.78 (d, J=8.2 Hz, 2H), 7.75 (s, 1H), 7.49 (s, 1H), 7.33 (d, J=8.4 Hz, 2H), 2.93-2.83 (m, 1H), 2.81-2.72 (m, 4H), 2.19-2.07 (m, 1H), 1.84-1.73 (m, 1H). $^{19}$F NMR (376 MHz, DMSO-d6) δ −74.48.

Example 286. 3-((2S,2S)-2-(6-(2,4-dioxo-1,2,3,4-tetrahydropyrimidin-5-yl)imidazo[1,2-b]pyridazin-8-yl)cyclopropyl)-N-methylbenzamide

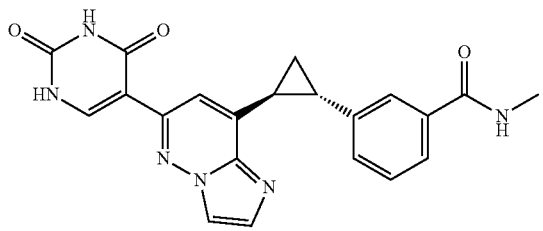 [SMILES: CNC(=O)c1cccc([C@H]2C[C@@H]2c2cc(-c3c[nH]c(=O)[nH]c3=O)nn3ccnc23)c1]

3-((2S,2S)-2-(6-(2,4-dioxo-1,2,3,4-tetrahydropyrimidin-5-yl)imidazo[1,2-b]pyridazin-8-yl)cyclopropyl)-N-methylbenzamide as a racemate was prepared in the manner described for Example 283, but replacing racemic 4-((2S, 2S)-2-(6-(2,4-dimethoxypyrimidin-5-yl)imidazo[1,2-b]pyridazin-8-yl)cyclopropyl)benzoic acid with racemic 3-((2S,2S)-2-(6-(2,4-dimethoxypyrimidin-5-yl)imidazo[1,2-b]pyridazin-8-yl)cyclopropyl)benzoic acid and 0.5 M ammonia in THF with 2 M methylamine in THF and purified by RP-HPLC (10-90% MeCN/H$_2$O with TFA, Gemini-NX column) as a TFA salt. ES/MS m/z: 403.10 [M+H]. $^1$H NMR (400 MHz, DMSO-d6) δ 11.61-11.44 (m, 2H), 8.51-8.40 (m, 1H), 8.35 (s, 1H), 8.03 (d, J=6.3 Hz, 1H), 7.89 (s, 1H), 7.70-7.64 (m, 2H), 7.59 (s, 1H), 7.46-7.36 (m, 2H), 2.87 (dt, J=9.5, 5.6 Hz, 1H), 2.82-2.75 (m, 4H), 2.10-2.01 (m, 1H), 1.88-1.79 (m, 1H). $^{19}$F NMR (376 MHz, DMSO-d6) δ −75.12.

Example 287. 3-((2S,2S)-2-(6-(2,4-dioxo-1,2,3,4-tetrahydropyrimidin-5-yl)imidazo[1,2-b]pyridazin-8-yl)cyclopropyl)-N,N-dimethylbenzamide

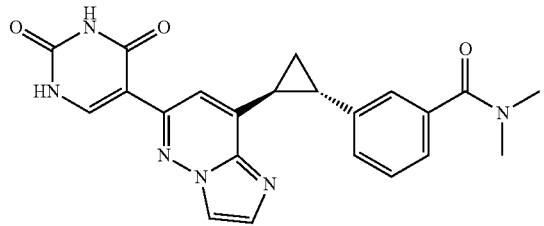

4-((2S,2S)-2-(6-(2,4-dioxo-1,2,3,4-tetrahydropyrimidin-5-yl)imidazo[1,2-b]pyridazin-8-yl)cyclopropyl)-N,N-dimethylbenzamide as a racemate was prepared in the manner described for Example 283, but replacing racemic 4-((2S,2S)-2-(6-(2,4-dimethoxypyrimidin-5-yl)imidazo[1,2-b]pyridazin-8-yl)cyclopropyl)benzoic acid with racemic 3-((2S,2S)-2-(6-(2,4-dimethoxypyrimidin-5-yl)imidazo[1,2-b]pyridazin-8-yl)cyclopropyl)benzoic acid and 0.5 M ammonia in THF with 2 M dimethylamine in THF and purified by RP-HPLC (5-50% MeCN/H$_2$O with TFA, Gemini-NX column) as a TFA salt. ES/MS m/z: 417.20 [M+H]. $^1$H NMR (400 MHz, DMSO-d6) δ 11.62-11.49 (m, 2H), 8.37 (s, 1H), 8.04 (d, J=6.1 Hz, 1H), 7.92 (s, 1H), 7.60 (s, 1H), 7.43-7.31 (m, 2H), 7.28-7.26 (m, 1H), 7.24 (dt, J=7.2, 1.5 Hz, 1H), 2.98 (s, 3H), 2.91 (s, 3H), 2.88-2.81 (m, 1H), 2.81-2.74 (m, 1H), 2.04 (dt, J=10.5, 5.3 Hz, 1H), 1.82 (dt, J=8.5, 5.3 Hz, 1H). $^{19}$F NMR (376 MHz, DMSO-d6) δ −75.14.

Example 288. 4-((2S,2S)-2-(6-(2,4-dioxo-1,2,3,4-tetrahydropyrimidin-5-yl)imidazo[1,2-b]pyridazin-8-yl)cyclopropyl)-N,N-dimethylbenzamide

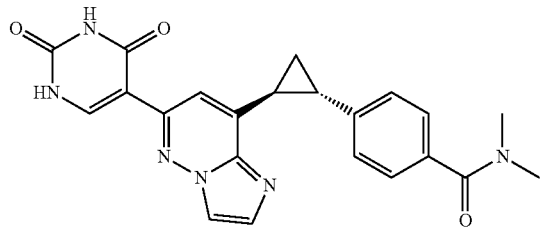 [SMILES: CN(C)C(=O)c1ccc([C@H]2C[C@@H]2c2cc(-c3c[nH]c(=O)[nH]c3=O)nn3ccnc23)cc1]

4-((2S,2S)-2-(6-(2,4-dioxo-1,2,3,4-tetrahydropyrimidin-5-yl)imidazo[1,2-b]pyridazin-8-yl)cyclopropyl)-N,N-dimethylbenzamide as a racemate was prepared in the manner described for Example 283, but replacing 0.5 M ammonia in THF with 2 M dimethylamine in THF and purified by RP-HPLC (5-50% MeCN/H$_2$O with TFA, Gemini-NX column) as a TFA salt. ES/MS m/z: 417.20 [M+H]. $^1$H NMR (400 MHz, DMSO-d6) δ 11.54 (d, J=3.9 Hz, 2H), 8.32 (d, J=1.4 Hz, 1H), 8.02 (d, J=6.4 Hz, 1H), 7.85 (s, 1H), 7.55 (s, 1H), 7.35 (d, J=8.3 Hz, 2H), 7.30 (d, J=8.3 Hz, 2H), 2.95 (d, J=11.8 Hz, 6H), 2.83 (ddd, J=9.0, 6.2, 4.4 Hz, 1H), 2.80 2.73 (m, 1H), 2.08 (dt, J=8.8, 5.2 Hz, 1H), 1.80 (dt, J=8.5, 5.3 Hz, 1H). $^{19}$F NMR (376 MHz, DMSO-d6) δ −74.95.

Example 289. 5-(8-((2S,2S)-2-(4-(azetidine-1-carbonyl)phenyl)cyclopropyl)imidazo[1,2-b]pyridazin-6-yl)pyrimidine-2,4(1H,3H)-dione

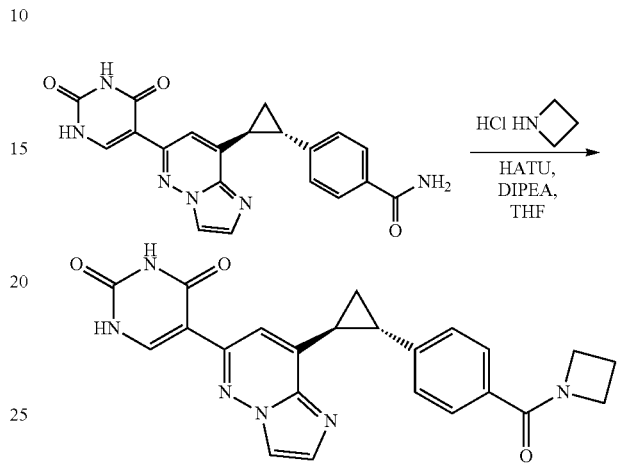

To 4-((2S,2S)-2-(6-(2,4-dioxo-1,2,3,4-tetrahydropyrimidin-5-yl)imidazo[1,2-b]pyridazin-8-yl)cyclopropyl)benzoic acid (20 mg, 0.05 mmol), azetidine hydrochloride (14 mg, 0.15 mmol, 3 equiv), HATU (59 mg, 0.15 mmol, 3 equiv) in DMF (1 mL) followed by DIPEA (0.05 mL, 0.26 mmol, 5 equiv) and stirred for 16 h. Purification was accomplished by RP-HPLC (5-90% MeCN/H$_2$O with TFA, Gemini-NX column) affording racemic 5-(8-((1S,2S)-2-(4-(azetidine-1-carbonyl)phenyl)cyclopropyl)imidazo[1,2-b]pyridazin-6-yl)pyrimidine-2,4(1H,3H)-dione as a TFA salt. ES/MS m/z: 429.10 [M+H]. $^1$H NMR (400 MHz, DMSO-d6) δ 11.53 (s, 2H), 8.32 (s, 1H), 8.02 (d, J=6.4 Hz, 1H), 7.84 (s, 1H), 7.62-7.50 (m, 3H), 7.37-7.25 (m, 2H), 4.30 (t, J=7.6 Hz, 2H), 4.03 (t, J=7.8 Hz, 2H), 2.87-2.81 (m, 1H), 2.81-2.74 (m, 1H), 2.25 (p, J=7.7 Hz, 2H), 2.10 (dt, J=8.9, 5.4 Hz, 1H), 1.81 (dt, J=8.3, 5.2 Hz, 1H). $^{19}$F NMR (376 MHz, DMSO-d6) δ −75.00.

Example 290. 5-(8-((2S,2S)-2-(4-(3-methylazetidine-1-carbonyl)phenyl)cyclopropyl)imidazo[1,2-b]pyridazin-6-yl)pyrimidine-2,4(1H,3H)-dione

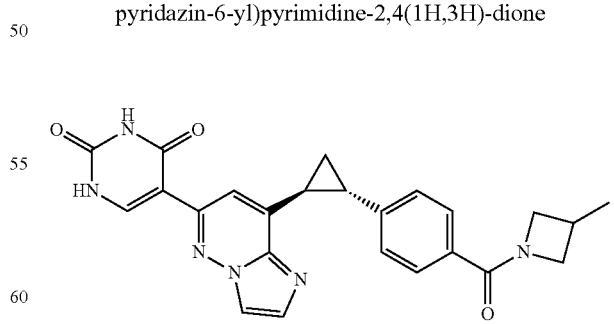

5-(8-((1S,2S)-2-(4-(3-methylazetidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with 3-methylazetidine benzenesulfonate and purified by RP-HPLC (5-90% MeCN/H₂O with TFA, Gemini-NX column) as a TFA salt. ES/MS m/z: 443.10 [M+H]. ¹H NMR (400 MHz, DMSO-d6) δ 11.53 (s, 2H), 8.31 (s, 1H), 8.02 (d, J=6.4 Hz, 1H), 7.83 (s, 1H), 7.57 (d, J=8.1 Hz, 2H), 7.54 (s, 1H), 7.31 (d, J=8.2 Hz, 2H), 4.39 (t, J=8.5 Hz, 1H), 4.14 (t, J=9.2 Hz, 1H), 3.86 (t, J=7.0 Hz, 1H), 3.62-3.56 (m, 1H), 2.84 (dt, J=9.8, 5.5 Hz, 1H), 2.77 (dt, J=10.0, 5.4 Hz, 1H), 2.74 2.64 (m, 1H), 2.10 (dt, J=9.9, 5.4 Hz, 1H), 1.81 (dd, J=9.6, 5.2 Hz, 1H), 1.20 (d, J=6.9 Hz, 3H). ¹⁹F NMR (376 MHz, DMSO-d6) δ −74.96.

Example 291. 5-(8-((1S,2S)-2-(4-(3-(trifluoromethyl)azetidine-1-carbonyl)phenyl)cyclopropyl)imidazo[1,2-b]pyridazin-6-yl)pyrimidine-2,4(1H,3H)-dione

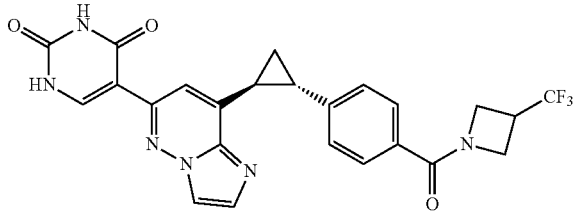 [SMILES: O=C(c1ccc([C@H]2C[C@@H]2c2cc(-c3c[nH]c(=O)[nH]c3=O)nn3ccnc23)cc1)N1CC(C(F)(F)F)C1]

5-(8-((2S,2S)-2-(4-(3-(trifluoromethyl)azetidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with 3-(trifluoromethyl)azetidine and purified by RP-HPLC (5-90% MeCN/H₂O with TFA, Gemini-NX column) as a TFA salt. ES/MS m/z: 497.13 [M+H]. ¹H NMR (400 MHz, DMSO-d6) δ 11.64-11.47 (m, 2H), 8.36 (d, J=1.5 Hz, 1H), 8.04 (d, J=6.0 Hz, 1H), 7.91 (s, 1H), 7.62 (d, J=8.3 Hz, 2H), 7.60 (s, 1H), 7.39-7.30 (m, 2H), 4.59-4.49 (m, 1H), 4.40-4.33 (m, 1H), 4.28 (d, J=9.8 Hz, 1H), 4.06-3.97 (m, 1H), 3.67 (ddt, J=18.2, 9.5, 5.3 Hz, 1H), 2.84 (tq, J=13.5, 5.1 Hz, 2H), 2.10 (dt, J=8.8, 5.3 Hz, 1H), 1.84 (dt, J=8.3, 5.3 Hz, 1H). ¹⁹F NMR (376 MHz, DMSO-d6) δ −72.83 (d, J=9.2 Hz), −75.18.

Example 292. 5-(8-((1S,2S)-2-(4-(3,3-difluoroazetidine-1-carbonyl)phenyl)cyclopropyl)imidazo[1,2-b]pyridazin-6-yl)pyrimidine-2,4(1H,3H)-dione

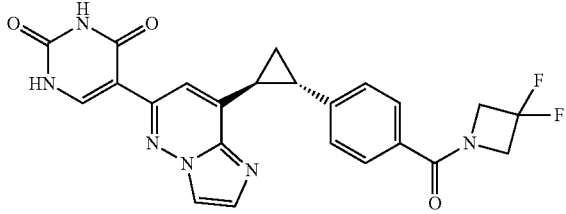 [SMILES: O=C(c1ccc([C@H]2C[C@@H]2c2cc(-c3c[nH]c(=O)[nH]c3=O)nn3ccnc23)cc1)N1CC(F)(F)C1]

5-(8-((1S,2S)-2-(4-(3,3-difluoroazetidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with 3,3-difluoroazetidine hydrochloride and purified by RP-HPLC (5-90% MeCN/H₂O with TFA, Gemini-NX column) as a TFA salt. ES/MS m/z: 465.10 [M+H]. ¹H NMR (400 MHz, DMSO-d6) δ 11.61-11.41 (m, 2H), 8.30 (s, 1H), 8.02 (d, J=6.4 Hz, 1H), 7.82 (s, 1H), 7.64 (d, J=8.2 Hz, 2H), 7.54 (s, 1H), 7.35 (d, J=8.2 Hz, 2H), 4.96-4.62 (m, 2H), 4.62-4.34 (m, 2H), 2.91-2.83 (m, 1H), 2.83 2.75 (m, 1H), 2.18-2.07 (m, 1H), 1.82 (dt, J=8.7, 5.2 Hz, 1H). ¹⁹F NMR (376 MHz, DMSO-d6) δ −74.94, −100.10 (p, J=12.6 Hz).

Example 293. 5-(8-((2S,2S)-2-(4-(3,3-dimethylazetidine-1-carbonyl)phenyl)cyclopropyl)imidazo[1,2-b]pyridazin-6-yl)pyrimidine-2,4(1H,3H)-dione

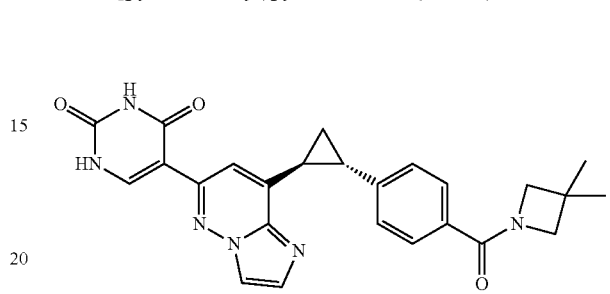

5-(8-((2S,2S)-2-(4-(3,3-dimethylazetidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with 3,3-dimethylazetidine hydrochloride and purified by RP-HPLC (5-90% MeCN/H₂O with TFA, Gemini-NX column) as a TFA salt. ES/MS m/z: 457.12 [M+H]. ¹H NMR (400 MHz, DMSO-d6) δ 11.64-11.41 (m, 2H), 8.33 (d, J=1.4 Hz, 1H), 8.02 (d, J=6.4 Hz, 1H), 7.85 (s, 1H), 7.62-7.56 (m, 2H), 7.56 (s, 1H), 7.35-7.26 (m, 2H), 3.98 (s, 2H), 3.72 (s, 2H), 2.84 (dt, J=8.8, 3.7 Hz, 1H), 2.81-2.74 (m, 1H), 2.13-2.05 (m, 1H), 1.81 (dt, J=8.4, 5.2 Hz, 1H), 1.24 (s, 6H). ¹⁹F NMR (376 MHz, DMSO-d6) δ −75.06.

Example 294. 5-(8-((2S,2S)-2-(3-(azetidine-1-carbonyl)phenyl)cyclopropyl)imidazo[1,2-b]pyridazin-6-yl)pyrimidine-2,4(1H,3H)-dione

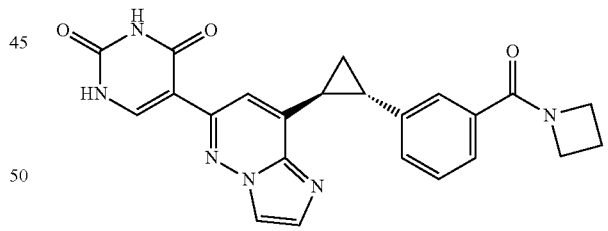

5-(8-((2S,2S)-2-(3-(azetidine-1-carbonyl)phenyl)cyclopropyl)imidazo[1,2-b]pyridazin-6-yl)pyrimidine-2,4(1H, 3H)-dione as a racemate was prepared in the manner described for Example 289, but replacing 4-((1S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((1S,2S)-2-(6-(2,4-dioxo-1,2,3,4-tetrahydropyrimidin-5-yl)imidazo[1,2-b]pyridazin-8-yl)cyclopropyl)benzoic acid and purified by RP-HPLC (5-90% MeCN/H₂O with TFA, Gemini-NX column) as a TFA salt.

ES/MS m/z: 429.10 [M+H]. ¹H NMR (400 MHz, DMSO-d6) δ 11.70-11.46 (m, 2H), 8.41 (d, J=1.6 Hz, 1H), 8.05 (d, J=6.1 Hz, 1H), 7.98 (s, 1H), 7.64 (s, 1H), 7.48-7.45 (m, 1H), 7.45-7.42 (m, 1H), 7.42-7.36 (m, 2H), 4.29 (t, J=7.7 Hz,

2H), 4.04 (t, J=7.8 Hz, 2H), 2.87-2.73 (m, 2H), 2.25 (p, J=7.7 Hz, 2H), 2.01 (dt, J=8.9, 5.4 Hz, 1H), 1.82 (dt, J=8.6, 5.4 Hz, 1H). $^{19}$F NMR (376 MHz, DMSO-d6) δ −75.27.

Example 295. 5-(8-((1S,2S)-2-(3-(3-methylazetidine-1-carbonyl)phenyl)cyclopropyl)imidazo[1,2-b]pyridazin-6-yl)pyrimidine-2,4(1H,3H)-dione

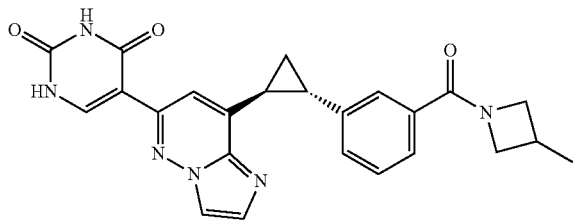 [SMILES: CC1CN(C(=O)c2cccc([C@H]3C[C@@H]3c3cc(-c4c[nH]c(=O)[nH]c4=O)nn4ccnc34)c2)C1]

5-(8-((2S,2S)-2-(3-(3-methylazetidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-((2S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((2S,2S)-2-(6-(2,4-dioxo-1,2,3,4-tetrahydropyrimidin-5-yl)imidazo[1,2-b]pyridazin-8-yl)cyclopropyl)benzoic acid and azetidine hydrochloride with 3-methylazetidine benzenesulfonate and purified by RP-HPLC (5-90% MeCN/H$_2$O with TFA, Gemini-NX column) as a TFA salt. ES/MS m/z: 443.10 [M+H]. $^1$H NMR (400 MHz, DMSO-d6) δ 11.67-11.50 (m, 2H), 8.42 (d, J=1.6 Hz, 1H), 8.06 (d, J=6.1 Hz, 1H), 7.99 (s, 1H), 7.65 (s, 1H), 7.47 (s, 1H), 7.47-7.43 (m, 1H), 7.43-7.38 (m, 2H), 4.44-4.34 (m, 1H), 4.15 (t, J=9.1 Hz, 1H), 3.87 (t, J=7.4, 6.1 Hz, 1H), 3.60 (dd, J=9.8, 5.7 Hz, 1H), 2.88-2.75 (m, 2H), 2.75-2.66 (m, 1H), 2.02 (dt, J=8.9, 5.4 Hz, 1H), 1.88-1.80 (m, 1H), 1.21 (d, J=6.9 Hz, 3H). $^{19}$F NMR (376 MHz, DMSO-d6) δ −75.29.

Example 296. 5-(8-((2S,2S)-2-(3-(3-(trifluoromethyl)azetidine-1-carbonyl)phenyl)cyclopropyl)imidazo[1,2-b]pyridazin-6-yl)pyrimidine-2,4(1H,3H)-dione

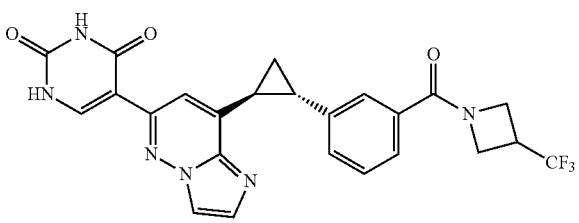 [SMILES: O=C(c1cccc([C@H]2C[C@@H]2c2cc(-c3c[nH]c(=O)[nH]c3=O)nn3ccnc23)c1)N1CC(C(F)(F)F)C1]

5-(8-((2S,2S)-2-(3-(3-(trifluoromethyl)azetidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-((2S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((1S,2S)-2-(6-(2,4-dioxo-1,2,3,4-tetrahydropyrimidin-5-yl)imidazo[1,2-b]pyridazin-8-yl)cyclopropyl)benzoic acid and azetidine hydrochloride with 3-(trifluoromethyl)azetidine and purified by RP-HPLC (5-90% MeCN/H$_2$O with TFA, Gemini-NX column) as a TFA salt. ES/MS m/z: 497.08 [M+H]. $^1$H NMR (400 MHz, DMSO-d6) δ11.65-11.48 (m, 2H), 8.38 (s, 1H), 8.05 (d, J=6.1 Hz, 1H), 7.94 (s, 1H), 7.62 (s, 1H), 7.51 (s, 1H), 7.51-7.48 (m, 1H), 7.45-7.40 (m, 2H), 4.59-4.48 (m, 1H), 4.40-4.33 (m, 1H), 4.29 (t, J=9.7 Hz, 1H), 4.00 (s, 1H), 3.71-3.61 (m, 1H), 2.91-2.82 (m, 1H), 2.79 (dt, J=10.1, 5.1 Hz, 1H), 2.03 (dt, J=9.6, 5.3 Hz, 1H), 1.87-1.78 (m, 1H). $^{19}$F NMR (376 MHz, DMSO-d6) δ −72.73 (d, J=7.2 Hz), −75.24.

Example 297. 5-(8-((2S,2S)-2-(3-(3,3-difluoroazetidine-1-carbonyl)phenyl)cyclopropyl)imidazo[1,2-b]pyridazin-6-yl)pyrimidine-2,4(1H,3H)-dione

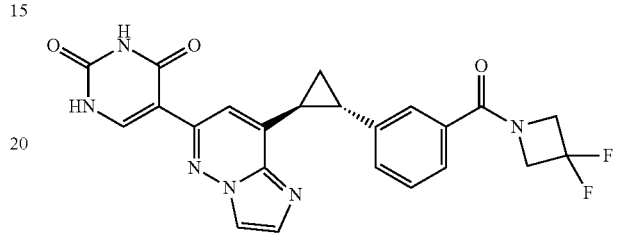

5-(8-((2S,2S)-2-(3-(3,3-difluoroazetidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-((2S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((2S,2S)-2-(6-(2,4-dioxo-1,2,3,4-tetrahydropyrimidin-5-yl)imidazo[1,2-b]pyridazin-8-yl)cyclopropyl)benzoic acid and azetidine hydrochloride with 3,3-difluoroazetidine hydrochloride and purified by RP-HPLC (5-90% MeCN/H$_2$O with TFA, Gemini-NX column) as a TFA salt. ES/MS m/z: 465.10 [M+H]. $^1$H NMR (400 MHz, DMSO-d6) δ 11.54 (s, 2H), 8.33 (s, 1H), 8.03 (d, J=6.3 Hz, 1H), 7.86 (s, 1H), 7.57 (s, 1H), 7.55-7.51 (m, 2H), 7.47-7.39 (m, 2H), 4.88-4.71 (m, 2H), 4.57-4.40 (m, 2H), 2.89 (p, J=5.3 Hz, 1H), 2.78 (dt, J=10.2, 5.1 Hz, 1H), 2.07 (dt, J=9.2, 5.0 Hz, 1H), 1.86-1.77 (m, 1H). $^{19}$F NMR (376 MHz, DMSO-d6) δ −75.02, −100.16 (p, J=12.6 Hz).

Example 298. 5-(8-((2S,2S)-2-(3-(3,3-dimethylazetidine-1-carbonyl)phenyl)cyclopropyl)imidazo[1,2-b]pyridazin-6-yl)pyrimidine-2,4(1H,3H)-dione

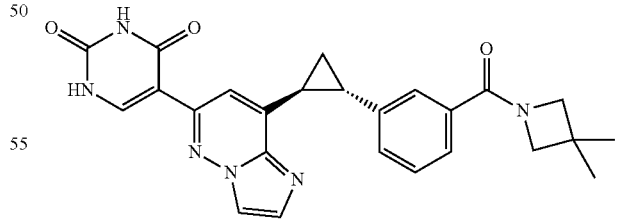

5-(8-((2S,2S)-2-(3-(3,3-dimethylazetidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-(1S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((2S,2S)-2-(6-(2,4-dioxo-1,2,3,4-tetrahydropyrimidin-5-yl)imidazo[1,2-b]pyridazin-8-yl)

cyclopropyl)benzoic acid and azetidine hydrochloride with 3,3-dimethylazetidine hydrochloride and purified by RP-HPLC (5-90% MeCN/H₂O with TFA, Gemini-NX column) as a TFA salt. ES/MS m/z: 457.13 [M+H]. ¹H NMR (400 MHz, DMSO-d6) δ 11.61-11.47 (m, 2H), 8.36 (d, J=1.5 Hz, 1H), 8.04 (d, J=6.1 Hz, 1H), 7.91 (s, 1H), 7.59 (s, 1H), 7.50-7.47 (m, 1H), 7.47-7.43 (m, 1H), 7.42-7.34 (m, 2H), 3.98 (s, 2H), 3.72 (s, 2H), 2.85 (ddd, J=8.9, 6.3, 4.4 Hz, 1H), 2.80-2.73 (m, 1H), 2.04 (dt, J=8.9, 5.4 Hz, 1H), 1.81 (dt, J=8.8, 5.5 Hz, 1H), 1.24 (s, 6H). ¹⁹F NMR (376 MHz, DMSO-d6) δ −75.12.

Example 299. 5-(8-((2S,2S)-2-(4-((3R,4R)-3,4-difluoropyrrolidine-1-carbonyl)phenyl)cyclopropyl)imidazo[1,2-b]pyridazin-6-yl)pyrimidine-2,4(1H,3H)-dione

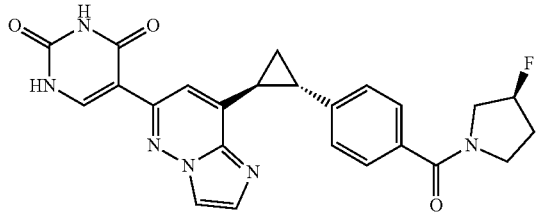

5-(8-((1S,2S)-2-(4-((3R,4R)-3,4-difluoropyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with (3R,4R)-3,4-difluoropyrrolidine hydrochloride and purified by RP-HPLC (5-90% MeCN/H₂O with TFA, Gemini-NX column) as a TFA salt. ES/MS m/z: 479.09 [M+H]. ¹H NMR (400 MHz, DMSO-d6) δ 11.54 (s, 2H), 8.32 (s, 1H), 8.02 (d, J=6.4 Hz, 1H), 7.85 (s, 1H), 7.56 (s, 1H), 7.54 (d, J=8.1 Hz, 2H), 7.38-7.29 (m, 2H), 5.37 (dd, J=48.7, 32.8 Hz, 2H), 4.04 3.76 (m, 4H), 2.91-2.83 (m, 1H), 2.79 (t, J=10.9 Hz, 2H), 2.10 (dt, J=9.6, 5.3 Hz, 1H). ¹⁹F NMR (376 MHz, DMSO-d6) δ −75.01, −188.33 (dd, J=71.3, 34.2 Hz), −190.01-190.64 (m).

Example 300. 5-(8-((2S,2S)-2-(3-((3R,4R)-3,4-difluoropyrrolidine-1-carbonyl)phenyl)cyclopropyl)imidazo[1,2-b]pyridazin-6-yl)pyrimidine-2,4(1H,3H)-dione

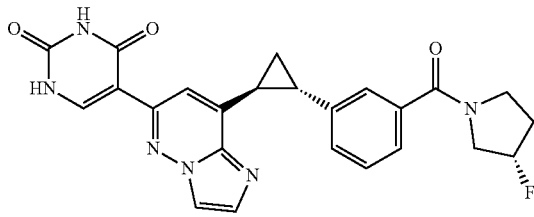

5-(8-((1S,2S)-2-(3-((3R,4R)-3,4-difluoropyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-(1S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((2S,2S)-2-(6-(2,4-dioxo-1,2,3,4-tetrahydro-pyrimidin-5-yl)imidazo[1,2-b]pyridazin-8-yl)cyclopropyl)benzoic acid and azetidine hydrochloride with (3R,4R)-3,4-difluoropyrrolidine hydrochloride and purified by RP-HPLC (5-90% MeCN/H₂O with TFA, Gemini-NX column) as a TFA salt. ES/MS m/z: 479.09 [M+H]. ¹H NMR (400 MHz, DMSO-d6) δ 11.53 (s, 2H), 8.31 (s, 1H), 8.02 (d, J=6.4 Hz, 1H), 7.83 (s, 1H), 7.55 (s, 1H), 7.46-7.43 (m, 1H), 7.43-7.35 (m, 3H), 5.36 (dd, J=49.1, 34.2 Hz, 2H), 4.07-3.69 (m, 4H), 2.88 (dtd, J=8.8, 6.1, 5.5, 3.0 Hz, 1H), 2.78 (tt, J=9.4, 5.0 Hz, 1H), 2.07 (td, J=9.0, 4.3 Hz, 1H), 1.82 (dq, J=10.7, 5.5 Hz, 1H). ¹⁹F NMR (376 MHz, DMSO-d6) δ −74.89, −188.04-188.56 (m), −190.04-190.60 (m).

Example 301. 5-(8-((2S,2S)-2-(4-((3S,4R)-3,4-difluoropyrrolidine-1-carbonyl)phenyl)cyclopropyl)imidazo[1,2-b]pyridazin-6-yl)pyrimidine-2,4(1H,3H)-dione

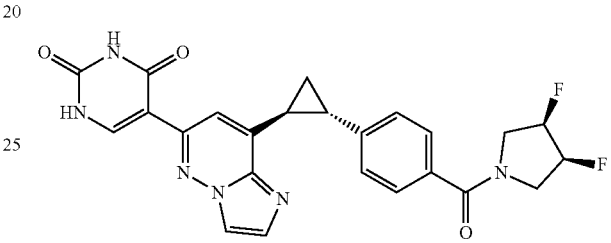

5-(8-((1S,2S)-2-(4-((3S,4R)-3,4-difluoropyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with (3S,4R)-3,4-difluoropyrrolidine hydrochloride and purified by RP-HPLC (5-90% MeCN/H₂O with TFA, Gemini-NX column) as a TFA salt. ES/MS m/z: 479.07 [M+H]. ¹H NMR (400 MHz, DMSO-d6) δ 11.64-11.42 (m, 2H), 8.34 (d, J=1.5 Hz, 1H), 8.03 (d, J=6.4 Hz, 1H), 7.87 (s, 1H), 7.57 (s, 1H), 7.54-7.46 (m, 2H), 7.33 (dd, J=8.6, 2.4 Hz, 2H), 5.50-5.09 (m, 2H), 3.95-3.80 (m, 4H), 2.83 (ddq, J=22.6, 13.5, 4.6 Hz, 2H), 2.13-2.05 (m, 1H), 1.87-1.77 (m, 1H). ¹⁹F NMR (376 MHz, DMSO-d6) δ −75.08, −204.12-−204.79 (m), −206.15-206.59 (m).

Example 302. 5-(8-((2S,2S)-2-(3-((3S,4R)-3,4-difluoropyrrolidine-1-carbonyl)phenyl)cyclopropyl)imidazo[1,2-b]pyridazin-6-yl)pyrimidine-2,4(1H,3H)-dione

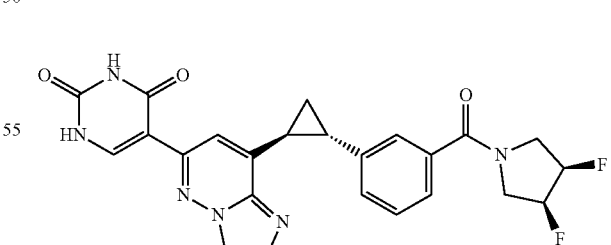

5-(8-((1S,2S)-2-(3-((3S,4R)-3,4-difluoropyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-(1S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((2S,2S)-2-(6-(2,4-dioxo-1,2,3,4-tetrahydropyrimidin-5-yl)imidazo[1,2-b]pyridazin-8-yl)cyclopropyl)benzoic acid and azetidine hydrochloride with (3S,4R)-3,4-difluoropyrrolidine hydrochloride and purified by RP-HPLC (5-90% MeCN/H$_2$O with TFA, Gemini-NX column) as a TFA salt. ES/MS m/z: 479.10 [M+H]. $^1$H NMR (400 MHz, DMSO-d6) δ 11.62-11.48 (m, 2H), 8.35 (s, 1H), 8.03 (d, J=6.1 Hz, 1H), 7.90 (s, 1H), 7.59 (s, 1H), 7.45-7.36 (m, 4H), 5.49-5.15 (m, 2H), 3.87 (dq, J=18.2, 6.8, 5.3 Hz, 2H), 3.64 (dd, J=22.4, 14.3 Hz, 2H), 2.90-2.82 (m, 1H), 2.82-2.74 (m, 1H), 2.04 (dt, J=10.3, 5.3 Hz, 1H), 1.83 (dt, J=8.6, 5.4 Hz, 1H). $^{19}$F NMR (376 MHz, DMSO-d6) δ −75.10, −204.21-204.79 (m), −205.91-206.60 (m).

Example 303. 5-(8-((1S,2S)-2-(4-(3,3,4,4-tetrafluoropyrrolidine-1-carbonyl)phenyl)cyclopropyl)imidazo[1,2-b]pyridazin-6-yl)pyrimidine-2,4(1H,3H)-dione

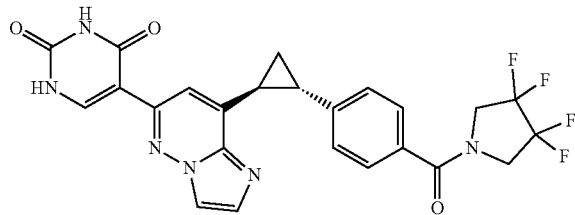 [SMILES: O=C(c1ccc([C@H]2C[C@@H]2c2cc(-c3c[nH]c(=O)[nH]c3=O)nn3ccnc23)cc1)N1CC(F)(F)C(F)(F)C1]

5-(8-((1S,2S)-2-(4-(3,3,4,4-tetrafluoropyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with 3,3,4,4-tetrafluoropyrrolidine hydrochloride and purified by RP-HPLC (5-90% MeCN/H$_2$O with TFA, Gemini-NX column) as a TFA salt. ES/MS m/z: 515.09 [M+H]. $^1$H NMR (400 MHz, DMSO-d6) δ 11.53 (s, 2H), 8.29 (s, 1H), 8.01 (d, J=6.2 Hz, 1H), 7.80 (s, 1H), 7.56 (d, J=8.0 Hz, 2H), 7.53 (s, 1H), 7.36 (d, J=8.1 Hz, 2H), 4.36-4.14 (m, 4H), 2.88 (dt, J=9.6, 5.5 Hz, 1H), 2.79 (dt, J=9.8, 5.2 Hz, 1H), 2.14 (dt, J=9.7, 5.2 Hz, 1H), 1.85-1.77 (m, 1H). $^{19}$F NMR (376 MHz, DMSO-d6) δ −74.89, −122.40--123.00 (m), −123.80--124.44 (m).

Example 304. 5-(8-((2S,2S)-2-(3-(3,3,4,4-tetrafluoropyrrolidine-1-carbonyl)phenyl)cyclopropyl)imidazo[1,2-b]pyridazin-6-yl)pyrimidine-2,4(1H,3H)-dione

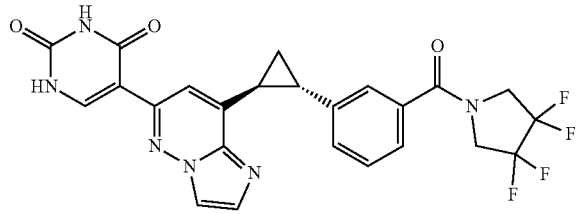 [SMILES: O=C(c1cccc([C@H]2C[C@@H]2c2cc(-c3c[nH]c(=O)[nH]c3=O)nn3ccnc23)c1)N1CC(F)(F)C(F)(F)C1]

5-(8-((1S,2S)-2-(3-(3,3,4,4-tetrafluoropyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-((2S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((1S,2S)-2-(6-(2,4-dioxo-1,2,3,4-tetrahydropyrimidin-5-yl)imidazo[1,2-b]pyridazin-8-yl)cyclopropyl)benzoic acid and azetidine hydrochloride with 3,3,4,4-tetrafluoropyrrolidine hydrochloride and purified by RP-HPLC (5-90% MeCN/H$_2$O with TFA, Gemini-NX column) as a TFA salt. ES/MS m/z: 515.09 [M+H]. $^1$H NMR (400 MHz, DMSO-d6) δ 11.56-11.46 (m, 2H), 8.28 (s, 1H), 8.01 (d, J=6.2 Hz, 1H), 7.78 (s, 1H), 7.52 (s, 1H), 7.47 (s, 1H), 7.45-7.38 (m, 3H), 4.38-4.12 (m, 4H), 2.91 (dt, J=9.6, 5.5 Hz, 1H), 2.77 (dt, J=10.1, 5.3 Hz, 1H), 2.11 (dt, J=9.6, 5.3 Hz, 1H), 1.85-1.78 (m, 1H). $^{19}$F NMR (376 MHz, DMSO-d6) δ −74.74, −122.55-122.89 (m), −123.85-124.18 (m).

Example 305. 5-(8-((2S,2S)-2-(4-(3,3-difluoropyrrolidine-1-carbonyl)phenyl)cyclopropyl)imidazo[1,2-b]pyridazin-6-yl)pyrimidine-2,4(1H,3H)-dione

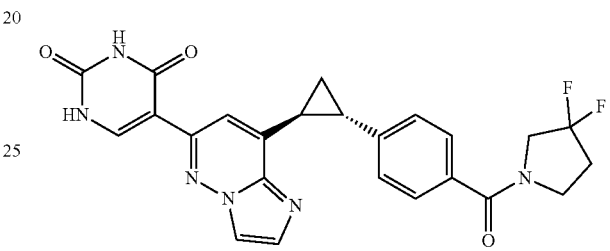

5-(8-((1S,2S)-2-(4-(3,3-difluoropyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with 3,3-difluoropyrrolidine hydrochloride and purified by RP-HPLC (5-90% MeCN/H$_2$O with TFA, Gemini-NX column) as a TFA salt. ES/MS m/z: 479.10 [M+H]. $^1$H NMR (400 MHz, DMSO-d6) δ 11.53 (s, 2H), 8.31 (d, J=1.4 Hz, 1H), 8.02 (d, J=6.4 Hz, 1H), 7.82 (s, 1H), 7.53 (d, J=9.4 Hz, 1H), 7.50 (s, 1H), 7.37-7.25 (m, 2H), 3.90 (t, J=13.1 Hz, 2H), 3.74-3.66 (m, 4H), 2.90-2.81 (m, 1H), 2.81-2.73 (m, 1H), 2.44-2.35 (m, 2H), 2.11 (dt, J=9.4, 5.2 Hz, 1H), 1.81 (dt, J=10.5, 5.3 Hz, 1H). $^{19}$F NMR (376 MHz, DMSO-d6) δ −74.93, −100.62-101.02 (m), −101.82-102.23 (m).

Example 306. 5-(8-((2S,2S)-2-(3-(3,3-difluoropyrrolidine-1-carbonyl)phenyl)cyclopropyl)imidazo[1,2-b]pyridazin-6-yl)pyrimidine-2,4(1H,3H)-dione

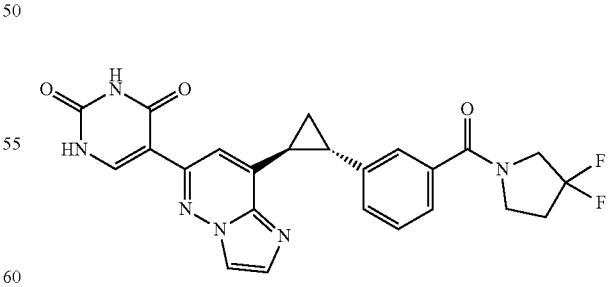

5-(8-((2S,2S)-2-(3-(3,3-difluoropyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-((2S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((1S,2S)-2-(6-(2,4-dioxo-1,2,3,4-tetrahydropyrimidin-5-yl)imidazo[1,2-b]pyridazin-8-yl)cyclopropyl)benzoic acid and azetidine hydrochloride with 3,3-difluoropyrrolidine hydrochloride and purified by RP-HPLC (5-90% MeCN/H₂O with TFA, Gemini-NX column) as a TFA salt. ES/MS m/z: 479.04 [M+H]. ¹H NMR (400 MHz, DMSO-d6) δ 11.63-11.49 (m, 2H), 8.36 (s, 1H), 8.04 (d, J=6.1 Hz, 1H), 7.90 (s, 1H), 7.59 (s, 1H), 7.46-7.35 (m, 4H), 3.90 (t, J=13.1 Hz, 2H), 3.76-3.64 (m, 2H), 2.91-2.82 (m, 1H), 2.78 (dt, J=10.0, 5.3 Hz, 1H), 2.48-2.37 (m, 2H), 2.06 (dt, J=9.8, 5.3 Hz, 1H), 1.83 (dt, J=10.9, 5.5 Hz, 1H). ¹⁹F NMR (376 MHz, DMSO-d6) δ −75.10, −100.54−−100.75 (m), −101.78−102.00 (m).

Example 307. 5-(8-((2S,2S)-2-(4-(3,3-dimethylpyrrolidine-1-carbonyl)phenyl)cyclopropyl)imidazo[1,2-b]pyridazin-6-yl)pyrimidine-2,4(1H,3H)-dione

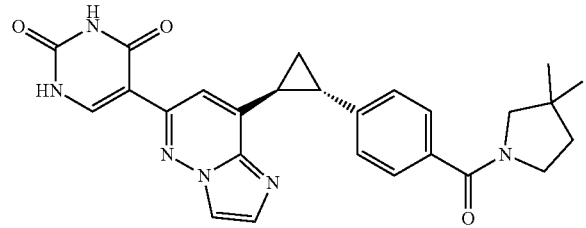 [SMILES: CC1(C)CCN(C(=O)c2ccc([C@H]3C[C@@H]3c3cc(-c4c[nH]c(=O)[nH]c4=O)nn4ccnc34)cc2)C1]

5-(8-((1S,2S)-2-(4-(3,3-dimethylpyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing azetidine hydrochloride with 3,3-dimethylpyrrolidine hydrochloride and purified by RP-HPLC (5-90% MeCN/H₂O with TFA, Gemini-NX column) as a TFA salt. ES/MS m/z: 471.15 [M+H]. ¹H NMR (400 MHz, DMSO-d6) δ 11.53 (s, 2H), 8.31 (s, 1H), 8.02 (d, J=6.4 Hz, 1H), 7.84 (s, 1H), 7.55 (s, 1H), 7.46 (dd, J=15.7, 7.9 Hz, 2H), 7.30 (d, J=8.1 Hz, 2H), 3.57-3.51 (m, 1H), 3.51 3.46 (m, 1H), 3.22 (s, 1H), 3.17 (s, 1H), 2.87-2.80 (m, 1H), 2.77 (dt, J=9.9, 5.5 Hz, 1H), 2.13-2.05 (m, 1H), 1.83-1.76 (m, 1H), 1.68 (t, J=7.3 Hz, 1H), 1.64 (t, J=7.3 Hz, 1H), 1.10 (s, 3H), 0.97 (s, 3H). ¹⁹F NMR (376 MHz, DMSO-d6) δ −74.97.

Example 308. 5-(8-((1S,2S)-2-(3-(3,3-dimethylpyrrolidine-1-carbonyl)phenyl)cyclopropyl)imidazo[1,2-b]pyridazin-6-yl)pyrimidine-2,4(1H,3H)-dione

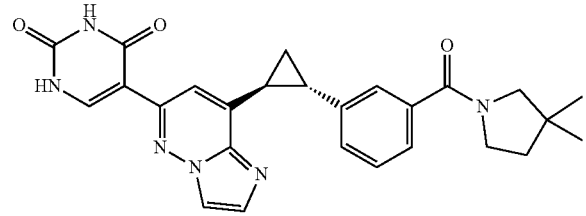 [SMILES: CC1(C)CCN(C(=O)c2cccc([C@H]3C[C@@H]3c3cc(-c4c[nH]c(=O)[nH]c4=O)nn4ccnc34)c2)C1]

5-(8-((1S,2S)-2-(3-(3,3-dimethylpyrrolidine-1-carbonyl)phenyl)cyclopropyl)imidazo[1,2-b]pyridazin-6-yl)pyrimidine-2,4(1H,3H)-dione as a racemate was prepared in the manner described for Example 289, but replacing 4-(1S,2S)-2-(6-(2,4-dioxo-1,2,3,4-tetrahydropyrimidin-5-yl)imidazo[1,2-b]pyridazin-8-yl)cyclopropyl)benzoic acid with racemic 3-((2S,2S)-2-(6-(2,4-dioxo-1,2,3,4-tetrahydropyrimidin-5-yl)imidazo[1,2-b]pyridazin-8-yl)cyclopropyl)benzoic acid and azetidine hydrochloride with 3,3-dimethylpyrrolidine hydrochloride and purified by RP-HPLC (5-90% MeCN/H₂O with TFA, Gemini-NX column) as a TFA salt. ES/MS m/z: 471.16 [M+H]. ¹H NMR (400 MHz, DMSO-d6) δ 11.54 (s, 2H), 8.32 (s, 1H), 8.03 (d, J=6.4 Hz, 1H), 7.84 (s, 1H), 7.54 (s, 1H), 7.41-7.31 (m, 4H), 3.55 (t, J=7.3 Hz, 1H), 3.48 (t, J=7.0 Hz, 1H), 3.23 (s, 1H), 3.16 (s, 1H), 2.86 (dt, J=10.0, 5.8 Hz, 1H), 2.77 (dt, J=9.8, 5.4 Hz, 1H), 2.07 (dt, J=11.1, 5.4 Hz, 1H), 1.85-1.77 (m, 1H), 1.69 (t, J=7.2 Hz, 1H), 1.64 (t, J=7.0 Hz, 1H), 1.11 (s, 3H), 0.98 (d, J=2.9 Hz, 3H). ¹⁹F NMR (376 MHz, DMSO-d6) δ −74.89.

Example 309. 5-(8-((1S,2S)-2-(2-(trifluoromethoxy)phenyl)cyclopropyl)imidazo[1,2-b]pyridazin-6-yl)pyrimidine-2,4(1H,3H)-dione

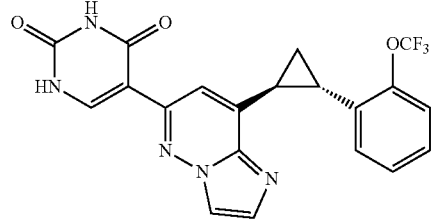 [SMILES: O=c1[nH]cc(-c2cc([C@H]3C[C@@H]3c3ccccc3OC(F)(F)F)c3nccn3n2)c(=O)[nH]1]

5-(8-((1S,2S)-2-(2-(trifluoromethoxy)phenyl)cyclopropyl)imidazo[1,2-b]pyridazin-6-yl)pyrimidine-2,4(1H,3H)-dione as a racemate was prepared in the manner described for Example 1, but replacing 8-cyclopropyl-6-(2,4-dimethoxypyrimidin-5-yl)-2-methyl-imidazo[1,2-b]pyridazine with racemic 6-(2,4-dimethoxypyrimidin-5-yl)-8-((1S,2S)-2-(2-(trifluoromethoxy)phenyl)cyclopropyl)imidazo[1,2-b]pyridazine and purified by RP-HPLC (10-90% MeCN/H₂O with TFA, Gemini-NX column) as a TFA salt. ES/MS m/z: 430.05 [M+H]. ¹H NMR (400 MHz, DMSO-d6) δ 11.55 (d, J=7.7 Hz, 2H), 8.36 (s, 1H), 8.05 (d, J=6.0 Hz, 1H), 7.91 (s, 1H), 7.66 (s, 1H), 7.51-7.25 (m, 4H), 3.04 (dt, J=9.6, 5.8 Hz, 1H), 2.74 (dt, J=9.9, 5.5 Hz, 1H), 2.09 (dt, J=9.1, 5.4 Hz, 1H), 1.84 (dt, J=8.3, 5.3 Hz, 1H). ¹⁹F NMR (376 MHz, DMSO-d6) δ −56.92, −75.19.

Example 310. 4-((1S,2S)-2-(6-(2,4-dioxo-1,2,3,4-tetrahydropyrimidin-5-yl)-3-fluoroimidazo[1,2-b]pyridazin-8-yl)cyclopropyl)-3-fluorobenzonitrile

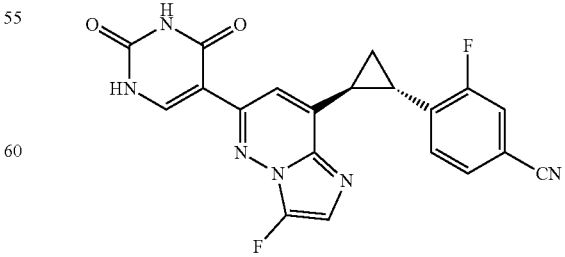

4-((1S,2S)-2-(6-(2,4-dioxo-1,2,3,4-tetrahydropyrimidin-5-yl)-3-fluoroimidazo[1,2-b]pyridazin-8-yl)cyclopropyl)-3- fluorobenzonitrile was prepared in the manner described for Example 1, but replacing 8-cyclopropyl-6-(2,4-dimethoxypyrimidin-5-yl)-2-methyl-imidazo[1,2-b]pyridazine with 4-((1S,2S)-2-(6-(2,4-dimethoxypyrimidin-5-yl)-3-fluoroimidazo[1,2-b]pyridazin-8-yl)cyclopropyl)-3-fluorobenzonitrile and purified by RP-HPLC (10-90% MeCN/H₂O with TFA, Gemini-NX column) as a TFA salt. ES/MS m/z: 407.00 [M+H]. ¹H NMR (400 MHz, DMSO-d6) δ 11.53 (s, 2H), 8.02 (d, J=6.4 Hz, 1H), 7.82 (dd, J=10.2, 1.6 Hz, 1H), 7.69 (dd, J=8.1, 1.6 Hz, 1H), 7.57-7.52 (m, 2H), 7.49 (t, J=7.9 Hz, 1H), 3.11 (dt, J=9.2, 5.8 Hz, 1H), 2.86-2.77 (m, 1H), 2.23 (ddd, J=9.0, 6.1, 4.8 Hz, 1H), 1.94 1.85 (m, 1H). ¹⁹F NMR (376 MHz, DMSO-d6) δ −75.03, −118.11 (dd, J=10.2, 7.7 Hz), −155.57 (d, J=7.0 Hz).

Example 311. 5-((2S,2S)-2-(6-(2,4-dioxo-1,2,3,4-tetrahydropyrimidin-5-yl)imidazo[1,2-b]pyridazin-8-yl)cyclopropyl)nicotinonitrile

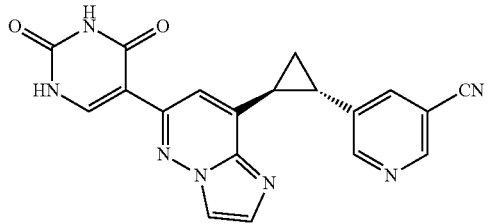 [SMILES: N#Cc1cncc([C@H]2C[C@@H]2c2cc(-c3c[nH]c(=O)[nH]c3=O)nn3ccnc23)c1]

5-((1S,2S)-2-(6-(2,4-dioxo-1,2,3,4-tetrahydropyrimidin-5-yl)imidazo[1,2-b]pyridazin-8-yl)cyclopropyl)nicotinonitrile as a racemate was prepared in the manner described for Example 1, but replacing 8-cyclopropyl-6-(2,4-dimethoxypyrimidin-5-yl)-2-methyl-imidazo[1,2-b]pyridazine with racemic 5-((1S,2S)-2-(6-(2,4-dimethoxypyrimidin-5-yl)imidazo[1,2-b]pyridazin-8-yl)cyclopropyl)nicotinonitrile and purified by RP-HPLC (10-60% MeCN/H₂O with TFA, Gemini-NX column) as a TFA salt. ES/MS m/z: 372.20 [M+H]. ¹H NMR (400 MHz, DMSO-d6) δ 11.67-11.48 (m, 2H), 8.87 (d, J=1.9 Hz, 1H), 8.85 (d, J=2.3 Hz, 1H), 8.38 (d, J=1.5 Hz, 1H), 8.21 (t, J=2.1 Hz, 1H), 8.05 (d, J=6.1 Hz, 1H), 7.93 (s, 1H), 7.67 (s, 1H), 2.98-2.90 (m, 1H), 2.90-2.83 (m, 1H), 2.19 (dt, J=8.9, 5.4 Hz, 1H), 1.94 (dt, J=8.6, 5.5 Hz, 1H). ¹⁹F NMR (376 MHz, DMSO-d6) δ −75.29.

Example 312. 4-((2S,2S)-2-(6-(2,4-dioxo-1,2,3,4-tetrahydropyrimidin-5-yl)-3-fluoroimidazo[1,2-b]pyridazin-8-yl)cyclopropyl)-N-methylbenzamide

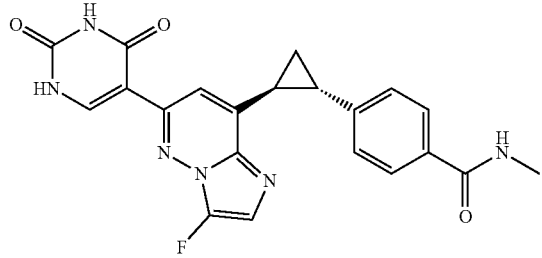 [SMILES: CNC(=O)c1ccc([C@H]2C[C@@H]2c2cc(-c3c[nH]c(=O)[nH]c3=O)nn3c(F)cnc23)cc1]

4-((1S,2S)-2-(6-(2,4-dioxo-1,2,3,4-tetrahydropyrimidin-5-yl)-3-fluoroimidazo[1,2-b]pyridazin-8-yl)cyclopropyl)-N-methylbenzamide as a racemate was prepared in the manner described for Example 289, but replacing 4-((2S,2S)-2-(6-(2,4-dioxo-1,2,3,4-tetrahydropyrimidin-5-yl)imidazo[1,2-b]pyridazin-8-yl)cyclopropyl)benzoic acid with racemic 4-((2S,2S)-2-(6-(2,4-dioxo-1,2,3,4-tetrahydropyrimidin-5-yl)-3-fluoroimidazo[1,2-b]pyridazin-8-yl)cyclopropyl)benzoic acid and azetidine hydrochloride with 2 M methylamine in THF and purified by RP-HPLC (5-90% MeCN/H₂O with TFA, Gemini-NX column) as a TFA salt. ES/MS m/z: 421.04 [M+H]. ¹H NMR (400 MHz, DMSO-d6) δ 11.58-11.48 (m, 2H), 8.37 (q, J=4.4 Hz, 1H), 8.02 (d, J=6.4 Hz, 1H), 7.83-7.74 (m, 2H), 7.54 (d, J=7.1 Hz, 1H), 7.47 (s, 1H), 7.34-7.30 (m, 2H), 2.88 (ddd, J=9.0, 6.5, 4.8 Hz, 1H), 2.77 (d, J=4.5 Hz, 3H), 2.76-2.71 (m, 1H), 2.13 (dt, J=8.9, 5.3 Hz, 1H), 1.85-1.77 (m, 1H). ¹⁹F NMR (376 MHz, DMSO-d6) δ −74.89, −155.59 (d, J=7.3 Hz).

Example 313. 5-(8-((1S,2S)-2-(4-(3,3-difluoroazetidine-1-carbonyl)phenyl)cyclopropyl)-3-fluoroimidazo[1,2-b]pyridazin-6-yl)pyrimidine-2,4(1H,3H)-dione

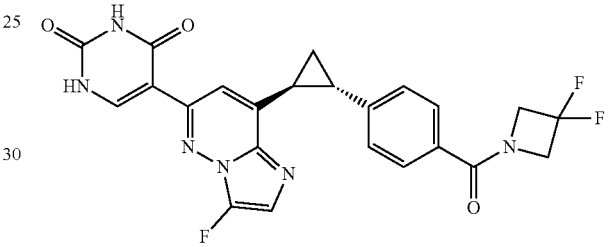

5-(8-((1S,2S)-2-(4-(3,3-difluoroazetidine-1-carbonyl)phenyl)cyclopropyl)-3-fluoroimidazo[1,2-b]pyridazin-6-yl)pyrimidine-2,4(1H,3H)-dione and 5-(8-((1R,2R)-2-(4-(3,3-difluoroazetidine-1-carbonyl)phenyl)cyclopropyl)-3-fluoroimidazo[1,2-b]pyridazin-6-yl)pyrimidine-2,4(1H,3H)-dione were prepared as a racemic mixture in the manner described for Example 289, but replacing 4-((2S,2S)-2-(6-(2,4-dioxo-1,2,3,4-tetrahydropyrimidin-5-yl)imidazo[1,2-b]pyridazin-8-yl)cyclopropyl)benzoic acid with racemic 4-(1S,2S)-2-(6-(2,4-dioxo-1,2,3,4-tetrahydropyrimidin-5-yl)-3-fluoroimidazo[1,2-b]pyridazin-8-yl)cyclopropyl)benzoic acid and azetidine hydrochloride with 3,3-difluoroazetidine hydrochloride and isolated by filtration as an HCl salt. ES/MS m/z: 483.01 [M+H]. ¹H NMR (400 MHz, DMSO-d6) δ 11.53 (s, 2H), 8.02 (s, 1H), 7.66-7.61 (m, 2H), 7.54 (d, J=7.1 Hz, 1H), 7.48 (s, 1H), 7.38-7.32 (m, 2H), 4.97-4.64 (m, 2H), 4.64-4.26 (m, 2H), 2.92-2.85 (m, 1H), 2.79-2.71 (m, 1H), 2.16 (dt, J=10.6, 5.5 Hz, 1H), 1.81 (dt, J=8.7, 5.3 Hz, 1H). ¹⁹F NMR (376 MHz, DMSO-d6) δ −100.10 (p, J=12.6 Hz), −155.57 (d, J=7.1 Hz).

5-(8-((1S,2S)-2-(4-(3,3-difluoroazetidine-1-carbonyl)phenyl)cyclopropyl)-3-fluoroimidazo[1,2-b]pyridazin-6-yl)pyrimidine-2,4(1H,3H)-dione was separated by SFC using 35% EtOH on a OJ-H column. Example 313 was the second eluting peak. ES/MS m/z: 483.02 [M+H]. ¹H NMR (400 MHz, DMSO-d6) δ 11.60-11.49 (m, 2H), 8.03 (d, J=6.4 Hz, 1H), 7.67-7.60 (m, 2H), 7.54 (d, J=7.1 Hz, 1H), 7.48 (s, 1H), 7.37-7.31 (m, 2H), 4.84-4.67 (m, 2H), 4.55-4.41 (m, 2H), 2.88 (ddd, J=9.0, 6.5, 4.4 Hz, 1H), 2.78-2.72 (m, 1H), 2.16 (dt, J=8.9, 5.3 Hz, 1H), 1.81 (dt, J=8.8, 5.5 Hz, 1H). ¹⁹F NMR (376 MHz, DMSO-d6) δ −75.18, −100.11 (p, J=12.6 Hz), −155.56 (d, J=7.1 Hz).

Example 314. methyl (1R,5S,6r)-3-(6-(2,4-dioxo-1,2,3,4-tetrahydropyrimidin-5-yl)imidazo[1,2-b]pyridazin-8-yl)-3-azabicyclo[3.1.0]hexane-6-carboxylate

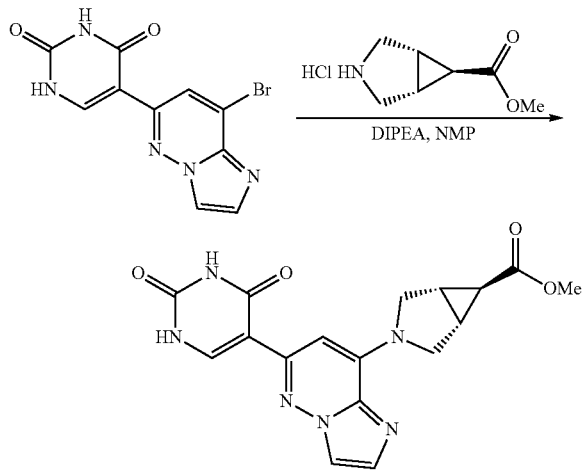

To 5-(8-bromoimidazo[1,2-b]pyridazin-6-yl)pyrimidine-2,4(1H,3H)-dione (100 mg, 0.33 mmol) and methyl (1R,5S,6r)-3-azabicyclo[3.1.0]hexane-6-carboxylate hydrochloride (64 mg, 0.36 mmol, 1.1 equiv) in NMP (3 mL) was added DIPEA (0.13 mL, 0.71 mmol, 2.2 equiv) and the mixture was heated to 130° C. After 24 h, the material was purified by RP-HPLC (5-60% MeCN/H₂O with TFA, Gemini-NX column) to afford methyl (1R,5S,6r)-3-(6-(2,4-dioxo-1,2,3,4-tetrahydropyrimidin-5-yl)imidazo[1,2-b]pyridazin-8-yl)-3-azabicyclo[3.1.0]hexane-6-carboxylate as a TFA salt. ES/MS m/z: 369.08 [M+H]. ¹H NMR (400 MHz, DMSO-d6) δ 11.39 (d, J=2.0 Hz, 1H), 11.35 (d, J=6.4 Hz, 1H), 8.02 (d, J=1.2 Hz, 1H), 7.92 (d, J=6.2 Hz, 1H), 7.54 (d, J=1.2 Hz, 1H), 6.57 (s, 1H), 4.45-4.23 (m, 2H), 3.85-3.77 (m, 2H), 3.63 (s, 3H), 2.32-2.26 (m, 2H), 1.62 (t, J=3.1 Hz, 1H). ¹⁹F NMR (376 MHz, DMSO-d6) δ −74.90.

Example 315. 5-(8-(2-azaspiro[4.4]nonan-2-yl)imidazo[1,2-b]pyridazin-6-yl)pyrimidine-2,4(1H,3H)-dione

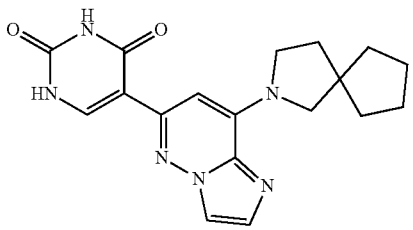 [SMILES: O=c1[nH]cc(-c2cc(N3CCC4(CCCC4)C3)c3nccn3n2)c(=O)[nH]1]

5-(8-(2-azaspiro[4.4]nonan-2-yl)imidazo[1,2-b]pyridazin-6-yl)pyrimidine-2,4(1H,3H)-dione was prepared in the manner described for Example 314, but replacing methyl (1R,5S,6R)-3-azabicyclo[3.1.0]hexane-6-carboxylate hydrochloride with 2-azaspiro[4.4]nonane and purified by RP-HPLC (5-90% MeCN/H₂O with TFA, Gemini-NX column) as a TFA salt. ES/MS m/z: 353.10 [M+H]. ¹H NMR (400 MHz, DMSO-d6) δ 11.39 (s, 1H), 11.36 (d, J=6.2 Hz, 1H), 8.06-8.01 (m, 1H), 7.94 (d, J=6.0 Hz, 1H), 7.59 (s, 1H), 6.59 (s, 1H), 3.88-3.49 (m, 4H), 1.91 (t, J=6.9 Hz, 2H), 1.73-1.64 (m, 4H), 1.64-1.51 (m, 4H). ¹⁹F NMR (376 MHz, DMSO-d6) δ −75.15.

Example 316. 5-(8-((2S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione

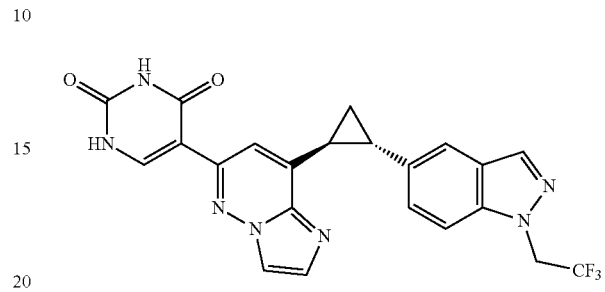

5-(8-((1S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(1-(2,2,2-trifluoroethyl)-1H-indazol-5-yl)cyclopropyl)imidazo[1,2-b]pyridazine and isolated by filtration as a HCl salt. ES/MS m/z: 468.00 [M+H]. ¹H NMR (400 MHz, DMSO-d6) δ 11.62-11.48 (m, 2H), 8.35 (s, 1H), 8.14 (s, 1H), 8.04 (d, J=6.0 Hz, 1H), 7.90 (s, 1H), 7.75 (d, J=8.7 Hz, 1H), 7.68 (s, 1H), 7.59 (s, 1H), 7.39 (dd, J=8.8, 1.6 Hz, 1H), 5.44 (q, J=9.2 Hz, 2H), 2.96-2.89 (m, 1H), 2.81-2.74 (m, 1H), 2.04 (dt, J=10.0, 5.3 Hz, 1H), 1.85 (dt, J=8.6, 5.4 Hz, 1H). ¹⁹F NMR (376 MHz, DMSO-d6) δ −70.15 (t, J=9.1 Hz).

Example 317. 5-(3-fluoro-8-((2S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione

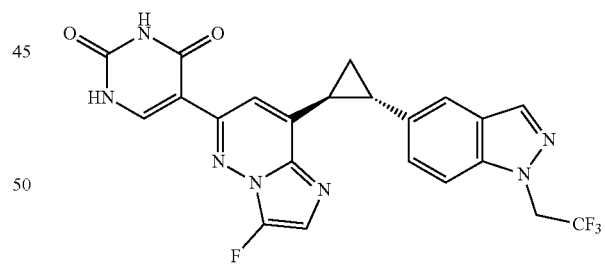

5-(3-fluoro-8-((1S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((1S,2S)-2-(1-(2,2,2-trifluoroethyl)-1H-indazol-5-yl)cyclopropyl)imidazo[1,2-b]pyridazine and isolated by filtration as a HCl salt. ES/MS m/z: 486.00 [M+H]. ¹H NMR (400 MHz, DMSO-d6) δ 11.58 11.47 (m, 2H), 8.13 (s, 1H), 8.03 (d, J=6.5 Hz, 1H), 7.74 (d, J=8.7 Hz, 1H), 7.68 (s, 1H), 7.54 (d, J=7.1 Hz, 1H), 7.47 (s, 1H), 7.39 (dd, J=8.7, 1.6 Hz, 1H), 5.43 (q, J=9.2 Hz, 2H), 2.95 (ddd, J=9.1, 6.3, 4.4 Hz, 1H), 2.76-2.68 (m, 1H), 2.14-2.03 (m, 1H), 1.81 (ddd, J=8.7, 6.3, 4.8 Hz, 1H). ¹⁹F NMR (376 MHz, DMSO-d6) δ −70.16 (t, J=9.2 Hz), −155.62 (d, J=7.0 Hz).

Example 318. 5-(8-((2S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione

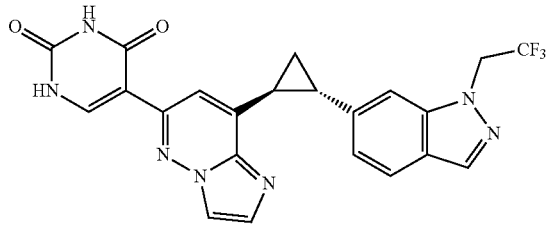 [SMILES: O=c1[nH]cc(-c2cc([C@H]3C[C@@H]3c3ccc4cnn(CC(F)(F)F)c4c3)c3nccn3n2)c(=O)[nH]1]

5-(8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(1-(2,2,2-trifluoroethyl)-1H-indazol-6-yl)cyclopropyl)imidazo[1,2-b]pyridazine and purified by RP-HPLC (10-90% MeCN/H₂O with TFA, Gemini-NX column) as a TFA salt. ES/MS m/z: 468.00 [M+H]. ¹H NMR (400 MHz, DMSO-d6) δ 11.61 (dd, J=6.2, 2.0 Hz, 1H), 11.57 (d, J=2.0 Hz, 1H), 8.40 (d, J=1.5 Hz, 1H), 8.16 (s, 1H), 8.06 (d, J=6.2 Hz, 1H), 7.97 (d, J=1.6 Hz, 1H), 7.74 (d, J=8.1 Hz, 2H), 7.67 (s, 1H), 7.11 (dd, J=8.3, 1.3 Hz, 1H), 5.41 (q, J=9.1 Hz, 2H), 2.96 (ddd, J=9.0, 6.4, 4.3 Hz, 1H), 2.83 (dt, J=9.9, 5.4 Hz, 1H), 2.08 (dt, J=8.9, 5.3 Hz, 1H), 1.94 (dt, J=8.5, 5.4 Hz, 1H). ¹⁹F NMR (376 MHz, DMSO-d6) δ −70.07 (t, J=9.1 Hz), −75.32.

Example 319. 5-(3-fluoro-8-((2S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione

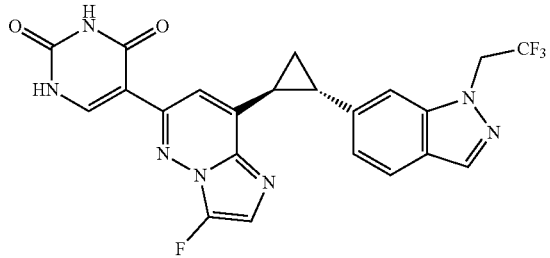 [SMILES: O=c1[nH]cc(-c2cc([C@H]3C[C@@H]3c3ccc4cnn(CC(F)(F)F)c4c3)c3ncc(F)n3n2)c(=O)[nH]1]

5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((1S,2S)-2-(1-(2,2,2-trifluoroethyl)-1H-indazol-6-yl)cyclopropyl)imidazo[1,2-b]pyridazine and isolated by filtration as a HCl salt. ES/MS m/z: 486.00 [M+H]. ¹H NMR (400 MHz, DMSO-d6) δ 11.58-11.47 (m, 2H), 8.13 (s, 1H), 8.03 (d, J=6.5 Hz, 1H), 7.74 (d, J=8.7 Hz, 1H), 7.68 (s, 1H), 7.54 (d, J=7.1 Hz, 1H), 7.47 (s, 1H), 7.39 (dd, J=8.7, 1.6 Hz, 1H), 5.43 (q, J=9.2 Hz, 2H), 2.95 (ddd, J=9.1, 6.3, 4.4 Hz, 1H), 2.76-2.68 (m, 1H), 2.14-2.03 (m, 1H), 1.81 (ddd, J=8.7, 6.3, 4.8 Hz, 1H). ¹⁹F NMR (376 MHz, DMSO-d6) δ −70.16 (t, J=9.2 Hz), −155.62 (d, J=7.0 Hz).

Example 320. 5-(8-(3,3-difluoro-5,5-dimethylpiperidin-1-yl)imidazo[1,2-b]pyridazin-6-yl)pyrimidine-2,4(1H,3H)-dione

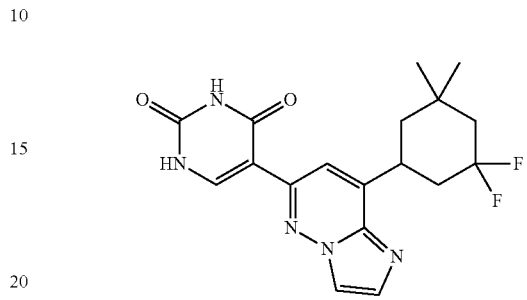

5-(8-(3,3-difluoro-5,5-dimethylpiperidin-1-yl)imidazo[1,2-b]pyridazin-6-yl)pyrimidine-2,4(1H,3H)-dione was prepared in the manner described for Example 314, but replacing methyl (1R,5S,6r)-3-azabicyclo[3.1.0]hexane-6-carboxylate hydrochloride with 3,3-difluoro-5,5-dimethylpiperidine heated for 48 h and purified by RP-HPLC (5-90% MeCN/H₂O with TFA, Gemini-NX column) as a TFA salt. ES/MS m/z: 377.10 [M+H]. ¹H NMR (400 MHz, DMSO-d6) δ 11.40 (d, J=2.0 Hz, 1H), 11.39-11.33 (m, 1H), 8.05 (d, J=1.1 Hz, 1H), 7.93 (d, J=6.1 Hz, 1H), 7.58 (d, J=1.2 Hz, 1H), 7.01 (s, 1H), 4.64 (t, J=12.4 Hz, 2H), 3.77 (s, 2H), 1.98 (t, J=15.0 Hz, 2H), 1.03 (s, 6H). ¹⁹F NMR (376 MHz, DMSO-d6) δ −75.15, −94.90 (p, J=13.7, 13.3 Hz).

Example 321. 5-(8-((2S,2S)-2-(2-methylbenzo[d]thiazol-5-yl)cyclopropyl)imidazo[1,2-b]pyridazin-6-yl)pyrimidine-2,4(1H,3H)-dione

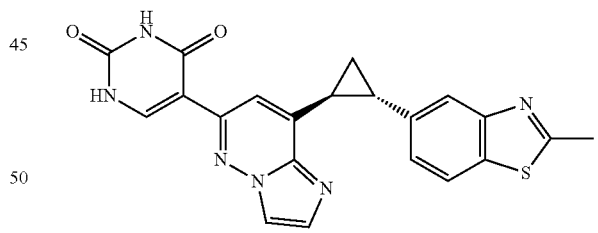

5-(8-((2S,2S)-2-(2-methylbenzo[d]thiazol-5-yl)cyclopropyl)imidazo[1,2-b]pyridazin-6-yl)pyrimidine-2,4(1H,3H)-dione as a racemate was prepared in the manner described for Example 1, but replacing 8-cyclopropyl-6-(2,4-dimethoxypyrimidin-5-yl)-2-methyl-imidazo[1,2-b]pyridazine with racemic 5-((1S,2S)-2-(6-(2,4-dimethoxypyrimidin-5-yl)imidazo[1,2-b]pyridazin-8-yl)cyclopropyl)-2-methyl-benzo[d]thiazole and purified by RP-HPLC (10-90% MeCN/H₂O with TFA, Gemini-NX column) as a TFA salt. ES/MS m/z: 417.02 [M+H]. ¹H NMR (400 MHz, DMSO-d6) δ 11.65-11.50 (m, 2H), 8.39 (d, J=1.6 Hz, 1H), 8.06 (d, J=6.1 Hz, 1H), 8.00-7.91 (m, 2H), 7.82 (d, J=1.6 Hz, 1H), 7.64 (s, 1H), 7.31 (dd, J=8.4, 1.8 Hz, 1H), 2.93 (ddd, J=9.1, 6.3, 4.4 Hz, 1H), 2.83 (ddd, J=8.7, 5.8, 4.2 Hz, 1H), 2.80 (s, 3H), 2.08 (dt, J=9.1, 5.3 Hz, 1H), 1.89 (ddd, J=8.7, 6.4, 5.0 Hz, 1H). $^{19}$F NMR (376 MHz, DMSO-d6) δ −75.16.

Example 322. 5-(8-((1S,2S)-2-(1-(2,2,2-trifluoroethyl)-1H-benzo[d]imidazol-6-yl)cyclopropyl)imidazo[1,2-b]pyridazin-6-yl)pyrimidine-2,4(1H,3H)-dione

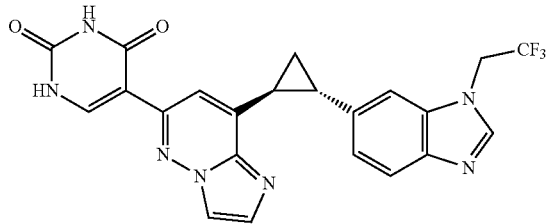 [SMILES: O=c1[nH]cc(-c2cc([C@H]3C[C@@H]3c3ccc4ncn(CC(F)(F)F)c4c3)c3nccn3n2)c(=O)[nH]1]

5-(8-((1S,2S)-2-(1-(2,2,2-trifluoroethyl)-1H-benzo[d]imidazol-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(1-(2,2,2-trifluoroethyl)-1H-benzo[d]imidazol-6-yl)cyclopropyl)imidazo[1,2-b]pyridazine and purified by RP-HPLC (10-90% MeCN/H$_2$O with TFA, Gemini-NX column) as a TFA salt. ES/MS m/z: 468.04 [M+H]. $^1$H NMR (400 MHz, DMSO-d6) δ 11.61 (dd, J=6.2, 2.0 Hz, 1H), 11.57 (d, J=1.9 Hz, 1H), 8.63 (s, 1H), 8.41 (d, J=1.6 Hz, 1H), 8.06 (d, J=6.2 Hz, 1H), 7.99 (d, J=1.6 Hz, 1H), 7.77 (s, 1H), 7.70 (d, J=8.4 Hz, 1H), 7.67 (s, 1H), 7.27 (dd, J=8.5, 1.6 Hz, 1H), 5.41 (q, J=9.2 Hz, 2H), 2.96 (ddd, J=9.1, 6.4, 4.3 Hz, 1H), 2.84-2.75 (m, 1H), 2.06 (dt, J=9.0, 5.3 Hz, 1H), 1.95-1.86 (m, 1H). $^{19}$F NMR (376 MHz, DMSO-d6) δ −70.70 (t, J=9.2 Hz), −75.38.

Example 323. 5-(3-fluoro-8-((2S,2S)-2-(1-(2,2,2-trifluoroethyl)-1H-benzo[d]imidazol-6-yl)cyclopropyl)imidazo[1,2-b]pyridazin-6-yl)pyrimidine-2,4(1H,3H)-dione

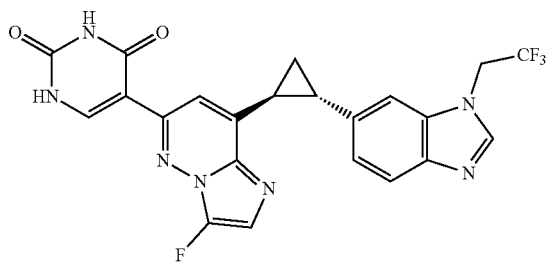 [SMILES: O=c1[nH]cc(-c2cc([C@H]3C[C@@H]3c3ccc4ncn(CC(F)(F)F)c4c3)c3ncc(F)n3n2)c(=O)[nH]1]

5-(3-fluoro-8-((1S,2S)-2-(1-(2,2,2-trifluoroethyl)-1H-benzo[d]imidazol-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((2S,2S)-2-(1-(2,2,2-trifluoroethyl)-1H-benzo[d]imidazol-6-yl)cyclopropyl)imidazo[1,2-b]pyridazine and purified by RP-HPLC (10-90% MeCN/H$_2$O with TFA, Gemini-NX column) as a TFA salt. ES/MS m/z: 486.00 [M+H]. $^1$H NMR (400 MHz, DMSO-d6) δ 11.58-11.47 (m, 2H), 8.56 (s, 1H), 8.03 (d, J=6.4 Hz, 1H), 7.74 (s, 1H), 7.66 (d, J=8.4 Hz, 1H), 7.54 (d, J=7.1 Hz, 1H), 7.48 (s, 1H), 7.26 (dd, J=8.4, 1.5 Hz, 1H), 5.39 (q, J=9.2 Hz, 2H), 3.02 (ddd, J=9.2, 6.2, 4.3 Hz, 1H), 2.73 (dt, J=9.5, 5.3 Hz, 1H), 2.14 (dt, J=8.9, 5.2 Hz, 1H), 1.84 (dt, J=8.5, 5.2 Hz, 1H). $^{19}$F NMR (376 MHz, DMSO-d6) δ −70.74 (t, J=9.1 Hz), −75.32, −155.55 (d, J=7.0 Hz).

Example 324. 5-(8-((2S,2S)-2-(1-(2,2,2-trifluoroethyl)-1H-benzo[d]imidazol-5-yl)cyclopropyl)imidazo[1,2-b]pyridazin-6-yl)pyrimidine-2,4(1H,3H)-dione

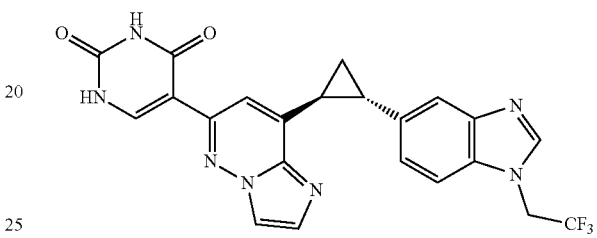

5-(8-((1S,2S)-2-(1-(2,2,2-trifluoroethyl)-1H-benzo[d]imidazol-5-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(1-(2,2,2-trifluoroethyl)-1H-benzo[d]imidazol-5-yl)cyclopropyl)imidazo[1,2-b]pyridazine and purified by RP-HPLC (10-90% MeCN/H$_2$O with TFA, Gemini-NX column) as a TFA salt. ES/MS m/z: 468.03 [M+H]. $^1$H NMR (400 MHz, DMSO-d6) δ 11.64 (dd, J=6.3, 2.0 Hz, 1H), 11.59 (d, J=2.0 Hz, 1H), 8.65 (s, 1H), 8.46 (d, J=1.6 Hz, 1H), 8.08 (d, J=6.2 Hz, 1H), 8.07 (d, J=1.7 Hz, 1H), 7.76 (d, J=8.5 Hz, 1H), 7.71 (s, 1H), 7.65 (d, J=1.5 Hz, 1H), 7.35 (dd, J=8.5, 1.6 Hz, 1H), 5.43 (q, J=9.2 Hz, 2H), 2.90 (ddd, J=9.1, 6.4, 4.3 Hz, 1H), 2.86-2.78 (m, 1H), 2.01 (dt, J=8.9, 5.4 Hz, 1H), 1.92 (dt, J=8.5, 5.4 Hz, 1H). $^{19}$F NMR (376 MHz, DMSO-d6) δ −70.74 (t, J=9.2 Hz), −75.37.

Example 325. 5-(8-(8,8-difluoro-6-azaspiro[3.4]octan-6-yl)imidazo[1,2-b]pyridazin-6-yl)pyrimidine-2,4(1H,3H)-dione

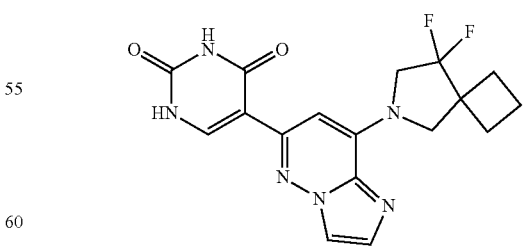

5-(8-(8,8-difluoro-6-azaspiro[3.4]octan-6-yl)imidazo[1,2-b]pyridazin-6-yl)pyrimidine-2,4(1H,3H)-dione was prepared in the manner described for Example 314, but replacing methyl (1R,5S,6r)-3-azabicyclo[3.1.0]hexane-6-carboxylate hydrochloride with 8,8-difluoro-6-azaspiro[3.4]

octane and purified by filtration as a HCl salt. ES/MS m/z: 375.10 [M+H]. $^1$H NMR (400 MHz, DMSO-d6) δ 11.40 (s, 1H), 11.37 (d, J=5.4 Hz, 1H), 8.05 (d, J=1.1 Hz, 1H), 7.92 (d, J=5.9 Hz, 1H), 7.56 (d, J=1.1 Hz, 1H), 6.57 (s, 1H), 4.42-4.22 (m, 2H), 4.16-3.97 (m, 2H), 2.39-2.28 (m, 2H), 2.10-2.01 (m, 2H), 2.01-1.93 (m, 1H), 1.94-1.79 (m, 1H). $^{19}$F NMR (376 MHz, DMSO-d6) δ −116.97.

Example 326. 5-(8-((1S,2S)-2-(1-methyl-1H-indazol-6-yl)cyclopropyl)imidazo[1,2-b]pyridazin-6-yl)pyrimidine-2,4(1H,3H)-dione

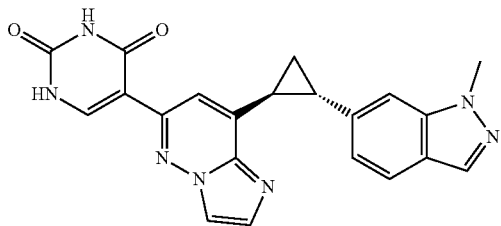 [SMILES: Cn1ncc2ccc([C@H]3C[C@@H]3c3cc(-c4c[nH]c(=O)[nH]c4=O)nn4ccnc34)cc21]

5-(8-((1S,2S)-2-(1-methyl-1H-indazol-6-yl)cyclopropyl)imidazo[1,2-b]pyridazin-6-yl)pyrimidine-2,4(1H,3H)-dione as a racemate was prepared in the manner described for Example 1, but replacing 8-cyclopropyl-6-(2,4-dimethoxypyrimidin-5-yl)-2-methyl-imidazo[1,2-b]pyridazine with racemic 6-(2,4-dimethoxypyrimidin-5-yl)-8-((2S,2S)-2-(1-methyl-1H-indazol-6-yl)cyclopropyl)imidazo[1,2-b]pyridazine and purified by RP-HPLC (10-90% MeCN/H$_2$O with TFA, Gemini-NX column) as a TFA salt. ES/MS m/z: 400.02 [M+H]. $^1$H NMR (400 MHz, DMSO-d6) δ 11.53 (s, 2H), 8.30 (s, 1H), 8.02 (d, J=6.3 Hz, 1H), 7.98 (s, 1H), 7.82 (s, 1H), 7.68 (d, J=8.4 Hz, 1H), 7.56 (s, 1H), 7.53 (s, 1H), 7.03 (d, J=8.6 Hz, 1H), 4.02 (s, 3H), 2.98 (dt, J=9.4, 5.7 Hz, 1H), 2.81 (dt, J=9.8, 5.4 Hz, 1H), 2.17-2.08 (m, 1H), 1.96-1.87 (m, 1H). $^{19}$F NMR (376 MHz, DMSO-d6) δ −74.91.

Example 327. 5-(8-((2S,2S)-2-(3-(trifluoromethyl)benzo[d]isoxazol-5-yl)cyclopropyl)imidazo[1,2-b]pyridazin-6-yl)pyrimidine-2,4(1H,3H)-dione

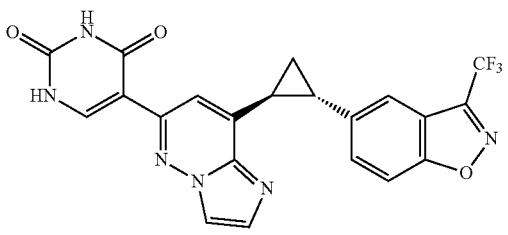 [SMILES: O=c1[nH]cc(-c2cc([C@H]3C[C@@H]3c3ccc4onc(C(F)(F)F)c4c3)c3nccn3n2)c(=O)[nH]1]

5-(8-((1S,2S)-2-(3-(trifluoromethyl)benzo[d]isoxazol-5-yl)cyclopropyl)imidazo[1,2-b]pyridazin-6-yl)pyrimidine-2,4(1H,3H)-dione as a racemate was prepared in the manner described for Example 1, but replacing 8-cyclopropyl-6-(2,4-dimethoxypyrimidin-5-yl)-2-methyl-imidazo[1,2-b]pyridazine with racemic 5-((2S,2S)-2-(6-(2,4-dimethoxypyrimidin-5-yl)imidazo[1,2-b]pyridazin-8-yl)cyclopropyl)-3-(trifluoromethyl)benzo[d]isoxazole and purified by RP-HPLC (10-90% MeCN/H$_2$O with TFA, Gemini-NX column) as a TFA salt. ES/MS m/z: 455.00 [M+H]. $^1$H NMR (400 MHz, DMSO-d6) δ 11.53 (s, 2H), 8.31 (d, J=1.4 Hz, 1H), 8.02 (d, J=6.4 Hz, 1H), 7.98 (d, J=8.9 Hz, 1H), 7.88 (s, 1H), 7.82 (s, 1H), 7.78 (dd, J=9.0, 1.8 Hz, 1H), 7.57 (s, 1H), 3.09 (ddd, J=9.0, 6.2, 4.6 Hz, 1H), 2.87-2.80 (m, 1H), 2.18-2.10 (m, 1H), 1.93 (dt, J=8.8, 5.5 Hz, 1H). $^{19}$F NMR (376 MHz, DMSO-d6) δ −62.09, −74.93.

Example 328. 5-(2-chloro-8-(3,3-difluoro-4,4-dimethylpyrrolidin-1-yl)imidazo[1,2-b]pyridazin-6-yl)pyrimidine-2,4(1H,3H)-dione

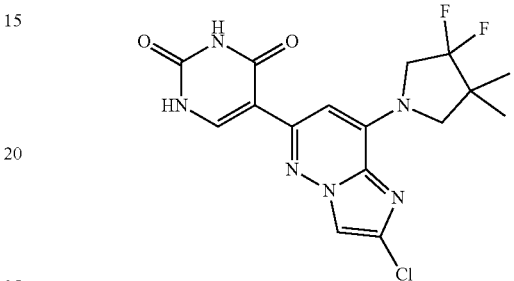

To 2-chloro-8-(3,3-difluoro-4,4-dimethylpyrrolidin-1-yl)-6-(2,4-dimethoxypyrimidin-5-yl)imidazo[1,2-b]pyridazine (40 mg, 0.09 mmol) in DMF (0.5 mL) was added TMSI (0.09 mL, 0.63 mmol). After 4 h, additional TMSI (0.05 mL, 0.35 mmol) was added. After an additional 17 h, MeOH was added to the mixture and the solids were isolated by filtration to afford 5-(2-chloro-8-(3,3-difluoro-4,4-dimethylpyrrolidin-1-yl)imidazo[1,2-b]pyridazin-6-yl)pyrimidine-2,4(1H,3H)-dione as a HI salt. ES/MS m/z: 397.00 [M+H]. $^1$H NMR (400 MHz, DMSO-d6) δ 11.49-11.36 (m, 2H), 8.23 (s, 1H), 7.93 (d, J=6.1 Hz, 1H), 6.67 (s, 1H), 4.54-4.18 (m, 2H), 3.99-3.66 (m, 2H), 1.20 (s, 6H). $^{19}$F NMR (376 MHz, DMSO-d6) δ −115.35 (t, J=12.8 Hz).

Example 329. 5-(3-fluoro-8-((2S,2S)-2-(1-(2,2,2-trifluoroethyl)-3-(trifluoromethyl)-1H-indazol-6-yl)cyclopropyl)imidazo[1,2-b]pyridazin-6-yl)pyrimidine-2,4(1H,3H)-dione

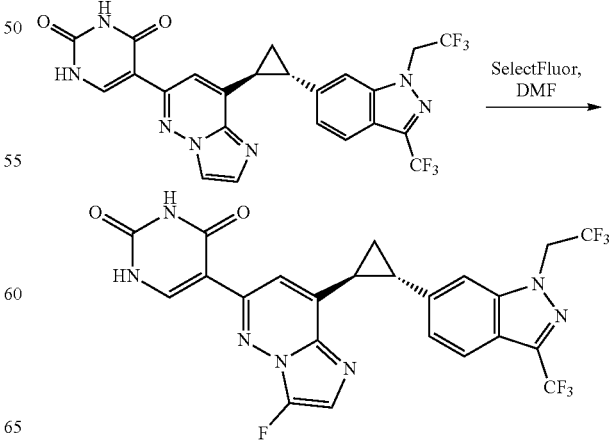

To a solution of Example 607 (115.6 mg, 0.02 mmol) in DMF (0.7 mL) was added SelectFluor (11 mg, 0.03 mmol) and stirred for 16 h. Direct purification of the reaction mixture was accomplished by reverse phase HPLC (5-90% MeCN/H$_2$O with 0.1% TFA) affording 5-(3-fluoro-8-((1S, 2S)-2-(1-(2,2,2-trifluoroethyl)-3-(trifluoromethyl)-1H-indazol-6-yl)cyclopropyl)imidazo[1,2-b]pyridazin-6-yl)pyrimidine-2,4(1H,3H)-dione. ES/MS m/z: 554.00 [M+H]. $^1$H NMR (400 MHz, DMSO-d6) δ 11.63-11.42 (m, 2H), 8.04 (d, J=6.4 Hz, 1H), 7.94 (s, 1H), 7.79 (d, J=8.5 Hz, 1H), 7.56 (d, J=7.1 Hz, 1H), 7.52 (s, 1H), 7.37 (dd, J=8.6, 1.1 Hz, 1H), 5.62 (q, J=9.2, 8.8 Hz, 2H), 3.16-3.06 (m, 1H), 2.88-2.76 (m, 1H), 2.26-2.17 (m, 1H), 1.97-1.82 (m, 1H). $^{19}$F NMR (376 MHz, DMSO-d6) δ −60.43, −70.03 (t, J=9.0 Hz), −155.55 (d, J=7.0 Hz).

Examples 330 and 331. (S)-5-(8-(3,3-difluoro-4-((4-(trifluoromethyl)pyridin-2-yl)oxy)pyrrolidin-1-yl)imidazo[1,2-b]pyridazin-6-yl)pyrimidine-2,4(1H,3H)-dione and (R)-5-(8-(3,3-difluoro-4-(4-(trifluoromethyl)pyridin-2-yl)oxy)pyrrolidin-1-yl)imidazo[1,2-b]pyridazin-6-yl)pyrimidine-2,4(1H,3H)-dione

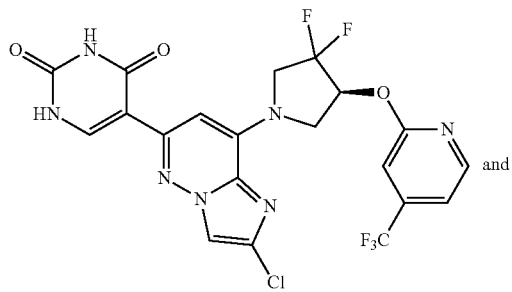

and

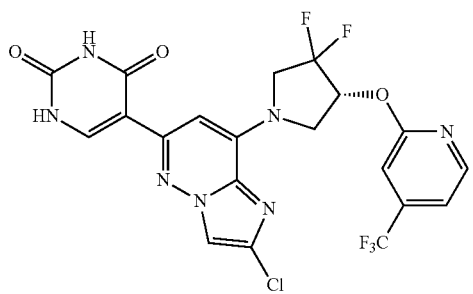

A solution of 8-(3,3-difluoro-4-(4-(trifluoromethyl)pyridin-2-yl)oxy)pyrrolidin-1-yl)-6-(2,4-dimethoxypyrimidin-5-yl)imidazo[1,2-b]pyridazine (100 mg, 0.19 mmol) in 1:1 1N HCl:MeOH (2 mL) was heated to 80° C. After 3 hours, the reaction solvent was evaporated and the residue was purified with Prep HPLC, affording 5-(8-(3,3-difluoro-4-((4-(trifluoromethyl)pyridin-2-yl)oxy)pyrrolidin-1-yl)imidazo[1,2-b]pyridazin-6-yl)pyrimidine-2,4(1H,3H)-dione. ES/MS m/z: 496.10 [M+H]. $^1$H NMR (400 MHz, DMSO-d6) δ 11.49-11.28 (m, 2H), 8.53 (d, J=5.3 Hz, 1H), 8.09 (d, J=1.1 Hz, 1H), 7.95 (d, J=6.1 Hz, 1H), 7.59 (d, J=1.1 Hz, 1H), 7.49 (dd, J=5.4, 1.4 Hz, 1H), 7.43 (s, 1H), 6.65 (s, 1H), 6.01 (dd, J=8.9, 5.2 Hz, 1H), 4.82-4.36 (m, 4H). $^{19}$F NMR (376 MHz, DMSO-d6) δ −64.03, −75.18, −108.34, −119.74 (d, J=236.7 Hz).

5-(8-(3,3-difluoro-4-((4-(trifluoromethyl)pyridin-2-yl)oxy)pyrrolidin-1-yl)imidazo[1,2-b]pyridazin-6-yl)pyrimidine-2,4(1H,3H)-dione was purified with chiral SFC column to afford two single enantiomers (S)-5-(8-(3,3-difluoro-4-(4-(trifluoromethyl)pyridin-2-yl)oxy)pyrrolidin-1-yl)imidazo[1,2-b]pyridazin-6-yl)pyrimidine-2,4(1H,3H)-dione and (R)-5-(8-(3,3-difluoro-4-((4-(trifluoromethyl)pyridin-2-yl)oxy)pyrrolidin-1-yl)imidazo[1,2-b]pyridazin-6-yl)pyrimidine-2,4(1H,3H)-dione.

Example 330 (S)-5-(8-(3,3-difluoro-4-((4-(trifluoromethyl)pyridin-2-yl)oxy)pyrrolidin-1-yl)imidazo[1,2-b]pyridazin-6-yl)pyrimidine-2,4(1H,3H)-dione. ES/MS m/z: 496.10 [M+H]. $^1$H NMR (400 MHz, DMSO-d6) δ 11.49-11.28 (m, 2H), 8.53 (d, J=5.3 Hz, 1H), 8.09 (d, J=1.1 Hz, 1H), 7.95 (d, J=6.1 Hz, 1H), 7.59 (d, J=1.1 Hz, 1H), 7.49 (dd, J=5.4, 1.4 Hz, 1H), 7.43 (s, 1H), 6.65 (s, 1H), 6.01 (dd, J=8.9, 5.2 Hz, 1H), 4.82-4.36 (m, 4H). $^{19}$F NMR (376 MHz, DMSO-d6) δ −64.03, −75.18, −108.34, −119.74 (d, J=236.7 Hz). And Example 331 (R)-5-(8-(3,3-difluoro-4-((4-(trifluoromethyl)pyridin-2-yl)oxy)pyrrolidin-1-yl)imidazo[1,2-b]pyridazin-6-yl)pyrimidine-2,4(1H,3H)-dione. ES/MS m/z: 496.10 [M+H]. $^1$H NMR (400 MHz, DMSO-d6) δ 11.49-11.28 (m, 2H), 8.53 (d, J=5.3 Hz, 1H), 8.09 (d, J=1.1 Hz, 1H), 7.95 (d, J=6.1 Hz, 1H), 7.59 (d, J=1.1 Hz, 1H), 7.49 (dd, J=5.4, 1.4 Hz, 1H), 7.43 (s, 1H), 6.65 (s, 1H), 6.01 (dd, J=8.9, 5.2 Hz, 1H), 4.82-4.36 (m, 4H). $^{19}$F NMR (376 MHz, DMSO-d6) δ −64.03, −75.18, −108.34, −119.74 (d, J=236.7 Hz).

Examples 332 and 333. (R)-5-(8-(4-(5-(difluoromethoxy)pyridin-2-yl)oxy)-3,3-difluoropyrrolidin-1-yl)imidazo[1,2-b]pyridazin-6-yl)pyrimidine-2,4(1H,3H)-dione and (S)-5-(8-(4-(5-(difluoromethoxy)pyridin-2-yl)oxy)-3,3-difluoropyrrolidin-1-yl)imidazo[1,2-b]pyridazin-6-yl)pyrimidine-2,4(1H,3H)-dione

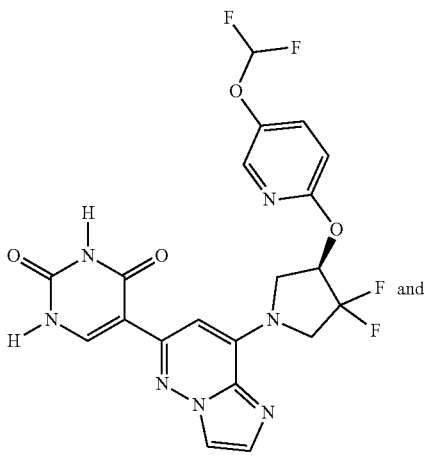

and

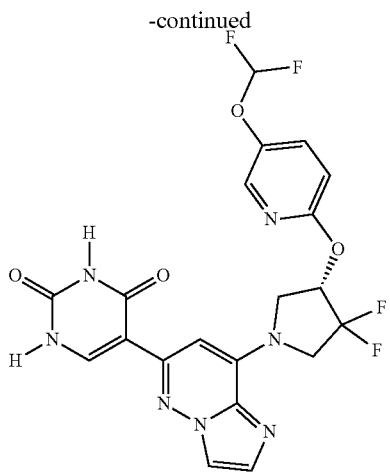

5-(8-(4-((5-(difluoromethoxy)pyridin-2-yl)oxy)-3,3-difluoropyrrolidin-1-yl)imidazo[1,2-b]pyridazin-6-yl)pyrimidine-2,4(1H,3H)-dione was purified with chiral SFC column to afford two single enantiomer (R)-5-(8-(4-((5-(difluoromethoxy)pyridin-2-yl)oxy)-3,3-difluoropyrrolidin-1-yl)imidazo[1,2-b]pyridazin-6-yl)pyrimidine-2,4(1H,3H)-dione ES/MS m/z: 494.20 [M+H]. $^1$H NMR (400 MHz, Acetonitrile-d3) δ 9.18 (s, 2H), 8.11 (d, J=3.0 Hz, 1H), 8.04 (d, J=6.4 Hz, 1H), 7.97 (d, J=1.6 Hz, 1H), 7.70 (d, J=1.6 Hz, 1H), 7.62 (dd, J=9.0, 3.0 Hz, 1H), 7.01 (s, 1H), 6.98-6.47 (m, 2H), 5.88 (dq, J=8.3, 4.3 Hz, 1H), 4.59-4.32 (m, 3H). $^{19}$F NMR (377 MHz, Acetonitrile-d3) δ −77.24, −83.60 (d, J=73.9 Hz), −108.66−−110.24 (m), −121.52−−122.84 (m). and (S)-5-(8-(4-((5-(difluoromethoxy)pyridin-2-yl)oxy)-3,3-difluoropyrrolidin-1-yl)imidazo[1,2-b]pyridazin-6-yl)pyrimidine-2,4(1H,3H)-dione. ES/MS m/z: 494.20 [M+H]. $^1$H NMR (400 MHz, Acetonitrile-d3) δ 9.18 (s, 2H), 8.11 (d, J=3.0 Hz, 1H), 8.04 (d, J=6.4 Hz, 1H), 7.97 (d, J=1.6 Hz, 1H), 7.70 (d, J=1.6 Hz, 1H), 7.62 (dd, J=9.0, 3.0 Hz, 1H), 7.01 (s, 1H), 6.98-6.47 (m, 2H), 5.88 (dq, J=8.3, 4.3 Hz, 1H), 4.59-4.32 (m, 3H). $^{19}$F NMR (377 MHz, Acetonitrile-d3) δ −77.24, −83.60 (d, J=73.9 Hz), −108.66-110.24 (m), −121.52−−122.84 (m).

Examples 334 and 335. (R)-5-(8-(3,3-difluoro-4-(5-(trifluoromethoxy)pyridin-2-yl)oxy)pyrrolidin-1-yl)imidazo[1,2-b]pyridazin-6-yl)pyrimidine-2,4(1H,3H)-dione and (S)-5-(8-(3,3-difluoro-4-(5-(trifluoromethoxy)pyridin-2-yl)oxy)pyrrolidin-1-yl)imidazo[1,2-b]pyridazin-6-yl)pyrimidine-2,4(1H,3H)-dione

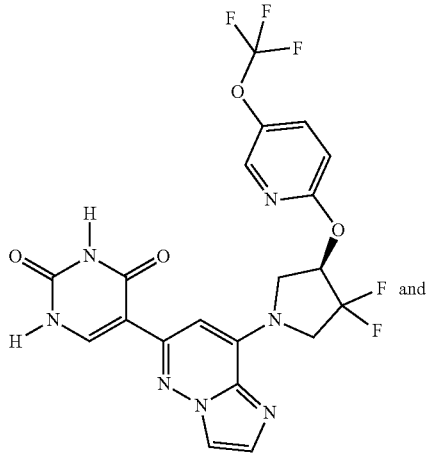

and

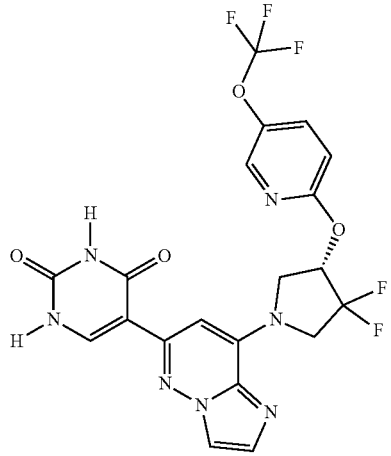

5-(8-(3,3-difluoro-4-((5-(trifluoromethoxy)pyridin-2-yl)oxy)pyrrolidin-1-yl)imidazo[1,2-b]pyridazin-6-yl)pyrimidine-2,4(1H,3H)-dione was prepared in the manner described for Examples 330 and 331 replacing Intermediate 514 with Intermediate 516 and purified by RP-HPLC as a TFA salt.

5-(8-(3,3-difluoro-4-((5-(trifluoromethoxy)pyridin-2-yl)oxy)pyrrolidin-1-yl)imidazo[1,2-b]pyridazin-6-yl)pyrimidine-2,4(1H,3H)-dione was separated with chiral SFC column to afford two single enantiomers (S)-5-(8-(4-((5-(1,1-difluoroethoxy)pyridin-2-yl)oxy)-3,3-difluoropyrrolidin-1-yl)imidazo[1,2-b]pyridazin-6-yl)pyrimidine-2,4(1H,3H)-dione and (R)-5-(8-(3,3-difluoro-4-((5-(trifluoromethoxy)pyridin-2-yl)oxy)pyrrolidin-1-yl)imidazo[1,2-b]pyridazin-6-yl)pyrimidine-2,4(1H,3H)-dione.

Example 334 (R)-5-(8-(4-((5-(1,1-trifluoromethoxy)pyridin-2-yl)oxy)-3,3-difluoropyrrolidin-1-yl)imidazo[1,2-b]pyridazin-6-yl)pyrimidine-2,4(1H,3H)-dione ES/MS m/z: 512.20 [M+H]. $^1$H NMR (400 MHz, Acetonitrile-d3) δ 9.16 (s, 2H), 8.24 (d, J=2.9 Hz, 1H), 8.03 (d, J=6.4 Hz, 1H), 7.95 (d, J=1.5 Hz, 1H), 7.77-7.70 (m, 1H), 7.68 (d, J=1.5 Hz, 1H), 7.08-6.87 (m, 2H), 5.90 (tt, J=8.6, 3.9 Hz, 1H), 4.61-4.34 (m, 3H), 4.21 (d, J=12.4 Hz, 1H). $^{19}$F NMR (376 MHz, Acetonitrile-d3) δ −60.13, −77.24 (d, J=1.5 Hz), −106.81−−111.83 (m), −122.07 (d, J=240.9 Hz).

Example 335 (S)-5-(8-(3,3-difluoro-4-(5-(trifluoromethoxy)pyridin-2-yl)oxy)pyrrolidin-1-yl)imidazo[1,2-b]pyridazin-6-yl)pyrimidine-2,4(1H,3H)-dione ES/MS m/z: 512.20 [M+H]. $^1$H NMR (400 MHz, Acetonitrile-d3) δ 9.16 (s, 2H), 8.24 (d, J=2.9 Hz, 1H), 8.03 (d, J=6.4 Hz, 1H), 7.95 (d, J=1.5 Hz, 1H), 7.77-7.70 (m, 1H), 7.68 (d, J=1.5 Hz, 1H), 7.08-6.87 (m, 2H), 5.90 (tt, J=8.6, 3.9 Hz, 1H), 4.61-4.34 (m, 3H), 4.21 (d, J=12.4 Hz, 1H). $^{19}$F NMR (376 MHz, Acetonitrile-d3) δ −60.13, −77.24 (d, J=1.5 Hz), −106.81−−111.83 (m), −122.07 (d, J=240.9 Hz).

Examples 336 and 337. (R)-5-(8-(3,3-difluoro-4-(5-(perfluoroethoxy)pyridin-2-yl)oxy)pyrrolidin-1-yl)imidazo[1,2-b]pyridazin-6-yl)pyrimidine-2,4(1H,3H)-dione and (S)-5-(8-(3,3-difluoro-4-(5-(perfluoroethoxy)pyridin-2-yl)oxy)pyrrolidin-1-yl)imidazo[1,2-b]pyridazin-6-yl)pyrimidine-2,4(1H,3H)-dione

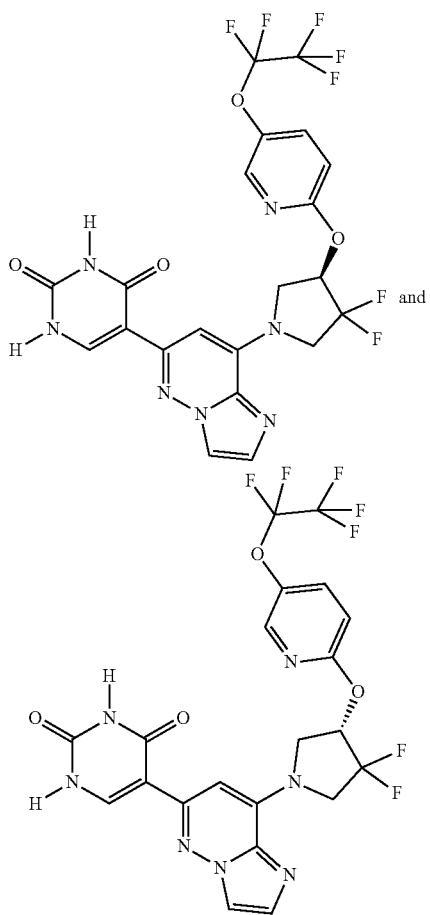

5-(8-(3,3-difluoro-4-((5-(perfluoroethoxy)pyridin-2-yl)oxy)pyrrolidin-1-yl)imidazo[1,2-b]pyridazin-6-yl)pyrimidine-2,4(1H,3H)-dione was prepared as in the manner described for Examples 330 and 331 replacing Intermediate 514 with Intermediate 517 and purified by RP-HPLC as a TFA salt.

5-(8-(3,3-difluoro-4-((5-(perfluoroethoxy)pyridin-2-yl)oxy)pyrrolidin-1-yl)imidazo[1,2-b]pyridazin-6-yl)pyrimidine-2,4(1H,3H)-dione was purified with chiral SFC column to afford two single enantiomers (S)-5-(8-(3,3-difluoro-4-((5-(perfluoroethoxy)pyridin-2-yl)oxy)pyrrolidin-1-yl)imidazo[1,2-b]pyridazin-6-yl)pyrimidine-2,4(1H,3H)-dione and (R)-5-(8-(3,3-difluoro-4-(5-(perfluoroethoxy)pyridin-2-yl)oxy)pyrrolidin-1-yl)imidazo[1,2-b]pyridazin-6-yl)pyrimidine-2,4(1H,3H)-dione.

Example 336 (R)-5-(8-(3,3-difluoro-4-((5-(perfluoroethoxy)pyridin-2-yl)oxy)pyrrolidin-1-yl)imidazo[1,2-b]pyridazin-6-yl)pyrimidine-2,4(1H,3H)-dione ES/MS m/z: 562.10. $^1$H NMR (400 MHz, Acetonitrile-d3) δ 9.17 (s, 2H), 8.23 (d, J=2.9 Hz, 1H), 8.06 (d, J=6.4 Hz, 1H), 7.98 (d, J=1.6 Hz, 1H), 7.74 (dd, J=10.3, 2.3 Hz, 2H), 7.13-6.81 (m, 2H), 5.91 (h, J=4.3 Hz, 1H), 4.54-4.34 (m, 3H), 4.20 (dt, J=12.3, 2.6 Hz, 1H). $^{19}$F NMR (376 MHz, Acetonitrile-d3) δ −77.25, −87.18, −89.01, −108.05−−111.75 (m), −120.35−−123.36 (m). Example 337: (S)-5-(8-(3,3-difluoro-4-(5-(perfluoroethoxy)pyridin-2-yl)oxy)pyrrolidin-1-yl)imidazo[1,2-b]pyridazin-6-yl)pyrimidine-2,4(1H,3H)-dione ES/MS m/z: 562.10. $^1$H NMR (400 MHz, Acetonitrile-d3) δ 9.17 (s, 2H), 8.23 (d, J=2.9 Hz, 1H), 8.06 (d, J=6.4 Hz, 1H), 7.98 (d, J=1.6 Hz, 1H), 7.74 (dd, J=10.3, 2.3 Hz, 2H), 7.13-6.81 (m, 2H), 5.91 (h, J=4.3 Hz, 1H), 4.54-4.34 (m, 3H), 4.20 (dt, J=12.3, 2.6 Hz, 1H). $^{19}$F NMR (376 MHz, Acetonitrile-d3) δ −77.25, −87.18, −89.01, −108.05−−111.75 (m), −120.35−−123.36 (m).

Examples 338 and 339. (R)-6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile and (S)-6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile

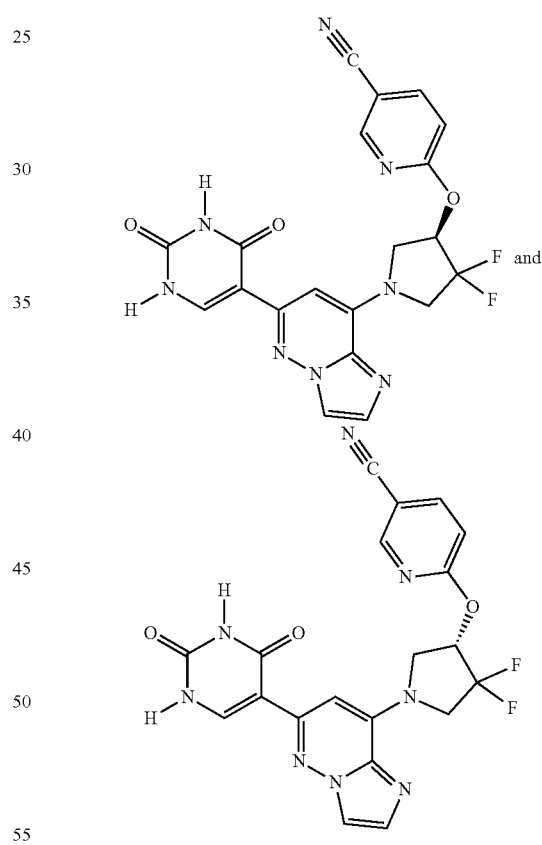

6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile was prepared in the manner described for Examples 330 and 331 replacing Intermediate 514 with Intermediate 518 and purified by RP-HPLC as a TFA salt.

6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile was purified with chiral SFC column to afford two single enantiomers (S)-6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile and (R)-6-

((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile.

Example 338 (R)-6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile. ES/MS m/z: 453.20. $^{1}$H NMR (400 MHz, Acetonitrile-d3) δ 9.30 (d, J=12.5 Hz, 2H), 8.61 (d, J=2.3 Hz, 1H), 8.15-8.02 (m, 2H), 8.02 (d, J=1.8 Hz, 1H), 7.79 (d, J=1.8 Hz, 1H), 7.17 (s, 1H), 7.04 (d, J=8.7 Hz, 1H), 6.00 (ddt, J=8.3, 4.9, 3.1 Hz, 1H), 4.46 (td, J=18.2, 10.3 Hz, 3H), 4.19 (dt, J=12.1, 2.7 Hz, 1H). $^{19}$F NMR (377 MHz, Acetonitrile-d3) δ −77.23, −109.58 (d, J=241.9 Hz), −121.92 (d, J=241.8 Hz).

(S)-6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile. ES/MS m/z: 453.20. $^{1}$H NMR (400 MHz, Acetonitrile-d3) δ 9.30 (d, J=12.5 Hz, 2H), 8.61 (d, J=2.3 Hz, 1H), 8.15-8.02 (m, 2H), 8.02 (d, J=1.8 Hz, 1H), 7.79 (d, J=1.8 Hz, 1H), 7.17 (s, 1H), 7.04 (d, J=8.7 Hz, 1H), 6.00 (ddt, J=8.3, 4.9, 3.1 Hz, 1H), 4.46 (td, J=18.2, 10.3 Hz, 3H), 4.19 (dt, J=12.1, 2.7 Hz, 1H). $^{19}$F NMR (377 MHz, Acetonitrile-d3) δ −77.23, −109.58 (d, J=241.9 Hz), −121.92 (d, J=241.8 Hz).

Example 340. 5-(8-(3,3-difluoro-4-((5-(trifluoromethyl)pyrazin-2-yl)oxy)pyrrolidin-1-yl)imidazo[1,2-b]pyridazin-6-yl)pyrimidine-2,4(1H,3H)-dione

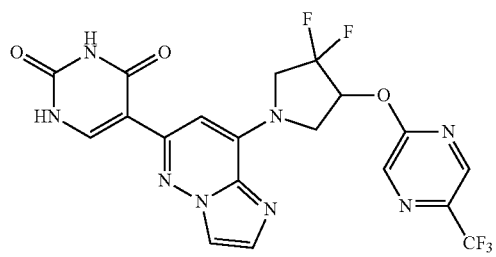 [SMILES: O=c1[nH]cc(-c2cc(N3CC(Oc4cnc(C(F)(F)F)cn4)C(F)(F)C3)c3nccn3n2)c(=O)[nH]1]

5-(8-(3,3-difluoro-4-((5-(trifluoromethyl)pyrazin-2-yl)oxy)pyrrolidin-1-yl)imidazo[1,2-b]pyridazin-6-yl)pyrimidine-2,4(1H,3H)-dione was prepared in the manner described for Example 330, but replacing 8-(3,3-difluoro-4-((4-(trifluoromethyl)pyridin-2-yl)oxy)pyrrolidin-1-yl)-6-(2,4-dimethoxypyrimidin-5-yl)imidazo[1,2-b]pyridazine with 8-(3,3-difluoro-4-((5-(trifluoromethyl)pyrazin-2-yl)oxy)pyrrolidin-1-yl)-6-(2,4-dimethoxypyrimidin-5-yl)imidazo[1,2-b]pyridazine and purified by RP-HPLC as a TFA salt. ES/MS m/z: 497.10. $^{1}$H NMR (400 MHz, Acetonitrile-d3) δ 9.22 (s, 2H), 8.65 (s, 1H), 8.45 (d, J=1.3 Hz, 1H), 8.07 (d, J=6.4 Hz, 1H), 8.00 (d, J=1.6 Hz, 1H), 7.75 (d, J=1.6 Hz, 1H), 7.10 (s, 1H), 6.04-5.84 (m, 1H), 4.61-4.37 (m, 3H), 4.26 (dt, J=12.5, 2.7 Hz, 1H). $^{19}$F NMR (376 MHz, Acetonitrile-d3) δ−68.01, −77.26, −106.97-−111.19 (m), −118.61-−123.19 (m).

Example 341. (S)-5-(8-(4-(4-(difluoromethyl)pyridin-2-yl)oxy)-3,3-difluoropyrrolidin-1-yl)imidazo[1,2-b]pyridazin-6-yl)pyrimidine-2,4(1H,3H)-dione

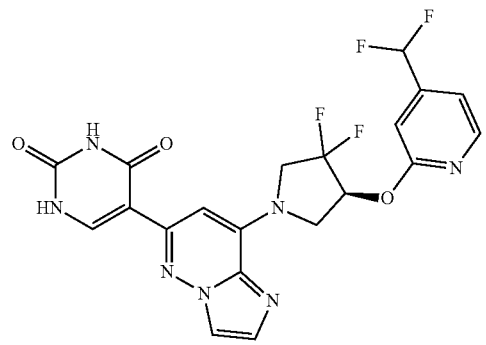 [SMILES: O=c1[nH]cc(-c2cc(N3C[C@H](Oc4cc(C(F)F)ccn4)C(F)(F)C3)c3nccn3n2)c(=O)[nH]1]

(S)-5-(8-(4-((4-(difluoromethyl)pyridin-2-yl)oxy)-3,3-difluoropyrrolidin-1-yl)imidazo[1,2-b]pyridazin-6-yl)pyrimidine-2,4(1H,3H)-dione in the manner described for Example 1, but replacing 8-cyclopropyl-6-(2,4-dimethoxypyrimidin-5-yl)-2-methyl-imidazo[1,2-b]pyridazine with (S)-8-(4-((4-(difluoromethyl)pyridin-2-yl)oxy)-3,3-difluoropyrrolidin-1-yl)-6-(2,4-dimethoxypyrimidin-5-yl)imidazo[1,2-b]pyridazine and purified by RP-HPLC as a TFA salt. ES/MS m/z: 478.20. $^{1}$H NMR (400 MHz, Acetonitrile-d3) δ 9.09 (d, J=14.7 Hz, 2H), 8.36 (d, J=5.3 Hz, 1H), 8.00 (d, J=6.4 Hz, 1H), 7.92 (d, J=1.4 Hz, 1H), 7.62 (d, J=1.4 Hz, 1H), 7.23 (d, J=5.3 Hz, 1H), 7.05 (s, 1H), 6.99-6.51 (m, 2H), 5.95 (d, J=4.6 Hz, 1H), 4.49 (td, J=20.8, 8.3 Hz, 3H), 4.23 (d, J=12.4 Hz, 1H). $^{19}$F NMR (376 MHz, Acetonitrile-d3) δ −77.27, −108.96-−109.60 (m), −117.17 (d, J=55.4 Hz), −121.70-−122.36 (m).

Example 342. 2-[(3S)-1-[6-(2,4-dioxo-1H-pyrimidin-5-yl)imidazo[1,2-b]pyridazin-8-yl]-4,4-difluoropyrrolidin-3-yl]oxypyridine-4-carbonitrile

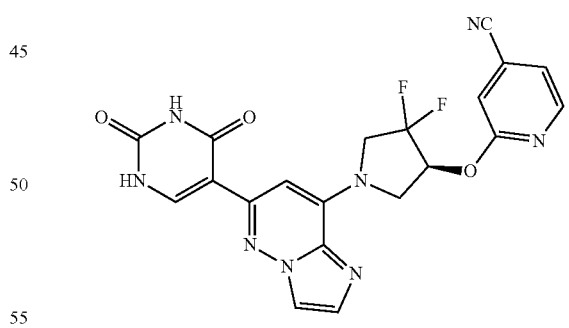

2-[(3S)-1-[6-(2,4-dioxo-1H-pyrimidin-5-yl)imidazo[1,2-b]pyridazin-8-yl]-4,4-difluoro-pyrrolidin-3-yl]oxypyridine-4-carbonitrile in the manner described for Example 1, but replacing 8-cyclopropyl-6-(2,4-dimethoxypyrimidin-5-yl)-2-methyl-imidazo[1,2-b]pyridazine with (S)-2-((1-(6-(2,4-dimethoxypyrimidin-5-yl)imidazo[1,2-b]pyridazin-8-yl)-4,4-difluoropyrrolidin-3-yl)oxy)isonicotinonitrile and purified by RP-HPLC as a TFA salt. ES/MS m/z: 453.10. $^{1}$H NMR (400 MHz, Acetonitrile-d3) δ 9.12 (d, J=15.2 Hz, 2H), 8.41 (dd, J=5.2, 0.8 Hz, 1H), 8.03-7.93 (m, 1H), 7.89 (d, J=1.2 Hz, 1H), 7.57 (d, J=1.2 Hz, 1H), 7.36 (dd, J=5.2, 1.3 Hz, 1H), 7.25 (d, J=1.1 Hz, 1H), 6.76 (s, 1H), 5.92 (d, J=4.3 Hz, 1H), 4.67-4.33 (m, 3H), 4.26 (d, J=12.8 Hz, 1H). ¹⁹F NMR (376 MHz, Acetonitrile-d3) δ −77.18, −109.11 (d, J=246.1 Hz), −120.61−−123.05 (m).

Example 343. 5-[8-[7-(difluoromethoxy)-5-azaspiro[2.4]heptan-5-yl]imidazo[1,2-b]pyridazin-6-yl]-1H-pyrimidine-2,4-dione

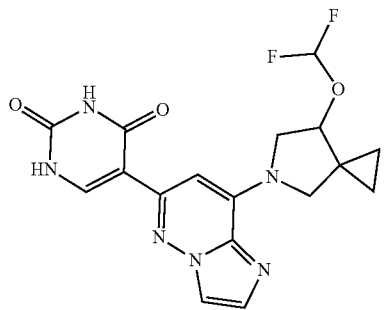 [SMILES: O=c1[nH]cc(-c2cc(N3CC(OC(F)F)C4(CC4)C3)c3nccn3n2)c(=O)[nH]1]

5-(8-(7-(difluoromethoxy)-5-azaspiro[2.4]heptan-5-yl)imidazo[1,2-b]pyridazin-6-yl)pyrimidine-2,4(1H,3H)-dione was prepared in the manner described for Example 342, but replacing 6-azabicyclo[3.2.0]heptane with 7-(difluoromethoxy)-5-azaspiro[2.4]heptane and purified by RP-HPLC as a TFA salt. ES/MS m/z: 391.10. ¹H NMR (400 MHz, Acetonitrile-d3) δ 9.11 (s, 2H), 7.99 (d, J=6.2 Hz, 1H), 7.88 (d, J=1.3 Hz, 1H), 7.59 (d, J=1.3 Hz, 1H), 6.76 (s, 1H), 6.48 (t, J=75.5 Hz, 1H), 4.44 (s, 1H), 4.36 (d, J=4.0 Hz, 1H), 4.27 (d, J=12.1 Hz, 1H), 4.11 (d, J=10.7 Hz, 1H), 3.64 (m, 1H), 1.11-0.83 (m, 3H), 0.79 (dt, J=10.0, 5.0 Hz, 1H). ¹⁹F NMR (376 MHz, Acetonitrile-d3) δ −77.04, −80.78−−82.87 (m).

Example 344. 5-[8-(7-hydroxy-5-azaspiro[2.4]heptan-5-yl)imidazo[1,2-b]pyridazin-6-yl]-1H-pyrimidine-2,4-dione

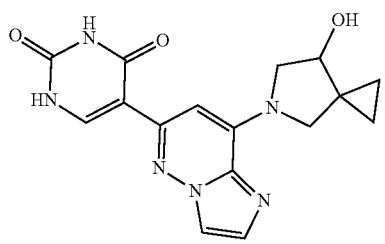 [SMILES: O=c1[nH]cc(-c2cc(N3CC(O)C4(CC4)C3)c3nccn3n2)c(=O)[nH]1]

5-(8-(7-hydroxy-5-azaspiro[2.4]heptan-5-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-[6-(2,4-dimethoxypyrimidin-5-yl)imidazo[1,2-b]pyridazin-8-yl]-5-azaspiro[2.4]heptan-7-ol. ES/MS m/z: 341.20. ¹H NMR (400 MHz, DMSO-d6) δ 11.37 (dd, J=10.7, 4.1 Hz, 2H), 8.04 (d, J=1.3 Hz, 1H), 7.94 (d, J=6.1 Hz, 1H), 7.58 (d, J=1.3 Hz, 1H), 6.57 (s, 1H), 3.79 (d, J=6.5 Hz, 1H), 2.58-2.51 (m, 4H), 0.89 (dt, J=11.1, 5.0 Hz, 1H), 0.66 (dt, J=16.5, 5.5 Hz, 3H).

Example 345. 5-[8-[7-[[5-(trifluoromethyl)-2-pyridyl]oxy]-5-azaspiro[2.4]heptan-5-yl]imidazo[1,2-b]pyridazin-6-yl]-1H-pyrimidine-2,4-dione

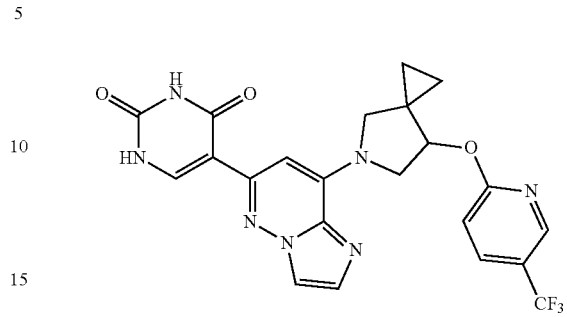

5-(8-(7-((5-(trifluoromethyl)pyrazin-2-yl)oxy)-5-azaspiro[2.4]heptan-5-yl)imidazo[1,2-b]pyridazin-6-yl)pyrimidine-2,4(1H,3H)-dione in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(7-((5-(trifluoromethyl)pyridin-2-yl)oxy)-5-azaspiro[2.4]heptan-5-yl)imidazo[1,2-b] and purified by RP-HPLC as a TFA salt. ES/MS m/z: 486.20. ¹H NMR (400 MHz, Acetonitrile-d3) δ 9.20 (d, J=33.4 Hz, 2H), 8.51 (d, J=2.4 Hz, 1H), 8.05-7.98 (m, 1H), 7.96 (dd, J=8.8, 2.6 Hz, 1H), 7.91 (d, J=1.5 Hz, 1H), 7.66 (d, J=1.4 Hz, 1H), 7.03-6.84 (m, 2H), 4.79 (d, J=12.8 Hz, 1H), 4.21 (d, J=10.9 Hz, 1H), 4.17-4.01 (m, 2H), 3.34 (q, J=7.8 Hz, 1H), 2.80-2.62 (m, 1H), 2.41 (q, J=10.8 Hz, 1H), 2.35-2.19 (m, 1H), 1.68 (dq, J=11.9, 8.8 Hz, 1H). ¹⁹F NMR (376 MHz, Acetonitrile-d3) δ −62.59, −77.09.

Example 346. 5-(8-(3,3-difluoro-4-phenylpyrrolidin-1-yl)imidazo[1,2-b]pyridazin-6-yl)pyrimidine-2,4(1H,3H)-dione

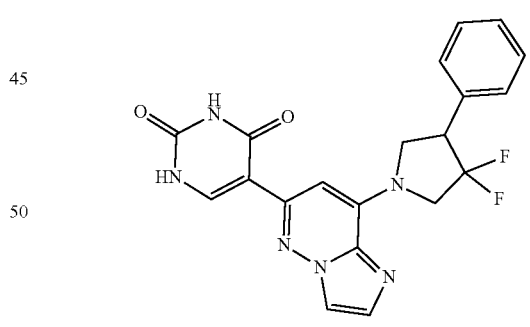

5-(8-((3,3-difluoro-4-phenylpyrrolidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3,3-difluoro-4-phenylpyrrolidine replacing 3,3,4,4-tetrafluoropyrrolidine and purified by RP-HPLC. ES/MS m/z: 411.20 [M+H]. ¹H NMR (400 MHz, DMSO-d6) δ 11.51-11.28 (m, 2H), 8.09 (d, J=1.2 Hz, 1H), 7.96 (d, J=6.1 Hz, 1H), 7.59 (d, J=1.2 Hz, 1H), 7.47-7.22 (m, 6H), 6.68 (s, 1H), 4.52 (d, J=30.3 Hz, 2H), 4.18 (s, 2H). ¹⁹F NMR (377 MHz, DMSO-d6) δ −75.10, −108.01.

Example 347. (R)-5-(8-(3-(difluoromethoxy)pyrrolidin-1-yl)imidazo[1,2-b]pyridazin-6-yl)pyrimidine-2,4(1H,3H)-dione

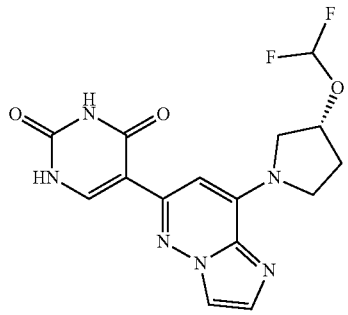 [SMILES: O=c1[nH]cc(-c2cc(N3CC[C@@H](OC(F)F)C3)c3nccn3n2)c(=O)[nH]1]

(R)-5-(8-(3-(difluoromethoxy)pyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with (R)-8-(3-(difluoromethoxy)pyrrolidin-1-yl)-6-(2,4-dimethoxypyrimidin-5-yl)imidazo[1,2-b]pyridazine and purified by RP-HPLC. ES/MS m/z: 365.20. $^1$H NMR (400 MHz, DMSO-d6) δ11.50-11.10 (m, 2H), 8.06 (d, J=1.3 Hz, 1H), 7.95 (d, J=6.1 Hz, 1H), 7.59 (d, J=1.3 Hz, 1H), 7.05-6.50 (m, 2H), 5.16-4.90 (m, 1H), 2.26 (dddd, J=19.5, 10.7, 8.0, 4.0 Hz, 2H). $^{19}$F NMR (377 MHz, DMSO-d6) δ −75.33, −81.14 (d, J=75.5 Hz).

Example 348. (S)-5-(8-(3-(difluoromethoxy)pyrrolidin-1-yl)imidazo[1,2-b]pyridazin-6-yl)pyrimidine-2,4(1H,3H)-dione

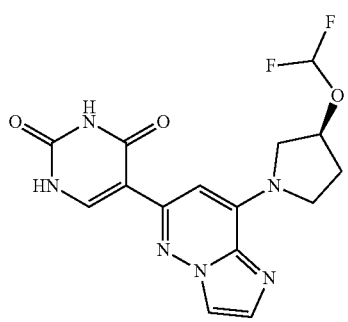 [SMILES: O=c1[nH]cc(-c2cc(N3CC[C@H](OC(F)F)C3)c3nccn3n2)c(=O)[nH]1]

(S)-5-(8-(3-(difluoromethoxy)pyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with (S)-8-(3-(difluoromethoxy)pyrrolidin-1-yl)-6-(2,4-dimethoxypyrimidin-5-yl)imidazo[1,2-b]pyridazine. ES/MS m/z: 365.20. $^1$H NMR (400 MHz, Acetonitrile-d3) δ 9.16 (s, 2H), 8.03 (d, J=6.3 Hz, 1H), 7.93 (d, J=1.6 Hz, 1H), 7.69 (d, J=1.5 Hz, 1H), 6.94 (s, 1H), 6.50 (t, J=75.3 Hz, 1H), 5.02 (p, J=3.7 Hz, 1H), 4.12 (d, J=4.8 Hz, 2H), 3.90 (q, J=9.5, 9.0 Hz, 2H), 2.32 (tt, J=6.1, 3.7 Hz, 2H). $^{19}$F NMR (376 MHz, Acetonitrile-d3) δ −77.12, −83.13 (dd, J=75.2, 5.4 Hz).

Example 349. 5-(8-(7-methoxy-5-azaspiro[2.4]heptan-5-yl)imidazo[1,2-b]pyridazin-6-yl)pyrimidine-2,4(1H,3H)-dione

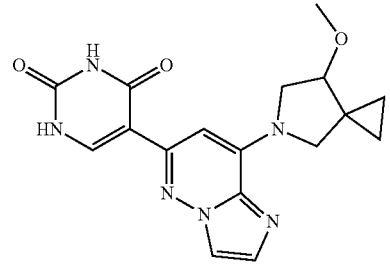 [SMILES: COC1CN(c2cc(-c3c[nH]c(=O)[nH]c3=O)nn3ccnc23)CC12CC2]

5-(8-(7-methoxy-5-azaspiro[2.4]heptan-5-yl)imidazo[1,2-b]pyridazin-6-yl)pyrimidine-2,4(1H,3H)-dione was prepared in the manner described for Example 442, but replacing 6-azabicyclo[3.2.0]heptane with 7-methoxy-5-azaspiro[2.4]heptane. ES/MS m/z: 355.20. $^1$H NMR (400 MHz, DMSO-d6) δ 11.38 (dd, J=10.5, 4.1 Hz, 2H), 8.05 (d, J=1.3 Hz, 1H), 7.94 (d, J=6.1 Hz, 1H), 7.59 (s, 1H), 6.57 (s, 1H), 3.52 (d, J=3.7 Hz, 1H), 3.29 (s, 3H), 2.70 (s, 1H), 2.18 (t, J=8.1 Hz, 1H), 2.02-1.81 (m, 1H), 1.04-0.93 (m, 1H), 0.84 (dt, J=9.3, 5.4 Hz, 1H), 0.74 0.54 (m, 2H).

Example 350. 5-(7-(7,7-difluoro-5-azaspiro[2.4]heptan-5-yl)pyrazolo[1,5-a]pyrimidin-5-yl)pyrimidine-2,4(1H,3H)-dione

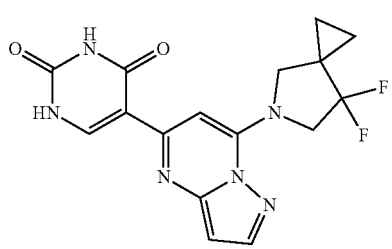 [SMILES: O=c1[nH]cc(-c2cc(N3CC(F)(F)C4(CC4)C3)n3nccc3n2)c(=O)[nH]1]

5-(7-(7,7-difluoro-5-azaspiro[2.4]heptan-5-yl)pyrazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-(7,7-difluoro-5-azaspiro[2.4]heptan-5-yl)-5-(2,4-dimethoxypyrimidin-5-yl)pyrazolo[1,5-a]pyrimidine. ES/MS m/z: 361.14. $^1$H NMR (400 MHz, DMSO-d6) δ 12.04 (s, 1H), 11.74 (s, 1H), 8.56 (d, J=6.0 Hz, 1H), 8.18 (d, J=2.2 Hz, 1H), 6.88 (s, 1H), 6.56 (d, J=2.2 Hz, 1H), 4.76 (s, 2H), 1.25-0.88 (m, 4H). $^{19}$F NMR (376 MHz, DMSO-d6) δ −107.89.

Example 351. 5-(3-fluoro-8-(3,3,4,4-tetrafluoropyrrolidin-1-yl)imidazo[1,2-b]pyridazin-6-yl)pyrimidine-2,4(1H,3H)-dione

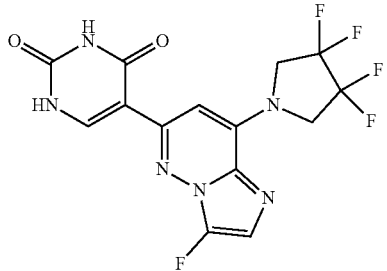 [SMILES: O=c1[nH]cc(-c2cc(N3CC(F)(F)C(F)(F)C3)c3ncc(F)n3n2)c(=O)[nH]1]

5-(3-fluoro-8-(3,3,4,4-tetrafluoropyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-(3,3,4,4-tetrafluoropyrrolidin-1-yl)imidazo[1,2-b]pyridazine. ES/MS m/z: 389.00. $^1$H NMR (400 MHz, DMSO-d6) δ 11.56-11.23 (m, 2H), 7.99 (d, J=6.1 Hz, 1H), 7.48 (d, J=7.2 Hz, 1H), 6.70 (s, 1H), 4.65 (t, J=12.4 Hz, 4H). $^{19}$F NMR (376 MHz, DMSO-d6) δ −74.91, −122.77, −122.72--122.93 (m), −155.26 (d, J=7.6 Hz).

Example 352. 5-(8-((1R,5S,6r)-6-(trifluoromethyl)-3-azabicyclo[3.1.0]hexan-3-yl)imidazo[1,2-b]pyridazin-6-yl)pyrimidine-2,4(1H,3H)-dione

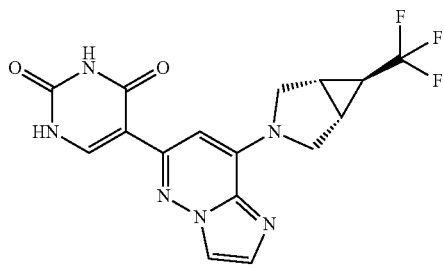 [SMILES: O=c1[nH]cc(-c2cc(N3C[C@@H]4[C@H](C3)[C@H]4C(F)(F)F)c3nccn3n2)c(=O)[nH]1]

5-(8-((1R,5S,6r)-6-(trifluoromethyl)-3-azabicyclo[3.1.0]hexan-3-yl)imidazo[1,2-b]pyridazin-6-yl)pyrimidine-2,4(1H,3H)-dione was prepared in the manner described for Example 442, but replacing 6-azabicyclo[3.2.0]heptane with (1R,5S,6r)-6-(trifluoromethyl)-3-azabicyclo[3.1.0]hexane. ES/MS m/z: 379.10. $^1$H NMR (400 MHz, DMSO-d6) δ 11.56-11.20 (m, 2H), 8.03 (d, J=1.2 Hz, 1H), 7.93 (d, J=6.1 Hz, 1H), 7.55 (d, J=1.1 Hz, 1H), 6.60 (s, 1H), 4.39 (s, 1H), 3.76 (d, J=11.3 Hz, 3H), 2.26 (d, J=3.2 Hz, 2H), 1.89 (tt, J=7.4, 3.6 Hz, 1H). $^{19}$F NMR (376 MHz, DMSO-d6) δ −63.87 (d, J=7.5 Hz), −75.07.

Example 353. 5-(8-(3,3-bis(trifluoromethyl)pyrrolidin-1-yl)imidazo[1,2-b]pyridazin-6-yl)pyrimidine-2,4(1H,3H)-dione

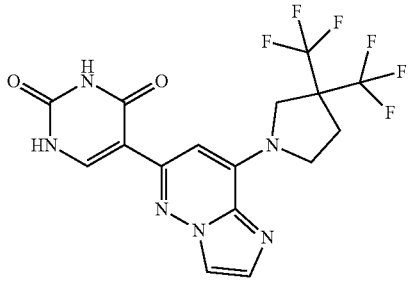 [SMILES: O=c1[nH]cc(-c2cc(N3CCC(C(F)(F)F)(C(F)(F)F)C3)c3nccn3n2)c(=O)[nH]1]

5-(8-(3,3-bis(trifluoromethyl)pyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 3 8-[3,3-bis(trifluoromethyl)pyrrolidin-1-yl]-6-(2,4-dimethoxypyrimidin-5-yl)imidazo[1,2-b]pyridazine. ES/MS m/z: 435.10. $^1$H NMR (400 MHz, Methanol-d4) δ 8.17 (s, 1H), 8.09 (d, J=1.5 Hz, 1H), 7.75 (d, J=1.5 Hz, 1H), 7.04 (s, 1H), 4.53 (s, 2H), 4.09 (t, J=7.3 Hz, 2H), 2.72 (t, J=7.3 Hz, 2H). $^{19}$F NMR (376 MHz, Methanol-d4) δ −73.55, −78.07.

Example 354. 3-(6-(2,4-dioxo-1,2,3,4-tetrahydropyrimidin-5-yl)imidazo[1,2-b]pyridazin-8-yl)-3-azabicyclo[3.1.0]hexane-1-carbonitrile

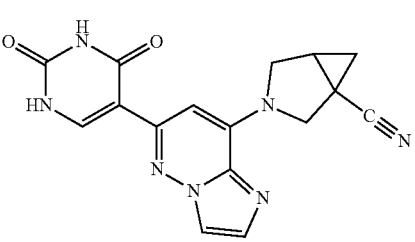 [SMILES: N#CC12CC1CN(c1cc(-c3c[nH]c(=O)[nH]c3=O)nn3ccnc13)C2]

3-(6-(2,4-dioxo-1,2,3,4-tetrahydropyrimidin-5-yl)imidazo[1,2-b]pyridazin-8-yl)-3-azabicyclo[3.1.0]hexane-1-carbonitrile was prepared in the manner described for Example 442, but replacing 6-azabicyclo[3.2.0]heptane with 3-azabicyclo[3.1.0]hexane-1-carbonitrile. ES/MS m/z: 336.10. $^1$H NMR (400 MHz, DMSO-d6) δ 11.39 (d, J=18.6 Hz, 2H), 8.04 (d, J=1.2 Hz, 1H), 7.92 (d, J=6.1 Hz, 1H), 7.55 (d, J=1.2 Hz, 1H), 6.61 (s, 1H), 3.89 (d, J=10.7 Hz, 1H), 3.82-3.73 (m, 1H), 2.60 (dt, J=9.0, 5.0 Hz, 1H), 1.58 (dd, J=8.6, 5.4 Hz, 1H), 1.12 (t, J=5.5 Hz, 1H).

Example 355. 5-(8-(1-fluoro-3-azabicyclo[3.1.0] hexan-3-yl)imidazo[1,2-b]pyridazin-6-yl)pyrimidine-2,4(1H,3H)-dione

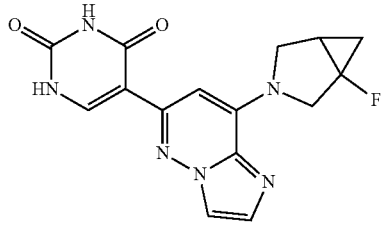 [SMILES: O=c1[nH]cc(-c2cc(N3CC4CC4(F)C3)c3nccn3n2)c(=O)[nH]1]

5-(8-(1-fluoro-3-azabicyclo[3.1.0]hexan-3-yl)imidazo[1,2-b]pyridazin-6-yl)pyrimidine-2,4(1H,3H)-dione was prepared in the manner described for Example Example 442, but replacing 6-azabicyclo[3.2.0]heptane with 1-fluoro-3-azabicyclo[3.1.0]hexane. ES/MS m/z: 329.10. $^1$H NMR (400 MHz, DMSO-d6) δ 11.42 (s, 2H), 8.11 (d, J=1.3 Hz, 1H), 7.95 (d, J=6.4 Hz, 1H), 7.65 (d, J=1.3 Hz, 1H), 6.68 (s, 1H), 4.11 (t, J=10.6 Hz, 2H), 3.92 (s, 2H), 2.37 2.19 (m, 1H), 1.63 (dddd, J=16.5, 11.6, 8.1, 4.4 Hz, 1H), 1.02-0.72 (m, 1H). $^{19}$F NMR (376 MHz, DMSO-d6) δ −199.67.

Example 356. 5-(7-(3,3,4,4-tetrafluoropyrrolidin-1-yl)-[1,2,4]triazolo[1,5-a]pyrimidin-5-yl)pyrimidine-2,4(1H,3H)-dione

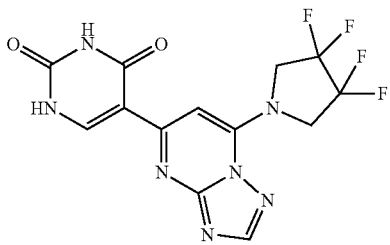 [SMILES: O=c1[nH]cc(-c2cc(N3CC(F)(F)C(F)(F)C3)n3ncnc3n2)c(=O)[nH]1]

5-(7-(3,3,4,4-tetrafluoropyrrolidin-1-yl)-[1,2,4]triazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-(2,4-dimethoxypyrimidin-5-yl)-7-(3,3,4,4-tetrafluoropyrrolidin-1-yl)-[1,2,4]triazolo[1,5-a]pyrimidine. ES/MS m/z: 372.10. $^1$H NMR (400 MHz, DMSO-d6) δ 11.68 (s, 1H), 11.55 (s, 1H), 8.48 (d, J=7.6 Hz, 2H), 7.51 (s, 1H), 4.73 (ddd, J=14.9, 10.2, 3.8 Hz, 5H). $^{19}$F NMR (376 MHz, DMSO-d6) δ −122.69-122.82 (m).

Example 357. 5-(7-(7,7-difluoro-5-azaspiro[2.4] heptan-5-yl)-[1,2,4]triazolo[1,5-a]pyrimidin-5-yl)pyrimidine-2,4(1H,3H)-dione

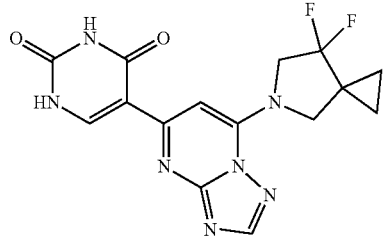 [SMILES: O=c1[nH]cc(-c2cc(N3CC(F)(F)C4(CC4)C3)n3ncnc3n2)c(=O)[nH]1]

5-(7-(7,7-difluoro-5-azaspiro[2.4]heptan-5-yl)-[1,2,4]triazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-(7,7-difluoro-5-azaspiro[2.4]heptan-5-yl)-5-(2,4-dimethoxypyrimidin-5-yl)-[1,2,4]triazolo[1,5-a]pyrimidine. ES/MS m/z: 362.10. $^1$H NMR (400 MHz, DMSO-d6) δ 11.63 (s, 1H), 11.50 (s, 1H), 8.48 (s, 1H), 8.39 (s, 1H), 7.42 (s, 1H), 4.66 (t, J=12.3 Hz, 2H), 4.10 (s, 2H), 1.06 (dd, J=4.8, 3.1 Hz, 4H). $^{19}$F NMR (376 MHz, DMSO-d6) δ −107.51 (t, J=12.5 Hz).

Example 358. 5-(7-(3,3,4,4-tetrafluoropyrrolidin-1-yl)pyrazolo[1,5-a]pyrimidin-5-yl)pyrimidine-2,4(1H,3H)-dione

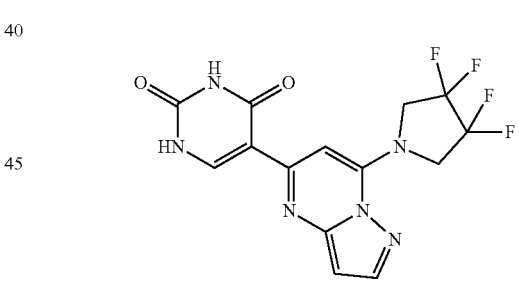

5-(3-fluoro-8-(3,3,4,4-tetrafluoropyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-(2,4-dimethoxypyrimidin-5-yl)-7-(3,3,4,4-tetrafluoropyrrolidin-1-yl)pyrazolo[1,5-a]pyrimidine ES/MS m/z: 371.10. $^1$H NMR (400 MHz, DMSO-d6) δ 11.60 (d, J=6.3 Hz, 1H), 11.50 (d, J=2.0 Hz, 1H), 8.37 (d, J=6.4 Hz, 1H), 8.14 (d, J=2.3 Hz, 1H), 7.22 (s, 1H), 6.49 (d, J=2.3 Hz, 1H), 4.70 (td, J=11.3, 10.8, 5.3 Hz, 4H). $^{19}$F NMR (376 MHz, DMSO-d6) δ−75.06, −122.08 (td, J=13.8, 12.6, 5.2 Hz).

Example 359. 5-(8-((2S,2S)-2-(4-(trifluoromethoxy)phenyl)cyclopropyl)imidazo[1,2-b]pyridazin-6-yl)pyrimidine-2,4(1H,3H)-dione

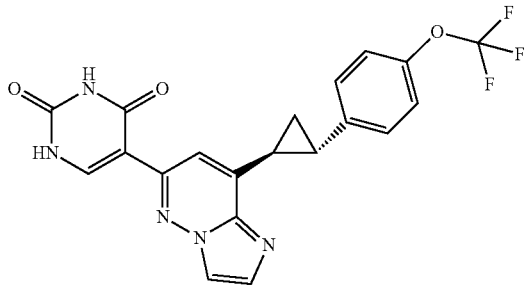 [SMILES: O=c1[nH]cc(-c2cc([C@H]3C[C@@H]3c3ccc(OC(F)(F)F)cc3)c3nccn3n2)c(=O)[nH]1]

5-(8-((1S,2S)-2-(4-(trifluoromethoxy)phenyl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(4-(trifluoromethoxy)phenyl)cyclopropyl)imidazo[1,2-b]pyridazine. Purification was accomplished via RP-HPLC (10-90% MeCN/H$_2$O with TFA modifier, Gemini column). ES/MS m/z: 430.10 [M+H]. 1H NMR (400 MHz, Methanol-d4) δ 8.27 (d, J=1.6 Hz, 1H), 8.24 (s, 1H), 7.91 (s, 1H), 7.82 (s, 1H), 7.44-7.33 (m, 2H), 7.29-7.20 (m, 2H), 2.88-2.71 (m, 2H), 2.03-1.81 (m, 2H). 19F NMR (376 MHz, Methanol-d4) δ −60.15, −77.61.

Example 360. 5-(8-((2S,2S)-2-(2,2-difluorobenzo[d][1,3]dioxol-5-yl)cyclopropyl)imidazo[1,2-b]pyridazin-6-yl)pyrimidine-2,4(1H,3H)-dione

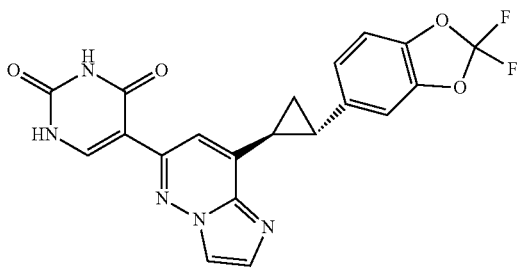 [SMILES: O=c1[nH]cc(-c2cc([C@H]3C[C@@H]3c3ccc4c(c3)OC(F)(F)O4)c3nccn3n2)c(=O)[nH]1]

5-(8-((1S,2S)-2-(2,2-difluorobenzo[d][1,3]dioxol-5-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((1S,2S)-2-(2,2-difluorobenzo[d][1,3]dioxol-5-yl)cyclopropyl)-6-(2,4-dimethoxypyrimidin-5-yl)imidazo[1,2-b]pyridazine. Purification was accomplished via RP-HPLC (10-90% MeCN/H$_2$O with TFA modifier, Gemini column). ES/MS m/z: 426.10 [M+H]. $^1$H NMR (400 MHz, DMSO-d6) δ 11.54 (s, 2H), 8.32 (d, J=1.3 Hz, 1H), 8.03 (d, J=6.4 Hz, 1H), 7.85 (s, 1H), 7.55 (s, 1H), 7.41-7.28 (m, 2H), 7.15 (dd, J=8.4, 1.8 Hz, 1H), 2.93-2.82 (m, 1H), 2.72 (ddd, J=9.0, 5.9, 4.3 Hz, 1H), 2.09 (dt, J=8.0, 5.2 Hz, 1H), 1.79 (dt, J=8.9, 5.3 Hz, 1H). $^{19}$F NMR (376 MHz, DMSO-d6) δ −49.75 (d, J=2.3 Hz), −74.85.

Example 361. 5-(8-((1S,2S)-2-(1-(3,3,3-trifluoropropyl)-1H-indazol-6-yl)cyclopropyl)imidazo[1,2-b]pyridazin-6-yl)pyrimidine-2,4(1H,3H)-dione

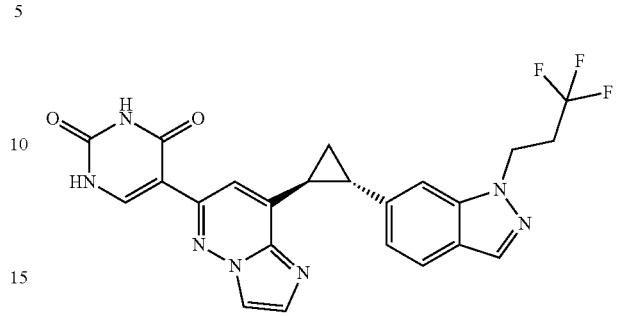

5-(8-((1S,2S)-2-(1-(3,3,3-trifluoropropyl)-1H-indazol-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(1-(3,3,3-trifluoropropyl)-1H-indazol-6-yl)cyclopropyl)imidazo[1,2-b]pyridazine. Purification was accomplished via RP-HPLC (10-90% MeCN/H$_2$O with TFA modifier, Gemini column). ES/MS m/z: 482.20 [M+H]. $^1$H NMR (400 MHz, Acetonitrile-d3) δ 9.45 (s, 1H), 9.36 (s, 1H), 8.24-8.13 (m, 3H), 8.09 (t, J=2.6 Hz, 1H), 7.97 (d, J=2.1 Hz, 1H), 7.69 (d, J=8.7 Hz, 1H), 7.53 (s, 1H), 7.00 (dd, J=8.8, 1.4 Hz, 1H), 4.70 (td, J=7.0, 1.8 Hz, 2H), 2.98 (qt, J=10.9, 6.9 Hz, 2H), 2.81 (q, J=4.6 Hz, 1H), 2.70 (ddd, J=11.0, 6.5, 4.3 Hz, 1H), 2.54 (s, OH), 2.06-1.98 (m, 1H), 1.90 (dq, J=9.5, 6.6, 5.7 Hz, 1H). $^{19}$F NMR (376 MHz, Acetonitrile-d3) δ −66.76 (t, J=10.9 Hz), −77.25 (d, J=6.6 Hz).

Example 362. 6-((1S,2S)-2-(6-(2,4-dioxo-1,2,3,4-tetrahydropyrimidin-5-yl)imidazo[1,2-b]pyridazin-8-yl)cyclopropyl)-1-(2,2,2-trifluoroethyl)-1H-indazole-3-carbonitrile

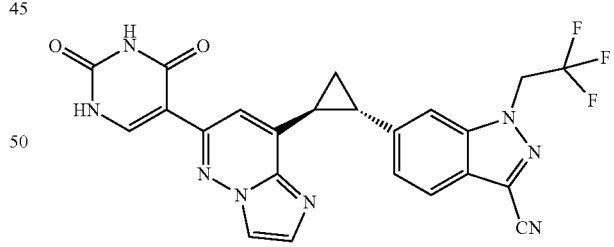

6-((2S,2S)-2-(6-(2,4-dioxo-1,2,3,4-tetrahydropyrimidin-5-yl)imidazo[1,2-b]pyridazin-8-yl)cyclopropyl)-1-(2,2,2-trifluoroethyl)-1H-indazole-3-carbonitrile was prepared as a racemic mixture in the manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-indazole-3-carbonitrile. Purification was accomplished via RP-HPLC (10-90% MeCN/H$_2$O with TFA modifier, Gemini column). ES/MS m/z: 493.20 [M+H]. $^1$H NMR (400 MHz, Acetonitrile-d3) δ 9.40 (s, 1H), 9.25 (s, 1H), 8.09 (s, 2H), 7.84 (d, J=9.4 Hz, 2H), 7.73 (d, J=13.1 Hz, 2H), 7.40 (d, J=8.5 Hz, 1H), 5.29 (d, J=9.3 Hz, 2H), 3.13 (dd, J=7.3, 4.7 Hz, 4H). ¹⁹F NMR (376 MHz, Acetonitrile-d3) δ −71.88 (t, J=8.7 Hz), −76.87.

Example 363. 5-(8-((1S,2S)-2-(5-(2,2,2-trifluoroethoxy)pyridin-2-yl)cyclopropyl)imidazo[1,2-b]pyridazin-6-yl)pyrimidine-2,4(1H,3H)-dione

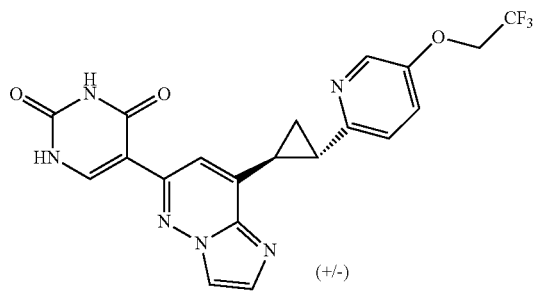 [SMILES: O=c1[nH]cc(-c2cc([C@H]3C[C@@H]3c3ccc(OCC(F)(F)F)cn3)c3nccn3n2)c(=O)[nH]1]

5-(8-((1S,2S)-2-(5-(2,2,2-trifluoroethoxy)pyridin-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(5-(2,2,2-trifluoroethoxy)pyridin-2-yl)cyclopropyl)imidazo[1,2-b]pyridazine. Purification was accomplished via RP-HPLC (10-90% MeCN/H₂O with TFA modifier, Gemini column). ES/MS m/z: 445.20 [M+H]. ¹H NMR (400 MHz, Acetonitrile-d3) δ 9.54 (s, 1H), 9.34 (s, 1H), 8.34 (d, J=2.9 Hz, 1H), 8.23-8.11 (m, 2H), 8.06 (s, 1H), 7.99 (d, J=2.0 Hz, 1H), 7.65-7.44 (m, 2H), 4.66 (q, J=8.4 Hz, 2H), 3.20 (dt, J=9.3, 5.2 Hz, 1H), 2.82 (ddd, J=9.1, 6.2, 4.4 Hz, 1H), 2.02 (ddd, J=8.9, 6.3, 5.2 Hz, 1H), 1.92-1.87 (m, 1H). ¹⁹F NMR (376 MHz, Acetonitrile-d3) δ −75.34 (t, J=8.4 Hz), −77.10.

Example 364. 5-(8-((2S,2S)-2-(5-(trifluoromethyl)thiazol-2-yl)cyclopropyl)imidazo[1,2-b]pyridazin-6-yl)pyrimidine-2,4(1H,3H)-dione

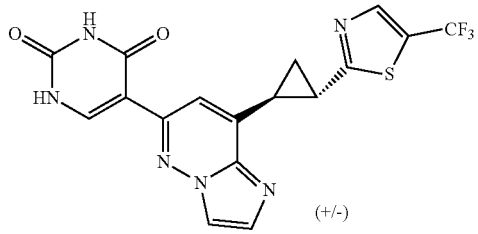 [SMILES: O=c1[nH]cc(-c2cc([C@H]3C[C@@H]3c3ncc(C(F)(F)F)s3)c3nccn3n2)c(=O)[nH]1]

5-(8-((1S,2S)-2-(5-(trifluoromethyl)thiazol-2-yl)cyclopropyl)imidazo[1,2-b]pyridazin-6-yl)pyrimidine-2,4(1H, 3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 2-((1S,2S)-2-(6-(2,4-dimethoxypyrimidin-5-yl)imidazo[1,2-b]pyridazin-8-yl)cyclopropyl)-5-(trifluoromethyl)thiazole. Purification was accomplished via RP-HPLC (10-90% MeCN/H₂O with TFA modifier, Gemini column). ES/MS m/z: 421.10 [M+H]. ¹H NMR (400 MHz, Acetonitrile-d3) δ 9.44 (s, 1H), 9.33 (s, 1H), 8.19 (d, J=2.0 Hz, 1H), 8.15 (d, J=6.4 Hz, 1H), 8.12 (q, J=1.3 Hz, 1H), 8.03 (s, 1H), 7.97 (d, J=2.0 Hz, 1H), 2.31-1.99 (m, 4H). ¹⁹F NMR (377 MHz, Acetonitrile-d3) δ −55.58, −77.15.

Example 365. 5-(8-((2S,2S)-2-(2-(trifluoromethyl)thiazol-5-yl)cyclopropyl)imidazo[1,2-b]pyridazin-6-yl)pyrimidine-2,4(1H,3H)-dione

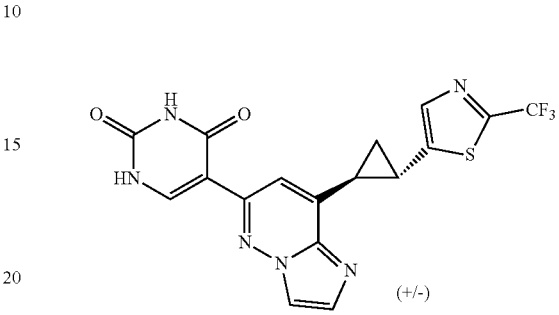

5-(8-((2S,2S)-2-(2-(trifluoromethyl)thiazol-5-yl)cyclopropyl)imidazo[1,2-b]pyridazin-6-yl)pyrimidine-2,4(1H, 3H)-dione was prepared as a racemic mixture in the manner described for Example 1, but replacing 8-cyclopropyl-6-(2, 4-dimethoxypyrimidin-5-yl)-2-methyl-imidazo[1,2-b]pyridazine with 5-((2S,2S)-2-(6-(2,4-dimethoxypyrimidin-5-yl)imidazo[1,2-b]pyridazin-8-yl)cyclopropyl)-2-(trifluoromethyl)thiazole. Purification was accomplished via RP-HPLC (10-90% MeCN/H₂O with TFA modifier, Gemini column). ES/MS m/z: 421.10 [M+H]. ¹H NMR (400 MHz, DMSO-d6) δ 11.55 (d, J=3.8 Hz, 2H), 8.34 (d, J=1.4 Hz, 1H), 8.08 (t, J=1.0 Hz, 1H), 8.02 (d, J=6.4 Hz, 1H), 7.86 (s, 1H), 7.63 (s, 1H), 3.31 (dt, J=9.8, 5.4 Hz, 1H), 2.88 (ddd, J=9.0, 6.1, 4.4 Hz, 1H), 2.29 (dt, J=8.8, 5.4 Hz, 1H), 1.88 (dt, J=9.0, 5.4 Hz, 1H). ¹⁹F NMR (376 MHz, DMSO-d6) δ −60.32, −75.15.

Example 366. 5-(8-((2S,2S)-2-(1-(trifluoromethyl)-1H-pyrazol-4-yl)cyclopropyl)imidazo[1,2-b]pyridazin-6-yl)pyrimidine-2,4(1H,3H)-dione

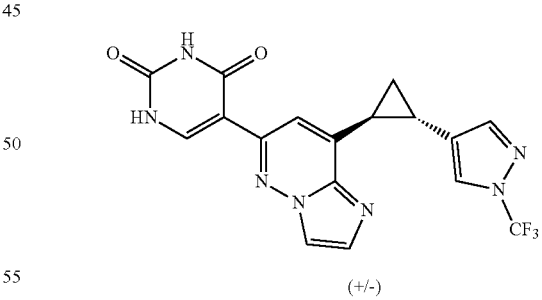

5-(8-((1S,2S)-2-(1-(trifluoromethyl)-1H-pyrazol-4-yl)cyclopropyl)imidazo[1,2-b]pyridazin-6-yl)pyrimidine-2,4(1H, 3H)-dione was prepared as a racemic mixture in the manner described for Example 1, but replacing 8-cyclopropyl-6-(2, 4-dimethoxypyrimidin-5-yl)-2-methyl-imidazo[1,2-b]pyridazine with 6-(2,4-dimethoxypyrimidin-5-yl)-8-((1S, 2S)-2-(1-(trifluoromethyl)-1H-pyrazol-4-yl)cyclopropyl)imidazo[1,2-b]pyridazine. Purification was accomplished via RP-HPLC (10-90% MeCN/H₂O with TFA modifier, Gemini column). ES/MS m/z: 404.10 [M+H]. ¹H NMR (400

MHz, DMSO-d6) δ 11.53 (s, 2H), 8.44 (s, 1H), 8.32 (d, J=1.4 Hz, 1H), 8.09-7.90 (m, 2H), 7.84 (s, 1H), 7.55 (s, 1H), 2.77 (dq, J=12.3, 5.9 Hz, 1H), 2.71-2.59 (m, 1H), 2.11-1.91 (m, 1H), 1.79-1.59 (m, 1H). $^{19}$F NMR (377 MHz, DMSO-d6) δ −59.68, −75.03.

Example 367. 5-(8-((2S,2S)-2-(4-(trifluoromethyl)thiazol-2-yl)cyclopropyl)imidazo[1,2-b]pyridazin-6-yl)pyrimidine-2,4(1H,3H)-dione

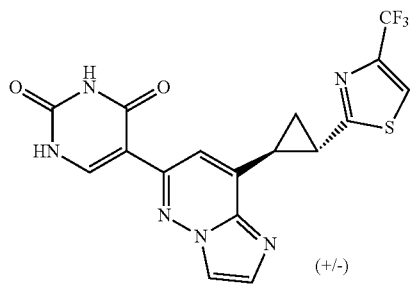 [SMILES: O=c1[nH]cc(-c2cc([C@H]3C[C@@H]3c3nc(C(F)(F)F)cs3)c3nccn3n2)c(=O)[nH]1]

(+/−)

5-(8-((2S,2S)-2-(4-(trifluoromethyl)thiazol-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 2-((2S,2S)-2-(6-(2,4-dimethoxypyrimidin-5-yl)imidazo[1,2-b]pyridazin-8-yl)cyclopropyl)-4-(trifluoromethyl)thiazole. Purification was accomplished via RP-HPLC (10-90% MeCN/H$_2$O with TFA modifier, Gemini column). ES/MS m/z: 421.10 [M+H]. $^1$H NMR (400 MHz, DMSO-d6) δ 11.55 (s, 2H), 8.34 (dd, J=5.4, 1.2 Hz, 2H), 8.02 (d, J=6.4 Hz, 1H), 7.85 (s, 1H), 7.63 (s, 1H), 3.51 (ddd, J=8.8, 5.9, 4.3 Hz, 1H), 3.06 (ddd, J=9.1, 6.3, 4.3 Hz, 1H), 2.27-2.16 (m, 1H), 2.06-1.83 (m, 1H). $^{19}$F NMR (377 MHz, DMSO-d6) δ −62.89, −75.11.

Example 368. 5-(8-((2S,2S)-2-(1-(difluoromethyl)-1H-pyrazol-4-yl)cyclopropyl)imidazo[1,2-b]pyridazin-6-yl)pyrimidine-2,4(1H,3H)-dione

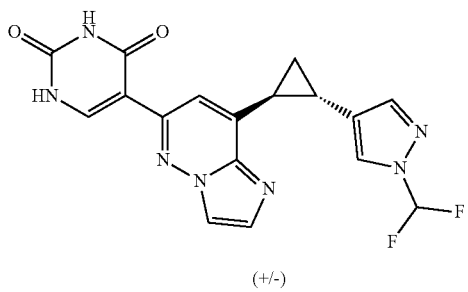 [SMILES: O=c1[nH]cc(-c2cc([C@H]3C[C@@H]3c3cnn(C(F)F)c3)c3nccn3n2)c(=O)[nH]1]

(+/−)

5-(8-((2S,2S)-2-(1-(difluoromethyl)-1H-pyrazol-4-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((2S,2S)-2-(1-(difluoromethyl)-1H-pyrazol-4-yl)cyclopropyl)-6-(2,4-dimethoxypyrimidin-5-yl)imidazo[1,2-b]pyridazine. Purification was accomplished via RP-HPLC (10-90% MeCN/H$_2$O with TFA modifier, Gemini column). ES/MS m/z: 386.10 [M+H]. $^1$H NMR (400 MHz, Acetonitrile-d3) δ 9.53 (s, 1H), 9.38 (s, 1H), 8.20 (d, J=2.1 Hz, 1H), 8.16 (d, J=6.1 Hz, 1H), 8.02 (d, J=2.1 Hz, 1H), 7.97 (d, J=5.6 Hz, 2H), 7.70 (s, 1H), 7.33 (t, J=60.0 Hz, 1H), 2.84 (dt, J=8.6, 5.1 Hz, 1H), 2.51 (ddd, J=9.2, 6.5, 4.4 Hz, 1H), 1.86-1.64 (m, 2H). $^{19}$F NMR (377 MHz, Acetonitrile-d3) δ −77.11, −95.58, −95.74.

Example 369. 5-(8-((1S,2S)-2-(1-(difluoromethyl)-1H-pyrazol-3-yl)cyclopropyl)imidazo[1,2-b]pyridazin-6-yl)pyrimidine-2,4(1H,3H)-dione

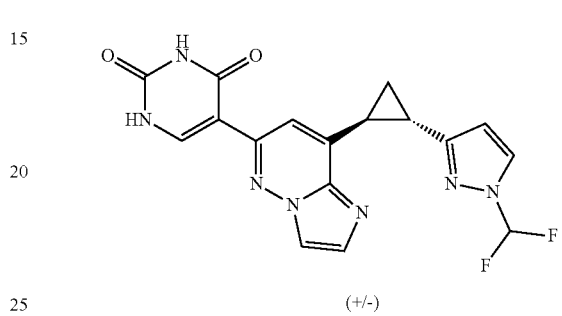

(+/−)

5-(8-((1S,2S)-2-(1-(difluoromethyl)-1H-pyrazol-3-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((2S,2S)-2-(1-(difluoromethyl)-1H-pyrazol-3-yl)cyclopropyl)-6-(2,4-dimethoxypyrimidin-5-yl)imidazo[1,2-b]pyridazine. Purification was accomplished via RP-HPLC (10-90% MeCN/H$_2$O with TFA modifier, Gemini column). ES/MS m/z: 386.10 [M+H]. $^1$H NMR (400 MHz, DMSO-d6) δ 11.53 (s, 2H), 8.31 (s, 1H), 8.16 (d, J=2.6 Hz, 1H), 7.95-7.57 (m, 2H), 7.54 (s, 1H), 6.50 (d, J=2.7 Hz, 1H), 2.92 (dt, J=9.1, 5.8 Hz, 1H), 2.88-2.76 (m, 1H), 2.02 (dt, J=9.5, 4.9 Hz, 1H), 1.81-1.66 (m, 1H). $^{19}$F NMR (376 MHz, DMSO-d6) δ −74.93, −94.15 (d, J=2.7 Hz), −94.31.

Example 370. 5-(8-((2S,2S)-2-(1-(difluoromethyl)-1H-pyrazol-4-yl)cyclopropyl)-3-fluoroimidazo[1,2-b]pyridazin-6-yl)pyrimidine-2,4(1H,3H)-dione

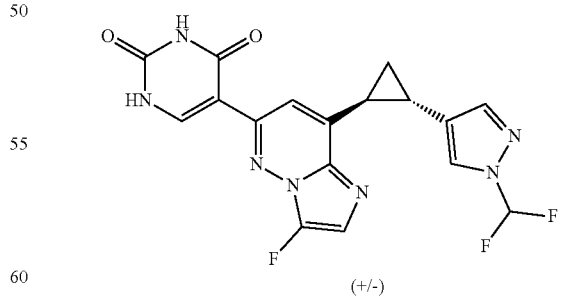

(+/−)

5-(8-((1S,2S)-2-(1-(difluoromethyl)-1H-pyrazol-4-yl)cyclopropyl)-3-fluoroimidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo

[1,2-b]pyridazine with 8-((2S,2S)-2-(1-(difluoromethyl)-1H-pyrazol-4-yl)cyclopropyl)-6-(2,4-dimethoxypyrimidin-5-yl)-3-fluoroimidazo[1,2-b]pyridazine. Purification was accomplished via RP-HPLC (10-90% MeCN/H₂O with TFA modifier, Gemini column). ES/MS m/z: 404.10 [M+H]. ¹H NMR (400 MHz, DMSO-d6) δ 11.53 (d, J=4.6 Hz, 2H), 8.19 (s, 1H), 8.02 (d, J=6.4 Hz, 1H), 7.93-7.58 (m, 2H), 7.55 (d, J=7.1 Hz, 1H), 7.46 (s, 1H), 2.77 (ddd, J=9.0, 6.2, 4.4 Hz, 1H), 2.62 (ddd, J=8.8, 5.7, 4.3 Hz, 1H), 2.05-1.95 (m, 1H), 1.65 (ddd, J=8.7, 6.3, 4.5 Hz, 1H). ¹⁹F NMR (376 MHz, DMSO-d6) δ -75.20, -93.98, -94.14, -155.65 (d, J=7.3 Hz).

Example 371. 5-(8-((2S,2S)-2-(1-(difluoromethyl)-1H-pyrazol-4-yl)cyclopropyl)-3-fluoroimidazo[1,2-b]pyridazin-6-yl)pyrimidine-2,4(1H,3H)-dione

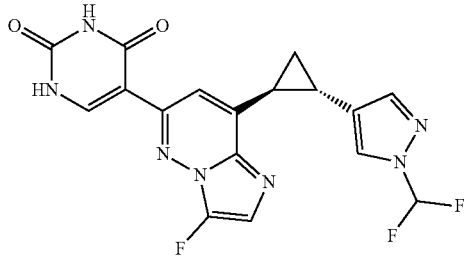 [SMILES: O=c1[nH]cc(-c2cc([C@H]3C[C@@H]3c3cnn(C(F)F)c3)c3ncc(F)n3n2)c(=O)[nH]1]

5-(8-((1S,2S)-2-(1-(difluoromethyl)-1H-pyrazol-4-yl)cyclopropyl)-3-fluoroimidazo[1,2-b]pyridazin-6-yl)pyrimidine-2,4(1H,3H)-dione was prepared by chiral separation of 8-((1S,2S)-2-(1-(difluoromethyl)-1H-pyrazol-4-yl)cyclopropyl)-6-(2,4-dimethoxypyrimidin-5-yl)-3-fluoroimidazo[1,2-b]pyridazine (Racemic Mixture) with SFC column (peak 1). ES/MS m/z: 404.10 [M+H]. ¹H NMR (400 MHz, DMSO-d6) δ 11.53 (d, J=4.6 Hz, 2H), 8.19 (s, 1H), 8.02 (d, J=6.4 Hz, 1H), 7.93-7.58 (m, 2H), 7.55 (d, J=7.1 Hz, 1H), 7.46 (s, 1H), 2.77 (ddd, J=9.0, 6.2, 4.4 Hz, 1H), 2.62 (ddd, J=8.8, 5.7, 4.3 Hz, 1H), 2.05-1.95 (m, 1H), 1.65 (ddd, J=8.7, 6.3, 4.5 Hz, 1H). ¹⁹F NMR (376 MHz, DMSO-d6) δ -75.20, -93.98, -94.14, -155.65 (d, J=7.3 Hz).

Example 372. 5-(8-((2S,2S)-2-(5-(trifluoromethoxy)pyridin-2-yl)cyclopropyl)imidazo[1,2-b]pyridazin-6-yl)pyrimidine-2,4(1H,3H)-dione

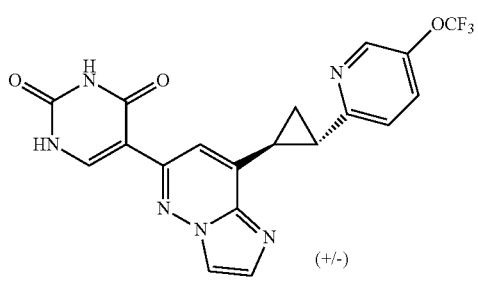 [SMILES: O=c1[nH]cc(-c2cc([C@H]3C[C@@H]3c3ccc(OC(F)(F)F)cn3)c3nccn3n2)c(=O)[nH]1]

5-(8-((2S,2S)-2-(5-(trifluoromethoxy)pyridin-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(5-(trifluoromethoxy)pyridin-2-yl)cyclopropyl)imidazo[1,2-b]pyridazine. Purification was accomplished via RP-HPLC (10-90% MeCN/H₂O with TFA modifier, Gemini column). ES/MS m/z: 431.10. ¹H NMR (400 MHz, DMSO-d6) δ 11.85-11.68 (m, 1H), 11.63 (d, J=1.9 Hz, 1H), 8.63 (d, J=2.8 Hz, 1H), 8.55 (d, J=1.8 Hz, 1H), 8.18 (s, 1H), 8.11 (d, J=6.2 Hz, 1H), 7.89-7.79 (m, 2H), 7.63 (d, J=8.6 Hz, 1H), 3.16-2.96 (m, 2H), 2.05-1.84 (m, 2H). ¹⁹F NMR (376 MHz, DMSO-d6) δ -57.85.

Example 373. 5-(8-((2S,2S)-2-(5-(trifluoromethoxy)pyridin-2-yl)cyclopropyl)imidazo[1,2-b]pyridazin-6-yl)pyrimidine-2,4(1H,3H)-dione

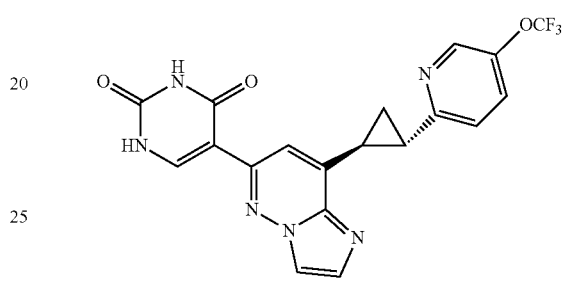

5-(8-((1S,2S)-2-(5-(trifluoromethoxy)pyridin-2-yl)cyclopropyl)imidazo[1,2-b]pyridazin-6-yl)pyrimidine-2,4(1H,3H)-dione was prepared by chiral separation of racemic mixture of 5-(8-((2S,2S)-2-(5-(trifluoromethoxy)pyridin-2-yl)cyclopropyl)imidazo[1,2-b]pyridazin-6-yl)pyrimidine-2,4(1H,3H)-dione by SFC column (peak 1). ES/MS m/z: 431.10. ¹H NMR (400 MHz, DMSO-d6) δ 11.85-11.68 (m, 1H), 11.63 (d, J=1.9 Hz, 1H), 8.63 (d, J=2.8 Hz, 1H), 8.55 (d, J=1.8 Hz, 1H), 8.18 (s, 1H), 8.11 (d, J=6.2 Hz, 1H), 7.89-7.79 (m, 2H), 7.63 (d, J=8.6 Hz, 1H), 3.16-2.96 (m, 2H), 2.05-1.84 (m, 2H). ¹⁹F NMR (376 MHz, DMSO-d6) δ -57.85.

Example 374. 5-(3-fluoro-8-((2S,2S)-2-(5-(trifluoromethoxy)pyridin-2-yl)cyclopropyl)imidazo[1,2-b]pyridazin-6-yl)pyrimidine-2,4(1H,3H)-dione

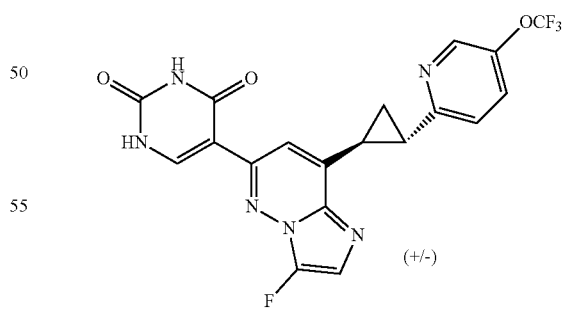

5-(3-fluoro-84(1S,2S)-2-(5-(trifluoromethoxy)pyridin-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-84(1S,2S)-2-(5-(trifluoromethoxy)pyridin-2-yl)

cyclopropyl)imidazo[1,2-b]pyridazine. Purification was accomplished via RP-HPLC (10-90% MeCN/H₂O with TFA modifier, Gemini column). ES/MS m/z: 449.10. ¹H NMR (400 MHz, DMSO-d6) δ 11.57-11.51 (m, 2H), 8.60 (d, J=2.7 Hz, 1H), 8.03 (d, J=6.4 Hz, 1H), 7.86-7.78 (m, 1H), 7.62 (d, J=8.6 Hz, 1H), 7.58-7.48 (m, 2H), 3.12 (ddd, J=8.7, 5.8, 4.2 Hz, 1H), 2.96 (ddd, J=9.0, 6.1, 4.1 Hz, 1H), 2.18-2.06 (m, 1H), 1.87 (ddd, J=9.4, 5.8, 4.0 Hz, 1H). ¹⁹F NMR (376 MHz, DMSO-d6) δ −57.86, −75.39, −155.54 (d, J=7.0 Hz).

Example 375. 5-((2S,2S)-2-(6-(2,4-dioxo-1,2,3,4-tetrahydropyrimidin-5-yl)-3-fluoroimidazo[1,2-b]pyridazin-8-yl)cyclopropyl)picolinonitrile

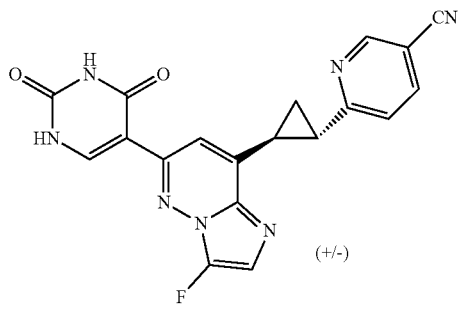 [SMILES: N#Cc1ccc([C@H]2C[C@@H]2c2cc(-c3c[nH]c(=O)[nH]c3=O)nn3c(F)cnc23)nc1]

(+/−)

5-((1S,2S)-2-(6-(2,4-dioxo-1,2,3,4-tetrahydropyrimidin-5-yl)-3-fluoroimidazo[1,2-b]pyridazin-8-yl)cyclopropyl)picolinonitrile was prepared as a racemic mixture in the manner described for Example 1, but replacing 8-cyclopropyl-6-(2,4-dimethoxypyrimidin-5-yl)-2-methyl-imidazo[1,2-b]pyridazine with 5-((1S,2S)-2-(6-(2,4-dimethoxypyrimidin-5-yl)-3-fluoroimidazo[1,2-b]pyridazin-8-yl)cyclopropyl)picolinonitrile. Purification was accomplished via RP-HPLC (10-90% MeCN/H₂O with TFA modifier, Gemini column). ES/MS m/z: 390.10. ¹H NMR (400 MHz, DMSO-d6) δ 11.56 (d, J=9.5 Hz, 2H), 8.74 (s, 1H), 8.01 (dd, J=16.7, 7.1 Hz, 2H), 7.92 (dd, J=8.1, 2.1 Hz, 1H), 7.60-7.53 (m, 2H), 3.04 (q, J=6.5, 6.0 Hz, 1H), 2.87 (dt, J=9.9, 5.4 Hz, 1H), 2.29 (dt, J=10.2, 5.6 Hz, 1H), 1.92 (dt, J=10.4, 5.7 Hz, 1H). ¹⁹F NMR (376 MHz, DMSO-d6) δ −75.43, −155.57 (d, J=7.0 Hz).

Example 376. 5-(8-((2S,2S)-2-(6-(trifluoromethoxy)pyridin-3-yl)cyclopropyl)imidazo[1,2-b]pyridazin-6-yl)pyrimidine-2,4(1H,3H)-dione

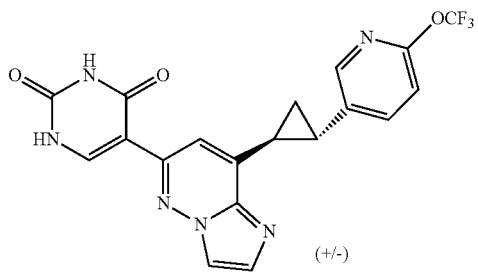 [SMILES: O=c1[nH]cc(-c2cc([C@H]3C[C@@H]3c3ccc(OC(F)(F)F)nc3)c3nccn3n2)c(=O)[nH]1]

(+/−)

5-(8-((2S,2S)-2-(6-(trifluoromethoxy)pyridin-3-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(6-(trifluoromethoxy)pyridin-3-yl)cyclopropyl)imidazo[1,2-b]pyridazine. Purification was accomplished via RP-HPLC (10-90% MeCN/H₂O with TFA modifier, Gemini column). ES/MS m/z: 431.10. ¹H NMR (400 MHz, DMSO-d6) δ 11.55 (d, J=4.7 Hz, 2H), 8.44-8.26 (m, 2H), 8.03 (d, J=6.3 Hz, 1H), 7.95-7.77 (m, 2H), 7.60 (s, 1H), 7.28 (d, J=8.5 Hz, 1H), 3.00-2.88 (m, 1H), 2.80 (dt, J=8.9, 5.6 Hz, 1H), 2.15 (dt, J=8.9, 5.4 Hz, 1H), 1.85 (dt, J=8.7, 5.5 Hz, 1H). ¹⁹F NMR (376 MHz, DMSO-d6) δ −55.65, −75.08.

Example 377. 5-(8-((2S,2S)-2-(5-(trifluoromethyl)pyrimidin-2-yl)cyclopropyl)imidazo[1,2-b]pyridazin-6-yl)pyrimidine-2,4(1H,3H)-dione

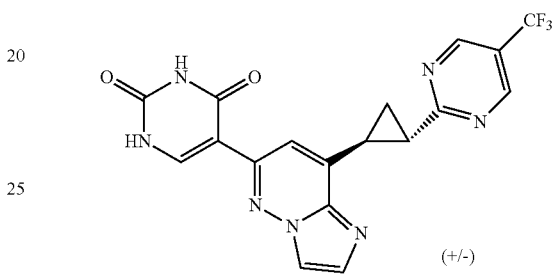

(+/−)

5-(8-((1S,2S)-2-(5-(trifluoromethyl)pyrimidin-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(5-(trifluoromethyl)pyrimidin-2-yl)cyclopropyl)imidazo[1,2-b]pyridazine. Purification was accomplished via RP-HPLC (10-90% MeCN/H₂O with TFA modifier, Gemini column). ES/MS m/z: 416.10. ¹H NMR (400 MHz, DMSO-d6) δ 11.56 (d, J=3.9 Hz, 2H), 9.20 (d, J=1.0 Hz, 2H), 8.36 (d, J=1.4 Hz, 1H), 8.04 (d, J=6.4 Hz, 1H), 7.88 (s, 1H), 7.67 (s, 1H), 3.34-3.01 (m, 2H), 2.30-2.15 (m, 1H), 2.01 (ddd, J=9.4, 5.7, 4.1 Hz, 1H). ¹⁹F NMR (376 MHz, DMSO-d6) δ −61.20, −75.17.

Example 378. 5-(3-fluoro-8-((2S,2S)-2-(5-(trifluoromethyl)pyrimidin-2-yl)cyclopropyl)imidazo[1,2-b]pyridazin-6-yl)pyrimidine-2,4(1H,3H)-dione

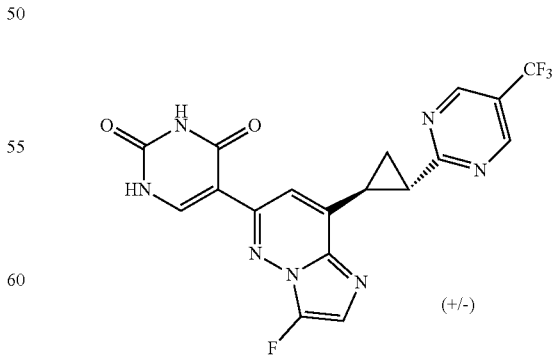

(+/−)

5-(3-fluoro-8-((1S,2S)-2-(5-(trifluoromethyl)pyrimidin-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((1S,2S)-2-(5-(trifluoromethyl)pyrimidin-2-yl)cyclopropyl)imidazo[1,2-b]pyridazine. Purification was accomplished via RP-HPLC (10-90% MeCN/H₂O with TFA modifier, Gemini column). ES/MS m/z: 434.10. ¹H NMR (400 MHz, DMSO-d6) δ 11.54 (s, 2H), 9.18 (s, 2H), 8.03 (s, 1H), 7.56 (t, J=3.5 Hz, 2H), 3.26 (ddd, J=9.1, 5.6, 4.1 Hz, 1H), 3.16-3.00 (m, 1H), 2.29 (ddd, J=8.7, 6.1, 4.0 Hz, 1H), 2.11-1.88 (m, 1H). ¹⁹F NMR (377 MHz, DMSO-d6) δ -61.23, -73.95, -155.48 (d, J=7.3 Hz).

Example 379. 5-(8-((2S,2S)-2-(5-(difluoromethyl)pyridin-2-yl)cyclopropyl)imidazo[1,2-b]pyridazin-6-yl)pyrimidine-2,4(1H,3H)-dione

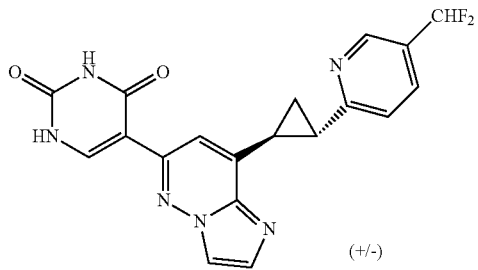 [SMILES: O=c1[nH]cc(-c2cc([C@H]3C[C@@H]3c3ccc(C(F)F)cn3)c3nccn3n2)c(=O)[nH]1]

(+/-)

5-(8-((1S,2S)-2-(5-(difluoromethyl)pyridin-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((1S,2S)-2-(5-(difluoromethyl)pyridin-2-yl)cyclopropyl)-6-(2,4-dimethoxypyrimidin-5-yl)imidazo[1,2-b]pyridazine. Purification was accomplished via RP-HPLC (10-90% MeCN/H₂O with TFA modifier, Gemini column). ES/MS m/z: 397.20. ¹H NMR (400 MHz, DMSO-d6) δ 11.57 (d, J=5.9 Hz, 2H), 8.73 (d, J=2.0 Hz, 1H), 8.37 (s, 1H), 8.05 (d, J=6.1 Hz, 1H), 8.00-7.82 (m, 2H), 7.72-7.52 (m, 2H), 7.14 (t, J=55.4 Hz, 1H), 3.16-2.93 (m, 2H), 2.15-2.01 (m, 1H), 2.00-1.86 (m, 1H). ¹⁹F NMR (376 MHz, DMSO-d6) δ -75.24 (d, J=2.2 Hz), -110.86, -111.01.

Example 380. 5-(8-((2S,2S)-2-(5-bromopyrimidin-2-yl)cyclopropyl)imidazo[1,2-b]pyridazin-6-yl)pyrimidine-2,4(1H,3H)-dione

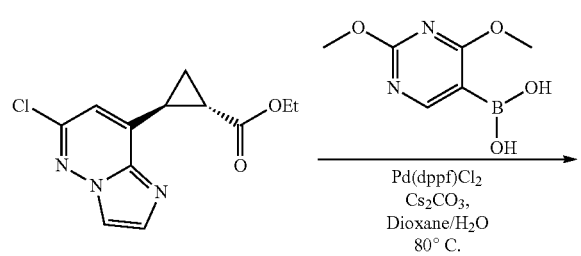

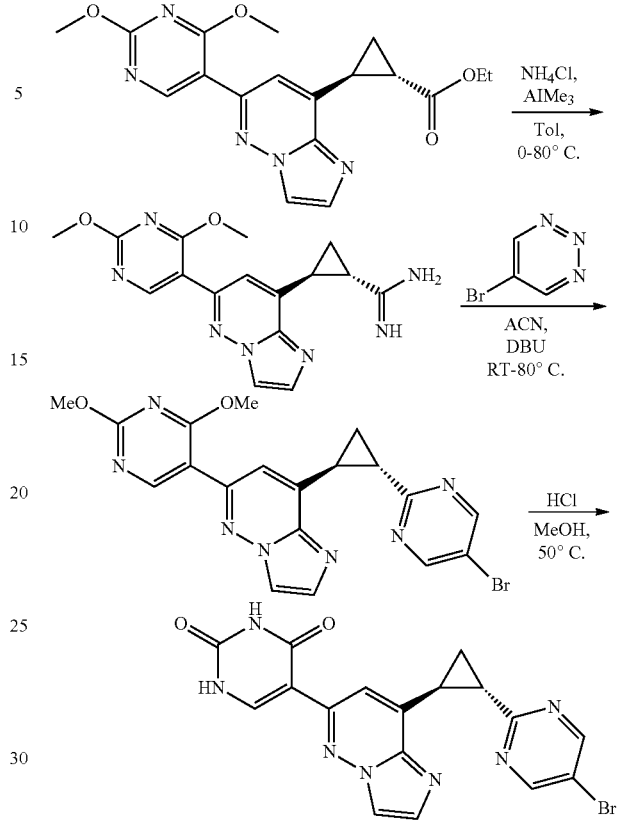

Step 1. (2,4-dimethoxypyrimidin-5-yl)boronic acid (1.38 g, 7.53 mmol), ethyl (1S,2S)-2-(6-chloroimidazo[1,2-b]pyridazin-8-yl)cyclopropanecarboxylate (2 g, 7.53 mmol), ferrous;cyclopenta-2,4-dien-1-yl(diphenyl)phosphane;dichloromethane;dichloropalladium (615 mg, 0.75 mmol), cesium carbonate (4.9 g, 15.1 mmol) were mixed in 1,4-dioxane (8 mL) and water (4 mL) in microwave vial and charged with argon, the reaction mixture was heated at 80 degree for 1 h. Reaction mixture was filtered and filtrate was evaporated. The residue was purified with combi-flash column to afford ethyl (1S,2S)-2-(6-(2,4-dimethoxypyrimidin-5-yl)imidazo[1,2-b]pyridazin-8-yl)cyclopropane-1-carboxylate. ES/MS m/z: 370.20.

Step 2. A suspension of ammonium chloride (0.45 g, 8.53 mmol) in Toluene (10 mL) was slowly mixed with 2M solution of trimethylalumininum (0.615 g, 8.53 mmol) in toluene at 0 degree. After completion of gas evolution, the mixture was stirred at RT for 15 min. Then ethyl (1S,2S)-2-(6-(2,4-dimethoxypyrimidin-5-yl)imidazo[1,2-b]pyridazin-8-yl)cyclopropane-1-carboxylate (0.7 g, 1.9 mmo) was added and heated at 100 degree for 2 h. Quenched the reaction with MeOH. Filtered, washed with MeOH, evaporated solvent and the residue was purified with Prep HPLC to afford (1S,2S)-2-(6-(2,4-dimethoxypyrimidin-5-yl)imidazo[1,2-b]pyridazin-8-yl)cyclopropane-1-carboximidamide. ES/MS m/z: 340.10. ¹H NMR (400 MHz, Acetonitrile-d3) δ8.94 (s, 1H), 8.73 (s, 1H), 8.24 (d, J=1.9 Hz, 1H), 7.99 (d, J=1.8 Hz, 1H), 7.89 (s, 2H), 7.65 (s, 1H), 4.09 (d, J=16.3 Hz, 6H), 3.46 (dd, J=9.8, 5.4 Hz, 1H), 2.61 (dt, J=10.5, 5.6 Hz, 1H), 2.04 (dt, J=9.3, 6.2 Hz, 1H), 1.94 (t, J=4.2 Hz, 1H).

Step 3. 1,8-Diazabicyclo[5.4.0]undec-7-ene (0.3 g, 2 mmol) was added to (1S,2S)-2-[6-(2,4-dimethoxypyrimidin-5-yl)imidazo[1,2-b]pyridazin-8-yl]cyclopropanecarboxamidine (0.34 g, 1 mmol) solution in ACN (5 ml), the reaction mixture was stirred at RT for 5 min, then 5-bromotriazine was added, the reaction mixture was heated at 80 degree for 1 h. The solvent was evaporated and the residue was purified with combi-flash column to afford 8-((2S,2S)-2-(5-bromopyrimidin-2-yl)cyclopropyl)-6-(2,4-dimethoxypyrimidin-5-yl)imidazo[1,2-b]pyridazine. ES/MS m/z: 454.10.

Step 4. A solution of 8-((2S,2S)-2-(5-bromopyrimidin-2-yl)cyclopropyl)-6-(2,4-dimethoxypyrimidin-5-yl)imidazo[1,2-b]pyridazine (21 mg, 0.046 mmol) was dissolved in 1:1 1N HCl/MeOH (2 mL) was heated to 80° C. for 1 h. The solvent was then evaporated and the residue was purified with prep HPLC to afford 5-[8-[(1S,2S)-2-(5-bromopyrimidin-2-yl)cyclopropyl]imidazo[1,2-b]pyridazin-6-yl]-1H-pyrimidine-2,4-dione. ES/MS m/z: 426.00. $^1$H NMR (400 MHz, DMSO-d6) δ 11.59 (dd, J=11.6, 4.2 Hz, 2H), 8.93 (s, 2H), 8.43 (d, J=1.6 Hz, 1H), 8.06 (d, J=6.2 Hz, 1H), 7.99 (s, 1H), 7.72 (s, 1H), 3.03 (ddt, J=10.2, 6.4, 3.3 Hz, 2H), 2.11 (ddd, J=9.0, 7.1, 3.5 Hz, 1H), 1.93 (ddd, J=8.3, 6.2, 4.2 Hz, 1H).

Example 381. 5-(3-fluoro-8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione

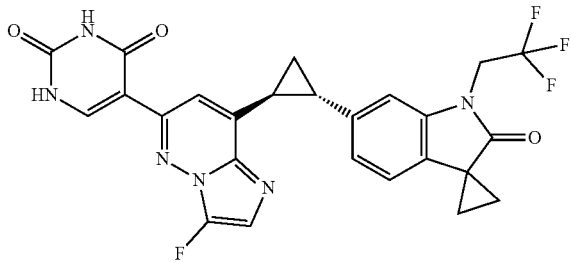

5-(3-fluoro-8-((1S,2S)-2-(2'-oxo-F-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclopropane-1,3'-indolin]-2'-one. ES/MS m/z: 527.20. $^1$H NMR (400 MHz, Acetonitrile-d3) δ 9.21 (s, 2H), 8.03 (d, J=6.3 Hz, 1H), 7.56 (s, 1H), 7.41 (d, J=6.8 Hz, 1H), 7.03-6.89 (m, 3H), 4.51 (q, J=9.2 Hz, 2H), 2.79 (ddq, J=19.6, 9.9, 4.6 Hz, 2H), 2.06 (dt, J=9.1, 5.5 Hz, 1H), 1.77 (dd, J=8.7, 5.5 Hz, 1H), 1.64 (t, J=4.1 Hz, 4H). $^{19}$F NMR (376 MHz, Acetonitrile-d3) δ −71.20 (t, J=9.2 Hz), −77.29, −157.06 (d, J=6.8 Hz).

Example 382. 5-(8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione (racemate)

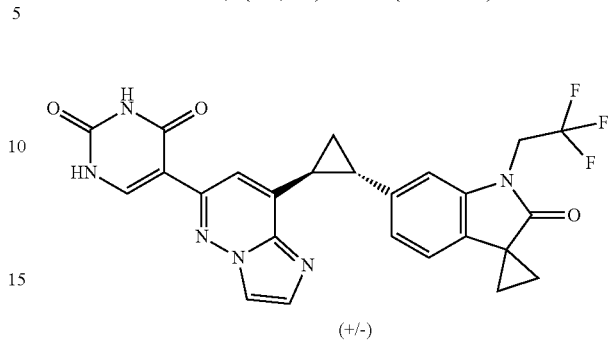

(+/−)

5-(8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclopropane-1,3'-indolin]-2'-one (racemate). ES/MS m/z: 509.10. $^1$H NMR (400 MHz, Acetonitrile-d3) δ 9.41 (s, 1H), 9.29 (s, 1H), 8.18-8.10 (m, 2H), 7.96-7.88 (m, 2H), 7.08 (s, 1H), 7.01 (dd, J=7.8, 1.5 Hz, 1H), 6.93 (d, J=7.7 Hz, 1H), 4.56 (q, J=9.2 Hz, 2H), 3.04 (dt, J=9.3, 5.3 Hz, 1H), 2.76-2.66 (m, 1H), 1.94-1.79 (m, 2H), 1.70-1.59 (m, 4H). $^{19}$F NMR (376 MHz, Acetonitrile-d3) δ −71.16 (t, J=9.1 Hz), −77.07.

Example 383. 5-(8-((2S,2S)-2-(1-(5-(trifluoromethyl)pyridin-2-yl)-1H-indazol-6-yl)cyclopropyl)imidazo[1,2-b]pyridazin-6-yl)pyrimidine-2,4(1H,3H)-dione (racemate)

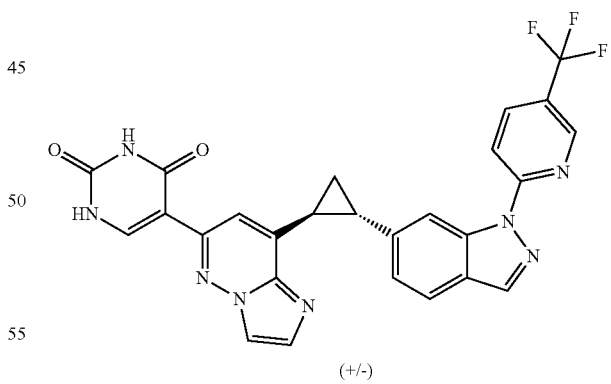

(+/−)

5-(8-((1S,2S)-2-(1-(5-(trifluoromethyl)pyridin-2-yl)-1H-indazol-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[1-[5-(trifluoromethyl)-2-pyridyl]indazol-6-yl]cyclopropyl]imidazo[1,2-b]pyridazine (racemate). ES/MS m/z: 531.10. $^1$H NMR (400 MHz, DMSO-d6) δ

11.57 (d, J=4.8 Hz, 2H), 9.00 (d, J=2.3 Hz, 1H), 8.71 (s, 1H), 8.53 (s, 1H), 8.41-8.33 (m, 2H), 8.18 (d, J=8.8 Hz, 1H), 8.09-8.02 (m, 1H), 7.90 (d, J=8.1 Hz, 2H), 7.64 (s, 1H), 7.31-7.24 (m, 1H), 3.05 (t, J=7.3 Hz, 1H), 2.87 (dt, J=9.5, 5.1 Hz, 1H), 2.18 (dt, J=10.6, 5.5 Hz, 1H), 1.95 (dt, J=10.8, 5.5 Hz, 1H). $^{19}$F NMR (376 MHz, DMSO-d6) δ −60.88, −75.17.

Example 384. 5-(8-((2S,2S)-2-(2'-oxo-1'-(2,2,2-trifluoroethyl)spiro[cyclobutane-1,3'-indolin]-6'-yl)cyclopropyl)imidazo[1,2-b]pyridazin-6-yl)pyrimidine-2,4(1H,3H)-dione

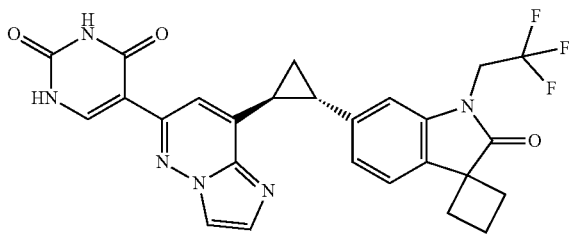 [SMILES: O=C1N(CC(F)(F)F)c2cc([C@H]3C[C@@H]3c3cc(-c4c[nH]c(=O)[nH]c4=O)nn4ccnc34)ccc2C12CCC2]

5-(8-((1S,2S)-2-(2'-oxo-1'-(2,2,2-trifluoroethyl)spiro[cyclobutane-1,3'-indolin]-6'-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclobutane-1,3'-indolin]-2'-one. ES/MS m/z: 523.10. $^{1}$H NMR (400 MHz, Acetonitrile-d3) δ 9.31 (s, 1H), 9.25 (s, 1H), 8.16-8.02 (m, 2H), 7.88 (d, J=1.8 Hz, 1H), 7.82 (s, 1H), 7.55 (d, J=7.6 Hz, 1H), 7.07 (dd, J=7.7, 1.6 Hz, 1H), 6.91 (s, 1H), 4.51-4.29 (m, 2H), 2.97-2.85 (m, 1H), 2.80-2.66 (m, 1H), 2.60-2.46 (m, 2H), 2.45-2.17 (m, 4H), 1.90-1.73 (m, 2H). $^{19}$F NMR (376 MHz, Acetonitrile-d3) δ −71.20 (t, J=9.1 Hz), −76.96.

Example 385. 5-(3-fluoro-8-((2S,2S)-2-(2'-oxo-1'-(2,2,2-trifluoroethyl)spiro[cyclopentane-1,3'-indolin]-6'-yl)cyclopropyl)imidazo[1,2-b]pyridazin-6-yl)pyrimidine-2,4(1H,3H)-dione

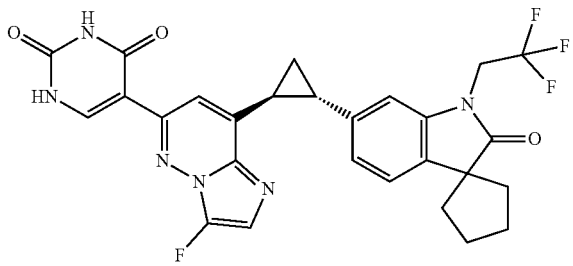 [SMILES: O=C1N(CC(F)(F)F)c2cc([C@H]3C[C@@H]3c3cc(-c4c[nH]c(=O)[nH]c4=O)nn4c(F)cnc34)ccc2C12CCCC2]

5-(3-fluoro-8-((1S,2S)-2-(2'-oxo-1'-(2,2,2-trifluoroethyl)spiro[cyclopentane-1,3'-indolin]-6'-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclopentane-1,3'-indolin]-2'-one. ES/MS m/z: 555.20. $^{1}$H NMR (400 MHz, Acetonitrile-d3) δ 9.18 (s, 2H), 8.03 (d, J=6.3 Hz, 1H), 7.55 (s, 1H), 7.41 (d, J=6.8 Hz, 1H), 7.25 (d, J=7.7 Hz, 1H), 7.00 (dd, J=7.7, 1.5 Hz, 1H), 6.91 (s, 1H), 4.43 (q, J=9.2 Hz, 2H), 2.87-2.65 (m, 2H), 2.05 (ddt, J=13.1, 8.7, 4.5 Hz, 7H), 1.90-1.83 (m, 2H), 1.83-1.65 (m, 1H). $^{19}$F NMR (376 MHz, Acetonitrile-d3) δ −71.20 (t, J=9.1 Hz), −77.30, −157.08 (d, J=6.9 Hz).

Example 386. 5-(3-fluoro-8-((2S,2S)-2-(2'-oxo-1'-(2,2,2-trifluoroethyl)spiro[cyclobutane-1,3'-indolin]-6'-yl)cyclopropyl)imidazo[1,2-b]pyridazin-6-yl)pyrimidine-2,4(1H,3H)-dione

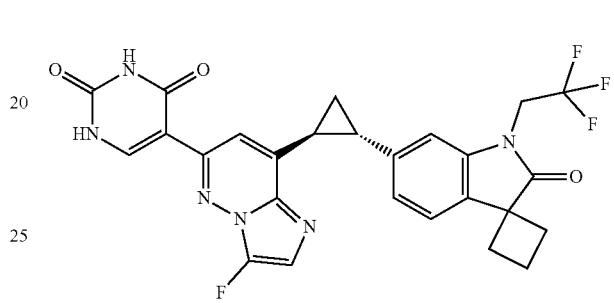

5-(3-fluoro-8-((1S,2S)-2-(2'-oxo-F-(2,2,2-trifluoroethyl)spiro[cyclobutane-1,3'-indolin]-6'-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)-3-fluoroimidazo[1,2-b]pyridazin-8-yl)cyclopropyl)-1'-(2,2,2-trifluoroethyl)spiro[cyclobutane-1,3'-indolin]-2'-one. ES/MS m/z: 541.20. $^{1}$H NMR (400 MHz, Acetonitrile-d3) δ 9.19 (s, 2H), 8.03 (d, J=6.4 Hz, 1H), 7.55 (d, J=9.0 Hz, 2H), 7.41 (d, J=6.8 Hz, 1H), 7.05 (dd, J=7.7, 1.5 Hz, 1H), 6.88 (s, 1H), 4.41 (q, J=9.2 Hz, 2H), 2.87-2.68 (m, 2H), 2.62-2.46 (m, 2H), 2.47-2.17 (m, 4H), 2.07 (dt, J=8.9, 5.6 Hz, 1H), 1.86-1.69 (m, 1H). $^{19}$F NMR (376 MHz, Acetonitrile-d3) δ −71.20 (t, J=9.1 Hz), −77.29, −157.04 (d, J=6.8 Hz).

Example 387. 5-(8-((2S,2S)-2-(2'-oxo-1'-(2,2,2-trifluoroethyl)spiro[cyclopentane-1,3'-indolin]-6'-yl)cyclopropyl)imidazo[1,2-b]pyridazin-6-yl)pyrimidine-2,4(1H,3H)-dione

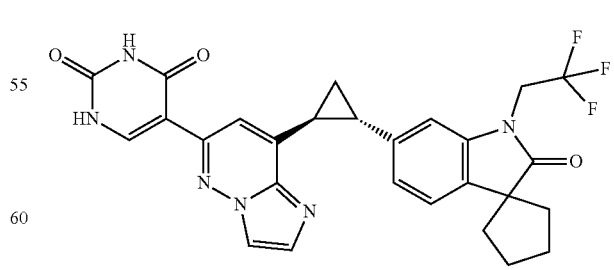

5-(8-((2S,2S)-2-(2'-oxo-1'-(2,2,2-trifluoroethyl)spiro[cyclopentane-1,3'-indolin]-6'-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-1'-(2,2,2-trifluoroethyl)spiro[cyclopentane-1,3'-indolin]-2'-one. ES/MS m/z: 537.10. ¹H NMR (400 MHz, Acetonitrile-d3) δ 9.33 (s, 1H), 9.26 (s, 1H), 8.16-8.07 (m, 2H), 7.93-7.83 (m, 2H), 7.25 (d, J=7.7 Hz, 1H), 7.06-6.98 (m, 1H), 6.96 (s, 1H), 4.45 (q, J=9.2 Hz, 2H), 2.92-2.85 (m, 1H), 2.69 (d, J=6.4 Hz, 1H), 2.04 (dd, J=10.4, 6.1 Hz, 5H), 1.93-1.82 (m, 5H). ¹⁹F NMR (376 MHz, Acetonitrile-d3) δ −71.18 (t, J=9.2 Hz), −77.04.

Example 388. 5-(3-chloro-8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione

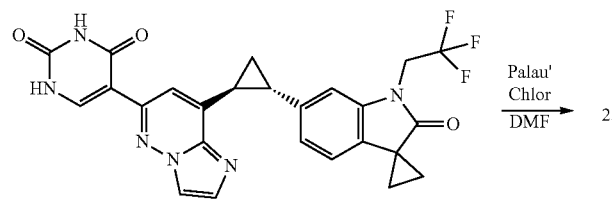

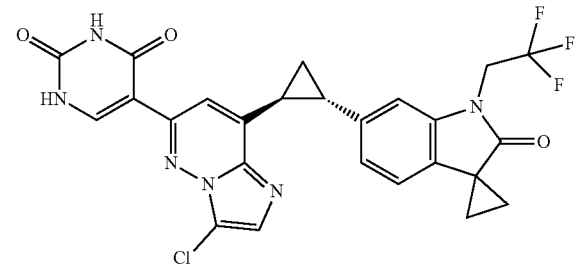

Palau'Chlor (35 mg, 0.165 mmol) was added to solution of 5-(8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione (84 mg, 0.165 mmol) in DMF at RT. The reaction mixture was stirred at RT for 2 h and then purified with Prep HPLC to afford 5-(3-chloro-8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione. ES/MS m/z: 543.10. ¹H NMR (400 MHz, DMSO-d6) δ 11.58-11.50 (m, 2H), 8.04 (d, J=6.1 Hz, 1H), 7.85 (s, 1H), 7.56 (s, 1H), 7.18 (s, 1H), 7.03-6.93 (m, 2H), 4.70 (q, J=9.4 Hz, 2H), 2.88 (ddd, J=9.0, 6.3, 4.3 Hz, 1H), 2.74 (ddd, J=8.8, 5.9, 4.4 Hz, 1H), 2.11 (dt, J=8.9, 5.2 Hz, 1H), 1.87-1.74 (m, 1H), 1.66 (q, J=4.0, 3.1 Hz, 2H), 1.58 (q, J=4.7, 3.8 Hz, 2H). ¹⁹F NMR (376 MHz, DMSO-d6) δ −69.25 (t, J=9.4 Hz), −75.25.

Example 389. (S)-5-(8-(4-(4-(difluoromethyl)-5-fluoropyridin-2-yl)oxy)-3,3-difluoropyrrolidin-1-yl)imidazo[1,2-b]pyridazin-6-yl)pyrimidine-2,4(1H,3H)-dione

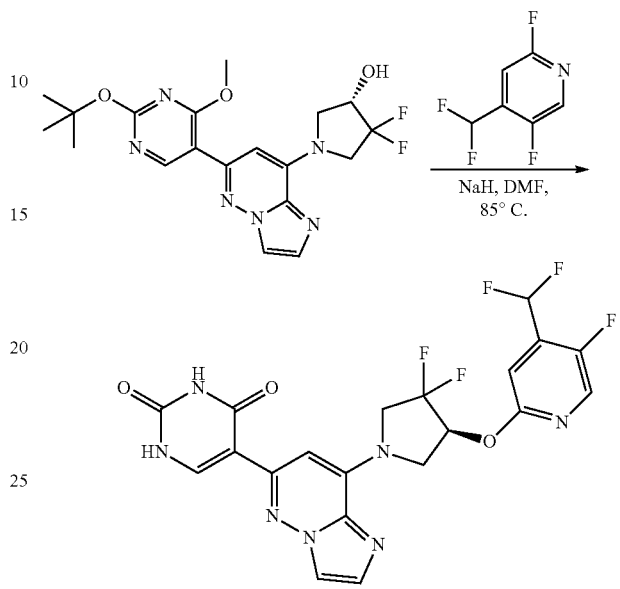

Added NaH (7.5 mg, 0.195 mmol) to (3S)-1-[6-(2,4-ditert-butoxypyrimidin-5-yl)imidazo[1,2-b]pyridazin-8-yl]-4,4-difluoro-pyrrolidin-3-431 (30 mg, 0.065 mmol) in DMF (2 ml), stirred at RT for 10 mins, then to the reaction mixture was added 4-(difluoromethyl)-2,5-difluoro-pyridine (21 mg, 0.12 mmol). The reaction mixture was stirred at 85 degree for 30 mins and was then quenched with water and purified with Prep HPLC to afford (S)-5-(8-(4-((4-(difluoromethyl)-5-fluoropyridin-2-yl)oxy)-3,3-difluoropyrrolidin-1-yl)imidazo[1,2-b]pyridazin-6-yl)pyrimidine-2,4(1H,3H)-dione. ES/MS m/z: 496.10. ¹H NMR (400 MHz, Acetonitrile-d3) δ9.34 (d, J=24.1 Hz, 2H), 8.23 (d, J=1.5 Hz, 1H), 8.12 (d, J=6.0 Hz, 1H), 8.05 (d, J=2.0 Hz, 1H), 7.84 (s, 1H), 7.26 (s, 1H), 7.15-6.80 (m, 2H), 5.90 (q, J=7.9, 5.8 Hz, 1H), 4.55-4.46 (m, 3H), 4.15 (dt, J=12.1, 2.7 Hz, 1H). ¹⁹F NMR (376 MHz, Acetonitrile-d3) δ −77.27 (d, J=4.7 Hz), −109.77 (d, J=240.3 Hz), −119.60 (ddd, J=53.8, 40.3, 5.0 Hz), −122.22 (d, J=241.8 Hz), −144.87 (t, J=5.2 Hz).

Example 390. (S)-5-(8-(4-(4,5-difluoropyridin-2-yl)oxy)-3,3-difluoropyrrolidin-1-yl)imidazo[1,2-b]pyridazin-6-yl)pyrimidine-2,4(1H,3H)-dione

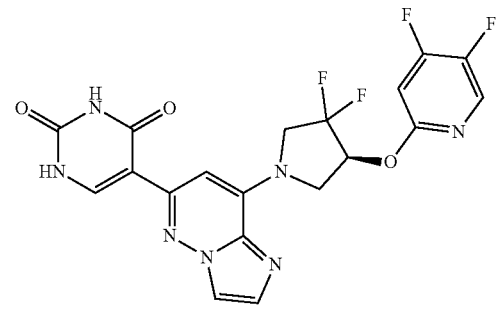 [SMILES: O=c1[nH]cc(-c2cc(N3C[C@H](Oc4cc(F)c(F)cn4)C(F)(F)C3)c3nccn3n2)c(=O)[nH]1]

(S)-5-(8-(4-((4,5-difluoropyridin-2-yl)oxy)-3,3-difluoro-pyrrolidin-1-yl)imidazo[1,2-b]pyridazin-6-yl)pyrimidine-2,4(1H,3H)-dione was prepared in the manner described for Example 389, but replacing 4-(difluoromethyl)-2,5-difluoro-pyridine with 2,4,5-trifluoropyridine. ES/MS m/z: 464.20. ¹H NMR (400 MHz, Acetonitrile-d3) δ 9.34 (d, J=14.9 Hz, 2H), 8.15-8.07 (m, 1H), 8.05 (dd, J=4.2, 1.6 Hz, 2H), 7.83 (t, J=3.5 Hz, 1H), 7.25 (s, 1H), 6.95 (dd, J=5.5, 1.3 Hz, 1H), 5.42 (tt, J=5.0, 2.5 Hz, 1H), 4.56-4.35 (m, 3H), 4.35-4.17 (m, 1H). ¹⁹F NMR (376 MHz, Acetonitrile-d3) δ −70.42 (d, J=23.2 Hz), −77.23, −108.15 (dtd, J=243.9, 20.3, 8.0 Hz), −120.09−−124.78 (m), −154.77 (ddd, J=23.1, 5.4, 2.7 Hz).

Example 391. 5-(8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione

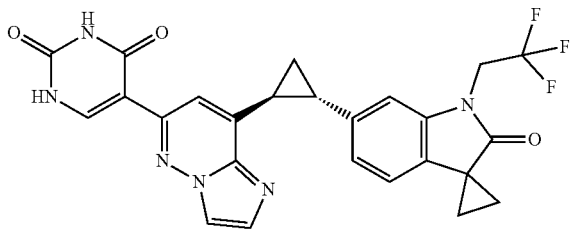 [SMILES: O=C1N(CC(F)(F)F)c2cc([C@H]3C[C@@H]3c3cc(-c4c[nH]c(=O)[nH]c4=O)nn4ccnc34)ccc2C12CC2]

5-(8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione was obtained through SFC chiral HPLC separation (peak 1) with racemic 5-(8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione. ES/MS m/z: 509.10. ¹H NMR (400 MHz, Acetonitrile-d3) δ 9.27 (s, 1H), 9.18 (s, 1H), 7.99 (d, J=9.3 Hz, 2H), 7.67 (s, 1H), 7.49 (s, 1H), 6.99 (d, J=8.2 Hz, 2H), 6.92 (d, J=7.6 Hz, 1H), 4.50 (q, J=9.2 Hz, 2H), 2.91-2.81 (m, 1H), 2.76 (dt, J=10.2, 5.5 Hz, 1H), 2.11 (dt, J=8.9, 5.5 Hz, 1H), 1.73 (dt, J=8.6, 5.5 Hz, 1H), 1.63 (t, J=3.8 Hz, 4H), 1.30 (s, 1H). ¹⁹F NMR (376 MHz, Acetonitrile-d3) δ −71.19 (t, J=9.2 Hz)

Example 392. 5-(8-((2S,2S)-2-(3-fluoro-1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione

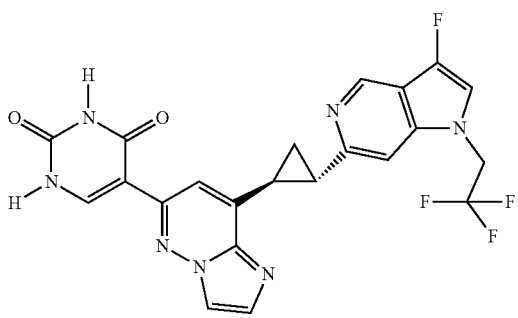 [SMILES: O=c1[nH]cc(-c2cc([C@H]3C[C@@H]3c3cc4c(cn3)c(F)cn4CC(F)(F)F)c3nccn3n2)c(=O)[nH]1]

5-(8-((2S,2S)-2-(3-fluoro-1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[3-fluoro-1-(2,2,2-trifluoroethyl)pyrrolo[3,2-c]pyridin-6-yl]cyclopropyl]imidazo[1,2-b]pyridazine. ES/MS m/z: 486.20 [M+H]. ¹H NMR (400 MHz, DMSO-d6) δ 11.57 (dd, J=10.2, 4.1 Hz, 2H), 9.27 (s, 1H), 8.35 (d, J=1.4 Hz, 1H), 8.13 (s, 1H), 8.05 (d, J=6.1 Hz, 1H), 7.91 (d, J=2.4 Hz, 1H), 7.85 (d, J=1.4 Hz, 1H), 7.68 (s, 1H), 5.33 (q, J=8.9 Hz, 2H), 3.39 (dt, J=9.5, 5.5 Hz, 1H), 3.00 (ddd, J=9.2, 6.2, 4.3 Hz, 1H), 2.35-2.26 (m, 1H), 2.14-2.04 (m, 1H). ¹⁹F NMR (376 MHz, DMSO-d6) δ −70.74 (t, J=9.0 Hz), −75.24 (d, J=2.8 Hz).

Example 393. 5-(8-((2S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione

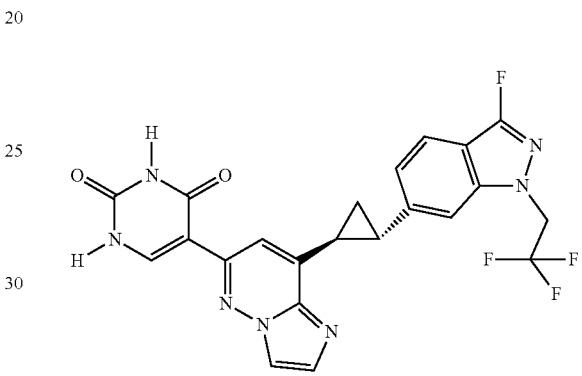

5-(8-((1S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[3-fluoro-1-(2,2,2-trifluoroethyl)indazol-6-yl]cyclopropyl]imidazo[1,2-b]pyridazine. ES/MS m/z: 486.2 [M+H]. ¹H NMR (400 MHz, DMSO-d6) δ 11.65 (dd, J=34.2, 4.1 Hz, 2H), 8.51 (s, 1H), 8.17-8.08 (m, 2H), 7.89-7.66 (m, 3H), 7.21 (dd, J=8.5, 1.2 Hz, 1H), 5.34 (q, J=9.0 Hz, 2H), 3.07-2.90 (m, 2H), 2.09-1.93 (m, 2H). ¹⁹F NMR (376 MHz, DMSO-d6) δ −70.24 (t, J=9.0 Hz), −133.85.

Example 394. 5-(8-((2S,2S)-2-(5-(trifluoromethyl)quinolin-7-yl)cyclopropyl)imidazo[1,2-b]pyridazin-6-yl)pyrimidine-2,4(1H,3H)-dione

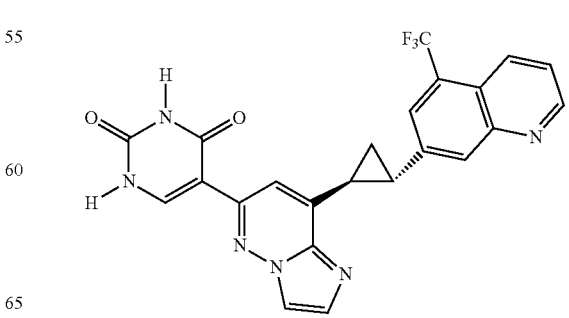

5-(8-((2S,2S)-2-(5-(trifluoromethyl)quinolin-7-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-[(1S,2S)-2-[6-(2,4-dimethoxypyrimidin-5-yl)imidazo[1,2-b]pyridazin-8-yl]cyclopropyl]-5-(trifluoromethyl)quinoline. ES/MS m/z: 465.10 [M+H]. $^1$H NMR (400 MHz, DMSO-d6) δ 11.60 (d, J=10.1 Hz, 2H), 9.06 (dd, J=4.3, 1.5 Hz, 1H), 8.51-8.40 (m, 2H), 8.21 (s, 1H), 8.08 (d, J=6.1 Hz, 1H), 8.06-7.97 (m, 2H), 7.76-7.67 (m, 2H), 3.15 (dt, J=9.7, 5.6 Hz, 1H), 3.00 (dt, J=9.6, 5.4 Hz, 1H), 2.20 (dt, J=9.9, 5.7 Hz, 1H), 2.10 (dt, J=8.7, 5.7 Hz, 1H). $^{19}$F NMR (376 MHz, DMSO-d6) δ −58.50, −75.27 (d, J=4.6 Hz).

Example 395. 5-(8-((2S,2S)-2-(8-(trifluoromethyl)quinolin-3-yl)cyclopropyl)imidazo[1,2-b]pyridazin-6-yl)pyrimidine-2,4(1H,3H)-dione

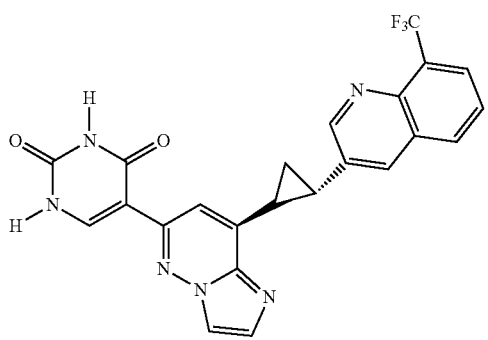

5-(8-((2S,2S)-2-(8-(trifluoromethyl)quinolin-3-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 3-[(1S,2S)-2-[6-(2,4-dimethoxypyrimidin-5-yl)imidazo[1,2-b]pyridazin-8-yl]cyclopropyl]-8-(trifluoromethyl)quinoline. ES/MS m/z: 465.10 [M+H]. $^1$H NMR (400 MHz, DMSO-d6) δ 11.64-11.56 (m, 2H), 9.05 (d, J=2.3 Hz, 1H), 8.40 (dd, J=16.9, 2.0 Hz, 2H), 8.28-8.21 (m, 1H), 8.11 (dd, J=25.4, 6.7 Hz, 2H), 7.98 (s, 1H), 7.80-7.71 (m, 2H), 3.06 (dt, J=9.4, 5.6 Hz, 1H), 3.01-2.91 (m, 1H), 2.24 (dt, J=9.3, 5.5 Hz, 1H), 2.07 (dt, J=8.5, 5.5 Hz, 1H).

Example 396. 5-(8-((1S,2S)-2-(3-isopropyl-1-(2,2,2-trifluoroethyl)-1H-indazol-6-yl)cyclopropyl)imidazo[1,2-b]pyridazin-6-yl)pyrimidine-2,4(1H,3H)-dione

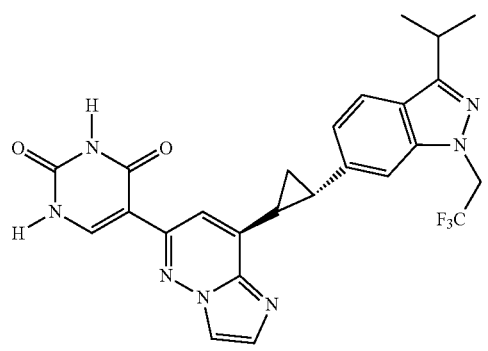

5-(8-((1S,2S)-2-(3-isopropyl-1-(2,2,2-trifluoroethyl)-1H-indazol-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-[(1S,2S)-2-[3-isopropyl-1-(2,2,2-trifluoroethyl)indazol-6-yl]cyclopropyl]imidazo[1,2-b]pyridazine(racemic). ES/MS m/z: 510.20 [M+H]. $^1$H NMR (400 MHz, DMSO-d6) δ 11.56 (d, J=4.9 Hz, 2H), 8.35 (d, J=1.5 Hz, 1H), 8.04 (d, J=6.3 Hz, 1H), 7.88 (s, 1H), 7.77 (d, J=8.4 Hz, 1H), 7.62 (d, J=16.2 Hz, 2H), 7.07 (dd, J=8.4, 1.4 Hz, 1H), 5.31 (q, J=9.1 Hz, 2H), 3.35 (h, J=6.9 Hz, 1H), 2.98 (ddd, J=9.2, 6.3, 4.3 Hz, 1H), 2.84-2.75 (m, 1H), 2.11 (dq, J=12.5, 4.5, 3.7 Hz, 1H), 1.97-1.87 (m, 1H), 1.37 (d, J=7.0 Hz, 6H). $^{19}$F NMR (376 MHz, DMSO-d6) δ−69.99 (t, J=9.1 Hz), −75.16.

Example 397. 5-(8-(3-fluoro-3-(trifluoromethyl)azetidin-1-yl)imidazo[1,2-b]pyridazin-6-yl)pyrimidine-2,4(1H,3H)-dione

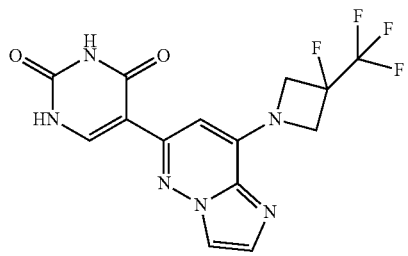

5-(8-(3-fluoro-3-(trifluoromethyl)azetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-fluoro-3-(trifluoromethyl)azetidin-1-yl)imidazo[1,2-b]pyridazine, and running the reaction at 60° C. for 16 h. Purification was accomplished by RP-HPLC (10-90% MeCN/H$_2$O with TFA modifier, Gemini column). ES/MS m/z: 371.1 [M+H]. $^1$H NMR (400 MHz, DMSO-d6) δ 11.51-11.34 (m, 2H), 8.10 (d, J=1.2 Hz, 1H), 7.94 (d, J=6.1 Hz, 1H), 7.60 (d, J=1.2 Hz, 1H), 6.61 (s, 1H), 4.93-4.71 (m, 4H). $^{19}$F NMR (376 MHz, DMSO-d6) δ −75.26, −82.92 (d, J=7.5 Hz), −172.25-−172.66 (m).

Example 398. 5-(8-(2-azaspiro[3.3]heptan-2-yl)imidazo[1,2-b]pyridazin-6-yl)pyrimidine-2,4(1H,3H)-dione

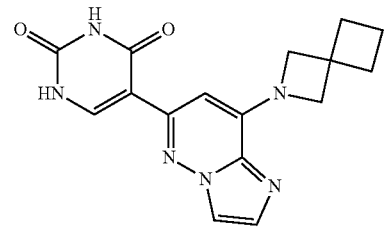

5-(8-(2-azaspiro[3.3]heptan-2-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(2-azaspiro[3.3]heptan-2-yl)imidazo[1,2-b]pyridazine, and running the reaction at 60° C. for 16 h. Purification was accomplished by RP-HPLC (10-90% MeCN/H₂O with TFA modifier, Gemini column). ES/MS m/z: 325.2 [M+H]. ¹H NMR (400 MHz, DMSO-d6) δ 11.39 (d, J=7.6 Hz, 2H), 8.08 (s, 1H), 7.94 (d, J=6.0 Hz, 1H), 7.66 (s, 1H), 6.52 (s, 1H), 4.34 (s, 4H), 2.23 (t, J=7.6 Hz, 4H), 1.82 (p, J=7.6 Hz, 2H).

Example 399. 5-(8-(3-(difluoromethyl)-3-methylazetidin-1-yl)imidazo[1,2-b]pyridazin-6-yl)pyrimidine-2,4(1H,3H)-dione

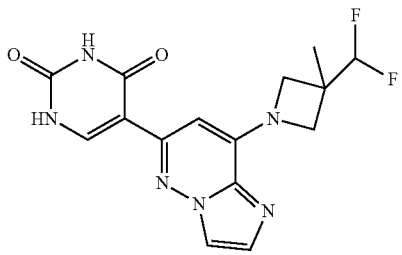

5-(8-(3-(difluoromethyl)-3-methylazetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(3-(difluoromethyl)-3-methylazetidin-1-yl)-6-(2,4-dimethoxypyrimidin-5-yl)imidazo[1,2-b]pyridazine, and running the reaction at 60° C. for 16 h. Purification was accomplished by RP-HPLC (10-90% MeCN/H₂O with TFA modifier, Gemini column). ES/MS m/z: 349.2 [M+H]. ¹H NMR (400 MHz, DMSO-d6) δ 11.53-11.22 (m, 2H), 8.04 (d, J=1.3 Hz, 1H), 7.92 (d, J=6.1 Hz, 1H), 7.57 (d, J=1.2 Hz, 1H), 6.48 (s, 1H), 6.33 (t, J=56.4 Hz, 1H), 4.38 (br s, 2H), 4.11 (br s, 2H), 1.41 (s, 3H). ¹⁹F NMR (376 MHz, DMSO-d6) δ -75.21 (d, J=2.9 Hz), -129.98 (d, J=56.3 Hz).

Example 400. 5-(8-(3-(2,2-difluorocyclopropyl)azetidin-1-yl)imidazo[1,2-b]pyridazin-6-yl)pyrimidine-2,4(1H,3H)-dione

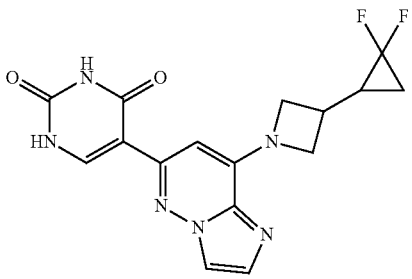

5-(8-(3-(2,2-difluorocyclopropyl)azetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(3-(2,2-difluorocyclopropyl)azetidin-1-yl)-6-(2,4-dimethoxypyrimidin-5-yl)imidazo[1,2-b]pyridazine, and running the reaction at 60° C. for 16 h. Purification was accomplished by RP-HPLC (10-90% MeCN/H₂O with TFA modifier, Gemini column). ES/MS m/z: 361.1 [M+H]. ¹H NMR (400 MHz, DMSO-d6) δ 11.47-11.32 (m, 2H), 8.05 (d, J=1.2 Hz, 1H), 7.94 (d, J=6.1 Hz, 1H), 7.60 (d, J=1.2 Hz, 1H), 6.49 (s, 1H), 4.52 (br s, 2H), 4.19 (br s, 2H), 2.84 (h, J=7.6 Hz, 1H), 2.22 (tt, J=11.4, 7.9 Hz, 1H), 1.63 (tdd, J=12.3, 7.9, 4.5 Hz, 1H), 1.37 (dtd, J=11.5, 7.7, 3.6 Hz, 1H). ¹⁹F NMR (376 MHz, DMSO-d6) δ -75.19, -126.51--127.27 (m), -141.33--142.11 (m).

Example 401. 5-(8-(3-cyclobutylazetidin-1-yl)imidazo[1,2-b]pyridazin-6-yl)pyrimidine-2,4(1H,3H)-dione

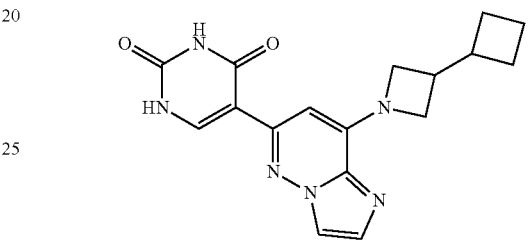

5-(8-(3-cyclobutylazetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(3-cyclobutylazetidin-1-yl)-6-(2,4-dimethoxypyrimidin-5-yl)imidazo[1,2-b]pyridazine, and running the reaction at 60° C. for 16 h. Purification was accomplished by RP-HPLC (10-90% MeCN/H₂O with TFA modifier, Gemini column). ES/MS m/z: 339.1 [M+H]. ¹H NMR (400 MHz, DMSO-d6) δ 11.45-11.31 (m, 2H), 8.03 (s, 1H), 7.93 (d, J=6.1 Hz, 1H), 7.57 (s, 1H), 6.45 (s, 1H), 4.40 (br s, 2H), 3.99 (br s, 2H), 2.87 (dq, J=11.0, 4.1, 2.9 Hz, 1H), 2.66 (p, J=8.0 Hz, 1H), 2.04 (ddd, J=14.2, 10.5, 6.1 Hz, 2H), 1.85 (tdd, J=18.9, 9.5, 4.6 Hz, 2H), 1.77-1.65 (m, 2H).

Example 402. 5-(7-(3-fluoro-3-(trifluoromethyl)azetidin-1-yl)-[1,2,4]triazolo[1,5-a]pyrimidin-5-yl)pyrimidine-2,4(1H,3H)-dione

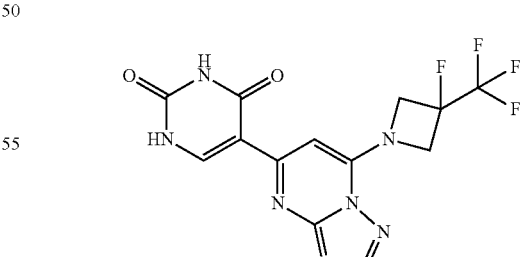

5-(7-(3-fluoro-3-(trifluoromethyl)azetidin-1-yl)-[1,2,4]triazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-(2,4-dimethoxypyrimidin-5-yl)-7-(3-fluoro-3-(trifluoromethyl)azetidin-1- yl)-[1,2,4]triazolo[1,5-a]pyrimidine, and running the reaction at 60° C. for 16 h. Purification was accomplished by RP-HPLC (10-90% MeCN/H₂O with TFA modifier, Gemini column). ES/MS m/z: 372.1 [M+H]. ¹H NMR (400 MHz, DMSO-d6) δ 11.72-11.57 (m, 1H), 11.51 (s, 1H), 8.47 (d, J=6.4 Hz, 1H), 8.42 (s, 1H), 7.33 (s, 1H), 4.98 (dq, J=22.9, 11.7 Hz, 4H). ¹⁹F NMR (376 MHz, DMSO-d6) δ −74.13, −82.62 (d, J=7.7 Hz), −172.61.

Example 403. 5-(8-(3-(difluoromethyl)azetidin-1-yl)imidazo[1,2-b]pyridazin-6-yl)pyrimidine-2,4(1H,3H)-dione

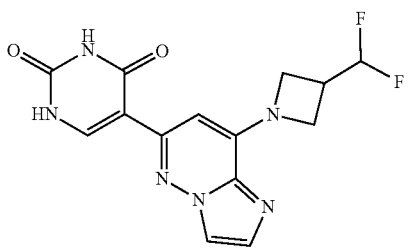 [SMILES: O=c1[nH]cc(-c2cc(N3CC(C(F)F)C3)c3nccn3n2)c(=O)[nH]1]

5-(8-(3-(difluoromethyl)azetidin-1-yl)pyridazin-6-yl)pyrimidine-2,4(1H,3H)-dione was prepared in the manner described for Example 1, but replacing 8-cyclopropyl-6-(2,4-dimethoxypyrimidin-5-yl)-2-methylimidazo[1,2-b]pyridazine with 8-(3-(difluoromethyl)azetidin-1-yl)-6-(2,4-dimethoxypyrimidin-5-yl)imidazo[1,2-b]pyridazine, and running the reaction at 70° C. for 3 h. Purification was accomplished by RP-HPLC (10-90% MeCN/H₂O with TFA modifier, Gemini column). ES/MS m/z: 335.1 [M+H]. ¹H NMR (400 MHz, DMSO-d6) δ 11.46-11.29 (m, 2H), 8.03 (s, 1H), 7.92 (d, J=6.0 Hz, 1H), 7.56 (s, 1H), 6.46 (s, 1H), 6.43 (t, J=56.3, 4.3 Hz, 1H), 4.48 (br s, 2H), 4.30 (br s, 2H). ¹⁹F NMR (376 MHz, DMSO-d6) δ −75.05, −125.00 (dd, J=56.4, 14.8 Hz).

Example 404. 5-(8-(3-cyclopropylazetidin-1-yl)imidazo[1,2-b]pyridazin-6-yl)pyrimidine-2,4(1H,3H)-dione

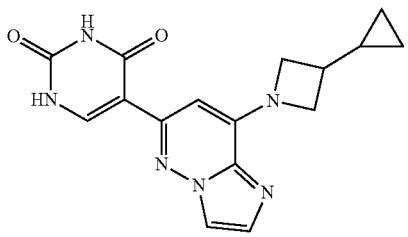 [SMILES: O=c1[nH]cc(-c2cc(N3CC(C4CC4)C3)c3nccn3n2)c(=O)[nH]1]

5-(8-(3-cyclopropylazetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methylimidazo[1,2-b]pyridazine with 8-(3-cyclopropylazetidin-1-yl)-6-(2,4-dimethoxypyrimidin-5-yl)imidazo[1,2-b]pyridazine, and running the reaction at 60° C. for 16 h. Purification was accomplished by RP-HPLC (10-90% MeCN/H₂O with TFA modifier, Gemini column). ES/MS m/z: 325.2 [M+H]. ¹H NMR (400 MHz, DMSO-d6) δ 11.52-11.30 (m, 2H), 8.05 (d, J=4.4 Hz, 1H), 7.94 (d, J=5.8 Hz, 1H), 7.61 (s, 1H), 6.47 (d, J=4.4 Hz, 1H), 4.42 (br s, 2H), 4.01 (br s, 2H), 1.24-0.98 (m, 1H), 0.50 (d, J=7.7 Hz, 2H), 0.22 (d, J=5.0 Hz, 2H).

Example 405. 5-(8-(5,5-difluoro-2-azaspiro[3.3]heptan-2-yl)imidazo[1,2-b]pyridazin-6-yl)pyrimidine-2,4(1H,3H)-dione

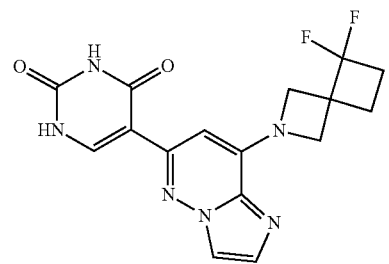 [SMILES: O=c1[nH]cc(-c2cc(N3CC4(CCC4(F)F)C3)c3nccn3n2)c(=O)[nH]1]

5-(8-(5,5-difluoro-2-azaspiro[3.3]heptan-2-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methylimidazo[1,2-b]pyridazine with 8-(5,5-difluoro-2-azaspiro[3.3]heptan-2-yl)-6-(2,4-dimethoxypyrimidin-5-yl)imidazo[1,2-b]pyridazine, and running the reaction at 60° C. for 16 h. Purification was accomplished by RP-HPLC (10-90% MeCN/H₂O with TFA modifier, Gemini column). ES/MS m/z: 361.2 [M+H]. ¹H NMR (400 MHz, DMSO-d6) δ 11.50-11.28 (m, 2H), 8.06 (d, J=1.3 Hz, 1H), 7.94 (d, J=6.1 Hz, 1H), 7.60 (d, J=1.3 Hz, 1H), 6.53 (s, 1H), 4.55 (d, J=9.9 Hz, 2H), 4.33 (d, J=9.7 Hz, 2H), 2.60-2.51 (m, 2H), 2.17-2.07 (m, 2H). ¹⁹F NMR (376 MHz, DMSO-d6) δ −75.25, −101.34.

Example 406. 5-(8-(1,1-difluoro-5-azaspiro[2.3]hexan-5-yl)imidazo[1,2-b]pyridazin-6-yl)pyrimidine-2,4(1H,3H)-dione

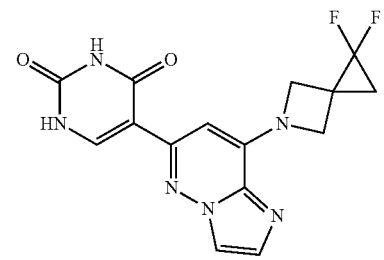 [SMILES: O=c1[nH]cc(-c2cc(N3CC4(C3)CC4(F)F)c3nccn3n2)c(=O)[nH]1]

5-(8-(1,1-difluoro-5-azaspiro[2.3]hexan-5-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methylimidazo[1,2-b]pyridazine with 8-(1,1-difluoro-5-azaspiro[2.3]hexan-5-yl)-6-(2,4-dimethoxypyrimidin-5-yl)imidazo[1,2-b]pyridazine, and running the reaction at 60° C. for 16 h. Purification was accomplished by RP-HPLC (10-90% MeCN/H₂O with TFA modifier, Gemini column). ES/MS m/z: 347.1 [M+H]. ¹H NMR (400 MHz, DMSO-d6) δ 11.48-11.33 (m, 2H), 8.06 (s, 1H), 7.94 (d, J=6.1 Hz, 1H), 7.59 (s, 1H), 6.55 (s, 1H), 4.51 (s, 4H), 1.84 (t, J=8.9 Hz, 2H). $^{19}$F NMR (376 MHz, DMSO-d6) δ −75.22, −138.15 (t, J=9.5 Hz).

Example 407. 4-((2S,2S)-2-(6-(2,4-dioxo-1,2,3,4-tetrahydropyrimidin-5-yl)imidazo[1,2-b]pyridazin-8-yl)cyclopropyl)-3-fluorobenzonitrile

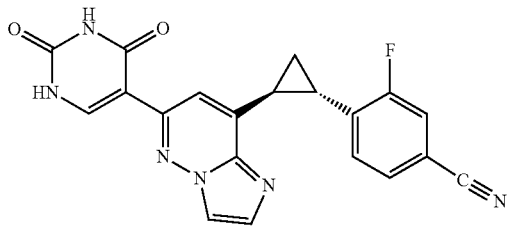 [SMILES: N#Cc1ccc([C@H]2C[C@@H]2c2cc(-c3c[nH]c(=O)[nH]c3=O)nn3ccnc23)c(F)c1]

4-((2S,2S)-2-(6-(2,4-dioxo-1,2,3,4-tetrahydropyrimidin-5-yl)imidazo[1,2-b]pyridazin-8-yl)cyclopropyl)-3-fluorobenzonitrile (Racemic Mixture) was prepared in the manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)imidazo[1,2-b]pyridazin-8-yl)cyclopropyl)-3-fluorobenzonitrile, and running the reaction at 70° C. for 3 h. Purification was accomplished by RP-HPLC (10-90% MeCN/H$_2$O with TFA modifier, Gemini column). ES/MS m/z: 389.1 [M+H]. $^1$H NMR (400 MHz, DMSO-d6) δ 11.55 (d, J=5.5 Hz, 2H), 8.35 (d, J=1.5 Hz, 1H), 8.03 (d, J=6.1 Hz, 1H), 7.93-7.86 (m, 1H), 7.83 (dd, J=10.2, 1.6 Hz, 1H), 7.71 (dd, J=8.0, 1.6 Hz, 1H), 7.65 (s, 1H), 7.49 (t, J=7.9 Hz, 1H), 3.09-3.00 (m, 1H), 2.86 (ddd, J=8.9, 6.1, 4.5 Hz, 1H), 2.18 (dt, J=8.9, 5.3 Hz, 1H), 1.91 (ddd, J=8.9, 6.3, 4.8 Hz, 1H). $^{19}$F NMR (376 MHz, DMSO-d6) δ −75.21, −117.94 (t, J=8.9 Hz).

Example 408. 3-((1S,2S)-2-(6-(2,4-dioxo-1,2,3,4-tetrahydropyrimidin-5-yl)imidazo[1,2-b]pyridazin-8-yl)cyclopropyl)-2-fluorobenzonitrile

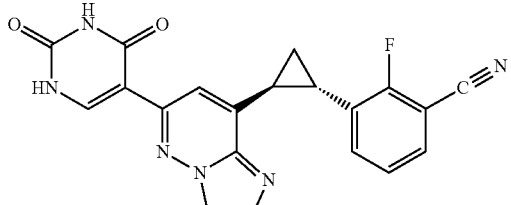

3-((2S,2S)-2-(6-(2,4-dioxo-1,2,3,4-tetrahydropyrimidin-5-yl)imidazo[1,2-b]pyridazin-8-yl)cyclopropyl)-2-fluorobenzonitrile (Racemic Mixture) was prepared in the manner described for Example 1, but replacing 8-cyclopropyl-6-(2,4-dimethoxypyrimidin-5-yl)-2-methyl-imidazo[1,2-b]pyridazine with 3-((2S,2S)-2-(6-(2,4-dimethoxypyrimidin-5-yl)imidazo[1,2-b]pyridazin-8-yl)cyclopropyl)-2-fluorobenzonitrile, and running the reaction at 70° C. for 3 h. Purification was accomplished by RP-HPLC (10-90% MeCN/H$_2$O with TFA modifier, Gemini column). ES/MS m/z: 389.1 [M+H]. $^1$H NMR (400 MHz, DMSO-d6) δ 11.56 (d, J=5.9 Hz, 2H), 8.36 (d, J=1.4 Hz, 1H), 8.03 (d, J=6.1 Hz, 1H), 7.91 (s, 1H), 7.80 (ddd, J=7.8, 6.1, 1.7 Hz, 1H), 7.71-7.63 (m, 2H), 7.41 (t, J=7.8 Hz, 1H), 3.01 (dt, J=9.1, 5.6 Hz, 1H), 2.85-2.77 (m, 1H), 2.13 (dt, J=8.9, 5.3 Hz, 1H), 1.92-1.84 (m, 1H). $^{19}$F NMR (376 MHz, DMSO-d6) δ −75.19, −115.20.

Example 409. 5-(8-(3-(2-fluoropropan-2-yl)azetidin-1-yl)imidazo[1,2-b]pyridazin-6-yl)pyrimidine-2,4(1H,3H)-dione

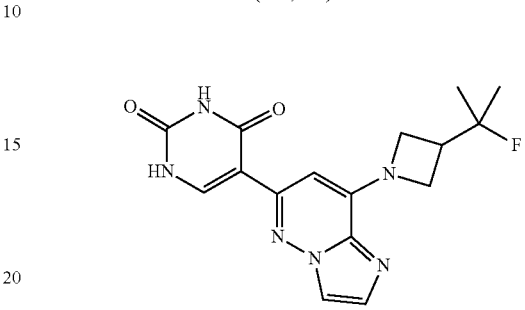

5-(8-(3-(2-fluoropropan-2-yl)azetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-(2-fluoropropan-2-yl)azetidin-1-yl)imidazo[1,2-b]pyridazine, and running the reaction at 60° C. for 16 h. Purification was accomplished by RP-HPLC (10-90% MeCN/H$_2$O with TFA modifier, Gemini column). ES/MS m/z: 345.2 [M+H]. $^1$H NMR (400 MHz, DMSO-d6) δ 11.46-11.28 (m, 2H), 8.03 (s, 1H), 7.92 (d, J=6.1 Hz, 1H), 7.56 (s, 1H), 6.45 (s, 1H), 4.41 (br s, 2H), 4.24 (br s, 2H), 3.14-2.95 (m, 1H), 1.36 (s, 3H), 1.31 (s, 3H). $^{19}$F NMR (376 MHz, DMSO-d6) δ −75.07, −152.62−−153.15 (m).

Example 410. 5-(8-(tetrahydro-2H-pyran-4-yl)imidazo[1,2-b]pyridazin-6-yl)pyrimidine-2,4(1H,3H)-dione

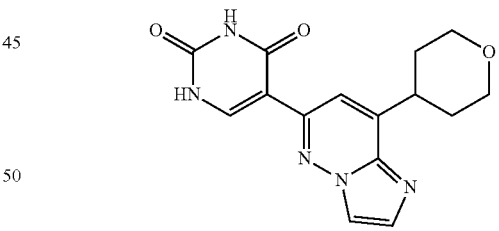

5-(8-(tetrahydro-2H-pyran-4-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(tetrahydro-2H-pyran-4-yl)imidazo[1,2-b]pyridazine, and running the reaction at 60° C. for 16 h. Purification was accomplished by RP-HPLC (10-90% MeCN/H$_2$O with TFA modifier, Gemini column). ES/MS m/z: 314.1 [M+H]. $^1$H NMR (400 MHz, DMSO-d6) δ 11.81 (dd, J=6.5, 2.0 Hz, 1H), 11.63 (d, J=1.9 Hz, 1H), 8.59 (d, J=1.9 Hz, 1H), 8.27 (d, J=1.9 Hz, 1H), 8.14 (d, J=6.3 Hz, 1H), 8.09 (s, 1H), 4.11-3.93 (m, 2H), 3.64-3.47 (m, 3H), 1.91 (ddd, J=12.4, 4.0, 1.8 Hz, 2H), 1.77 (qd, J=12.2, 4.3 Hz, 2H).

Example 411. 4-((1S,2S)-2-(6-(2,4-dioxo-1,2,3,4-tetrahydropyrimidin-5-yl)imidazo[1,2-b]pyridazin-8-yl)cyclopropyl)-2-(trifluoromethyl)benzonitrile

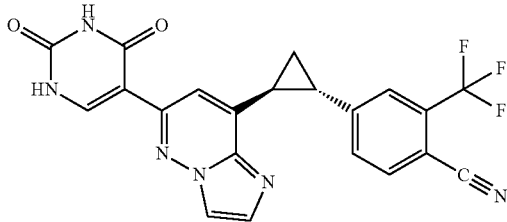 [SMILES: N#Cc1ccc([C@H]2C[C@@H]2c2cc(-c3c[nH]c(=O)[nH]c3=O)nn3ccnc23)cc1C(F)(F)F]

4-((2S,2S)-2-(6-(2,4-dioxo-1,2,3,4-tetrahydropyrimidin-5-yl)imidazo[1,2-b]pyridazin-8-yl)cyclopropyl)-2-(trifluoromethyl)benzonitrile (Racemic Mixture) was prepared in the manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)imidazo[1,2-b]pyridazin-8-yl)cyclopropyl)-2-(trifluoromethyl)benzonitrile, and running the reaction at 70° C. for 16 h. Purification was accomplished by RP-HPLC (10-90% MeCN/H$_2$O with TFA modifier, Gemini column). ES/MS m/z: 439.1 [M+H]. $^1$H NMR (400 MHz, DMSO-d6) δ 11.56 (d, J=7.6 Hz, 2H), 8.35 (d, J=1.4 Hz, 1H), 8.11 (d, J=8.0 Hz, 1H), 8.04 (d, J=6.1 Hz, 1H), 7.90 (dd, J=7.9, 1.5 Hz, 2H), 7.78 (dd, J=8.1, 1.7 Hz, 1H), 7.64 (s, 1H), 3.06 (ddd, J=9.1, 6.1, 4.3 Hz, 1H), 2.92 (ddd, J=9.0, 6.1, 4.3 Hz, 1H), 2.24 (dt, J=8.8, 5.5 Hz, 1H), 1.99 (dt, J=8.8, 5.5 Hz, 1H). $^{19}$F NMR (376 MHz, DMSO-d6) δ −61.15, −75.21.

Example 412. 5-((2S,2S)-2-(6-(2,4-dioxo-1,2,3,4-tetrahydropyrimidin-5-yl)imidazo[1,2-b]pyridazin-8-yl)cyclopropyl)-2-(trifluoromethyl)benzonitrile

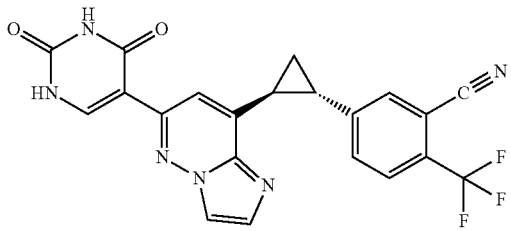 [SMILES: N#Cc1cc([C@H]2C[C@@H]2c2cc(-c3c[nH]c(=O)[nH]c3=O)nn3ccnc23)ccc1C(F)(F)F]

5-((2S,2S)-2-(6-(2,4-dioxo-1,2,3,4-tetrahydropyrimidin-5-yl)imidazo[1,2-b]pyridazin-8-yl)cyclopropyl)-2-(trifluoromethyl)benzonitrile (Racemic Mixture) was prepared in the manner described for Example 1, but replacing 8-cyclopropyl-6-(2,4-dimethoxypyrimidin-5-yl)-2-methyl-imidazo[1,2-b]pyridazine with 5-((2S,2S)-2-(6-(2,4-dimethoxypyrimidin-5-yl)imidazo[1,2-b]pyridazin-8-yl)cyclopropyl)-2-(trifluoromethyl)benzonitrile, and running the reaction at 70° C. for 16 h. Purification was accomplished by RP-HPLC (10-90% MeCN/H$_2$O with TFA modifier, Gemini column). ES/MS m/z: 439.1 [M+H]. $^1$H NMR (400 MHz, DMSO-d6) δ 11.54 (s, 2H), 8.31 (s, 1H), 8.09 (d, J=1.6 Hz, 1H), 8.02 (d, J=6.4 Hz, 1H), 7.93 (d, J=8.4 Hz, 1H), 7.88-7.78 (m, 2H), 7.60 (s, 1H), 3.07-3.00 (m, 1H), 2.90 (ddd, J=8.9, 6.2, 4.4 Hz, 1H), 2.25 (dt, J=8.8, 5.4 Hz, 1H), 1.94 (dt, J=8.8, 5.5 Hz, 1H). $^{19}$F NMR (376 MHz, DMSO-d6) δ −60.80, −75.02.

Example 413. 4-((2S,2S)-2-(6-(2,4-dioxo-1,2,3,4-tetrahydropyrimidin-5-yl)imidazo[1,2-b]pyridazin-8-yl)cyclopropyl)-2-(trifluoromethoxy)benzonitrile

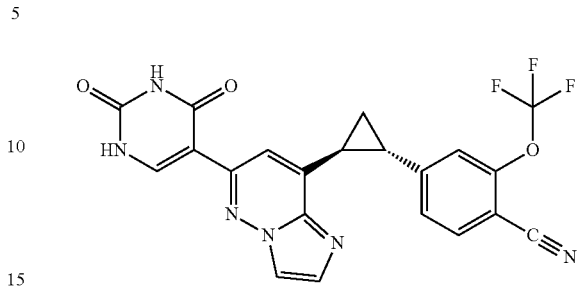

4-((2S,2S)-2-(6-(2,4-dioxo-1,2,3,4-tetrahydropyrimidin-5-yl)imidazo[1,2-b]pyridazin-8-yl)cyclopropyl)-2-(trifluoromethoxy)benzonitrile (Racemic Mixture) was prepared in the manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)imidazo[1,2-b]pyridazin-8-yl)cyclopropyl)-2-(trifluoromethoxy)benzonitrile, and running the reaction at 70° C. for 16 h. Purification was accomplished by RP-HPLC (10-90% MeCN/H$_2$O with TFA modifier, Gemini column). ES/MS m/z: 455.1 [M+H]. $^1$H NMR (400 MHz, DMSO-d6) δ 11.56 (d, J=6.6 Hz, 2H), 8.35 (d, J=1.4 Hz, 1H), 8.03 (d, J=6.0 Hz, 1H), 7.99 (d, J=8.1 Hz, 1H), 7.92-7.83 (m, 1H), 7.68-7.58 (m, 2H), 7.51 (dd, J=8.2, 1.6 Hz, 1H), 3.03 (ddd, J=9.0, 6.2, 4.3 Hz, 1H), 2.89 (ddd, J=9.0, 6.3, 4.3 Hz, 1H), 2.22 (dt, J=9.0, 5.6 Hz, 1H), 1.92 (dt, J=8.8, 5.4 Hz, 1H). $^{19}$F NMR (376 MHz, DMSO-d6) δ −57.52, −75.23.

Example 414. 5-((2S,2S)-2-(6-(2,4-dioxo-1,2,3,4-tetrahydropyrimidin-5-yl)imidazo[1,2-b]pyridazin-8-yl)cyclopropyl)-2-(trifluoromethoxy)benzonitrile

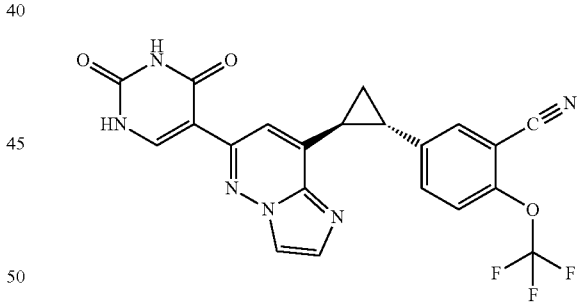

5-((2S,2S)-2-(6-(2,4-dioxo-1,2,3,4-tetrahydropyrimidin-5-yl)imidazo[1,2-b]pyridazin-8-yl)cyclopropyl)-2-(trifluoromethoxy)benzonitrile (Racemic Mixture) was prepared in the manner described for Example 1, but replacing 8-cyclopropyl-6-(2,4-dimethoxypyrimidin-5-yl)-2-methyl-imidazo[1,2-b]pyridazine with 5-((2S,2S)-2-(6-(2,4-dimethoxypyrimidin-5-yl)imidazo[1,2-b]pyridazin-8-yl)cyclopropyl)-2-(trifluoromethoxy)benzonitrile, and running the reaction at 70° C. for 16 h. Purification was accomplished by RP-HPLC (10-90% MeCN/H$_2$O with TFA modifier, Gemini column). ES/MS m/z: 455.1 [M+H]. $^1$H NMR (400 MHz, DMSO-d6) δ 11.69-11.45 (m, 2H), 8.37 (d, J=1.5 Hz, 1H), 8.05 (d, J=6.1 Hz, 1H), 7.97 (d, J=2.4 Hz, 1H), 7.92 (d, J=1.5 Hz, 1H), 7.79 (dd, J=8.8, 2.4 Hz, 1H), 7.64 (d, J=7.2 Hz, 2H), 2.93 (ddd, J=9.0, 6.2, 4.3 Hz, 1H), 2.84 (ddd, J=8.9, 6.1, 4.4 Hz, 1H), 2.15 (dt, J=8.8, 5.5 Hz, 1H), 1.90 (dt, J=8.8, 5.5 Hz, 1H). $^{19}$F NMR (376 MHz, DMSO-d6) δ −57.81, −75.22.

Example 415. 4-((2S,2S)-2-(6-(2,4-dioxo-1,2,3,4-tetrahydropyrimidin-5-yl)-3-fluoroimidazo[1,2-b]pyridazin-8-yl)cyclopropyl)-2-fluorobenzonitrile

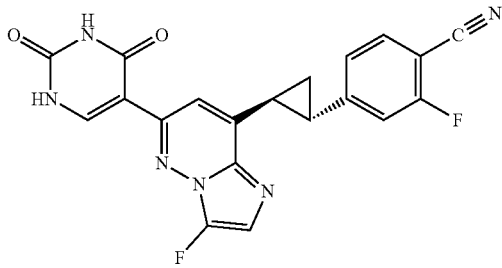 [SMILES: N#Cc1ccc([C@H]2C[C@@H]2c2cc(-c3c[nH]c(=O)[nH]c3=O)nn3c(F)cnc23)cc1F]

4-((2S,2S)-2-(6-(2,4-dioxo-1,2,3,4-tetrahydropyrimidin-5-yl)-3-fluoroimidazo[1,2-b]pyridazin-8-yl)cyclopropyl)-2-fluorobenzonitrile was prepared in the manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)-3-fluoroimidazo[1,2-b]pyridazin-8-yl)cyclopropyl)-2-fluorobenzonitrile, and running the reaction at 70° C. for 16 h. Purification was accomplished by RP-HPLC (10-90% MeCN/H$_2$O with TFA modifier, Gemini column). ES/MS m/z: 407.1 [M+H]. $^1$H NMR (400 MHz, DMSO-d6) δ 11.54 (d, J=4.2 Hz, 2H), 8.02 (d, J=6.4 Hz, 1H), 7.84 (dd, J=8.1, 7.1 Hz, 1H), 7.55 (d, J=7.1 Hz, 1H), 7.52 (s, 1H), 7.48 (dd, J=11.1, 1.6 Hz, 1H), 7.34 (dd, J=8.1, 1.6 Hz, 1H), 2.99 (dt, J=9.4, 5.4 Hz, 1H), 2.83 (ddd, J=8.9, 6.2, 4.3 Hz, 1H), 2.27 (ddd, J=8.8, 6.2, 4.9 Hz, 1H), 1.87 (dt, J=8.8, 5.3 Hz, 1H). $^{19}$F NMR (376 MHz, DMSO-d6) δ −75.24, −109.46 (dd, J=11.1, 7.0 Hz), −155.57 (d, J=7.0 Hz).

Example 416. 5-(7-((2S,2S)-2-(2,4-difluorophenyl)cyclopropyl)-[1,2,4]triazolo[1,5-a]pyrimidin-5-yl)pyrimidine-2,4(1H,3H)-dione

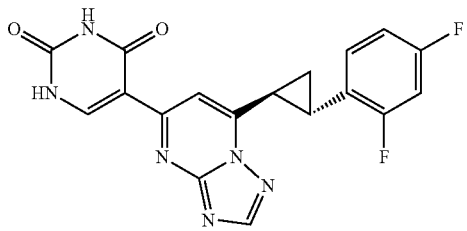 [SMILES: O=c1[nH]cc(-c2cc([C@H]3C[C@@H]3c3ccc(F)cc3F)n3ncnc3n2)c(=O)[nH]1]

5-(7-((2S,2S)-2-(2,4-difluorophenyl)cyclopropyl)-[1,2,4]triazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-((1S,2S)-2-(2,4-difluorophenyl)cyclopropyl)-5-(2,4-dimethoxypyrimidin-5-yl)-[1,2,4]triazolo[1,5-a]pyrimidine, and running the reaction at 70° C. for 3 h. Purification was accomplished by RP-HPLC (10-90% MeCN/H$_2$O with TFA modifier, Gemini column). ES/MS m/z: 383.1 [M+H]. $^1$H NMR (400 MHz, DMSO-d6) δ 11.76 (d, J=6.2 Hz, 1H), 11.59 (d, J=1.9 Hz, 1H), 8.61 (s, 1H), 8.50 (d, J=6.4 Hz, 1H), 8.04 (s, 1H), 7.45 (td, J=8.8, 6.4 Hz, 1H), 7.25 (ddd, J=10.7, 9.2, 2.6 Hz, 1H), 7.10 (td, J=8.6, 2.5 Hz, 1H), 2.99 (dt, J=8.9, 5.6 Hz, 1H), 2.79 (dt, J=9.3, 6.0 Hz, 1H), 1.92 (ddt, J=23.8, 8.7, 5.6 Hz, 2H). $^{19}$F NMR (376 MHz, DMSO-d6) δ −112.84 (ddd, J=15.4, 8.6, 6.4 Hz), −115.28 (td, J=9.9, 7.1 Hz).

Example 417. 5-(7-((2S,2S)-2-(4-(trifluoromethyl)phenyl)cyclopropyl)-[1,2,4]triazolo[1,5-a]pyrimidin-5-yl)pyrimidine-2,4(1H,3H)-dione

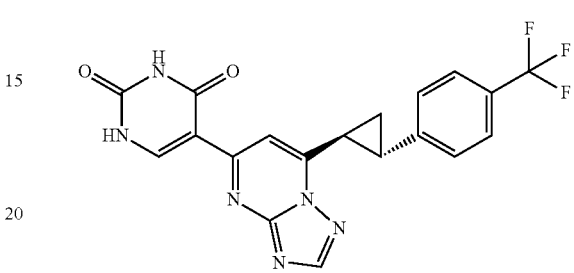

5-(7-((1S,2S)-2-(4-(trifluoromethyl)phenyl)cyclopropyl)-[1,2,4]triazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-(2,4-dimethoxypyrimidin-5-yl)-7-((2S,2S)-2-(4-(trifluoromethyl)phenyl)cyclopropyl)-[1,2,4]triazolo[1,5-a]pyrimidine. Purification was accomplished by RP-HPLC (10-90% MeCN/H$_2$O with TFA modifier, Gemini column). ES/MS m/z: 415.1 [M+H]. $^1$H NMR (400 MHz, Methanol-d4) δ 8.72 (s, 1H), 8.51 (s, 1H), 8.17 (s, 1H), 7.65 (d, J=8.2 Hz, 2H), 7.53 (d, J=8.2 Hz, 2H), 3.30-3.23 (m, 2H), 2.95-2.81 (m, 1H), 2.18-2.05 (m, 1H), 2.00-1.90 (m, 2H). $^{19}$F NMR (376 MHz, Methanol-d4) δ −64.48, −77.54.

Example 418. 5-(8-((2S,2S)-2-(4-(difluoromethyl)phenyl)cyclopropyl)imidazo[1,2-b]pyridazin-6-yl)pyrimidine-2,4(1H,3H)-dione

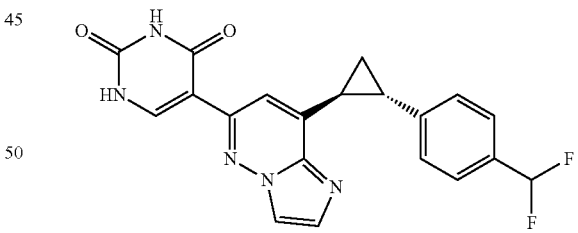

5-(8-((1S,2S)-2-(4-(difluoromethyl)phenyl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-((2S,2S)-2-(4-(difluoromethyl)phenyl)cyclopropyl)-6-(2,4-dimethoxypyrimidin-5-yl)imidazo[1,2-b]pyridazine. Purification was accomplished by RP-HPLC (10-90% MeCN/H$_2$O with TFA modifier, Gemini column). ES/MS m/z: 396.1 [M+H]. $^1$H NMR (400 MHz, DMSO-d6) δ 11.56 (d, J=6.3 Hz, 2H), 8.35 (d, J=1.5 Hz, 1H), 8.03 (d, J=6.1 Hz, 1H), 7.92-7.86 (m, 1H), 7.60 (s, 1H), 7.52 (d, J=8.0 Hz, 2H), 7.40 (d, J=8.0 Hz, 2H), 7.01 (t, J=56.0 Hz, 1H), 2.86 (ddd, J=9.0, 6.3, 4.4 Hz, 1H), 2.79 (ddd, J=8.8, 6.0, 4.4 Hz, 1H), 2.12-2.04 (m, 1H), 1.82 (ddd, J=8.7, 6.3, 4.9 Hz, 1H). $^{19}$F NMR (376 MHz, DMSO-d6) δ −75.13, −109.27 (d, J=56.1 Hz).

Example 419. 5-(8-((2S,2S)-2-(4-(difluoromethyl)phenyl)cyclopropyl)-3-fluoroimidazo[1,2-b]pyridazin-6-yl)pyrimidine-2,4(1H,3H)-dione

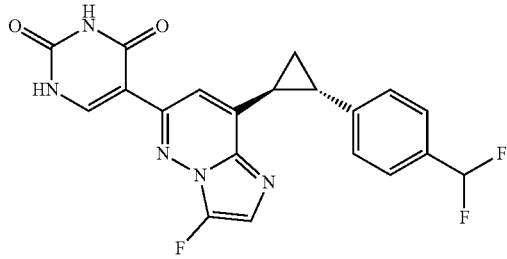 [SMILES: O=c1[nH]cc(-c2cc([C@H]3C[C@@H]3c3ccc(C(F)F)cc3)c3ncc(F)n3n2)c(=O)[nH]1]

5-(8-((1S,2S)-2-(4-(difluoromethyl)phenyl)cyclopropyl)-3-fluoroimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-((2S,2S)-2-(4-(difluoromethyl)phenyl)cyclopropyl)-6-(2,4-dimethoxypyrimidin-5-yl)-3-fluoroimidazo[1,2-b]pyridazine. Purification was accomplished by RP-HPLC (10-90% MeCN/H$_2$O with TFA modifier, Gemini column). ES/MS m/z: 414.1 [M+H]. $^1$H NMR (400 MHz, DMSO-d6) δ 11.53 (d, J=3.1 Hz, 2H), 8.02 (d, J=6.3 Hz, 1H), 7.54 (d, J=7.0 Hz, 1H), 7.53-7.45 (m, 3H), 7.39 (d, J=8.0 Hz, 2H), 7.00 (t, J=56.0 Hz, 1H), 2.89 (dt, J=9.4, 5.6 Hz, 1H), 2.78-2.69 (m, 1H), 2.13 (dt, J=8.8, 5.3 Hz, 1H), 1.79 (dq, J=12.9, 4.9, 4.4 Hz, 1H). $^{19}$F NMR (376 MHz, DMSO-d6) δ −75.47, −109.28 (d, J=56.1 Hz), −155.56 (d, J=7.0 Hz).

Example 420. 5-(7-(3,3-difluoro-4,4-dimethylpyrrolidin-1-yl)-[1,2,4]triazolo[1,5-a]pyrimidin-5-yl)pyrimidine-2,4(1H,3H)-dione

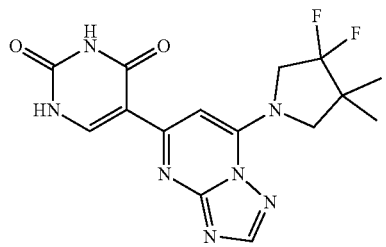 [SMILES: CC1(C)CN(c2cc(-c3c[nH]c(=O)[nH]c3=O)nc3ncnn23)CC1(F)F]

5-(7-(3,3-difluoro-4,4-dimethylpyrrolidin-1-yl)-[1,2,4]triazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-(3,3-difluoro-4,4-dimethylpyrrolidin-1-yl)-5-(2,4-dimethoxypyrimidin-5-yl)-[1,2,4]triazolo[1,5-a]pyrimidine, and running the reaction at 60° C. for 16 h. Purification was accomplished by RP-HPLC (10-90% MeCN/H$_2$O with TFA modifier, Gemini column). ES/MS m/z: 364.1 [M+H]. $^1$H NMR (400 MHz, DMSO-d6) δ 11.62 (d, J=6.5 Hz, 1H), 11.50 (d, J=1.9 Hz, 1H), 8.47 (d, J=6.4 Hz, 1H), 8.37 (s, 1H), 7.39 (s, 1H), 4.56 (t, J=13.5 Hz, 2H), 3.89 (s, 2H), 1.22 (s, 6H). $^{19}$F NMR (376 MHz, DMSO-d6) δ −74.24, −115.21 (t, J=13.6 Hz).

Example 421. 5-(5-(3,3-difluoro-4,4-dimethylpyrrolidin-1-yl)imidazo[1,2-a]pyrimidin-7-yl)pyrimidine-2,4(1H,3H)-dione

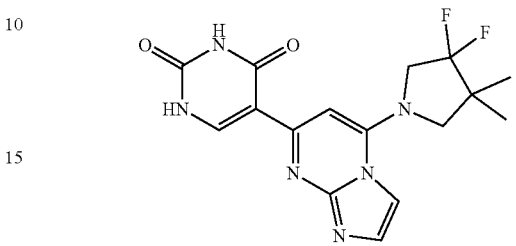

5-(5-(3,3-difluoro-4,4-dimethylpyrrolidin-1-yl)imidazo[1,2-a]pyrimidin-7-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 5-(3,3-difluoro-4,4-dimethylpyrrolidin-1-yl)-7-(2,4-dimethoxypyrimidin-5-yl)imidazo[1,2-a]pyrimidine, and running the reaction at 70° C. for 2 h. Purification was accomplished by RP-HPLC (10-90% MeCN/H$_2$O with TFA modifier, Gemini column). ES/MS m/z: 363.1 [M+H]. $^1$H NMR (400 MHz, DMSO-d6) δ 12.03-11.81 (m, 1H), 11.64 (s, 1H), 8.47 (d, J=4.8 Hz, 1H), 8.23 (d, J=2.8 Hz, 1H), 8.01 (d, J=2.7 Hz, 1H), 7.67 (s, 1H), 4.58 (t, J=13.1 Hz, 2H), 3.82 (s, 2H), 1.24 (s, 6H). $^{19}$F NMR (376 MHz, DMSO-d6) δ −74.15, −115.51 (t, J=13.2 Hz).

Example 422. 5-(8-(3,3-difluoro-4,4-dimethylpyrrolidin-1-yl)-3-fluoro-2-methylimidazo[1,2-b]pyridazin-6-yl)pyrimidine-2,4(1H,3H)-dione

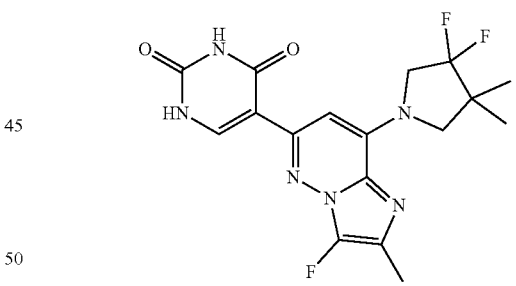

5-(8-(3,3-difluoro-4,4-dimethylpyrrolidin-1-yl)-3-fluoro-2-methylimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(3,3-difluoro-4,4-dimethylpyrrolidin-1-yl)-6-(2,4-dimethoxypyrimidin-5-yl)-3-fluoro-2-methylimidazo[1,2-b]pyridazine, and running the reaction for 16 h. Purification was accomplished by RP-HPLC (10-90% MeCN/H$_2$O with TFA modifier, Gemini column). ES/MS m/z: 395.1 [M+H]. $^1$H NMR (400 MHz, DMSO-d6) δ 11.42 (d, J=2.0 Hz, 1H), 11.38 (dd, J=6.1, 2.1 Hz, 1H), 7.94 (d, J=6.1 Hz, 1H), 6.55 (s, 1H), 4.37 (br s, 2H), 3.83 (br s, 2H), 2.32 (s, 3H), 1.20 (s, 6H). $^{19}$F NMR (376 MHz, DMSO-d6) δ −75.17, −115.45, −158.59.

Example 423. 5-(8-(3-fluoro-3-(hydroxymethyl) azetidin-1-yl)imidazo[1,2-b]pyridazin-6-yl)pyrimidine-2,4(1H,3H)-dione

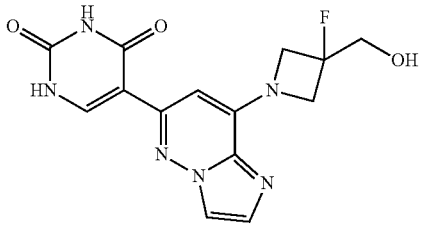 [SMILES: O=c1[nH]cc(-c2cc(N3CC(F)(CO)C3)c3nccn3n2)c(=O)[nH]1]

5-(8-(3-fluoro-3-(hydroxymethyl)azetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with (1-(6-(2,4-dimethoxypyrimidin-5-yl)imidazo[1,2-b]pyridazin-8-yl)-3-fluoroazetidin-3-yl)methanol, and running the reaction at 70° C. for 16 h. Purification was accomplished by RP-HPLC (10-90% MeCN/H$_2$O with TFA modifier, Gemini column). ES/MS m/z: 333.2 [M+H]. $^1$H NMR (400 MHz, DMSO-d6) δ 11.45-11.35 (m, 2H), 8.08 (d, J=1.3 Hz, 1H), 7.95 (d, J=6.1 Hz, 1H), 7.61 (d, J=1.2 Hz, 1H), 6.55 (s, 1H), 4.52 (d, J=15.6 Hz, 2H), 4.39 (dd, J=20.6, 10.6 Hz, 2H), 3.80-3.72 (m, 3H). $^{19}$F NMR (376 MHz, DMSO-d6) δ −75.32, −157.16 (tt, J=21.0, 18.4 Hz).

Example 424. 4-((2S,2S)-2-(6-(2,4-dioxo-1,2,3,4-tetrahydropyrimidin-5-yl)imidazo[1,2-b]pyridazin-8-yl)cyclopropyl)-3,5-difluorobenzonitrile

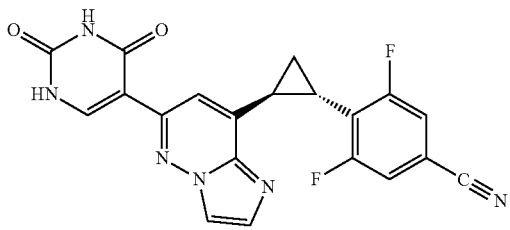 [SMILES: N#Cc1cc(F)c([C@H]2C[C@@H]2c2cc(-c3c[nH]c(=O)[nH]c3=O)nn3ccnc23)c(F)c1]

4-((1S,2S)-2-(6-(2,4-dioxo-1,2,3,4-tetrahydropyrimidin-5-yl)imidazo[1,2-b]pyridazin-8-yl)cyclopropyl)-3,5-difluorobenzonitrile was prepared in the manner described for Example 1, but replacing 8-cyclopropyl-6-(2,4-dimethoxypyrimidin-5-yl)-2-methyl-imidazo[1,2-b]pyridazine with 4-((1S,2S)-2-(6-(2,4-dimethoxypyrimidin-5-yl)imidazo[1,2-b]pyridazin-8-yl)cyclopropyl)-3,5-difluorobenzonitrile. Purification was accomplished by RP-HPLC (10-90% MeCN/H$_2$O with TFA modifier, Gemini column). ES/MS m/z: 407.1 [M+H]. $^1$H NMR (400 MHz, DMSO-d6) δ 11.55 (d, J=5.7 Hz, 2H), 8.35 (d, J=1.4 Hz, 1H), 8.03 (d, J=6.1 Hz, 1H), 7.87 (s, 1H), 7.82-7.77 (m, 2H), 7.66 (s, 1H), 3.02 (dt, J=8.9, 5.6 Hz, 1H), 2.95 (ddd, J=9.3, 6.6, 4.9 Hz, 1H), 2.16 (dt, J=10.2, 5.5 Hz, 1H), 1.95 (ddd, J=8.8, 6.6, 4.8 Hz, 1H). $^{19}$F NMR (376 MHz, DMSO-d6) δ −75.17, −112.26 (d, J=8.2 Hz).

Example 425. 4-((2S,2S)-2-(6-(2,4-dioxo-1,2,3,4-tetrahydropyrimidin-5-yl)-3-fluoroimidazo[1,2-b]pyridazin-8-yl)cyclopropyl)-3,5-difluorobenzonitrile

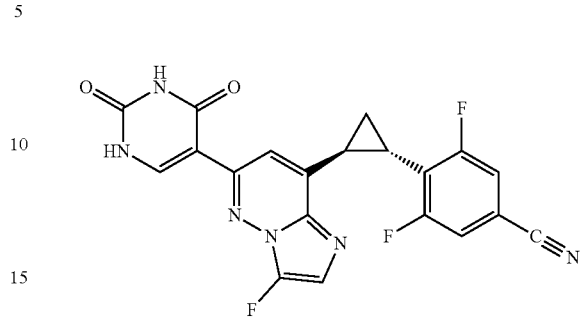

4-((2S,2S)-2-(6-(2,4-dioxo-1,2,3,4-tetrahydropyrimidin-5-yl)-3-fluoroimidazo[1,2-b]pyridazin-8-yl)cyclopropyl)-3,5-difluorobenzonitrile was prepared in the manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)-3-fluoroimidazo[1,2-b]pyridazin-8-yl)cyclopropyl)-3,5-difluorobenzonitrile. Purification was accomplished by RP-HPLC (10-90% MeCN/H$_2$O with TFA modifier, Gemini column). ES/MS m/z: 425.1 [M+H]. $^1$H NMR (400 MHz, DMSO-d6) δ 11.54 (d, J=4.6 Hz, 2H), 8.03 (d, J=6.3 Hz, 1H), 7.82-7.75 (m, 2H), 7.58-7.52 (m, 2H), 3.04-2.95 (m, 2H), 2.19 (dt, J=9.9, 5.3 Hz, 1H), 1.92 (ddd, J=8.9, 6.6, 4.7 Hz, 1H). $^{19}$F NMR (376 MHz, DMSO-d6) δ −75.38, −112.20 (d, J=7.6 Hz), −155.57 (d, J=7.1 Hz).

Example 426. 5-(8-(3,3-difluoro-4,4-dimethylpyrrolidin-1-yl)-[1,2,4]triazolo[1,5-b]pyridazin-6-yl)pyrimidine-2,4(1H,3H)-dione

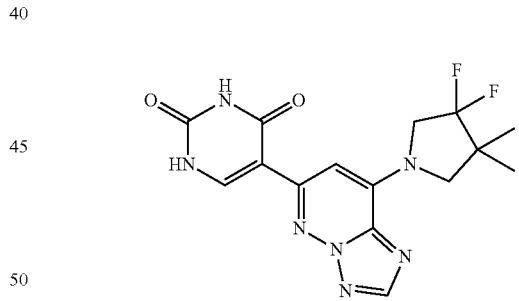

5-(8-(3,3-difluoro-4,4-dimethylpyrrolidin-1-yl)-[1,2,4]triazolo[1,5-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(3,3-difluoro-4,4-dimethylpyrrolidin-1-yl)-6-(2,4-dimethoxypyrimidin-5-yl)-[1,2,4]triazolo[1,5-b]pyridazine. Purification was accomplished by RP-HPLC (10-90% MeCN/H$_2$O with TFA modifier, Gemini column). ES/MS m/z: 364.1 [M+H]. $^1$H NMR (400 MHz, DMSO-d6) δ 11.47 (d, J=5.4 Hz, 2H), 8.44 (s, 1H), 8.05 (d, J=5.3 Hz, 1H), 6.98 (s, 1H), 4.39 (br s, 2H), 3.86 (br s, 2H), 1.21 (s, 6H). $^{19}$F NMR (376 MHz, DMSO-d6) δ −115.17.

Example 427. 5-(8-((1S,2S)-2-(4-(trifluoromethyl)phenyl)cyclopropyl)-[1,2,4]triazolo[1,5-b]pyridazin-6-yl)pyrimidine-2,4(1H,3H)-dione

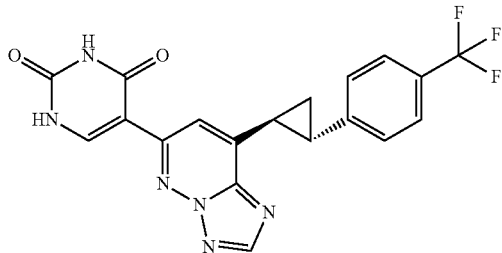 [SMILES: O=c1[nH]cc(-c2cc([C@H]3C[C@@H]3c3ccc(C(F)(F)F)cc3)c3ncnn3n2)c(=O)[nH]1]

5-(8-((1S,2S)-2-(4-(trifluoromethyl)phenyl)cyclopropyl)[1,2,4]triazolo[1,5-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(4-(trifluoromethyl)phenyl)cyclopropyl)-[1,2,4]triazolo[1,5-b]pyridazine. Purification was accomplished by RP-HPLC (10-90% MeCN/H$_2$O with TFA modifier, Gemini column). ES/MS m/z: 415.1 [M+H]. $^1$H NMR (400 MHz, DMSO-d6) δ 11.60 (d, J=7.9 Hz, 2H), 8.61 (s, 1H), 8.12 (d, J=6.1 Hz, 1H), 7.97 (s, 1H), 7.67 (d, J=8.1 Hz, 2H), 7.51 (d, J=8.1 Hz, 2H), 3.03 (ddd, J=9.1, 6.2, 4.4 Hz, 1H), 2.80 (ddd, J=9.0, 6.0, 4.4 Hz, 1H), 2.25 (dt, J=8.9, 5.3 Hz, 1H), 1.87 (dt, J=8.7, 5.3 Hz, 1H). $^{19}$F NMR (376 MHz, DMSO-d6) δ −61.26.

Example 428. 4-((1S,2S)-2-(6-(2,4-dioxo-1,2,3,4-tetrahydropyrimidin-5-yl)-[1,2,4]triazolo[1,5-b]pyridazin-8-yl)cyclopropyl)-3,5-difluorobenzonitrile

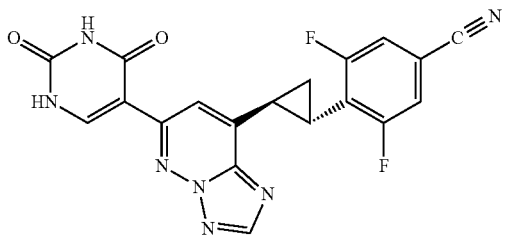 [SMILES: N#Cc1cc(F)c([C@H]2C[C@@H]2c2cc(-c3c[nH]c(=O)[nH]c3=O)nn3ncnc23)c(F)c1]

4-((2S,2S)-2-(6-(2,4-dioxo-1,2,3,4-tetrahydropyrimidin-5-yl)-[1,2,4]triazolo[1,5-b]pyridazin-8-yl)cyclopropyl)-3,5-difluorobenzonitrile was prepared in the manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)-[1,2,4]triazolo[1,5-b]pyridazin-8-yl)cyclopropyl)-3,5-difluorobenzonitrile. Purification was accomplished by RP-HPLC (10-90% MeCN/H$_2$O with TFA modifier, Gemini column). ES/MS m/z: 408.1 [M+H]. $^1$H NMR (400 MHz, DMSO-d6) δ 11.59 (d, J=10.2 Hz, 2H), 8.62 (s, 1H), 8.12 (d, J=6.1 Hz, 1H), 8.03 (s, 1H), 7.80 (d, J=7.2 Hz, 2H), 3.02 (ddt, J=13.4, 8.8, 5.4 Hz, 2H), 2.23 (dt, J=10.4, 5.2 Hz, 1H), 2.00-1.90 (m, 1H). $^{19}$F NMR (376 MHz, DMSO-d6) δ −112.04 (d, J=7.6 Hz).

Example 429. (R)-5-(8-(3-(trifluoromethoxy)pyrrolidin-1-yl)-[1,2,4]triazolo[1,5-b]pyridazin-6-yl)pyrimidine-2,4(1H,3H)-dione

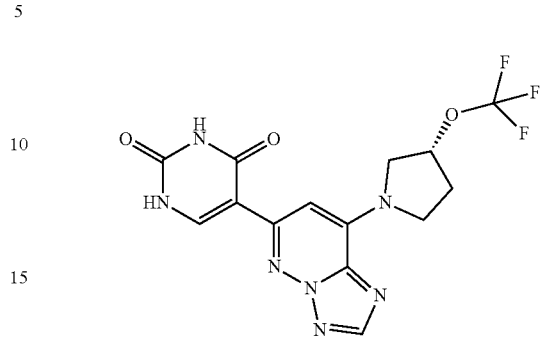

(R)-5-(8-(3-(trifluoromethoxy)pyrrolidin-1-yl)-[1,2,4]triazolo[1,5-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with (R)-6-(2,4-dimethoxypyrimidin-5-yl)-8-(3-(trifluoromethoxy)pyrrolidin-1-yl)-[1,2,4]triazolo[1,5-b]pyridazine. Purification was accomplished by RP-HPLC (10-90% MeCN/H$_2$O with TFA modifier, Gemini column). ES/MS m/z: 384.1 [M+H]. $^1$H NMR (400 MHz, DMSO-d6) δ 11.45 (d, J=6.7 Hz, 2H), 8.42 (s, 1H), 8.05 (d, J=6.0 Hz, 1H), 6.99 (s, 1H), 5.32 (dq, J=6.0, 3.6, 2.9 Hz, 1H), 4.13 (br s, 1H), 3.79 (br s, 1H), 3.42-3.25 (m, 2H), 2.44-2.27 (m, 2H). $^{19}$F NMR (376 MHz, DMSO-d6) δ −57.32.

Example 430. 5-(8-((2S,2S)-2-(1-(2,2,2-trifluoroethyl)-1H-indazol-5-yl)cyclopropyl)-[1,2,4]triazolo[1,5-b]pyridazin-6-yl)pyrimidine-2,4(1H,3H)-dione

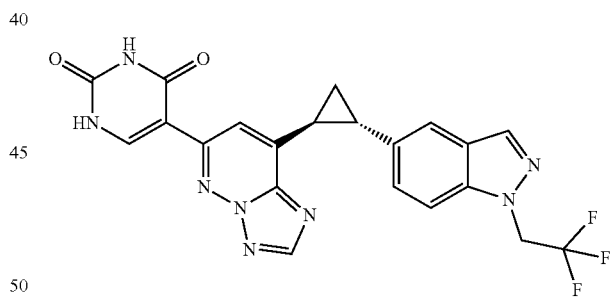

5-(8-((1S,2S)-2-(1-(2,2,2-trifluoroethyl)-1H-indazol-5-yl)cyclopropyl)-[1,2,4]triazolo[1,5-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(1-(2,2,2-trifluoroethyl)-1H-indazol-5-yl)cyclopropyl)-[1,2,4]triazolo[1,5-b]pyridazine. Purification was accomplished by RP-HPLC (10-90% MeCN/H$_2$O with TFA modifier, Gemini column). ES/MS m/z: 469.2 [M+H]. $^1$H NMR (400 MHz, DMSO-d6) δ 11.65-11.49 (m, 2H), 8.60 (s, 1H), 8.14 (d, J=0.9 Hz, 1H), 8.11 (d, J=6.1 Hz, 1H), 7.93 (s, 1H), 7.75 (d, J=8.7 Hz, 1H), 7.69 (d, J=1.5 Hz, 1H), 7.40 (dd, J=8.8, 1.7 Hz, 1H), 5.43 (q, J=9.1 Hz, 2H), 3.03 (ddd, J=9.1, 6.4, 4.4 Hz, 1H), 2.73 (ddd, J=8.7, 5.8, 4.4 Hz, 1H), 2.17 (dt, J=9.0, 5.2 Hz, 1H), 1.86 (ddd, J=8.8, 6.5, 4.9 Hz, 1H). $^{19}$F NMR (376 MHz, DMSO-d6) δ −70.16 (t, J=9.2 Hz).

Example 431. 5-(8-((2S,2S)-2-(1-(2,2,2-trifluoroethyl)-1H-indazol-6-yl)cyclopropyl)-[1,2,4]triazolo[1,5-b]pyridazin-6-yl)pyrimidine-2,4(1H,3H)-dione

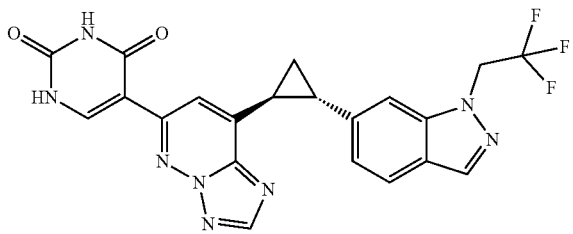 [SMILES: O=c1[nH]cc(-c2cc([C@H]3C[C@@H]3c3ccc4cnn(CC(F)(F)F)c4c3)c3ncnn3n2)c(=O)[nH]1]

5-(8-((1S,2S)-2-(1-(2,2,2-trifluoroethyl)-1H-indazol-6-yl)cyclopropyl)-[1,2,4]triazolo[1,5-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(1-(2,2,2-trifluoroethyl)-1H-indazol-6-yl)cyclopropyl)-[1,2,4]triazolo[1,5-b]pyridazine. Purification was accomplished by RP-HPLC (10-90% MeCN/H$_2$O with TFA modifier, Gemini column). ES/MS m/z: 469.2 [M+H]. $^1$H NMR (400 MHz, DMSO-d6) δ 11.67-11.47 (m, 2H), 8.61 (s, 1H), 8.15 (d, J=0.8 Hz, 1H), 8.12 (d, J=6.1 Hz, 1H), 7.96 (s, 1H), 7.76-7.70 (m, 2H), 7.13 (dd, J=8.5, 1.2 Hz, 1H), 5.40 (q, J=9.2 Hz, 2H), 3.09 (ddd, J=9.0, 6.3, 4.4 Hz, 1H), 2.79 (ddd, J=8.8, 5.8, 4.3 Hz, 1H), 2.23 (dt, J=8.9, 5.2 Hz, 1H), 1.92 (ddd, J=8.8, 6.4, 4.8 Hz, 1H). $^{19}$F NMR (376 MHz, DMSO-d6) δ −70.08 (t, J=9.1 Hz).

Example 432. 5-(8-(3,3-difluoro-4-((5-(trifluoromethyl)pyridin-2-yl)oxy)pyrrolidin-1-yl)-[1,2,4]triazolo[1,5-b]pyridazin-6-yl)pyrimidine-2,4(1H,3H)-dione

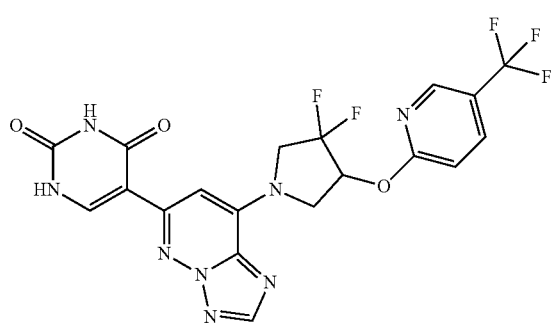 [SMILES: O=c1[nH]cc(-c2cc(N3CC(Oc4ccc(C(F)(F)F)cn4)C(F)(F)C3)c3ncnn3n2)c(=O)[nH]1]

5-(8-(3,3-difluoro-4-((5-(trifluoromethyl)pyridin-2-yl)oxy)pyrrolidin-1-yl)-[1,2,4]triazolo[1,5-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-(3,3-difluoro-4-((5-(trifluoromethyl)pyridin-2-yl)oxy)pyrrolidin-1-yl)-6-(2,4-dimethoxypyrimidin-5-yl)-[1,2,4]triazolo[1,5-b]pyridazine. Purification was accomplished by RP-HPLC (10-90% MeCN/H$_2$O with TFA modifier, Gemini column). ES/MS m/z: 497.1 [M+H]. $^1$H NMR (400 MHz, DMSO-d6) δ 11.48 (d, J=4.7 Hz, 2H), 8.70 (dt, J=2.1, 1.0 Hz, 1H), 8.46 (s, 1H), 8.19 (dd, J=8.7, 2.6 Hz, 1H), 8.06 (d, J=6.3 Hz, 1H), 7.20 (d, J=8.8 Hz, 1H), 7.04 (s, 1H), 6.04 (t, J=4.3 Hz, 1H), 4.73-4.35 (m, 3H), 4.20 (s, 1H). $^{19}$F NMR (376 MHz, DMSO-d6) δ −60.56, −108.00 (d, J=241.1 Hz), −119.20 (d, J=238.2 Hz).

Example 433. 5-(8-(3-fluoro-3-(trifluoromethyl)azetidin-1-yl)-[1,2,4]triazolo[1,5-b]pyridazin-6-yl)pyrimidine-2,4(1H,3H)-dione

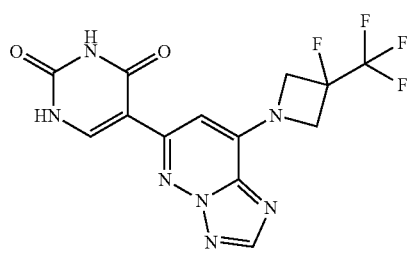 [SMILES: O=c1[nH]cc(-c2cc(N3CC(F)(C(F)(F)F)C3)c3ncnn3n2)c(=O)[nH]1]

5-(8-(3-fluoro-3-(trifluoromethyl)azetidin-1-yl)-[1,2,4]triazolo[1,5-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-fluoro-3-(trifluoromethyl)azetidin-1-yl)-[1,2,4]triazolo[1,5-b]pyridazine. Purification was accomplished by RP-HPLC (10-90% MeCN/H$_2$O with TFA modifier, Gemini column). ES/MS m/z: 372.1 [M+H]. $^1$H NMR (400 MHz, DMSO-d6) δ 11.50 (s, 2H), 8.48 (s, 1H), 8.06 (d, J=5.1 Hz, 1H), 7.00 (s, 1H), 4.86 (dq, J=25.4, 11.8 Hz, 4H). $^{19}$F NMR (376 MHz, DMSO-d6) δ −82.83 (d, J=7.6 Hz), −172.26-172.72 (m).

Example 434. 5-(8-(3-(trifluoromethyl)-3-((5-(trifluoromethyl)pyridin-2-yl)oxy)azetidin-1-yl)imidazo[1,2-b]pyridazin-6-yl)pyrimidine-2,4(1H,3H)-dione

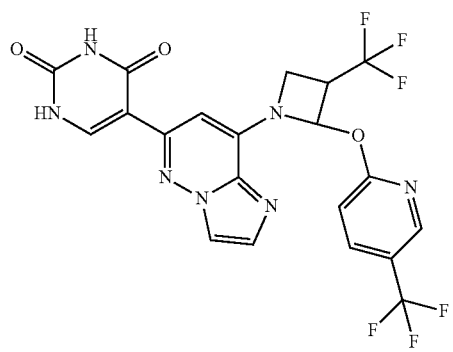 [SMILES: O=c1[nH]cc(-c2cc(N3CC(C(F)(F)F)C3Oc3ccc(C(F)(F)F)cn3)c3nccn3n2)c(=O)[nH]1]

5-(8-(3-(trifluoromethyl)-3-((5-(trifluoromethyl)pyridin-2-yl)oxy)azetidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-(trifluoromethyl)-3-((5-(trifluoromethyl)pyridin-2-yl)oxy)

azetidin-1-yl)imidazo[1,2-b]pyridazine. Purification was accomplished by RP-HPLC (10-90% MeCN/H₂O with TFA modifier, Gemini column). ES/MS m/z: 514.1 [M+H]. ¹H NMR (400 MHz, DMSO-d6) δ 11.47-11.33 (m, 2H), 8.65 (d, J=2.4 Hz, 1H), 8.22 (dd, J=8.8, 2.6 Hz, 1H), 8.09 (d, J=1.3 Hz, 1H), 7.93 (d, J=6.1 Hz, 1H), 7.61 (d, J=1.3 Hz, 1H), 7.24 (d, J=8.7 Hz, 1H), 6.63 (s, 1H), 4.94 (br s, 4H). ¹⁹F NMR (376 MHz, DMSO-d6) δ −60.70, −75.39, −78.68.

Example 435. 5-(8-(3-fluoro-3-(((5-(trifluoromethyl)pyridin-2-yl)oxy)methyl)azetidin-1-yl)imidazo[1,2-b]pyridazin-6-yl)pyrimidine-2,4(1H,3H)-dione

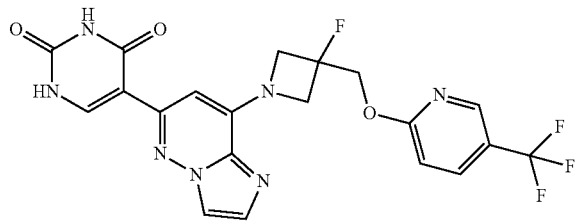 [SMILES: O=c1[nH]cc(-c2cc(N3CC(F)(COc4ccc(C(F)(F)F)cn4)C3)c3nccn3n2)c(=O)[nH]1]

5-(8-(3-fluoro-3-(((5-(trifluoromethyl)pyridin-2-yl)oxy)methyl)azetidin-1-yl)imidazo[1,2-b]pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-fluoro-3-(((5-(trifluoromethyl)pyridin-2-yl)oxy)methyl)azetidin-1-yl)imidazo[1,2-b]pyridazine. Purification was accomplished by RP-HPLC (10-90% MeCN/H₂O with TFA modifier, Gemini column). ES/MS m/z: 478.2 [M+H]. ¹H NMR (400 MHz, DMSO-d6) δ 11.49-11.29 (m, 2H), 8.61 (s, 1H), 8.12 (dd, J=8.8, 2.5 Hz, 1H), 8.07 (s, 1H), 7.94 (d, J=6.0 Hz, 1H), 7.60 (s, 1H), 7.13 (d, J=8.7 Hz, 1H), 6.58 (s, 1H), 4.87 (d, J=23.1 Hz, 2H), 4.69 (d, J=17.2 Hz, 2H), 4.54 (dd, J=21.4, 10.7 Hz, 2H). ¹⁹F NMR (376 MHz, DMSO-d6) δ −60.47, −75.32, −155.75 (dt, J=42.3, 21.3 Hz).

Example 436. 1-(6-(2,4-dioxo-1,2,3,4-tetrahydropyrimidin-5-yl)-[1,2,4]triazolo[1,5-b]pyridazin-8-yl)-4,4-difluoropyrrolidin-3-yl (2,2,2-trifluoroethyl)carbamate

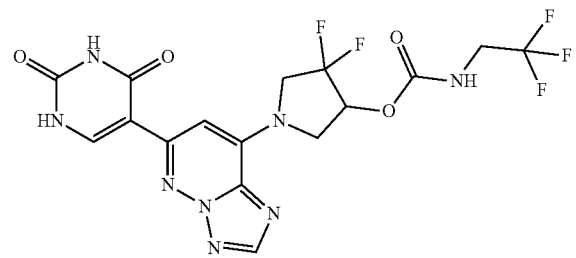 [SMILES: O=C(NCC(F)(F)F)OC1CN(c2cc(-c3c[nH]c(=O)[nH]c3=O)nn3ncnc23)CC1(F)F]

1-(6-(2,4-dioxo-1,2,3,4-tetrahydropyrimidin-5-yl)-[1,2,4]triazolo[1,5-b]pyridazin-8-yl)-4,4-difluoropyrrolidin-3-yl (2,2,2-trifluoroethyl)carbamate was prepared as a racemic mixture in the manner described for Example 1, but replacing 8-cyclopropyl-6-(2,4-dimethoxypyrimidin-5-yl)-2-methyl-imidazo[1,2-b]pyridazine with 1-(6-(2,4-dimethoxypyrimidin-5-yl)[1,2,4]triazolo[1,5-b]pyridazin-8-yl)-4,4-difluoropyrrolidin-3-yl (2,2,2-trifluoroethyl)carbamate. Purification was accomplished by RP-HPLC (10-90% MeCN/H₂O with TFA modifier, Gemini column). ES/MS m/z: 477.1 [M+H]. ¹H NMR (400 MHz, DMSO-d6) δ 11.50 (d, J=6.7 Hz, 2H), 8.48 (s, 1H), 8.45 (t, J=6.4 Hz, 1H), 8.06 (d, J=6.0 Hz, 1H), 7.03 (s, 1H), 5.55 (s, 1H), 4.64-3.95 (m, 4H), 3.95-3.75 (m, 2H). ¹⁹F NMR (376 MHz, DMSO-d6) δ −71.98 (t, J=9.5 Hz), −108.32 (d, J=251.2 Hz), −119.76 (d, J=243.5 Hz).

Example 437. (1-(6-(2,4-dioxo-1,2,3,4-tetrahydropyrimidin-5-yl)imidazo[1,2-b]pyridazin-8-yl)-3-fluoroazetidin-3-yl)methyl (2,2,2-trifluoroethyl)carbamate

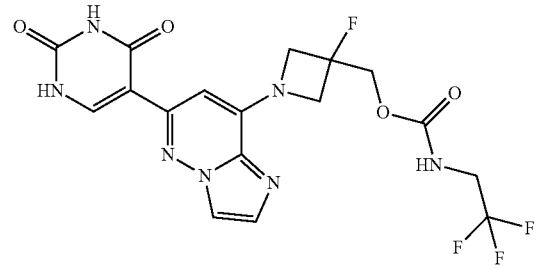 [SMILES: O=C(NCC(F)(F)F)OCC1(F)CN(c2cc(-c3c[nH]c(=O)[nH]c3=O)nn3ccnc23)C1]

(1-(6-(2,4-dioxo-1,2,3,4-tetrahydropyrimidin-5-yl)imidazo[1,2-b]pyridazin-8-yl)-3-fluoroazetidin-3-yl)methyl (2,2,2-trifluoroethyl)carbamate was prepared in the manner described for Example 1, but replacing 8-cyclopropyl-6-(2,4-dimethoxypyrimidin-5-yl)-2-methyl-imidazo[1,2-b]pyridazine with (1-(6-(2,4-dimethoxypyrimidin-5-yl)imidazo[1,2-b]pyridazin-8-yl)-3-fluoroazetidin-3-yl)methyl (2,2,2-trifluoroethyl)carbamate. Purification was accomplished by RP-HPLC (10-90% MeCN/H₂O with TFA modifier, Gemini column). ES/MS m/z: 458.2 [M+H]. ¹H NMR (400 MHz, DMSO-d6) δ 11.48-11.26 (m, 2H), 8.22 (t, J=6.5 Hz, 1H), 8.06 (d, J=1.2 Hz, 1H), 7.94 (d, J=6.1 Hz, 1H), 7.58 (d, J=1.2 Hz, 1H), 6.54 (s, 1H), 4.70-4.36 (m, 6H), 3.82 (qd, J=9.6, 6.3 Hz, 2H). ¹⁹F NMR (376 MHz, DMSO-d6) δ −72.03 (t, J=9.6 Hz), −75.21, −156.20 (p, J=20.9 Hz).

Example 438. 3-((6-(2,4-dioxo-1,2,3,4-tetrahydropyrimidin-5-yl)-[1,2,4]triazolo[1,5-b]pyridazin-8-yl)oxy)-2,2-difluoropropyl isopropylcarbamate

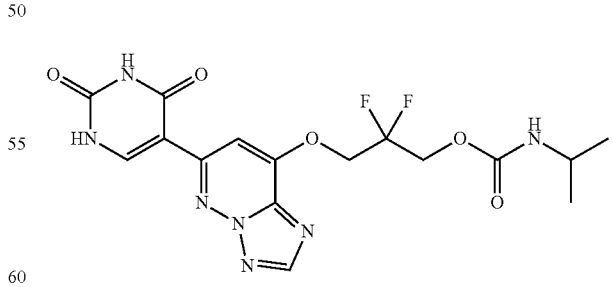

3-((6-(2,4-dioxo-1,2,3,4-tetrahydropyrimidin-5-yl)-[1,2,4]triazolo[1,5-b]pyridazin-8-yl)oxy)-2,2-difluoropropyl isopropylcarbamate was prepared in the manner described for Example 1, but replacing 8-cyclopropyl-6-(2,4-dimethoxypyrimidin-5-yl)-2-methyl-imidazo[1,2-b]pyridazine with 3-((6-(2,4-dimethoxypyrimidin-5-yl)-[1,2,4]triazolo[1,5-b]

pyridazin-8-yl)oxy)-2,2-difluoropropyl isopropylcarbamate. Purification was accomplished by RP-HPLC (10-90% MeCN/H₂O with TFA modifier, Gemini column). ES/MS m/z: 426.1 [M+H]. ¹H NMR (400 MHz, DMSO-d6) δ 11.73-11.51 (m, 2H), 8.59 (s, 1H), 8.15 (d, J=6.2 Hz, 1H), 7.77 (s, 1H), 7.42 (d, J=7.7 Hz, 1H), 4.87 (t, J=12.9 Hz, 2H), 4.49 (t, J=14.1 Hz, 2H), 3.57 (dq, J=13.4, 6.7 Hz, 1H), 1.04 (d, J=6.5 Hz, 6H). ¹⁹F NMR (376 MHz, DMSO-d6) δ -113.57 (p, J=13.6 Hz).

Example 439. 5-(8-((2S,2S)-2-(5-chloropyridin-2-yl)cyclopropyl)-[1,2,4]triazolo[1,5-b]pyridazin-6-yl)pyrimidine-2,4(1H,3H)-dione

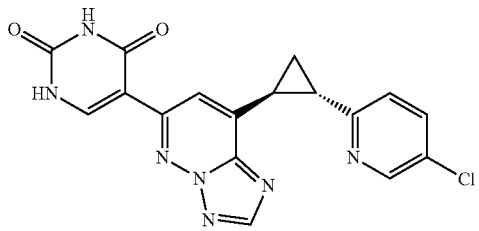 [SMILES: O=c1[nH]cc(-c2cc([C@H]3C[C@@H]3c3ccc(Cl)cn3)c3ncnn3n2)c(=O)[nH]1]

5-(8-((1S,2S)-2-(5-chloropyridin-2-yl)cyclopropyl)-[1,2,4]triazolo[1,5-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-((2S,2S)-2-(5-chloropyridin-2-yl)cyclopropyl)-6-(2,4-dimethoxypyrimidin-5-yl)-[1,2,4]triazolo[1,5-b]pyridazine. Purification was accomplished by RP-HPLC (10-90% MeCN/H₂O with TFA modifier, Gemini column). ES/MS m/z: 382.0 [M+H]. ¹H NMR (400 MHz, DMSO-d6) δ 11.59 (d, J=7.3 Hz, 2H), 8.60 (s, 1H), 8.56 (d, J=2.5 Hz, 1H), 8.11 (d, J=6.1 Hz, 1H), 7.94 (s, 1H), 7.84 (dd, J=8.4, 2.5 Hz, 1H), 7.51 (d, J=8.3 Hz, 1H), 3.12 (ddd, J=8.8, 5.9, 4.1 Hz, 1H), 2.96-2.88 (m, 1H), 2.17 (ddd, J=8.7, 6.0, 4.0 Hz, 1H), 1.88 (ddd, J=9.6, 5.9, 4.0 Hz, 1H).

Example 440. 5-(2-cyclopropyl-8-(3,3-difluoro-4,4-dimethylpyrrolidin-1-yl)-3-fluoroimidazo[1,2-b]pyridazin-6-yl)pyrimidine-2,4(1H,3H)-dione

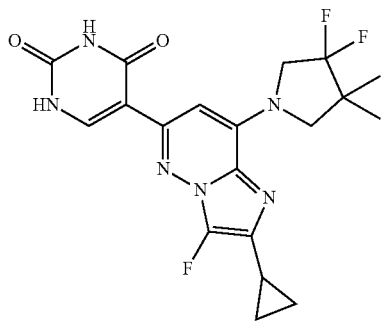

5-(2-cyclopropyl-8-(3,3-difluoro-4,4-dimethylpyrrolidin-1-yl)-3-fluoroimidazo[1,2-b]pyridazin-6-yl)pyrimidine-2,4(1H,3H)-dione was prepared as follows: To a mixture of 2-cyclopropyl-8-(3,3-difluoro-4,4-dimethylpyrrolidin-1-yl)-6-(2,4-dimethoxypyrimidin-5-yl)-3-fluoroimidazo[1,2-b]pyridazine (60 mg, 0.134 mmol) in MeCN (3 mL) was added iodotrimethylsilane (0.19 mL, 1.34 mmol). The mixture was stirred at rt for 45 min, after which it was concentrated in vacuo and the resulting residue purified by RP-HPLC (10-90% MeCN/H₂O with TFA modifier, Gemini column) to afford 5-(2-cyclopropyl-8-(3,3-difluoro-4,4-dimethylpyrrolidin-1-yl)-3-fluoroimidazo[1,2-b]pyridazin-6-yl)pyrimidine-2,4(1H,3H)-dione. ES/MS m/z: 421.2 [M+H]. ¹H NMR (400 MHz, DMSO-d6) δ 11.41 (d, J=2.0 Hz, 1H), 11.37 (dd, J=6.2, 2.0 Hz, 1H), 7.94 (d, J=6.1 Hz, 1H), 6.55 (s, 1H), 4.38 (br s, 2H), 3.76 (br s, 2H), 2.02 (tt, J=8.3, 5.0 Hz, 1H), 1.19 (s, 6H), 0.95 (dt, J=8.3, 2.8 Hz, 2H), 0.92-0.84 (m, 2H). ¹⁹F NMR (376 MHz, DMSO-d6) δ -75.28, -115.44 (t, J=13.9 Hz), -159.35.

Example 441. 5-(8-(3,3-difluoro-4,4-dimethylpyrrolidin-1-yl)-2-(1-(trifluoromethyl)cyclopropyl)imidazo[1,2-b]pyridazin-6-yl)pyrimidine-2,4(1H,3H)-dione

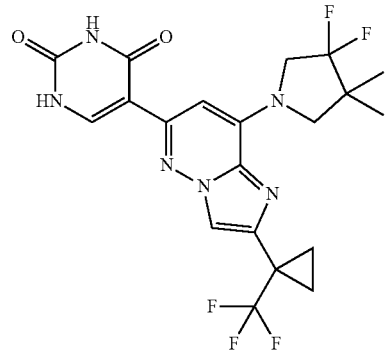

5-(8-(3,3-difluoro-4,4-dimethylpyrrolidin-1-yl)-2-(1-(trifluoromethyl)cyclopropyl)imidazo[1,2-b]pyridazin-6-yl)pyrimidine-2,4(1H,3H)-dione was prepared in the manner described for Example 440, but replacing 2-cyclopropyl-8-(3,3-difluoro-4,4-dimethylpyrrolidin-1-yl)-6-(2,4-dimethoxypyrimidin-5-yl)-3-fluoroimidazo[1,2-b]pyridazine with 8-(3,3-difluoro-4,4-dimethylpyrrolidin-1-yl)-6-(2,4-dimethoxypyrimidin-5-yl)-2-(1-(trifluoromethyl)cyclopropyl)imidazo[1,2-b]pyridazine. Purification was accomplished by RP-HPLC (10-90% MeCN/H₂O with TFA modifier, Gemini column). ES/MS m/z: 471.1 [M+H]. ¹H NMR (400 MHz, DMSO-d6) δ 11.41 (d, J=2.0 Hz, 1H), 11.38 (dd, J=6.2, 2.0 Hz, 1H), 8.03 (s, 1H), 7.93 (d, J=6.1 Hz, 1H), 6.60 (s, 1H), 4.42 (br s, 2H), 3.76 (br s, 2H), 1.40 (t, J=3.8 Hz, 4H), 1.20 (s, 6H). ¹⁹F NMR (376 MHz, DMSO-d6) δ -68.12, -75.41, -115.39 (t, J=13.8 Hz).

Example 442. 5-(8-(6-azabicyclo[3.2.0]heptan-6-yl)imidazo[1,2-b]pyridazin-6-yl)pyrimidine-2,4(1H,3H)-dione

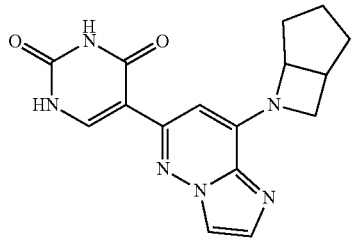

5-(8-(6-azabicyclo[3.2.0]heptan-6-yl)imidazo[1,2-b]pyridazin-6-yl)pyrimidine-2,4(1H,3H)-dione was prepared as follows: To a solution of 5-(8-bromoimidazo[1,2-b]pyridazin-6-yl)pyrimidine-2,4(1H,3H)-dione (50 mg, 0.162 mmol) in NMP (1 mL) was added DIPEA (0.034 mL, 0.195 mmol), followed by 6-azabicyclo[3.2.0]heptane (0.018 mL, 0.179 mmol). The vial was sealed and heated to 130° C. for 4 h, after which more 6-azabicyclo[3.2.0]heptane (0.018 mL, 0.179 mmol) was added. The mixture was heated to 130° C. for 2 h, then cooled to rt. Purification was accomplished by RP-HPLC (10-90% MeCN/H$_2$O with TFA modifier, Gemini column) to afford 5-(8-(6-azabicyclo[3.2.0]heptan-6-yl)imidazo[1,2-b]pyridazin-6-yl)pyrimidine-2,4(1H,3H)-dione. ES/MS m/z: 325.1 [M+H]. $^1$H NMR (400 MHz, DMSO-d6) δ 11.36 (d, J=2.1 Hz, 1H), 11.33 (d, J=6.4 Hz, 1H), 7.99 (s, 1H), 7.91 (d, J=6.1 Hz, 1H), 7.55 (s, 1H), 6.41 (s, 1H), 5.07 (br s, 1H), 4.36 (br s, 1H), 3.13 (q, J=10.8, 8.7 Hz, 1H), 2.23 (d, J=13.4 Hz, 1H), 1.89-1.74 (m, 4H), 1.55 (q, J=10.9, 9.3 Hz, 2H).

Example 443. 5-(8-(3-(2,2-difluoroethyl)azetidin-1-yl)imidazo[1,2-b]pyridazin-6-yl)pyrimidine-2,4(1H,3H)-dione

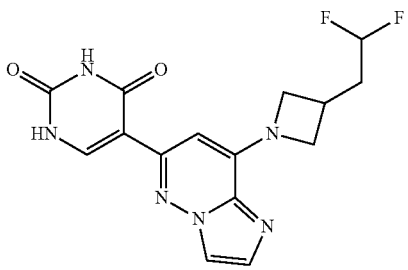

5-(8-(3-(2,2-difluoroethyl)azetidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3-(2,2-difluoroethyl)azetidine, 2,2,2-trifluoroacetate. Purification was accomplished by RP-HPLC (10-90% MeCN/H$_2$O with TFA modifier, Gemini column). ES/MS m/z: 349.1 [M+H]. $^1$H NMR (400 MHz, DMSO-d6) δ 11.38 (d, J=2.1 Hz, 1H), 11.35 (d, J=6.8 Hz, 1H), 8.00 (d, J=1.2 Hz, 1H), 7.92 (d, J=6.1 Hz, 1H), 7.54 (d, J=1.2 Hz, 1H), 6.43 (s, 1H), 6.33-5.97 (m, 1H), 4.49 (br s, 2H), 4.11 (br s, 2H), 3.08-2.97 (m, 2H), 2.30 2.21 (m, 2H). $^{19}$F NMR (376 MHz, DMSO-d6) δ −74.87, −116.56 (dt, J=56.1, 18.3 Hz).

Example 444. 5-(8-(3-(2,2-difluoroethyl)-3-methylazetidin-1-yl)imidazo[1,2-b]pyridazin-6-yl)pyrimidine-2,4(1H,3H)-dione

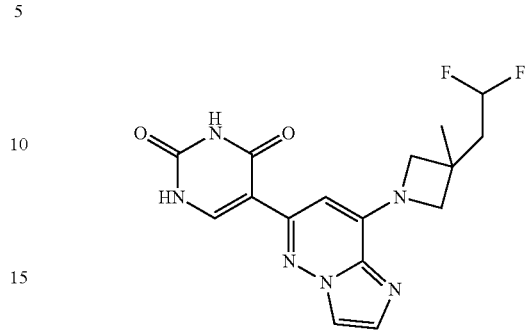

5-(8-(3-(2,2-difluoroethyl)-3-methylazetidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3-(2,2-difluoroethyl)-3-methyl-azetidine hydrochloride. Purification was accomplished by RP-HPLC (10-90% MeCN/H$_2$O with TFA modifier, Gemini column). ES/MS m/z: 363.1 [M+H]. $^1$H NMR (400 MHz, DMSO-d6) δ 11.46-11.23 (m, 2H), 8.03 (d, J=1.3 Hz, 1H), 7.93 (d, J=6.1 Hz, 1H), 7.57 (d, J=1.3 Hz, 1H), 6.47 (s, 1H), 6.26 (tt, J=55.8, 4.8 Hz, 1H), 4.23 (br s, 2H), 4.05 (br s, 2H), 2.28 (td, J=18.0, 4.7 Hz, 2H), 1.43 (s, 3H). $^{19}$F NMR (376 MHz, DMSO-d6) δ −75.15, −114.55 (dt, J=56.0, 17.9 Hz).

Example 445. 5-(8-(3-methyl-3-(2,2,2-trifluoroethyl)azetidin-1-yl)imidazo[1,2-b]pyridazin-6-yl)pyrimidine-2,4(1H,3H)-dione

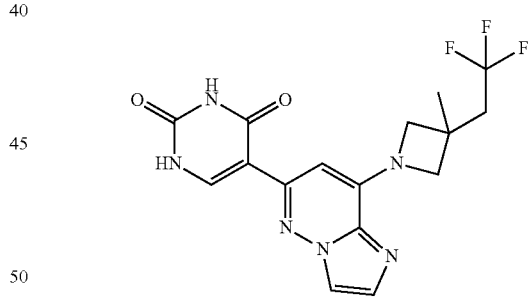

5-(8-(3-methyl-3-(2,2,2-trifluoroethyl)azetidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3-methyl-3-(2,2,2-trifluoroethyl)azetidine hydrochloride. Purification was accomplished by RP-HPLC (10-90% MeCN/H$_2$O with TFA modifier, Gemini column). ES/MS m/z: 381.1 [M+H]. $^1$H NMR (400 MHz, DMSO-d6) δ 11.39 (d, J=2.0 Hz, 1H), 11.38-11.31 (m, 1H), 8.03 (d, J=1.2 Hz, 1H), 7.93 (d, J=6.1 Hz, 1H), 7.56 (d, J=1.2 Hz, 1H), 6.47 (s, 1H), 4.27 (br s, 2H), 4.09 (br s, 2H), 2.80 (q, J=12.0 Hz, 2H), 1.47 (s, 3H). $^{19}$F NMR (376 MHz, DMSO-d6) δ −60.86 (t, J=11.9 Hz), −75.09.

Example 446. 5-(8-(3-(bicyclo[1.1.1]pentan-1-yl)azetidin-1-yl)imidazo[1,2-b]pyridazin-6-yl)pyrimidine-2,4(1H,3H)-dione

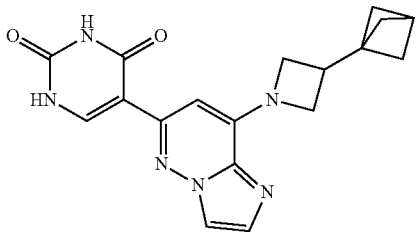

5-(8-(3-(bicyclo[1.1.1]pentan-1-yl)azetidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3-(1-bicyclo[1.1.1]pentanyl)azetidine, 2,2,2-trifluoroacetate. Purification was accomplished by RP-HPLC (10-90% MeCN/H$_2$O with TFA modifier, Gemini column). ES/MS m/z: 351.1 [M+H]. $^1$H NMR (400 MHz, DMSO-d6) δ 11.42-11.33 (m, 2H), 8.04 (d, J=1.3 Hz, 1H), 7.93 (d, J=6.1 Hz, 1H), 7.59 (d, J=1.3 Hz, 1H), 6.46 (s, 1H), 4.36 (br s, 2H), 4.06 (br s, 2H), 2.87 (ddt, J=10.8, 8.2, 4.2 Hz, 1H), 1.80-1.68 (m, 7H).

Example 447. 5-(8-(3-(2,2,2-trifluoroethoxy)azetidin-1-yl)imidazo[1,2-b]pyridazin-6-yl)pyrimidine-2,4(1H,3H)-dione

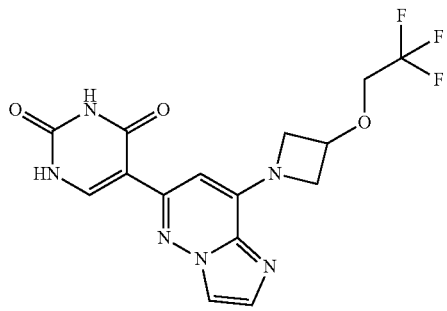

5-(8-(3-(2,2,2-trifluoroethoxy)azetidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3-(2,2,2-trifluoroethoxy)azetidine hydrochloride. Purification was accomplished by RP-HPLC (10-90% MeCN/H$_2$O with TFA modifier, Gemini column). ES/MS m/z: 383.1 [M+H]. $^1$H NMR (400 MHz, DMSO-d6) δ 11.40 (d, J=7.5 Hz, 2H), 8.05 (d, J=1.3 Hz, 1H), 7.94 (d, J=5.9 Hz, 1H), 7.60 (d, J=1.3 Hz, 1H), 6.50 (s, 1H), 4.69 (tt, J=6.6, 3.7 Hz, 1H), 4.60 (t, J=8.1 Hz, 2H), 4.28-4.13 (m, 4H). $^{19}$F NMR (376 MHz, DMSO-d6) δ −73.39 (t, J=9.3 Hz), −75.09.

Example 448. 5-(8-(6-(difluoromethyl)-2-azaspiro[3.3]heptan-2-yl)imidazo[1,2-b]pyridazin-6-yl)pyrimidine-2,4(1H,3H)-dione

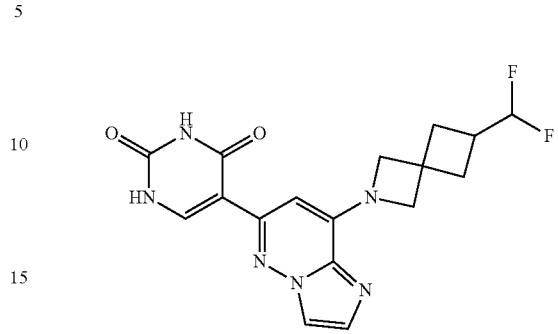

5-(8-(6-(difluoromethyl)-2-azaspiro[3.3]heptan-2-yl)imidazo[1,2-b]pyridazin-6-yl)pyrimidine-2,4(1H,3H)-dione was prepared in the manner described for Example 442, but replacing 6-azabicyclo[3.2.0]heptane with 6-(difluoromethyl)-2-azaspiro[3.3]heptane hydrochloride. Purification was accomplished by RP-HPLC (10-90% MeCN/H$_2$O with TFA modifier, Gemini column). ES/MS m/z: 375.1 [M+H]. $^1$H NMR (400 MHz, DMSO-d6) δ 11.38 (d, J=2.0 Hz, 1H), 11.36 (dd, J=6.2, 2.0 Hz, 1H), 8.01 (d, J=1.2 Hz, 1H), 7.92 (d, J=6.1 Hz, 1H), 7.55 (d, J=1.2 Hz, 1H), 6.43 (s, 1H), 6.08 (td, J=57.2, 4.1 Hz, 1H), 4.34 (br d, J=36.5 Hz, 4H), 2.74-2.62 (m, 1H), 2.42-2.34 (m, 2H), 2.30-2.19 (m, 2H). $^{19}$F NMR (376 MHz, DMSO-d6) δ −74.94, −123.55 (dd, J=57.1, 16.1 Hz).

Example 449. 5-(8-(7,7-difluoro-5-oxa-2-azaspiro[3.4]octan-2-yl)imidazo[1,2-b]pyridazin-6-yl)pyrimidine-2,4(1H,3H)-dione

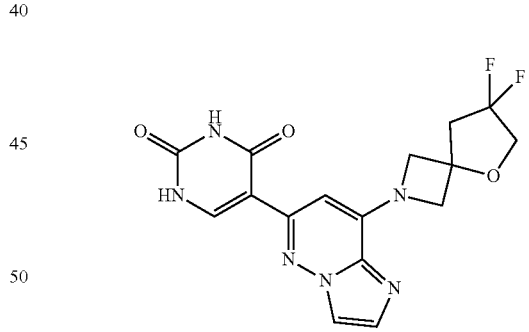

5-(8-(7,7-difluoro-5-oxa-2-azaspiro[3.4]octan-2-yl)imidazo[1,2-b]pyridazin-6-yl)pyrimidine-2,4(1H,3H)-dione was prepared in the manner described for Example 442, but replacing 6-azabicyclo[3.2.0]heptane with 7,7-difluoro-5-oxa-2-azaspiro[3.4]octane, 2,2,2-trifluoroacetate. Purification was accomplished by RP-HPLC (10-90% MeCN/H$_2$O with TFA modifier, Gemini column). ES/MS m/z: 377.1 [M+H]. $^1$H NMR (400 MHz, DMSO-d6) δ 11.44-11.32 (m, 2H), 8.05 (d, J=1.2 Hz, 1H), 7.94 (d, J=6.1 Hz, 1H), 7.58 (d, J=1.2 Hz, 1H), 6.51 (s, 1H), 4.56 (br s, 2H), 4.40 (d, J=10.0 Hz, 2H), 4.10 (t, J=13.1 Hz, 2H), 2.87 (t, J=14.4 Hz, 2H). $^{19}$F NMR (376 MHz, DMSO-d6) δ −75.21, −100.84 (p, J=13.7 Hz).

Example 450. 5-(8-(3-(2,4-difluorobenzyl)azetidin-1-yl)imidazo[1,2-b]pyridazin-6-yl)pyrimidine-2,4(1H,3H)-dione

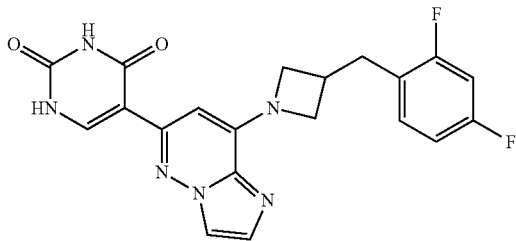

5-(8-(3-(2,4-difluorobenzyl)azetidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3-[(2,4-difluorophenyl)methyl]azetidine, hydrochloride. Purification was accomplished by RP-HPLC (10-90% MeCN/H$_2$O with TFA modifier, Gemini column). ES/MS m/z: 411.1 [M+H]. $^1$H NMR (400 MHz, DMSO-d6) δ 11.43-11.32 (m, 2H), 8.05 (d, J=1.3 Hz, 1H), 7.93 (d, J=6.0 Hz, 1H), 7.59 (s, 1H), 7.43 (td, J=8.7, 6.6 Hz, 1H), 7.22 (td, J=9.9, 2.6 Hz, 1H), 7.05 (td, J=8.5, 2.6 Hz, 1H), 6.48 (s, 1H), 4.43 (br s, 2H), 4.08 (br s, 2H), 3.09 (h, J=6.9 Hz, 1H), 3.00 (d, J=7.8 Hz, 2H). $^{19}$F NMR (376 MHz, DMSO-d6) δ −75.22, −113.33 (ddd, J=15.7, 8.8, 6.7 Hz), −114.36 (q, J=8.5 Hz).

Example 451. 5-(8-(7-azabicyclo[4.2.0]octan-7-yl)imidazo[1,2-b]pyridazin-6-yl)pyrimidine-2,4(1H,3H)-dione

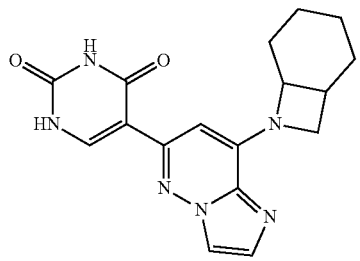

5-(8-(7-azabicyclo[4.2.0]octan-7-yl)imidazo[1,2-b]pyridazin-6-yl)pyrimidine-2,4(1H,3H)-dione was prepared in the manner described for Example 442, but replacing 6-azabicyclo[3.2.0]heptane with 7-azabicyclo[4.2.0]octane. Purification was accomplished by RP-HPLC (10-90% MeCN/H$_2$O with TFA modifier, Gemini column). ES/MS m/z: 339.2 [M+H]. $^1$H NMR (400 MHz, DMSO-d6) δ 11.38 (d, J=5.3 Hz, 2H), 8.05 (d, J=1.3 Hz, 1H), 7.95 (d, J=6.1 Hz, 1H), 7.61 (d, J=1.3 Hz, 1H), 6.63 (s, 1H), 4.73-4.62 (m, 1H), 4.29 (t, J=8.6 Hz, 1H), 4.18-4.12 (m, 1H), 2.91-2.80 (m, 1H), 2.06-1.85 (m, 2H), 1.85-1.51 (m, 4H), 1.51-1.34 (m, 2H).

Example 452. 5-(8-(3-(2,2,2-trifluoroethyl)pyrrolidin-1-yl)imidazo[1,2-b]pyridazin-6-yl)pyrimidine-2,4(1H,3H)-dione

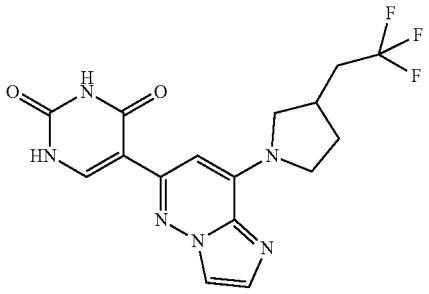

5-(8-(3-(2,2,2-trifluoroethyl)pyrrolidin-1-yl)imidazo[1,2-b]pyridazin-6-yl)pyrimidine-2,4(1H,3H)-dione was prepared as a racemic mixture in the manner described for Example 442, but replacing 6-azabicyclo[3.2.0]heptane with 3-(2,2,2-trifluoroethyl)pyrrolidine hydrochloride. Purification was accomplished by RP-HPLC (10-90% MeCN/H$_2$O with TFA modifier, Gemini column). ES/MS m/z: 381.1 [M+H]. $^1$H NMR (400 MHz, DMSO-d6) δ 11.47-11.19 (m, 2H), 8.02 (s, 1H), 7.93 (d, J=6.1 Hz, 1H), 7.55 (s, 1H), 6.58 (s, 1H), 3.69 (br s, 2H), 3.50 (br s, 2H), 2.57 (m, 3H), 2.28-2.15 (m, 1H), 1.78 (t, J=10.6 Hz, 1H). $^{19}$F NMR (376 MHz, DMSO-d6) δ −63.82 (t, J=11.3 Hz), −75.16 (d, J=3.3 Hz).

Example 453. 5-(8-(3-(2,2-difluoroethyl)pyrrolidin-1-yl)imidazo[1,2-b]pyridazin-6-yl)pyrimidine-2,4(1H,3H)-dione

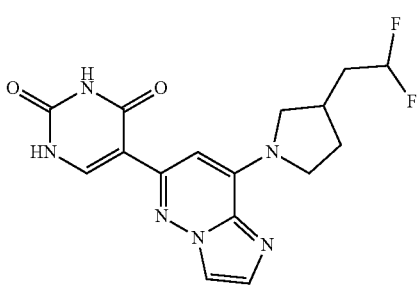

5-(8-(3-(2,2-difluoroethyl)pyrrolidin-1-yl)imidazo[1,2-b]pyridazin-6-yl)pyrimidine-2,4(1H,3H)-dione was prepared as a racemic mixture in the manner described for Example 442, but replacing 6-azabicyclo[3.2.0]heptane with 3-(2,2-difluoroethyl)pyrrolidine hydrochloride. Purification was accomplished by RP-HPLC (10-90% MeCN/H$_2$O with TFA modifier, Gemini column). ES/MS m/z: 363.2 [M+H]. $^1$H NMR (400 MHz, DMSO-d6) δ 11.48-11.23 (m, 2H), 8.04 (d, J=1.2 Hz, 1H), 7.93 (d, J=6.1 Hz, 1H), 7.58 (d, J=1.2 Hz, 1H), 6.59 (s, 1H), 6.21 (tt, J=56.3, 4.4 Hz, 1H), 3.70 (br s, 2H), 3.44 (br s, 2H), 2.48-2.39 (m, 1H), 2.26-2.15 (m, 1H), 2.15-1.98 (m, 2H), 1.80-1.65 (m, 1H). $^{19}$F NMR (376 MHz, DMSO-d6) δ −75.23, −115.09 (dtd, J=56.7, 18.6, 6.6 Hz).

Example 454. (R)-5-(8-(3-(2,2-difluoroethyl)pyrrolidin-1-yl)imidazo[1,2-b]pyridazin-6-yl)pyrimidine-2,4(1H,3H)-dione

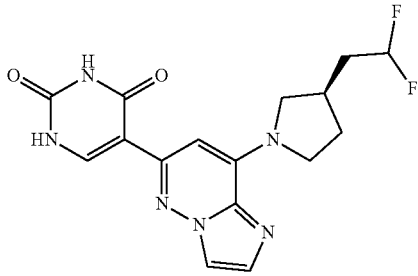

(R)-5-(8-(3-(2,2-difluoroethyl)pyrrolidin-1-yl)imidazo[1,2-b]pyridazin-6-yl)pyrimidine-2,4(1H,3H)-dione was prepared in the manner described for Example 442, but replacing 6-azabicyclo[3.2.0]heptane with (3R)-3-(2,2-difluoroethyl)pyrrolidine hydrochloride. Purification was accomplished by RP-HPLC (10-90% MeCN/H₂O with TFA modifier, Gemini column). ES/MS m/z: 363.1 [M+H]. ¹H NMR (400 MHz, DMSO-d6) δ 11.44-11.28 (m, 2H), 8.04 (d, J=1.2 Hz, 1H), 7.94 (d, J=6.1 Hz, 1H), 7.59 (d, J=1.3 Hz, 1H), 6.60 (s, 1H), 6.21 (tt, J=56.4, 4.4 Hz, 1H), 3.72 (m, 2H), 3.60-3.23 (m, 2H), 2.48-2.41 (m, 1H), 2.26-2.15 (m, 1H), 2.15-1.98 (m, 2H), 1.74 (dq, J=12.0, 9.5 Hz, 1H). ¹⁹F NMR (376 MHz, DMSO-d6) δ -75.27, -115.09 (dtd, J=56.5, 18.5, 5.9 Hz).

Example 455. 5-(3-chloro-8-(3-fluoro-3-(trifluoromethyl)azetidin-1-yl)imidazo[1,2-b]pyridazin-6-yl)pyrimidine-2,4(1H,3H)-dione

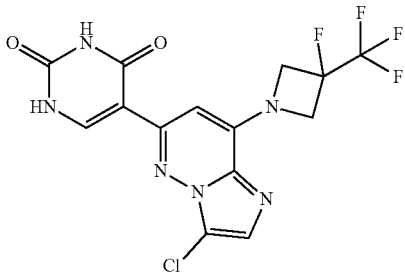 [SMILES: O=c1[nH]cc(-c2cc(N3CC(F)(C(F)(F)F)C3)c3ncc(Cl)n3n2)c(=O)[nH]1]

5-(3-chloro-8-(3-fluoro-3-(trifluoromethyl)azetidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3-fluoro-3-(trifluoromethyl)azetidine hydrochloride. Purification was accomplished by RP-HPLC (10-90% MeCN/H₂O with TFA modifier, Gemini column). ES/MS m/z: 405.0 [M+H]. ¹H NMR (400 MHz, DMSO-d6) δ 11.47 (d, J=2.1 Hz, 1H), 11.43 (dd, J=6.2, 2.1 Hz, 1H), 7.99 (d, J=6.1 Hz, 1H), 7.72 (s, 1H), 6.71 (s, 1H), 4.97-4.73 (m, 4H). ¹⁹F NMR (376 MHz, DMSO-d6) δ -75.15, -82.88 (d, J=7.6 Hz), -172.18--172.69 (m).

Example 456. 5-(7-((2S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione

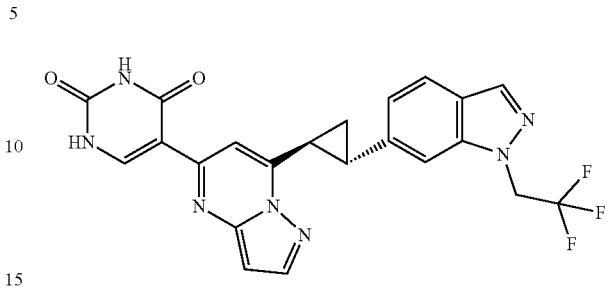

5-(7-((2S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione was prepared as follows: 5-bromo-7-((2S, 2S)-2-(1-(2,2,2-trifluoroethyl)-1H-indazol-6-yl)cyclopropyl)pyrazolo[1,5-a]pyrimidine (120 mg, 0.275 mmol), (2,4-ditert-butoxypyrimidin-5-yl)boronic acid (88.5 mg, 0.330 mmol), cesium carbonate (269 mg, 0.825 mmol), and Pd(dppf)Cl₂—CH₂Cl₂ (22.5 mg, 0.0275 mmol) were weighed into a microwave vial, and dioxane (2 mL) and water (0.5 mL) were added. The mixture was degassed with N2, and the vial was sealed and heated to 80° C. for 16 h. The mixture was then cooled to room temperature, and TFA (1 mL) was added slowly. The mixture was stirred at room temperature for an additional 20 min, then concentrated and purified by RP-HPLC (10-90% MeCN/H₂O with TFA modifier, Gemini column). ES/MS m/z: 468.1 [M+H]. ¹H NMR (400 MHz, DMSO-d6) δ 11.62 (dd, J=6.4, 2.0 Hz, 1H), 11.52 (d, J=1.9 Hz, 1H), 8.35 (d, J=6.3 Hz, 1H), 8.19-8.07 (m, 2H), 7.80-7.65 (m, 3H), 7.18 (dd, J=8.4, 1.4 Hz, 1H), 6.63 (d, J=2.3 Hz, 1H), 5.41 (q, J=9.1 Hz, 2H), 3.15 (ddd, J=8.3, 6.6, 4.5 Hz, 1H), 2.84-2.74 (m, 1H), 1.95 (ddd, J=8.3, 6.6, 1.5 Hz, 2H). ¹⁹F NMR (376 MHz, DMSO-d6) δ -70.08 (t, J=9.0 Hz), -75.62.

Example 457. 5-((6-(2,4-dioxo-1,2,3,4-tetrahydropyrimidin-5-yl)imidazo[1,2-b]pyridazin-8-yl)oxy)-4,4-difluoro-N-isopropylpentanamide

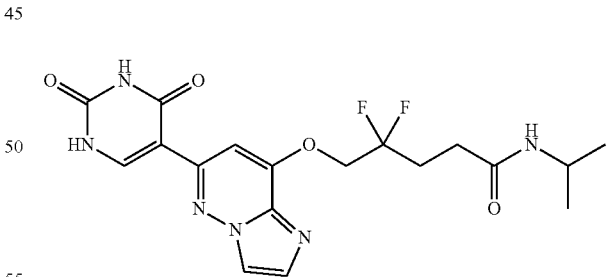

5-((6-(2,4-dioxo-1,2,3,4-tetrahydropyrimidin-5-yl)imidazo[1,2-b]pyridazin-8-yl)oxy)-4,4-difluoro-N-isopropylpentanamide was prepared in the manner described for Example 1, but replacing 8-cyclopropyl-6-(2,4-dimethoxypyrimidin-5-yl)-2-methyl-imidazo[1,2-b]pyridazine with 54(6-(2,4-dimethoxypyrimidin-5-yl)imidazo[1,2-b]pyridazin-8-yl)oxy)-4,4-difluoro-N-isopropylpentanamide. Purification was accomplished by RP-HPLC (10-90% MeCN/H₂O with TFA modifier, Gemini column). ES/MS m/z: 423.2 [M+H]. ¹H NMR (400 MHz, DMSO-d6) δ11.66-11.48 (m, 2H), 8.33 (d, J=1.3 Hz, 1H), 8.06 (d, J=6.1 Hz, 1H), 7.88-7.80 (m, 2H), 7.46 (s, 1H), 4.75 (t, J=12.7 Hz, 2H), 3.86-3.77 (m, 1H), 2.43-2.27 (m, 4H), 1.03 (d, J=6.5 Hz, 6H). $^{19}$F NMR (376 MHz, DMSO-d6) δ −75.17, −105.77 (tt, J=17.7, 12.2 Hz).

Example 458. 5-((6-(2,4-dioxo-1,2,3,4-tetrahydro-pyrimidin-5-yl)imidazo[1,2-b]pyridazin-8-yl)oxy)-4,4-difluoro-N-(2,2,2-trifluoroethyl)pentanamide

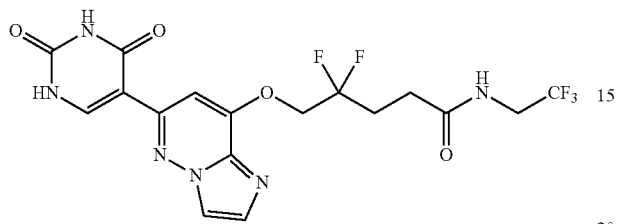

5-((6-(2,4-dioxo-1,2,3,4-tetrahydropyrimidin-5-yl)imidazo[1,2-b]pyridazin-8-yl)oxy)-4,4-difluoro-N-(2,2,2-trifluoroethyl)pentanamide was prepared in the manner described for Example 1, but replacing 8-cyclopropyl-6-(2,4-dimethoxypyrimidin-5-yl)-2-methyl-imidazo[1,2-b]pyridazine with 54(6-(2,4-dimethoxypyrimidin-5-yl)imidazo[1,2-b]pyridazin-8-yl)oxy)-4,4-difluoro-N-(2,2,2-trifluoroethyl)pentanamide. Purification was accomplished by RP-HPLC (10-90% MeCN/H$_2$O with TFA modifier, Gemini column). ES/MS m/z: 463.1 [M+H]. $^1$H NMR (400 MHz, DMSO-d6) δ 11.56 (d, J=6.1 Hz, 2H), 8.69 (t, J=6.4 Hz, 1H), 8.31 (d, J=1.4 Hz, 1H), 8.05 (d, J=6.1 Hz, 1H), 7.80 (d, J=1.4 Hz, 1H), 7.43 (s, 1H), 4.76 (t, J=12.7 Hz, 2H), 3.91 (qd, J=9.9, 6.3 Hz, 2H), 2.49-2.31 (m, 4H). $^{19}$F NMR (376 MHz, DMSO-d6) δ−71.26--71.51 (m), −75.07, −106.02 (ddd, J=26.1, 17.2, 12.4 Hz).

Example 459. 5-(8-((2S,2S)-2-(3-chloro-1-(2,2,2-trifluoroethyl)-1H-indazol-6-yl)cyclopropyl)imidazo[1,2-b]pyridazin-6-yl)pyrimidine-2,4(1H,3H)-dione

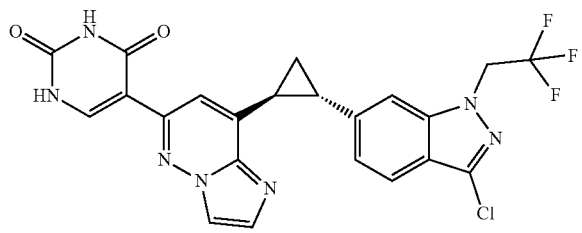 [SMILES: O=c1[nH]cc(-c2cc([C@H]3C[C@@H]3c3ccc4c(Cl)nn(CC(F)(F)F)c4c3)c3nccn3n2)c(=O)[nH]1]

5-(8-((2S,2S)-2-(3-chloro-1-(2,2,2-trifluoroethyl)-1H-indazol-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-((2S,2S)-2-(3-chloro-1-(2,2,2-trifluoroethyl)-1H-indazol-6-yl)cyclopropyl)-6-(2,4-dimethoxypyrimidin-5-yl)imidazo[1,2-b]pyridazine. Purification was accomplished by RP-HPLC (10-90% MeCN/H$_2$O with TFA modifier, Gemini column). ES/MS m/z: 502.2 [M+H]. $^1$H NMR (400 MHz, DMSO-d6) δ 11.55 (d, J=3.8 Hz, 2H), 8.33 (d, J=1.4 Hz, 1H), 8.04 (d, J=6.4 Hz, 1H), 7.86 (s, 1H), 7.81 (s, 1H), 7.66 (d, J=8.4 Hz, 1H), 7.60 (s, 1H), 7.25 (dd, J=8.5, 1.2 Hz, 1H), 5.44 (q, J=9.0 Hz, 2H), 3.04 (ddd, J=9.3, 6.1, 4.3 Hz, 1H), 2.87-2.79 (m, 1H), 2.17 (dt, J=9.0, 5.3 Hz, 1H), 1.93 (dt, J=8.5, 5.2 Hz, 1H). $^{19}$F NMR (376 MHz, DMSO-d6) δ −70.17 (t, J=9.0 Hz), −75.13.

Example 460. 5-(8-((2S,2S)-2-(4-chloro-1-(2,2,2-trifluoroethyl)-1H-indazol-6-yl)cyclopropyl)imidazo[1,2-b]pyridazin-6-yl)pyrimidine-2,4(1H,3H)-dione

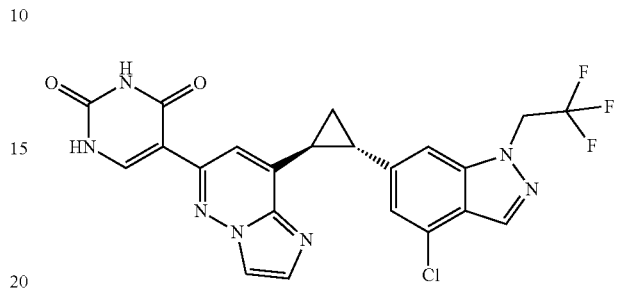

5-(8-((2S,2S)-2-(4-chloro-1-(2,2,2-trifluoroethyl)-1H-indazol-6-yl)cyclopropyl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-((1S,2S)-2-(4-chloro-1-(2,2,2-trifluoroethyl)-1H-indazol-6-yl)cyclopropyl)-6-(2,4-dimethoxypyrimidin-5-yl)imidazo[1,2-b]pyridazine. Purification was accomplished by RP-HPLC (10-90% MeCN/H$_2$O with TFA modifier, Gemini column). ES/MS m/z: 502.1 [M+H]. $^1$H NMR (400 MHz, DMSO-d6) δ 11.52 (d, J=5.3 Hz, 2H), 8.30 (s, 1H), 8.23 (s, 1H), 8.02 (d, J=6.1 Hz, 1H), 7.80 (s, 1H), 7.77 (s, 1H), 7.56 (s, 1H), 7.25 (s, 1H), 5.45 (q, J=9.1 Hz, 2H), 3.04 (dt, J=9.4, 5.4 Hz, 1H), 2.82 (dt, J=10.0, 5.5 Hz, 1H), 2.17 (dt, J=10.6, 5.2 Hz, 1H), 1.96-1.88 (m, 1H). $^{19}$F NMR (376 MHz, DMSO-d6) δ −70.09 (t, J=9.1 Hz), −74.90.

Example 461. 5-(8-((1S,2S)-2-(1H-benzo[d]imidazol-2-yl)cyclopropyl)imidazo[1,2-b]pyridazin-6-yl)pyrimidine-2,4(1H,3H)-dione

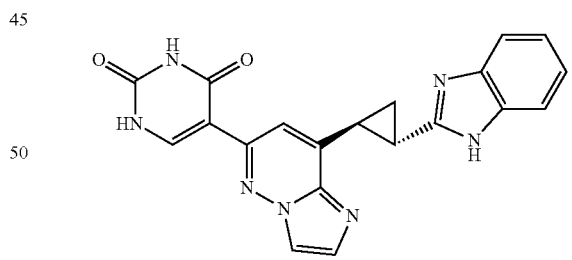

5-(8-((1S,2S)-2-(1H-benzo[d]imidazol-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 8-((1S,2S)-2-(1H-benzo[d]imidazol-2-yl)cyclopropyl)-6-(2,4-dimethoxypyrimidin-5-yl)imidazo[1,2-b]pyridazine (Racemic Mixture) and purified by RP-HPLC (10-90% MeCN/H$_2$O with TFA, Gemini column). ES/MS m/z: 386.2 [M+H]. $^1$H NMR (400 MHz, DMSO-d6) δ 11.81 (dd, J=6.2, 2.0 Hz, 1H), 11.62 (d, J=2.0 Hz, 1H), 8.55 (d, J=1.7 Hz, 1H), 8.20-8.07 (m, 2H), 7.97 (s, 1H), 7.76 (dt, J=6.7, 3.3 Hz, 2H), 7.53 (dd, J=6.1, 3.1 Hz, 2H), 3.50 (td, J=7.4, 4.4 Hz, 1H), 3.32-3.22 (m, 1H), 2.48 (d, J=10.8 Hz, 2H).

Example 462. (1S,2S)-2-(6-(2,4-dioxo-1,2,3,4-tetrahydropyrimidin-5-yl)imidazo[1,2-b]pyridazin-8-yl)-N-phenylcyclopropane-1-carboxamide

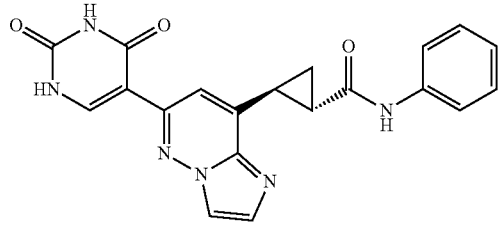 [SMILES: O=C(Nc1ccccc1)[C@H]1C[C@@H]1c1cc(-c2c[nH]c(=O)[nH]c2=O)nn2ccnc12]

(1S,2S)-2-(6-(2,4-dioxo-1,2,3,4-tetrahydropyrimidin-5-yl)imidazo[1,2-b]pyridazin-8-yl)-N-phenylcyclopropane-1-carboxamide was prepared as a racemic mixture in the manner described for Example 1, but replacing 8-cyclopropyl-6-(2,4-dimethoxypyrimidin-5-yl)-2-methyl-imidazo[1,2-b]pyridazine with (1S,2S)-2-(6-(2,4-dimethoxypyrimidin-5-yl)imidazo[1,2-b]pyridazin-8-yl)-N-phenylcyclopropane-1-carboxamide (Racemic Mixture) and purified by RP-HPLC (10-90% MeCN/H₂O with TFA, Gemini column). ES/MS m/z: 389.1 [M+H]. ¹H NMR (400 MHz, DMSO-d6) δ 11.65-11.53 (m, 2H), 10.43 (s, 1H), 8.38 (d, J=1.4 Hz, 1H), 8.05 (d, J=6.1 Hz, 1H), 7.93 (d, J=1.5 Hz, 1H), 7.65 (s, 1H), 7.64-7.56 (m, 2H), 7.34-7.26 (m, 2H), 7.04 (td, J=7.3, 1.2 Hz, 1H), 2.86 (ddd, J=9.5, 6.1, 4.0 Hz, 1H), 2.82-2.74 (m, 1H), 1.90 (ddd, J=8.5, 6.2, 3.9 Hz, 1H), 1.68 (ddd, J=9.3, 5.6, 3.8 Hz, 1H).

Example 463. 5-(8-((2S,2S)-2-(2-hydroxypropan-2-yl)cyclopropyl)imidazo[1,2-b]pyridazin-6-yl)pyrimidine-2,4(1H,3H)-dione

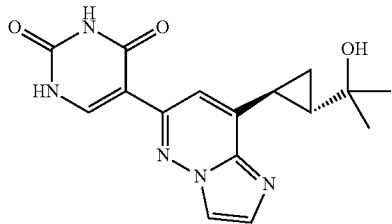 [SMILES: CC(C)(O)[C@H]1C[C@@H]1c1cc(-c2c[nH]c(=O)[nH]c2=O)nn2ccnc12]

5-(8-((1S,2S)-2-(2-hydroxypropan-2-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 2-((2S,2S)-2-(6-(2,4-dimethoxypyrimidin-5-yl)imidazo[1,2-b]pyridazin-8-yl)cyclopropyl)propan-2-ol (Racemic Mixture) and purified by RP-HPLC (10-90% MeCN/H₂O with TFA, Gemini column). ES/MS m/z: 328.2 [M+H]. ¹H NMR (400 MHz, DMSO-d6) δ 11.63-11.47 (m, 2H), 8.36 (s, 1H), 8.02 (d, J=6.1 Hz, 1H), 7.95 (s, 1H), 7.48 (s, 1H), 2.47 (d, J=5.4 Hz, 1H), 1.78-1.67 (m, 1H), 1.41-1.31 (m, 1H), 1.27 (dd, J=9.2, 4.7 Hz, 1H), 1.21 (s, 3H), 1.19 (s, 3H).

Example 464. 5-(8-((2S,2S)-2-(2,3,4-trifluorophenyl)cyclopropyl)imidazo[1,2-b]pyridazin-6-yl)pyrimidine-2,4(1H,3H)-dione

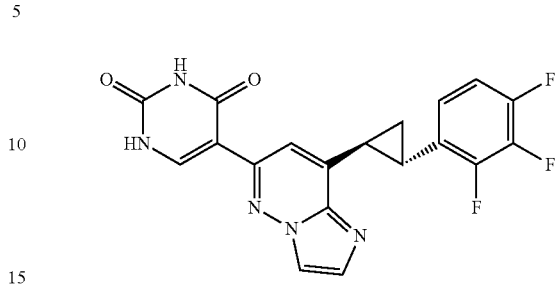

5-(8-((1S,2S)-2-(2,3,4-trifluorophenyl)cyclopropyl)imidazo[1,2-b]pyridazin-6-yl)pyrimidine-2,4(1H,3H)-dione was prepared as a racemic mixture in the manner described for Intermediate 81, but replacing 8-bromo-6-chloro-imidazo[1,2-b]pyridazine with 5-(8-bromoimidazo[1,2-b]pyridazin-6-yl)pyrimidine-2,4(1H,3H)-dione and racemic 2-[(1S,2S)-2-(3,5-difluorophenyl)cyclopropyl]-4,4,5,5-tetramethyl-1,3,2-dioxaborolane with 4,4,5,5-tetramethyl-2-((1S,2S)-2-(2,3,4-trifluorophenyl)cyclopropyl)-1,3,2-dioxaborolane, and purified by RP-HPLC (10-90% MeCN/H₂O with TFA, Gemini column). ES/MS m/z: 400.1 [M+H]. ¹H NMR (400 MHz, DMSO-d6) δ 11.50 (d, J=6.3 Hz, 2H), 8.27 (s, 1H), 8.00 (d, J=6.0 Hz, 1H), 7.76 (s, 1H), 7.55 (s, 1H), 7.37-7.25 (m, 1H), 7.22-7.12 (m, 1H), 3.02 (dt, J=10.3, 5.6 Hz, 1H), 2.74 (q, J=4.4 Hz, 1H), 2.13 (dt, J=9.9, 5.2 Hz, 1H), 1.79 (dt, J=8.8, 5.2 Hz, 1H). ¹⁹F NMR (376 MHz, DMSO-d6) δ -74.56 (s, 3F), -138.66 (m, 1F), -141.38 (m, 1F), -162.67 (m, 1F).

Example 465. 4-((2S,2S)-2-(6-(2,4-dioxo-1,2,3,4-tetrahydropyrimidin-5-yl)imidazo[1,2-b]pyridazin-8-yl)cyclopropyl)benzonitrile

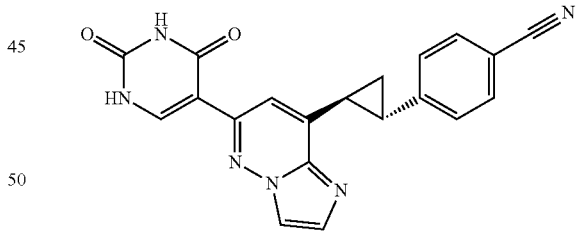

4-((2S,2S)-2-(6-(2,4-dioxo-1,2,3,4-tetrahydropyrimidin-5-yl)imidazo[1,2-b]pyridazin-8-yl)cyclopropyl)benzonitrile was prepared in the manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)imidazo[1,2-b]pyridazin-8-yl)cyclopropyl)benzonitrile and purified by RP-HPLC (10-90% MeCN/H₂O with TFA, Gemini column). ES/MS m/z: 371.1 [M+H]. ¹H NMR (400 MHz, DMSO-d6) δ 11.55 (d, J=6.3 Hz, 2H), 8.34 (s, 1H), 8.03 (d, J=6.0 Hz, 1H), 7.87 (s, 1H), 7.78 (d, J=8.2 Hz, 2H), 7.59 (s, 1H), 7.46 (d, J=8.3 Hz, 2H), 2.95-2.86 (m, 1H), 2.83 (dt, J=9.8, 5.4 Hz, 1H), 2.16 (dt, J=8.7, 5.5 Hz, 1H), 1.86 (dt, J=8.8, 5.5 Hz, 1H).

Example 466. 3-((2S,2S)-2-(6-(2,4-dioxo-1,2,3,4-tetrahydropyrimidin-5-yl)imidazo[1,2-b]pyridazin-8-yl)cyclopropyl)-4-fluorobenzonitrile

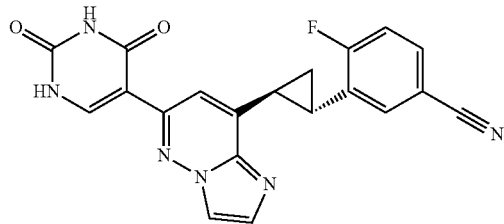 [SMILES: N#Cc1ccc(F)c([C@H]2C[C@@H]2c2cc(-c3c[nH]c(=O)[nH]c3=O)nn3ccnc23)c1]

3-((2S,2S)-2-(6-(2,4-dioxo-1,2,3,4-tetrahydropyrimidin-5-yl)imidazo[1,2-b]pyridazin-8-yl)cyclopropyl)-4-fluorobenzonitrile was prepared as a racemic mixture in the manner described for Example 1, but replacing 8-cyclopropyl-6-(2,4-dimethoxypyrimidin-5-yl)-2-methyl-imidazo[1,2-b]pyridazine with 3-((2S,2S)-2-(6-(2,4-dimethoxypyrimidin-5-yl)imidazo[1,2-b]pyridazin-8-yl)cyclopropyl)-4-fluorobenzonitrile and purified by RP-HPLC (10-90% MeCN/H$_2$O with TFA, Gemini column). ES/MS m/z: 389.1 [M+H]. $^1$H NMR (400 MHz, DMSO-d6) δ 11.55 (d, J=5.5 Hz, 2H), 8.36 (d, J=1.4 Hz, 1H), 8.03 (d, J=6.1 Hz, 1H), 7.90 (s, 1H), 7.86 (dd, J=7.1, 2.1 Hz, 1H), 7.81 (ddd, J=8.5, 4.8, 2.1 Hz, 1H), 7.66 (s, 1H), 7.43 (dd, J=10.0, 8.5 Hz, 1H), 3.02 (ddd, J=9.0, 6.2, 4.5 Hz, 1H), 2.88-2.79 (m, 1H), 2.13 (dt, J=8.9, 5.3 Hz, 1H), 2.02-1.85 (m, 1H). $^{19}$F NMR (376 MHz, DMSO-d6) δ −75.18 (s, 3F), −110.52 (p, J=5.4 Hz, 1F).

Example 467. 4-((2S,2S)-2-(6-(2,4-dioxo-1,2,3,4-tetrahydropyrimidin-5-yl)imidazo[1,2-b]pyridazin-8-yl)cyclopropyl)-2-fluorobenzonitrile

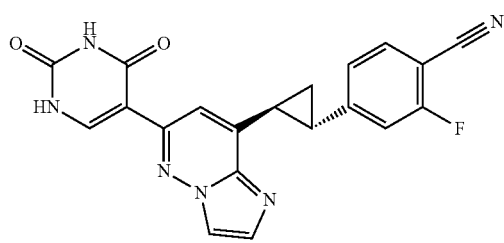 [SMILES: N#Cc1ccc([C@H]2C[C@@H]2c2cc(-c3c[nH]c(=O)[nH]c3=O)nn3ccnc23)cc1F]

4-((1S,2S)-2-(6-(2,4-dioxo-1,2,3,4-tetrahydropyrimidin-5-yl)imidazo[1,2-b]pyridazin-8-yl)cyclopropyl)-2-fluorobenzonitrile was prepared in the manner described for Example 1, but replacing 8-cyclopropyl-6-(2,4-dimethoxypyrimidin-5-yl)-2-methyl-imidazo[1,2-b]pyridazine with 4-(1S,2S)-2-(6-(2,4-dimethoxypyrimidin-5-yl)imidazo[1,2-b]pyridazin-8-yl)cyclopropyl)-2-fluorobenzonitrile and purified by RP-HPLC (10-90% MeCN/H$_2$O with TFA, Gemini column). ES/MS m/z: 389.1 [M+H]. $^1$H NMR (400 MHz, DMSO-d6) δ 11.54 (d, J=4.2 Hz, 2H), 8.32 (d, J=1.4 Hz, 1H), 8.02 (d, J=6.3 Hz, 1H), 7.90-7.81 (m, 2H), 7.59 (s, 1H), 7.47 (dd, J=11.0, 1.6 Hz, 1H), 7.34 (dd, J=8.1, 1.6 Hz, 1H), 2.96 (m, 1H), 2.85 (m, 1H), 2.23 (dt, J=8.8, 5.5 Hz, 1H), 1.89 (dt, J=8.8, 5.3 Hz, 1H). $^{19}$F NMR (376 MHz, DMSO-d6) δ −75.15 (s, 3F), −109.51 (dd, J=11.1, 7.1 Hz, 1F).

Example 468. 5-(8-((2S,2S)-2-(2,3,6-trifluorophenyl)cyclopropyl)imidazo[1,2-b]pyridazin-6-yl)pyrimidine-2,4(1H,3H)-dione

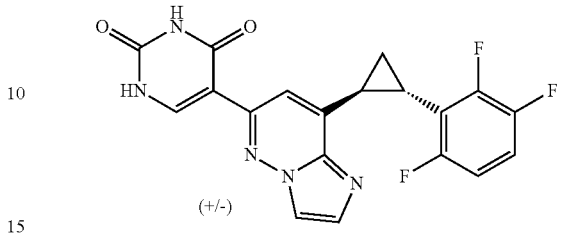

(+/-)

To a reaction vessel containing 5-(8-bromoimidazo[1,2-b]pyridazin-6-yl)pyrimidine-2,4(1H,3H)-dione (124 mg, 0.40 mmol, 1.2 equiv.), racemic 4,4,5,5-tetramethyl-2-((2S,2S)-2-(2,3,6-trifluorophenyl)cyclopropyl)-1,3,2-dioxaborolane (100 mg, 0.34 mmol, 1 equiv.), CataCXium A Pd G3 (12 mg, 0.017 mmol, 5 mol %) and K$_3$PO$_4$ (214 mg, 1.0 mmol, 3 equiv.) was added a mixture of freshly degassed dioxane/water (1.98 mL, 5:1 ratio) under an atmosphere of nitrogen. The reaction was heated to 120° C. and stirred overnight. The reaction mixture was subsequently cooled to room temperature, diluted with DMF/water, filtered and purified by RP-HPLC (10-90% MeCN/H$_2$O with TFA, Gemini column). 400.1 [M+H]. $^1$H NMR (400 MHz, DMSO-d6) δ 11.54 (m, 2H), 8.33 (d, J=1.4 Hz, 1H), 8.02 (d, J=6.3 Hz, 1H), 7.85 (s, 1H), 7.63 (s, 1H), 7.41 (qd, J=9.5, 5.0 Hz, 1H), 7.13 (tdd, J=9.5, 4.1, 2.1 Hz, 1H), 2.99-2.89 (m, 2H), 2.12 (dt, J=9.7, 5.3 Hz, 1H), 1.89 (ddd, J=8.6, 6.8, 4.7 Hz, 1H). $^{19}$F NMR (376 MHz, DMSO-d6) δ −75.03 (s, 3F), −119.95 (ddt, J=14.7, 9.3, 4.3 Hz, 1F), −139.15−−139.84 (m, 1F), −143.41 (dddd, J=21.7, 14.5, 10.1, 4.1 Hz, 1F).

Example 469. 5-(7-((2S,2S)-2-(2,4-difluorophenyl)cyclopropyl)pyrazolo[1,5-a]pyrimidin-5-yl)pyrimidine-2,4(1H,3H)-dione

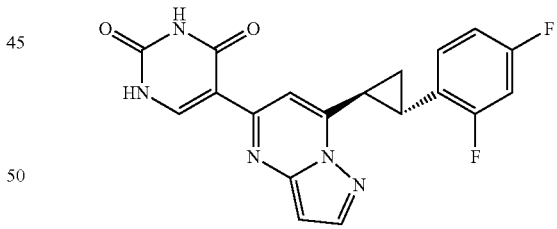

5-(7-((1S,2S)-2-(2,4-difluorophenyl)cyclopropyl)pyrazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-((2S,2S)-2-(2,4-difluorophenyl)cyclopropyl)-5-(2,4-dimethoxypyrimidin-5-yl)pyrazolo[1,5-a]pyrimidine. The reaction was stirred at 80° C. for only 1 hour before workup and purification by RP-HPLC (10-90% MeCN/H$_2$O with TFA, Gemini column). ES/MS m/z: 382.1 [M+H]. $^1$H NMR (400 MHz, DMSO-d6) δ 11.64-11.54 (m, 1H), 11.50 (d, J=2.0 Hz, 1H), 8.33 (d, J=6.4 Hz, 1H), 8.20 (d, J=2.3 Hz, 1H), 7.69 (s, 1H), 7.46 (td, J=8.8, 6.5 Hz, 1H), 7.24 (ddd, J=10.7, 9.3, 2.6 Hz, 1H), 7.15-7.03 (m, 1H), 6.65 (d, J=2.3 Hz, 1H), 3.06 (ddd, J=8.8, 6.1, 4.7 Hz, 1H), 2.71-2.61 (m, 1H), 1.93-1.77 (m, 2H). ¹⁹F NMR (376 MHz, DMSO-d6) δ −75.08 (s, 3F), −113.08 (ddd, J=15.2, 8.8, 6.4 Hz, 1F), −115.44 (td, J=9.8, 7.0 Hz, 1F).

Example 470. 5-(3-chloro-8-((2S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione

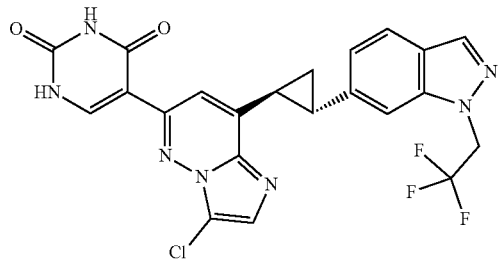 [SMILES: O=c1[nH]cc(-c2cc([C@H]3C[C@@H]3c3ccc4cnn(CC(F)(F)F)c4c3)c3ncc(Cl)n3n2)c(=O)[nH]1]

To a solution of 5-(8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione (25 mg, 0.043 mmol, 1 equiv.) in DMF (0.5 mL) was added Palau'Chlor (9 mg, 0.043 mmol, 1 equiv) at room temperature. The reaction was stirred for 4 hours before being diluted with DMF/water and purified by RP-HPLC (10-90% MeCN/H₂O with TFA, Gemini column). ES/MS m/z: 502.10 [M+H]. ¹H NMR (400 MHz, DMSO-d6) δ 11.63-11.49 (m, 2H), 8.15 (s, 1H), 8.04 (d, J=6.0 Hz, 1H), 7.84 (s, 1H), 7.77-7.67 (m, 2H), 7.59 (s, 1H), 7.12 (dd, J=8.5, 1.1 Hz, 1H), 5.40 (q, J=9.1 Hz, 2H), 3.01 (ddd, J=9.0, 6.2, 4.3 Hz, 1H), 2.81 (ddd, J=8.9, 5.9, 4.4 Hz, 1H), 2.16 (dt, J=8.8, 5.2 Hz, 1H), 1.95-1.84 (m, 1H). ¹⁹F NMR (376 MHz, DMSO-d6) δ −70.08 (t, J=9.2 Hz, 3F), −75.40 (s, 3F).

Example 471. 5-(3-chloro-8-((2S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione

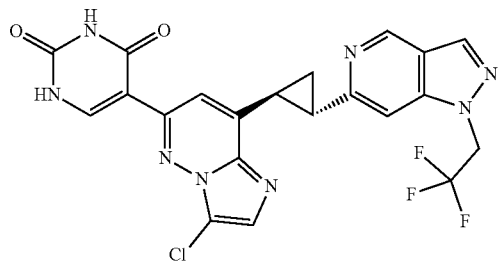 [SMILES: O=c1[nH]cc(-c2cc([C@H]3C[C@@H]3c3cc4c(cn3)cnn4CC(F)(F)F)c3ncc(Cl)n3n2)c(=O)[nH]1]

5-(3-chloro-8-((2S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione was prepared as racemic mixture in the manner described for Example 470, but replacing 5-(8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione with racemic 5-(8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione and purified by RP-HPLC (10-90% MeCN/H₂O with TFA, Gemini column). ES/MS m/z: 503.10 [M+H]. ¹H NMR (400 MHz, DMSO-d6) δ 11.58-11.51 (m, 2H), 9.14 (s, 1H), 8.46 (s, 1H), 8.05 (d, J=6.1 Hz, 1H), 7.93 (s, 1H), 7.85 (s, 1H), 7.63 (s, 1H), 5.46 (q, J=9.1 Hz, 2H), 3.19 (q, J=7.4, 6.2 Hz, 1H), 3.06 (ddd, J=9.8, 6.0, 4.1 Hz, 1H), 2.16 (dt, J=9.4, 5.0 Hz, 1H), 2.01 (dt, J=9.6, 4.5 Hz, 1H). ¹⁹F NMR (376 MHz, DMSO-d6) δ −70.14 (t, J=9.2 Hz, 3F), −74.82 (s, 3F).

Example 472. 5-(7-((3R,4S)-3,4-difluoropyrrolidin-1-yl)-[1,2,4]triazolo[1,5-a]pyrimidin-5-yl)pyrimidine-2,4(1H,3H)-dione

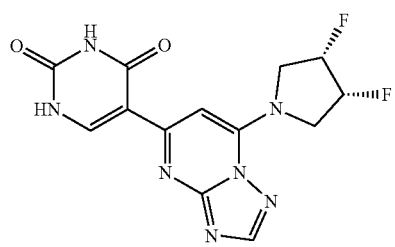 [SMILES: O=c1[nH]cc(-c2cc(N3C[C@@H](F)[C@@H](F)C3)n3ncnc3n2)c(=O)[nH]1]

5-(7-((3R,4S)-3,4-difluoropyrrolidin-1-yl)-[1,2,4]triazolo[1,5-a]pyrimidin-5-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 7-((3R,4S)-3,4-difluoropyrrolidin-1-yl)-5-(2,4-dimethoxypyrimidin-5-yl)-[1,2,4]triazolo[1,5-a]pyrimidine and purified by RP-HPLC (10-90% MeCN/H₂O with TFA, Gemini column). ES/MS m/z: 336.1 [M+H]. ¹H NMR (400 MHz, DMSO-d6) δ 11.71-11.57 (m, 1H), 11.51 (d, J=2.0 Hz, 1H), 8.47 (d, J=6.4 Hz, 1H), 8.42 (s, 1H), 7.42 (s, 1H), 5.56 (dt, J=11.4, 4.9 Hz, 1H), 5.49-5.35 (m, 1H), 4.35 (d, J=17.4 Hz, 2H), 4.13 (t, J=16.5 Hz, 2H). ¹⁹F NMR (376 MHz, DMSO-d6) δ −75.17 (s, 3F), −205.98 (m, 2F).

Example 473. 5-(8-(3,3-difluoro-4-methoxypyrrolidin-1-yl)imidazo[1,2-b]pyridazin-6-yl)pyrimidine-2,4(1H,3H)-dione

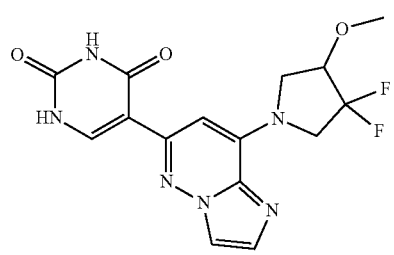 [SMILES: COC1CN(c2cc(-c3c[nH]c(=O)[nH]c3=O)nn3ccnc23)CC1(F)F]

5-(8-(3,3-difluoro-4-methoxypyrrolidin-1-yl)imidazo[1,2-b]pyridazin-6-yl)pyrimidine-2,4(1H,3H)-dione was prepared in the manner described for Example 442, but replacing 6-azabicyclo[3.2.0]heptane with 3,3-difluoro-4-methoxypyrrolidine hydrochloride and purified by RP-HPLC (10-90% MeCN/H₂O with TFA, Gemini column). ES/MS m/z: 365.1 [M+H]. ¹H NMR (400 MHz, DMSO-d6) δ 11.41 (d, J=2.0 Hz, 1H), 11.39-11.34 (m, 1H), 8.07 (d, J=1.2 Hz, 1H), 7.93 (d, J=6.1 Hz, 1H), 7.57 (d, J=1.2 Hz, 1H), 6.59 (s, 1H), 4.45 (d, J=11.6 Hz, 1H), 4.35-4.20 (m, 2H), 4.05-3.85 (m, 2H), 3.48 (s, 3H). $^{19}$F NMR (376 MHz, DMSO-d6) δ −75.14 (s, 3F), −107.10 (d, J=234.7 Hz, 1F), −121.69 (d, J=235.0 Hz, 1F).

Example 474. 5-(8-(3,3-difluoro-4-methoxypyrrolidin-1-yl)-3-fluoroimidazo[1,2-b]pyridazin-6-yl)pyrimidine-2,4(1H,3H)-dione

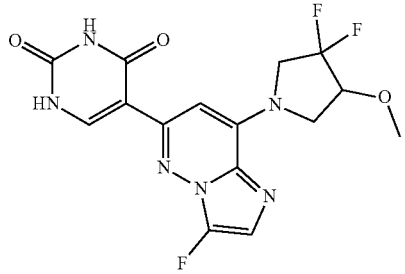 [SMILES: COC1CN(c2cc(-c3c[nH]c(=O)[nH]c3=O)nn3c(F)cnc23)CC1(F)F]

5-(8-(3,3-difluoro-4-methoxypyrrolidin-1-yl)-3-fluoroimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(3,3-difluoro-4-methoxypyrrolidin-1-yl)-6-(2,4-dimethoxypyrimidin-5-yl)-3-fluoroimidazo[1,2-b]pyridazine and purified by RP-HPLC (10-90% MeCN/H$_2$O with TFA, Gemini column). ES/MS m/z: 383.1 [M+H]. $^1$H NMR (400 MHz, DMSO-d6) δ 11.43 (d, J=2.0 Hz, 1H), 11.42-11.36 (m, 1H), 7.96 (d, J=6.1 Hz, 1H), 7.41 (d, J=7.2 Hz, 1H), 6.59 (s, 1H), 4.42 (s, 1H), 4.35-4.22 (m, 2H), 4.15 (s, 1H), 3.95 (s, 1H), 3.48 (s, 3H). $^{19}$F NMR (376 MHz, DMSO-d6) δ −107.22 (d, J=237.3 Hz, 1F), −121.87 (d, J=236.2 Hz, 1F), −155.44 (d, J=7.3 Hz, 1F).

Example 475. 5-(8-(7,7-difluoro-5-azaspiro[2.4]heptan-5-yl)-2-isobutylimidazo[1,2-b]pyridazin-6-yl)pyrimidine-2,4(1H,3H)-dione

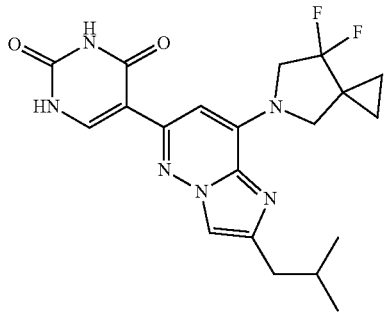 [SMILES: CC(C)Cc1cn2nc(-c3c[nH]c(=O)[nH]c3=O)cc(N3CC(F)(F)C4(CC4)C3)c2n1]

5-(8-(7,7-difluoro-5-azaspiro[2.4]heptan-5-yl)-2-isobutylimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 8-(7,7-difluoro-5-azaspiro[2.4]heptan-5-yl)-6-(2,4-dimethoxypyrimidin-5-yl)-2-isobutylimidazo[1,2-b]pyridazine and isolated by filtration as a hydrochloride salt. ES/MS m/z: 417.2 [M+H]. $^1$H NMR (400 MHz, DMSO-d6) δ 11.42 (d, J=3.8 Hz, 2H), 7.95 (d, J=6.3 Hz, 1H), 7.92 (s, 1H), 6.67 (s, 1H), 4.57 (t, J=12.4 Hz, 2H), 3.95 (s, 2H), 2.58 (d, J=7.0 Hz, 2H), 2.03 (dq, J=13.5, 6.7 Hz, 1H), 1.08-1.02 (m, 2H), 1.00 (t, J=3.1 Hz, 2H), 0.93 (d, J=6.6 Hz, 6H). $^{19}$F NMR (376 MHz, DMSO-d6) δ −107.32 (t, J=12.5 Hz, 2F).

Example 476. 5-(8-(cis-3-azabicyclo[3.2.0]heptan-3-yl)imidazo[1,2-b]pyridazin-6-yl)pyrimidine-2,4(1H,3H)-dione

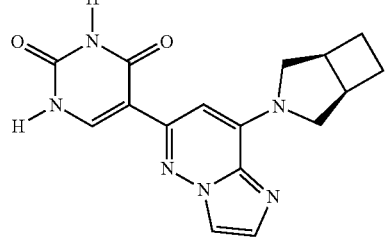

5-(8-bromoimidazo[1,2-b]pyridazin-6-yl)-1H-pyrimidine-2,4-dione (45 mg, 0.15 mmol), 3-azabicyclo[3.2.0]heptane hydrochloride (33 mg, 0.25 mmol), and DIPEA (0.10 mL, 0.60 mmol) were combined in NMP (0.3 mL) and stirred at 120° C. for 3 hours. The mixture was cooled, diluted with water, TFA, and MeCN, and purified by RP-HPLC (5-40% MeCN/H$_2$O with TFA modifier) affording 5-(8-(cis-3-azabicyclo[3.2.0]heptan-3-yl)imidazo[1,2-b]pyridazin-6-yl)pyrimidine-2,4(1H,3H)-dione as a TFA salt. ES/MS m/z: 325.2 [M+H]. $^1$H NMR (400 MHz, DMSO-d6) δ 11.40 (d, J=2.0 Hz, 1H), 11.37 (d, J=6.4 Hz, 1H), 8.05 (d, J=1.2 Hz, 1H), 7.95 (d, J=6.1 Hz, 1H), 7.58 (s, 1H), 6.73 (s, 1H), 4.29 (s, 2H), 3.08 (d, J=7.1 Hz, 2H), 2.24 (dt, J=9.6, 5.7 Hz, 2H), 1.74 (qd, J=6.6, 3.9 Hz, 2H).

Example 477. (S)-5-(8-(2-(methoxymethyl)pyrrolidin-1-yl)imidazo[1,2-b]pyridazin-6-yl)pyrimidine-2,4(1H,3H)-dione

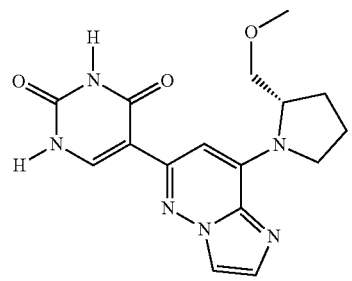 [SMILES: COC[C@@H]1CCCN1c1cc(-c2c[nH]c(=O)[nH]c2=O)nn2ccnc12]

(S)-5-(8-(2-(methoxymethyl)pyrrolidin-1-yl)imidazo[1,2-b]pyridazin-6-yl)pyrimidine-2,4(1H,3H)-dione was prepared in the manner described for Example 476, but replacing 3-azabicyclo[3.2.0]heptane with (S)-2-(methoxymethyl)pyrrolidine. ES/MS m/z: 343.2 [M+H]. $^1$H NMR (400 MHz, DMSO-d6) δ 11.39 (d, J=2.0 Hz, 1H), 11.36 (dd, J=6.2, 2.0 Hz, 1H), 8.03 (d, J=1.2 Hz, 1H), 7.94 (d, J=6.1 Hz, 1H), 7.59 (d, J=1.3 Hz, 1H), 6.69 (s, 1H), 5.04 (s, 1H), 3.79 (s, 1H), 3.57 (dd, J=9.5, 3.7 Hz, 1H), 3.39 (dd, J=9.4, 7.5 Hz, 1H), 3.33-3.22 (m, 4H), 2.15-1.70 (m, 4H).

Example 478. 5-(8-(1-fluoro-3-azabicyclo[3.2.0] heptan-3-yl)imidazo[1,2-b]pyridazin-6-yl)pyrimidine-2,4(1H,3H)-dione

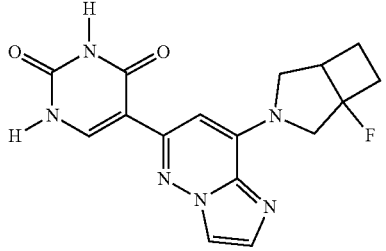 [SMILES: O=c1[nH]cc(-c2cc(N3CC4CCC4(F)C3)c3nccn3n2)c(=O)[nH]1]

5-(8-(1-fluoro-3-azabicyclo[3.2.0]heptan-3-yl)imidazo[1,2-b]pyridazin-6-yl)pyrimidine-2,4(1H,3H)-dione was prepared in the manner described for Example 476, but replacing 3-azabicyclo[3.2.0]heptane with 1-fluoro-3-azabicyclo[3.2.0]heptane. ES/MS m/z: 343.2 [M+H]. $^1$H NMR (400 MHz, DMSO-d6) δ 11.45-11.30 (m, 2H), 8.10 (d, J=1.3 Hz, 1H), 7.96 (d, J=6.1 Hz, 1H), 7.63 (d, J=1.3 Hz, 1H), 6.70 (s, 1H), 4.50 (t, J=15.5 Hz, 1H), 3.88 (dd, J=11.5, 6.4 Hz, 1H), 3.24 (ddt, J=23.4, 15.5, 7.3 Hz, 1H), 2.48-2.31 (m, 2H), 2.22-2.06 (m, 1H), 1.34 (p, J=9.7 Hz, 1H).

Example 479. 5-(8-(3,3-difluoro-4-methylpyrrolidin-1-yl)imidazo[1,2-b]pyridazin-6-yl)pyrimidine-2,4(1H,3H)-dione

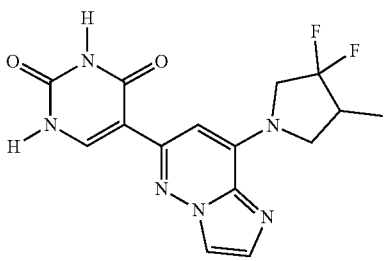 [SMILES: CC1CN(c2cc(-c3c[nH]c(=O)[nH]c3=O)nn3ccnc23)CC1(F)F]

5-(8-(3,3-difluoro-4-methylpyrrolidin-1-yl)imidazo[1,2-b]pyridazin-6-yl)pyrimidine-2,4(1H,3H)-dione was prepared in the manner described for Example 476, but replacing 3-azabicyclo[3.2.0]heptane with 3,3-difluoro-4-methylpyrrolidine. ES/MS m/z: 349.2 [M+H]. $^1$H NMR (400 MHz, DMSO-d6) δ 11.41 (d, J=1.9 Hz, 1H), 11.40-11.30 (m, 1H), 8.06 (d, J=1.2 Hz, 1H), 7.94 (d, J=6.1 Hz, 1H), 7.58 (d, J=1.2 Hz, 1H), 6.60 (s, 1H), 4.53-4.17 (m, 4H), 2.85 (dq, J=17.7, 8.9, 8.1 Hz, 1H), 1.15 (d, J=6.9 Hz, 3H).

Example 480. 5-(8-(3-oxopyrazolidin-1-yl)imidazo[1,2-b]pyridazin-6-yl)pyrimidine-2,4(1H,3H)-dione

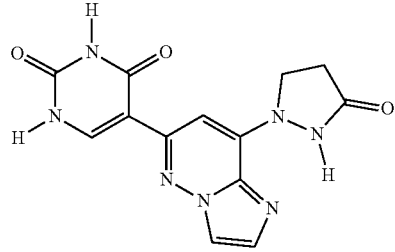 [SMILES: O=C1CCN(c2cc(-c3c[nH]c(=O)[nH]c3=O)nn3ccnc23)N1]

5-(8-(3-oxopyrazolidin-1-yl)imidazo[1,2-b]pyridazin-6-yl)pyrimidine-2,4(1H,3H)-dione was prepared in the manner described for Example 476, but replacing 3-azabicyclo[3.2.0]heptane with pyrazolidin-3-one. ES/MS m/z: 314.1 [M+H]. $^1$H NMR (400 MHz, DMSO-d6) δ 11.45 (s, 2H), 10.83 (s, 1H), 8.13 (s, 1H), 7.98 (d, J=6.1 Hz, 1H), 7.64 (s, 1H), 7.07 (s, 1H), 4.58 (s, 2H), 2.77-2.65 (m, 2H).

Example 481. 5-(8-(3,3-difluoroazetidin-1-yl)imidazo[1,2-b]pyridazin-6-yl)pyrimidine-2,4(1H,3H)-dione

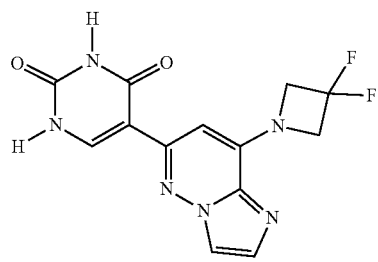 [SMILES: O=c1[nH]cc(-c2cc(N3CC(F)(F)C3)c3nccn3n2)c(=O)[nH]1]

5-(8-(3,3-difluoroazetidin-1-yl)imidazo[1,2-b]pyridazin-6-yl)pyrimidine-2,4(1H,3H)-dione was prepared in the manner described for Example 476, but replacing 3-azabicyclo[3.2.0]heptane with 3,3-difluoroazetidine. ES/MS m/z: 321.2 [M+H]. $^1$H NMR (400 MHz, DMSO-d6) δ 11.43 (d, J=2.0 Hz, 1H), 11.40 (d, J=6.6 Hz, 1H), 8.09 (d, J=1.2 Hz, 1H), 7.95 (d, J=6.1 Hz, 1H), 7.59 (d, J=1.2 Hz, 1H), 6.60 (s, 1H), 4.79 (t, J=12.3 Hz, 4H).

Example 482. 5-(8-(4-(4-fluorobenzyl)-3-oxopiperazin-1-yl)imidazo[1,2-b]pyridazin-6-yl)pyrimidine-2,4(1H,3H)-dione

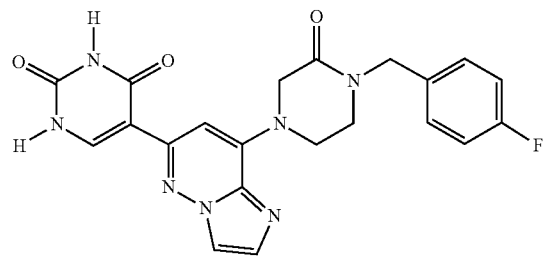 [SMILES: O=C1CN(c2cc(-c3c[nH]c(=O)[nH]c3=O)nn3ccnc23)CCN1Cc1ccc(F)cc1]

5-(8-(4-(4-fluorobenzyl)-3-oxopiperazin-1-yl)imidazo[1,2-b]pyridazin-6-yl)pyrimidine-2,4(1H,3H)-dione was prepared in the manner described for Example 476, but replacing 3-azabicyclo[3.2.0]heptane with 1-(4-fluorobenzyl)piperazin-2-one. ES/MS m/z: 436.1 [M+H]. $^1$H NMR (400 MHz, DMSO-d6) δ 11.44 (d, J=2.0 Hz, 1H), 11.40 (dd, J=6.2, 2.0 Hz, 1H), 8.08 (d, J=1.2 Hz, 1H), 7.96 (d, J=6.1 Hz, 1H), 7.58 (d, J=1.2 Hz, 1H), 7.35 (dd, J=8.6, 5.6 Hz, 2H), 7.23-7.13 (m, 2H), 6.90 (s, 1H), 4.59 (d, J=2.8 Hz, 4H), 4.37 (t, J=5.4 Hz, 2H), 3.50-3.40 (m, 2H).

Example 483. 5-(8-(azepan-1-yl)imidazo[1,2-b]pyridazin-6-yl)pyrimidine-2,4(1H,3H)-dione

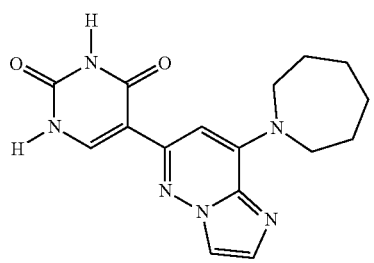 [SMILES: O=c1[nH]cc(-c2cc(N3CCCCCC3)c3nccn3n2)c(=O)[nH]1]

5-(8-(azepan-1-yl)imidazo[1,2-b]pyridazin-6-yl)pyrimidine-2,4(1H,3H)-dione was prepared in the manner described for Example 476, but replacing 3-azabicyclo[3.2.0]heptane with azepane. ES/MS m/z: 327.2 [M+H]. $^1$H NMR (400 MHz, DMSO-d6) δ 11.37 (d, J=2.0 Hz, 1H), 11.34 (d, J=6.6 Hz, 1H), 7.99 (d, J=1.1 Hz, 1H), 7.94 (d, J=6.1 Hz, 1H), 7.53 (d, J=1.2 Hz, 1H), 6.77 (s, 1H), 4.07 (s, 4H), 1.89-1.72 (m, 4H), 1.52 (p, J=2.7 Hz, 4H).

Example 484. 5-(8-(4,4-difluoro-5-methylazepan-1-yl)imidazo[1,2-b]pyridazin-6-yl)pyrimidine-2,4(1H,3H)-dione

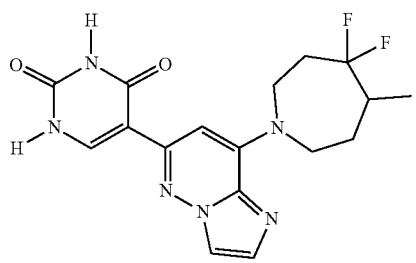 [SMILES: CC1CCN(c2cc(-c3c[nH]c(=O)[nH]c3=O)nn3ccnc23)CCC1(F)F]

5-(8-(4,4-difluoro-5-methylazepan-1-yl)imidazo[1,2-b]pyridazin-6-yl)pyrimidine-2,4(1H,3H)-dione was prepared in the manner described for Example 476, but replacing 3-azabicyclo[3.2.0]heptane with 4,4-difluoro-5-methylazepane. ES/MS m/z: 377.1 [M+H]. $^1$H NMR (400 MHz, DMSO-d6) δ 8.01 (d, J=1.2 Hz, 1H), 7.94 (s, 1H), 7.55 (d, J=1.2 Hz, 1H), 6.72 (s, 1H), 4.37-4.21 (m, 1H), 4.19-3.92 (m, 2H), 3.91-3.71 (m, 1H), 2.45-2.17 (m, 3H), 2.03-1.82 (m, 2H), 0.99 (d, J=6.9 Hz, 3H).

Example 485. 5-(8-((3-hydroxy-3-methylbutyl)amino)imidazo[1,2-b]pyridazin-6-yl)pyrimidine-2,4(1H,3H)-dione

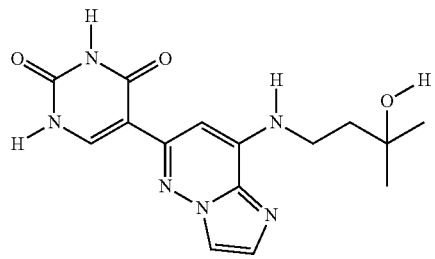 [SMILES: CC(C)(O)CCNc1cc(-c2c[nH]c(=O)[nH]c2=O)nn2ccnc12]

5-(8-((3-hydroxy-3-methylbutyl)amino)imidazo[1,2-b]pyridazin-6-yl)pyrimidine-2,4(1H,3H)-dione was prepared in the manner described for Example 476, but replacing 3-azabicyclo[3.2.0]heptane with 4-amino-2-methylbutan-2-ol. ES/MS m/z: 331.1 [M+H]. $^1$H NMR (400 MHz, DMSO-d6) δ 11.43 (s, 1H), 11.41 (d, J=8.1 Hz, 1H), 8.09 (s, 1H), 7.98 (d, J=6.1 Hz, 1H), 7.66 (s, 1H), 7.43 (t, J=4.2 Hz, 1H), 6.86 (s, 1H), 3.41-3.32 (m, 2H), 1.77 (dd, J=8.7, 6.4 Hz, 2H), 1.18 (s, 6H).

Example 486. 5-(8-((3-phenylpropyl)amino)imidazo[1,2-b]pyridazin-6-yl)pyrimidine-2,4(1H,3H)-dione

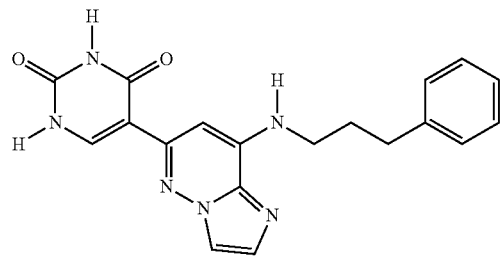 [SMILES: O=c1[nH]cc(-c2cc(NCCCc3ccccc3)c3nccn3n2)c(=O)[nH]1]

5-(8-((3-phenylpropyl)amino)imidazo[1,2-b]pyridazin-6-yl)pyrimidine-2,4(1H,3H)-dione was prepared in the manner described for Example 476, but replacing 3-azabicyclo[3.2.0]heptane with 3-phenylpropan-1-amine. ES/MS m/z: 363.2 [M+H]. $^1$H NMR (400 MHz, DMSO-d6) δ 11.50-11.27 (m, 2H), 8.12 (d, J=1.5 Hz, 1H), 7.96 (d, J=6.1 Hz, 1H), 7.72 (s, 1H), 7.53 (t, J=5.8 Hz, 1H), 7.32-7.22 (m, 4H), 7.22-7.16 (m, 1H), 6.84 (s, 1H), 3.38-3.27 (m, 2H), 2.77-2.65 (m, 2H), 1.97 (td, J=8.6, 8.1, 6.2 Hz, 2H).

Example 487. 5-(8-(phenethylamino)imidazo[1,2-b]pyridazin-6-yl)pyrimidine-2,4(1H,3H)-dione

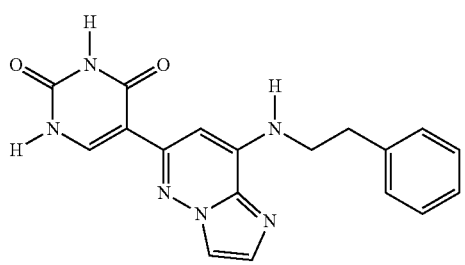 [SMILES: O=c1[nH]cc(-c2cc(NCCc3ccccc3)c3nccn3n2)c(=O)[nH]1]

5-(8-(phenethylamino)imidazo[1,2-b]pyridazin-6-yl)pyrimidine-2,4(1H,3H)-dione was prepared in the manner described for Example 476, but replacing 3-azabicyclo[3.2.0]heptane with 2-phenylethan-1-amine. ES/MS m/z: 349.1 [M+H]. ¹H NMR (400 MHz, DMSO-d6) δ11.43 (s, 1H), 11.39 (d, J=6.7 Hz, 1H), 8.05 (d, J=1.4 Hz, 1H), 7.97 (d, J=6.1 Hz, 1H), 7.59 (s, 1H), 7.46 (d, J=6.2 Hz, 1H), 7.32 (d, J=4.3 Hz, 4H), 7.23 (q, J=4.3 Hz, 1H), 6.91 (s, 1H), 2.98 (q, J=7.4, 7.0 Hz, 2H), 2.49 (m, 2H).

Example 488. tert-butyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate

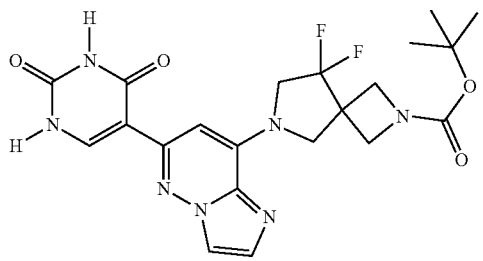 [SMILES: CC(C)(C)OC(=O)N1CC2(C1)CN(c1cc(-c3c[nH]c(=O)[nH]c3=O)nn3ccnc13)CC2(F)F]

tert-butyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate was prepared in the manner described for Example 476, but replacing 3-azabicyclo[3.2.0]heptane with tert-butyl 8,8-difluoro-2,6-diazaspiro[3.4]octane-2-carboxylate. ES/MS m/z: 475.9 [M+H]. ¹H NMR (400 MHz, DMSO-d6) δ 8.05 (d, J=1.2 Hz, 1H), 7.94 (s, 1H), 7.57 (d, J=1.2 Hz, 1H), 6.59 (s, 1H), 4.43 (s, 2H), 4.25 (s, 2H), 4.12-3.91 (m, 4H), 1.40 (s, 9H).

Example 489. 5-(8-((3-(trifluoromethyl)phenethyl)amino)imidazo[1,2-b]pyridazin-6-yl)pyrimidine-2,4(1H,3H)-dione

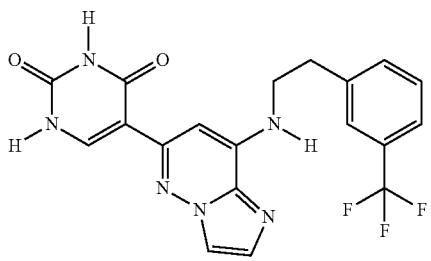 [SMILES: O=c1[nH]cc(-c2cc(NCCc3cccc(C(F)(F)F)c3)c3nccn3n2)c(=O)[nH]1]

5-(8-((3-(trifluoromethyl)phenethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2-(3-(trifluoromethyl)phenyl)ethan-1-amine. ES/MS m/z: 417.2 [M+H]. ¹H NMR (400 MHz, DMSO-d6+D2O) δ 8.13 (d, J=1.5 Hz, 1H), 7.98 (s, 1H), 7.73 (s, 1H), 7.68 (d, J=7.7 Hz, 1H), 7.62 (d, J=7.7 Hz, 1H), 7.60-7.49 (m, 2H), 6.96 (s, 1H), 3.62 (t, J=7.1 Hz, 2H), 3.08 (t, J=7.2 Hz, 2H). ¹⁹F NMR (376 MHz, DMSO-d6+D2O) δ −61.49, −74.74.

Example 490. 5-(8-((3-chlorophenethyl)amino)imidazo[1,2-b]pyridazin-6-yl)pyrimidine-2,4(1H,3H)-dione

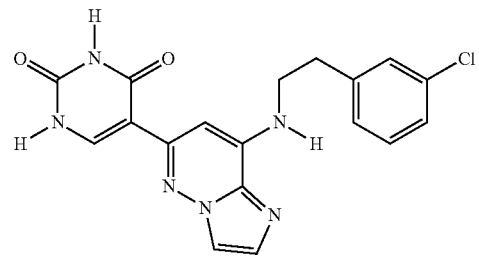 [SMILES: O=c1[nH]cc(-c2cc(NCCc3cccc(Cl)c3)c3nccn3n2)c(=O)[nH]1]

5-(8-((3-chlorophenethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2-(3-chlorophenyl)ethan-1-amine. ES/MS m/z: 383.2 [M+1-1]. ¹H NMR (400 MHz, DMSO-d6+D2O) δ 8.13 (s, 1H), 7.99 (s, 1H), 7.72 (s, 1H), 7.41 (t, J=1.8 Hz, 1H), 7.37-7.23 (m, 3H), 6.98 (s, 1H), 3.58 (t, J=7.4 Hz, 2H), 2.98 (t, J=7.3 Hz, 2H).

Example 491. 5-(8-((2-chlorophenethyl)amino)imidazo[1,2-b]pyridazin-6-yl)pyrimidine-2,4(1H,3H)-dione

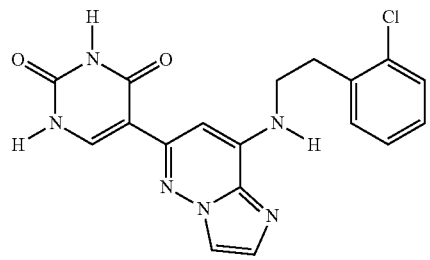

5-(8-((2-chlorophenethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2-(2-chlorophenyl)ethan-1-amine. ES/MS m/z: 383.1 [M+H]. ¹H NMR (400 MHz, DMSO-d6+D2O) δ 8.09 (s, 1H), 7.98 (s, 1H), 7.68 (s, 1H), 7.50-7.38 (m, 2H), 7.33-7.23 (m, 2H), 6.97 (s, 1H), 3.57 (t, J=7.6 Hz, 2H), 3.14-3.05 (m, 2H).

Example 492. 5-(8-((3-fluorophenethyl)amino)imidazo[1,2-b]pyridazin-6-yl)pyrimidine-2,4(1H,3H)-dione

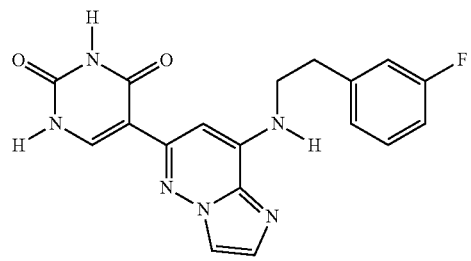 [SMILES: O=c1[nH]cc(-c2cc(NCCc3cccc(F)c3)c3nccn3n2)c(=O)[nH]1]

5-(8-((3-fluorophenethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2-(3-fluorophenyl)ethan-1-amine. ES/MS m/z: 367.2 [M+H]. ¹H NMR (400 MHz, DMSO-d6+D2O) δ 8.10 (s, 1H), 7.99 (s, 1H), 7.68 (s, 1H), 7.40-7.30 (m, 1H), 7.23-7.11 (m, 2H), 7.09-7.01 (m, 1H), 6.96 (s, 1H), 3.58 (t, J=7.5 Hz, 2H), 2.99 (t, J=7.4 Hz, 2H). ¹⁹F NMR (376 MHz, DMSO-d6+D2O) δ −74.59, −113.99-−114.12 (m)

Example 493. 5-(8-((2-fluorophenethyl)amino)imidazo[1,2-b]pyridazin-6-yl)pyrimidine-2,4(1H,3H)-dione

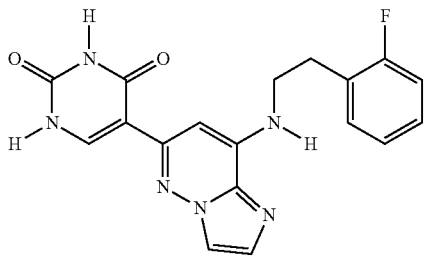

5-(8-((2-fluorophenethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2-(2-fluorophenyl)ethan-1-amine. ES/MS m/z: 367.2 [M+H]. ¹H NMR (400 MHz, DMSO-d6+D2O) δ 8.10 (s, 1H), 7.98 (s, 1H), 7.68 (s, 1H), 7.39 (t, J=7.7 Hz, 1H), 7.29 (q, J=6.2 Hz, 1H), 7.21-7.10 (m, 2H), 6.94 (s, 1H), 3.57 (t, J=7.5 Hz, 2H), 3.00 (t, J=7.3 Hz, 2H). ¹⁹F NMR (376 MHz, DMSO-d6+D2O) δ −74.56, −116.41-−121.72 (m).

Example 494. (S)-5-(8-((2-fluoro-2-phenylethyl)amino)imidazo[1,2-b]pyridazin-6-yl)pyrimidine-2,4(1H,3H)-dione

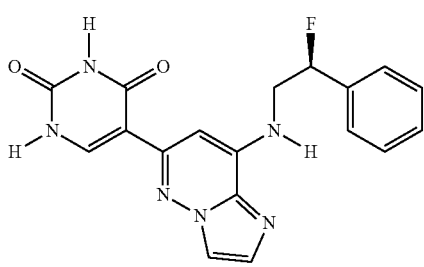 [SMILES: O=c1[nH]cc(-c2cc(NC[C@@H](F)c3ccccc3)c3nccn3n2)c(=O)[nH]1]

(S)-5-(8-((2-fluoro-2-phenylethyl)amino)imidazo[1,2-b]pyridazin-6-yl)pyrimidine-2,4(1H,3H)-dione was prepared in the manner described for Example 476, but replacing 3-azabicyclo[3.2.0]heptane with (S)-2-fluoro-2-phenylethan-1-amine. ES/MS m/z: 367.1 [M+H]. ¹H NMR (400 MHz, DMSO-d6+D2O) δ 8.11 (s, 1H), 7.98 (s, 1H), 7.69 (s, 1H), 7.56-7.36 (m, 5H), 7.00 (s, 1H), 5.96-5.75 (m, 1H), 3.97-3.73 (m, 2H).

Example 495. 5-(8-((2-(5-chloro-1H-indol-3-yl)ethyl)amino)imidazo[1,2-b]pyridazin-6-yl)pyrimidine-2,4(1H,3H)-dione

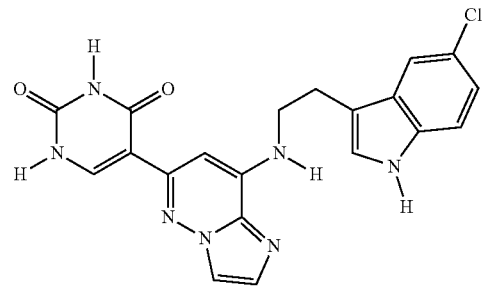 [SMILES: O=c1[nH]cc(-c2cc(NCCc3c[nH]c4ccc(Cl)cc34)c3nccn3n2)c(=O)[nH]1]

5-(8-((2-(5-chloro-1H-indol-3-yl)ethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2-(5-chloro-1H-indol-3-yl)ethan-1-amine. ES/MS m/z: 422.1 [M+H]. ¹H NMR (400 MHz, DMSO-d6+D2O) δ 8.04 (s, 1H), 7.94 (s, 1H), 7.64-7.62 (m, 1H), 7.58 (d, J=20.3 Hz, 2H), 7.42-7.29 (m, 3H), 7.17-7.02 (m, 1H), 6.83 (s, 1H), 3.65-3.54 (m, 2H), 3.06 (t, J=7.3 Hz, 2H).

Example 496. 5-(8-((4-fluorophenethyl)amino)imidazo[1,2-b]pyridazin-6-yl)pyrimidine-2,4(1H,3H)-dione

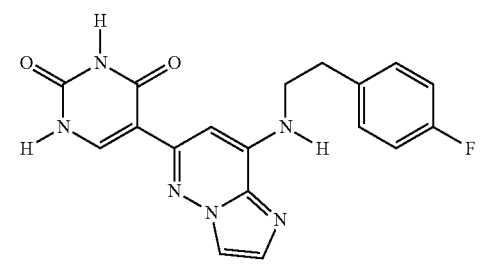 [SMILES: O=c1[nH]cc(-c2cc(NCCc3ccc(F)cc3)c3nccn3n2)c(=O)[nH]1]

5-(8-((4-fluorophenethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2-(4-fluorophenyl)ethan-1-amine. ES/MS m/z: 367.2 [M+H]. ¹H NMR (400 MHz, DMSO-d6+D2O) δ 8.07 (s, 1H), 7.98 (s, 1H), 7.64 (s, 1H), 7.34 (dd, J=8.6, 5.6 Hz, 2H), 7.12 (t, J=8.8 Hz, 2H), 6.91 (s, 1H), 3.53 (t, J=7.8 Hz, 2H), 2.95 (t, J=7.4 Hz, 2H). ¹⁹F NMR (376 MHz, DMSO-d6+D2O) δ −74.45, −117.41.

Example 497. 5-(8-((4-chlorophenethyl)amino)imidazo[1,2-b]pyridazin-6-yl)pyrimidine-2,4(1H,3H)-dione

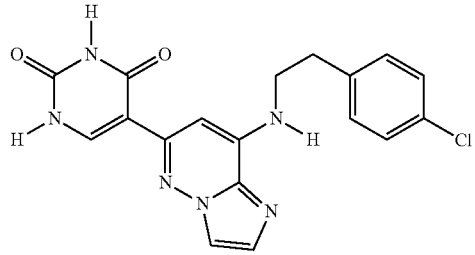 [SMILES: O=c1[nH]cc(-c2cc(NCCc3ccc(Cl)cc3)c3nccn3n2)c(=O)[nH]1]

5-(8-((4-chlorophenethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2-(4-chlorophenyl)ethan-1-amine. ES/MS m/z: 383.1 [M+H]. ¹H NMR (400 MHz, DMSO-d6+D2O) δ 8.03 (s, 1H), 7.96 (s, 1H), 7.59 (s, 1H), 7.40-7.28 (m, 4H), 6.84 (s, 1H), 3.54 (s, 2H), 2.95 (t, J=7.4 Hz, 2H).

Example 498. 5-(8-((2,2-difluoro-2-phenylethyl)amino)imidazo[1,2-b]pyridazin-6-yl)pyrimidine-2,4(1H,3H)-dione

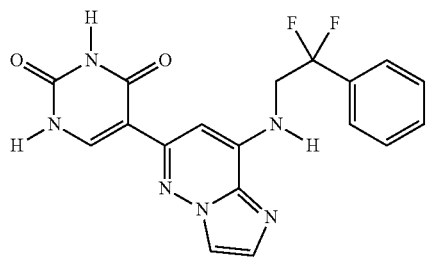 [SMILES: O=c1[nH]cc(-c2cc(NCC(F)(F)c3ccccc3)c3nccn3n2)c(=O)[nH]1]

5-(8-((2,2-difluoro-2-phenylethyl)amino)imidazo[1,2-b]pyridazin-6-yl)pyrimidine-2,4(1H,3H)-dione was prepared in the manner described for Example 476, but replacing 3-azabicyclo[3.2.0]heptane with 2,2-difluoro-2-phenylethan-1-amine. ES/MS m/z: 385.1 [M+H]. ¹H NMR (400 MHz, DMSO-d6+D2O) δ 8.13 (d, J=1.4 Hz, 1H), 7.96 (s, 1H), 7.71 (s, 1H), 7.64-7.57 (m, 2H), 7.56-7.48 (m, 3H), 7.09 (s, 1H), 4.35-4.11 (m, 2H). ¹⁹F NMR (376 MHz, DMSO-d6+D2O) δ -74.81, -99.32.

Example 499. (S)-5-(8-((2-phenylpropyl)amino)imidazo[1,2-b]pyridazin-6-yl)pyrimidine-2,4(1H,3H)-dione

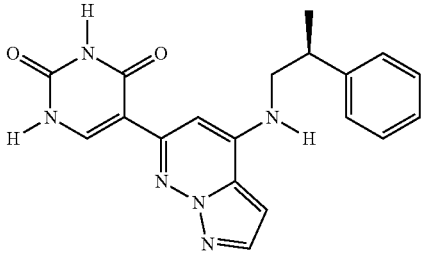 [SMILES: C[C@H](CNc1cc(-c2c[nH]c(=O)[nH]c2=O)nn2nccc12)c1ccccc1]

(S)-5-(8-((2-phenylpropyl)amino)imidazo[1,2-b]pyridazin-6-yl)pyrimidine-2,4(1H,3H)-dione was prepared in the manner described for Example 476, but replacing 3-azabicyclo[3.2.0]heptane with (S)-2-phenylpropan-1-amine. ES/MS m/z: 363.2 [M+H]. ¹H NMR (400 MHz, DMSO-d6+D2O) δ 8.11 (s, 1H), 7.99 (s, 1H), 7.70 (s, 1H), 7.37-7.28 (m, 4H), 7.26-7.18 (m, 1H), 6.99 (s, 1H), 3.57-3.44 (m, 2H), 3.22 (q, J=7.2 Hz, 1H), 1.29 (d, J=6.9 Hz, 3H).

Example 500. (R)-5-(8-((2-phenylpropyl)amino)imidazo[1,2-b]pyridazin-6-yl)pyrimidine-2,4(1H,3H)-dione

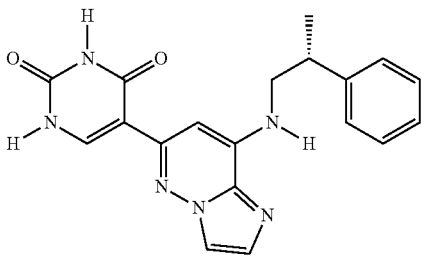 [SMILES: C[C@@H](CNc1cc(-c2c[nH]c(=O)[nH]c2=O)nn2ccnc12)c1ccccc1]

(R)-5-(8-((2-phenylpropyl)amino)imidazo[1,2-b]pyridazin-6-yl)pyrimidine-2,4(1H,3H)-dione was prepared in the manner described for Example 476, but replacing 3-azabicyclo[3.2.0]heptane with (R)-2-phenylpropan-1-amine. ES/MS m/z: 363.2 [M+1-1]. ¹H NMR (400 MHz, DMSO-d6+D2O) δ 8.11 (s, 1H), 7.99 (s, 1H), 7.70 (s, 1H), 7.37-7.28 (m, 4H), 7.26-7.18 (m, 1H), 6.99 (s, 1H), 3.57-3.44 (m, 2H), 3.22 (q, J=7.2 Hz, 1H), 1.29 (d, J=6.9 Hz, 3H).

Example 501. 5-(8-(8,8-difluoro-2,6-diazaspiro[3.4]octan-6-yl)imidazo[1,2-b]pyridazin-6-yl)pyrimidine-2,4(1H,3H)-dione

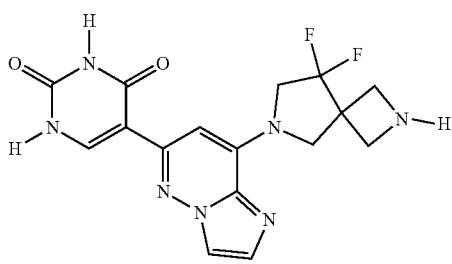 [SMILES: O=c1[nH]cc(-c2cc(N3CC(F)(F)C4(CNC4)C3)c3nccn3n2)c(=O)[nH]1]

To a suspension of tert-butyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate (148 mg, 0.31 mmol) in MeOH (2 mL) was added 4 M aq HCl (0.8 mL) and the reaction was stirred at 45° C. After 3 hours, the methanol was removed in vacuo and the remaining reaction was lyophilized. The resulting solids were rinsed with MeOH and dried in vacuo to afford 5-(8-(8,8-difluoro-2,6-diazaspiro[3.4]octan-6-yl)imidazo[1,2-b]pyridazin-6-yl)pyrimidine-2,4(1H,3H)-dione as a bis HCl salt. $^1$H NMR (400 MHz, DMSO-d6+D2O) δ 8.08 (d, J=1.2 Hz, 1H), 7.97 (s, 1H), 7.59 (d, J=1.2 Hz, 1H), 6.64 (s, 1H), 4.54-4.33 (m, 4H), 4.20 (app q, J=11.8 Hz, 4H). $^{19}$F NMR (376 MHz, DMSO-d6+D2O) δ −115.45. ES/MS m/z: 376.2 [M+H].

Example 502. 5-(8-(8,8-difluoro-2-(3-fluorobenzyl)-2,6-diazaspiro[3.4]octan-6-yl)imidazo[1,2-b]pyridazin-6-yl)pyrimidine-2,4(1H,3H)-dione

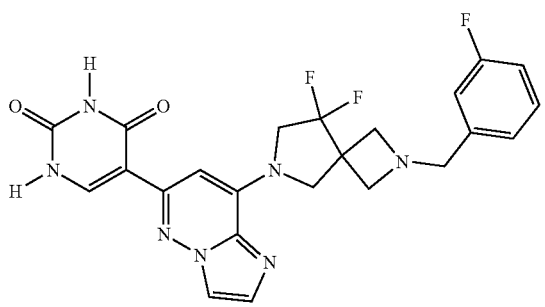 [SMILES: O=c1[nH]cc(-c2cc(N3CC(F)(F)C4(CN(Cc5cccc(F)c5)C4)C3)c3nccn3n2)c(=O)[nH]1]

To a suspension of 5-(8-(8,8-difluoro-2,6-diazaspiro[3.4]octan-6-yl)imidazo[1,2-b]pyridazin-6-yl)pyrimidine-2,4(1H,3H)-dione bis HCl (15 mg, 0.034 mmol), 3-fluorobenzaldehyde (12.5 mg, 0.10 mmol), and DIPEA (13 mg, 0.10 mmol) in DMF (0.5 mL) was added sodium triacetoxyborohydride (35.5 mg, 0.17 mmol). The reaction was warmed to 60° C. and stirred for 30 minutes. The mixture was cooled, diluted with water and TFA, and purified by RP-HPLC (MeCN/H$_2$O gradient with TFA modifier) affording 5-(8-(8,8-difluoro-2-(3-fluorobenzyl)-2,6-diazaspiro[3.4]octan-6-yl)imidazo[1,2-b]pyridazin-6-yl)pyrimidine-2,4(1H,3H)-dione as a TFA salt. $^1$H NMR (400 MHz, DMSO-d6) δ 8.08 (d, J=1.2 Hz, 1H), 7.97 (s, 1H), 7.58 (d, J=1.2 Hz, 1H), 7.53 (td, J=8.0, 6.1 Hz, 1H), 7.45-7.35 (m, 2H), 7.32 (td, J=8.6, 2.7 Hz, 1H), 6.64 (s, 1H), 4.64-4.15 (m, 10H). ES/MS m/z: 484.1 [M+H].

Example 503. 5-(8-(2-acetyl-8,8-difluoro-2,6-diazaspiro[3.4]octan-6-yl)imidazo[1,2-b]pyridazin-6-yl)pyrimidine-2,4(1H,3H)-dione

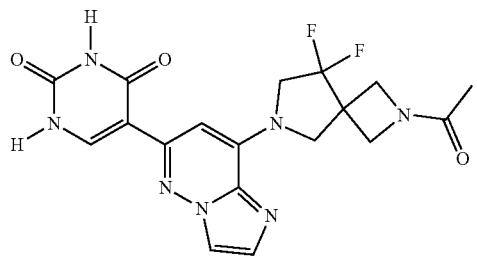 [SMILES: CC(=O)N1CC2(C1)CN(c1cc(-c3c[nH]c(=O)[nH]c3=O)nn3ccnc13)CC2(F)F]

To a solution of 5-(8-(8,8-difluoro-2,6-diazaspiro[3.4]octan-6-yl)imidazo[1,2-b]pyridazin-6-yl)pyrimidine-2,4(1H,3H)-dione bis HCl (15 mg, 0.034 mmol) and pyridine (21 mg, 0.27 mmol) in DCM (0.5 mL) was added acetic anhydride (20 mg, 0.10 mmol). The reaction was stirred at room temperature overnight. Additional acetic anhydride (20 mg, 0.10 mmol) was added and the reaction was stirred an additional 4 hours. The reaction was concentrated to dryness, treated with aq 1M LiOH (0.5 mL) and DMF (0.5 mL), stirred for 10 min, then diluted with TFA and purified by RP-HPLC (MeCN/H$_2$O gradient with TFA modifier) affording 5-(8-(2-acetyl-8,8-difluoro-2,6-diazaspiro[3.4]octan-6-yl)imidazo[1,2-b]pyridazin-6-yl)pyrimidine-2,4(1H,3H)-dione as a TFA salt. $^1$H NMR (400 MHz, DMSO-d6+D2O) δ 8.07 (d, J=1.2 Hz, 1H), 7.95 (s, 1H), 7.59 (d, J=1.2 Hz, 1H), 6.62 (s, 1H), 4.43 (t, J=13.1 Hz, 2H), 4.35 (d, J=9.3 Hz, 1H), 4.32-4.23 (m, 3H), 4.04 (d, J=10.3 Hz, 1H), 3.95 (d, J=10.3 Hz, 1H), 1.81 (s, 3H). ES/MS m/z: 418.2 [M+H].

Example 504. Methyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate

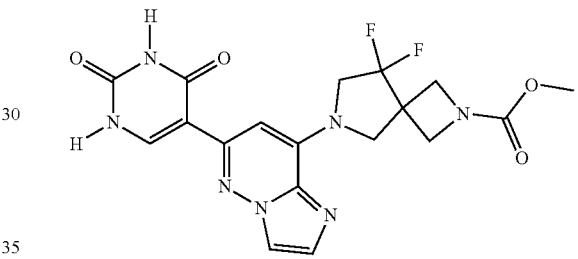

Methyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate was prepared in the manner described for Example 503, but replacing acetic anhydride with methyl chloroformate. $^1$H NMR (400 MHz, DMSO-d6+D2O) δ 8.06 (d, J=1.2 Hz, 1H), 7.94 (s, 1H), 7.57 (d, J=1.2 Hz, 1H), 6.60 (s, 1H), 4.53-4.32 (m, 2H), 4.26 (s, 2H), 4.13-4.00 (m, 4H), 3.59 (s, 3H). ES/MS m/z: 434.2 [M+H].

Example 505. benzyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate

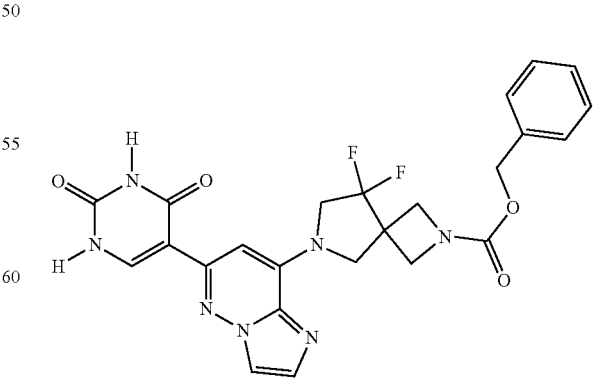

To a solution of 5-(8-(8,8-difluoro-2,6-diazaspiro[3.4]octan-6-yl)imidazo[1,2-b]pyridazin-6-yl)pyrimidine-2,4

(1H,3H)-dione bis HCl (7 mg, 0.016 mmol) and DIPEA (6 mg, 0.046 mmol) in DMF (0.3 mL) was added N-(Benzyloxycarbonyloxy)succinimide (4.9 mg, 0.020 mmol). After 30 min, the reaction was dilute with aq TFA, and purified by RP-HPLC (MeCN/H$_2$O gradient with TFA modifier) affording benzyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate as a TFA salt. $^1$H NMR (400 MHz, DMSO-d6+D2O) δ 8.08 (d, J=1.1 Hz, 1H), 7.95 (s, 1H), 7.59 (d, J=1.2 Hz, 1H), 7.41-7.30 (m, 5H), 6.62 (s, 1H), 5.08 (s, 2H), 4.53-4.36 (m, 2H), 4.28 (s, 2H), 4.14 (s, 4H). $^{19}$F NMR (376 MHz, DMSO-d6+D2O) δ −75.16, −116.95. ES/MS m/z: 510.1 [M+H].

Example 506. 2,2,2-trifluoroethyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate

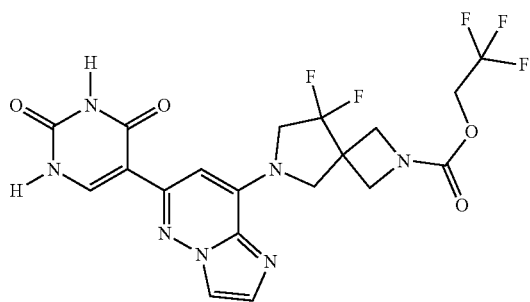 [SMILES: O=C(OCC(F)(F)F)N1CC2(C1)CN(c1cc(-c3c[nH]c(=O)[nH]c3=O)nn3ccnc13)CC2(F)F]

2,2,2-trifluoroethyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate was prepared in the manner described for Example 505, but replacing N-(Benzyloxycarbonyloxy)succinimide with N-(2,2,2-trifluoroethoxycarbonyloxy)succinimide. $^1$H NMR (400 MHz, DMSO-d6+D2O) δ 8.07 (d, J=1.2 Hz, 1H), 7.95 (s, 1H), 7.58 (d, J=1.2 Hz, 1H), 6.61 (s, 1H), 4.84-4.62 (m, 2H), 4.45 (s, 2H), 4.29 (s, 2H), 4.26-4.11 (m, 4H). ES/MS m/z: 502.2 [M+H].

Example 507. 5-(8-(2-(2,2-difluoroethyl)-8,8-difluoro-2,6-diazaspiro[3.4]octan-6-yl)imidazo[1,2-b]pyridazin-6-yl)pyrimidine-2,4(1H,3H)-dione

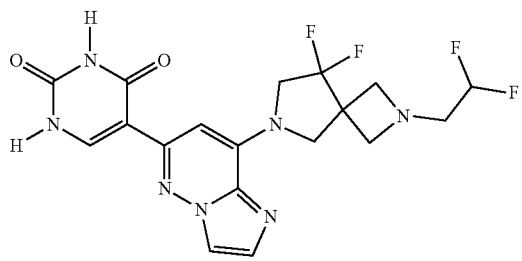 [SMILES: O=c1[nH]cc(-c2cc(N3CC(F)(F)C4(CN(CC(F)F)C4)C3)c3nccn3n2)c(=O)[nH]1]

To a solution of tert-butyl 8,8-difluoro-2,6-diazaspiro[3.4]octane-6-carboxylate (75 mg, 0.30 mmol) and DIPEA (87 mg, 0.67 mmol) in MeCN (0.5 mL) was added 2,2-difluoroethyl trifluoromethanesulfonate (97 mg, 0.45 mmol). The reaction was stirred at 40° C. for 20 min, then concentrated to dryness. The residue was treated with aq NH$_4$Cl (1 mL) and extracted into diethyl ether (1 mL). The organic fraction was dried over sodium sulfate, filter, and concentrated in vacuo. The resulting crude material was dissolved in DCM (1 mL) and treated with TFA (0.5 mL). After 10 min, the reaction was again concentrated to dryness. 5-(8-bromoimidazo[1,2-b]pyridazin-6-yl)-1H-pyrimidine-2,4-dione (116 mg, 0.34 mmol), DIPEA (0.16 g, 1.2 mmol), and NMP (0.6 mL) were added and the reaction was stirred at 130° C. for 2 hours. The reaction was cooled to rt and excess DIPEA was removed in vacuo. The reaction was diluted with water and TFA, and purified by RP-HPLC (MeCN/H$_2$O gradient with TFA modifier) affording 5-(8-(2-(2,2-difluoroethyl)-8,8-difluoro-2,6-diazaspiro[3.4]octan-6-yl)imidazo[1,2-b]pyridazin-6-yl)pyrimidine-2,4(1H,3H)-dione as a TFA salt. $^1$H NMR (400 MHz, DMSO-d6+D2O) δ 8.09 (d, J=1.2 Hz, 1H), 7.97 (s, 1H), 7.59 (d, J=1.2 Hz, 1H), 6.65 (s, 1H), 6.30 (tt, J=54.0, 3.5 Hz, 1H), 4.43 (s, 4H), 4.36 (d, J=11.1 Hz, 2H), 4.26 (d, J=10.9 Hz, 2H), 3.73 (t, J=15.1 Hz, 2H). ES/MS m/z: 440.2 [M+H].

Example 508. 5-(8-(8,8-difluoro-2-(2,2,2-trifluoroethyl)-2,6-diazaspiro[3.4]octan-6-yl)imidazo[1,2-b]pyridazin-6-yl)pyrimidine-2,4(1H,3H)-dione

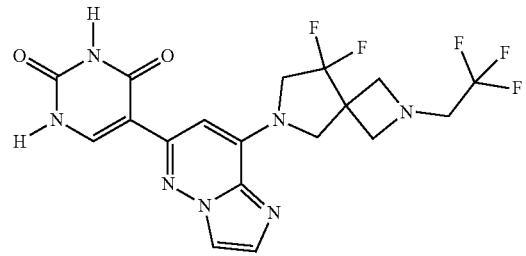 [SMILES: O=c1[nH]cc(-c2cc(N3CC(F)(F)C4(CN(CC(F)(F)F)C4)C3)c3nccn3n2)c(=O)[nH]1]

5-(8-(8,8-difluoro-2-(2,2,2-trifluoroethyl)-2,6-diazaspiro[3.4]octan-6-yl)imidazo[1,2-b]pyridazin-6-yl)pyrimidine-2,4(1H,3H)-dione was prepared in the manner described for Example 507, but replacing 2,2-difluoroethyl trifluoromethanesulfonate with 2,2,2-trifluoroethyl trifluoromethanesulfonate. $^1$H NMR (400 MHz, DMSO-d6+D2O) δ 8.08 (d, J=1.2 Hz, 1H), 7.95 (s, 1H), 7.59 (d, J=1.2 Hz, 1H), 6.62 (s, 1H), 4.35 (t, J=13.7 Hz, 2H), 4.27 (s, 2H), 3.68 (d, J=8.1 Hz, 2H), 3.53 (d, J=8.2 Hz, 2H), 3.35 (q, J=10.2 Hz, 2H). ES/MS m/z: 458.2 [M+H].

Example 509. 5-(8-(1-(difluoromethyl)-1H-pyrazol-4-yl)imidazo[1,2-b]pyridazin-6-yl)pyrimidine-2,4(1H,3H)-dione

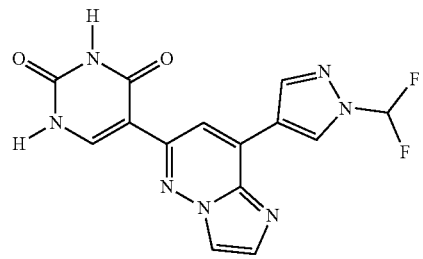 [SMILES: O=c1[nH]cc(-c2cc(-c3cnn(C(F)F)c3)c3nccn3n2)c(=O)[nH]1]

5-(8-bromoimidazo[1,2-b]pyridazin-6-yl)-1H-pyrimidine-2,4-dione (45 mg, 0.15 mmol), 1-(difluoromethyl)-4-

(4,4,5,5-tetramethyl-1,3,2-dioxaborolan-2-yl)-1H-pyrazole (71 mg, 0.29 mmol), potassium carbonate (40 mg, 0.29 mmol), and [1,1'-Bis(diphenylphosphino)ferrocene]palladium(II) dichloride (5.4 mg, 0.0073 mmol) were combined in DMF:water (3:1, 0.5 mL), degassed with argon, and stirred at 120° C. for 20 minutes. The mixture was cooled, diluted with water (0.5 mL) and MeCN (0.5 mL) and the precipitated product was collected by filtration. $^1$H NMR (400 MHz, DMSO-d6) δ 9.96 (d, J=66.7 Hz, 1H), 9.31 (s, 1H), 8.63 (s, 1H), 8.36 (s, 1H), 8.32 (s, 1H), 8.20 (d, J=1.2 Hz, 1H), 7.99 (t, J=58.8 Hz, 1H), 7.70 (d, J=1.2 Hz, 1H). ES/MS m/z: 346.1 [M+H].

Example 510. 5-(8-(1-(2-methoxyethyl)-1H-pyrazol-4-yl)imidazo[1,2-b]pyridazin-6-yl)pyrimidine-2,4(1H,3H)-dione

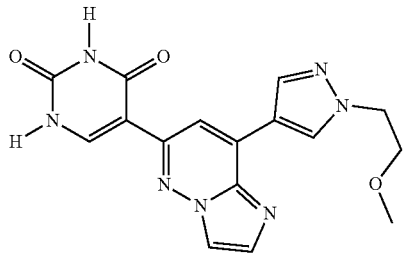 [SMILES: COCCn1cc(-c2cc(-c3c[nH]c(=O)[nH]c3=O)nn3ccnc23)cn1]

5-(8-(1-(2-methoxyethyl)-1H-pyrazol-4-yl)imidazo[1,2-b]pyridazin-6-yl)pyrimidine-2,4(1H,3H)-dione was prepared in the manner described for Example 509, but replacing 1-(difluoromethyl)-4-(4,4,5,5-tetramethyl-1,3,2-dioxaborolan-2-yl)-1H-pyrazole with (1-(2-methoxyethyl)-1H-pyrazol-4-yl)boronic acid. The desired product was purified by RP-HPLC (MeCN/H$_2$O gradient with TFA modifier). $^1$H NMR (400 MHz, DMSO-d6) δ 11.53 (d, J=1.8 Hz, 1H), 11.49 (d, J=6.6 Hz, 1H), 8.87 (s, 1H), 8.43 (s, 1H), 8.28 (d, J=1.2 Hz, 1H), 8.02 (d, J=6.1 Hz, 1H), 7.91 (s, 1H), 7.80 (d, J=1.2 Hz, 1H), 4.41 (t, J=5.2 Hz, 2H), 3.75 (t, J=5.2 Hz, 2H), 3.26 (s, 3H). ES/MS m/z: 354.2 [M+H].

Example 511. 5-(8-(1-(2-morpholinoethyl)-1H-pyrazol-4-yl)imidazo[1,2-b]pyridazin-6-yl)pyrimidine-2,4(1H,3H)-dione

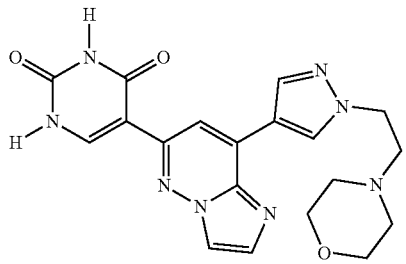 [SMILES: O=c1[nH]cc(-c2cc(-c3cnn(CCN4CCOCC4)c3)c3nccn3n2)c(=O)[nH]1]

5-(8-(1-(2-morpholinoethyl)-1H-pyrazol-4-yl)imidazo[1,2-b]pyridazin-6-yl)pyrimidine-2,4(1H,3H)-dione was prepared in the manner described for Example 509, but replacing 1-(difluoromethyl)-4-(4,4,5,5-tetramethyl-1,3,2-dioxaborolan-2-yl)-1H-pyrazole with 4-(2-(4-(4,4,5,5-tetramethyl-1,3,2-dioxaborolan-2-yl)-1H-pyrazol-1-yl)ethyl)morpholine. The desired product was purified by RP-HPLC (MeCN/H$_2$O gradient with TFA modifier). $^1$H NMR (400 MHz, DMSO-d6) δ 11.54 (s, 2H), 11.52 (s, 1H), 9.06 (s, 1H), 8.53 (s, 1H), 8.30 (d, J=1.2 Hz, 1H), 8.03 (d, J=6.0 Hz, 1H), 7.96 (s, 1H), 7.81 (d, J=1.2 Hz, 1H), 4.72 (t, J=6.4 Hz, 2H), 4.17-3.90 (m, 4H), 3.19 (s, 4H). ES/MS m/z: 409.2 [M+H].

Example 512. 5-(8-(1-methyl-1H-pyrazol-3-yl)imidazo[1,2-b]pyridazin-6-yl)pyrimidine-2,4(1H,3H)-dione

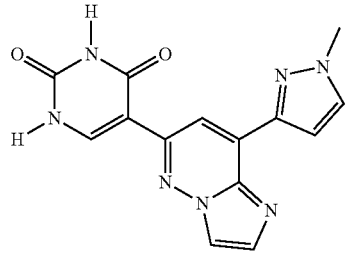 [SMILES: Cn1ccc(-c2cc(-c3c[nH]c(=O)[nH]c3=O)nn3ccnc23)n1]

5-(8-bromoimidazo[1,2-b]pyridazin-6-yl)-1H-pyrimidine-2,4-dione (20 mg, 0.065 mmol), 1-methyl-3-(tributylstannyl)-1H-pyrazole (48 mg, 0.13 mmol), cesium carbonate (42 mg, 0.13 mmol), and [1,1'-Bis(diphenylphosphino)ferrocene]palladium(II) dichloride (2.4 mg, 0.0033 mmol) were combined in DMF (0.3 mL), degassed with argon, and stirred at 110° C. for 3 hours. The mixture was cooled, rinsed with hexanes (2×1 mL), diluted with water and TFA and purified by RP-HPLC (MeCN/H$_2$O gradient with TFA modifier) affording 5-(8-(1-methyl-1H-pyrazol-3-yl)imidazo[1,2-b]pyridazin-6-yl)pyrimidine-2,4(1H,3H)-dione as a TFA salt. $^1$H NMR (400 MHz, DMSO-d6) δ 11.57 (d, J=4.7 Hz, 2H), 8.41 (s, 1H), 8.36 (s, 1H), 8.09 (d, J=6.3 Hz, 1H), 7.94 (d, J=2.3 Hz, 2H), 7.52 (d, J=2.3 Hz, 1H), 4.03 (s, 3H). ES/MS m/z: 310.1 [M+H].

Example 513. 5-(8-(4,4-dimethyl-2-oxopyrrolidin-1-yl)imidazo[1,2-b]pyridazin-6-yl)pyrimidine-2,4(1H,3H)-dione

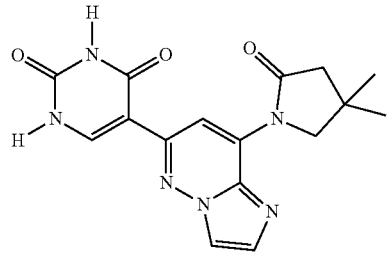 [SMILES: CC1(C)CC(=O)N(c2cc(-c3c[nH]c(=O)[nH]c3=O)nn3ccnc23)C1]

5-(8-bromoimidazo[1,2-b]pyridazin-6-yl)-1H-pyrimidine-2,4-dione (25 mg, 0.081 mmol), 4,4-dimethylpyrrolidin-2-one (18 mg, 0.16 mmol), cesium carbonate (79 mg, 0.24 mmol), and Xantphos Pd G3 (3.9 mg, 0.0041 mmol) were combined in DMF (0.5 mL), degassed with argon, and stirred at 110° C. for 2 hours. The mixture was cooled, diluted with water and TFA and purified by RP-HPLC (MeCN/H$_2$O gradient with TFA modifier) affording 5-(8-(4,4-dimethyl-2-oxopyrrolidin-1-yl)imidazo[1,2-b]pyridazin-6-yl)pyrimidine-2,4(1H,3H)-dione as a TFA salt. $^1$H NMR (400 MHz, DMSO-d6) δ 11.56-11.52 (m, 1H), 11.51 (s, 1H), 8.36 (s, 1H), 8.33 (d, J=1.3 Hz, 1H), 8.03 (d, J=6.1 Hz, 1H), 7.82 (d, J=1.3 Hz, 1H), 4.25 (s, 2H), 2.46 (s, 2H), 1.21 (s, 6H). ES/MS m/z: 341.2 [M+H].

Example 514. 5-(8-(5,5-dimethyl-2-oxooxazolidin-3-yl)imidazo[1,2-b]pyridazin-6-yl)pyrimidine-2,4(1H,3H)-dione

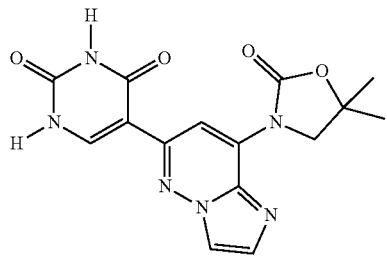 [SMILES: CC1(C)CN(c2cc(-c3c[nH]c(=O)[nH]c3=O)nn3ccnc23)C(=O)O1]

5-(8-(5,5-dimethyl-2-oxooxazolidin-3-yl)imidazo[1,2-b]pyridazin-6-yl)pyrimidine-2,4(1H,3H)-dione was prepared in the manner described for Example 513, but replacing 4,4-dimethylpyrrolidin-2-one with 5,5-dimethyloxazolidin-2-one. ¹H NMR (400 MHz, DMSO-d6) δ11.49 (d, J=4.8 Hz, 2H), 8.37 (s, 1H), 8.29 (d, J=1.2 Hz, 1H), 8.00 (d, J=6.3 Hz, 1H), 7.74 (d, J=1.2 Hz, 1H), 4.64 (s, 2H), 1.53 (s, 6H). ES/MS m/z: 343.1 [M+H].

Example 515. 5-(2,3-dichloro-8-(3,3-difluoro-4,4-dimethylpyrrolidin1-yl)imidazo[1,2-b]pyridazin-6-yl)pyrimidine-2,4(1H,3H)-dione

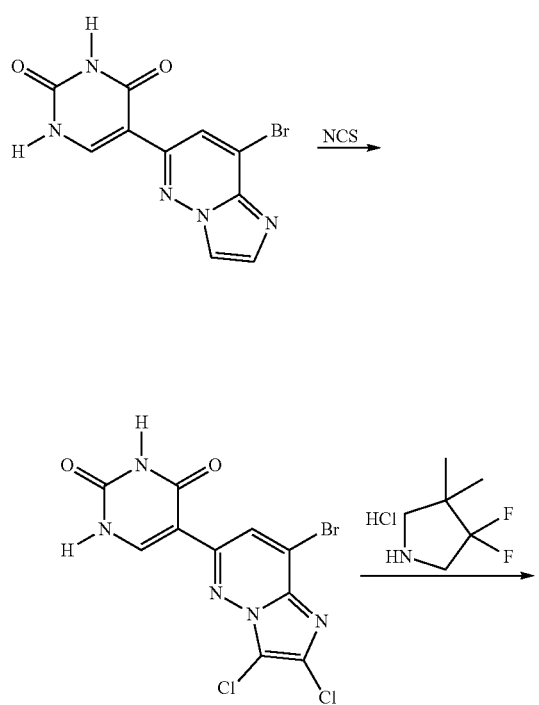

-continued

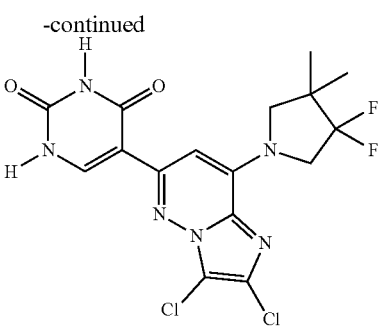

5-(8-bromoimidazo[1,2-b]pyridazin-6-yl)-1H-pyrimidine-2,4-dione (72 mg, 0.23 mmol) and N-chlorosuccinimide (53 mg, 0.40 mmol) were combined in DMF (1 mL) and stirred overnight at 50° C. The mixture was quenched with aq Na₂S₂O₃ (0.3 mL), stirred for 15 min, then diluted with additional water (1 mL). was added and the mixture was stirred at room temperature for 30 minutes. 5-(8-bromo-2,3-dichloro-imidazo[1,2-b]pyridazin-6-yl)-1H-pyrimidine-2,4-dione was collected by filtration and dried in vacuo. ¹H NMR (400 MHz, DMSO-d6+D2O) δ 8.30 (s, 1H), 8.12 (s, 1H). ES/MS m/z: 377.9 [M+H].

The resulting solids were combined with 3,3-difluoro-4,4-dimethyl-pyrrolidine hydrochloride (37 mg, 0.22 mmol), DIPEA (0.1 mL, 0.58 mmol), and NMP (0.5 mL) and stirred at 120° C. for 25 minutes. The mixture was cooled to room temperature and diluted with water and TFA. The precipitated solids were collected, dissolved in DMF and purified by RP-HPLC (MeCN/H₂O gradient with TFA modifier) affording 5-(2,3-dichloro-8-(3,3-difluoro-4,4-dimethylpyrrolidin-1-yl)imidazo[1,2-b]pyridazin-6-yl)pyrimidine-2,4(1H,3H)-dione. ¹H NMR (400 MHz, DMSO-d6) δ 11.63-11.35 (m, 2H), 8.01 (d, J=6.2 Hz, 1H), 6.82 (s, 1H), 4.36 (s, 2H), 3.84 (s, 2H), 1.21 (s, 6H). ES/MS m/z: 431.1 [M+H].

Examples 516 and 517. (S)-5-(8-(3,3-difluoro-4-methylpyrrolidin-1-yl)imidazo[1,2-b]pyridazin-6-yl)pyrimidine-2,4(1H,3H)-dione and (R)-5-(8-(3,3-difluoro-4-methylpyrrolidin-1-yl)imidazo[1,2-b]pyridazin-6-yl)pyrimidine-2,4(1H,3H)-dione

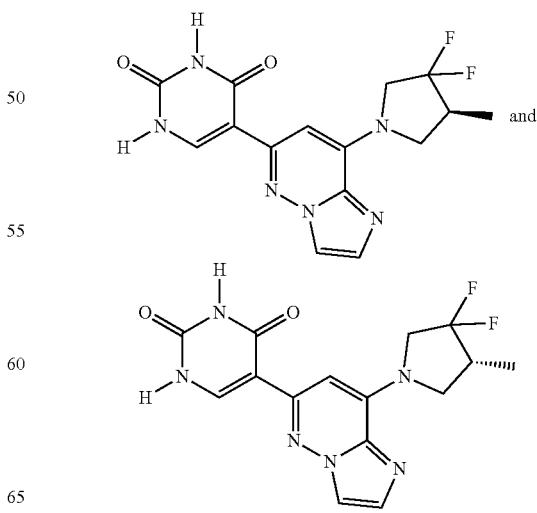

Rac-5-(8-(3,3-difluoro-4-methylpyrrolidin-1-yl)imidazo[1,2-b]pyridazin-6-yl)pyrimidine-2,4(1H,3H)-dione was prepared in the manner described for Example 476, then separated by chiral SFC chromatography (AD-H column, 30% EtOH cosolvent) affording enantiomers (S)-5-(8-(3,3-difluoro-4-methylpyrrolidin-1-yl)imidazo[1,2-b]pyridazin-6-yl)pyrimidine-2,4(1H,3H)-dione and (R)-5-(8-(3,3-difluoro-4-methylpyrrolidin-1-yl)imidazo[1,2-b]pyridazin-6-yl)pyrimidine-2,4(1H,3H)-dione. $^1$H NMR (400 MHz, DMSO-d6) δ11.41 (d, J=1.9 Hz, 1H), 11.40-11.30 (m, 1H), 8.06 (d, J=1.2 Hz, 1H), 7.94 (d, J=6.1 Hz, 1H), 7.58 (d, J=1.2 Hz, 1H), 6.60 (s, 1H), 4.53-4.17 (m, 4H), 2.85 (dq, J=17.7, 8.9, 8.1 Hz, 1H), 1.15 (d, J=6.9 Hz, 3H). ES/MS m/z: 349.2 [M+H].

Example 518 and 519

(S)-5-(8-(3,3-difluoro-4-methylpyrrolidin-1-yl)-3-fluoroimidazo[1,2-b]pyridazin-6-yl)pyrimidine-2,4(1H,3H)-dione and (R)-5-(8-(3,3-difluoro-4-methylpyrrolidin-1-yl)-3-fluoroimidazo[1,2-b]pyridazin-6-yl)pyrimidine-2,4(1H,3H)-dione 80° C. for 35 minutes. The mixture was cooled, diluted with water, and extracted into DCM. The organic layer was rinsed with aq NH$_4$Cl and brine, dried over Na$_2$SO$_4$, and concentrated in vacuo affording 6-chloro-8-(3,3-difluoro-4-methylpyrrolidin-1-yl)-3-fluoroimidazo[1,2-b]pyridazine. $^1$H NMR (400 MHz, Chloroform-d) δ 7.17 (d, J=7.2 Hz, 1H), 5.76 (s, 1H), 4.31 (s, 3H), 3.66 (s, 1H), 2.73 (tt, J=16.3, 8.1 Hz, 1H), 1.28-1.20 (m, 3H). $^{19}$F NMR (376 MHz, Chloroform-d) δ −110.09 (q, J=9.6 Hz), −110.71 (td, J=9.9, 6.9 Hz), −152.96 (d, J=7.2 Hz). ES/MS m/z: 291.2 [M+H].

6-chloro-8-(3,3-difluoro-4-methylpyrrolidin-1-yl)-3-fluoroimidazo[1,2-b]pyridazine (291 mg, 0.88 mmol), (2,4-di-tert-butoxypyrimidin-5-yl)boronic acid (483 mg, 1.8 mmol), potassium carbonate (335 mg, 2.42 mmol), and [1,1'-Bis(diphenylphosphino)ferrocene]palladium(II) dichloride (52 mg, 0.07 mmol) were combined in dioxane:water (5:1, 5 mL), degassed with argon, and stirred at 105° C. for 3 hours. The reaction was cooled, and additional (2,4-di-tert-butoxypyrimidin-5-yl)boronic acid (483 mg, 1.8 mmol), potassium carbonate (335 mg, 2.42 mmol), and [1,1'-Bis(diphenylphosphino)ferrocene]palladium(II) dichloride (52 mg, 0.07 mmol) were added. The reaction was degassed with

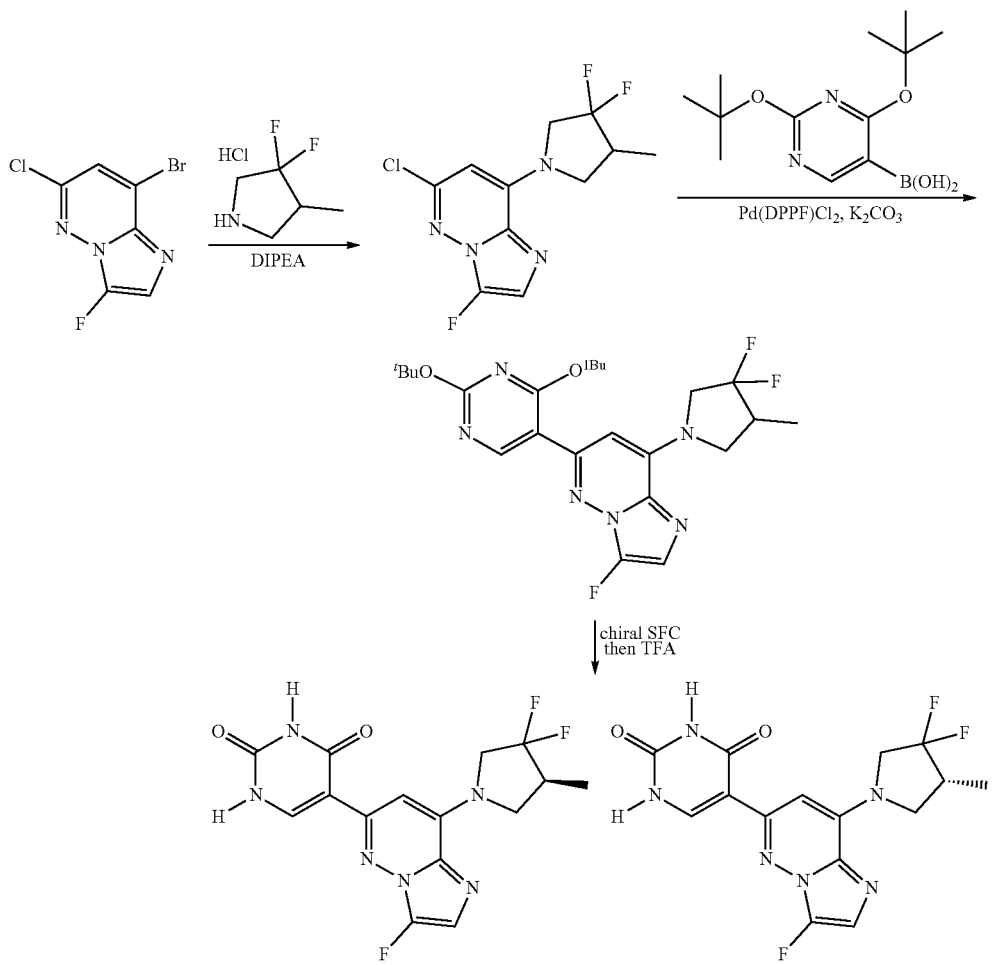

8-bromo-6-chloro-3-fluoro-imidazo[1,2-b]pyridazine (220 mg, 0.88 mmol), 3,3-difluoro-4-methyl-pyrrolidine hydrochloride (159 mg, 1.0 mmol), and DIPEA (0.46 mL, 2.6 mmol) were combined in MeCN (2 mL) and stirred at argon, and stirring was continued at 105° C. for 1.5 hours. The reaction was cooled, diluted with EtOAc, rinsed with brine, dried over Na$_2$SO$_4$, and concentrated in vacuo. The residue was purified by flash column chromatography (3%

EtOAc in hexanes 4-20% EtOAc in hexanes) to provide 6-(2,4-di-tert-butoxypyrimidin-5-yl)-8-(3,3-difluoro-4-methylpyrrolidin-1-yl)-3-fluoroimidazo[1,2-b]pyridazine. ¹H NMR (400 MHz, Chloroform-d) δ8.69 (s, 1H), 7.19 (d, J=7.2 Hz, 1H), 6.22 (s, 1H), 4.60-4.14 (m, 3H), 3.70-3.56 (m, 1H), 2.74 (tt, J=16.2, 8.1 Hz, 1H), 1.69 (s, 9H), 1.68 (s, 9H), 1.27 (d, J=6.8 Hz, 3H). ES/MS m/z: 479.1 [M+H].

The enantiomers of 6-(2,4-di-tert-butoxypyrimidin-5-yl)-8-(3,3-difluoro-4-methylpyrrolidin-1-yl)-3-fluoroimidazo[1,2-b]pyridazine were then separated by chiral SFC chromatography (AD-H column, 5% EtOH-NH₃ cosolvent) and treated with TFA (0.2 mL) in DCM/MeCN (1:1, 1 mL). After 30 minutes, the reaction was concentrated to provide enantiomers (S)-5-(8-(3,3-difluoro-4-methylpyrrolidin-1-yl)-3-fluoroimidazo[1,2-b]pyridazin-6-yl)pyrimidine-2,4(1H,3H)-dione and (R)-5-(8-(3,3-difluoro-4-methylpyrrolidin-1-yl)-3-fluoroimidazo[1,2-b]pyridazin-6-yl)pyrimidine-2,4(1H,3H)-dione. ¹H NMR (400 MHz, DMSO-d6) δ 11.44 (s, 1H), 11.41 (d, J=6.7 Hz, 1H), 7.97 (d, J=6.1 Hz, 1H), 7.41 (d, J=7.2 Hz, 1H), 6.60 (s, 1H), 4.32 (s, 1H), 3.80 (s, 2H), 3.52 (s, 1H), 2.86 (dt, J=18.0, 8.9 Hz, 1H), 1.15 (d, J=6.8 Hz, 3H). ¹⁹F NMR (376 MHz, DMSO-d6) δ −109.94 (d, J=225.7 Hz), −113.75 (d, J=222.6 Hz), −155.51 (d, J=7.3 Hz). ES/MS m/z: 367.2 [M+H].

Example 520 and 521

(S)-5-(3-chloro-8-(3,3-difluoro-4-methylpyrrolidin-1-yl)imidazo[1,2-b]pyridazin-6-yl)pyrimidine-2,4 (1H,3H)-dione and (R)-5-(3-chloro-8-(3,3-difluoro-4-methylpyrrolidin-1-yl)imidazo[1,2-b]pyridazin-6-yl)pyrimidine-2,4(1H,3H)-dione

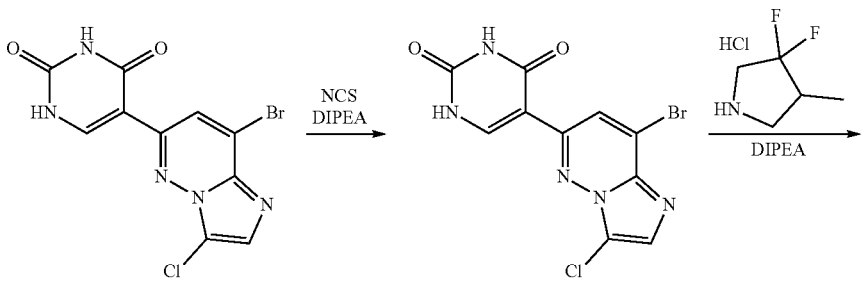

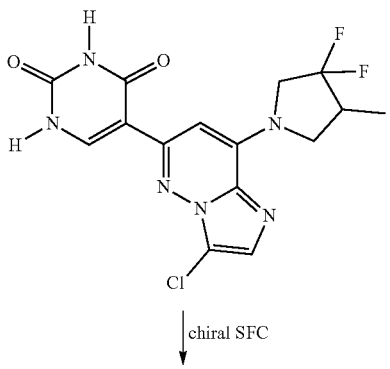

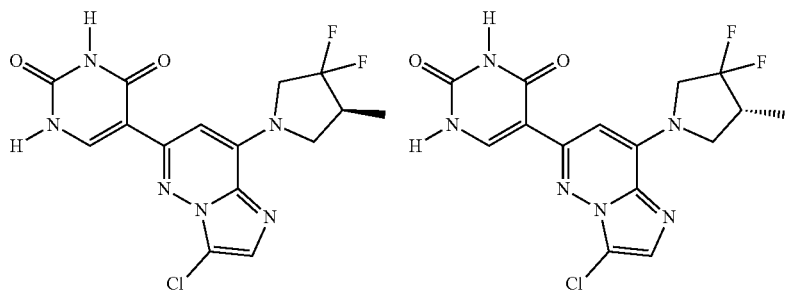

5-(8-bromoimidazo[1,2-b]pyridazin-6-yl)-1H-pyrimidine-2,4-dione hydrochloride (72 mg, 0.21 mmol) and DIPEA (0.23 mL, 1.3 mmol) were combined in DMF (1 mL). N-chlorosuccinimide (27 mg, 0.20 mmol) was added and the reaction was stirred overnight room temperature. An additional aliquot of N-chlorosuccinimide (27 mg, 0.20 mmol) was added, and stirring was continued at 30° C. for 6 hours. The reaction was quenched with aq $Na_2S_2O_3$ (0.3 mL), stirred for 2 min, then diluted with additional water (1 mL) and stirred at room temperature for 10 minutes. 5-(8-bromo-3-chloro-imidazo[1,2-b]pyridazin-6-yl)-1H-pyrimidine-2,4-dione was collected by filtration and dried in vacuo. $^1$H NMR (400 MHz, DMSO-d6+D2O) δ 8.22 (s, 1H), 8.11 (s, 1H), 7.97 (s, 1H). ES/MS m/z: 344.0 [M+H].

5-(8-bromo-3-chloro-imidazo[1,2-b]pyridazin-6-yl)-1H-pyrimidine-2,4-dione (49 mg, 0.10 mmol), 3,3-difluoro-4-methyl-pyrrolidine hydrochloride (36 mg, 0.23 mmol), and DIPEA (0.09 mL, 0.50 mmol) were combined in NMP (0.5 mL) and stirred at 125° C. for 3 hours. The mixture was cooled, diluted with water and TFA, the purified by RP-HPLC (MeCN/$H_2O$ gradient with TFA modifier) affording 5-(8-(3,3-difluoro-4-methylpyrrolidin-1-yl)-3-chloroimidazo[1,2-b]pyridazin-6-yl)pyrimidine-2,4(1H,3H)-dione. $^1$H NMR (400 MHz, DMSO-d6+D2O) δ 8.00 (s, 1H), 7.70 (s, 1H), 6.70 (s, 1H), 4.61-4.16 (m, 3H), 3.52 (s, 1H), 2.94 2.79 (m, 1H), 1.15 (d, J=6.8 Hz, 3H). ES/MS m/z: 383.2 [M+H].

The enantiomers of 5-(8-(3,3-difluoro-4-methylpyrrolidin-1-yl)-3-chloroimidazo[1,2-b]pyridazin-6-yl)pyrimidine-2,4(1H,3H)-dione were then separated by chiral SFC chromatography (AD-H column, 35% EtOH-TFA cosolvent) and purified by RP-HPLC (MeCN/$H_2O$ gradient with TFA modifier) affording enantiomers (S)-5-(3-chloro-8-(3,3-difluoro-4-methylpyrrolidin-1-yl)imidazo[1,2-b]pyridazin-6-yl)pyrimidine-2,4(1H,3H)-dione and (R)-5-(3-chloro-8-(3,3-difluoro-4-methylpyrrolidin-1-yl)imidazo[1,2-b]pyridazin-6-yl)pyrimidine-2,4(1H,3H)-dione. $^1$H NMR (400 MHz, DMSO-d6+D2O) δ 8.00 (s, 1H), 7.70 (s, 1H), 6.70 (s, 1H), 4.61-4.16 (m, 3H), 3.52 (s, 1H), 2.94-2.79 (m, 1H), 1.15 (d, J=6.8 Hz, 3H). ES/MS m/z: 383.2 [M+H].

Example 522. 5-(3-chloro-8-(3,3-difluoro-4,4-dimethylpyrrolidin-1-yl)imidazo[1,2-b]pyridazin-6-yl)pyrimidine-2,4(1H,3H)-dione

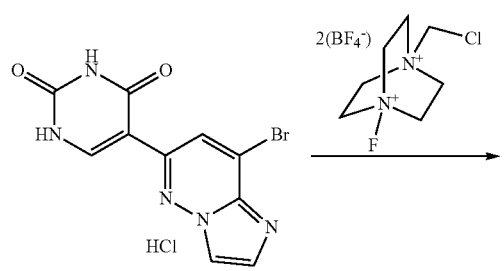

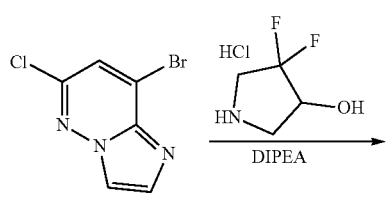

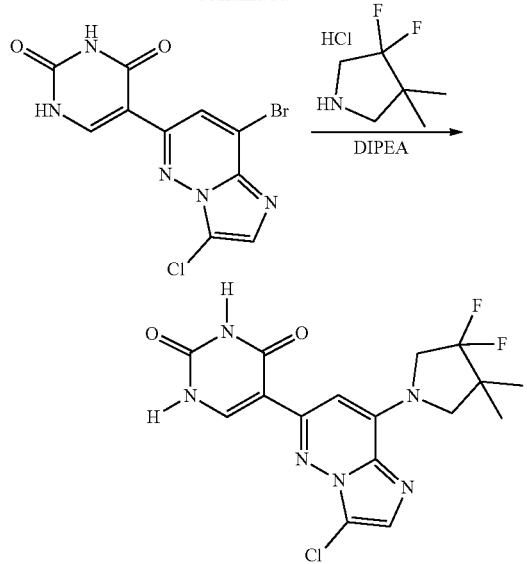

5-(8-bromoimidazo[1,2-b]pyridazin-6-yl)-1H-pyrimidine-2,4-dione hydrochloride (50 mg, 0.16 mmol) was combined with N-Fluoro-N'-chloromethyltriethylenediamine bis(tetrafluoroborate) (115 mg, 0.32 mmol) in DMF and the reaction was stirred at 50° C. for 30 minutes. The reaction was quenched with aq Na2S2O3 (0.3 mL), stirred for 15 min, then diluted with additional water (1 mL) and stirred at room temperature for 10 minutes. 5-(8-bromo-3-chloro-imidazo[1,2-b]pyridazin-6-yl)-1H-pyrimidine-2,4-dione was collected by filtration and dried in vacuo. $^1$H NMR (400 MHz, DMSO-d6) δ 11.62 (s, 2H), 8.24 (s, 1H), 8.11 (s, 1H), 7.98 (s, 1H). $^1$H NMR (400 MHz, DMSO-d6+D2O) δ 8.22 (s, 1H), 8.12 (s, 1H), 7.97 (s, 1H). ES/MS m/z: 344.0 [M+H].

5-(8-bromo-3-chloro-imidazo[1,2-b]pyridazin-6-yl)-1H-pyrimidine-2,4-dione (36 mg, 0.11 mmol), 3,3-difluoro-4,4-dimethyl-pyrrolidine hydrochloride (27 mg, 0.16 mmol), and DIPEA (0.04 mL, 0.21 mmol) were combined in NMP (0.5 mL) and stirred at 120° C. for 1 hour. The mixture was cooled, diluted with water and TFA, the purified by RP-HPLC (MeCN/$H_2O$ gradient with TFA modifier) affording 5-(3-chloro-8-(3,3-difluoro-4,4-dimethylpyrrolidin-1-yl)imidazo[1,2-b]pyridazin-6-yl)pyrimidine-2,4(1H,3H)-dione. $^1$H NMR (400 MHz, DMSO-d6) δ7.99 (s, 1H), 7.69 (s, 1H), 6.67 (s, 1H), 4.39 (s, 2H), 3.85 (s, 2H), 1.20 (s, 6H). ES/MS m/z: 397.2 [M+H].

Example 523. 5-(8-(3,3-difluoro-4-((5-(trifluoromethyl)pyridin-2-yl)oxy)pyrrolidin-1-yl)imidazo[1,2-b]pyridazin-6-yl)pyrimidine-2,4(1H,3H)-dione

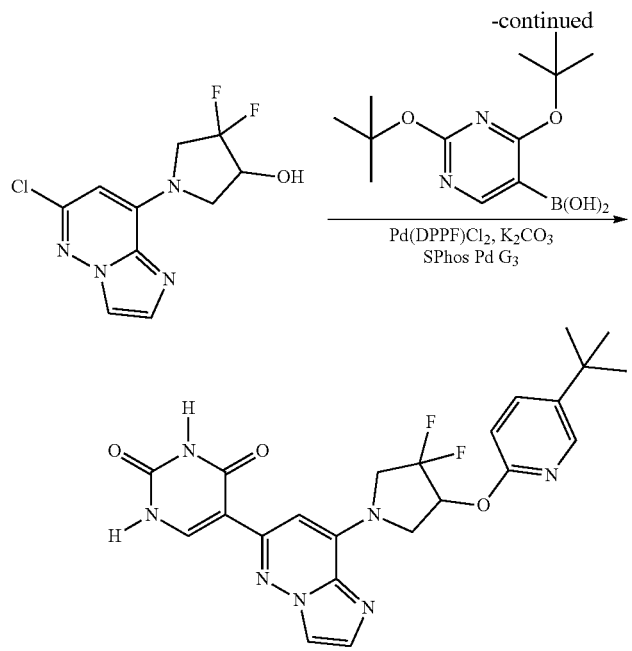

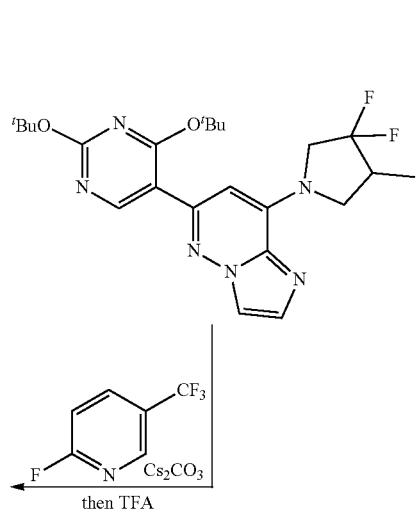

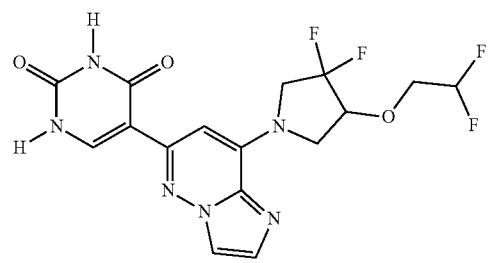 [SMILES: O=c1[nH]cc(-c2cc(N3CC(OCC(F)F)C(F)(F)C3)c3nccn3n2)c(=O)[nH]1]

8-bromo-6-chloro-imidazo[1,2-b]pyridazine (650 mg, 2.8 mmol), 4,4-difluoropyrrolidin-3-ol hydrochloride (490 mg, 3.1 mmol), and DIPEA (1.5 mL, 8.4 mmol) were combined in MeCN (5 mL) and stirred at 55° C. for 3 hours. The mixture was cooled, diluted with water, and extracted into DCM. The organic layer was rinsed with aq NH$_4$Cl and brine, dried over Na$_2$SO$_4$, and concentrated in vacuo. Purification using flash column chromatography (10% EtOAc→50% EtOAc in hexanes) afforded 1-(6-chloroimidazo[1,2-b]pyridazin-8-yl)-4,4-difluoropyrrolidin-3-ol. ES/MS m/z: 275.2 [M+H].

1-(6-chloroimidazo[1,2-b]pyridazin-8-yl)-4,4-difluoropyrrolidin-3-ol (708 mg, 2.58 mmol), (2,4-di-tert-butoxypyrimidin-5-yl)boronic acid (2.77 g, 10.3 mmol), potassium carbonate (1.8 g, 12.9 mmol), and [1,1'-Bis(diphenylphosphino)ferrocene]palladium(II) dichloride (287 mg, 0.39 mmol) were combined in dioxane:water (5:1, 20 mL), degassed with argon, and stirred at 90° C. for 2 hours. The reaction was cooled, and additional (2,4-di-tert-butoxypyrimidin-5-yl)boronic acid (1.5 g, 5.6 mmol), potassium carbonate (1.5 g, 11 mmol), and SPhos Pd G3 (150 mg, 0.19 mmol) were added. The reaction was degassed with argon, and stirring was continued at 90° C. for 1 hour. The reaction was cooled, diluted with EtOAc, rinsed with brine, dried over Na$_2$SO$_4$, and concentrated in vacuo. The residue was purified by flash column affording 1-(6-(2,4-di-tert-butoxypyrimidin-5-yl)imidazo[1,2-b]pyridazin-8-yl)-4,4-difluoropyrrolidin-3-ol. $^1$H NMR (400 MHz, Chloroform-d) δ 8.66 (s, 1H), 7.87 (d, J=1.2 Hz, 1H), 7.59 (d, J=1.2 Hz, 1H), 6.32 (s, 1H), 4.62-4.32 (m, 3H), 4.26-4.06 (m, 2H), 2.58 (s, 1H), 1.70 (s, 9H), 1.68 (s, 9H). $^{19}$F NMR (376 MHz, Chloroform-d) δ −109.56 (d, J=242.5 Hz), −123.80--126.09 (m). $^{19}$F NMR (376 MHz, Chloroform-d) δ −108.49--111.08 (m), −123.79--126.52 (m). ES/MS m/z: 463.1 [M+H].

1-(6-(2,4-di-tert-butoxypyrimidin-5-yl)imidazo[1,2-b]pyridazin-8-yl)-4,4-difluoropyrrolidin-3-ol (30 mg, 0.065 mmol), cesium carbonate (63 mg, 0.19 mmol), and 2-fluoro-5-(trifluoromethyl)pyridine (21 mg, 0.13 mmol) were combined in NMP (0.1 mL) and stirred at 85° C. for 80 minutes. The reaction was cooled to rt, treated with TFA (0.4 mL), then diluted with water and purified by RP-HPLC (MeCN/H$_2$O gradient with TFA modifier) affording 5-(8-(3,3-difluoro-4-((5-(trifluoromethyl)pyridin-2-yl)oxy)pyrrolidin-1-yl)imidazo[1,2-b]pyridazin-6-yl)pyrimidine-2,4(1H,3H)-dione. $^1$H NMR (400 MHz, DMSO-d6) δ8.68 (dd, J=2.3, 1.2 Hz, 1H), 8.18 (dd, J=8.8, 2.6 Hz, 1H), 8.09 (d, J=1.2 Hz, 1H), 7.95 (s, 1H), 7.60 (d, J=1.1 Hz, 1H), 7.20 (d, J=8.7 Hz, 1H), 6.64 (s, 1H), 6.26-5.95 (m, 1H), 4.91-4.36 (m, 3H), 4.20 (d, J=12.7 Hz, 1H). $^{19}$F NMR (377 MHz, DMSO-d6) δ −60.58, −75.26, −107.94 (d, J=237.8 Hz), −119.52 (d, J=238.5 Hz). ES/MS m/z: 496.1 [M+H].

Example 524. 5-(8-(4-(2,2-difluoroethoxy)-3,3-difluoropyrrolidin-1-yl)imidazo[1,2-b]pyridazin-6-yl)pyrimidine-2,4(1H,3H)-dione 1-(6-(2,4-di-tert-butoxypyrimidin-5-yl)imidazo[1,2-b]pyridazin-8-yl)-4,4-difluoropyrrolidin-3-ol (30 mg, 0.065 mmol) and sodium hydride (60% dispersion in oil, 7.5 mg, 0.20 mmol) were combined in THF (0.8 mL) at 5° C. After 15 minutes, 2,2-difluoroethyl trifluoromethanesulfonate (28 mg, 0.13 mmol) was added. The reaction was stirred overnight, while allowing to slowly warm to room temperature. The reaction was treated with water (0.2 mL) and TFA (0.2 mL), concentrated to dryness, then purified by RP-HPLC (MeCN/H$_2$O gradient with TFA modifier) affording 5-(8-(4-(2,2-difluoroethoxy)-3,3-difluoropyrrolidin-1-yl)imidazo[1, 2-b]pyridazin-6-yl)pyrimidine-2,4(1H,3H)-dione. ¹H NMR (400 MHz, DMSO-d6+D2O) δ 8.07 (d, J=1.2 Hz, 1H), 7.94 (s, 1H), 7.59 (d, J=1.2 Hz, 1H), 6.60 (s, 1H), 6.19 (tt, J=54.6, 3.5 Hz, 1H), 4.66-4.51 (m, 1H), 4.53-4.38 (m, 1H), 4.37-4.24 (m, 1H), 4.24-4.14 (m, 1H), 4.01 (app s, 1H), 3.99 (td, J=15.1, 3.6 Hz, 2H). ¹⁹F NMR (376 MHz, DMSO-d6+D2O) δ -75.03 (d, J=2.0 Hz), -107.59 (d, J=237.3 Hz), -121.91 (d, J=237.1 Hz), -126.77 (dt, J=54.5, 15.0 Hz). ES/MS m/z: 415.6 [M+H].

Example 525. 1-(6-(2,4-dioxo-1,2,3,4-tetrahydropyrimidin-5-yl)imidazo[1,2-b]pyridazin-8-yl)-4,4-difluoropyrrolidin-3-yl ethyl carbonate

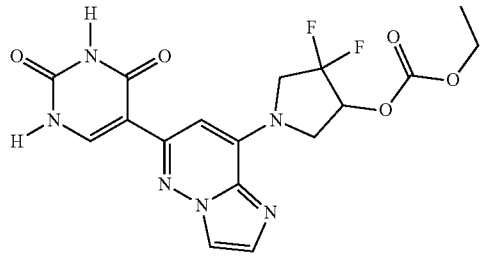 [SMILES: CCOC(=O)OC1CN(c2cc(-c3c[nH]c(=O)[nH]c3=O)nn3ccnc23)CC1(F)F]

1-(6-(2,4-di-tert-butoxypyrimidin-5-yl)imidazo[1,2-b]pyridazin-8-yl)-4,4-difluoropyrrolidin-3-ol (20 mg, 0.043 mmol) and DIPEA (0.05 mL) were combined in CHCl₃/water (3:1, 0.5 mL). Ethyl chloroformate (14 mg, 0.13 mmol) was added and the reaction was warmed to 40° C. After 45 minutes, the reaction was concentrated to dryness, treated with TFA (0.2 mL), the purified by RP-HPLC (MeCN/H₂O gradient with TFA modifier) affording 1-(6-(2,4-dioxo-1,2,3,4-tetrahydropyrimidin-5-yl)imidazo[1,2-b]pyridazin-8-yl)-4,4-difluoropyrrolidin-3-yl ethyl carbonate. ¹H NMR (400 MHz, DMSO-d6+D2O) δ 8.08 (d, J=1.2 Hz, 1H), 7.95 (s, 1H), 7.59 (d, J=1.2 Hz, 1H), 6.61 (s, 1H), 5.49 (s, 1H), 4.62-4.43 (m, 1H), 4.43-4.26 (m, 2H), 4.25-4.11 (m, 3H), 1.24 (t, J=7.1 Hz, 3H). ES/MS m/z: 423.2 [M+H].

Example 526. 1-(6-(2,4-dioxo-1,2,3,4-tetrahydropyrimidin-5-yl)imidazo[1,2-b]pyridazin-8-yl)-4,4-difluoropyrrolidin-3-yl ethylcarbamate

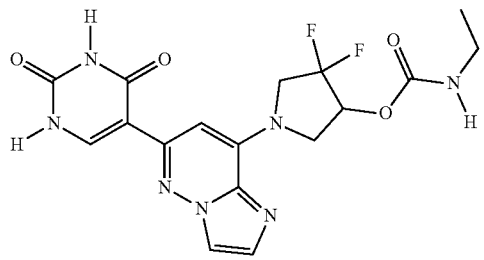 [SMILES: CCNC(=O)OC1CN(c2cc(-c3c[nH]c(=O)[nH]c3=O)nn3ccnc23)CC1(F)F]

1-(6-(2,4-di-tert-butoxypyrimidin-5-yl)imidazo[1,2-b]pyridazin-8-yl)-4,4-difluoropyrrolidin-3-ol (20 mg, 0.043 mmol) and DIPEA (0.05 mL) were combined in DCM (0.5 mL). Ethyl isocyanate (10 mg, 0.14 mmol) was added and the reaction was warmed to 40° C. After 45 minutes, the reaction was warmed to 50° C. After 1.5 hours, the reaction was concentrated to dryness, treated with TFA (0.2 mL), the purified by RP-HPLC (MeCN/H₂O gradient with TFA modifier) affording 1-(6-(2,4-dioxo-1,2,3,4-tetrahydropyrimidin-5-yl)imidazo[1,2-b]pyridazin-8-yl)-4,4-difluoropyrrolidin-3-yl ethylcarbamate. ¹H NMR (400 MHz, DMSO-d6+D2O) δ 8.08 (d, J=1.2 Hz, 1H), 7.94 (s, 1H), 7.58 (d, J=1.2 Hz, 1H), 6.60 (s, 1H), 5.55-5.28 (m, 1H), 4.48 (s, 1H), 4.42-4.20 (m, 2H), 4.06 (s, 1H), 3.04 (q, J=7.2 Hz, 2H), 1.02 (t, J=7.2 Hz, 3H). ES/MS m/z: 422.2 [M+H].

Examples 527 and 528. (S)-5-(8-(3,3-difluoro-4-hydroxypyrrolidin-1-yl)imidazo[1,2-b]pyridazin-6-yl)pyrimidine-2,4(1H,3H)-dione and (R)-5-(8-(3,3-difluoro-4-hydroxypyrrolidin-1-yl)imidazo[1,2-b]pyridazin-6-yl)pyrimidine-2,4(1H,3H)-dione

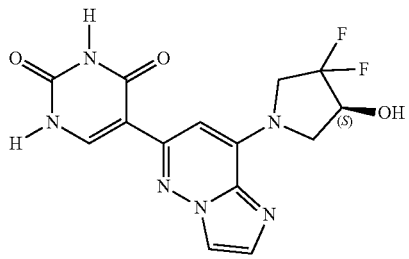

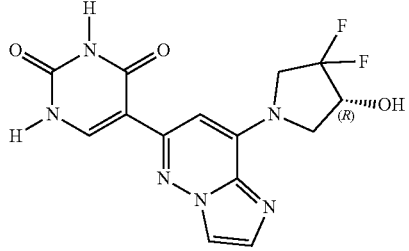

1-(6-(2,4-di-tert-butoxypyrimidin-5-yl)imidazo[1,2-b]pyridazin-8-yl)-4,4-difluoropyrrolidin-3-ol was separated by chiral SFC chromatography (AD-H column, 10% IPA-NH₃ cosolvent) affording (S)-1-(6-(2,4-di-tert-butoxypyrimidin-5-yl)imidazo[1,2-b]pyridazin-8-yl)-4,4-difluoropyrrolidin-3-ol (peak 1), ES/MS m/z: 463.3 [M+H], and (R)-1-(6-(2,4-di-tert-butoxypyrimidin-5-yl)imidazo[1,2-b]pyridazin-8-yl)-4,4-difluoropyrrolidin-3-ol (peak 2), ES/MS m/z: 422.2 [M+H]. The separated enantiomers were treated with TFA and concentrated to provide (S)-5-(8-(3,3-difluoro-4-hydroxypyrrolidin-1-yl)imidazo[1,2-b]pyridazin-6-yl)pyrimidine-2,4(1H,3H)-dione. ¹H NMR (400 MHz, DMSO-d6+D2O) δ 8.07 (d, J=1.2 Hz, 1H), 7.94 (s, 1H), 7.58 (d, J=1.2 Hz, 1H), 6.59 (s, 1H), 4.52-4.17 (m, 3H), 4.11 (s, 1H), 3.84 (s, 1H). ES/MS m/z: 351.2 [M+H]. And (R)-5-(8-(3,3-difluoro-4-hydroxypyrrolidin-1-yl)imidazo[1,2-b]pyridazin-6-yl)pyrimidine-2,4(1H,3H)-dione. ¹H NMR (400 MHz, DMSO-d6+D2O) δ 8.07 (d, J=1.2 Hz, 1H), 7.95 (s, 1H), 7.59 (d, J=1.2 Hz, 1H), 6.60 (s, 1H), 4.50 4.33 (m, 2H), 4.33-4.18 (m, 1H), 4.10 (s, 1H), 3.84 (s, 1H). ES/MS m/z: 351.2 [M+H].

Example 529. (S)-5-(8-(3,3-difluoro-4-(5-(trifluoromethyl)pyridin-2-yl)oxy)pyrrolidin-1-yl)imidazo[1,2-b]pyridazin-6-yl)pyrimidine-2,4(1H,3H)-dione

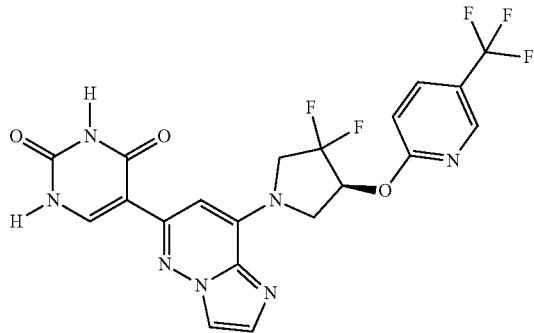 [SMILES: O=c1[nH]cc(-c2cc(N3C[C@H](Oc4ccc(C(F)(F)F)cn4)C(F)(F)C3)c3nccn3n2)c(=O)[nH]1]

(S)-5-(8-(3,3-difluoro-4-((5-(trifluoromethyl)pyridin-2-yl)oxy)pyrrolidin-1-yl)imidazo[1,2-b]pyridazin-6-yl)pyrimidine-2,4(1H,3H)-dione was prepared in the manner described for Example 523, but replacing 1-(6-(2,4-di-tert-butoxypyrimidin-5-yl)imidazo[1,2-b]pyridazin-8-yl)-4,4-difluoropyrrolidin-3-ol with (S)-1-(6-(2,4-di-tert-butoxypyrimidin-5-yl)imidazo[1,2-b]pyridazin-8-yl)-4,4-difluoropyrrolidin-3-ol. $^1$H NMR (400 MHz, Methanol-d4) δ 8.58 (dt, J=2.8, 0.9 Hz, 1H), 8.16 (s, 1H), 8.09-8.03 (m, 2H), 7.73 (d, J=1.5 Hz, 1H), 7.11 (d, J=8.7 Hz, 1H), 7.01 (s, 1H), 6.10-6.01 (m, 1H), 4.64-4.41 (m, 3H), 4.26 (d, J=12.2 Hz, 1H). ES/MS m/z: 496.2 [M+H].

Example 530. (R)-5-(8-(3,3-difluoro-4-((5-(trifluoromethyl)pyridin-2-yl)oxy)pyrrolidin-1-yl)imidazo[1,2-b]pyridazin-6-yl)pyrimidine-2,4(1H,3H)-dione

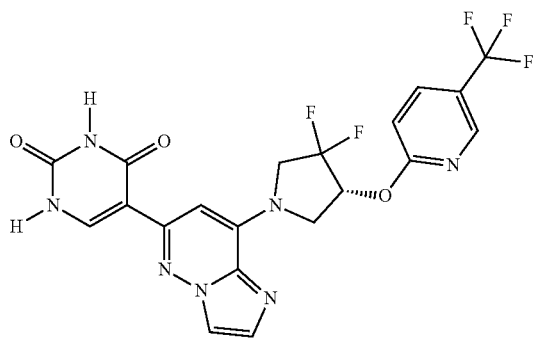 [SMILES: O=c1[nH]cc(-c2cc(N3C[C@@H](Oc4ccc(C(F)(F)F)cn4)C(F)(F)C3)c3nccn3n2)c(=O)[nH]1]

(R)-5-(8-(3,3-difluoro-4-(5-(trifluoromethyl)pyridin-2-yl)oxy)pyrrolidin-1-yl)imidazo[1,2-b]pyridazin-6-yl)pyrimidine-2,4(1H,3H)-dione was prepared in the manner described for Example 523, but replacing 1-(6-(2,4-di-tert-butoxypyrimidin-5-yl)imidazo[1,2-b]pyridazin-8-yl)-4,4-difluoropyrrolidin-3-ol with (R)-1-(6-(2,4-di-tert-butoxypyrimidin-5-yl)imidazo[1,2-b]pyridazin-8-yl)-4,4-difluoropyrrolidin-3-ol. $^1$H NMR (400 MHz, DMSO-d6+ D2O) δ 8.69 (dt, J=1.9, 1.0 Hz, 1H), 8.19 (dd, J=8.8, 2.6 Hz, 1H), 8.09 (d, J=1.2 Hz, 1H), 7.95 (s, 1H), 7.60 (d, J=1.2 Hz, 1H), 7.20 (d, J=8.7 Hz, 1H), 6.65 (s, 1H), 6.18-5.90 (m, 1H), 4.74-4.36 (m, 3H), 4.20 (d, J=12.8 Hz, 1H). ES/MS m/z: 496.1 [M+H].

Example 531. (S)-5-(8-(3,3-difluoro-4-((5-(trifluoromethyl)pyrimidin-2-yl)oxy)pyrrolidin-1-yl)imidazo[1,2-b]pyridazin-6-yl)pyrimidine-2,4(1H,3H)-dione

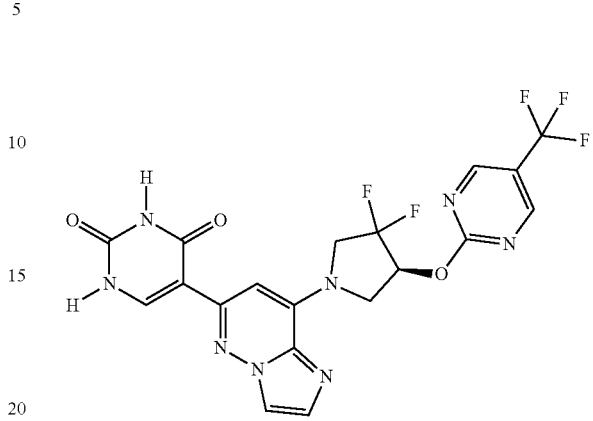

(S)-5-(8-(3,3-difluoro-4-((5-(trifluoromethyl)pyrimidin-2-yl)oxy)pyrrolidin-1-yl)imidazo[1,2-b]pyridazin-6-yl)pyrimidine-2,4(1H,3H)-dione was prepared in the manner described for Example 529, but replacing 2-fluoro-5-(trifluoromethyl)pyridine with 2-chloro-5-(trifluoromethyl)pyrimidine. $^1$H NMR (400 MHz, Methanol-d4) δ 9.01 (d, J=0.9 Hz, 2H), 8.12 (s, 1H), 8.02 (d, J=1.4 Hz, 1H), 7.65 (d, J=1.4 Hz, 1H), 6.90 (s, 1H), 6.16-5.94 (m, 1H), 4.67-4.43 (m, 3H), 4.37 (d, J=12.9 Hz, 1H). ES/MS m/z: 497.1 [M+H].

Example 532. (R)-5-(8-(3,3-difluoro-4-(5-(trifluoromethyl)pyrimidin-2-yl)oxy)pyrrolidin-1-yl)imidazo[1,2-b]pyridazin-6-yl)pyrimidine-2,4(1H,3H)-dione

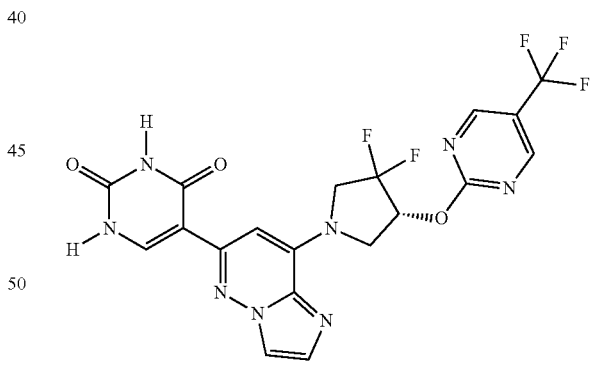

(R)-5-(8-(3,3-difluoro-4-((5-(trifluoromethyl)pyrimidin-2-yl)oxy)pyrrolidin-1-yl)imidazo[1,2-b]pyridazin-6-yl)pyrimidine-2,4(1H,3H)-dione in the manner described for Example in the manner described for Example 530, but replacing 2-fluoro-5-(trifluoromethyl)pyridine with 2-chloro-5-(trifluoromethyl)pyrimidine. $^1$H NMR (400 MHz, Methanol-d4) δ 9.15-8.86 (m, 2H), 8.13 (s, 1H), 8.02 (d, J=1.4 Hz, 1H), 7.65 (d, J=1.4 Hz, 1H), 6.90 (s, 1H), 6.15-5.93 (m, 1H), 4.73-4.44 (m, 3H), 4.38 (d, J=13.0 Hz, 1H). ES/MS m/z: 497.2 [M+H].

Example 533. (S)-1-(6-(2,4-dioxo-1,2,3,4-tetrahydropyrimidin-5-yl)imidazo[1,2-b]pyridazin-8-yl)-4,4-difluoropyrrolidin-3-yl isopropylcarbamate

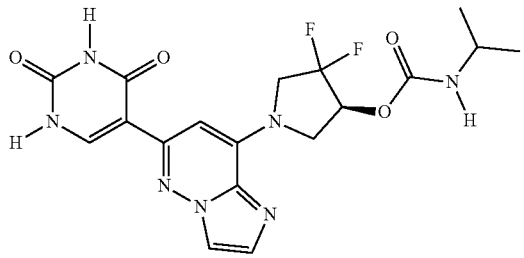 [SMILES: CC(C)NC(=O)O[C@H]1CN(c2cc(-c3c[nH]c(=O)[nH]c3=O)nn3ccnc23)CC1(F)F]

(S)-1-(6-(2,4-di-tert-butoxypyrimidin-5-yl)imidazo[1,2-b]pyridazin-8-yl)-4,4-difluoropyrrolidin-3-ol (51 mg, 0.11 mmol) was combined with isopropylisocyanate (24 mg, 0.28 mmol) and DIPEA (43 mg, 0.33 mmol) in DCM (0.5 mL) and stirred at 35° C. After 2 hours, additional isopropylisocyanate (24 mg, 0.28 mmol) was added, and the reaction was stirred overnight at 45° C. The next day, additional isopropylisocyanate (24 mg, 0.28 mmol) was added, and the reaction was stirred at 45° C. for 4 hours. The reaction was concentrate to dryness, treated with 0.3 mL TFA for 30 min, then diluted with MeCN and water and purified by RP-HPLC (MeCN/H$_2$O gradient with TFA modifier) affording (S)-1-(6-(2,4-dioxo-1,2,3,4-tetrahydropyrimidin-5-yl)imidazo[1,2-b]pyridazin-8-yl)-4,4-difluoropyrrolidin-3-yl isopropylcarbamate. $^1$H NMR (400 MHz, Methanol-d4) δ 8.16 (s, 1H), 8.08 (d, J=1.5 Hz, 1H), 7.73 (d, J=1.5 Hz, 1H), 6.98 (s, 1H), 5.46 (s, 1H), 4.58-4.24 (m, 3H), 4.13 (d, J=12.4 Hz, 1H), 3.76 (hept, J=6.6 Hz, 1H), 1.17 (dd, J=8.1, 6.6 Hz, 6H). ES/MS m/z: 436.1 [M+H].

Example 534. (R)-1-(6-(2,4-dioxo-1,2,3,4-tetrahydropyrimidin-5-yl)imidazo[1,2-b]pyridazin-8-yl)-4,4-difluoropyrrolidin-3-yl isopropylcarbamate

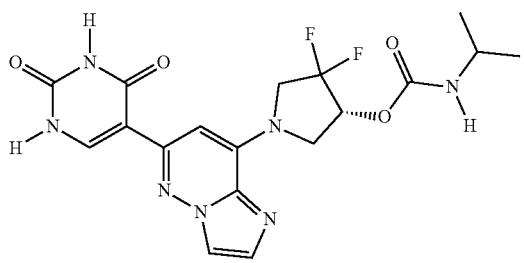 [SMILES: CC(C)NC(=O)O[C@@H]1CN(c2cc(-c3c[nH]c(=O)[nH]c3=O)nn3ccnc23)CC1(F)F]

(R)-1-(6-(2,4-dioxo-1,2,3,4-tetrahydropyrimidin-5-yl)imidazo[1,2-b]pyridazin-8-yl)-4,4-difluoropyrrolidin-3-yl isopropylcarbamate in the manner described for Example 526, but replacing 1-(6-(2,4-di-tert-butoxypyrimidin-5-yl)imidazo[1,2-b]pyridazin-8-yl)-4,4-difluoropyrrolidin-3-ol with (R)-1-(6-(2,4-di-tert-butoxypyrimidin-5-yl)imidazo[1,2-b]pyridazin-8-yl)-4,4-difluoropyrrolidin-3-ol and replacing ethylisocyanate with isopropylisocyanate. $^1$H NMR (400 MHz, Methanol-d4) δ 8.12 (s, 1H), 8.01 (d, J=1.4 Hz, 1H), 7.65 (d, J=1.4 Hz, 1H), 6.85 (s, 1H), 5.52-5.39 (m, 1H), 4.55-4.42 (m, 1H), 4.42-4.25 (m, 2H), 4.14 (d, J=12.1 Hz, 1H), 3.76 (hept, J=6.6 Hz, 1H), 1.17 (t, J=7.1 Hz, 6H). ES/MS m/z: 436.1 [M+H].

Examples 535

1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl)carbamate

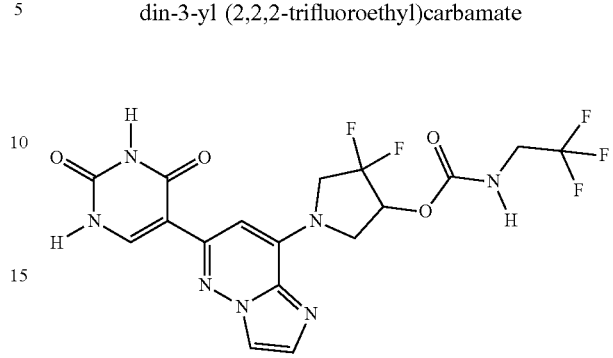

1-(6-(2,4-di-tert-butoxypyrimidin-5-yl)imidazo[1,2-b]pyridazin-8-yl)-4,4-difluoropyrrolidin-3-ol (14.5 mg, 0.0314 mmol) was combined with DIPEA (20 mg, 0.16 mmol) in DCM (0.5 mL) at 5° C. 4-Nitrophenyl chloroformate (8.9 mg, 0.044 mmol) was added and the reaction was allowed to warm to room temperature. After 3 hours, 2,2,2-trifluoroethan-1-amine hydrochloride (8.5 mg, 0.063 mmol) was added and the reaction was stirred overnight at room temperature. The next day, aq NH4Cl (1 mL) was added, and the mixture was stirred for 10 minutes. The aqueous layer was removed, and the organic layer was rinsed with aq NaHCO$_3$ (2×1 mL), dried, filtered, and concentrated. The residue was treated with TFA (0.2 mL). After 10 minutes, the reaction was diluted with MeCN and water and purified by RP-HPLC (MeCN/H$_2$O gradient with TFA modifier) affording 1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl)carbamate. {$^1$H NMR (400 MHz, Methanol-d4) δ 8.20 (s, 1H), 8.18-8.13 (m, 1H), 7.82 (d, J=1.6 Hz, 1H), 7.12 (s, 1H), 5.56 (s, 1H), 4.57-4.25 (m, 5H), 4.16 (d, J=12.4 Hz, 1H), 3.94-3.71 (m, 1H). ES/MS m/z: 476.1 [M+H].}

Example 536. 1-(6-(2,4-dioxo-1,2,3,4-tetrahydropyrimidin-5-yl)imidazo[1,2-b]pyridazin-8-yl)-4,4-difluoropyrrolidin-3-yl 3,3-difluoroazetidine-1-carboxylate

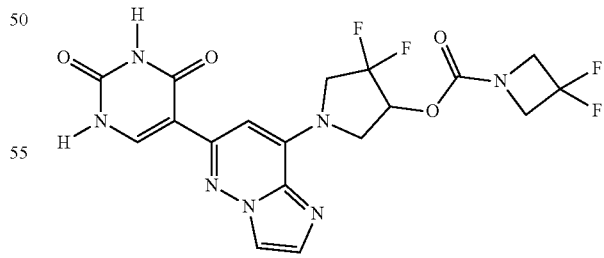

1-(6-(2,4-dioxo-1,2,3,4-tetrahydropyrimidin-5-yl)imidazo[1,2-b]pyridazin-8-yl)-4,4-difluoropyrrolidin-3-yl 3,3-difluoroazetidine-1-carboxylate in the manner described for Example 535, but replacing 2,2,2-trifluoroethan-1-amine hydrochloride with 3,3-difluoroazetidine hydrochloride. $^1$H NMR (400 MHz, Methanol-d4) δ 8.20 (s, 1H), 8.15 (d, J=1.7 Hz, 1H), 7.82 (d, J=1.7 Hz, 1H), 7.13 (s, 1H), 5.63-5.46 (m, 1H), 4.56-4.30 (m, 7H), 4.18 (dt, J=12.5, 2.5 Hz, 1H). $^{19}$F NMR (376 MHz, Methanol-d4) δ −78.14, −103.39 (h, J=12.0 Hz), −108.90−−111.06 (m), −124.19 (ddq, J=243.5, 8.2, 3.7 Hz). ES/MS m/z: 470.1 [M+H].

Example 537. (S)-5-(8-(3,3-difluoro-4-(pyridin-2-yloxy)pyrrolidin-1-yl)imidazo[1,2-b]pyridazin-6-yl)pyrimidine-2,4(1H,3H)-dione

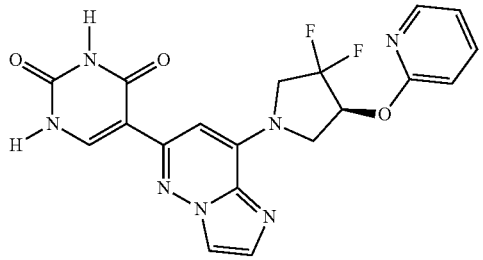 [SMILES: O=c1[nH]cc(-c2cc(N3C[C@H](Oc4ccccn4)C(F)(F)C3)c3nccn3n2)c(=O)[nH]1]

(S)-1-(6-(2,4-di-tert-butoxypyrimidin-5-yl)imidazo[1,2-b]pyridazin-8-yl)-4,4-difluoropyrrolidin-3-ol (9 mg, 0.020 mmol), sodium hydride (60% dispersion in mineral oil, 2.2 mg, 0.058 mmol), and 2-fluoropyridine (3.8 mg, 0.039 mmol) were combined in NMP (0.1 mL) and stirred at 85° C. for 60 minutes. The reaction was cooled to rt, treated with TFA (0.3 mL), then diluted with water and purified by RP-HPLC (MeCN/H$_2$O gradient with TFA modifier) affording (S)-5-(8-(3,3-difluoro-4-(pyridin-2-yloxy)pyrrolidin-1-yl)imidazo[1,2-b]pyridazin-6-yl)pyrimidine-2,4(1H,3H)-dione as a TFA salt. $^1$H NMR (400 MHz, Methanol-d4) δ 8.24-8.17 (m, 3H), 7.89 (d, J=1.9 Hz, 1H), 7.77 (ddd, J=8.3, 7.2, 2.0 Hz, 1H), 7.27 (s, 1H), 7.08 (ddd, J=7.2, 5.1, 0.9 Hz, 1H), 6.93 (dt, J=8.3, 0.9 Hz, 1H), 6.09-5.86 (m, 1H), 4.63-4.35 (m, 3H), 4.19 (dt, J=12.1, 2.6 Hz, 1H). ES/MS m/z: 428.1 [M+H].

Example 538 and 539

(R)-5-(8-(3,3-difluoro-4-(pyridin-2-yloxy)pyrrolidin-1-yl)imidazo[1,2-b]pyridazin-6-yl)pyrimidine-2,4(1H,3H)-dione and 5-(8-(3-fluoro-1H-pyrrol-1-yl)imidazo[1,2-b]pyridazin-6-yl)pyrimidine-2,4(1H,3H)-dione and 5-(8-(3-fluoro-1H-pyrrol-1-yl)imidazo[1,2-b]pyridazin-6-yl)pyrimidine-2,4(1H,3H)-dione

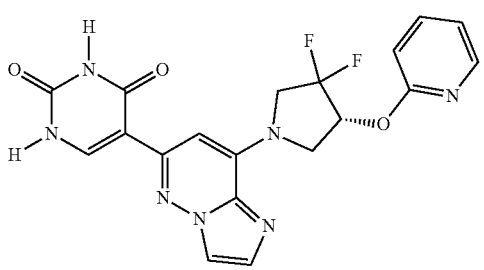

-continued

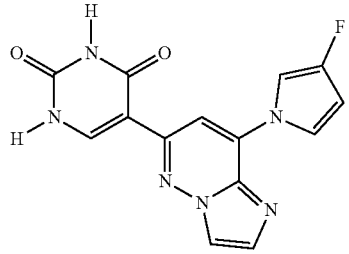

(R)-1-(6-(2,4-di-tert-butoxypyrimidin-5-yl)imidazo[1,2-b]pyridazin-8-yl)-4,4-difluoropyrrolidin-3-ol (9 mg, 0.020 mmol), sodium hydride (60% dispersion in mineral oil, 2.2 mg, 0.058 mmol), and 2-fluoropyridine (3.8 mg, 0.039 mmol) were combined in NMP (0.1 mL) and stirred at 85° C. for 60 minutes. The reaction was cooled to rt, treated with TFA (0.3 mL), then diluted with water and purified by RP-HPLC (MeCN/H$_2$O gradient with TFA modifier) affording (R)-5-(8-(3,3-difluoro-4-(pyridin-2-yloxy)pyrrolidin-1-yl)imidazo[1,2-b]pyridazin-6-yl)pyrimidine-2,4(1H,3H)-dione as a TFA salt. $^1$H NMR (400 MHz, Methanol-d4) δ 8.38-8.14 (m, 3H), 7.90 (d, J=1.9 Hz, 1H), 7.77-7.68 (m, 1H), 7.28 (s, 1H), 7.08 (ddd, J=7.2, 5.1, 0.9 Hz, 1H), 6.93 (dt, J=8.3, 0.9 Hz, 1H), 6.04-5.91 (m, 1H), 4.58-4.37 (m, 3H), 4.19 (d, J=11.8 Hz, 1H). ES/MS m/z: 428.1 [M+H]. 5-(8-(3-fluoro-1H-pyrrol-1-yl)imidazo[1,2-b]pyridazin-6-yl)pyrimidine-2,4(1H,3H)-dione was also isolated. $^1$H NMR (400 MHz, DMSO-d6+D2O) δ 8.36 (d, J=1.2 Hz, 1H), 8.18-8.10 (m, 1H), 8.08 (q, J=2.6 Hz, 1H), 8.05 (s, 1H), 7.84 (d, J=1.2 Hz, 1H), 7.81 (s, 1H), 6.43 (dd, J=3.5, 1.9 Hz, 1H). $^{19}$F NMR (377 MHz, DMSO-d6) δ −74.18, −161.99−−162.10 (m). ES/MS m/z: 313.2 [M+H].

Example 540. (S)-2,2-difluoroethyl (1-(6-(2,4-dioxo-1,2,3,4-tetrahydropyrimidin-5-yl)imidazo[1,2-b]pyridazin-8-yl)-4,4-difluoropyrrolidin-3-yl) carbonate

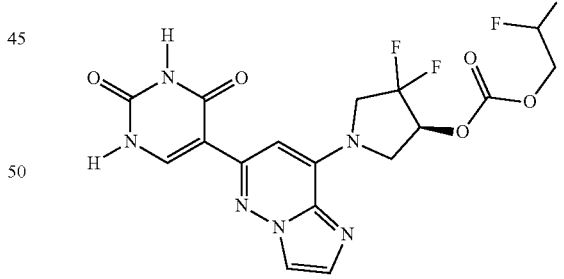

(S)-1-(6-(2,4-di-tert-butoxypyrimidin-5-yl)imidazo[1,2-b]pyridazin-8-yl)-4,4-difluoropyrrolidin-3-ol (7.8 mg, 0.017 mmol) and DIPEA (15 mg, 0.12 mmol) were combined in DCM/water (5:1, 0.2 mL). 2,2-Difluoroethyl chloroformate (11 mg, 0.076 mmol) was added and the reaction was stirred at 35° C. for 1 hour. Additional 2,2-Difluoroethyl chloroformate (11 mg, 0.076 mmol) was added and the reaction was stirred for 45 minutes. The reaction was concentrated, treated with TFA (0.3 mL), then diluted with water and purified by RP-HPLC (MeCN/H$_2$O gradient with TFA modifier) to yield an over-acylated product. This product was treated with concentrated HCl (2 drops), water (2 drops) and TFA (0.5 mL) at 70° C. overnight, then repurified by RP-HPLC (MeCN/H₂O gradient with TFA modifier) to yield (S)-2,2-difluoroethyl (1-(6-(2,4-dioxo-1,2,3,4-tetrahydropyrimidin-5-yl)imidazo[1,2-b]pyridazin-8-yl)-4,4-difluoropyrrolidin-3-yl) carbonate as a TFA salt. ¹H NMR (400 MHz, Methanol-d4) δ 8.14 (s, 1H), 8.05 (d, J=1.4 Hz, 1H), 7.69 (d, J=1.5 Hz, 1H), 6.92 (s, 1H), 6.12 (tt, J=54.4, 3.6 Hz, 1H), 5.53 (td, J=5.5, 2.8 Hz, 1H), 4.63-4.22 (m, 6H). ES/MS m/z: 459.2 [M+H].

Example 541. (S)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl) carbonate

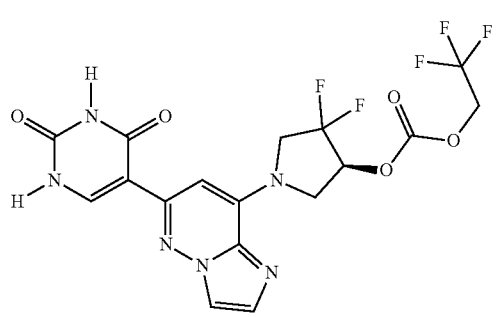 [SMILES: O=C(OCC(F)(F)F)O[C@H]1CN(c2cc(-c3c[nH]c(=O)[nH]c3=O)nn3ccnc23)CC1(F)F]

(S)-1-(6-(2,4-di-tert-butoxypyrimidin-5-yl)imidazo[1,2-b]pyridazin-8-yl)-4,4-difluoropyrrolidin-3-ol (7.8 mg, 0.017 mmol) and DIPEA (15 mg, 0.12 mmol) were combined in DCM/water (5:1, 0.2 mL). 2,2,2-trifluoroethyl chloroformate (11 mg, 0.076 mmol) was added and the reaction was stirred at 35° C. for 1 hour. Additional 2,2,2-trifluoroethyl chloroformate (11 mg, 0.076 mmol) was added and the reaction was stirred for 45 minutes. The reaction was concentrated, treated with TFA (0.3 mL), then diluted with water and purified by RP-HPLC (MeCN/H₂O gradient with TFA modifier) to yield an over-acylated product. This product was treated with concentrated HCl (2 drops), water (2 drops) and TFA (0.5 mL) at 70° C. overnight, then repurified by RP-HPLC (MeCN/H₂O gradient with TFA modifier) to yield (S)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl) carbonate as a TFA salt. ¹H NMR (400 MHz, Methanol-d4) δ 8.14 (s, 1H), 8.05 (d, J=1.4 Hz, 1H), 7.69 (d, J=1.4 Hz, 1H), 6.92 (s, 1H), 5.64-5.49 (m, 1H), 4.84-4.71 (m, 2H), 4.61-4.49 (m, 1H), 4.49-4.23 (m, 3H). ES/MS m/z: 477.2 [M+H].

Example 542. (R)-2,2-difluoroethyl (1-(6-(2,4-dioxo-1,2,3,4-tetrahydropyrimidin-5-yl)imidazo[1,2-b]pyridazin-8-yl)-4,4-difluoropyrrolidin-3-yl) carbonate

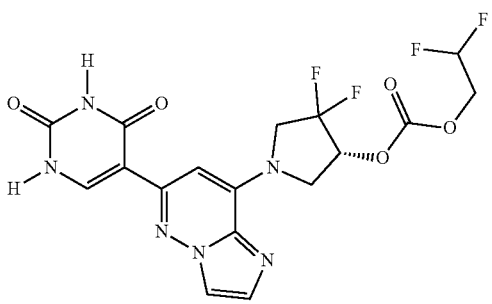 [SMILES: O=C(OCC(F)F)O[C@@H]1CN(c2cc(-c3c[nH]c(=O)[nH]c3=O)nn3ccnc23)CC1(F)F]

(R)-2,2-difluoroethyl (1-(6-(2,4-dioxo-1,2,3,4-tetrahydropyrimidin-5-yl)imidazo[1,2-b]pyridazin-8-yl)-4,4-difluoropyrrolidin-3-yl) carbonate in the manner described for Example 540, but replacing (S)-1-(6-(2,4-di-tert-butoxypyrimidin-5-yl)imidazo[1,2-b]pyridazin-8-yl)-4,4-difluoropyrrolidin-3-ol with (R)-1-(6-(2,4-di-tert-butoxypyrimidin-5-yl)imidazo[1,2-b]pyridazin-8-yl)-4,4-difluoropyrrolidin-3-ol. ¹H NMR (400 MHz, Methanol-d4) δ 8.13 (s, 1H), 8.03 (d, J=1.4 Hz, 1H), 7.67 (d, J=1.4 Hz, 1H), 6.90 (s, 1H), 6.12 (tt, J=54.5, 3.6 Hz, 1H), 5.70-5.48 (m, 1H), 4.64-4.23 (m, 6H). ES/MS m/z: 459.2 [M+H].

Example 543. (R)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl) carbonate

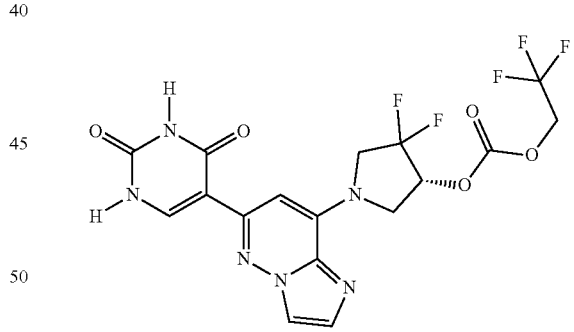

(R)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl) carbonate in the manner described for Example 541, but replacing (S)-1-(6-(2,4-di-tert-butoxypyrimidin-5-yl)imidazo[1,2-b]pyridazin-8-yl)-4,4-difluoropyrrolidin-3-ol with (R)-1-(6-(2,4-di-tert-butoxypyrimidin-5-yl)imidazo[1,2-b]pyridazin-8-yl)-4,4-difluoropyrrolidin-3-ol. ¹H NMR (400 MHz, Methanol-d4) δ 8.16 (s, 1H), 8.08 (d, J=1.5 Hz, 1H), 7.73 (d, J=1.5 Hz, 1H), 6.98 (s, 1H), 5.57 (td, J=5.4, 2.7 Hz, 1H), 4.83-4.71 (m, 2H), 4.61-4.48 (m, 1H), 4.48-4.26 (m, 3H). ¹⁹F NMR (376 MHz, Methanol-d4) δ −74.94−−77.33 (m), −78.08, −107.67−−111.41 (m), −124.29 (d, J=245.9 Hz). ES/MS m/z: 477.1 [M+H].

Example 544. (S)-1-(6-(2,4-dioxo-1,2,3,4-tetrahydropyrimidin-5-yl)imidazo[1,2-b]pyridazin-8-yl)-4,4-difluoropyrrolidin-3-yl tert-butylcarbamate

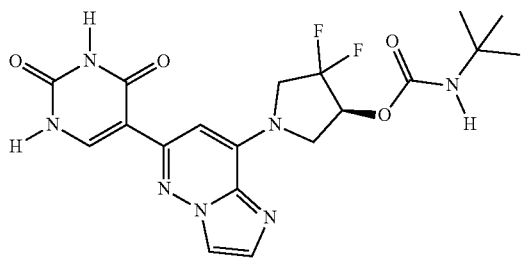 [SMILES: CC(C)(C)NC(=O)O[C@H]1CN(c2cc(-c3c[nH]c(=O)[nH]c3=O)nn3ccnc23)CC1(F)F]

(S)-1-(6-(2,4-di-tert-butoxypyrimidin-5-yl)imidazo[1,2-b]pyridazin-8-yl)-4,4-difluoropyrrolidin-3-ol (7 mg, 0.015 mmol) was combined with tert-butylisocyanate (30 mg, 0.30 mmol) and DIPEA (59 mg, 0.45 mmol) in 1,2-DCE (0.5 mL) and stirred at 60° C. overnight. The next day, the reaction was warmed to 70° C. and stirred an addition 6 hours. The reaction was concentrated to dryness, treated with 0.3 mL TFA for 30 min, then diluted with MeCN and water and purified by RP-HPLC (MeCN/H$_2$O gradient with TFA modifier) affording (S)-1-(6-(2,4-dioxo-1,2,3,4-tetrahydropyrimidin-5-yl)imidazo[1,2-b]pyridazin-8-yl)-4,4-difluoropyrrolidin-3-yl tert-butylcarbamate. $^1$H NMR (400 MHz, Methanol-d4) δ 8.14 (s, 1H), 8.06 (d, J=1.5 Hz, 1H), 7.70 (d, J=1.5 Hz, 1H), 6.94 (s, 1H), 5.42 (s, 1H), 4.56-4.25 (m, 3H), 4.12 (d, J=12.3 Hz, 1H), 1.32 (s, 9H). ES/MS m/z: 450.1 [M+H].

Example 545. (S)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl)carbamate

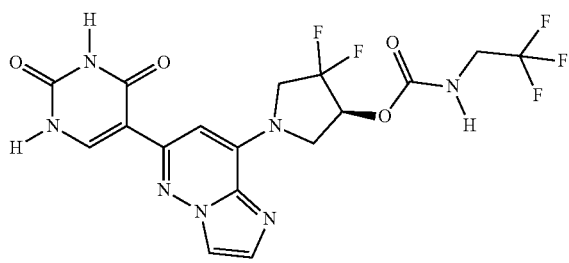 [SMILES: O=C(NCC(F)(F)F)O[C@H]1CN(c2cc(-c3c[nH]c(=O)[nH]c3=O)nn3ccnc23)CC1(F)F]

(S)-1-(6-(2,4-di-tert-butoxypyrimidin-5-yl)imidazo[1,2-b]pyridazin-8-yl)-4,4-difluoropyrrolidin-3-ol (50 mg, 0.11 mmol) was combined with DIPEA (140 mg, 1.1 mmol) in DCM (0.5 mL) at rt. 4-Nitrophenyl chloroformate (52 mg, 0.26 mmol) was added and the reaction was stirred for 2 hours. 2,2,2-trifluoroethan-1-amine hydrochloride (73 mg, 0.54 mmol) was added and the reaction was stirred overnight at room temperature. The next day, aq NH$_4$Cl (1 mL) was added, and the mixture was stirred for 10 minutes. The aqueous layer was removed, and the organic layer was rinsed with aq NaHCO$_3$ (2×1 mL), dried, filtered, and concentrated. The residue was treated with TFA (0.2 mL). After 10 minutes, the reaction was diluted with MeCN and water and purified by RP-HPLC (MeCN/H$_2$O gradient with TFA modifier) affording (S)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl)carbamate. $^1$H NMR (400 MHz, Methanol-d4) δ 8.21-8.11 (m, 2H), 8.05 (d, J=1.5 Hz, 1H), 7.69 (d, J=1.5 Hz, 1H), 6.92 (s, 1H), 5.64-5.37 (m, 1H), 4.57-4.44 (m, 1H), 4.44-4.27 (m, 2H), 4.18 (d, J=12.5 Hz, 1H), 3.91-3.77 (m, 2H). ES/MS m/z: 476.2 [M+H].

Example 546. (S)-1-(6-(2,4-dioxo-1,2,3,4-tetrahydropyrimidin-5-yl)imidazo[1,2-b]pyridazin-8-yl)-4,4-difluoropyrrolidin-3-yl ((R)-1,1,1-trifluoropropan-2-yl)carbamate

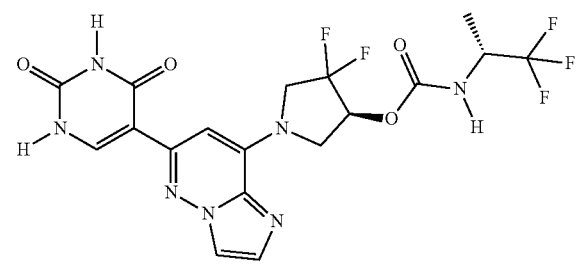 [SMILES: C[C@@H](NC(=O)O[C@H]1CN(c2cc(-c3c[nH]c(=O)[nH]c3=O)nn3ccnc23)CC1(F)F)C(F)(F)F]

(S)-1-(6-(2,4-dioxo-1,2,3,4-tetrahydropyrimidin-5-yl)imidazo[1,2-b]pyridazin-8-yl)-4,4-difluoropyrrolidin-3-yl ((R)-1,1,1-trifluoropropan-2-yl)carbamate in the manner described for Example 545, but replacing 2,2,2-trifluoroethan-1-amine hydrochloride with (R)-1,1,1-trifluoropropan-2-amine. $^1$H NMR (400 MHz, Methanol-d4) δ 8.20-8.08 (m, 2H), 8.02 (d, J=1.4 Hz, 1H), 7.66 (d, J=1.4 Hz, 1H), 6.87 (s, 1H), 5.49 (s, 1H), 4.63-4.46 (m, 1H), 4.46-4.26 (m, 2H), 4.19 (d, J=12.8 Hz, 1H), 1.32 (d, J=7.2 Hz, 3H). ES/MS m/z: 490.2 [M+H].

Example 547. (S)-1-(6-(2,4-dioxo-1,2,3,4-tetrahydropyrimidin-5-yl)imidazo[1,2-b]pyridazin-8-yl)-4,4-difluoropyrrolidin-3-yl ((S)-1,1,1-trifluoropropan-2-yl)carbamate

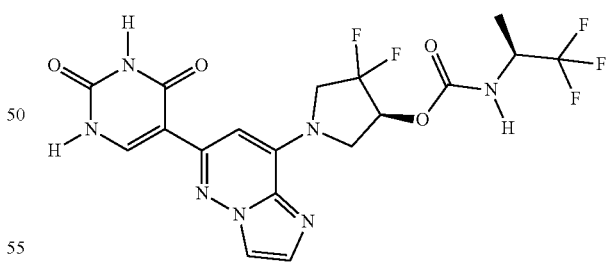

(S)-1-(6-(2,4-dioxo-1,2,3,4-tetrahydropyrimidin-5-yl)imidazo[1,2-b]pyridazin-8-yl)-4,4-difluoropyrrolidin-3-yl ((S)-1,1,1-trifluoropropan-2-yl)carbamate in the manner described for Example 545, but replacing 2,2,2-trifluoroethan-1-amine hydrochloride with (S)-1,1,1-trifluoropropan-2-amine. $^1$H NMR (400 MHz, Methanol-d4) δ 8.18 (s, 1H), 8.15 (d, J=9.2 Hz, 1H), 8.13 (d, J=1.6 Hz, 1H), 7.79 (d, J=1.7 Hz, 1H), 7.08 (s, 1H), 5.54 (s, 1H), 4.59-4.27 (m, 3H), 4.15 (d, J=12.1 Hz, 1H), 1.35 (d, J=7.1 Hz, 3H). ES/MS m/z: 490.2 [M+H].

Example 548. (S)-1-(6-(2,4-dioxo-1,2,3,4-tetrahydropyrimidin-5-yl)imidazo[1,2-b]pyridazin-8-yl)-4,4-difluoropyrrolidin-3-yl ((R)-1-methoxypropan-2-yl)carbamate

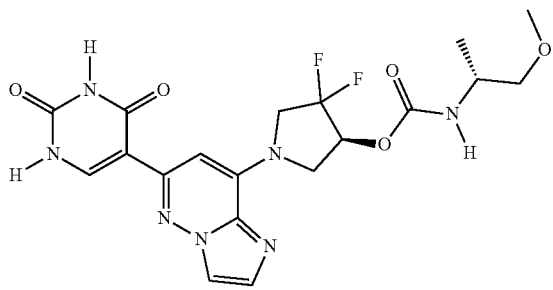 [SMILES: COC[C@@H](C)NC(=O)O[C@H]1CN(c2cc(-c3c[nH]c(=O)[nH]c3=O)nn3ccnc23)CC1(F)F]

(S)-1-(6-(2,4-dioxo-1,2,3,4-tetrahydropyrimidin-5-yl)imidazo[1,2-b]pyridazin-8-yl)-4,4-difluoropyrrolidin-3-yl ((R)-1-methoxypropan-2-yl)carbamate in the manner described for Example 545, but replacing 2,2,2-trifluoroethan-1-amine hydrochloride with (R)-1-methoxypropan-2-amine hydrochloride. $^1$H NMR (400 MHz, Methanol-d4+CF3COOH) δ 8.33 (d, J=2.2 Hz, 1H), 8.31 (s, 1H), 8.05 (d, J=2.2 Hz, 1H), 7.52 (s, 1H), 5.52 (s, 2H), 4.37 (td, J=18.5, 16.7, 6.1 Hz, 3H), 4.10 (d, J=11.7 Hz, 1H), 3.84 (h, J=6.3 Hz, 1H), 3.36 (s, 3H), 1.14 (d, J=6.8 Hz, 3H). ES/MS m/z: 466.2 [M+H].

Example 549. (S)-1-(6-(2,4-dioxo-1,2,3,4-tetrahydropyrimidin-5-yl)imidazo[1,2-b]pyridazin-8-yl)-4,4-difluoropyrrolidin-3-yl ((S)-1-methoxypropan-2-yl)carbamate

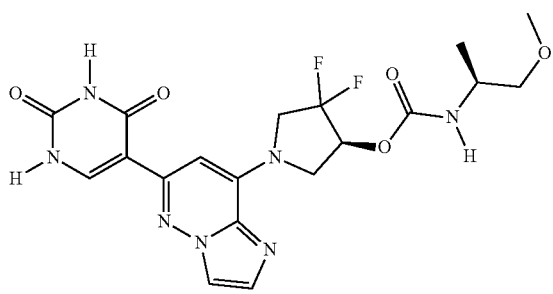 [SMILES: COC[C@H](C)NC(=O)O[C@H]1CN(c2cc(-c3c[nH]c(=O)[nH]c3=O)nn3ccnc23)CC1(F)F]

(S)-1-(6-(2,4-dioxo-1,2,3,4-tetrahydropyrimidin-5-yl)imidazo[1,2-b]pyridazin-8-yl)-4,4-difluoropyrrolidin-3-yl ((S)-1-methoxypropan-2-yl)carbamate in the manner described for Example 545, but replacing 2,2,2-trifluoroethan-1-amine hydrochloride with (S)-1-methoxypropan-2-amine hydrochloride. $^1$H NMR (400 MHz, Methanol-d4+CF3COOH) δ 8.33 (d, J=2.2 Hz, 1H), 8.31 (s, 1H), 8.05 (d, J=2.2 Hz, 1H), 7.52 (s, 1H), 5.52 (s, 2H), 4.37 (td, J=18.5, 16.7, 6.1 Hz, 3H), 4.10 (d, J=11.7 Hz, 1H), 3.84 (h, J=6.3 Hz, 1H), 3.36 (s, 3H), 1.14 (d, J=6.8 Hz, 3H). ES/MS m/z: 466.2 [M+H].

Example 550. (S)-1-(6-(2,4-dioxo-1,2,3,4-tetrahydropyrimidin-5-yl)imidazo[1,2-b]pyridazin-8-yl)-4,4-difluoropyrrolidin-3-yl (1,1-difluoropropan-2-yl)carbamate

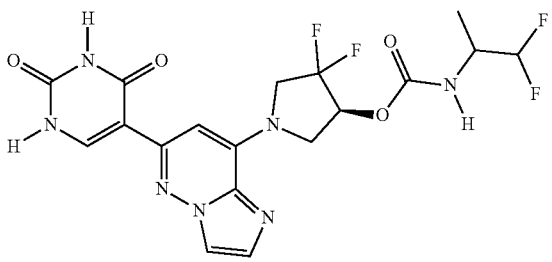 [SMILES: CC(NC(=O)O[C@H]1CN(c2cc(-c3c[nH]c(=O)[nH]c3=O)nn3ccnc23)CC1(F)F)C(F)F]

(S)-1-(6-(2,4-dioxo-1,2,3,4-tetrahydropyrimidin-5-yl)imidazo[1,2-b]pyridazin-8-yl)-4,4-difluoropyrrolidin-3-yl (1,1-difluoropropan-2-yl)carbamate in the manner described for Example 545, but replacing 2,2,2-trifluoroethan-1-amine hydrochloride with 1,1-difluoropropan-2-amine hydrochloride. $^1$H NMR (400 MHz, Methanol-d4+CF3COOH) δ 8.33 (d, J=2.1 Hz, 1H), 8.30 (s, 1H), 8.03 (d, J=2.1 Hz, 1H), 7.46 (s, 1H), 5.83 (tdd, J=56.1, 9.1, 2.8 Hz, 1H), 5.56 (s, 1H), 4.49-4.29 (m, 3H), 4.20-4.09 (m, 1H), 4.06-3.93 (m, 1H), 1.23 (dd, J=10.3, 7.0 Hz, 3H). ES/MS m/z: 472.2 [M+H].

Example 551. (S)-1-(6-(2,4-dioxo-1,2,3,4-tetrahydropyrimidin-5-yl)imidazo[1,2-b]pyridazin-8-yl)-4,4-difluoropyrrolidin-3-yl bicyclo[1.1.1]pentan-1-ylcarbamate

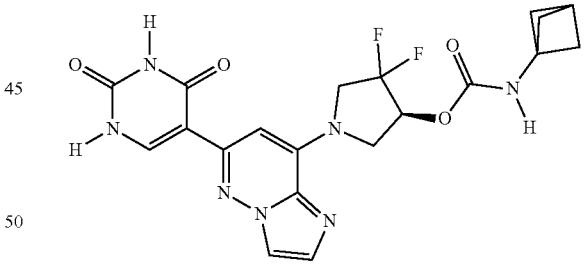

(S)-1-(6-(2,4-dioxo-1,2,3,4-tetrahydropyrimidin-5-yl)imidazo[1,2-b]pyridazin-8-yl)-4,4-difluoropyrrolidin-3-yl-bicyclo[1.1.1]pentan-1-ylcarbamate in the manner described for Example 545, but replacing 2,2,2-trifluoroethan-1-amine hydrochloride with bicyclo[1.1.1]pentan-1-amine hydrochloride. $^1$H NMR (400 MHz, Methanol-d4) δ 8.13 (s, 1H), 8.03 (d, J=1.4 Hz, 1H), 7.67 (d, J=1.4 Hz, 1H), 6.89 (s, 1H), 5.43 (s, 1H), 4.59-4.43 (m, 1H), 4.42-4.24 (m, 2H), 4.12 (d, J=12.6 Hz, 1H), 2.41 (s, 1H), 2.05 (s, 6H). ES/MS m/z: 460.1 [M+H].

Example 552. 5-(8-((1S,3S)-3-(3,4-difluorophenyl)-2,2-difluorocyclopropyl)imidazo[1,2-b]pyridazin-6-yl)pyrimidine-2,4(1H,3H)-dione (Racemic Mixture)

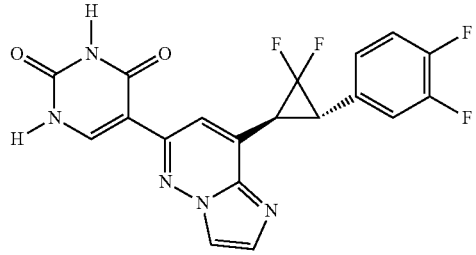 [SMILES: O=c1[nH]cc(-c2cc([C@@H]3[C@@H](c4ccc(F)c(F)c4)C3(F)F)c3nccn3n2)c(=O)[nH]1]

5-(8-((1S,3S)-3-(3,4-difluorophenyl)-2,2-difluorocyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,3S)-3-(3,4-difluorophenyl)-2,2-difluorocyclopropyl)-6-(2,4-dimethoxypyrimidin-5-yl)imidazo[1,2-b]pyridazine (Racemic Mixture). ES/MS m/z: 418.12 [M+H]. $^{1}$H NMR (400 MHz, DMSO-d6) δ 11.63-11.50 (m, 2H), 8.36 (d, J=1.3 Hz, 1H), 8.05 (d, J=6.1 Hz, 1H), 7.86 (d, J=1.3 Hz, 1H), 7.78 (s, 1H), 7.71-7.61 (m, 1H), 7.55-7.45 (m, 1H), 7.41-7.34 (m, 1H). $^{19}$F NMR (376 MHz, DMSO-d6) δ −75.25, −132.32–−133.28 (m), −133.74–−134.93 (m), −138.59–−139.01 (m), −140.38–−140.69 (m).

Example 553. 2-chloro-5-((1S,2S)-2-(6-(2,4-dioxo-1,2,3,4-tetrahydropyrimidin-5-yl)imidazo[1,2-b]pyridazin-8-yl)cyclopropyl)benzonitrile

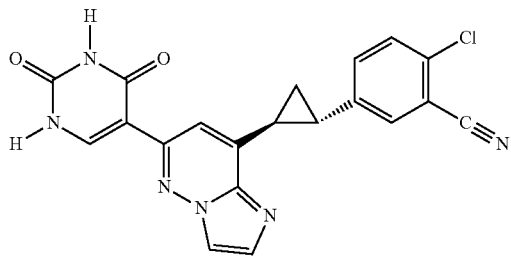 [SMILES: N#Cc1cc([C@H]2C[C@@H]2c2cc(-c3c[nH]c(=O)[nH]c3=O)nn3ccnc23)ccc1Cl]

2-chloro-5-((1S,2S)-2-(6-(2,4-dioxo-1,2,3,4-tetrahydropyrimidin-5-yl)imidazo[1,2-b]pyridazin-8-yl)cyclopropyl)benzonitrile was prepared in a manner described for Example 1, but replacing 8-cyclopropyl-6-(2,4-dimethoxypyrimidin-5-yl)-2-methyl-imidazo[1,2-b]pyridazine with 2-chloro-5-((2S,2S)-2-(6-(2,4-dimethoxypyrimidin-5-yl)imidazo[1,2-b]pyridazin-8-yl)cyclopropyl)benzonitrile. ES/MS m/z: 405.10 [M+H]. $^{1}$H NMR (400 MHz, DMSO-d6) δ 11.60-11.50 (m, 2H), 8.35 (s, 1H), 8.03 (d, J=6.0 Hz, 1H), 7.92-7.86 (m, 2H), 7.72-7.59 (m, 3H), 2.95-2.85 (m, 1H), 2.85-2.74 (m, 1H), 2.19-2.08 (m, 1H), 1.93-1.80 (m, 1H).

Example 554. 5-(8-((1S,2S)-2-(4-(trifluoromethyl)phenyl)cyclopropyl)imidazo[1,2-b]pyridazin-6-yl)pyrimidine-2,4(1H,3H)-dione

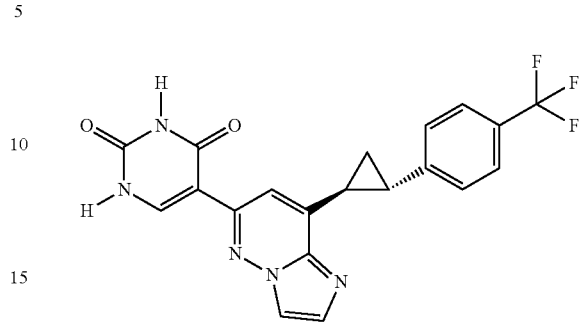

5-(8-((2S,2S)-2-(4-(trifluoromethyl)phenyl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(4-(trifluoromethyl)phenyl)cyclopropyl)imidazo[1,2-b]pyridazine. ES/MS m/z: 414.10 [M+H]. $^{1}$H NMR (400 MHz, DMSO-d6) δ 11.62-11.52 (m, 2H), 8.38 (d, J=1.5 Hz, 1H), 8.05 (d, J=6.1 Hz, 1H), 7.97-7.91 (m, 1H), 7.70-7.62 (m, 3H), 7.51-7.44 (m, 2H), 2.94-2.86 (m, 1H), 2.86-2.78 (m, 1H), 2.16-2.04 (m, 1H), 1.91-1.80 (m, 1H). $^{19}$F NMR (376 MHz, DMSO-d6) δ−61.27, −75.21.

Example 555. 5-(8-((2S,2S)-2-(2-chlorophenyl)cyclopropyl)imidazo[1,2-b]pyridazin-6-yl)pyrimidine-2,4(1H,3H)-dione (Racemic Mixture)

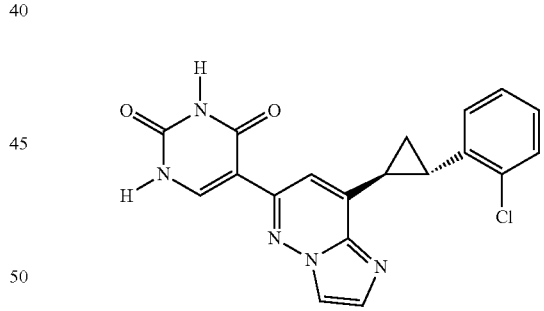

5-(8-((1S,2S)-2-(2-chlorophenyl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(2-chlorophenyl)cyclopropyl)-6-(2,4-dimethoxypyrimidin-5-yl)imidazo[1,2-b]pyridazine (Racemic Mixture). ES/MS m/z: 380.10 [M+H]. $^{1}$H NMR (400 MHz, Methanol-d4) δ 8.38-8.33 (m, 1H), 8.29 (s, 1H), 8.08 (s, 1H), 8.05 (s, 1H), 7.46-7.40 (m, 1H), 7.36-7.23 (m, 3H), 2.99-2.86 (m, 1H), 2.62-2.52 (m, 1H), 2.06-1.96 (m, 1H), 1.95-1.85 (m, 1H). $^{19}$F NMR (376 MHz, Methanol-d4) δ −77.75.

Example 556. 5-(8-((2S,2S)-2-(4-(difluoromethoxy)phenyl)cyclopropyl)imidazo[1,2-b]pyridazin-6-yl)pyrimidine-2,4(1H,3H)-dione (Racemic Mixture)

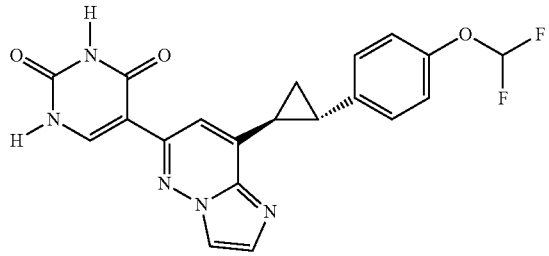 [SMILES: O=c1[nH]cc(-c2cc([C@H]3C[C@@H]3c3ccc(OC(F)F)cc3)c3nccn3n2)c(=O)[nH]1]

5-(8-((1S,2S)-2-(4-(difluoromethoxy)phenyl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(4-(difluoromethoxy)phenyl)cyclopropyl)-6-(2,4-dimethoxypyrimidin-5-yl)imidazo[1,2-b]pyridazine (Racemic Mixture). ES/MS m/z: 412.10 [M+H]. $^1$H NMR (400 MHz, Methanol-d4) δ 8.40 (d, J=2.0 Hz, 1H), 8.31 (s, 1H), 8.09 (d, J=2.0 Hz, 1H), 8.04 (s, 1H), 7.38-7.29 (m, 2H), 7.18-7.09 (m, 2H), 6.81 (t, J=74.1 Hz, 1H), 2.80-2.66 (m, 2H), 1.98-1.88 (m, 2H). $^{19}$F NMR (376 MHz, Methanol-d4) δ −77.85, −83.91 (d, J=74.2 Hz).

Example 557. 4-((2S,2S)-2-(6-(2,4-dioxo-1,2,3,4-tetrahydropyrimidin-5-yl)imidazo[1,2-b]pyridazin-8-yl)cyclopropyl)-2,6-difluorobenzonitrile

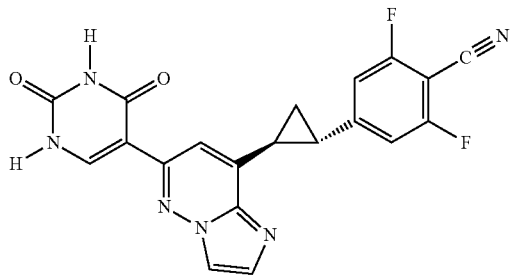 [SMILES: N#Cc1c(F)cc([C@H]2C[C@@H]2c2cc(-c3c[nH]c(=O)[nH]c3=O)nn3ccnc23)cc1F]

4-((1S,2S)-2-(6-(2,4-dioxo-1,2,3,4-tetrahydropyrimidin-5-yl)imidazo[1,2-b]pyridazin-8-yl)cyclopropyl)-2,6-difluorobenzonitrile was prepared in a manner described for Example 1, but replacing 8-cyclopropyl-6-(2,4-dimethoxypyrimidin-5-yl)-2-methyl-imidazo[1,2-b]pyridazine with 4-((1S,2S)-2-(6-(2,4-dimethoxypyrimidin-5-yl)imidazo[1,2-b]pyridazin-8-yl)cyclopropyl)-2,6-difluorobenzonitrile. ES/MS m/z: 407.10 [M+H]. $^1$H NMR (400 MHz, Methanol-d4) δ 8.40 (d, J=1.9 Hz, 1H), 8.30 (s, 1H), 8.10 (d, J=1.9 Hz, 1H), 8.06 (s, 1H), 7.25-7.15 (m, 2H), 2.92-2.75 (m, 2H), 2.12-1.94 (m, 2H). $^{19}$F NMR (376 MHz, Methanol-d4) δ −77.95, −107.99 (d, J=9.6 Hz).

Example 558. 4-((2S,2S)-2-(6-(2,4-dioxo-1,2,3,4-tetrahydropyrimidin-5-yl)imidazo[1,2-b]pyridazin-8-yl)cyclopropyl)-2,3-difluorobenzonitrile

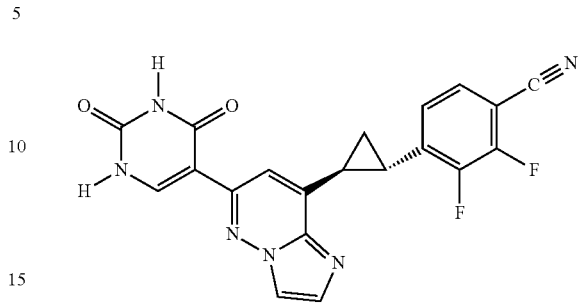

4-((1S,2S)-2-(6-(2,4-dioxo-1,2,3,4-tetrahydropyrimidin-5-yl)imidazo[1,2-b]pyridazin-8-yl)cyclopropyl)-2,3-difluorobenzonitrile was prepared in a manner described for Example 1, but replacing 8-cyclopropyl-6-(2,4-dimethoxypyrimidin-5-yl)-2-methyl-imidazo[1,2-b]pyridazine with 4-((1S,2S)-2-(6-(2,4-dimethoxypyrimidin-5-yl)imidazo[1,2-b]pyridazin-8-yl)cyclopropyl)-2,3-difluorobenzonitrile. ES/MS m/z: 407.10 [M+H]. $^1$H NMR (400 MHz, Methanol-d4) δ 8.39 (d, J=2.0 Hz, 1H), 8.29 (s, 1H), 8.10 (s, 1H), 8.09 (d, J=2.0 Hz, 1H), 7.62-7.53 (m, 1H), 7.28-7.19 (m, 1H), 2.99-2.80 (m, 2H), 2.13-1.95 (m, 2H). $^{19}$F NMR (376 MHz, Methanol-d4) δ −77.96, −135.73--135.87 (m), −143.81--144.01 (m).

Example 559. 4-((2S,2S)-2-(6-(2,4-dioxo-1,2,3,4-tetrahydropyrimidin-5-yl)imidazo[1,2-b]pyridazin-8-yl)cyclopropyl)-2-methoxybenzonitrile

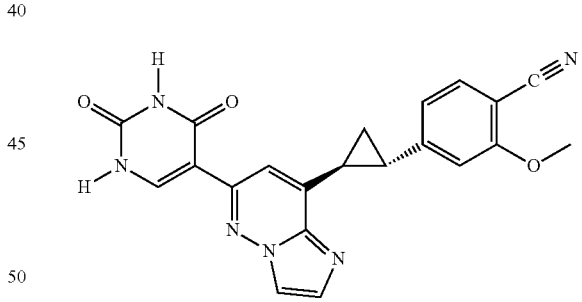

4-((2S,2S)-2-(6-(2,4-dioxo-1,2,3,4-tetrahydropyrimidin-5-yl)imidazo[1,2-b]pyridazin-8-yl)cyclopropyl)-2-methoxybenzonitrile was prepared in a manner described for Example 1, but replacing 8-cyclopropyl-6-(2,4-dimethoxypyrimidin-5-yl)-2-methyl-imidazo[1,2-b]pyridazine with 4-((1S,2S)-2-(6-(2,4-dimethoxypyrimidin-5-yl)imidazo[1,2-b]pyridazin-8-yl)cyclopropyl)-2-methoxybenzonitrile. ES/MS m/z: 401.10 [M+H]. $^1$H NMR (400 MHz, Methanol-d4) δ 8.39 (d, J=2.0 Hz, 1H), 8.30 (s, 1H), 8.09 (d, J=2.0 Hz, 1H), 8.05 (s, 1H), 7.57 (d, J=8.0 Hz, 1H), 7.11-7.05 (m, 1H), 7.00-6.92 (m, 1H), 3.97 (s, 3H), 2.88-2.75 (m, 2H), 2.03-1.96 (m, 2H).

Example 560. 4-((2S,2S)-2-(6-(2,4-dioxo-1,2,3,4-tetrahydropyrimidin-5-yl)imidazo[1,2-b]pyridazin-8-yl)cyclopropyl)-2-methylbenzonitrile

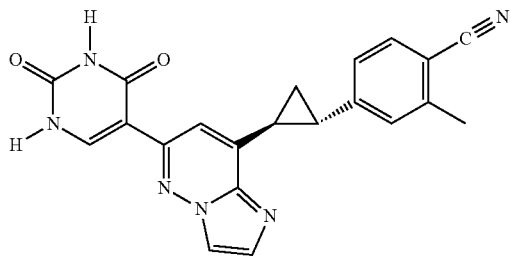 [SMILES: Cc1cc([C@H]2C[C@@H]2c2cc(-c3c[nH]c(=O)[nH]c3=O)nn3ccnc23)ccc1C#N]

4-((2S,2S)-2-(6-(2,4-dioxo-1,2,3,4-tetrahydropyrimidin-5-yl)imidazo[1,2-b]pyridazin-8-yl)cyclopropyl)-2-methylbenzonitrile was prepared in a manner described for Example 1, but replacing 8-cyclopropyl-6-(2,4-dimethoxypyrimidin-5-yl)-2-methyl-imidazo[1,2-b]pyridazine with 4-(1S,2S)-2-(6-(2,4-dimethoxypyrimidin-5-yl)imidazo[1,2-b]pyridazin-8-yl)cyclopropyl)-2-methylbenzonitrile. ES/MS m/z: 385.10 [M+H]. $^1$H NMR (400 MHz, Methanol-d4) δ 8.35 (d, J=1.9 Hz, 1H), 8.27 (s, 1H), 8.03 (d, J=1.9 Hz, 1H), 7.98 (s, 1H), 7.62 (d, J=8.0 Hz, 1H), 7.33 (s, 1H), 7.27-7.20 (m, 1H), 2.86-2.70 (m, 2H), 2.53 (s, 3H), 2.03-1.89 (m, 2H).

Example 561. 5-(8-((2S,2S)-2-(4-(difluoromethoxy)phenyl)cyclopropyl)imidazo[1,2-b]pyridazin-6-yl)pyrimidine-2,4(1H,3H)-dione

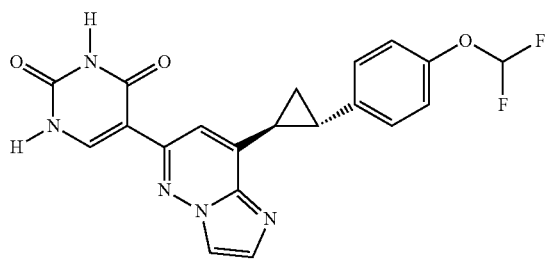 [SMILES: O=c1[nH]cc(-c2cc([C@H]3C[C@@H]3c3ccc(OC(F)F)cc3)c3nccn3n2)c(=O)[nH]1]

5-(8-((2S,2S)-2-(4-(difluoromethoxy)phenyl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(4-(difluoromethoxy)phenyl)cyclopropyl)-6-(2,4-dimethoxypyrimidin-5-yl)imidazo[1,2-b]pyridazine. ES/MS m/z: 412.10 [M+H]. $^1$H NMR (400 MHz, Methanol-d4) δ 8.36 (d, J=1.9 Hz, 1H), 8.28 (s, 1H), 8.05 (d, J=1.9 Hz, 1H), 7.99 (s, 1H), 7.35-7.27 (m, 2H), 7.16-7.08 (m, 2H), 6.79 (t, J=74.1 Hz, 1H), 2.79-2.65 (m, 2H), 1.95-1.85 (m, 2H). $^{19}$F NMR (376 MHz, Methanol-d4) δ −77.78, −83.90 (d, J=74.2 Hz).

Example 562. 5-(8-((2S,2S)-2-(2-(trifluoromethyl)benzo[d]thiazol-6-yl)cyclopropyl)imidazo[1,2-b]pyridazin-6-yl)pyrimidine-2,4(1H,3H)-dione

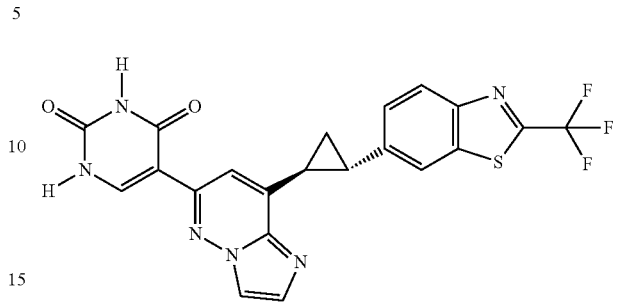

5-(8-((1S,2S)-2-(2-(trifluoromethyl)benzo[d]thiazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-2-(trifluoromethyl)benzo[d]thiazole. ES/MS m/z: 471.10 [M+H]. $^1$H NMR (400 MHz, Methanol-d4) δ 8.32 (d, J=1.8 Hz, 1H), 8.26 (s, 1H), 8.15 (d, J=8.6 Hz, 1H), 8.10 (d, J=1.8 Hz, 1H), 7.98 (d, J=1.8 Hz, 1H), 7.95 (s, 1H), 7.61 (dd, J=8.6, 1.8 Hz, 1H), 2.96-2.83 (m, 2H), 2.10-1.97 (m, 2H). $^{19}$F NMR (376 MHz, Methanol-d4) δ −63.97, −77.76.

Example 563. 2-cyclopropyl-4-(1S,2S)-2-(6-(2,4-dioxo-1,2,3,4-tetrahydropyrimidin-5-yl)imidazo[1,2-b]pyridazin-8-yl)cyclopropyl)benzonitrile

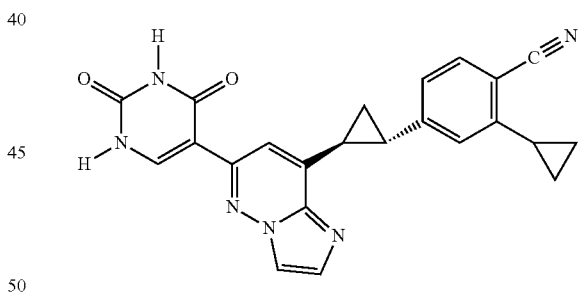

2-cyclopropyl-4-((2S,2S)-2-(6-(2,4-dioxo-1,2,3,4-tetrahydropyrimidin-5-yl)imidazo[1,2-b]pyridazin-8-yl)cyclopropyl)benzonitrile was prepared in a manner described for Example 1, but replacing 8-cyclopropyl-6-(2,4-dimethoxypyrimidin-5-yl)-2-methyl-imidazo[1,2-b]pyridazine with 2-cyclopropyl-4-((2S,2S)-2-(6-(2,4-dimethoxypyrimidin-5-yl)imidazo[1,2-b]pyridazin-8-yl)cyclopropyl)benzonitrile. ES/MS m/z: 411.20 [M+H]. $^1$H NMR (400 MHz, Methanol-d4) δ 8.37 (d, J=2.0 Hz, 1H), 8.28 (s, 1H), 8.06 (d, J=2.0 Hz, 1H), 8.01 (s, 1H), 7.61 (d, J=8.1 Hz, 1H), 7.18 (dd, J=8.1, 1.7 Hz, 1H), 6.97 (d, J=1.7 Hz, 1H), 2.82-2.71 (m, 2H), 2.29-2.20 (m, 1H), 2.01-1.88 (m, 2H), 1.22-1.09 (m, 2H), 0.94-0.80 (m, 2H). $^{19}$F NMR (376 MHz, Methanol-d4) δ −77.90.

Example 564. 5-(8-((1S,2S)-2-(4-(2,2,2-trifluoroethoxy)phenyl)cyclopropyl)imidazo[1,2-b]pyridazin-6-yl)pyrimidine-2,4(1H,3H)-dione (Racemic Mixture)

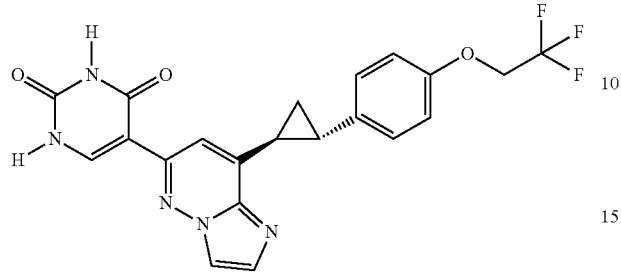

5-(8-((1S,2S)-2-(4-(2,2,2-trifluoroethoxy)phenyl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(4-(2,2,2-trifluoroethoxy)phenyl)cyclopropyl)imidazo[1,2-b]pyridazine (Racemic Mixture). ES/MS m/z: 444.10 [M+H]. $^1$H NMR (400 MHz, Methanol-d4) δ 8.34 (d, J=1.9 Hz, 1H), 8.27 (s, 1H), 8.03 (d, J=1.9 Hz, 1H), 7.95 (s, 1H), 4.52 (q, J=8.5 Hz, 2H), 2.76-2.61 (m, 2H), 1.87 (t, J=7.5 Hz, 2H). $^{19}$F NMR (376 MHz, Methanol-d4) δ −76.35 (t, J=8.5 Hz), −77.73.

Example 565. 4-((2S,2S)-2-(6-(2,4-dioxo-1,2,3,4-tetrahydropyrimidin-5-yl)imidazo[1,2-b]pyridazin-8-yl)cyclopropyl)-2,5-difluorobenzonitrile

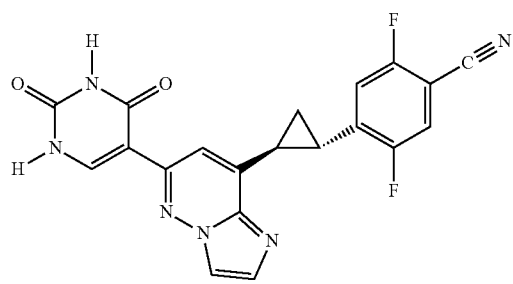 [SMILES: N#Cc1cc(F)c([C@H]2C[C@@H]2c2cc(-c3c[nH]c(=O)[nH]c3=O)nn3ccnc23)cc1F]

4-((2S,2S)-2-(6-(2,4-dioxo-1,2,3,4-tetrahydropyrimidin-5-yl)imidazo[1,2-b]pyridazin-8-yl)cyclopropyl)-2,5-difluorobenzonitrile was prepared in a manner described for Example 1, but replacing 8-cyclopropyl-6-(2,4-dimethoxypyrimidin-5-yl)-2-methyl-imidazo[1,2-b]pyridazine with 4-((1S,2S)-2-(6-(2,4-dimethoxypyrimidin-5-yl)imidazo[1,2-b]pyridazin-8-yl)cyclopropyl)-2,5-difluorobenzonitrile. ES/MS m/z: 407.10 [M+H]. $^1$H NMR (400 MHz, DMSO-d6) δ 11.60-11.50 (m, 2H), 8.35 (s, 1H), 8.02 (d, J=6.1 Hz, 1H), 7.95 (dd, J=9.4, 5.4 Hz, 1H), 7.88 (bs, 1H), 7.66 (s, 1H), 7.53 (dd, J=10.2, 6.0 Hz, 1H), 3.14-3.03 (m, 1H), 2.96-2.87 (m, 1H), 2.28-2.19 (m, 1H), 2.01-1.90 (m, 1H). $^{19}$F NMR (376 MHz, DMSO-d6) δ −113.84--113.99 (m), −123.11--123.32 (m).

Example 566. 2-chloro-4-((2S,2S)-2-(6-(2,4-dioxo-1,2,3,4-tetrahydropyrimidin-5-yl)imidazo[1,2-b]pyridazin-8-yl)cyclopropyl)benzonitrile

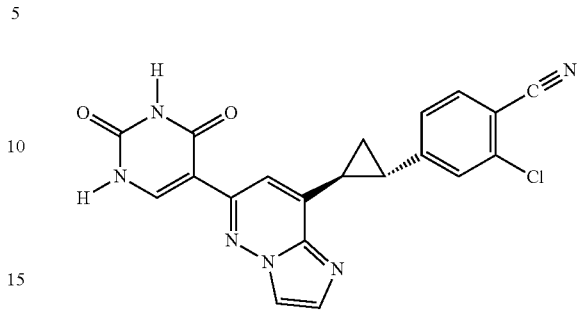

2-chloro-4-((2S,2S)-2-(6-(2,4-dioxo-1,2,3,4-tetrahydropyrimidin-5-yl)imidazo[1,2-b]pyridazin-8-yl)cyclopropyl)benzonitrile was prepared in a manner described for Example 1, but replacing 8-cyclopropyl-6-(2,4-dimethoxypyrimidin-5-yl)-2-methyl-imidazo[1,2-b]pyridazine with 2-chloro-4-((2S,2S)-2-(6-(2,4-dimethoxypyrimidin-5-yl)imidazo[1,2-b]pyridazin-8-yl)cyclopropyl)benzonitrile. ES/MS m/z: 405.10 [M+H]. $^1$H NMR (400 MHz, Methanol-d4) δ 8.36 (d, J=1.8 Hz, 1H), 8.28 (s, 1H), 8.04 (d, J=1.8 Hz, 1H), 7.98 (s, 1H), 7.78 (d, J=8.1 Hz, 1H), 7.59 (d, J=1.7 Hz, 1H), 7.41 (dd, J=8.1, 1.7 Hz, 1H), 2.92-2.76 (m, 2H), 2.10-1.93 (m, 2H). $^{19}$F NMR (376 MHz, Methanol-d4) δ −77.86.

Example 567. 4-((2S,2S)-2-(6-(2,4-dioxo-1,2,3,4-tetrahydropyrimidin-5-yl)imidazo[1,2-b]pyridazin-8-yl)cyclopropyl)-2-fluoro-6-methylbenzonitrile

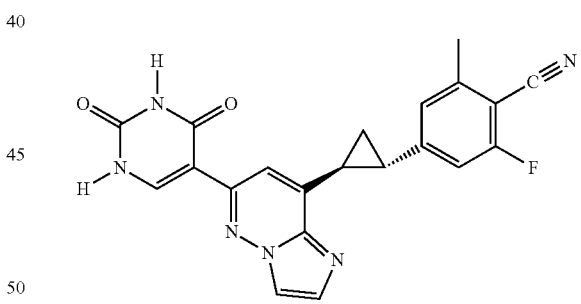

4-((2S,2S)-2-(6-(2,4-dioxo-1,2,3,4-tetrahydropyrimidin-5-yl)imidazo[1,2-b]pyridazin-8-yl)cyclopropyl)-2-fluoro-6-methylbenzonitrile was prepared in a manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)imidazo[1,2-b]pyridazin-8-yl)cyclopropyl)-2-fluoro-6-methylbenzonitrile. ES/MS m/z: 403.20 [M+H]. $^1$H NMR (400 MHz, Methanol-d4) δ 8.38 (d, J=2.0 Hz, 1H), 8.29 (s, 1H), 8.07 (d, J=2.0 Hz, 1H), 8.02 (s, 1H), 7.18 (s, 1H), 7.09 (d, J=10.2 Hz, 1H), 2.87-2.80 (m, 1H), 2.79-2.72 (m, 1H), 2.54 (s, 3H), 2.05-1.91 (m, 2H). $^{19}$F NMR (376 MHz, Methanol-d4) δ −77.90, −110.59 (d, J=10.3 Hz).

Example 568. 5-(8-((2S,2S)-2-(6-chloropyridin-3-yl)cyclopropyl)imidazo[1,2-b]pyridazin-6-yl)pyrimidine-2,4(1H,3H)-dione (Racemic Mixture)

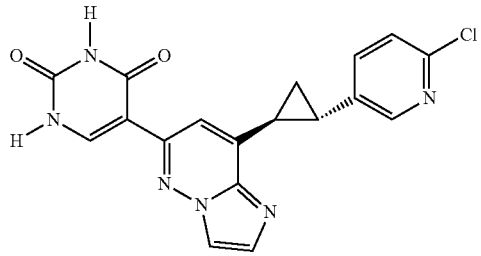

5-(8-((1S,2S)-2-(6-chloropyridin-3-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(6-chloropyridin-3-yl)cyclopropyl)-6-(2,4-dimethoxypyrimidin-5-yl)imidazo[1,2-b]pyridazine (Racemic Mixture). ES/MS m/z: 381.10 [M+H]. $^1$H NMR (400 MHz, Methanol-d4) δ 8.42 (d, J=2.1 Hz, 1H), 8.36 (d, J=2.6 Hz, 1H), 8.31 (s, 1H), 8.14 (d, J=2.1 Hz, 1H), 8.11 (s, 1H), 7.71 (dd, J=8.3, 2.6 Hz, 1H), 7.45 (d, J=8.3 Hz, 1H), 2.82-2.71 (m, 2H), 2.03-1.91 (m, 2H).

Example 569. 5-(8-(6-azaspiro[3.4]octan-6-yl)imidazo[1,2-b]pyridazin-6-yl)pyrimidine-2,4(1H,3H)-dione

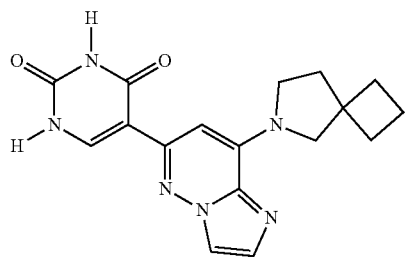 [SMILES: O=c1[nH]cc(-c2cc(N3CCC4(CCC4)C3)c3nccn3n2)c(=O)[nH]1]

5-(8-(6-azaspiro[3.4]octan-6-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(6-azaspiro[3.4]octan-6-yl)imidazo[1,2-b]pyridazine. ES/MS m/z: 339.20 [M+H]. $^1$H NMR (400 MHz, Methanol-d4) δ 8.26 (s, 1H), 8.24 (d, J=2.1 Hz, 1H), 7.96 (d, J=2.1 Hz, 1H), 7.31 (s, 1H), 3.90-3.82 (m, 4H), 2.26-2.14 (m, 4H), 2.16-2.00 (m, 4H).

Example 570. 5-(8-((2S,2S)-2-(2-methylbenzo[d]thiazol-6-yl)cyclopropyl)imidazo[1,2-b]pyridazin-6-yl)pyrimidine-2,4(1H,3H)-dione (Racemic Mixture)

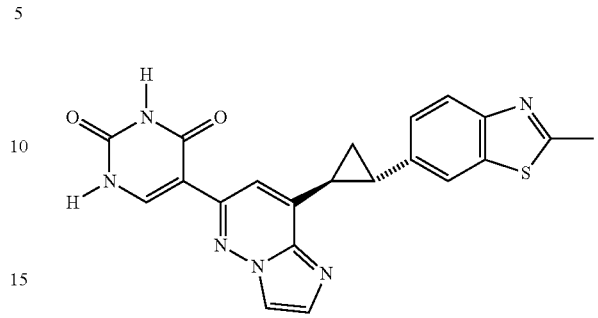

5-(8-((1S,2S)-2-(2-methylbenzo[d]thiazol-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-2-methylbenzo[d]thiazole (Racemic Mixture). ES/MS m/z: 417.10 [M+H]. $^1$H NMR (400 MHz, Methanol-d4) δ 8.38 (d, J=2.0 Hz, 1H), 8.30 (s, 1H), 8.07 (d, J=2.0 Hz, 1H), 8.06 (s, 1H), 7.87 (d, J=1.8 Hz, 1H), 7.85 (d, J=8.5 Hz, 1H), 7.41 (dd, J=8.5, 1.8 Hz, 1H), 2.90-2.84 (m, 1H), 2.83 (s, 3H), 2.81-2.74 (m, 1H), 2.04-1.95 (m, 2H).

Example 571. 5-(8-(2,2-difluoro-6-azaspiro[3.4]octan-6-yl)imidazo[1,2-b]pyridazin-6-yl)pyrimidine-2,4(1H,3H)-dione

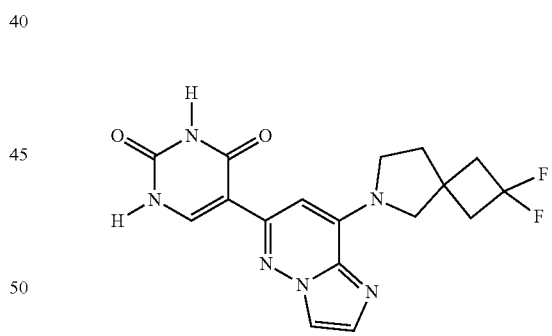

5-(8-(2,2-difluoro-6-azaspiro[3.4]octan-6-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 8-(2,2-difluoro-6-azaspiro[3.4]octan-6-yl)-6-(2,4-dimethoxypyrimidin-5-yl)imidazo[1,2-b]pyridazine. ES/MS m/z: 375.20 [M+H]. $^1$H NMR (400 MHz, Methanol-d4) δ 8.25 (s, 1H), 8.23 (d, J=2.0 Hz, 1H), 7.94 (d, J=2.0 Hz, 1H), 7.28 (s, 1H), 3.98 (s, 2H), 3.93 (d, J=6.8 Hz, 2H), 2.85-2.61 (m, 4H), 2.30 (t, J=6.8 Hz, 2H). $^{19}$F NMR (376 MHz, Methanol-d4) δ −91.22-93.35 (m).

Example 572. 5-(8-(3-(methoxymethyl)-3-methylpyrrolidin-1-yl)imidazo[1,2-b]pyridazin-6-yl)pyrimidine-2,4(1H,3H)-dione

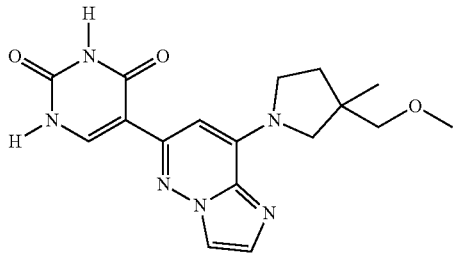 [SMILES: COCC1(C)CCN(c2cc(-c3c[nH]c(=O)[nH]c3=O)nn3ccnc23)C1]

5-(8-(3-(methoxymethyl)-3-methylpyrrolidin-1-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-(methoxymethyl)-3-methylpyrrolidin-1-yl)imidazo[1,2-b]pyridazine. ES/MS m/z: 357.20 [M+H]. $^1$H NMR (400 MHz, Methanol-d4) δ8.21 (s, 1H), 8.16 (d, J=2.0 Hz, 1H), 7.86 (d, J=2.0 Hz, 1H), 7.19 (s, 1H), 3.94 (t, J=7.2 Hz, 2H), 3.85 (d, J=10.4 Hz, 1H), 3.58 (d, J=10.4 Hz, 1H), 3.38 (s, 3H), 3.36 (s, 2H), 2.20-2.11 (m, 1H), 1.96-1.83 (m, 1H), 1.23 (s, 3H).

Example 573. 4-((2S,2S)-2-(6-(2,4-dioxo-1,2,3,4-tetrahydropyrimidin-5-yl)-3-fluoroimidazo[1,2-b]pyridazin-8-yl)cyclopropyl)-2,5-difluorobenzonitrile

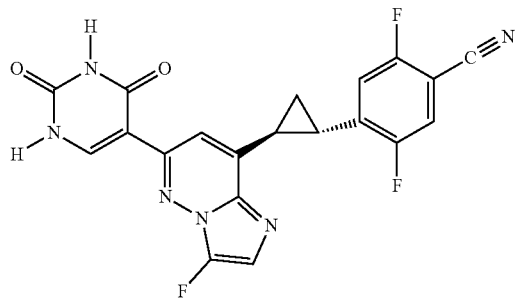 [SMILES: N#Cc1cc(F)c([C@H]2C[C@@H]2c2cc(-c3c[nH]c(=O)[nH]c3=O)nn3c(F)cnc23)cc1F]

4-((2S,2S)-2-(6-(2,4-dioxo-1,2,3,4-tetrahydropyrimidin-5-yl)-3-fluoroimidazo[1,2-b]pyridazin-8-yl)cyclopropyl)-2,5-difluorobenzonitrile was prepared in a manner described for Example 1, but replacing 8-cyclopropyl-6-(2,4-dimethoxypyrimidin-5-yl)-2-methyl-imidazo[1,2-b]pyridazine with 4-((2S,2S)-2-(6-(2,4-dimethoxypyrimidin-5-yl)-3-fluoroimidazo[1,2-b]pyridazin-8-yl)cyclopropyl)-2,5-difluorobenzonitrile. ES/MS m/z: 425.10 [M+H]. $^1$H NMR (400 MHz, Methanol-d4) δ 8.20 (s, 1H), 7.68 (s, 1H), 7.57 (dd, J=9.2, 5.3 Hz, 1H), 7.47 (d, J=6.7 Hz, 1H), 7.31 (dd, J=9.8, 5.9 Hz, 1H), 3.01-2.93 (m, 1H), 2.92-2.83 (m, 1H), 2.17-2.08 (m, 1H), 1.93-1.85 (m, 1H). $^{19}$F NMR (376 MHz, Methanol-d4) δ −78.16, −115.24--115.40 (m), −124.37--124.55 (m), −157.10 (d, J=6.7 Hz).

Example 574. 5-(8-((2S,2S)-2-(4-(2,2-difluoroethoxy)phenyl)cyclopropyl)imidazo[1,2-b]pyridazin-6-yl)pyrimidine-2,4(1H,3H)-dione (Racemic Mixture)

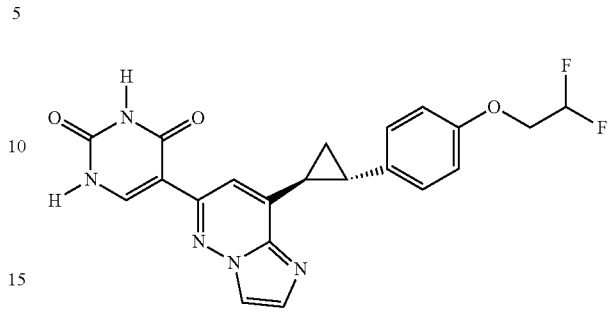

5-(8-((1S,2S)-2-(4-(2,2-difluoroethoxy)phenyl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((2S,2S)-2-(4-(2,2-difluoroethoxy)phenyl)cyclopropyl)-6-(2,4-dimethoxypyrimidin-5-yl)imidazo[1,2-b]pyridazine (Racemic Mixture). ES/MS m/z: 426.20 [M+H]. $^1$H NMR (400 MHz, Methanol-d4) δ 8.35 (d, J=2.0 Hz, 1H), 8.27 (s, 1H), 8.04 (d, J=2.0 Hz, 1H), 7.96 (s, 1H), 6.15 (tt, J=55.0, 3.8 Hz, 1H), 4.21 (td, J=13.8, 3.8 Hz, 2H), 2.73-2.61 (m, 2H), 1.90-1.82 (m, 2H). $^{19}$F NMR (376 MHz, Methanol-d4) δ −77.73, −128.19 (dt, J=54.9, 13.8 Hz).

Example 575. 5-(8-(6,6-difluoro-3-azabicyclo[3.1.1]heptan-3-yl)imidazo[1,2-b]pyridazin-6-yl)pyrimidine-2,4(1H,3H)-dione

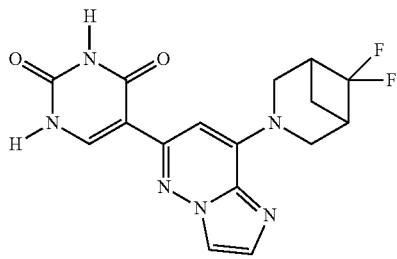 [SMILES: O=c1[nH]cc(-c2cc(N3CC4CC(C3)C4(F)F)c3nccn3n2)c(=O)[nH]1]

5-(8-(6,6-difluoro-3-azabicyclo[3.1.1]heptan-3-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 3-(6-(2,4-dimethoxypyrimidin-5-yl)imidazo[1,2-b]pyridazin-8-yl)-6,6-difluoro-3-azabicyclo[3.1.1]heptane. ES/MS m/z: 361.10 [M+H]. $^1$H NMR (400 MHz, Methanol-d4) δ 8.22 (s, 1H), 8.16 (s, 1H), 7.84 (s, 1H), 7.28 (s, 1H), 4.57-4.46 (m, 1H), 4.38-4.24 (m, 1H), 3.79-3.67 (m, 2H), 3.67-3.54 (m, 1H), 3.17-3.06 (m, 1H), 3.02-2.85 (m, 1H), 2.55-2.37 (m, 1H). $^{19}$F NMR (376 MHz, Methanol-d4) δ −95.74--98.79 (m).

Example 576. 5-(8-((2S,2S)-2-(5-chloropyridin-2-yl)cyclopropyl)imidazo[1,2-b]pyridazin-6-yl)pyrimidine-2,4(1H,3H)-dione (Racemic Mixture)

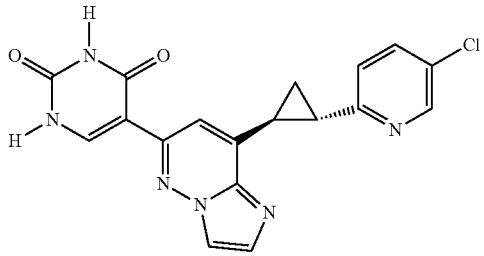 [SMILES: O=c1[nH]cc(-c2cc([C@H]3C[C@@H]3c3ccc(Cl)cn3)c3nccn3n2)c(=O)[nH]1]

5-(8-((1S,2S)-2-(5-chloropyridin-2-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(5-chloropyridin-2-yl)cyclopropyl)-6-(2,4-dimethoxypyrimidin-5-yl)imidazo[1,2-b]pyridazine (Racemic Mixture). ES/MS m/z: 381.10 [M+H]. $^1$H NMR (400 MHz, Methanol-d4) δ 8.54-8.50 (m, 1H), 8.42 (d, J=2.0 Hz, 1H), 8.32 (s, 1H), 8.13 (s, 1H), 8.11 (d, J=2.0 Hz, 1H), 7.77 (dd, J=8.4, 2.5 Hz, 1H), 7.46 (dd, J=8.4, 0.6 Hz, 1H), 3.09-2.98 (m, 1H), 2.93-2.86 (m, 1H), 2.16-2.08 (m, 1H), 1.96-1.88 (m, 1H).

Example 577. 5-(8-(3-cyclopropylpyrrolidin-1-yl)imidazo[1,2-b]pyridazin-6-yl)pyrimidine-2,4(1H,3H)-dione

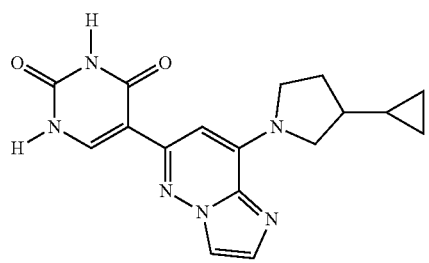 [SMILES: O=c1[nH]cc(-c2cc(N3CCC(C4CC4)C3)c3nccn3n2)c(=O)[nH]1]

5-(8-(3-cyclopropylpyrrolidin-1-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 8-(3-cyclopropylpyrrolidin-1-yl)-6-(2,4-dimethoxypyrimidin-5-yl)imidazo[1,2-b]pyridazine. ES/MS m/z: 339.20 [M+H]. $^1$H NMR (400 MHz, Methanol-d4) δ 8.19 (s, 1H), 8.17-8.09 (m, 1H), 7.86-7.78 (m, 1H), 7.14 (s, 1H), 4.11-3.90 (m, 2H), 3.87-3.74 (m, 1H), 3.70-3.60 (m, 1H), 2.34-2.20 (m, 1H), 2.02-1.90 (m, 1H), 1.88-1.73 (m, 1H), 0.92-0.76 (m, 1H), 0.62-0.51 (m, 2H), 0.32-0.22 (m, 2H).

Example 578. 5-(8-(3-(3,3-difluorocyclobutyl)pyrrolidin-1-yl)imidazo[1,2-b]pyridazin-6-yl)pyrimidine-2,4(1H,3H)-dione

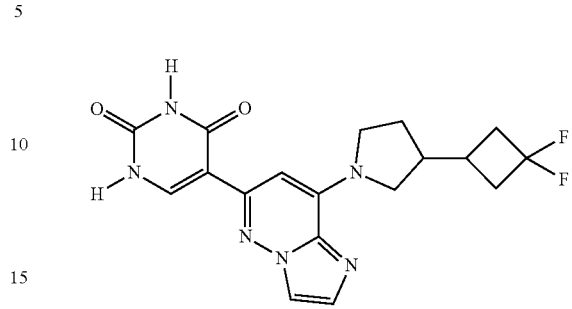

5-(8-(3-(3,3-difluorocyclobutyl)pyrrolidin-1-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 8-(3-(3,3-difluorocyclobutyl)pyrrolidin-1-yl)-6-(2,4-dimethoxypyrimidin-5-yl)imidazo[1,2-b]pyridazine. ES/MS m/z: 389.20 [M+H]. $^1$H NMR (400 MHz, Methanol-d4) δ 8.24 (s, 1H), 8.21 (s, 1H), 7.91 (s, 1H), 7.24 (s, 1H), 4.12-3.77 (m, 3H), 3.57-3.48 (m, 1H), 2.84-2.68 (m, 2H), 2.60-2.51 (m, 1H), 2.50-2.34 (m, 2H), 2.35-2.21 (m, 2H), 1.93-1.80 (m, 1H). $^{19}$F NMR (377 MHz, Methanol-d4) δ −84.25--85.21 (m), −96.91--98.31 (m).

Example 579. 5-(8-(1-fluoro-3-azabicyclo[3.1.1]heptan-3-yl)imidazo[1,2-b]pyridazin-6-yl)pyrimidine-2,4(1H,3H)-dione

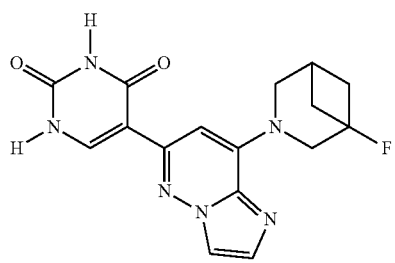 [SMILES: O=c1[nH]cc(-c2cc(N3CC4CC(F)(C4)C3)c3nccn3n2)c(=O)[nH]1]

5-(8-(1-fluoro-3-azabicyclo[3.1.1]heptan-3-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 3-(6-(2,4-dimethoxypyrimidin-5-yl)imidazo[1,2-b]pyridazin-8-yl)-1-fluoro-3-azabicyclo[3.1.1]heptane. ES/MS m/z: 342.20 [M+H]. $^1$H NMR (400 MHz, Methanol-d4) δ 8.23 (s, 1H), 8.19 (d, J=1.9 Hz, 1H), 7.86 (d, J=1.9 Hz, 1H), 7.33 (s, 1H), 4.15 (d, J=3.8 Hz, 2H), 3.99-3.91 (m, 2H), 2.84-2.68 (m, 1H), 2.53-2.41 (m, 2H), 2.08-1.91 (m, 2H). $^{19}$F NMR (376 MHz, Methanol-d4) δ −143.44--143.86 (m).

Example 580. 5-(3-fluoro-8-((2S,2S)-2-(2-methyl-benzo[d]thiazol-6-yl)cyclopropyl)imidazo[1,2-b]pyridazin-6-yl)pyrimidine-2,4(1H,3H)-dione (Racemic Mixture)

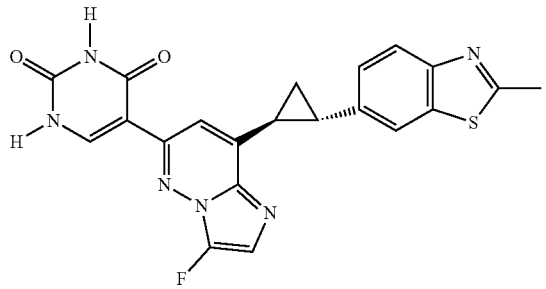 [SMILES: Cc1nc2ccc([C@H]3C[C@@H]3c3cc(-c4c[nH]c(=O)[nH]c4=O)nn4c(F)cnc34)cc2s1]

5-(3-fluoro-8-((1S,2S)-2-(2-methylbenzo[d]thiazol-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((2S,2S)-2-(6-(2,4-dimethoxypyrimidin-5-yl)-3-fluoroimidazo[1,2-b]pyridazin-8-yl)cyclopropyl)-2-methylbenzo[d]thiazole (Racemic Mixture). ES/MS m/z: 435.10 [M+H]. $^1$H NMR (400 MHz, DMSO-d6) δ 11.56-11.49 (m, 1H), 8.03 (d, J=6.4 Hz, 1H), 7.93 (d, J=1.8 Hz, 1H), 7.83 (d, J=8.4 Hz, 1H), 7.54 (d, J=7.1 Hz, 1H), 7.49 (s, 1H), 7.37 (dd, J=8.4, 1.8 Hz, 1H), 2.99-2.90 (m, 1H), 2.78 (s, 3H), 2.82-2.71 (m, 1H), 2.19-2.10 (m, 1H), 1.87-1.79 (m, 1H). $^{19}$F NMR (376 MHz, DMSO-d6) δ −155.60 (d, J=7.1 Hz).

Example 581. 5-(8-((2S,2S)-2-(benzo[d]thiazol-6-yl)cyclopropyl)-3-fluoroimidazo[1,2-b]pyridazin-6-yl)pyrimidine-2,4(1H,3H)-dione (Racemic Mixture)

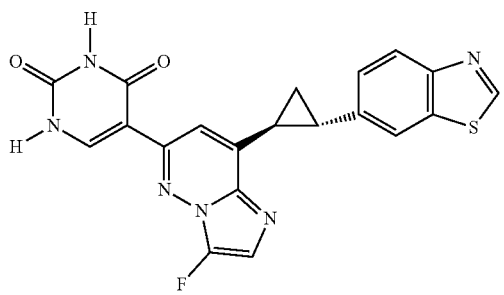 [SMILES: O=c1[nH]cc(-c2cc([C@H]3C[C@@H]3c3ccc4ncsc4c3)c3ncc(F)n3n2)c(=O)[nH]1]

5-(8-((1S,2S)-2-(benzo[d]thiazol-6-yl)cyclopropyl)-3-fluoroimidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)-3-fluoroimidazo[1,2-b]pyridazin-8-yl)cyclopropyl)benzo[d]thiazole (Racemic Mixture). ES/MS m/z: 421.10 [M+H]. $^1$H NMR (400 MHz, DMSO-d6) δ 11.59-11.50 (m, 2H), 9.33 (s, 1H), 8.07 (d, J=1.8 Hz, 1H), 8.05-7.96 (m, 2H), 7.57 (d, J=7.0 Hz, 1H), 7.51 (s, 1H), 7.44 (dd, J=8.5, 1.8 Hz, 1H), 3.03-2.93 (m, 1H), 2.82-2.73 (m, 1H), 2.23-2.11 (m, 1H), 1.91-1.81 (m, 1H). $^{19}$F NMR (376 MHz, DMSO-d6) δ −155.52 (d, J=7.0 Hz).

Example 582. 5-(8-((2S,2S)-2-(3-fluoro-5-(trifluoromethyl)pyridin-2-yl)cyclopropyl)imidazo[1,2-b]pyridazin-6-yl)pyrimidine-2,4(1H,3H)-dione (Racemic Mixture)

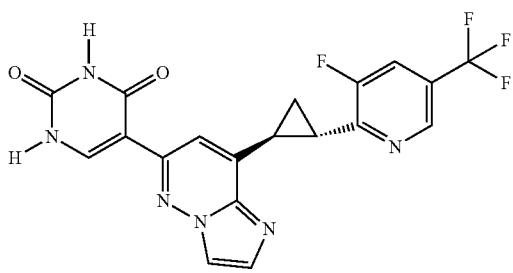 [SMILES: O=c1[nH]cc(-c2cc([C@H]3C[C@@H]3c3ncc(C(F)(F)F)cc3F)c3nccn3n2)c(=O)[nH]1]

5-(8-((1S,2S)-2-(3-fluoro-5-(trifluoromethyl)pyridin-2-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(3-fluoro-5-(trifluoromethyl)pyridin-2-yl)cyclopropyl)imidazo[1,2-b]pyridazine (Racemic Mixture). ES/MS m/z: 433.10 [M+H]. $^1$H NMR (400 MHz, Methanol-d4) δ 8.71 (s, 1H), 8.30 (s, 1H), 8.25 (s, 1H), 8.02-7.97 (m, 1H), 7.97-7.90 (m, 2H), 3.22-3.14 (m, 2H), 2.24-2.14 (m, 1H), 2.11 2.02 (m, 1H). $^{19}$F NMR (376 MHz, Methanol-d4) δ −64.00, −77.76, −129.81-130.33 (m).

Example 583. 5-(8-((2S,2S)-2-(5-chloro-3-fluoropyridin-2-yl)cyclopropyl)-3-fluoroimidazo[1,2-b]pyridazin-6-yl)pyrimidine-2,4(1H,3H)-dione (Racemic Mixture)

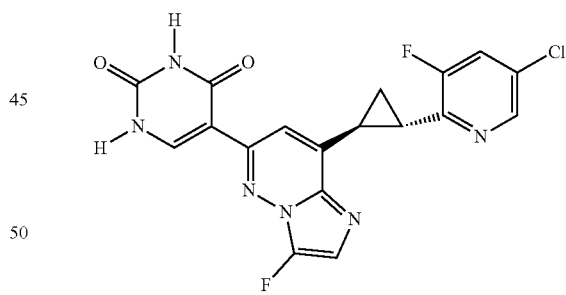

5-(8-((2S,2S)-2-(5-chloro-3-fluoropyridin-2-yl)cyclopropyl)-3-fluoroimidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((2S,2S)-2-(5-chloro-3-fluoropyridin-2-yl)cyclopropyl)-6-(2,4-dimethoxypyrimidin-5-yl)-3-fluoroimidazo[1,2-b]pyridazine (racemic mixture). ES/MS m/z: 417.10 [M+H]. $^1$H NMR (400 MHz, Methanol-d4) δ 8.37 (d, J=2.0 Hz, 1H), 8.21 (s, 1H), 7.74 (s, 1H), 7.69 (dd, J=9.4, 2.0 Hz, 1H), 7.51 (d, J=6.6 Hz, 1H), 3.16-2.99 (m, 2H), 2.11-1.97 (m, 2H). $^{19}$F NMR (376 MHz, Methanol-d4) δ −78.15, −129.11 (d, J=9.2 Hz), −156.91 (d, J=6.8 Hz).

Example 584. 5-(8-((2S,2S)-2-(5-chloropyridin-2-yl)cyclopropyl)-3-fluoroimidazo[1,2-b]pyridazin-6-yl)pyrimidine-2,4(1H,3H)-dione

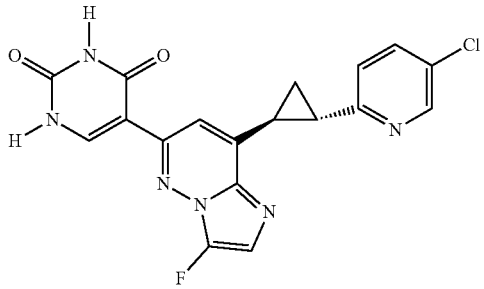 [SMILES: O=c1[nH]cc(-c2cc([C@H]3C[C@@H]3c3ccc(Cl)cn3)c3ncc(F)n3n2)c(=O)[nH]1]

5-(8-((1S,2S)-2-(5-chloropyridin-2-yl)cyclopropyl)-3-fluoroimidazo[1,2-b]pyridazin-6-yl)pyrimidine-2,4(1H, 3H)-dione was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(5-chloropyridin-2-yl)cyclopropyl)-6-(2,4-dimethoxypyrimidin-5-yl)-3-fluoroimidazo[1,2-b]pyridazine. ES/MS m/z: 399.10 [M+H]. $^1$H NMR (400 MHz, Methanol-d4) δ 8.48 (d, J=2.5 Hz, 1H), 8.21 (s, 1H), 7.74 (dd, J=8.4, 2.5 Hz, 1H), 7.70 (s, 1H), 7.53-7.46 (m, 1H), 7.40 (d, J=8.4 Hz, 1H), 3.06-2.97 (m, 1H), 2.94-2.86 (m, 1H), 2.05-1.92 (m, 2H).

Example 585. 5-(8-((2S,2S)-2-(5-chloropyridin-2-yl)cyclopropyl)imidazo[1,2-b]pyridazin-6-yl)pyrimidine-2,4(1H,3H)-dione

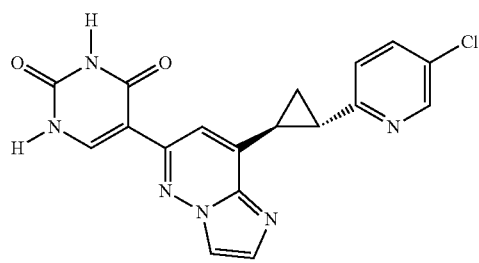 [SMILES: O=c1[nH]cc(-c2cc([C@H]3C[C@@H]3c3ccc(Cl)cn3)c3nccn3n2)c(=O)[nH]1]

5-(8-((1S,2S)-2-(5-chloropyridin-2-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(5-chloropyridin-2-yl)cyclopropyl)-6-(2,4-dimethoxypyrimidin-5-yl)imidazo[1,2-b]pyridazine. ES/MS m/z: 381.10 [M+H]. $^1$H NMR (400 MHz, Methanol-d4) δ8.51 (d, J=2.5 Hz, 1H), 8.40 (d, J=2.0 Hz, 1H), 8.30 (s, 1H), 8.11 (s, 1H), 8.10 (d, J=2.0 Hz, 1H), 7.76 (dd, J=8.3, 2.5 Hz, 1H), 7.47-7.41 (m, 1H), 3.05-2.96 (m, 1H), 2.92-2.81 (m, 1H), 2.14-2.06 (m, 1H), 1.96-1.85 (m, 1H).

Example 586. 5-(8-((2S,2S)-2-(5-chloro-3-fluoropyridin-2-yl)cyclopropyl)imidazo[1,2-b]pyridazin-6-yl)pyrimidine-2,4(1H,3H)-dione

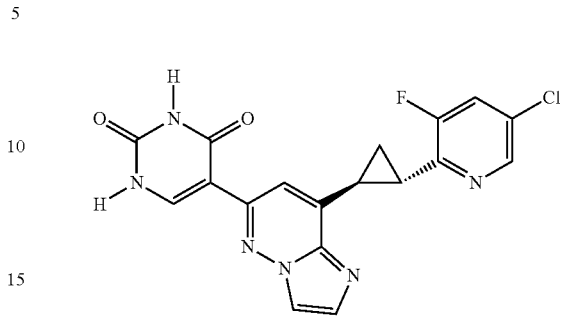

5-(8-((1S,2S)-2-(5-chloro-3-fluoropyridin-2-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(5-chloro-3-fluoropyridin-2-yl)cyclopropyl)-6-(2,4-dimethoxypyrimidin-5-yl)imidazo[1,2-b]pyridazine. ES/MS m/z: 399.10 [M+H]. $^1$H NMR (400 MHz, Methanol-d4) δ8.40 (d, J=2.0 Hz, 2H), 8.30 (s, 1H), 8.14 (s, 1H), 8.09 (d, J=2.0 Hz, 1H), 7.74 (dd, J=9.4, 2.0 Hz, 1H), 3.12-3.01 (m, 2H), 2.19-2.10 (m, 1H), 2.01-1.92 (m, 1H).

Example 587. 5-(8-(8,8-difluoro-2-azaspiro[4.5]decan-2-yl)imidazo[1,2-b]pyridazin-6-yl)pyrimidine-2,4(1H,3H)-dione

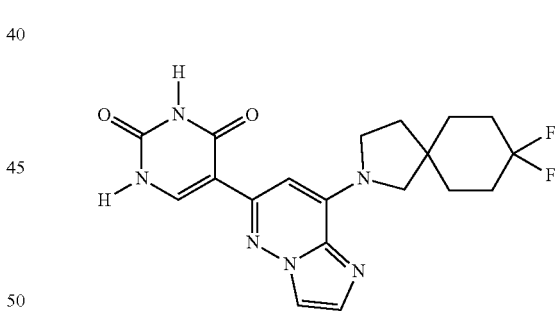

5-(8-(8,8-difluoro-2-azaspiro[4.5]decan-2-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 2-(6-(2,4-dimethoxypyrimidin-5-yl)imidazo[1,2-b]pyridazin-8-yl)-8,8-difluoro-2-azaspiro[4.5]decane. ES/MS m/z: 403.10 [M+H]. $^1$H NMR (400 MHz, Methanol-d4) δ 8.15 (s, 1H), 8.09-8.05 (m, 1H), 7.79-7.71 (m, 1H), 6.98 (s, 1H), 3.99-3.87 (m, 2H), 3.87-3.77 (m, 2H), 2.12-1.91 (m, 6H), 1.85-1.70 (m, 4H). $^{19}$F NMR (376 MHz, Methanol-d4) δ −97.66--101.57 (m).

Example 588. 5-(8-((2S,2S)-2-(5-chloro-3-fluoropyridin-2-yl)cyclopropyl)-3-fluoroimidazo[1,2-b]pyridazin-6-yl)pyrimidine-2,4(1H,3H)-dione

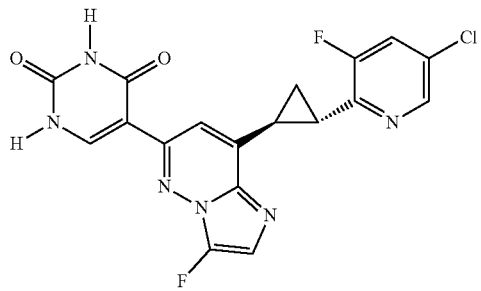 [SMILES: O=c1[nH]cc(-c2cc([C@H]3C[C@@H]3c3ncc(Cl)cc3F)c3ncc(F)n3n2)c(=O)[nH]1]

5-(8-((1S,2S)-2-(5-chloro-3-fluoropyridin-2-yl)cyclopropyl)-3-fluoroimidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 8-((2S,2S)-2-(5-chloro-3-fluoropyridin-2-yl)cyclopropyl)-6-(2,4-dimethoxypyrimidin-5-yl)-3-fluoroimidazo[1,2-b]pyridazine. ES/MS m/z: 417.10 [M+H]. $^1$H NMR (400 MHz, Methanol-d4) δ 8.38 (d, J=2.0 Hz, 1H), 8.21 (s, 1H), 7.74 (s, 1H), 7.69 (dd, J=9.4, 2.0 Hz, 1H), 7.50 (d, J=6.6 Hz, 1H), 3.15-3.01 (m, 2H), 2.11-1.99 (m, 2H).

Example 589. 5-(8-((2S,2S)-2-(2-(difluoromethyl)benzo[d]thiazol-6-yl)cyclopropyl)imidazo[1,2-b]pyridazin-6-yl)pyrimidine-2,4(1H,3H)-dione (Racemic Mixture)

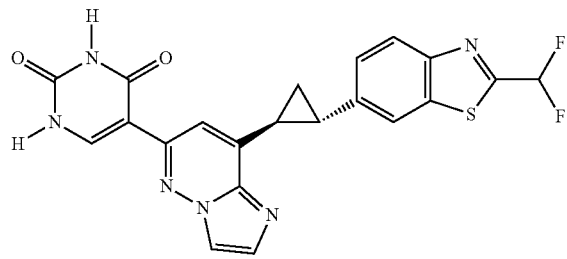 [SMILES: O=c1[nH]cc(-c2cc([C@H]3C[C@@H]3c3ccc4nc(C(F)F)sc4c3)c3nccn3n2)c(=O)[nH]1]

5-(8-((1S,2S)-2-(2-(difluoromethyl)benzo[d]thiazol-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 2-(difluoromethyl)-6-((1S,2S)-2-(6-(2,4-dimethoxypyrimidin-5-yl)imidazo[1,2-b]pyridazin-8-yl)cyclopropyl)benzo[d]thiazole (racemic mixture). ES/MS m/z: 453.10 [M+H]. $^1$H NMR (400 MHz, Methanol-d4) δ 8.36 (d, J=1.9 Hz, 1H), 8.29 (s, 1H), 8.12-7.98 (m, 4H), 7.54 (dd, J=8.6, 1.8 Hz, 1H), 7.13 (t, J=54.3 Hz, 1H), 2.97-2.88 (m, 1H), 2.87-2.79 (m, 1H), 2.08-1.97 (m, 2H). $^{19}$F NMR (376 MHz, Methanol-d4) δ −77.80, −112.83 (d, J=54.7 Hz).

Example 590. 5-(8-((2S,2S)-2-(5-(2,2-difluoroethoxy)pyridin-2-yl)cyclopropyl)imidazo[1,2-b]pyridazin-6-yl)pyrimidine-2,4(1H,3H)-dione (Racemic Mixture)

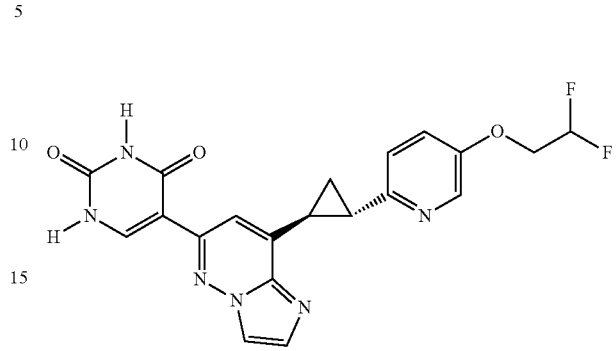

5-(8-((2S,2S)-2-(5-(2,2-difluoroethoxy)pyridin-2-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(5-(2,2-difluoroethoxy)pyridin-2-yl)cyclopropyl)-6-(2,4-dimethoxypyrimidin-5-yl)imidazo[1,2-b]pyridazine (Racemic Mixture). ES/MS m/z: 427.20 [M+H]. $^1$H NMR (400 MHz, Methanol-d4) δ 8.36 (d, J=2.0 Hz, 1H), 8.29 (d, J=2.9 Hz, 1H), 8.28 (s, 1H), 8.05-8.01 (m, 2H), 7.52-7.39 (m, 2H), 6.20 (tt, J=54.7, 3.7 Hz, 1H), 4.34 (td, J=13.8, 3.7 Hz, 2H), 2.09-2.02 (m, 1H), 1.95-1.86 (m, 1H). $^{19}$F NMR (376 MHz, Methanol-d4) δ −77.81, −128.44 (dt, J=54.8, 13.8 Hz).

Example 591. 5-(8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture)

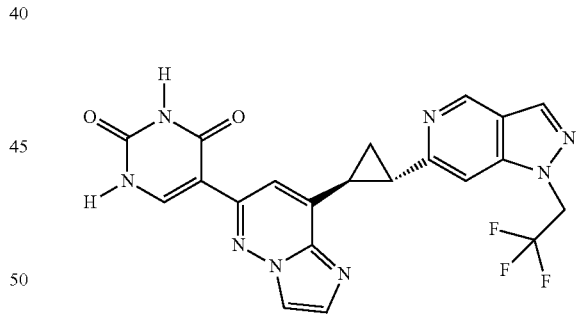

5-(8-((2S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[4,3-c]pyridine (Racemic Mixture). ES/MS m/z: 469.20 [M+H]. $^1$H NMR (400 MHz, Methanol-d4) δ 9.38 (s, 1H), 8.66 (s, 1H), 8.40 (d, J=1.9 Hz, 1H), 8.32 (s, 1H), 8.14 (s, 1H), 8.13 (s, 1H), 8.08 (d, J=1.9 Hz, 1H), 5.44 (q, J=8.6 Hz, 2H), 3.13 (t, J=7.5 Hz, 2H), 2.34 2.22 (m, 1H), 2.22-2.12 (m, 1H). $^{19}$F NMR (376 MHz, Methanol-d4) δ −72.77 (t, J=8.6 Hz), −78.01.

Example 592. 5-(8-(3-((1H-1,2,3-triazol-1-yl)methyl)pyrrolidin-1-yl)imidazo[1,2-b]pyridazin-6-yl)pyrimidine-2,4(1H,3H)-dione

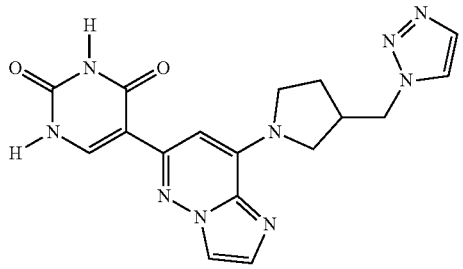 [SMILES: O=c1[nH]cc(-c2cc(N3CCC(Cn4ccnn4)C3)c3nccn3n2)c(=O)[nH]1]

5-(8-(3-((1H-1,2,3-triazol-1-yl)methyl)pyrrolidin-1-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 8-(3-((1H-1,2,3-triazol-1-yl)methyl)pyrrolidin-1-yl)-6-(2,4-dimethoxypyrimidin-5-yl)imidazo[1,2-b]pyridazine. ES/MS m/z: 380.20 [M+H]. $^1$H NMR (400 MHz, Methanol-d4) δ 8.22 (s, 1H), 8.19 (d, J=2.0 Hz, 1H), 8.11-8.07 (m, 1H), 7.89 (d, J=2.0 Hz, 1H), 7.79-7.76 (m, 1H), 7.23 (s, 1H), 4.65 (d, J=7.2 Hz, 2H), 4.06-3.94 (m, 2H), 3.94-3.83 (m, 1H), 3.79-3.65 (m, 1H), 3.16-3.02 (m, 1H), 2.35-2.21 (m, 1H), 2.07-1.93 (m, 1H). $^{19}$F NMR (376 MHz, Methanol-d4) δ −77.95.

Example 593. 5-(8-(3-(prop-2-yn-1-yl)pyrrolidin-1-yl)imidazo[1,2-b]pyridazin-6-yl)pyrimidine-2,4(1H,3H)-dione

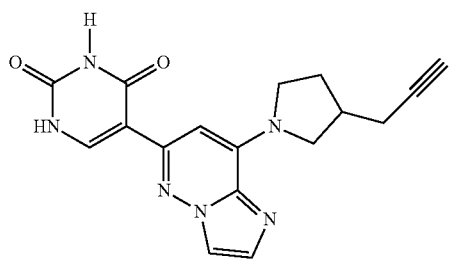 [SMILES: C#CCC1CCN(c2cc(-c3c[nH]c(=O)[nH]c3=O)nn3ccnc23)C1]

5-(8-(3-(prop-2-yn-1-yl)pyrrolidin-1-yl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-(3-(prop-2-yn-1-yl)pyrrolidin-1-yl)imidazo[1,2-b]pyridazine. ES/MS m/z: 337.20 [M+H]. $^1$H NMR (400 MHz, Methanol-d4) δ 8.18 (s, 1H), 8.11 (d, J=1.8 Hz, 1H), 7.80 (d, J=1.8 Hz, 1H), 7.10 (s, 1H), 4.11-3.94 (m, 2H), 3.93-3.80 (m, 1H), 3.71-3.61 (m, 1H), 2.73-2.56 (m, 1H), 2.50-2.43 (m, 2H), 2.38 (t, J=2.6 Hz, 1H), 2.35-2.25 (m, 1H), 2.07-1.96 (m, 1H).

Example 594. 5-(8-((2S,2S)-2-(7-fluoro-1-(2,2,2-trifluoroethyl)-1H-indazol-6-yl)cyclopropyl)imidazo[1,2-b]pyridazin-6-yl)pyrimidine-2,4(1H,3H)-dione

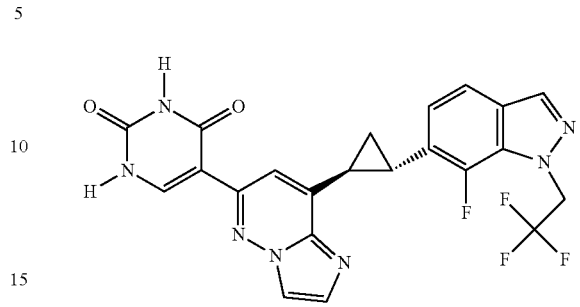

5-(8-((1S,2S)-2-(7-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(7-fluoro-1-(2,2,2-trifluoroethyl)-1H-indazol-6-yl)cyclopropyl)imidazo[1,2-b]pyridazine. ES/MS m/z: 486.20 [M+H]. $^1$H NMR (400 MHz, Methanol-d4) δ 8.37 (d, J=1.9 Hz, 1H), 8.29 (s, 1H), 8.14 (d, J=2.3 Hz, 1H), 8.09 (s, 1H), 8.06 (d, J=1.9 Hz, 1H), 7.61 (d, J=8.4 Hz, 1H), 7.07 (dd, J=8.4, 6.0 Hz, 1H), 5.22 (q, J=8.5 Hz, 2H), 3.09-2.99 (m, 1H), 2.91-2.80 (m, 1H), 2.08-1.96 (m, 2H). $^{19}$F NMR (376 MHz, Methanol-d4) δ −73.69--73.79 (m), −77.83, −143.15--143.26 (m).

Example 595. 5-(8-((2S,2S)-2-(5-fluoro-1-(2,2,2-trifluoroethyl)-1H-indazol-6-yl)cyclopropyl)imidazo[1,2-b]pyridazin-6-yl)pyrimidine-2,4(1H,3H)-dione

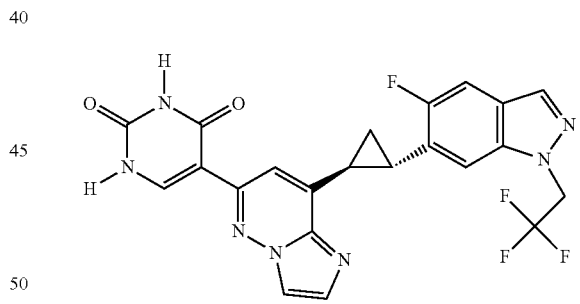

5-(8-((2S,2S)-2-(5-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(5-fluoro-1-(2,2,2-trifluoroethyl)-1H-indazol-6-yl)cyclopropyl)imidazo[1,2-b]pyridazine. ES/MS m/z: 486.20 [M+H]. $^1$H NMR (400 MHz, Methanol-d4) δ 8.36 (d, J=1.9 Hz, 1H), 8.28 (s, 1H), 8.09 (s, 1H), 8.05 (s, 1H), 8.03 (d, J=1.9 Hz, 1H), 7.63 (d, J=5.8 Hz, 1H), 7.49 (d, J=10.0 Hz, 1H), 5.24 (q, J=8.7 Hz, 2H), 2.99-2.90 (m, 1H), 2.80-2.72 (m, 1H), 2.16-2.05 (m, 1H), 2.02-1.94 (m, 1H). $^{19}$F NMR (376 MHz, Methanol-d4) δ −72.97 (t, J=8.7 Hz), −77.81, −128.41 (dd, J=10.0, 5.8 Hz).

Example 596. 5-(8-((2S,2S)-2-(4-fluoro-1-(2,2,2-trifluoroethyl)-1H-indazol-6-yl)cyclopropyl)imidazo[1,2-b]pyridazin-6-yl)pyrimidine-2,4(1H,3H)-dione

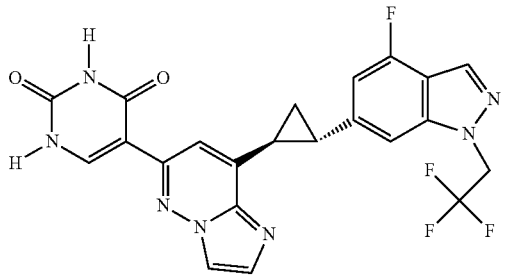 [SMILES: O=c1[nH]cc(-c2cc([C@H]3C[C@@H]3c3cc(F)c4cnn(CC(F)(F)F)c4c3)c3nccn3n2)c(=O)[nH]1]

5-(8-((1S,2S)-2-(4-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(4-fluoro-1-(2,2,2-trifluoroethyl)-1H-indazol-6-yl)cyclopropyl)imidazo[1,2-b]pyridazine. ES/MS m/z: 486.10 [M+H]. $^1$H NMR (400 MHz, Methanol-d4) δ 8.37 (d, J=1.9 Hz, 1H), 8.29 (s, 1H), 8.16-8.14 (m, 1H), 8.05 (d, J=1.9 Hz, 1H), 8.03 (s, 1H), 7.45 (s, 1H), 6.90-6.84 (m, 1H), 5.22 (q, J=8.7 Hz, 2H), 2.98-2.88 (m, 1H), 2.87-2.78 (m, 1H), 2.08-1.95 (m, 2H). $^{19}$F NMR (376 MHz, Methanol-d4) δ −72.90 (t, J=8.6 Hz), −77.85, −120.87 (d, J=11.0 Hz).

Example 597. 5-(8-((2S,2S)-2-(5-chloro-4-(2,2-difluorocyclopropyl)methoxy)pyridin-2-yl)cyclopropyl)imidazo[1,2-b]pyridazin-6-yl)pyrimidine-2,4(1H,3H)-dione (Racemic Mixture)

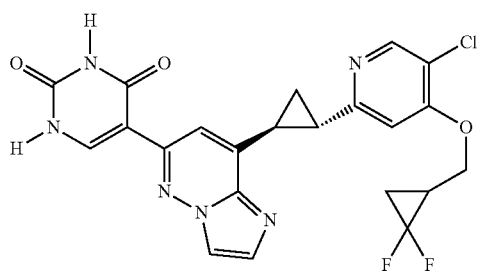 [SMILES: O=c1[nH]cc(-c2cc([C@H]3C[C@@H]3c3cc(OCC4CC4(F)F)c(Cl)cn3)c3nccn3n2)c(=O)[nH]1]

5-(8-((1S,2S)-2-(5-chloro-4-((2,2-difluorocyclopropyl)methoxy)pyridin-2-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(5-chloro-4-((2,2-difluorocyclopropyl)methoxy)pyridin-2-yl)cyclopropyl)-6-(2,4-dimethoxypyrimidin-5-yl)imidazo[1,2-b]pyridazine (Racemic Mixture). ES/MS m/z: 487.10 [M+H]. $^1$H NMR (400 MHz, Methanol-d4) δ 8.41 (s, 1H), 8.39 (d, J=2.0 Hz, 1H), 8.30 (s, 1H), 8.09 (s, 1H), 8.08 (d, J=2.0 Hz, 1H), 7.24 (s, 1H), 4.42-4.32 (m, 1H), 4.32-4.20 (m, 1H), 3.07-2.96 (m, 1H), 2.90-2.82 (m, 1H), 2.32-2.17 (m, 1H), 2.16-2.07 (m, 1H), 1.98-1.90 (m, 1H), 1.77-1.64 (m, 1H), 1.50-1.37 (m, 1H). $^{19}$F NMR (376 MHz, Methanol-d4) δ −77.97, −131.12−−131.83 (m), −145.29−−145.94 (m).

Example 598. 5-(8-((2S,2S)-2-(2-oxo-1-(2,2,2-trifluoroethyl)-1,2-dihydroquinolin-7-yl)cyclopropyl)imidazo[1,2-b]pyridazin-6-yl)pyrimidine-2,4(1H,3H)-dione (Racemic Mixture)

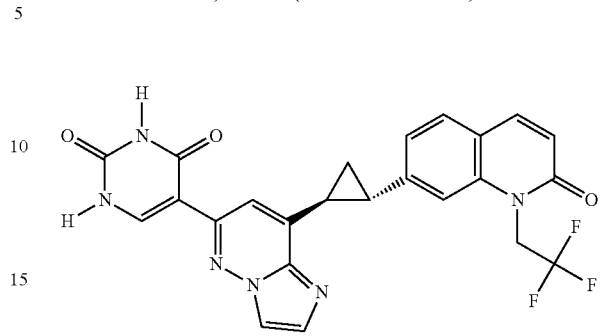

5-(8-((1S,2S)-2-(2-oxo-1-(2,2,2-trifluoroethyl)-1,2-dihydroquinolin-7-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 7-((1S,2S)-2-(6-(2,4-dimethoxypyrimidin-5-yl)imidazo[1,2-b]pyridazin-8-yl)cyclopropyl)-1-(2,2,2-trifluoroethyl)quinolin-2(1H)-one (Racemic Mixture). ES/MS m/z: 495.20 [M+H]. $^1$H NMR (400 MHz, Methanol-d4) δ 8.41 (d, J=2.0 Hz, 1H), 8.31 (s, 1H), 8.13-8.07 (m, 2H), 7.96 (d, J=9.5 Hz, 1H), 7.72 (d, J=8.1 Hz, 1H), 7.58 (s, 1H), 7.29-7.18 (m, 1H), 6.67 (d, J=9.5 Hz, 1H), 5.34-5.10 (m, 2H), 2.96-2.88 (m, 1H), 2.88-2.81 (m, 1H), 2.10-1.98 (m, 2H). $^{19}$F NMR (376 MHz, Methanol-d4) δ −69.85 (t, J=8.7 Hz).

Example 599. 5-(8-((1S,2S)-2-(2-(2,2,2-trifluoroethoxy)quinolin-7-yl)cyclopropyl)imidazo[1,2-b]pyridazin-6-yl)pyrimidine-2,4(1H,3H)-dione (Racemic Mixture)

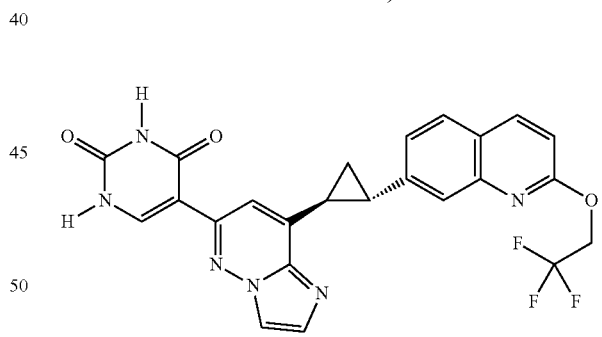

5-(8-((1S,2S)-2-(2-(2,2,2-trifluoroethoxy)quinolin-7-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 7-((1S,2S)-2-(6-(2,4-dimethoxypyrimidin-5-yl)imidazo[1,2-b]pyridazin-8-yl)cyclopropyl)-2-(2,2,2-trifluoroethoxy)quinoline (racemic mixture). ES/MS m/z: 495.10 [M+H]. $^1$H NMR (400 MHz, Methanol-d4) δ 8.36-8.32 (m, 1H), 8.28 (s, 1H), 8.20 (d, J=8.8 Hz, 1H), 8.03-7.99 (m, 1H), 7.82 (d, J=8.4 Hz, 1H), 7.75-7.72 (m, 1H), 7.40 (dd, J=8.4, 1.8 Hz, 1H), 7.02 (d, J=8.8 Hz, 1H), 5.08-4.97 (m, 2H), 2.94-2.86 (m, 2H), 2.09-1.96 (m, 2H). $^{19}$F NMR (376 MHz, Methanol-d4) δ −75.96 (t, J=8.7 Hz), −77.74.

Example 600. 5-(8-((2S,2S)-2-(5-chloro-4-(2,2,2-trifluoroethoxy)pyridin-2-yl)cyclopropyl)imidazo[1,2-b]pyridazin-6-yl)pyrimidine-2,4(1H,3H)-dione (Racemic Mixture)

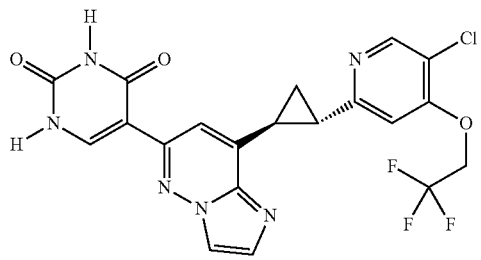 [SMILES: O=c1[nH]cc(-c2cc([C@H]3C[C@@H]3c3cc(OCC(F)(F)F)c(Cl)cn3)c3nccn3n2)c(=O)[nH]1]

5-(8-((2S,2S)-2-(5-chloro-4-(2,2,2-trifluoroethoxy)pyridin-2-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(5-chloro-4-(2,2,2-trifluoroethoxy)pyridin-2-yl)cyclopropyl)-6-(2,4-dimethoxypyrimidin-5-yl)imidazo[1,2-b]pyridazine (Racemic Mixture). ES/MS m/z: 479.10 [M+H]. $^1$H NMR (400 MHz, Methanol-d4) δ 8.43 (s, 1H), 8.40 (d, J=2.0 Hz, 1H), 8.31 (s, 1H), 8.11 (s, 1H), 8.10 (d, J=2.0 Hz, 1H), 7.30 (s, 1H), 4.84-4.75 (m, 2H), 3.07-2.98 (m, 1H), 2.92-2.78 (m, 1H), 2.16-2.05 (m, 1H), 1.96 1.86 (m, 1H). $^{19}$F NMR (376 MHz, Methanol-d4) δ −76.13 (t, J=8.2 Hz), −77.93.

Example 601. 5-(8-((2S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione (Racemic Mixture)

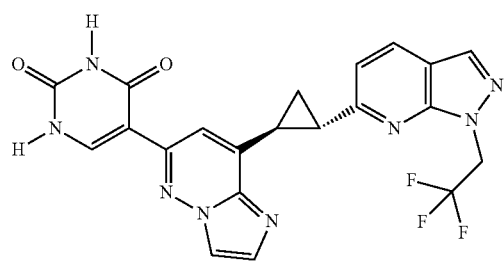

5-(8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[3,4-b]pyridine (Racemic Mixture). ES/MS m/z: 469.20 [M+H]. $^1$H NMR (400 MHz, Methanol-d4) δ 8.36 (d, J=1.9 Hz, 1H), 8.29 (s, 1H), 8.14 (d, J=8.2 Hz, 1H), 8.14 (s, 1H), 8.08 (s, 1H), 8.03 (d, J=1.9 Hz, 1H), 7.37 (d, J=8.2 Hz, 1H), 5.35-5.09 (m, 2H), 3.21-3.13 (m, 1H), 3.09-3.00 (m, 1H), 2.29-2.20 (m, 1H), 2.00-1.91 (m, 1H). $^{19}$F NMR (376 MHz, Methanol-d4) δ −72.76 (t, J=8.8 Hz), −77.73.

Example 602. 5-(3-fluoro-8-((2S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione (Racemic Mixture)

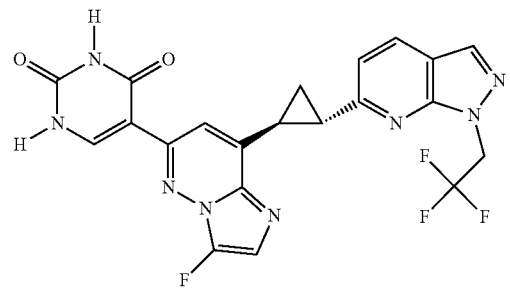 [SMILES: O=c1[nH]cc(-c2cc([C@H]3C[C@@H]3c3ccc4cnn(CC(F)(F)F)c4n3)c3ncc(F)n3n2)c(=O)[nH]1]

5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((2S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[3,4-b]pyridine (Racemic Mixture). ES/MS m/z: 487.10 [M+H]. $^1$H NMR (400 MHz, Methanol-d4) δ 8.21 (s, 1H), 8.12 (s, 1H), 8.12 (d, J=8.2 Hz, 1H), 7.71 (s, 1H), 7.48 (d, J=6.6 Hz, 1H), 7.33 (d, J=8.2 Hz, 1H), 5.36-5.08 (m, 2H), 3.27-3.18 (m, 1H), 3.12-3.04 (m, 1H), 2.20-2.12 (m, 1H), 2.07-1.99 (m, 1H). $^{19}$F NMR (376 MHz, Methanol-d4) δ −72.81 (t, J=8.8 Hz), −78.13, −157.05 (d, J=6.6 Hz).

Example 603. 5-(8-((2S,2S)-2-(1-(2,2,2-trifluoroethyl)-2-(trifluoromethyl)-1H-benzo[d]imidazol-6-yl)cyclopropyl)imidazo[1,2-b]pyridazin-6-yl)pyrimidine-2,4(1H,3H)-dione (Racemic Mixture)

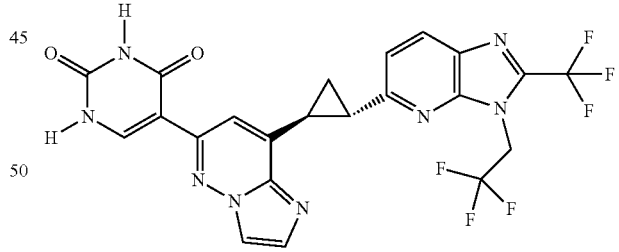

5-(8-((1S,2S)-2-(1-(2,2,2-trifluoroethyl)-2-(trifluoromethyl)-1H-benzo[d]imidazol-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(1-(2,2,2-trifluoroethyl)-2-(trifluoromethyl)-1H-benzo[d]imidazol-6-yl)cyclopropyl)imidazo[1,2-b]pyridazine (Racemic Mixture). ES/MS m/z: 536.10 [M+H]. $^1$H NMR (400 MHz, Methanol-d4) δ 8.33 (d, J=1.8 Hz, 1H), 8.27 (s, 1H), 8.00 (d, J=1.8 Hz, 1H), 7.97 (s, 1H), 7.81 (d, J=8.6 Hz, 1H), 7.72 (s, 1H), 7.40 (dd, J=8.6, 1.6 Hz, 1H), 5.31 (q, J=8.4 Hz, 2H), 3.00-2.90

(m, 1H), 2.88-2.78 (m, 1H), 2.08-1.95 (m, 2H). $^{19}$F NMR (376 MHz, Methanol-d4) δ −63.38 (q, J=5.1 Hz), −72.15--72.27 (m), −77.80.

Example 604. 5-(3-fluoro-8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture)

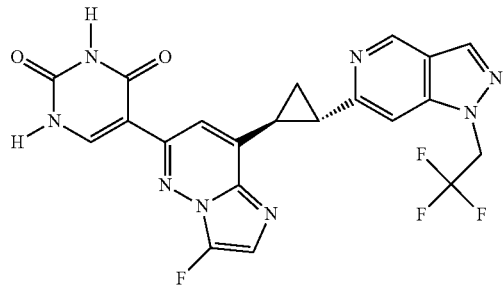 [SMILES: O=c1[nH]cc(-c2cc([C@H]3C[C@@H]3c3cc4c(cn3)cnn4CC(F)(F)F)c3ncc(F)n3n2)c(=O)[nH]1]

5-(3-fluoro-8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((2S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine (Racemic Mixture). ES/MS m/z: 487.00 [M+H]. $^1$H NMR (400 MHz, Methanol-d4) δ 9.37 (s, 1H), 8.68 (s, 1H), 8.22 (s, 1H), 8.15 (s, 1H), 7.75 (s, 1H), 7.45 (d, J=6.8 Hz, 1H), 5.46 (q, J=8.6 Hz, 2H), 3.29-3.20 (m, 1H), 3.11-3.03 (m, 1H), 2.35-2.26 (m, 1H), 2.19-2.09 (m, 1H). $^{19}$F NMR (376 MHz, Methanol-d4) δ −72.77 (t, J=8.6 Hz), −77.92, −157.20 (d, J=7.0 Hz).

Example 605. 5-(8-((2S,2S)-2-(3-(2,2,2-trifluoroethyl)imidazo[1,5-a]pyridin-6-yl)cyclopropyl)imidazo[1,2-b]pyridazin-6-yl)pyrimidine-2,4(1H,3H)-dione (Racemic Mixture)

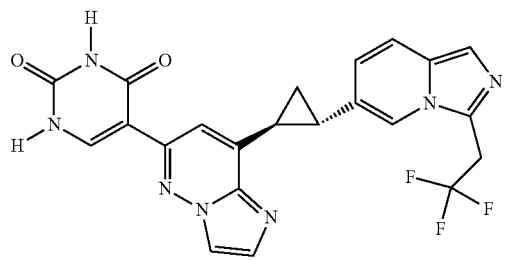 [SMILES: O=c1[nH]cc(-c2cc([C@H]3C[C@@H]3c3ccc4cnc(CC(F)(F)F)n4c3)c3nccn3n2)c(=O)[nH]1]

5-(8-((1S,2S)-2-(3-(2,2,2-trifluoroethyl)imidazo[1,5-a]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(3-(2,2,2-trifluoroethyl)imidazo[1,5-a]pyridin-6-yl)cyclopropyl)imidazo[1,2-b]pyridazine (Racemic Mixture). ES/MS m/z: 468.10 [M+H]. $^1$H NMR (400 MHz, Methanol-d4) δ8.41 (s, 1H), 8.32 (d, J=1.8 Hz, 1H), 8.27 (s, 1H), 7.99 (d, J=1.8 Hz, 1H), 7.94 (s, 1H), 7.74-7.68 (m, 2H), 6.99 (d, J=9.6 Hz, 1H), 4.31 (q, J=10.1 Hz, 2H), 2.92-2.70 (m, 2H), 2.01 1.88 (m, 2H). $^{19}$F NMR (376 MHz, Methanol-d4) δ −66.51 (t, J=10.1 Hz), −77.93.

Example 606. 5-(8-((2S,2S)-2-(2-(difluoromethyl)-1-(2,2,2-trifluoroethyl)-1H-benzo[d]imidazol-6-yl)cyclopropyl)imidazo[1,2-b]pyridazin-6-yl)pyrimidine-2,4(1H,3H)-dione (Racemic Mixture)

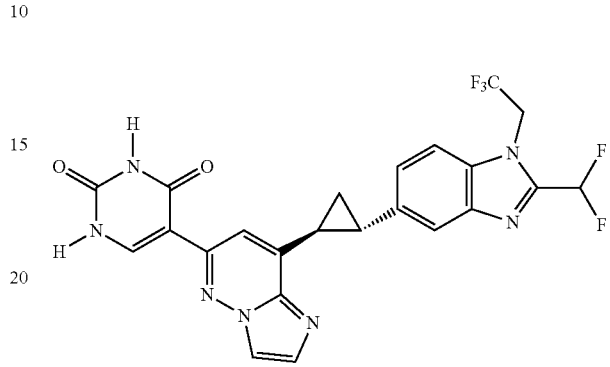

5-(8-((1S,2S)-2-(2-(difluoromethyl)-1-(2,2,2-trifluoroethyl)-1H-benzo[d]imidazol-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(2-(difluoromethyl)-1-(2,2,2-trifluoroethyl)-1H-benzo[d]imidazol-5-yl)cyclopropyl)-6-(2,4-dimethoxypyrimidin-5-yl)imidazo[1,2-b]pyridazine (Racemic Mixture). ES/MS m/z: 518.20 [M+H]. $^1$H NMR (400 MHz, Methanol-d4) δ 8.40 (d, J=2.0 Hz, 1H), 8.31 (s, 1H), 8.08 (d, J=2.0 Hz, 1H), 8.07 (s, 1H), 7.75-7.68 (m, 2H), 7.51-7.46 (m, 1H), 7.21 (t, J=52.1 Hz, 1H), 5.31 (q, J=8.5 Hz, 2H), 2.97-2.89 (m, 1H), 2.84-2.75 (m, 1H), 2.09-1.92 (m, 2H). $^{19}$F NMR (376 MHz, Methanol-d4) δ −72.28--72.39 (m), −77.83, −117.55--117.86 (m).

Example 607. 5-(8-((2S,2S)-2-(1-(2,2,2-trifluoroethyl)-3-(trifluoromethyl)-1H-indazol-6-yl)cyclopropyl)imidazo[1,2-b]pyridazin-6-yl)pyrimidine-2,4(1H,3H)-dione

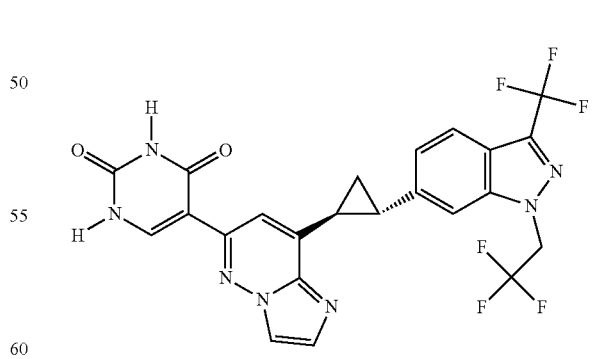

5-(8-((2S,2S)-2-(1-(2,2,2-trifluoroethyl)-3-(trifluoromethyl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5- yl)-8-((1S,2S)-2-(1-(2,2,2-trifluoroethyl)-3-(trifluoromethyl)-1H-indazol-6-yl)cyclopropyl)imidazo[1,2-b]pyridazine. ES/MS m/z: 536.20 [M+H]. ¹H NMR (400 MHz, Methanol-d4) δ 8.34 (d, J=1.8 Hz, 1H), 8.27 (s, 1H), 8.00 (d, J=1.8 Hz, 1H), 7.99 (s, 1H), 7.82 (d, J=8.6 Hz, 1H), 7.73 (s, 1H), 7.40-7.29 (m, 1H), 5.34 (q, J=8.6 Hz, 2H), 3.00-2.91 (m, 1H), 2.90-2.83 (m, 1H), 2.11-1.97 (m, 2H). ¹⁹F NMR (376 MHz, Methanol-d4) δ −63.29, −72.80 (t, J=8.6 Hz), −77.82.

Example 608. 5-(8-((2S,2S)-2-(1-(2,2,2-trifluoroethyl)-3-(trifluoromethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture)

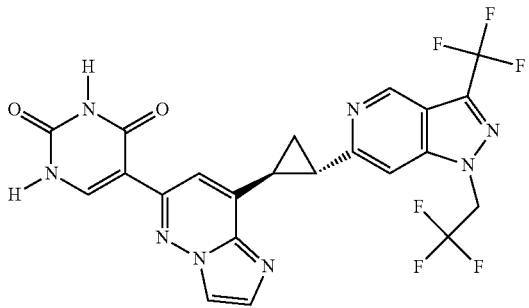 [SMILES: O=c1[nH]cc(-c2cc([C@H]3C[C@@H]3c3cc4c(cn3)c(C(F)(F)F)nn4CC(F)(F)F)c3nccn3n2)c(=O)[nH]1]

5-(8-((1S,2S)-2-(1-(2,2,2-trifluoroethyl)-3-(trifluoromethyl)-1H-pyrazolo[4,3-c]pyridin-6-yl)cyclopropyl)imidazo[1,2-b]pyridazin-6-yl)pyrimidine-2,4(1H,3H)-dione (racemic mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-1-(2,2,2-trifluoroethyl)-3-(trifluoromethyl)-1H-pyrazolo[4,3-c]pyridine (Racemic Mixture). ES/MS m/z: 537.10 [M+H]. ¹H NMR (400 MHz, Methanol-d4) δ 9.15 (s, 1H), 8.40 (d, J=2.0 Hz, 1H), 8.31 (s, 1H), 8.14 (s, 1H), 8.08 (d, J=2.0 Hz, 1H), 7.85 (s, 1H), 5.45-5.32 (m, 2H), 3.20-3.13 (m, 1H), 3.07-2.99 (m, 1H), 2.29-2.20 (m, 1H), 2.02-1.93 (m, 1H). ¹⁹F NMR (376 MHz, Methanol-d4) δ −63.29, −72.85 (t, J=8.6 Hz), −77.90.

Example 609. 5-(8-((1S,2S)-2-(3-(2,2,2-trifluoroethyl)-1-(trifluoromethyl)imidazo[1,5-a]pyridin-6-yl)cyclopropyl)imidazo[1,2-b]pyridazin-6-yl)pyrimidine-2,4(1H,3H)-dione (Racemic Mixture)

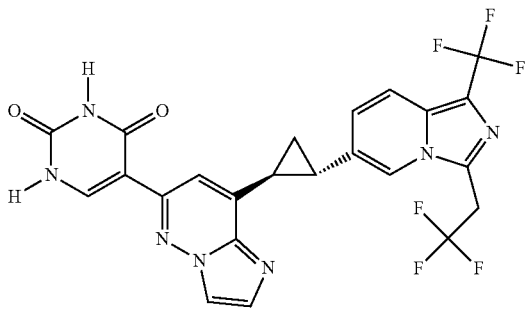 [SMILES: O=c1[nH]cc(-c2cc([C@H]3C[C@@H]3c3ccc4c(C(F)(F)F)nc(CC(F)(F)F)n4c3)c3nccn3n2)c(=O)[nH]1]

5-(8-((1S,2S)-2-(3-(2,2,2-trifluoroethyl)-1-(trifluoromethyl)imidazo[1,5-a]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(3-(2,2,2-trifluoroethyl)-1-(trifluoromethyl)imidazo[1,5-a]pyridin-6-yl)cyclopropyl)imidazo[1,2-b]pyridazine (Racemic Mixture). ES/MS m/z: 536.10 [M+H]. ¹H NMR (400 MHz, Methanol-d4) δ 8.42 (s, 1H), 8.36 (d, J=1.9 Hz, 1H), 8.28 (s, 1H), 8.04 (d, J=1.9 Hz, 1H), 8.01 (s, 1H), 7.76-7.68 (m, 1H), 7.17-7.08 (m, 1H), 4.20 (q, J=10.2 Hz, 2H), 2.86-2.77 (m, 2H), 2.04-1.89 (m, 2H). ¹⁹F NMR (376 MHz, Methanol-d4) δ −61.40, −66.48 (t, J=10.2 Hz), −77.90.

Example 610. 5-(3-fluoro-8-((2S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione

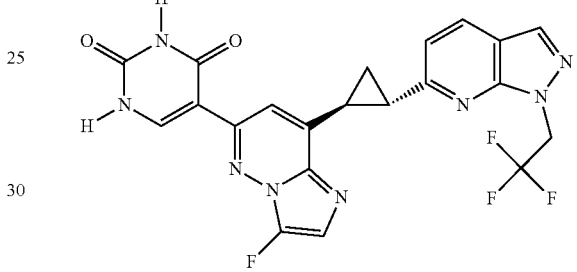

5-(3-fluoro-8-((2S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[3,4-b]pyridine. ES/MS m/z: 487.10 [M+H]. ¹H NMR (400 MHz, Methanol-d4) δ 8.20 (s, 1H), 8.12 (s, 1H), 8.12 (d, J=8.2 Hz, 1H), 7.67 (s, 1H), 7.43 (d, J=6.7 Hz, 1H), 7.33 (d, J=8.2 Hz, 1H), 5.35-5.07 (m, 2H), 3.26-3.20 (m, 1H), 3.11-3.04 (m, 1H), 2.20-2.11 (m, 1H), 2.07-1.98 (m, 1H).

Example 611. 5-(3-fluoro-8-((2S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione

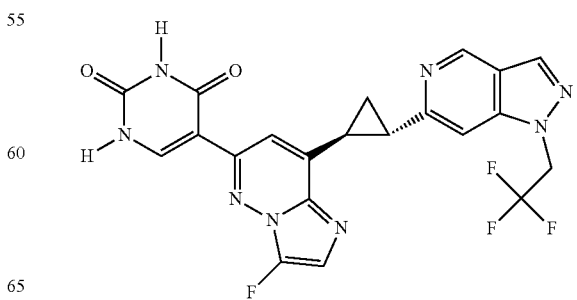

5-(3-fluoro-8-((2S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine. ES/MS m/z: 487.10 [M+H]. ¹H NMR (400 MHz, Methanol-d4) δ 9.42 (s, 1H), 8.74 (s, 1H), 8.24-8.20 (m, 2H), 7.77 (s, 1H), 7.47 (d, J=6.8 Hz, 1H), 5.49 (q, J=8.5 Hz, 2H), 3.30-3.25 (m, 1H), 3.15-3.02 (m, 1H), 2.40-2.27 (m, 1H), 2.19-2.11 (m, 1H).

Example 612. 5-(3-fluoro-8-((1R,2R)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione

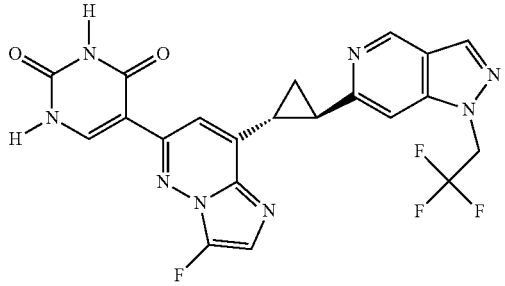 [SMILES: O=c1[nH]cc(-c2cc([C@@H]3C[C@H]3c3cc4c(cn3)cnn4CC(F)(F)F)c3ncc(F)n3n2)c(=O)[nH]1]

5-(3-fluoro-8-((1R,2R)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1R,2R)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-c]pyridine. ES/MS m/z: 487.10 [M+H]. ¹H NMR (400 MHz, Methanol-d4) δ 9.42 (d, J=0.9 Hz, 1H), 8.74 (d, J=0.9 Hz, 1H), 8.24-8.19 (m, 2H), 7.77 (s, 1H), 7.47 (d, J=6.8 Hz, 1H), 5.49 (q, J=8.5 Hz, 2H), 3.11-3.03 (m, 1H), 2.41-2.27 (m, 1H), 2.21-2.09 (m, 1H).

Example 613. 5-(3-fluoro-8-((1S,2S)-2-(5-fluoro-1-(2,2,2-trifluoroethyl)-1H-indazol-6-yl)cyclopropyl)imidazo[1,2-b]pyridazin-6-yl)pyrimidine-2,4(1H,3H)-dione

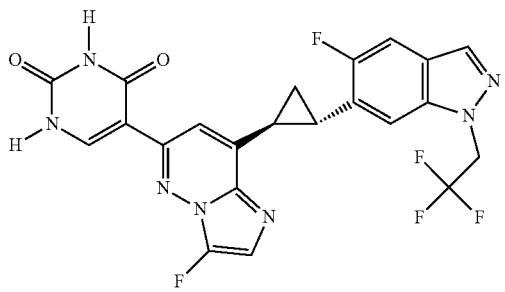 [SMILES: O=c1[nH]cc(-c2cc([C@H]3C[C@@H]3c3cc4c(cnn4CC(F)(F)F)cc3F)c3ncc(F)n3n2)c(=O)[nH]1]

5-(3-fluoro-8-((1S,2S)-2-(5-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((1S,2S)-2-(5-fluoro-1-(2,2,2-trifluoroethyl)-1H-indazol-6-yl)cyclopropyl)imidazo[1,2-b]pyridazine. ES/MS m/z: 504.10 [M+H]. ¹H NMR (400 MHz, Methanol-d4) δ 8.24 (s, 1H), 8.09 (d, J=1.0 Hz, 1H), 7.74 (s, 1H), 7.63 (d, J=5.8 Hz, 1H), 7.53 (d, J=6.6 Hz, 1H), 7.48 (d, J=9.9 Hz, 1H), 5.32-5.21 (m, 2H), 3.07-2.97 (m, 1H), 2.91-2.81 (m, 1H), 2.08-1.93 (m, 2H). ¹⁹F NMR (376 MHz, Methanol-d4) δ −73.00 (t, J=8.7 Hz), −78.15, −128.62−−128.72 (m), −157.01 (d, J=6.8 Hz).

Example 614. 5-(8-((2S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione (Racemic Mixture)

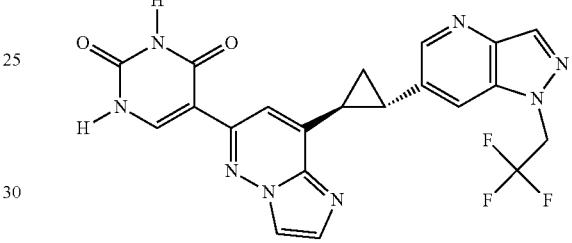

5-(8-((1S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-1-(2,2,2-trifluoroethyl)-1H-pyrazolo[4,3-b]pyridine (Racemic Mixture). ES/MS m/z: 469.20 [M+H]. ¹H NMR (400 MHz, Methanol-d4) δ 8.63 (d, J=1.5 Hz, 1H), 8.47 (d, J=2.0 Hz, 1H), 8.35 (s, 1H), 8.32 (s, 1H), 8.21 (s, 1H), 8.16 (d, J=2.0 Hz, 1H), 8.13 (s, 1H), 5.31 (q, J=8.7 Hz, 2H), 3.07-2.97 (m, 1H), 2.91 2.84 (m, 1H), 2.21-2.13 (m, 1H), 2.13-2.06 (m, 1H). ¹⁹F NMR (376 MHz, Methanol-d4) δ −72.99 (t, J=8.7 Hz), −78.12.

Example 615. 5-(8-((2S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture)

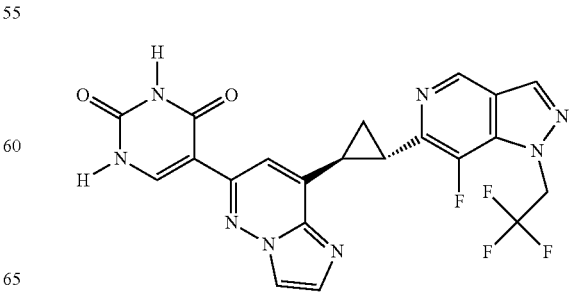

5-(8-((1S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-7-fluoro-1-(2,2,2-trifluoroethyl)-1H-pyrazolo[4,3-c]pyridine (Racemic Mixture). ES/MS m/z: 487.10 [M+H]. ¹H NMR (400 MHz, Methanol-d4) δ 8.90 (d, J=1.6 Hz, 1H), 8.42 (d, J=2.0 Hz, 1H), 8.35 (d, J=2.4 Hz, 1H), 8.32 (s, 1H), 8.21 (s, 1H), 8.10 (d, J=2.2 Hz, 1H), 5.27 (q, J=8.5 Hz, 2H), 3.24-3.13 (m, 2H), 2.29-2.17 (m, 1H), 2.07-1.97 (m, 1H). ¹⁹F NMR (376 MHz, Methanol-d4) δ −73.70−−73.81 (m), −77.98, −155.45−−155.76 (m).

Example 616. 5-(8-((2S,2S)-2-(1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione (Racemic Mixture)

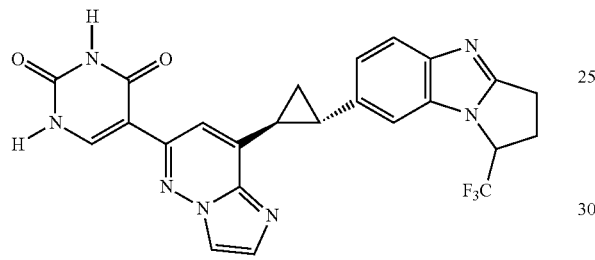

5-(8-((2S,2S)-2-(1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 7-((1S,2S)-2-(6-(2,4-dimethoxypyrimidin-5-yl)imidazo[1,2-b]pyridazin-8-yl)cyclopropyl)-1-(trifluoromethyl)-2,3-dihydro-1H-benzo[d]pyrrolo[1,2-a]imidazole (Racemic Mixture). ES/MS m/z: 494.20 [M+H]. ¹H NMR (400 MHz, Methanol-d4) δ 8.46-8.39 (m, 1H), 8.36-8.31 (m, 1H), 8.17-8.09 (m, 1H), 7.80-7.74 (m, 1H), 7.72-7.66 (m, 1H), 7.55-7.45 (m, 1H), 5.76-5.56 (m, 1H), 3.61-3.48 (m, 1H), 3.47-3.35 (m, 1H), 3.33-3.18 (m, 1H), 3.08-2.93 (m, 2H), 2.93-2.80 (m, 1H), 2.11-1.95 (m, 2H). ¹⁹F NMR (376 MHz, Methanol-d4) δ −76.50−−76.67 (m), −77.96.

Example 617. 5-(8-((2S,2S)-2-(1-(1,1,1-trifluoropropan-2-yl)-1H-indazol-6-yl)cyclopropyl)imidazo[1,2-b]pyridazin-6-yl)pyrimidine-2,4(1H,3H)-dione

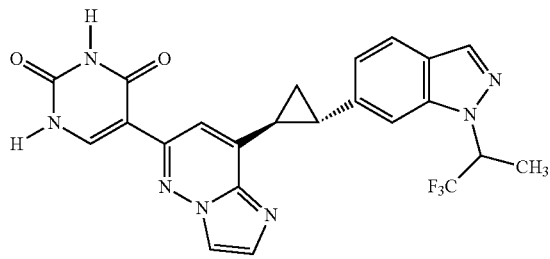 [SMILES: CC(n1ncc2ccc([C@H]3C[C@@H]3c3cc(-c4c[nH]c(=O)[nH]c4=O)nn4ccnc34)cc21)C(F)(F)F]

5-(8-((1S,2S)-2-(1-(1,1,1-trifluoropropan-2-yl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(1-(1,1,1-trifluoropropan-2-yl)-1H-indazol-6-yl)cyclopropyl)imidazo[1,2-b]pyridazine. ES/MS m/z: 482.20 [M+H]. ¹H NMR (400 MHz, Methanol-d4) δ 8.41-8.34 (m, 1H), 8.32-8.28 (m, 1H), 8.09 (s, 1H), 8.07-8.05 (m, 2H), 7.77-7.72 (m, 1H), 7.60 (s, 1H), 7.20-7.10 (m, 1H), 5.61-5.48 (m, 1H), 2.98-2.88 (m, 1H), 2.86-2.76 (m, 1H), 2.12-2.02 (m, 1H), 2.02-1.94 (m, 1H), 1.90-1.82 (m, 3H). ¹⁹F NMR (376 MHz, Methanol-d4) δ −77.17 (d, J=7.1 Hz), −77.26 (d, J=7.1 Hz), −77.82.

Example 618. 5-(3-fluoro-8-((2S,2S)-2-(4-fluoro-1-(2,2,2-trifluoroethyl)-1H-indazol-6-yl)cyclopropyl)imidazo[1,2-b]pyridazin-6-yl)pyrimidine-2,4(1H,3H)-dione

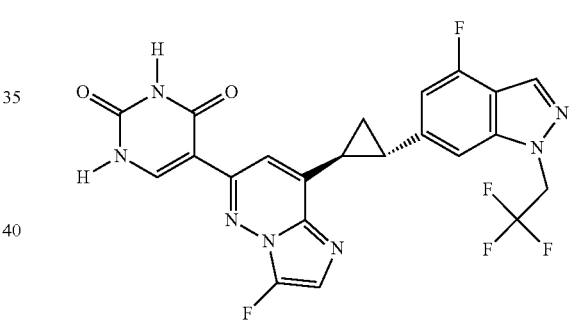

5-(3-fluoro-8-((2S,2S)-2-(4-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((2S,2S)-2-(4-fluoro-1-(2,2,2-trifluoroethyl)-1H-indazol-6-yl)cyclopropyl)imidazo[1,2-b]pyridazine. ES/MS m/z: 504.20 [M+H]. ¹H NMR (400 MHz, Methanol-d4) δ 8.22 (s, 1H), 8.13 (s, 1H), 7.68 (s, 1H), 7.51 (d, J=6.6 Hz, 1H), 7.42 (s, 1H), 6.86 (d, J=11.1 Hz, 1H), 5.22 (q, J=8.8 Hz, 2H), 2.97-2.80 (m, 2H), 2.07-1.97 (m, 1H), 1.95-1.84 (m, 1H). ¹⁹F NMR (376 MHz, Methanol-d4) δ −72.92 (t, J=8.7 Hz), −78.17, −121.17 (d, J=11.1 Hz), −156.97 (d, J=6.7 Hz).

Example 619. 5-(3-fluoro-8-((2S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione (Racemic Mixture)

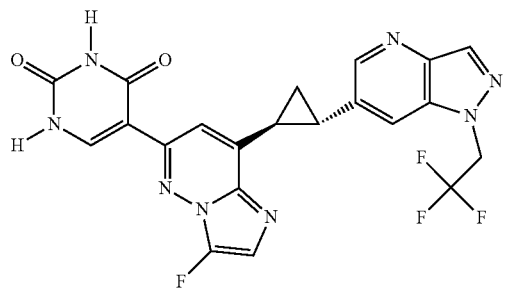 [SMILES: O=c1[nH]cc(-c2cc([C@H]3C[C@@H]3c3cnc4cnn(CC(F)(F)F)c4c3)c3ncc(F)n3n2)c(=O)[nH]1]

5-(3-fluoro-8-((1S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-b]pyridine (Racemic Mixture). ES/MS m/z: 487.10 [M+H]. $^1$H NMR (400 MHz, Methanol-d4) δ 8.63 (d, J=1.8 Hz, 1H), 8.29 (s, 1H), 8.22 (s, 1H), 8.14 (s, 1H), 7.70 (s, 1H), 7.49 (d, J=6.7 Hz, 1H), 5.31 (q, J=8.6 Hz, 2H), 3.07-2.98 (m, 1H), 2.97-2.88 (m, 1H), 2.16-2.08 (m, 1H), 2.01-1.93 (m, 1H). $^{19}$F NMR (376 MHz, Methanol-d4) δ −72.98--−73.13 (m), −78.18, −157.07 (d, J=6.9 Hz).

Example 620. 5-(8-((2S,2S)-2-(1-(2,2,2-trifluoroethyl)-2-(trifluoromethyl)-1H-benzo[d]imidazol-6-yl)cyclopropyl)imidazo[1,2-b]pyridazin-6-yl)pyrimidine-2,4(1H,3H)-dione

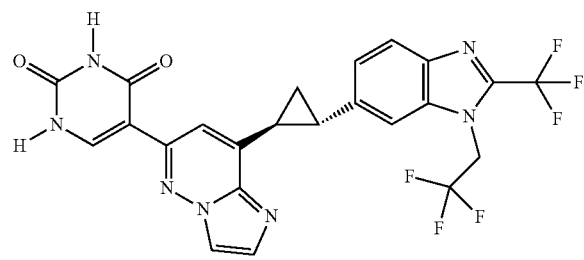 [SMILES: O=c1[nH]cc(-c2cc([C@H]3C[C@@H]3c3ccc4nc(C(F)(F)F)n(CC(F)(F)F)c4c3)c3nccn3n2)c(=O)[nH]1]

5-(8-((2S,2S)-2-(1-(2,2,2-trifluoroethyl)-2-(trifluoromethyl)-1H-benzo[d]imidazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(1-(2,2,2-trifluoroethyl)-2-(trifluoromethyl)-1H-benzo[d]imidazol-6-yl)cyclopropyl)imidazo[1,2-b]pyridazine. ES/MS m/z: 536.10 [M+H]. $^1$H NMR (400 MHz, Methanol-d4) δ 8.35 (d, J=1.9 Hz, 1H), 8.28 (s, 1H), 8.03 (d, J=1.9 Hz, 1H), 8.01 (s, 1H), 7.81 (d, J=8.5 Hz, 1H), 7.72 (s, 1H), 7.40 (dd, J=8.5, 1.4 Hz, 1H), 5.31 (q, J=8.5 Hz, 2H), 3.00-2.91 (m, 1H), 2.87-2.77 (m, 1H), 2.09-1.95 (m, 2H). $^{19}$F NMR (376 MHz, Methanol-d4) δ −63.38 (q, J=5.2 Hz), −72.14--−72.27 (m), −77.84.

Example 621. 5-(3-fluoro-8-((2S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture)

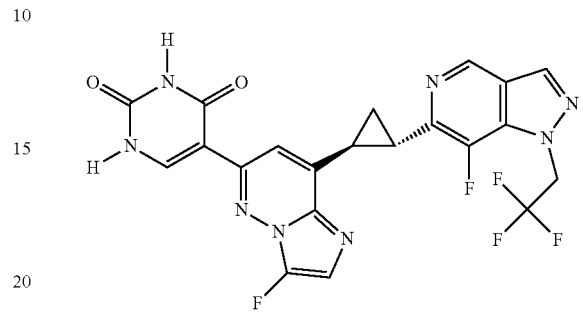

5-(3-fluoro-8-((1S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)-3-fluoroimidazo[1,2-b]pyridazin-8-yl)cyclopropyl)-7-fluoro-1-(2,2,2-trifluoroethyl)-1H-pyrazolo[4,3-c]pyridine (Racemic Mixture). ES/MS m/z: 505.10 [M+H]. $^1$H NMR (400 MHz, Methanol-d4) δ 8.89 (s, 1H), 8.35 (d, J=2.2 Hz, 1H), 8.24 (s, 1H), 7.84 (s, 1H), 7.57 (d, J=6.4 Hz, 1H), 5.26 (q, J=8.5 Hz, 2H), 3.30-3.20 (m, 1H), 3.20-3.12 (m, 1H), 2.20-2.13 (m, 1H), 2.12-2.05 (m, 1H). $^{19}$F NMR (376 MHz, Methanol-d4) δ −73.68--−73.80 (m), −78.21, −155.36--−155.48 (m), −156.64 (d, J=6.6 Hz).

Example 622. 5-(8-((2S,2S)-2-(4-(2-(trifluoromethyl)phenyl)pyridin-2-yl)cyclopropyl)imidazo[1,2-b]pyridazin-6-yl)pyrimidine-2,4(1H,3H)-dione (Racemic Mixture)

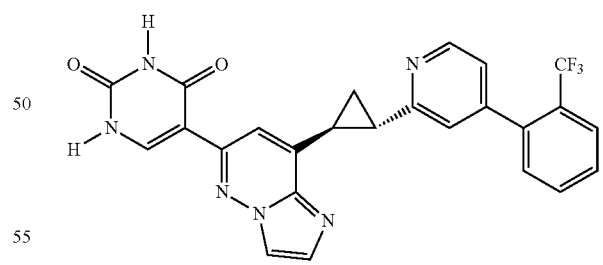

5-(8-((2S,2S)-2-(4-(2-(trifluoromethyl)phenyl)pyridin-2-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((2S,2S)-2-(4-(2-(trifluoromethyl)phenyl)pyridin-2-yl)cyclopropyl)imidazo[1,2-b]pyridazine (Racemic Mixture). ES/MS m/z: 490.80 [M+H]. $^1$H NMR (400 MHz, Methanol-d4) δ 8.60 (d, J=5.3 Hz, 1H), 8.38 (d, J=2.0 Hz, 1H), 8.28

(s, 1H), 8.07 (s, 1H), 8.06 (d, J=2.0 Hz, 1H), 7.88-7.81 (m, 1H), 7.76-7.70 (m, 1H), 7.69-7.62 (m, 1H), 7.50 (s, 1H), 7.45-7.40 (m, 1H), 7.34-7.30 (m, 1H), 3.15-3.06 (m, 1H), 3.01-2.94 (m, 1H), 2.21-2.13 (m, 1H), 2.03-1.96 (m, 1H). $^{19}$F NMR (376 MHz, Methanol-d4) δ −58.41, −77.91.

Example 623. 5-(8-((1S,2S)-2-(4-(2,4-difluorophenyl)pyridin-2-yl)cyclopropyl)imidazo[1,2-b]pyridazin-6-yl)pyrimidine-2,4(1H,3H)-dione (Racemic Mixture)

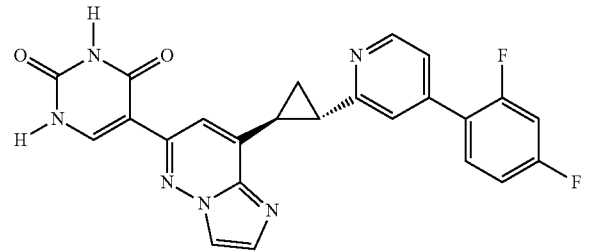 [SMILES: O=c1[nH]cc(-c2cc([C@H]3C[C@@H]3c3cc(-c4ccc(F)cc4F)ccn3)c3nccn3n2)c(=O)[nH]1]

5-(8-((1S,2S)-2-(4-(2,4-difluorophenyl)pyridin-2-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(4-(2,4-difluorophenyl)pyridin-2-yl)cyclopropyl)-6-(2,4-dimethoxypyrimidin-5-yl)imidazo[1,2-b]pyridazine (Racemic Mixture). ES/MS m/z: 459.10 [M+H]. $^1$H NMR (400 MHz, Methanol-d4) δ 8.61 (d, J=5.4 Hz, 1H), 8.33 (d, J=1.9 Hz, 1H), 8.27 (s, 1H), 8.02 (s, 1H), 8.00 (d, J=1.9 Hz, 1H), 7.75-7.66 (m, 2H), 7.61-7.56 (m, 1H), 7.20-7.11 (m, 2H), 3.14-3.06 (m, 1H), 3.04-2.95 (m, 1H), 2.23-2.12 (m, 1H), 2.08-2.00 (m, 1H). $^{19}$F NMR (376 MHz, Methanol-d4) δ −77.81, −109.90−−110.16 (m), −114.35−−114.66 (m).

Example 624. 5-(8-((2S,2S)-2-(1-(2,2,2-trifluoroethyl)-2-(trifluoromethyl)-1H-imidazo[4,5-c]pyridin-6-yl)cyclopropyl)imidazo[1,2-b]pyridazin-6-yl)pyrimidine-2,4(1H,3H)-dione (Racemic Mixture)

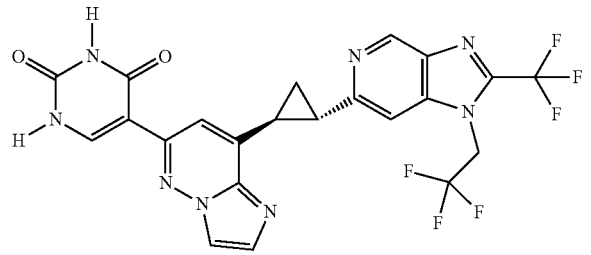 [SMILES: O=c1[nH]cc(-c2cc([C@H]3C[C@@H]3c3cc4c(cn3)nc(C(F)(F)F)n4CC(F)(F)F)c3nccn3n2)c(=O)[nH]1]

5-(8-((2S,2S)-2-(1-(2,2,2-trifluoroethyl)-2-(trifluoromethyl)-1H-imidazo[4,5-c]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-1-(2,2,2-trifluoroethyl)-2-(trifluoromethyl)-1H-imidazo[4,5-c]pyridine (Racemic Mixture). ES/MS m/z: 537.20 [M+H]. $^1$H NMR (400 MHz, Methanol-d4) δ 9.12 (s, 1H), 8.37 (d, J=1.9 Hz, 1H), 8.30 (s, 1H), 8.09 (s, 1H), 8.04 (d, J=1.9 Hz, 1H), 7.89 (s, 1H), 5.34 (q, J=8.5 Hz, 1H), 3.19-2.97 (m, 2H), 2.26-2.17 (m, 1H), 2.02-1.94 (m, 1H). $^{19}$F NMR (376 MHz, Methanol-d4) δ −63.74−−63.89 (m), −72.24−−72.39 (m), −77.82.

Example 625. 5-(8-((2S,2S)-2-(3-(trifluoromethyl)imidazo[1,5-a]pyridin-7-yl)cyclopropyl)imidazo[1,2-b]pyridazin-6-yl)pyrimidine-2,4(1H,3H)-dione (Racemic Mixture)

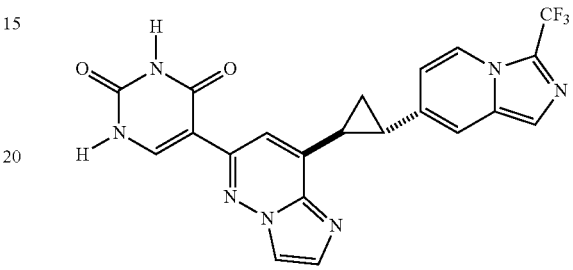

5-(8-((1S,2S)-2-(3-(trifluoromethyl)imidazo[1,5-a]pyridin-7-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(3-(trifluoromethyl)imidazo[1,5-a]pyridin-7-yl)cyclopropyl)imidazo[1,2-b]pyridazine (Racemic Mixture). ES/MS m/z: 454.20 [M+H]. $^1$H NMR (400 MHz, Methanol-d4) δ 8.36 (d, J=1.9 Hz, 1H), 8.34 (d, J=7.5 Hz, 1H), 8.28 (s, 1H), 8.04 (d, J=1.9 Hz, 1H), 8.00 (s, 1H), 7.67 (s, 1H), 7.52 (s, 1H), 6.93 (dd, J=7.5, 1.8 Hz, 1H), 2.87-2.73 (m, 2H), 1.99 (t, J=7.5 Hz, 2H). $^{19}$F NMR (376 MHz, Methanol-d4) δ −64.76, −77.89.

Example 626. 5-(8-((2S,2S)-2-(2-(difluoromethyl)-1-(2,2,2-trifluoroethyl)-1H-benzo[d]imidazol-6-yl)cyclopropyl)imidazo[1,2-b]pyridazin-6-yl)pyrimidine-2,4(1H,3H)-dione (Racemic Mixture)

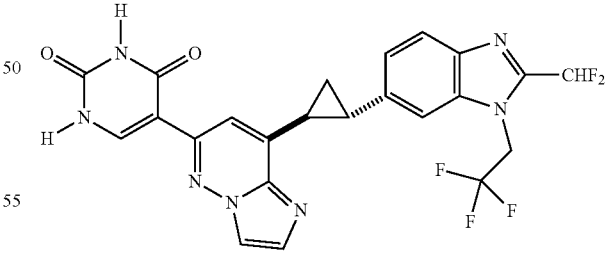

5-(8-((2S,2S)-2-(2-(difluoromethyl)-1-(2,2,2-trifluoroethyl)-1H-benzo[d]imidazol-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((2S,2S)-2-(2-(difluoromethyl)-1-(2,2,2-trifluoroethyl)-1H-benzo[d]imidazol-6-yl)cyclopropyl)-6-(2,4-dimethoxypyrimidin-5-yl)imidazo[1,2-b]pyridazine (Racemic Mixture). ES/MS m/z: 518.20 [M+H]. $^1$H NMR (400 MHz, Methanol-d4) δ 8.36 (d, J=2.0 Hz, 1H), 8.29 (s, 1H), 8.04 (d, J=2.0 Hz, 1H), 8.03 (s, 1H), 7.76 (d, J=8.5 Hz, 1H), 7.67 (s, 1H), 7.35 (dd, J=8.5, 1.6 Hz, 1H), 7.18 (t, J=52.1 Hz, 1H), 5.29 (q, J=8.6 Hz, 2H), 2.99-2.89 (m, 1H), 2.85-2.75 (m, 1H), 2.10-1.95 (m, 2H). $^{19}$F NMR (376 MHz, Methanol-d4) δ −72.12-72.31 (m), −77.84, −117.52 (dq, J=52.0, 5.5 Hz).

Example 627. 5-(8-((2S,2S)-2-(5-(2,2,2-trifluoroethoxy)quinolin-7-yl)cyclopropyl)imidazo[1,2-b]pyridazin-6-yl)pyrimidine-2,4(1H,3H)-dione

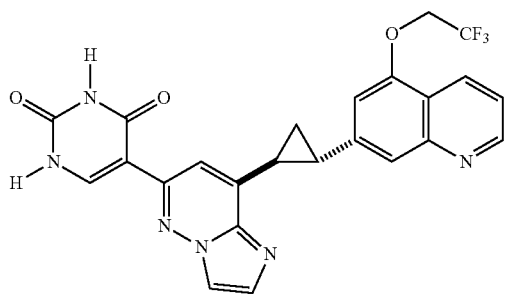

5-(8-((1S,2S)-2-(5-(2,2,2-trifluoroethoxy)quinolin-7-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 7-((1S,2S)-2-(6-(2,4-dimethoxypyrimidin-5-yl)imidazo[1,2-b]pyridazin-8-yl)cyclopropyl)-5-(2,2,2-trifluoroethoxy)quinoline (Racemic Mixture). ES/MS m/z: 495.10 [M+H]. $^1$H NMR (400 MHz, Methanol-d4) δ 9.04 (dd, J=5.0, 1.6 Hz, 1H), 9.02-8.98 (m, 1H), 8.28 (d, J=1.7 Hz, 1H), 8.25 (s, 1H), 7.92 (d, J=1.7 Hz, 1H), 7.91 (s, 1H), 7.80 (dd, J=8.5, 5.0 Hz, 1H), 7.66 (s, 1H), 7.26 (s, 1H), 4.94 (q, J=8.3 Hz, 2H), 3.10-2.94 (m, 2H), 2.18-2.06 (m, 2H). $^{19}$F NMR (376 MHz, Methanol-d4) δ −75.99 (t, J=8.3 Hz), −77.84.

Example 628. 5-(3-fluoro-8-((2S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione

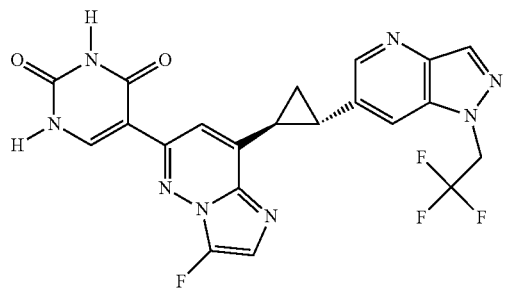 [SMILES: O=c1[nH]cc(-c2cc([C@H]3C[C@@H]3c3cnc4cnn(CC(F)(F)F)c4c3)c3ncc(F)n3n2)c(=O)[nH]1]

5-(3-fluoro-8-((2S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)-3-fluoroimidazo[1,2-b]pyridazin-8-yl)cyclopropyl)-1-(2,2,2-trifluoroethyl)-1H-pyrazolo[4,3-b]pyridine. ES/MS m/z: 487.10 [M+H]. $^1$H NMR (400 MHz, Methanol-d4) δ 8.64 (d, J=1.9 Hz, 1H), 8.32-8.27 (m, 1H), 8.22 (s, 1H), 8.15 (s, 1H), 7.71 (s, 1H), 7.49 (d, J=6.7 Hz, 1H), 5.31 (q, J=8.7 Hz, 2H), 3.08-2.98 (m, 1H), 2.98-2.87 (m, 1H), 2.17-2.09 (m, 1H), 2.04-1.91 (m, 1H). $^{19}$F NMR (376 MHz, Methanol-d4) δ −73.03 (t, J=8.7 Hz), −78.18, −157.05 (d, J=6.5 Hz).

Example 629. 5-(8-((2S,2S)-2-(7-fluoro-1-(2,2,2-trifluoroethyl)-1H-indazol-6-yl)cyclopropyl)-[1,2,4]triazolo[1,5-b]pyridazin-6-yl)pyrimidine-2,4(1H,3H)-dione

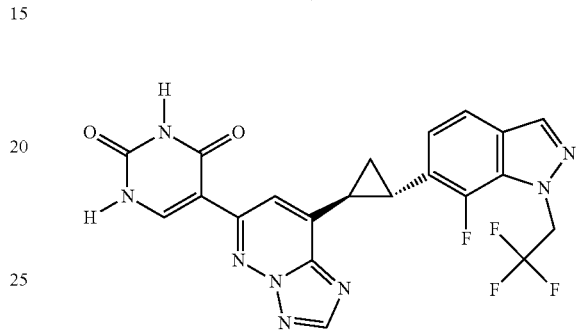

5-(8-((1S,2S)-2-(7-fluoro-1-(2,2,2-trifluoroethyl)-1H-indazol-6-yl)cyclopropyl)-[1,2,4]triazolo[1,5-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(7-fluoro-1-(2,2,2-trifluoroethyl)-1H-indazol-6-yl)cyclopropyl)[1,2,4]triazolo[1,5-b]pyridazine. ES/MS m/z: 487.20 [M+H]. $^1$H NMR (400 MHz, Methanol-d4) δ 8.50 (s, 1H), 8.27 (s, 1H), 8.12 (d, J=2.3 Hz, 1H), 8.10 (s, 1H), 7.59 (d, J=8.4 Hz, 1H), 7.07 (dd, J=8.4, 5.9 Hz, 1H), 5.21 (q, J=8.5 Hz, 2H), 3.26-3.18 (m, 1H), 2.92-2.83 (m, 1H), 2.25-2.16 (m, 1H), 1.98-1.89 (m, 1H). $^{19}$F NMR (376 MHz, Methanol-d4) δ −73.70--73.83 (m), −78.18, −143.42--143.63 (m).

Example 630. 5-(3-fluoro-8-((2S,2S)-2-(7-fluoro-1-(2,2,2-trifluoroethyl)-1H-indazol-6-yl)cyclopropyl)imidazo[1,2-b]pyridazin-6-yl)pyrimidine-2,4(1H,3H)-dione

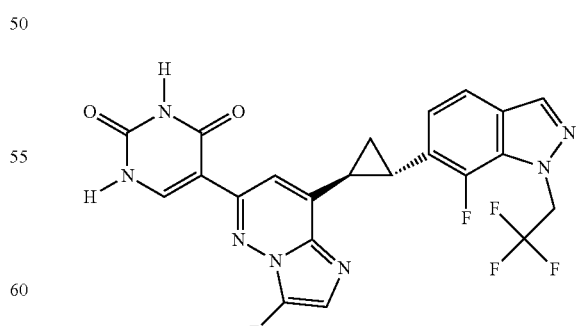

5-(3-fluoro-8-((1S,2S)-2-(7-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((1S,2S)-2-(7-fluoro-1-(2,2,2-trifluoroethyl)-1H-indazol-6-yl)cyclopropyl)imidazo[1,2-b]pyridazine. ES/MS m/z: 505.20 [M+H]. $^1$H NMR (400 MHz, Methanol-d4) δ 8.88 (s, 1H), 8.34 (d, J=2.2 Hz, 1H), 8.22 (s, 1H), 7.77 (s, 1H), 7.49 (d, J=6.6 Hz, 1H), 5.26 (q, J=8.5 Hz, 3H), 3.34-3.21 (m, 1H), 3.22-3.11 (m, 1H), 2.19-2.13 (m, 1H), 2.13-2.06 (m, 1H). $^{19}$F NMR (376 MHz, Methanol-d4) δ −73.76 (td, J=8.4, 5.1 Hz), −78.15, −155.66--155.77 (m), −156.98 (d, J=6.4 Hz).

Example 631. 5-(8-((2S,2S)-2-(4,7-difluoro-1-(2,2,2-trifluoroethyl)-1H-indazol-6-yl)cyclopropyl)imidazo[1,2-b]pyridazin-6-yl)pyrimidine-2,4(1H,3H)-dione (Racemic Mixture)

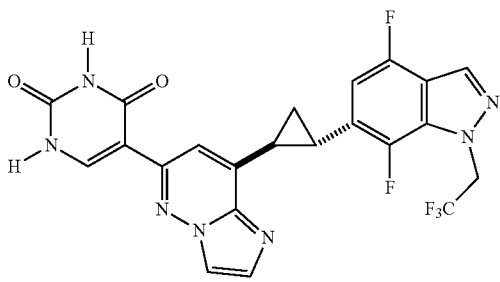

5-(8-((1S,2S)-2-(4,7-difluoro-1-(2,2,2-trifluoroethyl)-1H-indazol-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 8-((1S,2S)-2-(4,7-difluoro-1-(2,2,2-trifluoroethyl)-1H-indazol-6-yl)cyclopropyl)-6-(2,4-dimethoxypyrimidin-5-yl)imidazo[1,2-b]pyridazine (Racemic Mixture). ES/MS m/z: 504.10 [M+H]. $^1$H NMR (400 MHz, Methanol-d4) δ 8.36 (d, J=1.9 Hz, 1H), 8.28 (s, 1H), 8.21 (d, J=2.1 Hz, 1H), 8.06-8.01 (m, 2H), 6.80 (dd, J=10.2, 4.3 Hz, 1H), 5.24 (q, J=8.5 Hz, 2H), 3.08-2.96 (m, 1H), 2.90 2.81 (m, 1H), 2.08-1.95 (m, 2H). $^{19}$F NMR (376 MHz, Methanol-d4) δ −73.69 (td, J=8.4, 5.5 Hz), −77.84, −125.10 (dd, J=23.9, 10.2 Hz), −147.40-147.65 (m).

Example 632. 5-(8-((2S,2S)-2-(3-(2,2,2-trifluoroethyl)-2-(trifluoromethyl)imidazo[1,2-a]pyridin-6-yl)cyclopropyl)imidazo[1,2-b]pyridazin-6-yl)pyrimidine-2,4(1H,3H)-dione (Racemic Mixture)

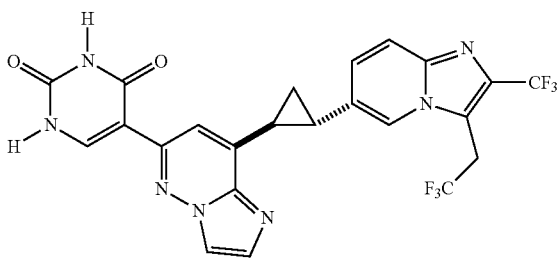

5-(8-((1S,2S)-2-(3-(2,2,2-trifluoroethyl)-2-(trifluoromethyl)imidazo[1,2-a]pyridin-6-yl)cyclopropyl)imidazo[1,2-b]pyridazin-6-yl)pyrimidine-2,4(1H,3H)-dione (Racemic Mixture) was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(3-(2,2,2-trifluoroethyl)-2-(trifluoromethyl)imidazo[1,2-a]pyridin-6-yl)cyclopropyl)imidazo[1,2-b]pyridazine (Racemic Mixture). ES/MS m/z: 536.10 [M+H]. $^1$H NMR (400 MHz, Methanol-d4) δ 8.59 (s, 1H), 8.36 (d, J=1.8 Hz, 1H), 8.29 (s, 1H), 8.05-8.01 (m, 2H), 7.72 (d, J=9.5 Hz, 1H), 7.44 (d, J=9.5 Hz, 1H), 4.49-4.30 (m, 2H), 2.97-2.91 (m, 1H), 2.91-2.82 (m, 1H), 2.11-2.02 (m, 1H), 2.02-1.94 (m, 1H). $^{19}$F NMR (376 MHz, Methanol-d4) δ −64.78, −65.01 (t, J=10.1 Hz), −77.91.

Examples 633 and 634. 5-(8-((1S,2S)-2-(4-chlorophenyl)cyclopropyl)imidazo[1,2-b]pyridazin-6-yl)pyrimidine-2,4(1H,3H)-dione and 5-(8-((1R,2R)-2-(4-chlorophenyl)cyclopropyl)imidazo[1,2-b]pyridazin-6-yl)pyrimidine-2,4(1H,3H)-dione

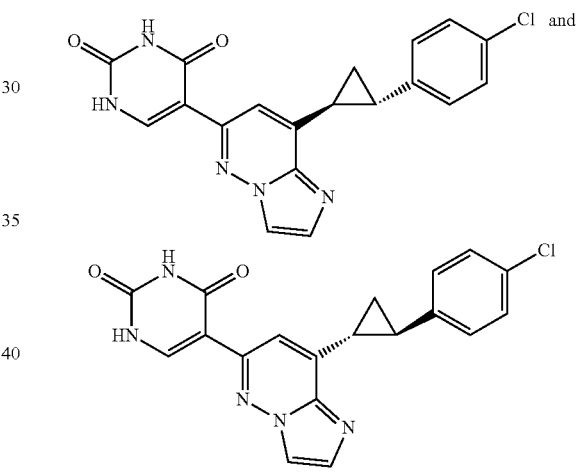

5-(8-((2S,2S)-2-(4-chlorophenyl)cyclopropyl)imidazo[1,2-b]pyridazin-6-yl)pyrimidine-2,4(1H,3H)-dione and 5-(8-((1R,2R)-2-(4-chlorophenyl)cyclopropyl)imidazo[1,2-b]pyridazin-6-yl)pyrimidine-2,4(1H,3H)-dione were chirally separated from the Example 39 by SFC AD-H column (35% MeOH).

Example 633 5-(8-((2S,2S)-2-(4-chlorophenyl)cyclopropyl)imidazo[1,2-b]pyridazin-6-yl)pyrimidine-2,4(1H,3H)-dione. ES/MS m/z: 380.10 [M+H]. $^1$H NMR (400 MHz, DMSO-d6) δ 11.53-11.45 (m, 2H), 8.25 (s, 1H), 7.99 (d, J=6.0 Hz, 1H), 7.74 (s, 1H), 7.47 (s, 1H), 7.39-7.25 (m, 4H), 2.87-2.78 (m, 1H), 2.75-2.65 (m, 1H), 2.14-2.04 (m, 1H), 1.77-1.67 (m, 1H).

Example 634 5-(8-((1R,2R)-2-(4-chlorophenyl)cyclopropyl)imidazo[1,2-b]pyridazin-6-yl)pyrimidine-2,4(1H,3H)-dione. ES/MS m/z: 380.10 [M+H]. $^1$H NMR (400 MHz, DMSO-d6) δ 11.58-11.50 (m, 2H), 8.37-8.30 (m, 1H), 8.03 (d, J=6.2 Hz, 1H), 7.88 (s, 1H), 7.57 (s, 1H), 7.40-7.34 (m, 2H), 7.32-7.25 (m, 2H), 2.85-2.76 (m, 1H), 2.76-2.68 (m, 1H), 2.10-2.00 (m, 1H), 1.82-1.70 (m, 1H).

Example 635. 5-(8-((2S,2S)-2-(3-fluoro-5-(trifluoromethyl)pyridin-2-yl)cyclopropyl)imidazo[1,2-b]pyridazin-6-yl)pyrimidine-2,4(1H,3H)-dione

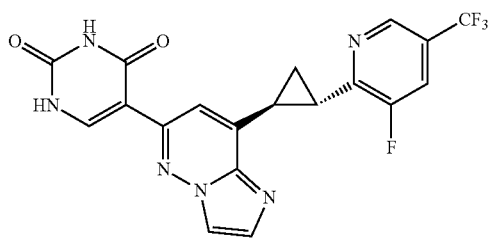 [SMILES: O=c1[nH]cc(-c2cc([C@H]3C[C@@H]3c3ncc(C(F)(F)F)cc3F)c3nccn3n2)c(=O)[nH]1]

5-(8-((1S,2S)-2-(3-fluoro-5-(trifluoromethyl)pyridin-2-yl)cyclopropyl)imidazo[1,2-b]pyridazin-6-yl)pyrimidine-2,4(1H,3H)-dione was chirally separated from the racemic mixture Example 582 by SFC AD-H column (30% EtOH). ES/MS m/z: 433.20 [M+H]. $^1$H NMR (400 MHz, Methanol-d4) δ 8.68 (s, 1H), 8.15 (s, 1H), 8.11-8.08 (m, 1H), 7.93-7.83 (m, 1H), 7.69-7.66 (m, 1H), 7.64 (s, 1H), 3.27-3.08 (m, 2H), 2.17-2.05 (m, 2H).

Example 636. 5-(8-((2S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione

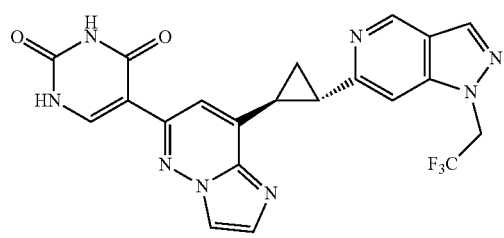 [SMILES: O=c1[nH]cc(-c2cc([C@H]3C[C@@H]3c3cc4c(cn3)cnn4CC(F)(F)F)c3nccn3n2)c(=O)[nH]1]

5-(8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione was chirally separated from the racemic mixture Example 591 by SFC AD-H column (35% EtOH). ES/MS m/z: 469.10 [M+H]. $^1$H NMR (400 MHz, Methanol-d4) δ 9.05 (s, 1H), 8.32 (s, 1H), 8.16 (s, 1H), 8.11 (d, J=1.4 Hz, 1H), 7.69 (d, J=1.4 Hz, 1H), 7.69 (s, 1H), 7.64 (s, 1H), 5.25 (q, J=8.7 Hz, 2H), 3.20-3.10 (m, 1H), 3.04-2.95 (m, 1H), 2.15-2.07 (m, 1H), 2.05-1.97 (m, 1H). $^{19}$F NMR (376 MHz, Methanol-d4) δ -72.97 (t, J=8.8 Hz).

Example 637. 5-(8-((2S,2S)-2-(1-(2,2,2-trifluoroethyl)-3-(trifluoromethyl)-1H-pyrazolo[4,3-c]pyridin-6-yl)cyclopropyl)imidazo[1,2-b]pyridazin-6-yl)pyrimidine-2,4(1H,3H)-dione

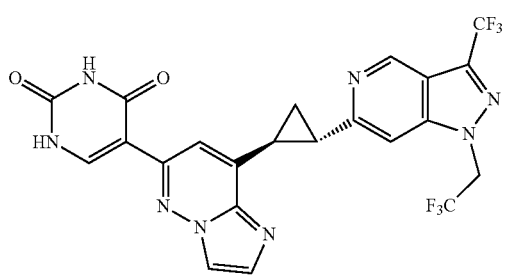 [SMILES: O=c1[nH]cc(-c2cc([C@H]3C[C@@H]3c3cc4c(cn3)c(C(F)(F)F)nn4CC(F)(F)F)c3nccn3n2)c(=O)[nH]1]

5-(8-((2S,2S)-2-(1-(2,2,2-trifluoroethyl)-3-(trifluoromethyl)-1H-pyrazolo[4,3-c]pyridin-6-yl)cyclopropyl)imidazo[1,2-b]pyridazin-6-yl)pyrimidine-2,4(1H,3H)-dione was chirally separated from the racemic mixture Example 608 by SFC AD-H column (25% EtOH). ES/MS m/z: 537.20 [M+H]. $^1$H NMR (400 MHz, Methanol-d4) δ 9.10 (s, 1H), 8.16 (s, 1H), 8.11 (s, 1H), 7.79 (s, 1H), 7.69 (s, 1H), 7.64 (s, 1H), 5.37 (q, J=8.6 Hz, 2H), 3.25-3.16 (m, 1H), 3.06-2.98 (m, 1H), 2.18-2.09 (m, 1H), 2.05-1.97 (m, 1H). $^{19}$F NMR (376 MHz, Methanol-d4) δ -63.30, -72.88 (t, J=8.7 Hz).

Example 638. 5-(3-fluoro-8-((2S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione

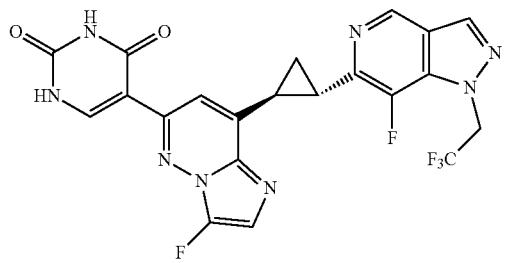 [SMILES: O=c1[nH]cc(-c2cc([C@H]3C[C@@H]3c3ncc4cnn(CC(F)(F)F)c4c3F)c3ncc(F)n3n2)c(=O)[nH]1]

5-(3-fluoro-8-((1S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione was chirally separated from the racemic mixture Example 621 by SFC AD-H column (25% MeOH). ES/MS m/z: 505.20 [M+H]. $^1$H NMR (400 MHz, Methanol-d4) δ 8.88 (s, 1H), 8.34 (d, J=2.2 Hz, 1H), 8.22 (s, 1H), 7.77 (s, 1H), 7.49 (d, J=6.6 Hz, 1H), 5.26 (q, J=8.5 Hz, 2H), 3.30-3.21 (m, 1H), 3.22-3.10 (m, 1H), 2.20-2.13 (m, 1H), 2.13-2.06 (m, 1H). $^{19}$F NMR (376 MHz, Methanol-d4) δ -73.76 (td, J=8.5, 5.2 Hz), -78.15, -155.66--155.78 (m), -156.98 (d, J=6.4 Hz).

Example 639 and 640

5-(8-((2S,2S)-2-((S)-1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione and 5-(8-((2S,2S)-2-((R)-1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione

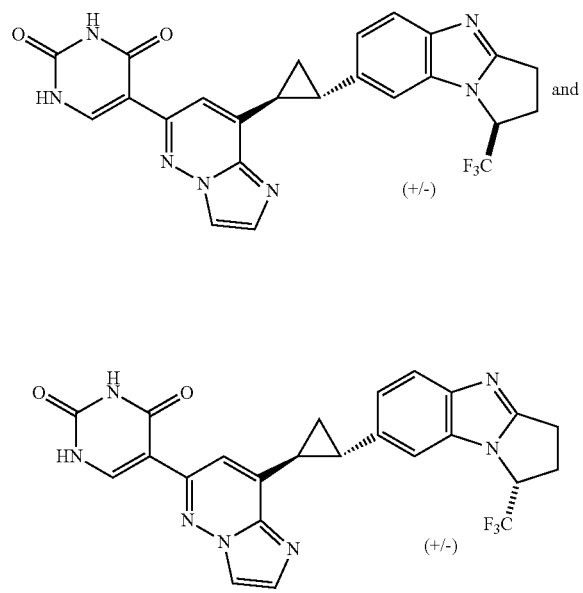

5-(8-((1S,2S)-2-((S)-1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione and 5-(8-((1S,2S)-2-((R)-1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione were diastereomerically separated (racemic compounds) from the mixture Example 616 by repeated RP-HPLC purification. The diastereomeric structures were arbitrarily assigned.

5-(8-((1S,2S)-2-((S)-1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione. ES/MS m/z: 494.20 [M+H]. $^1$H NMR (400 MHz, Methanol-d4) δ 8.33 (d, J=1.8 Hz, 1H), 8.27 (s, 1H), 7.99 (d, J=1.8 Hz, 1H), 7.96 (s, 1H), 7.66 (d, J=8.5 Hz, 1H), 7.57 (s, 1H), 7.41-7.33 (m, 1H), 5.56-5.43 (m, 1H), 3.00-2.88 (m, 2H), 2.82-2.73 (m, 1H), 2.06-1.89 (m, 2H). $^{19}$F NMR (376 MHz, Methanol-d4) δ −76.79 (d, J=6.8 Hz), −77.86.

5-(8-((1S,2S)-2-((R)-1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione. ES/MS m/z: 494.10 [M+H]. $^1$H NMR (400 MHz, Methanol-d4) δ 8.34 (d, J=1.9 Hz, 1H), 8.27 (s, 1H), 8.01 (d, J=1.9 Hz, 1H), 7.97 (s, 1H), 7.67 (d, J=8.5 Hz, 1H), 7.58 (s, 1H), 7.39-7.34 (m, 1H), 5.58-5.45 (m, 1H), 3.02-2.88 (m, 2H), 2.87-2.76 (m, 1H), 2.03-1.88 (m, 2H). $^{19}$F NMR (376 MHz, Methanol-d4) δ −76.81 (d, J=6.9 Hz), −77.87.

Example 641. 5-(8-(2-azabicyclo[2.1.1]hexan-2-yl)imidazo[1,2-b]pyridazin-6-yl)pyrimidine-2,4(1H,3H)-dione

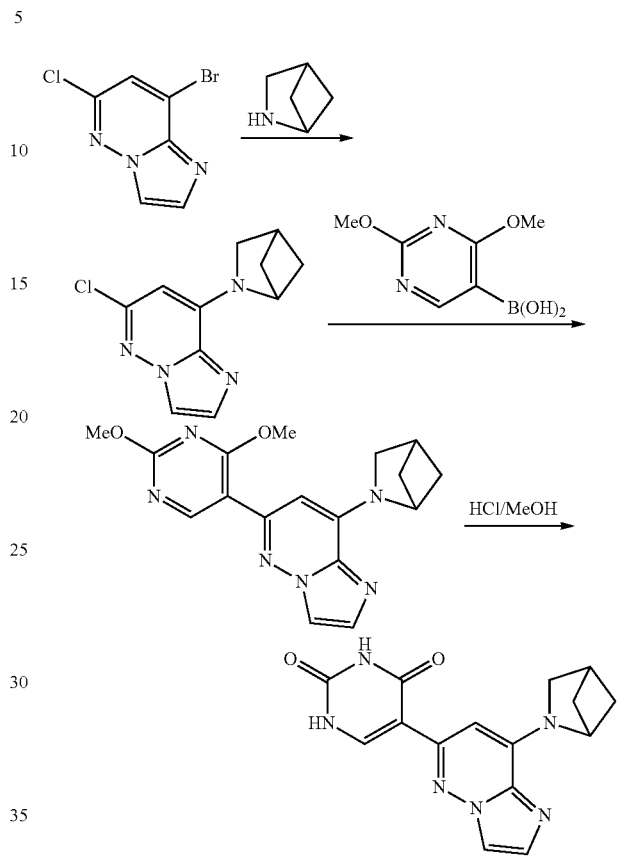

Step 1: A solution of 8-bromo-6-chloroimidazo[1,2-b]pyridazine (350 mg, 1.51 mmol, 1 equiv), 2-azabicyclo[2.1.1]hexane hydrochloride (138 mg, 1.66 mmol, 1 equiv), DIPEA (0.63 mL, 3.61 mmol, 2.4 equiv), and MeCN (6 mL) was heated to 85° C. After 4 hours, the reaction mixture was directly purified by SiO$_2$ chromatography (0-100% EtOAc/Hex), affording 2-(6-chloroimidazo[1,2-b]pyridazin-8-yl)-2-azabicyclo[2.1.1]hexane. ES/MS m/z: 235.10 [M+H].

Step 2: A solution of 2-(6-chloroimidazo[1,2-b]pyridazin-8-yl)-2-azabicyclo[2.1.1]hexane (379 mg, 1.61 mmol, 1 equiv), (2,4-dimethoxypyrimidin-5-yl)boronic acid (446 mg, 2.42 mol, 1.5 equiv), cesium carbonate (1052 mg, 3.23 mmol, 2 equiv), and PdCl$_2$(dppf)-CH$_2$Cl$_2$ (118 mg, 10 mol %) in 1:2 water/1,4-dioxane (8 mL) was heated to 80° C. After 90 minutes, the reaction mixture was directly purified by SiO$_2$ chromatography (0-100% EtOAc/Hex), affording 2-(6-(2,4-dimethoxypyrimidin-5-yl)imidazo[1,2-b]pyridazin-8-yl)-2-azabicyclo[2.1.1]hexane. ES/MS m/z: 339.20 [M+H].

Step 3: A solution of 2-(6-(2,4-dimethoxypyrimidin-5-yl)imidazo[1,2-b]pyridazin-8-yl)-2-azabicyclo[2.1.1]hexane (112 mg) in 1:1 1N HCl:MeOH (2 mL) was heated to 80° C. After 14 hours, the reaction mixture was filtered and washed with MeCN. The remaining solids were dried under vacuum, affording 5-(8-(2-azabicyclo[2.1.1]hexan-2-yl)imidazo[1,2-b]pyridazin-6-yl)pyrimidine-2,4(1H,3H)-dione. ES/MS m/z: 311.10 [M+H]. $^1$H NMR (400 MHz, Methanol-d4) δ

8.26-8.21 (m, 2H), 7.96 (d, J=2.1 Hz, 1H), 7.51 (s, 1H), 3.86 (s, 2H), 3.16-3.10 (m, 1H), 2.29-2.17 (m, 2H), 1.64-1.53 (m, 2H).

Example 642. 5-(8-((1R,4S)-2-azabicyclo[2.2.1]heptan-2-yl)imidazo[1,2-b]pyridazin-6-yl)pyrimidine-2,4(1H,3H)-dione

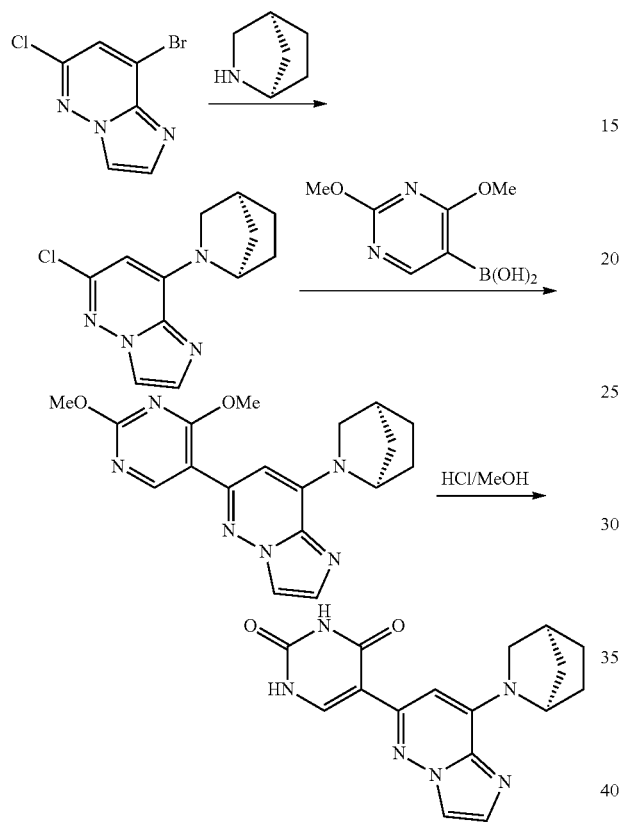

Step 1: A solution of 8-bromo-6-chloroimidazo[1,2-b]pyridazine (150 mg, 0.65 mmol, 1 equiv), (1R,4S)-2-azabicyclo[2.2.1]heptane hydrochloride (63 mg, 0.65 mmol, 1 equiv), DIPEA (0.27 mL, 1.55 mmol, 2.4 equiv), and MeCN (2.5 mL) was heated to 85° C. After 20 hours, the reaction mixture was directly purified by SiO₂ chromatography (0-100% EtOAc/Hex), affording 8-((1R,4S)-2-azabicyclo[2.2.1]heptan-2-yl)-6-chloroimidazo[1,2-b]pyridazine. ES/MS m/z: 249.10 [M+H].

Step 2: A solution of 8-((1R,4S)-2-azabicyclo[2.2.1]heptan-2-yl)-6-chloroimidazo[1,2-b]pyridazine (159 mg, 0.64 mmol, 1 equiv), (2,4-dimethoxypyrimidin-5-yl)boronic acid (176 mg, 0.96 mol, 1.5 equiv), cesium carbonate (417 mg, 1.28 mmol, 2 equiv), and PdCl₂(dppf)-CH₂Cl₂ (47 mg, 10 mol %) in 1:2 water/1,4-dioxane (3 mL) was heated to 80° C. After 18 hours, the reaction mixture was directly purified by SiO₂ chromatography (0-100% EtOAc/Hex), affording 8-((1R,4S)-2-azabicyclo[2.2.1]heptan-2-yl)-6-(2,4-dimethoxypyrimidin-5-yl)imidazo[1,2-b]pyridazine. ES/MS m/z: 353.20 [M+H].

Step 3: A solution of 8-((1R,4S)-2-azabicyclo[2.2.1]heptan-2-yl)-6-(2,4-dimethoxypyrimidin-5-yl)imidazo[1,2-b]pyridazine (167 mg) in 1:1 1N HCl:MeOH (2.5 mL) was heated to 70° C. After 10 hours, the reaction mixture was filtered and purified by RP-HPLC (5-80% MeCN/H₂O with TFA modifier), affording 5-(8-((1R,4S)-2-azabicyclo[2.2.1]heptan-2-yl)imidazo[1,2-b]pyridazin-6-yl)pyrimidine-2,4(1H,3H)-dione. ES/MS m/z: 325.10 [M+H]. ¹H NMR (400 MHz, DMSO-d6) δ 11.37 (s, 1H), 11.35 (d, J=6.1 Hz, 1H), 8.04 (s, 1H), 7.92 (d, J=6.1 Hz, 1H), 7.60 (s, 1H), 6.58 (bs, 1H), 3.61 (bs, 1H), 3.19 (bs, 1H), 2.70 (s, 1H), 1.83-1.61 (m, 4H), 1.61-1.53 (m, 1H), 1.45-1.33 (m, 1H).

Example 643. 5-(8-(2-azabicyclo[2.2.1]heptan-2-yl)imidazo[1,2-b]pyridazin-6-yl)pyrimidine-2,4(1H,3H)-dione

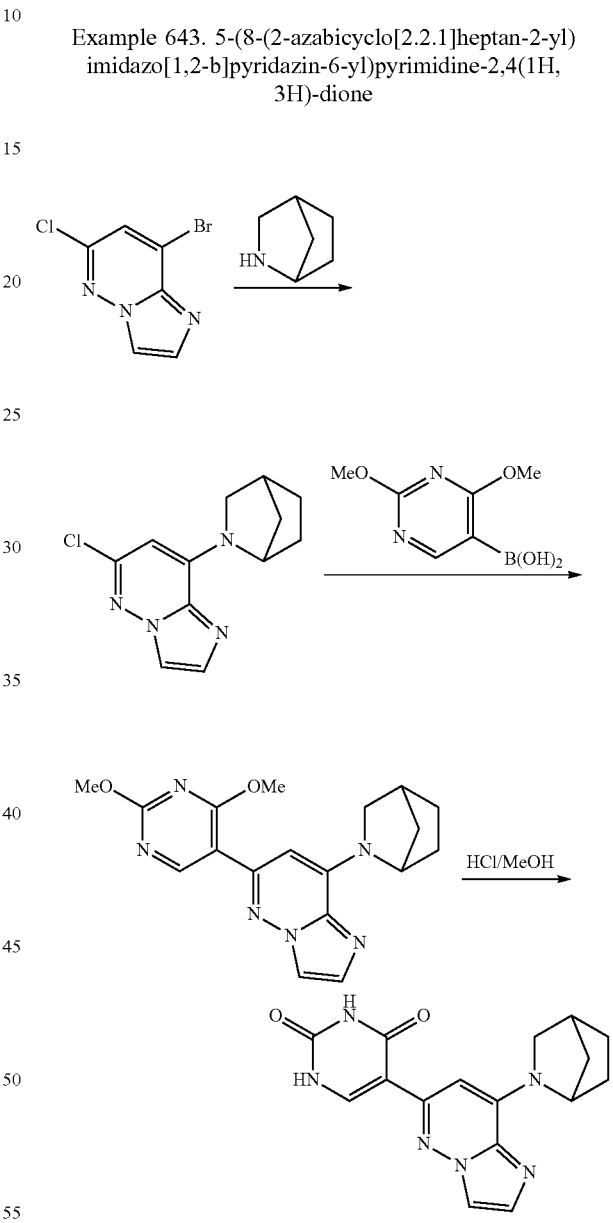

5-(8-(2-azabicyclo[2.2.1]heptan-2-yl)imidazo[1,2-b]pyridazin-6-yl)pyrimidine-2,4(1H,3H)-dione in the manner described for Example 642, but replacing (1R,4S)-2-azabicyclo[2.2.1]heptane hydrochloride with racemic 2-azabicyclo[2.2.1]heptane hydrochloride. ES/MS m/z: 325.20 [M+H]. ¹H NMR (400 MHz, DMSO-d6) δ 11.47 (d, J=6.2 Hz, 1H), 11.42 (s, 1H), 8.17 (s, 1H), 7.97 (d, J=6.2 Hz, 1H), 7.78 (s, 1H), 6.78 (s, 1H), 3.73 (bs, 1H), 3.27 (bs, 1H), 2.72 (s, 1H), 1.83-1.64 (m, 4H), 1.63-1.55 (m, 1H), 1.49-1.35 (m, 1H).

Example 644. 5-(8-(6,6-difluoro-2-azabicyclo[2.2.1]heptan-2-yl)imidazo[1,2-b]pyridazin-6-yl)pyrimidine-2,4(1H,3H)-dione

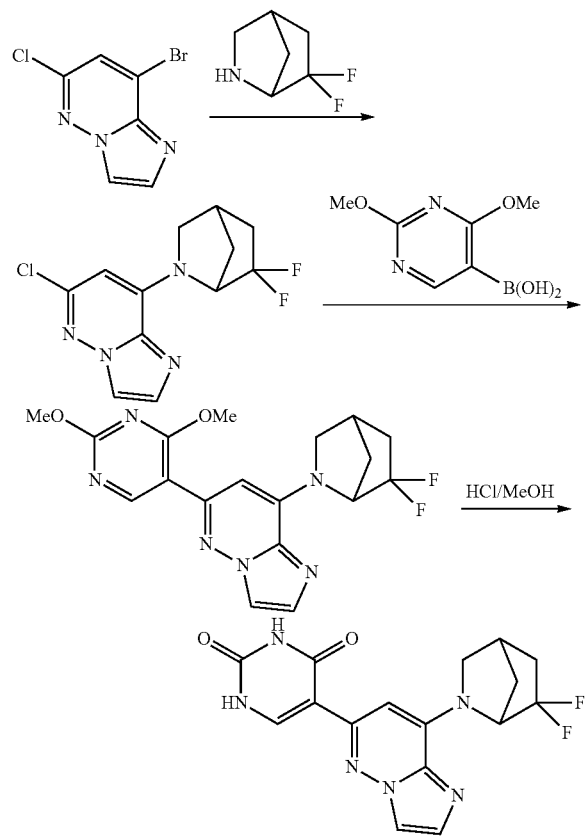

Step 1: A solution of 8-bromo-6-chloroimidazo[1,2-b]pyridazine (350 mg, 1.51 mmol, 1 equiv), 6,6-difluoro-2-azabicyclo[2.2.1]heptane hydrochloride (221 mg, 1.66 mmol, 1.1 equiv), DIPEA (0.63 mL, 3.61 mmol, 2.4 equiv), and MeCN (6 mL) was heated to 85° C. After 20 hours, the reaction mixture was directly purified by SiO₂ chromatography (0-100% EtOAc/Hex), affording 6-chloro-8-(6,6-difluoro-2-azabicyclo[2.2.1]heptan-2-yl)imidazo[1,2-b]pyridazine. ES/MS m/z: 285.10 [M+H].

Step 2: A solution of 6-chloro-8-(6,6-difluoro-2-azabicyclo[2.2.1]heptan-2-yl)imidazo[1,2-b]pyridazine (462 mg, 1.62 mmol, 1 equiv), (2,4-dimethoxypyrimidin-5-yl)boronic acid (448 mg, 2.43 mol, 1.5 equiv), cesium carbonate (1057 mg, 3.25 mmol, 2 equiv), and PdCl₂(dppf)-CH₂Cl₂ (119 mg, 10 mol %) in 1:2 water/1,4-dioxane (25 mL) was heated to 80° C. After 3 hours, the reaction mixture was directly purified by SiO₂ chromatography (0-100% EtOAc/Hex), affording 8-(6,6-difluoro-2-azabicyclo[2.2.1]heptan-2-yl)-6-(2,4-dimethoxypyrimidin-5-yl)imidazo[1,2-b]pyridazine. ES/MS m/z: 389.20 [M+H].

Step 3: A solution of 8-(6,6-difluoro-2-azabicyclo[2.2.1]heptan-2-yl)-6-(2,4-dimethoxypyrimidin-5-yl)imidazo[1,2-b]pyridazine (368 mg) in 1:1 1N HCl:MeOH (4 mL) was heated to 80° C. After 20 hours, the reaction mixture was filtered and purified by RP-HPLC (5-80% MeCN/H₂O with TFA modifier), affording 5-(8-(6,6-difluoro-2-azabicyclo[2.2.1]heptan-2-yl)imidazo[1,2-b]pyridazin-6-yl)pyrimidine-2,4(1H,3H)-dione. ES/MS m/z: 361.10 [M+H]. $^1$H NMR (400 MHz, Methanol-d4) δ 8.20 (s, 1H), 8.16 (s, 1H), 7.86 (s, 1H), 7.33 (s, 1H), 5.30 (s, 1H), 3.98-3.84 (m, 1H), 3.53-3.47 (m, 1H), 2.95 (s, 1H), 2.40-2.21 (m, 1H), 2.14-1.89 (m, 3H).; $^{19}$F NMR (376 MHz, Methanol-d4) δ −78.15, −92.03−−93.17 (m), −114.17−−115.45 (m).

Example 645. 5-(8-(1-(trifluoromethyl)-3-azabicyclo[3.1.0]hexan-3-yl)imidazo[1,2-b]pyridazin-6-yl)pyrimidine-2,4(1H,3H)-dione

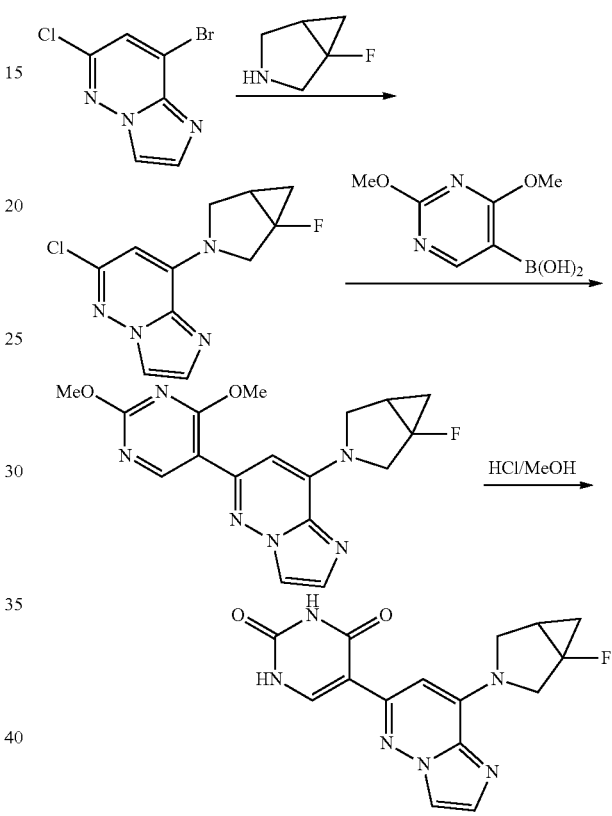

Step 1: A solution of 8-bromo-6-chloroimidazo[1,2-b]pyridazine (350 mg, 1.51 mmol, 1 equiv), 1-(trifluoromethyl)-3-azabicyclo[3.1.0]hexane hydrochloride (250 mg, 1.66 mmol, 1.1 equiv), DIPEA (0.63 mL, 3.61 mmol, 2.4 equiv), and MeCN (6 mL) was heated to 85° C. After 6 hours, the reaction mixture was directly purified by SiO₂ chromatography (0-100% EtOAc/Hex), affording 6-chloro-8-(1-(trifluoromethyl)-3-azabicyclo[3.1.0]hexan-3-yl)imidazo[1,2-b]pyridazine. ES/MS m/z: 303.10 [M+H].

Step 2: A solution of 6-chloro-8-(1-(trifluoromethyl)-3-azabicyclo[3.1.0]hexan-3-yl)imidazo[1,2-b]pyridazine (313 mg, 1.03 mmol, 1 equiv), (2,4-dimethoxypyrimidin-5-yl)boronic acid (228 mg, 1.24 mol, 1.2 equiv), cesium carbonate (674 mg, 2.07 mmol, 2 equiv), and PdCl₂(dppf)-CH₂Cl₂ (76 mg, 10 mol %) in 1:2 water/1,4-dioxane (5 mL) was heated to 80° C. After 16 hours, the reaction mixture was directly purified by SiO₂ chromatography (0-100% EtOAc/Hex), affording 6-(2,4-dimethoxypyrimidin-5-yl)-8-(1-(trifluoromethyl)-3-azabicyclo[3.1.0]hexan-3-yl)imidazo[1,2-b]pyridazine. ES/MS m/z: 407.20 [M+H].

Step 3: A solution of 6-(2,4-dimethoxypyrimidin-5-yl)-8-(1-(trifluoromethyl)-3-azabicyclo[3.1.0]hexan-3-yl)imidazo[1,2-b]pyridazine (305 mg) in 1:1 1N HCl:MeOH (4 mL)

was heated to 80° C. After 20 hours, the reaction mixture was filtered and washed with MeCN. The remaining solids were dried under vacuum, affording 5-(8-(1-(trifluoromethyl)-3-azabicyclo[3.1.0]hexan-3-yl)imidazo[1,2-b]pyridazin-6-yl)pyrimidine-2,4(1H,3H)-dione. ES/MS m/z: 379.10 [M+H]. $^1$H NMR (400 MHz, Methanol-d4) δ 8.25-8.22 (m, 2H), 7.93 (d, J=2.0 Hz, 1H), 7.34 (s, 1H), 4.38-4.31 (m, 1H), 4.21-4.12 (m, 2H), 4.06-3.98 (m, 1H), 2.41-2.32 (m, 1H), 1.60-1.51 (m, 1H), 1.07-0.98 (m, 1H). $^{19}$F NMR (376 MHz, Methanol-d4) δ −70.11.

Example 646. 5-(8-(7-azabicyclo[2.2.1]heptan-7-yl)imidazo[1,2-b]pyridazin-6-yl)pyrimidine-2,4(1H,3H)-dione

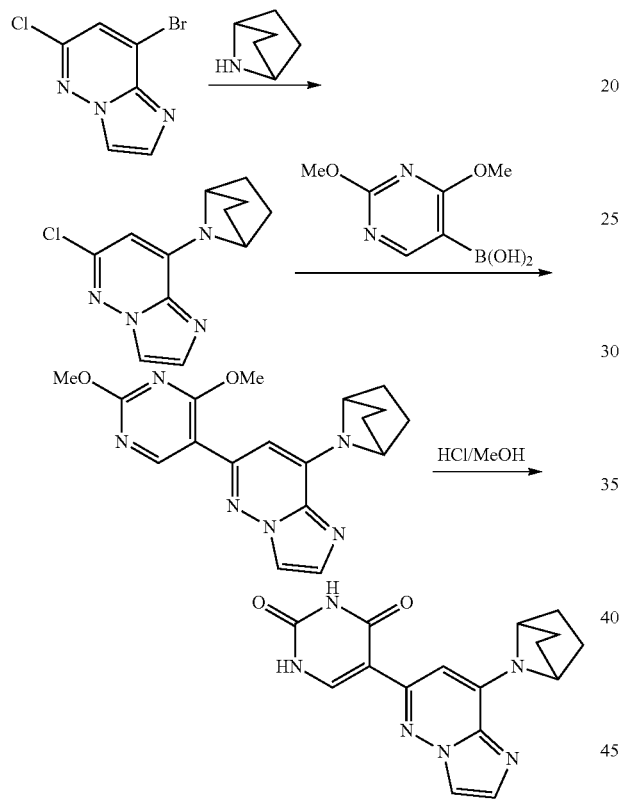

Step 1: A solution of 8-bromo-6-chloroimidazo[1,2-b]pyridazine (350 mg, 1.51 mmol, 1 equiv), 7-azabicyclo[2.2.1]heptane hydrochloride (161 mg, 1.66 mmol, 1.1 equiv), DIPEA (0.63 mL, 3.61 mmol, 2.4 equiv), and MeCN (6 mL) was heated to 85° C. After 5 hours, the reaction mixture was directly purified by SiO$_2$ chromatography (0-100% EtOAc/Hex), affording 8-(7-azabicyclo[2.2.1]heptan-7-yl)-6-chloroimidazo[1,2-b]pyridazine. ES/MS m/z: 249.10 [M+H].

Step 2: A solution of 8-(7-azabicyclo[2.2.1]heptan-7-yl)-6-chloroimidazo[1,2-b]pyridazine (114 mg, 0.46 mmol, 1 equiv), (2,4-dimethoxypyrimidin-5-yl)boronic acid (102 mg, 0.55 mol, 1.2 equiv), cesium carbonate (300 mg, 0.92 mmol, 2 equiv), and PdCl$_2$(dppf)-CH$_2$Cl$_2$ (34 mg, 10 mol %) in 1:2 water/1,4-dioxane (2.4 mL) was heated to 80° C. After 1 hour, the reaction mixture was directly purified by SiO$_2$ chromatography (0-100% EtOAc/Hex), affording 8-(7-azabicyclo[2.2.1]heptan-7-yl)-6-(2,4-dimethoxypyrimidin-5-yl)imidazo[1,2-b]pyridazine. ES/MS m/z: 353.20 [M+H].

Step 3: A solution of 8-(7-azabicyclo[2.2.1]heptan-7-yl)-6-(2,4-dimethoxypyrimidin-5-yl)imidazo[1,2-b]pyridazine (118 mg) in 1:1 1N HCl:MeOH (2 mL) was heated to 80° C. After 20 hours, the reaction mixture was filtered and washed with MeCN. The remaining solids were dried under vacuum, affording 5-(8-(7-azabicyclo[2.2.1]heptan-7-yl)imidazo[1,2-b]pyridazin-6-yl)pyrimidine-2,4(1H,3H)-dione. ES/MS m/z: 325.20 [M+H]. $^1$H NMR (400 MHz, Methanol-d4) δ 8.25-8.14 (m, 2H), 7.92 (bs, 1H), 7.63 (bs, 1H), 4.77-4.68 (m, 2H), 2.00-1.90 (m, 4H), 1.70-1.62 (m, 4H).

Example 647. 5-(8-(2-azabicyclo[2.2.2]octan-2-yl)imidazo[1,2-b]pyridazin-6-yl)pyrimidine-2,4(1H,3H)-dione

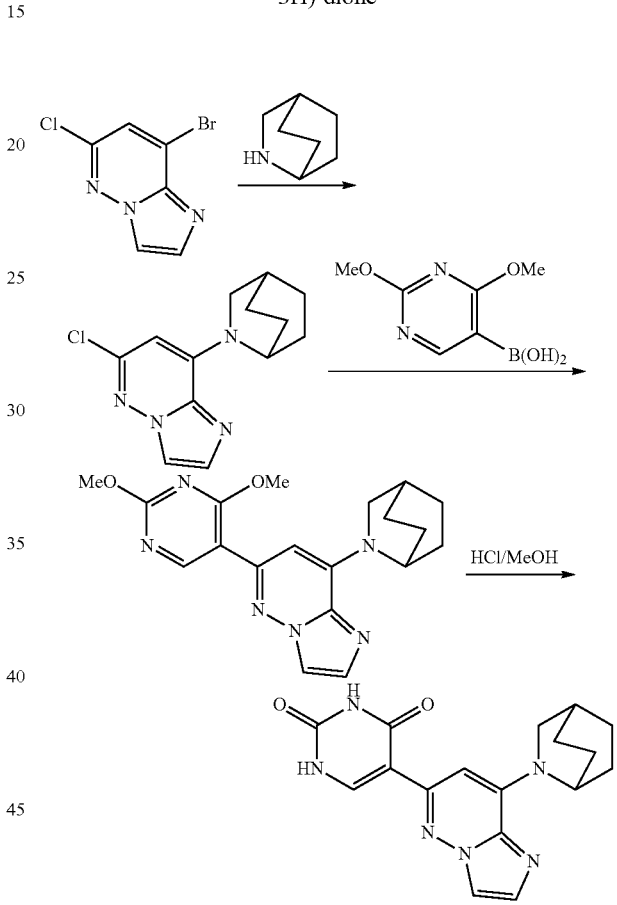

Step 1: A solution of 8-bromo-6-chloroimidazo[1,2-b]pyridazine (350 mg, 1.51 mmol, 1 equiv), 2-azabicyclo[2.2.2]octane hydrochloride (184 mg, 1.66 mmol, 1.1 equiv), DIPEA (0.63 mL, 3.61 mmol, 2.4 equiv), and MeCN (6 mL) was heated to 85° C. After 5 hours, the reaction mixture was directly purified by SiO$_2$ chromatography (0-100% EtOAc/Hex), affording 2-(6-chloroimidazo[1,2-b]pyridazin-8-yl)-2-azabicyclo[2.2.2]octane. ES/MS m/z: 263.10 [M+H].

Step 2: A solution of 2-(6-chloroimidazo[1,2-b]pyridazin-8-yl)-2-azabicyclo[2.2.2]octane (426 mg, 1.62 mmol, 1 equiv), (2,4-dimethoxypyrimidin-5-yl)boronic acid (358 mg, 1.95 mol, 1.2 equiv), cesium carbonate (1057 mg, 3.24 mmol, 2 equiv), and PdCl$_2$(dppf)-CH$_2$Cl$_2$ (119 mg, 10 mol %) in 1:2 water/1,4-dioxane (8 mL) was heated to 80° C. After 16 hours, the reaction mixture was directly purified by SiO$_2$ chromatography (0-100% EtOAc/Hex), affording 2-(6-

(2,4-dimethoxypyrimidin-5-yl)imidazo[1,2-b]pyridazin-8-yl)-2-azabicyclo[2.2.2]octane. ES/MS m/z: 367.20 [M+H].

Step 3: A solution of 2-(6-(2,4-dimethoxypyrimidin-5-yl)imidazo[1,2-b]pyridazin-8-yl)-2-azabicyclo[2.2.2]octane (365 mg) in 1:1 1N HCl:MeOH (4 mL) was heated to 80° C. After 20 hours, the reaction mixture was filtered and washed with MeCN. The remaining solids were dried under vacuum, affording 5-(8-(2-azabicyclo[2.2.2]octan-2-yl)imidazo[1,2-b]pyridazin-6-yl)pyrimidine-2,4(1H,3H)-dione. ES/MS m/z: 339.10 [M+H]. $^1$H NMR (400 MHz, Methanol-d4) δ 8.23 (s, 1H), 8.20 (d, J=2.0 Hz, 1H), 7.91 (d, J=2.0 Hz, 1H), 7.41 (s, 1H), 4.38 (s, 1H), 3.89-3.76 (m, 2H), 2.18-2.07 (m, 3H), 1.99-1.77 (m, 6H).

Example 648. 5-(8-(8-azabicyclo[3.2.1]octan-8-yl)imidazo[1,2-b]pyridazin-6-yl)pyrimidine-2,4(1H,3H)-dione

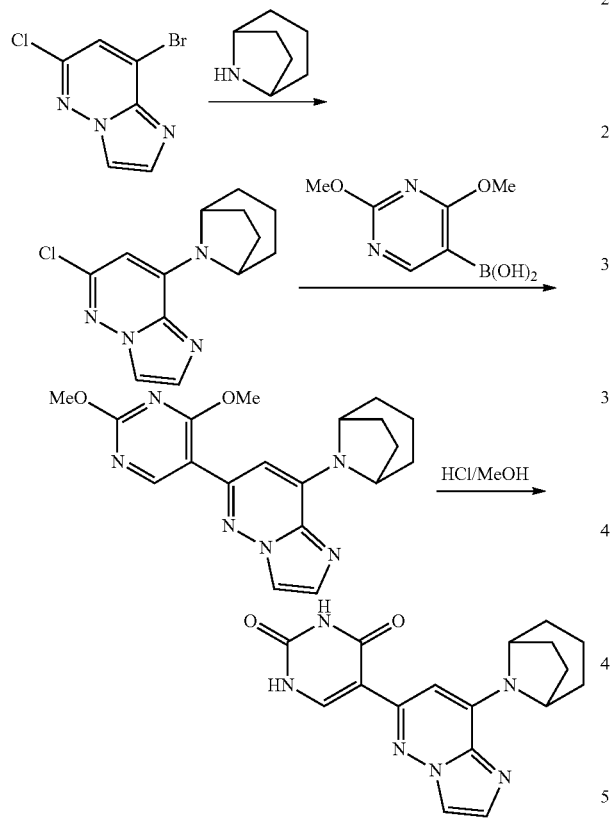

Step 1: A solution of 8-bromo-6-chloroimidazo[1,2-b]pyridazine (350 mg, 1.51 mmol, 1 equiv), 8-azabicyclo[3.2.1]octane hydrochloride (192 mg, 1.73 mmol, 1.15 equiv), DIPEA (0.63 mL, 3.61 mmol, 2.4 equiv), and MeCN (6 mL) was heated to 85° C. After 6 hours, the reaction mixture was directly purified by SiO$_2$ chromatography (0-100% EtOAc/Hex), affording 8-(8-azabicyclo[3.2.1]octan-8-yl)-6-chloroimidazo[1,2-b]pyridazine. ES/MS m/z: 263.10 [M+H].

Step 2: A solution of 8-(8-azabicyclo[3.2.1]octan-8-yl)-6-chloroimidazo[1,2-b]pyridazine (313 mg, 1.19 mmol, 1 equiv), (2,4-dimethoxypyrimidin-5-yl)boronic acid (263 mg, 1.43 mol, 1.2 equiv), cesium carbonate (776 mg, 2.38 mmol, 2 equiv), and PdCl$_2$(dppf)-CH$_2$Cl$_2$ (87 mg, 10 mol %) in 1:2 water/1,4-dioxane (8 mL) was heated to 80° C. After 2 hours, the reaction mixture was directly purified by SiO$_2$ chromatography (0-100% EtOAc/Hex), affording 8-(8-azabicyclo[3.2.1]octan-8-yl)-6-(2,4-dimethoxypyrimidin-5-yl)imidazo[1,2-b]pyridazine. ES/MS m/z: 367.20 [M+H].

Step 3: A solution of 8-(8-azabicyclo[3.2.1]octan-8-yl)-6-(2,4-dimethoxypyrimidin-5-yl)imidazo[1,2-b]pyridazine (310 mg) in 1:1 1N HCl:MeOH (4 mL) was heated to 80° C. After 20 hours, the reaction mixture was filtered and washed with MeCN. The remaining solids were dried under vacuum, affording 5-(8-(8-azabicyclo[3.2.1]octan-8-yl)imidazo[1,2-b]pyridazin-6-yl)pyrimidine-2,4(1H,3H)-dione. ES/MS m/z: 339.20 [M+H]. $^1$H NMR (400 MHz, Methanol-d4) δ 8.24 (s, 1H), 8.22 (d, J=2.0 Hz, 1H), 7.93 (d, J=2.0 Hz, 1H), 7.58 (s, 1H), 4.76 (bs, 2H), 2.22 (dd, J=8.8, 4.6 Hz, 2H), 2.09-1.88 (m, 5H), 1.68-1.57 (m, 3H).

Example 649. 1-(6-(2,4-dioxo-1,2,3,4-tetrahydropyrimidin-5-yl)imidazo[1,2-b]pyridazin-8-yl)-3-methylpyrrolidine-3-carbonitrile

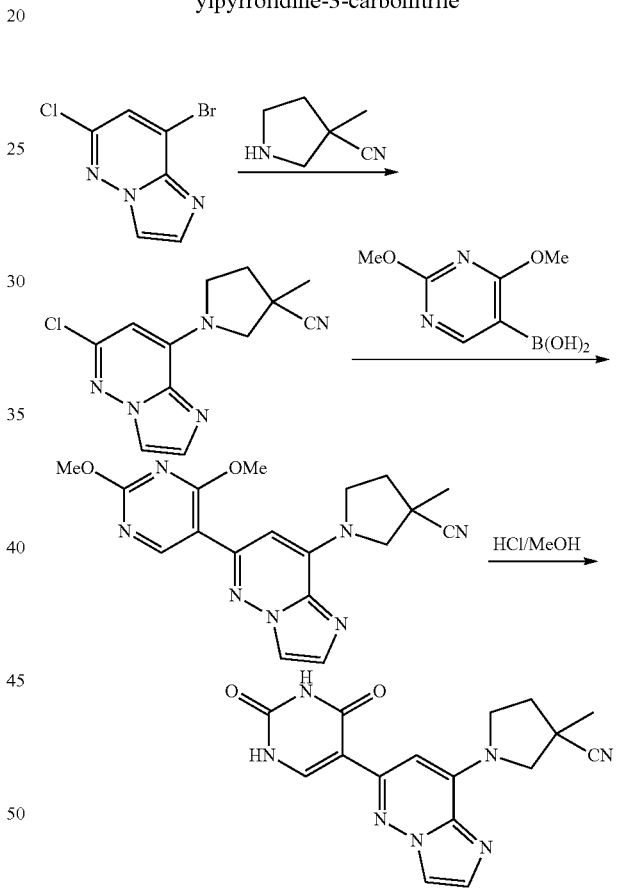

Step 1: A solution of 8-bromo-6-chloroimidazo[1,2-b]pyridazine (350 mg, 1.51 mmol, 1 equiv), 3-methylpyrrolidine-3-carbonitrile hydrochloride (182 mg, 1.66 mmol, 1.1 equiv), DIPEA (0.63 mL, 3.61 mmol, 2.4 equiv), and MeCN (6 mL) was heated to 85° C. After 6 hours, the reaction mixture was directly purified by SiO$_2$ chromatography (0-100% EtOAc/Hex), affording 1-(6-chloroimidazo[1,2-b]pyridazin-8-yl)-3-methylpyrrolidine-3-carbonitrile. ES/MS m/z: 262.10 [M+H].

Step 2: A solution of 1-(6-chloroimidazo[1,2-b]pyridazin-8-yl)-3-methylpyrrolidine-3-carbonitrile (447 mg, 1.71 mmol, 1 equiv), (2,4-dimethoxypyrimidin-5-yl)boronic acid (377 mg, 2.05 mol, 1.2 equiv), cesium carbonate (1113 mg, 3.42 mmol, 2 equiv), and PdCl$_2$(dppf)-CH$_2$Cl$_2$ (125 mg, 10 mol %) in 1:2 water/1,4-dioxane (5 mL) was heated to 80° C. After 16 hours, the reaction mixture was directly purified by SiO$_2$ chromatography (0-100% EtOAc/Hex), affording 1-(6-(2,4-dimethoxypyrimidin-5-yl)imidazo[1,2-b]pyridazin-8-yl)-3-methylpyrrolidine-3-carbonitrile. ES/MS m/z: 366.10 [M+H].

Step 3: A solution of 1-(6-(2,4-dimethoxypyrimidin-5-yl)imidazo[1,2-b]pyridazin-8-yl)-3-methylpyrrolidine-3-carbonitrile (274 mg) in 1:1 1N HCl:MeOH (4 mL) was heated to 80° C. After 20 hours, the reaction mixture was filtered and purified by RP-HPLC (5-80% MeCN/H$_2$O with TFA modifier), affording 1-(6-(2,4-dioxo-1,2,3,4-tetrahydropyrimidin-5-yl)imidazo[1,2-b]pyridazin-8-yl)-3-methylpyrrolidine-3-carbonitrile. ES/MS m/z: 338.20 [M+H]. $^1$H NMR (400 MHz, Methanol-d4) δ 8.19 (s, 1H), 8.12 (d, J=1.7 Hz, 1H), 7.79 (d, J=1.7 Hz, 1H), 7.08 (s, 1H), 4.47 (d, J=11.0 Hz, 1H), 4.13-4.02 (m, 2H), 3.91 (d, J=11.0 Hz, 1H), 2.66-2.56 (m, 1H), 2.35-2.21 (m, 1H), 1.65 (s, 3H).

Example 650. 5-(8-(3-azabicyclo[3.1.1]heptan-3-yl)imidazo[1,2-b]pyridazin-6-yl)pyrimidine-2,4(1H,3H)-dione

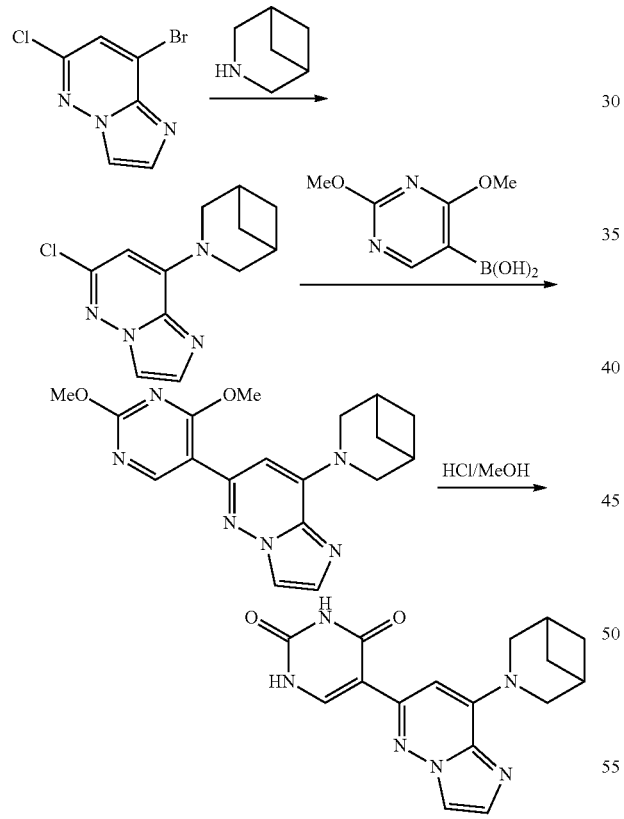

Step 1: A solution of 8-bromo-6-chloroimidazo[1,2-b]pyridazine (350 mg, 1.51 mmol, 1 equiv), 3-azabicyclo[3.1.1]heptane hydrochloride (161 mg, 1.66 mmol, 1.1 equiv), DIPEA (0.63 mL, 3.61 mmol, 2.4 equiv), and MeCN (6 mL) was heated to 85° C. After 6 hours, the reaction mixture was directly purified by SiO$_2$ chromatography (0-100% EtOAc/Hex), affording 3-(6-chloroimidazo[1,2-b]pyridazin-8-yl)-3-azabicyclo[3.1.1]heptane. ES/MS m/z: 249.10 [M+H].

Step 2: A solution of 3-(6-chloroimidazo[1,2-b]pyridazin-8-yl)-3-azabicyclo[3.1.1]heptane (333 mg, 1.34 mmol, 1 equiv), (2,4-dimethoxypyrimidin-5-yl)boronic acid (296 mg, 1.61 mol, 1.2 equiv), cesium carbonate (872 mg, 2.68 mmol, 2 equiv), and PdCl$_2$(dppf)-CH$_2$Cl$_2$ (98 mg, 10 mol %) in 1:2 water/1,4-dioxane (8 mL) was heated to 80° C. After 4 hours, the reaction mixture was directly purified by SiO$_2$ chromatography (0-100% EtOAc/Hex), affording 3-(6-(2,4-dimethoxypyrimidin-5-yl)imidazo[1,2-b]pyridazin-8-yl)-3-azabicyclo[3.1.1]heptane. ES/MS m/z: 353.20 [M+H].

Step 3: A solution of 3-(6-(2,4-dimethoxypyrimidin-5-yl)imidazo[1,2-b]pyridazin-8-yl)-3-azabicyclo[3.1.1]heptane (246 mg) in 1:1 1N HCl:MeOH (4 mL) was heated to 80° C. After 20 hours, the reaction mixture was filtered and washed with MeCN. The remaining solids were dried under vacuum, affording 5-(8-(3-azabicyclo[3.1.1]heptan-3-yl)imidazo[1,2-b]pyridazin-6-yl)pyrimidine-2,4(1H,3H)-dione. ES/MS m/z: 325.20 [M+H]. $^1$H NMR (400 MHz, Methanol-d4) δ 8.27 (s, 1H), 8.25 (d, J=2.0 Hz, 1H), 7.94 (d, J=2.0 Hz, 1H), 7.47 (s, 1H), 4.12 (s, 4H), 2.77-2.69 (m, 2H), 2.42-2.32 (m, 2H), 1.61-1.52 (m, 2H).

Example 651. 5-(8-(2-azabicyclo[3.2.1]octan-2-yl)imidazo[1,2-b]pyridazin-6-yl)pyrimidine-2,4(1H,3H)-dione

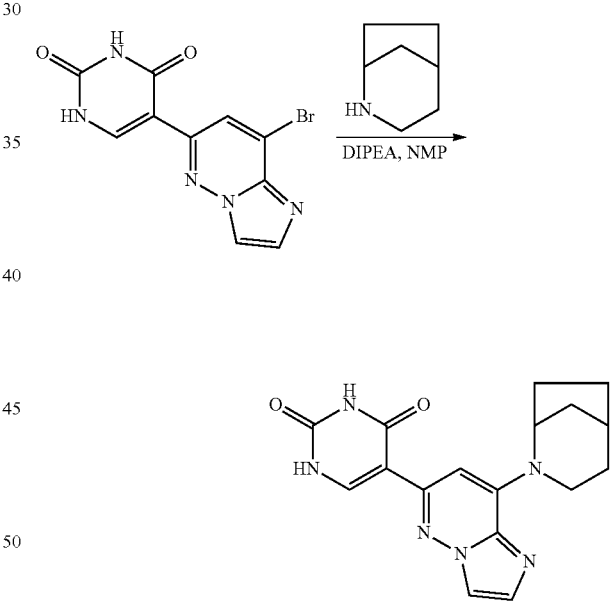

A solution of 5-(8-bromoimidazo[1,2-b]pyridazin-6-yl)pyrimidine-2,4(1H,3H)-dione (50 mg, 0.16 mmol, 1 equiv), 2-azabicyclo[3.2.1]octane hydrochloride (27 mg, 0.24 mmol, 1.5 equiv), and DIPEA (0.071 mL, 0.41 mmol, 2.5 equiv) in NMP (2 mL) was microwaved at 120° C. After 90 minutes, the reaction mixture was directly purified by SiO$_2$ chromatography (0-100% EtOAc/Hex), affording 5-(8-(2-azabicyclo[3.2.1]octan-2-yl)imidazo[1,2-b]pyridazin-6-yl)pyrimidine-2,4(1H,3H)-dione. ES/MS m/z: 339.20 [M+H]. $^1$H NMR (400 MHz, Methanol-d4) δ 8.21 (s, 1H), 8.16 (d, J=1.9 Hz, 1H), 7.87 (d, J=1.9 Hz, 1H), 7.51 (s, 1H), 4.79-4.75 (m, 1H), 3.79-3.65 (m, 1H), 3.53-3.38 (m, 1H), 2.58-2.44 (m, 1H), 2.01-1.58 (m, 8H).

Example 652. 5-(8-(3-(chloromethyl)-3-(hydroxymethyl)pyrrolidin-1-yl)imidazo[1,2-b]pyridazin-6-yl)pyrimidine-2,4(1H,3H)-dione

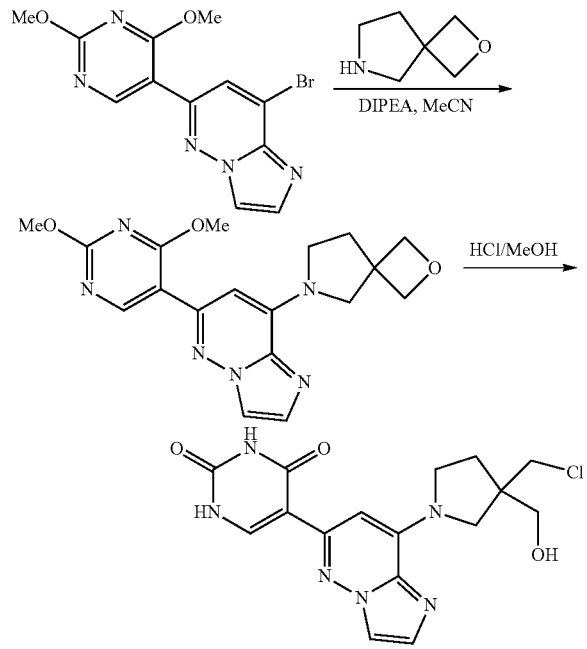

Step 1: A solution of 8-bromo-6-(2,4-dimethoxypyrimidin-5-yl)imidazo[1,2-b]pyridazine (150 mg, 0.45 mmol, 1 equiv), 2-oxa-7-azaspiro[3.4]octane (76 mg, 0.67 mmol, 1.5 equiv), and DIPEA (0.23 mL, 1.34 mmol, 3 equiv) in MeCN (3.75 mL) was heated to 100° C. After 16 hours, the reaction mixture was directly purified by SiO₂ chromatography (0-100% EtOAc/Hex), affording 6-(6-(2,4-dimethoxypyrimidin-5-yl)imidazo[1,2-b]pyridazin-8-yl)-2-oxa-6-azaspiro[3.4]octane. ES/MS m/z: 377.10 [M+H].

Step 2: A solution of 6-(6-(2,4-dimethoxypyrimidin-5-yl)imidazo[1,2-b]pyridazin-8-yl)-2-oxa-6-azaspiro[3.4]octane (58 mg) in 1:1 1N HCl:MeOH (1 mL) was heated to 80° C. After 4 hours, the reaction mixture was filtered and purified by RP-HPLC (10-90% MeCN/H₂O with TFA modifier), affording 5-(8-(3-(chloromethyl)-3-(hydroxymethyl)pyrrolidin-1-yl)imidazo[1,2-b]pyridazin-6-yl)pyrimidine-2,4(1H,3H)-dione. ES/MS m/z: 377.10 [M+H]. ¹H NMR (400 MHz, Methanol-d4) δ 8.20 (s, 1H), 8.16 (d, J=1.9 Hz, 1H), 7.85 (d, J=1.9 Hz, 1H), 7.17 (s, 1H), 4.04-3.94 (m, 2H), 3.84 (s, 2H), 3.81 (s, 2H), 3.69 (s, 2H), 2.22-2.11 (m, 2H).

Example 653. 5-(8-(2-oxa-6-azaspiro[3.4]octan-6-yl)imidazo[1,2-b]pyridazin-6-yl)pyrimidine-2,4(1H,3H)-dione

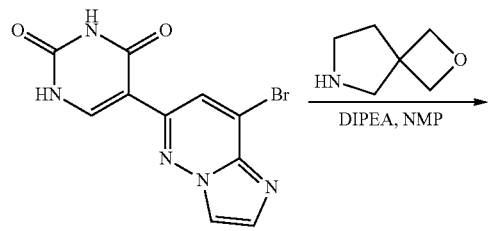

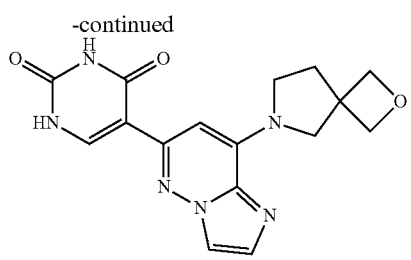

A solution of 5-(8-bromoimidazo[1,2-b]pyridazin-6-yl)pyrimidine-2,4(1H,3H)-dione (20 mg, 0.065 mmol, 1 equiv) and 2-oxa-7-azaspiro[3.4]octane (15 mg, 0.13 mmol, 2 equiv) in NMP (1 mL) was heated to 100° C. After 2 hours, the reaction mixture was filtered and purified by RP-HPLC (10-90% MeCN/H₂O with TFA modifier), affording 5-(8-(2-oxa-6-azaspiro[3.4]octan-6-yl)imidazo[1,2-b]pyridazin-6-yl)pyrimidine-2,4(1H,3H)-dione. ES/MS m/z: 341.10 [M+H]. ¹H NMR (400 MHz, Methanol-d4) δ 8.17 (s, 1H), 8.11-8.08 (m, 1H), 7.80-7.76 (m, 1H), 7.06 (s, 1H), 4.81-4.67 (m, 4H), 4.17 (s, 2H), 3.88 (t, J=7.0 Hz, 2H), 2.43 (t, J=7.0 Hz, 2H). ¹⁹F NMR (376 MHz, Methanol-d4) δ −77.82.

Example 654. 2-(1-(6-(2,4-dioxo-1,2,3,4-tetrahydropyrimidin-5-yl)imidazo[1,2-b]pyridazin-8-yl)pyrrolidin-3-yl)-N-isopropylacetamide

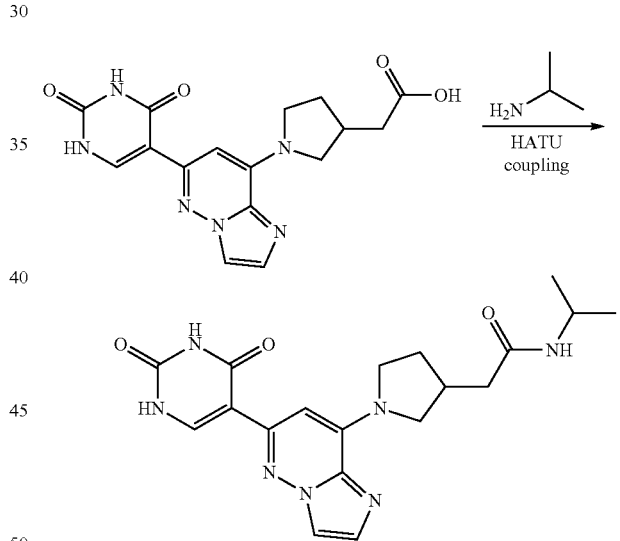

To a solution of 2-(1-(6-(2,4-dioxo-1,2,3,4-tetrahydropyrimidin-5-yl)imidazo[1,2-b]pyridazin-8-yl)pyrrolidin-3-yl)acetic acid (20 mg, 0.056 mmol, 1 equiv), propan-2-amine (0.01 mL, 0.11 mmol, 2 equiv), and HATU (32 mg, 0.084 mmol, 1.5 equiv) in DMF (1 mL) was added DIPEA (0.05 mL, 0.28 mmol, 5 equiv). After 14 hours, the reaction mixture was purified by RP-HPLC (10-90% MeCN/H₂O with TFA modifier), affording 2-(1-(6-(2,4-dioxo-1,2,3,4-tetrahydropyrimidin-5-yl)imidazo[1,2-b]pyridazin-8-yl)pyrrolidin-3-yl)-N-isopropylacetamide. ES/MS m/z: 398.20 [M+H]. ¹H NMR (400 MHz, Methanol-d4) δ 8.20 (s, 1H), 8.14 (d, J=1.8 Hz, 1H), 7.84 (d, J=1.8 Hz, 1H), 7.14 (s, 1H), 4.15-4.05 (m, 1H), 4.07-3.93 (m, 2H), 3.91-3.79 (m, 1H), 3.64-3.54 (m, 1H), 2.86-2.73 (m, 1H), 2.41 (d, J=7.4 Hz, 2H), 2.37-2.26 (m, 1H), 1.94-1.77 (m, 1H), 1.18 (d, J=6.6 Hz, 3H), 1.17 (d, J=6.6 Hz, 3H).

Example 655. 5-(8-(1-(3,3,3-trifluoropropanoyl)-1,6-diazaspiro[3.4]octan-6-yl)imidazo[1,2-b]pyridazin-6-yl)pyrimidine-2,4(1H,3H)-dione

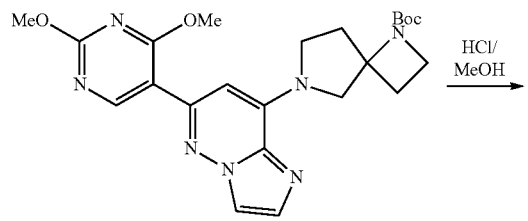

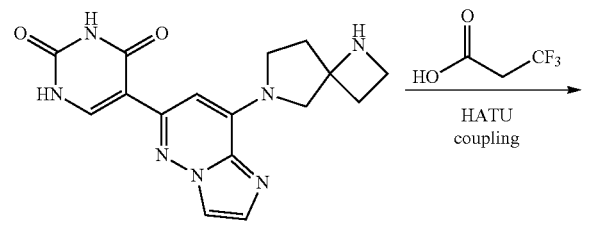

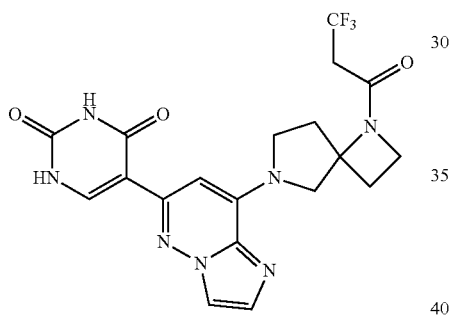

Example 656. 5-(8-(1-acetyl-1,6-diazaspiro[3.4]octan-6-yl)imidazo[1,2-b]pyridazin-6-yl)pyrimidine-2,4(1H,3H)-dione

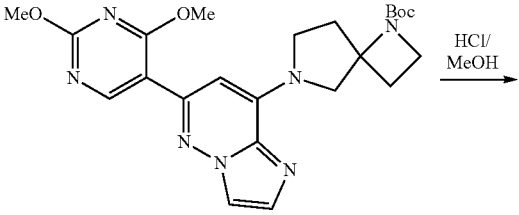

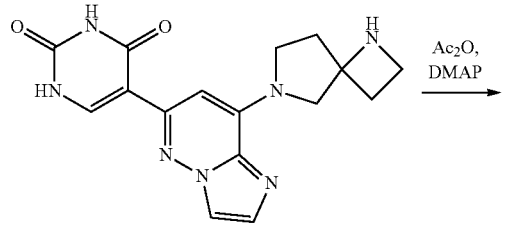

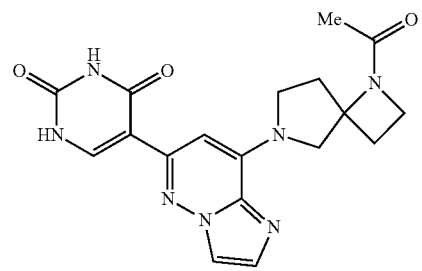

Step 1: To a solution of tert-butyl 6-(6-(2,4-dimethoxypyrimidin-5-yl)imidazo[1,2-b]pyridazin-8-yl)-1,6-diazaspiro[3.4]octane-1-carboxylate (690 mg) in 1:1 1N HCl: MeOH (5 mL) was heated to 80° C. After 24 hours, the reaction mixture was concentrated to afford 5-(8-(1,6-diazaspiro[3.4]octan-6-yl)imidazo[1,2-b]pyridazin-6-yl)pyrimidine-2,4(1H,3H)-dione. This material was used in the next step without purification. ES/MS m/z: 4340.20 [M+H].

Step 2: To a solution of 5-(8-(1,6-diazaspiro[3.4]octan-6-yl)imidazo[1,2-b]pyridazin-6-yl)pyrimidine-2,4(1H,3H)-dione (30 mg, 0.088 mmol, 1 equiv), 3,3,3-trifluoropropanoic acid (23 mg, 0.18 mmol, 2 equiv), and HATU (50 mg, 0.13 mmol, 1.5 equiv) in DMF (1 mL) was added DIPEA (1 drop). After 1 hour, the reaction mixture was purified by RP-HPLC (10-90% MeCN/H$_2$O with TFA modifier), affording 5-(8-(1-(3,3,3-trifluoropropanoyl)-1,6-diazaspiro[3.4]octan-6-yl)imidazo[1,2-b]pyridazin-6-yl)pyrimidine-2,4(1H,3H)-dione. ES/MS m/z: 450.20 [M+H]. $^1$H NMR (400 MHz, Methanol-d4) δ 8.22 (s, 1H), 8.17 (d, J=2.0 Hz, 1H), 7.86 (d, J=2.0 Hz, 1H), 7.21 (s, 1H), 4.45 (d, J=11.6 Hz, 1H), 4.26-4.14 (m, 3H), 4.07 (d, J=11.6 Hz, 1H), 4.03-3.94 (m, 1H), 3.24-3.13 (m, 2H), 2.89-2.82 (m, 1H), 2.63-2.53 (m, 1H), 2.51-2.43 (m, 1H), 2.43-2.33 (m, 1H). $^{19}$F NMR (376 MHz, Methanol-d4) δ −64.61 (t, J=10.7 Hz), −77.91.

Step 1: To a solution of tert-butyl 6-(6-(2,4-dimethoxypyrimidin-5-yl)imidazo[1,2-b]pyridazin-8-yl)-1,6-diazaspiro[3.4]octane-1-carboxylate (690 mg) in 1:1 1N HCl: MeOH (5 mL) was heated to 80° C. After 24 hours, the reaction mixture was concentrated to afford 5-(8-(1,6-diazaspiro[3.4]octan-6-yl)imidazo[1,2-b]pyridazin-6-yl)pyrimidine-2,4(1H,3H)-dione. This material was used in the next step without purification. ES/MS m/z: 340.20 [M+H].

Step 2: To a solution of 5-(8-(1,6-diazaspiro[3.4]octan-6-yl)imidazo[1,2-b]pyridazin-6-yl)pyrimidine-2,4(1H,3H)-dione (30 mg, 0.088 mmol, 1 equiv), acetic anhydride (9 mg, 0.088 mmol, 1 equiv) in CH$_2$Cl$_2$ (1 mL) was added DMAP (54 mg, 0.44 mmol, 5 equiv). After 1 hour, the reaction mixture was purified by RP-HPLC (10-90% MeCN/H$_2$O with TFA modifier), affording 5-(8-(1-acetyl-1,6-diazaspiro[3.4]octan-6-yl)imidazo[1,2-b]pyridazin-6-yl)pyrimidine-2,4(1H,3H)-dione. ES/MS m/z: 382.20 [M+H]. $^1$H NMR (400 MHz, Methanol-d4) δ 8.21 (s, 1H), 8.14 (d, J=1.8 Hz, 1H), 7.82 (d, J=1.8 Hz, 1H), 7.13 (s, 1H), 4.48 (d, J=11.4 Hz, 1H), 4.26-4.04 (m, 4H), 4.02-3.90 (m, 1H), 2.95-2.80 (m, 1H), 2.59-2.50 (m, 1H), 2.49-2.40 (m, 1H), 2.40-2.29 (m, 1H), 1.87 (s, 3H).

Example 657. 5-(8-(1-isobutyryl-1,6-diazaspiro[3.4]octan-6-yl)imidazo[1,2-b]pyridazin-6-yl)pyrimidine-2,4(1H,3H)-dione

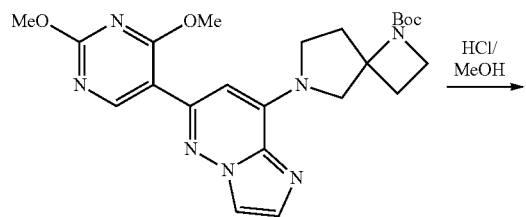

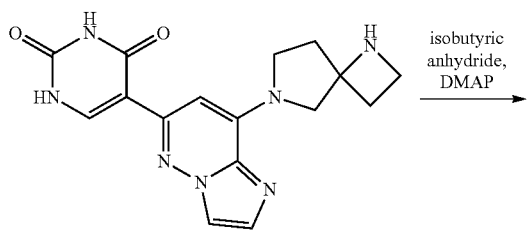

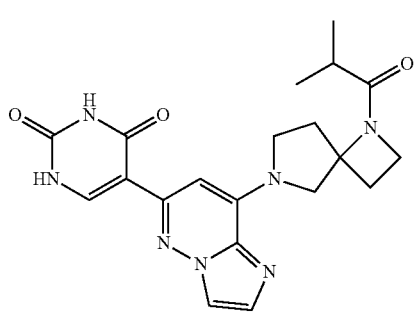

Step 1: To a solution of tert-butyl 6-(6-(2,4-dimethoxypyrimidin-5-yl)imidazo[1,2-b]pyridazin-8-yl)-1,6-diazaspiro[3.4]octane-1-carboxylate (690 mg) in 1:1 1N HCl:MeOH (5 mL) was heated to 80° C. After 24 hours, the reaction mixture was concentrated to afford 5-(8-(1,6-diazaspiro[3.4]octan-6-yl)imidazo[1,2-b]pyridazin-6-yl)pyrimidine-2,4(1H,3H)-dione. This material was used in the next step without purification. ES/MS m/z: 340.20 [M+H].

Step 2: To a solution of 5-(8-(1,6-diazaspiro[3.4]octan-6-yl)imidazo[1,2-b]pyridazin-6-yl)pyrimidine-2,4(1H,3H)-dione (30 mg, 0.088 mmol, 1 equiv), isobutyric anhydride (28 mg, 0.18 mmol, 2 equiv) in $CH_2Cl_2$ (1 mL) was added DMAP (54 mg, 0.44 mmol, 5 equiv). After 1 hour, the reaction mixture was purified by RP-HPLC (10-90% MeCN/$H_2O$ with TFA modifier), affording 5-(8-(1-isobutyryl-1,6-diazaspiro[3.4]octan-6-yl)imidazo[1,2-b]pyridazin-6-yl)pyrimidine-2,4(1H,3H)-dione. ES/MS m/z: 410.20 [M+H]. $^1$H NMR (400 MHz, Methanol-d4) δ 8.20 (s, 1H), 8.14 (d, J=1.8 Hz, 1H), 7.82 (d, J=1.8 Hz, 1H), 7.15 (s, 1H), 4.43 (d, J=11.4 Hz, 1H), 4.25-4.11 (m, 3H), 4.07 (d, J=11.4 Hz, 1H), 4.01-3.89 (m, 1H), 2.88-2.77 (m, 1H), 2.61-2.38 (m, 3H), 2.39-2.30 (m, 1H), 1.07 (d, J=6.8 Hz, 3H), 1.04 (d, J=6.8 Hz, 3H).

Example 658. 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-(1-(trifluoromethyl)cyclopropyl)acetamide

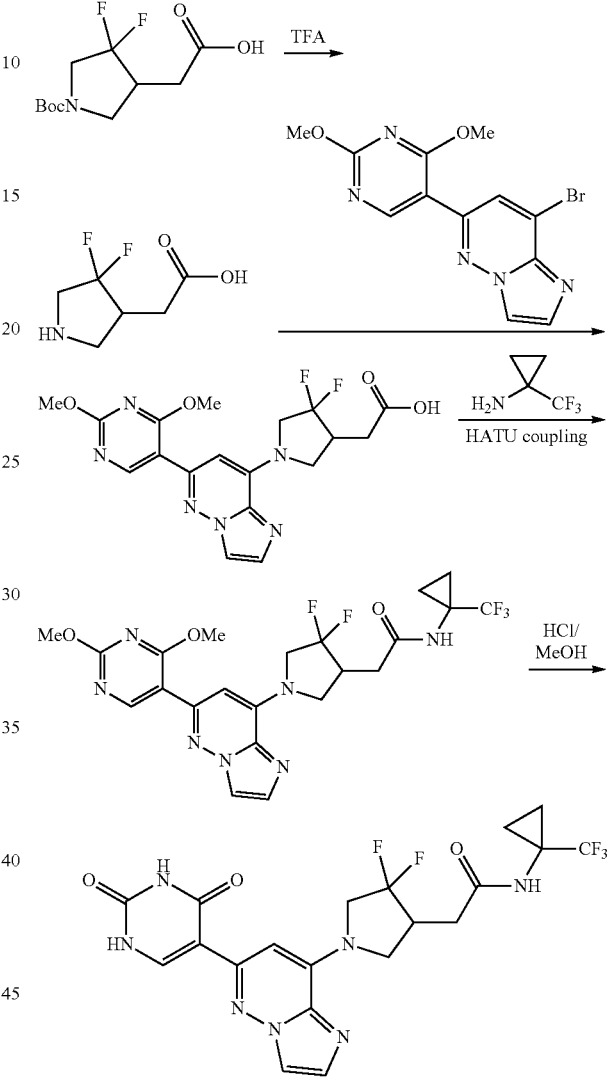

Step 1: To a solution of 2-(1-(tert-butoxycarbonyl)-4,4-difluoropyrrolidin-3-yl)acetic acid (1000 mg, 3.77 mmol, 1 equiv) in $CH_2Cl_2$ (7.5 mL) was added trifluoroacetic acid (2.5 mL). After 6 hours, the reaction mixture was concentrated to afford 2-(4,4-difluoropyrrolidin-3-yl)acetic acid TFA salt. This material was used in the next step without purification. $^1$H NMR (400 MHz, DMSO-d6) δ 3.84-3.60 (m, 3H), 3.18 (t, J=11.0 Hz, 1H), 3.08-2.86 (m, 1H), 2.69-2.48 (m, 2H).

Step 2: To a solution of 8-bromo-6-(2,4-dimethoxypyrimidin-5-yl)imidazo[1,2-b]pyridazine (1040 mg, 3.09 mmol, 1 equiv) in NMP (10 mL) was added DIPEA (1.29 mL, 7.43 mmol, 2.4 equiv) and crude 2-(4,4-difluoropyrrolidin-3-yl)acetic acid (562 mg, 3.40 mmol, 1.1 equiv). The reaction mixture was heated to 115° C. After 48 hours, the reaction mixture was cooled to room temperature and acidified with 1N HCl (10 mL). The layers were separated, and the aqueous layer was exhaustively extracted with EtOAc. The combined organic layers were dried over Na₂SO₄, filtered, and concentrated. Purification was accomplished by SiO₂ chromatography (0-40% MeOH/CH₂Cl₂), affording 2-(1-(6-(2,4-dimethoxypyrimidin-5-yl)imidazo[1,2-b]pyridazin-8-yl)-4,4-difluoropyrrolidin-3-yl)acetic acid. ES/MS m/z: 421.20 [M+H].

Step 3: To a solution of 2-(1-(6-(2,4-dimethoxypyrimidin-5-yl)imidazo[1,2-b]pyridazin-8-yl)-4,4-difluoropyrrolidin-3-yl)acetic acid (30 mg, 0.071 mmol, 1 equiv), 1-(trifluoromethyl)cyclopropan-1-amine hydrochloride (18 mg, 0.14 mmol, 2 equiv), and HATU (41 mg, 0.11 mmol, 1.5 equiv) in DMF (1 mL) was added DIPEA (0.06 mL, 0.36 mmol, 5 equiv). After 1 hour, the reaction mixture was directly purified by SiO₂ chromatography (0-15% MeOH/CH₂Cl₂), affording 2-(1-(6-(2,4-dimethoxypyrimidin-5-yl)imidazo[1,2-b]pyridazin-8-yl)-4,4-difluoropyrrolidin-3-yl)-N-(1-(trifluoromethyl)cyclopropyl)acetamide. ES/MS m/z: 428.20 [M+H].

Step 4: A solution of 2-(1-(6-(2,4-dimethoxypyrimidin-5-yl)imidazo[1,2-b]pyridazin-8-yl)-4,4-difluoropyrrolidin-3-yl)-N-(1-(trifluoromethyl)cyclopropyl)acetamide (63 mg) in 1:1 1N HCl:MeOH (2 mL) was heated to 80° C. After 14 hours, the reaction mixture was purified by RP-HPLC (10-90% MeCN/H₂O with TFA modifier), affording 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-(1-(trifluoromethyl)cyclopropyl)acetamide. ES/MS m/z: 500.20 [M+H]. ¹H NMR (400 MHz, Methanol-d4) δ 8.13 (s, 1H), 8.04 (s, 1H), 7.70 (s, 1H), 6.92 (s, 1H), 4.46-4.28 (m, 3H), 3.78-3.67 (m, 1H), 3.26-3.13 (m, 1H), 2.79-2.64 (m, 1H), 2.57-2.40 (m, 1H), 1.32-1.26 (m, 2H), 1.16-1.06 (m, 2H). ¹⁹F NMR (376 MHz, Methanol-d4) δ −75.71, −77.96, −110.80-114.52 (m).

Example 659. 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-isopropylacetamide

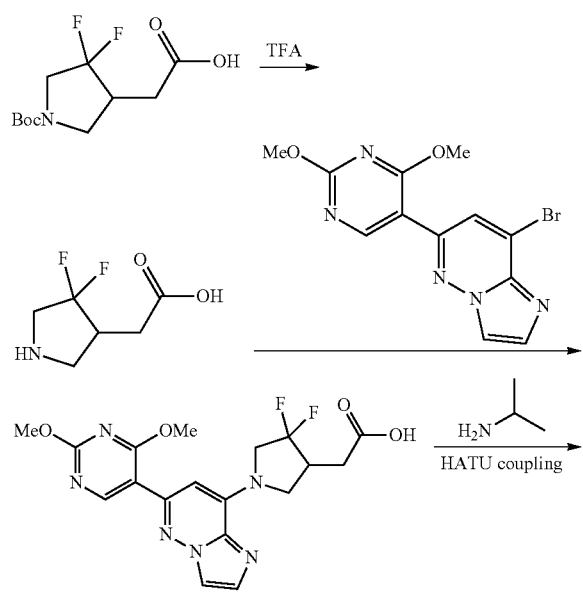

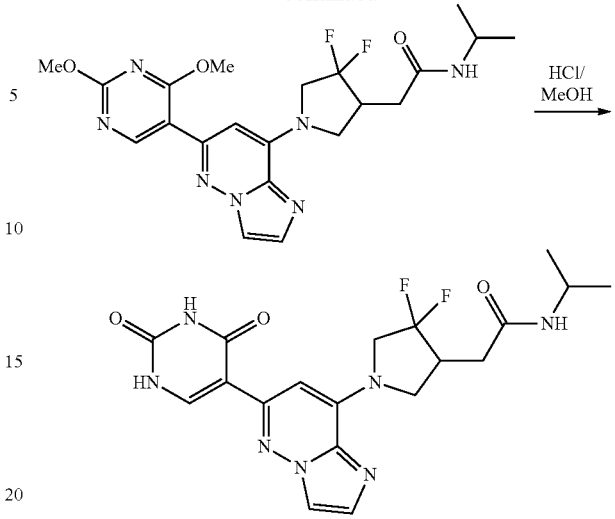

Step 1: To a solution of 2-(1-(tert-butoxycarbonyl)-4,4-difluoropyrrolidin-3-yl)acetic acid (1000 mg, 3.77 mmol, 1 equiv) in CH₂Cl₂ (7.5 mL) was added trifluoroacetic acid (2.5 mL). After 6 hours, the reaction mixture was concentrated to afford 2-(4,4-difluoropyrrolidin-3-yl)acetic acid. This material was used in the next step without purification. ¹H NMR (400 MHz, DMSO-d6) δ 3.84-3.60 (m, 3H), 3.18 (t, J=11.0 Hz, 1H), 3.08-2.86 (m, 1H), 2.69-2.48 (m, 2H).

Step 2: To a solution of 8-bromo-6-(2,4-dimethoxypyrimidin-5-yl)imidazo[1,2-b]pyridazine (1040 mg, 3.09 mmol, 1 equiv) in NMP (10 mL) was added DIPEA (1.29 mL, 7.43 mmol, 2.4 equiv) and 2-(4,4-difluoropyrrolidin-3-yl)acetic acid TFA salt (562 mg, 3.40 mmol, 1.1 equiv). The reaction mixture was heated to 115° C. After 48 hours, the reaction mixture was cooled to room temperature and acidified with 1N HCl (10 mL). The layers were separated, and the aqueous layer was exhaustively extracted with EtOAc. The combined organic layers were dried over Na₂SO₄, filtered, and concentrated. Purification was accomplished by SiO₂ chromatography (0-40% MeOH/CH₂Cl₂), affording 2-(1-(6-(2,4-dimethoxypyrimidin-5-yl)imidazo[1,2-b]pyridazin-8-yl)-4,4-difluoropyrrolidin-3-yl)acetic acid. ES/MS m/z: 421.20 [M+H].

Step 3: To a solution of 2-(1-(6-(2,4-dimethoxypyrimidin-5-yl)imidazo[1,2-b]pyridazin-8-yl)-4,4-difluoropyrrolidin-3-yl)acetic acid (50 mg, 0.12 mmol, 1 equiv), propan-2-amine (0.02 mL, 0.24 mmol, 2 equiv), and HATU (68 mg, 0.18 mmol, 1.5 equiv) in DMF (1 mL) was added DIPEA (0.04 mL, 0.24 mmol, 2 equiv). After 1 hour, the reaction mixture was directly purified by SiO₂ chromatography (0-15% MeOH/CH₂Cl₂), affording 2-(1-(6-(2,4-dimethoxypyrimidin-5-yl)imidazo[1,2-b]pyridazin-8-yl)-4,4-difluoropyrrolidin-3-yl)-N-isopropylacetamide. ES/MS m/z: 462.30 [M+H].

Step 4: A solution of 2-(1-(6-(2,4-dimethoxypyrimidin-5-yl)imidazo[1,2-b]pyridazin-8-yl)-4,4-difluoropyrrolidin-3-yl)-N-isopropylacetamide (75 mg) in 1:1 1N HCl:MeOH (2 mL) was heated to 80° C. After 14 hours, the reaction mixture was purified by RP-HPLC (10-90% MeCN/H₂O with TFA modifier), affording 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-isopropylacetamide. ES/MS m/z: 434.20 [M+H]. ¹H NMR (400 MHz, Methanol-d4) δ 8.18 (s, 1H), 8.12 (m, 1H), 7.82-7.78 (m, 1H), 7.12-7.03 (m, 1H), 4.44-4.28 (m, 3H), 4.04-3.93 (m, 1H), 3.82-3.72 (m, 1H), 2.74-2.64 (m, 1H), 2.51-2.37 (m, 1H), 1.17 (d, J=6.6 Hz, 3H), 1.16 (d, J=6.6 Hz, 3H). ¹⁹F NMR (376 MHz, Methanol-d4) δ −78.09, −111.05−−114.49 (m).

Example 660. 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-(3-fluorobicyclo[1.1.1]pentan-1-yl)acetamide

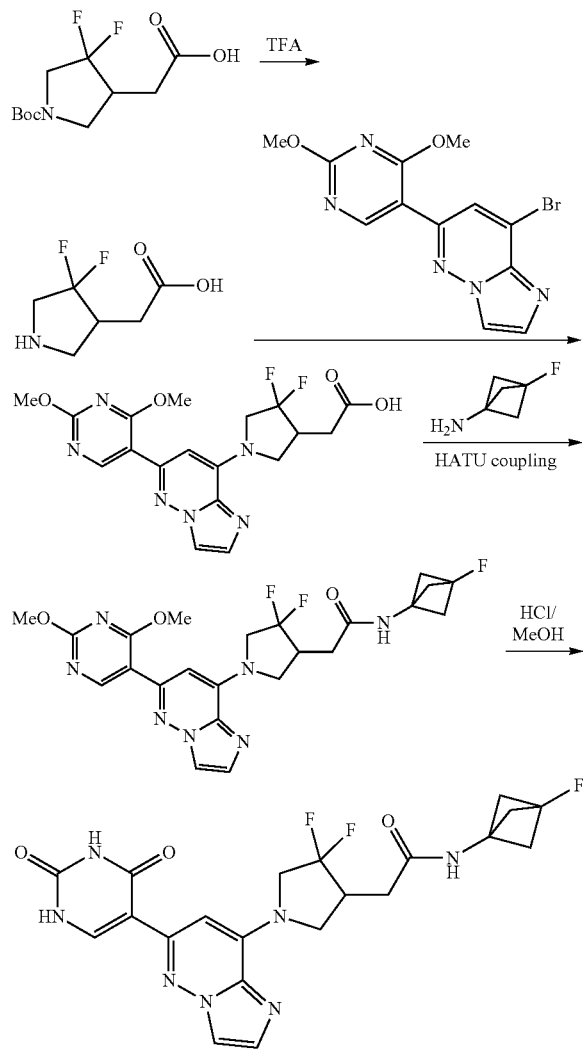

Step 1: To a solution of 2-(1-(tert-butoxycarbonyl)-4,4-difluoropyrrolidin-3-yl)acetic acid (1000 mg, 3.77 mmol, 1 equiv) in CH₂Cl₂ (7.5 mL) was added trifluoroacetic acid (2.5 mL). After 6 hours, the reaction mixture was concentrated to afford 2-(4,4-difluoropyrrolidin-3-yl)acetic acid. This material was used in the next step without purification. ¹H NMR (400 MHz, DMSO-d6) δ 3.84-3.60 (m, 3H), 3.18 (t, J=11.0 Hz, 1H), 3.08-2.86 (m, 1H), 2.69-2.48 (m, 2H).

Step 2: To a solution of 8-bromo-6-(2,4-dimethoxypyrimidin-5-yl)imidazo[1,2-b]pyridazine (1040 mg, 3.09 mmol, 1 equiv) in NMP (10 mL) was added DIPEA (1.29 mL, 7.43 mmol, 2.4 equiv) and 2-(4,4-difluoropyrrolidin-3-yl)acetic acid TFA salt (562 mg, 3.40 mmol, 1.1 equiv). The reaction mixture was heated to 115° C. After 48 hours, the reaction mixture was cooled to room temperature and acidified with 1N HCl (10 mL). The layers were separated, and the aqueous layer was exhaustively extracted with EtOAc. The combined organic layers were dried over Na₂SO₄, filtered, and concentrated. Purification was accomplished by SiO₂ chromatography (0-40% MeOH/CH₂Cl₂), affording 2-(1-(6-(2,4-dimethoxypyrimidin-5-yl)imidazo[1,2-b]pyridazin-8-yl)-4,4-difluoropyrrolidin-3-yl)acetic acid. ES/MS m/z: 421.20 [M+H].

Step 3: To a solution of 2-(1-(6-(2,4-dimethoxypyrimidin-5-yl)imidazo[1,2-b]pyridazin-8-yl)-4,4-difluoropyrrolidin-3-yl)acetic acid (30 mg, 0.071 mmol, 1 equiv), 3-fluorobicyclo[1.1.1]pentan-1-amine hydrochloride (14 mg, 0.14 mmol, 2 equiv), and HATU (41 mg, 0.11 mmol, 1.5 equiv) in DMF (1 mL) was added DIPEA (0.06 mL, 0.36 mmol, 5 equiv). After 30 minutes, the reaction mixture was directly purified by SiO₂ chromatography (0-100% EtOAc/Hex), affording 2-(1-(6-(2,4-dimethoxypyrimidin-5-yl)imidazo[1,2-b]pyridazin-8-yl)-4,4-difluoropyrrolidin-3-yl)-N-(3-fluorobicyclo[1.1.1]pentan-1-yl)acetamide. ES/MS m/z: 504.20 [M+H].

Step 4: A solution of 2-(1-(6-(2,4-dimethoxypyrimidin-5-yl)imidazo[1,2-b]pyridazin-8-yl)-4,4-difluoropyrrolidin-3-yl)-N-(3-fluorobicyclo[1.1.1]pentan-1-yl)acetamide (18 mg) in 1:1 1N HCl:MeOH (1 mL) was heated to 80° C. After 14 hours, the reaction mixture was purified by RP-HPLC (10-90% MeCN/H₂O with TFA modifier), affording 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-(3-fluorobicyclo[1.1.1]pentan-1-yl)acetamide. ES/MS m/z: 476.20 [M+H]. ¹H NMR (400 MHz, Methanol-d4) δ 8.14 (s, 1H), 8.07 (d, J=1.6 Hz, 1H), 7.73 (d, J=1.6 Hz, 1H), 6.98 (s, 1H), 4.45-4.29 (m, 3H), 3.78-3.69 (m, 1H), 3.23-3.13 (m, 1H), 2.77-2.65 (m, 1H), 2.51-2.41 (m, 1H), 2.38-2.33 (m, 6H). ¹⁹F NMR (376 MHz, Methanol-d4) δ −78.00, −111.09−−114.51 (m), −169.13−−169.21 (m).

Example 661. N-(bicyclo[1.1.1]pentan-1-yl)-2-(1-(6-(2,4-dioxo-1,2,3,4-tetrahydropyrimidin-5-yl)imidazo[1,2-b]pyridazin-8-yl)-4,4-difluoropyrrolidin-3-yl)acetamide

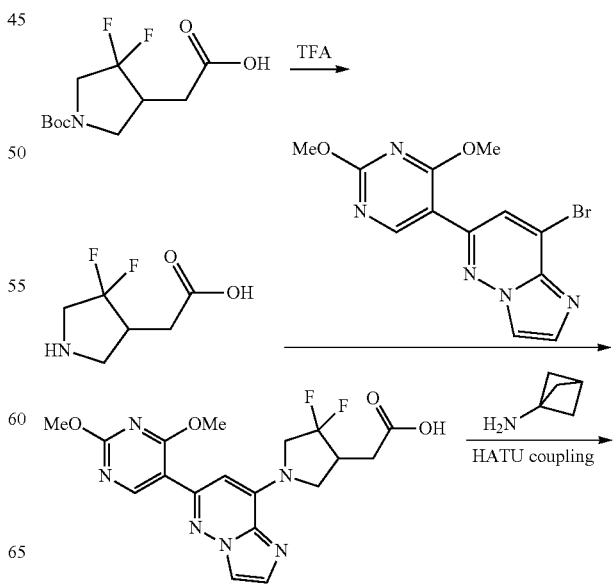

-continued

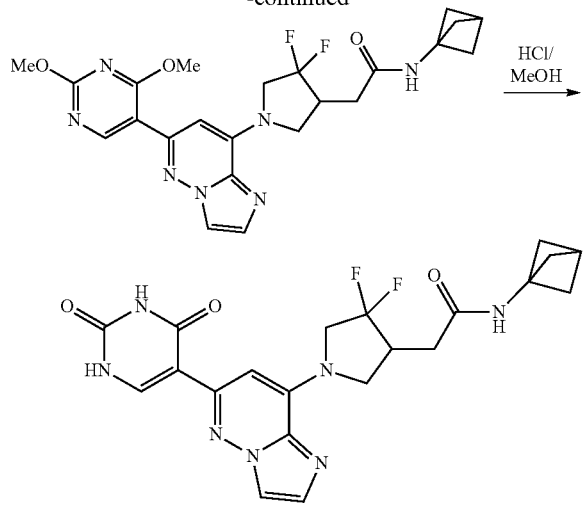

Step 1: To a solution of 2-(1-(tert-butoxycarbonyl)-4,4-difluoropyrrolidin-3-yl)acetic acid (1000 mg, 3.77 mmol, 1 equiv) in $CH_2Cl_2$ (7.5 mL) was added trifluoroacetic acid (2.5 mL). After 6 hours, the reaction mixture was concentrated to afford 2-(4,4-difluoropyrrolidin-3-yl)acetic acid. This material was used in the next step without purification. $^1$H NMR (400 MHz, DMSO-d6) δ 3.84-3.60 (m, 3H), 3.18 (t, J=11.0 Hz, 1H), 3.08-2.86 (m, 1H), 2.69-2.48 (m, 2H).

Step 2: To a solution of 8-bromo-6-(2,4-dimethoxypyrimidin-5-yl)imidazo[1,2-b]pyridazine (1040 mg, 3.09 mmol, 1 equiv) in NMP (10 mL) was added DIPEA (1.29 mL, 7.43 mmol, 2.4 equiv) and 2-(4,4-difluoropyrrolidin-3-yl)acetic acid TFA salt (562 mg, 3.40 mmol, 1.1 equiv). The reaction mixture was heated to 115° C. After 48 hours, the reaction mixture was cooled to room temperature and acidified with 1N HCl (10 mL). The layers were separated, and the aqueous layer was exhaustively extracted with EtOAc. The combined organic layers were dried over $Na_2SO_4$, filtered, and concentrated. Purification was accomplished by $SiO_2$ chromatography (0-40% MeOH/$CH_2Cl_2$), affording 2-(1-(6-(2,4-dimethoxypyrimidin-5-yl)imidazo[1,2-b]pyridazin-8-yl)-4,4-difluoropyrrolidin-3-yl)acetic acid. ES/MS m/z: 421.20 [M+H].

Step 3: To a solution of 2-(1-(6-(2,4-dimethoxypyrimidin-5-yl)imidazo[1,2-b]pyridazin-8-yl)-4,4-difluoropyrrolidin-3-yl)acetic acid (30 mg, 0.071 mmol, 1 equiv), bicyclo[1.1.1]pentan-1-amine (12 mg, 0.14 mmol, 2 equiv), and HATU (41 mg, 0.11 mmol, 1.5 equiv) in DMF (1 mL) was added DIPEA (0.06 mL, 0.36 mmol, 5 equiv). After 30 minutes, the reaction mixture was directly purified by $SiO_2$ chromatography (0-100% EtOAc/Hex), affording N-(bicyclo[1.1.1]pentan-1-yl)-2-(1-(6-(2,4-dimethoxypyrimidin-5-yl)imidazo[1,2-b]pyridazin-8-yl)-4,4-difluoropyrrolidin-3-yl)acetamide. ES/MS m/z: 486.20 [M+H].

Step 4: A solution of N-(bicyclo[1.1.1]pentan-1-yl)-2-(1-(6-(2,4-dimethoxypyrimidin-5-yl)imidazo[1,2-b]pyridazin-8-yl)-4,4-difluoropyrrolidin-3-yl)acetamide (38 mg) in 1:1 1N HCl:MeOH (1 mL) was heated to 80° C. After 14 hours, the reaction mixture was purified by RP-HPLC (10-90% MeCN/$H_2O$ with TFA modifier), affording N-(bicyclo[1.1.1]pentan-1-yl)-2-(1-(6-(2,4-dioxo-1,2,3,4-tetrahydropyrimidin-5-yl)imidazo[1,2-b]pyridazin-8-yl)-4,4-difluoropyrrolidin-3-yl)acetamide. ES/MS m/z: 458.20 [M+H]. $^1$H NMR (400 MHz, Methanol-d4) δ 8.15 (s, 1H), 8.07 (d, J=1.6 Hz, 1H), 7.73 (d, J=1.6 Hz, 1H), 6.97 (s, 1H), 4.46-4.30 (m, 3H), 3.80-3.70 (m, 1H), 3.24-3.10 (m, 1H), 2.71-2.62 (m, 1H), 2.44 (s, 1H), 2.48-2.36 (m, 1H), 2.11 (s, 6H). $^{19}$F NMR (376 MHz, Methanol-d4) δ −77.96, −110.95-114.72 (m).

Example 662. 2-(1-(6-(2,4-dioxo-1,2,3,4-tetrahydropyrimidin-5-yl)imidazo[1,2-b]pyridazin-8-yl)pyrrolidin-3-yl)-2,2-difluoro-N-isopropylacetamide

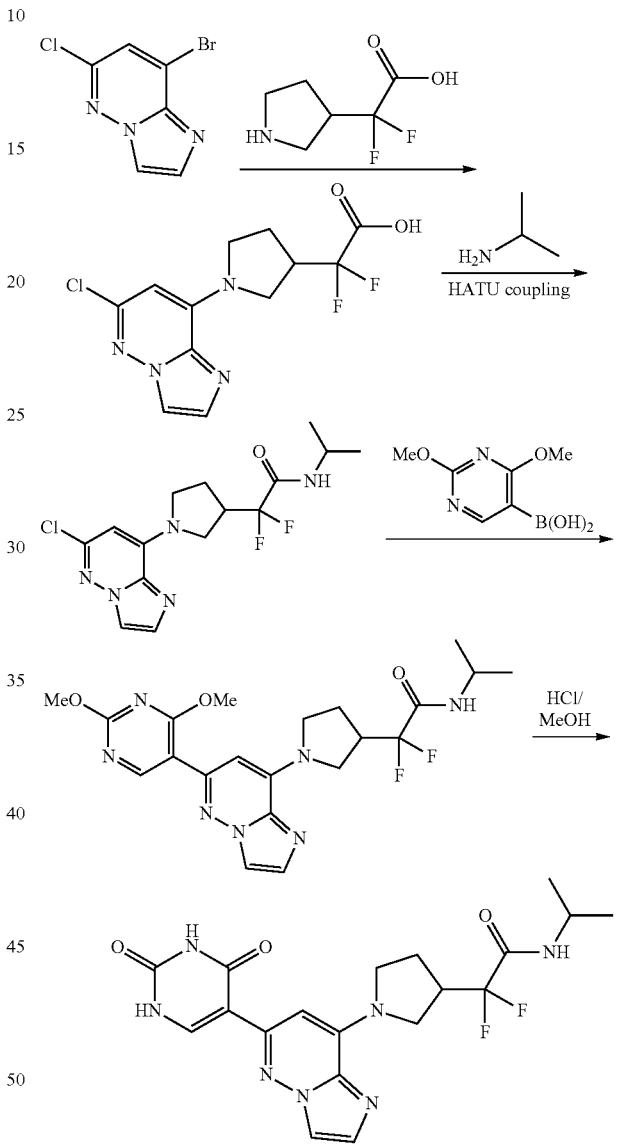

Step 1: A solution of 8-bromo-6-chloroimidazo[1,2-b]pyridazine (719 mg, 3.09 mmol, 1 equiv), 2,2-difluoro-2-(pyrrolidin-3-yl)acetic acid hydrochloride (511 mg, 3.09 mmol, 1 equiv), DIPEA (1.29 mL, 7.43 mmol, 2.4 equiv), and MeCN (20 mL) was heated to 80° C. After 24 hours, the reaction mixture was concentrated and directly purified by $SiO_2$ chromatography (0-100% EtOAc/Hex), affording 2-(1-(6-chloroimidazo[1,2-b]pyridazin-8-yl)pyrrolidin-3-yl)-2,2-difluoroacetic acid. ES/MS m/z: 317.10 [M+H].

Step 2: To a solution of 2-(1-(6-chloroimidazo[1,2-b]pyridazin-8-yl)pyrrolidin-3-yl)-2,2-difluoroacetic acid (100 mg, 0.32 mmol, 1 equiv), propan-2-amine (0.05 mL, 0.63 mmol, 2 equiv), and HATU (180 mg, 0.47 mmol, 1.5 equiv)

in DMF (3 mL) was added DIPEA (0.04 mL, 0.24 mmol, 0.75 equiv). After 1 hour, the reaction mixture was directly purified by SiO₂ chromatography (0-15% MeOH/CH₂Cl₂), affording 2-(1-(6-chloroimidazo[1,2-b]pyridazin-8-yl)pyrrolidin-3-yl)-2,2-difluoro-N-isopropylacetamide. ES/MS m/z: 458.20 [M+H].

Step 3: A solution of 2-(1-(6-chloroimidazo[1,2-b]pyridazin-8-yl)pyrrolidin-3-yl)-2,2-difluoro-N-isopropylacetamide (271 mg total mass, 30% purity, 0.23 mmol, 1 equiv), (2,4-dimethoxypyrimidin-5-yl)boronic acid (42 mg, 0.23 mol, 1 equiv), cesium carbonate (148 mg, 0.45 mmol, 2 equiv), and PdCl₂(dppf-CH₂Cl₂ (17 mg, 10 mol %) in 1:2 water/1,4-dioxane (3 mL) was heated to 80° C. After 30 minutes, the reaction mixture was directly purified by SiO₂ chromatography (0-15% MeOH/CH₂Cl₂), affording 2-(1-(6-(2,4-dimethoxypyrimidin-5-yl)imidazo[1,2-b]pyridazin-8-yl)pyrrolidin-3-yl)-2,2-difluoro-N-isopropylacetamide. ES/MS m/z: 462.20 [M+H].

Step 4: A solution of 2-(1-(6-(2,4-dimethoxypyrimidin-5-yl)imidazo[1,2-b]pyridazin-8-yl)pyrrolidin-3-yl)-2,2-difluoro-N-isopropylacetamide (157 mg total mass, 30% purity) in 1:1 1N HCl:MeOH (1 mL) was heated to 80° C. After 8 hours, the reaction mixture was filtered and purified by RP-HPLC (10-90% MeCN/H₂O with TFA modifier), affording 2-(1-(6-(2,4-dioxo-1,2,3,4-tetrahydropyrimidin-5-yl)imidazo[1,2-b]pyridazin-8-yl)pyrrolidin-3-yl)-2,2-difluoro-N-isopropylacetamide. ES/MS m/z: 434.20 [M+H]. ¹H NMR (400 MHz, Methanol-d4) δ 8.18 (s, 1H), 8.10 (d, J=1.6 Hz, 1H), 7.77 (d, J=1.6 Hz, 1H), 7.06 (s, 1H), 4.18-3.99 (m, 4H), 3.96-3.85 (m, 1H), 2.42-2.19 (m, 2H), 1.23 (d, J=6.6 Hz, 3H), 1.20 (d, J=6.6 Hz, 3H). ¹⁹F NMR (376 MHz, Methanol-d4) δ −77.82, −111.64−−116.10 (m).

Example 663. 5-(8-(3-((1-isopropyl-1H-1,2,3-triazol-4-yl)methyl)pyrrolidin-1-yl)imidazo[1,2-b]pyridazin-6-yl)pyrimidine-2,4(1H,3H)-dione

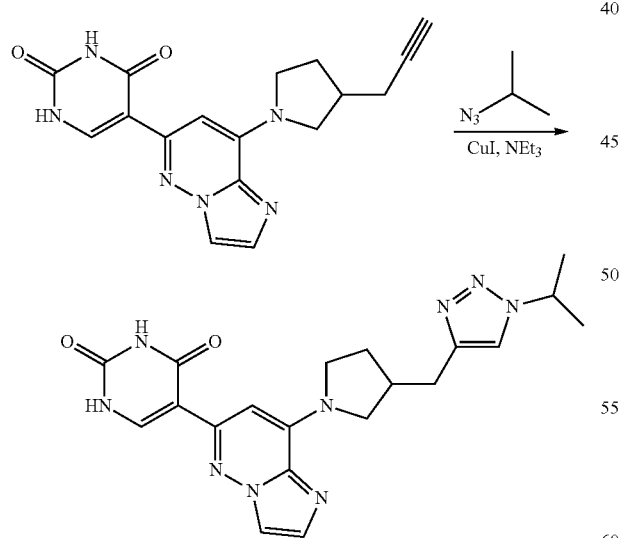

A solution of 5-(8-(3-(prop-2-yn-1-yl)pyrrolidin-1-yl)imidazo[1,2-b]pyridazin-6-yl)pyrimidine-2,4(1H,3H)-dione (50 mg, 0.15 mmol, 1 equiv), 2-azidopropane (11 mg, 0.13 mmol, 0.9 equiv), triethylamine (one drop), and CuI (1.4 mg, 5 mol %) in MeCN was heated to 80° C. After 16 hours, the reaction mixture was filtered and purified by RP-HPLC (10-90% MeCN/H₂O with TFA modifier), affording 5-(8-(3-((1-isopropyl-1H-1,2,3-triazol-4-yl)methyl)pyrrolidin-1-yl)imidazo[1,2-b]pyridazin-6-yl)pyrimidine-2,4(1H,3H)-dione. ES/MS m/z: 422.20 [M+H]. ¹H NMR (400 MHz, Methanol-d4) δ 8.22 (s, 1H), 8.19 (d, J=1.9 Hz, 1H), 7.93 (s, 1H), 7.90 (d, J=1.9 Hz, 1H), 7.20 (s, 1H), 4.18-4.02 (m, 1H), 4.03-3.89 (m, 1H), 3.90-3.77 (m, 1H), 3.78-3.64 (m, 1H), 3.03-2.88 (m, 2H), 2.87-2.72 (m, 1H), 2.38-2.24 (m, 1H), 2.02-1.88 (m, 1H), 1.59 (d, J=6.8 Hz, 3H), 1.59 (d, J=6.8 Hz, 3H).

Example 664. (S)-1-(6-(2,4-dioxo-1,2,3,4-tetrahydropyrimidin-5-yl)-3-fluoroimidazo[1,2-b]pyridazin-8-yl)-4,4-difluoropyrrolidin-3-yl (1-(trifluoromethyl)cyclopropyl)carbamate

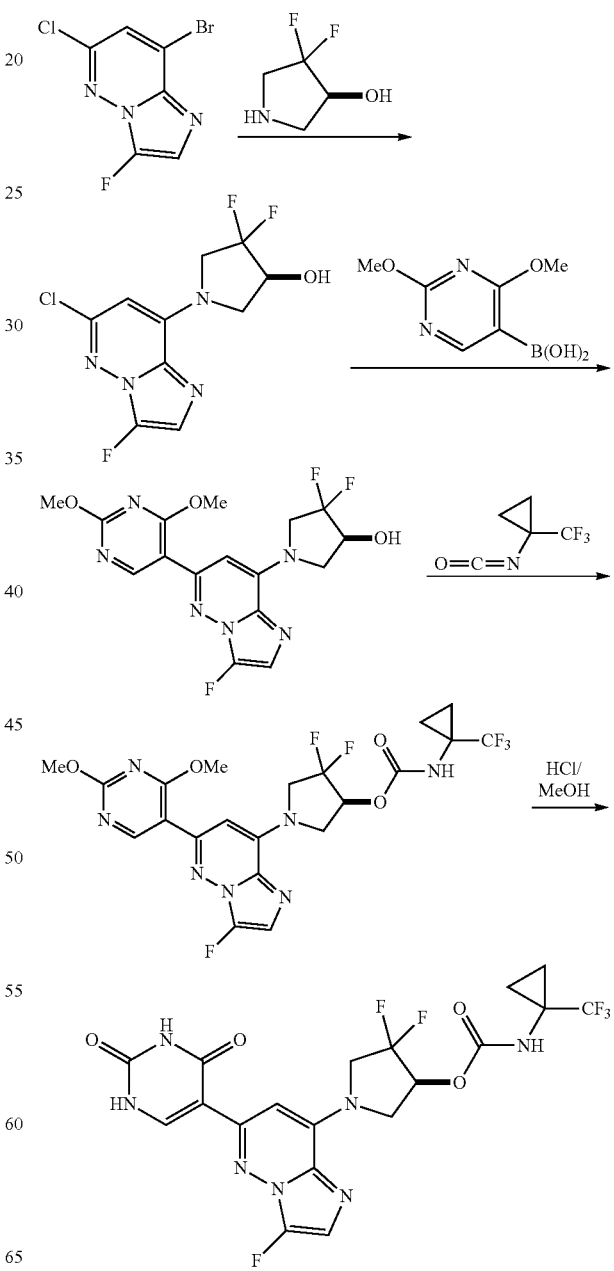

Step 1: A solution of 8-bromo-6-chloro-3-fluoroimidazo[1,2-b]pyridazine (2238 mg, 8.94 mmol, 1.1 equiv), (S)-4,4-difluoropyrrolidin-3-ol hydrochloride (1000 mg, 8.12 mmol, 1 equiv), DIPEA (3.40 mL, 19.5 mmol, 2.4 equiv), and MeCN (20 mL) was heated to 85° C. After 20 hours, the reaction mixture was concentrated and directly purified by SiO₂ chromatography (0-100% EtOAc/Hex), affording (S)-1-(6-chloro-3-fluoroimidazo[1,2-b]pyridazin-8-yl)-4,4-difluoropyrrolidin-3-ol. ES/MS m/z: 293.10 [M+H].

Step 2: A solution of (S)-1-(6-chloro-3-fluoroimidazo[1,2-b]pyridazin-8-yl)-4,4-difluoropyrrolidin-3-ol (2330 mg, 7.96 mmol, 1 equiv), (2,4-dimethoxypyrimidin-5-yl)boronic acid (1611 mg, 8.76 mol, 1.1 equiv), cesium carbonate (5188 mg, 15.9 mmol, 2 equiv), and PdCl₂(dppf)-CH₂Cl₂ (291 mg, 5 mol %) in 1:4 water/1,4-dioxane (40 mL) was heated to 80° C. After 24 hours, the reaction mixture was cooled to room temperature. The layers were separated, and the aqueous layer was extracted with EtOAc (3×200 mL). The combined organic layers were dried over Na₂SO₄, filtered, and concentrated. Purification was accomplished by SiO₂ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-ol. ES/MS m/z: 397.20 [M+H].

Step 3: A solution of (S)-1-(6-(2,4-dimethoxypyrimidin-5-yl)-3-fluoroimidazo[1,2-b]pyridazin-8-yl)-4,4-difluoropyrrolidin-3-ol (130 mg, 0.33 mmol, 1 equiv), 1-isocyanato-1-(trifluoromethyl)cyclopropane (248 mg, 1.64 mmol, 5 equiv), DIPEA (0.29 mL, 1.64 mmol, 5 equiv), and CH₂Cl₂ (1 mL) was heated to 60° C. After 2 hours, the reaction mixture was directly purified by SiO₂ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-yl (1-(trifluoromethyl)cyclopropyl)carbamate. ES/MS m/z: 548.20 [M+H].

Step 4: A solution of (S)-1-(6-(2,4-dimethoxypyrimidin-5-yl)-3-fluoroimidazo[1,2-b]pyridazin-8-yl)-4,4-difluoropyrrolidin-3-yl (1-(trifluoromethyl)cyclopropyl)carbamate (221 mg) in 1:1 1N HCl:MeOH (2 mL) was heated to 80° C. After 20 hours, the reaction mixture was filtered and washed with 5:1 MeCN/H₂O (20 mL). The remaining solids were dried under vacuum, affording (S)-1-(6-(2,4-dioxo-1,2,3,4-tetrahydropyrimidin-5-yl)-3-fluoroimidazo[1,2-b]pyridazin-8-yl)-4,4-difluoropyrrolidin-3-yl (1-(trifluoromethyl)cyclopropyl)carbamate. ES/MS m/z: 520.10 [M+H]. ¹H NMR (400 MHz, Methanol-d4) δ 8.11 (s, 1H), 7.23 (d, J=7.0 Hz, 1H), 6.71 (s, 1H), 5.51-5.37 (m, 1H), 4.61-4.44 (m, 1H), 4.40-4.09 (m, 3H), 1.32-1.20 (m, 2H), 1.19-1.06 (m, 2H). ¹⁹F NMR (376 MHz, Methanol-d4) δ −76.35, −78.10, −108.98−−110.78 (m), −124.10−−125.53 (m), −157.66 (d, J=7.3 Hz).

Example 665. (S)-1-(6-(2,4-dioxo-1,2,3,4-tetrahydropyrimidin-5-yl)-3-fluoroimidazo[1,2-b]pyridazin-8-yl)-4,4-difluoropyrrolidin-3-yl (3-(trifluoromethyl)bicyclo[1.1.1]pentan-1-yl)carbamate

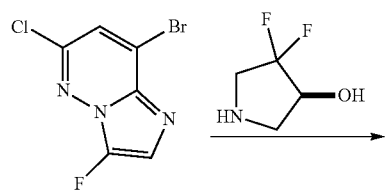

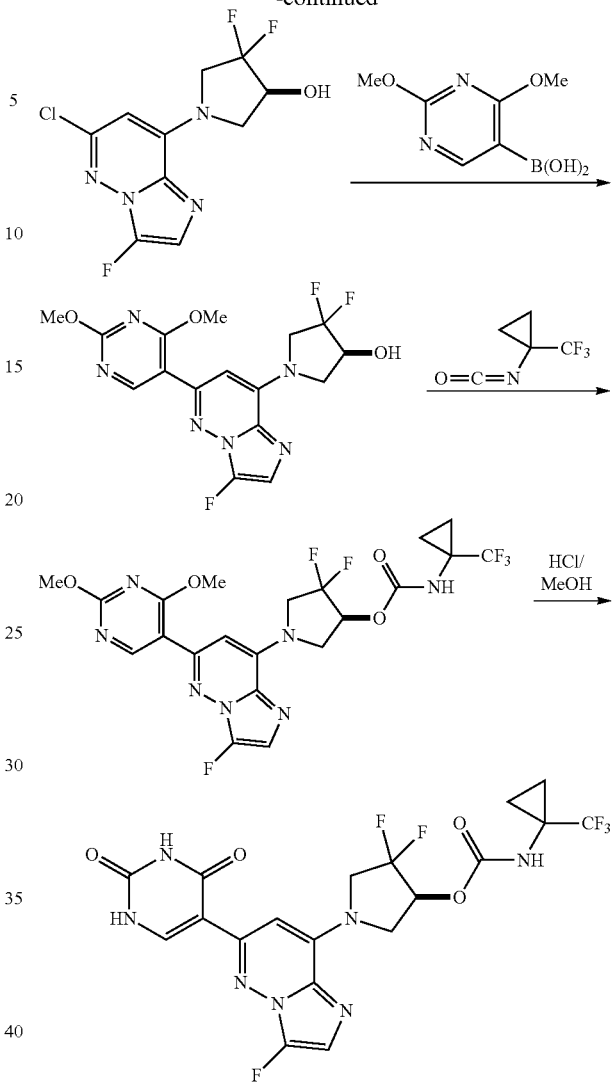

Step 1: A solution of 8-bromo-6-chloro-3-fluoroimidazo[1,2-b]pyridazine (2238 mg, 8.94 mmol, 1.1 equiv), (S)-4,4-difluoropyrrolidin-3-ol hydrochloride (1000 mg, 8.12 mmol, 1 equiv), DIPEA (3.40 mL, 19.5 mmol, 2.4 equiv), and MeCN (20 mL) was heated to 85° C. After 20 hours, the reaction mixture was concentrated and directly purified by SiO₂ chromatography (0-100% EtOAc/Hex), affording (S)-1-(6-chloro-3-fluoroimidazo[1,2-b]pyridazin-8-yl)-4,4-difluoropyrrolidin-3-ol. ES/MS m/z: 293.10 [M+H].

Step 2: A solution of (S)-1-(6-chloro-3-fluoroimidazo[1,2-b]pyridazin-8-yl)-4,4-difluoropyrrolidin-3-ol (2330 mg, 7.96 mmol, 1 equiv), (2,4-dimethoxypyrimidin-5-yl)boronic acid (1611 mg, 8.76 mol, 1.1 equiv), cesium carbonate (5188 mg, 15.9 mmol, 2 equiv), and PdCl₂(dppf)-CH₂Cl₂ (291 mg, 5 mol %) in 1:4 water/1,4-dioxane (40 mL) was heated to 80° C. After 24 hours, the reaction mixture was cooled to room temperature. The layers were separated, and the aqueous layer was extracted with EtOAc (3×200 mL). The combined organic layers were dried over Na₂SO₄, filtered, and concentrated. Purification was accomplished by SiO₂ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-ol. ES/MS m/z: 397.20 [M+H].

Step 3: A solution of (S)-1-(6-(2,4-dimethoxypyrimidin-5-yl)-3-fluoroimidazo[1,2-b]pyridazin-8-yl)-4,4-difluoropyrrolidin-3-ol (100 mg, 0.25 mmol, 1 equiv), 1-isocyanato-3-(trifluoromethyl)bicyclo[1.1.1]pentane (197 mg, 1.11 mmol, 4.4 equiv), DIPEA (0.22 mL, 1.26 mmol, 5 equiv), and CH$_2$Cl$_2$ (2.5 mL) was heated to 60° C. After 1 hour, the reaction mixture was directly purified by SiO$_2$ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-yl (3-(trifluoromethyl)bicyclo[1.1.1]pentan-1-yl)carbamate. ES/MS m/z: 574.20 [M+H].

Step 4: A solution of (S)-1-(6-(2,4-dimethoxypyrimidin-5-yl)-3-fluoroimidazo[1,2-b]pyridazin-8-yl)-4,4-difluoropyrrolidin-3-yl (3-(trifluoromethyl)bicyclo[1.1.1]pentan-1-yl)carbamate (163 mg) in 1:1 1N HCl:MeOH (3 mL) was heated to 80° C. After 20 hours, the reaction mixture was filtered and washed with 5:1 MeCN/H$_2$O (10 mL). The remaining solids were dried under vacuum, affording (S)-1-(6-(2,4-dioxo-1,2,3,4-tetrahydropyrimidin-5-yl)-3-fluoroimidazo[1,2-b]pyridazin-8-yl)-4,4-difluoropyrrolidin-3-yl (3-(trifluoromethyl)bicyclo[1.1.1]pentan-1-yl)carbamate. ES/MS m/z: 546.20 [M+H]. $^1$H NMR (400 MHz, Methanol-d4) δ 8.11 (s, 1H), 7.24 (d, J=7.1 Hz, 1H), 6.71 (s, 1H), 5.46-5.35 (m, 1H), 4.62-4.43 (m, 1H), 4.41-4.02 (m, 3H), 2.24 (s, 6H). $^{19}$F NMR (376 MHz, Methanol-d4) δ −73.59, −78.24, −109.20-110.65 (m), −123.90-125.78 (m), −157.61 (d, J=7.1 Hz).

Example 666. (S)-5-(8-(3,3-difluoro-4-((5-(trifluoromethyl)pyridazin-3-yl)oxy)pyrrolidin-1-yl)-3-fluoroimidazo[1,2-b]pyridazin-6-yl)pyrimidine-2,4(1H,3H)-dione

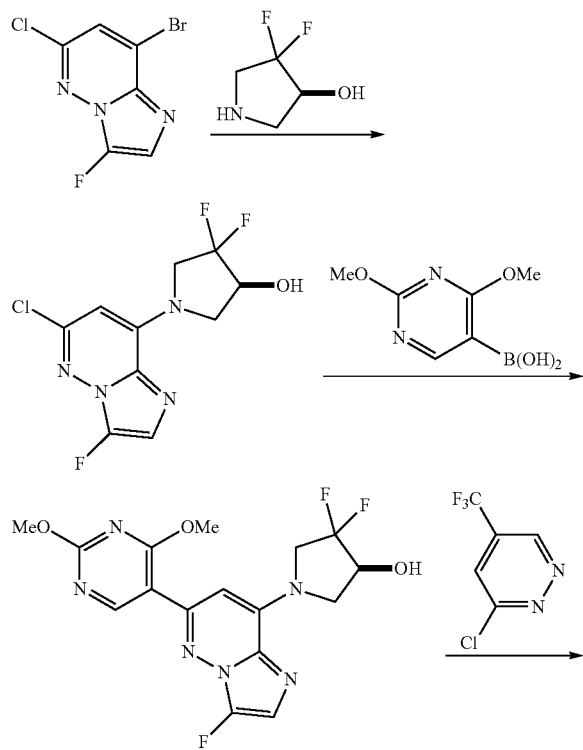

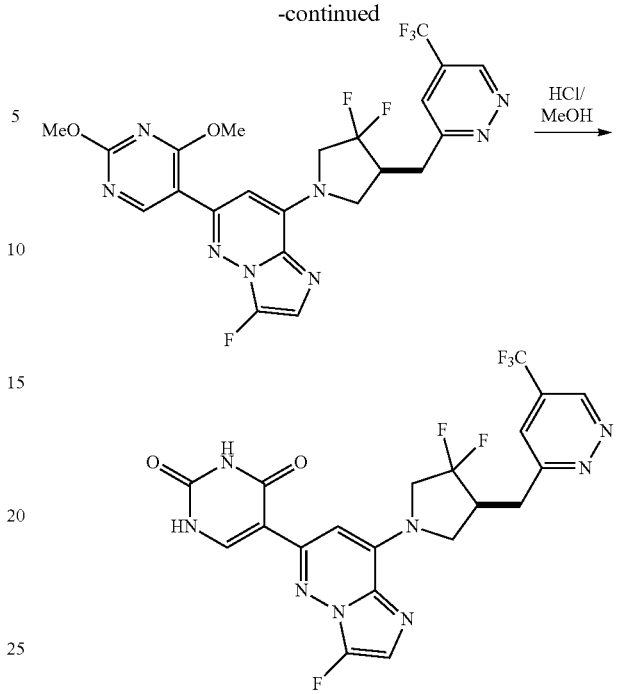

Step 1: A solution of 8-bromo-6-chloro-3-fluoroimidazo[1,2-b]pyridazine (2238 mg, 8.94 mmol, 1.1 equiv), (S)-4,4-difluoropyrrolidin-3-ol hydrochloride (1000 mg, 8.12 mmol, 1 equiv), DIPEA (3.40 mL, 19.5 mmol, 2.4 equiv), and MeCN (20 mL) was heated to 85° C. After 20 hours, the reaction mixture was concentrated and directly purified by SiO$_2$ chromatography (0-100% EtOAc/Hex), affording (S)-1-(6-chloro-3-fluoroimidazo[1,2-b]pyridazin-8-yl)-4,4-difluoropyrrolidin-3-ol. ES/MS m/z: 293.10 [M+H].

Step 2: A solution of (S)-1-(6-chloro-3-fluoroimidazo[1,2-b]pyridazin-8-yl)-4,4-difluoropyrrolidin-3-ol (2330 mg, 7.96 mmol, 1 equiv), (2,4-dimethoxypyrimidin-5-yl)boronic acid (1611 mg, 8.76 mol, 1.1 equiv), cesium carbonate (5188 mg, 15.9 mmol, 2 equiv), and PdCl$_2$(dppf)-CH$_2$Cl$_2$ (291 mg, 5 mol %) in 1:4 water/1,4-dioxane (40 mL) was heated to 80° C. After 24 hours, the reaction mixture was cooled to room temperature. The layers were separated, and the aqueous layer was extracted with EtOAc (3×200 mL). The combined organic layers were dried over Na$_2$SO$_4$, filtered, and concentrated. Purification was accomplished by SiO$_2$ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-ol. ES/MS m/z: 397.20 [M+H].

Step 3: To a solution of (S)-1-(6-(2,4-dimethoxypyrimidin-5-yl)-3-fluoroimidazo[1,2-b]pyridazin-8-yl)-4,4-difluoropyrrolidin-3-ol (100 mg, 0.25 mmol, 1 equiv) in DMF (1 mL) was added 60% sodium hydride (19 mg, 0.51 mmol, 2 equiv). After 10 minutes, 3-chloro-5-(trifluoromethyl)pyridazine (138 mg, 0.76 mmol, 3 equiv) was added, and the reaction mixture was heated to 80° C. After 4 hours, the reaction mixture was cooled to room temperature, quenched with H$_2$O (2 mL), and directly purified by SiO$_2$ chromatography (0-100% EtOAc/Hex), affording (S)-8-(3,3-difluoro-4-((5-(trifluoromethyl)pyridazin-3-yl)oxy)pyrrolidin-1-yl)-6-(2,4-dimethoxypyrimidin-5-yl)-3-fluoroimidazo[1,2-b]pyridazine. ES/MS m/z: 543.20 [M+H].

Step 4: A solution of (S)-8-(3,3-difluoro-4-((5-(trifluoromethyl)pyridazin-3-yl)oxy)pyrrolidin-1-yl)-6-(2,4-dimethoxypyrimidin-5-yl)-3-fluoroimidazo[1,2-b]pyridazine (65 mg) in 1:1 1N HCl:MeOH (2 mL) was heated to 80° C. After 5 hours, the reaction mixture was purified by RP-HPLC (10-90% MeCN/H₂O with TFA modifier), affording (S)-5-(8-(3,3-difluoro-4-((5-(trifluoromethyl)pyridazin-3-yl)oxy) pyrrolidin-1-yl)-3-fluoroimidazo[1,2-b]pyridazin-6-yl)pyrimidine-2,4(1H,3H)-dione. ES/MS m/z: 515.10 [M+H]. ¹H NMR (400 MHz, Methanol-d4) δ 9.27 (d, J=1.7 Hz, 1H), 8.11 (s, 1H), 7.76-7.72 (m, 1H), 7.24 (d, J=7.1 Hz, 1H), 6.75 (s, 1H), 6.24-6.15 (m, 1H), 4.72-4.33 (m, 4H). ¹⁹F NMR (376 MHz, Methanol-d4) δ −66.64, −77.87, −109.13-−110.34 (m), −109.15-−124.05 (m), −157.68 (d, J=6.4 Hz).

Example 667. 5-(8-(isobutylamino)imidazo[1,2-b]pyridazin-6-yl)pyrimidine-2,4(1H,3H)-dione

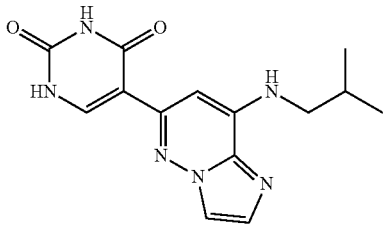 [SMILES: CC(C)CNc1cc(-c2c[nH]c(=O)[nH]c2=O)nn2ccnc12]

5-(8-(isobutylamino)imidazo[1,2-b]pyridazin-6-yl)pyrimidine-2,4(1H,3H)-dione was prepared as follows: To a solution of 6-(2,4-di-tert-butoxypyrimidin-5-yl)-N-isobutylimidazo[1,2-b]pyridazin-8-amine (20 mg, 0.05 mmol, 1 equiv) in DCM (1 mL) was added TFA solution (0.5 mL). The reaction was stirred until complete (0.5 hr), the mixture was then concentrated, redissolved in ACN and water, frozen and lyophilized to give title compound. ES/MS: 301.20 [M+1]. ¹H NMR (400 MHz, DMSO-d6) δ 11.46 (d, 2H), 8.18 (s, 1H), 8.00 (d, 1H), 7.82 (s, 1H), 7.52 (t, 1H), 6.98 (s, 1H), 3.15 (t, 2H), 2.02 (dt, 1H), 0.97 (d, 6H).

Example 668. 5-(8-(neopentylamino)imidazo[1,2-b]pyridazin-6-yl)pyrimidine-2,4(1H,3H)-dione

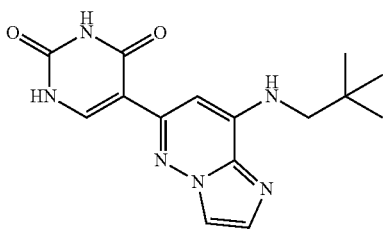 [SMILES: CC(C)(C)CNc1cc(-c2c[nH]c(=O)[nH]c2=O)nn2ccnc12]

5-(8-(neopentylamino)imidazo[1,2-b]pyridazin-6-yl)pyrimidine-2,4(1H,3H)-dione was prepared in the manner described for Example 667, but replacing of 6-(2,4-di-tert-butoxypyrimidin-5-yl)-N-isobutylimidazo[1,2-b]pyridazin-8-amine with 6-(2,4-di-tert-butoxypyrimidin-5-yl)-N-neopentylimidazo[1,2-b]pyridazin-8-amine. ES/MS m/z: 315.18 [M+H]. ¹H NMR (400 MHz, DMSO-d6) δ 11.53-11.44 (m, 2H), 8.25 (d, 1H), 8.01 (d, 1H), 7.93 (d, 1H), 7.27 (t, 1H), 7.16 (s, 1H), 3.19 (d, 2H), 1.00 (s, 9H).

Example 669. 5-(8-((2-methoxyethyl)amino)imidazo[1,2-b]pyridazin-6-yl)pyrimidine-2,4(1H,3H)-dione

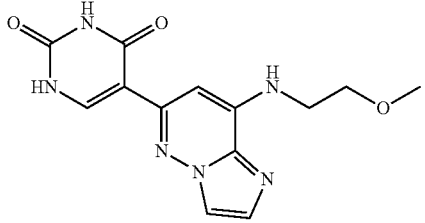 [SMILES: COCCNc1cc(-c2c[nH]c(=O)[nH]c2=O)nn2ccnc12]

5-(8-((2-methoxyethyl)amino)imidazo[1,2-b]pyridazin-6-yl)pyrimidine-2,4(1H,3H)-dione was prepared in the manner described for Example 667, but replacing of 6-(2,4-di-tert-butoxypyrimidin-5-yl)-N-isobutylimidazo[1,2-b]pyridazin-8-amine with 6-(2,4-di-tert-butoxypyrimidin-5-yl)-N-(2-methoxyethyl)imidazo[1,2-b]pyridazin-8-amine. ES/MS m/z: 303.13 [M+H]. ¹H NMR (400 MHz, DMSO-d6) δ 11.44 (d, 2H), 8.16 (d, 1H), 7.98 (d, 1H), 7.76 (s, 1H), 7.37 (s, 1H), 6.95 (s, 1H), 3.61 (t, 2H), 3.54-3.46 (m, 2H), 3.31 (s, 3H).

Example 670. 5-(8-((2,2-difluoroethyl)amino)imidazo[1,2-b]pyridazin-6-yl)pyrimidine-2,4(1H,3H)-dione

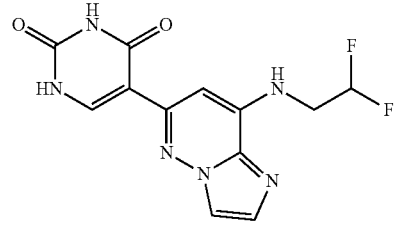 [SMILES: O=c1[nH]cc(-c2cc(NCC(F)F)c3nccn3n2)c(=O)[nH]1]

5-(8-((2,2-difluoroethyl)amino)imidazo[1,2-b]pyridazin-6-yl)pyrimidine-2,4(1H,3H)-dione was prepared as follows: To a solution of 6-(2,4-di-tert-butoxypyrimidin-5-yl)-N-(2,2-difluoroethyl)-N-(4-methoxybenzyl)imidazo[1,2-b]pyridazin-8-amine (45 mg, 0.08 mmol, 1 equiv) in DCM (1 mL) was added TFA solution (0.5 mL). The reaction was stirred until complete (0.5 hr), the mixture was then concentrated, redissolved in ACN and water, frozen and lyophilized to give title compound. ES/MS: 309.09 [M+1]. ¹H NMR (400 MHz, DMSO-d6) δ11.46-11.26 (m, 2H), 8.11 (d, 1H), 7.95 (d, 1H), 7.67 (d, 1H), 7.61 (t, 1H), 6.24 (tt, 1H), 3.86 (s, 1H), 3.76-3.56 (m, 2H).

Example 671. 5-(8-((2,2-difluoroethyl)(4-methoxy-benzyl)amino)imidazo[1,2-b]pyridazin-6-yl)pyrimidine-2,4(1H,3H)-dione

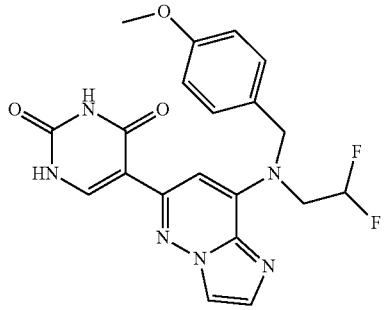 [SMILES: COc1ccc(CN(CC(F)F)c2cc(-c3c[nH]c(=O)[nH]c3=O)nn3ccnc23)cc1]

5-(8-((2,2-difluoroethyl)(4-methoxybenzyl)amino)imidazo[1,2-b]pyridazin-6-yl)pyrimidine-2,4(1H,3H)-dione was prepared as follows: To a solution of 6-(2,4-di-tert-butoxypyrimidin-5-yl)-N-(2,2-difluoroethyl)-N-(4-methoxybenzyl)imidazo[1,2-b]pyridazin-8-amine (45 mg, 0.08 mmol, 1 equiv) in ACN (1 mL) was added TFA solution (2 drops). The reaction vessel was stirred until complete (0.5 hr), the mixture was then diluted with water, frozen and lyophilized to give title compound. ES/MS: 428.96 [M+1]. $^1$H NMR (400 MHz, DMSO-d6) δ 11.37 (s, 2H), 8.08 (d, 1H), 7.97-7.89 (m, 1H), 7.60 (d, 1H), 7.25 (d, 2H), 6.95 (s, 1H), 6.89 (d, 1H), 6.87 (d, 1H), 4.94 (s, 2H), 4.71 (t, 2H), 3.72 (s, 3H).

Example 672. 5-(8-((2,2,2-trifluoroethyl)amino)imidazo[1,2-b]pyridazin-6-yl)pyrimidine-2,4(1H,3H)-dione

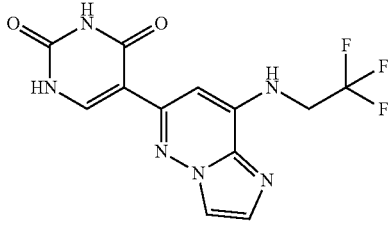 [SMILES: O=c1[nH]cc(-c2cc(NCC(F)(F)F)c3nccn3n2)c(=O)[nH]1]

5-(8-((2,2,2-trifluoroethyl)amino)imidazo[1,2-b]pyridazin-6-yl)pyrimidine-2,4(1H,3H)-dione was prepared in the manner described for Example 670, but replacing 6-(2,4-di-tert-butoxypyrimidin-5-yl)-N-(2,2-difluoroethyl)-N-(4-methoxybenzyl)imidazo[1,2-b]pyridazin-8-amine with 6-(2,4-di-tert-butoxypyrimidin-5-yl)-N-(4-methoxybenzyl)-N-(2,2,2-trifluoroethyl)imidazo[1,2-b]pyridazin-8-amine. ES/MS m/z: 327.13 [M+H]. $^1$H NMR (400 MHz, DMSO-d6) δ 11.41 (dd, 2H), 8.15-8.08 (m, 1H), 7.95 (dd, 1H), 7.85 (t, 1H), 7.64 (d, 1H), 4.36-4.31 (m, 2H).

Example 673. 5-(8-phenethoxyimidazo[1,2-b]pyridazin-6-yl)pyrimidine-2,4(1H,3H)-dione

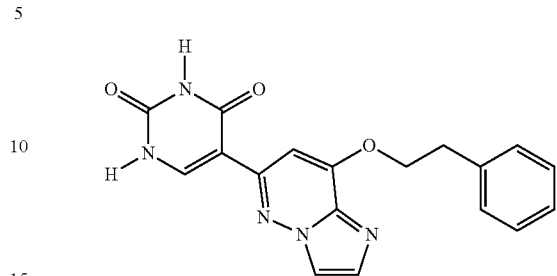

5-(8-phenethoxyimidazo[1,2-b]pyridazin-6-yl)pyrimidine-2,4(1H,3H)-dione was prepared as follows: To a microwave vial was added 2-phenylethanol (59 mg, 0.49 mmol) and NMP (2 ml), then sodium hydride 60% dispersion in mineral oil (7.5 mg, 0.19 mmol), allowing to stir for 10 minutes before adding 5-(8-bromoimidazo[1,2-b]pyridazin-6-yl)pyrimidine-2,4(1H,3H)-dione (30 mg, 0.10 mmol). The reaction was then heated to 100° C. for 5 hr. The reaction was cooled, quenched with water, filtered and purified by HPLC to give the title compound. ES/MS m/z: 350.21 [M+H]. $^1$H NMR (400 MHz, DMSO-d6) δ 11.55 (d, 2H), 8.28 (d, 1H), 8.05 (d, 1H), 7.78 (s, 1H), 7.47-7.37 (m, 3H), 7.33 (dd, 2H), 7.30-7.20 (m, 1H), 4.56 (t, 2H), 3.19 (t, 2H).

Example 674. 5-(8-(2-phenylpropoxy)imidazo[1,2-b]pyridazin-6-yl)pyrimidine-2,4(1H,3H)-dione

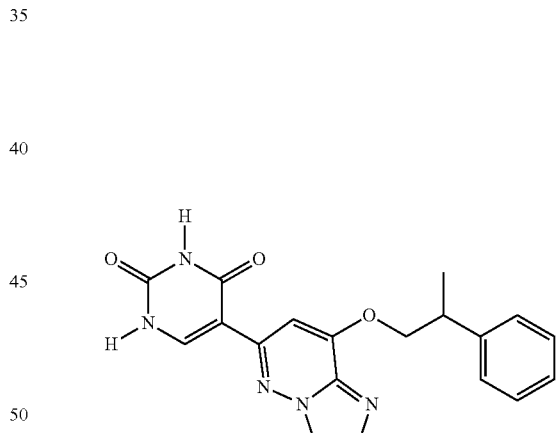

5-(8-(2-phenylpropoxy)imidazo[1,2-b]pyridazin-6-yl)pyrimidine-2,4(1H,3H)-dione was prepared in the manner described for Example 673, but replacing 2-phenylethanol with 2-phenylpropan-1-ol. ES/MS m/z: 364.12 [M+H]. $^1$H NMR (400 MHz, DMSO-d6) δ 11.60 11.52 (m, 2H), 8.31 (d, 1H), 8.05 (d, 1H), 7.83 (s, 1H), 7.48-7.40 (m, 3H), 7.34 (dd, 2H), 7.30 7.21 (m, 1H), 4.49 (dd, 1H), 4.40 (dd, 1H), 3.39 (p, 1H), 1.41 (d, 3H).

Example 675. 5-(8-(2,2,2-trifluoroethoxy)imidazo[1,2-b]pyridazin-6-yl)pyrimidine-2,4(1H,3H)-dione

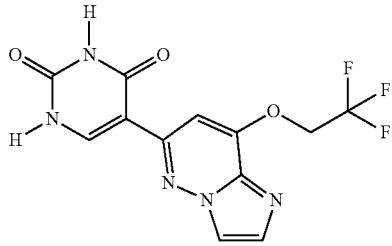 [SMILES: O=c1[nH]cc(-c2cc(OCC(F)(F)F)c3nccn3n2)c(=O)[nH]1]

5-(8-(2,2,2-trifluoroethoxy)imidazo[1,2-b]pyridazin-6-yl)pyrimidine-2,4(1H,3H)-dione was prepared in the manner described for Example 673, but replacing 2-phenylethanol with 2,2,2-trifluoroethanol. ES/MS m/z: 328.15 [M+H]. $^1$H NMR (400 MHz, DMSO-d6) δ 11.55 (d, 2H), 8.29 (d, 1H), 8.05 (d, 1H), 7.74 (d, 1H), 7.41 (s, 1H), 5.26 (q, 2H).

Example 676. 5-(8-(3,3,3-trifluoro-2,2-dimethylpropoxy)imidazo[1,2-b]pyridazin-6-yl)pyrimidine-2,4(1H,3H)-dione

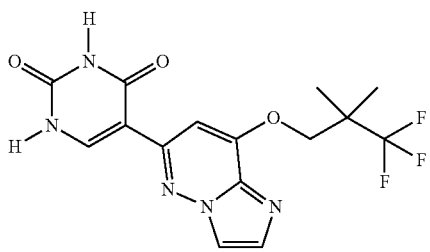 [SMILES: CC(C)(COc1cc(-c2c[nH]c(=O)[nH]c2=O)nn2ccnc12)C(F)(F)F]

5-(8-(3,3,3-trifluoro-2,2-dimethylpropoxy)imidazo[1,2-b]pyridazin-6-yl)pyrimidine-2,4(1H,3H)-dione was prepared in the manner described for Example 670, but replacing 6-(2,4-di-tert-butoxypyrimidin-5-yl)-N-(2,2-difluoroethyl)-N-(4-methoxybenzyl)imidazo[1,2-b]pyridazin-8-amine with 6-(2,4-di-tert-butoxypyrimidin-5-yl)-8-(3,3,3-trifluoro-2,2-dimethylpropoxy)imidazo[1,2-b]pyridazine. ES/MS m/z: 370.16 [M+H]. $^1$H NMR (400 MHz, DMSO-d6) δ 11.56 (d, 2H), 8.31 (d, 1H), 8.04 (d, 1H), 7.82 (s, 1H), 7.42 (s, 1H), 4.39 (s, 2H), 1.32 (s, 6H).

Example 677. 5-(8-(2,2-difluoropropoxy)imidazo[1,2-b]pyridazin-6-yl)pyrimidine-2,4(1H,3H)-dione

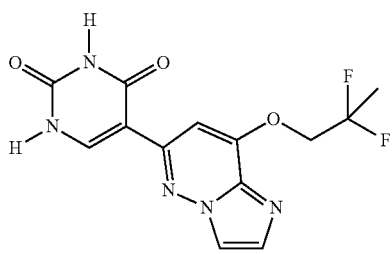 [SMILES: CC(F)(F)COc1cc(-c2c[nH]c(=O)[nH]c2=O)nn2ccnc12]

5-(8-(2,2-difluoropropoxy)imidazo[1,2-b]pyridazin-6-yl)pyrimidine-2,4(1H,3H)-dione was prepared in the manner described for Example 676, but replacing 6-(2,4-di-tert-butoxypyrimidin-5-yl)-8-(3,3,3-trifluoro-2,2-dimethylpropoxy)imidazo[1,2-b]pyridazine with 6-(2,4-di-tert-butoxypyrimidin-5-yl)-8-(2,2-difluoropropoxy)imidazo[1,2-b]pyridazine. ES/MS m/z: 324.13 [M+H]. $^1$H NMR (400 MHz, DMSO-d6) δ 11.63-11.54 (m, 2H), 8.35 (d, 1H), 8.07 (d, 1H), 7.86 (d, 1H), 7.49 (s, 1H), 4.74 (t, 2H), 1.83 (t, 3H).

Example 678. 5-(8-isobutoxyimidazo[1,2-b]pyridazin-6-yl)pyrimidine-2,4(1H,3H)-dione

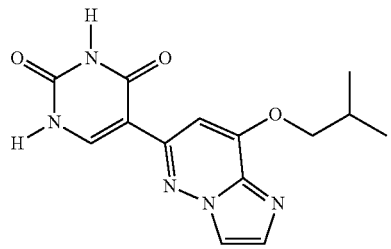 [SMILES: CC(C)COc1cc(-c2c[nH]c(=O)[nH]c2=O)nn2ccnc12]

5-(8-isobutoxyimidazo[1,2-b]pyridazin-6-yl)pyrimidine-2,4(1H,3H)-dione was prepared in the manner described for Example 676, but replacing 6-(2,4-di-tert-butoxypyrimidin-5-yl)-8-(3,3,3-trifluoro-2,2-dimethylpropoxy)imidazo[1,2-b]pyridazine with 6-(2,4-di-tert-butoxypyrimidin-5-yl)-8-isobutoxyimidazo[1,2-b]pyridazine. ES/MS m/z: 302.14 [M+H]. $^1$H NMR (400 MHz, DMSO-d6) δ 11.65-11.50 (m, 2H), 8.34 (d, 1H), 8.07 (d, 1H), 7.88 (s, 1H), 7.46 (s, 1H), 4.13 (d, 2H), 2.18 (dq, 1H), 1.06 (d, 6H).

Example 679. 5-(8-(neopentyloxy)imidazo[1,2-b]pyridazin-6-yl)pyrimidine-2,4(1H,3H)-dione

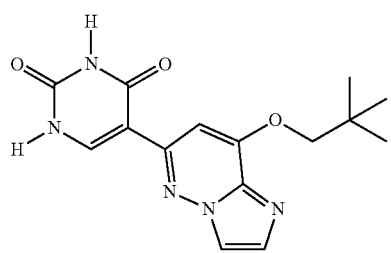 [SMILES: CC(C)(C)COc1cc(-c2c[nH]c(=O)[nH]c2=O)nn2ccnc12]

5-(8-(neopentyloxy)imidazo[1,2-b]pyridazin-6-yl)pyrimidine-2,4(1H,3H)-dione was prepared in the manner described for Example 676, but replacing 6-(2,4-di-tert-butoxypyrimidin-5-yl)-8-(3,3,3-trifluoro-2,2-dimethylpropoxy)imidazo[1,2-b]pyridazine with 6-(2,4-di-tert-butoxypyrimidin-5-yl)-8-(neopentyloxy)imidazo[1,2-b]pyridazine. ES/MS m/z: 315.10 [M+H]. $^1$H NMR (400 MHz, DMSO-d6) δ 11.64 (dd, 1H), 11.58 (d, 1H), 8.39 (d, 1H), 8.09 (d, 1H), 7.97 (d, 1H), 7.52 (s, 1H), 4.02 (s, 2H), 1.09 (s, 9H).

Example 680. 5-(8-((3-methylbutan-2-yl)oxy)imidazo[1,2-b]pyridazin-6-yl)pyrimidine-2,4(1H,3H)-dione

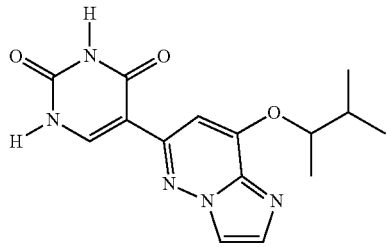 [SMILES: CC(C)C(C)Oc1cc(-c2c[nH]c(=O)[nH]c2=O)nn2ccnc12]

5-(8-((3-methylbutan-2-yl)oxy)imidazo[1,2-b]pyridazin-6-yl)pyrimidine-2,4(1H,3H)-dione was prepared in the manner described for Example 676, but replacing 6-(2,4-di-tert-butoxypyrimidin-5-yl)-8-(3,3,3-trifluoro-2,2-dimethylpropoxy)imidazo[1,2-b]pyridazine with 6-(2,4-di-tert-butoxypyrimidin-5-yl)-8-((3-methylbutan-2-yl)oxy)imidazo[1,2-b]pyridazine. ES/MS m/z: 316.07 [M+H]. $^1$H NMR (400 MHz, DMSO-d6) δ 11.60 (dd, 1H), 11.56 (d, 1H), 8.36 (d, 1H), 8.07 (d, 1H), 7.92 (d, 1H), 7.50 (s, 1H), 4.74 (p, 1H), 2.08-1.98 (m, 1H), 1.35 (d, 3H), 1.01 (dd, 6H).

Example 681. 5-(8-(3,3,3-trifluoropropoxy)imidazo[1,2-b]pyridazin-6-yl)pyrimidine-2,4(1H,3H)-dione Example 682. 5-(8-(2,2-difluoro-2-phenylethoxy)imidazo[1,2-b]pyridazin-6-yl)pyrimidine-2,4(1H,3H)-dione

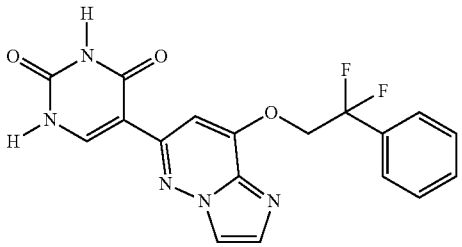

5-(8-(2,2-difluoro-2-phenylethoxy)imidazo[1,2-b]pyridazin-6-yl)pyrimidine-2,4(1H,3H)-dione was prepared in the manner described for Example 673, but replacing 2-phenylethanol with 2,2-difluoro-2-phenyl-ethanol. ES/MS m/z: 386.10 [M+H]. $^1$H NMR (400 MHz, DMSO-d6) δ 11.55 (d, 2H), 8.30 (d, 1H), 8.04 (d, 1H), 7.77 (d, 1H), 7.71 (dd, 2H), 7.63-7.51 (m, 3H), 7.46 (s, 1H), 5.09 (t, 2H).

Example 683. 5-(8-(3-ethynyl-3-methylpyrrolidin-1-yl)imidazo[1,2-b]pyridazin-6-yl)pyrimidine-2,4(1H,3H)-dione

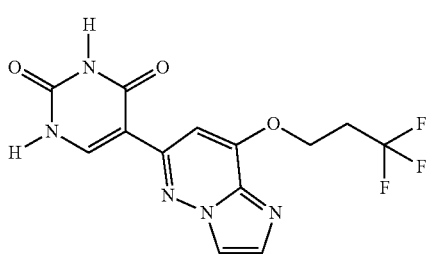 [SMILES: O=c1[nH]cc(-c2cc(OCCC(F)(F)F)c3nccn3n2)c(=O)[nH]1]

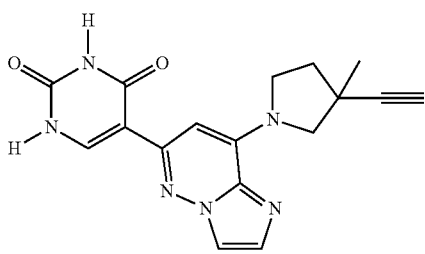 [SMILES: C#CC1(C)CCN(c2cc(-c3c[nH]c(=O)[nH]c3=O)nn3ccnc23)C1]

5-(8-(3,3,3-trifluoropropoxy)imidazo[1,2-b]pyridazin-6-yl)pyrimidine-2,4(1H,3H)-dione was prepared in the manner described for Example 676, but replacing 6-(2,4-di-tert-butoxypyrimidin-5-yl)-8-(3,3,3-trifluoro-2,2-dimethylpropoxy)imidazo[1,2-b]pyridazine with 6-(2,4-di-tert-butoxypyrimidin-5-yl)-8-(3,3,3-trifluoropropoxy)imidazo[1,2-b]pyridazine. ES/MS m/z: 342.15 [M+H]. $^1$H NMR (400 MHz, DMSO-d6) δ 11.53 (s, 2H), 8.25 (d, 1H), 8.04 (d, 1H), 7.72 (s, 1H), 7.36 (s, 1H), 4.59 (t, 2H), 2.97 (qt, 2H).

5-(8-(3-ethynyl-3-methylpyrrolidin-1-yl)imidazo[1,2-b]pyridazin-6-yl)pyrimidine-2,4(1H,3H)-dione was prepared in the manner described for Example 671, but replacing 6-(2,4-di-tert-butoxypyrimidin-5-yl)-N-(2,2-difluoroethyl)-N-(4-methoxybenzyl)imidazo[1,2-b]pyridazin-8-amine with 6-(2,4-di-tert-butoxypyrimidin-5-yl)-8-(3-ethynyl-3-methylpyrrolidin-1-yl)imidazo[1,2-b]pyridazine. ES/MS m/z: 337.17 [M+H]. $^1$H NMR (400 MHz, DMSO-d6) δ11.42-11.33 (m, 2H), 8.07 (d, 1H), 7.95 (d, 1H), 7.62 (d, 1H), 6.64 (s, 1H), 4.39-4.08 (m, 1H), 3.97-3.67 (m, 3H), 3.13 (s, 1H), 2.21 (dt, 1H), 2.02 (dt, 1H), 1.74 (s, 3H).

Example 684. 5-(8-(3-ethynylpyrrolidin-1-yl)imidazo[1,2-b]pyridazin-6-yl)pyrimidine-2,4(1H,3H)-dione

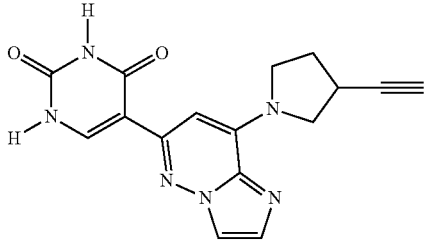 [SMILES: C#CC1CCN(c2cc(-c3c[nH]c(=O)[nH]c3=O)nn3ccnc23)C1]

5-(8-(3-ethynylpyrrolidin-1-yl)imidazo[1,2-b]pyridazin-6-yl)pyrimidine-2,4(1H,3H)-dione was prepared in the manner described for Example 683, but replacing 6-(2,4-di-tert-butoxypyrimidin-5-yl)-8-(3-ethynyl-3-methylpyrrolidin-1-yl)imidazo[1,2-b]pyridazine with 6-(2,4-di-tert-butoxypyrimidin-5-yl)-8-(3-ethynylpyrrolidin-1-yl)imidazo[1,2-b]pyridazine. ES/MS m/z: 323.18 [M+H]. $^1$H NMR (400 MHz, DMSO-d6) δ 11.38 (dd, 2H), 8.05 (d, 1H), 7.94 (d, 1H), 7.59 (d, 1H), 6.61 (s, 1H), 4.30-4.07 (m, 1H), 3.95-3.60 (m, 3H), 3.28-3.19 (m, 1H), 3.10 (d, 1H), 2.35-2.22 (m, 1H), 2.10-1.97 (m, 1H).

Example 685. 5-(8-(3-hydroxy-3-methylbut-1-yn-1-yl)imidazo[1,2-b]pyridazin-6-yl)pyrimidine-2,4(1H,3H)-dione

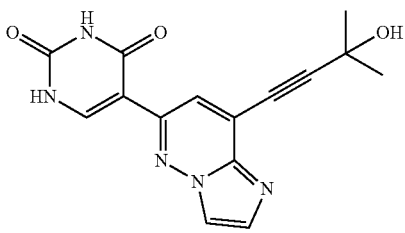 [SMILES: CC(C)(O)C#Cc1cc(-c2c[nH]c(=O)[nH]c2=O)nn2ccnc12]

5-(8-(3-hydroxy-3-methylbut-1-yn-1-yl)imidazo[1,2-b]pyridazin-6-yl)pyrimidine-2,4(1H,3H)-dione was prepared in the manner described for Example 683, but replacing 6-(2,4-di-tert-butoxypyrimidin-5-yl)-8-(3-ethynyl-3-methylpyrrolidin-1-yl)imidazo[1,2-b]pyridazine with 4-(6-(2,4-di-tert-butoxypyrimidin-5-yl)imidazo[1,2-b]pyridazin-8-yl)-2-methylbut-3-yn-2-ol. ES/MS m/z: 312.10 [M+H]. $^1$H NMR (400 MHz, DMSO-d6) δ 11.58 (d, 2H), 8.36 (s, 1H), 8.08 (d, 1H), 7.84 (s, 2H), 1.55 (s, 6H).

Example 686. 5-(8-(3,3-dimethylbut-1-yn-1-yl)imidazo[1,2-b]pyridazin-6-yl)pyrimidine-2,4(1H,3H)-dione

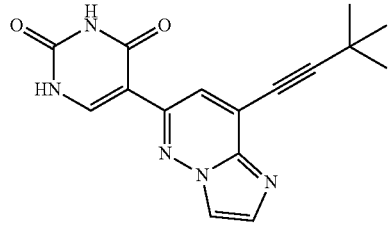 [SMILES: CC(C)(C)C#Cc1cc(-c2c[nH]c(=O)[nH]c2=O)nn2ccnc12]

5-(8-(3,3-dimethylbut-1-yn-1-yl)imidazo[1,2-b]pyridazin-6-yl)pyrimidine-2,4(1H,3H)-dione was prepared in the manner described for Example 685, but replacing 4-(6-(2,4-di-tert-butoxypyrimidin-5-yl)imidazo[1,2-b]pyridazin-8-yl)-2-methylbut-3-yn-2-ol with 6-(2,4-di-tert-butoxypyrimidin-5-yl)-8-(3,3-dimethylbut-1-yn-1-yl)imidazo[1,2-b]pyridazine. ES/MS m/z: 310.19 [M+H]. $^1$H NMR (400 MHz, DMSO-d6) δ 11.57 (d, 2H), 8.32 (d, 1H), 8.06 (d, 1H), 7.82 (s, 1H), 7.78 (s, 1H), 1.38 (s, 9H).

Example 687. 5-(8-(2,2-difluoro-3-hydroxypropoxy)imidazo[1,2-b]pyridazin-6-yl)pyrimidine-2,4(1H,3H)-dione

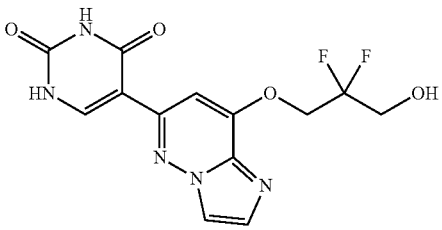 [SMILES: O=c1[nH]cc(-c2cc(OCC(F)(F)CO)c3nccn3n2)c(=O)[nH]1]

5-(8-(2,2-difluoro-3-hydroxypropoxy)imidazo[1,2-b]pyridazin-6-yl)pyrimidine-2,4(1H,3H)-dione was prepared in the manner described for Example 683, but replacing 6-(2,4-di-tert-butoxypyrimidin-5-yl)-8-(3-ethynyl-3-methylpyrrolidin-1-yl)imidazo[1,2-b]pyridazine with 3-((6-(2,4-di-tert-butoxypyrimidin-5-yl)imidazo[1,2-b]pyridazin-8-yl)oxy)-2,2-difluoropropan-1-ol. ES/MS m/z: 340.12 [M+H]. $^1$H NMR (400 MHz, DMSO-d6) δ 11.63 11.50 (m, 2H), 8.34 (d, 1H), 8.07 (d, 1H), 7.90-7.80 (m, 1H), 7.47 (s, 1H), 4.76 (t, 2H), 3.85 (t, 2H).

Example 688. 5-(8-(2,2-difluorobutoxy)imidazo[1,2-b]pyridazin-6-yl)pyrimidine-2,4(1H,3H)-dione

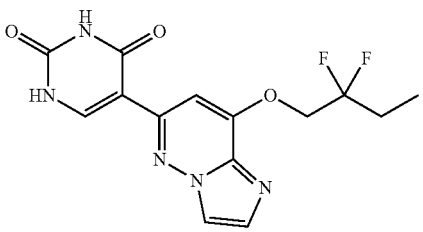 [SMILES: CCC(F)(F)COc1cc(-c2c[nH]c(=O)[nH]c2=O)nn2ccnc12]

5-(8-(2,2-difluorobutoxy)imidazo[1,2-b]pyridazin-6-yl)pyrimidine-2,4(1H,3H)-dione was prepared in the manner described for Example 683, but replacing 6-(2,4-di-tert-butoxypyrimidin-5-yl)-8-(3-ethynyl-3-methylpyrrolidin-1-yl)imidazo[1,2-b]pyridazine with 6-(2,4-di-tert-butoxypyrimidin-5-yl)-8-(2,2-difluorobutoxy)imidazo[1,2-b]pyridazine. ES/MS m/z: 338.14 [M+H]. ¹H NMR (400 MHz, DMSO-d6) δ 11.69-11.53 (m, 2H), 8.41 (d, 1H), 8.08 (d, 1H), 7.94 (d, 1H), 7.58 (s, 1H), 4.76 (t, 2H), 2.14 (tq, 2H), 1.04 (t, 3H).

Example 689. 5-(8-(2-cyclopropyl-2,2-difluoroethoxy)imidazo[1,2-b]pyridazin-6-yl)pyrimidine-2,4(1H,3H)-dione

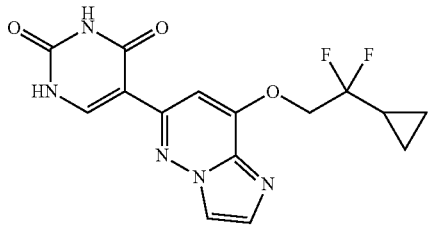 [SMILES: O=c1[nH]cc(-c2cc(OCC(F)(F)C3CC3)c3nccn3n2)c(=O)[nH]1]

5-(8-(2-cyclopropyl-2,2-difluoroethoxy)imidazo[1,2-b]pyridazin-6-yl)pyrimidine-2,4(1H,3H)-dione was prepared in the manner described for Example 688, but replacing 6-(2,4-di-tert-butoxypyrimidin-5-yl)-8-(2,2-difluorobutoxy)imidazo[1,2-b]pyridazine with 8-(2-cyclopropyl-2,2-difluoroethoxy)-6-(2,4-di-tert-butoxypyrimidin-5-yl)imidazo[1,2-b]pyridazine. ES/MS m/z: 350.12 [M+H]. ¹H NMR (400 MHz, DMSO-d6) δ 11.59 (dd, 2H), 8.38 (d, 1H), 8.08 (d, 1H), 7.90 (d, 1H), 7.56 (s, 1H), 4.85 (t, 2H), 1.63 (s, 1H), 0.77-0.61 (m, 4H).

Example 690. 5-(8-(2,2,3,3,3-pentafluoropropoxy)imidazo[1,2-b]pyridazin-6-yl)pyrimidine-2,4(1H,3H)-dione

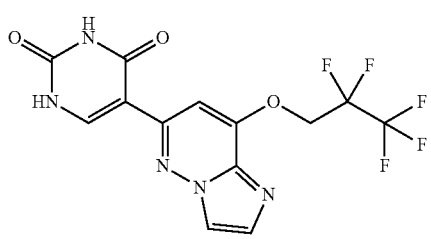 [SMILES: O=c1[nH]cc(-c2cc(OCC(F)(F)C(F)(F)F)c3nccn3n2)c(=O)[nH]1]

5-(8-(2,2,3,3,3-pentafluoropropoxy)imidazo[1,2-b]pyridazin-6-yl)pyrimidine-2,4(1H,3H)-dione was prepared in the manner described for Example 688, but replacing 6-(2,4-di-tert-butoxypyrimidin-5-yl)-8-(2,2-difluorobutoxy)imidazo[1,2-b]pyridazine with 6-(2,4-di-tert-butoxypyrimidin-5-yl)-8-(2,2,3,3,3-pentafluoropropoxy)imidazo[1,2-b]pyridazine. ES/MS m/z: 378.12 [M+H]. ¹H NMR (400 MHz, DMSO-d6) δ 11.62-11.52 (m, 2H), 8.35 (d, 1H), 8.06 (d, 1H), 7.83 (d, 1H), 7.53 (s, 1H), 5.37 (t, 2H).

Example 691. (S)-5-(8-(2-phenylpropoxy)imidazo[1,2-b]pyridazin-6-yl)pyrimidine-2,4(1H,3H)-dione

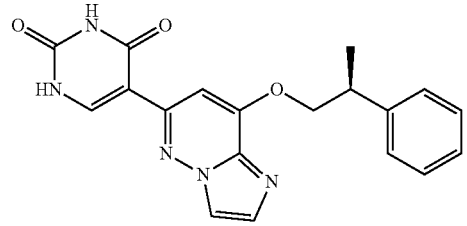 [SMILES: C[C@H](COc1cc(-c2c[nH]c(=O)[nH]c2=O)nn2ccnc12)c1ccccc1]

(S)-5-(8-(2-phenylpropoxy)imidazo[1,2-b]pyridazin-6-yl)pyrimidine-2,4(1H,3H)-dione was prepared in the manner described for Example 688, but replacing 6-(2,4-di-tert-butoxypyrimidin-5-yl)-8-(2,2-difluorobutoxy)imidazo[1,2-b]pyridazine with (S)-6-(2,4-di-tert-butoxypyrimidin-5-yl)-8-(2-phenylpropoxy)imidazo[1,2-b]pyridazine. ES/MS m/z: 364.11 [M+H]. ¹H NMR (400 MHz, DMSO-d6) δ 11.70-11.63 (m, 1H), 11.59 (d, 1H), 8.44 (d, 1H), 8.10 (d, 1H), 8.04 (d, 1H), 7.64 (s, 1H), 7.43 (d, 3H), 7.34 (t, 2H), 7.28-7.22 (m, 1H), 4.52 (dd, 1H), 4.42 (dd, 1H), 3.39 (q, 1H), 1.43 (d, 3H).

Example 692. 5-(8-(2,2-difluoro-2-(pyridin-2-yl)ethoxy)imidazo[1,2-b]pyridazin-6-yl)pyrimidine-2,4(1H,3H)-dione

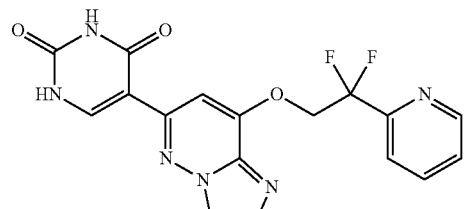

5-(8-(2,2-difluoro-2-(pyridin-2-yl)ethoxy)imidazo[1,2-b]pyridazin-6-yl)pyrimidine-2,4(1H,3H)-dione was prepared in the manner described for Example 688, but replacing 6-(2,4-di-tert-butoxypyrimidin-5-yl)-8-(2,2-difluorobutoxy)imidazo[1,2-b]pyridazine with 6-(2,4-di-tert-butoxypyrimidin-5-yl)-8-(2,2-difluoro-2-(pyridin-2-yl)ethoxy)imidazo[1,2-b]pyridazine. ES/MS m/z: 387.12 [M+H]. ¹H NMR (400 MHz, DMSO-d6) δ 11.65-11.60 (m, 1H), 11.58 (d, 1H), 8.73 (dd, 1H), 8.38 (d, 1H), 8.11-8.05 (m, 2H), 7.92-7.86 (m, 2H), 7.66-7.60 (m, 2H), 5.25 (t, 2H).

Example 693. 5-(8-(2,2-difluoro-2-(1-methyl-1H-imidazol-2-yl)ethoxy)imidazo[1,2-b]pyridazin-6-yl)pyrimidine-2,4(1H,3H)-dione

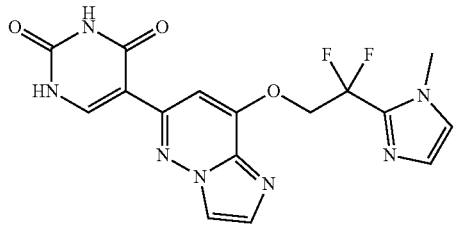 [SMILES: Cn1ccnc1C(F)(F)COc1cc(-c2c[nH]c(=O)[nH]c2=O)nn2ccnc12]

5-(8-(2,2-difluoro-2-(1-methyl-1H-imidazol-2-yl)ethoxy)imidazo[1,2-b]pyridazin-6-yl)pyrimidine-2,4(1H,3H)-dione was prepared in the manner described for Example 688, but replacing 6-(2,4-di-tert-butoxypyrimidin-5-yl)-8-(2,2-difluorobutoxy)imidazo[1,2-b]pyridazine with 6-(2,4-di-tert-butoxypyrimidin-5-yl)-8-(2,2-difluoro-2-(1-methyl-1H-imidazol-2-yl)ethoxy)imidazo[1,2-b]pyridazine. ES/MS m/z: 390.12 [M+H]. $^1$H NMR (400 MHz, DMSO-d6) δ 11.57 (s, 1H), 11.55 (s, 1H), 8.31 (d, 1H), 8.07 (d, 1H), 7.78 (d, 1H), 7.51 (s, 1H), 7.43 (s, 1H), 7.01 (d, 1H), 5.32 (t, 2H), 3.88 (s, 3H).

Example 694. 3-((6-(2,4-dioxo-1,2,3,4-tetrahydropyrimidin-5-yl)imidazo[1,2-b]pyridazin-8-yl)oxy)-2,2-difluoropropyl isopropylcarbamate

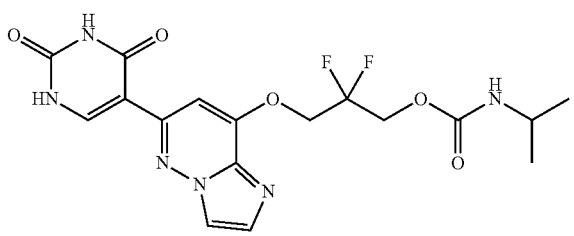

3-((6-(2,4-dioxo-1,2,3,4-tetrahydropyrimidin-5-yl)imidazo[1,2-b]pyridazin-8-yl)oxy)-2,2-difluoropropyl isopropylcarbamate was prepared in the manner described for Example 683, but replacing 6-(2,4-di-tert-butoxypyrimidin-5-yl)-8-(2,2-difluorobutoxy)imidazo[1,2-b]pyridazine with 3-((6-(2,4-di-tert-butoxypyrimidin-5-yl)imidazo[1,2-b]pyridazin-8-yl)oxy)-2,2-difluoropropyl isopropylcarbamate. ES/MS m/z: 425.12 [M+H]. $^1$H NMR (400 MHz, DMSO-d6) δ 11.59 (d, 2H), 8.34 (d, 1H), 8.07 (d, 1H), 7.83 (s, 1H), 7.47 (s, 1H), 7.43 (d, 1H), 4.84 (t, 2H), 4.51 (t, 2H), 3.71-3.63 (m, 1H), 1.15 (d, 6H).

Example 695. 5-(8-(2,2-difluoro-3-(pyridin-2-yloxy)propoxy)imidazo[1,2-b]pyridazin-6-yl)pyrimidine-2,4(1H,3H)-dione

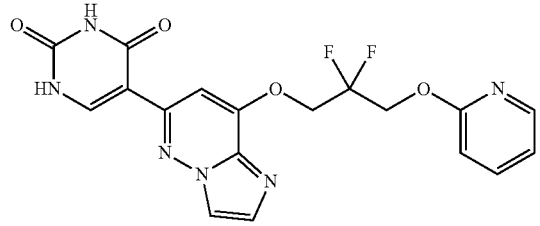 [SMILES: O=c1[nH]cc(-c2cc(OCC(F)(F)COc3ccccn3)c3nccn3n2)c(=O)[nH]1]

5-(8-(2,2-difluoro-3-(pyridin-2-yloxy)propoxy)imidazo[1,2-b]pyridazin-6-yl)pyrimidine-2,4(1H,3H)-dione was prepared in the manner described for Example 683, but replacing 6-(2,4-di-tert-butoxypyrimidin-5-yl)-8-(2,2-difluorobutoxy)imidazo[1,2-b]pyridazine with 6-(2,4-di-tert-butoxypyrimidin-5-yl)-8-(2,2-difluoro-3-(pyridin-2-yloxy)propoxy)imidazo[1,2-b]pyridazine. ES/MS m/z: 417.06 [M+H]. $^1$H NMR (400 MHz, DMSO-d6) δ 11.68-11.63 (m, 1H), 11.61 (d, 1H), 8.44 (d, 1H), 8.16 (ddd, 1H), 8.09 (d, 1H), 8.01 (d, 1H), 7.77 (ddd, 1H), 7.67 (s, 1H), 7.45-7.38 (m, 1H), 7.06 (ddd, 1H), 6.99-6.90 (m, 1H), 4.98 (t, 2H), 4.87 (t, 2H).

Example 696. 3-((6-(2,4-dioxo-1,2,3,4-tetrahydropyrimidin-5-yl)imidazo[1,2-b]pyridazin-8-yl)oxy)-2,2-difluoropropyl (2,2,2-trifluoroethyl) carbonate

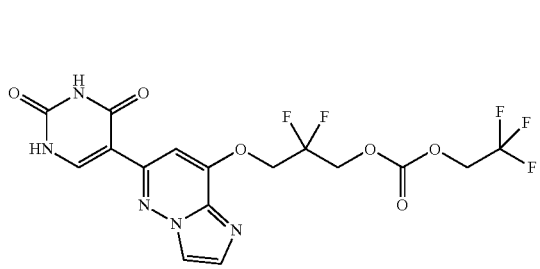 [SMILES: O=C(OCC(F)(F)F)OCC(F)(F)COc1cc(-c2c[nH]c(=O)[nH]c2=O)nn2ccnc12]

3-((6-(2,4-dioxo-1,2,3,4-tetrahydropyrimidin-5-yl)imidazo[1,2-b]pyridazin-8-yl)oxy)-2,2-difluoropropyl (2,2,2-trifluoroethyl) carbonate was prepared in the manner described for Example 683, but replacing 6-(2,4-di-tert-butoxypyrimidin-5-yl)-8-(2,2-difluorobutoxy)imidazo[1,2-b]pyridazine with 3-((6-(2,4-di-tert-butoxypyrimidin-5-yl)imidazo[1,2-b]pyridazin-8-yl)oxy)-2,2-difluoropropyl (2,2,2-trifluoroethyl) carbonate. ES/MS m/z: 466.16 [M+H]. $^1$H NMR (400 MHz, DMSO-d6) δ 11.62-11.54 (m, 2H), 8.35 (d, 1H), 8.06 (d, 1H), 7.84 (d, 1H), 7.48 (s, 1H), 4.98-4.86 (m, 4H), 4.80 (t, 2H).

Example 697. 5-(3-fluoro-8-((2S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione

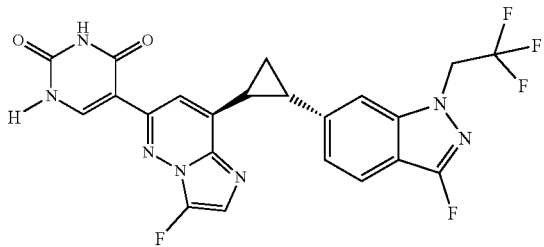

5-(3-fluoro-8-((2S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-3-fluoro-8-((2S,2S)-2-(3-fluoro-1-(2,2,2-trifluoroethyl)-1H-indazol-6-yl)cyclopropyl)imidazo[1,2-b]pyridazine. ES/MS m/z: 504.10 [M+H]. $^1$H NMR (400 MHz, DMSO-d6) δ 11.62-11.52 (m, 2H), 8.04 (d, J=6.2 Hz, 1H), 7.76 (s, 1H), 7.69 (d, J=8.5 Hz, 1H), 7.63-7.50 (m, 2H), 7.20 (dd, J=8.5, 1.3 Hz, 1H), 5.31 (q, J=9.0 Hz, 2H), 3.04 (ddd, J=9.0, 6.3, 4.4 Hz, 1H), 2.83 (ddd, J=8.9, 6.0, 4.4 Hz, 1H), 2.24-2.10 (m, 1H), 1.95-1.85 (m, 1H).

Example 698. 5-(8-((2S,2S)-2-(3,3-dimethyl-2-oxo-1-(2,2,2-trifluoroethyl)-2,3-dihydro-1H-pyrrolo[3,2-b]pyridin-6-yl)cyclopropyl)imidazo[1,2-b]pyridazin-6-yl)pyrimidine-2,4(1H,3H)-dione

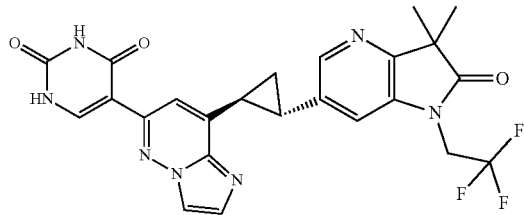 [SMILES: CC1(C)C(=O)N(CC(F)(F)F)c2cc([C@H]3C[C@@H]3c3cc(-c4c[nH]c(=O)[nH]c4=O)nn4ccnc34)cnc21]

5-(8-((2S,2S)-2-(3,3-dimethyl-2-oxo-1-(2,2,2-trifluoroethyl)-2,3-dihydro-1H-pyrrolo[3,2-b]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((2S,2S)-2-(6-(2,4-dimethoxypyrimidin-5-yl)imidazo[1,2-b]pyridazin-8-yl)cyclopropyl)-3,3-dimethyl-1-(2,2,2-trifluoroethyl)-1,3-dihydro-2H-pyrrolo[3,2-b]pyridin-2-one. ES/MS m/z: 512.20 [M+H]. $^1$H NMR (400 MHz, DMSO-d6) δ 11.57 (d, J=7.1 Hz, 2H), 8.36 (d, J=1.5 Hz, 1H), 8.21 (d, J=1.8 Hz, 1H), 8.04 (d, J=6.0 Hz, 1H), 7.90 (s, 1H), 7.61 (s, 1H), 7.52 (d, J=1.7 Hz, 1H), 4.68 (q, J=9.3 Hz, 2H), 2.89 (ddd, J=9.4, 6.3, 4.4 Hz, 1H), 2.84-2.74 (m, 1H), 2.13 (dt, J=9.0, 5.4 Hz, 1H), 1.88 (dt, J=8.8, 5.6 Hz, 1H), 1.32 (s, 6H).

Example 699. 5-(8-((2S,2S)-2-(3,3-dimethyl-2-oxo-1-(2,2,2-trifluoroethyl)-2,3-dihydro-1H-pyrrolo[3,2-b]pyridin-6-yl)cyclopropyl)imidazo[1,2-b]pyridazin-6-yl)pyrimidine-2,4(1H,3H)-dione

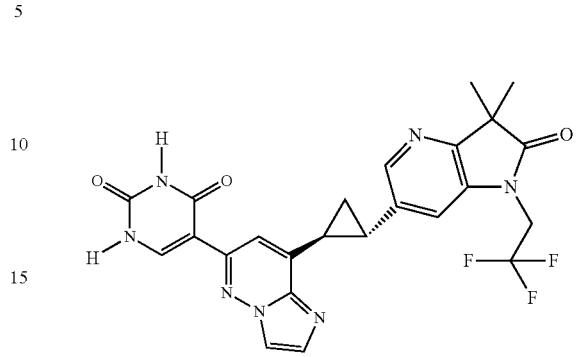

5-(8-((1S,2S)-2-(3,3-dimethyl-2-oxo-1-(2,2,2-trifluoroethyl)-2,3-dihydro-1H-pyrrolo[3,2-b]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-3,3-dimethyl-1-(2,2,2-trifluoroethyl)-1,3-dihydro-2H-pyrrolo[3,2-b]pyridin-2-one. ES/MS m/z: 512.20 [M+H]. $^1$H NMR (400 MHz, DMSO-d6) δ 11.74 (d, J=6.4 Hz, 1H), 11.63 (d, J=1.9 Hz, 1H), 8.56 (d, J=1.8 Hz, 1H), 8.24-8.21 (m, 2H), 8.11 (d, J=6.3 Hz, 1H), 7.81 (s, 1H), 7.60 (d, J=1.7 Hz, 1H), 4.71 (q, J=9.4 Hz, 2H), 3.05 (dd, J=9.1, 4.9 Hz, 1H), 2.91-2.76 (m, 1H), 2.06-1.84 (m, 2H), 1.33 (d, J=1.1 Hz, 6H).

Example 700. 5-(8-((2S,2S)-2-(3,3-dimethyl-2-oxo-1-(2,2,2-trifluoroethyl)-2,3-dihydro-1H-pyrrolo[3,2-c]pyridin-6-yl)cyclopropyl)imidazo[1,2-b]pyridazin-6-yl)pyrimidine-2,4(1H,3H)-dione

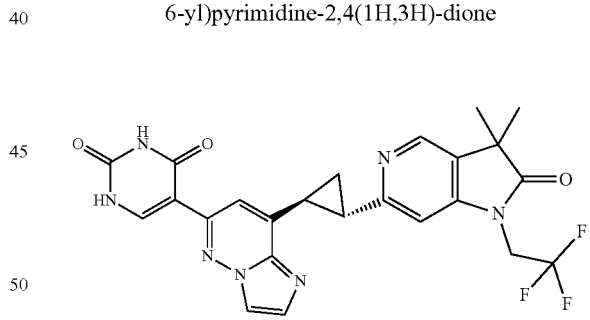

5-(8-((2S,2S)-2-(3,3-dimethyl-2-oxo-1-(2,2,2-trifluoroethyl)-2,3-dihydro-1H-pyrrolo[3,2-c]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((2S,2S)-2-(6-(2,4-dimethoxypyrimidin-5-yl)imidazo[1,2-b]pyridazin-8-yl)cyclopropyl)-3,3-dimethyl-1-(2,2,2-trifluoroethyl)-1,3-dihydro-2H-pyrrolo[3,2-c]pyridin-2-one. ES/MS m/z: 512.20 [M+H]. $^1$H NMR (400 MHz, Acetonitrile-d3) δ 9.35 (s, 1H), 9.25 (s, 1H), 8.44 (s, 1H), 8.19-8.09 (m, 2H), 7.98-7.89 (m, 2H), 7.44 (s, 1H), 4.59 (q, J=8.9 Hz, 2H), 3.43-3.33 (m, 1H), 3.19-3.09 (m, 1H), 2.21 (dt, J=9.2, 5.9 Hz, 1H), 2.10-1.97 (m, 1H), 1.49 (s, 6H).

Example 701. 5-(8-((2S,2S)-2-(1-(2,2,2-trifluoroethyl)-3-(trifluoromethyl)-1H-pyrrolo[2,3-b]pyridin-6-yl)cyclopropyl)imidazo[1,2-b]pyridazin-6-yl)pyrimidine-2,4(1H,3H)-dione

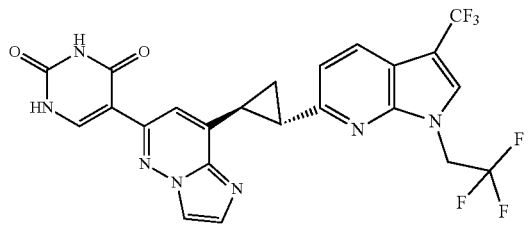 [SMILES: O=c1[nH]cc(-c2cc([C@H]3C[C@@H]3c3ccc4c(C(F)(F)F)cn(CC(F)(F)F)c4n3)c3nccn3n2)c(=O)[nH]1]

5-(8-((2S,2S)-2-(1-(2,2,2-trifluoroethyl)-3-(trifluoromethyl)-1H-pyrrolo[2,3-b]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(1-(2,2,2-trifluoroethyl)-3-(trifluoromethyl)-1H-pyrrolo[2,3-b]pyridin-6-yl)cyclopropyl)imidazo[1,2-b]pyridazine. ES/MS m/z: 536.20 [M+H]. $^1$H NMR (400 MHz, DMSO-d6) δ 11.67 (d, J=6.1 Hz, 1H), 11.60 (s, 1H), 8.48 (s, 1H), 8.26 (d, J=1.6 Hz, 1H), 8.07 (dd, J=15.3, 7.2 Hz, 3H), 7.76 (s, 1H), 7.44 (d, J=8.2 Hz, 1H), 5.44-5.18 (m, 2H), 3.16-3.06 (m, 2H), 2.12-2.01 (m, 2H).

Example 702. 5-(8-((2S,2S)-2-(3,3-dimethyl-2-oxo-1-(2,2,2-trifluoroethyl)indolin-6-yl)cyclopropyl)-3-fluoroimidazo[1,2-b]pyridazin-6-yl)pyrimidine-2,4(1H,3H)-dione

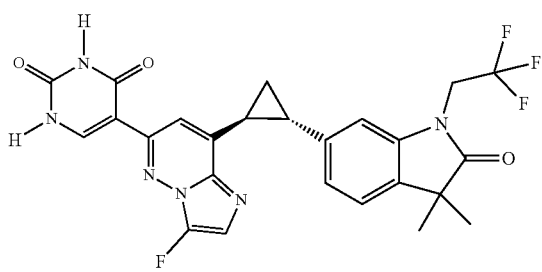 [SMILES: CC1(C)C(=O)N(CC(F)(F)F)c2cc([C@H]3C[C@@H]3c3cc(-c4c[nH]c(=O)[nH]c4=O)nn4c(F)cnc34)ccc21]

5-(8-((2S,2S)-2-(3,3-dimethyl-2-oxo-1-(2,2,2-trifluoroethyl)indolin-6-yl)cyclopropyl)-3-fluoroimidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((2S,2S)-2-(6-(2,4-dimethoxypyrimidin-5-yl)-3-fluoroimidazo[1,2-b]pyridazin-8-yl)cyclopropyl)-3,3-dimethyl-1-(2,2,2-trifluoroethyl)indolin-2-one. ES/MS m/z: 529.20 [M+H]. $^1$H NMR (400 MHz, DMSO-d6) δ 11.53 (d, J=3.8 Hz, 2H), 8.03 (d, J=6.5 Hz, 1H), 7.55 (d, J=7.1 Hz, 1H), 7.47 (s, 1H), 7.31 (d, J=7.7 Hz, 1H), 7.13 (s, 1H), 7.00 (dd, J=7.8, 1.4 Hz, 1H), 4.63 (q, J=9.4 Hz, 2H), 2.92-2.82 (m, 1H), 2.76-2.67 (m, 1H), 2.12 (dt, J=9.8, 5.3 Hz, 1H), 1.86-1.74 (m, 1H), 1.30 (s, 6H).

Example 703. 5-(8-((2S,2S)-2-(3,3-dimethyl-2-oxo-1-(2,2,2-trifluoroethyl)indolin-6-yl)cyclopropyl)imidazo[1,2-b]pyridazin-6-yl)pyrimidine-2,4(1H,3H)-dione

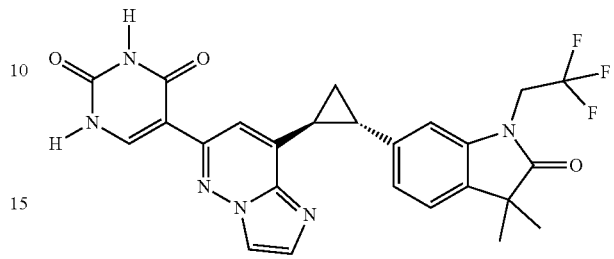

5-(8-((1S,2S)-2-(3,3-dimethyl-2-oxo-1-(2,2,2-trifluoroethyl)indolin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((2S,2S)-2-(6-(2,4-dimethoxypyrimidin-5-yl)imidazo[1,2-b]pyridazin-8-yl)cyclopropyl)-3,3-dimethyl-1-(2,2,2-trifluoroethyl)indolin-2-one. ES/MS m/z: 511.20 [M+H]. $^1$H NMR (400 MHz, DMSO-d6) δ 11.62 (dd, J=24.9, 4.1 Hz, 2H), 8.46 (s, 1H), 8.08 (d, J=6.2 Hz, 2H), 7.69 (s, 1H), 7.34 (d, J=7.7 Hz, 1H), 7.16 (s, 1H), 7.05-6.98 (m, 1H), 4.65 (q, J=9.4 Hz, 2H), 2.91-2.77 (m, 2H), 2.04-1.79 (m, 2H).

Example 704. 5-(8-((2S,2S)-2-(1-(2,2,2-trifluoroethyl)-1H-pyrrolo[2,3-b]pyridin-6-yl)cyclopropyl)imidazo[1,2-b]pyridazin-6-yl)pyrimidine-2,4(1H,3H)-dione

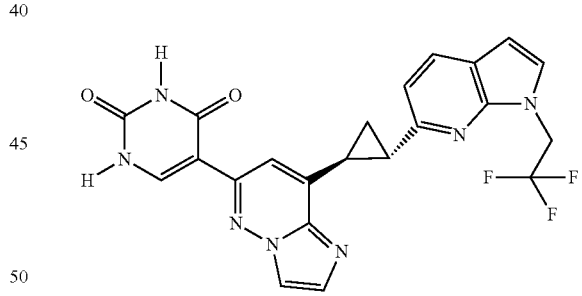

5-(8-((1S,2S)-2-(1-(2,2,2-trifluoroethyl)-1H-pyrrolo[2,3-b]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(1-(2,2,2-trifluoroethyl)-1H-pyrrolo[2,3-b]pyridin-6-yl)cyclopropyl)imidazo[1,2-b]pyridazine. ES/MS m/z: 468.10 [M+H]. $^1$H NMR (400 MHz, DMSO-d6) δ 11.69 (dd, J=45.4, 3.7 Hz, 2H), 8.57 (d, J=1.8 Hz, 1H), 8.22 (s, 1H), 8.12 (d, J=6.2 Hz, 1H), 8.00-7.83 (m, 2H), 7.54 (d, J=3.6 Hz, 1H), 7.23 (d, J=8.0 Hz, 1H), 6.58 (d, J=3.6 Hz, 1H), 5.22 (ddq, J=53.4, 15.3, 9.2 Hz, 2H), 3.18 (dt, J=9.5, 5.5 Hz, 1H), 3.00 (ddd, J=9.4, 6.1, 4.0 Hz, 1H), 2.09 (d, J=8.0 Hz, 1H), 2.02-1.90 (m, 1H).

Example 705. 5-(8-((2S,2S)-2-(1-(2,2,2-trifluoro-ethyl)-1H-pyrrolo[3,2-c]pyridin-6-yl)cyclopropyl)imidazo[1,2-b]pyridazin-6-yl)pyrimidine-2,4(1H,3H)-dione

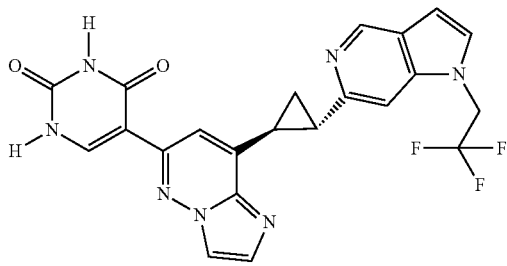 [SMILES: O=c1[nH]cc(-c2cc([C@H]3C[C@@H]3c3cc4c(ccn4CC(F)(F)F)cn3)c3nccn3n2)c(=O)[nH]1]

5-(8-((1S,2S)-2-(1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(1-(2,2,2-trifluoroethyl)-1H-pyrrolo[3,2-c]pyridin-6-yl)cyclopropyl)imidazo[1,2-b]pyridazine. ES/MS m/z: 468.10 [M+H]. $^1$H NMR (400 MHz, DMSO-d6) δ 15.52 (s, 1H), 11.82-11.75 (m, 1H), 11.61 (d, J=1.9 Hz, 1H), 9.24 (s, 1H), 8.52 (s, 1H), 8.39 (s, 1H), 8.12 (d, J=6.3 Hz, 2H), 7.95 (d, J=3.5 Hz, 1H), 7.86 (s, 1H), 7.13 (d, J=3.4 Hz, 1H), 5.54 (q, J=9.1 Hz, 2H), 3.31 (d, J=19.1 Hz, 2H), 2.33 (dt, J=9.1, 5.7 Hz, 1H), 2.22 (dt, J=8.8, 5.7 Hz, 1H).

Example 706. 5-(8-((2S,2S)-2-(3-fluoro-1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione

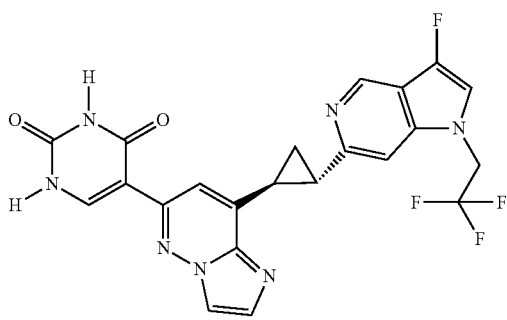 [SMILES: O=c1[nH]cc(-c2cc([C@H]3C[C@@H]3c3cc4c(cn3)c(F)cn4CC(F)(F)F)c3nccn3n2)c(=O)[nH]1]

5-(8-((1S,2S)-2-(3-fluoro-1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-(2,4-dimethoxypyrimidin-5-yl)-8-((1S,2S)-2-(3-fluoro-1-(2,2,2-trifluoroethyl)-1H-pyrrolo[3,2-c]pyridin-6-yl)cyclopropyl)imidazo[1,2-b]pyridazine. ES/MS m/z: 486.20 [M+H]. $^1$H NMR (400 MHz, DMSO-d6) δ 11.73-11.66 (m, 1H), 11.60 (d, J=2.0 Hz, 1H), 9.36 (s, 1H), 8.47 (s, 1H), 8.29 (s, 1H), 8.10 (d, J=6.2 Hz, 1H), 8.05-7.98 (m, 2H), 7.80 (s, 1H), 5.41 (q, J=8.9 Hz, 2H), 3.15 (s, 2H), 2.35-2.27 (m, 1H), 2.17 (dt, J=8.9, 5.6 Hz, 1H).

Example 707. 5-(8-((2S,2S)-2-(1-oxo-2-(2,2,2-trifluoroethyl)-1,2-dihydroisoquinolin-7-yl)cyclopropyl)imidazo[1,2-b]pyridazin-6-yl)pyrimidine-2,4(1H,3H)-dione

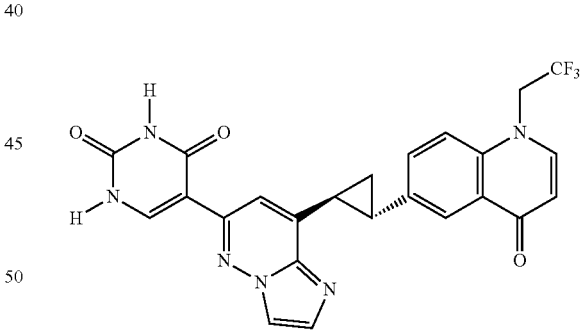

5-(8-((1S,2S)-2-(1-oxo-2-(2,2,2-trifluoroethyl)-1,2-dihydroisoquinolin-7-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 7-((1S,2S)-2-(6-(2,4-dimethoxypyrimidin-5-yl)imidazo[1,2-b]pyridazin-8-yl)cyclopropyl)-2-(2,2,2-trifluoroethyl)isoquinolin-1(2H)-one. ES/MS m/z: 495.20 [M+H]. $^1$H NMR (400 MHz, DMSO-d6) δ 11.56 (d, J=3.8 Hz, 2H), 8.36 (s, 1H), 8.11-8.01 (m, 2H), 7.90 (s, 1H), 7.73-7.59 (m, 3H), 7.43 (d, J=7.4 Hz, 1H), 6.72 (d, J=7.4 Hz, 1H), 4.94 (qd, J=9.3, 2.6 Hz, 2H), 2.99 (ddd, J=9.4, 6.2, 4.4 Hz, 1H), 2.85 (dt, J=9.8, 5.1 Hz, 1H), 2.10 (dt, J=8.9, 5.3 Hz, 1H), 1.88 (dt, J=8.6, 5.4 Hz, 1H).

Example 708. 5-(8-((2S,2S)-2-(4-oxo-1-(2,2,2-trifluoroethyl)-1,4-dihydroquinolin-6-yl)cyclopropyl)imidazo[1,2-b]pyridazin-6-yl)pyrimidine-2,4(1H,3H)-dione 5-(8-((2S,2S)-2-(4-oxo-1-(2,2,2-trifluoroethyl)-1,4-dihydroquinolin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-1-(2,2,2-trifluoroethyl)quinolin-4(1H)-one. ES/MS m/z: 495.10 [M+H]. $^1$H NMR (400 MHz, DMSO-d6) δ 11.58 (s, 1H), 8.41 (s, 1H), 8.10-8.03 (m, 1H), 8.08-7.94 (m, 3H), 7.89 (d, J=9.0 Hz, 1H), 7.74-7.64 (m, 2H), 6.18 (d, J=7.8 Hz, 1H), 5.35 (q, J=8.8 Hz, 2H), 2.99-2.90 (m, 1H), 2.85 (s, 1H), 2.05 (d, J=7.5 Hz, 1H), 1.94-1.85 (m, 1H).

Example 709. 5-(8-((2S,2S)-2-(4-(2,2,2-trifluoroethoxy)quinolin-6-yl)cyclopropyl)imidazo[1,2-b]pyridazin-6-yl)pyrimidine-2,4(1H,3H)-dione

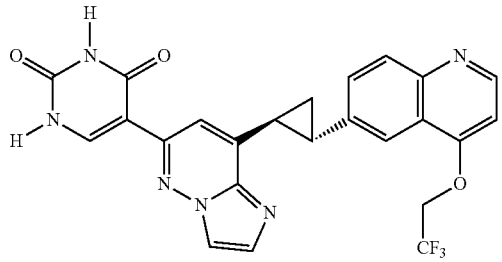 [SMILES: O=c1[nH]cc(-c2cc([C@H]3C[C@@H]3c3ccc4nccc(OCC(F)(F)F)c4c3)c3nccn3n2)c(=O)[nH]1]

5-(8-((2S,2S)-2-(4-(2,2,2-trifluoroethoxy)quinolin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-4-(2,2,2-trifluoroethoxy)quinoline. ES/MS m/z: 495.10 [M+1-1]. $^1$H NMR (400 MHz, DMSO-d6) δ 11.70 (d, J=6.3 Hz, 1H), 11.60 (d, J=2.0 Hz, 1H), 9.24 (d, J=6.4 Hz, 1H), 8.48 (s, 1H), 8.28 (d, J=8.9 Hz, 1H), 8.21 (d, J=1.9 Hz, 1H), 8.09 (dd, J=7.5, 4.3 Hz, 2H), 8.00 (dd, J=9.0, 2.0 Hz, 1H), 7.76 (s, 1H), 7.67 (d, J=6.5 Hz, 1H), 5.41 (q, J=8.5 Hz, 2H), 3.19 (ddd, J=9.1, 6.2, 4.5 Hz, 1H), 3.11 (s, 1H), 2.14 (dt, J=9.0, 5.6 Hz, 1H), 2.00 (dt, J=8.5, 5.6 Hz, 1H).

Example 710. 5-(8-((1S,2S)-2-(4-(2,2,2-trifluoroethoxy)isoquinolin-6-yl)cyclopropyl)imidazo[1,2-b]pyridazin-6-yl)pyrimidine-2,4(1H,3H)-dione

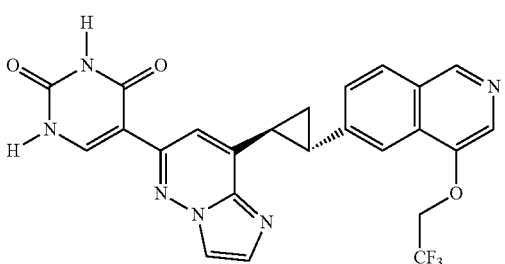

5-(8-((1S,2S)-2-(4-(2,2,2-trifluoroethoxy)isoquinolin-6-yl)cyclopropyl)imidazo[1,2-b]pyridazin-6-yl)pyrimidine-2,4(1H,3H)-dione was prepared in a manner described for Example 1, but replacing 8-cyclopropyl-6-(2,4-dimethoxypyrimidin-5-yl)-2-methyl-imidazo[1,2-b]pyridazine with 6-((1S,2S)-2-(6-(2,4-dimethoxypyrimidin-5-yl)imidazo[1,2-b]pyridazin-8-yl)cyclopropyl)-4-(2,2,2-trifluoroethoxy)isoquinoline. ES/MS m/z: 495.1 [M+H]. $^1$NMR (400 MHz, DMSO-d6) δ 11.68 (d, J=6.4 Hz, 1H), 11.61 (d, J=2.0 Hz, 1H), 9.41 (s, 1H), 8.51-8.38 (m, 3H), 8.16-8.05 (m, 3H), 7.86-7.75 (m, 2H), 5.18 (q, J=8.7 Hz, 2H), 3.26-3.09 (m, 2H), 2.19 (dt, J=9.1, 5.5 Hz, 1H), 2.06 (dt, J=8.6, 5.5 Hz, 1H).

Example 711. (S)-5-(8-(3,3-difluoro-4-(1-(2,2,2-trifluoroethyl)-1H-indazol-6-yl)oxy)pyrrolidin-1-yl)imidazo[1,2-b]pyridazin-6-yl)pyrimidine-2,4(1H,3H)-dione

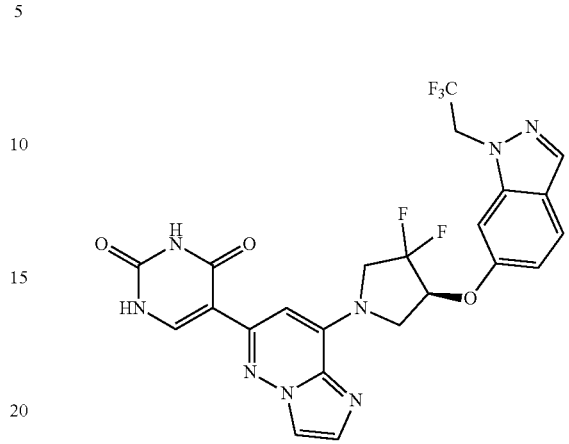

(S)-5-(8-(3,3-difluoro-4-((1-(2,2,2-trifluoroethyl)-1H-indazol-6-yl)oxy)pyrrolidin-1-yl)imidazo[1,2-b]pyridazin-6-yl)pyrimidine-2,4(1H,3H)-dione as the TFA salt was prepared in the manner described for Example 216, but replacing 7-(3,3-difluoro-4,4-dimethylpyrrolidin-1-yl)-5-(2,4-dimethoxypyrimidin-5-yl)pyrazolo[1,5-a]pyrimidine with (S)-8-(3,3-difluoro-4-((1-(2,2,2-trifluoroethyl)-1H-indazol-6-yl)oxy)pyrrolidin-1-yl)-6-(2,4-dimethoxypyrimidin-5-yl)imidazo[1,2-b]pyridazine. ES/MS m/z: 549.0 [M+H]. $^1$H NMR (400 MHz, DMSO-d6) δ11.43-11.36 (m, 2H), 8.14-8.13 (m, 1H), 8.08 (d, J=1.2 Hz, 1H), 7.94 (d, J=6.1 Hz, 1H), 7.75 (d, J=8.8 Hz, 1H), 7.61-7.59 (m, 1H), 7.57 (d, J=1.3 Hz, 1H), 7.00 (dd, J=8.8, 2.1 Hz, 1H), 6.64 (s, 1H), 5.54-5.29 (m, 3H), 4.73-4.09 (m, 4H).

Example 712. (S)-4-(1-(6-(2,4-dioxo-1,2,3,4-tetrahydropyrimidin-5-yl)imidazo[1,2-b]pyridazin-8-yl)-4,4-difluoropyrrolidin-3-yl)oxy)-2-(trifluoromethyl)benzonitrile

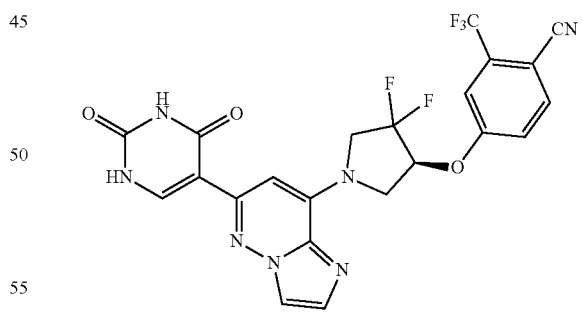

(S)-4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)-2-(trifluoromethyl)benzonitrile was prepared as follows: To a solution of (S)-4-((1-(6-(2,4-dimethoxypyrimidin-5-yl)imidazo[1,2-b]pyridazin-8-yl)-4,4-difluoropyrrolidin-3-yl)oxy)-2-(trifluoromethyl)benzonitrile (32 mg, 0.059 mmol, 1 equiv) in MeOH (1.0 mL) was added 1 N HCl (1.0 mL). The solution was heated to 80° C. and stirred for 3 h and 15 min prior to purification by RP-HPLC (10-90% MeCN/H$_2$O with TFA, Gemini-NX column) to afford the title compound as the TFA salt. ES/MS m/z: 520.0 [M+H]. $^1$H NMR (400 MHz, DMSO-d6) δ 11.44-11.35 (m, 2H), 8.19 (d, J=8.7 Hz, 1H), 8.09 (d, J=1.2 Hz, 1H), 7.93 (d, J=6.1 Hz, 1H), 7.73 (d, J=2.6 Hz, 1H), 7.65 (dd, J=8.7, 2.6 Hz, 1H), 7.58 (d, J=1.2 Hz, 1H), 6.64 (s, 1H), 5.84-5.76 (m, 1H), 4.70-3.76 (m, 4H). $^{19}$F NMR (376 MHz, DMSO-d6) δ −61.47, −75.30, −106.17−−107.76 (m), −119.74−−121.39 (m).

Example 713. (S)-1-(5-(2,4-dioxo-1,2,3,4-tetrahydropyrimidin-5-yl)pyrazolo[1,5-a]pyrimidin-7-yl)-4,4-difluoropyrrolidin-3-yl isopropylcarbamate

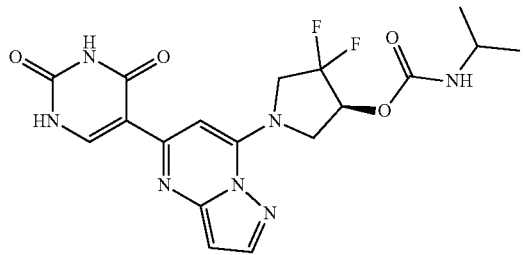 [SMILES: CC(C)NC(=O)O[C@H]1CN(c2cc(-c3c[nH]c(=O)[nH]c3=O)nc3ccnn23)CC1(F)F]

(S)-1-(5-(2,4-dioxo-1,2,3,4-tetrahydropyrimidin-5-yl)pyrazolo[1,5-a]pyrimidin-7-yl)-4,4-difluoropyrrolidin-3-yl isopropylcarbamate was prepared as follows: To a solution of (S)-1-(5-(2,4-dimethoxypyrimidin-5-yl)pyrazolo[1,5-a]pyrimidin-7-yl)-4,4-difluoropyrrolidin-3-yl isopropylcarbamate (26 mg, 0.056 mmol, 1 equiv) in MeOH (2.0 mL) was added 1 N HCl (2.0 mL). The solution was heated to 80° C. and stirred for 2 h prior to purification by RP-HPLC (10-90% MeCN/H$_2$O with TFA, Gemini-NX column) to afford the title compound as the TFA salt. ES/MS m/z: 436.0 [M+H]. $^1$H NMR (400 MHz, DMSO-d6) δ 11.85-11.53 (m, 2H), 8.43 (d, J=5.9 Hz, 1H), 8.12 (d, J=2.3 Hz, 1H), 7.56 (d, J=7.7 Hz, 1H), 7.00 (s, 1H), 6.47 (d, J=2.3 Hz, 1H), 5.52-5.39 (m, 1H), 4.70-4.35 (m, 3H), 4.22-3.49 (m, 2H), 1.09-1.03 (m, 6H). $^{19}$F NMR (376 MHz, DMSO-d6) δ −75.24, −108.68 (d, J=238.0 Hz), −119.93 (d, J=237.6 Hz).

Example 714. 5-(8-((2S,2S)-2-(4-methyl-1-(2,2,2-trifluoroethyl)-1H-indazol-6-yl)cyclopropyl)imidazo[1,2-b]pyridazin-6-yl)pyrimidine-2,4(1H,3H)-dione

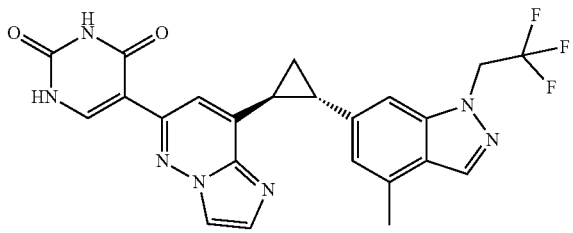 [SMILES: Cc1cc([C@H]2C[C@@H]2c2cc(-c3c[nH]c(=O)[nH]c3=O)nn3ccnc23)cc2c1cnn2CC(F)(F)F]

5-(8-((2S,2S)-2-(4-methyl-1-(2,2,2-trifluoroethyl)-1H-indazol-6-yl)cyclopropyl)imidazo[1,2-b]pyridazin-6-yl)pyrimidine-2,4(1H,3H)-dione was prepared in the manner described for Example 456, but replacing 5-bromo-7-((2S,2S)-2-(1-(2,2,2-trifluoroethyl)-1H-indazol-6-yl)cyclopropyl)pyrazolo[1,5-a]pyrimidine with 6-chloro-8-((1S,2S)-2-(4-methyl-1-(2,2,2-trifluoroethyl)-1H-indazol-6-yl)cyclopropyl)imidazo[1,2-b]pyridazine. Purification was accomplished by RP-HPLC (10-90% MeCN/H$_2$O with TFA modifier, Gemini column). ES/MS m/z: 482.2 [M+H]. $^1$H NMR (400 MHz, DMSO-d6) δ 11.53 (d, J=4.1 Hz, 2H), 8.31 (s, 1H), 8.19 (s, 1H), 8.02 (d, J=6.3 Hz, 1H), 7.82 (s, 1H), 7.54 (d, J=11.6 Hz, 2H), 6.89 (s, 1H), 5.37 (q, J=9.1 Hz, 2H), 2.95 (ddd, J=9.3, 6.3, 4.4 Hz, 1H), 2.78 (dt, J=9.5, 5.4 Hz, 1H), 2.54 (s, 3H), 2.14-2.04 (m, 1H), 1.89 (dt, J=11.0, 5.3 Hz, 1H). $^{19}$F NMR (376 MHz, DMSO-d6) δ −70.06 (t, J=9.2 Hz), −74.98.

Example 715. 5-(7-((2S,2S)-2-(2'-oxo-1'-(2,2,2-trifluoroethyl)spiro[cyclopropane-1,3'-indolin]-6'-yl)cyclopropyl)pyrazolo[1,5-a]pyrimidin-5-yl)pyrimidine-2,4(1H,3H)-dione

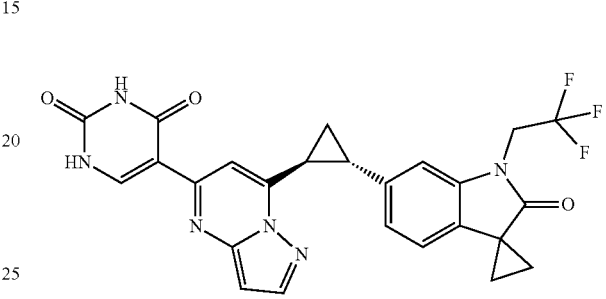

5-(7-((1S,2S)-2-(2'-oxo-1'-(2,2,2-trifluoroethyl)spiro[cyclopropane-1,3'-indolin]-6'-yl)cyclopropyl)pyrazolo[1,5-a]pyrimidin-5-yl)pyrimidine-2,4(1H,3H)-dione was prepared in the manner described for Example 456, but replacing 5-bromo-74(1S,2S)-2-(1-(2,2,2-trifluoroethyl)-1H-indazol-6-yl)cyclopropyl)pyrazolo[1,5-a]pyrimidine with 6'-((1S,2S)-2-(5-bromopyrazolo[1,5-a]pyrimidin-7-yl)cyclopropyl)-1'-(2,2,2-trifluoroethyl)spiro[cyclopropane-1,3'-indolin]-2'-one. Purification was accomplished by RP-HPLC (10-90% MeCN/H$_2$O with TFA modifier, Gemini column), followed by silica gel chromatography (0-100% EtOAc/hexanes). ES/MS m/z: 509.2 [M+H]. $^1$H NMR (400 MHz, Methanol-d4) δ 8.45 (s, 1H), 8.14 (d, J=2.4 Hz, 1H), 7.68 (s, 1H), 7.18 (s, 1H), 7.09 (dd, J=7.8, 1.4 Hz, 1H), 6.97 (d, J=7.8 Hz, 1H), 6.63 (d, J=2.3 Hz, 1H), 4.61 (q, J=9.0 Hz, 2H), 3.16-3.09 (m, 1H), 2.78-2.69 (m, 1H), 1.95-1.80 (m, 2H), 1.75-1.65 (m, 4H).

Example 716. 5-(3-fluoro-7-((1S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione

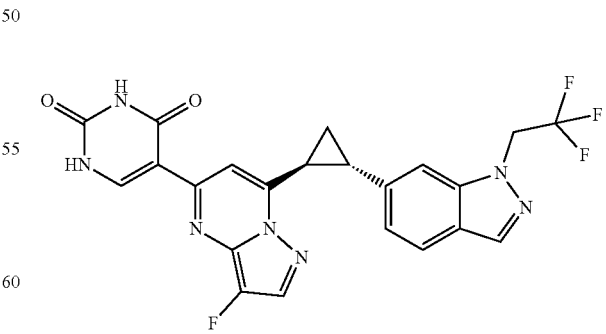

5-(3-fluoro-74(1S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione was prepared in the manner described for Example 456, but replacing 5-bromo-7-((2S, 2S)-2-(1-(2,2,2-trifluoroethyl)-1H-indazol-6-yl)cyclopropyl)pyrazolo[1,5-a]pyrimidine with 5-bromo-3-fluoro-(1S,2S)-2-(1-(2,2,2-trifluoroethyl)-1H-indazol-6-yl)cyclopropyl)pyrazolo[1,5-a]pyrimidine. Purification was accomplished by RP-HPLC (10-90% MeCN/H$_2$O with TFA modifier, Gemini column). ES/MS m/z: 486.1 [M+H]. $^1$H NMR (400 MHz, DMSO-d6) δ 11.66 (s, 1H), 11.55 (s, 1H), 8.36 (s, 1H), 8.30 (d, J=3.4 Hz, 1H), 8.16 (s, 1H), 7.79-7.67 (m, 3H), 7.18 (d, J=8.3 Hz, 1H), 5.41 (q, J=8.9 Hz, 2H), 3.10 (q, J=7.0 Hz, 1H), 2.78 (q, J=7.1, 6.6 Hz, 1H), 1.95 (t, J=7.5 Hz, 2H). $^{19}$F NMR (376 MHz, DMSO-d6) δ −70.06 (t, J=9.1 Hz), −184.76 (d, J=3.5 Hz).

Example 717. 5-[8-[(1S,2S)-2-[3-fluoro-1-(2,2,2-trifluoroethyl)pyrazolo[4,3-b]pyridin-6-yl]cyclopropyl]imidazo[1,2-b]pyridazin-6-yl]-1H-pyrimidine-2,4-dione

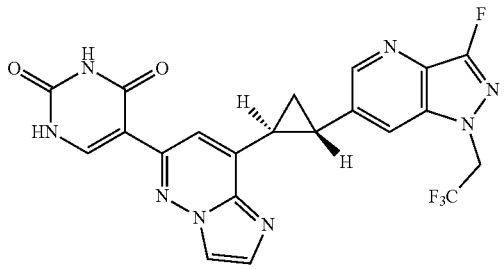 [SMILES: O=c1[nH]cc(-c2cc([C@H]3C[C@@H]3c3cnc4c(F)nn(CC(F)(F)F)c4c3)c3nccn3n2)c(=O)[nH]1]

5-[8-[(1S,2S)-2-[3-fluoro-1-(2,2,2-trifluoroethyl)pyrazolo[4,3-b]pyridin-6-yl]cyclopropyl]imidazo[1,2-b]pyridazin-6-yl]-1H-pyrimidine-2,4-dione was prepared in the manner described for Example 1, but replacing 8-cyclopropyl-6-(2,4-dimethoxypyrimidin-5-yl)-2-methyl-imidazo[1,2-b]pyridazine with 6-[(1S,2S)-2-[6-(2,4-dimethoxypyrimidin-5-yl)imidazo[1,2-b]pyridazin-8-yl]cyclopropyl]-3-fluoro-1-(2,2,2-trifluoroethyl)pyrazolo[4,3-b]pyridine. ES/MS m/z: 487.1 [M+H]. $^1$H NMR (400 MHz, DMSO-d6) δ 11.68 (d, J=6.3 Hz, 1H), 11.61 (d, J=2.0 Hz, 1H), 8.66 (d, J=1.7 Hz, 1H), 8.49 (s, 1H), 8.28 (d, J=2.0 Hz, 1H), 8.13-8.06 (m, 2H), 7.78 (s, 1H), 5.39 (q, J=9.0 Hz, 2H), 3.10-2.98 (m, 2H), 2.18-2.16 (m, 1H), 2.02-2.00 (m, 1H).

Example 718. 5-[8-[(1S,2S)-2-[3,3-dimethyl-2-oxo-1-(2,2,2-trifluoroethyl)pyrrolo[3,2-c]pyridin-6-yl]cyclopropyl]imidazo[1,2-b]pyridazin-6-yl]-1H-pyrimidine-2,4-dione

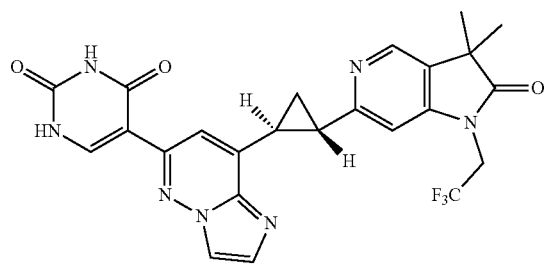 [SMILES: CC1(C)C(=O)N(CC(F)(F)F)c2cc([C@H]3C[C@@H]3c3cc(-c4c[nH]c(=O)[nH]c4=O)nn4ccnc34)ncc21]

5-[8-[(1S,2S)-2-[3,3-dimethyl-2-oxo-1-(2,2,2-trifluoroethyl)pyrrolo[3,2-c]pyridin-6-yl]cyclopropyl]imidazo[1,2-b]pyridazin-6-yl]-1H-pyrimidine-2,4-dione was chirally separated from the racemic mixture by SFC Cell 2 column (35% EtOH). ES/MS m/z: 512.20 [M+H]. 1H NMR (400 MHz, DMSO-d6) δ 11.55 (d, J=6.3 Hz, 2H), 8.63 (s, 1H), 8.31 (d, J=1.2 Hz, 1H), 8.03 (d, J=6.0 Hz, 1H), 7.80 (d, J=1.3 Hz, 1H), 7.62 (d, J=6.3 Hz, 2H), 4.73 (q, J=9.2 Hz, 2H), 3.26 (d, J=8.9 Hz, 1H), 3.03 (ddd, J=9.0, 6.3, 4.2 Hz, 1H), 2.34 (s, 1H), 2.04 (dt, J=9.9, 4.9 Hz, 1H), 1.41 (s, 6H).

Example 719. 5-[3-chloro-8-[(1S,2S)-2-[3-fluoro-1-(2,2,2-trifluoroethyl)pyrazolo[4,3-b]pyridin-6-yl]cyclopropyl]imidazo[1,2-b]pyridazin-6-yl]-1H-pyrimidine-2,4-dione

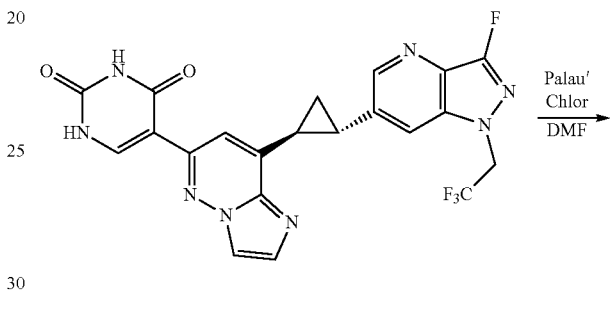

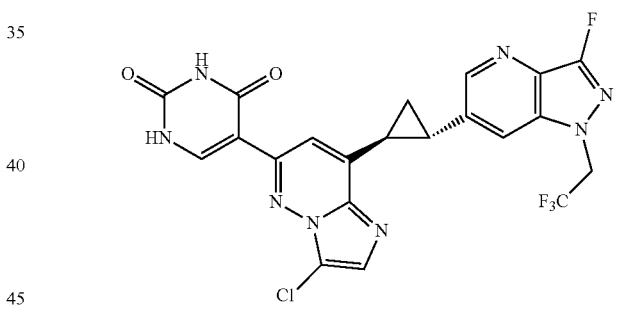

Palau'Chlor (8 mg, 0.04 mmoL, 1 equiv) was added to a solution of 5-[8-[(1S,2S)-2-[3-fluoro-1-(2,2,2-trifluoroethyl)pyrazolo[4,3-b]pyridin-6-yl]cyclopropyl]imidazo[1,2-b]pyridazin-6-yl]-1H-pyrimidine-2,4-dione;hydrochloride (20 mg, 0.04 mmol, 1 equiv) in DMF (1 mL). After 1 h, the reaction mixture was directly purified by RP-HPLC (10-80% MeCN/H$_2$O with TFA modifier), affording 5-[3-chloro-8-[(1S,2S)-2-[3-fluoro-1-(2,2,2-trifluoroethyl)pyrazolo[4,3-b]pyridin-6-yl]cyclopropyl]imidazo[1,2-b]pyridazin-6-yl]-1H-pyrimidine-2,4-dione. ES/MS m/z: 521.10 [M+H]. 1H NMR (400 MHz, DMSO-d6) δ 11.56 (s, 1H), 11.54 (d, J=2.1 Hz, 1H), 8.67 (d, J=1.7 Hz, 1H), 8.22 (d, J=2.1 Hz, 1H), 8.06 (d, J=6.1 Hz, 1H), 7.87 (s, 1H), 7.65 (s, 1H), 5.36 (q, J=8.5 Hz, 2H), 3.16 (ddd, J=9.0, 6.2, 4.4 Hz, 1H), 2.90 (ddd, J=9.1, 6.1, 4.4 Hz, 1H), 2.27 (dt, J=9.1, 5.4 Hz, 1H), 1.99-1.89 (m, 1H)

Example 720. Preparation of 5-[3-fluoro-8-[(1S, 2S)-2-[3-fluoro-1-(2,2,2-trifluoroethyl)pyrazolo[4,3-b]pyridin-6-yl]cyclopropyl]imidazo[1,2-b]pyridazin-6-yl]-1H-pyrimidine-2,4-dione

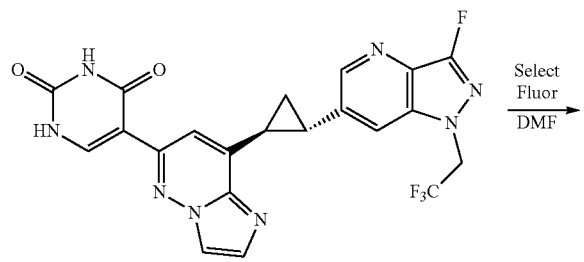

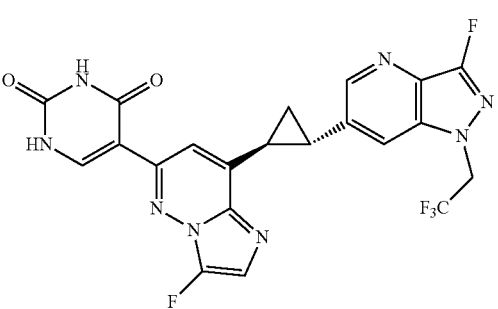

SelectFluor (24.5 mg, 0.069 mmoL, 1.3 equiv) was added to a solution of 5-[8-[(1S,2S)-2-[3-fluoro-1-(2,2,2-trifluoroethyl)pyrazolo[4,3-b]pyridin-6-yl]cyclopropyl]imidazo[1,2-b]pyridazin-6-yl]-1H-pyrimidine-2,4-dione;2,2,2-trifluoroacetic acid (32 mg, 0.05 mmol, 1 equiv) in DMF (1 mL). After 16 h, the reaction mixture was directly purified by RP-HPLC (10-80% MeCN/H₂O with TFA modifier), affording 5-[3-fluoro-8-[(1S,2S)-2-[3-fluoro-1-(2,2,2-trifluoroethyl)pyrazolo[4,3-b]pyridin-6-yl]cyclopropyl]imidazo[1,2-b]pyridazin-6-yl]-1H-pyrimidine-2,4-dione. ES/MS m/z: 505.10 [M+H]. 1H NMR (400 MHz, DMSO-d6) δ 11.58-11.52 (m, 2H), 8.67 (d, J=1.8 Hz, 1H), 8.22 (d, J=2.0 Hz, 1H), 8.08-8.01 (m, 1H), 7.60-7.53 (m, 2H), 5.36 (q, J=8.9 Hz, 2H), 3.17 (ddd, J=9.0, 6.2, 4.4 Hz, 1H), 2.86 (ddd, J=8.9, 6.0, 4.3 Hz, 1H), 2.27 (dt, J=9.1, 5.4 Hz, 1H), 1.98-1.88 (m, 1H).

Example 721. 5-[3-chloro-8-[(1S,2S)-2-[3-fluoro-1-(2,2,2-trifluoroethyl)indazol-6-yl]cyclopropyl]imidazo[1,2-b]pyridazin-6-yl]-1H-pyrimidine-2,4-dione

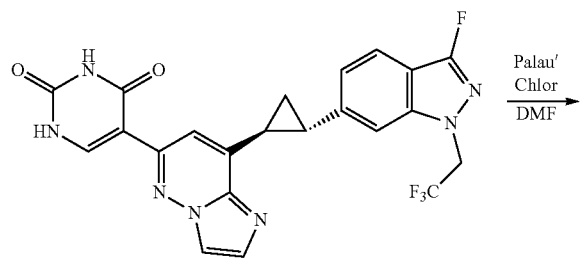

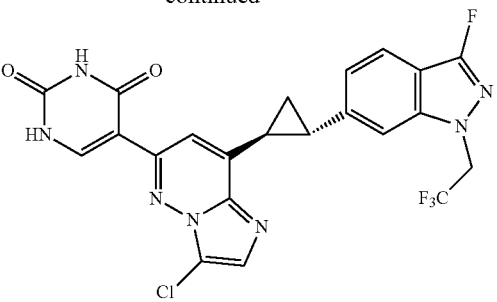

Palau'Chlor (21 mg, 0.1 mmoL, 1 equiv) was added to a solution of 5-[8-[(1S,2S)-2-[3-fluoro-1-(2,2,2-trifluoroethyl)indazol-6-yl]cyclopropyl]imidazo[1,2-b]pyridazin-6-yl]-1H-pyrimidine-2,4-dione;hydrochloride (52 mg, 0.1 mmol, 1 equiv) in DMF (1 mL). After 20 minutes, the reaction mixture was directly purified by RP-HPLC (15-95% MeCN/H₂O with TFA modifier), affording 5-[3-chloro-8-[(1S,2S)-2-[3-fluoro-1-(2,2,2-trifluoroethyl)indazol-6-yl]cyclopropyl]imidazo[1,2-b]pyridazin-6-yl]-1H-pyrimidine-2,4-dione. ES/MS m/z: 520.10 [M+H]. 1H NMR (400 MHz, DMSO-d6) δ 11.55 (d, J=5.7 Hz, 2H), 8.05 (d, J=6.1 Hz, 1H), 7.86 (s, 1H), 7.77-7.65 (m, 2H), 7.62 (s, 1H), 7.20 (dd, J=8.5, 1.3 Hz, 1H), 5.31 (q, J=9.0 Hz, 2H), 3.04 (ddd, J=9.0, 6.3, 4.4 Hz, 1H), 2.84 (ddd, J=8.9, 5.9, 4.4 Hz, 1H), 2.19 (ddd, J=8.9, 6.1, 4.8 Hz, 1H), 1.91 (ddd, J=8.8, 6.3, 4.8 Hz, 1H).

Example 722. 5-[3-chloro-8-[(1S,2S)-2-[3,3-dimethyl-2-oxo-1-(2,2,2-trifluoroethyl)indolin-6-yl]cyclopropyl]imidazo[1,2-b]pyridazin-6-yl]-1H-pyrimidine-2,4-dione

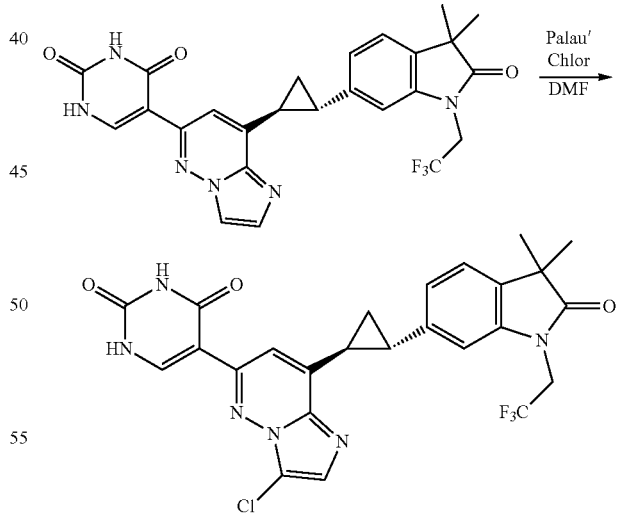

Palau'Chlor (8 mg, 0.04 mmol, 1 equiv) was added to a solution of 5-[8-[(1S,2S)-2-[3,3-dimethyl-2-oxo-1-(2,2,2-trifluoroethyl)indolin-6-yl]cyclopropyl]imidazo[1,2-b]pyridazin-6-yl]-1H-pyrimidine-2,4-dione;hydrochloride (20 mg, 0.04 mmol, 1 equiv) in DMF (1 mL). After 20 minutes, the reaction mixture was directly purified by RP-HPLC (10-90% MeCN/H₂O with TFA modifier), affording 5-[3-chloro-8-[(1S,2S)-2-[3,3-dimethyl-2-oxo-1-(2,2,2-trifluoroethyl)indolin-6-yl]cyclopropyl]imidazo[1,2-b]pyridazin-6-yl]-1H-pyrimidine-2,4-dione. ES/MS m/z: 545.20 [M+H]. 1H NMR (400 MHz, DMSO-d6) δ 11.54 (d, J=7.2 Hz, 2H), 8.05 (d, J=6.0 Hz, 1H), 7.85 (s, 1H), 7.56 (s, 1H), 7.31 (d, J=7.6 Hz, 1H), 7.13 (s, 1H), 7.01 (dd, J=7.7, 1.4 Hz, 1H), 4.63 (q, J=9.4 Hz, 2H), 2.94-2.67 (m, 2H), 2.16-2.07 (m, 1H), 1.89 1.79 (m, 1H), 1.30 (s, 6H).

Example 723. Preparation of 5-[8-[(1S,2S)-2-[3,3-dimethyl-2-oxo-1-(2,2,2-trifluoroethyl)pyrrolo[3,2-b]pyridin-6-yl]cyclopropyl]-3-fluoro-imidazo[1,2-b]pyridazin-6-yl]-1H-pyrimidine-2,4-dione

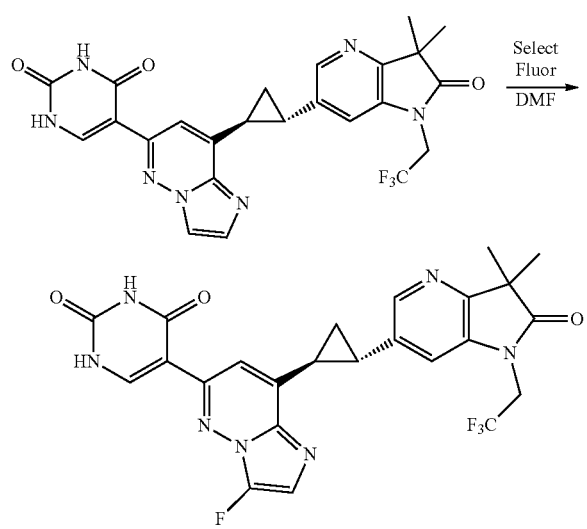

SelectFluor (33 mg, 0.093 mmoL, 1.3 equiv) was added to a solution of 5-[8-[(1S,2S)-2-[3,3-dimethyl-2-oxo-1-(2,2,2-trifluoroethyl)pyrrolo[3,2-b]pyridin-6-yl]cyclopropyl]imidazo[1,2-b]pyridazin-6-yl]-1H-pyrimidine-2,4-dione;2,2,2-trifluoroacetic acid (45 mg, 0.07 mmol, 1 equiv) in DMF (1 mL). After 16 h, the reaction mixture was directly purified by RP-HPLC (10-80% MeCN/H$_2$O with TFA modifier), affording 5-[8-[(1S,2S)-2-[3,3-dimethyl-2-oxo-1-(2,2,2-trifluoroethyl)pyrrolo[3,2-b]pyridin-6-yl]cyclopropyl]-3-fluoro-imidazo[1,2-b]pyridazin-6-yl]-1H-pyrimidine-2,4-dione. ES/MS m/z: 530.20 [M+H]. 1H NMR (400 MHz, DMSO-d6) δ 11.55 (d, J=3.7 Hz, 2H), 8.21 (d, J=1.6 Hz, 1H), 8.04 (d, J=6.4 Hz, 1H), 7.60-7.48 (m, 3H), 4.67 (q, J=9.4 Hz, 2H), 2.95 (ddd, J=9.5, 6.2, 4.4 Hz, 1H), 2.76 (dt, J=10.0, 5.4 Hz, 1H), 2.23-2.13 (m, 1H), 1.89-1.74 (m, 1H), 1.31 (s, 6H).

Example 724. Preparation of (S)-5-(8-(4-(6-(difluoromethyl)pyridin-2-yl)oxy)-3,3-difluoropyrrolidin-1-yl)-3-fluoroimidazo[1,2-b]pyridazin-6-yl)pyrimidine-2,4(1H,3H)-dione

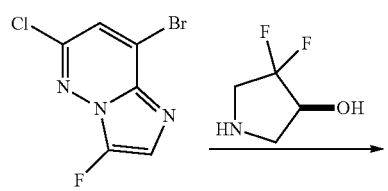

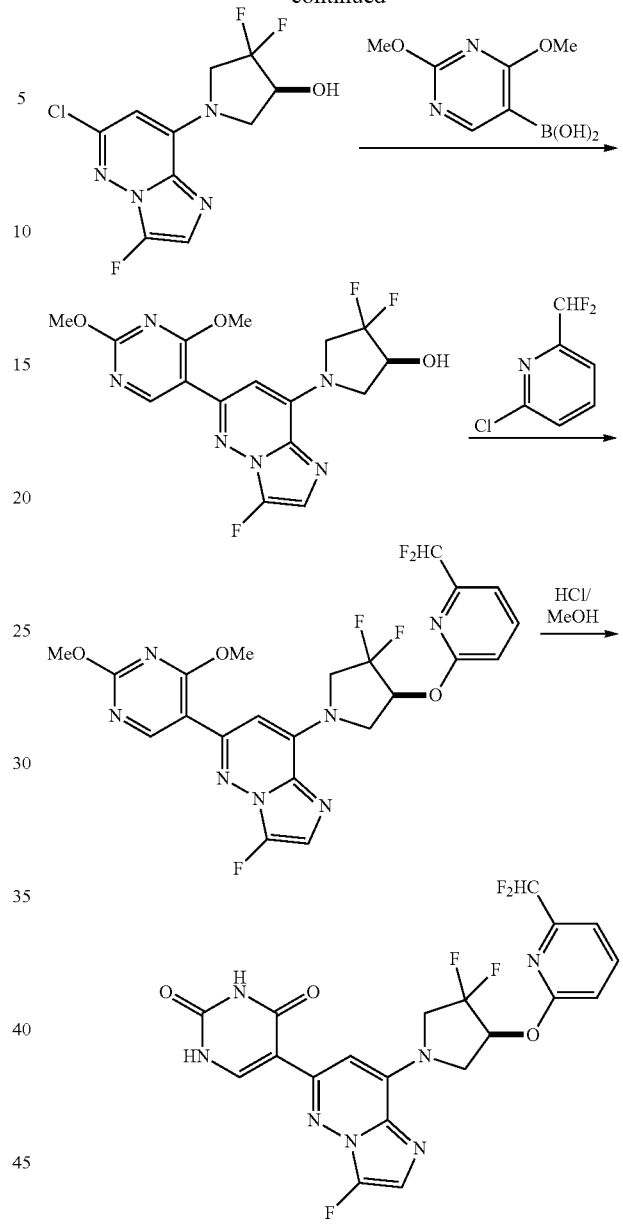

Step 1: A solution of 8-bromo-6-chloro-3-fluoroimidazo[1,2-b]pyridazine (2238 mg, 8.94 mmol, 1.1 equiv), (S)-4,4-difluoropyrrolidin-3-ol hydrochloride (1000 mg, 8.12 mmol, 1 equiv), DIPEA (3.40 mL, 19.5 mmol, 2.4 equiv), and MeCN (20 mL) was heated to 85 C. After 20 hours, the reaction mixture was concentrated and directly purified by SiO$_2$ chromatography (0-100% EtOAc/Hex), affording (S)-1-(6-chloro-3-fluoroimidazo[1,2-b]pyridazin-8-yl)-4,4-difluoropyrrolidin-3-ol. ES/MS m/z: 293.10 [M+H].

Step 2: A solution of (S)-1-(6-chloro-3-fluoroimidazo[1,2-b]pyridazin-8-yl)-4,4-difluoropyrrolidin-3-ol (2330 mg, 7.96 mmol, 1 equiv), (2,4-dimethoxypyrimidin-5-yl)boronic acid (1611 mg, 8.76 mol, 1.1 equiv), cesium carbonate (5188 mg, 15.9 mmol, 2 equiv), and (dppf)-PdCl$_2$—CH$_2$Cl$_2$ (291 mg, 5 mol %) in 1:4 water/1,4-dioxane (40 mL) was heated to 80 C. After 24 hours, the reaction mixture was cooled to room temperature. The layers were separated, and the aqueous layer was extracted with EtOAc (3×200 mL). The combined organic layers were dried over Na₂SO₄, filtered, and concentrated. Purification was accomplished by SiO₂ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-ol. ES/MS m/z: 397.20 [M+H].

Step 3: To a cooled (0 C) solution (S)-1-(6-(2,4-dimethoxypyrimidin-5-yl)-3-fluoroimidazo[1,2-b]pyridazin-8-yl)-4,4-difluoropyrrolidin-3-ol (50 mg, 0.13 mmol, 1 equiv) in DMF (1 mL) was added 60% sodium hydride (5.8 mg, 0.25 mmol, 2 equiv). After 10 minutes, 2-chloro-6-(difluoromethyl)pyridine (62 mg, 0.38 mmol, 3 equiv) was added, and the reaction mixture was heated to 80 C. After 1 hour, the reaction mixture was quenched with water at 0° C. and directly purified by SiO₂ chromatography (0-100% EtOAc/Hex), affording (S)-8-(4-(((6-(difluoromethyl)pyridin-2-yl)oxy)-3,3-difluoropyrrolidin-1-yl)-6-(2,4-dimethoxypyrimidin-5-yl)-3-fluoroimidazo[1,2-b]pyridazine. ES/MS m/z: 524.10 [M+H].

Step 4: A solution of (S)-8-(4-(((6-(difluoromethyl)pyridin-2-yl)oxy)-3,3-difluoropyrrolidin-1-yl)-6-(2,4-dimethoxypyrimidin-5-yl)-3-fluoroimidazo[1,2-b]pyridazine (10 mg) in 1:1 1N HCl:MeOH (2 mL) was heated to 80 C. After 6 hours, the reaction mixture was directly purified by RP-HPLC (10-90% MeCN/H₂O with TFA modifier), affording (S)-5-(8-(4-(((6-(difluoromethyl)pyridin-2-yl)oxy)-3,3-difluoropyrrolidin-1-yl)-3-fluoroimidazo[1,2-b]pyridazin-6-yl)pyrimidine-2,4(1H,3H)-dione. ES/MS m/z: 496.10 [M+H]. 1H NMR (400 MHz, Methanol-d4) δ 8.11 (s, 1H), 7.90 (t, J=7.8 Hz, 1H), 7.36 (d, J=7.4 Hz, 1H), 7.23 (d, J=7.0 Hz, 1H), 7.05 (d, J=8.4 Hz, 1H), 6.72 (s, 1H), 6.66 (t, J=55.3 Hz, 1H), 6.04-5.89 (m, 1H), 4.69-4.16 (m, 4H). 19F NMR (376 MHz, Methanol-d4) δ −77.74, −109.55-−119.07 (m), −118.63 (dd, J=55.3, 13.9 Hz), −123.69-−124.60 (m), −157.71 (d, J=7.0 Hz).

Example 725. Preparation of (S)-5-(8-(4-((2-(difluoromethyl)pyridin-4-yl)oxy)-3,3-difluoropyrrolidin-1-yl)-3-fluoroimidazo[1,2-b]pyridazin-6-yl)pyrimidine-2,4(1H,3H)-dione

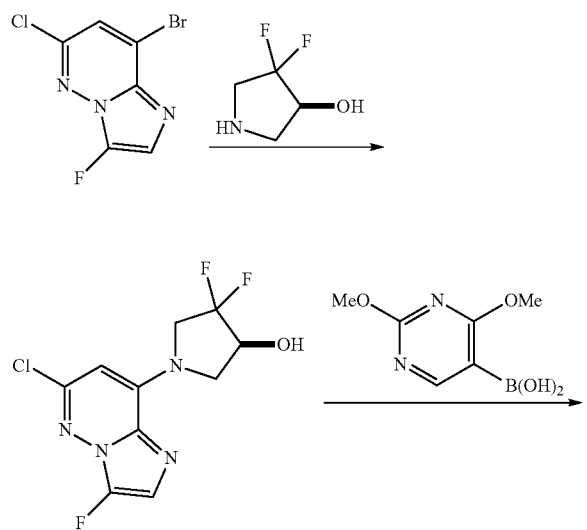

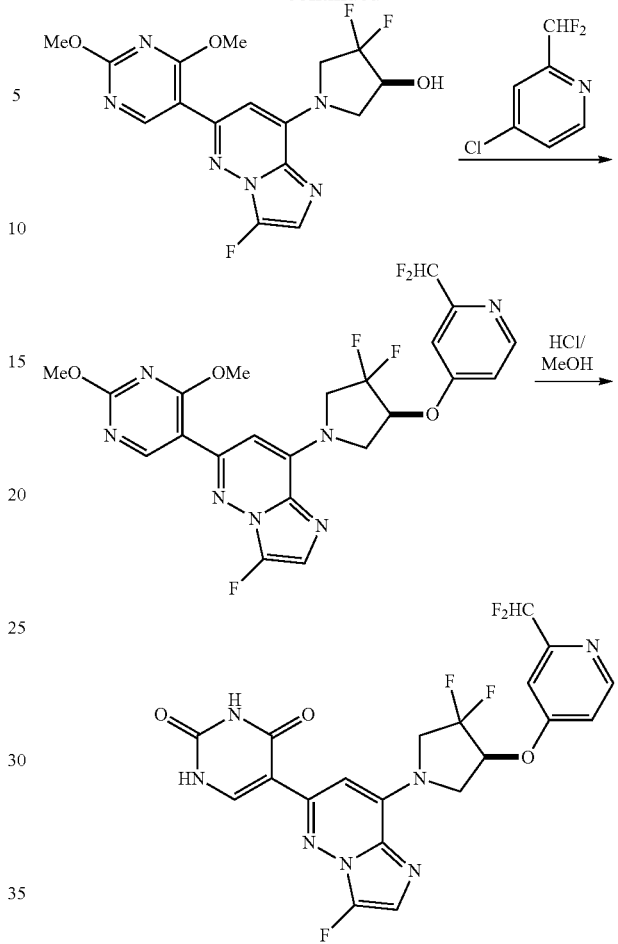

Step 1: A solution of 8-bromo-6-chloro-3-fluoroimidazo[1,2-b]pyridazine (2238 mg, 8.94 mmol, 1.1 equiv), (S)-4,4-difluoropyrrolidin-3-ol hydrochloride (1000 mg, 8.12 mmol, 1 equiv), DIPEA (3.40 mL, 19.5 mmol, 2.4 equiv), and MeCN (20 mL) was heated to 85 C. After 20 hours, the reaction mixture was concentrated and directly purified by SiO₂ chromatography (0-100% EtOAc/Hex), affording (S)-1-(6-chloro-3-fluoroimidazo[1,2-b]pyridazin-8-yl)-4,4-difluoropyrrolidin-3-ol. ES/MS m/z: 293.10 [M+H].

Step 2: A solution of (S)-1-(6-chloro-3-fluoroimidazo[1,2-b]pyridazin-8-yl)-4,4-difluoropyrrolidin-3-ol (2330 mg, 7.96 mmol, 1 equiv), (2,4-dimethoxypyrimidin-5-yl)boronic acid (1611 mg, 8.76 mol, 1.1 equiv), cesium carbonate (5188 mg, 15.9 mmol, 2 equiv), and (dppf)-PdCl₂—CH₂Cl₂ (291 mg, 5 mol %) in 1:4 water/1,4-dioxane (40 mL) was heated to 80 C. After 24 hours, the reaction mixture was cooled to room temperature. The layers were separated, and the aqueous layer was extracted with EtOAc (3×200 mL). The combined organic layers were dried over Na₂SO₄, filtered, and concentrated. Purification was accomplished by SiO₂ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-ol. ES/MS m/z: 397.20 [M+H].

Step 3: To a cooled (0 C) solution (S)-1-(6-(2,4-dimethoxypyrimidin-5-yl)-3-fluoroimidazo[1,2-b]pyridazin-8-yl)-4,4-difluoropyrrolidin-3-ol (50 mg, 0.13 mmol, 1 equiv) in DMF (1 mL) was added 60% sodium hydride (5.8 mg, 0.25 mmol, 2 equiv). After 10 minutes, 4-chloro-2-(difluoromethyl)pyridine (62 mg, 0.38 mmol, 3 equiv) was added, and the reaction mixture was heated to 80 C. After 1 hour, the reaction mixture was quenched with water at 0° C. and directly purified by SiO₂ chromatography (0-100% EtOAc/Hex), affording (S)-8-(4-((2-(difluoromethyl)pyridin-4-yl)oxy)-3,3-difluoropyrrolidin-1-yl)-6-(2,4-dimethoxypyrimidin-5-yl)-3-fluoroimidazo[1,2-b]pyridazine. ES/MS m/z: 524.10 [M+H].

Step 4: A solution of (S)-8-(4-((2-(difluoromethyl)pyridin-4-yl)oxy)-3,3-difluoropyrrolidin-1-yl)-6-(2,4-dimethoxypyrimidin-5-yl)-3-fluoroimidazo[1,2-b]pyridazine (60 mg) in 1:1 1N HCl:MeOH (2 mL) was heated to 80 C. After 20 hours, the reaction mixture was directly purified by RP-HPLC (10-90% MeCN/H₂O with TFA modifier), affording (S)-5-(8-(4-((2-(difluoromethyl)pyridin-4-yl)oxy)-3,3-difluoropyrrolidin-1-yl)-3-fluoroimidazo[1,2-b]pyridazin-6-yl)pyrimidine-2,4(1H,3H)-dione. ES/MS m/z: 496.00 [M+H]. 1H NMR (400 MHz, Methanol-d4) δ 8.53 (d, J=5.8 Hz, 1H), 8.12 (s, 1H), 7.42 (d, J=2.6 Hz, 1H), 7.31-7.27 (m, 1H), 7.24 (d, J=7.1 Hz, 1H), 6.75 (s, 1H), 6.71 (t, J=55.0 Hz, 1H), 5.60-5.49 (m, 1H), 4.68-4.27 (m, 4H). 19F NMR (376 MHz, Methanol-d4) δ −78.09, −108.06-−119.07 (m), −118.79 (dd, J=55.0, 2.9 Hz), −123.23-−124.01 (m), −157.63 (d, J=7.1 Hz).

Example 726. Preparation of (S)-5-(8-(3,3-difluoro-4-((2-(trifluoromethyl)pyridin-4-yl)oxy)pyrrolidin-1-yl)-3-fluoroimidazo[1,2-b]pyridazin-6-yl)pyrimidine-2,4(1H,3H)-dione

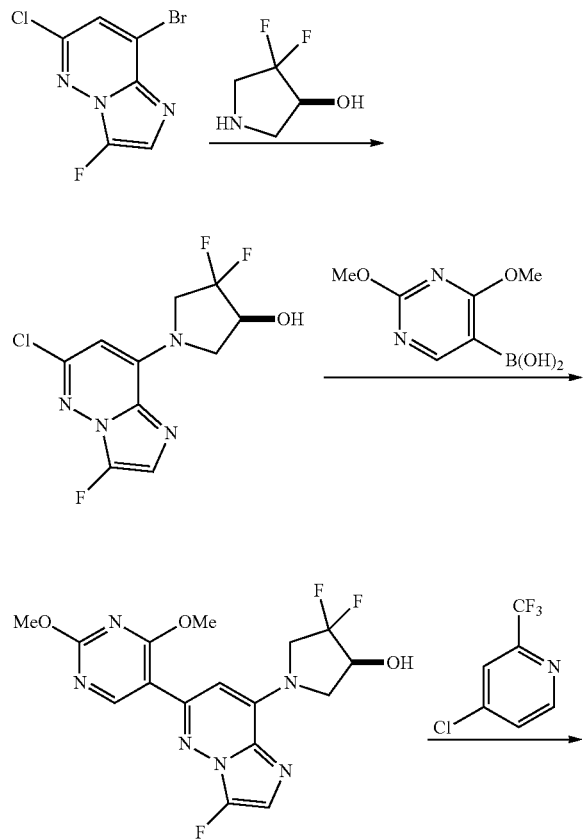

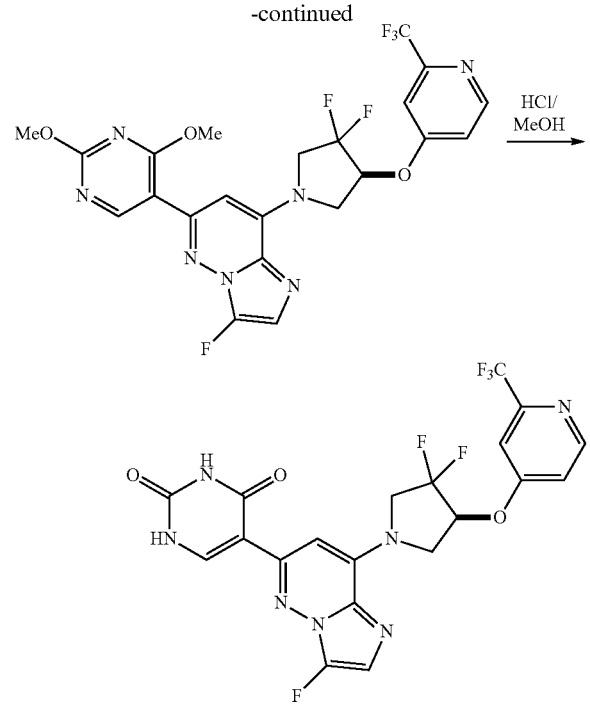

Step 1: A solution of 8-bromo-6-chloro-3-fluoroimidazo[1,2-b]pyridazine (2238 mg, 8.94 mmol, 1.1 equiv), (S)-4,4-difluoropyrrolidin-3-ol hydrochloride (1000 mg, 8.12 mmol, 1 equiv), DIPEA (3.40 mL, 19.5 mmol, 2.4 equiv), and MeCN (20 mL) was heated to 85 C. After 20 hours, the reaction mixture was concentrated and directly purified by SiO₂ chromatography (0-100% EtOAc/Hex), affording (S)-1-(6-chloro-3-fluoroimidazo[1,2-b]pyridazin-8-yl)-4,4-difluoropyrrolidin-3-ol. ES/MS m/z: 293.10 [M+H].

Step 2: A solution of (S)-1-(6-chloro-3-fluoroimidazo[1,2-b]pyridazin-8-yl)-4,4-difluoropyrrolidin-3-ol (2330 mg, 7.96 mmol, 1 equiv), (2,4-dimethoxypyrimidin-5-yl)boronic acid (1611 mg, 8.76 mol, 1.1 equiv), cesium carbonate (5188 mg, 15.9 mmol, 2 equiv), and (dppf)-PdCl₂—CH₂Cl₂ (291 mg, 5 mol %) in 1:4 water/1,4-dioxane (40 mL) was heated to 80 C. After 24 hours, the reaction mixture was cooled to room temperature. The layers were separated, and the aqueous layer was extracted with EtOAc (3×200 mL). The combined organic layers were dried over Na₂SO₄, filtered, and concentrated. Purification was accomplished by SiO₂ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-ol. ES/MS m/z: 397.20 [M+H].

Step 3: To a cooled (0 C) solution (S)-1-(6-(2,4-dimethoxypyrimidin-5-yl)-3-fluoroimidazo[1,2-b]pyridazin-8-yl)-4,4-difluoropyrrolidin-3-ol (100 mg, 0.25 mmol, 1 equiv) in DMF (1 mL) was added 60% sodium hydride (12 mg, 0.51 mmol, 2 equiv). After 10 minutes, 4-chloro-2-(trifluoromethyl)pyridine (137 mg, 0.76 mmol, 3 equiv) was added, and the reaction mixture was heated to 80 C. After 1 hour, the reaction mixture was quenched with water at 0° C. and directly purified by SiO₂ chromatography (0-100% EtOAc/Hex), affording (S)-8-(3,3-difluoro-4-((2-(trifluoromethyl)pyridin-4-yl)oxy)pyrrolidin-1-yl)-6-(2,4-dimethoxypyrimidin-5-yl)-3-fluoroimidazo[1,2-b]pyridazine. ES/MS m/z: 542.10 [M+H].

Step 4: A solution of (S)-8-(3,3-difluoro-4-((2-(trifluoromethyl)pyridin-4-yl)oxy)pyrrolidin-1-yl)-6-(2,4-dimethoxypyrimidin-5-yl)-3-fluoroimidazo[1,2-b]pyridazine (110 mg) in 1:1 1N HCl:MeOH (2 mL) was heated to 80 C. After 14 hours, the reaction mixture was directly purified by RP-HPLC (10-90% MeCN/H$_2$O with TFA modifier), affording (S)-5-(8-(3,3-difluoro-4-((2-(trifluoromethyl)pyridin-4-yl)oxy)pyrrolidin-1-yl)-3-fluoroimidazo[1,2-b]pyridazin-6-yl)pyrimidine-2,4(1H,3H)-dione. ES/MS m/z: 514.10 [M+H]. 1H NMR (400 MHz, Methanol-d4) δ 8.60 (d, J=5.8 Hz, 1H), 8.12 (s, 1H), 7.54 (d, J=2.5 Hz, 1H), 7.38 (dd, J=5.8, 2.5 Hz, 1H), 7.24 (d, J=7.1 Hz, 1H), 6.75 (s, 1H), 5.64-5.52 (m, 1H), 4.68-4.28 (m, 4H). 19F NMR (376 MHz, Methanol-d4) δ −70.19, −107.91-−108.98 (m), −123.16-−124.07 (m), −157.65 (d, J=7.0 Hz).

Example 727. Preparation of (S)-5-(8-(3,3-difluoro-4-(6-(trifluoromethyl)pyrimidin-4-yl)oxy)pyrrolidin-1-yl)-3-fluoroimidazo[1,2-b]pyridazin-6-yl)pyrimidine-2,4(1H,3H)-dione

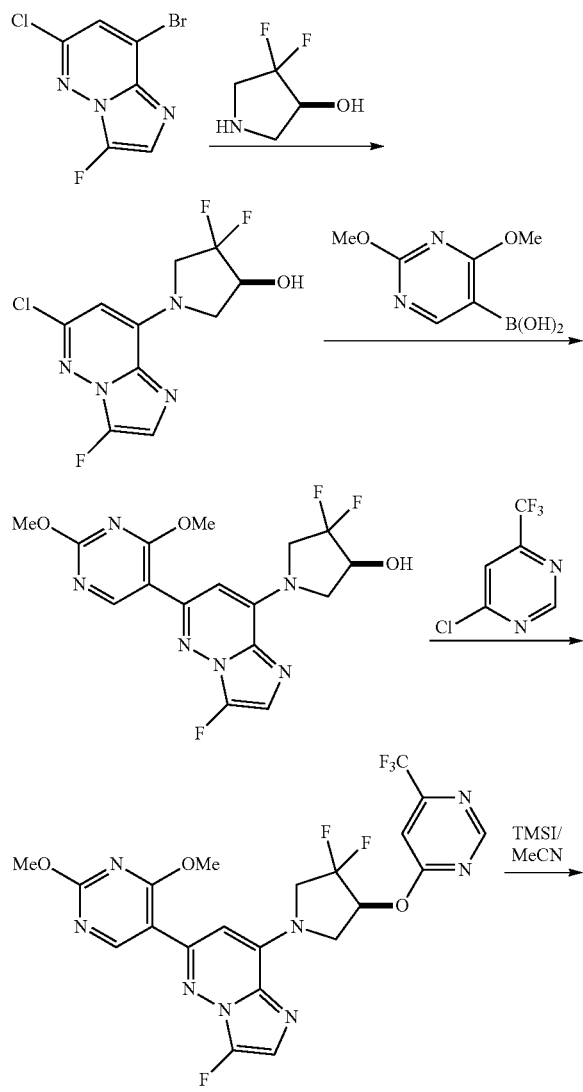

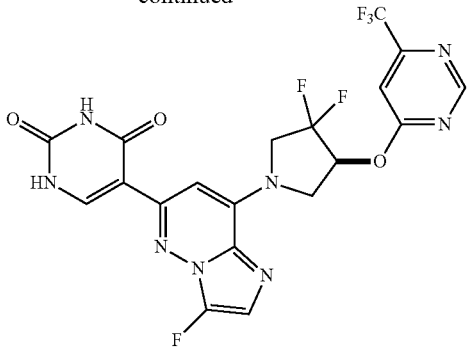

Step 1: A solution of 8-bromo-6-chloro-3-fluoroimidazo[1,2-b]pyridazine (2238 mg, 8.94 mmol, 1.1 equiv), (S)-4,4-difluoropyrrolidin-3-ol hydrochloride (1000 mg, 8.12 mmol, 1 equiv), DIPEA (3.40 mL, 19.5 mmol, 2.4 equiv), and MeCN (20 mL) was heated to 85 C. After 20 hours, the reaction mixture was concentrated and directly purified by SiO$_2$ chromatography (0-100% EtOAc/Hex), affording (S)-1-(6-chloro-3-fluoroimidazo[1,2-b]pyridazin-8-yl)-4,4-difluoropyrrolidin-3-ol. ES/MS m/z: 293.10 [M+H].

Step 2: A solution of (S)-1-(6-chloro-3-fluoroimidazo[1,2-b]pyridazin-8-yl)-4,4-difluoropyrrolidin-3-ol (2330 mg, 7.96 mmol, 1 equiv), (2,4-dimethoxypyrimidin-5-yl)boronic acid (1611 mg, 8.76 mol, 1.1 equiv), cesium carbonate (5188 mg, 15.9 mmol, 2 equiv), and (dppf)-PdCl$_2$—CH$_2$Cl$_2$ (291 mg, 5 mol %) in 1:4 water/1,4-dioxane (40 mL) was heated to 80 C. After 24 hours, the reaction mixture was cooled to room temperature. The layers were separated, and the aqueous layer was extracted with EtOAc (3×200 mL). The combined organic layers were dried over Na$_2$SO$_4$, filtered, and concentrated. Purification was accomplished by SiO$_2$ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-ol. ES/MS m/z: 397.20 [M+H].

Step 3: To a cooled (0 C) solution (S)-1-(6-(2,4-dimethoxypyrimidin-5-yl)-3-fluoroimidazo[1,2-b]pyridazin-8-yl)-4,4-difluoropyrrolidin-3-ol (50 mg, 0.13 mmol, 1 equiv) in DMF (1 mL) was added 60% sodium hydride (5.8 mg, 0.25 mmol, 2 equiv). After 10 minutes, 4-chloro-6-(trifluoromethyl)pyrimidine (69 mg, 0.38 mmol, 3 equiv) was added, and the reaction mixture was heated to 80 C. After 1 hour, the reaction mixture was quenched with water at 0° C. and directly purified by SiO$_2$ chromatography (0-100% EtOAc/Hex), affording (S)-8-(3,3-difluoro-4-((6-(trifluoromethyl)pyrimidin-4-yl)oxy)pyrrolidin-1-yl)-6-(2,4-dimethoxypyrimidin-5-yl)-3-fluoroimidazo[1,2-b]pyridazine. ES/MS m/z: 543.00 [M+H].

Step 4: To a solution of (S)-8-(3,3-difluoro-4-((6-(trifluoromethyl)pyrimidin-4-yl)oxy)pyrrolidin-1-yl)-6-(2,4-dimethoxypyrimidin-5-yl)-3-fluoroimidazo[1,2-b]pyridazine (55 mg) in MeCN (1 mL) was added iodotrimethylsilane (0.14 mL). After 1 hour, the reaction mixture was quenched with water at 0° C. and directly purified by RP-HPLC (10-90% MeCN/H$_2$O with TFA modifier), affording (S)-5-(8-(3,3-difluoro-4-((6-(trifluoromethyl)pyrimidin-4-yl)oxy)pyrrolidin-1-yl)-3-fluoroimidazo[1,2-b]pyridazin-6-yl)pyrimidine-2,4(1H,3H)-dione. ES/MS m/z: 515.10 [M+H]. 1H NMR (400 MHz, Methanol-d4) δ 8.99 (s, 1H), 8.12 (s, 1H), 7.46 (d, J=0.9 Hz, 1H), 7.24 (d, J=7.1 Hz, 1H), 6.75 (s, 1H), 6.16-6.05 (m, 1H), 4.71-4.26 (m, 4H). 19F NMR (376 MHz, Methanol-d4) δ −72.23, −78.22, −108.88—109.95 (m), −122.74—124.16 (m), −157.61 (d, J=7.0 Hz).

Example 728. Preparation of (S)-5-(8-(3,3-difluoro-4-((2-(trifluoromethyl)pyrimidin-4-yl)oxy)pyrrolidin-1-yl)-3-fluoroimidazo[1,2-b]pyridazin-6-yl)pyrimidine-2,4(1H,3H)-dione

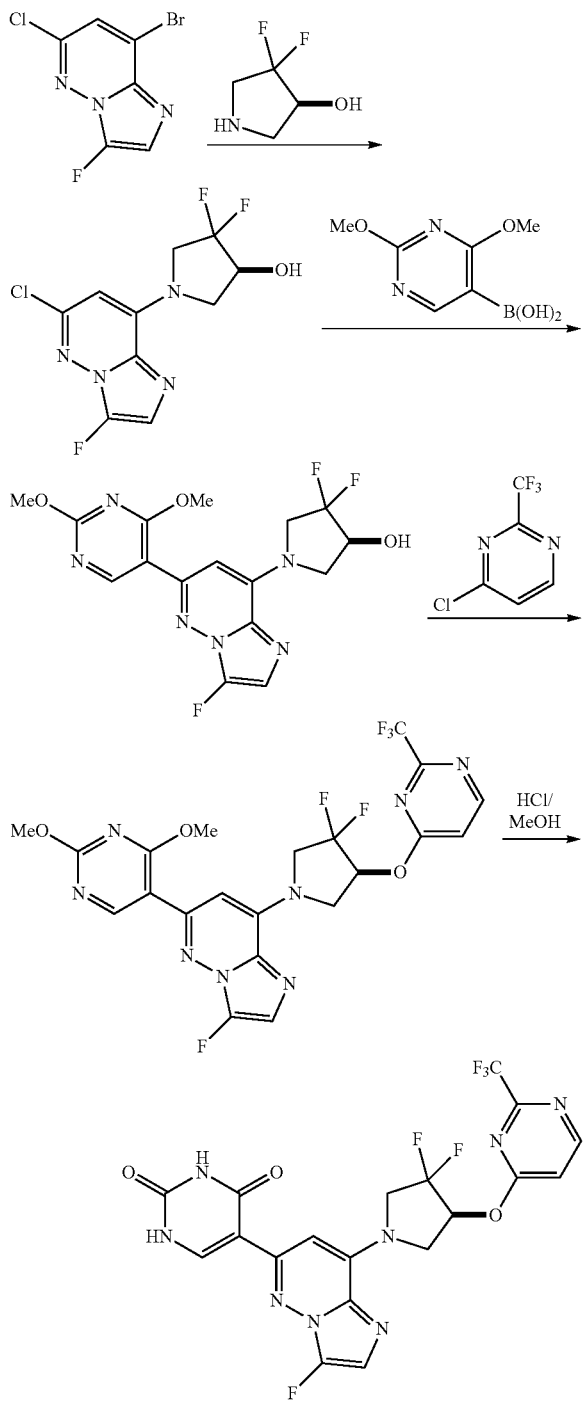

Step 1: A solution of 8-bromo-6-chloro-3-fluoroimidazo[1,2-b]pyridazine (2238 mg, 8.94 mmol, 1.1 equiv), (S)-4,4-difluoropyrrolidin-3-ol hydrochloride (1000 mg, 8.12 mmol, 1 equiv), DIPEA (3.40 mL, 19.5 mmol, 2.4 equiv), and MeCN (20 mL) was heated to 85 C. After 20 hours, the reaction mixture was concentrated and directly purified by SiO₂ chromatography (0-100% EtOAc/Hex), affording (S)-1-(6-chloro-3-fluoroimidazo[1,2-b]pyridazin-8-yl)-4,4-difluoropyrrolidin-3-ol. ES/MS m/z: 293.10 [M+H].

Step 2: A solution of (S)-1-(6-chloro-3-fluoroimidazo[1,2-b]pyridazin-8-yl)-4,4-difluoropyrrolidin-3-ol (2330 mg, 7.96 mmol, 1 equiv), (2,4-dimethoxypyrimidin-5-yl)boronic acid (1611 mg, 8.76 mol, 1.1 equiv), cesium carbonate (5188 mg, 15.9 mmol, 2 equiv), and (dppf)-PdCl₂—CH₂Cl₂ (291 mg, 5 mol %) in 1:4 water/1,4-dioxane (40 mL) was heated to 80° C. After 24 hours, the reaction mixture was cooled to room temperature. The layers were separated, and the aqueous layer was extracted with EtOAc (3×200 mL). The combined organic layers were dried over Na₂SO₄, filtered, and concentrated. Purification was accomplished by SiO₂ chromatography (0-100% EtOAc/Hex), affording (S)-1-(6-(2,4-dimethoxypyrimidin-5-yl)-3-fluoroimidazo[1,2-b]pyridazin-8-yl)-4,4-difluoropyrrolidin-3-ol. ES/MS m/z: 397.20 [M+H].

Step 3: To a cooled (0 C) solution (S)-1-(6-(2,4-dimethoxypyrimidin-5-yl)-3-fluoroimidazo[1,2-b]pyridazin-8-yl)-4,4-difluoropyrrolidin-3-ol (50 mg, 0.13 mmol, 1 equiv) in DMF (1 mL) was added 60% sodium hydride (5.8 mg, 0.25 mmol, 2 equiv). After 10 minutes, 4-chloro-2-(trifluoromethyl)pyrimidine (69 mg, 0.38 mmol, 3 equiv) was added, and the reaction mixture was heated to 80 C. After 1 hour, the reaction mixture was quenched with water at 0° C. and directly purified by SiO₂ chromatography (0-100% EtOAc/Hex), affording (S)-8-(3,3-difluoro-4-((2-(trifluoromethyl)pyrimidin-4-yl)oxy)pyrrolidin-1-yl)-6-(2,4-dimethoxypyrimidin-5-yl)-3-fluoroimidazo[1,2-b]pyridazine. ES/MS m/z: 543.10 [M+H].

Step 4: A solution of (S)-8-(3,3-difluoro-4-((2-(trifluoromethyl)pyrimidin-4-yl)oxy)pyrrolidin-1-yl)-6-(2,4-dimethoxypyrimidin-5-yl)-3-fluoroimidazo[1,2-b]pyridazine (55 mg) in 1:1 1N HCl:MeOH (2 mL) was heated to 80 C. After 6 hours, the reaction mixture was directly purified by RP-HPLC (10-90% MeCN/H₂O with TFA modifier), affording (S)-5-(8-(3,3-difluoro-4-((2-(trifluoromethyl)pyrimidin-4-yl)oxy)pyrrolidin-1-yl)-3-fluoroimidazo[1,2-b]pyridazin-6-yl)pyrimidine-2,4(1H,3H)-dione. ES/MS m/z: 515.10 [M+H]. 1H NMR (400 MHz, Methanol-d4) δ 8.75 (d, J=5.8 Hz, 1H), 8.12 (s, 1H), 7.25 (d, J=7.0 Hz, 1H), 7.24 (d, J=5.8 Hz, 1H), 6.75 (s, 1H), 6.12-6.03 (m, 1H), 4.70-4.54 (m, 1H), 4.54-4.30 (m, 3H). 19F NMR (376 MHz, Methanol-d4) δ −72.90, −78.25, −108.98—110.32 (m), −122.69—124.37 (m), −157.62 (d, J=7.0 Hz).

Example 729. Preparation of 5-(7-((1S,2S)-2-(4-fluoro-1-(2,2,2-trifluoroethyl)-1H-indazol-6-yl)cyclopropyl)pyrazolo[1,5-a]pyrimidin-5-yl)pyrimidine-2,4(1H,3H)-dione

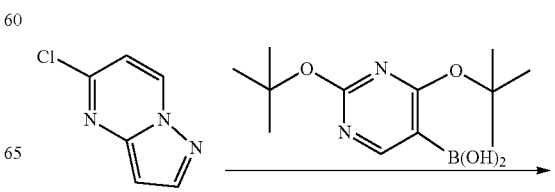

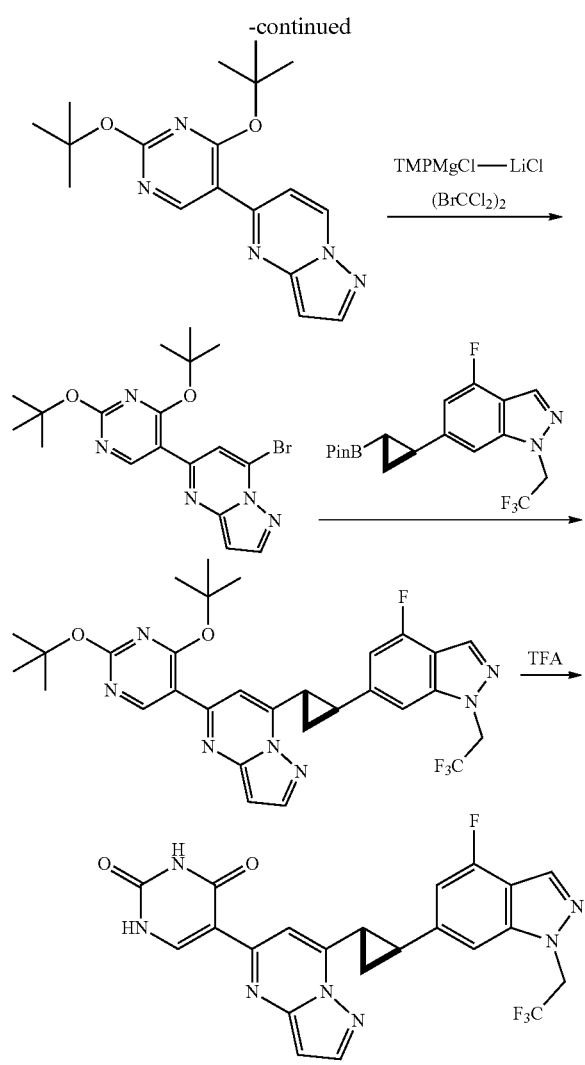

Step 1: To a solution of 5-chloropyrazolo[1,5-a]pyrimidine (1000 mg, 6.51 mmol, 1 equiv) and (2,4-di-tert-butoxypyrimidin-5-yl)boronic acid (1746 mg, 6.51 mmol, 1 equiv) in 4:1 1,4-dioxane:H$_2$O (30 mL) was added cesium carbonate (5304 mg, 16.3 mmol, 2.5 equiv) and (dppf)-PdCl$_2$—CH$_2$Cl$_2$ (238 mg, 5 mol %). The reaction mixture was heated to 80 C. After 2 hours, the reaction mixture was filtered, concentrated and directly purified by SiO$_2$ chromatography (0-100% EtOAc/Hex), affording 5-(2,4-di-tert-butoxypyrimidin-5-yl)pyrazolo[1,5-a]pyrimidine. $^1$H NMR (400 MHz, DMSO-d6) δ 9.10 (d, J=7.4 Hz, 1H), 8.79 (s, 1H), 8.22 (d, J=2.3 Hz, 1H), 7.46 (d, J=7.4 Hz, 1H), 6.72 (d, J=2.3 Hz, 1H), 1.66 (s, 9H), 1.61 (s, 9H).

Step 2: To a cooled (−78 C) solution of 5-(2,4-di-tert-butoxypyrimidin-5-yl)pyrazolo[1,5-a]pyrimidine (200 mg, 0.59 mmol, 1 equiv) in THF (1.5 mL) was added a 1M THF/Toluene solution of TMPMgCl·LiCl (0.70 mL, 0.70 mmol, 1.2 equiv). After 15 minutes at −78 C, a solution of 1,2-dibromotetrachloroethane (286 mg, 0.88 mmol, 1.5 equiv) in THF (1 mL) was added dropwise. The reaction mixture was gradually allowed to warm to room temperature over two hours. At t=5 hours, the reaction mixture was quenched with saturated aqueous NH$_4$Cl and directly purified by SiO$_2$ chromatography (0-100% EtOAc/Hex), affording 7-bromo-5-(2,4-di-tert-butoxypyrimidin-5-yl)pyrazolo[1,5-a]pyrimidine. $^1$H NMR (400 MHz, DMSO-d6) δ 8.83 (s, 1H), 8.34 (d, J=2.4 Hz, 1H), 7.90 (s, 1H), 6.93 (d, J=2.4 Hz, 1H), 1.67 (s, 9H), 1.61 (s, 9H).

Step 3: A degassed solution of 7-bromo-5-(2,4-di-tert-butoxypyrimidin-5-yl)pyrazolo[1,5-a]pyrimidine (30 mg, 0.071 mmol, 1 equiv), 4-fluoro-6-((2S,2S)-2-(4,4,5,5-tetramethyl-1,3,2-dioxaborolan-2-yl)cyclopropyl)-1-(2,2,2-trifluoroethyl)-1H-indazole (55 mg, 0.14 mmol, 2 equiv), potassium phosphate tribasic (30 mg, 0.14 mmol, 2 equiv), and cataCXium A Pd G3 (10 mg, 20 mol %) in 3:1 1,4-dioxane:H$_2$O (1 mL) was heated to 90 C. After 3 hours, the reaction mixture was directly purified by SiO$_2$ chromatography (0-100% EtOAc/Hex), affording 5-(2,4-di-tert-butoxypyrimidin-5-yl)-7-((2S,2S)-2-(4-fluoro-1-(2,2,2-trifluoroethyl)-1H-indazol-6-yl)cyclopropyl)pyrazolo[1,5-a]pyrimidine. ES/MS m/z: 486.10 [M+H], product mass minus tert-butyl groups.

Step 4: To a cooled (0 C) solution of 5-(2,4-di-tert-butoxypyrimidin-5-yl)-7-((2S,2S)-2-(4-fluoro-1-(2,2,2-trifluoroethyl)-1H-indazol-6-yl)cyclopropyl)pyrazolo[1,5-a]pyrimidine in 1:1 H$_2$O/MeCN (2 mL) was added 10 drops of TFA. After 30 minutes, the reaction mixture was purified by RP-HPLC (10-90% MeCN/H$_2$O with TFA modifier), affording 5-(7-((2S,2S)-2-(4-fluoro-1-(2,2,2-trifluoroethyl)-1H-indazol-6-yl)cyclopropyl)pyrazolo[1,5-a]pyrimidin-5-yl)pyrimidine-2,4(1H,3H)-dione. ES/MS m/z: 486.10 [M+H]. 1H NMR (400 MHz, Methanol-d4) δ 8.45 (s, 1H), 8.16-8.12 (m, 1H), 7.70 (s, 1H), 7.48 (s, 1H), 6.94 (d, J=11.0 Hz, 1H), 6.64 (d, J=2.4 Hz, 1H), 5.22 (q, J=8.8 Hz, 2H), 3.22-3.15 (m, 1H), 2.89-2.77 (m, 1H), 2.02-1.87 (m, 2H). 19F NMR (376 MHz, Methanol-d4) δ −72.92 (t, J=8.7 Hz), −78.00, −121.19 (d, J=11.0 Hz).

Example 730. Preparation of 5-(7-((2S,2S)-2-(1-(2,2,2-trifluoroethyl)-1H-pyrazolo[4,3-c]pyridin-6-yl)cyclopropyl)pyrazolo[1,5-a]pyrimidin-5-yl)pyrimidine-2,4(1H,3H)-dione (Racemic Mixture)

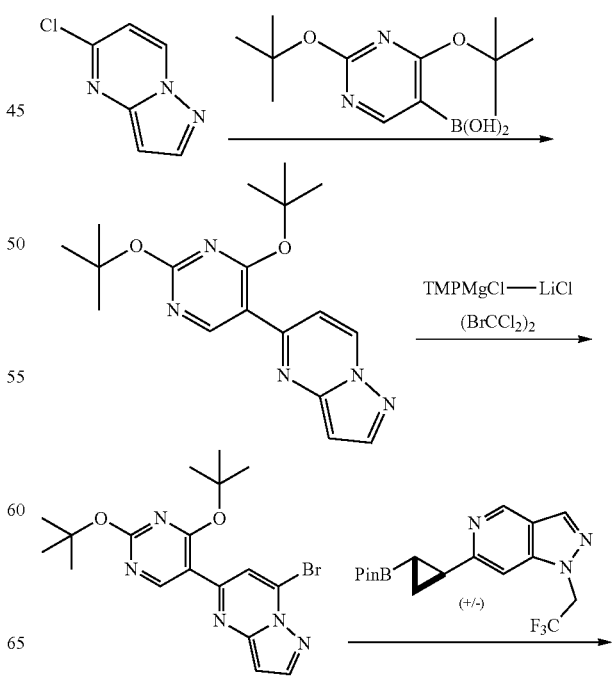

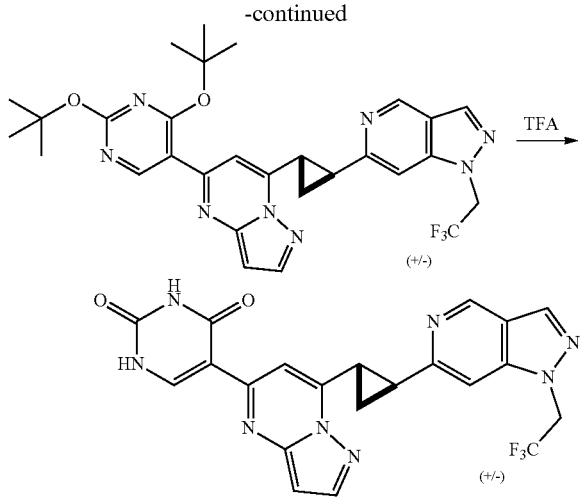

added 10 drops of TFA. After 30 minutes, the reaction mixture was purified by RP-HPLC (10-90% MeCN/H₂O with TFA modifier), affording 5-(7-((2S,2S)-2-(1-(2,2,2-trifluoroethyl)-1H-pyrazolo[4,3-c]pyridin-6-yl)cyclopropyl)pyrazolo[1,5-a]pyrimidin-5-yl)pyrimidine-2,4(1H,3H)-dione (Racemic Mixture). ES/MS m/z: 469.00 [M+H]. 1H NMR (400 MHz, Methanol-d4) δ 9.36 (s, 1H), 8.64 (s, 1H), 8.49 (s, 1H), 8.16 (d, J=2.4 Hz, 1H), 8.15 (s, 1H), 7.84 (s, 1H), 6.67 (d, J=2.4 Hz, 1H), 5.43 (q, J=8.6 Hz, 2H), 3.10-3.02 (m, 1H), 2.25-2.11 (m, 2H). 19F NMR (376 MHz, Methanol-d4) δ −72.78 (t, J=8.6 Hz), −77.85.

Example 731. Preparation of 5-(7-((1S,2S)-2-(1-(2,2,2-trifluoroethyl)-1H-pyrazolo[4,3-b]pyridin-6-yl)cyclopropyl)pyrazolo[1,5-a]pyrimidin-5-yl)pyrimidine-2,4(1H,3H)-dione (Racemic Mixture)

Step 1: To a solution of 5-chloropyrazolo[1,5-a]pyrimidine (1000 mg, 6.51 mmol, 1 equiv) and (2,4-di-tert-butoxypyrimidin-5-yl)boronic acid (1746 mg, 6.51 mmol, 1 equiv) in 4:1 1,4-dioxane:H₂O (30 mL) was added cesium carbonate (5304 mg, 16.3 mmol, 2.5 equiv) and (dppf)-PdCl₂—CH₂Cl₂ (238 mg, 5 mol %). The reaction mixture was heated to 80 C. After 2 hours, the reaction mixture was filtered, concentrated and directly purified by SiO₂ chromatography (0-100% EtOAc/Hex), affording 5-(2,4-di-tert-butoxypyrimidin-5-yl)pyrazolo[1,5-a]pyrimidine. ¹H NMR (400 MHz, DMSO-d6) δ 9.10 (d, J=7.4 Hz, 1H), 8.79 (s, 1H), 8.22 (d, J=2.3 Hz, 1H), 7.46 (d, J=7.4 Hz, 1H), 6.72 (d, J=2.3 Hz, 1H), 1.66 (s, 9H), 1.61 (s, 9H).

Step 2: To a cooled (−78° C.) solution of 5-(2,4-di-tert-butoxypyrimidin-5-yl)pyrazolo[1,5-a]pyrimidine (200 mg, 0.59 mmol, 1 equiv) in THF (1.5 mL) was added a 1M THF/Toluene solution of TMPMgCl·LiCl (0.70 mL, 0.70 mmol, 1.2 equiv). After 15 minutes at −78 C, a solution of 1,2-dibromotetrachloroethane (286 mg, 0.88 mmol, 1.5 equiv) in THF (1 mL) was added dropwise. The reaction mixture was gradually allowed to warm to room temperature over two hours. At t=5 hours, the reaction mixture was quenched with saturated aqueous NH₄Cl and directly purified by SiO₂ chromatography (0-100% EtOAc/Hex), affording 7-bromo-5-(2,4-di-tert-butoxypyrimidin-5-yl)pyrazolo[1,5-a]pyrimidine. ¹H NMR (400 MHz, DMSO-d6) δ 8.83 (s, 1H), 8.34 (d, J=2.4 Hz, 1H), 7.90 (s, 1H), 6.93 (d, J=2.4 Hz, 1H), 1.67 (s, 9H), 1.61 (s, 9H).

Step 3: A degassed solution of 7-bromo-5-(2,4-di-tert-butoxypyrimidin-5-yl)pyrazolo[1,5-a]pyrimidine (30 mg, 0.071 mmol, 1 equiv), racemic 6-((2S,2S)-2-(4,4,5,5-tetramethyl-1,3,2-dioxaborolan-2-yl)cyclopropyl)-1-(2,2,2-trifluoroethyl)-1H-pyrazolo[4,3-c]pyridine (52 mg, 0.14 mmol, 2 equiv), potassium phosphate tribasic (30 mg, 0.14 mmol, 2 equiv), and cataCXium A Pd G3 (10 mg, 20 mol %) in 3:1 1,4-dioxane:H₂O (1 mL) was heated to 100 C. After 3 hours, the reaction mixture was directly purified by SiO₂ chromatography (0-100% EtOAc/Hex), affording 6-((2S,2S)-2-(5-(2,4-di-tert-butoxypyrimidin-5-yl)pyrazolo[1,5-a]pyrimidin-7-yl)cyclopropyl)-1-(2,2,2-trifluoroethyl)-1H-pyrazolo[4,3-c]pyridine (racemic mixture). ES/MS m/z: 469.10 [M+H], product mass minus tert-butyl groups.

Step 4: To a cooled (0 C) solution of 64(1S,2S)-2-(5-(2,4-di-tert-butoxypyrimidin-5-yl)pyrazolo [1,5-a]pyrimidin-7-yl)cyclopropyl)-1-(2,2,2-trifluoroethyl)-1H-pyrazolo[4,3-c]pyridine (Racemic Mixture) in 1:1 H₂/MeCN (2 mL) was

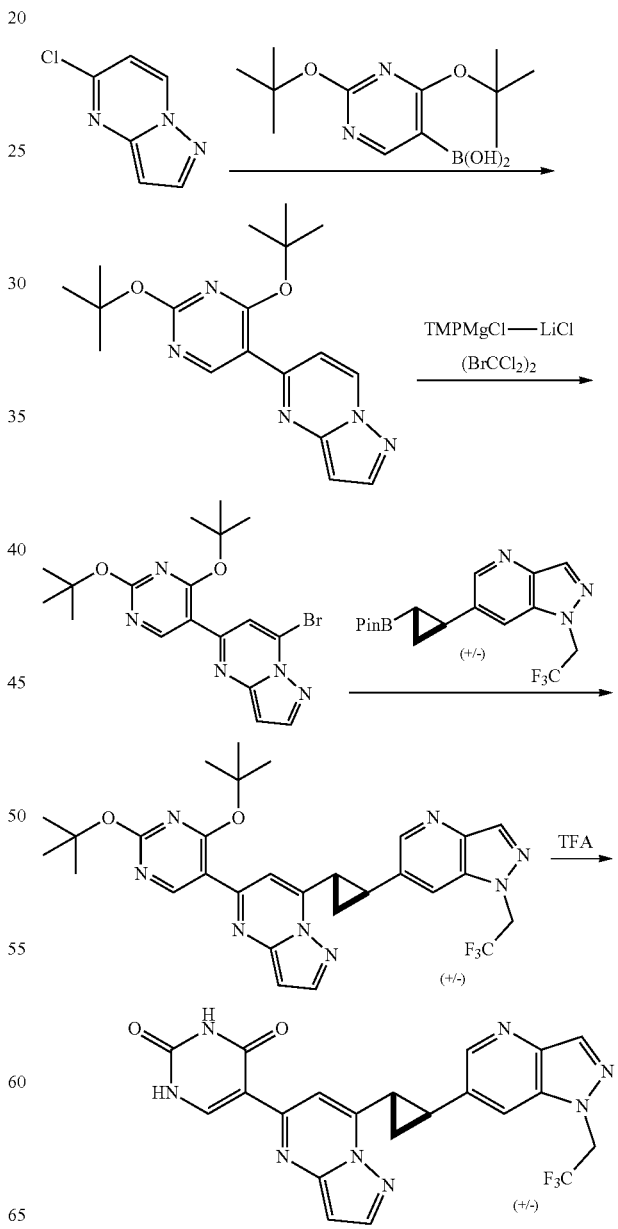

Step 1: To a solution of 5-chloropyrazolo[1,5-a]pyrimidine (1000 mg, 6.51 mmol, 1 equiv) and (2,4-di-tert-butoxypyrimidin-5-yl)boronic acid (1746 mg, 6.51 mmol, 1 equiv) in 4:1 1,4-dioxane:H₂O (30 mL) was added cesium carbonate (5304 mg, 16.3 mmol, 2.5 equiv) and (dppf)-PdCl₂—CH₂Cl₂ (238 mg, 5 mol %). The reaction mixture was heated to 80 C. After 2 hours, the reaction mixture was filtered, concentrated and directly purified by SiO₂ chromatography (0-100% EtOAc/Hex), affording 5-(2,4-di-tert-butoxypyrimidin-5-yl)pyrazolo[1,5-a]pyrimidine. ¹H NMR (400 MHz, DMSO-d6) δ 9.10 (d, J=7.4 Hz, 1H), 8.79 (s, 1H), 8.22 (d, J=2.3 Hz, 1H), 7.46 (d, J=7.4 Hz, 1H), 6.72 (d, J=2.3 Hz, 1H), 1.66 (s, 9H), 1.61 (s, 9H).

Step 2: To a cooled (−78 C) solution of 5-(2,4-di-tert-butoxypyrimidin-5-yl)pyrazolo[1,5-a]pyrimidine (200 mg, 0.59 mmol, 1 equiv) in THF (1.5 mL) was added a 1M THF/Toluene solution of TMPMgCl·LiCl (0.70 mL, 0.70 mmol, 1.2 equiv). After 15 minutes at −78 C, a solution of 1,2-dibromotetrachloroethane (286 mg, 0.88 mmol, 1.5 equiv) in THF (1 mL) was added dropwise. The reaction mixture was gradually allowed to warm to room temperature over two hours. At t=5 hours, the reaction mixture was quenched with saturated aqueous NH₄Cl and directly purified by SiO₂ chromatography (0-100% EtOAc/Hex), affording 7-bromo-5-(2,4-di-tert-butoxypyrimidin-5-yl)pyrazolo[1,5-a]pyrimidine. ¹H NMR (400 MHz, DMSO-d6) δ 8.83 (s, 1H), 8.34 (d, J=2.4 Hz, 1H), 7.90 (s, 1H), 6.93 (d, J=2.4 Hz, 1H), 1.67 (s, 9H), 1.61 (s, 9H).

Step 3: A degassed solution of 7-bromo-5-(2,4-di-tert-butoxypyrimidin-5-yl)pyrazolo[1,5-a]pyrimidine (50 mg, 0.12 mmol, 1 equiv), racemic 64(1S,2S)-2-(4,4,5,5-tetramethyl-1,3,2-dioxaborolan-2-yl)cyclopropyl)-1-(2,2,2-trifluoroethyl)-1H-pyrazolo[4,3-b]pyridine (87 mg, 0.24 mmol, 2 equiv), potassium phosphate tribasic (51 mg, 0.24 mmol, 2 equiv), and cataCXium A Pd G3 (9 mg, 10 mol %) in 3:1 1,4-dioxane:H₂O (2 mL) was heated to 100 C. After 8 hours, the reaction mixture was directly purified by SiO₂ chromatography (0-100% EtOAc/Hex), affording 6-((2S,2S)-2-(5-(2,4-di-tert-butoxypyrimidin-5-yl)pyrazolo[1,5-a]pyrimidin-7-yl)cyclopropyl)-1-(2,2,2-trifluoroethyl)-1H-pyrazolo[4,3-b]pyridine (racemic mixture). ES/MS m/z: 469.10 [M+H], product mass minus tert-butyl groups.

Step 4: To a cooled (0° C.) solution of 64(1S,2S)-2-(5-(2,4-di-tert-butoxypyrimidin-5-yl)pyrazolo[1,5-a]pyrimidin-7-yl)cyclopropyl)-1-(2,2,2-trifluoroethyl)-1H-pyrazolo[4,3-b]pyridine (Racemic Mixture) in 1:1 H₂O MeCN (2 mL) was added 10 drops of TFA. After 30 minutes, the reaction mixture was purified by RP-HPLC (10-90% MeCN/H₂O with TFA modifier), affording 5-(7-((2S,2S)-2-(1-(2,2,2-trifluoroethyl)-1H-pyrazolo[4,3-b]pyridin-6-yl)cyclopropyl)pyrazolo[1,5-a]pyrimidin-5-yl)pyrimidine-2,4(1H,3H)-dione (Racemic Mixture). ES/MS m/z: 469.10 [M+H]. 1H NMR (400 MHz, Methanol-d4) δ 8.72-8.67 (m, 1H), 8.46 (s, 1H), 8.29 (s, 1H), 8.19-8.17 (m, 1H), 8.15 (d, J=2.4 Hz, 1H), 7.76 (s, 1H), 6.65 (d, J=2.4 Hz, 1H), 5.30 (q, J=8.7 Hz, 2H), 3.25-3.16 (m, 1H), 2.96-2.85 (m, 1H), 2.11-2.02 (m, 1H), 2.00-1.94 (m, 1H). 19F NMR (376 MHz, Methanol-d4) δ −73.03 (t, J=8.7 Hz), −77.99.

Example 732. 5-(8-((2S,2S)-2-(8-(2,2,2-trifluoroethoxy)quinolin-6-yl)cyclopropyl)imidazo[1,2-b]pyridazin-6-yl)pyrimidine-2,4(1H,3H)-dione

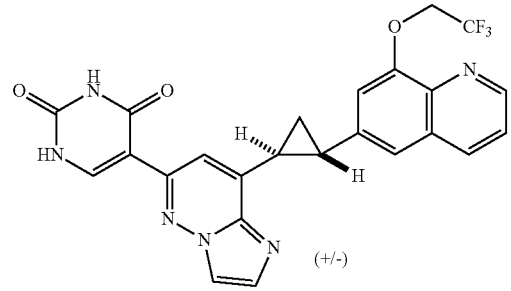 [SMILES: O=c1[nH]cc(-c2cc([C@H]3C[C@@H]3c3cc(OCC(F)(F)F)c4ncccc4c3)c3nccn3n2)c(=O)[nH]1]

5-(8-((1S,2S)-2-(8-(2,2,2-trifluoroethoxy)quinolin-6-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6-((2S,2S)-2-(6-(2,4-dimethoxypyrimidin-5-yl)imidazo[1,2-b]pyridazin-8-yl)cyclopropyl)-8-(2,2,2-trifluoroethoxy)quinoline. ES/MS m/z: 495.20 [M+H]. 1H NMR (400 MHz, Methanol-d4) δ 8.96 (dd, J=4.9, 1.4 Hz, 1H), 8.80-8.74 (m, 1H), 8.27 (d, J=1.6 Hz, 1H), 8.25 (s, 1H), 7.92-7.84 (m, 3H), 7.74 (s, 1H), 7.53 (s, 1H), 5.00 (q, J=8.4 Hz, 2H), 3.02-2.93 (m, 2H), 2.08 (t, J=7.5 Hz, 2H). 19F NMR (376 MHz, Methanol-d4) δ −75.48 (t, J=8.5 Hz), −77.85.

Example 733. 5-(8-((2S,2S)-2-(1'-(2,2-difluoropropyl)-2'-oxospiro[cyclopropane-1,3'-indolin]-6'-yl)cyclopropyl)imidazo[1,2-b]pyridazin-6-yl)pyrimidine-2,4(1H,3H)-dione (Racemic Mixture)

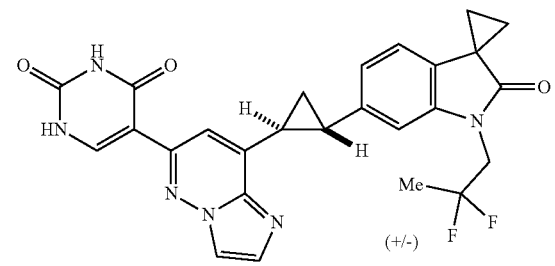 [SMILES: CC(F)(F)CN1C(=O)C2(CC2)c2ccc([C@H]3C[C@@H]3c3cc(-c4c[nH]c(=O)[nH]c4=O)nn4ccnc34)cc21]

5-(8-((1S,2S)-2-(1'-(2,2-difluoropropyl)-T-oxospiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 1'-(2,2-difluoropropyl)-6'-((1S,2S)-2-(6-(2,4-dimethoxypyrimidin-5-yl)imidazo[1,2-b]pyridazin-8-yl)cyclopropyl)spiro[cyclopropane-1,3'-indolin]-2'-one (Racemic Mixture). ES/MS m/z: 505.20 [M+H]. 1H NMR (400 MHz, Methanol-d4) δ 8.35 (d, J=1.9 Hz, 1H), 8.27 (s, 1H), 8.03 (d, J=1.9 Hz, 1H), 7.98 (s, 1H), 7.07 (s, 1H), 7.03-6.91 (m, 2H), 4.30-4.14 (m, 2H), 2.84-2.69 (m, 2H), 1.98-1.86 (m, 2H), 1.72-1.60 (m, 7H). 19F NMR (376 MHz, Methanol-d4) δ −77.82, −94.82--95.15 (m).

Example 734. 5-(8-((2S,2S)-2-(1'-((1-fluorocyclopropyl)methyl)-2'-oxospiro[cyclopropane-1,3'-indolin]-6'-yl)cyclopropyl)imidazo[1,2-b]pyridazin-6-yl)pyrimidine-2,4(1H,3H)-dione (Racemic Mixture)

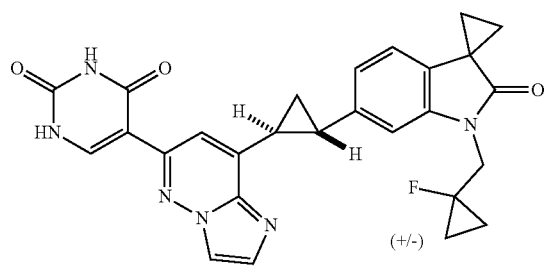 [SMILES: O=C1N(CC2(F)CC2)c2cc([C@H]3C[C@@H]3c3cc(-c4c[nH]c(=O)[nH]c4=O)nn4ccnc34)ccc2C12CC2]

5-(8-((1S,2S)-2-(1'-((1-fluorocyclopropyl)methyl)-2'-oxospiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6'-((2S,2S)-2-(6-(2,4-dimethoxypyrimidin-5-yl)imidazo[1,2-b]pyridazin-8-yl)cyclopropyl)-1'-((1-fluorocyclopropyl)methyl)spiro[cyclopropane-1,3'-indolin]-2'-one (Racemic Mixture). ES/MS m/z: 499.20 [M+H]. 1H NMR (400 MHz, Methanol-d4) δ 8.35 (d, J=1.9 Hz, 1H), 8.27 (s, 1H), 8.03 (d, J=1.9 Hz, 1H), 7.98 (s, 1H), 7.11 (s, 1H), 7.01-6.91 (m, 2H), 4.21 (d, J=21.0 Hz, 2H), 2.84-2.67 (m, 2H), 1.98-1.86 (m, 2H), 1.70-1.59 (m, 4H), 1.13-0.99 (m, 2H), 0.96-0.85 (m, 2H). 19F NMR (376 MHz, Methanol-d4) δ −77.81, −184.03−−184.30 (m).

Example 735. 5-(3-fluoro-8-((2S,2S)-2-(1'-((1-fluorocyclopropyl)methyl)-2'-oxospiro[cyclopropane-1,3'-indolin]-6'-yl)cyclopropyl)imidazo[1,2-b]pyridazin-6-yl)pyrimidine-2,4(1H,3H)-dione (Racemic Mixture)

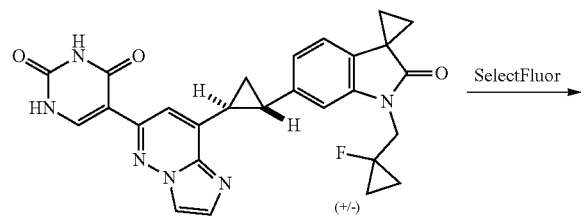

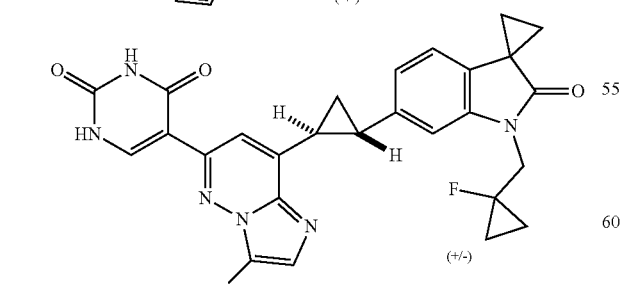

To a solution of racemic 5-(8-((1S,2S)-2-(1'-((1-fluorocyclopropyl)methyl)-2'-oxospiro[cyclopropane-1,3'-indolin]-6'-yl)cyclopropyl)imidazo[1,2-b]pyridazin-6-yl)pyrimidine-2,4(1H,3H)-dione (13 mg, 0.026 mmol, 1 equiv) in DMF (0.6 mL) was added Selectfluor (19 mg, 0.052 mmol, 2 equiv). After 18 hours, the reaction mixture was directly purified by RP-HPLC (10-90% MeCN/H₂O with TFA modifier), affording 5-(3-fluoro-8-((1S,2S)-2-(1'-((1-fluorocyclopropyl)methyl)-2'-oxospiro[cyclopropane-1,3'-indolin]-6'-yl)cyclopropyl)imidazo[1,2-b]pyridazin-6-yl)pyrimidine-2,4(1H,3H)-dione (Racemic Mixture). ES/MS m/z: 517.20 [M+H]. 1H NMR (400 MHz, Methanol-d4) δ 8.19 (s, 1H), 7.56 (s, 1H), 7.42 (d, J=6.8 Hz, 1H), 7.08 (s, 1H), 7.00-6.87 (m, 2H), 4.33-4.13 (m, 2H), 2.85-2.74 (m, 2H), 1.97-1.88 (m, 1H), 1.83-1.73 (m, 1H), 1.70-1.56 (m, 4H), 1.11-0.99 (m, 2H), 0.95-0.85 (m, 2H). 19F NMR (376 MHz, Methanol-d4) δ −77.82, −157.36 (d, J=6.8 Hz), −184.17−−184.52 (m).

Example 736. 5-(8-((2S,2S)-2-(2'-oxo-1'-(2,2,3,3-tetrafluoropropyl)spiro[cyclopropane-1,3'-indolin]-6'-yl)cyclopropyl)imidazo[1,2-b]pyridazin-6-yl)pyrimidine-2,4(1H,3H)-dione (Racemic Mixture)

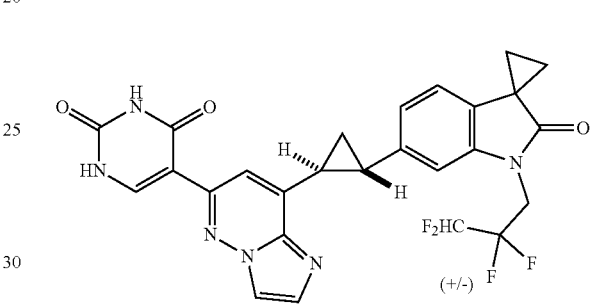

5-(8-((2S,2S)-2-(2'-oxo-1'-(2,2,3,3-tetrafluoropropyl)spiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-1'-(2,2,3,3-tetrafluoropropyl)spiro[cyclopropane-1,3'-indolin]-2'-one (Racemic Mixture). ES/MS m/z: 541.20 [M+H]. 1H NMR (400 MHz, Methanol-d4) δ 8.34 (d, J=1.9 Hz, 1H), 8.27 (s, 1H), 8.01 (d, J=1.9 Hz, 1H), 7.96 (s, 1H), 7.06 (s, 1H), 7.04-6.94 (m, 2H), 6.24 (tt, J=52.6, 4.4 Hz, 1H), 4.57-4.37 (m, 2H), 2.84-2.69 (m, 2H), 1.97-1.87 (m, 2H), 1.75-1.61 (m, 4H). 19F NMR (376 MHz, Methanol-d4) δ −77.80, −121.57−−121.82 (m), −139.57 (d, J=52.5 Hz).

Example 737. 5-(8-((2S,2S)-2-(2'-oxo-1'-(2,2,3,3,3-pentafluoropropyl)spiro[cyclopropane-1,3'-indolin]-6'-yl)cyclopropyl)imidazo[1,2-b]pyridazin-6-yl)pyrimidine-2,4(1H,3H)-dione (Racemic Mixture)

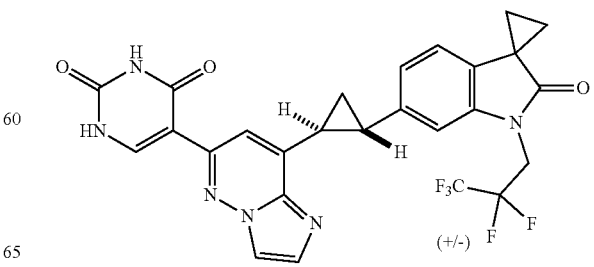

5-(8-((1S,2S)-2-(2'-oxo-1'-(2,2,3,3,3-pentafluoropropyl)spiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-1'-(2,2,3,3,3-pentafluoropropyl)spiro[cyclopropane-1,3'-indolin]-2'-one (Racemic Mixture). ES/MS m/z: 559.20 [M+H]. 1H NMR (400 MHz, Methanol-d4) δ 8.33 (d, J=1.8 Hz, 1H), 8.26 (s, 1H), 8.00 (d, J=1.8 Hz, 1H), 7.94 (s, 1H), 7.09-7.06 (m, 1H), 7.05-6.95 (m, 2H), 4.69-4.57 (m, 2H), 2.88-2.67 (m, 2H), 1.96-1.89 (m, 2H), 1.73-1.64 (m, 4H). 19F NMR (376 MHz, Methanol-d4) δ −77.80, −86.44, −120.52-120.71 (m).

Example 738. 5-(8-((2S,2S)-2-(1'-(2-cyclopropyl-2,2-difluoroethyl)-2'-oxospiro[cyclopropane-1,3'-indolin]-6'-yl)cyclopropyl)imidazo[1,2-b]pyridazin-6-yl)pyrimidine-2,4(1H,3H)-dione (Racemic Mixture)

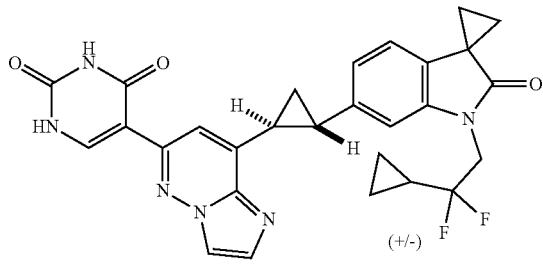 [SMILES: O=C1N(CC(F)(F)C2CC2)c2cc([C@H]3C[C@@H]3c3cc(-c4c[nH]c(=O)[nH]c4=O)nn4ccnc34)ccc2C12CC2]

5-(8-((1S,2S)-2-(1'-(2-cyclopropyl-2,2-difluoroethyl)-2'-oxospiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 1'-(2-cyclopropyl-2,2-difluoroethyl)-6'-((1S,2S)-2-(6-(2,4-dimethoxypyrimidin-5-yl)imidazo[1,2-b]pyridazin-8-yl)cyclopropyl)spiro[cyclopropane-1,3'-indolin]-2'-one (Racemic Mixture). ES/MS m/z: 531.20 [M+H]. 1H NMR (400 MHz, Methanol-d4) δ 8.36-8.31 (m, 1H), 8.27 (s, 1H), 8.01 (s, 1H), 7.95 (s, 1H), 7.09-7.05 (m, 1H), 7.01-6.93 (m, 2H), 4.39-4.25 (m, 2H), 2.82-2.71 (m, 2H), 1.94-1.87 (m, 2H), 1.73-1.55 (m, 5H), 0.90-0.86 (m, 4H). 19F NMR (376 MHz, Methanol-d4) δ −77.80, −106.91-−107.21 (m).

Example 739. 5-(8-((2S,2S)-2-(1'-(2,2-difluoropropyl)-2'-oxospiro[cyclopropane-1,3'-indolin]-6'-yl)cyclopropyl)-3-fluoroimidazo[1,2-b]pyridazin-6-yl)pyrimidine-2,4(1H,3H)-dione

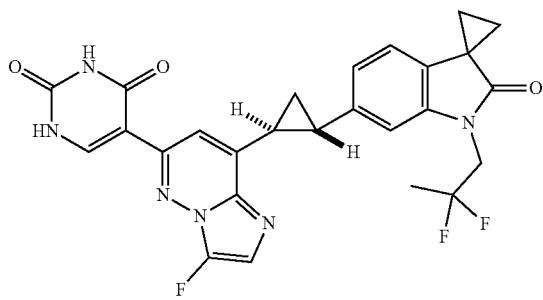 [SMILES: CC(F)(F)CN1C(=O)C2(CC2)c2ccc([C@H]3C[C@@H]3c3cc(-c4c[nH]c(=O)[nH]c4=O)nn4c(F)cnc34)cc21]

5-(8-((2S,2S)-2-(1'-(2,2-difluoropropyl)-2'-oxospiro[cyclopropane-1,3'-indolin]-6'-yl)cyclopropyl)-3-fluoroimidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with 1'-(2,2-difluoropropyl)-6'-((1S,2S)-2-(6-(2,4-dimethoxypyrimidin-5-yl)-3-fluoroimidazo[1,2-b]pyridazin-8-yl)cyclopropyl)spiro[cyclopropane-1,3'-indolin]-2'-one. ES/MS m/z: 523.20 [M+H]. 1H NMR (400 MHz, Methanol-d4) δ 8.21 (s, 1H), 7.66 (s, 1H), 7.52 (d, J=6.6 Hz, 1H), 7.05 (s, 1H), 7.01-6.85 (m, 2H), 4.32-4.14 (m, 2H), 2.83-2.72 (m, 2H), 1.97-1.89 (m, 1H), 1.86-1.78 (m, 1H), 1.72-1.59 (m, 7H). 19F NMR (376 MHz, Methanol-d4) δ −78.16, −94.84-−95.17 (m), −156.91 (d, J=6.7 Hz).

Example 740. 5-(3-chloro-8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione

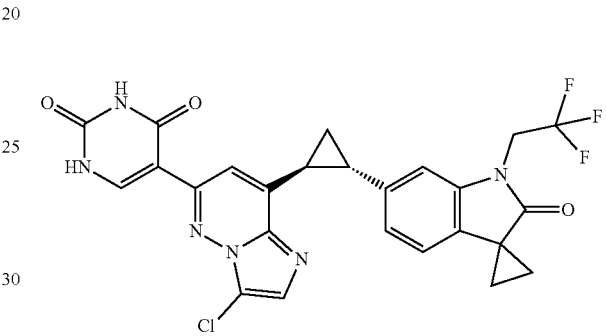

Palau'Chlor (20 mg, 0.1 mmol) was added to solution of 5-(8-((1S,2S)-2-(2'-oxo-F-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione (single enantiomer, 49 mg, 0.1 mmol) in DMF (1 ml) at RT. The reaction mixture was stirred at RT for 2 h and then purified with Prep HPLC to afford 5-(3-chloro-8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione as single enantiomer. ES/MS m/z: 543.10 [M+H]. 1H NMR (400 MHz, Acetonitrile-d3) δ 9.23 (s, 2H), 8.11 (d, J=6.4 Hz, 1H), 7.77 (s, 1H), 7.72 (s, 1H), 7.09-6.82 (m, 3H), 4.51 (q, J=9.3 Hz, 2H), 2.78 (s, 2H), 2.05-2.01 (m, 1H), 1.83 (d, J=7.4 Hz, 1H), 1.65 (dt, J=5.1, 3.5 Hz, 4H). 19F NMR (377 MHz, Acetonitrile-d3) δ −71.19 (t, J=9.2 Hz), −77.32.

Example 741. 5-(2,3-dichloro-8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione

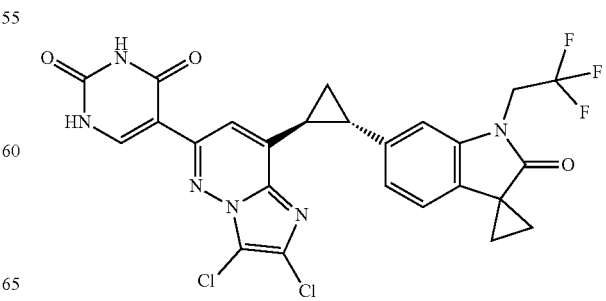

Palau'Chlor (20 mg, 0.1 mmol) was added to solution of 5-(8-((2S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione (single enantiomer, 49 mg, 0.1 mmol) in DMF (1 ml) at RT. The reaction mixture was stirred at RT for 2 h and then purified with Prep HPLC to afford 5-(2,3-dichloro-8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione dione as single enantiomer. ES/MS m/z: 577.10 [M+H]. 1H NMR (400 MHz, DMSO-d6) δ 11.57 (d, J=4.3 Hz, 2H), 8.05 (d, J=6.4 Hz, 1H), 7.65 (s, 1H), 7.19 (s, 1H), 7.03-6.91 (m, 2H), 4.69 (td, J=9.3, 3.4 Hz, 2H), 2.75 (ddt, J=36.8, 10.0, 4.8 Hz, 2H), 2.13-1.97 (m, 1H), 1.83 (dt, J=8.4, 5.3 Hz, 1H), 1.68-1.47 (m, 4H). 19F NMR (376 MHz, DMSO-d6) δ −69.25 (t, J=9.4 Hz), −74.01.

Example 742. (S)-4-(1-(6-(2,4-dioxo-1,2,3,4-tetrahydropyrimidin-5-yl)-3-fluoroimidazo[1,2-b]pyridazin-8-yl)-4,4-difluoropyrrolidin-3-yl)oxy)-2-(trifluoromethoxy)benzonitrile

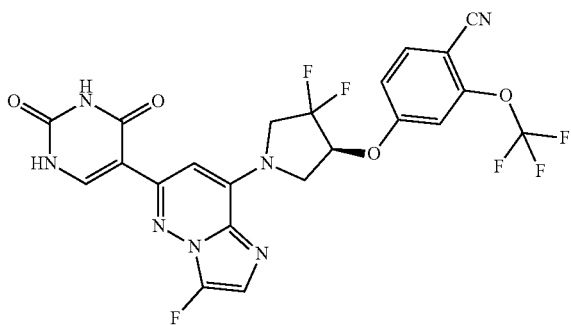 [SMILES: N#Cc1ccc(O[C@H]2CN(c3cc(-c4c[nH]c(=O)[nH]c4=O)nn4c(F)cnc34)CC2(F)F)cc1OC(F)(F)F]

(S)-4-((1-(6-(2,4-dioxo-1,2,3,4-tetrahydropyrimidin-5-yl)-3-fluoroimidazo[1,2-b]pyridazin-8-yl)-4,4-difluoropyrrolidin-3-yl)oxy)-2-(trifluoromethoxy)benzonitrile was prepared in the manner described for Example 1, but replacing 8-cyclopropyl-6-(2,4-dimethoxypyrimidin-5-yl)-2-methyl-imidazo[1,2-b]pyridazine with (S)-4-((1-(6-(2,4-dimethoxypyrimidin-5-yl)-3-fluoroimidazo[1,2-b]pyridazin-8-yl)-4,4-difluoropyrrolidin-3-yl)oxy)-2-(trifluoromethoxy)benzonitrile. ES/MS m/z: 554.10 [M+H]. 1H NMR (400 MHz, DMSO-d6) δ 11.54-11.12 (m, 2H), 8.07 (d, J=8.8 Hz, 1H), 7.97 (d, J=6.0 Hz, 1H), 7.48 (dd, J=2.5, 1.4 Hz, 1H), 7.45-7.38 (m, 2H), 6.65 (s, 1H), 5.83-5.56 (m, 1H), 4.49 (d, J=64.0 Hz, 4H). 19F NMR (376 MHz, DMSO-d6) δ −57.67, −75.32, −106.91 (d, J=241.3 Hz), −120.56 (d, J=239.7 Hz), −155.33 (d, J=7.1 Hz).

Example 743. (S)-4-(1-(6-(2,4-dioxo-1,2,3,4-tetrahydropyrimidin-5-yl)imidazo[1,2-b]pyridazin-8-yl)-4,4-difluoropyrrolidin-3-yl)oxy)-2-(trifluoromethoxy)benzonitrile

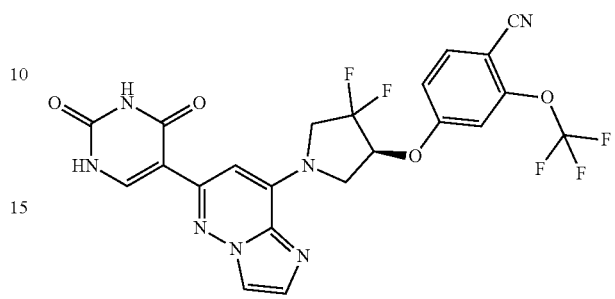

(S)-4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)-2-(trifluoromethoxy)benzonitrile was prepared in the manner described for Example 1, but replacing 8-cyclopropyl-6-(2,4-dimethoxypyrimidin-5-yl)-2-methyl-imidazo[1,2-b]pyridazine with (S)-4-((1-(6-(2,4-dimethoxypyrimidin-5-yl)imidazo[1,2-b]pyridazin-8-yl)-4,4-difluoropyrrolidin-3-yl)oxy)-2-(trifluoromethoxy)benzonitrile. ES/MS m/z: 536.10 [M+H]. 1H NMR (400 MHz, DMSO-d6) δ11.52-11.31 (m, 2H), 8.09 (d, J=1.1 Hz, 1H), 8.08 (d, J=8.8 Hz, 1H), 7.94 (d, J=6.1 Hz, 1H), 7.59 (d, J=1.1 Hz, 1H), 7.48 (dd, J=2.5, 1.3 Hz, 1H), 7.42 (dd, J=8.8, 2.4 Hz, 1H), 6.65 (s, 1H), 5.73 (dt, J=8.0, 4.1 Hz, 1H), 4.50-4.18 (m, 4H). 19F NMR (376 MHz, DMSO-d6) δ −57.67, −75.37, −106.84 (d, J=239.4 Hz), −120.31 (d, J=238.7 Hz).

Example 744. (S)-5-(8-(4-(4-(difluoromethyl)-5-fluoropyridin-2-yl)oxy)-3,3-difluoropyrrolidin-1-yl)-3-fluoroimidazo[1,2-b]pyridazin-6-yl)pyrimidine-2,4(1H,3H)-dione

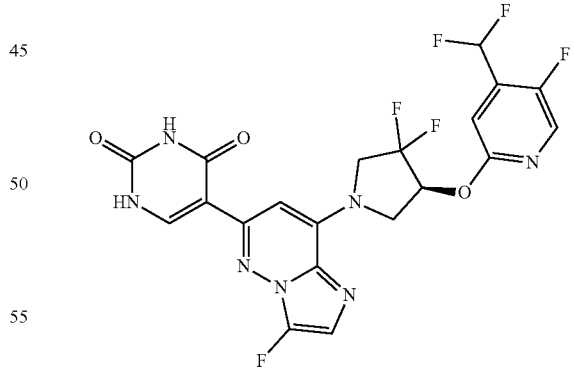

(S)-5-(8-(4-(4-(difluoromethyl)-5-fluoropyridin-2-yl)oxy)-3,3-difluoropyrrolidin-1-yl)-3-fluoroimidazo[1,2-b]pyridazin-6-yl)pyrimidine-2,4(1H,3H)-dionewas prepared in the manner described for Example 1, but replacing 8-cyclopropyl-6-(2,4-dimethoxypyrimidin-5-yl)-2-methyl-imidazo[1,2-b]pyridazine with (S)-8-(4-(4-(difluoromethyl)-5-fluoropyridin-2-yl)oxy)-3,3-difluoropyrrolidin-1-yl)-6-(2,4-dimethoxypyrimidin-5-yl)-3-fluoroimidazo[1,2-b]pyridazine. ES/MS m/z: 514.10 [M+H]. 1H NMR (400

MHz, DMSO-d6) δ 11.55-11.22 (m, 2H), 8.45 (d, J=1.5 Hz, 1H), 7.98 (d, J=6.1 Hz, 1H), 7.43 (d, J=7.1 Hz, 1H), 7.39-7.08 (m, 2H), 6.65 (s, 1H), 5.91 (d, J=7.5 Hz, 1H), 4.51 (d, J=43.7 Hz, 3H), 4.19 (s, 1H). 19F NMR (376 MHz, DMSO-d6) δ -74.95, -107.75--108.38 (m), -117.95 (ddd, J=53.4, 11.7, 6.2 Hz), -119.93 (d, J=238.6 Hz), -143.15 (q, J=5.7, 5.2 Hz), -155.37 (d, J=7.4 Hz).

Example 745. (S)-5-(8-(4-(3-(difluoromethyl)-4-fluorophenoxy)-3,3-difluoropyrrolidin-1-yl)imidazo[1,2-b]pyridazin-6-yl)pyrimidine-2,4(1H,3H)-dione

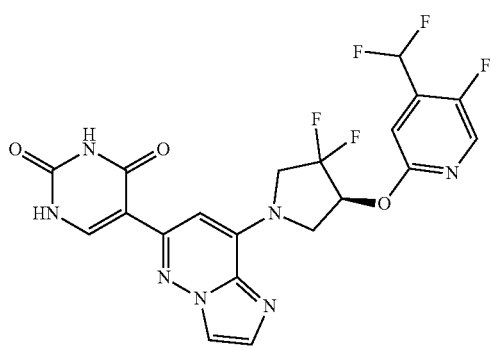 [SMILES: O=c1[nH]cc(-c2cc(N3C[C@H](Oc4cc(C(F)F)c(F)cn4)C(F)(F)C3)c3nccn3n2)c(=O)[nH]1]

(S)-5-(8-(4-(3-(difluoromethyl)-4-fluorophenoxy)-3,3-difluoropyrrolidin-1-yl)imidazo[1,2-b]pyridazin-6-yl)pyrimidine-2,4(1H,3H)-dione was prepared in the manner described for Example 1, but replacing 8-cyclopropyl-6-(2,4-dimethoxypyrimidin-5-yl)-2-methyl-imidazo[1,2-b]pyridazine with (S)-8-(4-(3-(difluoromethyl)-4-fluorophenoxy)-3,3-difluoropyrrolidin-1-yl)-6-(2,4-dimethoxypyrimidin-5-yl)imidazo[1,2-b]pyridazine. ES/MS m/z: 495.20 [M+H]. 1H NMR (400 MHz, Acetonitrile-d3) δ 9.23 (s, 2H), 8.06 (d, J=6.3 Hz, 1H), 7.98 (d, J=1.6 Hz, 1H), 7.74 (d, J=1.6 Hz, 1H), 7.30 (d, J=5.7 Hz, 1H), 7.26-7.21 (m, 2H), 7.15-6.79 (m, 2H), 5.23 (tt, J=7.7, 3.1 Hz, 1H), 4.55-4.32 (m, 3H), 4.32-4.12 (m, 1H). 19F NMR (377 MHz, Acetonitrile-d3) δ -77.23, -106.24--109.63 (m), -115.75 (dt, J=54.4, 4.0 Hz), -122.73 (d, J=241.3 Hz), -129.16 (dt, J=11.3, 3.9 Hz).

Example 746. 5-(8-((2S,2S)-2-(2'-oxo-1'-(3,3,3-trifluoropropyl)spiro[cyclopropane-1,3'-indolin]-6'-yl)cyclopropyl)imidazo[1,2-b]pyridazin-6-yl)pyrimidine-2,4(1H,3H)-dione (Racemate)

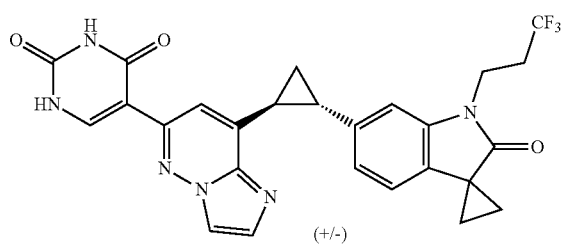 [SMILES: O=C1N(CCC(F)(F)F)c2cc([C@H]3C[C@@H]3c3cc(-c4c[nH]c(=O)[nH]c4=O)nn4ccnc34)ccc2C12CC2]

5-(8-((2S,2S)-2-(2'-oxo-1'-(3,3,3-trifluoropropyl)spiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-1'-(3,3,3-trifluoropropyl)spiro[cyclopropane-1,3'-indolin]-2'-one (racemate). ES/MS m/z: 523.20 [M+H]. 1H NMR (400 MHz, Acetonitrile-d3) δ 9.53 (s, 1H), 9.41 (s, 1H), 8.24-8.15 (m, 2H), 8.06 (s, 1H), 7.99 (d, J=2.1 Hz, 1H), 6.98-6.87 (m, 3H), 4.05 (td, J=7.0, 2.8 Hz, 2H), 2.82 (dt, J=9.1, 5.2 Hz, 1H), 2.64 (qt, J=11.0, 6.7 Hz, 3H), 1.97-1.90 (m, 1H), 1.85 (dt, J=9.1, 5.7 Hz, 1H), 1.58 (dd, J=5.1, 3.6 Hz, 4H). 19F NMR (377 MHz, Acetonitrile-d3) δ -66.52 (t, J=11.1 Hz), -77.19.

Example 747. 5-(8-((2S,2S)-2-(7'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione

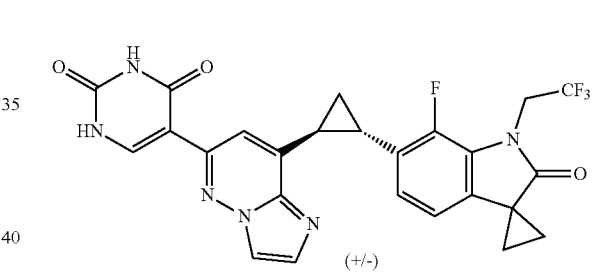

5-(8-((2S,2S)-2-(7'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-7'-fluoro-1'-(2,2,2-trifluoroethyl)spiro[cyclopropane-1,3'-indolin]-2'-one (racemate). ES/MS m/z: 527.10 [M+H]. 1H NMR (400 MHz, Acetonitrile-d3) δ 9.47 (s, 1H), 9.37 (s, 1H), 8.22 (d, J=2.1 Hz, 1H), 8.17 (d, J=6.2 Hz, 1H), 8.11 (s, 1H), 8.01 (d, J=2.2 Hz, 1H), 6.93 (t, J=7.1 Hz, 1H), 6.80 (d, J=7.9 Hz, 1H), 4.64 (q, J=8.9 Hz, 2H), 2.89-2.67 (m, 2H), 1.95-1.89 (m, 1H), 1.88-1.82 (m, 1H), 1.75-1.65 (m, 4H). 19F NMR (376 MHz, Acetonitrile-d3) δ -72.12 (q, J=9.1 Hz), -77.22, -143.08 (qd, J=10.1, 6.4 Hz).

Example 748. 5-(8-((2S,2S)-2-(5'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione

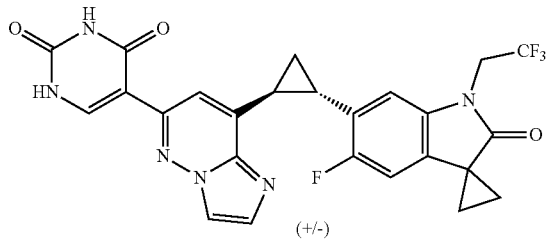 [SMILES: O=C1N(CC(F)(F)F)c2cc([C@H]3C[C@@H]3c3cc(-c4c[nH]c(=O)[nH]c4=O)nn4ccnc34)c(F)cc2C12CC2]

(+/-)

5-(8-((1S,2S)-2-(5'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-5'-fluoro-1'-(2,2,2-trifluoroethyl)spiro[cyclopropane-1,3'-indolin]-2'-one (racemate). ES/MS m/z: 527.20 [M+H]. 1H NMR (400 MHz, Acetonitrile-d3) δ 9.32 (s, 1H), 9.26 (s, 1H), 8.15 (d, J=1.9 Hz, 1H), 8.11 (d, J=6.5 Hz, 1H), 7.95 (s, 1H), 7.92 (d, J=1.9 Hz, 1H), 6.96 (d, J=5.9 Hz, 1H), 6.81 (d, J=9.7 Hz, 1H), 4.55 (qd, J=9.2, 3.1 Hz, 2H), 2.85 (t, J=6.9 Hz, 2H), 1.75-1.53 (m, 4H). 19F NMR (376 MHz, Acetonitrile-d3) δ −71.21 (t, J=9.2 Hz), −77.04, −127.92 (dd, J=9.7, 5.8 Hz).

Example 749. 5-(8-((2S,2S)-2-(4'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione

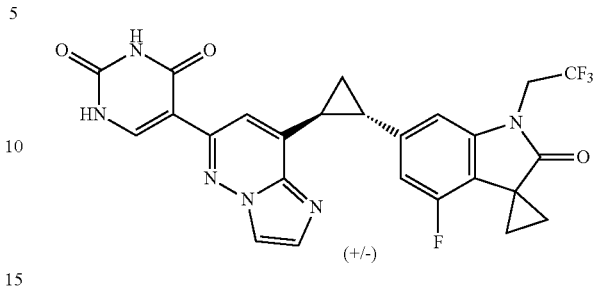

(+/-)

5-(8-((2S,2S)-2-(4'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione was prepared as a racemic mixture in the manner described for Example 1, but replacing 8-cyclopropyl-6-(2,4-dimethoxypyrimidin-5-yl)-2-methyl-imidazo[1,2-b]pyridazine with 6'-((1S,2S)-2-(6-(2,4-dimethoxypyrimidin-5-yl)imidazo[1,2-b]pyridazin-8-yl)cyclopropyl)-4'-fluoro-1'-(2,2,2-trifluoroethyl)spiro[cyclopropane-1,3'-indolin]-2'-one (racemate). ES/MS m/z: 527.20 [M+H]. 1H NMR (400 MHz, Acetonitrile-d3) δ 9.37 (s, 1H), 9.31 (s, 1H), 8.20 (d, J=1.9 Hz, 1H), 8.16 (d, J=6.5 Hz, 1H), 8.03 (s, 1H), 7.98 (d, J=2.1 Hz, 1H), 6.94 (s, 1H), 6.75 (d, J=11.1 Hz, 1H), 4.52 (q, J=9.2 Hz, 2H), 2.69-2.59 (m, 1H), 1.93-1.82 (m, 4H), 1.64 (q, J=4.0 Hz, 2H). 19F NMR (376 MHz, Acetonitrile-d3) δ −71.19 (t, J=9.2 Hz), −77.24 (d, J=3.8 Hz), −128.71 (d, J=11.3 Hz).

CD73 inhibitor compounds made as described herein are summarized in Table 2.

TABLE 2

Examples

| Ex. No. | Structure | IUPAC Name |
|---|---|---|
| 1 | 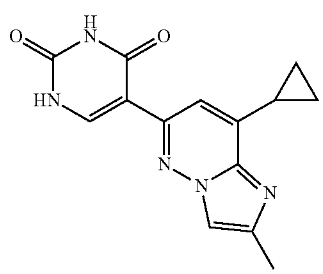 [SMILES: Cc1cn2nc(-c3c[nH]c(=O)[nH]c3=O)cc(C3CC3)c2n1] | 5-(8-cyclopropyl-2-methyl-imidazo[1,2-b]pyridazin-6-yl)-1H-pyrimidine-2,4-dione |
| 2 | 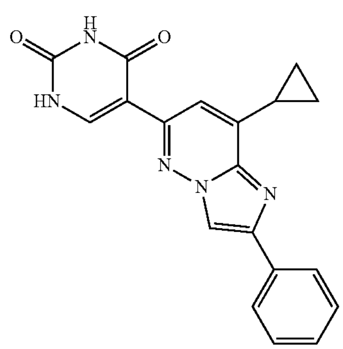 [SMILES: O=c1[nH]cc(-c2cc(C3CC3)c3nc(-c4ccccc4)cn3n2)c(=O)[nH]1] | 5-(8-cyclopropyl-2-phenyl-imidazo[1,2-b]pyridazin-6-yl)-1H-pyrimidine-2,4-dione |

TABLE 2-continued

| Ex. No. | Structure | IUPAC Name |
|---|---|---|
| 3 | 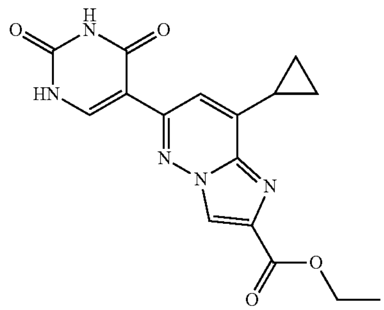 [SMILES: CCOC(=O)c1cn2nc(-c3c[nH]c(=O)[nH]c3=O)cc(C3CC3)c2n1] | Ethyl 8-cyclopropyl-6-(2,4-dioxo-1H-pyrimidin-5-yl)imidazo[1,2-b]pyridazine-2-carboxylate |
| 4 | | 5-(8-((1S,2S)-2-(methoxymethyl)cyclopropyl)imidazo[1,2-b]pyridazin-6-yl)pyrimidine-2,4(1H,3H)-dione<br>and<br>5-(8-((1R,2R)-2-(methoxymethyl)cyclopropyl)imidazo[1,2-b]pyridazin-6-yl)pyrimidine-2,4(1H,3H)-dione |
| 5 | | (S)-5-(8-(spiro[2.3]hexan-1-yl)imidazo[1,2-b]pyridazin-6-yl)pyrimidine-2,4(1H,3H)-dione<br>and<br>(R)-5-(8-(spiro[2.3]hexan-1-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 6 | 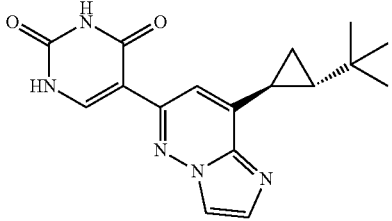 [SMILES: CC(C)(C)[C@H]1C[C@@H]1c1cc(-c2c[nH]c(=O)[nH]c2=O)nn2ccnc12] and 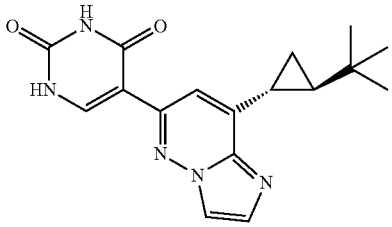 [SMILES: CC(C)(C)[C@@H]1C[C@H]1c1cc(-c2c[nH]c(=O)[nH]c2=O)nn2ccnc12] | 5-(8-((1S,2S)-2-(tert-butyl)cyclopropyl)imidazo[1,2-b]pyridazin-6-yl)pyrimidine-2,4-(1H,3H)-dione and 5-(8-((1R,2R)-2-(tert-butyl)cyclopropyl)imidazo[1,2-b]pyridazin-6-yl)pyrimidine-2,4-(1H,3H)-dione |
| 7 | 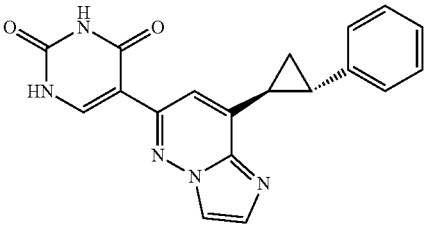 [SMILES: O=c1[nH]cc(-c2cc([C@H]3C[C@@H]3c3ccccc3)c3nccn3n2)c(=O)[nH]1] and 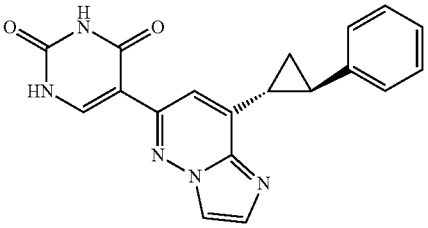 [SMILES: O=c1[nH]cc(-c2cc([C@@H]3C[C@H]3c3ccccc3)c3nccn3n2)c(=O)[nH]1] | 5-(8-((1S,2S)-2-phenylcyclopropyl)imidazo[1,2-b]pyridazin-6-yl)pyrimidine-2,4-(1H,3H)-dione and 5-(8-((1R,2R)-2-phenylcyclopropyl)imidazo[1,2-b]pyridazin-6-yl)pyrimidine-2,4-(1H,3H)-dione |
| 8 | 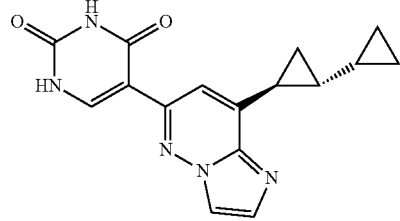 [SMILES: O=c1[nH]cc(-c2cc([C@H]3C[C@@H]3C3CC3)c3nccn3n2)c(=O)[nH]1] and 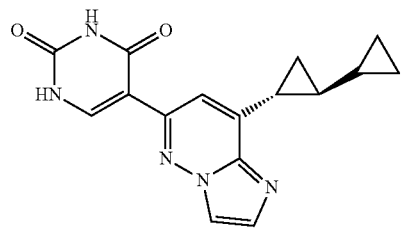 [SMILES: O=c1[nH]cc(-c2cc([C@@H]3C[C@H]3C3CC3)c3nccn3n2)c(=O)[nH]1] | 5-(8-((1R,2S)-[1,1'-bi(cyclopropan)]-2-yl)imidazo[1,2-b]pyridazin-6-yl)pyrimidine-2,4(1H,3H)-dione and 5-(8-((1S,2R)-[1,1'-bi(cyclopropan)]-2-yl)imidazo[1,2-b]pyridazin-6-yl)pyrimidine-2,4(1H,3H)-dione |

TABLE 2-continued

| Ex. No. | Structure | IUPAC Name |
|---|---|---|
| 9 | 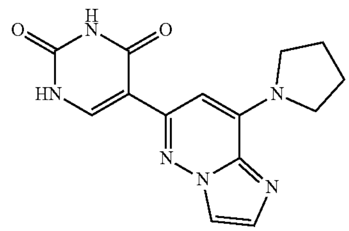 [SMILES: O=c1[nH]cc(-c2cc(N3CCCC3)c3nccn3n2)c(=O)[nH]1] | 5-(8-pyrrolidin-1-ylimidazo[1,2-b]pyridazin-6-yl)-1H-pyrimidine-2,4-dione |
| 10 | 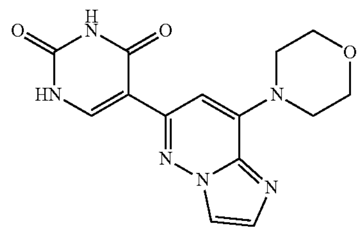 [SMILES: O=c1[nH]cc(-c2cc(N3CCOCC3)c3nccn3n2)c(=O)[nH]1] | 5-(8-morpholinoimidazo[1,2-b]pyridazin-6-yl)-1H-pyrimidine-2,4-dione |
| 11 | 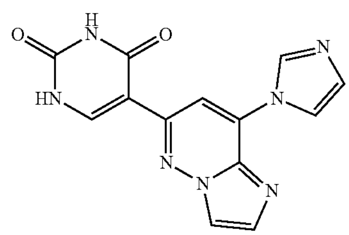 [SMILES: O=c1[nH]cc(-c2cc(-n3ccnc3)c3nccn3n2)c(=O)[nH]1] | 5-(8-imidazol-1-ylimidazo[1,2-b]pyridazin-6-yl)-1H-pyrimidine-2,4-dione |
| 12 | 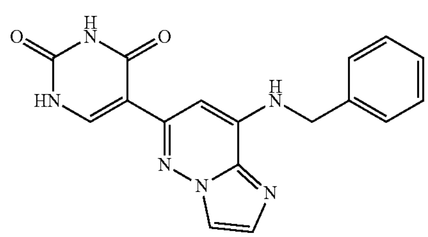 [SMILES: O=c1[nH]cc(-c2cc(NCc3ccccc3)c3nccn3n2)c(=O)[nH]1] | 5-(8-(benzylamino)imidazo[1,2-b]pyridazin-6-yl)pyrimidine-2,4(1H,3H)-dione |
| 13 | 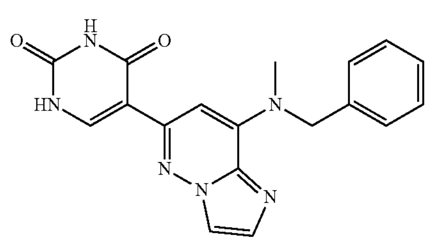 [SMILES: CN(Cc1ccccc1)c1cc(-c2c[nH]c(=O)[nH]c2=O)nn2ccnc12] | 5-(8-(benzyl(methyl)amino)imidazo[1,2-b]pyridazin-6-yl)pyrimidine-2,4(1H,3H)-dione |
| 14 | 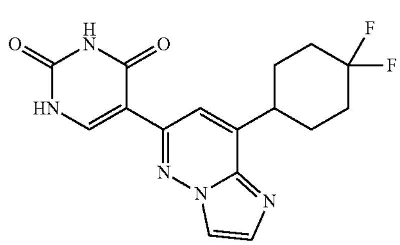 [SMILES: O=c1[nH]cc(-c2cc(C3CCC(F)(F)CC3)c3nccn3n2)c(=O)[nH]1] | 5-(8-(4,4-difluorocyclohexyl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 15 | 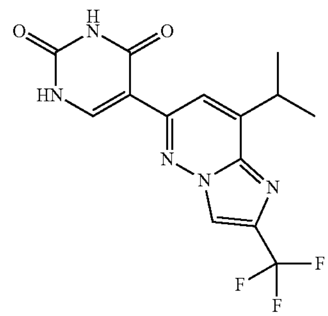 [SMILES: CC(C)c1cc(-c2c[nH]c(=O)[nH]c2=O)nn2cc(C(F)(F)F)nc12] | 5-(8-isopropyl-2-(trifluoromethyl)imidazo[1,2-b]pyridazin-6-yl)pyrimidine-2,4(1H,3H)-dione |
| 16 | 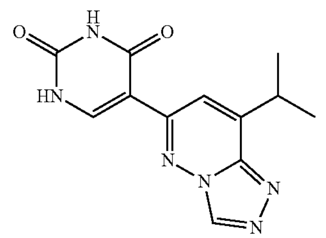 [SMILES: CC(C)c1cc(-c2c[nH]c(=O)[nH]c2=O)nn2cnnc12] | 5-(8-isopropyl-[1,2,4]triazolo[4,3-b]pyridazin-6-yl)pyrimidine-2,4(1H,3H)-dione |
| 17 | 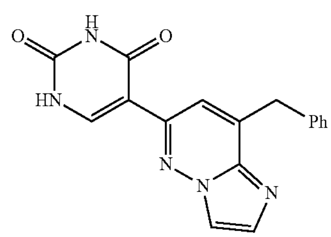 [SMILES: O=c1[nH]cc(-c2cc(Cc3ccccc3)c3nccn3n2)c(=O)[nH]1] | 5-(8-benzylimidazo[1,2-b]pyridazin-6-yl)-1H-pyrimidine-2,4-dione |
| 18 | 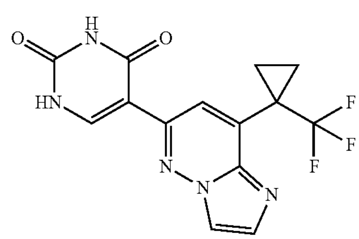 [SMILES: O=c1[nH]cc(-c2cc(C3(C(F)(F)F)CC3)c3nccn3n2)c(=O)[nH]1] | 5-[8-[1-(trifluoromethyl)cyclopropyl]imidazo[1,2-b]pyridazin-6-yl]-1H-pyrimidine-2,4-dione |
| 19 | 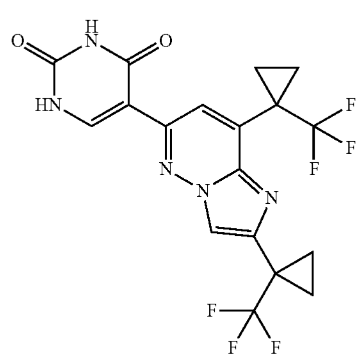 [SMILES: O=c1[nH]cc(-c2cc(C3(C(F)(F)F)CC3)c3nc(C4(C(F)(F)F)CC4)cn3n2)c(=O)[nH]1] | 5-[2,8-bis[1-(trifluoromethyl)cyclopropyl]imidazo[1,2-b]pyridazin-6-yl]-1H-pyrimidine-2,4-dione |

TABLE 2-continued

| Ex. No. | Structure | IUPAC Name |
|---|---|---|
| 20 | 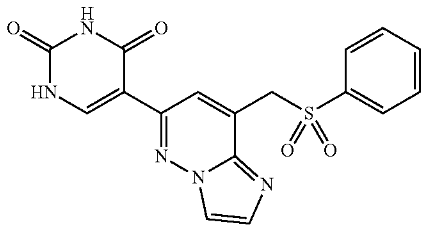 [SMILES: O=c1[nH]cc(-c2cc(CS(=O)(=O)c3ccccc3)c3nccn3n2)c(=O)[nH]1] | 5-[8-(benzenesulfonylmethyl)imidazo[1,2-b]pyridazin-6-yl]-1H-pyrimidine-2,4-dione |
| 21 | 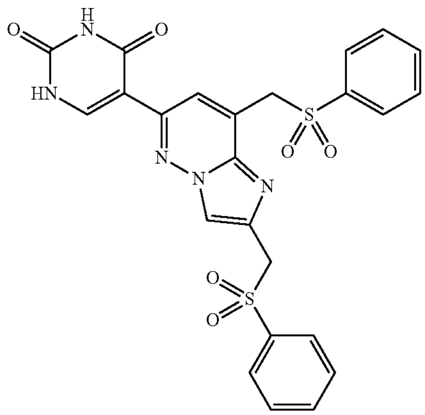 [SMILES: O=c1[nH]cc(-c2cc(CS(=O)(=O)c3ccccc3)c3nc(CS(=O)(=O)c4ccccc4)cn3n2)c(=O)[nH]1] | 5-[2,8-bis(benzenesulfonylmethyl)imidazo[1,2-b]pyridazin-6-yl]-1H-pyrimidine-2,4-dione |
| 22 | 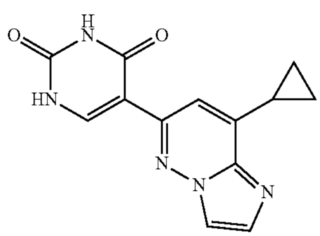 [SMILES: O=c1[nH]cc(-c2cc(C3CC3)c3nccn3n2)c(=O)[nH]1] | 5-(8-cyclopropylimidazo[1,2-b]pyridazin-6-yl)pyrimidine-2,4(1H,3H)-dione |
| 23 | 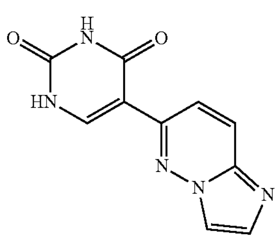 [SMILES: O=c1[nH]cc(-c2ccc3nccn3n2)c(=O)[nH]1] | 5-(imidazo[1,2-b]pyridazin-6-yl)pyrimidine-2,4(1H,3H)-dione |
| 24 | 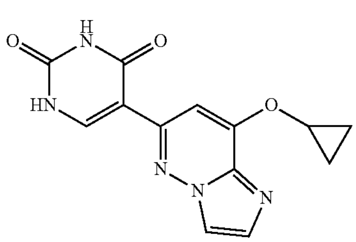 [SMILES: O=c1[nH]cc(-c2cc(OC3CC3)c3nccn3n2)c(=O)[nH]1] | 5-(8-cyclopropoxyimidazo[1,2-b]pyridazin-6-yl)pyrimidine-2,4(1H,3H)-dione |

TABLE 2-continued

Examples

| Ex. No. | Structure | IUPAC Name |
|---|---|---|
| 25 | 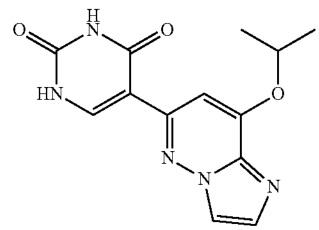 [SMILES: CC(C)Oc1cc(-c2c[nH]c(=O)[nH]c2=O)nn2ccnc12] | 5-(8-isopropoxyimidazo[1,2-b]pyridazin-6-yl)pyrimidine-2,4(1H,3H)-dione |
| 26 | 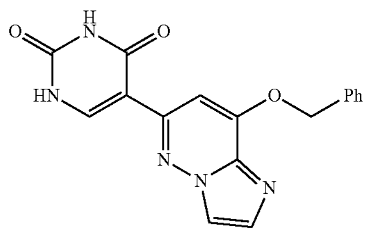 [SMILES: O=c1[nH]cc(-c2cc(OCc3ccccc3)c3nccn3n2)c(=O)[nH]1] | 5-(8-(benzyloxy)imidazo[1,2-b]pyridazin-6-yl)pyrimidine-2,4(1H,3H)-dione |
| 27 | | 5-(7-cyclopropylpyrazolo[1,5-a]pyrimidin-5-yl)pyrimidine-2,4(1H,3H)-dione |
| 27 | | 5-(7-cyclopropylpyrazolo[1,5-a]pyrimidin-5-yl)pyrimidine-2,4(1H,3H)-dione |
| 28 | | 5-(8-((1S,2S)-2-(2-fluorophenyl)cyclopropyl)imidazo[1,2-b]pyridazin-6-yl)pyrimidine-2,4(1H,3H)-dione and 5-(8-((1R,2R)-2-(2-fluorophenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 29 | 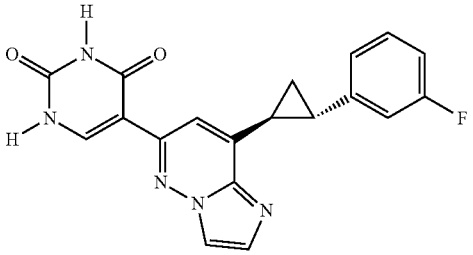 [SMILES: O=c1[nH]cc(-c2cc([C@H]3C[C@@H]3c3cccc(F)c3)c3nccn3n2)c(=O)[nH]1] | 5-(8-((1S,2S)-2-(3-fluorophenyl)cyclopropyl)imidazo[1,2-b]pyridazin-6-yl)pyrimidine-2,4(1H,3H)-dione<br>and<br>5-(8-((1R,2R)-2-(3-fluorophenyl)cyclopropyl)imidazo[1,2-b]pyridazin-6-yl)pyrimidine-2,4(1H,3H)-dione |
| 30 | 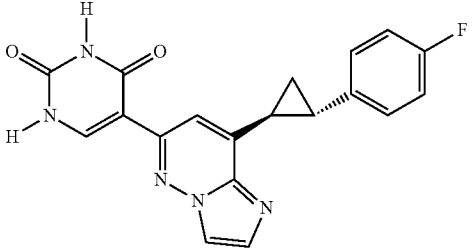 [SMILES: O=c1[nH]cc(-c2cc([C@H]3C[C@@H]3c3ccc(F)cc3)c3nccn3n2)c(=O)[nH]1] | 5-(8-((1S,2S)-2-(4-fluorophenyl)cyclopropyl)imidazo[1,2-b]pyridazin-6-yl)pyrimidine-2,4(1H,3H)-dione<br>and<br>5-(8-((1R,2R)-2-(4-fluorophenyl)cyclopropyl)imidazo[1,2-b]pyridazin-6-yl)pyrimidine-2,4(1H,3H)-dione |
| 31 | 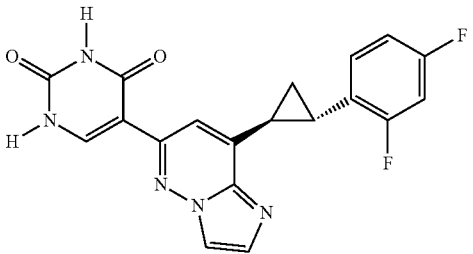 [SMILES: O=c1[nH]cc(-c2cc([C@H]3C[C@@H]3c3ccc(F)cc3F)c3nccn3n2)c(=O)[nH]1] | 5-(8-((1S,2S)-2-(2,4-difluorophenyl)cyclopropyl)imidazo[1,2-b]pyridazin-6-yl)pyrimidine-2,4(1H,3H)-dione<br>and<br>5-(8-((1R,2R)-2-(2,4-difluorophenyl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---------|-----------|------------|
|  | 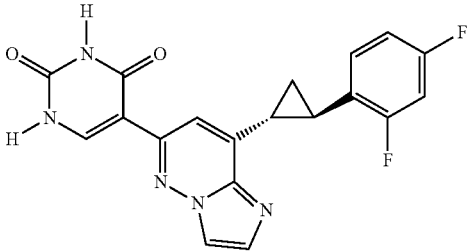 [SMILES: O=c1[nH]cc(-c2cc([C@@H]3C[C@H]3c3ccc(F)cc3F)c3nccn3n2)c(=O)[nH]1] |  |
| 32 | 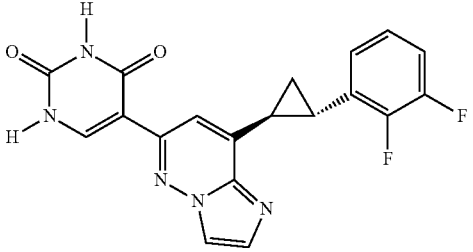 [SMILES: O=c1[nH]cc(-c2cc([C@H]3C[C@@H]3c3cccc(F)c3F)c3nccn3n2)c(=O)[nH]1]

and

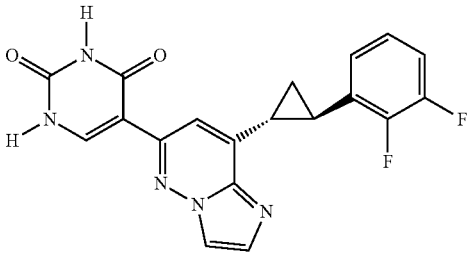 [SMILES: O=c1[nH]cc(-c2cc([C@@H]3C[C@H]3c3cccc(F)c3F)c3nccn3n2)c(=O)[nH]1] | 5-(8-((1S,2S)-2-(2,3-difluorophenyl)cyclopropyl)imidazo[1,2-b]pyridazin-6-yl)pyrimidine-2,4(1H,3H)-dione
and
5-(8-((1R,2R)-2-(2,3-difluorophenyl)cyclopropyl)imidazo[1,2-b]pyridazin-6-yl)pyrimidine-2,4(1H,3H)-dione |
| 33 | 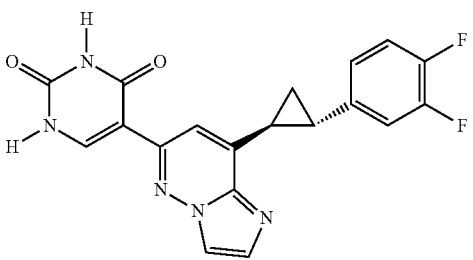 [SMILES: O=c1[nH]cc(-c2cc([C@H]3C[C@@H]3c3ccc(F)c(F)c3)c3nccn3n2)c(=O)[nH]1]

and

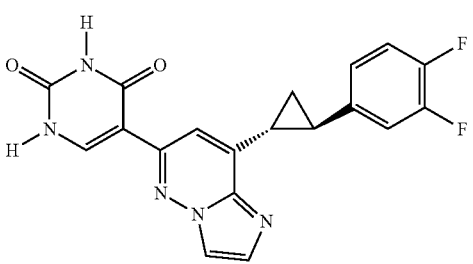 [SMILES: O=c1[nH]cc(-c2cc([C@@H]3C[C@H]3c3ccc(F)c(F)c3)c3nccn3n2)c(=O)[nH]1] | 5-(8-((1S,2S)-2-(3,4-difluorophenyl)cyclopropyl)imidazo[1,2-b]pyridazin-6-yl)pyrimidine-2,4(1H,3H)-dione
and
5-(8-((1R,2R)-2-(3,4-difluorophenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 34 | 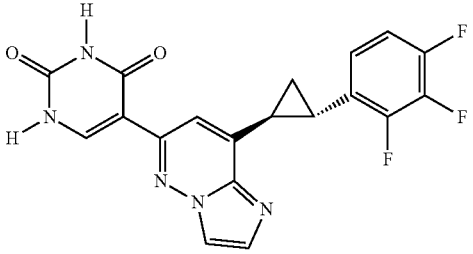 [SMILES: O=c1[nH]cc(-c2cc([C@H]3C[C@@H]3c3ccc(F)c(F)c3F)c3nccn3n2)c(=O)[nH]1] 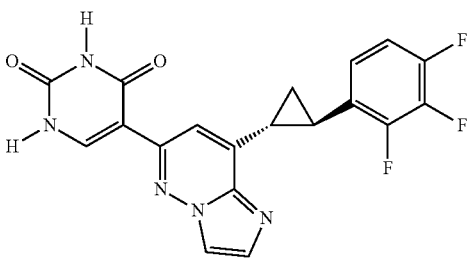 [SMILES: O=c1[nH]cc(-c2cc([C@@H]3C[C@H]3c3ccc(F)c(F)c3F)c3nccn3n2)c(=O)[nH]1] and | 5-(8-((1S,2S)-2-(2,3,4-trifluorophenyl)cyclopropyl)imidazo[1,2-b]pyridazin-6-yl)pyrimidine-2,4(1H,3H)-dione and 5-(8-((1R,2R)-2-(2,3,4-trifluorophenyl)cyclopropyl)imidazo[1,2-b]pyridazin-6-yl)pyrimidine-2,4(1H,3H)-dione |
| 35 | 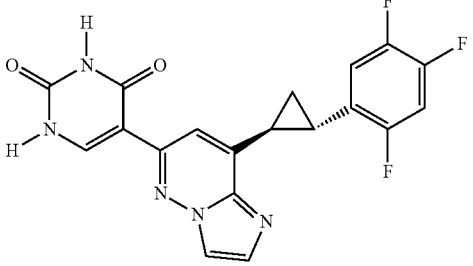 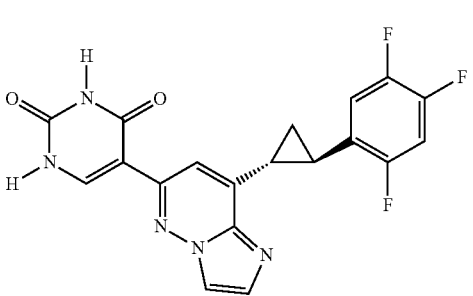 [SMILES: O=c1[nH]cc(-c2cc([C@@H]3C[C@H]3c3cc(F)c(F)cc3F)c3nccn3n2)c(=O)[nH]1] and | 5-(8-((1S,2S)-2-(2,4,5-trifluorophenyl)cyclopropyl)imidazo[1,2-b]pyridazin-6-yl)pyrimidine-2,4(1H,3H)-dione and 5-(8-((1R,2R)-2-(2,4,5-trifluorophenyl)cyclopropyl)imidazo[1,2-b]pyridazin-6-yl)pyrimidine-2,4(1H,3H)-dione |
| 36 | 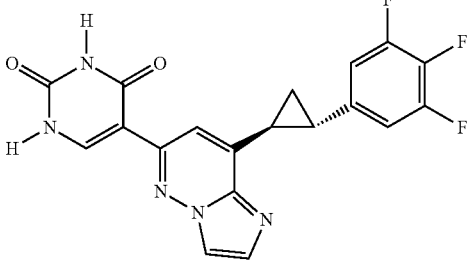  and | 5-(8-((1S,2S)-2-(3,4,5-trifluorophenyl)cyclopropyl)imidazo[1,2-b]pyridazin-6-yl)pyrimidine-2,4(1H,3H)-dione and 5-(8-((1R,2R)-2-(3,4,5-trifluorophenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| | (structure) | |
| 38 | (structures) | 5-(8-((1S,2S)-2-(3-chlorophenyl)cyclopropyl)imidazo[1,2-b]pyridazin-6-yl)pyrimidine-2,4(1H,3H)-dione<br>and<br>5-(8-((1R,2R)-2-(3-chlorophenyl)cyclopropyl)imidazo[1,2-b]pyridazin-6-yl)pyrimidine-2,4(1H,3H)-dione |
| 39 | (structures) | 5-(8-((1S,2S)-2-(4-chlorophenyl)cyclopropyl)imidazo[1,2-b]pyridazin-6-yl)pyrimidine-2,4(1H,3H)-dione<br>and<br>5-(8-((1R,2R)-2-(4-chlorophenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 41 | 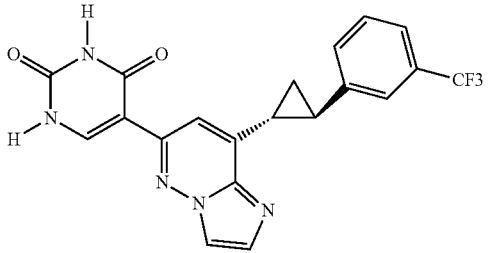 [SMILES: O=c1[nH]cc(-c2cc([C@@H]3C[C@H]3c3cccc(C(F)(F)F)c3)c3nccn3n2)c(=O)[nH]1] | 5-[8-[(1S,2S)-2-[3-(trifluoromethyl)phenyl]cyclopropyl]imidazo[1,2-b]pyridazin-6-yl]-1H-pyrimidine-2,4-dione<br>and<br>5-[8-[(1R,2R)-2-[3-(trifluoromethyl)phenyl]cyclopropyl]imidazo[1,2-b]pyridazin-6-yl]-1H-pyrimidine-2,4-dione |
| 42 | 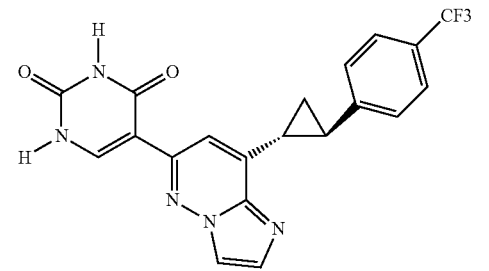 [SMILES: O=c1[nH]cc(-c2cc([C@@H]3C[C@H]3c3ccc(C(F)(F)F)cc3)c3nccn3n2)c(=O)[nH]1] | 5-[8-[(1S,2S)-2-[4-(trifluoromethyl)phenyl]cyclopropyl]imidazo[1,2-b]pyridazin-6-yl]-1H-pyrimidine-2,4-dione<br>and<br>5-[8-[(1R,2R)-2-[4-(trifluoromethyl)phenyl]cyclopropyl]imidazo[1,2-b]pyridazin-6-yl]-1H-pyrimidine-2,4-dione |
| 45 | 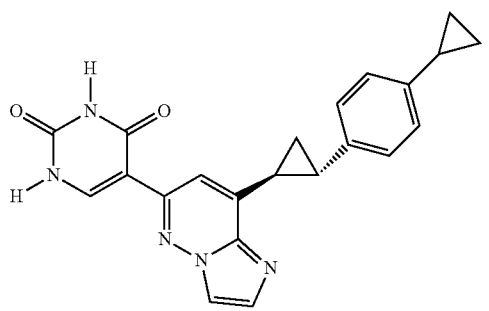 [SMILES: O=c1[nH]cc(-c2cc([C@H]3C[C@@H]3c3ccc(C4CC4)cc3)c3nccn3n2)c(=O)[nH]1] | 5-(8-((1S,2S)-2-(4-cyclopropylphenyl)cyclopropyl)imidazo[1,2-b]pyridazin-6-yl)pyrimidine-2,4(1H,3H)-dione<br>and<br>5-(8-((1R,2R)-2-(4-cyclopropylphenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| | 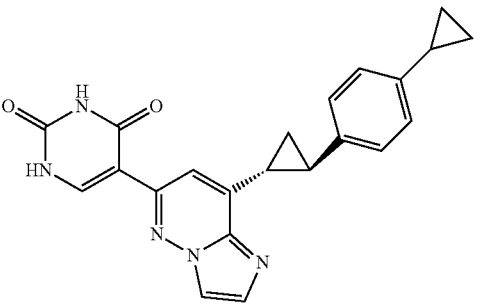 [SMILES: O=c1[nH]cc(-c2cc([C@@H]3C[C@H]3c3ccc(C4CC4)cc3)c3nccn3n2)c(=O)[nH]1] | |
| 47 | 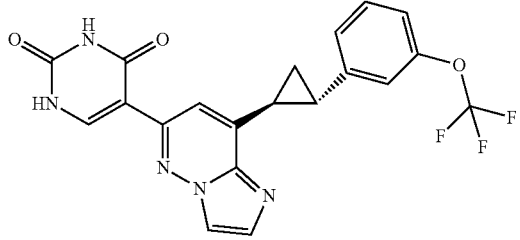 [SMILES: O=c1[nH]cc(-c2cc([C@H]3C[C@@H]3c3cccc(OC(F)(F)F)c3)c3nccn3n2)c(=O)[nH]1] and 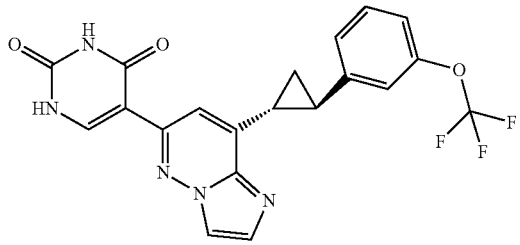 [SMILES: O=c1[nH]cc(-c2cc([C@@H]3C[C@H]3c3cccc(OC(F)(F)F)c3)c3nccn3n2)c(=O)[nH]1] | 5-(8-((1S,2S)-2-(3-(trifluoromethoxy)phenyl)cyclopropyl) imidazo[1,2-b]pyridazin-6-yl) pyrimidine-2,4(1H,3H)-dione and 5-(8-((1R,2R)-2-(3-(trifluoromethoxy)phenyl)cyclopropyl) imidazo[1,2-b]pyridazin-6-yl) pyrimidine-2,4(1H,3H)-dione |
| 48 | 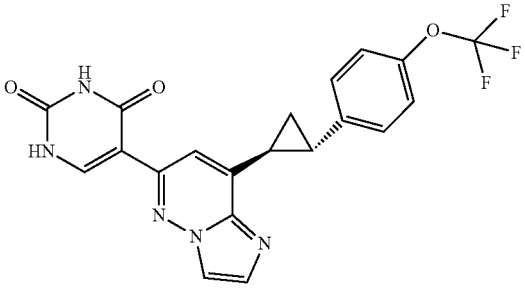 [SMILES: O=c1[nH]cc(-c2cc([C@H]3C[C@@H]3c3ccc(OC(F)(F)F)cc3)c3nccn3n2)c(=O)[nH]1] and 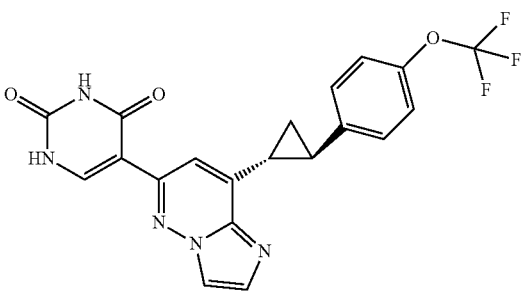 [SMILES: O=c1[nH]cc(-c2cc([C@@H]3C[C@H]3c3ccc(OC(F)(F)F)cc3)c3nccn3n2)c(=O)[nH]1] | 5-(8-((1S,2S)-2-(4-(trifluoromethoxy)phenyl)cyclopropyl) imidazo[1,2-b]pyridazin-6-yl)pyrimidine-2,4(1H,3H)-dione and 5-(8-((1R,2R)-2-(4-(trifluoromethoxy)phenyl)cyclopropyl) imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 49 | 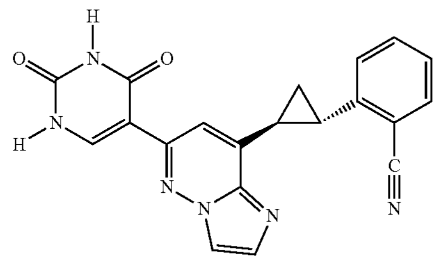 [SMILES: N#Cc1ccccc1[C@H]1C[C@@H]1c1cc(-c2c[nH]c(=O)[nH]c2=O)nn2ccnc12] | 2-((1S,2S)-2-(6-(2,4-dioxo-1,2,3,4-tetrahydropyrimidin-5-yl)imidazo[1,2-b]pyridazin-8-yl)cyclopropyl)benzonitrile |
| 50 | 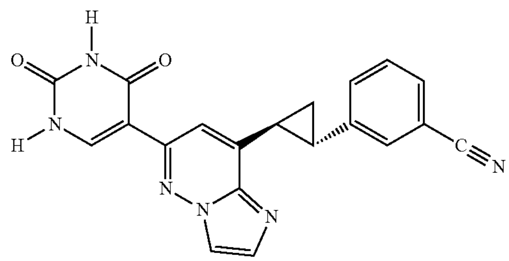 [SMILES: N#Cc1cccc([C@H]2C[C@@H]2c2cc(-c3c[nH]c(=O)[nH]c3=O)nn3ccnc23)c1] | 3-((1S,2S)-2-(6-(2,4-dioxo-1,2,3,4-tetrahydropyrimidin-5-yl)imidazo[1,2-b]pyridazin-8-yl)cyclopropyl)benzonitrile |
| 52 | | 5-[8-[(1S,2S)-2-(2-pyridyl)cyclopropyl]imidazo[1,2-b]pyridazin-6-yl]-1H-pyrimidine-2,4-dione and 5-[8-[(1R,2R)-2-(2-pyridyl)cyclopropyl]imidazo[1,2-b]pyridazin-6-yl]-1H-pyrimidine-2,4-dione |
| 53 | | 5-[8-[(1S,2S)-2-(3-pyridyl)cyclopropyl]imidazo[1,2-b]pyridazin-6-yl]-1H-pyrimidine-2,4-dione and 5-[8-[(1R,2R)-2-(3-pyridyl)cyclopropyl]imidazo[1,2-b]pyridazin-6-yl]-1H-pyrimidine-2,4-dione |

TABLE 2-continued

| Ex. No. | Structure | IUPAC Name |
|---|---|---|
| 54 | 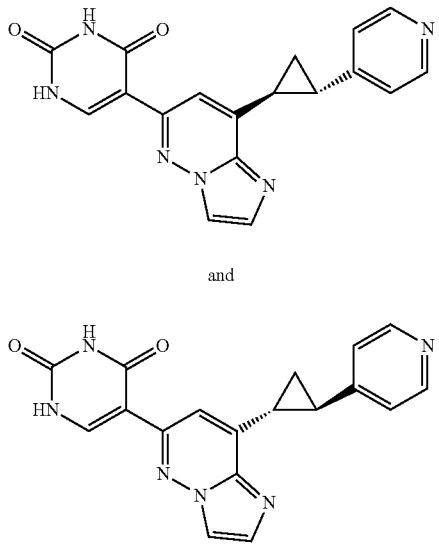 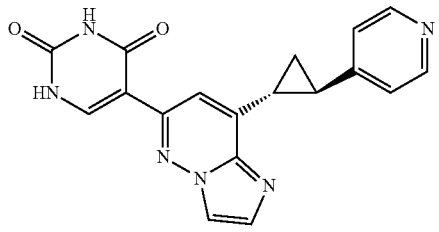 [SMILES: O=c1[nH]cc(-c2cc([C@@H]3C[C@H]3c3ccncc3)c3nccn3n2)c(=O)[nH]1] | 5-[8-[(1S,2S)-2-(4-pyridyl)cyclopropyl]imidazo[1,2-b]pyridazin-6-yl]-1H-pyrimidine-2,4-dione and 5-[8-[(1R,2R)-2-(4-pyridyl)cyclopropyl]imidazo[1,2-b]pyridazin-6-yl]-1H-pyrimidine-2,4-dione |
| 55 | 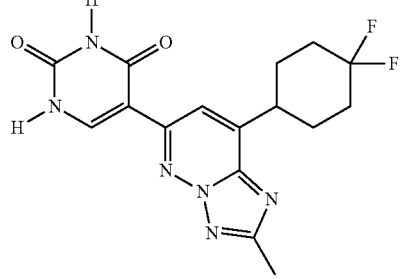 | 5-(8-(4,4-difluorocyclohexyl)-2-methyl-[1,2,4]triazolo[1,5-b]pyridazin-6-yl)pyrimidine-2,4(1H,3H)-dione |
| 56 | 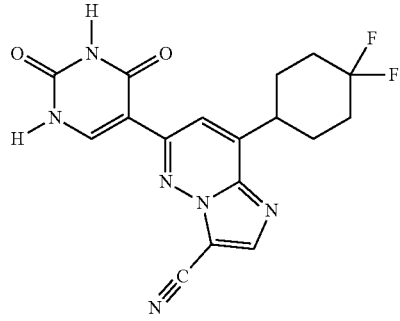 [SMILES: N#Cc1cnc2c(C3CCC(F)(F)CC3)cc(-c3c[nH]c(=O)[nH]c3=O)nn12] | 8-(4,4-difluorocyclohexyl)-6-(2,4-dioxo-1,2,3,4-tetrahydropyrimidin-5-yl)imidazo[1,2-b]pyridazine-3-carbonitrile |
| 57 | 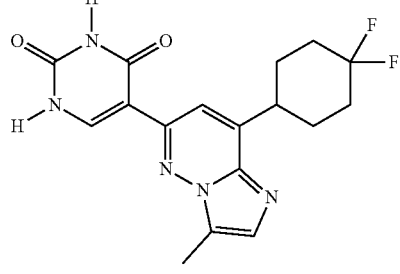 | 5-(8-(4,4-difluorocyclohexyl)-3-methylimidazo[1,2-b]pyridazin-6-yl)pyrimidine-2,4(1H,3H)-dione |

TABLE 2-continued

| Ex. No. | Structure | IUPAC Name |
| --- | --- | --- |
| 58 | 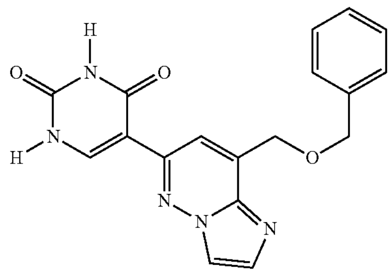 [SMILES: O=c1[nH]cc(-c2cc(COCc3ccccc3)c3nccn3n2)c(=O)[nH]1] | 5-(8-((benzyloxy)methyl)imidazo[1,2-b]pyridazin-6-yl)pyrimidine-2,4(1H,3H)-dione |
| 59 | 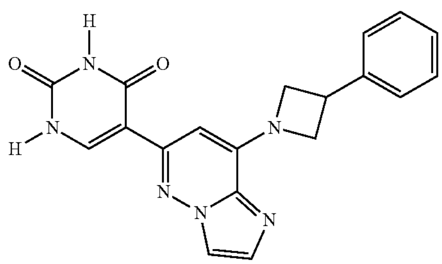 [SMILES: O=c1[nH]cc(-c2cc(N3CC(c4ccccc4)C3)c3nccn3n2)c(=O)[nH]1] | 5-(8-(3-phenylazetidin-1-yl)imidazo[1,2-b]pyridazin-6-yl)pyrimidine-2,4(1H,3H)-dione |
| 60 | and | 5-(8-((1S,2S)-2-(3,5-difluorophenyl)cyclopropyl)imidazo[1,2-b]pyridazin-6-yl)pyrimidine-2,4(1H,3H)-dione<br>5-(8-((1R,2R)-2-(3,5-difluorophenyl)cyclopropyl)imidazo[1,2-b]pyridazin-6-yl)pyrimidine-2,4(1H,3H)-dione |
| 61 | and | 5-(8-((1S,2S)-2-(2,3,5-trifluorophenyl)cyclopropyl)imidazo[1,2-b]pyridazin-6-yl)pyrimidine-2,4(1H,3H)-dione<br>and<br>5-(8-((1R,2R)-2-(2,3,5-trifluorophenyl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 62 | 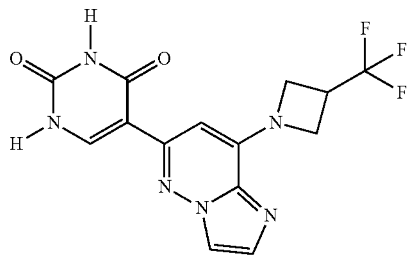 [SMILES: O=c1[nH]cc(-c2cc(N3CC(C(F)(F)F)C3)c3nccn3n2)c(=O)[nH]1] | 5-(8-(3-(trifluoromethyl)azetidin-1-yl)imidazo[1,2-b]pyridazin-6-yl)pyrimidine-2,4(1H,3H)-dione |
| 63 | 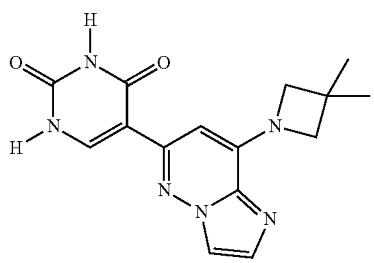 [SMILES: CC1(C)CN(c2cc(-c3c[nH]c(=O)[nH]c3=O)nn3ccnc23)C1] | 5-(8-(3,3-dimethylazetidin-1-yl)imidazo[1,2-b]pyridazin-6-yl)pyrimidine-2,4(1H,3H)-dione |
| 64 | | 5-((1S,2S)-2-(6-(2,4-dioxo-1,2,3,4-tetrahydropyrimidin-5-yl)imidazo[1,2-b]pyridazin-8-yl)cyclopropyl)-2-fluorobenzonitrile and 5-((1R,2R)-2-(6-(2,4-dioxo-1,2,3,4-tetrahydropyrimidin-5-yl)imidazo[1,2-b]pyridazin-8-yl)cyclopropyl)-2-fluorobenzonitrile |
| 65 | 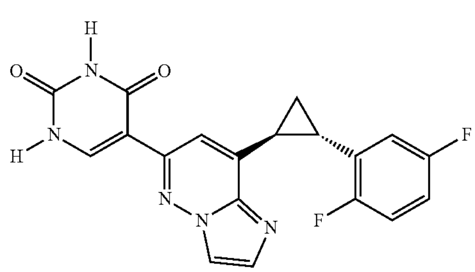 [SMILES: O=c1[nH]cc(-c2cc([C@H]3C[C@@H]3c3cc(F)ccc3F)c3nccn3n2)c(=O)[nH]1] | 5-(8-((1S,2S)-2-(2,5-difluorophenyl)cyclopropyl)imidazo[1,2-b]pyridazin-6-yl)pyrimidine-2,4(1H,3H)-dione and 5-(8-((1R,2R)-2-(2,5-difluorophenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| | and | |
| 66 | 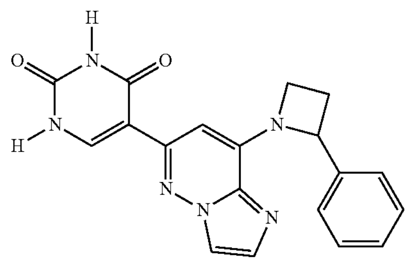 [SMILES: O=c1[nH]cc(-c2cc(N3CCC3c3ccccc3)c3nccn3n2)c(=O)[nH]1] | 5-(8-(2-phenylazetidin-1-yl)imidazo[1,2-b]pyridazin-6-yl)pyrimidine-2,4(1H,3H)-dione |
| 67 | 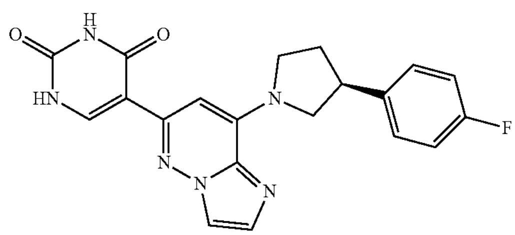 [SMILES: O=c1[nH]cc(-c2cc(N3CC[C@@H](c4ccc(F)cc4)C3)c3nccn3n2)c(=O)[nH]1] | (S)-5-(8-(3-(4-fluorophenyl)pyrrolidin-1-yl)imidazo[1,2-b]pyridazin-6-yl)pyrimidine-2,4(1H,3H)-dione |
| 68 | 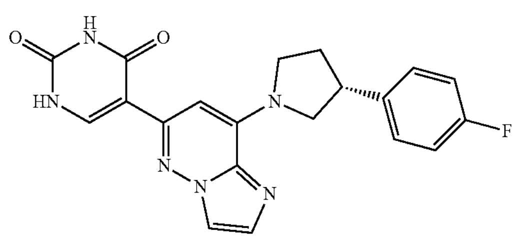 [SMILES: O=c1[nH]cc(-c2cc(N3CC[C@H](c4ccc(F)cc4)C3)c3nccn3n2)c(=O)[nH]1] | (R)-5-(8-(3-(4-fluorophenyl)pyrrolidin-1-yl)imidazo[1,2-b]pyridazin-6-yl)pyrimidine-2,4(1H,3H)-dione |
| 69 | 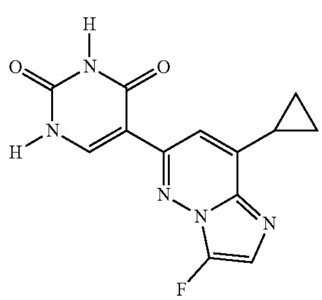 [SMILES: O=c1[nH]cc(-c2cc(C3CC3)c3ncc(F)n3n2)c(=O)[nH]1] | 5-(8-cyclopropyl-3-fluoro-imidazo[1,2-b]pyridazin-6-yl)-1H-pyrimidine-2,4-dione |

TABLE 2-continued

Examples

| Ex. No. | Structure | IUPAC Name |
|---|---|---|
| 70 | 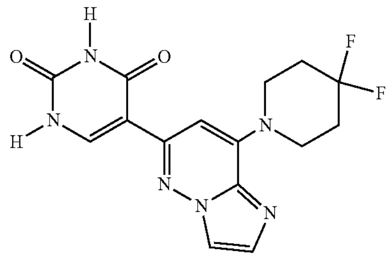 [SMILES: O=c1[nH]cc(-c2cc(N3CCC(F)(F)CC3)c3nccn3n2)c(=O)[nH]1] | 5-[8-(4,4-difluoro-1-piperidyl)imidazo[1,2-b]pyridazin-6-yl]-1H-pyrimidine-2,4-dione |
| 71 | 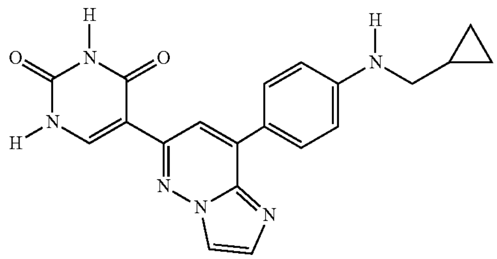 [SMILES: O=c1[nH]cc(-c2cc(-c3ccc(NCC4CC4)cc3)c3nccn3n2)c(=O)[nH]1] | 5-[8-[4-(cyclopropylmethylamino)phenyl]imidazo[1,2-b]pyridazin-6-yl]-1H-pyrimidine-2,4-dione |
| 72 | 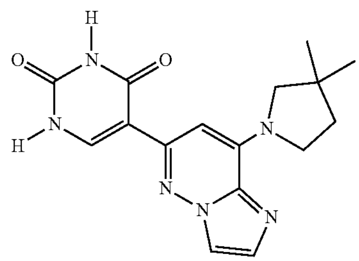 [SMILES: CC1(C)CCN(c2cc(-c3c[nH]c(=O)[nH]c3=O)nn3ccnc23)C1] | 5-[8-(3,3-dimethylpyrrolidin-1-yl)imidazo[1,2-b]pyridazin-6-yl]-1H-pyrimidine-2,4-dione |
| 73 | | 5-[8-[(3S,4S)-3,4-difluoropyrrolidin-1-yl]imidazo[1,2-b]pyridazin-6-yl]-1H-pyrimidine-2,4-dione and 5-[8-[(3R,4R)-3,4-difluoropyrrolidin-1-yl]imidazo[1,2-b]pyridazin-6-yl]-1H-pyrimidine-2,4-dione |
| 74 | 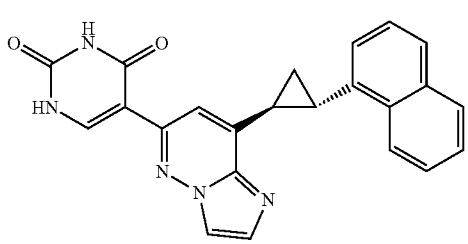 [SMILES: O=c1[nH]cc(-c2cc([C@H]3C[C@@H]3c3cccc4ccccc34)c3nccn3n2)c(=O)[nH]1] | 5-[8-[(1S,2S)-2-(1-naphthyl)cyclopropyl]imidazo[1,2-b]pyridazin-6-yl]-1H-pyrimidine-2,4-dione and 5-[8-[(1R,2R)-2-(1-naphthyl)cyclopropyl]imidazo[1,2-b]pyridazin-6-yl]-1H-pyrimidine-2,4-dione |

TABLE 2-continued

| Ex. No. | Structure | IUPAC Name |
|---|---|---|
| | and (structure shown) | |
| 75 | (structure shown) | 5-(2,8-dicyclopropylimidazo[1,2-b]pyridazin-6-yl)-1H-pyrimidine-2,4-dione |
| 76 | (structures shown) and | 5-[3-fluoro-8-[(1S,2S)-2-(4-fluorophenyl)cyclopropyl]imidazo[1,2-b]pyridazin-6-yl]-1H-pyrimidine-2,4-dione and 5-[3-fluoro-8-[(1R,2R)-2-(4-fluorophenyl)cyclopropyl]imidazo[1,2-b]pyridazin-6-yl]-1H-pyrimidine-2,4-dione |
| 77 | (structure shown) and | 5-[8-[(3S,4R)-3,4-difluoropyrrolidin-1-yl]imidazo[1,2-b]pyridazin-6-yl]-1H-pyrimidine-2,4-dione and 5-[8-[(3R,4S)-3,4-difluoropyrrolidin-1-yl]imidazo[1,2-b]pyridazin-6-yl]-1H-pyrimidine-2,4-dione |

TABLE 2-continued
| Ex. No. | Structure | IUPAC Name |
|---|---|---|
| | 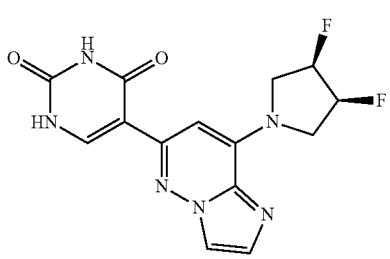 | |
| 78 | 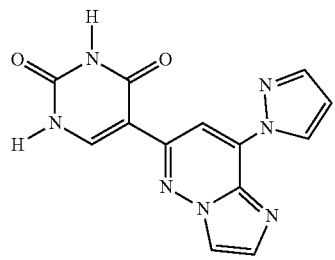 [SMILES: O=c1[nH]cc(-c2cc(-n3cccn3)c3nccn3n2)c(=O)[nH]1] | 5-(8-pyrazol-1-ylimidazo[1,2-b]pyridazin-6-yl)-1H-pyrimidine-2,4-dione |
| 79 | 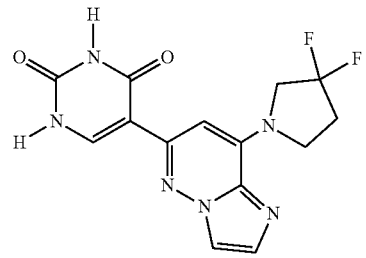 [SMILES: O=c1[nH]cc(-c2cc(N3CCC(F)(F)C3)c3nccn3n2)c(=O)[nH]1] | 5-[8-(3,3-difluoropyrrolidin-1-yl)imidazo[1,2-b]pyridazin-6-yl]-1H-pyrimidine-2,4-dione |
| 80 | 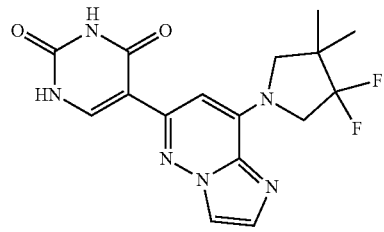 | 5-[8-(3,3-difluoro-4,4-dimethyl-pyrrolidin-1-yl)imidazo[1,2-b]pyridazin-6-yl]-1H-pyrimidine-2,4-dione |
| 81 | 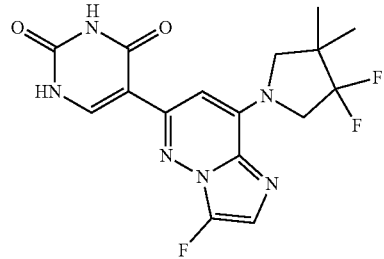 | 5-[8-(3,3-difluoro-4,4-dimethyl-pyrrolidin-1-yl)-3-fluoro-imidazo[1,2-b]pyridazin-6-yl]-1H-pyrimidine-2,4-dione |

TABLE 2-continued

| Ex. No. | Structure | IUPAC Name |
|---|---|---|
| 82 | 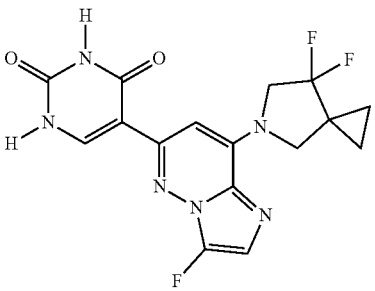 [SMILES: O=c1[nH]cc(-c2cc(N3CC(F)(F)C4(CC4)C3)c3ncc(F)n3n2)c(=O)[nH]1] | 5-(8-(7,7-difluoro-5-azaspiro[2.4]heptan-5-yl)-3-fluoroimidazo[1,2-b]pyridazin-6-yl)pyrimidine-2,4(1H,3H)-dione |
| 83 | 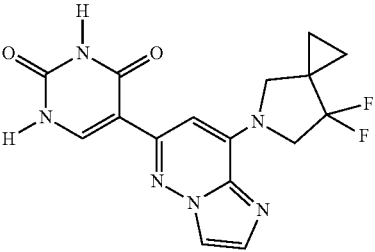 [SMILES: O=c1[nH]cc(-c2cc(N3CC(F)(F)C4(CC4)C3)c3nccn3n2)c(=O)[nH]1] | 5-(8-(7,7-difluoro-5-azaspiro[2.4]heptan-5-yl)imidazo[1,2-b]pyridazin-6-yl)pyrimidine-2,4(1H,3H)-dione |
| 84 | 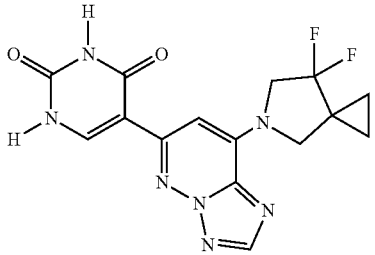 [SMILES: O=c1[nH]cc(-c2cc(N3CC(F)(F)C4(CC4)C3)c3ncnn3n2)c(=O)[nH]1] | 5-(8-(7,7-difluoro-5-azaspiro[2.4]heptan-5-yl)-[1,2,4]triazolo[1,5-b]pyridazin-6-yl)pyrimidine-2,4(1H,3H)-dione |
| 85 | 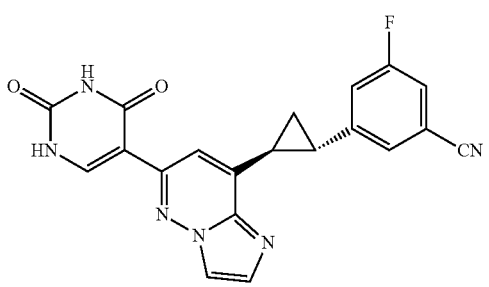 [SMILES: N#Cc1cc(F)cc([C@H]2C[C@@H]2c2cc(-c3c[nH]c(=O)[nH]c3=O)nn3ccnc23)c1] | 3-[(1S,2S)-2-[6-(2,4-dioxo-1H-pyrimidin-5-yl)imidazo[1,2-b]pyridazin-8-yl]cyclopropyl]-5-fluoro-benzonitrile<br>and<br>3-[(1R,2R)-2-[6-(2,4-dioxo-1H-pyrimidin-5-yl)imidazo[1,2-b]pyridazin-8-yl]cyclopropyl]-5-fluoro-benzonitrile |

TABLE 2-continued

Examples

| Ex. No. | Structure | IUPAC Name |
|---|---|---|
| 86 | 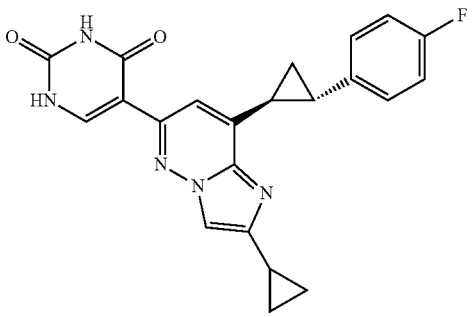 [SMILES: O=c1[nH]cc(-c2cc([C@H]3C[C@@H]3c3ccc(F)cc3)c3nc(C4CC4)cn3n2)c(=O)[nH]1] and 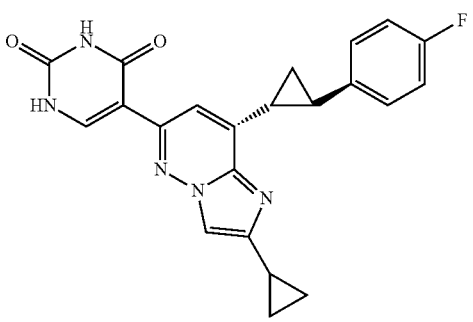 | 5-[2-cyclopropyl-8-[(1S,2S)-2-(4-fluorophenyl)cyclopropyl]imidazo[1,2-b]pyridazin-6-yl]-1H-pyrimidine-2,4-dione and 5-[2-cyclopropyl-8-[(1R,2R)-2-(4-fluorophenyl)cyclopropyl]imidazo[1,2-b]pyridazin-6-yl]-1H-pyrimidine-2,4-dione |
| 87 | 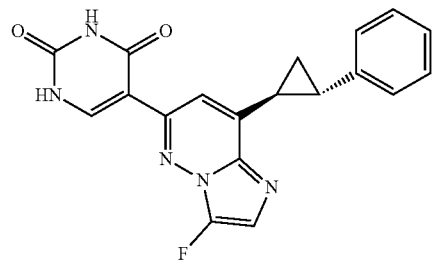 [SMILES: O=c1[nH]cc(-c2cc([C@H]3C[C@@H]3c3ccccc3)c3ncc(F)n3n2)c(=O)[nH]1] and 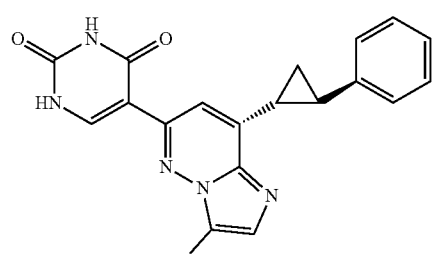 | 5-[3-fluoro-8-[(1S,2S)-2-phenylcyclopropyl]imidazo[1,2-b]pyridazin-6-yl]-1H-pyrimidine-2,4-dione and 5-[3-fluoro-8-[(1R,2R)-2-phenylcyclopropyl]imidazo[1,2-b]pyridazin-6-yl]-1H-pyrimidine-2,4-dione |
| 88 | 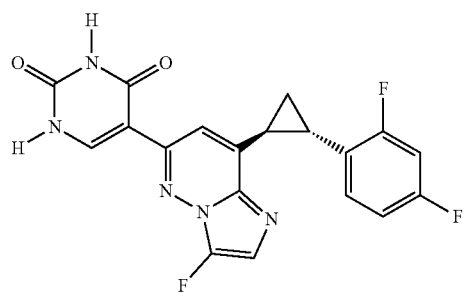 [SMILES: O=c1[nH]cc(-c2cc([C@H]3C[C@@H]3c3ccc(F)cc3F)c3ncc(F)n3n2)c(=O)[nH]1] | 5-[8-[(1S,2S)-2-(2,4-difluorophenyl)cyclopropyl]-3-fluoro-imidazo[1,2-b]pyridazin-6-yl]-1H-pyrimidine-2,4-dione |

TABLE 2-continued

| Ex. No. | Structure | IUPAC Name |
|---|---|---|
| 89 | 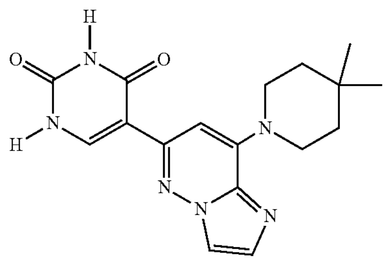 [SMILES: CC1(C)CCN(c2cc(-c3c[nH]c(=O)[nH]c3=O)nn3ccnc23)CC1] | 5-[8-(4,4-dimethyl-1-piperidyl)imidazo[1,2-b]pyridazin-6-yl]-1H-pyrimidine-2,4-dione |
| 90 | 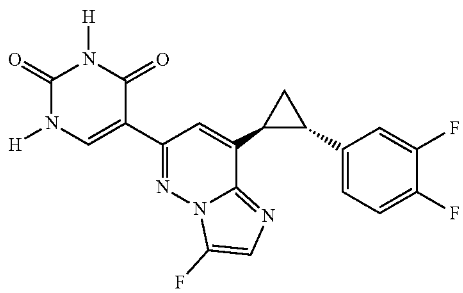 [SMILES: O=c1[nH]cc(-c2cc([C@H]3C[C@@H]3c3ccc(F)c(F)c3)c3ncc(F)n3n2)c(=O)[nH]1] | 5-[8-[(1S,2S)-2-(3,4-difluorophenyl)cyclopropyl]-3-fluoro-imidazo[1,2-b]pyridazin-6-yl]-1H-pyrimidine-2,4-dione |
| 91 | 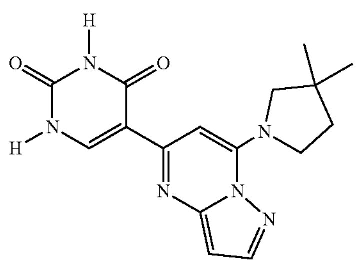 [SMILES: CC1(C)CCN(c2cc(-c3c[nH]c(=O)[nH]c3=O)nc3ccnn23)C1] | 5-(7-(3,3-dimethylpyrrolidin-1-yl)pyrazolo[1,5-a]pyrimidin-5-yl)pyrimidine-2,4(1H,3H)-dione |
| 92 | 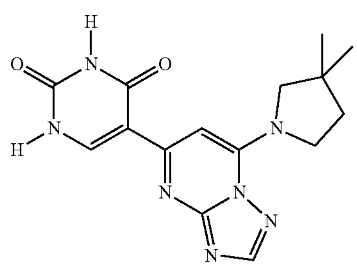 [SMILES: CC1(C)CCN(c2cc(-c3c[nH]c(=O)[nH]c3=O)nc3ncnn23)C1] | 5-(7-(3,3-dimethylpyrrolidin-1-yl)-[1,2,4]triazolo[1,5-a]pyrimidin-5-yl)pyrimidine-2,4(1H,3H)-dione |
| 93 | 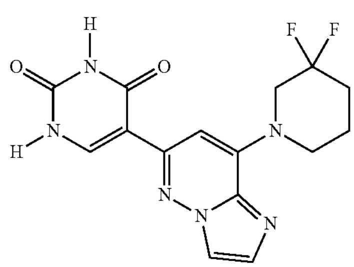 [SMILES: O=c1[nH]cc(-c2cc(N3CCCC(F)(F)C3)c3nccn3n2)c(=O)[nH]1] | 5-(8-(3,3-difluoropiperidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 94 | 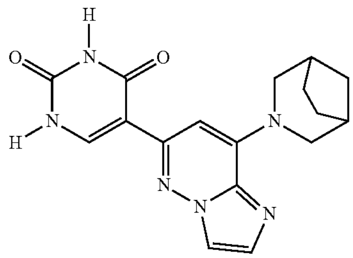 [SMILES: O=c1[nH]cc(-c2cc(N3CC4CCC(C4)C3)c3nccn3n2)c(=O)[nH]1] | 5-(8-(3-azabicyclo[3.2.1]octan-3-yl)imidazo[1,2-b]pyridazin-6-yl)pyrimidine-2,4(1H,3H)-dione |
| 95 | | 5-(8-((1S,2S)-2-(4-fluoro-3-(trifluoromethyl)phenyl)cyclopropyl)imidazo[1,2-b]pyridazin-6-yl)pyrimidine-2,4(1H,3H)-dione<br>and<br>5-(8-((1R,2R)-2-(4-fluoro-3-(trifluoromethyl)phenyl)cyclopropyl)imidazo[1,2-b]pyridazin-6-yl)pyrimidine-2,4(1H,3H)-dione |
| 96 | 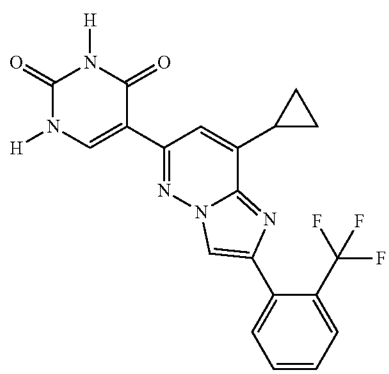 [SMILES: O=c1[nH]cc(-c2cc(C3CC3)c3nc(-c4ccccc4C(F)(F)F)cn3n2)c(=O)[nH]1] | 5-(8-cyclopropyl-2-(2-(trifluoromethyl)phenyl)imidazo[1,2-b]pyridazin-6-yl)pyrimidine-2,4(1H,3H)-dione |
| 97 | 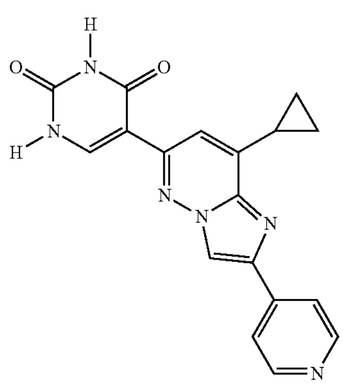 [SMILES: O=c1[nH]cc(-c2cc(C3CC3)c3nc(-c4ccncc4)cn3n2)c(=O)[nH]1] | 5-(8-cyclopropyl-2-(pyridin-4-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 98 | 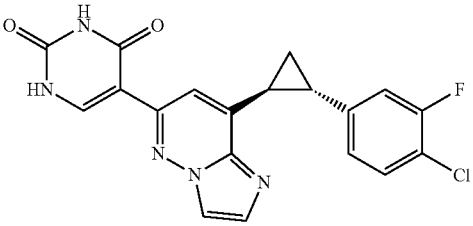 [SMILES: O=c1[nH]cc(-c2cc([C@H]3C[C@@H]3c3ccc(Cl)c(F)c3)c3nccn3n2)c(=O)[nH]1] and 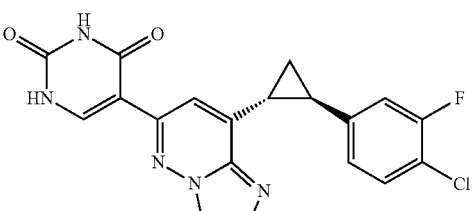 | 5-(8-((1S,2S)-2-(4-chloro-3-fluorophenyl)cyclopropyl)imidazo[1,2-b]pyridazin-6-yl)pyrimidine-2,4(1H,3H)-dione and 5-(8-((1R,2R)-2-(4-chloro-3-fluorophenyl)cyclopropyl)imidazo[1,2-b]pyridazin-6-yl)pyrimidine-2,4(1H,3H)-dione |
| 99 | 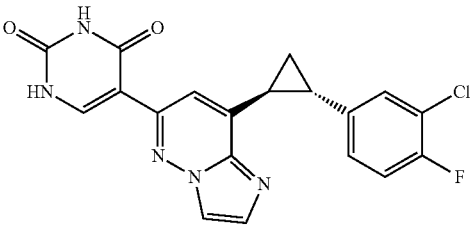 [SMILES: O=c1[nH]cc(-c2cc([C@H]3C[C@@H]3c3ccc(F)c(Cl)c3)c3nccn3n2)c(=O)[nH]1] and 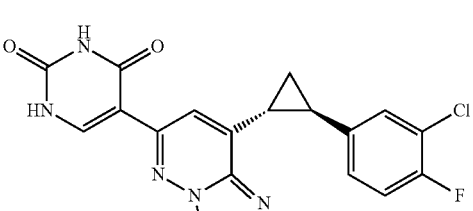 | 5-(8-((1S,2S)-2-(3-chloro-4-fluorophenyl)cyclopropyl)imidazo[1,2-b]pyridazin-6-yl)pyrimidine-2,4(1H,3H)-dione and 5-(8-((1R,2R)-2-(3-chloro-4-fluorophenyl)cyclopropyl)imidazo[1,2-b]pyridazin-6-yl)pyrimidine-2,4(1H,3H)-dione |
| 100 | 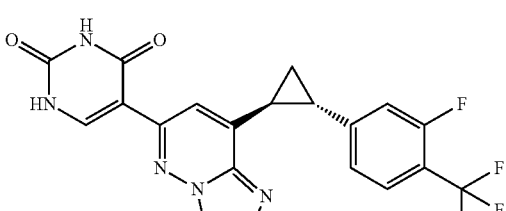 and 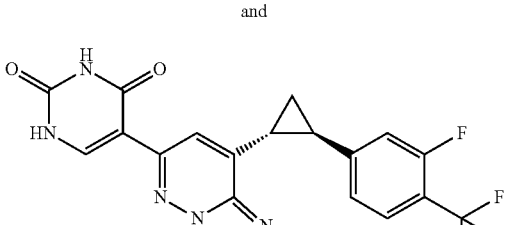 | 5-(8-((1S,2S)-2-(3-fluoro-4-(trifluoromethyl)phenyl)cyclopropyl)imidazo[1,2-b]pyridazin-6-yl)pyrimidine-2,4(1H,3H)-dione and 5-(8-((1R,2R)-2-(3-fluoro-4-(trifluoromethyl)phenyl)cyclopropyl)imidazo[1,2-b]pyridazin-6-yl)pyrimidine-2,4(1H,3H)-dione |

TABLE 2-continued
Examples
| Ex. No. | Structure | IUPAC Name |
|---|---|---|
| 101 | 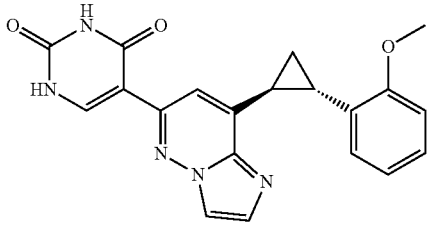 [SMILES: COc1ccccc1[C@H]1C[C@@H]1c1cc(-c2c[nH]c(=O)[nH]c2=O)nn2ccnc12] and 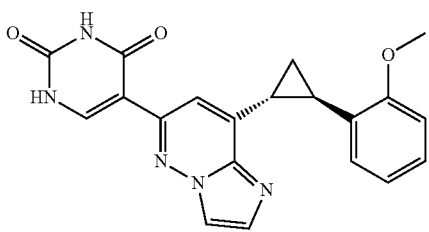 [SMILES: COc1ccccc1[C@@H]1C[C@H]1c1cc(-c2c[nH]c(=O)[nH]c2=O)nn2ccnc12] | 5-(8-((1S,2S)-2-(2-methoxyphenyl)cyclopropyl)imidazo[1,2-b]pyridazin-6-yl)pyrimidine-2,4(1H,3H)-dione and 5-(8-((1R,2R)-2-(2-methoxyphenyl)cyclopropyl)imidazo[1,2-b]pyridazin-6-yl)pyrimidine-2,4(1H,3H)-dione |
| 102 | 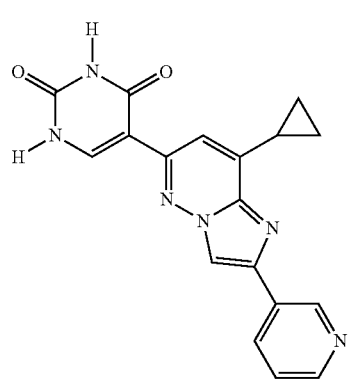 [SMILES: O=c1[nH]cc(-c2cc(C3CC3)c3nc(-c4cccnc4)cn3n2)c(=O)[nH]1] | 5-(8-cyclopropyl-2-(pyridin-3-yl)imidazo[1,2-b]pyridazin-6-yl)pyrimidine-2,4(1H,3H)-dione |
| 103 | 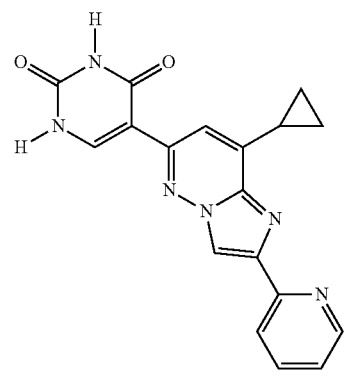 [SMILES: O=c1[nH]cc(-c2cc(C3CC3)c3nc(-c4ccccn4)cn3n2)c(=O)[nH]1] | 5-(8-cyclopropyl-2-(pyridin-2-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 104 | 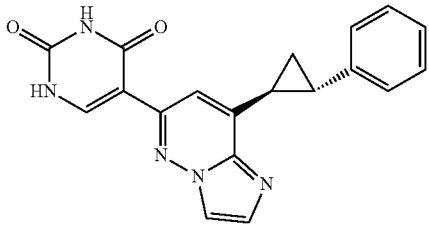 [SMILES: O=c1[nH]cc(-c2cc([C@H]3C[C@@H]3c3ccccc3)c3nccn3n2)c(=O)[nH]1] and 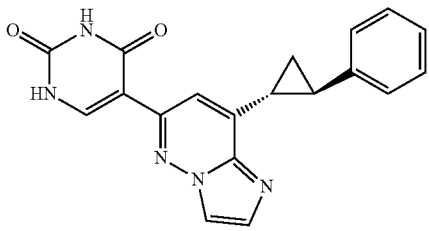 [SMILES: O=c1[nH]cc(-c2cc([C@@H]3C[C@H]3c3ccccc3)c3nccn3n2)c(=O)[nH]1] | 5-(8-((1S,2S)-2-phenylcyclopropyl)imidazo[1,2-b]pyridazin-6-yl)pyrimidine-2,4-(1H,3H)-dione and 5-(8-((1R,2R)-2-phenylcyclopropyl)imidazo[1,2-b]pyridazin-6-yl)pyrimidine-2,4-(1H,3H)-dione |
| 105 | 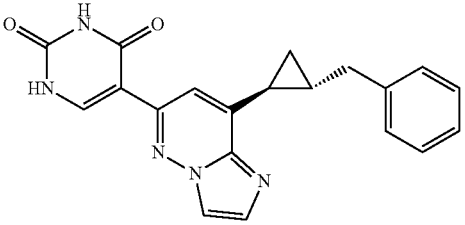 [SMILES: O=c1[nH]cc(-c2cc([C@H]3C[C@@H]3Cc3ccccc3)c3nccn3n2)c(=O)[nH]1] and 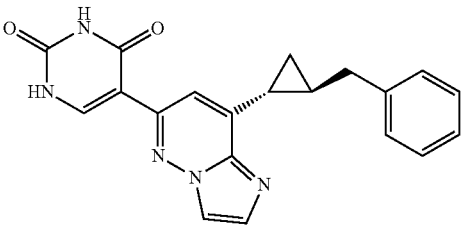 [SMILES: O=c1[nH]cc(-c2cc([C@@H]3C[C@H]3Cc3ccccc3)c3nccn3n2)c(=O)[nH]1] | 5-(8-((1S,2R)-2-benzylcyclopropyl)imidazo[1,2-b]pyridazin-6-yl)pyrimidine-2,4(1H,3H)-dione and 5-(8-((1R,2S)-2-benzylcyclopropyl)imidazo[1,2-b]pyridazin-6-yl)pyrimidine-2,4(1H,3H)-dione |
| 106 | 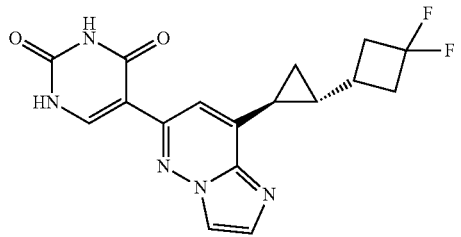 [SMILES: O=c1[nH]cc(-c2cc([C@H]3C[C@@H]3C3CC(F)(F)C3)c3nccn3n2)c(=O)[nH]1] and 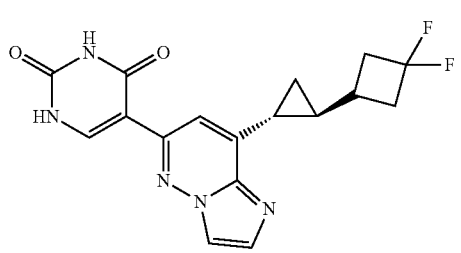 [SMILES: O=c1[nH]cc(-c2cc([C@@H]3C[C@H]3C3CC(F)(F)C3)c3nccn3n2)c(=O)[nH]1] | 5-(8-((1S,2R)-2-(3,3-difluorocyclobutyl)cyclopropyl)imidazo[1,2-b]pyridazin-6-yl)pyrimidine-2,4(1H,3H)-dione and 5-(8-((1R,2S)-2-(3,3-difluorocyclobutyl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 107 | 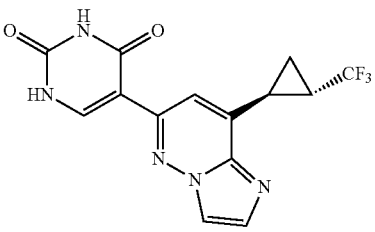 [SMILES: O=c1[nH]cc(-c2cc([C@H]3C[C@@H]3C(F)(F)F)c3nccn3n2)c(=O)[nH]1] | 5-(8-((1S,2S)-2-(trifluoromethyl)cyclopropyl)imidazo[1,2-b]pyridazin-6-yl)pyrimidine-2,4(1H,3H)-dione and 5-(8-((1R,2R)-2-(trifluoromethyl)cyclopropyl)imidazo[1,2-b]pyridazin-6-yl)pyrimidine-2,4(1H,3H)-dione |
| 108 | 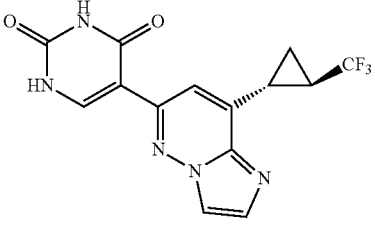 [SMILES: O=c1[nH]cc(-c2cc([C@@H]3C[C@H]3C(F)(F)F)c3nccn3n2)c(=O)[nH]1] | 5-(8-((1R,2R)-2-fluoro-2-phenylcyclopropyl)imidazo[1,2-b]pyridazin-6-yl)pyrimidine-2,4(1H,3H)-dione and 5-(8-((1S,2S)-2-fluoro-2-phenylcyclopropyl)imidazo[1,2-b]pyridazin-6-yl)pyrimidine-2,4(1H,3H)-dione |
| 109 | 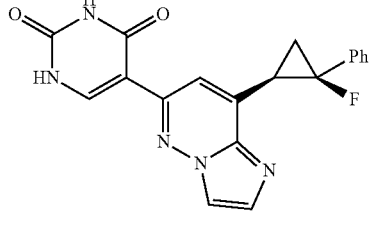 | 5-(8-(3,3,4,4-tetrafluoropyrrolidin-1-yl)imidazo[1,2-b]pyridazin-6-yl)pyrimidine-2,4(1H,3H)-dione |
| 110 | 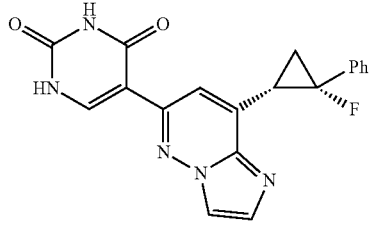 [SMILES: O=c1[nH]cc(-c2cc([C@@H]3C[C@@]3(F)c3ccccc3)c3nccn3n2)c(=O)[nH]1] | 5-(8-((1S,2S)-2-(2,2-difluorobenzo[d][1,3]dioxol-5-yl)cyclopropyl)imidazo[1,2-b]pyridazin-6-yl)pyrimidine-2,4(1H,3H)-dione and 5-(8-((1R,2R)-2-(2,2-difluorobenzo[d][1,3]dioxol-5-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| | and | |
| 111 | | 4-(((1R,2S)-2-(6-(2,4-dioxo-1,2,3,4-tetrahydropyrimidin-5-yl)imidazo[1,2-b]pyridazin-8-yl)cyclopropyl)methyl)benzonitrile and 4-(((1S,2R)-2-(6-(2,4-dioxo-1,2,3,4-tetrahydropyrimidin-5-yl)imidazo[1,2-b]pyridazin-8-yl)cyclopropyl)methyl)benzonitrile |
| | and | |
| 112 | 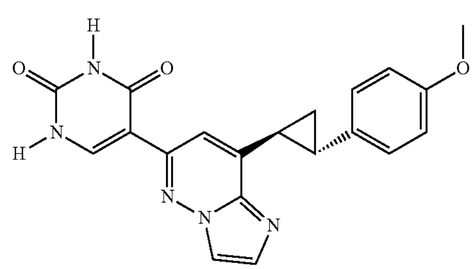 [SMILES: COc1ccc([C@H]2C[C@@H]2c2cc(-c3c[nH]c(=O)[nH]c3=O)nn3ccnc23)cc1] | 5-(8-((1S,2S)-2-(4-methoxyphenyl)cyclopropyl)imidazo[1,2-b]pyridazin-6-yl)pyrimidine-2,4(1H,3H)-dione |
| 113 | 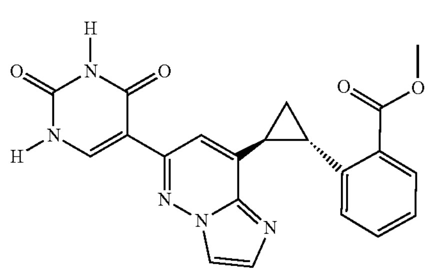 [SMILES: COC(=O)c1ccccc1[C@H]1C[C@@H]1c1cc(-c2c[nH]c(=O)[nH]c2=O)nn2ccnc12] | methyl 2-((1S,2S)-2-(6-(2,4-dioxo-1,2,3,4-tetrahydropyrimidin-5-yl)imidazo[1,2-b]pyridazin-8-yl)cyclopropyl)benzoate |

TABLE 2-continued

| Ex. No. | Structure | IUPAC Name |
| --- | --- | --- |
| 114 | 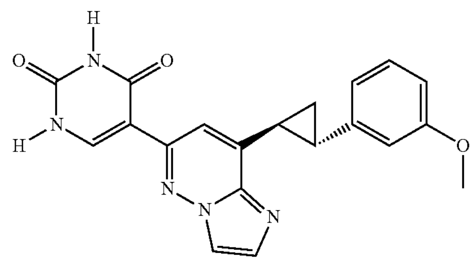 [SMILES: COc1cccc([C@H]2C[C@@H]2c2cc(-c3c[nH]c(=O)[nH]c3=O)nn3ccnc23)c1] | 5-(8-((1S,2S)-2-(3-methoxyphenyl)cyclopropyl)imidazo[1,2-b]pyridazin-6-yl)pyrimidine-2,4(1H,3H)-dione |
| 115 | 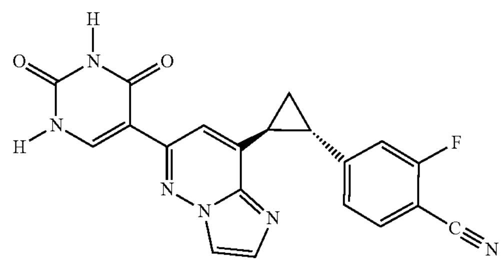 [SMILES: N#Cc1ccc([C@H]2C[C@@H]2c2cc(-c3c[nH]c(=O)[nH]c3=O)nn3ccnc23)cc1F] | 4-((1S,2S)-2-(6-(2,4-dioxo-1,2,3,4-tetrahydropyrimidin-5-yl)imidazo[1,2-b]pyridazin-8-yl)cyclopropyl)-2-fluorobenzonitrile |
| 116 | 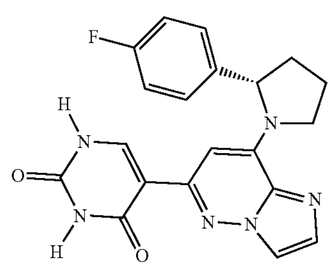 [SMILES: O=c1[nH]cc(-c2cc(N3CCC[C@H]3c3ccc(F)cc3)c3nccn3n2)c(=O)[nH]1] | (S)-5-(8-(2-(4-fluorophenyl)pyrrolidin-1-yl)imidazo[1,2-b]pyridazin-6-yl)pyrimidine-2,4(1H,3H)-dione |
| 117 | 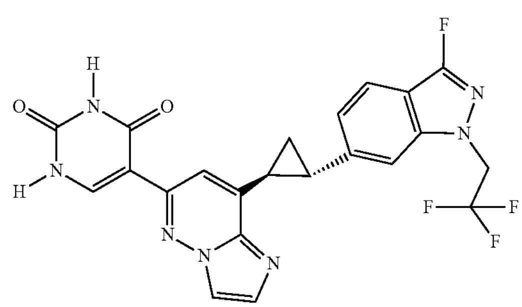 [SMILES: O=c1[nH]cc(-c2cc([C@H]3C[C@@H]3c3ccc4c(F)nn(CC(F)(F)F)c4c3)c3nccn3n2)c(=O)[nH]1] | 5-(8-((1S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 118 | 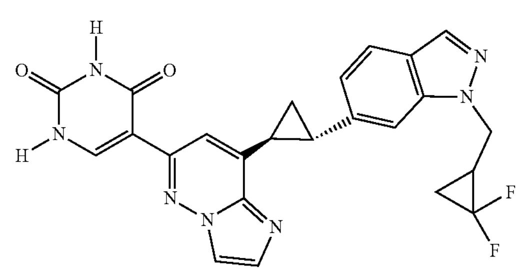 [SMILES: O=c1[nH]cc(-c2cc([C@H]3C[C@@H]3c3ccc4cnn(CC5CC5(F)F)c4c3)c3nccn3n2)c(=O)[nH]1] | 5-(8-((1S,2S)-2-(1-((2,2-difluorocyclopropyl)methyl)-1H-indazol-6-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 119 |  and  | 5-(8-((1S,2S)-2-(1-isopropyl-1H-indazol-6-yl)cyclopropyl)imidazo[1,2-b]pyridazin-6-yl)pyrimidine-2,4(1H,3H)-dione and 5-(8-((1R,2R)-2-(1-isopropyl-1H-indazol-6-yl)cyclopropyl)imidazo[1,2-b]pyridazin-6-yl)pyrimidine-2,4(1H,3H)-dione |
| 120 | 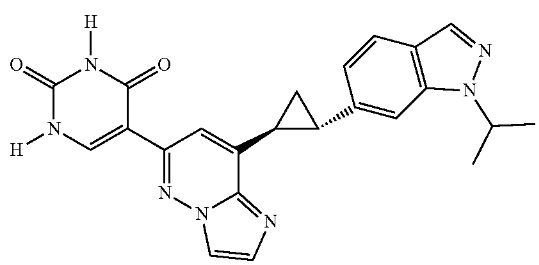 [SMILES: CC(C)n1ncc2ccc([C@H]3C[C@@H]3c3cc(-c4c[nH]c(=O)[nH]c4=O)nn4ccnc34)cc21] | 5-(8-((1S,2S)-2-(1-isopropyl-1H-indazol-6-yl)cyclopropyl)imidazo[1,2-b]pyridazin-6-yl)pyrimidine-2,4(1H,3H)-dione |
| 121 | 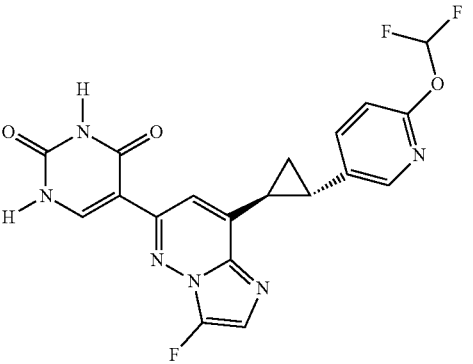 [SMILES: O=c1[nH]cc(-c2cc([C@H]3C[C@@H]3c3ccc(OC(F)F)nc3)c3ncc(F)n3n2)c(=O)[nH]1] | 5-(8-((1S,2S)-2-(6-(difluoromethoxy)pyridin-3-yl)cyclopropyl)-3-fluoroimidazo[1,2-b]pyridazin-6-yl)pyrimidine-2,4(1H,3H)-dione and 5-(8-((1R,2R)-2-(6-(difluoromethoxy)pyridin-3-yl)cyclopropyl)-3-fluoroimidazo[1,2-b]pyridazin-6-yl)pyrimidine-2,4(1H,3H)-dione |

TABLE 2-continued

| Ex. No. | Structure | IUPAC Name |
|---|---|---|
| | and | |
| 122 | 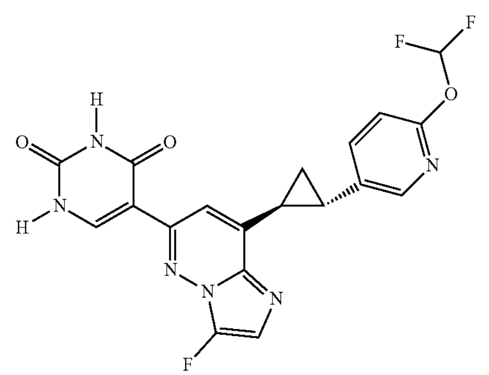 [SMILES: O=c1[nH]cc(-c2cc([C@H]3C[C@@H]3c3ccc(OC(F)F)nc3)c3ncc(F)n3n2)c(=O)[nH]1] | 5-(8-((1S,2S)-2-(6-(difluoromethoxy)pyridin-3-yl)cyclopropyl)-3-fluoroimidazo[1,2-b]pyridazin-6-yl)pyrimidine-2,4(1H,3H)-dione |
| 123 | 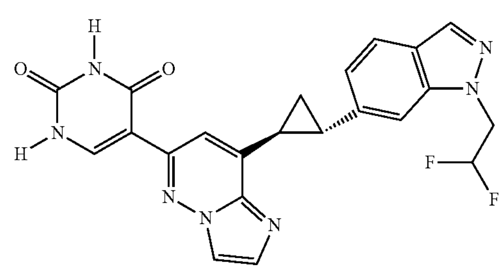 [SMILES: O=c1[nH]cc(-c2cc([C@H]3C[C@@H]3c3ccc4cnn(CC(F)F)c4c3)c3nccn3n2)c(=O)[nH]1] | 5-(8-((1S,2S)-2-(1-(2,2-difluoroethyl)-1H-indazol-6-yl)cyclopropyl)imidazo[1,2-b]pyridazin-6-yl)pyrimidine-2,4(1H,3H)-dione and 5-(8-((1R,2R)-2-(1-(2,2-difluoroethyl)-1H-indazol-6-yl)cyclopropyl)imidazo[1,2-b]pyridazin-6-yl)pyrimidine-2,4(1H,3H)-dione |
| | and | |

TABLE 2-continued

| Ex. No. | Structure | IUPAC Name |
|---|---|---|
| 124 | 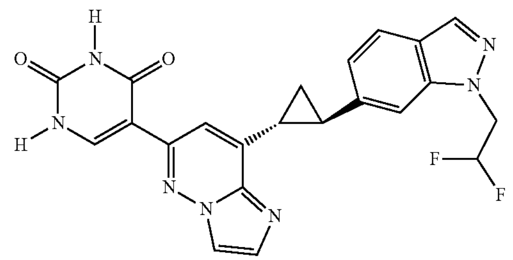 [SMILES: O=c1[nH]cc(-c2cc([C@@H]3C[C@H]3c3ccc4cnn(CC(F)F)c4c3)c3nccn3n2)c(=O)[nH]1] | 5-(8-((1R,2R)-2-(1-(2,2-difluoroethyl)-1H-indazol-6-yl)cyclopropyl)imidazo[1,2-b]pyridazin-6-yl)pyrimidine-2,4(1H,3H)-dione |
| 125 | 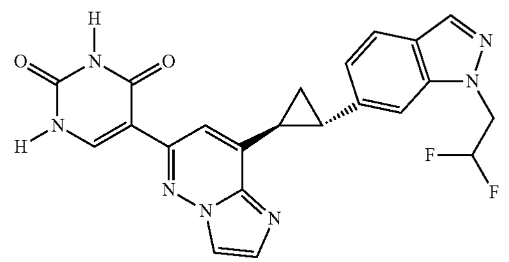 [SMILES: O=c1[nH]cc(-c2cc([C@H]3C[C@@H]3c3ccc4cnn(CC(F)F)c4c3)c3nccn3n2)c(=O)[nH]1] | 5-(8-((1S,2S)-2-(1-(2,2-difluoroethyl)-1H-indazol-6-yl)cyclopropyl)imidazo[1,2-b]pyridazin-6-yl)pyrimidine-2,4(1H,3H)-dione |
| 126 | 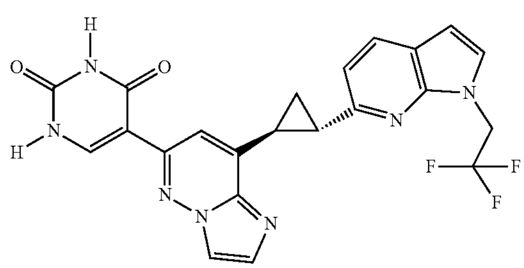 [SMILES: O=c1[nH]cc(-c2cc([C@H]3C[C@@H]3c3ccc4ccn(CC(F)(F)F)c4n3)c3nccn3n2)c(=O)[nH]1] | 5-(8-((1S,2S)-2-(1-(2,2,2-trifluoroethyl)-1H-pyrrolo[2,3-b]pyridin-6-yl)cyclopropyl)imidazo[1,2-b]pyridazin-6-yl)pyrimidine-2,4(1H,3H)-dione |
| 127 | 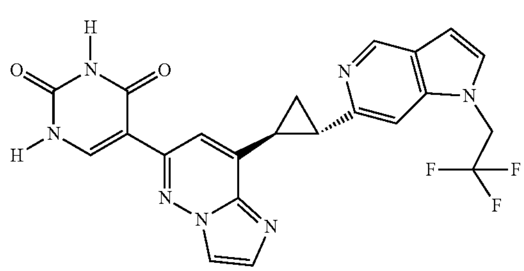 [SMILES: O=c1[nH]cc(-c2cc([C@H]3C[C@@H]3c3cc4c(ccn4CC(F)(F)F)cn3)c3nccn3n2)c(=O)[nH]1] | 5-(8-((1S,2S)-2-(1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione |
| 128 | 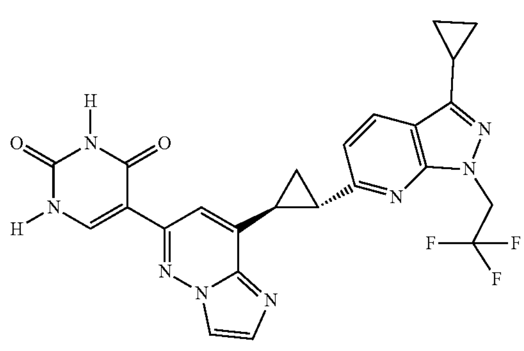 [SMILES: O=c1[nH]cc(-c2cc([C@H]3C[C@@H]3c3ccc4c(C5CC5)nn(CC(F)(F)F)c4n3)c3nccn3n2)c(=O)[nH]1] | 5-(8-((1S,2S)-2-(3-cyclopropyl-1-(2,2,2-trifluoroethyl)-1H-indazol-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 129 | 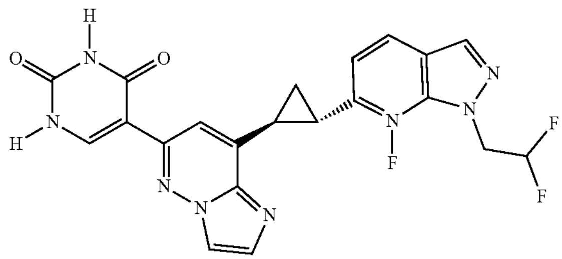 | 5-(8-((1S,2S)-2-(1-(2,2-difluoroethyl)-7-fluoro-1H-indazol-6-yl)cyclopropyl)imidazo[1,2-b]pyridazin-6-yl)pyrimidine-2,4(1H,3H)-dione |
| 130 | 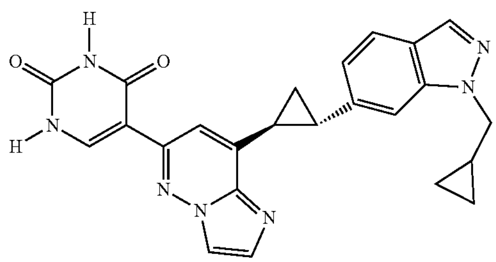 [SMILES: O=c1[nH]cc(-c2cc([C@H]3C[C@@H]3c3ccc4cnn(CC5CC5)c4c3)c3nccn3n2)c(=O)[nH]1] | 5-(8-((1S,2S)-2-(1-(cyclopropylmethyl)-1H-indazol-6-yl)cyclopropyl)imidazo[1,2-b]pyridazin-6-yl)pyrimidine-2,4(1H,3H)-dione |
| 131 | 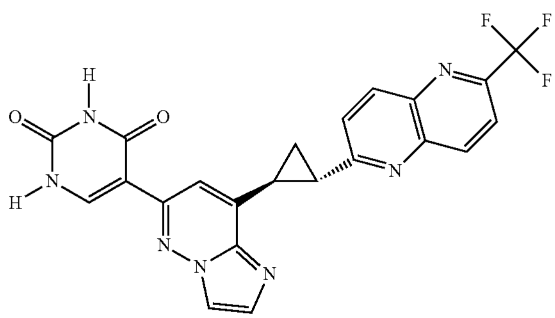 [SMILES: O=c1[nH]cc(-c2cc([C@H]3C[C@@H]3c3ccc4nc(C(F)(F)F)ccc4n3)c3nccn3n2)c(=O)[nH]1] | 5-(8-((1S,2S)-2-(2-(trifluoromethyl)quinolin-6-yl)cyclopropyl)imidazo[1,2-b]pyridazin-6-yl)pyrimidine-2,4(1H,3H)-dione |
| 132 | 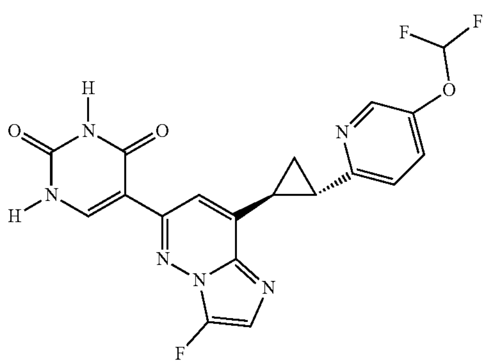 [SMILES: O=c1[nH]cc(-c2cc([C@H]3C[C@@H]3c3ccc(OC(F)F)cn3)c3ncc(F)n3n2)c(=O)[nH]1] | 5-(8-((1S,2S)-2-(5-(difluoromethoxy)pyridin-2-yl)cyclopropyl)-3-fluoroimidazo[1,2-b]pyridazin-6-yl)pyrimidine-2,4(1H,3H)-dione |
| 133 | 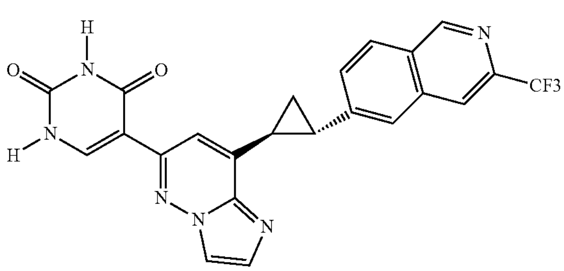 [SMILES: O=c1[nH]cc(-c2cc([C@H]3C[C@@H]3c3ccc4cnc(C(F)(F)F)cc4c3)c3nccn3n2)c(=O)[nH]1] | 5-(8-((1S,2S)-2-(3-(trifluoromethyl)isoquinolin-6-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 134 | 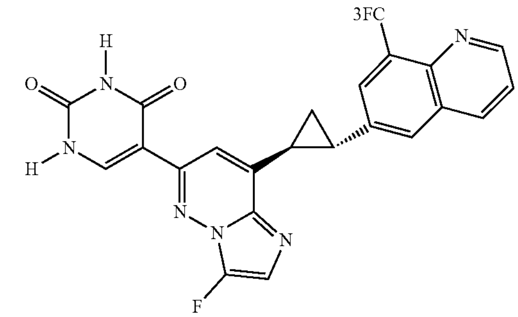 | 5-(3-fluoro-8-((1S,2S)-2-(8-(trifluoromethyl)quinolin-6-yl)cyclopropyl)imidazo[1,2-b]pyridazin-6-yl)pyrimidine-2,4(1H,3H)-dione |
| 135 | 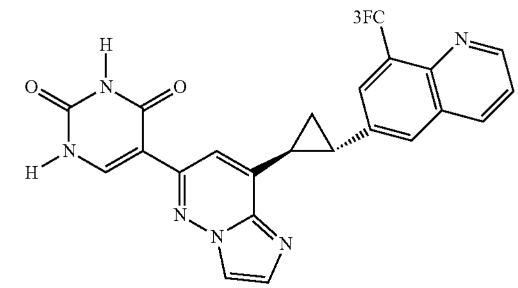 | 5-(8-((1S,2S)-2-(8-(trifluoromethyl)quinolin-6-yl)cyclopropyl)imidazo[1,2-b]pyridazin-6-yl)pyrimidine-2,4(1H,3H)-dione |
| 136 | and | 5-(8-((1S,2S)-2-(5-(difluoromethoxy)pyridin-2-yl)cyclopropyl)imidazo[1,2-b]pyridazin-6-yl)pyrimidine-2,4(1H,3H)-dione and 5-(8-((1R,2R)-2-(5-(difluoromethoxy)pyridin-2-yl)cyclopropyl)imidazo[1,2-b]pyridazin-6-yl)pyrimidine-2,4(1H,3H)-dione |
| 137 | 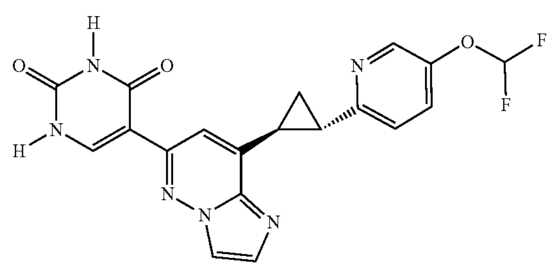 [SMILES: O=c1[nH]cc(-c2cc([C@H]3C[C@@H]3c3ccc(OC(F)F)cn3)c3nccn3n2)c(=O)[nH]1] | 5-(8-((1S,2S)-2-(5-(difluoromethoxy)pyridin-2-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 138 | 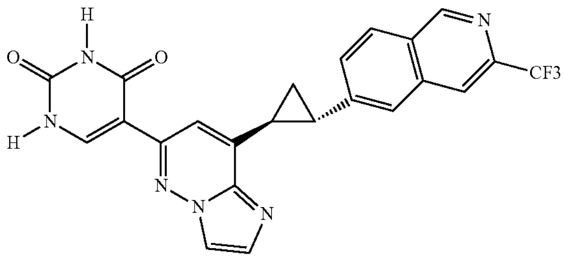 [SMILES: O=c1[nH]cc(-c2cc([C@H]3C[C@@H]3c3ccc4cnc(C(F)(F)F)cc4c3)c3nccn3n2)c(=O)[nH]1] | 5-(8-((1S,2S)-2-(3-(trifluoromethyl)isoquinolin-6-yl)cyclopropyl)imidazo[1,2-b]pyridazin-6-yl)pyrimidine-2,4(1H,3H)-dione |
| 139 | 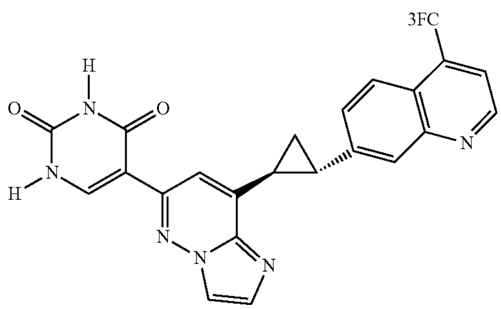 | 5-(8-((1S,2S)-2-(4-(trifluoromethyl)quinolin-7-yl)cyclopropyl)imidazo[1,2-b]pyridazin-6-yl)pyrimidine-2,4(1H,3H)-dione |
| 140 | 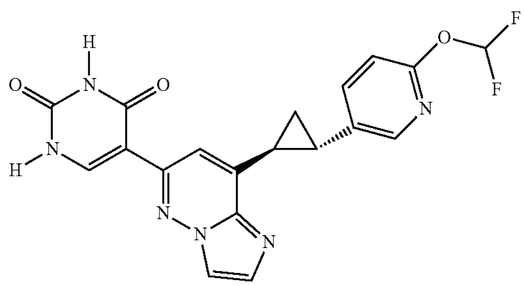 [SMILES: O=c1[nH]cc(-c2cc([C@H]3C[C@@H]3c3ccc(OC(F)F)nc3)c3nccn3n2)c(=O)[nH]1] | 5-(8-((1S,2S)-2-(6-(difluoromethoxy)pyridin-3-yl)cyclopropyl)imidazo[1,2-b]pyridazin-6-yl)pyrimidine-2,4(1H,3H)-dione |
| 141 | 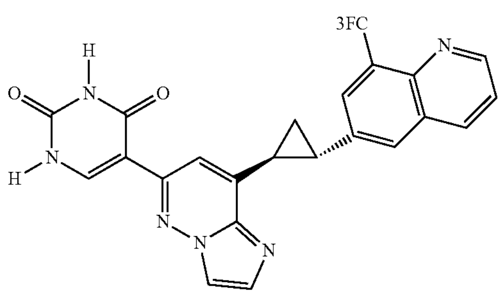 | 5-(8-((1S,2S)-2-(8-(trifluoromethyl)quinolin-6-yl)cyclopropyl)imidazo[1,2-b]pyridazin-6-yl)pyrimidine-2,4(1H,3H)-dione |
| 142 | 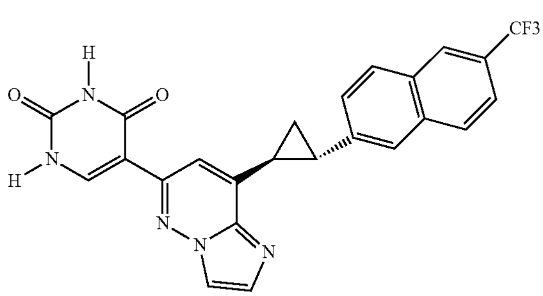 [SMILES: O=c1[nH]cc(-c2cc([C@H]3C[C@@H]3c3ccc4cc(C(F)(F)F)ccc4c3)c3nccn3n2)c(=O)[nH]1] | 5-(8-((1S,2S)-2-(2-(trifluoromethyl)quinolin-6-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 143 | 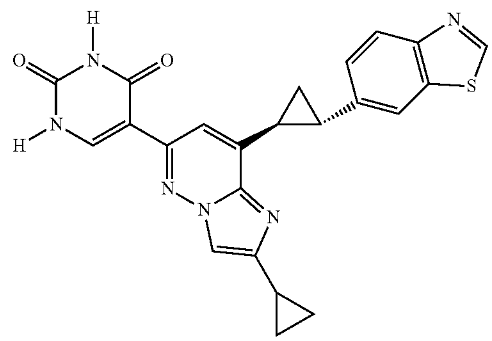 [SMILES: O=c1[nH]cc(-c2cc([C@H]3C[C@@H]3c3ccc4ncsc4c3)c3nc(C4CC4)cn3n2)c(=O)[nH]1] | 5-(8-((1S,2S)-2-(benzo[d]thiazol-6-yl)cyclopropyl)-2-cyclopropylimidazo[1,2-b]pyridazin-6-yl)pyrimidine-2,4(1H,3H)-dione |
| 144 | 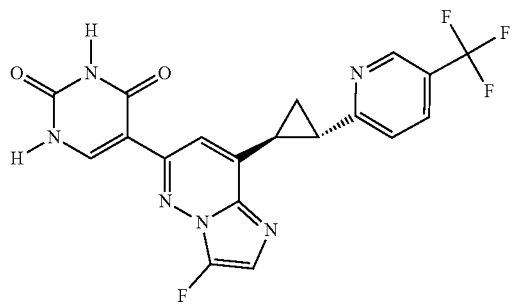 [SMILES: O=c1[nH]cc(-c2cc([C@H]3C[C@@H]3c3ccc(C(F)(F)F)cn3)c3ncc(F)n3n2)c(=O)[nH]1] | 5-(3-fluoro-8-((1S,2S)-2-(5-(trifluoromethyl)pyridin-2-yl)cyclopropyl)imidazo[1,2-b]pyridazin-6-yl)pyrimidine-2,4(1H,3H)-dione |
| 145 | 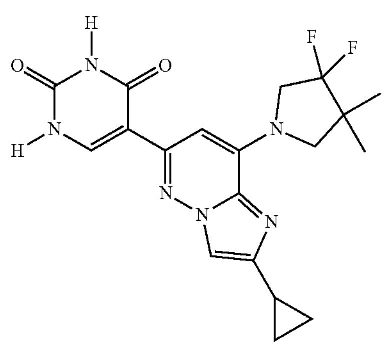 [SMILES: CC1(C)CN(c2cc(-c3c[nH]c(=O)[nH]c3=O)nn3cc(C4CC4)nc23)CC1(F)F] | 5-(2-cyclopropyl-8-(3,3-difluoro-4,4-dimethylpyrrolidin-1-yl)imidazo[1,2-b]pyridazin-6-yl)pyrimidine-2,4(1H,3H)-dione |
| 146 | 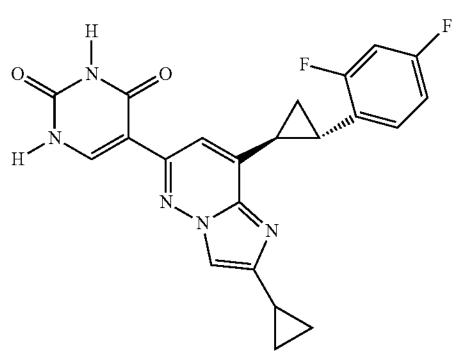 [SMILES: O=c1[nH]cc(-c2cc([C@H]3C[C@@H]3c3ccc(F)cc3F)c3nc(C4CC4)cn3n2)c(=O)[nH]1] | 5-(2-cyclopropyl-8-((1S,2S)-2-(2,4-difluorophenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 147 | 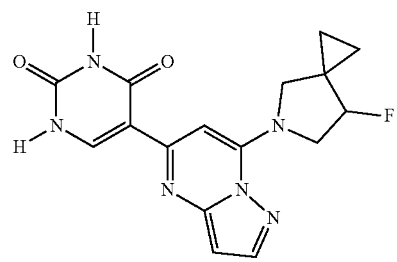 [SMILES: O=c1[nH]cc(-c2cc(N3CC(F)C4(CC4)C3)n3nccc3n2)c(=O)[nH]1] | 5-(7-(7-fluoro-5-azaspiro[2.4]heptan-5-yl)pyrazolo[1,5-a]pyrimidin-5-yl)pyrimidine-2,4(1H,3H)-dione |
| 148 | 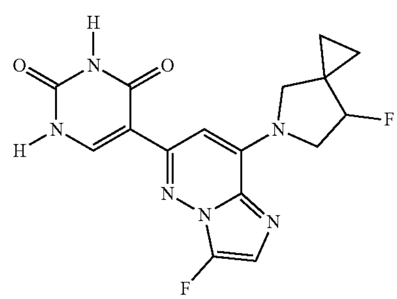 [SMILES: O=c1[nH]cc(-c2cc(N3CC(F)C4(CC4)C3)c3ncc(F)n3n2)c(=O)[nH]1] | 5-(3-fluoro-8-(7-fluoro-5-azaspiro[2.4]heptan-5-yl)imidazo[1,2-b]pyridazin-6-yl)pyrimidine-2,4(1H,3H)-dione |
| 149 | | 5-(8-((1S,2S)-2-(5-(trifluoromethyl)pyridin-2-yl)cyclopropyl)imidazo[1,2-b]pyridazin-6-yl)pyrimidine-2,4(1H,3H)-dione and 5-(8-((1R,2R)-2-(5-(trifluoromethyl)pyridin-2-yl)cyclopropyl)imidazo[1,2-b]pyridazin-6-yl)pyrimidine-2,4(1H,3H)-dione |
| 150 | 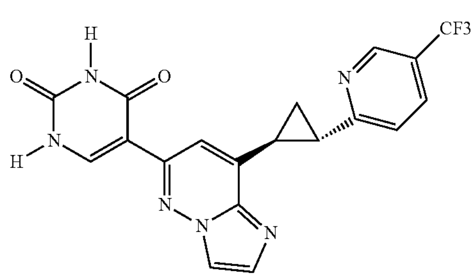 [SMILES: O=c1[nH]cc(-c2cc([C@H]3C[C@@H]3c3ccc(C(F)(F)F)cn3)c3nccn3n2)c(=O)[nH]1] | 5-(8-((1S,2S)-2-(5-(trifluoromethyl)pyridin-2-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 151 | 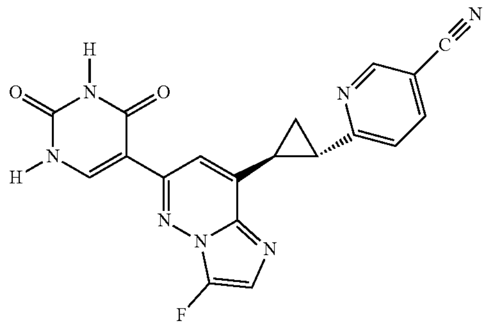 [SMILES: N#Cc1ccc([C@H]2C[C@@H]2c2cc(-c3c[nH]c(=O)[nH]c3=O)nn3c(F)cnc23)nc1] | 6-((1S,2S)-2-(6-(2,4-dioxo-1,2,3,4-tetrahydropyrimidin-5-yl)-3-fluoroimidazo[1,2-b]pyridazin-8-yl)cyclopropyl)nicotinonitrile |
| 152 | | 5-(8-((1S,2S)-2-(6-(trifluoromethyl)pyridin-3-yl)cyclopropyl)imidazo[1,2-b]pyridazin-6-yl)pyrimidine-2,4(1H,3H)-dione and 5-(8-((1R,2R)-2-(6-(trifluoromethyl)pyridin-3-yl)cyclopropyl)imidazo[1,2-b]pyridazin-6-yl)pyrimidine-2,4(1H,3H)-dione |
| 153 | 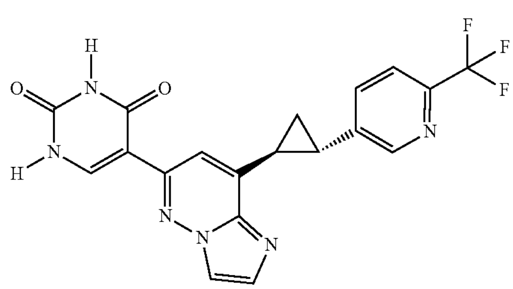 [SMILES: O=c1[nH]cc(-c2cc([C@H]3C[C@@H]3c3ccc(C(F)(F)F)nc3)c3nccn3n2)c(=O)[nH]1] | 5-(8-((1S,2S)-2-(6-(trifluoromethyl)pyridin-3-yl)cyclopropyl)imidazo[1,2-b]pyridazin-6-yl)pyrimidine-2,4(1H,3H)-dione |
| 154 | 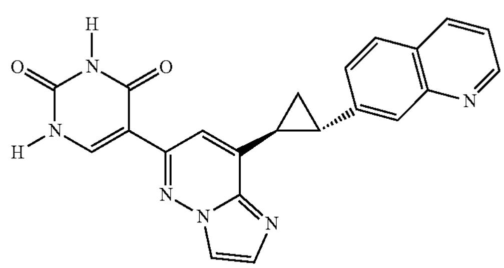 [SMILES: O=c1[nH]cc(-c2cc([C@H]3C[C@@H]3c3ccc4cccnc4c3)c3nccn3n2)c(=O)[nH]1] | 5-(8-((1S,2S)-2-(quinolin-7-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 155 | 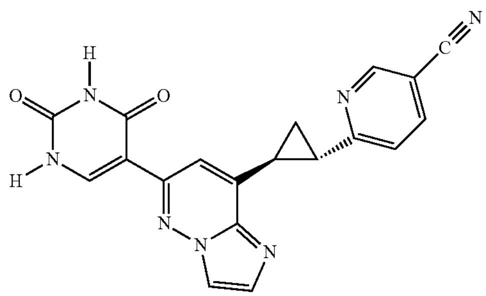 [SMILES: N#Cc1ccc([C@H]2C[C@@H]2c2cc(-c3c[nH]c(=O)[nH]c3=O)nn3ccnc23)nc1] | 6-((1S,2S)-2-(6-(2,4-dioxo-1,2,3,4-tetrahydropyrimidin-5-yl)imidazo[1,2-b]pyridazin-8-yl)cyclopropyl)nicotinonitrile |
| 156 | 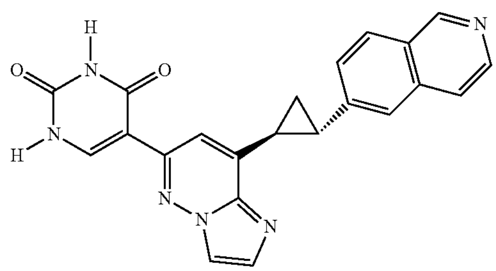 [SMILES: O=c1[nH]cc(-c2cc([C@H]3C[C@@H]3c3ccc4cnccc4c3)c3nccn3n2)c(=O)[nH]1] | 5-(8-((1S,2S)-2-(isoquinolin-6-yl)cyclopropyl)imidazo[1,2-b]pyridazin-6-yl)pyrimidine-2,4(1H,3H)-dione |
| 157 | 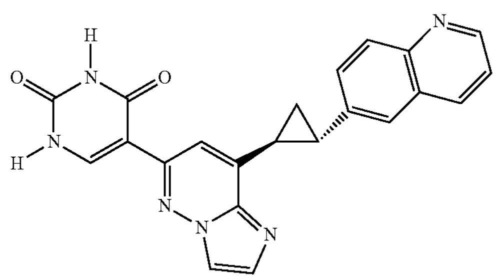 [SMILES: O=c1[nH]cc(-c2cc([C@H]3C[C@@H]3c3ccc4ncccc4c3)c3nccn3n2)c(=O)[nH]1] | 5-(8-((1S,2S)-2-(quinolin-6-yl)cyclopropyl)imidazo[1,2-b]pyridazin-6-yl)pyrimidine-2,4(1H,3H)-dione |
| 158 | 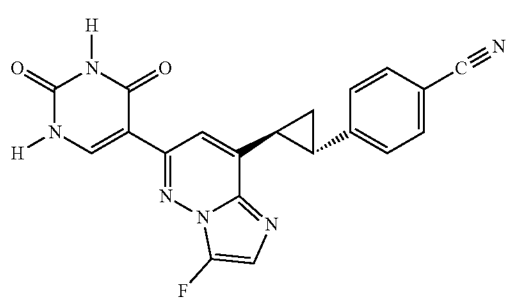 [SMILES: N#Cc1ccc([C@H]2C[C@@H]2c2cc(-c3c[nH]c(=O)[nH]c3=O)nn3c(F)cnc23)cc1] | 4-((1S,2S)-2-(6-(2,4-dioxo-1,2,3,4-tetrahydropyrimidin-5-yl)-3-fluoroimidazo[1,2-b]pyridazin-8-yl)cyclopropyl)benzonitrile |
| 159 | 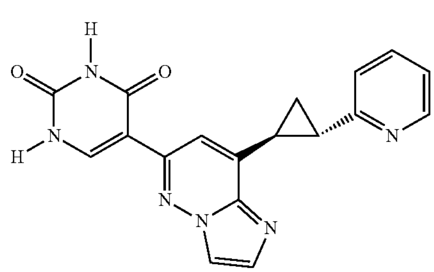 [SMILES: O=c1[nH]cc(-c2cc([C@H]3C[C@@H]3c3ccccn3)c3nccn3n2)c(=O)[nH]1] | 5-(8-((1S,2S)-2-(pyridin-2-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 160 | 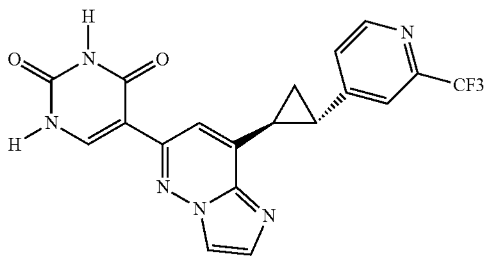 [SMILES: O=c1[nH]cc(-c2cc([C@H]3C[C@@H]3c3ccnc(C(F)(F)F)c3)c3nccn3n2)c(=O)[nH]1] | 5-(8-((1S,2S)-2-(2-(trifluoromethyl)pyridin-4-yl)cyclopropyl)imidazo[1,2-b]pyridazin-6-yl)pyrimidine-2,4(1H,3H)-dione |
| 161 | 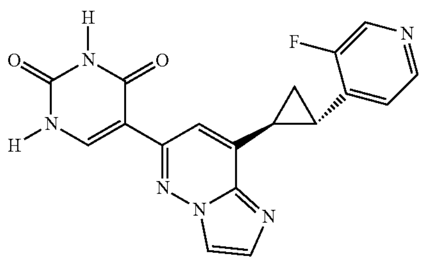 [SMILES: O=c1[nH]cc(-c2cc([C@H]3C[C@@H]3c3ccncc3F)c3nccn3n2)c(=O)[nH]1] | 5-(8-((1S,2S)-2-(3-fluoropyridin-4-yl)cyclopropyl)imidazo[1,2-b]pyridazin-6-yl)pyrimidine-2,4(1H,3H)-dione |
| 162 | 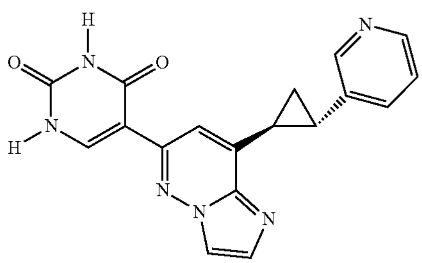 [SMILES: O=c1[nH]cc(-c2cc([C@H]3C[C@@H]3c3cccnc3)c3nccn3n2)c(=O)[nH]1] | 5-(8-((1S,2S)-2-(pyridin-3-yl)cyclopropyl)imidazo[1,2-b]pyridazin-6-yl)pyrimidine-2,4(1H,3H)-dione |
| 163 | 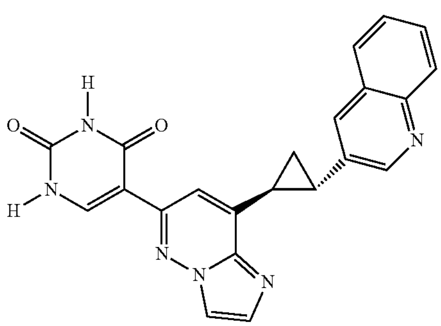 [SMILES: O=c1[nH]cc(-c2cc([C@H]3C[C@@H]3c3cnc4ccccc4c3)c3nccn3n2)c(=O)[nH]1] | 5-(8-((1S,2S)-2-(quinolin-3-yl)cyclopropyl)imidazo[1,2-b]pyridazin-6-yl)pyrimidine-2,4(1H,3H)-dione |
| 164 | 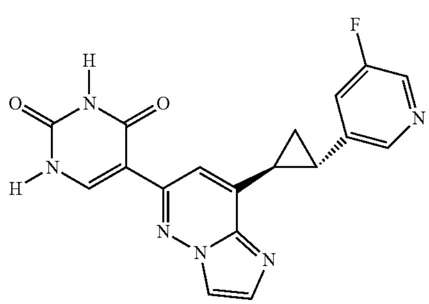 [SMILES: O=c1[nH]cc(-c2cc([C@H]3C[C@@H]3c3cncc(F)c3)c3nccn3n2)c(=O)[nH]1] | 5-(8-((1S,2S)-2-(5-fluoropyridin-3-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 165 | 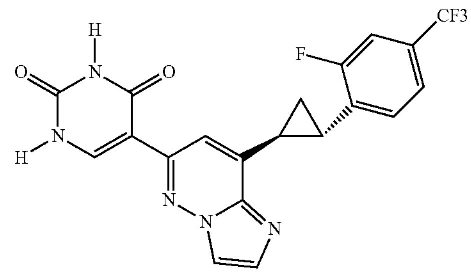 [SMILES: O=c1[nH]cc(-c2cc([C@H]3C[C@@H]3c3ccc(C(F)(F)F)cc3F)c3nccn3n2)c(=O)[nH]1] | 5-(8-((1S,2S)-2-(2-fluoro-4-(trifluoromethyl)phenyl)cyclopropyl)imidazo[1,2-b]pyridazin-6-yl)pyrimidine-2,4(1H,3H)-dione |
| 166 | 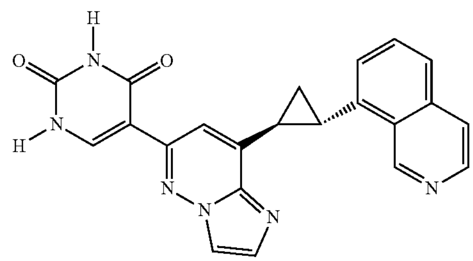 [SMILES: O=c1[nH]cc(-c2cc([C@H]3C[C@@H]3c3cccc4ccncc34)c3nccn3n2)c(=O)[nH]1] | 5-(8-((1S,2S)-2-(isoquinolin-8-yl)cyclopropyl)imidazo[1,2-b]pyridazin-6-yl)pyrimidine-2,4(1H,3H)-dione |
| 167 | 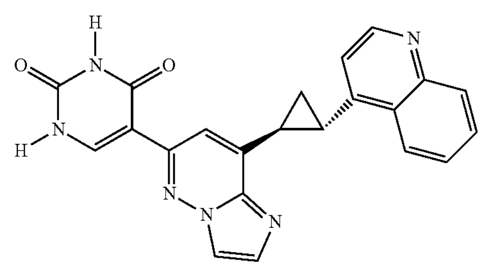 [SMILES: O=c1[nH]cc(-c2cc([C@H]3C[C@@H]3c3ccnc4ccccc34)c3nccn3n2)c(=O)[nH]1] | 5-(8-((1S,2S)-2-(quinolin-4-yl)cyclopropyl)imidazo[1,2-b]pyridazin-6-yl)pyrimidine-2,4(1H,3H)-dione |
| 168 | 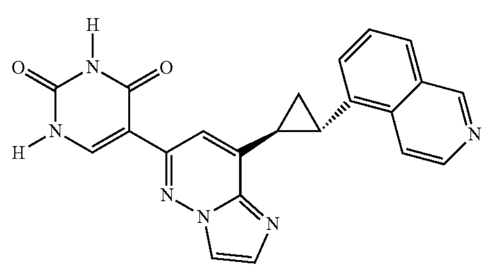 [SMILES: O=c1[nH]cc(-c2cc([C@H]3C[C@@H]3c3cccc4cnccc34)c3nccn3n2)c(=O)[nH]1] | 5-(8-((1S,2S)-2-(isoquinolin-5-yl)cyclopropyl)imidazo[1,2-b]pyridazin-6-yl)pyrimidine-2,4(1H,3H)-dione |
| 169 | 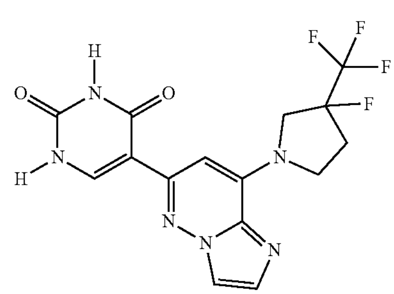 [SMILES: O=c1[nH]cc(-c2cc(N3CCC(F)(C(F)(F)F)C3)c3nccn3n2)c(=O)[nH]1] | 5-(8-(3-fluoro-3-(trifluoromethyl)pyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 170 | 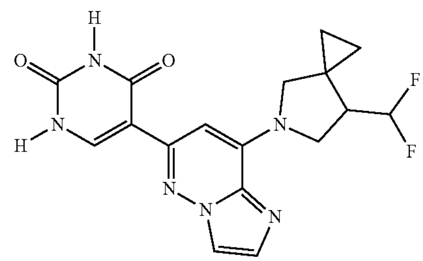 [SMILES: O=c1[nH]cc(-c2cc(N3CC(C(F)F)C4(CC4)C3)c3nccn3n2)c(=O)[nH]1] | 5-(8-(7-(difluoromethyl)-5-azaspiro[2.4]heptan-5-yl)imidazo[1,2-b]pyridazin-6-yl)pyrimidine-2,4(1H,3H)-dione |
| 171 | 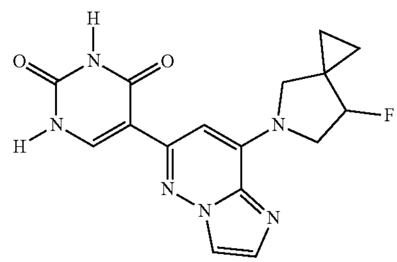 [SMILES: O=c1[nH]cc(-c2cc(N3CC(F)C4(CC4)C3)c3nccn3n2)c(=O)[nH]1] | 5-(8-(7-fluoro-5-azaspiro[2.4]heptan-5-yl)imidazo[1,2-b]pyridazin-6-yl)pyrimidine-2,4(1H,3H)-dione |
| 172 | 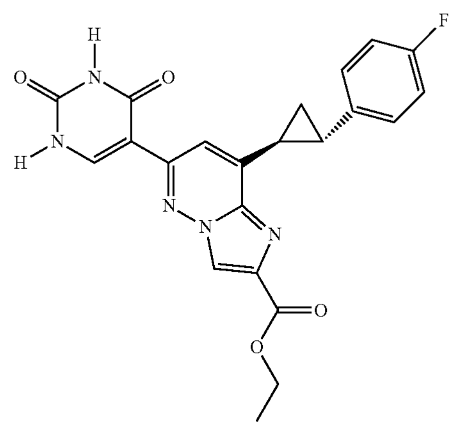 [SMILES: CCOC(=O)c1cn2nc(-c3c[nH]c(=O)[nH]c3=O)cc([C@H]3C[C@@H]3c3ccc(F)cc3)c2n1] | ethyl 6-(2,4-dioxo-1,2,3,4-tetrahydropyrimidin-5-yl)-8-((1S,2S)-2-(4-fluorophenyl)cyclopropyl)imidazo[1,2-b]pyridazine-2-carboxylate |
| 173 | 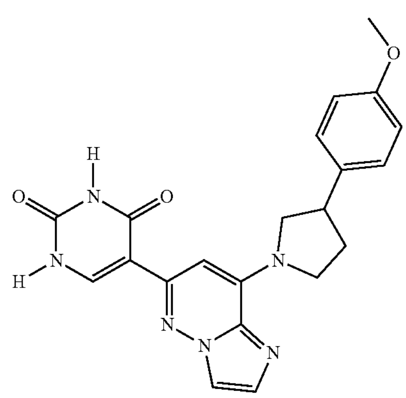 [SMILES: COc1ccc(C2CCN(c3cc(-c4c[nH]c(=O)[nH]c4=O)nn4ccnc34)C2)cc1] | 5-(8-(3-(4-methoxyphenyl)pyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 174 | 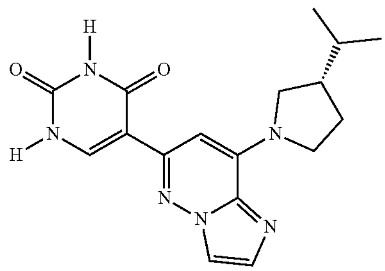 [SMILES: CC(C)[C@@H]1CCN(c2cc(-c3c[nH]c(=O)[nH]c3=O)nn3ccnc23)C1] | (S)-5-(8-(3-isopropylpyrrolidin-1-yl)imidazo[1,2-b]pyridazin-6-yl)pyrimidine-2,4(1H,3H)-dione |
| 175 | 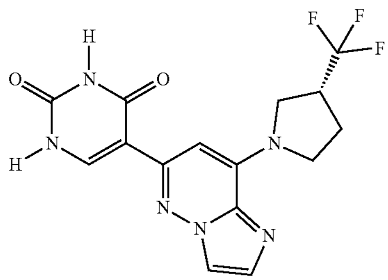 [SMILES: O=c1[nH]cc(-c2cc(N3CC[C@@H](C(F)(F)F)C3)c3nccn3n2)c(=O)[nH]1] | (R)-5-(8-(3-(trifluoromethyl)pyrrolidin-1-yl)imidazo[1,2-b]pyridazin-6-yl)pyrimidine-2,4(1H,3H)-dione |
| 176 | 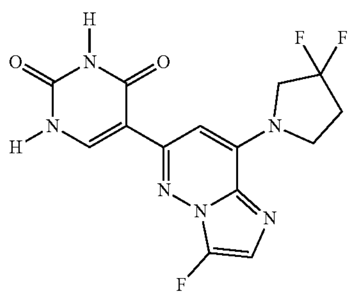 [SMILES: O=c1[nH]cc(-c2cc(N3CCC(F)(F)C3)c3ncc(F)n3n2)c(=O)[nH]1] | 5-(8-(3,3-difluoropyrrolidin-1-yl)-3-fluoroimidazo[1,2-b]pyridazin-6-yl)pyrimidine-2,4(1H,3H)-dione |
| 177 | 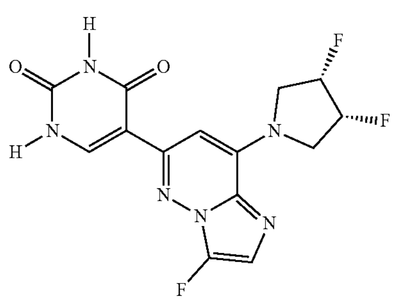 [SMILES: O=c1[nH]cc(-c2cc(N3C[C@@H](F)[C@@H](F)C3)c3ncc(F)n3n2)c(=O)[nH]1] | 5-(8-((3R,4S)-3,4-difluoropyrrolidin-1-yl)-3-fluoroimidazo[1,2-b]pyridazin-6-yl)pyrimidine-2,4(1H,3H)-dione |
| 178 | 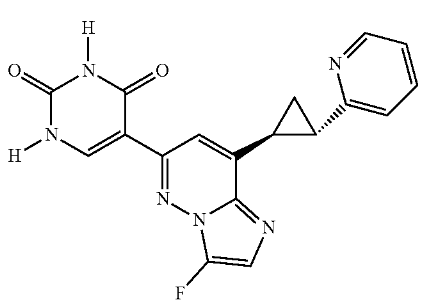 [SMILES: O=c1[nH]cc(-c2cc([C@H]3C[C@@H]3c3ccccn3)c3ncc(F)n3n2)c(=O)[nH]1] | 5-(3-fluoro-8-((1S,2S)-2-(pyridin-2-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 179 | 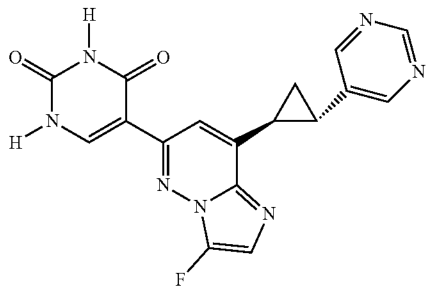 [SMILES: O=c1[nH]cc(-c2cc([C@H]3C[C@@H]3c3cncnc3)c3ncc(F)n3n2)c(=O)[nH]1] | 5-(3-fluoro-8-((1S,2S)-2-(pyrimidin-5-yl)cyclopropyl)imidazo[1,2-b]pyridazin-6-yl)pyrimidine-2,4(1H,3H)-dione |
| 180 | 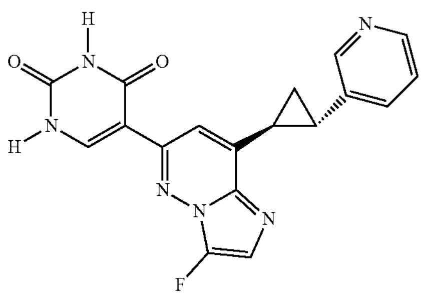 [SMILES: O=c1[nH]cc(-c2cc([C@H]3C[C@@H]3c3cccnc3)c3ncc(F)n3n2)c(=O)[nH]1] | 5-(3-fluoro-8-((1S,2S)-2-(pyridin-3-yl)cyclopropyl)imidazo[1,2-b]pyridazin-6-yl)pyrimidine-2,4(1H,3H)-dione |
| 181 | 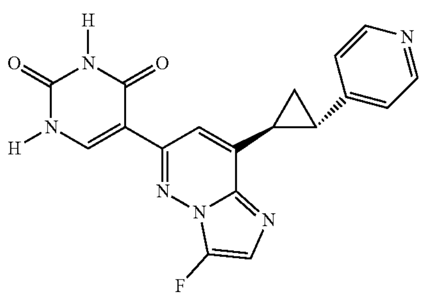 [SMILES: O=c1[nH]cc(-c2cc([C@H]3C[C@@H]3c3ccncc3)c3ncc(F)n3n2)c(=O)[nH]1] | 5-(3-fluoro-8-((1S,2S)-2-(pyridin-4-yl)cyclopropyl)imidazo[1,2-b]pyridazin-6-yl)pyrimidine-2,4(1H,3H)-dione |
| 182 | 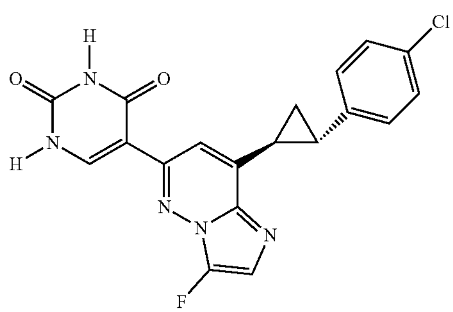 [SMILES: O=c1[nH]cc(-c2cc([C@H]3C[C@@H]3c3ccc(Cl)cc3)c3ncc(F)n3n2)c(=O)[nH]1] | 5-(8-((1S,2S)-2-(4-chlorophenyl)cyclopropyl)-3-fluoroimidazo[1,2-b]pyridazin-6-yl)pyrimidine-2,4(1H,3H)-dione |
| 183 | 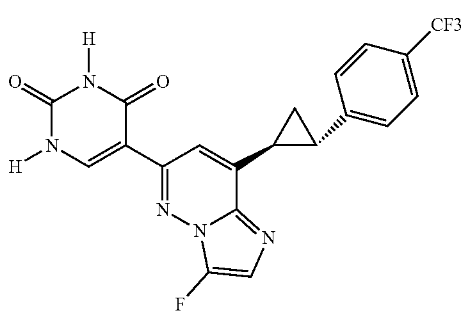 [SMILES: O=c1[nH]cc(-c2cc([C@H]3C[C@@H]3c3ccc(C(F)(F)F)cc3)c3ncc(F)n3n2)c(=O)[nH]1] | 5-(3-fluoro-8-((1S,2S)-2-(4-(trifluoromethyl)phenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 184 | 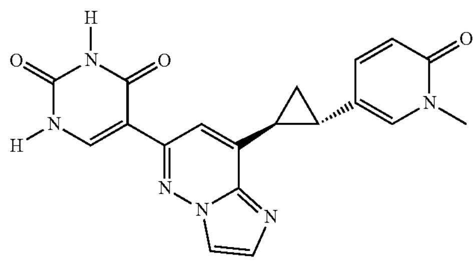 [SMILES: Cn1cc([C@H]2C[C@@H]2c2cc(-c3c[nH]c(=O)[nH]c3=O)nn3ccnc23)ccc1=O] | 5-(8-((1S,2S)-2-(1-methyl-6-oxo-1,6-dihydropyridin-3-yl)cyclopropyl)imidazo[1,2-b]pyridazin-6-yl)pyrimidine-2,4(1H,3H)-dione |
| 185 | 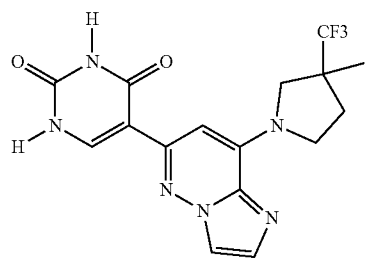 [SMILES: CC1(C(F)(F)F)CCN(c2cc(-c3c[nH]c(=O)[nH]c3=O)nn3ccnc23)C1] | 5-(8-(3-methyl-3-(trifluoromethyl)pyrrolidin-1-yl)imidazo[1,2-b]pyridazin-6-yl)pyrimidine-2,4(1H,3H)-dione |
| 186 | 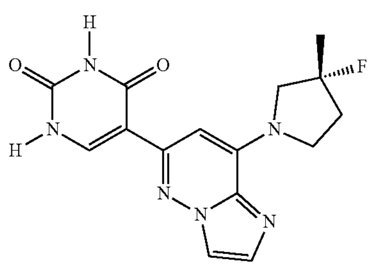 [SMILES: C[C@@]1(F)CCN(c2cc(-c3c[nH]c(=O)[nH]c3=O)nn3ccnc23)C1] | (R)-5-(8-(3-fluoro-3-methylpyrrolidin-1-yl)imidazo[1,2-b]pyridazin-6-yl)pyrimidine-2,4(1H,3H)-dione |
| 187 | 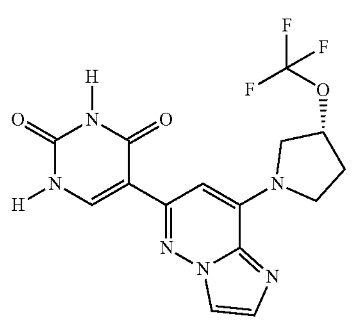 [SMILES: O=c1[nH]cc(-c2cc(N3CC[C@@H](OC(F)(F)F)C3)c3nccn3n2)c(=O)[nH]1] | (R)-5-(8-(3-(trifluoromethoxy)pyrrolidin-1-yl)imidazo[1,2-b]pyridazin-6-yl)pyrimidine-2,4(1H,3H)-dione |
| 188 | 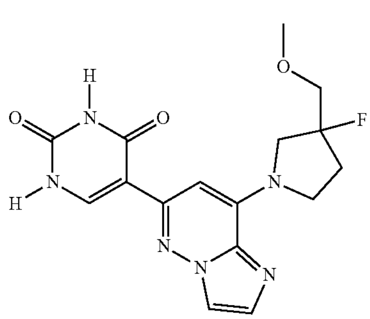 [SMILES: COCC1(F)CCN(c2cc(-c3c[nH]c(=O)[nH]c3=O)nn3ccnc23)C1] | 5-(8-(3-fluoro-3-(methoxymethyl)pyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 189 | 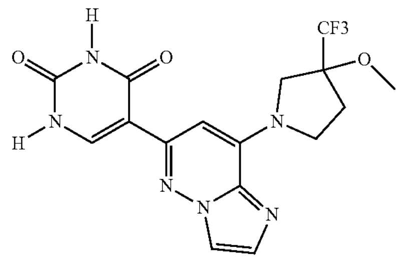 [SMILES: COC1(C(F)(F)F)CCN(c2cc(-c3c[nH]c(=O)[nH]c3=O)nn3ccnc23)C1] | 5-(8-(3-methoxy-3-(trifluoromethyl)pyrrolidin-1-yl)imidazo[1,2-b]pyridazin-6-yl)pyrimidine-2,4(1H,3H)-dione |
| 190 | 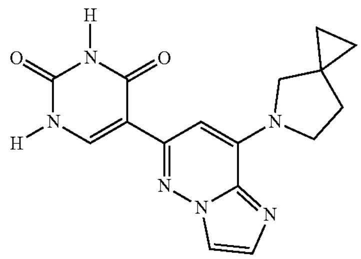 [SMILES: O=c1[nH]cc(-c2cc(N3CCC4(CC4)C3)c3nccn3n2)c(=O)[nH]1] | 5-(8-(5-azaspiro[2.4]heptan-5-yl)imidazo[1,2-b]pyridazin-6-yl)pyrimidine-2,4(1H,3H)-dione |
| 191 | 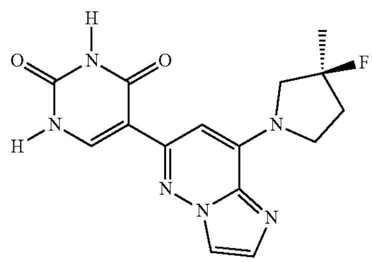 [SMILES: C[C@]1(F)CCN(c2cc(-c3c[nH]c(=O)[nH]c3=O)nn3ccnc23)C1] | (S)-5-(8-(3-fluoro-3-methylpyrrolidin-1-yl)imidazo[1,2-b]pyridazin-6-yl)pyrimidine-2,4(1H,3H)-dione |
| 192 | 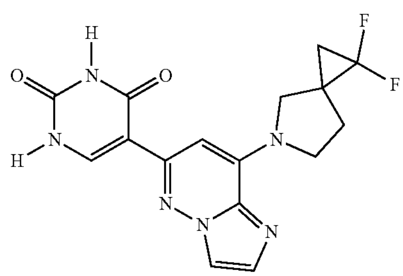 [SMILES: O=c1[nH]cc(-c2cc(N3CCC4(C3)CC4(F)F)c3nccn3n2)c(=O)[nH]1] | 5-(8-(1,1-difluoro-5-azaspiro[2.4]heptan-5-yl)imidazo[1,2-b]pyridazin-6-yl)pyrimidine-2,4(1H,3H)-dione |
| 193 | 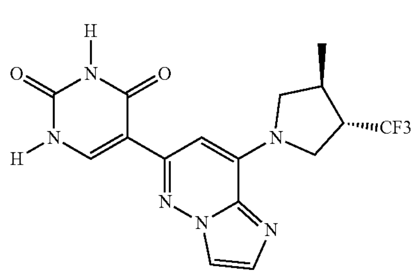 [SMILES: C[C@@H]1CN(c2cc(-c3c[nH]c(=O)[nH]c3=O)nn3ccnc23)C[C@H]1C(F)(F)F] | 5-(8-((3S,4S)-3-methyl-4-(trifluoromethyl)pyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 194 | 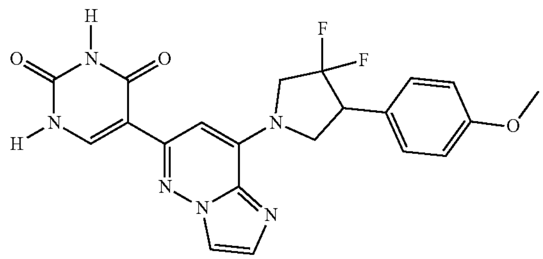 [SMILES: COc1ccc(C2CN(c3cc(-c4c[nH]c(=O)[nH]c4=O)nn4ccnc34)CC2(F)F)cc1] | 5-(8-(3,3-difluoro-4-(4-methoxyphenyl)pyrrolidin-1-yl)imidazo[1,2-b]pyridazin-6-yl)pyrimidine-2,4(1H,3H)-dione |
| 195 | 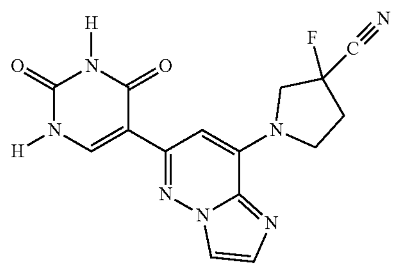 [SMILES: N#CC1(F)CCN(c2cc(-c3c[nH]c(=O)[nH]c3=O)nn3ccnc23)C1] | 1-(6-(2,4-dioxo-1,2,3,4-tetrahydropyrimidin-5-yl)imidazo[1,2-b]pyridazin-8-yl)-3-fluoropyrrolidine-3-carbonitrile |
| 196 | 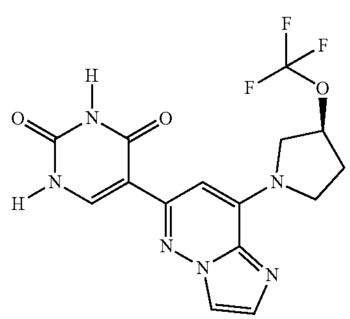 [SMILES: O=c1[nH]cc(-c2cc(N3CC[C@H](OC(F)(F)F)C3)c3nccn3n2)c(=O)[nH]1] | (S)-5-(8-(3-(trifluoromethoxy)pyrrolidin-1-yl)imidazo[1,2-b]pyridazin-6-yl)pyrimidine-2,4(1H,3H)-dione |
| 197 | 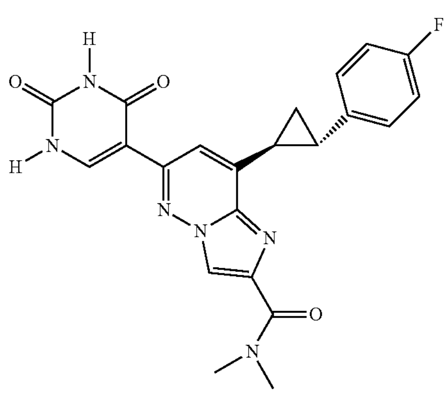 [SMILES: CN(C)C(=O)c1cn2nc(-c3c[nH]c(=O)[nH]c3=O)cc([C@H]3C[C@@H]3c3ccc(F)cc3)c2n1] | 6-(2,4-dioxo-1,2,3,4-tetrahydropyrimidin-5-yl)-8-((1S,2S)-2-(4-fluorophenyl)cyclopropyl)-N,N-dimethylimidazo[1,2-b]pyridazine-2-carboxamide |

TABLE 2-continued

| Ex. No. | Structure | IUPAC Name |
|---|---|---|
| 198 | 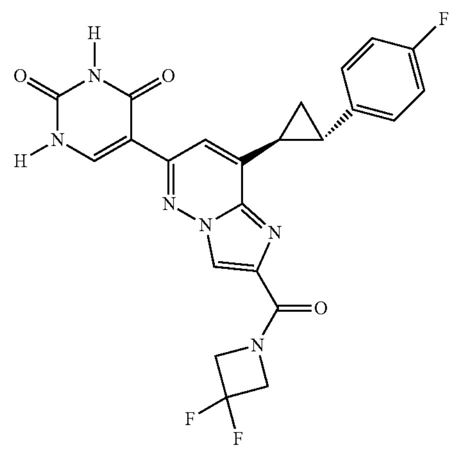 [SMILES: O=C(c1cn2nc(-c3c[nH]c(=O)[nH]c3=O)cc([C@H]3C[C@@H]3c3ccc(F)cc3)c2n1)N1CC(F)(F)C1] | 5-(2-(3,3-difluoroazetidine-1-carbonyl)-8-((1S,2S)-2-(4-fluorophenyl)cyclopropyl)imidazo[1,2-b]pyridazin-6-yl)pyrimidine-2,4(1H,3H)-dione |
| 199 | 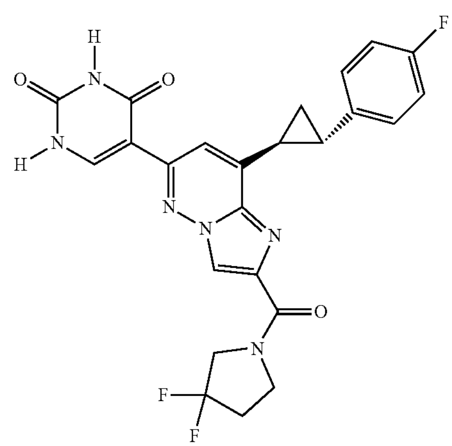 [SMILES: O=C(c1cn2nc(-c3c[nH]c(=O)[nH]c3=O)cc([C@H]3C[C@@H]3c3ccc(F)cc3)c2n1)N1CCC(F)(F)C1] | 5-(2-(3,3-difluoropyrrolidine-1-carbonyl)-8-((1S,2S)-2-(4-fluorophenyl)cyclopropyl)imidazo[1,2-b]pyridazin-6-yl)pyrimidine-2,4(1H,3H)-dione |
| 200 | 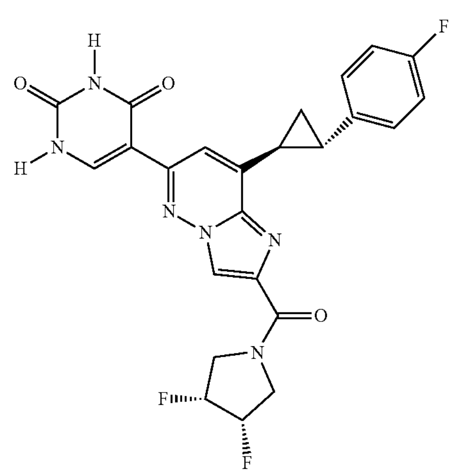 [SMILES: O=C(c1cn2nc(-c3c[nH]c(=O)[nH]c3=O)cc([C@H]3C[C@@H]3c3ccc(F)cc3)c2n1)N1C[C@@H](F)[C@@H](F)C1] | 5-(2-((3R,4S)-3,4-difluoropyrrolidine-1-carbonyl)-8-((1S,2S)-2-(4-fluorophenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 201 | 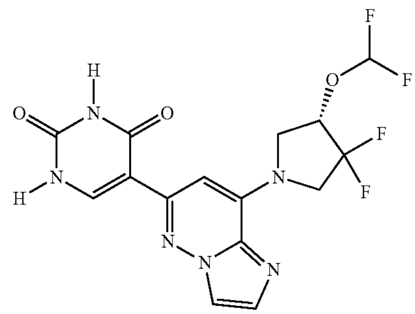 [SMILES: O=c1[nH]cc(-c2cc(N3C[C@H](OC(F)F)C(F)(F)C3)c3nccn3n2)c(=O)[nH]1] | (S)-5-(8-(4-(difluoromethoxy)-3,3-difluoropyrrolidin-1-yl)imidazo[1,2-b]pyridazin-6-yl)pyrimidine-2,4(1H,3H)-dione |
| 202 | 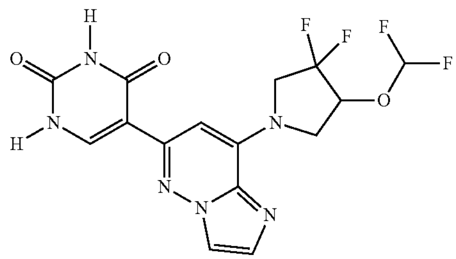 [SMILES: O=c1[nH]cc(-c2cc(N3CC(OC(F)F)C(F)(F)C3)c3nccn3n2)c(=O)[nH]1] | 5-(8-(4-(difluoromethoxy)-3,3-difluoropyrrolidin-1-yl)imidazo[1,2-b]pyridazin-6-yl)pyrimidine-2,4(1H,3H)-dione |
| 203 | 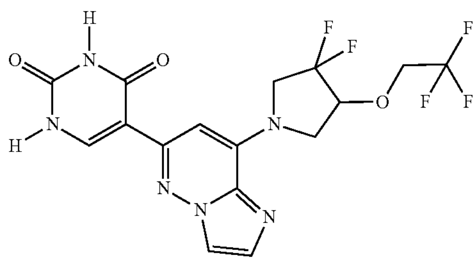 [SMILES: O=c1[nH]cc(-c2cc(N3CC(OCC(F)(F)F)C(F)(F)C3)c3nccn3n2)c(=O)[nH]1] | 5-(8-(3,3-difluoro-4-(2,2,2-trifluoroethoxy)pyrrolidin-1-yl)imidazo[1,2-b]pyridazin-6-yl)pyrimidine-2,4(1H,3H)-dione |
| 204 | 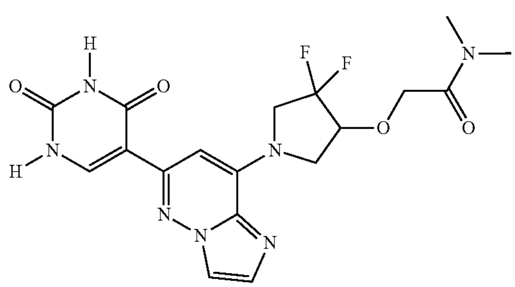 [SMILES: CN(C)C(=O)COC1CN(c2cc(-c3c[nH]c(=O)[nH]c3=O)nn3ccnc23)CC1(F)F] | 2-((1-(6-(2,4-dioxo-1,2,3,4-tetrahydropyrimidin-5-yl)imidazo[1,2-b]pyridazin-8-yl)-4,4-difluoropyrrolidin-3-yl)oxy)-N,N-dimethylacetamide |
| 205 | 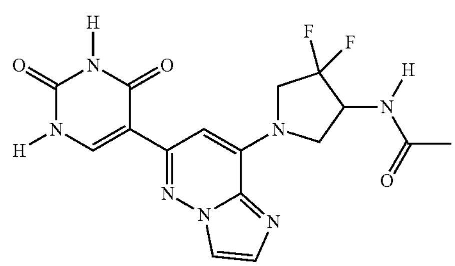 [SMILES: CC(=O)NC1CN(c2cc(-c3c[nH]c(=O)[nH]c3=O)nn3ccnc23)CC1(F)F] | N-(1-(6-(2,4-dioxo-1,2,3,4-tetrahydropyrimidin-5-yl)imidazo[1,2-b]pyridazin-8-yl)-4,4-difluoropyrrolidin-3-yl)acetamide |

TABLE 2-continued

| Ex. No. | Structure | IUPAC Name |
|---|---|---|
| 206 | 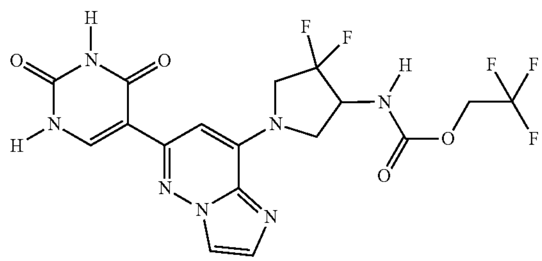 [SMILES: O=C(NC1CN(c2cc(-c3c[nH]c(=O)[nH]c3=O)nn3ccnc23)CC1(F)F)OCC(F)(F)F] | 2,2,2-trifluoroethyl (1-(6-(2,4-dioxo-1,2,3,4-tetrahydropyrimidin-5-yl)imidazo[1,2-b]pyridazin-8-yl)-4,4-difluoropyrrolidin-3-yl)carbamate |
| 207 | 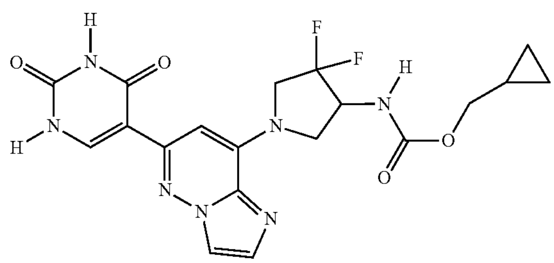 [SMILES: O=C(NC1CN(c2cc(-c3c[nH]c(=O)[nH]c3=O)nn3ccnc23)CC1(F)F)OCC1CC1] | cyclopropylmethyl (1-(6-(2,4-dioxo-1,2,3,4-tetrahydropyrimidin-5-yl)imidazo[1,2-b]pyridazin-8-yl)-4,4-difluoropyrrolidin-3-yl)carbamate |
| 208 | 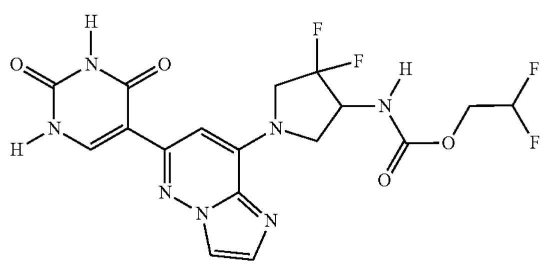 [SMILES: O=C(NC1CN(c2cc(-c3c[nH]c(=O)[nH]c3=O)nn3ccnc23)CC1(F)F)OCC(F)F] | 2,2-difluoroethyl (1-(6-(2,4-dioxo-1,2,3,4-tetrahydropyrimidin-5-yl)imidazo[1,2-b]pyridazin-8-yl)-4,4-difluoropyrrolidin-3-yl)carbamate |
| 209 | 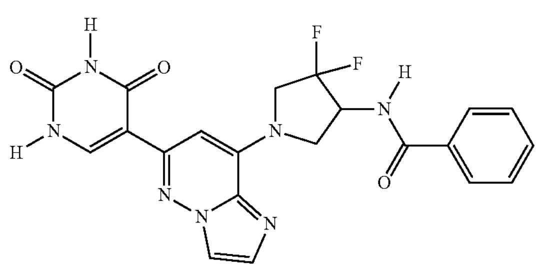 [SMILES: O=C(NC1CN(c2cc(-c3c[nH]c(=O)[nH]c3=O)nn3ccnc23)CC1(F)F)c1ccccc1] | N-(1-(6-(2,4-dioxo-1,2,3,4-tetrahydropyrimidin-5-yl)imidazo[1,2-b]pyridazin-8-yl)-4,4-difluoropyrrolidin-3-yl)benzamide |
| 210 | 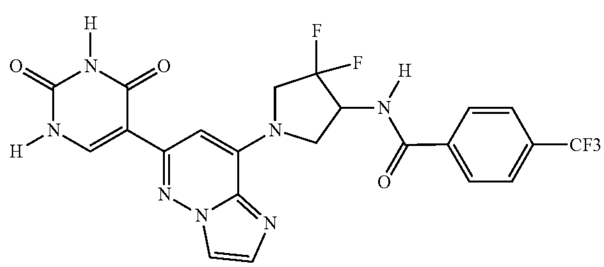 [SMILES: O=C(NC1CN(c2cc(-c3c[nH]c(=O)[nH]c3=O)nn3ccnc23)CC1(F)F)c1ccc(C(F)(F)F)cn1] | N-(1-(6-(2,4-dioxo-1,2,3,4-tetrahydropyrimidin-5-yl)imidazo[1,2-b]pyridazin-8-yl)-4,4-difluoropyrrolidin-3-yl)-4-(trifluoromethyl)benzamide |

TABLE 2-continued

| Ex. No. | Structure | IUPAC Name |
|---|---|---|
| 211 | 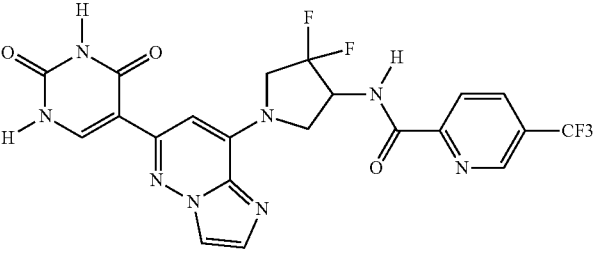 | N-(1-(6-(2,4-dioxo-1,2,3,4-tetrahydropyrimidin-5-yl)imidazo[1,2-b]pyridazin-8-yl)-4,4-difluoropyrrolidin-3-yl)-5-(trifluoromethyl)picolinamide |
| 212 | 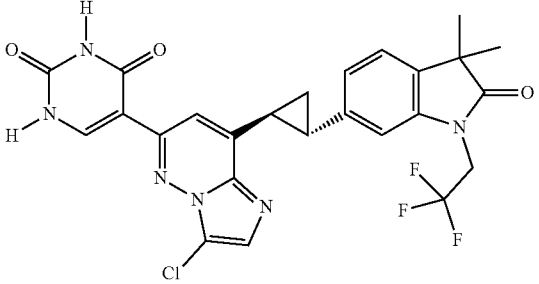 [SMILES: CC1(C)C(=O)N(CC(F)(F)F)c2cc([C@H]3C[C@@H]3c3cc(-c4c[nH]c(=O)[nH]c4=O)nn4c(Cl)cnc34)ccc21] | 5-(3-chloro-8-((1S,2S)-2-(3,3-dimethyl-2-oxo-1-(2,2,2-trifluoroethyl)indolin-6-yl)cyclopropyl)imidazo[1,2-b]pyridazin-6-yl)pyrimidine-2,4(1H,3H)-dione |
| 213 | 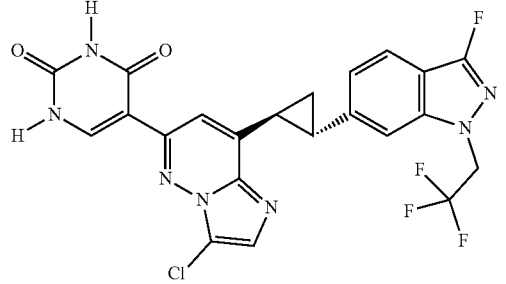 [SMILES: O=c1[nH]cc(-c2cc([C@H]3C[C@@H]3c3ccc4c(F)nn(CC(F)(F)F)c4c3)c3ncc(Cl)n3n2)c(=O)[nH]1] | 5-(3-chloro-8-((1S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 214 | 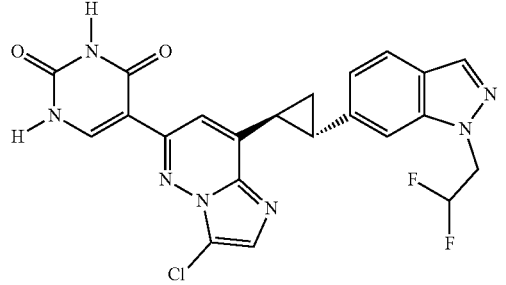 [SMILES: O=c1[nH]cc(-c2cc([C@H]3C[C@@H]3c3ccc4cnn(CC(F)F)c4c3)c3ncc(Cl)n3n2)c(=O)[nH]1] | 5-(8-((1S,2S)-2-(1-(2,2-difluoroethyl)-1H-indazol-6-yl)cyclopropyl)-3-fluoroimidazo[1,2-b]pyridazin-6-yl)pyrimidine-2,4(1H,3H)-dione |
| 215 | 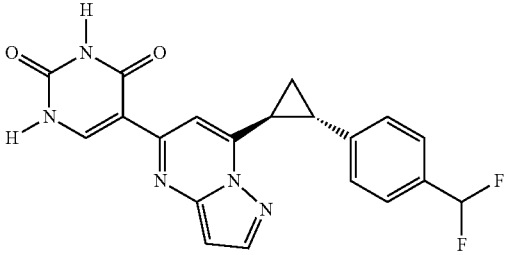 [SMILES: O=c1[nH]cc(-c2cc([C@H]3C[C@@H]3c3ccc(C(F)F)cc3)n3nccc3n2)c(=O)[nH]1] | 5-(7-((1S,2S)-2-(4-(difluoromethyl)phenyl)cyclopropyl)pyrazolo[1,5-a]pyrimidin-5-yl)pyrimidine-2,4(1H,3H)-dione |

TABLE 2-continued

| Ex. No. | Structure | IUPAC Name |
|---|---|---|
| 216 | 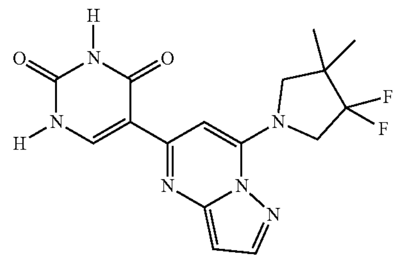 [SMILES: CC1(C)CN(c2cc(-c3c[nH]c(=O)[nH]c3=O)nc3ccnn23)CC1(F)F] | 5-(7-(3,3-difluoro-4,4-dimethylpyrrolidin-1-yl)pyrazolo[1,5-a]pyrimidin-5-yl)pyrimidine-2,4(1H,3H)-dione |
| 217 | 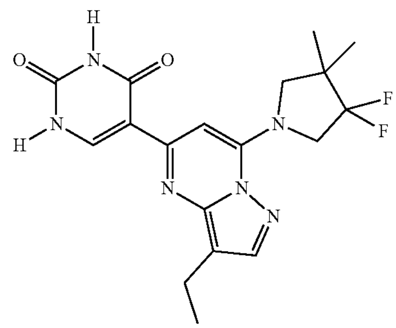 [SMILES: CCc1cnn2c(N3CC(C)(C)C(F)(F)C3)cc(-c3c[nH]c(=O)[nH]c3=O)nc12] | 5-(7-(3,3-difluoro-4,4-dimethylpyrrolidin-1-yl)-3-ethylpyrazolo[1,5-a]pyrimidin-5-yl)pyrimidine-2,4(1H,3H)-dione |
| 218 | 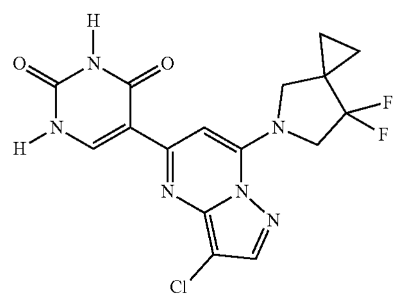 [SMILES: O=c1[nH]cc(-c2cc(N3CC(F)(F)C4(CC4)C3)n3ncc(Cl)c3n2)c(=O)[nH]1] | 5-(3-chloro-7-(7,7-difluoro-5-azaspiro[2.4]heptan-5-yl)pyrazolo[1,5-a]pyrimidin-5-yl)pyrimidine-2,4(1H,3H)-dione |
| 219 | 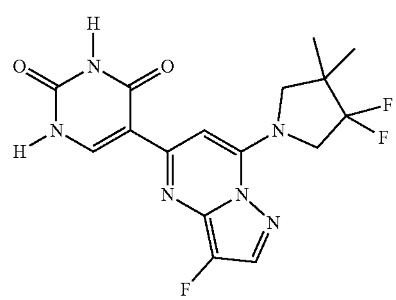 [SMILES: CC1(C)CN(c2cc(-c3c[nH]c(=O)[nH]c3=O)nc3c(F)cnn23)CC1(F)F] | 5-(7-(3,3-difluoro-4,4-dimethylpyrrolidin-1-yl)-3-fluoropyrazolo[1,5-a]pyrimidin-5-yl)pyrimidine-2,4(1H,3H)-dione |
| 220 | 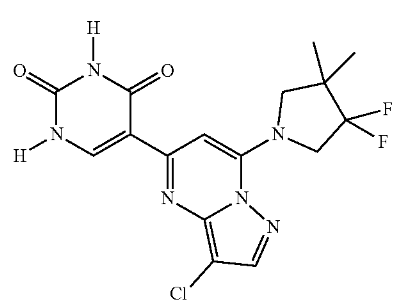 [SMILES: CC1(C)CN(c2cc(-c3c[nH]c(=O)[nH]c3=O)nc3c(Cl)cnn23)CC1(F)F] | 5-(3-chloro-7-(3,3-difluoro-4,4-dimethylpyrrolidin-1-yl)pyrazolo[1,5-a]pyrimidin-5-yl)pyrimidine-2,4(1H,3H)-dione |

TABLE 2-continued

| Ex. No. | Structure | IUPAC Name |
| --- | --- | --- |
| 221 | 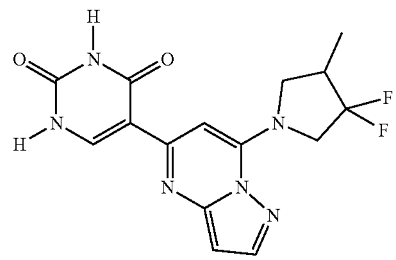 [SMILES: CC1CN(c2cc(-c3c[nH]c(=O)[nH]c3=O)nc3ccnn23)CC1(F)F] | 5-(7-(3,3-difluoro-4-methylpyrrolidin-1-yl)pyrazolo[1,5-a]pyrimidin-5-yl)pyrimidine-2,4(1H,3H)-dione |
| 222 | 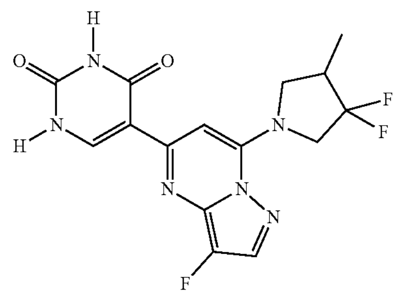 [SMILES: CC1CN(c2cc(-c3c[nH]c(=O)[nH]c3=O)nc3c(F)cnn23)CC1(F)F] | 5-(7-(3,3-difluoro-4-methylpyrrolidin-1-yl)-3-fluoropyrazolo[1,5-a]pyrimidin-5-yl)pyrimidine-2,4(1H,3H)-dione |
| 223 | 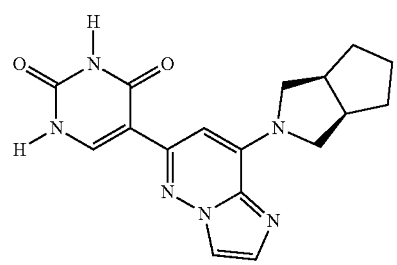 [SMILES: O=c1[nH]cc(-c2cc(N3C[C@H]4CCC[C@H]4C3)c3nccn3n2)c(=O)[nH]1] | 5-(8-((3aR,6aS)-hexahydrocyclopenta[c]pyrrol-2(1H)-yl)imidazo[1,2-b]pyridazin-6-yl)pyrimidine-2,4(1H,3H)-dione |
| 224 | 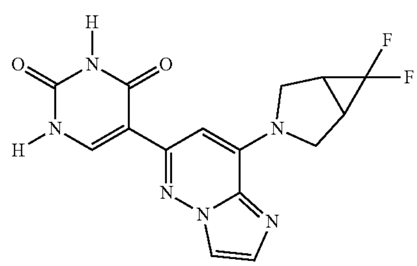 [SMILES: O=c1[nH]cc(-c2cc(N3CC4C(C3)C4(F)F)c3nccn3n2)c(=O)[nH]1] | 5-(8-(6,6-difluoro-3-azabicyclo[3.1.0]hexan-3-yl)imidazo[1,2-b]pyridazin-6-yl)pyrimidine-2,4(1H,3H)-dione |
| 225 | 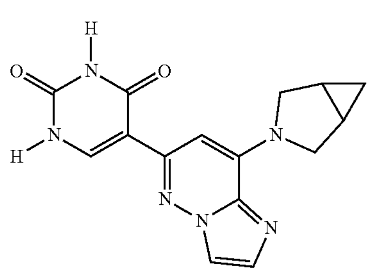 [SMILES: O=c1[nH]cc(-c2cc(N3CC4CC4C3)c3nccn3n2)c(=O)[nH]1] | 5-(8-(3-azabicyclo[3.1.0]hexan-3-yl)imidazo[1,2-b]pyridazin-6-yl)pyrimidine-2,4(1H,3H)-dione |

TABLE 2-continued

| Ex. No. | Structure | IUPAC Name |
|---|---|---|
| 226 | 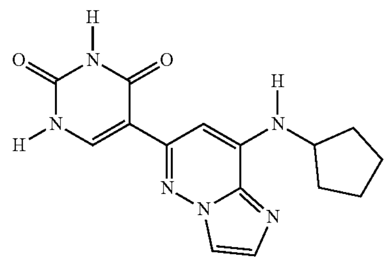 [SMILES: O=c1[nH]cc(-c2cc(NC3CCCC3)c3nccn3n2)c(=O)[nH]1] | 5-(8-(cyclopentylamino)imidazo[1,2-b]pyridazin-6-yl)pyrimidine-2,4(1H,3H)-dione |
| 227 | 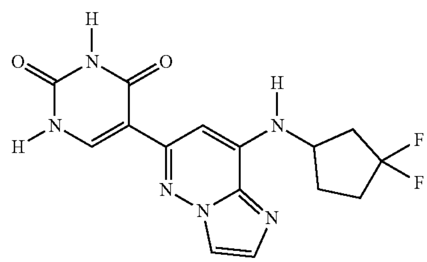 [SMILES: O=c1[nH]cc(-c2cc(NC3CCC(F)(F)C3)c3nccn3n2)c(=O)[nH]1] | 5-(8-((3,3-difluorocyclopentyl)amino)imidazo[1,2-b]pyridazin-6-yl)pyrimidine-2,4(1H,3H)-dione |
| 228 | 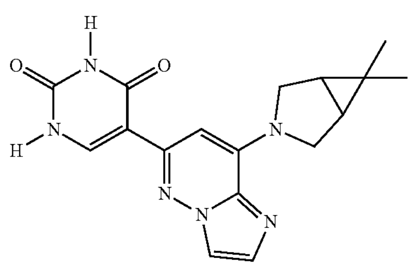 [SMILES: CC1(C)C2CN(c3cc(-c4c[nH]c(=O)[nH]c4=O)nn4ccnc34)CC21] | 5-(8-(6,6-dimethyl-3-azabicyclo[3.1.0]hexan-3-yl)imidazo[1,2-b]pyridazin-6-yl)pyrimidine-2,4(1H,3H)-dione |
| 229 | 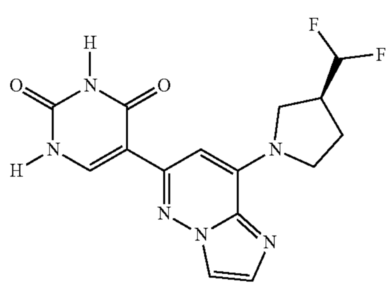 [SMILES: O=c1[nH]cc(-c2cc(N3CC[C@H](C(F)F)C3)c3nccn3n2)c(=O)[nH]1] | (S)-5-(8-(3-(difluoromethyl)pyrrolidin-1-yl)imidazo[1,2-b]pyridazin-6-yl)pyrimidine-2,4(1H,3H)-dione |
| 230 | 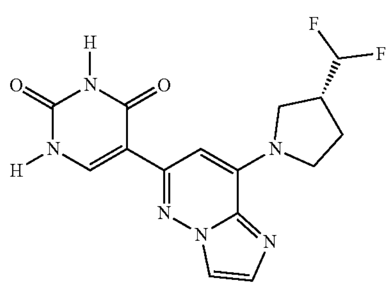 [SMILES: O=c1[nH]cc(-c2cc(N3CC[C@@H](C(F)F)C3)c3nccn3n2)c(=O)[nH]1] | (R)-5-(8-(3-(difluoromethyl)pyrrolidin-1-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 231 | 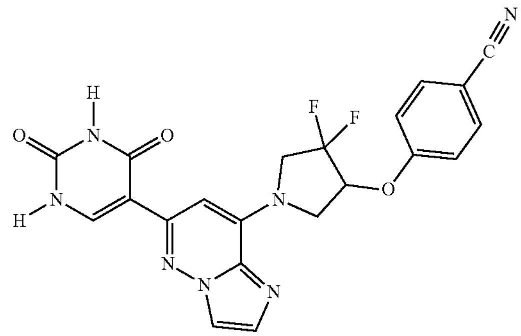 [SMILES: N#Cc1ccc(OC2CN(c3cc(-c4c[nH]c(=O)[nH]c4=O)nn4ccnc34)CC2(F)F)cc1] | 4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)benzonitrile |
| 232 | 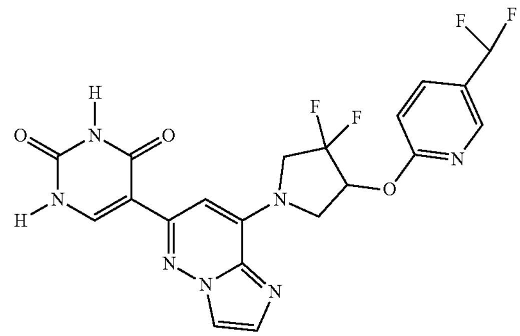 [SMILES: O=c1[nH]cc(-c2cc(N3CC(Oc4ccc(C(F)F)cn4)C(F)(F)C3)c3nccn3n2)c(=O)[nH]1] | 5-(8-(4-((5-(difluoromethyl)pyridin-2-yl)oxy)-3,3-difluoropyrrolidin-1-yl)imidazo[1,2-b]pyridazin-6-yl)pyrimidine-2,4(1H,3H)-dione |
| 233 | 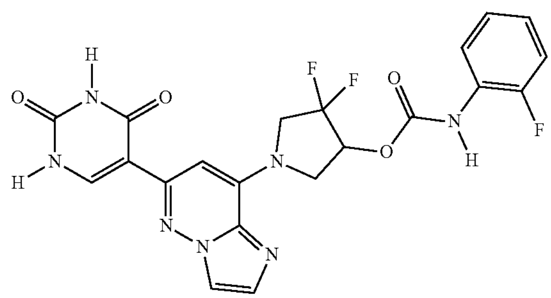 [SMILES: O=C(Nc1ccccc1F)OC1CN(c2cc(-c3c[nH]c(=O)[nH]c3=O)nn3ccnc23)CC1(F)F] | 1-(6-(2,4-dioxo-1,2,3,4-tetrahydropyrimidin-5-yl)imidazo[1,2-b]pyridazin-8-yl)-4,4-difluoropyrrolidin-3-yl (2-fluorophenyl)carbamate |
| 234 | 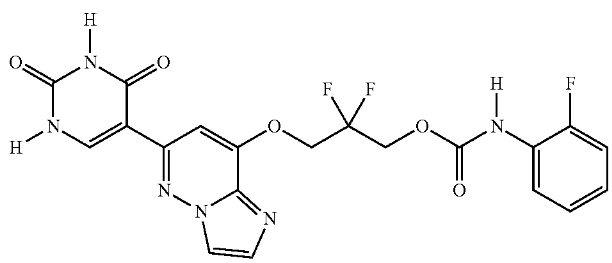 [SMILES: O=C(Nc1ccccc1F)OCC(F)(F)COc1cc(-c2c[nH]c(=O)[nH]c2=O)nn2ccnc12] | 3-((6-(2,4-dioxo-1,2,3,4-tetrahydropyrimidin-5-yl)imidazo[1,2-b]pyridazin-8-yl)oxy)-2,2-difluoropropyl (2-fluorophenyl)carbamate |
| 235 | 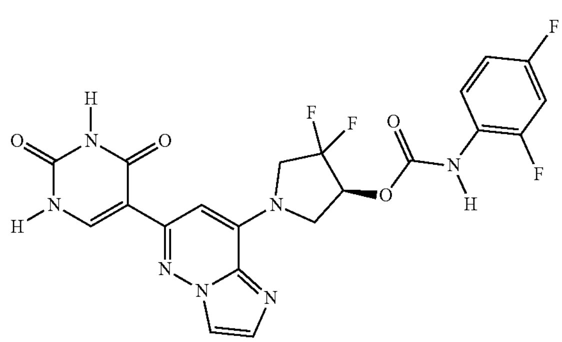 [SMILES: O=C(Nc1ccc(F)cc1F)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl (2,4-difluorophenyl)carbamate |

TABLE 2-continued

Examples

| Ex. No. | Structure | IUPAC Name |
|---|---|---|
| 236 | 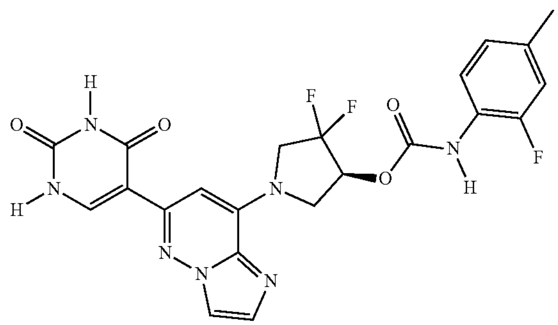 [SMILES: Cc1ccc(NC(=O)O[C@H]2CN(c3cc(-c4c[nH]c(=O)[nH]c4=O)nn4ccnc34)CC2(F)F)c(F)c1] | (S)-1-(6-(2,4-dioxo-1,2,3,4-tetrahydropyrimidin-5-yl)imidazo[1,2-b]pyridazin-8-yl)-4,4-difluoropyrrolidin-3-yl (2-fluoro-4-methylphenyl)carbamate |
| 237 | 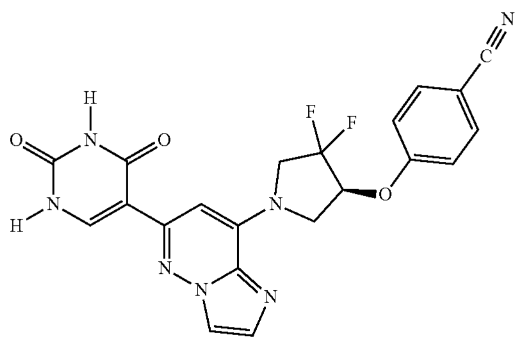 [SMILES: N#Cc1ccc(O[C@H]2CN(c3cc(-c4c[nH]c(=O)[nH]c4=O)nn4ccnc34)CC2(F)F)cc1] | (S)-4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)benzonitrile |
| 238 | 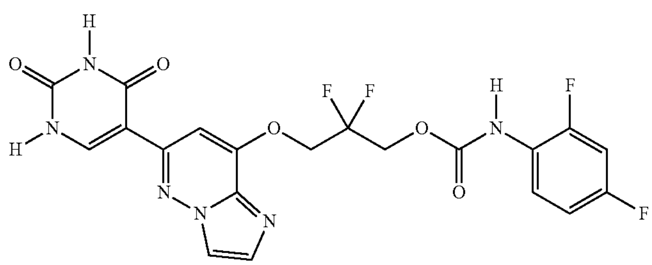 [SMILES: O=C(Nc1ccc(F)cc1F)OCC(F)(F)COc1cc(-c2c[nH]c(=O)[nH]c2=O)nn2ccnc12] | 3-((6-(2,4-dioxo-1,2,3,4-tetrahydropyrimidin-5-yl)imidazo[1,2-b]pyridazin-8-yl)oxy)-2,2-difluoropropyl (2,4-difluorophenyl)carbamate |
| 239 | 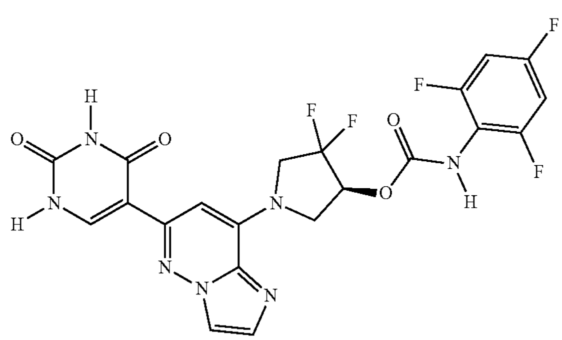 [SMILES: O=C(Nc1c(F)cc(F)cc1F)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl (2,4,6-trifluorophenyl)carbamate |
| 240 | 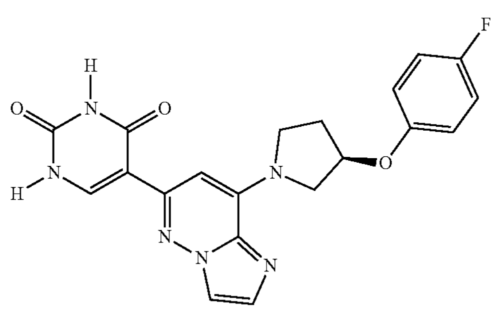 [SMILES: O=c1[nH]cc(-c2cc(N3CC[C@@H](Oc4ccc(F)cc4)C3)c3nccn3n2)c(=O)[nH]1] | (R)-5-(8-(3-(4-fluorophenoxy)pyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 241 | 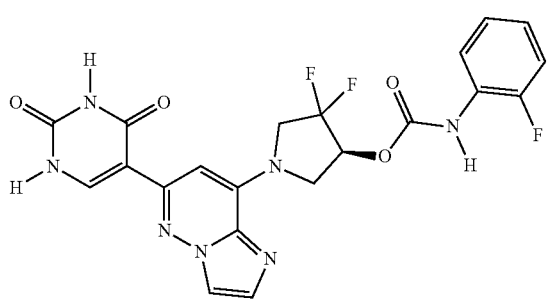 [SMILES: O=C(Nc1ccccc1F)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl (2-fluorophenyl)carbamate |
| 242 | 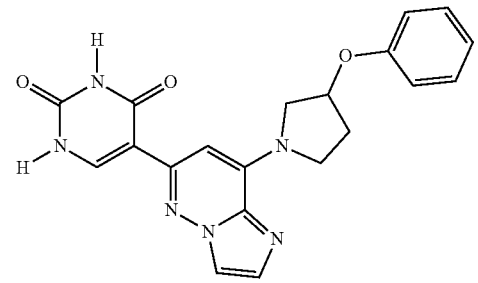 [SMILES: O=c1[nH]cc(-c2cc(N3CCC(Oc4ccccc4)C3)c3nccn3n2)c(=O)[nH]1] | 5-(8-(3-phenoxypyrrolidin-1-yl)imidazo[1,2-b]pyridazin-6-yl)pyrimidine-2,4(1H,3H)-dione |
| 243 | 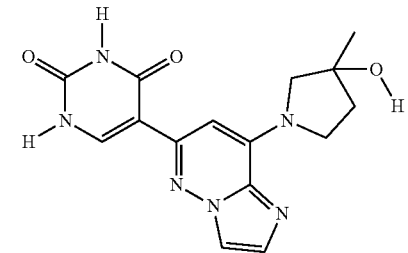 [SMILES: CC1(O)CCN(c2cc(-c3c[nH]c(=O)[nH]c3=O)nn3ccnc23)C1] | 5-(8-(3-hydroxy-3-methylpyrrolidin-1-yl)imidazo[1,2-b]pyridazin-6-yl)pyrimidine-2,4(1H,3H)-dione |
| 244 | 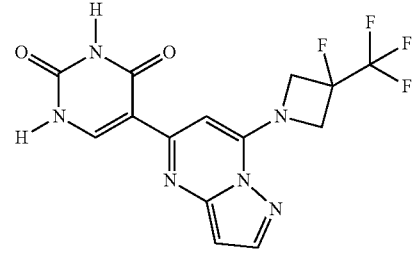 [SMILES: O=c1[nH]cc(-c2cc(N3CC(F)(C(F)(F)F)C3)n3nccc3n2)c(=O)[nH]1] | 5-(7-(3-fluoro-3-(trifluoromethyl)azetidin-1-yl)pyrazolo[1,5-a]pyrimidin-5-yl)pyrimidine-2,4(1H,3H)-dione |
| 245 | 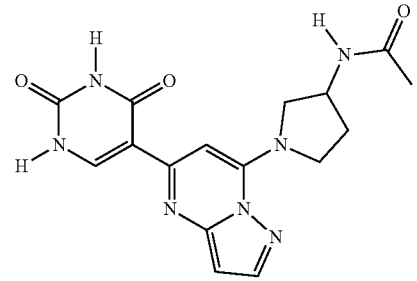 [SMILES: CC(=O)NC1CCN(c2cc(-c3c[nH]c(=O)[nH]c3=O)nc3ccnn23)C1] | N-(1-(5-(2,4-dioxo-1,2,3,4-tetrahydropyrimidin-5-yl)pyrazolo[1,5-a]pyrimidin-7-yl)pyrrolidin-3-yl)acetamide |

TABLE 2-continued

| Ex. No. | Structure | IUPAC Name |
| --- | --- | --- |
| 246 | 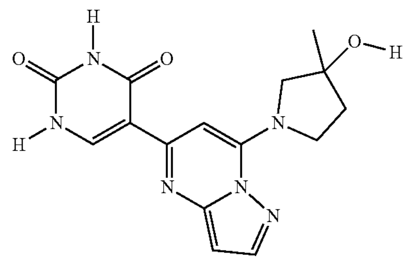 [SMILES: CC1(O)CCN(c2cc(-c3c[nH]c(=O)[nH]c3=O)nc3ccnn23)C1] | 5-(7-(3-hydroxy-3-methylpyrrolidin-1-yl)pyrazolo[1,5-a]pyrimidin-5-yl)pyrimidine-2,4(1H,3H)-dione |
| 247 | 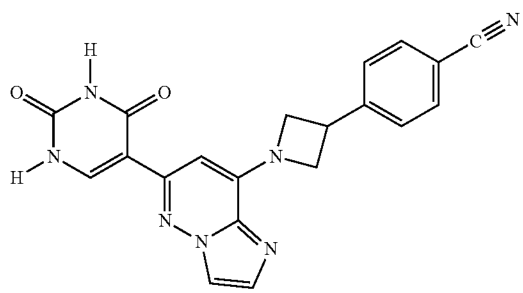 [SMILES: N#Cc1ccc(C2CN(c3cc(-c4c[nH]c(=O)[nH]c4=O)nn4ccnc34)C2)cc1] | 4-(1-(6-(2,4-dioxo-1,2,3,4-tetrahydropyrimidin-5-yl)imidazo[1,2-b]pyridazin-8-yl)azetidin-3-yl)benzonitrile |
| 248 | 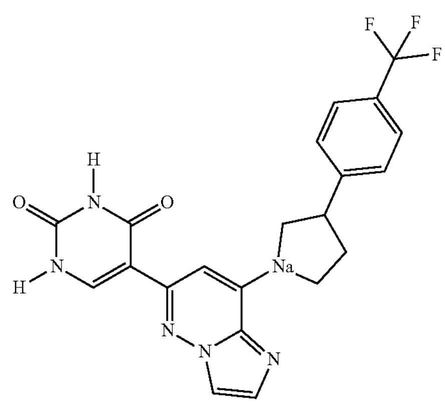 | 5-(8-(3-(4-(trifluoromethyl)phenyl)pyrrolidin-1-yl)imidazo[1,2-b]pyridazin-6-yl)pyrimidine-2,4(1H,3H)-dione |
| 249 | 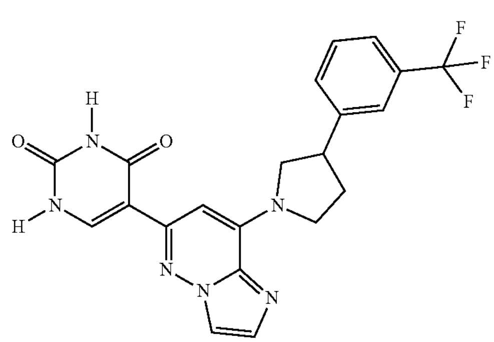 [SMILES: O=c1[nH]cc(-c2cc(N3CCC(c4cccc(C(F)(F)F)c4)C3)c3nccn3n2)c(=O)[nH]1] | 5-(8-(3-(3-(trifluoromethyl)phenyl)pyrrolidin-1-yl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 250 | 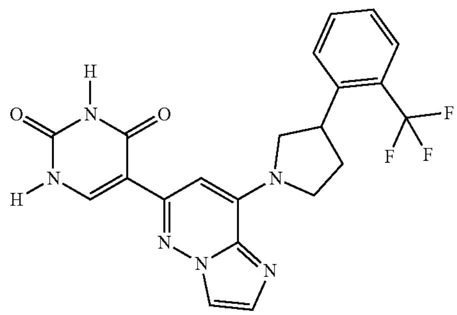 [SMILES: O=c1[nH]cc(-c2cc(N3CCC(c4ccccc4C(F)(F)F)C3)c3nccn3n2)c(=O)[nH]1] | 5-(8-(3-(2-(trifluoromethyl)phenyl)pyrrolidin-1-yl)imidazo[1,2-b]pyridazin-6-yl)pyrimidine-2,4(1H,3H)-dione |
| 251 | 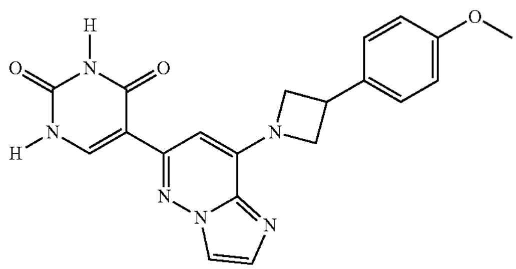 [SMILES: COc1ccc(C2CN(c3cc(-c4c[nH]c(=O)[nH]c4=O)nn4ccnc34)C2)cc1] | 5-(8-(3-(4-methoxyphenyl)azetidin-1-yl)imidazo[1,2-b]pyridazin-6-yl)pyrimidine-2,4(1H,3H)-dione |
| 252 | 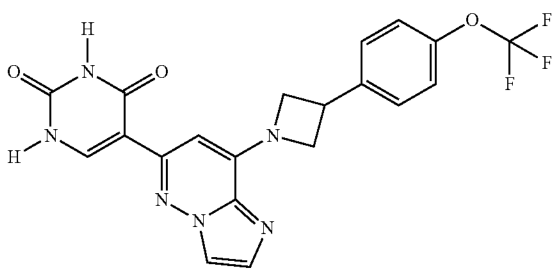 [SMILES: O=c1[nH]cc(-c2cc(N3CC(c4ccc(OC(F)(F)F)cc4)C3)c3nccn3n2)c(=O)[nH]1] | 5-(8-(3-(4-(trifluoromethoxy)phenyl)azetidin-1-yl)imidazo[1,2-b]pyridazin-6-yl)pyrimidine-2,4(1H,3H)-dione |
| 253 | 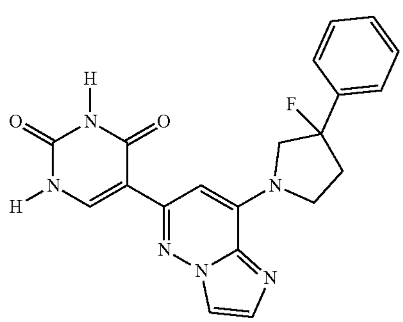 [SMILES: O=c1[nH]cc(-c2cc(N3CCC(F)(c4ccccc4)C3)c3nccn3n2)c(=O)[nH]1] | 5-(8-(3-fluoro-3-phenylpyrrolidin-1-yl)imidazo[1,2-b]pyridazin-6-yl)pyrimidine-2,4(1H,3H)-dione |
| 254 | 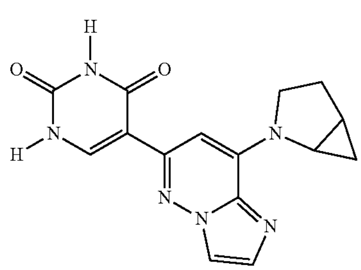 [SMILES: O=c1[nH]cc(-c2cc(N3CCC4CC43)c3nccn3n2)c(=O)[nH]1] | 5-(8-(2-azabicyclo[3.1.0]hexan-2-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 255 | 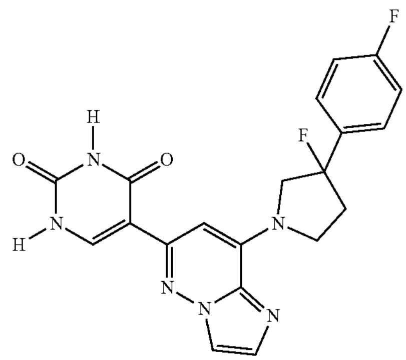 [SMILES: O=c1[nH]cc(-c2cc(N3CCC(F)(c4ccc(F)cc4)C3)c3nccn3n2)c(=O)[nH]1] | 5-(8-(3-fluoro-3-(4-fluorophenyl)pyrrolidin-1-yl)imidazo[1,2-b]pyridazin-6-yl)pyrimidine-2,4(1H,3H)-dione |
| 256 | 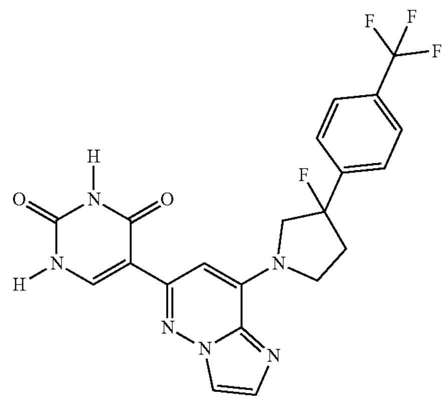 [SMILES: O=c1[nH]cc(-c2cc(N3CCC(F)(c4ccc(C(F)(F)F)cc4)C3)c3nccn3n2)c(=O)[nH]1] | 5-(8-(3-fluoro-3-(4-(trifluoromethyl)phenyl)pyrrolidin-1-yl)imidazo[1,2-b]pyridazin-6-yl)pyrimidine-2,4(1H,3H)-dione |
| 257 | 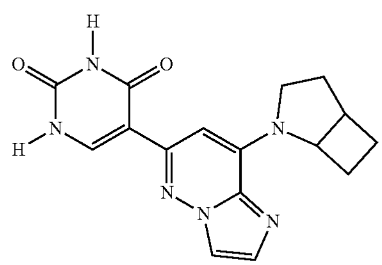 [SMILES: O=c1[nH]cc(-c2cc(N3CCC4CCC43)c3nccn3n2)c(=O)[nH]1] | 5-(8-(2-azabicyclo[3.2.0]heptan-2-yl)imidazo[1,2-b]pyridazin-6-yl)pyrimidine-2,4(1H,3H)-dione |
| 258 | 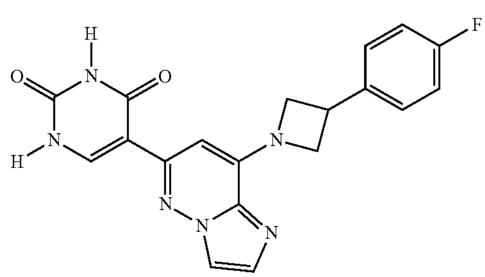 [SMILES: O=c1[nH]cc(-c2cc(N3CC(c4ccc(F)cc4)C3)c3nccn3n2)c(=O)[nH]1] | 5-(8-(3-(4-fluorophenyl)azetidin-1-yl)imidazo[1,2-b]pyridazin-6-yl)pyrimidine-2,4(1H,3H)-dione |
| 259 | 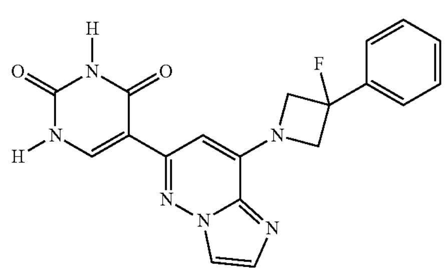 [SMILES: O=c1[nH]cc(-c2cc(N3CC(F)(c4ccccc4)C3)c3nccn3n2)c(=O)[nH]1] | 5-(8-(3-fluoro-3-phenylazetidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 260 | 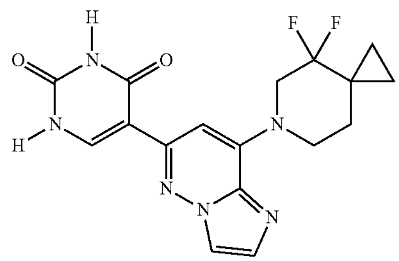 [SMILES: O=c1[nH]cc(-c2cc(N3CCC4(CC4)C(F)(F)C3)c3nccn3n2)c(=O)[nH]1] | 5-(8-(4,4-difluoro-6-azaspiro[2.5]octan-6-yl)imidazo[1,2-b]pyridazin-6-yl)pyrimidine-2,4(1H,3H)-dione |
| 261 | 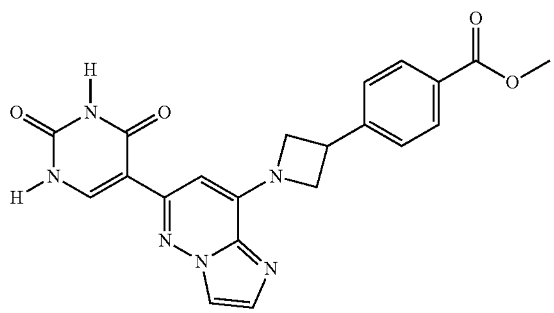 [SMILES: COC(=O)c1ccc(C2CN(c3cc(-c4c[nH]c(=O)[nH]c4=O)nn4ccnc34)C2)cc1] | methyl 4-(1-(6-(2,4-dioxo-1,2,3,4-tetrahydropyrimidin-5-yl)imidazo[1,2-b]pyridazin-8-yl)azetidin-3-yl)benzoate |
| 262 | 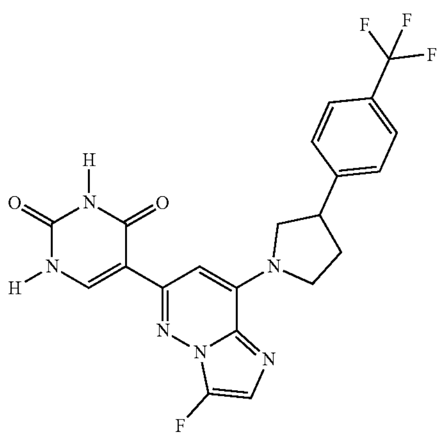 [SMILES: O=c1[nH]cc(-c2cc(N3CCC(c4ccc(C(F)(F)F)cc4)C3)c3ncc(F)n3n2)c(=O)[nH]1] | 5-(3-fluoro-8-(3-(4-(trifluoromethyl)phenyl)pyrrolidin-1-yl)imidazo[1,2-b]pyridazin-6-yl)pyrimidine-2,4(1H,3H)-dione |
| 263 | 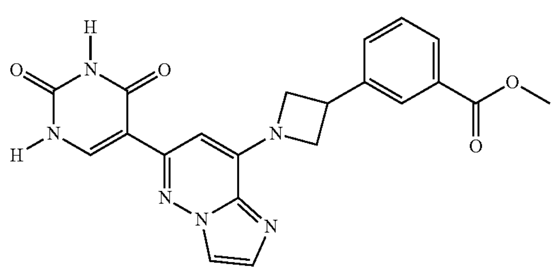 [SMILES: COC(=O)c1cccc(C2CN(c3cc(-c4c[nH]c(=O)[nH]c4=O)nn4ccnc34)C2)c1] | methyl 3-(1-(6-(2,4-dioxo-1,2,3,4-tetrahydropyrimidin-5-yl)imidazo[1,2-b]pyridazin-8-yl)azetidin-3-yl)benzoate |

TABLE 2-continued

| Ex. No. | Structure | IUPAC Name |
| --- | --- | --- |
| 264 | 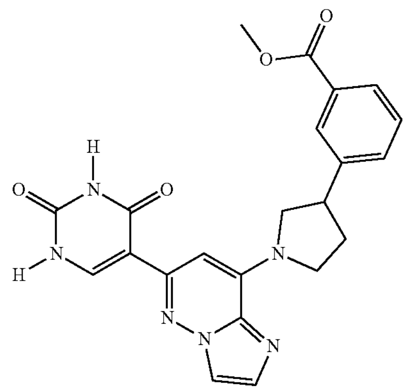 [SMILES: COC(=O)c1cccc(C2CCN(c3cc(-c4c[nH]c(=O)[nH]c4=O)nn4ccnc34)C2)c1] | methyl 3-(1-(6-(2,4-dioxo-1,2,3,4-tetrahydropyrimidin-5-yl)imidazo[1,2-b]pyridazin-8-yl)pyrrolidin-3-yl)benzoate |
| 265 | 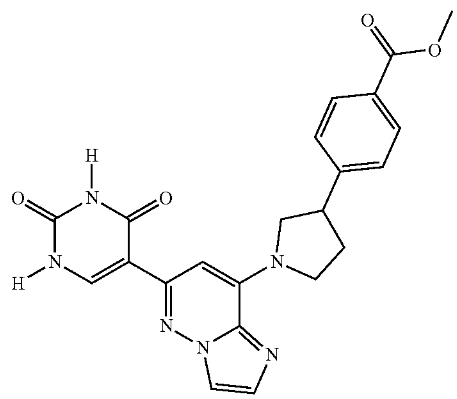 [SMILES: COC(=O)c1ccc(C2CCN(c3cc(-c4c[nH]c(=O)[nH]c4=O)nn4ccnc34)C2)cc1] | methyl 4-(1-(6-(2,4-dioxo-1,2,3,4-tetrahydropyrimidin-5-yl)imidazo[1,2-b]pyridazin-8-yl)pyrrolidin-3-yl)benzoate |
| 266 | 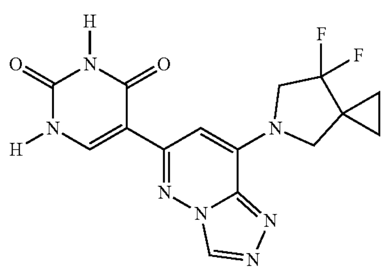 [SMILES: O=c1[nH]cc(-c2cc(N3CC(F)(F)C4(CC4)C3)c3nncn3n2)c(=O)[nH]1] | 5-(8-(7,7-difluoro-5-azaspiro[2.4]heptan-5-yl)-[1,2,4]triazolo[4,3-b]pyridazin-6-yl)pyrimidine-2,4(1H,3H)-dione |
| 267 | 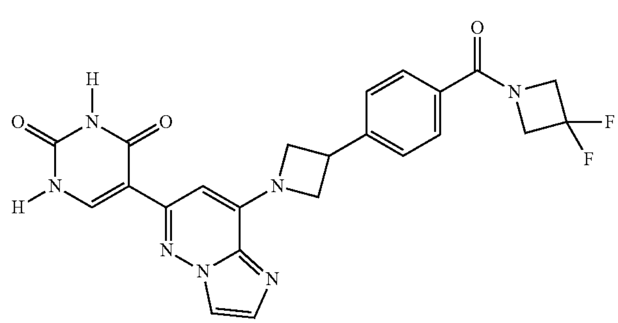 [SMILES: O=C(c1ccc(C2CN(c3cc(-c4c[nH]c(=O)[nH]c4=O)nn4ccnc34)C2)cc1)N1CC(F)(F)C1] | 5-(8-(3-(4-(3,3-difluoroazetidine-1-carbonyl)phenyl)azetidin-1-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 268 | 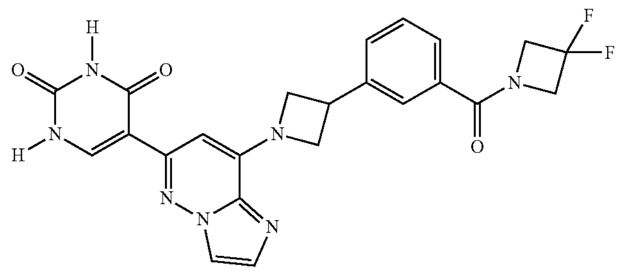 [SMILES: O=C(c1cccc(C2CN(c3cc(-c4c[nH]c(=O)[nH]c4=O)nn4ccnc34)C2)c1)N1CC(F)(F)C1] | 5-(8-(3-(3-(3,3-difluoroazetidine-1-carbonyl)phenyl)azetidin-1-yl)imidazo[1,2-b]pyridazin-6-yl)pyrimidine-2,4(1H,3H)-dione |
| 269 | 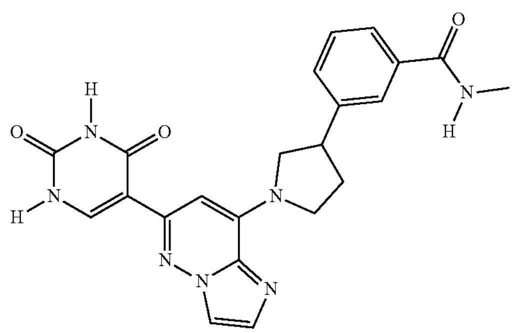 [SMILES: CNC(=O)c1cccc(C2CCN(c3cc(-c4c[nH]c(=O)[nH]c4=O)nn4ccnc34)C2)c1] | 3-(1-(6-(2,4-dioxo-1,2,3,4-tetrahydropyrimidin-5-yl)imidazo[1,2-b]pyridazin-8-yl)pyrrolidin-3-yl)-N-methylbenzamide |
| 270 | 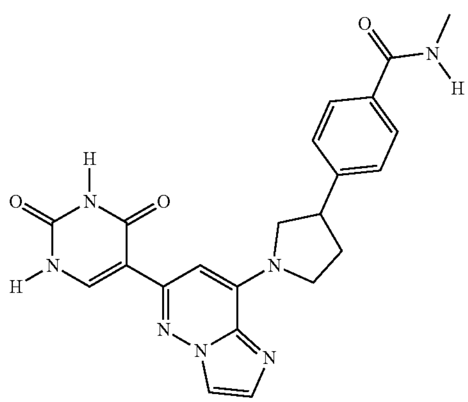 [SMILES: CNC(=O)c1ccc(C2CCN(c3cc(-c4c[nH]c(=O)[nH]c4=O)nn4ccnc34)C2)cc1] | 4-(1-(6-(2,4-dioxo-1,2,3,4-tetrahydropyrimidin-5-yl)imidazo[1,2-b]pyridazin-8-yl)pyrrolidin-3-yl)-N-methylbenzamide |
| 271 | 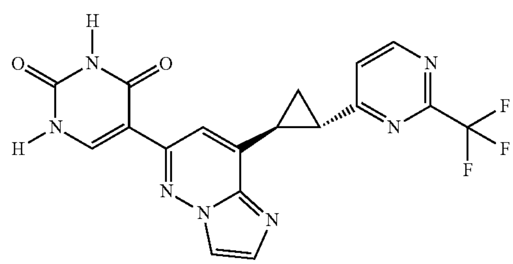 [SMILES: O=c1[nH]cc(-c2cc([C@H]3C[C@@H]3c3ccnc(C(F)(F)F)n3)c3nccn3n2)c(=O)[nH]1] | 5-(8-((1S,2S)-2-(2-(trifluoromethyl)pyrimidin-4-yl)cyclopropyl)imidazo[1,2-b]pyridazin-6-yl)pyrimidine-2,4(1H,3H)-dione |
| 272 | 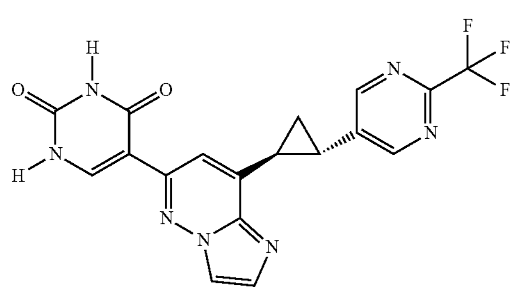 [SMILES: O=c1[nH]cc(-c2cc([C@H]3C[C@@H]3c3cnc(C(F)(F)F)nc3)c3nccn3n2)c(=O)[nH]1] | 5-(8-((1S,2S)-2-(2-(trifluoromethyl)pyrimidin-5-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 273 | 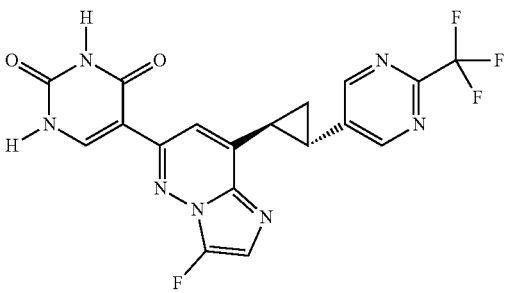 [SMILES: O=c1[nH]cc(-c2cc([C@H]3C[C@@H]3c3cnc(C(F)(F)F)nc3)c3ncc(F)n3n2)c(=O)[nH]1] | 5-(3-fluoro-8-((1R,2R)-2-(2-(trifluoromethyl)pyrimidin-5-yl)cyclopropyl)imidazo[1,2-b]pyridazin-6-yl)pyrimidine-2,4(1H,3H)-dione |
| 274 | 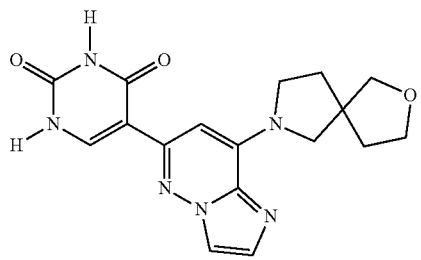 [SMILES: O=c1[nH]cc(-c2cc(N3CCC4(CCOC4)C3)c3nccn3n2)c(=O)[nH]1] | 5-(8-(2-oxa-7-azaspiro[4.4]nonan-7-yl)imidazo[1,2-b]pyridazin-6-yl)pyrimidine-2,4(1H,3H)-dione |
| 275 | 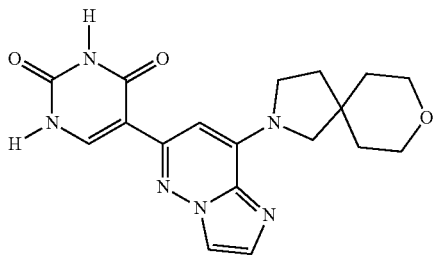 [SMILES: O=c1[nH]cc(-c2cc(N3CCC4(CCOCC4)C3)c3nccn3n2)c(=O)[nH]1] | 5-(8-(8-oxa-2-azaspiro[4.5]decan-2-yl)imidazo[1,2-b]pyridazin-6-yl)pyrimidine-2,4(1H,3H)-dione |
| 276 | 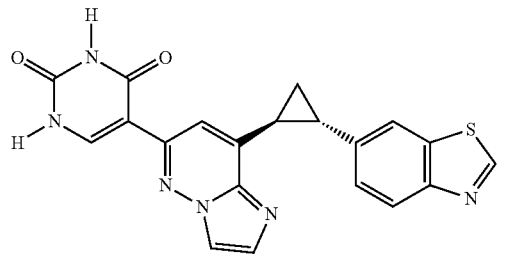 [SMILES: O=c1[nH]cc(-c2cc([C@H]3C[C@@H]3c3ccc4ncsc4c3)c3nccn3n2)c(=O)[nH]1] | 5-(8-((1S,2S)-2-(benzo[d]thiazol-6-yl)cyclopropyl)imidazo[1,2-b]pyridazin-6-yl)pyrimidine-2,4(1H,3H)-dione |
| 277 | 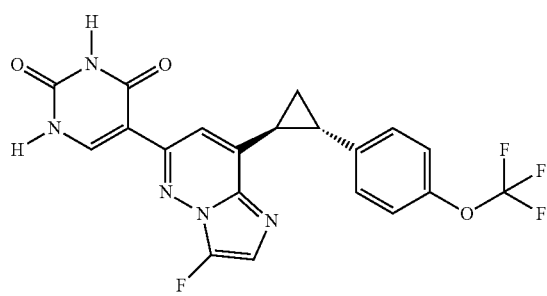 [SMILES: O=c1[nH]cc(-c2cc([C@H]3C[C@@H]3c3ccc(OC(F)(F)F)cc3)c3ncc(F)n3n2)c(=O)[nH]1] | 5-(3-fluoro-8-((1S,2S)-2-(4-(trifluoromethoxy)phenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 278 | 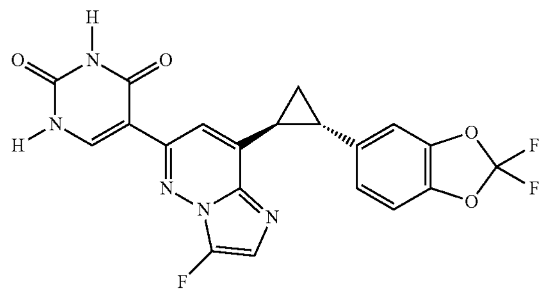 [SMILES: O=c1[nH]cc(-c2cc([C@H]3C[C@@H]3c3ccc4c(c3)OC(F)(F)O4)c3ncc(F)n3n2)c(=O)[nH]1] | 5-(8-((1S,2S)-2-(2,2-difluorobenzo[d][1,3]dioxol-5-yl)cyclopropyl)-3-fluoroimidazo[1,2-b]pyridazin-6-yl)pyrimidine-2,4(1H,3H)-dione |
| 279 | 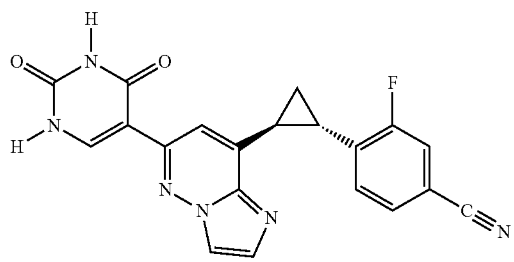 [SMILES: N#Cc1ccc([C@H]2C[C@@H]2c2cc(-c3c[nH]c(=O)[nH]c3=O)nn3ccnc23)c(F)c1] | 4-((1S,2S)-2-(6-(2,4-dioxo-1,2,3,4-tetrahydropyrimidin-5-yl)imidazo[1,2-b]pyridazin-8-yl)cyclopropyl)-3-fluorobenzonitrile |
| 280 | 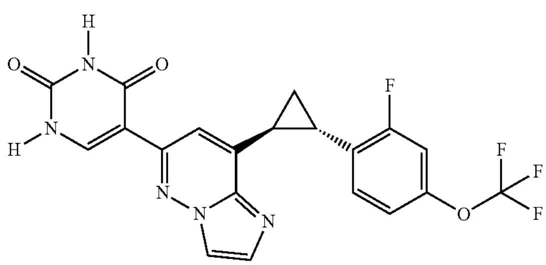 [SMILES: O=c1[nH]cc(-c2cc([C@H]3C[C@@H]3c3ccc(OC(F)(F)F)cc3F)c3nccn3n2)c(=O)[nH]1] | 5-(8-((1S,2S)-2-(2-fluoro-4-(trifluoromethoxy)phenyl)cyclopropyl)imidazo[1,2-b]pyridazin-6-yl)pyrimidine-2,4(1H,3H)-dione |
| 281 | 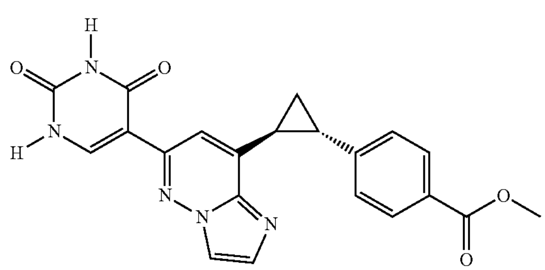 [SMILES: COC(=O)c1ccc([C@H]2C[C@@H]2c2cc(-c3c[nH]c(=O)[nH]c3=O)nn3ccnc23)cc1] | methyl 4-((1S,2S)-2-(6-(2,4-dioxo-1,2,3,4-tetrahydropyrimidin-5-yl)imidazo[1,2-b]pyridazin-8-yl)cyclopropyl)benzoate |
| 282 | 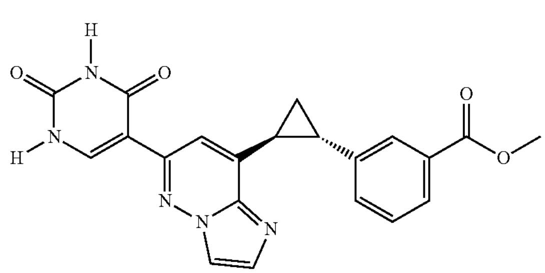 [SMILES: COC(=O)c1cccc([C@H]2C[C@@H]2c2cc(-c3c[nH]c(=O)[nH]c3=O)nn3ccnc23)c1] | methyl 3-((1S,2S)-2-(6-(2,4-dioxo-1,2,3,4-tetrahydropyrimidin-5-yl)imidazo[1,2-b]pyridazin-8-yl)cyclopropyl)benzoate |

TABLE 2-continued

| Ex. No. | Structure | IUPAC Name |
|---|---|---|
| 283 | 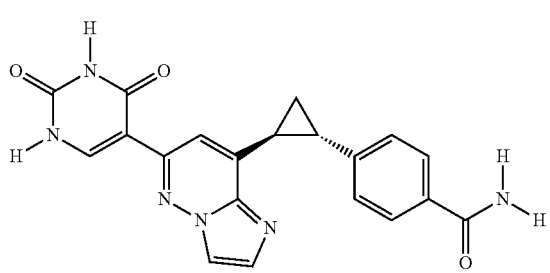 [SMILES: NC(=O)c1ccc([C@H]2C[C@@H]2c2cc(-c3c[nH]c(=O)[nH]c3=O)nn3ccnc23)cc1] | 4-((1S,2S)-2-(6-(2,4-dioxo-1,2,3,4-tetrahydropyrimidin-5-yl)imidazo[1,2-b]pyridazin-8-yl)cyclopropyl)benzamide |
| 284 | 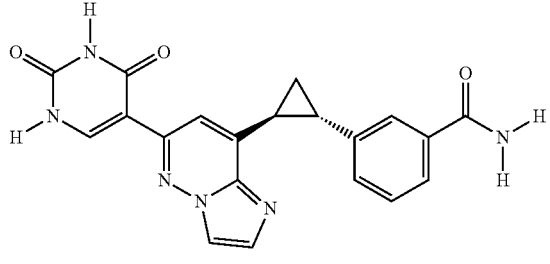 [SMILES: NC(=O)c1cccc([C@H]2C[C@@H]2c2cc(-c3c[nH]c(=O)[nH]c3=O)nn3ccnc23)c1] | 3-((1S,2S)-2-(6-(2,4-dioxo-1,2,3,4-tetrahydropyrimidin-5-yl)imidazo[1,2-b]pyridazin-8-yl)cyclopropyl)benzamide |
| 285 | 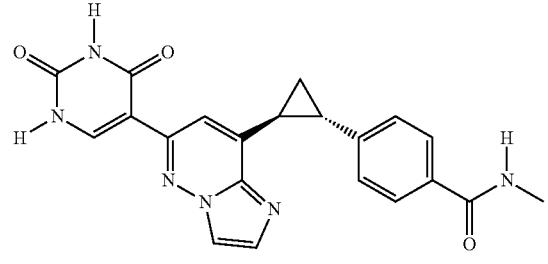 [SMILES: CNC(=O)c1ccc([C@H]2C[C@@H]2c2cc(-c3c[nH]c(=O)[nH]c3=O)nn3ccnc23)cc1] | 4-((1S,2S)-2-(6-(2,4-dioxo-1,2,3,4-tetrahydropyrimidin-5-yl)imidazo[1,2-b]pyridazin-8-yl)cyclopropyl)-N-methylbenzamide |
| 286 | 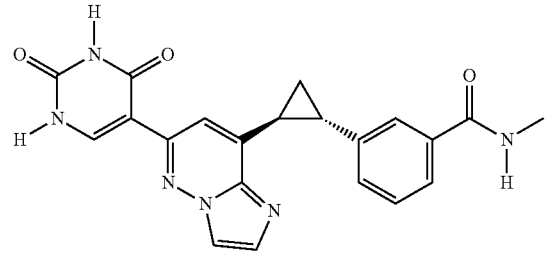 [SMILES: CNC(=O)c1cccc([C@H]2C[C@@H]2c2cc(-c3c[nH]c(=O)[nH]c3=O)nn3ccnc23)c1] | 3-((1S,2S)-2-(6-(2,4-dioxo-1,2,3,4-tetrahydropyrimidin-5-yl)imidazo[1,2-b]pyridazin-8-yl)cyclopropyl)-N-methylbenzamide |
| 287 | 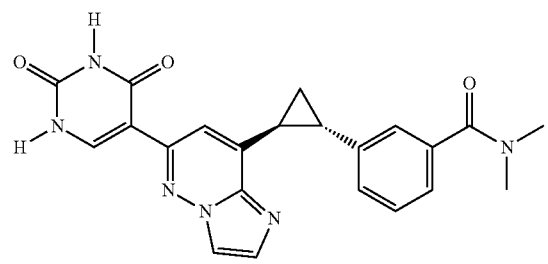 [SMILES: CN(C)C(=O)c1cccc([C@H]2C[C@@H]2c2cc(-c3c[nH]c(=O)[nH]c3=O)nn3ccnc23)c1] | 3-((1S,2S)-2-(6-(2,4-dioxo-1,2,3,4-tetrahydropyrimidin-5-yl)imidazo[1,2-b]pyridazin-8-yl)cyclopropyl)-N,N-dimethylbenzamide |

TABLE 2-continued

| Ex. No. | Structure | IUPAC Name |
|---|---|---|
| 288 | 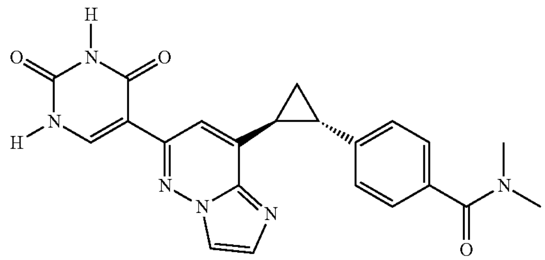 [SMILES: CN(C)C(=O)c1ccc([C@H]2C[C@@H]2c2cc(-c3c[nH]c(=O)[nH]c3=O)nn3ccnc23)cc1] | 4-((1S,2S)-2-(6-(2,4-dioxo-1,2,3,4-tetrahydropyrimidin-5-yl)imidazo[1,2-b]pyridazin-8-yl)cyclopropyl)-N,N-dimethylbenzamide |
| 289 | 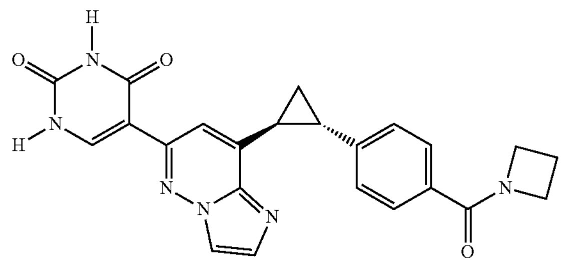 [SMILES: O=C(c1ccc([C@H]2C[C@@H]2c2cc(-c3c[nH]c(=O)[nH]c3=O)nn3ccnc23)cc1)N1CCC1] | 5-(8-((1S,2S)-2-(4-(azetidine-1-carbonyl)phenyl)cyclopropyl)imidazo[1,2-b]pyridazin-6-yl)pyrimidine-2,4(1H,3H)-dione |
| 290 | 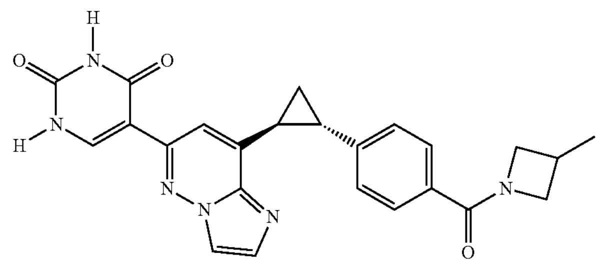 [SMILES: CC1CN(C(=O)c2ccc([C@H]3C[C@@H]3c3cc(-c4c[nH]c(=O)[nH]c4=O)nn4ccnc34)cc2)C1] | 5-(8-((1S,2S)-2-(4-(3-methylazetidine-1-carbonyl)phenyl)cyclopropyl)imidazo[1,2-b]pyridazin-6-yl)pyrimidine-2,4(1H,3H)-dione |
| 291 | 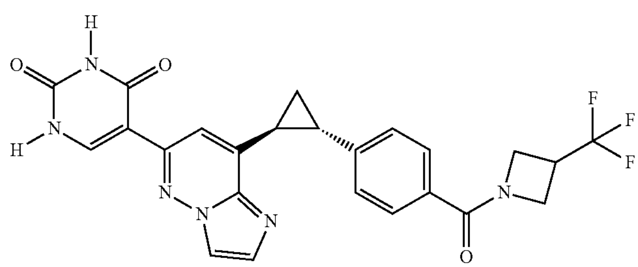 [SMILES: O=C(c1ccc([C@H]2C[C@@H]2c2cc(-c3c[nH]c(=O)[nH]c3=O)nn3ccnc23)cc1)N1CC(C(F)(F)F)C1] | 5-(8-((1S,2S)-2-(4-(3-(trifluoromethyl)azetidine-1-carbonyl)phenyl)cyclopropyl)imidazo[1,2-b]pyridazin-6-yl)pyrimidine-2,4(1H,3H)-dione |
| 292 | 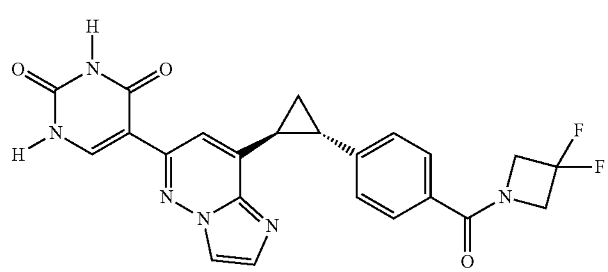 [SMILES: O=C(c1ccc([C@H]2C[C@@H]2c2cc(-c3c[nH]c(=O)[nH]c3=O)nn3ccnc23)cc1)N1CC(F)(F)C1] | 5-(8-((1S,2S)-2-(4-(3,3-difluoroazetidine-1-carbonyl)phenyl)cyclopropyl)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 293 | 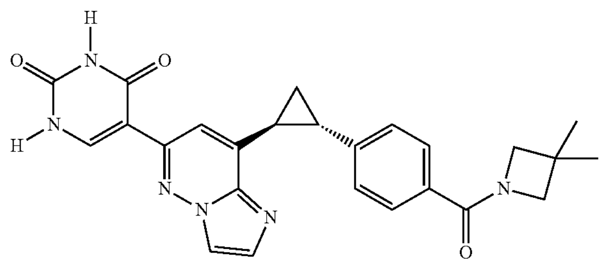 [SMILES: CC1(C)CN(C(=O)c2ccc([C@H]3C[C@@H]3c3cc(-c4c[nH]c(=O)[nH]c4=O)nn4ccnc34)cc2)C1] | 5-(8-((1S,2S)-2-(4-(3,3-dimethylazetidine-1-carbonyl)phenyl)cyclopropyl)imidazo[1,2-b]pyridazin-6-yl)pyrimidine-2,4(1H,3H)-dione |
| 294 | 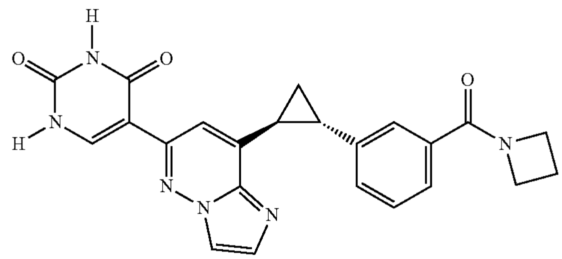 [SMILES: O=C(c1cccc([C@H]2C[C@@H]2c2cc(-c3c[nH]c(=O)[nH]c3=O)nn3ccnc23)c1)N1CCC1] | 5-(8-((1S,2S)-2-(3-(azetidine-1-carbonyl)phenyl)cyclopropyl)imidazo[1,2-b]pyridazin-6-yl)pyrimidine-2,4(1H,3H)-dione |
| 295 | 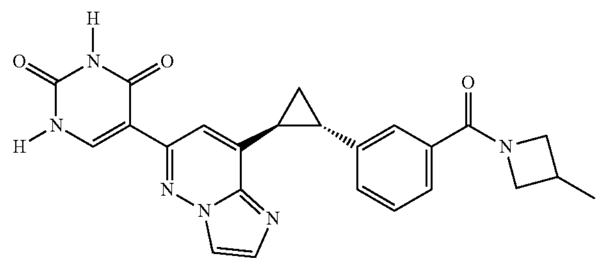 [SMILES: CC1CN(C(=O)c2cccc([C@H]3C[C@@H]3c3cc(-c4c[nH]c(=O)[nH]c4=O)nn4ccnc34)c2)C1] | 5-(8-((1S,2S)-2-(3-(3-methylazetidine-1-carbonyl)phenyl)cyclopropyl)imidazo[1,2-b]pyridazin-6-yl)pyrimidine-2,4(1H,3H)-dione |
| 296 | 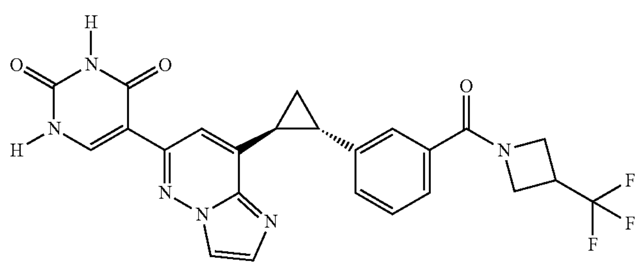 [SMILES: O=C(c1cccc([C@H]2C[C@@H]2c2cc(-c3c[nH]c(=O)[nH]c3=O)nn3ccnc23)c1)N1CC(C(F)(F)F)C1] | 5-(8-((1S,2S)-2-(3-(3-(trifluoromethyl)azetidine-1-carbonyl)phenyl)cyclopropyl)imidazo[1,2-b]pyridazin-6-yl)pyrimidine-2,4(1H,3H)-dione |
| 297 | 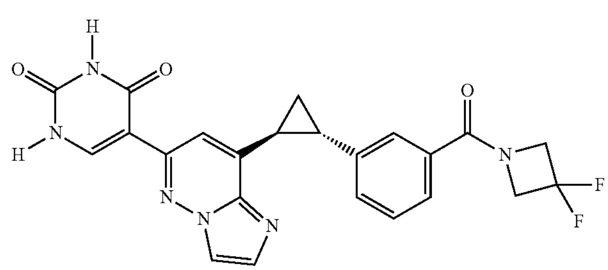 [SMILES: O=C(c1cccc([C@H]2C[C@@H]2c2cc(-c3c[nH]c(=O)[nH]c3=O)nn3ccnc23)c1)N1CC(F)(F)C1] | 5-(8-((1S,2S)-2-(3-(3,3-difluoroazetidine-1-carbonyl)phenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 298 | 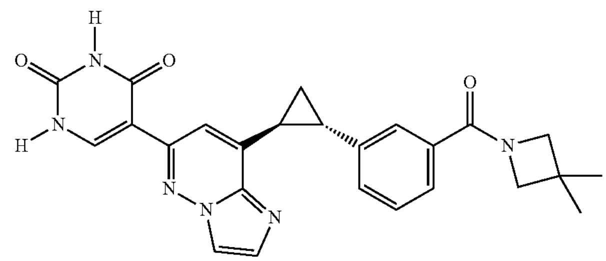 [SMILES: CC1(C)CN(C(=O)c2cccc([C@H]3C[C@@H]3c3cc(-c4c[nH]c(=O)[nH]c4=O)nn4ccnc34)c2)C1] | 5-(8-((1S,2S)-2-(3-(3,3-dimethylazetidine-1-carbonyl)phenyl)cyclopropyl)imidazo[1,2-b]pyridazin-6-yl)pyrimidine-2,4(1H,3H)-dione |
| 299 | 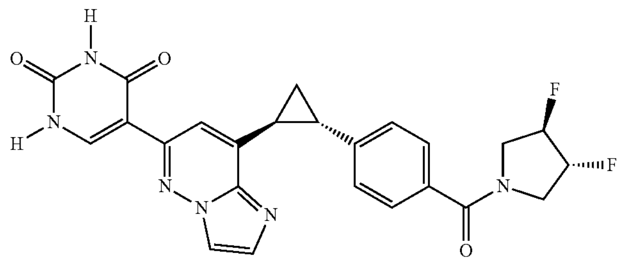 [SMILES: O=C(c1ccc([C@H]2C[C@@H]2c2cc(-c3c[nH]c(=O)[nH]c3=O)nn3ccnc23)cc1)N1C[C@@H](F)[C@H](F)C1] | 5-(8-((1S,2S)-2-(4-((3R,4R)-3,4-difluoropyrrolidine-1-carbonyl)phenyl)cyclopropyl)imidazo[1,2-b]pyridazin-6-yl)pyrimidine-2,4(1H,3H)-dione |
| 300 | 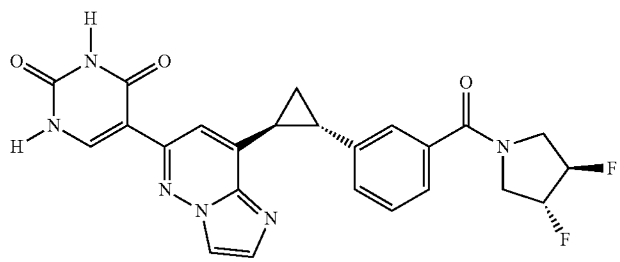 [SMILES: O=C(c1cccc([C@H]2C[C@@H]2c2cc(-c3c[nH]c(=O)[nH]c3=O)nn3ccnc23)c1)N1C[C@@H](F)[C@H](F)C1] | 5-(8-((1S,2S)-2-(3-((3R,4R)-3,4-difluoropyrrolidine-1-carbonyl)phenyl)cyclopropyl)imidazo[1,2-b]pyridazin-6-yl)pyrimidine-2,4(1H,3H)-dione |
| 301 | 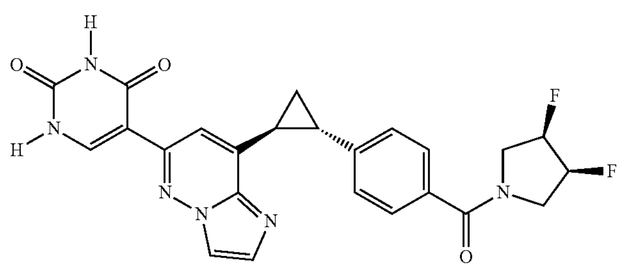 [SMILES: O=C(c1ccc([C@H]2C[C@@H]2c2cc(-c3c[nH]c(=O)[nH]c3=O)nn3ccnc23)cc1)N1C[C@@H](F)[C@@H](F)C1] | 5-(8-((1S,2S)-2-(4-((3S,4R)-3,4-difluoropyrrolidine-1-carbonyl)phenyl)cyclopropyl)imidazo[1,2-b]pyridazin-6-yl)pyrimidine-2,4(1H,3H)-dione |
| 302 | 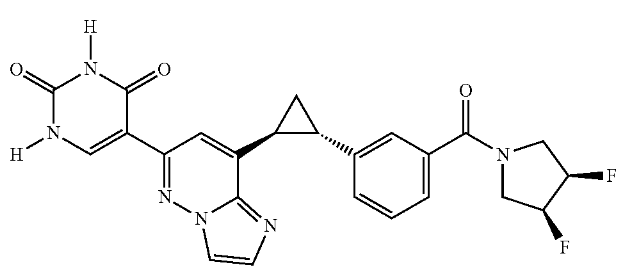 [SMILES: O=C(c1cccc([C@H]2C[C@@H]2c2cc(-c3c[nH]c(=O)[nH]c3=O)nn3ccnc23)c1)N1C[C@@H](F)[C@@H](F)C1] | 5-(8-((1S,2S)-2-(3-((3S,4R)-3,4-difluoropyrrolidine-1-carbonyl)phenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 303 | 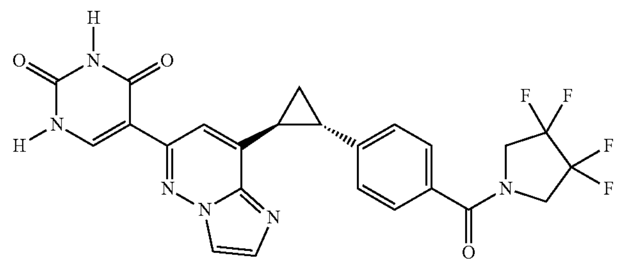 [SMILES: O=C(c1ccc([C@H]2C[C@@H]2c2cc(-c3c[nH]c(=O)[nH]c3=O)nn3ccnc23)cc1)N1CC(F)(F)C(F)(F)C1] | 5-(8-((1S,2S)-2-(4-(3,3,4,4-tetrafluoropyrrolidine-1-carbonyl)phenyl)cyclopropyl)imidazo[1,2-b]pyridazin-6-yl)pyrimidine-2,4(1H,3H)-dione |
| 304 | 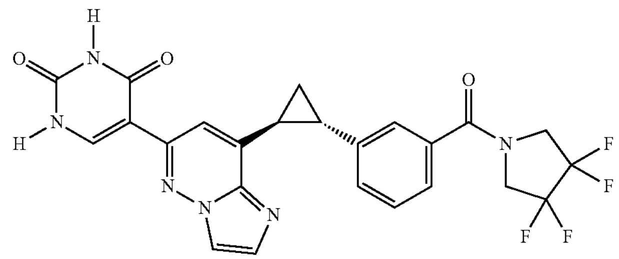 [SMILES: O=C(c1cccc([C@H]2C[C@@H]2c2cc(-c3c[nH]c(=O)[nH]c3=O)nn3ccnc23)c1)N1CC(F)(F)C(F)(F)C1] | 5-(8-((1S,2S)-2-(3-(3,3,4,4-tetrafluoropyrrolidine-1-carbonyl)phenyl)cyclopropyl)imidazo[1,2-b]pyridazin-6-yl)pyrimidine-2,4(1H,3H)-dione |
| 305 | 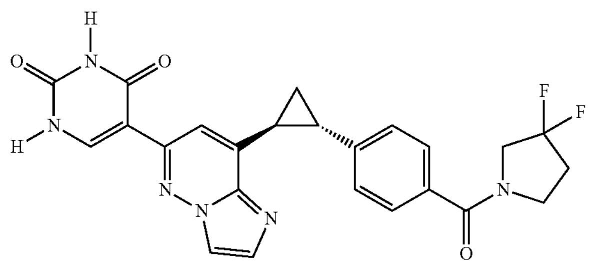 [SMILES: O=C(c1ccc([C@H]2C[C@@H]2c2cc(-c3c[nH]c(=O)[nH]c3=O)nn3ccnc23)cc1)N1CCC(F)(F)C1] | 5-(8-((1S,2S)-2-(4-(3,3-difluoropyrrolidine-1-carbonyl)phenyl)cyclopropyl)imidazo[1,2-b]pyridazin-6-yl)pyrimidine-2,4(1H,3H)-dione |
| 306 | 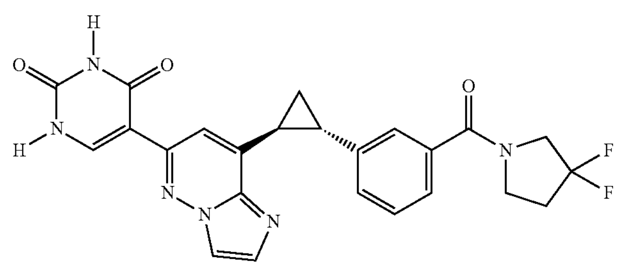 [SMILES: O=C(c1cccc([C@H]2C[C@@H]2c2cc(-c3c[nH]c(=O)[nH]c3=O)nn3ccnc23)c1)N1CCC(F)(F)C1] | 5-(8-((1S,2S)-2-(3-(3,3-difluoropyrrolidine-1-carbonyl)phenyl)cyclopropyl)imidazo[1,2-b]pyridazin-6-yl)pyrimidine-2,4(1H,3H)-dione |
| 307 | 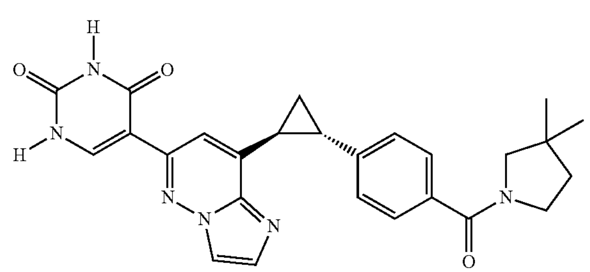 [SMILES: CC1(C)CCN(C(=O)c2ccc([C@H]3C[C@@H]3c3cc(-c4c[nH]c(=O)[nH]c4=O)nn4ccnc34)cc2)C1] | 5-(8-((1S,2S)-2-(4-(3,3-dimethylpyrrolidine-1-carbonyl)phenyl)cyclopropyl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 308 | 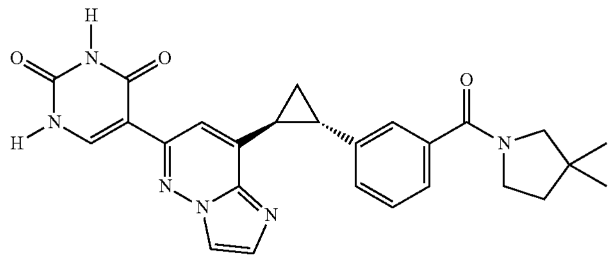 [SMILES: CC1(C)CCN(C(=O)c2cccc([C@H]3C[C@@H]3c3cc(-c4c[nH]c(=O)[nH]c4=O)nn4ccnc34)c2)C1] | 5-(8-((1S,2S)-2-(3-(3,3-dimethylpyrrolidine-1-carbonyl)phenyl)cyclopropyl)imidazo[1,2-b]pyridazin-6-yl)pyrimidine-2,4(1H,3H)-dione |
| 309 | 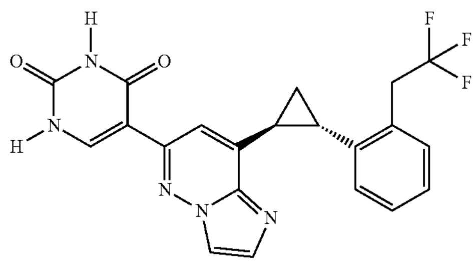 [SMILES: O=c1[nH]cc(-c2cc([C@H]3C[C@@H]3c3ccccc3CC(F)(F)F)c3nccn3n2)c(=O)[nH]1] | 5-(8-((1S,2S)-2-(2-(trifluoromethoxy)phenyl)cyclopropyl)imidazo[1,2-b]pyridazin-6-yl)pyrimidine-2,4(1H,3H)-dione |
| 310 | 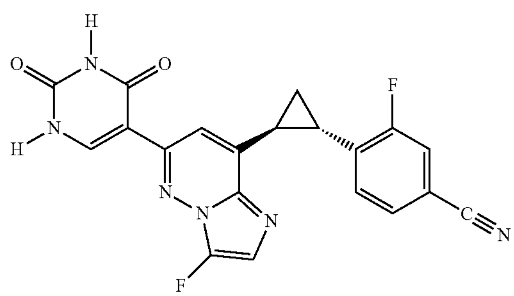 [SMILES: N#Cc1ccc([C@H]2C[C@@H]2c2cc(-c3c[nH]c(=O)[nH]c3=O)nn3c(F)cnc23)c(F)c1] | 4-((1S,2S)-2-(6-(2,4-dioxo-1,2,3,4-tetrahydropyrimidin-5-yl)-3-fluoroimidazo[1,2-b]pyridazin-8-yl)cyclopropyl)-3-fluorobenzonitrile |
| 311 | 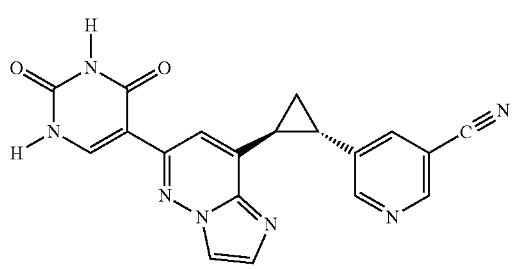 [SMILES: N#Cc1cncc([C@H]2C[C@@H]2c2cc(-c3c[nH]c(=O)[nH]c3=O)nn3ccnc23)c1] | 5-((1S,2S)-2-(6-(2,4-dioxo-1,2,3,4-tetrahydropyrimidin-5-yl)imidazo[1,2-b]pyridazin-8-yl)cyclopropyl)nicotinonitrile |
| 312 | 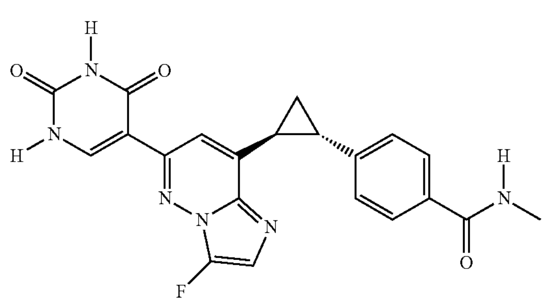 [SMILES: CNC(=O)c1ccc([C@H]2C[C@@H]2c2cc(-c3c[nH]c(=O)[nH]c3=O)nn3c(F)cnc23)cc1] | 4-((1S,2S)-2-(6-(2,4-dioxo-1,2,3,4-tetrahydropyrimidin-5-yl)-3-fluoroimidazo[1,2-b]pyridazin-8-yl)cyclopropyl)-N-methylbenzamide |

TABLE 2-continued

Examples

| Ex. No. | Structure | IUPAC Name |
| --- | --- | --- |
| 313 | 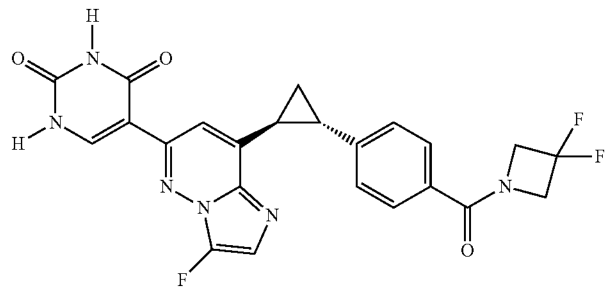 [SMILES: O=C(c1ccc([C@H]2C[C@@H]2c2cc(-c3c[nH]c(=O)[nH]c3=O)nn3c(F)cnc23)cc1)N1CC(F)(F)C1] | 5-(8-((1S,2S)-2-(4-(3,3-difluoroazetidine-1-carbonyl)phenyl)cyclopropyl)-3-fluoroimidazo[1,2-b]pyridazin-6-yl)pyrimidine-2,4(1H,3H)-dione |
| 314 | 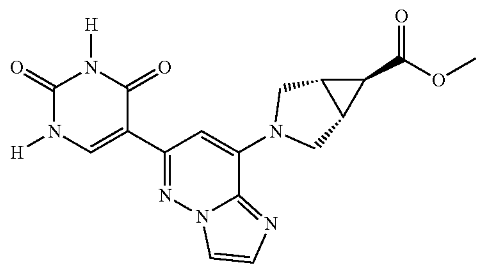 [SMILES: COC(=O)[C@H]1[C@@H]2CN(c3cc(-c4c[nH]c(=O)[nH]c4=O)nn4ccnc34)C[C@@H]21] | (1R,5S,6r)-methyl 3-(6-(2,4-dioxo-1,2,3,4-tetrahydropyrimidin-5-yl)imidazo[1,2-b]pyridazin-8-yl)-3-azabicyclo[3.1.0]hexane-6-carboxylate |
| 315 | 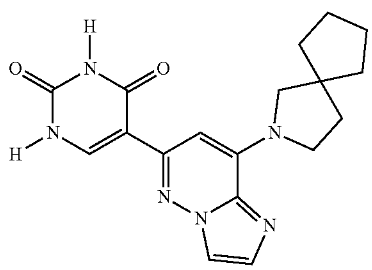 [SMILES: O=c1[nH]cc(-c2cc(N3CCC4(CCCC4)C3)c3nccn3n2)c(=O)[nH]1] | 5-(8-(2-azaspiro[4.4]nonan-2-yl)imidazo[1,2-b]pyridazin-6-yl)pyrimidine-2,4(1H,3H)-dione |
| 316 | 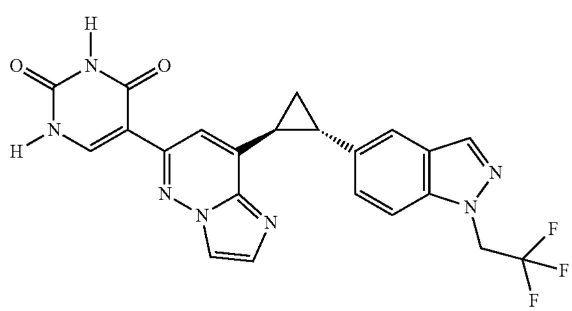 | 5-(8-((1S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione |
| 317 | 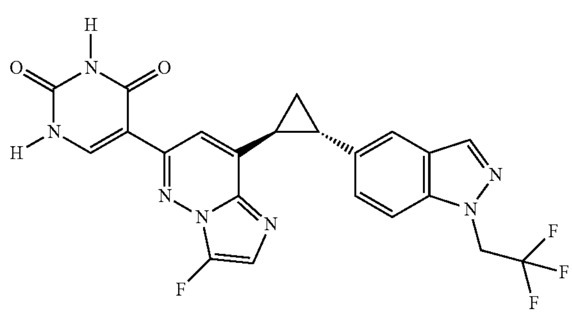 [SMILES: O=c1[nH]cc(-c2cc([C@H]3C[C@@H]3c3ccc4c(cnn4CC(F)(F)F)c3)c3ncc(F)n3n2)c(=O)[nH]1] | 5-(3-fluoro-8-((1S,2S)-2-(1-(2,2,2-trifluoroethyl)-1H-indazol-5-yl)cyclopropyl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 318 | 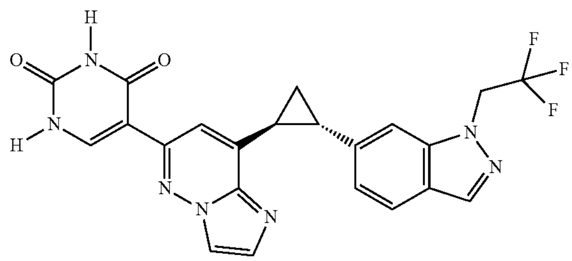 [SMILES: O=c1[nH]cc(-c2cc([C@H]3C[C@@H]3c3ccc4cnn(CC(F)(F)F)c4c3)c3nccn3n2)c(=O)[nH]1] | 5-(8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione |
| 319 | 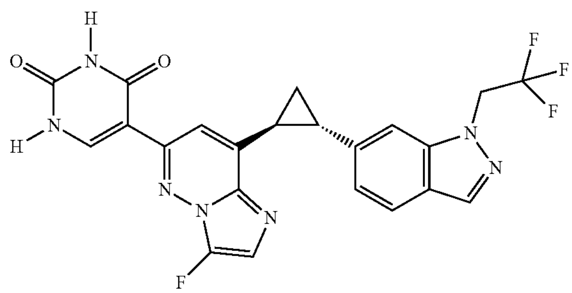 [SMILES: O=c1[nH]cc(-c2cc([C@H]3C[C@@H]3c3ccc4cnn(CC(F)(F)F)c4c3)c3ncc(F)n3n2)c(=O)[nH]1] | 5-(3-fluoro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione |
| 320 | 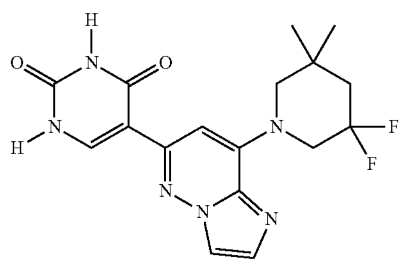 [SMILES: CC1(C)CN(c2cc(-c3c[nH]c(=O)[nH]c3=O)nn3ccnc23)CC(F)(F)C1] | 5-(8-(3,3-difluoro-5,5-dimethylpiperidin-1-yl)imidazo[1,2-b]pyridazin-6-yl)pyrimidine-2,4(1H,3H)-dione |
| 321 | 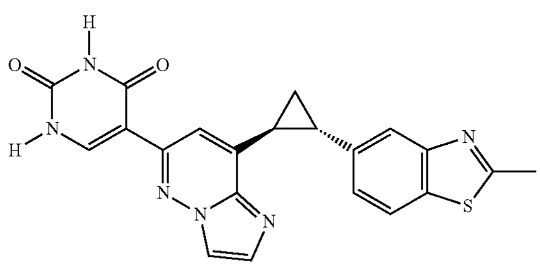 [SMILES: Cc1nc2cc([C@H]3C[C@@H]3c3cc(-c4c[nH]c(=O)[nH]c4=O)nn4ccnc34)ccc2s1] | 5-(8-((1S,2S)-2-(2-methylbenzo[d]thiazol-5-yl)cyclopropyl)imidazo[1,2-b]pyridazin-6-yl)pyrimidine-2,4(1H,3H)-dione |
| 322 | 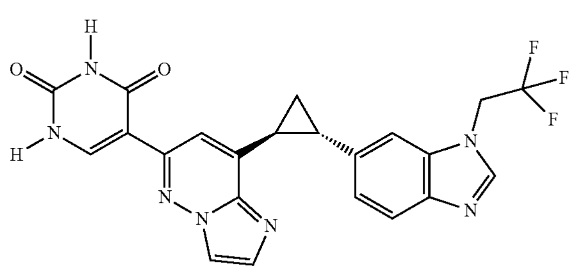 [SMILES: O=c1[nH]cc(-c2cc([C@H]3C[C@@H]3c3ccc4ncn(CC(F)(F)F)c4c3)c3nccn3n2)c(=O)[nH]1] | 5-(8-((1S,2S)-2-(1-(2,2,2-trifluoroethyl)-1H-benzo[d]imidazol-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 323 | 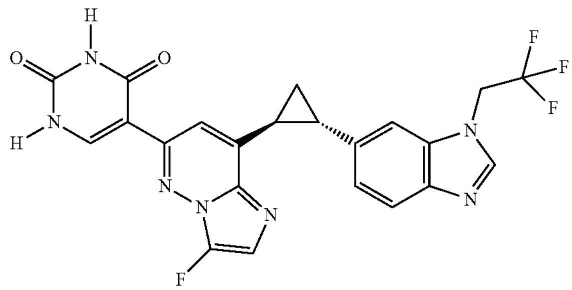 [SMILES: O=c1[nH]cc(-c2cc([C@H]3C[C@@H]3c3ccc4ncn(CC(F)(F)F)c4c3)c3ncc(F)n3n2)c(=O)[nH]1] | 5-(3-fluoro-8-((1S,2S)-2-(1-(2,2,2-trifluoroethyl)-1H-benzo[d]imidazol-6-yl)cyclopropyl)imidazo[1,2-b]pyridazin-6-yl)pyrimidine-2,4(1H,3H)-dione |
| 324 | 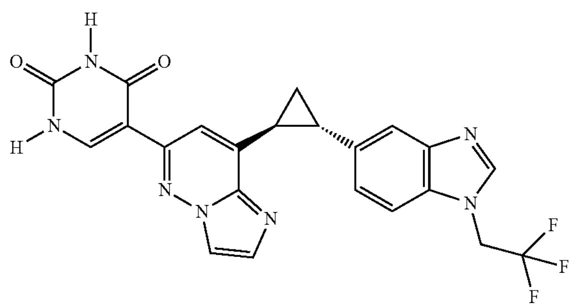 [SMILES: O=c1[nH]cc(-c2cc([C@H]3C[C@@H]3c3ccc4c(c3)ncn4CC(F)(F)F)c3nccn3n2)c(=O)[nH]1] | 5-(8-((1S,2S)-2-(1-(2,2,2-trifluoroethyl)-1H-benzo[d]imidazol-5-yl)cyclopropyl)imidazo[1,2-b]pyridazin-6-yl)pyrimidine-2,4(1H,3H)-dione |
| 325 | 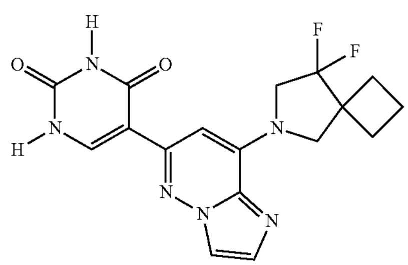 [SMILES: O=c1[nH]cc(-c2cc(N3CC(F)(F)C4(CCC4)C3)c3nccn3n2)c(=O)[nH]1] | 5-(8-(8,8-difluoro-6-azaspiro[3.4]octan-6-yl)imidazo[1,2-b]pyridazin-6-yl)pyrimidine-2,4(1H,3H)-dione |
| 326 | 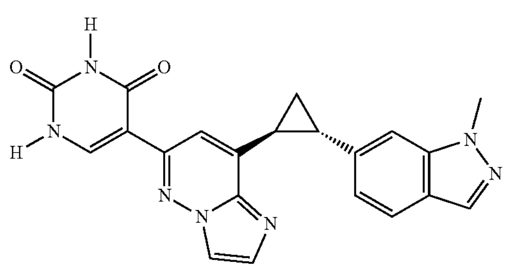 [SMILES: Cn1ncc2ccc([C@H]3C[C@@H]3c3cc(-c4c[nH]c(=O)[nH]c4=O)nn4ccnc34)cc21] | 5-(8-((1R,2S)-2-(1-methyl-1H-indazol-6-yl)cyclopropyl)imidazo[1,2-b]pyridazin-6-yl)pyrimidine-2,4(1H,3H)-dione |
| 327 | 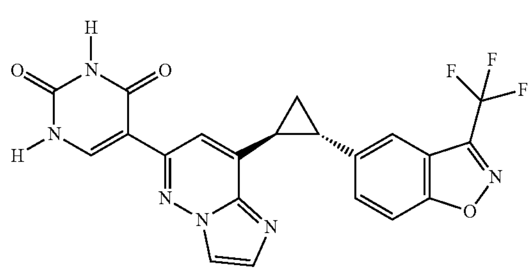 [SMILES: O=c1[nH]cc(-c2cc([C@H]3C[C@@H]3c3ccc4onc(C(F)(F)F)c4c3)c3nccn3n2)c(=O)[nH]1] | 5-(8-((1R,2S)-2-(3-(trifluoromethyl)benzo[d]isoxazol-5-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 328 | 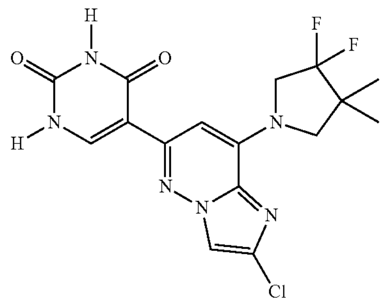 [SMILES: CC1(C)CN(c2cc(-c3c[nH]c(=O)[nH]c3=O)nn3cc(Cl)nc23)CC1(F)F] | 5-(2-chloro-8-(3,3-difluoro-4,4-dimethylpyrrolidin-1-yl)imidazo[1,2-b]pyridazin-6-yl)pyrimidine-2,4(1H,3H)-dione |
| 329 | 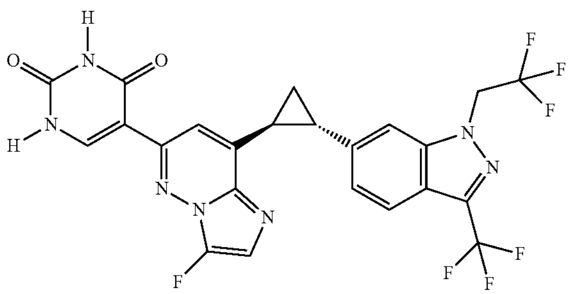 [SMILES: O=c1[nH]cc(-c2cc([C@H]3C[C@@H]3c3ccc4c(C(F)(F)F)nn(CC(F)(F)F)c4c3)c3ncc(F)n3n2)c(=O)[nH]1] | 5-(3-fluoro-8-((1S,2S)-2-(1-(2,2,2-trifluoroethyl)-3-(trifluoromethyl)-1H-indazol-6-yl)cyclopropyl)imidazo[1,2-b]pyridazin-6-yl)pyrimidine-2,4(1H,3H)-dione |
| 330 | 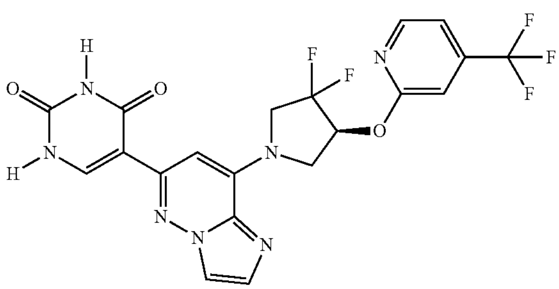 [SMILES: O=c1[nH]cc(-c2cc(N3C[C@H](Oc4cc(C(F)(F)F)ccn4)C(F)(F)C3)c3nccn3n2)c(=O)[nH]1] | (S)-5-(8-(3,3-difluoro-4-((4-(trifluoromethyl)pyridin-2-yl)oxy)pyrrolidin-1-yl)imidazo[1,2-b]pyridazin-6-yl)pyrimidine-2,4(1H,3H)-dione |
| 331 | 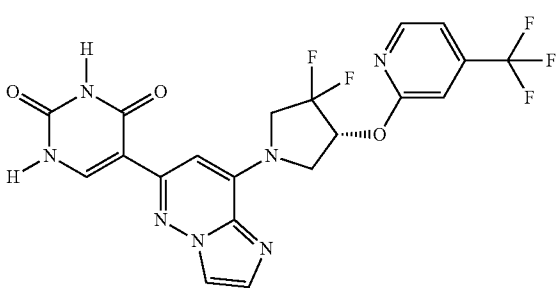 [SMILES: O=c1[nH]cc(-c2cc(N3C[C@@H](Oc4cc(C(F)(F)F)ccn4)C(F)(F)C3)c3nccn3n2)c(=O)[nH]1] | (R)-5-(8-(3,3-difluoro-4-((4-(trifluoromethyl)pyridin-2-yl)oxy)pyrrolidin-1-yl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 332 | 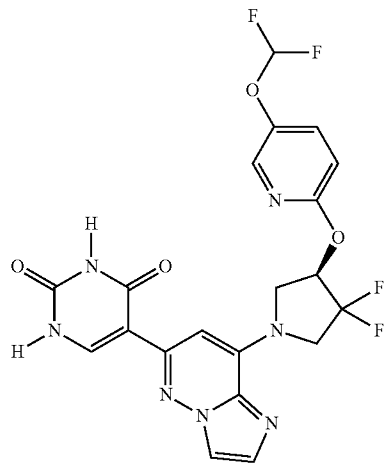 [SMILES: O=c1[nH]cc(-c2cc(N3C[C@@H](Oc4ccc(OC(F)F)cn4)C(F)(F)C3)c3nccn3n2)c(=O)[nH]1] | (R)-5-(8-(4-((5-(difluoromethoxy)pyridin-2-yl)oxy)-3,3-difluoropyrrolidin-1-yl)imidazo[1,2-b]pyridazin-6-yl)pyrimidine-2,4(1H,3H)-dione |
| 333 | 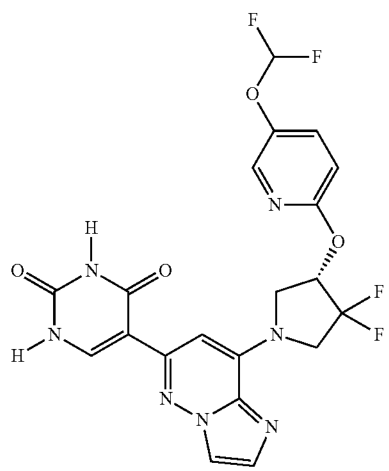 [SMILES: O=c1[nH]cc(-c2cc(N3C[C@H](Oc4ccc(OC(F)F)cn4)C(F)(F)C3)c3nccn3n2)c(=O)[nH]1] | (S)-5-(8-(4-((5-(difluoromethoxy)pyridin-2-yl)oxy)-3,3-difluoropyrrolidin-1-yl)imidazo[1,2-b]pyridazin-6-yl)pyrimidine-2,4(1H,3H)-dione |
| 334 | 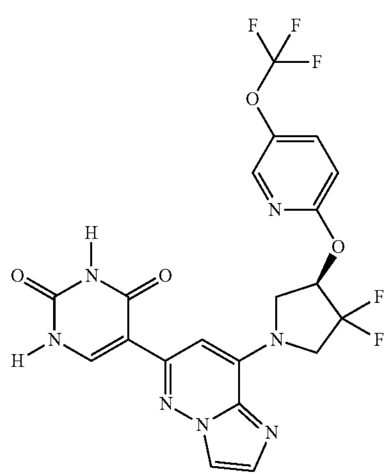 [SMILES: O=c1[nH]cc(-c2cc(N3C[C@@H](Oc4ccc(OC(F)(F)F)cn4)C(F)(F)C3)c3nccn3n2)c(=O)[nH]1] | (R)-5-(8-(3,3-difluoro-4-((5-(trifluoromethoxy)pyridin-2-yl)oxy)pyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 335 | 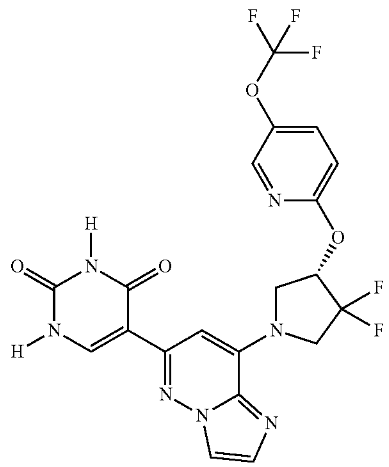 [SMILES: O=c1[nH]cc(-c2cc(N3C[C@H](Oc4ccc(OC(F)(F)F)cn4)C(F)(F)C3)c3nccn3n2)c(=O)[nH]1] | (S)-5-(8-(3,3-difluoro-4-((5-(trifluoromethoxy)pyridin-2-yl)oxy)pyrrolidin-1-yl)imidazo[1,2-b]pyridazin-6-yl)pyrimidine-2,4(1H,3H)-dione |
| 336 | 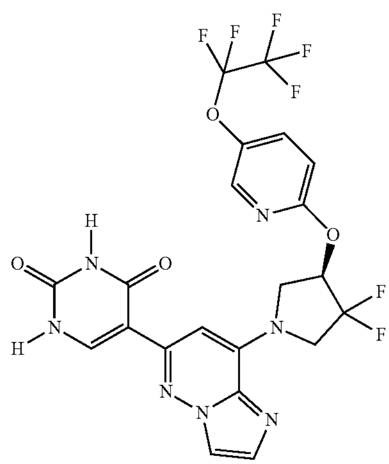 [SMILES: O=c1[nH]cc(-c2cc(N3C[C@@H](Oc4ccc(OC(F)(F)C(F)(F)F)cn4)C(F)(F)C3)c3nccn3n2)c(=O)[nH]1] | (R)-5-(8-(3,3-difluoro-4-((5-(perfluoroethoxy)pyridin-2-yl)oxy)pyrrolidin-1-yl)imidazo[1,2-b]pyridazin-6-yl)pyrimidine-2,4(1H,3H)-dione |
| 337 | 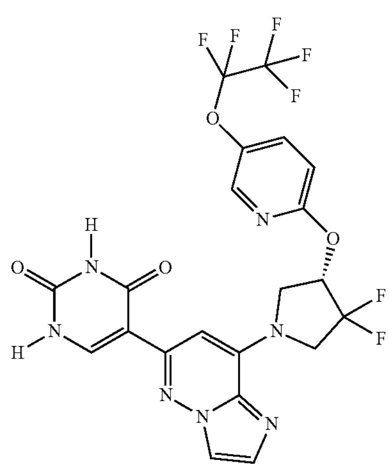 [SMILES: O=c1[nH]cc(-c2cc(N3C[C@H](Oc4ccc(OC(F)(F)C(F)(F)F)cn4)C(F)(F)C3)c3nccn3n2)c(=O)[nH]1] | (S)-5-(8-(3,3-difluoro-4-((5-(perfluoroethoxy)pyridin-2-yl)oxy)pyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 338 | 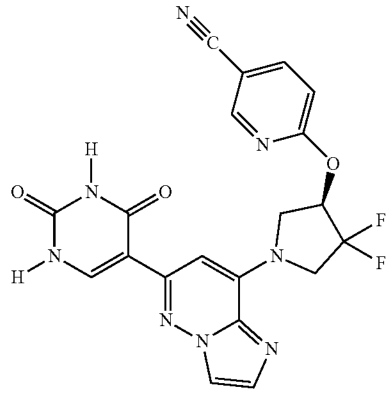 [SMILES: N#Cc1ccc(O[C@@H]2CN(c3cc(-c4c[nH]c(=O)[nH]c4=O)nn4ccnc34)CC2(F)F)nc1] | (R)-6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile |
| 339 | 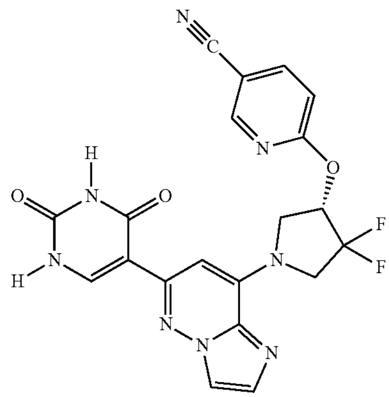 [SMILES: N#Cc1ccc(O[C@H]2CN(c3cc(-c4c[nH]c(=O)[nH]c4=O)nn4ccnc34)CC2(F)F)nc1] | (S)-6-((1-(6-(2,4-dioxo-1,2,3,4-tetrahydropyrimidin-5-yl)imidazo[1,2-b]pyridazin-8-yl)-4,4-difluoropyrrolidin-3-yl)oxy)nicotinonitrile |
| 340 | 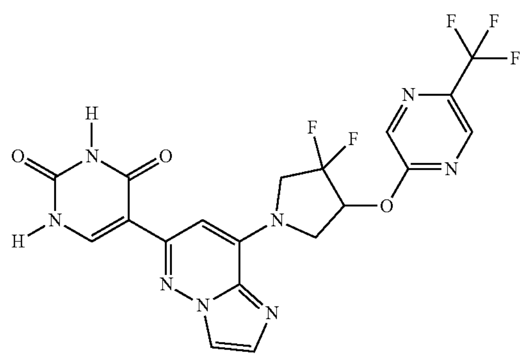 [SMILES: O=c1[nH]cc(-c2cc(N3CC(Oc4cnc(C(F)(F)F)cn4)C(F)(F)C3)c3nccn3n2)c(=O)[nH]1] | 5-(8-(3,3-difluoro-4-((5-(trifluoromethyl)pyrazin-2-yl)oxy)pyrrolidin-1-yl)imidazo[1,2-b]pyridazin-6-yl)pyrimidine-2,4(1H,3H)-dione |
| 341 | 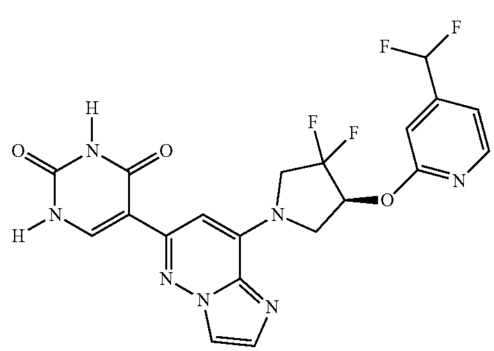 [SMILES: O=c1[nH]cc(-c2cc(N3C[C@H](Oc4cc(C(F)F)ccn4)C(F)(F)C3)c3nccn3n2)c(=O)[nH]1] | (S)-5-(8-(4-((4-(difluoromethyl)pyridin-2-yl)oxy)-3,3-difluoropyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 342 | 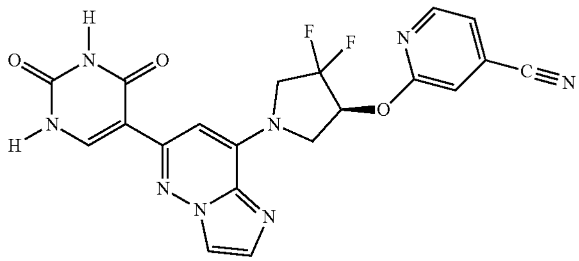 [SMILES: N#Cc1ccnc(O[C@H]2CN(c3cc(-c4c[nH]c(=O)[nH]c4=O)nn4ccnc34)CC2(F)F)c1] | (S)-2-((1-(6-(2,4-dioxo-1,2,3,4-tetrahydropyrimidin-5-yl)imidazo[1,2-b]pyridazin-8-yl)-4,4-difluoropyrrolidin-3-yl)oxy)isonicotinonitrile |
| 343 | 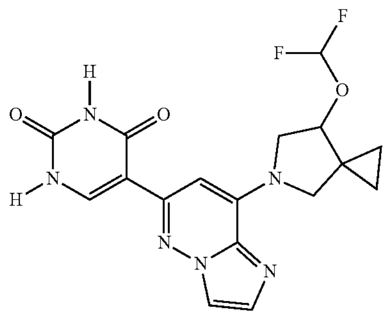 [SMILES: O=c1[nH]cc(-c2cc(N3CC(OC(F)F)C4(CC4)C3)c3nccn3n2)c(=O)[nH]1] | 5-(8-(7-(difluoromethoxy)-5-azaspiro[2.4]heptan-5-yl)imidazo[1,2-b]pyridazin-6-yl)pyrimidine-2,4(1H,3H)-dione |
| 344 | 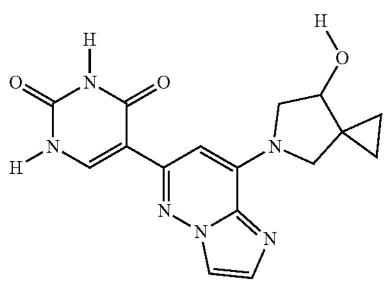 [SMILES: O=c1[nH]cc(-c2cc(N3CC(O)C4(CC4)C3)c3nccn3n2)c(=O)[nH]1] | 5-(8-(7-hydroxy-5-azaspiro[2.4]heptan-5-yl)imidazo[1,2-b]pyridazin-6-yl)pyrimidine-2,4(1H,3H)-dione |
| 345 | 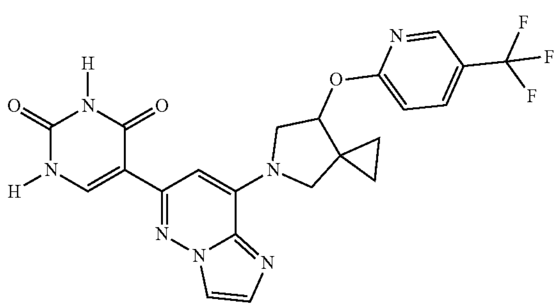 [SMILES: O=c1[nH]cc(-c2cc(N3CC(Oc4ccc(C(F)(F)F)cn4)C4(CC4)C3)c3nccn3n2)c(=O)[nH]1] | 5-(8-(7-((5-(trifluoromethyl)pyridin-2-yl)oxy)-5-azaspiro[2.4]heptan-5-yl)imidazo[1,2-b]pyridazin-6-yl)pyrimidine-2,4(1H,3H)-dione |
| 346 | 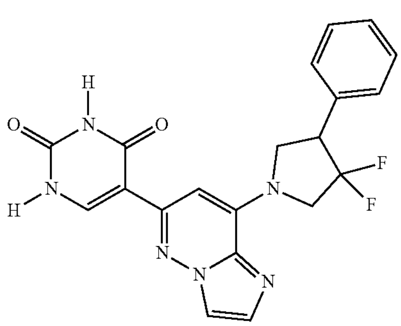 [SMILES: O=c1[nH]cc(-c2cc(N3CC(c4ccccc4)C(F)(F)C3)c3nccn3n2)c(=O)[nH]1] | 5-(8-(3,3-difluoro-4-phenylpyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 347 | 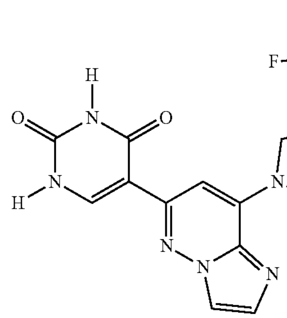 | (R)-5-(8-(3-(difluoromethoxy)pyrrolidin-1-yl)imidazo[1,2-b]pyridazin-6-yl)pyrimidine-2,4(1H,3H)-dione |
| 348 | 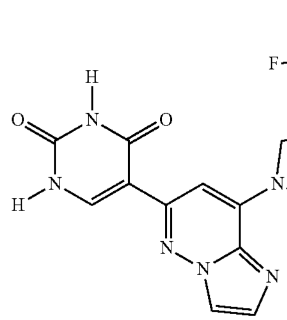 | (S)-5-(8-(3-(difluoromethoxy)pyrrolidin-1-yl)imidazo[1,2-b]pyridazin-6-yl)pyrimidine-2,4(1H,3H)-dione |
| 349 | 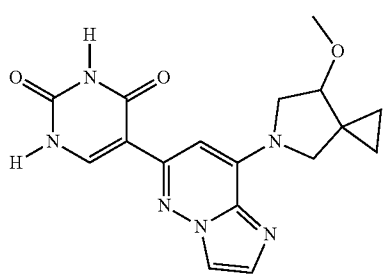 [SMILES: COC1CN(c2cc(-c3c[nH]c(=O)[nH]c3=O)nn3ccnc23)CC12CC2] | 5-(8-(7-methoxy-5-azaspiro[2.4]heptan-5-yl)imidazo[1,2-b]pyridazin-6-yl)pyrimidine-2,4(1H,3H)-dione |
| 350 | 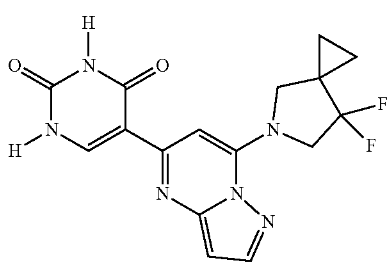 [SMILES: O=c1[nH]cc(-c2cc(N3CC(F)(F)C4(CC4)C3)n3nccc3n2)c(=O)[nH]1] | 5-(7-(7,7-difluoro-5-azaspiro[2.4]heptan-5-yl)pyrazolo[1,5-a]pyrimidin-5-yl)pyrimidine-2,4(1H,3H)-dione |
| 351 | 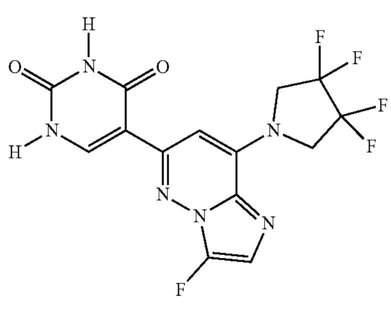 [SMILES: O=c1[nH]cc(-c2cc(N3CC(F)(F)C(F)(F)C3)c3ncc(F)n3n2)c(=O)[nH]1] | 5-(3-fluoro-8-(3,3,4,4-tetrafluoropyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 352 | 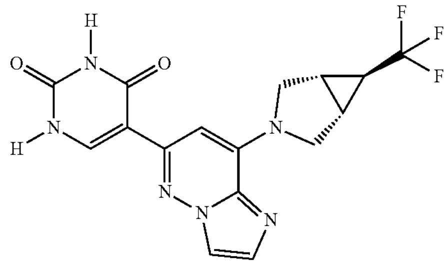 [SMILES: O=c1[nH]cc(-c2cc(N3C[C@@H]4[C@H](C3)[C@H]4C(F)(F)F)c3nccn3n2)c(=O)[nH]1] | 5-(8-((1R,5S,6r)-6-(trifluoromethyl)-3-azabicyclo[3.1.0]hexan-3-yl)imidazo[1,2-b]pyridazin-6-yl)pyrimidine-2,4(1H,3H)-dione |
| 353 | 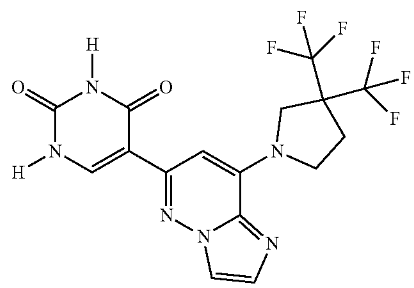 [SMILES: O=c1[nH]cc(-c2cc(N3CCC(C(F)(F)F)(C(F)(F)F)C3)c3nccn3n2)c(=O)[nH]1] | 5-(8-(3,3-bis(trifluoromethyl)pyrrolidin-1-yl)imidazo[1,2-b]pyridazin-6-yl)pyrimidine-2,4(1H,3H)-dione |
| 354 | 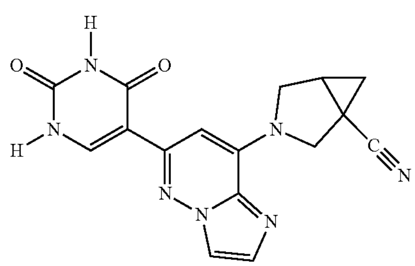 [SMILES: N#CC12CC1CN(c1cc(-c3c[nH]c(=O)[nH]c3=O)nn3ccnc13)C2] | 3-(6-(2,4-dioxo-1,2,3,4-tetrahydropyrimidin-5-yl)imidazo[1,2-b]pyridazin-8-yl)-3-azabicyclo[3.1.0]hexane-1-carbonitrile |
| 355 | 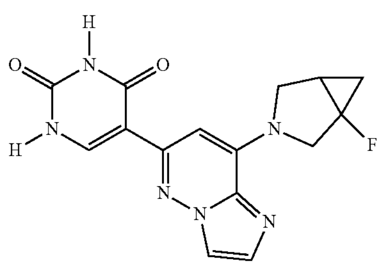 [SMILES: O=c1[nH]cc(-c2cc(N3CC4CC4(F)C3)c3nccn3n2)c(=O)[nH]1] | 5-(8-(1-fluoro-3-azabicyclo[3.1.0]hexan-3-yl)imidazo[1,2-b]pyridazin-6-yl)pyrimidine-2,4(1H,3H)-dione |
| 356 | 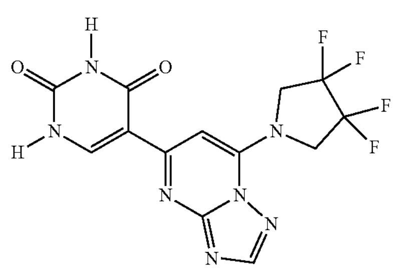 [SMILES: O=c1[nH]cc(-c2cc(N3CC(F)(F)C(F)(F)C3)n3ncnc3n2)c(=O)[nH]1] | 5-(7-(3,3,4,4-tetrafluoropyrrolidin-1-yl)-[1,2,4]triazolo[1,5-a]pyrimidin-5-yl)pyrimidine-2,4(1H,3H)-dione |

TABLE 2-continued

| Ex. No. | Structure | IUPAC Name |
|---|---|---|
| 357 | 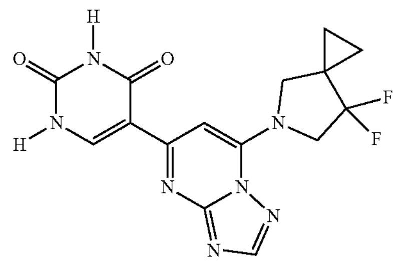 [SMILES: O=c1[nH]cc(-c2cc(N3CC(F)(F)C4(CC4)C3)n3ncnc3n2)c(=O)[nH]1] | 5-(7-(7,7-difluoro-5-azaspiro[2.4]heptan-5-yl)-[1,2,4]triazolo[1,5-a]pyrimidin-5-yl)pyrimidine-2,4(1H,3H)-dione |
| 358 | 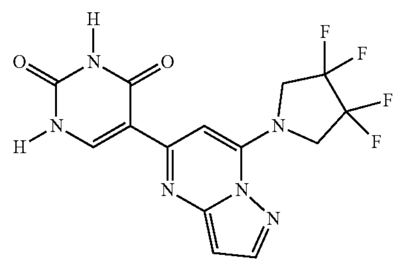 [SMILES: O=c1[nH]cc(-c2cc(N3CC(F)(F)C(F)(F)C3)n3nccc3n2)c(=O)[nH]1] | 5-(7-(3,3,4,4-tetrafluoropyrrolidin-1-yl)pyrazolo[1,5-a]pyrimidin-5-yl)pyrimidine-2,4(1H,3H)-dione |
| 359 | 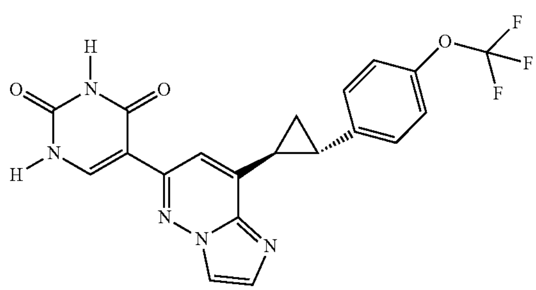 [SMILES: O=c1[nH]cc(-c2cc([C@H]3C[C@@H]3c3ccc(OC(F)(F)F)cc3)c3nccn3n2)c(=O)[nH]1] | 5-(8-((1S,2S)-2-(4-(trifluoromethoxy)phenyl)cyclopropyl)imidazo[1,2-b]pyridazin-6-yl)pyrimidine-2,4(1H,3H)-dione |
| 360 | 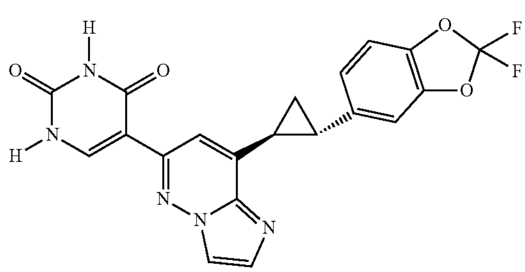 [SMILES: O=c1[nH]cc(-c2cc([C@H]3C[C@@H]3c3ccc4c(c3)OC(F)(F)O4)c3nccn3n2)c(=O)[nH]1] | 5-(8-((1S,2S)-2-(2,2-difluorobenzo[d][1,3]dioxol-5-yl)cyclopropyl)imidazo[1,2-b]pyridazin-6-yl)pyrimidine-2,4(1H,3H)-dione |
| 361 | 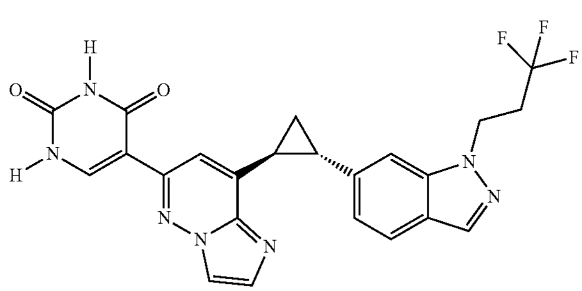 [SMILES: O=c1[nH]cc(-c2cc([C@H]3C[C@@H]3c3ccc4cnn(CCC(F)(F)F)c4c3)c3nccn3n2)c(=O)[nH]1] | 5-(8-((1S,2S)-2-(1-(3,3,3-trifluoropropyl)-1H-indazol-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 362 | 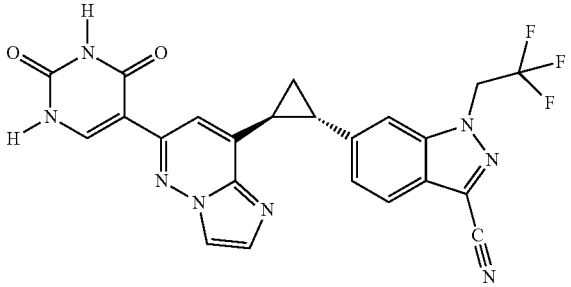 [SMILES: N#Cc1nn(CC(F)(F)F)c2cc([C@H]3C[C@@H]3c3cc(-c4c[nH]c(=O)[nH]c4=O)nn4ccnc34)ccc12] | 6-((1S,2S)-2-(6-(2,4-dioxo-1,2,3,4-tetrahydropyrimidin-5-yl)imidazo[1,2-b]pyridazin-8-yl)cyclopropyl)-1-(2,2,2-trifluoroethyl)-1H-indazole-3-carbonitrile |
| 363 | 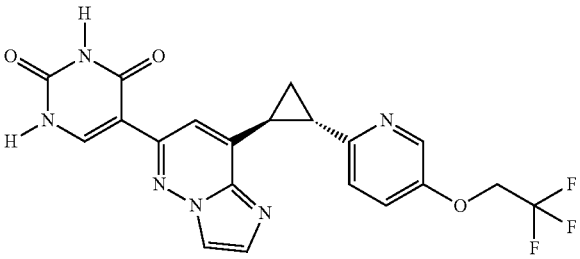 [SMILES: O=c1[nH]cc(-c2cc([C@H]3C[C@@H]3c3ccc(OCC(F)(F)F)cn3)c3nccn3n2)c(=O)[nH]1] | 5-(8-((1S,2S)-2-(5-(2,2,2-trifluoroethoxy)pyridin-2-yl)cyclopropyl)imidazo[1,2-b]pyridazin-6-yl)pyrimidine-2,4(1H,3H)-dione |
| 364 | 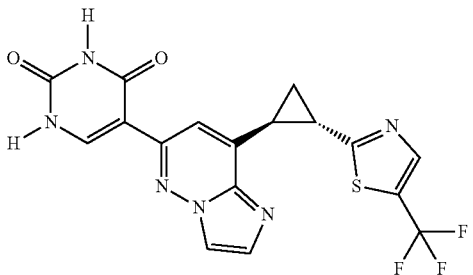 [SMILES: O=c1[nH]cc(-c2cc([C@H]3C[C@@H]3c3ncc(C(F)(F)F)s3)c3nccn3n2)c(=O)[nH]1] | 5-(8-((1S,2S)-2-(5-(trifluoromethyl)thiazol-2-yl)cyclopropyl)imidazo[1,2-b]pyridazin-6-yl)pyrimidine-2,4(1H,3H)-dione |
| 365 | 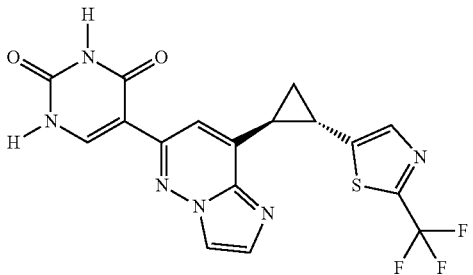 [SMILES: O=c1[nH]cc(-c2cc([C@H]3C[C@@H]3c3cnc(C(F)(F)F)s3)c3nccn3n2)c(=O)[nH]1] | 5-(8-((1S,2S)-2-(2-(trifluoromethyl)thiazol-5-yl)cyclopropyl)imidazo[1,2-b]pyridazin-6-yl)pyrimidine-2,4(1H,3H)-dione |
| 366 | 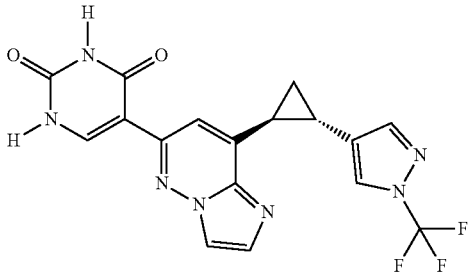 [SMILES: O=c1[nH]cc(-c2cc([C@H]3C[C@@H]3c3cnn(C(F)(F)F)c3)c3nccn3n2)c(=O)[nH]1] | 5-(8-((1S,2S)-2-(1-(trifluoromethyl)-1H-pyrazol-4-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 367 | 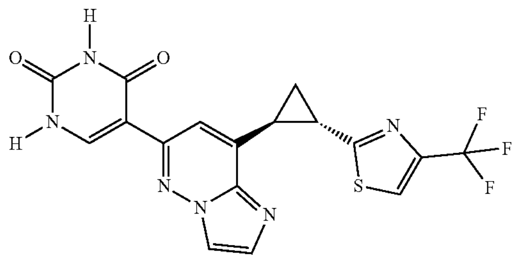 [SMILES: O=c1[nH]cc(-c2cc([C@H]3C[C@@H]3c3nc(C(F)(F)F)cs3)c3nccn3n2)c(=O)[nH]1] | 5-(8-((1S,2S)-2-(4-(trifluoromethyl)thiazol-2-yl)cyclopropyl)imidazo[1,2-b]pyridazin-6-yl)pyrimidine-2,4(1H,3H)-dione |
| 368 | 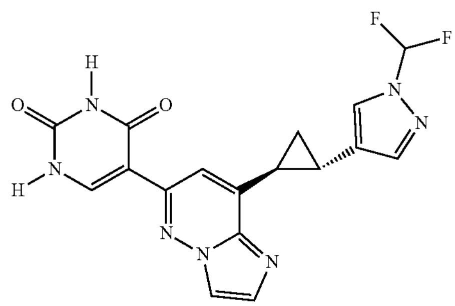 [SMILES: O=c1[nH]cc(-c2cc([C@H]3C[C@@H]3c3cnn(C(F)F)c3)c3nccn3n2)c(=O)[nH]1] | 5-(8-((1S,2S)-2-(1-(difluoromethyl)-1H-pyrazol-4-yl)cyclopropyl)imidazo[1,2-b]pyridazin-6-yl)pyrimidine-2,4(1H,3H)-dione |
| 369 | 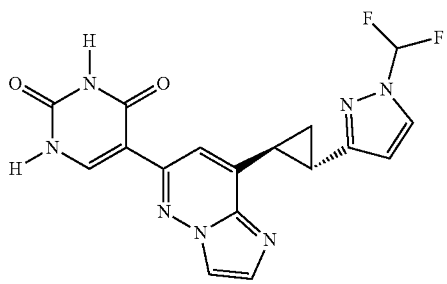 [SMILES: O=c1[nH]cc(-c2cc([C@H]3C[C@@H]3c3ccn(C(F)F)n3)c3nccn3n2)c(=O)[nH]1] | 5-(8-((1S,2S)-2-(1-(difluoromethyl)-1H-pyrazol-3-yl)cyclopropyl)imidazo[1,2-b]pyridazin-6-yl)pyrimidine-2,4(1H,3H)-dione |
| 370 | 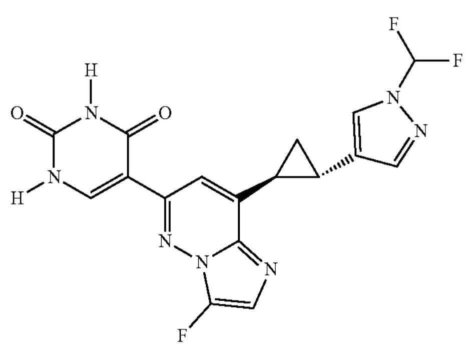 [SMILES: O=c1[nH]cc(-c2cc([C@H]3C[C@@H]3c3cnn(C(F)F)c3)c3ncc(F)n3n2)c(=O)[nH]1] | 5-(8-((1S,2S)-2-(1-(difluoromethyl)-1H-pyrazol-4-yl)cyclopropyl)-3-fluoroimidazo[1,2-b]pyridazin-6-yl)pyrimidine-2,4(1H,3H)-dione |
| 371 | 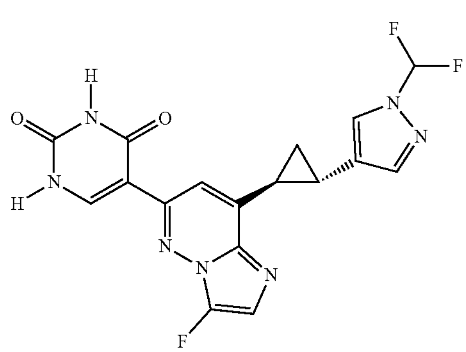 [SMILES: O=c1[nH]cc(-c2cc([C@H]3C[C@@H]3c3cnn(C(F)F)c3)c3ncc(F)n3n2)c(=O)[nH]1] | 5-(8-((1S,2S)-2-(1-(difluoromethyl)-1H-pyrazol-4-yl)cyclopropyl)-3-fluoroimidazo[1,2-b]pyridazin-6-yl)pyrimidine-2,4(1H,3H)-dione |

TABLE 2-continued

| Ex. No. | Structure | IUPAC Name |
|---|---|---|
| 372 | 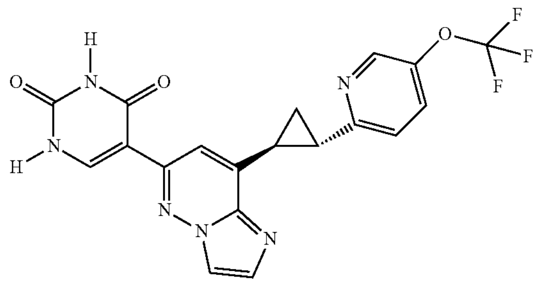 | 5-(8-((1S,2S)-2-(5-(trifluoromethoxy)pyridin-2-yl)cyclopropyl)imidazo[1,2-b]pyridazin-6-yl)pyrimidine-2,4(1H,3H)-dione |
| 373 | 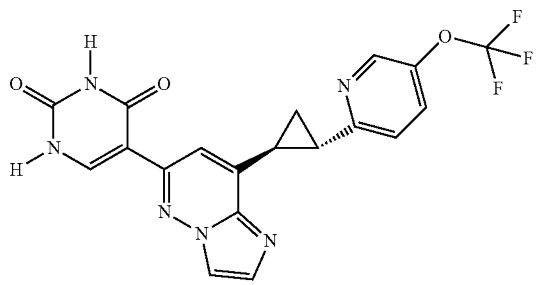 [SMILES: O=c1[nH]cc(-c2cc([C@H]3C[C@@H]3c3ccc(OC(F)(F)F)cn3)c3nccn3n2)c(=O)[nH]1] | 5-(8-((1S,2S)-2-(5-(trifluoromethoxy)pyridin-2-yl)cyclopropyl)imidazo[1,2-b]pyridazin-6-yl)pyrimidine-2,4(1H,3H)-dione |
| 374 | 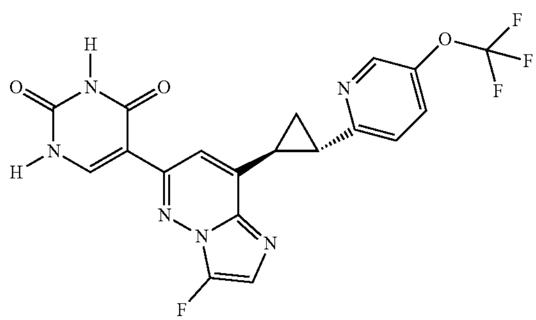 [SMILES: O=c1[nH]cc(-c2cc([C@H]3C[C@@H]3c3ccc(OC(F)(F)F)cn3)c3ncc(F)n3n2)c(=O)[nH]1] | 5-(3-fluoro-8-((1S,2S)-2-(5-(trifluoromethoxy)pyridin-2-yl)cyclopropyl)imidazo[1,2-b]pyridazin-6-yl)pyrimidine-2,4(1H,3H)-dione |
| 375 | 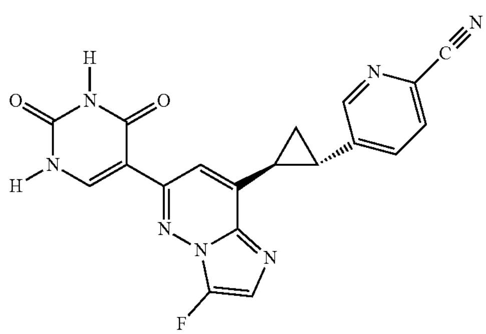 [SMILES: N#Cc1ccc([C@H]2C[C@@H]2c2cc(-c3c[nH]c(=O)[nH]c3=O)nn3c(F)cnc23)cn1] | 5-((1S,2S)-2-(6-(2,4-dioxo-1,2,3,4-tetrahydropyrimidin-5-yl)-3-fluoroimidazo[1,2-b]pyridazin-8-yl)cyclopropyl)picolinonitrile |
| 376 | 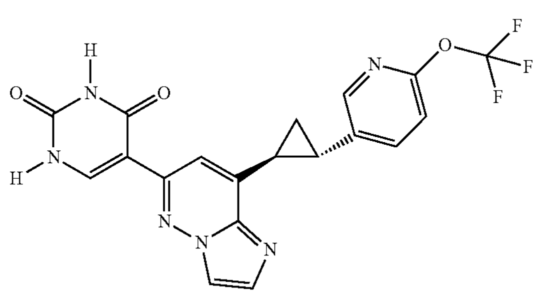 [SMILES: O=c1[nH]cc(-c2cc([C@H]3C[C@@H]3c3ccc(OC(F)(F)F)nc3)c3nccn3n2)c(=O)[nH]1] | 5-(8-((1S,2S)-2-(6-(trifluoromethoxy)pyridin-3-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 377 | 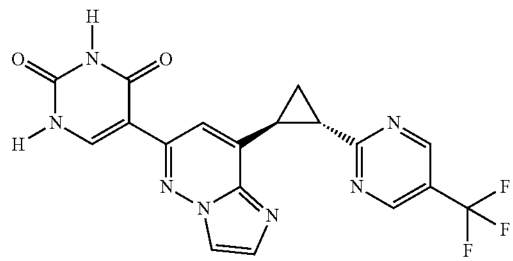 [SMILES: O=c1[nH]cc(-c2cc([C@H]3C[C@@H]3c3ncc(C(F)(F)F)cn3)c3nccn3n2)c(=O)[nH]1] | 5-(8-((1S,2S)-2-(5-(trifluoromethyl)pyrimidin-2-yl)cyclopropyl)imidazo[1,2-b]pyridazin-6-yl)pyrimidine-2,4(1H,3H)-dione |
| 378 | 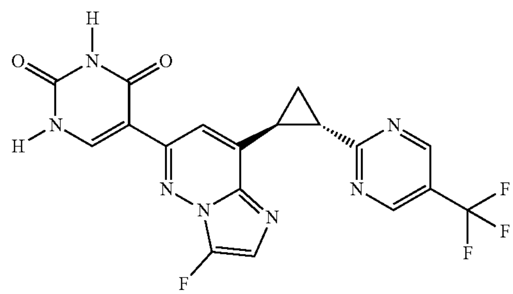 [SMILES: O=c1[nH]cc(-c2cc([C@H]3C[C@@H]3c3ncc(C(F)(F)F)cn3)c3ncc(F)n3n2)c(=O)[nH]1] | 5-(3-fluoro-8-((1S,2S)-2-(5-(trifluoromethyl)pyrimidin-2-yl)cyclopropyl)imidazo[1,2-b]pyridazin-6-yl)pyrimidine-2,4(1H,3H)-dione |
| 379 | 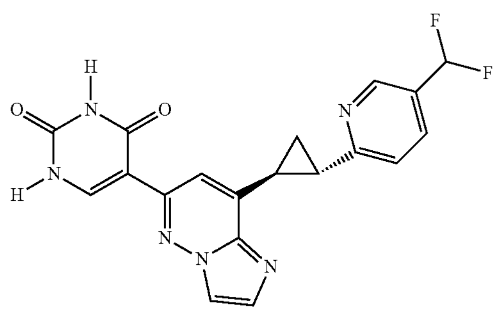 [SMILES: O=c1[nH]cc(-c2cc([C@H]3C[C@@H]3c3ccc(C(F)F)cn3)c3nccn3n2)c(=O)[nH]1] | 5-(8-((1S,2S)-2-(5-(difluoromethyl)pyridin-2-yl)cyclopropyl)imidazo[1,2-b]pyridazin-6-yl)pyrimidine-2,4(1H,3H)-dione |
| 380 | 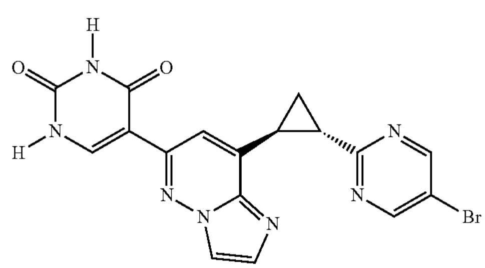 [SMILES: O=c1[nH]cc(-c2cc([C@H]3C[C@@H]3c3ncc(Br)cn3)c3nccn3n2)c(=O)[nH]1] | 5-(8-((1S,2S)-2-(5-bromopyrimidin-2-yl)cyclopropyl)imidazo[1,2-b]pyridazin-6-yl)pyrimidine-2,4(1H,3H)-dione |
| 381 | 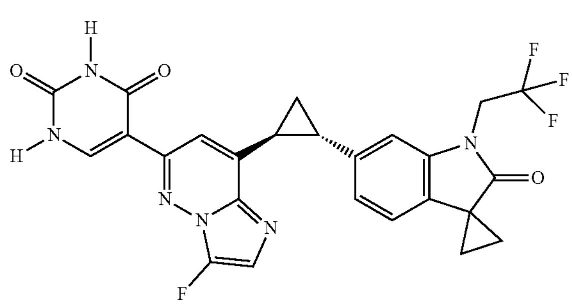 [SMILES: O=C1N(CC(F)(F)F)c2cc([C@H]3C[C@@H]3c3cc(-c4c[nH]c(=O)[nH]c4=O)nn4c(F)cnc34)ccc2C12CC2] | 5-(3-fluoro-8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 382 | 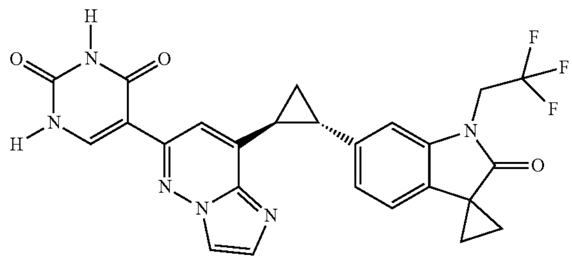 [SMILES: O=C1N(CC(F)(F)F)c2cc([C@H]3C[C@@H]3c3cc(-c4c[nH]c(=O)[nH]c4=O)nn4ccnc34)ccc2C12CC2] | 5-(8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |
| 383 | 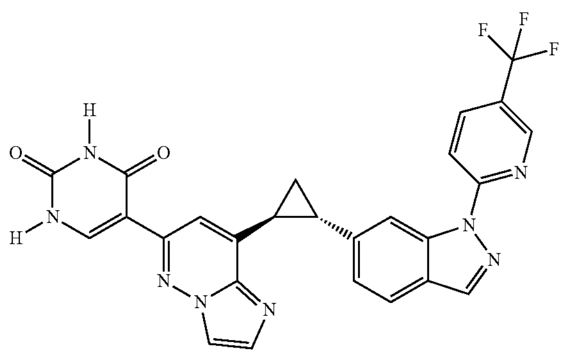 [SMILES: O=c1[nH]cc(-c2cc([C@H]3C[C@@H]3c3ccc4cnn(-c5ccc(C(F)(F)F)cn5)c4c3)c3nccn3n2)c(=O)[nH]1] | 5-(8-((1S,2S)-2-(1-(5-(trifluoromethyl)pyridin-2-yl)-1H-indazol-6-yl)cyclopropyl)imidazo[1,2-b]pyridazin-6-yl)pyrimidine-2,4(1H,3H)-dione |
| 384 | 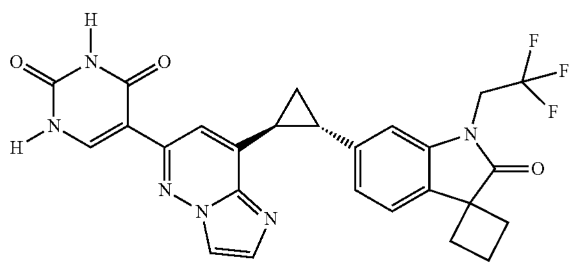 [SMILES: O=C1N(CC(F)(F)F)c2cc([C@H]3C[C@@H]3c3cc(-c4c[nH]c(=O)[nH]c4=O)nn4ccnc34)ccc2C12CCC2] | 5-(8-((1S,2S)-2-(2'-oxo-1'-(2,2,2-trifluoroethyl)spiro[cyclobutane-1,3'-indolin]-6'-yl)cyclopropyl)imidazo[1,2-b]pyridazin-6-yl)pyrimidine-2,4(1H,3H)-dione |
| 385 | 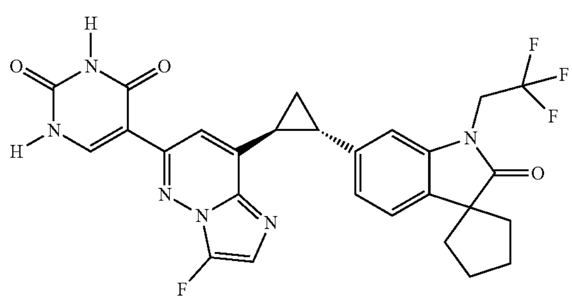 [SMILES: O=C1N(CC(F)(F)F)c2cc([C@H]3C[C@@H]3c3cc(-c4c[nH]c(=O)[nH]c4=O)nn4c(F)cnc34)ccc2C12CCCC2] | 5-(3-fluoro-8-((1S,2S)-2-(2'-oxo-1'-(2,2,2-trifluoroethyl)spiro[cyclopentane-1,3'-indolin]-6'-yl)cyclopropyl)imidazo[1,2-b]pyridazin-6-yl)pyrimidine-2,4(1H,3H)-dione |
| 386 | 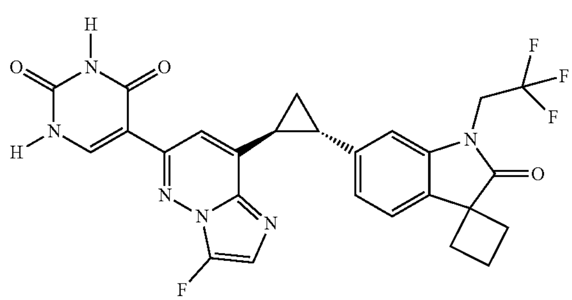 [SMILES: O=C1N(CC(F)(F)F)c2cc([C@H]3C[C@@H]3c3cc(-c4c[nH]c(=O)[nH]c4=O)nn4c(F)cnc34)ccc2C12CCC2] | 5-(3-fluoro-8-((1S,2S)-2-(2'-oxo-1'-(2,2,2-trifluoroethyl)spiro[cyclobutane-1,3'-indolin]-6'-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 387 | 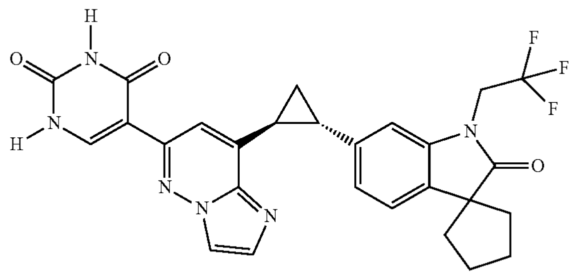 [SMILES: O=C1N(CC(F)(F)F)c2cc([C@H]3C[C@@H]3c3cc(-c4c[nH]c(=O)[nH]c4=O)nn4ccnc34)ccc2C12CCCC2] | 5-(8-((1S,2S)-2-(2'-oxo-1'-(2,2,2-trifluoroethyl)spiro[cyclopentane-1,3'-indolin]-6'-yl)cyclopropyl)imidazo[1,2-b]pyridazin-6-yl)pyrimidine-2,4(1H,3H)-dione |
| 388 | 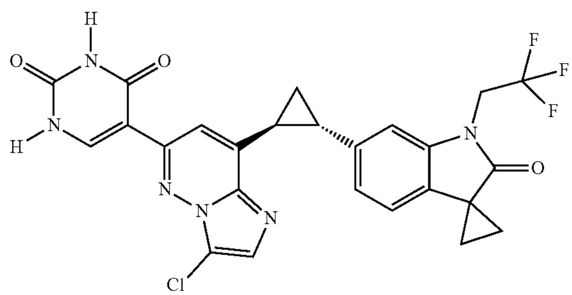 [SMILES: O=C1N(CC(F)(F)F)c2cc([C@H]3C[C@@H]3c3cc(-c4c[nH]c(=O)[nH]c4=O)nn4c(Cl)cnc34)ccc2C12CC2] | 5-(3-chloro-8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |
| 389 | 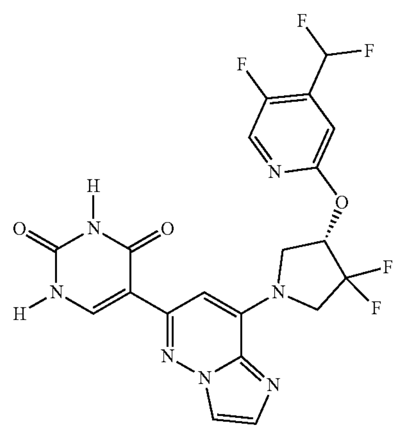 [SMILES: O=c1[nH]cc(-c2cc(N3C[C@H](Oc4cc(C(F)F)c(F)cn4)C(F)(F)C3)c3nccn3n2)c(=O)[nH]1] | (S)-5-(8-(4-((4-(difluoromethyl)-5-fluoropyridin-2-yl)oxy)-3,3-difluoropyrrolidin-1-yl)imidazo[1,2-b]pyridazin-6-yl)pyrimidine-2,4(1H,3H)-dione |
| 390 | 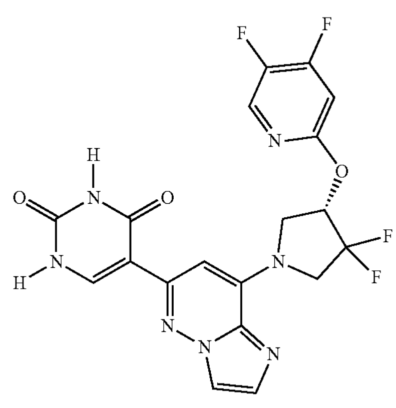 [SMILES: O=c1[nH]cc(-c2cc(N3C[C@H](Oc4cc(F)c(F)cn4)C(F)(F)C3)c3nccn3n2)c(=O)[nH]1] | (S)-5-(8-(4-((4,5-difluoropyridin-2-yl)oxy)-3,3-difluoropyrrolidin-1-yl)imidazo[1,2-b]pyridazin-6-yl)pyrimidine-2,4(1H,3H)-dione |

US 12,110,294 B2

TABLE 2-continued

Examples

| Ex. No. | Structure | IUPAC Name |
|---|---|---|
| 391 | 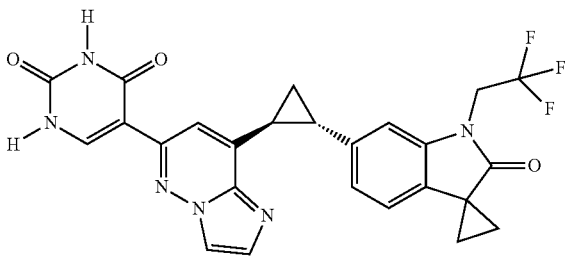 [SMILES: O=C1N(CC(F)(F)F)c2cc([C@H]3C[C@@H]3c3cc(-c4c[nH]c(=O)[nH]c4=O)nn4ccnc34)ccc2C12CC2] | 5-(8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |
| 392 | 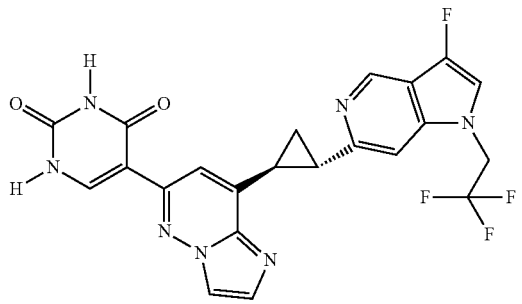 [SMILES: O=c1[nH]cc(-c2cc([C@H]3C[C@@H]3c3cc4c(cn3)c(F)cn4CC(F)(F)F)c3nccn3n2)c(=O)[nH]1] | 5-(8-((1S,2S)-2-(3-fluoro-1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione |
| 393 | 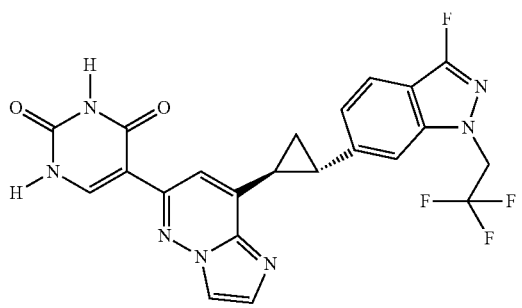 [SMILES: O=c1[nH]cc(-c2cc([C@H]3C[C@@H]3c3ccc4c(F)nn(CC(F)(F)F)c4c3)c3nccn3n2)c(=O)[nH]1] | 5-(8-((1S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 394 | 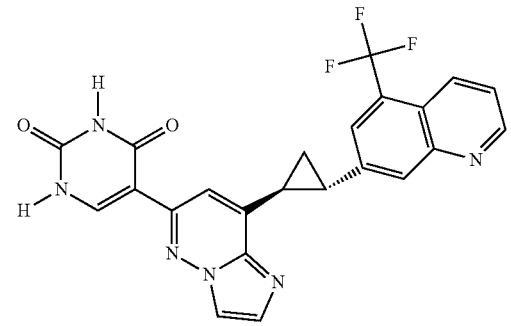 [SMILES: O=c1[nH]cc(-c2cc([C@H]3C[C@@H]3c3cc(C(F)(F)F)c4cccnc4c3)c3nccn3n2)c(=O)[nH]1] | 5-(8-((1S,2S)-2-(5-(trifluoromethyl)quinolin-7-yl)cyclopropyl)imidazo[1,2-b]pyridazin-6-yl)pyrimidine-2,4(1H,3H)-dione |
| 395 | 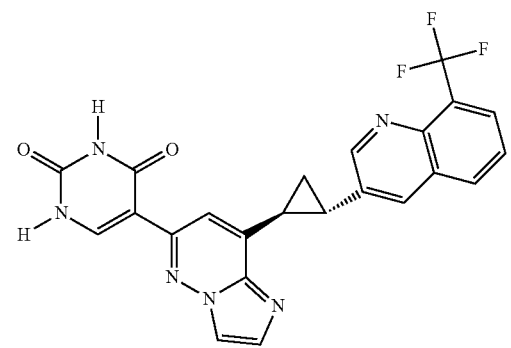 [SMILES: O=c1[nH]cc(-c2cc([C@H]3C[C@@H]3c3cnc4c(C(F)(F)F)cccc4c3)c3nccn3n2)c(=O)[nH]1] | 5-(8-((1S,2S)-2-(8-(trifluoromethyl)quinolin-3-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 396 | 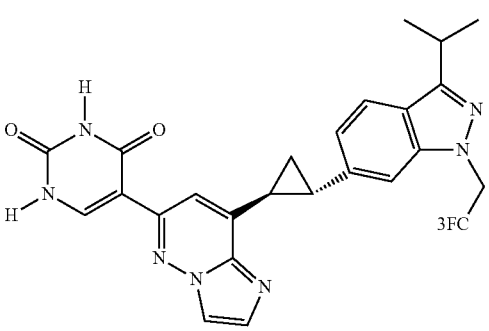 | 5-(8-((1S,2S)-2-(3-isopropyl-1-(2,2,2-trifluoroethyl)-1H-indazol-6-yl)cyclopropyl)imidazo[1,2-b]pyridazin-6-yl)pyrimidine-2,4(1H,3H)-dione |
| 397 | 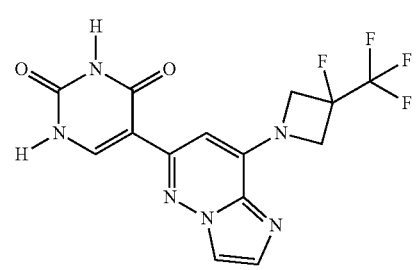 | 5-(8-(3-fluoro-3-(trifluoromethyl)azetidin-1-yl)imidazo[1,2-b]pyridazin-6-yl)pyrimidine-2,4(1H,3H)-dione |
| 398 | 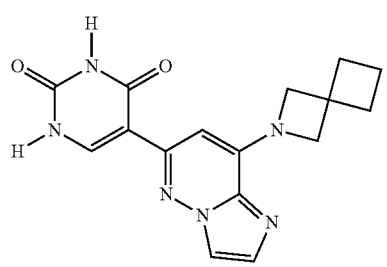 [SMILES: O=c1[nH]cc(-c2cc(N3CC4(CCC4)C3)c3nccn3n2)c(=O)[nH]1] | 5-(8-(2-azaspiro[3.3]heptan-2-yl)imidazo[1,2-b]pyridazin-6-yl)pyrimidine-2,4(1H,3H)-dione |
| 399 | 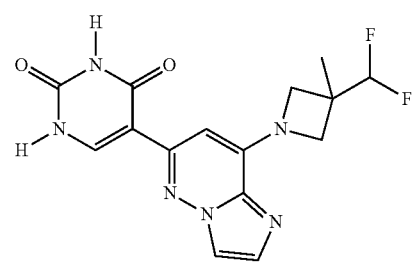 | 5-(8-(3-(difluoromethyl)-3-methylazetidin-1-yl)imidazo[1,2-b]pyridazin-6-yl)pyrimidine-2,4(1H,3H)-dione |
| 400 | 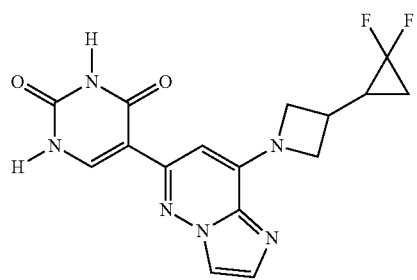 [SMILES: O=c1[nH]cc(-c2cc(N3CC(C4CC4(F)F)C3)c3nccn3n2)c(=O)[nH]1] | 5-(8-(3-(2,2-difluorocyclopropyl)azetidin-1-yl)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 401 | 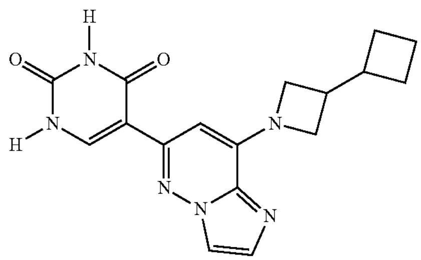 [SMILES: O=c1[nH]cc(-c2cc(N3CC(C4CCC4)C3)c3nccn3n2)c(=O)[nH]1] | 5-(8-(3-cyclobutylazetidin-1-yl)imidazo[1,2-b]pyridazin-6-yl)pyrimidine-2,4(1H,3H)-dione |
| 402 | 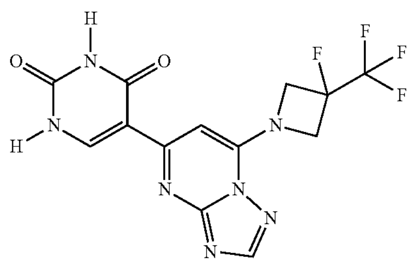 [SMILES: O=c1[nH]cc(-c2cc(N3CC(F)(C(F)(F)F)C3)n3ncnc3n2)c(=O)[nH]1] | 5-(7-(3-fluoro-3-(trifluoromethyl)azetidin-1-yl)-[1,2,4]triazolo[1,5-a]pyrimidin-5-yl)pyrimidine-2,4(1H,3H)-dione |
| 403 | 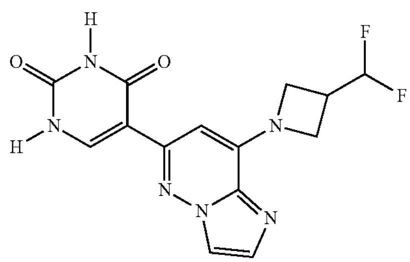 [SMILES: O=c1[nH]cc(-c2cc(N3CC(C(F)F)C3)c3nccn3n2)c(=O)[nH]1] | 5-(8-(3-(difluoromethyl)azetidin-1-yl)imidazo[1,2-b]pyridazin-6-yl)pyrimidine-2,4(1H,3H)-dione |
| 404 | 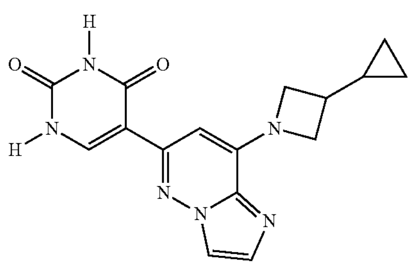 [SMILES: O=c1[nH]cc(-c2cc(N3CC(C4CC4)C3)c3nccn3n2)c(=O)[nH]1] | 5-(8-(3-cyclopropylazetidin-1-yl)imidazo[1,2-b]pyridazin-6-yl)pyrimidine-2,4(1H,3H)-dione |
| 405 | 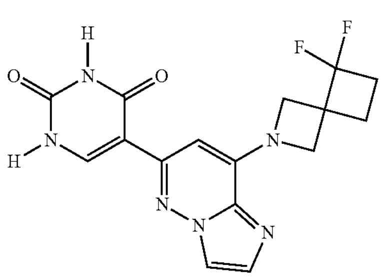 [SMILES: O=c1[nH]cc(-c2cc(N3CC4(CCC4(F)F)C3)c3nccn3n2)c(=O)[nH]1] | 5-(8-(5,5-difluoro-2-azaspiro[3.3]heptan-2-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 406 | 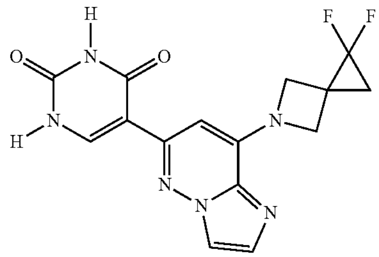 [SMILES: O=c1[nH]cc(-c2cc(N3CC4(C3)CC4(F)F)c3nccn3n2)c(=O)[nH]1] | 5-(8-(1,1-difluoro-5-azaspiro[2.3]hexan-5-yl)imidazo[1,2-b]pyridazin-6-yl)pyrimidine-2,4(1H,3H)-dione |
| 407 | 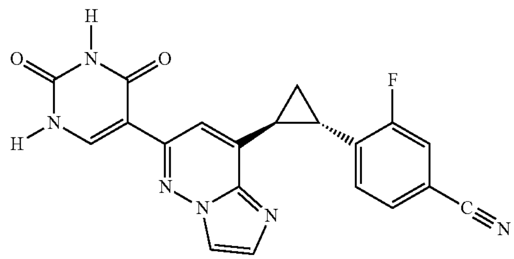 [SMILES: N#Cc1ccc([C@H]2C[C@@H]2c2cc(-c3c[nH]c(=O)[nH]c3=O)nn3ccnc23)c(F)c1] | 4-((1S,2S)-2-(6-(2,4-dioxo-1,2,3,4-tetrahydropyrimidin-5-yl)imidazo[1,2-b]pyridazin-8-yl)cyclopropyl)-3-fluorobenzonitrile |
| 408 | 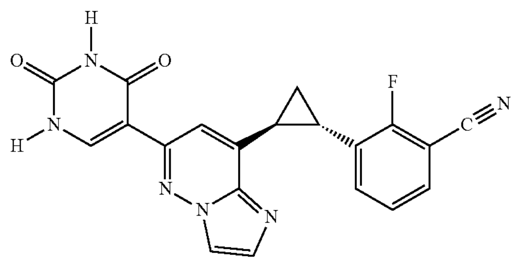 [SMILES: N#Cc1cccc([C@H]2C[C@@H]2c2cc(-c3c[nH]c(=O)[nH]c3=O)nn3ccnc23)c1F] | 3-((1S,2S)-2-(6-(2,4-dioxo-1,2,3,4-tetrahydropyrimidin-5-yl)imidazo[1,2-b]pyridazin-8-yl)cyclopropyl)-2-fluorobenzonitrile |
| 409 | 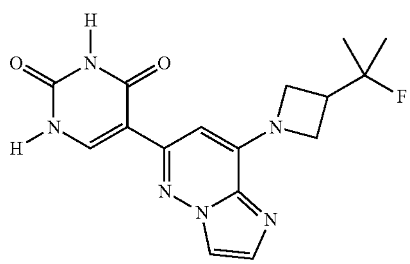 [SMILES: CC(C)(F)C1CN(c2cc(-c3c[nH]c(=O)[nH]c3=O)nn3ccnc23)C1] | 5-(8-(3-(2-fluoropropan-2-yl)azetidin-1-yl)imidazo[1,2-b]pyridazin-6-yl)pyrimidine-2,4(1H,3H)-dione |
| 410 | 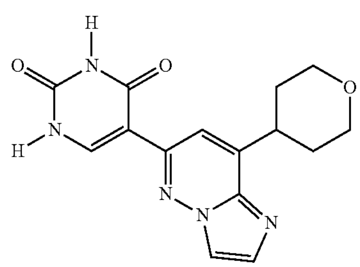 [SMILES: O=c1[nH]cc(-c2cc(C3CCOCC3)c3nccn3n2)c(=O)[nH]1] | 5-(8-(tetrahydro-2H-pyran-4-yl)imidazo[1,2-b]pyridazin-6-yl)pyrimidine-2,4(1H,3H)-dione |
| 411 | 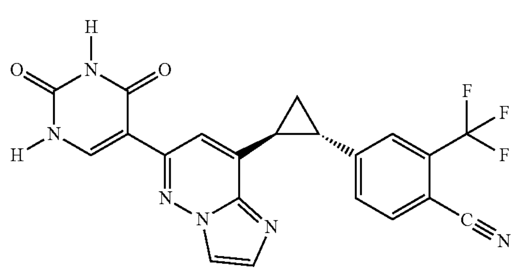 [SMILES: N#Cc1ccc([C@H]2C[C@@H]2c2cc(-c3c[nH]c(=O)[nH]c3=O)nn3ccnc23)cc1C(F)(F)F] | 4-((1S,2S)-2-(6-(2,4-dioxo-1,2,3,4-tetrahydropyrimidin-5-yl)imidazo[1,2-b]pyridazin-8-yl)cyclopropyl)-2-(trifluoromethyl)benzonitrile |

TABLE 2-continued

| Ex. No. | Structure | IUPAC Name |
|---|---|---|
| 412 | 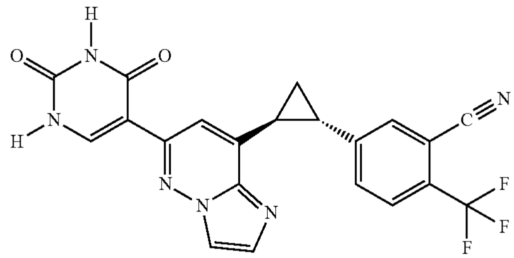 [SMILES: N#Cc1cc([C@H]2C[C@@H]2c2cc(-c3c[nH]c(=O)[nH]c3=O)nn3ccnc23)ccc1C(F)(F)F] | 5-((1S,2S)-2-(6-(2,4-dioxo-1,2,3,4-tetrahydropyrimidin-5-yl)imidazo[1,2-b]pyridazin-8-yl)cyclopropyl)-2-(trifluoromethyl)benzonitrile |
| 413 | 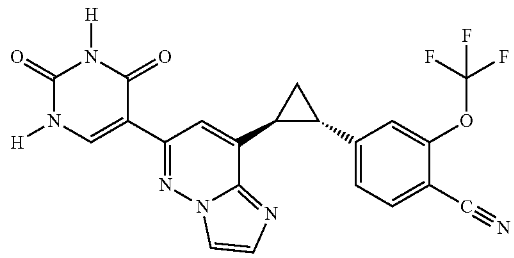 [SMILES: N#Cc1ccc([C@H]2C[C@@H]2c2cc(-c3c[nH]c(=O)[nH]c3=O)nn3ccnc23)cc1OC(F)(F)F] | 4-((1S,2S)-2-(6-(2,4-dioxo-1,2,3,4-tetrahydropyrimidin-5-yl)imidazo[1,2-b]pyridazin-8-yl)cyclopropyl)-2-(trifluoromethoxy)benzonitrile |
| 414 | 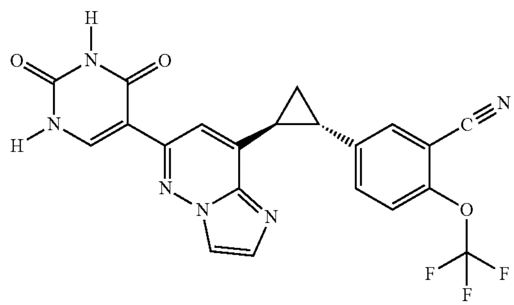 [SMILES: N#Cc1cc([C@H]2C[C@@H]2c2cc(-c3c[nH]c(=O)[nH]c3=O)nn3ccnc23)ccc1OC(F)(F)F] | 5-((1S,2S)-2-(6-(2,4-dioxo-1,2,3,4-tetrahydropyrimidin-5-yl)imidazo[1,2-b]pyridazin-8-yl)cyclopropyl)-2-(trifluoromethoxy)benzonitrile |
| 415 | 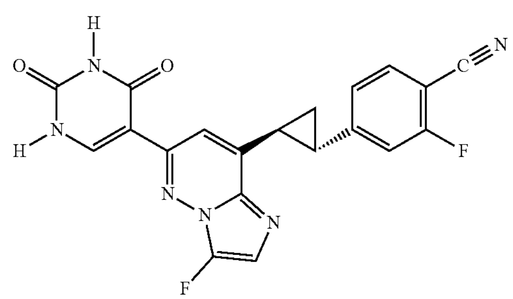 [SMILES: N#Cc1ccc([C@H]2C[C@@H]2c2cc(-c3c[nH]c(=O)[nH]c3=O)nn3c(F)cnc23)cc1F] | 4-((1S,2S)-2-(6-(2,4-dioxo-1,2,3,4-tetrahydropyrimidin-5-yl)-3-fluoroimidazo[1,2-b]pyridazin-8-yl)cyclopropyl)-2-fluorobenzonitrile |
| 416 | 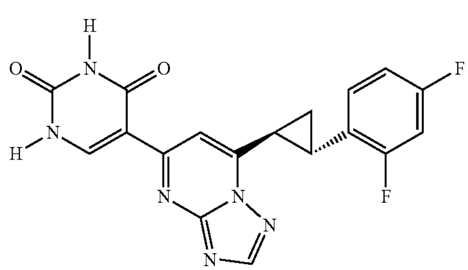 [SMILES: O=c1[nH]cc(-c2cc([C@H]3C[C@@H]3c3ccc(F)cc3F)n3ncnc3n2)c(=O)[nH]1] | 5-(7-((1S,2S)-2-(2,4-difluorophenyl)cyclopropyl)-[1,2,4]triazolo[1,5-a]pyrimidin-5-yl)pyrimidine-2,4(1H,3H)-dione |

TABLE 2-continued

| Ex. No. | Structure | IUPAC Name |
| --- | --- | --- |
| 417 | 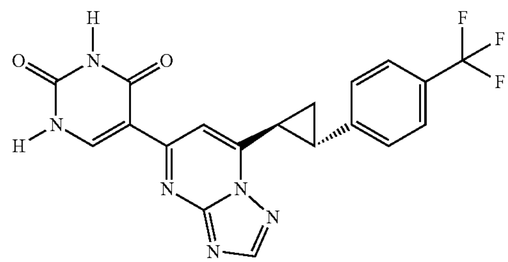 [SMILES: O=c1[nH]cc(-c2cc([C@H]3C[C@@H]3c3ccc(C(F)(F)F)cc3)n3ncnc3n2)c(=O)[nH]1] | 5-(7-((1S,2S)-2-(4-(trifluoromethyl)phenyl)cyclopropyl)-[1,2,4]triazolo[1,5-a]pyrimidin-5-yl)pyrimidine-2,4(1H,3H)-dione |
| 418 | 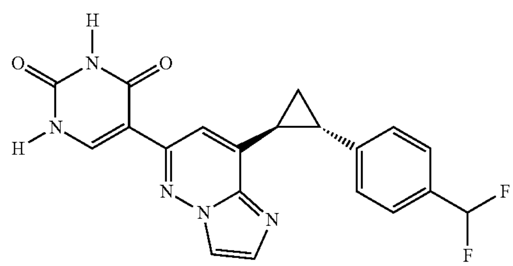 [SMILES: O=c1[nH]cc(-c2cc([C@H]3C[C@@H]3c3ccc(C(F)F)cc3)c3nccn3n2)c(=O)[nH]1] | 5-(8-((1S,2S)-2-(4-(difluoromethyl)phenyl)cyclopropyl)imidazo[1,2-b]pyridazin-6-yl)pyrimidine-2,4(1H,3H)-dione |
| 419 | 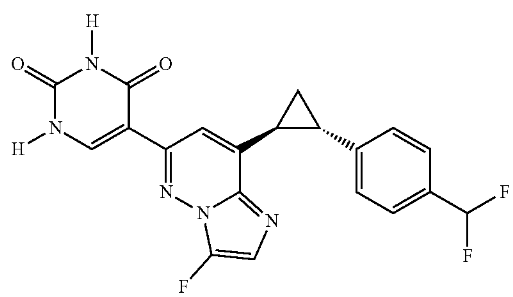 [SMILES: O=c1[nH]cc(-c2cc([C@H]3C[C@@H]3c3ccc(C(F)F)cc3)c3ncc(F)n3n2)c(=O)[nH]1] | 5-(8-((1S,2S)-2-(4-(difluoromethyl)phenyl)cyclopropyl)-3-fluoroimidazo[1,2-b]pyridazin-6-yl)pyrimidine-2,4(1H,3H)-dione |
| 420 | 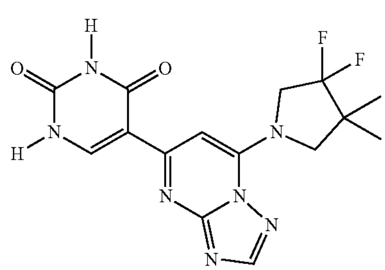 | 5-(7-(3,3-difluoro-4,4-dimethylpyrrolidin-1-yl)-[1,2,4]triazolo[1,5-a]pyrimidin-5-yl)pyrimidine-2,4(1H,3H)-dione |
| 421 | 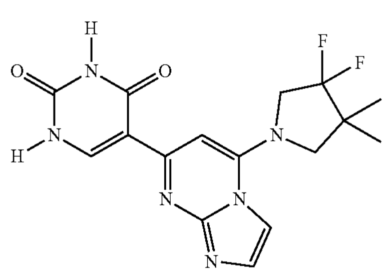 [SMILES: CC1(C)CN(c2cc(-c3c[nH]c(=O)[nH]c3=O)nc3nccn23)CC1(F)F] | 5-(5-(3,3-difluoro-4,4-dimethylpyrrolidin-1-yl)imidazo[1,2-a]pyrimidin-7-yl)pyrimidine-2,4(1H,3H)-dione |

TABLE 2-continued

| Ex. No. | Structure | IUPAC Name |
|---|---|---|
| 422 | 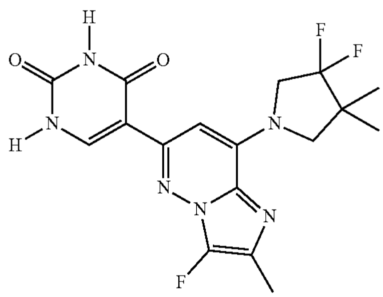 [SMILES: Cc1nc2c(N3CC(C)(C)C(F)(F)C3)cc(-c3c[nH]c(=O)[nH]c3=O)nn2c1F] | 5-(8-(3,3-difluoro-4,4-dimethylpyrrolidin-1-yl)-3-fluoro-2-methylimidazo[1,2-b]pyridazin-6-yl)pyrimidine-2,4(1H,3H)-dione |
| 423 | 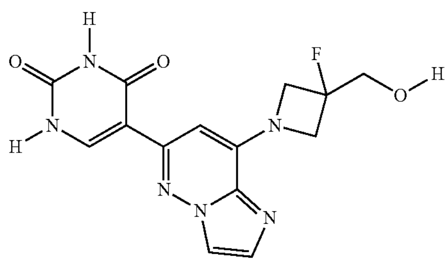 [SMILES: O=c1[nH]cc(-c2cc(N3CC(F)(CO)C3)c3nccn3n2)c(=O)[nH]1] | 5-(8-(3-fluoro-3-(hydroxymethyl)azetidin-1-yl)imidazo[1,2-b]pyridazin-6-yl)pyrimidine-2,4(1H,3H)-dione |
| 424 | 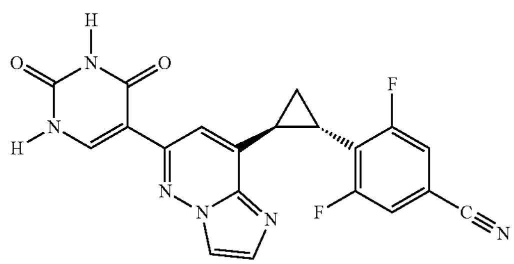 [SMILES: N#Cc1cc(F)c([C@H]2C[C@@H]2c2cc(-c3c[nH]c(=O)[nH]c3=O)nn3ccnc23)c(F)c1] | 4-((1S,2S)-2-(6-(2,4-dioxo-1,2,3,4-tetrahydropyrimidin-5-yl)imidazo[1,2-b]pyridazin-8-yl)cyclopropyl)-3,5-difluorobenzonitrile |
| 425 | 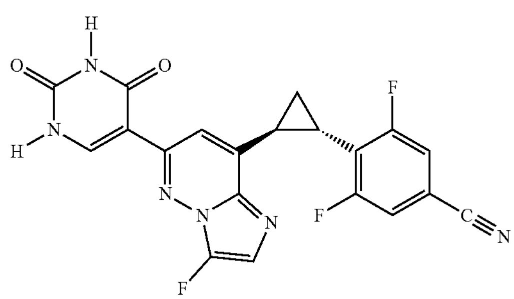 [SMILES: N#Cc1cc(F)c([C@H]2C[C@@H]2c2cc(-c3c[nH]c(=O)[nH]c3=O)nn3c(F)cnc23)c(F)c1] | 4-((1S,2S)-2-(6-(2,4-dioxo-1,2,3,4-tetrahydropyrimidin-5-yl)-3-fluoroimidazo[1,2-b]pyridazin-8-yl)cyclopropyl)-3,5-difluorobenzonitrile |
| 426 | 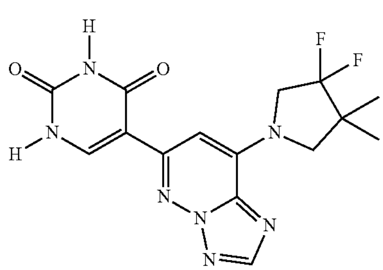 [SMILES: CC1(C)CN(c2cc(-c3c[nH]c(=O)[nH]c3=O)nn3ncnc23)CC1(F)F] | 5-(8-(3,3-difluoro-4,4-dimethylpyrrolidin-1-yl)-[1,2,4]triazolo[1,5-b]pyridazin-6-yl)pyrimidine-2,4(1H,3H)-dione |

TABLE 2-continued

| Ex. No. | Structure | IUPAC Name |
|---|---|---|
| 427 | 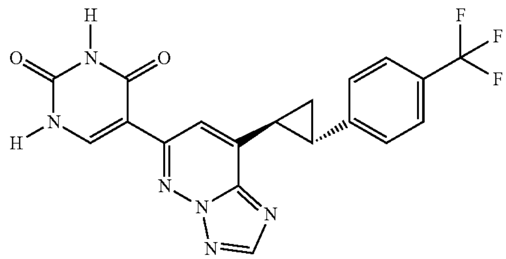 [SMILES: O=c1[nH]cc(-c2cc([C@H]3C[C@@H]3c3ccc(C(F)(F)F)cc3)c3ncnn3n2)c(=O)[nH]1] | 5-(8-((1S,2S)-2-(4-(trifluoromethyl)phenyl)cyclopropyl)-[1,2,4]triazolo[1,5-b]pyridazin-6-yl)pyrimidine-2,4(1H,3H)-dione |
| 428 | 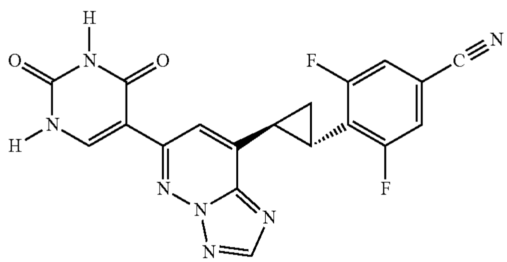 [SMILES: N#Cc1cc(F)c([C@H]2C[C@@H]2c2cc(-c3c[nH]c(=O)[nH]c3=O)nn3ncnc23)c(F)c1] | 4-((1S,2S)-2-(6-(2,4-dioxo-1,2,3,4-tetrahydropyrimidin-5-yl)-[1,2,4]triazolo[1,5-b]pyridazin-8-yl)cyclopropyl)-3,5-difluorobenzonitrile |
| 429 | 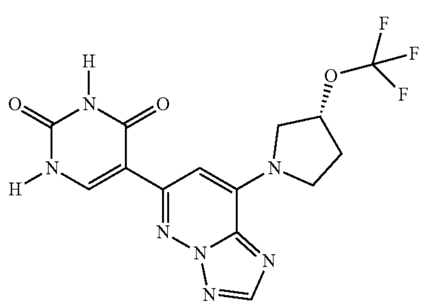 [SMILES: O=c1[nH]cc(-c2cc(N3CC[C@@H](OC(F)(F)F)C3)c3ncnn3n2)c(=O)[nH]1] | (R)-5-(8-(3-(trifluoromethoxy)pyrrolidin-1-yl)-[1,2,4]triazolo[1,5-b]pyridazin-6-yl)pyrimidine-2,4(1H,3H)-dione |
| 430 | 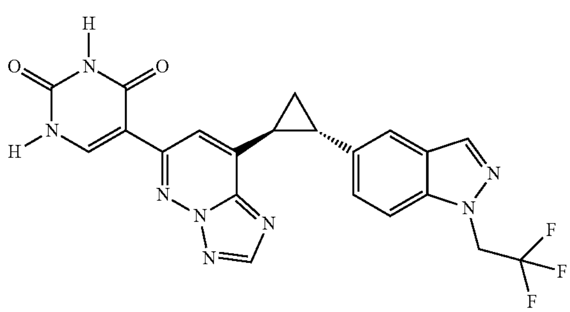 [SMILES: O=c1[nH]cc(-c2cc([C@H]3C[C@@H]3c3ccc4c(cnn4CC(F)(F)F)c3)c3ncnn3n2)c(=O)[nH]1] | 5-(8-((1S,2S)-2-(1-(2,2,2-trifluoroethyl)-1H-indazol-5-yl)cyclopropyl)-[1,2,4]triazolo[1,5-b]pyridazin-6-yl)pyrimidine-2,4(1H,3H)-dione |
| 431 | 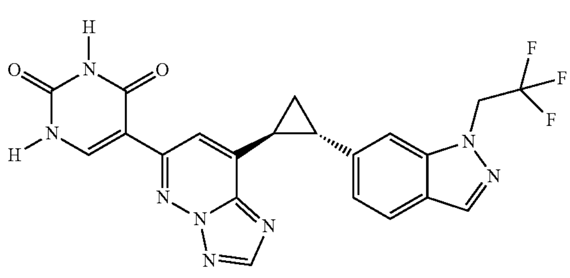 [SMILES: O=c1[nH]cc(-c2cc([C@H]3C[C@@H]3c3ccc4cnn(CC(F)(F)F)c4c3)c3ncnn3n2)c(=O)[nH]1] | 5-(8-((1S,2S)-2-(1-(2,2,2-trifluoroethyl)-1H-indazol-6-yl)cyclopropyl)-[1,2,4]triazolo[1,5-b]pyridazin-6-yl)pyrimidine-2,4(1H,3H)-dione |

TABLE 2-continued

| Ex. No. | Structure | IUPAC Name |
|---|---|---|
| 432 | 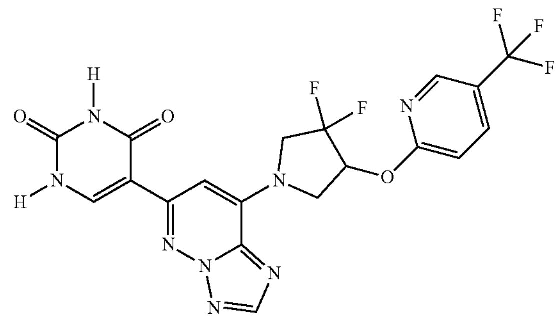 [SMILES: O=c1[nH]cc(-c2cc(N3CC(Oc4ccc(C(F)(F)F)cn4)C(F)(F)C3)c3ncnn3n2)c(=O)[nH]1] | 5-(8-(3,3-difluoro-4-((5-(trifluoromethyl)pyridin-2-yl)oxy)pyrrolidin-1-yl)-[1,2,4]triazolo[1,5-b]pyridazin-6-yl)pyrimidine-2,4(1H,3H)-dione |
| 433 | 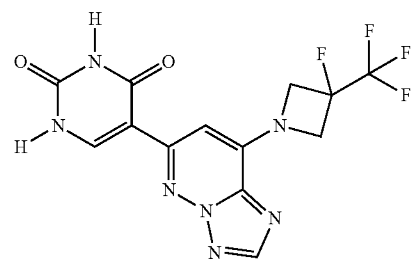 [SMILES: O=c1[nH]cc(-c2cc(N3CC(F)(C(F)(F)F)C3)c3ncnn3n2)c(=O)[nH]1] | 5-(8-(3-fluoro-3-(trifluoromethyl)azetidin-1-yl)-[1,2,4]triazolo[1,5-b]pyridazin-6-yl)pyrimidine-2,4(1H,3H)-dione |
| 434 | 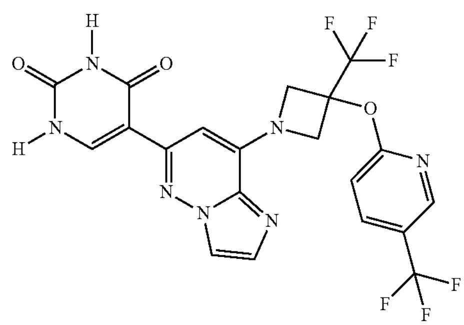 [SMILES: O=c1[nH]cc(-c2cc(N3CC(Oc4ccc(C(F)(F)F)cn4)(C(F)(F)F)C3)c3nccn3n2)c(=O)[nH]1] | 5-(8-(3-(trifluoromethyl)-3-((5-(trifluoromethyl)pyridin-2-yl)oxy)azetidin-1-yl)imidazo[1,2-b]pyridazin-6-yl)pyrimidine-2,4(1H,3H)-dione |
| 435 | 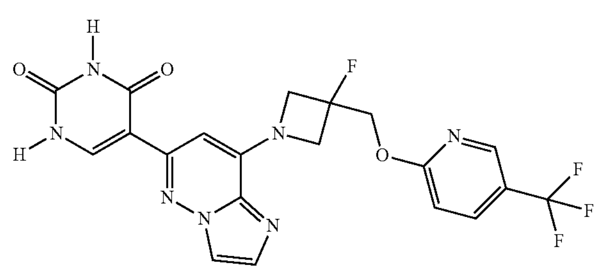 [SMILES: O=c1[nH]cc(-c2cc(N3CC(F)(COc4ccc(C(F)(F)F)cn4)C3)c3nccn3n2)c(=O)[nH]1] | 5-(8-(3-fluoro-3-(((5-(trifluoromethyl)pyridin-2-yl)oxy)methyl)azetidin-1-yl)imidazo[1,2-b]pyridazin-6-yl)pyrimidine-2,4(1H,3H)-dione |
| 436 | 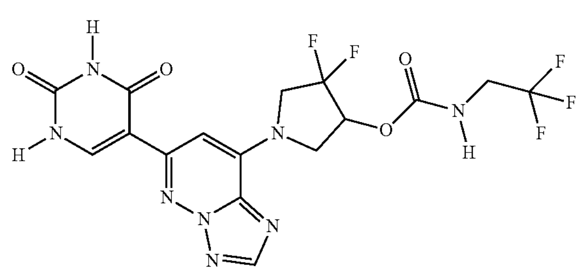 [SMILES: O=C(NCC(F)(F)F)OC1CN(c2cc(-c3c[nH]c(=O)[nH]c3=O)nn3ncnc23)CC1(F)F] | 1-(6-(2,4-dioxo-1,2,3,4-tetrahydropyrimidin-5-yl)-[1,2,4]triazolo[1,5-b]pyridazin-8-yl)-4,4-difluoropyrrolidin-3-yl (2,2,2-trifluoroethyl)carbamate |

TABLE 2-continued

| Ex. No. | Structure | IUPAC Name |
|---|---|---|
| 437 | 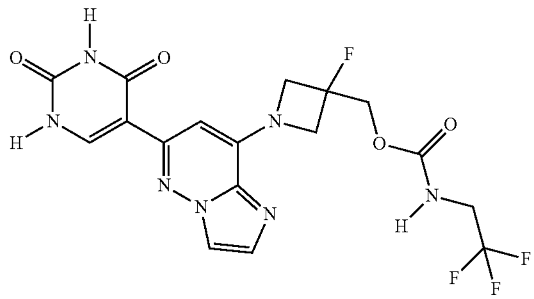 [SMILES: O=C(NCC(F)(F)F)OCC1(F)CN(c2cc(-c3c[nH]c(=O)[nH]c3=O)nn3ccnc23)C1] | (1-(6-(2,4-dioxo-1,2,3,4-tetrahydropyrimidin-5-yl)imidazo[1,2-b]pyridazin-8-yl)-3-fluoroazetidin-3-yl)methyl (2,2,2-trifluoroethyl)carbamate |
| 438 | 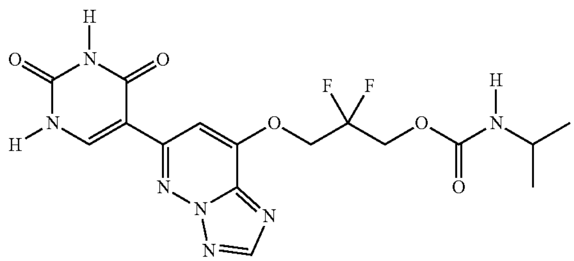 [SMILES: CC(C)NC(=O)OCC(F)(F)COc1cc(-c2c[nH]c(=O)[nH]c2=O)nn2ncnc12] | 3-((6-(2,4-dioxo-1,2,3,4-tetrahydropyrimidin-5-yl)-[1,2,4]triazolo[1,5-b]pyridazin-8-yl)oxy)-2,2-difluoropropyl isopropylcarbamate |
| 439 | 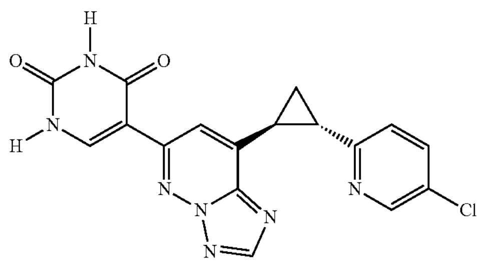 [SMILES: O=c1[nH]cc(-c2cc([C@H]3C[C@@H]3c3ccc(Cl)cn3)c3ncnn3n2)c(=O)[nH]1] | 5-(8-((1S,2S)-2-(5-chloropyridin-2-yl)cyclopropyl)-[1,2,4]triazolo[1,5-b]pyridazin-6-yl)pyrimidine-2,4(1H,3H)-dione |
| 440 | 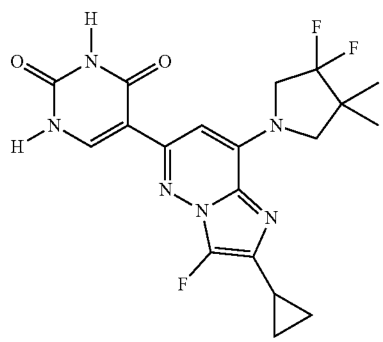 [SMILES: CC1(C)CN(c2cc(-c3c[nH]c(=O)[nH]c3=O)nn3c(F)c(C4CC4)nc23)CC1(F)F] | 5-(2-cyclopropyl-8-(3,3-difluoro-4,4-dimethylpyrrolidin-1-yl)-3-fluoroimidazo[1,2-b]pyridazin-6-yl)pyrimidine-2,4(1H,3H)-dione |
| 441 | 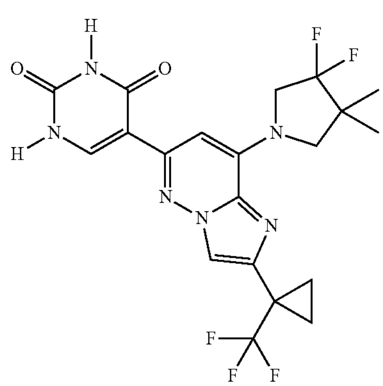 [SMILES: CC1(C)CN(c2cc(-c3c[nH]c(=O)[nH]c3=O)nn3cc(C4(C(F)(F)F)CC4)nc23)CC1(F)F] | 5-(8-(3,3-difluoro-4,4-dimethylpyrrolidin-1-yl)-2-(1-(trifluoromethyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 442 | 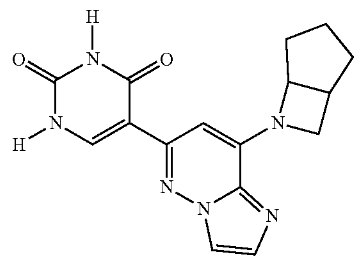 [SMILES: O=c1[nH]cc(-c2cc(N3CC4CCCC43)c3nccn3n2)c(=O)[nH]1] | 5-(8-(6-azabicyclo[3.2.0]heptan-6-yl)imidazo[1,2-b]pyridazin-6-yl)pyrimidine-2,4(1H,3H)-dione |
| 443 | 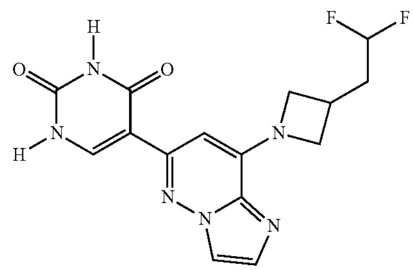 [SMILES: O=c1[nH]cc(-c2cc(N3CC(CC(F)F)C3)c3nccn3n2)c(=O)[nH]1] | 5-(8-(3-(2,2-difluoroethyl)azetidin-1-yl)imidazo[1,2-b]pyridazin-6-yl)pyrimidine-2,4(1H,3H)-dione |
| 444 | 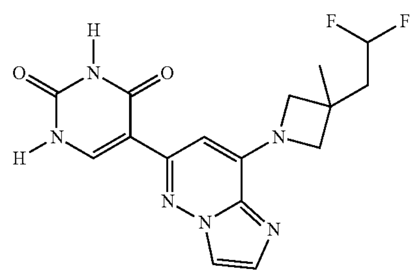 [SMILES: CC1(CC(F)F)CN(c2cc(-c3c[nH]c(=O)[nH]c3=O)nn3ccnc23)C1] | 5-(8-(3-(2,2-difluoroethyl)-3-methylazetidin-1-yl)imidazo[1,2-b]pyridazin-6-yl)pyrimidine-2,4(1H,3H)-dione |
| 445 | 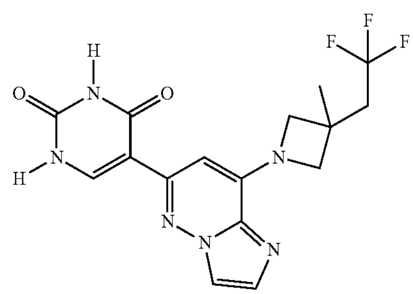 [SMILES: CC1(CC(F)(F)F)CN(c2cc(-c3c[nH]c(=O)[nH]c3=O)nn3ccnc23)C1] | 5-(8-(3-methyl-3-(2,2,2-trifluoroethyl)azetidin-1-yl)imidazo[1,2-b]pyridazin-6-yl)pyrimidine-2,4(1H,3H)-dione |
| 446 | 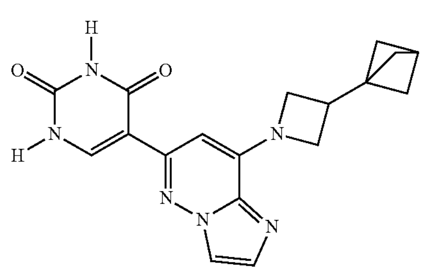 [SMILES: O=c1[nH]cc(-c2cc(N3CC(C45CC(C4)C5)C3)c3nccn3n2)c(=O)[nH]1] | 5-(8-(3-(bicyclo[1.1.1]pentan-1-yl)azetidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 447 | 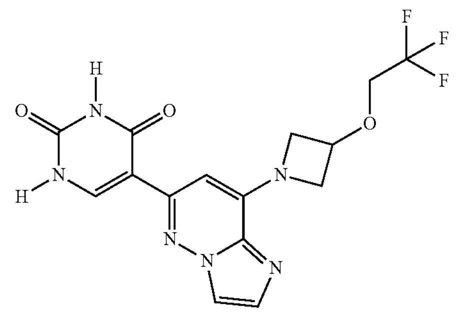 [SMILES: O=c1[nH]cc(-c2cc(N3CC(OCC(F)(F)F)C3)c3nccn3n2)c(=O)[nH]1] | 5-(8-(3-(2,2,2-trifluoroethoxy)azetidin-1-yl)imidazo[1,2-b]pyridazin-6-yl)pyrimidine-2,4(1H,3H)-dione |
| 448 | 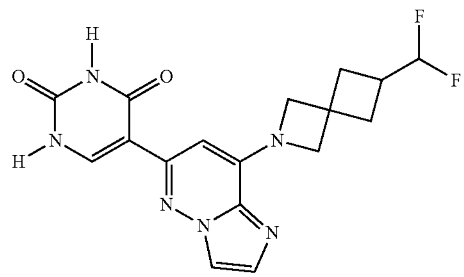 [SMILES: O=c1[nH]cc(-c2cc(N3CC4(CC(C(F)F)C4)C3)c3nccn3n2)c(=O)[nH]1] | 5-(8-(6-(difluoromethyl)-2-azaspiro[3.3]heptan-2-yl)imidazo[1,2-b]pyridazin-6-yl)pyrimidine-2,4(1H,3H)-dione |
| 449 | 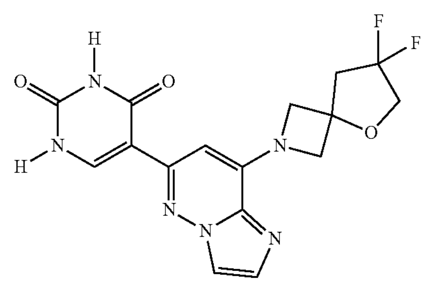 [SMILES: O=c1[nH]cc(-c2cc(N3CC4(C3)CC(F)(F)CO4)c3nccn3n2)c(=O)[nH]1] | 5-(8-(7,7-difluoro-5-oxa-2-azaspiro[3.4]octan-2-yl)imidazo[1,2-b]pyridazin-6-yl)pyrimidine-2,4(1H,3H)-dione |
| 450 | 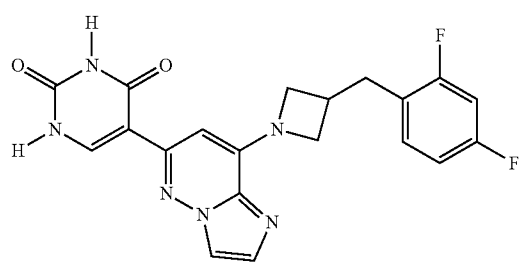 [SMILES: O=c1[nH]cc(-c2cc(N3CC(Cc4ccc(F)cc4F)C3)c3nccn3n2)c(=O)[nH]1] | 5-(8-(3-(2,4-difluorobenzyl)azetidin-1-yl)imidazo[1,2-b]pyridazin-6-yl)pyrimidine-2,4(1H,3H)-dione |
| 451 | 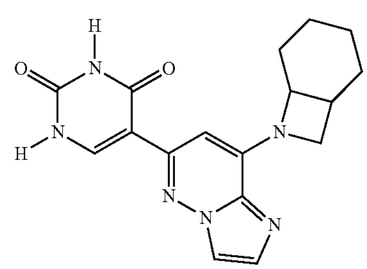 [SMILES: O=c1[nH]cc(-c2cc(N3CC4CCCCC43)c3nccn3n2)c(=O)[nH]1] | 5-(8-(7-azabicyclo[4.2.0]octan-7-yl)imidazo[1,2-b]pyridazin-6-yl)pyrimidine-2,4(1H,3H)-dione |

TABLE 2-continued

| Ex. No. | Structure | IUPAC Name |
|---|---|---|
| 452 | 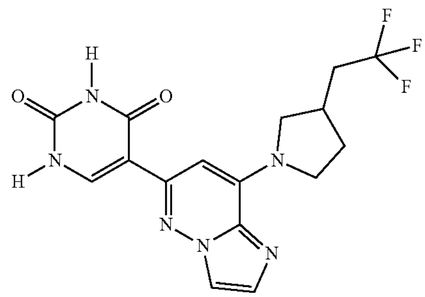 [SMILES: O=c1[nH]cc(-c2cc(N3CCC(CC(F)(F)F)C3)c3nccn3n2)c(=O)[nH]1] | 5-(8-(3-(2,2,2-trifluoroethyl)pyrrolidin-1-yl)imidazo[1,2-b]pyridazin-6-yl)pyrimidine-2,4(1H,3H)-dione |
| 453 | 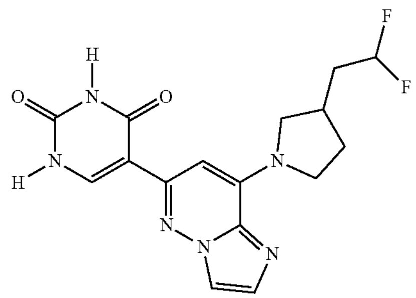 [SMILES: O=c1[nH]cc(-c2cc(N3CCC(CC(F)F)C3)c3nccn3n2)c(=O)[nH]1] | 5-(8-(3-(2,2-difluoroethyl)pyrrolidin-1-yl)imidazo[1,2-b]pyridazin-6-yl)pyrimidine-2,4(1H,3H)-dione |
| 454 | 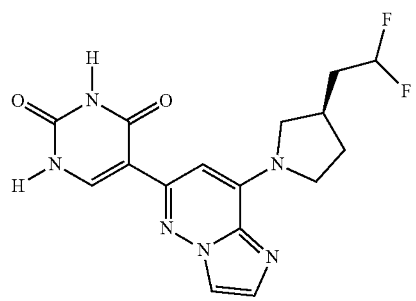 [SMILES: O=c1[nH]cc(-c2cc(N3CC[C@H](CC(F)F)C3)c3nccn3n2)c(=O)[nH]1] | (R)-5-(8-(3-(2,2-difluoroethyl)pyrrolidin-1-yl)imidazo[1,2-b]pyridazin-6-yl)pyrimidine-2,4(1H,3H)-dione |
| 455 | 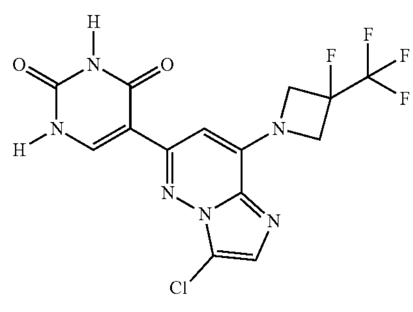 [SMILES: O=c1[nH]cc(-c2cc(N3CC(F)(C(F)(F)F)C3)c3ncc(Cl)n3n2)c(=O)[nH]1] | 5-(3-chloro-8-(3-fluoro-3-(trifluoromethyl)azetidin-1-yl)imidazo[1,2-b]pyridazin-6-yl)pyrimidine-2,4(1H,3H)-dione |
| 456 | 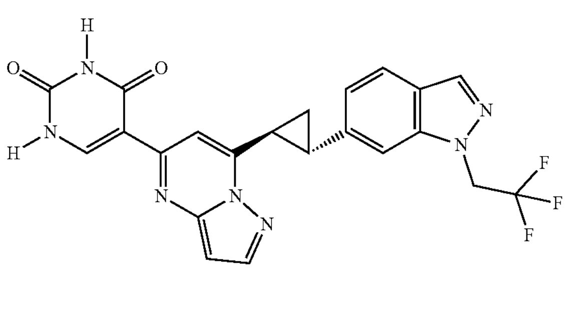 [SMILES: O=c1[nH]cc(-c2cc([C@H]3C[C@@H]3c3ccc4cnn(CC(F)(F)F)c4c3)n3nccc3n2)c(=O)[nH]1] | 5-(7-((1S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione |

TABLE 2-continued

| Ex. No. | Structure | IUPAC Name |
|---|---|---|
| 457 | 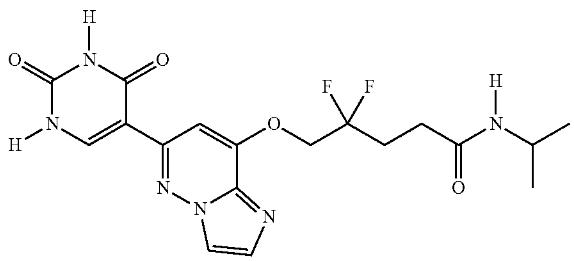 | 5-((6-(2,4-dioxo-1,2,3,4-tetrahydropyrimidin-5-yl)imidazo[1,2-b]pyridazin-8-yl)oxy)-4,4-difluoro-N-isopropylpentanamide |
| 458 | 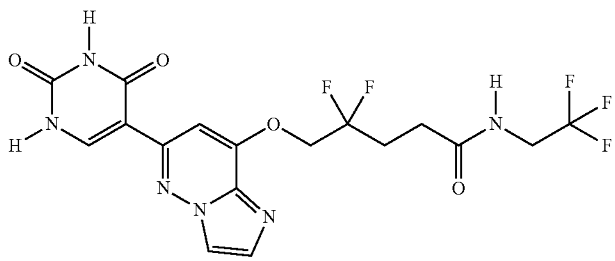 [SMILES: O=C(CCC(F)(F)COc1cc(-c2c[nH]c(=O)[nH]c2=O)nn2ccnc12)NCC(F)(F)F] | 5-((6-(2,4-dioxo-1,2,3,4-tetrahydropyrimidin-5-yl)imidazo[1,2-b]pyridazin-8-yl)oxy)-4,4-difluoro-N-(2,2,2-trifluoroethyl)pentanamide |
| 459 | 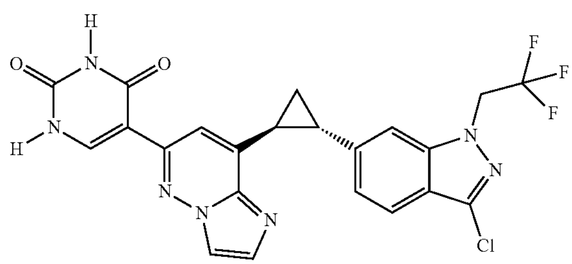 [SMILES: O=c1[nH]cc(-c2cc([C@H]3C[C@@H]3c3ccc4c(Cl)nn(CC(F)(F)F)c4c3)c3nccn3n2)c(=O)[nH]1] | 5-(8-((1S,2S)-2-(3-chloro-1-(2,2,2-trifluoroethyl)-1H-indazol-6-yl)cyclopropyl)imidazo[1,2-b]pyridazin-6-yl)pyrimidine-2,4(1H,3H)-dione |
| 460 | 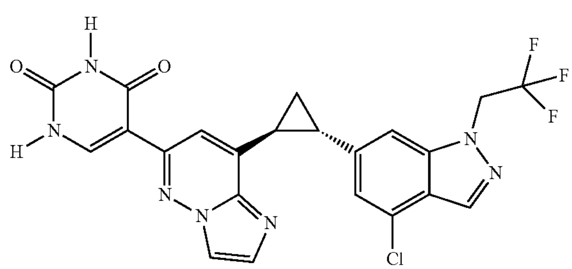 [SMILES: O=c1[nH]cc(-c2cc([C@H]3C[C@@H]3c3cc(Cl)c4cnn(CC(F)(F)F)c4c3)c3nccn3n2)c(=O)[nH]1] | 5-(8-((1S,2S)-2-(4-chloro-1-(2,2,2-trifluoroethyl)-1H-indazol-6-yl)cyclopropyl)imidazo[1,2-b]pyridazin-6-yl)pyrimidine-2,4(1H,3H)-dione |
| 461 | 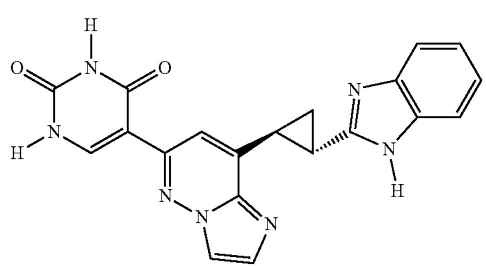 [SMILES: O=c1[nH]cc(-c2cc([C@H]3C[C@@H]3c3nc4ccccc4[nH]3)c3nccn3n2)c(=O)[nH]1] | 5-(8-((1S,2S)-2-(1H-benzo[d]imidazol-2-yl)cyclopropyl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 462 | 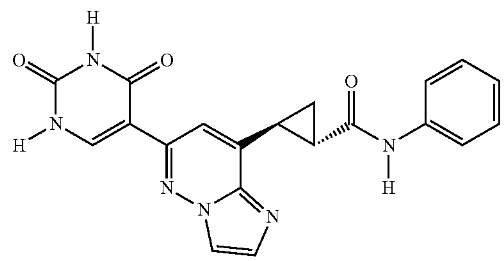 [SMILES: O=C(Nc1ccccc1)[C@H]1C[C@@H]1c1cc(-c2c[nH]c(=O)[nH]c2=O)nn2ccnc12] | (1S,2S)-2-(6-(2,4-dioxo-1,2,3,4-tetrahydropyrimidin-5-yl)imidazo[1,2-b]pyridazin-8-yl)-N-phenylcyclopropane-1-carboxamide |
| 463 | 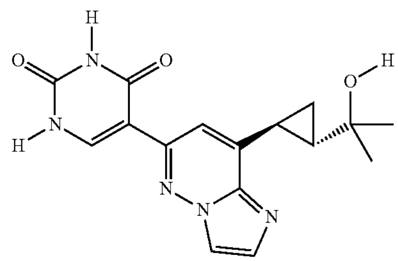 [SMILES: CC(C)(O)[C@H]1C[C@@H]1c1cc(-c2c[nH]c(=O)[nH]c2=O)nn2ccnc12] | 5-(8-((1S,2S)-2-(2-hydroxypropan-2-yl)cyclopropyl)imidazo[1,2-b]pyridazin-6-yl)pyrimidine-2,4(1H,3H)-dione |
| 464 | 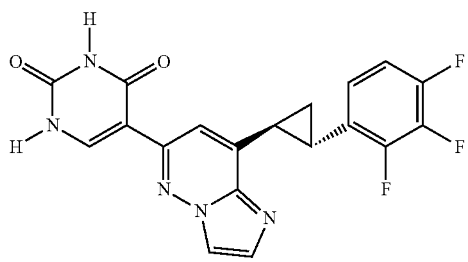 [SMILES: O=c1[nH]cc(-c2cc([C@H]3C[C@@H]3c3ccc(F)c(F)c3F)c3nccn3n2)c(=O)[nH]1] | 5-(8-((1S,2S)-2-(2,3,4-trifluorophenyl)cyclopropyl)imidazo[1,2-b]pyridazin-6-yl)pyrimidine-2,4(1H,3H)-dione |
| 465 | 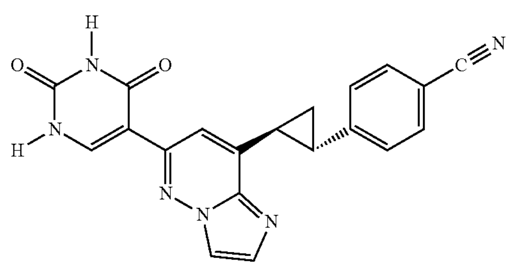 [SMILES: N#Cc1ccc([C@H]2C[C@@H]2c2cc(-c3c[nH]c(=O)[nH]c3=O)nn3ccnc23)cc1] | 4-((1S,2S)-2-(6-(2,4-dioxo-1,2,3,4-tetrahydropyrimidin-5-yl)imidazo[1,2-b]pyridazin-8-yl)cyclopropyl)benzonitrile |
| 466 | 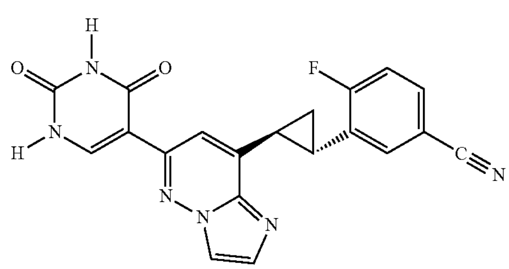 [SMILES: N#Cc1ccc(F)c([C@H]2C[C@@H]2c2cc(-c3c[nH]c(=O)[nH]c3=O)nn3ccnc23)c1] | 3-((1S,2S)-2-(6-(2,4-dioxo-1,2,3,4-tetrahydropyrimidin-5-yl)imidazo[1,2-b]pyridazin-8-yl)cyclopropyl)-4-fluorobenzonitrile |

TABLE 2-continued

| Ex. No. | Structure | IUPAC Name |
|---|---|---|
| 467 | 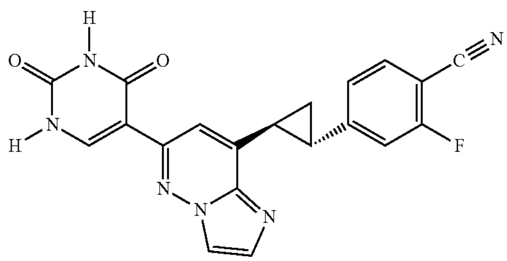 [SMILES: N#Cc1ccc([C@H]2C[C@@H]2c2cc(-c3c[nH]c(=O)[nH]c3=O)nn3ccnc23)cc1F] | 4-((1S,2S)-2-(6-(2,4-dioxo-1,2,3,4-tetrahydropyrimidin-5-yl)imidazo[1,2-b]pyridazin-8-yl)cyclopropyl)-2-fluorobenzonitrile |
| 468 | 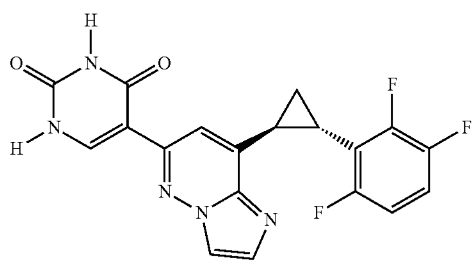 [SMILES: O=c1[nH]cc(-c2cc([C@H]3C[C@@H]3c3c(F)ccc(F)c3F)c3nccn3n2)c(=O)[nH]1] | 5-(8-((1S,2S)-2-(2,3,6-trifluorophenyl)cyclopropyl)imidazo[1,2-b]pyridazin-6-yl)pyrimidine-2,4(1H,3H)-dione |
| 469 | 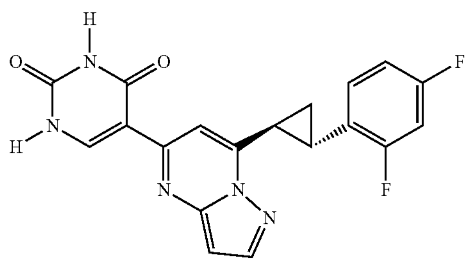 [SMILES: O=c1[nH]cc(-c2cc([C@H]3C[C@@H]3c3ccc(F)cc3F)n3nccc3n2)c(=O)[nH]1] | 5-(7-((1S,2S)-2-(2,4-difluorophenyl)cyclopropyl)pyrazolo[1,5-a]pyrimidin-5-yl)pyrimidine-2,4(1H,3H)-dione |
| 470 | 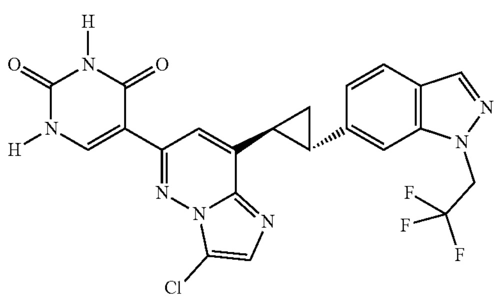 [SMILES: O=c1[nH]cc(-c2cc([C@H]3C[C@@H]3c3ccc4cnn(CC(F)(F)F)c4c3)c3ncc(Cl)n3n2)c(=O)[nH]1] | 5-(3-chloro-8-((1S,2S)-2-(1-(2,2,2-trifluoroethyl)-1H-indazol-6-yl)cyclopropyl)imidazo[1,2-b]pyridazin-6-yl)pyrimidine-2,4(1H,3H)-dione |
| 471 | 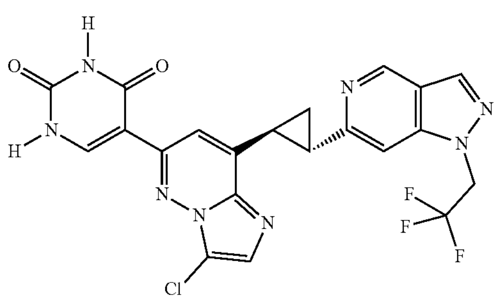 [SMILES: O=c1[nH]cc(-c2cc([C@H]3C[C@@H]3c3cc4c(cn3)cnn4CC(F)(F)F)c3ncc(Cl)n3n2)c(=O)[nH]1] | 5-(3-chloro-8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 472 | 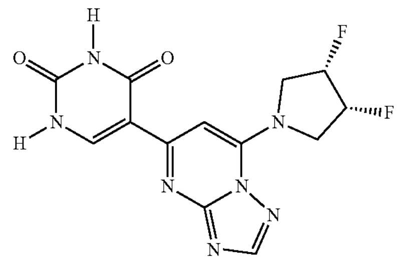 [SMILES: O=c1[nH]cc(-c2cc(N3C[C@@H](F)[C@@H](F)C3)n3ncnc3n2)c(=O)[nH]1] | 5-(7-((3R,4S)-3,4-difluoropyrrolidin-1-yl)-[1,2,4]triazolo[1,5-a]pyrimidin-5-yl)pyrimidine-2,4(1H,3H)-dione |
| 473 | 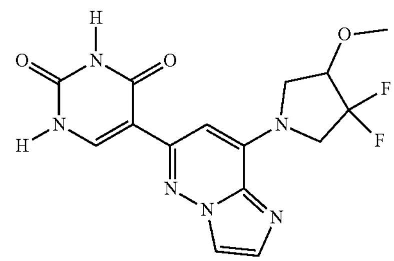 [SMILES: COC1CN(c2cc(-c3c[nH]c(=O)[nH]c3=O)nn3ccnc23)CC1(F)F] | 5-(8-(3,3-difluoro-4-methoxypyrrolidin-1-yl)imidazo[1,2-b]pyridazin-6-yl)pyrimidine-2,4(1H,3H)-dione |
| 474 | 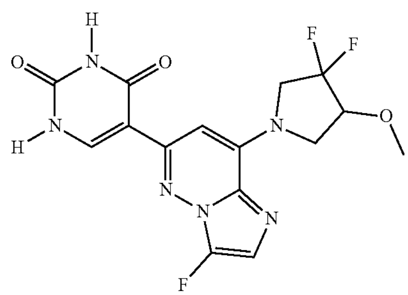 [SMILES: COC1CN(c2cc(-c3c[nH]c(=O)[nH]c3=O)nn3c(F)cnc23)CC1(F)F] | 5-(8-(3,3-difluoro-4-methoxypyrrolidin-1-yl)-3-fluoroimidazo[1,2-b]pyridazin-6-yl)pyrimidine-2,4(1H,3H)-dione |
| 475 | 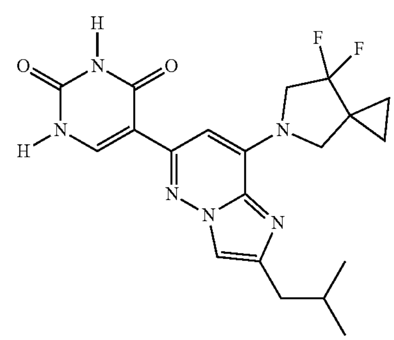 [SMILES: CC(C)Cc1cn2nc(-c3c[nH]c(=O)[nH]c3=O)cc(N3CC(F)(F)C4(CC4)C3)c2n1] | 5-(8-(7,7-difluoro-5-azaspiro[2.4]heptan-5-yl)-2-isobutylimidazo[1,2-b]pyridazin-6-yl)pyrimidine-2,4(1H,3H)-dione |
| 476 | 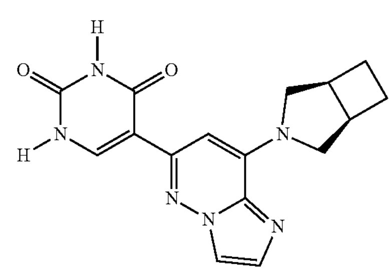 [SMILES: O=c1[nH]cc(-c2cc(N3C[C@H]4CC[C@H]4C3)c3nccn3n2)c(=O)[nH]1] | 5-(8-((1R,5S)-3-azabicyclo[3.2.0]heptan-3-yl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 477 | 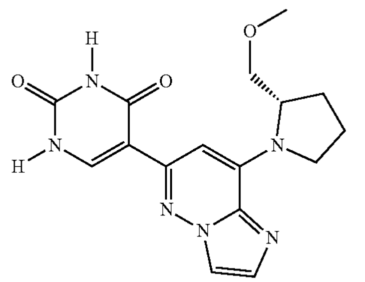 [SMILES: COC[C@@H]1CCCN1c1cc(-c2c[nH]c(=O)[nH]c2=O)nn2ccnc12] | (S)-5-(8-(2-(methoxymethyl)pyrrolidin-1-yl)imidazo[1,2-b]pyridazin-6-yl)pyrimidine-2,4(1H,3H)-dione |
| 478 | 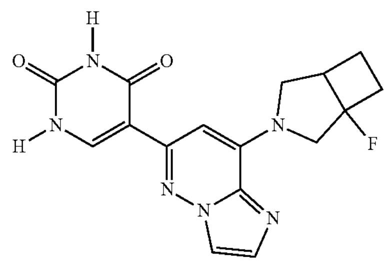 [SMILES: O=c1[nH]cc(-c2cc(N3CC4CCC4(F)C3)c3nccn3n2)c(=O)[nH]1] | 5-(8-(1-fluoro-3-azabicyclo[3.2.0]heptan-3-yl)imidazo[1,2-b]pyridazin-6-yl)pyrimidine-2,4(1H,3H)-dione |
| 479 | 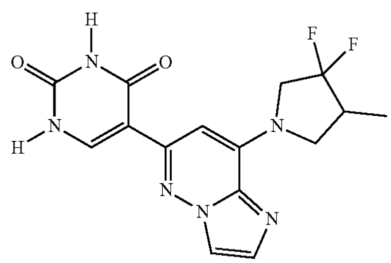 [SMILES: CC1CN(c2cc(-c3c[nH]c(=O)[nH]c3=O)nn3ccnc23)CC1(F)F] | 5-(8-(3,3-difluoro-4-methylpyrrolidin-1-yl)imidazo[1,2-b]pyridazin-6-yl)pyrimidine-2,4(1H,3H)-dione |
| 480 | 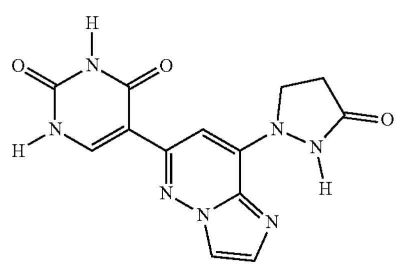 [SMILES: O=C1CCN(c2cc(-c3c[nH]c(=O)[nH]c3=O)nn3ccnc23)N1] | 5-(8-(3-oxopyrazolidin-1-yl)imidazo[1,2-b]pyridazin-6-yl)pyrimidine-2,4(1H,3H)-dione |
| 481 | 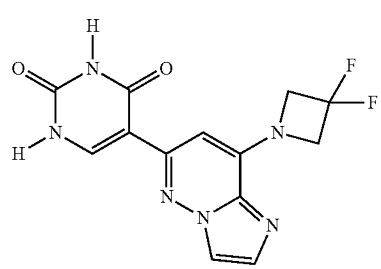 [SMILES: O=c1[nH]cc(-c2cc(N3CC(F)(F)C3)c3nccn3n2)c(=O)[nH]1] | 5-(8-(3,3-difluoroazetidin-1-yl)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 482 | 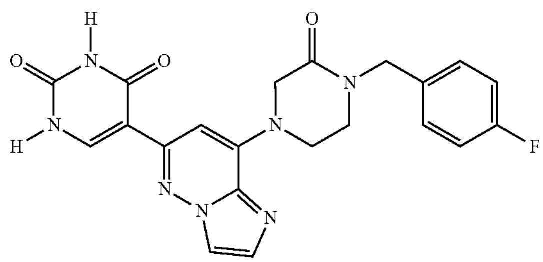 [SMILES: O=C1CN(c2cc(-c3c[nH]c(=O)[nH]c3=O)nn3ccnc23)CCN1Cc1ccc(F)cc1] | 5-(8-(4-(4-fluorobenzyl)-3-oxopiperazin-1-yl)imidazo[1,2-b]pyridazin-6-yl)pyrimidine-2,4(1H,3H)-dione |
| 483 | 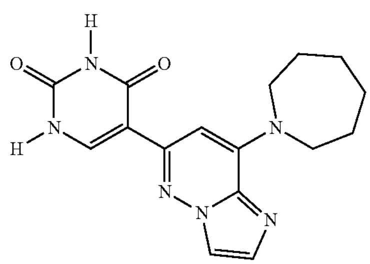 [SMILES: O=c1[nH]cc(-c2cc(N3CCCCCC3)c3nccn3n2)c(=O)[nH]1] | 5-(8-(azepan-1-yl)imidazo[1,2-b]pyridazin-6-yl)pyrimidine-2,4(1H,3H)-dione |
| 484 | 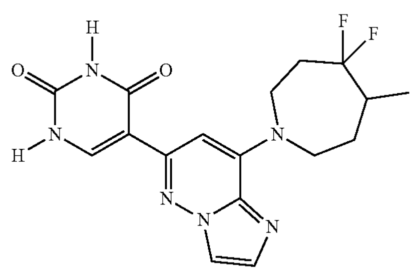 [SMILES: CC1CCN(c2cc(-c3c[nH]c(=O)[nH]c3=O)nn3ccnc23)CCC1(F)F] | 5-(8-(4,4-difluoro-5-methylazepan-1-yl)imidazo[1,2-b]pyridazin-6-yl)pyrimidine-2,4(1H,3H)-dione |
| 485 | 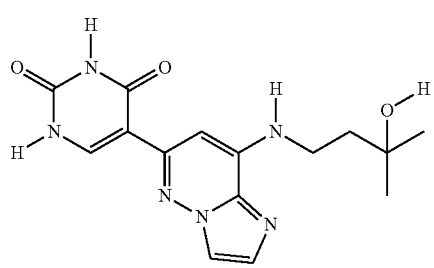 [SMILES: CC(C)(O)CCNc1cc(-c2c[nH]c(=O)[nH]c2=O)nn2ccnc12] | 5-(8-((3-hydroxy-3-methylbutyl)amino)imidazo[1,2-b]pyridazin-6-yl)pyrimidine-2,4(1H,3H)-dione |
| 486 | 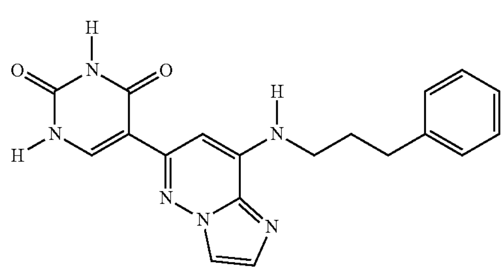 [SMILES: O=c1[nH]cc(-c2cc(NCCCc3ccccc3)c3nccn3n2)c(=O)[nH]1] | 5-(8-((3-phenylpropyl)amino)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 487 | 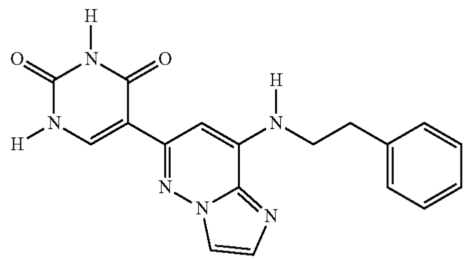 [SMILES: O=c1[nH]cc(-c2cc(NCCc3ccccc3)c3nccn3n2)c(=O)[nH]1] | 5-(8-(phenethylamino)imidazo[1,2-b]pyridazin-6-yl)pyrimidine-2,4(1H,3H)-dione |
| 488 | 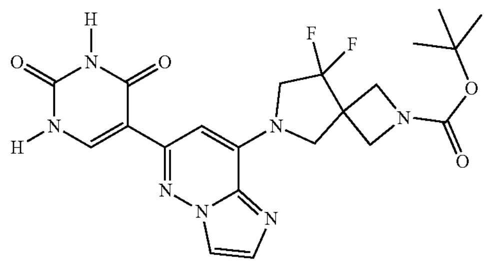 [SMILES: CC(C)(C)OC(=O)N1CC2(C1)CN(c1cc(-c3c[nH]c(=O)[nH]c3=O)nn3ccnc13)CC2(F)F] | tert-butyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate |
| 489 | 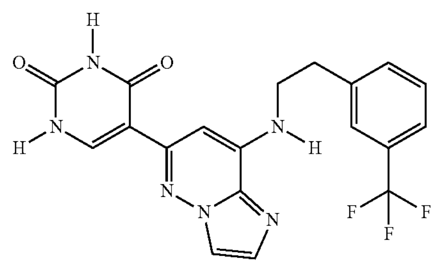 [SMILES: O=c1[nH]cc(-c2cc(NCCc3cccc(C(F)(F)F)c3)c3nccn3n2)c(=O)[nH]1] | 5-(8-((3-(trifluoromethyl)phenethyl)amino)imidazo[1,2-b]pyridazin-6-yl)pyrimidine-2,4(1H,3H)-dione |
| 490 | 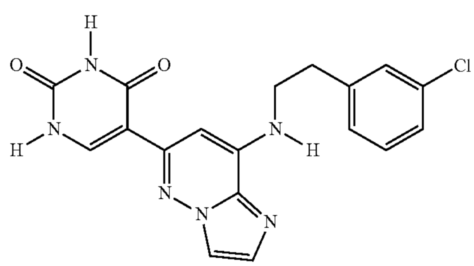 [SMILES: O=c1[nH]cc(-c2cc(NCCc3cccc(Cl)c3)c3nccn3n2)c(=O)[nH]1] | 5-(8-((3-chlorophenethyl)amino)imidazo[1,2-b]pyridazin-6-yl)pyrimidine-2,4(1H,3H)-dione |
| 491 | 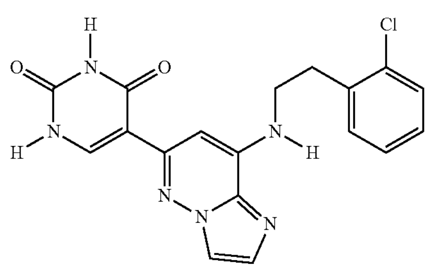 [SMILES: O=c1[nH]cc(-c2cc(NCCc3ccccc3Cl)c3nccn3n2)c(=O)[nH]1] | 5-(8-((2-chlorophenethyl)amino)imidazo[1,2-b]pyridazin-6-yl)pyrimidine-2,4(1H,3H)-dione |

TABLE 2-continued

| Ex. No. | Structure | IUPAC Name |
|---|---|---|
| 492 | 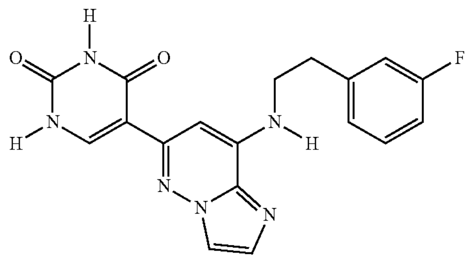 [SMILES: O=c1[nH]cc(-c2cc(NCCc3cccc(F)c3)c3nccn3n2)c(=O)[nH]1] | 5-(8-((3-fluorophenethyl)amino)imidazo[1,2-b]pyridazin-6-yl)pyrimidine-2,4(1H,3H)-dione |
| 493 | 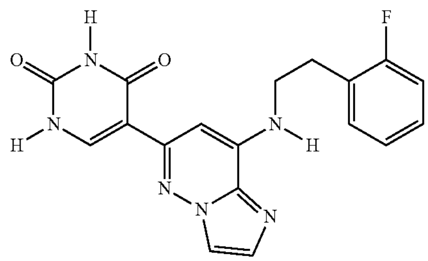 [SMILES: O=c1[nH]cc(-c2cc(NCCc3ccccc3F)c3nccn3n2)c(=O)[nH]1] | 5-(8-((2-fluorophenethyl)amino)imidazo[1,2-b]pyridazin-6-yl)pyrimidine-2,4(1H,3H)-dione |
| 494 | 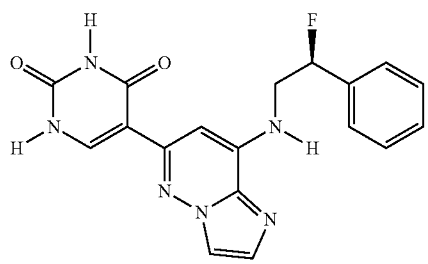 [SMILES: O=c1[nH]cc(-c2cc(NC[C@@H](F)c3ccccc3)c3nccn3n2)c(=O)[nH]1] | (S)-5-(8-((2-fluoro-2-phenylethyl)amino)imidazo[1,2-b]pyridazin-6-yl)pyrimidine-2,4(1H,3H)-dione |
| 495 | 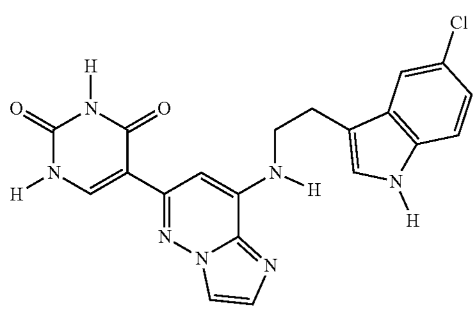 [SMILES: O=c1[nH]cc(-c2cc(NCCc3c[nH]c4ccc(Cl)cc34)c3nccn3n2)c(=O)[nH]1] | 5-(8-((2-(5-chloro-1H-indol-3-yl)ethyl)amino)imidazo[1,2-b]pyridazin-6-yl)pyrimidine-2,4(1H,3H)-dione |
| 496 | 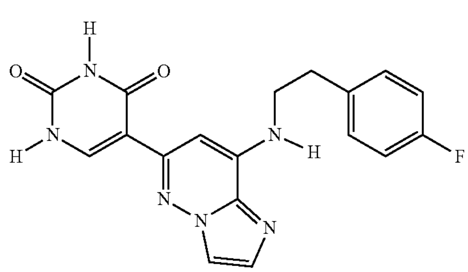 [SMILES: O=c1[nH]cc(-c2cc(NCCc3ccc(F)cc3)c3nccn3n2)c(=O)[nH]1] | 5-(8-((4-fluorophenethyl)amino)imidazo[1,2-b]pyridazin-6-yl)pyrimidine-2,4(1H,3H)-dione |

TABLE 2-continued

| Ex. No. | Structure | IUPAC Name |
|---|---|---|
| 497 | 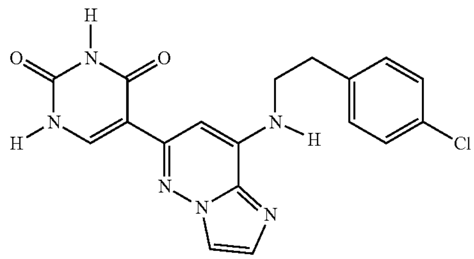 [SMILES: O=c1[nH]cc(-c2cc(NCCc3ccc(Cl)cc3)c3nccn3n2)c(=O)[nH]1] | 5-(8-((4-chlorophenethyl)amino)imidazo[1,2-b]pyridazin-6-yl)pyrimidine-2,4(1H,3H)-dione |
| 498 | 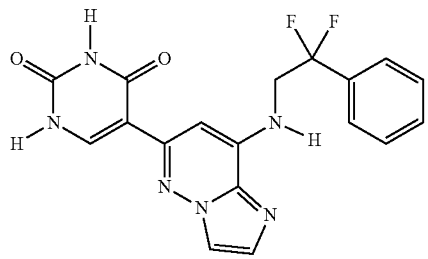 [SMILES: O=c1[nH]cc(-c2cc(NCC(F)(F)c3ccccc3)c3nccn3n2)c(=O)[nH]1] | 5-(8-((2,2-difluoro-2-phenylethyl)amino)imidazo[1,2-b]pyridazin-(6-yl)pyrimidine-2,4(1H,3H)-dione |
| 499 | 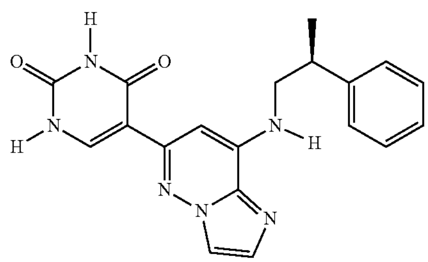 [SMILES: C[C@H](CNc1cc(-c2c[nH]c(=O)[nH]c2=O)nn2ccnc12)c1ccccc1] | (S)-5-(8-((2-phenylpropyl)amino)imidazo[1,2-b]pyridazin-6-yl)pyrimidine-2,4(1H,3H)-dione |
| 500 | 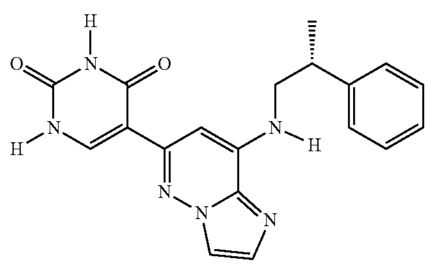 [SMILES: C[C@@H](CNc1cc(-c2c[nH]c(=O)[nH]c2=O)nn2ccnc12)c1ccccc1] | (R)-5-(8-((2-phenylpropyl)amino)imidazo[1,2-b]pyridazin-6-yl)pyrimidine-2,4(1H,3H)-dione |
| 501 | 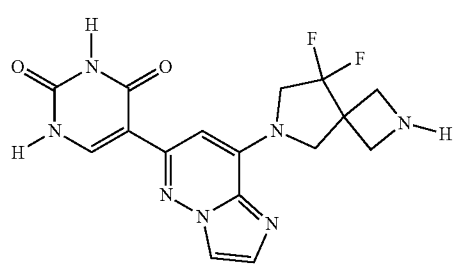 [SMILES: O=c1[nH]cc(-c2cc(N3CC(F)(F)C4(CNC4)C3)c3nccn3n2)c(=O)[nH]1] | 5-(8-(8,8-difluoro-2,6-diazaspiro[3.4]octan-6-yl)imidazo[1,2-b]pyridazin-6-yl)pyrimidine-2,4(1H,3H)-dione |

TABLE 2-continued

| Ex. No. | Structure | IUPAC Name |
|---|---|---|
| 502 | 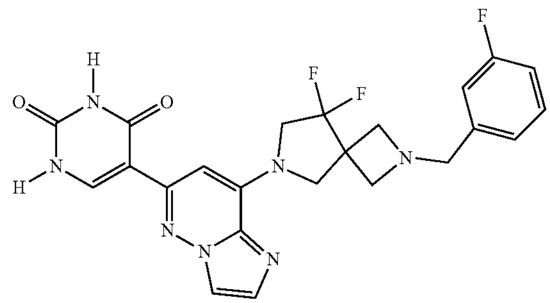 [SMILES: O=c1[nH]cc(-c2cc(N3CC(F)(F)C4(CN(Cc5cccc(F)c5)C4)C3)c3nccn3n2)c(=O)[nH]1] | 5-(8-(8,8-difluoro-2-(3-fluorobenzyl)-2,6-diazaspiro[3.4]octan-6-yl)imidazo[1,2-b]pyridazin-6-yl)pyrimidine-2,4(1H,3H)-dione |
| 503 | 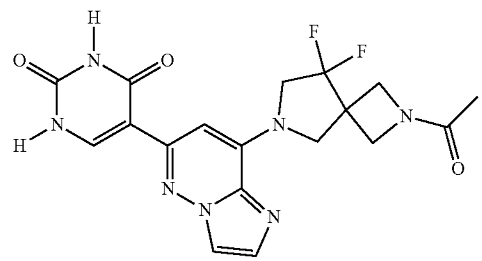 [SMILES: CC(=O)N1CC2(C1)CN(c1cc(-c3c[nH]c(=O)[nH]c3=O)nn3ccnc13)CC2(F)F] | 5-(8-(2-acetyl-8,8-difluoro-2,6-diazaspiro[3.4]octan-6-yl)imidazo[1,2-b]pyridazin-6-yl)pyrimidine-2,4(1H,3H)-dione |
| 504 | 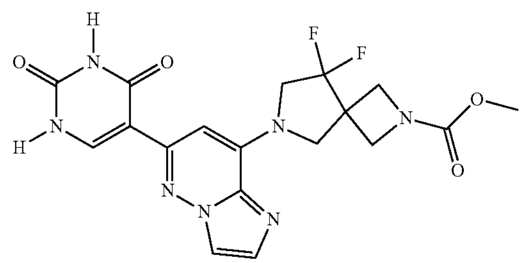 [SMILES: COC(=O)N1CC2(C1)CN(c1cc(-c3c[nH]c(=O)[nH]c3=O)nn3ccnc13)CC2(F)F] | methyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate |
| 505 | 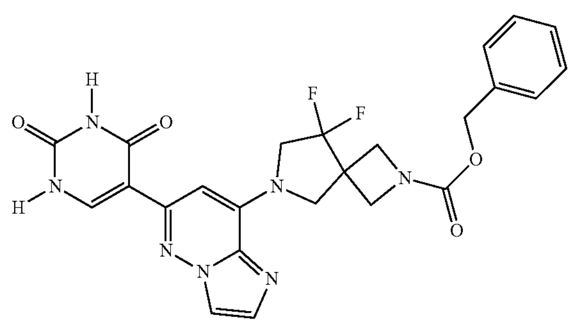 [SMILES: O=C(OCc1ccccc1)N1CC2(C1)CN(c1cc(-c3c[nH]c(=O)[nH]c3=O)nn3ccnc13)CC2(F)F] | benzyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate |
| 506 | 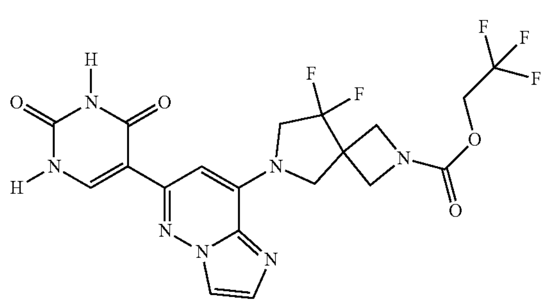 [SMILES: O=C(OCC(F)(F)F)N1CC2(C1)CN(c1cc(-c3c[nH]c(=O)[nH]c3=O)nn3ccnc13)CC2(F)F] | 2,2,2-trifluoroethyl 6-(6-(2,4-dioxo-1,2,3,4-tetrahydropyrimidin-5-yl)imidazo[1,2-b]pyridazin-8-yl)-8,8-difluoro-2,6-diazaspiro[3.4]octane-2-carboxylate |

TABLE 2-continued

| Ex. No. | Structure | IUPAC Name |
|---|---|---|
| 507 | 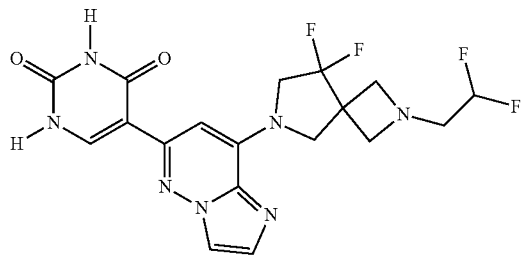 [SMILES: O=c1[nH]cc(-c2cc(N3CC(F)(F)C4(CN(CC(F)F)C4)C3)c3nccn3n2)c(=O)[nH]1] | 5-(8-(2-(2,2-difluoroethyl)-8,8-difluoro-2,6-diazaspiro[3.4]octan-6-yl)imidazo[1,2-b]pyridazin-6-yl)pyrimidine-2,4(1H,3H)-dione |
| 508 | 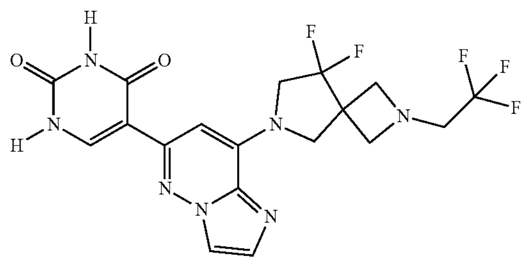 [SMILES: O=c1[nH]cc(-c2cc(N3CC(F)(F)C4(CN(CC(F)(F)F)C4)C3)c3nccn3n2)c(=O)[nH]1] | 5-(8-(8,8-difluoro-2-(2,2,2-trifluoroethyl)-2,6-diazaspiro[3.4]octan-6-yl)imidazo[1,2-b]pyridazin-6-yl)pyrimidine-2,4(1H,3H)-dione |
| 509 | 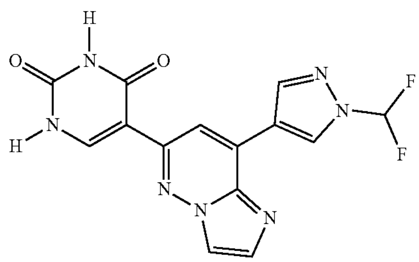 [SMILES: O=c1[nH]cc(-c2cc(-c3cnn(C(F)F)c3)c3nccn3n2)c(=O)[nH]1] | 5-(8-(1-(difluoromethyl)-1H-pyrazol-4-yl)imidazo[1,2-b]pyridazin-6-yl)pyrimidine-2,4(1H,3H)-dione |
| 510 | 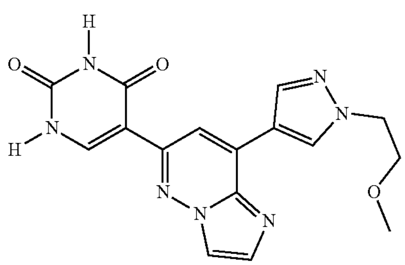 [SMILES: COCCn1cc(-c2cc(-c3c[nH]c(=O)[nH]c3=O)nn3ccnc23)cn1] | 5-(8-(1-(2-methoxyethyl)-1H-pyrazol-4-yl)imidazo[1,2-b]pyridazin-6-yl)pyrimidine-2,4(1H,3H)-dione |
| 511 | 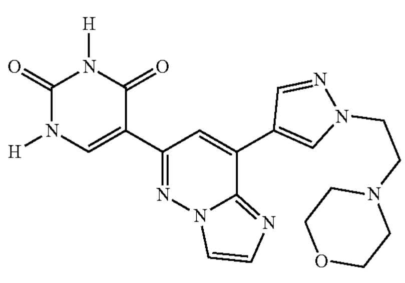 [SMILES: O=c1[nH]cc(-c2cc(-c3cnn(CCN4CCOCC4)c3)c3nccn3n2)c(=O)[nH]1] | 5-(8-(1-(2-morpholinoethyl)-1H-pyrazol-4-yl)imidazo[1,2-b]pyridazin-6-yl)pyrimidine-2,4(1H,3H)-dione |

TABLE 2-continued

| Ex. No. | Structure | IUPAC Name |
|---|---|---|
| 512 | 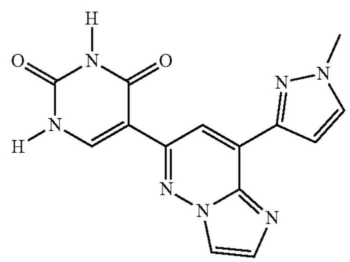 [SMILES: Cn1ccc(-c2cc(-c3c[nH]c(=O)[nH]c3=O)nn3ccnc23)n1] | 5-(8-(1-methyl-1H-pyrazol-3-yl)imidazo[1,2-b]pyridazin-6-yl)pyrimidine-2,4(1H,3H)-dione |
| 513 | 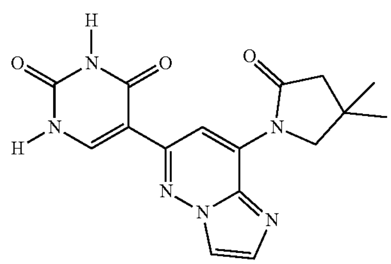 [SMILES: CC1(C)CC(=O)N(c2cc(-c3c[nH]c(=O)[nH]c3=O)nn3ccnc23)C1] | 5-(8-(4,4-dimethyl-2-oxopyrrolidin-1-yl)imidazo[1,2-b]pyridazin-6-yl)pyrimidine-2,4(1H,3H)-dione |
| 514 | 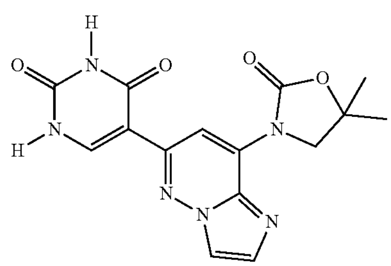 [SMILES: CC1(C)CN(c2cc(-c3c[nH]c(=O)[nH]c3=O)nn3ccnc23)C(=O)O1] | 5-(8-(5,5-dimethyl-2-oxooxazolidin-3-yl)imidazo[1,2-b]pyridazin-6-yl)pyrimidine-2,4(1H,3H)-dione |
| 515 | 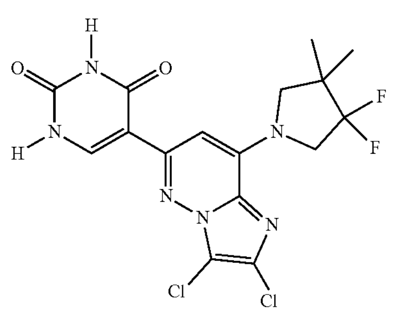 [SMILES: CC1(C)CN(c2cc(-c3c[nH]c(=O)[nH]c3=O)nn3c(Cl)c(Cl)nc23)CC1(F)F] | 5-(2,3-dichloro-8-(3,3-difluoro-4,4-dimethylpyrrolidin-1-yl)imidazo[1,2-b]pyridazin-6-yl)pyrimidine-2,4(1H,3H)-dione |
| 516 | 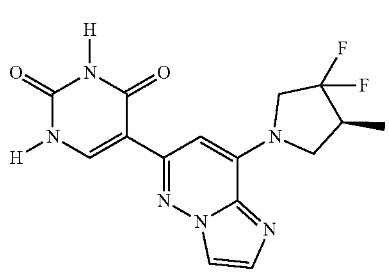 [SMILES: C[C@H]1CN(c2cc(-c3c[nH]c(=O)[nH]c3=O)nn3ccnc23)CC1(F)F] | (S)-5-(8-(3,3-difluoro-4-methylpyrrolidin-1-yl)imidazo[1,2-b]pyridazin-6-yl)pyrimidine-2,4(1H,3H)-dione |

TABLE 2-continued

| Ex. No. | Structure | IUPAC Name |
|---|---|---|
| 517 | 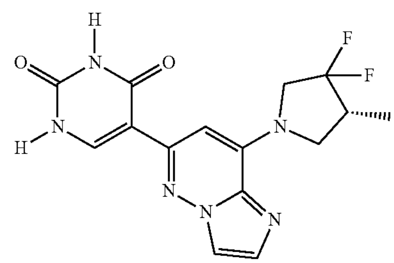 [SMILES: C[C@@H]1CN(c2cc(-c3c[nH]c(=O)[nH]c3=O)nn3ccnc23)CC1(F)F] | (R)-5-(8-(3,3-difluoro-4-methylpyrrolidin-1-yl)imidazo[1,2-b]pyridazin-6-yl)pyrimidine-2,4(1H,3H)-dione |
| 518 | 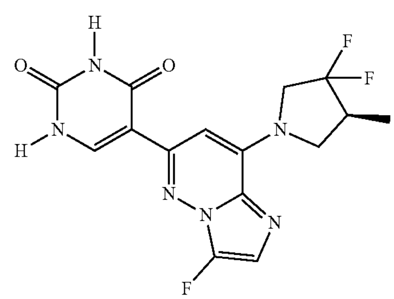 [SMILES: C[C@H]1CN(c2cc(-c3c[nH]c(=O)[nH]c3=O)nn3c(F)cnc23)CC1(F)F] | (S)-5-(8-(3,3-difluoro-4-methylpyrrolidin-1-yl)-3-fluoroimidazo[1,2-b]pyridazin-6-yl)pyrimidine-2,4(1H,3H)-dione |
| 519 | 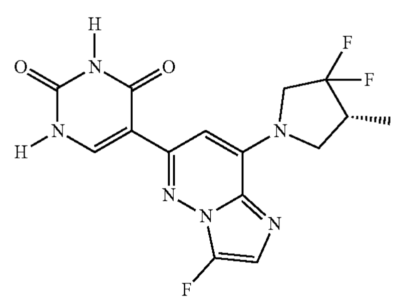 [SMILES: C[C@@H]1CN(c2cc(-c3c[nH]c(=O)[nH]c3=O)nn3c(F)cnc23)CC1(F)F] | (R)-5-(8-(3,3-difluoro-4-methylpyrrolidin-1-yl)-3-fluoroimidazo[1,2-b]pyridazin-6-yl)pyrimidine-2,4(1H,3H)-dione |
| 520 | 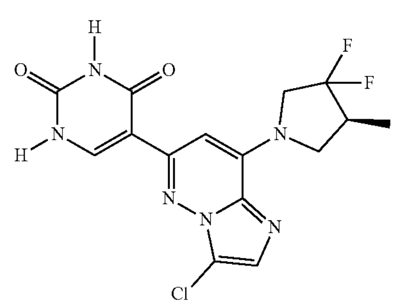 [SMILES: C[C@H]1CN(c2cc(-c3c[nH]c(=O)[nH]c3=O)nn3c(Cl)cnc23)CC1(F)F] | (S)-5-(3-chloro-8-(3,3-difluoro-4-methylpyrrolidin-1-yl)imidazo[1,2-b]pyridazin-6-yl)pyrimidine-2,4(1H,3H)-dione |
| 521 | 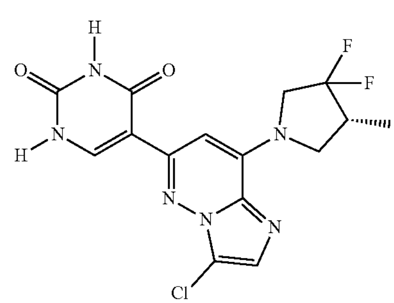 | (R)-5-(3-chloro-8-(3,3-difluoro-4-methylpyrrolidin-1-yl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 522 | 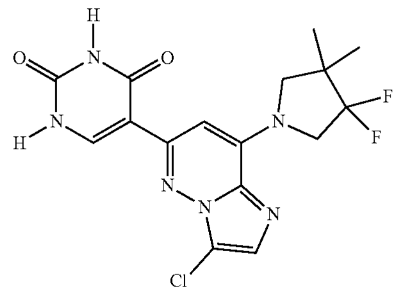 [SMILES: CC1(C)CN(c2cc(-c3c[nH]c(=O)[nH]c3=O)nn3c(Cl)cnc23)CC1(F)F] | 5-(3-chloro-8-(3,3-difluoro-4,4-dimethylpyrrolidin-1-yl)imidazo[1,2-b]pyridazin-6-yl)pyrimidine-2,4(1H,3H)-dione |
| 523 | 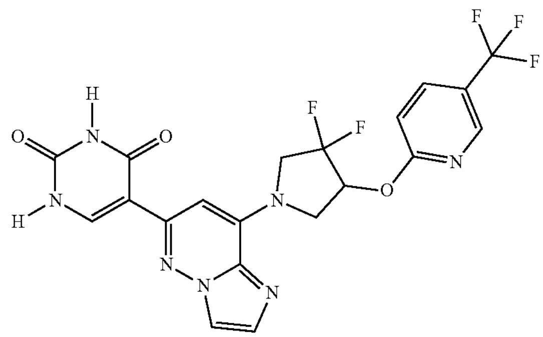 [SMILES: O=c1[nH]cc(-c2cc(N3CC(Oc4ccc(C(F)(F)F)cn4)C(F)(F)C3)c3nccn3n2)c(=O)[nH]1] | 5-(8-(3,3-difluoro-4-((5-(trifluoromethyl)pyridin-2-yl)oxy)pyrrolidin-1-yl)imidazo[1,2-b]pyridazin-6-yl)pyrimidine-2,4(1H,3H)-dione |
| 524 | 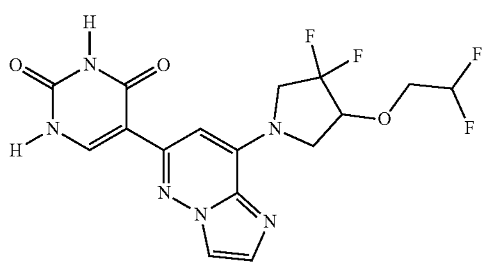 [SMILES: O=c1[nH]cc(-c2cc(N3CC(OCC(F)F)C(F)(F)C3)c3nccn3n2)c(=O)[nH]1] | 5-(8-(4-(2,2-difluoroethoxy)-3,3-difluoropyrrolidin-1-yl)imidazo[1,2-b]pyridazin-6-yl)pyrimidine-2,4(1H,3H)-dione |
| 525 | 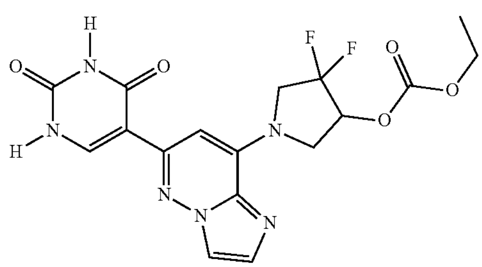 [SMILES: CCOC(=O)OC1CN(c2cc(-c3c[nH]c(=O)[nH]c3=O)nn3ccnc23)CC1(F)F] | 1-(6-(2,4-dioxo-1,2,3,4-tetrahydropyrimidin-5-yl)imidazo[1,2-b]pyridazin-8-yl)-4,4-difluoropyrrolidin-3-yl ethyl carbonate |
| 526 | 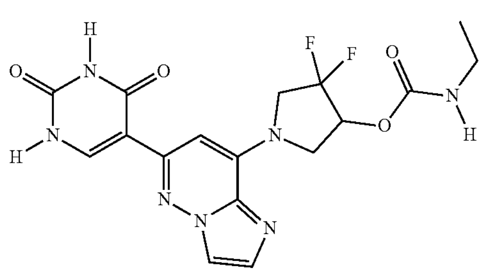 [SMILES: CCNC(=O)OC1CN(c2cc(-c3c[nH]c(=O)[nH]c3=O)nn3ccnc23)CC1(F)F] | 1-(6-(2,4-dioxo-1,2,3,4-tetrahydropyrimidin-5-yl)imidazo[1,2-b]pyridazin-8-yl)-4,4-difluoropyrrolidin-3-yl ethylcarbamate |

TABLE 2-continued

| Ex. No. | Structure | IUPAC Name |
|---|---|---|
| 527 | 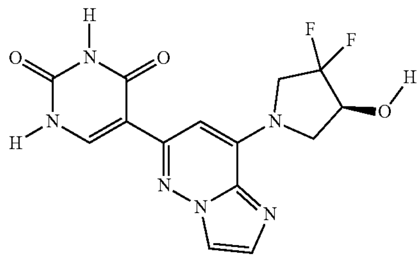 [SMILES: O=c1[nH]cc(-c2cc(N3C[C@H](O)C(F)(F)C3)c3nccn3n2)c(=O)[nH]1] | (S)-5-(8-(3,3-difluoro-4-hydroxypyrrolidin-1-yl)imidazo[1,2-b]pyridazin-6-yl)pyrimidine-2,4(1H,3H)-dione |
| 528 | 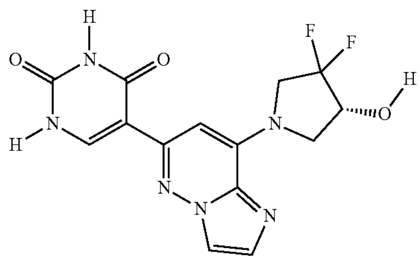 [SMILES: O=c1[nH]cc(-c2cc(N3C[C@@H](O)C(F)(F)C3)c3nccn3n2)c(=O)[nH]1] | (R)-5-(8-(3,3-difluoro-4-hydroxypyrrolidin-1-yl)imidazo[1,2-b]pyridazin-6-yl)pyrimidine-2,4(1H,3H)-dione |
| 529 | 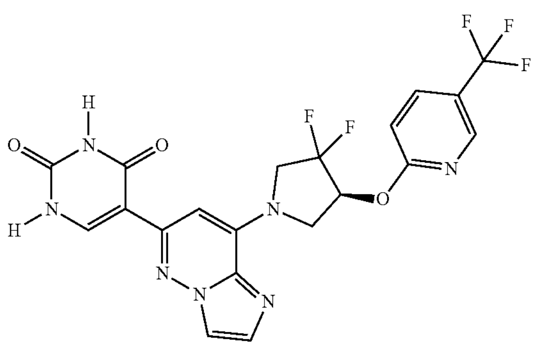 [SMILES: O=c1[nH]cc(-c2cc(N3C[C@H](Oc4ccc(C(F)(F)F)cn4)C(F)(F)C3)c3nccn3n2)c(=O)[nH]1] | (S)-5-(8-(3,3-difluoro-4-((5-(trifluoromethyl)pyridin-2-yl)oxy)pyrrolidin-1-yl)imidazo[1,2-b]pyridazin-6-yl)pyrimidine-2,4(1H,3H)-dione |
| 530 | 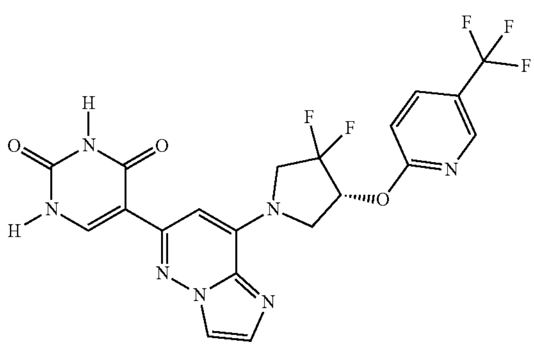 [SMILES: O=c1[nH]cc(-c2cc(N3C[C@@H](Oc4ccc(C(F)(F)F)cn4)C(F)(F)C3)c3nccn3n2)c(=O)[nH]1] | (R)-5-(8-(3,3-difluoro-4-((5-(trifluoromethyl)pyridin-2-yl)oxy)pyrrolidin-1-yl)imidazo[1,2-b]pyridazin-6-yl)pyrimidine-2,4(1H,3H)-dione |
| 531 | 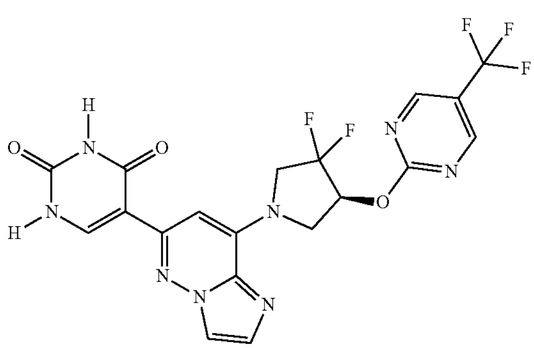 [SMILES: O=c1[nH]cc(-c2cc(N3C[C@H](Oc4ncc(C(F)(F)F)cn4)C(F)(F)C3)c3nccn3n2)c(=O)[nH]1] | (S)-5-(8-(3,3-difluoro-4-((5-(trifluoromethyl)pyrimidin-2-yl)oxy)pyrrolidin-1-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 532 | 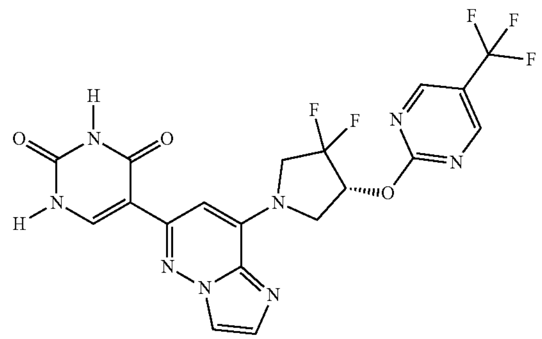 [SMILES: O=c1[nH]cc(-c2cc(N3C[C@@H](Oc4ncc(C(F)(F)F)cn4)C(F)(F)C3)c3nccn3n2)c(=O)[nH]1] | (R)-5-(8-(3,3-difluoro-4-((5-(trifluoromethyl)pyrimidin-2-yl)oxy)pyrrolidin-1-yl)imidazo[1,2-b]pyridazin-6-yl)pyrimidine-2,4(1H,3H)-dione |
| 533 | 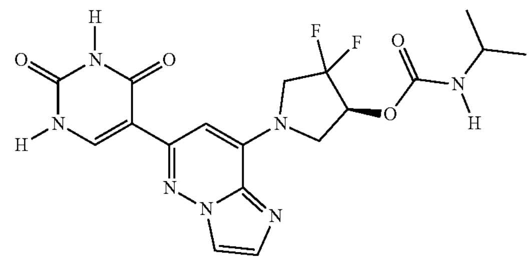 [SMILES: CC(C)NC(=O)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl isopropylcarbamate |
| 534 | 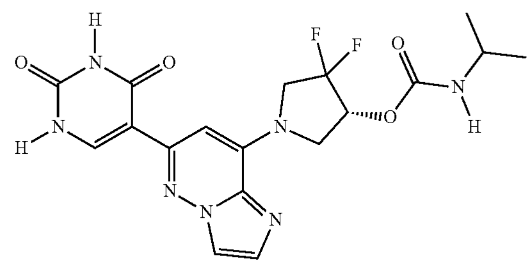 [SMILES: CC(C)NC(=O)O[C@@H]1CN(c2cc(-c3c[nH]c(=O)[nH]c3=O)nn3ccnc23)CC1(F)F] | (R)-1-(6-(2,4-dioxo-1,2,3,4-tetrahydropyrimidin-5-yl)imidazo[1,2-b]pyridazin-8-yl)-4,4-difluoropyrrolidin-3-yl isopropylcarbamate |
| 535 | 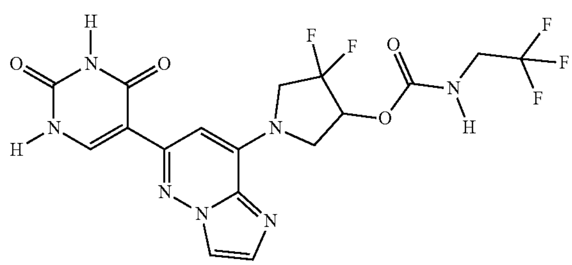 [SMILES: O=C(NCC(F)(F)F)OC1CN(c2cc(-c3c[nH]c(=O)[nH]c3=O)nn3ccnc23)CC1(F)F] | 1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl)carbamate |
| 536 | 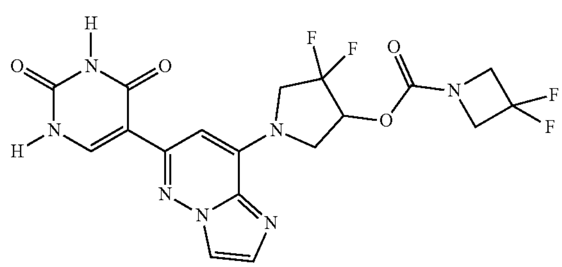 [SMILES: O=C(OC1CN(c2cc(-c3c[nH]c(=O)[nH]c3=O)nn3ccnc23)CC1(F)F)N1CC(F)(F)C1] | 1-(6-(2,4-dioxo-1,2,3,4-tetrahydropyrimidin-5-yl)imidazo[1,2-b]pyridazin-8-yl)-4,4-difluoropyrrolidin-3-yl 3,3-difluoroazetidine-1-carboxylate |

TABLE 2-continued

| Ex. No. | Structure | IUPAC Name |
| --- | --- | --- |
| 537 | 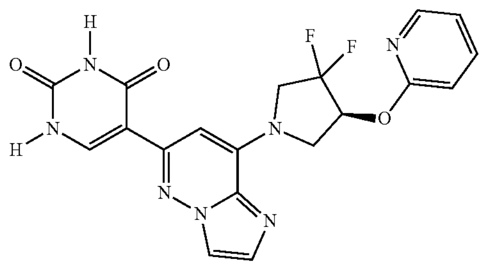 [SMILES: O=c1[nH]cc(-c2cc(N3C[C@H](Oc4ccccn4)C(F)(F)C3)c3nccn3n2)c(=O)[nH]1] | (S)-5-(8-(3,3-difluoro-4-(pyridin-2-yloxy)pyrrolidin-1-yl)imidazo[1,2-b]pyridazin-6-yl)pyrimidine-2,4(1H,3H)-dione |
| 538 | 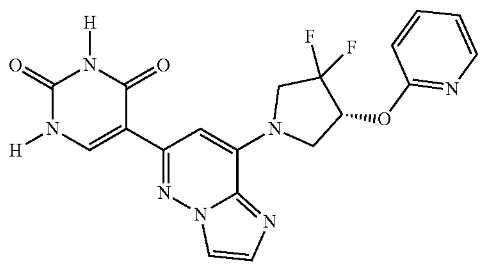 [SMILES: O=c1[nH]cc(-c2cc(N3C[C@@H](Oc4ccccn4)C(F)(F)C3)c3nccn3n2)c(=O)[nH]1] | (R)-5-(8-(3,3-difluoro-4-(pyridin-2-yloxy)pyrrolidin-1-yl)imidazo[1,2-b]pyridazin-6-yl)pyrimidine-2,4(1H,3H)-dione |
| 539 | 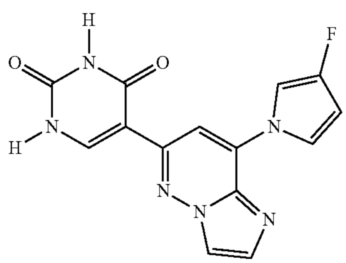 [SMILES: O=c1[nH]cc(-c2cc(-n3ccc(F)c3)c3nccn3n2)c(=O)[nH]1] | 5-(8-(3-fluoro-1H-pyrrol-1-yl)imidazo[1,2-b]pyridazin-6-yl)pyrimidine-2,4(1H,3H)-dione |
| 540 | 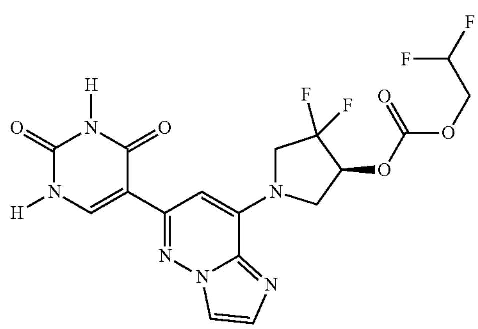 [SMILES: O=C(OCC(F)F)O[C@H]1CN(c2cc(-c3c[nH]c(=O)[nH]c3=O)nn3ccnc23)CC1(F)F] | (S)-2,2-difluoroethyl (1-(6-(2,4-dioxo-1,2,3,4-tetrahydropyrimidin-5-yl)imidazo[1,2-b]pyridazin-8-yl)-4,4-difluoropyrrolidin-3-yl) carbonate |
| 541 | 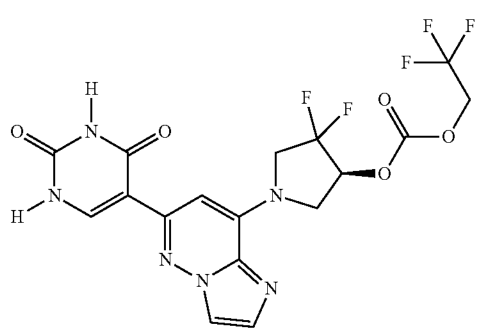 [SMILES: O=C(OCC(F)(F)F)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl) carbonate |

TABLE 2-continued

| Ex. No. | Structure | IUPAC Name |
|---|---|---|
| 542 | 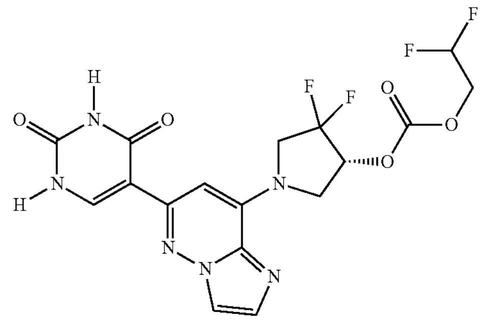 [SMILES: O=C(OCC(F)F)O[C@@H]1CN(c2cc(-c3c[nH]c(=O)[nH]c3=O)nn3ccnc23)CC1(F)F] | (R)-2,2-difluoroethyl (1-(6-(2,4-dioxo-1,2,3,4-tetrahydropyrimidin-5-yl)imidazo[1,2-b]pyridazin-8-yl)-4,4-difluoropyrrolidin-3-yl) carbonate |
| 543 | 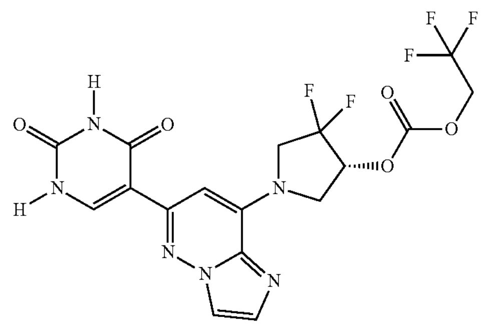 [SMILES: O=C(OCC(F)(F)F)O[C@@H]1CN(c2cc(-c3c[nH]c(=O)[nH]c3=O)nn3ccnc23)CC1(F)F] | (R)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl) carbonate |
| 544 | 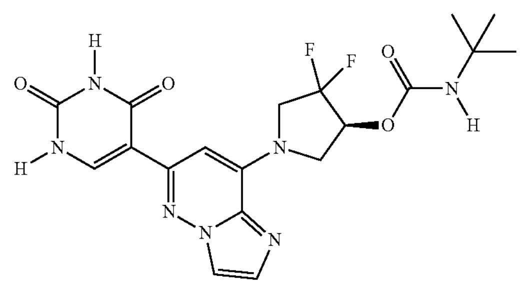 [SMILES: CC(C)(C)NC(=O)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl tert-butylcarbamate |
| 545 | 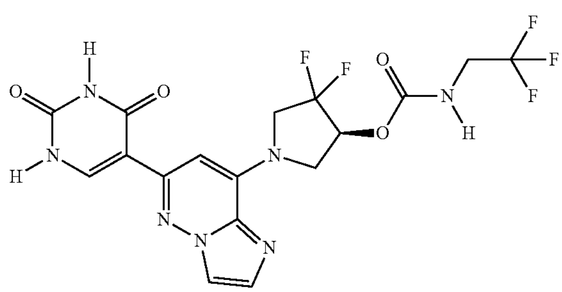 [SMILES: O=C(NCC(F)(F)F)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl (2,2,2-trifluoroethyl)carbamate |
| 546 | 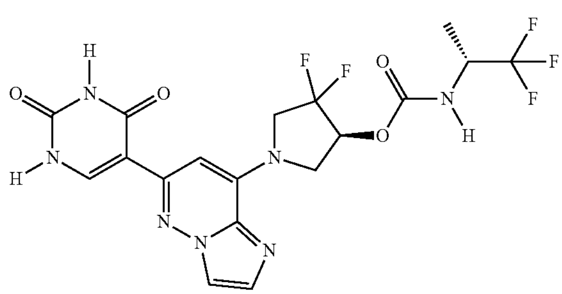 [SMILES: C[C@@H](NC(=O)O[C@H]1CN(c2cc(-c3c[nH]c(=O)[nH]c3=O)nn3ccnc23)CC1(F)F)C(F)(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl ((R)-1,1,1-trifluoropropan-2-yl)carbamate |

TABLE 2-continued

| Ex. No. | Structure | IUPAC Name |
|---|---|---|
| 547 | 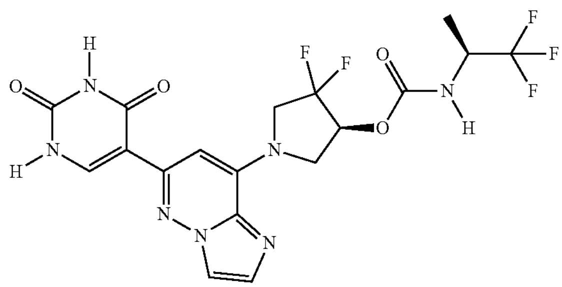 [SMILES: C[C@H](NC(=O)O[C@H]1CN(c2cc(-c3c[nH]c(=O)[nH]c3=O)nn3ccnc23)CC1(F)F)C(F)(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl ((S)-1,1,1-trifluoropropan-2-yl)carbamate |
| 548 | 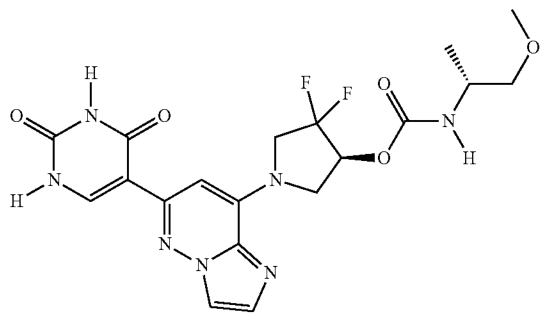 [SMILES: COC[C@@H](C)NC(=O)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl ((R)-1-methoxypropan-2-yl)carbamate |
| 549 | 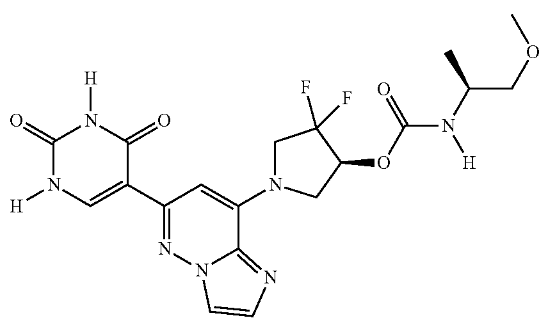 [SMILES: COC[C@H](C)NC(=O)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl ((S)-1-methoxypropan-2-yl)carbamate |
| 550 | 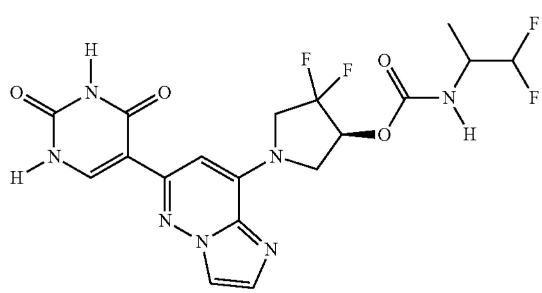 [SMILES: CC(NC(=O)O[C@H]1CN(c2cc(-c3c[nH]c(=O)[nH]c3=O)nn3ccnc23)CC1(F)F)C(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl (1,1-difluoropropan-2-yl)carbamate |
| 551 | 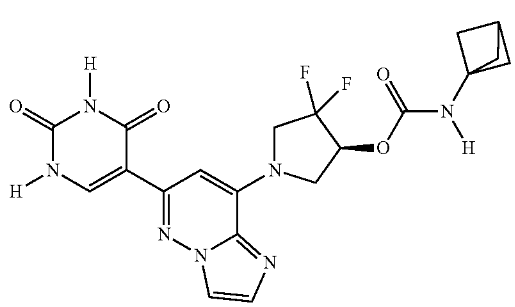 [SMILES: O=C(NC12CC(C1)C2)O[C@H]1CN(c2cc(-c3c[nH]c(=O)[nH]c3=O)nn3ccnc23)CC1(F)F] | (S)-1-(6-(2,4-dioxo-1,2,3,4-tetrahydropyrimidin-5-yl)imidazo[1,2-b]pyridazin-8-yl)-4,4-difluoropyrrolidin-3-yl bicyclo[1.1.1]pentan-1-ylcarbamate |

TABLE 2-continued

| Ex. No. | Structure | IUPAC Name |
| --- | --- | --- |
| 552 | 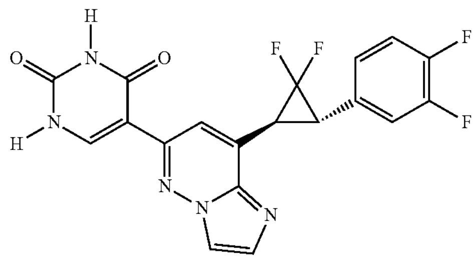 [SMILES: O=c1[nH]cc(-c2cc([C@@H]3[C@@H](c4ccc(F)c(F)c4)C3(F)F)c3nccn3n2)c(=O)[nH]1] | 5-(8-((1S,3S)-3-(3,4-difluorophenyl)-2,2-difluorocyclopropyl)imidazo[1,2-b]pyridazin-6-yl)pyrimidine-2,4(1H,3H)-dione |
| 553 | 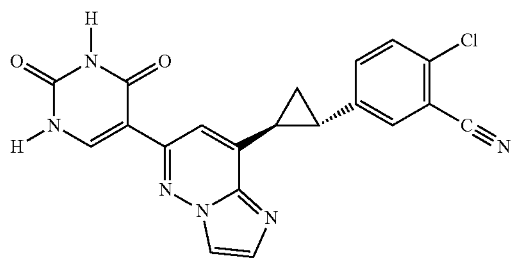 [SMILES: N#Cc1cc([C@H]2C[C@@H]2c2cc(-c3c[nH]c(=O)[nH]c3=O)nn3ccnc23)ccc1Cl] | 2-chloro-5-((1S,2S)-2-(6-(2,4-dioxo-1,2,3,4-tetrahydropyrimidin-5-yl)imidazo[1,2-b]pyridazin-8-yl)cyclopropyl)benzonitrile |
| 554 | 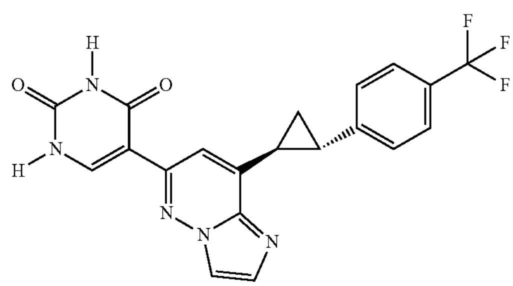 [SMILES: O=c1[nH]cc(-c2cc([C@H]3C[C@@H]3c3ccc(C(F)(F)F)cc3)c3nccn3n2)c(=O)[nH]1] | 5-(8-((1S,2S)-2-(4-(trifluoromethyl)phenyl)cyclopropyl)imidazo[1,2-b]pyridazin-6-yl)pyrimidine-2,4(1H,3H)-dione |
| 555 | 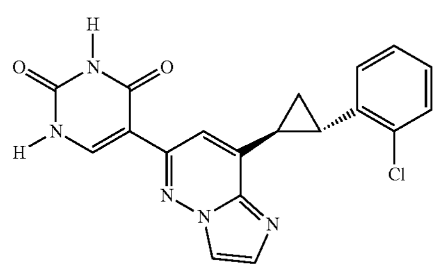 | 5-(8-((1S,2S)-2-(2-chlorophenyl)cyclopropyl)imidazo[1,2-b]pyridazin-6-yl)pyrimidine-2,4(1H,3H)-dione |
| 556 | 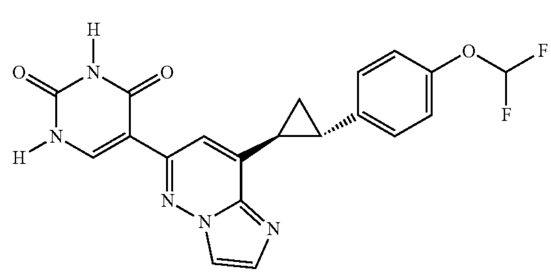 [SMILES: O=c1[nH]cc(-c2cc([C@H]3C[C@@H]3c3ccc(OC(F)F)cc3)c3nccn3n2)c(=O)[nH]1] | 5-(8-((1S,2S)-2-(4-(difluoromethoxy)phenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 557 | 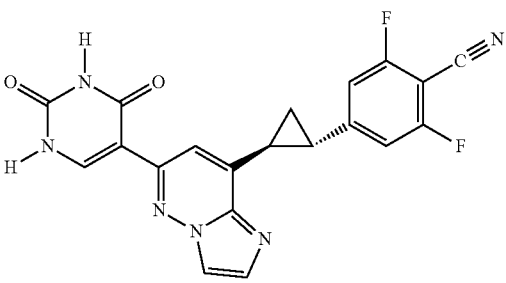 [SMILES: N#Cc1c(F)cc([C@H]2C[C@@H]2c2cc(-c3c[nH]c(=O)[nH]c3=O)nn3ccnc23)cc1F] | 4-((1S,2S)-2-(6-(2,4-dioxo-1,2,3,4-tetrahydropyrimidin-5-yl)imidazo[1,2-b]pyridazin-8-yl)cyclopropyl)-2,6-difluorobenzonitrile |
| 558 | 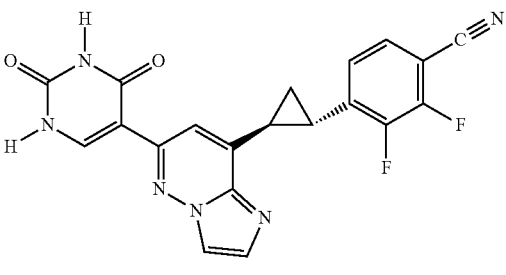 [SMILES: N#Cc1ccc([C@H]2C[C@@H]2c2cc(-c3c[nH]c(=O)[nH]c3=O)nn3ccnc23)c(F)c1F] | 4-((1S,2S)-2-(6-(2,4-dioxo-1,2,3,4-tetrahydropyrimidin-5-yl)imidazo[1,2-b]pyridazin-8-yl)cyclopropyl)-2,3-difluorobenzonitrile |
| 559 | 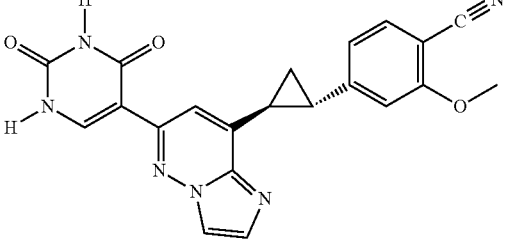 | 4-((1S,2S)-2-(6-(2,4-dioxo-1,2,3,4-tetrahydropyrimidin-5-yl)imidazo[1,2-b]pyridazin-8-yl)cyclopropyl)-2-methoxybenzonitrile |
| 560 | 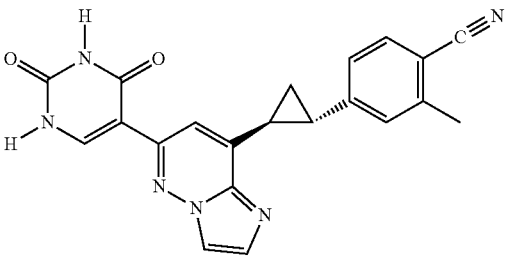 | 4-((1S,2S)-2-(6-(2,4-dioxo-1,2,3,4-tetrahydropyrimidin-5-yl)imidazo[1,2-b]pyridazin-8-yl)cyclopropyl)-2-methylbenzonitrile |
| 561 | 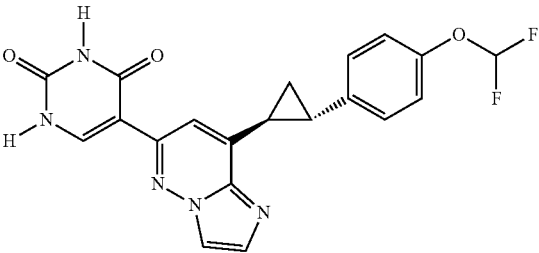 [SMILES: O=c1[nH]cc(-c2cc([C@H]3C[C@@H]3c3ccc(OC(F)F)cc3)c3nccn3n2)c(=O)[nH]1] | 5-(8-((1S,2S)-2-(4-(difluoromethoxy)phenyl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 562 | 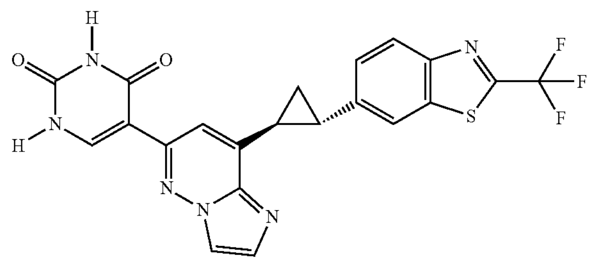 [SMILES: O=c1[nH]cc(-c2cc([C@H]3C[C@@H]3c3ccc4nc(C(F)(F)F)sc4c3)c3nccn3n2)c(=O)[nH]1] | 5-(8-((1S,2S)-2-(2-(trifluoromethyl)benzo[d]thiazol-6-yl)cyclopropyl)imidazo[1,2-b]pyridazin-6-yl)pyrimidine-2,4(1H,3H)-dione |
| 563 | 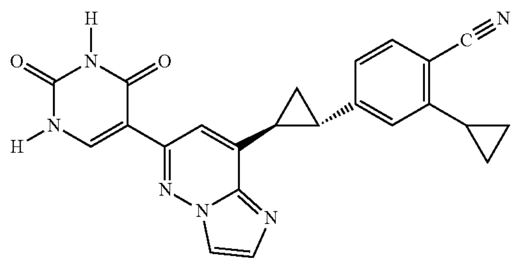 [SMILES: N#Cc1ccc([C@H]2C[C@@H]2c2cc(-c3c[nH]c(=O)[nH]c3=O)nn3ccnc23)cc1C1CC1] | 2-cyclopropyl-4-((1S,2S)-2-(6-(2,4-dioxo-1,2,3,4-tetrahydropyrimidin-5-yl)imidazo[1,2-b]pyridazin-8-yl)cyclopropyl)benzonitrile |
| 564 | 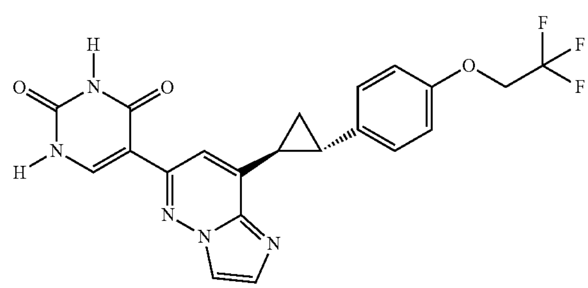 [SMILES: O=c1[nH]cc(-c2cc([C@H]3C[C@@H]3c3ccc(OCC(F)(F)F)cc3)c3nccn3n2)c(=O)[nH]1] | 5-(8-((1S,2S)-2-(4-(2,2,2-trifluoroethoxy)phenyl)cyclopropyl)imidazo[1,2-b]pyridazin-6-yl)pyrimidine-2,4(1H,3H)-dione |
| 565 | 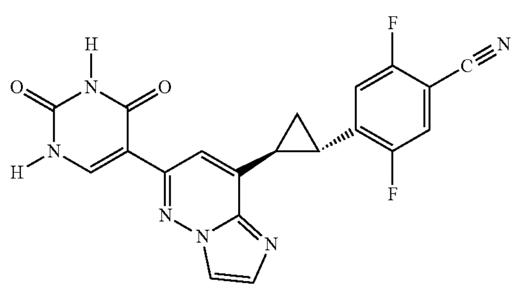 [SMILES: N#Cc1cc(F)c([C@H]2C[C@@H]2c2cc(-c3c[nH]c(=O)[nH]c3=O)nn3ccnc23)cc1F] | 4-((1S,2S)-2-(6-(2,4-dioxo-1,2,3,4-tetrahydropyrimidin-5-yl)imidazo[1,2-b]pyridazin-8-yl)cyclopropyl)-2,5-difluorobenzonitrile |
| 566 | 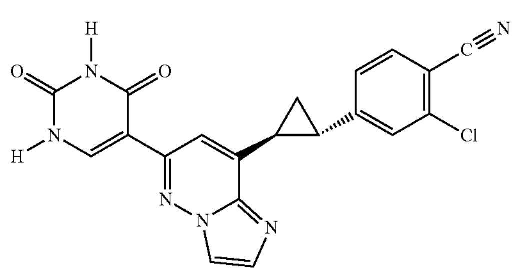 [SMILES: N#Cc1ccc([C@H]2C[C@@H]2c2cc(-c3c[nH]c(=O)[nH]c3=O)nn3ccnc23)cc1Cl] | 2-chloro-4-((1S,2S)-2-(6-(2,4-dioxo-1,2,3,4-tetrahydropyrimidin-5-yl)imidazo[1,2-b]pyridazin-8-yl)cyclopropyl)benzonitrile |

TABLE 2-continued

| Ex. No. | Structure | IUPAC Name |
| --- | --- | --- |
| 567 | 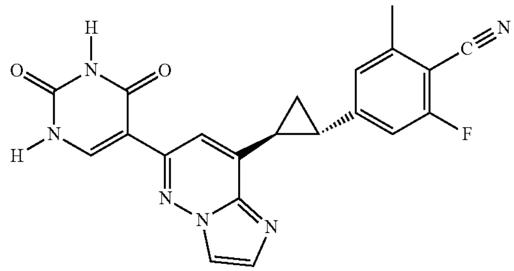 [SMILES: Cc1cc([C@H]2C[C@@H]2c2cc(-c3c[nH]c(=O)[nH]c3=O)nn3ccnc23)cc(F)c1C#N] | 4-((1S,2S)-2-(6-(2,4-dioxo-1,2,3,4-tetrahydropyrimidin-5-yl)imidazo[1,2-b]pyridazin-8-yl)cyclopropyl)-2-fluoro-6-methylbenzonitrile |
| 568 | 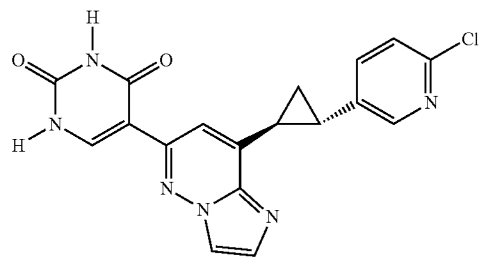 | 5-(8-((1S,2S)-2-(6-chloropyridin-3-yl)cyclopropyl)imidazo[1,2-b]pyridazin-6-yl)pyrimidine-2,4(1H,3H)-dione |
| 569 | 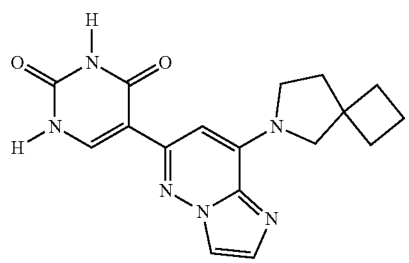 [SMILES: O=c1[nH]cc(-c2cc(N3CCC4(CCC4)C3)c3nccn3n2)c(=O)[nH]1] | 5-(8-(6-azaspiro[3.4]octan-6-yl)imidazo[1,2-b]pyridazin-6-yl)pyrimidine-2,4(1H,3H)-dione |
| 570 | 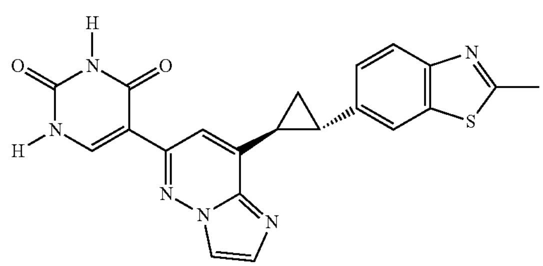 [SMILES: Cc1nc2ccc([C@H]3C[C@@H]3c3cc(-c4c[nH]c(=O)[nH]c4=O)nn4ccnc34)cc2s1] | 5-(8-((1S,2S)-2-(2-methylbenzo[d]thiazol-6-yl)cyclopropyl)imidazo[1,2-b]pyridazin-6-yl)pyrimidine-2,4(1H,3H)-dione |
| 571 | 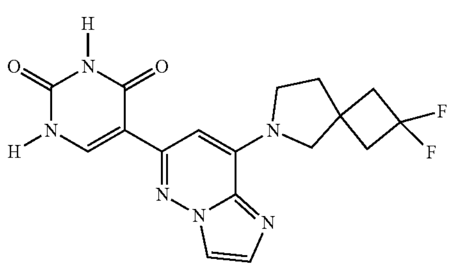 [SMILES: O=c1[nH]cc(-c2cc(N3CCC4(C3)CC(F)(F)C4)c3nccn3n2)c(=O)[nH]1] | 5-(8-(2,2-difluoro-6-azaspiro[3.4]octan-6-yl)imidazo[1,2-b]pyridazin-6-yl)pyrimidine-2,4(1H,3H)-dione |

TABLE 2-continued

| Ex. No. | Structure | IUPAC Name |
|---|---|---|
| 572 | 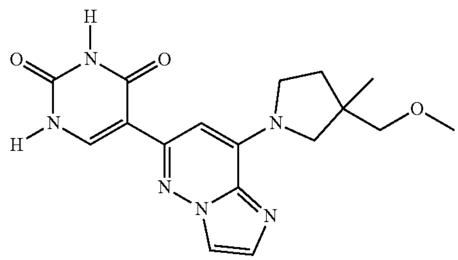 [SMILES: COCC1(C)CCN(c2cc(-c3c[nH]c(=O)[nH]c3=O)nn3ccnc23)C1] | 5-(8-(3-(methoxymethyl)-3-methylpyrrolidin-1-yl)imidazo[1,2-b]pyridazin-6-yl)pyrimidine-2,4(1H,3H)-dione |
| 573 | 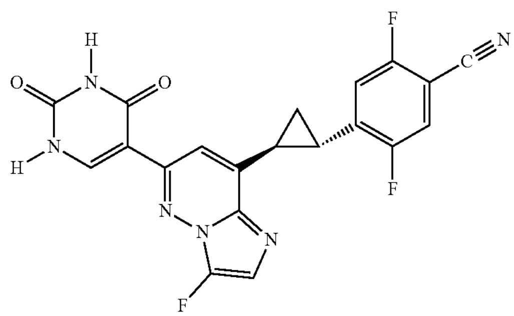 [SMILES: N#Cc1cc(F)c([C@H]2C[C@@H]2c2cc(-c3c[nH]c(=O)[nH]c3=O)nn3c(F)cnc23)cc1F] | 4-((1S,2S)-2-(6-(2,4-dioxo-1,2,3,4-tetrahydropyrimidin-5-yl)-3-fluoroimidazo[1,2-b]pyridazin-8-yl)cyclopropyl)-2,5-difluorobenzonitrile |
| 574 | 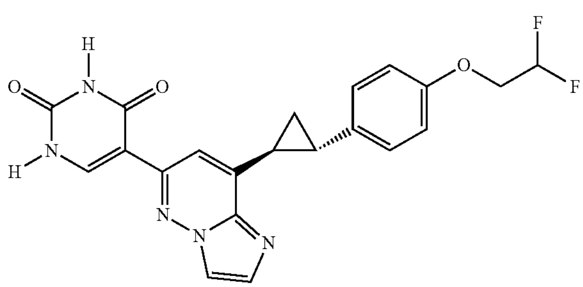 [SMILES: O=c1[nH]cc(-c2cc([C@H]3C[C@@H]3c3ccc(OCC(F)F)cc3)c3nccn3n2)c(=O)[nH]1] | 5-(8-((1S,2S)-2-(4-(2,2-difluoroethoxy)phenyl)cyclopropyl)imidazo[1,2-b]pyridazin-6-yl)pyrimidine-2,4(1H,3H)-dione |
| 575 | 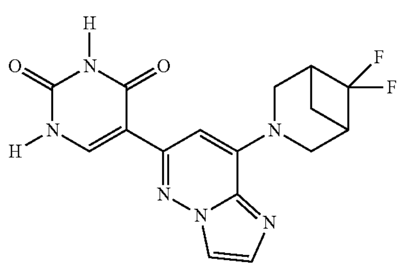 [SMILES: O=c1[nH]cc(-c2cc(N3CC4CC(C3)C4(F)F)c3nccn3n2)c(=O)[nH]1] | 5-(8-(6,6-difluoro-3-azabicyclo[3.1.1]heptan-3-yl)imidazo[1,2-b]pyridazin-6-yl)pyrimidine-2,4(1H,3H)-dione |
| 576 | 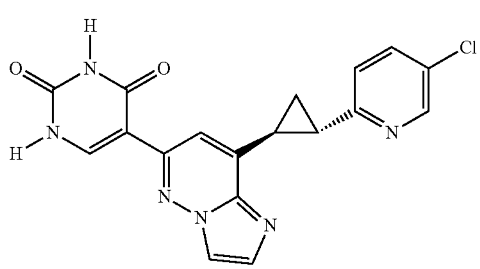 | 5-(8-((1S,2S)-2-(5-chloropyridin-2-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 577 | 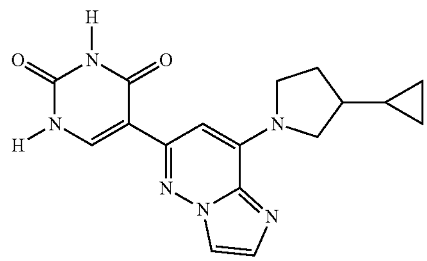 [SMILES: O=c1[nH]cc(-c2cc(N3CCC(C4CC4)C3)c3nccn3n2)c(=O)[nH]1] | 5-(8-(3-cyclopropylpyrrolidin-1-yl)imidazo[1,2-b]pyridazin-6-yl)pyrimidine-2,4(1H,3H)-dione |
| 578 | 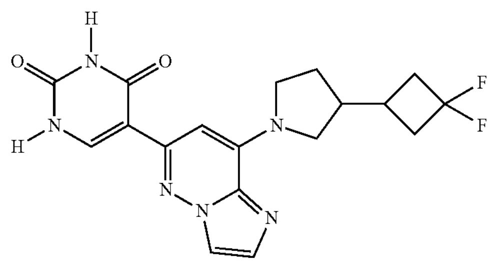 [SMILES: O=c1[nH]cc(-c2cc(N3CCC(C4CC(F)(F)C4)C3)c3nccn3n2)c(=O)[nH]1] | 5-(8-(3-(3,3-difluorocyclobutyl)pyrrolidin-1-yl)imidazo[1,2-b]pyridazin-6-yl)pyrimidine-2,4(1H,3H)-dione |
| 579 | 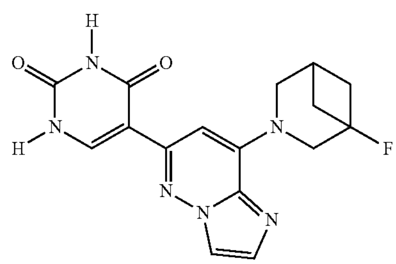 [SMILES: O=c1[nH]cc(-c2cc(N3CC4CC(F)(C4)C3)c3nccn3n2)c(=O)[nH]1] | 5-(8-(1-fluoro-3-azabicyclo[3.1.1]heptan-3-yl)imidazo[1,2-b]pyridazin-6-yl)pyrimidine-2,4(1H,3H)-dione |
| 580 | 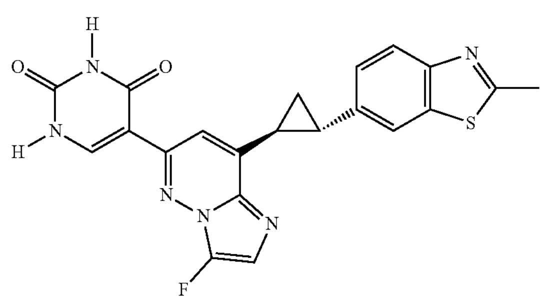 [SMILES: Cc1nc2ccc([C@H]3C[C@@H]3c3cc(-c4c[nH]c(=O)[nH]c4=O)nn4c(F)cnc34)cc2s1] | 5-(3-fluoro-8-((1S,2S)-2-(2-methylbenzo[d]thiazol-6-yl)cyclopropyl)imidazo[1,2-b]pyridazin-6-yl)pyrimidine-2,4(1H,3H)-dione |
| 581 | 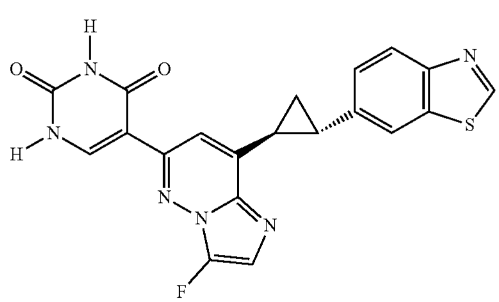 [SMILES: O=c1[nH]cc(-c2cc([C@H]3C[C@@H]3c3ccc4ncsc4c3)c3ncc(F)n3n2)c(=O)[nH]1] | 5-(8-((1S,2S)-2-(benzo[d]thiazol-6-yl)cyclopropyl)-3-fluoroimidazo[1,2-b]pyridazin-6-yl)pyrimidine-2,4(1H,3H)-dione |

TABLE 2-continued

| Ex. No. | Structure | IUPAC Name |
|---|---|---|
| 582 | 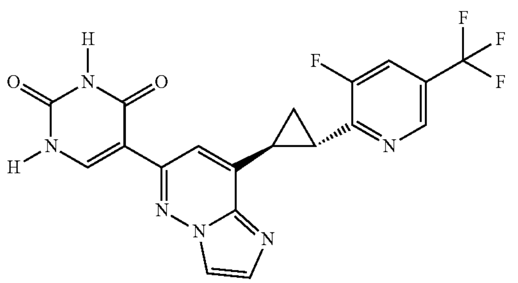 [SMILES: O=c1[nH]cc(-c2cc([C@H]3C[C@@H]3c3ncc(C(F)(F)F)cc3F)c3nccn3n2)c(=O)[nH]1] | 5-(8-((1S,2S)-2-(3-fluoro-5-(trifluoromethyl)pyridin-2-yl)cyclopropyl)imidazo[1,2-b]pyridazin-6-yl)pyrimidine-2,4(1H,3H)-dione |
| 583 | 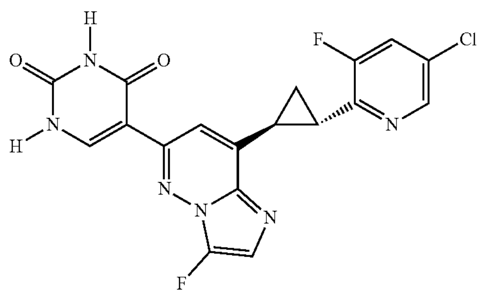 [SMILES: O=c1[nH]cc(-c2cc([C@H]3C[C@@H]3c3ncc(Cl)cc3F)c3ncc(F)n3n2)c(=O)[nH]1] | 5-(8-((1S,2S)-2-(5-chloro-3-fluoropyridin-2-yl)cyclopropyl)-3-fluoroimidazo[1,2-b]pyridazin-6-yl)pyrimidine-2,4(1H,3H)-dione |
| 584 | 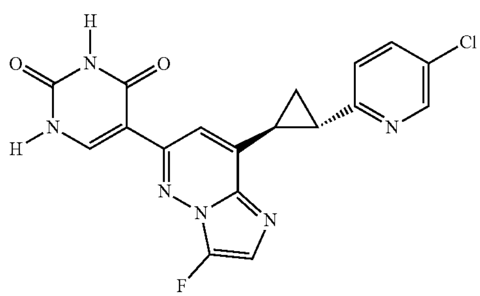 [SMILES: O=c1[nH]cc(-c2cc([C@H]3C[C@@H]3c3ccc(Cl)cn3)c3ncc(F)n3n2)c(=O)[nH]1] | 5-(8-((1S,2S)-2-(5-chloropyridin-2-yl)cyclopropyl)-3-fluoroimidazo[1,2-b]pyridazin-6-yl)pyrimidine-2,4(1H,3H)-dione |
| 585 | 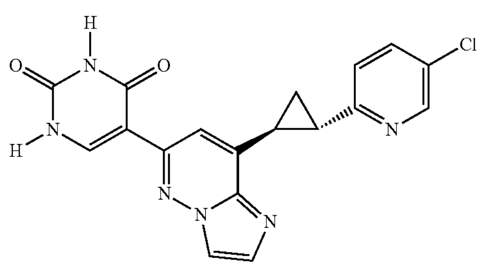 [SMILES: O=c1[nH]cc(-c2cc([C@H]3C[C@@H]3c3ccc(Cl)cn3)c3nccn3n2)c(=O)[nH]1] | 5-(8-((1S,2S)-2-(5-chloropyridin-2-yl)cyclopropyl)imidazo[1,2-b]pyridazin-6-yl)pyrimidine-2,4(1H,3H)-dione |
| 586 | 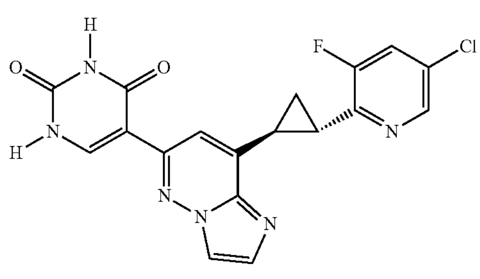 [SMILES: O=c1[nH]cc(-c2cc([C@H]3C[C@@H]3c3ncc(Cl)cc3F)c3nccn3n2)c(=O)[nH]1] | 5-(8-((1S,2S)-2-(5-chloro-3-fluoropyridin-2-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 587 | 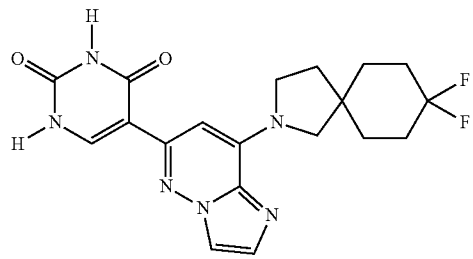 [SMILES: O=c1[nH]cc(-c2cc(N3CCC4(CCC(F)(F)CC4)C3)c3nccn3n2)c(=O)[nH]1] | 5-(8-(8,8-difluoro-2-azaspiro[4.5]decan-2-yl)imidazo[1,2-b]pyridazin-6-yl)pyrimidine-2,4(1H,3H)-dione |
| 588 | 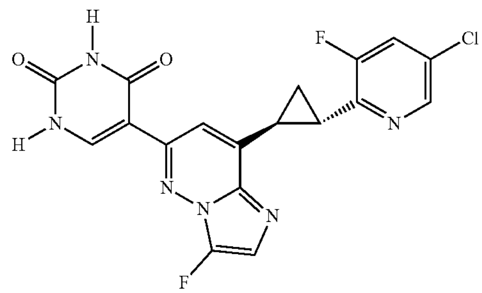 [SMILES: O=c1[nH]cc(-c2cc([C@H]3C[C@@H]3c3ncc(Cl)cc3F)c3ncc(F)n3n2)c(=O)[nH]1] | 5-(8-((1S,2S)-2-(5-chloro-3-fluoropyridin-2-yl)cyclopropyl)-3-fluoroimidazo[1,2-b]pyridazin-6-yl)pyrimidine-2,4(1H,3H)-dione |
| 589 | 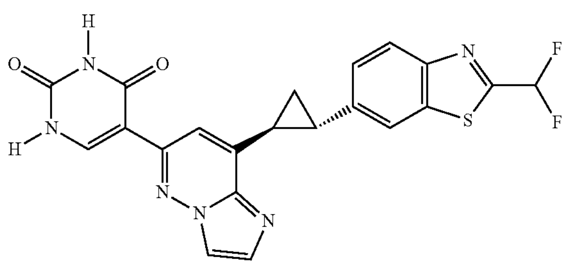 [SMILES: O=c1[nH]cc(-c2cc([C@H]3C[C@@H]3c3ccc4nc(C(F)F)sc4c3)c3nccn3n2)c(=O)[nH]1] | 5-(8-((1S,2S)-2-(2-(difluoromethyl)benzo[d]thiazol-6-yl)cyclopropyl)imidazo[1,2-b]pyridazin-6-yl)pyrimidine-2,4(1H,3H)-dione |
| 590 | 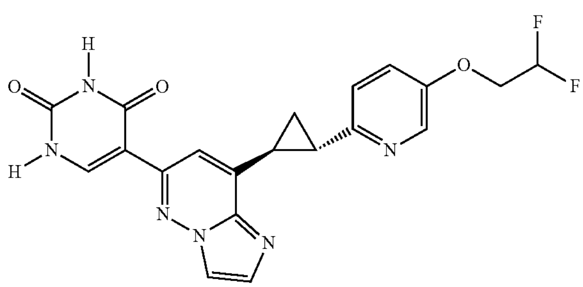 [SMILES: O=c1[nH]cc(-c2cc([C@H]3C[C@@H]3c3ccc(OCC(F)F)cn3)c3nccn3n2)c(=O)[nH]1] | 5-(8-((1S,2S)-2-(5-(2,2-difluoroethoxy)pyridin-2-yl)cyclopropyl)imidazo[1,2-b]pyridazin-6-yl)pyrimidine-2,4(1H,3H)-dione |
| 591 | 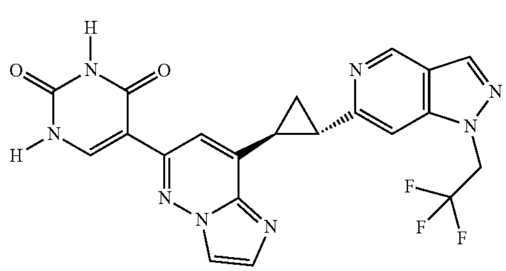 | 5-(8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 592 | 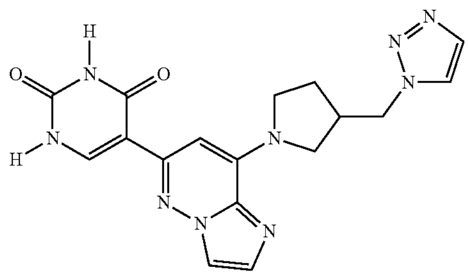 [SMILES: O=c1[nH]cc(-c2cc(N3CCC(Cn4ccnn4)C3)c3nccn3n2)c(=O)[nH]1] | 5-(8-(3-((1H-1,2,3-triazol-1-yl)methyl)pyrrolidin-1-yl)imidazo[1,2-b]pyridazin-6-yl)pyrimidine-2,4(1H,3H)-dione |
| 593 | 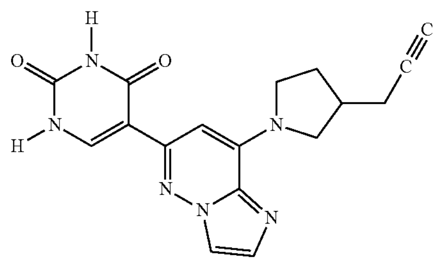 [SMILES: C#CCC1CCN(c2cc(-c3c[nH]c(=O)[nH]c3=O)nn3ccnc23)C1] | 5-(8-(3-(prop-2-yn-1-yl)pyrrolidin-1-yl)imidazo[1,2-b]pyridazin-6-yl)pyrimidine-2,4(1H,3H)-dione |
| 594 | 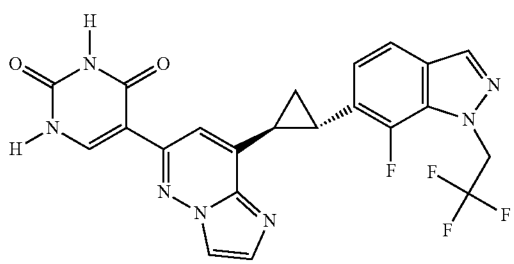 | 5-(8-((1S,2S)-2-(7-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 595 | 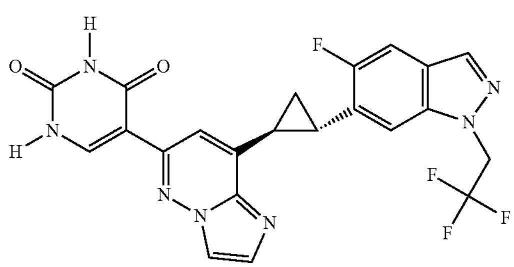 [SMILES: O=c1[nH]cc(-c2cc([C@H]3C[C@@H]3c3cc4c(cnn4CC(F)(F)F)cc3F)c3nccn3n2)c(=O)[nH]1] | 5-(8-((1S,2S)-2-(5-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 596 | 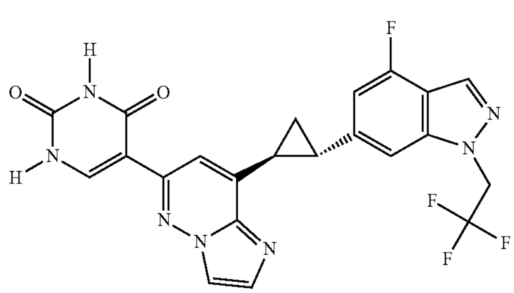 [SMILES: O=c1[nH]cc(-c2cc([C@H]3C[C@@H]3c3cc(F)c4cnn(CC(F)(F)F)c4c3)c3nccn3n2)c(=O)[nH]1] | 5-(8-((1S,2S)-2-(4-fluoro-1-(2,2,2-trifluoroethyl)-1H-indazol-6-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 597 | 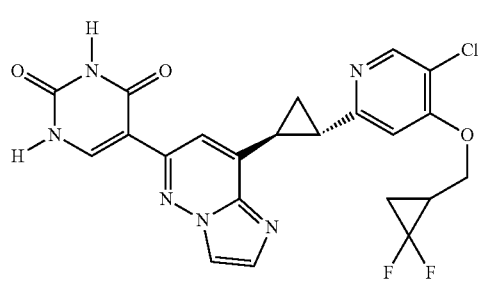 [SMILES: O=c1[nH]cc(-c2cc([C@H]3C[C@@H]3c3cc(OCC4CC4(F)F)c(Cl)cn3)c3nccn3n2)c(=O)[nH]1] | 5-(8-((1S,2S)-2-(5-chloro-4-((2,2-difluorocyclopropyl)methoxy)pyridin-2-yl)cyclopropyl)imidazo[1,2-b]pyridazin-6-yl)pyrimidine-2,4(1H,3H)-dione |
| 598 | 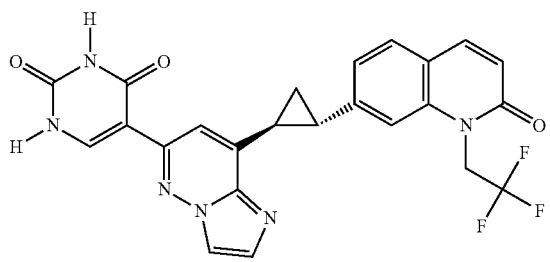 [SMILES: O=c1[nH]cc(-c2cc([C@H]3C[C@@H]3c3ccc4ccc(=O)n(CC(F)(F)F)c4c3)c3nccn3n2)c(=O)[nH]1] | 5-(8-((1S,2S)-2-(2-oxo-1-(2,2,2-trifluoroethyl)-1,2-dihydroquinolin-7-yl)cyclopropyl)imidazo[1,2-b]pyridazin-6-yl)pyrimidine-2,4(1H,3H)-dione |
| 599 | 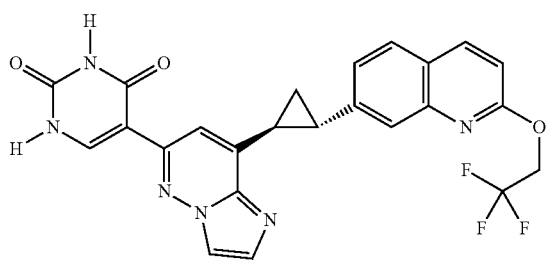 [SMILES: O=c1[nH]cc(-c2cc([C@H]3C[C@@H]3c3ccc4ccc(OCC(F)(F)F)nc4c3)c3nccn3n2)c(=O)[nH]1] | 5-(8-((1S,2S)-2-(2-(2,2,2-trifluoroethoxy)quinolin-7-yl)cyclopropyl)imidazo[1,2-b]pyridazin-6-yl)pyrimidine-2,4(1H,3H)-dione |
| 600 | 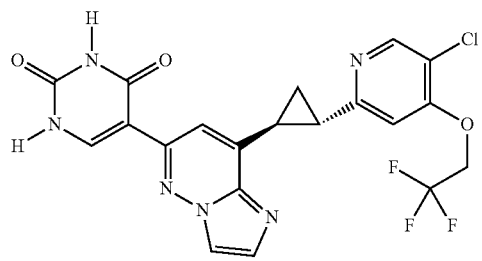 [SMILES: O=c1[nH]cc(-c2cc([C@H]3C[C@@H]3c3cc(OCC(F)(F)F)c(Cl)cn3)c3nccn3n2)c(=O)[nH]1] | 5-(8-((1S,2S)-2-(5-chloro-4-(2,2,2-trifluoroethoxy)pyridin-2-yl)cyclopropyl)imidazo[1,2-b]pyridazin-6-yl)pyrimidine-2,4(1H,3H)-dione |
| 601 | 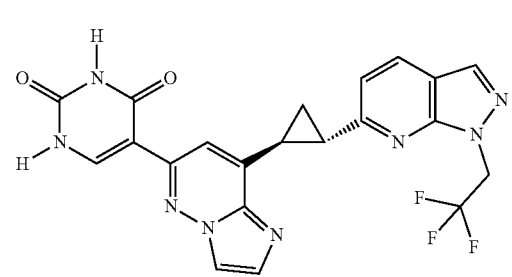 [SMILES: O=c1[nH]cc(-c2cc([C@H]3C[C@@H]3c3ccc4cnn(CC(F)(F)F)c4n3)c3nccn3n2)c(=O)[nH]1] | 5-(8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 602 | 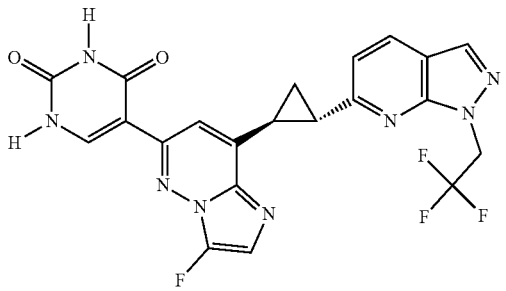 | 5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione |
| 603 | 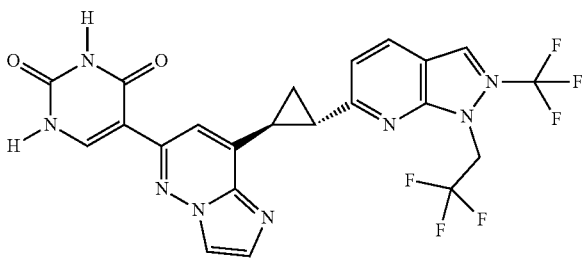 | 5-(8-((1S,2S)-2-(1-(2,2,2-trifluoroethyl)-2-(trifluoromethyl)-1H-benzo[d]imidazol-6-yl)cyclopropyl)imidazo[1,2-b]pyridazin-6-yl)pyrimidine-2,4(1H,3H)-dione |
| 604 | 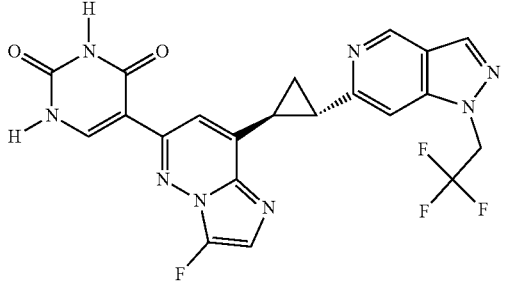 [SMILES: O=c1[nH]cc(-c2cc([C@H]3C[C@@H]3c3cc4c(cn3)cnn4CC(F)(F)F)c3ncc(F)n3n2)c(=O)[nH]1] | 5-(3-fluoro-8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |
| 605 | 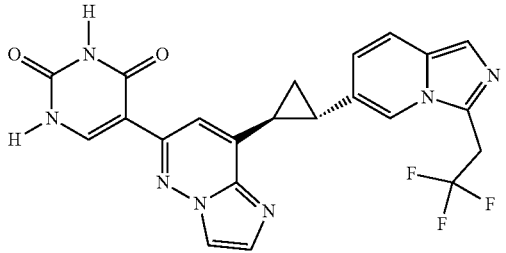 [SMILES: O=c1[nH]cc(-c2cc([C@H]3C[C@@H]3c3ccc4cnc(CC(F)(F)F)n4c3)c3nccn3n2)c(=O)[nH]1] | 5-(8-((1S,2S)-2-(3-(2,2,2-trifluoroethyl)imidazo[1,5-a]pyridin-6-yl)cyclopropyl)imidazo[1,2-b]pyridazin-6-yl)pyrimidine-2,4(1H,3H)-dione |
| 606 | 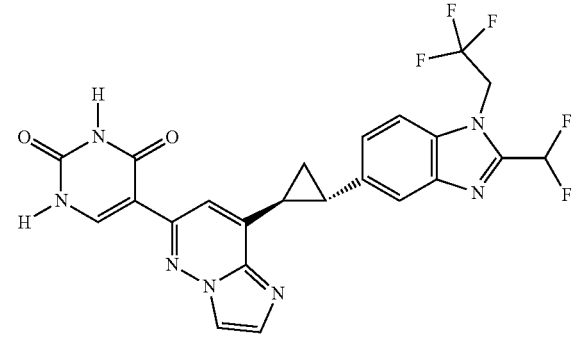 [SMILES: O=c1[nH]cc(-c2cc([C@H]3C[C@@H]3c3ccc4c(c3)nc(C(F)F)n4CC(F)(F)F)c3nccn3n2)c(=O)[nH]1] | 5-(8-((1S,2S)-2-(2-(difluoromethyl)-1-(2,2,2-trifluoroethyl)-1H-benzo[d]imidazol-5-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 607 | 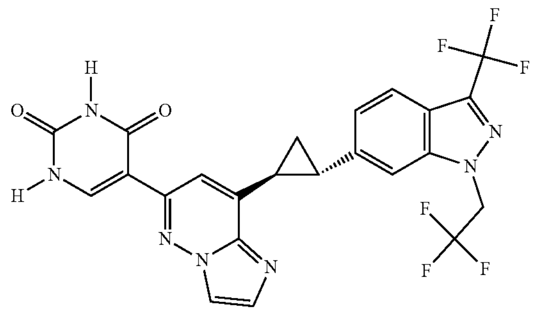 [SMILES: O=c1[nH]cc(-c2cc([C@H]3C[C@@H]3c3ccc4c(C(F)(F)F)nn(CC(F)(F)F)c4c3)c3nccn3n2)c(=O)[nH]1] | 5-(8-((1S,2S)-2-(1-(2,2,2-trifluoroethyl)-3-(trifluoromethyl)-1H-indazol-6-yl)cyclopropyl)imidazo[1,2-b]pyridazin-6-yl)pyrimidine-2,4(1H,3H)-dione |
| 608 | 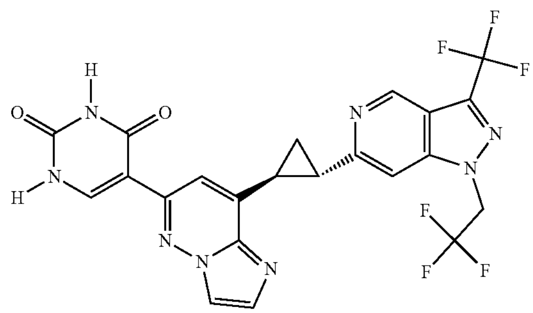 [SMILES: O=c1[nH]cc(-c2cc([C@H]3C[C@@H]3c3cc4c(cn3)c(C(F)(F)F)nn4CC(F)(F)F)c3nccn3n2)c(=O)[nH]1] | 5-(8-((1S,2S)-2-(1-(2,2,2-trifluoroethyl)-3-(trifluoromethyl)-1H-pyrazolo[4,3-c]pyridin-6-yl)cyclopropyl)imidazo[1,2-b]pyridazin-6-yl)pyrimidine-2,4(1H,3H)-dione |
| 609 | 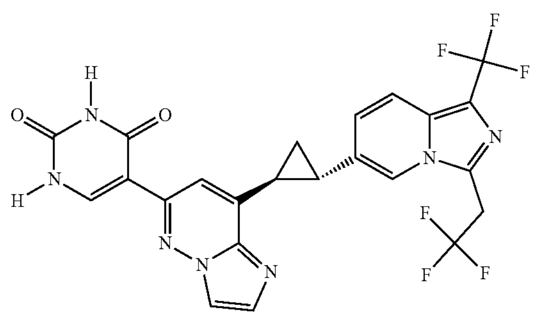 [SMILES: O=c1[nH]cc(-c2cc([C@H]3C[C@@H]3c3ccc4c(C(F)(F)F)nc(CC(F)(F)F)n4c3)c3nccn3n2)c(=O)[nH]1] | 5-(8-((1S,2S)-2-(3-(2,2,2-trifluoroethyl)-1-(trifluoromethyl)imidazo[1,5-a]pyridin-6-yl)cyclopropyl)imidazo[1,2-b]pyridazin-6-yl)pyrimidine-2,4(1H,3H)-dione |
| 610 | 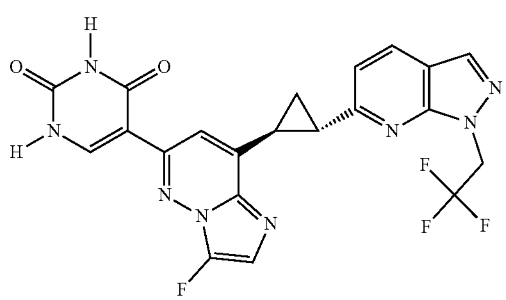 [SMILES: O=c1[nH]cc(-c2cc([C@H]3C[C@@H]3c3ccc4cnn(CC(F)(F)F)c4n3)c3ncc(F)n3n2)c(=O)[nH]1] | 5-(3-fluoro-8-((1S,2S)-2-(1-(2,2,2-trifluoroethyl)-1H-pyrazolo[3,4-b]pyridin-6-yl)cyclopropyl)imidazo[1,2-b]pyridazin-6-yl)pyrimidine-2,4(1H,3H)-dione |
| 611 | 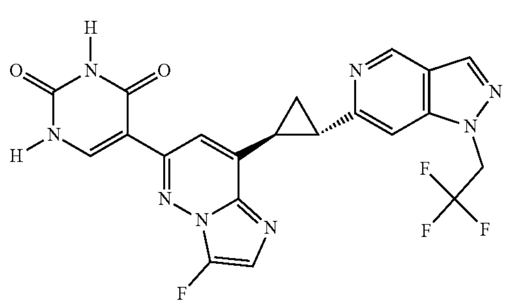 [SMILES: O=c1[nH]cc(-c2cc([C@H]3C[C@@H]3c3cc4c(cn3)cnn4CC(F)(F)F)c3ncc(F)n3n2)c(=O)[nH]1] | 5-(3-fluoro-8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 612 | 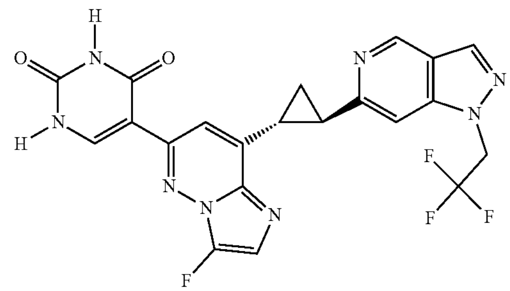 [SMILES: O=c1[nH]cc(-c2cc([C@@H]3C[C@H]3c3cc4c(cn3)cnn4CC(F)(F)F)c3ncc(F)n3n2)c(=O)[nH]1] | 5-(3-fluoro-8-((1R,2R)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |
| 613 | 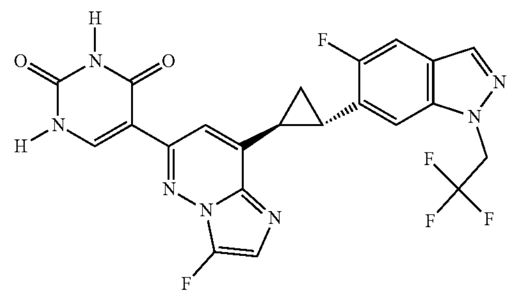 [SMILES: O=c1[nH]cc(-c2cc([C@H]3C[C@@H]3c3cc4c(cnn4CC(F)(F)F)cc3F)c3ncc(F)n3n2)c(=O)[nH]1] | 5-(3-fluoro-8-((1S,2S)-2-(5-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 614 | 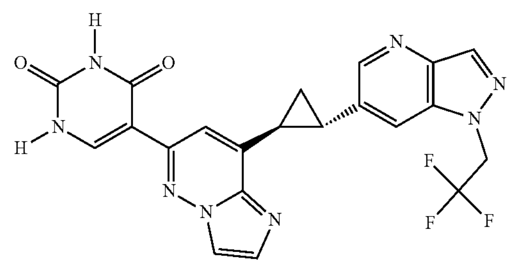 [SMILES: O=c1[nH]cc(-c2cc([C@H]3C[C@@H]3c3cnc4cnn(CC(F)(F)F)c4c3)c3nccn3n2)c(=O)[nH]1] | 5-(8-((1S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione |
| 615 | 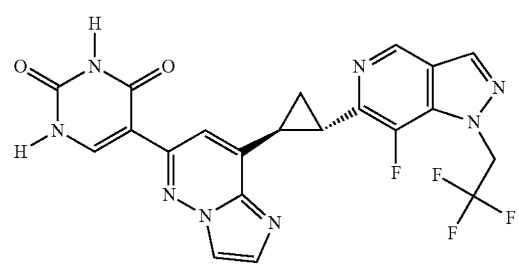 [SMILES: O=c1[nH]cc(-c2cc([C@H]3C[C@@H]3c3ncc4cnn(CC(F)(F)F)c4c3F)c3nccn3n2)c(=O)[nH]1] | 5-(8-((1S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |
| 616 | 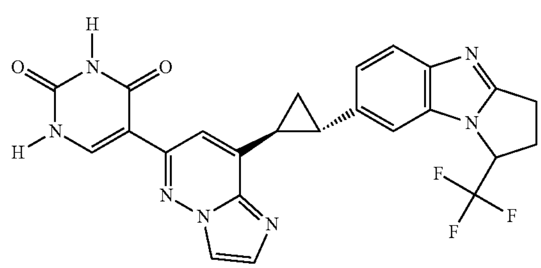 [SMILES: O=c1[nH]cc(-c2cc([C@H]3C[C@@H]3c3ccc4nc5n(c4c3)C(C(F)(F)F)CC5)c3nccn3n2)c(=O)[nH]1] | 5-(8-((1S,2S)-2-(1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 617 | 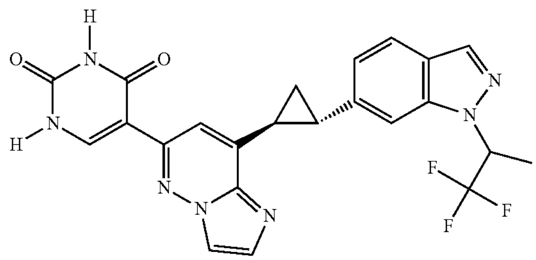 [SMILES: CC(n1ncc2ccc([C@H]3C[C@@H]3c3cc(-c4c[nH]c(=O)[nH]c4=O)nn4ccnc34)cc21)C(F)(F)F] | 5-(8-((1S,2S)-2-(1-(1,1,1-trifluoropropan-2-yl)-1H-indazol-6-yl)cyclopropyl)imidazo[1,2-b]pyridazin-6-yl)pyrimidine-2,4(1H,3H)-dione |
| 618 | 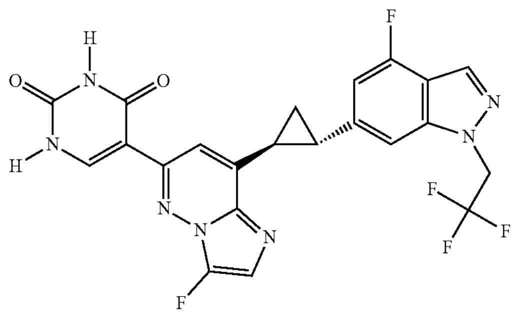 [SMILES: O=c1[nH]cc(-c2cc([C@H]3C[C@@H]3c3cc(F)c4cnn(CC(F)(F)F)c4c3)c3ncc(F)n3n2)c(=O)[nH]1] | 5-(3-fluoro-8-((1S,2S)-2-(4-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 619 | 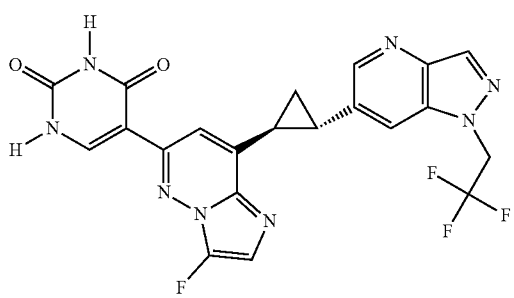 [SMILES: O=c1[nH]cc(-c2cc([C@H]3C[C@@H]3c3cnc4cnn(CC(F)(F)F)c4c3)c3ncc(F)n3n2)c(=O)[nH]1] | 5-(3-fluoro-8-((1S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione |
| 620 | 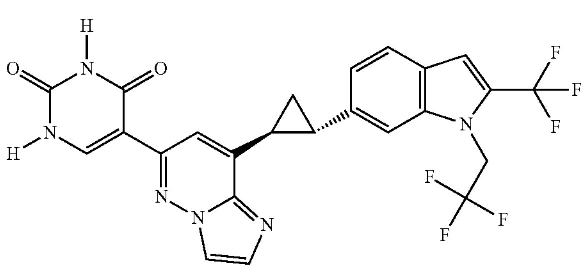 [SMILES: O=c1[nH]cc(-c2cc([C@H]3C[C@@H]3c3ccc4cc(C(F)(F)F)n(CC(F)(F)F)c4c3)c3nccn3n2)c(=O)[nH]1] | 5-(8-((1S,2S)-2-(1-(2,2,2-trifluoroethyl)-2-(trifluoromethyl)-1H-benzo[d]imidazol-6-yl)cyclopropyl)imidazo[1,2-b]pyridazin-6-yl)pyrimidine-2,4(1H,3H)-dione |
| 621 | 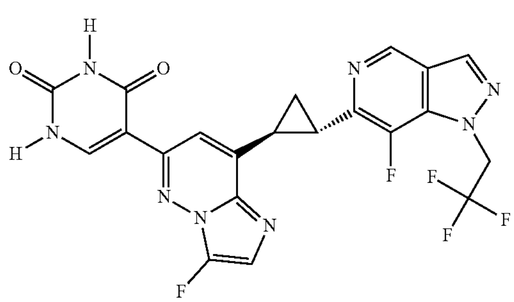 | 5-(3-fluoro-8-((1S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 622 | 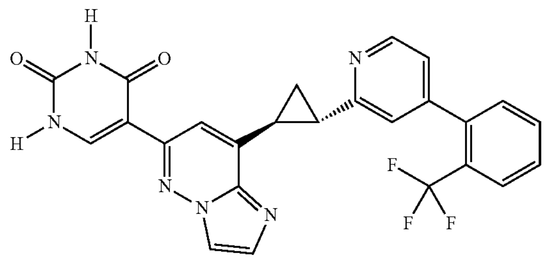 [SMILES: O=c1[nH]cc(-c2cc([C@H]3C[C@@H]3c3cc(-c4ccccc4C(F)(F)F)ccn3)c3nccn3n2)c(=O)[nH]1] | 5-(8-((1S,2S)-2-(4-(2-(trifluoromethyl)phenyl)pyridin-2-yl)cyclopropyl)imidazo[1,2-b]pyridazin-6-yl)pyrimidine-2,4(1H,3H)-dione |
| 623 | 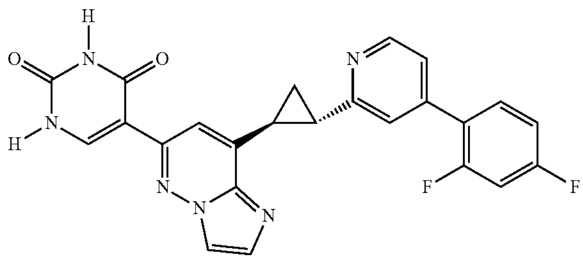 [SMILES: O=c1[nH]cc(-c2cc([C@H]3C[C@@H]3c3cc(-c4ccc(F)cc4F)ccn3)c3nccn3n2)c(=O)[nH]1] | 5-(8-((1S,2S)-2-(4-(2,4-difluorophenyl)pyridin-2-yl)cyclopropyl)imidazo[1,2-b]pyridazin-6-yl)pyrimidine-2,4(1H,3H)-dione |
| 624 | 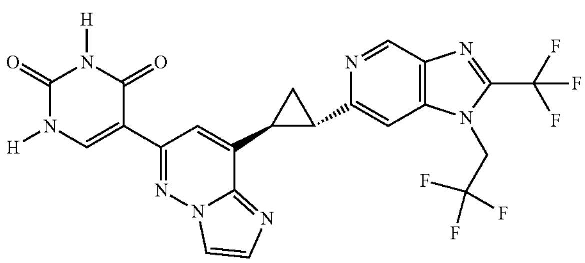 [SMILES: O=c1[nH]cc(-c2cc([C@H]3C[C@@H]3c3cc4c(cn3)nc(C(F)(F)F)n4CC(F)(F)F)c3nccn3n2)c(=O)[nH]1] | 5-(8-((1S,2S)-2-(1-(2,2,2-trifluoroethyl)-2-(trifluoromethyl)-1H-imidazo[4,5-c]pyridin-6-yl)cyclopropyl)imidazo[1,2-b]pyridazin-6-yl)pyrimidine-2,4(1H,3H)-dione |
| 625 | 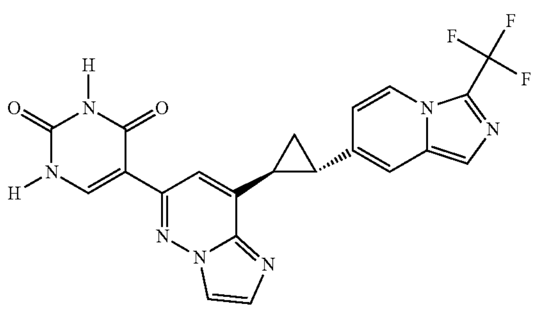 [SMILES: O=c1[nH]cc(-c2cc([C@H]3C[C@@H]3c3ccn4c(C(F)(F)F)ncc4c3)c3nccn3n2)c(=O)[nH]1] | 5-(8-((1S,2S)-2-(3-(trifluoromethyl)imidazo[1,5-a]pyridin-7-yl)cyclopropyl)imidazo[1,2-b]pyridazin-6-yl)pyrimidine-2,4(1H,3H)-dione |
| 626 | 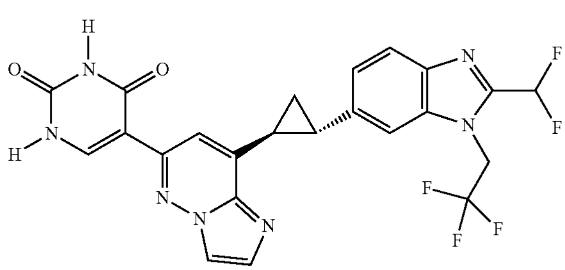 [SMILES: O=c1[nH]cc(-c2cc([C@H]3C[C@@H]3c3ccc4nc(C(F)F)n(CC(F)(F)F)c4c3)c3nccn3n2)c(=O)[nH]1] | 5-(8-((1S,2S)-2-(2-(difluoromethyl)-1-(2,2,2-trifluoroethyl)-1H-benzo[d]imidazol-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 627 | 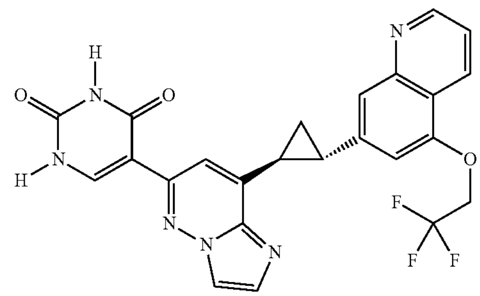 | 5-(8-((1S,2S)-2-(5-(2,2,2-trifluoroethoxy)quinolin-7-yl)cyclopropyl)imidazo[1,2-b]pyridazin-6-yl)pyrimidine-2,4(1H,3H)-dione |
| 628 | 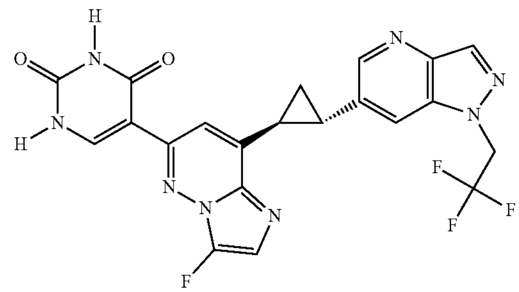 [SMILES: O=c1[nH]cc(-c2cc([C@H]3C[C@@H]3c3cnc4cnn(CC(F)(F)F)c4c3)c3ncc(F)n3n2)c(=O)[nH]1] | 5-(3-fluoro-8-((1S,2S)-2-(1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione |
| 629 | 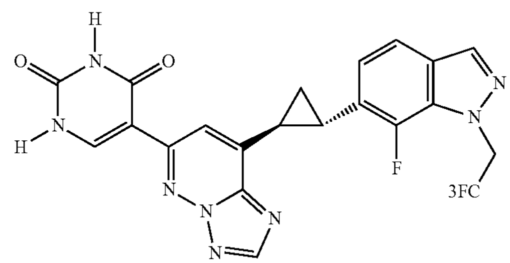 | 5-(8-((1S,2S)-2-(7-fluoro-1-(2,2,2-trifluoroethyl)-1H-indazol-6-yl)cyclopropyl)-[1,2,4]triazolo[1,5-b]pyridazin-6-yl)pyrimidine-2,4(1H,3H)-dione |
| 630 | 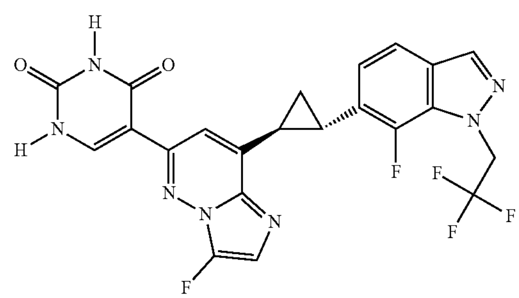 [SMILES: O=c1[nH]cc(-c2cc([C@H]3C[C@@H]3c3ccc4cnn(CC(F)(F)F)c4c3F)c3ncc(F)n3n2)c(=O)[nH]1] | 5-(3-fluoro-8-((1S,2S)-2-(7-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 631 | 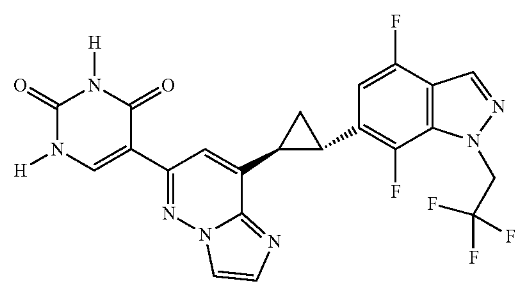 [SMILES: O=c1[nH]cc(-c2cc([C@H]3C[C@@H]3c3cc(F)c4cnn(CC(F)(F)F)c4c3F)c3nccn3n2)c(=O)[nH]1] | 5-(8-((1S,2S)-2-(4,7-difluoro-1-(2,2,2-trifluoroethyl)-1H-indazol-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 632 | 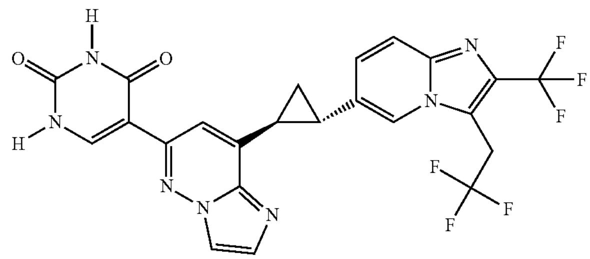 [SMILES: O=c1[nH]cc(-c2cc([C@H]3C[C@@H]3c3ccc4nc(C(F)(F)F)c(CC(F)(F)F)n4c3)c3nccn3n2)c(=O)[nH]1] | 5-(8-((1S,2S)-2-(3-(2,2,2-trifluoroethyl)-2-(trifluoromethyl)imidazo[1,2-a]pyridin-6-yl)cyclopropyl)imidazo[1,2-b]pyridazin-6-yl)pyrimidine-2,4(1H,3H)-dione |
| 633 | 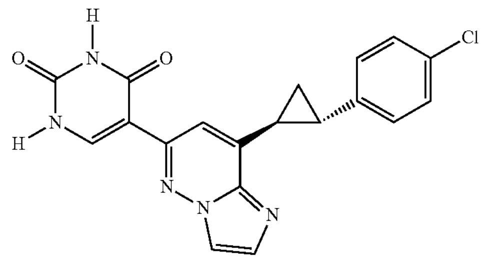 [SMILES: O=c1[nH]cc(-c2cc([C@H]3C[C@@H]3c3ccc(Cl)cc3)c3nccn3n2)c(=O)[nH]1] | 5-(8-((1S,2S)-2-(4-chlorophenyl)cyclopropyl)imidazo[1,2-b]pyridazin-6-yl)pyrimidine-2,4(1H,3H)-dione |
| 634 | 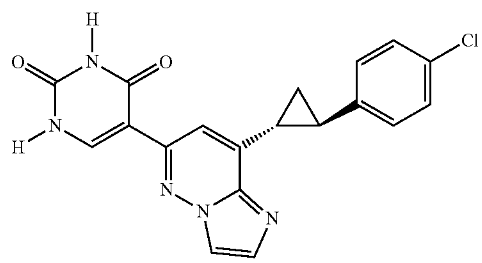 [SMILES: O=c1[nH]cc(-c2cc([C@@H]3C[C@H]3c3ccc(Cl)cc3)c3nccn3n2)c(=O)[nH]1] | 5-(8-((1R,2R)-2-(4-chlorophenyl)cyclopropyl)imidazo[1,2-b]pyridazin-6-yl)pyrimidine-2,4(1H,3H)-dione |
| 635 | 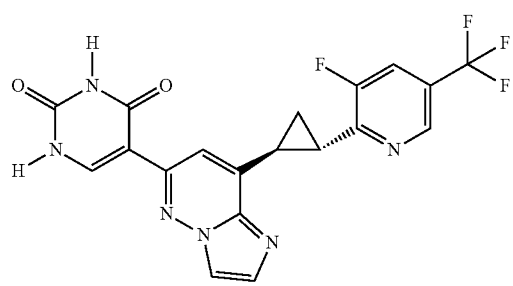 [SMILES: O=c1[nH]cc(-c2cc([C@H]3C[C@@H]3c3ncc(C(F)(F)F)cc3F)c3nccn3n2)c(=O)[nH]1] | 5-(8-((1S,2S)-2-(3-fluoro-5-(trifluoromethyl)pyridin-2-yl)cyclopropyl)imidazo[1,2-b]pyridazin-6-yl)pyrimidine-2,4(1H,3H)-dione |
| 636 | 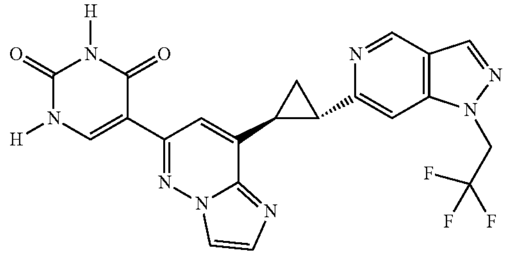 [SMILES: O=c1[nH]cc(-c2cc([C@H]3C[C@@H]3c3cc4c(cn3)cnn4CC(F)(F)F)c3nccn3n2)c(=O)[nH]1] | 5-(8-((1S,2S)-2-(1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 637 | 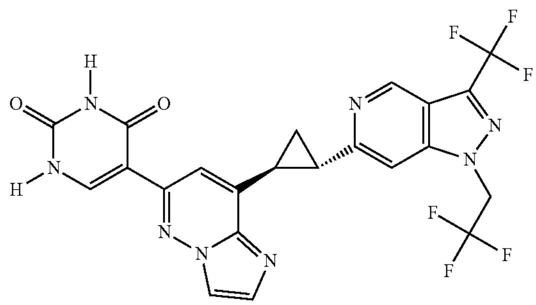 [SMILES: O=c1[nH]cc(-c2cc([C@H]3C[C@@H]3c3cc4c(cn3)c(C(F)(F)F)nn4CC(F)(F)F)c3nccn3n2)c(=O)[nH]1] | 5-(8-((1S,2S)-2-(1-(2,2,2-trifluoroethyl)-3-(trifluoromethyl)-1H-pyrazolo[4,3-c]pyridin-6-yl)cyclopropyl)imidazo[1,2-b]pyridazin-6-yl)pyrimidine-2,4(1H,3H)-dione |
| 638 | 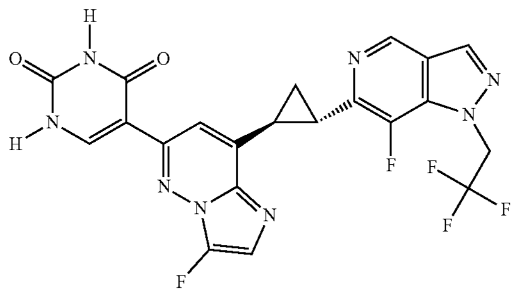 [SMILES: O=c1[nH]cc(-c2cc([C@H]3C[C@@H]3c3ncc4cnn(CC(F)(F)F)c4c3F)c3ncc(F)n3n2)c(=O)[nH]1] | 5-(3-fluoro-8-((1S,2S)-2-(7-fluoro-1-(2,2,2-trifluoroethyl)-1H-pyrazolo[4,3-c]pyridin-6-yl)cyclopropyl)imidazo[1,2-b]pyridazin-6-yl)pyrimidine-2,4(1H,3H)-dione |
| 639 | 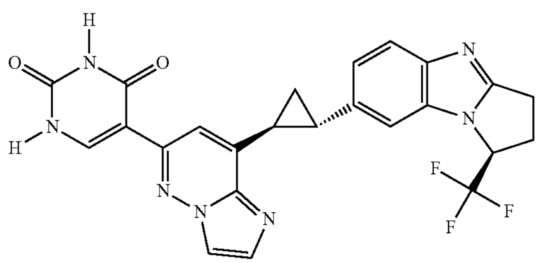 [SMILES: O=c1[nH]cc(-c2cc([C@H]3C[C@@H]3c3ccc4nc5n(c4c3)[C@H](C(F)(F)F)CC5)c3nccn3n2)c(=O)[nH]1] | 5-(8-((1S,2S)-2-((S)-1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione |
| 640 | 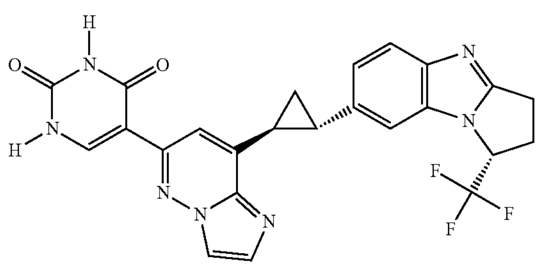 [SMILES: O=c1[nH]cc(-c2cc([C@H]3C[C@@H]3c3ccc4nc5n(c4c3)[C@@H](C(F)(F)F)CC5)c3nccn3n2)c(=O)[nH]1] | 5-(8-((1S,2S)-2-((R)-1-(trifluoromethyl)-2,3-dihydro-1H-benzo[d]pyrrolo[1,2-a]imidazol-7-yl)cyclopropyl)imidazo[1,2-b]pyridazin-6-yl)pyrimidine-2,4(1H,3H)-dione |
| 641 | 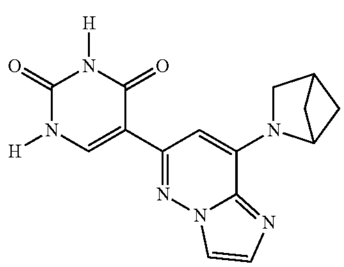 [SMILES: O=c1[nH]cc(-c2cc(N3CC4CC3C4)c3nccn3n2)c(=O)[nH]1] | 5-(8-(2-azabicyclo[2.1.1]hexan-2-yl)imidazo[1,2-b]pyridazin-6-yl)pyrimidine-2,4(1H,3H)-dione |

TABLE 2-continued

| Ex. No. | Structure | IUPAC Name |
|---|---|---|
| 642 | 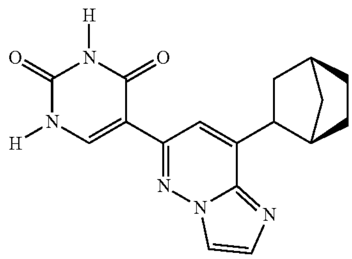 [SMILES: O=c1[nH]cc(-c2cc(C3C[C@H]4CC[C@@H]3C4)c3nccn3n2)c(=O)[nH]1] | 5-(8-((1R,4S)-2-azabicyclo[2.2.1]heptan-2-yl)imidazo[1,2-b]pyridazin-6-yl)pyrimidine-2,4(1H,3H)-dione |
| 643 | 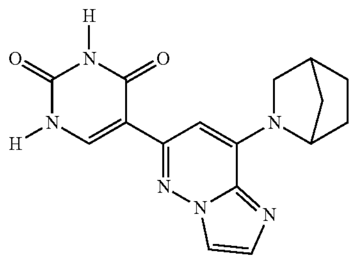 [SMILES: O=c1[nH]cc(-c2cc(N3CC4CCC3C4)c3nccn3n2)c(=O)[nH]1] | 5-(8-(2-azabicyclo[2.2.1]heptan-2-yl)imidazo[1,2-b]pyridazin-6-yl)pyrimidine-2,4(1H,3H)-dione |
| 644 | 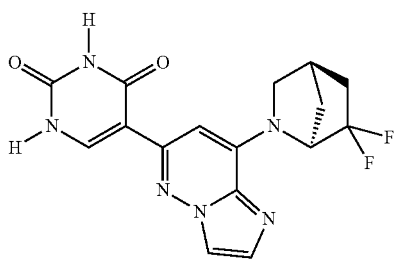 [SMILES: O=c1[nH]cc(-c2cc(N3C[C@@H]4C[C@H]3C(F)(F)C4)c3nccn3n2)c(=O)[nH]1] | 5-(8-((1S,4R)-6,6-difluoro-2-azabicyclo[2.2.1]heptan-2-yl)imidazo[1,2-b]pyridazin-6-yl)pyrimidine-2,4(1H,3H)-dione |
| 645 | 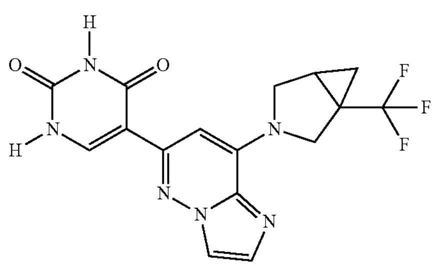 [SMILES: O=c1[nH]cc(-c2cc(N3CC4CC4(C(F)(F)F)C3)c3nccn3n2)c(=O)[nH]1] | 5-(8-(1-(trifluoromethyl)-3-azabicyclo[3.1.0]hexan-3-yl)imidazo[1,2-b]pyridazin-6-yl)pyrimidine-2,4(1H,3H)-dione |
| 646 | 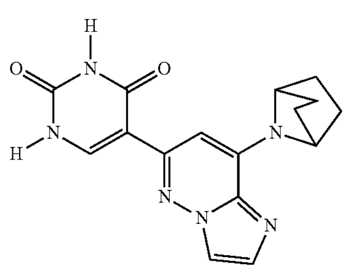 [SMILES: O=c1[nH]cc(-c2cc(N3C4CCC3CC4)c3nccn3n2)c(=O)[nH]1] | 5-(8-(7-azabicyclo[2.2.1]heptan-7-yl)imidazo[1,2-b]pyridazin-6-yl)pyrimidine-2,4(1H,3H)-dione |

TABLE 2-continued

| Ex. No. | Structure | IUPAC Name |
|---|---|---|
| 647 | 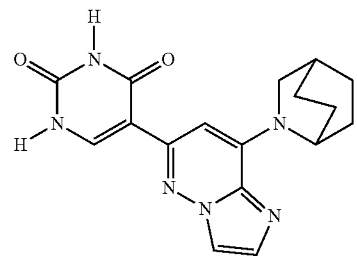 [SMILES: O=c1[nH]cc(-c2cc(N3CC4CCC3CC4)c3nccn3n2)c(=O)[nH]1] | 5-(8-(2-azabicyclo[2.2.2]octan-2-yl)imidazo[1,2-b]pyridazin-6-yl)pyrimidine-2,4(1H,3H)-dione |
| 648 | 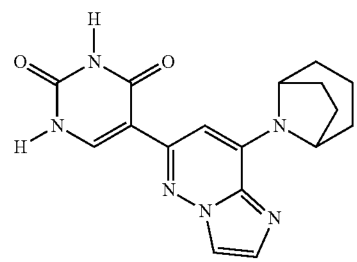 [SMILES: O=c1[nH]cc(-c2cc(N3C4CCCC3CC4)c3nccn3n2)c(=O)[nH]1] | 5-(8-(8-azabicyclo[3.2.1]octan-8-yl)imidazo[1,2-b]pyridazin-6-yl)pyrimidine-2,4(1H,3H)-dione |
| 649 | 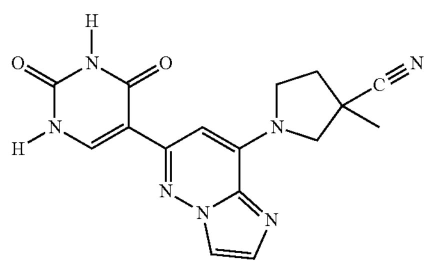 [SMILES: CC1(C#N)CCN(c2cc(-c3c[nH]c(=O)[nH]c3=O)nn3ccnc23)C1] | 1-(6-(2,4-dioxo-1,2,3,4-tetrahydropyrimidin-5-yl)imidazo[1,2-b]pyridazin-8-yl)-3-methylpyrrolidine-3-carbonitrile |
| 650 | 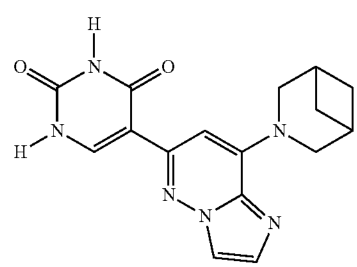 [SMILES: O=c1[nH]cc(-c2cc(N3CC4CC(C4)C3)c3nccn3n2)c(=O)[nH]1] | 5-(8-(3-azabicyclo[3.1.1]heptan-3-yl)imidazo[1,2-b]pyridazin-6-yl)pyrimidine-2,4(1H,3H)-dione |
| 651 | 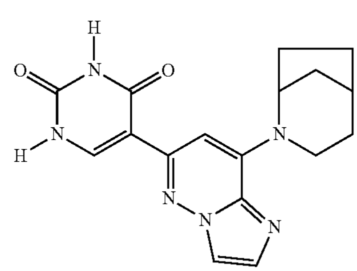 [SMILES: O=c1[nH]cc(-c2cc(N3CCC4CCC3C4)c3nccn3n2)c(=O)[nH]1] | 5-(8-(2-azabicyclo[3.2.1]octan-2-yl)imidazo[1,2-b]pyridazin-6-yl)pyrimidine-2,4(1H,3H)-dione |

TABLE 2-continued

| Ex. No. | Structure | IUPAC Name |
|---|---|---|
| 652 | 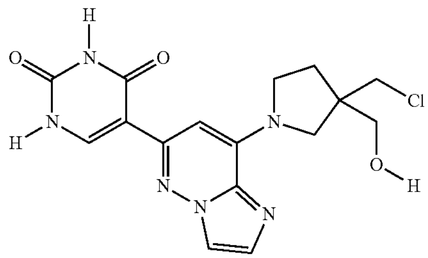 [SMILES: O=c1[nH]cc(-c2cc(N3CCC(CO)(CCl)C3)c3nccn3n2)c(=O)[nH]1] | 5-(8-(3-(chloromethyl)-3-(hydroxymethyl)pyrrolidin-1-yl)imidazo[1,2-b]pyridazin-6-yl)pyrimidine-2,4(1H,3H)-dione |
| 653 | 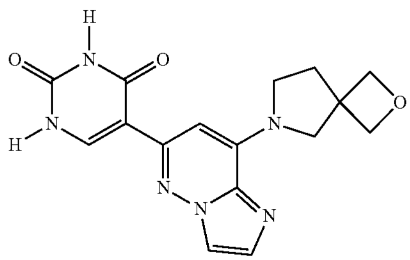 [SMILES: O=c1[nH]cc(-c2cc(N3CCC4(COC4)C3)c3nccn3n2)c(=O)[nH]1] | 5-(8-(2-oxa-6-azaspiro[3.4]octan-6-yl)imidazo[1,2-b]pyridazin-6-yl)pyrimidine-2,4(1H,3H)-dione |
| 654 | 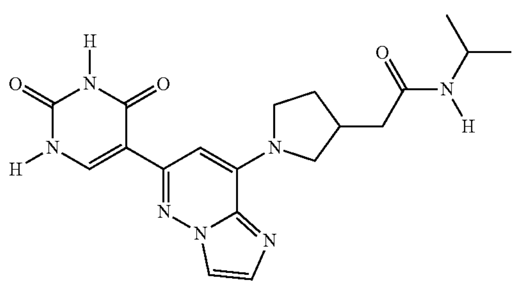 [SMILES: CC(C)NC(=O)CC1CCN(c2cc(-c3c[nH]c(=O)[nH]c3=O)nn3ccnc23)C1] | 2-(1-(6-(2,4-dioxo-1,2,3,4-tetrahydropyrimidin-5-yl)imidazo[1,2-b]pyridazin-8-yl)pyrrolidin-3-yl)-N-isopropylacetamide |
| 655 | 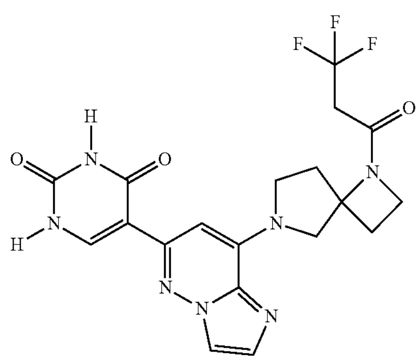 [SMILES: O=C(CC(F)(F)F)N1CCC12CCN(c1cc(-c3c[nH]c(=O)[nH]c3=O)nn3ccnc13)C2] | 5-(8-(1-(3,3,3-trifluoropropanoyl)-1,6-diazaspiro[3.4]octan-6-yl)imidazo[1,2-b]pyridazin-6-yl)pyrimidine-2,4(1H,3H)-dione |
| 656 | 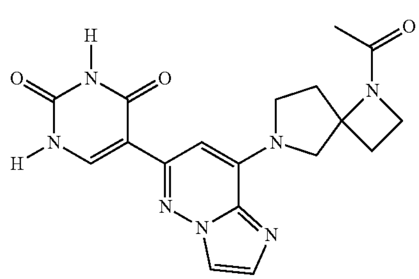 [SMILES: CC(=O)N1CCC12CCN(c1cc(-c3c[nH]c(=O)[nH]c3=O)nn3ccnc13)C2] | 5-(8-(1-acetyl-1,6-diazaspiro[3.4]octan-6-yl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 657 | 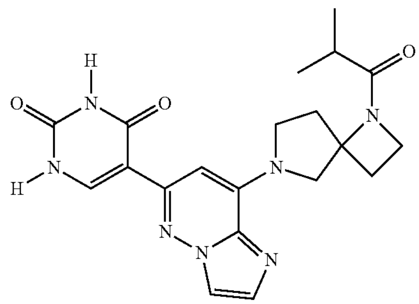 [SMILES: CC(C)C(=O)N1CCC12CCN(c1cc(-c3c[nH]c(=O)[nH]c3=O)nn3ccnc13)C2] | 5-(8-(1-isobutyryl-1,6-diazaspiro[3.4]octan-6-yl)imidazo[1,2-b]pyridazin-6-yl)pyrimidine-2,4(1H,3H)-dione |
| 658 | 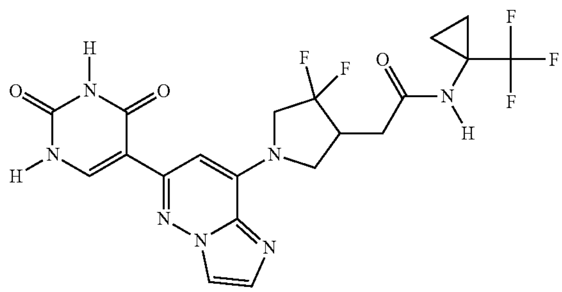 [SMILES: O=C(CC1CN(c2cc(-c3c[nH]c(=O)[nH]c3=O)nn3ccnc23)CC1(F)F)NC1(C(F)(F)F)CC1] | 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-(1-(trifluoromethyl)cyclopropyl)acetamide |
| 659 | 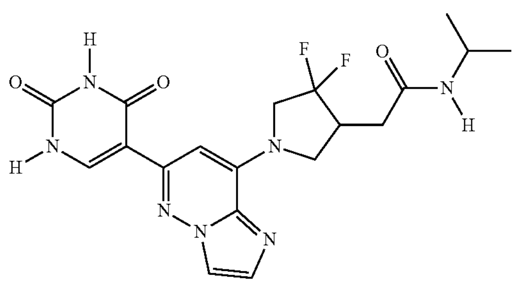 [SMILES: CC(C)NC(=O)CC1CN(c2cc(-c3c[nH]c(=O)[nH]c3=O)nn3ccnc23)CC1(F)F] | 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-isopropylacetamide |
| 660 | 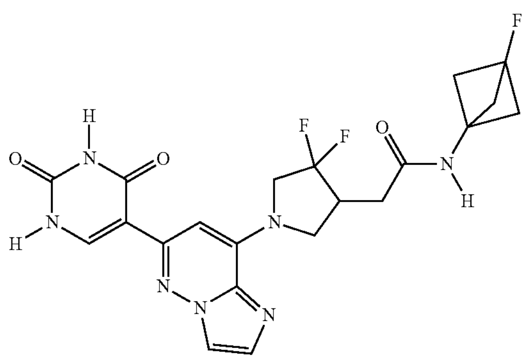 [SMILES: O=C(CC1CN(c2cc(-c3c[nH]c(=O)[nH]c3=O)nn3ccnc23)CC1(F)F)NC12CC(F)(C1)C2] | 2-(1-(6-(2,4-dioxo-1,2,3,4-tetrahydropyrimidin-5-yl)imidazo[1,2-b]pyridazin-8-yl)-4,4-difluoropyrrolidin-3-yl)-N-(3-fluorobicyclo[1.1.1]pentan-1-yl)acetamide |
| 661 | 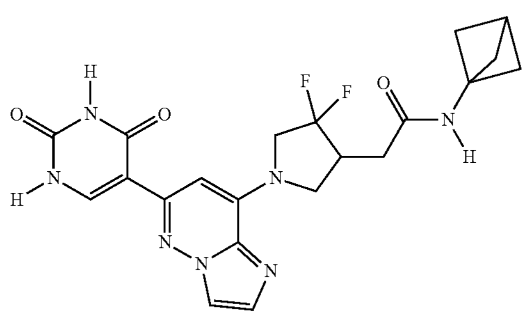 [SMILES: O=C(CC1CN(c2cc(-c3c[nH]c(=O)[nH]c3=O)nn3ccnc23)CC1(F)F)NC12CC(C1)C2] | N-(bicyclo[1.1.1]pentan-1-yl)-2-(1-(6-(2,4-dioxo-1,2,3,4-tetrahydropyrimidin-5-yl)imidazo[1,2-b]pyridazin-8-yl)-4,4-difluoropyrrolidin-3-yl)acetamide |

TABLE 2-continued

| Ex. No. | Structure | IUPAC Name |
|---|---|---|
| 662 | 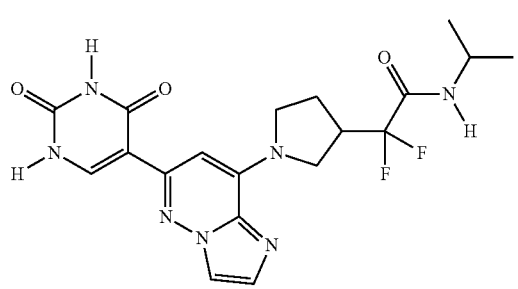 [SMILES: CC(C)NC(=O)C(F)(F)C1CCN(c2cc(-c3c[nH]c(=O)[nH]c3=O)nn3ccnc23)C1] | 2-(1-(6-(2,4-dioxo-1,2,3,4-tetrahydropyrimidin-5-yl)imidazo[1,2-b]pyridazin-8-yl)pyrrolidin-3-yl)-2,2-difluoro-N-isopropylacetamide |
| 663 | 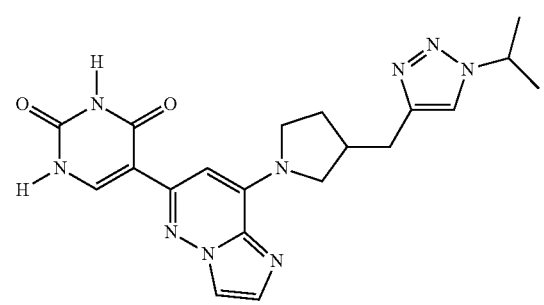 [SMILES: CC(C)n1cc(CC2CCN(c3cc(-c4c[nH]c(=O)[nH]c4=O)nn4ccnc34)C2)nn1] | 5-(8-(3-((1-isopropyl-1H-1,2,3-triazol-4-yl)methyl)pyrrolidin-1-yl)imidazo[1,2-b]pyridazin-6-yl)pyrimidine-2,4(1H,3H)-dione |
| 664 | 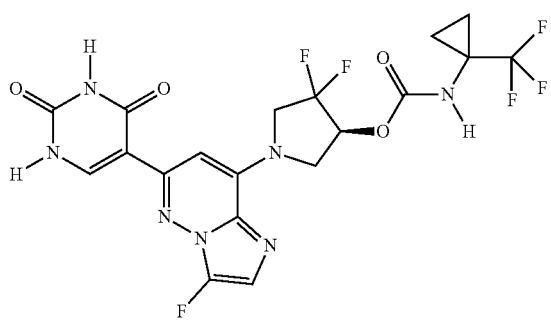 [SMILES: O=C(NC1(C(F)(F)F)CC1)O[C@H]1CN(c2cc(-c3c[nH]c(=O)[nH]c3=O)nn3c(F)cnc23)CC1(F)F] | (S)-1-(6-(2,4-dioxo-1,2,3,4-tetrahydropyrimidin-5-yl)-3-fluoroimidazo[1,2-b]pyridazin-8-yl)-4,4-difluoropyrrolidin-3-yl (1-(trifluoromethyl)cyclopropyl)carbamate |
| 665 | 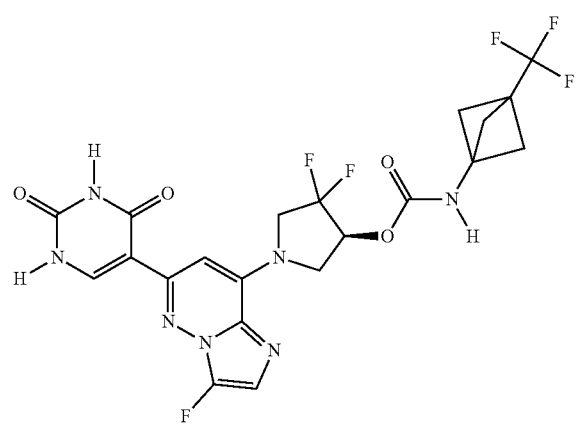 [SMILES: O=C(NC12CC(C(F)(F)F)(C1)C2)O[C@H]1CN(c2cc(-c3c[nH]c(=O)[nH]c3=O)nn3c(F)cnc23)CC1(F)F] | (S)-1-(6-(2,4-dioxo-1,2,3,4-tetrahydropyrimidin-5-yl)-3-fluoroimidazo[1,2-b]pyridazin-8-yl)-4,4-difluoropyrrolidin-3-yl (3-(trifluoromethyl)bicyclo[1.1.1]pentan-1-yl)carbamate |

TABLE 2-continued

Examples

| Ex. No. | Structure | IUPAC Name |
|---|---|---|
| 666 | 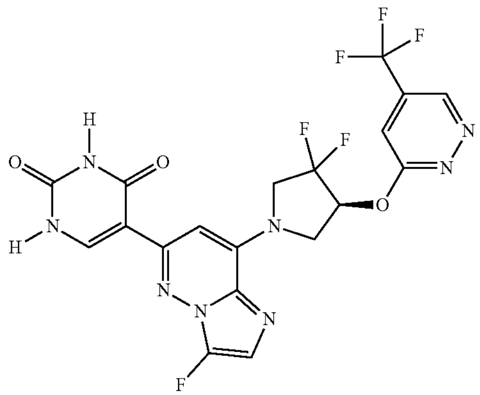 [SMILES: O=c1[nH]cc(-c2cc(N3C[C@H](Oc4cc(C(F)(F)F)cnn4)C(F)(F)C3)c3ncc(F)n3n2)c(=O)[nH]1] | (S)-5-(8-(3,3-difluoro-4-((5-(trifluoromethyl)pyridazin-3-yl)oxy)pyrrolidin-1-yl)-3-fluoroimidazo[1,2-b]pyridazin-6-yl)pyrimidine-2,4(1H,3H)-dione |
| 667 | 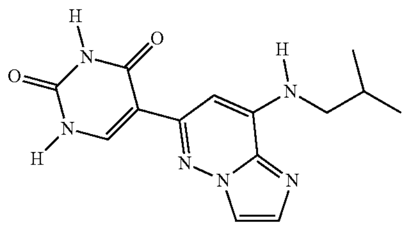 [SMILES: CC(C)CNc1cc(-c2c[nH]c(=O)[nH]c2=O)nn2ccnc12] | 5-(8-(isobutylamino)imidazo[1,2-b]pyridazin-6-yl)pyrimidine-2,4(1H,3H)-dione |
| 668 | 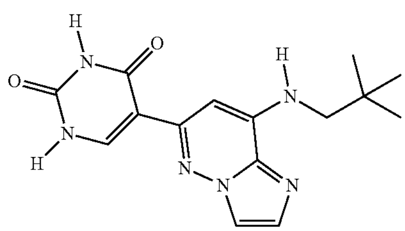 [SMILES: CC(C)(C)CNc1cc(-c2c[nH]c(=O)[nH]c2=O)nn2ccnc12] | 5-(8-(neopentylamino)imidazo[1,2-b]pyridazin-6-yl)pyrimidine-2,4(1H,3H)-dione |
| 669 | 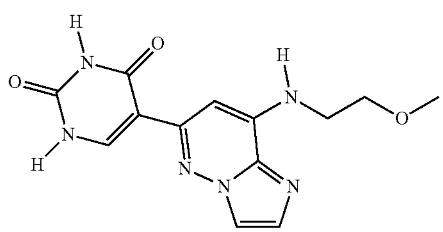 [SMILES: COCCNc1cc(-c2c[nH]c(=O)[nH]c2=O)nn2ccnc12] | 5-(8-((2-methoxyethyl)amino)imidazo[1,2-b]pyridazin-6-yl)pyrimidine-2,4(1H,3H)-dione |
| 670 | 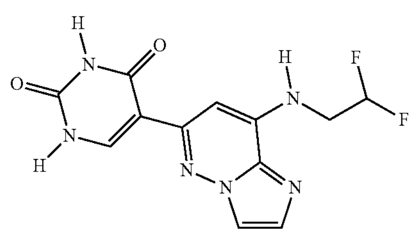 [SMILES: O=c1[nH]cc(-c2cc(NCC(F)F)c3nccn3n2)c(=O)[nH]1] | 5-(8-((2,2-difluoroethyl)amino)imidazo[1,2-b]pyridazin-6-yl)pyrimidine-2,4(1H,3H)-dione |
| 671 | 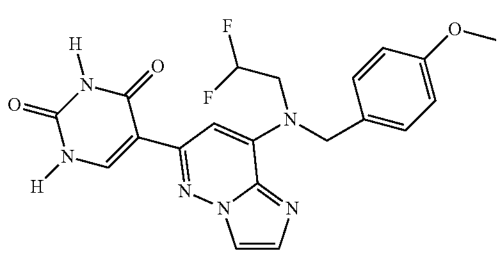 [SMILES: COc1ccc(CN(CC(F)F)c2cc(-c3c[nH]c(=O)[nH]c3=O)nn3ccnc23)cc1] | 5-(8-((2,2-difluoroethyl)(4-methoxybenzyl)amino)imidazo[1,2-b]pyridazin-6-yl)pyrimidine-2,4(1H,3H)-dione |

TABLE 2-continued

| Ex. No. | Structure | IUPAC Name |
|---|---|---|
| 672 | 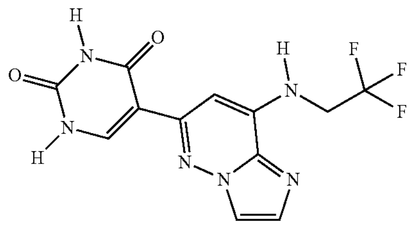 [SMILES: O=c1[nH]cc(-c2cc(NCC(F)(F)F)c3nccn3n2)c(=O)[nH]1] | 5-(8-((2,2,2-trifluoroethyl)amino)imidazo[1,2-b]pyridazin-6-yl)pyrimidine-2,4(1H,3H)-dione |
| 673 | 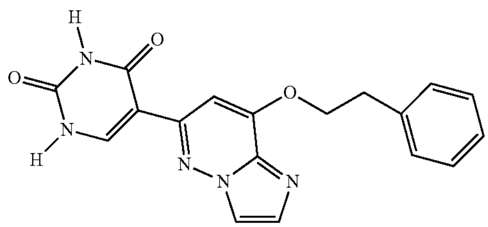 [SMILES: O=c1[nH]cc(-c2cc(OCCc3ccccc3)c3nccn3n2)c(=O)[nH]1] | 5-(8-phenethoxyimidazo[1,2-b]pyridazin-6-yl)pyrimidine-2,4(1H,3H)-dione |
| 674 | 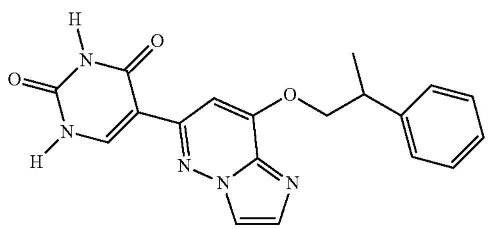 [SMILES: CC(COc1cc(-c2c[nH]c(=O)[nH]c2=O)nn2ccnc12)c1ccccc1] | 5-(8-(2-phenylpropoxy)imidazo[1,2-b]pyridazin-6-yl)pyrimidine-2,4(1H,3H)-dione |
| 675 | 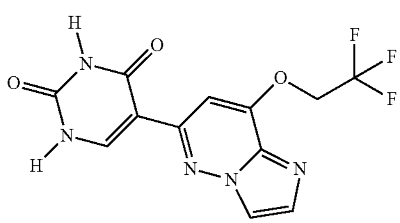 [SMILES: O=c1[nH]cc(-c2cc(OCC(F)(F)F)c3nccn3n2)c(=O)[nH]1] | 5-(8-(2,2,2-trifluoroethoxy)imidazo[1,2-b]pyridazin-6-yl)pyrimidine-2,4(1H,3H)-dione |
| 676 | 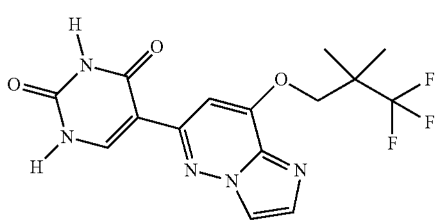 [SMILES: CC(C)(COc1cc(-c2c[nH]c(=O)[nH]c2=O)nn2ccnc12)C(F)(F)F] | 5-(8-(3,3,3-trifluoro-2,2-dimethylpropoxy)imidazo[1,2-b]pyridazin-6-yl)pyrimidine-2,4(1H,3H)-dione |
| 677 | 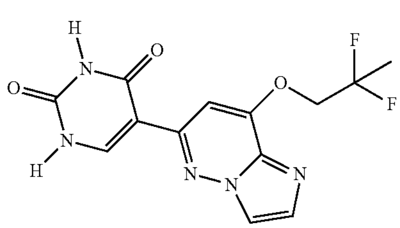 [SMILES: CC(F)(F)COc1cc(-c2c[nH]c(=O)[nH]c2=O)nn2ccnc12] | 5-(8-(2,2-difluoropropoxy)imidazo[1,2-b]pyridazin-6-yl)pyrimidine-2,4(1H,3H)-dione |

TABLE 2-continued

Examples

| Ex. No. | Structure | IUPAC Name |
| --- | --- | --- |
| 678 | 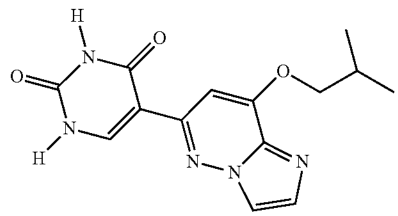 [SMILES: CC(C)COc1cc(-c2c[nH]c(=O)[nH]c2=O)nn2ccnc12] | 5-(8-isobutoxyimidazo[1,2-b]pyridazin-6-yl)pyrimidine-2,4(1H,3H)-dione |
| 679 | 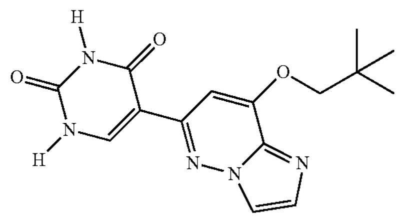 [SMILES: CC(C)(C)COc1cc(-c2c[nH]c(=O)[nH]c2=O)nn2ccnc12] | 5-(8-(neopentyloxy)imidazo[1,2-b]pyridazin-6-yl)pyrimidine-2,4(1H,3H)-dione |
| 680 | 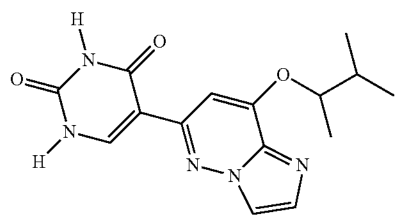 [SMILES: CC(C)C(C)Oc1cc(-c2c[nH]c(=O)[nH]c2=O)nn2ccnc12] | 5-(8-((3-methylbutan-2-yl)oxy)imidazo[1,2-b]pyridazin-6-yl)pyrimidine-2,4(1H,3H)-dione |
| 681 | 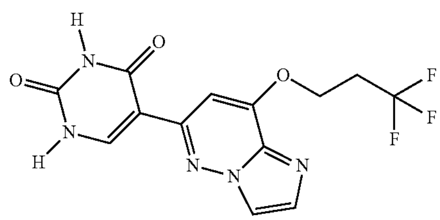 [SMILES: O=c1[nH]cc(-c2cc(OCCC(F)(F)F)c3nccn3n2)c(=O)[nH]1] | 5-(8-(3,3,3-trifluoropropoxy)imidazo[1,2-b]pyridazin-6-yl)pyrimidine-2,4(1H,3H)-dione |
| 682 | 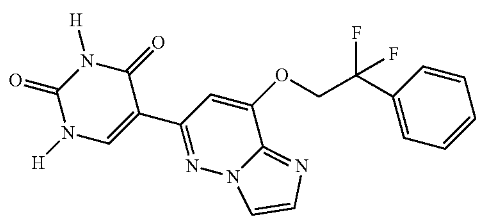 [SMILES: O=c1[nH]cc(-c2cc(OCC(F)(F)c3ccccc3)c3nccn3n2)c(=O)[nH]1] | 5-(8-(2,2-difluoro-2-phenylethoxy)imidazo[1,2-b]pyridazin-6-yl)pyrimidine-2,4(1H,3H)-dione |
| 683 | 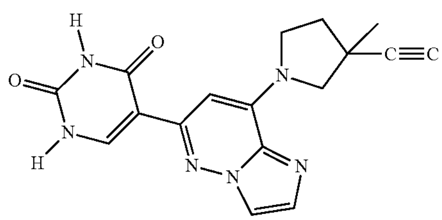 [SMILES: C#CC1(C)CCN(c2cc(-c3c[nH]c(=O)[nH]c3=O)nn3ccnc23)C1] | 5-(8-(3-ethynyl-3-methylpyrrolidin-1-yl)imidazo[1,2-b]pyridazin-6-yl)pyrimidine-2,4(1H,3H)-dione |
| 684 | 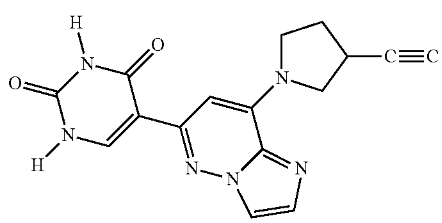 [SMILES: C#CC1CCN(c2cc(-c3c[nH]c(=O)[nH]c3=O)nn3ccnc23)C1] | 5-(8-(3-ethynylpyrrolidin-1-yl)imidazo[1,2-b]pyridazin-6-yl)pyrimidine-2,4(1H,3H)-dione |

TABLE 2-continued

| Ex. No. | Structure | IUPAC Name |
| --- | --- | --- |
| 685 | 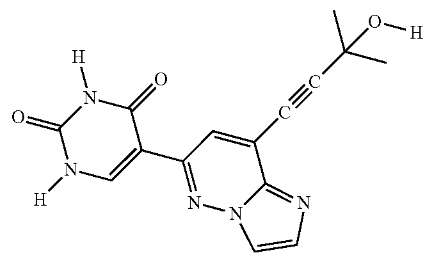 [SMILES: CC(C)(O)C#Cc1cc(-c2c[nH]c(=O)[nH]c2=O)nn2ccnc12] | 5-(8-(3-hydroxy-3-methylbut-1-yn-1-yl)imidazo[1,2-b]pyridazin-6-yl)pyrimidine-2,4(1H,3H)-dione |
| 686 | 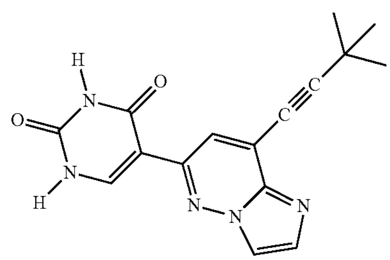 [SMILES: CC(C)(C)C#Cc1cc(-c2c[nH]c(=O)[nH]c2=O)nn2ccnc12] | 5-(8-(3,3-dimethylbut-1-yn-1-yl)imidazo[1,2-b]pyridazin-6-yl)pyrimidine-2,4(1H,3H)-dione |
| 687 | 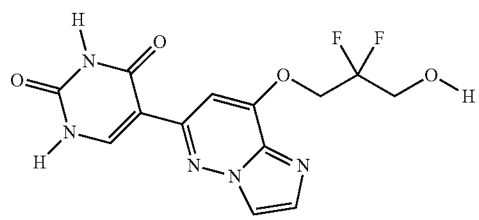 [SMILES: O=c1[nH]cc(-c2cc(OCC(F)(F)CO)c3nccn3n2)c(=O)[nH]1] | 5-(8-(2,2-difluoro-3-hydroxypropoxy)imidazo[1,2-b]pyridazin-6-yl)pyrimidine-2,4(1H,3H)-dione |
| 688 | 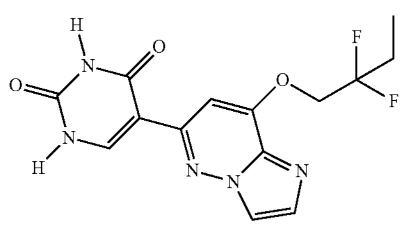 [SMILES: CCC(F)(F)COc1cc(-c2c[nH]c(=O)[nH]c2=O)nn2ccnc12] | 5-(8-(2,2-difluorobutoxy)imidazo[1,2-b]pyridazin-6-yl)pyrimidine-2,4(1H,3H)-dione |
| 689 | 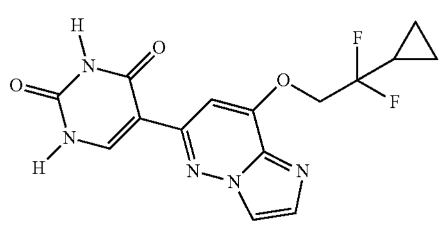 [SMILES: O=c1[nH]cc(-c2cc(OCC(F)(F)C3CC3)c3nccn3n2)c(=O)[nH]1] | 5-(8-(2-cyclopropyl-2,2-difluoroethoxy)imidazo[1,2-b]pyridazin-6-yl)pyrimidine-2,4(1H,3H)-dione |
| 690 | 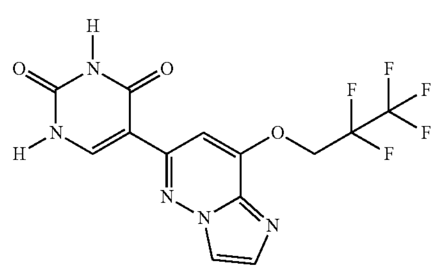 [SMILES: O=c1[nH]cc(-c2cc(OCC(F)(F)C(F)(F)F)c3nccn3n2)c(=O)[nH]1] | 5-(8-(2,2,3,3,3-pentafluoropropoxy)imidazo[1,2-b]pyridazin-6-yl)pyrimidine-2,4(1H,3H)-dione |

TABLE 2-continued

| Ex. No. | Structure | IUPAC Name |
| --- | --- | --- |
| 691 | 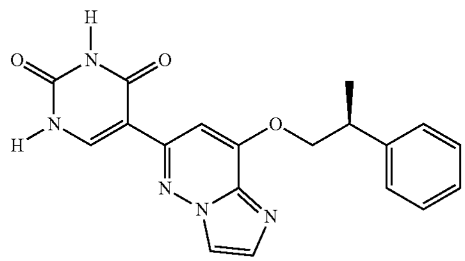 [SMILES: C[C@H](COc1cc(-c2c[nH]c(=O)[nH]c2=O)nn2ccnc12)c1ccccc1] | (S)-5-(8-(2-phenylpropoxy)imidazo[1,2-b]pyridazin-6-yl)pyrimidine-2,4(1H,3H)-dione |
| 692 | 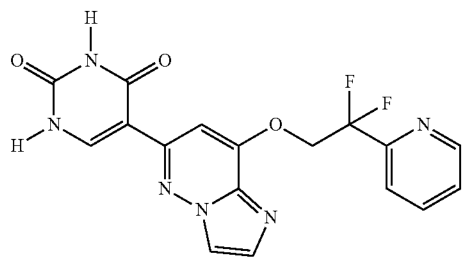 [SMILES: O=c1[nH]cc(-c2cc(OCC(F)(F)c3ccccn3)c3nccn3n2)c(=O)[nH]1] | 5-(8-(2,2-difluoro-2-(pyridin-2-yl)ethoxy)imidazo[1,2-b]pyridazin-6-yl)pyrimidine-2,4(1H,3H)-dione |
| 693 | 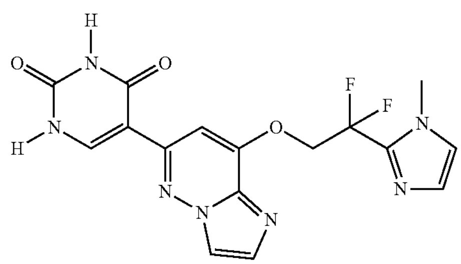 [SMILES: Cn1ccnc1C(F)(F)COc1cc(-c2c[nH]c(=O)[nH]c2=O)nn2ccnc12] | 5-(8-(2,2-difluoro-2-(1-methyl-1H-imidazol-2-yl)ethoxy)imidazo[1,2-b]pyridazin-6-yl)pyrimidine-2,4(1H,3H)-dione |
| 694 | 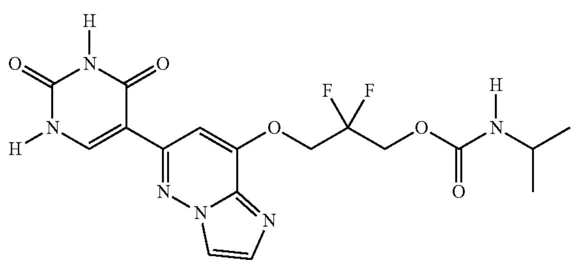 [SMILES: CC(C)NC(=O)OCC(F)(F)COc1cc(-c2c[nH]c(=O)[nH]c2=O)nn2ccnc12] | 3-((6-(2,4-dioxo-1,2,3,4-tetrahydropyrimidin-5-yl)imidazo[1,2-b]pyridazin-8-yl)oxy)-2,2-difluoropropyl isopropylcarbamate |
| 695 | 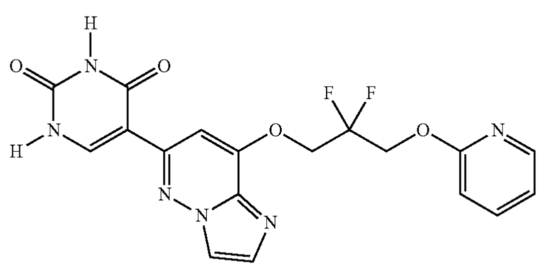 [SMILES: O=c1[nH]cc(-c2cc(OCC(F)(F)COc3ccccn3)c3nccn3n2)c(=O)[nH]1] | 5-(8-(2,2-difluoro-3-(pyridin-2-yloxy)propoxy)imidazo[1,2-b]pyridazin-6-yl)pyrimidine-2,4(1H,3H)-dione |

TABLE 2-continued

| Ex. No. | Structure | IUPAC Name |
|---|---|---|
| 696 | 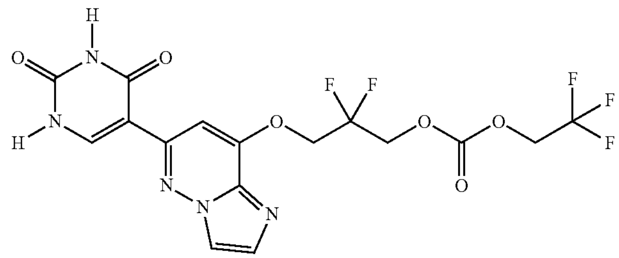 [SMILES: O=C(OCC(F)(F)F)OCC(F)(F)COc1cc(-c2c[nH]c(=O)[nH]c2=O)nn2ccnc12] | 3-((6-(2,4-dioxo-1,2,3,4-tetrahydropyrimidin-5-yl)imidazo[1,2-b]pyridazin-8-yl)oxy)-2,2-difluoropropyl (2,2,2-trifluoroethyl) carbonate |
| 697 | 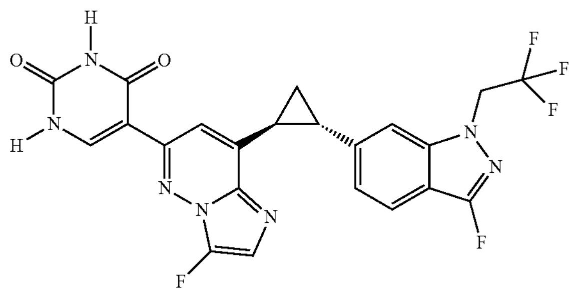 [SMILES: O=c1[nH]cc(-c2cc([C@H]3C[C@@H]3c3ccc4c(F)nn(CC(F)(F)F)c4c3)c3ncc(F)n3n2)c(=O)[nH]1] | 5-(3-fluoro-8-((1S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 698 | 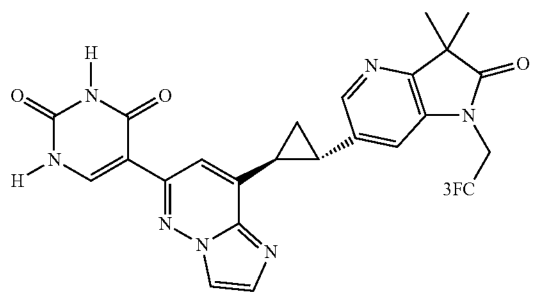 | 5-(8-((1S,2S)-2-(3,3-dimethyl-2-oxo-1-(2,2,2-trifluoroethyl)-2,3-dihydro-1H-pyrrolo[3,2-b]pyridin-6-yl)cyclopropyl)imidazo[1,2-b]pyridazin-6-yl)pyrimidine-2,4(1H,3H)-dione |
| 699 | 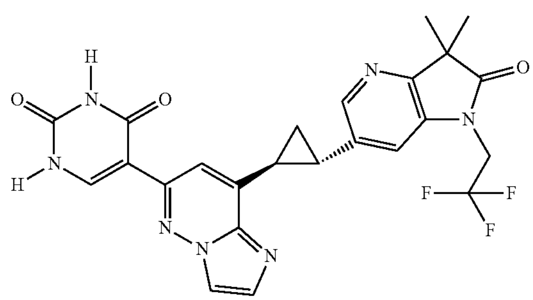 [SMILES: CC1(C)C(=O)N(CC(F)(F)F)c2cc([C@H]3C[C@@H]3c3cc(-c4c[nH]c(=O)[nH]c4=O)nn4ccnc34)cnc21] | 5-(8-((1S,2S)-2-(3,3-dimethyl-2-oxo-1-(2,2,2-trifluoroethyl)-2,3-dihydro-1H-pyrrolo[3,2-b]pyridin-6-yl)cyclopropyl)imidazo[1,2-b]pyridazin-6-yl)pyrimidine-2,4(1H,3H)-dione |
| 700 | 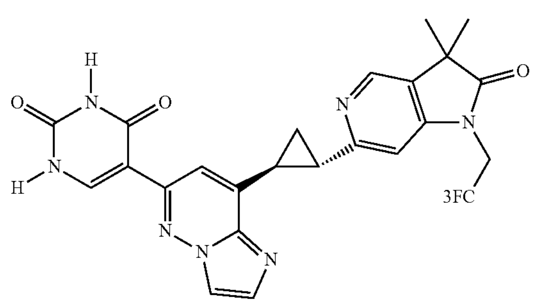 | 5-(8-((1S,2S)-2-(3,3-dimethyl-2-oxo-1-(2,2,2-trifluoroethyl)-2,3-dihydro-1H-pyrrolo[3,2-c]pyridin-6-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 701 | 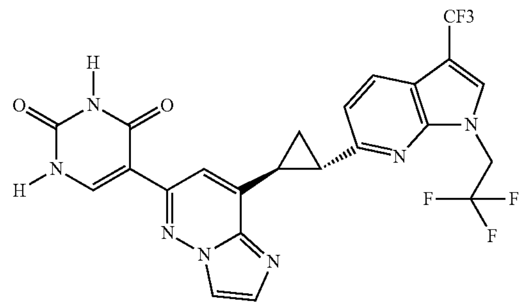 [SMILES: O=c1[nH]cc(-c2cc([C@H]3C[C@@H]3c3ccc4c(C(F)(F)F)cn(CC(F)(F)F)c4n3)c3nccn3n2)c(=O)[nH]1] | 5-(8-((1S,2S)-2-(1-(2,2,2-trifluoroethyl)-3-(trifluoromethyl)-1H-pyrrolo[2,3-b]pyridin-6-yl)cyclopropyl)imidazo[1,2-b]pyridazin-6-yl)pyrimidine-2,4(1H,3H)-dione |
| 702 | 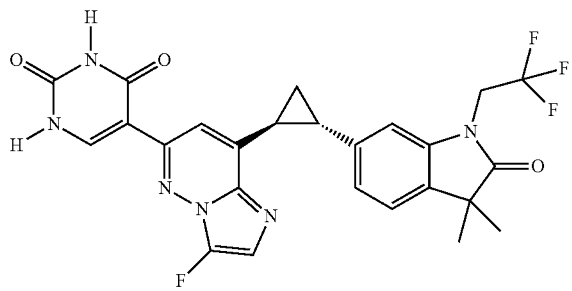 [SMILES: CC1(C)C(=O)N(CC(F)(F)F)c2cc([C@H]3C[C@@H]3c3cc(-c4c[nH]c(=O)[nH]c4=O)nn4c(F)cnc34)ccc21] | 5-(8-((1S,2S)-2-(3,3-dimethyl-2-oxo-1-(2,2,2-trifluoroethyl)indolin-6-yl)cyclopropyl)-3-fluoroimidazo[1,2-b]pyridazin-6-yl)pyrimidine-2,4(1H,3H)-dione |
| 703 | 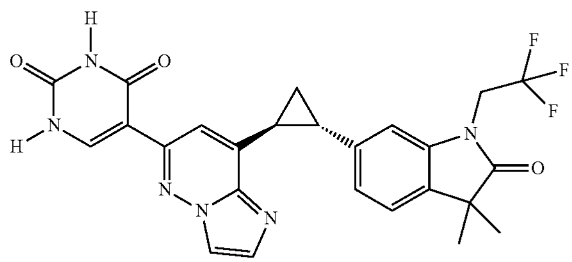 [SMILES: CC1(C)C(=O)N(CC(F)(F)F)c2cc([C@H]3C[C@@H]3c3cc(-c4c[nH]c(=O)[nH]c4=O)nn4ccnc34)ccc21] | 5-(8-((1S,2S)-2-(3,3-dimethyl-2-oxo-1-(2,2,2-trifluoroethyl)indolin-6-yl)cyclopropyl)imidazo[1,2-b]pyridazin-6-yl)pyrimidine-2,4(1H,3H)-dione |
| 704 | 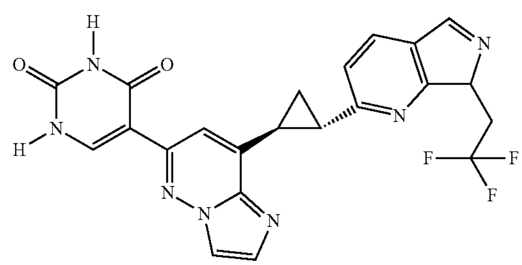 [SMILES: O=c1[nH]cc(-c2cc([C@H]3C[C@@H]3c3ccc4c(n3)C(CC(F)(F)F)N=C4)c3nccn3n2)c(=O)[nH]1] | 5-(8-((1S,2S)-2-(1-(2,2,2-trifluoroethyl)-1H-pyrrolo[2,3-b]pyridin-6-yl)cyclopropyl)imidazo[1,2-b]pyridazin-6-yl)pyrimidine-2,4(1H,3H)-dione |
| 705 | 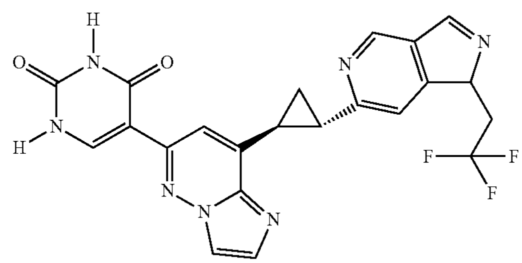 [SMILES: O=c1[nH]cc(-c2cc([C@H]3C[C@@H]3c3cc4c(cn3)C=NC4CC(F)(F)F)c3nccn3n2)c(=O)[nH]1] | 5-(8-((1S,2S)-2-(1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 706 | 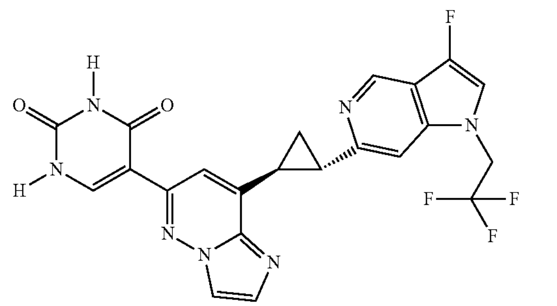 [SMILES: O=c1[nH]cc(-c2cc([C@H]3C[C@@H]3c3cc4c(cn3)c(F)cn4CC(F)(F)F)c3nccn3n2)c(=O)[nH]1] | 5-(8-((1S,2S)-2-(3-fluoro-1-(2,2,2-trifluoroethyl)-1H-pyrrolo[3,2-c]pyridin-6-yl)cyclopropyl)imidazo[1,2-b]pyridazin-6-yl)pyrimidine-2,4(1H,3H)-dione |
| 707 | 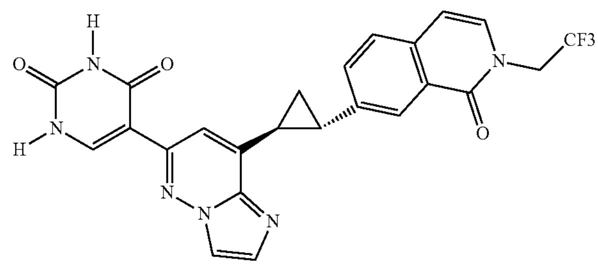 [SMILES: O=c1[nH]cc(-c2cc([C@H]3C[C@@H]3c3ccc4ccn(CC(F)(F)F)c(=O)c4c3)c3nccn3n2)c(=O)[nH]1] | 5-(8-((1S,2S)-2-(1-oxo-2-(2,2,2-trifluoroethyl)-1,2-dihydroisoquinolin-7-yl)cyclopropyl)imidazo[1,2-b]pyridazin-6-yl)pyrimidine-2,4(1H,3H)-dione |
| 708 | 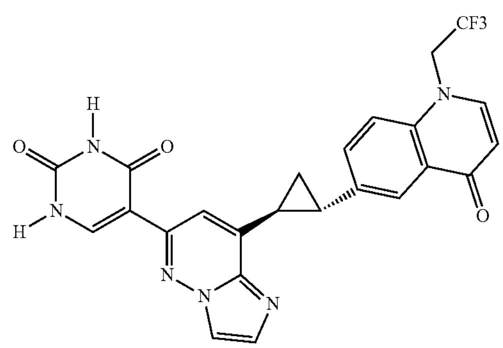 [SMILES: O=c1[nH]cc(-c2cc([C@H]3C[C@@H]3c3ccc4c(c3)c(=O)ccn4CC(F)(F)F)c3nccn3n2)c(=O)[nH]1] | 5-(8-((1S,2S)-2-(4-oxo-1-(2,2,2-trifluoroethyl)-1,4-dihydroquinolin-6-yl)cyclopropyl)imidazo[1,2-b]pyridazin-6-yl)pyrimidine-2,4(1H,3H)-dione |
| 709 | 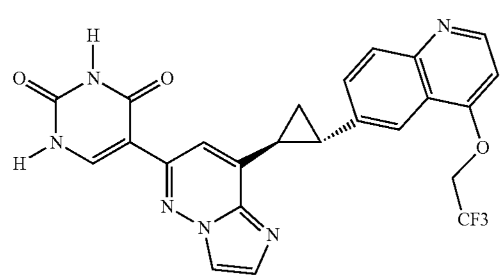 [SMILES: O=c1[nH]cc(-c2cc([C@H]3C[C@@H]3c3ccc4nccc(OCC(F)(F)F)c4c3)c3nccn3n2)c(=O)[nH]1] | 5-(8-((1S,2S)-2-(4-(2,2,2-trifluoroethoxy)quinolin-6-yl)cyclopropyl)imidazo[1,2-b]pyridazin-6-yl)pyrimidine-2,4(1H,3H)-dione |
| 710 | 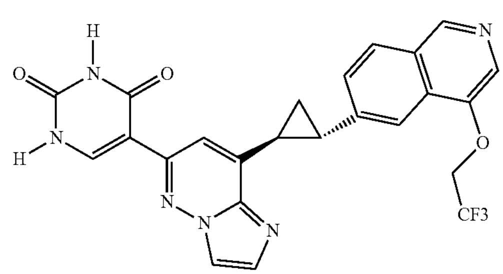 [SMILES: O=c1[nH]cc(-c2cc([C@H]3C[C@@H]3c3ccc4cncc(OCC(F)(F)F)c4c3)c3nccn3n2)c(=O)[nH]1] | 5-(8-((1S,2S)-2-(4-(2,2,2-trifluoroethoxy)isoquinolin-6-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 711 | 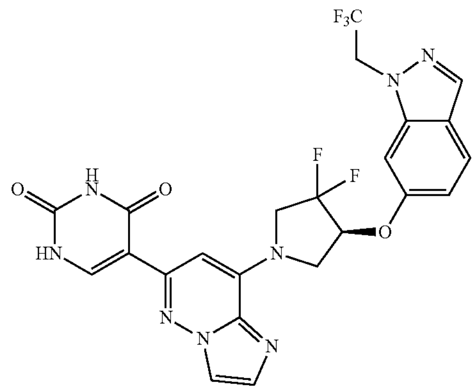 [SMILES: O=c1[nH]cc(-c2cc(N3C[C@H](Oc4ccc5cnn(CC(F)(F)F)c5c4)C(F)(F)C3)c3nccn3n2)c(=O)[nH]1] | (S)-5-(8-(3,3-difluoro-4-((1-(2,2,2-trifluoroethyl)-1H-indazol-6-yl)oxy)pyrrolidin-1-yl)imidazo[1,2-b]pyridazin-6-yl)pyrimidine-2,4(1H,3H)-dione |
| 712 | 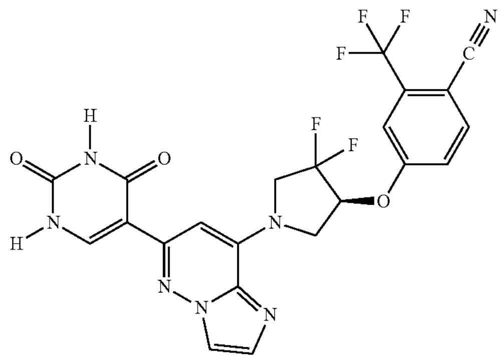 [SMILES: N#Cc1ccc(O[C@H]2CN(c3cc(-c4c[nH]c(=O)[nH]c4=O)nn4ccnc34)CC2(F)F)cc1C(F)(F)F] | (S)-4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)-2-(trifluoromethyl)benzonitrile |
| 713 | 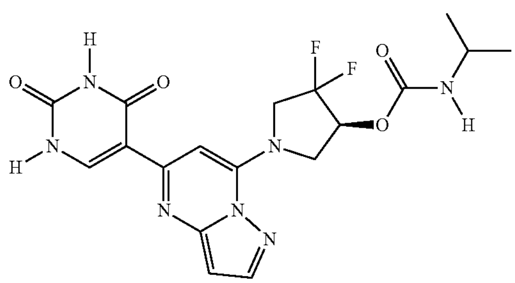 [SMILES: CC(C)NC(=O)O[C@H]1CN(c2cc(-c3c[nH]c(=O)[nH]c3=O)nc3ccnn23)CC1(F)F] | (S)-1-(5-(2,4-dioxo-1,2,3,4-tetrahydropyrimidin-5-yl)pyrazolo[1,5-a]pyrimidin-7-yl)-4,4-difluoropyrrolidin-3-yl isopropylcarbamate |
| 714 | 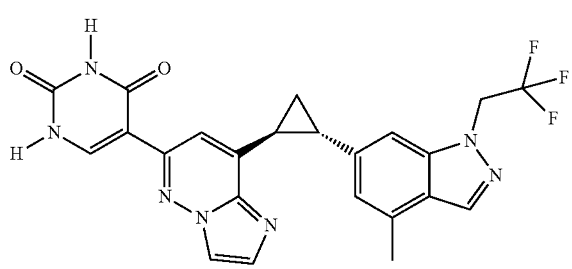 [SMILES: Cc1cc([C@H]2C[C@@H]2c2cc(-c3c[nH]c(=O)[nH]c3=O)nn3ccnc23)cc2c1cnn2CC(F)(F)F] | 5-(8-((1S,2S)-2-(4-methyl-1-(2,2,2-trifluoroethyl)-1H-indazol-6-yl)cyclopropyl)imidazo[1,2-b]pyridazin-6-yl)pyrimidine-2,4(1H,3H)-dione |
| 715 | 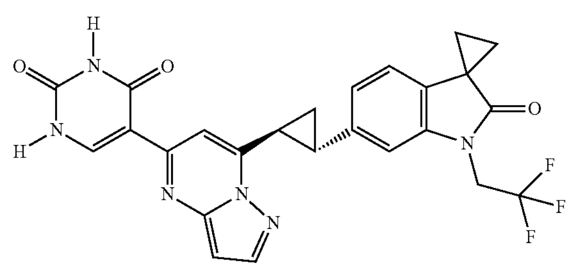 [SMILES: O=C1N(CC(F)(F)F)c2cc([C@H]3C[C@@H]3c3cc(-c4c[nH]c(=O)[nH]c4=O)nc4ccnn34)ccc2C12CC2] | 5-(7-((1S,2S)-2-(2'-oxo-1'-(2,2,2-trifluoroethyl)spiro[cyclopropane-1,3'-indolin]-6'-yl)cyclopropyl)pyrazolo[1,5-a]pyrimidin-5-yl)pyrimidine-2,4(1H,3H)-dione |

TABLE 2-continued

| Ex. No. | Structure | IUPAC Name |
|---|---|---|
| 716 | 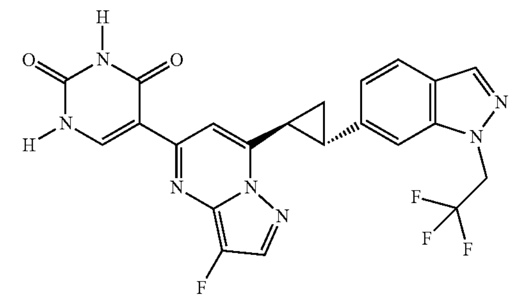 [SMILES: O=c1[nH]cc(-c2cc([C@H]3C[C@@H]3c3ccc4cnn(CC(F)(F)F)c4c3)n3ncc(F)c3n2)c(=O)[nH]1] | 5-(3-fluoro-7-((1S,2S)-2-(1-(2,2,2-trifluoroethyl)-1H-indazol-6-yl)cyclopropyl)pyrazolo[1,5-a]pyrimidin-5-yl)pyrimidine-2,4(1H,3H)-dione |
| 717 | 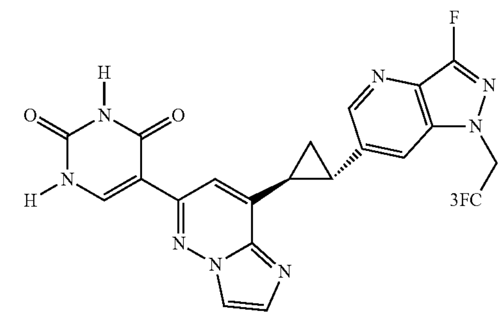 | 5-(8-((1S,2S)-2-(3-fluoro-1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione |
| 718 | 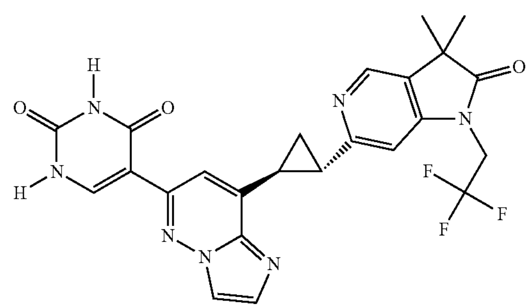 [SMILES: CC1(C)C(=O)N(CC(F)(F)F)c2cc([C@H]3C[C@@H]3c3cc(-c4c[nH]c(=O)[nH]c4=O)nn4ccnc34)ncc21] | 5-(8-((1S,2S)-2-(3,3-dimethyl-2-oxo-1-(2,2,2-trifluoroethyl)-2,3-dihydro-1H-pyrrolo[3,2-c]pyridin-6-yl)cyclopropyl)imidazo[1,2-b]pyridazin-6-yl)pyrimidine-2,4(1H,3H)-dione |
| 719 | 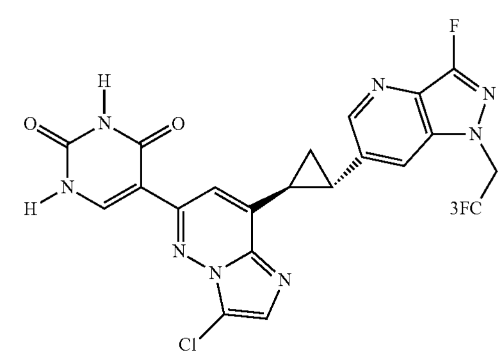 | 5-(3-chloro-8-((1S,2S)-2-(3-fluoro-1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 720 | 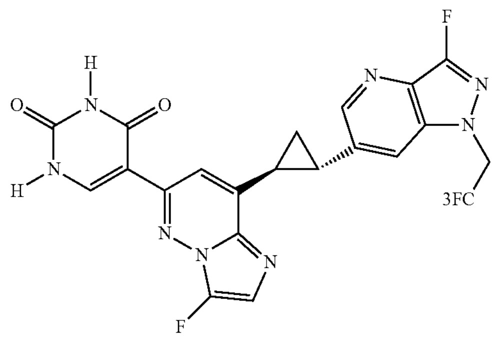 | 5-(3-fluoro-8-((1S,2S)-2-(3-fluoro-1-(2,2,2-trifluoroethyl)-1H-pyrazolo[4,3-b]pyridin-6-yl)cyclopropyl)imidazo[1,2-b]pyridazin-6-yl)pyrimidine-2,4(1H,3H)-dione |
| 721 | 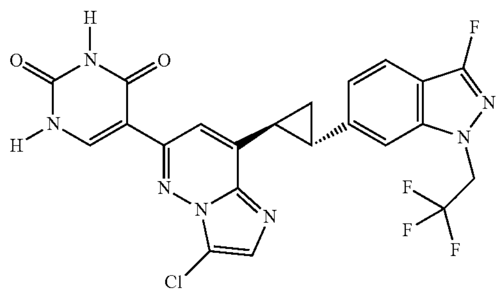 [SMILES: O=c1[nH]cc(-c2cc([C@H]3C[C@@H]3c3ccc4c(F)nn(CC(F)(F)F)c4c3)c3ncc(Cl)n3n2)c(=O)[nH]1] | 5-(3-chloro-8-((1S,2S)-2-(3-fluoro-1-(2,2,2-trifluoroethyl)-1H-indazol-6-yl)cyclopropyl)imidazo[1,2-b]pyridazin-6-yl)pyrimidine-2,4(1H,3H)-dione |
| 722 | 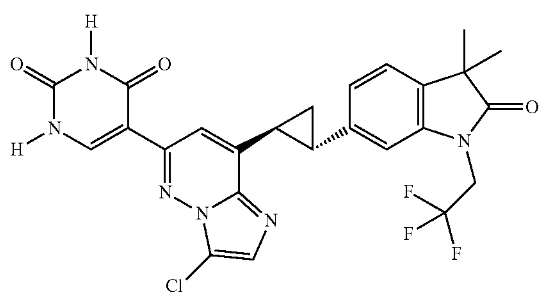 [SMILES: CC1(C)C(=O)N(CC(F)(F)F)c2cc([C@H]3C[C@@H]3c3cc(-c4c[nH]c(=O)[nH]c4=O)nn4c(Cl)cnc34)ccc21] | 5-(3-chloro-8-((1S,2S)-2-(3,3-dimethyl-2-oxo-1-(2,2,2-trifluoroethyl)indolin-6-yl)cyclopropyl)imidazo[1,2-b]pyridazin-6-yl)pyrimidine-2,4(1H,3H)-dione |
| 723 | 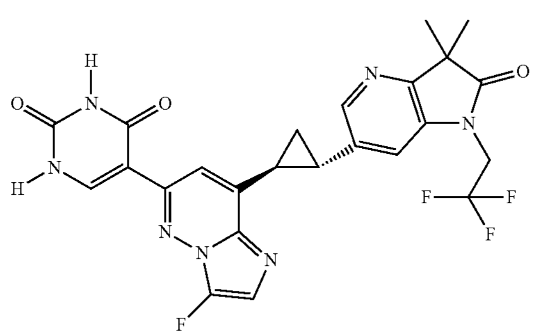 [SMILES: CC1(C)C(=O)N(CC(F)(F)F)c2cc([C@H]3C[C@@H]3c3cc(-c4c[nH]c(=O)[nH]c4=O)nn4c(F)cnc34)cnc21] | 5-(8-((1S,2S)-2-(3,3-dimethyl-2-oxo-1-(2,2,2-trifluoroethyl)-2,3-dihydro-1H-pyrrolo[3,2-b]pyridin-6-yl)cyclopropyl)-3-fluoroimidazo[1,2-b]pyridazin-6-yl)pyrimidine-2,4(1H,3H)-dione |

TABLE 2-continued

| Ex. No. | Structure | IUPAC Name |
|---|---|---|
| 724 | 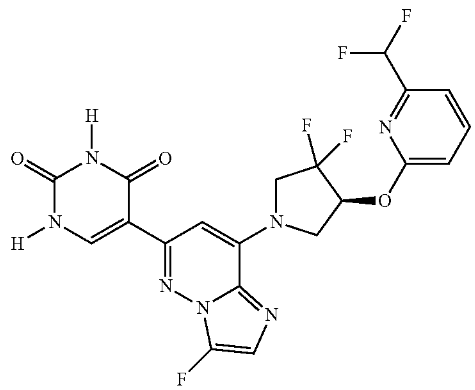 [SMILES: O=c1[nH]cc(-c2cc(N3C[C@H](Oc4cccc(C(F)F)n4)C(F)(F)C3)c3ncc(F)n3n2)c(=O)[nH]1] | (S)-5-(8-(4-((6-(difluoromethyl)pyridin-2-yl)oxy)-3,3-difluoropyrrolidin-1-yl)-3-fluoroimidazo[1,2-b]pyridazin-6-yl)pyrimidine-2,4(1H,3H)-dione |
| 725 | 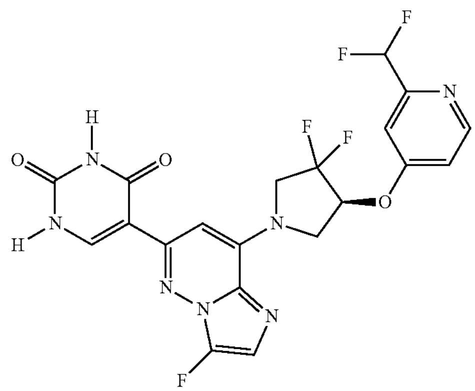 [SMILES: O=c1[nH]cc(-c2cc(N3C[C@H](Oc4ccnc(C(F)F)c4)C(F)(F)C3)c3ncc(F)n3n2)c(=O)[nH]1] | (S)-5-(8-(4-((2-(difluoromethyl)pyridin-4-yl)oxy)-3,3-difluoropyrrolidin-1-yl)-3-fluoroimidazo[1,2-b]pyridazin-6-yl)pyrimidine-2,4(1H,3H)-dione |
| 726 | 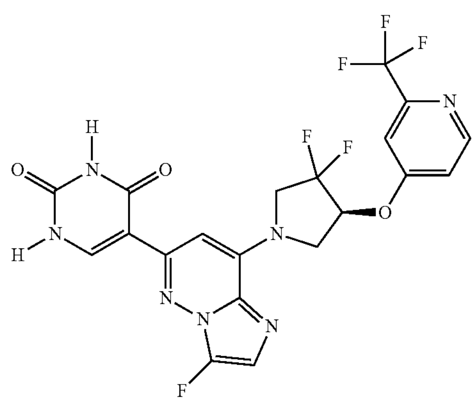 [SMILES: O=c1[nH]cc(-c2cc(N3C[C@H](Oc4ccnc(C(F)(F)F)c4)C(F)(F)C3)c3ncc(F)n3n2)c(=O)[nH]1] | (S)-5-(8-(3,3-difluoro-4-((2-(trifluoromethyl)pyridin-4-yl)oxy)pyrrolidin-1-yl)-3-fluoroimidazo[1,2-b]pyridazin-6-yl)pyrimidine-2,4(1H,3H)-dione |
| 727 | 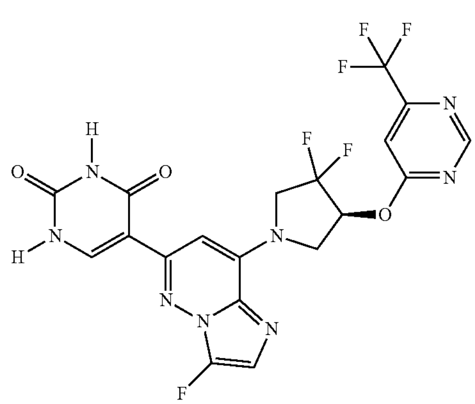 [SMILES: O=c1[nH]cc(-c2cc(N3C[C@H](Oc4cc(C(F)(F)F)ncn4)C(F)(F)C3)c3ncc(F)n3n2)c(=O)[nH]1] | (S)-5-(8-(3,3-difluoro-4-((6-(trifluoromethyl)pyrimidin-4-yl)oxy)pyrrolidin-1-yl)-3-fluoroimidazo[1,2-b]pyridazin-6-yl)pyrimidine-2,4(1H,3H)-dione |

TABLE 2-continued

| Ex. No. | Structure | IUPAC Name |
|---|---|---|
| 728 | 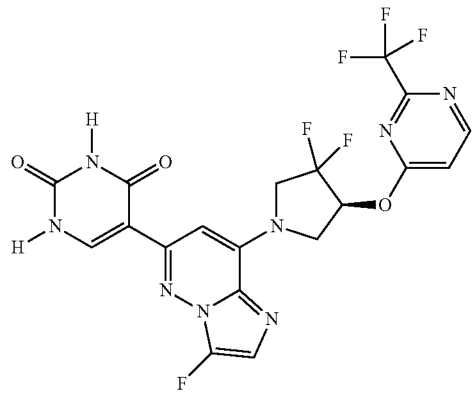 [SMILES: O=c1[nH]cc(-c2cc(N3C[C@H](Oc4ccnc(C(F)(F)F)n4)C(F)(F)C3)c3ncc(F)n3n2)c(=O)[nH]1] | (S)-5-(8-(3,3-difluoro-4-((2-(trifluoromethyl)pyrimidin-4-yl)oxy)pyrrolidin-1-yl)-3-fluoroimidazo[1,2-b]pyridazin-6-yl)pyrimidine-2,4(1H,3H)-dione |
| 729 | 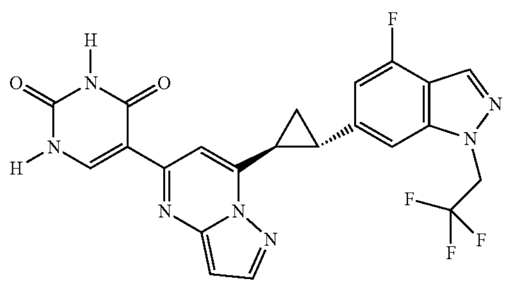 [SMILES: O=c1[nH]cc(-c2cc([C@H]3C[C@@H]3c3cc(F)c4cnn(CC(F)(F)F)c4c3)n3nccc3n2)c(=O)[nH]1] | 5-(7-((1S,2S)-2-(4-fluoro-1-(2,2,2-trifluoroethyl)-1H-indazol-6-yl)cyclopropyl)pyrazolo[1,5-a]pyrimidin-5-yl)pyrimidine-2,4(1H,3H)-dione |
| 730 | 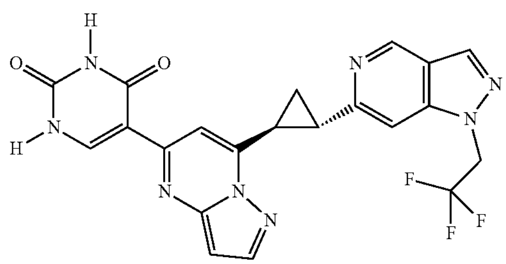 [SMILES: O=c1[nH]cc(-c2cc([C@H]3C[C@@H]3c3cc4c(cn3)cnn4CC(F)(F)F)n3nccc3n2)c(=O)[nH]1] | 5-(7-((1S,2S)-2-(1-(2,2,2-trifluoroethyl)-1H-pyrazolo[4,3-c]pyridin-6-yl)cyclopropyl)pyrazolo[1,5-a]pyrimidin-5-yl)pyrimidine-2,4(1H,3H)-dione |
| 731 | 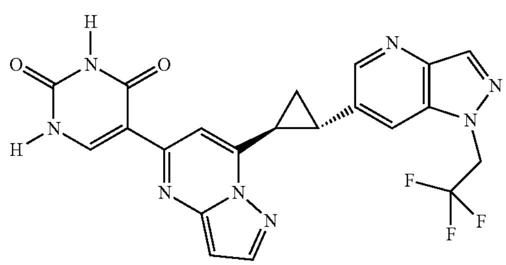 [SMILES: O=c1[nH]cc(-c2cc([C@H]3C[C@@H]3c3cnc4cnn(CC(F)(F)F)c4c3)n3nccc3n2)c(=O)[nH]1] | 5-(7-((1S,2S)-2-(1-(2,2,2-trifluoroethyl)-1H-pyrazolo[4,3-b]pyridin-6-yl)cyclopropyl)pyrazolo[1,5-a]pyrimidin-5-yl)pyrimidine-2,4(1H,3H)-dione |
| 732 | 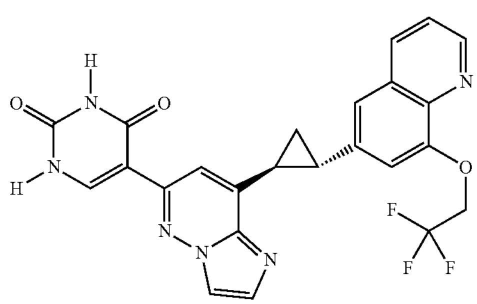 [SMILES: O=c1[nH]cc(-c2cc([C@H]3C[C@@H]3c3cc(OCC(F)(F)F)c4ncccc4c3)c3nccn3n2)c(=O)[nH]1] | 5-(8-((1S,2S)-2-(8-(2,2,2-trifluoroethoxy)quinolin-6-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 733 | 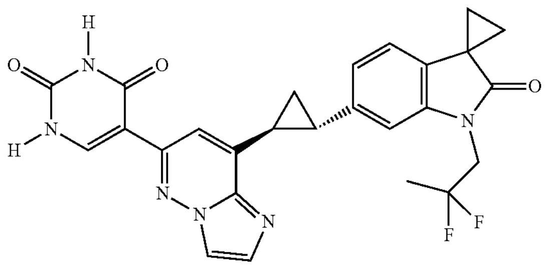 [SMILES: CC(F)(F)CN1C(=O)C2(CC2)c2ccc([C@H]3C[C@@H]3c3cc(-c4c[nH]c(=O)[nH]c4=O)nn4ccnc34)cc21] | 5-(8-((1S,2S)-2-(1'-(2,2-difluoropropyl)-2'-oxospiro[cyclopropane-1,3'-indolin]-6'-yl)cyclopropyl)imidazo[1,2-b]pyridazin-6-yl)pyrimidine-2,4(1H,3H)-dione |
| 734 | 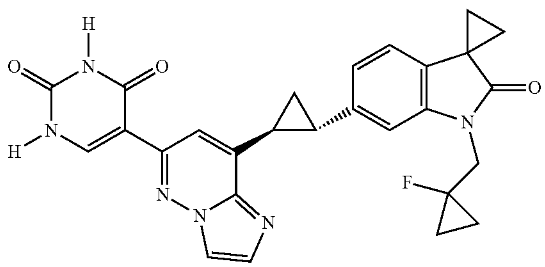 [SMILES: O=C1N(CC2(F)CC2)c2cc([C@H]3C[C@@H]3c3cc(-c4c[nH]c(=O)[nH]c4=O)nn4ccnc34)ccc2C12CC2] | 5-(8-((1S,2S)-2-(1'-((1-fluorocyclopropyl)methyl)-2'-oxospiro[cyclopropane-1,3'-indolin]-6'-yl)cyclopropyl)imidazo[1,2-b]pyridazin-6-yl)pyrimidine-2,4(1H,3H)-dione |
| 735 | 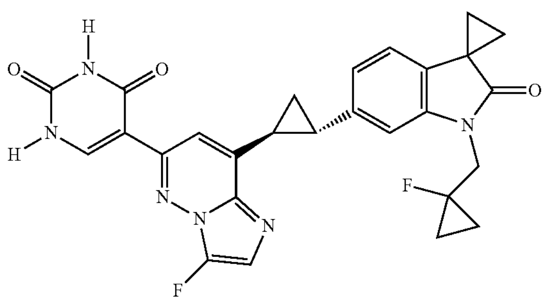 [SMILES: O=C1N(CC2(F)CC2)c2cc([C@H]3C[C@@H]3c3cc(-c4c[nH]c(=O)[nH]c4=O)nn4c(F)cnc34)ccc2C12CC2] | 5-(3-fluoro-8-((1S,2S)-2-(1'-((1-fluorocyclopropyl)methyl)-2'-oxospiro[cyclopropane-1,3'-indolin]-6'-yl)cyclopropyl)imidazo[1,2-b]pyridazin-6-yl)pyrimidine-2,4(1H,3H)-dione |
| 736 | 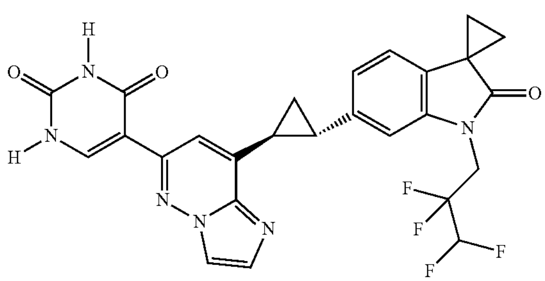 [SMILES: O=C1N(CC(F)(F)C(F)F)c2cc([C@H]3C[C@@H]3c3cc(-c4c[nH]c(=O)[nH]c4=O)nn4ccnc34)ccc2C12CC2] | 5-(8-((1S,2S)-2-(2'-oxo-1'-(2,2,3,3-tetrafluoropropyl)spiro[cyclopropane-1,3'-indolin]-6'-yl)cyclopropyl)imidazo[1,2-b]pyridazin-6-yl)pyrimidine-2,4(1H,3H)-dione |
| 737 | 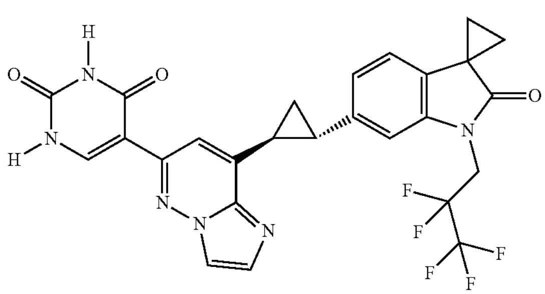 [SMILES: O=C1N(CC(F)(F)C(F)(F)F)c2cc([C@H]3C[C@@H]3c3cc(-c4c[nH]c(=O)[nH]c4=O)nn4ccnc34)ccc2C12CC2] | 5-(8-((1S,2S)-2-(2'-oxo-1'-(2,2,3,3,3-pentafluoropropyl)spiro[cyclopropane-1,3'-indolin]-6'-yl)cyclopropyl)imidazo[1,2-b]pyridazin-6-yl)pyrimidine-2,4(1H,3H)-dione |

TABLE 2-continued

| Ex. No. | Structure | IUPAC Name |
|---|---|---|
| 738 | 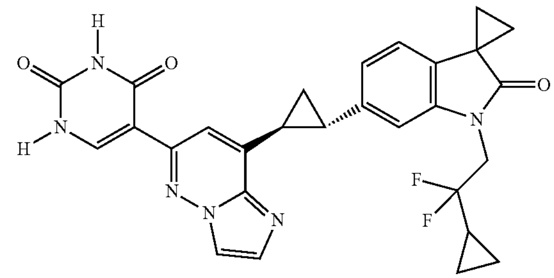 [SMILES: O=C1N(CC(F)(F)C2CC2)c2cc([C@H]3C[C@@H]3c3cc(-c4c[nH]c(=O)[nH]c4=O)nn4ccnc34)ccc2C12CC2] | 5-(8-((1S,2S)-2-(1'-(2-cyclopropyl-2,2-difluoroethyl)-2'-oxospiro[cyclopropane-1,3'-indolin]-6'-yl)cyclopropyl)imidazo[1,2-b]pyridazin-6-yl)pyrimidine-2,4(1H,3H)-dione |
| 739 | 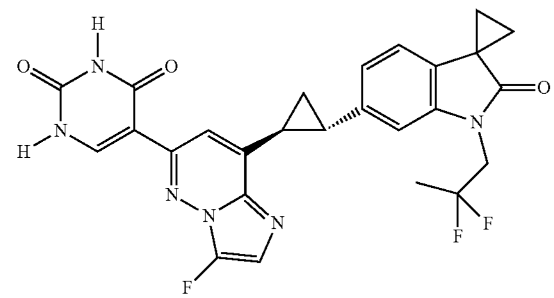 [SMILES: CC(F)(F)CN1C(=O)C2(CC2)c2ccc([C@H]3C[C@@H]3c3cc(-c4c[nH]c(=O)[nH]c4=O)nn4c(F)cnc34)cc21] | 5-(8-((1S,2S)-2-(1'-(2,2-difluoropropyl)-2'-oxospiro[cyclopropane-1,3'-indolin]-6'-yl)cyclopropyl)-3-fluoroimidazo[1,2-b]pyridazin-6-yl)pyrimidine-2,4(1H,3H)-dione |
| 740 | 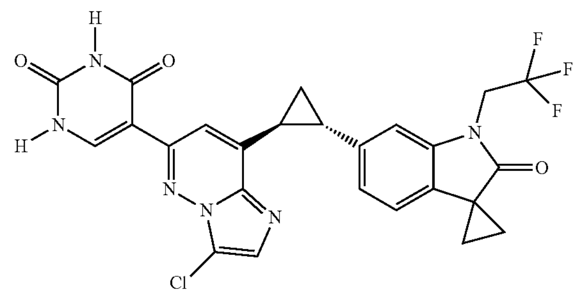 [SMILES: O=C1N(CC(F)(F)F)c2cc([C@H]3C[C@@H]3c3cc(-c4c[nH]c(=O)[nH]c4=O)nn4c(Cl)cnc34)ccc2C12CC2] | 5-(3-chloro-8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |
| 741 | 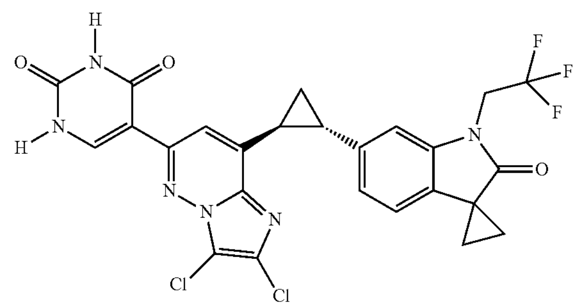 [SMILES: O=C1N(CC(F)(F)F)c2cc([C@H]3C[C@@H]3c3cc(-c4c[nH]c(=O)[nH]c4=O)nn4c(Cl)c(Cl)nc34)ccc2C12CC2] | 5-(2,3-dichloro-8-((1S,2S)-2-(2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |
| 742 | 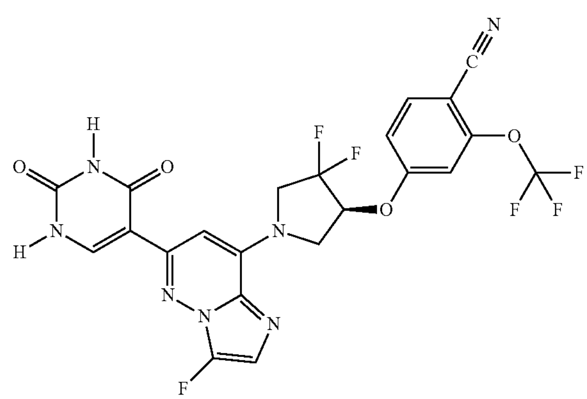 [SMILES: N#Cc1ccc(O[C@H]2CN(c3cc(-c4c[nH]c(=O)[nH]c4=O)nn4c(F)cnc34)CC2(F)F)cc1OC(F)(F)F] | (S)-4-((1-(6-(2,4-dioxo-1,2,3,4-tetrahydropyrimidin-5-yl)-3-fluoroimidazo[1,2-b]pyridazin-8-yl)-4,4-difluoropyrrolidin-3-yl)oxy)-2-(trifluoromethoxy)benzonitrile |

TABLE 2-continued

Examples

| Ex. No. | Structure | IUPAC Name |
|---|---|---|
| 743 | 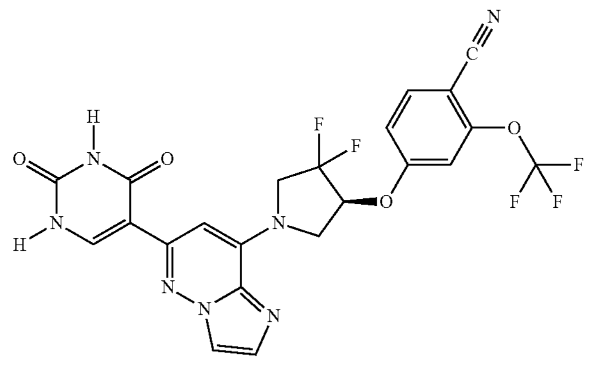 [SMILES: N#Cc1ccc(O[C@H]2CN(c3cc(-c4c[nH]c(=O)[nH]c4=O)nn4ccnc34)CC2(F)F)cc1OC(F)(F)F] | (S)-4-((1-(6-(2,4-dioxo-1,2,3,4-tetrahydropyrimidin-5-yl)imidazo[1,2-b]pyridazin-8-yl)-4,4-difluoropyrrolidin-3-yl)oxy)-2-(trifluoromethoxy)benzonitrile |
| 744 | 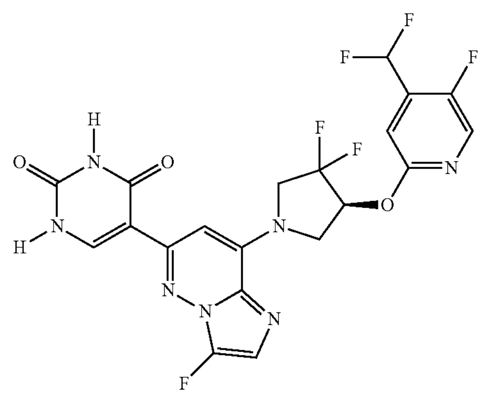 [SMILES: O=c1[nH]cc(-c2cc(N3C[C@H](Oc4cc(C(F)F)c(F)cn4)C(F)(F)C3)c3ncc(F)n3n2)c(=O)[nH]1] | (S)-5-(8-(4-((4-(difluoromethyl)-5-fluoropyridin-2-yl)oxy)-3,3-difluoropyrrolidin-1-yl)-3-fluoroimidazo[1,2-b]pyridazin-6-yl)pyrimidine-2,4(1H,3H)-dione |
| 745 | 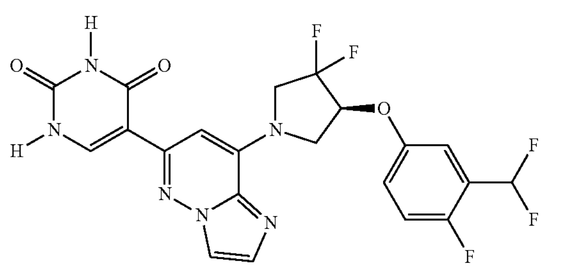 [SMILES: O=c1[nH]cc(-c2cc(N3C[C@H](Oc4ccc(F)c(C(F)F)c4)C(F)(F)C3)c3nccn3n2)c(=O)[nH]1] | (S)-5-(8-(4-(3-(difluoromethyl)-4-fluorophenoxy)-3,3-difluoropyrrolidin-1-yl)imidazo[1,2-b]pyridazin-6-yl)pyrimidine-2,4(1H,3H)-dione |
| 746 | 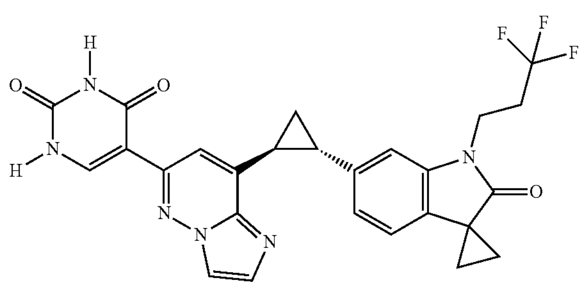 [SMILES: O=C1N(CCC(F)(F)F)c2cc([C@H]3C[C@@H]3c3cc(-c4c[nH]c(=O)[nH]c4=O)nn4ccnc34)ccc2C12CC2] | 5-(8-((1S,2S)-2-(2'-oxo-1'-(3,3,3-trifluoropropyl)spiro[cyclopropane-1,3'-indolin]-6'-yl)cyclopropyl)imidazo[1,2-b]pyridazin-6-yl)pyrimidine-2,4(1H,3H)-dione |
| 747 | 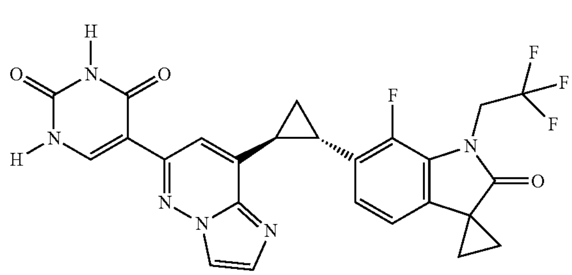 [SMILES: O=C1N(CC(F)(F)F)c2c(ccc([C@H]3C[C@@H]3c3cc(-c4c[nH]c(=O)[nH]c4=O)nn4ccnc34)c2F)C12CC2] | 5-(8-((1S,2S)-2-(7'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |

TABLE 2-continued

Examples

| Ex. No. | Structure | IUPAC Name |
|---|---|---|
| 748 | 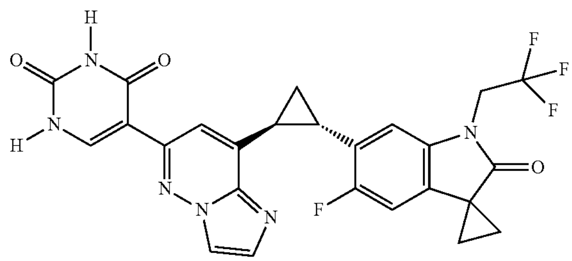 [SMILES: O=C1N(CC(F)(F)F)c2cc([C@H]3C[C@@H]3c3cc(-c4c[nH]c(=O)[nH]c4=O)nn4ccnc34)c(F)cc2C12CC2] | 5-(8-((1S,2S)-2-(5'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |
| 749 | 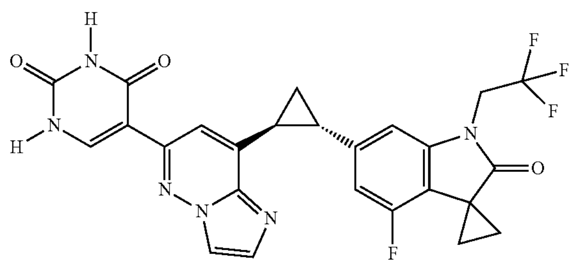 [SMILES: O=C1N(CC(F)(F)F)c2cc([C@H]3C[C@@H]3c3cc(-c4c[nH]c(=O)[nH]c4=O)nn4ccnc34)cc(F)c2C12CC2] | 5-(8-((1S,2S)-2-(4'-fluoro-2'-oxo-1'-(2,2,2-trifluoroethyl)spiro[cyclopropane-1,3'-indolin]-6'-yl)cyclopropyl)imidazo[1,2-b]pyridazin-6-yl)pyrimidine-2,4(1H,3H)-dione |

TABLE 3

Characterization Data

| Example No. | ES/MS m/z | NMR |
|---|---|---|
| 1 | 284.10 [M + H] | $^1$H NMR (400 MHz, DMSO-d6) δ 11.71 (d, J = 6.4 Hz, 1H), 11.62 (s, 1H), 8.34 (s, 1H), 8.08 (d, J = 6.2 Hz, 1H), 7.65 (s, 1H), 2.53 (s, 3H), 1.34-1.30 (m, 2H), 1.15-1.06 (m, 2H). |
| 2 | 346.20 [M + H] | $^1$H NMR (400 MHz, DMSO-d6) δ 11.66-11.54 (m, 2H), 8.91 (s, 1H), 8.14-8.06 (m, 2H), 8.04 (d, J = 6.2 Hz, 1H), 7.52 (dd, J = 8.4, 6.9 Hz, 2H), 7.48-7.37 (m, 2H), 2.67 (td, J = 8.4, 4.2 Hz, 1H), 1.35-1.20 (m, 4H). |
| 3 | 342.10 [M + H] | $^1$H NMR (400 MHz, DMSO-d6) δ 11.56 (d, J = 4.9 Hz, 2H), 8.74 (s, 1H), 8.00 (d, J = 6.3 Hz, 1H), 7.38 (s, 1H), 4.34 (q, J = 7.1 Hz, 2H), 1.34 (t, J = 7.1 Hz, 3H), 1.22 (ddt, J = 15.3, 5.1, 2.5 Hz, 4H). |
| 4 | 314.10 [M + H] | $^1$H NMR (400 MHz, Methanol-d4) δ 8.12 (s, 1H), 8.08 (d, J = 1.3 Hz, 1H), 7.69 (d, J = 1.3 Hz, 1H), 7.40 (s, 1H), 3.60-3.53 (m, 1H), 3.50-3.43 (m, 1H), 3.38 (s, 3H), 2.53-2.46 (m, 1H), 1.90-1.81 (m, 1H), 1.42-1.34 (m, 1H), 1.30-1.22 (m, 1H). |
| 5 | 310.20 [M + H] | $^1$H NMR (400 MHz, Methanol-d4) δ 8.38 (d, J = 2.0 Hz, 1H), 8.28 (s, 1H), 8.13 (d, J = 2.0 Hz, 1H), 7.65 (s, 1H), 2.56-2.44 (m, 1H), 2.42 (dd, J = 8.6, 5.7 Hz, 1H), 2.38-2.26 (m, 1H), 2.27-2.10 (m, 2H), 2.08-1.92 (m, 2H), 1.60 (dd, J = 8.6, 5.7 Hz, 1H), 1.42 (t, J = 5.7 Hz, 1H). |
| 6 | 326.20 [M + H] | $^1$H NMR (400 MHz, Methanol-d4) δ 8.34-8.30 (m, 1H), 8.24 (s, 1H), 8.06-8.02 (m, 1H), 7.78 (s, 1H), 2.44-2.36 (m, 1H), 1.60-1.51 (m, 1H), 1.47-1.39 (m, 1H), 1.31-1.22 (m, 1H), 1.01 (s, 9H). |
| 7 | 346.10 [M + H] | $^1$H NMR (400 MHz, Methanol-d4) δ 8.38 (d, J = 1.9 Hz, 1H), 8.30 (s, 1H), 8.07 (d, J = 1.9 Hz, 1H), 8.01 (s, 1H), 7.38-7.22 (m, 5H), 2.74 (t, J = 7.5 Hz, 2H), 1.93 (tt, J = 7.5, 3.7 Hz, 2H). |
| 8 | 310.10 [M + H] | $^1$H NMR (400 MHz, Methanol-d4) δ 8.14 (s, 1H), 8.06 (d, J = 1.3 Hz, 1H), 7.68 (d, J = 1.3 Hz, 1H), 7.32 (s, 1H), 2.43-2.34 (m, 1H), 1.63-1.52 (m, 1H), 1.28-1.21 (m, 1H), 1.15-1.10 (m, 1H), 1.12-0.99 (m, 1H), 0.55-0.43 (m, 2H), 0.32-0.21 (m, 2H). |
| 9 | 299.20 [M + H] | $^1$H NMR (400 MHz, DMSO-d6) δ 11.61 (dd, J = 6.4, 2.0 Hz, 1H), 11.49 (d, J = 2.0 Hz, 1H), 8.31 (d, J = 1.7 Hz, 1H), 8.03 (d, J = 6.2 Hz, 1H), 7.93 (s, 1H), 6.95 (s, 1H), 3.79 (brs, 4H), 2.08-1.95 (m, 4H). |
| 10 | 315.20 [M + H] | $^1$H NMR (400 MHz, DMSO-d6) δ 11.60 (dd, J = 6.2, 2.0 Hz, 1H), 11.52 (d, J = 2.0 Hz, 1H), 8.26 (d, J = 1.5 Hz, 1H), 8.02 (d, J = 6.2 Hz, 1H), 7.83 (s, 1H), 7.18 (s, 1H), 3.85-3.73 (m, 8H). |
| 11 | 296.10 [M + H] | $^1$H NMR (400 MHz, DMSO-d6) δ 11.82 (dd, J = 6.3, 2.0 Hz, 1H), 11.67 (d, J = 1.9 Hz, 1H), 10.06 (t, J = 1.4 Hz, 1H), 8.66 (t, J = 1.8 Hz, 1H), 8.55 (d, J = 1.3 Hz, 1H), 8.24 (s, 1H), 8.14 (d, J = 6.2 Hz, 1H), 7.96 (d, J = 1.3 Hz, 1H), 7.90 (dd, J = 2.0, 1.2 Hz, 1H). |

TABLE 3-continued

Characterization Data

| Example No. | ES/MS m/z | NMR |
|---|---|---|
| 12 | 335.1 [M + 1] | $^1$H NMR (400 MHz, DMSO-d6) δ 11.52-11.40 (m, 2H), 8.18 (dd, J = 8.0, 3.9 Hz, 2H), 7.97 (d, J = 6.1 Hz, 1H), 7.79 (s, 1H), 7.44-7.38 (m, 2H), 7.38-7.31 (m, 2H), 7.31-7.23 (m, 1H), 6.99 (s, 1H), 4.56 (d, J = 5.9 Hz, 2H). |
| 13 | 349.1 [M + 1] | $^1$H NMR (400 MHz, DMSO-d6) δ 11.38 (d, J = 6.6 Hz, 2H), 8.05 (d, J = 1.2 Hz, 1H), 7.96 (d, J = 6.0 Hz, 1H), 7.56 (d, J = 1.2 Hz, 1H), 7.35-7.27 (m, 2H), 7.27-7.20 (m, 3H), 6.80 (s, 1H), 5.55 (s, 2H), 3.14 (s, 3H). |
| 14 | 348.1 [M + 1] | $^1$H NMR (400 MHz, DMSO-d6) δ 11.63 (dd, J = 6.2, 2.0 Hz, 1H), 11.59 (d, J = 2.0 Hz, 1H), 8.40 (d, J = 1.6 Hz, 1H), 8.07 (d, J = 6.2 Hz, 1H), 8.04-7.96 (m, 1H), 7.81 (s, 1H), 3.39-3.27 (m, 1H), 2.25-1.95 (m, 6H), 1.87 (dt, J = 14.5, 11.1 Hz, 2H). $^{19}$F NMR (376 MHz, DMSO-d6) δ −75.13 (s, 3F), −89.97 (d, J = 233.5 Hz, 1F), −99.92-101.11 (m, 1F). |
| 15 | 340.1 [M + 1] | $^1$H NMR (400 MHz, DMSO-d6) δ 11.61 (d, J = 1.9 Hz, 1H), 11.59 (s, 1H), 8.90 (d, J = 1.0 Hz, 1H), 8.03 (d, J = 6.0 Hz, 1H), 7.76 (s, 1H), 3.51 (p, J = 6.9 Hz, 1H), 1.36 (d, J = 6.9 Hz, 6H). $^{19}$F NMR (376 MHz, DMSO-d6) δ −61.57 (s, 3F). |
| 16 | 273.1 [M + 1] | $^1$H NMR (400 MHz, DMSO-d6) δ 11.64-11.58 (m, 1H), 11.57 (d, J = 2.0 Hz, 1H), 9.59 (s, 1H), 8.05 (d, J = 6.2 Hz, 1H), 7.65 (d, J = 0.9 Hz, 1H), 3.52-3.45 (m, 2H), 1.41 (d, J = 6.9 Hz, 6H). |
| 17 | 320.1 [M + 1] | $^1$H NMR (400 MHz, DMSO-d$_6$) δ 11.59-11.53 (m, 1H), 11.51 (d, J = 2.0 Hz, 1H), 8.37 (d, J = 1.4 Hz, 1H), 8.01 (d, J = 6.2 Hz, 1H), 7.94 (d, J = 10.9 Hz, 1H), 7.64 (s, 1H), 7.44-7.35 (m, 2H), 7.31 (dd, J = 8.3, 6.6 Hz, 2H), 7.27-7.19 (m, 1H), 4.34 (s, 2H). |
| 18 | 338.1 [M + 1] | $^1$H NMR (400 MHz, DMSO-d$_6$) δ 11.60 (d, J = 10.0 Hz, 2H), 8.35 (s, 1H), 8.07 (d, J = 6.1 Hz, 1H), 7.95 (s, 1H), 7.84 (s, 1H), 1.60-1.52 (m, 2H), 1.49 (d, J = 12.1 Hz, 2H). |
| 19 | 446.1 [M + 1] | $^1$H NMR (400 MHz, DMSO-d$_6$) δ 11.62 (d, J = 2.0 Hz, 1H), 11.54 (dd, J = 6.3, 2.0 Hz, 1H), 8.03 (s, 1H), 8.01 (d, J = 6.3 Hz, 1H), 7.93 (s, 1H), 1.55 (td, J = 7.5, 5.1 Hz, 4H), 1.48-1.36 (m, 4H). |
| 20 | 384.0 [M + 1] | $^1$H NMR (400 MHz, DMSO-d$_6$) δ 11.71-11.63 (m, 1H), 11.57 (d, J = 2.0 Hz, 1H), 8.09 (d, J = 9.7 Hz, 1H), 7.98 (d, J = 6.2 Hz, 1H), 7.88 (d, J = 9.6 Hz, 1H), 7.69 (s, 1H), 7.64-7.55 (m, 3H), 7.45 (t, J = 7.6 Hz, 2H), 5.27 (s, 2H). |
| 21 | 538.1 [M + 1] | $^1$H NMR (400 MHz, DMSO-d$_6$) δ 11.67 (d, J = 6.0 Hz, 1H), 11.55 (s, 1H), 7.96 (d, J = 6.3 Hz, 1H), 7.84 (s, 1H), 7.79-7.74 (m, 2H), 7.73-7.66 (m, 1H), 7.62-7.51 (m, 5H), 7.49-7.41 (m, 3H), 5.21 (s, 2H), 5.08 (s, 2H). |
| 22 | 270.10 [M + 1]. | $^1$H NMR (400 MHz, DMSO-d$_6$) δ 11.68-11.28 (m, 2H), 8.33 (s, 1H), 8.01 (d, J = 6.2 Hz, 1H), 7.89 (s, 1H), 7.45 (s, 1H), 2.47-2.42 (m, 1H), 1.27-1.15 (m, 4H). |
| 23 | 230.10 [M + H] | $^1$H NMR (400 MHz, DMSO-d6) δ 9.65 (s, 1H), 8.41 (s, 1H), 8.13 (d, J = 9.7 Hz, 1H), 8.09 (s, 1H), 7.85 (d, J = 9.7 Hz, 1H), 7.58 (d, J = 1.1 Hz, 1H). |
| 24 | 286.10 [M + H] | $^1$H NMR (400 MHz, DMSO-d6) δ 9.57 (s, 1H), 8.43 (s, 1H), 8.09-7.99 (m, 2H), 7.44 (d, J = 1.1 Hz, 1H), 4.08 (tt, J = 6.2, 3.0 Hz, 1H), 0.94-0.78 (m, 4H). |
| 25 | 288.10 [M + H] | $^1$H NMR (400 MHz, Methanol-d4) δ 8.34 (d, J = 2.0 Hz, 1H), 8.33 (s, 1H), 8.02 (d, J = 2.0 Hz, 1H), 7.95 (s, 1H), 5.19-5.08 (m, 1H), 1.58 (d, J = 6.1 Hz, 6H). |
| 26 | 336.1 [M + 1] | $^1$H NMR (400 MHz, DMSO-d6) δ 11.68-11.46 (m, 2H), 8.30 (s, 1H), 8.07 (d, J = 6.1 Hz, 1H), 7.79 (s, 1H), 7.60-7.51 (m, 3H), 7.48-7.36 (m, 3H), 5.45 (s, 2H). |
| 27 | 270.10 [M + H] | $^1$H NMR (400 MHz, DMSO-d6) δ 11.63-11.57 (m, 1H), 11.50 (s, 1H), 8.32 (d, J = 6.3 Hz, 1H), 8.21 (d, J = 2.3 Hz, 1H), 7.51 (s, 1H), 6.62 (d, J = 2.3 Hz, 1H), 2.85-2.74 (m, 1H), 1.34-1.27 (m, 2H), 1.10-1.03 (m, 2H). |
| 41 | 414.10 [M + H] | $^1$H NMR (400 MHz, Methanol-d4) δ 8.39-8.38 (m, 1H), 8.31-8.30 (m, 1H), 8.11-8.02 (m, 2H), 7.64-7.53 (m, 4H), 2.89-2.80 (m, 2H), 1.99-1.96 (m, 2H). $^{19}$F NMR (376 MHz, Methanol-d4) δ −64.67 (s, 3F), −77.72 (s, 3F). |
| 42 | 414.10 [M + H] | $^1$H NMR (400 MHz, Methanol-d4) δ 8.40 (d, J = 2.0 Hz, 1H), 8.31 (s, 1H), 8.12-8.04 (m, 2H), 7.69-7.62 (m, 2H), 7.49-7.47 (m, 2H), 2.85-2.81 (m, 2H), 2.03-1.96 (td, J = 7.4, 2.1 Hz, 2H). $^{19}$F NMR (376 MHz, Methanol-d4) δ −64.47 (s, 3F), −77.75 (s, 3F). |
| 45 | 386.10 [M + H] | $^1$H NMR (400 MHz, Acetonitrile-d3) δ 7.06 (d, J = 2.1 Hz, 1H), 6.96 (s, 1H), 6.77 (d, J = 2.1 Hz, 1H), 6.72 (s, 1H), 5.87-5.76 (m, 2H), 5.75-5.64 (m, 2H), 1.40-1.18 (m, 2H), 0.67-0.43 (m, 3H), −0.34--0.52 (m, 2H), −0.60--0.81 (m, 2H). |

TABLE 3-continued

Characterization Data

| Example No. | ES/MS m/z | NMR |
|---|---|---|
| 47 | 430.10 [M + H] | $^1$H NMR (400 MHz, Methanol-d4) δ 8.37 (d, J = 1.9 Hz, 1H), 8.29 (s, 1H), 8.06 (d, J = 1.9 Hz, 1H), 8.00 (s, 1H), 7.45 (t, J = 8.0 Hz, 1H), 7.30 (dt, J = 7.9, 1.3 Hz, 1H), 7.22 (s, 1H), 7.18 (ddt, J = 8.0, 2.3, 1.1 Hz, 1H), 2.81 (ddt, J = 9.0, 6.4, 3.5 Hz, 2H), 2.04-1.86 (m, 2H). $^{19}$F NMR (376 MHz, Methanol-d4) δ −59.86 (s, 3F), −77.69 (s, 3F). |
| 48 | 430.10 [M + H] | $^1$H NMR (400 MHz, Methanol-d4) δ 8.38 (d, J = 1.9 Hz, 1H), 8.30 (s, 1H), 8.07 (d, J = 1.9 Hz, 1H), 8.02 (s, 1H), 7.46-7.34 (m, 2H), 7.27 (d, J = 8.2 Hz, 2H), 2.89-2.70 (m, 2H), 2.01-1.86 (m, 2H). $^{19}$F NMR (376 MHz, Methanol-d4) δ −60.15 (s, 3F), −77.77 (s, 3F). |
| 52 | 347.10 [M + H] | $^1$H NMR (400 MHz, DMSO-d6) δ 11.78-11.76 (m, 1H), 11.64-11.63 (m, 1H), 8.69-8.67 (m, 1H), 8.56-8.55 (m, 1H), 8.24-8.14 (m, 2H), 8.13-8.11 (m, 1H), 7.88 (s, 1H), 7.76-7.74 (m, 1H), 7.64-7.61 (m, 1H), 3.25-3.21 (m, 1H), 3.13-3.10 (m, 1H), 2.23-2.11 (m, 2H). |
| 53 | 347.10 [M + H] | $^1$H NMR (400 MHz, Methanol-d4) δ 8.84-8.83 (m, 1H), 8.74-8.67 (m, 1H), 8.42-8.39 (m, 1H), 8.37-8.24 (m, 2H), 7.98-7.95 (m, 3H), 3.03-2.91 (m, 2H), 2.17-2.12 (m, 1H), 2.06-2.01 (m, 1H). |
| 54 | 347.10 [M + H] | $^1$H NMR (400 MHz, Methanol-d4) 8.75-8.73 (m, 2H), 8.31-8.27 (m, 2H), 7.96-7.94 (m, 4H), 3.23-3.18 (m, 1H), 3.05-3.01 (m, 1H), 2.38-2.32 (m, 1H), 2.18-2.13 (m, 1H). |
| 55 | 363.1 [M + 1] | $^1$H NMR (400 MHz, DMSO-d6) δ 11.60 (d, J = 3.9 Hz, 2H), 8.09 (d, J = 6.5 Hz, 1H), 7.97 (s, 1H), 3.31-3.24 (m, 1H), 2.53 (s, 3H), 2.20-1.86 (m, 8H). $^{19}$F NMR (376 MHz, DMSO-d6) δ −90.03 (d, J = 233.5 Hz, 1F), −99.94 (m, 1F). |
| 56 | 373.1 [M + 1] | $^1$H NMR (400 MHz, DMSO-d6) δ 11.64 (d, J = 6.8 Hz, 2H), 8.55 (s, 1H), 8.12 (d, J = 6.1 Hz, 1H), 7.94 (s, 1H), 3.32-3.23 (m, 1H), 2.24-1.86 (m, 8H). $^{19}$F NMR (376 MHz, DMSO-d6) δ −90.04 (d, J = 233.4 Hz, 1F), −101.02 (m, 1F). |
| 57 | 362.1 [M + 1] | $^1$H NMR (400 MHz, DMSO-d6) δ 11.67 (d, J = 6.3 Hz, 1H), 11.61 (d, J = 2.0 Hz, 1H), 8.19 (d, J = 6.2 Hz, 1H), 7.90 (s, 2H), 3.32 (t, J = 12.1 Hz, 1H), 2.55 (d, J = 1.0 Hz, 3H), 2.26-2.13 (m, 2H), 2.13-2.03 (m, 3H), 2.03-1.93 (m, 1H), 1.93-1.78 (m, 2H). $^{19}$F NMR (376 MHz, DMSO-d6) δ −74.95 (s, 3F), −90.00 (d, J = 233.9 Hz, 1F), −99.99 (m, 1F). |
| 58 | 350.10 [M + H] | $^1$H NMR (400 MHz, DMSO-d6) δ 11.64 (dd, J = 6.2, 2.0 Hz, 1H), 11.60 (d, J = 2.0 Hz, 1H), 8.42 (d, J = 1.5 Hz, 1H), 8.09 (d, J = 6.2 Hz, 1H), 8.04 (s, 1H), 7.95 (d, J = 1.5 Hz, 1H), 7.46-7.41 (m, 2H), 7.41-7.35 (m, 2H), 7.35-7.28 (m, 1H), 4.96 (s, 2H), 4.72 (s, 2H). |
| 59 | 361.1 [M + 1] | $^1$H NMR (400 MHz, DMSO-d6) δ 11.47-11.33 (m, 2H), 8.07 (d, J = 1.3 Hz, 1H), 7.94 (d, J = 6.1 Hz, 1H), 7.61 (s, 1H), 7.47-7.41 (m, 2H), 7.38 (dd, J = 8.4, 6.8 Hz, 2H), 7.31-7.25 (m, 1H), 6.54 (s, 1H), 4.87-4.74 (m, 2H), 4.41-4.31 (m, 2H), 4.11 (tt, J = 8.6, 6.1 Hz, 1H). |
| 60 | 382.1 [M + 1] | $^1$H NMR (400 MHz, DMSO-d6) δ 11.52 (d, J = 4.1 Hz, 2H), 8.30 (d, J = 1.3 Hz, 1H), 8.01 (d, J = 6.4 Hz, 1H), 7.81 (s, 1H), 7.54 (s, 1H), 7.05 (td, J = 8.2, 7.4, 3.2 Hz, 3H), 2.88 (dt, J = 9.3, 5.5 Hz, 1H), 2.77 (ddd, J = 8.8, 6.1, 4.3 Hz, 1H), 2.14 (dt, J = 8.7, 5.4 Hz, 1H), 1.81 (dt, J = 8.7, 5.3 Hz, 1H). $^{19}$F NMR (376 MHz, DMSO-d6) δ −74.90 (m, 3F), −110.76 (dd, J = 10.3, 7.6 Hz, 2F). |
| 61 | 389.1 [M + 1] | $^1$H NMR (400 MHz, DMSO-d6) δ 11.54 (d, J = 3.7 Hz, 2H), 8.31 (d, J = 1.4 Hz, 1H), 8.02 (d, J = 6.4 Hz, 1H), 7.88-7.79 (m, 2H), 7.58 (s, 1H), 7.47 (dd, J = 11.1, 1.5 Hz, 1H), 7.34 (dd, J = 8.2, 1.6 Hz, 1H), 2.96 (dd, J = 8.8, 5.1 Hz, 1H), 2.86 (ddd, J = 8.9, 6.2, 4.4 Hz, 1H), 2.24 (dt, J = 8.7, 5.4 Hz, 1H), 1.89 (dt, J = 8.8, 5.5 Hz, 1H). $^{19}$F NMR (376 MHz, DMSO-d6) δ −75.04 (s, 3F), −109.50 (dd, J = 11.0, 7.2 Hz, 1F). |
| 62 | 353.1 [M + 1] | $^1$H NMR (400 MHz, DMSO-d6) δ 11.43 (dt, J = 6.1, 2.0 Hz, 2H), 8.09 (d, J = 1.3 Hz, 1H), 7.94 (d, J = 6.1 Hz, 1H), 7.62 (d, J = 1.3 Hz, 1H), 6.53 (s, 1H), 4.62 (t, J = 9.2 Hz, 2H), 4.41-4.33 (m, 2H), 3.83 (dh, J = 14.1, 5.0 Hz, 1H). $^{19}$F NMR (376 MHz, DMSO-d6) δ −72.74 (d, J = 9.3 Hz, 3F), −75.39 (s, 3F). |
| 63 | 313.2 [M + 1] | $^1$H NMR (400 MHz, DMSO-d6) δ 11.42 (d, J = 6.7 Hz, 2H), 8.09 (d, J = 1.3 Hz, 1H), 7.94 (d, J = 6.0 Hz, 1H), 7.64 (d, J = 1.3 Hz, 1H), 6.50 (s, 1H), 4.10-4.03 (m, 4H), 1.32 (s, 6H). |
| 64 | 389.1 [M + 1] | $^1$H NMR (400 MHz, DMSO-d6) δ 11.59 (d, J = 7.5 Hz, 2H), 8.37 (d, J = 1.5 Hz, 1H), 8.04 (d, J = 6.0 Hz, 1H), 7.91 (s, 1H), 7.85 (dd, J = 6.1, 2.4 Hz, 1H), 7.71 (ddd, J = 7.9, 5.2, 2.4 Hz, 1H), 7.60 (s, 1H), 7.49 (t, J = 9.0 Hz, 1H), 2.88 (ddd, J = 9.3, 6.2, 4.4 Hz, 1H), 2.81-2.73 (m, 1H), 2.10 (dt, J = 9.0, 5.4 Hz, 1H), 1.85 (dt, J = 8.6, 5.5 Hz, 1H). $^{19}$F NMR (376 MHz, DMSO-d6) δ −75.13 (s, 3F), −113.01 (q, J = 6.2 Hz, 1F). |

TABLE 3-continued

Characterization Data

| Example No. | ES/MS m/z | NMR |
|---|---|---|
| 65 | 382.1 [M + 1] | $^1$H NMR (400 MHz, DMSO-d6) δ 11.58 (d, J = 5.5 Hz, 2H), 8.36 (s, 1H), 8.03 (d, J = 6.2 Hz, 1H), 7.90 (s, 1H), 7.62 (s, 1H), 7.28-7.14 (m, 2H), 7.14-7.07 (m, 1H), 2.97 (dd, J = 9.3, 5.1 Hz, 1H), 2.78 (dt, J = 9.7, 5.4 Hz, 1H), 2.10 (dt, J = 10.1, 5.5 Hz, 1H), 1.86 (dt, J = 10.6, 5.6 Hz, 1H). $^{19}$F NMR (376 MHz, DMSO-d6) δ −75.04 (s, 3F), −118.79 (dtd, J = 17.8, 8.8, 4.7 Hz, 1F), −126.06 (m, 1F). |
| 66 | 361.1 [M + 1] | $^1$H NMR (400 MHz, Methanol-d4) δ 8.25 (s, 1H), 8.23 (d, J = 2.3 Hz, 1H), 7.70 (s, 1H), 7.60 (d, J = 2.4 Hz, 1H), 7.46-7.39 (m, 3H), 7.26-7.22 (m, 2H), 5.87 (dd, J = 7.4, 3.7 Hz, 1H), 3.61-3.51 (m, 2H), 2.75-2.65 (m, 2H). |
| 67 | 393.10 [M + 1] | $^1$H NMR (400 MHz, DMSO-d6) δ 11.58-11.51 (m, 1H), 11.46-11.45 (m, 1H), 8.26-8.25 (m, 1H), 8.03-8.01 (m, 1H), 7.86 (s, 1H), 7.50-7.40 (m, 2H), 7.25-7.14 (m, 2H), 6.92 (s, 1H), 4.38 (brs, 1H), 4.00 (brs, 1H), 3.82 (brs, 2H), 3.68-3.56 (m, 1H), 2.45-2.42 (m, 1H), 2.22-2.07 (m, 1H). $^{19}$F NMR (376 MHz, DMSO-d6) δ −116.67 (m, 1F). |
| 68 | 393.10 [M + 1] | $^1$H NMR (400 MHz, DMSO-d6) δ 11.56-11.54 (m, 1H), 11.46-11.45 (m, 1H), 8.27-8.26 (m, 1H), 8.03-8.01 (m, 1H), 7.87 (s, 1H), 7.47-7.43 (m, 2H), 7.22-7.17 (m, 2H), 6.92 (s, 1H), 4.38 (brs, 1H), 3.96 (brs, 1H), 3.81 (brs, 2H), 3.68-3.56 (m, 1H), 2.47-2.42 (m, 1H), 2.19-2.09 (m, 1H). $^{19}$F NMR (376 MHz, DMSO-d6) δ −116.67 (m, 1F). |
| 69 | 288.10 [M + H] | $^1$H NMR (400 MHz, DMSO-d6) δ 11.60-11.58 (m, 1H), 11.53-11.52 (m, 1H), 8.03-8.02 (m, 1H), 7.68-7.66 (m, 1H), 7.40 (s, 1H), 2.51-2.42 (m, 1H), 1.26-1.23 (m, 4H). $^{19}$F NMR (376 MHz, DMSO-d6) δ −155.46 (d, J = 6.9 Hz, 1F). |
| 70 | 349.10 [M + 1] | $^1$H NMR (400 MHz, DMSO-d6) δ 11.55-11.54 (m, 1H), 11.48-11.47 (m, 1H), 8.22-8.21 (m, 1H), 8.01-7.97 (m, 1H), 7.80-7.75 (m, 1H), 7.18 (s, 1H), 4.00-3.98 (m, 4H), 2.22-2.12 (m, 4H). $^{19}$F NMR (376 MHz, DMSO-d6) δ −95.83 (m, 2F). |
| 71 | 375.20 [M + 1] | $^1$H NMR (400 MHz, DMSO-d6) δ 11.84-11.82 (m, 1H), 11.63-11.62 (m, 1H), 8.61-8.60 (m, 1H), 8.28-8.08 (m, 3H), 7.87-7.85 (m, 2H), 6.98-6.96 (m, 2H), 3.07-3.06 (m, 2H), 1.18-1.06 (m, 1H), 0.56-0.47 (m, 2H), 0.35-0.22 (m, 2H). |
| 72 | 327.20 [M + 1] | $^1$H NMR (400 MHz, DMSO-d6) δ 11.43-11.40 (m, 2H), 8.09-8.08 (m, 1H), 7.95-7.94 (m, 1H), 7.63-7.62 (m, 1H), 6.63 (s, 1H), 3.84-3.68 (m, 4H), 1.85-1.77 (m, 2H), 1.13 (s, 6H). |
| 73 | 335.10 [M + H] | $^1$H NMR (400 MHz, DMSO-d6) δ 11.59-11.57 (m, 1H), 11.47-1.46 (m, 1H), 8.28-8.23 (m, 1H), 8.03-8.01 (m, 1H), 7.83-7.82 (m, 1H), 6.89 (s, 1H), 5.71-5.45 (m, 2H), 4.41-4.05 (m, 4H). $^{19}$F NMR (377 MHz, DMSO-d6) δ −188.83(m, 2F). |
| 74 | 396.20 [M + H] | $^1$H NMR (400 MHz, Methanol-d4) δ 8.46-8.45 (m, 1H), 8.36 (s, 1H), 8.24 (s, 1H), 8.16-8.08 (m, 2H), 7.96-7.88 (m, 1H), 7.85-7.83 m, 1H), 7.56-7.42 (m, 4H), 3.30-3.26 (m, 1H), 2.68-2.63 (m, 1H), 2.17-2.11 (m, 1H), 2.08-1.93 (m, 1H). |
| 75 | 310.20 [M + 1] | $^1$H NMR (400 MHz, DMSO-d6) δ 11.62-11.55 (m, 2H), 8.27 (s, 1H), 8.02-8.01 (m, 1H), 7.53 (s, 1H), 2.58-2.51 (m, 1H), 2.20-2.08 (m, 1H), 1.34-1.22 (m, 2H), 1.17-1.08 (m, 4H), 1.05-0.93 (m, 2H). $^{19}$F NMR (376 MHz, DMSO-d6) δ −75.35. |
| 76 | 382.10 [M + H] | $^1$H NMR (400 MHz, DMSO-d6) δ 11.63-11.61 (m, 1H), 11.55-1.54 (m, 1H), 8.05-8.04 (m, 1H), 7.66-7.64 (m, 1H), 7.51 (s, 1H), 7.36-7.25 (m, 2H), 7.19-7.08 (m, 2H), 2.85-2.80 (m, 1H), 2.73-2.68 (m, 1H), 2.06-2.01 (m, 1H), 1.77-1.72 (m, 1H). $^{19}$F NMR (376 MHz, DMSO-d6) δ −117.32 (m, 1F), −155.36 (d, J = 7.1 Hz, 1F). |
| 77 | 335.10 [M + H] | $^1$H NMR (400 MHz, DMSO-d6) δ 11.59-11.57 (m, 1H), 11.46-11.45 (m, 1H), 8.25-8.22 (m, 1H), 8.02-7.97 (m, 1H), 7.83-7.82 (m, 1H), 6.86 (s, 1H), 5.64-5.40 (m, 2H), 4.37-3.95 (m, 4H). $^{19}$F NMR (377 MHz, DMSO-d6) δ −205.69 (m, 2F). |
| 78 | 296.10 [M + 1] | $^1$H NMR (400 MHz, DMSO-d6) δ 11.63-11.61 (m, 2H), 9.58-9.57 (m, 1H), 8.48-8.37 (m, 2H), 8.14-8.11 (m, 1H), 8.04-8.03 (m, 1H), 7.91-7.88 (m, 1H), 6.75-6.74 (m, 1H). |
| 79 | 335.10 [M + 1] | $^1$H NMR (400 MHz, DMSO-d6) δ 11.57-11.43 (m, 2H), 8.18-8.17 (m, 1H), 7.99-7.96 (m, 1H), 7.73-7.71 (m, 1H), 6.77 (s, 1H), 4.40-4.37 (m, 2H), 4.00-3.96 (m, 2H), 2.67-2.56 (m, 2H). $^{19}$F NMR (377 MHz, DMSO-d6) δ −101.14(m, 2F). |
| 80 | 363.10 [M + 1] | $^1$H NMR (400 MHz, DMSO-d6) δ 11.58-11.46 (m, 2H), 8.23-8.22 (m, 1H), 8.01-7.97 (m, 1H), 7.81-7.80 (m, 1H), 6.81 (s, 1H), 4.47-4.41(m, 2H), 3.83-3.82 (m, 2H), 1.22-1.20 (m, 6H). $^{19}$F NMR (377 MHz, DMSO-d6) δ −115.19 (m, 2F). |
| 81 | 381.10 [M + 1] | $^1$H NMR (400 MHz, DMSO-d6) δ 11.50-11.36 (m, 2H), 7.98-7.96 (m, 1H), 7.42-7.40 (m, 1H), 6.59-6.58 (m, 1H), 4.40 (brs, 2H), 3.85 (brs, 2H), 1.21 (s, 6H). $^{19}$F NMR (377 MHz, DMSO-d6) δ −115.42 (m, 2F), −155.50 (d, J = 7.4 Hz, 1F). |

TABLE 3-continued

Characterization Data

| Example No. | ES/MS m/z | NMR |
|---|---|---|
| 82 | 379.10 [M + H] | $^1$H NMR (400 MHz, Methanol-d4) δ 8.13 (s, 1H), 7.24 (d, J = 7.1 Hz, 1H), 6.70 (s, 1H), 4.56 (t, J = 12.5 Hz, 2H), 4.06 (s, 2H), 1.19-1.14 (m, 2H), 1.01-0.91 (m, 3H); $^{19}$F NMR (376 MHz, Methanol-d4) δ −111.24 (t, J = 12.4 Hz, 2F), −157.79 (d, J = 7.4 Hz, 1F). |
| 83 | 361.10 [M + H] | $^1$H NMR (400 MHz, DMSO-d6) δ 11.40 (dd, J = 9.5, 4.1 Hz, 2H), 8.08 (d, J = 1.1 Hz, 1H), 7.95 (d, J = 6.1 Hz, 1H), 7.58 (d, J = 1.1 Hz, 1H), 6.61 (s, 1H), 4.57 (t, J = 12.4 Hz, 2H), 4.02 (s, 2H), 1.10-0.96 (m, 4H). $^{19}$F NMR (376 MHz, DMSO-d6) δ −75.28 (s, 3F), −107.45 (t, J = 12.6 Hz, 2F). |
| 84 | 362.1 [M + 1] | $^1$H NMR (400 MHz, DMSO-d6) δ 11.48 (d, J = 3.6 Hz, 2H), 8.45 (s, 1H), 8.06 (d, J = 6.4 Hz, 1H), 7.00 (s, 1H), 4.53 (s, 2H), 4.03 (s, 2H), 1.12-0.91 (m, 4H). $^{19}$F NMR (376 MHz, DMSO-d6) δ −107.36 (t, J = 12.6 Hz, 2F). |
| 85 | 389.10 [M + H] | $^1$H NMR (400 MHz, DMSO-d6) δ 11.78-11.74 (m, 1H), 11.63-11.62 (m, 1H), 8.57-8.56 (m, 1H), 8.22 (s, 1H), 8.12-8.11 (m, 1H), 7.81 (s, 1H), 7.75-7.65 (m, 2H), 7.60-7.57 (m, 1H), 3.13-3.03 (m, 1H), 2.87-2.82 (m, 1H), 2.06-1.95 (m, 2H). $^{19}$F NMR (377 MHz, DMSO-d6) δ −111.39 (m, 1F). |
| 86 | 404.10 [M + H] | $^1$H NMR (400 MHz, DMSO-d6) δ 11.74-11.73 (m, 1H), 11.60-11.59 (m, 1H), 8.34 (s, 1H), 8.07-8.06 (m, 1H), 7.72 (s, 1H), 7.39-7.29 (m, 2H), 7.22-7.11 (m, 2H), 3.03-3.02 (m, 1H), 2.76-2.71 (m, 1H), 2.22-2.15 (m, 1H), 1.83-1.80 (m, 2H), 1.15-1.10 (m, 2H), 1.06-1.00 (m, 2H). $^{19}$F NMR (376 MHz, DMSO-d6) δ −117.27 (m, 1F). |
| 87 | 364.10 [M + H] | $^1$H NMR (400 MHz, DMSO-d6) δ 11.53-11.52 (m, 2H), 8.04-8.02 (m, 1H), 7.55-7.50 (m, 1H), 7.46 (s, 1H), 7.36-7.13 (m, 5H), 2.84-2.79 (m, 1H), 2.74-2.64 (m, 1H), 2.13-2.03 (m, 1H), 1.78-1.73 (m, 1H). $^{19}$F NMR (376 MHz, DMSO-d6) δ −74.87 (s, 3F), −155.60 (d, J = 7.0 Hz, 1F). |
| 88 | 400.10 [M + 1] | $^1$H NMR (400 MHz, DMSO-d6) δ 11.64-11.48 (m, 2H), 8.06-8.02 (m, 1H), 7.63-7.61 (m, 1H), 7.55 (s, 1H), 7.36-7.32 (m, 1H), 7.25-7.19 (m, 1H), 7.14-7.04 (m, 1H), 3.02-2.92 (m, 1H), 2.79-2.66 (m, 1H), 2.13-2.05 (m, 1H), 1.82-1.77 (m, 1H). $^{19}$F NMR (377 MHz, DMSO-d6) δ −113.39 (m, 1F), −115.89(m, 1F), −155.44 (d, J = 7.1 Hz, 1F). |
| 89 | 341.20 [M + 1] | $^1$H NMR (400 MHz, DMSO-d6) δ 11.61-11.54 (m, 1H), 11.48-11.47 (m, 1H), 8.48- 8.47 (m, 2H), 8.24-8.23 (m, 1H), 8.03-8.01 (m, 1H), 7.86-7.81 (m, 1H), 7.22 (s, 1H), 3.82-3.74 (m, 4H), 2.08 (s, 0H), 1.54-1.46 (m, 4H), 1.01 (s, 6H). |
| 90 | 400.10 [M + 1] | $^1$H NMR (400 MHz, DMSO-d6) δ 11.56-11.54 (s, 2H), 8.04-8.02 (m, 1H), 7.56-7.53 (m, 1H), 7.48 (s, 1H), 7.42-7.29 (m, 2H), 7.18-7.09 (m, 1H), 2.89-2.84 (m, 1H), 2.71-2.67 (m, 1H), 2.13-2.08 (m, 1H), 1.78-1.73 (m, 1H). $^{19}$F NMR (377 MHz, DMSO-d6) δ −139.37 (m, 1F), −142.87 (m, 1F), −155.62 (d, J = 7.0 Hz, 1F). |
| 91 | 327.20 [M + H] | $^1$H NMR (400 MHz, DMSO-d6) δ 12.13 (s, 1H), 11.82 (s, 1H), 8.56 (d, J = 6.0 Hz, 1H), 8.16 (d, J = 2.2 Hz, 1H), 6.71 (s, 1H), 6.53 (s, 1H), 3.98 (m, 4H), 1.90-1.78 (m, 2H), 1.14 (s, 6H). |
| 92 | 328.13 [M + H] | $^1$H NMR (400 MHz, DMSO-d6) δ 11.66 (dd, J = 6.4, 2.0 Hz, 1H), 11.53 (d, J = 1.9 Hz, 1H), 8.53-8.39 (m, 2H), 7.41 (s, 1H), 3.87-3.55 (m, 4H), 1.82 (t, J = 7.1 Hz, 2H), 1.13 (s, 6H). |
| 93 | 349.10 [M + H] | $^1$H NMR (400 MHz, DMSO-d6) δ 11.50-11.37 (m, 2H), 8.07 (d, J = 1.2 Hz, 1H), 7.95 (d, J = 6.0 Hz, 1H), 7.59 (d, J = 1.2 Hz, 1H), 6.96 (s, 1H), 4.68 (t, J = 12.0 Hz, 2H), 3.80 (t, J = 5.3 Hz, 2H), 2.14 (tt, J = 14.4, 6.6 Hz, 2H), 1.91-1.79 (m, 2H). $^{19}$F NMR (376 MHz, DMSO-d6) δ −75.42 (s, 3F), −100.53 (p, J = 13.2 Hz, 2F). |
| 94 | 339.1 [M + H] | $^1$H NMR (400 MHz, DMSO-d6) δ 11.44-11.34 (m, 2H), 8.04 (d, J = 1.2 Hz, 1H), 7.93 (d, J = 6.1 Hz, 1H), 7.58 (t, J = 1.4 Hz, 1H), 6.84 (d, J = 1.5 Hz, 1H), 4.57 (d, J = 11.7 Hz, 2H), 3.07 (dd, J = 12.0, 1.5 Hz, 2H), 2.37 (d, J = 5.0 Hz, 2H), 1.73-1.53 (m, 6H). |
| 95 | 432.07 [M + H] | $^1$H NMR (400 MHz, DMSO-d6) δ 11.60-11.51 (m, 2H), 8.36 (d, J = 1.4 Hz, 1H), 8.04 (d, J = 6.1 Hz, 1H), 7.90 (d, J = 1.5 Hz, 1H), 7.70-7.62 (m, 2H), 7.61 (s, 1H), 7.47 (dd, J = 10.7, 8.5 Hz, 1H), 2.93 (ddd, J = 9.1, 6.3, 4.4 Hz, 1H), 2.78 (ddd, J = 9.0, 6.0, 4.4 Hz, 1H), 2.08 (q, J = 5.0, 4.4 Hz, 1H), 1.86 (ddd, J = 8.8, 6.4, 5.1 Hz, 1H). $^{19}$F NMR (376 MHz, DMSO-d6) δ −60.42 (d, J = 12.5 Hz, 3F), −75.14, −120.29 (dtq, J = 17.1, 11.6, 6.0, 5.4 Hz, 1F). |
| 96 | 414.10 [M + H] | $^1$H NMR (400 MHz, DMSO-d6) δ 11.50 (s, 2H), 8.37 (s, 1H), 8.02 (s, 1H), 7.89 (t, J = 7.8 Hz, 2H), 7.78 (t, J = 7.6 Hz, 1H), 7.64 (t, J = 7.7 Hz, 1H), 7.41 (s, 1H), 2.44 (td, J = 8.6, 4.4 Hz, 1H), 1.39 (dt, J = 6.1, 3.2 Hz, 2H), 1.21 (dt, J = 8.4, 3.3 Hz, 2H). $^{19}$F NMR (376 MHz, DMSO-d6) δ −57.14 (s, 3F). |
| 97 | 347.10 [M + H] | $^1$H NMR (400 MHz, DMSO-d6) δ 11.59 (d, J = 6.3 Hz, 1H), 11.54 (d, J = 1.9 Hz, 1H), 9.31 (d, J = 1.2 Hz, 1H), 8.90 (d, J = 6.6 Hz, 2H), 8.48 (d, J = 6.7 Hz, 2H), 8.04 (d, J = 6.2 Hz, 1H), 7.45 (s, 1H), 2.56 (ddd, J = 8.4, 6.3, 4.1 Hz, 1H), 1.38-1.21 (m, 4H). |

TABLE 3-continued

Characterization Data

| Example No. | ES/MS m/z | NMR |
|---|---|---|
| 98 | 398.10 [M + H] | $^1$H NMR (400 MHz, DMSO-d6) δ 11.59-11.51 (m, 2H), 8.34 (d, J = 1.5 Hz, 1H), 8.03 (d, J = 6.1 Hz, 1H), 7.89 (s, 1H), 7.59 (s, 1H), 7.51 (t, J = 8.2 Hz, 1H), 7.35 (dd, J = 10.9, 2.1 Hz, 1H), 7.16 (dd, J = 8.4, 2.0 Hz, 1H), 2.84 (ddd, J = 9.0, 6.2, 4.4 Hz, 1H), 2.76 (ddd, J = 8.8, 6.0, 4.3 Hz, 1H), 2.09 (dt, J = 8.8, 5.3 Hz, 1H), 1.81 (ddd, J = 8.7, 6.3, 5.0 Hz, 1H). $^{19}$F NMR (376 MHz, DMSO-d6) δ −75.15 (s, 3F), −117.14 (dd, J = 10.8, 8.0 Hz, 1F). |
| 99 | 398.08 [M + H] | $^1$H NMR (400 MHz, DMSO-d6) δ 11.60 (dd, J = 6.3, 1.9 Hz, 1H), 11.56 (d, J = 1.9 Hz, 1H), 8.39 (d, J = 1.5 Hz, 1H), 8.05 (d, J = 6.2 Hz, 1H), 7.96 (d, J = 1.6 Hz, 1H), 7.63 (s, 1H), 7.50 (dd, J = 7.1, 2.2 Hz, 1H), 7.35 (t, J = 8.9 Hz, 1H), 7.29 (ddd, J = 8.6, 4.8, 2.2 Hz, 1H), 2.78 (dddd, J = 19.0, 8.8, 6.1, 4.4 Hz, 2H), 2.02 (dt, J = 8.8, 5.4 Hz, 1H), 1.82 (ddd, J = 8.7, 6.4, 5.0 Hz, 1H). $^{19}$F NMR (376 MHz, DMSO-d6) δ −75.19 (s, 3F), −120.53 (ddd, J = 9.0, 7.0, 4.7 Hz, 1F). |
| 100 | 432.10 [M + H] | $^1$H NMR (400 MHz, DMSO-d6) δ 11.53 (s, 2H), 8.30 (s, 1H), 8.01 (d, J = 6.3 Hz, 1H), 7.81 (s, 1H), 7.69 (t, J = 8.0 Hz, 1H), 7.57 (s, 1H), 7.44 (d, J = 12.4 Hz, 1H), 7.33 (d, J = 8.1 Hz, 1H), 2.97 (dt, J = 9.6, 5.5 Hz, 1H), 2.84 (dt, J = 9.7, 5.6 Hz, 1H), 2.21 (dt, J = 9.0, 5.5 Hz, 1H), 1.86 (dt, J = 8.7, 5.4 Hz, 1H). $^{19}$F NMR (376 MHz, DMSO-d6) δ −60.12 (d, J = 12.0 Hz, 3F), −74.93, −116.77 (pd, J = 12.0, 7.6 Hz, 1F). |
| 101 | 376.20 [M + H] | $^1$H NMR (400 MHz, DMSO-d6) δ 11.61-11.47 (m, 2H), 8.37 (s, 1H), 8.04 (d, J = 6.0 Hz, 1H), 7.93 (s, 1H), 7.61 (s, 1H), 7.22 (ddd, J = 8.5, 7.4, 1.7 Hz, 1H), 7.11 (dd, J = 7.7, 1.7 Hz, 1H), 7.01-6.88 (m, 2H), 3.74 (s, 3H), 2.91 (td, J = 9.2, 5.6 Hz, 1H), 2.65 (dt, J = 8.8, 5.3 Hz, 1H), 1.96 (dt, J = 9.8, 5.1 Hz, 1H), 1.74 (ddd, J = 8.6, 6.6, 4.7 Hz, 1H). |
| 102 | 347.11 [M + H] | $^1$H NMR (400 MHz, DMSO-d6) δ 11.49 (d, J = 7.0 Hz, 2H), 9.27 (d, J = 2.1 Hz, 1H), 8.91 (s, 1H), 8.59 (d, J = 4.7 Hz, 1H), 8.47 (d, J = 8.0 Hz, 1H), 8.00 (d, J = 6.0 Hz, 1H), 7.59 (dd, J = 7.6, 5.2 Hz, 1H), 7.35 (s, 1H), 2.60-2.53 (m, 1H), 1.35-1.20 (m, 4H). |
| 103 | 347.14 [M + H]. | $^1$H NMR (400 MHz, DMSO-d6) δ 11.63-11.38 (m, 2H), 8.66 (s, 1H), 8.64 (ddd, J = 4.9, 1.6, 0.9 Hz, 1H), 8.19 (d, J = 7.8 Hz, 1H), 8.01 (d, J = 6.4 Hz, 1H), 7.95 (td, J = 7.9, 1.6 Hz, 1H), 7.40 (ddd, J = 7.5, 5.1, 1.2 Hz, 1H), 7.36 (s, 1H), 2.57-2.54 (m, 1H), 1.35-1.20 (m, 4H). |
| 104 | 346.10 [M + H] | $^1$H NMR (400 MHz, Methanol-d4) δ 8.38 (d, J = 1.9 Hz, 1H), 8.30 (s, 1H), 8.07 (d, J = 1.9 Hz, 1H), 8.01 (s, 1H), 7.38-7.22 (m, 5H), 2.74 (t, J = 7.5 Hz, 2H), 1.93 (tt, J = 7.5, 3.7 Hz, 2H). |
| 105 | 360.20 [M + H] | $^1$H NMR (400 MHz, Methanol-d4) δ 8.34 (d, J = 2.0 Hz, 1H), 8.24 (s, 1H), 8.08 (d, J = 1.6 Hz, 1H), 7.82 (s, 1H), 7.34-7.14 (m, 5H), 3.02-2.78 (m, 2H), 2.42-2.32 (m, 1H), 1.93-1.85 (m, 1H), 1.50-1.38 (m, 2H). |
| 106 | 360.10 [M + H] | $^1$H NMR (400 MHz, Methanol-d4) δ 8.36 (d, J = 2.0 Hz, 1H), 8.27 (s, 1H), 8.09 (d, J = 2.0 Hz, 1H), 7.86 (s, 1H), 2.85-2.66 (m, 2H), 2.51-2.35 (m, 2H), 2.36-2.28 (m, 1H), 2.26-2.11 (m, 1H), 1.86-1.75 (m, 1H), 1.48-1.33 (m, 2H). $^{19}$F NMR (376 MHz, Methanol-d4) δ −77.71 (s, 3F), −84.96--85.76 (m, 1F), −98.02--98.82 (m, 1F). |
| 107 | 338.10 [M + H] | $^1$H NMR (400 MHz, Methanol-d4) δ 8.22 (s, 1H), 8.10 (s, 1H), 7.69 (s, 1H), 7.59 (s, 1H), 2.96-2.85 (m, 1H), 2.72-2.62 (m, 1H), 1.72-1.57 (m, 2H). $^{19}$F NMR (376 MHz, Methanol-d4) δ −69.25 (d, J = 6.6 Hz, 3F), −77.49 (s, 3F). |
| 108 | 364.10 [M + H] | $^1$H NMR (400 MHz, Methanol-d4) δ 8.35 (d, J = 1.9 Hz, 1H), 8.30 (s, 1H), 8.22 (s, 1H), 8.00 (d, J = 1.9 Hz, 1H), 7.50-7.35 (m, 5H), 3.10-2.99 (m, 1H), 2.36 (dt, J = 20.8, 8.0 Hz, 1H), 2.29-2.19 (m, 1H). $^{19}$F NMR (377 MHz, Methanol-d4) δ −77.80 (s, 3F), −188.55 (m, 1F). |
| 109 | 371.10 [M + H] | $^1$H NMR (400 MHz, DMSO-d6) δ 11.44 (s, 1H), 8.12 (d, J = 1.2 Hz, 1H), 7.95 (td, J = 3.1, 1.1 Hz, 1H), 7.62 (d, J = 1.2 Hz, 1H), 6.69 (s, 1H), 4.65 (t, J = 13.1 Hz, 4H). $^{19}$F NMR (376 MHz, DMSO-d6) δ −74.15 (s, 3F), −122.65 (td, J = 13.9, 12.3, 5.2 Hz, 4F). |
| 110 | 426.10 [M + H] | $^1$H NMR (400 MHz, Methanol-d4) δ 8.39 (d, J = 2.0 Hz, 1H), 8.30 (s, 1H), 8.09 (d, J = 2.0 Hz, 1H), 8.02 (s, 1H), 7.21-7.09 (m, 3H), 2.84-2.67 (m, 2H), 1.93 (ddd, J = 8.1, 6.6, 1.4 Hz, 2H). $^{19}$F NMR (376 MHz, DMSO-d6) δ −52.99 (d, J = 4.1 Hz, 2F), −77.78 (s, 3F) |
| 111 | 385.10 [M + H] | $^1$H NMR (400 MHz, Acetonitrile-d3) δ 8.15 (d, J = 1.9 Hz, 1H), 8.08 (d, J = 6.5 Hz, 1H), 7.97 (d, J = 1.9 Hz, 1H), 7.76 (s, 1H), 7.72-7.61 (m, 2H), 7.57-7.42 (m, 2H), 3.08-2.88 (m, 3H), 1.86-1.75 (m, 1H), 1.54-1.37 (m, 2H). |
| 117 | 486.20 [M + H] | $^1$H NMR (400 MHz, DMSO-d6) δ 11.54 (s, 2H), 8.31 (s, 1H), 8.03 (d, J = 6.3 Hz, 1H), 7.85-7.80 (m, 1H), 7.78-7.67 (m, 2H), 7.58 (s, 1H), 7.24-7.17 (m, 1H), 5.31 (q, J = 9.0 Hz, 2H), 3.03 (dt, J = 9.6, 5.7 Hz, 1H), 2.83 (dt, J = 9.6, 5.3 Hz, 1H), 2.18 (dt, J = 10.0, 5.3 Hz, 1H), 2.08 (s, 0H), 1.91 (q, J = 6.3 Hz, 1H). $^{19}$F NMR (376 MHz, DMSO-d6) δ −70.27 (t, J = 9.0 Hz), −74.98--75.08 (m), −133.91. |

TABLE 3-continued

Characterization Data

| Example No. | ES/MS m/z | NMR |
|---|---|---|
| 118 | 476.10 [M + H] | $^1$H NMR (400 MHz, DMSO-d6) δ 11.58 (d, J = 8.3 Hz, 2H), 8.38 (d, J = 4.5 Hz, 1H), 8.06 (q, J = 3.5, 2.7 Hz, 2H), 7.94 (d, J = 7.9 Hz, 1H), 7.71 (d, J = 8.3 Hz, 1H), 7.63 (d, J = 3.5 Hz, 2H), 7.06 (d, J = 8.4 Hz, 1H), 4.62-4.45 (m, 1H), 3.02-2.92 (m, 1H), 2.88-2.79 (m, 1H), 2.29 (ddq, J = 14.8, 12.0, 7.3 Hz, 1H), 2.11 (dt, J = 11.0, 5.6 Hz, 1H), 1.99-1.91 (m, 1H), 1.66 (dq, J = 11.4, 5.3 Hz, 1H), 1.55-1.42 (m, 1H). $^{19}$F NMR (376 MHz, DMSO-d6) δ −75.24 (d, J = 8.6 Hz), −127.40--128.51 (m), −141.38 (ddt, J = 155.3, 13.4, 4.4 Hz). |
| 119 | 428.20 [M + H] | $^1$H NMR (400 MHz, DMSO-d6) δ 11.58-11.52 (m, 2H), 8.36-8.31 (m, 1H), 8.07-7.98 (m, 2H), 7.86 (s, 1H), 7.68 (d, J = 8.4 Hz, 1H), 7.62-7.56 (m, 2H), 7.02 (dd, J = 8.5, 1.4 Hz, 1H), 5.00 (p, J = 6.6 Hz, 1H), 2.97 (ddd, J = 9.0, 6.2, 4.2 Hz, 1H), 2.87-2.77 (m, 1H), 2.16-2.06 (m, 1H), 1.93 (dt, J = 8.8, 5.6 Hz, 1H), 1.47 (dd, J = 9.3, 6.6 Hz, 6H). $^{19}$F NMR (376 MHz, DMSO-d6) δ −75.03. |
| 120 | 428.20 [M + H] | $^1$H NMR (400 MHz, DMSO-d6) δ 11.54 (s, 2H), 8.33 (d, J = 1.4 Hz, 1H), 8.07-7.98 (m, 2H), 7.85 (s, 1H), 7.68 (d, J = 8.3 Hz, 1H), 7.59 (d, J = 4.8 Hz, 2H), 7.02 (dd, J = 8.4, 1.3 Hz, 1H), 5.00 (p, J = 6.6 Hz, 1H), 3.03-2.93 (m, 1H), 2.86-2.77 (m, 1H), 2.11 (dq, J = 9.5, 4.8 Hz, 1H), 1.93 (dt, J = 8.6, 5.5 Hz, 1H), 1.47 (dd, J = 9.3, 6.6 Hz, 6H). |
| 121 | 431.20 [M + H] | $^1$H NMR (400 MHz, DMSO-d6) δ 11.54 (d, J = 4.0 Hz, 2H), 8.24 (d, J = 2.5 Hz, 1H), 8.03 (d, J = 6.4 Hz, 1H), 7.86-7.50 (m, 1H), 7.80 (dd, J = 8.5, 2.5 Hz, 1H), 7.55 (d, J = 7.1 Hz, 1H), 7.52-7.50 (m, 1H), 7.06 (d, J = 8.5 Hz, 1H), 2.92-2.87 (m, 1H), 2.79-2.66 (m, 1H), 2.14 (dt, J = 9.1, 5.4 Hz, 1H), 1.79 (ddd, J = 8.8, 6.3, 4.8 Hz, 1H). $^{19}$F NMR (376 MHz, DMSO-d6) δ −87.51 (d, J = 72.9 Hz), −155.62 (d, J = 7.4 Hz). |
| 122 | 431.10 [M + H] | $^1$H NMR (400 MHz, DMSO-d6) δ 11.55 (d, J = 4.7 Hz, 2H), 8.24 (d, J = 2.4 Hz, 1H), 8.03 (d, J = 6.3 Hz, 1H), 7.86-7.49 (m, 1H), 7.80 (dd, J = 8.6, 2.6 Hz, 1H), 7.56 (d, J = 7.1 Hz, 1H), 7.51 (s, 1H), 7.06 (d, J = 8.5 Hz, 1H), 2.91 (ddd, J = 9.0, 6.3, 4.4 Hz, 1H), 2.71 (ddd, J = 8.9, 5.9, 4.5 Hz, 1H), 2.14 (dt, J = 8.9, 5.3 Hz, 1H), 1.84-1.74 (m, 1H). $^{19}$F NMR (376 MHz, DMSO-d6) δ −75.46, −87.52 (d, J = 73.3 Hz), −155.60 (d, J = 7.0 Hz). |
| 123 | 450.20 [M + H] | $^1$H NMR (400 MHz, DMSO-d6) δ 11.55 (s, 2H), 8.34 (s, 1H), 8.14-7.99 (m, 2H), 7.86 (s, 1H), 7.77-7.54 (m, 3H), 7.09 (d, J = 8.4 Hz, 1H), 6.43 (t, J = 54.9 Hz, 1H), 4.91 (t, J = 14.9 Hz, 2H), 3.00 (s, 1H), 2.82 (d, J = 7.9 Hz, 1H), 2.13 (d, J = 8.2 Hz, 1H), 1.93 (s, 1H). $^{19}$F NMR (376 MHz, DMSO-d6) δ −75.08, −122.34 (dt, J = 55.1, 15.3 Hz). |
| 124 | 450.20 [M + H] | $^1$H NMR (400 MHz, DMSO-d6) δ 11.53 (d, J = 4.7 Hz, 2H), 8.31 (d, J = 1.3 Hz, 1H), 8.10 (d, J = 0.9 Hz, 1H), 8.06-7.99 (m, 1H), 7.82 (s, 1H), 7.75-7.64 (m, 2H), 7.56 (s, 1H), 7.08 (dd, J = 8.4, 1.3 Hz, 1H), 6.57-6.29 (t, J = 3.9 Hz, 1H), 4.91 (td, J = 15.0, 3.8 Hz, 2H), 3.05-2.96 (m, 1H), 2.81 (dt, J = 8.9, 5.4 Hz, 1H), 2.19-2.06 (m, 1H), 1.91 (dt, J = 8.5, 5.3 Hz, 1H) $^{19}$F NMR (376 MHz, DMSO-d6) δ −74.89, −122.34 (dt, J = 54.8, 15.1 Hz). |
| 125 | 450.20 [M + H] | $^1$H NMR (400 MHz, DMSO-d6) δ 11.53 (s, 2H), 8.30 (s, 1H), 8.10 (s, 1H), 8.02 (d, J = 6.2 Hz, 1H), 7.85-7.65 (m, 3H), 7.55 (s, 1H), 7.08 (dd, J = 8.4, 1.3 Hz, 1H), 6.43 (tt, J = 54.9, 3.7 Hz, 1H), 4.91 (td, J = 15.1, 3.8 Hz, 2H), 3.05-2.93 (m, 1H), 2.86-2.77 (m, 1H), 2.20-2.10 (m, 1H), 1.96-1.83 (m, 1H). $^{19}$F NMR (376 MHz, DMSO-d6) δ −74.81, −122.34 (dt, J = 54.8, 15.0 Hz). |
| 126 | 468.20 [M + H] | $^1$H NMR (400 MHz, DMSO-d6) δ 11.55 (s, 2H), 8.33 (d, J = 1.5 Hz, 1H), 8.07-8.00 (m, 1H), 7.94 (d, J = 8.0 Hz, 1H), 7.86 (s, 1H), 7.59 (s, 1H), 7.53 (d, J = 3.7 Hz, 1H), 7.22 (d, J = 8.0 Hz, 1H), 6.57 (d, J = 3.6 Hz, 1H), 5.18 (h, J = 8.3 Hz, 2H), 3.04 (dddd, J = 28.6, 9.7, 6.0, 4.1 Hz, 2H), 2.13-1.98 (m, 2H). $^{19}$F NMR (376 MHz, DMSO-d6) δ −70.62 (t, J = 9.4 Hz), −75.12. |
| 127 | 468.10 [M + H] | $^1$H NMR (400 MHz, DMSO-d6) δ 11.59-11.51 (m, 2H), 9.21 (s, 1H), 8.31 (d, J = 1.3 Hz, 1H), 8.24 (s, 1H), 8.04 (d, J = 6.1 Hz, 1H), 7.93 (d, J = 3.5 Hz, 1H), 7.78 (d, J = 1.3 Hz, 1H), 7.65 (s, 1H), 7.10 (d, J = 3.5 Hz, 1H), 5.46 (q, J = 9.0 Hz, 2H), 3.53 (dd, J = 9.2, 5.0 Hz, 1H), 3.05-2.95 (m, 1H), 2.43 (dd, J = 9.4, 5.6 Hz, 1H), 2.11 (dt, J = 9.5, 5.5 Hz, 1H). $^{19}$F NMR (376 MHz, DMSO-d6) δ −70.70 (t, J = 9.1 Hz), −74.81. |
| 128 | 508.20 [M + H] | $^1$H NMR (400 MHz, DMSO-d6) δ 11.54 (s, 2H), 8.32 (s, 1H), 8.06-7.99 (m, 1H), 7.83 (s, 1H), 7.74 (d, J = 8.4 Hz, 1H), 7.63 (s, 1H), 7.56 (s, 1H), 7.07 (dd, J = 8.4, 1.4 Hz, 1H), 5.27 (q, J = 9.1 Hz, 2H), 2.99 (dt, J = 9.2, 5.5 Hz, 1H), 2.79 (dt, J = 9.6, 5.4 Hz, 1H), 2.34-2.23 (m, 1H), 2.18-2.06 (m, 1H), 1.90 (dd, J = 8.8, 5.3 Hz, 1H), 1.07-0.91 (m, 4H). $^{19}$F NMR (376 MHz, DMSO-d6) δ −70.04 (t, J = 9.2 Hz), −75.00. |

TABLE 3-continued

Characterization Data

| Example No. | ES/MS m/z | NMR |
|---|---|---|
| 129 | 468.20 [M + H] | $^1$H NMR (400 MHz, DMSO-d6) δ 11.57 (d, J = 6.0 Hz, 2H), 8.38 (d, J = 1.5 Hz, 1H), 8.22 (d, J = 2.3 Hz, 1H), 8.04 (d, J = 6.0 Hz, 1H), 7.92 (s, 1H), 7.69-7.56 (m, 2H), 7.02 (dd, J = 8.5, 6.0 Hz, 1H), 6.44 (tt, J = 54.7, 3.6 Hz, 1H), 4.91 (td, J = 15.0, 3.6 Hz, 2H), 3.16 (dt, J = 8.7, 5.4 Hz, 1H), 2.85 (dt, J = 8.9, 5.4 Hz, 1H), 2.15 (dt, J = 8.9, 5.3 Hz, 1H), 1.98-1.85 (m, 1H). $^{19}$F NMR (376 MHz, DMSO-d6) δ −75.20, −75.24 (d, J = 20.0 Hz), −123.46 (dtd, J = 54.7, 15.1, 5.8 Hz), −141.44−−141.52 (m). |
| 130 | 440.20 [M + H] | $^1$H NMR (400 MHz, DMSO-d6) δ 11.57 (d, J = 5.5 Hz, 2H), 8.36 (d, J = 1.4 Hz, 1H), 8.08-7.97 (m, 2H), 7.90 (s, 1H), 7.69 (d, J = 8.4 Hz, 1H), 7.61 (s, 2H), 7.02 (dd, J = 8.4, 1.3 Hz, 1H), 4.28 (d, J = 6.9 Hz, 2H), 2.97 (ddd, J = 9.4, 6.3, 4.4 Hz, 1H), 2.87-2.77 (m, 1H), 2.10 (dt, J = 8.9, 5.3 Hz, 1H), 1.99-1.89 (m, 1H), 1.28 (tq, J = 7.4, 4.8 Hz, 1H), 0.54-0.42 (m, 2H), 0.46-0.34 (m, 2H), 0.08 (s, 0H). |
| 131 | 465.10 [M + H] | $^1$H NMR (400 MHz, DMSO-d6) δ 11.57 (d, J = 6.1 Hz, 2H), 8.63 (d, J = 8.6 Hz, 1H), 8.36 (d, J = 1.5 Hz, 1H), 8.14 (d, J = 8.8 Hz, 1H), 8.09-8.02 (m, 2H), 7.97 (d, J = 8.6 Hz, 1H), 7.92-7.81 (m, 2H), 7.66 (s, 1H), 3.09 (ddd, J = 9.0, 6.2, 4.4 Hz, 1H), 2.94 (ddd, J = 8.9, 6.0, 4.4 Hz, 1H), 2.22 (dt, J = 8.8, 5.4 Hz, 1H), 1.99 (dt, J = 8.7, 5.4 Hz, 1H). $^{19}$F NMR (376 MHz, DMSO-d6) δ −66.40, −75.16 |
| 132 | 431.20 [M + H] | $^1$H NMR (400 MHz, DMSO-d6) δ 11.65-11.46 (m, 2H), 8.44 (d, J = 2.8 Hz, 1H), 8.04 (d, J = 6.2 Hz, 1H), 7.65-7.49 (m, 4H), 7.28 (t, J = 73.6 Hz, 1H), 3.06 (ddd, J = 8.7, 5.9, 4.2 Hz, 1H), 2.93 (ddd, J = 8.9, 6.0, 4.1 Hz, 1H), 2.08 (ddd, J = 8.4, 6.0, 4.0 Hz, 1H), 1.91-1.84 (m, 1H). $^{19}$F NMR (376 MHz, DMSO-d6) δ −82.66, −82.86, −155.42 (d, J = 7.0 Hz). |
| 133 | 465.10 [M + H] | $^1$H NMR (400 MHz, DMSO-d6) δ 11.63 (dd, J = 23.1, 4.1 Hz, 2H), 9.45 (s, 1H), 8.47 (s, 1H), 8.36 (s, 1H), 8.27 (d, J = 8.6 Hz, 1H), 8.14-8.04 (m, 3H), 7.84-7.75 (m, 2H), 3.05 (t, J = 7.4 Hz, 2H), 2.24-2.14 (m, 1H), 2.03 (td, J = 7.7, 5.1 Hz, 1H). $^{19}$F NMR (376 MHz, DMSO-d6) δ −66.37, −221.04. |
| 134 | 483.10 [M + H] | $^1$H NMR (400 MHz, DMSO-d6) δ 11.60-11.53 (m, 2H), 9.00 (dd, J = 4.4, 1.5 Hz, 1H), 8.44 (dd, J = 8.4, 1.7 Hz, 1H), 8.19 (d, J = 1.9 Hz, 1H), 8.11 (d, J = 1.9 Hz, 1H), 8.05 (d, J = 6.0 Hz, 1H), 7.68 (dd, J = 8.4, 4.2 Hz, 1H), 7.58 (d, J = 7.4 Hz, 2H), 3.25-3.15 (m, 1H), 2.91 (dt, J = 10.0, 5.4 Hz, 1H), 2.24 (dt, J = 9.0, 5.4 Hz, 1H), 1.99 (dt, J = 8.8, 5.5 Hz, 1H). $^{19}$F NMR (376 MHz, DMSO-d6) δ −59.07, −155.55 (d, J = 7.0 Hz). |
| 135 | 465.10 [M + H] | $^1$H NMR (400 MHz, DMSO-d6) δ 11.58 (d, J = 7.1 Hz, 2H), 9.04-8.98 (m, 1H), 8.45 (dd, J = 8.5, 1.6 Hz, 1H), 8.38 (s, 1H), 8.19 (s, 1H), 8.13-8.02 (m, 2H), 7.91 (s, 1H), 7.73-7.65 (m, 2H), 3.15 (dt, J = 10.0, 5.7 Hz, 1H), 2.93 (dt, J = 10.0, 5.2 Hz, 1H), 2.20 (dt, J = 10.4, 5.6 Hz, 1H), 2.03 (dt, J = 11.1, 5.7 Hz, 1H). $^{19}$F NMR (376 MHz, DMSO-d6) δ −59.07, −75.13. |
| 136 | 413.10 [M + H] | $^1$H NMR (400 MHz, DMSO-d6) δ 11.85-11.61 (m, 2H), 8.59 (d, J = 1.9 Hz, 1H), 8.46 (d, J = 2.8 Hz, 1H), 8.23 (d, J = 1.9 Hz, 1H), 8.12 (d, J = 6.3 Hz, 1H), 7.86 (s, 1H), 7.69-7.54 (m, 2H), 7.30 (t, J = 73.5 Hz, 1H), 3.12-2.92 (m, 2H), 1.94 (dddd, J = 32.7, 8.7, 6.0, 4.3 Hz, 2H). $^{19}$F NMR (376 MHz, DMSO-d6) δ −82.93 (d, J = 73.5 Hz). |
| 137 | 413.10 [M + H] | $^1$H NMR (400 MHz, DMSO-d6) δ 11.63-11.54 (m, 2H), 8.42 (dd, J = 17.0, 2.1 Hz, 2H), 8.06 (d, J = 6.2 Hz, 1H), 7.95 (s, 1H), 7.70-7.50 (m, 3H), 7.28 (t, J = 73.6 Hz, 1H), 3.05-2.92 (m, 2H), 2.02-1.89 (m, 2H). $^{19}$F NMR (376 MHz, DMSO-d6) δ −75.29, −82.79 (d, J = 73.6 Hz). |
| 138 | 465.10 [M + H] | $^1$H NMR (400 MHz, DMSO-d6) δ 11.62 (dd, J = 20.3, 4.1 Hz, 2H), 9.45 (s, 1H), 8.46 (s, 1H), 8.36 (s, 1H), 8.27 (d, J = 8.6 Hz, 1H), 8.13-8.02 (m, 3H), 7.84-7.72 (m, 2H), 3.05 (ddd, J = 9.0, 6.6, 2.4 Hz, 2H), 2.24-2.14 (m, 1H), 2.03 (td, J = 8.3, 7.8, 5.1 Hz, 1H). $^{19}$F NMR (376 MHz, DMSO-d6) δ −66.38. |
| 139 | 465.10 [M + H] | $^1$H NMR (400 MHz, DMSO-d6) δ 11.65-11.56 (m, 2H), 9.06 (dd, J = 4.3, 1.5 Hz, 1H), 8.51-8.40 (m, 2H), 8.21 (s, 1H), 8.08 (d, J = 6.2 Hz, 1H), 8.05-7.97 (m, 2H), 7.76-7.67 (m, 2H), 3.15 (ddd, J = 9.0, 6.3, 4.4 Hz, 1H), 3.05-2.95 (m, 1H), 2.20 (dt, J = 9.0, 5.5 Hz, 1H), 2.10 (dt, J = 8.6, 5.6 Hz, 1H). $^{19}$F NMR (376 MHz, DMSO-d6) δ −58.50 (d, J = 2.0 Hz), −75.26. |
| 140 | 413.10 [M + H] | $^1$H NMR (400 MHz, DMSO-d6) δ 11.62 (dd, J = 22.1, 3.9 Hz, 2H), 8.46 (s, 1H), 8.25 (d, J = 2.5 Hz, 1H), 8.08-8.07 (m, 2H), 7.87-7.51 (m, 1H), 7.81 (dd, J = 8.6, 2.6 Hz, 1H), 7.71 (s, 1H), 7.08 (d, J = 8.5 Hz, 1H), 2.83 (dt, J = 8.6, 5.5 Hz, 2H), 2.04 (dt, J = 8.9, 5.4 Hz, 1H), 1.92-1.82 (m, 1H). $^{19}$F NMR (376 MHz, DMSO-d6) δ −87.58 (d, J = 72.9 Hz). |
| 141 | 465.10 [M + H] | $^1$H NMR (400 MHz, DMSO-d6) δ 11.58 (d, J = 6.8 Hz, 2H), 9.01 (dd, J = 4.2, 1.8 Hz, 1H), 8.45 (dd, J = 8.5, 1.8 Hz, 1H), 8.38 (d, J = 1.5 Hz, 1H), 8.19 (d, J = 2.0 Hz, 1H), 8.14-8.03 (m, 2H), 7.92 (s, 1H), 7.73-7.65 (m, 2H), 3.14 (ddd, J = 8.9, 6.2, 4.4 Hz, 1H), 2.93 |

TABLE 3-continued

Characterization Data

| Example No. | ES/MS m/z | NMR |
|---|---|---|
| | | (ddd, J = 8.8, 6.0, 4.4 Hz, 1H), 2.19 (dt, J = 8.9, 5.5 Hz, 1H), 2.04 (dt, J = 8.7, 5.5 Hz, 1H). $^{19}$F NMR (376 MHz, DMSO-d6) δ −59.07, −75.16 |
| 142 | 465.10 [M + H] | $^{1}$H NMR (400 MHz, DMSO-d6) δ 11.56 (s, 2H), 8.63 (d, J = 8.6 Hz, 1H), 8.36 (d, J = 1.4 Hz, 1H), 8.14 (d, J = 8.8 Hz, 1H), 8.08-8.02 (m, 2H), 7.97 (d, J = 8.6 Hz, 1H), 7.91-7.81 (m, 2H), 7.65 (s, 1H), 3.09 (ddd, J = 9.0, 6.2, 4.4 Hz, 1H), 2.94 (ddd, J = 8.8, 5.9, 4.3 Hz, 1H), 2.22 (dt, J = 8.8, 5.3 Hz, 1H), 1.99 (dt, J = 8.6, 5.3 Hz, 1H). $^{19}$F NMR (376 MHz, DMSO-d6) δ −66.40, −75.14. |
| 143 | 443.20 [M + H] | $^{1}$H NMR (400 MHz, Methanol-d4) δ 9.24 (s, 1H), 8.28 (s, 1H), 8.15 (s, 1H), 8.10-8.01 (m, 3H), 7.51 (dd, J = 8.5, 1.9 Hz, 1H), 2.96-2.86 (m, 1H), 2.82 (dt, J = 9.9, 5.1 Hz, 1H), 2.23-2.11 (m, 1H), 2.11-1.93 (m, 2H), 1.26-1.16 (m, 2H), 1.02 (dt, J = 6.6, 4.4 Hz, 2H). |
| 144 | 433.10 [M + H] | $^{1}$H NMR (400 MHz, DMSO-d6) δ 11.55 (d, J = 4.3 Hz, 2H), 8.90 (dd, J = 2.3, 1.2 Hz, 1H), 8.14-7.98 (m, 2H), 7.70 (d, J = 8.2 Hz, 1H), 7.58-7.43 (m, 2H), 3.18 (ddd, J = 8.7, 5.8, 4.1 Hz, 1H), 3.03 (ddd, J = 8.9, 6.2, 4.1 Hz, 1H), 2.19 (ddd, J = 8.6, 6.2, 4.0 Hz, 1H), 1.93 (ddd, J = 9.3, 5.8, 3.9 Hz, 1H). $^{19}$F NMR (376 MHz, DMSO-d6) δ −61.11, −155.53 (d, J = 7.1 Hz). |
| 145 | 403.20 [M + H] | $^{1}$H NMR (400 MHz, DMSO-d6) δ 11.41-11.30 (m, 2H), 7.89 (d, J = 6.2 Hz, 1H), 7.81 (s, 1H), 6.53 (s, 1H), 4.40 (s, 2H), 3.78 (s, 2H), 2.00 (tt, J = 8.3, 5.0 Hz, 1H), 1.21 (s, 6H), 0.96-0.85 (m, 2H), 0.88-0.77 (m, 2H). $^{19}$F NMR (376 MHz, DMSO-d6) δ −115.35 (t, J = 13.8 Hz). |
| 146 | 422.10 [M + H] | $^{1}$H NMR (400 MHz, DMSO-d6) δ 11.67-11.61 (m, 1H), 11.57 (d, J = 2.0 Hz, 1H), 8.28 (s, 1H), 8.03 (d, J = 6.2 Hz, 1H), 7.69 (s, 1H), 7.39 (td, J = 8.8, 6.4 Hz, 1H), 7.25 (ddd, J = 10.7, 9.3, 2.6 Hz, 1H), 7.16-7.06 (m, 1H), 2.83-2.75 (m, 2H), 2.21-2.06 (m, 1H), 1.88 (dt, J = 15.4, 6.2 Hz, 2H), 1.09 (dq, J = 6.2, 3.8 Hz, 2H), 0.96 (dq, J = 7.1, 4.5, 4.1 Hz, 2H). $^{19}$F NMR (376 MHz, DMSO-d6) δ −113.19, −115.50. |
| 147 | 343.10 [M + H] | $^{1}$H NMR (400 MHz, DMSO-d6) δ 11.68 (d, J = 63.9 Hz, 2H), 8.43 (d, J = 6.1 Hz, 1H), 8.09 (d, J = 2.3 Hz, 1H), 6.92 (s, 1H), 6.43 (s, 1H), 4.59-4.21 (m, 2H), 3.93-3.70 (m, 3H), 1.20-0.81 (m, 4H). $^{19}$F NMR (376 MHz, DMSO-d6) δ −74.79, −171.56. |
| 148 | 361.20 [M + H] | $^{1}$H NMR (400 MHz, DMSO-d6) δ 11.54-11.29 (m, 2H), 7.97 (d, J = 6.1 Hz, 1H), 7.38 (d, J = 7.3 Hz, 1H), 6.56 (s, 1H), 3.88-3.86 (m, 5H), 1.16-0.66 (m, 4H). $^{19}$F NMR (376 MHz, DMSO-d6) δ −75.10, −155.57 (d, J = 7.4 Hz). |
| 149 | 415.10 [M + H] | $^{1}$H NMR (400 MHz, DMSO-d6) δ 11.56 (d, J = 4.8 Hz, 2H), 8.91 (s, 1H), 8.34 (s, 1H), 8.12 (d, J = 8.4 Hz, 1H), 8.04 (d, J = 6.1 Hz, 1H), 7.86 (s, 1H), 7.71 (d, J = 8.2 Hz, 1H), 7.62 (s, 1H), 3.15 (dt, J = 9.3, 5.0 Hz, 1H), 3.05 (dt, J = 9.7, 5.2 Hz, 1H), 2.15 (dt, J = 9.6, 4.9 Hz, 1H), 1.96 (dt, J = 9.4, 4.8 Hz, 1H). $^{19}$F NMR (376 MHz, DMSO-d6) δ −61.09, −75.14. |
| 150 | 415.10 [M + H] | $^{1}$H NMR (400 MHz, DMSO-d6) δ 11.53 (d, J = 4.7 Hz, 2H), 8.97-8.84 (m, 1H), 8.31 (d, J = 1.4 Hz, 1H), 8.11 (dd, J = 8.4, 2.4 Hz, 1H), 8.02 (d, J = 6.3 Hz, 1H), 7.81 (s, 1H), 7.71 (d, J = 8.2 Hz, 1H), 7.58 (s, 1H), 3.20-3.02 (m, 2H), 2.18 (ddd, J = 9.0, 6.1, 3.9 Hz, 1H), 1.95 (ddd, J = 9.2, 5.7, 4.0 Hz, 1H). $^{19}$F NMR (376 MHz, DMSO-d6) δ −61.08, −74.92. |
| 151 | 390.10 [M + H] | $^{1}$H NMR (400 MHz, DMSO-d6) δ 11.57-11.51 (m, 2H), 8.96 (d, J = 2.2 Hz, 1H), 8.20 (dd, J = 8.2, 2.2 Hz, 1H), 8.03 (d, J = 6.4 Hz, 1H), 7.69 (dd, J = 8.3, 0.9 Hz, 1H), 7.59-7.50 (m, 2H), 3.16 (ddd, J = 8.6, 5.7, 4.1 Hz, 1H), 3.02 (ddd, J = 9.1, 6.3, 4.1 Hz, 1H), 2.23 (ddd, J = 8.6, 6.3, 4.0 Hz, 1H), 1.93 (ddd, J = 9.3, 5.7, 4.0 Hz, 1H). $^{19}$F NMR (376 MHz, DMSO-d6) δ −75.26, −155.51 (d, J = 7.4 Hz). |
| 152 | 415.10 [M + H] | $^{1}$H NMR (400 MHz, DMSO-d6) δ 11.59-11.56 (m, 2H), 8.74 (d, J = 2.1 Hz, 1H), 8.37 (d, J = 1.5 Hz, 1H), 8.05 (d, J = 6.1 Hz, 1H), 7.98-7.88 (m, 2H), 7.86 (d, J = 8.2 Hz, 1H), 7.66 (s, 1H), 2.99 (ddd, J = 9.0, 6.2, 4.4 Hz, 1H), 2.89 (ddd, J = 8.8, 6.1, 4.5 Hz, 1H), 2.22 (dt, J = 8.9, 5.4 Hz, 1H), 1.99-1.89 (m, 1H). $^{19}$F NMR (377 MHz, DMSO-d6) δ −66.64, −75.19 |
| 153 | 415.10 [M + H] | $^{1}$H NMR (400 MHz, DMSO-d6) δ 11.56 (d, J = 4.7 Hz, 2H), 8.75 (d, J = 2.1 Hz, 1H), 8.34 (d, J = 1.4 Hz, 1H), 8.04 (d, J = 6.3 Hz, 1H), 7.94 (dd, J = 8.2, 2.2 Hz, 1H), 7.89-7.82 (m, 2H), 7.63 (s, 1H), 3.01 (ddd, J = 9.3, 6.2, 4.4 Hz, 1H), 2.89 (ddd, J = 8.9, 6.1, 4.3 Hz, 1H), 2.24 (dt, J = 8.9, 5.3 Hz, 1H), 1.93 (dt, J = 8.7, 5.3 Hz, 1H). $^{19}$F NMR (376 MHz, DMSO-d6) δ −66.57--66.63 (m), −66.63, −75.09. |
| 154 | 397.10 [M + H] | $^{1}$H NMR (400 MHz, DMSO-d6) δ 11.71 (d, J = 6.2 Hz, 1H), 11.61 (d, J = 2.0 Hz, 1H), 9.18 (dd, J = 5.1, 1.6 Hz, 1H), 8.97 (d, J = 8.3 Hz, 1H), 8.50 (d, J = 1.7 Hz, 1H), 8.27 (d, J = 8.6 Hz, 1H), 8.18-8.07 (m, 3H), 7.91 (dd, J = 8.3, 5.1 Hz, 1H), 7.83-7.75 (m, 2H), 3.20-3.08 (m, 2H), 2.25-2.15 (m, 1H), 2.05 (dt, J = 8.5, 5.5 Hz, 1H). |

TABLE 3-continued

Characterization Data

| Example No. | ES/MS m/z | NMR |
|---|---|---|
| 155 | 372.10 [M + H] | ¹H NMR (400 MHz, DMSO-d6) δ 11.71-11.65 (m, 1H), 11.60 (d, J = 2.0 Hz, 1H), 8.99 (dd, J = 2.3, 0.8 Hz, 1H), 8.49 (d, J = 1.7 Hz, 1H), 8.23 (dd, J = 8.2, 2.2 Hz, 1H), 8.09 (d, J = 6.3 Hz, 2H), 7.78 (s, 1H), 7.69 (d, J = 8.2, 0.9 Hz, 1H), 3.10 (ddt, J = 8.9, 6.4, 3.4 Hz, 2H), 2.05 (dddd, J = 31.9, 8.2, 6.4, 4.1 Hz, 2H). |
| 156 | 397.20 [M + H] | ¹H NMR (400 MHz, DMSO-d6) δ 11.84-11.76 (m, 1H), 11.63 (d, J = 2.0 Hz, 1H), 9.21 (dd, J = 5.2, 1.5 Hz, 1H), 8.97 (d, J = 8.3 Hz, 1H), 8.57 (d, J = 1.8 Hz, 1H), 8.38-8.25 (m, 2H), 8.21 (s, 1H), 8.13 (d, J = 6.2 Hz, 1H), 8.03 (ddd, J = 16.3, 8.7, 3.5 Hz, 2H), 7.87 (s, 1H), 3.28 (dt, J = 9.8, 5.2 Hz, 1H), 3.11-3.01 (m, 1H), 2.12 (dt, J = 8.9, 5.5 Hz, 1H), 2.04 (dt, J = 8.6, 5.6 Hz, 1H). |
| 157 | 397.20 [M + H] | ¹H NMR (400 MHz, DMSO-d6) δ 11.82 (dd, J = 6.4, 2.0 Hz, 1H), 11.63 (d, J = 2.0 Hz, 1H), 9.86 (s, 1H), 8.66 (d, J = 6.6 Hz, 1H), 8.58-8.48 (m, 2H), 8.37 (d, J = 6.5 Hz, 1H), 8.28 (d, J = 1.6 Hz, 1H), 8.20-8.09 (m, 2H), 7.96 (dd, J = 8.7, 1.7 Hz, 1H), 7.87 (s, 1H), 3.39 (dd, J = 8.8, 4.9 Hz, 1H), 3.11 (ddd, J = 9.1, 6.3, 4.3 Hz, 1H), 2.21 (dt, J = 8.7, 5.4 Hz, 1H), 2.11 (dt, J = 8.8, 5.5 Hz, 1H). |
| 158 | 389.10 [M + H] | ¹H NMR (400 MHz, DMSO-d6) δ 11.63 (dd, J = 6.2, 2.0 Hz, 1H), 11.55 (d, J = 2.0 Hz, 1H), 8.04 (d, J = 6.2 Hz, 1H), 7.77 (d, J = 8.3 Hz, 2H), 7.64 (d, J = 6.9 Hz, 1H), 7.55 (s, 1H), 7.51-7.44 (m, 2H), 2.93 (ddd, J = 9.0, 6.2, 4.4 Hz, 1H), 2.84 (ddd, J = 8.9, 6.1, 4.4 Hz, 1H), 2.18 (dt, J = 8.7, 5.3 Hz, 1H), 1.90-1.80 (m, 1H). ¹⁹F NMR (376 MHz, DMSO-d6) δ −75.39, −155.56 (d, J = 7.3 Hz). |
| 159 | 347.10 [M + H] | ¹H NMR (400 MHz, DMSO-d6) δ 11.76 (dd, J = 6.3, 2.0 Hz, 1H), 11.62 (d, J = 2.0 Hz, 1H), 8.67 (dd, J = 5.5, 1.6 Hz, 1H), 8.54 (d, J = 1.7 Hz, 1H), 8.21-8.08 (m, 3H), 7.86 (s, 1H), 7.74 (d, J = 8.0 Hz, 1H), 7.61 (t, J = 6.5 Hz, 1H), 3.27-3.17 (m, 1H), 3.13 (ddd, J = 8.7, 6.3, 4.3 Hz, 1H), 2.22-2.10 (m, 2H). |
| 160 | 415.10 [M + H] | ¹H NMR (400 MHz, DMSO-d6) δ 11.74-11.66 (m, 1H), 11.61 (d, J = 2.0 Hz, 1H), 8.67 (d, J = 5.1 Hz, 1H), 8.51 (d, J = 1.7 Hz, 1H), 8.15-8.06 (m, 2H), 7.86-7.77 (m, 2H), 7.63 (dd, J = 5.2, 1.7 Hz, 1H), 3.20-3.05 (m, 1H), 2.96 (ddd, J = 9.0, 6.2, 4.3 Hz, 1H), 2.15 (dt, J = 8.9, 5.6 Hz, 1H), 2.03 (dt, J = 8.8, 5.6 Hz, 1H). ¹⁹F NMR (376 MHz, DMSO-d6) δ −66.95. |
| 161 | 365.10 [M + H] | ¹H NMR (400 MHz, DMSO-d6) δ 11.77 (d, J = 6.3 Hz, 1H), 11.63 (d, J = 1.9 Hz, 1H), 8.65 (d, J = 2.2 Hz, 1H), 8.59 (d, J = 1.8 Hz, 1H), 8.50 (d, J = 5.2 Hz, 1H), 8.25 (s, 1H), 8.11 (d, J = 6.2 Hz, 1H), 7.91 (s, 1H), 7.51 (t, J = 6.0 Hz, 1H), 3.20 (d, J = 10.3 Hz, 1H), 2.97-2.87 (m, 1H), 2.13 (dt, J = 8.9, 5.5 Hz, 1H), 2.02 (dt, J = 8.7, 5.5 Hz, 1H). ¹⁹F NMR (376 MHz, DMSO-d6) δ −75.65, −133.73. |
| 162 | 347.10 [M + H] | ¹H NMR (400 MHz, DMSO-d6) δ 11.55 (d, J = 6.8 Hz, 1H), 8.78 (d, J = 2.1 Hz, 1H), 8.64 (dd, J = 5.3, 1.4 Hz, 1H), 8.32 (d, J = 1.3 Hz, 1H), 8.14 (d, J = 8.0 Hz, 1H), 8.03 (d, J = 6.0 Hz, 1H), 7.83 (d, J = 1.3 Hz, 1H), 7.75 (dd, J = 8.1, 5.3 Hz, 1H), 7.61 (s, 1H), 3.05 (dt, J = 9.5, 5.7 Hz, 1H), 2.88 (d, J = 8.9, 6.1, 4.5 Hz, 1H), 2.25 (dt, J = 8.8, 5.3 Hz, 1H), 1.91 (m, 1H). ¹⁹F NMR (376 MHz, DMSO-d6) δ −75.05. |
| 163 | 397.20 [M + H] | ¹H NMR (400 MHz, DMSO-d6) δ 11.64-11.55 (m, 2H), 9.06 (d, J = 2.1 Hz, 1H), 8.47 (s, 1H), 8.40 (s, 1H), 8.11-7.97 (m, 3H), 7.94 (s, 1H), 7.84 (dd, J = 8.5, 6.8 Hz, 1H), 7.76-7.68 (m, 2H), 3.13 (ddd, J = 9.4, 6.1, 4.4 Hz, 1H), 3.01-2.91 (m, 1H), 2.24 (dt, J = 8.8, 5.4 Hz, 1H), 2.06 (dt, J = 8.5, 5.5 Hz, 1H). ¹⁹F NMR (377 MHz, DMSO-d6) δ −75.23. |
| 164 | 365.20 [M + H] | ¹H NMR (400 MHz, DMSO-d6) δ 11.81 (d, J = 6.2 Hz, 1H), 11.64 (d, J = 1.8 Hz, 1H), 8.62 (d, J = 1.8 Hz, 1H), 8.51 (d, J = 2.4 Hz, 2H), 8.31 (s, 1H), 8.14 (d, J = 6.2 Hz, 1H), 7.88 (s, 1H), 7.74 (dt, J = 10.4, 2.1 Hz, 1H), 3.16 (dt, J = 9.7, 5.4 Hz, 1H), 2.88-2.78 (m, 1H), 2.00 (dq, J = 11.7, 5.3 Hz, 2H). ¹⁹F NMR (376 MHz, DMSO-d6) δ −127.70 (d, J = 10.1 Hz). |
| 165 | 432.10 [M + H] | ¹H NMR (400 MHz, DMSO-d6) δ 11.72 (dd, J = 6.4, 2.0 Hz, 1H), 11.61 (d, J = 1.9 Hz, 1H), 8.54 (d, J = 1.8 Hz, 1H), 8.22-8.06 (m, 2H), 7.84 (s, 1H), 7.71-7.47 (m, 3H), 2.98 (ddt, J = 39.4, 10.2, 5.4 Hz, 2H), 2.13-1.90 (m, 2H). ¹⁹F NMR (376 MHz, DMSO-d6) δ −61.43, −117.55 (t, J = 8.9 Hz). |
| 166 | 397.20 [M + H] | ¹H NMR (400 MHz, DMSO-d6) δ 11.65-11.54 (m, 2H), 9.80 (s, 1H), 8.65 (d, J = 6.1 Hz, 1H), 8.40 (d, J = 1.4 Hz, 1H), 8.30 (d, J = 6.2 Hz, 1H), 8.12 (d, J = 8.3 Hz, 1H), 8.11-8.01 (m, 2H), 7.93-7.81 (m, 2H), 7.74 (s, 1H), 3.56 (dt, J = 8.7, 5.8 Hz, 1H), 2.90 (dt, J = 8.8, 5.5 Hz, 1H), 2.19 (dt, J = 8.8, 5.3 Hz, 1H), 2.01 (ddd, J = 8.8, 6.4, 4.8 Hz, 1H). |
| 167 | 397.20 [M + H] | ¹H NMR (400 MHz, DMSO-d6) δ 11.63-11.54 (m, 2H), 9.13 (d, J = 5.2 Hz, 1H), 8.43-8.35 (m, 2H), 8.20 (d, J = 8.5 Hz, 1H), 8.07 (d, J = 6.1 Hz, 1H), 7.99 (dd, J = 8.4, 6.8 Hz, 1H), 7.88 (s, 1H), 7.83-7.71 (m, 3H), 3.75-3.73 (m, 1H), 3.04 (dt, J = 9.0, 5.7 Hz, 1H), 2.40-2.30 (m, 1H), 2.17 (dt, J = 8.7, 5.2 Hz, 1H). |

TABLE 3-continued

Characterization Data

| Example No. | ES/MS m/z | NMR |
|---|---|---|
| 168 | 397.20 [M + H] | $^1$H NMR (400 MHz, DMSO-d6) δ 11.64-11.54 (m, 2H), 9.70 (s, 1H), 8.60 (d, J = 6.4 Hz, 1H), 8.40 (d, J = 1.4 Hz, 1H), 8.34-8.27 (m, 2H), 8.08 (d, J = 6.1 Hz, 1H), 8.01 (d, J = 7.2 Hz, 1H), 7.95-7.86 (m, 2H), 7.75 (s, 1H), 3.46 (dt, J = 9.0, 6.0 Hz, 1H), 2.82 (dt, J = 8.9, 5.4 Hz, 1H), 2.17 (dt, J = 8.9, 5.2 Hz, 1H), 1.99 (ddd, J = 8.7, 6.4, 4.8 Hz, 1H). |
| 169 | 385.10 [M + H] | $^1$H NMR (400 MHz, DMSO-d6) δ 11.55 (dd, J = 6.2, 2.0 Hz, 1H), 11.45 (d, J = 2.0 Hz, 1H), 8.21 (d, J = 1.4 Hz, 1H), 8.00 (d, J = 6.2 Hz, 1H), 7.78 (d, J = 1.5 Hz, 1H), 6.85 (s, 1H), 4.64-4.39 (m, 2H), 4.12 (d, J = 9.9 Hz, 1H), 4.02-3.86 (m, 1H), 2.77-2.52 (m, 2H). $^{19}$F NMR (376 MHz, DMSO-d6) δ −79.42 (d, J = 6.6 Hz), −165.61-−166.13 (m). |
| 170 | 375.10 [M + H] | $^1$H NMR (400 MHz, DMSO-d6) δ 11.56-11.37 (m, 2H), 8.20 (d, J = 1.5 Hz, 1H), 8.00 (d, J = 6.2 Hz, 1H), 7.82-7.74 (m, 1H), 6.78 (s, 1H), 6.24 (td, J = 55.8, 4.2 Hz, 1H), 4.15 (s, 2H), 3.95-3.88 (m, 1H), 3.64 (s, 1H), 1.08 (dt, J = 9.9, 5.5 Hz, 1H), 0.90-0.68 (m, 4H). $^{19}$F NMR (376 MHz, DMSO-d6) δ −119.97 (ddd, J = 283.3, 55.5, 11.4 Hz), −124.24 (ddd, J = 283.4, 56.0, 20.9 Hz). |
| 171 | 343.10 [M + H] | $^1$H NMR (400 MHz, DMSO-d6) δ 11.44-11.30 (m, 2H), 8.07 (q, J = 1.3 Hz, 1H), 7.95 (d, J = 6.0 Hz, 1H), 7.60 (dt, J = 2.4, 1.4 Hz, 1H), 6.61 (t, J = 2.0 Hz, 1H), 4.83 (dd, J = 54.5, 3.3 Hz, 1H), 4.62-3.98 (m, 3H), 3.70 (s, 1H), 1.11-0.73 (m, 4H). $^{19}$F NMR (376 MHz, DMSO-d6) δ −74.91-−75.77 (m), −171.06. |
| 172 | 436.10 [M + H] | $^1$H NMR (400 MHz, DMSO-d6) δ 11.57-11.55 (m, 2H), 8.75 (s, 1H), 8.02 (d, J = 6.3 Hz, 1H), 7.52 (s, 1H), 7.32 (ddd, J = 8.6, 5.4, 2.6 Hz, 2H), 7.20-7.09 (m, 2H), 4.34 (q, J = 7.1 Hz, 2H), 2.74 (dddd, J = 19.7, 8.8, 6.1, 4.4 Hz, 2H), 2.01 (dt, J = 9.0, 5.3 Hz, 1H), 1.84-1.74 (m, 1H), 1.33 (t, J = 7.1 Hz, 3H). $^{19}$F NMR (376 MHz, DMSO-d6) δ −75.42, −117.01-−117.55 (m). |
| 173 | 405.20 [M + H] | $^1$H NMR (400 MHz, DMSO-d6) δ 11.58 (d, J = 6.3 Hz, 1H), 11.46 (d, J = 2.0 Hz, 1H), 8.29 (d, J = 1.7 Hz, 1H), 8.03 (d, J = 6.2 Hz, 1H), 7.90 (s, 1H), 7.38-7.28 (m, 2H), 6.94 (dd, J = 9.4, 7.4 Hz, 3H), 4.33 (s, 2H), 3.75 (s, 5H), 3.60-3.47 (m, 1H), 2.47-2.35 (m, 1H), 2.17-2.05 (m, 1H). |
| 174 | 341.20 [M + H] | $^1$H NMR (400 MHz, DMSO-d6) δ 11.58 (d, J = 6.3 Hz, 1H), 11.46 (d, J = 2.0 Hz, 1H), 8.29 (s, 1H), 8.02 (d, J = 6.2 Hz, 1H), 7.92 (s, 1H), 6.92 (s, 1H), 4.18-3.82 (m, 2H), 3.68 (s, 1H), 3.44 (s, 1H), 2.18 (dt, J = 12.3, 6.3 Hz, 1H), 2.01 (p, J = 8.9 Hz, 1H), 1.74-1.55 (m, 2H), 0.99 (t, J = 7.2 Hz, 6H). |
| 175 | 367.10 [M + H] | $^1$H NMR (400 MHz, DMSO-d6) δ 11.57 (d, J = 6.2 Hz, 1H), 11.45 (d, J = 1.9 Hz, 1H), 8.24 (s, 1H), 8.01 (d, J = 6.1 Hz, 1H), 7.83 (s, 1H), 6.88 (s, 1H), 4.19 (t, J = 10.0 Hz, 3H), 4.07-3.75 (m, 3H), 3.49 (h, J = 8.4 Hz, 1H), 2.37 (dtd, J = 12.7, 7.6, 5.0 Hz, 1H), 2.23-2.09 (m, 1H). $^{19}$F NMR (376 MHz, DMSO-d6) δ −70.12 (d, J = 9.2 Hz). |
| 176 | 353.10 [M + H] | $^1$H NMR (400 MHz, DMSO-d6) δ 11.46-11.37 (m, 2H), 7.97 (d, J = 6.1 Hz, 1H), 7.40 (d, J = 7.2 Hz, 1H), 6.63 (s, 1H), 4.37 (d, J = 13.8 Hz, 2H), 3.97 (d, J = 7.7 Hz, 2H), 2.60 (tt, J = 14.5, 7.4 Hz, 2H). $^{19}$F NMR (376 MHz, DMSO-d6) δ −101.39 (p, J = 13.7 Hz), −155.49 (d, J = 7.4 Hz). |
| 177 | 353.10 [M + H] | $^1$H NMR (400 MHz, DMSO-d6) δ 11.46-11.37 (m, 2H), 7.97 (d, J = 6.1 Hz, 1H), 7.41 (d, J = 7.2 Hz, 1H), 6.60 (s, 1H), 5.60-5.50 (m, 1H), 5.47-5.37 (m, 1H), 4.27 (s, 2H), 4.00 (d, J = 29.5 Hz, 2H), 3.58 (s, 2H). $^{19}$F NMR (376 MHz, DMSO-d6) δ −155.52 (d, J = 7.1 Hz), −205.72-−206.06 (m). |
| 178 | 365.20 [M + H] | $^1$H NMR (400 MHz, DMSO-d6) δ 11.65 (dd, J = 6.2, 1.9 Hz, 1H), 11.56 (d, J = 2.0 Hz, 1H), 8.69 (dd, J = 5.6, 1.5 Hz, 1H), 8.31 (t, J = 8.0 Hz, 1H), 8.06 (d, J = 6.2 Hz, 1H), 7.84 (d, J = 8.1 Hz, 1H), 7.72 (t, J = 6.6 Hz, 1H), 7.66-7.58 (m, 2H), 3.38 (dt, J = 9.5, 5.5 Hz, 1H), 3.13 (ddd, J = 9.2, 6.4, 4.3 Hz, 1H), 2.40 (dt, J = 8.6, 5.3 Hz, 1H), 2.18-2.08 (m, 1H). $^{19}$F NMR (376 MHz, DMSO-d6) δ −155.40 (d, J = 7.0 Hz). |
| 179 | 366.10 [M + H | $^1$H NMR (400 MHz, DMSO-d6) δ 11.62 (d, J = 6.3 Hz, 1H), 11.55 (d, J = 1.9 Hz, 1H), 9.07 (s, 1H), 8.78 (s, 2H), 8.05 (d, J = 6.1 Hz, 1H), 7.68-7.57 (m, 2H), 2.91 (ddt, J = 14.6, 10.6, 5.4 Hz, 2H), 2.20 (dt, J = 8.9, 5.5 Hz, 1H), 1.92 (dt, J = 8.6, 5.4 Hz, 1H). $^{19}$F NMR (376 MHz, DMSO-d6) δ −155.45 (d, J = 7.0 Hz). |
| 180 | 365.20 [M + H] | $^1$H NMR (400 MHz, DMSO-d6) δ 11.63 (dd, J = 6.3, 2.0 Hz, 1H), 11.55 (d, J = 1.9 Hz, 1H), 8.94 (d, J = 2.0 Hz, 1H), 8.77 (dd, J = 5.6, 1.2 Hz, 1H), 8.48 (dt, J = 8.3, 1.6 Hz, 1H), 8.09-7.96 (m, 2H), 7.60 (t, J = 3.5 Hz, 2H), 3.19 (ddd, J = 9.0, 6.1, 4.5 Hz, 1H), 2.96 (ddd, J = 9.0, 6.2, 4.5 Hz, 1H), 2.32 (dt, J = 8.9, 5.4 Hz, 1H), 1.98 (dt, J = 8.8, 5.4 Hz, 1H). $^{19}$F NMR (376 MHz, DMSO-d6) δ −155.48 (d, J = 7.1 Hz). |

TABLE 3-continued

Characterization Data

| Example No. | ES/MS m/z | NMR |
|---|---|---|
| 181 | 365.20 [M + H] | $^1$H NMR (400 MHz, DMSO-d6) δ 11.62 (dd, J = 6.3, 2.0 Hz, 1H), 11.56 (d, J = 2.0 Hz, 1H), 8.84-8.78 (m, 2H), 8.05 (d, J = 6.2 Hz, 1H), 8.02-7.95 (m, 2H), 7.64-7.55 (m, 2H), 3.24 (ddd, J = 8.8, 5.9, 4.2 Hz, 1H), 3.10 (ddd, J = 9.1, 6.6, 4.3 Hz, 1H), 2.54 (s, 1H), 2.08 (dt, J = 9.0, 5.3 Hz, 1H). $^{19}$F NMR (376 MHz, DMSO-d6) δ −75.55, −155.41 (d, J = 7.0 Hz). |
| 182 | 398.10 [M + H] | $^1$H NMR (400 MHz, DMSO-d6) δ 11.63-11.51 (m, 2H), 8.04 (d, J = 6.2 Hz, 1H), 7.62 (d, J = 6.9 Hz, 1H), 7.51 (s, 1H), 7.40-7.32 (m, 2H), 7.29 (d, J = 8.6 Hz, 2H), 2.83 (ddd, J = 9.0, 6.2, 4.4 Hz, 1H), 2.76-2.66 (m, 1H), 2.08 (dt, J = 8.8, 5.3 Hz, 1H), 1.75 (ddd, J = 8.7, 6.3, 4.9 Hz, 1H). $^{19}$F NMR (376 MHz, DMSO-d6) δ −155.42 (d, J = 6.9 Hz). |
| 183 | 432.10 [M + H] | $^1$H NMR (400 MHz, DMSO-d6) δ 11.56 (dd, J = 10.4, 4.1 Hz, 2H), 8.04 (d, J = 6.1 Hz, 1H), 7.66 (d, J = 8.1 Hz, 2H), 7.58 (d, J = 7.0 Hz, 1H), 7.54-7.46 (m, 3H), 2.95 (ddd, J = 9.0, 6.2, 4.4 Hz, 1H), 2.84-2.74 (m, 1H), 2.18 (dt, J = 8.7, 5.3 Hz, 1H), 1.83 (dt, J = 8.6, 5.2 Hz, 1H). $^{19}$F NMR (376 MHz, DMSO-d6) δ −61.25, −155.50 (d, J = 7.0 Hz), −221.07. |
| 184 | 377.20 [M + H] | $^1$H NMR (400 MHz, DMSO-d6) δ 11.69-11.62 (m, 1H), 11.59 (d, J = 1.9 Hz, 1H), 8.47 (s, 1H), 8.12-8.04 (m, 2H), 7.72 (d, J = 2.6 Hz, 1H), 7.67 (s, 1H), 7.37 (dd, J = 9.4, 2.6 Hz, 1H), 6.39 (d, J = 9.3 Hz, 1H), 3.41 (s, 3H), 2.74-2.66 (m, 1H), 2.55 (t, J = 5.5 Hz, 1H), 1.87 (dt, J = 9.0, 5.3 Hz, 1H), 1.73 (dt, J = 8.4, 5.5 Hz, 1H). |
| 185 | 381.10 [M + H] | $^1$H NMR (400 MHz, DMSO-d6) δ 11.43-11.33 (m, 2H), 8.05 (s, 1H), 7.94 (d, J = 6.1 Hz, 1H), 7.57 (s, 1H), 6.61 (s, 1H), 4.26-3.99 (m, 4H), 2.41-2.29 (m, 1H), 2.06 (ddd, J = 13.0, 7.9, 5.2 Hz, 1H), 1.37 (s, 3H). $^{19}$F NMR (376 MHz, DMSO-d6) δ −75.17 (t, J = 7.6 Hz), −75.97. |
| 186 | 331.10 [M + H] | $^1$H NMR (400 MHz, DMSO-d6) δ 11.38 (dd, J = 12.4, 4.1 Hz, 2H), 8.05 (d, J = 1.3 Hz, 1H), 7.94 (d, J = 6.1 Hz, 1H), 7.58 (t, J = 1.4 Hz, 1H), 6.60 (d, J = 2.3 Hz, 1H), 4.57-3.71 (m, 4H), 2.38-2.06 (m, 2H), 1.62 (d, J = 20.9 Hz, 3H). $^{19}$F NMR (376 MHz, DMSO-d6) δ −74.98--75.61 (m), −140.81. |
| 187 | 383.10 [M + H] | $^1$H NMR (400 MHz, DMSO-d6) δ 11.38 (dd, J = 14.7, 4.1 Hz, 2H), 8.04 (d, J = 1.2 Hz, 1H), 7.94 (d, J = 6.1 Hz, 1H), 7.56 (d, J = 1.2 Hz, 1H), 6.61 (s, 1H), 5.30 (d, J = 4.0 Hz, 1H), 4.40-4.14 (m, 4H), 2.32 (s, 2H). $^{19}$F NMR (376 MHz, DMSO-d6) δ −57.25, −75.00. |
| 188 | 361.10 [M + H] | $^1$H NMR (400 MHz, DMSO-d6) δ 11.43-11.33 (m, 2H), 8.04 (d, J = 1.1 Hz, 1H), 7.95 (d, J = 6.1 Hz, 1H), 7.57 (d, J = 1.1 Hz, 1H), 6.60 (s, 1H), 4.04-3.71 (m, J = 5.6 Hz, 6H), 3.39 (s, 3H), 2.31-2.13 (m, 2H). $^{19}$F NMR (376 MHz, DMSO-d6) δ −75.22 (d, J = 3.5 Hz), −154.09. |
| 189 | 397.10 [M + H] | $^1$H NMR (400 MHz, DMSO-d6) δ 11.39 (dd, J = 14.1, 4.0 Hz, 2H), 8.05 (d, J = 1.2 Hz, 1H), 7.94 (d, J = 6.1 Hz, 1H), 7.57 (d, J = 1.1 Hz, 1H), 6.62 (s, 1H), 4.56 (s, 2H), 4.14 (d, J = 12.9 Hz, 2H), 3.42 (s, 3H), 2.44-2.33 (m, 2H) $^{19}$F NMR (376 MHz, DMSO-d6) δ −75.07 (d, J = 4.5 Hz), −75.56 |
| 190 | 325.10 [M + H] | $^1$H NMR (400 MHz, DMSO-d6) δ 11.41-11.33 (m, 2H), 8.05 (d, J = 1.3 Hz, 1H), 7.95 (d, J = 6.1 Hz, 1H), 7.58 (d, J = 1.3 Hz, 1H), 6.60 (s, 1H), 3.87-3.80 (m, 4H), 1.95 (t, J = 6.9 Hz, 2H), 0.74-0.61 (m, 4H). $^{19}$F NMR (376 MHz, DMSO-d6) δ −75.22. |
| 191 | 331.10 [M + H] | $^1$H NMR (400 MHz, DMSO-d6) δ 11.43-11.31 (m, 2H), 8.05 (d, J = 1.2 Hz, 1H), 7.94 (d, J = 6.1 Hz, 1H), 7.58 (d, J = 1.2 Hz, 1H), 6.60 (s, 1H), 4.10-3.71 (m, 4H), 2.36-2.06 (m, 2H), 1.62 (d, J = 20.9 Hz, 3H). $^{19}$F NMR (376 MHz, DMSO-d6) δ −75.26, −140.83 |
| 192 | 361.10 [M + H] | $^1$H NMR (400 MHz, DMSO-d6) δ 11.43-11.30 (m, 2H), 8.05 (d, J = 1.1 Hz, 1H), 7.95 (d, J = 6.1 Hz, 1H), 7.57 (d, J = 1.2 Hz, 1H), 6.62 (s, 1H), 4.28-3.85 (m, 4H), 2.21 (ddt, J = 33.2, 12.5, 6.2 Hz, 2H), 1.74 (dddd, J = 41.4, 13.3, 8.4, 4.6 Hz, 2H). $^{19}$F NMR (376 MHz, DMSO-d6) δ −75.30, −135.85--138.31 (m). |
| 193 | 381.10 [M + H] | $^1$H NMR (400 MHz, DMSO-d6) δ 11.43-11.33 (m, 2H), 8.04 (d, J = 1.2 Hz, 1H), 7.94 (d, J = 6.1 Hz, 1H), 7.57 (d, J = 1.1 Hz, 1H), 6.60 (s, 1H), 4.30-4.01 (m, 4H) 3.11 (h, J = 8.7 Hz, 1H), 2.59 (p, J = 7.6 Hz, 1H), 1.21 (d, J = 6.6 Hz, 3H). $^{19}$F NMR (376 MHz, DMSO-d6) δ −68.87 (d, J = 9.3 Hz), −75.16. |
| 194 | 441.10 [M + H] | $^1$H NMR (400 MHz, DMSO-d6) δ 11.44-11.35 (m, 2H), 8.09 (d, J = 1.1 Hz, 1H), 7.95 (d, J = 6.1 Hz, 1H), 7.59 (d, J = 1.1 Hz, 1H), 7.39-7.27 (m, 2H), 7.03-6.94 (m, 2H), 6.67 (s, 1H), 4.52-4.47 (m, 3H), 4.12-4.10 (m, 2H), 3.33 (s, 3H). $^{19}$F NMR (376 MHz, DMSO-d6) δ −75.07, −108.42. |
| 195 | 342.10 [M + H] | $^1$H NMR (400 MHz, DMSO-d6) δ 11.40 (dd, J = 14.1, 4.2 Hz, 2H), 8.08 (d, J = 1.2 Hz, 1H), 7.95 (d, J = 6.1 Hz, 1H), 7.59 (d, J = 1.2 Hz, 1H), 6.64 (s, 1H), 4.92 (s, 2H), 4.47 (dd, J = 34.8, 13.6 Hz, 1H), 4.10 (s, 1H), 3.81 (d, J = 10.0 Hz, 1H), 2.91-2.66 (m, 2H). $^{19}$F NMR (376 MHz, DMSO-d6) δ −115.35 (t, J = 13.8 Hz). |

TABLE 3-continued

Characterization Data

| Example No. | ES/MS m/z | NMR |
|---|---|---|
| 196 | 383.10 [M + H] | $^1$H NMR (400 MHz, DMSO-d6) δ 11.42-11.33 (m, 2H), 8.05 (s, 1H), 7.94 (d, J = 5.9 Hz, 1H), 7.58 (s, 1H), 6.62 (s, 1H), 5.30 (s, 1H), 4.14 (d, J = 12.8 Hz, 1H), 3.95 (s, 1H), 3.78 (s, 1H), 2.41-2.26 (m, 2H). $^{19}$F NMR (376 MHz, DMSO-d6) δ −57.25, −75.26 |
| 197 | 435.20 [M + H] | $^1$H NMR (400 MHz, DMSO-d6) δ 11.53 (s, 2H), 8.48 (d, J = 1.7 Hz, 1H), 8.01 (d, J = 6.2 Hz, 1H), 7.55 (s, 1H), 7.36-7.27 (m, 2H), 7.14 (t, J = 8.7 Hz, 2H), 3.38 (s, 3H), 3.02 (s, 3H), 2.89 (dd, J = 9.1, 5.3 Hz, 1H), 2.63 (dt, J = 10.0, 5.5 Hz, 1H), 2.12 (dt, J = 9.9, 5.6 Hz, 1H), 1.74 (dt, J = 8.0, 5.6 Hz, 1H). $^{19}$F NMR (376 MHz, DMSO-d6) δ −117.40 (tt, J = 9.8, 5.6 Hz). |
| 198 | 483.10 [M + H] | $^1$H NMR (400 MHz, DMSO-d6) δ 11.54 (s, 2H), 8.66 (s, 1H), 8.02 (s, 1H), 7.63 (s, 1H), 7.38-7.28 (m, 2H), 7.21-7.06 (m, 2H), 5.03 (p, J = 12.4 Hz, 2H), 4.51 (t, J = 12.6 Hz, 2H), 3.01 (dd, J = 6.3, 3.1 Hz, 1H), 2.63 (dt, J = 9.0, 5.4 Hz, 1H), 2.33-2.17 (m, 1H), 1.74-1.68 (m, 1H). $^{19}$F NMR (376 MHz, DMSO-d6) δ −100.54 (p, J = 12.6 Hz), −117.47 (ddd, J = 14.4, 9.2, 5.5 Hz). |
| 199 | 497.10 [M + H] | $^1$H NMR (400 MHz, DMSO-d6) δ 11.54 (s, 2H), 8.62 (s, 1H), 8.02 (d, J = 4.9 Hz, 1H), 7.61 (d, J = 2.1 Hz, 1H), 7.32 (ddd, J = 8.9, 5.5, 3.3 Hz, 2H), 7.14 (t, J = 8.8 Hz, 2H), 4.55-4.45 (m, 1H), 4.30 (td, J = 7.4, 2.8 Hz, 1H), 4.08-3.86 (m, 1H), 3.77 (t, J = 7.5 Hz, 1H), 3.08-2.87 (m, OH), 2.72-2.55 (m, 1H), 2.43 (dd, J = 14.4, 7.2 Hz, 1H), 2.22-2.14 (m, 1H), 1.74 (ddd, J = 8.8, 6.4, 4.8 Hz, 1H). $^{19}$F NMR (376 MHz, DMSO-d6) δ −101.33−−101.53 (m), −102.26 (h, J = 13.7 Hz), −117.40 (ddt, J = 14.5, 8.9, 5.5 Hz). |
| 200 | 497.10 [M + H] | $^1$H NMR (400 MHz, DMSO-d6) δ 11.54 (s, 2H), 8.62 (s, 1H), 8.02 (s, 1H), 7.62 (d, J = 3.7 Hz, 1H), 7.33 (ddd, J = 8.5, 5.4, 2.7 Hz, 2H), 7.14 (td, J = 8.8, 1.3 Hz, 2H), 5.40 (ddd, J = 49.4, 11.9, 6.3 Hz, 2H), 4.51 (ddt, J = 19.9, 13.3, 6.4 Hz, 1H), 4.30-4.07 (m, 1H), 4.06-3.65 (m, 2H), 2.98 (td, J = 9.9, 9.1, 5.1 Hz, 1H), 2.62 (tt, J = 9.1, 4.1 Hz, 1H), 2.19 (dt, J = 10.0, 5.4 Hz, 1H), 1.74 (dtd, J = 8.8, 4.8, 2.6 Hz, 1H). $^{19}$F NMR (376 MHz, DMSO-d6) δ −117.39 (dtd, J = 14.3, 9.1, 4.4 Hz), −205.30−−205.62 (m), −205.98−−206.31 (m). |
| 201 | 401.10 [M + H] | $^1$H NMR (400 MHz, DMSO-d6) δ 11.41 (dd, J = 13.2, 4.1 Hz, 2H), 8.09 (d, J = 1.2 Hz, 1H), 7.94 (d, J = 6.1 Hz, 1H), 7.59 (d, J = 1.1 Hz, 1H), 7.16 (s, 0H), 6.98 (s, 0H), 6.80 (s, 0H), 6.62 (s, 1H), 5.25 (q, J = 7.4, 6.6 Hz, 1H), 4.41 (q, J = 15.4 Hz, 3H), 4.06 (d, J = 12.2 Hz, 1H), 3.45 (q, J = 7.0 Hz, 1H). $^{19}$F NMR (376 MHz, DMSO-d6) δ −74.85, −82.06−−82.60 (m), −111.07 (d, J = 235.7 Hz), −119.30 (d, J = 236.6 Hz). |
| 202 | 401.10 [M + H] | $^1$H NMR (400 MHz, DMSO-d6) δ 11.45-11.36 (m, 2H), 8.09 (s, 1H), 7.95 (d, J = 5.9 Hz, 1H), 7.60 (s, 1H), 7.16 (s, 0H), 6.98 (s, 0H), 6.80 (s, 0H), 6.63 (s, 1H), 5.31-5.22 (m, 1H), 4.39 (t, J = 15.0 Hz, 3H), 4.06 (d, J = 11.8 Hz, 1H). $^{19}$F NMR (376 MHz, DMSO-d6) δ −75.39, −82.37 (dd, J = 73.5, 5.4 Hz), −111.07 (d, J = 236.5 Hz), −119.31 (d, J = 236.2 Hz). |
| 203 | 433.10 [M + H] | $^1$H NMR (400 MHz, DMSO-d6) δ 11.45-11.35 (m, 2H), 8.08 (d, J = 1.1 Hz, 1H), 7.94 (d, J = 6.1 Hz, 1H), 7.58 (d, J = 1.1 Hz, 1H), 6.61 (s, 1H), 4.73-4.62 (m, 1H), 4.57-4.18 (m, 4H), 4.06 (s, 1H). $^{19}$F NMR (376 MHz, DMSO-d6) δ −74.04 (t, J = 9.1 Hz), −74.92, −107.83 (d, J = 237.1 Hz), −121.93 (d, J = 237.7 Hz). |
| 204 | 436.20 [M + H] | $^1$H NMR (400 MHz, DMSO-d6) δ 11.46-11.35 (m, 2H), 8.08 (s, 1H), 7.95 (d, J = 6.0 Hz, 1H), 7.58 (s, 1H), 6.61 (s, 1H), 4.54-4.09 (m, 7H), 2.87 (d, J = 25.8 Hz, 6H). $^{19}$F NMR (376 MHz, DMSO-d6) δ −75.16 (t, J = 4.2 Hz), −107.83 (d, J = 236.3 Hz), −121.91 (d, J = 236.1 Hz). |
| 205 | 392.10 [M + H] | $^1$H NMR (400 MHz, DMSO-d6) δ 11.45-11.31 (m, 2H), 8.50 (d, J = 8.6 Hz, 1H), 8.08 (d, J = 1.2 Hz, 1H), 7.95 (d, J = 6.1 Hz, 1H), 7.59 (d, J = 1.2 Hz, 1H), 6.62 (s, 1H), 5.00-4.84 (m, 1H), 4.39 (t, J = 27.3 Hz, 3H), 3.85-3.65 (m, 1H), 1.92 (d, J = 3.2 Hz, 3H). $^{19}$F NMR (376 MHz, DMSO-d6) δ −75.37 , −111.06 (dq, J = 229.5, 9.8 Hz), −114.79 (d, J = 229.8 Hz). |
| 206 | 476.20 [M + H] | $^1$H NMR (400 MHz, DMSO-d6) δ 11.52-11.30 (m, 2H), 8.50 (d, J = 8.7 Hz, 1H), 8.08 (d, J = 1.1 Hz, 1H), 7.95 (d, J = 6.1 Hz, 1H), 7.62-7.56 (m, 1H), 6.61 (s, 1H), 4.75 (q, J = 9.1 Hz, 3H), 4.39 (d, J = 32.5 Hz, 3H), 3.76 (d, J = 38.3 Hz, 1H). $^{19}$F NMR (376 MHz, DMSO-d6) δ −73.29 (t, J = 9.2 Hz), −75.04−−75.71 (m), −111.17 (dq, J = 230.4, 10.0 Hz), −115.28 (d, J = 229.7 Hz). |
| 207 | 448.20 [M + H] | $^1$H NMR (400 MHz, DMSO-d6) δ 11.50-11.33 (m, 2H), 8.07 (d, J = 1.1 Hz, 1H), 7.96 (dd, J = 7.8, 5.4 Hz, 2H), 7.58 (d, J = 1.2 Hz, 1H), 6.60 (s, 1H), 4.72 (dt, J = 15.2, 8.0 Hz, 1H), 4.37 (d, J = 48.8 Hz, 3H), 3.94-3.68 (m, 3H), 1.18-1.08 (m, 1H), 0.58-0.48 (m, 2H), 0.35-0.24 (m, 2H). $^{19}$F NMR (376 MHz, DMSO-d6) δ −73.56−−76.30 (m), −111.39 (dd, J = 230.3, 10.1 Hz), −115.23 (d, J = 229.7 Hz). |

TABLE 3-continued

Characterization Data

| Example No. | ES/MS m/z | NMR |
|---|---|---|
| 208 | 458.20 [M + H] | $^1$H NMR (400 MHz, DMSO-d6) δ 11.46-11.36 (m, 2H), 8.32 (d, J = 8.7 Hz, 1H), 8.08 (d, J = 1.1 Hz, 1H), 7.95 (d, J = 6.1 Hz, 1H), 7.58 (d, J = 1.1 Hz, 1H), 6.61 (s, 1H), 6.27 (tt, J = 54.3, 3.3 Hz, 1H), 4.73 (dq, J = 16.1, 8.2 Hz, 1H), 4.52-4.29 (m, 5H), 3.86-3.70 (m, 1H). $^{19}$F NMR (376 MHz, DMSO-d6) δ −75.38 (d, J = 6.2 Hz), −110.86-−111.69 (m), −115.21 (d, J = 229.0 Hz), −126.66 (dt, J = 54.3, 15.6 Hz). |
| 209 | 454.20 [M + H] | $^1$H NMR (400 MHz, DMSO-d6) δ 11.45-11.36 (m, 2H), 8.91 (d, J = 8.4 Hz, 1H), 8.08 (s, 1H), 7.99-7.88 (m, 3H), 7.63-7.52 (m, 2H), 7.50 (t, J = 7.5 Hz, 2H), 6.65 (s, 1H), 5.26-5.16 (m, 1H), 4.52 (s, 3H), 4.02 (s, 1H) $^{19}$F NMR (376 MHz, DMSO-d6) δ −75.10, −108.31-−109.39 (m), −115.27 (d, J = 229.6 Hz). |
| 210 | 522.20 [M + H] | $^1$H NMR (400 MHz, DMSO-d6) δ 11.41 (d, J = 14.6 Hz, 2H), 9.16 (d, J = 8.3 Hz, 1H), 8.15-8.03 (m, 3H), 7.93 (dd, J = 25.6, 7.1 Hz, 3H), 7.59 (s, 1H), 6.65 (s, 1H), 5.26-5.17 (m, 1H), 4.53 (s, 2H), 4.40 (s, 1H), 4.04 (s, 1H). $^{19}$F NMR (376 MHz, DMSO-d6) δ −61.90, −74.59, −108.94 (dd, J = 230.2, 11.2 Hz), −115.25 (d, J = 231.3 Hz). |
| 211 | 523.20 [M + H] | $^1$H NMR (400 MHz, DMSO-d6) δ 11.45-11.36 (m, 2H), 9.54 (d, J = 8.9 Hz, 1H), 9.13-9.05 (m, 1H), 8.48 (dd, J = 8.2, 2.3 Hz, 1H), 8.29 (d, J = 8.2 Hz, 1H), 8.09 (d, J = 1.2 Hz, 1H), 7.96 (d, J = 6.1 Hz, 1H), 7.59 (d, J = 1.2 Hz, 1H), 6.65 (s, 1H), 5.24 (q, J = 9.4 Hz, 1H), 5.09 (s, 0H), 4.54 (s, 2H), 4.42 (s, 1H), 4.12 (s, 1H). $^{19}$F NMR (376 MHz, DMSO-d6) δ −61.56, −75.29 (d, J = 3.1 Hz), −106.96-−108.41 (m), −114.63 (d, J = 231.2 Hz). |
| 212 | 545.10 [M + H] | $^1$H NMR (400 MHz, DMSO-d6) δ 11.58-11.50 (m, 2H), 8.08-8.01 (m, 1H), 7.85 (s, 1H), 7.56 (s, 1H), 7.31 (d, J = 7.6 Hz, 1H), 7.13 (s, 1H), 7.01 (dd, J = 7.7, 1.5 Hz, 1H), 4.63 (q, J = 9.4 Hz, 2H), 2.86 (dt, J = 9.3, 5.8 Hz, 1H), 2.76 (dd, J = 8.9, 5.1 Hz, 1H), 2.17-2.06 (m, 1H), 1.87-1.74 (m, 1H), 1.30 (s, 6H). $^{19}$F NMR (376 MHz, DMSO-d6) δ −69.31 (t, J = 9.3 Hz), −74.69 |
| 213 | 520.10 [M + H] | $^1$H NMR (400 MHz, Acetonitrile-d3) δ 9.24 (s, 2H), 8.13 (d, J = 6.4 Hz, 1H), 7.78 (d, J = 4.3 Hz, 2H), 7.66 (d, J = 8.5 Hz, 1H), 7.45 (d, J = 2.1 Hz, 1H), 7.17 (dd, J = 8.5, 1.3 Hz, 1H), 4.98 (q, J = 8.7 Hz, 2H), 2.98-2.78 (m, 2H), 2.11 (dt, J = 9.1, 5.7 Hz, 1H), 1.90 (dt, J = 8.9, 5.8 Hz, 1H). $^{19}$F NMR (376 MHz, Acetonitrile-d3) δ −72.34 (t, J = 8.8 Hz), −77.32, −135.42 (d, J = 2.1 Hz). |
| 214 | 468.20 [M + H] | $^1$H NMR (400 MHz, DMSO-d6) δ 11.53 (d, J = 4.6 Hz, 2H), 8.14-8.02 (m, 2H), 7.78-7.63 (m, 2H), 7.61-7.46 (m, 2H), 7.08 (dd, J = 8.4, 1.4 Hz, 1H), 6.61-6.25 (m, 1H), 4.91 (td, J = 15.0, 3.8 Hz, 2H), 3.02 (ddd, J = 9.1, 6.2, 4.4 Hz, 1H), 2.79 (dt, J = 9.6, 5.5 Hz, 1H), 2.17 (dt, J = 8.7, 5.2 Hz, 1H), 1.90 (dt, J = 8.7, 5.5 Hz, 1H). $^{19}$F NMR (376 MHz, DMSO-d6) δ −74.68, −122.27 (t, J = 15.0 Hz), −122.41 (t, J = 15.1 Hz), −155.59 (d, J = 7.4 Hz). |
| 215 | 396.0 [M + H]. | $^1$H NMR (400 MHz, DMSO-d6) δ 11.64-11.48 (m, 2H), 8.34 (d, J = 6.3 Hz, 1H), 8.16 (d, J = 2.3 Hz, 1H), 7.68 (s, 1H), 7.52 (d, J = 8.1 Hz, 2H), 7.45 (d, J = 8.1 Hz, 2H), 7.01 (t, J = 56.0 Hz, 1H), 6.63 (d, J = 2.3 Hz, 1H), 3.14-3.05 (m, 1H), 2.72-2.61 (m, 1H), 1.98-1.79 (m, 2H). $^{19}$F NMR (376 MHz, DMSO-d6) δ −75.10, −109.35. |
| 216 | 363.1 [M + H]. | $^1$H NMR (400 MHz, DMSO-d6) δ 11.65 (s, 1H), 11.52 (s, 1H), 8.38 (d, J = 6.0 Hz, 1H), 8.07 (s, 1H), 7.00 (s, 1H), 6.41 (s, 1H), 4.59 (t, J = 13.7 Hz, 2H), 3.91 (s, 2H), 1.22 (s, 6H). $^{19}$F NMR (376 MHz, DMSO-d6) δ −74.85, −115.20. |
| 217 | 391.1 [M + H]. | $^1$H NMR (400 MHz, DMSO-d6) δ 11.75-11.45 (m, 2H), 8.40 (d, J = 5.9 Hz, 1H), 7.98 (s, 1H), 6.92 (s, 1H), 4.58 (t, J = 13.8 Hz, 2H), 3.90 (s, 2H), 2.67 (q, J = 7.6 Hz, 2H), 1.27-1.18 (m, 9H). $^{19}$F NMR (376 MHz, DMSO-d6) δ −75.18, −115.17. |
| 218 | 395.0 [M + H]. | $^1$H NMR (400 MHz, DMSO-d6) δ 11.55 (d, J = 6.4 Hz, 1H), 11.47 (s, 1H), 8.40 (d, J = 6.3 Hz, 1H), 8.19 (s, 1H), 7.21 (s, 1H), 4.64 (t, J = 12.5 Hz, 2H), 4.06 (s, 2H), 1.08-1.00 (m, 4H). $^{19}$F NMR (376 MHz, DMSO-d6) δ −107.33. |
| 219 | 381.1 [M + H]. | $^1$H NMR (400 MHz, DMSO-d6) δ 11.58-11.43 (m, 2H), 8.35 (d, J = 6.3 Hz, 1H), 8.19 (d, J = 3.5 Hz, 1H), 7.08 (s, 1H), 4.56 (t, J = 13.8 Hz, 2H), 3.84 (s, 2H), 1.21 (s, 6H). $^{19}$F NMR (376 MHz, DMSO-d6) δ −75.35, −115.25, −187.82. |
| 220 | 397.1 [M + H]. | $^1$H NMR (400 MHz, DMSO-d6) δ 11.57-11.45 (m, 2H), 8.39 (d, J = 6.4 Hz, 1H), 8.19 (s, 1H), 7.19 (s, 1H), 4.56 (t, J = 13.7 Hz, 2H), 3.85 (s, 2H), 1.22 (s, 6H). $^{19}$F NMR (376 MHz, DMSO-d6) δ −74.85, −115.25. |
| 221 | 349.1 [M + H]. | $^1$H NMR (400 MHz, DMSO-d6) δ 11.73 (s, 1H), 11.58 (s, 1H), 8.42 (d, J = 6.1 Hz, 1H), 8.10 (d, J = 2.3 Hz, 1H), 6.97 (s, 1H), 6.44 (d, J = 2.3 Hz, 1H), 4.63-4.51 (m, 2H), 4.37-4.30 (m, 1H), 3.71-3.63 (m, 1H), 2.97-2.79 (m, 1H), 1.16 (d, J = 6.8 Hz, 3H). $^{19}$F NMR (376 MHz, DMSO-d6) δ −75.07, −109.83 (d, J = 226.5 Hz), −113.68 (d, J = 227.8 Hz). |

TABLE 3-continued

Characterization Data

| Example No. | ES/MS m/z | NMR |
|---|---|---|
| 222 | 367.0 [M + H]. | $^1$H NMR (400 MHz, DMSO-d6) δ 11.57-11.42 (m, 2H), 8.35 (d, J = 6.3 Hz, 1H), 8.19 (d, J = 3.5 Hz, 1H), 7.09 (s, 1H), 4.59-4.44 (m, 2H), 4.28-4.17 (m, 1H), 3.62-3.52 (m, 1H), 2.93-2.75 (m, 1H), 1.15 (d, J = 6.8 Hz, 3H). $^{19}$F NMR (376 MHz, DMSO-d6) δ −75.30, −109.72 (d, J = 227.4 Hz), −113.69 (d, J = 227.5 Hz), −187.84. |
| 223 | 339.1 [M + H]. | $^1$H NMR (400 MHz, DMSO-d6) δ 11.44-11.32 (m, 2H), 8.06 (s, 1H), 7.94 (d, J = 6.0 Hz, 1H), 7.61 (s, 1H), 6.65 (s, 1H), 4.10-3.95 (m, 2H), 3.77-3.55 (m, 2H), 2.83-2.74 (m, 2H), 1.90-1.46 (m, 6H). $^{19}$F NMR (376 MHz, DMSO-d6) δ −75.27. |
| 224 | 347.0 [M + H]. | $^1$H NMR (400 MHz, DMSO-d6) δ 11.44-11.31 (m, 2H), 8.04 (s, 1H), 7.92 (d, J = 6.1 Hz, 1H), 7.55 (s, 1H), 6.55 (s, 1H), 4.56-3.91 (m, 4H), 2.81-2.72 (m, 2H). $^{19}$F NMR (376 MHz, DMSO-d6) δ −75.29, −129.84 (d, J = 157.9 Hz), −155.12 (d, J = 158.0 Hz). |
| 225 | 311.1 [M + H]. | $^1$H NMR (400 MHz, Methanol-d4) δ 8.17 (s, 1H), 8.11 (d, J = 1.8 Hz, 1H), 7.79 (d, J = 1.8 Hz, 1H), 7.10 (s, 1H), 4.15-4.06 (m, 2H), 3.91-3.84 (m, 2H), 1.91-1.84 (m, 2H), 0.98-0.87 (m, 1H), 0.36-0.28 (m, 1H). $^{19}$F NMR (376 MHz, Methanol-d4) δ −77.78. |
| 226 | 313.1 [M + H]. | $^1$H NMR (400 MHz, DMSO-d6) δ 11.51-11.43 (m, 2H), 8.19 (d, J = 1.6 Hz, 1H), 8.00 (d, J = 6.1 Hz, 1H), 7.84 (s, 1H), 7.33 (d, J = 6.6 Hz, 1H), 7.02 (s, 1H), 4.05-3.94 (m, 1H), 2.10-1.98 (m, 2H), 1.78-1.58 (m, 6H). $^{19}$F NMR (376 MHz, DMSO-d6) δ −74.80. |
| 227 | 349.1 [M + H]. | $^1$H NMR (400 MHz, DMSO-d6) δ 11.50-11.38 (m, 2H), 8.14 (s, 1H), 7.97 (d, J = 5.8 Hz, 1H), 7.74 (s, 1H), 7.59 (d, J = 7.0 Hz, 1H), 6.90 (s, 1H), 4.30-4.23 (m, 1H), 2.73-2.59 (m, 1H), 2.37-2.09 (m, 4H), 2.00-1.85 (m, 1H). $^{19}$F NMR (376 MHz, DMSO-d6) δ −74.99, −88.82. |
| 228 | 339.1 [M + H]. | $^1$H NMR (400 MHz, DMSO-d6) δ 11.40-11.32 (m, 2H), 8.03 (d, J = 1.2 Hz, 1H), 7.93 (d, J = 6.1 Hz, 1H), 7.57 (d, J = 1.2 Hz, 1H), 6.54 (s, 1H), 4.91-3.47 (m, 4H), 1.63-1.59 (m, 2H), 1.07 (s, 3H), 0.86 (s, 3H). $^{19}$F NMR (376 MHz, DMSO-d6) δ −75.23. |
| 229 | 349.1 [M + H]. | $^1$H NMR (400 MHz, Methanol-d4) δ 8.15 (s, 1H), 8.06 (d, J = 1.7 Hz, 1H), 7.72 (d, J = 1.7 Hz, 1H), 7.00 (s, 1H), 6.22-5.87 (m, 1H), 4.14-3.85 (m, 4H), 3.02-2.88 (m, 1H), 2.36-2.26 (m, 1H), 2.24-2.11 (m, 1H). $^{19}$F NMR (376 MHz, Methanol-d4) δ −77.70, −121.85-−124.29 (m). |
| 230 | 349.1 [M + H]. | $^1$H NMR (400 MHz, DMSO-d6) δ 11.42-11.33 (m, 2H), 8.03 (d, J = 1.2 Hz, 1H), 7.94 (d, J = 6.1 Hz, 1H), 7.57 (d, J = 1.2 Hz, 1H), 6.61 (s, 1H), 6.38-6.05 (m, 1H), 4.19-3.54 (m, 4H), 2.99-2.82 (m, 1H), 2.24-2.12 (m, 1H), 2.09-1.96 (m, 1H). $^{19}$F NMR (376 MHz, DMSO-d6) δ −75.14, −120.45-−120.63 (m). |
| 231 | 452.00 [M + H] | $^1$H NMR (400 MHz, DMSO-d6) δ 11.45-11.33 (m, 2H), 8.08 (d, J = 1.2 Hz, 1H), 7.93 (d, J = 6.1 Hz, 1H), 7.88-7.82 (m, 2H), 7.57 (d, J = 1.2 Hz, 1H), 7.33-7.28 (m, 2H), 6.63 (s, 1H), 5.68-5.56 (m, 1H), 4.71-4.06 (m, 4H). $^{19}$F NMR (376 MHz, DMSO-d6) δ −75.16, −106.94 (d, J = 242.9 Hz), −120.26 (d, J = 238.8 Hz). |
| 232 | 478.00 [M + H] | $^1$H NMR (400 MHz, Methanol-d4) δ 8.40-8.37 (m, 1H), 8.12 (s, 1H), 8.02 (d, J = 1.5 Hz, 1H), 7.93 (dd, J = 8.7, 2.4 Hz, 1H), 7.66 (d, J = 1.5 Hz, 1H), 7.02 (d, J = 8.6 Hz, 1H), 6.99-6.69 (m, 2H), 6.04-5.97 (m, 1H), 4.62-4.39 (m, 3H), 4.27-4.19 (m, 1H). $^{19}$F NMR (376 MHz, Methanol-d4) δ −77.92, −109.78 (d, J = 242.6 Hz), −112.51, −123.83 (d, J = 242.6 Hz). |
| 233 | 488.00 [M + H] | $^1$H NMR (400 MHz, DMSO-d6) δ 11.46-11.35 (m, 2H), 9.79 (s, 1H), 8.11-8.07 (m, 1H), 7.97-7.91 (m, 1H), 7.67-7.56 (m, 2H), 7.29-7.13 (m, 3H), 6.67-6.62 (m, 1H), 5.62-5.53 (m, 1H), 4.60-4.14 (m, 4H). $^{19}$F NMR (376 MHz, DMSO-d6) δ −75.32-−75.49 (m), −107.37-−108.88 (m), −120.37 (d, J = 239.0 Hz), −124.64. |
| 234 | 477.00 [M + H] | $^1$H NMR (400 MHz, DMSO-d6) δ 11.58-11.52 (m, 2H), 9.70 (s, 1H), 8.29 (s, 1H), 8.03 (d, J = 6.4 Hz, 1H), 7.75 (s, 1H), 7.64-7.54 (m, 1H), 7.42 (s, 1H), 7.27-7.13 (m, 3H), 4.90 (t, J = 12.8 Hz, 2H), 4.66 (t, J = 13.8 Hz, 2H). |
| 235 | 506.00 [M + H] | $^1$H NMR (400 MHz, DMSO-d6) δ 11.45-11.36 (m, 2H), 9.79 (s, 1H), 8.09 (s, 1H), 7.94 (d, J = 6.1 Hz, 1H), 7.66-7.54 (m, 2H), 7.31 (ddd, J = 11.2, 9.0, 2.9 Hz, 1H), 7.12-7.04 (m, 1H), 6.63 (s, 1H), 5.61-5.51 (m, 1H), 4.63-3.60 (m, 4H). |
| 236 | 502.00 [M + H] | $^1$H NMR (400 MHz, DMSO-d6) δ 11.44-11.36 (m, 2H), 9.65 (s, 1H), 8.09 (d, J = 1.2 Hz, 1H), 7.94 (d, J = 6.1 Hz, 1H), 7.59 (d, J = 1.2 Hz, 1H), 7.50-7.39 (m, 1H), 7.10-7.03 (m, 1H), 6.98 (d, J = 7.6 Hz, 1H), 6.63 (s, 1H), 5.60-5.51 (m, 1H), 4.60-3.51 (m, 4H), 2.28 (s, 3H). |
| 237 | 452.00 [M + H] | $^1$H NMR (400 MHz, DMSO-d6) δ 11.43-11.35 (m, 2H), 8.07 (d, J = 1.2 Hz, 1H), 7.93 (d, J = 5.2 Hz, 1H), 7.88-7.82 (m, 2H), 7.57 (d, J = 1.2 Hz, 1H), 7.33-7.27 (m, 2H), 6.62 (s, 1H), 5.67-5.56 (m, 1H), 4.63-4.13 (m, 4H). $^{19}$F NMR (376 MHz, DMSO-d6) δ −73.96, −106.93 (d, J = 240.7 Hz), −120.26 (d, J = 238.7 Hz). |

TABLE 3-continued

Characterization Data

| Example No. | ES/MS m/z | NMR |
|---|---|---|
| 238 | 495.00 [M + H] | $^1$H NMR (400 MHz, DMSO-d6) δ 11.58-11.46 (m, 2H), 9.71 (s, 1H), 8.23 (s, 1H), 8.02 (d, J = 5.8 Hz, 1H), 7.67 (s, 1H), 7.63-7.51 (m, 1H), 7.39-7.24 (m, 2H), 7.14-7.02 (m, 1H), 4.88 (t, J = 13.1 Hz, 2H), 4.64 (t, J = 14.0 Hz, 2H). $^{19}$F NMR (376 MHz, DMSO-d6) δ −74.04, −113.53, −115.01, −119.65. |
| 239 | 524.00 [M + H] | $^1$H NMR (400 MHz, DMSO-d6) δ 11.46-11.35 (m, 2H), 9.69 (s, 1H), 8.09 (d, J = 1.2 Hz, 1H), 7.94 (d, J = 6.1 Hz, 1H), 7.59 (d, J = 1.2 Hz, 1H), 7.36-7.24 (m, 2H), 6.63 (s, 1H), 5.61-5.50 (m, 1H), 4.59-4.08 (m, 4H). $^{19}$F NMR (376 MHz, DMSO-d6) δ −75.35, −108.09 (d, J = 247.5 Hz), −109.72, −116.20, −119.87 (d, J = 241.9 Hz). |
| 240 | 409.10 [M + H] | $^1$H NMR (400 MHz, DMSO-d6) δ 11.41-11.31 (m, 2H), 8.03 (s, 1H), 7.93 (d, J = 6.0 Hz, 1H), 7.55 (s, 1H), 7.18-7.10 (m, 2H), 7.05-6.98 (m, 2H), 6.60 (s, 1H), 5.22-5.14 (m, 1H), 4.26-3.64 (m, 4H), 2.36-2.19 (m, 2H). $^{19}$F NMR (376 MHz, DMSO-d6) δ −75.21, −123.95. |
| 241 | 488.00 [M + H] | $^1$H NMR (400 MHz, DMSO-d6) δ 11.46-11.36 (m, 2H), 9.79 (s, 1H), 8.09 (d, J = 1.2 Hz, 1H), 7.94 (d, J = 6.1 Hz, 1H), 7.69-7.55 (m, 2H), 7.30-7.13 (m, 3H), 6.64 (s, 1H), 5.61-5.53 (m, 1H), 4.58-4.15 (m, 4H). $^{19}$F NMR (376 MHz, DMSO-d6) δ −75.21, −107.21--109.15 (m), −120.37 (d, J = 239.0 Hz), −124.63. |
| 242 | 391.1 [M + H] | $^1$H NMR (400 MHz, DMSO-d6) δ 11.47-11.23 (m, 2H), 8.03 (s, 1H), 7.93 (d, J = 6.1 Hz, 1H), 7.55 (s, 1H), 7.39-7.23 (m, 2H), 7.05-6.89 (m, 3H), 6.60 (s, 1H), 5.23 (s, 1H), 4.28-3.70 (m, 4H), 2.39-2.18 (m, 2H). $^{19}$F NMR (400 MHz, DMSO-d6) δ −75.10. |
| 243 | 329.1 [M + H] | $^1$H NMR (400 MHz, DMSO-d6) δ 11.40-11.27 (m, 2H), 8.01 (s, 1H), 7.93 (d, J = 6.1 Hz, 1H), 7.54 (s, 1H), 6.54 (s, 1H), 4.14-3.46 (m, 4H), 2.03-1.86 (m, 2H), 1.39 (s, 3H). $^{19}$F NMR (400 MHz, DMSO-d6) δ −74.89. |
| 244 | 371.00 [M + H] | $^1$H NMR (400 MHz, DMSO-d6) δ 11.44 (s, 2H), 8.33 (d, J = 6.3 Hz, 1H), 8.07 (d, J = 2.3 Hz, 1H), 7.04 (s, 1H), 6.53 (s, 1H), 6.40 (d, J = 2.3 Hz, 1H), 5.01-4.82 (m, 4H). $^{19}$F NMR (400 MHz, DMSO-d6) δ −73.95, −82.72 |
| 245 | 356.1 [M + H] | $^1$H NMR (400 MHz, DMSO-d6) δ 11.98-11.41 (m, 2H), 8.46 (d, J = 6.1 Hz, 1H), 8.23 (d, J = 6.4 Hz, 1H), 8.10 (s, 1H), 6.87 (s, 1H), 6.43 (s, 1H), 4.45-3.81 (m, 5H), 2.30-2.12 (m, 1H), 2.05-1.88 (m, 1H), 1.83 (s, 3H). $^{19}$F NMR (400 MHz, DMSO-d6) δ −74.71. |
| 246 | 329.1 [M + H] | $^1$H NMR (400 MHz, DMSO-d6) δ 12.03-11.45 (m, 2H), 8.46 (d, J = 5.9 Hz, 1H), 8.10 (s, 1H), 6.81 (s, 1H), 6.44 (s, 1H), 4.62-3.07 (m, 4H), 2.07-1.86 (m, 2H), 1.40 (s, 3H). $^{19}$F NMR (400 MHz, DMSO-d6) δ −74.63 |
| 247 | 386.1 [M + H] | $^1$H NMR (400 MHz, DMSO-d6) δ 11.51-11.22 (m, 2H), 8.03 (d, J = 1.2 Hz, 1H), 7.93 (d, J = 6.1 Hz, 1H), 7.89-7.81 (m, 2H), 7.73-7.60 (m, 2H), 7.55 (d, J = 1.2 Hz, 1H), 6.50 (s, 1H), 4.81 (s, 2H), 4.37 (s, 2H), 4.25-4.15 (m, 1H). |
| 248 | 443.2 [M + H] | $^1$H NMR (400 MHz, DMSO-d6) δ 11.37 (d, J = 2.0 Hz, 1H), 11.34 (d, J = 6.2 Hz, 1H), 8.01 (d, J = 1.1 Hz, 1H), 7.94 (d, J = 6.1 Hz, 1H), 7.72 (d, J = 8.1 Hz, 2H), 7.61 (d, J = 8.1 Hz, 2H), 7.53 (s, 1H), 6.61 (s, 1H), 4.35-3.74 (m, 2H), 3.75-3.40 (m, 3H), 2.43 (s, 1H), 2.17 (p, J = 9.4 Hz, 1H). |
| 249 | 443.2 [M + H] | $^1$H NMR (400 MHz, Methanol-d4) δ 8.09 (s, 1H), 7.95 (d, J = 1.4 Hz, 1H), 7.71 (s, 1H), 7.67 (d, J = 6.9 Hz, 1H), 7.62-7.52 (m, 3H), 6.81 (s, 1H), 4.51 (s, 1H), 4.15 (s, 1H), 3.95 (s, 2H), 3.83-3.61 (m, 1H), 2.67-2.44 (m, 1H), 2.27 (q, J = 10.2 Hz, 1H). |
| 250 | 443.2 [M + H] | $^1$H NMR (400 MHz, Methanol-d4) δ 8.20 (s, 1H), 8.14 (d, J = 1.8 Hz, 1H), 7.79 (d, J = 1.9 Hz, 1H), 7.77-7.71 (m, 2H), 7.67 (t, J = 7.6 Hz, 1H), 7.47 (t, J = 7.6 Hz, 1H), 7.16 (s, 1H), 4.34 (s, 1H), 4.15 (t, J = 9.0 Hz, 1H), 4.01 (h, J = 9.4, 8.9 Hz, 3H), 2.53 (d, J = 5.5 Hz, 1H), 2.37 (t, J = 10.8 Hz, 1H). |
| 251 | 391.1 [M + H] | $^1$H NMR (400 MHz, Methanol-d4) δ 8.15 (s, 1H), 8.07 (s, 1H), 7.74 (s, 1H), 7.37 (d, J = 8.6 Hz, 2H), 6.94 (d, J = 8.7 Hz, 2H), 6.88 (s, 1H), 4.91-4.87 (m, 2H), 4.45 (t, J = 7.7 Hz, 2H), 4.12 (q, J = 7.1, 6.5 Hz, 1H), 3.79 (s, 3H). |
| 252 | 445.1 [M + H] | $^1$H NMR (400 MHz, Methanol-d4) δ 8.10 (s, 1H), 7.99 (d, J = 1.4 Hz, 1H), 7.64 (s, 1H), 7.57 (d, J = 8.6 Hz, 2H), 7.33-7.23 (m, 2H), 6.75 (s, 1H), 4.90 (d, J = 9.0 Hz, 2H), 4.46 (d, J = 8.1 Hz, 2H), 4.24-4.09 (m, 1H). |
| 253 | 392.9 [M + H] | $^1$H NMR (400 MHz, DMSO-d6) δ 11.45-11.28 (m, 2H), 8.04 (d, J = 1.1 Hz, 1H), 7.94 (d, J = 6.1 Hz, 1H), 7.61 (d, J = 7.2 Hz, 2H), 7.55 (d, J = 1.1 Hz, 1H), 7.51-7.40 (m, 3H), 6.64 (s, 1H), 5.23-3.49 (m, 4H), 2.81-2.54 (m, 2H). |

TABLE 3-continued

Characterization Data

| Example No. | ES/MS m/z | NMR |
|---|---|---|
| 254 | 311.1 [M + H] | ¹H NMR (400 MHz, Methanol-d4) δ 8.20 (s, 1H), 8.15 (d, J = 1.8 Hz, 1H), 7.84 (d, J = 1.8 Hz, 1H), 7.33 (s, 1H), 4.26 (td, J = 10.6, 3.8 Hz, 1H), 3.95 (d, J = 6.7 Hz, 1H), 3.52-3.37 (m, 1H), 2.54-2.38 (m, 1H), 2.21 (ddd, J = 12.7, 8.6, 3.8 Hz, 1H), 1.96 (dt, J = 14.9, 6.2 Hz, 1H), 1.09 (dt, J = 8.7, 5.6 Hz, 1H), 0.74 (td, J = 5.4, 2.5 Hz, 1H). |
| 255 | 410.9 [M + H] | ¹H NMR (400 MHz, Methanol-d4) δ 8.06 (s, 1H), 7.90 (d, J = 1.3 Hz, 1H), 7.64 (dd, J = 8.6, 5.2 Hz, 2H), 7.51 (d, J = 1.3 Hz, 1H), 7.19 (t, J = 8.7 Hz, 2H), 6.70 (s, 1H), 4.77-4.51 (m, 1H), 4.29 (dd, J = 36.5, 13.1 Hz, 2H), 4.04 (s, 1H), 2.81-2.50 (m, 2H). |
| 256 | 461.1 [M + H] | ¹H NMR (400 MHz, Methanol-d4) δ 8.22 (s, 1H), 8.17 (d, J = 1.8 Hz, 1H), 7.85 (s, 1H), 7.82 (q, J = 8.6, 7.3 Hz, 4H), 7.23 (s, 1H), 4.65-4.32 (m, 2H), 4.31-4.07 (m, 2H), 2.93-2.60 (m, 2H). |
| 257 | 325.1 [M + H] | ¹H NMR (400 MHz, DMSO-d6) δ 11.35 (s, 2H), 7.98 (d, J = 1.1 Hz, 1H), 7.93 (s, 1H), 7.51 (d, J = 1.1 Hz, 1H), 6.57 (s, 1H), 4.23-3.49 (m, 2H), 3.32 (s, 1H), 3.18 (h, J = 6.4, 6.0 Hz, 1H), 2.36 (dq, J = 11.7, 6.6, 5.8 Hz, 1H), 2.09 (d, J = 10.8 Hz, 1H), 2.05-1.95 (m, 1H), 1.93-1.82 (m, 1H), 1.71 (d, J = 14.7 Hz, 2H). |
| 258 | 379.1 [M + H]. | ¹H NMR (400 MHz, Methanol-d4) δ 8.13 (s, 1H), 8.04 (s, 1H), 7.70 (s, 1H), 7.54-7.41 (m, 2H), 7.18-7.05 (m, 2H), 6.82 (s, 1H), 4.89 (d, J = 9.3 Hz, 2H), 4.46 (t, J = 7.5 Hz, 2H), 4.22-4.07 (m, 1H). |
| 259 | 379.1 [M + H]. | ¹H NMR (400 MHz, Methanol-d4) δ 8.29-8.13 (m, 2H), 7.91 (d, J = 1.8 Hz, 1H), 7.62 (d, J = 7.9 Hz, 2H), 7.47 (dt, J = 23.4, 7.2 Hz, 3H), 7.18 (s, 1H), 4.96 (s, 2H), 4.90 (s, 2H). |
| 260 | 375.1 [M + H]. | ¹H NMR (400 MHz, Methanol-d4) δ 8.26 (d, J = 2.5 Hz, 2H), 7.96 (d, J = 1.9 Hz, 1H), 7.76 (s, 1H), 4.06 (t, J = 10.8 Hz, 2H), 3.88-3.71 (m, 2H), 1.97-1.85 (m, 2H), 1.07-0.89 (m, 2H), 0.72-0.50 (m, 2H). |
| 261 | 419.1 [M + H]. | ¹H NMR (400 MHz, Methanol-d4) δ 8.10 (s, 1H), 8.04 (d, J = 8.1 Hz, 2H), 7.98 (s, 1H), 7.62 (s, 1H), 7.58 (d, J = 8.2 Hz, 2H), 6.72 (s, 1H), 4.94-4.87 (m, 2H), 4.56-4.42 (m, 2H), 4.22 (d, J = 7.9 Hz, 1H), 3.91 (s, 3H). |
| 262 | 461.1 [M + H]. | ¹H NMR (400 MHz, Methanol-d4) δ 8.22 (s, 1H), 7.68 (d, J = 8.1 Hz, 2H), 7.63-7.56 (m, 3H), 7.12 (s, 1H), 4.43 (s, 1H), 4.12 (s, 1H), 3.95 (s, 2H), 3.83-3.69 (m, 1H), 2.58 (s, 1H), 2.29 (p, J = 9.7 Hz, 1H). |
| 263 | 419.1 [M + H]. | ¹H NMR (400 MHz, Methanol-d4) δ 8.18 (s, 1H), 8.13 (q, J = 1.9 Hz, 2H), 7.96 (dt, J = 7.7, 1.4 Hz, 1H), 7.80 (d, J = 1.8 Hz, 1H), 7.73 (d, J = 7.7 Hz, 1H), 7.53 (t, J = 7.8 Hz, 1H), 6.98 (s, 1H), 4.92 (q, J = 8.3, 7.7 Hz, 2H), 4.59-4.46 (m, 2H), 4.26 (ddd, J = 14.6, 8.6, 5.9 Hz, 1H), 3.91 (s, 3H). |
| 264 | 433.1 [M + H]. | ¹H NMR (400 MHz, Methanol-d4) δ 8.26 (s, 1H), 8.23 (d, J = 2.0 Hz, 1H), 8.11-8.05 (m, 1H), 7.96 (dt, J = 7.8, 1.4 Hz, 1H), 7.92 (d, J = 2.0 Hz, 1H), 7.68 (dt, J = 7.7, 1.5 Hz, 1H), 7.51 (t, J = 7.7 Hz, 1H), 7.35 (s, 1H), 4.37 (t, J = 8.8 Hz, 1H), 4.09 (t, J = 9.3 Hz, 1H), 4.03-3.91 (m, 2H), 3.92 (s, 3H), 3.84-3.72 (m, 1H), 2.67-2.52 (m, 1H), 2.35 (p, J = 10.3 Hz, 1H). |
| 265 | 433.2 [M + H] | ¹H NMR (400 MHz, Methanol-d4) δ 8.24 (s, 1H), 8.21 (d, J = 2.0 Hz, 1H), 8.08-7.99 (m, 2H), 7.89 (d, J = 2.0 Hz, 1H), 7.60-7.49 (m, 2H), 7.30 (s, 1H), 4.37 (t, J = 8.9 Hz, 1H), 4.08 (d, J = 5.6 Hz, 1H), 3.98 (dd, J = 17.3, 9.0 Hz, 2H), 3.91 (s, 3H), 3.77 (td, J = 15.6, 14.3, 7.1 Hz, 1H), 2.66-2.53 (m, 1H), 2.33 (p, J = 10.0 Hz, 1H). |
| 266 | 362.1 [M + H]. | ¹H NMR (400 MHz, DMSO-d6) δ 11.47 (s, 2H), 9.45 (s, 1H), 7.99 (s, 1H), 6.60 (s, 1H), 4.56 (s, 2H), 4.09 (q, J = 5.2 Hz, 2H), 1.06 (d, J = 3.6 Hz, 2H), 1.03 (d, J = 3.7 Hz, 2H). |
| 267 | 480.1 [M + H]. | ¹H NMR (400 MHz, Methanol-d4) δ 8.19 (s, 1H), 8.14 (d, J = 1.7 Hz, 1H), 7.82 (d, J = 1.7 Hz, 1H), 7.78-7.69 (m, 2H), 7.60 (d, J = 8.2 Hz, 2H), 7.01 (s, 1H), 4.92 (t, J = 8.9 Hz, 2H), 4.77-4.40 (m, 6H), 4.32-4.18 (m, 1H). |
| 268 | 480.1 [M + H]. | ¹H NMR (400 MHz, Methanol-d4) δ 8.06 (s, 1H), 7.90 (d, J = 1.3 Hz, 1H), 7.77 (s, 1H), 7.66 (d, J = 7.6 Hz, 1H), 7.63-7.58 (m, 1H), 7.55-7.48 (m, 2H), 6.59 (s, 1H), 4.73-4.43 (m, 8H), 4.25-4.10 (m, 1H). |
| 269 | 432.1 [M + H]. | ¹H NMR (400 MHz, DMSO-d6) δ 11.34 (s, 2H), 8.45 (d, J = 4.8 Hz, 1H), 7.99 (d, J = 1.2 Hz, 1H), 7.94 (s, 1H), 7.84 (d, J = 1.8 Hz, 1H), 7.72 (dt, J = 7.6, 1.4 Hz, 1H), 7.57-7.48 (m, 2H), 7.43 (t, J = 7.6 Hz, 1H), 6.59 (s, 1H), 4.03-3.69 (m, 3H), 3.61 (p, J = 8.2 Hz, 1H), 2.78 (d, J = 4.5 Hz, 3H), 2.47-2.37 (m, 2H), 2.17 (p, J = 10.2 Hz, 1H). |
| 270 | 432.1 [M + H]. | ¹H NMR (400 MHz, DMSO-d6) δ 11.36 (s, 1H), 11.33 (d, J = 6.0 Hz, 1H), 8.39 (d, J = 4.7 Hz, 1H), 7.99 (d, J = 1.1 Hz, 1H), 7.93 (d, J = 6.1 Hz, 1H), 7.85-7.75 (m, 2H), 7.50 (d, J = 1.2 Hz, 1H), 7.45 (d, J = 8.3 Hz, 2H), 6.58 (s, 1H), 3.82 (s, 3H), 3.62 (q, J = 8.3 Hz, 1H), 2.78 (d, J = 4.5 Hz, 3H), 2.46-2.36 (m, 2H), 2.24-2.07 (m, 1H). |

TABLE 3-continued

Characterization Data

| Example No. | ES/MS m/z | NMR |
|---|---|---|
| 271 | 416.2 [M + H]. | $^1$H NMR (400 MHz, Methanol-d4) δ 8.76 (d, J = 5.2 Hz, 1H), 8.17 (s, 1H), 8.09 (d, J = 1.3 Hz, 1H), 7.70 (d, J = 5.2 Hz, 1H), 7.66 (d, J = 1.3 Hz, 1H), 7.64 (s, 1H), 3.27-3.19 (m, 1H), 3.03-2.91 (m, 1H), 2.12 (dd, J = 8.2, 6.6 Hz, 2H). |
| 272 | 416.1 [M + H]. | $^1$H NMR (400 MHz, DMSO-d6) δ 11.55 (d, J = 4.5 Hz, 2H), 9.01 (s, 2H), 8.34 (d, J = 1.3 Hz, 1H), 8.03 (d, J = 6.3 Hz, 1H), 7.86 (s, 1H), 7.66 (s, 1H), 3.05 (dt, J = 9.2, 5.6 Hz, 1H), 2.97 (ddd, J = 8.8, 6.1, 4.4 Hz, 1H), 2.36-2.26 (m, 1H), 2.02 (dt, J = 8.9, 5.5 Hz, 1H). |
| 273 | 434.0 [M + H]. | $^1$H NMR (400 MHz, DMSO-d6) δ 11.55 (d, J = 3.7 Hz, 2H), 9.02 (s, 2H), 8.03 (d, J = 6.5 Hz, 1H), 7.59 (s, 1H), 7.56 (d, J = 7.1 Hz, 1H), 3.12 (ddd, J = 9.0, 6.1, 4.5 Hz, 1H), 2.96 (ddd, J = 8.9, 6.0, 4.4 Hz, 1H), 2.37-2.28 (m, 1H), 2.06-1.95 (m, 1H). |
| 274 | 355.17 [M + H] | $^1$H NMR (400 MHz, DMSO-d6) δ 11.38 (s, 1H), 11.35 (d, J = 6.1 Hz, 1H), 8.02 (s, 1H), 7.93 (d, J = 6.1 Hz, 1H), 7.55 (s, 1H), 6.58 (s, 1H), 3.85-3.80 (m, 4H), 3.66-3.57 (m, 4H), 2.02 (td, J = 7.1, 2.6 Hz, 2H), 1.99-1.86 (m, 2H). |
| 275 | 369.20 [M + H] | $^1$H NMR (400 MHz, DMSO-d6) δ 11.45-11.34 (m, 2H), 8.09 (d, J = 1.3 Hz, 1H), 7.94 (d, J = 6.0 Hz, 1H), 7.67 (d, J = 1.4 Hz, 1H), 6.66 (s, 1H), 4.05-3.68 (m, 4H), 3.61 (qdd, J = 11.4, 6.4, 4.2 Hz, 4H), 1.95 (t, J = 7.1 Hz, 2H), 1.66-1.48 (m, 4H). |
| 276 | 403.10 [M + H] | $^1$H NMR (400 MHz, DMSO-d6) δ 11.60-11.44 (m, 2H), 9.33 (s, 1H), 8.30 (s, 1H), 8.07 (d, J = 1.7 Hz, 1H), 8.03 (s, 1H), 8.01 (d, J = 2.6 Hz, 1H), 7.81 (s, 1H), 7.55 (s, 1H), 7.45 (dd, J = 8.5, 1.8 Hz, 1H), 2.97 (ddd, J = 9.3, 6.1, 4.4 Hz, 1H), 2.81 (dt, J = 9.0, 5.3 Hz, 1H), 2.15 (dt, J = 8.7, 5.4 Hz, 1H), 1.87 (dt, J = 8.6, 5.5 Hz, 1H). |
| 277 | 446.13 [M + H]. | $^1$H NMR (400 MHz, DMSO-d6) δ 11.52 (s, 2H), 8.02 (s, 1H), 7.53 (d, J = 7.1 Hz, 1H), 7.47 (s, 1H), 7.42-7.34 (m, 2H), 7.34-7.26 (m, 2H), 2.88 (ddd, J = 9.0, 6.2, 4.4 Hz, 1H), 2.70 (ddd, J = 8.9, 6.0, 4.5 Hz, 1H), 2.12 (dt, J = 8.9, 5.1 Hz, 1H), 1.76 (ddd, J = 8.8, 6.2, 4.8 Hz, 1H). $^{19}$F NMR (376 MHz, DMSO-d6) δ −57.40, −155.61 (d, J = 7.2 Hz). |
| 278 | 444.10 [M + H] | $^1$H NMR (400 MHz, DMSO-d6) δ 11.63-11.47 (m, 2H), 8.02 (d, J = 6.4 Hz, 1H), 7.54 (d, J = 7.1 Hz, 1H), 7.47 (s, 1H), 7.35 (d, J = 1.8 Hz, 1H), 7.32 (d, J = 8.3 Hz, 1H), 7.13 (dd, J = 8.4, 1.8 Hz, 1H), 2.89 (ddd, J = 9.0, 6.3, 4.4 Hz, 1H), 2.68 (ddd, J = 8.9, 5.9, 4.3 Hz, 1H), 2.11 (dt, J = 8.9, 5.3 Hz, 1H), 1.76 (ddd, J = 8.8, 6.1, 4.8 Hz, 1H). $^{19}$F NMR (376 MHz, DMSO-d6) δ −49.74, −75.33, −155.61 (d, J = 7.1 Hz). |
| 279 | 389.10 [M + H] | $^1$H NMR (400 MHz, DMSO-d6) δ 11.62-11.46 (m, 2H), 8.36 (d, J = 1.5 Hz, 1H), 8.03 (d, J = 6.1 Hz, 1H), 7.91 (s, 1H), 7.83 (dd, J = 10.2, 1.6 Hz, 1H), 7.71 (dd, J = 8.1, 1.6 Hz, 1H), 7.66 (s, 1H), 7.49 (t, J = 7.9 Hz, 1H), 3.09-2.97 (m, 1H), 2.86 (ddd, J = 8.9, 6.1, 4.5 Hz, 1H), 2.17 (dt, J = 9.0, 5.4 Hz, 1H), 1.97-1.84 (m, 1H). $^{19}$F NMR (376 MHz, DMSO-d6) δ −75.27, −117.79--118.08 (m). |
| 280 | 448.11 [M + H] | $^1$H NMR (400 MHz, DMSO-d6) δ 11.58 (d, J = 6.2 Hz, 1H), 11.56 (s, 1H), 8.40 (d, J = 1.6 Hz, 1H), 8.05 (d, J = 6.2 Hz, 1H), 7.97 (d, J = 1.5 Hz, 1H), 7.68 (s, 1H), 7.43 (t, J = 8.6 Hz, 1H), 7.38 (dd, J = 10.5, 2.5 Hz, 1H), 7.29-7.20 (m, 1H), 2.97-2.86 (m, 1H), 2.79 (dt, J = 8.9, 5.6 Hz, 1H), 2.07 (dt, J = 9.0, 5.4 Hz, 1H), 1.87 (ddd, J = 8.7, 6.3, 5.0 Hz, 1H). $^{19}$F NMR (376 MHz, DMSO-d6) δ −57.65, −75.32, −115.92 (t, J = 9.6 Hz). |
| 281 | 404.13 [M + H] | $^1$H NMR (400 MHz, Acetonitrile-d3) δ 9.43 (s, 1H), 9.32 (s, 1H), 8.19 (d, J = 2.0 Hz, 1H), 8.16 (d, J = 6.4 Hz, 1H), 8.01 (s, 1H), 7.98-7.91 (m, 3H), 7.39-7.33 (m, 2H), 3.89 (s, 3H), 2.94 (dt, J = 8.7, 5.4 Hz, 1H), 2.68 (ddd, J = 9.0, 6.7, 4.4 Hz, 1H), 1.93-1.86 (m, 2H). |
| 282 | 404.19 [M + H] | $^1$H NMR (400 MHz, Acetonitrile-d3) δ 9.39 (s, 1H), 9.29 (s, 1H), 8.18 (d, J = 1.8 Hz, 1H), 8.15 (d, J = 6.5 Hz, 1H), 7.99 (s, 1H), 7.95 (d, J = 1.9 Hz, 1H), 7.93-7.84 (m, 2H), 7.53 (d, J = 7.7 Hz, 1H), 7.48 (t, J = 7.6 Hz, 1H), 3.90 (s, 3H), 2.91 (q, J = 6.9 Hz, 1H), 2.73 (dq, J = 7.6, 4.4 Hz, 1H), 1.94-1.87 (m, 2H). |
| 283 | 389.11 [M + H] | $^1$H NMR (400 MHz, DMSO-d6) δ 11.64-11.51 (m, 2H), 8.41 (d, J = 1.5 Hz, 1H), 8.05 (d, J = 6.1 Hz, 1H), 7.98 (s, 2H), 7.76-7.69 (m, 2H), 7.66 (s, 1H), 7.45-7.33 (m, 3H), 2.88-2.77 (m, 2H), 2.03 (dt, J = 8.6, 5.3 Hz, 1H), 1.92-1.82 (m, 1H). $^{19}$F NMR (376 MHz, DMSO-d6) δ −75.30. |
| 284 | 389.11 [M + H] | $^1$H NMR (400 MHz, DMSO-d6) δ 11.64-11.51 (m, 2H), 8.41 (d, J = 1.5 Hz, 1H), 8.05 (d, J = 6.1 Hz, 1H), 7.98 (s, 2H), 7.76-7.69 (m, 2H), 7.66 (s, 1H), 7.45-7.33 (m, 3H), 2.88-2.77 (m, 2H), 2.03 (dt, J = 8.6, 5.3 Hz, 1H), 1.92-1.82 (m, 1H). |
| 285 | 403.10 [M + H] | $^1$H NMR (400 MHz, DMSO-d6) δ 11.57-11.45 (m, 2H), 8.46-8.32 (m, 1H), 8.26 (s, 1H), 8.00 (d, J = 6.0 Hz, 1H), 7.78 (d, J = 8.2 Hz, 2H), 7.75 (s, 1H), 7.49 (s, 1H), 7.33 (d, J = 8.4 Hz, 2H), 2.93-2.83 (m, 1H), 2.81-2.72 (m, 4H), 2.19-2.07 (m, 1H), 1.84-1.73 (m, 1H). |

TABLE 3-continued

Characterization Data

| Example No. | ES/MS m/z | NMR |
|---|---|---|
| 286 | 403.10 [M + H] | ¹H NMR (400 MHz, DMSO-d6) δ 11.61-11.44 (m, 2H), 8.51-8.40 (m, 1H), 8.35 (s, 1H), 8.03 (d, J = 6.3 Hz, 1H), 7.89 (s, 1H), 7.70-7.64 (m, 2H), 7.59 (s, 1H), 7.46-7.36 (m, 2H), 2.87 (dt, J = 9.5, 5.6 Hz, 1H), 2.82-2.75 (m, 4H), 2.10-2.01 (m, 1H), 1.88-1.79 (m, 1H). |
| 287 | 417.20 [M + H] | ¹H NMR (400 MHz, DMSO-d6) δ 11.62-11.49 (m, 2H), 8.37 (s, 1H), 8.04 (d, J = 6.1 Hz, 1H), 7.92 (s, 1H), 7.60 (s, 1H), 7.43-7.31 (m, 2H), 7.28-7.26 (m, 1H), 7.24 (t, J = 7.2, 1.5 Hz, 1H), 2.98 (s, 3H), 2.91 (s, 3H), 2.88-2.81 (m, 1H), 2.81-2.74 (m, 1H), 2.04 (dt, J = 10.5, 5.3 Hz, 1H), 1.82 (dt, J = 8.5, 5.3 Hz, 1H). |
| 288 | 417.20 [M + H] | ¹H NMR (400 MHz, DMSO-d6) δ 11.54 (d, J = 3.9 Hz, 2H), 8.32 (d, J = 1.4 Hz, 1H), 8.02 (d, J = 6.4 Hz, 1H), 7.85 (s, 1H), 7.55 (s, 1H), 7.35 (d, J = 8.3 Hz, 2H), 7.30 (d, J = 8.3 Hz, 2H), 2.95 (d, J = 11.8 Hz, 6H), 2.83 (ddd, J = 9.0, 6.2, 4.4 Hz, 1H), 2.80-2.73 (m, 1H), 2.08 (dt, J = 8.8, 5.2 Hz, 1H), 1.80 (dt, J = 8.5, 5.3 Hz, 1H). |
| 289 | 429.10 [M + H] | ¹H NMR (400 MHz, DMSO-d6) δ 11.53 (s, 2H), 8.32 (s, 1H), 8.02 (d, J = 6.4 Hz, 1H), 7.84 (s, 1H), 7.62-7.50 (m, 3H), 7.37-7.25 (m, 2H), 4.30 (t, J = 7.6 Hz, 2H), 4.03 (t, J = 7.8 Hz, 2H), 2.87-2.81 (m, 1H), 2.81-2.74 (m, 1H), 2.25 (p, J = 7.7 Hz, 2H), 2.10 (dt, J = 8.9, 5.4 Hz, 1H), 1.81 (dt, J = 8.3, 5.2 Hz, 1H). |
| 290 | 443.10 [M + H] | ¹H NMR (400 MHz, DMSO-d6) δ 11.53 (s, 2H), 8.31 (s, 1H), 8.02 (d, J = 6.4 Hz, 1H), 7.83 (s, 1H), 7.57 (d, J = 8.1 Hz, 2H), 7.54 (s, 1H), 7.31 (d, J = 8.2 Hz, 2H), 4.39 (t, J = 8.5 Hz, 1H), 4.14 (t, J = 9.2 Hz, 1H), 3.86 (t, J = 7.0 Hz, 1H), 3.62-3.56 (m, 1H), 2.84 (dt, J = 9.8, 5.5 Hz, 1H), 2.77 (dt, J = 10.0, 5.4 Hz, 1H), 2.74-2.64 (m, 1H), 2.10 (dt, J = 9.9, 5.4 Hz, 1H), 1.81 (dd, J = 9.6, 5.2 Hz, 1H), 1.20 (d, J = 6.9 Hz, 3H). |
| 291 | 497.13 [M + H] | ¹H NMR (400 MHz, DMSO-d6) δ 11.64-11.47 (m, 2H), 8.36 (d, J = 1.5 Hz, 1H), 8.04 (d, J = 6.0 Hz, 1H), 7.91 (s, 1H), 7.62 (d, J = 8.3 Hz, 2H), 7.60 (s, 1H), 7.39-7.30 (m, 2H), 4.59-4.49 (m, 1H), 4.40-4.33 (m, 1H), 4.28 (d, J = 9.8 Hz, 1H), 4.06-3.97 (m, 1H), 3.67 (ddt, J = 18.2, 9.5, 5.3 Hz, 1H), 2.84 (tq, J = 13.5, 5.1 Hz, 2H), 2.10 (dt, J = 8.8, 5.3 Hz, 1H), 1.84 (dt, J = 8.3, 5.3 Hz, 1H). ¹⁹F NMR (376 MHz, DMSO-d6) δ −72.83 (d, J = 9.2 Hz), −75.18. |
| 292 | 457.12 [M + H] | ¹H NMR (400 MHz, DMSO-d6) δ 11.61-11.41 (m, 2H), 8.30 (s, 1H), 8.02 (d, J = 6.4 Hz, 1H), 7.82 (s, 1H), 7.64 (d, J = 8.2 Hz, 2H), 7.54 (s, 1H), 7.35 (d, J = 8.2 Hz, 2H), 4.96-4.62 (m, 2H), 2.91-2.83 (m, 1H), 2.83-2.75 (m, 1H), 2.18-2.07 (m, 1H), 1.82 (dt, J = 8.7, 5.2 Hz, 1H). ¹⁹F NMR (376 MHz, DMSO-d6) δ −74.94, −100.10 (p, J = 12.6 Hz). |
| 293 | 465.10 [M + H] | ¹H NMR (400 MHz, DMSO-d6) δ 11.64-11.41 (m, 2H), 8.33 (d, J = 1.4 Hz, 1H), 8.02 (d, J = 6.4 Hz, 1H), 7.85 (s, 1H), 7.62-7.56 (m, 2H), 7.56 (s, 1H), 7.35-7.26 (m, 2H), 3.98 (s, 2H), 3.72 (s, 2H), 2.84 (dt, J = 8.8, 3.7 Hz, 1H), 2.81-2.74 (m, 1H), 2.13-2.05 (m, 1H), 1.81 (dt, J = 8.4, 5.2 Hz, 1H), 1.24 (s, 6H). |
| 294 | 429.10 [M + H] | ¹H NMR (400 MHz, DMSO-d6) δ 11.70-11.46 (m, 2H), 8.41 (d, J = 1.6 Hz, 1H), 8.05 (d, J = 6.1 Hz, 1H), 7.98 (s, 1H), 7.64 (s, 1H), 7.48-7.45 (m, 1H), 7.45-7.42 (m, 1H), 7.42-7.36 (m, 2H), 4.29 (t, J = 7.7 Hz, 2H), 4.04 (t, J = 7.8 Hz, 2H), 2.87-2.73 (m, 2H), 2.25 (p, J = 7.7 Hz, 2H), 2.01 (dt, J = 8.9, 5.4 Hz, 1H), 1.82 (dt, J = 8.6, 5.4 Hz, 1H). |
| 295 | 443.10 [M + H] | ¹H NMR (400 MHz, DMSO-d6) δ 11.67-11.50 (m, 2H), 8.42 (d, J = 1.6 Hz, 1H), 8.06 (d, J = 6.1 Hz, 1H), 7.99 (s, 1H), 7.65 (s, 1H), 7.47 (s, 1H), 7.47-7.43 (m, 1H), 7.43-7.38 (m, 2H), 4.44-4.34 (m, 1H), 4.15 (t, J = 9.1 Hz, 1H), 3.87 (t, J = 7.4, 6.1 Hz, 1H), 3.60 (dd, J = 9.8, 5.7 Hz, 1H), 2.88-2.75 (m, 2H), 2.75-2.66 (m, 1H), 2.02 (dt, J = 8.9, 5.4 Hz, 1H), 1.88-1.80 (m, 1H), 1.21 (d, J = 6.9 Hz, 3H). |
| 296 | 497.08 [M + H] | ¹H NMR (400 MHz, DMSO-d6) δ 11.65-11.48 (m, 2H), 8.38 (s, 1H), 8.05 (d, J = 6.1 Hz, 1H), 7.94 (s, 1H), 7.62 (s, 1H), 7.51 (s, 1H), 7.51-7.48 (m, 1H), 7.45-7.40 (m, 2H), 4.59-4.48 (m, 1H), 4.40-4.33 (m, 1H), 4.29 (t, J = 9.7 Hz, 1H), 4.00 (s, 1H), 3.71-3.61 (m, 1H), 2.91-2.82 (m, 1H), 2.79 (dt, J = 10.1, 5.1 Hz, 1H), 2.03 (dt, J = 9.6, 5.3 Hz, 1H), 1.87-1.78 (m, 1H). ¹⁹F NMR (376 MHz, DMSO-d6) δ −72.73 (d, J = 7.2 Hz), −75.24. |
| 297 | 465.10 [M + H] | ¹H NMR (400 MHz, DMSO-d6) δ 11.54 (s, 2H), 8.33 (s, 1H), 8.03 (d, J = 6.3 Hz, 1H), 7.86 (s, 1H), 7.57 (s, 1H), 7.55-7.51 (m, 2H), 7.47-7.39 (m, 2H), 4.88-4.71 (m, 2H), 4.57-4.40 (m, 2H), 2.89 (p, J = 5.3 Hz, 1H), 2.78 (dt, J = 10.2, 5.1 Hz, 1H), 2.07 (dt, J = 9.2, 5.0 Hz, 1H), 1.86-1.77 (m, 1H). ¹⁹F NMR (376 MHz, DMSO-d6) δ −75.02, −100.16 (p, J = 12.6 Hz). |
| 298 | 457.13 [M + H] | ¹H NMR (400 MHz, DMSO-d6) δ 11.61-11.47 (m, 2H), 8.36 (d, J = 1.5 Hz, 1H), 8.04 (d, J = 6.1 Hz, 1H), 7.91 (s, 1H), 7.59 (s, 1H), 7.50-7.47 (m, 1H), 7.47-7.43 (m, 1H), 7.42-7.34 (m, 2H), 3.98 (s, 2H), 3.72 (s, 2H), 2.85 (ddd, J = 8.9, 6.3, 4.4 Hz, 1H), 2.80-2.73 |

TABLE 3-continued

Characterization Data

| Example No. | ES/MS m/z | NMR |
|---|---|---|
| | | (m, 1H), 2.04 (dt, J = 8.9, 5.4 Hz, 1H), 1.81 (dt, J = 8.8, 5.5 Hz, 1H), 1.24 (s, 6H). |
| 299 | 479.09 [M + H] | $^1$H NMR (400 MHz, DMSO-d6) δ 11.54 (s, 2H), 8.32 (s, 1H), 8.02 (d, J = 6.4 Hz, 1H), 7.85 (s, 1H), 7.56 (s, 1H), 7.54 (d, J = 8.1 Hz, 2H), 7.38-7.29 (m, 2H), 5.37 (dd, J = 48.7, 32.8 Hz, 2H), 4.04-3.76 (m, 4H), 2.91-2.83 (m, 1H), 2.79 (t, J = 10.9 Hz, 2H), 2.10 (dt, J = 9.6, 5.3 Hz, 1H). $^{19}$F NMR (376 MHz, DMSO-d6) δ −75.01, −188.33 (dd, J = 71.3, 34.2 Hz), −190.01−−190.64 (m). |
| 300 | 479.09 [M + H] | $^1$H NMR (400 MHz, DMSO-d6) δ 11.53 (s, 2H), 8.31 (s, 1H), 8.02 (d, J = 6.4 Hz, 1H), 7.83 (s, 1H), 7.55 (s, 1H), 7.46-7.43 (m, 1H), 7.43-7.35 (m, 3H), 5.36 (dd, J = 49.1, 34.2 Hz, 2H), 4.07-3.69 (m, 4H), 2.88 (dtd, J = 8.8, 6.1, 5.5, 3.0 Hz, 1H), 2.78 (tt, J = 9.4, 5.0 Hz, 1H), 2.07 (td, J = 9.0, 4.3 Hz, 1H), 1.82 (dq, J = 10.7, 5.5 Hz, 1H). $^{19}$F NMR (376 MHz, DMSO-d6) δ −74.89, −188.04−−188.56 (m), −190.04−−190.60 (m). |
| 301 | 479.07 [M + H] | $^1$H NMR (400 MHz, DMSO-d6) δ 11.64-11.42 (m, 2H), 8.34 (d, J = 1.5 Hz, 1H), 8.03 (d, J = 6.4 Hz, 1H), 7.87 (s, 1H), 7.57 (s, 1H), 7.54-7.46 (m, 2H), 7.33 (dd, J = 8.6, 2.4 Hz, 2H), 5.50-5.09 (m, 2H), 3.95-3.80 (m, 4H), 2.83 (ddq, J = 22.6, 13.5, 4.6 Hz, 2H), 2.13-2.05 (m, 1H), 1.87-1.77 (m, 1H). $^{19}$F NMR (376 MHz, DMSO-d6) δ −75.08, −204.12−−204.79 (m), −206.15−−206.59 (m). |
| 302 | 479.10 [M + H] | $^1$H NMR (400 MHz, DMSO-d6) δ 11.62-11.48 (m, 2H), 8.35 (s, 1H), 8.03 (d, J = 6.1 Hz, 1H), 7.90 (s, 1H), 7.59 (s, 1H), 7.45-7.36 (m, 4H), 5.49-5.15 (m, 2H), 3.87 (dq, J = 18.2, 6.8, 5.3 Hz, 2H), 3.64 (dd, J = 22.4, 14.3 Hz, 2H), 2.90-2.82 (m, 1H), 2.82-2.74 (m, 1H), 2.04 (dt, J = 10.3, 5.3 Hz, 1H), 1.83 (dt, J = 8.6, 5.4 Hz, 1H). $^{19}$F NMR (376 MHz, DMSO-d6) δ −75.10, −204.21−−204.79 (m), −205.91−−206.60 (m). |
| 303 | 515.09 [M + H] | $^1$H NMR (400 MHz, DMSO-d6) δ 11.53 (s, 2H), 8.29 (s, 1H), 8.01 (d, J = 6.2 Hz, 1H), 7.80 (s, 1H), 7.56 (d, J = 8.0 Hz, 2H), 7.53 (s, 1H), 7.36 (d, J = 8.1 Hz, 2H), 4.36-4.14 (m, 4H), 2.88 (dt, J = 9.6, 5.5 Hz, 1H), 2.79 (dt, J = 9.8, 5.2 Hz, 1H), 2.14 (dt, J = 9.7, 5.2 Hz, 1H), 1.85-1.77 (m, 1H). $^{19}$F NMR (376 MHz, DMSO-d6) δ −74.89, −122.40−−123.00 (m), −123.80−−124.44 (m). |
| 304 | 515.09 [M + H]. | $^1$H NMR (400 MHz, DMSO-d6) δ 11.56-11.46 (m, 2H), 8.28 (s, 1H), 8.01 (d, J = 6.2 Hz, 1H), 7.78 (s, 1H), 7.52 (s, 1H), 7.47 (s, 1H), 7.45-7.38 (m, 3H), 4.38-4.12 (m, 4H), 2.91 (dt, J = 9.6, 5.3 Hz, 1H), 2.77 (dt, J = 10.1, 5.3 Hz, 1H), 2.11 (dt, J = 9.6, 5.3 Hz, 1H), 1.85-1.78 (m, 1H). $^{19}$F NMR (376 MHz, DMSO-d6) δ −74.74, −122.55−−122.89 (m), −123.85−−124.18 (m). |
| 305 | 479.10 [M + H] | $^1$H NMR (400 MHz, DMSO-d6) δ 11.53 (s, 2H), 8.31 (d, J = 1.4 Hz, 1H), 8.02 (d, J = 6.4 Hz, 1H), 7.82 (s, 1H), 7.53 (d, J = 9.4 Hz, 2H), 7.50 (s, 1H), 7.37-7.25 (m, 2H), 3.90 (t, J = 13.1 Hz, 2H), 3.74-3.66 (m, 4H), 2.90-2.81 (m, 1H), 2.81-2.73 (m, 1H), 2.44-2.35 (m, 2H), 2.11 (dt, J = 9.4, 5.2 Hz, 1H), 1.81 (dt, J = 10.5, 5.3 Hz, 1H). $^{19}$F NMR (376 MHz, DMSO-d6) δ −74.93, −100.62−−101.02 (m), −101.82−−102.23 (m). |
| 306 | 479.04 [M + H] | $^1$H NMR (400 MHz, DMSO-d6) δ 11.63-11.49 (m, 2H), 8.36 (s, 1H), 8.04 (d, J = 6.1 Hz, 1H), 7.90 (s, 1H), 7.59 (s, 1H), 7.46-7.35 (m, 4H), 3.90 (t, J = 13.1 Hz, 2H), 3.76-3.64 (m, 2H), 2.91-2.82 (m, 1H), 2.78 (dt, J = 10.0, 5.3 Hz, 1H), 2.48-2.37 (m, 2H), 2.06 (dt, J = 9.8, 5.3 Hz, 1H), 1.83 (dt, J = 10.9, 5.5 Hz, 1H). $^{19}$F NMR (376 MHz, DMSO-d6) δ −75.10, −100.54−−100.75 (m), −101.78−−102.00 (m). |
| 307 | 471.15 [M + H] | $^1$H NMR (400 MHz, DMSO-d6) δ 11.53 (s, 2H), 8.31 (s, 1H), 8.02 (d, J = 6.4 Hz, 1H), 7.84 (s, 1H), 7.55 (s, 1H), 7.46 (dd, J = 15.7, 7.9 Hz, 2H), 7.30 (d, J = 8.1 Hz, 2H), 3.57-3.51 (m, 1H), 3.51-3.46 (m, 1H), 3.22 (s, 1H), 3.17 (s, 1H), 2.87-2.80 (m, 1H), 2.77 (dt, J = 9.9, 5.5 Hz, 1H), 2.13-2.05 (m, 1H), 1.83-1.76 (m, 1H), 1.68 (t, J = 7.3 Hz, 1H), 1.64 (t, J = 7.3 Hz, 1H), 1.10 (s, 3H), 0.97 (s, 3H). |
| 308 | 471.16 [M + H] | $^1$H NMR (400 MHz, DMSO-d6) δ 11.54 (s, 2H), 8.32 (s, 1H), 8.03 (d, J = 6.4 Hz, 1H), 7.84 (s, 1H), 7.54 (s, 1H), 7.41-7.31 (m, 4H), 3.55 (t, J = 7.3 Hz, 1H), 3.48 (t, J = 7.0 Hz, 1H), 3.23 (s, 1H), 3.16 (s, 1H), 2.86 (dt, J = 10.0, 5.8 Hz, 1H), 2.77 (dt, J = 9.8, 5.4 Hz, 1H), 2.07 (dt, J = 11.1, 5.4 Hz, 1H), 1.85-1.77 (m, 1H), 1.69 (t, J = 7.2 Hz, 1H), 1.64 (t, J = 7.0 Hz, 1H), 1.11 (s, 3H), 0.98 (d, J = 2.9 Hz, 3H). |
| 309 | 430.05 [M + H] | $^1$H NMR (400 MHz, DMSO-d6) δ 11.55 (d, J = 7.7 Hz, 2H), 8.36 (s, 1H), 8.05 (d, J = 6.0 Hz, 1H), 7.91 (s, 1H), 7.66 (s, 1H), 7.51-7.25 (m, 4H), 3.04 (dt, J = 9.6, 5.8 Hz, 1H), 2.74 (dt, J = 9.9, 5.5 Hz, 1H), 2.09 (dt, J = 9.1, 5.4 Hz, 1H), 1.84 (dt, J = 8.3, 5.3 Hz, 1H). $^{19}$F NMR (376 MHz, DMSO-d6) δ −56.92, −75.19. |
| 310 | 407.00 [M + H] | $^1$H NMR (400 MHz, DMSO-d6) δ 11.53 (s, 2H), 8.02 (d, J = 6.4 Hz, 1H), 7.82 (dd, J = 10.2, 1.6 Hz, 1H), 7.69 (dd, J = 8.1, 1.6 Hz, 1H), 7.57-7.52 (m, 2H), 7.49 (t, J = 7.9 Hz, 1H), 3.11 (dt, J = 9.2, 5.8 |

TABLE 3-continued

Characterization Data

| Example No. | ES/MS m/z | NMR |
|---|---|---|
| | | Hz, 1H), 2.86-2.77 (m, 1H), 2.23 (ddd, J = 9.0, 6.1, 4.8 Hz, 1H), 1.94-1.85 (m, 1H). $^{19}$F NMR (376 MHz, DMSO-d6) δ −75.03, −118.11 (dd, J = 10.2, 7.7 Hz), −155.57 (d, J = 7.0 Hz). |
| 311 | 372.20 [M + H] | $^{1}$H NMR (400 MHz, DMSO-d6) δ 11.67-11.48 (m, 2H), 8.87 (d, J = 1.9 Hz, 1H), 8.85 (d, J = 2.3 Hz, 1H), 8.38 (d, J = 1.5 Hz, 1H), 8.21 (t, J = 2.1 Hz, 1H), 8.05 (d, J = 6.1 Hz, 1H), 7.93 (s, 1H), 7.67 (s, 1H), 2.98-2.90 (m, 1H), 2.90-2.83 (m, 1H), 2.19 (dt, J = 8.9, 5.4 Hz, 1H), 1.94 (dt, J = 8.6, 5.5 Hz, 1H). |
| 312 | 421.04 [M + H] | $^{1}$H NMR (400 MHz, DMSO-d6) δ 11.58-11.48 (m, 2H), 8.37 (q, J = 4.4 Hz, 1H), 8.02 (d, J = 6.4 Hz, 1H), 7.83-7.74 (m, 2H), 7.54 (d, J = 7.1 Hz, 1H), 7.47 (s, 1H), 7.34-7.30 (m, 2H), 2.88 (ddd, J = 9.0, 6.5, 4.8 Hz, 1H), 2.77 (d, J = 4.5 Hz, 3H), 2.76-2.71 (m, 1H), 2.13 (dt, J = 8.9, 5.3 Hz, 1H), 1.85-1.77 (m, 1H). $^{19}$F NMR (376 MHz, DMSO-d6) δ −74.89, −155.59 (d, J = 7.3 Hz). |
| 313 | 483.02 [M + H] | $^{1}$H NMR (400 MHz, DMSO-d6) δ 11.60-11.49 (m, 2H), 8.03 (d, J = 6.4 Hz, 1H), 7.67-7.60 (m, 2H), 7.54 (d, J = 7.1 Hz, 1H), 7.48 (s, 1H), 7.37-7.31 (m, 2H), 4.84-4.67 (m, 2H), 4.55-4.41 (m, 2H), 2.88 (ddd, J = 9.0, 6.5, 4.4 Hz, 1H), 2.78-2.72 (m, 1H), 2.16 (dt, J = 8.9, 5.3 Hz, 1H), 1.81 (dt, J = 8.8, 5.5 Hz, 1H). $^{19}$F NMR (376 MHz, DMSO-d6) δ −75.18, −100.11 (p, J = 12.6 Hz), −155.56 (d, J = 7.1 Hz). |
| 314 | 369.08 [M + H] | $^{1}$H NMR (400 MHz, DMSO-d6) δ 11.39 (d, J = 2.0 Hz, 1H), 11.35 (d, J = 6.4 Hz, 1H), 8.02 (d, J = 1.2 Hz, 1H), 7.92 (d, J = 6.2 Hz, 1H), 7.54 (d, J = 1.2 Hz, 1H), 6.57 (s, 1H), 4.45-4.23 (m, 2H), 3.85-3.77 (m, 2H), 3.63 (s, 3H), 2.32-2.26 (m, 2H), 1.62 (t, J = 3.1 Hz, 1H). |
| 315 | 353.10 [M + H] | $^{1}$H NMR (400 MHz, DMSO-d6) δ 11.39 (s, 1H), 11.36 (d, J = 6.2 Hz, 1H), 8.06-8.01 (m, 1H), 7.94 (d, J = 6.0 Hz, 1H), 7.59 (s, 1H), 6.59 (s, 1H), 3.88-3.49 (m, 4H), 1.91 (t, J = 6.9 Hz, 2H), 1.73-1.64 (m, 4H), 1.64-1.51 (m, 4H). |
| 316 | 468.00 [M + H] | $^{1}$H NMR (400 MHz, DMSO-d6) δ 11.62-11.48 (m, 2H), 8.35 (s, 1H), 8.14 (s, 1H), 8.04 (d, J = 6.0 Hz, 1H), 7.90 (s, 1H), 7.75 (d, J = 8.7 Hz, 1H), 7.68 (s, 1H), 7.59 (s, 1H), 7.39 (dd, J = 8.8, 1.6 Hz, 1H), 5.44 (q, J = 9.2 Hz, 2H), 2.96-2.89 (m, 1H), 2.81-2.74 (m, 1H), 2.04 (dt, J = 10.0, 5.3 Hz, 1H), 1.85 (dt, J = 8.6, 5.4 Hz, 1H). |
| 317 | 486.00 [M + H] | $^{1}$H NMR (400 MHz, DMSO-d6) δ 11.58-11.47 (m, 2H), 8.13 (s, 1H), 8.03 (d, J = 6.5 Hz, 1H), 7.74 (d, J = 8.7 Hz, 1H), 7.68 (s, 1H), 7.54 (d, J = 7.1 Hz, 1H), 7.47 (s, 1H), 7.39 (dd, J = 8.7, 1.6 Hz, 1H), 5.43 (q, J = 9.2 Hz, 2H), 2.95 (ddd, J = 9.1, 6.3, 4.4 Hz, 1H), 2.76-2.68 (m, 1H), 2.14-2.03 (m, 1H), 1.81 (ddd, J = 8.7, 6.3, 4.8 Hz, 1H). $^{19}$F NMR (376 MHz, DMSO-d6) δ −70.16 (t, J = 9.2 Hz), −155.62 (d, J = 7.0 Hz). |
| 318 | 468.00 [M + H] | $^{1}$H NMR (400 MHz, DMSO-d6) δ 11.62-11.48 (m, 2H), 8.35 (s, 1H), 8.14 (s, 1H), 8.04 (d, J = 6.0 Hz, 1H), 7.90 (s, 1H), 7.75 (d, J = 8.7 Hz, 1H), 7.68 (s, 1H), 7.59 (s, 1H), 7.39 (dd, J = 8.8, 1.6 Hz, 1H), 5.44 (q, J = 9.2 Hz, 2H), 2.96-2.89 (m, 1H), 2.81-2.74 (m, 1H), 2.04 (dt, J = 10.0, 5.3 Hz, 1H), 1.85 (dt, J = 8.6, 5.4 Hz, 1H). |
| 319 | 486.00 [M + H] | $^{1}$H NMR (400 MHz, DMSO-d6) δ 11.58-11.47 (m, 2H), 8.13 (s, 1H), 8.03 (d, J = 6.5 Hz, 1H), 7.74 (d, J = 8.7 Hz, 1H), 7.68 (s, 1H), 7.54 (d, J = 7.1 Hz, 1H), 7.47 (s, 1H), 7.39 (dd, J = 8.7, 1.6 Hz, 1H), 5.43 (q, J = 9.2 Hz, 2H), 2.95 (ddd, J = 9.1, 6.3, 4.4 Hz, 1H), 2.76-2.68 (m, 1H), 2.14-2.03 (m, 1H), 1.81 (ddd, J = 8.7, 6.3, 4.8 Hz, 1H). $^{19}$F NMR (376 MHz, DMSO-d6) δ −70.16 (t, J = 9.2 Hz), −155.62 (d, J = 7.0 Hz). |
| 320 | 377.10 [M + H] | $^{1}$H NMR (400 MHz, DMSO-d6) δ 11.40 (d, J = 2.0 Hz, 1H), 11.39-11.33 (m, 1H), 8.05 (d, J = 1.1 Hz, 1H), 7.93 (d, J = 6.1 Hz, 1H), 7.58 (d, J = 1.2 Hz, 1H), 7.01 (s, 1H), 4.64 (t, J = 12.4 Hz, 2H), 3.77 (s, 2H), 1.98 (t, J = 15.0 Hz, 2H), 1.03 (s, 6H). $^{19}$F NMR (376 MHz, DMSO-d6) δ −75.15, −94.90 (p, J = 13.7, 13.3 Hz). |
| 321 | 417.02 [M + H] | $^{1}$H NMR (400 MHz, DMSO-d6) δ 11.65-11.50 (m, 2H), 8.39 (d, J = 1.6 Hz, 1H), 8.06 (d, J = 6.1 Hz, 1H), 8.00-7.91 (m, 2H), 7.82 (d, J = 1.6 Hz, 1H), 7.64 (s, 1H), 7.31 (dd, J = 8.4, 1.8 Hz, 1H), 2.93 (ddd, J = 9.1, 6.3, 4.4 Hz, 1H), 2.83 (ddd, J = 8.7, 5.8, 4.2 Hz, 1H), 2.80 (s, 3H), 2.08 (dt, J = 9.1, 5.3 Hz, 1H), 1.89 (ddd, J = 8.7, 6.4, 5.0 Hz, 1H). |
| 322 | 468.04 [M + H] | $^{1}$H NMR (400 MHz, DMSO-d6) δ 11.61 (dd, J = 6.2, 2.0 Hz, 1H), 11.57 (d, J = 1.9 Hz, 1H), 8.63 (s, 1H), 8.41 (d, J = 1.6 Hz, 1H), 8.06 (d, J = 6.2 Hz, 1H), 7.99 (d, J = 1.6 Hz, 1H), 7.77 (s, 1H), 7.70 (d, J = 8.4 Hz, 1H), 7.67 (s, 1H), 7.27 (dd, J = 8.5, 1.6 Hz, 1H), 5.41 (q, J = 9.2 Hz, 2H), 2.96 (ddd, J = 9.1, 6.4, 4.3 Hz, 1H), 2.84-2.75 (m, 1H), 2.06 (dt, J = 9.0, 5.3 Hz, 1H), 1.95-1.86 (m, 1H). $^{19}$F NMR (376 MHz, DMSO-d6) δ −70.70 (t, J = 9.2 Hz), −75.38. |
| 323 | 486.00 [M + H] | $^{1}$H NMR (400 MHz, DMSO-d6) δ 11.58-11.47 (m, 2H), 8.56 (s, 1H), 8.03 (d, J = 6.4 Hz, 1H), 7.74 (s, 1H), 7.66 (d, J = 8.4 Hz, 1H), 7.54 (d, J = 7.1 Hz, 1H), 7.48 (s, 1H), 7.26 (dd, J = 8.4, 1.5 Hz, 1H), |

TABLE 3-continued

Characterization Data

| Example No. | ES/MS m/z | NMR |
|---|---|---|
| | | 5.39 (q, J = 9.2 Hz, 2H), 3.02 (ddd, J = 9.2, 6.2, 4.3 Hz, 1H), 2.73 (dt, J = 9.5, 5.3 Hz, 1H), 2.14 (dt, J = 8.9, 5.2 Hz, 1H), 1.84 (dt, J = 8.5, 5.2 Hz, 1H). $^{19}$F NMR (376 MHz, DMSO-d6) δ −70.74 (t, J = 9.1 Hz), −75.32, −155.55 (d, J = 7.0 Hz). |
| 324 | 468.03 [M + H] | $^{1}$H NMR (400 MHz, DMSO-d6) δ 11.64 (dd, J = 6.3, 2.0 Hz, 1H), 11.59 (d, J = 2.0 Hz, 1H), 8.65 (s, 1H), 8.46 (d, J = 1.6 Hz, 1H), 8.08 (d, J = 6.2 Hz, 1H), 8.07 (d, J = 1.7 Hz, 1H), 7.76 (d, J = 8.5 Hz, 1H), 7.71 (s, 1H), 7.65 (d, J = 1.5 Hz, 1H), 7.35 (dd, J = 8.5, 1.6 Hz, 1H), 5.43 (q, J = 9.2 Hz, 2H), 2.90 (ddd, J = 9.1, 6.4, 4.3 Hz, 1H), 2.86-2.78 (m, 1H), 2.01 (dt, J = 8.9, 5.4 Hz, 1H), 1.92 (dt, J = 8.5, 5.4 Hz, 1H). $^{19}$F NMR (376 MHz, DMSO-d6) δ −70.74 (t, J = 9.2 Hz), −75.37. |
| 325 | 375.10 [M + H] | $^{1}$H NMR (400 MHz, DMSO-d6) δ 11.40 (s, 1H), 11.37 (d, J = 5.4 Hz, 1H), 8.05 (d, J = 1.1 Hz, 1H), 7.92 (d, J = 5.9 Hz, 1H), 7.56 (d, J = 1.1 Hz, 1H), 6.57 (s, 1H), 4.42-4.22 (m, 2H), 4.16-3.97 (m, 2H), 2.39-2.28 (m, 2H), 2.10-2.01 (m, 2H), 2.01-1.93 (m, 1H), 1.94-1.79 (m, 1H). $^{19}$F NMR (376 MHz, DMSO-d6) δ −116.97. |
| 326 | 400.02 [M + H] | $^{1}$H NMR (400 MHz, DMSO-d6) δ 11.53 (s, 2H), 8.30 (s, 1H), 8.02 (d, J = 6.3 Hz, 1H), 7.98 (s, 1H), 7.82 (s, 1H), 7.68 (d, J = 8.4 Hz, 1H), 7.56 (s, 1H), 7.53 (s, 1H), 7.03 (d, J = 8.6 Hz, 1H), 4.02 (s, 3H), 2.98 (dt, J = 9.4, 5.7 Hz, 1H), 2.81 (dt, J = 9.8, 5.4 Hz, 1H), 2.17-2.08 (m, 1H), 1.96-1.87 (m, 1H). $^{19}$F NMR (376 MHz, DMSO-d6) δ −74.91. |
| 327 | 455.00 [M + H] | $^{1}$H NMR (400 MHz, DMSO-d6) δ 11.53 (s, 2H), 8.31 (d, J = 1.4 Hz, 1H), 8.02 (d, J = 6.4 Hz, 1H), 7.98 (d, J = 8.9 Hz, 1H), 7.88 (s, 1H), 7.82 (s, 1H), 7.78 (dd, J = 9.0, 1.8 Hz, 1H), 7.57 (s, 1H), 3.09 (ddd, J = 9.0, 6.2, 4.6 Hz, 1H), 2.87-2.80 (m, 1H), 2.18-2.10 (m, 1H), 1.93 (dt, J = 8.8, 5.5 Hz, 1H). $^{19}$F NMR (376 MHz, DMSO-d6) δ −62.09, −74.93. |
| 328 | 397 [M + H] | $^{1}$H NMR (400 MHz, DMSO-d6) δ 11.49-11.36 (m, 2H), 8.23 (s, 1H), 7.93 (d, J = 6.1 Hz, 1H), 6.67 (s, 1H), 4.54-4.18 (m, 2H), 3.99-3.66 (m, 2H), 1.20 (s, 6H). $^{19}$F NMR (376 MHz, DMSO-d6) δ −115.35 (t, J = 12.8 Hz). |
| 329 | 554.00 [M + H] | $^{1}$H NMR (400 MHz, DMSO-d6) δ 11.63-11.42 (m, 2H), 8.04 (d, J = 6.4 Hz, 1H), 7.94 (s, 1H), 7.79 (d, J = 8.5 Hz, 1H), 7.56 (d, J = 7.1 Hz, 1H), 7.52 (s, 1H), 7.37 (dd, J = 8.6, 1.1 Hz, 1H), 5.62 (q, J = 9.2, 8.8 Hz, 2H), 3.16-3.06 (m, 1H), 2.88-2.76 (m, 1H), 2.26-2.17 (m, 1H), 1.97-1.82 (m, 1H). $^{19}$F NMR (376 MHz, DMSO-d6) δ −60.43, −70.03 (t, J = 9.0 Hz), −155.55 (d, J = 7.0 Hz). |
| 330 | 496.10 [M + H] | $^{1}$H NMR (400 MHz, DMSO-d6) δ 11.49-11.28 (m, 2H), 8.53 (d, J = 5.3 Hz, 1H), 8.09 (d, J = 1.1 Hz, 1H), 7.95 (d, J = 6.1 Hz, 1H), 7.59 (d, J = 1.1 Hz, 1H), 7.49 (dd, J = 5.4, 1.4 Hz, 1H), 7.43 (s, 1H), 6.65 (s, 1H), 6.01 (dd, J = 8.9, 5.2 Hz, 1H), 4.82-4.36 (m, 4H). $^{19}$F NMR (376 MHz, DMSO-d6) δ −64.03, −75.18 |
| 331 | 496.10 [M + H] | $^{1}$H NMR (400 MHz, DMSO-d6) δ 11.49-11.28 (m, 2H), 8.53 (d, J = 5.3 Hz, 1H), 8.09 (d, J = 1.1 Hz, 1H), 7.95 (d, J = 6.1 Hz, 1H), 7.59 (d, J = 1.1 Hz, 1H), 7.49 (dd, J = 5.4, 1.4 Hz, 1H), 7.43 (s, 1H), 6.65 (s, 1H), 6.01 (dd, J = 8.9, 5.2 Hz, 1H), 4.82-4.36 (m, 4H). $^{19}$F NMR (376 MHz, DMSO-d6) δ −64.03, −75.18. |
| 332 | 494.20 [M + H] | $^{1}$H NMR (400 MHz, Acetonitrile-d3) δ 9.18 (s, 2H), 8.11 (d, J = 3.0 Hz, 1H), 8.04 (d, J = 6.4 Hz, 1H), 7.97 (d, J = 1.6 Hz, 1H), 7.70 (d, J = 1.6 Hz, 1H), 7.62 (dd, J = 9.0, 3.0 Hz, 1H), 7.01 (s, 1H), 6.98-6.47 (m, 2H), 5.88 (dq, J = 8.3, 4.3 Hz, 1H), 4.59-4.32 (m, 3H). |
| 333 | 494.20 [M + H] | $^{1}$H NMR (400 MHz, Acetonitrile-d3) δ 9.18 (s, 2H), 8.11 (d, J = 3.0 Hz, 1H), 8.04 (d, J = 6.4 Hz, 1H), 7.97 (d, J = 1.6 Hz, 1H), 7.70 (d, J = 1.6 Hz, 1H), 7.62 (dd, J = 9.0, 3.0 Hz, 1H), 7.01 (s, 1H), 6.98-6.47 (m, 2H), 5.88 (dq, J = 8.3, 4.3 Hz, 1H), 4.59-4.32 (m, 3H). |
| 334 | 512.20 [M + H] | $^{1}$H NMR (400 MHz, Acetonitrile-d3) δ 9.16 (s, 2H), 8.24 (d, J = 2.9 Hz, 1H), 8.03 (d, J = 6.4 Hz, 1H), 7.95 (d, J = 1.5 Hz, 1H), 7.77-7.70 (m, 1H), 7.68 (d, J = 1.5 Hz, 1H), 7.08-6.87 (m, 2H), 5.90 (tt, J = 8.6, 3.9 Hz, 1H), 4.61-4.34 (m, 3H), 4.21 (d, J = 12.4 Hz, 1H). |
| 335 | 512.20 [M + H] | $^{1}$H NMR (400 MHz, Acetonitrile-d3) δ 9.16 (s, 2H), 8.24 (d, J = 2.9 Hz, 1H), 8.03 (d, J = 6.4 Hz, 1H), 7.95 (d, J = 1.5 Hz, 1H), 7.77-7.70 (m, 1H), 7.68 (d, J = 1.5 Hz, 1H), 7.08-6.87 (m, 2H), 5.90 (tt, J = 8.6, 3.9 Hz, 1H), 4.61-4.34 (m, 3H), 4.21 (d, J = 12.4 Hz, 1H). |
| 336 | 562.10 [M + H] | $^{1}$H NMR (400 MHz, Acetonitrile-d3) δ 9.17 (s, 2H), 8.23 (d, J = 2.9 Hz, 1H), 8.06 (d, J = 6.4 Hz, 1H), 7.98 (d, J = 1.6 Hz, 1H), 7.74 (dd, J = 10.3, 2.3 Hz, 2H), 7.13-6.81 (m, 2H), 5.91 (h, J = 4.3 Hz, 1H), 4.54-4.34 (m, 3H), 4.20 (dt, J = 12.3, 2.6 Hz, 1H). $^{19}$F NMR (376 MHz, Acetonitrile-d3) δ −77.25, −87.18, −89.01 |
| 337 | 562.10 [M + H] | $^{1}$H NMR (400 MHz, Acetonitrile-d3) δ 9.17 (s, 2H), 8.23 (d, J = 2.9 Hz, 1H), 8.06 (d, J = 6.4 Hz, 1H), 7.98 (d, J = 1.6 Hz, 1H), 7.74 (dd, J = 10.3, 2.3 Hz, 2H), 7.13-6.81 (m, 2H), 5.91 (h, J = 4.3 Hz, 1H), 4.54-4.34 (m, 3H), 4.20 (dt, J = 12.3, 2.6 Hz, 1H). |

TABLE 3-continued

Characterization Data

| Example No. | ES/MS m/z | NMR |
|---|---|---|
| 338 | 453.20 [M + H] | $^1$H NMR (400 MHz, Acetonitrile-d3) δ 9.30 (d, J = 12.5 Hz, 2H), 8.61 (d, J = 2.3 Hz, 1H), 8.15-8.02 (m, 2H), 8.02 (d, J = 1.8 Hz, 1H), 7.79 (d, J = 1.8 Hz, 1H), 7.17 (s, 1H), 7.04 (d, J = 8.7 Hz, 1H), 6.00 (ddt, J = 8.3, 4.9, 3.1 Hz, 1H), 4.46 (td, J = 18.2, 10.3 Hz, 3H), 4.19 (dt, J = 12.1, 2.7 Hz, 1H). |
| 339 | 453.20 [M + H]. | $^1$H NMR (400 MHz, Acetonitrile-d3) δ 9.30 (d, J = 12.5 Hz, 2H), 8.61 (d, J = 2.3 Hz, 1H), 8.15-8.02 (m, 2H), 8.02 (d, J = 1.8 Hz, 1H), 7.79 (d, J = 1.8 Hz, 1H), 7.17 (s, 1H), 7.04 (d, J = 8.7 Hz, 1H), 6.00 (ddt, J = 8.3, 4.9, 3.1 Hz, 1H), 4.46 (td, J = 18.2, 10.3 Hz, 3H), 4.19 (dt, J = 12.1, 2.7 Hz, 1H). |
| 340 | 497.10 [M + H] | $^1$H NMR (400 MHz, Acetonitrile-d3) δ 9.22 (s, 2H), 8.65 (s, 1H), 8.45 (d, J = 1.3 Hz, 1H), 8.07 (d, J = 6.4 Hz, 1H), 8.00 (d, J = 1.6 Hz, 1H), 7.75 (d, J = 1.6 Hz, 1H), 7.10 (s, 1H), 6.04-5.84 (m, 1H), 4.61-4.37 (m, 3H), 4.26 (dt, J = 12.5, 2.7 Hz, 1H). $^{19}$F NMR (376 MHz, Acetonitrile-d3) δ −68.01, −77.26, −106.97--111.19 (m), −118.61--123.19 (m). |
| 341 | 478.2 [M + H] | $^1$H NMR (400 MHz, Acetonitrile-d3) δ 9.09 (d, J = 14.7 Hz, 2H), 8.36 (d, J = 5.3 Hz, 1H), 8.00 (d, J = 6.4 Hz, 1H), 7.92 (d, J = 1.4 Hz, 1H), 7.62 (d, J = 1.4 Hz, 1H), 7.23 (d, J = 5.3 Hz, 1H), 7.05 (s, 1H), 6.99-6.51 (m, 2H), 5.95 (d, J = 4.6 Hz, 1H), 4.49 (td, J = 20.8, 8.3 Hz, 3H), 4.23 (d, J = 12.4 Hz, 1H). $^{19}$F NMR (376 MHz, Acetonitrile-d3) δ −77.27, −108.96−109.60 (m), −117.17 (d, J = 55.4 Hz), −121.70--122.36 (m). |
| 342 | 453.1 [M + H] | $^1$H NMR (400 MHz, Acetonitrile-d3) δ 9.12 (d, J = 15.2 Hz, 2H), 8.41 (dd, J = 5.2, 0.8 Hz, 1H), 8.03-7.93 (m, 1H), 7.89 (d, J = 1.2 Hz, 1H), 7.57 (d, J = 1.2 Hz, 1H), 7.36 (dd, J = 5.2, 1.3 Hz, 1H), 7.25 (d, J = 1.1 Hz, 1H), 6.76 (s, 1H), 5.92 (d, J = 4.3 Hz, 1H), 4.67-4.33 (m, 3H), 4.26 (d, J = 12.8 Hz, 1H). $^{19}$F NMR (376 MHz, Acetonitrile-d3) δ −77.18, −109.11 (d, J = 246.1 Hz), −120.61--123.05 (m). |
| 343 | 391.10 [M + H] | $^1$H NMR (400 MHz, Acetonitrile-d3) δ 9.11 (s, 2H), 7.99 (d, J = 6.2 Hz, 1H), 7.88 (d, J = 1.3 Hz, 1H), 7.59 (d, J = 1.3 Hz, 1H), 6.76 (s, 1H), 6.48 (t, J = 75.5 Hz, 1H), 4.44 (s, 1H), 4.36 (d, J = 4.0 Hz, 1H), 4.27 (d, J = 12.1 Hz, 1H), 4.11 (d, J = 10.7 Hz, 1H), 3.64 (m, 1H), 1.11-0.83 (m, 3H), 0.79 (dt, J = 10.0, 5.0 Hz, 1H). $^{19}$F NMR (376 MHz, Acetonitrile-d3) δ −77.04, −80.78--82.87 (m). |
| 344 | 341.20 [M + H] | $^1$H NMR (400 MHz, DMSO-d6) δ 11.37 (dd, J = 10.7, 4.1 Hz, 2H), 8.04 (d, J = 1.3 Hz, 1H), 7.94 (d, J = 6.1 Hz, 1H), 7.58 (d, J = 1.3 Hz, 1H), 6.57 (s, 1H), 3.79 (d, J = 6.5 Hz, 1H), 2.58-2.51 (m, 4H), 0.89 (dt, J = 11.1, 5.0 Hz, 1H), 0.66 (dt, J = 16.5, 5.5 Hz, 3H). |
| 345 | 486.20 [M + H] | $^1$H NMR (400 MHz, Acetonitrile-d3) δ 9.20 (d, J = 33.4 Hz, 2H), 8.51 (d, J = 2.4 Hz, 1H), 8.05-7.98 (m, 1H), 7.96 (dd, J = 8.8, 2.6 Hz, 1H), 7.91 (d, J = 1.5 Hz, 1H), 7.66 (d, J = 1.4 Hz, 1H), 7.03-6.84 (m, 2H), 4.79 (d, J = 12.8 Hz, 1H), 4.21 (d, J = 10.9 Hz, 1H), 4.17-4.01 (m, 2H), 3.34 (q, J = 7.8 Hz, 1H), 2.80-2.62 (m, 1H), 2.41 (q, J = 10.8 Hz, 1H), 2.35-2.19 (m, 1H), 1.68 (dq, J = 11.9, 8.8 Hz, 1H). $^{19}$F NMR (376 MHz, Acetonitrile-d3) δ −62.59, −77.09. |
| 346 | 411.20 [M + H] | $^1$H NMR (400 MHz, DMSO-d6) δ 11.51-11.28 (m, 2H), 8.09 (d, J = 1.2 Hz, 1H), 7.96 (d, J = 6.1 Hz, 1H), 7.59 (d, J = 1.2 Hz, 1H), 7.47-7.22 (m, 6H), 6.68 (s, 1H), 4.52 (d, J = 30.3 Hz, 2H), 4.18 (s, 2H). $^{19}$F. NMR (377 MHz, DMSO-d6) δ −75.10, −108.01 |
| 347 | 365.20 [M + H] | $^1$H NMR (400 MHz, DMSO-d6) δ 11.50-11.10 (m, 2H), 8.06 (d, J = 1.3 Hz, 1H), 7.95 (d, J = 6.1 Hz, 1H), 7.59 (d, J = 1.3 Hz, 1H), 7.05-6.50 (m, 2H), 5.16-4.90 (m, 1H), 2.26 (dddd, J = 19.5, 10.7, 8.0, 4.0 Hz, 2H). $^{19}$F NMR (377 MHz, DMSO-d6) δ −75.33, −81.14 (d, J = 75.5 Hz). |
| 348 | 365.20 [M + H] | 1H NMR (400 MHz, Acetonitrile-d3) δ 9.16 (s, 2H), 8.03 (d, J = 6.3 Hz, 1H), 7.93 (d, J = 1.6 Hz, 1H), 7.69 (d, J = 1.5 Hz, 1H), 6.94 (s, 1H), 6.50 (t, J = 75.3 Hz, 1H), 5.02 (p, J = 3.7 Hz, 1H), 4.12 (d, J = 4.8 Hz, 2H), 3.90 (q, J = 9.5, 9.0 Hz, 2H), 2.32 (tt, J = 6.1, 3.7 Hz, 2H). $^{19}$F NMR (376 MHz, Acetonitrile-d3) δ −77.12, −83.13 (dd, J = 75.2, 5.4 Hz). |
| 349 | 355.20 [M + H] | $^1$H NMR (400 MHz, DMSO-d6) δ 11.38 (dd, J = 10.5, 4.1 Hz, 2H), 8.05 (d, J = 1.3 Hz, 1H), 7.94 (d, J = 6.1 Hz, 1H), 7.59 (s, 1H), 6.57 (s, 1H), 3.52 (d, J = 3.7 Hz, 1H), 3.29 (s, 3H), 2.70 (s, 1H), 2.18 (t, J = 8.1 Hz, 1H), 2.02-1.81 (m, 1H), 1.04-0.93 (m, 1H), 0.84 (dt, J = 9.3, 5.4 Hz, 1H), 0.74-0.54 (m, 2H). |
| 350 | 361.14 [M + H] | $^1$H NMR (400 MHz, DMSO-d6) δ 12.04 (s, 1H), 11.74 (s, 1H), 8.56 (d, J = 6.0 Hz, 1H), 8.18 (d, J = 2.2 Hz, 1H), 6.88 (s, 1H), 6.56 (d, J = 2.2 Hz, 1H), 4.76 (s, 2H), 1.25-0.88 (m, 4H). $^{19}$F NMR (376 MHz, DMSO-d6) δ −107.89. |
| 351 | 389.00 [M + H] | $^1$H NMR (400 MHz, DMSO-d6) δ 11.56-11.23 (m, 2H), 7.99 (d, J = 6.1 Hz, 1H), 7.48 (d, J = 7.2 Hz, 1H), 6.70 (s, 1H), 4.65 (t, J = 12.4 Hz, 4H). $^{19}$F NMR (376 MHz, DMSO-d6) δ −74.91, −122.77, −122.72--122.93 (m), −155.26 (d, J = 7.6 Hz). |

TABLE 3-continued

Characterization Data

| Example No. | ES/MS m/z | NMR |
|---|---|---|
| 352 | 379.10 [M + H] | ¹H NMR (400 MHz, DMSO-d6) δ 11.56-11.20 (m, 2H), 8.03 (d, J = 1.2 Hz, 1H), 7.93 (d, J = 6.1 Hz, 1H), 7.55 (d, J = 1.1 Hz, 1H), 6.60 (s, 1H), 4.39 (s, 1H), 3.76 (d, J = 11.3 Hz, 3H), 2.26 (d, J = 3.2 Hz, 2H), 1.89 (tt, J = 7.4, 3.6 Hz, 1H). ¹⁹F NMR (376 MHz, DMSO-d6) δ −63.87 (d, J = 7.5 Hz), −75.07. |
| 353 | 435.10 [M + H] | ¹H NMR (400 MHz, Methanol-d4) δ 8.17 (s, 1H), 8.09 (d, J = 1.5 Hz, 1H), 7.75 (d, J = 1.5 Hz, 1H), 7.04 (s, 1H), 4.53 (s, 2H), 4.09 (t, J = 7.3 Hz, 2H), 2.72 (t, J = 7.3 Hz, 2H). ¹⁹F NMR (376 MHz, Methanol-d4) δ −73.55, −78.07. |
| 354 | 336.10 [M + H] | ¹H NMR (400 MHz, DMSO-d6) δ 11.39 (d, J = 18.6 Hz, 2H), 8.04 (d, J = 1.2 Hz, 1H), 7.92 (d, J = 6.1 Hz, 1H), 7.55 (d, J = 1.2 Hz, 1H), 6.61 (s, 1H), 3.89 (d, J = 10.7 Hz, 1H), 3.82-3.73 (m, 1H), 2.60 (dt, J = 9.0, 5.0 Hz, 1H), 1.58 (dd, J = 8.6, 5.4 Hz, 1H), 1.12 (t, J = 5.5 Hz, 1H). |
| 355 | 329.10 [M + H] | ¹H NMR (400 MHz, DMSO-d6) δ 11.42 (s, 2H), 8.11 (d, J = 1.3 Hz, 1H), 7.95 (d, J = 6.4 Hz, 1H), 7.65 (d, J = 1.3 Hz, 1H), 6.68 (s, 1H), 4.11 (t, J = 10.6 Hz, 2H), 3.92 (s, 2H), 2.37-2.19 (m, 1H), 1.63 (dddd, J = 16.5, 11.6, 8.1, 4.4 Hz, 1H), 1.02-0.72 (m, 1H). ¹⁹F NMR (376 MHz, DMSO-d6) δ −199.67. |
| 356 | 372.10 [M + H] | ¹H NMR (400 MHz, DMSO-d6) δ 11.68 (s, 1H), 11.55 (s, 1H), 8.48 (d, J = 7.6 Hz, 2H), 7.51 (s, 1H), 4.73 (ddd, J = 14.9, 10.2, 3.8 Hz, 5H). ¹⁹F NMR (376 MHz, DMSO-d6) δ −122.69--122.82 (m). |
| 357 | 362.10 [M + H] | ¹H NMR (400 MHz, DMSO-d6) δ 11.63 (s, 1H), 11.50 (s, 1H), 8.48 (s, 1H), 8.39 (s, 1H), 7.42 (s, 1H), 4.66 (t, J = 12.3 Hz, 2H), 4.10 (s, 2H), 1.06 (dd, J = 4.8, 3.1 Hz, 4H). ¹⁹F NMR (376 MHz, DMSO-d6) δ −107.51 (t, J = 12.5 Hz). |
| 358 | 371.10 [M + H] | ¹H NMR (400 MHz, DMSO-d6) δ 11.60 (d, J = 6.3 Hz, 1H), 11.50 (d, J = 2.0 Hz, 1H), 8.37 (d, J = 6.4 Hz, 1H), 8.14 (d, J = 2.3 Hz, 1H), 7.22 (s, 1H), 6.49 (d, J = 2.3 Hz, 1H), 4.70 (td, J = 11.3, 10.8, 5.3 Hz, 4H). ¹⁹F NMR (376 MHz, DMSO-d6) δ −75.06, −122.08 (td, J = 13.8, 12.6, 5.2 Hz). |
| 359 | 430.10 [M + H] | ¹H NMR (400 MHz, Methanol-d4) δ 8.27 (d, J = 1.6 Hz, 1H), 8.24 (s, 1H), 7.91 (s, 1H), 7.82 (s, 1H), 7.44-7.33 (m, 2H), 7.29-7.20 (m, 2H), 2.88-2.71 (m, 2H), 2.03-1.81 (m, 2H) ¹⁹F NMR (376 MHz, Methanol-d4) δ −60.15, −77.61. |
| 360 | 426.10 [M + H] | ¹H NMR (400 MHz, DMSO-d6) δ 11.54 (s, 2H), 8.32 (d, J = 1.3 Hz, 1H), 8.03 (d, J = 6.4 Hz, 1H), 7.85 (s, 1H), 7.55 (s, 1H), 7.41-7.28 (m, 2H), 7.15 (dd, J = 8.4, 1.8 Hz, 1H), 2.93-2.82 (m, 1H), 2.72 (ddd, J = 9.0, 5.9, 4.3 Hz, 1H), 2.09 (dt, J = 8.0, 5.2 Hz, 1H), 1.79 (dt, J = 8.9, 5.3 Hz, 1H). ¹⁹F NMR (376 MHz, DMSO-d6) δ −49.75 (d, J = 2.3 Hz), −74.85. |
| 361 | 482.20 [M + H] | ¹H NMR (400 MHz, Acetonitrile-d3) δ 9.45 (s, 1H), 9.36 (s, 1H), 8.24-8.13 (m, 3H), 8.09 (t, J = 2.6 Hz, 1H), 7.97 (d, J = 2.1 Hz, 1H), 7.69 (d, J = 8.7 Hz, 1H), 7.53 (s, 1H), 7.00 (dd, J = 8.8, 1.4 Hz, 1H), 4.70 (td, J = 7.0, 1.8 Hz, 2H), 2.98 (qt, J = 10.9, 6.9 Hz, 2H), 2.81 (q, J = 4.6 Hz, 1H), 2.70 (ddd, J = 11.0, 6.5, 4.3 Hz, 1H), 2.54 (s, 0H), 2.06-1.98 (m, 1H), 1.90 (dq, J = 9.5, 6.6, 5.7 Hz, 1H). ¹⁹F NMR (376 MHz, Acetonitrile-d3) δ −66.76 (t, J = 10.9 Hz), −77.25 (d, J = 6.6 Hz). |
| 362 | 493.20 [M + H] | ¹H NMR (400 MHz, Acetonitrile-d3) δ 9.40 (s, 1H), 9.25 (s, 1H), 8.09 (s, 2H), 7.84 (d, J = 9.4 Hz, 2H), 7.73 (d, J = 13.1 Hz, 2H), 7.40 (d, J = 8.5 Hz, 1H), 5.29 (d, J = 9.3 Hz, 2H), 3.13 (dd, J = 7.3, 4.7 Hz, 4H). ¹⁹F NMR (376 MHz, Acetonitrile-d3) δ −71.88 (t, J = 8.7 Hz), −76.87. |
| 363 | 445.20 [M + H] | ¹H NMR (400 MHz, Acetonitrile-d3) δ 9.54 (s, 1H), 9.34 (s, 1H), 8.34 (d, J = 2.9 Hz, 1H), 8.23-8.11 (m, 2H), 8.06 (s, 1H), 7.99 (d, J = 2.0 Hz, 1H), 7.65-7.44 (m, 2H), 4.66 (q, J = 8.4 Hz, 2H), 3.20 (dt, J = 9.3, 5.2 Hz, 1H), 2.82 (ddd, J = 9.1, 6.2, 4.4 Hz, 1H), 2.02 (ddd, J = 8.9, 6.3, 5.2 Hz, 1H), 1.92-1.87 (m, 1H). ¹⁹F NMR (376 MHz, Acetonitrile-d3) δ −75.34 (t, J = 8.4 Hz), −77.10. |
| 364 | 421.10 [M + H] | ¹H NMR (400 MHz, Acetonitrile-d3) δ 9.44 (s, 1H), 9.33 (s, 1H), 8.19 (d, J = 2.0 Hz, 1H), 8.15 (d, J = 6.4 Hz, 1H), 8.12 (q, J = 1.3 Hz, 1H), 8.03 (s, 1H), 7.97 (d, J = 2.0 Hz, 1H), 2.31-1.99 (m, 4H). ¹⁹F NMR (377 MHz, Acetonitrile-d3) δ −55.58, −77.15. |
| 365 | 421.10 [M + H] | ¹H NMR (400 MHz, DMSO-d6) δ 11.55 (d, J = 3.8 Hz, 2H), 8.34 (d, J = 1.4 Hz, 1H), 8.08 (t, J = 1.0 Hz, 1H), 8.02 (d, J = 6.4 Hz, 1H), 7.86 (s, 1H), 7.63 (s, 1H), 3.31 (dt, J = 9.8, 5.4 Hz, 1H), 2.88 (ddd, J = 9.0, 6.1, 4.4 Hz, 1H), 2.29 (dt, J = 8.8, 5.4 Hz, 1H), 1.88 (dt, J = 9.0, 5.4 Hz, 1H). ¹⁹F NMR (376 MHz, DMSO-d6) δ −60.32, −75.15. |
| 366 | 404.10 [M + H] | ¹H NMR (400 MHz, DMSO-d6) δ 11.53 (s, 2H), 8.44 (s, 1H), 8.32 (d, J = 1.4 Hz, 1H), 8.09-7.90 (m, 2H), 7.84 (s, 1H), 7.55 (s, 1H), 2.77 (dq, J = 12.3, 5.9 Hz, 1H), 2.71-2.59 (m, 1H), 2.11-1.91 (m, 1H), 1.79-1.59 (m, 1H). ¹⁹F NMR (377 MHz, DMSO-d6) δ −59.68, −75.03. |

TABLE 3-continued

Characterization Data

| Example No. | ES/MS m/z | NMR |
|---|---|---|
| 367 | 421.10 [M + H] | $^1$H NMR (400 MHz, DMSO-d6) δ 11.55 (s, 2H), 8.34 (dd, J = 5.4, 1.2 Hz, 2H), 8.02 (d, J = 6.4 Hz, 1H), 7.85 (s, 1H), 7.63 (s, 1H), 3.51 (ddd, J = 8.8, 5.9, 4.3 Hz, 1H), 3.06 (ddd, J = 9.1, 6.3, 4.3 Hz, 1H), 2.27-2.16 (m, 1H), 2.06-1.83 (m, 1H). $^{19}$F NMR (377 MHz, DMSO-d6) δ −62.89, −75.11. |
| 368 | 386.10 [M + H] | $^1$H NMR (400 MHz, Acetonitrile-d3) δ 9.53 (s, 1H), 9.38 (s, 1H), 8.20 (d, J = 2.1 Hz, 1H), 8.16 (d, J = 6.1 Hz, 1H), 8.02 (d, J = 2.1 Hz, 1H), 7.97 (d, J = 5.6 Hz, 1H), 7.70 (s, 1H), 7.33 (t, J = 60.0 Hz, 1H), 2.84 (dt, J = 8.6, 5.1 Hz, 1H), 2.51 (ddd, J = 9.2, 6.5, 4.4 Hz, 1H), 1.86-1.64 (m, 2H). $^{19}$F NMR (377 MHz, Acetonitrile-d3) δ −77.11, −95.58, −95.74. |
| 369 | 386.10 [M + H] | $^1$H NMR (400 MHz, DMSO-d6) δ 11.53 (s, 2H), 8.31 (s, 1H), 8.16 (d, J = 2.6 Hz, 1H), 7.95-7.57 (m, 2H), 7.54 (s, 1H), 6.50 (d, J = 2.7 Hz, 1H), 2.92 (dt, J = 9.1, 5.8 Hz, 1H), 2.88-2.76 (m, 1H), 2.02 (dt, J = 9.5, 4.9 Hz, 1H), 1.81-1.66 (m, 1H). $^{19}$F NMR (376 MHz, DMSO-d6) δ −74.93, −94.15 (d, J = 2.7 Hz), −94.31. |
| 370 | 404.10 [M + H] | $^1$H NMR (400 MHz, DMSO-d6) δ 11.53 (d, J = 4.6 Hz, 2H), 8.19 (s, 1H), 8.02 (d, J = 6.4 Hz, 1H), 7.93-7.58 (m, 2H), 7.55 (d, J = 7.1 Hz, 1H), 7.46 (s, 1H), 2.77 (ddd, J = 9.0, 6.2, 4.4 Hz, 1H), 2.62 (ddd, J = 8.8, 5.7, 4.3 Hz, 1H), 2.05-1.95 (m, 1H), 1.65 (ddd, J = 8.7, 6.3, 4.5 Hz, 1H). $^{19}$F NMR (376 MHz, DMSO-d6) δ −75.20, −93.98, −94.14, −155.65 (d, J = 7.3 Hz). |
| 371 | 404.10 [M + H] | $^1$H NMR (400 MHz, DMSO-d6) δ 11.53 (d, J = 4.6 Hz, 2H), 8.19 (s, 1H), 8.02 (d, J = 6.4 Hz, 1H), 7.93-7.58 (m, 2H), 7.55 (d, J = 7.1 Hz, 1H), 7.46 (s, 1H), 2.77 (ddd, J = 9.0, 6.2, 4.4 Hz, 1H), 2.62 (ddd, J = 8.8, 5.7, 4.3 Hz, 1H), 2.05-1.95 (m, 1H), 1.65 (ddd, J = 8.7, 6.3, 4.5 Hz, 1H). $^{19}$F NMR (376 MHz, DMSO-d6) δ −75.20, −93.98, −94.14, −155.65 (d, J = 7.3 Hz). |
| 372 | 431.10 [M + H] | $^1$H NMR (400 MHz, DMSO-d6) δ 11.85-11.68 (m, 1H), 11.63 (d, J = 1.9 Hz, 1H), 8.63 (d, J = 2.8 Hz, 1H), 8.55 (d, J = 1.8 Hz, 1H), 8.18 (s, 1H), 8.11 (d, J = 6.2 Hz, 1H), 7.89-7.79 (m, 2H), 7.63 (d, J = 8.6 Hz, 1H), 3.16-2.96 (m, 2H), 2.05-1.84 (m, 2H). $^{19}$F NMR (376 MHz, DMSO-d6) δ −57.85. |
| 373 | 431.10 [M + H] | $^1$H NMR (400 MHz, DMSO-d6) δ 11.85-11.68 (m, 1H), 11.63 (d, J = 1.9 Hz, 1H), 8.63 (d, J = 2.8 Hz, 1H), 8.55 (d, J = 1.8 Hz, 1H), 8.18 (s, 1H), 8.11 (d, J = 6.2 Hz, 1H), 7.89-7.79 (m, 2H), 7.63 (d, J = 8.6 Hz, 1H), 3.16-2.96 (m, 2H), 2.05-1.84 (m, 2H). $^{19}$F NMR (376 MHz, DMSO-d6) δ −57.85. |
| 374 | 449.10 [M + H] | $^1$H NMR (400 MHz, DMSO-d6) δ 11.57-11.51 (m, 2H), 8.60 (d, J = 2.7 Hz, 1H), 8.03 (d, J = 6.4 Hz, 1H), 7.86-7.78 (m, 1H), 7.62 (d, J = 8.6 Hz, 1H), 7.58-7.48 (m, 2H), 3.12 (ddd, J = 8.7, 5.8, 4.2 Hz, 1H), 2.96 (ddd, J = 9.0, 6.1, 4.1 Hz, 1H), 2.18-2.06 (m, 1H), 1.87 (ddd, J = 9.4, 5.8, 4.0 Hz, 1H). $^{19}$F NMR (376 MHz, DMSO-d6) δ −57.86, −75.39, −155.54 (d, J = 7.0 Hz). |
| 375 | 390.10 [M + H] | $^1$H NMR (400 MHz, DMSO-d6) δ 11.56 (d, J = 9.5 Hz, 2H), 8.74 (s, 1H), 8.01 (dd, J = 16.7, 7.1 Hz, 2H), 7.92 (dd, J = 8.1, 2.1 Hz, 1H), 7.60-7.53 (m, 2H), 3.04 (q, J = 6.5, 6.0 Hz, 1H), 2.87 (dt, J = 9.9, 5.4 Hz, 1H), 2.29 (dt, J = 10.2, 5.6 Hz, 1H), 1.92 (dt, J = 10.4, 5.7 Hz, 1H). $^{19}$F NMR (376 MHz, DMSO-d6) δ −75.43, −155.57 (d, J = 7.0 Hz). |
| 376 | 431.10 [M + H] | $^1$H NMR (400 MHz, DMSO-d6) δ 11.55 (d, J = 4.7 Hz, 2H), 8.44-8.26 (m, 2H), 8.03 (d, J = 6.3 Hz, 1H), 7.95-7.77 (m, 2H), 7.60 (s, 1H), 7.28 (d, J = 8.5 Hz, 1H), 3.00-2.88 (m, 1H), 2.80 (dt, J = 9.5, 5.6 Hz, 1H), 2.15 (dt, J = 8.9, 5.4 Hz, 1H), 1.85 (dt, J = 8.7, 5.5 Hz, 1H). $^{19}$F NMR (376 MHz, DMSO-d6) δ −55.65, −75.08. |
| 377 | 416.1 [M + H] | $^1$H NMR (400 MHz, DMSO-d6) δ 11.56 (d, J = 3.9 Hz, 2H), 9.20 (d, J = 1.0 Hz, 2H), 8.36 (d, J = 1.4 Hz, 1H), 8.04 (d, J = 6.4 Hz, 1H), 7.88 (s, 1H), 7.67 (s, 1H), 3.34-3.01 (m, 2H), 2.30-2.15 (m, 1H), 2.01 (ddd, J = 9.4, 5.7, 4.1 Hz, 1H). $^{19}$F NMR (376 MHz, DMSO-d6) δ −61.20, −75.17. |
| 378 | 434.1 [M + H] | $^1$H NMR (400 MHz, DMSO-d6) δ 11.54 (s, 2H), 9.18 (s, 2H), 8.03 (s, 1H), 7.56 (t, J = 3.5 Hz, 2H), 3.26 (ddd, J = 9.1, 5.6, 4.1 Hz, 1H), 3.16-3.00 (m, 1H), 2.29 (ddd, J = 8.7, 6.1, 4.0 Hz, 1H), 2.11-1.88 (m, 1H). $^{19}$F NMR (377 MHz, DMSO-d6) δ −61.23, −73.95, −155.48 (d, J = 7.3 Hz). |
| 379 | 397.20 [M + H] | $^1$H NMR (400 MHz, DMSO-d6) δ 11.57 (d, J = 5.9 Hz, 2H), 8.73 (d, J = 2.0 Hz, 1H), 8.37 (s, 1H), 8.05 (d, J = 6.1 Hz, 1H), 8.00-7.82 (m, 2H), 7.72-7.52 (m, 2H), 7.14 (t, J = 55.4 Hz, 1H), 3.16-2.93 (m, 2H), 2.15-2.01 (m, 1H), 2.00-1.86 (m, 1H). $^{19}$F NMR (376 MHz, DMSO-d6) δ −75.24 (d, J = 2.2 Hz), −110.86, −111.01. |
| 380 | 426 [M + H] | $^1$H NMR (400 MHz, DMSO-d6) δ 11.59 (dd, J = 11.6, 4.2 Hz, 2H), 8.93 (s, 2H), 8.43 (d, J = 1.6 Hz, 1H), 8.06 (d, J = 6.2 Hz, 1H), 7.99 (s, 1H), 7.72 (s, 1H), 3.03 (ddt, J = 10.2, 6.4, 3.3 Hz, 2H), 2.11 (ddd, J = 9.0, 7.1, 3.5 Hz, 1H), 1.93 (ddd, J = 8.3, 6.2, 4.2 Hz, 1H). |

TABLE 3-continued

Characterization Data

| Example No. | ES/MS m/z | NMR |
|---|---|---|
| 381 | 527.2 [M + H] | $^1$H NMR (400 MHz, Acetonitrile-d3) δ 9.21 (s, 2H), 8.03 (d, J = 6.3 Hz, 1H), 7.56 (s, 1H), 7.41 (d, J = 6.8 Hz, 1H), 7.03-6.89 (m, 3H), 4.51 (q, J = 9.2 Hz, 2H), 2.79 (ddq, J = 19.6, 9.9, 4.6 Hz, 2H), 2.06 (dt, J = 9.1, 5.5 Hz, 1H), 1.77 (dd, J = 8.7, 5.5 Hz, 1H), 1.64 (t, J = 4.1 Hz, 4H). $^{19}$F NMR (376 MHz, Acetonitrile-d3) δ −71.20 (t, J = 9.2 Hz), −77.29, −157.06 (d, J = 6.8 Hz). |
| 382 | 509.1 [M + H] | $^1$H NMR (400 MHz, Acetonitrile-d3) δ 9.41 (s, 1H), 9.29 (s, 1H), 8.18-8.10 (m, 2H), 7.96-7.88 (m, 2H), 7.08 (s, 1H), 7.01 (dd, J = 7.8, 1.5 Hz, 1H), 6.93 (d, J = 7.7 Hz, 1H), 4.56 (q, J = 9.2 Hz, 2H), 3.04 (dt, J = 9.3, 5.3 Hz, 1H), 2.76-2.66 (m, 1H), 1.94-1.79 (m, 2H), 1.70-1.59 (m, 4H). $^{19}$F NMR (376 MHz, Acetonitrile-d3) δ −71.16 (t, J = 9.1 Hz), −77.07. |
| 383 | 531.1 [M + H] | $^1$H NMR (400 MHz, DMSO-d6) δ 11.57 (d, J = 4.8 Hz, 2H), 9.00 (d, J = 2.3 Hz, 1H), 8.71 (s, 1H), 8.53 (s, 1H), 8.41-8.33 (m, 2H), 8.18 (d, J = 8.8 Hz, 1H), 8.09-8.02 (m, 1H), 7.90 (d, J = 8.1 Hz, 2H), 7.64 (s, 1H), 7.31-7.24 (m, 1H), 3.05 (t, J = 7.3 Hz, 1H), 2.87 (dt, J = 9.5, 5.1 Hz, 1H), 2.18 (dt, J = 10.6, 5.5 Hz, 1H), 1.95 (dt, J = 10.8, 5.5 Hz, 1H). $^{19}$F NMR (376 MHz, DMSO-d6) δ −60.88, −75.17. |
| 384 | 523.1 [M + H] | $^1$H NMR (400 MHz, Acetonitrile-d3) δ 9.31 (s, 1H), 9.25 (s, 1H), 8.16-8.02 (m, 2H), 7.88 (d, J = 1.8 Hz, 1H), 7.82 (s, 1H), 7.55 (d, J = 7.6 Hz, 1H), 7.07 (dd, J = 7.7, 1.6 Hz, 1H), 6.91 (s, 1H), 4.51-4.29 (m, 2H), 2.97-2.85 (m, 1H), 2.80-2.66 (m, 1H), 2.60-2.46 (m, 2H), 2.45-2.17 (m, 4H), 1.90-1.73 (m, 2H). $^{19}$F NMR (376 MHz, Acetonitrile-d3) δ −71.20 (t, J = 9.1 Hz), −76.96. |
| 385 | 555.2 [M + H] | $^1$H NMR (400 MHz, Acetonitrile-d3) δ 9.18 (s, 2H), 8.03 (d, J = 6.3 Hz, 1H), 7.55 (s, 1H), 7.41 (d, J = 6.8 Hz, 1H), 7.25 (d, J = 7.7 Hz, 1H), 7.00 (dd, J = 7.7, 1.5 Hz, 1H), 6.91 (s, 1H), 4.43 (q, J = 9.2 Hz, 2H), 2.87-2.65 (m, 2H), 2.05 (ddt, J = 13.1, 8.7, 4.5 Hz, 7H), 1.90-1.83 (m, 2H), 1.83-1.65 (m, 1H). $^{19}$F NMR (376 MHz, Acetonitrile-d3) δ −71.20 (t, J = 9.1 Hz), −77.30, −157.08 (d, J = 6.9 Hz). |
| 386 | 541.2 [M + H] | $^1$H NMR (400 MHz, Acetonitrile-d3) δ 9.19 (s, 2H), 8.03 (d, J = 6.4 Hz, 1H), 7.55 (d, J = 9.0 Hz, 2H), 7.41 (d, J = 6.8 Hz, 1H), 7.05 (dd, J = 7.7, 1.5 Hz, 1H), 6.88 (s, 1H), 4.41 (q, J = 9.2 Hz, 2H), 2.87-2.68 (m, 2H), 2.62-2.46 (m, 2H), 2.47-2.17 (m, 4H), 2.07 (dt, J = 8.9, 5.6 Hz, 1H), 1.86-1.69 (m, 1H). $^{19}$F NMR (376 MHz, Acetonitrile-d3) δ −71.20 (t, J = 9.1 Hz), −77.29, −157.04 (d, J = 6.8 Hz). |
| 387 | 537.1 [M + H] | $^1$H NMR (400 MHz, Acetonitrile-d3) δ 9.33 (s, 1H), 9.26 (s, 1H), 8.16-8.07 (m, 2H), 7.93-7.83 (m, 2H), 7.25 (d, J = 7.7 Hz, 1H), 7.06-6.98 (m, 1H), 6.96 (s, 1H), 4.45 (q, J = 9.2 Hz, 2H), 2.92-2.85 (m, 1H), 2.69 (d, J = 6.4 Hz, 1H), 2.04 (dd, J = 10.4, 6.1 Hz, 5H), 1.93-1.82 (m, 5H). $^{19}$F NMR (376 MHz, Acetonitrile-d3) δ −71.18 (t, J = 9.2 Hz), −77.04. |
| 388 | 543.1 [M + H] | $^1$H NMR (400 MHz, DMSO-d6) δ 11.58-11.50 (m, 2H), 8.04 (d, J = 6.1 Hz, 1H), 7.85 (s, 1H), 7.56 (s, 1H), 7.18 (s, 1H), 7.03-6.93 (m, 2H), 4.70 (q, J = 9.4 Hz, 2H), 2.88 (ddd, J = 9.0, 6.3, 4.3 Hz, 1H), 2.74 (ddd, J = 8.8, 5.9, 4.4 Hz, 1H), 2.11 (dt, J = 8.9, 5.2 Hz, 1H), 1.87-1.74 (m, 1H), 1.66 (q, J = 4.0, 3.1 Hz, 2H), 1.58 (q, J = 4.7, 3.8 Hz, 2H). $^{19}$F NMR (376 MHz, DMSO-d6) δ −69.25 (t, J = 9.4 Hz), −75.25. |
| 389 | 496.1 [M + H] | $^1$H NMR (400 MHz, Acetonitrile-d3) δ 9.34 (d, J = 24.1 Hz, 2H), 8.23 (d, J = 1.5 Hz, 1H), 8.12 (d, J = 6.0 Hz, 1H), 8.05 (d, J = 2.0 Hz, 1H), 7.84 (s, 1H), 7.26 (s, 1H), 7.15-6.80 (m, 2H), 5.90 (q, J = 7.9, 5.8 Hz, 1H), 4.55-4.46 (m, 3H), 4.15 (dt, J = 12.1, 2.7 Hz, 1H). $^{19}$F NMR (376 MHz, Acetonitrile-d3) δ −77.27 (d, J = 4.7 Hz), −109.77 (d, J = 240.3 Hz), −119.60 (ddd, J = 53.8, 40.3, 5.0 Hz), −122.22 (d, J = 241.8 Hz), −144.87 (t, J = 5.2 Hz). |
| 390 | 464.2 [M + H] | $^1$H NMR (400 MHz, Acetonitrile-d3) δ 9.34 (d, J = 14.9 Hz, 2H), 8.15-8.07 (m, 1H), 8.05 (dd, J = 4.2, 1.6 Hz, 2H), 7.83 (t, J = 3.5 Hz, 1H), 7.25 (s, 1H), 6.95 (dd, J = 5.5, 1.3 Hz, 1H), 5.42 (tt, J = 5.0, 2.5 Hz, 1H), 4.56-4.35 (m, 3H), 4.35-4.17 (m, 1H). $^{19}$F NMR (376 MHz, Acetonitrile-d3) δ −70.42 (d, J = 23.2 Hz), −77.23, −108.15 (dtd, J = 243.9, 20.3, 8.0 Hz), −120.09−124.78 (m), −154.77 (ddd, J = 23.1, 5.4, 2.7 Hz). |
| 391 | 509.10 [M + H] | $^1$H NMR (400 MHz, Acetonitrile-d3) δ 9.27 (s, 1H), 9.18 (s, 1H), 7.99 (d, J = 9.3 Hz, 2H), 7.67 (s, 1H), 7.49 (s, 1H), 6.99 (d, J = 8.2 Hz, 2H), 6.92 (d, J = 7.6 Hz, 1H), 4.50 (q, J = 9.2 Hz, 2H), 2.91-2.81 (m, 1H), 2.76 (dt, J = 10.2, 5.5 Hz, 1H), 2.11 (dt, J = 8.9, 5.5 Hz, 1H), 1.73 (dt, J = 8.6, 5.5 Hz, 1H), 1.63 (t, J = 3.8 Hz, 4H), 1.30 (s, 1H). $^{19}$F NMR (376 MHz, Acetonitrile-d3) δ −71.19 (t, J = 9.2 Hz) |
| 392 | 486.20 [M + H] | $^1$H NMR (400 MHz, DMSO-d6) δ 11.57 (dd, J = 10.2, 4.1 Hz, 2H), 9.27 (s, 1H), 8.35 (d, J = 1.4 Hz, 1H), 8.13 (s, 1H), 8.05 (d, J = 6.1 Hz, 1H), 7.91 (d, J = 2.4 Hz, 1H), 7.85 (d, J = 1.4 Hz, 1H), 7.68 (s, |

TABLE 3-continued

Characterization Data

| Example No. | ES/MS m/z | NMR |
|---|---|---|
| | | 1H), 5.33 (q, J = 8.9 Hz, 2H), 3.39 (dt, J = 9.5, 5.5 Hz, 1H), 3.00 (ddd, J = 9.2, 6.2, 4.3 Hz, 1H), 2.35-2.26 (m, 1H), 2.14-2.04 (m, 1H). $^{19}$F NMR (376 MHz, DMSO-d6) δ −70.74 (t, J = 9.0 Hz), −75.24 (d, J = 2.8 Hz). |
| 393 | 486.2 [M + H] | $^1$H NMR (400 MHz, DMSO-d6) δ 11.65 (dd, J = 34.2, 4.1 Hz, 2H), 8.51 (s, 1H), 8.17-8.08 (m, 2H), 7.89-7.66 (m, 3H), 7.21 (dd, J = 8.5, 1.2 Hz, 1H), 5.34 (q, J = 9.0 Hz, 2H), 3.07-2.90 (m, 2H), 2.09-1.93 (m, 2H). $^{19}$F NMR (376 MHz, DMSO-d6) δ −70.24 (t, J = 9.0 Hz), −133.85. |
| 394 | 465.10 [M + H] | $^1$H NMR (400 MHz, DMSO-d6) δ 11.60 (d, J = 10.1 Hz, 2H), 9.06 (dd, J = 4.3, 1.5 Hz, 1H), 8.51-8.40 (m, 2H), 8.21 (s, 1H), 8.08 (d, J = 6.1 Hz, 1H), 8.06-7.97 (m, 2H), 7.76-7.67 (m, 2H), 3.15 (dt, J = 9.7, 5.6 Hz, 1H), 3.00 (dt, J = 9.6, 5.4 Hz, 1H), 2.20 (dt, J = 9.9, 5.7 Hz, 1H), 2.10 (dt, J = 8.7, 5.7 Hz, 1H). $^{19}$F NMR (376 MHz, DMSO-d6) δ −58.50, −75.27 (d, J = 4.6 Hz). |
| 395 | 465.10 [M + H] | $^1$H NMR (400 MHz, DMSO-d6) δ 11.64-11.56 (m, 2H), 9.05 (d, J = 2.3 Hz, 1H), 8.40 (dd, J = 16.9, 2.0 Hz, 2H), 8.28-8.21 (m, 1H), 8.11 (dd, J = 25.4, 6.7 Hz, 2H), 7.98 (s, 1H), 7.80-7.71 (m, 2H), 3.06 (dt, J = 9.4, 5.6 Hz, 1H), 3.01-2.91 (m, 1H), 2.24 (dt, J = 9.3, 5.5 Hz, 1H), 2.07 (dt, J = 8.5, 5.5 Hz, 1H). $^{19}$F NMR (376 MHz, DMSO-d6) δ −59.17, −75.30 (d, J = 5.4 Hz). |
| 396 | 510.20 [M + H] | $^1$H NMR (400 MHz, DMSO-d6) δ 11.56 (d, J = 4.9 Hz, 2H), 8.35 (d, J = 1.5 Hz, 1H), 8.04 (d, J = 6.3 Hz, 1H), 7.88 (s, 1H), 7.77 (d, J = 8.4 Hz, 1H), 7.62 (d, J = 16.2 Hz, 2H), 7.07 (dd, J = 8.4, 1.4 Hz, 1H), 5.31 (q, J = 9.1 Hz, 2H), 3.35 (h, J = 6.9 Hz, 1H), 2.98 (ddd, J = 9.2, 6.3, 4.3 Hz, 1H), 2.84-2.75 (m, 1H), 2.11 (dq, J = 12.5, 4.5, 3.7 Hz, 1H), 1.97-1.87 (m, 1H), 1.37 (d, J = 7.0 Hz, 6H). $^{19}$F NMR (376 MHz, DMSO-d6) δ −69.99 (t, J = 9.1 Hz), −75.16 |
| 397 | 371.1 [M + H] | $^1$H NMR (400 MHz, DMSO-d6) δ 11.51-11.34 (m, 2H), 8.10 (d, J = 1.2 Hz, 1H), 7.94 (d, J = 6.1 Hz, 1H), 7.60 (d, J = 1.2 Hz, 1H), 6.61 (s, 1H), 4.93-4.71 (m, 4H). $^{19}$F NMR (376 MHz, DMSO-d6) δ −75.26, −82.92 (d, J = 7.5 Hz), −172.25--172.66 (m). |
| 398 | 325.2 [M + H] | $^1$H NMR (400 MHz, DMSO-d6) δ 11.39 (d, J = 7.6 Hz, 2H), 8.08 (s, 1H), 7.94 (d, J = 6.0 Hz, 1H), 7.66 (s, 1H), 6.52 (s, 1H), 4.34 (s, 4H), 2.23 (t, J = 7.6 Hz, 4H), 1.82 (p, J = 7.6 Hz, 2H). |
| 399 | 349.2 [M + H] | $^1$H NMR (400 MHz, DMSO-d6) δ 11.53-11.22 (m, 2H), 8.04 (d, J = 1.3 Hz, 1H), 7.92 (d, J = 6.1 Hz, 1H), 7.57 (d, J = 1.2 Hz, 1H), 6.48 (s, 1H), 6.33 (t, J = 56.4 Hz, 1H), 4.38 (br s, 2H), 4.11 (br s, 2H), 1.41 (s, 3H). $^{19}$F NMR (376 MHz, DMSO-d6) δ −75.21 (d, J = 2.9 Hz), −129.98 (d, J = 56.3 Hz). |
| 400 | 361.1 [M + H] | $^1$H NMR (400 MHz, DMSO-d6) δ 11.47-11.32 (m, 2H), 8.05 (d, J = 1.2 Hz, 1H), 7.94 (d, J = 6.1 Hz, 1H), 7.60 (d, J = 1.2 Hz, 1H), 6.49 (s, 1H), 4.52 (br s, 2H), 4.19 (br s, 2H), 2.84 (h, J = 7.6 Hz, 1H), 2.22 (tt, J = 11.4, 7.9 Hz, 1H), 1.63 (tdd, J = 12.3, 7.9, 4.5 Hz, 1H), 1.37 (dtd, J = 11.5, 7.7, 3.6 Hz, 1H). $^{19}$F NMR (376 MHz, DMSO-d6) δ −75.19, −126.51--127.27 (m), −141.33--142.11 (m). |
| 401 | 339.1 [M + H] | $^1$H NMR (400 MHz, DMSO-d6) δ 11.45-11.31 (m, 2H), 8.03 (s, 1H), 7.93 (d, J = 6.1 Hz, 1H), 7.57 (s, 1H), 6.45 (s, 1H), 4.40 (br s, 2H), 3.99 (br s, 2H), 2.87 (dq, J = 11.0, 4.1, 2.9 Hz, 1H), 2.66 (p, J = 8.0 Hz, 1H), 2.04 (ddd, J = 14.2, 10.5, 6.1 Hz, 2H), 1.85 (tdd, J = 18.9, 9.5, 4.6 Hz, 2H), 1.77-1.65 (m, 2H). |
| 402 | 372.1 [M + H] | $^1$H NMR (400 MHz, DMSO-d6) δ 11.72-11.57 (m, 1H), 11.51 (s, 1H), 8.47 (d, J = 6.4 Hz, 1H), 8.42 (s, 1H), 7.33 (s, 1H), 4.98 (dq, J = 22.9, 11.7 Hz, 4H). $^{19}$F NMR (376 MHz, DMSO-d6) δ −74.13, −82.62 (d, J = 7.7 Hz), −172.61. |
| 403 | 335.1 [M + H] | $^1$H NMR (400 MHz, DMSO-d6) δ 11.46-11.29 (m, 2H), 8.03 (s, 1H), 7.92 (d, J = 6.0 Hz, 1H), 7.56 (s, 1H), 6.46 (s, 1H), 6.43 (t, J = 56.3, 4.3 Hz, 1H), 4.48 (br s, 2H), 4.30 (br s, 2H). $^{19}$F NMR (376 MHz, DMSO-d6) δ −75.05, −125.00 (dd, J = 56.4, 14.8 Hz). |
| 404 | 325.2 [M + H] | $^1$H NMR (400 MHz, DMSO-d6) δ 11.52-11.30 (m, 2H), 8.05 (d, J = 4.4 Hz, 1H), 7.94 (d, J = 5.8 Hz, 1H), 7.61 (s, 1H), 6.47 (d, J = 4.4 Hz, 1H), 4.42 (br s, 2H), 4.01 (br s, 2H), 1.24-0.98 (m, 1H), 0.50 (d, J = 7.7 Hz, 2H), 0.22 (d, J = 5.0 Hz, 2H). |
| 405 | 361.2 [M + H] | $^1$H NMR (400 MHz, DMSO-d6) δ 11.50-11.28 (m, 2H), 8.06 (d, J = 1.3 Hz, 1H), 7.94 (d, J = 6.1 Hz, 1H), 7.60 (d, J = 1.3 Hz, 1H), 6.53 (s, 1H), 4.55 (d, J = 9.9 Hz, 2H), 4.33 (d, J = 9.7 Hz, 2H), 2.60-2.51 (m, 2H), 2.17-2.07 (m, 2H). $^{19}$F NMR (376 MHz, DMSO-d6) δ −75.25, −101.34. |
| 406 | 347.1 [M + H] | $^1$H NMR (400 MHz, DMSO-d6) δ 11.48-11.33 (m, 2H), 8.06 (s, 1H), 7.94 (d, J = 6.1 Hz, 1H), 7.59 (s, 1H), 6.55 (s, 1H), 4.51 (s, 4H), 1.84 (t, J = 8.9 Hz, 2H). $^{19}$F NMR (376 MHz, DMSO-d6) δ −75.22, −138.15 (t, J = 9.5 Hz). |
| 407 | 389.1 [M + H] | $^1$H NMR (400 MHz, DMSO-d6) δ 11.55 (d, J = 5.5 Hz, 2H), 8.35 (d, J = 1.5 Hz, 1H), 8.03 (d, J = 6.1 Hz, 1H), 7.93-7.86 (m, 1H), 7.83 (dd, J = 10.2, 1.6 Hz, 1H), 7.71 (dd, J = 8.0, 1.6 Hz, 1H), 7.65 (s, |

TABLE 3-continued

Characterization Data

| Example No. | ES/MS m/z | NMR |
|---|---|---|
| | | 1H), 7.49 (t, J = 7.9 Hz, 1H), 3.09-3.00 (m, 1H), 2.86 (ddd, J = 8.9, 6.1, 4.5 Hz, 1H), 2.18 (dt, J = 8.9, 5.3 Hz, 1H), 1.91 (ddd, J = 8.9, 6.3, 4.8 Hz, 1H). $^{19}$F NMR (376 MHz, DMSO-d6) δ −75.21, −117.94 (t, J = 8.9 Hz). |
| 408 | 389.1 [M + H] | $^{1}$H NMR (400 MHz, DMSO-d6) δ 11.56 (d, J = 5.9 Hz, 2H), 8.36 (d, J = 1.4 Hz, 1H), 8.03 (d, J = 6.1 Hz, 1H), 7.91 (s, 1H), 7.80 (ddd, J = 7.8, 6.1, 1.7 Hz, 1H), 7.71-7.63 (m, 2H), 7.41 (t, J = 7.8 Hz, 1H), 3.01 (dt, J = 9.1, 5.6 Hz, 1H), 2.85-2.77 (m, 1H), 2.13 (dt, J = 8.9, 5.3 Hz, 1H), 1.92-1.84 (m, 1H). $^{19}$F NMR (376 MHz, DMSO-d6) δ −75.19, −115.20. |
| 409 | 345.2 [M + H] | $^{1}$H NMR (400 MHz, DMSO-d6) δ 11.46-11.28 (m, 2H), 8.03 (s, 1H), 7.92 (d, J = 6.1 Hz, 1H), 7.56 (s, 1H), 6.45 (s, 1H), 4.41 (br s, 2H), 4.24 (br s, 2H), 3.14-2.95 (m, 1H), 1.36 (s, 3H), 1.31 (s, 3H). $^{19}$F NMR (376 MHz, DMSO-d6) δ −75.07, −152.62−−153.15 (m). |
| 410 | 314.1 [M + H] | $^{1}$H NMR (400 MHz, DMSO-d6) δ 11.81 (dd, J = 6.5, 2.0 Hz, 1H), 11.63 (d, J = 1.9 Hz, 1H), 8.59 (d, J = 1.9 Hz, 1H), 8.27 (d, J = 1.9 Hz, 1H), 8.14 (d, J = 6.3 Hz, 1H), 8.09 (s, 1H), 4.11-3.93 (m, 2H), 3.64-3.47 (m, 3H), 1.91 (ddd, J = 12.4, 4.0, 1.8 Hz, 2H), 1.77 (qd, J = 12.2, 4.3 Hz, 2H). |
| 411 | 439.1 [M + H] | $^{1}$H NMR (400 MHz, DMSO-d6) δ 11.56 (d, J = 7.6 Hz, 2H), 8.35 (d, J = 1.4 Hz, 1H), 8.11 (d, J = 8.0 Hz, 1H), 8.04 (d, J = 6.1 Hz, 1H), 7.90 (dd, J = 7.9, 1.5 Hz, 2H), 7.78 (dd, J = 8.1, 1.7 Hz, 1H), 7.64 (s, 1H), 3.06 (ddd, J = 9.1, 6.1, 4.3 Hz, 1H), 2.92 (ddd, J = 9.0, 6.1, 4.3 Hz, 1H), 2.24 (dt, J = 8.8, 5.5 Hz, 1H), 1.99 (dt, J = 8.8, 5.5 Hz, 1H). $^{19}$F NMR (376 MHz, DMSO-d6) δ −61.15, −75.21. |
| 412 | 439.1 [M + H] | $^{1}$H NMR (400 MHz, DMSO-d6) δ 11.54 (s, 2H), 8.31 (s, 1H), 8.09 (d, J = 1.6 Hz, 1H), 8.02 (d, J = 6.4 Hz, 1H), 7.93 (d, J = 8.4 Hz, 1H), 7.88-7.78 (m, 2H), 7.60 (s, 1H), 3.07-3.00 (m, 1H), 2.90 (ddd, J = 8.9, 6.2, 4.4 Hz, 1H), 2.25 (dt, J = 8.8, 5.4 Hz, 1H), 1.94 (dt, J = 8.8, 5.5 Hz, 1H). $^{19}$F NMR (376 MHz, DMSO-d6) δ −60.80, −75.02. |
| 413 | 455.1 [M + H] | $^{1}$H NMR (400 MHz, DMSO-d6) δ 11.56 (d, J = 6.6 Hz, 2H), 8.35 (d, J = 1.4 Hz, 1H), 8.03 (d, J = 6.0 Hz, 1H), 7.99 (d, J = 8.1 Hz, 1H), 7.92-7.83 (m, 1H), 7.68-7.58 (m, 2H), 7.51 (dd, J = 8.2, 1.6 Hz, 1H), 3.03 (ddd, J = 9.0, 6.2, 4.3 Hz, 1H), 2.89 (ddd, J = 9.0, 6.3, 4.3 Hz, 1H), 2.22 (dt, J = 9.0, 5.6 Hz, 1H), 1.92 (dt, J = 8.8, 5.4 Hz, 1H). $^{19}$F NMR (376 MHz, DMSO-d6) δ −57.52, −75.23. |
| 414 | 455.1 [M + H] | $^{1}$H NMR (400 MHz, DMSO-d6) δ 11.69-11.45 (m, 2H), 8.37 (d, J = 1.5 Hz, 1H), 8.05 (d, J = 6.1 Hz, 1H), 7.97 (d, J = 2.4 Hz, 1H), 7.92 (d, J = 1.5 Hz, 1H), 7.79 (dd, J = 8.8, 2.4 Hz, 1H), 7.64 (d, J = 7.2 Hz, 2H), 2.93 (ddd, J = 9.0, 6.2, 4.3 Hz, 1H), 2.84 (ddd, J = 8.9, 6.1, 4.4 Hz, 1H), 2.15 (dt, J = 8.8, 5.5 Hz, 1H), 1.90 (dt, J = 8.8, 5.5 Hz, 1H). $^{19}$F NMR (376 MHz, DMSO-d6) δ −57.81, −75.22. |
| 415 | 407.1 [M + H] | $^{1}$H NMR (400 MHz, DMSO-d6) δ 11.54 (d, J = 4.2 Hz, 2H), 8.02 (d, J = 6.4 Hz, 1H), 7.84 (dd, J = 8.1, 7.1 Hz, 1H), 7.55 (d, J = 7.1 Hz, 1H), 7.52 (s, 1H), 7.48 (dd, J = 11.1, 1.6 Hz, 1H), 7.34 (dd, J = 8.1, 1.6 Hz, 1H), 2.99 (dt, J = 9.4, 5.4 Hz, 1H), 2.83 (ddd, J = 8.9, 6.2, 4.3 Hz, 1H), 2.27 (dt, J = 8.8, 6.2, 4.9 Hz, 1H), 1.87 (dt, J = 8.8, 5.3 Hz, 1H). $^{19}$F NMR (376 MHz, DMSO-d6) δ −75.24, −109.46 (dd, J = 11.1, 7.0 Hz), −155.57 (d, J = 7.0 Hz). |
| 416 | 383.1 [M + H] | $^{1}$H NMR (400 MHz, DMSO-d6) δ 11.76 (d, J = 6.2 Hz, 1H), 11.59 (d, J = 1.9 Hz, 1H), 8.61 (s, 1H), 8.50 (d, J = 6.4 Hz, 1H), 8.04 (s, 1H), 7.45 (td, J = 8.8, 6.4 Hz, 1H), 7.25 (ddd, J = 10.7, 9.2, 2.6 Hz, 1H), 7.10 (td, J = 8.6, 2.5 Hz, 1H), 2.99 (dt, J = 8.9, 5.6 Hz, 1H), 2.79 (dt, J = 9.3, 6.0 Hz, 1H), 1.92 (ddt, J = 23.8, 8.7, 5.6 Hz, 2H). $^{19}$F NMR (376 MHz, DMSO-d6) δ −112.84 (ddd, J = 15.4, 8.6, 6.4 Hz), −115.28 (td, J = 9.9, 7.1 Hz). |
| 417 | 415.1 [M + H] | $^{1}$H NMR (400 MHz, Methanol-d4) δ 8.72 (s, 1H), 8.51 (s, 1H), 8.17 (s, 1H), 7.65 (d, J = 8.2 Hz, 2H), 7.53 (d, J = 8.2 Hz, 2H), 3.30-3.23 (m, 2H), 2.95-2.81 (m, 1H), 2.18-2.05 (m, 1H), 2.00-1.90 (m, 2H). $^{19}$F NMR (376 MHz, Methanol-d4) δ −64.48, −77.54. |
| 418 | 396.1 [M + H] | $^{1}$H NMR (400 MHz, DMSO-d6) δ 11.56 (d, J = 6.3 Hz, 2H), 8.35 (d, J = 1.5 Hz, 1H), 8.03 (d, J = 6.1 Hz, 1H), 7.92-7.86 (m, 1H), 7.60 (s, 1H), 7.52 (d, J = 8.0 Hz, 2H), 7.40 (d, J = 8.0 Hz, 2H), 7.01 (t, J = 56.0 Hz, 1H), 2.86 (ddd, J = 9.0, 6.3, 4.4 Hz, 1H), 2.79 (ddd, J = 8.8, 6.0, 4.4 Hz, 1H), 2.12-2.04 (m, 1H), 1.82 (ddd, J = 8.7, 6.3, 4.9 Hz, 1H). $^{19}$F NMR (376 MHz, DMSO-d6) δ −75.13, −109.27 (d, J = 56.1 Hz). |
| 419 | 414.1 [M + H] | $^{1}$H NMR (400 MHz, DMSO-d6) δ 11.53 (d, J = 3.1 Hz, 2H), 8.02 (d, J = 6.3 Hz, 1H), 7.54 (d, J = 7.0 Hz, 1H), 7.53-7.45 (m, 3H), 7.39 (d, J = 8.0 Hz, 2H), 7.00 (t, J = 56.0 Hz, 1H), 2.89 (dt, J = 9.4, 5.6 Hz, 1H), 2.78-2.69 (m, 1H), 2.13 (dt, J = 8.8, 5.3 Hz, 1H), 1.79 (dq, J = 12.9, 4.9, 4.4 Hz, 1H). $^{19}$F NMR (376 MHz, DMSO-d6) δ −75.47, −109.28 (d, J = 56.1 Hz), −155.56 (d, J = 7.0 Hz). |

TABLE 3-continued

Characterization Data

| Example No. | ES/MS m/z | NMR |
|---|---|---|
| 420 | 364.1 [M + H] | $^1$H NMR (400 MHz, DMSO-d6) δ 11.62 (d, J = 6.5 Hz, 1H), 11.50 (d, J = 1.9 Hz, 1H), 8.47 (d, J = 6.4 Hz, 1H), 8.37 (s, 1H), 7.39 (s, 1H), 4.56 (t, J = 13.5 Hz, 2H), 3.89 (s, 2H), 1.22 (s, 6H). $^{19}$F NMR (376 MHz, DMSO-d6) δ −74.24, −115.21 (t, J = 13.6 Hz). |
| 421 | 363.1 [M + H] | $^1$H NMR (400 MHz, DMSO-d6) δ 12.03-11.81 (m, 1H), 11.64 (s, 1H), 8.47 (d, J = 4.8 Hz, 1H), 8.23 (d, J = 2.8 Hz, 1H), 8.01 (d, J = 2.7 Hz, 1H), 7.67 (s, 1H), 4.58 (t, J = 13.1 Hz, 2H), 3.82 (s, 2H), 1.24 (s, 6H). $^{19}$F NMR (376 MHz, DMSO-d6) δ −74.15, −115.51 (t, J = 13.2 Hz). |
| 422 | 395.1 [M + H] | $^1$H NMR (400 MHz, DMSO-d6) δ 11.42 (d, J = 2.0 Hz, 1H), 11.38 (dd, J = 6.1, 2.1 Hz, 1H), 7.94 (d, J = 6.1 Hz, 1H), 6.55 (s, 1H), 4.37 (br s, 2H), 3.83 (br s, 2H), 2.32 (s, 3H), 1.20 (s, 6H). $^{19}$F NMR (376 MHz, DMSO-d6) δ −75.17, −115.45, −158.59. |
| 423 | 333.2 [M + H] | $^1$H NMR (400 MHz, DMSO-d6) δ 11.45-11.35 (m, 2H), 8.08 (d, J = 1.3 Hz, 1H), 7.95 (d, J = 6.1 Hz, 1H), 7.61 (d, J = 1.2 Hz, 1H), 6.55 (s, 1H), 4.52 (d, J = 15.6 Hz, 2H), 4.39 (dd, J = 20.6, 10.6 Hz, 2H), 3.80-3.72 (m, 3H). $^{19}$F NMR (376 MHz, DMSO-d6) δ −75.32, −157.16 (tt, J = 21.0, 18.4 Hz). |
| 424 | 407.1 [M + H] | $^1$H NMR (400 MHz, DMSO-d6) δ 11.55 (d, J = 5.7 Hz, 2H), 8.35 (d, J = 1.4 Hz, 1H), 8.03 (d, J = 6.1 Hz, 1H), 7.87 (s, 1H), 7.82-7.77 (m, 2H), 7.66 (s, 1H), 3.02 (dt, J = 8.9, 5.6 Hz, 1H), 2.95 (ddd, J = 9.3, 6.6, 4.9 Hz, 1H), 2.16 (dt, J = 10.2, 5.5 Hz, 1H), 1.95 (ddd, J = 8.8, 6.6, 4.8 Hz, 1H). $^{19}$F NMR (376 MHz, DMSO-d6) δ −75.17, −112.26 (d, J = 8.2 Hz). |
| 425 | 425.1 [M + H] | $^1$H NMR (400 MHz, DMSO-d6) δ 11.54 (d, J = 4.6 Hz, 2H), 8.03 (d, J = 6.3 Hz, 1H), 7.82-7.75 (m, 2H), 7.58-7.52 (m, 2H), 3.04-2.95 (m, 2H), 2.19 (dt, J = 9.9, 5.3 Hz, 1H), 1.92 (ddd, J = 8.9, 6.6, 4.7 Hz, 1H). $^{19}$F NMR (376 MHz, DMSO-d6) δ −75.38, −112.20 (d, J = 7.6 Hz), −155.57 (d, J = 7.1 Hz). |
| 426 | 364.1 [M + H] | $^1$H NMR (400 MHz, DMSO-d6) δ 11.47 (d, J = 5.4 Hz, 2H), 8.44 (s, 1H), 8.05 (d, J = 5.3 Hz, 1H), 6.98 (s, 1H), 4.39 (br s, 2H), 3.86 (br s, 2H), 1.21 (s, 6H). $^{19}$F NMR (376 MHz, DMSO-d6) δ −115.17. |
| 427 | 415.1 [M + H] | $^1$H NMR (400 MHz, DMSO-d6) δ 11.60 (d, J = 7.9 Hz, 2H), 8.61 (s, 1H), 8.12 (d, J = 6.1 Hz, 1H), 7.97 (s, 1H), 7.67 (d, J = 8.1 Hz, 2H), 7.51 (d, J = 8.1 Hz, 2H), 3.03 (ddd, J = 9.1, 6.2, 4.4 Hz, 1H), 2.80 (ddd, J = 9.0, 6.0, 4.4 Hz, 1H), 2.25 (dt, J = 8.9, 5.3 Hz, 1H), 1.87 (dt, J = 8.7, 5.3 Hz, 1H). $^{19}$F NMR (376 MHz, DMSO-d6) δ −61.26. |
| 428 | 408.1 [M + H] | $^1$H NMR (400 MHz, DMSO-d6) δ 11.59 (d, J = 10.2 Hz, 2H), 8.62 (s, 1H), 8.12 (d, J = 6.1 Hz, 1H), 8.03 (s, 1H), 7.80 (d, J = 7.2 Hz, 2H), 3.02 (ddt, J = 13.4, 8.8, 5.4 Hz, 2H), 2.23 (dt, J = 10.4, 5.2 Hz, 1H), 2.00-1.90 (m, 1H). $^{19}$F NMR (376 MHz, DMSO-d6) δ −112.04 (d, J = 7.6 Hz). |
| 429 | 384.1 [M + H] | $^1$H NMR (400 MHz, DMSO-d6) δ 11.45 (d, J = 6.7 Hz, 2H), 8.42 (s, 1H), 8.05 (d, J = 6.0 Hz, 1H), 6.99 (s, 1H), 5.32 (dq, J = 6.0, 3.6, 2.9 Hz, 1H), 4.13 (br s, 1H), 3.79 (br s, 1H), 3.42-3.25 (m, 2H), 2.44-2.27 (m, 2H). $^{19}$F NMR (376 MHz, DMSO-d6) δ −57.32. |
| 430 | 469.2 [M + H] | $^1$H NMR (400 MHz, DMSO-d6) δ 11.65-11.49 (m, 2H), 8.60 (s, 1H), 8.14 (d, J = 0.9 Hz, 1H), 8.11 (d, J = 6.1 Hz, 1H), 7.93 (s, 1H), 7.75 (d, J = 8.7 Hz, 1H), 7.69 (d, J = 1.5 Hz, 1H), 7.40 (dd, J = 8.8, 1.7 Hz, 1H), 5.43 (q, J = 9.1 Hz, 2H), 3.03 (ddd, J = 9.1, 6.4, 4.4 Hz, 1H), 2.73 (ddd, J = 8.7, 5.8, 4.4 Hz, 1H), 2.17 (dt, J = 9.0, 5.2 Hz, 1H), 1.86 (ddd, J = 8.8, 6.5, 4.9 Hz, 1H). $^{19}$F NMR (376 MHz, DMSO-d6) δ −70.16 (t, J = 9.2 Hz). |
| 431 | 469.2 [M + H] | $^1$H NMR (400 MHz, DMSO-d6) δ 11.67-11.47 (m, 2H), 8.61 (s, 1H), 8.15 (d, J = 0.8 Hz, 1H), 8.12 (d, J = 6.1 Hz, 1H), 7.96 (s, 1H), 7.76-7.70 (m, 2H), 7.13 (dd, J = 8.5, 1.2 Hz, 1H), 5.40 (q, J = 9.2 Hz, 2H), 3.09 (ddd, J = 9.0, 6.3, 4.4 Hz, 1H), 2.79 (ddd, J = 8.8, 5.8, 4.3 Hz, 1H), 2.23 (dt, J = 8.9, 5.2 Hz, 1H), 1.92 (ddd, J = 8.8, 6.4, 4.8 Hz, 1H). $^{19}$F NMR (376 MHz, DMSO-d6) δ −70.08 (t, J = 9.1 Hz). |
| 432 | 497.1 [M + H] | $^1$H NMR (400 MHz, DMSO-d6) δ 11.48 (d, J = 4.7 Hz, 2H), 8.70 (dt, J = 2.1, 1.0 Hz, 1H), 8.46 (s, 1H), 8.19 (dd, J = 8.7, 2.6 Hz, 1H), 8.06 (d, J = 6.3 Hz, 1H), 7.20 (d, J = 8.8 Hz, 1H), 7.04 (s, 1H), 6.04 (t, J = 4.3 Hz, 1H), 4.73-4.35 (m, 3H), 4.20 (s, 1H). $^{19}$F NMR (376 MHz, DMSO-d6) δ −60.56, −108.00 (d, J = 241.1 Hz), −119.20 (d, J = 238.2 Hz). |
| 433 | 372.1 [M + H] | $^1$H NMR (400 MHz, DMSO-d6) δ 11.50 (s, 2H), 8.48 (s, 1H), 8.06 (d, J = 5.1 Hz, 1H), 7.00 (s, 1H), 4.86 (dq, J = 25.4, 11.8 Hz, 4H). $^{19}$F NMR (376 MHz, DMSO-d6) δ −82.83 (d, J = 7.6 Hz), −172.26−172.72 (m). |
| 434 | 514.1 [M + H] | $^1$H NMR (400 MHz, DMSO-d6) δ 11.47-11.33 (m, 2H), 8.65 (d, J = 2.4 Hz, 1H), 8.22 (dd, J = 8.8, 2.6 Hz, 1H), 8.09 (d, J = 1.3 Hz, 1H), 7.93 (d, J = 6.1 Hz, 1H), 7.61 (d, J = 1.3 Hz, 1H), 7.24 (d, J = 8.7 Hz, 1H), 6.63 (s, 1H), 4.94 (br s, 4H). $^{19}$F NMR (376 MHz, DMSO-d6) δ −60.70, −75.39, −78.68. |

TABLE 3-continued

Characterization Data

| Example No. | ES/MS m/z | NMR |
|---|---|---|
| 435 | 478.2 [M + H] | $^1$H NMR (400 MHz, DMSO-d6) δ 11.49-11.29 (m, 2H), 8.61 (s, 1H), 8.12 (dd, J = 8.8, 2.5 Hz, 1H), 8.07 (s, 1H), 7.94 (d, J = 6.0 Hz, 1H), 7.60 (s, 1H), 7.13 (d, J = 8.7 Hz, 1H), 6.58 (s, 1H), 4.87 (d, J = 23.1 Hz, 2H), 4.69 (d, J = 17.2 Hz, 2H), 4.54 (dd, J = 21.4, 10.7 Hz, 2H). $^{19}$F NMR (376 MHz, DMSO-d6) δ −60.47, −75.32, −155.75 (dt, J = 42.3, 21.3 Hz). |
| 436 | 477.1 [M + H] | $^1$H NMR (400 MHz, DMSO-d6) δ 11.50 (d, J = 6.7 Hz, 2H), 8.48 (s, 1H), 8.45 (t, J = 6.4 Hz, 1H), 8.06 (d, J = 6.0 Hz, 1H), 7.03 (s, 1H), 5.55 (s, 1H), 4.64-3.95 (m, 4H), 3.95-3.75 (m, 2H). $^{19}$F NMR (376 MHz, DMSO-d6) δ −71.98 (t, J = 9.5 Hz), −108.32 (d, J = 251.2 Hz), −119.76 (d, J = 243.5 Hz). |
| 437 | 458.2 [M + H] | $^1$H NMR (400 MHz, DMSO-d6) δ 11.48-11.26 (m, 2H), 8.22 (t, J = 6.5 Hz, 1H), 8.06 (d, J = 1.2 Hz, 1H), 7.94 (d, J = 6.1 Hz, 1H), 7.58 (d, J = 1.2 Hz, 1H), 6.54 (s, 1H), 4.70-4.36 (m, 6H), 3.82 (qd, J = 9.6, 6.3 Hz, 2H). $^{19}$F NMR (376 MHz, DMSO-d6) δ −72.03 (t, J = 9.6 Hz), −75.21, −156.20 (p, J = 20.9 Hz). |
| 438 | 426.1 [M + H] | $^1$H NMR (400 MHz, DMSO-d6) δ 11.73-11.51 (m, 2H), 8.59 (s, 1H), 8.15 (d, J = 6.2 Hz, 1H), 7.77 (s, 1H), 7.42 (d, J = 7.7 Hz, 1H), 4.87 (t, J = 12.9 Hz, 2H), 4.49 (t, J = 14.1 Hz, 2H), 3.57 (dq, J = 13.4, 6.7 Hz, 1H), 1.04 (d, J = 6.5 Hz, 6H). $^{19}$F NMR (376 MHz, DMSO-d6) δ −113.57 (p, J = 13.6 Hz). |
| 439 | 382.0 [M + H]. | $^1$H NMR (400 MHz, DMSO-d6) δ 11.59 (d, J = 7.3 Hz, 2H), 8.60 (s, 1H), 8.56 (d, J = 2.5 Hz, 1H), 8.11 (d, J = 6.1 Hz, 1H), 7.94 (s, 1H), 7.84 (dd, J = 8.4, 2.5 Hz, 1H), 7.51 (d, J = 8.3 Hz, 1H), 3.12 (ddd, J = 8.8, 5.9, 4.1 Hz, 1H), 2.96-2.88 (m, 1H), 2.17 (ddd, J = 8.7, 6.0, 4.0 Hz, 1H), 1.88 (ddd, J = 9.6, 5.9, 4.0 Hz, 1H). |
| 440 | 421.2 [M + H] | $^1$H NMR (400 MHz, DMSO-d6) δ 11.41 (d, J = 2.0 Hz, 1H), 11.37 (dd, J = 6.2, 2.0 Hz, 1H), 7.94 (d, J = 6.1 Hz, 1H), 6.55 (s, 1H), 4.38 (br s, 2H), 3.76 (br s, 2H), 2.02 (tt, J = 8.3, 5.0 Hz, 1H), 1.19 (s, 6H), 0.95 (dt, J = 8.3, 2.8 Hz, 2H), 0.92-0.84 (m, 2H). $^{19}$F NMR (376 MHz, DMSO-d6) δ −75.28, −115.44 (t, J = 13.9 Hz), −159.35. |
| 441 | 471.1 [M + H] | $^1$H NMR (400 MHz, DMSO-d6) δ 11.41 (d, J = 2.0 Hz, 1H), 11.38 (dd, J = 6.2, 2.0 Hz, 1H), 8.03 (s, 1H), 7.93 (d, J = 6.1 Hz, 1H), 6.60 (s, 1H), 4.42 (br s, 2H), 3.76 (br s, 2H), 1.40 (t, J = 3.8 Hz, 4H), 1.20 (s, 6H). $^{19}$F NMR (376 MHz, DMSO-d6) δ −68.12, −75.41, −115.39 (t, J = 13.8 Hz). |
| 442 | 325.1 [M + H] | $^1$H NMR (400 MHz, DMSO-d6) δ 11.36 (d, J = 2.1 Hz, 1H), 11.33 (d, J = 6.4 Hz, 1H), 7.99 (s, 1H), 7.91 (d, J = 6.1 Hz, 1H), 7.55 (s, 1H), 6.41 (s, 1H), 5.07 (br s, 1H), 4.36 (br s, 1H), 3.13 (q, J = 10.8, 8.7 Hz, 1H), 2.23 (d, J = 13.4 Hz, 1H), 1.89-1.74 (m, 4H), 1.55 (q, J = 10.9, 9.3 Hz, 2H). |
| 443 | 349.1 [M + H] | $^1$H NMR (400 MHz, DMSO-d6) δ 11.38 (d, J = 2.1 Hz, 1H), 11.35 (d, J = 6.8 Hz, 1H), 8.00 (d, J = 1.2 Hz, 1H), 7.92 (d, J = 6.1 Hz, 1H), 7.54 (d, J = 1.2 Hz, 1H), 6.43 (s, 1H), 6.33-5.97 (m, 1H), 4.49 (br s, 2H), 4.11 (br s, 2H), 3.08-2.97 (m, 1H), 2.30-2.21 (m, 2H). $^{19}$F NMR (376 MHz, DMSO-d6) δ −74.87, −116.56 (dt, J = 56.1, 18.3 Hz). |
| 444 | 363.1 [M + H] | $^1$H NMR (400 MHz, DMSO-d6) δ 11.46-11.23 (m, 2H), 8.03 (d, J = 1.3 Hz, 1H), 7.93 (d, J = 6.1 Hz, 1H), 7.57 (d, J = 1.3 Hz, 1H), 6.47 (s, 1H), 6.26 (tt, J = 55.8, 4.8 Hz, 1H), 4.23 (br s, 2H), 4.05 (br s, 2H), 2.28 (td, J = 18.0, 4.7 Hz, 2H), 1.43 (s, 3H). $^{19}$F NMR (376 MHz, DMSO-d6) δ −75.15, −114.55 (dt, J = 56.0, 17.9 Hz). |
| 445 | 381.1 [M + H] | $^1$H NMR (400 MHz, DMSO-d6) δ 11.39 (d, J = 2.0 Hz, 1H), 11.38-11.31 (m, 1H), 8.03 (d, J = 1.2 Hz, 1H), 7.93 (d, J = 6.1 Hz, 1H), 7.56 (d, J = 1.2 Hz, 1H), 6.47 (s, 1H), 4.27 (br s, 2H), 4.09 (br s, 2H), 2.80 (q, J = 12.0 Hz, 2H), 1.47 (s, 3H). $^{19}$F NMR (376 MHz, DMSO-d6) δ −60.86 (t, J = 11.9 Hz), −75.09. |
| 446 | 351.1 [M + H] | $^1$H NMR (400 MHz, DMSO-d6) δ 11.42-11.33 (m, 2H), 8.04 (d, J = 1.3 Hz, 1H), 7.93 (d, J = 6.1 Hz, 1H), 7.59 (d, J = 1.3 Hz, 1H), 6.46 (s, 1H), 4.36 (br s, 2H), 4.06 (br s, 2H), 2.87 (ddt, J = 10.8, 8.2, 4.2 Hz, 1H), 1.80-1.68 (m, 7H). |
| 447 | 383.1 [M + H] | $^1$H NMR (400 MHz, DMSO-d6) δ 11.40 (d, J = 7.5 Hz, 2H), 8.05 (d, J = 1.3 Hz, 1H), 7.94 (d, J = 5.9 Hz, 1H), 7.60 (d, J = 1.3 Hz, 1H), 6.50 (s, 1H), 4.69 (tt, J = 6.6, 3.7 Hz, 1H), 4.60 (t, J = 8.1 Hz, 2H), 4.28-4.13 (m, 4H). $^{19}$F NMR (376 MHz, DMSO-d6) δ −73.39 (t, J = 9.3 Hz), −75.09. |
| 448 | 375.1 [M + H] | $^1$H NMR (400 MHz, DMSO-d6) δ 11.38 (d, J = 2.0 Hz, 1H), 11.36 (dd, J = 6.2, 2.0 Hz, 1H), 8.01 (d, J = 1.2 Hz, 1H), 7.92 (d, J = 6.1 Hz, 1H), 7.55 (d, J = 1.2 Hz, 1H), 6.43 (s, 1H), 6.08 (td, J = 57.2, 4.1 Hz, 1H), 4.34 (br d, J = 36.5 Hz, 4H), 2.74-2.62 (m, 1H), 2.42-2.34 (m, 2H), 2.30-2.19 (m, 2H). $^{19}$F NMR (376 MHz, DMSO-d6) δ −74.94, −123.55 (dd, J = 57.1, 16.1 Hz). |
| 449 | 377.1 [M + H] | $^1$H NMR (400 MHz, DMSO-d6) δ 11.44-11.32 (m, 2H), 8.05 (d, J = 1.2 Hz, 1H), 7.94 (d, J = 6.1 Hz, 1H), 7.58 (d, J = 1.2 Hz, 1H), 6.51 (s, 1H), 4.56 (br s, 2H), 4.40 (d, J = 10.0 Hz, 2H), 4.10 (t, J = 13.1 |

TABLE 3-continued

Characterization Data

| Example No. | ES/MS m/z | NMR |
|---|---|---|
| | | Hz, 2H), 2.87 (t, J = 14.4 Hz, 2H) $^{19}$F NMR (376 MHz, DMSO-d6) δ −75.21, −100.84 (p, J = 13.7 Hz). |
| 450 | 411.1 [M + H] | $^1$H NMR (400 MHz, DMSO-d6) δ 11.43-11.32 (m, 2H), 8.05 (d, J = 1.3 Hz, 1H), 7.93 (d, J = 6.0 Hz, 1H), 7.59 (s, 1H), 7.43 (td, J = 8.7, 6.6 Hz, 1H), 7.22 (td, J = 9.9, 2.6 Hz, 1H), 7.05 (td, J = 8.5, 2.6 Hz, 1H), 6.48 (s, 1H), 4.43 (br s, 2H), 4.08 (br s, 2H), 3.09 (h, J = 6.9 Hz, 1H), 3.00 (d, J = 7.8 Hz, 2H). $^{19}$F NMR (376 MHz, DMSO-d6) δ −75.22, −113.33 (ddd, J = 15.7, 8.8, 6.7 Hz), −114.36 (q, J = 8.5 Hz). |
| 451 | 339.2 [M + H] | $^1$H NMR (400 MHz, DMSO-d6) δ 11.38 (d, J = 5.3 Hz, 2H), 8.05 (d, J = 1.3 Hz, 1H), 7.95 (d, J = 6.1 Hz, 1H), 7.61 (d, J = 1.3 Hz, 1H), 6.63 (s, 1H), 4.73-4.62 (m, 1H), 4.29 (t, J = 8.6 Hz, 1H), 4.18-4.12 (m, 1H), 2.91-2.80 (m, 1H), 2.06-1.85 (m, 2H), 1.85-1.51 (m, 4H), 1.51-1.34 (m, 2H). |
| 452 | 381.1 [M + H] | $^1$H NMR (400 MHz, DMSO-d6) δ 11.47-11.19 (m, 2H), 8.02 (s, 1H), 7.93 (d, J = 6.1 Hz, 1H), 7.55 (s, 1H), 6.58 (s, 1H), 3.69 (br s, 2H), 3.50 (br s, 2H), 2.57 (m, 3H), 2.28-2.15 (m, 1H), 1.78 (t, J = 10.6 Hz, 1H). $^{19}$F NMR (376 MHz, DMSO-d6) δ −63.82 (t, J = 11.3 Hz), −75.16 (d, J = 3.3 Hz). |
| 453 | 363.2 [M + H] | $^1$H NMR (400 MHz, DMSO-d6) δ 11.48-11.23 (m, 2H), 8.04 (d, J = 1.2 Hz, 1H), 7.93 (d, J = 6.1 Hz, 1H), 7.58 (d, J = 1.2 Hz, 1H), 6.59 (s, 1H), 6.21 (tt, J = 56.3, 4.4 Hz, 1H), 3.70 (br s, 2H), 3.44 (br s, 2H), 2.48-2.39 (m, 1H), 2.26-2.15 (m, 1H), 2.15-1.98 (m, 2H), 1.80-1.65 (m, 1H). $^{19}$F NMR (376 MHz, DMSO-d6) δ −75.23, −115.09 (dtd, J = 56.7, 18.6, 6.6 Hz). |
| 454 | 363.1 [M + H] | $^1$H NMR (400 MHz, DMSO-d6) δ 11.44-11.28 (m, 2H), 8.04 (d, J = 1.2 Hz, 1H), 7.94 (d, J = 6.1 Hz, 1H), 7.59 (d, J = 1.3 Hz, 1H), 6.60 (s, 1H), 6.21 (tt, J = 56.4, 4.4 Hz, 1H), 3.72 (m, 2H), 3.60-3.23 (m, 2H), 2.48-2.41 (m, 1H), 2.26-2.15 (m, 1H), 2.15-1.98 (m, 2H), 1.74 (dq, J = 12.0, 9.5 Hz, 1H). $^{19}$F NMR (376 MHz, DMSO-d6) δ −75.27, −115.09 (dtd, J = 56.5, 18.5, 5.9 Hz). |
| 455 | 405.0 [M + H] | $^1$H NMR (400 MHz, DMSO-d6) δ 11.47 (d, J = 2.1 Hz, 1H), 11.43 (dd, J = 6.2, 2.1 Hz, 1H), 7.99 (d, J = 6.1 Hz, 1H), 7.72 (s, 1H), 6.71 (s, 1H), 4.97-4.73 (m, 4H). $^{19}$F NMR (376 MHz, DMSO-d6) δ −75.15, −82.88 (d, J = 7.6 Hz), −172.18−−172.69 (m). |
| 456 | 468.1 [M + H] | $^1$H NMR (400 MHz, DMSO-d6) δ 11.62 (dd, J = 6.4, 2.0 Hz, 1H), 11.52 (d, J = 1.9 Hz, 1H), 8.35 (d, J = 6.3 Hz, 1H), 8.19-8.07 (m, 2H), 7.80-7.65 (m, 3H), 7.18 (dd, J = 8.4, 1.4 Hz, 1H), 6.63 (d, J = 2.3 Hz, 1H), 5.41 (q, J = 9.1 Hz, 2H), 3.15 (ddd, J = 8.3, 6.6, 4.5 Hz, 1H), 2.84-2.74 (m, 1H), 1.95 (ddd, J = 8.3, 6.6, 1.5 Hz, 2H). $^{19}$F NMR (376 MHz, DMSO-d6) δ −70.08 (t, J = 9.0 Hz), −75.62. |
| 457 | 423.2 [M + H] | $^1$H NMR (400 MHz, DMSO-d6) δ 11.66-11.48 (m, 2H), 8.33 (d, J = 1.3 Hz, 1H), 8.06 (d, J = 6.1 Hz, 1H), 7.88-7.80 (m, 2H), 7.46 (s, 1H), 4.75 (t, J = 12.7 Hz, 2H), 3.86-3.77 (m, 1H), 2.43-2.27 (m, 4H), 1.03 (d, J = 6.5 Hz, 6H). $^{19}$F NMR (376 MHz, DMSO-d6) δ −75.17, −105.77 (tt, J = 17.7, 12.2 Hz). |
| 458 | 463.1 [M + H] | $^1$H NMR (400 MHz, DMSO-d6) δ 11.56 (d, J = 6.1 Hz, 2H), 8.69 (t, J = 6.4 Hz, 1H), 8.31 (d, J = 1.4 Hz, 1H), 8.05 (d, J = 6.1 Hz, 1H), 7.80 (d, J = 1.4 Hz, 1H), 7.43 (s, 1H), 4.76 (t, J = 12.7 Hz, 2H), 3.91 (qd, J = 9.9, 6.3 Hz, 2H), 2.49-2.31 (m, 4H). $^{19}$F NMR (376 MHz, DMSO-d6) δ −71.26−−71.51 (m), −75.07, −106.02 (ddd, J = 26.1, 17.2, 12.4 Hz). |
| 459 | 502.2 [M + H] | $^1$H NMR (400 MHz, DMSO-d6) δ 11.55 (d, J = 3.8 Hz, 2H), 8.33 (d, J = 1.4 Hz, 1H), 8.04 (d, J = 6.4 Hz, 1H), 7.86 (s, 1H), 7.81 (s, 1H), 7.66 (d, J = 8.4 Hz, 1H), 7.60 (s, 1H), 7.25 (dd, J = 8.5, 1.2 Hz, 1H), 5.44 (q, J = 9.0 Hz, 2H), 3.04 (ddd, J = 9.3, 6.1, 4.3 Hz, 1H), 2.87-2.79 (m, 1H), 2.17 (dt, J = 9.0, 5.3 Hz, 1H), 1.93 (dt, J = 8.5, 5.2 Hz, 1H). $^{19}$F NMR (376 MHz, DMSO-d6) δ −70.17 (t, J = 9.0 Hz), −75.13. |
| 460 | 502.1 [M + H] | $^1$H NMR (400 MHz, DMSO-d6) δ 11.52 (d, J = 5.3 Hz, 2H), 8.30 (s, 1H), 8.23 (s, 1H), 8.02 (d, J = 6.1 Hz, 1H), 7.80 (s, 1H), 7.77 (s, 1H), 7.56 (s, 1H), 7.25 (s, 1H), 5.45 (q, J = 9.1 Hz, 2H), 3.04 (dt, J = 9.4, 5.4 Hz, 1H), 2.82 (dt, J = 10.0, 5.5 Hz, 1H), 2.17 (dt, J = 10.6, 5.2 Hz, 1H), 1.96-1.88 (m, 1H). $^{19}$F NMR (376 MHz, DMSO-d6) δ −70.09 (t, J = 9.1 Hz), −74.90. |
| 461 | 386.2 [M + H] | $^1$H NMR (400 MHz, DMSO-d6) δ 11.81 (dd, J = 6.2, 2.0 Hz, 1H), 11.62 (d, J = 2.0 Hz, 1H), 8.55 (d, J = 1.7 Hz, 1H), 8.20-8.07 (m, 2H), 7.97 (s, 1H), 7.76 (dt, J = 6.7, 3.3 Hz, 2H), 7.53 (dd, J = 6.1, 3.1 Hz, 2H), 3.50 (td, J = 7.4, 4.4 Hz, 1H), 3.32-3.22 (m, 1H), 2.48 (d, J = 10.8 Hz, 2H). |
| 462 | 389.1 [M + H] | (1S, 2S)-2-(6-(2, 4-dioxo-1, 2, 3, 4-tetrahydropyrimidin-5-yl)imidazo[1, 2-b]pyridazin-8-yl)-N-phenylcyclopropane-1-carboxamide |

TABLE 3-continued

Characterization Data

| Example No. | ES/MS m/z | NMR |
|---|---|---|
| 463 | 328.2 [M + H] | ¹H NMR (400 MHz, DMSO-d6) δ 11.63-11.47 (m, 2H), 8.36 (s, 1H), 8.02 (d, J = 6.1 Hz, 1H), 7.95 (s, 1H), 7.48 (s, 1H), 2.47 (d, J = 5.4 Hz, 1H), 1.78-1.67 (m, 1H), 1.41-1.31 (m, 1H), 1.27 (dd, J = 9.2, 4.7 Hz, 1H), 1.21 (s, 3H), 1.19 (s, 3H). |
| 464 | 400.1 [M + H] | ¹H NMR (400 MHz, DMSO-d6) δ 11.50 (d, J = 6.3 Hz, 2H), 8.27 (s, 1H), 8.00 (d, J = 6.0 Hz, 1H), 7.76 (s, 1H), 7.55 (s, 1H), 7.37-7.25 (m, 1H), 7.22-7.12 (m, 1H), 3.02 (dt, J = 10.3, 5.6 Hz, 1H), 2.74 (q, J = 4.4 Hz, 1H), 2.13 (dt, J = 9.9, 5.2 Hz, 1H), 1.79 (dt, J = 8.8, 5.2 Hz, 1H). ¹⁹F NMR (376 MHz, DMSO-d6) δ −74.56 (s, 3F), −138.66 (m, 1F), −141.38 (m, 1F), −162.67 (m, 1F). |
| 465 | 371.1 [M + H] | ¹H NMR (400 MHz, DMSO-d6) δ 11.55 (d, J = 6.3 Hz, 2H), 8.34 (s, 1H), 8.03 (d, J = 6.0 Hz, 1H), 7.87 (s, 1H), 7.78 (d, J = 8.2 Hz, 2H), 7.59 (s, 1H), 7.46 (d, J = 8.3 Hz, 2H), 2.95-2.86 (m, 1H), 2.83 (dt, J = 9.8, 5.4 Hz, 1H), 2.16 (dt, J = 8.7, 5.5 Hz, 1H), 1.86 (dt, J = 8.8, 5.5 Hz, 1H). |
| 466 | 389.1 [M + H] | ¹H NMR (400 MHz, DMSO-d6) δ 11.55 (d, J = 5.5 Hz, 2H), 8.36 (d, J = 1.4 Hz, 1H), 8.03 (d, J = 6.1 Hz, 1H), 7.90 (s, 1H), 7.86 (dd, J = 7.1, 2.1 Hz, 1H), 7.81 (ddd, J = 8.5, 4.8, 2.1 Hz, 1H), 7.66 (s, 1H), 7.43 (dd, J = 10.0, 8.5 Hz, 1H), 3.02 (ddd, J = 9.0, 6.2, 4.5 Hz, 1H), 2.88-2.79 (m, 1H), 2.13 (dt, J = 8.9, 5.3 Hz, 1H), 2.02-1.85 (m, 1H). ¹⁹F NMR (376 MHz, DMSO-d6) δ −75.18 (s, 3F), −110.52 (p, J = 5.4 Hz, 1F). |
| 467 | 389.1 [M + H] | ¹H NMR (400 MHz, DMSO-d6) δ 11.54 (d, J = 4.2 Hz, 2H), 8.32 (d, J = 1.4 Hz, 1H), 8.02 (d, J = 6.3 Hz, 1H), 7.90-7.81 (m, 2H), 7.59 (s, 1H), 7.47 (dd, J = 11.0, 1.6 Hz, 1H), 7.34 (dd, J = 8.1, 1.6 Hz, 1H), 2.96 (m, 1H), 2.85 (m, 1H), 2.23 (dt, J = 8.8, 5.5 Hz, 1H), 1.89 (dt, J = 8.8, 5.3 Hz, 1H). ¹⁹F NMR (376 MHz, DMSO-d6) δ −75.15 (s, 3F), −109.51 (dd, J = 11.1, 7.1 Hz, 1F). |
| 468 | 400.1 [M + H] | ¹H NMR (400 MHz, DMSO-d6) δ 11.54 (m, 2H), 8.33 (d, J = 1.4 Hz, 1H), 8.02 (d, J = 6.3 Hz, 1H), 7.85 (s, 1H), 7.63 (s, 1H), 7.41 (qd, J = 9.5, 5.0 Hz, 1H), 7.13 (tdd, J = 9.5, 4.1, 2.1 Hz, 1H), 2.99-2.89 (m, 2H), 2.12 (dt, J = 9.7, 5.3 Hz, 1H), 1.89 (ddd, J = 8.6, 6.8, 4.7 Hz, 1H). ¹⁹F NMR (376 MHz, DMSO-d6) δ −75.03 (s, 3F), −119.95 (ddt, J = 14.7, 9.3, 4.3 Hz, 1F), −139.15--139.84 (m, 1F), −143.41 (dddd, J = 21.7, 14.5, 10.1, 4.1 Hz, 1F). |
| 469 | 382.1 [M + H] | ¹H NMR (400 MHz, DMSO-d6) δ 11.64-11.54 (m, 1H), 11.50 (d, J = 2.0 Hz, 1H), 8.33 (d, J = 6.4 Hz, 1H), 8.20 (d, J = 2.3 Hz, 1H), 7.69 (s, 1H), 7.46 (td, J = 8.8, 6.5 Hz, 1H), 7.24 (ddd, J = 10.7, 9.3, 2.6 Hz, 1H), 7.15-7.03 (m, 1H), 6.65 (d, J = 2.3 Hz, 1H), 3.06 (ddd, J = 8.8, 6.1, 4.7 Hz, 1H), 2.71-2.61 (m, 1H), 1.93-1.77 (m, 2H). ¹⁹F NMR (376 MHz, DMSO-d6) δ −75.08 (s, 3F), −113.08 (ddd, J = 15.2, 8.8, 6.4 Hz, 1F), −115.44 (td, J = 9.8, 7.0 Hz, 1F). |
| 470 | 502.10 [M + H] | ¹H NMR (400 MHz, DMSO-d6) δ 11.63-11.49 (m, 2H), 8.15 (s, 1H), 8.04 (d, J = 6.0 Hz, 1H), 7.84 (s, 1H), 7.77-7.67 (m, 2H), 7.59 (s, 1H), 7.12 (dd, J = 8.5, 1.1 Hz, 1H), 5.40 (q, J = 9.1 Hz, 2H), 3.01 (ddd, J = 9.0, 6.2, 4.3 Hz, 1H), 2.81 (ddd, J = 8.9, 5.9, 4.4 Hz, 1H), 2.16 (dt, J = 8.8, 5.2 Hz, 1H), 1.95-1.84 (m, 1H). ¹⁹F NMR (376 MHz, DMSO-d6) δ −70.08 (t, J = 9.2 Hz, 3F), −75.40 (s, 3F). |
| 471 | 503.10 [M + H] | ¹H NMR (400 MHz, DMSO-d6) δ 11.58-11.51 (m, 2H), 9.14 (s, 1H), 8.46 (s, 1H), 8.05 (d, J = 6.1 Hz, 1H), 7.93 (s, 1H), 7.85 (s, 1H), 7.63 (s, 1H), 5.46 (q, J = 9.1 Hz, 2H), 3.19 (q, J = 7.4, 6.2 Hz, 1H), 3.06 (ddd, J = 9.8, 6.0, 4.1 Hz, 1H), 2.16 (dt, J = 9.4, 5.0 Hz, 1H), 2.01 (dt, J = 9.6, 4.5 Hz, 1H). ¹⁹F NMR (376 MHz, DMSO-d6) δ −70.14 (t, J = 9.2 Hz, 3F), −74.82 (s, 3F). |
| 472 | 336.1 [M + H] | ¹H NMR (400 MHz, DMSO-d6) δ 11.71-11.57 (m, 1H), 11.51 (d, J = 2.0 Hz, 1H), 8.47 (d, J = 6.4 Hz, 1H), 8.42 (s, 1H), 7.42 (s, 1H), 5.56 (dt, J = 11.4, 4.9 Hz, 1H), 5.49-5.35 (m, 1H), 4.35 (d, J = 17.4 Hz, 2H), 4.13 (t, J = 16.5 Hz, 2H). ¹⁹F NMR (376 MHz, DMSO-d6) δ −75.17 (s, 3F), −205.98 (m, 2F). |
| 473 | 365.1 [M + H] | ¹H NMR (400 MHz, DMSO-d6) δ 11.41 (d, J = 2.0 Hz, 1H), 11.39-11.34 (m, 1H), 8.07 (d, J = 1.2 Hz, 1H), 7.93 (d, J = 6.1 Hz, 1H), 7.57 (d, J = 1.2 Hz, 1H), 6.59 (s, 1H), 4.45 (d, J = 11.6 Hz, 1H), 4.35-4.20 (m, 2H), 4.05-3.85 (m, 2H), 3.48 (s, 3H). ¹⁹F NMR (376 MHz, DMSO-d6) δ −75.14 (s, 3F), −107.10 (d, J = 234.7 Hz, 1F), −121.69 (d, J = 235.0 Hz, 1F). |
| 474 | 383.1 [M + H] | ¹H NMR (400 MHz, DMSO-d6) δ 11.43 (d, J = 2.0 Hz, 1H), 11.42-11.36 (m, 1H), 7.96 (d, J = 6.1 Hz, 1H), 7.41 (d, J = 7.2 Hz, 1H), 6.59 (s, 1H), 4.42 (s, 1H), 4.35-4.22 (m, 2H), 4.15 (s, 1H), 3.95 (s, 1H), 3.48 (s, 3H). ¹⁹F NMR (376 MHz, DMSO-d6) δ −107.22 (d, J = 237.3 Hz, 1F), −121.87 (d, J = 236.2 Hz, 1F), −155.44 (d, J = 7.3 Hz, 1F). |

TABLE 3-continued

Characterization Data

| Example No. | ES/MS m/z | NMR |
|---|---|---|
| 475 | 417.2 [M + H] | ¹H NMR (400 MHz, DMSO-d6) δ 11.42 (d, J = 3.8 Hz, 2H), 7.95 (d, J = 6.3 Hz, 1H), 7.92 (s, 1H), 6.67 (s, 1H), 4.57 (t, J = 12.4 Hz, 2H), 3.95 (s, 2H), 2.58 (d, J = 7.0 Hz, 2H), 2.03 (dq, J = 13.5, 6.7 Hz, 1H), 1.08-1.02 (m, 2H), 1.00 (t, J = 3.1 Hz, 2H), 0.93 (d, J = 6.6 Hz, 6H). ¹⁹F NMR (376 MHz, DMSO-d6) δ −107.32 (t, J = 12.5 Hz, 2F). |
| 476 | 325.2 [M + H] | ¹H NMR (400 MHz, DMSO-d6) δ 11.40 (d, J = 2.0 Hz, 1H), 11.37 (d, J = 6.4 Hz, 1H), 8.05 (d, J = 1.2 Hz, 1H), 7.95 (d, J = 6.1 Hz, 1H), 7.58 (d, J = 1.2 Hz, 1H), 6.73 (s, 1H), 4.29 (s, 2H), 3.08 (d, J = 7.1 Hz, 2H), 2.24 (dt, J = 9.6, 5.7 Hz, 2H), 1.74 (qd, J = 6.6, 3.9 Hz, 2H). |
| 477 | 343.2 [M + H] | ¹H NMR (400 MHz, DMSO-d6) δ 11.39 (d, J = 2.0 Hz, 1H), 11.36 (dd, J = 6.2, 2.0 Hz, 1H), 8.03 (d, J = 1.2 Hz, 1H), 7.94 (d, J = 6.1 Hz, 1H), 7.59 (d, J = 1.3 Hz, 1H), 6.69 (s, 1H), 5.04 (s, 1H), 3.79 (s, 1H), 3.57 (dd, J = 9.5, 3.7 Hz, 1H), 3.39 (dd, J = 9.4, 7.5 Hz, 1H), 3.33-3.22 (m, 4H), 2.15-1.70 (m, 4H). |
| 478 | 343.2 [M + H] | ¹H NMR (400 MHz, DMSO-d6) δ 11.45-11.30 (m, 2H), 8.10 (d, J = 1.3 Hz, 1H), 7.96 (d, J = 6.1 Hz, 1H), 7.63 (d, J = 1.3 Hz, 1H), 6.70 (s, 1H), 4.50 (t, J = 15.5 Hz, 1H), 3.88 (dd, J = 11.5, 6.4 Hz, 1H), 3.24 (ddt, J = 23.4, 15.5, 7.3 Hz, 1H), 2.48-2.31 (m, 2H), 2.22-2.06 (m, 1H), 1.34 (p, J = 9.7 Hz, 1H). |
| 479 | 349.2 [M + H] | ¹H NMR (400 MHz, DMSO-d6) δ 11.41 (d, J = 1.9 Hz, 1H), 11.40-11.30 (m, 1H), 8.06 (d, J = 1.2 Hz, 1H), 7.94 (d, J = 6.1 Hz, 1H), 7.58 (d, J = 1.2 Hz, 1H), 6.60 (s, 1H), 4.53-4.17 (m, 4H), 2.85 (dq, J = 17.7, 8.9, 8.1 Hz, 1H), 1.15 (d, J = 6.9 Hz, 3H). |
| 480 | 314.1 [M + H] | ¹H NMR (400 MHz, DMSO-d6) δ 11.45 (s, 2H), 10.83 (s, 1H), 8.13 (s, 1H), 7.98 (d, J = 6.1 Hz, 1H), 7.64 (s, 1H), 7.07 (s, 1H), 4.58 (s, 2H), 2.77-2.65 (m, 2H). |
| 481 | 321.2 [M + H] | ¹H NMR (400 MHz, DMSO-d6) δ 11.43 (d, J = 2.0 Hz, 1H), 11.40 (d, J = 6.6 Hz, 1H), 8.09 (d, J = 1.2 Hz, 1H), 7.95 (d, J = 6.1 Hz, 1H), 7.59 (d, J = 1.2 Hz, 1H), 6.60 (s, 1H), 4.79 (t, J = 12.3 Hz, 4H). |
| 482 | 436.1 [M + H] | ¹H NMR (400 MHz, DMSO-d6) δ 11.44 (d, J = 2.0 Hz, 1H), 11.40 (dd, J = 6.2, 2.0 Hz, 1H), 8.08 (d, J = 1.2 Hz, 1H), 7.96 (d, J = 6.1 Hz, 1H), 7.58 (d, J = 1.2 Hz, 1H), 7.35 (dd, J = 8.6, 5.6 Hz, 2H), 7.23-7.13 (m, 2H), 6.90 (s, 1H), 4.59 (d, J = 2.8 Hz, 4H), 4.37 (t, J = 5.4 Hz, 2H), 3.50-3.40 (m, 2H). |
| 483 | 327.2 [M + H] | ¹H NMR (400 MHz, DMSO-d6) δ 11.37 (d, J = 2.0 Hz, 1H), 11.34 (d, J = 6.6 Hz, 1H), 7.99 (d, J = 1.1 Hz, 1H), 7.94 (d, J = 6.1 Hz, 1H), 7.53 (d, J = 1.2 Hz, 1H), 6.77 (s, 1H), 4.07 (s, 4H), 1.89-1.72 (m, 4H), 1.52 (p, J = 2.7 Hz, 4H). |
| 484 | 377.1 [M + H] | ¹H NMR (400 MHz, DMSO-d6) δ 8.01 (d, J = 1.2 Hz, 1H), 7.94 (s, 1H), 7.55 (d, J = 1.2 Hz, 1H), 6.72 (s, 1H), 4.37-4.21 (m, 1H), 4.19-3.92 (m, 2H), 3.91-3.71 (m, 1H), 2.45-2.17 (m, 3H), 2.03-1.82 (m, 2H), 0.99 (d, J = 6.9 Hz, 3H). |
| 485 | 331.1 [M + H] | ¹H NMR (400 MHz, DMSO-d6) δ 11.43 (s, 1H), 11.41 (d, J = 8.1 Hz, 1H), 8.09 (s, 1H), 7.98 (d, J = 6.1 Hz, 1H), 7.66 (s, 1H), 7.43 (t, J = 4.2 Hz, 1H), 6.86 (s, 1H), 3.41-3.32 (m, 2H), 1.77 (dd, J = 8.7, 6.4 Hz, 2H), 1.18 (s, 6H). |
| 486 | 363.2 [M + H] | ¹H NMR (400 MHz, DMSO-d6) δ 11.50-11.27 (m, 2H), 8.12 (d, J = 1.5 Hz, 1H), 7.96 (d, J = 6.1 Hz, 1H), 7.72 (s, 1H), 7.53 (t, J = 5.8 Hz, 1H), 7.32-7.22 (m, 4H), 7.22-7.16 (m, 1H), 6.84 (s, 1H), 3.38-3.27 (m, 2H), 2.77-2.65 (m, 2H), 1.97 (td, J = 8.6, 8.1, 6.2 Hz, 2H). |
| 487 | 349.1 [M + H] | ¹H NMR (400 MHz, DMSO-d6) δ 11.43 (s, 1H), 11.39 (d, J = 6.7 Hz, 1H), 8.05 (d, J = 1.4 Hz, 1H), 7.97 (d, J = 6.1 Hz, 1H), 7.59 (s, 1H), 7.46 (d, J = 6.2 Hz, 1H), 7.32 (d, J = 4.3 Hz, 4H), 7.23 (q, J = 4.3 Hz, 1H), 6.91 (s, 1H), 2.98 (q, J = 7.4, 7.0 Hz, 2H). |
| 488 | 475.9 [M + H] | ¹H NMR (400 MHz, DMSO-d6) δ 8.05 (d, J = 1.2 Hz, 1H), 7.94 (s, 1H), 7.57 (d, J = 1.2 Hz, 1H), 6.59 (s, 1H), 4.43 (s, 2H), 4.25 (s, 2H), 4.12-3.91 (m, 4H), 1.40 (s, 9H). |
| 489 | 417.2 [M + H] | ¹H NMR (400 MHz, DMSO-d6 + D2O) δ 8.13 (d, J = 1.5 Hz, 1H), 7.98 (s, 1H), 7.73 (s, 1H), 7.68 (s, 1H), 7.62 (d, J = 7.7 Hz, 1H), 7.60-7.49 (m, 2H), 6.96 (s, 1H), 3.62 (t, J = 7.1 Hz, 2H), 3.08 (t, J = 7.2 Hz, 2H). ¹⁹F NMR (376 MHz, DMSO-d6 + D2O) δ −61.49, −74.74. |
| 490 | 383.2 [M + H] | ¹H NMR (400 MHz, DMSO-d6 + D2O) δ 8.13 (s, 1H), 7.99 (s, 1H), 7.72 (s, 1H), 7.41 (t, J = 1.8 Hz, 1H), 7.37-7.23 (m, 3H), 6.98 (s, 1H), 3.58 (t, J = 7.4 Hz, 2H), 2.98 (t, J = 7.3 Hz, 2H). |
| 491 | 383.1 [M + H] | ¹H NMR (400 MHz, DMSO-d6 + D2O) δ 8.09 (s, 1H), 7.98 (s, 1H), 7.68 (s, 1H), 7.50-7.38 (m, 2H), 7.33-7.23 (m, 2H), 6.97 (s, 1H), 3.57 (t, J = 7.6 Hz, 2H), 3.14-3.05 (m, 2H). |
| 492 | 367.2 [M + H] | ¹H NMR (400 MHz, DMSO-d6 + D2O) δ 8.10 (s, 1H), 7.99 (s, 1H), 7.68 (s, 1H), 7.40-7.30 (m, 1H), 7.23-7.11 (m, 2H), 7.09-7.01 (m, 1H), 6.96 (s, 1H), 3.58 (t, J = 7.5 Hz, 2H), 2.99 (t, J = 7.4 Hz, 2H). ¹⁹F NMR (376 MHz, DMSO-d6 + D2O) δ −74.59, −113.99 − −114.12 (m) |

TABLE 3-continued

Characterization Data

| Example No. | ES/MS m/z | NMR |
|---|---|---|
| 493 | 367.2 [M + H] | ¹H NMR (400 MHz, DMSO-d6 + D2O) δ 8.10 (s, 1H), 7.98 (s, 1H), 7.68 (s, 1H), 7.39 (t, J = 7.7 Hz, 1H), 7.29 (q, J = 6.2 Hz, 1H), 7.21-7.10 (m, 2H), 6.94 (s, 1H), 3.57 (t, J = 7.5 Hz, 2H), 3.00 (t, J = 7.3 Hz, 2H). ¹⁹F NMR (376 MHz, DMSO-d6 + D2O) δ −74.56, −116.41- −121.72 (m). |
| 494 | 367.1 [M + H] | ¹H NMR (400 MHz, DMSO-d6 + D2O) δ − 8.11 (s, 1H), 7.98 (s, 1H), 7.69 (s, 1H), 7.56-7.36 (m, 5H), 7.00 (s, 1H), 5.96-5.75 (m, 1H), 3.97-3.73 (m, 2H). |
| 495 | 422.1 [M + H] | ¹H NMR (400 MHz, DMSO-d6 + D2O) 8 8.04 (s, 1H), 7.94 (s, 1H), 7.64-7.62 (m, 1H), 7.58 (d, J = 20.3 Hz, 2H), 7.42-7.29 (m, 3H), 7.17-7.02 (m, 1H), 6.83 (s, 1H), 3.65-3.54 (m, 2H), 3.06 (t, J = 7.3 Hz, 2H). |
| 496 | 367.2 [M + H] | ¹H NMR (400 MHz, DMSO-d6 + D2O) δ 8.07 (s, 1H), 7.98 (s, 1H), 7.64 (s, 1H), 7.34 (dd, J = 8.6, 5.6 Hz, 2H), 7.12 (t, J = 8.8 Hz, 2H), 6.91 (s, 1H), 3.53 (t, J = 7.8 Hz, 2H), 2.95 (t, J = 7.4 Hz, 2H). ¹⁹F NMR (376 MHz, DMSO-d6 + D2O) δ −74.45, −117.41. |
| 497 | 383.1 [M + H] | ¹H NMR (400 MHz, DMSO-d6 + D2O) δ 8.03 (s, 1H), 7.96 (s, 1H), 7.59 (s, 1H), 7.40-7.28 (m, 4H), 6.84 (s, 1H), 3.54 (s, 2H), 2.95 (t, J = 7.4 Hz, 2H). |
| 498 | 385.1 [M + H] | ¹H NMR (400 MHz, DMSO-d6 + D2O) δ 8.13 (d, J = 1.4 Hz, 1H), 7.96 (s, 1H), 7.71 (s, 1H), 7.64-7.57 (m, 2H), 7.56-7.48 (m, 3H), 7.09 (s, 1H), 4.35-4.11 (m, 2H). ¹⁹F NMR (376 MHz, DMSO-d6 + D2O) δ −74.81, −99.32. |
| 499 | 363.2 [M + H] | ¹H NMR (400 MHz, DMSO-d6 + D2O) δ 8.11 (s, 1H), 7.99 (s, 1H), 7.70 (s, 1H), 7.37-7.28 (m, 4H), 7.26-7.18 (m, 1H), 6.99 (s, 1H), 3.57-3.44 (m, 2H), 3.22 (q, J = 7.2 Hz, 1H), 1.29 (d, J = 6.9 Hz, 3H). |
| 500 | 363.2 [M + H] | ¹H NMR (400 MHz, DMSO-d6 + D2O) δ 8.11 (s, 1H), 7.99 (s, 1H), 7.70 (s, 1H), 7.37-7.28 (m, 4H), 7.26-7.18 (m, 1H), 6.99 (s, 1H), 3.57-3.44 (m, 2H), 3.22 (q, J = 7.2 Hz, 1H), 1.29 (d, J = 6.9 Hz, 3H). |
| 501 | 376.2 [M + H] | ¹H NMR (400 MHz, DMSO-d6 + D2O) δ 8.08 (d, J = 1.2 Hz, 1H), 7.97 (s, 1H), 7.59 (d, J = 1.2 Hz, 1H), 6.64 (s, 1H), 4.54-4.33 (m, 4H), 4.20 (app q, J = 11.8 Hz, 4H). ¹⁹F NMR (376 MHz, DMSO-d6 + D2O) δ −115.45. ES/MS m/z: 376.2 [M + H]. |
| 502 | 484.1 [M + H] | ¹H NMR (400 MHz, DMSO-d6) δ 8.08 (d, J = 1.2 Hz, 1H), 7.97 (s, 1H), 7.58 (d, J = 1.2 Hz, 1H), 7.53 (td, J = 8.0, 6.1 Hz, 1H), 7.45-7.35 (m, 2H), 7.32 (td, J = 8.6, 2.7 Hz, 1H), 6.64 (s, 1H), 4.64-4.15 (m, 10H). |
| 503 | 418.2 [M + H] | ¹H NMR (400 MHz, DMSO-d6 + D2O) δ 8.07 (d, J = 1.2 Hz, 1H), 7.95 (s, 1H), 7.59 (d, J = 1.2 Hz, 1H), 6.62 (s, 1H), 4.43 (t, J = 13.1 Hz, 2H), 4.35 (d, J = 9.3 Hz, 1H), 4.32-4.23 (m, 3H), 4.04 (d, J = 10.3 Hz, 1H), 3.95 (d, J = 10.3 Hz, 1H), 1.81 (s, 3H). |
| 504 | 434.2 [M + H] | ¹H NMR (400 MHz, DMSO-d6 + D2O) δ −8.06 (d, J = 1.2 Hz, 1H), 7.94 (s, 1H), 7.57 (d, J = 1.2 Hz, 1H), 6.60 (s, 1H), 4.53-4.32 (m, 2H), 4.26 (s, 2H), 4.13-4.00 (m, 4H), 3.59 (s, 3H). |
| 505 | 510.1 [M + H] | ¹H NMR (400 MHz, DMSO-d6 + D2O) 8 8.08 (d, J = 1.1 Hz, 1H), 7.95 (s, 1H), 7.59 (d, J = 1.2 Hz, 1H), 7.41-7.30 (m, 5H), 6.62 (s, 1H), 5.08 (s, 2H), 4.53-4.36 (m, 2H), 4.28 (s, 2H), 4.14 (s, 4H). ¹⁹F NMR (376 MHz, DMSO-d6 + D2O) δ −75.16, −116.95. ES/MS m/z: 510.1 [M + H]. |
| 506 | 502.2 [M + H] | ¹H NMR (400 MHz, DMSO-d6 + D2O) δ 8.07 (d, J = 1.2 Hz, 1H), 7.95 (s, 1H), 7.58 (d, J = 1.2 Hz, 1H), 6.61 (s, 1H), 4.84-4.62 (m, 2H), 4.45 (s, 2H), 4.29 (s, 2H), 4.26-4.11 (m, 4H). |
| 507 | 440.2 [M + H] | ¹H NMR (400 MHz, DMSO-d6 + D2O) δ 8.09 (d, J = 1.2 Hz, 1H), 7.97 (s, 1H), 7.59 (d, J = 1.2 Hz, 1H), 6.65 (s, 1H), 6.30 (tt, J = 54.0, 3.5 Hz, 1H), 4.43 (s, 4H), 4.36 (t, J = 11.1 Hz, 2H), 4.26 (d, J = 10.9 Hz, 2H), 3.73 (t, J = 15.1 Hz, 2H). |
| 508 | 458.2 [M + H] | ¹H NMR (400 MHz, DMSO-d6 + D2O) 8 8.08 (d, J = 1.2 Hz, 1H), 7.95 (s, 1H), 7.59 (d, J = 1.2 Hz, 1H), 6.62 (s, 1H), 4.35 (t, J = 13.7 Hz, 2H), 4.27 (s, 2H), 3.68 (d, J = 8.1 Hz, 2H), 3.53 (d, J = 8.2 Hz, 2H), 3.35 (q, J = 10.2 Hz, 2H). |
| 509 | 346.1 [M + H] | ¹H NMR (400 MHz, DMSO-d6) δ 9.96 (d, J = 66.7 Hz, 1H), 9.31 (s, 1H), 8.63 (s, 1H), 8.36 (s, 1H), 8.32 (s, 1H), 8.20 (d, J = 1.2 Hz, 1H), 7.99 (t, J = 58.8 Hz, 1H), 7.70 (d, J = 1.2 Hz, 1H). |
| 510 | 354.2 [M + H] | ¹H NMR (400 MHz, DMSO-d6) δ 11.53 (d, J = 1.8 Hz, 1H), 11.49 (d, J = 6.6 Hz, 1H), 8.87 (s, 1H), 8.43 (s, 1H), 8.28 (d, J = 1.2 Hz, 1H), 8.02 (d, J = 6.1 Hz, 1H), 7.91 (s, 1H), 7.80 (d, J = 1.2 Hz, 1H), 4.41 (t, J = 5.2 Hz, 2H), 3.75 (t, J = 5.2 Hz, 2H), 3.26 (s, 3H). |
| 511 | 409.2 [M + H] | ¹H NMR (400 MHz, DMSO-d6) δ 11.54 (s, 2H), 11.52 (s, 1H), 9.06 (s, 1H), 8.53 (s, 1H), 8.30 (d, J = 1.2 Hz, 1H), 8.03 (d, J = 6.0 Hz, 1H), 7.96 (s, 1H), 7.81 (d, J = 1.2 Hz, 1H), 4.72 (t, J = 6.4 Hz, 2H), 4.17-3.90 (m, 4H), 3.19 (s, 4H). |

TABLE 3-continued

Characterization Data

| Example No. | ES/MS m/z | NMR |
|---|---|---|
| 512 | 310.1 [M + H] | ¹H NMR (400 MHz, DMSO-d6) δ 11.57 (d, J = 4.7 Hz, 2H), 8.41 (s, 1H), 8.36 (s, 1H), 8.09 (d, J = 6.3 Hz, 1H), 7.94 (d, J = 2.3 Hz, 2H), 7.52 (d, J = 2.3 Hz, 1H), 4.03 (s, 3H). |
| 513 | 341.2 [M + H] | ¹H NMR (400 MHz, DMSO-d6) δ 11.56-11.52 (m, 1H), 11.51 (s, 1H), 8.36 (s, 1H), 8.33 (d, J = 1.3 Hz, 1H), 8.03 (d, J = 6.1 Hz, 1H), 7.82 (d, J = 1.3 Hz, 1H), 4.25 (s, 2H), 2.46 (s, 2H), 1.21 (s, 6H). |
| 514 | 343.1 [M + H] | ¹H NMR (400 MHz, DMSO-d6) δ 11.49 (d, J = 4.8 Hz, 2H), 8.37 (s, 1H), 8.29 (d, J = 1.2 Hz, 1H), 8.00 (d, J = 6.3 Hz, 1H), 7.74 (d, J = 1.2 Hz, 1H), 4.64 (s, 2H), 1.53 (s, 6H). |
| 515 | 431.1 [M + H] | ¹H NMR (400 MHz, DMSO-d6) δ 11.63-11.35 (m, 2H), 8.01 (d, J = 6.2 Hz, 1H), 6.82 (s, 1H), 4.36 (s, 2H), 3.84 (s, 2H), 1.21 (s, 6H). |
| 516 | 349.2 [M + H]. | ¹H NMR (400 MHz, DMSO-d6) δ 11.41 (d, J = 1.9 Hz, 1H), 11.40-11.30 (m, 1H), 8.06 (d, J = 1.2 Hz, 1H), 7.94 (d, J = 6.1 Hz, 1H), 7.58 (d, J = 1.2 Hz, 1H), 6.60 (s, 1H), 4.53-4.17 (m, 4H), 2.85 (dq, J = 17.7, 8.9, 8.1 Hz, 1H), 1.15 (d, J = 6.9 Hz, 3H). |
| 517 | 349.2 [M + H]. | ¹H NMR (400 MHz, DMSO-d6) δ 11.41 (d, J = 1.9 Hz, 1H), 11.40-11.30 (m, 1H), 8.06 (d, J = 1.2 Hz, 1H), 7.94 (d, J = 6.1 Hz, 1H), 7.58 (d, J = 1.2 Hz, 1H), 6.60 (s, 1H), 4.53-4.17 (m, 4H), 2.85 (dq, J = 17.7, 8.9, 8.1 Hz, 1H), 1.15 (d, J = 6.9 Hz, 3H). |
| 518 | 367.2 [M + H]. | ¹H NMR (400 MHz, DMSO-d6) δ 11.44 (s, 1H), 11.41 (d, J = 6.7 Hz, 1H), 7.97 (d, J = 6.1 Hz, 1H), 7.41 (d, J = 7.2 Hz, 1H), 6.60 (s, 1H), 4.32 (s, 1H), 3.80 (s, 2H), 3.52 (s, 1H), 2.86 (dt, J = 18.0, 8.9 Hz, 1H), 1.15 (d, J = 6.8 Hz, 3H). ¹⁹F NMR (376 MHz, DMSO-d6) δ −109.94 (d, J = 225.7 Hz), −113.75 (d, J = 222.6 Hz), −155.51 (d, J = 7.3 Hz). |
| 519 | 367.2 [M + H]. | ¹H NMR (400 MHz, DMSO-d6) δ 11.44 (s, 1H), 11.41 (d, J = 6.7 Hz, 1H), 7.97 (d, J = 6.1 Hz, 1H), 7.41 (d, J = 7.2 Hz, 1H), 6.60 (s, 1H), 4.32 (s, 1H), 3.80 (s, 2H), 3.52 (s, 1H), 2.86 (dt, J = 18.0, 8.9 Hz, 1H), 1.15 (d, J = 6.8 Hz, 3H). ¹⁹F NMR (376 MHz, DMSO-d6) δ −109.94 (d, J = 225.7 Hz), −113.75 (d, J = 222.6 Hz), −155.51 (d, J = 7.3 Hz). |
| 520 | 383.2 [M + H]. | ¹H NMR (400 MHz, DMSO-d6 + D2O) δ 8.00 (s, 1H), 7.70 (s, 1H), 6.70 (s, 1H), 4.61-4.16 (m, 3H), 3.52 (s, 1H), 2.94-2.79 (m, 1H), 1.15 (d, J = 6.8 Hz, 3H). |
| 521 | 383.2 [M + H]. | ¹H NMR (400 MHz, DMSO-d6 + D2O) δ 8.00 (s, 1H), 7.70 (s, 1H), 6.70 (s, 1H), 4.61-4.16 (m, 3H), 3.52 (s, 1H), 2.94-2.79 (m, 1H), 1.15 (d, J = 6.8 Hz, 3H). |
| 522 | 397.2 [M + H]. | ¹H NMR (400 MHz, DMSO-d6) δ 7.99 (s, 1H), 7.69 (s, 1H), 6.67 (s, 1H), 4.39 (s, 2H), 3.85 (s, 2H), 1.20 (s, 6H). |
| 523 | 496.1 [M + H]. | ¹H NMR (400 MHz, DMSO-d6) δ 8.68 (dd, J = 2.3, 1.2 Hz, 1H), 8.18 (dd, J = 8.8, 2.6 Hz, 1H), 8.09 (d, J = 1.2 Hz, 1H), 7.95 (s, 1H), 7.60 (d, J = 1.1 Hz, 1H), 7.20 (d, J = 8.7 Hz, 1H), 6.64 (s, 1H), 6.26-5.95 (m, 1H), 4.91-4.36 (m, 3H), 4.20 (d, J = 12.7 Hz, 1H). ¹⁹F NMR (377 MHz, DMSO-d6) δ −60.58, −75.26, −107.94 (d, J = 237.8 Hz), −119.52 (d, J = 238.5 Hz). |
| 524 | 415.6 [M + H]. | ¹H NMR (400 MHz, DMSO-d6 + D2O) δ − 8.07 (d, J = 1.2 Hz, 1H), 7.94 (s, 1H), 7.59 (d, J = 1.2 Hz, 1H), 6.60 (s, 1H), 6.19 (tt, J = 54.6, 3.5 Hz, 1H), 4.66-4.51 (m, 1H), 4.53-4.38 (m, 1H), 4.37-4.24 (m, 1H), 4.24-4.14 (m, 1H), 4.01 (app s, 1H), 3.99 (td, J = 15.1, 3.6 Hz, 2H). ¹⁹F NMR (376 MHz, DMSO-d6 + D2O) δ −75.03 (d, J = 2.0 Hz), −107.59 (d, J = 237.3 Hz), −121.91 (d, J = 237.1 Hz), −126.77 (dt, J = 54.5, 15.0 Hz). |
| 525 | 423.2 [M + H]. | ¹H NMR (400 MHz, DMSO-d6 + D2O) δ 8.08 (d, J = 1.2 Hz, 1H), 7.95 (s, 1H), 7.59 (d, J = 1.2 Hz, 1H), 6.61 (s, 1H), 5.49 (s, 1H), 4.62-4.43 (m, 1H), 4.43-4.26 (m, 2H), 4.25-4.11 (m, 3H), 1.24 (t, J = 7.1 Hz, 3H). |
| 526 | 422.2 [M + H]. | ¹H NMR (400 MHz, DMSO-d6 + D2O) δ 8.08 (d, J = 1.2 Hz, 1H), 7.94 (s, 1H), 7.58 (d, J = 1.2 Hz, 1H), 6.60 (s, 1H), 5.55-5.28 (m, 1H), 4.48 (s, 1H), 4.42-4.20 (m, 2H), 4.06 (s, 1H), 3.04 (q, J = 7.2 Hz, 2H), 1.02 (t, J = 7.2 Hz, 3H). |
| 527 | 351.2 [M + H] | ¹H NMR (400 MHz, DMSO-d6 + D2O) δ 8.07 (d, J = 1.2 Hz, 1H), 7.94 (s, 1H), 7.58 (d, J = 1.2 Hz, 1H), 6.59 (s, 1H), 4.52-4.17 (m, 3H), 4.11 (s, 1H), 3.84 (s, 1H). |
| 528 | 351.2 [M + H] | ¹H NMR (400 MHz, DMSO-d6 + D2O) 8 8.07 (d, J = 1.2 Hz, 1H), 7.95 (s, 1H), 7.59 (d, J = 1.2 Hz, 1H), 6.60 (s, 1H), 4.50-4.33 (m, 2H), 4.33-4.18 (m, 1H), 4.10 (s, 1H), 3.84 (s, 1H). |
| 529 | 496.2 [M + H] | ¹H NMR (400 MHz, Methanol-d4) δ 8.58 (dt, J = 2.8, 0.9 Hz, 1H), 8.16 (s, 1H), 8.09-8.03 (m, 2H), 7.73 (d, J = 1.5 Hz, 1H), 7.11 (d, J = 8.7 Hz, 1H), 7.01 (s, 1H), 6.10-6.01 (m, 1H), 4.64-4.41 (m, 3H), 4.26 (d, J = 12.2 Hz, 1H). |
| 530 | 496.1 [M + H] | ¹H NMR (400 MHz, DMSO-d6 + D2O) δ 8.69 (dt, J = 1.9, 1.0 Hz, 1H), 8.19 (dd, J = 8.8, 2.6 Hz, 1H), 8.09 (d, J = 1.2 Hz, 1H), 7.95 (s, 1H), 7.60 (d, J = 1.2 Hz, 1H), 7.20 (d, J = 8.7 Hz, 1H), 6.65 (s, 1H), 6.18-5.90 (m, 1H), 4.74-4.36 (m, 3H), 4.20 (d, J = 12.8 Hz, 1H). |

TABLE 3-continued

Characterization Data

| Example No. | ES/MS m/z | NMR |
|---|---|---|
| 531 | 497.1 [M + H] | ¹H NMR (400 MHz, Methanol-d4) δ 9.01 (d, J = 0.9 Hz, 2H), 8.12 (s, 1H), 8.02 (d, J = 1.4 Hz, 1H), 7.65 (d, J = 1.4 Hz, 1H), 6.90 (s, 1H), 6.16-5.94 (m, 1H), 4.67-4.43 (m, 3H), 4.37 (d, J = 12.9 Hz, 1H). |
| 532 | 497.2 [M + H] | ¹H NMR (400 MHz, Methanol-d4) δ 9.15-8.86 (m, 2H), 8.13 (s, 1H), 8.02 (d, J = 1.4 Hz, 1H), 7.65 (d, J = 1.4 Hz, 1H), 6.90 (s, 1H), 6.15-5.93 (m, 1H), 4.73-4.44 (m, 3H), 4.38 (d, J = 13.0 Hz, 1H). |
| 533 | 436.1 [M + H]. | ¹H NMR (400 MHz, Methanol-d4) δ 8.16 (s, 1H), 8.08 (d, J = 1.5 Hz, 1H), 7.73 (d, J = 1.5 Hz, 1H), 6.98 (s, 1H), 5.46 (s, 1H), 4.58-4.24 (m, 3H), 4.13 (d, J = 12.4 Hz, 1H), 3.76 (hept, J = 6.6 Hz, 1H), 1.17 (dd, J = 8.1, 6.6 Hz, 6H). |
| 534 | ES/MS m/z: 436.1 [M + H]. | ¹H NMR (400 MHz, Methanol-d4) δ 8.12 (s, 1H), 8.01 (d, J = 1.4 Hz, 1H), 7.65 (d, J = 1.4 Hz, 1H), 6.85 (s, 1H), 5.52-5.39 (m, 1H), 4.55-4.42 (m, 1H), 4.42-4.25 (m, 2H), 4.14 (d, J = 12.1 Hz, 1H), 3.76 (hept, J = 6.6 Hz, 1H), 1.17 (t, J = 7.1 Hz, 6H). |
| 535 | 476.1 [M + H]. | ¹H NMR (400 MHz, Methanol-d4) δ 8.20 (s, 1H), 8.18-8.13 (m, 1H), 7.82 (d, J = 1.6 Hz, 1H), 7.12 (s, 1H), 5.56 (s, 1H), 4.57-4.25 (m, 5H), 4.16 (d, J = 12.4 Hz, 1H), 3.94-3.71 (m, 1H). |
| 536 | 470.1 [M + H] | ¹H NMR (400 MHz, Methanol-d4) δ 8.20 (s, 1H), 8.15 (d, J = 1.7 Hz, 1H), 7.82 (d, J = 1.7 Hz, 1H), 7.13 (s, 1H), 5.63-5.46 (m, 1H), 4.56-4.30 (m, 7H), 4.18 (dt, J = 12.5, 2.5 Hz, 1H). ¹⁹F NMR (376 MHz, Methanol-d4) δ −78.14, −103.39 (h, J = 12.0 Hz), −108.90-−111.06 (m), −124.19 (ddq, J = 243.5, 8.2, 3.7 Hz). |
| 537 | 428.1 [M + H]. | ¹H NMR (400 MHz, Methanol-d4) δ 8.24-8.17 (m, 3H), 7.89 (d, J = 1.9 Hz, 1H), 7.77 (ddd, J = 8.3, 7.2, 2.0 Hz, 1H), 7.27 (s, 1H), 7.08 (ddd, J = 7.2, 5.1, 0.9 Hz, 1H), 6.93 (dt, J = 8.3, 0.9 Hz, 1H), 6.09-5.86 (m, 1H), 4.63-4.35 (m, 3H), 4.19 (dt, J = 12.1, 2.6 Hz, 1H). |
| 538 | 428.1 [M + H]. | ¹H NMR (400 MHz, Methanol-d4) δ 8.38-8.14 (m, 3H), 7.90 (d, J = 1.9 Hz, 1H), 7.77-7.68 (m, 1H), 7.28 (s, 1H), 7.08 (ddd, J = 7.2, 5.1, 0.9 Hz, 1H), 6.93 (dt, J = 8.3, 0.9 Hz, 1H), 6.04-5.91 (m, 1H), 4.58-4.37 (m, 3H), 4.19 (d, J = 11.8 Hz, 1H). |
| 539 | 313.2 [M + H]. | ¹H NMR (400 MHz, DMSO-d6 + D2O) δ 8.36 (d, J = 1.2 Hz, 1H), 8.18-8.10 (m, 1H), 8.08 (q, J = 2.6 Hz, 1H), 8.05 (s, 1H), 7.84 (d, J = 1.2 Hz, 1H), 7.81 (s, 1H), 6.43 (dd, J = 3.5, 1.9 Hz, 1H). Multiplet Report ¹⁹F NMR (377 MHz, DMSO-d6) δ −74.18, −161.99-−162.10 (m). |
| 540 | 459.2 [M + H]. | ¹H NMR (400 MHz, Methanol-d4) δ 8.14 (s, 1H), 8.05 (d, J = 1.4 Hz, 1H), 7.69 (d, J = 1.5 Hz, 1H), 6.92 (s, 1H), 6.12 (tt, J = 54.4, 3.6 Hz, 1H), 5.53 (td, J = 5.5, 2.8 Hz, 1H), 4.63-4.22 (m, 6H). |
| 541 | 477.2 [M + H]. | ¹H NMR (400 MHz, Methanol-d4) δ 8.14 (s, 1H), 8.05 (d, J = 1.4 Hz, 1H), 7.69 (d, J = 1.4 Hz, 1H), 6.92 (s, 1H), 5.64-5.49 (m, 1H), 4.84-4.71 (m, 2H), 4.61-4.49 (m, 1H), 4.49-4.23 (m, 3H). |
| 542 | 459.2 [M + H]. | ¹H NMR (400 MHz, Methanol-d4) δ 8.13 (s, 1H), 8.03 (d, J = 1.4 Hz, 1H), 7.67 (d, J = 1.4 Hz, 1H), 6.90 (s, 1H), 6.12 (tt, J = 54.5, 3.6 Hz, 1H), 5.70-5.48 (m, 1H), 4.64-4.23 (m, 6H). |
| 543 | 477.1 [M + H] | ¹H NMR (400 MHz, Methanol-d4) δ 8.16 (s, 1H), 8.08 (d, J = 1.5 Hz, 1H), 7.73 (d, J = 1.5 Hz, 1H), 6.98 (s, 1H), 5.57 (td, J = 5.4, 2.7 Hz, 1H), 4.83-4.71 (m, 2H), 4.61-4.48 (m, 1H), 4.48-4.26 (m, 3H). ¹⁹F NMR (376 MHz, Methanol-d4) δ −74.94-−77.33 (m), −78.08, −107.67-−111.41 (m), −124.29 (d, J = 245.9 Hz). |
| 544 | 450.1 [M + H]. | ¹H NMR (400 MHz, Methanol-d4) δ 8.14 (s, 1H), 8.06 (d, J = 1.5 Hz, 1H), 7.70 (d, J = 1.5 Hz, 1H), 6.94 (s, 1H), 5.42 (s, 1H), 4.56-4.25 (m, 3H), 4.12 (d, J = 12.3 Hz, 1H), 1.32 (s, 9H). |
| 545 | 476.2 [M + H]. | ¹H NMR (400 MHz, Methanol-d4) δ 8.21-8.11 (m, 2H), 8.05 (d, J = 1.5 Hz, 1H), 7.69 (d, J = 1.5 Hz, 1H), 6.92 (s, 1H), 5.64-5.37 (m, 1H), 4.57-4.44 (m, 1H), 4.44-4.27 (m, 2H), 4.18 (d, J = 12.5 Hz, 1H), 3.91-3.77 (m, 2H). |
| 546 | 490.2 [M + H]. | ¹H NMR (400 MHz, Methanol-d4) δ 8.20-8.08 (m, 2H), 8.02 (d, J = 1.4 Hz, 1H), 7.66 (d, J = 1.4 Hz, 1H), 6.87 (s, 1H), 5.49 (s, 1H), 4.63-4.46 (m, 1H), 4.46-4.26 (m, 2H), 4.19 (d, J = 12.8 Hz, 1H), 1.32 (d, J = 7.2 Hz, 3H). |
| 547 | 490.2 [M + H]. | ¹H NMR (400 MHz, Methanol-d4) δ 8.18 (s, 1H), 8.15 (d, J = 9.2 Hz, 1H), 8.13 (d, J = 1.6 Hz, 1H), 7.79 (d, J = 1.7 Hz, 1H), 7.08 (s, 1H), 5.54 (s, 1H), 4.59-4.27 (m, 3H), 4.15 (d, J = 12.1 Hz, 1H), 1.35 (d, J = 7.1 Hz, 3H). |
| 548 | 466.2 [M + H]. | ¹H NMR (400 MHz, Methanol-d4 + CF3COOH) δ 8.33 (d, J = 2.2 Hz, 1H), 8.31 (s, 1H), 8.05 (d, J = 2.2 Hz, 1H), 7.52 (s, 1H), 5.52 (s, 2H), 4.37 (td, J = 18.5, 16.7, 6.1 Hz, 3H), 4.10 (d, J = 11.7 Hz, 1H), 3.84 (h, J = 6.3 Hz, 1H), 3.36 (s, 3H), 1.14 (d, J = 6.8 Hz, 3H). |
| 549 | 466.2 [M + H]. | ¹H NMR (400 MHz, Methanol-d4 + CF3COOH) δ 8.33 (d, J = 2.2 Hz, 1H), 8.31 (s, 1H), 8.05 (d, J = 2.2 Hz, 1H), 7.52 (s, 1H), 5.52 (s, 2H), 4.37 (td, J = 18.5, 16.7, 6.1 Hz, 3H), 4.10 (d, J = 11.7 Hz, 1H), 3.84 (h, J = 6.3 Hz, 1H), 3.36 (s, 3H), 1.14 (d, J = 6.8 Hz, 3H). |

TABLE 3-continued

Characterization Data

| Example No. | ES/MS m/z | NMR |
|---|---|---|
| 550 | 472.2 [M + H]. | $^1$H NMR (400 MHz, Methanol-d4 + CF3COOH) δ 8.33 (d, J = 2.1 Hz, 1H), 8.30 (s, 1H), 8.03 (d, J = 2.1 Hz, 1H), 7.46 (s, 1H), 5.83 (tdd, J = 56.1, 9.1, 2.8 Hz, 1H), 5.56 (s, 1H), 4.49-4.29 (m, 3H), 4.20-4.09 (m, 1H), 4.06-3.93 (m, 1H), 1.23 (dd, J = 10.3, 7.0 Hz, 3H). |
| 551 | 460.1 [M + H]. | $^1$H NMR (400 MHz, Methanol-d4) δ 8.13 (s, 1H), 8.03 (d, J = 1.4 Hz, 1H), 7.67 (d, J = 1.4 Hz, 1H), 6.89 (s, 1H), 5.43 (s, 1H), 4.59-4.43 (m, 1H), 4.42-4.24 (m, 2H), 4.12 (d, J = 12.6 Hz, 1H), 2.41 (s, 1H), 2.05 (s, 6H). |
| 552 | 418.12 [M + H] | $^1$H NMR (400 MHz, DMSO-d6) δ 11.63-11.50 (m, 2H), 8.36 (d, J = 1.3 Hz, 1H), 8.05 (d, J = 6.1 Hz, 1H), 7.86 (d, J = 1.3 Hz, 1H), 7.78 (s, 1H), 7.71-7.61 (m, 1H), 7.55-7.45 (m, 1H), 7.41-7.34 (m, 1H). $^{19}$F NMR (376 MHz, DMSO-d6) δ −75.25, −132.32--133.28 (m), −133.74--134.93 (m), −138.59--139.01 (m), −140.38--140.69 (m). |
| 553 | 405.10 [M + H] | $^1$H NMR (400 MHz, DMSO-d6) δ 11.60-11.50 (m, 2H), 8.35 (s, 1H), 8.03 (d, J = 6.0 Hz, 1H), 7.92-7.86 (m, 2H), 7.72-7.59 (m, 3H), 2.95-2.85 (m, 1H), 2.85-2.74 (m, 1H), 2.19-2.08 (m, 1H), 1.93-1.80 (m, 1H). |
| 554 | 414.10 [M + H] | $^1$H NMR (400 MHz, DMSO-d6) δ 11.62-11.52 (m, 2H), 8.38 (d, J = 1.5 Hz, 1H), 8.05 (d, J = 6.1 Hz, 1H), 7.97-7.91 (m, 1H), 7.70-7.62 (m, 3H), 7.51-7.44 (m, 2H), 2.94-2.86 (m, 1H), 2.86-2.78 (m, 1H), 2.16-2.04 (m, 1H), 1.91-1.80 (m, 1H). $^{19}$F NMR (376 MHz, DMSO-d6) δ −61.27, −75.21. |
| 555 | 380.10 [M + H] | $^1$H NMR (400 MHz, Methanol-d4) δ 8.38-8.33 (m, 1H), 8.29 (s, 1H), 8.08 (s, 1H), 8.05 (s, 1H), 7.46-7.40 (m, 1H), 7.36-7.23 (m, 3H), 2.99-2.86 (m, 2H), 2.62-2.52 (m, 1H), 2.06-1.96 (m, 1H), 1.95-1.85 (m, 1H). $^{19}$F NMR (376 MHz, Methanol-d4) δ −77.75. |
| 556 | 412.10 [M + H] | $^1$H NMR (400 MHz, Methanol-d4) δ 8.40 (d, J = 2.0 Hz, 1H), 8.31 (s, 1H), 8.09 (d, J = 2.0 Hz, 1H), 8.04 (s, 1H), 7.38-7.29 (m, 2H), 7.18-7.09 (m, 2H), 6.81 (t, J = 74.1 Hz, 1H), 2.80-2.66 (m, 2H), 1.98-1.88 (m, 2H). $^{19}$F NMR (376 MHz, Methanol-d4) δ −77.85, −83.91 (d, J = 74.2 Hz). |
| 557 | 407.10 [M + H] | $^1$H NMR (400 MHz, Methanol-d4) δ 8.40 (d, J = 1.9 Hz, 1H), 8.30 (s, 1H), 8.10 (d, J = 1.9 Hz, 1H), 8.06 (s, 1H), 7.25-7.15 (m, 2H), 2.92-2.75 (m, 2H), 2.12-1.94 (m, 2H). $^{19}$F NMR (376 MHz, Methanol-d4) δ −77.95, −107.99 (d, J = 9.6 Hz). |
| 558 | 407.10 [M + H] | $^1$H NMR (400 MHz, Methanol-d4) δ 8.39 (d, J = 2.0 Hz, 1H), 8.29 (s, 1H), 8.10 (s, 1H), 8.09 (d, J = 2.0 Hz, 1H), 7.62-7.53 (m, 1H), 7.28-7.19 (m, 1H), 2.99-2.80 (m, 2H), 2.13-1.95 (m, 2H). $^{19}$F NMR (376 MHz, Methanol-d4) δ −77.96, −135.73--135.87 (m), −143.81--144.01 (m). |
| 559 | 401.10 [M + H] | $^1$H NMR (400 MHz, Methanol-d4) δ 8.39 (d, J = 2.0 Hz, 1H), 8.30 (s, 1H), 8.09 (d, J = 2.0 Hz, 1H), 8.05 (s, 1H), 7.57 (d, J = 8.0 Hz, 1H), 7.11-7.05 (m, 1H), 7.00-6.92 (m, 1H), 3.97 (s, 3H), 2.88-2.75 (m, 2H), 2.03-1.96 (m, 2H). |
| 560 | 385.10 [M + H] | $^1$H NMR (400 MHz, Methanol-d4) δ 8.35 (d, J = 1.9 Hz, 1H), 8.27 (s, 1H), 8.03 (d, J = 1.9 Hz, 1H), 7.98 (s, 1H), 7.62 (d, J = 8.0 Hz, 1H), 7.33 (s, 1H), 7.27-7.20 (m, 1H), 2.86-2.70 (m, 2H), 2.53 (s, 3H), 2.03-1.89 (m, 2H). |
| 561 | 412.10 [M + H] | $^1$H NMR (400 MHz, Methanol-d4) δ 8.36 (d, J = 1.9 Hz, 1H), 8.28 (s, 1H), 8.05 (d, J = 1.9 Hz, 1H), 7.99 (s, 1H), 7.35-7.27 (m, 2H), 7.16-7.08 (m, 2H), 6.79 (t, J = 74.1 Hz, 1H), 2.79-2.65 (m, 2H), 1.95-1.85 (m, 2H). $^{19}$F NMR (376 MHz, Methanol-d4) δ −77.78, −83.90 (d, J = 74.2 Hz). |
| 562 | 471.10 [M + H] | $^1$H NMR (400 MHz, Methanol-d4) δ 8.32 (d, J = 1.8 Hz, 1H), 8.26 (s, 1H), 8.15 (d, J = 8.6 Hz, 1H), 8.10 (d, J = 1.8 Hz, 1H), 7.98 (d, J = 1.8 Hz, 1H), 7.95 (s, 1H), 7.61 (dd, J = 8.6, 1.8 Hz, 1H), 2.96-2.83 (m, 2H), 2.10-1.97 (m, 2H). $^{19}$F NMR (376 MHz, Methanol-d4) δ −63.97, −77.76. |
| 563 | 411.20 [M + H] | $^1$H NMR (400 MHz, Methanol-d4) δ 8.37 (d, J = 2.0 Hz, 1H), 8.28 (s, 1H), 8.06 (d, J = 2.0 Hz, 1H), 8.01 (s, 1H), 7.61 (d, J = 8.1 Hz, 1H), 7.18 (dd, J = 8.1, 1.7 Hz, 1H), 6.97 (d, J = 1.7 Hz, 1H), 2.82-2.71 (m, 2H), 2.29-2.20 (m, 1H), 2.01-1.88 (m, 2H), 1.22-1.09 (m, 2H), 0.94-0.80 (m, 2H). $^{19}$F NMR (376 MHz, Methanol-d4) δ −77.90. |
| 564 | 444.10 [M + H] | $^1$H NMR (400 MHz, Methanol-d4) δ 8.34 (d, J = 1.9 Hz, 1H), 8.27 (s, 1H), 8.03 (d, J = 1.9 Hz, 1H), 7.95 (s, 1H), 4.52 (q, J = 8.5 Hz, 2H), 2.76-2.61 (m, 2H), 1.87 (t, J = 7.5 Hz, 2H). $^{19}$F NMR (376 MHz, Methanol-d4) δ −76.35 (t, J = 8.5 Hz), −77.73. |

TABLE 3-continued

Characterization Data

| Example No. | ES/MS m/z | NMR |
|---|---|---|
| 565 | 407.10 [M + H] | $^1$H NMR (400 MHz, DMSO-d6) δ 11.60-11.50 (m, 2H), 8.35 (s, 1H), 8.02 (d, J = 6.1 Hz, 1H), 7.95 (dd, J = 9.4, 5.4 Hz, 1H), 7.88 (bs, 1H), 7.66 (s, 1H), 7.53 (dd, J = 10.2, 6.0 Hz, 1H), 3.14-3.03 (m, 1H), 2.96-2.87 (m, 1H), 2.28-2.19 (m, 1H), 2.01-1.90 (m, 1H). $^{19}$F NMR (376 MHz, DMSO-d6) δ −113.84−−113.99 (m), −123.11−−123.32 (m). |
| 566 | 405.10 [M + H] | $^1$H NMR (400 MHz, Methanol-d4) δ 8.36 (d, J = 1.8 Hz, 1H), 8.28 (s, 1H), 8.04 (d, J = 1.8 Hz, 1H), 7.98 (s, 1H), 7.78 (d, J = 8.1 Hz, 1H), 7.59 (d, J = 1.7 Hz, 1H), 7.41 (dd, J = 8.1, 1.7 Hz, 1H), 2.92-2.76 (m, 2H), 2.10-1.93 (m, 2H). $^{19}$F NMR (376 MHz, Methanol-d4) δ −77.86. |
| 567 | 403.20 [M + H] | $^1$H NMR (400 MHz, Methanol-d4) δ 8.38 (d, J = 2.0 Hz, 1H), 8.29 (s, 1H), 8.07 (d, J = 2.0 Hz, 1H), 8.02 (s, 1H), 7.18 (s, 1H), 7.09 (d, J = 10.2 Hz, 1H), 2.87-2.80 (m, 1H), 2.79-2.72 (m, 1H), 2.54 (s, 3H), 2.05-1.91 (m, 2H). $^{19}$F NMR (376 MHz, Methanol-d4) δ −77.90, −110.59 (d, J = 10.3 Hz). |
| 568 | 381.10 [M + H] | $^1$H NMR (400 MHz, Methanol-d4) δ 8.42 (d, J = 2.1 Hz, 1H), 8.36 (d, J = 2.6 Hz, 1H), 8.31 (s, 1H), 8.14 (d, J = 2.1 Hz, 1H), 8.11 (s, 1H), 7.71 (dd, J = 8.3, 2.6 Hz, 1H), 7.45 (d, J = 8.3 Hz, 1H), 2.82-2.71 (m, 2H), 2.03-1.91 (m, 2H). |
| 569 | 339.20 [M + H] | $^1$H NMR (400 MHz, Methanol-d4) δ 8.26 (s, 1H), 8.24 (d, J = 2.1 Hz, 1H), 7.96 (d, J = 2.1 Hz, 1H), 7.31 (s, 1H), 3.90-3.82 (m, 4H), 2.26-2.14 (m, 4H), 2.16-2.00 (m, 4H). |
| 570 | 417.10 [M + H] | $^1$H NMR (400 MHz, Methanol-d4) δ 8.38 (d, J = 2.0 Hz, 1H), 8.30 (s, 1H), 8.07 (d, J = 2.0 Hz, 1H), 8.06 (s, 1H), 7.87 (d, J = 1.8 Hz, 1H), 7.85 (d, J = 8.5 Hz, 1H), 7.41 (dd, J = 8.5, 1.8 Hz, 1H), 2.90-2.84 (m, 1H), 2.83 (s, 3H), 2.81-2.74 (m, 1H), 2.04-1.95 (m, 2H). |
| 571 | 375.20 [M + H] | $^1$H NMR (400 MHz, Methanol-d4) δ 8.25 (s, 1H), 8.23 (d, J = 2.0 Hz, 1H), 7.94 (d, J = 2.0 Hz, 1H), 7.28 (s, 1H), 3.98 (s, 2H), 3.93 (d, J = 6.8 Hz, 2H), 2.85-2.61 (m, 4H), 2.30 (t, J = 6.8 Hz, 2H). $^{19}$F NMR (376 MHz, Methanol-d4) δ −91.22−−93.35 (m). |
| 572 | 357.20 [M + H] | $^1$H NMR (400 MHz, Methanol-d4) δ 8.21 (s, 1H), 8.16 (d, J = 2.0 Hz, 1H), 7.86 (d, J = 2.0 Hz, 1H), 7.19 (s, 1H), 3.94 (t, J = 7.2 Hz, 2H), 3.85 (d, J = 10.4 Hz, 1H), 3.58 (d, J = 10.4 Hz, 1H), 3.38 (s, 3H), 3.36 (s, 2H), 2.20-2.11 (m, 1H), 1.96-1.83 (m, 1H), 1.23 (s, 3H). |
| 573 | 425.10 [M + H] | $^1$H NMR (400 MHz, Methanol-d4) δ 8.20 (s, 1H), 7.68 (s, 1H), 7.57 (dd, J = 9.2, 5.3 Hz, 1H), 7.47 (d, J = 6.7 Hz, 1H), 7.31 (dd, J = 9.8, 5.9 Hz, 1H), 3.01-2.93 (m, 1H), 2.92-2.83 (m, 1H), 2.17-2.08 (m, 1H), 1.93-1.85 (m, 1H). $^{19}$F NMR (376 MHz, Methanol-d4) δ −78.16, −115.24−−115.40 (m), −124.37−−124.55 (m), −157.10 (d, J = 6.7 Hz). |
| 574 | 426.20 [M + H] | $^1$H NMR (400 MHz, Methanol-d4) δ 8.35 (d, J = 2.0 Hz, 1H), 8.27 (s, 1H), 8.04 (d, J = 2.0 Hz, 1H), 7.96 (s, 1H), 6.15 (tt, J = 55.0, 3.8 Hz, 1H), 4.21 (td, J = 13.8, 3.8 Hz, 2H), 2.73-2.61 (m, 2H), 1.90-1.82 (m, 2H). $^{19}$F NMR (376 MHz, Methanol-d4) δ −77.73, −128.19 (dt, J = 54.9, 13.8 Hz). |
| 575 | 361.10 [M + H] | $^1$H NMR (400 MHz, Methanol-d4) δ 8.22 (s, 1H), 8.16 (s, 1H), 7.84 (s, 1H), 7.28 (s, 1H), 4.57-4.46 (m, 1H), 4.38-4.24 (m, 1H), 3.79-3.67 (m, 2H), 3.67-3.54 (m, 1H), 3.17-3.06 (m, 1H), 3.02-2.85 (m, 1H), 2.55-2.37 (m, 1H). $^{19}$F NMR (376 MHz, Methanol-d4) δ −95.74−−98.79 (m). |
| 576 | 381.10 [M + H] | $^1$H NMR (400 MHz, Methanol-d4) δ 8.54-8.50 (m, 1H), 8.42 (d, J = 2.0 Hz, 1H), 8.32 (s, 1H), 8.13 (s, 1H), 8.11 (d, J = 2.0 Hz, 1H), 7.77 (dd, J = 8.4, 2.5 Hz, 1H), 7.46 (dd, J = 8.4, 0.6 Hz, 1H), 3.09-2.98 (m, 1H), 2.93-2.86 (m, 1H), 2.16-2.08 (m, 1H), 1.96-1.88 (m, 1H). |
| 577 | 339.20 [M + H] | $^1$H NMR (400 MHz, Methanol-d4) δ 8.19 (s, 1H), 8.17-8.09 (m, 1H), 7.86-7.78 (m, 1H), 7.14 (s, 1H), 4.11-3.90 (m, 2H), 3.87-3.74 (m, 1H), 3.70-3.60 (m, 1H), 2.34-2.20 (m, 1H), 2.02-1.90 (m, 1H), 1.88-1.73 (m, 1H), 0.92-0.76 (m, 1H), 0.62-0.51 (m, 2H), 0.32-0.22 (m, 2H). |
| 578 | 389.20 [M + H] | $^1$H NMR (400 MHz, Methanol-d4) δ 8.24 (s, 1H), 8.21 (s, 1H), 7.91 (s, 1H), 7.24 (s, 1H), 4.12-3.77 (m, 3H), 3.57-3.48 (m, 1H), 2.84-2.68 (m, 2H), 2.60-2.51 (m, 1H), 2.50-2.34 (m, 2H), 2.35-2.21 (m, 2H), 1.93-1.80 (m, 1H). $^{19}$F NMR (377 MHz, Methanol-d4) δ −84.25−−85.21 (m), −96.91−−98.31 (m). |
| 579 | 342.20 [M + H] | $^1$H NMR (400 MHz, Methanol-d4) δ 8.23 (s, 1H), 8.19 (d, J = 1.9 Hz, 1H), 7.86 (d, J = 1.9 Hz, 1H), 7.33 (s, 1H), 4.15 (d, J = 3.8 Hz, 2H), 3.99-3.91 (m, 2H), 2.84-2.68 (m, 1H), 2.53-2.41 (m, 2H), 2.08-1.91 (m, 2H). $^{19}$F NMR (376 MHz, Methanol-d4) δ −143.44−−143.86 (m). |
| 580 | 435.10 [M + H] | $^1$H NMR (400 MHz, DMSO-d6) δ 11.56-11.49 (m, 1H), 8.03 (d, J = 6.4 Hz, 1H), 7.93 (d, J = 1.8 Hz, 1H), 7.83 (d, J = 8.4 Hz, 1H), 7.54 (d, J = 7.1 Hz, 1H), 7.49 (s, 1H), 7.37 (dd, J = 8.4, 1.8 Hz, 1H), 2.99- |

TABLE 3-continued

Characterization Data

| Example No. | ES/MS m/z | NMR |
|---|---|---|
| | | 2.90 (m, 1H), 2.78 (s, 3H), 2.82-2.71 (m, 1H), 2.19-2.10 (m, 1H), 1.87-1.79 (m, 1H). $^{19}$F NMR (376 MHz, DMSO-d6) δ −155.60 (d, J = 7.1 Hz). |
| 581 | 421.10 [M + H] | $^1$H NMR (400 MHz, DMSO-d6) δ 11.59-11.50 (m, 2H), 9.33 (s, 1H), 8.07 (d, J = 1.8 Hz, 1H), 8.05-7.96 (m, 2H), 7.57 (d, J = 7.0 Hz, 1H), 7.51 (s, 1H), 7.44 (dd, J = 8.5, 1.8 Hz, 1H), 3.03-2.93 (m, 1H), 2.82-2.73 (m, 1H), 2.23-2.11 (m, 1H), 1.91-1.81 (m, 1H). $^{19}$F NMR (376 MHz, DMSO-d6) δ −155.52 (d, J = 7.0 Hz). |
| 582 | 433.10 [M + H] | $^1$H NMR (400 MHz, Methanol-d4) δ 8.71 (s, 1H), 8.30 (s, 1H), 8.25 (s, 1H), 8.02-7.97 (m, 1H), 7.97-7.90 (m, 2H), 3.22-3.14 (m, 2H), 2.24-2.14 (m, 1H), 2.11-2.02 (m, 1H). $^{19}$F NMR (376 MHz, Methanol-d4) δ −64.00, −77.76, −129.81--130.33 (m). |
| 583 | 417.10 [M + H] | $^1$H NMR (400 MHz, Methanol-d4) δ 8.37 (d, J = 2.0 Hz, 1H), 8.21 (s, 1H), 7.74 (s, 1H), 7.69 (dd, J = 9.4, 2.0 Hz, 1H), 7.51 (d, J = 6.6 Hz, 1H), 3.16-2.99 (m, 2H), 2.11-1.97 (m, 2H). $^{19}$F NMR (376 MHz, Methanol-d4) δ −78.15, −129.11 (d, J = 9.2 Hz), −156.91 (d, J = 6.8 Hz). |
| 584 | 399.10 [M + H] | $^1$H NMR (400 MHz, Methanol-d4) δ 8.48 (d, J = 2.5 Hz, 1H), 8.21 (s, 1H), 7.74 (dd, J = 8.4, 2.5 Hz, 1H), 7.70 (s, 1H), 7.53-7.46 (m, 1H), 7.40 (d, J = 8.4 Hz, 1H), 3.06-2.97 (m, 1H), 2.94-2.86 (m, 1H), 2.05-1.92 (m, 2H). |
| 585 | 381.10 [M + H] | $^1$H NMR (400 MHz, Methanol-d4) δ 8.51 (d, J = 2.5 Hz, 1H), 8.40 (d, J = 2.0 Hz, 1H), 8.30 (s, 1H), 8.11 (s, 1H), 8.10 (d, J = 2.0 Hz, 1H), 7.76 (dd, J = 8.3, 2.5 Hz, 1H), 7.47-7.41 (m, 1H), 3.05-2.96 (m, 1H), 2.92-2.81 (m, 1H), 2.14-2.06 (m, 1H), 1.96-1.85 (m, 1H). |
| 586 | 399.10 [M + H] | $^1$H NMR (400 MHz, Methanol-d4) δ 8.40 (d, J = 2.0 Hz, 2H), 8.30 (s, 1H), 8.14 (s, 1H), 8.09 (d, J = 2.0 Hz, 1H), 7.74 (dd, J = 9.4, 2.0 Hz, 1H), 3.12-3.01 (m, 2H), 2.19-2.10 (m, 1H), 2.01-1.92 (m, 1H). |
| 587 | 403.10 [M + H] | $^1$H NMR (400 MHz, Methanol-d4) δ 8.15 (s, 1H), 8.09-8.05 (m, 1H), 7.79-7.71 (m, 1H), 6.98 (s, 1H), 3.99-3.87 (m, 2H), 3.87-3.77 (m, 2H), 2.12-1.91 (m, 6H), 1.85-1.70 (m, 4H). $^{19}$F NMR (376 MHz, Methanol-d4) δ −97.66--101.57 (m). |
| 588 | 417.10 [M + H] | $^1$H NMR (400 MHz, Methanol-d4) δ 8.38 (d, J = 2.0 Hz, 1H), 8.21 (s, 1H), 7.74 (s, 1H), 7.69 (dd, J = 9.4, 2.0 Hz, 1H), 7.50 (d, J = 6.6 Hz, 1H), 3.15-3.01 (m, 2H), 2.11-1.99 (m, 2H). |
| 589 | 453.10 [M + H] | $^1$H NMR (400 MHz, Methanol-d4) δ 8.36 (d, J = 1.9 Hz, 1H), 8.29 (s, 1H), 8.12-7.98 (m, 4H), 7.54 (dd, J = 8.6, 1.8 Hz, 1H), 7.13 (t, J = 54.3 Hz, 1H), 2.97-2.88 (m, 1H), 2.87-2.79 (m, 1H), 2.08-1.97 (m, 2H). $^{19}$F NMR (376 MHz, Methanol-d4) δ −77.80, −112.83 (d, J = 54.7 Hz). |
| 590 | 427.20 [M + H] | $^1$H NMR (400 MHz, Methanol-d4) δ 8.36 (d, J = 2.0 Hz, 1H), 8.29 (d, J = 2.9 Hz, 1H), 8.28 (s, 1H), 8.05-8.01 (m, 2H), 7.52-7.39 (m, 2H), 6.20 (tt, J = 54.7, 3.7 Hz, 1H), 4.34 (td, J = 13.8, 3.7 Hz, 2H), 2.09-2.02 (m, 1H), 1.95-1.86 (m, 1H). $^{19}$F NMR (376 MHz, Methanol-d4) δ −77.81, −128.44 (dt, J = 54.8, 13.8 Hz). |
| 591 | 469.20 [M + H] | $^1$H NMR (400 MHz, Methanol-d4) δ 9.38 (s, 1H), 8.66 (s, 1H), 8.40 (d, J = 1.9 Hz, 1H), 8.32 (s, 1H), 8.14 (s, 1H), 8.13 (s, 1H), 8.08 (d, J = 1.9 Hz, 1H), 5.44 (q, J = 8.6 Hz, 2H), 3.13 (t, J = 7.5 Hz, 2H), 2.34-2.22 (m, 1H), 2.22-2.12 (m, 1H). $^{19}$F NMR (376 MHz, Methanol-d4) δ −72.77 (t, J = 8.6 Hz), −78.01. |
| 592 | 380.20 [M + H] | $^1$H NMR (400 MHz, Methanol-d4) δ 8.22 (s, 1H), 8.19 (d, J = 2.0 Hz, 1H), 8.11-8.07 (m, 1H), 7.89 (d, J = 2.0 Hz, 1H), 7.79-7.76 (m, 1H), 7.23 (s, 1H), 4.65 (d, J = 7.2 Hz, 2H), 4.06-3.94 (m, 2H), 3.94-3.83 (m, 1H), 3.79-3.65 (m, 1H), 3.16-3.02 (m, 1H), 2.35-2.21 (m, 1H), 2.07-1.93 (m, 1H). $^{19}$F NMR (376 MHz, Methanol-d4) δ −77.95. |
| 593 | 337.20 [M + H] | $^1$H NMR (400 MHz, Methanol-d4) δ 8.18 (s, 1H), 8.11 (d, J = 1.8 Hz, 1H), 7.80 (d, J = 1.8 Hz, 1H), 7.10 (s, 1H), 4.11-3.94 (m, 2H), 3.93-3.80 (m, 1H), 3.71-3.61 (m, 1H), 2.73-2.56 (m, 1H), 2.50-2.43 (m, 2H), 2.38 (t, J = 2.6 Hz, 1H), 2.35-2.25 (m, 1H), 2.07-1.96 (m, 1H). |
| 594 | 486.20 [M + H] | $^1$H NMR (400 MHz, Methanol-d4) δ 8.37 (d, J = 1.9 Hz, 1H), 8.29 (s, 1H), 8.14 (d, J = 2.3 Hz, 1H), 8.09 (s, 1H), 8.06 (d, J = 1.9 Hz, 1H), 7.61 (d, J = 8.4 Hz, 1H), 7.07 (dd, J = 8.4, 6.0 Hz, 1H), 5.22 (q, J = 8.5 Hz, 2H), 3.09-2.99 (m, 1H), 2.91-2.80 (m, 1H), 2.08-1.96 (m, 2H). $^{19}$F NMR (376 MHz, Methanol-d4) δ −73.69--73.79 (m), −77.83, −143.15--143.26 (m). |
| 595 | 486.20 [M + H] | $^1$H NMR (400 MHz, Methanol-d4) δ 8.36 (d, J = 1.9 Hz, 1H), 8.28 (s, 1H), 8.09 (s, 1H), 8.05 (s, 1H), 8.03 (d, J = 1.9 Hz, 1H), 7.63 (d, J = 5.8 Hz, 1H), 7.49 (d, J = 10.0 Hz, 1H), 5.24 (q, J = 8.7 Hz, 2H), 2.99-2.90 (m, 1H), 2.80-2.72 (m, 1H), 2.16-2.05 (m, 1H), 2.02-1.94 (m, 1H). $^{19}$F NMR (376 MHz, Methanol-d4) δ −72.97 (t, J = 8.7 Hz), −77.81, −128.41 (dd, J = 10.0, 5.8 Hz). |

TABLE 3-continued

Characterization Data

| Example No. | ES/MS m/z | NMR |
|---|---|---|
| 596 | 486.10 [M + H] | $^1$H NMR (400 MHz, Methanol-d4) δ 8.37 (d, J = 1.9 Hz, 1H), 8.29 (s, 1H), 8.16-8.14 (m, 1H), 8.05 (d, J = 1.9 Hz, 1H), 8.03 (s, 1H), 7.45 (s, 1H), 6.90-6.84 (m, 1H), 5.22 (q, J = 8.7 Hz, 2H), 2.98-2.88 (m, 1H), 2.87-2.78 (m, 1H), 2.08-1.95 (m, 2H). $^{19}$F NMR (376 MHz, Methanol-d4) δ −72.90 (t, J = 8.6 Hz), −77.85, −120.87 (d, J = 11.0 Hz). |
| 597 | 487.10 [M + H] | $^1$H NMR (400 MHz, Methanol-d4) δ 8.41 (s, 1H), 8.39 (d, J = 2.0 Hz, 1H), 8.30 (s, 1H), 8.09 (s, 1H), 8.08 (d, J = 2.0 Hz, 1H), 7.24 (s, 1H), 4.42-4.32 (m, 1H), 4.32-4.20 (m, 1H), 3.07-2.96 (m, 1H), 2.90-2.82 (m, 1H), 2.32-2.17 (m, 1H), 2.16-2.07 (m, 1H), 1.98-1.90 (m, 1H), 1.77-1.64 (m, 1H), 1.50-1.37 (m, 1H). $^{19}$F NMR (376 MHz, Methanol-d4) δ −77.97, −131.12--131.83 (m), −145.29--145.94 (m). |
| 598 | 495.20 [M + H] | $^1$H NMR (400 MHz, Methanol-d4) δ 8.41 (d, J = 2.0 Hz, 1H), 8.31 (s, 1H), 8.13-8.07 (m, 2H), 7.96 (d, J = 9.5 Hz, 1H), 7.72 (d, J = 8.1 Hz, 1H), 7.58 (s, 1H), 7.29-7.18 (m, 1H), 6.67 (d, J = 9.5 Hz, 1H), 5.34-5.10 (m, 2H), 2.96-2.88 (m, 1H), 2.88-2.81 (m, 1H), 2.10-1.98 (m, 2H). $^{19}$F NMR (376 MHz, Methanol-d4) δ −69.85 (t, J = 8.7 Hz). |
| 599 | 495.10 [M + H] | $^1$H NMR (400 MHz, Methanol-d4) δ 8.36-8.32 (m, 1H), 8.28 (s, 1H), 8.20 (d, J = 8.8 Hz, 1H), 8.03-7.99 (m, 2H), 7.82 (d, J = 8.4 Hz, 1H), 7.75-7.72 (m, 1H), 7.40 (dd, J = 8.4, 1.8 Hz, 1H), 7.02 (d, J = 8.8 Hz, 1H), 5.08-4.97 (m, 2H), 2.94-2.86 (m, 2H), 2.09-1.96 (m, 2H). $^{19}$F NMR (376 MHz, Methanol-d4) δ −75.96 (t, J = 8.7 Hz), −77.74. |
| 600 | 479.10 [M + H] | $^1$H NMR (400 MHz, Methanol-d4) δ 8.43 (s, 1H), 8.40 (d, J = 2.0 Hz, 1H), 8.31 (s, 1H), 8.11 (s, 1H), 8.10 (d, J = 2.0 Hz, 1H), 7.30 (s, 1H), 4.84-4.75 (m, 2H), 3.07-2.98 (m, 1H), 2.92-2.78 (m, 1H), 2.16-2.05 (m, 1H), 1.96-1.86 (m, 1H). $^{19}$F NMR (376 MHz, Methanol-d4) δ −76.13 (t, J = 8.2 Hz), −77.93. |
| 601 | 469.20 [M + H] | $^1$H NMR (400 MHz, Methanol-d4) δ 8.36 (d, J = 1.9 Hz, 1H), 8.29 (s, 1H), 8.14 (d, J = 8.2 Hz, 1H), 8.14 (s, 1H), 8.08 (s, 1H), 8.03 (d, J = 1.9 Hz, 1H), 7.37 (d, J = 8.2 Hz, 1H), 5.35-5.09 (m, 2H), 3.21-3.13 (m, 1H), 3.09-3.00 (m, 1H), 2.29-2.20 (m, 1H), 2.00-1.91 (m, 1H). $^{19}$F NMR (376 MHz, Methanol-d4) δ −72.76 (t, J = 8.8 Hz), −77.73. |
| 602 | 487.10 [M + H] | $^1$H NMR (400 MHz, Methanol-d4) δ 8.21 (s, 1H), 8.12 (s, 1H), 8.12 (d, J = 8.2 Hz, 1H), 7.71 (s, 1H), 7.48 (d, J = 6.6 Hz, 1H), 7.33 (d, J = 8.2 Hz, 1H), 5.36-5.08 (m, 2H), 3.27-3.18 (m, 1H), 3.12-3.04 (m, 1H), 2.20-2.12 (m, 1H), 2.07-1.99 (m, 1H). $^{19}$F NMR (376 MHz, Methanol-d4) δ −72.81 (t, J = 8.8 Hz), −78.13, −157.05 (d, J = 6.6 Hz). |
| 603 | 536.10 [M + H] | $^1$H NMR (400 MHz, Methanol-d4) δ 8.33 (d, J = 1.8 Hz, 1H), 8.27 (s, 1H), 8.00 (d, J = 1.8 Hz, 1H), 7.97 (s, 1H), 7.81 (d, J = 8.6 Hz, 1H), 7.72 (s, 1H), 7.40 (dd, J = 8.6, 1.6 Hz, 1H), 5.31 (q, J = 8.4 Hz, 2H), 3.00-2.90 (m, 1H), 2.88-2.78 (m, 1H), 2.08-1.95 (m, 2H). $^{19}$F NMR (376 MHz, Methanol-d4) δ −63.38 (q, J = 5.1 Hz), −72.15--72.27 (m), −77.80. |
| 604 | 487.00 [M + H] | $^1$H NMR (400 MHz, Methanol-d4) δ 9.37 (s, 1H), 8.68 (s, 1H), 8.22 (s, 1H), 8.15 (s, 1H), 7.75 (s, 1H), 7.45 (d, J = 6.8 Hz, 1H), 5.46 (q, J = 8.6 Hz, 2H), 3.29-3.20 (m, 1H), 3.11-3.03 (m, 1H), 2.35-2.26 (m, 1H), 2.19-2.09 (m, 1H). $^{19}$F NMR (376 MHz, Methanol-d4) δ −72.77 (t, J = 8.6 Hz), −77.92, −157.20 (d, J = 7.0 Hz). |
| 605 | 468.10 [M + H] | $^1$H NMR (400 MHz, Methanol-d4) δ 8.41 (s, 1H), 8.32 (d, J = 1.8 Hz, 1H), 8.27 (s, 1H), 7.99 (d, J = 1.8 Hz, 1H), 7.94 (s, 1H), 7.74-7.68 (m, 2H), 6.99 (d, J = 9.6 Hz, 1H), 4.31 (q, J = 10.1 Hz, 2H), 2.92-2.70 (m, 2H), 2.01-1.88 (m, 2H). $^{19}$F NMR (376 MHz, Methanol-d4) δ −66.51 (t, J = 10.1 Hz), −77.93. |
| 606 | 518.20 [M + H] | $^1$H NMR (400 MHz, Methanol-d4) δ 8.40 (d, J = 2.0 Hz, 1H), 8.31 (s, 1H), 8.08 (d, J = 2.0 Hz, 1H), 8.07 (s, 1H), 7.75-7.68 (m, 2H), 7.51-7.46 (m, 1H), 7.21 (t, J = 52.1 Hz, 1H), 5.31 (q, J = 8.5 Hz, 2H), 2.97-2.89 (m, 1H), 2.84-2.75 (m, 1H), 2.09-1.92 (m, 2H). $^{19}$F NMR (376 MHz, Methanol-d4) δ −72.28--72.39 (m), −77.83, −117.55--117.86 (m). |
| 607 | 536.20 [M + H] | $^1$H NMR (400 MHz, Methanol-d4) δ 8.34 (d, J = 1.8 Hz, 1H), 8.27 (s, 1H), 8.00 (d, J = 1.8 Hz, 1H), 7.99 (s, 1H), 7.82 (d, J = 8.6 Hz, 1H), 7.73 (s, 1H), 7.40-7.29 (m, 1H), 5.34 (q, J = 8.6 Hz, 2H), 3.00-2.91 (m, 1H), 2.90-2.83 (m, 1H), 2.11-1.97 (m, 2H). $^{19}$F NMR (376 MHz, Methanol-d4) δ −63.29, −72.80 (t, J = 8.6 Hz), −77.82. |
| 608 | 537.10 [M + H] | $^1$H NMR (400 MHz, Methanol-d4) δ 9.15 (s, 1H), 8.40 (d, J = 2.0 Hz, 1H), 8.31 (s, 1H), 8.14 (s, 1H), 8.08 (d, J = 2.0 Hz, 1H), 7.85 (s, 1H), 5.45-5.32 (m, 2H), 3.20-3.13 (m, 1H), 3.07-2.99 (m, 1H), 2.29-2.20 (m, 1H), 2.02-1.93 (m, 1H). $^{19}$F NMR (376 MHz, Methanol-d4) δ −63.29, −72.85 (t, J = 8.6 Hz), −77.90. |

TABLE 3-continued

Characterization Data

| Example No. | ES/MS m/z | NMR |
|---|---|---|
| 609 | 536.10 [M + H] | ¹H NMR (400 MHz, Methanol-d4) δ 8.42 (s, 1H), 8.36 (d, J = 1.9 Hz, 1H), 8.28 (s, 1H), 8.04 (d, J = 1.9 Hz, 1H), 8.01 (s, 1H), 7.76-7.68 (m, 1H), 7.17-7.08 (m, 1H), 4.20 (q, J = 10.2 Hz, 2H), 2.86-2.77 (m, 2H), 2.04-1.89 (m, 2H). ¹⁹F NMR (376 MHz, Methanol-d4) δ −61.40, −66.48 (t, J = 10.2 Hz), −77.90. |
| 610 | 487.10 [M + H] | ¹H NMR (400 MHz, Methanol-d4) δ 8.20 (s, 1H), 8.12 (s, 1H), 8.12 (d, J = 8.2 Hz, 1H), 7.67 (s, 1H), 7.43 (d, J = 6.7 Hz, 1H), 7.33 (d, J = 8.2 Hz, 1H), 5.35-5.07 (m, 2H), 3.26-3.20 (m, 1H), 3.11-3.04 (m, 1H), 2.20-2.11 (m, 1H), 2.07-1.98 (m, 1H). |
| 611 | 487.10 [M + H] | ¹H NMR (400 MHz, Methanol-d4) δ 9.42 (s, 1H), 8.74 (s, 1H), 8.24-8.20 (m, 2H), 7.77 (s, 1H), 7.47 (d, J = 6.8 Hz, 1H), 5.49 (q, J = 8.5 Hz, 2H), 3.30-3.25 (m, 1H), 3.15-3.02 (m, 1H), 2.40-2.27 (m, 1H), 2.19-2.11 (m, 1H). |
| 612 | 487.10 [M + H] | ¹H NMR (400 MHz, Methanol-d4) δ 9.42 (d, J = 0.9 Hz, 1H), 8.74 (d, J = 0.9 Hz, 1H), 8.24-8.19 (m, 2H), 7.77 (s, 1H), 7.47 (d, J = 6.8 Hz, 1H), 5.49 (q, J = 8.5 Hz, 2H), 3.11-3.03 (m, 1H), 2.41-2.27 (m, 1H), 2.21-2.09 (m, 1H). |
| 613 | 504.10 [M + H] | ¹H NMR (400 MHz, Methanol-d4) δ 8.24 (s, 1H), 8.09 (d, J = 1.0 Hz, 1H), 7.74 (s, 1H), 7.63 (d, J = 5.8 Hz, 1H), 7.53 (d, J = 6.6 Hz, 1H), 7.48 (d, J = 9.9 Hz, 1H), 5.32-5.21 (m, 2H), 3.07-2.97 (m, 1H), 2.91-2.81 (m, 1H), 2.08-1.93 (m, 2H). ¹⁹F NMR (376 MHz, Methanol-d4) δ −73.00 (t, J = 8.7 Hz), −78.15, −128.62--128.72 (m), −157.01 (d, J = 6.8 Hz). |
| 614 | 469.20 [M + H] | ¹H NMR (400 MHz, Methanol-d4) δ 8.63 (d, J = 1.5 Hz, 1H), 8.47 (d, J = 2.0 Hz, 1H), 8.35 (s, 1H), 8.32 (s, 1H), 8.21 (s, 1H), 8.16 (d, J = 2.0 Hz, 1H), 8.13 (s, 1H), 5.31 (q, J = 8.7 Hz, 2H), 3.07-2.97 (m, 1H), 2.91-2.84 (m, 1H), 2.21-2.13 (m, 1H), 2.13-2.06 (m, 1H). ¹⁹F NMR (376 MHz, Methanol-d4) δ −72.99 (t, J = 8.7 Hz), −78.12. |
| 615 | 487.10 [M + H] | ¹H NMR (400 MHz, Methanol-d4) δ 8.90 (d, J = 1.6 Hz, 1H), 8.42 (d, J = 2.0 Hz, 1H), 8.35 (d, J = 2.4 Hz, 1H), 8.32 (s, 1H), 8.21 (s, 1H), 8.10 (d, J = 2.2 Hz, 1H), 5.27 (q, J = 8.5 Hz, 2H), 3.24-3.13 (m, 2H), 2.29-2.17 (m, 1H), 2.07-1.97 (m, 1H). ¹⁹F NMR (376 MHz, Methanol-d4) δ −73.70--73.81 (m), −77.98, −155.45--155.76 (m) |
| 616 | 494.20 [M + H] | ¹H NMR (400 MHz, Methanol-d4) δ 8.46-8.39 (m, 1H), 8.36-8.31 (m, 1H), 8.17-8.09 (m, 1H), 7.80-7.74 (m, 1H), 7.72-7.66 (m, 1H), 7.55-7.45 (m, 1H), 5.76-5.56 (m, 1H), 3.61-3.48 (m, 1H), 3.47-3.35 (m, 1H), 3.33-3.18 (m, 1H), 3.08-2.93 (m, 2H), 2.93-2.80 (m, 1H), 2.11-1.95 (m, 2H). ¹⁹F NMR (376 MHz, Methanol-d4) δ −76.50--76.67 (m), −77.96. |
| 617 | 482.20 [M + H] | ¹H NMR (400 MHz, Methanol-d4) δ 8.41-8.34 (m, 1H), 8.32-8.28 (m, 1H), 8.09 (s, 1H), 8.07-8.05 (m, 2H), 7.77-7.72 (m, 1H), 7.60 (s, 1H), 7.20-7.10 (m, 1H), 5.61-5.48 (m, 1H), 2.98-2.88 (m, 1H), 2.86-2.76 (m, 1H), 2.12-2.02 (m, 1H), 2.02-1.94 (m, 1H), 1.90-1.82 (m, 3H). ¹⁹F NMR (376 MHz, Methanol-d4) δ −77.17 (d, J = 7.1 Hz), −77.26 (d, J = 7.1 Hz), −77.82. |
| 618 | 504.20 [M + H] | ¹H NMR (400 MHz, Methanol-d4) δ 8.22 (s, 1H), 8.13 (s, 1H), 7.68 (s, 1H), 7.51 (d, J = 6.6 Hz, 1H), 7.42 (s, 1H), 6.86 (d, J = 11.1 Hz, 1H), 5.22 (q, J = 8.8 Hz, 2H), 2.97-2.80 (m, 2H), 2.07-1.97 (m, 1H), 1.95-1.84 (m, 1H). ¹⁹F NMR (376 MHz, Methanol-d4) δ −72.92 (t, J = 8.7 Hz), −78.17, −121.17 (d, J = 11.1 Hz), −156.97 (d, J = 6.7 Hz). |
| 619 | 487.10 [M + H] | ¹H NMR (400 MHz, Methanol-d4) δ 8.63 (d, J = 1.8 Hz, 1H), 8.29 (s, 1H), 8.22 (s, 1H), 8.14 (s, 1H), 7.70 (s, 1H), 7.49 (d, J = 6.7 Hz, 1H), 5.31 (q, J = 8.6 Hz, 2H), 3.07-2.98 (m, 1H), 2.97-2.88 (m, 1H), 2.16-2.08 (m, 1H), 2.01-1.93 (m, 1H). ¹⁹F NMR (376 MHz, Methanol-d4) δ −72.98--73.13 (m), −78.18, −157.07 (d, J = 6.9 Hz). |
| 620 | 536.10 [M + H] | ¹H NMR (400 MHz, Methanol-d4) δ 8.35 (d, J = 1.9 Hz, 1H), 8.28 (s, 1H), 8.03 (d, J = 1.9 Hz, 1H), 8.01 (s, 1H), 7.81 (d, J = 8.5 Hz, 1H), 7.72 (s, 1H), 7.40 (dd, J = 8.5, 1.4 Hz, 1H), 5.31 (q, J = 8.5 Hz, 2H), 3.00-2.91 (m, 1H), 2.87-2.77 (m, 1H), 2.09-1.95 (m, 2H). ¹⁹F NMR (376 MHz, Methanol-d4) δ −63.38 (q, J = 5.2 Hz), −72.14--72.27 (m), −77.84. |
| 621 | 505.10 [M + H] | ¹H NMR (400 MHz, Methanol-d4) δ 8.89 (s, 1H), 8.35 (d, J = 2.2 Hz, 1H), 8.24 (s, 1H), 7.84 (s, 1H), 7.57 (d, J = 6.4 Hz, 1H), 5.26 (q, J = 8.5 Hz, 2H), 3.30-3.20 (m, 1H), 3.20-3.12 (m, 1H), 2.20-2.13 (m, 1H), 2.12-2.05 (m, 1H). ¹⁹F NMR (376 MHz, Methanol-d4) δ −73.68--73.80 (m), −78.21, −155.36--155.48 (m), −156.64 (d, J = 6.6 Hz). |
| 622 | 490.80 [M + H] | ¹H NMR (400 MHz, Methanol-d4) δ 8.60 (d, J = 5.3 Hz, 1H), 8.38 (d, J = 2.0 Hz, 1H), 8.28 (s, 1H), 8.07 (s, 1H), 8.06 (d, J = 2.0 Hz, 1H), 7.88-7.81 (m, 1H), 7.76-7.70 (m, 1H), 7.69-7.62 (m, 1H), 7.50 (s, 1H), 7.45-7.40 (m, 1H), 7.34-7.30 (m, 1H), 3.15-3.06 (m, 1H), 3.01-2.94 (m, 1H), 2.21-2.13 (m, 1H), 2.03-1.96 (m, 1H). ¹⁹F NMR (376 MHz, Methanol-d4) δ −58.41, −77.91. |

TABLE 3-continued

Characterization Data

| Example No. | ES/MS m/z | NMR |
|---|---|---|
| 623 | 459.10 [M + H] | $^1$H NMR (400 MHz, Methanol-d4) δ 8.61 (d, J = 5.4 Hz, 1H), 8.33 (d, J = 1.9 Hz, 1H), 8.27 (s, 1H), 8.02 (s, 1H), 8.00 (d, J = 1.9 Hz, 1H), 7.75-7.66 (m, 2H), 7.61-7.56 (m, 1H), 7.20-7.11 (m, 2H), 3.14-3.06 (m, 1H), 3.04-2.95 (m, 1H), 2.23-2.12 (m, 1H), 2.08-2.00 (m, 1H). $^{19}$F NMR (376 MHz, Methanol-d4) δ −77.81, −109.90-−110.16 (m), −114.35-−114.66 (m). |
| 624 | 537.20 [M + H] | $^1$H NMR (400 MHz, Methanol-d4) δ 9.12 (s, 1H), 8.37 (d, J = 1.9 Hz, 1H), 8.30 (s, 1H), 8.09 (s, 1H), 8.04 (d, J = 1.9 Hz, 1H), 7.89 (s, 1H), 5.34 (q, J = 8.5 Hz, 1H), 3.19-2.97 (m, 2H), 2.26-2.17 (m, 1H), 2.02-1.94 (m, 1H). $^{19}$F NMR (376 MHz, Methanol-d4) δ −63.74-−63.89 (m), −72.24-−72.39 (m), −77.82. |
| 625 | 454.20 [M + H] | $^1$H NMR (400 MHz, Methanol-d4) δ 8.36 (d, J = 1.9 Hz, 1H), 8.34 (d, J = 7.5 Hz, 1H), 8.28 (s, 1H), 8.04 (d, J = 1.9 Hz, 1H), 8.00 (s, 1H), 7.67 (s, 1H), 7.52 (s, 1H), 6.93 (dd, J = 7.5, 1.8 Hz, 1H), 2.87-2.73 (m, 2H), 1.99 (t, J = 7.5 Hz, 2H). $^{19}$F NMR (376 MHz, Methanol-d4) δ −64.76, −77.89. |
| 626 | 518.20 [M + H] | $^1$H NMR (400 MHz, Methanol-d4) δ 8.36 (d, J = 2.0 Hz, 1H), 8.29 (s, 1H), 8.04 (d, J = 2.0 Hz, 1H), 8.03 (s, 1H), 7.76 (d, J = 8.5 Hz, 1H), 7.67 (s, 1H), 7.35 (dd, J = 8.5, 1.6 Hz, 1H), 7.18 (t, J = 52.1 Hz, 1H), 5.29 (q, J = 8.6 Hz, 2H), 2.99-2.89 (m, 1H), 2.85-2.75 (m, 1H), 2.10-1.95 (m, 2H). $^{19}$F NMR (376 MHz, Methanol-d4) δ −72.12-−72.31 (m), −77.84, −117.52 (dq, J = 52.0, 5.5 Hz). |
| 627 | 495.10 [M + H] | $^1$H NMR (400 MHz, Methanol-d4) δ 9.04 (dd, J = 5.0, 1.6 Hz, 1H), 9.02-8.98 (m, 1H), 8.28 (d, J = 1.7 Hz, 1H), 8.25 (s, 1H), 7.92 (d, J = 1.7 Hz, 1H), 7.91 (s, 1H), 7.80 (dd, J = 8.5, 5.0 Hz, 1H), 7.66 (s, 1H), 7.26 (s, 1H), 4.94 (q, J = 8.3 Hz, 2H), 3.10-2.94 (m, 2H), 2.18-2.06 (m, 2H). $^{19}$F NMR (376 MHz, Methanol-d4) δ −75.99 (t, J = 8.3 Hz), −77.84. |
| 628 | 487.10 [M + H] | $^1$H NMR (400 MHz, Methanol-d4) δ 8.64 (d, J = 1.9 Hz, 1H), 8.32-8.27 (m, 1H), 8.22 (s, 1H), 8.15 (s, 1H), 7.71 (s, 1H), 7.49 (d, J = 6.7 Hz, 1H), 5.31 (q, J = 8.7 Hz, 2H), 3.08-2.98 (m, 1H), 2.98-2.87 (m, 1H), 2.17-2.09 (m, 1H), 2.04-1.91 (m, 1H). $^{19}$F NMR (376 MHz, Methanol-d4) δ −73.03 (t, J = 8.7 Hz), −78.18, −157.05 (d, J = 6.5 Hz). |
| 629 | 487.20 [M + H] | $^1$H NMR (400 MHz, Methanol-d4) δ 8.50 (s, 1H), 8.27 (s, 1H), 8.12 (d, J = 2.3 Hz, 1H), 8.10 (s, 1H), 7.59 (d, J = 8.4 Hz, 1H), 7.07 (dd, J = 8.4, 5.9 Hz, 1H), 5.21 (q, J = 8.5 Hz, 2H), 3.26-3.18 (m, 1H), 2.92-2.83 (m, 1H), 2.25-2.16 (m, 1H), 1.98-1.89 (m, 1H). $^{19}$F NMR (376 MHz, Methanol-d4) δ −73.70-−73.83 (m), −78.18, −143.42-−143.63 (m). |
| 630 | 505.20 [M + H] | $^1$H NMR (400 MHz, Methanol-d4) δ 8.88 (s, 1H), 8.34 (d, J = 2.2 Hz, 1H), 8.22 (s, 1H), 7.77 (s, 1H), 7.49 (d, J = 6.6 Hz, 1H), 5.26 (q, J = 8.5 Hz, 3H), 3.34-3.21 (m, 1H), 3.22-3.11 (m, 1H), 2.19-2.13 (m, 1H), 2.13-2.06 (m, 1H). $^{19}$F NMR (376 MHz, Methanol-d4) δ −73.76 (td, J = 8.4, 5.1 Hz), −78.15, −155.66-−155.77 (m), −156.98 (d, J = 6.4 Hz). |
| 631 | 504.10 [M + H] | $^1$H NMR (400 MHz, Methanol-d4) δ 8.36 (d, J = 1.9 Hz, 1H), 8.28 (s, 1H), 8.21 (d, J = 2.1 Hz, 1H), 8.06-8.01 (m, 2H), 6.80 (dd, J = 10.2, 4.3 Hz, 1H), 5.24 (q, J = 8.5 Hz, 2H), 3.08-2.96 (m, 1H), 2.90-2.81 (m, 1H), 2.08-1.95 (m, 2H). $^{19}$F NMR (376 MHz, Methanol-d4) δ −73.69 (td, J = 8.4, 5.5 Hz), −77.84, −125.10 (dd, J = 23.9, 10.2 Hz), −147.40-−147.65 (m). |
| 632 | 536.10 [M + H] | $^1$H NMR (400 MHz, Methanol-d4) δ 8.59 (s, 1H), 8.36 (d, J = 1.8 Hz, 1H), 8.29 (s, 1H), 8.05-8.01 (m, 2H), 7.72 (d, J = 9.5 Hz, 1H), 7.44 (d, J = 9.5 Hz, 1H), 4.49-4.30 (m, 2H), 2.97-2.91 (m, 1H), 2.91-2.82 (m, 1H), 2.11-2.02 (m, 1H), 2.02-1.94 (m, 1H). $^{19}$F NMR (376 MHz, Methanol-d4) δ −64.78, −65.01 (t, J = 10.1 Hz), −77.91. |
| 633 | 380.10 [M + H] | $^1$H NMR (400 MHz, DMSO-d6) δ 11.53-11.45 (m, 2H), 8.25 (s, 1H), 7.99 (d, J = 6.0 Hz, 1H), 7.74 (s, 1H), 7.47 (s, 1H), 7.39-7.25 (m, 4H), 2.87-2.78 (m, 1H), 2.75-2.65 (m, 1H), 2.14-2.04 (m, 1H), 1.77-1.67 (m, 1H). |
| 634 | 380.10 [M + H] | $^1$H NMR (400 MHz, DMSO-d6) δ 11.58-11.50 (m, 2H), 8.37-8.30 (m, 1H), 8.03 (d, J = 6.2 Hz, 1H), 7.88 (s, 1H), 7.57 (s, 1H), 7.40-7.34 (m, 2H), 7.32-7.25 (m, 2H), 2.85-2.76 (m, 1H), 2.76-2.68 (m, 1H), 2.10-2.00 (m, 1H), 1.82-1.70 (m, 1H). |
| 635 | 433.20 [M + H] | $^1$H NMR (400 MHz, Methanol-d4) δ 8.68 (s, 1H), 8.15 (s, 1H), 8.11-8.08 (m, 1H), 7.93-7.83 (m, 1H), 7.69-7.66 (m, 1H), 7.64 (s, 1H), 3.27-3.08 (m, 2H), 2.17-2.05 (m, 2H). |
| 636 | 469.10 [M + H] | $^1$H NMR (400 MHz, Methanol-d4) δ 9.05 (s, 1H), 8.32 (s, 1H), 8.16 (s, 1H), 8.11 (d, J = 1.4 Hz, 1H), 7.69 (d, J = 1.4 Hz, 1H), 7.69 (s, 1H), 7.64 (s, 1H), 5.25 (q, J = 8.7 Hz, 2H), 3.20-3.10 (m, 1H), 3.04-2.95 (m, 1H), 2.15-2.07 (m, 1H), 2.05-1.97 (m, 1H). $^{19}$F NMR (376 MHz, Methanol-d4) δ −72.97 (t, J = 8.8 Hz). |
| 637 | 537.20 [M + H] | $^1$H NMR (400 MHz, Methanol-d4) δ 9.10 (s, 1H), 8.16 (s, 1H), 8.11 (s, 1H), 7.79 (s, 1H), 7.69 (s, 1H), 7.64 (s, 1H), 5.37 (q, J = 8.6 Hz, 2H), 3.25-3.16 (m, 1H), 3.06-2.98 (m, 1H), 2.18-2.09 (m, 1H), 2.05-1.97 (m, 1H). $^{19}$F NMR (376 MHz, Methanol-d4) δ −63.30, −72.88 (t, J = 8.7 Hz). |

TABLE 3-continued

Characterization Data

| Example No. | ES/MS m/z | NMR |
|---|---|---|
| 638 | 505.20 [M + H] | $^1$H NMR (400 MHz, Methanol-d4) δ 8.88 (s, 1H), 8.34 (d, J = 2.2 Hz, 1H), 8.22 (s, 1H), 7.77 (s, 1H), 7.49 (d, J = 6.6 Hz, 1H), 5.26 (q, J = 8.5 Hz, 2H), 3.30-3.21 (m, 1H), 3.22-3.10 (m, 1H), 2.20-2.13 (m, 1H), 2.13-2.06 (m, 1H). $^{19}$F NMR (376 MHz, Methanol-d4) δ −73.76 (td, J = 8.5, 5.2 Hz), −78.15, −155.66--155.78 (m), −156.98 (d, J = 6.4 Hz). |
| 639 | 494.20 [M + H] | $^1$H NMR (400 MHz, Methanol-d4) δ 8.33 (d, J = 1.8 Hz, 1H), 8.27 (s, 1H), 7.99 (d, J = 1.8 Hz, 1H), 7.96 (s, 1H), 7.66 (d, J = 8.5 Hz, 1H), 7.57 (s, 1H), 7.41-7.33 (m, 1H), 5.56-5.43 (m, 1H), 3.00-2.88 (m, 2H), 2.82-2.73 (m, 1H), 2.06-1.89 (m, 2H). $^{19}$F NMR (376 MHz, Methanol-d4) δ −76.79 (d, J = 6.8 Hz), −77.86. |
| 640 | 494.10 [M + H] | $^1$H NMR (400 MHz, Methanol-d4) δ 8.34 (d, J = 1.9 Hz, 1H), 8.27 (s, 1H), 8.01 (d, J = 1.9 Hz, 1H), 7.97 (s, 1H), 7.67 (d, J = 8.5 Hz, 1H), 7.58 (s, 1H), 7.39-7.34 (m, 1H), 5.58-5.45 (m, 1H), 3.02-2.88 (m, 2H), 2.87-2.76 (m, 1H), 2.03-1.88 (m, 2H). $^{19}$F NMR (376 MHz, Methanol-d4) δ −76.81 (d, J = 6.9 Hz), −77.87. |
| 641 | 311.10 [M + H] | $^1$H NMR (400 MHz, Methanol-d4) δ 8.26-8.21 (m, 2H), 7.96 (d, J = 2.1 Hz, 1H), 7.51 (s, 1H), 3.86 (s, 2H), 3.16-3.10 (m, 1H), 2.29-2.17 (m, 2H), 1.64-1.53 (m, 2H). |
| 642 | 325.10 [M + H] | $^1$H NMR (400 MHz, DMSO-d6) δ 11.37 (s, 1H), 11.35 (d, J = 6.1 Hz, 1H), 8.04 (s, 1H), 7.92 (d, J = 6.1 Hz, 1H), 7.60 (s, 1H), 6.58 (bs, 1H), 3.61 (bs, 1H), 3.19 (bs, 1H), 2.70 (s, 1H), 1.83-1.61 (m, 4H), 1.61-1.53 (m, 1H), 1.45-1.33 (m, 1H). |
| 643 | 325.20 [M + H] | $^1$H NMR (400 MHz, DMSO-d6) δ 11.47 (d, J = 6.2 Hz, 1H), 11.42 (s, 1H), 8.17 (s, 1H), 7.97 (d, J = 6.2 Hz, 1H), 7.78 (s, 1H), 6.78 (s, 1H), 3.73 (bs, 1H), 3.27 (bs, 1H), 2.72 (s, 1H), 1.83-1.64 (m, 4H), 1.63-1.55 (m, 1H), 1.49-1.35 (m, 1H). |
| 644 | 361.10 [M + H] | $^1$H NMR (400 MHz, Methanol-d4) δ 8.20 (s, 1H), 8.16 (s, 1H), 7.86 (s, 1H), 7.33 (s, 1H), 5.30 (s, 1H), 3.98-3.84 (m, 1H), 3.53-3.47 (m, 1H), 2.95 (s, 1H), 2.40-2.21 (m, 1H), 2.14-1.89 (m, 3H) .; $^{19}$F NMR (376 MHz, Methanol-d4) δ −78.15, −92.03--93.17 (m), −114.17--115.45 (m). |
| 645 | 379.10 [M + H] | $^1$H NMR (400 MHz, Methanol-d4) δ 8.25-8.22 (m, 2H), 7.93 (d, J = 2.0 Hz, 1H), 7.34 (s, 1H), 4.38-4.31 (m, 1H), 4.21-4.12 (m, 2H), 4.06-3.98 (m, 1H), 2.41-2.32 (m, 1H), 1.60-1.51 (m, 1H), 1.07-0.98 (m, 1H). $^{19}$F NMR (376 MHz, Methanol-d4) δ −70.11. |
| 646 | 325.20 [M + H] | $^1$H NMR (400 MHz, Methanol-d4) δ 8.25-8.14 (m, 2H), 7.92 (bs, 1H), 7.63 (bs, 1H), 4.77-4.68 (m, 2H), 2.00-1.90 (m, 4H), 1.70-1.62 (m, 4H). |
| 647 | 339.10 [M + H] | $^1$H NMR (400 MHz, Methanol-d4) δ 8.23 (s, 1H), 8.20 (d, J = 2.0 Hz, 1H), 7.91 (d, J = 2.0 Hz, 1H), 7.41 (s, 1H), 4.38 (s, 1H), 3.89-3.76 (m, 2H), 2.18-2.07 (m, 3H), 1.99-1.77 (m, 6H). |
| 648 | 339.20 [M + H] | $^1$H NMR (400 MHz, Methanol-d4) δ 8.24 (s, 1H), 8.22 (d, J = 2.0 Hz, 1H), 7.93 (d, J = 2.0 Hz, 1H), 7.58 (s, 1H), 4.76 (bs, 2H), 2.22 (dd, J = 8.8, 4.6 Hz, 2H), 2.09-1.88 (m, 5H), 1.68-1.57 (m, 3H). |
| 649 | 338.20 [M + H] | $^1$H NMR (400 MHz, Methanol-d4) δ 8.19 (s, 1H), 8.12 (d, J = 1.7 Hz, 1H), 7.79 (d, J = 1.7 Hz, 1H), 7.08 (s, 1H), 4.47 (d, J = 11.0 Hz, 1H), 4.13-4.02 (m, 2H), 3.91 (d, J = 11.0 Hz, 1H), 2.66-2.56 (m, 1H), 2.35-2.21 (m, 1H), 1.65 (s, 3H). |
| 650 | 325.20 [M + H] | $^1$H NMR (400 MHz, Methanol-d4) δ 8.27 (s, 1H), 8.25 (d, J = 2.0 Hz, 1H), 7.94 (d, J = 2.0 Hz, 1H), 7.47 (s, 1H), 4.12 (s, 4H), 2.77-2.69 (m, 2H), 2.42-2.32 (m, 2H), 1.61-1.52 (m, 2H). |
| 651 | 339.20 [M + H] | $^1$H NMR (400 MHz, Methanol-d4) δ 8.21 (s, 1H), 8.16 (d, J = 1.9 Hz, 1H), 7.87 (d, J = 1.9 Hz, 1H), 7.51 (s, 1H), 4.79-4.75 (m, 1H), 3.79-3.65 (m, 1H), 3.53-3.38 (m, 1H), 2.58-2.44 (m, 1H), 2.01-1.58 (m, 8H). |
| 652 | 377.10 [M + H] | $^1$H NMR (400 MHz, Methanol-d4) δ 8.20 (s, 1H), 8.16 (d, J = 1.9 Hz, 1H), 7.85 (d, J = 1.9 Hz, 1H), 7.17 (s, 1H), 4.04-3.94 (m, 2H), 3.84 (s, 2H), 3.81 (s, 2H), 3.69 (s, 2H), 2.22-2.11 (m, 2H). |
| 653 | 341.10 [M + H] | $^1$H NMR (400 MHz, Methanol-d4) δ 8.17 (s, 1H), 8.11-8.08 (m, 1H), 7.80-7.76 (m, 1H), 7.06 (s, 1H), 4.81-4.67 (m, 4H), 4.17 (s, 2H), 3.88 (t, J = 7.0 Hz, 2H), 2.43 (t, J = 7.0 Hz, 2H). $^{19}$F NMR (376 MHz, Methanol-d4) δ −77.82. |
| 654 | 398.20 [M + H] | $^1$H NMR (400 MHz, Methanol-d4) δ 8.20 (s, 1H), 8.14 (d, J = 1.8 Hz, 1H), 7.84 (d, J = 1.8 Hz, 1H), 7.14 (s, 1H), 4.15-4.05 (m, 1H), 4.07-3.93 (m, 2H), 3.91-3.79 (m, 1H), 3.64-3.54 (m, 1H), 2.86-2.73 (m, 1H), 2.41 (d, J = 7.4 Hz, 2H), 2.37-2.26 (m, 1H), 1.94-1.77 (m, 1H), 1.18 (d, J = 6.6 Hz, 3H), 1.17 (d, J = 6.6 Hz, 3H). |
| 655 | 450.20 [M + H] | $^1$H NMR (400 MHz, Methanol-d4) δ 8.22 (s, 1H), 8.17 (d, J = 2.0 Hz, 1H), 7.86 (d, J = 2.0 Hz, 1H), 7.21 (s, 1H), 4.45 (d, J = 11.6 Hz, 1H), 4.26-4.14 (m, 3H), 4.07 (d, J = 11.6 Hz, 1H), 4.03-3.94 (m, 1H), 3.24-3.13 (m, 2H), 2.89-2.82 (m, 1H), 2.63-2.53 (m, 1H), 2.51-2.43 (m, 1H), 2.43-2.33 (m, 1H). $^{19}$F NMR (376 MHz, Methanol-d4) δ −64.61 (t, J = 10.7 Hz), −77.91. |

TABLE 3-continued

Characterization Data

| Example No. | ES/MS m/z | NMR |
|---|---|---|
| 656 | 382.20 [M + H] | $^1$H NMR (400 MHz, Methanol-d4) δ 8.21 (s, 1H), 8.14 (d, J = 1.8 Hz, 1H), 7.82 (d, J = 1.8 Hz, 1H), 7.13 (s, 1H), 4.48 (d, J = 11.4 Hz, 1H), 4.26-4.04 (m, 4H), 4.02-3.90 (m, 1H), 2.95-2.80 (m, 1H), 2.59-2.50 (m, 1H), 2.49-2.40 (m, 1H), 2.40-2.29 (m, 1H), 1.87 (s, 3H). |
| 657 | 410.20 [M + H] | $^1$H NMR (400 MHz, Methanol-d4) δ 8.20 (s, 1H), 8.14 (d, J = 1.8 Hz, 1H), 7.82 (d, J = 1.8 Hz, 1H), 7.15 (s, 1H), 4.43 (d, J = 11.4 Hz, 1H), 4.25-4.11 (m, 3H), 4.07 (d, J = 11.4 Hz, 1H), 4.01-3.89 (m, 1H), 2.88-2.77 (m, 1H), 2.61-2.38 (m, 3H), 2.39-2.30 (m, 1H), 1.07 (d, J = 6.8 Hz, 3H), 1.04 (d, J = 6.8 Hz, 3H). |
| 658 | 500.20 [M + H] | $^1$H NMR (400 MHz, Methanol-d4) δ 8.13 (s, 1H), 8.04 (s, 1H), 7.70 (s, 1H), 6.92 (s, 1H), 4.46-4.28 (m, 3H), 3.78-3.67 (m, 1H), 3.26-3.13 (m, 1H), 2.79-2.64 (m, 1H), 2.57-2.40 (m, 1H), 1.32-1.26 (m, 2H), 1.16-1.06 (m, 2H). $^{19}$F NMR (376 MHz, Methanol-d4) δ −75.71, −77.96, −110.80−−114.52 (m). |
| 659 | 434.20 [M + H] | $^1$H NMR (400 MHz, Methanol-d4) δ 8.18 (s, 1H), 8.12 (m, 1H), 7.82-7.78 (m, 1H), 7.12-7.03 (m, 1H), 4.44-4.28 (m, 3H), 4.04-3.93 (m, 1H), 3.82-3.72 (m, 1H), 2.74-2.64 (m, 1H), 2.51-2.37 (m, 1H), 1.17 (d, J = 6.6 Hz, 3H), 1.16 (d, J = 6.6 Hz, 3H). $^{19}$F NMR (376 MHz, Methanol-d4) δ −78.09, −111.05−−114.49 (m). |
| 660 | 476.20 [M + H] | $^1$H NMR (400 MHz, Methanol-d4) δ 8.14 (s, 1H), 8.07 (d, J = 1.6 Hz, 1H), 7.73 (d, J = 1.6 Hz, 1H), 6.98 (s, 1H), 4.45-4.29 (m, 3H), 3.78-3.69 (m, 1H), 3.23-3.13 (m, 1H), 2.77-2.65 (m, 1H), 2.51-2.41 (m, 1H), 2.38-2.33 (m, 6H). $^{19}$F NMR (376 MHz, Methanol-d4) δ −78.00, −111.09−−114.51 (m), −169.13−−169.21 (m). |
| 661 | 458.20 [M + H] | $^1$H NMR (400 MHz, Methanol-d4) δ 8.15 (s, 1H), 8.07 (d, J = 1.6 Hz, 1H), 7.73 (d, J = 1.6 Hz, 1H), 6.97 (s, 1H), 4.46-4.30 (m, 3H), 3.80-3.70 (m, 1H), 3.24-3.10 (m, 1H), 2.71-2.62 (m, 1H), 2.44 (s, 1H), 2.48-2.36 (m, 1H), 2.11 (s, 6H). $^{19}$F NMR (376 MHz, Methanol-d4) δ −77.96, −110.95−−114.72 (m). |
| 662 | 434.20 [M + H] | $^1$H NMR (400 MHz, Methanol-d4) δ 8.18 (s, 1H), 8.10 (d, J = 1.6 Hz, 1H), 7.77 (d, J = 1.6 Hz, 1H), 7.06 (s, 1H), 4.18-3.99 (m, 4H), 3.96-3.85 (m, 1H), 2.42-2.19 (m, 2H), 1.23 (d, J = 6.6 Hz, 3H), 1.20 (d, J = 6.6 Hz, 3H). $^{19}$F NMR (376 MHz, Methanol-d4) δ −77.82, −111.64−−116.10 (m). |
| 663 | 422.20 [M + H] | $^1$H NMR (400 MHz, Methanol-d4) δ 8.22 (s, 1H), 8.19 (d, J = 1.9 Hz, 1H), 7.93 (s, 1H), 7.90 (d, J = 1.9 Hz, 1H), 7.20 (s, 1H), 4.18-4.02 (m, 1H), 4.03-3.89 (m, 1H), 3.90-3.77 (m, 1H), 3.78-3.64 (m, 1H), 3.03-2.88 (m, 2H), 2.87-2.72 (m, 1H), 2.38-2.24 (m, 1H), 2.02-1.88 (m, 1H), 1.59 (d, J = 6.8 Hz, 3H), 1.59 (d, J = 6.8 Hz, 3H). |
| 664 | 520.10 [M + H] | $^1$H NMR (400 MHz, Methanol-d4) δ 8.11 (s, 1H), 7.23 (d, J = 7.0 Hz, 1H), 6.71 (s, 1H), 5.51-5.37 (m, 1H), 4.61-4.44 (m, 1H), 4.40-4.09 (m, 3H), 1.32-1.20 (m, 2H), 1.19-1.06 (m, 2H). $^{19}$F NMR (376 MHz, Methanol-d4) δ −76.35, −78.10, −108.98−−110.78 (m), −124.10−−125.53 (m), −157.66 (d, J = 7.3 Hz). |
| 665 | 546.20 [M + H] | $^1$H NMR (400 MHz, Methanol-d4) δ 8.11 (s, 1H), 7.24 (d, J = 7.1 Hz, 1H), 6.71 (s, 1H), 5.46-5.35 (m, 1H), 4.62-4.43 (m, 1H), 4.41-4.02 (m, 3H), 2.24 (s, 6H). $^{19}$F NMR (376 MHz, Methanol-d4) δ −73.59, −78.24, −109.20−−110.65 (m), −123.90−−125.78 (m), −157.61 (d, J = 7.1 Hz). |
| 666 | 515.10 [M + H] | $^1$H NMR (400 MHz, Methanol-d4) δ 9.27 (d, J = 1.7 Hz, 1H), 8.11 (s, 1H), 7.76-7.72 (m, 1H), 7.24 (d, J = 7.1 Hz, 1H), 6.75 (s, 1H), 6.24-6.15 (m, 1H), 4.72-4.33 (m, 4H). $^{19}$F NMR (376 MHz, Methanol-d4) δ −66.64, −77.87, −109.13−−110.34 (m), −109.15−−124.05 (m), −157.68 (d, J = 6.4 Hz). |
| 667 | 301.20 [M + H] | $^1$H NMR (400 MHz, DMSO-d6) δ 11.46 (d, 2H), 8.18 (s, 1H), 8.00 (d, 1H), 7.82 (s, 1H), 7.52 (t, 1H), 6.98 (s, 1H), 3.15 (t, 2H), 2.02 (dt, 1H), 0.97 (d, 6H). |
| 668 | 315.18 [M + H] | $^1$H NMR (400 MHz, DMSO-d6) δ 11.53-11.44 (m, 2H), 8.25 (d, 1H), 8.01 (d, 1H), 7.93 (d, 1H), 7.27 (t, 1H), 7.16 (s, 1H), 3.19 (d, 2H), 1.00 (s, 9H). |
| 669 | 303.13 [M + H] | $^1$H NMR (400 MHz, DMSO-d6) δ 11.44 (d, 2H), 8.16 (d, 1H), 7.98 (d, 1H), 7.76 (s, 1H), 7.37 (s, 1H), 6.95 (s, 1H), 3.61 (t, 2H), 3.54-3.46 (m, 2H), 3.31 (s, 3H). |
| 670 | 309.09 [M + H] | $^1$H NMR (400 MHz, DMSO-d6) δ 11.46-11.26 (m, 2H), 8.11 (d, 1H), 7.95 (d, 1H), 7.67 (d, 1H), 7.61 (t, 1H), 6.24 (tt, 1H), 3.86 (s, 1H), 3.76-3.56 (m, 2H). |
| 671 | 428.96 [M + H] | $^1$H NMR (400 MHz, DMSO-d6) δ 11.37 (s, 2H), 8.08 (d, 1H), 7.97-7.89 (m, 1H), 7.60 (d, 1H), 7.25 (d, 2H), 6.95 (s, 1H), 6.89 (d, 1H), 6.87 (d, 1H), 4.94 (s, 2H), 4.71 (t, 2H), 3.72 (s, 3H). |
| 672 | 327.13 [M + H] | $^1$H NMR (400 MHz, DMSO-d6) δ 11.41 (dd, 2H), 8.15-8.08 (m, 1H), 7.95 (dd, 1H), 7.85 (t, 1H), 7.64 (d, 1H), 4.36-4.31 (m, 2H). |

TABLE 3-continued

Characterization Data

| Example No. | ES/MS m/z | NMR |
|---|---|---|
| 673 | 350.21 [M + H] | ¹H NMR (400 MHz, DMSO-d6) δ 11.55 (d, 2H), 8.28 (d, 1H), 8.05 (d, 1H), 7.78 (s, 1H), 7.47-7.37 (m, 3H), 7.33 (dd, 2H), 7.30-7.20 (m, 1H), 4.56 (t, 2H), 3.19 (t, 2H). |
| 674 | 364.12 [M + H] | ¹H NMR (400 MHz, DMSO-d6) δ 11.60-11.52 (m, 2H), 8.31 (d, 1H), 8.05 (d, 1H), 7.83 (s, 1H), 7.48-7.40 (m, 3H), 7.34 (dd, 2H), 7.30-7.21 (m, 1H), 4.49 (dd, 1H), 4.40 (dd, 1H), 3.39 (p, 1H), 1.41 (d, 3H). |
| 675 | 328.15 [M + H] | ¹H NMR (400 MHz, DMSO-d6) δ 11.55 (d, 2H), 8.29 (d, 1H), 8.05 (d, 1H), 7.74 (d, 1H), 7.41 (s, 1H), 5.26 (q, 2H). |
| 676 | 370.16 [M + H] | ¹H NMR (400 MHz, DMSO-d6) δ 11.56 (d, 2H), 8.31 (d, 1H), 8.04 (d, 1H), 7.82 (s, 1H), 7.42 (s, 1H), 4.39 (s, 2H), 1.32 (s, 6H). |
| 677 | 324.13 [M + H] | ¹H NMR (400 MHz, DMSO-d6) δ 11.63-11.54 (m, 2H), 8.35 (d, 1H), 8.07 (d, 1H), 7.86 (d, 1H), 7.49 (s, 1H), 4.74 (t, 2H), 1.83 (t, 3H). |
| 678 | 302.14 [M + H] | ¹H NMR (400 MHz, DMSO-d6) δ 11.65-11.50 (m, 2H), 8.34 (d, 1H), 8.07 (d, 1H), 7.88 (s, 1H), 7.46 (s, 1H), 4.13 (d, 2H), 2.18 (dq, 1H), 1.06 (d, 6H). |
| 679 | 315.10 [M + H] | ¹H NMR (400 MHz, DMSO-d6) δ 11.64 (dd, 1H), 11.58 (d, 1H), 8.39 (d, 1H), 8.09 (d, 1H), 7.97 (d, 1H), 7.52 (s, 1H), 4.02 (s, 2H), 1.09 (s, 9H). |
| 680 | 316.07 [M + H] | ¹H NMR (400 MHz, DMSO-d6) δ 11.60 (dd, 1H), 11.56 (d, 1H), 8.36 (d, 1H), 8.07 (d, 1H), 7.92 (d, 1H), 7.50 (s, 1H), 4.74 (p, 1H), 2.08-1.98 (m, 1H), 1.35 (d, 3H), 1.01 (dd, 6H). |
| 681 | 342.15 [M + H] | ¹H NMR (400 MHz, DMSO-d6) δ 11.53 (s, 2H), 8.25 (d, 1H), 8.04 (d, 1H), 7.72 (s, 1H), 7.36 (s, 1H), 4.59 (t, 2H), 2.97 (qt, 2H). |
| 682 | 386.10 [M + H] | ¹H NMR (400 MHz, DMSO-d6) δ 11.55 (d, 2H), 8.30 (d, 1H), 8.04 (d, 1H), 7.77 (d, 1H), 7.71 (dd, 2H), 7.63-7.51 (m, 3H), 7.46 (s, 1H), 5.09 (t, 2H). |
| 683 | 337.17 [M + H] | ¹H NMR (400 MHz, DMSO-d6) δ 11.42-11.33 (m, 2H), 8.07 (d, 1H), 7.95 (d, 1H), 7.62 (d, 1H), 6.64 (s, 1H), 4.39-4.08 (m, 1H), 3.97-3.67 (m, 3H), 3.13 (s, 1H), 2.21 (dt, 1H), 2.02 (dt, 1H), 1.74 (s, 3H). |
| 684 | 323.18 [M + H] | ¹H NMR (400 MHz, DMSO-d6) δ 11.38 (dd, 2H), 8.05 (d, 1H), 7.94 (d, 1H), 7.59 (d, 1H), 6.61 (s, 1H), 4.30-4.07 (m, 1H), 3.95-3.60 (m, 3H), 3.28-3.19 (m, 1H), 3.10 (d, 1H), 2.35-2.22 (m, 1H), 2.10-1.97 (m, 1H). |
| 685 | 312.10 [M + H] | ¹H NMR (400 MHz, DMSO-d6) δ 11.58 (d, 2H), 8.36 (s, 1H), 8.08 (d, 1H), 7.84 (s, 2H), 1.55 (s, 6H). |
| 686 | 310.19 [M + H] | ¹H NMR (400 MHz, DMSO-d6) δ 11.57 (d, 2H), 8.32 (d, 1H), 8.06 (d, 1H), 7.82 (s, 1H), 7.78 (s, 1H), 1.38 (s, 9H). |
| 687 | 340.12 [M + H] | ¹H NMR (400 MHz, DMSO-d6) δ 11.63-11.50 (m, 2H), 8.34 (d, 1H), 8.07 (d, 1H), 7.90-7.80 (m, 1H), 7.47 (s, 1H), 4.76 (t, 2H), 3.85 (t, 2H). |
| 688 | 338.14 [M + H] | ¹H NMR (400 MHz, DMSO-d6) δ 11.69-11.53 (m, 2H), 8.41 (d, 1H), 8.08 (d, 1H), 7.94 (d, 1H), 7.58 (s, 1H), 4.76 (t, 2H), 2.14 (tq, 2H), 1.04 (t, 3H). |
| 689 | 350.12 [M + H] | ¹H NMR (400 MHz, DMSO-d6) δ 11.59 (dd, 2H), 8.38 (d, 1H), 8.08 (d, 1H), 7.90 (d, 1H), 7.56 (s, 1H), 4.85 (t, 2H), 1.63 (s, 1H), 0.77-0.61 (m, 4H). |
| 690 | 378.12 [M + H] | ¹H NMR (400 MHz, DMSO-d6) δ 11.62-11.52 (m, 2H), 8.35 (d, 1H), 8.06 (d, 1H), 7.83 (d, 1H), 7.53 (s, 1H), 5.37 (t, 2H). |
| 691 | 364.11 [M + H] | ¹H NMR (400 MHz, DMSO-d6) δ 11.70-11.63 (m, 1H), 11.59 (d, 1H), 8.44 (d, 1H), 8.10 (d, 1H), 8.04 (d, 1H), 7.64 (s, 1H), 7.43 (d, 3H), 7.34 (t, 2H), 7.28-7.22 (m, 1H), 4.52 (dd, 1H), 4.42 (dd, 1H), 3.39 (q, 1H), 1.43 (d, 3H). |
| 692 | 387.12 [M + H] | ¹H NMR (400 MHz, DMSO-d6) δ 11.65-11.60 (m, 1H), 11.58 (d, 1H), 8.73 (dd, 1H), 8.38 (d, 1H), 8.11-8.05 (m, 2H), 7.92-7.86 (m, 2H), 7.66-7.60 (m, 2H), 5.25 (t, 2H). |
| 693 | 390.12 [M + H] | ¹H NMR (400 MHz, DMSO-d6) δ 11.57 (s, 1H), 11.55 (s, 1H), 8.31 (d, 1H), 8.07 (d, 1H), 7.78 (d, 1H), 7.51 (s, 1H), 7.43 (s, 1H), 7.01 (d, 1H), 5.32 (t, 2H), 3.88 (s, 3H). |
| 694 | 425.12 [M + H] | ¹H NMR (400 MHz, DMSO-d6) δ 11.59 (d, 2H), 8.34 (d, 1H), 8.07 (d, 1H), 7.83 (s, 1H), 7.47 (s, 1H), 7.43 (d, 1H), 4.84 (t, 2H), 4.51 (t, 2H), 3.71-3.63 (m, 1H), 1.15 (d, 6H). |
| 695 | 417.06 [M + H] | ¹H NMR (400 MHz, DMSO-d6) δ 11.68-11.63 (m, 1H), 11.61 (d, 1H), 8.44 (d, 1H), 8.16 (ddd, 1H), 8.09 (d, 1H), 8.01 (d, 1H), 7.77 (ddd, 1H), 7.67 (s, 1H), 7.45-7.38 (m, 1H), 7.06 (ddd, 1H), 6.99-6.90 (m, 1H), 4.98 (t, 2H), 4.87 (t, 2H). |
| 696 | 466.16 [M + H] | ¹H NMR (400 MHz, DMSO-d6) δ 11.62-11.54 (m, 2H), 8.35 (d, 1H), 8.06 (d, 1H), 7.84 (d, 1H), 7.48 (s, 1H), 4.98-4.86 (m, 4H), 4.80 (t, 2H). |
| 697 | 504.10 [M + H] | ¹H NMR (400 MHz, DMSO-d6) δ 11.62-11.52 (m, 2H), 8.04 (d, J = 6.2 Hz, 1H), 7.76 (s, 1H), 7.69 (d, J = 8.5 Hz, 1H), 7.63-7.50 (m, 2H), 7.20 (dd, J = 8.5, 1.3 Hz, 1H), 5.31 (q, J = 9.0 Hz, 2H), 4.03 (q, J = 7.1 Hz, 0H), 3.04 (ddd, J = 9.0, 6.3, 4.4 Hz, 1H), 2.83 (ddd, J = |

TABLE 3-continued

Characterization Data

| Example No. | ES/MS m/z | NMR |
|---|---|---|
| | | 8.9, 6.0, 4.4 Hz, 1H), 2.24-2.10 (m, 1H), 1.99 (s, 0H), 1.95-1.85 (m, 1H), $^{19}$F NMR (376 MHz, DMSO-d6) δ −70.28 (t, J = 8.9 Hz), −133.91, −155.45 (d, J = 7.1 Hz). |
| 698 | 512.20 [M + H] | $^1$H NMR (400 MHz, DMSO-d6) δ 11.57 (d, J = 7.1 Hz, 2H), 8.36 (d, J = 1.5 Hz, 1H), 8.21 (d, J = 1.8 Hz, 1H), 8.04 (d, J = 6.0 Hz, 1H), 7.90 (s, 1H), 7.61 (s, 1H), 7.52 (d, J = 1.7 Hz, 1H), 4.68 (q, J = 9.3 Hz, 2H), 2.89 (ddd, J = 9.4, 6.3, 4.4 Hz, 1H), 2.84-2.74 (m, 1H), 2.13 (dt, J = 9.0, 5.4 Hz, 1H), 1.88 (dt, J = 8.8, 5.6 Hz, 1H), 1.32 (s, 6H). $^{19}$F NMR (377 MHz, DMSO-d6) δ −69.45 (t, J = 9.3 Hz), −75.33 |
| 699 | 512.20 [M + H] | $^1$H NMR (400 MHz, DMSO-d6) δ 11.74 (d, J = 6.4 Hz, 1H), 11.63 (d, J = 1.9 Hz, 1H), 8.56 (d, J = 1.8 Hz, 1H), 8.24-8.21 (m, 2H), 8.11 (d, J = 6.3 Hz, 1H), 7.81 (s, 1H), 7.60 (d, J = 1.7 Hz, 1H), 4.71 (q, J = 9.4 Hz, 2H), 3.05 (dd, J = 9.1, 4.9 Hz, 1H), 2.91-2.76 (m, 1H), 2.06-1.84 (m, 2H), 1.33 (d, J = 1.1 Hz, 6H). $^{19}$F NMR (376 MHz, DMSO-d6) δ −69.39 (t, J = 9.3 Hz), −71.64. |
| 700 | 512.20 [M + H] | $^1$H NMR (400 MHz, Acetonitrile-d3) δ 9.35 (s, 1H), 9.25 (s, 1H), 8.44 (s, 1H), 8.19-8.09 (m, 2H), 7.98-7.89 (m, 2H), 7.44 (s, 1H), 4.59 (q, J = 8.9 Hz, 2H), 3.43-3.33 (m, 1H), 3.19-3.09 (m, 1H), 2.21 (dt, J = 9.2, 5.9 Hz, 1H), 2.10-1.97 (m, 1H), 1.49 (s, 6H). $^{19}$F NMR (376 MHz, Acetonitrile-d3) δ −71.20 (t, J = 9.0 Hz), −76.99. |
| 701 | 536.20 [M + H] | $^1$H NMR (400 MHz, DMSO-d6) δ 11.67 (d, J = 6.1 Hz, 1H), 11.60 (s, 1H), 8.48 (s, 1H), 8.26 (d, J = 1.6 Hz, 1H), 8.07 (dd, J = 15.3, 7.2 Hz, 3H), 7.76 (s, 1H), 7.44 (d, J = 8.2 Hz, 1H), 5.44-5.18 (m, 2H), 3.16-3.06 (m, 2H), 2.12-2.01 (m, 2H). $^{19}$F NMR (376 MHz, DMSO-d6) δ −56.63, −70.50 (t, J = 9.2 Hz). |
| 702 | 529.20 [M + H] | $^1$H NMR (400 MHz, DMSO-d6) δ 11.53 (d, J = 3.8 Hz, 2H), 8.03 (d, J = 6.5 Hz, 1H), 7.55 (d, J = 7.1 Hz, 1H), 7.47 (s, 1H), 7.31 (d, J = 7.7 Hz, 1H), 7.13 (s, 1H), 7.00 (dd, J = 7.8, 1.4 Hz, 1H), 4.63 (q, J = 9.4 Hz, 2H), 2.92-2.82 (m, 1H), 2.76-2.67 (m, 1H), 2.12 (dt, J = 9.8, 5.3 Hz, 1H), 1.86-1.74 (m, 1H), 1.30 (s, 6H). $^{19}$F NMR (376 MHz, DMSO-d6) δ −69.31 (t, J = 9.3 Hz), −74.96, −155.58 (d, J = 7.2 Hz). |
| 703 | 511.20 [M + H] | $^1$H NMR (400 MHz, DMSO-d6) δ 11.62 (dd, J = 24.9, 4.1 Hz, 2H), 8.46 (s, 1H), 8.08 (d, J = 6.2 Hz, 2H), 7.69 (s, 1H), 7.34 (d, J = 7.7 Hz, 1H), 7.16 (s, 1H), 7.05-6.98 (m, 1H), 4.65 (q, J = 9.4 Hz, 2H), 2.91-2.77 (m, 2H), 2.04-1.79 (m, 2H). $^{19}$F NMR (376 MHz, DMSO-d6) δ −69.26 (t, J = 9.4 Hz). |
| 704 | 468.10 [M + H] | $^1$H NMR (400 MHz, DMSO-d6) δ 11.69 (dd, J = 45.4, 3.7 Hz, 2H), 8.57 (d, J = 1.8 Hz, 1H), 8.22 (s, 1H), 8.12 (d, J = 6.2 Hz, 1H), 8.00-7.83 (m, 2H), 7.54 (d, J = 3.6 Hz, 1H), 7.23 (d, J = 8.0 Hz, 1H), 6.58 (d, J = 3.6 Hz, 1H), 5.22 (ddq, J = 53.4, 15.3, 9.2 Hz, 2H), 3.18 (dt, J = 9.5, 5.5 Hz, 1H), 3.00 (ddd, J = 9.4, 6.1, 4.0 Hz, 1H), 2.09 (d, J = 8.0 Hz, 1H), 2.02-1.90 (m, 1H). $^{19}$F NMR (376 MHz, DMSO-d6) δ −70.59 (t, J = 9.4 Hz). |
| 705 | 468.10 [M + H] | $^1$H NMR (400 MHz, DMSO-d6) δ 15.52 (s, 1H), 11.82-11.75 (m, 1H), 11.61 (d, J = 1.9 Hz, 1H), 9.24 (s, 1H), 8.52 (s, 1H), 8.39 (s, 1H), 8.12 (d, J = 6.3 Hz, 2H), 7.95 (d, J = 3.5 Hz, 1H), 7.86 (s, 1H), 7.13 (d, J = 3.4 Hz, 1H), 5.54 (q, J = 9.1 Hz, 2H), 3.31 (d, J = 19.1 Hz, 2H), 2.33 (dt, J = 9.1, 5.7 Hz, 1H), 2.22 (dt, J = 8.8, 5.7 Hz, 1H). $^{19}$F NMR (376 MHz, DMSO-d6) δ −70.64 (t, J = 9.0 Hz). |
| 706 | 486.20 [M + H] | $^1$H NMR (400 MHz, DMSO-d6) δ 11.73-11.66 (m, 1H), 11.60 (d, J = 2.0 Hz, 1H), 9.36 (s, 1H), 8.47 (s, 1H), 8.29 (s, 1H), 8.10 (d, J = 6.2 Hz, 1H), 8.05-7.98 (m, 2H), 7.80 (s, 1H), 5.41 (q, J = 8.9 Hz, 2H), 3.15 (s, 1H), 2.35-2.27 (m, 1H), 2.17 (dt, J = 8.9, 5.6 Hz, 1H). $^{19}$F NMR (376 MHz, DMSO-d6) δ −70.67 (t, J = 9.0 Hz), −168.57. |
| 707 | 495.20 [M + H] | $^1$H NMR (400 MHz, DMSO-d6) δ 11.56 (d, J = 3.8 Hz, 2H), 8.36 (s, 1H), 8.11-8.01 (m, 2H), 7.90 (s, 1H), 7.73-7.59 (m, 3H), 7.43 (d, J = 7.4 Hz, 1H), 6.72 (d, J = 7.4 Hz, 1H), 4.94 (qd, J = 9.3, 2.6 Hz, 2H), 2.99 (ddd, J = 9.4, 6.2, 4.4 Hz, 1H), 2.85 (dt, J = 9.8, 5.1 Hz, 1H), 2.10 (dt, J = 8.9, 5.3 Hz, 1H), 1.88 (dt, J = 8.6, 5.4 Hz, 1H). $^{19}$F NMR (376 MHz, DMSO-d6) δ −69.93 (t, J = 9.2 Hz), −74.99. |
| 708 | 495.10 [M + H] | $^1$H NMR (400 MHz, DMSO-d6) δ 11.58 (s, 1H), 8.41 (s, 1H), 8.10-8.03 (m, 1H), 8.08-7.94 (m, 3H), 7.89 (d, J = 9.0 Hz, 1H), 7.74-7.64 (m, 2H), 7.53 (s, 0H), 6.18 (d, J = 7.8 Hz, 1H), 5.35 (q, J = 8.8 Hz, 2H), 2.99-2.90 (m, 1H), 2.85 (s, 1H), 2.90-2.80 (m, 0H), 2.63 (s, 0H), 2.05 (d, J = 7.5 Hz, 1H), 1.94-1.85 (m, 1H). $^{19}$F NMR (376 MHz, DMSO-d6) δ −69.77 (t, J = 9.0 Hz), −75.07-−75.22 (m). |
| 709 | 495.10 [M + H] | $^1$H NMR (400 MHz, DMSO-d6) δ 11.70 (d, J = 6.3 Hz, 1H), 11.60 (d, J = 2.0 Hz, 1H), 9.24 (d, J = 6.4 Hz, 1H), 8.48 (s, 1H), 8.28 (d, J = 8.9 Hz, 1H), 8.21 (d, J = 1.9 Hz, 1H), 8.09 (dd, J = 7.5, 4.3 Hz, 2H), 8.00 (dd, J = 9.0, 2.0 Hz, 1H), 7.76 (s, 1H), 7.67 (d, J = 6.5 Hz, 1H), 5.41 (q, J = 8.5 Hz, 2H), 3.19 (ddd, J = 9.1, 6.2, 4.5 Hz, 1H), 3.11 (s, 1H), 2.14 (dt, J = 9.0, 5.6 Hz, 1H), 2.00 (dt, J = 8.5, 5.6 Hz, 1H). $^{19}$F NMR (376 MHz, DMSO-d6) δ −72.63 (t, J = 8.6 Hz). |

TABLE 3-continued

Characterization Data

| Example No. | ES/MS m/z | NMR |
|---|---|---|
| 710 | 495.1 [M + H] | 1NMR (400 MHz, DMSO-d6) δ 11.68 (d, J = 6.4 Hz, 1H), 11.61 (d, J = 2.0 Hz, 1H), 9.41 (s, 1H), 8.51-8.38 (m, 3H), 8.16-8.05 (m, 3H), 7.86-7.75 (m, 2H), 5.18 (q, J = 8.7 Hz, 2H), 3.26-3.09 (m, 2H), 2.19 (dt, J = 9.1, 5.5 Hz, 1H), 2.06 (dt, J = 8.6, 5.5 Hz, 1H). $^{19}$F NMR (376 MHz, DMSO-d6) δ −72.93 (t, J = 8.8 Hz). |
| 711 | 549.0 [M + H] | $^1$H NMR (400 MHz, DMSO-d6) δ 11.43-11.36 (m, 2H), 8.14-8.13 (m, 1H), 8.08 (d, J = 1.2 Hz, 1H), 7.94 (d, J = 6.1 Hz, 1H), 7.75 (d, J = 8.8 Hz, 1H), 7.61-7.59 (m, 1H), 7.57 (d, J = 1.3 Hz, 1H), 7.00 (dd, J = 8.8, 2.1 Hz, 1H), 6.64 (s, 1H), 5.54-5.29 (m, 3H), 4.73-4.09 (m, 4H). |
| 712 | 520.0 [M + H] | $^1$H NMR (400 MHz, DMSO-d6) δ 11.44-11.35 (m, 2H), 8.19 (d, J = 8.7 Hz, 1H), 8.09 (d, J = 1.2 Hz, 1H), 7.93 (d, J = 6.1 Hz, 1H), 7.73 (d, J = 2.6 Hz, 1H), 7.65 (dd, J = 8.7, 2.6 Hz, 1H), 7.58 (d, J = 1.2 Hz, 1H), 6.64 (s, 1H), 5.84-5.76 (m, 1H), 4.70-3.76 (m, 4H). $^{19}$F NMR (376 MHz, DMSO-d6) δ −61.47, −75.30, −106.17--107.76 (m), −119.74--121.39 (m). |
| 713 | 436.0 [M + H] | $^1$H NMR (400 MHz, DMSO-d6) δ 11.85-11.53 (m, 2H), 8.43 (d, J = 5.9 Hz, 1H), 8.12 (d, J = 2.3 Hz, 1H), 7.56 (d, J = 7.7 Hz, 1H), 7.00 (s, 1H), 6.47 (d, J = 2.3 Hz, 1H), 5.52-5.39 (m, 1H), 4.70-4.35 (m, 3H), 4.22-3.49 (m, 2H), 1.09-1.03 (m, 6H). $^{19}$F NMR (376 MHz, DMSO-d6) δ −75.24, −108.68 (d, J = 238.0 Hz), −119.93 (d, J = 237.6 Hz). |
| 714 | 482.2 [M + H] | $^1$H NMR (400 MHz, DMSO-d6) δ 11.53 (d, J = 4.1 Hz, 2H), 8.31 (s, 1H), 8.19 (s, 1H), 8.02 (d, J = 6.3 Hz, 1H), 7.82 (s, 1H), 7.54 (d, J = 11.6 Hz, 2H), 6.89 (s, 1H), 5.37 (q, J = 9.1 Hz, 2H), 2.95 (ddd, J = 9.3, 6.3, 4.4 Hz, 1H), 2.78 (dt, J = 9.5, 5.4 Hz, 1H), 2.54 (s, 3H), 2.14-2.04 (m, 1H), 1.89 (dt, J = 11.0, 5.3 Hz, 1H). $^{19}$F NMR (376 MHz, DMSO-d6) δ −70.06 (t, J = 9.2 Hz), −74.98. |
| 715 | 509.2 [M + H] | $^1$H NMR (400 MHz, Methanol-d4) δ 8.45 (s, 1H), 8.14 (d, J = 2.4 Hz, 1H), 7.68 (s, 1H), 7.18 (s, 1H), 7.09 (dd, J = 7.8, 1.4 Hz, 1H), 6.97 (d, J = 7.8 Hz, 1H), 6.63 (d, J = 2.3 Hz, 1H), 4.61 (q, J = 9.0 Hz, 2H), 3.16-3.09 (m, 1H), 2.78-2.69 (m, 1H), 1.95-1.80 (m, 2H), 1.75-1.65 (m, 4H). |
| 716 | 486.1 [M + H] | $^1$H NMR (400 MHz, DMSO-d6) δ 11.66 (s, 1H), 11.55 (s, 1H), 8.36 (s, 1H), 8.30 (d, J = 3.4 Hz, 1H), 8.16 (s, 1H), 7.79-7.67 (m, 3H), 7.18 (d, J = 8.3 Hz, 1H), 5.41 (q, J = 8.9 Hz, 2H), 3.10 (q, J = 7.0 Hz, 1H), 2.78 (q, J = 7.1, 6.6 Hz, 1H), 1.95 (t, J = 7.5 Hz, 2H). $^{19}$F NMR (376 MHz, DMSO-d6) δ −70.06 (t, J = 9.1 Hz), −184.76 (d, J = 3.5 Hz). |
| 717 | 432.10 [M + H] | $^1$H NMR (400 MHz, DMSO-d6) δ 11.68 (d, J = 6.3 Hz, 1H), 11.61 (d, J = 2.0 Hz, 1H), 8.66 (d, J = 1.7 Hz, 1H), 8.49 (s, 1H), 8.28 (d, J = 2.0 Hz, 1H), 8.13-8.06 (m, 2H), 7.78 (s, 1H), 5.39 (q, J = 9.0 Hz, 2H), 3.10-2.98 (m, 2H), 2.18-2.16 (m, 1H), 2.02-2.00 (m, 1H). $^{19}$F NMR (376 MHz, DMSO-d6) δ −70.31--70.38 (m), −136.55. |
| 718 | 512.20 [M + H] | $^1$H NMR (400 MHz, DMSO-d6) δ 11.55 (d, J = 6.3 Hz, 2H), 8.63 (s, 1H), 8.31 (d, J = 1.2 Hz, 1H), 8.03 (d, J = 6.0 Hz, 1H), 7.80 (d, J = 1.3 Hz, 1H), 7.62 (d, J = 6.3 Hz, 2H), 4.73 (q, J = 9.2 Hz, 2H), 3.26 (d, J = 8.9 Hz, 1H), 3.03 (ddd, J = 9.0, 6.3, 4.2 Hz, 1H), 2.34 (s, 1H), 2.04 (dt, J = 9.9, 4.9 Hz, 1H), 1.41 (s, 6H). $^{19}$F NMR (376 MHz, DMSO-d6) δ −69.48 (t, J = 9.2 Hz), −74.92. |
| 719 | 521.10 [M + H] | $^1$H NMR (400 MHz, DMSO-d6) δ 11.56 (s, 1H), 11.54 (d, J = 2.1 Hz, 1H), 8.67 (d, J = 1.7 Hz, 1H), 8.22 (d, J = 2.1 Hz, 1H), 8.06 (d, J = 6.1 Hz, 1H), 7.87 (s, 1H), 7.65 (s, 1H), 5.36 (q, J = 8.5 Hz, 2H), 3.16 (ddd, J = 9.0, 6.2, 4.4 Hz, 1H), 2.90 (ddd, J = 9.1, 6.1, 4.4 Hz, 1H), 2.27 (dt, J = 9.1, 5.4 Hz, 1H), 1.99-1.89 (m, 1H) $^{19}$F NMR (376 MHz, DMSO-d6) δ −70.38 (t, J = 9.0 Hz), −75.36 , −136.60. |
| 720 | 505.10 [M + H] | $^1$H NMR (400 MHz, DMSO-d6) δ 11.58-11.52 (m, 2H), 8.67 (d, J = 1.8 Hz, 1H), 8.22 (d, J = 2.0 Hz, 1H), 8.08-8.01 (m, 1H), 7.60-7.53 (m, 2H), 5.36 (q, J = 8.9 Hz, 2H), 3.17 (ddd, J = 9.0, 6.2, 4.4 Hz, 1H), 2.86 (ddd, J = 8.9, 6.0, 4.3 Hz, 1H), 2.27 (dt, J = 9.1, 5.4 Hz, 1H), 1.98-1.88 (m, 1H). $^{19}$F NMR (376 MHz, DMSO-d6) δ −70.38 (t, J = 9.0 Hz), −75.13, −136.61, −155.54 (d, J = 7.0 Hz). |
| 721 | 520.10 [M + H] | $^1$H NMR (400 MHz, DMSO-d6) δ 11.55 (d, J = 5.7 Hz, 2H), 8.05 (d, J = 6.1 Hz, 1H), 7.86 (s, 1H), 7.77-7.65 (m, 2H), 7.62 (s, 1H), 7.20 (dd, J = 8.5, 1.3 Hz, 1H), 5.31 (q, J = 9.0 Hz, 2H), 3.04 (ddd, J = 9.0, 6.3, 4.4 Hz, 1H), 2.84 (ddd, J = 8.9, 5.9, 4.4 Hz, 1H), 2.19 (ddd, J = 8.9, 6.1, 4.8 Hz, 1H), 1.91 (ddd, J = 8.8, 6.3, 4.8 Hz, 1H). $^{19}$F NMR (376 MHz, DMSO-d6) δ −70.30 (t, J = 9.0 Hz), −75.61, −133.92. |
| 722 | 545.20 [M + H] | $^1$H NMR (400 MHz, DMSO-d6) δ 11.54 (d, J = 7.2 Hz, 2H), 8.05 (d, J = 6.0 Hz, 1H), 7.85 (s, 1H), 7.56 (s, 1H), 7.31 (d, J = 7.6 Hz, 1H), 7.13 (s, 1H), 7.01 (dd, J = 7.7, 1.4 Hz, 1H), 4.63 (q, J = 9.4 Hz, 2H), 2.94-2.67 (m, 2H), 2.16-2.07 (m, 1H), 1.89-1.79 (m, 1H), 1.30 (s, 6H). $^{19}$F NMR (376 MHz, DMSO-d6) δ −69.30 (t, J = 9.4 Hz), −75.35. |

TABLE 3-continued

Characterization Data

| Example No. | ES/MS m/z | NMR |
|---|---|---|
| 723 | 530.20 [M + H] | ¹H NMR (400 MHz, DMSO-d6) δ 11.55 (d, J = 3.7 Hz, 2H), 8.21 (d, J = 1.6 Hz, 1H), 8.04 (d, J = 6.4 Hz, 1H), 7.60-7.48 (m, 3H), 4.67 (q, J = 9.4 Hz, 2H), 2.95 (ddd, J = 9.5, 6.2, 4.4 Hz, 1H), 2.76 (dt, J = 10.0, 5.4 Hz, 1H), 2.23-2.13 (m, 1H), 1.89-1.74 (m, 1H), 1.31 (s, 6H). ¹⁹F NMR (376 MHz, DMSO-d6) δ −69.48 (t, J = 9.3 Hz), −75.38, −155.54 (d, J = 7.1 Hz). |
| 724 | 496.10 [M + H] | ¹H NMR (400 MHz, Methanol-d4) δ 8.11 (s, 1H), 7.90 (t, J = 7.8 Hz, 1H), 7.36 (d, J = 7.4 Hz, 1H), 7.23 (d, J = 7.0 Hz, 1H), 7.05 (d, J = 8.4 Hz, 1H), 6.72 (s, 1H), 6.66 (t, J = 55.3 Hz, 1H), 6.04-5.89 (m, 1H), 4.69-4.16 (m, 4H). ¹⁹F NMR (376 MHz, Methanol-d4) δ −77.74, −109.55−−119.07 (m), −118.63 (dd, J = 55.3, 13.9 Hz), −123.69−−124.60 (m), −157.71 (d, J = 7.0 Hz). |
| 725 | 496.00 [M + H] | ¹H NMR (400 MHz, Methanol-d4) δ 8.53 (d, J = 5.8 Hz, 1H), 8.12 (s, 1H), 7.42 (d, J = 2.6 Hz, 1H), 7.31-7.27 (m, 1H), 7.24 (d, J = 7.1 Hz, 1H), 6.75 (s, 1H), 6.71 (t, J = 55.0 Hz, 1H), 5.60-5.49 (m, 1H), 4.68-4.27 (m, 4H). ¹⁹F NMR (376 MHz, Methanol-d4) δ −78.09, −108.06−−119.07 (m), −118.79 (dd, J = 55.0, 2.9 Hz), −123.23−−124.01 (m), −157.63 (d, J = 7.1 Hz). |
| 726 | 514.10 [M + H] | ¹H NMR (400 MHz, Methanol-d4) δ 8.60 (d, J = 5.8 Hz, 1H), 8.12 (s, 1H), 7.54 (d, J = 2.5 Hz, 1H), 7.38 (dd, J = 5.8, 2.5 Hz, 1H), 7.24 (d, J = 7.1 Hz, 1H), 6.75 (s, 1H), 5.64-5.52 (m, 1H), 4.68-4.28 (m, 4H). ¹⁹F NMR (376 MHz, Methanol-d4) δ −70.19, −107.91−−108.98 (m), −123.16−−124.07 (m), −157.65 (d, J = 7.0 Hz). |
| 727 | 515.10 [M + H] | ¹H NMR (400 MHz, Methanol-d4) δ 8.99 (s, 1H), 8.12 (s, 1H), 7.46 (d, J = 0.9 Hz, 1H), 7.24 (d, J = 7.1 Hz, 1H), 6.75 (s, 1H), 6.16-6.05 (m, 1H), 4.71-4.26 (m, 4H). ¹⁹F NMR (376 MHz, Methanol-d4) δ −72.23, −78.22, −108.88−−109.95 (m), −122.74−−124.16 (m), −157.61 (d, J = 7.0 Hz). |
| 728 | 515.10 [M + H] | ¹H NMR (400 MHz, Methanol-d4) δ 8.75 (d, J = 5.8 Hz, 1H), 8.12 (s, 1H), 7.25 (d, J = 7.0 Hz, 1H), 7.24 (d, J = 5.8 Hz, 1H), 6.75 (s, 1H), 6.12-6.03 (m, 1H), 4.70-4.54 (m, 1H), 4.54-4.30 (m, 3H). ¹⁹F NMR (376 MHz, Methanol-d4) δ −72.90, −78.25, −108.98−−110.32 (m), −122.69−−124.37 (m), −157.62 (d, J = 7.0 Hz). |
| 729 | 486.10 [M + H] | ¹H NMR (400 MHz, Methanol-d4) δ 8.45 (s, 1H), 8.16-8.12 (m, 1H), 7.70 (s, 1H), 7.48 (s, 1H), 6.94 (d, J = 11.0 Hz, 1H), 6.64 (d, J = 2.4 Hz, 1H), 5.22 (q, J = 8.8 Hz, 2H), 3.22-3.15 (m, 1H), 2.89-2.77 (m, 1H), 2.02-1.87 (m, 2H). ¹⁹F NMR (376 MHz, Methanol-d4) δ −72.92 (t, J = 8.7 Hz), −78.00, −121.19 (d, J = 11.0 Hz). |
| 730 | 469.00 [M + H] | ¹H NMR (400 MHz, Methanol-d4) δ 9.36 (s, 1H), 8.64 (s, 1H), 8.49 (s, 1H), 8.16 (d, J = 2.4 Hz, 1H), 8.15 (s, 1H), 7.84 (s, 1H), 6.67 (d, J = 2.4 Hz, 1H), 5.43 (q, J = 8.6 Hz, 2H), 3.10-3.02 (m, 1H), 2.25-2.11 (m, 2H). ¹⁹F NMR (376 MHz, Methanol-d4) δ −72.78 (t, J = 8.6 Hz), −77.85. |
| 731 | 469.10 [M + H] | ¹H NMR (400 MHz, Methanol-d4) δ 8.72-8.67 (m, 1H), 8.46 (s, 1H), 8.29 (s, 1H), 8.19-8.17 (m, 1H), 8.15 (d, J = 2.4 Hz, 1H), 7.76 (s, 1H), 6.65 (d, J = 2.4 Hz, 1H), 5.30 (q, J = 8.7 Hz, 2H), 3.25-3.16 (m, 1H), 2.96-2.85 (m, 1H), 2.11-2.02 (m, 1H), 2.00-1.94 (m, 1H). ¹⁹F NMR (376 MHz, Methanol-d4) δ −73.03 (t, J = 8.7 Hz), −77.99. |
| 732 | 495.20 [M + H] | ¹H NMR (400 MHz, Methanol-d4) δ 8.96 (dd, J = 4.9, 1.4 Hz, 1H), 8.80-8.74 (m, 1H), 8.27 (d, J = 1.6 Hz, 1H), 8.25 (s, 1H), 7.92-7.84 (m, 3H), 7.74 (s, 1H), 7.53 (s, 1H), 5.00 (q, J = 8.4 Hz, 2H), 3.02-2.93 (m, 2H), 2.08 (t, J = 7.5 Hz, 2H). ¹⁹F NMR (376 MHz, Methanol-d4) δ −75.48 (t, J = 8.5 Hz), −77.85. |
| 733 | 505.20 [M + H] | ¹H NMR (400 MHz, Methanol-d4) δ 8.35 (d, J = 1.9 Hz, 1H), 8.27 (s, 1H), 8.03 (d, J = 1.9 Hz, 1H), 7.98 (s, 1H), 7.07 (s, 1H), 7.03-6.91 (m, 2H), 4.30-4.14 (m, 2H), 2.84-2.69 (m, 2H), 1.98-1.86 (m, 2H), 1.72-1.60 (m, 7H). ¹⁹F NMR (376 MHz, Methanol-d4) δ −77.82, −94.82−−95.15 (m). |
| 734 | 499.20 [M + H] | ¹H NMR (400 MHz, Methanol-d4) δ 8.35 (d, J = 1.9 Hz, 1H), 8.27 (s, 1H), 8.03 (d, J = 1.9 Hz, 1H), 7.98 (s, 1H), 7.11 (s, 1H), 7.01-6.91 (m, 2H), 4.21 (d, J = 21.0 Hz, 2H), 2.84-2.67 (m, 2H), 1.98-1.86 (m, 2H), 1.70-1.59 (m, 4H), 1.13-0.99 (m, 2H), 0.96-0.85 (m, 2H). ¹⁹F NMR (376 MHz, Methanol-d4) δ −77.81, −184.03−−184.30 (m). |
| 735 | 517.20 [M + H] | ¹H NMR (400 MHz, Methanol-d4) δ 8.19 (s, 1H), 7.56 (s, 1H), 7.42 (d, J = 6.8 Hz, 1H), 7.08 (s, 1H), 7.00-6.87 (m, 2H), 4.33-4.13 (m, 2H), 2.85-2.74 (m, 2H), 1.97-1.88 (m, 1H), 1.83-1.73 (m, 1H), 1.70-1.56 (m, 4H), 1.11-0.99 (m, 2H), 0.95-0.85 (m, 2H). ¹⁹F NMR (376 MHz, Methanol-d4) δ −77.82, −157.36 (d, J = 6.8 Hz), −184.17−−184.52 (m). |
| 736 | 541.20 [M + H] | ¹H NMR (400 MHz, Methanol-d4) δ 8.34 (d, J = 1.9 Hz, 1H), 8.27 (s, 1H), 8.01 (d, J = 1.9 Hz, 1H), 7.96 (s, 1H), 7.06 (s, 1H), 7.04-6.94 (m, 2H), 6.24 (tt, J = 52.6, 4.4 Hz, 1H), 4.57-4.37 (m, 2H), 2.84-2.69 (m, 2H), 1.97-1.87 (m, 2H), 1.75-1.61 (m, 4H). ¹⁹F |

TABLE 3-continued

Characterization Data

| Example No. | ES/MS m/z | NMR |
|---|---|---|
| | | NMR (376 MHz, Methanol-d4) δ −77.80, −121.57−−121.82 (m), −139.57 (d, J = 52.5 Hz). |
| 737 | 559.20 [M + H] | $^1$H NMR (400 MHz, Methanol-d4) δ 8.33 (d, J = 1.8 Hz, 1H), 8.26 (s, 1H), 8.00 (d, J = 1.8 Hz, 1H), 7.94 (s, 1H), 7.09-7.06 (m, 1H), 7.05-6.95 (m, 2H), 4.69-4.57 (m, 2H), 2.88-2.67 (m, 2H), 1.96-1.89 (m, 2H), 1.73-1.64 (m, 4H). $^{19}$F NMR (376 MHz, Methanol-d4) δ −77.80, −86.44, −120.52−−120.71 (m). |
| 738 | 531.20 [M + H] | $^1$H NMR (400 MHz, Methanol-d4) δ 8.36-8.31 (m, 1H), 8.27 (s, 1H), 8.01 (s, 1H), 7.95 (s, 1H), 7.09-7.05 (m, 1H), 7.01-6.93 (m, 2H), 4.39-4.25 (m, 2H), 2.82-2.71 (m, 2H), 1.94-1.87 (m, 2H), 1.73-1.55 (m, 5H), 0.90-0.86 (m, 4H). $^{19}$F NMR (376 MHz, Methanol-d4) δ −77.80, −106.91−−107.21 (m). |
| 739 | 523.20 [M + H] | $^1$H NMR (400 MHz, Methanol-d4) δ 8.21 (s, 1H), 7.66 (s, 1H), 7.52 (d, J = 6.6 Hz, 1H), 7.05 (s, 1H), 7.01-6.85 (m, 2H), 4.32-4.14 (m, 2H), 2.83-2.72 (m, 2H), 1.97-1.89 (m, 1H), 1.86-1.78 (m, 1H), 1.72-1.59 (m, 7H). $^{19}$F NMR (376 MHz, Methanol-d4) δ −78.16, −94.84−−95.17 (m), −156.91 (d, J = 6.7 Hz). |
| 740 | 543.10 [M + H] | $^1$H NMR (400 MHz, Acetonitrile-d3) δ 9.23 (s, 2H), 8.11 (d, J = 6.4 Hz, 1H), 7.77 (s, 1H), 7.72 (s, 1H), 7.09-6.82 (m, 3H), 4.51 (q, J = 9.3 Hz, 2H), 2.78 (s, 2H), 2.05-2.01 (m, 1H), 1.83 (d, J = 7.4 Hz, 1H), 1.65 (dt, J = 5.1, 3.5 Hz, 4H). $^{19}$F NMR (377 MHz, Acetonitrile-d3) δ −71.19 (t, J = 9.2 Hz), −77.32. |
| 741 | 577.10 [M + H] | $^1$H NMR (400 MHz, DMSO-d6) δ 11.57 (d, J = 4.3 Hz, 2H), 8.05 (d, J = 6.4 Hz, 1H), 7.65 (s, 1H), 7.19 (s, 1H), 7.03-6.91 (m, 2H), 4.69 (td, J = 9.3, 3.4 Hz, 2H), 2.75 (ddt, J = 36.8, 10.0, 4.8 Hz, 2H), 2.13-1.97 (m, 1H), 1.83 (dt, J = 8.4, 5.3 Hz, 1H), 1.68-1.47 (m, 4H). $^{19}$F NMR (376 MHz, DMSO-d6) δ −69.25 (t, J = 9.4 Hz), −74.01. |
| 742 | 554.10 [M + H] | $^1$H NMR (400 MHz, DMSO-d6) δ 11.54-11.12 (m, 2H), 8.07 (d, J = 8.8 Hz, 1H), 7.97 (d, J = 6.0 Hz, 1H), 7.48 (dd, J = 2.5, 1.4 Hz, 1H), 7.45-7.38 (m, 2H), 6.65 (s, 1H), 5.83-5.56 (m, 1H), 4.49 (d, J = 64.0 Hz, 4H). $^{19}$F NMR (376 MHz, DMSO-d6) δ −57.67, −75.32, −106.91 (d, J = 241.3 Hz), −120.56 (d, J = 239.7 Hz), −155.33 (d, J = 7.1 Hz). |
| 743 | 536.10 [M + H] | $^1$H NMR (400 MHz, DMSO-d6) δ 11.52-11.31 (m, 2H), 8.09 (d, J = 1.1 Hz, 1H), 8.08 (d, J = 8.8 Hz, 1H), 7.94 (d, J = 6.1 Hz, 1H), 7.59 (d, J = 1.1 Hz, 1H), 7.48 (dd, J = 2.5, 1.3 Hz, 1H), 7.42 (dd, J = 8.8, 2.4 Hz, 1H), 6.65 (s, 1H), 5.73 (dt, J = 8.0, 4.1 Hz, 1H), 4.50-4.18 (m, 4H). $^{19}$F NMR (376 MHz, DMSO-d6) δ −57.67, −75.37, −106.84 (d, J = 239.4 Hz), −120.31 (d, J = 238.7 Hz). |
| 744 | 514.10 [M + H] | $^1$H NMR (400 MHz, DMSO-d6) δ 11.55-11.22 (m, 2H), 8.45 (d, J = 1.5 Hz, 1H), 7.98 (d, J = 6.1 Hz, 1H), 7.43 (d, J = 7.1 Hz, 1H), 7.39-7.08 (m, 2H), 6.65 (s, 1H), 5.91 (d, J = 7.5 Hz, 1H), 4.51 (d, J = 43.7 Hz, 3H), 4.19 (s, 1H). $^{19}$F NMR (376 MHz, DMSO-d6) δ −74.95, −107.75−−108.38 (m), −117.95 (ddd, J = 53.4, 11.7, 6.2 Hz), −119.93 (d, J = 238.6 Hz), −143.15 (q, J = 5.7, 5.2 Hz), −155.37 (d, J = 7.4 Hz). |
| 745 | 495.20 [M + H] | $^1$H NMR (400 MHz, Acetonitrile-d3) δ 9.23 (s, 2H), 8.06 (d, J = 6.3 Hz, 1H), 7.98 (d, J = 1.6 Hz, 1H), 7.74 (d, J = 1.6 Hz, 1H), 7.30 (d, J = 5.7 Hz, 1H), 7.26-7.21 (m, 2H), 7.15-6.79 (m, 2H), 5.23 (tt, J = 7.7, 3.1 Hz, 1H), 4.55-4.32 (m, 3H), 4.32-4.12 (m, 1H). $^{19}$F NMR (377 MHz, Acetonitrile-d3) δ −77.23, −106.24−−109.63 (m), −115.75 (dt, J = 54.4, 4.0 Hz), −122.73 (d, J = 241.3 Hz), −129.16 (dt, J = 11.3, 3.9 Hz). |
| 746 | 523.20 [M + H] | $^1$H NMR (400 MHz, Acetonitrile-d3) δ 9.53 (s, 1H), 9.41 (s, 1H), 8.24-8.15 (m, 2H), 8.06 (s, 1H), 7.99 (d, J = 2.1 Hz, 1H), 6.98-6.87 (m, 3H), 4.05 (td, J = 7.0, 2.8 Hz, 2H), 2.82 (dt, J = 9.1, 5.2 Hz, 1H), 2.64 (qt, J = 11.0, 6.7 Hz, 3H), 1.97-1.90 (m, 1H), 1.85 (dt, J = 9.1, 5.7 Hz, 1H), 1.58 (dd, J = 5.1, 3.6 Hz, 4H). $^{19}$F NMR (377 MHz, Acetonitrile-d3) δ −66.52 (t, J = 11.1 Hz), −77.19. |
| 747 | 527.10 [M + H] | $^1$H NMR (400 MHz, Acetonitrile-d3) δ 9.47 (s, 1H), 9.37 (s, 1H), 8.22 (d, J = 2.1 Hz, 1H), 8.17 (d, J = 6.2 Hz, 1H), 8.11 (s, 1H), 8.01 (d, J = 2.2 Hz, 1H), 6.93 (t, J = 7.1 Hz, 1H), 6.80 (d, J = 7.9 Hz, 1H), 4.64 (q, J = 8.9 Hz, 2H), 2.89-2.67 (m, 2H), 1.95-1.89 (m, 1H), 1.88-1.82 (m, 1H), 1.75-1.65 (m, 4H). $^{19}$F NMR (376 MHz, Acetonitrile-d3) δ −72.12 (q, J = 9.1 Hz), −77.22, −143.08 (qd, J = 10.1, 6.4 Hz). |
| 748 | 527.20 [M + H] | $^1$H NMR (400 MHz, Acetonitrile-d3) δ 9.32 (s, 1H), 9.26 (s, 1H), 8.15 (d, J = 1.9 Hz, 1H), 8.11 (d, J = 6.5 Hz, 1H), 7.95 (s, 1H), 7.92 (d, J = 1.9 Hz, 1H), 6.96 (d, J = 5.9 Hz, 1H), 6.81 (d, J = 9.7 Hz, 1H), 4.55 (qd, J = 9.2, 3.1 Hz, 2H), 2.85 (t, J = 6.9 Hz, 2H), 1.75-1.53 (m, 4H). $^{19}$F NMR (376 MHz, Acetonitrile-d3) δ −71.21 (t, J = 9.2 Hz), −77.04, −127.92 (dd, J = 9.7, 5.8 Hz). |

TABLE 3-continued

Characterization Data

| Example No. | ES/MS m/z | NMR |
|---|---|---|
| 749 | 527.20 [M + H] | $^1$H NMR (400 MHz, Acetonitrile-d3) δ 9.37 (s, 1H), 9.31 (s, 1H), 8.20 (d, J = 1.9 Hz, 1H), 8.16 (d, J = 6.5 Hz, 1H), 8.03 (s, 1H), 7.98 (d, J = 2.1 Hz, 1H), 6.94 (s, 1H), 6.75 (d, J = 11.1 Hz, 1H), 4.52 (q, J = 9.2 Hz, 2H), 2.69-2.59 (m, 1H), 1.93-1.82 (m, 4H), 1.64 (q, J = 4.0 Hz, 2H). $^{19}$F NMR (376 MHz, Acetonitrile-d3) δ −71.19 (t, J = 9.2 Hz), −77.24 (d, J = 3.8 Hz), −128.71 (d, J = 11.3 Hz). |

C. PROPHETIC EXAMPLES

The following additional examples may be made using analogous methods. For instance, and further to the disclosure above, synthesis of (2-phenylcyclopropyl)boronic acid derivates has been reported in the literature, see e.g., Montesinos-Magraner, Marc; et al. Angewandte Chemie Int. Ed. (2019), 58, 5930-5935; Zhong, Chongmin; et al. Journal of the American Chemical Society (2010), 132(33), 11440-11442; Shi, Xiaonan; et al. Angewandte Chemie, International Edition (2019), 58(45), 16167-16171; and Fawcett, Alexander; et al. Science (Washington, DC, United States) (2017), 357(6348), 283-286.

Example 37. 5-(8-(2-(2-chlorophenyl)cyclopropyl)imidazo[1,2-b]pyridazin-6-yl)pyrimidine-2,4(1H,3H)-dione

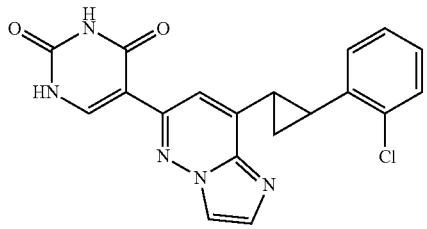 [SMILES: O=c1[nH]cc(-c2cc(C3CC3c3ccccc3Cl)c3nccn3n2)c(=O)[nH]1]

Example 40. 5-(8-(2-(2-(trifluoromethyl)phenyl)cyclopropyl)imidazo[1,2-b]pyridazin-6-yl)pyrimidine-2,4(1H,3H)-dione

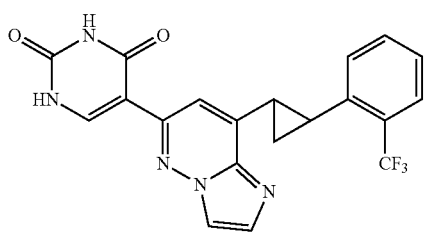 [SMILES: O=c1[nH]cc(-c2cc(C3CC3c3ccccc3C(F)(F)F)c3nccn3n2)c(=O)[nH]1]

Example 43. 5-(8-(2-(2-cyclopropylphenyl)cyclopropyl)imidazo[1,2-b]pyridazin-6-yl)pyrimidine-2,4(1H,3H)-dione

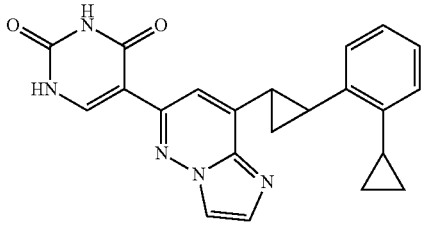 [SMILES: O=c1[nH]cc(-c2cc(C3CC3c3ccccc3C3CC3)c3nccn3n2)c(=O)[nH]1]

Example 44. 5-(8-(2-(3-cyclopropylphenyl)cyclopropyl)imidazo[1,2-b]pyridazin-6-yl)pyrimidine-2,4(1H,3H)-dione

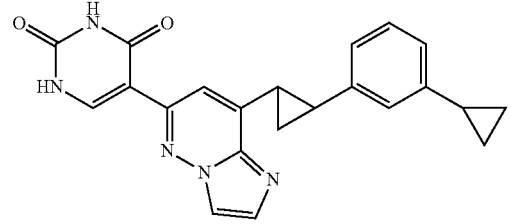 [SMILES: O=c1[nH]cc(-c2cc(C3CC3c3cccc(C4CC4)c3)c3nccn3n2)c(=O)[nH]1]

Example 46. 5-[8-[2-[2-(trifluoromethoxy)phenyl]cyclopropyl]imidazo[1,2-b]pyridazin-6-yl]-1-{H}-pyrimidine-2,4-dione

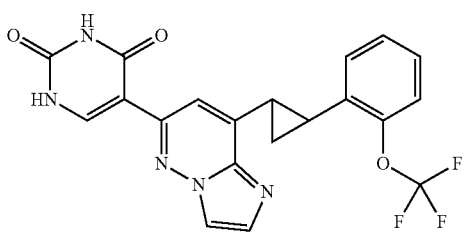 [SMILES: O=c1[nH]cc(-c2cc(C3CC3c3ccccc3OC(F)(F)F)c3nccn3n2)c(=O)[nH]1]

Example 51. 4-(2-(6-(2,4-dioxo-1,2,3,4-tetrahydro-pyrimidin-5-yl)imidazo[1,2-b]pyridazin-8-3/1)cyclopropyl)benzonitrile

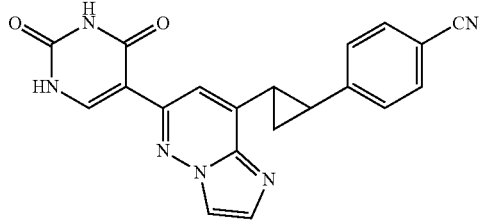 [SMILES: N#Cc1ccc(C2CC2c2cc(-c3c[nH]c(=O)[nH]c3=O)nn3ccnc23)cc1]

D. BIOCHEMICAL AND BIOLOGICAL ASSAYS

CD73 Biochemical IC50 Assay

Compound serial dilutions were pre-spotted into Thermo Nunc assay plate. 50 μL CD73 enzyme buffer (CD73 purchased from R&D system=0.6 nM, 25 mM Tris, pH 7.4, 5 mM $MgCl_2$) was added into the assay plate and incubated for 15 mins. 50 μL AMP buffer (AMP=30 uM in 25 mM Tris, pH 7.4, 5 mM $MgCl_2$, final AMP=15 uM, 2XKm, final CD73=0.3 nM) was added into assay plate. After incubation for 60 mins, the supernatant 20 uL was transferred into 384-well NUNC plate pre-filled with 60 ul Quench buffer (80% organic and 20% water+0.1% FA) with internal standard. The plate was spun down at 4500 rpm for 20 mins, then 200 of supernatant was transferred to another Nunc plate prefilled with 800 of water. The samples were run using Rapid fire.

MDA-MB-231 Cell Based CD73 Activity Assay

MDA-MB-231-GFP cells were seeded in 384-well plates (Greiner 781946) at a density of 10000 cells per well in 50 μL of RPMI medium with 10% HP (human plasma). Cells were plated into assay plate with compounds pre-spotted, for an overnight compound treatment. 50 μL of 400 μM AMP (final concentration 200 μM) using a Bio-tek dispenser. Plates were incubated for 100 mins. 20 uL supernatant was transferred into 384-well NUNC plates pre-filled with 600 Quench buffer (80% organic and 20% water+0.1% FA) with internal standard. The plates were spun down at 4500 rpm for 20 mins, then 20 μl of supernatant was transferred to another Nunc plate prefilled with 80 μl of water. The samples were run using Rapid fire.

Results of biochemical and biological assays described above are included in Table 4 below.

TABLE 4

Activity Data from CD73 Biochemical IC50 assay and MDA-MB-231 Cell based CD73 activity assay

| Example No. | IC50-CD73 (nM) | EC50 (nM) |
| --- | --- | --- |
| 1 | 506.91 | 412.80 |
| 2 | 32.36 | 53.28 |
| 3 | 235.34 | 195.19 |
| 4 | 195.46/230.84 | 190.85/285.49 |
| 5 | 1550.50/2500 | 2017.80/2534.1 |
| 6 | 163.76 | 183.85 |
| 7 | 13.63/13.00 | 2.08/1.876 |
| 8 | 29.00/45.78 | 36.14/47.21 |
| 9 | 105.60 | 29.15 |
| 10 | 980.35 | 472.65 |
| 11 | 109.79 | 74.11 |
| 12 | 478.83/653.27 | 507.83/688.82 |
| 13 | 368.31/607.33 | 692.26/896.44 |
| 14 | 301.21 | 79.15 |
| 15 | 2351.10 | 920.43 |
| 16 | 362.09 | 332.76 |
| 17 | >2500.00 | 3674.10 |
| 18 | >2500.00 | 20414.00 |
| 19 | >2500.00 | >25000.00 |
| 20 | >2500.00 | >25000.00 |
| 21 | >2500.00 | >25000.00 |
| 22 | 55.78/64.87 | 46.29/45.14 |
| 23 | >2500.00 | >25000.00 |
| 24 | 1255.50 | 1225.90 |
| 25 | 657.12/556.90 | 361.47/428.69 |
| 26 | 161.19 | 184.12 |
| 27 | 90.39 | 145.13 |
| 28 | 16.83 | 3.59 |
| 29 | 16.32 | 7.08 |
| 30 | 2.36 | 2.56 |
| 31 | 5.49 | 3.84 |
| 32 | 18.61 | 6.84 |
| 33 | 9.38 | 2.04 |
| 34 | 18.19 | 11.28 |
| 36 | 24.16 | 6.51 |
| 38 | 14.34 | 7.29 |
| 41 | 61.61 | 18.64 |
| 42 | 28.72 | 7.59 |
| 45 | 32.63 | 6.59 |
| 47 | 47.17 | 13.70 |
| 48 | 52.55 | 16.72 |
| 49 | 17.48 | 18.99 |
| 50 | 10.69 | 2.45 |
| 52 | 20.11 | 2.69 |
| 53 | 20.75 | 5.16 |
| 54 | 17.67 | 3.40 |
| 55 | >2500.00 | 872.31 |
| 56 | >2500.00 | 4459.70 |
| 57 | >2500.00 | 3304.40 |
| 58 | 547.72 | 703.80 |
| 59 | 64.99 | 71.66 |
| 60 | 12.57 | 6.43 |
| 61 | 12.13 | 16.64 |
| 62 | 27.25 | 25.12 |
| 63 | 70.48 | 34.69 |
| 64 | 14.70 | 2.87 |
| 65 | 13.16 | 6.71 |
| 66 | >2500.00 | 4466.30 |
| 67 | 30.05 | 14.27 |
| 68 | 69.48 | 67.54 |
| 69 | 55.40 | 47.83 |
| 70 | 221.26 | 240.15 |
| 71 | 1491.20 | 648.56 |
| 72 | 26.46 | 12.42 |
| 73 | 39.69 | 17.44 |
| 74 | 169.83 | 539.77 |
| 75 | 125.72 | 136.01 |
| 76 | 26.45 | 2.48 |
| 77 | 22.58 | 13.36 |
| 78 | 1916.80 | 1227.30 |
| 79 | 25.20 | 11.65 |
| 85 | 43.29 | 6.08 |
| 86 | 151.62 | 21.75 |
| 87 | 15.69 | 3.24 |
| 88 | 9.16 | 2.93 |
| 89 | 211.40 | 247.92 |
| 90 | 9.91 | 1.79 |
| 91 | 104.09 | 62.23 |
| 92 | 15.62 | 23.57 |
| 93 | 521.90 | 556.17 |
| 94 | 131.72 | 75.99 |
| 95 | 49.48 | 39.09 |
| 96 | 773.04 | 66.64 |
| 97 | >2500.00 | 2053.60 |
| 98 | 16.44 | 7.23 |
| 99 | 19.26 | 6.05 |

TABLE 4-continued

Activity Data from CD73 Biochemical IC50 assay
and MDA-MB-231 Cell based CD73 activity assay

| Example No. | IC50-CD73 (nM) | EC50 (nM) |
| --- | --- | --- |
| 100 | 98.36 | 27.48 |
| 101 | 15.87 | 3.25 |
| 102 | 473.03 | 258.09 |
| 103 | 70.76 | 45.13 |
| 104 | 195.84 | 23.16 |
| 105 | 284.54 | 38.52 |
| 106 | 105.06 | 93.50 |
| 107 | 46.82 | 55.02 |
| 108 | 34.98 | 23.78 |
| 109 | 44.47 | 13.03 |
| 110 | 31.41 | 7.50 |
| 111 | 205.08 | 71.48 |
| 112 | 20.54 | 2.23 |
| 113 | 146.89 | 210.35 |
| 114 | 31.09 | 5.38 |
| 115 | 13.26 | 4.21 |
| 116 | >2500.00 | 717.54 |

CD73 Biochemical IC50 Assay (1 mM $NaH_2PO_4$)

Compound serial dilutions were pre-spotted into Thermo Nunc assay plate. 50 uL CD73 enzyme buffer (CD73 purchased from R&D system=0.6 nM, 25 mM Tris, pH 7.4, 5 mM $MgCl_2$, 1 mM $NaH_2PO_4$) was added into the assay plate and incubate for 15 mins. 50 uL AMP buffer (AMP=30 uM in 25 mM Tris, pH 7.4, 5 mM $MgCl_2$, final AMP=15 uM, 2XKm, final CD73=0.3 nM) was added into assay plate. After incubation for 60 mins, the supernatant (20 uL) was transferred into 384-well NUNC plate pre-filled with 60 uL Quench buffer (80% organic and 20% water+0.1% FA) with internal standard. The plate was spun down at 4500 rpm for 20 mins, then 20 uL of supernatant was transferred to another Nunc plate prefilled with 80 uL of water. The samples were analyzed using Rapid fire.

MDA-MB-231 Cell Based CD73 Activity Assay (DMEM)

MDA-MB-231-GFP cells were seeded in 384-well plates (Greiner 781946) at a density of 3000 cells per well in 50 μL of DMEM medium with 10% HP (human plasma). Cells were plated into assay plate with compounds pre-spotted, for an overnight compound treatment. 50 uL of 400 uM AMP (final concentration will be 200 uM) was added using Bio-tek dispenser. Plates were incubated for 100 mins. 20 uL of supernatant was transfered into 384-well NUNC plate pre-filled with 60 ul Quench buffer (80% organic and 20% water+0.1% FA) with internal standard. The plates were spun down at 4500 rpm for 20 mins, then 20 ul of supernatant was transferred to another Nunc plate prefilled with 80 ul of water. The samples were analyzed using Rapid fire.

Results of biochemical and biological assays described above are included in Table 5 below.

TABLE 5

Activity Data from CD73 Biochemical IC50 assay (1 mM $NaH_2PO_4$) and MDA-MB-231 Cell based CD73 activity assay (DMEM)

| Example No. | IC50-CD73 (nM) | EC50 (nM) |
| --- | --- | --- |
| 7 | 0.94 | 4.15 |
| 9 | 19.43 | 58.80 |
| 22 | 35.55 | 104.01 |
| 30 | 2.08 | 5.11 |
| 31 | 0.93 | 4.83 |
| 33 | 0.93 | 4.71 |
| 42 | 2.08 | NA |
| 48 | 2.73 | NA |
| 50 | 1.37 | 5.84 |
| 52 | 1.14 | NA |
| 53 | 1.52 | NA |
| 54 | 1.98 | NA |
| 62 | 8.47 | 32.25 |
| 63 | 29.09 | 47.41 |
| 64 | 1.50 | 7.67 |
| 67 | 4.83 | 30.32 |
| 70 | 134.43 | 285.22 |
| 72 | 6.97 | 25.88 |
| 73 | 9.87 | 31.67 |
| 77 | 3.50 | 28.43 |
| 79 | 4.58 | 20.85 |
| 80 | 1.81 | 6.79 |
| 81 | 1.93 | 8.22 |
| 82 | 3.49 | 16.38 |
| 83 | 1.47 | 6.65 |
| 84 | 1.10 | 6.56 |
| 85 | 1.34 | 17.74 |
| 86 | 5.66 | 16.61 |
| 92 | 6.57 | NA |
| 93 | >250.00 | 684.62 |
| 98 | 2.00 | 17.74 |
| 109 | 2.97 | NA |
| 110 | 2.96 | 28.73 |
| 115 | 1.77 | 12.89 |
| 117 | 0.89 | 0.14 |
| 118 | 0.79 | 0.10 |
| 119 | 0.56 | 1.09 |
| 120 | 0.85 | 0.85 |
| 121 | 1.08 | 19.72 |
| 122 | 2.39 | 11.13 |
| 123 | 0.69 | 0.37 |
| 124 | 2.60 | 0.62 |
| 125 | 0.71 | 0.17 |
| 126 | 1.13 | 0.46 |
| 127 | 1.13 | 0.17 |
| 128 | 1.84 | 0.40 |
| 129 | 1.11 | 0.30 |
| 130 | 1.01 | 0.13 |
| 131 | 0.78 | 6.10 |
| 132 | 1.21 | 19.38 |
| 133 | 0.92 | 1.60 |
| 134 | 1.17 | 22.75 |
| 135 | 1.99 | 43.96 |
| 136 | 3.11 | 6.37 |
| 137 | 1.28 | 4.68 |
| 138 | 0.95 | 0.64 |
| 139 | 4.55 | 295.79 |
| 140 | 1.68 | 5.25 |
| 141 | 2.10 | 24.82 |
| 142 | 0.96 | 3.76 |
| 143 | 5.69 | 13.05 |
| 144 | 2.30 | 6.17 |
| 145 | 20.50 | 41.74 |
| 146 | 6.12 | 46.69 |
| 147 | 39.00 | 96.12 |
| 148 | 8.00 | 17.88 |
| 149 | 3.34 | 7.61 |
| 150 | 1.93 | 4.79 |
| 151 | 1.36 | 1.94 |
| 152 | 3.45 | 17.55 |
| 153 | 2.30 | 8.85 |
| 154 | 1.56 | 5.75 |
| 155 | 2.04 | 5.42 |
| 156 | 0.95 | 1.87 |
| 157 | 1.06 | 2.81 |
| 158 | 0.55 | 2.52 |
| 159 | 1.76 | 2.62 |
| 160 | 15.39 | 27.80 |
| 161 | 4.48 | 11.02 |
| 162 | 1.64 | 4.41 |
| 163 | 2.13 | 10.57 |
| 164 | 3.58 | 13.98 |
| 165 | 5.06 | 38.72 |
| 166 | 43.04 | 378.50 |

TABLE 5-continued

Activity Data from CD73 Biochemical IC50 assay (1 mM NaH$_2$PO$_4$) and MDA-MB-231 Cell based CD73 activity assay (DMEM)

| Example No. | IC50-CD73 (nM) | EC50 (nM) |
| --- | --- | --- |
| 167 | 33.00 | 152.18 |
| 168 | 72.53 | 305.54 |
| 169 | 73.87 | 188.57 |
| 170 | 35.41 | 135.53 |
| 171 | 3.17 | 14.08 |
| 172 | 13.88 | 65.08 |
| 173 | 3.59 | 88.18 |
| 174 | 68.95 | 214.08 |
| 175 | 3.60 | 23.10 |
| 176 | 10.99 | 59.48 |
| 177 | 7.27 | 33.25 |
| 178 | 2.65 | 4.35 |
| 179 | 16.74 | 60.50 |
| 180 | 2.20 | 4.67 |
| 181 | 2.42 | 6.42 |
| 182 | 1.24 | 10.36 |
| 183 | 2.52 | 23.86 |
| 184 | 2.86 | 9.45 |
| 185 | 13.46 | 57.43 |
| 186 | 7.57 | 22.31 |
| 187 | 2.76 | 12.60 |
| 188 | 17.48 | 62.54 |
| 189 | 18.09 | 49.05 |
| 190 | 3.05 | 12.80 |
| 191 | 21.77 | 45.84 |
| 192 | 6.41 | 20.88 |
| 193 | 150.68 | 682.12 |
| 194 | 3.32 | 468.57 |
| 195 | 62.86 | 217.89 |
| 196 | 98.60 | 243.13 |
| 197 | 10.98 | 30.22 |
| 198 | 85.25 | 191.45 |
| 199 | >250 | 754.69 |
| 200 | >250 | 809.15 |
| 201 | 1.11 | 6.39 |
| 202 | 1.04 | 4.25 |
| 203 | 3.03 | 10.32 |
| 204 | 1.63 | 9.31 |
| 205 | 4.42 | 16.01 |
| 206 | 4.97 | 28.69 |
| 207 | 6.05 | 20.33 |
| 208 | 5.88 | 25.42 |
| 209 | 2.80 | 24.22 |
| 210 | 4.59 | 24.35 |
| 211 | 2.33 | 10.85 |
| 212 | 1.24 | 0.72 |
| 213 | 0.92 | 0.45 |
| 215 | 1.41 | 12.10 |
| 216 | 8.01 | 31.65 |
| 217 | 111.27 | 583.80 |
| 218 | 3.29 | 455.16 |
| 219 | 8.26 | 62.59 |
| 220 | 5.34 | 114.02 |
| 221 | 13.09 | 74.90 |
| 222 | 17.40 | 133.18 |
| 223 | 31.42 | 66.38 |
| 224 | 11.95 | 32.59 |
| 225 | 15.18 | 105.99 |
| 226 | 121.18 | 409.61 |
| 227 | >250 | 487.38 |
| 228 | 31.22 | 145.75 |
| 229 | 56.93 | 174.53 |
| 230 | 39.46 | 64.73 |
| 231 | 1.62 | 2.00 |
| 232 | 2.15 | 6.18 |
| 233 | 1.17 | 0.80 |
| 234 | 0.62 | 6.56 |
| 235 | 0.96 | 0.82 |
| 236 | 1.02 | 3.04 |
| 237 | 0.70 | 1.10 |
| 238 | 0.36 | 5.18 |
| 239 | 0.86 | 1.17 |
| 240 | 0.28 | 3.79 |
| 241 | 2.13 | 1.41 |
| 242 | 0.22 | 2.43 |
| 243 | 22.17 | 56.11 |
| 244 | 108.16 | 573.58 |
| 245 | 169.85 | 746.74 |
| 246 | 167.68 | 212.88 |
| 247 | 41.90 | 93.60 |
| 248 | 15.07 | 36.33 |
| 249 | 46.14 | 249.04 |
| 250 | 109.51 | 686.84 |
| 251 | 17.64 | 124.63 |
| 252 | 174.47 | 1242.20 |
| 253 | 20.03 | 159.65 |
| 254 | 26.55 | 136.31 |
| 255 | 17.49 | 112.96 |
| 256 | 43.11 | 184.62 |
| 257 | 51.69 | 102.77 |
| 258 | 52.44 | 105.81 |
| 259 | 14.73 | 80.70 |
| 260 | >250 | 962.74 |
| 261 | 13.94 | 139.48 |
| 262 | 73.41 | 564.98 |
| 263 | 10.72 | 31.42 |
| 264 | 5.59 | 88.01 |
| 265 | 3.22 | 77.90 |
| 266 | 1.93 | 13.46 |
| 267 | 34.73 | 66.59 |
| 268 | 97.03 | 134.76 |
| 269 | 3.62 | 27.04 |
| 270 | 1.13 | 13.67 |
| 271 | 33.58 | 101.75 |
| 272 | 9.90 | 72.62 |
| 273 | 9.39 | 58.13 |
| 274 | 16.47 | 39.44 |
| 275 | 8.64 | 36.24 |
| 276 | 0.91 | 2.78 |
| 277 | 3.77 | 78.98 |
| 278 | 3.69 | 38.94 |
| 279 | 1.07 | 6.64 |
| 280 | 5.97 | 77.80 |
| 281 | 1.54 | 8.23 |
| 282 | 1.81 | 11.65 |
| 283 | 0.87 | 2.75 |
| 284 | 1.07 | 3.49 |
| 285 | 1.42 | 2.99 |
| 286 | 1.19 | 2.42 |
| 287 | 3.90 | 12.46 |
| 288 | 6.86 | 35.72 |
| 289 | 2.27 | 7.24 |
| 290 | 3.46 | 9.64 |
| 291 | 3.25 | 18.62 |
| 292 | 2.08 | 5.72 |
| 293 | 4.75 | 8.80 |
| 294 | 1.02 | 1.32 |
| 295 | 1.92 | 1.97 |
| 296 | 2.14 | 4.38 |
| 297 | 1.51 | 1.31 |
| 298 | 3.78 | 2.81 |
| 299 | 7.85 | 24.51 |
| 300 | 1.80 | 1.34 |
| 301 | 4.45 | 19.24 |
| 302 | 3.08 | 6.99 |
| 303 | 7.74 | 27.69 |
| 304 | 3.59 | 3.04 |
| 305 | 4.81 | 21.23 |
| 306 | 1.67 | 1.41 |
| 307 | 16.05 | 96.12 |
| 308 | 5.47 | 6.47 |
| 309 | 42.27 | 207.60 |
| 310 | 0.63 | 3.40 |
| 311 | 4.72 | 11.57 |
| 312 | 1.29 | 4.17 |
| 313 | 2.35 | 9.78 |
| 314 | >250 | NA |
| 315 | 6.64 | 27.63 |
| 316 | 0.65 | 1.21 |
| 317 | 1.01 | 2.00 |

TABLE 5-continued

Activity Data from CD73 Biochemical IC50 assay (1 mM NaH$_2$PO$_4$) and MDA-MB-231 Cell based CD73 activity assay (DMEM)

| Example No. | IC50-CD73 (nM) | EC50 (nM) |
|---|---|---|
| 318 | 0.43 | 0.06 |
| 319 | 0.34 | 0.07 |
| 320 | >250 | 1145.70 |
| 321 | 1.12 | 11.19 |
| 322 | 0.80 | 0.07 |
| 323 | 0.51 | 0.06 |
| 324 | 1.15 | 1.59 |
| 325 | 1.70 | 11.23 |
| 326 | 0.91 | 2.66 |
| 327 | 1.79 | 50.00 |
| 328 | 3.68 | 40.55 |
| 329 | 0.64 | 0.71 |
| 330 | 1.07 | 0.51 |
| 331 | 16.16 | 11.06 |
| 332 | 8.61 | 26.95 |
| 333 | 0.89 | 1.91 |
| 334 | 24.35 | 117.98 |
| 335 | 2.80 | 6.77 |
| 336 | 34.91 | >250 |
| 337 | 3.29 | 15.92 |
| 338 | 10.92 | 72.82 |
| 339 | 0.91 | 2.60 |
| 340 | 1.48 | 18.98 |
| 341 | 0.43 | 0.53 |
| 342 | 1.40 | 3.82 |
| 343 | 48.17 | 128.66 |
| 344 | 38.35 | 97.05 |
| 345 | 10.25 | 97.98 |
| 346 | 6.08 | 24.40 |
| 347 | 4.39 | 11.90 |
| 348 | 53.99 | 121.43 |
| 349 | 147.76 | 124.50 |
| 350 | 12.03 | 99.31 |
| 351 | 10.64 | 56.39 |
| 352 | >250 | 1002.00 |
| 353 | 69.61 | 109.49 |
| 354 | 90.76 | 401.47 |
| 355 | 7.56 | 14.46 |
| 356 | >250 | 915.68 |
| 357 | >250 | 402.47 |
| 358 | 27.79 | 82.20 |
| 359 | 1.74 | 22.01 |
| 360 | 0.92 | 7.56 |
| 361 | 2.72 | 2.53 |
| 362 | 2.98 | 1.00 |
| 363 | 2.00 | 5.50 |
| 364 | 7.17 | 34.04 |
| 365 | 7.62 | 32.82 |
| 366 | 6.60 | 16.39 |
| 367 | 17.50 | 67.63 |
| 368 | 3.73 | 20.25 |
| 369 | 21.47 | 27.51 |
| 370 | 4.02 | 15.68 |
| 371 | 4.95 | 17.93 |
| 372 | 3.40 | 9.23 |
| 373 | 2.56 | 9.61 |
| 374 | 4.10 | 13.78 |
| 375 | 2.83 | 11.17 |
| 376 | 8.07 | 19.31 |
| 377 | 7.66 | 22.65 |
| 378 | 6.45 | 18.87 |
| 379 | 1.98 | 5.89 |
| 380 | 3.43 | 14.26 |
| 381 | 0.69 | 0.16 |
| 382 | 1.63 | 0.13 |
| 383 | 1.83 | 49.26 |
| 384 | 1.27 | 0.24 |
| 385 | 0.68 | 0.25 |
| 386 | 0.92 | 0.28 |
| 387 | 1.27 | 0.36 |
| 388 | 0.41 | 0.21 |
| 391 | 1.01 | 0.10 |
| 392 | 1.25 | 0.34 |
| 393 | 0.74 | 0.16 |
| 394 | 5.94 | >250 |
| 395 | 2.10 | 29.93 |
| 396 | 2.00 | 0.24 |
| 397 | 15.26 | 22.48 |
| 398 | 17.10 | 29.49 |
| 399 | 12.21 | 26.98 |
| 400 | 206.94 | 547.23 |
| 401 | 12.61 | 52.97 |
| 402 | 53.19 | 135.50 |
| 403 | 8.94 | 28.48 |
| 404 | 22.93 | 77.63 |
| 405 | 8.30 | 21.64 |
| 406 | 25.65 | 98.16 |
| 407 | 1.90 | 14.71 |
| 408 | 2.35 | 7.44 |
| 409 | 10.66 | 37.85 |
| 410 | 816.70 | 928.30 |
| 411 | 6.11 | 42.56 |
| 412 | 6.00 | 38.34 |
| 413 | 3.01 | 34.61 |
| 414 | 2.84 | 43.84 |
| 415 | 0.79 | 3.93 |
| 416 | 0.71 | 33.46 |
| 417 | 0.87 | 12.60 |
| 418 | 0.96 | 4.71 |
| 419 | 1.23 | 8.90 |
| 420 | 4.87 | 13.74 |
| 421 | 31.02 | 65.09 |
| 422 | 72.73 | 155.14 |
| 423 | 39.24 | 76.38 |
| 424 | 1.64 | 4.10 |
| 425 | 1.63 | 5.63 |
| 426 | 0.23 | 4.50 |
| 427 | 0.48 | 7.40 |
| 428 | 1.38 | 14.72 |
| 429 | 2.22 | 8.89 |
| 430 | 0.18 | 0.71 |
| 431 | 0.15 | 0.13 |
| 432 | 0.15 | 2.58 |
| 433 | 9.71 | 44.56 |
| 434 | 2.78 | 14.41 |
| 435 | 6.00 | 66.05 |
| 436 | 0.13 | 0.43 |
| 437 | 12.76 | 43.56 |
| 438 | 0.14 | 0.10 |
| 439 | 0.77 | 2.63 |
| 440 | 38.17 | 139.79 |
| 441 | 46.30 | 239.06 |
| 442 | 6.46 | 19.55 |
| 443 | 156.91 | 188.03 |
| 444 | 70.98 | 356.17 |
| 445 | 147.60 | 256.15 |
| 446 | 90.98 | 1097.10 |
| 447 | >250 | 718.46 |
| 448 | 193.67 | 1361.40 |
| 449 | 131.52 | 473.02 |
| 450 | 229.94 | 249.52 |
| 451 | 67.61 | 167.23 |
| 452 | 95.35 | 94.77 |
| 453 | 76.04 | 112.29 |
| 454 | 28.74 | 50.56 |
| 455 | 14.88 | 45.96 |
| 456 | 0.53 | 0.15 |
| 457 | 3.52 | 9.67 |
| 458 | 4.04 | 13.16 |
| 459 | 0.75 | 0.38 |
| 460 | 0.46 | 0.38 |
| 461 | 2.56 | 11.55 |
| 462 | 9.39 | NA |
| 463 | 61.90 | NA |
| 464 | 1.47 | 16.22 |
| 465 | 0.86 | 3.24 |
| 466 | 3.47 | 19.96 |
| 467 | 0.85 | 3.86 |
| 468 | 1.67 | 13.28 |
| 469 | 1.73 | 14.99 |

TABLE 5-continued

Activity Data from CD73 Biochemical IC50 assay (1 mM NaH$_2$PO$_4$) and MDA-MB-231 Cell based CD73 activity assay (DMEM)

| Example No. | IC50-CD73 (nM) | EC50 (nM) |
| --- | --- | --- |
| 470 | 0.23 | 0.13 |
| 471 | 0.70 | 0.24 |
| 472 | 15.60 | 58.59 |
| 473 | 5.76 | 18.30 |
| 474 | 7.47 | 26.68 |
| 475 | 32.08 | 931.87 |
| 476 | 38.83 | 32.20 |
| 477 | >250 | 951.52 |
| 478 | 32.11 | 53.66 |
| 479 | 2.60 | 9.06 |
| 480 | >250 | 1924.30 |
| 481 | 26.05 | 44.41 |
| 482 | >250 | 1227.00 |
| 483 | >250 | 565.97 |
| 484 | 68.69 | 179.80 |
| 485 | >250 | 700.32 |
| 486 | >250 | 1009.60 |
| 487 | 27.86 | 81.03 |
| 488 | 16.91 | 12.99 |
| 489 | >250 | 1676.90 |
| 490 | 95.00 | 463.24 |
| 491 | >250 | 1680.00 |
| 492 | 25.64 | 58.44 |
| 493 | 193.77 | 836.68 |
| 494 | 102.32 | 290.97 |
| 495 | >250 | 747.51 |
| 496 | 64.01 | 154.23 |
| 497 | 64.50 | 568.51 |
| 498 | 50.67 | 259.54 |
| 499 | 163.43 | 500.79 |
| 500 | 107.96 | 457.00 |
| 501 | 20.86 | 108.40 |
| 502 | 9.06 | 44.35 |
| 503 | 5.22 | 5.47 |
| 504 | 6.78 | 5.62 |
| 505 | 5.61 | 10.05 |
| 506 | 8.82 | 8.67 |
| 507 | 9.83 | 19.68 |
| 508 | 14.99 | 29.01 |
| 509 | 49.53 | 90.08 |
| 510 | 245.60 | 382.06 |
| 511 | >250 | 431.47 |
| 512 | >250 | 1137.50 |
| 513 | >250 | 933.78 |
| 514 | 212.47 | 269.01 |
| 515 | 1.72 | 228.47 |
| 516 | 3.17 | 12.75 |
| 517 | 5.23 | 21.35 |
| 518 | 5.50 | 19.62 |
| 519 | 6.58 | 18.33 |
| 520 | 43.78 | 420.57 |
| 521 | 33.30 | 222.54 |
| 522 | 1.26 | 23.59 |
| 523 | 1.92 | 3.96 |
| 524 | 3.75 | 11.02 |
| 525 | 1.54 | 4.43 |
| 526 | 1.32 | 1.13 |
| 527 | 5.66 | 16.31 |
| 528 | 6.25 | 12.93 |
| 529 | 0.70 | 2.25 |
| 530 | 12.45 | 50.75 |
| 531 | 1.34 | 11.38 |
| 532 | 4.42 | 21.46 |
| 533 | 0.78 | 0.17 |
| 534 | 9.80 | 5.18 |
| 535 | 1.63 | 0.71 |
| 536 | 3.83 | 5.05 |
| 537 | 0.42 | 2.09 |
| 538 | 11.51 | 48.93 |
| 539 | 16.96 | 83.68 |
| 540 | 0.36 | 13.52 |
| 541 | 0.55 | 36.26 |
| 542 | 0.47 | 11.67 |
| 543 | 1.43 | 17.35 |
| 544 | 1.01 | 0.13 |
| 545 | 0.40 | 0.22 |
| 546 | 1.23 | 0.69 |
| 547 | 0.31 | 0.13 |
| 548 | 0.63 | 0.13 |
| 549 | 0.99 | 0.28 |
| 550 | 1.67 | 0.83 |
| 551 | 0.24 | 0.13 |
| 552 | 2.76 | 15.20 |
| 553 | 1.39 | 6.89 |
| 554 | 1.57 | 12.00 |
| 555 | 13.26 | 266.85 |
| 556 | 3.41 | 13.95 |
| 557 | 1.71 | 9.73 |
| 558 | 2.87 | 20.44 |
| 559 | 0.97 | 7.77 |
| 560 | 0.85 | 2.86 |
| 561 | 0.71 | 3.06 |
| 562 | 0.97 | 2.64 |
| 563 | 0.66 | 10.63 |
| 564 | 2.53 | 31.30 |
| 565 | 1.98 | 9.24 |
| 566 | 0.78 | 4.46 |
| 567 | 1.73 | 7.93 |
| 568 | 2.84 | 8.10 |
| 569 | 6.66 | 11.16 |
| 570 | 0.80 | 0.84 |
| 571 | 30.40 | 62.31 |
| 572 | 25.28 | 93.92 |
| 573 | 1.21 | 7.46 |
| 574 | 0.73 | 17.30 |
| 575 | 57.08 | 141.99 |
| 576 | 2.05 | 6.90 |
| 577 | 19.55 | 81.16 |
| 578 | 160.78 | 1867.50 |
| 579 | 19.12 | 110.87 |
| 580 | 1.63 | 5.79 |
| 581 | 0.89 | 2.16 |
| 582 | 4.96 | 15.61 |
| 583 | 2.63 | 9.53 |
| 584 | 0.91 | 2.98 |
| 585 | 0.69 | 1.90 |
| 586 | 0.85 | 2.94 |
| 587 | 23.33 | 66.14 |
| 588 | 0.69 | 2.33 |
| 589 | 0.63 | 2.56 |
| 590 | 1.05 | 2.04 |
| 591 | 0.72 | 0.17 |
| 592 | 96.22 | 773.99 |
| 593 | 7.24 | 33.00 |
| 594 | 0.58 | 0.12 |
| 595 | 1.27 | 0.52 |
| 596 | 0.70 | 0.14 |
| 597 | 2.79 | 5.93 |
| 598 | 1.11 | 0.11 |
| 599 | 2.38 | 41.16 |
| 600 | 2.59 | 6.64 |
| 601 | 1.16 | 0.17 |
| 602 | 0.93 | 0.53 |
| 603 | 1.94 | 0.09 |
| 604 | 0.83 | 0.12 |
| 605 | 1.26 | 0.12 |
| 606 | 3.08 | 2.42 |
| 607 | 0.90 | 0.23 |
| 608 | 2.36 | 0.48 |
| 609 | 2.36 | 0.39 |
| 610 | 0.37 | 0.23 |
| 611 | 0.40 | 0.07 |
| 612 | 6.06 | 1.02 |
| 613 | 0.58 | 0.71 |
| 614 | 2.06 | 0.13 |
| 615 | 1.54 | 0.28 |
| 616 | 2.30 | 0.20 |
| 617 | 0.78 | 0.22 |
| 618 | 0.34 | 0.13 |
| 619 | 0.95 | 0.14 |

TABLE 5-continued

Activity Data from CD73 Biochemical IC50 assay (1 mM NaH$_2$PO$_4$) and MDA-MB-231 Cell based CD73 activity assay (DMEM)

| Example No. | IC50-CD73 (nM) | EC50 (nM) |
|---|---|---|
| 620 | 1.22 | 0.07 |
| 621 | 1.32 | 0.32 |
| 622 | 2.87 | 27.26 |
| 623 | 2.27 | 22.03 |
| 624 | 5.81 | 0.32 |
| 625 | 2.47 | 10.12 |
| 626 | 5.16 | 0.26 |
| 627 | 2.57 | >50 |
| 628 | 0.73 | 0.23 |
| 629 | 0.20 | 0.05 |
| 630 | 0.32 | 0.08 |
| 633 | 1.55 | 7.08 |
| 634 | 5.19 | 38.98 |
| 635 | 2.08 | 2.75 |
| 636 | 0.34 | 0.13 |
| 637 | 2.06 | 0.39 |
| 639 | 2.42 | 0.58 |
| 640 | 1.60 | 0.12 |
| 641 | 77.54 | 206.57 |
| 642 | 37.83 | 153.96 |
| 643 | 36.42 | 98.88 |
| 644 | >250 | 1416.80 |
| 645 | 48.95 | 79.64 |
| 646 | >250 | 338.27 |
| 647 | 128.54 | 233.79 |
| 648 | >250 | 1947.60 |
| 649 | 11.75 | 21.72 |
| 650 | 6.86 | 18.76 |
| 651 | 128.75 | 480.48 |
| 652 | 19.56 | 79.60 |
| 653 | 25.34 | 129.75 |
| 654 | 54.53 | 133.41 |
| 655 | 40.37 | 253.74 |
| 656 | 10.14 | 56.95 |
| 657 | 81.34 | 226.69 |
| 658 | 1.87 | 7.88 |
| 659 | 3.98 | 38.15 |
| 660 | 6.05 | 33.57 |
| 661 | 4.68 | 25.48 |
| 662 | 19.16 | 88.62 |
| 663 | 24.53 | 159.53 |
| 664 | 0.92 | 0.21 |
| 665 | 1.46 | 2.79 |
| 666 | 1.80 | 2.80 |
| 667 | 100.42 | 413.82 |
| 668 | >250 | 857.30 |
| 669 | >250 | 690.37 |
| 670 | 154.42 | 572.73 |
| 671 | >250 | 1618.60 |
| 672 | 147.66 | 382.84 |
| 673 | 5.46 | 31.58 |
| 674 | 16.34 | 48.11 |
| 675 | 49.50 | 78.74 |
| 676 | 141.12 | 429.31 |
| 677 | 12.23 | 22.24 |
| 678 | 23.86 | 38.83 |
| 679 | 67.92 | 124.25 |
| 680 | 224.61 | 453.73 |
| 681 | 61.26 | 94.03 |
| 682 | 1.59 | 17.89 |
| 683 | 1.31 | 10.87 |
| 684 | 1.29 | 5.84 |
| 685 | >250 | 551.08 |
| 686 | 45.03 | 285.26 |
| 687 | 8.72 | 53.47 |
| 688 | 7.02 | 34.16 |
| 689 | 3.02 | 10.59 |
| 690 | 12.70 | 21.94 |
| 691 | 43.34 | 348.80 |
| 692 | 3.20 | 23.15 |
| 693 | 9.78 | 49.41 |
| 694 | 0.61 | 0.23 |
| 695 | 1.82 | 17.44 |
| 696 | 0.51 | 105.12 |
| 697 | 0.65 | 0.27 |
| 698 | 3.84 | 0.81 |
| 699 | 3.15 | 0.56 |
| 700 | 4.37 | 0.54 |
| 701 | 3.04 | 2.56 |
| 702 | 1.70 | 0.26 |
| 703 | 1.24 | 0.14 |
| 704 | 0.73 | 0.36 |
| 705 | 0.40 | 0.07 |
| 706 | 0.33 | 0.15 |
| 707 | 2.65 | 8.88 |
| 708 | 3.30 | 6.21 |
| 709 | 1.24 | 0.40 |
| 710 | 1.43 | 4.06 |
| 713 | NA | 0.39 |
| 714 | 0.70 | 0.19 |
| 715 | 1.42 | 0.32 |
| 716 | 0.35 | 0.28 |
| 717 | 0.69 | 0.26 |
| 718 | 3.07 | 0.33 |
| 719 | 0.51 | 0.46 |
| 721 | 0.77 | 0.32 |
| 722 | 1.10 | 0.58 |
| 723 | 2.75 | 1.04 |
| 732 | 2.66 | 2.52 |
| 733 | 2.72 | 0.11 |
| 734 | 1.69 | 0.19 |
| 735 | 2.94 | 0.38 |
| 736 | 1.91 | 0.21 |
| 737 | 1.79 | 0.18 |
| 738 | 1.74 | 0.21 |
| 740 | 0.61 | 0.28 |
| 741 | 0.49 | 0.68 |
| 745 | 0.62 | 0.69 |
| 746 | 2.37 | 0.84 |
| 748 | 2.50 | 1.76 |

NA: not available

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound selected from the group consisting of:

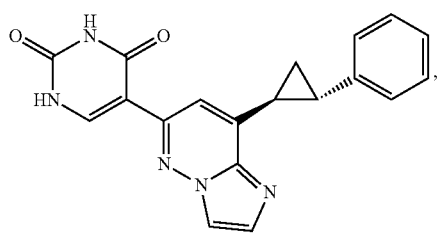

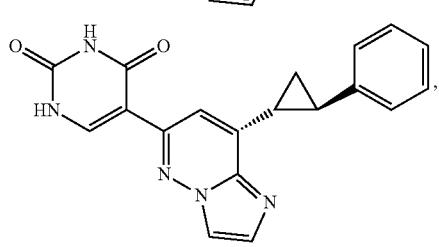

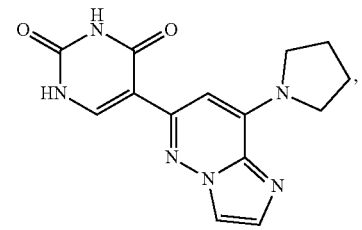

-continued

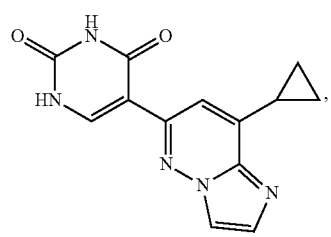

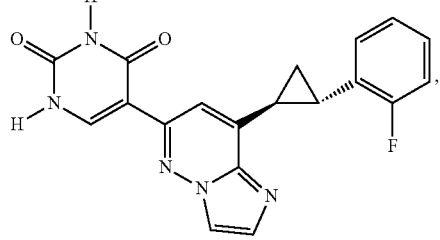

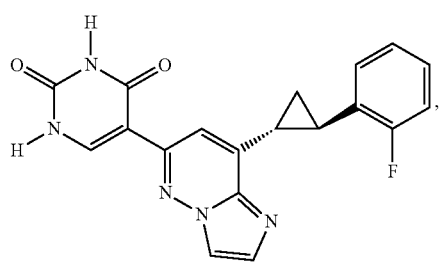

1611
-continued
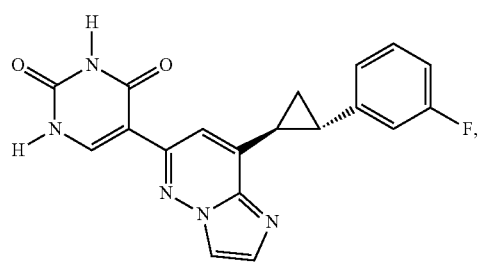
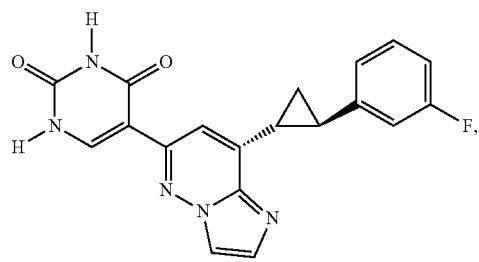
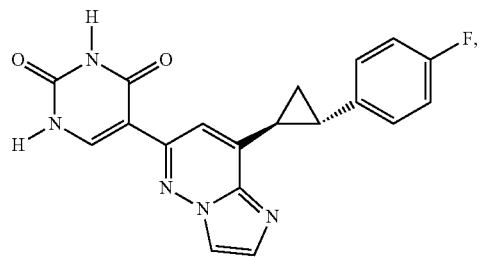
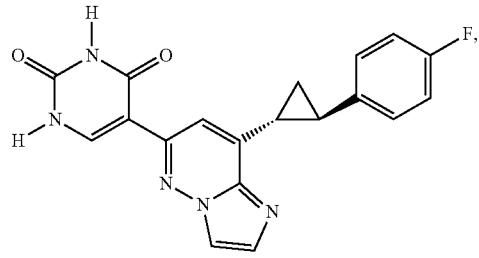
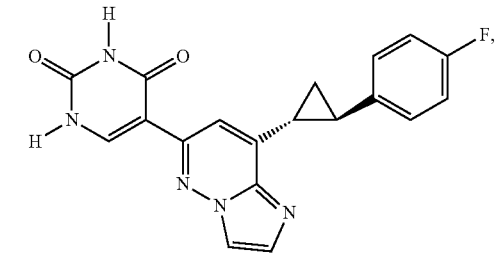
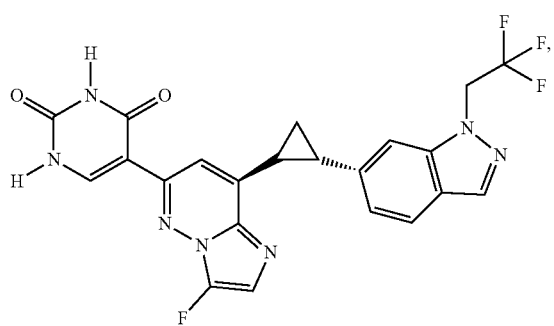
1612
-continued
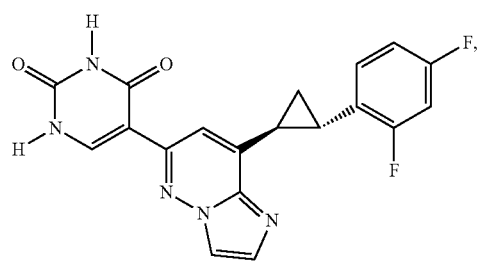
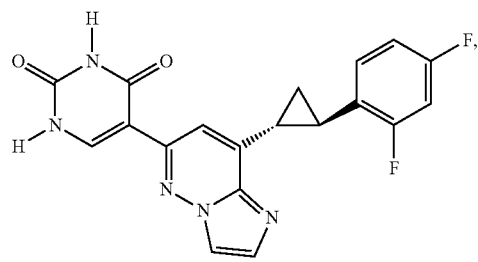
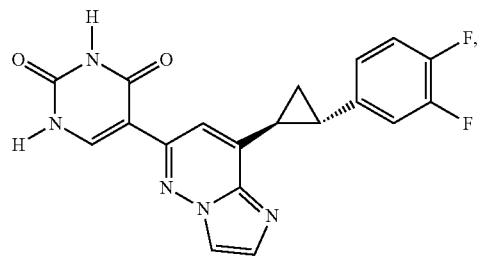
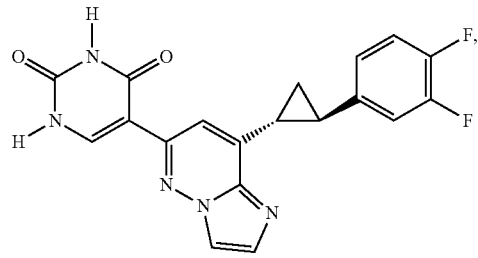
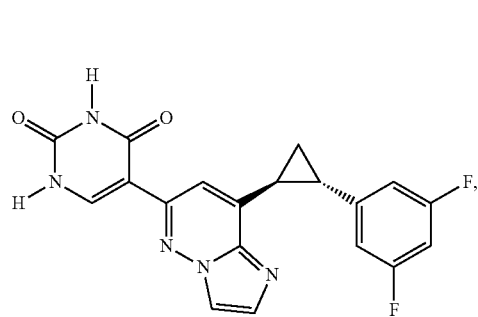
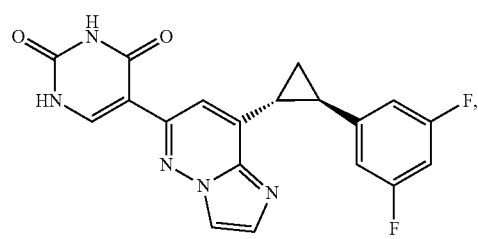

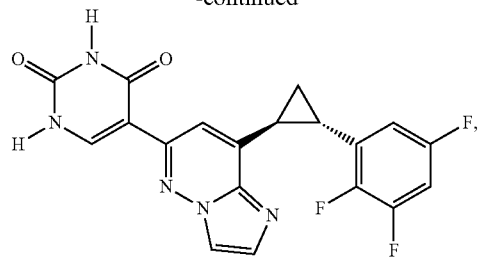

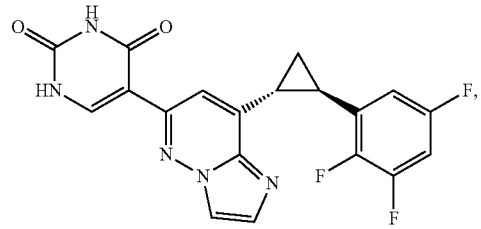

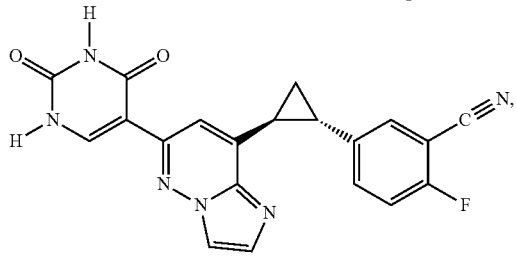

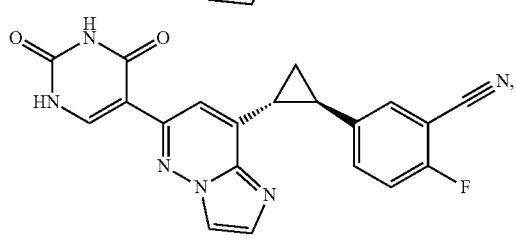

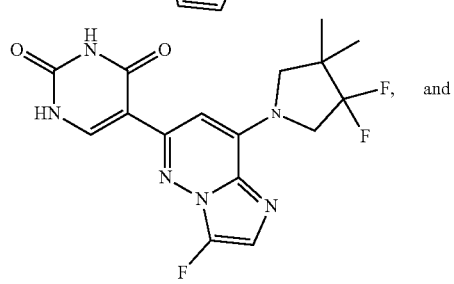

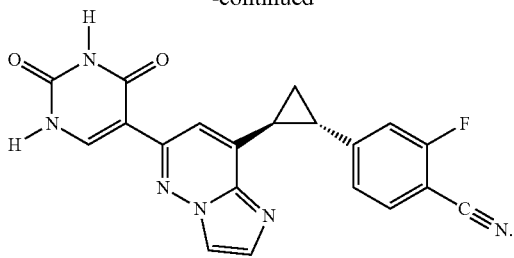

2. The compound of claim 1, which is:

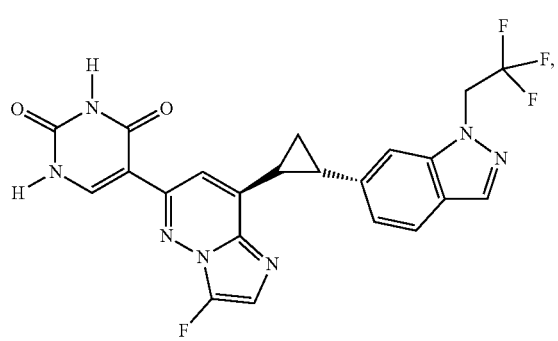

or a pharmaceutically acceptable salt thereof.

3. A pharmaceutical composition comprising a compound of claim 1 or a pharmaceutically acceptable salt thereof, and a pharmaceutically acceptable carrier or excipient.

4. The pharmaceutical composition of claim 3, further comprising one or more additional therapeutic agents.

5. The pharmaceutical composition of claim 4, wherein the additional therapeutic agent is independently an antineoplastic agent, chemotherapy, radiation therapy, or resection therapy.

6. The pharmaceutical composition of claim 5, wherein the additional therapeutic agent is independently rituxan, doxorubicin, gemcitabine, nivolumab, pembrolizumab, nivolumab, atezolizumab or ipilimumab.

7. The pharmaceutical composition of claim 5, wherein the additional therapeutic agent is a PD-1 or PD-L1 inhibitor.

* * * * *

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Cys Pro Leu Tyr Ile Ser Tyr Asp Pro Val Cys Arg Arg
1               5                   10                  15

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Arg Cys Pro Leu Tyr Ile Ser Tyr Asp Pro Val Cys Arg
1               5                   10                  15

Arg Arg Arg
```